(12) United States Patent
Polyak et al.

(10) Patent No.: US 11,644,466 B2
(45) Date of Patent: May 9, 2023

(54) METHODS FOR TREATING, PREVENTING AND PREDICTING RISK OF DEVELOPING BREAST CANCER

(71) Applicant: Dana-Farber Cancer Institute, Inc., Boston, MA (US)

(72) Inventors: Kornelia Polyak, Brookline, MA (US); Vanessa Almendro, Brookline, MA (US); Sibgat Choudhury, Chestnut Hill, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 143 days.

(21) Appl. No.: 16/704,941

(22) Filed: Dec. 5, 2019

(65) Prior Publication Data

US 2020/0256873 A1 Aug. 13, 2020

Related U.S. Application Data

(63) Continuation of application No. 14/414,674, filed as application No. PCT/US2013/032384 on Mar. 15, 2013, now abandoned.

(60) Provisional application No. 61/672,973, filed on Jul. 18, 2012.

(51) Int. Cl.
*G01N 33/53* (2006.01)
*G01N 33/574* (2006.01)

(52) U.S. Cl.
CPC ... *G01N 33/57415* (2013.01); *G01N 2333/47* (2013.01); *G01N 2333/705* (2013.01); *G01N 2333/70585* (2013.01); *G01N 2333/70596* (2013.01); *G01N 2800/50* (2013.01)

(58) Field of Classification Search
CPC .............................................. G01N 33/57415
USPC ...................................................... 435/7.23
See application file for complete search history.

(56) References Cited

U.S. PATENT DOCUMENTS

| | | | |
|---|---|---|---|
| 4,046,722 A | 9/1977 | Rowland |
| 4,046,784 A | 9/1977 | Gipson |
| 4,331,647 A | 5/1982 | Goldenberg |
| 4,348,376 A | 9/1982 | Goldenberg |
| 4,361,544 A | 11/1982 | Goldenberg |
| 4,444,744 A | 4/1984 | Goldenberg |
| 4,460,459 A | 7/1984 | Shaw et al. |
| 4,460,561 A | 7/1984 | Goldenberg |
| 4,468,457 A | 8/1984 | Goldenberg |
| 4,624,846 A | 11/1986 | Goldenberg |
| 4,671,958 A | 6/1987 | Rodwell et al. |
| 4,814,470 A | 3/1989 | Colin |
| 4,818,709 A | 4/1989 | Primus |
| 4,857,653 A | 7/1989 | Colin |
| 4,924,011 A | 5/1990 | Denis |
| 5,034,506 A | 7/1991 | Summerton |
| 5,093,246 A | 3/1992 | Cech |
| 5,270,163 A | 12/1993 | Gold et al. |
| 5,290,957 A | 3/1994 | Correa |
| 5,292,921 A | 3/1994 | Correa |
| 5,332,567 A | 7/1994 | Goldenberg |
| 5,438,072 A | 8/1995 | Bobee |
| 5,443,953 A | 8/1995 | Hansen |
| 5,541,297 A | 7/1996 | Hansen |
| 5,587,493 A | 12/1996 | Bouchard |
| 5,601,825 A | 2/1997 | Hansen |
| 5,637,288 A | 6/1997 | Goldenberg |
| 5,637,684 A | 6/1997 | Cook |
| 5,677,427 A | 10/1997 | Goldenberg |
| 5,677,437 A | 10/1997 | Teng |
| 5,686,578 A | 11/1997 | Goldenberg |
| 5,698,178 A | 12/1997 | Goldenberg |
| 5,780,607 A | 7/1998 | Goodnow, Jr. |
| 5,783,682 A | 7/1998 | Cook |
| 5,792,844 A | 7/1998 | Sanghvi |
| 5,789,554 A | 8/1998 | Leung |
| 5,811,234 A | 9/1998 | Roninson |
| 5,814,500 A | 9/1998 | Dietz |
| 5,922,302 A | 7/1999 | Goldenberg |
| 6,004,940 A | 12/1999 | Marasco |
| 6,187,287 B1 | 2/2001 | Leung |
| 6,319,500 B1 | 11/2001 | Goldenberg |
| 8,097,645 B2 | 1/2012 | Wyss-Coray |
| 8,211,634 B2 | 7/2012 | Depinho et al. |
| 2001/0024831 A1 | 9/2001 | Der Maur |
| 2005/0208500 A1 | 9/2005 | Erlander et al. |
| 2008/0085874 A1 | 4/2008 | Kushner et al. |
| 2010/0255470 A1 | 10/2010 | Bankaitis-Davis et al. |
| 2010/0285995 A1 | 11/2010 | Russo et al. |
| 2011/0229504 A1 | 9/2011 | Fritsche et al. |
| 2012/0003639 A1 | 1/2012 | Kerlikowske |
| 2015/0285802 A1 | 10/2015 | Polyak et al. |

FOREIGN PATENT DOCUMENTS

| | | |
|---|---|---|
| EP | 0253738 | 1/1988 |
| WO | WO 91/17976 | 11/1991 |
| WO | WO 91/19813 | 12/1991 |
| WO | WO 93/00928 | 1/1993 |

(Continued)

OTHER PUBLICATIONS

Warner et al (JAMA, 2004, 292(11): 1317-1325).*
Harris et al (BMC Cancer, 2006, 6(27): 1-5).*
Barnes et al (British Journal of Cancer, 2007, 96: 575-582).*
Li et al (Cancer Management and Research, 2018, 10: 4653-4667).*
Amerongen et al (Cell Stem Cell, 2012, 11: 387-400).*
Arora et al., c-Myc antisense limits rat liver regeneration and indicates role for c-Myc in regulating cytochrome P-450 3A activity, J. Pharmacol. Exp. Ther.;292(3):921-928 (2000).
Asztalos et al. Gene expression patterns in the human breast after pregnancy, Cancer Prev Res (Phila) 3(3):301-311 (2010).
Asztalos et al., Gene Expression Patterns in the Human Breast after Pregnancy, Cancer Prev Res; 3(3):301-311 (Mar. 2010).

(Continued)

*Primary Examiner* — Sean E Aeder
(74) *Attorney, Agent, or Firm* — Fish & Richardson P.C.

(57) ABSTRACT

Methods for treating, preventing and predicting a subject's risk of developing breast cancer are provided.

10 Claims, 38 Drawing Sheets

Specification includes a Sequence Listing.

(56) References Cited

FOREIGN PATENT DOCUMENTS

| | | |
|---|---|---|
| WO | WO 93/00929 | 1/1993 |
| WO | WO 94/02610 | 2/1994 |
| WO | WO 96/01815 | 1/1996 |
| WO | WO 96/39154 | 12/1996 |
| WO | WO 97/03211 | 1/1997 |
| WO | WO 2000/70349 | 11/2000 |

OTHER PUBLICATIONS

Barringer et al.. Blunt-end and single-strand ligations by *Escherichia coli* ligase: influence on an in vitro amplification scheme, Gene 89(1):117 (1990).
Belitskaya-Levy et al. Characterization of a genomic signature of pregnancy identified in the breast, Cancer Prev Res (Phila) 4(9):1457-1464 (2011).
Belitskaya-Lévy et al., Characterization of a Genomic Signature of Pregnancy in the Breast, Cancer Prev Res, 4(9): 1457-1464 (Sep. 2011).
Bernstein et al., Role for a bidentate ribonuclease in the initiation step of RNA interference, Nature, 409(6818):363-366 (2001).
Bessarabova, M., et al. Functional synergies yet distinct modulators affected by genetic alterations in common human cancers , Cancer Res 71(10):3471-3481 (2011).
Blakely, C.M., et al. Hormone-induced protection against mammary tumorigenesis is conserved in multiple rat strains and identifies a core gene expression signature induced by pregnancy, Cancer Res 66(12):6421-6431 (2006).
Bloushtain-Qimron, et al. Cell type-specific DNA methylation patterns in the human breast, Proc Natl Acad Sci USA 105(37):14076-14081 (2008).
Brady et al., Therapeutic and diagnostic uses of modified monoclonal antibodies, nt. J. Rad. Oncol. Biol. Phys. 13(10):1535-1544 (1987).
Brummelkamp et al., A system for stable expression of short interfering RNAs in mammalian cells, Science; 296(5567):550-553 (2002).
Chehab et al. Detection of specific DNA sequences by fluorescence amplification: a color complementation assay Proc. Natl. Acad. Sci. USA, 86:9178-9182 (1989).
Cohen, J. A Coefficient of Agreement for Nominal Scales, Educational and Psychological Measurement, 20(1):37-46 (1960).
Desmedt, C., et al. Strong time dependence of the 76-gene prognostic signature for node-negative breast cancer patients in the TRANSBIG multicenter independent validation series , Clin Cancer Res 13(11):3207-3214 (2007).
Donzé and Picard, RNA interference in mammalian cells using siRNAs synthesized with T7 RNA polymerase, Nucleic Acids Res. 30(10):e46 (2002).
Egholm, M., et al. PNA Hybridizes to Complementary Oligonucleotides Obeying the Watson-Crick Hydrogen Bonding Rules, Nature, 365(6446):566-568 (1993).
Elbashir et al., RNA interference is mediated by 21- and 22-nucleotide RNAs, Genes Dev. 15(2):188-200 (2001).
Elbashir et al., Duplexes of 21-nucleotide RNAs mediate RNA interference in cultured mammalian cells, Nature; 411(6836): 494-498 (2001).
Garbe, J.C., et al. Molecular distinctions between stasis and telomere attrition senescence barriers shown by long-term culture of normal human mammary epithelial cells, Cancer Res 69(19):7557-7568 (2009).
Gautier et al., Alpha-DNA. IV: Alpha-anomeric and beta-anomeric tetrathymidylates covalently linked to intercalating oxazolopyridocarbazole. Synthesis, physicochemical properties and poly (rA) binding, Nucl. Acids Res. 15(16):6625-6641 (1987).
Gianni et al.. J. Clin. Oncol., 27:15:2474-2481 (2009).
Giatromanolaki et al (Mol Oncol, 2011, 28: 745-752).
Gibson et al., A novel method for real time quantitative RT-PCR, Genome Research 6(10):995-1001, (1996).
Gong et al (PLoS ONE, 2010, 5(12): e15630, pp. 1-11).
Guatelli et al. Isothermal, in vitro amplification of nucleic acids by a multienzyme reaction modeled after retroviral replication, Proc. Nat. Acad. Sci. USA 87(5):1874-8 (1990).
Haakensen, V.D., et al. Gene expression profiles of breast biopsies from healthy women identify a group with claudin-low features, BMC Medical Genomics 4:77 (2011).
Haakensen, V.D., et al. Serum estradiol levels associated with specific gene expression patterns in normal breast tissue and in breast carcinomas, BMC Cancer 11:332 ( Aug. 2011).
Hambardzumyan, et al., The probable cell of origin of NF1- and PDGF-driven glioblastomas, PLoS One 6(9): e24454 (2011).
Hammond et al., Post-transcriptional gene silencing by double-stranded RNA, Nature Genet; 2(2):110-119 (2001).
Haseloff and Gerlach, Simple RNA enzymes with new and highly specific endoribonuclease activities, Nature 334(6183):585-591 (1988).
Heasman et al., Beta-catenin signaling activity dissected in the early Xenopus embryo: a novel antisense approach, Dev. Biol., 222(1):124-134 (2000).
Heid et al., Real time quantitative PCR, Genome Research 6(10):986-994 (1996).
Heller, DNA microarray technology: Devices, Systems, and Applications, Annual Review of Biomedical Engineering; 4:129-153 (2002).
Hu, M., et al. Distinct epigenetic changes in the stromal cells of breast cancers. Nat Genet 37(8), 899-905 (2005).
Huang et al. Total synthesis of the potent cAMP signaling agonist (-)-alotaketal A, J. Am. Chem. Soc., 134(21):8806-8809 (2012).
Huang, et al. The DAVID Gene Functional Classification Tool: a novel biological module-centric algorithm to functionally analyze large gene lists, Genome Biol 8(9): R183 (2007).
International Preliminary Report on Patentability in International Application No. PCT/US2013/032384, dated Jan. 20, 2015, 13 pages.
International Search Report and Written Opinion of the International Searching Authority for PCT/US2013/032384 dated Jun. 14, 2013.
Jaggupilli et al., "Significance of CD44 and CD24 as Cancer Stem Cell Markers: An Enduring Ambiguity," Clinical and Development Immunology, vol. 2012, pp. 1-11.
Jepsen and Wengel, LNA-antisense rivals siRNA for gene silencing, Curr. Opin. Drug Discov. Devel., 7(2):188-194 (2004).
Kordon and Smith, An entire functional mammary gland may comprise the progeny from a single cell, Development 125(10):1921-1930 (1998).
Kwoh et al. Transcription-based amplification system and detection of amplified human immunodeficiency virus type 1 with a bead-based sandwich hybridization format, Proc. Natl. Acad. Sci. USA 86(4):1173-7 (1989).
Landegren et al. A ligase-mediated gene detection technique, Science 241(4869):1077-80 (1988).
Lee et al (Br J Cancer, 2011, 104(11 ): 1730-1738).
Lin et al., "CD44+/CD24-Phenotype Contributes to Malignant Relapse Following Surgical Resection and Chemotherapy in Patients with Ductal Carcinoma," Journal of Experimental and Clinical Cancer Research, Jul. 4, 2012, 31:59, pp. 1-9.
Lin, et a, Image-guided sampling reveals increased stroma and lower glandular complexity in mammographically dense breast tissue, Breast Cancer Res Treat 128(2): 505-516 (2011).
Lockhart et al. Expression monitoring by hybridization to high-density oligonucleotide arrays Nature Biotechnology, 14: 1675-1680 (1996).
Lu et al, Ultrastruct Patho, 2011, 35(2): 72-78).
Marasco, W.A. Intrabodies: turning the humoral immune system outside in for intracellular immunization, Gene Therapy 4(1):11-15 (1997).
Maruyama, R. et al. Epigenetic regulation of cell type-specific expression patterns in the human mammary epithelium, PLoS Genetics 7(4): e1001369 (2011).
Mata A hexameric phosphorothioate oligonucleotide telomerase inhibitor arrests growth of Burkitt's lymphoma cells in vitro and in vivo, Toxicol. Appl. Pharmacol. 144(1):189-197 (1997).

(56) References Cited

OTHER PUBLICATIONS

McManus et al., Gene silencing in mammals by small interfering RNAs, Nature Reviews Genetics, 3(10):737-47 (2002).
McManus et al., Gene silencing using micro-RNA designed hairpins, RNA 8(6):842-850 (2002).
Milligan et al., Current concepts in antisense drug design, J. Med. Chem. 36(14):1923-1937 (1993).
Mylona et al (Human Pathology, 2008, 39: 1096-1102).
Nasevicius and Ekker, Effective targeted gene 'knockdown' in zebrafish, Nat. Genet. 26(2):216-220 (2000).
Nielsen et al., Sequence-selective recognition of DNA by strand displacement with a thymine-substituted polyamide, Science 254(5037):1497-500 (1991).
Nielsen, P.E. PNA Technology, Mol Biotechnol. 26(3):233-48 (2004).
Nielsen. P.E. Triple Helix: Designing a New Molecule of Life, Scientific American, (Dec. 2008).
Nikolsky, Y., et al., Functional analysis of OMICs data and small molecule compounds in an integrated "knowledge-based" platform, Methods Mol Biol 563:177-196 (2009).
Nikolsky, Y., et al.., Genome-wide functional synergy between amplified and mutated genes in human breast cancer, Cancer Res 68(22):9532-9540 (2008).
Paddison et al., Short hairpin RNAs (shRNAs) induce sequence-specific silencing in mammalian cells, Genes Dev. 16(8): 948-958 (2002).
Pastan et al. Immunotoxins. Cell 47(5):641-8 (1986).
Paul et al., Effective expression of small interfering RNA in human cells, Nature Biotechnol. 20(5):505-508 (2002).
Phillips et al (Journal of National Cancer Institute, 2006, 98(24): 1777-1785).
Rademann ad Jung, Integrating Combinatorial Synthesis and Bioassays, Science, 287:1947-1948 (2000).
Rossi, Practical ribozymes. Making ribozymes work in cells, Current Biology 4(5):469-471 (1994).
Russo et al., Full-term pregnancy induces a specific genomic signature in the human breast, Cancer Epidemiol Biomarkers Prev 17(1):51-66 (2008).
Russo et al., Full-term Pregnancy Induces a Specific Genomic Signature in the Human Breast, Cancer Epidemiol Biomarkers Prev 2008;17(1):51-66. (Jan. 2008).
Russo et al., Pregnancy-induced chromatin remodeling in the breast of postmenopausal women, Int J Cancer, 131(5):1059-1070 (Sep. 2012).
Samstag, Synthesis and properties of new antisense oligodeoxynucleotides containing benzylphosphonate linkages, Antisense Nucleic Acid Drug Dev 6(3):153-156 (1996).
Satchi-Fainaro et al., Inhibition of vessel permeability by TNP-470 and its polymer conjugate, caplostatin, Cancer Cell 7(3), 251-61 (2005).
Schena et al. Parallel human genome analysis: Microarray-based expression monitoring of 1000 genes Proc. Natl. Acad. Sci. USA, 93:10614-10619 (1996).
Schmidt, Robert A. Stereotactic Breast Biopsy, CA Cancer J Clin, 44:172-191 (1994).
Schreiber, Target-Oriented and Diversity-Oriented Organic Synthesis in Drug Discovery, Science 287:1964-1969 (2000).
Sharp, RNAi and double-strand RNA, Genes Dev. 13(2):139-141 (1999).
Sheridan et al., "CD44+CD24-Breast Cancer Cells Exhibit Enhanced Invasive Properties: An Early Step Necessary for Metastasis," Breast Cancer Research, 2006, pp. 1-13.
Shi, W., et al. Functional analysis of multiple genomic signatures demonstrates that classification algorithms choose phenotype-related genes, Pharmacogenomics J 10(4):310-323 (2010).
Shipitsin, M., et al. Molecular definition of breast tumor heterogeneity, Cancer Cell 11(3):259-273 (2007).
Sotiriou, C., et al. Gene expression profiling in breast cancer: understanding the molecular basis of histologic grade to improve prognosis, J Natl Cancer Inst 98(4): 262-272 (2006).
Southern, Detection of specific sequences among DNA fragments separated by gel electrophoresis, J. Mol. Biol. 98(3):503 (1975).
Strauss-Soukup Effects of neutralization pattern and stereochemistry on DNA bending by methylphosphonate substitutions, Biochemistry 36(29):8692-8698 (1997).
Subramanian et al. Gene set enrichment analysis: a knowledge-based approach for interpreting genome-wide expression profiles, Proc Natl Acad Sci USA 102(43):15545-15550 (2005).
Sui et al., A DNA vector-based RNAi technology to suppress gene expression in mammalian cells, Proc. Natl. Acad. Sci. USA 99(8):5515-5520 (2002).
Summerton and Weller, Morpholino antisense oligomers: design, preparation, and properties, Antisense Nucleic Acid Drug Dev. 7(3):187-195 (1997).
Summerton, Morpholino antisense oligomers: the case for an RNase H-independent structural type, Biochim. Biophys. Acta 1489(1):141-158 (1999).
Tamimi, R.M., et al., Comparison of molecular phenotypes of ductal carcinoma in situ and invasive breast cancer, Breast Cancer Res 10(4): R67 (2008).
Tibshirani, R., et al. Sample classification from protein mass spectrometry, by peak probability contrasts, Bioinformatics 20(17):3034-3044 (2004).
Tuschl, RNA interference and small interfering RNAs, Chem. Biochem, 2(4):239-245 (2001).
Tusher, et al., Significance analysis of microarrays applied to the ionizing radiation response, Proc Natl Acad Sci USA 98(9):5116-5121 (2001).
Van de Vijver, M.J et al. A gene-expression signature as a predictor of survival in breast cancer, N Engl J Med 347(25):1999-2009 (2002).
Vitetta et al. Redesigning nature's poisons to create anti-tumor reagents, Science 238(4830):1098-1104 (1987).
Wang, Y., et al. Gene-expression profiles to predict distant metastasis of lymph-node-negative primary breast cancer, Lancet 365(9460): 671-679 (2005).
Watson et al. Technology for microarray analysis of gene expression. Curr Opin Biotechnol (1998) 9(6):609-14 (1998).
Wu and Wallace, The ligation amplification reaction (LAR)-amplification of specific DNA sequences using sequential rounds of template-dependent ligation, Genomics 4(4):560-569 (1989).
Wu, et al. Gene expression profiling of human breast tissue samples using SAGE-Seq, Genome Res 20(12):1730-1739 (2010).
Yu et al., RNA interference by expression of short-interfering RNAs and hairpin RNAs in mammalian cells, Proc. Natl. Acad. Sci. USA 99:6047-6052 (2002).
Anderson, "The role of oestrogen and progesterone receptors in human mammary development and tumorigenesis," Breast cancer research: BCR, Jul. 24, 2002, 4(5):197-201.
Anothaisintawee et al., "Risk prediction models of breast cancer: a systematic review of model performances," Breast cancer research and treatment, May 2012, 133(1):1-0.
Chen et al., "Risk factors and hormone-receptor status: epidemiology, risk-prediction models and treatment implications for breast cancer," Nat. Clin, Pract. Oncol. Jul. 2007, 4(7):415-23.
Cheng et al., "Stem cell repopulation efficiency but not pool size is governed by p27 kip1," Nature medicine, Nov. 2000, 6(11):1235-40.
Chung et al., "Breast epithelial cell proliferation is markedly increased with short-term high levels of endogenous estrogen secondary to controlled ovarian hyperstimulation," Breast cancer research and treatment, Apr. 2012, 132(2):653-60.
Clarke et al., "Dissociation between steroid receptor expression and cell proliferation in the human breast," Cancer research, Nov. 15, 1997, 57(22):4987-91.
Colditz, et al. "Risk factors for breast cancer according to estrogen and progesterone receptor status," Journal of the national cancer institute, Feb. 4, 2004 96(3):218-28.
Collins et al., "Potential role of tissue microarrays for the study of biomarker expression in benign breast disease and normal breast tissue," Applied immunohistochemistry & molecular morphology: AIMM/official publication of the Society for Applied Immunohistochemistry, Oct. 2009, 17(5):438.

(56) References Cited

OTHER PUBLICATIONS

Collins et al., "The influence of family history on breast cancer risk in women with biopsy-confirmed benign breast disease: results from the Nurses' Health Study," Cancer, Sep. 15, 2006, 107(6):1240-7.
Dickson et al., "Chapter 8: Estrogen receptor-mediated processes in normal and cancer cells," JNCI Monographs, Jul. 2000, 2000(27):135-45.
Dowsett et al., "Short-term changes in Ki-67 during neoadjuvant treatment of primary breast cancer with anastrozole or tamoxifen alone or combined correlate with recurrence-free survival," Clinical Cancer Research, Jan. 15, 2005, 11(2):951s-8s.
Fero et al., "A syndrome of multiorgan hyperplasia with features of gigantism, tumorigenesis, and female sterility in p27Kip1-deficient mice," Cell, May 31, 1996, 85(5):733-44.
Feuerhake et al., "Cell proliferation, apoptosis, and expression of Bcl-2 and Bax in non-lactating human breast epithelium in relation to the menstrual cycle and reproductive history," Breast cancer research and treatment, Jan. 2003, 77(1):37-48.
Guan et al., "p27Kip1 as a prognostic factor in breast cancer: a systematic review and meta-analysis," Journal of cellular and molecular medicine, Apr. 2010, 14(4):944-53.
Hameed et al., "Immunohistochemical staining for cyclin D1 and Ki-67 aids in the stratification of atypical ductal hyperplasia diagnosed on breast core biopsy," American journal of clinical pathology, Dec. 2005, 124(6):862-72.
Iqbal et al., "Subgroups of non-atypical hyperplasia of breast defined by proliferation of oestrogen receptor-positive cells," The Journal of pathology, Mar. 2001, 193(3):333-8.
Khan et al., "Estrogen receptor expression in benign breast epithelium and breast cancer risk," JNCI: Journal of the National Cancer Institute, Jan. 7, 1998 90(1):37-42.
Khan et al., "The normal breast epithelium of women with breast cancer displays an aberrant response to estradiol," Cancer Epidemiology and Prevention Biomarkers, Oct. 1999, 8(10):867-72.
Kiyokawa et al., "Enhanced growth of mice lacking the cyclin-dependent kinase inhibitor function of p27Kip1," Cell, May 31, 1996, 85(5):721-32.
Krishnamurthy et al., "Molecular and biologic markers of premalignant lesions of human breast," Advances in anatomic pathology, May 2002, 9(3):185-97.
Lee et al., "Hormones, receptors, and growth in hyperplastic enlarged lobular units: early potential precursors of breast cancer," Breast Cancer Research. Feb. 2005, 8(1):1-9.
Lim et al., "Aberrant luminal progenitors as the candidate target population for basal tumor development in BRCA1 mutation carriers," Nature medicine, Aug. 2009, 15(8):907-13.
Page et al., "Atypical hyperplastic lesions of the female breast. A long-term follow-up study. Cancer," Jun. 1985, 55(11):2698-708.
Polyak et al., "Cloning of p27Kip1, a cyclin-dependent kinase inhibitor and a potential mediator of extracellular antimitogenic signals," Cell, Jul. 15, 1994, 78(1):59-66.
Ricketts et al., "Estrogen and progesterone receptors in the normal female breast," Cancer research, Apr. 1991, 51(7):1817-22.
Santisteban et al., "Ki67: a time-varying biomarker of risk of breast cancer in atypical hyperplasia," Breast cancer research and treatment, Jun. 2010, 121(2):431-7.
Shaaban et al., "Breast cancer risk in usual ductal hyperplasia is defined by estrogen receptor-α and Ki-67 expression," The American journal of pathology, Feb. 2002, 160(2):597-604.
Shoker et al., "Estrogen receptor-positive proliferating cells in the normal and precancerous breast," The American journal of pathology, Dec. 1999, 155(6):1811-5.
Suzuki et al., "Proliferation and differentiation in the human breast during pregnancy," Differentiation, Oct. 2000, 66(2-3):106-15.
Tamimi et al., "Expression of IGF1R in normal breast tissue and subsequent risk of breast cancer," Breast cancer research and treatment, Jul. 2011, 128(1):243-50.
Tan et al., "The cell cycle inhibitor p27 is an independent prognostic marker in small (T1a, b) invasive breast carcinomas," Cancer research, Apr. 1997, 57(7):1259-63.
Taylor et al., "Progesterone and estrogen receptors in pregnant and premenopausal non-pregnant normal human breast," Breast cancer research and treatment, Nov. 2009, 118(1):161-8.
Van Dierendonck et al., "Nuclear distribution of the Ki-67 antigen during the cell cycle: comparison with growth fraction in human breast cancer cells," Cancer research, Jun. 1989, 49(11):2999-3006.
Yerushalmi et al., "Ki67 in breast cancer: prognostic and predictive potential," The lancet oncology, Feb. 2010, 11(2):174-83.

\* cited by examiner

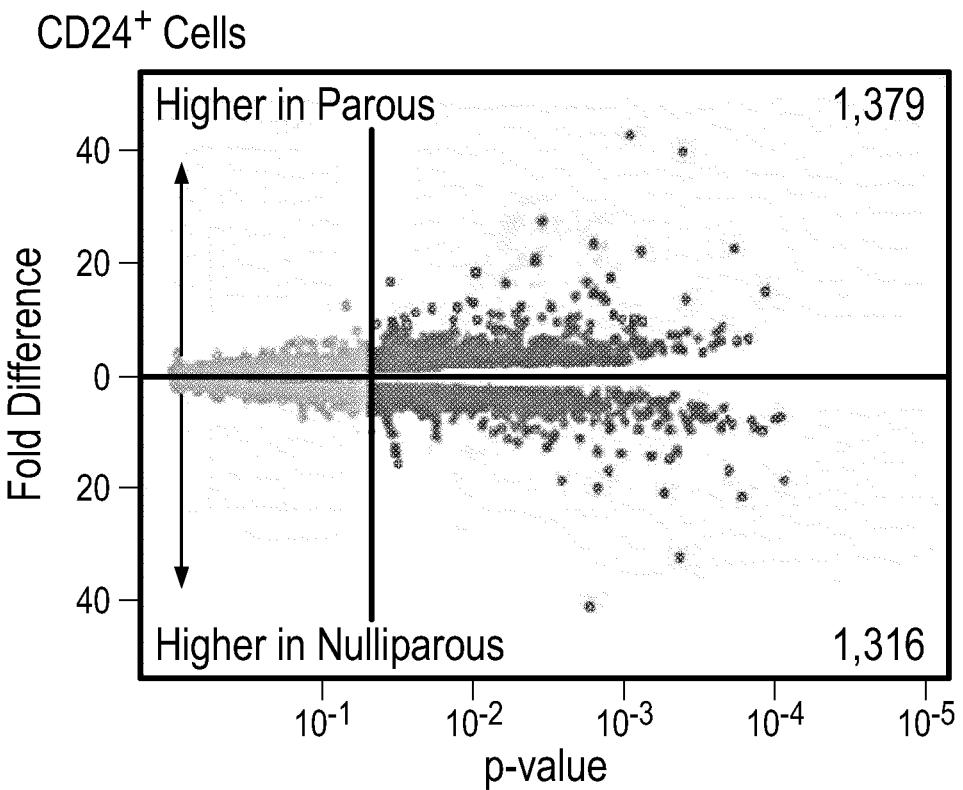
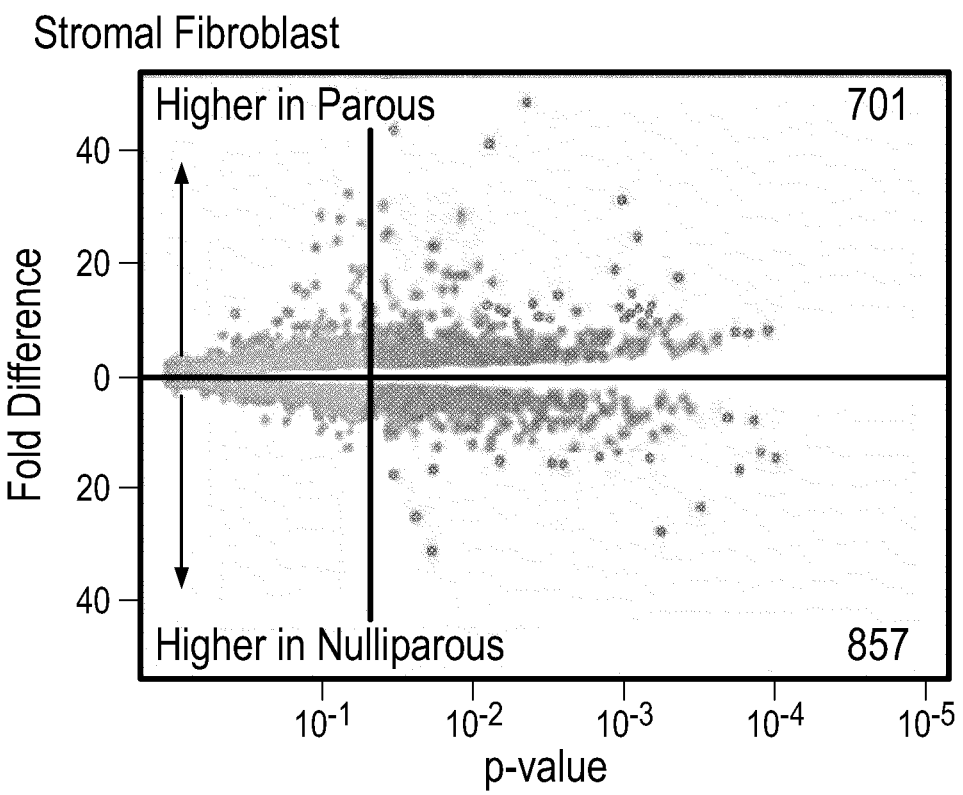
FIG. 3 (Cont.)

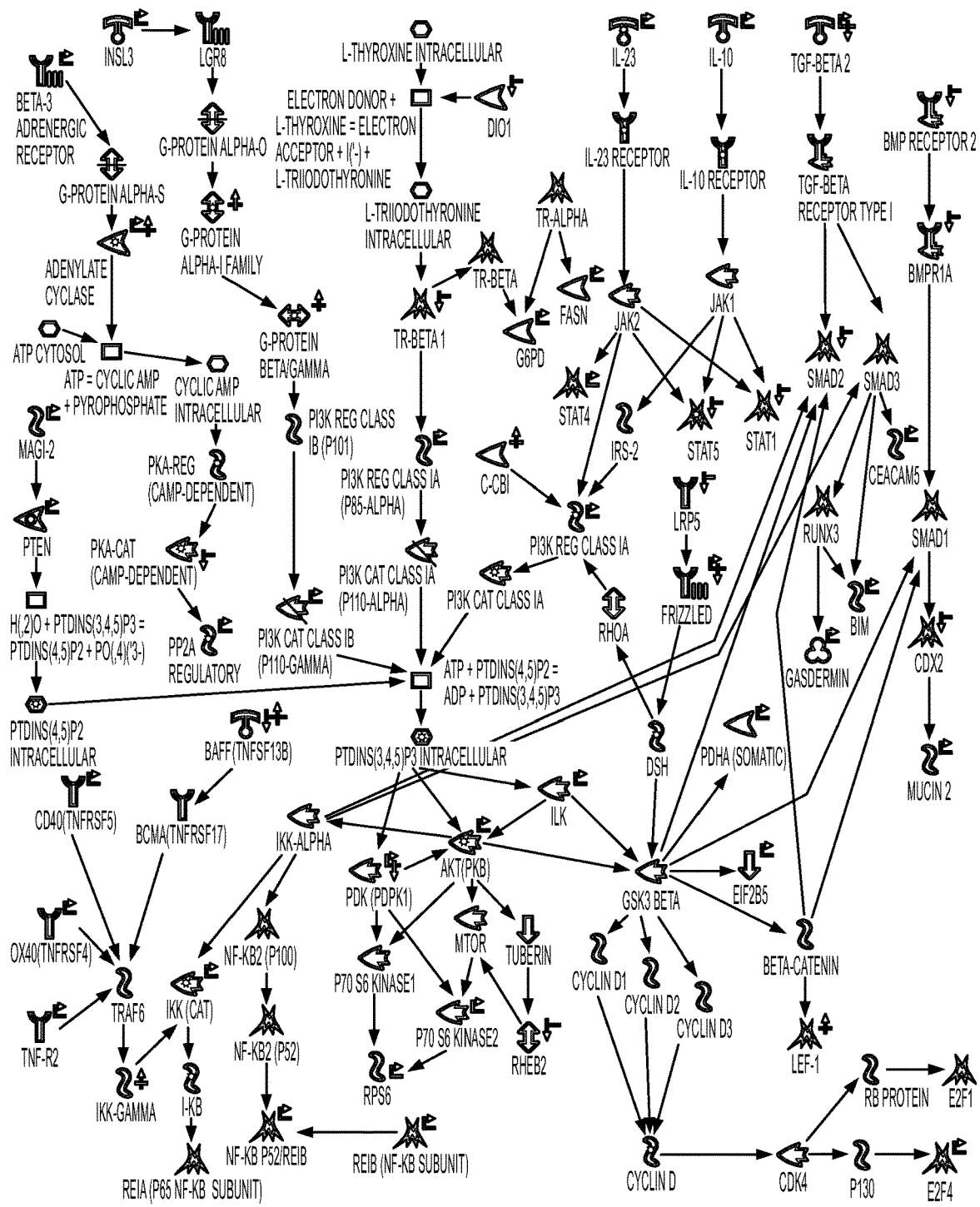
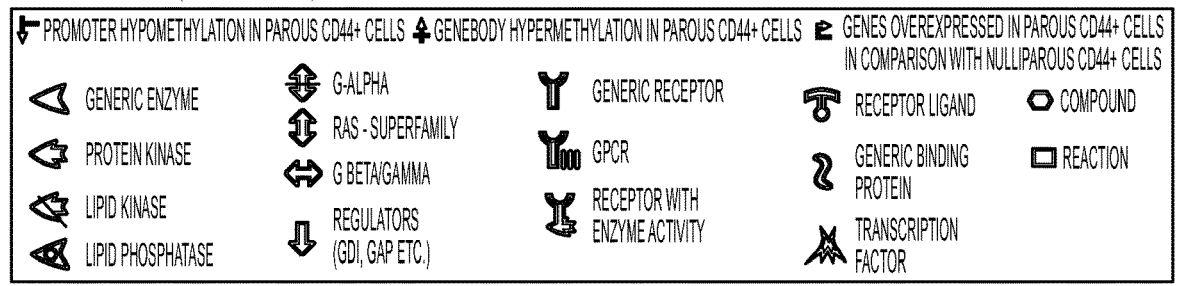
FIG. 13

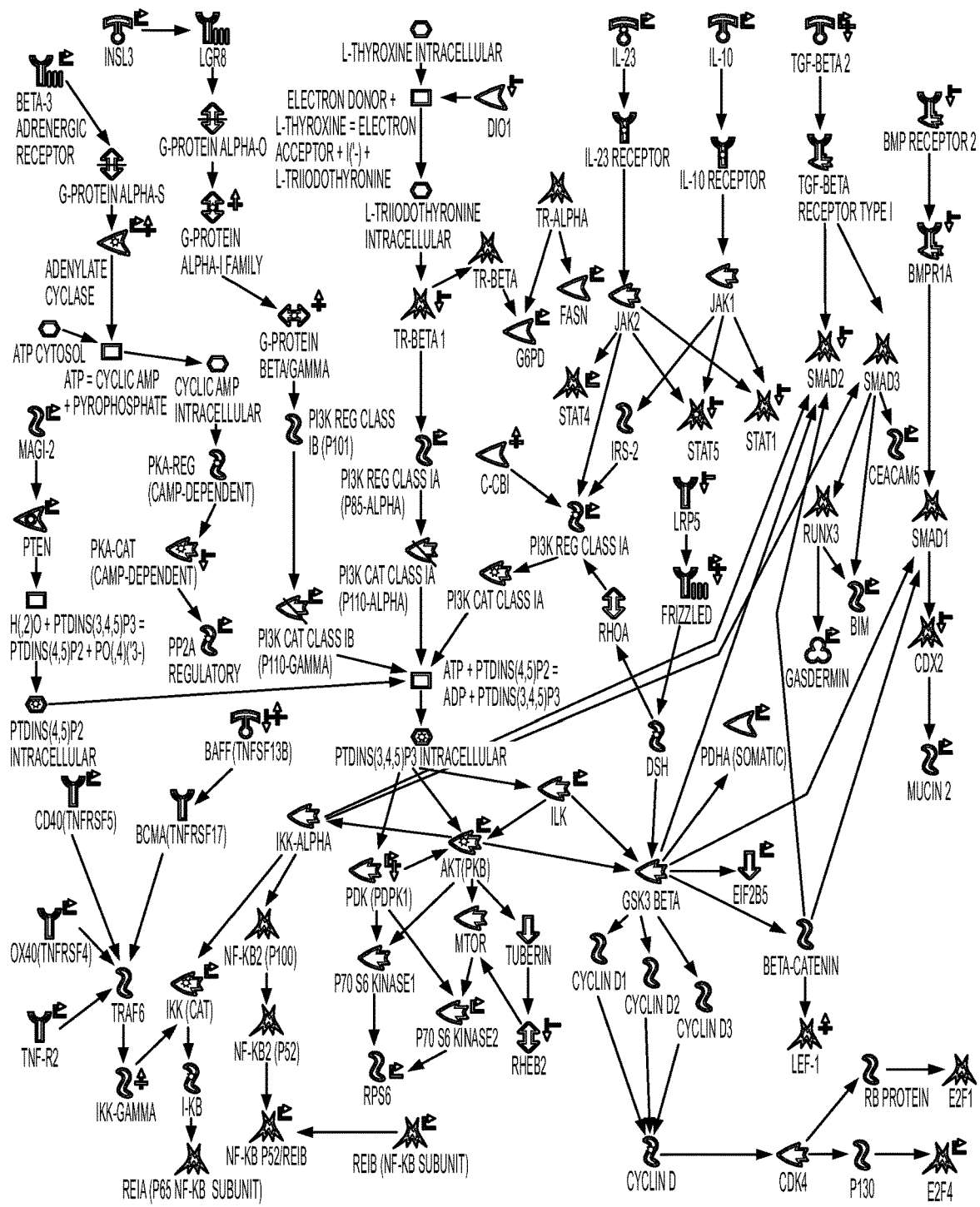
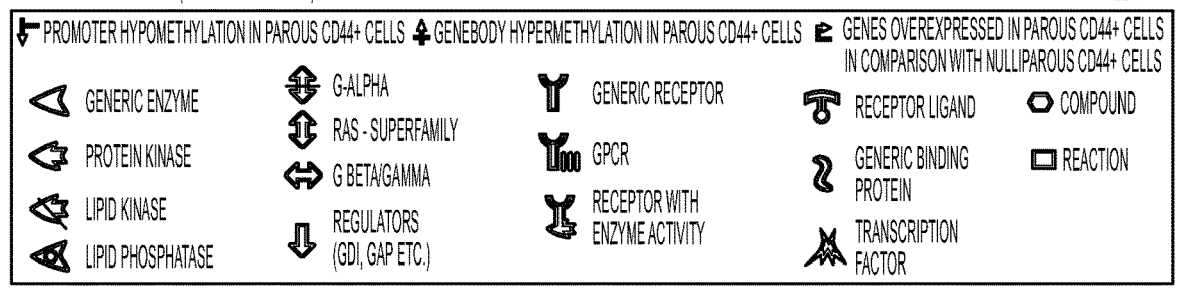
FIG. 14

| Common Pathways | P-val in Human | P-val in Rat |
|---|---|---|
| Cytoskeleton Remodeling | 1.02E-09 | 3.76E-04 |
| Cytoskeleton Remodeling_Regulation of Actin Cytoskeleton by Rho GTPases | 1.32E-09 | 9.98E-07 |
| Cytoskeleton Remodeling_TGF_WNT and Cytoskeleton Remodeling | 1.82E-09 | 2.68E-03 |
| Cell Adhesion_Chemokines and Adhesion | 2.62E-07 | 3.88E-03 |
| Cytoskeletal Remodeling_Role of PKA in Cytoskeletal Reorganization | 6.32E-07 | 9.01E-05 |
| Cell Adhesion_Histamine H1 Receptor Signaling in Interrupting Barrier Integrity | 3.19E-06 | 6.00E-03 |
| Cell Adhesion_Alpha-4 Integrins in Cell Migration and Adhesion | 3.66E-06 | 7.84E-03 |
| Development_Slit-Robo Signaling | 6.10E-06 | 4.53E-03 |

FIG. 15B

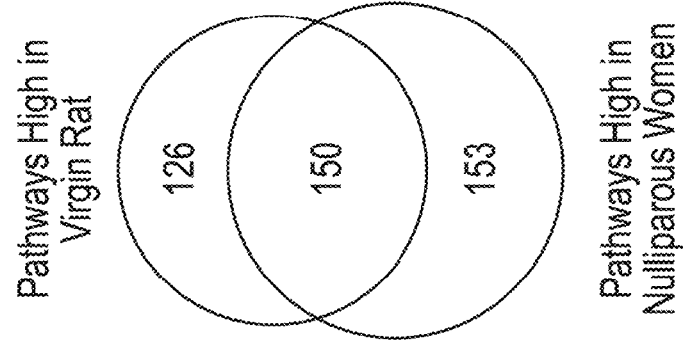

FIG. 15A

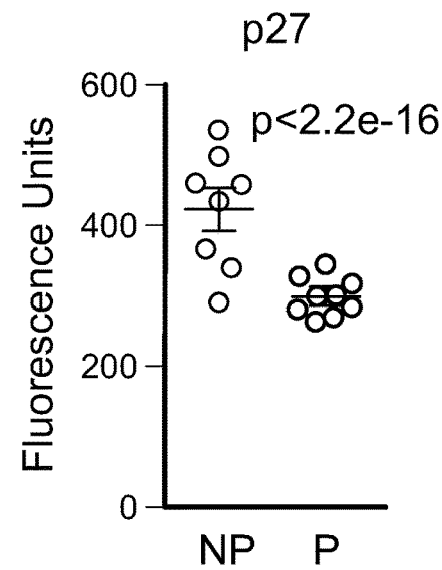
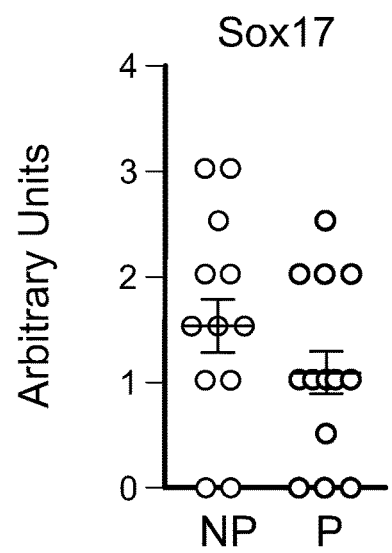
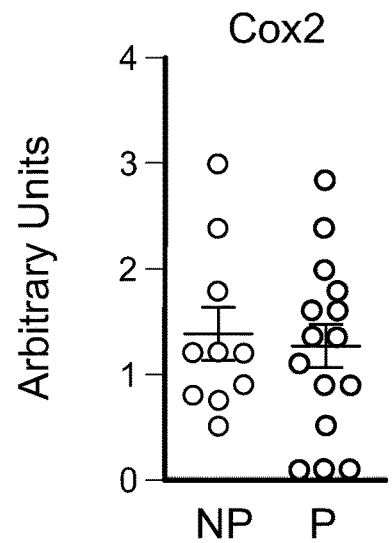
FIG. 18

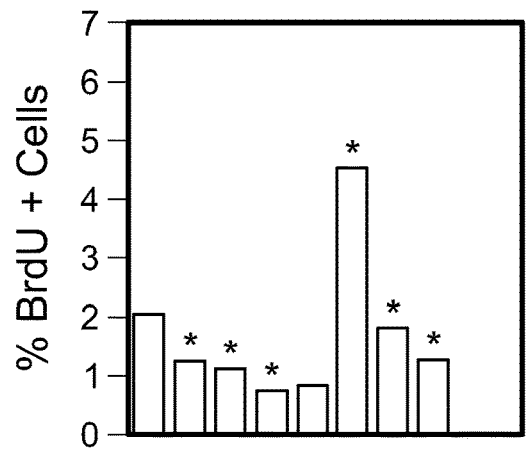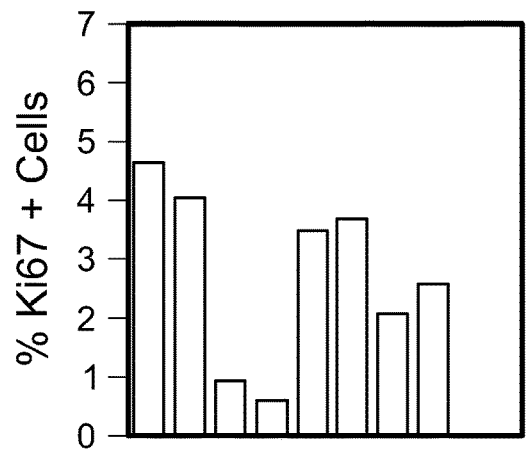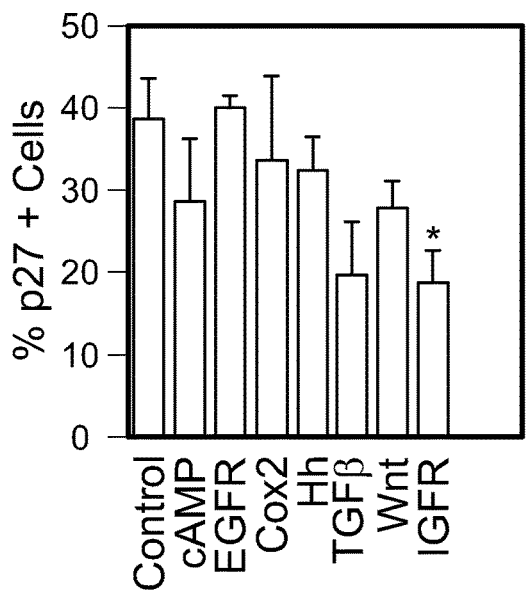
FIG. 24

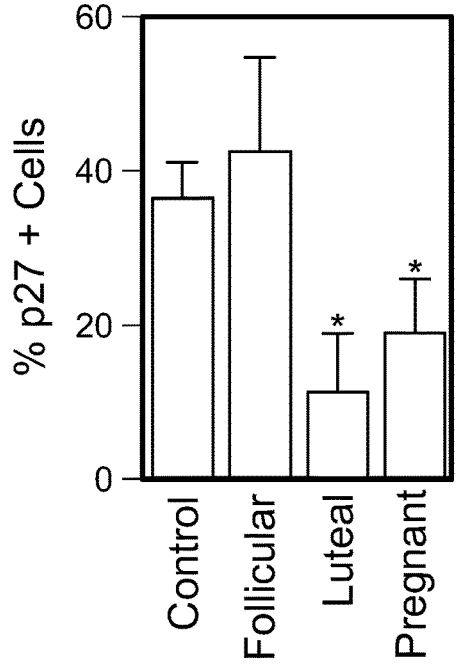
FIG. 26B
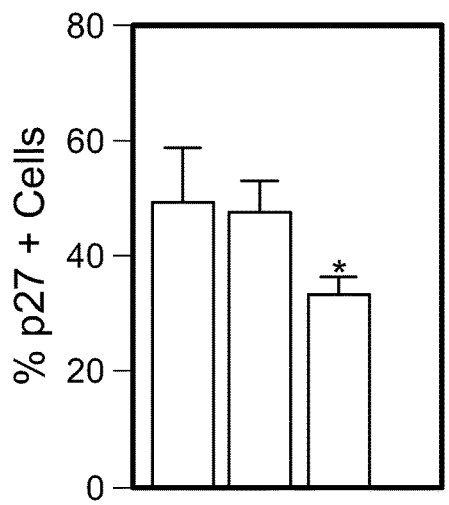
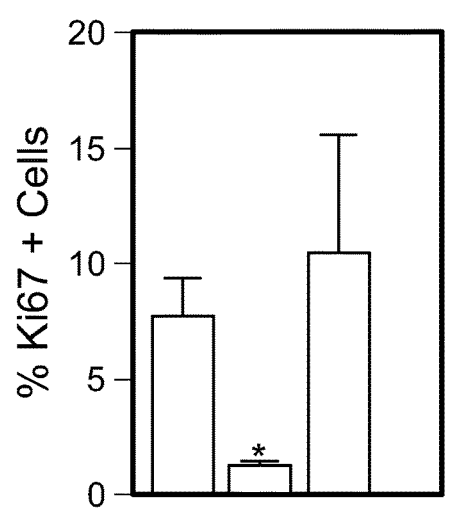
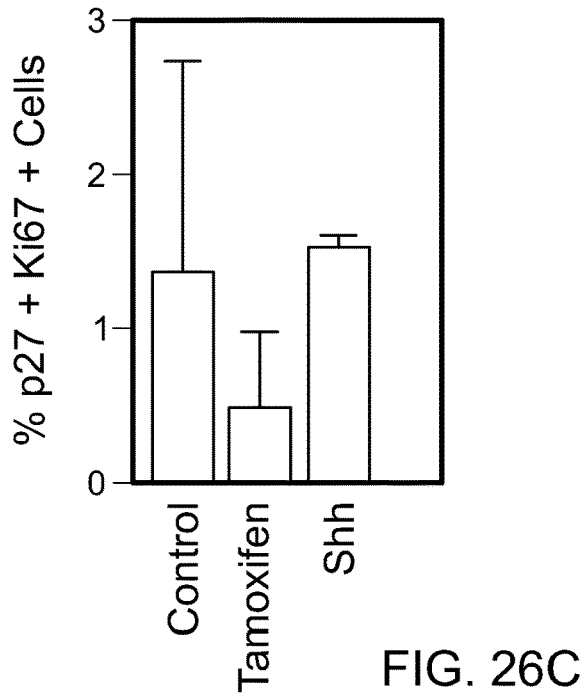
FIG. 26C

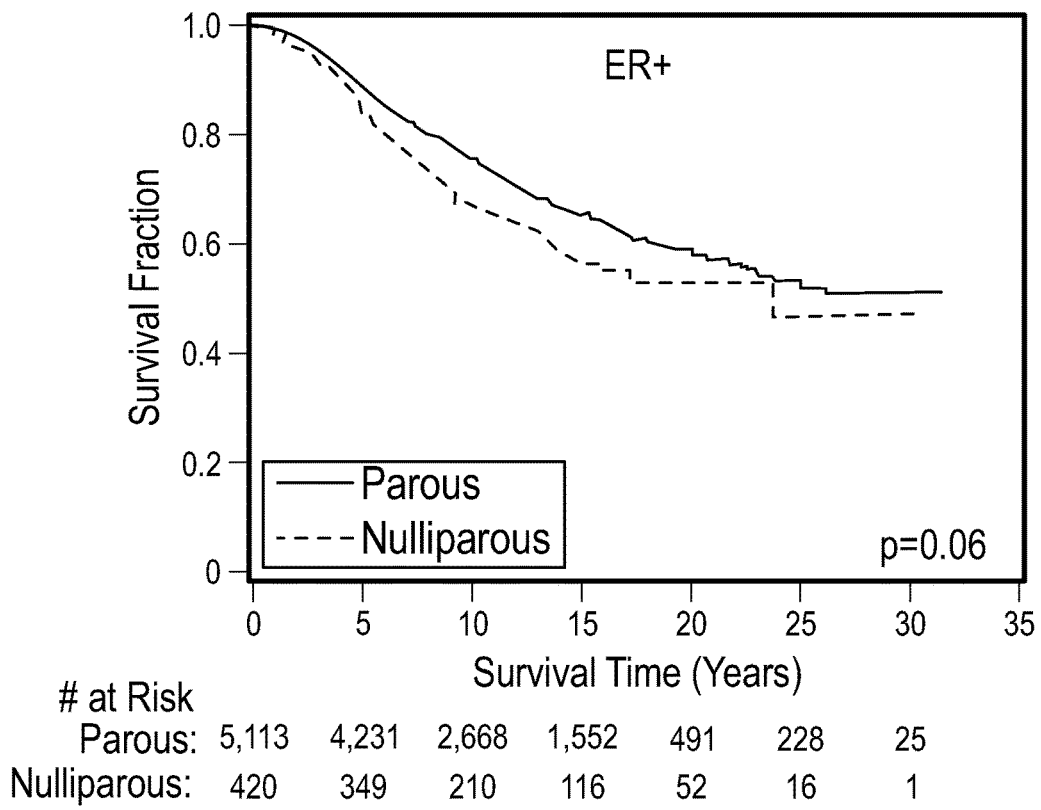
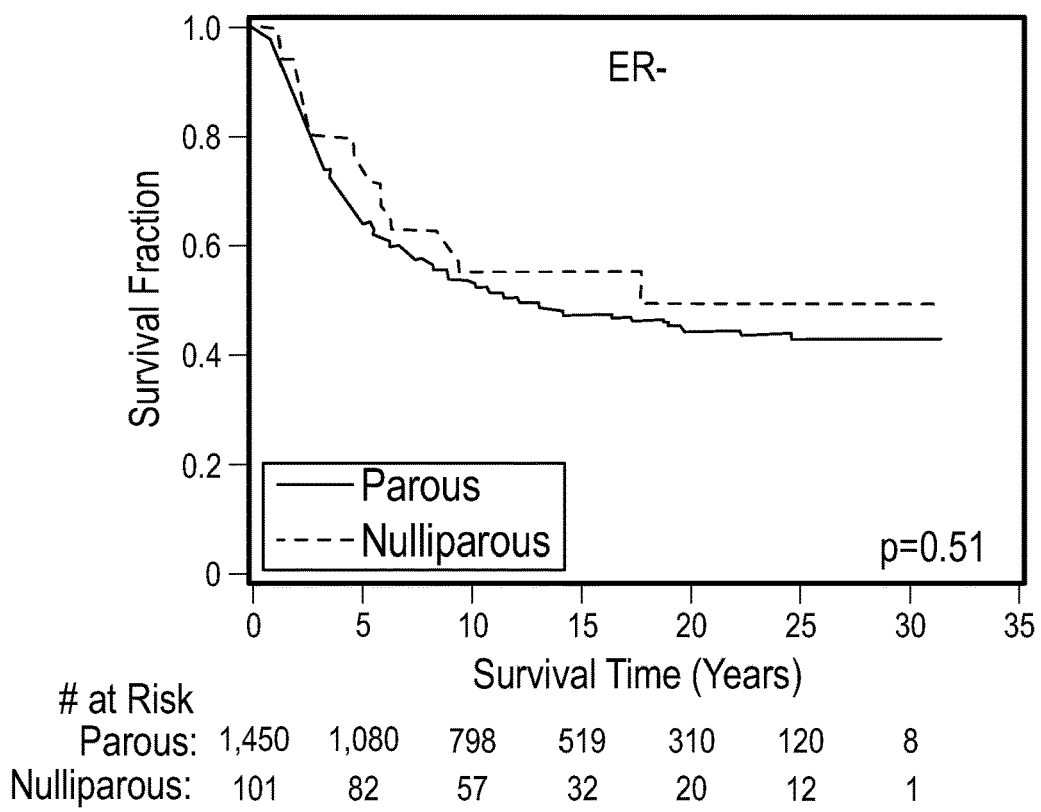
FIG. 27

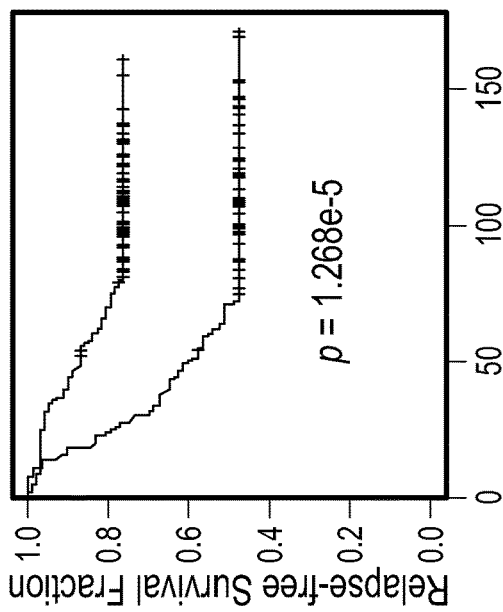
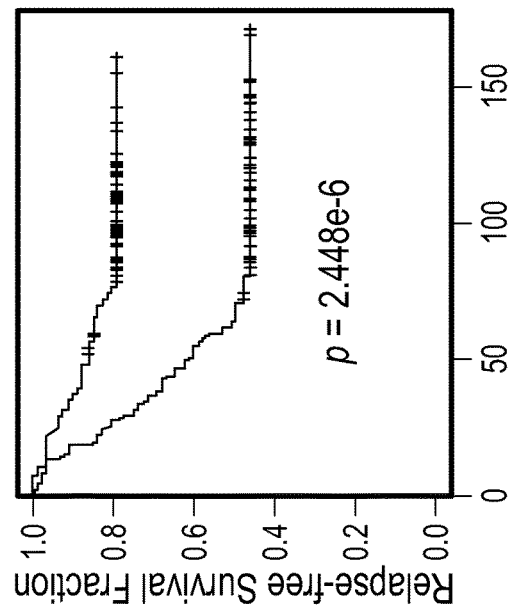
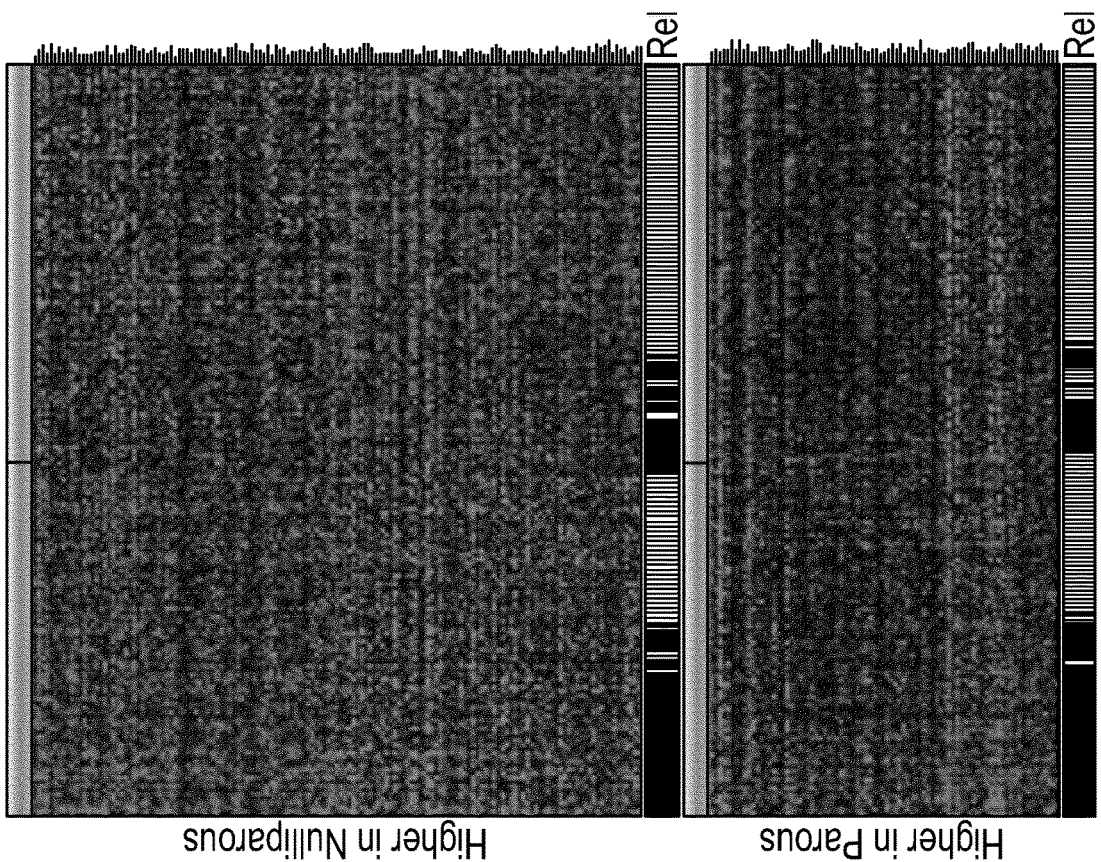
FIG. 29A

METHODS FOR TREATING, PREVENTING AND PREDICTING RISK OF DEVELOPING BREAST CANCER

RELATED APPLICATIONS

The present application is a continuation of U.S. patent application Ser. No. 14/414,674, filed Jan. 13, 2015, which is a U.S. National Stage patent application of International Application No. PCT/US2013/032384, filed Mar. 15, 2013, which claims the benefit of U.S. Provisional Patent Application Ser. No. 61/672,973, filed Jul. 18, 2012. The contents of all the prior applications are herein incorporated by reference in their entireties.

STATEMENT REGARDING FEDERALLY SPONSORED RESEARCH OR DEVELOPMENT

This invention was made with government support under grant numbers P01 CA117969, P50 CA089383, P01 CA080111, CA116235, CA087969, awarded by the National Institutes of Health and grant number W81XWH-07-1-0294 awarded by the Department of Defense. The government has certain rights in the invention.

TECHNICAL FIELD

Methods for treating, preventing and predicting a subject's risk of developing breast cancer are provided.

BACKGROUND

Breast cancer is the most common type of cancer among women in the United States, accounting for more than a quarter of all cancers in women. Approximately 2.5 million women in this country are breast cancer survivors, and an estimated 192,370 new cases of breast cancer were diagnosed in women in 2009. Further, estrogen receptor positive (ER+) postmenopausal breast cancer is the most common form of the disease. While advances in treatment have enabled more women to live longer overall and to live longer without disease progression, what is needed in the art are methods for identifying subjects at risk of developing breast cancer before they develop it, and for preventing the development of the disease altogether. Presently, however, very few reliable predictive markers for identifying subjects at high risk for developing breast cancer, such as ER+ or ER− breast cancer, are known.

BRCA1 and BRCA2 mutations are examples of predictive markers that have been correlated with an increased risk of developing breast cancer; however, only 5-10% of breast cancers are thought to be caused by inherited abnormalities in BRCA1 and BRCA2 (i.e. hereditary breast cancer). The remaining approximately 90-95% of all breast cancers are sporadic. Thus, what is needed in the art are novel markers that are useful for identifying subjects having an elevated risk of developing breast cancer, as well as novel targets of breast cancer therapies.

SUMMARY OF THE INVENTION

As follows from the Background section above, there remains a need in the art for methods for predicting a subject's risk of developing breast cancer. Such methods, as well as other, related benefits, are presently provided, as discussed in detail below.

In one aspect, a method of predicting a subject's risk of developing breast cancer is provided, wherein the method includes: (a) determining the frequency in a breast tissue sample of CD44+, CD24− breast epithelial cells, and (b) predicting that the subject has a relatively elevated risk of developing breast cancer if the frequency of CD44+, CD24− breast epithelial cells is decreased compared to a first control frequency of CD44+, CD24− breast epithelial cells; or (c) predicting that the subject has a relatively reduced risk of developing breast cancer if the frequency of CD44+ breast epithelial cells is increased compared to a second control frequency of CD44+, CD24− breast epithelial cells.

In another aspect, the method further includes determining the frequency of CD24+ breast epithelial cells. In one aspect, step (b) includes predicting that the subject has a relatively elevated risk of developing breast cancer if: (i) the frequency of CD44+, CD24− breast epithelial cells is decreased compared to a first control frequency of CD44+, CD24− breast epithelial cells, and (ii) the frequency of CD24+ breast epithelial cells is increased compared to a first control frequency of CD24+ breast epithelial cells; and step (c) includes predicting that the subject has a relatively reduced risk of developing breast cancer if: (i) the frequency of CD44+ breast epithelial cells is increased compared to a second control frequency of CD44+, CD24− breast epithelial cells, and (ii) the frequency of CD24+ breast epithelial cells is decreased compared to a second control frequency of CD24+ breast epithelial cells. In another aspect, step (b) includes: predicting that the subject has a relatively elevated risk of developing breast cancer if the frequency of CD24+ breast epithelial cells is greater than the frequency of CD44+, CD24− breast epithelial cells in the sample; and step (c) includes predicting that the subject has a relatively reduced risk of developing breast cancer if the frequency of CD24+ breast epithelial cells is equal to or less than the frequency of CD44+, CD24− breast epithelial cells in the sample. In still another aspect, the subject is in need of such predicting.

In another aspect, a method of predicting a subject's risk of developing breast cancer is provided. The method includes: (a) determining the frequency in a breast tissue sample of cells of one or more types selected from the group consisting of p27+ breast epithelial cells, Sox17+ breast epithelial cells, Cox2+ breast epithelial cells, Ki67+ breast epithelial cells, ER+, p27+ breast epithelial cells, ER+, Sox17+ breast epithelial cells, ER+, Cox2+ breast epithelial cells, ER+, Ki67+ breast epithelial cells; androgen-receptor-positive (AR+), p27+ breast epithelial cells, AR+, Sox17+ breast epithelial cells, AR+, Cox2+ breast epithelial cells, and AR+, Ki67+ breast epithelial cells; and (b) predicting that the subject has a relatively elevated risk of developing breast cancer if the frequency of the cells of the type is increased compared to a first control frequency of cells of the type; or (c) predicting that the subject has a relatively reduced risk of developing breast cancer if the frequency of the cells of the type is decreased compared to a second control frequency of the cells of the type.

In certain aspects, step (b) includes predicting that the subject has a relatively elevated risk of developing breast cancer if the frequency of p27+ breast epithelial cells is 15 percent (%) or greater of the breast epithelial cells in the sample; and step (c) includes predicting that the subject has a relatively reduced risk of developing breast cancer if the frequency of p27+ breast epithelial cells is less than 15% of the breast epithelial cells in the sample. In other aspects, step (b) includes predicting that the subject has a relatively elevated risk of developing breast cancer if the frequency of p27+ breast epithelial cells is 20 percent (%) or greater of the breast epithelial cells in the sample; and step (c) includes predicting that the subject has a relatively reduced risk of developing breast cancer if the frequency of p27+ breast epithelial cells is less than 20% of the breast epithelial cells in the sample. In still another aspect, step (b) includes predicting that the subject has a relatively elevated risk of developing breast cancer if the frequency of p27+ breast epithelial cells is 25 percent (%) or greater of the breast epithelial cells in the sample; and step (c) includes predicting that the subject has a relatively reduced risk of developing breast cancer if the frequency of p27+ breast epithelial cells is less than 25% of the breast epithelial cells in the sample. In certain aspects, step (b) includes predicting that the subject has a relatively elevated risk of developing breast cancer if the frequency of Ki67+ breast epithelial cells is 2 percent (%) or greater of the breast epithelial cells in the sample; and step (c) includes predicting that the subject has a relatively reduced risk of developing breast cancer if the frequency of Ki67+ breast epithelial cells is less than 2% of the breast epithelial cells in the sample. In yet other aspects, step (b) includes predicting that the subject has a relatively elevated risk of developing breast cancer if: (i) the frequency of p27+ breast epithelial cells is increased compared to a first control frequency of p27+ breast epithelial cells, and (ii) the frequency of Ki67+ breast epithelial cells is increased compared to a first control frequency of Ki67+ breast epithelial cells; and step (c) includes predicting that the subject has a relatively reduced risk of developing breast cancer if: (i) the frequency of p27+ breast epithelial cells is decreased compared to a second control frequency of p27+ breast epithelial cells, and (ii) the frequency of Ki67+ breast epithelial cells is decreased compared to a second control frequency of Ki67+ breast epithelial cells.

In another aspect, a method of predicting a subject's risk of developing breast cancer is provided. The method includes: (a) determining the expression level in a breast tissue sample from a subject of at least one marker selected from the group consisting of p27, Sox17 and Cox2; and (b) predicting that the subject has a relatively elevated risk of developing breast cancer if the expression level of the at least one marker is increased compared to a first control level of the at least one marker; or (c) predicting that the subject has a relatively reduced risk of developing breast cancer if the expression level of the at least one marker is decreased compared to a second control level of the at least one marker. In certain aspects, the expression level determined is the mRNA expression level of the at least one marker. In other aspects, the expression level determined is the protein expression level of the at least one marker. In certain aspects, step (a) includes determining the expression level of at least two (2) markers or all 3 markers selected from the group consisting of p27, Sox17 and Cox2.

In some aspects, step (a) further includes determining the expression level of one or more additional markers having an expression level that is modulated in breast epithelial cells of parous women compared to the levels in breast epithelial cells of nulliparous women. In certain aspects, the sample is enriched for CD44+, CD24− breast epithelial cells or for CD24+ breast epithelial cells prior to the determining. In still other aspects, the sample is enriched for Ki67+ breast epithelial cells or CD44+ Ki67+ breast epithelial cells prior to the determining.

In certain aspects, the subject for whom the risk of developing an estrogen-receptor-positive (ER+) breast cancer is being predicted has a BRCA1 and/or a BRCA2 mutation.

In other aspects, a method of predicting a subject's risk of developing breast cancer is provided, which includes determining a parity/nulliparity-associated gene expression signature in a sample containing breast epithelial cells. In certain aspects, the sample is enriched for CD44+ cells, CD24+ cells, or CD10+ cells.

In one aspect, a method of predicting breast cancer disease outcome is provided, including testing for a parity/nulliparity-associated gene expression signature in breast cancer cells.

In another aspect, a method of treating estrogen-receptor-positive (ER+) breast cancer in a subject is provided. The method includes administering to the subject a composition that includes an inhibitor of a pathway that has increased activity in CD44+, CD24− breast epithelial cells of nulliparous women compared to the activity in CD44+, CD24− breast epithelial cells of parous women. In certain aspects, the pathway can be cytoskeleton remodeling, chemokines, androgen signaling, cell adhesion, or Wnt signaling.

In yet another aspect, a method of preventing breast cancer in a subject is provided. The method includes administering to a subject at risk of developing breast cancer an inhibitor of a pathway that has increased activity in breast epithelial cells of nulliparous women compared to breast epithelial cells of parous women. In some aspects, the pathway can be cytoskeleton remodeling, chemokines, androgen signaling, cell adhesion, or Wnt signaling. In certain aspects, the pathway includes a mediator molecule that can be cAMP, EGFR, Cox2, hedgehog (Hh), TGFβ receptor (TGFBR) or IGF receptor (IGFR). In still other aspects, the inhibitor selectively targets CD44+, CD24− breast epithelial cells, CD24+ breast epithelial cells, p27+ breast epithelial cells, or Ki67+ breast epithelial cells. In certain aspects, the cells selectively targeted by the inhibitor are also ER+. In certain aspects, the subject has a BRCA1 or BRCA2 mutation.

In certain aspects, methods of treating or preventing breast cancer in a subject are provided. The methods include administering to a subject an agonist of a pathway that has decreased activity in CD44+, CD24− breast epithelial cells of nulliparous women compared to CD44+, CD24− breast epithelial cells of parous women. In certain aspects, the pathway can be tumor suppression (Hakai/CBLL1, CASP8, SCRIB, LLGL2), DNA repair, PI3K/AKT signaling, or apoptosis. In certain aspects, the agonist selectively targets CD44+, CD24− breast epithelial cells, CD24+ breast epithelial cells, p27+ breast epithelial cells, or Ki67+ breast epithelial cells. In another aspect, the cells selectively targeted by the agonist are also ER+. In certain aspects, the subject has a BRCA1 or BRCA2 mutation.

In any of the above aspects, the breast cancer can be an ER+ or an ER− breast cancer.

Unless otherwise defined, all technical and scientific terms used herein have the same meaning as commonly understood by one of ordinary skill in the art to which this invention pertains. In case of conflict, the present document, including definitions, will control.

All publications, patent applications, patents, and other references mentioned herein are incorporated by reference in their entirety. The materials, methods, and examples disclosed herein are illustrative only and not intended to be limiting.

The details of one or more embodiments of the invention are set forth in the accompanying drawings and the description below. Preferred methods and materials are described below, although methods and materials similar or equivalent to those described herein can also be used in the practice or testing of the present invention. Other features, objects, and advantages of the invention will be apparent from the description and drawings, and from the claims.

DESCRIPTION OF DRAWINGS

FIG. 13 is an integrated map of statistically significant (P-val<0.05) pathways enriched in genes highly expressed in CD44+ nulliparous cells along with DNA methylation patterns. Important pathways highly active in CD44+ nulliparous cells potentially regulated by DNA methylation include PI3K signaling and TCF/Lef signaling. Highly expressed genes, and promoter and gene body hypo and hyper-methylation are indicated.

FIG. 14 is an integrated map of statistically significant (P-val<0.05) pathways enriched in genes highly expressed in CD44+ parous cells along with DNA methylation patterns. Active pathways potentially regulated by DNA methylation in CD44+ parous cells include TGFB2 signaling. Highly expressed genes, and promoter and gene body hypo and hyper-methylation are indicated.

FIG. 15A is a Venn diagram depicting the number of unique and common pathways high in CD44+ nulliparous cells and in mammary glands of virgin rats, respectively.

FIG. 15B is a list of top common pathways downregulated in CD44+ cells and mammary glands from parous women and rats, respectively. Names of the pathways and p-values of enrichment are indicated.

FIG. 18 contains graphs quantifying (in arbitrary units) the expression of p27, Sox17 and Cox2 in CD44+ and CD24+ breast epithelial cells in premenopausal nulliparous (NP) and parous (P) women. Horizontal bars indicate the median, vertical bars indicate SEM, and p-values indicate the statistical significance of the observed differences.

FIG. 24 contains bar graphs quantifying the frequency (% of total breast epithelial cells) of BrdU+, Ki67+, and p27+ cells in each of the indicated conditions (control, inhibition of cAMP, EGFR, Cox2, Hh, TGFβ, Wnt, or IGFR in normal breast tissues incubated in a tissue explant culture model with the relevant inhibitor); * indicates p<0.05 and bars indicate SEM.

FIG. 26B contains a bar graph quantifying the frequency (%) of p27+ cells in tissue slices from 3-4 independent cases treated with hormones mimicking the indicated physiologic levels (control, follicular phase, luteal phase, and pregnancy) in women. Asterisks indicated significant (p≤0.05) differences.

FIG. 26C contains bar graphs quantifying the frequency (% of all breast epithelial cells) of p27+, Ki67+, and p27+Ki67+ cells in tissue slice cultures treated with Shh or Tamoxifen; asterisks indicate a statistical significance of p≤0.05.

FIG. 27 contains Kaplan-Meier plots depicting the probability of breast cancer-specific survival among women with invasive ER+(left panel) or ER– (right panel) breast cancer by parity in the Nurses' Health Study (1976-2006). The p-value of the difference between the two survival curves overall was calculated with use of the log-rank test. Beneath each plot the number of parous and nulliparous women alive at each of the time points shown on the x-axes of the plots (beginning at 5 years) is shown.

FIGS. 28 and 29A-C contain heat maps (left panel) and Kaplan-Meier plots with their corresponding log-rank test p-values (right panel) showing a significant association of the presence of a parity/nulliparity-related gene signature with overall survival in the indicated cohorts of breast cancer patients with ER+ tumors. In each figure, the top heat map shows the signature from down regulated genes in parous subjects and the bottom heat map from up group genes. The bars above the heat maps indicate the two distinct patients groups separated by the co-expression of the signature (light gray (left bar on heat map, upper line on Kaplan-Meier plots): better survival group; dark gray (right bar on heat map, lower line on Kaplan-Meier plots): worse survival group). The bar at the right side of heat map, divided into an upper and lower group, indicates effect of parity on genes in breast cancer progression. The upper group indicates parity induces gene expression level change in the same trend as breast cancer progression. The lower group indicates parity induces gene expression level change in the opposite trend as breast cancer progression. Black bars (beneath the heat maps) indicate death. The genes shown in the heat maps (the parity/nulliparity-related gene signature) are shown in Table 18, below, which shows the gene symbol, gene description, gene expression pattern (i.e., high in parous and nulliparous samples), and prognostic values (good or bad prognosis) for each of the genes.

In FIG. 31, initially, there are N wild-type stem cells (top of schematic), which give rise to a differentiation cascade of $2^{z+1}-1$ wild-type luminal progenitor cells (triangular, lower region). Darkening gray gradations refer to successively more differentiated cells and serve to clarify a single time step of the stochastic process. In FIG. 32, "WT" means wild-type (non-mutated) stem cell and "$f_{mut}$" means mutant progenitor cell. Division during pregnancy is indicated by "$z_{preg}$"; z is the number of cell divisions; K indicates the number of cell divisions from the first progeny of the stem cell (k=0) to the terminally differentiated cell (darkest gray).

DETAILED DESCRIPTION

Figure 1:
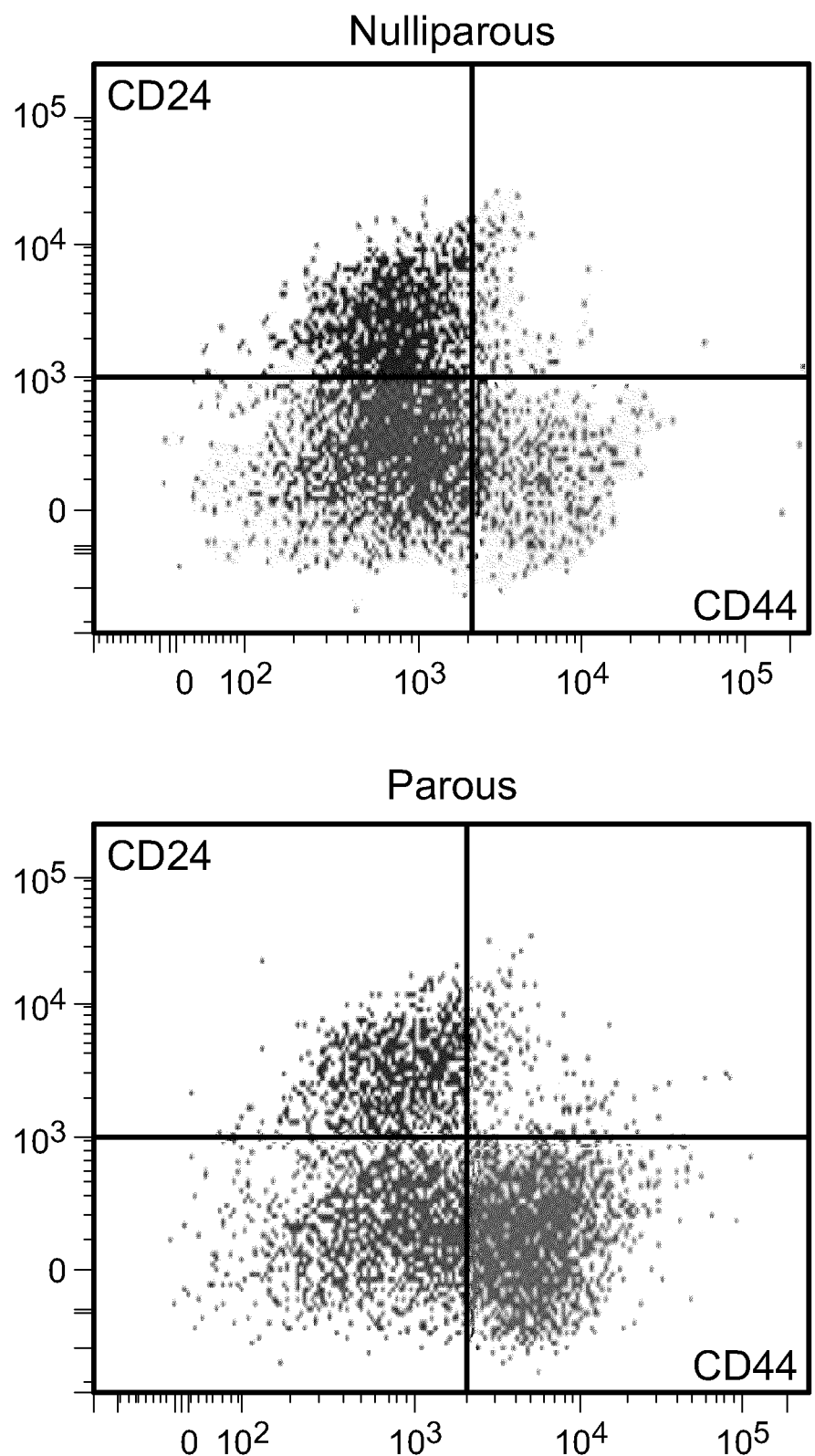
FIG. 1 contains representative FACS plots for cells stained with fluorescent antibodies specific for CD24 and CD44 from normal breast tissue of nulliparous (upper plot) and parous (lower plot) women.

Various aspects of the invention are described below.

I. Overview

A single full-term pregnancy in early adulthood decreases the risk of estrogen receptor (ER)-positive (+) postmenopausal breast cancer, the most common form of the disease. Age at first pregnancy is critical, as the protective effect decreases after the mid 20 s, and women aged >35 years at first birth have increased risk of both ER+ and ER− breast cancer. Parity-associated risk is also influenced by germline variants, as BRCA1 and BRCA2 mutation carriers do not experience the same decrease in risk reduction as does the general population. These human epidemiological data suggest that pregnancy induces long-lasting effects in the normal breast epithelium and that ER+ and ER− tumors might have a different cell of origin. The protective effect of parity is also observed in animal models, where its protective effect can be mimicked by hormonal factors in the absence of gestation.

The cellular and molecular mechanisms that underlie pregnancy and hormone-induced refractoriness to carcinogens are largely undefined. Several hypotheses have been proposed including the induction of differentiation, decreased susceptibility to carcinogens, a decrease in cell proliferation and in the number of mammary epithelial stem cells, an altered systemic environment due to a decrease in circulating growth hormone and other endocrine factors, and permanent molecular changes leading to alterations in cell fate. Almost all studies investigating pregnancy-induced changes and the breast cancer preventative effects of pregnancy have been conducted in rodent models and most of them have focused only on the mammary gland. Global gene expression profiling of mammary glands from virgin and parous rats identified changes in TGFβ and IGF signaling, and in the expression of extracellular matrix proteins.

Related studies conducted in humans also identified consistent differences in gene expression profiles between nulliparous and parous women (see Asztalos et al. (2010) *Cancer Prev Res (Phila)* 3, 301-311; Belitskaya-Levy et al. (2011) *Cancer Prev Res (Phila)* 4, 1457-1464; Russo et al. (2008) *Cancer Epidemiol Biomarkers Prev* 17, 51-66; and Russo et al. (2011) *Int J Cancer*; October 25; E-pub ahead of print). Because those studies used total mammary gland or mammary organoids, which are composed of multiple cell types the cellular origin of these gene expression differences remains unknown. Emerging data indicate that mammary epithelial progenitor or stem cells are the cell of origin of breast carcinomas. Studies assessing changes in mammary epithelial stem cells following pregnancy, however, have been conducted only in mice and thus far have been inconclusive. Thus, the effect of pregnancy on the number and functional properties of murine mammary epithelial progenitors is still elusive and it has not yet been analyzed in humans.

It is presently discovered that parity has a pronounced effect on CD44+ cells with progenitor features. As demonstrated in the present Examples, most of the differences in CD44+ cells between nulliparous and parous samples related to transcriptional repression and downregulation of genes and pathways important for stem cell function, many of which also play a role in tumorigenesis, including EGF, IGF, Hh, and TGFβ signaling. High circulating IGF-1 levels have been associated with increased risk of ER+ breast cancer, and germline polymorphism in members of the TGFβ signaling pathway have also been described to influence breast cancer susceptibility.

The present Examples also demonstrate that parity not only influences the risk of developing breast cancer, but potentially even the type of tumor and associated clinical outcome in breast cancer patients. Moreover, based on the genomic profiling and functional validation results in tissue explant cultures shown in the present Examples, the pathways that were identified as less active in parous women can be used for risk stratification and for chemoprevention in high-risk women, as their inhibition will mimic the cancer-reducing effects of parity.

The present Examples also demonstrate a significant decrease in the number of p27+ cells in breast tissues of parous women, which seems paradoxical as p27 (also known as CDKN1B/p27(kip1)) is a bona fide tumor suppressor and potent inhibitor of cell cycle progression. p27 has been shown to play an important role in stem cells, best characterized in the hematopoietic system, where loss of p27 increases the number of transit amplifying progenitors but not that of stem cells. In the mouse mammary gland, p27 deficiency leads to hypoplasia and impaired ductal branching and lobulo-alveolar differentiation, a phenotype consistent with a putative role in regulating the number and proliferation of mammary epithelial progenitors, although this has not been investigated.

While not intending to be bound by any one particular theory or mechanism of action, based on the data in the present Examples, it is thought that p27 regulates the proliferation and pool size of hormone-responsive breast epithelial progenitors; thus, the lower number of p27+ cells in parous women reflects a decrease in the number of quiescent progenitors with proliferative potential, which may contribute to their decrease in breast cancer risk. High p27 levels and quiescence are maintained in these cells by TGFβ signaling, as implied by the co-expression of pSmad2 with p27 and the increase in BrdU incorporation with concomitant decrease in p27 (Example 9).

It is also presently discovered that the frequency of p27+ cells was high in control nulliparous women and even higher in BRCA1 and BRCA2 mutation carriers even though these different groups of women are predisposed to different types of breast cancer (Example 2). Nulliparous women have increased risk of postmenopausal ER+ breast cancer, whereas BRCA1 mutation carriers most commonly have ER− basal-like tumors. However, recently published studies analyzing the potential cell-of-origin of BRCA1-associated breast cancer in animal models and in humans have found that even these basal-like tumors may initiate from luminal progenitors. The present Examples demonstrate increased frequency of hormone responsive p27+ cells in all high-risk women, supporting these hypotheses.

Thus, the number of p27+ breast epithelial progenitor (CD44+) cells in the normal breast and the activity of pathways that regulate the number of p27+ cells can be used as markers for predicting the risk of developing breast cancer (e.g., ER+ breast cancer or ER− breast cancer), as novel targets for cancer preventive and treatment strategies (e.g. therapeutic intervention), and for monitoring the efficacy of such preventive and treatment strategies. Furthermore, the pathways identified herein, e.g., a TGFβ pathway, can be exploited for breast cancer prevention, as they can be modulated to deplete p27+ cells with progenitor features and consequently decrease breast cancer risk.

II. Definitions

As used herein, the term "estrogen-receptor-positive (ER+) breast cancer" means a cancer wherein at least one cancer cell expresses the estrogen receptor. As used herein, the term "estrogen-receptor-negative (ER−) breast cancer" means a cancer wherein the cancer cells do not express the estrogen receptor.

As used herein, a "breast tissue sample" can include, but is not limited to, histological sections of normal breast tissue, e.g., healthy breast tissue, tumors or cancer cell-containing tissue, whole or soluble fractions of tissue or cell (e.g., cancer cell) lysates, cell subfractions (e.g., mitochondrial or nuclear subfractions), whole or soluble fractions of tissue or cell (e.g., cancer cell) subfraction lysates can be analyzed.

As used herein, a cell that is "positive" for a marker, such as, e.g., a CD44+, p27+, CD24+, or CD10+ cell, expresses the marker at the mRNA and/or protein level.

As used herein, breast "stromal cells" are breast cells other than epithelial cells.

As used herein, the term "subject" means any animal, including any vertebrate or mammal, and, in particular, a human, and can also be referred to, e.g., as an individual or patient. Typically, not necessarily, the subject is female. A subject in "need of such predicting" i.e., a subject in need of predicting the subject's risk of developing breast cancer, can be, e.g., a subject with a family history of breast cancer, a subject who has not been tested for and/or has not been diagnosed with breast cancer, a subject who wishes to know their risk of developing breast cancer, e.g., ER+ or ER− breast cancer, and/or a subject undergoing a routine health screen by, e.g., their attending physician, and/or a subject undergoing a therapy (e.g., raloxifen or tamoxifen) for the treatment and/or prevention of cancer (e.g., breast cancer).

As used herein, a subject (e.g., patient) having a characteristic (as described herein) that results in a "relatively elevated risk of developing breast cancer," (e.g., ER+ or ER− breast cancer) has a greater risk of developing breast cancer than a subject not having that characteristic. Conversely, a subject having a characteristic (as described herein) that results in a "relatively reduced risk of developing breast cancer," has a lesser risk of developing breast cancer than a subject not having that characteristic.

As used herein, a "parous" subject is a woman who has carried a pregnancy for at least 37 weeks of gestation, one or more times. As used herein, a "nulliparous" subject is a woman who has never carried a pregnancy for at least 37 weeks gestation.

As used herein, a "first control frequency" of a cell type (e.g., CD44+ or CD24+ cells) is the frequency of the cell type in a comparable sample from a patient or the average frequency in comparable samples from a plurality of patients known to be at low risk of developing breast cancer (e.g., parous women not expressing BRCA1 or BRCA2 mutations). "Comparable sample" typically means the same sample type (e.g., tumor biopsy or histological section from the same tissue (e.g. breast tissue). The first control frequency can also be a "predetermined reference frequency" (i.e., standard) to which the frequency of the cell type in a test sample is compared. As used herein, a "second control frequency" of a cell type (e.g., CD44+ or CD24+ cells) is the frequency of the cell type in a comparable sample from a patient or the average frequency in comparable samples from a plurality of patients known to be at high risk of developing breast cancer (e.g., nulliparous women).

As used herein, the "expression level" of a marker, such as, e.g., CD44, CD24, CD10, p27, Ki67, Sox17, Cox2, cAMP, EGFR, TGFBR, Cox2, Hh, and IGFR, etc. means the mRNA and/or protein expression level of the marker, or the measurable level of the marker in a sample (e.g., the level of cAMP can be detected by immunoassay), which can be determined by any suitable method known in the art, such as, but not limited to Northern blot, polymerase chain reaction (PCR), e.g., quantitative real-time, "QPCR", Western blot, immunoassay (e.g., ELISA), immunohistochemistry, cell immunostaining and fluorescence activated cell sorting (FACS), etc.

As used herein, a "substantially altered" level of expression of a gene in a first cell (or first tissue) compared to a second cell (or second tissue) is an at least 2-fold (e.g., at least: 2-; 3-; 4-; 5-; 6-; 7-; 8-; 9-; 10-; 15-; 20-; 30-; 40-; 50-; 75-; 100-; 200-; 500-; 1,000-; 2000-; 5,000-; or 10,000-fold) altered level of expression of the gene. It is understood that the alteration can be an increase or a decrease.

As used herein, the term "selectively targets", e.g., in the context of a specific cell type (e.g., CD44+, CD24− breast epithelial cells, p27+ breast epithelial cells, etc.) means the targeting agent (e.g., an inhibitor or agonist) mediates an effect on the specific target cell, but not on other cells. Thus, for example, an inhibitor that selectively targets CD44+ cells will mediate an effect (e.g. inhibition, e.g., of proliferation) on CD44+ cells, but not on CD44− cells. Such selective targeting can be achieved, e.g., by conjugating the inhibitor to an antibody that specifically binds to the target cell (e.g., an anti-CD44 antibody), as well as by other methods known in the art.

As used herein, "treating" or "treatment" of a state, disorder or condition includes: (1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; and/or (2) inhibiting the state, disorder or condition, i.e., arresting, reducing or delaying the development of the disease or a relapse thereof (in case of maintenance treatment) or at least one clinical or sub-clinical symptom thereof; and/or (3) relieving the disease, i.e., causing regression of the state, disorder or condition or at least one of its clinical or sub-clinical symptoms; and/or (4) causing a decrease in the severity of one or more symptoms of the disease. The benefit to a subject to be treated is either statistically significant or at least perceptible to the patient or to the physician.

As used herein, the term "treating cancer" (e.g., treating an ER+ or ER− breast cancer) means causing a partial or complete decrease in the rate of growth of a tumor, and/or in the size of the tumor and/or in the rate of local or distant tumor metastasis in the presence of an inhibitor of the invention, and/or any decrease in tumor survival.

As used herein, the term "preventing a disease" (e.g., preventing ER+ or ER− breast cancer) in a subject means for example, to stop the development of one or more symptoms of a disease in a subject before they occur or are detectable, e.g., by the patient or the patient's doctor. Preferably, the disease (e.g., cancer) does not develop at all, i.e., no symptoms of the disease are detectable. However, it can also result in delaying or slowing of the development of one or more symptoms of the disease. Alternatively, or in addition, it can result in the decreasing of the severity of one or more subsequently developed symptoms.

As used herein, a "pathway that has decreased activity", e.g., in breast epithelial cells (e.g., CD44+, CD24− breast epithelial cells)) of parous or nulliparous women means a pathway involving one or more genes or polypeptides mediating a function in the pathway that have reduced level of expression and/or activity. Non-limiting examples of such pathways are exemplified in Tables 10 and 11.

Figure 28:
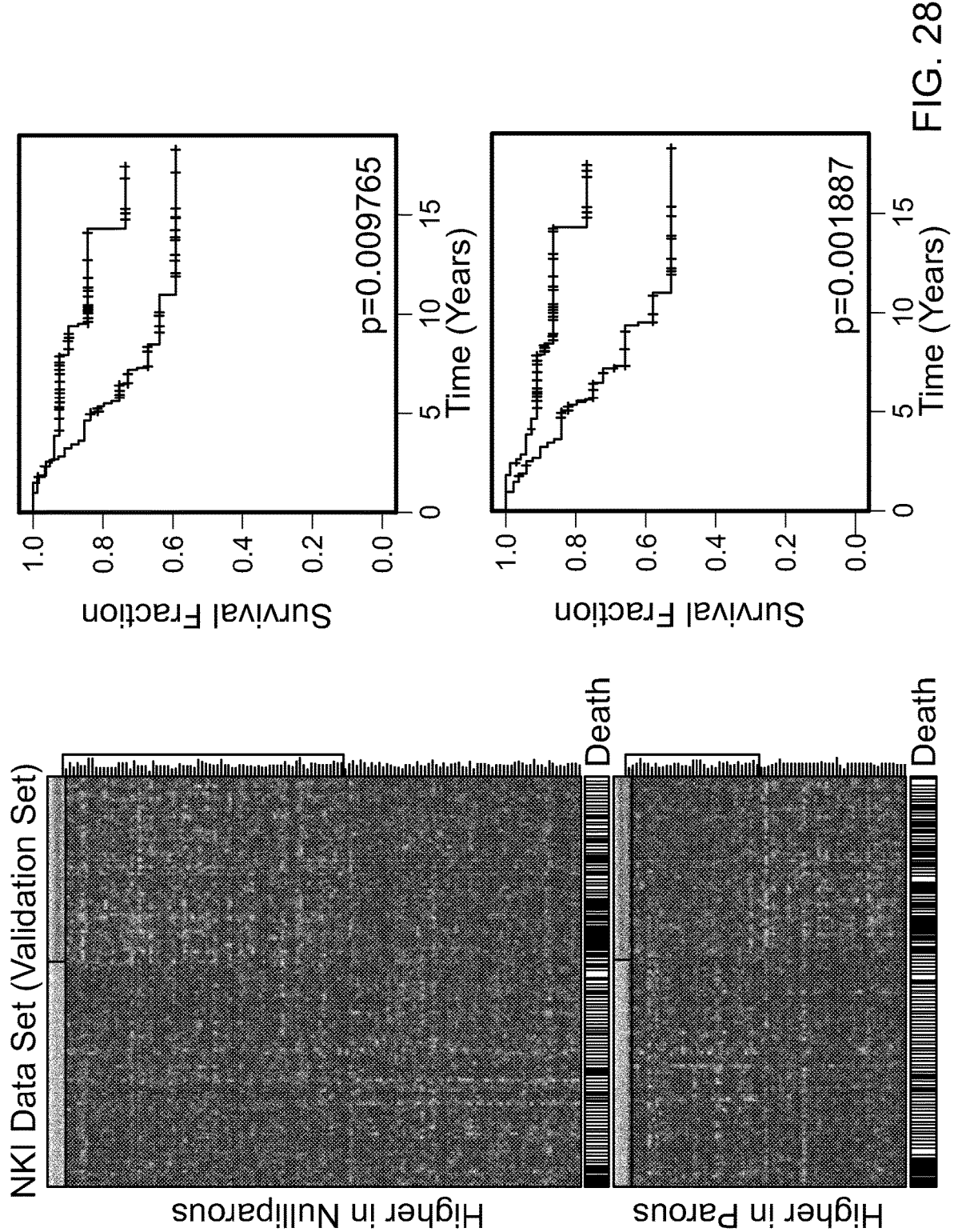

As used herein, the term "parity/nulliparity-related gene signature" means the known expression level of a group of two or more genes in breast epithelial cells of parous and nulliparous women (as disclosed herein). For example, the group of genes that were shown to be upregulated or downregulated in FIG. 28, or a subgroup of the genes, are part of such parity/nulliparity-related gene signature. The genes shown in FIG. 28 are summarized in Table 18. Of course, the skilled artisan will appreciate that a parity/nulliparity-related gene signature can, but does not necessarily, include all of the genes shown in Table 18. Preferably, the signature includes 2 or more, 3 or more, 4 or more, 5 or more, 10 or more, 15 or more, 20 or more, 30 or more, 40 or more, 50 or more, or 100 or more of the genes shown in Table 18.

As used herein "combination therapy" means the treatment of a subject in need of treatment with a certain composition or drug in which the subject is treated or given one or more other compositions or drugs for the disease in conjunction with the first and/or in conjunction with one or more other therapies, such as, e.g., a cancer therapy such as chemotherapy, radiation therapy, and/or surgery. Such combination therapy can be sequential therapy wherein the patient is treated first with one treatment modality (e.g., drug or therapy), and then the other (e.g., drug or therapy), and so on, or all drugs and/or therapies can be administered simultaneously. In either case, these drugs and/or therapies are said to be "coadministered." It is to be understood that "coadministered" does not necessarily mean that the drugs and/or therapies are administered in a combined form (i.e., they may be administered separately or together to the same or different sites at the same or different times).

The term "pharmaceutically acceptable derivative" as used herein means any pharmaceutically acceptable salt, solvate or prodrug, e.g., ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Pharmaceutically acceptable derivatives include salts, solvates, esters, carbamates, and/or phosphate esters.

As used herein the terms "therapeutically effective" and "effective amount", used interchangeably, applied to a dose or amount refer to a quantity of a composition, compound or pharmaceutical formulation that is sufficient to result in a desired activity upon administration to an animal in need thereof. Within the context of the present invention, the term "therapeutically effective" refers to that quantity of a composition, compound or pharmaceutical formulation that is sufficient to reduce or eliminate at least one symptom of a disease or condition specified herein, e.g., breast cancer such as ER+ or ER− breast cancer. When a combination of active ingredients is administered, the effective amount of the combination may or may not include amounts of each ingredient that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level.

Therapeutically effective dosages can be determined stepwise by combinations of approaches such as (i) characterization of effective doses of the composition or compound in in vitro cell culture assays using tumor cell growth and/or survival as a readout followed by (ii) characterization in animal studies using tumor growth inhibition and/or animal survival as a readout, followed by (iii) characterization in human trials using enhanced tumor growth inhibition and/or enhanced cancer survival rates as a readout.

The term "nucleic acid hybridization" refers to the pairing of complementary strands of nucleic acids. The mechanism of pairing involves hydrogen bonding, which may be Watson-Crick, Hoogsteen or reversed Hoogsteen hydrogen bonding, between complementary nucleoside or nucleotide bases (nucleobases) of the strands of nucleic acids. For example, adenine and thymine are complementary nucleobases that pair through the formation of hydrogen bonds. Hybridization can occur under varying circumstances. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO4, 7% SDS, 1 mM EDTA at 65° C., followed by washing in 0.1×SSC/0.1% SDS (where 1×SSC is 0.15 M NaCl, 0.15 M Na citrate) at 68° C. or for oligonucleotide (oligo) inhibitors washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos).

Conditions of intermediate or moderate stringency (such as, for example, an aqueous solution of 2×SSC at 65° C.; alternatively, for example, hybridization to filter-bound DNA in 0.5 M NaHPO$_4$, 7% SDS, 1 mM EDTA at 65° C. followed by washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA or RNA molecule and length and base composition of the probe, and are normally determined empirically in preliminary experiments, which are routine (see Southern, J. Mol. Biol. 1975; 98:503; Sambrook et al., Molecular Cloning: A Laboratory Manual, 2nd ed., vol. 2, ch. 9.50, CSH Laboratory Press, 1989; Ausubel et al. (eds.), 1989, Current Protocols in Molecular Biology, Vol. I, Green Publishing Associates, Inc., and John Wiley & Sons, Inc., New York, at p. 2.10.3). An extensive guide to the hybridization of nucleic acids is found in, e.g., Tijssen (1993) Laboratory Techniques in Biochemistry and Molecular Biology—Hybridization with Nucleic Acid Probes part 1, chapt 2, "Overview of principles of hybridization and the strategy of nucleic acid probe assays," Elsevier, N.Y. ("Tijssen").

As used herein, the term "standard hybridization conditions" refers to hybridization conditions that allow hybridization of two nucleotide molecules having at least 50% sequence identity. According to a specific embodiment, hybridization conditions of higher stringency may be used to allow hybridization of only sequences having at least 75% sequence identity, at least 80% sequence identity, at least 90% sequence identity, at least 95% sequence identity, or at least 99% sequence identity.

As used herein, the phrase "under hybridization conditions" means under conditions that facilitate specific hybridization of a subset of capture oligonucleotides to complementary sequences present in the cDNA or cRNA. The terms "hybridizing specifically to" and "specific hybridization" and "selectively hybridize to," as used herein refer to the binding, duplexing, or hybridizing of a nucleic acid molecule preferentially to a particular nucleotide sequence under at least moderately stringent conditions, and preferably, highly stringent conditions, as discussed above.

"Polypeptide" and "protein" are used interchangeably and mean any peptide-linked chain of amino acids, regardless of length or post-translational modification.

As used herein, the term "nucleic acid" or "oligonucleotide" refers to a deoxyribonucleotide or ribonucleotide in either single- or double-stranded form. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (Strauss-Soukup (1997) Biochemistry 36:8692-8698), and benzylphosphonate linkages (Samstag (1996) Antisense Nucleic Acid Drug Dev 6:153-156). The term nucleic acid is used interchangeably with cDNA, cRNA, mRNA, oligonucleotide, probe and amplification product.

III. Cell Markers

In certain embodiments, it is desirable to detect the presence and/or expression level of one or more cell markers (e.g., estrogen receptor (ER), p27, CD24, CD44, CD10, Ki67, BRCA1, BRCA2, etc.) associated with breast epithelial cells and/or breast cancer (e.g., ER+ or ER− breast cancer). Moreover, the present document features methods in which the relative numbers of cells expressing one or more of these markers are determined. The nucleic acid and amino acid sequences for such markers are known and have been described, and the GenBank® Accession Nos. of exemplary nucleic acid and amino acid sequences for the human markers are provided in Table 1, below.

TABLE 1

Exemplary GenBank® Accession Numbers Breast Cancer-Associated Markers

| Gene Name | Nucleic Acid GenBank® Accession No. | SEQ ID NO | Corresponding Polypeptide Name | Amino Acid GenBank® Accession No. | SEQ ID NO |
|---|---|---|---|---|---|
| CD24 | BG327863 | 1 | Sialoglycoprotein | ACI46150.1 | 2 |
| CD10 | NM_007289.2 | 3 | Neprilysin | NP_009220.2 | 4 |

TABLE 1-continued

Exemplary GenBank® Accession Numbers Breast Cancer-Associated Markers

| Gene Name | Nucleic Acid GenBank® Accession No. | SEQ ID NO | Corresponding Polypeptide Name | Amino Acid GenBank® Accession No. | SEQ ID NO |
|---|---|---|---|---|---|
| CD44 | BC004372 | 5 | CD44 | AAB30429.1 | 6 |
| P27/CDKN1B | BC001971 | 7 | CDKN1B | CAG33680.1 | 8 |
| Ki67 (MKI67) | AU152107 | 9 | KI67 antigen | CAD99007.1 | 10 |
| Homo sapiens SRY (sex determining region Y)-box 17 (SOX17) | NM_022454.3 | 11 | transcription factor SOX-17 | NP_071899 | 12 |
| Prostaglandin-endoperoxide synthase 2 (prostaglandin G/H synthase and cyclooxygenase) (PTGS2) | NM_000963 | 13 | prostaglandin G/H synthase 2 precursor | NP_000954 | 14 |
| Epidermal Growth Factor Receptor P (EGFR) | NM_005228 NM_201282 NM_201283.1 NM_201284 | 15 16 17 18 | Epidermal growth factor receptor | NP_005219.2 NP_958439.1 NP_958440.1 NP_958441.1 | 19 20 21 22 |
| sonic hedgehog protein (SHH) | NM_000193 | 23 | Sonic hedgehog protein | NP_000184 | 24 |
| insulin-like growth factor 1 receptor (IGF1R) | NM_000875 | 25 | Insulin like Growth factor receptor | NP000866 | 26 |
| transforming growth factor, beta receptor 1 (TGFBR1) | NM_004612 NM_001130916 | 27 28 | Transforming Growth factor receptor beta receptor | NP_004603 NP_001124388 | 29 30 |
| estrogen receptor 1 (ESR1) | NM_000125.3 NM_001122740.1 NM_001122741.1 NM_001122742.1 | 31 32 33 34 | Estrogen Receptor I | NP_000116 NP_001116212 NP_001116213 NP_001116214 | 35 36 37 38 |
| breast cancer type 1 susceptibility protein (BRCA1) | NM_007294.3 NM_007300.3 NM_007297.3 NM_007298.3 NM_007299.3 | 39 40 41 42 43 | breast cancer type 1 susceptibility protein (BRCA1) | NP_009225 NP_009231.2 NP_009228.2 NP_009229.2 NP_009230.2 | 44 45 46 47 48 |
| Homo sapiens breast cancer 2, early onset (BRCA2), | NM_000059 | 49 | breast cancer type 2 susceptibility protein (BRCA2) | NP_000050 | 50 |
| Androgen Receptor (AR) | NM_000044 NM_001011645 | 51 52 | Androgen Receptor (AR) | NP_000035 NP_001011645 | 53 54 |

In certain embodiments, it is desirable to determine (e.g., assay, measure, approximate) the level (e.g., expression or activity), e.g., one of the above-identified markers. The expression level of such markers may be determined according to any suitable method known in the art. A non-limiting example of such a method includes real-time PCR (RT-PCR), e.g., quantitative RT-PCR (QPCR), which measures the expression level of the mRNA encoding the polypeptide. Real-time PCR evaluates the level of PCR product accumulation during amplification. RNA (or total genomic DNA for detection of germline mutations) is isolated from a sample. RT-PCR can be performed, for example, using a Perkin Elmer/Applied Biosystems (Foster City, Calif.) 7700 Prism instrument. Matching primers and fluorescent probes can be designed for genes of interest using, based on the genes' nucleic acid sequences (e.g., as described above), for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.).

To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from 10-$10^6$ copies of the gene of interest are generally sufficient. In addition, a standard curve is generated for the control sequence. This permits standardization of initial content of the nucleic acid of interest in a tissue sample to the amount of control for comparison purposes. Methods of QPCR using TaqMan probes are well known in the art. Detailed protocols for QPCR are provided, for example, for RNA in: Gibson et al., 1996, *Genome Res.*, 10:995-1001; and for DNA in: Heid et al., 1996, *Genome Res.*, 10:986-994; and in Innis et al. (1990) Academic Press, Inc. N.Y.

Expression of mRNA, as well as expression of peptides and other biological factors can also be determined using microarray, methods for which are well known in the art [see, e.g., Watson et al. Curr Opin Biotechnol (1998) 9:

609-14; "DNA microarray technology: Devices, Systems, and Applications" *Annual Review of Biomedical Engineering*; Vol. 4: 129-153 (2002); Chehab et al. (1989) "Detection of specific DNA sequences by fluorescence amplification: a color complementation assay" *Proc. Natl. Acad. Sci. USA*, 86: 9178-9182; Lockhart et al. (1996) "Expression monitoring by hybridization to high-density oligonucleotide arrays" *Nature Biotechnology*, 14: 1675-1680; and M. Schena et al. (1996) "Parallel human genome analysis: Microarray-based expression monitoring of 1000 genes" *Proc. Natl. Acad. Sci. USA*, 93:10614-10619; *Peptide Microarrays Methods and Protocols; Methods in Molecular Biology*; Volume 570, 2009, Humana Press; and *Small Molecule Microarrays Methods and Protocols; Series: Methods in Molecular Biology*, Vol. 669, Uttamchandani, Mahesh; Yao, Shao Q. (Eds.) 2010, 2010, Humana Press]. For example, mRNA expression profiling can be performed to identify differentially expressed genes, wherein the raw intensities determined by microarray are $\log_2$-transformed and quantile normalized and gene set enrichment analysis (GSEA) is performed according, e.g., to Subramanian et al. (2005) *Proc Natl Acad Sci USA* 102:15545-15550).

Other suitable amplification methods include, but are not limited to ligase chain reaction (LCR) (see Wu and Wallace (1989) Genomics 4:560, Landegren et al. (1988) Science 241:1077, and Barringer et al. (1990) Gene 89:117), transcription amplification (Kwoh et al. (1989) Proc. Natl. Acad. Sci. USA 86:1173), self-sustained sequence replication (Guatelli et al. (1990) Proc. Nat. Acad. Sci. USA 87:1874), dot PCR, and linker adapter PCR, etc. In another embodiment, DNA sequencing may be used to determine the presence of ER in a genome. Methods for DNA sequencing are known to those of skill in the art.

Other methods for detecting gene expression (e.g., mRNA levels) include Serial Analysis of Gene Expression applied to high-throughput sequencing (SAGEseq), as described in the present Examples and in Wu Z J et al. Genome Res. 2010 December; 20(12):1730-9. 2.

For the detection of germline mutations (e.g., in BRCA1, BRCA2), Southern blotting can also be used. Methods for Southern blotting are known to those of skill in the art (see, e.g., Current Protocols in Molecular Biology, Chapter 19, Ausubel, et al., Eds., Greene Publishing and Wiley-Interscience, New York, 1995, or Sambrook et al., Molecular Cloning: A Laboratory Manual, 2d Ed. vol. 1-3, Cold Spring Harbor Press, N Y, 1989). In such an assay, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., genomic DNA from the same or related cell, tissue, organ, etc.) provides an estimate of the relative copy number of the target nucleic acid. Arrays of nucleic probes can also be employed to detect single or multiple germline or somatic mutations by methods known in the art.

Other examples of suitable methods for detecting expression levels of the cell markers described herein include, e.g., Western blot, ELISA and/or immunohistochemistry, which can be used to measure protein expression level. Such methods are well known in the art.

The frequency of cells that are specific for one or more particular markers (e.g., the frequency of CD44+ or CD24+ breast epithelial cells) can be detected according to any suitable method known in the art. For example, flow cytometry is widely used for analyzing the expression of cell surface and intracellular molecules (on a per cell basis), characterizing and defining different cell types in heterogeneous populations, assessing the purity of isolated subpopulations, and analyzing cell size and volume. This technique is predominantly used to measure fluorescence intensity produced by fluorescent-labeled antibodies or ligands that bind to specific cell-associated molecules, and is described in detail in, e.g., Holmes, K. et al. "Preparation of Cells and Reagents for Flow Cytometry" *Current Protocols in Immunology*, Unit 5.3.

Non-limiting examples of primary antibodies that may be used to identify the expression of certain markers by one or more assays, e.g., by flow cytometry, immunohistochemistry (IHC), and/or Western blot are listed in Table 2, below:

TABLE 2

Exemplary Cell Marker Primary Antibodies

| Cell Marker | Primary Antibody | Application (e.g., Western blot, flow cytometry, IHC) | Commercial Source |
| --- | --- | --- | --- |
| CD24 | clone SN3b | IHC | Neomarkers |
| CD24 | clone ML5 | FACS | Biolegend |
| CD10 | 56C6 clone | IHC | Dako |
| CD10 | Clone HI10a | FACS | Biolegend |
| CD44 | clone 156-3C11 | IHC | Neomarkers |
| CD44 | Clone 515 | FACS | BD |
| P27 | clone 57/Kip1/p27 | IHC | Bd Biosciences |
| Ki67 | N/A | IHC | Abcam |
| Sox17 | clone 245013 | IHC | R&D Systems |
| Cox2 | clone CX229 | IHC | Cayman Chemical |
| pEGFR | 53A5 (Tyr1173) | IHC | Cell Signaling Technology |
| Shh | Cat# 06-1106 | WB, IHC | Millipore |
| IGF-1R | Clone 24-31 | IHC (P) | Imgenex |
| pTGFBR | Phospho S165 | ICC/IF | Abcam |
| ER | Estrogen Receptor (clone SP1) | IHC | Thermo Scientific |
| AR | Androgen receptor (clone D6F11, #5153) | WB/IHC-P/IF/IC/F | Cell Signaling Technology |
| BRCA1 | MS110 clone | IF/IP/WB | Calbiochem |
| BRCA2 | Cst#CA1033 | WB/IP/IHC(P) | Millipore |

Abbreviations:
WB: Western blotting;
IHC: Immunohistochemistry;
IHC-P: immunohistochemistry-paraffin;
ICC: immunocytochemistry;
IF: immunofluorescence;
F: flow cytometry

IV. Genes and Pathways Differentially Regulated by Parity Status

In certain embodiments, it is desirable to decrease (e.g., inhibit) the expression and/or activity of genes and/or polypeptides encoded by those genes that are discovered herein to be upregulated in breast epithelial cells of nulliparous women relative to parous women. For example, one or more of the genes that are upregulated in CD44+, CD24+, CD10+ and stromal breast epithelial cells of nulliparous women, in Tables 4, 5, 6 and 7, respectively, can be targeted with an inhibitor as described herein in order to treat or prevent breast cancer (e.g., ER+ or ER− breast cancer). Further, for example, one or more of the genes that are upregulated in CD44+ breast epithelial cells of BRCA1 and/or BRCA2 mutation carriers compared to control (normal) breast epithelial cells), as shown, e.g., in Tables 8 and 9 can be targeted with an inhibitor as described herein in order to treat or prevent breast cancer (e.g., ER+ or ER− breast cancer). By way of non-limiting example, asp27 expression is higher in BRCA1 mutation carriers and in BRCA2 mutation carriers compared to control (non-mutation carriers, normal cells), and is an exemplary target for an inhibitor as discussed above.

In other embodiments, it is desirable to increase the expression and/or activity of genes and/or polypeptides encoded by those genes that are discovered herein to be upregulated in breast epithelial cells of parous women relative to nulliparous women. For example, one or more of the genes that are upregulated in CD44+, CD24+, CD10+ and stromal breast epithelial cells of parous women, in Tables 4, 5, 6 and 7, respectively, can be targeted with an agonist as described herein in order to treat or prevent breast cancer (e.g., ER+ or ER− breast cancer). Further, for example, one or more of the genes that are downregulated in CD44+ breast epithelial cells of BRCA1 and/or BRCA2 mutation carriers compared to control (normal) breast epithelial cells), as shown, e.g., in Tables 8 and 9, can be targeted with an agonist as described herein in order to treat or prevent breast cancer (e.g., ER+ or ER− breast cancer).

In certain embodiments, methods for treating breast cancer (e.g., ER+ or ER− breast cancer) involve targeting (e.g., inhibiting) one or more pathways that have increased activity in breast epithelial cells (e.g., CD44+, CD24− breast epithelial cells) of nulliparous women compared to the activity in the breast epithelial cells of parous women (such pathways are also referred to herein as "pathways active in nulliparous (NP) breast epithelial cells"). The identification of such pathways is described in detail in Example 3, below, and the pathways are listed in Tables 10 and 11, below. In a specific embodiment, the pathway is a member selected from the group consisting of cytoskeleton remodeling, chemokine, androgen signaling, cell adhesion, and Wnt signaling. In another embodiment, the pathway includes a mediator molecule selected from the group consisting of cyclic AMP (cAmp) (Signal transduction cAMP signaling pathway), EGFR (e.g., Development EGFR signaling via small GTPases pathway, EGFR signaling pathway), Cox2 (e.g., Role and regulation of Prostaglandin E2 in gastric cancer pathway, Hh (e.g., hedgehog signaling pathways), and IGFR (IGFR-IGF signaling pathways).

In other embodiments, methods for treating breast cancer involve targeting (e.g., administering an agonist of) one or more pathways that have decreased activity in breast epithelial cells (e.g., CD44+, CD24− breast epithelial cells) of nulliparous women compared to the breast epithelial cells of parous women (i.e., pathways that have increased activity in breast epithelial cells of parous women, which also referred to herein as "pathways active in parous (P) breast epithelial cells). Such pathways are identified in Example 3 and Tables 10 and 12.

Exemplary pathways are pathways active in nulliparous CD44+, CD24− breast epithelial cells, as shown in Table 11, although pathways active in other nulliparous breast epithelial cells types (e.g., CD24+, CD10+ and/or stromal breast epithelial cells) are also encompassed herein, and include, but are not limited to, Cytoskeleton remodeling_Role of PKA in cytoskeleton reorganisation, Development_MAG-dependent inhibition of neurite outgrowth, Role of DNA methylation in progression of multiple myeloma, Cell adhesion_Histamine H1 receptor signaling in the interruption of cell barrier integrity, Stem cells_Response to hypoxia in glioblastoma stem cells, Development_WNT signaling pathway. Part 2, Development_Slit-Robo signaling, Cytoskeleton remodeling_Fibronectin-binding integrins in cell motility, Oxidative phosphorylation, etc. The genes and the polypeptides encoded by those genes that mediate one or more functions in these pathways are known in the art and can be determined using, e.g., Metaminer software (GeneGo). Thus, the following genes are provided as non-limiting examples of genes involved in the pathways active in nulliparous CD44+, CD24− breast epithelial cells.

For example, genes involved in metabolic pathways active in nulliparous CD44+, CD24− breast epithelial cells (e.g., the pathways: Transcription_Transcription regulation of amino acid metabolism, Regulation of lipid metabolism_Stimulation of Arachidonic acid production by ACM receptors, Ubiquinone metabolism, and Mitochondrial ketone bodies biosynthesis and metabolism), include, but are not limited to, HSD17B11 (GenBank Accession No. BC014327, CA775960), HSD17B12 (GenBank Accession No. AF078850), and HSD17B14 (GenBank Accession No. AF126781), which are involved in regulation of lipid metabolism pathways.

Genes involved in androgen signaling pathways active in nulliparous CD44+, CD24− breast epithelial cells (e.g., the pathways: "Putative role of Estrogen receptor and Androgen receptor signaling in progression of lung cancer", "Androgen signaling in HCC" (see Tables 10 and 11)) include, but are not limited to, PSA (KLK3) (GenBank Accession Nos. AC011523, BC005307), which are involved in the androgen signaling.

Genes involved in developmental and thyroid signaling pathways active in nulliparous CD44+, CD24− breast epithelial cells (e.g., the pathways: Development_Glucocorticoid receptor signaling, Development_Hedgehog and PTH signaling pathways in bone and cartilage development) include, but are not limited to, NCOR1 (GenBank Accession No. AC002553), NCOR2 (GenBank Accession No. AB209089, AC073916), NCOA4 (GenBank Accession No. AL162047), and NCOA7 (GenBank Accession No. AJ420542).

Genes involved in Wnt signaling pathways active in nulliparous CD44+, CD24− breast epithelial cells (e.g., the pathways: Development_WNT signaling pathway, Cytoskeleton remodeling_TGF, WNT and cytoskeletal remodeling, Stem cells_WNT/Beta-catenin and NOTCH in induction of osteogenesis) include, but are not limited to, SFRP2 (GenBank Accession No. AA449032, AF311912), SFRP4 (GenBank Accession No. AC018634, BT019679), VEGFA (GenBank Accession Nos. AF024710, BF700556), HIF1A (GenBank Accession Nos. BC012527, CN264320), NOTCH1 (GenBank Accession Nos. AB209873, AF308602, AL592301), FN1 (GenBank Accession Nos AI033037, AJ535086).

Genes involved in chemokine pathways active in nulliparous CD44+, CD24− breast epithelial cells (e.g., the pathways: Cell adhesion_Chemokines and adhesion, Cell adhesion_Alpha-4 integrins in cell migration and adhesion, Cell adhesion_Plasmin signaling, Cell adhesion_ECM remodeling, Cell adhesion_Role of tetraspanins in the integrin-mediated cell adhesion) include, but are not limited to, ITGA4 (GenBank Accession No., AC020595) (ITGB1 (GenBank Accession No., A1261443), and TSPAN6 (GenBank Accession Nos. AF043906, BC012389).

Genes involved in cytoskeleton remodeling pathways active in nulliparous CD44+, CD24− breast epithelial cells (e.g., the pathways: Cytoskeleton remodeling_Regulation of actin cytoskeleton by Rho GTPases, Cytoskeleton remodeling_Fibronectin-binding integrins in cell motility, Cytoskeleton remodeling_Reverse signaling by ephrin B, Cytoskeleton remodeling_Role of PKA in cytoskeleton reorganisation) include, but are not limited to, RhoA (GenBank Accession Nos. AK130066, BC000946), RAC1 (Gen- Bank Accession No. AC009412), CDC42 (GenBank Accession No., NM_001039802), and EPHB4 (GenBank Accession Nos. AY056048, BC052804).

The pathways for DNA repair, PI3K/AKT signaling, and apoptosis have been demonstrated herein to be active in parous CD44+, CD24– breast epithelial cells. Other non-limiting examples of pathways active in parous breast epithelial cells include, e.g., TTP metabolism, Resistance of pancreatic cancer cells to death receptor signaling, Transcription_Assembly of RNA Polymerase II preinitiation complex on TATA-less promoters, Development_PIP3 signaling in cardiac myocytes, HCV-dependent regulation of RNA polymerases leading to HCC, Stem cells_H3K9 demethylases in pluripotency maintenance of stem cells, Inhibition of apoptosis in gastric cancer, Cell cycle_Start of DNA replication in early S phase, Apoptosis and survival_Caspase cascade, Immune response_BCR pathway, Immune response_ICOS pathway in T-helper cell, Cell cycle_The metaphase checkpoint, Inhibitory action of Lipoxins on neutrophil migration, Cytoskeleton remodeling_Alpha-1A adrenergic receptor-dependent inhibition of PI3K, DNA damage_NHEJ mechanisms of DSBs repair, Regulation of metabolism_Triiodothyronine and Thyroxine signaling, Cell cycle_Chromosome condensation in prometaphase, Development_IGF-1 receptor signaling, dCTP/dUTP metabolism, dGTP metabolism, Inhibition of RUNX3 signaling in gastric cancer, Apoptosis and survival_Beta-2 adrenergic receptor anti-apoptotic action, Signal transduction_Activin A signaling regulation, Stem cells_Fetal brown fat cell differentiation, Immune response_CXCR4 signaling via second messenger, dATP/dITP metabolism, Signal transduction_PTEN pathway, Microsatellite instability in gastric cancer, Inhibition of TGF-beta signaling in gastric cancer, Immune response_Regulation of T cell function by CTLA-4, DNA damage_DNA-damage-induced responses, etc. (see Tables 10 and 12). The genes and proteins encoded by those genes that mediate functions in these pathways are well known in the art. Thus, the skilled artisan will know which specific genes and/or polypeptides to target (e.g., with an agonist) as described herein (e.g., for the treatment or prevention of breast cancer (e.g., ER+ or ER– breast cancer)).

By way of example, genes involved in apoptosis pathways active in parous CD44+, CD24– breast epithelial cells (e.g., the pathways, Apoptosis and survival_FAS signaling cascades, Apoptosis and survival_Caspase cascade, Apoptosis and survival HTR1A signaling, Apoptosis and survival_Beta-2 adrenergic receptor anti-apoptotic action, Apoptosis and survival_Granzyme A signaling, Apoptosis and survival_Cytoplasmic/mitochondrial transport of pro-apoptotic proteins Bid, Bmf and Bim) upregulated in parous breast epithelial cells included, but are not limited to, BCL2L11 (GenBank Accession Nos. AC096670, AI268146, AK290377, AY428962), TNFRSF4 (GenBank Accession Nos. AW290885, BC105070), BMPR2 (GenBank Accession Nos. AC009960, BC035097), CASP8 (GenBank Accession Nos. BF439983, AC007256, AF422927), and PP2A (GenBank Accession Nos. AL158151, CD630703, DA052599, X73478).

Genes involve in PI3K/AKT signaling pathways active in parous CD44+, CD24– breast epithelial cells (e.g., the pathways, Cytoskeleton remodeling_Alpha-1A adrenergic receptor-dependent inhibition of PI3K, Signal transduction_AKT signaling, PI3K signaling in gastric cancer) that are upregulated in parous breast epithelial cells included, but are not limited to, PIK3CG (GenBank Accession No. X83368), p85 (GenBank Accession No. AC016564, BC094795, CA427864, CT003423), ILK (GenBank Accession No. BC001554, CB113885, U40282), PDPK1 (GenBank Accession No. AC093525, AC141586, BC012103).

Genes involved in tumor suppressor pathways active in parous breast epithelial cells (e.g., the pathways: Apoptosis and survival_Cytoplasmic/mitochondrial transport of pro-apoptotic proteins Bid, Bmf and Bim, Apoptosis and survival_Caspase cascade, Cytoskeleton remodeling_Alpha-1A adrenergic receptor-dependent inhibition of PI3K, Cell cycle_The metaphase checkpoint) include, but are not limited to, Hakai/CBLL1 (GenBank Accession Nos. AC002467, AK026762, AK293352), CASP8 (GenBank Accession No. BF439983), SCRIB (GenBank Accession No. A1469403), and LLGL2 (GenBank Accession Nos. AC100787, BC031842).

The skilled artisan will appreciate that the foregoing are non-limiting examples of pathways, as well as genes and polypeptides mediating functions in those pathways, that can be targeted (e.g., by an inhibitor or agonist) for the treatment of breast cancer, and other targets, such as those set forth in Tables 10, 11, and 12, below, are also encompassed by the present invention.

V. Inhibitors and Agonists

Inhibitors and agonists may be used to treat or prevent breast cancer in a subject, as described herein. One of skill in the art will appreciate that the design of such inhibitors and agonists will depend on the specific pathway (e.g., metabolic pathways androgen signaling pathways, tumor suppression, etc., as described above) being targeted. The skilled artisan will understand how to design such inhibitors and agonists, based on methods well known in the art.

The following are thus provided as non-limiting examples (e.g., antisense nucleic acids, RNAi, ribozymes, triple helix forming oligonucleotides (TFOs), antibodies (including, but not limited to intrabodies), aptamers, and other small molecules), and other inhibitors that target pathways (e.g., inhibit expression and/or activity of specific genes and/or polypeptides encoded by those genes that mediate a function in the pathway) that are active in breast epithelial cells of nulliparous women, and agonists that target pathways (e.g., increase expression and/or activity of specific genes and/or polypeptides that mediate a function in the pathway) that are active in parous women, are also encompassed by the present disclosure.

Antisense Nucleic Acids

Antisense oligonucleotides can be used to inhibit the expression of a target polypeptide of the invention (e.g., HSD17B11, HSD17B12, HSD17B14, etc.). Antisense oligonucleotides typically are about 5 nucleotides to about 30 nucleotides in length, about 10 to about 25 nucleotides in length, or about 20 to about 25 nucleotides in length. For a general discussion of antisense technology, see, e.g., Antisense DNA and RNA, (Cold Spring Harbor Laboratory, D. Melton, ed., 1988).

Appropriate chemical modifications of the inhibitors are made to ensure stability of the antisense oligonucleotide, as described below. Changes in the nucleotide sequence and/or in the length of the antisense oligonucleotide can be made to ensure maximum efficiency and thermodynamic stability of the inhibitor. Such sequence and/or length modifications are readily determined by one of ordinary skill in the art.

The antisense oligonucleotides can be DNA or RNA or chimeric mixtures, or derivatives or modified versions thereof, and can be single-stranded or double-stranded. Thus, for example, in the antisense oligonucleotides set forth in herein, when a sequence includes thymidine residues, one or more of the thymidine residues may be replaced by uracil residues and, conversely, when a sequence includes uracil residues, one or more of the uracil residues may be replaced by thymidine residues.

Antisense oligonucleotides comprise sequences complementary to at least a portion of the corresponding target polypeptide. However, 100% sequence complementarity is not required so long as formation of a stable duplex (for single stranded antisense oligonucleotides) or triplex (for double stranded antisense oligonucleotides) can be achieved. The ability to hybridize will depend on both the degree of complementarity and the length of the antisense oligonucleotides. Generally, the longer the antisense oligonucleotide, the more base mismatches with the corresponding nucleic acid target can be tolerated. One skilled in the art can ascertain a tolerable degree of mismatch by use of standard procedures to determine the melting point of the hybridized complex.

Antisense nucleic acid molecules can be encoded by a recombinant gene for expression in a cell (see, e.g., U.S. Pat. Nos. 5,814,500 and 5,811,234), or alternatively they can be prepared synthetically (see, e.g., U.S. Pat. No. 5,780,607).

The antisense oligonucleotides can be modified at the base moiety, sugar moiety, or phosphate backbone, or a combination thereof. In one embodiment, the antisense oligonucleotide comprises at least one modified sugar moiety, e.g., a sugar moiety such as arabinose, 2-fluoroarabinose, xylulose, and hexose.

In another embodiment, the antisense oligonucleotide comprises at least one modified phosphate backbone such as a phosphorothioate, a phosphorodithioate, a phosphoramidothioate, a phosphoramidate, a phosphorodiamidate, a methylphosphonate, an alkyl phosphotriester, and a formacetal or analog thereof. Examples include, without limitation, phosphorothioate antisense oligonucleotides (e.g., an antisense oligonucleotide phosphothioate modified at 3' and 5' ends to increase its stability) and chimeras between methylphosphonate and phosphodiester oligonucleotides. These oligonucleotides provide good in vivo activity due to solubility, nuclease resistance, good cellular uptake, ability to activate RNase H, and high sequence selectivity.

Other examples of synthetic antisense oligonucleotides include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with CH2-NH—O—CH2, CH2-N(CH3)-O—CH2, CH2-O—N(CH3)-CH2, CH2-N(CH3)-N(CH3)-CH2 and O—N(CH3)-CH2-CH2 backbones (where phosphodiester is O—PO2-O—CH2). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds.

In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 1991; 254:1497). Other synthetic oligonucleotides may contain substituted sugar moieties comprising one of the following at the 2' position: OH, SH, SCH3, F, OCN, O(CH2)nNH2 or O(CH2)nCH3 where n is from 1 to about 10; C1 to C10 lower alkyl, substituted lower alkyl, alkaryl or aralkyl; Cl; Br; CN; CF3; OCF3; O—; S—, or N-alkyl; O-, S-, or N-alkenyl; SOCH3; SO2CH3; ONO2; NO2; N3; NH2; heterocycloalkyl; heterocycloalkaryl; aminoalkylamino; polyalkylamino; substituted sialyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties.

Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine. In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752). LNA are nucleic acid analog(s) with a 2'-O, 4'-C methylene bridge. This bridge restricts the flexibility of the ribofuranose ring and locks the structure into a rigid C3-endo conformation, conferring enhanced hybridization performance and exceptional biostability. LNA allows the use of very short oligonucleotides (less than 10 bp) for efficient hybridization in vivo.

In one embodiment, an antisense oligonucleotide can comprise at least one modified base moiety such as a group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueuosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueuosine, 5-methoxycarboxymethyluracil, 5-methoxyuracil, 2-methylthio-N6-isopentenyladenine, uracil-5-oxyacetic acid (v), pseudouracil, queuosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the antisense oligonucleotide can include α-anomeric oligonucleotides. An α-anomeric oligonucleotide forms specific double-stranded hybrids with complementary RNA in which, contrary to the usual β-units, the strands run parallel to each other (Gautier et al., Nucl. Acids Res. 1987; 15:6625-6641).

Oligonucleotides may have morpholino backbone structures (U.S. Pat. No. 5,034,506). Thus, in yet another embodiment, the antisense oligonucleotide can be a morpholino antisense oligonucleotide (i.e., an oligonucleotide in which the bases are linked to 6-membered morpholine rings, which are connected to other morpholine-linked bases via nonionic phosphorodiamidate intersubunit linkages). Morpholino oligonucleotides are highly resistant to nucleases and have good targeting predictability, high in-cell efficacy and high sequence specificity (U.S. Pat. No. 5,034,506; Summerton, Biochim. Biophys. Acta 1999; 1489:141-158; Summerton and Weller, Antisense Nucleic Acid Drug Dev. 1997; 7:187-195; Arora et al., J. Pharmacol. Exp. Ther. 2000; 292:921-928; Qin et al., Antisense Nucleic Acid Drug Dev. 2000; 10:11-16; Heasman et al., Dev. Biol. 2000; 222:124-134; Nasevicius and Ekker, Nat. Genet. 2000; 26:216-220).

Antisense oligonucleotides may be chemically synthesized, for example using appropriately protected ribonucleoside phosphoramidites and a conventional DNA/RNA synthesizer. Antisense nucleic acid oligonucleotides can also be produced intracellularly by transcription from an exogenous sequence. For example, a vector can be introduced in vivo such that it is taken up by a cell within which the vector or a portion thereof is transcribed to produce an antisense RNA. Such a vector can remain episomal or become chromosomally integrated, so long as it can be transcribed to produce the desired antisense RNA. Such vectors can be constructed by recombinant DNA technology methods standard in the art. Vectors can be plasmid, viral, or others known in the art, used for replication and expression in mammalian cells. In another embodiment, "naked" antisense nucleic acids can be delivered to adherent cells via "scrape delivery", whereby the antisense oligonucleotide is added to a culture of adherent cells in a culture vessel, the cells are scraped from the walls of the culture vessel, and the scraped cells are transferred to another plate where they are allowed to re-adhere. Scraping the cells from the culture vessel walls serves to pull adhesion plaques from the cell membrane, generating small holes that allow the antisense oligonucleotides to enter the cytosol.

RNAi

Reversible short inhibition of a target polypeptide (e.g., Gfpt1, RPIA, RPE, etc.) of the invention may also be useful. Such inhibition can be achieved by use of siRNAs. RNA interference (RNAi) technology prevents the expression of genes by using small RNA molecules such as small interfering RNAs (siRNAs). This technology in turn takes advantage of the fact that RNAi is a natural biological mechanism for silencing genes in most cells of many living organisms, from plants to insects to mammals (McManus et al., Nature Reviews Genetics, 2002, 3(10) p. 737). RNAi prevents a gene from producing a functional protein by ensuring that the molecule intermediate, the messenger RNA copy of the gene is destroyed siRNAs can be used in a naked form and incorporated in a vector, as described below.

RNA interference (RNAi) is a process of sequence-specific post-transcriptional gene silencing by which double stranded RNA (dsRNA) homologous to a target locus can specifically inactivate gene function in plants, fungi, invertebrates, and vertebrates, including mammals (Hammond et al., Nature Genet. 2001; 2:110-119; Sharp, Genes Dev. 1999; 13:139-141). This dsRNA-induced gene silencing is mediated by short double-stranded small interfering RNAs (siRNAs) generated from longer dsRNAs by ribonuclease III cleavage (Bernstein et al., Nature 2001; 409:363-366 and Elbashir et al., Genes Dev. 2001; 15:188-200). RNAi-mediated gene silencing is thought to occur via sequence-specific RNA degradation, where sequence specificity is determined by the interaction of an siRNA with its complementary sequence within a target RNA (see, e.g., Tuschl, Chem. Biochem. 2001; 2:239-245).

For mammalian systems, RNAi commonly involves the use of dsRNAs that are greater than 500 bp; however, it can also be activated by introduction of either siRNAs (Elbashir, et al., Nature 2001; 411: 494-498) or short hairpin RNAs (shRNAs) bearing a fold back stem-loop structure (Paddison et al., Genes Dev. 2002; 16: 948-958; Sui et al., Proc. Natl. Acad. Sci. USA 2002; 99:5515-5520; Brummelkamp et al., Science 2002; 296:550-553; Paul et al., Nature Biotechnol. 2002; 20:505-508).

The siRNAs are preferably short double stranded nucleic acid duplexes comprising annealed complementary single stranded nucleic acid molecules. Preferably, the siRNAs are short dsRNAs comprising annealed complementary single strand RNAs. siRNAs may also comprise an annealed RNA:DNA duplex, wherein the sense strand of the duplex is a DNA molecule and the antisense strand of the duplex is a RNA molecule.

Preferably, each single stranded nucleic acid molecule of the siRNA duplex is of from about 19 nucleotides to about 27 nucleotides in length. In preferred embodiments, duplexed siRNAs have a 2 or 3 nucleotide 3' overhang on each strand of the duplex. In preferred embodiments, siRNAs have 5'-phosphate and 3'-hydroxyl groups.

RNAi molecules may include one or more modifications, either to the phosphate-sugar backbone or to the nucleoside. For example, the phosphodiester linkages of natural RNA may be modified to include at least one heteroatom other than oxygen, such as nitrogen or sulfur. In this case, for example, the phosphodiester linkage may be replaced by a phosphothioester linkage. Similarly, bases may be modified to block the activity of adenosine deaminase. Where the RNAi molecule is produced synthetically, or by in vitro transcription, a modified ribonucleoside may be introduced during synthesis or transcription. The skilled artisan will understand that many of the modifications described above for antisense oligonucleotides may also be made to RNAi molecules. Such modifications are well known in the art.

siRNAs may be introduced to a target cell as an annealed duplex siRNA, or as single stranded sense and antisense nucleic acid sequences that, once within the target cell, anneal to form the siRNA duplex. Alternatively, the sense and antisense strands of the siRNA may be encoded on an expression construct that is introduced to the target cell. Upon expression within the target cell, the transcribed sense and antisense strands may anneal to reconstitute the siRNA.

shRNAs typically comprise a single stranded "loop" region connecting complementary inverted repeat sequences that anneal to form a double stranded "stem" region. Structural considerations for shRNA design are discussed, for example, in McManus et al., RNA 2002; 8:842-850. In certain embodiments the shRNA may be a portion of a larger RNA molecule, e.g., as part of a larger RNA that also contains U6 RNA sequences (Paul et al., supra).

In preferred embodiments, the loop of the shRNA is from about 1 to about 9 nucleotides in length. In preferred embodiments the double stranded stem of the shRNA is from about 19 to about 33 base pairs in length. In preferred embodiments, the 3' end of the shRNA stem has a 3' overhang. In particularly preferred embodiments, the 3' overhang of the shRNA stem is from 1 to about 4 nucleotides in length. In preferred embodiments, shRNAs have 5'-phosphate and 3'-hydroxyl groups.

Although RNAi molecules preferably contain nucleotide sequences that are fully complementary to a portion of the target nucleic acid, 100% sequence complementarity between the RNAi probe and the target nucleic acid is not required.

Similar to the above-described antisense oligonucleotides, RNAi molecules can be synthesized by standard methods known in the art, e.g., by use of an automated synthesizer. RNAs produced by such methodologies tend to be highly pure and to anneal efficiently to form siRNA duplexes or shRNA hairpin stem-loop structures. Following chemical synthesis, single stranded RNA molecules are deprotected, annealed to form siRNAs or shRNAs, and purified (e.g., by gel electrophoresis or HPLC). Alternatively, standard procedures may be used for in vitro transcription of RNA from DNA templates carrying RNA polymerase promoter sequences (e.g., T7 or SP6 RNA polymerase promoter sequences). Efficient in vitro protocols for preparation of siRNAs using T7 RNA polymerase have been described (Done and Picard, Nucleic Acids Res. 2002; 30:e46; and Yu et al., Proc. Natl. Acad. Sci. USA 2002; 99:6047-6052). Similarly, an efficient in vitro protocol for preparation of shRNAs using T7 RNA polymerase has been described (Yu et al., supra). The sense and antisense transcripts may be synthesized in two independent reactions and annealed later, or may be synthesized simultaneously in a single reaction.

RNAi molecules may be formed within a cell by transcription of RNA from an expression construct introduced into the cell. For example, both a protocol and an expression construct for in vivo expression of siRNAs are described in Yu et al., supra. The delivery of siRNA to tumors can potentially be achieved via any of several gene delivery "vehicles" that are currently available. These include viral vectors, such as adenovirus, lentivirus, herpes simplex virus, vaccinia virus, and retrovirus, as well as chemical-mediated gene delivery systems (for example, liposomes), or mechanical DNA delivery systems (DNA guns). The oligonucleotides to be expressed for such siRNA-mediated inhibition of gene expression would be between 18 and 28 nucleotides in length. Protocols and expression constructs for in vivo expression of shRNAs have been described (Brummelkamp et al., Science 2002; 296:550-553; Sui et al., supra; Yu et al., supra; McManus et al., supra; Paul et al., supra).

The expression constructs for in vivo production of RNAi molecules comprise RNAi encoding sequences operably linked to elements necessary for the proper transcription of the RNAi encoding sequence(s), including promoter elements and transcription termination signals. Preferred promoters for use in such expression constructs include the polymerase-III HI-RNA promoter (see, e.g., Brummelkamp et al., supra) and the U6 polymerase-III promoter (see, e.g., Sui et al., supra; Paul, et al. supra; and Yu et al., supra). The RNAi expression constructs can further comprise vector sequences that facilitate the cloning of the expression constructs. Standard vectors are known in the art (e.g., pSilencer 2.0-U6 vector, Ambion Inc., Austin, Tex.).

Ribozyme Inhibition

The level of expression of a target polypeptide of the invention can also be inhibited by ribozymes designed based on the nucleotide sequence thereof.

Ribozymes are enzymatic RNA molecules capable of catalyzing the sequence-specific cleavage of RNA (for a review, see Rossi, Current Biology 1994; 4:469-471). The mechanism of ribozyme action involves sequence-specific hybridization of the ribozyme molecule to complementary target RNA, followed by an endonucleolytic cleavage event. The composition of ribozyme molecules must include: (i) one or more sequences complementary to the target RNA; and (ii) a catalytic sequence responsible for RNA cleavage (see, e.g., U.S. Pat. No. 5,093,246).

The use of hammerhead ribozymes is preferred. Hammerhead ribozymes cleave RNAs at locations dictated by flanking regions that form complementary base pairs with the target RNA. The sole requirement is that the target RNA has the following sequence of two bases: 5'-UG-3'. The construction of hammerhead ribozymes is known in the art, and described more fully in Myers, Molecular Biology and Biotechnology: A Comprehensive Desk Reference, VCH Publishers, New York, 1995 (see especially FIG. 4, page 833) and in Haseloff and Gerlach, Nature 1988; 334:585-591.

As in the case of antisense oligonucleotides, ribozymes can be composed of modified oligonucleotides (e.g., for improved stability, targeting, etc.). These can be delivered to cells which express the target polypeptide in vivo. A preferred method of delivery involves using a DNA construct "encoding" the ribozyme under the control of a strong constitutive pol III or pol II promoter, so that transfected cells will produce sufficient quantities of the ribozyme to catalyze cleavage of the target mRNA encoding the target polypeptide. However, because ribozymes, unlike antisense molecules, are catalytic, a lower intracellular concentration may be required to achieve an adequate level of efficacy.

Ribozymes can be prepared by any method known in the art for the synthesis of DNA and RNA molecules, as discussed above. Ribozyme technology is described further in Intracellular Ribozyme Applications: Principals and Protocols, Rossi and Couture eds., Horizon Scientific Press, 1999.

Triple Helix Forming Oligonucleotides (TFOs)

Nucleic acid molecules useful to inhibit expression level of a target polypeptide of the invention via triple helix formation are preferably composed of deoxynucleotides. The base composition of these oligonucleotides is typically designed to promote triple helix formation via Hoogsteen base pairing rules, which generally require sizeable stretches of either purines or pyrimidines to be present on one strand of a duplex. Nucleotide sequences may be pyrimidine-based, resulting in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, e.g., those containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, sequences can be targeted for triple helix formation by creating a so-called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

Similarly to RNAi molecules, antisense oligonucleotides, and ribozymes, described above, triple helix molecules can be prepared by any method known in the art. These include techniques for chemically synthesizing oligodeoxyribonucleotides and oligoribonucleotides such as, e.g., solid phase phosphoramidite chemical synthesis. Alternatively, RNA molecules can be generated by in vitro or in vivo transcription of DNA sequences "encoding" the particular RNA molecule. Such DNA sequences can be incorporated into a wide variety of vectors that incorporate suitable RNA polymerase promoters such as the T7 or SP6 polymerase promoters. See, Nielsen, P. E. "Triple Helix: Designing a New Molecule of Life", Scientific American, December, 2008; Egholm, M., et al. "PNA Hybridizes to Complementary Oligonucleotides Obeying the Watson-Crick Hydrogen Bonding Rules." (1993) Nature, 365, 566-568; Nielsen, P. E. 'PNA Technology'. Mol Biotechnol. 2004; 26:233-48.

Antibodies and Aptamers

The polypeptide targets described herein, e.g., HSD17B11, HSD17B12, HSD17B14, etc.) can be inhibited (e.g., the level can be reduced) by the administration to or expression in a subject or a cell or tissue thereof, of blocking antibodies or aptamers against the polypeptide.

Antibodies, or their equivalents and derivatives, e.g., intrabodies, or other antagonists of the polypeptide, may be used in accordance with the present methods. Methods for engineering intrabodies (intracellular single chain antibodies) are well known. Intrabodies are specifically targeted to a particular compartment within the cell, providing control over where the inhibitory activity of the treatment is focused. This technology has been successfully applied in the art (for review, see Richardson and Marasco, 1995, TIBTECH vol. 13; Lo et al. (2009) *Handb Exp Pharmacol.* 181:343-73; Maraasco, W. A. (1997) *Gene Therapy* 4:11-15; see also, U.S. Pat. Appln. Pub. No. 2001/0024831 by Der Maur et al. and U.S. Pat. No. 6,004,940 by Marasco et al.).

Administration of a suitable dose of the antibody or the antagonist (e.g., aptamer) may serve to block the level (expression or activity) of the polypeptide in order to treat or prevent cancer, e.g., inhibit growth of a breast cancer cell or tumor (e.g., ER+ or ER− breast cancer cell or tumor).

In addition to using antibodies and aptamers to inhibit the levels and/or activity of a target polypeptide, it may also be possible to use other forms of inhibitors. For example, it may be possible to identify antagonists that functionally inhibit the target polypeptide (e.g., HSD17B11, HSD17B12, HSD17B14, etc.). In addition, it may also be possible to interfere with the interaction of the polypeptide with its substrate. Other suitable inhibitors will be apparent to the skilled person.

The antibody (or other inhibitors and antagonists) can be administered by a number of methods. For example, for the administration of intrabodies, one method is set forth by Marasco and Haseltine in PCT WO 94/02610. This method discloses the intracellular delivery of a gene encoding the intrabody. In one embodiment, a gene encoding a single chain antibody is used. In another embodiment, the antibody would contain a nuclear localization sequence. By this method, one can intracellularly express an antibody, which can block activity of the target polypeptide in desired cells.

Aptamers are oligonucleic acid or peptide molecules that bind to a specific target molecule. Aptamers can be used to inhibit gene expression and to interfere with protein interactions and activity. Nucleic acid aptamers are nucleic acid species that have been engineered through repeated rounds of in vitro selection (e.g., by SELEX (systematic evolution of ligands by exponential enrichment)) to bind to various molecular targets such as small molecules, proteins, nucleic acids, and even cells, tissues and organisms. Peptide aptamers consist of a variable peptide loop attached at both ends to a protamersein scaffold. Aptamers are useful in biotechnological and therapeutic applications as they offer molecular recognition properties that rival that of antibodies. Aptamers can be engineered completely in a test tube, are readily produced by chemical synthesis, possess desirable storage properties, and elicit little or no immunogenicity in therapeutic application. Aptamers can be produced using the methodology disclosed in a U.S. Pat. No. 5,270,163 and WO 91/19813.

Small Molecules

Chemical agents, referred to in the art as "small molecule" compounds are typically organic, non-peptide molecules, having a molecular weight less than 10,000 Da, preferably less than 5,000 Da, more preferably less than 1,000 Da, and most preferably less than 500 Da. This class of modulators includes chemically synthesized molecules, for instance, compounds from combinatorial chemical libraries. Synthetic compounds may be rationally designed or identified utilizing the screening methods described below. Methods for generating and obtaining small molecules are well known in the art (Schreiber, Science 2000; 151:1964-1969; Radmann et al., Science 2000; 151:1947-1948).

Non-limiting of small molecule inhibitors (and exemplary dosages for in vitro use in cell-based assays) include, e.g., cyclopamine (e.g., 10 µM) (Selleck Chemicals, cat #S1146), an inhibitor of Smo receptor of Hh ligands; LY2109761 (e.g., 500 nM) (Eli Lilly), an inhibitor of TGFBR kinases; celecoxib (e.g., 100 µM) (LKT laboratories, cat #C1644), an inhibitor of Cox2; 2-5dideoxyadenosine (e.g., 100 µM) (Enzo Life Sciences, cat #BML-CN110-005), an inhibitor of adenylate cyclase; tyrphostin AG1478 (e.g., 10 µM) (Cayman Chemicals, cat #10010244), an inhibitor of EGFR; XAV939 (e.g., 104)(Tocris Bioscience, cat #3748), a Tankyrase (TNKS) inhibitor that antagonizes Wnt signaling via stimulation of β-catenin degradation and stabilization of axin; and picropodophyllotoxin (e.g., 0.5 µM) (Tocris Bioscience, cat #2956), an IGFR inhibitor in which stock solutions (1,000×) are prepared in DMSO.

Non-limiting examples of small molecule agonists include, e.g., the TFGb agonists described in detail in U.S. Pat. No. 8,097,645 to Wyss-Coray et al., the hedgehog (Hh) agonist cyclopaminc (see, King, W K. Journal of Biology 2002, 1:8); the Wnt agonist Calbiochem (EMD Millipore), and the cAMP agonist Alotaketal A described in Huang et al. (J. Am. Chem. Soc., 2012, 134 (21), pp 8806-8809).

In certain embodiments, the above described inhibitors and agonists can be directly targeted to a specific cell type (e.g., CD44+ or CD24+ breast epithelial cells, p27+ or Ki67+ breast epithelial cells, AR+ cells (e.g., AR+ breast epithelial cells), ER+ breast epithelial cells, ER− breast epithelial cells, and combinations thereof, e.g., ER+p27+ cells (e.g., ER+p27+ breast epithelial cells), or AR+p27+ cells (e.g., AR+p27+ breast epithelial cells), etc. The skilled artisan will appreciate that methods for specific cell targeting are well known in the art. By way of non-limiting example, antibodies, e.g., an anti-CD44, anti-CD24, anti-AR, or anti-ER antibody, etc., may be conjugated to an inhibitor or agonist described herein, in order to target the inhibitor or agonist to, for example and without limitation, CD44+, CD24+ or ER+ cells. Further the site of administration (e.g., direct injection into breast tissue and/or breast tumor) can further increase the specificity of cell targeting.

VI. Methods for Predicting a Subject's Risk of Developing Breast Cancer

Provided herein are methods for predicting a subject's risk of developing breast cancer (e.g., ER+ or ER− breast cancer).

In one embodiment, the method comprises (a) determining the frequency in a breast tissue sample of CD44+, CD24− breast epithelial cells and (b) predicting that the subject has a relatively elevated risk of developing breast cancer if the frequency of CD44+, CD24− breast epithelial cells is decreased compared to a first control frequency of CD44+, CD24− breast epithelial cells; or (c) predicting that the subject has a relatively reduced risk of developing breast cancer if the frequency of CD44+ breast epithelial cells is increased compared to a second control frequency of CD44+, CD24− breast epithelial cells.

In another embodiment, the method comprises: (a) determining the frequency in a breast tissue sample of CD24+ breast epithelial cells and (b) predicting that the subject has a relatively elevated risk of developing breast cancer if the frequency of CD24+ breast epithelial cells is increased compared to a first control frequency of CD24+ breast epithelial cells; or (c) predicting that the subject has a relatively reduced risk of developing breast cancer if the frequency of CD24+ breast epithelial cells is decreased compared to a second control frequency of CD24+ breast epithelial cells.

As discussed in the Definitions section, above, a "first control frequency" of a cell type (e.g., CD44+ or CD24+ cells, or p27+ cells, Ki67+ cells, etc.) is the frequency of that cell type in a comparable sample from a patient or the average frequency in comparable samples from a plurality of patients known to be at low risk of developing breast cancer (e.g., parous women not expressing BRCA1 or BRCA2 mutations, where the women are premenopausal and/or postmenopausal). In other words, the first control frequency is a "negative" control for an elevated risk of developing breast cancer. As also discussed above, a "second control frequency" of a cell type is the frequency of that cell type in a comparable sample from a patient or the average frequency in comparable samples from a plurality of patients known to be at high risk of developing breast cancer (e.g., pre and/or postmenopausal nulliparous women). In other words, the second control frequency is a "positive" control for an elevated risk of developing the breast cancer. The first and second control frequencies can be simultaneously determined or can be determined before or after the frequency of the relevant cell is determined in the breast cells from the subject for whom the risk prediction is being made.

In a particularly preferred embodiment, the frequency of both CD44+ and CD24+ breast epithelial cells in the sample is determined as described above, and the method comprises predicting that the subject has a relatively elevated risk of developing breast cancer if: (i) the frequency of CD44+, CD24− breast epithelial cells is decreased compared to a first control frequency of CD44+, CD24− breast epithelial cells, and (ii) the frequency of CD24+ breast epithelial cells is increased compared to a first control frequency of CD24+ breast epithelial cells; and step (c) comprises predicting that the subject has a relatively reduced risk of developing breast cancer if: (i) the frequency of CD44+ breast epithelial cells is increased compared to a second control frequency of CD44+, CD24− breast epithelial cells, and (ii) the frequency of CD24+ breast epithelial cells is decreased compared to a second control frequency of CD24+ breast epithelial cells.

In other embodiments, the first and second control frequencies of CD44+ and CD24+ breast epithelial cells, described above, can also be first and second predetermined reference frequencies, respectively (i.e., standards) to which the frequency of the cell type in a test sample is compared.

For example, the predetermined reference frequency for a first control frequency, of CD44+, CD24− breast epithelial cells is preferably in the range of 15-30% or higher of the total breast epithelial cells in the sample. Further, as disclosed herein, a subject considered to have a relatively elevated risk of developing breast cancer will have a decreased frequency of CD44+, CD24− breast epithelial cells relative to that predetermined reference frequency; thus, a subject determined to have a frequency of CD44+, CD24− breast epithelial cells less than 15% would be predicted to have a relatively elevated risk of developing breast cancer. More preferably, a subject determined to have a frequency of CD44+, CD24− breast epithelial cells less than 14%, less than 13%, less than 12%, less than 11%, less than 10%, less than 9%, less than 8%, less than 7%, less than 6%, or less than 5%, is predicted to have a relatively elevated risk of developing breast cancer.

The predetermined reference frequency for a second control frequency of CD44+, CD24− breast epithelial cells is preferably in the range of 15% or less (e.g., less than 15%, less than 14%, less than 13%, less than 12%, less than 11%, less than 10%, etc.) of the total breast epithelial cells in the sample. As disclosed herein, a subject considered to have a relatively reduced risk of developing breast cancer will have an increased frequency of CD44+, CD24− breast epithelial cells relative to the second predetermined reference frequency; thus, a subject determined to have a frequency of CD44+, CD24− breast epithelial cells greater than 15%, preferably greater than 16%, greater than 17%, greater than 18%, greater than 19%, greater than 20%, greater than 21%, greater than 22%, greater than 23%, greater than 24%, greater than 25%, greater than 26%, greater than 27%, greater than 28%, greater than 29%, or greater than 30% is predicted to have a relatively reduced risk of developing breast cancer.

The first predetermined reference frequency of CD24+ breast epithelial cells is preferably 20%, or less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, or less than 5% of the total breast epithelial cells in the sample. As disclosed herein, a subject considered to have a relatively elevated risk of developing breast cancer will have an increased frequency of CD24+ breast epithelial cells relative to the first predetermined reference frequency of CD24+ breast epithelial cells; thus, a subject determined to have a frequency of CD24+ breast epithelial cells greater than 20%, greater than 21%, greater than 22%, greater than 23%, greater than 24%, greater than 25%, greater than 26%, greater than 27%, greater than 28%, greater than 29%, greater than 30%, greater than 31%, greater than 32%, greater than 33%, greater than 34%, greater than 35%, greater than 36%, greater than 37%, greater than 38%, greater than 39%, greater than 40%, greater than 41%, greater than 42%, greater than 43%, greater than 44%, greater than 45%, greater than 46%, greater than 47%, greater than 48%, greater than 49%, or greater than 50% of the total breast epithelial cells in the sample, is predicted to have a relatively elevated risk of developing breast cancer.

The second predetermined reference frequency of CD24+ breast epithelial cells is preferably 20%, or greater than 20%, greater than 21%, greater than 22%, greater than 23%, greater than 24%, greater than 25%, greater than 26%, greater than 27%, greater than 28%, greater than 29%, greater than 30%, greater than 31%, greater than 32%, greater than 33%, greater than 34%, greater than 35%, greater than 36%, greater than 37%, greater than 38%, greater than 39%, greater than 40%, greater than 41%, greater than 42%, greater than 43%, greater than 44%, greater than 45%, greater than 46%, greater than 47%, greater than 48%, greater than 49%, or greater than 50%, of the total breast epithelial cells in the sample. As disclosed herein, a subject considered to have a relatively reduced risk of developing breast cancer will have a decreased frequency of CD24+ breast epithelial cells relative to the second predetermined reference frequency; thus, a subject determined to have a frequency of CD24+ breast epithelial cells less than 20% (e.g., less than 20%, less than 19%, less than 18%, less than 17%, less than 16%, less than 15%, less than 14%, less than 13%, less than 12%, less than 11%, less than 10%, less than 5%, etc.) would be predicted to have a relatively reduced risk of developing breast cancer.

In yet other embodiments, the method for predicting a subject's risk of developing an breast cancer comprises: predicting that the subject has a relatively elevated risk of developing breast cancer if the frequency of CD24+ breast epithelial cells is greater than the frequency of CD44+, CD24− breast epithelial cells in the sample; and step (c) comprises predicting that the subject has a relatively reduced risk of developing breast cancer if the frequency of CD24+ breast epithelial cells is equal to or less than the frequency of CD44+, CD24− breast epithelial cells in the sample. In still other embodiments, the method for predicting a subject's risk of developing an breast cancer comprises predicting that the subject has a relatively elevated risk of developing breast cancer if the ratio of CD24+ breast epithelial cells to CD44+, CD24− breast epithelial cells in a breast epithelial cell-containing sample from the subject is 2, or greater than 2, greater than 3, greater than 4, greater than 5, greater than 6, greater than 7, greater than 8, greater than 9, or greater than 10; or, predicting that the subject has a relatively reduced risk of developing breast cancer if the ratio of CD24+ breast epithelial cells to CD44+, CD24− breast epithelial cells in a breast epithelial cell-containing sample from the subject is less than 2, preferably less than 1.5, less than 1, less than 0.9, less than 0.8, less than 0.7, less than 0.6, less than 0.5, less than 0.4, less than 0.3, less than 0.2, less than 0.1, less than 0.05, or less than 0.01.

In other embodiments, a method of predicting a subject's risk of developing an estrogen-receptor-positive (ER+) breast cancer is provided, wherein the method comprises: (a) determining the frequency in a breast tissue sample of cells of one or more types of cells, such as, e.g., p27+ breast epithelial cells, Sox17+ breast epithelial cells, Cox2+ breast epithelial cells, Ki67+ breast epithelial cells, ER+, p27+ breast epithelial cells, ER+, Sox17+ breast epithelial cells, ER+, Cox2+ breast epithelial cells, ER+, Ki67+ breast epithelial cells, AR+, p27+ breast epithelial cells, AR+, Sox17+ breast epithelial cells, AR+, Cox2+ breast epithelial cells, and AR+, Ki67+ breast epithelial cells; and (b) predicting that the subject has a relatively elevated risk of developing breast cancer if the frequency of the cells of the type is increased compared to a first control frequency of cells of the type; or (c) predicting that the subject has a relatively reduced risk of developing breast cancer if the frequency of the cells of the type is decreased compared to a second control frequency of the cells of the type. In a preferred embodiment, the frequencies of two or more, three or more, or all of the cell types (e.g., p27+, Ki67+, Sox17 and/or Cox2+ breast epithelial cells and/or ER+, p27+ breast epithelial cells, ER+, Sox17+ breast epithelial cells, ER+, Cox2+ breast epithelial cells, ER+, Ki67+ breast epithelial cells, AR+, p27+ breast epithelial cells, AR+, Sox17+ breast epithelial cells, AR+, Cox2+ breast epithelial cells, and/or AR+, Ki67+ breast epithelial cells are determined, as described above.

In one embodiment of the above method, the frequency of the p27+ breast epithelial cells, Ki67+ breast epithelial cells, Sox17+ breast epithelial cells, Cox2+ breast epithelial cells, ER+, p27+ breast epithelial cells, ER+, Sox17+ breast epithelial cells, ER+, Cox2+ breast epithelial cells, ER+, Ki67+ breast epithelial cells, AR+, p27+ breast epithelial cells, AR+, Sox17+ breast epithelial cells, AR+, Cox2+ breast epithelial cells, and/or AR+, Ki67+ breast epithelial cells is increased relative to the first control frequency by at least 2-fold, at least 3-fold, at least 4-fold, at least 5-fold, at least 10-fold, or more. Also preferably, in the above method, the frequency of the p27+, Ki67+, Sox17 and/or Cox2+ breast epithelial cells is decreased relative to the second control frequency by at least 2-fold, at least 3-fold, at least 4-fold, at least 5-fold, at least 10-fold, or more.

In another embodiment, step (b) of the method described above comprises predicting that the subject has a relatively elevated risk of developing breast cancer if the frequency of p27+ breast epithelial cells is 15% or greater (e.g., 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% or greater) of the breast epithelial cells in the sample; and step (c) comprises predicting that the subject has a relatively reduced risk of developing breast cancer if the frequency of p27+ breast epithelial cells is less than 15% (e.g., 14%, 13%, 12%, 11%, 10%, 9%, 8%, 7%, 6%, 5%, 4%, 3%, 2%, 1% or less) of the breast epithelial cells in the sample.

In another embodiment, step (b) of the method described above comprises predicting that the subject has a relatively elevated risk of developing breast cancer if the frequency of Ki67+ breast epithelial cells is 2% or greater or 3% of greater of the breast epithelial cells in the sample, and step (c) comprises predicting that the subject has a relatively reduced risk of developing breast cancer if the frequency of Ki67+ breast epithelial cells is less than 2% (e.g., 1.9%, 1.8%, 1.7%, 1.6%, 1.5%, 1.0%, 0.5%, or 0%) of the breast epithelial cells in the sample.

In another embodiment, step (b) of the method described above comprises predicting that the subject has a relatively elevated risk of developing breast cancer if the frequency of p27+ breast epithelial cells is 15% or greater (e.g., 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% or greater) of the breast epithelial cells in the sample; and step (c) comprises predicting that the subject has a relatively reduced risk of developing breast cancer if the frequency of p27+ breast epithelial cells is less than 15% (e.g., 14%, 13%, 12%, 11%, 10%, 9%, 8%, 7%, 6%, 5%, 4%, 3%, 2%, 1% or less) of the breast epithelial cells in the sample.

In another embodiment, step (b) of the method described above comprises predicting that the subject has a relatively elevated risk of developing breast cancer if the frequency of p27+, AR+ breast epithelial cells is 10% or greater (e.g., 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% or greater) of the breast epithelial cells in the sample; and step (c) comprises predicting that the subject has a relatively reduced risk of developing breast cancer if the frequency of p27+ breast epithelial cells is less than 10% (e.g., 9%, 8%, 7%, 6%, 5%, 4%, 3%, 2%, 1% or less) of the breast epithelial cells in the sample.

In yet other embodiments, a method of predicting a subject's risk of developing an breast cancer is provided, wherein the method comprises: (a) determining the expression level in a breast tissue sample from a subject of at least one marker, e.g., p27, Sox17 and Cox2; and (b) predicting that the subject has a relatively elevated risk of developing breast cancer if the expression level of the at least one marker is increased compared to a first control level of the at least one marker; or (c) predicting that the subject has a relatively reduced risk of developing breast cancer if the expression level of the at least one marker is decreased compared to a second control level of the at least one marker. Methods for determining the expression level of markers p27, Sox17 and Cox2 (e.g., QPCR, FACS, immunohistochemistry, Western blot, ELISA) are described above.

In step (b) in the above method, preferably, the expression level of p27, Sox17 and/or Cox2 (e.g., mRNA and/or polypeptide) is increased by at least 2-fold, at least 3-fold, at least 4-fold, at least 5-fold, at least 6-fold, at least 7-fold, at least 8-fold, at least 9-fold, at least 10-fold, at least 20-fold or greater, compared to the first control level (i.e., a control level from a subject known to be at low risk of developing breast cancer). In step (c) in the above method, preferably, the expression level of p27, Sox17 and/or Cox2 (e.g., mRNA and/or polypeptide) is decreased by at least 2-fold, at least 3-fold, at least 4-fold, at least 5-fold, at least 6-fold, at least 7-fold, at least 8-fold, at least 9-fold, at least 10-fold, at least 20-fold or more, compared to the second control level (i.e., a control level from a subject known to be at high risk of developing breast cancer).

In still other embodiments, methods of predicting the risk of developing breast cancer are provided, which comprise determining a parity/nulliparity-associated gene expression signature in a sample comprising breast epithelial cells. Also provided are methods of predicting breast cancer disease outcome by testing for a parity/nulliparity-associated gene expression signature in breast cancer cells.

As described above and in Example 10, the genes that were shown to be upregulated or downregulated in FIG. 28 make up a parity/nulliparity-related gene signature. Further, the genes for which the expression profile is shown in FIG. 28 are described in detail in Table 18, below. Of course, the skilled artisan will appreciate that a parity/nulliparity-related gene signature can, but does not necessarily comprise all of the genes shown in Table 18. Such gene signature comprises 2 or more, 3 or more, 4 or more, 5 or more, 10 or more, 15 or more, 20 or more, 30 or more, 40 or more, 50 or more, or 100 or more of the genes shown in Table 18.

Further, for each of the genes shown in Table 18, the disease outcome based on the expression of a particular gene in the expression is shown (i.e., a prognosis of "good" or "bad"). Thus, the skilled artisan can select one or more genes from the list of genes in Table 18 that are correlated with a "good" prognosis and/or one or more genes associated with a "bad" prognosis, and assemble the selected genes in a custom gene signature. A subject's gene expression profile for the genes in the custom signature can be determined, and for example, if the subject expresses more of the genes associated with a "bad" prognosis than the genes associated with a "good" prognosis, then the patient's disease outcome is predicted to be "bad" or "poor", whereas as subject expressing more of the "good" prognosis genes is predicted to have a "good" prognosis (i.e., more likely to survive the disease).

The above described methods of predicting a subject's risk of developing cancer and for determining a disc outcome (e.g., prognosis), can be used, e.g., by the subject's physician to determine the best course of treatment or prophylaxis to administer to the subject in need thereof, as well as other courses of action. For example, such methods can further comprise administering to a subject identified as having an increased risk of developing breast cancer, or a subject diagnosed with breast cancer and determined according to the above methods to have a bad prognosis, a therapy or therapeutic agent for treating, reducing the risk of developing, or preventing breast cancer (e.g., ER+ or ER− breast cancer). In other embodiments, the methods can comprise performing additional diagnostic assays to confirm the diagnosis (e.g., imaging, biopsy, etc.), recording the diagnosis in a database or medical history (e.g., medical records) of the subject, performing diagnostic tests on a family member of the subject, selecting the subject for increased monitoring or periodically monitoring the health of the subject (e.g., for development of signs or symptoms of breast cancer, e.g., tumor development or tumor size changes (e.g., increased or decreased size), such as e.g., clinical breast exam, mammography, MRI, or other suitable imaging or other diagnostic method(s) known in the art.

VII. Administration

Compositions and formulations comprising an inhibitor or agonist of the invention (e.g., an inhibitor or agonist of a gene or polypeptide mediating a function in a pathway that is upregulated or downregulated in breast epithelial cells of nulliparous women), can be administered topically, parenterally, orally, by inhalation, as a suppository, or by other methods known in the art. The term "parenteral" includes injection (for example, intravenous, intraperitoneal, epidural, intrathecal, intramuscular, intraluminal, intratracheal or subcutaneous). Exemplary routes of administration include, e.g., intravenous, intraductal, and intratumoral.

While it is possible to use an inhibitor or agonist of the invention for therapy as is, it may be preferable to administer an inhibitor or agonist as a pharmaceutical formulation, e.g., in admixture with a suitable pharmaceutical excipient, diluent, or carrier selected with regard to the intended route of administration and standard pharmaceutical practice. Pharmaceutical formulations comprise at least one active compound, or a pharmaceutically acceptable derivative thereof, in association with a pharmaceutically acceptable excipient, diluent, and/or carrier. The excipient, diluent and/or carrier must be "acceptable," as defined above.

Administration of a composition or formulation of the invention can be once a day, twice a day, or more often. Frequency may be decreased during a treatment maintenance phase of the disease or disorder, e.g., once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the present compounds.

It will be appreciated that the amount of an inhibitor required for use in treatment will vary with the route of administration, the nature of the condition for which treatment is required, and the age, body weight and condition of the patient, and will be ultimately at the discretion of the attendant physician or veterinarian. Compositions will typically contain an effective amount of the active agent(s), alone or in combination. Preliminary doses can be determined according to animal tests, and the scaling of dosages for human administration can be performed according to art-accepted practices.

Length of treatment, i.e., number of days, will be readily determined by a physician treating the subject; however the number of days of treatment may range from 1 day to about 20 days. As provided by the present methods, and discussed below, the efficacy of treatment can be monitored during the course of treatment to determine whether the treatment has been successful, or whether additional (or modified) treatment is necessary.

VIII. Methods of Treating and Preventing Breast Cancer

Provided herein are methods for treating and preventing estrogen-receptor-positive (ER+) breast cancer in a subject. Typically, a subject that can be administered an inhibitor or agonist, or composition, e.g., pharmaceutical composition, comprising one or more inhibitors or agonists described above is a premenopausal or postmenopausal woman. In some embodiments, the subject has a BRCA-1 or BRCA-2 germline mutation.

In certain embodiments, methods of treating breast cancer (e.g., ER+ or ER− breast cancer) in a subject are provided that comprise administering to the subject a composition comprising an inhibitor of a pathway that has increased activity in breast epithelial cells (e.g., CD44+, CD24− breast epithelial cells) of nulliparous women compared to the activity in breast epithelial cells of parous women (i.e. a pathway active in nulliparous breast epithelial cells). In other embodiments an agonist of a pathway that has decreased activity in breast epithelial cells (e.g., CD44+, CD24− breast epithelial cells) of nulliparous women compared to the activity in breast epithelial cells of parous women (i.e. a pathway active in parous breast epithelial cells) can be administered. Such inhibitors and agonists and the target pathways and genes in those pathways are described in detail above.

In other embodiments, methods of preventing breast cancer (e.g., ER+ or ER− breast cancer) in a subject are provided that comprise administering to a subject at risk of developing breast cancer an inhibitor of a pathway active in nulliparous breast epithelial cells (e.g., CD44+, CD24− breast epithelial cells). For example, the pathway can include a mediator molecule such as cAMP, EGFR, Cox2, Hh, TGFBR, and IGFR, as described above. In another embodiment, the method of preventing breast cancer in a subject comprises administering to the subject an agonist of a pathway active in parous breast epithelial cells (e.g., CD44+, CD24− breast epithelial cells) (e.g., an agonist of Hakai/CBLL1, CASP8, SCR1B, LLGL2, PI3K/AKT signaling, and apoptosis).

In certain embodiments, an inhibitor or agonist or any combination of 2 or more, 3 or more, 4 or more, or 5 or more inhibitors and/or agonists of the above-described target genes and/or polypeptides can be administered in a combination therapy to a subject for the treatment or prevention of breast cancer (e.g., ER+ or ER− breast cancer).

The skilled artisan will appreciate that other combinations of inhibitors and/or agonists are possible, so long as the combination results in the treatment or prevention of breast cancer.

The skilled artisan will also appreciate that the methods of treating breast cancer described herein (e.g., administration of one or more of the inhibitors and agonists described above) may also be administered in a combination therapy with other treatments, e.g. other cancer therapies. Non-limiting examples of such cancer therapies include, e.g., chemotherapy, radiation therapy, biological therapy (e.g., antibodies, biological modifiers (cytokines, growth factors, lymphokines, chemokines, etc.), immune cell therapies (LAK cells, tumor specific CTL, etc.), anti-angiogenic therapy, surgery, and combinations thereof.

Chemotherapeutic agents, include for example: taxanes such as taxol, taxotere or their analogues; alkylating agents such as cyclophosphamide, isosfamide, melphalan, hexamethylmelamine, thiotepa or dacarbazine; antimetabolites such as pyrimidine analogues, for instance 5-fluorouracil, cytarabine, capecitabine, and gemcitabine or its analogues such as 2-fluorodeoxycytidine; folic acid analogues such as methotrexate, idatrexate or trimetrexate; spindle poisons including vinca alkaloids such as vinblastine, vincristine, vinorelbine and vindesine, or their synthetic analogues such as navelbine, or estramustine and a taxoid; platinum compounds such as cisplatin; epipodophyllotoxins such as etoposide or teniposide; antibiotics such as daunorubicin, doxorubicin, bleomycin or mitomycin, enzymes such as L-asparaginase, topoisomerase inhibitors such as topotecan or pyridobenzoindole derivatives; and various agents such as procarbazine, mitoxantrone, and biological response modifiers or growth factor inhibitors such as interferons or interleukins. Other chemotherapeutic agents include, though are not limited to, a p38/JAK kinase inhibitor, e.g., SB203580; a phosphatidyl inositol-3 kinase (PI3K) inhibitor, e.g., LY294002; a MAPK inhibitor, e.g. PD98059; a JAK inhibitor, e.g., AG490; preferred chemotherapeutics such as UCN-01, NCS, mitomycin C (MMC), NCS, and anisomycin; taxoids in addition to those describe above (e.g., as disclosed in U.S. Pat. Nos. 4,857,653; 4,814,470; 4,924,011, 5,290,957; 5,292,921; 5,438,072; 5,587,493; European Patent No. 0 253 738; and PCT Publication Nos. WO 91/17976, WO 93/00928, WO 93/00929, and WO 96/01815. In other embodiments, a cancer therapy can include but is not limited to administration of cytokines and growth factors such as interferon (IFN)-gamma, tumor necrosis factor (TNF)-alpha, TNF-beta, and/or similar cytokines, or an antagonist of a tumor growth factor (e.g., TGF-β and IL-10). Antiangiogenic agents, include, e.g., endostatin, angiostatin, TNP-470, Caplostatin (Stachi-Fainaro et al., Cancer Cell 7(3), 251 (2005)). Drugs that interfere with intracellular protein synthesis can also be used in the methods of the present invention; such drugs are known to those skilled in the art and include puromycin, cycloheximide, and ribonuclease.

For radiation therapy, common sources of radiation used for cancer treatment include, but are not limited to, high-energy photons that come from radioactive sources such as cobalt, cesium, iodine, palladium, or a linear accelerator, proton beams; neutron beams (often used for cancers of the head, neck, and prostate and for inoperable tumors), x or gamma radiation, electron beams, etc.

It is well known that radioisotopes, drugs, and toxins can be conjugated to antibodies or antibody fragments which specifically bind to markers which are produced by or associated with cancer cells, and that such antibody conjugates can be used to target the radioisotopes, drugs or toxins to tumor sites to enhance their therapeutic efficacy and minimize side effects. Examples of these agents and methods are reviewed in Wawrzynczak and Thorpe (in Introduction to the Cellular and Molecular Biology of Cancer, L. M. Franks and N. M. Teich, eds, Chapter 18, pp. 378-410, Oxford University Press. Oxford, 1986), in Immunoconjugates: Antibody Conjugates in Radioimaging and Therapy of Cancer (C. W. Vogel, ed., 3-300, Oxford University Press, N.Y., 1987), in Dillman, R. O. (CRC Critical Reviews in Oncology/Hematology 1:357, CRC Press, Inc., 1984), in Pastan et al. (Cell 47:641, 1986) in Vitetta et al. (Science 238:1098-1104, 1987) and in Brady et al. (Int. J. Rad. Oncol. Biol. Phys. 13:1535-1544, 1987). Other examples of the use of immunoconjugates for cancer and other forms of therapy have been disclosed, inter alia, in U.S. Pat. Nos. 4,331,647, 4,348,376, 4,361,544, 4,468,457, 4,444,744, 4,460,459, 4,460,561 4,624,846, 4,818,709, 4,046,722, 4,671,958, 4,046,784, 5,332,567, 5,443,953, 5,541,297, 5,601,825, 5,637,288, 5,677,427, 5,686,578, 5,698,178, 5,789,554, 5,922,302, 6,187,287, and 6,319,500.

IX. Methods for Determining Efficacy of a Breast Cancer Therapy

In certain embodiments, methods for determining the efficacy of a breast cancer therapy (including prophylactic therapy) are provided. The therapy can be a therapy described herein or any other conventional breast cancer therapy. In one embodiment, the efficacy of a cancer therapy is determined by comparing a subject's parity/nulliparity-related gene expression profile before treatment for the breast cancer to the subject's parity/nulliparity-related gene expression profile during or after the treatment. Typically, a subject that is in need of breast cancer treatment (including prophylactic therapy, e.g., for a subject determined to have an elevated risk of developing breast cancer) will have a parity/nulliparity-related gene expression profile that most closely resembles (i.e., is the same or similar to) the gene signature for nulliparous women. After a successful therapy, it is expected that the subject's gene expression profile will more closely resemble the parity/nulliparity-related gene expression profile of parous women, as described herein (e.g., FIG. 28 and Table 18). A gene signature not resembling the gene expression profile of parous women is an indication that the treatment was not successful, and further treatment or a different treatment is needed.

In other embodiments, a method for determining efficacy of an breast cancer therapy (including prophylactic therapy) comprises measuring the level of a specific gene and/or polypeptide before and after (or during the therapy). For example, as described above, in certain embodiments a method for treating or preventing breast cancer comprises administering an inhibitor or agonist of a specific gene or polypeptide. The level or activity of the target gene or polypeptide can be measured before or at the beginning of treatment, and then again during of or after treatment; typically, when an inhibitor is administered as a cancer therapy, the inhibition and therapy is deemed effective if the level or activity of the target gene or polypeptide is decreased by at least 2-fold, at least 3-fold, at least 4-fold, at least 5-fold, at least 10-fold, or more, relative to the level of the target gene or polypeptide at the beginning of or before commencement of the cancer therapy. Typically, when an agonist is administered as a cancer therapy, the inhibition and therapy is deemed effective if the level or activity of the target gene or polypeptide is increased by at least 2-fold, at least 3-fold, at least 4-fold, at least 5-fold, at least 10-fold, or more, relative to the level of the target gene or polypeptide at the beginning of or before commencement of the cancer therapy.

The above described methods can further comprise administering to the subject (e.g., a subject in which the efficacy of the breast cancer therapy was determined to be poor or not optimal) an additional therapy or therapeutic agent for treating, reducing the risk of developing, or preventing breast cancer (e.g., ER+ or ER− breast cancer). In other embodiments, the methods can comprise recording the results in a database or medical history (e.g., medical records) of the subject, selecting the subject for increased monitoring or periodically monitoring the health of the subject (e.g., for development or changes in the signs or symptoms of the breast cancer, e.g., tumor development and/or changes in tumor size (e.g., increased or decreased size), such as e.g., clinical breast exam, mammography, MRI, or other suitable imaging or other diagnostic method(s) known in the art.

Methods for determining the level of a target gene or polypeptide are well known in the art, as described above.

As above, such methods can be conducted in parallel, or before or after, conventional methods for determining success of a treatment, such as, e.g. measuring tumor size or other symptoms of breast cancer known in the art.

X. Kits

In certain embodiments, kits are provided for predicting a subject's risk of developing breast cancer. In other embodiments, kits are provided for predicting a subject's breast cancer disease outcome (i.e., prognosis, e.g., likeliness to survive the disease). In other embodiments, kits are provided for treating breast cancer. In still other embodiments, kits are provided for determining the efficacy of a cancer therapy.

The above kits can comprise means (e.g., reagents, dishes, solid substrates (e.g., microarray slides, ELISA plates, multiplex beads), solutions, media, buffers, etc.) for determining the level of expression or activity of one or more of the genes and/or pathways described herein. Such kits can further comprise instructions for use, e.g., guidelines for determining the efficacy of a cancer therapy, or for predicting a subject's risk of developing breast cancer, based on the level of expression or activity of the one or more genes detected using the kit.

Other kits comprise means for determining (e.g., reagents, dishes, solid substrates (e.g., microarray slides, ELISA plates, multiplex beads), solutions, media, buffers, etc.) the frequency of breast epithelial cell types (e.g., the frequency of CD44+, CD24− breast epithelial cells, CD24+ breast epithelial cells, CD10+ breast epithelial cells, p27+ breast epithelial cells, Ki67+ breast epithelial cells, Sox17+ breast epithelial cells and/or Cox2+ breast epithelial cells, and/or ER+, p27+ breast epithelial cells, ER+, Sox17+ breast epithelial cells, ER+, Cox2+ breast epithelial cells, ER+, Ki67+ breast epithelial cells, AR+, p27+ breast epithelial cells, AR+, Sox17+ breast epithelial cells, AR+, Cox2+ breast epithelial cells, and/or AR+, Ki67+ breast epithelial cells). Such kits can comprise means for detecting expression (e.g., mRNA and/or protein) levels of one or more of the markers (e.g., CD44, CD24, CD10, p27, Ki67, Sox17, and/or Cox2) of the cell types described above. Such kits can also comprise instructions for determining a subject's risk of developing breast cancer based on the frequencies of those cell types determined. The frequencies that indicate an elevated or reduced risk of developing breast cancer are disclosed above and in the present Examples.

Other kits can comprise means for determining a parity/nulliparity gene expression profile. For example, such kits can comprise a microarray slide or slides comprising probes for two or more genes making up the parity/nulliparity gene expression profile, or means for performing PCR (e.g., QPCR), such as forward and reverse primers, reverse transcriptase, plates, and/or other PCR reagents. Such kits can further comprise instructions for determining a subject's disease outcome based on the subject's parity/nulliparity gene expression profile, as described above and in the present Examples, and may also provide a standard or reference gene expression profile for comparison.

Other kits comprise one or more inhibitors or agonists of pathways active in nulliparous or parous breast epithelial cells (e.g. CD44+, CD24− breast epithelial cells), as described herein, for the treatment or prevention of breast cancer (e.g., ER+ or ER− breast cancer), and, optionally instructions for use (e.g. administration and/or dosage).

In other embodiments, a kit comprises an array containing a substrate having at least 10, 25, 50, 100, 200, 500, or 1,000 addresses, wherein each address has disposed thereon a capture probe that includes: (a) a nucleic acid sequence consisting of a tag nucleotide sequence for the detection of a gene identified in Tables 4, 5, 6, 7 and/or 18 (e.g., HSD17B11, HSD17B12, HSD17B14, HSP90AB1 (GenBank Accession No. AAH09206), PSA (KLK3), NCOR1, NCOR2, NCOA4, NCOA7, SFRP2, SFRP4, VEGFA, NOTCH1, FN1, ITGA4, ITGB1, TSPAN6, RhoA, RAC1, CDC42, PHB4, BCL2L11, TNFRSF4, BMPR2, CASP8, PP2A, PIK3CG, ILK, PDPK1, Hakai/CBLL1, SCRIB, and LLGL2, MAP2K4 (GenBank Accession No. NM_003010.2), PTP4A2 (GenBank Accession No. NM_080391.3), EPHB4 (GenBank Accession No. NM_004444), SPARC (GenBank Accession No. NM_003118.3), RAB32 (GenBank Accession No. NM_006834.3), FIGF (GenBank Accession No. NM_004469.4), SNX3 (GenBank Accession Nos. NM_003795.4, NM_152827.2), GADD45A (GenBank Accession Nos. NM_001924.3, NM_001199741.1, NM_001199742.1), ANXA3 (GenBank Accession Nos. NM_005139.2), and HSPA2 (GenBank Accession No. NM_021979.3)); and (b) the complement of the nucleic acid sequence.

Another kit provided herein contains at least 10 antibodies each of which is specific for a different protein encoded by a gene identified in Tables 4, 5, 6, 7 and/or 18. The antibodies can be, for example, but not limited to, specific for a protein such as HSD17B11, HSD17B12, HSD17B14, HSP90AB1 (GenBank Accession No. AAH09206), PSA (KLK3), NCOR1, NCOR2, NCOA4, NCOA7, SFRP2, SFRP4, VEGFA, NOTCH1, FN1, ITGA4, ITGB1, TSPAN6, RhoA, RAC1, CDC42, PHB4, BCL2L11, TNFRSF4, BMPR2, CASP8, PP2A, PIK3CG, ILK, PDPK1, Hakai/CBLL1, SCRIB, and LLGL2, MAP2K4 (GenBank Accession No. NM_003010.2), PTP4A2 (GenBank Accession No. NM_080391.3), EPHB4 (GenBank Accession No. NM_004444), SPARC (GenBank Accession No. NM_003118.3), RAB32 (GenBank Accession No. NM_006834.3), FIGF (GenBank Accession No. NM_004469.4), SNX3 (GenBank Accession Nos. NM_003795.4, NM_152827.2), GADD45A (GenBank Accession Nos. NM_001924.3, NM_001199741.1, NM_001199742.1), ANXA3 (GenBank Accession Nos. NM_005139.2), and HSPA2 (GenBank Accession No. NM_021979.3). The kit can contain at least 5 antibodies, at least 10 antibodies, at least 15 antibodies, at least 25 antibodies; at least 50 antibodies; at least 100 antibodies; at least 200 antibodies; or at least 500 antibodies.

The kits, regardless of type, will generally comprise one or more containers into which the biological agents (e.g. inhibitors) are placed and, preferably, suitably aliquoted. The components of the kits may be packaged either in aqueous media or in lyophilized form.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

The following examples are meant to illustrate, not limit, the invention.

EXAMPLES

Example 1: Materials and Methods

The following are the materials and methods used in the Examples set forth below.

FACS (Fluorescence Activated Cell Sorting)

A single-cell suspension of human mammary epithelial cells was obtained from organoids after trypsinization (5 mins, 37° C.) and filtration through 40 μm cell strainers. Leukocytes, fibroblasts, and endothelial cells were removed by immuno-magnetic bead purification using cell-type-specific surface markers essentially as previously described [Bloushtain-Qimron, et al. (2008). Proc Natl Acad Sci USA 105, 14076-14081; Shipitsin, M., et al. (2007). Cancer Cell 11, 259-273]. Cells were re-suspended in ice cold PBE (0.5% BSA and 2 mM EDTA in PBS) at $2\times10^6$ cells/ml. $2\times10^5$ cells from each sample were used for multicolor FACS analysis. Cells were stained with propidium iodine (PI, Sigma), FITC conjugated anti-human EpCAM (Dako, clone Ber-Ep4), PE-conjugated anti-human CD49f (BD, clone GoH3), PE/Cy7-conjugated anti-human CD10 (Biolegend, Clone HI10a), APC-conjugated anti-human CD24 (Biolegend, clone ML5), and purified anti-human CD44 (BD, Clone 515). CD44 antibody was pre-labeled with Zenon Alexa 405 mouse IgG1 kit (Invitrogen). Only PI-negative (viable cells) were used to calculate the relative fraction of each cell population.

Multicolor Immunofluorescence and Immunohistochemical Analyses

Multicolor immunofluorescence for CD44 (Neomarkers, clone 156-3C11, mouse monoclonal IgG2), CD24 (SWAII clone, generously provided by Dr. Peter Altevogt (German Cancer Research Center, Heidelberg, Germany), mouse monoclonal IgG2), p27 (BD Biosciences, clone 57/Kip1/p27, mouse monoclonal IgG1), Sox17 (R&D Systems, clone 245013, mouse monoclonal IgG3), COX2 (Cayman Chemical, clone CX229, mouse monoclonal IgG1), Ki67 (DAKO, clone MIB-1, mouse monoclonal IgG1), Ki67 (Abeam, #16667, rabbit monoclonal) and bromodeoxyuridine (BrdU, Roche, clone BMC9318, mouse monoclonal IgG1), CD10 (DAKO M7308), p63 clone 4A4 (Santa Cruz SC-8431), SMA clone 1A4 (DAKO M0851), Axin2 clone 354214 (R&D systems MAB6078), Phosphor-EGF Receptor (Tyr1173) clone 53A5 (Cell Signaling #4407), Phospho-Smad2 (Ser 465/467) (Cell Signaling #3101), Gata3 (Santa Cruz SC-268), estrogen receptor (clone SP1, Thermo Scientific RM-9101), androgen receptor (clone D6F11, Cell Signalling #5153), and bromodeoxyuridine (BrdU, Roche, clone BMC9318), was performed using whole sections of formalin fixed paraffin embedded (FFPE) normal human breast tissue.

The tissues were deparaffinized in xylene and hydrated in a series of 100%, 70%, 50% and 0% ethanol solutions. After heat-induced antigen retrieval in citrate buffer (pH 6), the samples were blocked with goat serum and sequentially stained with the different primary and secondary antibodies. The sequential staining was optimized to avoid cross-reaction between antibodies and was performed as follows: monoclonal (IgG2a) antibody anti-CD44 (1:100 dilution) for one hour at room temperature; goat anti-mouse IgG2a Alexa555-conjugated (Invitrogen, 1:100 dilution) for 30 minutes at room temperature; monoclonal antibody anti-p27 (1:100 dilution) or monoclonal antibody anti-Sox17 (1:50 dilution) or anti-COX2 (1:50 dilution), and monoclonal antibody anti-CD24 (1:25 dilution) biotin labeled (Zenon® Biotin-XX Rabbit IgG Labeling Kit, Invitrogen), p63 (1:100 dilution), SMA (1:80 dilution), CD10 (1:100 dilution), Gata3 (1:50 dilution) for one hour at room temperature; goat anti-mouse IgG1 Alexa 488-conjugated (Invitrogen, 1:100 dilution, for detection of p27 or COX2), goat anti-mouse Alexa 488/555/647 (Invitrogen 1:100 dilution, for detection of p63, SMA, CD10 and Gata3) or goat anti-mouse IgG3 Alexa 488-conjugated (Invitrogen, 1:100 dilution, for detection of Sox17) and streptavidin Alexa-647 conjugated for 30 minutes at room temperature.

The multicolor immunofluorescence for p27 and Ki67 was performed by incubating the samples with monoclonal antibody anti-p27 (1:100 dilution) and polyclonal antibody anti-Ki67 (1:50 dilution) for one hour at room temperature followed by goat anti-mouse IgG1 Alexa 555-conjugated (Invitrogen, 1:100 dilution, for detection of p27) and goat anti-rabbit Alexa 488-conjugated (Invitrogen, 1:100 dilution, for detection of Ki67) for 30 minutes at room temperature. Multicolor immunofluorescence for pSMAD2 (1:50 dilution), pEGFR (1:50 dilution) and Axin2 (1:20 dilution) were performed by incubation for 2 h at room temperature or overnight at 4° C. followed by secondary antibody Rabbit Alexa 488 conjugated (Invitrogen, 1:100 dilution for pSMAD2 and pEGFR) or mouse IgG1 Alexa-488 conjugated (Invitrogen 1:100 dilution) for Axin2 for 30 minutes at room temperature.

The samples were washed twice with PBS-Tween 0.05% between incubations and protected for long-term storage with VECTASHIELD HardSet Mounting Medium with DAPI (Vector laboratories, cat #H-1500). Before image analysis, the samples were stored at −20° C. for at least 48 hours. Different immunofluorescence images from multiple areas of each sample were acquired with a Nikon Ti microscope attached to a Yokogawa spinning-disk confocal unit, 60× plan apo objective, and Orca-ER camera controlled by Andor iQ software. For the immunohistochemical detection of Sox17 and COX2 the samples were stained with antibodies against Sox17 and COX2 as above, and then incubated with anti-mouse IgG biotinylated antibody (1:100 dilution) for 30 minutes at room temperature followed by the ABC peroxidase System (Vectastain®, ABC System Vector Laboratories). DAB (3,3'-diaminodbenzidine) was used as colorimetric substrate and the signal was enhanced by the addition of 0.04% of nickel chloride. The slides were finally counterstained with Methyl green.

Scoring for the expression of each marker was done as follows: p27 fluorescence intensity was scored in the nuclei of 20 randomly selected cells using the ImageJ 1.43r software; Sox17 and COX2 expression was inferred by the combination of two variables: 1) the percentage cells expressing each marker, and 2) the intensity of each marker transformed into a categorical variable based on 0 no expression, 1 weak expression, 2 moderate expression and 3 high expression; the percentage of p27+, Ki67+ and BrdU+ cells was estimated by counting an average of 1000 cells/sample in the case of the mammary epithelium for premenopausal, postmenopausal and high-low density cases, and an average of 2,000 cells in the case of the tissue slices cultures. % of pSMAD2+ cells was estimated by counting an average of 600 cells/sample. For pEGFR and Axin2 fluorescence intensity measurement, mean fluorescence intensity was measured using Image J 1.43r software by counting an average of 600 cells/sample corrected by area and subtracting the average of background fluorescence intensity. RGB profile was also generated using Image J 1.43 software. For multicolor immunofluorescence of p27 and ER, p27 (1:100 dilution) and ER (1:500 dilution) antibodies were incubated overnight at 40 C followed by incubation at RT for 1 h with subsequent staining by goat anti-mouse IgG1 Alexa 555-conjugated (Invitrogen, 1:100 dilution, for detection of p27) while detection of ER antibody was performed by Biotinylated anti Rabbit 20 antibody (1:100 dilution) using Perkin Elmer TSATM INDIRECT tyramide amplification kit (NEL700001KT) and streptavidin conjugated Alexa 647 from Invitrogen (1:80 dilution). For p27 and AR staining, p27 (1:100 dilution and AR (1:30 dilution) antibodies were incubated overnight at 40 C followed by incubation at RT for 1 h with subsequent staining by goat anti-mouse IgG1 Alexa 555-conjugated (Invitrogen, 1:100 dilution, for detection of p27) and anti-rabbit IgG Alexa 488-conjugated (Invitrogen, 1:80 dilution). Percentage of p27+, AR+, ER+ cells was estimated by counting 500-1000 cells/sample. Nuclear staining with DAPI and multiple fluorescence images from each section were acquired with 40× plan apo objective, following procedure described above.

Culture of Tissue Slices

Normal human breast tissues were collected from reduction mammoplasties, transported in ice-cold DMEM-F12 medium, and processed within 24 hrs. For organ cultures, thin (~1 mm thick) slices of tissue were cut from epithelium-enriched areas and cultured for 8 days in 6-well plates using co-culture inserts to optimize the tissue/medium contact surface and changing medium (2 ml/well) every 24 hrs. The M87A medium previously optimized for human primary mammary epithelial cultures was used [see, Bloushtain-Qimron, et al. (2008) supra; Garbe, J. C., et al. (2009). Cancer Res 69, 7557-7568]. Inhibitors used included cyclopamine (Selleck Chemicals, cat #S1146)—inhibitor of Smo receptor of Hh ligands, LY2109761 (Eli Lilly)—inhibitor of TGFBR kinases, celecoxib (LKT laboratories, cat #C1644)—inhibitor of Cox2, 2-5dideoxyadenosine (Enzo Life Sciences, cat #BML-CN110-005)—adenylate cyclase inhibitor, tyrphostin AG1478 (Cayman Chemicals, cat #10010244)—EGFR inhibitor, XAV939 (Tocris Bioscience, cat #3748)—Tankyrase (TNKS) inhibitor—antagonizes Wnt signaling via stimulation of β-catenin degradation and stabilization of axin, picropodophylotoxin (Tocris Bioscience, cat #2956)—IGFR inhibitor Stock solutions (1,000×) were prepared in DMSO. Final drug concentrations were as follows: cyclopamine—10 µM, LY2109761—500 nM, celecoxib—100 µM, 2-5dideoxyadenosine—100 µM, AG1478—10 µM, XAV939—1 µM and Picropodophylotoxin—0.5 µM. Following 8 days of culture, labeled tissue slices were pulse with bromo-deoxy-uridine (30 µM final concentration) for 5 hrs before fixing the tissue in buffered formalin at room temperature for 24 hrs followed by embedding in paraffin. Experiments were performed in triplicates using tissue from different regions of the same breast, uncultured tissue and tissue cultured without any drugs as controls. To experimentally reproduce hormone levels in follicular and luteal phase of the menstrual cycle and in mid-pregnancy, the following was used: 0.5 µM of estradiol for 8 days to mimic follicular phase; 1.2 nM of estradiol for 2 days (representing ovulation) followed by 0.7 nM of estradiol and 50 nM of progesterone for 6 days to mimic luteal phase; and a combination of 250 nM estradiol, 600 nM progesterone, 600 ng/mL prolactin, and 10 IU/mL HCG for 8 days to mimic pregnancy in the normal breast.

PCA Analysis and Plot

Unsupervised principle component analysis (PCA) was applied using R package 'pcurve' to gene expression profiles of different cell types from parous and nulliparous tissues. The mean of each sample was centered to zero before PCA analysis. Genes were the feature variables and samples were projected to the principle components. OpenGL was used to plot PCA results by projecting each sample to the first three principal components. Using the projected value on the largest 3 principal component as the Euclidean coordinates for each individual, paired Euclidean distance between nulliparous and parous individuals for each cell type was calculated. The distance is a global measurement of the difference between individuals. It indicated, for example, that the gene expression of $CD44^+$ cells changed the most, as it has the most significant distance between nulliparous and parous samples.

Rat Gene Expression Data Analysis and Comparison with Human

Previously published gene expression data from virgin and parous rats was reanalyzed using four (WistarFurth, Copenhagen, Fischer 344, and Lewis) inbred strains of rats [Blakely, C. M., et al. (2006). Cancer Res 66, 6421-6431]. The raw data (generated using RG_U34A array) was obtained online and normalized by RMA using default parameters followed by the selection of differentially expressed genes using SAM (significance analysis of microarray) algorithm [Tusher, et al. (2001) Proc Natl Acad Sci USA 98, 5116-5121]. Differentially expressed genes for each strain was called using p value cutoff 0.05 and the union of these was used defined as "rat differential gene list". Genes that appeared in both up and down union groups were excluded. Only genes that had homologues in both species were used for comparisons.

Supervised Principal Component Analysis with Randomized Input

Supervised principal component analysis (SPCA) was used for selection of a subset of genes with prognostic value from differentially expressed genes [Tibshirani, R., et al. (2004). Bioinformatics 20:3034-3044]. The training (Wang's) cohort [Wang, Y., et al. (2005) Lancet 365, 671-679] was randomly split after appropriate filtering of patients into training set and testing set of the same size (the same number of individual patients). Traditional PCA uses all genes to identify principal components in an unsupervised way. However, the $1^{st}$ principal component of unsupervised PCA might not be the projection direction of interested. SPCA in this study finds the principal components using only genes correlated with survival (ex, log rank test p value 0.05 as cutoff using univariate cox regression). The 1st principal component was used to predict the survival outcome. The correlation between a gene and the predicted outcome was used as the importance score to rank genes of importance. Cross-validation was applied to determine cut-off for significance. Genes with importance score higher than this cut-off formed the gene signature. For each random split configuration, a parity signature was obtained using SPCA. To get a robust gene signature, Wang's data was randomly split into training and testing sets 1,000 times and a signature for each configuration was obtained. It was argued that the genes that significantly contribute to breast cancer progression should appear in signatures multiple times more than randomly expected. Those genes whose frequency appearing in signature 5 times higher than random background were chosen as the final parity gene signature.

Prognostic Signature 3,515 genes were identified that were differentially expressed after pregnancy in CD44+ cells at p value cut-off 0.05 using SageExpress pipeline [Wu, Z. J., et al. (2010). Genome Res 20, 1730-1739]. Pregnancy resulted in multifaceted alterations of the mRNA expression levels in cells. Applying univariate Cox regression, 1899 genes were identified to have significant (log rank p value <0.05) correlation with survival in Wang's cohort, among which 441 genes were shown to be differentially expressed after pregnancy (p value <1.75c-10 using hypergeometric distribution for significance test). Those results suggested that the alterations of pregnancy on cell factory are likely associated with carcinogenesis and cancer progression.

In order to elucidate the parity-induced differential genes that were not only expressed together but also correlated with survival (parity-induced breast cancer signature), supervised principal component analysis described above was applied. Simply using univariate cox regression to identify genes correlated with breast cancer as the parity-induced breast cancer signature has the following drawbacks. First, univariate analysis excludes the contributions of other covariates (genes). Thus significant genes in univariate analysis might not be significant when considering other covariates. Second, gene expression often changes in a coherent way such that genes that are functionally related in one or several pathways often show strong correlation in expression levels, which is not captured by univariate analysis. Parity-induced breast cancer signature was obtained using SPCA on up and down genes after pregnancy separately. Wang's cohort was used as the training set and the signatures were validated in three other widely used breast cancer cohorts (NKI, GSE7390 (Transbig), GSE2990 (Tamoxifen) [Desmedt, C., et al. (2007). Clin Cancer Res 13, 3207-3214; Sotiriou, C., et al. (2006) J Natl Cancer Inst 98, 262-272; van de Vijver, M. J et al. (2002) N Engl J Med 347, 1999-2009]. K-mean clustering (k=2) of these signatures separated patients into two groups with significant survival difference.

Norwegian Cohort

GSE18672 cohort [Haakensen, V. D., et al. (2011a) BMC Cancer 11, 332; Haakensen, V. D., et al. (2011b). BMC medical genomics 4, 77] was used to validate the expression patterns of parity-related genes identified in this study. The following criteria were applied for sample selection from this cohort in order to match the samples used in this study: for nulliparous samples—pre-menopausal and age<40; for parous samples—pre-menopausal, number of parity with live birth=2, age<40, age at 1st birth<30. The following procedures were taken to preprocess the public data cohort GSE18672: 1—Missing value estimation using local least squares (R package pacMethods: llsimpute), 2—All genes were centered to zero followed by a loess normalization (R package affy: normalize.loess).

Statistical Analyses

The differences between the percentage of p27+ and Ki67+ cells in the samples from nulliparous and parous women were analyzed by Fisher exact test. The differences between high and low-density samples were analyzed by binomial test. P value of overlap between two groups was obtained by statistical test on hypergeometric distribution. The differences between the percentages of p27+ in the tissue slices experiments were analyzed by t-test, and the differences in BrdU+ cells were analyzed by Fisher exact test.

Kappa Statistics

Kappa statistics are a statistical measure of inter-rater agreement [Cohen, J. (1960). Educat Psych Meas 20, 37-46]. The input for kappa involves a couple of raters or learners, which classify a set of objects into categories. Here, it was used to compare lists of differentially expressed genes for their congruency. Hierarchical clustering of signaling pathways significantly down or upregulated in the four cell types was performed. Distance between two enrichments was assessed using the kappa statistics. Similar to the design in previous publications [Bessarabova, M., et al. (2011) *Cancer Res* 71, 3471-3481; Huang da, W., et al. (2007) *Genome Biol* 8, R183; Shi, W., et al. (2010) *Pharmacogenomics J* 10, 310-323], the value of 1 was assigned to a map if it was significant for an experiment and the value of 0 if the significant enrichment was not observed. Pathways determined to have significant enrichment are referred to herein as "statistically significant pathways." Kappa value was calculated as $$\kappa = \frac{Pr(a) - Pr(e)}{1 - Pr(e)},$$

where Pr(a) is the relative observed agreement among two enrichments, and Pr(e) is the hypothetical probability of chance agreement, using the observed data to calculate the probabilities of randomly calling maps significant in each experiment. As the higher values of kappa mean better agreement between enrichments and the maximal possible value of kappa is 1, the value (1-κ) was used as a distance between two experiments. Average linkage was used to construct cluster dendrogram depicted in FIG. 10.

Generation of SAGEseq, MSDKseq, and ChIPseq Libraries

Detailed protocols for cell purification and the generation of SAGEseq (Serial Analysis of Gene Expression applied to high-throughput sequencing) [Genome Res. 2010 December; 20(12):1730-9. Epub 2010 Nov. 2., Proc Natl Acad Sci USA. 2012 Feb. 21; 109(8):2820-4. Epub 2010 Nov. 22. (http://research4 dfci.harvard.edu/polyaklab/protocols_linkpage.php)], MSDKseq (Methylation-Specific Digital Karyotyping [Hu, M., et al. (2005) *Nat Genet* 37, 899-905], and ChIPseq (Chromatin Immunoprecipitation applied to high-throughput sequencing) [Maruyama, R. et al. (2011) *PLoS genetics* 7, e1001369] libraries are posted on the web-site (http://research4.dfci.harvard.edu/polyaklab/protocols_linkpage.php). Genomic data were analyzed as described before [Kowalczyk, A., et al. (2011) *J Comput Biol* 18, 391-400; Maruyama, R., et al. (2011) supra; Wu, Z. J., et al. (2010) *Genome Res* 20, 1730-1739].

Integrated View of ChIPseq, SAGEseq, and MSDKseq Data

Differentially Methylated Regions across parity groups were identified using the Poisson margin test [Kowalczyk, A., et al. (2011) supra]. Genes were ordered as a spectrum going from higher in parous to higher in nulliparous, based on p-values. Fisher exact tests were performed using sum of target gene numbers in 1,000-gene window and total count of target genes outside of the window, testing the enrichment of targets inside the windows.

Protein Interactome Analyses

In order to determine overall activation of specific biological functions due to parity in the cell types analyzed, pathway enrichment, network, and protein interactome analyses were performed using the MetaCore platform as described in Bessarabova et al., supra; Ekins, S., et al. (2006) Book Chapter in In *High Content Screening* (Humana Press), pp. 319-350; Nikolsky, Y., et al. (2009) Methods Mol Biol 563, 177-196).

Nurses' Health Study Data

The Nurses' Health Study (NHS) is a prospective cohort study established in 1976 when 121,700 female registered nurses from across the United States, aged 30-55 years, completed a mailed questionnaire on factors that influence women's health. Follow-up questionnaires have since been sent out every two years to the NHS participants to update exposure information and ascertain non-fatal incident diseases. Incident breast cancer was ascertained by the biennial questionnaire to study participants. For any report of breast cancer, written permission was obtained from participants to review their medical records to confirm the diagnosis and to classify cancers as in situ or invasive, by histological type, size and presence or absence of metastases. Overall, 99% of self-reported breast cancers have been confirmed. To identify breast cancer cases in non-respondents who died, death certificates and medical records for all deceased participants were obtained to ascertain cause of death. This study was approved by the Human Subjects Committee at Brigham and Women's Hospital in Boston, Mass. Breast cancer cases were followed from the date of diagnosis until Jan. 1, 2008 or death, whichever came first. Ascertainment of deaths included reporting by next of kin or postal authorities or searching the National Death Index.

Approximately 98% of deaths in the NHS have been identified by these methods. Cause of death was ascertained from death certificates and physician review of medical records. Information on estrogen receptor (ER) status was extracted from the medical record and pathology reports. If data were missing for ER status, scoring from immunohistochemical staining for ER on 5 μm paraffin sections cut from tissue microarray (TMA) blocks was used [Tamimi, R. M., et al. (2008) *Breast Cancer Res* 10, R67]. There were 8,055 women with invasive breast cancer diagnosed after return of the 1976 baseline questionnaire through 2006 questionnaire. One woman was excluded due to missing information on parity. Thus, our final analysis included 8,054 women with invasive breast cancer and information on parity. Survival curves were estimated by the Kaplan-Meier method and statistical significance was assessed with the log-rank test. Multivariate cox proportional hazards regression models were used to evaluate the relationship between parity and breast cancer-specific mortality after adjusting for age at diagnosis, aspirin use, date of diagnosis, disease stage, grade, radiation treatment, chemotherapy and hormonal treatment. All analyses were performed using SAS version 9.1. All statistical tests were two sided and P<0.05 was considered statistically significant.

Accession Numbers

Raw data files and methodological details have been submitted to GEO with accession number GSE32017.

Example 2: Parity-Related Differences in Gene Expression in Multiple Cell Types

This example demonstrates the effect parity has on the cellular composition of normal human breast.

Figure 2:
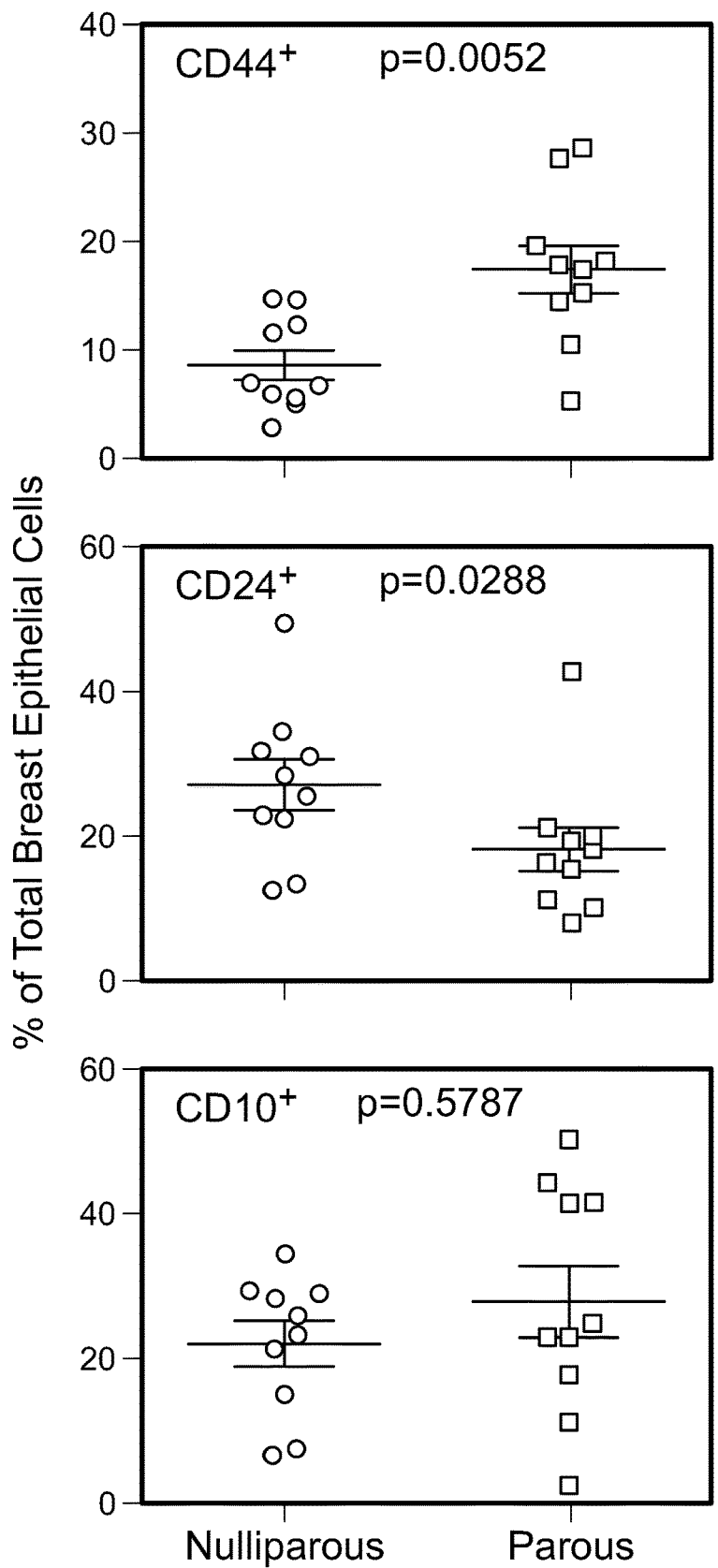
FIG. 2 contains graphs plotting the frequency (%) of CD44+, CD24+, and CD10+ human breast epithelial cells relative to total human breast epithelial cells from nulliparous and parous women. 10 samples each from nulliparous and parous groups were analyzed, and each dot represents an individual sample. Error bars represent mean±SEM.

To investigate if parity affects the cellular composition of normal human breast, first breast epithelial cells from nulliparous and parous women were analyzed by FACS (fluorescence-activated cell sorting) for cell surface markers previously associated with luminal epithelial (CD24), myoepithelial (CD10), and progenitor features (lin−/CD44+) [Bloushtain-Qimron et al., supra; Mani et al. (2008) *Cell* 16; 133(4):704-15; Shipitsin et al., (2007) *Cancer Cell* 11, 259-273]. It was found that CD24+, CD44+, and CD10+ cells represent three distinct cell populations with minimal overlap both in nulliparous and parous tissues. FIG. 1 shows the FACS plot for CD24+ versus CD44+ cells, and it could be seen that there were very few cells that stained positive for both markers. (FIG. 1). Multicolor immunofluorescence analyses was also performed for these three cell surface markers alone or in combinations, and additional known markers for a subset of luminal (GATA3) and myoepithelial (SMA) cells, which further confirmed the identity of the cells. Subsequent FACS analysis of multiple tissue samples showed significant differences in the relative frequency of CD44+ and CD24+ cells between parous and nulliparous samples, whereas the relative frequency of CD10+ cells was essentially the same (FIG. 2). The changes in the relative frequency of CD24+ and CD44+ cells could potentially have been due to the increased number of lobulo-alveolar structures observed in parous women.

To investigate parity-related differences in global gene expression profiles, immuno-magnetic bead purified (Bloushtain-Qimron et al., 2008 supra; Shipitsin et al., 2007, supra) CD24+, CD10+, and CD44+ cells (captured sequentially, thus, CD44+ fraction was CD24-CD10-CD44+, but the CD24+ fraction may have contained some CD24+ CD44+ cells), and fibroblast-enriched stroma from multiple nulliparous and parous women were analyzed using SAGEseq (Serial Analysis of Gene Expression applied to high-throughput sequencing). To minimize variability among individuals unrelated to parity status, women were closely matched for age, the number of pregnancies, time at first and since last pregnancy, and ethnicity. The analysis is summarized in Table 3, below, which shows the tissue code, age, parity, ethnicity, and menopausal status of the patient, type of surgery for tissue acquisition, mammographic breast density, cell type analyzed, raw and aligned tag/read counts for Sageseq, MSDKseq, and ChIPseq data below, in which an "x" in qRT-PCR, qMSP, FACS, and IF/IHC (immunofluorescence/immunohistochemistry) columns indicate the use of that sample for the analysis.

Figure 3:
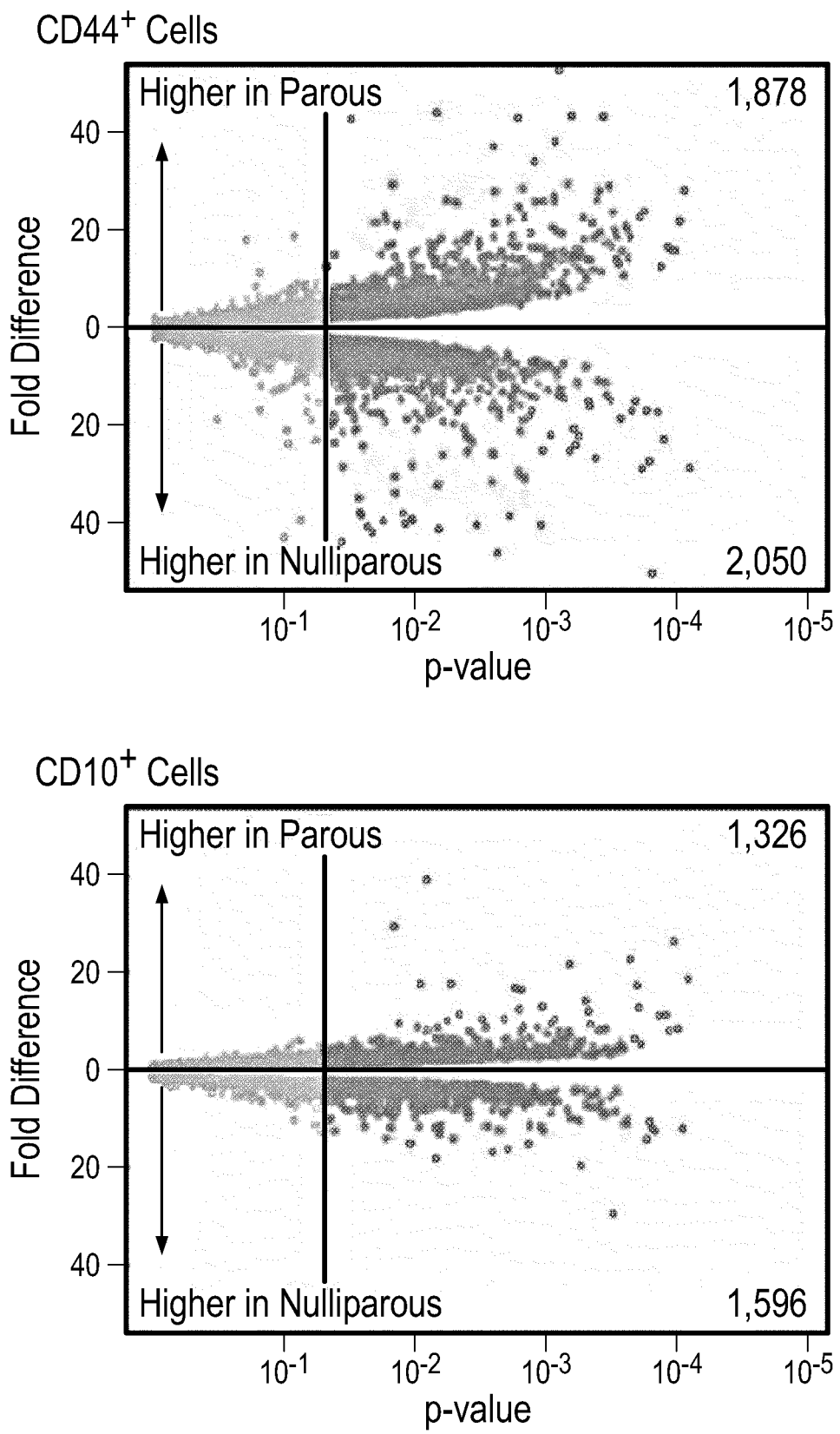
FIG. 3 contains dot plots showing a genome-wide view of genes differentially expressed between nulliparous (N) and parous (P) samples in CD44+, CD24− breast epithelial cells (upper left quadrant), CD10+ breast epithelial cells (upper right quadrant), CD24+ breast epithelial cells (lower left quadrant), and stromal fibroblasts (lower right quadrant). Each dot represents a gene. Fold differences between averaged N and P samples and their corresponding p-values are plotted on the y and x-axis, respectively. Vertical lines indicate p=0.05, numbers indicate the number of genes differentially expressed at p<0.05.

The expression of known cell type-specific genes (e.g., luminal cell markers KRT8 and MUC1, myoepithelial cell markers ACTG2 and CNN1, and progenitor cell markers ZEB2 and TWIST1) was consistently observed in each of the three respective epithelial cell types both from nulliparous and parous samples based on SAGEseq confirming the purity and identity of the cells. Comparison of each cell type between nulliparous and parous samples revealed the most pronounced differences in CD44+ cells (FIG. 3 and Table 4, below), where the numbers of significantly ($p<0.05$) differentially expressed genes and the fold differences were the largest between groups. Tables 4, 5, 6 and 7 list the differentially expressed genes in CD44+, CD24+, CD10+, and stromal breast epithelial cells, respectively, from normal human reduction mammoplasty samples of nulliparous (NP) and parous (P) women. The tables list gene symbols, log transformed normalized tag counts in CD44+, CD24+, CD10+ or stromal breast epithelial cells from nulliparous (columns 2-4) and parous (columns 5-7) with fold change between nulliparous and parous samples (based on average of actual normalized tag count of the three tissues), p-value ($<0.05$) and gene description.

Figure 4A:
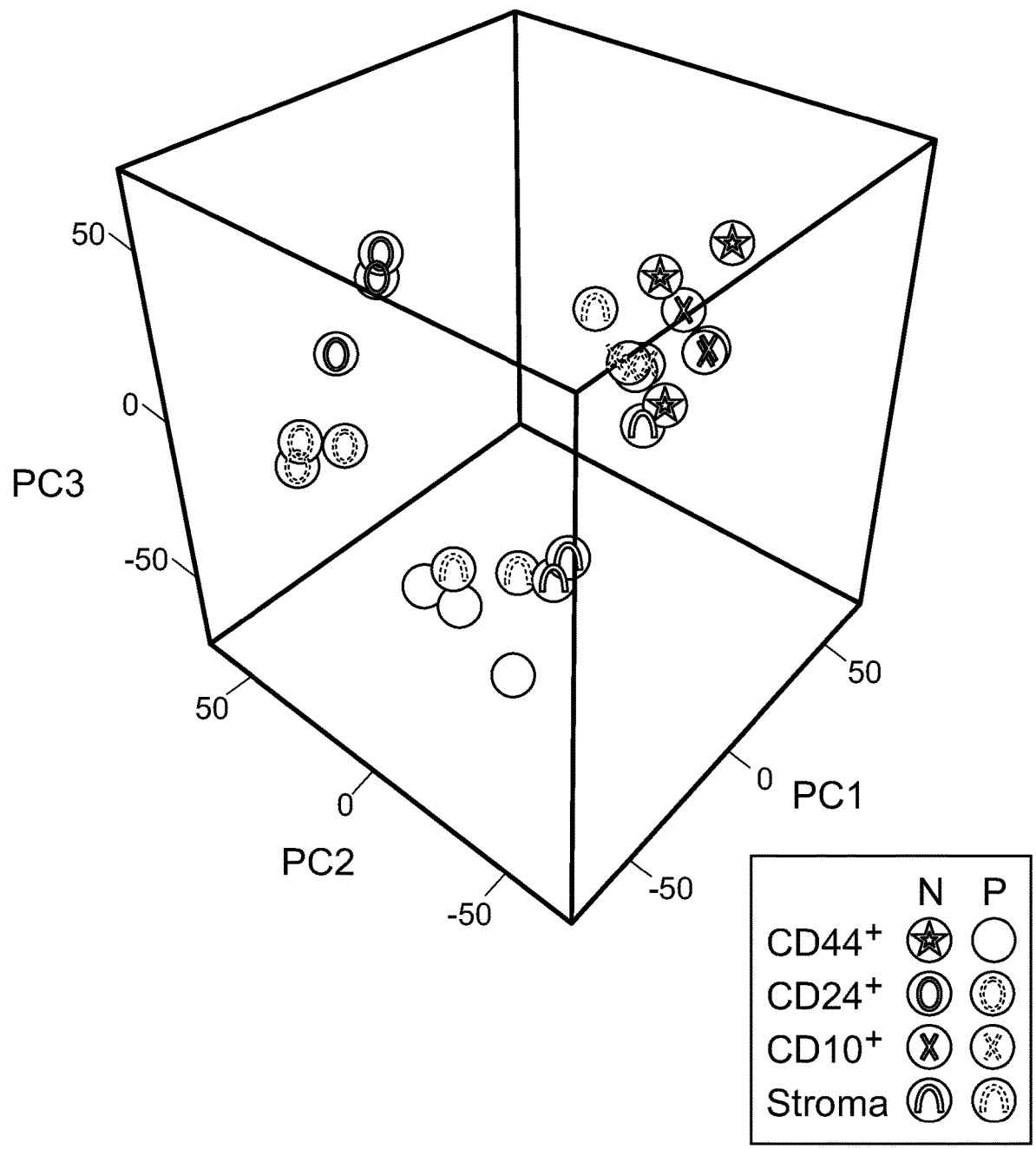
FIG. 4A is a three-dimensional projection of the gene expression data onto the first three principal components. Each ball is a different sample; cell type and parity are indicated.
Figure 4B:
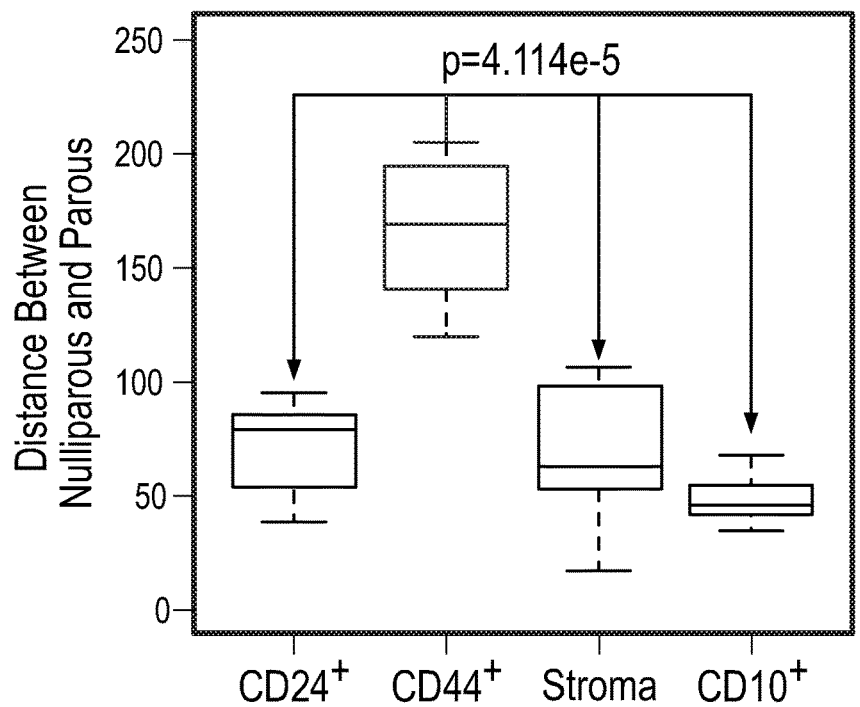
FIG. 4B is a box-and-whisker diagram of the paired Euclidean distance for each of the indicated cell types: CD44+, CD24+, CD10+, and stromal fibroblasts ("stroma"). The middle line within a box represents the median value. The Box is the IQR (interquartile range, 25th and 75th percentile). The top and bottom line of each box plot is the data range: the lowest data still within 1.5 IQR of the lower quantile and the highest data still within 1.5 IQR of the upper quantile. Data shown outside the range are plotted as circles. The Kolmogorov-Smirnov (KS) test was used to determine the significance of difference between CD44+ and other cell types. Statistical significance (p) is indicated.
Figure 5:
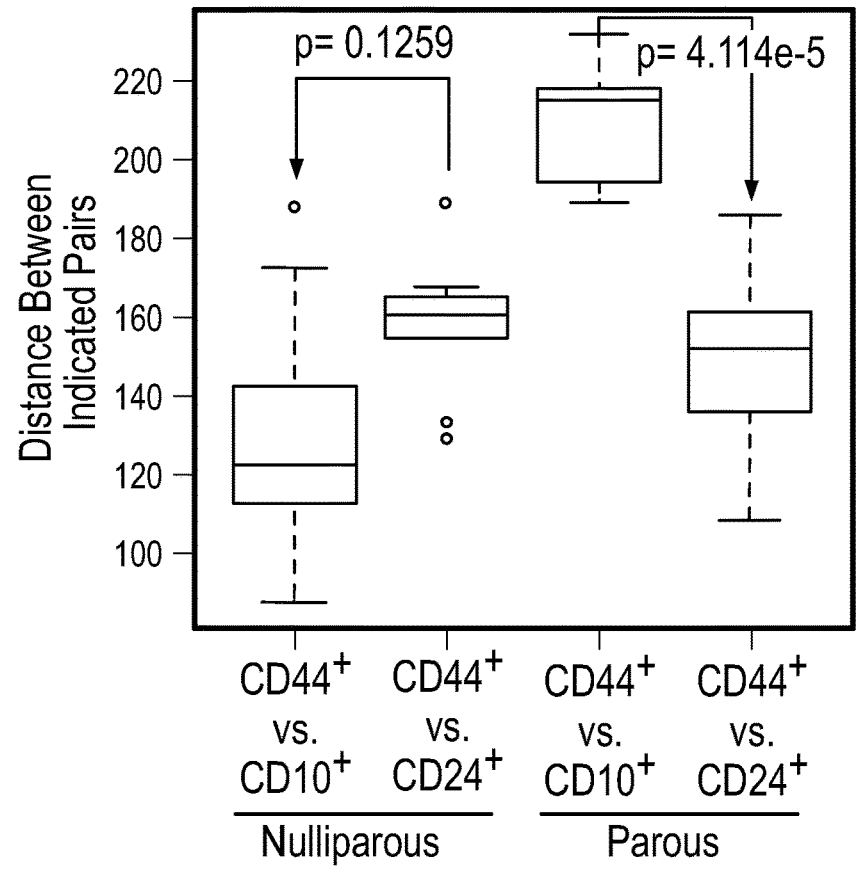
FIG. 5 is a box-and-whisker diagram of the paired Euclidean distance for the following pair-wise comparisons (from left to right on the x-axis): CD44+, CD24− nulliparous vs. CD10+ nulliparous; CD44+, CD24− nulliparous vs. CD24+ nulliparous; CD44+, CD24− parous vs. CD10+ nulliparous, CD44+, CD24− parous vs. CD24+ nulliparous; (N: nulliparous. P: parous). The middle line within a box represents the median value. The Box is the IQR (interquartile range, 25th and 75th percentile). The top and bottom line of each box plot is the data range: the lowest data still within 1.5 IQR of the lower quantile and the highest data still within 1.5 IQR of the upper quantile. Data shown outside the range are plotted as circles. The Kolmogorov-Smirnov (KS) test was used to determine significance of differences, indicated on the plot (p).

The degrees of differences were smaller and similar in CD10+ and CD24+ cells, whereas stromal fibroblasts had the fewest differentially expressed genes (Tables 5 and 6). Further examination of parity-related differences in expression patterns using principal component analysis (PCA) confirmed that CD24+ and CD10+ cells and fibroblasts from nulliparous and parous women were similar, whereas CD44+ cells formed very distinct nulliparous and parous clusters (FIGS. 4A and 4B). Interestingly, CD44+ cells from nulliparous women were more similar to CD10+ cells, whereas from parous cases they were more similar to CD24+ cells. This implied a shift from a more basal to a more luminal gene expression pattern in CD44+ cells after parity (FIG. 5).

TABLE 3

Parity-related Differences in Global Gene Expression Profiles

| Tissue | Age | Parity | Ethnicity | Menopausal status | Type of surgery | Breast density | Cell type | SAGE-Seq raw tag | SAGE-Seq alligned tag | MSDK-Seq raw tag | MSDK-Seq alligned tag | ChIP-Seq K27 raw tag | ChIP-Seq K27 alligned tag |
|---|---|---|---|---|---|---|---|---|---|---|---|---|---|
| N33 | 19 | PAR-0 | AA | Pre | Rdx | | CD24+ | 9,618,916 | 6,401,701 | 10,777,438 | 6,554,664 | | |
| | | | | | | | CD44+ | | | 4,147,642 | 2,356,179 | | |
| | | | | | | | stroma | 9,548,881 | 7,188,232 | | | | |
| N34 | 27 | UK | AA | Pre | Rdx | | CD24+ | | | | | | |
| | | | | | | | CD44+ | 8,945,148 | 5,668,737 | | | | |
| N35 | 18 | PAR-0 | AA | Pre | Rdx | | CD24+ | 13,522,703 | 9,518,916 | 7,907,066 | 5,669,764 | | |
| | | | | | | | CD44+ | | | 3,981,235 | 2,507,858 | | |
| | | | | | | | CD10+ | 23,303,110 | 18,244,367 | | | | |
| | | | | | | | stroma | 12,435,941 | 9,436,721 | | | | |
| N37 | 24 | PAR-2 | AA | Pre | Rdx | | CD24+ | 4,861,324 | 3,295,244 | 7,269,319 | 5,180,418 | | |
| | | | | | | | CD44+ | 4,170,428 | 2,696,351 | 8,657,890 | 7,048,887 | | |
| | | | | | | | stroma | 4,874,878 | 3,247,011 | | | | |
| N39 | 32 | PAR-3 | CU | Pre | Rdx | | CD24+ | 4,189,542 | 2,831,627 | 8,556,003 | 6,928,902 | | |
| | | | | | | | CD44+ | 4,278,041 | 2,820,466 | 8,259,680 | 5,878,487 | | |
| | | | | | | | CD10+ | 20,005,642 | 14,772,311 | | | | |
| | | | | | | | stroma | 8,726,273 | 6,737,622 | | | | |
| N40 | 29 | PAR-2 | AA | Pre | Rdx | | CD24+ | 3,540,368 | 2,311,370 | 7,491,800 | 6,277,412 | | |
| | | | | | | | CD44+ | 3,979,209 | 2,463,398 | 8,335,235 | 6,910,263 | | |
| | | | | | | | CD10+ | 16,842,503 | 10,224,177 | | | | |
| | | | | | | | stroma | 4,131,771 | 2,899,771 | | | | |
| N43 | 28 | PAR-0 | AA | Pre | Rdx | | CD24+ | 11,645,900 | 8,062,235 | | | | |
| | | | | | | | CD44+ | 13026527 | 9835625 | | | | |
| | | | | | | | CD10+ | 23,754,619 | 16,664,431 | | | | |
| N47 | 21 | UK | AA | Pre | Rdx | | CD24+ | 2,983,207 | 1,933,928 | | | | |
| | | | | | | | CD44+ | 1,824,933 | 1,137,819 | | | | |

TABLE 3-continued

Parity-related Differences in Global Gene Expression Profiles

| ID | Age | Parity | Ethnicity | Pre/Post | Type | Marker | Val1 | Val2 | Val3 | Val4 | Val5 | Val6 |
|---|---|---|---|---|---|---|---|---|---|---|---|---|
| N48 | 26 | PAR-0 | CU | Pre | Rdx | CD24+ | 1,800,069 | 1,098,424 | 14,849,010 | 8,402,630 | | |
| | | | | | | CD44+ | 1,045,874 | 695,300 | 10,935,565 | 4,166,534 | | |
| | | | | | | CD10+ | 23100428 | 15163719 | | | | |
| N58 | 23 | PAR-0 | AA | Pre | Rdx | CD24+ | 9,720,068 | 6,197,805 | | | | |
| | | | | | | CD44+ | 11,007,864 | 7,066,583 | | | | |
| | | | | | | stroma | 11,466,462 | 8,276,113 | | | | |
| N66 | 21 | PAR-1 | AA | Pre | Rdx | CD24+ | | | | | 17,669,447 | 10,633,724 |
| | | | | | | CD44+ | | | | | 115,374,101 | 59,596,544 |
| N74 | 20 | PAR-0 | AA | Pre | Rdx | CD24+ | | | | | 16,760,143 | 9,086,702 |
| | | | | | | CD44+ | | | | | 125,461,312 | 66,593,764 |
| N123 | 31 | PAR-2 | AA | Pre | Rdx | CD10+ | 25,194,642 | 17,423,893 | | | | |
| N27 | 23 | PAR-0 | AA | Pre | Rdx | | | | | | | |
| N28 | 35 | PAR-2 | AA | Pre | Rdx | | | | | | | |
| N29 | 26 | PAR-0 | CU | Pre | Rdx | | | | | | | |
| N31 | 31 | PAR-2 | AA | Pre | Rdx | | | | | | | |
| N38 | 32 | PAR-0 | CU | Pre | Rdx | | | | | | | |
| N42 | 17 | PAR-0 | CU | Pre | Rdx | | | | | | | |
| N44 | 21 | PAR-0 | CU | Pre | Rdx | | | | | | | |
| N53 | 41 | PAR-2 | AA | Pre | Rdx | | | | | | | |
| N55 | 22 | PAR-0 | CU | Pre | Rdx | | | | | | | |
| N57 | 27 | PAR-0 | CU | Pre | Rdx | | | | | | | |
| N61 | 20 | PAR-1 | AA | Pre | Rdx | | | | | | | |
| N63 | 21 | PAR-0 | CU | Pre | Rdx | | | | | | | |
| N65 | 55 | PAR-4 | AA | | Rdx | | | | | | | |
| N69 | 27 | PAR-0 | CU | Pre | Rdx | | | | | | | |
| N71 | 29 | PAR-1 | AA | Pre | Rdx | | | | | | | |
| N72 | 23 | PAR-2 | AA | Pre | Rdx | | | | | | | |
| N78 | 23 | PAR-1 | AA | Pre | Rdx | | | | | | | |
| N84 | 29 | PAR | AA | Pre | Rdx | | | | | | | |
| N85 | 25 | PAR-0 | CU | Pre | Rdx | | | | | | | |
| N91 | 23 | PAR-0 | HP | Pre | Rdx | | | | | | | |
| N93 | 29 | PAR | ? | Pre | Rdx | | | | | | | |
| N95 | 34 | PAR-2 | CU | Pre | Rdx | | | | | | | |
| N99 | 29 | PAR-2 | ? | Pre | Rdx | | | | | | | |
| N102 | 16 | PAR-0 | CU | Pre | Rdx | | | | | | | |
| N103 | 17 | PAR-0 | AA | Pre | Rdx | | | | | | | |
| N104 | 17 | PAR-0 | AA | Pre | Rdx | | | | | | | |
| N106 | 20 | PAR-0 | CU | Pre | Rdx | | | | | | | |
| N108 | 27 | PAR-3 | AA | Pre | Rdx | | | | | | | |
| N109 | 36 | PAR-2 | AS | Pre | Rdx | | | | | | | |
| N111 | 27 | PAR-2 | HP | Pre | Rdx | | | | | | | |
| N112 | 26 | PAR-2 | AA | Pre | Rdx | | | | | | | |
| N113 | 23 | PAR-1 | CU | Pre | Rdx | | | | | | | |
| N114 | 19 | PAR-0 | CU | Pre | Rdx | | | | | | | |
| N115 | 27 | PAR-2 | AA | Pre | Rdx | | | | | | | |
| N116 | 22 | PAR-2 | AA | Pre | Rdx | | | | | | | |
| N117 | 22 | PAR-0 | CU | Pre | Rdx | | | | | | | |
| N121 | 39 | PAR-2 | CU | Pre | Rdx | | | | | | | |
| N135 | 53 | PAR-2 | CU | | Rdx | | | | | | | |
| N136 | 20 | PAR-0 | CU | Pre | Rdx | | | | | | | |
| N141 | 21 | UK | CU | Pre | Rdx | | | | | | | |
| N165 | 24 | PAR-1 | CU | Pre | Rdx | | | | | | | |
| N166 | 28 | PAR-2 | AA | Pre | Rdx | | | | | | | |
| N175 | 20 | PAR-0 | CU | Pre | Rdx | | | | | | | |
| N178 | 21 | PAR-0 | cu | Pre | Rdx | | | | | | | |
| 275L | 52 | PAR-4 | AA | Post | Rdx | | | | | | | |
| 269R | 53 | PAR | ? | Post | Rdx | | | | | | | |
| 186L | 62 | PAR-2 | AA | Post | Rdx | | | | | | | |
| 219L | 73 | PAR-3 | CU | Post | Rdx | | | | | | | |
| 272 | 60 | PAR-1 | CU | Post | Rdx | | | | | | | |
| 227R | 55 | PAR-2 | ? | Post | prophylactic | | | | | | | |
| 188 | 54 | PAR-2 | AA | Post | prophylactic | | | | | | | |
| 204R | 56 | PAR-2 | CU | Post | prophylactic | | | | | | | |
| 213L | 57 | PAR-3 | CU | Post | prophylactic | | | | | | | |
| 241 | 57 | PAR-5 | CU | Post | prophylactic | | | | | | | |
| 190 | 49 | PAR-0 | CU | Post | prophylactic | | | | | | | |
| 207R | 52 | PAR-0 | CU | Post | prophylactic | | | | | | | |
| 221 L | 54 | PAR-0 | CU | Post | prophylactic | | | | | | | |
| 212 | 60 | PAR-0 | AA | Post | prophylactic | | | | | | | |

TABLE 3-continued

Parity-related Differences in Global Gene Expression Profiles

| | | | | | | |
|---|---|---|---|---|---|---|
| 288 | 41 | PAR-0 | CU | Post | prophy-lactic | |
| 307 | 61 | PAR-0 | CU | Post | prophy-lactic | |
| 313 | 63 | PAR-0 | CU | Post | prophy-lactic | |
| MDB11 | 52 | PAR-2 | CU | | biopsy | High |
| MDB17 | 61 | PAR-2 | CU | Post | biopsy | High |
| MDB27 | 49 | PAR-1 | CU | Pre | biopsy | High |
| MDB29 | | PAR-1 | ? | | biopsy | Low |
| MDB32 | 37 | PAR-2 | AS | Pre | biopsy | Low |
| MDB34 | | PAR-2 | ? | | biopsy | Low |
| MDB35 | 31 | PAR-5 | CU | Pre | biopsy | High |
| MDB48 | 35 | PAR-2 | CU | Pre | biopsy | Low |
| MDB51 | | PAR-2 | ? | | biopsy | High |
| MDB56 | 40 | PAR-2 | CU | Pre | biopsy | Low |
| MDB59 | | PAR-2 | 9 | | biopsy | High |
| MDS19 | | PAR-2 | 9 | | slice | Low |
| MDS35 | | PAR-2 | 9 | | slice | Low |
| MDS48 | 35 | PAR-3 | CU | Pre | slice | High |
| MDS52 | | PAR-3 | 9 | | slice | Low |
| MDS60 | 48 | PAR-2 | CU | Pre | slice | High |
| MDS61 | | PAR-2 | 9 | | slice | Low |
| MDS71 | 43 | PAR-2 | CU | Pre | slice | High |
| MDS74 | | PAR-2 | 9 | | slice | Low |
| MDS8 | 34 | PAR-2 | CU | Pre | slice | High |

| Tissue | qRT-PCR | qMSP | FACS | IF/IHC | CULT | Notes |
|---|---|---|---|---|---|---|
| N33 | x | x | | x | | |
| N34 | | | | | | |
| N35 | x | x | | x | | |
| N37 | x | x | | | | |
| N39 | x | x | | | | |
| N40 | x | x | | | | |
| N43 | x | x | | | | |
| N47 | | | | | | |
| N48 | x | x | | | | |
| N58 | x | x | | | | |
| N66 | | | | | | |
| N74 | | | x | | | |
| N123 | x | x | | | | |
| N27 | | | | x | | |
| N28 | | | | x | | |
| N29 | | | | x | | |
| N31 | | | | x | | |
| N38 | | | | x | | |
| N42 | x | x | | x | | |
| N44 | x | x | | x | | |
| N53 | | | | x | | |
| N55 | x | x | | | | |
| N57 | | | | x | | |
| N61 | x | x | | | | |
| N63 | | | x | | | |
| N65 | | | | x | | |
| N69 | | | x | | | |
| N71 | | | x | | | |
| N72 | | | x | x | | |
| N78 | | | x | | | |
| N84 | | | x | | | |
| N85 | x | x | x | | | |
| N91 | | | x | x | | |
| N93 | | | x | | | |
| N95 | x | x | | | | |
| N99 | | | | x | | |
| N102 | | | x | | | |
| N103 | | | | x | | |
| N104 | | | x | x | | |
| N106 | | | x | x | | |
| N108 | | | x | x | | |
| N109 | | | | x | | |
| N111 | x | x | | x | | |
| N112 | | | | x | | |
| N113 | | | x | x | | |
| N114 | | | x | x | | |
| N115 | x | x | x | x | | |
| N116 | | | x | x | | |

TABLE 3-continued

Parity-related Differences in Global Gene Expression Profiles

| ID | | | | Notes |
|---|---|---|---|---|
| N117 | x | x | | |
| N121 | x | x | | |
| N135 | | x | | |
| N136 | | x | | |
| N141 | | x | | |
| N165 | | | x | |
| N166 | | | x | |
| N175 | | | x | |
| N178 | | | x | |
| 275L | | x | | |
| 269R | | x | | |
| 186L | | x | | 30 Atypical LH33 Usual DH35 Papilloma40 Prolif. fibrocystic changes61 Mammoplasty |
| 219L | | x | | |
| 272 | | x | | |
| 227R | | x | | |
| 188 | | x | | 45 Non-prolif. fibrocystic or other changes47 Inflammation |
| 204R | | x | | |
| 213L | | x | | 30 Atypical LH |
| 241 | | x | | left breast (left total mastectomy): no invasive carcinoma seen, marked atypical lobular hyperplasia approaching criteria for lobular carcinoma in situ and focal atypical ductal hyperplasia, residual intraductal papilloma with biopsy site changes, multiple micropapillomas, columnar cell hyperplasia with cytologic atypia, and fibrocystic changes including usual ductal hyperplasia, ~ microcalcifications identified in upper outer, upper inner, lower outer and lower inner quadrants.; right breast not sampled: 31 atypical dh 30 atypical lh 35 papilloma 33 usual dh; no contralateral bc and this breast was totally removed and has marked alh |
| 190 | | x | | 2. LEFT BREAST (TOTAL MASTECTOMY): FOCAL ATYPICAL LOBULAR HYPERPLASIA IDENTIFIED. RADIAL SCAR AND FOCAL COLLAGENOUS SPHERULOSIS. FIBROCYSTIC CHANGES, INCLUDING DUCT ECTASIA AND APOCRINE METAPLASIA. MICROCALCIFICATIONS SEEN WITHIN BENIGN GLANDS. ~ NEGATIVE FOR TUMOR. 3. RIGHT BREAST (TOTAL MASTECTOMY): Ductal carcinoma in situ (DCIS). 1.3 cm grossly; the largest single focus of DCIS is 0.3 cm. M160; 22 DCIS 230 Atypical LH43 Radial scar62 Collagenous Spherulosis |
| 207R | | x | | |
| 221 L | | x | | LEFT BREAST: EXTENSIVE ATYPICAL LOBULAR HYPERPLASIA WITH FIBROCYSTIC CHANGES, COLUMNAR CELL CHANGE, SCLEROSING ADENOSIS, AND MICROCALCIFICATIONS SEEN IN ASSOCIATION WITH BENIGN BREAST PARENCHYMA. NEGATIVE FOR INVASIVE CARCINOMA; RIGHT BREAST Infiltrating mammary carcinoma with ductal and lobular features; 08 Inv. mammary CA45 Non-prolif. fibrocystic or other changes |
| 212 | | x | | 45 Non-prolif. fibrocystic or other changes |
| 288 | | x | | |
| 307 | | x | | |
| 313 | | x | | |
| MDB11 | | x | | BRCA2, PHx BC |
| MDB17 | | x | | DCIS, FHx Mother BC 45 |
| MDB27 | | x | | BRCA2, PHx bilateral oophorectomy |
| MDB29 | | x | | |
| MDB32 | | x | | BRCA1, BC |
| MDB34 | | x | | |
| MDB35 | | x | | BRCA2 |
| MDB48 | | x | | BRCA1 |
| MDB51 | | x | | |
| MDB56 | | x | | BRCA1, R breast ca, L SSM, BPO |
| MDB59 | | x | | |

TABLE 3-continued

Parity-related Differences in Global Gene Expression Profiles

| | | |
|---|---|---|
| MDS19 | x | |
| MDS35 | x | |
| MDS48 | x | BRCA2 |
| MDS52 | x | |
| MDS60 | x | BRCA2, L DCIS |
| MDS61 | x | |
| MDS71 | x | BRCA1 |
| MDS74 | x | |
| MDS8 | x | strong FHx: 7/9 women BC |

Abbreviations: "AA": African American; "CU": Caucasian; "HP": Hispanic; "AS": Asian; "?": unknown; "Rdxn": reduction; "Pre": premenopausal; "Post": postmenopausal. PAR-0 means 0 live births, PAR-1 means 1 live birth, PAR-2 means 2 live births, etc.; "UK", "?" or empty field means unknown.

TABLE 4

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| Higher Expression in Nulliparous | | | | | | | | | |
| HBB | 8.647 | 16.805 | 13.823 | 7.618 | 6.519 | 6.320 | −158.005 | 0.0081376 | hemoglobin, beta |
| SEC61B | 0.648 | 8.071 | 7.682 | 0.648 | 0.648 | 0.648 | −131.001 | 0.0204697 | Sec61 beta subunit |
| HBA1 | 4.972 | 13.737 | 10.850 | 4.529 | 3.871 | 4.389 | −88.112 | 0.0150652 | hemoglobin, alpha 1 |
| KRTAP4-12 | 0.648 | 7.519 | 7.072 | 0.648 | 0.648 | 0.648 | −85.830 | 0.0222555 | keratin associated protein 4-12 |
| COX17 | 0.648 | 7.215 | 6.821 | 0.648 | 0.648 | 0.648 | −72.130 | 0.0232128 | COX17 cytochrome c oxidase assembly homolog (S. cerevisiae) |
| NCRNA00188 | 7.097 | 11.959 | 11.406 | 5.245 | 4.754 | 5.237 | −71.960 | 0.0055269 | non-protein coding RNA 188 |
| RPS29 | 7.658 | 12.828 | 12.402 | 4.981 | 5.508 | 6.679 | −70.970 | 0.0066430 | ribosomal protein S29 |
| RPL27A | 8.098 | 12.704 | 12.477 | 5.652 | 5.732 | 6.635 | −67.139 | 0.0053321 | ribosomal protein L27a |
| COL3A1 | 15.562 | 12.000 | 11.854 | 5.787 | 7.350 | 8.068 | −67.080 | 0.0013099 | collagen, type III, alpha 1 |
| ERH | 3.422 | 8.682 | 7.643 | 2.625 | 0.648 | 1.648 | −63.771 | 0.0099352 | enhancer of rudimentary homolog (Drosophila) |
| SRP19 | 0.648 | 6.638 | 6.666 | 0.648 | 0.648 | 0.648 | −63.530 | 0.0242693 | signal recognition particle 19 kDa |
| MTND3 | 9.246 | 13.456 | 13.535 | 6.682 | 7.613 | 6.556 | −60.630 | 0.0044010 | No description |
| LOC728640 | 3.194 | 6.597 | 6.494 | 0.648 | 0.648 | 0.648 | −57.528 | 0.0028697 | No description |
| CD9 | 6.906 | 10.132 | 9.475 | 4.023 | 3.659 | 3.303 | −56.360 | 0.0010860 | CD9 molecule |
| ITM2A | 10.733 | 11.707 | 11.583 | 4.951 | 5.344 | 6.820 | −55.036 | 0.0001563 | integral membrane protein 2A |
| FAM10A4 | 4.972 | 9.120 | 9.050 | 3.351 | 2.353 | 3.043 | −54.534 | 0.0054458 | No description |
| HNRNPA1 | 3.619 | 8.990 | 7.992 | 3.278 | 2.233 | 2.233 | −52.447 | 0.0136315 | heterogeneous nuclear ribonucleoprotein A1 |
| TRMT5 | 5.235 | 9.979 | 9.956 | 2.970 | 2.970 | 4.327 | −50.282 | 0.0073147 | TRM5tRNA methyltransferase 5 homolog (S. cerevisiae) |
| TXN | 3.619 | 11.152 | 10.795 | 5.256 | 3.559 | 5.147 | −50.124 | 0.0435317 | thioredoxin |
| TUBA1B | 6.689 | 11.666 | 11.390 | 5.660 | 5.914 | 5.749 | −49.875 | 0.0139955 | tubulin, alpha 1b |
| YBX1 | 6.196 | 10.489 | 10.347 | 4.869 | 4.697 | 4.323 | −49.183 | 0.0082811 | Y box binding protein 1 |
| MYEOV2 | 0.648 | 7.122 | 6.202 | 0.648 | 0.648 | 0.648 | −46.973 | 0.0245799 | myeloma overexpressed 2 |
| NDUFB4 | 7.531 | 9.476 | 9.845 | 3.284 | 3.284 | 2.370 | −44.414 | 0.0005064 | NADH dehydrogenase (ubiquinone) 1 beta subcomplex, 4, 15 kDa |
| LUM | 9.317 | 13.167 | 10.563 | 4.504 | 4.504 | 6.235 | −43.086 | 0.0012558 | lumican |
| RAB6C | 0.648 | 7.611 | 6.395 | 2.202 | 0.648 | 0.648 | −42.502 | 0.0368516 | RAB6C, member RAS oncogene family |
| TMEM11 | 3.860 | 7.125 | 6.054 | 0.648 | 0.648 | 0.648 | −42.405 | 0.0011387 | transmembrane protein 11 |
| LOC653566 | 5.739 | 8.703 | 8.889 | 3.351 | 0.648 | 3.351 | −40.858 | 0.0029397 | No description |
| UBE2NL | 6.312 | 10.364 | 5.977 | 0.648 | 3.284 | 3.351 | −40.180 | 0.0065709 | ubiquitin-conjugating enzyme E2N-like |
| GPR89A | 0.648 | 6.549 | 5.956 | 0.648 | 0.648 | 0.648 | −39.615 | 0.0258277 | G protein-coupled receptor 89A |
| COL1A1 | 14.250 | 12.168 | 11.083 | 5.822 | 7.572 | 8.793 | −38.367 | 0.0029757 | collagen, type I, alpha 1 |
| NUDT4P1 | 3.860 | 8.958 | 7.461 | 2.202 | 0.648 | 3.043 | −38.311 | 0.0087220 | nudix (nucleoside diphosphate linked moiety X)-type motif 4 pseudogene 1 |
| ISCA1 | 0.648 | 6.177 | 5.899 | 0.648 | 0.648 | 0.648 | −38.081 | 0.0267386 | iron-sulfur cluster assembly 1 homolog (S. cerevisiae) |
| HSPA2 | 5.870 | 6.981 | 6.117 | 2.714 | 0.648 | 0.648 | −37.314 | 0.0006194 | heat shock 70 kDa protein 2 |
| PCBP1 | 8.603 | 11.285 | 11.391 | 6.087 | 5.763 | 6.197 | −36.600 | 0.0025071 | poly(rC) binding protein 1 |
| KRT10 | 0.648 | 5.870 | 5.761 | 0.648 | 0.648 | 0.648 | −34.605 | 0.0279262 | keratin 10 |
| INS-IGF2 | 10.308 | 9.204 | 9.134 | 4.021 | 4.043 | 6.006 | −34.586 | 0.0007324 | No description |
| ANXA3 | 3.194 | 5.754 | 6.378 | 0.648 | 0.648 | 0.648 | −34.443 | 0.0027900 | annexin A3 |
| RPL7 | 10.636 | 13.028 | 12.983 | 7.244 | 7.929 | 7.722 | −34.262 | 0.0012738 | ribosomal protein L7 |
| KLK3 | 5.739 | 5.521 | 5.754 | 0.648 | 0.648 | 0.648 | −34.075 | 0.0000738 | kallikrein-related peptidase 3 |
| SHFM1 | 1.648 | 7.890 | 6.701 | 1.648 | 2.739 | 1.648 | −33.198 | 0.0371744 | split hand/foot malformation (ectrodactyly) type 1 |
| SEP2 | 10.248 | 10.425 | 10.374 | 6.570 | 5.325 | 5.140 | −33.102 | 0.0001972 | septin 2 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| RPL26 | 8.606 | 12.693 | 12.085 | 6.947 | 7.056 | 7.316 | −32.643 | 0.0092225 | ribosomal protein L26 |
| GABARAP | 7.394 | 10.012 | 10.092 | 5.102 | 3.499 | 3.929 | −31.765 | 0.0015040 | GABA(A) receptor-associated protein |
| BUD31 | 3.194 | 8.066 | 7.993 | 3.081 | 2.353 | 2.370 | −31.676 | 0.0183061 | BUD31 homolog (S. cerevisiae) |
| UBAC1 | 3.194 | 6.126 | 5.544 | 0.648 | 0.648 | 0.648 | −29.759 | 0.0027088 | UBA domain containing 1 |
| ALKBH5 | 9.928 | 11.367 | 11.055 | 6.503 | 5.518 | 5.311 | −29.126 | 0.0002513 | alkB, alkylation repair homolog 5 (E. coli) |
| RPL37 | 10.581 | 13.131 | 13.029 | 7.164 | 8.072 | 8.275 | −28.974 | 0.0022485 | ribosomal protein L37 |
| PCNP | 2.233 | 7.899 | 7.875 | 2.233 | 2.233 | 3.054 | −28.731 | 0.0325213 | PEST proteolytic signal containing nuclear protein |
| RCN2 | 5.972 | 7.462 | 7.136 | 2.625 | 1.648 | 1.648 | −28.583 | 0.0002693 | reticulocalbin 2, EF-hand calcium binding domain |
| TPT1 | 9.340 | 12.721 | 12.261 | 6.968 | 7.443 | 7.857 | −28.210 | 0.0062811 | tumor protein, translationally-controlled 1 |
| RAB32 | 5.503 | 7.826 | 8.100 | 3.278 | 3.043 | 2.233 | −27.537 | 0.0026458 | RAB32, member RAS oncogene family |
| COX6A1 | 2.233 | 8.695 | 7.823 | 3.278 | 2.233 | 3.054 | −27.262 | 0.0416541 | cytochrome c oxidase subunit VIa polypeptide 1 |
| SLC38A5 | 6.689 | 8.619 | 9.360 | 3.797 | 4.508 | 3.859 | −27.100 | 0.0026139 | solute carrier family 38, member 5 |
| PMAIP1 | 5.104 | 7.419 | 7.489 | 1.648 | 1.648 | 1.648 | −26.916 | 0.0014270 | phorbol-12-myristate-13-acetate-induced protein 1 |
| MYL9 | 9.593 | 10.372 | 8.270 | 4.492 | 5.654 | 3.859 | −26.330 | 0.0009730 | myosin, light chain 9, regulatory |
| GLT8D2 | 6.948 | 7.589 | 6.972 | 2.233 | 2.233 | 4.481 | −26.267 | 0.0020842 | glycosyltransferase 8 domain containing 2 |
| TCN2 | 6.202 | 5.544 | 5.359 | 0.648 | 0.648 | 2.370 | −26.181 | 0.0007414 | transcobalamin II |
| TMEM14C | 6.734 | 8.339 | 7.435 | 3.326 | 2.739 | 2.752 | −25.679 | 0.0003414 | transmembrane protein 14C |
| PPP1CA | 5.861 | 8.464 | 8.699 | 4.017 | 2.648 | 2.648 | −25.658 | 0.0027629 | protein phosphatase 1, catalytic subunit, alpha isozyme |
| TMEM93 | 4.008 | 7.416 | 7.691 | 3.023 | 1.648 | 1.648 | −25.421 | 0.0071733 | transmembrane protein 93 |
| MTCO1 | 12.874 | 13.692 | 13.863 | 9.044 | 9.612 | 7.985 | −25.073 | 0.0004704 | No description |
| GADD45A | 6.069 | 9.577 | 8.737 | 2.648 | 4.097 | 4.647 | −24.932 | 0.0058582 | growth arrest and DNA-damage-inducible, alpha |
| ACTG1 | 13.979 | 14.085 | 13.590 | 9.279 | 9.936 | 8.967 | −24.639 | 0.0001473 | actin, gamma 1 |
| DNTTIP1 | 1.648 | 6.232 | 6.244 | 1.648 | 1.648 | 1.648 | −23.986 | 0.0317369 | deoxynucleotidyltransferase, terminal, interacting protein 1 |
| PENK | 7.941 | 7.204 | 2.841 | 2.648 | 2.648 | 2.648 | −23.518 | 0.0260981 | proenkephalin |
| KIAA0114 | 1.648 | 7.055 | 7.571 | 3.023 | 1.648 | 1.648 | −23.390 | 0.0402596 | KIAA0114 |
| AZGP1 | 5.821 | 7.886 | 8.813 | 2.951 | 4.265 | 2.233 | −23.389 | 0.0040939 | alpha-2-glycoprotein 1, zinc-binding |
| DAP | 6.777 | 9.285 | 8.177 | 4.678 | 3.648 | 3.648 | −23.077 | 0.0026908 | death-associated protein |
| MRPL15 | 0.648 | 6.723 | 5.961 | 2.202 | 0.648 | 0.648 | −22.956 | 0.0431463 | mitochondrial ribosomal protein L15 |
| SNX3 | 3.619 | 8.838 | 8.092 | 3.871 | 3.043 | 3.574 | −22.917 | 0.0277834 | sorting nexin 3 |
| SEPP1 | 8.967 | 9.118 | 9.243 | 3.838 | 4.618 | 5.019 | −22.637 | 0.0001383 | selenoprotein P, plasma, 1 |
| MRPL44 | 7.257 | 9.680 | 9.785 | 5.018 | 4.508 | 5.297 | −22.436 | 0.0037529 | mitochondrial ribosomal protein L44 |
| EEF1G | 12.169 | 13.523 | 13.689 | 8.514 | 9.210 | 8.857 | −22.303 | 0.0006104 | eukaryotic translation elongation factor 1 gamma |
| SLC2A14 | 8.465 | 6.340 | 6.562 | 4.017 | 1.648 | 3.929 | −21.820 | 0.0061133 | solute carrier family 2 (facilitated glucose transporter), member 14 |
| ERO1L | 8.074 | 9.537 | 9.526 | 5.117 | 4.600 | 4.013 | −21.396 | 0.0005785 | ERO1-like (S. cerevisiae) |
| NGRN | 5.552 | 8.281 | 8.108 | 3.718 | 3.852 | 3.303 | −20.964 | 0.0058943 | neugrin, neurite outgrowth associated |
| C5orf13 | 9.154 | 7.541 | 7.609 | 3.233 | 3.233 | 3.233 | −20.757 | 0.0002423 | chromosome 5 open reading frame 13 |
| ATP1B1 | 5.885 | 8.675 | 8.958 | 3.818 | 4.585 | 4.146 | −20.719 | 0.0079826 | ATPase, Na+/K+ transporting, beta 1 polypeptide |
| YWHAE | 5.645 | 9.950 | 9.172 | 4.775 | 4.800 | 5.290 | −20.698 | 0.0197203 | tyrosine 3-monooxygenase/tryptophan 5-monooxygenase activation protein, epsilon polypeptide |
| CHMP5 | 6.576 | 8.576 | 8.805 | 4.477 | 1.648 | 4.205 | −20.689 | 0.0040218 | chromatin modifying protein 5 |
| PNRC1 | 10.505 | 12.324 | 12.179 | 7.958 | 6.663 | 7.685 | −20.618 | 0.0014451 | proline-rich nuclear receptor coactivator 1 |
| TMEM66 | 6.512 | 9.520 | 8.515 | 4.151 | 3.508 | 5.008 | −20.591 | 0.0052960 | transmembrane protein 66 |
| EEF1E1 | 1.648 | 6.003 | 6.178 | 1.648 | 1.648 | 1.648 | −20.465 | 0.0330832 | eukaryotic translation elongation factor 1 epsilon 1 |
| COX6C | 4.142 | 8.087 | 8.031 | 2.951 | 2.233 | 3.737 | −20.391 | 0.0136135 | cytochrome c oxidase subunit VIc |
| H1FX | 9.181 | 10.411 | 11.038 | 7.775 | 4.838 | 5.939 | −20.288 | 0.0052870 | H1 histone family, member X |
| BMS1P5 | 4.972 | 5.514 | 6.308 | 2.202 | 0.648 | 0.648 | −20.022 | 0.0008045 | BMS1 pseudogene 5 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| MRPL36 | 0.648 | 5.748 | 4.972 | 0.648 | 0.648 | 0.648 | −20.022 | 0.0313778 | mitochondrial ribosomal protein L36 |
| SNRNP27 | 4.264 | 7.866 | 8.174 | 3.494 | 3.852 | 2.648 | −19.997 | 0.0164995 | small nuclear ribonucleoprotein 27 kDa (U4/U6.U5) |
| C8orf59 | 3.422 | 7.273 | 7.343 | 3.023 | 2.739 | 1.648 | −19.970 | 0.0162825 | chromosome 8 open reading frame 59 |
| TUBA1C | 6.967 | 11.132 | 10.008 | 5.691 | 6.454 | 5.400 | −19.937 | 0.0149882 | tubulin, alpha 1c |
| TMSB10 | 10.463 | 12.314 | 12.473 | 7.183 | 8.161 | 7.927 | −19.867 | 0.0021383 | thymosin beta 10 |
| CXCL6 | 6.470 | 10.026 | 10.054 | 5.602 | 4.618 | 5.749 | −19.766 | 0.0140343 | chemokine (C-X-C motif) ligand 6 (granulocyte chemotactic protein 2) |
| SURF1 | 1.648 | 6.251 | 5.940 | 1.648 | 1.648 | 1.648 | −19.583 | 0.0331400 | surfeit 1 |
| DERL2 | 2.648 | 7.725 | 7.507 | 3.218 | 2.648 | 3.303 | −19.549 | 0.0442350 | Der1-like domain family, member 2 |
| ITPA | 4.657 | 7.543 | 6.960 | 3.278 | 2.739 | 2.233 | −19.237 | 0.0058028 | inosine triphosphatase (nucleoside triphosphate pyrophosphatase) |
| RPLP1 | 6.711 | 11.703 | 10.309 | 6.056 | 5.848 | 6.416 | −19.068 | 0.0211289 | ribosomal protein, large, P1 |
| C7orf23 | 1.648 | 5.897 | 6.033 | 1.648 | 1.648 | 1.648 | −19.014 | 0.0342707 | chromosome 7 open reading frame 23 |
| FBXO7 | 5.423 | 8.077 | 7.855 | 3.838 | 3.294 | 2.648 | −18.884 | 0.0050340 | F-box protein 7 |
| C14orf147 | 8.217 | 10.423 | 10.475 | 5.864 | 6.170 | 6.288 | −18.218 | 0.0045376 | chromosome 14 open reading frame 147 |
| FAM162A | 3.422 | 7.320 | 6.924 | 1.648 | 2.739 | 2.752 | −18.187 | 0.0153570 | family with sequence similarity 162, member A |
| SYPL1 | 4.482 | 9.210 | 9.108 | 4.930 | 4.772 | 5.005 | −18.090 | 0.0484003 | synaptophysin-like 1 |
| CENPH | 7.001 | 8.255 | 7.839 | 3.737 | 3.686 | 3.054 | −17.781 | 0.0004433 | centromere protein H |
| MRFAP1 | 2.648 | 7.851 | 6.795 | 3.218 | 2.648 | 2.648 | −17.716 | 0.0396808 | Mof4 family associated protein 1 |
| TUBA1A | 8.428 | 10.140 | 9.793 | 4.529 | 6.006 | 5.014 | −17.565 | 0.0011657 | tubulin, alpha 1a |
| KCTD9 | 7.090 | 9.444 | 9.585 | 4.954 | 4.581 | 5.451 | −17.552 | 0.0050610 | potassium channel tetramerisation domain containing 9 |
| COX6B1 | 4.008 | 8.325 | 8.507 | 4.376 | 4.174 | 3.929 | −17.530 | 0.0395192 | cytochrome c oxidase subunit VIb polypeptide 1 (ubiquitous) |
| RPS8 | 9.220 | 11.925 | 12.160 | 7.022 | 7.798 | 7.945 | −17.475 | 0.0088794 | ribosomal protein S8 |
| CUL4B | 6.848 | 6.936 | 6.356 | 2.951 | 2.233 | 2.233 | −17.425 | 0.0001744 | cullin 4B |
| MTND5 | 8.549 | 11.299 | 10.476 | 6.856 | 6.357 | 5.893 | −17.373 | 0.0050520 | No description |
| UGDH | 7.690 | 11.658 | 10.444 | 6.380 | 6.178 | 6.327 | −17.351 | 0.0112565 | UDP-glucose 6-dehydrogenase |
| MRPL51 | 0.648 | 6.318 | 6.279 | 2.202 | 0.648 | 0.648 | −17.342 | 0.0431172 | mitochondrial ribosomal protein L51 |
| RBM3 | 8.937 | 10.422 | 10.580 | 6.401 | 6.320 | 5.155 | −17.170 | 0.0016981 | RNA binding motif (RNP1, RRM) protein 3 |
| NDUFA4 | 5.808 | 8.849 | 8.402 | 4.067 | 4.757 | 4.104 | −17.059 | 0.0103373 | NADH dehydrogenase (ubiquinone) 1 alpha subcomplex, 4, 9 kDa |
| NCSTN | 7.148 | 8.445 | 7.058 | 3.881 | 2.970 | 3.859 | −17.003 | 0.0010180 | nicastrin |
| KRT6B | 6.829 | 10.079 | 8.896 | 4.376 | 7.613 | 2.752 | −16.869 | 0.0229771 | keratin 6B |
| HMGCL | 5.204 | 3.959 | 4.713 | 0.648 | 0.648 | 0.648 | −16.736 | 0.0004523 | 3-hydroxymethyl-3-methylglutaryl-CoA lyase |
| E2F5 | 0.648 | 4.713 | 5.256 | 0.648 | 0.648 | 0.648 | −16.736 | 0.0345099 | E2F transcription factor 5, p130-binding |
| PTP4A2 | 9.512 | 11.322 | 10.748 | 6.773 | 6.340 | 6.685 | −16.723 | 0.0011567 | protein tyrosine phosphatase type IVA, member 2 |
| SPARC | 12.921 | 13.011 | 11.241 | 8.708 | 8.558 | 8.963 | −16.538 | 0.0023269 | secreted protein, acidic, cysteine-rich (osteonectin) |
| ATPIF1 | 6.251 | 7.671 | 7.429 | 3.625 | 3.294 | 3.303 | −16.520 | 0.0010589 | ATPase inhibitory factor 1 |
| LITAF | 10.529 | 11.665 | 11.017 | 6.839 | 6.973 | 7.032 | −16.506 | 0.0002873 | lipopolysaccharide-induced TNF factor |
| HBP1 | 4.634 | 8.807 | 8.714 | 4.764 | 4.108 | 4.580 | −16.490 | 0.0312482 | HMG-box transcription factor 1 |
| PPP6C | 7.663 | 9.523 | 9.349 | 5.482 | 5.272 | 4.293 | −16.468 | 0.0027179 | protein phosphatase 6, catalytic subunit |
| COL1A2 | 13.816 | 11.981 | 11.457 | 8.141 | 7.421 | 8.682 | −16.413 | 0.0018049 | collagen, type I, alpha 2 |
| USMG5 | 6.262 | 9.240 | 8.839 | 4.804 | 5.183 | 3.737 | −16.400 | 0.0095220 | up-regulated during skeletal muscle growth 5 homolog (mouse) |
| FOS | 11.330 | 13.047 | 13.231 | 7.738 | 8.344 | 9.221 | −16.117 | 0.0020752 | FBJ murine osteosarcoma viral oncogene homolog |
| LRRC41 | 10.097 | 11.106 | 10.589 | 6.579 | 6.727 | 6.197 | −16.115 | 0.0002964 | leucine rich repeat containing 41 |
| LGALS3 | 5.322 | 9.705 | 9.129 | 5.120 | 5.050 | 5.407 | −16.107 | 0.0321050 | lectin, galactoside-binding, soluble, 3 |
| BRD7P3 | 4.647 | 7.288 | 6.037 | 0.648 | 3.284 | 0.648 | −16.050 | 0.0045737 | bromodomain containing 7 pseudogene 3 |

TABLE 4-continued

Differentially Expressed Genes in CD44+ Breast Epithelial Cells

| Gene Symbol | Nulliparous (NP) Samples | | | | Parous (P) Samples | | | | Pseudo fold change | P value | Gene description |
|---|---|---|---|---|---|---|---|---|---|---|---|
| | CD44+ N48 | CD44+ N58 | CD44+ N43 | | CD44+ N37 | CD44+ N39 | CD44+ N40 | | | | |
| VKORC1 | 6.347 | 8.151 | 6.648 | | 3.625 | 2.648 | 2.648 | | −15.994 | 0.0014721 | vitamin K epoxide reductase complex, subunit 1 |
| CSTF1 | 4.647 | 5.403 | 6.142 | | 0.648 | 2.353 | 0.648 | | −15.982 | 0.0016260 | cleavage stimulation factor, 3′ pre-RNA, subunit 1, 50 kDa |
| C1orf43 | 4.525 | 7.872 | 7.788 | | 3.877 | 3.467 | 2.233 | | −15.950 | 0.0131088 | chromosome 1 open reading frame 43 |
| RPL27 | 8.900 | 11.804 | 11.213 | | 7.308 | 7.147 | 7.222 | | −15.895 | 0.0080614 | ribosomal protein L27 |
| F3 | 5.936 | 8.691 | 8.283 | | 4.026 | 4.701 | 4.007 | | −15.891 | 0.0082971 | coagulation factor III (thromboplastin, tissue factor) |
| FIGF | 8.763 | 7.210 | 4.425 | | 3.233 | 3.233 | 4.553 | | −15.746 | 0.0238977 | c-fos induced growth factor (vascular endothelial growth factor D) |
| PPP1R15A | 9.690 | 11.015 | 10.841 | | 6.209 | 6.767 | 7.039 | | −15.741 | 0.0010000 | protein phosphatase 1, regulatory (inhibitor) subunit 15A |
| PPP2R2A | 5.936 | 8.906 | 8.406 | | 4.026 | 4.490 | 4.436 | | −15.675 | 0.0087082 | protein phosphatase 2, regulatory subunit B, alpha |
| ID4 | 5.809 | 9.133 | 6.939 | | 3.442 | 2.970 | 2.970 | | −15.661 | 0.0041605 | Description |
| CDKN1B | 7.367 | 7.407 | 7.471 | | 3.442 | 2.970 | 3.859 | | −15.612 | 0.0002333 | cyclin-dependent kinase inhibitor 1B (p27, Kip1) |
| RPS20 | 11.289 | 12.945 | 11.949 | | 7.891 | 8.161 | 7.986 | | −15.602 | 0.0007504 | ribosomal protein S20 |
| VASP | 6.741 | 8.742 | 7.454 | | 4.273 | 4.784 | 2.648 | | −15.545 | 0.0051380 | vasodilator-stimulated phosphoprotein |
| LILRB3 | 6.340 | 8.555 | 8.128 | | 4.477 | 4.174 | 2.752 | | −15.495 | 0.0042790 | leukocyte immunoglobulin-like receptor, subfamily B (with TM and ITIM domains), member 3 |
| RAB13 | 7.177 | 8.862 | 8.599 | | 5.093 | 3.233 | 4.007 | | −15.384 | 0.0021293 | RAB13, member RAS oncogene family |
| SC4MOL | 6.873 | 9.429 | 9.263 | | 5.489 | 4.791 | 3.701 | | −15.349 | 0.0058173 | sterol-C4-methyl oxidase-like |
| RPS18 | 12.062 | 14.408 | 14.030 | | 9.707 | 10.357 | 10.104 | | −15.203 | 0.0055518 | ribosomal protein S18 |
| RPS19 | 7.761 | 12.478 | 11.500 | | 7.339 | 7.771 | 7.574 | | −15.197 | 0.0297189 | ribosomal protein S19 |
| GNG11 | 6.911 | 7.182 | 6.392 | | 4.972 | 2.987 | 0.648 | | −15.186 | 0.0097619 | guanine nucleotide binding protein (G protein), gamma 11 |
| DCN | 11.356 | 13.930 | 12.077 | | 8.162 | 8.030 | 8.978 | | −15.082 | 0.0030028 | decorin |
| HSP90AB1 | 12.747 | 14.232 | 14.095 | | 9.664 | 10.274 | 10.180 | | −15.080 | 0.0016440 | heat shock protein 90 kDa alpha (cytosolic), class B member 1 |
| SFRS9 | 8.226 | 10.361 | 10.536 | | 6.518 | 6.447 | 6.036 | | −15.072 | 0.0061633 | No description |
| MED28 | 4.734 | 7.470 | 7.582 | | 1.648 | 2.739 | 3.557 | | −15.067 | 0.0069300 | mediator complex subunit 28 |
| C11orf10 | 10.342 | 10.380 | 10.555 | | 7.203 | 6.469 | 6.124 | | −15.048 | 0.0004974 | chromosome 11 open reading frame 10 |
| H3F3C | 8.402 | 10.636 | 9.974 | | 6.728 | 5.600 | 5.889 | | −15.018 | 0.0043830 | H3 histone, family 3C |
| PITRM1 | 4.378 | 6.913 | 7.405 | | 2.970 | 3.508 | 2.970 | | −14.896 | 0.0137106 | pitrilysin metallopeptidase 1 |
| CPE | 8.958 | 9.792 | 8.563 | | 5.451 | 4.678 | 5.786 | | −14.777 | 0.0010770 | carboxypeptidase E |
| CCNG1 | 6.275 | 7.621 | 7.582 | | 3.218 | 3.739 | 2.648 | | −14.740 | 0.0010499 | cyclin G1 |
| PLEKHA9 | 0.648 | 4.529 | 4.632 | | 0.648 | 0.648 | 0.648 | | −14.735 | 0.0382638 | No description |
| PSMA2 | 7.473 | 9.614 | 9.563 | | 5.734 | 5.557 | 5.176 | | −14.724 | 0.0054998 | proteasome (prosome, macropain) subunit, alpha type, 2 |
| RPL38 | 4.734 | 9.696 | 8.685 | | 4.154 | 4.811 | 5.459 | | −14.660 | 0.0390305 | ribosomal protein L38 |
| LDHA | 9.890 | 12.239 | 11.456 | | 7.584 | 8.005 | 7.146 | | −14.644 | 0.0041425 | lactate dehydrogenase A |
| EIF4A1 | 6.955 | 11.946 | 11.064 | | 6.927 | 7.202 | 7.197 | | −14.589 | 0.0388794 | eukaryotic translation initiation factor 4A1 |
| RRP7A | 4.734 | 6.882 | 5.570 | | 3.023 | 1.648 | 1.648 | | −14.506 | 0.0046402 | ribosomal RNA processing 7 homolog A (S. cerevisiae) |
| CSRP2 | 4.008 | 6.618 | 5.502 | | 1.648 | 1.648 | 1.648 | | −14.460 | 0.0038229 | cysteine and glycine-rich protein 2 |
| BET1 | 3.422 | 5.502 | 6.151 | | 1.648 | 1.648 | 1.648 | | −14.458 | 0.0073834 | blocked early in transport 1 homolog (S. cerevisiae) |
| ZMYND19 | 2.233 | 6.080 | 6.284 | | 2.233 | 2.233 | 2.233 | | −14.387 | 0.0379962 | zinc finger, MYND-type containing 19 |
| DDOST | 5.619 | 8.444 | 7.877 | | 4.600 | 3.294 | 2.648 | | −14.361 | 0.0072967 | dolichyl-diphosphooligosaccharide–protein glycosyltransferase |
| MAP2K4 | 4.817 | 6.886 | 7.127 | | 2.951 | 3.043 | 3.054 | | −14.347 | 0.0068253 | mitogen-activated protein kinase kinase 4 |
| EBPL | 2.233 | 6.072 | 6.120 | | 2.233 | 2.233 | 2.233 | | −14.310 | 0.0392392 | emopamil binding protein-like |
| PTGS2 | 9.624 | 10.879 | 11.105 | | 5.802 | 5.804 | 7.275 | | −14.230 | 0.0011927 | prostaglandin-endoperoxide synthase 2 (prostaglandin G/H synthase and cyclooxygenase) |
| TSPAN13 | 4.264 | 6.763 | 7.124 | | 2.648 | 3.294 | 2.648 | | −14.218 | 0.0114236 | tetraspanin 13 |
| TAC1 | 4.482 | 7.903 | 8.109 | | 3.233 | 3.233 | 4.299 | | −14.023 | 0.0178395 | tachykinin, precursor 1 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| RAB10 | 6.016 | 9.289 | 9.277 | 5.306 | 5.480 | 5.308 | −14.015 | 0.0226894 | RAB10, member RAS oncogene family |
| LIMS1 | 1.648 | 6.093 | 5.456 | 1.648 | 1.648 | 1.648 | −13.999 | 0.0366790 | LIM and senescent cell antigen-like domains 1 |
| ST8SIA2 | 6.070 | 6.849 | 4.889 | 2.233 | 3.043 | 2.233 | −13.983 | 0.0038998 | ST8 alpha-N-acetyl-neuraminide alpha-2,8-sialyltransferase 2 |
| AKR1B1 | 4.948 | 9.096 | 9.005 | 5.291 | 3.648 | 4.013 | −13.976 | 0.0220385 | aldo-keto reductase family 1, member B1 (aldose reductase) |
| MSX1 | 10.601 | 10.691 | 9.834 | 6.036 | 6.772 | 7.784 | −13.910 | 0.0028787 | msh homeobox 1 |
| LARS2 | 2.233 | 6.027 | 6.032 | 2.233 | 2.233 | 2.233 | −13.872 | 0.0402180 | isoleucyl-tRNA synthetase 2, mitochondrial |
| TFF1 | 5.870 | 5.996 | 6.744 | 2.202 | 5.462 | 0.648 | −13.871 | 0.0202742 | trefoil factor 1 |
| GBE1 | 5.688 | 7.352 | 7.507 | 3.718 | 3.294 | 2.648 | −13.823 | 0.0032711 | glucan (1,4-alpha-), branching enzyme 1 |
| EFNA4 | 0.648 | 4.435 | 5.053 | 0.648 | 0.648 | 0.648 | −13.805 | 0.0369882 | ephrin-A4 |
| AGK | 0.648 | 4.435 | 4.713 | 0.648 | 0.648 | 0.648 | −13.805 | 0.0385348 | acylglycerol kinase |
| KCNMB4 | 6.735 | 3.192 | 4.428 | 2.202 | 0.648 | 0.648 | −13.734 | 0.0111567 | potassium large conductance calcium-activated channel, subfamily M, beta member 4 |
| C18orf32 | 4.008 | 6.943 | 6.532 | 3.023 | 1.648 | 2.752 | −13.731 | 0.0111837 | chromosome 18 open reading frame 32 |
| KHSRP | 8.790 | 10.874 | 10.278 | 6.443 | 6.745 | 6.503 | −13.692 | 0.0039539 | KH-type splicing regulatory protein |
| TIMP2 | 12.402 | 12.959 | 11.428 | 8.074 | 7.958 | 9.195 | −13.590 | 0.0017161 | TIMP metallopeptidase inhibitor 2 |
| RAB23 | 1.648 | 5.502 | 5.412 | 1.648 | 1.648 | 1.648 | −13.587 | 0.0400308 | RAB23, member RAS oncogene family |
| OLFML1 | 8.845 | 6.725 | 3.702 | 2.970 | 2.970 | 2.970 | −13.497 | 0.0212510 | olfactomedin-like 1 |
| FUS | 8.319 | 10.917 | 10.446 | 7.165 | 6.238 | 6.364 | −13.473 | 0.0085064 | fused in sarcoma |
| BMP3 | 5.861 | 7.687 | 7.405 | 3.218 | 3.659 | 3.694 | −13.417 | 0.0032953 | bone morphogenetic protein 3 |
| MBD2 | 5.264 | 8.614 | 8.720 | 4.624 | 4.529 | 4.975 | −13.404 | 0.0243823 | methyl-CpG binding domain protein 2 |
| LASP1 | 8.565 | 9.202 | 8.478 | 4.824 | 4.108 | 5.814 | −13.369 | 0.0014090 | LIM and SH3 protein 1 |
| C1orf55 | 7.612 | 10.360 | 8.788 | 5.164 | 5.022 | 5.049 | −13.352 | 0.0036988 | chromosome 1 open reading frame 55 |
| C7orf68 | 3.233 | 6.967 | 7.798 | 3.233 | 3.233 | 3.233 | −13.306 | 0.0367546 | chromosome 7 open reading frame 68 |
| CYP7B1 | 0.648 | 5.119 | 4.381 | 0.648 | 0.648 | 0.648 | −13.295 | 0.0371497 | cytochrome P450, family 7, subfamily B, polypeptide 1 |
| SCARB2 | 8.340 | 9.123 | 8.591 | 5.384 | 4.667 | 4.875 | −13.139 | 0.0005605 | scavenger receptor class B, member 2 |
| MARCH7 | 3.233 | 7.351 | 7.317 | 3.637 | 3.233 | 3.233 | −13.130 | 0.0429702 | membrane-associated ring finger (C3HC4) 7 |
| MXRA8 | 11.216 | 10.021 | 10.434 | 5.899 | 6.732 | 8.137 | −13.010 | 0.0041154 | matrix-remodelling associated 8 |
| SLC7A3 | 6.522 | 4.335 | 2.714 | 0.648 | 0.648 | 0.648 | −12.876 | 0.0076530 | solute carrier family 7 (cationic amino acid transporter, y+ system), member 3 |
| LAPTM4B | 7.259 | 9.287 | 9.101 | 5.604 | 5.343 | 5.279 | −12.842 | 0.0064031 | lysosomal protein transmembrane 4 beta |
| CCNI | 8.217 | 11.531 | 9.815 | 6.692 | 5.140 | 6.137 | −12.807 | 0.0070922 | cyclin I |
| ECHDC3 | 1.648 | 6.265 | 5.314 | 1.648 | 1.648 | 1.648 | −12.694 | 0.0372302 | enoyl CoA hydratase domain containing 3 |
| C3orf14 | 4.314 | 3.644 | 4.908 | 0.648 | 0.648 | 0.648 | −12.687 | 0.0007955 | chromosome 3 open reading frame 14 |
| C7orf55 | 4.314 | 5.514 | 5.222 | 2.202 | 0.648 | 0.648 | −12.687 | 0.0020163 | chromosome 7 open reading frame 55 |
| MRPS11 | 4.314 | 4.372 | 4.901 | 0.648 | 2.353 | 0.648 | −12.687 | 0.0042056 | mitochondrial ribosomal protein S11 |
| C17orf95 | 4.314 | 5.761 | 5.742 | 3.081 | 0.648 | 0.648 | −12.687 | 0.0056558 | chromosome 17 open reading frame 95 |
| CSTA | 0.648 | 4.632 | 4.314 | 0.648 | 0.648 | 0.648 | −12.684 | 0.0399830 | cystatin A (stefin A) |
| P4HA2 | 5.109 | 5.898 | 6.235 | 2.233 | 2.233 | 2.233 | −12.629 | 0.0008634 | prolyl 4-hydroxylase, alpha polypeptide II |
| SRPRB | 5.423 | 8.814 | 8.027 | 4.886 | 4.368 | 4.294 | −12.456 | 0.0190021 | signal recognition particle receptor, B subunit |
| PAPSS1 | 7.297 | 6.785 | 6.412 | 3.494 | 3.659 | 2.648 | −12.453 | 0.0011040 | 3'-phosphoadenosine 5'-phosphosulfate synthase 1 |
| CAMLG | 6.047 | 7.646 | 8.254 | 3.648 | 4.007 | 4.013 | −12.403 | 0.0044510 | calcium modulating ligand |
| SNX25 | 3.422 | 5.404 | 5.281 | 1.648 | 1.648 | 1.648 | −12.393 | 0.0070652 | sorting nexin 25 |
| TMED7 | 6.463 | 10.098 | 8.564 | 6.235 | 4.591 | 4.932 | −12.393 | 0.0183719 | transmembrane emp24 protein transport domain containing 7 |
| MRPS33 | 4.734 | 5.789 | 5.272 | 1.648 | 1.648 | 1.648 | −12.329 | 0.0006284 | mitochondrial ribosomal protein S33 |
| SLC25A32 | 4.657 | 8.217 | 7.180 | 3.871 | 3.559 | 2.233 | −12.309 | 0.0132627 | solute carrier family 25, member 32 |
| WISP2 | 4.793 | 8.437 | 8.036 | 3.233 | 4.135 | 4.817 | −12.298 | 0.0229619 | WNT1 inducible signaling pathway protein 2 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| COX8A | 9.285 | 10.229 | 10.127 | 6.609 | 6.264 | 6.323 | −12.288 | 0.0008315 | cytochrome c oxidase subunit VIIA (ubiquitous) |
| ISCU | 6.845 | 7.814 | 8.173 | 4.165 | 4.247 | 4.199 | −12.249 | 0.0015269 | iron-sulfur cluster scaffold homolog (E. coli) |
| VEZT | 6.610 | 7.777 | 7.582 | 3.951 | 3.978 | 4.007 | −12.158 | 0.0014541 | vezatin, adherens junctions transmembrane protein |
| S100A8 | 2.648 | 6.239 | 7.006 | 2.648 | 2.648 | 2.648 | −12.049 | 0.0388288 | S100 calcium binding protein A8 |
| GEM | 8.856 | 10.606 | 10.092 | 5.267 | 6.230 | 7.827 | −12.036 | 0.0085272 | GTP binding protein overexpressed in skeletal muscle |
| RPSAP58 | 11.590 | 13.231 | 12.770 | 8.898 | 9.182 | 9.570 | −12.019 | 0.0033258 | ribosomal protein SA pseudogene 58 |
| LY96 | 6.001 | 4.235 | 3.718 | 0.648 | 0.648 | 0.648 | −12.017 | 0.0019802 | lymphocyte antigen 96 |
| SLC7A6OS | 0.648 | 4.795 | 4.235 | 0.648 | 0.648 | 0.648 | −12.017 | 0.0397362 | solute carrier family 7, member 6 opposite strand |
| RRAS2 | 5.904 | 8.600 | 7.859 | 4.273 | 4.378 | 4.049 | −12.013 | 0.0085986 | related RAS viral (r-ras) oncogene homolog 2 |
| PTGES3 | 8.652 | 11.824 | 11.781 | 7.942 | 7.497 | 8.251 | −11.902 | 0.0212281 | prostaglandin E synthase 3 (cytosolic) |
| SOD1 | 6.887 | 9.505 | 9.175 | 5.782 | 5.250 | 5.606 | −11.874 | 0.0123338 | superoxide dismutase 1, soluble |
| GNAS | 8.818 | 11.815 | 11.623 | 8.059 | 8.198 | 7.983 | −11.826 | 0.0223497 | GNAS complex locus |
| WBP5 | 5.550 | 7.951 | 8.387 | 4.262 | 4.602 | 4.389 | −11.810 | 0.0152364 | WW domain binding protein 5 |
| AMIGO2 | 6.418 | 7.391 | 7.989 | 3.830 | 5.783 | 1.648 | −11.803 | 0.0150319 | adhesion molecule with Ig-like domain 2 |
| EEF1A1 | 8.720 | 10.129 | 10.204 | 6.464 | 5.658 | 6.647 | −11.772 | 0.0032440 | eukaryotic translation elongation factor 1 alpha 1 |
| HNRNPUL1 | 7.595 | 9.714 | 9.222 | 5.668 | 5.052 | 5.718 | −11.747 | 0.0049563 | heterogeneous nuclear ribonucleoprotein U-like 1 |
| GBAS | 2.648 | 6.196 | 6.205 | 2.648 | 2.648 | 2.648 | −11.693 | 0.0438208 | glioblastoma amplified sequence |
| SGK1 | 7.602 | 10.239 | 9.861 | 5.784 | 6.350 | 6.315 | −11.682 | 0.0109854 | serum/glucocorticoid regulated kinase 1 |
| SLBP | 4.620 | 7.890 | 7.643 | 3.494 | 3.852 | 4.346 | −11.665 | 0.0224870 | stem-loop binding protein |
| GNAI3 | 6.704 | 8.598 | 8.589 | 5.056 | 4.865 | 4.623 | −11.643 | 0.0063941 | guanine nucleotide binding protein (G protein), alpha inhibiting activity polypeptide 3 |
| THBS4 | 10.886 | 8.717 | 7.042 | 5.137 | 5.250 | 5.176 | −11.642 | 0.0095040 | thrombospondin 4 |
| YEATS4 | 1.648 | 5.413 | 5.190 | 1.648 | 1.648 | 1.648 | −11.642 | 0.0423886 | YEATS domain containing 4 |
| RPLP2 | 13.366 | 14.996 | 14.847 | 11.198 | 11.371 | 11.320 | −11.526 | 0.0044967 | ribosomal protein, large, P2 |
| RNF130 | 5.683 | 8.099 | 6.073 | 3.023 | 1.648 | 3.294 | −11.425 | 0.0031671 | ring finger protein 130 |
| GULP1 | 3.456 | 6.963 | 7.763 | 3.456 | 3.456 | 3.456 | −11.369 | 0.0397785 | GULP, engulfment adaptor PTB domain containing 1 |
| ZBED3 | 6.911 | 4.154 | 5.246 | 3.351 | 2.353 | 0.648 | −11.356 | 0.0142236 | zinc finger, BED-type containing 3 |
| MRPL13 | 4.895 | 5.411 | 4.154 | 0.648 | 2.648 | 0.648 | −11.356 | 0.0381889 | mitochondrial ribosomal protein L13 |
| PI16 | 8.889 | 9.884 | 7.940 | 3.808 | 5.384 | 6.499 | −11.350 | 0.0071061 | peptidase inhibitor 16 |
| OTUD1 | 6.466 | 8.662 | 7.356 | 3.988 | 2.970 | 4.533 | −11.283 | 0.0045286 | OTU domain containing 1 |
| LGALS3BP | 7.493 | 8.314 | 6.636 | 3.997 | 4.383 | 3.865 | −11.279 | 0.0026638 | lectin, galactoside-binding, soluble, 3 binding protein |
| POSTN | 7.307 | 8.035 | 7.141 | 3.818 | 3.818 | 3.818 | −11.229 | 0.0004884 | periostin, osteoblast specific factor |
| MMGT1 | 6.388 | 8.099 | 7.436 | 4.625 | 3.648 | 3.648 | −11.111 | 0.0040399 | membrane magnesium transporter 1 |
| LRP12 | 4.895 | 7.131 | 6.122 | 2.648 | 2.648 | 3.303 | −11.107 | 0.0065348 | low density lipoprotein receptor-related protein 12 |
| CHMP2B | 5.923 | 8.099 | 8.028 | 3.648 | 3.456 | 4.631 | −11.069 | 0.0066880 | chromatin modifying protein 2B |
| PHLDA3 | 4.895 | 6.748 | 6.116 | 2.648 | 2.648 | 0.648 | −11.060 | 0.0137439 | pleckstrin homology-like domain, family A, member 3 |
| C2orf40 | 9.640 | 8.820 | 6.264 | 3.981 | 5.384 | 3.737 | −11.000 | 0.0137688 | chromosome 2 open reading frame 40 |
| CAPN6 | 8.455 | 6.163 | 6.427 | 2.970 | 2.970 | 3.859 | −10.982 | 0.0040038 | calpain 6 |
| LOXL3 | 6.232 | 5.228 | 5.102 | 3.023 | 1.648 | 1.648 | −10.960 | 0.0034049 | lysyl oxidase-like 3 |
| FEN1 | 4.620 | 6.101 | 6.151 | 2.648 | 2.648 | 2.648 | −10.947 | 0.0051650 | flap structure-specific endonuclease 1 |
| NAMPT | 8.550 | 10.702 | 10.016 | 7.255 | 6.481 | 6.222 | −10.906 | 0.0078471 | nicotinamide phosphoribosyltransferase |
| TMEM45A | 2.233 | 6.054 | 5.679 | 2.233 | 2.233 | 2.233 | −10.895 | 0.0428912 | transmembrane protein 45A |
| GYPC | 9.157 | 9.098 | 8.221 | 6.736 | 5.282 | 4.778 | −10.873 | 0.0057577 | glycophorin C (Gerbich blood group) |
| SUB1 | 6.898 | 8.231 | 8.010 | 5.417 | 4.504 | 3.456 | −10.870 | 0.0061903 | SUB1 homolog (S. cerevisiae) |
| MTA1P6 | 11.596 | 13.166 | 13.325 | 9.651 | 9.814 | 9.727 | −10.851 | 0.0062402 | No description |
| PHKG2 | 1.648 | 5.568 | 5.082 | 1.648 | 1.648 | 1.648 | −10.806 | 0.0424205 | phosphorylase kinase, gamma 2 (testis) |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| PGCP | 6.227 | 7.185 | 4.878 | 2.648 | 2.648 | 3.752 | −10.795 | 0.0092773 | No description |
| MRC2 | 10.923 | 10.598 | 10.016 | 6.301 | 7.171 | 8.415 | −10.757 | 0.0059934 | mannose receptor, C type 2 |
| GNG5 | 5.826 | 8.593 | 8.834 | 5.408 | 4.781 | 4.458 | −10.749 | 0.0186340 | guanine nucleotide binding protein (G protein), gamma 5 |
| STOML2 | 8.248 | 9.444 | 9.433 | 6.532 | 5.405 | 4.830 | −10.687 | 0.0038818 | stomatin (EPB72)-like 2 |
| EIF6 | 7.692 | 9.635 | 9.601 | 6.224 | 6.154 | 5.009 | −10.636 | 0.0079456 | eukaryotic translation initiation factor 6 |
| RPS27 | 13.292 | 14.938 | 14.687 | 10.606 | 10.822 | 11.528 | −10.634 | 0.0039629 | ribosomal protein S27 |
| CXCL14 | 8.889 | 10.897 | 7.529 | 4.124 | 6.103 | 5.980 | −10.597 | 0.0105397 | chemokine (C-X-C motif) ligand 14 |
| DYNLRB1 | 7.533 | 8.553 | 8.121 | 5.735 | 4.717 | 3.516 | −10.589 | 0.0050700 | dynein, light chain, roadblock-type 1 |
| LOC154761 | 6.444 | 4.845 | 5.718 | 2.233 | 3.043 | 2.233 | −10.565 | 0.0042880 | No description |
| KEAP1 | 4.214 | 7.786 | 8.349 | 4.385 | 4.447 | 3.865 | −10.559 | 0.0416426 | kelch-like ECH-associated protein 1 |
| PON2 | 4.142 | 6.454 | 5.945 | 2.233 | 2.233 | 3.054 | −10.555 | 0.0100912 | paraoxonase 2 |
| CHMP2A | 6.368 | 8.541 | 8.819 | 5.256 | 3.958 | 5.147 | −10.512 | 0.0112835 | chromatin modifying protein 2A |
| HOXD8 | 5.042 | 6.042 | 5.183 | 1.648 | 1.648 | 3.294 | −10.511 | 0.0053050 | homeobox D8 |
| CPZ | 8.970 | 7.638 | 6.306 | 4.248 | 4.383 | 3.456 | −10.482 | 0.0053827 | carboxypeptidase Z |
| LOC388796 | 5.552 | 9.155 | 8.702 | 4.117 | 5.766 | 4.579 | −10.476 | 0.0238166 | No description |
| DUSP6 | 7.928 | 9.233 | 9.378 | 5.961 | 5.846 | 5.597 | −10.461 | 0.0041875 | dual specificity phosphatase 6 |
| SH3BGRL | 6.798 | 7.959 | 6.603 | 3.218 | 3.852 | 3.897 | −10.450 | 0.0020253 | SH3 domain binding glutamic acid-rich protein like |
| LGALS1 | 11.317 | 11.360 | 10.355 | 7.977 | 7.435 | 7.902 | −10.435 | 0.0018541 | lectin, galactoside-binding, soluble, 1 |
| HEPH | 7.097 | 5.617 | 5.317 | 2.233 | 2.233 | 2.233 | −10.435 | 0.0015900 | hephaestin |
| GLUD2 | 0.648 | 4.757 | 4.021 | 0.648 | 0.648 | 0.648 | −10.361 | 0.0421064 | glutamate dehydrogenase 2 |
| C11orf1 | 0.648 | 4.021 | 4.389 | 0.648 | 0.648 | 0.648 | −10.361 | 0.0440371 | chromosome 11 open reading frame 1 |
| CSRNP2 | 6.667 | 8.380 | 7.170 | 4.165 | 3.294 | 4.199 | −10.357 | 0.0030208 | cysteine-serine-rich nuclear protein 2 |
| HNRNPAB | 8.494 | 11.314 | 10.605 | 6.996 | 7.350 | 7.239 | −10.310 | 0.0132378 | heterogeneous nuclear ribonucleoprotein A/B |
| IL28RA | 4.423 | 5.008 | 5.591 | 1.648 | 1.648 | 1.648 | −10.264 | 0.0011747 | interleukin 28 receptor, alpha (interferon, lambda receptor) |
| S100A4 | 4.264 | 8.960 | 6.663 | 3.494 | 3.294 | 3.303 | −10.262 | 0.0211380 | S100 calcium binding protein A4 |
| LOXL2 | 8.577 | 8.370 | 8.803 | 6.860 | 5.012 | 5.186 | −10.251 | 0.0079276 | lysyl oxidase-like 2 |
| ISG15 | 8.331 | 6.016 | 7.042 | 4.151 | 3.686 | 3.508 | −10.237 | 0.0054277 | ISG15 ubiquitin-like modifier |
| DNAJB9 | 6.705 | 9.387 | 8.699 | 5.450 | 4.383 | 5.347 | −10.211 | 0.0103012 | DnaJ (Hsp40) homolog, subfamily B, member 9 |
| ATXN10 | 6.145 | 7.652 | 7.661 | 4.315 | 3.852 | 3.303 | −10.168 | 0.0038908 | ataxin 10 |
| DPM1 | 2.233 | 5.659 | 5.578 | 2.233 | 2.233 | 2.233 | −10.158 | 0.0467227 | dolichyl-phosphate mannosyltransferase polypeptide 1, catalytic subunit |
| SF3B14 | 6.829 | 8.560 | 8.726 | 4.624 | 5.304 | 5.220 | −10.130 | 0.0077411 | No description |
| SCARA5 | 7.510 | 8.184 | 7.448 | 4.659 | 4.108 | 4.580 | −10.124 | 0.0010950 | scavenger receptor class A, member 5 (putative) |
| KCNH6 | 7.008 | 9.021 | 9.843 | 5.853 | 4.432 | 5.686 | −10.090 | 0.0107685 | potassium voltage-gated channel, subfamily H (eag-related), member 6 |
| CCDC53 | 5.598 | 6.012 | 4.979 | 3.023 | 1.648 | 1.648 | −10.062 | 0.0030388 | coiled-coil domain containing 53 |
| PVRL2 | 9.881 | 8.883 | 9.698 | 6.363 | 6.552 | 5.934 | −10.048 | 0.0018631 | poliovirus receptor-related 2 (herpesvirus entry mediator B) |
| CDK2AP1 | 9.528 | 10.140 | 10.195 | 7.417 | 6.812 | 5.726 | −10.039 | 0.0035123 | cyclin-dependent kinase 2 associated protein 1 |
| DBI | 6.418 | 8.282 | 8.295 | 4.721 | 4.529 | 4.975 | −9.987 | 0.0082721 | diazepam binding inhibitor (GABA receptor modulator, acyl-CoA binding protein) |
| CFDP1 | 4.936 | 6.361 | 7.082 | 3.670 | 3.043 | 2.233 | −9.971 | 0.0083061 | craniofacial development protein 1 |
| COTL1 | 6.406 | 10.131 | 9.864 | 5.555 | 6.818 | 6.045 | −9.941 | 0.0339844 | coactosin-like 1 (Dictyostelium) |
| MFN2 | 5.345 | 7.585 | 7.319 | 4.132 | 4.007 | 3.648 | −9.930 | 0.0116801 | mitofusin 2 |
| LOC100216001 | 0.648 | 4.587 | 3.959 | 0.648 | 0.648 | 0.648 | −9.921 | 0.0434520 | No description |
| PPP1R2P3 | 0.648 | 3.959 | 4.428 | 0.648 | 0.648 | 0.648 | −9.921 | 0.0444794 | protein phosphatase 1, regulatory (inhibitor) subunit 2 pseudogene 3 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| HES1 | 7.851 | 8.462 | 8.874 | 6.474 | 4.515 | 5.155 | −9.891 | 0.0075809 | hairy and enhancer of split 1, (*Drosophila*) |
| TMEM173 | 5.539 | 6.009 | 3.381 | 2.233 | 2.233 | 2.233 | −9.890 | 0.0153958 | transmembrane protein 173 |
| FGFR1OP2 | 6.135 | 6.798 | 7.153 | 2.970 | 2.970 | 3.859 | −9.805 | 0.0016350 | FGFR1 oncogene partner 2 |
| LOC550643 | 4.008 | 6.617 | 6.031 | 3.326 | 1.648 | 1.648 | −9.790 | 0.0105674 | No description |
| NDUFAB1 | 4.423 | 7.381 | 6.535 | 3.707 | 3.247 | 1.648 | −9.768 | 0.0141938 | NADH dehydrogenase (ubiquinone) 1, alpha/beta subcomplex, 1,8 kDa |
| YIF1A | 8.300 | 7.727 | 8.150 | 5.966 | 4.863 | 3.516 | −9.760 | 0.0064988 | Yip1 interacting factor homolog A (*S. cerevisiae*) |
| RPF2 | 4.312 | 8.055 | 7.893 | 4.610 | 4.722 | 3.905 | −9.734 | 0.0494534 | ribosome production factor 2 homolog (*S. cerevisiae*) |
| RAB1A | 6.898 | 10.273 | 9.662 | 6.380 | 6.353 | 6.418 | −9.733 | 0.0277536 | RAB1A, member RAS oncogene family |
| UAP1 | 5.997 | 10.459 | 9.086 | 5.773 | 5.804 | 6.616 | −9.731 | 0.0493958 | UDP-N-acetylglucosamine pyrophosphorylase 1 |
| PTPLAD2 | 4.423 | 5.615 | 4.930 | 1.648 | 1.648 | 1.648 | −9.724 | 0.0013009 | protein tyrosine phosphatase-like A domain containing 2 |
| SH3BGR | 3.422 | 5.042 | 4.930 | 1.648 | 1.648 | 1.648 | −9.724 | 0.0071463 | SH3 domain binding glutamic acid-rich protein |
| TACR1 | 3.422 | 4.930 | 5.264 | 1.648 | 1.648 | 1.648 | −9.724 | 0.0073057 | tachykinin receptor 1 |
| CCDC90B | 5.042 | 5.420 | 4.930 | 4.400 | 0.648 | 0.648 | −9.724 | 0.0237189 | coiled-coil domain containing 90B |
| MRPL21 | 3.860 | 5.996 | 5.444 | 2.714 | 1.648 | 1.648 | −9.705 | 0.0060024 | mitochondrial ribosomal protein L21 |
| CCL28 | 1.648 | 4.927 | 5.808 | 1.648 | 1.648 | 1.648 | −9.705 | 0.0427955 | chemokine (C-C motif) ligand 28 |
| TMEM69 | 5.452 | 4.927 | 5.038 | 3.830 | 1.648 | 1.648 | −9.702 | 0.0132198 | transmembrane protein 69 |
| PPP1R14A | 6.983 | 4.925 | 3.294 | 1.648 | 1.648 | 1.648 | −9.692 | 0.0115692 | protein phosphatase 1, regulatory (inhibitor) subunit 14A |
| TP53 | 6.820 | 7.740 | 7.575 | 4.302 | 4.474 | 2.970 | −9.670 | 0.0028336 | tumor protein p53 |
| PPT2 | 5.503 | 6.182 | 4.859 | 2.233 | 2.233 | 2.233 | −9.646 | 0.0018139 | palmitoyl-protein thioesterase 2 |
| PPP1CC | 8.533 | 9.689 | 8.895 | 5.269 | 6.240 | 5.698 | −9.605 | 0.0022728 | protein phosphatase 1, catalytic subunit, gamma isozyme |
| SSBP1 | 3.422 | 6.012 | 5.413 | 1.648 | 1.648 | 2.752 | −9.579 | 0.0137418 | single-stranded DNA binding protein 1 |
| IMPDH2 | 7.925 | 9.132 | 9.300 | 5.686 | 5.923 | 5.877 | −9.546 | 0.0042971 | IMP (inosine 5′-monophosphate) dehydrogenase 2 |
| HNRNPA0 | 10.474 | 11.491 | 10.726 | 7.575 | 7.221 | 7.530 | −9.529 | 0.0009050 | heterogeneous nuclear ribonucleoprotein A0 |
| PLRG1 | 4.744 | 7.104 | 6.621 | 3.218 | 3.852 | 3.303 | −9.528 | 0.0143865 | pleiotropic regulator 1 (PRL1 homolog, *Arabidopsis*) |
| CAMK2N1 | 7.241 | 8.807 | 7.946 | 5.445 | 3.739 | 5.557 | −9.516 | 0.0087310 | calcium/calmodulin-dependent protein kinase II inhibitor 1 |
| C19orf56 | 8.040 | 9.559 | 9.060 | 6.295 | 5.561 | 5.811 | −9.506 | 0.0049113 | chromosome 19 open reading frame 56 |
| ACAT1 | 5.896 | 6.979 | 6.285 | 3.494 | 3.294 | 2.648 | −9.501 | 0.0021626 | acetyl-CoA acetyltransferase 1 |
| WDR33 | 7.072 | 8.377 | 8.668 | 5.045 | 5.129 | 5.234 | −9.496 | 0.0056468 | WD repeat domain 33 |
| PGD | 7.136 | 9.768 | 10.402 | 7.156 | 6.258 | 6.508 | −9.492 | 0.0310825 | phosphogluconate dehydrogenase |
| PLSCR4 | 7.096 | 7.808 | 7.851 | 4.392 | 4.355 | 4.608 | −9.468 | 0.0012017 | phospholipid scramblase4 |
| BAX | 4.008 | 6.499 | 6.742 | 1.648 | 3.499 | 2.752 | −9.466 | 0.0149279 | BCL2-associated X protein |
| SLC26A3 | 0.648 | 3.888 | 4.575 | 0.648 | 0.648 | 0.648 | −9.446 | 0.0443664 | solute carrier family 26, member 3 |
| DUSP16 | 4.620 | 5.886 | 5.896 | 2.648 | 2.648 | 2.648 | −9.434 | 0.0050971 | dual specificity phosphatase 16 |
| VPS37A | 4.214 | 7.614 | 6.691 | 3.456 | 3.456 | 3.456 | −9.420 | 0.0228308 | vacuolar protein sorting 37 homolog A (*S. cerevisiae*) |
| CD164 | 7.794 | 8.663 | 8.789 | 5.555 | 5.063 | 5.242 | −9.408 | 0.0020433 | CD164 molecule, sialomucin |
| ARF6 | 10.007 | 11.794 | 11.439 | 7.435 | 8.206 | 8.436 | −9.403 | 0.0067303 | ADP-ribosylation factor 6 |
| ASB13 | 0.648 | 4.043 | 3.881 | 0.648 | 0.648 | 0.648 | −9.403 | 0.0481314 | ankyrin repeat and SOCS box-containing 13 |
| FAM96A | 4.008 | 4.874 | 5.314 | 1.648 | 1.648 | 1.648 | −9.358 | 0.0027449 | family with sequence similarity 96, member A |
| CES8 | 1.648 | 4.874 | 5.466 | 0.648 | 0.648 | 0.648 | −9.358 | 0.0451269 | No description |
| C14orf129 | 4.314 | 4.347 | 3.873 | 0.648 | 0.648 | 2.370 | −9.351 | 0.0071373 | chromosome 14 open reading frame 129 |
| DPCD | 4.314 | 4.587 | 3.873 | 0.648 | 0.648 | 3.043 | −9.351 | 0.0146125 | deleted in primary ciliary dyskinesia homolog (mouse) |
| ANKRD30A | 0.648 | 3.871 | 4.235 | 0.648 | 0.648 | 0.648 | −9.332 | 0.0466492 | ankyrin repeat domain 30A |
| FGB | 0.648 | 3.871 | 4.021 | 0.648 | 0.648 | 0.648 | −9.332 | 0.0484340 | fibrinogen beta chain |
| KLK1 | 7.421 | 7.530 | 8.103 | 3.351 | 4.311 | 7.329 | −9.313 | 0.0311220 | kallikrein 1 |
| KDM5B | 5.235 | 6.187 | 6.278 | 2.970 | 2.970 | 2.970 | −9.299 | 0.0030118 | lysine (K)-specific demethylase 5B |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| PSMC4 | 6.753 | 9.903 | 9.783 | 6.568 | 6.636 | 5.678 | −9.285 | 0.0308073 | proteasome (prosome, macropain) 26S subunit, ATPase, 4 |
| C2orf76 | 3.860 | 3.980 | 3.511 | 0.648 | 0.648 | 0.648 | −9.262 | 0.0006374 | chromosome 2 open reading frame 76 |
| ZNF773 | 3.860 | 4.564 | 4.575 | 2.202 | 0.648 | 0.648 | −9.262 | 0.0047463 | zinc finger protein 773 |
| LOC139201 | 3.860 | 4.665 | 5.158 | 0.648 | 2.353 | 0.648 | −9.262 | 0.0052239 | No description |
| NDUFAF1 | 3.860 | 5.119 | 4.314 | 0.648 | 2.353 | 0.648 | −9.262 | 0.0061543 | NADH dehydrogenase (ubiquinone) 1 alpha subcomplex, assembly factor 1 |
| CCL26 | 3.860 | 4.389 | 4.428 | 0.648 | 0.648 | 2.370 | −9.262 | 0.0068163 | chemokine (C-C motif) ligand 26 |
| C12orf53 | 0.648 | 3.860 | 4.262 | 0.648 | 0.648 | 0.648 | −9.262 | 0.0465432 | chromosome 12 open reading frame 53 |
| CES1 | 0.648 | 3.860 | 4.021 | 0.648 | 0.648 | 0.648 | −9.262 | 0.0485369 | carboxylesterase 1 |
| EIF1 | 9.524 | 12.338 | 11.939 | 8.050 | 8.316 | 9.134 | −9.219 | 0.0186991 | eukaryotic translation initiation factor 1 |
| REEP5 | 7.695 | 10.028 | 9.629 | 5.934 | 6.426 | 6.480 | −9.207 | 0.0120031 | receptor accessory protein 5 |
| ITPRIPL2 | 8.774 | 10.452 | 9.681 | 6.984 | 6.479 | 6.465 | −9.199 | 0.0052419 | inositol 1,4,5-triphosphate receptor interacting protein-like 2 |
| GJA1 | 12.216 | 12.339 | 12.665 | 8.218 | 9.139 | 9.774 | −9.192 | 0.0023900 | gap junction protein, alpha 1,43 kDa |
| AP2A1 | 7.325 | 8.475 | 8.082 | 5.275 | 4.482 | 4.233 | −9.186 | 0.0026049 | adaptor-related protein complex 2, alpha 1 subunit |
| AZIN1 | 7.519 | 9.445 | 9.185 | 6.107 | 5.988 | 5.756 | −9.171 | 0.0098575 | antizyme inhibitor 1 |
| IL6 | 15.466 | 15.087 | 13.483 | 11.967 | 11.460 | 11.893 | −9.149 | 0.0083151 | interleukin 6 (interferon, beta 2) |
| APH1A | 8.257 | 9.469 | 9.787 | 6.422 | 6.277 | 5.698 | −9.137 | 0.0049023 | anterior pharynx defective 1 homolog A (C. elegans) |
| SERPINA3 | 6.545 | 10.678 | 11.209 | 5.002 | 8.025 | 5.348 | −9.094 | 0.0314208 | serpin peptidase inhibitor, clade A (alpha-1 antiproteinase, antitrypsin), members |
| DYRK3 | 5.109 | 7.277 | 5.412 | 2.233 | 2.233 | 2.233 | −9.054 | 0.0031491 | dual-specificity tyrosine-(Y)-phosphorylation regulated kinase 3 |
| PRMT5 | 5.587 | 8.698 | 8.906 | 5.729 | 4.869 | 4.467 | −9.048 | 0.0270776 | protein arginine methyltransferase 5 |
| MXRA5 | 9.005 | 7.512 | 7.405 | 4.684 | 4.233 | 5.431 | −9.012 | 0.0054548 | matrix-remodelling associated 5 |
| CLEC11A | 6.418 | 6.194 | 4.751 | 1.648 | 3.247 | 1.648 | −9.009 | 0.0043560 | C-type lectin domain family 11, member A |
| TMEM9 | 5.696 | 6.140 | 6.252 | 2.970 | 2.970 | 2.970 | −9.000 | 0.0008544 | transmembrane protein 9 |
| C14orf2 | 4.422 | 7.667 | 7.774 | 4.604 | 4.378 | 3.303 | −8.997 | 0.0353924 | chromosome 14 open reading frame 2 |
| DULLARD | 7.392 | 8.384 | 7.927 | 5.216 | 4.271 | 4.553 | −8.987 | 0.0021896 | No description |
| ITPKB | 7.190 | 7.979 | 7.548 | 4.593 | 4.108 | 4.382 | −8.981 | 0.0010679 | inositol 1,4,5-trisphosphate 3-kinase B |
| GPNMB | 10.423 | 10.299 | 9.251 | 6.007 | 7.133 | 7.429 | −8.976 | 0.0050430 | glycoprotein (transmembrane) nmb |
| TGIF2 | 10.252 | 9.310 | 8.443 | 5.945 | 5.742 | 7.087 | −8.969 | 0.0074104 | TGFB-induced factor homeobox 2 |
| GNB2L1 | 11.295 | 12.631 | 12.580 | 9.332 | 9.324 | 9.467 | −8.964 | 0.0056288 | guanine nucleotide binding protein (G protein), beta polypeptide 2-like 1 |
| NR2F2 | 10.927 | 9.894 | 9.214 | 8.576 | 5.277 | 6.730 | −8.962 | 0.0155040 | nuclear receptor subfamily 2, group F, member 2 |
| PRPS2 | 4.264 | 6.822 | 5.898 | 2.648 | 3.659 | 2.648 | −8.958 | 0.0167997 | phosphoribosyl pyrophosphate synthetase 2 |
| C7orf70 | 4.314 | 3.810 | 4.901 | 2.714 | 0.648 | 0.648 | −8.950 | 0.0102471 | chromosome 7 open reading frame 70 |
| PAQR4 | 3.860 | 4.934 | 4.593 | 3.351 | 3.247 | 2.970 | −8.950 | 0.0244308 | progestin and adipoQ receptor family member IV |
| MRPL50 | 5.696 | 3.810 | 3.810 | 2.970 | 2.970 | 2.970 | −8.950 | 0.0436163 | mitochondrial ribosomal protein L50 |
| S100P | 0.648 | 3.810 | 4.665 | 0.648 | 0.648 | 0.648 | −8.950 | 0.0449023 | S100 calcium binding protein P |
| DKK3 | 5.923 | 9.121 | 6.810 | 3.648 | 4.294 | 3.648 | −8.949 | 0.0098936 | dickkopf homolog 3 (Xenopus laevis) |
| MGMT | 4.314 | 5.514 | 5.870 | 3.351 | 2.353 | 0.648 | −8.947 | 0.0122929 | O-6-methylguanine-DNA methyltransferase |
| COX5B | 5.821 | 7.894 | 6.209 | 4.052 | 3.043 | 3.054 | −8.910 | 0.0064738 | cytochrome c oxidase subunit Vb |
| DARC | 9.735 | 6.293 | 6.125 | 2.970 | 3.508 | 4.933 | −8.906 | 0.0148558 | Duffy blood group, chemokine receptor |
| OLFML3 | 7.408 | 7.559 | 5.825 | 2.970 | 2.970 | 4.405 | −8.898 | 0.0049744 | olfactomedin-like 3 |
| LOC649330 | 8.143 | 8.607 | 8.261 | 5.133 | 4.990 | 5.343 | −8.890 | 0.0006915 | No description |
| HSPA1B | 9.079 | 11.668 | 11.684 | 5.929 | 7.260 | 9.522 | −8.875 | 0.0218464 | heat shock 70 kDa protein 1B |
| FAM83A | 1.648 | 4.797 | 5.311 | 1.648 | 1.648 | 1.648 | −8.868 | 0.0469501 | family with sequence similarity 83, member A |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| TMEM185A | 7.165 | 7.105 | 6.806 | 4.879 | 3.958 | 3.574 | −8.855 | 0.0042236 | transmembrane protein 185A |
| RPL11 | 12.263 | 13.261 | 13.545 | 9.940 | 10.056 | 10.399 | −8.853 | 0.0043421 | ribosomal protein L11 |
| TMEM176B | 9.106 | 8.986 | 7.960 | 5.462 | 5.776 | 5.963 | −8.835 | 0.0036537 | transmembrane protein 176B |
| STC1 | 12.598 | 9.876 | 9.593 | 7.502 | 6.895 | 6.450 | −8.834 | 0.0072787 | stanniocalcin 1 |
| COL6A1 | 10.999 | 11.594 | 10.443 | 8.181 | 7.604 | 7.857 | −8.826 | 0.0023088 | collagen, type VI, alpha 1 |
| RNF166 | 5.524 | 5.288 | 4.786 | 1.648 | 1.648 | 3.746 | −8.799 | 0.0114915 | ring finger protein 166 |
| DCX | 9.077 | 6.428 | 7.107 | 3.970 | 3.970 | 4.972 | −8.795 | 0.0095823 | doublecortin |
| TMEM189 | 5.982 | 8.700 | 7.540 | 5.656 | 4.405 | 2.648 | −8.787 | 0.0176995 | transmembrane protein 189 |
| ZNF217 | 6.135 | 8.657 | 8.787 | 5.522 | 4.707 | 5.606 | −8.787 | 0.0224433 | zinc finger protein 217 |
| EIF3K | 8.752 | 9.811 | 9.759 | 6.624 | 6.561 | 6.657 | −8.784 | 0.0037619 | eukaryotic translation initiation factor 3, subunit K |
| C6orf62 | 8.151 | 9.814 | 9.374 | 6.681 | 5.768 | 6.213 | −8.775 | 0.0071886 | chromosome 6 open reading frame 62 |
| PABPC1 | 9.000 | 11.528 | 11.200 | 7.839 | 8.067 | 8.203 | −8.773 | 0.0192371 | poly(A) binding protein, cytoplasmic 1 |
| C1orf77 | 4.264 | 6.728 | 6.825 | 3.494 | 2.648 | 3.694 | −8.757 | 0.0197750 | chromosome 1 open reading frame 77 |
| UQCRQ | 5.008 | 8.261 | 7.906 | 5.132 | 4.428 | 3.897 | −8.747 | 0.0296433 | ubiquinol-cytochrome c reductase, complex III subunit VII, 9.5 kDa |
| TGFBI | 9.491 | 9.818 | 8.698 | 6.200 | 5.569 | 6.753 | −8.746 | 0.0035393 | transforming growth factor, beta-induced, 68 kDa |
| PFDN5 | 7.618 | 10.611 | 9.976 | 6.704 | 6.850 | 7.184 | −8.735 | 0.0252142 | prefoldin subunit 5 |
| AP1AR | 6.280 | 7.535 | 7.684 | 3.797 | 3.899 | 4.557 | −8.734 | 0.0044101 | adaptor-related protein complex 1 associated regulatory protein |
| ARL4D | 6.773 | 7.019 | 6.223 | 3.718 | 2.648 | 3.897 | −8.701 | 0.0027539 | ADP-ribosylation factor-like 4D |
| NIPSNAP1 | 6.667 | 5.487 | 5.345 | 3.535 | 3.467 | 2.233 | −8.644 | 0.0095414 | nipsnap homolog 1 (*C. elegans*) |
| SRP9 | 5.499 | 8.783 | 8.277 | 5.673 | 4.926 | 4.932 | −8.636 | 0.0370333 | signal recognition particle 9 kDa |
| PMPCA | 6.070 | 7.840 | 7.887 | 4.664 | 4.777 | 3.508 | −8.634 | 0.0101723 | peptidase (mitochondrial processing) alpha |
| EGLN1 | 6.788 | 9.421 | 9.778 | 6.317 | 5.233 | 6.640 | −8.596 | 0.0263830 | egl nine homolog 1 (*C. elegans*) |
| PPP3R1 | 5.532 | 8.025 | 7.793 | 3.997 | 4.610 | 4.927 | −8.567 | 0.0190760 | protein phosphatase 3, regulatory subunit B, alpha |
| TRIM52 | 8.187 | 9.947 | 10.141 | 6.853 | 6.850 | 6.760 | −8.559 | 0.0124281 | tripartite motif-containing 52 |
| BACE2 | 5.282 | 6.567 | 6.924 | 2.970 | 3.827 | 2.970 | −8.553 | 0.0062492 | beta-site APP-cleaving enzyme 2 |
| POMC | 0.648 | 3.745 | 4.389 | 0.648 | 2.970 | 0.648 | −8.552 | 0.0471227 | proopiomelanocortin |
| UBE2Q2 | 2.970 | 6.943 | 6.065 | 2.970 | 2.970 | 2.970 | −8.544 | 0.0456745 | ubiquitin-conjugating enzyme E2Q family member 2 |
| HEBP1 | 4.895 | 6.066 | 5.742 | 2.648 | 2.648 | 2.648 | −8.534 | 0.0032530 | heme binding protein 1 |
| C7orf50 | 5.821 | 5.323 | 5.645 | 3.278 | 2.233 | 2.233 | −8.516 | 0.0030978 | chromosome 7 open reading frame 50 |
| RBPJ | 5.545 | 7.584 | 6.059 | 3.442 | 2.970 | 2.970 | −8.508 | 0.0050069 | recombination signal binding protein for immunoglobulin kappa J region |
| PHLPP1 | 6.767 | 7.912 | 7.771 | 4.682 | 4.785 | 4.141 | −8.507 | 0.0039269 | PH domain and leucine rich repeat protein phosphatase 1 |
| CTSK | 5.322 | 6.799 | 5.499 | 2.951 | 3.043 | 2.233 | −8.506 | 0.0044690 | cathepsin K |
| RFCS | 3.422 | 4.863 | 4.737 | 1.648 | 1.648 | 1.648 | −8.506 | 0.0072066 | replication factor C (activator 1) 3, 38 kDa |
| XPNPEP2 | 4.734 | 4.871 | 4.667 | 1.648 | 1.648 | 1.648 | −8.491 | 0.0003983 | X-prolyl aminopeptidase (aminopeptidase P) 2, membrane-bound |
| THBS1 | 10.432 | 11.878 | 12.075 | 6.879 | 9.093 | 8.797 | −8.462 | 0.0101542 | thrombospondin 1 |
| C17orf106 | 4.817 | 5.314 | 5.462 | 2.233 | 2.233 | 2.233 | −8.460 | 0.0012378 | chromosome 17 open reading frame 106 |
| TRAPPC3 | 6.470 | 7.177 | 7.695 | 4.797 | 4.097 | 2.648 | −8.457 | 0.0065439 | trafficking protein particle complex 3 |
| MARCKS | 12.283 | 11.804 | 11.368 | 9.690 | 7.835 | 8.725 | −8.450 | 0.0060614 | myristoylated alanine-rich protein kinase C substrate |
| DCAKD | 5.908 | 5.829 | 4.939 | 1.648 | 3.247 | 2.752 | −8.439 | 0.0059844 | dephospho-CoA kinase domain containing |
| RPS6KA1 | 3.947 | 6.047 | 6.108 | 2.970 | 2.970 | 2.970 | −8.438 | 0.0194957 | ribosomal protein S6 kinase, 90 kDa, polypeptide 1 |
| ZDHHC1 | 6.103 | 5.725 | 6.131 | 3.218 | 2.648 | 2.648 | −8.436 | 0.0010090 | zinc finger, DHHC-type containing 1 |
| TACSTD2 | 8.039 | 11.355 | 11.742 | 6.398 | 8.665 | 5.403 | −8.434 | 0.0199955 | tumor-associated calcium signal transducer 2 |

TABLE 4-continued

Differentially Expressed Genes in CD44+ Breast Epithelial Cells

| Gene Symbol | Nulliparous (NP) Samples | | | | Parous (P) Samples | | | | Pseudo fold change | P value | Gene description |
|---|---|---|---|---|---|---|---|---|---|---|---|
| | CD44+ N48 | CD44+ N58 | CD44+ N43 | | CD44+ N37 | CD44+ N39 | CD44+ N40 | | | | |
| NCBP2 | 6.283 | 8.588 | 7.745 | | 4.670 | 4.707 | 3.911 | | −8.426 | 0.0080433 | nuclear cap binding protein subunit 2, 20 kDa |
| NPC2 | 9.497 | 9.896 | 9.466 | | 6.181 | 6.823 | 6.820 | | −8.418 | 0.0016170 | Niemann-Pick disease, type C2 |
| ORAI3 | 6.395 | 6.365 | 5.718 | | 3.838 | 3.294 | 2.648 | | −8.397 | 0.0042326 | ORAI calcium release-activated calcium modulator 3 |
| RAB8B | 6.936 | 8.740 | 8.817 | | 5.747 | 4.580 | 5.514 | | −8.396 | 0.0106312 | RAB8B, member RAS oncogene family |
| TPM1 | 6.585 | 8.369 | 7.849 | | 4.508 | 6.400 | 3.516 | | −8.394 | 0.0200801 | tropomyosin 1 (alpha) |
| LOC93622 | 7.181 | 8.088 | 7.629 | | 4.647 | 4.015 | 5.019 | | −8.392 | 0.0029577 | No description |
| PLP1 | 6.042 | 4.963 | 5.717 | | 2.648 | 2.648 | 2.648 | | −8.389 | 0.0027809 | proteolipid protein 1 |
| SNRPD2 | 7.914 | 9.927 | 9.735 | | 6.860 | 6.204 | 5.926 | | −8.383 | 0.0106548 | small nuclear ribonucleoprotein D2 polypeptide 16.5 kDa |
| RPL31 | 10.628 | 12.515 | 12.683 | | 8.733 | 9.510 | 9.451 | | −8.366 | 0.0129993 | ribosomal protein L31 |
| TIA1 | 6.013 | 8.114 | 8.032 | | 5.051 | 4.879 | 4.895 | | −8.356 | 0.0175567 | TIA1 cytotoxic granule-associated RNA binding protein-like 1 |
| PPME1 | 6.898 | 7.714 | 8.479 | | 5.287 | 4.581 | 4.658 | | −8.319 | 0.0062991 | protein phosphatase methylesterase 1 |
| ARL5B | 7.204 | 6.693 | 6.512 | | 3.456 | 3.456 | 4.646 | | −8.317 | 0.0044600 | ADP-ribosylation factor-like 5B |
| CDH1 | 8.815 | 9.937 | 10.596 | | 6.245 | 8.422 | 5.762 | | −8.302 | 0.0156648 | cadherin 1, type 1, E-cadherin (epithelial) |
| EIF2S3 | 8.609 | 9.835 | 9.730 | | 6.786 | 6.618 | 6.304 | | −8.281 | 0.0049653 | eukaryotic translation initiation factor 2, subunit 3 gamma, 52 kDa |
| C13orf15 | 5.322 | 8.937 | 6.103 | | 3.278 | 3.043 | 3.054 | | −8.276 | 0.0096184 | chromosome 13 open reading frame 15 |
| GALT | 5.400 | 5.421 | 4.043 | | 2.202 | 2.353 | 2.370 | | −8.264 | 0.0076621 | galactose-1 -phosphate uridylyltransferase |
| RNF138P1 | 6.017 | 7.401 | 6.439 | | 3.797 | 2.970 | 3.516 | | −8.263 | 0.0033529 | ring finger protein 138 pseudogene 1 |
| DYNLT1 | 3.619 | 6.736 | 7.458 | | 2.951 | 4.413 | 2.233 | | −8.256 | 0.0351081 | dynein, light chain, Tctex-type 1 |
| LZTFL1 | 3.422 | 5.409 | 4.692 | | 1.648 | 1.648 | 1.648 | | −8.245 | 0.0079047 | leucine zipper transcription factor-like 1 |
| EID1 | 8.386 | 8.969 | 8.510 | | 5.715 | 4.097 | 5.928 | | −8.231 | 0.0039088 | EP300 interacting inhibitor of differentiation 1 |
| C9orf16 | 6.735 | 7.330 | 7.173 | | 4.117 | 5.189 | 3.694 | | −8.224 | 0.0070021 | chromosome 9 open reading frame 16 |
| MFAP2 | 5.688 | 5.081 | 5.729 | | 2.648 | 2.648 | 2.648 | | −8.224 | 0.0017958 | microfibrillar-associated protein 2 |
| VEGFB | 8.740 | 8.080 | 8.015 | | 6.231 | 5.040 | 4.937 | | −8.223 | 0.0055608 | vascular endothelial growth factor B |
| PMVK | 3.422 | 5.778 | 5.082 | | 1.648 | 2.739 | 1.648 | | −8.217 | 0.0146887 | phosphomevalonate kinase |
| DSC2 | 6.047 | 7.787 | 8.761 | | 4.442 | 5.725 | 4.603 | | −8.203 | 0.0209640 | desmocollin 2 |
| ABHD14B | 8.820 | 7.419 | 7.372 | | 5.384 | 4.339 | 5.579 | | −8.183 | 0.0098305 | abhydrolase domain containing 14B |
| BMI1 | 4.214 | 7.142 | 6.487 | | 3.456 | 3.456 | 3.865 | | −8.174 | 0.0285792 | BMI1 polycomb ring finger oncogene |
| GADD45B | 13.444 | 11.739 | 11.951 | | 8.605 | 10.110 | 10.414 | | −8.170 | 0.0157043 | growth arrest and DNA-damage-inducible, beta |
| SH3KBP1 | 7.476 | 7.038 | 7.538 | | 5.418 | 4.240 | 4.013 | | −8.144 | 0.0060953 | SH3-domain kinase binding protein 1 |
| PHF23 | 5.977 | 7.459 | 7.431 | | 4.273 | 4.135 | 4.436 | | −8.133 | 0.0081286 | PHD finger protein 23 |
| CDIPT | 7.511 | 8.289 | 8.227 | | 6.038 | 4.007 | 5.205 | | −8.128 | 0.0083421 | CDP-diacylglycerol inositol 3-phosphatidyltransferase |
| SLC39A7 | 7.347 | 8.720 | 8.186 | | 5.818 | 5.166 | 4.141 | | −8.110 | 0.0069841 | solute carrier family 39 (zinc transporter), member 7 |
| COX5A | 5.552 | 7.799 | 8.201 | | 4.482 | 5.085 | 4.781 | | −8.097 | 0.0247248 | cytochrome c oxidase subunit Va |
| SPTLC1 | 5.705 | 6.967 | 7.165 | | 3.951 | 3.978 | 3.701 | | −8.089 | 0.0068073 | serine palmitoyltransferase, long chain base subunit 1 |
| GTF2H2D | 0.648 | 3.664 | 4.972 | | 0.648 | 0.648 | 0.648 | | −8.088 | 0.0454139 | general transcription factor IIH, polypeptide 2D |
| TSPAN1 | 0.648 | 3.664 | 4.665 | | 0.648 | 0.648 | 0.648 | | −8.088 | 0.0466104 | tetraspanin 1 |
| MAGED1 | 1.648 | 6.253 | 4.663 | | 1.648 | 1.648 | 1.648 | | −8.083 | 0.0446873 | melanoma antigen family D, 1 |
| USP14 | 5.204 | 8.477 | 8.332 | | 5.412 | 5.318 | 4.409 | | −8.082 | 0.0436932 | ubiquitin specific peptidase 14 (tRNA-guanine transglycosylase) |
| TIMM8B | 4.423 | 7.733 | 7.388 | | 4.376 | 4.529 | 3.557 | | −8.067 | 0.0386735 | translocase of inner mitochondrial membrane 8 homolog B (yeast) |
| GPR124 | 8.639 | 7.485 | 6.863 | | 4.233 | 4.482 | 4.672 | | −8.014 | 0.0040849 | G protein-coupled receptor 124 |
| HOXC6 | 5.204 | 5.491 | 4.632 | | 2.202 | 0.648 | 3.351 | | −8.013 | 0.0110464 | homeobox C6 |
| EGFL6 | 7.531 | 3.644 | 2.714 | | 0.648 | 0.648 | 2.370 | | −7.974 | 0.0246582 | EGF-like-domain, multiple 6 |
| NAA50 | 6.160 | 9.178 | 8.920 | | 5.899 | 5.449 | 6.184 | | −7.965 | 0.0384676 | N(alpha)-acetyltransferase 50, NatE catalytic subunit |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| TOMM22 | 6.980 | 9.851 | 8.439 | 6.522 | 5.449 | 5.202 | −7.941 | 0.0197113 | translocase of outer mitochondrial membrane 22 homolog (yeast) |
| C22orf28 | 3.619 | 6.266 | 6.886 | 3.278 | 3.467 | 2.233 | −7.938 | 0.0280184 | chromosome 22 open reading frame 28 |
| STT3A | 7.652 | 8.133 | 8.130 | 6.601 | 5.143 | 4.579 | −7.929 | 0.0138360 | STT3, subunit of the oligosaccharyltransferase complex, homolog A (S. cerevisiae) |
| CNKSR3 | 5.169 | 6.771 | 6.029 | 2.951 | 3.043 | 3.054 | −7.924 | 0.0045556 | CNKSR family member 3 |
| TNFRSF10D | 4.872 | 7.197 | 7.277 | 3.997 | 3.859 | 4.293 | −7.909 | 0.0232939 | tumor necrosis factor receptor superfamily, member 10d, decoy with truncated death domain |
| SLC9A7 | 0.648 | 3.631 | 4.934 | 0.648 | 0.648 | 0.648 | −7.905 | 0.0458575 | solute carrier family 9 (sodium/hydrogen exchanger), member 7 |
| EBNA1BP2 | 3.619 | 6.992 | 6.517 | 3.535 | 2.233 | 3.737 | −7.901 | 0.0338839 | EBNA1 binding protein 2 |
| ATP6AP2 | 7.002 | 7.269 | 6.208 | 5.315 | 3.233 | 3.233 | −7.862 | 0.0115511 | ATPase, H+ transporting, lysosomal accessory protein 2 |
| MRPL24 | 6.470 | 6.818 | 7.067 | 3.897 | 4.097 | 2.648 | −7.837 | 0.0032170 | mitochondrial ribosomal protein L24 |
| SLC35B2 | 6.756 | 7.635 | 7.946 | 4.670 | 3.508 | 5.270 | −7.809 | 0.0077050 | solute carrier family 35, member B2 |
| ANKRD10 | 8.359 | 8.831 | 9.305 | 6.340 | 5.140 | 5.955 | −7.807 | 0.0039809 | ankyrin repeat domain 10 |
| DLK1 | 5.222 | 5.915 | 6.259 | 2.648 | 3.294 | 2.648 | −7.806 | 0.0034783 | delta-like 1 homolog (Drosophila) |
| CCDC82 | 4.620 | 6.299 | 5.607 | 2.648 | 2.648 | 4.293 | −7.776 | 0.0058763 | coiled-coil domain containing 82 |
| CAPZA2 | 5.690 | 8.482 | 7.823 | 4.463 | 5.525 | 4.293 | −7.767 | 0.0234513 | capping protein (actin filament) muscle Z-line, alpha 2 |
| PIM2 | 6.203 | 7.836 | 5.926 | 4.042 | 2.970 | 4.673 | −7.760 | 0.0141064 | pim-2 oncogene |
| SHMT2 | 5.107 | 8.348 | 7.540 | 5.395 | 4.447 | 4.141 | −7.745 | 0.0370062 | serine hydroxymethyltransferase 2 (mitochondrial) |
| FBXO32 | 4.826 | 8.354 | 7.627 | 4.675 | 5.034 | 3.516 | −7.740 | 0.0352246 | F-box protein 32 |
| GTF2H5 | 7.307 | 8.285 | 7.668 | 5.553 | 4.355 | 4.712 | −7.736 | 0.0051560 | general transcription factor IIH, polypeptide 5 |
| SFRP2 | 9.353 | 7.454 | 6.352 | 4.655 | 4.405 | 4.507 | −7.713 | 0.0104669 | secreted frizzled-related protein 2 |
| BRMS1 | 3.860 | 6.231 | 5.343 | 2.714 | 3.284 | 0.648 | −7.712 | 0.0190111 | breast cancer metastasis suppressor 1 |
| ELF1 | 8.259 | 8.835 | 8.361 | 5.421 | 4.600 | 6.178 | −7.674 | 0.0041335 | E74-like factor 1 (ets domain transcription factor) |
| TRMT112 | 7.304 | 9.727 | 8.958 | 6.457 | 6.019 | 4.581 | −7.672 | 0.0141847 | tRNA methyltransferase 11-2 homolog (S. cerevisiae) |
| RNPS1 | 5.107 | 8.215 | 8.199 | 4.728 | 5.011 | 5.277 | −7.664 | 0.0465023 | RNA binding protein S1, serine-rich domain |
| FN1 | 10.527 | 11.129 | 9.255 | 6.819 | 7.589 | 7.994 | −7.662 | 0.0098846 | fibronectin 1 |
| DUSP10 | 4.142 | 5.888 | 5.737 | 2.951 | 2.233 | 2.233 | −7.656 | 0.0094666 | dual specificity phosphatase 10 |
| ZNF593 | 4.525 | 7.754 | 7.575 | 4.378 | 4.818 | 3.737 | −7.654 | 0.0415657 | zinc finger protein 593 |
| DLC1 | 6.734 | 7.317 | 7.266 | 4.108 | 4.108 | 4.382 | −7.652 | 0.0015809 | deleted in liver cancer 1 |
| RBM15 | 4.422 | 6.723 | 5.584 | 2.648 | 2.648 | 3.303 | −7.651 | 0.0128412 | RNA binding motif protein 15 |
| PRPF31 | 4.817 | 6.502 | 5.886 | 2.951 | 3.043 | 2.233 | −7.647 | 0.0059393 | PRP31 pre-mRNA processing factor 31 homolog (S. cerevisiae) |
| CRIM1 | 4.672 | 8.063 | 7.065 | 4.132 | 4.294 | 3.648 | −7.635 | 0.0267095 | cysteine rich transmembrane BMP regulator 1 (chordin-like) |
| CD46 | 6.949 | 8.600 | 8.722 | 5.790 | 5.528 | 5.502 | −7.631 | 0.0133778 | CD46 molecule, complement regulatory protein |
| SCP2 | 5.934 | 5.902 | 5.990 | 2.970 | 3.508 | 2.970 | −7.629 | 0.0017570 | sterol carrier protein 2 |
| VCL | 10.585 | 10.343 | 9.939 | 7.407 | 7.654 | 7.127 | −7.626 | 0.0019893 | vinculin |
| MOBKL2A | 7.419 | 9.003 | 8.200 | 6.073 | 5.838 | 4.377 | −7.623 | 0.0018028 | MOB1, Mps One Binder kinase activator-like 2A (yeast) |
| C19orf10 | 6.912 | 9.232 | 9.829 | 6.900 | 5.896 | 4.579 | −7.618 | 0.0226014 | chromosome 19 open reading frame 10 |
| PVRL4 | 5.899 | 6.250 | 7.148 | 2.970 | 4.508 | 2.970 | −7.615 | 0.0079816 | poliovirus receptor-related 4 |
| GOLPH3 | 9.709 | 9.915 | 9.776 | 7.572 | 6.435 | 6.847 | −7.614 | 0.0035303 | golgi phosphoprotein 3 (coat-protein) |
| SOX17 | 7.983 | 5.896 | 5.263 | 4.156 | 2.970 | 2.970 | −7.600 | 0.0136558 | SRY (sex determining region Y)-box 17 |
| NCRNA00116 | 4.378 | 6.811 | 5.896 | 3.442 | 2.970 | 2.970 | −7.600 | 0.0161646 | non-protein coding RNA 116 |
| SAR1A | 8.769 | 10.199 | 9.662 | 7.046 | 6.155 | 6.740 | −7.575 | 0.0056648 | SAR1 homolog A (S. cerevisiae) |
| RIOK3 | 4.539 | 7.467 | 7.178 | 4.225 | 4.264 | 4.516 | −7.537 | 0.0456107 | RIO kinase 3 (yeast) |

TABLE 4-continued

Differentially Expressed Genes in CD44+ Breast Epithelial Cells

| | Nulliparous (NP) Samples | | | | Parous (P) Samples | | | | Pseudo fold change | P value | Gene description |
|---|---|---|---|---|---|---|---|---|---|---|---|
| Gene Symbol | CD44+ N48 | CD44+ N58 | CD44+ N43 | | CD44+ N37 | CD44+ N39 | CD44+ N40 | | | | |
| OLFML2A | 8.879 | 8.519 | 7.405 | | 5.134 | 4.989 | 5.967 | | −7.526 | 0.0064392 | olfactomedin-like 2A |
| FXYD1 | 5.644 | 7.288 | 5.143 | | 2.951 | 2.233 | 3.508 | | −7.516 | 0.0082631 | FXYD domain containing ion transport regulator 1 |
| RAB40B | 6.070 | 6.418 | 6.531 | | 2.233 | 4.500 | 3.508 | | −7.513 | 0.0090617 | RAB40B, member RAS oncogene family |
| C7orf60 | 4.969 | 6.806 | 6.815 | | 3.442 | 3.827 | 3.911 | | −7.486 | 0.0152544 | chromosome 7 open reading frame 60 |
| MTCYB | 13.951 | 9.184 | 9.953 | | 7.050 | 6.987 | 7.156 | | −7.478 | 0.0134229 | No description |
| PRKAR1A | 9.779 | 12.053 | 12.245 | | 9.344 | 8.338 | 8.978 | | −7.471 | 0.0230000 | protein kinase, cAMP-dependent, regulatory, type I, alpha (tissue specific extinguisher 1) |
| C19orf40 | 8.872 | 9.026 | 9.068 | | 6.565 | 5.817 | 6.125 | | −7.469 | 0.0021113 | chromosome 19 open reading frame 40 |
| C10orf116 | 9.685 | 9.896 | 8.607 | | 5.929 | 6.951 | 6.785 | | −7.467 | 0.0065258 | chromosome 10 open reading frame 116 |
| CCL2 | 12.696 | 11.505 | 10.195 | | 8.606 | 8.678 | 8.043 | | −7.464 | 0.0097439 | chemokine (C-C motif) ligand 2 |
| FKBP1A | 9.411 | 11.546 | 11.306 | | 8.647 | 7.493 | 7.539 | | −7.459 | 0.0124191 | FK506 binding protein 1A, 12 kDa |
| ZC3H11A | 7.886 | 9.203 | 8.855 | | 6.305 | 5.228 | 5.688 | | −7.455 | 0.0057300 | zinc finger CCCH-type containing 11A |
| MRPL54 | 4.423 | 6.222 | 5.997 | | 3.326 | 2.739 | 2.752 | | −7.445 | 0.0117182 | mitochondrial ribosomal protein L54 |
| CBLC | 2.233 | 5.126 | 6.294 | | 2.233 | 2.233 | 2.233 | | −7.427 | 0.0482250 | Gas-Br-M (murine) ecotropic retroviral transforming sequence c |
| GLT25D1 | 7.295 | 8.413 | 8.254 | | 5.522 | 5.247 | 5.125 | | −7.416 | 0.0052510 | glycosyltransferase 25 domain containing 1 |
| PRSS23 | 7.743 | 8.273 | 6.807 | | 5.384 | 4.108 | 4.382 | | −7.407 | 0.0064482 | protease, serine, 23 |
| PSMB10 | 3.422 | 4.536 | 6.042 | | 2.625 | 1.648 | 1.648 | | −7.402 | 0.0166735 | proteasome (prosome, macropain) subunit, beta type, 10 |
| EPAS1 | 11.122 | 11.919 | 9.707 | | 9.033 | 8.142 | 7.743 | | −7.394 | 0.0160655 | endothelial PAS domain protein 1 |
| YAP1 | 8.277 | 10.062 | 9.479 | | 6.904 | 6.442 | 6.594 | | −7.386 | 0.0101993 | Yes-associated protein 1 |
| TES | 9.259 | 10.515 | 10.264 | | 7.237 | 8.489 | 6.377 | | −7.374 | 0.0147026 | testis derived transcript (3 LIM domains) |
| DNAJC7 | 4.709 | 7.712 | 7.718 | | 4.240 | 4.149 | 4.836 | | −7.370 | 0.0374423 | DnaJ (Hsp40) homolog, subfamily C, member 7 |
| CHN1 | 5.109 | 6.465 | 5.998 | | 4.052 | 2.233 | 2.233 | | −7.341 | 0.0091560 | chimerin (chimaerin) 1 |
| TAF6 | 5.109 | 5.860 | 5.686 | | 4.575 | 2.233 | 2.233 | | −7.341 | 0.0197841 | TAF6 RNA polymerase II, TATA box binding protein (TBP)-associated factor, 80 kDa |
| ATP5F1 | 6.791 | 8.724 | 7.774 | | 5.472 | 3.739 | 5.851 | | −7.330 | 0.0166007 | ATP synthase, H+ transporting, mitochondrial Fo complex, subunit B1 |
| AR | 6.667 | 5.367 | 5.104 | | 3.278 | 3.043 | 2.233 | | −7.317 | 0.0078062 | androgen receptor |
| MLF1 | 4.524 | 7.059 | 5.836 | | 2.970 | 2.970 | 2.970 | | −7.290 | 0.0117452 | myeloid leukemia factor 1 |
| SPARCL1 | 8.267 | 10.199 | 7.614 | | 5.401 | 5.506 | 5.112 | | −7.287 | 0.0068794 | SPARC-like 1 (hevin) |
| PKIG | 10.339 | 9.699 | 9.496 | | 8.036 | 6.543 | 6.839 | | −7.264 | 0.0083962 | protein kinase (cAMP-dependent, catalytic) inhibitor gamma |
| SDCBP | 10.061 | 11.081 | 11.021 | | 8.225 | 7.755 | 8.132 | | −7.239 | 0.0051199 | syndecan binding protein (syntenin) |
| KIAA1467 | 3.619 | 5.321 | 5.088 | | 2.233 | 2.233 | 2.233 | | −7.232 | 0.0126263 | KIAA1467 |
| LAPTM4A | 12.501 | 13.235 | 12.288 | | 10.626 | 9.329 | 9.648 | | −7.223 | 0.0063130 | lysosomal protein transmembrane 4 alpha |
| PCOLCE | 7.672 | 9.106 | 7.785 | | 4.876 | 4.933 | 6.257 | | −7.202 | 0.0097529 | procollagen C-endopeptidase enhancer |
| RNF103 | 5.039 | 7.601 | 7.503 | | 3.637 | 4.135 | 4.759 | | −7.170 | 0.0233120 | ring finger protein 103 |
| LATS2 | 8.899 | 10.122 | 10.771 | | 6.975 | 7.283 | 7.500 | | −7.155 | 0.0101182 | LATS, large tumor suppressor, homolog 2 (Drosophila) |
| HSD17B11 | 8.818 | 8.712 | 7.227 | | 5.979 | 4.861 | 5.808 | | −7.154 | 0.0109314 | hydroxysteroid (17-beta) dehydrogenase 11 |
| ARL1 | 7.361 | 7.327 | 6.873 | | 5.564 | 4.490 | 3.233 | | −7.150 | 0.0118839 | ADP-ribosylation factor-like 1 |
| EFEMP1 | 5.596 | 9.170 | 6.703 | | 3.808 | 4.447 | 3.865 | | −7.147 | 0.0160399 | EGF-containing fibulin-like extracellular matrix protein 1 |
| MFAP5 | 8.490 | 8.657 | 6.638 | | 3.848 | 4.791 | 5.821 | | −7.139 | 0.0110797 | microfibrillar associated protein 5 |
| CXCL12 | 11.917 | 10.511 | 9.404 | | 7.399 | 7.543 | 9.082 | | −7.138 | 0.0215997 | chemokine (C-X-C motif) ligand 12 |
| IGFBP6 | 9.376 | 9.287 | 8.911 | | 6.567 | 6.035 | 6.454 | | −7.128 | 0.0019262 | insulin-like growth factor binding protein 6 |
| SRGN | 7.233 | 10.960 | 7.100 | | 6.131 | 4.273 | 5.682 | | −7.099 | 0.0261307 | serglycin |
| LRRC61 | 5.870 | 4.901 | 5.128 | | 0.648 | 2.353 | 3.043 | | −7.095 | 0.0072607 | leucine rich repeat containing 61 |
| RCAN1 | 5.482 | 7.775 | 6.461 | | 3.637 | 3.233 | 3.701 | | −7.086 | 0.0078811 | regulator of calcineurin 1 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| ERRFI1 | 8.265 | 11.804 | 11.440 | 7.483 | 7.122 | 8.985 | −7.056 | 0.0351539 | ERBB receptor feedback inhibitor 1 |
| SNAPC3 | 5.861 | 5.466 | 6.697 | 3.494 | 3.294 | 2.648 | −7.049 | 0.0050880 | small nuclear RNA activating complex, polypeptide 3, 50 kDa |
| TWSG1 | 4.826 | 7.856 | 6.857 | 3.442 | 4.289 | 4.042 | −7.038 | 0.0229099 | twisted gastrulation homolog 1 (Drosophila) |
| CCDC83 | 3.194 | 5.166 | 4.771 | 0.648 | 2.353 | 0.648 | −7.029 | 0.0098215 | coiled-coil domain containing 83 |
| CTDSP1 | 10.292 | 9.879 | 9.227 | 7.667 | 6.417 | 6.429 | −7.010 | 0.0055698 | CTD (carboxy-terminal domain, RNA polymerase II, polypeptide A) small phosphatase 1 |
| DNAJC14 | 5.204 | 6.918 | 6.264 | 3.456 | 3.456 | 3.865 | −7.006 | 0.0107373 | DnaJ (Hsp40) homolog, subfamily C, member 14 |
| INSIG1 | 8.532 | 7.890 | 8.078 | 5.157 | 5.083 | 6.309 | −6.994 | 0.0072336 | insulin induced gene 1 |
| EFCAB4A | 4.008 | 4.454 | 5.869 | 1.648 | 1.648 | 2.752 | −6.993 | 0.0113016 | EF-hand calcium binding domain 4A |
| PCDHB14 | 4.647 | 4.665 | 3.452 | 0.648 | 0.648 | 2.370 | −6.981 | 0.0084634 | protocadherin beta 14 |
| SHQ1 | 4.744 | 5.531 | 5.448 | 2.648 | 2.648 | 2.648 | −6.962 | 0.0039179 | SHQ1 homolog (S. cerevisiae) |
| C15orf44 | 5.600 | 7.136 | 7.184 | 4.385 | 4.149 | 2.970 | −6.960 | 0.0109494 | chromosome 15 open reading frame 44 |
| MKRN2 | 4.872 | 6.774 | 6.955 | 4.159 | 3.859 | 3.865 | −6.944 | 0.0228399 | makorin ring finger protein 2 |
| REST | 6.679 | 5.546 | 6.287 | 3.494 | 2.648 | 4.538 | −6.931 | 0.0128232 | RE1-silencing transcription factor |
| TBCB | 5.377 | 7.455 | 6.448 | 3.897 | 3.659 | 2.648 | −6.916 | 0.0087491 | tubulin folding cofactor B |
| CHRNE | 6.324 | 5.167 | 4.928 | 3.535 | 3.535 | 2.233 | −6.910 | 0.0092503 | cholinergic receptor, nicotinic, epsilon |
| PTP4A3 | 8.433 | 6.618 | 6.318 | 3.830 | 5.197 | 3.557 | −6.905 | 0.0129175 | protein tyrosine phosphatase type IVA, member 3 |
| EPHX2 | 6.829 | 4.600 | 5.648 | 1.648 | 3.892 | 4.043 | −6.894 | 0.0285314 | epoxide hydrolase 2, cytoplasmic |
| CCDC111 | 3.194 | 3.431 | 4.262 | 0.648 | 0.648 | 0.648 | −6.884 | 0.0025251 | coiled-coil domain containing 111 |
| ZFP36L1 | 13.356 | 12.879 | 11.506 | 10.422 | 8.720 | 10.575 | −6.873 | 0.0166187 | zinc finger protein 36, C3H type-like 1 |
| TMEM203 | 3.619 | 6.794 | 6.817 | 2.951 | 4.037 | 3.054 | −6.868 | 0.0381265 | transmembrane protein 203 |
| KDELR1 | 10.091 | 10.895 | 10.422 | 8.116 | 7.612 | 7.538 | −6.865 | 0.0037709 | KDEL (Lys-Asp-Glu-Leu) endoplasmic reticulum protein retention receptor 1 |
| APPL2 | 3.792 | 6.271 | 6.151 | 3.494 | 3.294 | 2.648 | −6.856 | 0.0297009 | adaptor protein, phosphotyrosine interaction, PH domain and leucine zipper containing 2 |
| KCNA6 | 4.423 | 4.117 | 5.010 | 1.648 | 1.648 | 1.648 | −6.844 | 0.0022818 | potassium voltage-gated channel, shaker-related subfamily, member 6 |
| PC | 4.423 | 4.975 | 5.191 | 3.023 | 1.648 | 1.648 | −6.844 | 0.0075449 | pyruvate carboxylase |
| FGFBP2 | 4.423 | 5.926 | 3.602 | 1.648 | 1.648 | 2.752 | −6.844 | 0.0162492 | fibroblast growth factor binding protein 2 |
| MIER2 | 4.423 | 5.811 | 6.706 | 3.494 | 3.499 | 3.929 | −6.844 | 0.0235179 | mesoderm induction early response 1, family member 2 |
| LYZ | 4.423 | 5.772 | 1.729 | 1.648 | 1.648 | 1.648 | −6.844 | 0.0464059 | lysozyme |
| KDELR2 | 10.055 | 11.338 | 10.908 | 8.566 | 7.736 | 7.616 | −6.831 | 0.0064121 | KDEL (Lys-Asp-Glu-Leu) endoplasmic reticulum protein retention receptor 2 |
| GNAI2 | 10.238 | 9.744 | 8.865 | 7.365 | 6.301 | 6.974 | −6.820 | 0.0076960 | guanine nucleotide binding protein (G protein), alpha inhibiting activity polypeptide 2 |
| TMEM138 | 5.160 | 5.807 | 5.910 | 4.234 | 3.043 | 2.233 | −6.793 | 0.0153868 | transmembrane protein 138 |
| OSBPL9 | 3.792 | 6.728 | 6.257 | 3.494 | 3.659 | 2.648 | −6.788 | 0.0329854 | oxysterol binding protein-like 9 |
| ETV6 | 8.062 | 8.001 | 8.000 | 5.245 | 6.196 | 5.092 | −6.755 | 0.0066610 | ets variant 6 |
| PCDH18 | 7.826 | 7.341 | 8.057 | 4.764 | 4.585 | 5.687 | −6.753 | 0.0055088 | protocadherin 18 |
| DSTN | 6.641 | 9.276 | 8.648 | 5.892 | 6.521 | 5.504 | −6.750 | 0.0315199 | destrin (actin depolymerizing factor) |
| GABARAPL2 | 6.262 | 7.079 | 7.011 | 4.033 | 4.624 | 3.508 | −6.746 | 0.0057487 | GABA(A) receptor-associated protein-like 2 |
| HERPUD1 | 7.540 | 9.647 | 9.440 | 6.894 | 6.500 | 5.525 | −6.740 | 0.0179816 | homocysteine-inducible, endoplasmic reticulum stress-inducible, ubiquitin-like domain member 1 |
| HADH | 6.798 | 6.354 | 7.363 | 4.182 | 4.015 | 4.049 | −6.723 | 0.0035213 | hydroxyacyl-CoA dehydrogenase |
| PPP1R1A | 3.422 | 4.395 | 4.930 | 1.648 | 1.648 | 1.648 | −6.711 | 0.0078381 | protein phosphatase 1, regulatory (inhibitor) subunit 1A |
| RFC2 | 3.422 | 4.395 | 5.228 | 1.648 | 1.648 | 1.648 | −6.711 | 0.0084544 | replication factor C (activator 1) 2, 40 kDa |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| STOM | 13.706 | 12.688 | 11.832 | 10.413 | 9.739 | 9.943 | −6.704 | 0.0097709 | stomatin |
| DBC1 | 5.396 | 5.405 | 4.977 | 2.233 | 3.686 | 2.233 | −6.698 | 0.0103747 | deleted in bladder cancer 1 |
| SCAND1 | 7.268 | 7.867 | 8.253 | 5.502 | 5.512 | 4.493 | −6.683 | 0.0075088 | SCAN domain containing 1 |
| PIN1 | 6.685 | 6.685 | 6.844 | 4.877 | 3.892 | 4.104 | −6.679 | 0.0052690 | peptidylprolyl cis/trans isomerase, NIMA-interacting 1 |
| HDAC11 | 6.291 | 5.464 | 5.385 | 3.718 | 2.648 | 2.648 | −6.668 | 0.0069660 | histone deacetylase 11 |
| SLC25A17 | 3.619 | 6.096 | 4.970 | 2.233 | 2.233 | 2.233 | −6.665 | 0.0141515 | solute carrier family 25 (mitochondrial carrier; peroxisomal membrane protein, 34 kDa), member 17 |
| SKP1 | 9.094 | 11.128 | 11.054 | 8.128 | 8.394 | 8.061 | −6.656 | 0.0230763 | S-phase kinase-associated protein 1 |
| MICAL2 | 6.320 | 7.510 | 6.415 | 3.682 | 5.518 | 3.516 | −6.649 | 0.0180724 | microtubule associated monoxygenase, calponin and LIM domain containing 2 |
| NME7 | 5.908 | 6.030 | 5.979 | 4.017 | 3.247 | 2.752 | −6.645 | 0.0057938 | non-metastatic cells 7, protein expressed in (nucleoside-diphosphate kinase) |
| FAM82A2 | 5.377 | 6.277 | 5.813 | 2.648 | 4.628 | 2.648 | −6.630 | 0.0166506 | family with sequence similarity 82, member A2 |
| SEMA3G | 7.157 | 6.868 | 7.072 | 4.463 | 4.259 | 4.141 | −6.618 | 0.0014180 | sema domain, immunoglobulin domain (ig), short basic domain, secreted, (semaphorin) 3G |
| PTGDS | 6.612 | 8.995 | 8.457 | 5.661 | 4.508 | 6.271 | −6.609 | 0.0227754 | prostaglandin D2 synthase 21 kDa (brain) |
| IRF2BP2 | 9.150 | 10.670 | 10.207 | 7.130 | 6.885 | 7.947 | −6.601 | 0.0093896 | interferon regulatory factor 2 binding protein 2 |
| MMP14 | 9.037 | 8.199 | 8.415 | 6.361 | 5.479 | 5.546 | −6.592 | 0.0048454 | matrix metallopeptidase 14 (membrane-inserted) |
| CD8B | 6.262 | 4.950 | 4.165 | 2.233 | 2.233 | 2.233 | −6.572 | 0.0080953 | CD8b molecule |
| AKR1C3 | 8.973 | 9.398 | 10.222 | 7.846 | 6.686 | 5.462 | −6.556 | 0.0124711 | aldo-keto reductase family 1, member C3 (3-alpha hydroxysteroid dehydrogenase, type II) |
| RBM14 | 7.483 | 9.097 | 8.468 | 6.069 | 5.634 | 5.757 | −6.549 | 0.0101452 | RNA binding motif protein 14 |
| SALL2 | 6.036 | 5.301 | 5.632 | 3.326 | 3.247 | 1.648 | −6.542 | 0.0074194 | sal-like 2 (Drosophila) |
| TXNL4A | 5.173 | 7.872 | 7.109 | 4.883 | 4.405 | 3.897 | −6.517 | 0.0275040 | thioredoxin-like 4A |
| NDUFA12 | 4.936 | 6.238 | 6.209 | 3.535 | 3.467 | 2.233 | −6.510 | 0.0103837 | NADH dehydrogenase (ubiquinone) 1 alpha subcomplex, 12 |
| TNNT3 | 4.972 | 6.597 | 5.687 | 0.648 | 2.987 | 4.602 | −6.499 | 0.0234284 | troponin T type 3 (skeletal, fast) |
| FMO1 | 9.006 | 5.348 | 5.909 | 2.648 | 3.294 | 4.199 | −6.498 | 0.0155615 | flavin containing monooxygenase 1 |
| PLK2 | 5.404 | 7.697 | 7.209 | 3.961 | 4.007 | 4.997 | −6.498 | 0.0207532 | polo-like kinase 2 |
| COL14A1 | 10.160 | 8.852 | 8.108 | 5.621 | 6.152 | 6.236 | −6.495 | 0.0070291 | collagen, type XIV, alpha 1 |
| NADSYN1 | 4.142 | 5.174 | 4.932 | 2.233 | 2.233 | 2.233 | −6.493 | 0.0057848 | NAD synthetase 1 |
| NGFR | 11.046 | 8.470 | 8.111 | 5.413 | 7.196 | 6.229 | −6.490 | 0.0190201 | nerve growth factor receptor |
| MPDU1 | 4.657 | 6.087 | 4.931 | 2.233 | 3.043 | 2.233 | −6.488 | 0.0080114 | mannose-P-dolichol utilization defect 1 |
| HMGB1 | 3.947 | 7.174 | 6.491 | 3.797 | 4.405 | 2.970 | −6.471 | 0.0357425 | high-mobility group box 1 |
| C16orf42 | 6.338 | 7.407 | 7.351 | 4.715 | 4.265 | 3.737 | −6.460 | 0.0057757 | chromosome 16 open reading frame 42 |
| ADM | 6.070 | 8.800 | 8.616 | 5.551 | 5.561 | 6.109 | −6.457 | 0.0414596 | adrenomedullin |
| RHOB | 8.967 | 11.265 | 10.619 | 8.575 | 7.868 | 7.792 | −6.451 | 0.0258749 | ras homolog gene family, member B |
| SPINT1 | 6.349 | 8.706 | 9.052 | 5.343 | 6.363 | 3.694 | −6.448 | 0.0229459 | serine peptidase inhibitor, Kunitz type 1 |
| SCOC | 5.008 | 5.336 | 6.205 | 2.648 | 2.648 | 2.648 | −6.443 | 0.0036718 | short coiled-coil protein |
| TJP2 | 6.013 | 7.256 | 7.412 | 4.728 | 4.383 | 4.409 | −6.427 | 0.0113660 | tight junction protein 2 (zona occludens 2) |
| RANBP3 | 5.171 | 7.619 | 7.439 | 4.935 | 4.699 | 4.264 | −6.426 | 0.0346208 | RAN binding protein 3 |
| CHST15 | 9.534 | 9.887 | 9.703 | 7.022 | 6.573 | 7.823 | −6.412 | 0.0067844 | carbohydrate (N-acetylgalactosamine 4-sulfate 6-O) sulfotransferase 15 |
| CXCL13 | 6.541 | 6.673 | 7.652 | 2.625 | 4.945 | 4.975 | −6.396 | 0.0159726 | chemokine (C-X-C motif) ligand 13 |
| CCL8 | 6.829 | 7.267 | 5.416 | 6.065 | 2.739 | 3.294 | −6.395 | 0.0375990 | chemokine (C-C motif) ligand 8 |
| RBBP7 | 6.689 | 7.649 | 8.190 | 4.946 | 4.972 | 5.087 | −6.393 | 0.0090458 | retinoblastoma binding protein 7 |
| PIGF | 4.008 | 5.903 | 6.232 | 3.557 | 2.739 | 2.752 | −6.390 | 0.0218894 | phosphatidylinositol glycan anchor biosynthesis, class F |

TABLE 4-continued

Differentially Expressed Genes in CD44+ Breast Epithelial Cells

| Gene Symbol | Nulliparous (NP) Samples | | Parous (P) Samples | | | Pseudo fold change | P value | Gene description |
|---|---|---|---|---|---|---|---|---|
| | CD44+ N48 | CD44+ N58 | CD44+ N43 | CD44+ N37 | CD44+ N39 | CD44+ N40 | | |
| ALKBH7 | 8.127 | 7.625 | 8.173 | 5.462 | 5.458 | 5.451 | −6.359 | 0.0033043 | alkB, alkylation repair homolog 7 (*E. coli*) |
| CAB39 | 5.690 | 7.768 | 7.939 | 4.159 | 5.272 | 4.924 | −6.350 | 0.0244059 | calcium binding protein 39 |
| YWHAH | 9.341 | 10.194 | 10.036 | 7.089 | 7.531 | 6.724 | −6.334 | 0.0044780 | tyrosine 3-monooxygenase/tryptophan 5-monooxygenase activation protein, eta polypeptide |
| ADAMTS4 | 12.322 | 14.494 | 11.383 | 9.723 | 9.167 | 9.660 | −6.332 | 0.0113750 | ADAM metallopeptidase with thrombospondin type 1 motif, 4 |
| AQP1 | 7.720 | 9.280 | 6.251 | 4.496 | 5.746 | 5.057 | −6.330 | 0.0218984 | aquaporin 1 (Colton blood group) |
| NFU1 | 5.908 | 6.123 | 5.706 | 4.687 | 3.247 | 2.752 | −6.326 | 0.0163068 | NFU1 iron-sulfur cluster scaffold homolog (*S. cerevisiae*) |
| SLFN11 | 6.811 | 7.258 | 5.562 | 4.151 | 3.508 | 4.327 | −6.322 | 0.0117723 | schlafen family member 11 |
| PARK7 | 5.967 | 6.781 | 6.678 | 5.378 | 4.017 | 2.752 | −6.321 | 0.0225376 | Parkinson disease (autosomal recessive, early onset) 7 |
| SFRS4 | 7.457 | 10.035 | 9.599 | 6.645 | 6.800 | 7.376 | −6.318 | 0.0363386 | No description |
| FAH | 5.941 | 5.624 | 6.191 | 3.442 | 3.508 | 2.970 | −6.294 | 0.0035754 | fumarylacetoacetate hydrolase (fumarylacetoacetase) |
| YPEL2 | 8.675 | 9.348 | 8.616 | 6.691 | 5.393 | 6.696 | −6.284 | 0.0087830 | yippee-like 2 (*Drosophila*) |
| MTMR11 | 7.217 | 5.390 | 5.525 | 4.529 | 2.739 | 3.370 | −6.281 | 0.0198499 | myotubularin related protein 11 |
| RPN2 | 7.053 | 9.003 | 8.696 | 6.353 | 5.308 | 4.553 | −6.276 | 0.0133868 | ribophorin II |
| PTPRS | 9.742 | 8.599 | 9.172 | 6.943 | 5.952 | 6.887 | −6.264 | 0.0085362 | protein tyrosine phosphatase, receptor type, S |
| IGFBP2 | 9.147 | 8.799 | 7.894 | 6.848 | 6.157 | 5.074 | −6.244 | 0.0131775 | insulin-like growth factor binding protein 2, 36 kDa |
| TMX2 | 5.941 | 7.951 | 7.426 | 4.784 | 4.844 | 4.327 | −6.239 | 0.0153390 | thioredoxin-related transmembrane protein 2 |
| SNX7 | 4.142 | 6.574 | 5.592 | 2.951 | 3.043 | 2.233 | −6.237 | 0.0146284 | sorting nexin 7 |
| METTL9 | 4.331 | 7.761 | 6.288 | 3.648 | 3.648 | 3.648 | −6.231 | 0.0286125 | methyltransferase like 9 |
| RPL35 | 12.189 | 12.878 | 13.182 | 10.181 | 10.545 | 10.070 | −6.223 | 0.0064572 | ribosomal protein L35 |
| C5orf62 | 7.512 | 10.089 | 7.789 | 6.377 | 4.876 | 6.432 | −6.217 | 0.0246159 | chromosome 5 open reading frame 62 |
| EFNA3 | 3.194 | 4.587 | 3.284 | 0.648 | 0.648 | 0.648 | −6.213 | 0.0038638 | ephrin-A3 |
| ACSL3 | 5.683 | 8.186 | 8.151 | 4.610 | 5.557 | 5.110 | −6.187 | 0.0314458 | acyl-CoA synthetase long-chain family member 3 |
| SUGT1 | 4.525 | 6.900 | 6.298 | 3.670 | 3.686 | 3.054 | −6.181 | 0.0196662 | SGT 1, suppressor of G2 allele of SKP1 (*S. cerevisiae*) |
| PIK3IP1 | 6.003 | 7.014 | 6.532 | 4.196 | 3.686 | 3.905 | −6.175 | 0.0054187 | phosphoinositide-3-kinase interacting protein 1 |
| RGS5 | 11.990 | 11.020 | 9.193 | 9.369 | 7.997 | 8.222 | −6.154 | 0.0365477 | regulator of G-protein signaling 5 |
| IMP3 | 6.755 | 8.170 | 7.637 | 5.551 | 5.183 | 3.737 | −6.142 | 0.0127920 | IMP3, U3 small nucleolar ribonucleoprotein, homolog (yeast) |
| BANF1 | 10.023 | 8.870 | 8.461 | 7.393 | 6.849 | 5.842 | −6.142 | 0.0167428 | barrier to autointegration factor 1 |
| ARAF | 5.293 | 6.286 | 5.846 | 3.637 | 3.233 | 3.233 | −6.119 | 0.0068523 | v-raf murine sarcoma 3611 viral oncogene homolog |
| TMEM8B | 5.489 | 5.916 | 5.231 | 2.648 | 2.648 | 3.303 | −6.115 | 0.0040489 | transmembrane protein 8B |
| C3orf21 | 6.247 | 5.976 | 4.451 | 3.637 | 3.233 | 3.233 | −6.107 | 0.0198021 | chromosome 3 open reading frame 21 |
| HDGFRP3 | 4.312 | 6.092 | 6.146 | 3.535 | 3.467 | 3.233 | −6.107 | 0.0194291 | No description |
| ARID5B | 8.374 | 10.696 | 10.742 | 7.198 | 3.686 | 8.132 | −6.105 | 0.0210894 | AT rich interactive domain 5B (MRF1-like) |
| CORO1C | 5.125 | 7.561 | 7.252 | 4.642 | 4.456 | 4.865 | −6.104 | 0.0384523 | coronin, actin binding protein, 1C |
| SELK | 8.371 | 10.072 | 10.082 | 7.474 | 6.953 | 7.181 | −6.098 | 0.0172399 | No description |
| PLAT | 6.877 | 8.662 | 7.327 | 5.147 | 4.600 | 4.724 | −6.076 | 0.0080773 | plasminogen activator, tissue |
| TRPT1 | 4.817 | 5.751 | 6.138 | 3.535 | 3.043 | 2.233 | −6.072 | 0.0102083 | tRNA phosphotransferase 1 |
| CMPK1 | 8.673 | 9.889 | 9.282 | 7.287 | 7.000 | 5.658 | −6.069 | 0.0117272 | cytidine monophosphate (UMP-CMP) kinase 1, cytosolic |
| NAB2 | 7.053 | 6.359 | 6.237 | 3.637 | 4.043 | 4.007 | −6.065 | 0.0040759 | NGFI-A binding protein 2 (EGR1 binding protein 2) |
| UBA2 | 6.318 | 8.304 | 7.939 | 5.357 | 5.339 | 4.697 | −6.062 | 0.0173847 | ubiquitin-like modifier activating enzyme 2 |
| IFT52 | 5.503 | 4.833 | 5.013 | 3.670 | 2.233 | 2.233 | −6.061 | 0.0129813 | intraflagellar transport 52 homolog (Chlamydomonas) |
| RPL13 | 13.742 | 14.792 | 14.180 | 11.461 | 11.580 | 11.650 | −6.060 | 0.0043061 | ribosomal protein L13 |
| PYGO2 | 6.851 | 6.851 | 7.028 | 4.678 | 4.240 | 4.264 | −6.009 | 0.0029487 | pygopus homolog 2 (*Drosophila*) |
| TMED9 | 5.173 | 5.804 | 5.327 | 3.218 | 2.648 | 2.648 | −6.005 | 0.0102146 | transmembrane emp24 protein transport domain containing 9 |
| EGLN3 | 5.809 | 5.830 | 6.626 | 3.442 | 2.970 | 4.042 | −5.998 | 0.0070832 | egl nine homolog 3 (*C. elegans*) |
| HSPC159 | 4.817 | 5.770 | 4.796 | 2.233 | 2.233 | 2.233 | −5.994 | 0.0030659 | No description |

TABLE 4-continued

Differentially Expressed Genes in CD44+ Breast Epithelial Cells

| Gene Symbol | Nulliparous (NP) Samples | | | | Parous (P) Samples | | | | Pseudo fold change | P value | Gene description |
|---|---|---|---|---|---|---|---|---|---|---|---|
| | CD44+ N48 | CD44+ N58 | CD44+ N43 | | CD44+ N37 | CD44+ N39 | CD44+ N40 | | | | |
| PLEKHF2 | 4.817 | 6.215 | 6.975 | | 4.151 | 4.037 | 2.233 | | -5.994 | 0.0230340 | pleckstrin homology domain containing, family F (with FYVE domain) member 2 |
| RAP2A | 7.243 | 8.050 | 8.038 | | 5.488 | 4.141 | 5.455 | | -5.991 | 0.0077612 | RAP2A, member of RAS oncogene family |
| SLC39A1 | 7.002 | 8.711 | 8.409 | | 6.372 | 5.828 | 4.007 | | -5.983 | 0.0199608 | solute carrier family 39 (zinc transporter), member 1 |
| RNF19B | 7.533 | 8.410 | 8.136 | | 4.966 | 5.700 | 5.556 | | -5.979 | 0.0054367 | ring finger protein 19B |
| SCAMP5 | 5.781 | 3.475 | 4.308 | | 3.202 | 1.648 | 1.648 | | -5.975 | 0.0263588 | secretory carrier membrane protein 5 |
| KLHL21 | 9.887 | 11.398 | 10.774 | | 7.104 | 8.195 | 9.235 | | -5.972 | 0.0184350 | kelch-like21 (*Drosophila*) |
| DNALI1 | 5.042 | 4.225 | 5.281 | | 3.830 | 1.648 | 1.648 | | -5.966 | 0.0208801 | dynein, axonemal, light intermediate chain 1 |
| OS9 | 6.612 | 7.923 | 7.187 | | 4.042 | 5.250 | 5.176 | | -5.939 | 0.0135816 | osteosarcoma amplified 9, endoplasmic reticulum lectin |
| FBLN7 | 6.818 | 6.418 | 6.481 | | 4.575 | 3.508 | 3.911 | | -5.937 | 0.0056738 | fibulin 7 |
| SLIT3 | 8.311 | 7.742 | 6.498 | | 5.476 | 4.580 | 5.173 | | -5.934 | 0.0147282 | slit homolog 3 (*Drosophila*) |
| FAM192A | 4.086 | 6.285 | 6.612 | | 3.637 | 4.043 | 3.701 | | -5.934 | 0.0491054 | family with sequence similarity 192, member A |
| HIF1A | 10.317 | 10.443 | 9.638 | | 8.472 | 7.234 | 7.074 | | -5.916 | 0.0104759 | hypoxia inducible factor 1, alpha subunit (basic helix-loop-helix transcription factor) |
| HNRNPR | 4.086 | 7.056 | 6.697 | | 4.173 | 4.135 | 3.233 | | -5.905 | 0.0467047 | heterogeneous nuclear ribonucleoprotein R |
| PAIP1 | 4.904 | 7.555 | 6.730 | | 4.173 | 4.490 | 3.701 | | -5.884 | 0.0276156 | poly(A) binding protein interacting protein 1 |
| C11orf59 | 6.072 | 7.542 | 6.996 | | 5.187 | 4.223 | 3.516 | | -5.879 | 0.0140184 | chromosome 11 open reading frame 59 |
| INSIG2 | 6.476 | 6.690 | 7.256 | | 5.562 | 4.135 | 3.701 | | -5.875 | 0.0170769 | insulin induced gene 2 |
| TMEM130 | 8.090 | 4.788 | 4.248 | | 2.233 | 2.233 | 3.737 | | -5.875 | 0.0257307 | transmembrane protein 130 |
| HK2 | 8.285 | 9.798 | 10.109 | | 6.771 | 7.555 | 6.867 | | -5.871 | 0.0175477 | hexokinase 2 |
| GNL3 | 6.671 | 9.531 | 8.646 | | 6.092 | 6.738 | 6.056 | | -5.870 | 0.0458860 | guanine nucleotide binding protein-like 3 (nucleolar) |
| FLJ36031 | 6.726 | 8.735 | 6.317 | | 4.124 | 4.400 | 4.173 | | -5.870 | 0.0097348 | No description |
| AP3S1 | 3.792 | 7.053 | 6.211 | | 3.838 | 3.659 | 2.648 | | -5.868 | 0.0387227 | adaptor-related protein complex 3, sigma 1 subunit |
| SERPINF1 | 7.193 | 10.266 | 7.539 | | 4.988 | 4.764 | 5.618 | | -5.862 | 0.0130083 | serpin peptidase inhibitor, clade F (alpha-2 antiplasmin, pigment epithelium derived factor), member 1 |
| COLEC12 | 5.393 | 6.309 | 6.415 | | 3.456 | 3.456 | 3.865 | | -5.854 | 0.0075719 | collectin sub-family member 12 |
| CPEB3 | 4.482 | 5.782 | 6.273 | | 3.637 | 3.233 | 3.233 | | -5.852 | 0.0200406 | cytoplasmic polyadenylation element binding protein 3 |
| SRP68 | 4.826 | 7.401 | 7.317 | | 4.854 | 2.970 | 3.516 | | -5.845 | 0.0222146 | signal recognition particle 68 kDa |
| RAB7A | 10.249 | 11.845 | 11.316 | | 8.769 | 9.065 | 8.581 | | -5.845 | 0.0134936 | RAB7A, member RAS oncogene family |
| BBS9 | 3.860 | 3.043 | 3.195 | | 0.648 | 0.648 | 0.648 | | -5.844 | 0.0031310 | Bardet-Biedl syndrome 9 |
| AMIGO1 | 3.860 | 1.387 | 3.195 | | 0.648 | 0.648 | 0.648 | | -5.844 | 0.0279442 | adhesion molecule with Ig-like domain 1 |
| POTEE | 3.194 | 3.195 | 2.552 | | 0.648 | 0.648 | 0.648 | | -5.837 | 0.0056378 | POTE ankyrin domain family, member E |
| B9D1 | 3.194 | 4.235 | 4.389 | | 0.648 | 0.648 | 0.648 | | -5.837 | 0.0104579 | B9 protein domain 1 |
| TST | 3.194 | 4.632 | 5.246 | | 2.714 | 0.648 | 0.648 | | -5.837 | 0.0137508 | thiosulfate sulfurtransferase (rhodanese) |
| ACPL2 | 3.194 | 5.681 | 2.329 | | 0.648 | 0.648 | 0.648 | | -5.837 | 0.0148648 | acid phosphatase-like 2 |
| C6orf26 | 3.194 | 3.871 | 3.881 | | 0.648 | 0.648 | 2.370 | | -5.837 | 0.0155463 | chromosome 6 open reading frame 26 |
| MT1F | 3.194 | 7.939 | 2.329 | | 0.648 | 0.648 | 0.648 | | -5.837 | 0.0208052 | metallothionein 1F |
| ZNF775 | 3.194 | 3.452 | 1.649 | | 0.648 | 0.648 | 0.648 | | -5.837 | 0.0216239 | zinc finger protein 775 |
| GSTO2 | 3.194 | 4.372 | 4.602 | | 0.648 | 3.284 | 0.648 | | -5.837 | 0.0263172 | glutathione S-transferase omega 2 |
| PLEKHH2 | 5.816 | 8.526 | 8.009 | | 5.526 | 5.464 | 5.429 | | -5.836 | 0.0434839 | pleckstrin homology domain containing, family H (with MyTH4 domain) member 2 |
| PRKCDBP | 7.818 | 5.588 | 4.777 | | 3.981 | 3.043 | 2.233 | | -5.835 | 0.0175726 | protein kinase C, delta binding protein |
| HSD3B7 | 7.579 | 8.670 | 6.819 | | 5.246 | 5.034 | 4.670 | | -5.835 | 0.0094076 | hydroxy-delta-5-steroid dehydrogenase, 3 beta-and steroid delta-isomerase 7 |
| RAB28 | 3.194 | 3.192 | 2.987 | | 0.648 | 0.648 | 0.648 | | -5.830 | 0.0019172 | RAB28, member RAS oncogene family |
| MSTO1 | 3.194 | 3.192 | 1.245 | | 0.648 | 0.648 | 0.648 | | -5.830 | 0.0355574 | misato homolog 1 (*Drosophila*) |

TABLE 4-continued

Differentially Expressed Genes in CD44+ Breast Epithelial Cells

| | Nulliparous (NP) Samples | | | Parous (P) Samples | | | | Pseudo fold change | P value | Gene description |
|---|---|---|---|---|---|---|---|---|---|---|
| Gene Symbol | CD44+ N48 | CD44+ N58 | CD44+ N43 | CD44+ N37 | CD44+ N39 | CD44+ N40 | | | | |
| STRAP | 8.127 | 10.013 | 9.747 | 6.931 | 7.042 | 7.475 | | −5.809 | 0.0230541 | serine/threonine kinase receptor associated protein |
| PUM1 | 7.687 | 8.136 | 8.295 | 5.598 | 5.692 | 5.447 | | −5.806 | 0.0040309 | pumilio homolog 1 (Drosophila) |
| PGM1 | 5.982 | 7.245 | 7.302 | 4.711 | 4.709 | 3.694 | | −5.801 | 0.0125633 | phosphoglucomutase 1 |
| MARCKSL1 | 8.745 | 9.044 | 8.764 | 5.514 | 6.666 | 6.231 | | −5.790 | 0.0046582 | MARCKS-like 1 |
| NDNL2 | 5.322 | 7.105 | 6.889 | 4.575 | 3.686 | 3.737 | | −5.774 | 0.0157695 | necdin-like 2 |
| C10orf32 | 6.768 | 7.243 | 7.005 | 4.984 | 4.240 | 4.404 | | −5.769 | 0.0053681 | chromosome 10 open reading frame 32 |
| CTHRC1 | 7.436 | 8.140 | 4.928 | 5.003 | 3.686 | 4.908 | | −5.768 | 0.0399019 | collagen triple helix repeat containing 1 |
| ZNF549 | 4.423 | 5.898 | 4.852 | 2.625 | 1.648 | 3.370 | | −5.765 | 0.0154404 | zinc finger protein 549 |
| GBP2 | 5.422 | 6.840 | 7.284 | 3.848 | 3.978 | 4.756 | | −5.765 | 0.0183560 | guanylate binding protein 2, interferon-inducible |
| CMTM8 | 7.353 | 5.821 | 6.229 | 3.830 | 4.529 | 3.294 | | −5.763 | 0.0116170 | CKLF-like MARVEL transmembrane domain containing 8 |
| HIBADH | 7.118 | 5.374 | 4.760 | 2.951 | 3.043 | 2.233 | | −5.761 | 0.0100073 | 3-hydroxyisobutyrate dehydrogenase |
| PDK3 | 4.264 | 5.743 | 5.330 | 3.218 | 2.648 | 2.648 | | −5.757 | 0.0142728 | pyruvate dehydrogenase kinase, isozyme 3 |
| CDCA4 | 6.220 | 5.272 | 5.577 | 3.871 | 2.233 | 3.054 | | −5.746 | 0.0102263 | cell division cycle associated 4 |
| GPM6B | 6.930 | 7.369 | 7.552 | 5.426 | 4.849 | 4.007 | | −5.734 | 0.0090936 | glycoprotein M6B |
| NEIL1 | 3.792 | 5.168 | 6.310 | 2.648 | 2.648 | 2.648 | | −5.733 | 0.0190381 | nei endonuclease VIII-like 1 (E. coli) |
| XRN2 | 7.015 | 8.976 | 8.492 | 6.457 | 5.783 | 5.780 | | −5.731 | 0.0237009 | 5'-3' exoribonuclease 2 |
| CUTA | 8.905 | 8.990 | 9.443 | 6.391 | 6.826 | 6.472 | | −5.726 | 0.0036627 | cutA divalent cation tolerance homolog (E. coli) |
| ARFIP1 | 5.235 | 6.898 | 7.113 | 4.385 | 4.385 | 3.516 | | −5.706 | 0.0196302 | ADP-ribosylation factor interacting protein 1 |
| COPB2 | 6.526 | 7.650 | 8.123 | 5.612 | 4.894 | 4.512 | | −5.699 | 0.0142326 | coatomer protein complex, subunit beta 2 (beta prime) |
| CYP51A1 | 7.161 | 8.890 | 8.400 | 6.382 | 5.413 | 5.009 | | −5.691 | 0.0144357 | cytochrome P450, family 51, subfamily A, polypeptide 1 |
| A2M | 9.226 | 9.732 | 7.953 | 6.341 | 6.760 | 6.718 | | −5.688 | 0.0146035 | alpha-2-macroglobulin |
| TMEM64 | 8.289 | 9.700 | 8.730 | 6.144 | 6.091 | 7.199 | | −5.661 | 0.0135726 | transmembrane protein 64 |
| ZNF32 | 6.133 | 6.651 | 5.487 | 4.632 | 3.633 | 2.370 | | −5.657 | 0.0169210 | zinc finger protein 32 |
| BHLHE41 | 5.369 | 7.700 | 6.602 | 4.385 | 4.289 | 4.327 | | −4.840 | 0.0233633 | basic helix-loop-helix family, member e41 |
| KIAA0247 | 10.670 | 10.146 | 9.229 | 8.399 | 7.671 | 6.954 | | −4.840 | 0.0165224 | KIAA0247 |
| UPP1 | 10.908 | 9.557 | 11.190 | 8.915 | 8.329 | 8.117 | | −4.839 | 0.0219893 | uridine phosphorylase 1 |
| UBTD2 | 7.216 | 9.294 | 9.186 | 6.363 | 5.962 | 7.021 | | −4.835 | 0.0300919 | ubiquitin domain containing 2 |
| FAM129B | 7.178 | 9.227 | 9.682 | 6.881 | 7.410 | 5.914 | | −4.831 | 0.0488759 | family with sequence similarity 129, member B |
| SLC17A5 | 6.137 | 7.185 | 6.244 | 4.854 | 4.879 | 3.865 | | −4.830 | 0.0215303 | solute carrier family 17 (anion/sugar transporter), member 5 |
| SCN4B | 8.545 | 7.378 | 8.210 | 5.181 | 4.587 | 4.536 | | −4.827 | 0.0116260 | sodium channel, voltage-gated, type IV, beta |
| FAT1 | 7.748 | 9.952 | 9.499 | 6.490 | 7.682 | 7.039 | | −4.824 | 0.0368073 | FAT tumor suppressor homolog 1 (Drosophila) |
| AK3 | 7.804 | 7.360 | 6.967 | 5.767 | 4.646 | 5.091 | | −4.817 | 0.0130998 | adenylate kinase 3 |
| TMEM183B | 4.647 | 7.172 | 6.138 | 3.871 | 3.871 | 3.966 | | −4.813 | 0.0310984 | transmembrane protein 183B |
| TRIP10 | 7.296 | 7.741 | 7.484 | 4.782 | 5.531 | 5.218 | | −4.812 | 0.0065889 | thyroid hormone receptor interactor 10 |
| TP53TG1 | 5.550 | 3.881 | 2.401 | 0.648 | 3.284 | 0.648 | | −4.812 | 0.0459317 | TP53 target 1 (non-protein coding) |
| CDKN2C | 5.416 | 5.652 | 6.164 | 3.625 | 2.648 | 3.897 | | −4.811 | 0.0113965 | cyclin-dependent kinase inhibitor 2C (p18, inhibits CDK4) |
| CBX1 | 6.640 | 7.378 | 8.210 | 4.756 | 5.308 | 5.118 | | −4.791 | 0.0127581 | chromobox homolog 1 |
| PSMA4 | 6.017 | 8.161 | 7.815 | 5.901 | 5.303 | 4.670 | | −4.787 | 0.0345917 | proteasome (prosome, macropain) subunit, alpha type, 4 |
| RGS2 | 5.945 | 6.053 | 5.834 | 2.951 | 3.686 | 4.858 | | −4.787 | 0.0215574 | regulator of G-protein signaling 2, 24 kDa |
| GPAA1 | 7.816 | 7.413 | 7.757 | 5.761 | 5.155 | 5.206 | | −4.782 | 0.0065799 | glycosylphosphatidylinositol anchor attachment protein 1 homolog (yeast) |
| AKIRIN1 | 8.894 | 8.784 | 8.501 | 6.632 | 6.384 | 6.529 | | −4.774 | 0.0052329 | akirin 1 |
| SPP1 | 5.293 | 5.709 | 5.949 | 3.233 | 3.694 | 3.233 | | −4.771 | 0.0073515 | secreted phosphoprotein 1 |
| C3orf58 | 5.977 | 6.298 | 6.215 | 3.961 | 4.240 | 3.648 | | −4.771 | 0.0066971 | chromosome 3 open reading frame 58 |
| TMC7 | 6.787 | 7.891 | 7.393 | 5.451 | 5.022 | 5.140 | | −4.769 | 0.0121709 | transmembrane channel-like 7 |
| ACLY | 4.672 | 6.137 | 5.902 | 3.648 | 3.648 | 3.648 | | −4.769 | 0.0231948 | ATP citrate lyase |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| RPL10A | 13.165 | 13.100 | 13.695 | 10.846 | 11.360 | 11.289 | −4.769 | 0.0089841 | ribosomal protein L10a |
| PLEKHA3 | 6.594 | 8.766 | 8.387 | 6.135 | 6.078 | 6.345 | −4.763 | 0.0490603 | pleckstrin homology domain containing, family A (phosphoinositide binding specific) member 3 |
| HIC1 | 11.438 | 7.730 | 8.577 | 6.269 | 6.328 | 6.656 | −4.751 | 0.0239296 | hypermethylated in cancer 1 |
| TMEM205 | 5.982 | 7.887 | 6.866 | 5.290 | 4.618 | 3.897 | −4.750 | 0.0209480 | transmembrane protein 205 |
| TMED2 | 9.676 | 11.149 | 10.815 | 8.902 | 8.419 | 7.697 | −4.748 | 0.0189383 | transmembrane emp24 domain trafficking protein 2 |
| CASP7 | 4.895 | 6.405 | 5.740 | 4.579 | 2.648 | 2.648 | −4.745 | 0.0227428 | caspase 7, apoptosis-related cysteine peptidase |
| MAP3K7IP2 | 6.010 | 8.042 | 7.761 | 5.653 | 5.517 | 5.145 | −4.740 | 0.0395802 | No description |
| CPNE3 | 6.717 | 6.868 | 6.062 | 4.099 | 4.968 | 3.818 | −4.736 | 0.0128322 | copine III |
| STK10 | 6.932 | 7.683 | 7.737 | 5.041 | 5.494 | 5.109 | −4.735 | 0.0091179 | serine/threonine kinase 10 |
| SPIN4 | 4.744 | 5.051 | 4.892 | 2.648 | 2.648 | 2.648 | −4.734 | 0.0038367 | spindlin family, member 4 |
| MYL12B | 10.073 | 11.106 | 10.901 | 8.662 | 9.197 | 7.666 | −4.720 | 0.0188211 | myosin, light chain 12B, regulatory |
| ANKRD46 | 5.976 | 5.634 | 4.916 | 3.737 | 3.686 | 2.233 | −4.720 | 0.0174360 | ankyrin repeat domain 46 |
| ARPC5L | 6.482 | 7.840 | 7.539 | 5.303 | 5.032 | 5.551 | −4.708 | 0.0197931 | actin related protein 2/3 complex, subunit 5-like |
| FBXO21 | 7.248 | 7.892 | 7.660 | 5.657 | 5.239 | 5.109 | −4.706 | 0.0074908 | F-box protein 21 |
| GYG1 | 8.087 | 8.244 | 6.554 | 6.013 | 5.807 | 4.837 | −4.693 | 0.0268828 | glycogenin 1 |
| RHOJ | 6.058 | 5.195 | 5.787 | 2.970 | 3.508 | 3.859 | −4.675 | 0.0111747 | ras homolog gene family, member J |
| QARS | 5.282 | 7.280 | 6.225 | 4.151 | 4.001 | 3.516 | −4.672 | 0.0163296 | glutaminyl-tRNA synthetase |
| TTC7B | 3.947 | 5.731 | 5.438 | 2.970 | 3.508 | 2.970 | −4.669 | 0.0312336 | tetratricopeptide repeat domain 7B |
| CYC1 | 4.214 | 6.297 | 6.338 | 3.456 | 4.115 | 3.456 | −4.668 | 0.0387865 | cytochrome c-1 |
| ATF1 | 6.645 | 6.245 | 6.813 | 4.424 | 4.611 | 3.516 | −4.661 | 0.0091470 | activating transcription factor 1 |
| CHP | 10.174 | 10.065 | 9.367 | 7.904 | 7.845 | 7.696 | −4.659 | 0.0112655 | No description |
| MTDH | 6.867 | 9.035 | 7.897 | 5.678 | 5.754 | 5.172 | −4.655 | 0.0173279 | metadherin |
| USP22 | 9.631 | 10.672 | 10.401 | 8.454 | 7.912 | 8.017 | −4.654 | 0.0135026 | ubiquitin specific peptidase 22 |
| CRMP1 | 6.735 | 4.866 | 4.793 | 2.648 | 2.648 | 3.897 | −4.653 | 0.0214873 | collapsin response mediator protein 1 |
| MPST | 6.368 | 6.975 | 7.102 | 5.167 | 4.151 | 4.481 | −4.650 | 0.0119941 | mercaptopyruvate sulfurtransferase |
| PSMD4 | 7.568 | 8.050 | 7.920 | 6.536 | 5.351 | 5.407 | −4.649 | 0.0160925 | proteasome (prosome, macropain) 26S subunit, non-ATPase, 4 |
| EIF3G | 7.555 | 8.990 | 8.471 | 6.495 | 6.259 | 5.670 | −4.631 | 0.0160835 | eukaryotic translation initiation factor 3, subunit G |
| CBR1 | 7.067 | 7.078 | 7.224 | 5.601 | 4.811 | 4.868 | −4.628 | 0.0117029 | carbonyl reductase 1 |
| ELL | 9.947 | 10.095 | 10.077 | 7.738 | 7.812 | 8.602 | −4.625 | 0.0134603 | elongation factor RNA polymerase II |
| NKRF | 6.023 | 6.481 | 6.057 | 3.494 | 3.852 | 5.367 | −4.611 | 0.0291095 | NFKB repressing factor |
| SELENBP1 | 8.400 | 6.185 | 6.345 | 3.981 | 4.777 | 5.279 | −4.608 | 0.0263678 | selenium binding protein 1 |
| LARP4 | 5.019 | 6.746 | 6.022 | 4.099 | 3.818 | 3.818 | −4.606 | 0.0225674 | La ribonucleoprotein domain family, member 4 |
| SLC2A1 | 10.418 | 10.351 | 11.211 | 8.888 | 9.010 | 8.023 | −4.598 | 0.0178631 | solute carrier family 2 (facilitated glucose transporter), member 1 |
| SLC25A11 | 4.525 | 5.244 | 5.693 | 4.417 | 3.043 | 2.233 | −4.597 | 0.0389667 | solute carrier family 25 (mitochondrial carrier; oxoglutarate carrier), member 11 |
| NRXN3 | 5.168 | 5.753 | 3.901 | 2.970 | 3.508 | 2.970 | −4.587 | 0.0362652 | neurexin 3 |
| RPL13AP5 | 7.959 | 8.814 | 8.373 | 6.177 | 6.202 | 6.173 | −4.582 | 0.00082125 | ribosomal protein L13a pseudogene 5 |
| CAT | 6.688 | 6.266 | 5.855 | 4.610 | 3.467 | 4.071 | −4.581 | 0.0129674 | catalase |
| FBN1 | 9.006 | 8.572 | 8.586 | 6.394 | 6.256 | 7.160 | −4.568 | 0.0118367 | fibrillin 1 |
| NCRNA00095 | 7.193 | 9.056 | 9.060 | 6.869 | 6.426 | 6.836 | −4.567 | 0.0459636 | non-protein coding RNA 95 |
| PCGF6 | 3.422 | 5.997 | 5.529 | 2.625 | 3.499 | 1.648 | −5.650 | 0.0298707 | polycomb group ring finger 6 |
| TCEAL4 | 4.525 | 6.368 | 6.871 | 3.871 | 3.559 | 3.905 | −5.645 | 0.0279692 | transcription elongation factor A (SH)-like 4 |
| ZNF581 | 6.103 | 7.163 | 7.472 | 4.667 | 4.168 | 4.857 | −5.639 | 0.0122568 | zinc finger protein 581 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| CD70 | 3.194 | 4.632 | 3.143 | 0.648 | 2.987 | 0.648 | −5.636 | 0.0351629 | CD70 molecule |
| PSMA6 | 8.000 | 9.344 | 9.392 | 6.971 | 5.653 | 5.510 | −5.620 | 0.0093806 | proteasome (prosome, macropain) subunit, alpha type, 6 |
| SFRP4 | 12.839 | 11.231 | 10.687 | 9.479 | 8.743 | 8.712 | −5.609 | 0.0144627 | secreted frizzled-related protein 4 |
| RPL15 | 10.934 | 12.654 | 12.144 | 9.708 | 9.513 | 9.656 | −5.609 | 0.0152454 | ribosomal protein L15 |
| TSPAN6 | 4.620 | 5.615 | 5.705 | 3.218 | 2.648 | 2.648 | −5.608 | 0.0082395 | tetraspanin 6 |
| UBAC2 | 4.936 | 3.898 | 4.717 | 2.233 | 2.233 | 2.233 | −5.594 | 0.0088884 | UBA domain containing 2 |
| LIMA1 | 5.938 | 7.799 | 5.713 | 3.456 | 5.011 | 3.456 | −5.589 | 0.0216392 | LIM domain and actin binding 1 |
| DDAH1 | 8.379 | 7.700 | 6.862 | 5.394 | 5.220 | 4.778 | −5.582 | 0.0099712 | dimethylarginine dimethylaminohydrolase 1 |
| GNPNAT1 | 4.086 | 7.377 | 5.713 | 3.233 | 3.694 | 3.233 | −5.579 | 0.0322853 | glucosamine-phosphate N-acetyltransferase 1 |
| C1S | 8.434 | 10.292 | 9.675 | 6.966 | 6.804 | 7.815 | −5.567 | 0.0197542 | complement component 1, s subcomponent |
| GEFT | 3.792 | 6.425 | 5.769 | 3.218 | 3.294 | 3.694 | −5.560 | 0.0450139 | No description |
| FMO5 | 3.792 | 5.813 | 6.326 | 2.648 | 3.852 | 2.648 | −5.554 | 0.0308981 | flavin containing monooxygenase 5 |
| ZDHHC4 | 6.089 | 6.089 | 5.516 | 4.276 | 3.043 | 3.508 | −5.553 | 0.0108315 | zinc finger, DHHC-type containing 4 |
| NUPL1 | 5.960 | 8.135 | 7.693 | 5.663 | 5.212 | 4.507 | −5.550 | 0.0294749 | nucleoporin like 1 |
| C22orf13 | 8.874 | 9.406 | 9.220 | 7.678 | 6.736 | 6.403 | −5.544 | 0.0129265 | chromosome 22 open reading frame 13 |
| TRA2B | 7.355 | 8.122 | 8.391 | 5.920 | 4.946 | 5.151 | −5.544 | 0.0073605 | transformer 2 beta homolog (Drosophila) |
| TMEM184A | 5.688 | 7.643 | 7.887 | 3.218 | 5.445 | 4.458 | −5.543 | 0.0207192 | transmembrane protein 184A |
| TSC22D2 | 8.380 | 8.904 | 7.746 | 5.277 | 5.804 | 6.642 | −5.536 | 0.0124101 | TSC22 domain family, member 2 |
| IGFBP7 | 9.173 | 11.325 | 7.793 | 7.053 | 5.635 | 6.704 | −5.535 | 0.0199518 | insulin-like growth factor binding protein 7 |
| TMED3 | 7.705 | 7.726 | 6.980 | 5.897 | 4.490 | 5.237 | −5.533 | 0.0143525 | transmembrane emp24 protein transport domain containing 3 |
| PDZRN3 | 6.135 | 7.870 | 6.348 | 3.881 | 3.827 | 4.670 | −5.530 | 0.0112745 | PDZ domain containing ring finger 3 |
| C17orf85 | 4.872 | 6.851 | 6.338 | 3.808 | 4.383 | 3.456 | −5.530 | 0.0248412 | chromosome 17 open reading frame 85 |
| IDH2 | 4.142 | 6.999 | 7.090 | 2.951 | 4.624 | 2.233 | −5.525 | 0.0266458 | Description |
| HNRPDL | 6.495 | 8.763 | 8.171 | 5.361 | 5.706 | 5.741 | −5.523 | 0.0243296 | heterogeneous nuclear ribonucleoprotein D-like |
| PHC2 | 10.494 | 10.999 | 10.454 | 8.785 | 8.028 | 7.525 | −5.522 | 0.0077702 | polyhomeotic homolog 2 (Drosophila) |
| MTCH2 | 3.947 | 5.711 | 5.435 | 2.970 | 2.970 | 2.970 | −5.522 | 0.0229189 | mitochondrial carrier homolog 2 (C. elegans) |
| MGAT4B | 7.903 | 8.382 | 8.816 | 6.352 | 5.872 | 5.815 | −5.518 | 0.0078957 | mannosyl (alpha-1,3-)-glycoprotein beta-1,4-N-acetylglucosaminyltransferase, isozyme B |
| CLIC1 | 9.182 | 10.361 | 10.203 | 7.858 | 7.739 | 7.694 | −5.515 | 0.0131594 | chloride intracellular channel 1 |
| C1orf122 | 5.739 | 7.166 | 6.505 | 3.351 | 4.043 | 4.262 | −5.512 | 0.0093716 | chromosome 1 open reading frame 122 |
| DDIT4 | 7.951 | 5.926 | 5.679 | 3.218 | 3.659 | 3.694 | −5.509 | 0.0097889 | DNA-damage-inducible transcript 4 |
| POLR1D | 6.420 | 9.086 | 8.082 | 5.776 | 5.621 | 5.444 | −5.507 | 0.0269542 | polymerase (RNA) I polypeptide D, 16 kDa |
| EPHB4 | 7.223 | 7.393 | 7.187 | 4.873 | 4.910 | 4.727 | −5.503 | 0.0024440 | EPH receptor B4 |
| MBNL2 | 8.177 | 9.161 | 8.099 | 5.642 | 5.735 | 6.524 | −5.489 | 0.0089335 | muscleblind-like 2 (Drosophila) |
| RAC1 | 11.568 | 11.897 | 11.492 | 9.441 | 9.179 | 8.660 | −5.487 | 0.0043740 | ras-related C3 botulinum toxin substrate 1 (rho family, small GTP binding protein Rac1) |
| TMEM50A | 6.274 | 6.661 | 6.689 | 4.688 | 3.818 | 4.146 | −5.487 | 0.0075629 | transmembrane protein 50A |
| DCAF8 | 6.943 | 7.668 | 7.913 | 4.959 | 4.488 | 6.545 | −5.485 | 0.0251047 | DDB1 and CUL4 associated factor 8 |
| PGF | 5.600 | 5.966 | 5.647 | 3.442 | 2.970 | 3.516 | −5.463 | 0.0045057 | placental growth factor |
| ZFYVE9 | 5.503 | 5.076 | 4.889 | 2.951 | 2.233 | 3.054 | −5.461 | 0.0072246 | zinc finger, FYVE domain containing 9 |
| HHAT | 4.860 | 4.097 | 3.379 | 1.648 | 1.648 | 1.648 | −5.460 | 0.0093508 | hedgehog acyltransferase |
| PDE4A | 7.009 | 6.933 | 5.763 | 4.561 | 3.648 | 4.264 | −5.457 | 0.0117938 | phosphodiesterase 4A, cAMP-specific |
| BDKRB2 | 4.744 | 5.512 | 6.344 | 3.897 | 2.648 | 2.648 | −5.451 | 0.0149730 | bradykinin receptor B2 |
| SNHG6 | 7.661 | 9.670 | 9.602 | 6.441 | 6.714 | 7.223 | −5.451 | 0.0252884 | small nucleolar RNA host gene 6 (non-protein coding) |
| CYP27A1 | 3.619 | 6.116 | 6.074 | 3.670 | 3.467 | 2.233 | −5.450 | 0.0407289 | cytochrome P450, family 27, subfamily A, polypeptide 1 |
| PPA1 | 6.280 | 9.481 | 8.044 | 5.747 | 5.600 | 5.561 | −5.441 | 0.0321279 | pyrophosphatase (inorganic) 1 |

TABLE 4-continued

Differentially Expressed Genes in CD44+ Breast Epithelial Cells

| Gene Symbol | Nulliparous (NP) Samples | | | | Parous (P) Samples | | | | Pseudo fold change | P value | Gene description |
|---|---|---|---|---|---|---|---|---|---|---|---|
| | CD44+ N48 | CD44+ N58 | CD44+ N43 | | CD44+ N37 | CD44+ N39 | CD44+ N40 | | | | |
| DEF6 | 4.423 | 5.992 | 5.736 | | 2.625 | 3.499 | 3.294 | | −5.432 | 0.0174090 | differentially expressed in FDCP 6 homolog (mouse) |
| C3orf59 | 6.454 | 7.730 | 4.845 | | 3.961 | 4.600 | 4.013 | | −5.430 | 0.0353314 | chromosome 3 open reading frame 59 |
| F11R | 6.220 | 8.124 | 7.913 | | 5.377 | 5.690 | 4.950 | | −5.404 | 0.0262270 | F11 receptor |
| FBXL5 | 4.709 | 6.874 | 5.402 | | 2.970 | 2.970 | 2.970 | | −5.395 | 0.0114555 | F-box and leucine-rich repeat protein 5 |
| WDR25 | 5.452 | 4.624 | 4.835 | | 3.023 | 2.739 | 1.648 | | −5.386 | 0.0105168 | WD repeat domain 25 |
| RTN2 | 5.452 | 4.477 | 4.087 | | 3.023 | 2.739 | 1.648 | | −5.386 | 0.0199111 | reticulon 2 |
| UBE2E2 | 8.331 | 7.788 | 7.019 | | 6.239 | 4.624 | 4.590 | | −5.385 | 0.0144267 | ubiquitin-conjugating enzyme E2E 2 (UBC4/5 homolog, yeast) |
| C14orf1 | 5.322 | 4.575 | 5.379 | | 2.951 | 2.233 | 2.233 | | −5.382 | 0.0056059 | chromosome 14 open reading frame 1 |
| CLEC3B | 9.612 | 9.703 | 11.368 | | 6.949 | 8.384 | 8.941 | | −5.378 | 0.0338631 | C-type lectin domain family 3, member B |
| SLC25A5 | 9.097 | 10.503 | 10.601 | | 7.675 | 8.174 | 7.959 | | −5.376 | 0.0186069 | solute carrier family 25 (mitochondrial carrier; adenine nucleotide translocator), member 5 |
| PFN2 | 8.368 | 8.589 | 8.711 | | 6.766 | 6.047 | 5.942 | | −5.376 | 0.0075900 | profilin 2 |
| TXNIP | 6.967 | 9.337 | 9.046 | | 6.619 | 5.686 | 6.688 | | −5.375 | 0.0341820 | thioredoxin interacting protein |
| CD2AP | 5.346 | 6.216 | 6.063 | | 3.637 | 3.694 | 3.233 | | −5.375 | 0.0076170 | CD2-associated protein |
| TMEM106B | 6.535 | 7.125 | 7.636 | | 4.902 | 4.653 | 4.701 | | −5.366 | 0.0082215 | transmembrane protein 106B |
| ANKRA2 | 3.422 | 4.072 | 4.314 | | 1.648 | 1.648 | 1.648 | | −5.364 | 0.0075179 | ankyrin repeat, family A (RFXANK-like), 2 |
| ANO7 | 6.907 | 7.534 | 7.722 | | 5.051 | 5.303 | 4.933 | | −5.350 | 0.0075359 | anoctamin 7 |
| ELK3 | 6.927 | 6.992 | 6.444 | | 4.580 | 4.508 | 3.859 | | −5.349 | 0.0057127 | ELK3, ETS-domain protein (SRF accessory protein 2) |
| C16orf57 | 5.346 | 7.198 | 7.110 | | 4.779 | 4.135 | 4.007 | | −5.347 | 0.0214111 | chromosome 16 open reading frame 57 |
| DAB2 | 8.218 | 10.388 | 10.550 | | 7.613 | 7.612 | 8.131 | | −5.347 | 0.0420794 | disabled homolog 2, mitogen-responsive phosphoprotein (Drosophila) |
| ARHGEF7 | 7.284 | 8.631 | 8.455 | | 6.162 | 5.915 | 6.037 | | −5.347 | 0.0165827 | Rho guanine nucleotide exchange factor (GEF) 7 |
| NDUFV2 | 6.570 | 7.969 | 7.883 | | 5.551 | 5.458 | 4.777 | | −5.344 | 0.0167248 | NADH dehydrogenase (ubiquinone) flavoprotein 2, 24 kDa |
| ZNF669 | 6.320 | 6.802 | 6.144 | | 3.682 | 3.694 | 4.317 | | −5.341 | 0.0081972 | zinc finger protein 669 |
| HABP4 | 5.552 | 5.719 | 5.120 | | 3.218 | 2.648 | 3.303 | | −5.335 | 0.0061314 | hyaluronan binding protein 4 |
| SPTBN1 | 10.029 | 9.217 | 9.100 | | 7.591 | 6.686 | 7.127 | | −5.331 | 0.0107775 | spectrin, beta, non-erythrocytic 1 |
| TWF2 | 6.565 | 5.122 | 6.216 | | 4.151 | 3.559 | 3.054 | | −5.330 | 0.0140433 | twinfilin, actin-binding protein, homolog 2 (Drosophila) |
| TBL1XR1 | 8.867 | 8.637 | 8.309 | | 6.191 | 5.946 | 6.453 | | −5.327 | 0.0049473 | transducin (beta)-like 1 X-linked receptor 1 |
| NDRG1 | 12.286 | 11.692 | 12.255 | | 9.842 | 8.785 | 10.130 | | −5.324 | 0.0096004 | N-myc downstream regulated 1 |
| KIAA1522 | 6.220 | 7.998 | 8.519 | | 4.653 | 6.111 | 5.093 | | −5.306 | 0.0270416 | KIAA1522 |
| TANC1 | 6.722 | 7.711 | 7.289 | | 4.840 | 5.285 | 4.882 | | −5.303 | 0.0099206 | tetratricopeptide repeat, ankyrin repeat and coiled-coil containing 1 |
| VAPA | 8.602 | 9.121 | 9.187 | | 6.716 | 6.782 | 6.491 | | −5.295 | 0.0056946 | VAMP (vesicle-associated membrane protein)-associated protein A, 33 kDa |
| CBX3 | 6.226 | 8.096 | 8.375 | | 5.082 | 5.970 | 5.441 | | −5.294 | 0.0311310 | chromobox homolog 3 |
| TAGLN2 | 9.473 | 11.280 | 10.668 | | 8.720 | 8.266 | 8.162 | | −5.287 | 0.0223317 | transgelin 2 |
| PICALM | 7.778 | 9.466 | 8.875 | | 6.476 | 7.024 | 6.343 | | −5.275 | 0.0211830 | phosphatidylinositol binding clathrin assembly protein |
| MEST | 8.068 | 7.668 | 6.523 | | 4.042 | 6.479 | 5.270 | | −5.272 | 0.0340912 | mesoderm specific transcript homolog (mouse) |
| GSTK1 | 6.594 | 7.510 | 8.025 | | 3.897 | 5.839 | 5.112 | | −5.271 | 0.0185404 | glutathione S-transferase kappa 1 |
| UROD | 5.688 | 6.255 | 6.429 | | 5.035 | 3.294 | 3.694 | | −5.256 | 0.0221064 | uroporphyrinogen decarboxylase |
| CRYZL1 | 3.422 | 5.191 | 4.041 | | 1.648 | 1.648 | 1.648 | | −5.252 | 0.0103282 | crystallin, zeta (quinone reductase)-like 1 |
| MAP2K3 | 11.671 | 12.062 | 11.686 | | 8.537 | 10.042 | 9.293 | | −5.252 | 0.0092683 | mitogen-activated protein kinase kinase 3 |
| SMARCD3 | 3.619 | 5.860 | 4.624 | | 3.429 | 2.233 | 2.233 | | −5.245 | 0.0334139 | SWI/SNF related, matrix associated, actin dependent regulator of chromatin, subfamily d, member 3 |
| ID2 | 3.619 | 5.989 | 4.624 | | 2.233 | 2.233 | 3.508 | | −5.245 | 0.0355976 | Description |
| ANXA7 | 6.735 | 8.111 | 7.897 | | 6.679 | 5.370 | 4.346 | | −5.238 | 0.0334319 | annexin A7 |

TABLE 4-continued

Differentially Expressed Genes in CD44+ Breast Epithelial Cells

| | Nulliparous (NP) Samples | | | Parous (P) Samples | | | Pseudo | | |
|---|---|---|---|---|---|---|---|---|---|
| Gene Symbol | CD44+ N48 | CD44+ N58 | CD44+ N43 | CD44+ N37 | CD44+ N39 | CD44+ N40 | fold change | P value | Gene description |
| LSM3 | 4.314 | 7.050 | 5.736 | 4.262 | 2.987 | 3.351 | -5.224 | 0.0356697 | LSM3 homolog, U6 small nuclear RNA associated (*S. cerevisiae*) |
| SLC2A4 | 6.219 | 5.618 | 4.456 | 3.233 | 3.233 | 3.701 | -5.223 | 0.0232308 | solute carrier family 2 (facilitated glucose transporter), member 4 |
| RASSF2 | 7.562 | 7.433 | 6.475 | 5.051 | 3.456 | 5.694 | -5.214 | 0.0203560 | Ras association (RalGDS/AF-6) domain family member 2 |
| CTNND1 | 7.795 | 9.011 | 9.247 | 6.093 | 6.866 | 6.366 | -5.210 | 0.0157196 | catenin (cadherin-associated protein), delta 1 |
| TM9SF3 | 9.175 | 10.230 | 10.334 | 7.954 | 7.714 | 6.918 | -5.206 | 0.0122749 | transmembrane 9 superfamily member 3 |
| PIGK | 8.258 | 6.871 | 5.240 | 4.492 | 4.611 | 4.453 | -5.200 | 0.0305425 | phosphatidylinositol glycan anchor biosynthesis, class K |
| TAP1 | 8.312 | 8.348 | 7.276 | 5.936 | 4.791 | 6.286 | -5.190 | 0.0165556 | transporter 1, ATP-binding cassette, sub-family B (MDR/TAP) |
| EPS8 | 6.785 | 8.972 | 8.072 | 6.416 | 5.696 | 5.523 | -5.189 | 0.0295539 | epidermal growth factor receptor pathway substrate 8 |
| RPL32 | 12.723 | 13.973 | 13.998 | 11.002 | 11.306 | 11.623 | -5.189 | 0.0139775 | ribosomal protein L32 |
| DPH5 | 6.547 | 5.409 | 6.543 | 3.202 | 4.174 | 3.557 | -5.179 | 0.0097979 | DPH5 homolog (*S. cerevisiae*) |
| CYFIP2 | 5.322 | 5.772 | 4.753 | 2.951 | 2.233 | 3.905 | -5.171 | 0.0177466 | cytoplasmic FMR1 interacting protein 2 |
| DPAGT1 | 4.709 | 6.196 | 6.049 | 3.442 | 3.827 | 2.970 | -5.166 | 0.0168315 | dolichyl-phosphate (UDP-N-acetylglucosamine) N-acetylglucosaminephosphotransferase 1 (GlcNAc-1-P transferase) |
| ETV5 | 7.352 | 7.346 | 8.046 | 5.197 | 4.576 | 5.678 | -5.163 | 0.0088350 | ets variant 5 |
| PROP | 6.949 | 6.535 | 6.397 | 4.587 | 4.259 | 3.456 | -5.141 | 0.0071976 | prolylcarboxypeptidase (angiotensinase C) |
| TNN | 9.132 | 8.840 | 8.730 | 5.122 | 6.479 | 6.959 | -5.138 | 0.0092932 | tenascin N |
| CMBL | 4.008 | 3.423 | 4.351 | 1.648 | 1.648 | 1.648 | -5.131 | 0.0077882 | carboxymethylenebutenolidase homolog (*Pseudomonas*) |
| GIMAP6 | 5.008 | 5.086 | 3.945 | 2.648 | 2.648 | 2.648 | -5.131 | 0.0156135 | GTPase, IMAP family member 6 |
| CBFB | 7.997 | 9.312 | 8.603 | 6.245 | 5.978 | 6.510 | -5.126 | 0.0100731 | core-binding factor, beta subunit |
| VIM | 13.008 | 15.405 | 12.193 | 10.652 | 10.596 | 11.747 | -5.119 | 0.0284101 | vimentin |
| VPS35 | 6.537 | 7.533 | 8.164 | 5.180 | 5.352 | 4.405 | -5.110 | 0.0136648 | vacuolar protein sorting 35 homolog (*S. cerevisiae*) |
| FBXL20 | 4.817 | 5.109 | 4.583 | 2.951 | 2.233 | 2.233 | -5.098 | 0.0069931 | F-box and leucine-rich repeat protein 20 |
| LPHN3 | 7.536 | 4.583 | 3.211 | 2.233 | 2.233 | 2.233 | -5.098 | 0.0275317 | latrophilin 3 |
| THBS2 | 9.034 | 11.015 | 10.779 | 8.666 | 7.741 | 8.279 | -5.096 | 0.0296919 | thrombospondin 2 |
| CLPP | 5.688 | 6.751 | 6.983 | 4.751 | 4.405 | 2.648 | -5.086 | 0.0179366 | ClpP caseinolytic peptidase, ATP-dependent, proteolytic subunit homolog (*E. coli*) |
| EIF3H | 8.682 | 9.415 | 9.847 | 6.607 | 7.177 | 7.070 | -5.082 | 0.0096600 | eukaryotic translation initiation factor 3, subunit H |
| GPX7 | 5.952 | 6.031 | 5.082 | 4.081 | 2.739 | 2.752 | -5.073 | 0.0119019 | glutathione peroxidase 7 |
| S1PR3 | 5.532 | 7.494 | 6.896 | 5.151 | 3.859 | 4.536 | -5.072 | 0.0270076 | sphingosine-1-phosphate receptor 3 |
| EIF3M | 4.264 | 7.273 | 7.367 | 4.017 | 5.026 | 2.648 | -5.067 | 0.0447768 | eukaryotic translation initiation factor 3, subunit M |
| STX3 | 5.683 | 7.576 | 8.177 | 5.053 | 5.836 | 4.969 | -5.067 | 0.0494672 | syntaxin 3 |
| TNFSF9 | 7.991 | 7.409 | 6.881 | 5.070 | 3.899 | 5.749 | -5.059 | 0.0141154 | tumor necrosis factor (ligand) superfamily, member 9 |
| KLF4 | 8.552 | 10.278 | 8.854 | 6.495 | 6.516 | 7.767 | -5.059 | 0.0209910 | Kruppel-like factor 4 (gut) |
| DPP4 | 5.204 | 5.830 | 2.987 | 3.351 | 0.648 | 3.043 | -5.057 | 0.0481723 | dipeptidyl-peptidase 4 |
| BGN | 11.207 | 11.651 | 8.508 | 6.920 | 6.306 | 9.314 | -5.054 | 0.0282818 | biglycan |
| COMP | 3.792 | 8.519 | 4.986 | 2.648 | 2.648 | 3.694 | -5.054 | 0.0396357 | cartilage oligomeric matrix protein |
| THY1 | 9.053 | 8.901 | 7.411 | 5.796 | 6.398 | 6.720 | -5.040 | 0.0218035 | Thy-1 cell surface antigen |
| SLC15A4 | 6.259 | 6.988 | 6.484 | 4.655 | 4.585 | 3.818 | -5.038 | 0.0108808 | solute carrier family 15, member 4 |
| HECTD1 | 5.386 | 7.520 | 7.697 | 5.189 | 4.555 | 5.225 | -5.033 | 0.0457432 | HECT domain containing 1 |
| RPS27L | 8.453 | 8.955 | 8.828 | 7.498 | 6.356 | 6.125 | -5.020 | 0.0175206 | ribosomal protein S27-like |
| OPN3 | 4.969 | 7.125 | 6.601 | 3.442 | 4.797 | 4.042 | -5.020 | 0.0300205 | opsin 3 |
| ABLIM1 | 7.737 | 8.444 | 7.479 | 5.812 | 6.116 | 5.081 | -5.020 | 0.0135366 | actin binding LIM protein 1 |
| LMCD1 | 8.478 | 8.126 | 6.986 | 5.691 | 6.151 | 5.210 | -5.018 | 0.0180406 | LIM and cysteine-rich domains 1 |

TABLE 4-continued

Differentially Expressed Genes in CD44+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD44+ N48 | CD44+ N58 | CD44+ N43 | CD44+ N37 | CD44+ N39 | CD44+ N40 | | | | |
| PAIP2 | 8.523 | 9.711 | 7.936 | 6.770 | 6.082 | 6.196 | | −5.017 | 0.0150471 | poly(A) binding protein interacting protein 2 |
| PPFIBP1 | 7.147 | 8.545 | 7.360 | 5.036 | 5.811 | 5.028 | | −5.009 | 0.0127338 | PTPRF interacting protein, binding protein 1 (liprin beta 1) |
| IGFBP3 | 8.376 | 8.465 | 8.183 | 6.507 | 5.859 | 5.866 | | −5.008 | 0.0069210 | insulin-like growth factor binding protein 3 |
| DYNLT3 | 5.999 | 7.872 | 7.474 | 5.548 | 3.694 | 4.054 | | −5.006 | 0.0162132 | dynein, light chain, Tctex-type 3 |
| CRIP1 | 4.620 | 8.749 | 4.971 | 2.648 | 2.648 | 2.648 | | −5.003 | 0.0164801 | cysteine-rich protein 1 (intestinal) |
| ZNF281 | 4.264 | 5.746 | 6.486 | 4.165 | 2.648 | 3.303 | | −4.999 | 0.0320912 | zinc finger protein 281 |
| STAU1 | 7.554 | 8.213 | 8.121 | 5.234 | 5.996 | 5.637 | | −4.994 | 0.0077231 | staufen, RNA binding protein, homolog 1 (Drosophila) |
| DUSP4 | 5.047 | 7.350 | 6.965 | 3.648 | 5.030 | 4.013 | | −4.993 | 0.0299047 | dual specificity phosphatase 4 |
| SPOCK1 | 7.683 | 6.434 | 5.535 | 4.501 | 4.115 | 3.456 | | −4.990 | 0.0159248 | sparc/osteonectin, cwcv and kazal-like domains proteoglycan (testican) 1 |
| DDB1 | 8.857 | 9.921 | 9.997 | 7.853 | 7.515 | 6.538 | | −4.990 | 0.0158742 | damage-specific DNA binding protein 1, 127 kDa |
| ETS2 | 8.823 | 10.662 | 8.965 | 7.659 | 6.504 | 6.773 | | −4.990 | 0.0161471 | v-ets erythroblastosis virus E26 oncogene homolog 2 (avian) |
| ECH1 | 7.127 | 6.505 | 6.126 | 3.808 | 4.853 | 3.865 | | −4.986 | 0.0107865 | enoyl CoA hydratase 1, peroxisomal |
| PAM | 7.010 | 8.371 | 8.151 | 6.054 | 5.229 | 5.262 | | −4.984 | 0.0139144 | peptidylglycine alpha-amidating monooxygenase |
| GMPR | 4.423 | 5.056 | 4.624 | 2.625 | 2.739 | 1.648 | | −4.983 | 0.0100551 | guanosine monophosphate reductase |
| NFYC | 5.904 | 6.810 | 7.164 | 4.397 | 3.978 | 4.848 | | −4.982 | 0.0145057 | nuclear transcription factor Y, gamma |
| HOPX | 8.532 | 5.783 | 5.472 | 3.278 | 3.467 | 5.279 | | −4.980 | 0.0322541 | HOP homeobox |
| TMEM101 | 7.032 | 7.005 | 7.206 | 6.103 | 4.717 | 3.859 | | −4.978 | 0.0237438 | transmembrane protein 101 |
| NFIL3 | 7.849 | 9.441 | 9.373 | 6.203 | 5.654 | 7.126 | | −4.977 | 0.0148468 | nuclear factor, interleukin 3 regulated |
| COL15A1 | 9.137 | 7.542 | 7.424 | 6.299 | 5.784 | 5.109 | | −4.977 | 0.0196842 | collagen, type XV, alpha 1 |
| RILPL2 | 4.142 | 7.007 | 5.592 | 3.278 | 2.233 | 3.508 | | −4.976 | 0.0229009 | Rab interacting lysosomal protein-like 2 |
| MFAP3 | 8.742 | 7.829 | 7.763 | 6.427 | 5.794 | 5.215 | | −4.975 | 0.0135276 | microfibrillar-associated protein 3 |
| IL33 | 6.169 | 7.249 | 5.562 | 4.935 | 3.648 | 3.648 | | −4.973 | 0.0214964 | interleukin 33 |
| ADCY3 | 7.330 | 9.122 | 7.772 | 5.911 | 5.460 | 5.112 | | −4.965 | 0.0118458 | adenylate cyclase 3 |
| MTND2 | 12.858 | 14.115 | 13.694 | 11.547 | 11.803 | 10.492 | | −4.963 | 0.0163386 | No description |
| TC2N | 4.331 | 6.111 | 6.550 | 3.648 | 4.240 | 3.648 | | −4.959 | 0.0449709 | tandem C2 domains, nuclear |
| LGMN | 8.273 | 8.959 | 8.602 | 6.425 | 5.967 | 6.638 | | −4.943 | 0.0081196 | legumain |
| PSMD8 | 8.568 | 10.496 | 10.041 | 8.046 | 7.737 | 6.492 | | −4.939 | 0.0247490 | proteasome (prosome, macropain) 26S subunit, non-ATPase, 8 |
| AGRN | 6.981 | 7.471 | 7.990 | 4.678 | 5.852 | 4.859 | | −4.936 | 0.0123428 | agrin |
| SETD7 | 5.151 | 6.881 | 6.650 | 4.549 | 4.349 | 4.349 | | −4.930 | 0.0330652 | SET domain containing (lysine methyltransferase) 7 |
| RP1A | 5.169 | 7.372 | 6.676 | 4.377 | 4.453 | 4.174 | | −4.920 | 0.0273605 | ribose 5-phosphate isomerase A |
| CCPG1 | 6.397 | 6.361 | 6.543 | 4.099 | 3.818 | 4.377 | | −4.917 | 0.0046492 | cell cycle progression 1 |
| SLC2A4RG | 7.638 | 6.653 | 6.764 | 4.357 | 4.876 | 5.005 | | −4.910 | 0.0108135 | SLC2A4 regulator |
| C6orf168 | 4.264 | 4.944 | 5.016 | 2.648 | 2.648 | 2.648 | | −4.910 | 0.0099622 | chromosome 6 open reading frame 168 |
| PTH1R | 6.017 | 3.859 | 5.266 | 2.970 | 2.970 | 2.970 | | −4.910 | 0.0259088 | parathyroid hormone 1 receptor |
| LRRN4CL | 5.786 | 6.409 | 5.979 | 3.456 | 4.115 | 3.865 | | −4.904 | 0.0080523 | LRRN4 C-terminal like |
| C7orf29 | 4.647 | 3.192 | 4.972 | 3.351 | 2.353 | 0.648 | | −4.903 | 0.0417133 | chromosome 7 open reading frame 29 |
| TRAM1 | 9.311 | 9.345 | 8.801 | 8.048 | 7.019 | 6.156 | | −4.898 | 0.0235657 | translocation associated membrane protein 1 |
| DCUN1D3 | 8.532 | 9.133 | 10.041 | 6.406 | 5.564 | 8.041 | | −4.898 | 0.0304052 | DCN1, defective in cullin neddylation 1, domain containing 3 (S. cerevisiae) |
| LUC7L2 | 7.971 | 8.499 | 8.457 | 6.207 | 6.046 | 5.911 | | −4.896 | 0.0059574 | LUC7-like 2 (S. cerevisiae) |
| GPN1 | 4.525 | 4.554 | 3.184 | 2.233 | 2.233 | 2.233 | | −4.896 | 0.0252974 | GPN-loop GTPase 1 |
| ISM1 | 4.525 | 4.586 | 2.820 | 2.233 | 2.233 | 2.233 | | −4.896 | 0.0397965 | isthmin 1 homolog (zebrafish) |
| SELPLG | 4.525 | 5.585 | 3.170 | 2.233 | 2.233 | 3.054 | | −4.896 | 0.0413293 | selectin P ligand |
| SS18 | 8.251 | 8.827 | 8.980 | 7.086 | 5.960 | 6.078 | | −4.894 | 0.0115421 | synovial sarcoma translocation, chromosome 18 |

TABLE 4-continued

Differentially Expressed Genes in CD44+ Breast Epithelial Cells

| | Nulliparous (NP) Samples | | | Parous (P) Samples | | | | Pseudo fold change | P value | Gene description |
|---|---|---|---|---|---|---|---|---|---|---|
| Gene Symbol | CD44+ N48 | CD44+ N58 | CD44+ N43 | CD44+ N37 | CD44+ N39 | CD44+ N40 | | | | |
| CHST14 | 6.312 | 5.963 | 5.522 | 3.848 | 3.978 | 3.233 | -4.886 | 0.0099532 | carbohydrate (N-acetylgalactosamine 4-0) sulfotransferase 14 |
| ULK3 | 4.620 | 6.184 | 6.591 | 4.273 | 3.659 | 3.897 | -4.877 | 0.0361404 | unc-51-like kinase 3 (C. elegans) |
| IFFO2 | 8.418 | 8.588 | 8.761 | 6.016 | 7.537 | 6.305 | -4.867 | 0.0226506 | intermediate filament family orphan 2 |
| NFKBIL1 | 5.644 | 5.904 | 6.333 | 4.052 | 3.686 | 2.233 | -4.859 | 0.0110936 | nuclear factor of kappa light polypeptide gene enhancer in B-cells inhibitor-like 1 |
| TP53RK | 4.904 | 7.155 | 6.551 | 4.737 | 4.271 | 4.054 | -4.859 | 0.0423373 | TP53 regulating kinase |
| USP33 | 6.506 | 7.772 | 7.393 | 5.494 | 4.653 | 4.862 | -4.852 | 0.0144808 | ubiquitin specific peptidase 33 |
| HIGD2A | 6.495 | 7.588 | 7.919 | 5.472 | 5.015 | 5.309 | -4.851 | 0.0179956 | HIG1 hypoxia inducible domain family, member 2A |
| FTO | 7.394 | 7.265 | 6.532 | 5.894 | 4.141 | 4.988 | -4.847 | 0.0241667 | fat mass and obesity associated |
| CBX4 | 7.088 | 7.039 | 7.195 | 4.017 | 4.812 | 6.390 | -4.844 | 0.0313078 | chromobox homolog 4 |
| B3GALNT1 | 4.312 | 4.509 | 4.508 | 2.233 | 2.233 | 2.233 | -4.840 | 0.0037258 | beta-1,3-N-acetylgalactosaminyltransferase 1 (globoside blood group) |
| DOPEY2 | 7.832 | 8.751 | 9.018 | 6.476 | 5.576 | 6.487 | -4.840 | 0.0123698 | dopey family member 2 |
| CLU | 7.000 | 9.281 | 6.843 | 4.653 | 6.262 | 5.452 | -4.563 | 0.0336336 | clusterin |
| CDYL | 6.202 | 6.982 | 6.492 | 4.868 | 4.294 | 4.013 | -4.561 | 0.0016939 | chromodomain protein, Y-like |
| PPP2CA | 9.159 | 9.986 | 9.926 | 7.496 | 7.719 | 7.797 | -4.559 | 0.0126783 | protein phosphatase 2, catalytic subunit, alpha isozyme |
| SMAD7 | 6.891 | 9.079 | 7.304 | 5.115 | 4.871 | 5.644 | -4.559 | 0.0159636 | SMAD family member 7 |
| SERPINH1 | 12.425 | 12.685 | 12.048 | 10.239 | 9.538 | 10.692 | -4.552 | 0.0119761 | serpin peptidase inhibitor, clade H (heat shock protein 47), member 1, (collagen binding protein 1) |
| SEC22C | 5.475 | 6.435 | 5.701 | 4.722 | 2.970 | 3.516 | -4.548 | 0.0225834 | SEC22 vesicle trafficking protein homolog C (S. cerevisiae) |
| EMILIN2 | 6.171 | 7.356 | 7.091 | 5.119 | 4.906 | 4.901 | -4.548 | 0.0193598 | elastin microfibril interfacer 2 |
| NAAA | 4.817 | 5.122 | 4.417 | 3.535 | 2.233 | 2.233 | -4.545 | 0.0178076 | N-acylethanolamine acid amidase |
| C19orf20 | 5.683 | 5.570 | 5.759 | 4.878 | 3.499 | 1.648 | -4.543 | 0.0314367 | chromosome 19 open reading frame 20 |
| MRPL22 | 4.734 | 4.950 | 3.832 | 3.023 | 1.648 | 1.648 | -4.542 | 0.0148073 | mitochondrial ribosomal protein L22 |
| C6orf108 | 6.770 | 5.472 | 6.334 | 4.664 | 4.151 | 3.054 | -4.541 | 0.0199005 | chromosome 6 open reading frame 108 |
| RPS5 | 11.941 | 13.370 | 12.737 | 10.554 | 10.977 | 10.542 | -4.540 | 0.0197293 | ribosomal protein S5 |
| IRAK2 | 8.103 | 9.276 | 7.684 | 7.078 | 5.510 | 5.920 | -4.539 | 0.0242000 | interleukin-1 receptor-associated kinase 2 |
| ATP1B2 | 8.801 | 7.247 | 6.567 | 6.220 | 4.385 | 5.857 | -4.538 | 0.0414270 | ATPase, Na+/K+ transporting, beta 2 polypeptide |
| RCN1 | 8.423 | 9.873 | 9.511 | 7.650 | 7.329 | 7.157 | -4.538 | 0.0243913 | reticulocalbin 1, EF-hand calcium binding domain |
| LOC728661 | 6.392 | 6.932 | 7.492 | 5.254 | 4.141 | 5.311 | -4.535 | 0.0211199 | No description |
| PRDX2 | 7.424 | 7.907 | 7.261 | 5.974 | 5.244 | 4.360 | -4.532 | 0.0138451 | peroxiredoxin 2 |
| C2orf28 | 7.949 | 7.550 | 7.226 | 5.773 | 5.561 | 4.071 | -4.517 | 0.0140523 | chromosome 2 open reading frame 28 |
| CYBA | 7.555 | 7.888 | 7.783 | 5.610 | 5.824 | 5.279 | -4.509 | 0.0070471 | cytochrome b-245, alpha polypeptide |
| IAH1 | 5.264 | 4.797 | 4.536 | 2.625 | 4.174 | 1.648 | -4.507 | 0.0347553 | isoamyl acetate-hydrolyzing esterase 1 homolog (S. cerevisiae) |
| EEF1B2 | 6.470 | 6.999 | 6.751 | 5.113 | 4.273 | 4.581 | -4.501 | 0.0115990 | eukaryotic translation elongation factor 1 beta 2 |
| RBM24 | 4.936 | 5.213 | 4.769 | 2.951 | 3.043 | 2.233 | -4.500 | 0.0088974 | RNA binding motif protein 24 |
| PMP22 | 10.730 | 11.016 | 9.588 | 8.303 | 8.561 | 8.742 | -4.499 | 0.0237099 | peripheral myelin protein 22 |
| GLUL | 8.763 | 10.521 | 9.851 | 7.682 | 7.318 | 7.916 | -4.497 | 0.0220704 | glutamate-ammonia ligase |
| DAB2IP | 6.138 | 6.813 | 6.740 | 3.970 | 5.221 | 4.516 | -4.493 | 0.0188600 | DAB2 interacting protein |
| FAF2 | 5.614 | 7.035 | 6.612 | 4.868 | 4.007 | 3.648 | -4.492 | 0.0174666 | Fas associated factor family member 2 |
| KCNS3 | 3.422 | 3.832 | 3.814 | 1.648 | 1.648 | 1.648 | -4.487 | 0.0074638 | potassium voltage-gated channel, delayed-rectifier, subfamily S, member 3 |
| GMCL1L | 5.042 | 3.814 | 3.832 | 3.557 | 1.648 | 1.648 | -4.487 | 0.0399650 | germ cell-less homolog 1 (Drosophila)-like |
| TPM4 | 7.962 | 10.442 | 9.373 | 7.336 | 7.208 | 5.800 | -4.486 | 0.0238693 | tropomyosin 4 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| BRF2 | 4.264 | 5.737 | 6.438 | 4.273 | 2.648 | 2.648 | −4.486 | 0.0281501 | BRF2, subunit of RNA polymerase III transcription initiation factor, BRF1-like |
| SPIN1 | 7.689 | 7.552 | 7.328 | 6.136 | 4.767 | 5.387 | −4.484 | 0.0157515 | spindlin 1 |
| ARSB | 6.517 | 7.318 | 6.309 | 4.587 | 4.405 | 4.146 | −4.477 | 0.0086513 | arylsulfatase B |
| UBE2D1 | 6.510 | 8.205 | 8.599 | 5.293 | 5.517 | 6.437 | −4.474 | 0.0339393 | ubiquitin-conjugating enzyme E2D 1 (UBC4/5 homolog, yeast) |
| TRADD | 4.314 | 4.647 | 5.444 | 3.081 | 3.284 | 0.648 | −4.471 | 0.0254707 | TNFRSF1 A-associated via death domain |
| DGCR2 | 6.958 | 7.625 | 7.716 | 6.077 | 5.465 | 4.486 | −4.470 | 0.0205397 | DiGeorge syndrome critical region gene 2 |
| PIK3R2 | 6.167 | 5.733 | 6.024 | 3.233 | 3.978 | 4.007 | −4.469 | 0.0087671 | phosphoinositide-3-kinase, regulatory subunit 2 (beta) |
| IDH1 | 6.547 | 5.453 | 5.183 | 3.023 | 3.805 | 3.929 | −4.468 | 0.0181674 | Description |
| MRPS30 | 6.418 | 6.688 | 6.535 | 4.376 | 5.256 | 4.104 | −4.467 | 0.0167518 | mitochondrial ribosomal protein S30 |
| S100A10 | 8.526 | 11.277 | 11.095 | 7.405 | 9.119 | 7.655 | −4.463 | 0.0417556 | S100 calcium binding protein A10 |
| ATG16L1 | 5.076 | 6.881 | 6.630 | 4.690 | 4.474 | 4.179 | −4.458 | 0.0398728 | ATG16 autophagy related 16-like 1 (S. cerevisiae) |
| YIPF5 | 6.985 | 7.482 | 7.317 | 5.327 | 4.899 | 5.083 | −4.455 | 0.0073924 | Yip1 domain family, member 5 |
| EFEMP2 | 10.199 | 7.986 | 8.731 | 7.683 | 6.358 | 6.575 | −4.455 | 0.0322451 | EGF-containing fibulin-like extracellular matrix protein 2 |
| FJX1 | 6.256 | 7.176 | 6.031 | 3.218 | 5.023 | 4.581 | −4.447 | 0.0224010 | four jointed box 1 (Drosophila) |
| CYB5B | 7.160 | 7.770 | 7.403 | 5.551 | 5.618 | 4.382 | −4.446 | 0.0131504 | cytochrome b5 type B (outer mitochondrial membrane) |
| RADIL | 6.425 | 5.420 | 5.863 | 4.273 | 2.648 | 4.199 | −4.444 | 0.0209820 | Ras association and DIL domains |
| SFRS2 | 9.856 | 11.408 | 11.199 | 8.519 | 9.236 | 9.047 | −4.444 | 0.0283830 | No description |
| CANX | 10.974 | 11.566 | 11.478 | 10.281 | 9.206 | 8.826 | −4.430 | 0.0246492 | calnexin |
| ADSS | 5.076 | 6.133 | 6.819 | 3.988 | 3.508 | 4.042 | −4.424 | 0.0188510 | adenylosuccinate synthase |
| RPL10 | 14.704 | 14.394 | 14.745 | 12.246 | 12.601 | 12.559 | −4.423 | 0.0065168 | ribosomal protein L10 |
| C11orf73 | 5.861 | 5.863 | 4.652 | 3.718 | 3.294 | 2.648 | −4.423 | 0.0159546 | chromosome 11 open reading frame 73 |
| SLC27A1 | 7.367 | 7.299 | 7.422 | 5.277 | 5.278 | 4.007 | −4.418 | 0.0085757 | solute carrier family 27 (fatty acid transporter), member 1 |
| KIAA0040 | 7.177 | 7.083 | 5.556 | 4.905 | 4.672 | 5.033 | −4.418 | 0.0369002 | KIAA0040 |
| BTG2 | 11.114 | 9.902 | 8.886 | 7.761 | 7.175 | 7.910 | −4.410 | 0.0196211 | BTG family, member 2 |
| DCTN3 | 7.283 | 7.096 | 6.526 | 4.956 | 5.681 | 3.508 | −4.408 | 0.0226159 | dynactin 3 (p22) |
| LIF | 8.986 | 11.390 | 10.953 | 8.815 | 8.906 | 7.628 | −4.403 | 0.0435158 | leukemia inhibitory factor (cholinergic differentiation factor) |
| RSU1 | 7.912 | 7.477 | 7.050 | 5.498 | 5.774 | 4.796 | −4.402 | 0.0141244 | Ras suppressor protein 1 |
| IFRD2 | 6.167 | 8.585 | 8.547 | 5.489 | 6.448 | 5.444 | −4.398 | 0.0461938 | interferon-related developmental regulator 2 |
| CHRDL1 | 7.347 | 7.501 | 6.272 | 5.136 | 4.135 | 6.104 | −4.398 | 0.0368842 | chordin-like 1 |
| MFF | 4.977 | 5.761 | 6.132 | 3.997 | 3.456 | 3.456 | −4.392 | 0.0175026 | mitochondrial fission factor |
| MRPS34 | 7.188 | 7.238 | 6.783 | 5.355 | 5.053 | 4.262 | −4.391 | 0.0120849 | mitochondrial ribosomal protein S34 |
| COMMD10 | 3.194 | 1.477 | 2.781 | 0.648 | 0.648 | 0.648 | −4.384 | 0.0298617 | COMM domain containing 10 |
| IGDCC4 | 7.007 | 4.944 | 5.587 | 3.456 | 3.456 | 4.409 | −4.382 | 0.0290298 | immunoglobulin superfamily, DCC subclass, member 4 |
| SCPEP1 | 4.142 | 7.421 | 4.364 | 2.233 | 2.233 | 2.233 | −4.379 | 0.0162222 | serine carboxypeptidase 1 |
| ZBTB41 | 5.899 | 5.570 | 5.570 | 3.442 | 4.385 | 2.970 | −4.372 | 0.0167858 | zinc finger and BTB domain containing 41 |
| CMPK2 | 5.683 | 5.671 | 4.115 | 3.557 | 2.739 | 3.294 | −4.365 | 0.0275497 | cytidine monophosphate (UMP-CMP) kinase 2, mitochondrial |
| SH2B3 | 9.833 | 9.224 | 8.476 | 7.707 | 6.450 | 6.472 | −4.365 | 0.0166915 | SH2B adaptor protein 3 |
| NXT2 | 3.619 | 5.641 | 5.658 | 3.535 | 3.467 | 2.233 | −4.355 | 0.0467948 | nuclear transport factor 2-like export factor 2 |
| GPR116 | 7.731 | 6.702 | 5.608 | 5.083 | 4.377 | 4.580 | −4.354 | 0.0299449 | G protein-coupled receptor 116 |
| TFPI | 9.010 | 11.614 | 11.216 | 9.492 | 7.081 | 7.492 | −4.353 | 0.0293660 | tissue factor pathway inhibitor (lipoprotein-associated coagulation inhibitor) |
| MAG 11 | 6.554 | 5.582 | 5.713 | 4.293 | 4.433 | 3.456 | −4.351 | 0.0232399 | membrane associated guanylate kinase, WW and PDZ domain containing 1 |
| FBLN1 | 12.034 | 12.031 | 10.631 | 9.066 | 9.634 | 9.915 | −4.344 | 0.0231386 | fibulin 1 |
| CCS | 5.109 | 4.294 | 4.352 | 2.233 | 2.233 | 2.233 | −4.343 | 0.0065529 | copper chaperone for superoxide dismutase |

TABLE 4-continued

Differentially Expressed Genes in CD44+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD44+ N48 | CD44+ N58 | CD44+ N43 | CD44+ N37 | CD44+ N39 | CD44+ N40 | | | | |
| SNX2 | 5.042 | 5.945 | 6.343 | 3.830 | 4.692 | 2.752 | | -4.332 | 0.0310083 | sorting nexin 2 |
| PLSCR3 | 7.637 | 7.236 | 7.514 | 5.838 | 5.400 | 4.007 | | -4.329 | 0.0149085 | phospholipid scramblase 3 |
| RARB | 5.346 | 6.711 | 5.730 | 3.951 | 3.694 | 3.233 | | -4.325 | 0.0129445 | retinoic acid receptor, beta |
| TBC1D5 | 8.350 | 6.945 | 6.886 | 6.238 | 4.659 | 6.007 | | -4.325 | 0.0478007 | TBC1 domain family, member 5 |
| SERPING1 | 7.904 | 9.121 | 7.715 | 5.792 | 5.718 | 5.873 | | -4.320 | 0.0100821 | serpin peptidase inhibitor, clade G (C1 inhibitor), member 1 |
| CMC1 | 3.194 | 2.758 | 2.593 | 0.648 | 0.648 | 0.648 | | -4.320 | 0.0063220 | COX assembly mitochondrial protein homolog (S. cerevisiae) |
| ROBO1 | 4.214 | 6.263 | 5.566 | 3.456 | 3.456 | 3.865 | | -4.317 | 0.0421820 | roundabout, axon guidance receptor, homolog 1 (Drosophila) |
| C11orf60 | 4.826 | 5.506 | 5.080 | 2.970 | 2.970 | 2.970 | | -4.315 | 0.0074307 | No description |
| GGT5 | 10.639 | 8.482 | 7.486 | 6.373 | 5.977 | 6.474 | | -4.313 | 0.0234194 | gamma-glutamyltransferase 5 |
| CCDC80 | 11.038 | 10.260 | 10.755 | 8.152 | 8.250 | 9.728 | | -4.312 | 0.0260620 | coiled-coil domain containing 80 |
| GOLGA4 | 5.431 | 6.497 | 6.215 | 4.108 | 4.108 | 4.382 | | -4.308 | 0.0192752 | golgin A4 |
| KLHL13 | 3.792 | 5.996 | 4.755 | 2.648 | 2.648 | 2.648 | | -4.308 | 0.0224960 | kelch-like 13 (Drosophila) |
| RRP1B | 6.182 | 8.123 | 7.238 | 4.603 | 5.206 | 5.132 | | -4.307 | 0.0202139 | ribosomal RNA processing 1 homolog B (S. cerevisiae) |
| NUP133 | 4.086 | 5.616 | 5.742 | 3.637 | 3.233 | 3.233 | | -4.305 | 0.0351913 | nucleoporin 133 kDa |
| C4orf46 | 7.695 | 8.035 | 6.941 | 5.346 | 4.837 | 6.349 | | -4.300 | 0.0235040 | chromosome 4 open reading frame 46 |
| BDKRB1 | 9.692 | 7.974 | 7.983 | 7.039 | 6.188 | 5.869 | | -4.300 | 0.0242333 | bradykinin receptor B1 |
| PSME1 | 9.912 | 9.668 | 9.383 | 8.316 | 7.291 | 7.279 | | -4.299 | 0.0161154 | proteasome (prosome, macropain) activator subunit 1 (PA28 alpha) |
| C3orf38 | 5.633 | 6.142 | 5.074 | 4.957 | 2.970 | 3.516 | | -4.298 | 0.0430458 | chromosome 3 open reading frame 38 |
| GAS1 | 6.773 | 5.966 | 4.735 | 4.501 | 3.859 | 3.865 | | -4.288 | 0.0435865 | growth arrest-specific 1 |
| MUSTN1 | 4.734 | 5.384 | 4.839 | 2.625 | 2.739 | 3.294 | | -4.286 | 0.0113341 | musculoskeletal, embryonic nuclear protein 1 |
| C8orf58 | 4.008 | 3.692 | 3.748 | 1.648 | 1.648 | 1.648 | | -4.286 | 0.0047643 | chromosome 8 open reading frame 58 |
| TMEM59 | 11.208 | 11.091 | 11.072 | 9.110 | 8.912 | 9.003 | | -4.281 | 0.0047283 | transmembrane protein 59 |
| NEK7 | 7.736 | 8.273 | 8.339 | 6.073 | 6.047 | 6.242 | | -4.278 | 0.0104939 | NIMA (never in mitosis gene a)-related kinase 7 |
| PARD3 | 4.378 | 5.208 | 5.064 | 2.970 | 2.970 | 2.970 | | -4.269 | 0.0142908 | par-3 partitioning defective 3 homolog (C. elegans) |
| ADAM12 | 8.698 | 7.204 | 6.999 | 4.905 | 5.538 | 5.944 | | -4.268 | 0.0223158 | ADAM metallopeptidase domain 12 |
| FAM36A | 6.381 | 7.907 | 7.694 | 5.086 | 5.813 | 4.987 | | -4.268 | 0.0237633 | family with sequence similarity 36, member A |
| PREB | 5.688 | 5.945 | 6.849 | 4.350 | 3.852 | 3.694 | | -4.265 | 0.0133626 | prolactin regulatory element binding |
| SLC25A39 | 3.947 | 6.062 | 5.062 | 3.682 | 2.970 | 2.970 | | -4.264 | 0.0408787 | solute carrier family 25, member 39 |
| TCF15 | 8.215 | 4.751 | 5.648 | 4.376 | 3.247 | 3.557 | | -4.262 | 0.0332385 | transcription factor 15 (basic helix-loop-helix) |
| HERC4 | 4.672 | 5.875 | 6.052 | 3.961 | 3.648 | 3.648 | | -4.261 | 0.0281778 | hect domain and RLD 4 |
| SH3BGRL3 | 9.266 | 9.841 | 10.338 | 8.019 | 8.249 | 6.606 | | -4.256 | 0.0209730 | SH3 domain binding glutamic acid-rich protein like 3 |
| ADD3 | 6.568 | 6.973 | 6.034 | 4.225 | 4.264 | 4.885 | | -4.249 | 0.0140614 | adducin 3 (gamma) |
| SEMA3C | 6.048 | 6.240 | 4.451 | 4.376 | 4.007 | 3.648 | | -4.248 | 0.0424475 | sema domain, immunoglobulin domain (ig), short basic domain, secreted, (semaphorin) 3C |
| B4GALT5 | 8.619 | 10.093 | 9.268 | 7.123 | 7.183 | 7.529 | | -4.241 | 0.0183241 | UDP-Gal:betaGlcNAc beta 1,4-galactosyltransferase, polypeptide 5 |
| FHL1 | 7.744 | 8.518 | 6.728 | 5.906 | 4.646 | 6.002 | | -4.235 | 0.0256600 | four and a half LIM domains 1 |
| LSM2 | 7.580 | 6.911 | 7.482 | 6.065 | 5.060 | 4.830 | | -4.232 | 0.0190291 | LSM2 homolog, U6 small nuclear RNA associated (S. cerevisiae) |
| JUP | 8.744 | 9.865 | 9.969 | 7.144 | 8.646 | 6.666 | | -4.223 | 0.0318867 | junction plakoglobin |
| CD44 | 12.394 | 13.237 | 12.364 | 10.607 | 10.286 | 10.448 | | -4.222 | 0.0096364 | CD44 molecule (Indian blood group) |
| RNF2 | 7.159 | 7.844 | 6.732 | 4.655 | 5.202 | 5.301 | | -4.219 | 0.0125362 | ring finger protein 2 |
| H2AFX | 7.460 | 7.940 | 8.588 | 5.522 | 5.863 | 6.107 | | -4.218 | 0.0126693 | H2A histone family, member X |
| MXRA7 | 10.309 | 10.391 | 9.298 | 8.315 | 7.910 | 7.860 | | -4.216 | 0.0177376 | matrix-remodelling associated 7 |
| MAGEH1 | 5.821 | 6.435 | 6.158 | 4.929 | 2.233 | 4.082 | | -4.215 | 0.0241036 | melanoma antigen family H, 1 |

TABLE 4-continued

Differentially Expressed Genes in CD44+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD44+ N48 | CD44+ N58 | CD44+ N43 | CD44+ N37 | CD44+ N39 | CD44+ N40 | | | | |
| PIK3CD | 5.339 | 6.874 | 7.206 | 5.132 | 4.467 | 4.436 | | −4.213 | 0.0393785 | phosphoinositide-3-kinase, catalytic, delta polypeptide |
| PROS1 | 5.769 | 7.022 | 7.360 | 3.718 | 3.659 | 3.694 | | −4.211 | 0.0132107 | protein S (alpha) |
| COPZ2 | 7.926 | 5.903 | 5.631 | 3.830 | 4.174 | 3.557 | | −4.211 | 0.0154860 | coatomer protein complex, subunit zeta 2 |
| GNPTG | 4.817 | 5.282 | 5.607 | 3.535 | 3.043 | 3.054 | | −4.204 | 0.0125452 | N-acetylglucosamine-1-phosphate transferase, gamma subunit |
| TRAPPC4 | 4.008 | 5.416 | 4.811 | 3.714 | 2.739 | 1.648 | | −4.204 | 0.0322062 | trafficking protein particle complex 4 |
| ARMCX1 | 6.679 | 7.394 | 8.034 | 5.323 | 4.988 | 5.939 | | −4.200 | 0.0234603 | armadillo repeat containing, X-linked 1 |
| MAP4K5 | 7.340 | 8.971 | 8.818 | 6.540 | 6.748 | 6.865 | | −4.198 | 0.0418697 | mitogen-activated protein kinase kinase kinase kinase 5 |
| C11orf24 | 5.938 | 7.375 | 6.252 | 5.306 | 4.259 | 3.456 | | −4.196 | 0.0251463 | chromosome 11 open reading frame 24 |
| LARGE | 6.081 | 7.034 | 6.177 | 4.342 | 4.108 | 4.108 | | −4.196 | 0.0095130 | like-glycosyltransferase |
| ZFR | 6.426 | 7.820 | 7.989 | 5.921 | 5.288 | 5.270 | | −4.195 | 0.0272981 | zinc finger RNA binding protein |
| MLST8 | 4.312 | 4.302 | 4.588 | 3.278 | 2.233 | 2.233 | | −4.194 | 0.0220163 | MTOR associated protein, LST8 homolog (S. cerevisiae) |
| INPP1 | 6.322 | 4.930 | 5.202 | 4.254 | 4.254 | 3.508 | | −4.193 | 0.0278742 | inositol polyphosphate-1-phosphatase |
| C3orf31 | 3.194 | 1.649 | 2.714 | 0.648 | 0.648 | 0.648 | | −4.187 | 0.0249508 | chromosome 3 open reading frame 31 |
| RPPH1 | 5.204 | 2.714 | 3.881 | 3.351 | 0.648 | 0.648 | | −4.187 | 0.0410173 | ribonuclease P RNA component H1 |
| GBP1 | 6.735 | 7.258 | 7.401 | 4.262 | 5.196 | 6.173 | | −4.178 | 0.0300385 | guanylate binding protein 1, interferon-inducible, 67 kDa |
| GCLM | 7.691 | 8.979 | 9.543 | 6.878 | 7.326 | 6.916 | | −4.178 | 0.0421910 | glutamate-cysteine ligase, modifier subunit |
| SAE1 | 8.119 | 8.060 | 7.929 | 6.949 | 5.783 | 5.997 | | −4.177 | 0.0230029 | SUMO1 activating enzyme subunit 1 |
| FOSB | 15.170 | 13.757 | 13.523 | 11.461 | 11.814 | 12.852 | | −4.176 | 0.0263081 | FBJ murine osteosarcoma viral oncogene homolog B |
| DCAF12 | 6.280 | 7.891 | 7.344 | 4.954 | 5.248 | 5.829 | | −4.175 | 0.0315969 | DDB1 and CUL4 associated factor 12 |
| SMARCD1 | 4.331 | 6.208 | 6.434 | 3.648 | 4.372 | 3.648 | | −4.175 | 0.0489993 | SWI/SNF related, matrix associated, actin dependent regulator of chromatin, subfamily d, member 1 |
| FKBP7 | 7.978 | 6.892 | 6.552 | 4.492 | 4.508 | 5.981 | | −4.169 | 0.0246943 | FK506 binding protein 7 |
| FLNB | 5.775 | 7.425 | 8.015 | 4.891 | 5.957 | 4.736 | | −4.165 | 0.0457570 | filamin B, beta |
| EDF1 | 8.386 | 9.240 | 9.575 | 7.519 | 7.355 | 5.963 | | −4.158 | 0.0236919 | endothelial differentiation-related factor 1 |
| UBE2G1 | 5.691 | 7.304 | 7.150 | 5.088 | 5.004 | 5.248 | | −4.157 | 0.0454797 | ubiquitin-conjugating enzyme E2G 1 (UBC7 homolog, yeast) |
| MFHAS1 | 7.275 | 7.034 | 6.222 | 4.912 | 4.871 | 5.221 | | −4.154 | 0.0198250 | malignant fibrous histiocytoma amplified sequence 1 |
| HLA-DPA1 | 8.797 | 7.409 | 6.580 | 5.357 | 5.170 | 6.420 | | −4.146 | 0.0398929 | major histocompatibility complex, class II, DP alpha 1 |
| OSBPL8 | 5.978 | 7.936 | 7.282 | 5.581 | 4.932 | 5.232 | | −4.142 | 0.0369501 | oxysterol binding protein-like 8 |
| MORC3 | 6.145 | 7.770 | 7.140 | 5.722 | 4.678 | 4.724 | | −4.135 | 0.0272593 | MORC family CW-type zinc finger 3 |
| IQCK | 3.619 | 4.281 | 4.692 | 2.233 | 2.233 | 2.233 | | −4.134 | 0.0152877 | IQ motif containing K |
| TBC1D20 | 8.409 | 9.355 | 9.372 | 7.328 | 6.761 | 6.908 | | −4.123 | 0.0151414 | TBC1 domain family, member 20 |
| SLC35B3 | 5.503 | 4.276 | 5.437 | 3.535 | 2.233 | 3.054 | | −4.120 | 0.0205924 | solute carrier family 35, member B3 |
| PALM | 6.851 | 6.133 | 4.498 | 4.091 | 3.456 | 4.141 | | −4.120 | 0.0389847 | paralemmin |
| KIAA1715 | 7.269 | 7.208 | 7.287 | 5.607 | 5.228 | 4.997 | | −4.117 | 0.0102173 | KIAA1715 |
| TNFRSF11B | 3.422 | 5.540 | 5.082 | 3.023 | 3.499 | 1.648 | | −4.115 | 0.0461473 | tumor necrosis factor receptor superfamily, member 11b |
| C6orf106 | 7.504 | 9.257 | 9.553 | 7.315 | 7.216 | 6.587 | | −4.115 | 0.0492454 | chromosome 6 open reading frame 106 |
| GOLM1 | 8.426 | 7.833 | 7.456 | 5.395 | 6.208 | 6.387 | | −4.112 | 0.0215906 | golgi membrane protein 1 |
| TP53INP1 | 5.690 | 6.333 | 6.894 | 4.859 | 3.456 | 4.293 | | −4.111 | 0.0208641 | tumor protein p53 inducible nuclear protein 1 |
| CPEB2 | 7.696 | 9.416 | 7.500 | 5.529 | 5.657 | 6.669 | | −4.110 | 0.0238832 | cytoplasmic polyadenylation element binding protein 2 |
| C2CD2 | 7.060 | 8.178 | 7.546 | 6.103 | 5.693 | 5.021 | | −4.110 | 0.0205744 | C2 calcium-dependent domain containing 2 |
| TAOK1 | 5.047 | 5.685 | 6.085 | 3.961 | 3.648 | 3.648 | | −4.103 | 0.0185750 | TAO kinase 1 |
| ST6GALNAC6 | 7.264 | 7.912 | 5.699 | 5.177 | 5.228 | 5.345 | | −4.102 | 0.0493438 | ST6 (alpha-N-acetyl-neuraminyl-2,3-beta-galactosyl-1,3)-N-acetylgalactosaminide alpha-2,6-sialyltransferase 6 |
| UBE2N | 5.809 | 7.670 | 6.953 | 4.457 | 5.182 | 4.917 | | −4.101 | 0.0280801 | ubiquitin-conjugating enzyme E2N (UBC13 homolog, yeast) |
| C7orf30 | 6.202 | 6.658 | 6.853 | 5.133 | 4.602 | 3.043 | | −4.101 | 0.0198679 | chromosome 7 open reading frame 30 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| PSAP | 10.066 | 11.226 | 10.791 | 8.830 | 8.237 | 8.757 | −4.095 | 0.0151844 | prosaposin |
| INSR | 6.133 | 7.711 | 7.499 | 5.678 | 5.237 | 5.127 | −4.093 | 0.0340308 | insulin receptor |
| ZBTB20 | 6.920 | 5.666 | 4.643 | 3.637 | 3.233 | 4.508 | −4.081 | 0.0398423 | zinc finger and BTB domain containing 20 |
| DYRK1A | 8.939 | 9.881 | 9.433 | 7.566 | 7.406 | 7.210 | −4.078 | 0.0129903 | dual-specificity tyrosine-(Y)-phosphorylation regulated kinase 1A |
| ITM2B | 11.201 | 11.172 | 9.972 | 8.985 | 8.803 | 9.173 | −4.076 | 0.0257979 | integral membrane protein 2B |
| ANTXR1 | 8.547 | 7.572 | 6.978 | 5.499 | 5.545 | 5.889 | −4.075 | 0.0194062 | anthrax toxin receptor 1 |
| PJA2 | 8.480 | 8.287 | 8.290 | 6.884 | 6.085 | 6.265 | −4.072 | 0.0133958 | praja ring finger 2 |
| PITPNA | 6.701 | 7.415 | 7.681 | 5.655 | 5.107 | 5.009 | −4.071 | 0.0157376 | phosphatidylinositol transfer protein, alpha |
| METTL12 | 4.008 | 4.764 | 5.058 | 1.648 | 2.739 | 3.557 | −4.070 | 0.0310173 | methyltransferase like 12 |
| POLR2C | 5.282 | 7.213 | 6.966 | 5.192 | 4.385 | 3.859 | −4.059 | 0.0340218 | polymerase (RNA) II (DNA directed) polypeptide C, 33 kDa |
| HEXIM1 | 7.809 | 8.727 | 7.706 | 5.617 | 5.788 | 6.788 | −4.057 | 0.0213896 | hexamethylene bis-acetamide inducible 1 |
| ARL8B | 7.685 | 9.183 | 9.488 | 6.882 | 7.163 | 7.261 | −4.056 | 0.0433889 | ADP-ribosylation factor-like 8B |
| SCHIP1 | 6.886 | 6.961 | 6.927 | 4.907 | 6.255 | 4.179 | −4.055 | 0.0375553 | schwannomin interacting protein 1 |
| ATG7 | 5.474 | 6.424 | 6.581 | 4.621 | 3.456 | 3.456 | −4.052 | 0.0147913 | ATG7 autophagy related 7 homolog (S. cerevisiae) |
| ANTXR2 | 6.892 | 6.533 | 6.894 | 4.515 | 4.664 | 5.181 | −4.052 | 0.0117542 | anthrax toxin receptor 2 |
| CBX8 | 4.423 | 4.536 | 4.757 | 2.625 | 2.739 | 1.648 | −4.051 | 0.0111026 | chromobox homolog 8 |
| PTTG1IP | 6.426 | 7.904 | 6.985 | 5.886 | 5.376 | 4.299 | −4.051 | 0.0333244 | pituitary tumor-transforming 1 interacting protein |
| BMPR2 | 7.696 | 7.416 | 6.905 | 5.518 | 5.319 | 5.402 | −4.041 | 0.0132537 | bone morphogenetic protein receptor, type II (serine/threonine kinase) |
| COBRA1 | 7.354 | 6.783 | 7.111 | 5.453 | 5.097 | 4.623 | −4.040 | 0.0130354 | cofactor of BRCA1 |
| CNNM4 | 5.832 | 6.775 | 6.566 | 4.099 | 3.818 | 5.145 | −4.040 | 0.0210541 | cyclin M4 |
| FLJ43663 | 3.792 | 5.487 | 4.661 | 2.648 | 2.648 | 2.648 | −4.035 | 0.0221584 | No description |
| TEX10 | 7.077 | 8.391 | 8.902 | 5.235 | 6.383 | 6.701 | −4.025 | 0.0322943 | testis expressed 10 |
| TCEB2 | 7.165 | 8.506 | 8.176 | 6.498 | 6.245 | 4.590 | −4.023 | 0.0268600 | transcription elongation factor B (SIII), polypeptide 2 (18 kDa, elongin B) |
| TSPAN4 | 7.986 | 7.238 | 7.237 | 5.962 | 3.827 | 5.981 | −4.014 | 0.0264010 | tetraspanin 4 |
| TNPO2 | 8.681 | 8.640 | 8.960 | 6.843 | 6.316 | 6.956 | −4.013 | 0.0101092 | transportin 2 |
| CEBPG | 6.753 | 8.102 | 7.386 | 5.051 | 5.650 | 5.382 | −4.011 | 0.0174000 | CCAAT/enhancer binding protein (C/EBP), gamma |
| MFGE8 | 11.262 | 11.000 | 11.056 | 9.149 | 9.259 | 8.780 | −4.009 | 0.0082541 | milk fat globule-EGF factor 8 protein |
| SRP14 | 6.422 | 7.034 | 6.671 | 5.453 | 3.508 | 4.670 | −4.003 | 0.0213272 | signal recognition particle 14 kDa (homologous Alu RNA binding protein) |
| NAA30 | 4.086 | 6.012 | 5.233 | 3.233 | 3.233 | 3.233 | −3.999 | 0.0304350 | N(alpha)-acetyltransferase 30, NatO catalytic subunit |
| KRR1 | 5.982 | 6.856 | 7.181 | 4.667 | 5.023 | 4.857 | −3.999 | 0.0226596 | KRR1, small subunit (SSU) processome component, homolog (yeast) |
| BBS1 | 4.969 | 4.956 | 5.748 | 2.970 | 3.508 | 2.970 | −3.996 | 0.0127740 | Bardet-Biedl syndrome 1 |
| NCOA7 | 7.596 | 8.741 | 9.014 | 6.501 | 6.743 | 6.875 | −3.995 | 0.0300295 | nuclear receptor coactivator 7 |
| NUDT11 | 3.619 | 5.557 | 5.486 | 2.951 | 3.559 | 2.233 | −3.994 | 0.0372870 | nudix (nucleoside diphosphate linked moiety X)-type motif 11 |
| FAM150B | 4.008 | 3.645 | 3.640 | 1.648 | 1.648 | 1.648 | −3.991 | 0.0059664 | family with sequence similarity 150, member B |
| ZNF213 | 4.423 | 3.645 | 5.110 | 3.557 | 1.648 | 1.648 | −3.990 | 0.0316634 | zinc finger protein 213 |
| CEBPZ | 6.128 | 7.509 | 7.132 | 5.137 | 5.859 | 3.818 | −3.987 | 0.0357106 | CCAAT/enhancer binding protein (C/EBP), zeta |
| ZFAND1 | 5.956 | 6.514 | 5.690 | 4.315 | 4.015 | 3.694 | −3.987 | 0.0128863 | zinc finger, AN1-type domain 1 |
| C10orf75 | 5.503 | 4.902 | 5.244 | 3.278 | 2.233 | 3.508 | −3.986 | 0.0139373 | No description |
| NCL | 9.396 | 10.743 | 9.451 | 7.402 | 7.911 | 7.908 | −3.985 | 0.0173508 | nucleolin |
| LSM1 | 5.781 | 6.010 | 6.613 | 4.017 | 4.017 | 3.929 | −3.980 | 0.0092315 | LSM1 homolog, U6 small nuclear RNA associated (S. cerevisiae) |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| CDC42 | 10.625 | 10.974 | 10.991 | 9.297 | 8.869 | 8.634 | −3.975 | 0.0126873 | cell division cycle 42 (GTP binding protein, 25 kDa) |
| CSRP1 | 11.817 | 10.780 | 11.434 | 8.789 | 10.112 | 9.068 | −3.975 | 0.0220565 | cysteine and glycine-rich protein 1 |
| MPV17 | 5.572 | 6.061 | 6.781 | 4.624 | 3.868 | 4.071 | −3.973 | 0.0201161 | MpV17 mitochondrial inner membrane protein |
| ARVCF | 4.895 | 4.637 | 3.494 | 2.648 | 2.648 | 2.648 | −3.969 | 0.0316059 | armadillo repeat gene deleted in velocardiofacial syndrome |
| CKAP4 | 11.076 | 10.513 | 10.806 | 10.076 | 8.749 | 8.525 | −3.967 | 0.0384766 | cytoskeleton-associated protein 4 |
| MLLT11 | 4.972 | 5.894 | 6.229 | 3.662 | 2.987 | 4.262 | −3.959 | 0.0217744 | myeloid/lymphoid or mixed-lineage leukemia (trithorax homolog, *Drosophila*); translocated to, 11 |
| GNS | 9.402 | 9.824 | 8.858 | 7.839 | 6.249 | 7.430 | −3.958 | 0.0188960 | glucosamine (N-acetyl)-6-sulfatase |
| PGLS | 7.914 | 6.785 | 7.585 | 5.601 | 5.823 | 4.975 | −3.957 | 0.0198860 | 6-phosphogluconolactonase |
| SLC2A3 | 12.429 | 10.812 | 10.874 | 9.040 | 8.830 | 10.355 | −3.951 | 0.0359490 | solute carrier family 2 (facilitated glucose transporter), member 3 |
| HTRA1 | 6.081 | 8.944 | 5.793 | 4.099 | 3.818 | 4.507 | −3.950 | 0.0210360 | HtrA serine peptidase 1 |
| COL12A1 | 7.244 | 8.533 | 8.230 | 5.852 | 5.727 | 6.552 | −3.946 | 0.0224780 | collagen, type XII, alpha 1 |
| GNG2 | 7.700 | 6.153 | 5.280 | 4.173 | 3.694 | 5.118 | −3.944 | 0.0382159 | guanine nucleotide binding protein (G protein), gamma 2 |
| FLJ45079 | 5.042 | 6.691 | 5.997 | 4.017 | 3.247 | 4.376 | −3.944 | 0.0253154 | No description |
| WDR12 | 4.008 | 4.308 | 3.627 | 1.648 | 2.739 | 1.648 | −3.942 | 0.0192662 | WD repeat domain 12 |
| SLC41A2 | 5.524 | 3.627 | 3.538 | 2.625 | 1.648 | 1.648 | −3.942 | 0.0242922 | solute carrier family 41, member 2 |
| MYO M2 | 4.008 | 3.627 | 3.832 | 1.648 | 1.648 | 3.294 | −3.942 | 0.0474215 | myomesin (M-protein) 2, 165 kDa |
| CNIH | 4.524 | 6.088 | 5.494 | 3.682 | 2.970 | 3.516 | −3.940 | 0.0236198 | cornichon homolog (*Drosophila*) |
| SERPINE1 | 10.229 | 11.288 | 11.136 | 9.978 | 8.252 | 9.117 | −3.937 | 0.0395560 | serpin peptidase inhibitor, clade E (nexin, plasminogen activator inhibitor type 1), member 1 |
| CLDND1 | 9.838 | 9.773 | 9.651 | 7.650 | 7.798 | 8.019 | −3.932 | 0.0088101 | claudin domain containing 1 |
| PPP1CB | 9.537 | 10.541 | 10.025 | 8.259 | 8.051 | 7.659 | −3.931 | 0.0143248 | protein phosphatase 1, catalytic subunit, beta isozyme |
| ELOVL5 | 9.633 | 10.725 | 10.416 | 7.931 | 7.849 | 8.751 | −3.929 | 0.0169362 | ELOVL family member 5, elongation of long chain fatty acids (FEN1/Elo2, SUR4/Elo3-like, yeast) |
| SMARCAL1 | 5.644 | 4.543 | 4.629 | 3.670 | 2.233 | 3.508 | −3.927 | 0.0358534 | SWI/SNF related, matrix associated, actin dependent regulator of chromatin, subfamily a-like 1 |
| APTX | 3.947 | 5.005 | 5.416 | 3.442 | 2.970 | 2.970 | −3.927 | 0.0361993 | aprataxin |
| ZHX1 | 6.599 | 6.501 | 6.092 | 4.681 | 3.456 | 4.528 | −3.926 | 0.0141334 | zinc fingers and homeoboxes 1 |
| FUCA2 | 5.620 | 7.062 | 5.698 | 4.280 | 4.240 | 3.648 | −3.922 | 0.0206873 | fucosidase, alpha-L-2, plasma |
| ACSS1 | 4.620 | 4.719 | 5.945 | 2.648 | 3.659 | 3.303 | −3.922 | 0.0273896 | acyl-CoA synthetase short-chain family member 1 |
| DPYSL2 | 9.550 | 9.475 | 8.999 | 7.733 | 6.131 | 7.504 | −3.920 | 0.0171435 | dihydropyrimidinase-like 2 |
| UCK2 | 7.183 | 9.537 | 8.103 | 5.213 | 7.098 | 6.381 | −3.919 | 0.0426867 | uridine-cytidine kinase 2 |
| C20orf11 | 7.682 | 8.766 | 8.750 | 6.796 | 6.329 | 6.290 | −3.918 | 0.0197023 | chromosome 20 open reading frame 11 |
| GOLPH3L | 4.524 | 5.486 | 6.302 | 4.302 | 2.970 | 3.516 | −3.918 | 0.0380620 | golgi phosphoprotein 3-like |
| TMEM14A | 6.453 | 5.851 | 5.109 | 2.233 | 4.294 | 4.483 | −3.916 | 0.0337002 | transmembrane protein 14A |
| RAP2B | 8.433 | 9.940 | 9.922 | 6.942 | 7.970 | 7.271 | −3.915 | 0.0251553 | RAP2B, member of RAS oncogene family |
| NEK5 | 6.072 | 8.119 | 6.482 | 4.830 | 4.529 | 4.104 | −3.911 | 0.0174846 | NIMA (never in mitosis gene a)-related kinase 5 |
| RWDD2B | 5.255 | 4.201 | 4.393 | 3.429 | 2.233 | 2.233 | −3.911 | 0.0239068 | RWD domain containing 2B |
| RRBP1 | 7.322 | 7.517 | 7.837 | 5.553 | 5.333 | 5.871 | −3.908 | 0.0113570 | ribosome binding protein 1 homolog 180 kDa (dog) |
| FOXA1 | 3.792 | 4.615 | 5.377 | 3.218 | 2.648 | 2.648 | −3.908 | 0.0325452 | forkhead box A1 |
| TMEM51 | 6.590 | 7.963 | 7.586 | 4.981 | 5.621 | 5.880 | −3.904 | 0.0259435 | transmembrane protein 51 |
| ASPH | 11.182 | 10.306 | 10.040 | 9.032 | 9.218 | 8.066 | −3.902 | 0.0339213 | aspartate beta-hydroxylase |
| HSPA5 | 10.115 | 12.209 | 12.325 | 10.361 | 8.799 | 8.527 | −3.901 | 0.0307983 | heat shock 70 kDa protein 5 (glucose-regulated protein, 78 kDa) |
| NOV | 5.861 | 7.042 | 4.181 | 2.648 | 4.273 | 3.897 | −3.899 | 0.0457785 | nephroblastoma overexpressed gene |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| ZFX | 6.345 | 7.578 | 7.114 | 5.576 | 5.103 | 5.151 | −3.898 | 0.0268114 | zinc finger protein, X-linked |
| MTCO3 | 16.809 | 16.093 | 16.318 | 14.473 | 14.847 | 14.026 | −3.894 | 0.0155130 | No description |
| SYTL2 | 6.741 | 5.193 | 5.096 | 3.637 | 3.233 | 3.233 | −3.889 | 0.0158055 | synaptotagmin-like 2 |
| GHDC | 6.208 | 5.191 | 5.584 | 3.637 | 3.233 | 3.701 | −3.889 | 0.0120253 | GH3 domain containing |
| TRAPPC6B | 4.482 | 5.773 | 5.191 | 3.233 | 3.233 | 3.233 | −3.885 | 0.0191331 | trafficking protein particle complex 6B |
| MARVELD2 | 4.264 | 5.874 | 6.054 | 3.494 | 4.097 | 3.303 | −3.883 | 0.0413605 | MARVEL domain containing 2 |
| MAF | 10.326 | 9.289 | 9.629 | 7.672 | 7.287 | 9.064 | −3.882 | 0.0433979 | v-maf musculoaponeurotic fibrosarcoma oncogene homolog (avian) |
| SIRT6 | 4.936 | 5.422 | 5.821 | 4.457 | 3.467 | 2.233 | −3.877 | 0.0321778 | sirtuin 6 |
| TMEM50B | 5.230 | 6.625 | 6.751 | 4.799 | 4.618 | 4.049 | −3.870 | 0.0384121 | transmembrane protein 50B |
| LOC552889 | 8.246 | 8.566 | 8.708 | 6.917 | 6.294 | 6.514 | −3.869 | 0.0126444 | No description |
| FBXW4 | 3.792 | 5.668 | 5.548 | 3.718 | 2.648 | 2.648 | −3.863 | 0.0335012 | F-box and WD repeat domain containing 4 |
| NUPR1 | 8.997 | 9.198 | 9.377 | 7.623 | 7.150 | 7.048 | −3.861 | 0.0123199 | nuclear protein, transcriptional regulator, 1 |
| PPAP2A | 6.906 | 7.559 | 6.146 | 4.957 | 4.734 | 5.156 | −3.861 | 0.0216572 | phosphatidic acid phosphatase type 2A |
| KIAA0090 | 5.293 | 6.574 | 6.121 | 3.637 | 4.324 | 4.173 | −3.860 | 0.0207282 | KIAA0090 |
| NUCB1 | 8.622 | 8.043 | 7.042 | 6.194 | 5.904 | 6.094 | −3.860 | 0.0268919 | nucleobindin 1 |
| IGFBP4 | 10.737 | 11.068 | 10.676 | 8.790 | 8.159 | 9.208 | −3.858 | 0.0124801 | insulin-like growth factor binding protein 4 |
| EHD2 | 12.903 | 11.224 | 10.190 | 10.039 | 9.277 | 8.466 | −3.856 | 0.0370555 | EH-domain containing 2 |
| C9orf21 | 8.812 | 9.093 | 7.915 | 7.142 | 6.784 | 6.866 | −3.852 | 0.0285640 | chromosome 9 open reading frame 21 |
| STK32B | 3.947 | 4.915 | 5.045 | 2.970 | 2.970 | 2.970 | −3.849 | 0.0274256 | serine/threonine kinase 32B |
| DFNA5 | 6.312 | 2.401 | 2.593 | 0.648 | 0.648 | 0.648 | −3.849 | 0.0217341 | deafness, autosomal dominant 5 |
| SMAD1 | 7.501 | 7.267 | 6.678 | 5.421 | 5.323 | 5.009 | −3.847 | 0.0154354 | SMAD family member 1 |
| RAB5C | 7.930 | 9.222 | 8.863 | 7.101 | 6.920 | 6.871 | −3.846 | 0.0283158 | RAB5C, member RAS oncogene family |
| LIMCH1 | 5.751 | 6.571 | 6.791 | 3.808 | 4.383 | 5.339 | −3.845 | 0.0304808 | LIM and calponin homology domains 1 |
| NCOA4 | 9.035 | 9.188 | 8.717 | 7.195 | 7.246 | 6.632 | −3.842 | 0.0125723 | nuclear receptor coactivator 4 |
| FGF13 | 4.860 | 2.926 | 3.588 | 1.648 | 1.648 | 1.648 | −3.837 | 0.0210000 | fibroblast growth factor 13 |
| SH3BP5 | 6.824 | 8.445 | 8.029 | 6.133 | 5.573 | 6.093 | −3.826 | 0.0301168 | SH3-domain binding protein 5 (BTK-associated) |
| PKDCC | 8.182 | 6.550 | 7.757 | 5.821 | 5.005 | 5.873 | −3.825 | 0.0283518 | protein kinase domain containing, cytoplasmic homolog (mouse) |
| ARF3 | 10.191 | 9.701 | 9.752 | 8.257 | 8.061 | 7.201 | −3.822 | 0.00152274 | ADP-ribosylation factor 3 |
| PPP1R2 | 5.768 | 6.944 | 6.645 | 4.713 | 4.784 | 3.897 | −3.817 | 0.0206645 | protein phosphatase 1, regulatory (inhibitor) subunit 2 |
| COQ2 | 4.647 | 3.881 | 1.962 | 2.714 | 0.648 | 0.648 | −3.817 | 0.0478146 | coenzyme Q2 homolog, prenyltransferase (yeast) |
| KLHL12 | 3.792 | 5.421 | 5.331 | 3.494 | 2.648 | 2.648 | −3.804 | 0.0309494 | kelch-like 12 (Drosophila) |
| SCCPDH | 5.572 | 5.322 | 5.462 | 3.535 | 3.958 | 3.054 | −3.801 | 0.0142998 | saccharopine dehydrogenase (putative) |
| TRA2A | 7.302 | 9.000 | 8.799 | 6.618 | 6.354 | 7.078 | −3.792 | 0.0439789 | transformer 2 alpha homolog (Drosophila) |
| PRR3 | 4.969 | 5.803 | 4.557 | 3.881 | 2.970 | 2.970 | −3.792 | 0.0273127 | proline rich 3 |
| NUDT5 | 5.204 | 5.222 | 5.053 | 4.529 | 3.284 | 0.648 | −3.785 | 0.0430867 | nudix (nucleoside diphosphate linked moiety X)-type motif 5 |
| ALDH7A1 | 6.190 | 6.158 | 5.100 | 4.026 | 4.271 | 3.701 | −3.782 | 0.0240191 | aldehyde dehydrogenase 7 family, member A1 |
| RNF146 | 6.949 | 7.443 | 7.554 | 5.525 | 5.005 | 5.651 | −3.778 | 0.0146797 | ring finger protein 146 |
| C4orf34 | 4.657 | 4.150 | 3.676 | 2.233 | 2.233 | 2.233 | −3.776 | 0.0150062 | chromosome 4 open reading frame 34 |
| RBM7 | 6.594 | 6.989 | 7.489 | 5.072 | 4.097 | 5.881 | −3.776 | 0.0257556 | RNA binding motif protein 7 |
| NTRK2 | 6.500 | 7.240 | 6.223 | 4.349 | 5.119 | 4.584 | −3.774 | 0.0177286 | neurotrophic tyrosine kinase, receptor, type 2 |
| LMAN1 | 5.594 | 7.252 | 7.376 | 5.461 | 4.108 | 4.382 | −3.772 | 0.0293432 | lectin, mannose-binding, 1 |
| FAM24B | 3.194 | 4.283 | 2.552 | 0.648 | 0.648 | 2.370 | −3.766 | 0.0311449 | family with sequence similarity 24, member B |
| RHOT1 | 5.901 | 5.607 | 5.727 | 4.640 | 3.694 | 3.701 | −3.765 | 0.0235837 | ras homolog gene family, member T1 |
| SETD3 | 6.141 | 5.800 | 5.144 | 3.951 | 4.135 | 3.233 | −3.760 | 0.0203650 | SET domain containing 3 |

TABLE 4-continued

Differentially Expressed Genes in CD44+ Breast Epithelial Cells

| | Nulliparous (NP) Samples | | | Parous (P) Samples | | | Pseudo | | |
|---|---|---|---|---|---|---|---|---|---|
| Gene Symbol | CD44+ N48 | CD44+ N58 | CD44+ N43 | CD44+ N37 | CD44+ N39 | CD44+ N40 | fold change | P value | Gene description |
| TSPYL4 | 3.792 | 5.213 | 4.863 | 2.648 | 2.648 | 3.303 | −3.758 | 0.0315470 | TSPY-like4 |
| NAALADL2 | 4.142 | 4.160 | 4.048 | 2.233 | 2.233 | 2.233 | −3.754 | 0.0069030 | N-acetylated alpha-linked acidic dipeptidase-like 2 |
| PCDHB5 | 4.142 | 4.225 | 3.881 | 2.233 | 2.233 | 2.233 | −3.754 | 0.0099802 | protocadherin beta 5 |
| SERPINF2 | 4.657 | 4.142 | 3.861 | 2.233 | 2.233 | 2.233 | −3.754 | 0.0116350 | serpin peptidase inhibitor, clade F (alpha-2 antiplasmin, pigment epithelium derived factor), member 2 |
| BATF3 | 4.142 | 5.002 | 4.767 | 2.233 | 3.467 | 2.233 | −3.754 | 0.0221425 | basic leucine zipper transcription factor, ATF-like 3 |
| HMGB2 | 4.142 | 5.798 | 5.917 | 2.951 | 2.233 | 4.071 | −3.754 | 0.0288537 | high-mobility group box 2 |
| TAF12 | 4.142 | 5.045 | 4.188 | 3.737 | 2.233 | 2.233 | −3.754 | 0.0414360 | TAF12 RNA polymerase II, TATA box binding protein (TBP)-associated factor, 20 kDa |
| CISH | 4.142 | 4.383 | 2.850 | 2.233 | 2.233 | 2.233 | −3.754 | 0.0451990 | cytokine inducible SH2-containing protein |
| ZBTB38 | 6.142 | 6.220 | 6.807 | 5.244 | 4.233 | 4.233 | −3.754 | 0.0240281 | zinc finger and BTB domain containing 38 |
| RDH10 | 5.142 | 6.962 | 5.368 | 3.233 | 3.233 | 5.159 | −3.754 | 0.0477681 | retinol dehydrogenase 10 (all-trans) |
| H6PD | 7.264 | 7.528 | 6.557 | 6.214 | 5.167 | 4.648 | −3.754 | 0.0352801 | hexose-6-phosphate dehydrogenase (glucose 1-dehydrogenase) |
| PSMD7 | 6.833 | 8.439 | 7.912 | 6.895 | 6.004 | 4.681 | −3.752 | 0.0487137 | proteasome (prosome, macropain) 26S subunit, non-ATPase, 7 |
| SLC9A3R2 | 6.291 | 5.604 | 5.428 | 4.240 | 4.385 | 2.970 | −3.747 | 0.0267934 | solute carrier family 9 (sodium/hydrogen exchanger), member 3 regulator 2 |
| SRPK1 | 6.534 | 7.544 | 7.995 | 5.638 | 5.808 | 4.804 | −3.747 | 0.0260114 | SRSF protein kinase 1 |
| KCNE4 | 9.418 | 11.308 | 10.322 | 8.421 | 8.411 | 9.003 | −3.734 | 0.0403705 | potassium voltage-gated channel, Isk-related family, member 4 |
| FAM76A | 4.378 | 5.942 | 5.111 | 4.042 | 2.970 | 2.970 | −3.734 | 0.0350146 | family with sequence similarity 76, member A |
| CA12 | 7.768 | 7.732 | 8.784 | 6.886 | 6.813 | 5.202 | −3.726 | 0.0420205 | carbonic anhydrase XII |
| SFRS2B | 6.217 | 7.499 | 6.831 | 5.473 | 4.561 | 4.935 | −3.722 | 0.0252614 | No description |
| MRPL9 | 3.422 | 5.456 | 3.544 | 1.648 | 1.648 | 1.648 | −3.721 | 0.0155220 | mitochondrial ribosomal protein L9 |
| GJC2 | 5.452 | 4.839 | 5.652 | 3.557 | 3.499 | 3.557 | −3.721 | 0.0174575 | gap junction protein, gamma 2, 47 kDa |
| MRPS23 | 3.619 | 5.544 | 4.950 | 3.429 | 2.233 | 3.054 | −3.721 | 0.0432808 | mitochondrial ribosomal protein S23 |
| SLCO4A1 | 5.751 | 6.826 | 6.969 | 4.681 | 4.259 | 5.074 | −3.719 | 0.0255532 | solute carrier organic anion transporter family, member 4A1 |
| NDUFA11 | 8.721 | 8.836 | 8.148 | 7.432 | 6.830 | 5.606 | −3.708 | 0.0284870 | NADH dehydrogenase (ubiquinone) 1 alpha subcomplex, 11, 14.7 kDa |
| STS | 5.293 | 4.908 | 5.124 | 3.233 | 3.233 | 3.233 | −3.708 | 0.0096690 | steroid sulfatase (microsomal), isozyme S |
| SPAG7 | 7.233 | 8.041 | 7.611 | 5.656 | 6.151 | 5.558 | −3.707 | 0.0178915 | sperm associated antigen 7 |
| IL13RA1 | 7.703 | 7.781 | 7.346 | 5.457 | 6.273 | 5.506 | −3.704 | 0.0171241 | interleukin 13 receptor, alpha 1 |
| PRKACB | 7.142 | 5.352 | 5.706 | 4.256 | 3.818 | 3.818 | −3.701 | 0.0223636 | protein kinase, cAMP-dependent, catalytic, beta |
| PKN1 | 8.027 | 6.999 | 7.629 | 6.533 | 4.361 | 5.742 | −3.698 | 0.0328718 | protein kinase N1 |
| RBP7 | 7.580 | 6.378 | 5.576 | 4.017 | 5.463 | 4.493 | −3.692 | 0.0434700 | retinol binding protein 7, cellular |
| KIAA1430 | 5.904 | 6.748 | 7.067 | 5.382 | 4.864 | 3.970 | −3.691 | 0.0312988 | KIAA1430 |
| FAM8A1 | 6.245 | 6.164 | 4.858 | 4.280 | 4.294 | 4.013 | −3.690 | 0.0433744 | family with sequence similarity 8, member A1 |
| N4BP2L1 | 5.661 | 4.610 | 5.399 | 3.682 | 2.970 | 3.516 | −3.689 | 0.0227282 | NEDD4 binding protein 2-like 1 |
| CAP2 | 5.255 | 4.115 | 3.581 | 2.233 | 2.233 | 2.233 | −3.686 | 0.0193834 | CAP, adenylate cyclase-associated protein, 2 (yeast) |
| SGCE | 7.791 | 8.436 | 6.863 | 5.196 | 5.189 | 6.555 | −3.685 | 0.0276246 | sarcoglycan, epsilon |
| VEGFA | 13.253 | 12.011 | 11.804 | 9.923 | 10.388 | 11.331 | −3.683 | 0.0379449 | vascular endothelial growth factor A |
| GHITM | 5.730 | 7.640 | 7.718 | 5.837 | 4.264 | 4.516 | −3.683 | 0.0321189 | growth hormone inducible transmembrane protein |
| TIMELESS | 5.173 | 4.722 | 5.471 | 3.218 | 3.294 | 3.303 | −3.678 | 0.0143615 | timeless homolog (Drosophila) |
| FPGS | 6.472 | 7.513 | 7.831 | 5.958 | 5.358 | 4.733 | −3.663 | 0.0273355 | folylpolyglutamate synthase |
| TMX1 | 6.663 | 6.691 | 7.164 | 4.820 | 4.587 | 5.553 | −3.660 | 0.0192017 | thioredoxin-related transmembrane protein 1 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| FSCN1 | 9.852 | 8.192 | 8.611 | 6.320 | 6.953 | 7.776 | −3.660 | 0.0372073 | fascin homolog 1, actin-bundling protein (Strongylocentrotus purpuratus) |
| MYO1B | 7.816 | 8.103 | 8.340 | 6.549 | 6.191 | 5.945 | −3.660 | 0.0146659 | myosin IB |
| PRR23A | 8.172 | 8.501 | 8.745 | 6.124 | 6.630 | 7.472 | −3.659 | 0.0294000 | proline rich 23A |
| NAA38 | 6.133 | 6.679 | 6.981 | 5.870 | 4.728 | 4.262 | −3.657 | 0.0437445 | N(alpha)-acetyltransferase 38, NatC auxiliary subunit |
| SLC25A28 | 6.315 | 8.181 | 7.171 | 5.629 | 5.302 | 5.285 | −3.654 | 0.0331220 | solute carrier family 25, member 28 |
| DPYD | 5.846 | 5.305 | 6.232 | 3.233 | 3.978 | 4.650 | −3.650 | 0.0280024 | dihydropyrimidine dehydrogenase |
| IFI6 | 11.376 | 10.183 | 10.594 | 9.050 | 8.318 | 8.830 | −3.643 | 0.0187227 | interferon, alpha-inducible protein 6 |
| ATP6V1F | 6.895 | 8.466 | 8.048 | 6.572 | 6.184 | 5.396 | −3.640 | 0.0395345 | ATPase, H+ transporting, lysosomal 14 kDa, V1 subunit F |
| C11orf95 | 6.967 | 6.659 | 6.324 | 4.496 | 4.462 | 5.262 | −3.636 | 0.0168690 | chromosome 11 open reading frame 95 |
| HSD17B14 | 6.133 | 5.213 | 5.452 | 3.662 | 3.633 | 3.351 | −3.635 | 0.0124440 | hydroxysteroid (17-beta) dehydrogenase 14 |
| RFK | 4.264 | 4.818 | 4.510 | 2.648 | 2.648 | 2.648 | −3.635 | 0.0112087 | riboflavin kinase |
| ANXA4 | 7.463 | 6.036 | 6.097 | 5.057 | 4.174 | 5.023 | −3.635 | 0.0351449 | annexin A4 |
| MFN1 | 3.792 | 5.642 | 4.510 | 2.648 | 2.648 | 3.303 | −3.633 | 0.0374035 | mitofusin 1 |
| ASCC2 | 4.525 | 6.166 | 4.915 | 2.951 | 3.686 | 3.054 | −3.633 | 0.0255442 | activating signal cointegrator 1 complex subunit 2 |
| SIX4 | 5.404 | 6.123 | 5.699 | 3.648 | 3.648 | 4.264 | −3.626 | 0.0162735 | SIX homeobox 4 |
| COPS7A | 5.107 | 6.488 | 5.717 | 4.515 | 3.859 | 3.456 | −3.625 | 0.0295449 | COP9 constitutive photomorphogenic homolog subunit 7A (Arabidopsis) |
| SLC25A34 | 6.118 | 7.776 | 7.310 | 5.453 | 4.659 | 5.467 | −3.622 | 0.0306340 | solute carrier family 25, member 34 |
| HMGCS1 | 6.198 | 7.021 | 7.294 | 5.438 | 4.865 | 4.694 | −3.620 | 0.0234811 | 3-hydroxy-3-methylglutaryl-CoA synthase 1 (soluble) |
| CTSB | 9.929 | 10.637 | 11.449 | 9.594 | 8.535 | 8.388 | −3.617 | 0.0343983 | cathepsin B |
| UXT | 7.460 | 8.807 | 8.417 | 6.952 | 5.977 | 6.388 | −3.617 | 0.0304440 | ubiquitously-expressed transcript |
| FAM18B | 3.194 | 3.810 | 4.934 | 3.081 | 2.353 | 0.648 | −3.613 | 0.0492059 | No description |
| RBP1 | 6.320 | 5.841 | 5.117 | 3.988 | 4.001 | 3.516 | −3.612 | 0.0193425 | retinol binding protein 1, cellular |
| CHSY1 | 10.405 | 10.193 | 9.687 | 8.343 | 8.135 | 8.526 | −3.607 | 0.0177778 | chondroitin sulfate synthase 1 |
| RUSC2 | 6.208 | 7.495 | 7.525 | 5.674 | 5.086 | 5.644 | −3.606 | 0.0409487 | RUN and SH3 domain containing 2 |
| NR3C1 | 7.529 | 7.789 | 7.416 | 5.833 | 5.093 | 5.939 | −3.606 | 0.0144537 | nuclear receptor subfamily 3, group C, member 1 (glucocorticoid receptor) |
| PUM2 | 7.704 | 8.349 | 8.553 | 5.881 | 6.152 | 6.704 | −3.602 | 0.0169452 | pumilio homolog 2 (Drosophila) |
| CFL1 | 12.625 | 12.901 | 12.668 | 10.819 | 11.353 | 10.370 | −3.602 | 0.0165646 | cofilin 1 (non-muscle) |
| LIMS2 | 8.052 | 6.627 | 6.636 | 4.778 | 5.553 | 5.430 | −3.601 | 0.0299886 | LIM and senescent cell antigen-like domains 2 |
| LRP1 | 12.146 | 11.071 | 11.708 | 9.978 | 9.114 | 10.300 | −3.595 | 0.0268024 | low density lipoprotein receptor-related protein 1 |
| NMNAT2 | 3.947 | 5.673 | 5.137 | 2.970 | 3.827 | 2.970 | −3.595 | 0.0463969 | nicotinamide nucleotide adenylyltransferase 2 |
| CCDC120 | 7.352 | 8.367 | 8.238 | 6.393 | 6.537 | 5.453 | −3.594 | 0.0257827 | coiled-coil domain containing 120 |
| NOTCH1 | 7.986 | 8.091 | 7.350 | 5.506 | 5.716 | 6.875 | −3.591 | 0.0307414 | notch 1 |
| PDGFC | 4.378 | 5.341 | 5.359 | 3.442 | 2.970 | 3.516 | −3.588 | 0.0262548 | platelet derived growth factor C |
| CCDC34 | 6.444 | 5.499 | 5.378 | 3.535 | 4.523 | 4.071 | −3.586 | 0.0303373 | coiled-coil domain containing 34 |
| C19orf62 | 4.817 | 6.254 | 6.760 | 4.748 | 4.413 | 3.054 | −3.582 | 0.0468406 | chromosome 19 open reading frame 62 |
| RSAD2 | 5.708 | 7.197 | 6.596 | 4.756 | 4.490 | 4.848 | −3.580 | 0.0270686 | radical S-adenosyl methionine domain containing 2 |
| ACVR1 | 8.692 | 8.141 | 8.988 | 7.761 | 6.852 | 6.227 | −3.579 | 0.0401334 | activin A receptor, type I |
| PFKFB3 | 10.900 | 11.092 | 10.364 | 8.524 | 8.788 | 9.353 | −3.579 | 0.0175969 | 6-phosphofructo-2-kinase/fructose-2,6-biphosphatase 3 |
| NFS1 | 5.109 | 6.133 | 5.163 | 4.276 | 4.294 | 3.054 | −3.579 | 0.0470957 | NFS1 nitrogen fixation 1 homolog (S. cerevisiae) |
| CDK11A | 3.422 | 5.540 | 5.340 | 2.625 | 3.704 | 1.648 | −3.570 | 0.0402360 | cyclin-dependent kinase 11A |
| TFPI2 | 5.587 | 6.742 | 5.358 | 4.017 | 3.659 | 3.752 | −3.567 | 0.0171151 | tissue factor pathway inhibitor 2 |
| CBX6 | 5.289 | 6.350 | 5.930 | 4.681 | 3.859 | 3.456 | −3.562 | 0.0263262 | chromobox homolog 6 |
| OBFC1 | 5.968 | 6.243 | 6.566 | 5.214 | 4.411 | 4.042 | −3.559 | 0.0288492 | oligonucleotide/oligosaccharide-binding fold containing 1 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| CAV1 | 11.402 | 11.375 | 9.824 | 9.551 | 9.544 | 7.994 | −3.559 | 0.0456253 | caveolin 1, caveolae protein, 22 kDa |
| COL5A1 | 11.883 | 9.199 | 9.090 | 7.369 | 7.282 | 8.055 | −3.557 | 0.0260711 | collagen, type V, alpha 1 |
| ITGA7 | 8.251 | 7.768 | 6.515 | 5.937 | 5.235 | 6.098 | −3.557 | 0.0391789 | integrin, alpha 7 |
| STAT1 | 7.798 | 7.641 | 7.829 | 7.000 | 5.968 | 5.769 | −3.555 | 0.0407040 | signal transducer and activator of transcription 1,91 kDa |
| DOLPP1 | 5.173 | 5.488 | 5.571 | 4.390 | 3.659 | 2.648 | −3.554 | 0.0295719 | dolichyl pyrophosphate phosphatase 1 |
| ZCCHC7 | 5.160 | 5.106 | 4.916 | 3.278 | 3.467 | 2.233 | −3.550 | 0.0155955 | zinc finger, CCHC domain containing 7 |
| COL7A1 | 4.948 | 5.476 | 6.115 | 3.648 | 4.007 | 3.648 | −3.550 | 0.0246763 | collagen, type VII, alpha 1 |
| SCNN1B | 3.422 | 3.475 | 4.429 | 1.648 | 1.648 | 1.648 | −3.547 | 0.0121397 | sodium channel, nonvoltage-gated 1, beta |
| CNOT10 | 3.619 | 4.719 | 4.778 | 2.951 | 2.233 | 2.233 | −3.546 | 0.0236468 | CCR4-NOT transcription complex, subunit 10 |
| PRKAA1 | 4.214 | 5.289 | 5.633 | 3.808 | 3.456 | 3.456 | −3.544 | 0.0497251 | protein kinase. AMP-activated, alpha 1 catalytic subunit |
| C17orf101 | 4.525 | 5.360 | 4.641 | 3.535 | 2.233 | 3.508 | −3.543 | 0.0335879 | chromosome 17 open reading frame 101 |
| YPEL3 | 6.545 | 7.998 | 8.486 | 6.356 | 5.199 | 6.174 | −3.543 | 0.0469196 | yippee-like 3 (Drosophila) |
| CHCHD3 | 6.770 | 7.213 | 6.475 | 5.628 | 4.946 | 4.351 | −3.542 | 0.0244565 | coiled-coil-helix-coiled-coil-helix domain containing 3 |
| PRINS | 5.644 | 5.252 | 6.070 | 3.429 | 4.294 | 3.508 | −3.539 | 0.0187726 | psoriasis associated RNA induced by stress (non-protein coding) |
| PM20D2 | 5.047 | 6.125 | 6.371 | 4.362 | 4.007 | 4.303 | −3.535 | 0.0353626 | peptidase M20 domain containing 2 |
| EHD4 | 4.619 | 6.191 | 5.458 | 3.637 | 3.694 | 3.233 | −3.534 | 0.0248641 | EH-domain containing 4 |
| PGAP2 | 4.709 | 4.791 | 5.937 | 2.970 | 2.970 | 2.970 | −3.532 | 0.0135456 | post-GPI attachment to proteins 2 |
| FAM3B | 4.647 | 4.901 | 6.198 | 3.081 | 4.602 | 0.648 | −3.530 | 0.0421730 | family with sequence similarity 3, member B |
| CASC4 | 10.130 | 9.494 | 9.065 | 8.213 | 7.642 | 7.674 | −3.530 | 0.0257161 | cancer susceptibility candidate 4 |
| CCDC152 | 10.040 | 7.718 | 8.005 | 6.186 | 6.101 | 7.632 | −3.529 | 0.0495650 | coiled-coil domain containing 152 |
| SFRS3 | 9.698 | 10.957 | 10.520 | 9.140 | 8.641 | 8.652 | −3.525 | 0.0367255 | No description |
| C6orf192 | 5.503 | 5.888 | 5.952 | 3.278 | 5.030 | 4.071 | −3.525 | 0.0419678 | chromosome 6 open reading frame 192 |
| SF1 | 11.276 | 12.211 | 11.883 | 9.708 | 10.212 | 10.066 | −3.523 | 0.0202471 | splicing factor 1 |
| EN1 | 5.341 | 6.002 | 5.314 | 3.557 | 3.499 | 3.557 | −3.520 | 0.0109154 | engrailed homeobox 1 |
| NBL1 | 7.036 | 8.704 | 7.369 | 6.889 | 5.304 | 5.445 | −3.519 | 0.0454319 | neuroblastoma, suppression of tumorigenicity 1 |
| C5orf32 | 8.745 | 9.438 | 9.450 | 7.636 | 7.428 | 7.294 | −3.516 | 0.0184842 | chromosome 5 open reading frame 32 |
| ETNK2 | 5.552 | 4.713 | 4.646 | 3.718 | 3.739 | 2.648 | −3.514 | 0.0404842 | ethanolamine kinase 2 |
| LPPR2 | 8.824 | 8.642 | 9.014 | 7.157 | 6.974 | 7.012 | −3.510 | 0.0121078 | No description |
| CD200 | 5.007 | 6.242 | 5.044 | 3.233 | 3.233 | 3.233 | −3.507 | 0.0134049 | CD200 molecule |
| ZAK | 9.957 | 9.022 | 8.113 | 7.847 | 7.212 | 7.018 | −3.506 | 0.0459227 | No description |
| C4orf3 | 10.365 | 10.049 | 9.959 | 8.664 | 8.243 | 7.383 | −3.499 | 0.0168135 | chromosome 4 open reading frame 3 |
| BLMH | 6.818 | 7.375 | 6.094 | 5.328 | 4.289 | 5.083 | −3.495 | 0.0268205 | bleomycin hydrolase |
| TSPAN7 | 7.233 | 5.656 | 5.021 | 3.494 | 3.852 | 4.579 | −3.491 | 0.0354541 | tetraspanin 7 |
| JAK1 | 7.020 | 8.486 | 7.562 | 6.183 | 5.217 | 6.651 | −3.490 | 0.0472551 | Janus kinase 1 |
| EIF3E | 5.915 | 6.684 | 6.832 | 4.581 | 5.029 | 4.820 | −3.489 | 0.0252704 | eukaryotic translation initiation factor 3, subunit E |
| SSPN | 8.319 | 5.604 | 5.451 | 3.648 | 4.007 | 4.303 | −3.488 | 0.0269009 | sarcospan (Kras oncogene-associated gene) |
| CASD1 | 7.053 | 5.975 | 5.578 | 5.200 | 4.135 | 4.173 | −3.487 | 0.0416745 | CAS1 domain containing 1 |
| PSPC1 | 4.708 | 5.917 | 5.410 | 3.456 | 4.115 | 3.456 | −3.487 | 0.0318021 | paraspeckle component 1 |
| MTND6 | 13.009 | 12.338 | 12.201 | 10.828 | 11.028 | 10.400 | −3.486 | 0.0213626 | No description |
| BTG1 | 10.912 | 11.456 | 11.607 | 9.362 | 9.113 | 10.474 | −3.480 | 0.0357667 | B-cell translocation gene 1, anti-proliferative |
| NRAS | 8.203 | 7.486 | 7.136 | 6.404 | 6.212 | 4.293 | −3.478 | 0.0374811 | neuroblastoma RAS viral (v-ras) oncogene homolog |
| UBQLN2 | 8.225 | 8.864 | 8.431 | 7.020 | 6.793 | 6.427 | −3.477 | 0.0185161 | ubiquilin 2 |
| CRLF3 | 5.525 | 7.535 | 6.882 | 5.086 | 4.339 | 5.290 | −3.473 | 0.0465924 | cytokine receptor-like factor 3 |
| WDR60 | 3.619 | 4.485 | 5.074 | 3.278 | 2.233 | 2.233 | −3.473 | 0.0332295 | WD repeat domain 60 |
| ZFP36L2 | 11.829 | 12.143 | 11.720 | 9.913 | 10.034 | 10.944 | −3.473 | 0.0311130 | zinc finger protein 36. C3H type-like 2 |

TABLE 4-continued

Differentially Expressed Genes in CD44+ Breast Epithelial Cells

| | Nulliparous (NP) Samples | | | Parous (P) Samples | | | Pseudo fold change | P value | Gene description |
|---|---|---|---|---|---|---|---|---|---|
| Gene Symbol | CD44+ N48 | CD44+ N58 | CD44+ N43 | CD44+ N37 | CD44+ N39 | CD44+ N40 | | | |
| TIMM10 | 7.081 | 7.298 | 7.859 | 5.502 | 6.232 | 4.830 | -3.472 | 0.0247581 | translocase of inner mitochondrial membrane 10 homolog (yeast) |
| ABT1 | 6.348 | 7.236 | 7.506 | 5.837 | 5.441 | 4.007 | -3.471 | 0.0337459 | activator of basal transcription 1 |
| STAC | 5.042 | 3.441 | 4.281 | 1.648 | 3.704 | 1.648 | -3.464 | 0.0470617 | SH3 and cysteine rich domain |
| EDEM2 | 4.969 | 4.508 | 5.235 | 3.442 | 2.970 | 2.970 | -3.464 | 0.0184260 | ER degradation enhancer, mannosidase alpha-like 2 |
| TPP3 | 8.553 | 7.982 | 7.295 | 5.109 | 6.190 | 7.222 | -3.462 | 0.0489903 | tubulin polymerization-promoting protein family member 3 |
| C1orf103 | 3.422 | 5.595 | 3.437 | 1.648 | 1.648 | 1.648 | -3.456 | 0.0173598 | chromosome 1 open reading frame 103 |
| PCMTD2 | 6.654 | 6.153 | 6.160 | 5.097 | 4.372 | 4.013 | -3.454 | 0.0215726 | protein-L-isoaspartate (D-aspartate) O-methyltransferase domain containing 2 |
| DYRK4 | 3.422 | 5.502 | 5.078 | 3.714 | 1.648 | 1.648 | -3.453 | 0.0313279 | dual-specificity tyrosine-(Y)-phosphorylation regulated kinase 4 |
| EEPD1 | 6.649 | 4.771 | 5.647 | 3.442 | 4.001 | 3.859 | -3.453 | 0.0289321 | endonuclease/exonuclease/phosphatase family domain containing 1 |
| NAP1L1 | 9.078 | 10.402 | 10.009 | 8.157 | 7.820 | 8.614 | -3.453 | 0.0373854 | nucleosome assembly protein 1-like 1 |
| FZD1 | 7.053 | 7.110 | 6.623 | 4.835 | 5.213 | 6.068 | -3.452 | 0.0377348 | frizzled homolog 1 (Drosophila) |
| SCMH1 | 4.793 | 5.743 | 5.911 | 4.124 | 3.233 | 3.233 | -3.451 | 0.0221903 | sex comb on midleg homolog 1 (Drosophila) |
| CCDC47 | 8.569 | 9.625 | 8.687 | 6.891 | 7.270 | 6.900 | -3.450 | 0.0176419 | coiled-coil domain containing 47 |
| FLNC | 6.769 | 7.329 | 8.120 | 4.984 | 5.358 | 6.428 | -3.446 | 0.0356364 | filamin C, gamma |
| LEF1 | 6.051 | 5.018 | 4.173 | 3.233 | 3.233 | 3.233 | -3.445 | 0.0309688 | lymphoid enhancer-binding factor 1 |
| EIF3D | 9.453 | 9.804 | 10.229 | 8.203 | 8.173 | 7.669 | -3.443 | 0.0181286 | eukaryotic translation initiation factor 3, subunit D |
| RB1 | 4.708 | 5.237 | 5.771 | 3.456 | 3.456 | 3.456 | -3.438 | 0.0204163 | retinoblastoma 1 |
| C14orf132 | 5.727 | 5.322 | 5.599 | 3.818 | 3.818 | 3.818 | -3.436 | 0.0131865 | chromosome 14 open reading frame 132 |
| TUBB | 13.026 | 11.486 | 11.832 | 10.982 | 10.052 | 9.901 | -3.435 | 0.0358187 | tubulin, beta |
| SNX17 | 4.672 | 6.489 | 6.360 | 4.710 | 3.648 | 3.648 | -3.432 | 0.0417043 | sorting nexin 17 |
| TXNDC9 | 3.422 | 5.208 | 5.793 | 4.017 | 1.648 | 1.648 | -3.423 | 0.0364801 | thioredoxin domain containing 9 |
| WASL | 6.209 | 8.015 | 7.480 | 6.239 | 4.964 | 5.362 | -3.423 | 0.0486541 | Wiskott-Aldrich syndrome-like |
| NEO1 | 6.221 | 6.694 | 5.201 | 4.091 | 4.447 | 4.604 | -3.419 | 0.0364939 | neogenin 1 |
| ZWINT | 3.422 | 3.294 | 3.544 | 1.648 | 1.648 | 1.648 | -3.419 | 0.0103927 | ZW10 interactor |
| TMEM144 | 3.422 | 3.209 | 4.395 | 1.648 | 1.648 | 1.648 | -3.419 | 0.0156225 | transmembrane protein 144 |
| PLN | 3.422 | 4.368 | 3.077 | 1.648 | 1.648 | 1.648 | -3.419 | 0.0179109 | phospholamban |
| TIGD3 | 3.422 | 3.832 | 2.943 | 1.648 | 1.648 | 1.648 | -3.419 | 0.0189050 | tigger transposable element derived 3 |
| BOLA1 | 3.422 | 3.557 | 2.776 | 1.648 | 1.648 | 1.648 | -3.419 | 0.0240783 | bolA homolog 1 (E. coli) |
| SLCO4C1 | 3.422 | 2.776 | 3.557 | 1.648 | 1.648 | 1.648 | -3.419 | 0.0240783 | solute carrier organic anion transporter family, member 4C1 |
| TMEM35 | 3.422 | 3.566 | 2.744 | 1.648 | 1.648 | 1.648 | -3.419 | 0.0249931 | transmembrane protein 35 |
| ZNF137 | 3.422 | 3.645 | 2.710 | 1.648 | 1.648 | 1.648 | -3.419 | 0.0259179 | No description |
| UQCRB | 3.422 | 4.262 | 4.686 | 3.023 | 1.648 | 1.648 | -3.419 | 0.0260801 | ubiquinol-cytochrome c reductase binding protein |
| UFSP2 | 4.422 | 4.405 | 5.529 | 3.718 | 2.648 | 2.648 | -3.419 | 0.0325875 | UFM1-specific peptidase 2 |
| DTD1 | 3.422 | 4.395 | 3.557 | 3.557 | 1.648 | 1.648 | -3.419 | 0.0382984 | D-tyrosyl-tRNA deacylase 1 homolog (S. cerevisiae) |
| ACAT2 | 3.422 | 4.008 | 3.627 | 3.023 | 1.648 | 1.648 | -3.417 | 0.0447976 | acetyl-CoA acetyltransferase 2 |
| IFNGR1 | 5.482 | 6.940 | 6.700 | 5.167 | 4.467 | 4.054 | -3.415 | 0.0337924 | interferon gamma receptor 1 |
| ALOX15 | 3.422 | 3.420 | 2.304 | 1.648 | 1.648 | 1.648 | -3.415 | 0.0493279 | arachidonate 15-lipoxygenase |
| SOCS1 | 5.982 | 5.420 | 4.826 | 4.182 | 2.648 | 4.210 | -3.415 | 0.0438867 | suppressor of cytokine signaling 1 |
| FAM110B | 5.775 | 6.329 | 5.913 | 4.762 | 4.141 | 3.818 | -3.414 | 0.0220863 | family with sequence similarity 110, member B |
| ANP32B | 8.093 | 8.910 | 8.947 | 7.176 | 6.788 | 6.752 | -3.413 | 0.0221744 | acidic (leucine-rich) nuclear phosphoprotein 32 family, member B |
| FAM160A2 | 4.793 | 6.125 | 5.867 | 4.357 | 3.978 | 4.007 | -3.406 | 0.0471872 | family with sequence similarity 160, member A2 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| NPDC1 | 8.877 | 7.481 | 8.258 | 6.472 | 6.497 | 6.491 | −3.406 | 0.0285404 | neural proliferation, differentiation and control, 1 |
| CHD1L | 3.947 | 5.626 | 4.738 | 2.970 | 2.970 | 2.970 | −3.405 | 0.0296738 | chromodomain helicase DNA binding protein 1-like |
| DDB2 | 5.503 | 5.160 | 4.142 | 2.951 | 3.043 | 3.737 | −3.401 | 0.0354679 | damage-specific DNA binding protein 2, 48 kDa |
| ETFA | 5.503 | 6.710 | 7.203 | 5.167 | 5.017 | 3.737 | −3.401 | 0.0417737 | electron-transfer-flavoprotein, alpha polypeptide |
| FAM20A | 6.460 | 6.925 | 6.227 | 5.015 | 4.462 | 4.698 | −3.399 | 0.0170139 | family with sequence similarity 20, member A |
| TMED10 | 6.038 | 5.556 | 5.219 | 4.385 | 3.456 | 3.456 | −3.395 | 0.0229861 | transmembrane emp24-like trafficking protein 10 (yeast) |
| LAMP1 | 9.810 | 10.376 | 9.563 | 9.020 | 7.824 | 7.801 | −3.392 | 0.0341279 | lysosomal-associated membrane protein 1 |
| OR51E2 | 7.353 | 8.009 | 7.544 | 6.994 | 5.591 | 5.591 | −3.391 | 0.0464288 | olfactory receptor, family 51, subfamily E, member 2 |
| PNP | 10.020 | 9.390 | 9.458 | 8.060 | 8.258 | 7.196 | −3.391 | 0.0244218 | purine nucleoside phosphorylase |
| CSTB | 8.305 | 9.421 | 9.749 | 7.731 | 7.661 | 6.983 | −3.387 | 0.0362471 | cystatin B (stefin B) |
| TFAP4 | 5.503 | 5.496 | 4.817 | 3.737 | 4.151 | 2.233 | −3.385 | 0.0336634 | transcription factor AP-4 (activating enhancer binding protein 4) |
| ZNF71 | 4.936 | 4.128 | 3.987 | 3.278 | 2.233 | 2.233 | −3.372 | 0.0294139 | zinc finger protein 71 |
| C1orf123 | 5.838 | 5.632 | 5.542 | 3.881 | 2.970 | 4.453 | −3.366 | 0.0231768 | chromosome 1 open reading frame 123 |
| UCP2 | 5.322 | 5.783 | 4.149 | 4.033 | 3.043 | 3.054 | −3.365 | 0.0431026 | uncoupling protein 2 (mitochondrial, proton carrier) |
| BRD7 | 3.947 | 6.354 | 5.192 | 3.442 | 3.508 | 2.970 | −3.364 | 0.0428364 | bromodomain containing 7 |
| SLC39A9 | 7.345 | 7.559 | 7.615 | 6.439 | 5.339 | 5.810 | −3.361 | 0.0273806 | solute carrier family 39 (zinc transporter), member 9 |
| EDC3 | 5.204 | 6.090 | 6.344 | 3.456 | 4.694 | 3.865 | −3.361 | 0.0271255 | enhancer of mRNA decapping 3 homolog (S. cerevisiae) |
| TMEM30A | 8.141 | 9.632 | 9.660 | 7.913 | 7.266 | 6.966 | −3.355 | 0.0379289 | transmembrane protein 30A |
| SGCB | 7.281 | 6.968 | 5.971 | 5.517 | 3.970 | 5.536 | −3.350 | 0.0468607 | sarcoglycan, beta (43 kDa dystrophin-associated glycoprotein) |
| GLTPD1 | 5.160 | 5.702 | 5.783 | 4.151 | 3.958 | 2.233 | −3.350 | 0.0254887 | glycolipid transfer protein domain containing 1 |
| TMCO1 | 5.877 | 7.619 | 6.747 | 5.193 | 5.005 | 4.173 | −3.344 | 0.0287567 | transmembrane and coiled-coil domains 1 |
| PCOLCE2 | 4.264 | 7.566 | 5.044 | 2.648 | 4.273 | 3.303 | −3.342 | 0.0474846 | procollagen C-endopeptidase enhancer 2 |
| WDR83 | 4.264 | 4.388 | 5.542 | 2.648 | 2.648 | 2.648 | −3.340 | 0.0158562 | WD repeat domain 83 |
| CCNT1 | 4.709 | 5.645 | 4.473 | 2.970 | 3.508 | 2.970 | −3.337 | 0.0250111 | cyclin T1 |
| ZNF117 | 4.709 | 5.019 | 4.901 | 3.988 | 2.970 | 2.970 | −3.337 | 0.0333868 | zinc finger protein 117 |
| C20orf30 | 9.320 | 8.709 | 8.701 | 7.990 | 6.971 | 6.522 | −3.336 | 0.0319435 | chromosome 20 open reading frame 30 |
| PRNP | 9.295 | 10.501 | 9.601 | 7.557 | 8.234 | 8.535 | −3.334 | 0.0344073 | prion protein |
| ZNF92 | 3.619 | 3.968 | 4.887 | 2.233 | 2.233 | 2.233 | −3.329 | 0.0190679 | zinc finger protein 92 |
| NDUFB11 | 7.390 | 7.390 | 7.244 | 6.032 | 5.513 | 5.509 | −3.329 | 0.0181924 | NADH dehydrogenase (ubiquinone) 1 beta subcomplex, 11, 17.3 kDa |
| RPL29 | 6.061 | 5.673 | 6.491 | 2.625 | 4.757 | 4.692 | −3.328 | 0.0329425 | ribosomal protein L29 |
| ZC3H4 | 6.730 | 7.161 | 7.582 | 5.153 | 5.429 | 5.564 | −3.322 | 0.0189231 | zinc finger CCCH-type containing 4 |
| EPB41L2 | 6.497 | 7.843 | 7.245 | 5.647 | 4.641 | 6.111 | −3.322 | 0.0412634 | erythrocyte membrane protein band 4.1-like 2 |
| SMG7 | 6.147 | 6.259 | 6.109 | 5.128 | 4.377 | 4.382 | −3.322 | 0.0275158 | Smg-7 homolog, nonsense mediated mRNA decay factor (C. elegans) |
| DCAF11 | 6.472 | 6.159 | 6.218 | 5.526 | 4.488 | 4.264 | −3.318 | 0.0408697 | DDB1 and CUL4 associated factor 11 |
| ZBTB2 | 6.818 | 7.188 | 6.401 | 5.088 | 4.504 | 5.458 | −3.317 | 0.0233792 | zinc finger and BTB domain containing 2 |
| RPS15A | 9.776 | 10.479 | 10.602 | 7.931 | 8.749 | 9.132 | −3.317 | 0.0328357 | ribosomal protein S15a |
| TPCN1 | 6.099 | 6.709 | 7.175 | 4.741 | 4.775 | 5.446 | −3.316 | 0.0297099 | two pore segment channel 1 |
| BACH1 | 6.503 | 7.853 | 7.846 | 5.477 | 5.506 | 6.124 | −3.314 | 0.0361903 | BTB and CNC homology 1, basic leucine zipper transcription factor 1 |
| RCOR3 | 6.137 | 5.950 | 5.536 | 3.808 | 4.115 | 4.409 | −3.312 | 0.0180544 | REST corepressor 3 |
| ZNF805 | 5.461 | 6.980 | 6.485 | 4.833 | 4.758 | 4.761 | −3.305 | 0.0453785 | zinc finger protein 805 |
| NCAM1 | 6.471 | 4.448 | 4.957 | 3.637 | 3.233 | 3.233 | −3.303 | 0.0319837 | neural cell adhesion molecule 1 |
| PHF13 | 7.172 | 6.946 | 6.536 | 4.814 | 5.009 | 6.122 | −3.300 | 0.0415795 | PHD finger protein 13 |

TABLE 4-continued

Differentially Expressed Genes in CD44+ Breast Epithelial Cells

| | Nulliparous (NP) Samples | | | Parous (P) Samples | | | Pseudo fold change | P value | |
|---|---|---|---|---|---|---|---|---|---|
| Gene Symbol | CD44+ N48 | CD44+ N58 | CD44+ N43 | CD44+ N37 | CD44+ N39 | CD44+ N40 | | | Gene description |
| BMP4 | 7.837 | 7.259 | 6.105 | 4.385 | 4.385 | 6.140 | −3.294 | 0.0328447 | bone morphogenetic protein 4 |
| SIKE1 | 4.580 | 5.646 | 5.716 | 3.997 | 3.859 | 3.456 | −3.292 | 0.0393875 | suppressor of IKBKE 1 |
| CHRNB1 | 5.377 | 5.370 | 5.555 | 3.838 | 2.648 | 3.694 | −3.289 | 0.0158652 | cholinergic receptor, nicotinic, beta 1 (muscle) |
| EI24 | 8.132 | 9.110 | 8.471 | 7.474 | 6.754 | 6.044 | −3.288 | 0.0300676 | etoposide induced 2.4 mRNA |
| LEPR | 8.861 | 9.485 | 9.064 | 7.348 | 7.175 | 7.699 | −3.287 | 0.0187567 | leptin receptor |
| C2orf29 | 4.524 | 5.867 | 5.959 | 4.242 | 3.508 | 3.859 | −3.287 | 0.0464766 | chromosome 2 open reading frame 29 |
| EFR3A | 5.620 | 6.277 | 6.300 | 4.562 | 4.600 | 3.648 | −3.283 | 0.0241577 | EFR3 homolog A (S. cerevisiae) |
| PSMB1 | 7.212 | 10.590 | 7.496 | 6.310 | 5.782 | 5.598 | −3.283 | 0.0314118 | proteasome (prosome, macropain) subunit, beta type, 1 |
| MACROD1 | 4.142 | 5.143 | 4.142 | 3.429 | 3.043 | 2.233 | −3.282 | 0.0448558 | MACRO domain containing 1 |
| NUDT16L1 | 4.008 | 4.376 | 4.339 | 2.625 | 1.648 | 2.752 | −3.280 | 0.0194201 | nudix (nucleoside diphosphate linked moiety X)-type motif 16-like 1 |
| B3GNT2 | 6.536 | 7.571 | 6.203 | 5.570 | 4.490 | 5.226 | −3.279 | 0.0399400 | UDP-GlcNAc:betaGal beta-1,3-N-acetylglucosaminyltransferase 2 |
| SLC36A4 | 4.872 | 5.297 | 5.572 | 3.456 | 3.859 | 3.456 | −3.279 | 0.0219075 | solute carrier family 36 (proton/amino acid symporter), member 4 |
| SET | 10.094 | 10.702 | 10.630 | 8.721 | 8.970 | 8.917 | −3.278 | 0.0218555 | SET nuclear oncogene |
| C16orf72 | 9.360 | 9.327 | 9.067 | 6.778 | 7.615 | 8.438 | −3.276 | 0.0396177 | chromosome 16 open reading frame 72 |
| TSC22D1 | 9.761 | 10.710 | 10.438 | 8.154 | 8.250 | 8.999 | −3.274 | 0.0230159 | TSC22 domain family, member 1 |
| RALA | 7.670 | 8.422 | 8.509 | 6.620 | 6.798 | 6.562 | −3.273 | 0.0292676 | v-ral simian leukemia viral oncogene homolog A (ras related) |
| RAB2A | 10.432 | 10.367 | 10.606 | 8.349 | 8.726 | 8.957 | −3.263 | 0.0147678 | RAB2A, member RAS oncogene family |
| SLC5A3 | 6.247 | 7.236 | 7.059 | 4.642 | 4.823 | 5.532 | −3.258 | 0.0235567 | solute carrier family 5 (sodium/myo-inositol cotransporter), member 3 |
| BBS10 | 5.008 | 5.309 | 5.601 | 3.897 | 3.659 | 3.303 | −3.257 | 0.0206492 | Bardet-Biedl syndrome 10 |
| CIR1 | 5.350 | 5.567 | 5.954 | 3.997 | 3.859 | 3.865 | −3.253 | 0.0162977 | corepressor interacting with RBPJ, 1 |
| SMAD4 | 6.620 | 7.253 | 7.269 | 6.027 | 5.325 | 4.919 | −3.252 | 0.0325542 | SMAD family member 4 |
| TAF7 | 5.847 | 6.551 | 6.081 | 4.850 | 4.453 | 2.233 | −3.251 | 0.0272503 | TAF7 RNA polymerase II, TATA box binding protein (TBP)-associated factor, 55 kDa |
| EIF4H | 11.021 | 12.110 | 11.626 | 9.927 | 9.993 | 9.704 | −3.248 | 0.0243733 | eukaryotic translation initiation factor 4H |
| NAPA | 9.892 | 9.000 | 9.296 | 7.989 | 7.597 | 7.445 | −3.246 | 0.0231678 | N-ethylmaleimide-sensitive factor attachment protein, alpha |
| PARVA | 7.602 | 6.960 | 7.478 | 5.780 | 5.481 | 5.789 | −3.244 | 0.0202049 | parvin, alpha |
| RAB2A | 6.667 | 6.660 | 6.007 | 5.290 | 4.963 | 3.897 | −3.242 | 0.0327310 | RAB2A, member RAS oncogene family |
| PDGFB | 5.702 | 4.666 | 4.610 | 3.442 | 2.970 | 2.970 | −3.239 | 0.0218125 | platelet-derived growth factor beta polypeptide (simian sarcoma viral (v-sis) oncogene homolog) |
| SH3GL1 | 8.501 | 8.897 | 9.173 | 7.599 | 7.202 | 6.256 | −3.238 | 0.0254797 | SH3-domain GRB2-like 1 |
| ABCB7 | 3.792 | 4.356 | 4.989 | 2.648 | 3.294 | 2.648 | −3.236 | 0.0423144 | ATP-binding cassette, sub-family B (MDR/TAP), member 7 |
| C17orf81 | 5.346 | 6.204 | 6.146 | 4.355 | 4.514 | 4.173 | −3.227 | 0.0298867 | chromosome 17 open reading frame 81 |
| TOB1 | 8.723 | 10.122 | 8.987 | 7.296 | 7.249 | 7.752 | −3.227 | 0.0258908 | transducer of ERBB2, 1 |
| TPM3 | 9.878 | 10.051 | 9.684 | 8.270 | 8.031 | 8.189 | −3.226 | 0.0141605 | tropomyosin 3 |
| ITGB1 | 12.123 | 12.748 | 11.397 | 10.433 | 10.621 | 9.720 | −3.225 | 0.0276974 | integrin, beta 1 (fibronectin receptor, beta polypeptide, antigen CD29 includes MDF2, MSK12) |
| ZZZ3 | 5.173 | 5.785 | 6.171 | 4.388 | 4.097 | 3.897 | −3.223 | 0.0303054 | zinc finger, ZZ-type containing 3 |
| LOXL1 | 9.666 | 8.067 | 7.339 | 6.379 | 6.011 | 6.402 | −3.223 | 0.0287899 | lysyl oxidase-like 1 |
| FNTA | 8.135 | 8.207 | 8.816 | 7.016 | 7.010 | 6.447 | −3.222 | 0.0288919 | farnesyltransferase, CAAX box, alpha |
| POMP | 9.346 | 9.985 | 10.316 | 8.765 | 8.297 | 7.187 | −3.222 | 0.0339546 | proteasome maturation protein |
| NUP93 | 6.470 | 6.806 | 6.320 | 5.854 | 4.784 | 3.897 | −3.219 | 0.0444974 | nucleoporin 93 kDa |
| LPXN | 6.190 | 6.554 | 6.267 | 4.124 | 4.581 | 5.005 | −3.219 | 0.0193744 | leupaxin |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| MYH10 | 6.046 | 5.084 | 5.701 | 3.881 | 4.361 | 3.516 | −3.215 | 0.0278922 | myosin, heavy chain 10, non-muscle |
| IMMP1L | 4.423 | 4.564 | 4.684 | 3.023 | 2.739 | 2.752 | −3.213 | 0.0136045 | IMP1 inner mitochondrial membrane peptidase-like (S. cerevisiae) |
| CDK9 | 8.990 | 9.257 | 9.228 | 7.498 | 7.545 | 7.566 | −3.211 | 0.0148308 | cyclin-dependent kinase 9 |
| PXMP2 | 3.194 | 1.962 | 2.329 | 0.648 | 0.648 | 0.648 | −3.207 | 0.0211740 | peroxisomal membrane protein 2, 22 kDa |
| SSR4 | 8.714 | 9.655 | 8.896 | 8.084 | 7.215 | 6.838 | −3.205 | 0.0355317 | signal sequence receptor, delta (translocon-associated protein delta) |
| SMARCD2 | 6.887 | 6.646 | 7.273 | 5.593 | 4.361 | 5.424 | −3.205 | 0.0256510 | SWI/SNF related, matrix associated, actin dependent regulator of chromatin, subfamily d, member 2 |
| COQ5 | 3.860 | 3.881 | 3.888 | 2.202 | 3.284 | 0.648 | −3.204 | 0.0486832 | coenzyme Q5 homolog, methyltransferase (S. cerevisiae) |
| FAM165B | 6.667 | 7.960 | 7.229 | 5.551 | 5.265 | 5.907 | −3.200 | 0.0298229 | family with sequence similarity 165, member B |
| CTSO | 9.117 | 6.762 | 6.748 | 5.072 | 5.733 | 5.558 | −3.196 | 0.0356925 | cathepsin O |
| C18orf10 | 5.482 | 5.816 | 6.202 | 4.526 | 4.043 | 4.007 | −3.196 | 0.0240101 | chromosome 18 open reading frame 10 |
| EMP1 | 11.445 | 12.546 | 12.363 | 9.769 | 10.666 | 10.881 | −3.194 | 0.0362977 | epithelial membrane protein 1 |
| TNFRSF10B | 7.864 | 9.846 | 8.110 | 6.434 | 6.392 | 6.807 | −3.194 | 0.0268295 | tumor necrosis factor receptor superfamily, member 10b |
| ACAA2 | 6.983 | 6.657 | 5.778 | 4.830 | 5.405 | 4.104 | −3.190 | 0.0386347 | acetyl-CoA acyltransferase 2 |
| ZHX2 | 6.626 | 7.116 | 6.682 | 5.443 | 5.288 | 4.693 | −3.188 | 0.0235269 | zinc fingers and homeoboxes 2 |
| SPRED2 | 6.311 | 7.149 | 6.734 | 5.078 | 4.784 | 5.062 | −3.186 | 0.0188870 | sprouty-related, EVH1 domain containing 2 |
| KIAA0391 | 6.038 | 5.203 | 5.439 | 4.350 | 4.368 | 2.648 | −3.181 | 0.0414180 | KIAA0391 |
| LPL | 7.610 | 6.617 | 7.221 | 6.194 | 4.447 | 5.553 | −3.179 | 0.0398638 | lipoprotein lipase |
| F5 | 7.791 | 8.585 | 8.247 | 6.364 | 6.582 | 6.626 | −3.171 | 0.0207872 | coagulation factor V (proaccelerin, labile factor) |
| XPOT | 7.212 | 7.854 | 7.363 | 6.668 | 5.698 | 4.553 | −3.171 | 0.0383144 | exportin, tRNA (nuclear export receptor for tRNAs) |
| INPP5E | 4.709 | 5.551 | 5.107 | 3.442 | 3.899 | 2.970 | −3.171 | 0.0274575 | inositol polyphosphate-5-phosphatase, 72 kDa |
| RDH14 | 6.291 | 6.228 | 6.321 | 4.667 | 4.628 | 3.897 | −3.168 | 0.0148995 | retinol dehydrogenase 14 (all-trans/9-cis/11-cis) |
| SGMS2 | 7.665 | 8.747 | 7.416 | 5.752 | 6.376 | 6.160 | −3.167 | 0.0253889 | sphingomyelin synthase 2 |
| MATR3 | 8.082 | 9.124 | 8.810 | 7.147 | 6.820 | 7.458 | −3.167 | 0.0365771 | matrin 3 |
| CADM3 | 5.877 | 4.590 | 4.895 | 3.848 | 3.233 | 3.233 | −3.163 | 0.0329244 | cell adhesion molecule 3 |
| APP | 11.417 | 11.575 | 11.666 | 9.756 | 10.260 | 9.875 | −3.162 | 0.0201390 | amyloid beta (A4) precursor protein |
| RNF152 | 5.661 | 6.192 | 6.655 | 4.907 | 4.001 | 4.670 | −3.161 | 0.0319588 | ring finger protein 152 |
| MRPL49 | 8.413 | 8.091 | 8.338 | 7.420 | 6.681 | 6.120 | −3.155 | 0.0384211 | mitochondrial ribosomal protein L49 |
| ERMAP | 4.895 | 4.281 | 4.951 | 2.648 | 3.294 | 2.648 | −3.153 | 0.0180974 | erythroblast membrane-associated protein (Scianna blood group) |
| LMNA | 12.627 | 12.228 | 12.564 | 10.750 | 10.574 | 11.748 | −3.146 | 0.0459088 | lamin A/C |
| C10orf78 | 5.160 | 4.481 | 3.871 | 2.233 | 2.233 | 3.508 | −3.143 | 0.0323622 | chromosome 10 open reading frame 78 |
| FBXO34 | 5.552 | 4.946 | 5.646 | 4.388 | 3.294 | 3.897 | −3.142 | 0.0396087 | F-box protein 34 |
| IER2 | 12.274 | 12.279 | 12.538 | 10.445 | 10.984 | 10.629 | −3.140 | 0.0174936 | immediate early response 2 |
| MYL12A | 10.475 | 10.618 | 10.820 | 8.969 | 9.459 | 7.829 | −3.137 | 0.0262111 | myosin, light chain 12A, regulatory, non-sarcomeric |
| TNFSF12 | 4.860 | 4.154 | 3.296 | 1.648 | 1.648 | 3.294 | −3.134 | 0.0391019 | tumor necrosis factor (ligand) superfamily, member 12 |
| CHCHD5 | 5.452 | 5.042 | 5.942 | 4.017 | 3.805 | 3.557 | −3.133 | 0.0236558 | coiled-coil-helix-coiled-coil-helix domain containing 5 |
| FLRT2 | 7.445 | 6.749 | 6.407 | 4.767 | 5.540 | 5.195 | −3.117 | 0.0278250 | fibronectin leucine rich transmembrane protein 2 |
| GTF2A1 | 6.202 | 4.990 | 4.529 | 4.262 | 2.987 | 3.351 | −3.116 | 0.0465612 | general transcription factor IIA, 1, 19/37 kDa |
| SLC39A14 | 9.051 | 10.866 | 9.789 | 8.351 | 8.150 | 8.070 | −3.114 | 0.0382250 | solute carrier family 39 (zinc transporter), member 14 |
| BCL6B | 4.142 | 3.799 | 3.870 | 2.233 | 2.233 | 2.233 | −3.110 | 0.0132898 | B-cell CLL/lymphoma 6, member B |
| APPL1 | 7.055 | 7.668 | 6.802 | 5.418 | 5.649 | 5.203 | −3.108 | 0.0206062 | adaptor protein, phosphotyrosine interaction, PH domain and leucine zipper containing 1 |
| FAM101B | 6.777 | 7.580 | 6.244 | 5.596 | 5.202 | 4.608 | −3.108 | 0.0332475 | family with sequence similarity 101, member B |

TABLE 4-continued

Differentially Expressed Genes in CD44+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD44+ N48 | CD44+ N58 | CD44+ N43 | CD44+ N37 | CD44+ N39 | CD44+ N40 | | | | |
| HERC3 | 4.948 | 6.110 | 5.643 | 3.961 | 4.007 | 4.264 | | -3.107 | 0.0389986 | hect domain and RLD 3 |
| LRIG1 | 5.076 | 6.146 | 5.945 | 3.442 | 3.508 | 5.030 | | -3.104 | 0.0437792 | leucine-rich repeats and immunoglobulin-like domains 1 |
| RASA1 | 6.280 | 5.675 | 6.399 | 4.782 | 4.385 | 4.042 | | -3.102 | 0.0234901 | RAS p21 protein activator (GTPase activating protein) 1 |
| ASNS | 5.322 | 6.225 | 5.720 | 4.508 | 4.592 | 3.054 | | -3.101 | 0.0414090 | asparagine synthetase (glutamine-hydrolyzing) |
| SCAMP1 | 6.815 | 6.484 | 6.089 | 4.456 | 4.456 | 5.293 | | -3.101 | 0.0248953 | secretory carrier membrane protein 1 |
| CSNK1G2 | 7.066 | 6.868 | 7.634 | 5.238 | 5.531 | 5.668 | | -3.094 | 0.0208142 | casein kinase 1, gamma 2 |
| C2orf79 | 4.817 | 5.989 | 5.850 | 3.278 | 3.467 | 4.360 | | -3.091 | 0.0280891 | chromosome 2 open reading frame 79 |
| TBC1D9 | 8.042 | 7.610 | 7.365 | 6.381 | 5.834 | 5.984 | | -3.086 | 0.0247802 | TBC1 domain family, member 9 (with GRAM domain) |
| DR1 | 7.261 | 7.805 | 7.056 | 5.736 | 5.432 | 5.962 | | -3.082 | 0.0233882 | down-regulator of transcription 1, TBP-binding (negative cofactor 2) |
| TMEM167A | 7.179 | 7.801 | 7.562 | 6.334 | 5.738 | 5.555 | | -3.081 | 0.0255754 | transmembrane protein 167A |
| RC3H1 | 7.091 | 8.438 | 8.423 | 6.110 | 6.400 | 6.815 | | -3.080 | 0.0480530 | ring finger and CCCH-type domains 1 |
| RGS4 | 6.492 | 5.687 | 4.856 | 3.637 | 3.233 | 4.914 | | -3.080 | 0.0489591 | regulator of G-protein signaling 4 |
| UGP2 | 6.833 | 8.557 | 7.031 | 5.861 | 5.508 | 5.210 | | -3.080 | 0.0283068 | UDP-glucose pyrophosphorylase 2 |
| C2orf18 | 6.537 | 8.117 | 7.603 | 6.495 | 5.569 | 5.039 | | -3.076 | 0.0459802 | chromosome 2 open reading frame 18 |
| CXorf38 | 3.860 | 2.202 | 2.268 | 0.648 | 0.648 | 0.648 | | -3.073 | 0.0201958 | chromosome X open reading frame 38 |
| CHGA | 3.860 | 1.649 | 2.268 | 0.648 | 0.648 | 0.648 | | -3.073 | 0.0333958 | chromogranin A (parathyroid secretory protein 1) |
| SUSD2 | 8.210 | 4.589 | 4.933 | 2.970 | 4.001 | 3.516 | | -3.071 | 0.0418589 | sushi domain containing 2 |
| PAN3 | 7.622 | 8.483 | 8.523 | 6.458 | 6.904 | 6.111 | | -3.071 | 0.0265737 | PAN3 poly(A) specific ribonuclease subunit homolog (S. cerevisiae) |
| ADAMTS1 | 8.005 | 9.147 | 8.605 | 7.378 | 6.387 | 7.226 | | -3.070 | 0.0404752 | ADAM metallopeptidase with thrombospondin type 1 motif, 1 |
| LY6E | 10.488 | 9.391 | 9.464 | 8.136 | 8.870 | 7.761 | | -3.070 | 0.0486395 | lymphocyte antigen 6 complex, locus E |
| FAM108B1 | 7.392 | 8.205 | 8.637 | 6.471 | 6.427 | 7.019 | | -3.070 | 0.0496489 | family with sequence similarity 108, member B1 |
| SDHAF2 | 6.887 | 7.780 | 7.879 | 6.374 | 5.752 | 5.270 | | -3.068 | 0.0315560 | succinate dehydrogenase complex assembly factor 2 |
| KIAA0146 | 4.264 | 4.622 | 4.969 | 3.897 | 2.648 | 2.648 | | -3.066 | 0.0444163 | KIAA0146 |
| NIT1 | 4.264 | 3.402 | 4.492 | 2.648 | 2.648 | 2.648 | | -3.066 | 0.0447172 | nitrilase 1 |
| URM1 | 4.264 | 6.004 | 6.073 | 4.927 | 4.529 | 2.648 | | -3.066 | 0.0491310 | ubiquitin related modifier 1 |
| TMEM223 | 4.264 | 5.845 | 4.948 | 4.388 | 5.376 | 2.648 | | -3.066 | 0.0496399 | transmembrane protein 223 |
| TSSC4 | 6.135 | 7.349 | 6.791 | 4.754 | 5.423 | 5.176 | | -3.063 | 0.0325362 | tumor suppressing subtransferable candidate 4 |
| FCGRT | 9.312 | 9.051 | 8.702 | 7.628 | 7.088 | 7.449 | | -3.061 | 0.0226804 | Fc fragment of IgG, receptor, transporter, alpha |
| HCFC1 | 8.453 | 8.750 | 8.777 | 7.140 | 6.987 | 7.153 | | -3.052 | 0.0180149 | host cell factor C1 (VP16-accessory protein) |
| MYL6 | 11.167 | 11.975 | 11.449 | 10.140 | 10.364 | 9.558 | | -3.052 | 0.0361584 | myosin, light chain 6, alkali, smooth muscle and non-muscle |
| SHOC2 | 7.337 | 7.732 | 7.442 | 5.822 | 6.122 | 5.821 | | -3.052 | 0.0195913 | soc-2 suppressor of clear homolog (C. elegans) |
| CCDC101 | 6.829 | 5.811 | 6.388 | 4.721 | 4.529 | 6.736 | | -3.050 | 0.0374582 | coiled-coil domain containing 101 |
| CCNG2 | 8.081 | 7.451 | 7.259 | 5.842 | 5.376 | 2.233 | | -3.050 | 0.0402742 | cyclin G2 |
| ACTR10 | 4.142 | 4.599 | 5.144 | 3.535 | 3.043 | 4.007 | | -3.049 | 0.0354014 | actin-related protein 10 homolog (S. cerevisiae) |
| RGL1 | 6.309 | 5.955 | 5.642 | 4.556 | 4.701 | 4.990 | | -3.048 | 0.0296253 | ral guanine nucleotide dissociation stimulator-like 1 |
| ATAD1 | 7.141 | 6.850 | 6.791 | 6.258 | 5.243 | 4.990 | | -3.046 | 0.0495421 | ATPase family, AAA domain containing 1 |
| TBC1D2B | 8.178 | 7.976 | 8.029 | 6.423 | 5.952 | 6.622 | | -3.043 | 0.0171823 | TBC1 domain family, member 2B |
| RAB11B | 8.331 | 7.197 | 7.546 | 6.726 | 6.034 | 4.590 | | -3.042 | 0.0391927 | RAB11B, member RAS oncogene family |
| ABTB1 | 5.293 | 5.305 | 5.683 | 4.490 | 3.233 | 3.701 | | -3.040 | 0.0329563 | ankyrin repeat and BTB (POZ) domain containing 1 |
| GPSM3 | 7.114 | 5.875 | 4.854 | 4.273 | 3.294 | 4.346 | | -3.036 | 0.0366610 | G-protein signaling modulator 3 |
| AFAP1 | 6.942 | 7.034 | 6.749 | 5.340 | 5.189 | 5.420 | | -3.036 | 0.0165737 | actin filament associated protein 1 |
| FAM102A | 10.025 | 9.531 | 9.614 | 7.913 | 8.017 | 8.466 | | -3.025 | 0.0239206 | family with sequence similarity 102, member A |
| PEAR1 | 7.521 | 6.372 | 6.880 | 5.621 | 3.970 | 5.925 | | -3.023 | 0.0487664 | platelet endothelial aggregation receptor 1 |
| CD59 | 10.620 | 11.427 | 12.120 | 9.832 | 9.867 | 9.810 | | -3.022 | 0.0417418 | CD59 molecule, complement regulatory protein |

TABLE 4-continued

Differentially Expressed Genes in CD44+ Breast Epithelial Cells

| Gene Symbol | Nulliparous (NP) Samples | | | | Parous (P) Samples | | | | Pseudo fold change | P value | Gene description |
|---|---|---|---|---|---|---|---|---|---|---|---|
| | CD44+ N48 | CD44+ N58 | CD44+ N43 | | CD44+ N37 | CD44+ N39 | CD44+ N40 | | | | |
| RPL14 | 10.710 | 11.421 | 11.256 | | 9.370 | 9.661 | 9.705 | | -3.021 | 0.0260891 | ribosomal protein L14 |
| RPL30 | 13.209 | 13.555 | 13.241 | | 11.614 | 11.674 | 11.945 | | -3.020 | 0.0189931 | ribosomal protein L30 |
| CES2 | 6.814 | 5.970 | 6.298 | | 5.614 | 4.628 | 4.377 | | -3.016 | 0.0490693 | carboxylesterase 2 |
| EXOC3 | 5.888 | 6.892 | 7.094 | | 5.526 | 5.302 | 3.865 | | -3.011 | 0.0461633 | exocyst complex component 3 |
| ELF2 | 6.277 | 6.321 | 6.156 | | 4.649 | 4.566 | 4.838 | | -3.009 | 0.0167678 | E74-like factor 2 (ets domain transcription factor) |
| ESD | 3.792 | 5.479 | 4.805 | | 3.218 | 2.648 | 3.303 | | -3.005 | 0.0439179 | esterase D |
| SFRS12IP1 | 7.522 | 8.344 | 7.484 | | 6.644 | 6.387 | 5.897 | | -3.004 | 0.0407844 | No description |
| LDLRAD3 | 7.054 | 8.598 | 6.343 | | 5.469 | 5.515 | 4.827 | | -3.001 | 0.0302666 | low density lipoprotein receptor class A domain containing 3 |
| NGFRAP1 | 4.142 | 3.817 | 4.290 | | 2.233 | 3.043 | 2.233 | | -2.997 | 0.0291185 | nerve growth factor receptor (TNFRSF16) associated protein 1 |
| AP1S2 | 5.229 | 6.390 | 6.392 | | 4.809 | 3.694 | 4.007 | | -2.997 | 0.0295359 | adaptor-related protein complex 1, sigma 2 subunit |
| MGAT3 | 6.777 | 4.499 | 3.815 | | 3.429 | 2.233 | 3.054 | | -2.994 | 0.0434610 | mannosyl (beta-1,4-)-glycoprotein beta-1,4-N-acetylglucosaminyltransferase |
| FAM198B | 8.082 | 8.737 | 7.636 | | 6.143 | 6.506 | 6.692 | | -2.982 | 0.0262728 | family with sequence similarity 198, member B |
| NEK6 | 4.086 | 4.807 | 4.922 | | 3.233 | 3.233 | 3.233 | | -2.977 | 0.0402894 | NIMA (never in mitosis gene a)-related kinase 6 |
| C1orf86 | 6.756 | 6.965 | 7.803 | | 5.409 | 5.304 | 5.398 | | -2.962 | 0.0204073 | chromosome 1 open reading frame 86 |
| CNN3 | 12.047 | 11.043 | 11.258 | | 9.693 | 9.656 | 10.055 | | -2.960 | 0.0271948 | calponin 3, acidic |
| MEIS2 | 6.551 | 7.510 | 7.318 | | 5.637 | 5.614 | 5.948 | | -2.952 | 0.0434977 | Meis homeobox 2 |
| STUB1 | 6.036 | 7.397 | 6.643 | | 5.196 | 4.811 | 5.082 | | -2.951 | 0.0319206 | STIP1 homology and U-box containing protein 1, E3 ubiquitin protein ligase |
| PHF11 | 5.076 | 6.251 | 5.913 | | 4.546 | 4.385 | 3.516 | | -2.949 | 0.0417827 | PHD finger protein 11 |
| SEC62 | 8.212 | 9.464 | 8.705 | | 7.572 | 7.146 | 6.679 | | -2.946 | 0.0348884 | SEC62 homolog (S. cerevisiae) |
| FAM109B | 6.713 | 6.039 | 5.595 | | 4.713 | 4.294 | 4.481 | | -2.945 | 0.0298478 | family with sequence similarity 109, member B |
| CDK2 | 6.507 | 7.377 | 7.801 | | 5.837 | 5.475 | 5.821 | | -2.939 | 0.0413203 | cyclin-dependent kinase 2 |
| FAM46B | 7.114 | 7.233 | 8.436 | | 5.558 | 6.424 | 5.682 | | -2.939 | 0.0361154 | family with sequence similarity 46, member B |
| FSTL1 | 13.885 | 12.483 | 12.426 | | 11.163 | 10.872 | 11.667 | | -2.936 | 0.0390783 | follistatin-like 1 |
| PPP2R4 | 6.401 | 6.807 | 5.760 | | 5.255 | 5.089 | 3.233 | | -2.932 | 0.0474076 | protein phosphatase 2A activator, regulatory subunit 4 |
| SLC25A6 | 12.075 | 11.862 | 12.392 | | 10.233 | 10.842 | 10.576 | | -2.928 | 0.0254201 | solute carrier family 25 (mitochondrial carrier; adenine nucleotide translocator), member 6 |
| NDUFAF3 | 6.710 | 6.867 | 6.326 | | 5.797 | 5.162 | 3.859 | | -2.924 | 0.0446416 | NADH dehydrogenase (ubiquinone) 1 alpha subcomplex, assembly factor 3 |
| RHBDF1 | 6.665 | 6.846 | 7.502 | | 5.822 | 5.517 | 5.118 | | -2.924 | 0.0346950 | rhomboid 5 homolog 1 (Drosophila) |
| C11orf51 | 4.142 | 5.013 | 4.417 | | 2.233 | 3.467 | 3.054 | | -2.918 | 0.0383636 | chromosome 11 open reading frame 51 |
| OR1J1 | 4.314 | 5.808 | 5.256 | | 3.081 | 2.987 | 4.262 | | -2.918 | 0.0460496 | olfactory receptor, family 1, subfamily J, member 1 |
| HTRA2 | 6.062 | 6.950 | 6.475 | | 5.153 | 4.646 | 4.933 | | -2.912 | 0.0282180 | HtrA serine peptidase 2 |
| TNXB | 7.168 | 6.242 | 6.941 | | 5.400 | 5.292 | 5.536 | | -2.911 | 0.0427484 | tenascin XB |
| C10orf46 | 6.893 | 7.404 | 7.206 | | 5.842 | 5.863 | 5.160 | | -2.911 | 0.0288392 | chromosome 10 open reading frame 46 |
| POLR1E | 6.852 | 7.606 | 6.156 | | 5.311 | 5.531 | 4.946 | | -2.910 | 0.0389334 | polymerase (RNA) I polypeptide E, 53 kDa |
| CSNK1A1 | 9.453 | 9.394 | 9.430 | | 7.890 | 8.367 | 7.786 | | -2.909 | 0.0295899 | casein kinase 1, alpha 1 |
| ZFP91 | 9.701 | 9.897 | 9.823 | | 8.452 | 7.398 | 8.282 | | -2.908 | 0.0277948 | zinc finger protein 91 homolog (mouse) |
| TBC1D10B | 6.814 | 7.569 | 7.160 | | 5.913 | 5.276 | 5.718 | | -2.904 | 0.0298319 | TBC1 domain family, member 10B |
| FLRT3 | 4.264 | 3.675 | 4.186 | | 2.648 | 2.648 | 2.648 | | -2.904 | 0.0312246 | fibronectin leucine rich transmembrane protein 3 |
| PPP2R1A | 10.151 | 9.564 | 9.607 | | 8.613 | 8.584 | 7.581 | | -2.904 | 0.0405979 | protein phosphatase 2, regulatory subunit A, alpha |
| SLC16A2 | 4.709 | 4.508 | 4.754 | | 2.970 | 3.827 | 2.970 | | -2.903 | 0.0411276 | solute carrier family 16, member 2 (monocarboxylic acid transporter 8) |
| NEK3 | 4.423 | 2.455 | 3.186 | | 1.648 | 1.648 | 1.648 | | -2.903 | 0.0422236 | NIMA (never in mitosis gene a)-related kinase 3 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| ZBTB8A | 9.600 | 10.194 | 10.311 | 8.523 | 8.391 | 8.775 | −2.900 | 0.0311990 | zinc finger and BTB domain containing 8A |
| RNF14 | 6.291 | 5.178 | 5.914 | 4.700 | 4.378 | 3.694 | −2.899 | 0.0436440 | ring finger protein 14 |
| HP1BP3 | 9.358 | 9.399 | 9.491 | 7.864 | 7.747 | 8.221 | −2.898 | 0.0241910 | heterochromatin protein 1, binding protein 3 |
| TMED4 | 6.262 | 6.336 | 5.545 | 4.804 | 4.254 | 4.071 | −2.892 | 0.0264253 | transmembrane emp24 protein transport domain containing 4 |
| ARF4 | 10.242 | 11.025 | 10.251 | 8.711 | 8.771 | 8.868 | −2.890 | 0.0203470 | ADP-ribosylation factor 4 |
| OSBPL5 | 7.680 | 8.327 | 7.468 | 6.929 | 6.150 | 5.902 | −2.888 | 0.0433161 | oxysterol binding protein-like 5 |
| FOXJ3 | 6.749 | 7.606 | 7.058 | 6.153 | 5.528 | 5.027 | −2.887 | 0.0381660 | forkhead box J3 |
| CAP1 | 9.823 | 10.131 | 9.506 | 8.601 | 8.497 | 7.320 | −2.886 | 0.0337771 | CAP, adenylate cyclase-associated protein 1 (yeast) |
| TRIM47 | 6.204 | 7.676 | 7.675 | 6.146 | 5.078 | 5.334 | −2.886 | 0.0463511 | tripartite motif-containing 47 |
| AADAT | 3.619 | 5.032 | 5.199 | 3.670 | 2.233 | 2.233 | −2.885 | 0.0378402 | aminoadipate aminotransferase |
| DDX50 | 3.947 | 5.211 | 4.498 | 2.970 | 2.970 | 2.970 | −2.884 | 0.0336426 | DEAD (Asp-Glu-Ala-Asp) box polypeptide 50 |
| ABCC9 | 5.937 | 7.035 | 6.336 | 4.824 | 4.812 | 4.580 | −2.878 | 0.0250617 | ATP-binding cassette, sub-family C (CFTR/MRP), member 9 |
| NOB1 | 5.952 | 6.657 | 6.083 | 4.892 | 5.133 | 4.404 | −2.875 | 0.0403317 | NIN1/RPN12 binding protein 1 homolog (S. cerevisiae) |
| NDRG4 | 4.378 | 4.842 | 4.491 | 2.970 | 2.970 | 2.970 | −2.870 | 0.0180634 | NDRG family member 4 |
| ISPD | 3.194 | 1.962 | 2.170 | 0.648 | 0.648 | 0.648 | −2.870 | 0.0241196 | isoprenoid synthase domain containing |
| ZNF165 | 3.619 | 3.754 | 4.933 | 2.233 | 2.233 | 2.233 | −2.869 | 0.0233286 | zinc finger protein 165 |
| MTUS1 | 7.861 | 7.887 | 8.866 | 5.518 | 6.421 | 7.346 | −2.869 | 0.0410492 | microtubule associated tumor suppressor 1 |
| TIFA | 4.214 | 5.606 | 4.974 | 3.456 | 3.456 | 3.456 | −2.866 | 0.0452544 | TRAF-interacting protein with forkhead-associated domain |
| MMD | 4.378 | 5.669 | 5.576 | 4.151 | 2.970 | 2.970 | −2.865 | 0.0331130 | monocyte to macrophage differentiation-associated |
| LOC100190939 | 7.394 | 7.424 | 7.731 | 5.908 | 6.308 | 5.802 | −2.865 | 0.0248503 | No description |
| SUMO3 | 8.849 | 8.541 | 8.288 | 7.711 | 7.027 | 6.318 | −2.857 | 0.0426617 | SMT3 suppressor of mif two 3 homolog 3 (S. cerevisiae) |
| PLEKHG3 | 5.973 | 6.194 | 5.931 | 4.463 | 4.951 | 4.409 | −2.848 | 0.0296828 | pleckstrin homology domain containing, family G (with RhoGef domain) member 3 |
| MPRIP | 8.719 | 8.954 | 8.868 | 7.210 | 7.824 | 7.356 | −2.846 | 0.0330381 | myosin phosphatase Rho interacting protein |
| SYNGR2 | 8.641 | 8.625 | 8.007 | 7.403 | 7.117 | 5.608 | −2.845 | 0.0432218 | synaptogyrin 2 |
| ZNF706 | 7.651 | 8.382 | 8.395 | 6.543 | 6.623 | 6.888 | −2.842 | 0.0338312 | zinc finger protein 706 |
| TXNDC5 | 7.292 | 9.196 | 7.060 | 5.774 | 6.040 | 5.786 | −2.841 | 0.0327948 | thioredoxin domain containing 5 (endoplasmic reticulum) |
| SGPP1 | 4.482 | 6.569 | 4.739 | 3.233 | 3.233 | 3.701 | −2.839 | 0.0385168 | sphingosine-1-phosphate phosphatase 1 |
| TNFRSF14 | 7.450 | 6.204 | 6.532 | 5.176 | 4.699 | 5.103 | −2.837 | 0.0274915 | tumor necrosis factor receptor superfamily, member 14 (herpesvirus entry mediator) |
| DEPDC6 | 3.619 | 3.737 | 4.624 | 2.233 | 2.233 | 2.233 | −2.836 | 0.0219234 | No description |
| PELI1 | 10.037 | 9.775 | 9.909 | 7.919 | 8.407 | 8.860 | −2.833 | 0.0313459 | pellino homolog 1 (Drosophila) |
| NUMBL | 6.599 | 6.676 | 6.854 | 5.279 | 5.098 | 5.337 | −2.830 | 0.0212891 | numb homolog (Drosophila)-like |
| IKBIP | 5.659 | 5.451 | 5.316 | 4.591 | 3.818 | 3.818 | −2.824 | 0.0392017 | IKBKB interacting protein |
| KDR | 5.639 | 5.654 | 4.861 | 4.159 | 3.456 | 3.865 | −2.818 | 0.0323373 | kinase insert domain receptor (a type III receptor tyrosine kinase) |
| PPIC | 10.003 | 7.443 | 6.891 | 6.232 | 6.086 | 5.398 | −2.815 | 0.0407199 | peptidylprolyl isomerase C (cyclophilin C) |
| C8orf84 | 5.107 | 5.224 | 4.946 | 3.456 | 4.174 | 3.456 | −2.809 | 0.0371317 | chromosome 8 open reading frame 84 |
| ASS1 | 7.319 | 7.355 | 8.170 | 6.147 | 6.680 | 4.042 | −2.808 | 0.0441189 | argininosuccinate synthase 1 |
| ADK | 6.135 | 6.625 | 6.831 | 5.137 | 5.466 | 3.859 | −2.805 | 0.0382069 | adenosine kinase |
| YES1 | 8.236 | 8.071 | 8.170 | 6.655 | 6.892 | 6.585 | −2.801 | 0.0225924 | v-yes-1 Yamaguchi sarcoma viral oncogene homolog 1 |
| PTPRG | 6.835 | 7.116 | 7.204 | 6.020 | 5.506 | 5.352 | −2.794 | 0.0329064 | protein tyrosine phosphatase, receptor type, G |
| GNAQ | 4.525 | 4.501 | 4.861 | 2.951 | 3.043 | 3.508 | −2.793 | 0.0287990 | guanine nucleotide binding protein (G protein), q polypeptide |
| PEX19 | 5.789 | 6.084 | 5.488 | 5.022 | 4.007 | 4.013 | −2.790 | 0.0460821 | peroxisomal biogenesis factor 19 |
| GSDMD | 6.753 | 6.638 | 6.332 | 5.157 | 5.291 | 4.536 | −2.790 | 0.0263352 | gasdermin D |
| WEE1 | 8.951 | 9.542 | 9.679 | 7.705 | 8.199 | 7.733 | −2.790 | 0.0308579 | WEE1 homolog (S. pombe) |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| LOC100233209 | 7.610 | 8.654 | 8.402 | 6.939 | 6.409 | 6.922 | −2.789 | 0.0420114 | No description |
| SAMD4B | 7.465 | 7.827 | 7.444 | 6.396 | 5.986 | 5.790 | −2.788 | 0.0261161 | sterile alpha motif domain containing 4B |
| RWDD1 | 8.608 | 8.943 | 8.220 | 7.070 | 7.505 | 6.743 | −2.783 | 0.0352891 | RWD domain containing 1 |
| MOBKL1B | 5.204 | 5.865 | 5.328 | 3.871 | 3.633 | 4.389 | −2.781 | 0.0337369 | MOB1, Mps One Binder kinase activator-like 1 B (yeast) |
| ARAP1 | 5.614 | 6.605 | 6.086 | 4.610 | 4.240 | 4.631 | −2.780 | 0.0282333 | ArfGAP with RhoGAP domain, ankyrin repeat and PH domain 1 |
| ARL6IP4 | 7.609 | 8.701 | 8.556 | 7.226 | 6.156 | 6.171 | −2.780 | 0.0315879 | ADP-ribosylation-like factor 6 interacting protein 4 |
| COL21A1 | 4.482 | 4.707 | 4.893 | 3.233 | 3.233 | 3.233 | −2.777 | 0.0229369 | collagen, type XXI, alpha 1 |
| CCNY | 8.699 | 8.816 | 7.758 | 7.343 | 6.824 | 6.623 | −2.776 | 0.0431317 | cyclin Y |
| EGR1 | 14.080 | 13.203 | 13.535 | 12.050 | 11.731 | 12.639 | −2.773 | 0.0428225 | early growth response 1 |
| BLOC1S3 | 6.667 | 6.908 | 6.911 | 5.795 | 5.437 | 4.952 | −2.773 | 0.0348385 | biogenesis of lysosomal organelles complex-1, subunit 3 |
| WIPF2 | 8.144 | 8.171 | 8.100 | 7.291 | 6.674 | 6.553 | −2.769 | 0.0436794 | WAS/WASL interacting protein family, member 2 |
| C19orf42 | 6.275 | 6.259 | 6.378 | 5.024 | 4.812 | 3.752 | −2.757 | 0.0254381 | chromosome 19 open reading frame 42 |
| IRF2 | 6.782 | 5.889 | 6.826 | 5.108 | 5.508 | 4.432 | −2.745 | 0.0482686 | interferon regulatory factor 2 |
| CHSY3 | 5.688 | 4.103 | 3.807 | 3.218 | 2.648 | 2.648 | −2.741 | 0.0464676 | chondroitin sulfate synthase 3 |
| C14orf126 | 3.619 | 3.687 | 4.160 | 2.233 | 2.233 | 2.233 | −2.740 | 0.0202652 | chromosome 14 open reading frame 126 |
| HSD17B12 | 4.969 | 5.932 | 6.099 | 4.884 | 3.827 | 3.516 | −2.738 | 0.0488288 | hydroxysteroid (17-beta) dehydrogenase 12 |
| ELOVL7 | 5.293 | 5.296 | 4.567 | 3.848 | 3.233 | 3.233 | −2.728 | 0.0282028 | ELOVL family member 7, elongation of long chain fatty acids (yeast) |
| C20orf199 | 9.828 | 9.891 | 10.549 | 8.382 | 8.667 | 8.791 | −2.725 | 0.0319678 | No description |
| METAP1 | 5.899 | 6.934 | 6.305 | 5.137 | 4.933 | 4.453 | −2.725 | 0.0362790 | methionyl aminopeptidase 1 |
| HIATL1 | 7.326 | 8.636 | 8.007 | 6.586 | 6.166 | 6.562 | −2.723 | 0.0387955 | hippocampus abundant transcript-like 1 |
| MTA1 | 7.732 | 7.945 | 7.035 | 6.288 | 6.323 | 5.809 | −2.721 | 0.0410354 | metastasis associated 1 |
| GUCY1A3 | 6.546 | 6.182 | 5.642 | 4.976 | 4.741 | 4.584 | −2.716 | 0.0442867 | guanylate cyclase 1, soluble, alpha 3 |
| MAP3K7 | 5.204 | 5.436 | 5.166 | 3.997 | 3.859 | 3.456 | −2.711 | 0.0250776 | mitogen-activated protein kinase kinase kinase 7 |
| JPH4 | 4.969 | 4.407 | 4.107 | 2.970 | 2.970 | 2.970 | −2.707 | 0.0285175 | junctophilin 4 |
| ARMC10 | 3.619 | 3.670 | 4.918 | 2.233 | 3.043 | 2.233 | −2.706 | 0.0472461 | armadillo repeat containing 10 |
| ZNF264 | 7.562 | 8.437 | 7.905 | 6.226 | 6.469 | 6.816 | −2.705 | 0.0367983 | zinc finger protein 264 |
| YWHAG | 10.827 | 11.779 | 11.556 | 9.486 | 10.049 | 10.344 | −2.704 | 0.0477466 | tyrosine 3-monooxygenase/tryptophan 5-monooxygenase activation protein, gamma polypeptide |
| RILP | 5.264 | 4.721 | 4.447 | 3.830 | 1.648 | 3.557 | −2.702 | 0.0480620 | Rab interacting lysosomal protein |
| PSMA3 | 3.619 | 5.222 | 5.311 | 3.877 | 2.233 | 2.233 | −2.701 | 0.0422090 | proteasome (prosome, macropain) subunit, alpha type, 3 |
| DIABLO | 6.875 | 7.790 | 7.244 | 6.371 | 5.564 | 5.442 | −2.701 | 0.0414451 | diablo homolog (Drosophila) |
| PLIN3 | 8.751 | 9.479 | 9.366 | 7.937 | 7.372 | 8.020 | −2.693 | 0.0401653 | perilipin 3 |
| NRSN2 | 4.619 | 5.600 | 4.868 | 4.173 | 3.233 | 3.233 | −2.689 | 0.0475144 | neurensin 2 |
| JOSD1 | 8.294 | 9.063 | 8.950 | 7.007 | 7.183 | 7.636 | −2.689 | 0.0346464 | Josephin domain containing 1 |
| SUPT7L | 6.028 | 6.457 | 6.328 | 5.035 | 4.515 | 4.934 | −2.680 | 0.0295900 | suppressor of Ty 7 (S. cerevisiae)-like |
| GTF3C1 | 7.699 | 7.649 | 8.127 | 6.598 | 6.705 | 6.061 | −2.679 | 0.0391601 | general transcription factor IHC, polypeptide 1, alpha 220 kDa |
| CTBP1 | 9.176 | 9.527 | 8.892 | 8.107 | 7.946 | 7.386 | −2.675 | 0.0414984 | C-terminal binding protein 1 |
| PIGN | 4.839 | 5.645 | 5.624 | 4.225 | 3.970 | 3.970 | −2.674 | 0.0478568 | phosphatidylinositol glycan anchor biosynthesis, class N |
| POLR2G | 7.394 | 6.882 | 7.007 | 6.259 | 5.591 | 5.082 | −2.668 | 0.0447678 | polymerase (RNA) II (DNA directed) polypeptide G |
| B4GALT1 | 10.277 | 10.815 | 10.355 | 8.862 | 9.119 | 9.361 | −2.665 | 0.0363636 | UDP-Gal:betaGlcNAc beta 1,4-galactosyltransferase, polypeptide 1 |
| GIPC1 | 7.227 | 7.147 | 7.677 | 5.812 | 6.490 | 4.646 | −2.665 | 0.0416336 | GIPC PDZ domain containing family, member 1 |
| USP6NL | 4.378 | 5.265 | 4.180 | 2.970 | 2.970 | 2.970 | −2.652 | 0.0280600 | USP6 N-terminal like |
| MEX3B | 4.378 | 5.538 | 4.350 | 2.970 | 3.508 | 2.970 | −2.652 | 0.0372960 | mex-3 homolog B (C. elegans) |

TABLE 4-continued

Differentially Expressed Genes in CD44+ Breast Epithelial Cells

| Gene Symbol | Nulliparous (NP) Samples | | | Parous (P) Samples | | | Pseudo | | Gene description |
| | CD44+ N48 | CD44+ N58 | CD44+ N43 | CD44+ N37 | CD44+ N39 | CD44+ N40 | fold change | P value | |
|---|---|---|---|---|---|---|---|---|---|
| SECTM1 | 4.378 | 4.957 | 5.235 | 4.042 | 2.970 | 2.970 | -2.652 | 0.0439588 | secreted and transmembrane 1 |
| EHBP1 | 5.378 | 6.149 | 5.826 | 4.225 | 3.970 | 4.803 | -2.652 | 0.0404932 | EH domain binding protein 1 |
| SPCS1 | 9.466 | 8.905 | 8.849 | 8.094 | 7.499 | 6.134 | -2.651 | 0.0366097 | signal peptidase complex subunit 1 homolog (*S. cerevisiae*) |
| FOSL2 | 10.562 | 9.175 | 9.312 | 8.031 | 7.770 | 8.574 | -2.648 | 0.0476482 | FOS-like antigen 2 |
| CALCRL | 5.745 | 5.692 | 5.744 | 4.835 | 4.339 | 4.173 | -2.647 | 0.0425196 | calcitonin receptor-like |
| CUL7 | 6.735 | 5.807 | 6.447 | 5.512 | 4.405 | 4.681 | -2.643 | 0.0493764 | cullin 7 |
| NDUFS3 | 6.165 | 6.232 | 6.344 | 5.102 | 4.346 | 4.830 | -2.643 | 0.0287206 | NADH dehydrogenase (ubiquinone) Fe-S protein 3, 30 kDa (NADH-coenzyme Q reductase) |
| TMEM167B | 6.259 | 6.919 | 6.923 | 5.683 | 5.034 | 4.861 | -2.636 | 0.0360489 | transmembrane protein 167B |
| PPP1R15B | 11.352 | 11.212 | 10.872 | 9.510 | 9.476 | 10.362 | -2.633 | 0.0478374 | protein phosphatase 1, regulatory (inhibitor) subunit 15B |
| CTBS | 6.027 | 5.968 | 6.558 | 4.981 | 4.572 | 4.650 | -2.632 | 0.0307844 | chitobiase, di-N-acetyl- |
| GUK1 | 8.421 | 9.073 | 8.667 | 7.272 | 7.226 | 7.489 | -2.631 | 0.0332877 | guanylate kinase 1 |
| MAD1L1 | 6.038 | 5.512 | 6.395 | 4.117 | 5.023 | 4.294 | -2.629 | 0.0405120 | MAD1 mitotic arrest deficient-like 1 (yeast) |
| VAT1 | 10.213 | 9.085 | 10.164 | 8.819 | 7.869 | 8.275 | -2.628 | 0.0488939 | vesicle amine transport protein 1 homolog (T. californica) |
| ARPC4 | 10.175 | 9.533 | 9.251 | 8.885 | 8.139 | 6.730 | -2.627 | 0.0497591 | actin related protein 2/3 complex, subunit 4, 20 kDa |
| AKR7A2 | 3.792 | 5.426 | 4.040 | 2.648 | 2.648 | 2.648 | -2.623 | 0.0326776 | aldo-keto reductase family 7, member A2 (aflatoxin aldehyde reductase) |
| ZNF148 | 5.872 | 6.440 | 5.894 | 4.845 | 4.845 | 4.482 | -2.620 | 0.0383941 | zinc finger protein 148 |
| MRPL40 | 3.619 | 4.481 | 3.467 | 2.233 | 2.233 | 2.233 | -2.612 | 0.0276066 | mitochondrial ribosomal protein L40 |
| ZNF75D | 3.619 | 3.426 | 4.544 | 2.233 | 2.233 | 2.233 | -2.612 | 0.0292336 | zinc finger protein 75D |
| LPAR4 | 3.619 | 3.362 | 4.052 | 2.233 | 2.233 | 2.233 | -2.612 | 0.0292925 | lysophosphatidic acid receptor 4 |
| ATG4A | 3.619 | 3.996 | 4.362 | 2.233 | 3.043 | 2.233 | -2.612 | 0.0384031 | ATG4 autophagy related 4 homolog A (*S. cerevisiae*) |
| ASH2L | 3.619 | 3.693 | 4.142 | 2.951 | 2.233 | 2.233 | -2.612 | 0.0456392 | ash2 (absent, small, or homeotic)-like (*Drosophila*) |
| C1orf15 | 3.619 | 4.224 | 2.991 | 2.233 | 2.233 | 2.233 | -2.612 | 0.0497452 | chromosome 1 open reading frame 115 |
| PLEKHB2 | 9.079 | 9.720 | 9.566 | 8.183 | 8.095 | 8.182 | -2.610 | 0.0395893 | pleckstrin homology domain containing, family B (evectins) member 2 |
| STARD4 | 4.008 | 3.878 | 2.894 | 2.625 | 1.648 | 1.648 | -2.608 | 0.0405723 | StAR-related lipid transfer (START) domain containing 4 |
| HNRNPUL2 | 4.378 | 5.252 | 5.282 | 3.442 | 3.899 | 3.516 | -2.608 | 0.0495026 | heterogeneous nuclear ribonucleoprotein U-like 2 |
| RHOA | 11.864 | 11.400 | 11.735 | 10.484 | 10.114 | 10.030 | -2.603 | 0.0281938 | ras homolog gene family, member A |
| GAA | 7.591 | 7.302 | 6.882 | 5.502 | 6.138 | 6.034 | -2.602 | 0.0431733 | glucosidase, alpha; acid |
| RPL22 | 11.036 | 11.640 | 11.304 | 9.766 | 9.881 | 10.265 | -2.595 | 0.0383449 | ribosomal protein L22 |
| ARPP19 | 9.715 | 10.422 | 9.821 | 9.047 | 8.647 | 8.148 | -2.594 | 0.0488378 | cAMP-regulated phosphoprotein, 19 kDa |
| TCF7L1 | 8.074 | 7.973 | 8.492 | 6.478 | 6.700 | 7.213 | -2.593 | 0.0401189 | transcription factor 7-like 1 (T-cell specific, HMG-box) |
| C12orf35 | 3.947 | 4.406 | 4.343 | 2.970 | 2.970 | 2.970 | -2.590 | 0.0376523 | chromosome 12 open reading frame 35 |
| RBBP4 | 8.145 | 8.760 | 9.177 | 7.453 | 7.238 | 7.387 | -2.589 | 0.0487906 | retinoblastoma binding protein 4 |
| LYAR | 6.001 | 7.069 | 6.594 | 4.632 | 5.351 | 5.230 | -2.582 | 0.0424634 | Ly1 antibody reactive homolog (mouse) |
| RYK | 7.895 | 7.194 | 7.431 | 6.294 | 6.264 | 5.831 | -2.573 | 0.0390076 | RYK receptor-like tyrosine kinase |
| CRIP2 | 8.360 | 7.544 | 7.546 | 6.316 | 6.812 | 6.184 | -2.567 | 0.0470707 | cysteine-rich protein 2 |
| FIBIN | 5.992 | 4.324 | 4.240 | 2.970 | 3.508 | 2.970 | -2.556 | 0.0445133 | fin bud initiation factor homolog (zebrafish) |
| RAB33B | 5.019 | 5.494 | 5.845 | 4.099 | 4.141 | 4.146 | -2.554 | 0.0424939 | RAB33B, member RAS oncogene family |
| ZNF292 | 6.828 | 6.286 | 6.970 | 5.259 | 4.935 | 5.690 | -2.551 | 0.0420024 | zinc finger protein 292 |
| B4GALT3 | 8.065 | 8.656 | 8.614 | 7.351 | 6.372 | 7.267 | -2.545 | 0.0441099 | UDP-Gal:betaGlcNAc beta 1,4-galactosyltransferase, polypeptide 3 |
| CS | 10.023 | 10.273 | 9.883 | 8.887 | 8.735 | 8.537 | -2.543 | 0.0320607 | citrate synthase |
| RORC | 4.008 | 2.926 | 4.097 | 1.648 | 1.648 | 2.752 | -2.540 | 0.0414846 | RAR-related orphan receptor C |
| PRKD3 | 6.497 | 6.909 | 6.425 | 5.083 | 5.151 | 5.637 | -2.535 | 0.0418451 | protein kinase D3 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| RNF170 | 5.039 | 4.573 | 5.350 | 4.124 | 3.233 | 3.233 | −2.531 | 0.0439497 | ring finger protein 170 |
| AGAP1 | 6.886 | 7.154 | 6.515 | 5.815 | 5.528 | 5.498 | −2.528 | 0.0480711 | ArfGAP with GTPase domain, ankyrin repeat and PH domain 1 |
| PIGC | 4.423 | 4.864 | 4.663 | 3.326 | 3.805 | 1.648 | −2.527 | 0.0488052 | phosphatidylinositol glycan anchor biosynthesis, class C |
| C1orf128 | 8.123 | 9.487 | 8.690 | 7.416 | 6.993 | 7.363 | −2.509 | 0.0437286 | chromosome 1 open reading frame 128 |
| MAPK1IP1L | 8.223 | 8.626 | 8.672 | 7.146 | 7.345 | 6.983 | −2.508 | 0.0338222 | mitogen-activated protein kinase 1 interacting protein 1-like |
| ATP1A1 | 10.412 | 10.973 | 11.413 | 9.658 | 9.478 | 9.647 | −2.506 | 0.0472198 | ATPase, Na+/K+ transporting, alpha 1 polypeptide |
| TMOD4 | 3.194 | 1.753 | 1.973 | 0.648 | 0.648 | 0.648 | −2.505 | 0.0352156 | tropomodulin 4 (muscle) |
| FBLN2 | 6.666 | 6.755 | 6.965 | 5.365 | 5.347 | 5.647 | −2.495 | 0.0300766 | fibulin 2 |
| XYLT2 | 4.264 | 3.965 | 4.188 | 3.218 | 2.648 | 2.648 | −2.492 | 0.0413383 | xylosyltransferase II |
| HAND2 | 4.620 | 4.588 | 4.311 | 2.648 | 3.294 | 3.303 | −2.491 | 0.0337231 | heart and neural crest derivatives expressed 2 |
| ZNF304 | 4.620 | 4.443 | 4.675 | 3.718 | 2.648 | 3.303 | −2.491 | 0.0480378 | zinc finger protein 304 |
| HNMT | 7.403 | 6.197 | 5.862 | 4.556 | 5.089 | 5.005 | −2.472 | 0.0432655 | histamine N-methyltransferase |
| UCHL5 | 3.792 | 3.951 | 4.662 | 2.648 | 2.648 | 2.648 | −2.468 | 0.0318638 | ubiquitin carboxyl-terminal hydrolase L5 |
| FAM107B | 8.072 | 8.765 | 8.185 | 6.771 | 7.286 | 7.050 | −2.463 | 0.0467705 | family with sequence similarity 107. member B |
| ABCE1 | 6.940 | 8.349 | 6.885 | 5.891 | 5.720 | 5.592 | −2.450 | 0.0382340 | ATP-binding cassette, sub-family E (OABP), member 1 |
| RAB37 | 3.422 | 2.936 | 2.625 | 1.648 | 1.648 | 1.648 | −2.442 | 0.0394229 | RAB37, member RAS oncogene family |
| ZBTB48 | 5.109 | 5.331 | 5.422 | 4.052 | 4.151 | 3.508 | −2.427 | 0.0352336 | zinc finger and BTB domain containing 48 |
| EARS2 | 5.076 | 4.623 | 4.705 | 3.797 | 3.508 | 2.970 | −2.427 | 0.0417965 | glutamyl-tRNA synthetase 2, mitochondrial (putative) |
| RAB5B | 9.640 | 9.423 | 9.394 | 8.391 | 7.830 | 8.145 | −2.425 | 0.0328537 | RAB5B, member RAS oncogene family |
| RETSAT | 7.036 | 6.574 | 7.136 | 5.859 | 5.371 | 5.654 | −2.424 | 0.0441674 | retinol saturase (all-trans-retinol 13,14-reductase) |
| KLHL5 | 4.524 | 4.393 | 4.244 | 3.442 | 2.970 | 2.970 | −2.418 | 0.0418222 | kelch-like5 (Drosophila) |
| PCBP4 | 6.566 | 6.299 | 6.117 | 4.248 | 5.026 | 5.387 | −2.417 | 0.0441875 | poly(rC) binding protein 4 |
| ROR1 | 7.283 | 6.967 | 7.013 | 5.284 | 5.743 | 6.075 | −2.411 | 0.0375761 | receptor tyrosine kinase-like orphan receptor 1 |
| VBP1 | 5.499 | 5.879 | 6.003 | 4.734 | 4.223 | 4.670 | −2.409 | 0.0478790 | von Hippel-Lindau binding protein 1 |
| FAM164A | 4.895 | 3.914 | 3.614 | 2.648 | 2.648 | 2.648 | −2.404 | 0.0422423 | family with sequence similarity 164, member A |
| MRPL45 | 7.421 | 7.085 | 7.946 | 6.070 | 6.352 | 6.156 | −2.402 | 0.0485834 | mitochondrial ribosomal protein L45 |
| TMEM158 | 7.488 | 7.628 | 7.738 | 6.480 | 5.583 | 6.364 | −2.402 | 0.0347296 | transmembrane protein 158 (gene/pseudogene) |
| SAMD9L | 4.264 | 3.910 | 3.706 | 2.648 | 2.648 | 2.648 | −2.398 | 0.0355130 | sterile alpha motif domain containing 9-like |
| CRYL1 | 3.947 | 5.398 | 4.230 | 2.970 | 2.970 | 2.970 | −2.395 | 0.0425473 | crystallin, lambda 1 |
| GSTP1 | 10.682 | 10.739 | 10.898 | 9.735 | 9.481 | 8.190 | −2.391 | 0.0393965 | glutathione S-transferase pi 1 |
| FLOT1 | 8.583 | 8.085 | 7.975 | 7.139 | 7.033 | 6.719 | −2.388 | 0.0483622 | flotillin 1 |
| CAPNS1 | 9.537 | 9.174 | 9.180 | 7.999 | 8.283 | 7.176 | −2.384 | 0.0402984 | calpain, small subunit 1 |
| KLHL25 | 4.482 | 4.881 | 4.127 | 3.233 | 3.233 | 3.233 | −2.377 | 0.0459407 | kelch-like 25 (Drosophila) |
| KIAA2013 | 8.407 | 7.627 | 7.662 | 6.582 | 6.645 | 6.378 | −2.376 | 0.0415449 | KIAA2013 |
| RAB3GAP1 | 7.480 | 7.571 | 7.590 | 6.209 | 6.552 | 6.324 | −2.372 | 0.0410263 | RAB3 GTPase activating protein subunit 1 (catalytic) |
| SSNA1 | 7.324 | 7.119 | 7.427 | 6.267 | 6.082 | 4.590 | −2.364 | 0.0439269 | Sjogren syndrome nuclear autoantigen 1 |
| RGPD3 | 5.204 | 5.491 | 4.728 | 4.021 | 3.633 | 3.966 | −2.358 | 0.0498714 | RANBP2-like and GRIP domain containing 3 |
| CSRP2BP | 4.142 | 3.467 | 3.197 | 2.233 | 2.233 | 2.233 | −2.352 | 0.0426437 | CSRP2 binding protein |
| CYB561D2 | 5.109 | 4.583 | 4.916 | 3.737 | 3.686 | 3.508 | −2.345 | 0.0442464 | cytochrome b-561 domain containing 2 |
| LRP5 | 5.805 | 5.574 | 5.606 | 4.099 | 4.585 | 4.377 | −2.343 | 0.0353224 | low density lipoprotein receptor-related protein 5 |
| GMCL1 | 4.194 | 2.522 | 2.868 | 1.648 | 1.648 | 1.648 | −2.328 | 0.0495199 | germ cell-less homolog 1 (Drosophila) |
| C7orf42 | 11.106 | 11.171 | 10.732 | 9.900 | 9.924 | 9.605 | −2.306 | 0.0481813 | chromosome 7 open reading frame 42 |
| C1orf126 | 6.419 | 5.979 | 6.024 | 4.989 | 4.827 | 4.796 | −2.292 | 0.0377258 | chromosome 1 open reading frame 126 |
| PHF2 | 7.898 | 8.291 | 8.425 | 7.234 | 6.824 | 6.754 | −2.283 | 0.0455400 | PHD finger protein 2 |
| TMEM200B | 4.264 | 4.490 | 3.800 | 2.648 | 2.648 | 3.303 | −2.276 | 0.0495740 | transmembrane protein 200B |

TABLE 4-continued

Differentially Expressed Genes in CD44+ Breast Epithelial Cells

| Gene Symbol | Nulliparous (NP) Samples | | | | Parous (P) Samples | | | | Pseudo | | Gene description |
|---|---|---|---|---|---|---|---|---|---|---|---|
| | CD44+ N48 | CD44+ N58 | CD44+ N43 | | CD44+ N37 | CD44+ N39 | CD44+ N40 | | fold change | P value | |
| PUF60 | 8.556 | 8.517 | 8.795 | | 7.614 | 7.498 | 6.916 | | −2.267 | 0.0458998 | poly-U binding splicing factor 60KDa |
| ST6GAL1 | 5.377 | 5.739 | 5.424 | | 4.579 | 4.273 | 3.303 | | −2.235 | 0.0462693 | ST6 beta-galactosamide alpha-2,6-sialyltranferase 1 |
| DCP1A | 6.733 | 7.135 | 6.652 | | 5.809 | 5.494 | 5.593 | | −2.231 | 0.0470867 | DCP1 decapping enzyme homolog A (S. cerevisiae) |
| CTDSPL | 6.945 | 6.293 | 6.074 | | 5.162 | 5.136 | 5.025 | | −2.231 | 0.0446277 | CTD (carboxy-terminal domain, RNA polymerase II, polypeptide A) small phosphatase-like |
| RBM11 | 3.792 | 4.313 | 3.800 | | 2.648 | 2.648 | 2.648 | | −2.222 | 0.0357334 | RNA binding motif protein 11 |
| EDIL3 | 3.792 | 3.925 | 3.674 | | 2.648 | 2.648 | 2.648 | | −2.209 | 0.0408010 | EGF-like repeats and discoidin 1-like domains 3 |
| GPD1L | 3.792 | 3.765 | 3.781 | | 2.648 | 2.648 | 2.648 | | −2.193 | 0.0349182 | glycerol-3-phosphate dehydrogenase 1-like |
| TGM2 | 4.871 | 4.940 | 5.666 | | 3.818 | 3.818 | 3.818 | | −2.176 | 0.0423588 | transglutaminase 2 (C polypeptide, protein-glutamine-gamma-glutamyltransferase) |
| CNNM2 | 7.893 | 7.772 | 7.912 | | 6.815 | 6.657 | 6.671 | | −2.166 | 0.0406173 | cyclin M2 |
| GSTM5 | 3.792 | 3.747 | 3.639 | | 2.648 | 2.648 | 2.648 | | −2.142 | 0.0454520 | glutathione S-transferase mu 5 |
| AQP7P3 | 3.194 | 1.649 | 1.719 | | 0.648 | 0.648 | 0.648 | | −2.100 | 0.0496149 | aquaporin 7 pseudogene 3 |
| | | | | | | | Higher Expression in Parous | | | | |
| VSTM2L | 1.648 | 1.648 | 1.689 | | 2.625 | 2.739 | 2.752 | | 2.089 | 0.0496059 | V-set and transmembrane domain containing 2 like |
| NDUFB1 | 1.648 | 1.648 | 1.648 | | 2.625 | 2.739 | 2.752 | | 2.130 | 0.0475667 | NADH dehydrogenase (ubiquinone) 1 beta subcomplex, 1, 7k Da |
| ZNF323 | 1.648 | 1.648 | 1.648 | | 2.625 | 2.739 | 2.752 | | 2.130 | 0.0475667 | zinc finger protein 323 |
| ALOXE3 | 1.648 | 1.648 | 1.689 | | 2.625 | 2.739 | 3.294 | | 2.130 | 0.0491809 | arachidonate lipoxygenase 3 |
| SLC24A2 | 1.648 | 1.648 | 1.648 | | 3.326 | 2.739 | 2.752 | | 2.149 | 0.0405529 | solute carrier family 24 (sodium/potassium/calcium exchanger), member 2 |
| CLIC6 | 1.648 | 1.648 | 1.648 | | 2.625 | 3.247 | 2.752 | | 2.149 | 0.0467501 | chloride intracellular channel 6 |
| POLB | 1.648 | 1.648 | 1.648 | | 2.625 | 3.247 | 2.752 | | 2.149 | 0.0467501 | polymerase (DNA directed), beta |
| TRIM11 | 6.667 | 6.487 | 6.413 | | 7.698 | 7.521 | 7.661 | | 2.154 | 0.0486971 | tripartite motif-containing 11 |
| RRP15 | 5.869 | 5.847 | 5.770 | | 6.965 | 7.071 | 6.852 | | 2.171 | 0.0421591 | ribosomal RNA processing 15 homolog (S. cerevisiae) |
| WDR77 | 6.784 | 6.487 | 6.791 | | 7.935 | 9.001 | 7.648 | | 2.236 | 0.0446062 | WD repeat domain 77 |
| STK32C | 4.142 | 2.822 | 4.395 | | 5.167 | 5.314 | 5.451 | | 2.254 | 0.0499941 | serine/threonine kinase 32C |
| CLPTM1 | 8.467 | 8.615 | 8.718 | | 9.893 | 9.803 | 9.567 | | 2.258 | 0.0463144 | cleft lip and palate associated transmembrane protein 1 |
| SFRS6 | 8.100 | 7.414 | 8.343 | | 9.278 | 9.218 | 9.372 | | 2.263 | 0.0455775 | No description |
| LOC400891 | 2.648 | 2.648 | 2.841 | | 3.838 | 3.739 | 4.049 | | 2.281 | 0.0441369 | No description |
| GAPVD1 | 7.485 | 7.322 | 7.499 | | 8.683 | 8.413 | 8.792 | | 2.294 | 0.0425764 | GTPase activating protein and VPS9 domains 1 |
| HNRPLL | 7.069 | 6.751 | 6.876 | | 8.076 | 7.872 | 8.717 | | 2.298 | 0.0457875 | heterogeneous nuclear ribonucleoprotein L-like |
| FLJ13197 | 2.648 | 2.648 | 2.669 | | 3.718 | 3.852 | 4.581 | | 2.303 | 0.0388620 | No description |
| PIH1D1 | 7.411 | 7.423 | 7.232 | | 9.807 | 8.370 | 8.615 | | 2.303 | 0.0411539 | PIH1 domain containing 1 |
| AKIRIN2 | 9.442 | 9.240 | 9.445 | | 10.448 | 10.485 | 10.973 | | 2.309 | 0.0423282 | akirin 2 |
| ZNF709 | 4.744 | 3.481 | 4.380 | | 5.599 | 5.562 | 5.682 | | 2.327 | 0.0486679 | zinc finger protein 709 |
| XIST | 8.848 | 9.100 | 9.339 | | 10.318 | 10.330 | 10.503 | | 2.345 | 0.0363726 | X (inactive)-specific transcript (non-protein coding) |
| SAPS3 | 8.256 | 7.990 | 8.127 | | 9.357 | 9.039 | 9.980 | | 2.345 | 0.0465251 | No description |
| MACC1 | 4.839 | 4.351 | 4.700 | | 5.932 | 5.948 | 5.821 | | 2.349 | 0.0376080 | metastasis associated in colon cancer 1 |
| C17orf77 | 2.233 | 2.233 | 2.233 | | 3.429 | 3.467 | 4.174 | | 2.352 | 0.0317640 | chromosome 17 open reading frame 77 |
| RPS17 | 12.815 | 12.592 | 12.922 | | 14.158 | 13.999 | 13.951 | | 2.355 | 0.0350471 | ribosomal protein S17 |
| EP400 | 6.915 | 6.974 | 6.349 | | 7.847 | 7.974 | 8.224 | | 2.378 | 0.0466672 | E1A binding protein p400 |
| RRAGD | 5.482 | 6.357 | 5.276 | | 7.612 | 7.505 | 6.529 | | 2.386 | 0.0496808 | Ras-related GTP binding D |
| CLIC2 | 6.532 | 6.472 | 6.650 | | 7.792 | 7.450 | 9.233 | | 2.395 | 0.0479477 | chloride intracellular channel 2 |
| MAP3K4 | 4.792 | 6.450 | 6.412 | | 7.714 | 7.432 | 7.678 | | 2.404 | 0.0391109 | mitogen-activated protein kinase kinase kinase 4 |

TABLE 4-continued

Differentially Expressed Genes in CD44+ Breast Epithelial Cells

| | Nulliparous (NP) Samples | | | Parous (P) Samples | | | Pseudo | | |
|---|---|---|---|---|---|---|---|---|---|
| Gene Symbol | CD44+ N48 | CD44+ N58 | CD44+ N43 | CD44+ N37 | CD44+ N39 | CD44+ N40 | fold change | P value | Gene description |
| SFRS2IP | 4.722 | 6.405 | 6.578 | 7.676 | 7.528 | 7.685 | 2.413 | 0.0422846 | No description |
| DLGAP3 | 2.233 | 2.233 | 2.607 | 4.276 | 3.467 | 3.508 | 2.420 | 0.0414000 | discs, large (Drosophila) homolog-associated protein 3 |
| PELP1 | 8.571 | 8.468 | 7.902 | 9.750 | 10.186 | 9.171 | 2.432 | 0.0492149 | proline, glutamate and leucine rich protein 1 |
| ABCF2 | 9.357 | 9.058 | 9.546 | 10.691 | 10.644 | 10.560 | 2.440 | 0.0339063 | ATP-binding cassette, sub-family F (GCN20), member 2 |
| DPP7 | 7.579 | 6.713 | 7.751 | 8.870 | 8.899 | 8.842 | 2.446 | 0.0340489 | dipeptidyl-peptidase 7 |
| MTA3 | 7.478 | 6.050 | 7.072 | 8.151 | 8.362 | 8.691 | 2.446 | 0.0450381 | metastasis associated 1 family, member 3 |
| GALNTL2 | 4.947 | 6.211 | 6.102 | 7.361 | 7.444 | 7.395 | 2.451 | 0.0324170 | UDP-N-acetyl-alpha-D-galactosamine:polypeptide N-acetylgalactosaminyltransferase-like 2 |
| VEZF1 | 8.093 | 7.929 | 7.933 | 9.092 | 9.227 | 9.747 | 2.452 | 0.0350055 | vascular endothelial zinc finger 1 |
| SLC19A1 | 5.973 | 5.316 | 5.312 | 6.809 | 7.149 | 6.607 | 2.454 | 0.0459983 | solute carrier family 19 (folate transporter), member 1 |
| NKTR | 7.130 | 7.218 | 7.727 | 9.380 | 8.428 | 8.481 | 2.459 | 0.0477133 | natural killer-tumor recognition sequence |
| C1orf144 | 7.347 | 7.878 | 7.768 | 9.277 | 9.066 | 8.585 | 2.459 | 0.0457965 | chromosome 1 open reading frame 144 |
| TAF1D | 8.308 | 8.105 | 8.655 | 9.521 | 9.560 | 9.955 | 2.462 | 0.0394381 | TATA box binding protein (TBP)-associated factor, RNA polymerase I, D, 41 kDa |
| REEP1 | 2.233 | 2.233 | 2.233 | 3.535 | 4.294 | 3.508 | 2.466 | 0.0276759 | receptor accessory protein 1 |
| HYAL3 | 2.233 | 2.233 | 2.524 | 3.535 | 4.413 | 3.508 | 2.466 | 0.0357016 | hyaluronoglucosaminidase 3 |
| GSDMA | 5.908 | 5.730 | 5.820 | 7.164 | 6.969 | 7.211 | 2.467 | 0.0297598 | gasdermin A |
| ARHGEF2 | 7.154 | 7.163 | 7.778 | 8.464 | 8.568 | 8.990 | 2.478 | 0.0462783 | Rho/Rac guanine nucleotide exchange factor (GEF) 2 |
| BAZ2A | 8.835 | 8.459 | 8.598 | 9.603 | 9.910 | 10.157 | 2.481 | 0.0437127 | bromodomain adjacent to zinc finger domain, 2A |
| RANBP2 | 5.232 | 5.625 | 5.272 | 6.592 | 6.484 | 7.121 | 2.496 | 0.0386943 | RAN binding protein 2 |
| ARRB2 | 4.378 | 4.231 | 3.697 | 5.555 | 4.970 | 6.026 | 2.504 | 0.0476156 | arrestin, beta 2 |
| OSTC | 2.233 | 2.360 | 2.360 | 3.535 | 3.686 | 3.737 | 2.508 | 0.0257646 | oligosaccharyltransferase complex subunit |
| MRPS16 | 7.175 | 6.978 | 7.434 | 8.390 | 8.765 | 8.403 | 2.515 | 0.0360946 | mitochondrial ribosomal protein S16 |
| SFRS13A | 7.065 | 7.809 | 7.828 | 8.571 | 9.163 | 9.139 | 2.522 | 0.0444315 | splicing factor, arginine/serine-rich 13A |
| PPP4C | 5.773 | 5.356 | 5.494 | 7.106 | 7.059 | 6.691 | 2.522 | 0.0296648 | protein phosphatase 4, catalytic subunit |
| DEF8 | 7.271 | 7.301 | 7.466 | 8.639 | 8.239 | 8.836 | 2.529 | 0.0462873 | differentially expressed in FDCP 8 homolog (mouse) |
| SLAMF1 | 4.969 | 4.378 | 4.761 | 6.101 | 5.526 | 7.051 | 2.532 | 0.0483851 | signaling lymphocytic activation molecule family member 1 |
| TBKBP1 | 3.947 | 3.111 | 4.042 | 5.287 | 5.352 | 5.083 | 2.533 | 0.0314548 | TBK1 binding protein 1 |
| GOSR1 | 8.268 | 7.620 | 7.914 | 9.255 | 9.000 | 9.419 | 2.534 | 0.0438527 | golgi SNAP receptor complex member 1 |
| LOC401093 | 5.339 | 4.713 | 4.553 | 5.897 | 6.259 | 6.458 | 2.538 | 0.0468211 | No description |
| KIAA1530 | 5.854 | 5.193 | 5.747 | 6.893 | 7.093 | 7.184 | 2.542 | 0.0299976 | KIAA1530 |
| HSCB | 5.861 | 6.081 | 6.537 | 7.429 | 7.290 | 7.816 | 2.547 | 0.0412315 | HscB iron-sulfur cluster co-chaperone homolog (E. coli)) |
| E4F1 | 3.818 | 3.818 | 3.938 | 5.344 | 5.167 | 4.807 | 2.547 | 0.0413002 | E4F transcription factor 1 |
| BID | 6.431 | 7.249 | 7.403 | 8.354 | 8.756 | 8.544 | 2.555 | 0.0340662 | BH3 interacting domain death agonist |
| APOD | 14.176 | 13.906 | 14.263 | 15.096 | 15.531 | 16.825 | 2.558 | 0.0387317 | apolipoprotein D |
| FAM40B | 4.709 | 3.818 | 4.301 | 5.177 | 5.907 | 5.882 | 2.565 | 0.0491899 | family with sequence similarity 40, member B |
| KIAA1875 | 9.970 | 9.118 | 10.386 | 11.331 | 11.399 | 11.293 | 2.568 | 0.0390395 | KIAA1875 |
| UBE2Q1 | 6.984 | 6.270 | 6.257 | 8.301 | 8.346 | 7.328 | 2.570 | 0.0449945 | ubiquitin-conjugating enzyme E2Q family member 1 |
| VPS53 | 6.544 | 6.500 | 6.545 | 7.721 | 7.906 | 8.005 | 2.571 | 0.0258998 | vacuolar protein sorting 53 homolog (S. cerevisiae) |
| FBXL18 | 5.307 | 5.315 | 5.243 | 6.588 | 6.674 | 7.273 | 2.578 | 0.0245244 | F-box and leucine-rich repeat protein 18 |
| RNF145 | 8.597 | 9.051 | 8.392 | 9.738 | 9.972 | 10.420 | 2.583 | 0.0429903 | ring finger protein 145 |
| PURA | 4.709 | 4.915 | 4.867 | 6.468 | 6.237 | 5.663 | 2.584 | 0.0463421 | purine-rich element binding protein A |
| TLN2 | 4.539 | 5.274 | 4.638 | 6.545 | 5.593 | 6.649 | 2.593 | 0.0486305 | talin 2 |
| KDM1B | 1.648 | 1.648 | 1.689 | 3.023 | 2.739 | 3.557 | 2.594 | 0.0323282 | lysine (K)-specific demethylase 1B |
| FAM186B | 1.648 | 1.648 | 1.648 | 3.023 | 2.739 | 3.929 | 2.594 | 0.0330246 | family with sequence similarity 186, member B |
| ZDHHC19 | 1.648 | 1.648 | 1.648 | 3.023 | 2.739 | 3.929 | 2.594 | 0.0330246 | zinc finger, DHHC-type containing 19 |

TABLE 4-continued

Differentially Expressed Genes in CD44+ Breast Epithelial Cells

| | Nulliparous (NP) Samples | | | Parous (P) Samples | | | Pseudo | | |
|---|---|---|---|---|---|---|---|---|---|
| Gene Symbol | CD44+ N48 | CD44+ N58 | CD44+ N43 | CD44+ N37 | CD44+ N39 | CD44+ N40 | fold change | P value | Gene description |
| FPR3 | 1.648 | 1.648 | 1.648 | 3.023 | 2.739 | 4.493 | 2.594 | 0.0354270 | formyl peptide receptor 3 |
| MEFV | 1.648 | 1.648 | 1.729 | 3.023 | 2.739 | 4.104 | 2.594 | 0.0357244 | Mediterranean fever |
| LOC55908 | 1.648 | 1.648 | 1.834 | 3.023 | 2.739 | 3.929 | 2.594 | 0.0377050 | No description |
| STK4 | 6.811 | 7.306 | 6.577 | 8.123 | 8.486 | 8.187 | 2.596 | 0.0386437 | serine/threonine kinase 4 |
| MIF4GD | 5.264 | 5.281 | 4.154 | 6.315 | 6.040 | 6.659 | 2.598 | 0.0499553 | MIF4G domain containing |
| MRPS15 | 6.418 | 5.576 | 5.264 | 7.796 | 7.576 | 6.634 | 2.598 | 0.0450229 | mitochondrial ribosomal protein S15 |
| ADAMTS2 | 4.331 | 4.774 | 4.614 | 6.130 | 5.994 | 5.726 | 2.602 | 0.0315289 | ADAM metallopeptidase with thrombospondin type 1 motif, 2 |
| ADNP | 6.482 | 6.338 | 6.878 | 7.883 | 7.727 | 8.028 | 2.620 | 0.0372634 | ADNP homeobox 2 |
| MON1A | 4.008 | 4.017 | 3.071 | 5.314 | 5.405 | 5.398 | 2.622 | 0.0251906 | MON1 homolog A (yeast) |
| MTMR10 | 7.747 | 6.113 | 7.310 | 8.908 | 8.462 | 8.704 | 2.628 | 0.0416038 | myotubularin related protein 10 |
| TCEA3 | 1.648 | 3.538 | 3.894 | 4.477 | 4.692 | 5.289 | 2.630 | 0.0494444 | transcription elongation factor A (SII), 3 |
| NCOR1 | 6.930 | 6.020 | 6.753 | 8.325 | 8.028 | 8.071 | 2.630 | 0.0286790 | nuclear receptor corepressor 1 |
| HDAC3 | 2.970 | 4.638 | 4.337 | 6.034 | 5.676 | 5.561 | 2.631 | 0.0343185 | histone deacetylase 3 |
| STRN4 | 8.435 | 7.238 | 9.030 | 9.588 | 10.045 | 9.832 | 2.632 | 0.0490839 | striatin. calmodulin binding protein 4 |
| KCTD2 | 6.906 | 6.770 | 6.930 | 8.302 | 8.361 | 8.091 | 2.632 | 0.0249841 | potassium channel tetramerisation domain containing 2 |
| ANKRD9 | 7.434 | 6.204 | 6.920 | 8.592 | 8.318 | 8.289 | 2.634 | 0.0362284 | ankyrin repeat domain 9 |
| C9orf23 | 6.036 | 4.275 | 5.926 | 7.433 | 7.260 | 7.303 | 2.635 | 0.0292156 | chromosome 9 open reading frame 23 |
| POLD1 | 5.350 | 3.648 | 4.924 | 6.522 | 6.323 | 6.051 | 2.637 | 0.0420399 | polymerase (DNA directed), delta 1, catalytic subunit 125 kDa |
| CLDN15 | 3.422 | 4.493 | 4.613 | 5.653 | 5.983 | 5.893 | 2.638 | 0.0303622 | claudin 15 |
| PLCD3 | 8.813 | 8.430 | 8.918 | 9.959 | 10.008 | 10.318 | 2.639 | 0.0325064 | phospholipase C, delta 3 |
| PANX2 | 3.818 | 5.048 | 5.544 | 6.808 | 6.324 | 6.453 | 2.649 | 0.0373473 | pannexin 2 |
| CTSS | 4.378 | 4.653 | 3.763 | 6.058 | 5.783 | 5.292 | 2.650 | 0.0422000 | cathepsin S |
| CCDC117 | 5.973 | 6.467 | 5.958 | 7.878 | 7.182 | 7.864 | 2.658 | 0.0317730 | coiled-coil domain containing 117 |
| ALDOA | 12.092 | 11.705 | 12.543 | 13.955 | 13.558 | 13.025 | 2.661 | 0.0483761 | aldolase A, fructose-bisphosphate |
| FRY | 5.503 | 5.013 | 4.034 | 6.600 | 6.428 | 6.074 | 2.667 | 0.0471615 | furry homolog (Drosophila) |
| TAOK2 | 6.879 | 6.347 | 7.174 | 7.992 | 8.590 | 8.197 | 2.668 | 0.0364267 | TAO kinase 2 |
| KLHDC4 | 3.792 | 3.793 | 4.273 | 4.981 | 5.948 | 5.210 | 2.670 | 0.0426707 | kelch domain containing 4 |
| FNIP1 | 7.114 | 7.739 | 7.748 | 9.166 | 8.638 | 9.104 | 2.673 | 0.0356787 | folliculin interacting protein 1 |
| SLC15A2 | 3.456 | 3.797 | 4.027 | 5.446 | 4.672 | 5.285 | 2.674 | 0.0428135 | solute carrier family 15 (H+/peptide transporter), member 2 |
| TEAD4 | 6.983 | 7.215 | 7.706 | 8.180 | 9.125 | 8.939 | 2.674 | 0.0435068 | TEA domain family member 4 |
| KIAA0892 | 7.858 | 7.518 | 7.700 | 9.604 | 9.122 | 8.649 | 2.681 | 0.0378971 | No description |
| DISP1 | 5.731 | 5.664 | 5.716 | 7.087 | 7.253 | 7.128 | 2.683 | 0.0188690 | dispatched homolog 1 (Drosophila) |
| BEAR | 5.499 | 4.679 | 5.230 | 6.655 | 6.293 | 6.701 | 2.685 | 0.0376960 | bifunctional apoptosis regulator |
| MAPKSP1 | 6.179 | 7.654 | 7.534 | 8.598 | 9.083 | 8.743 | 2.693 | 0.0368308 | MARK scaffold protein 1 |
| ITCH | 5.018 | 5.576 | 5.309 | 7.287 | 6.739 | 6.363 | 2.693 | 0.0352544 | itchy E3 ubiquitin protein ligase homolog (mouse) |
| GPATCH8 | 4.555 | 5.251 | 5.446 | 6.654 | 6.682 | 6.757 | 2.695 | 0.0252794 | G patch domain containing 8 |
| C16orf46 | 1.648 | 2.625 | 2.064 | 3.909 | 3.499 | 3.370 | 2.703 | 0.0373945 | chromosome 16 open reading frame 46 |
| SLC12A3 | 1.648 | 2.121 | 2.625 | 3.557 | 4.017 | 3.294 | 2.704 | 0.0389757 | solute carrier family 12 (sodium/chloride transporters), member 3 |
| MSH5 | 2.233 | 2.233 | 2.261 | 3.670 | 3.043 | 4.071 | 2.707 | 0.0460343 | mutS homolog 5 (E. coli) |
| TULP4 | 5.959 | 5.694 | 6.509 | 7.246 | 7.946 | 7.392 | 2.708 | 0.0374333 | tubby like protein 4 |
| AATF | 4.969 | 6.655 | 6.358 | 7.921 | 7.803 | 7.540 | 2.723 | 0.0351310 | apoptosis antagonizing transcription factor |
| CLPB | 2.648 | 2.648 | 2.744 | 5.512 | 4.097 | 3.897 | 2.729 | 0.0300586 | ClpB caseinolytic peptidase B homolog (E. coli) |
| CLASP1 | 6.037 | 6.199 | 6.695 | 8.379 | 7.365 | 7.649 | 2.733 | 0.0402451 | cytoplasmic linker associated protein 1 |
| FAM48A | 3.233 | 5.377 | 5.286 | 6.831 | 6.322 | 6.286 | 2.738 | 0.0439941 | family with sequence similarity 48, member A |

TABLE 4-continued

Differentially Expressed Genes in CD44+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD44+ N48 | CD44+ N58 | CD44+ N43 | CD44+ N37 | CD44+ N39 | CD44+ N40 | | | | |
| CTDP1 | 6.570 | 5.610 | 6.244 | 7.699 | 7.977 | | 7.307 | 2.742 | 0.0359740 | CTD (carboxy-terminal domain, RNA polymerase II, polypeptide A) phosphatase, subunit 1 |
| RSL1D1 | 5.926 | 6.860 | 6.449 | 7.694 | 7.810 | | 8.321 | 2.752 | 0.0344274 | ribosomal L1 domain containing 1 |
| CD55 | 7.788 | 9.110 | 8.391 | 10.066 | 9.644 | | 9.853 | 2.755 | 0.0498860 | CD55 molecule, decay accelerating factor for complement (Cromer blood group) |
| PAQR7 | 8.661 | 6.715 | 7.963 | 9.426 | 9.457 | | 9.285 | 2.756 | 0.0498236 | progestin and adipoQ receptor family member VII |
| KCTD13 | 6.949 | 6.092 | 6.502 | 8.238 | 8.048 | | 7.555 | 2.757 | 0.0408496 | potassium channel tetramerisation domain containing 13 |
| TMBIM1 | 10.605 | 9.938 | 11.104 | 12.568 | 11.856 | | 11.630 | 2.759 | 0.0497113 | transmembrane BAX inhibitor motif containing 1 |
| DHX9 | 7.842 | 8.345 | 8.547 | 9.726 | 9.681 | | 10.012 | 2.759 | 0.0253064 | DEAH (Asp-Glu-Ala-His) box polypeptide 9 |
| PPAPDC2 | 4.708 | 3.511 | 3.456 | 6.016 | 5.659 | | 4.920 | 2.760 | 0.0426236 | phosphatidic acid phosphatase type 2 domain containing 2 |
| RNF40 | 5.291 | 4.799 | 4.993 | 6.882 | 6.347 | | 6.265 | 2.761 | 0.0307144 | ring finger protein 40 |
| TTC38 | 5.039 | 4.897 | 4.602 | 6.512 | 6.073 | | 6.068 | 2.762 | 0.0338014 | tetratricopeptide repeat domain 38 |
| PLSCR2 | 4.142 | 3.197 | 3.521 | 4.664 | 4.875 | | 5.927 | 2.766 | 0.0475373 | phospholipid scramblase 2 |
| PARN | 6.667 | 6.258 | 6.284 | 8.638 | 7.753 | | 7.226 | 2.768 | 0.0489813 | poly(A)-specific ribonuclease (deadenylation nuclease) |
| RNPC3 | 2.970 | 3.953 | 4.268 | 5.626 | 5.427 | | 5.421 | 2.777 | 0.0260274 | RNA-binding region (RNP1, RRM) containing 3 |
| MYLK3 | 5.171 | 4.686 | 4.734 | 6.378 | 5.894 | | 6.646 | 2.780 | 0.0352003 | myosin light chain kinase 3 |
| TFRC | 7.644 | 8.124 | 8.172 | 9.119 | 10.128 | | 9.600 | 2.782 | 0.0284010 | transferrin receptor (p90, CD71) |
| TSC1 | 4.722 | 5.588 | 5.524 | 6.687 | 6.539 | | 7.067 | 2.788 | 0.0363227 | tuberous sclerosis 1 |
| CSK | 8.824 | 8.571 | 8.905 | 10.311 | 10.387 | | 9.801 | 2.794 | 0.0329154 | c-src tyrosine kinase |
| COX10 | 2.970 | 3.820 | 3.272 | 4.907 | 5.182 | | 4.453 | 2.795 | 0.0364017 | COX10 homolog, cytochrome c oxidase assembly protein, heme A: farnesyltransferase (yeast) |
| FZR1 | 5.988 | 5.623 | 6.082 | 7.352 | 7.443 | | 7.564 | 2.795 | 0.0206783 | fizzy/cell division cycle 20 related 1 (Drosophila) |
| WDR44 | 6.011 | 5.482 | 5.965 | 6.965 | 7.126 | | 7.959 | 2.796 | 0.0359830 | WD repeat domain 44 |
| NINL | 2.233 | 2.461 | 2.385 | 3.871 | 3.467 | | 4.230 | 2.800 | 0.0284593 | ninein-like |
| C17orf68 | 4.539 | 5.250 | 5.598 | 6.740 | 6.575 | | 6.904 | 2.807 | 0.0289231 | chromosome 17 open reading frame 68 |
| NME4 | 7.076 | 6.479 | 7.507 | 8.872 | 8.565 | | 8.078 | 2.808 | 0.0420558 | non-metastatic cells 4, protein expressed in |
| ZNF121 | 2.970 | 3.601 | 3.626 | 5.208 | 5.094 | | 4.405 | 2.815 | 0.0360399 | zinc finger protein 121 |
| SLC25A10 | 3.792 | 3.791 | 3.533 | 5.599 | 5.189 | | 5.026 | 2.815 | 0.0227574 | solute carrier family 25 (mitochondrial carrier; dicarboxylate transporter), member 10 |
| SEP9 | 11.830 | 10.336 | 11.508 | 13.324 | 12.827 | | 12.298 | 2.817 | 0.0486076 | septin 9 |
| ZNF276 | 5.828 | 5.364 | 5.729 | 6.659 | 7.224 | | 7.475 | 2.820 | 0.0334229 | zinc finger protein 276 |
| SUV420H1 | 4.793 | 4.984 | 4.530 | 5.822 | 6.294 | | 6.702 | 2.830 | 0.0321972 | suppressor of variegation 4-20 homolog 1 (Drosophila) |
| ALPK3 | 3.818 | 4.229 | 5.062 | 6.408 | 5.658 | | 5.732 | 2.833 | 0.0411095 | alpha-kinase 3 |
| TMEM63C | 2.233 | 2.233 | 2.702 | 3.429 | 4.777 | | 3.737 | 2.836 | 0.0388960 | transmembrane protein 63C |
| LOC100128239 | 2.233 | 2.233 | 2.360 | 3.737 | 3.043 | | 4.071 | 2.836 | 0.0480218 | No description |
| USP8 | 6.608 | 6.345 | 6.173 | 8.152 | 7.678 | | 7.806 | 2.839 | 0.0252523 | ubiquitin specific peptidase 8 |
| SLC4A2 | 6.110 | 6.934 | 6.032 | 8.382 | 7.539 | | 7.636 | 2.843 | 0.0427345 | solute carrier family 4, anion exchanger, member 2 (erythrocyte membrane protein band 3-like 1) |
| ATG2B | 5.047 | 5.479 | 5.440 | 7.054 | 6.225 | | 6.948 | 2.844 | 0.0393182 | ATG2 autophagy related 2 homolog B (S. cerevisiae) |
| BCAT2 | 7.598 | 6.436 | 7.770 | 8.585 | 8.519 | | 9.279 | 2.846 | 0.0488849 | branched chain amino-acid transaminase 2, mitochondrial |
| RACGAP1 | 4.972 | 5.253 | 5.411 | 6.329 | 6.764 | | 7.873 | 2.850 | 0.0303144 | Rac GTPase activating protein 1 |
| AGGF1 | 4.086 | 3.907 | 3.577 | 5.607 | 5.089 | | 5.159 | 2.853 | 0.0318548 | angiogenic factor with G patch and FHA domains 1 |
| KLF8 | 5.499 | 6.084 | 5.219 | 7.345 | 6.732 | | 7.574 | 2.855 | 0.0308163 | Kruppel-like factor 8 |
| ASAP2 | 5.659 | 5.419 | 5.367 | 7.123 | 6.881 | | 7.028 | 2.856 | 0.0193002 | ArfGAP with SH3 domain, ankyrin repeat and PH domain 2 |
| ACADS | 5.552 | 5.021 | 4.968 | 7.562 | 6.151 | | 6.535 | 2.857 | 0.0428641 | acyl-CoA dehydrogenase, C-2 to C-3 short chain |
| CCNL1 | 9.165 | 8.693 | 9.269 | 10.209 | 10.543 | | 11.090 | 2.859 | 0.0301348 | cyclin L1 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| PDCD11 | 5.789 | 6.630 | 6.003 | 7.519 | 8.050 | 7.483 | 2.860 | 0.0317549 | programmed cell death 11 |
| BAT2L1 | 10.283 | 9.736 | 10.620 | 11.636 | 11.799 | 11.889 | 2.860 | 0.0274825 | No description |
| METTL11A | 8.098 | 7.645 | 6.873 | 9.347 | 9.163 | 9.077 | 2.864 | 0.0292246 | methyltransferase like 11A |
| IVD | 5.151 | 5.173 | 5.511 | 7.140 | 6.692 | 6.341 | 2.865 | 0.0340399 | isovaleryl-CoA dehydrogenase |
| FTSJ3 | 6.072 | 6.940 | 6.692 | 8.212 | 7.638 | 8.234 | 2.867 | 0.0388468 | FtsJ homolog 3 (*E. coli*) |
| STMN1 | 7.744 | 7.043 | 8.225 | 8.633 | 9.264 | 9.614 | 2.868 | 0.0476981 | stathmin 1 |
| PRIC285 | 4.108 | 4.108 | 5.161 | 5.628 | 6.271 | 6.375 | 2.868 | 0.0348475 | No description |
| DKFZp686O2416 | 2.648 | 3.630 | 2.971 | 4.697 | 4.168 | 4.781 | 2.868 | 0.0406499 | No description |
| DRAM1 | 6.252 | 6.833 | 6.649 | 8.218 | 7.615 | 8.355 | 2.871 | 0.0335158 | DNA-damage regulated autophagy modulator 1 |
| RPS10 | 2.970 | 2.970 | 2.970 | 4.492 | 5.005 | 4.327 | 2.872 | 0.0202562 | ribosomal protein S10 |
| ZNF558 | 1.648 | 4.874 | 4.305 | 6.398 | 5.646 | 5.459 | 2.874 | 0.0425029 | zinc finger protein 558 |
| SSR2 | 10.361 | 9.031 | 9.571 | 11.886 | 11.011 | 10.845 | 2.878 | 0.0449203 | signal sequence receptor, beta (translocon-associated protein beta) |
| RHBDD3 | 6.103 | 4.910 | 5.549 | 7.132 | 7.074 | 6.925 | 2.879 | 0.0362562 | rhomboid domain containing 3 |
| LOC92659 | 7.036 | 6.105 | 6.924 | 8.124 | 8.131 | 8.562 | 2.881 | 0.0304260 | No description |
| C17orf73 | 5.952 | 5.238 | 6.365 | 7.382 | 7.585 | 7.479 | 2.882 | 0.0284683 | chromosome 17 open reading frame 73 |
| RAB4A | 6.985 | 6.914 | 6.499 | 7.787 | 8.696 | 8.442 | 2.885 | 0.0339934 | RAB4A, member RAS oncogene family |
| HIVEP1 | 5.938 | 5.230 | 3.984 | 6.657 | 6.209 | 7.467 | 2.886 | 0.0496648 | human immunodeficiency virus type I enhancer binding protein 1 |
| TMPRSS11B | 4.647 | 4.728 | 4.647 | 6.177 | 5.544 | 6.636 | 2.889 | 0.0394471 | transmembrane protease, serine 11B |
| ABCF3 | 6.167 | 6.279 | 6.927 | 7.726 | 7.967 | 7.811 | 2.891 | 0.0381175 | ATP-binding cassette, sub-family F (GCN20), members |
| OTX2OS1 | 2.970 | 3.111 | 3.627 | 4.753 | 4.508 | 5.006 | 2.903 | 0.0283248 | No description |
| MTAP | 5.596 | 5.752 | 5.956 | 7.291 | 7.421 | 7.266 | 2.906 | 0.0182340 | methylthioadenosine phosphorylase |
| B3GALT4 | 0.648 | 3.431 | 3.664 | 4.972 | 5.196 | 4.901 | 2.909 | 0.0289522 | UDP-Gal:betaGlcNAc beta 1,3-galactosyltransferase, polypeptide 4 |
| MFSD5 | 6.647 | 6.487 | 6.542 | 8.548 | 8.084 | 7.809 | 2.911 | 0.0236107 | major facilitator superfamily domain containing 5 |
| PRDM1 | 8.044 | 7.835 | 8.686 | 9.450 | 9.377 | 11.740 | 2.912 | 0.0409341 | PR domain containing 1, with ZNF domain |
| MARK4 | 7.556 | 6.924 | 7.134 | 8.534 | 9.429 | 8.471 | 2.922 | 0.0316399 | MAP/microtubule affinity-regulating kinase 4 |
| C21orf94 | 1.648 | 2.625 | 1.648 | 3.023 | 4.174 | 3.557 | 2.926 | 0.0399109 | chromosome 21 open reading frame 94 |
| SERPINB6 | 9.001 | 7.279 | 8.682 | 10.551 | 9.675 | 9.829 | 2.928 | 0.0445730 | serpin peptidase inhibitor, clade B (ovalbumin), member 6 |
| MED19 | 7.923 | 7.618 | 6.593 | 9.473 | 8.740 | 9.140 | 2.928 | 0.0306867 | mediator complex subunit 19 |
| LILRB1 | 5.908 | 5.281 | 5.768 | 7.013 | 6.889 | 7.459 | 2.929 | 0.0321487 | leukocyte immunoglobulin-like receptor, subfamily B (with TM and ITIM domains), member 1 |
| ZNF7 | 2.648 | 2.648 | 2.744 | 4.883 | 3.852 | 4.199 | 2.930 | 0.0264163 | zinc finger protein 7 |
| C20orf12 | 2.648 | 3.791 | 2.669 | 4.883 | 4.405 | 4.199 | 2.930 | 0.0494222 | chromosome 20 open reading frame 12 |
| INPP4A | 6.624 | 6.013 | 6.693 | 7.558 | 8.176 | 8.801 | 2.931 | 0.0287296 | inositol polyphosphate-4-phosphatase, type I, 107 kDa |
| LOC399815 | 0.648 | 0.648 | 1.245 | 2.202 | 2.353 | 2.370 | 2.935 | 0.0286652 | No description |
| REXO2 | 8.671 | 8.407 | 8.598 | 10.163 | 10.152 | 10.005 | 2.936 | 0.0174180 | REX2, RNA exonuclease 2 homolog (*S. cerevisiae*) |
| SEC22B | 7.781 | 6.370 | 7.186 | 9.335 | 8.555 | 8.286 | 2.936 | 0.0443296 | SEC22 vesicle trafficking protein homolog B (*S. cerevisiae*) (gene/pseudogene) |
| UBE3B | 4.331 | 4.853 | 4.518 | 6.453 | 5.726 | 6.072 | 2.937 | 0.0294458 | ubiquitin protein ligase E3B |
| TATDN3 | 3.792 | 4.595 | 5.221 | 6.731 | 6.151 | 5.608 | 2.939 | 0.0440551 | TatD DNase domain containing 3 |
| STX4 | 9.151 | 8.902 | 9.909 | 10.710 | 10.457 | 11.201 | 2.939 | 0.0430596 | syntaxin 4 |
| ZSWIM7 | 4.086 | 3.771 | 4.526 | 5.883 | 5.957 | 5.327 | 2.940 | 0.0277217 | zinc finger, SWIM-type containing 7 |
| RELB | 9.095 | 8.137 | 9.548 | 10.682 | 10.224 | 10.653 | 2.944 | 0.0391511 | v-rel reticuloendotheliosis viral oncogene homolog B |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| FAU | 13.231 | 12.684 | 13.522 | 14.789 | 14.877 | 14.790 | 2.946 | 0.0213716 | Finkel-Biskis-Reilly murine sarcoma virus (FBR-MuSV) ubiquitously expressed |
| ATG4B | 7.995 | 7.016 | 8.090 | 9.473 | 9.259 | 9.649 | 2.947 | 0.0243151 | ATG4 autophagy related 4 homolog B (S. cerevisiae) |
| FIP1L1 | 4.378 | 3.812 | 5.028 | 5.561 | 6.489 | 5.944 | 2.961 | 0.0393272 | FIP1 like 1 (S. cerevisiae) |
| ASH1L | 6.835 | 6.410 | 6.898 | 8.401 | 7.876 | 8.793 | 2.961 | 0.0259594 | ash1 (absent, small, or homeotic)-like (Drosophila) |
| HUNK | 6.608 | 4.782 | 5.803 | 7.652 | 7.285 | 7.370 | 2.963 | 0.0393023 | hormonally up-regulated Neu-associated kinase |
| RGS14 | 6.070 | 3.983 | 4.142 | 5.551 | 7.245 | 7.357 | 2.966 | 0.0473841 | regulator of G-protein signaling 14 |
| POM121L10P | 4.439 | 4.190 | 4.418 | 5.240 | 6.019 | 5.987 | 2.968 | 0.0380530 | POM121 membrane glycoprotein-like 10, pseudogene |
| PMS2 | 5.400 | 5.253 | 5.830 | 6.915 | 7.432 | 6.823 | 2.969 | 0.0266915 | PMS2 postmeiotic segregation increased 2 (S. cerevisiae) |
| PPP3CC | 8.154 | 6.987 | 7.252 | 9.393 | 8.847 | 8.557 | 2.970 | 0.0488142 | protein phosphatase 3, catalytic subunit, gamma isozyme |
| SLC25A26 | 7.687 | 7.081 | 6.838 | 8.413 | 9.035 | 8.741 | 2.978 | 0.0324842 | solute carrier family 25, member 26 |
| ZNF208 | 3.456 | 4.501 | 4.579 | 5.960 | 6.154 | 5.644 | 2.979 | 0.0266735 | zinc finger protein 208 |
| ACY1 | 6.967 | 5.414 | 6.580 | 7.976 | 8.541 | 7.471 | 2.979 | 0.0432010 | aminoacylase 1 |
| DGKD | 6.918 | 6.451 | 7.219 | 8.027 | 9.050 | 8.152 | 2.981 | 0.0380371 | diacylglycerol kinase, delta 130 kDa |
| C20orf29 | 4.620 | 4.492 | 4.025 | 7.547 | 6.068 | 5.501 | 2.983 | 0.0296163 | chromosome 20 open reading frame 29 |
| LOC150381 | 5.598 | 4.017 | 5.384 | 6.965 | 7.067 | 6.261 | 2.993 | 0.0365425 | No description |
| PPAN | 6.829 | 5.591 | 6.631 | 7.502 | 8.411 | 7.796 | 2.995 | 0.0449799 | peter pan homolog (Drosophila) |
| CASP9 | 6.470 | 3.431 | 6.071 | 7.391 | 7.580 | 8.053 | 2.996 | 0.0323532 | caspase 9, apoptosis-related cysteine peptidase |
| ZNF625 | 4.008 | 3.544 | 4.835 | 6.065 | 5.591 | 5.289 | 2.997 | 0.0451088 | zinc finger protein 625 |
| XRCC3 | 2.648 | 2.822 | 3.298 | 4.883 | 4.784 | 3.897 | 2.999 | 0.0326929 | X-ray repair complementing defective repair in Chinese hamster cells 3 |
| SHROOM3 | 6.343 | 6.369 | 7.229 | 7.954 | 9.858 | 7.750 | 3.000 | 0.0430319 | shroom family member 3 |
| TNFRSF9 | 3.947 | 4.342 | 3.572 | 5.532 | 4.884 | 6.111 | 3.002 | 0.0400641 | tumor necrosis factor receptor superfamily, member 9 |
| ZFYVE26 | 3.648 | 4.055 | 3.976 | 5.920 | 5.103 | 5.565 | 3.010 | 0.0241757 | zinc finger, FYVE domain containing 26 |
| DENND5A | 9.235 | 8.563 | 7.907 | 10.153 | 9.903 | 10.649 | 3.011 | 0.0341730 | DENN/MADD domain containing 5A |
| HTT | 7.683 | 6.819 | 6.715 | 8.409 | 8.316 | 8.590 | 3.011 | 0.0467858 | huntingtin |
| RNF207 | 4.214 | 4.176 | 3.649 | 5.769 | 4.664 | 6.222 | 3.015 | 0.0490319 | ring finger protein 207 |
| MEGF8 | 5.640 | 4.920 | 5.257 | 7.277 | 6.850 | 6.329 | 3.016 | 0.0342887 | multiple EGF-like-domains 8 |
| PRPF4 | 6.177 | 6.291 | 6.860 | 8.453 | 7.943 | 7.766 | 3.016 | 0.0267567 | PRP4 pre-mRNA processing factor 4 homolog (yeast) |
| FAM184B | 8.832 | 8.406 | 9.347 | 10.013 | 10.057 | 10.940 | 3.017 | 0.0455913 | family with sequence similarity 184, member B |
| GVIN1 | 1.648 | 1.648 | 1.648 | 3.023 | 3.247 | 3.929 | 3.029 | 0.0196482 | No description |
| RIMS1 | 1.648 | 1.648 | 1.834 | 3.830 | 3.247 | 2.752 | 3.029 | 0.0307754 | regulating synaptic membrane exocytosis 1 |
| C10orf111 | 1.648 | 1.648 | 1.648 | 2.625 | 3.247 | 3.929 | 3.029 | 0.0320416 | chromosome 10 open reading frame 111 |
| LOC100272228 | 1.648 | 1.648 | 1.648 | 2.625 | 3.247 | 3.929 | 3.029 | 0.0320416 | No description |
| RABL2B | 1.648 | 1.648 | 1.648 | 2.625 | 3.247 | 4.104 | 3.029 | 0.0323920 | RAB, member of RAS oncogene family-like 2B |
| APOBEC3H | 1.648 | 1.648 | 1.689 | 2.625 | 3.247 | 4.236 | 3.029 | 0.0336912 | apolipoprotein B mRNA editing enzyme, catalytic polypeptide-like 3H |
| ZNF134 | 1.648 | 2.926 | 1.834 | 4.405 | 3.247 | 3.929 | 3.029 | 0.0364357 | zinc finger protein 134 |
| CDKN2BAS | 1.648 | 1.879 | 1.648 | 2.625 | 3.247 | 3.929 | 3.029 | 0.0378139 | No description |
| RAD1 | 5.504 | 5.439 | 4.802 | 6.686 | 7.103 | 6.642 | 3.031 | 0.0274347 | RAD1 homolog (S. pombe) |
| ATMIN | 6.777 | 5.638 | 6.303 | 8.345 | 7.905 | 7.668 | 3.036 | 0.0266305 | ATM interactor |
| MYH14 | 4.378 | 4.859 | 5.401 | 6.163 | 8.754 | 5.981 | 3.038 | 0.0445972 | myosin, heavy chain 14, non-muscle |
| ADNP | 5.830 | 6.785 | 7.054 | 8.300 | 8.005 | 8.660 | 3.045 | 0.0270506 | activity-dependent neuroprotector homeobox |
| SLC43A1 | 5.645 | 4.992 | 6.160 | 7.253 | 6.441 | 7.821 | 3.047 | 0.0485633 | solute carrier family 43, member 1 |
| GRPEL1 | 8.296 | 8.985 | 7.879 | 9.487 | 10.132 | 10.039 | 3.047 | 0.0409965 | GrpE-like 1, mitochondrial (E. coli) |
| G8orf80 | 4.086 | 5.261 | 5.129 | 6.869 | 6.133 | 6.730 | 3.048 | 0.0288697 | chromosome 8 open reading frame 80 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| YRDC | 6.418 | 5.530 | 6.156 | 8.027 | 7.731 | 7.356 | 3.050 | 0.0259733 | yrdC domain containing (*E. coli*) |
| FAM189B | 6.283 | 5.852 | 7.238 | 8.286 | 7.893 | 7.702 | 3.052 | 0.0469820 | family with sequence similarity 189, member B |
| HUWE1 | 7.381 | 7.777 | 7.658 | 9.194 | 9.267 | 9.316 | 3.052 | 0.0154672 | HECT, UBA and WWE domain containing 1 |
| MURC | 2.970 | 3.406 | 3.552 | 4.580 | 4.611 | 6.377 | 3.052 | 0.0342977 | muscle-related coiled-coil protein |
| PER1 | 9.994 | 9.518 | 11.227 | 12.348 | 11.128 | 12.457 | 3.053 | 0.0479948 | period homolog 1 (*Drosophila*) |
| UBE2G2 | 7.961 | 8.575 | 9.061 | 10.118 | 10.398 | 10.186 | 3.054 | 0.0248322 | ubiquitin-conjugating enzyme E2G 2 (UBC7 homolog, yeast) |
| TRIM8 | 10.354 | 9.527 | 8.853 | 11.372 | 10.465 | 11.809 | 3.057 | 0.0489168 | tripartite motif-containing 8 |
| ZC3H18 | 6.349 | 5.474 | 5.872 | 7.484 | 7.481 | 7.749 | 3.058 | 0.0228218 | zinc finger CCCH-type containing 18 |
| SUV420H2 | 4.709 | 4.778 | 5.202 | 6.391 | 6.265 | 8.186 | 3.060 | 0.0272683 | suppressor of variegation 4-20 homolog 2 (*Drosophila*) |
| MRPL4 | 4.904 | 6.619 | 6.642 | 8.100 | 8.256 | 8.148 | 3.061 | 0.0225584 | mitochondrial ribosomal protein L4 |
| MINA | 6.769 | 5.963 | 4.690 | 7.618 | 7.474 | 7.579 | 3.066 | 0.0417646 | MYO induced nuclear antigen |
| USH1G | 2.648 | 3.540 | 4.170 | 4.446 | 5.576 | 5.156 | 3.066 | 0.0481633 | Usher syndrome 1G (autosomal recessive) |
| MLXIPL | 4.620 | 5.199 | 5.342 | 6.240 | 6.494 | 7.114 | 3.073 | 0.0328218 | MLX interacting protein-like |
| XPO4 | 3.818 | 5.143 | 4.674 | 6.296 | 6.513 | 5.687 | 3.077 | 0.0387643 | exportin 4 |
| C1orf21 | 8.738 | 7.810 | 7.911 | 9.452 | 9.533 | 9.781 | 3.078 | 0.0395102 | chromosome 1 open reading frame 21 |
| NLRP1 | 5.553 | 4.482 | 4.498 | 6.146 | 6.104 | 6.719 | 3.079 | 0.0453411 | NLR family, pyrin domain containing 1 |
| L2HGDH | 5.401 | 6.855 | 6.598 | 8.101 | 8.221 | 8.357 | 3.080 | 0.0224586 | L-2-hydroxyglutarate dehydrogenase |
| ZNF529 | 4.805 | 5.003 | 4.522 | 5.528 | 6.626 | 6.511 | 3.081 | 0.0453321 | zinc finger protein 529 |
| HCN2 | 2.233 | 2.524 | 2.991 | 3.278 | 4.151 | 6.439 | 3.089 | 0.0494825 | hyperpolarization activated cyclic nucleotide-gated potassium channel 2 |
| CCDC86 | 7.746 | 8.085 | 7.722 | 9.274 | 10.300 | 9.375 | 3.092 | 0.0221154 | coiled-coil domain containing 86 |
| CARD6 | 8.671 | 8.373 | 8.847 | 10.299 | 10.097 | 10.316 | 3.093 | 0.0186853 | caspase recruitment domain family, member 6 |
| BET1L | 5.107 | 4.770 | 5.011 | 7.734 | 6.399 | 6.608 | 3.094 | 0.0206153 | blocked early in transport 1 homolog (*S. cerevisiae*)-like |
| RAH | 8.282 | 7.633 | 8.036 | 9.070 | 9.666 | 9.993 | 3.096 | 0.0301945 | retinoic acid induced 1 |
| ZNF579 | 5.539 | 5.892 | 5.723 | 7.172 | 7.523 | 7.296 | 3.099 | 0.0178541 | zinc finger protein 579 |
| TMEM63B | 6.873 | 6.815 | 8.065 | 8.448 | 9.214 | 9.128 | 3.101 | 0.0359040 | transmembrane protein 63B |
| WDR19 | 2.970 | 5.666 | 5.090 | 6.970 | 6.422 | 6.724 | 3.103 | 0.0349744 | WD repeat domain 19 |
| BPNT1 | 11.316 | 10.810 | 10.888 | 13.080 | 12.419 | 12.525 | 3.109 | 0.0222977 | 3(2), 5'-bisphosphate nucleotidase 1 |
| ANKS3 | 4.895 | 5.008 | 6.025 | 7.075 | 7.264 | 6.535 | 3.117 | 0.0336073 | ankyrin repeat and sterile alpha motif domain containing 3 |
| USP35 | 2.233 | 2.932 | 2.949 | 4.276 | 3.958 | 4.590 | 3.119 | 0.0292066 | ubiquitin specific peptidase 35 |
| TCTEX1D4 | 1.648 | 1.648 | 2.121 | 4.376 | 3.247 | 3.294 | 3.130 | 0.0238014 | Tctex1 domain containing 4 |
| EXOC6B | 1.648 | 1.648 | 1.648 | 3.830 | 2.739 | 3.294 | 3.130 | 0.0266825 | exocyst complex component 6B |
| CR1 | 1.648 | 2.304 | 2.834 | 5.056 | 3.805 | 3.294 | 3.130 | 0.0404211 | complement component (3b/4b) receptor 1 (Knops blood group) |
| FXYD2 | 4.580 | 3.558 | 4.094 | 6.343 | 5.741 | 4.838 | 3.132 | 0.0497023 | FXYD domain containing ion transport regulator 2 |
| E2F2 | 2.648 | 2.904 | 3.424 | 5.072 | 4.405 | 4.346 | 3.133 | 0.0286998 | E2F transcription factor 2 |
| THAP7 | 6.570 | 7.334 | 4.575 | 8.788 | 8.221 | 7.742 | 3.139 | 0.0396267 | THAP domain containing 7 |
| CYTH2 | 9.298 | 8.475 | 8.275 | 10.127 | 10.403 | 10.024 | 3.142 | 0.0363137 | cytohesin 2 |
| APOOL | 6.036 | 5.272 | 5.736 | 7.516 | 6.812 | 7.688 | 3.144 | 0.0279601 | apolipoprotein O-like |
| ZNF662 | 3.947 | 4.464 | 3.694 | 5.600 | 5.507 | 5.708 | 3.146 | 0.0249598 | zinc finger protein 662 |
| ZFPM1 | 6.017 | 4.661 | 5.034 | 7.002 | 7.602 | 6.320 | 3.157 | 0.0376821 | zinc finger protein, multitype 1 |
| DHX37 | 5.322 | 6.087 | 6.981 | 7.748 | 8.564 | 7.410 | 3.161 | 0.0381355 | DEAH (Asp-Glu-Ala-His) box polypeptide 37 |
| AFMID | 3.456 | 4.706 | 4.501 | 5.476 | 5.669 | 6.370 | 3.170 | 0.0401425 | arylformamidase |
| GCDH | 6.167 | 5.264 | 5.587 | 7.796 | 7.359 | 6.929 | 3.172 | 0.0274166 | glutaryl-CoA dehydrogenase |
| GJB2 | 2.648 | 3.507 | 3.603 | 5.173 | 5.778 | 4.199 | 3.173 | 0.0343490 | gap junction protein, beta 2, 26 kDa |
| C19orf44 | 4.264 | 3.747 | 4.503 | 6.268 | 5.414 | 5.881 | 3.176 | 0.0256787 | chromosome 19 open reading frame 44 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| SYNRG | 4.839 | 5.151 | 5.883 | 6.470 | 6.822 | 7.700 | 3.184 | 0.0346007 | synergin, gamma |
| PDIA3 | 5.503 | 4.480 | 5.055 | 7.181 | 6.151 | 6.293 | 3.185 | 0.0440641 | protein disulfide isomerase family A, member 3 |
| LOC284276 | 2.233 | 2.233 | 2.261 | 4.151 | 3.043 | 3.905 | 3.186 | 0.0403075 | No description |
| TMEM184B | 7.419 | 7.045 | 7.654 | 9.290 | 9.091 | 8.810 | 3.188 | 0.0193182 | transmembrane protein 184B |
| DNASE1 | 4.817 | 5.045 | 5.178 | 6.719 | 6.562 | 6.748 | 3.190 | 0.0152184 | deoxyribonuclease I |
| TRPM7 | 5.854 | 6.415 | 6.498 | 7.739 | 7.562 | 8.171 | 3.190 | 0.0273217 | transient receptor potential cation channel, subfamily M, member 7 |
| CEACAM5 | 7.977 | 7.296 | 8.209 | 9.513 | 9.514 | 9.883 | 3.190 | 0.0190860 | carcinoembryonic antigen-related cell adhesion molecule 5 |
| FOXO1 | 8.791 | 8.733 | 8.167 | 10.730 | 9.386 | 10.407 | 3.185 | 0.0387033 | forkhead box O1 |
| CUL2 | 6.227 | 5.758 | 6.063 | 7.593 | 7.776 | 7.738 | 3.195 | 0.0156406 | cullin 2 |
| SLAMF6 | 1.648 | 1.648 | 1.648 | 3.326 | 3.247 | 3.746 | 3.199 | 0.0131414 | SLAM family member 6 |
| LRRC33 | 1.648 | 1.648 | 2.234 | 3.326 | 2.739 | 4.692 | 3.199 | 0.0426035 | leucine rich repeat containing 33 |
| CENPBD1 | 1.648 | 1.978 | 3.023 | 3.326 | 3.805 | 4.104 | 3.199 | 0.0475282 | CENPB DNA-binding domains containing 1 |
| NMUR1 | 4.214 | 4.213 | 4.672 | 5.696 | 6.350 | 6.051 | 3.199 | 0.0214783 | neuromedin U receptor 1 |
| STK11 | 6.842 | 5.878 | 6.936 | 8.237 | 8.274 | 8.615 | 3.202 | 0.0218305 | serine/threonine kinase 11 |
| MLL4 | 7.243 | 6.378 | 7.090 | 8.174 | 8.926 | 8.584 | 3.210 | 0.0277064 | ankyrin repeat and LEM domain containing 1 |
| SMC1A | 5.775 | 6.451 | 6.264 | 8.238 | 7.946 | 7.268 | 3.210 | 0.0283920 | structural maintenance of chromosomes 1A |
| FLJ44635 | 0.648 | 2.359 | 2.714 | 3.351 | 4.043 | 4.262 | 3.213 | 0.0339754 | No description |
| SETMAR | 3.619 | 4.495 | 4.417 | 6.015 | 6.181 | 5.571 | 3.216 | 0.0235927 | SET domain and mariner transposase fusion gene |
| C2orf68 | 6.917 | 6.672 | 5.737 | 8.603 | 8.162 | 8.109 | 3.218 | 0.0227192 | chromosome 2 open reading frame 68 |
| CD58 | 4.264 | 4.738 | 4.170 | 5.985 | 5.608 | 6.424 | 3.218 | 0.0265147 | CD58 molecule |
| ANKRD13B | 5.941 | 6.297 | 6.410 | 7.169 | 8.134 | 7.986 | 3.224 | 0.0332114 | ankyrin repeat domain 13B |
| ARGFX | 3.648 | 3.821 | 3.887 | 5.901 | 5.430 | 5.338 | 3.225 | 0.0151934 | arginine-fifty homeobox |
| SERPINC1 | 2.233 | 3.737 | 2.461 | 4.151 | 4.151 | 4.791 | 3.226 | 0.0493140 | serpin peptidase inhibitor, clade C (antithrombin), member 1 |
| MCCC2 | 7.579 | 6.220 | 6.526 | 8.762 | 8.715 | 7.911 | 3.229 | 0.0368752 | methylcrotonoyl-CoA carboxylase 2 (beta) |
| SPATA5L1 | 4.423 | 3.645 | 4.751 | 5.731 | 6.443 | 5.926 | 3.231 | 0.0256877 | spermatogenesis associated 5-like 1 |
| ANKLE1 | 5.633 | 5.912 | 5.059 | 7.389 | 6.718 | 7.606 | 3.234 | 0.0269168 | ankyrin repeat and LEM domain containing 1 |
| PPOX | 2.648 | 2.768 | 2.921 | 3.897 | 4.618 | 4.579 | 3.241 | 0.0250201 | protoporphyrinogen oxidase |
| SF3B4 | 9.275 | 8.976 | 8.460 | 10.999 | 10.391 | 10.161 | 3.250 | 0.0301258 | splicing factor 3b, subunit 4, 49 kDa |
| LOC339047 | 1.648 | 4.117 | 4.797 | 4.931 | 5.818 | 6.428 | 3.252 | 0.0447421 | No description |
| IRX1 | 6.103 | 6.586 | 7.024 | 8.288 | 10.744 | 7.688 | 3.253 | 0.0330471 | iroquois homeobox 1 |
| NUP214 | 5.731 | 6.834 | 5.991 | 7.693 | 7.680 | 7.850 | 3.253 | 0.0329993 | nucleoporin 214 kDa |
| SULT1B1 | 0.648 | 0.648 | 0.648 | 2.202 | 2.353 | 3.043 | 3.259 | 0.0151754 | sulfotransferase family, cytosolic, 1B, member 1 |
| MUC2 | 0.648 | 0.648 | 0.648 | 2.202 | 2.353 | 3.351 | 3.259 | 0.0164180 | mucin 2. oligomeric mucus/gel-forming |
| NAPSA | 0.648 | 0.648 | 0.648 | 2.202 | 2.353 | 3.351 | 3.259 | 0.0164180 | napsin A aspartic peptidase |
| OXNAD1 | 0.648 | 0.648 | 1.245 | 2.714 | 2.353 | 2.370 | 3.259 | 0.0222735 | oxidoreductase NAD-binding domain containing 1 |
| RNF216 | 6.091 | 6.137 | 6.823 | 8.118 | 8.260 | 7.797 | 3.261 | 0.0215484 | ring finger protein 216 |
| PTCD3 | 6.164 | 6.507 | 6.655 | 7.707 | 8.737 | 8.214 | 3.263 | 0.0220073 | Pentatricopeptide repeat domain 3 |
| SNAPC4 | 4.378 | 4.937 | 5.888 | 6.644 | 7.273 | 6.492 | 3.264 | 0.0344503 | small nuclear RNA activating complex, polypeptide 4, 190 kDa |
| RPTOR | 6.229 | 4.543 | 6.506 | 7.705 | 8.213 | 7.247 | 3.264 | 0.0334589 | regulatory associated protein of MTOR, complex 1 |
| ATP6VOD2 | 6.930 | 6.193 | 7.063 | 8.637 | 8.669 | 8.630 | 3.264 | 0.0148218 | ATPase, H+ transporting, lysosomal 38 kDa, VO subunit d2 |
| ODF3B | 6.756 | 6.358 | 7.577 | 8.232 | 8.738 | 8.465 | 3.268 | 0.0355380 | outer dense fiber of sperm tails 3B |
| ZNF530 | 2.233 | 2.814 | 3.067 | 4.276 | 4.523 | 4.777 | 3.270 | 0.0180239 | zinc finger protein 530 |
| TNFSF10 | 9.745 | 8.439 | 9.283 | 10.993 | 10.919 | 11.285 | 3.272 | 0.0206402 | tumor necrosis factor (ligand) superfamily, member 10 |
| PSPN | 0.648 | 2.552 | 3.664 | 4.262 | 4.043 | 5.343 | 3.272 | 0.0362132 | persephin |
| RBM23 | 8.040 | 6.513 | 7.729 | 9.750 | 9.204 | 9.103 | 3.272 | 0.0254471 | RNA binding motif protein 23 |

TABLE 4-continued

Differentially Expressed Genes in CD44+ Breast Epithelial Cells

| | Nulliparous (NP) Samples | | | Parous (P) Samples | | | | Pseudo fold change | P value | Gene description |
|---|---|---|---|---|---|---|---|---|---|---|
| Gene Symbol | CD44+ N48 | CD44+ N58 | CD44+ N43 | CD44+ N37 | CD44+ N39 | CD44+ N40 | | | | |
| DNAJB13 | 2.233 | 2.565 | 2.951 | 4.276 | 5.017 | 3.737 | | 3.273 | 0.0278471 | DnaJ (Hsp40) homolog, subfamily B, member 13 |
| LSG1 | 4.793 | 3.456 | 3.951 | 5.438 | 5.662 | 6.144 | | 3.274 | 0.0332669 | large subunit GTPase 1 homolog (S. cerevisiae) |
| ZNF251 | 4.142 | 4.437 | 2.233 | 5.943 | 5.458 | 5.853 | | 3.274 | 0.0269785 | zinc finger protein 251 |
| SIRT3 | 10.236 | 9.525 | 10.552 | 11.948 | 12.013 | 11.655 | | 3.276 | 0.0219435 | sirtuin 3 |
| RRAGA | 9.875 | 8.646 | 8.913 | 11.448 | 10.626 | 10.450 | | 3.277 | 0.0355289 | Ras-related GTP binding A |
| PLEKHF1 | 7.603 | 6.757 | 7.376 | 8.471 | 9.450 | 8.992 | | 3.282 | 0.0266215 | pleckstrin homology domain containing, family F (with FYVE domain) member 1 |
| POMGNT1 | 7.181 | 5.688 | 6.450 | 8.873 | 8.359 | 7.403 | | 3.282 | 0.0403615 | protein O-linked mannose beta1,2-N-acetylglucosaminyltransferase |
| ATAD3A | 5.598 | 5.803 | 7.021 | 7.827 | 8.042 | 7.313 | | 3.283 | 0.0445563 | ATPase family, AAA domain containing 3A |
| MTPAP | 9.214 | 9.010 | 10.030 | 10.886 | 11.029 | 10.929 | | 3.284 | 0.0328128 | mitochondrial poly(A) polymerase |
| PRRX2 | 9.669 | 7.471 | 9.079 | 10.588 | 10.150 | 11.385 | | 3.286 | 0.0379539 | paired related homeobox 2 |
| ZFAT | 3.947 | 3.937 | 3.655 | 6.345 | 4.797 | 5.654 | | 3.287 | 0.0302908 | zinc finger and AT hook domain containing |
| SIRT7 | 4.972 | 6.198 | 5.754 | 6.792 | 7.564 | 7.472 | | 3.288 | 0.0356454 | sirtuin 7 |
| EIF2B4 | 6.732 | 7.193 | 6.769 | 8.911 | 8.767 | 8.402 | | 3.291 | 0.0154582 | eukaryotic translation initiation factor 2B, subunit 4 delta, 67 kDa |
| TDRD7 | 3.792 | 3.520 | 3.402 | 5.715 | 4.499 | 5.239 | | 3.292 | 0.0343400 | tudor domain containing 7 |
| KIAA0355 | 8.189 | 7.198 | 8.193 | 9.914 | 9.750 | 9.641 | | 3.296 | 0.0178166 | KIAA0355 |
| EIF4G1 | 7.677 | 7.179 | 7.946 | 9.399 | 9.677 | 8.783 | | 3.299 | 0.0264607 | eukaryotic translation initiation factor 4 gamma, 1 |
| MOV10L1 | 0.648 | 0.648 | 0.729 | 2.202 | 4.043 | 2.370 | | 3.299 | 0.0201549 | Mov10l1, Moloney leukemia virus 10-like 1, homolog (mouse) |
| KIAA0101 | 0.648 | 0.648 | 0.648 | 2.202 | 4.428 | 2.370 | | 3.299 | 0.0211109 | KIAA0101 |
| ZNF167 | 3.194 | 0.648 | 0.648 | 4.748 | 4.602 | 2.370 | | 3.299 | 0.0392211 | zinc finger protein 167 |
| LMTK2 | 7.232 | 7.617 | 7.829 | 9.120 | 9.340 | 9.386 | | 3.301 | 0.0166097 | lemur tyrosine kinase 2 |
| DNAJC9 | 4.142 | 3.665 | 3.448 | 5.661 | 5.807 | 5.172 | | 3.303 | 0.0185979 | DnaJ (Hsp40) homolog, subfamily C, member 9 |
| RAB2B | 5.229 | 4.693 | 5.308 | 6.953 | 6.521 | 6.965 | | 3.303 | 0.0186430 | RAB2B, member RAS oncogene family |
| PIWIL4 | 2.233 | 2.233 | 2.570 | 3.535 | 3.958 | 5.147 | | 3.306 | 0.0270596 | piwi-like 4 (Drosophila) |
| TFIP11 | 6.689 | 7.447 | 7.025 | 8.869 | 8.750 | 8.538 | | 3.307 | 0.0212600 | tuftelin interacting protein 11 |
| POLR2I | 5.781 | 5.820 | 6.204 | 7.848 | 7.930 | 6.706 | | 3.308 | 0.0395650 | polymerase (RNA) II (DNA directed) polypeptide I, 14.5 kDa |
| HM13 | 7.766 | 6.884 | 7.285 | 9.627 | 9.013 | 8.292 | | 3.311 | 0.0358811 | histocompatibility (minor) 13 |
| FASN | 6.635 | 7.122 | 7.637 | 8.574 | 8.997 | 8.850 | | 3.313 | 0.0251137 | fatty acid synthase |
| NNT | 2.233 | 2.712 | 3.063 | 4.791 | 4.413 | 4.082 | | 3.314 | 0.0218756 | nicotinamide nucleotide transhydrogenase |
| ACAP1 | 4.086 | 4.482 | 4.876 | 6.001 | 5.816 | 8.251 | | 3.316 | 0.0301785 | ArfGAP with coiled-coil, ankyrin repeat and PH domains 1 |
| TEX264 | 8.285 | 6.089 | 7.621 | 9.828 | 9.154 | 9.351 | | 3.318 | 0.0269938 | testis expressed 264 |
| RAB17 | 1.648 | 2.744 | 3.077 | 4.477 | 4.811 | 4.376 | | 3.326 | 0.0181127 | RAB17, member RAS oncogene family |
| BAT3 | 10.663 | 9.409 | 9.727 | 12.184 | 11.676 | 11.144 | | 3.329 | 0.0328870 | No description |
| SYN2 | 4.619 | 3.233 | 4.018 | 5.001 | 6.049 | 5.755 | | 3.332 | 0.0410763 | synapsin II |
| DPYSL4 | 6.689 | 5.247 | 5.945 | 7.029 | 7.683 | 7.997 | | 3.336 | 0.0435407 | dihydropyrimidinase-like 4 |
| GALNT6 | 4.086 | 4.622 | 4.425 | 6.163 | 6.479 | 5.260 | | 3.336 | 0.0357757 | UDP-N-acetyl-alpha-D-galactosamine:polypeptide N-acetylgalactosaminyltransferase 6 (GalNAc-T6) |
| RHBDL1 | 2.233 | 4.224 | 3.520 | 5.003 | 5.017 | 5.963 | | 3.339 | 0.0307234 | rhomboid, veinlet-like 1 (Drosophila) |
| POLH | 6.335 | 7.220 | 6.917 | 8.659 | 8.522 | 8.927 | | 3.344 | 0.0162582 | polymerase (DNA directed), eta |
| HOXC8 | 7.681 | 5.653 | 5.210 | 9.425 | 6.736 | 9.169 | | 3.349 | 0.0476572 | homeobox C8 |
| LYPD3 | 5.572 | 5.879 | 6.430 | 7.317 | 9.532 | 7.566 | | 3.352 | 0.0277355 | LY6/PLAUR domain containing 3 |
| FBXL6 | 4.817 | 3.815 | 2.932 | 5.909 | 5.561 | 5.451 | | 3.354 | 0.0358388 | F-box and leucine-rich repeat protein 6 |
| RUFY1 | 6.818 | 5.569 | 6.004 | 8.037 | 7.750 | 7.573 | | 3.355 | 0.0308364 | RUN and FYVE domain containing 1 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| XRCC2 | 9.450 | 8.940 | 9.978 | 11.299 | 10.688 | 11.235 | 3.360 | 0.0306125 | X-ray repair complementing defective repair in Chinese hamster cells 2 |
| SLC35C2 | 7.052 | 5.990 | 6.798 | 9.582 | 8.056 | 7.742 | 3.368 | 0.0385730 | solute carrier family 35, member C2 |
| CENPT | 6.713 | 7.013 | 7.984 | 8.766 | 9.269 | 8.758 | 3.370 | 0.0307664 | centromere protein T |
| TUFM | 9.230 | 9.309 | 6.760 | 11.062 | 10.282 | 10.506 | 3.371 | 0.0342527 | Tu translation elongation factor, mitochondrial |
| MTFMT | 4.423 | 3.978 | 3.645 | 6.065 | 5.818 | 5.398 | 3.371 | 0.0213806 | mitochondrial methionyl-tRNA formyltransferase |
| PDHA1 | 7.666 | 7.561 | 7.553 | 9.642 | 9.317 | 8.925 | 3.379 | 0.0182014 | pyruvate dehydrogenase (lipoamide) alpha 1 |
| PRDM7 | 2.648 | 2.648 | 2.648 | 4.117 | 4.405 | 4.579 | 3.379 | 0.0142028 | PR domain containing 7 |
| C13orf34 | 2.648 | 3.295 | 4.108 | 5.341 | 4.405 | 5.210 | 3.379 | 0.0424385 | chromosome 13 open reading frame 34 |
| HSF1 | 8.871 | 8.403 | 9.661 | 10.626 | 11.419 | 10.339 | 3.380 | 0.0291359 | heat shock transcription factor 1 |
| SLC25A38 | 7.283 | 7.034 | 6.017 | 8.761 | 9.041 | 8.578 | 3.382 | 0.0177605 | solute carrier family 25, member 38 |
| FHL3 | 8.705 | 6.318 | 8.055 | 9.429 | 9.929 | 9.815 | 3.385 | 0.0333418 | four and a half LIM domains 3 |
| ZNF525 | 4.969 | 4.649 | 4.731 | 6.297 | 7.105 | 6.491 | 3.385 | 0.0161016 | zinc finger protein 525 |
| PPP1R13L | 7.340 | 8.010 | 8.594 | 9.104 | 10.989 | 9.640 | 3.397 | 0.0348676 | protein phosphatase 1, regulatory (inhibitor) subunit 13 like |
| EIF4G3 | 4.539 | 5.355 | 5.114 | 6.607 | 6.822 | 7.120 | 3.399 | 0.0170437 | eukaryotic translation initiation factor 4 gamma, 3 |
| CCDC55 | 7.629 | 7.867 | 7.910 | 9.395 | 9.512 | 9.898 | 3.401 | 0.0138693 | coiled-coil domain containing 55 |
| TRAF7 | 9.545 | 8.051 | 8.191 | 10.726 | 10.620 | 9.817 | 3.402 | 0.0349896 | TNF receptor-associated factor 7 |
| C3orf62 | 5.504 | 4.517 | 5.174 | 6.687 | 6.798 | 7.273 | 3.409 | 0.0196121 | chromosome 3 open reading frame 62 |
| MAN1A1 | 6.851 | 5.452 | 5.790 | 7.560 | 7.293 | 8.077 | 3.410 | 0.0411185 | mannosidase, alpha, class 1A, member 1 |
| PPP2CB | 10.861 | 11.026 | 11.350 | 12.521 | 12.798 | 13.235 | 3.414 | 0.0179456 | protein phosphatase 2, catalytic subunit, beta isozyme |
| DTNBP1 | 5.503 | 3.308 | 5.978 | 7.277 | 7.101 | 7.488 | 3.420 | 0.0254291 | dystrobrevin binding protein 1 |
| SNORD100 | 3.422 | 4.117 | 4.657 | 5.196 | 6.443 | 5.770 | 3.421 | 0.0347386 | small nucleolar RNA, C/D box 100 |
| SLAMF7 | 2.233 | 2.233 | 2.800 | 4.575 | 3.043 | 4.481 | 3.422 | 0.0456925 | SLAM family member 7 |
| C16orf54 | 3.947 | 4.768 | 4.387 | 6.163 | 6.039 | 6.257 | 3.424 | 0.0172003 | chromosome 16 open reading frame 54 |
| ZNF516 | 5.826 | 5.691 | 6.345 | 7.988 | 6.850 | 8.121 | 3.425 | 0.0326603 | zinc finger protein 516 |
| TRIM26 | 8.490 | 7.671 | 8.689 | 9.953 | 10.269 | 10.425 | 3.432 | 0.0171733 | tripartite motif-containing 26 |
| PLAGL2 | 7.663 | 8.235 | 7.638 | 9.417 | 9.930 | 9.505 | 3.433 | 0.0178825 | pleiomorphic adenoma gene-like 2 |
| ADAMTS10 | 7.906 | 5.428 | 6.771 | 7.955 | 8.551 | 9.579 | 3.434 | 0.0445882 | ADAM metallopeptidase with thrombospondin type 1 motif, 10 |
| RBM5 | 6.817 | 7.716 | 8.711 | 9.496 | 9.398 | 10.383 | 3.437 | 0.0285494 | RNA binding motif protein 5 |
| C6orf136 | 5.173 | 5.072 | 5.636 | 7.143 | 6.951 | 6.955 | 3.445 | 0.0162312 | chromosome 6 open reading frame 136 |
| NR5A2 | 5.039 | 4.350 | 3.830 | 6.132 | 6.134 | 6.462 | 3.446 | 0.0217251 | nuclear receptor subfamily 5, group A, member 2 |
| FAM38A | 7.395 | 8.234 | 9.086 | 9.482 | 10.019 | 10.200 | 3.448 | 0.0421390 | family with sequence similarity 38, member A |
| MLH1 | 4.423 | 2.894 | 2.744 | 6.064 | 4.529 | 5.398 | 3.449 | 0.0341508 | mutL homolog 1, colon cancer, nonpolyposis type 2 (E. coli) |
| ALDOC | 5.039 | 5.444 | 5.241 | 6.852 | 7.027 | 7.203 | 3.452 | 0.0133237 | aldolase C, fructose-bisphosphate |
| HPS6 | 5.042 | 5.110 | 4.852 | 7.653 | 6.830 | 6.333 | 3.453 | 0.0193092 | Hermansky-Pudlak syndrome 6 |
| GLO1 | 10.704 | 9.282 | 9.793 | 12.492 | 12.161 | 10.917 | 3.455 | 0.0324308 | glyoxalase I |
| WDR4 | 5.482 | 5.085 | 4.810 | 5.892 | 7.020 | 7.271 | 3.455 | 0.0407622 | WD repeat domain 4 |
| HNRNPH3 | 9.245 | 8.732 | 9.176 | 10.965 | 9.828 | 12.149 | 3.458 | 0.0361244 | heterogeneous nuclear ribonucleoprotein H3 (2H9) |
| ANXA5 | 7.231 | 8.086 | 8.103 | 9.893 | 9.470 | 9.551 | 3.464 | 0.0191172 | annexin A5 |
| CCDC41 | 2.970 | 3.923 | 3.901 | 4.999 | 5.759 | 4.763 | 3.465 | 0.0399560 | coiled-coil domain containing 41 |
| MYNN | 5.768 | 5.481 | 5.786 | 7.806 | 7.244 | 7.561 | 3.474 | 0.0129355 | myoneurin |
| FGF17 | 1.648 | 3.059 | 3.423 | 3.830 | 4.421 | 5.220 | 3.477 | 0.0450998 | fibroblast growth factor 17 |
| LOC100133991 | 3.422 | 3.059 | 2.281 | 4.376 | 4.529 | 5.220 | 3.480 | 0.0265300 | No description |
| SPHK1 | 9.575 | 9.692 | 10.659 | 11.321 | 12.458 | 12.269 | 3.480 | 0.0207726 | sphingosine kinase 1 |
| OGFOD2 | 5.109 | 4.388 | 5.818 | 7.180 | 6.908 | 6.290 | 3.480 | 0.0363816 | 2-oxoglutarate and iron-dependent oxygenase domain containing 2 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| WIPI1 | 4.482 | 4.924 | 5.726 | 7.175 | 6.516 | 6.723 | 3.481 | 0.0270166 | WD repeat domain, phosphoinositide interacting 1 |
| ZMIZ2 | 7.766 | 6.575 | 8.380 | 9.253 | 9.755 | 9.566 | 3.481 | 0.0265924 | zinc finger, MIZ-type containing 2 |
| UMPS | 2.970 | 5.603 | 4.680 | 5.971 | 6.479 | 6.530 | 3.482 | 0.0452149 | uridine monophosphate synthetase |
| MAP3K7IP3 | 6.375 | 6.558 | 5.657 | 8.175 | 7.605 | 8.231 | 3.482 | 0.0213050 | No description |
| C12orf76 | 4.647 | 3.888 | 2.593 | 5.688 | 4.870 | 5.889 | 3.483 | 0.0455601 | chromosome 12 open reading frame 76 |
| TROVE2 | 7.583 | 7.527 | 8.072 | 9.384 | 9.384 | 9.618 | 3.485 | 0.0161383 | TROVE domain family, member 2 |
| SLC17A9 | 2.970 | 3.233 | 3.311 | 5.035 | 5.288 | 4.670 | 3.486 | 0.0144447 | solute carrier family 17, member 9 |
| CHST2 | 4.378 | 4.364 | 5.444 | 7.257 | 5.902 | 6.649 | 3.490 | 0.0291886 | carbohydrate (N-acetylglucosamine-6-O) sulfotransferase 2 |
| RASA2 | 2.233 | 2.233 | 2.288 | 4.033 | 4.037 | 4.669 | 3.491 | 0.0108475 | RAS p21 protein activator 2 |
| QPCTL | 2.233 | 2.233 | 2.360 | 5.284 | 4.037 | 3.737 | 3.491 | 0.0187962 | glutaminyl-peptide cyclotransferase-like |
| ZNF737 | 5.378 | 4.697 | 5.415 | 6.583 | 7.027 | 7.219 | 3.493 | 0.0201071 | zinc finger protein 737 |
| MYST3 | 9.086 | 7.969 | 9.030 | 10.246 | 10.510 | 10.890 | 3.494 | 0.0233972 | MYST histone acetyltransferase (monocytic leukemia) 3 |
| ZNF589 | 4.972 | 3.256 | 4.602 | 6.031 | 5.246 | 6.777 | 3.495 | 0.0489029 | zinc finger protein 589 |
| ABCF1 | 7.460 | 7.458 | 8.469 | 9.764 | 10.021 | 9.264 | 3.497 | 0.0217549 | ATP-binding cassette, sub-family F (GCN20), member 1 |
| SRGAP1 | 8.241 | 9.046 | 8.545 | 9.639 | 10.458 | 10.854 | 3.501 | 0.0306776 | SLIT-ROBO Rho GTPase activating protein 1 |
| HADHA | 9.696 | 8.511 | 8.838 | 10.790 | 10.774 | 10.319 | 3.502 | 0.0332205 | hydroxyacyl-CoA dehydrogenase/3-ketoacyl-CoA thiolase/enoyl-CoA hydratase (trifunctional protein), alpha subunit |
| C19orf6 | 9.917 | 8.300 | 10.602 | 11.725 | 11.784 | 11.549 | 3.503 | 0.0286562 | chromosome 19 open reading frame 6 |
| C17orf69 | 2.648 | 2.648 | 2.648 | 4.326 | 4.515 | 4.458 | 3.505 | 0.0094527 | chromosome 17 open reading frame 69 |
| COMMD2 | 3.860 | 1.962 | 2.359 | 4.972 | 4.870 | 3.773 | 3.508 | 0.0443484 | COMM domain containing 2 |
| NDUFA3 | 8.313 | 6.758 | 7.297 | 10.124 | 9.655 | 8.096 | 3.509 | 0.0482887 | NADH dehydrogenase (ubiquinone) 1 alpha subcomplex, 3, 9 kDa |
| TRIM16 | 9.136 | 8.111 | 9.777 | 10.807 | 11.139 | 10.947 | 3.509 | 0.0239719 | tripartite motif-containing 16 |
| FAM178A | 4.619 | 4.688 | 4.796 | 6.587 | 5.909 | 6.609 | 3.513 | 0.0210180 | family with sequence similarity 178, member A |
| CUL9 | 6.198 | 4.283 | 5.578 | 6.983 | 7.239 | 8.012 | 3.516 | 0.0271858 | cullin 9 |
| CWF19L1 | 4.977 | 4.238 | 4.051 | 6.792 | 6.300 | 5.741 | 3.517 | 0.0236378 | CWF19-like 1, cell cycle control (S. pombe) |
| SFRS16 | 6.177 | 5.362 | 7.018 | 8.054 | 7.991 | 7.557 | 3.518 | 0.0377501 | No description |
| ADPRHL1 | 3.233 | 3.233 | 3.247 | 5.049 | 4.490 | 5.118 | 3.519 | 0.0185889 | ADP-ribosylhydrolase like 1 |
| CREB3 | 6.967 | 7.139 | 7.928 | 9.516 | 9.396 | 8.782 | 3.521 | 0.0200496 | cAMP responsive element binding protein 3 |
| ZNF765 | 5.598 | 5.409 | 5.903 | 7.414 | 8.424 | 7.039 | 3.521 | 0.0198409 | zinc finger protein 765 |
| UBTF | 8.561 | 7.021 | 7.495 | 8.902 | 9.313 | 9.425 | 3.526 | 0.0491400 | upstream binding transcription factor, RNA polymerase I |
| CCDC93 | 3.970 | 4.862 | 4.989 | 6.378 | 6.680 | 6.686 | 3.526 | 0.0158416 | coiled-coil domain containing 93 |
| NTN5 | 1.648 | 1.648 | 2.675 | 3.557 | 3.247 | 4.493 | 3.528 | 0.0323081 | netrin 5 |
| ESRP2 | 3.456 | 4.240 | 5.023 | 5.274 | 8.190 | 5.971 | 3.528 | 0.0386575 | epithelial splicing regulatory protein 2 |
| N4BP1 | 5.855 | 5.231 | 5.341 | 7.677 | 7.601 | 6.847 | 3.535 | 0.0175116 | NEDD4 binding protein 1 |
| MS4A7 | 5.235 | 5.146 | 5.927 | 7.374 | 6.969 | 7.176 | 3.537 | 0.0203088 | membrane-spanning 4-domains, subfamily A, member 7 |
| MUDENG | 3.792 | 4.414 | 3.533 | 6.088 | 5.615 | 5.557 | 3.538 | 0.0185889 | MU-2/AP1 M2 domain containing, death-inducing |
| NFYA | 8.520 | 7.105 | 7.581 | 9.407 | 9.030 | 9.662 | 3.547 | 0.0374243 | nuclear transcription factor Y, alpha |
| MRPS7 | 7.722 | 6.544 | 7.153 | 9.343 | 9.352 | 8.374 | 3.556 | 0.0251692 | mitochondrial ribosomal protein S7 |
| OPLAH | 6.798 | 5.400 | 6.775 | 8.630 | 8.576 | 8.264 | 3.562 | 0.0164045 | 5-oxoprolinase (ATP-hydrolysing) |
| NPM3 | 8.502 | 6.752 | 7.465 | 9.298 | 9.807 | 8.987 | 3.563 | 0.0354922 | nucleophosmin/nucleoplasmin 3 |
| GDAP2 | 5.604 | 4.333 | 4.868 | 6.701 | 6.943 | 6.528 | 3.565 | 0.0245057 | ganglioside induced differentiation associated protein 2 |
| ADRA2C | 6.770 | 6.505 | 6.561 | 11.073 | 8.396 | 7.604 | 3.568 | 0.0340752 | adrenergic, alpha-2C-, receptor |
| FAM185A | 2.233 | 2.233 | 2.233 | 3.278 | 4.624 | 4.071 | 3.573 | 0.0257737 | family with sequence similarity 185, member A |
| INO80 | 6.765 | 6.254 | 7.094 | 8.932 | 8.269 | 8.458 | 3.574 | 0.0184932 | INO80 homolog (S. cerevisiae) |

TABLE 4-continued

Differentially Expressed Genes in CD44+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD44+ N48 | CD44+ N58 | CD44+ N43 | CD44+ N37 | CD44+ N39 | CD44+ N40 | | | | |
| SLC5A5 | 5.142 | 6.012 | 6.396 | 7.372 | 7.185 | 8.235 | | 3.577 | 0.0329653 | solute carrier family 5 (sodium iodide symporter), member 5 |
| PAK1 | 4.378 | 5.858 | 6.068 | 7.027 | 7.697 | 7.850 | | 3.578 | 0.0238603 | p21 protein (Cdc42/Rac)-activated kinase 1 |
| PBX3 | 5.293 | 4.817 | 3.398 | 5.424 | 6.657 | 6.870 | | 3.580 | 0.0468121 | pre-B-cell leukemia homeobox 3 |
| DDX19A | 1.648 | 2.234 | 2.177 | 4.017 | 3.353 | 4.376 | | 3.580 | 0.0188052 | DEAD (Asp-Glu-Ala-As) box polypeptide 19A |
| PSKH1 | 2.970 | 4.917 | 4.407 | 6.180 | 6.251 | 6.409 | | 3.590 | 0.0206312 | protein serine kinase H1 |
| ATR | 4.793 | 3.945 | 4.947 | 6.712 | 6.791 | 5.598 | | 3.590 | 0.0300114 | ataxia telangiectasia and Rad3 related |
| LOC440944 | 5.532 | 5.992 | 6.367 | 7.799 | 7.836 | 8.135 | | 3.590 | 0.0135185 | No description |
| C16orf67 | 0.648 | 4.235 | 3.511 | 5.355 | 5.777 | 4.262 | | 3.591 | 0.0456482 | No description |
| HTATSF1 | 3.233 | 4.070 | 4.081 | 5.671 | 5.768 | 5.927 | | 3.594 | 0.0137328 | HIV-1 Tat specific factor 1 |
| TMEM43 | 8.660 | 7.806 | 8.399 | 10.118 | 10.571 | 9.652 | | 3.595 | 0.0221334 | transmembrane protein 43 |
| KIAA0467 | 4.948 | 4.744 | 5.274 | 7.121 | 6.694 | 6.625 | | 3.597 | 0.0150562 | KIAA0467 |
| PATL1 | 8.707 | 7.758 | 7.582 | 10.319 | 9.304 | 10.554 | | 3.597 | 0.0219802 | protein associated with topoisomerase II homolog 1 (yeast) |
| SCO1 | 6.196 | 5.644 | 4.916 | 7.492 | 7.523 | 6.811 | | 3.601 | 0.0322243 | SCO cytochrome oxidase deficient homolog 1 (yeast) |
| FAM100A | 6.808 | 7.534 | 8.615 | 8.790 | 9.383 | 9.956 | | 3.602 | 0.0450839 | family with sequence similarity 100, member A |
| DFFA | 4.977 | 5.044 | 5.454 | 6.893 | 7.479 | 6.013 | | 3.603 | 0.0367165 | DNA fragmentation factor, 45 kDa, alpha polypeptide |
| ATP5S | 1.648 | 2.304 | 3.557 | 4.154 | 4.017 | 4.376 | | 3.606 | 0.0437584 | ATP synthase, H+ transporting, mitochondrial Fo complex, subunit s (factor B) |
| RIC8B | 6.095 | 5.498 | 6.029 | 7.349 | 7.421 | 8.277 | | 3.606 | 0.0220475 | resistance to inhibitors of cholinesterase 8 homolog B (C. elegans) |
| SPG7 | 8.184 | 7.046 | 7.635 | 9.248 | 9.454 | 10.035 | | 3.606 | 0.0191927 | spastic paraplegia 7 (pure and complicated autosomal recessive) |
| ZNF544 | 4.580 | 4.448 | 5.104 | 6.624 | 6.954 | 5.766 | | 3.607 | 0.0277924 | zinc finger protein 544 |
| PAOX | 1.648 | 1.648 | 1.648 | 4.154 | 3.499 | 3.294 | | 3.607 | 0.0123518 | polyamine oxidase (exo-N4-amino) |
| PNCK | 1.648 | 1.648 | 1.648 | 3.023 | 3.499 | 5.082 | | 3.607 | 0.0210631 | pregnancy up-regulated non-ubiquitously expressed CaM kinase |
| ZNF484 | 1.648 | 1.648 | 1.648 | 4.017 | 3.499 | 2.752 | | 3.607 | 0.0241334 | zinc finger protein 484 |
| CLEC17A | 1.648 | 3.023 | 1.648 | 3.830 | 3.499 | 4.692 | | 3.607 | 0.0305813 | C-type lectin domain family 17, member A |
| SLC22A23 | 7.280 | 6.052 | 6.626 | 9.409 | 7.903 | 8.013 | | 3.607 | 0.0383289 | solute carrier family 22, member 23 |
| DOM3Z | 5.644 | 5.437 | 6.457 | 7.776 | 7.495 | 7.288 | | 3.607 | 0.0267657 | dom-3 homolog Z (C. elegans) |
| ENDOG | 6.829 | 6.040 | 6.433 | 8.422 | 8.564 | 7.891 | | 3.608 | 0.0177868 | endonuclease G |
| CNBP | 9.202 | 8.133 | 8.146 | 10.080 | 9.987 | 10.620 | | 3.615 | 0.0241334 | CCHC-type zinc finger, nucleic acid binding protein |
| KPNB1 | 8.923 | 8.926 | 9.242 | 10.572 | 11.106 | 10.785 | | 3.628 | 0.0145806 | karyopherin (importin) beta 1 |
| ZNF77 | 3.194 | 3.336 | 1.387 | 5.035 | 5.196 | 4.748 | | 3.629 | 0.0179678 | zinc finger protein 77 |
| DNER | 3.233 | 4.409 | 5.347 | 6.891 | 6.271 | 6.172 | | 3.636 | 0.0255303 | delta/notch-like EGF repeat containing |
| PSENEN | 7.650 | 7.645 | 7.258 | 9.737 | 9.510 | 8.691 | | 3.641 | 0.0219983 | presenilin enhancer 2 homolog (C. elegans) |
| ZGLP1 | 3.422 | 1.834 | 2.309 | 3.714 | 4.174 | 4.773 | | 3.643 | 0.0416655 | zinc finger, GATA-like protein 1 |
| FLJ42627 | 4.958 | 4.783 | 5.389 | 6.648 | 6.848 | 6.940 | | 3.644 | 0.0155705 | No description |
| USP13 | 6.288 | 6.040 | 6.284 | 8.161 | 8.419 | 8.068 | | 3.663 | 0.0083872 | ubiquitin specific peptidase 13 (isopeptidase T-3) |
| ILK | 10.084 | 7.862 | 9.432 | 11.306 | 11.285 | 11.425 | | 3.665 | 0.0230922 | integrin-linked kinase |
| GGNBP2 | 7.800 | 7.536 | 8.512 | 9.410 | 9.703 | 10.139 | | 3.665 | 0.0228489 | gametogenetin binding protein 2 |
| IFI30 | 5.109 | 6.479 | 5.819 | 6.983 | 7.319 | 8.933 | | 3.665 | 0.0375393 | interferon, gamma-inducible protein 30 |
| TUBGCP5 | 5.404 | 4.127 | 4.564 | 6.986 | 6.005 | 6.866 | | 3.676 | 0.0245979 | tubulin, gamma complex associated protein 5 |
| PCNT | 6.619 | 5.234 | 7.288 | 8.497 | 8.166 | 8.742 | | 3.678 | 0.0253591 | pericentrin |
| TCEB3 | 7.839 | 8.338 | 8.535 | 9.689 | 10.639 | 10.217 | | 3.678 | 0.0169050 | transcription elongation factor B (SIII), polypeptide 3 (110 kDa, elong in A) |
| ZDHHC14 | 7.452 | 7.148 | 6.871 | 8.750 | 9.326 | 9.094 | | 3.679 | 0.0138873 | zinc finger, DHHC-type containing 14 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| USP32 | 2.648 | 3.104 | 3.016 | 4.182 | 4.899 | 5.549 | 3.687 | 0.0200315 | ubiquitin specific peptidase 32 |
| MLEC | 9.687 | 8.317 | 8.346 | 10.419 | 10.199 | 10.893 | 3.688 | 0.0349542 | malectin |
| PARP8 | 4.264 | 4.719 | 4.264 | 6.268 | 6.151 | 6.479 | 3.697 | 0.0119671 | poly (ADP-ribose) polymerase family, member 8 |
| PLOD3 | 8.185 | 7.007 | 7.564 | 9.452 | 9.577 | 8.923 | 3.702 | 0.0272281 | procollagen-lysine, 2-oxoglutarate 5-dioxygenase 3 |
| PHF1 | 9.216 | 8.642 | 9.686 | 11.106 | 9.932 | 11.665 | 3.705 | 0.0428454 | PHD finger protein 1 |
| DHRS12 | 5.552 | 3.685 | 4.647 | 6.539 | 6.103 | 7.255 | 3.712 | 0.0291005 | dehydrogenase/reductase (SDR family) member 12 |
| ARHGAP27 | 5.619 | 4.281 | 6.536 | 7.512 | 7.959 | 7.218 | 3.713 | 0.0286423 | Rho GTPase activating protein 27 |
| ZC3H8 | 2.233 | 3.975 | 2.587 | 4.481 | 5.183 | 4.481 | 3.716 | 0.0372724 | zinc finger CCCH-type containing 8 |
| RHEBL1 | 3.619 | 5.075 | 2.814 | 5.256 | 5.513 | 6.290 | 3.718 | 0.0445473 | Ras homolog enriched in brain like 1 |
| OTUD4 | 9.996 | 9.664 | 9.698 | 10.719 | 11.593 | 11.999 | 3.719 | 0.0312731 | OTU domain containing 4 |
| CHEK1 | 4.936 | 3.983 | 4.676 | 6.050 | 6.831 | 6.290 | 3.721 | 0.0209002 | CHK1 checkpoint homolog (S. pombe) |
| ABI1 | 7.988 | 8.356 | 8.720 | 9.886 | 10.518 | 10.341 | 3.725 | 0.0157785 | abl-interactor 1 |
| ECD | 7.367 | 7.160 | 8.083 | 9.094 | 9.266 | 9.340 | 3.731 | 0.0230250 | ecdysoneless homolog (Drosophila) |
| GABBR1 | 7.671 | 7.107 | 7.957 | 9.565 | 9.296 | 9.857 | 3.733 | 0.0139865 | gamma-aminobutyric acid (GABA) B receptor, 1 |
| UBA5 | 6.950 | 6.261 | 6.305 | 8.850 | 8.364 | 7.802 | 3.734 | 0.0223775 | ubiquitin-like modifier activating enzyme 5 |
| RAI14 | 8.591 | 6.621 | 7.056 | 9.601 | 9.930 | 8.524 | 3.739 | 0.0393362 | retinoic acid induced 14 |
| SGIP1 | 4.422 | 4.359 | 3.218 | 6.291 | 5.562 | 6.264 | 3.746 | 0.0191546 | SH3-domain GRB2-like (endophilin) interacting protein 1 |
| HES6 | 6.262 | 3.983 | 5.109 | 7.514 | 6.785 | 7.016 | 3.750 | 0.0333154 | hairy and enhancer of split 6 (Drosophila) |
| ZC3H3 | 6.838 | 5.934 | 7.399 | 8.746 | 8.963 | 8.198 | 3.752 | 0.0248114 | zinc finger CCCH-type containing 3 |
| ASAP3 | 4.709 | 2.970 | 3.178 | 5.854 | 4.707 | 6.617 | 3.754 | 0.0326416 | ArfGAP with SH3 domain, ankyrin repeat and PH domain 3 |
| ARPM1 | 1.648 | 1.648 | 1.689 | 3.557 | 4.174 | 3.557 | 3.754 | 0.0086423 | No description |
| FRG2 | 1.648 | 1.834 | 1.648 | 3.830 | 3.247 | 3.557 | 3.754 | 0.0130776 | FSHD region gene 2 |
| GNAL | 1.648 | 1.648 | 1.834 | 3.557 | 3.499 | 5.512 | 3.754 | 0.0159816 | guanine nucleotide binding protein (G protein), alpha activating activity polypeptide, olfactory type |
| OR52R1 | 1.648 | 1.648 | 2.304 | 4.376 | 3.499 | 3.557 | 3.754 | 0.0175816 | olfactory receptor, family 52, subfamily R, member 1 |
| SLC6A7 | 1.648 | 1.648 | 1.834 | 3.023 | 4.017 | 3.557 | 3.754 | 0.0183470 | solute carrier family 6 (neurotransmitter transporter, L-proline), member 7 |
| TMED10P | 1.648 | 1.648 | 1.648 | 3.830 | 2.739 | 3.557 | 3.754 | 0.0239581 | No description |
| BAIAP2 | 7.982 | 8.407 | 9.175 | 9.586 | 10.503 | 11.084 | 3.755 | 0.0307324 | BAH-associated protein 2 |
| C12orf48 | 2.648 | 2.970 | 3.897 | 4.883 | 5.244 | 4.579 | 3.764 | 0.0290915 | chromosome 12 open reading frame 48 |
| PRELID1 | 6.418 | 6.578 | 6.689 | 8.490 | 8.717 | 7.712 | 3.764 | 0.0225099 | PRELI domain containing 1 |
| MMP12 | 4.895 | 9.347 | 9.598 | 11.512 | 10.387 | 10.215 | 3.767 | 0.0464198 | matrix metallopeptidase 12 (macrophage elastase) |
| UBL4A | 7.580 | 4.117 | 6.196 | 8.964 | 8.110 | 7.882 | 3.769 | 0.0369341 | ubiquitin-like 4A |
| GUF1 | 4.793 | 4.985 | 3.666 | 6.708 | 6.720 | 5.927 | 3.772 | 0.0231102 | GUF1 GTPase homolog (S. cerevisiae) |
| PRDX3 | 8.909 | 7.208 | 7.900 | 11.046 | 9.816 | 9.021 | 3.773 | 0.0404052 | peroxiredoxin 3 |
| SMUG1 | 4.423 | 4.325 | 4.477 | 6.340 | 6.443 | 5.997 | 3.777 | 0.0111927 | single-strand-selective monofunctional uracil-DNA glycosylase 1 |
| CD300C | 2.233 | 2.233 | 3.029 | 4.151 | 3.467 | 5.147 | 3.777 | 0.0370153 | CD300c molecule |
| TNIK | 2.233 | 2.951 | 3.966 | 4.151 | 4.889 | 5.147 | 3.784 | 0.0452288 | TRAF2 and NCK interacting kinase |
| GTF2B | 7.019 | 7.027 | 8.056 | 8.998 | 8.939 | 9.267 | 3.784 | 0.0265057 | general transcription factor IIB |
| RAVER2 | 4.264 | 2.648 | 2.937 | 4.797 | 5.977 | 4.857 | 3.785 | 0.0322153 | ribonucleoprotein, PTB-binding 2 |
| NBEAL2 | 6.118 | 5.382 | 6.684 | 7.165 | 8.220 | 8.605 | 3.789 | 0.0285882 | neurobeachin-like 2 |
| FRG1 | 5.042 | 5.652 | 4.339 | 7.303 | 7.162 | 6.261 | 3.792 | 0.0261071 | FSHD region gene 1 |
| TTL | 6.610 | 5.212 | 6.470 | 8.464 | 8.393 | 8.263 | 3.795 | 0.0131685 | tubulin tyrosine ligase |
| PPIL5 | 3.422 | 4.008 | 3.814 | 5.908 | 5.932 | 4.493 | 3.795 | 0.0371040 | peptidylprolyl isomerase (cyclophilin)-like 5 |
| DPP9 | 8.259 | 7.071 | 8.201 | 10.587 | 10.044 | 8.995 | 3.796 | 0.0263920 | dipeptidyl-peptidase 9 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| SRRM3 | 1.648 | 2.450 | 4.008 | 4.376 | 4.174 | 5.459 | 3.800 | 0.0418887 | serine/arginine repetitive matrix 3 |
| CCDC149 | 3.233 | 3.983 | 4.391 | 5.315 | 5.359 | 6.322 | 3.813 | 0.0290672 | coiled-coil domain containing 149 |
| SEC16A | 7.844 | 7.377 | 8.606 | 9.779 | 10.096 | 9.406 | 3.824 | 0.0245619 | SEC16 homolog A (S. cerevisiae) |
| NHEDC2 | 7.020 | 5.031 | 5.625 | 7.958 | 7.560 | 7.533 | 3.824 | 0.0385640 | Na+/H+ exchanger domain containing 2 |
| RNASEH1 | 6.444 | 4.667 | 4.799 | 8.253 | 6.851 | 6.603 | 3.825 | 0.0419289 | ribonuclease H1 |
| C1orf163 | 2.233 | 4.263 | 4.677 | 6.199 | 6.428 | 5.793 | 3.828 | 0.0218215 | chromosome 1 open reading frame 163 |
| DIO3 | 3.422 | 1.648 | 2.234 | 4.017 | 4.174 | 5.289 | 3.838 | 0.0279934 | deiodinase, iodothyronine, type III |
| ALKBH6 | 4.817 | 3.956 | 3.569 | 6.161 | 6.205 | 5.509 | 3.840 | 0.0247158 | alkB, alkylation repair homolog 6 (E. coli) |
| CUL4A | 7.781 | 7.426 | 8.913 | 9.370 | 9.900 | 9.951 | 3.849 | 0.0354104 | cullin 4A |
| TRABD | 7.434 | 7.857 | 7.690 | 9.500 | 9.636 | 9.656 | 3.853 | 0.0091317 | TraB domain containing |
| MDH1 | 8.010 | 7.886 | 7.762 | 10.077 | 9.832 | 9.489 | 3.853 | 0.0114326 | malate dehydrogenase 1, NAD (soluble) |
| POMT2 | 6.198 | 6.193 | 6.556 | 8.543 | 8.148 | 7.438 | 3.863 | 0.0246672 | protein-O-mannosyltransferase 2 |
| PIGS | 7.666 | 6.186 | 6.437 | 9.247 | 8.388 | 8.275 | 3.867 | 0.0301009 | phosphatidylinositol glycan anchor biosynthesis, class S |
| IL17RA | 5.580 | 5.495 | 5.861 | 7.778 | 7.769 | 7.449 | 3.873 | 0.0083601 | interleukin 17 receptor A |
| NUDT22 | 4.142 | 4.473 | 3.718 | 7.165 | 6.096 | 4.669 | 3.874 | 0.0453563 | nudix (nucleoside diphosphate linked moiety X)-type motif 22 |
| AKT1 | 9.221 | 8.268 | 9.283 | 11.238 | 10.720 | 10.638 | 3.876 | 0.0185660 | v-akt murine thymoma viral oncogene homolog 1 |
| CCDC57 | 5.861 | 5.370 | 6.207 | 7.488 | 8.164 | 7.482 | 3.881 | 0.0177147 | coiled-coil domain containing 57 |
| FOXC2 | 4.525 | 4.253 | 5.786 | 7.433 | 7.662 | 6.211 | 3.883 | 0.0215213 | forkhead box C2 (MFH-1, mesenchyme forkhead 1) |
| TPRKB | 6.001 | 5.770 | 6.505 | 8.505 | 7.959 | 7.209 | 3.885 | 0.0265646 | TP53RK binding protein |
| INCENP | 4.264 | 3.251 | 3.475 | 5.266 | 5.896 | 5.434 | 3.886 | 0.0200891 | inner centromere protein antigens 135/155 kDa |
| TBP | 5.293 | 5.118 | 5.997 | 7.859 | 7.742 | 7.078 | 3.891 | 0.0140974 | TATA box binding protein |
| TRPV1 | 2.233 | 2.814 | 3.170 | 4.151 | 5.183 | 4.777 | 3.899 | 0.0190950 | transient receptor potential cation channel, subfamily V, member 1 |
| GTF2I | 0.648 | 1.078 | 2.401 | 2.714 | 3.633 | 3.043 | 3.906 | 0.0401931 | general transcription factor Hi |
| GOLGB1 | 7.032 | 7.120 | 7.600 | 9.566 | 8.527 | 9.556 | 3.907 | 0.0182159 | golgin B1 |
| YTHDC1 | 9.741 | 8.974 | 9.799 | 11.351 | 10.942 | 11.947 | 3.914 | 0.0204364 | YTH domain containing 1 |
| SFRS13B | 2.648 | 2.648 | 2.999 | 4.981 | 4.618 | 4.579 | 3.916 | 0.0102679 | No description |
| ATP6V0A1 | 7.355 | 6.503 | 8.334 | 9.326 | 8.549 | 9.571 | 3.921 | 0.0421244 | ATPase, H+ transporting, lysosomal V0 subunit a1 |
| ARPC3 | 2.233 | 2.917 | 3.078 | 5.773 | 4.889 | 3.737 | 3.923 | 0.0272773 | actin related protein 2/3 complex, subunit 3, 21 kDa |
| LOC284578 | 3.422 | 3.645 | 3.638 | 7.142 | 5.304 | 5.610 | 3.924 | 0.0138270 | No description |
| SLC29A1 | 9.394 | 7.542 | 8.666 | 10.639 | 10.978 | 10.140 | 3.928 | 0.0249750 | solute carrier family 29 (nucleoside transporters), member 1 |
| CEP57 | 6.314 | 5.009 | 5.478 | 7.452 | 7.121 | 7.657 | 3.928 | 0.0250021 | centrosomal protein 57 kDa |
| NCRNA00085 | 4.008 | 2.744 | 2.177 | 4.154 | 5.120 | 5.289 | 3.937 | 0.0361494 | non-protein coding RNA 85 |
| HSPBP1 | 7.039 | 6.537 | 6.451 | 10.072 | 8.374 | 8.514 | 3.937 | 0.0165466 | HSPA (heat shock 70 kDa) binding protein, cytoplasmic cochaperone 1 |
| TNKS2 | 6.595 | 6.655 | 6.694 | 7.562 | 8.744 | 8.632 | 3.937 | 0.0295629 | tankyrase, TRF1-interacting ankyrin-related ADP-ribose polymerase 2 |
| MCF2L | 5.751 | 4.639 | 4.616 | 7.724 | 6.683 | 6.594 | 3.938 | 0.0238423 | MCF.2 cell line derived transforming sequence-like |
| CCDC154 | 1.648 | 3.420 | 4.008 | 5.459 | 4.529 | 5.398 | 3.939 | 0.0321640 | coiled-coil domain containing 154 |
| NICN1 | 5.171 | 3.842 | 4.455 | 6.135 | 6.433 | 6.856 | 3.940 | 0.0199095 | nicolin 1 |
| POU3F1 | 4.482 | 3.716 | 4.463 | 5.695 | 7.991 | 7.991 | 3.943 | 0.0195047 | POU class 3 homeobox 1 |
| ARHGAP11A | 2.648 | 3.579 | 3.090 | 5.558 | 4.915 | 4.755 | 3.943 | 0.0170049 | Rho GTPase activating protein 11A |
| RBAK | 3.233 | 4.348 | 4.652 | 5.799 | 5.213 | 6.763 | 3.943 | 0.0364503 | RB-associated KRAB zinc finger |
| MBOAT2 | 6.333 | 5.615 | 5.343 | 7.595 | 7.659 | 7.500 | 3.943 | 0.0186250 | membrane bound O-acyltransferase domain containing 2 |
| CDK16 | 9.995 | 8.357 | 9.617 | 11.598 | 11.697 | 11.495 | 3.949 | 0.0149369 | cyclin-dependent kinase 16 |
| LOC284232 | 7.790 | 7.097 | 7.385 | 9.292 | 9.366 | 9.757 | 3.949 | 0.0109584 | No description |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| FLU | 7.734 | 8.450 | 5.995 | 9.861 | 9.716 | 8.475 | 3.950 | 0.0462555 | flightless I homolog (*Drosophila*) |
| HAUS5 | 6.264 | 4.557 | 5.579 | 7.449 | 7.613 | 7.561 | 3.950 | 0.0199317 | HAUS augmin-like complex, subunit 5 |
| MOCS3 | 4.142 | 3.549 | 3.834 | 5.845 | 5.513 | 6.124 | 3.952 | 0.0121924 | molybdenum cofactor synthesis 3 |
| MBD4 | 8.343 | 7.706 | 8.086 | 10.075 | 10.031 | 10.069 | 3.952 | 0.0095553 | methyl-CpG binding domain protein 4 |
| C15orf17 | 7.166 | 6.541 | 6.604 | 8.523 | 9.123 | 8.851 | 3.953 | 0.0111657 | chromosome 15 open reading frame 17 |
| DAZAP2 | 10.824 | 10.127 | 10.325 | 13.205 | 12.225 | 12.111 | 3.958 | 0.0156315 | DAZ associated protein 2 |
| H2AFZ | 10.786 | 10.269 | 11.701 | 12.252 | 13.079 | 13.686 | 3.958 | 0.0239920 | H2A histone family, member Z |
| RAB4B | 3.422 | 2.926 | 2.721 | 5.409 | 5.304 | 4.376 | 3.966 | 0.0170589 | RAB4B, member RAS oncogene family |
| POLN | 0.648 | 0.648 | 0.999 | 2.714 | 2.987 | 2.370 | 3.966 | 0.0122839 | polymerase (DNA directed) nu |
| RNMTL1 | 5.600 | 5.937 | 5.018 | 7.925 | 7.492 | 7.462 | 3.969 | 0.0117633 | RNA methyltransferase like 1 |
| LRRC56 | 4.793 | 3.314 | 3.476 | 5.305 | 5.308 | 6.870 | 3.974 | 0.0350236 | leucine rich repeat containing 56 |
| ABCC13 | 4.817 | 4.153 | 4.083 | 6.168 | 6.074 | 6.234 | 3.976 | 0.0161931 | ATP-binding cassette, sub-family C (CFTR/MRP), member 13, pseudogene |
| HSPBAP1 | 2.233 | 4.309 | 5.738 | 6.474 | 6.301 | 5.973 | 3.977 | 0.0460073 | HSPB (heat shock 27 kDa) associated protein 1 |
| TM2D2 | 5.849 | 5.224 | 5.898 | 8.110 | 7.670 | 7.216 | 3.979 | 0.0151504 | TM2 domain containing 2 |
| ZNF876P | 0.648 | 0.648 | 2.268 | 4.262 | 2.987 | 2.370 | 3.984 | 0.0370243 | zinc finger protein 876, pseudogene |
| ERCC8 | 2.233 | 2.233 | 2.524 | 3.981 | 4.624 | 4.230 | 3.991 | 0.0116620 | excision repair cross-complementing rodent repair deficiency, complementation group 8 |
| ZNF414 | 2.233 | 3.956 | 3.508 | 6.336 | 5.017 | 4.230 | 3.991 | 0.0424724 | zinc finger protein 414 |
| MPHOSPH10 | 6.689 | 6.948 | 7.410 | 9.326 | 9.357 | 8.686 | 3.993 | 0.0116530 | M-phase phosphoprotein 10 (U3 small nucleolar ribonucleoprotein) |
| NXPH4 | 3.194 | 1.649 | 3.043 | 4.262 | 5.196 | 3.966 | 4.005 | 0.0359920 | neurexophilin 4 |
| KIAA2018 | 7.596 | 6.373 | 5.048 | 8.755 | 8.071 | 8.377 | 4.010 | 0.0338541 | KIAA2018 |
| MAD2L1BP | 5.690 | 4.094 | 5.822 | 8.067 | 6.099 | 7.403 | 4.012 | 0.0407380 | MAD2L1 binding protein |
| RAB11FIP5 | 5.378 | 5.139 | 5.219 | 7.225 | 6.676 | 7.485 | 4.016 | 0.0147523 | RAB11 family interacting protein 5 (class 1) |
| KDM6B | 11.701 | 11.274 | 12.262 | 12.943 | 13.707 | 14.828 | 4.017 | 0.0251997 | lysine (K)-specific demethylase 6B |
| UBE4B | 8.578 | 7.394 | 8.328 | 10.155 | 10.585 | 10.310 | 4.020 | 0.0114735 | ubiquitination factor E4B (UFD2 homolog, yeast) |
| AP2S1 | 9.645 | 7.544 | 8.317 | 11.652 | 10.446 | 9.420 | 4.021 | 0.0459893 | adaptor-related protein complex 2, sigma 1 subunit |
| PLLP | 0.648 | 1.387 | 3.046 | 4.262 | 5.053 | 2.370 | 4.021 | 0.0457016 | plasmolipin |
| TIPIN | 4.008 | 2.625 | 3.296 | 5.420 | 5.304 | 5.082 | 4.022 | 0.0195137 | TIMELESS interacting protein |
| CCDC146 | 2.648 | 3.104 | 4.009 | 5.435 | 4.857 | 5.112 | 4.022 | 0.0236773 | coiled-coil domain containing 146 |
| DCTN2 | 9.466 | 8.661 | 9.027 | 11.476 | 11.099 | 10.317 | 4.028 | 0.0212690 | dynactin 2 (p50) |
| FIBP | 6.985 | 5.596 | 7.327 | 9.337 | 8.899 | 8.672 | 4.029 | 0.0157605 | fibroblast growth factor (acidic) intracellular binding protein |
| ZC3H12B | 2.648 | 2.970 | 3.013 | 4.981 | 4.273 | 5.945 | 4.031 | 0.0166825 | zinc finger CCCH-type containing 12B |
| HSF4 | 4.142 | 2.702 | 4.165 | 4.713 | 5.858 | 7.213 | 4.035 | 0.0309071 | heat shock transcription factor 4 |
| PPEF2 | 0.648 | 3.351 | 1.649 | 3.662 | 3.633 | 4.389 | 4.042 | 0.0409113 | protein phosphatase, EF-hand calcium binding domain 2 |
| RASA4P | 7.133 | 5.349 | 6.308 | 8.065 | 7.613 | 9.148 | 4.043 | 0.0317043 | No description |
| ATP6V0C | 11.392 | 11.124 | 12.116 | 13.139 | 13.542 | 13.505 | 4.043 | 0.0188302 | ATPase, H+ transporting, lysosomal 16 kDa, V0 subunit c |
| APOL1 | 2.233 | 2.391 | 2.261 | 4.276 | 4.151 | 4.590 | 4.053 | 0.0075269 | apolipoprotein L, 1 |
| NCRNA00169 | 1.648 | 2.450 | 3.140 | 4.400 | 4.469 | 5.122 | 4.055 | 0.0150922 | non-protein coding RNA 169 |
| ZNF814 | 3.456 | 3.607 | 4.072 | 5.627 | 6.183 | 5.074 | 4.055 | 0.0189529 | zinc finger protein 814 |
| ZNF496 | 5.993 | 4.661 | 5.278 | 7.299 | 7.168 | 7.506 | 4.057 | 0.0172780 | zinc finger protein 496 |
| SLMAP | 4.672 | 5.517 | 6.512 | 7.648 | 7.538 | 7.154 | 4.058 | 0.0298957 | sarcolemma associated protein |
| RC3H2 | 4.793 | 6.098 | 6.583 | 8.120 | 7.755 | 8.308 | 4.061 | 0.0178256 | ring finger and CCCH-type domains 2 |
| PDLIM4 | 10.265 | 9.871 | 10.827 | 11.986 | 13.230 | 11.894 | 4.064 | 0.0214555 | PDZ and LIM domain 4 |
| ZNF70 | 1.648 | 3.247 | 2.601 | 4.624 | 5.060 | 4.376 | 4.065 | 0.0169861 | zinc finger protein 70 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| BCKDK | 8.242 | 7.557 | 8.335 | 10.857 | 10.056 | 9.581 | 4.069 | 0.0163893 | branched chain ketoacid dehydrogenase kinase |
| ZXDC | 7.569 | 6.806 | 7.344 | 9.595 | 8.936 | 8.923 | 4.073 | 0.0166596 | ZXD family zinc finger C |
| EIF2B5 | 6.735 | 6.855 | 8.332 | 9.285 | 9.767 | 8.763 | 4.078 | 0.0283338 | eukaryotic translation initiation factor 2B, subunit 5 epsilon, 82 kDa |
| PPARD | 8.702 | 6.253 | 8.222 | 9.963 | 10.730 | 10.219 | 4.079 | 0.0176905 | peroxisome proliferator-activated receptor delta |
| CEP250 | 5.431 | 3.861 | 4.079 | 7.160 | 5.889 | 6.724 | 4.080 | 0.0236288 | centrosomal protein 250 kDa |
| EDNRB | 11.826 | 11.306 | 11.616 | 14.958 | 13.335 | 13.629 | 4.082 | 0.0133147 | endothelin receptor type B |
| DENND1A | 7.605 | 5.415 | 6.636 | 9.635 | 8.411 | 8.180 | 4.086 | 0.0289667 | DENN/MADD domain containing 1A |
| PPP2R5B | 7.555 | 6.194 | 6.454 | 9.066 | 8.883 | 8.226 | 4.090 | 0.0224343 | protein phosphatase 2, regulatory subunit B', beta |
| MAP4K4 | 8.636 | 9.286 | 9.673 | 11.296 | 11.196 | 11.705 | 4.090 | 0.0111116 | mitogen-activated protein kinase kinase kinase kinase 4 |
| SLC25A22 | 4.378 | 3.500 | 4.115 | 6.101 | 6.410 | 5.889 | 4.090 | 0.0110284 | solute carrier family 25 (mitochondrial carrier; glutamate), member 22 |
| ABHD3 | 2.233 | 4.928 | 3.529 | 4.871 | 5.561 | 6.655 | 4.091 | 0.0412101 | abhydrolase domain containing 3 |
| DGKA | 6.340 | 3.544 | 5.648 | 7.529 | 7.681 | 8.063 | 4.092 | 0.0202936 | diacylglycerol kinase, alpha 80 kDa |
| ZNF563 | 4.008 | 2.121 | 2.177 | 4.154 | 4.421 | 5.398 | 4.092 | 0.0414686 | zinc finger protein 563 |
| CHMP4A | 6.262 | 4.858 | 6.008 | 8.295 | 7.505 | 7.566 | 4.093 | 0.0198769 | chromatin modifying protein 4A |
| ABCD1 | 5.899 | 5.391 | 5.855 | 7.534 | 7.425 | 8.257 | 4.094 | 0.0136898 | ATP-binding cassette, sub-family D (ALD), member 1 |
| PARG | 4.524 | 4.744 | 4.192 | 6.560 | 5.643 | 6.780 | 4.101 | 0.0225286 | poly (ADP-ribose) glycohydrolase |
| AP4S1 | 7.503 | 7.841 | 7.510 | 8.986 | 9.546 | 10.537 | 4.102 | 0.0186159 | adaptor-related protein complex4, sigma 1 subunit |
| C4orf42 | 3.947 | 3.621 | 4.761 | 5.966 | 5.985 | 6.188 | 4.107 | 0.0172627 | chromosome 4 open reading frame 42 |
| ALG12 | 5.936 | 5.181 | 5.658 | 8.266 | 7.696 | 6.640 | 4.109 | 0.0255893 | asparagine-linked glycosylation 12, alpha-1,6-mannosyltransferase homolog (S. cerevisiae) |
| UBE3C | 8.173 | 7.536 | 8.052 | 10.092 | 10.405 | 9.272 | 4.112 | 0.0172939 | ubiquitin protein ligase E3C |
| SRGAP2 | 6.994 | 6.284 | 7.097 | 9.034 | 8.239 | 9.778 | 4.114 | 0.0163158 | SLIT-ROBO Rho GTPase activating protein 2 |
| CCDC24 | 4.008 | 2.304 | 2.776 | 5.459 | 6.049 | 4.104 | 4.115 | 0.0290825 | coiled-coil domain containing 24 |
| SNHG10 | 2.233 | 4.336 | 4.206 | 5.968 | 5.017 | 6.378 | 4.119 | 0.0293813 | small nucleolar RNA host gene 10 (non-protein coding) |
| FOXP3 | 2.233 | 2.233 | 2.233 | 4.276 | 4.697 | 4.230 | 4.120 | 0.0060205 | forkhead box P3 |
| GPC2 | 2.233 | 2.233 | 2.233 | 4.276 | 4.413 | 4.071 | 4.120 | 0.0067574 | glypican 2 |
| DGCR11 | 1.648 | 2.450 | 3.077 | 4.830 | 3.805 | 4.493 | 4.122 | 0.0238513 | DiGeorge syndrome critical region gene 11 |
| BNIP2 | 6.224 | 6.031 | 6.154 | 8.267 | 8.256 | 7.923 | 4.122 | 0.0076350 | BCL2/adenovirus E1B 19 kDa interacting protein 2 |
| PDPK1 | 6.813 | 6.039 | 5.861 | 8.178 | 7.905 | 8.437 | 4.122 | 0.0165376 | 3-phosphoinositide dependent protein kinase-1 |
| SLC7A5P2 | 2.648 | 4.520 | 4.953 | 6.404 | 6.329 | 6.998 | 4.127 | 0.0171525 | solute carrier family 7 (cationic amino acid transporter, y+ system), member 5 pseudogene 2 |
| TNRC18 | 8.849 | 6.191 | 7.251 | 10.000 | 8.815 | 9.296 | 4.127 | 0.0472641 | trinucleotide repeat containing 18 |
| CCDC71 | 6.001 | 4.767 | 5.748 | 8.029 | 7.796 | 7.196 | 4.136 | 0.0154950 | coiled-coil domain containing 71 |
| KPNA5 | 2.648 | 3.567 | 3.894 | 4.981 | 5.414 | 5.945 | 4.142 | 0.0183990 | karyopherin alpha 5 (importin alpha 6) |
| TRMT61B | 4.142 | 4.142 | 2.628 | 5.905 | 6.192 | 5.738 | 4.142 | 0.0149972 | tRNA methyltransferase 61 homolog B (S. cerevisiae) |
| EPS8L1 | 4.142 | 2.951 | 2.814 | 5.003 | 7.330 | 4.230 | 4.145 | 0.0420884 | EPS8-like 1 |
| CENPM | 1.648 | 2.675 | 2.894 | 3.830 | 4.945 | 3.929 | 4.145 | 0.0305903 | centromere protein M |
| FGFR3 | 5.322 | 4.381 | 5.248 | 5.845 | 7.300 | 8.893 | 4.146 | 0.0298076 | fibroblast growth factor receptor 3 |
| ZNF397OS | 4.264 | 3.747 | 4.788 | 6.317 | 6.211 | 6.838 | 4.147 | 0.0118929 | No description |
| C14orf105 | 1.648 | 1.834 | 1.648 | 3.888 | 3.704 | 2.752 | 4.151 | 0.0249147 | chromosome 14 open reading frame 105 |
| SDF4 | 10.338 | 8.703 | 9.394 | 11.862 | 11.449 | 10.800 | 4.153 | 0.0302035 | stromal cell derived factor 4 |
| RPL23AP82 | 1.648 | 1.648 | 1.648 | 3.557 | 3.704 | 3.929 | 4.158 | 0.0060863 | ribosomal protein L23a pseudogene 82 |
| ELP2P | 1.648 | 1.648 | 2.064 | 2.625 | 3.704 | 4.607 | 4.158 | 0.0334853 | No description |
| MVK | 4.936 | 4.624 | 5.907 | 7.711 | 7.215 | 6.681 | 4.160 | 0.0203380 | mevalonate kinase |

TABLE 4-continued

Differentially Expressed Genes in CD44+ Breast Epithelial Cells

| | Nulliparous (NP) Samples | | | Parous (P) Samples | | | Pseudo fold change | P value | Gene description |
|---|---|---|---|---|---|---|---|---|---|
| Gene Symbol | CD44+ N48 | CD44+ N58 | CD44+ N43 | CD44+ N37 | CD44+ N39 | CD44+ N40 | | | |
| CABLES1 | 5.204 | 3.797 | 3.902 | 6.164 | 5.855 | 6.554 | 4.165 | 0.0261841 | Cdk5 and Abl enzyme substrate 1 |
| MGC3771 | 1.648 | 1.648 | 1.648 | 3.707 | 3.353 | 3.942 | 4.166 | 0.0088510 | No description |
| RNF125 | 5.107 | 4.214 | 3.808 | 6.273 | 5.984 | 6.367 | 4.167 | 0.0238333 | ring finger protein 125 |
| KTELC1 | 6.677 | 5.416 | 5.666 | 8.373 | 7.894 | 7.476 | 4.169 | 0.0210451 | No description |
| HEATR2 | 4.793 | 3.661 | 3.233 | 5.293 | 5.768 | 5.768 | 4.170 | 0.0350326 | HEAT repeat containing 2 |
| GPT2 | 5.377 | 3.884 | 4.178 | 6.240 | 8.365 | 5.608 | 4.173 | 0.0355712 | glutamic pyruvate transaminase (alanine aminotransferase) 2 |
| WHSC1 | 6.167 | 6.513 | 5.893 | 8.229 | 8.397 | 8.167 | 4.173 | 0.0086603 | Wolf-Hirschhorn syndrome candidate 1 |
| OFD1 | 6.510 | 6.659 | 6.864 | 8.090 | 8.927 | 8.848 | 4.178 | 0.0147192 | oral-facial-digital syndrome 1 |
| FCHSD1 | 3.456 | 4.151 | 4.547 | 6.151 | 5.593 | 6.610 | 4.178 | 0.0173369 | FCH and double SH3 domains 1 |
| TTLL4 | 5.482 | 6.844 | 7.584 | 8.907 | 9.456 | 8.801 | 4.178 | 0.0167158 | tubulin tyrosine ligase-like family, member 4 |
| RHCG | 2.970 | 4.686 | 3.859 | 6.437 | 5.034 | 6.188 | 4.181 | 0.0285029 | Rh family, C glycoprotein |
| TIMM17A | 9.253 | 8.712 | 9.246 | 11.310 | 11.478 | 10.705 | 4.182 | 0.0116080 | translocase of inner mitochondrial membrane 17 homolog A (yeast) |
| CNPY3 | 8.151 | 6.105 | 8.124 | 10.215 | 9.877 | 9.134 | 4.182 | 0.0244724 | canopy 3 homolog (zebrafish) |
| C8orf33 | 7.167 | 7.627 | 7.817 | 9.882 | 9.621 | 9.678 | 4.185 | 0.0074014 | chromosome 8 open reading frame 33 |
| MAGEA1 | 0.648 | 0.648 | 0.648 | 2.714 | 2.987 | 2.370 | 4.187 | 0.0087400 | melanoma antigen family A, 1 (directs expression of antigen MZ2-E) |
| FKSG83 | 0.648 | 0.648 | 0.648 | 2.714 | 2.353 | 3.773 | 4.187 | 0.0120669 | No description |
| ASF1B | 0.648 | 0.648 | 0.999 | 2.714 | 4.428 | 2.370 | 4.187 | 0.0169542 | ASF1 anti-silencing function 1 homolog B (S. cerevisiae) |
| FAM159A | 0.648 | 0.648 | 0.999 | 2.714 | 2.353 | 5.407 | 4.187 | 0.0209182 | family with sequence similarity 159, member A |
| ZMYND10 | 0.648 | 0.648 | 1.719 | 2.714 | 2.353 | 4.262 | 4.187 | 0.0276579 | zinc finger, MYND-type containing 10 |
| HSD17B10 | 8.285 | 7.070 | 7.997 | 10.351 | 10.247 | 8.995 | 4.187 | 0.0232849 | hydroxysteroid (17-beta) dehydrogenase 10 |
| CRX | 4.142 | 4.720 | 5.616 | 6.787 | 6.851 | 6.290 | 4.189 | 0.0275906 | cone-rod homeobox |
| C4orf14 | 7.661 | 4.975 | 6.259 | 8.292 | 8.941 | 8.330 | 4.202 | 0.0290028 | chromosome 4 open reading frame 14 |
| ZNF493 | 7.705 | 7.353 | 7.667 | 9.654 | 9.426 | 10.053 | 4.207 | 0.0082305 | zinc finger protein 493 |
| SEC31B | 4.948 | 4.265 | 4.678 | 6.751 | 6.591 | 7.001 | 4.207 | 0.0085508 | SEC31 homolog B (S. cerevisiae) |
| UPF3B | 6.070 | 5.010 | 5.777 | 7.850 | 8.032 | 7.836 | 4.208 | 0.0090756 | UPF3 regulator of nonsense transcripts homolog B (yeast) |
| EHMT2 | 7.498 | 4.420 | 5.933 | 8.998 | 7.833 | 8.006 | 4.209 | 0.0325737 | euchromatic histone-lysine N-methyltransferase 2 |
| PQLC1 | 9.647 | 8.598 | 9.636 | 10.672 | 11.309 | 12.088 | 4.211 | 0.0223068 | PQ loop repeat containing 1 |
| POLR2A | 10.569 | 9.289 | 8.914 | 11.618 | 11.056 | 11.363 | 4.212 | 0.0350991 | polymerase (RNA) II (DNA directed) polypeptide A, 220 kDa |
| CSTF3 | 4.525 | 3.899 | 3.571 | 5.647 | 6.119 | 6.570 | 4.216 | 0.0145237 | cleavage stimulation factor, 3' pre-RNA, subunit 3, 77 kDa |
| TMC8 | 4.194 | 2.121 | 3.435 | 3.909 | 5.511 | 7.191 | 4.217 | 0.0447331 | transmembrane channel-like 8 |
| GSS | 6.859 | 4.667 | 6.268 | 8.740 | 8.345 | 7.630 | 4.217 | 0.0231858 | glutathione synthetase |
| SV2A | 5.941 | 5.451 | 4.662 | 9.010 | 7.528 | 6.344 | 4.220 | 0.0295220 | synaptic vesicle glycoprotein 2A |
| PDDC1 | 4.233 | 5.060 | 5.102 | 6.674 | 6.807 | 7.180 | 4.223 | 0.0126173 | Parkinson disease 7 domain containing 1 |
| POLL | 6.227 | 3.104 | 4.850 | 7.195 | 6.852 | 6.929 | 4.224 | 0.0327019 | polymerase (DNA directed), lambda |
| C8orf46 | 4.734 | 3.294 | 2.206 | 5.381 | 5.380 | 5.220 | 4.246 | 0.0403858 | chromosome 8 open reading frame 46 |
| KIAA0368 | 8.292 | 8.703 | 9.555 | 10.527 | 10.789 | 11.206 | 4.247 | 0.0189778 | KIAA0368 |
| HPX | 1.648 | 2.744 | 3.880 | 4.830 | 4.174 | 5.220 | 4.248 | 0.0349092 | hemopexin |
| SLC27A5 | 5.452 | 2.926 | 5.384 | 6.847 | 7.539 | 6.261 | 4.248 | 0.0313958 | solute carrier family 27 (fatty acid transporter), member 5 |
| RANBP9 | 8.963 | 7.159 | 7.707 | 9.923 | 9.246 | 10.302 | 4.251 | 0.0341050 | RAN binding protein 9 |
| KRT80 | 4.672 | 5.700 | 6.593 | 6.761 | 8.885 | 7.456 | 4.254 | 0.0394839 | keratin 80 |
| WDR90 | 3.233 | 4.236 | 3.929 | 6.326 | 5.883 | 5.651 | 4.257 | 0.0124939 | WD repeat domain 90 |
| ZBTB39 | 3.648 | 4.300 | 4.484 | 6.625 | 5.977 | 5.739 | 4.258 | 0.0171913 | zinc finger and BTB domain containing 39 |
| COG1 | 6.444 | 4.784 | 5.551 | 8.388 | 7.647 | 7.618 | 4.274 | 0.0159158 | component of oligomeric golgi complex 1 |
| HLA-B | 13.748 | 12.382 | 12.842 | 15.517 | 14.790 | 14.938 | 4.277 | 0.0176683 | major histocompatibility complex, class I, B |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| SCNN1D | 5.008 | 3.218 | 4.104 | 5.314 | 6.612 | 7.019 | 4.278 | 0.0259345 | sodium channel, nonvoltage-gated 1, delta |
| CRTC2 | 5.619 | 6.693 | 7.222 | 8.790 | 8.528 | 9.291 | 4.278 | 0.0140094 | CREB regulated transcription coactivator 2 |
| MCM2 | 5.524 | 3.557 | 5.060 | 7.621 | 6.934 | 6.333 | 4.279 | 0.0237348 | minichromosome maintenance complex component 2 |
| ITK | 3.860 | 3.046 | 1.564 | 3.662 | 4.870 | 7.329 | 4.281 | 0.0439359 | IL2-inducible T-cell kinase |
| TCIRG1 | 8.038 | 6.967 | 7.892 | 10.141 | 9.254 | 9.545 | 4.296 | 0.0184530 | T-cell, immune regulator 1, ATPase, H+ transporting, lysosomal VO subunit A3 |
| ORC2L | 3.233 | 3.486 | 4.111 | 5.791 | 5.425 | 5.593 | 4.306 | 0.0134139 | No description |
| SMG6 | 8.387 | 5.654 | 7.342 | 9.452 | 9.410 | 9.808 | 4.316 | 0.0227102 | Smg-6 homolog, nonsense mediated mRNA decay factor (C. elegans) |
| UBE2J1 | 9.057 | 8.400 | 8.348 | 11.387 | 10.511 | 10.397 | 4.319 | 0.0134846 | ubiquitin-conjugating enzyme E2, J1 (UBC6 homolog, yeast) |
| ATP5J2 | 5.396 | 4.924 | 4.709 | 7.035 | 7.559 | 6.290 | 4.319 | 0.0202229 | ATP synthase, H+ transporting, mitochondrial Fo complex, subunit F2 |
| PNLDC1 | 4.314 | 2.941 | 3.284 | 5.739 | 5.053 | 5.889 | 4.325 | 0.0201868 | poly(A)-specific ribonuclease (PARN)-like domain containing 1 |
| VPS25 | 7.268 | 6.662 | 6.941 | 10.201 | 9.055 | 8.212 | 4.327 | 0.0208461 | vacuolar protein sorting 25 homolog (S. cerevisiae) |
| C15orf57 | 5.552 | 4.919 | 4.988 | 7.298 | 7.667 | 7.014 | 4.331 | 0.0095913 | chromosome 15 open reading frame 57 |
| MKLN1 | 7.895 | 7.414 | 8.140 | 9.529 | 9.935 | 10.438 | 4.331 | 0.0120343 | muskelin 1, intracellular mediator containing kelch motifs |
| CECR7 | 2.233 | 3.170 | 3.726 | 4.713 | 4.624 | 5.842 | 4.336 | 0.0258596 | cat eye syndrome chromosome region, candidate 7 (non-protein coding) |
| RAPGEFL1 | 5.600 | 3.802 | 4.715 | 7.659 | 6.949 | 5.919 | 4.338 | 0.0283678 | Rap guanine nucleotide exchange factor (GEF)-like 1 |
| MECR | 4.709 | 4.977 | 5.498 | 7.389 | 7.281 | 6.828 | 4.344 | 0.0112177 | mitochondrial trans-2-enoyl-CoA reductase |
| LOC728606 | 2.648 | 4.379 | 4.301 | 5.800 | 6.071 | 6.499 | 4.345 | 0.0166277 | No description |
| CYP2B6 | 2.648 | 2.904 | 3.015 | 5.024 | 4.896 | 5.026 | 4.346 | 0.0057036 | cytochrome P450, family 2. subfamily B. polypeptide 6 |
| ZNF394 | 2.233 | 2.360 | 2.499 | 4.481 | 4.624 | 4.071 | 4.350 | 0.0091650 | zinc finger protein 394 |
| SHROOM2 | 2.233 | 2.360 | 2.903 | 4.481 | 5.126 | 4.071 | 4.350 | 0.0151324 | shroom family member 2 |
| PDE4D | 5.926 | 6.705 | 6.239 | 8.594 | 7.887 | 8.826 | 4.350 | 0.0128953 | phosphodiesterase 4D, cAMP-specific |
| UNC45A | 8.030 | 6.836 | 7.577 | 10.153 | 9.200 | 9.238 | 4.358 | 0.0192156 | unc-45 homolog A (C. elegans) |
| ZC3H6 | 7.434 | 7.466 | 8.566 | 9.669 | 9.846 | 9.560 | 4.364 | 0.0211920 | zinc finger CCCH-type containing 6 |
| PIGL | 5.452 | 3.832 | 4.734 | 6.860 | 6.554 | 6.866 | 4.364 | 0.0189619 | phosphatidylinositol glycan anchor biosynthesis, class L |
| SH2B2 | 5.809 | 3.861 | 5.538 | 6.872 | 7.471 | 7.936 | 4.368 | 0.0194728 | SH2B adaptor protein 2 |
| BMS1P1 | 0.648 | 2.401 | 3.336 | 4.529 | 4.043 | 5.230 | 4.371 | 0.0236017 | BMS1 pseudogene 1 |
| PPP2R3B | 4.657 | 2.768 | 4.667 | 5.892 | 6.262 | 6.796 | 4.375 | 0.0217161 | protein phosphatase 2, regulatory subunit B", beta |
| KRTCAP3 | 3.422 | 3.209 | 1.978 | 4.109 | 5.730 | 4.493 | 4.381 | 0.0358672 | keratinocyte associated protein 3 |
| TPRG1L | 8.413 | 7.366 | 8.117 | 10.548 | 9.810 | 9.702 | 4.391 | 0.0166367 | tumor protein p63 regulated 1-like |
| SART1 | 8.073 | 7.520 | 8.416 | 10.211 | 10.449 | 9.758 | 4.400 | 0.0120759 | squamous cell carcinoma antigen recognized by T cells |
| VHL | 7.937 | 7.208 | 8.090 | 10.228 | 9.758 | 9.925 | 4.400 | 0.0096274 | von Hippel-Lindau tumor suppressor |
| REV1 | 6.317 | 6.239 | 6.230 | 7.702 | 8.490 | 8.427 | 4.404 | 0.0138541 | REV1 homolog (S. cerevisiae) |
| WDR5 | 3.947 | 5.174 | 4.755 | 7.083 | 7.313 | 6.011 | 4.405 | 0.0186589 | WD repeat domain 5 |
| LOC283731 | 3.194 | 0.648 | 2.170 | 3.351 | 4.311 | 5.230 | 4.412 | 0.0319047 | No description |
| STK39 | 7.181 | 3.702 | 6.072 | 8.215 | 9.060 | 8.022 | 4.415 | 0.0233376 | serine threonine kinase 39 |
| C14orf182 | 3.619 | 2.233 | 2.233 | 4.378 | 5.561 | 4.669 | 4.423 | 0.0206964 | chromosome 14 open reading frame 182 |
| ALG3 | 7.922 | 6.975 | 7.220 | 10.068 | 9.895 | 8.802 | 4.427 | 0.0157286 | asparagine-linked glycosylation 3, alpha-1,3-mannosyltransferase homolog (S. cerevisiae) |
| ARF1 | 12.826 | 12.100 | 12.895 | 15.110 | 14.522 | 14.247 | 4.429 | 0.0155795 | ADP-ribosylation factor 1 |
| KLB | 2.233 | 2.870 | 3.687 | 3.737 | 5.017 | 6.511 | 4.430 | 0.0376433 | klotho beta |
| C2orf60 | 5.142 | 4.009 | 3.940 | 6.749 | 6.089 | 6.335 | 4.434 | 0.0185071 | chromosome 2 open reading frame 60 |

TABLE 4-continued

Differentially Expressed Genes in CD44+ Breast Epithelial Cells

| Gene Symbol | Nulliparous (NP) Samples | | | Parous (P) Samples | | | Pseudo | | Gene description |
|---|---|---|---|---|---|---|---|---|---|
| | CD44+ N48 | CD44+ N58 | CD44+ N43 | CD44+ N37 | CD44+ N39 | CD44+ N40 | fold change | P value | |
| NCS1 | 9.287 | 8.828 | 9.232 | 11.077 | 11.436 | 11.160 | 4.436 | 0.0077792 | neuronal calcium sensor 1 |
| PNPLA2 | 9.021 | 7.968 | 8.369 | 10.241 | 10.902 | 10.522 | 4.447 | 0.0138964 | patatin-like phospholipase domain containing 2 |
| NCBP1 | 4.904 | 3.776 | 4.032 | 5.587 | 7.059 | 6.446 | 4.454 | 0.0205016 | nuclear cap binding protein subunit 1,80 kDa |
| REC8 | 4.817 | 5.252 | 5.593 | 6.187 | 7.407 | 8.409 | 4.454 | 0.0269633 | REC8 homolog (yeast) |
| PEBP4 | 4.314 | 0.648 | 3.195 | 4.972 | 5.351 | 5.606 | 4.457 | 0.0294298 | phosphatidylethanolamine-binding protein 4 |
| LOC440335 | 4.423 | 5.078 | 6.672 | 6.994 | 9.779 | 6.579 | 4.458 | 0.0438028 | No description |
| TBC1D10C | 1.648 | 2.450 | 2.450 | 3.830 | 3.805 | 5.926 | 4.458 | 0.0231192 | TBC1 domain family, member 10C |
| APOO | 1.648 | 3.420 | 1.648 | 4.721 | 3.805 | 4.104 | 4.458 | 0.0313369 | apolipoprotein O |
| EXD2 | 6.487 | 4.151 | 4.109 | 7.469 | 7.010 | 6.265 | 4.459 | 0.0442187 | exonuclease 3′-5′ domain containing 2 |
| IL23A | 3.194 | 4.435 | 5.459 | 6.666 | 5.351 | 6.722 | 4.461 | 0.0471477 | interleukin 23, alpha subunit p19 |
| SCN11A | 5.322 | 3.859 | 4.273 | 6.715 | 6.489 | 6.017 | 4.465 | 0.0243504 | sodium channel, voltage-gated, type XI, alpha subunit |
| KIF21B | 5.548 | 3.233 | 3.479 | 5.394 | 6.839 | 7.233 | 4.472 | 0.0280461 | kinesin family member 21B |
| VILL | 5.322 | 3.956 | 4.276 | 6.688 | 6.119 | 7.226 | 4.476 | 0.0184440 | villin-like |
| LRRC57 | 4.793 | 3.409 | 3.773 | 5.939 | 5.682 | 6.350 | 4.489 | 0.0204925 | leucine rich repeat containing 57 |
| SCAND2 | 5.431 | 5.626 | 6.260 | 7.723 | 7.996 | 7.797 | 4.504 | 0.0111206 | SCAN domain containing 2 pseudogene |
| SID1 | 7.170 | 6.106 | 6.466 | 8.638 | 8.404 | 9.265 | 4.507 | 0.0135636 | SID1 transmembrane family, member 2 |
| SAPS1 | 8.366 | 7.626 | 9.359 | 10.540 | 10.618 | 10.386 | 4.510 | 0.0207054 | No description |
| DUS1L | 7.162 | 6.422 | 7.900 | 9.557 | 9.881 | 8.595 | 4.510 | 0.0200045 | dihydrouridine synthase 1-like (S. cerevisiae) |
| HIRA | 6.150 | 5.658 | 5.685 | 7.596 | 8.354 | 7.859 | 4.513 | 0.0107955 | HIR histone cell cycle regulation defective homolog A (S. cerevisiae) |
| C6orf1 | 5.849 | 5.237 | 5.586 | 8.026 | 7.784 | 6.919 | 4.523 | 0.0163477 | chromosome 6 open reading frame 1 |
| ALPP | 8.402 | 7.559 | 8.360 | 9.752 | 10.259 | 10.581 | 4.531 | 0.0142478 | alkaline phosphatase, placental |
| PRPSAP1 | 6.476 | 4.984 | 5.319 | 6.859 | 8.613 | 8.656 | 4.531 | 0.0194499 | phosphoribosyl pyrophosphate synthetase-associated protein 1 |
| KIF9 | 2.648 | 4.719 | 3.283 | 5.463 | 5.813 | 5.233 | 4.532 | 0.0313598 | kinesin family member 9 |
| TRMT2A | 3.648 | 5.684 | 4.903 | 7.084 | 7.201 | 6.743 | 4.534 | 0.0190541 | TRM2 tRNA methyltransferase 2 homolog A (S. cerevisiae) |
| FBXO40 | 1.648 | 1.648 | 1.834 | 3.830 | 3.499 | 4.104 | 4.537 | 0.0080205 | F-box protein 40 |
| CNGB1 | 3.422 | 3.293 | 1.978 | 3.830 | 4.174 | 4.692 | 4.537 | 0.0327158 | cyclic nucleotide gated channel beta 1 |
| DZIP1L | 4.525 | 5.366 | 5.366 | 5.845 | 6.952 | 6.707 | 4.537 | 0.0277445 | DAZ interacting protein 1-like |
| MRPL20 | 4.709 | 6.341 | 5.637 | 7.822 | 8.305 | 7.303 | 4.548 | 0.0173688 | mitochondrial ribosomal protein L20 |
| IDH3G | 6.716 | 6.456 | 5.992 | 8.901 | 8.723 | 8.036 | 4.549 | 0.016711 | Description |
| ADCY2 | 5.482 | 4.094 | 5.426 | 6.326 | 6.544 | 7.669 | 4.553 | 0.0360205 | adenylate cyclase 2 (brain) |
| C7orf63 | 2.233 | 3.130 | 4.204 | 6.104 | 5.172 | 5.320 | 4.563 | 0.0181764 | chromosome 7 open reading frame 63 |
| POM121L8P | 4.482 | 4.603 | 4.225 | 6.418 | 6.418 | 6.877 | 4.573 | 0.0076080 | POM121 membrane glycoprotein-like 8 pseudogene |
| NOL12 | 5.661 | 4.699 | 5.004 | 7.499 | 7.197 | 7.085 | 4.575 | 0.0112475 | nucleolar protein 12 |
| XPO5 | 5.171 | 6.024 | 5.862 | 8.218 | 8.218 | 7.263 | 4.576 | 0.0132288 | exportin 5 |
| LOC642587 | 8.285 | 6.955 | 6.607 | 9.077 | 11.651 | 8.801 | 4.577 | 0.0278832 | No description |
| FLJ45445 | 7.991 | 6.827 | 2.401 | 9.159 | 9.022 | 9.017 | 4.578 | 0.0303282 | No description |
| BMS1 | 5.781 | 5.277 | 6.434 | 7.976 | 8.230 | 7.677 | 4.579 | 0.0136225 | BMS1 homolog, ribosome assembly protein (yeast) |
| HEBP2 | 5.644 | 4.907 | 5.151 | 7.839 | 7.748 | 6.528 | 4.580 | 0.0170908 | heme binding protein 2 |
| LYSMD2 | 4.734 | 4.317 | 4.363 | 6.560 | 6.952 | 5.516 | 4.583 | 0.0245397 | LysM, putative peptidoglycan-binding, domain containing 2 |
| PTRH1 | 5.503 | 6.234 | 6.910 | 8.873 | 9.106 | 7.668 | 4.584 | 0.0170679 | peptidyl-tRNA hydrolase 1 homolog (S. cerevisiae) |
| MCM7 | 7.417 | 7.184 | 7.722 | 8.941 | 9.614 | 10.258 | 4.585 | 0.0142568 | minichromosome maintenance complex component 7 |
| NUFIP1 | 4.142 | 4.547 | 5.199 | 7.471 | 6.744 | 5.674 | 4.586 | 0.0276669 | nuclear fragile X mental retardation protein interacting protein 1 |
| EIF3J | 8.143 | 8.585 | 9.281 | 10.051 | 11.480 | 11.148 | 4.593 | 0.0176059 | eukaryotic translation initiation factor 3, subunit J |

TABLE 4-continued

Differentially Expressed Genes in CD44+ Breast Epithelial Cells

| | Nulliparous (NP) Samples | | | Parous (P) Samples | | | Pseudo | | |
|---|---|---|---|---|---|---|---|---|---|
| Gene Symbol | CD44+ N48 | CD44+ N58 | CD44+ N43 | CD44+ N37 | CD44+ N39 | CD44+ N40 | fold change | P value | Gene description |
| LOC646851 | 7.073 | 5.762 | 5.884 | 8.020 | 8.355 | 8.086 | 4.604 | 0.0221993 | No description |
| UPP2 | 2.233 | 5.252 | 5.588 | 6.556 | 7.458 | 7.497 | 4.613 | 0.0237924 | uridine phosphorylase 2 |
| BLOC1S1 | 8.514 | 7.468 | 8.407 | 10.812 | 10.144 | 9.675 | 4.618 | 0.0183809 | biogenesis of lysosomal organelles complex-1, subunit 1 |
| TMUB1 | 7.443 | 5.375 | 7.975 | 10.091 | 9.651 | 9.253 | 4.620 | 0.0160260 | transmembrane and ubiquitin-like domain containing 1 |
| C19orf24 | 4.709 | 5.266 | 4.257 | 6.917 | 7.407 | 6.472 | 4.621 | 0.0132718 | chromosome 19 open reading frame 24 |
| CAPG | 7.165 | 6.818 | 7.603 | 9.292 | 9.335 | 9.813 | 4.625 | 0.0079955 | capping protein (actin filament), gelsolin-like |
| STOML1 | 3.860 | 0.648 | 3.046 | 5.256 | 5.894 | 5.158 | 4.630 | 0.0172489 | stomatin (EPB72)-like 1 |
| LAMA4 | 10.722 | 8.928 | 10.360 | 12.818 | 12.283 | 12.571 | 4.630 | 0.0118187 | laminin, alpha 4 |
| SDHAP2 | 3.860 | 4.189 | 5.613 | 6.631 | 6.052 | 7.825 | 4.635 | 0.0244967 | succinate dehydrogenase complex, subunit A, flavoprotein pseudogene 2 |
| RDH5 | 6.312 | 4.043 | 5.487 | 7.912 | 7.554 | 7.701 | 4.638 | 0.0169723 | retinol dehydrogenase 5 (11-cis/9-cis) |
| CD22 | 1.648 | 2.894 | 2.281 | 4.017 | 3.892 | 5.108 | 4.639 | 0.0216953 | CD22 molecule |
| DIO3OS | 1.648 | 1.648 | 2.894 | 4.725 | 2.739 | 5.108 | 4.639 | 0.0356607 | DIO3 opposite strand (non-protein coding) |
| MLX | 8.043 | 6.366 | 6.733 | 9.752 | 9.630 | 8.580 | 4.639 | 0.0196932 | MAX-like protein X |
| ZC3H7B | 6.260 | 5.253 | 5.530 | 8.222 | 7.744 | 7.551 | 4.639 | 0.0125542 | zinc finger CCCH-type containing 7B |
| RPL18 | 11.785 | 11.262 | 12.334 | 14.000 | 13.952 | 14.405 | 4.643 | 0.0090222 | ribosomal protein L18 |
| PHF20 | 7.331 | 6.885 | 6.107 | 9.547 | 9.053 | 8.953 | 4.644 | 0.0094756 | PHD finger protein 20 |
| MGC70857 | 7.295 | 4.189 | 6.800 | 9.412 | 9.015 | 8.258 | 4.645 | 0.0208232 | No description |
| DKFZp761E198 | 6.845 | 7.153 | 7.608 | 10.263 | 9.118 | 9.062 | 4.648 | 0.0131324 | No description |
| IL10 | 6.742 | 5.081 | 5.878 | 7.719 | 7.924 | 8.959 | 4.650 | 0.0183380 | interleukin 10 |
| RPS6KA4 | 6.776 | 5.828 | 7.737 | 8.993 | 9.496 | 8.823 | 4.652 | 0.0167338 | ribosomal protein S6 kinase, 90 kDa, polypeptide 4 |
| ZSCAN21 | 2.648 | 3.791 | 4.340 | 6.296 | 6.009 | 5.255 | 4.664 | 0.0183151 | zinc finger and SCAN domain containing 21 |
| LLGL2 | 3.233 | 4.122 | 5.577 | 6.344 | 7.702 | 6.300 | 4.664 | 0.0221244 | lethal giant larvae homolog 2 (Drosophila) |
| ARFGAP1 | 3.648 | 4.091 | 4.998 | 7.220 | 6.610 | 5.551 | 4.664 | 0.0214693 | ADP-ribosylation factor GTPase activating protein 1 |
| RHBDL3 | 4.108 | 4.334 | 4.799 | 6.331 | 6.551 | 8.147 | 4.670 | 0.0122104 | rhomboid, veinlet-like 3 (Drosophila) |
| LOC652276 | 3.947 | 4.427 | 3.290 | 6.171 | 5.854 | 6.239 | 4.674 | 0.0114146 | No description |
| LOC285456 | 1.648 | 2.304 | 2.926 | 4.477 | 4.529 | 5.082 | 4.676 | 0.0101272 | No description |
| DHX34 | 3.648 | 4.143 | 4.826 | 5.883 | 6.647 | 6.369 | 4.676 | 0.0156496 | DEAN (Asp-Glu-Ala-His) box polypeptide 34 |
| MED11 | 5.870 | 4.713 | 4.381 | 8.015 | 7.806 | 6.612 | 4.693 | 0.0147823 | mediator complex subunit 11 |
| RFXANK | 7.338 | 6.036 | 6.688 | 9.570 | 8.864 | 8.598 | 4.700 | 0.0130686 | regulatory factor X-associated ankyrin-containing protein |
| ILFS | 8.343 | 8.291 | 8.005 | 9.842 | 10.524 | 10.889 | 4.702 | 0.0106125 | interleukin enhancer binding factor 3, 90 kDa |
| ISOC2 | 6.495 | 6.422 | 6.904 | 9.137 | 8.999 | 8.137 | 4.702 | 0.0123109 | isochorismatase domain containing 2 |
| TMEM176A | 2.648 | 3.297 | 2.648 | 4.883 | 4.618 | 5.665 | 4.706 | 0.0125903 | transmembrane protein 176A |
| GPAT2 | 5.572 | 3.607 | 4.376 | 7.811 | 6.639 | 5.346 | 4.719 | 0.0429002 | glycerol-3-phosphate acyltransferase 2, mitochondrial |
| PMF1 | 7.726 | 6.546 | 6.453 | 8.965 | 9.082 | 8.693 | 4.724 | 0.0187317 | polyamine-modulated factor 1 |
| PHF5A | 6.692 | 6.670 | 7.021 | 9.262 | 9.090 | 8.654 | 4.726 | 0.0072877 | PHD finger protein 5A |
| HDAC6 | 6.499 | 5.544 | 6.473 | 7.841 | 7.832 | 8.741 | 4.730 | 0.0205487 | histone deacetylase 6 |
| MY019 | 5.291 | 5.819 | 6.158 | 8.050 | 8.401 | 7.563 | 4.733 | 0.0106638 | myosin XIX |
| RBM15B | 6.993 | 7.764 | 7.011 | 9.653 | 9.415 | 9.239 | 4.745 | 0.0096870 | RNA binding motif protein 15B |
| FAM 1640 | 2.233 | 2.233 | 2.524 | 4.276 | 4.777 | 4.481 | 4.748 | 0.0064898 | family with sequence similarity 164, member C |
| KCTD17 | 2.233 | 3.717 | 2.233 | 5.610 | 4.777 | 4.481 | 4.748 | 0.0196752 | potassium channel tetramerisation domain containing 17 |
| CHST5 | 4.525 | 2.233 | 2.461 | 5.041 | 5.479 | 5.665 | 4.748 | 0.0432898 | carbohydrate (N-acetylglucosamine 6-O) sulfotransferase 5 |
| OGDH | 8.375 | 6.828 | 7.553 | 10.007 | 9.804 | 9.075 | 4.750 | 0.0226354 | oxoglutarate (alpha-ketoglutarate) dehydrogenase (lipoamide) |
| PSMG4 | 5.861 | 5.256 | 5.170 | 7.420 | 8.091 | 8.087 | 4.757 | 0.0067393 | proteasome (prosome, macropain) assembly chaperone 4 |
| BCL2L11 | 8.932 | 8.235 | 9.134 | 10.769 | 10.528 | 11.385 | 4.759 | 0.0137598 | BCL2-like 11 (apoptosis facilitator) |
| MT1L | 4.008 | 5.576 | 5.658 | 6.259 | 7.144 | 8.187 | 4.760 | 0.0318957 | metallothionein 1L (gene/pseudogene) |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| ZNF592 | 6.576 | 6.534 | 7.101 | 9.223 | 8.785 | 9.323 | 4.761 | 0.0058853 | zinc finger protein 592 |
| ZBTB40 | 7.017 | 6.348 | 7.175 | 8.601 | 9.037 | 9.681 | 4.765 | 0.0120579 | zinc finger and BTB domain containing 40 |
| FBXL14 | 3.422 | 2.121 | 2.234 | 4.376 | 4.421 | 5.862 | 4.771 | 0.0195823 | F-box and leucine-rich repeat protein 14 |
| FOXF2 | 7.304 | 6.997 | 7.315 | 9.562 | 8.383 | 10.246 | 4.781 | 0.0188780 | forkhead box F2 |
| ZNF500 | 4.378 | 3.621 | 4.399 | 6.124 | 6.657 | 5.889 | 4.784 | 0.0134513 | zinc finger protein 500 |
| NDOR1 | 5.846 | 4.967 | 5.917 | 8.175 | 8.010 | 8.002 | 4.784 | 0.0061043 | NADPH dependent diflavin oxidoreductase 1 |
| ERAL1 | 4.709 | 5.655 | 5.086 | 8.460 | 7.344 | 6.617 | 4.785 | 0.0173029 | Era G-protein-like 1 (*E. coli*) |
| SRRD | 5.739 | 4.587 | 4.602 | 7.378 | 7.806 | 6.847 | 4.789 | 0.0122014 | SRR1 domain containing |
| PPP1R9B | 9.229 | 6.461 | 7.835 | 9.530 | 10.096 | 10.669 | 4.793 | 0.0306430 | protein phosphatase 1, regulatory (inhibitor) subunit 9B |
| USP40 | 7.140 | 5.094 | 5.951 | 8.327 | 8.214 | 8.198 | 4.800 | 0.0209390 | ubiquitin specific peptidase 40 |
| MARS | 9.247 | 9.005 | 8.605 | 11.772 | 11.270 | 9.812 | 4.806 | 0.0283428 | methionyl-tRNA synthetase |
| TP53I3 | 7.149 | 5.926 | 7.730 | 9.996 | 9.164 | 9.388 | 4.810 | 0.0118277 | tumor protein p53 inducible protein 13 |
| RPS6 | 14.301 | 13.212 | 15.081 | 16.567 | 16.806 | 15.813 | 4.810 | 0.0215816 | ribosomal protein S6 |
| VPS16 | 5.377 | 5.599 | 5.435 | 8.357 | 7.703 | 7.528 | 4.817 | 0.0060523 | vacuolar protein sorting 16 homolog (*S. cerevisiae*) |
| LIG4 | 1.648 | 4.952 | 4.485 | 7.220 | 6.665 | 5.082 | 4.819 | 0.0333598 | ligase IV, DNA, ATP-dependent |
| TRAF4 | 10.195 | 9.202 | 10.171 | 11.470 | 13.043 | 12.333 | 4.819 | 0.0139054 | TNF receptor-associated factor 4 |
| DYNLL1 | 10.730 | 9.630 | 10.886 | 11.903 | 12.513 | 13.209 | 4.834 | 0.0205175 | dynein, light chain, LC8-type 1 |
| TMEM86B | 2.970 | 3.601 | 3.111 | 5.385 | 4.361 | 6.297 | 4.836 | 0.0229279 | transmembrane protein 86B |
| GLG1 | 10.521 | 8.047 | 9.026 | 11.761 | 10.579 | 11.301 | 4.840 | 0.0385889 | golgi glycoprotein 1 |
| YTHDF2 | 9.809 | 8.829 | 9.921 | 12.011 | 12.124 | 12.087 | 4.850 | 0.0061723 | YTH domain family, member 2 |
| FBXL15 | 6.202 | 5.514 | 6.634 | 8.913 | 8.001 | 8.114 | 4.852 | 0.0137868 | F-box and leucine-rich repeat protein 15 |
| IDUA | 7.257 | 6.247 | 6.789 | 8.336 | 9.067 | 10.121 | 4.852 | 0.0152787 | Description |
| TAT | 7.421 | 5.349 | 6.318 | 8.597 | 8.558 | 8.707 | 4.852 | 0.0189140 | tyrosine aminotransferase |
| ZNF296 | 5.109 | 2.233 | 4.142 | 5.892 | 6.588 | 6.420 | 4.852 | 0.0240010 | zinc finger protein 296 |
| CYP2B7P1 | 1.648 | 1.648 | 1.648 | 5.064 | 3.805 | 3.929 | 4.860 | 0.0066520 | cytochrome P450, family 2, subfamily B, polypeptide 7 pseudogene 1 |
| PQLC2 | 1.648 | 1.648 | 2.776 | 4.624 | 4.945 | 3.929 | 4.860 | 0.0107054 | PQ loop repeat containing 2 |
| ST7OT1 | 5.400 | 4.021 | 4.189 | 7.148 | 6.666 | 6.304 | 4.866 | 0.0172260 | ST7 overlapping transcript 1 (non-protein coding) |
| NELF | 7.889 | 8.149 | 8.987 | 10.453 | 10.799 | 10.171 | 4.867 | 0.0138118 | nasal embryonic LHRH factor |
| CHCHD6 | 6.340 | 3.645 | 5.292 | 7.675 | 7.576 | 6.791 | 4.869 | 0.0291976 | coiled-coil-helix-coiled-coil-helix domain containing 6 |
| VPS72 | 7.661 | 5.604 | 7.377 | 9.661 | 9.664 | 8.402 | 4.870 | 0.0231012 | vacuolar protein sorting 72 homolog (*S. cerevisiae*) |
| AMZ1 | 4.264 | 4.119 | 3.802 | 6.549 | 6.302 | 6.227 | 4.871 | 0.0049834 | archaelysin family metallopeptidase 1 |
| FAM127A | 3.619 | 2.649 | 3.029 | 5.610 | 5.314 | 5.279 | 4.875 | 0.0081744 | family with sequence similarity 127, member A |
| COLQ | 2.648 | 4.178 | 4.340 | 5.861 | 5.813 | 6.626 | 4.877 | 0.0160101 | collagen-like tail subunit (single strand of homotrimer) of asymmetric acetylcholinesterase |
| LRCH1 | 8.554 | 7.720 | 8.194 | 10.007 | 10.254 | 10.946 | 4.880 | 0.0112267 | leucine-rich repeats and calponin homology (CH) domain containing 1 |
| IYD | 4.895 | 2.744 | 3.022 | 5.835 | 5.032 | 6.160 | 4.884 | 0.0304530 | iodotyrosine deiodinase |
| SHE | 4.456 | 4.853 | 4.546 | 6.832 | 6.744 | 7.323 | 4.886 | 0.0055359 | Src homology 2 domain containing E |
| POM121 | 5.377 | 4.681 | 4.850 | 6.970 | 7.314 | 7.289 | 4.887 | 0.0076801 | POM121 membrane glycoprotein |
| CLEC4E | 2.233 | 3.815 | 3.972 | 5.773 | 4.523 | 7.778 | 4.888 | 0.0263442 | C-type lectin domain family 4, member E |
| KDM4D | 4.657 | 2.233 | 2.461 | 5.231 | 4.523 | 5.637 | 4.888 | 0.0418360 | lysine (K)-specific demethylase 4D |
| C16orf68 | 5.821 | 5.346 | 6.723 | 8.572 | 8.313 | 7.635 | 4.889 | 0.0159407 | chromosome 16 open reading frame 68 |
| AFG3L1 | 4.826 | 4.356 | 5.500 | 7.745 | 7.117 | 7.089 | 4.892 | 0.0090367 | No description |
| APPBP2 | 5.507 | 5.804 | 5.967 | 7.884 | 7.800 | 8.414 | 4.901 | 0.0069120 | amyloid beta precursor protein (cytoplasmic tail) binding protein 2 |

TABLE 4-continued

Differentially Expressed Genes in CD44+ Breast Epithelial Cells

| | Nulliparous (NP) Samples | | | Parous (P) Samples | | | Pseudo fold change | P value | Gene description |
|---|---|---|---|---|---|---|---|---|---|
| Gene Symbol | CD44+ N48 | CD44+ N58 | CD44+ N43 | CD44+ N37 | CD44+ N39 | CD44+ N40 | | | |
| C10orf118 | 4.708 | 5.264 | 5.892 | 7.497 | 7.557 | 7.764 | 4.902 | 0.0094846 | chromosome 10 open reading frame 118 |
| IRF2BP1 | 6.931 | 5.389 | 6.491 | 8.784 | 8.905 | 8.384 | 4.902 | 0.0115899 | interferon regulatory factor 2 binding protein 1 |
| DGCR8 | 6.509 | 6.541 | 6.731 | 8.835 | 9.393 | 8.143 | 4.904 | 0.0121307 | DiGeorge syndrome critical region gene 8 |
| APOBEC3G | 4.525 | 4.294 | 3.620 | 5.330 | 6.588 | 7.742 | 4.905 | 0.0208551 | apolipoprotein B mRNA editing enzyme, catalytic polypeptide-like 3G |
| TRIM14 | 5.008 | 4.465 | 4.126 | 6.346 | 7.010 | 7.304 | 4.911 | 0.0098756 | tripartite motif-containing 14 |
| QTRT1 | 6.968 | 6.467 | 7.917 | 9.266 | 8.983 | 9.476 | 4.918 | 0.0163712 | queuine tRNA-ribosyltransferase 1 |
| DNM1L | 6.229 | 7.009 | 7.102 | 9.396 | 9.308 | 9.161 | 4.921 | 0.0053411 | dynamin 1-like |
| LSM10 | 5.452 | 4.792 | 5.313 | 7.751 | 7.454 | 7.224 | 4.921 | 0.0071643 | LSM10, U7 small nuclear RNA associated |
| RNH1 | 10.255 | 9.304 | 9.734 | 12.882 | 12.037 | 11.419 | 4.933 | 0.0136738 | ribonuclease/angiogenin inhibitor 1 |
| BAZ1B | 7.215 | 7.229 | 8.084 | 9.519 | 9.818 | 10.082 | 4.935 | 0.0091830 | bromodomain adjacent to zinc finger domain, 1B |
| LOC286467 | 2.233 | 4.564 | 5.189 | 6.288 | 6.950 | 6.870 | 4.948 | 0.0195400 | No description |
| EIF4ENIF1 | 6.135 | 5.310 | 5.848 | 7.889 | 8.402 | 8.157 | 4.956 | 0.0067123 | eukaryotic translation initiation factor 4E nuclear import factor 1 |
| ASF1A | 6.227 | 5.987 | 6.610 | 8.536 | 8.487 | 8.708 | 4.956 | 0.0055179 | ASF1 anti-silencing function 1 homolog A (*S. cerevisiae*) |
| ITGA10 | 3.456 | 5.477 | 5.468 | 7.210 | 7.427 | 7.788 | 4.964 | 0.0133057 | integrin, alpha 10 |
| FLJ39582 | 5.264 | 2.675 | 4.852 | 7.576 | 7.005 | 7.062 | 4.965 | 0.0123789 | No description |
| GPR25 | 4.647 | 2.941 | 3.860 | 5.256 | 6.173 | 6.522 | 4.970 | 0.0227664 | G protein-coupled receptor 25 |
| LOC643008 | 4.086 | 3.486 | 3.795 | 6.132 | 5.801 | 6.335 | 4.973 | 0.0064211 | No description |
| GDAP1 | 4.817 | 3.508 | 2.461 | 5.968 | 5.824 | 5.451 | 4.978 | 0.0264468 | ganglioside-induced differentiation-associated protein 1 |
| ZNF490 | 5.019 | 4.307 | 4.660 | 6.329 | 7.174 | 7.336 | 4.982 | 0.0102832 | zinc finger protein 490 |
| KHNYN | 7.544 | 6.693 | 8.143 | 9.679 | 10.115 | 9.863 | 4.990 | 0.0103657 | KH and NYN domain containing |
| XPC | 7.002 | 5.597 | 5.788 | 9.361 | 7.917 | 8.091 | 4.992 | 0.0183899 | xeroderma pigmentosum, complementation group C |
| COG2 | 4.860 | 3.957 | 4.493 | 7.275 | 6.812 | 5.398 | 4.992 | 0.0261542 | component of oligomeric golgi complex 2 |
| TSPAN31 | 5.781 | 5.634 | 5.646 | 7.968 | 7.445 | 8.114 | 5.000 | 0.0078652 | tetraspanin 31 |
| RRN3P3 | 8.852 | 8.122 | 9.266 | 11.378 | 11.156 | 11.175 | 5.004 | 0.0068433 | RNA polymerase I transcription factor homolog (*S. cerevisiae*) pseudogene 3 |
| SEC31A | 10.321 | 9.100 | 9.449 | 12.239 | 11.773 | 11.615 | 5.008 | 0.0123608 | SEC31 homolog A (*S. cerevisiae*) |
| FMNL3 | 8.130 | 6.765 | 6.695 | 9.703 | 8.851 | 10.455 | 5.010 | 0.0159068 | formin-like 3 |
| MAP7D1 | 10.382 | 9.309 | 11.191 | 12.709 | 13.169 | 12.636 | 5.018 | 0.0120433 | MAP7 domain containing 1 |
| FOXD1 | 3.422 | 2.894 | 1.689 | 5.196 | 4.017 | 6.454 | 5.022 | 0.0216087 | forkhead box D1 |
| ATRIP | 5.781 | 2.926 | 5.110 | 7.439 | 7.813 | 6.947 | 5.027 | 0.0168406 | ATR interacting protein |
| HOXB6 | 4.314 | 2.401 | 3.431 | 6.329 | 5.462 | 5.761 | 5.027 | 0.0145480 | homeobox B6 |
| MRPS25 | 7.061 | 6.435 | 6.649 | 8.279 | 8.979 | 10.334 | 5.028 | 0.0149640 | mitochondrial ribosomal protein S25 |
| LOC283174 | 3.233 | 3.991 | 3.685 | 4.590 | 6.632 | 6.017 | 5.035 | 0.0253730 | No description |
| TYMS | 3.792 | 2.648 | 2.648 | 5.024 | 5.977 | 4.981 | 5.037 | 0.0145147 | thymidylate synthetase |
| C22orf30 | 3.648 | 4.448 | 4.959 | 7.515 | 6.781 | 5.600 | 5.041 | 0.0215123 | chromosome 22 open reading frame 30 |
| PCMT1 | 9.241 | 8.437 | 8.383 | 11.233 | 10.883 | 10.718 | 5.043 | 0.0094166 | protein-L-isoaspartate (D-aspartate) O-methyltransferase |
| SH3KBP1 | 6.398 | 6.327 | 6.877 | 10.141 | 8.734 | 8.652 | 5.050 | 0.0089674 | SH3KBP1 binding protein 1 |
| ACTL7B | 0.648 | 0.648 | 0.729 | 3.351 | 2.987 | 2.370 | 5.057 | 0.0089931 | actin-like 7B |
| HAPLN2 | 0.648 | 0.648 | 0.648 | 3.662 | 2.987 | 2.370 | 5.057 | 0.0100211 | hyaluronan and proteoglycan link protein 2 |
| PLB1 | 0.648 | 0.648 | 0.648 | 2.202 | 2.987 | 3.351 | 5.057 | 0.0111341 | phospholipase B1 |
| SNORA24 | 0.648 | 0.648 | 0.648 | 2.202 | 2.987 | 3.351 | 5.057 | 0.0111341 | small nucleolar RNA, H/ACA box 24 |
| CYP46A1 | 0.648 | 0.648 | 0.729 | 2.202 | 2.987 | 3.773 | 5.057 | 0.0126083 | cytochrome P450, family 46, subfamily A, polypeptide 1 |
| MIR132 | 0.648 | 0.648 | 1.387 | 2.202 | 2.987 | 5.158 | 5.057 | 0.0235407 | microRNA 132 |
| ATP2A1 | 0.648 | 2.593 | 0.648 | 4.632 | 2.987 | 3.351 | 5.057 | 0.0249418 | ATPase, Ca++ transporting, cardiac muscle, fast twitch 1 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| TMEM132E | 0.648 | 2.359 | 2.987 | 4.854 | 2.987 | 5.230 | 5.057 | 0.0326003 | transmembrane protein 132E |
| PYCRL | 5.289 | 4.237 | 4.951 | 6.774 | 7.474 | 7.290 | 5.059 | 0.0095643 | pyrroline-5-carboxylate reductase-like |
| PRR12 | 6.735 | 4.901 | 5.402 | 8.499 | 7.480 | 7.744 | 5.068 | 0.0210090 | proline rich 12 |
| INTU | 3.860 | 1.477 | 2.714 | 3.351 | 5.351 | 6.202 | 5.071 | 0.0426527 | intumed planar cell polarity effector homolog (Drosophila) |
| ACHE | 3.792 | 3.424 | 3.016 | 5.748 | 6.001 | 5.767 | 5.073 | 0.0051470 | acetylcholinesterase |
| E2F4 | 2.648 | 3.722 | 4.495 | 6.066 | 6.828 | 5.400 | 5.077 | 0.0163567 | E2F transcription factor 4, p107/p130-binding |
| FAM32A | 7.787 | 7.990 | 7.912 | 10.382 | 10.133 | 10.142 | 5.086 | 0.0034603 | family with sequence similarity 32, member A |
| WDR27 | 2.970 | 3.827 | 2.970 | 5.919 | 3.827 | 6.174 | 5.086 | 0.0365192 | WD repeat domain 27 |
| TNFAIP8L1 | 7.740 | 7.161 | 7.756 | 9.951 | 10.080 | 10.103 | 5.086 | 0.0038548 | tumor necrosis factor, alpha-induced protein 8-like 1 |
| C9orf78 | 6.959 | 7.732 | 7.083 | 9.768 | 9.314 | 9.430 | 5.087 | 0.0083511 | chromosome 9 open reading frame 78 |
| CHD3 | 8.978 | 7.175 | 8.274 | 10.622 | 10.083 | 11.279 | 5.090 | 0.0141695 | chromodomain helicase DNA binding protein 3 |
| SP4 | 5.645 | 5.189 | 4.635 | 7.164 | 7.039 | 7.994 | 5.093 | 0.0128010 | Sp4 transcription factor |
| POP1 | 3.233 | 3.233 | 3.261 | 5.583 | 6.399 | 5.349 | 5.096 | 0.0057217 | processing of precursor 1, ribonuclease P/MRP subunit (S. cerevisiae) |
| IKZF2 | 3.233 | 4.673 | 3.877 | 5.583 | 5.970 | 7.062 | 5.099 | 0.0187081 | IKAROS family zinc finger 2 (Helios) |
| SMYD4 | 7.218 | 7.457 | 5.360 | 7.711 | 7.692 | 8.209 | 5.102 | 0.0315719 | SET and MYND domain containing 4 |
| KRT27 | 0.648 | 0.648 | 0.729 | 3.081 | 2.987 | 3.043 | 5.104 | 0.0021203 | keratin 27 |
| KDM2A | 9.284 | 8.699 | 9.261 | 11.636 | 11.186 | 11.575 | 5.105 | 0.0055969 | lysine (K)-specific demethylase 2A |
| C10orf140 | 3.456 | 3.456 | 3.523 | 5.903 | 4.871 | 5.809 | 5.108 | 0.0139463 | chromosome 10 open reading frame 140 |
| HCCS | 6.257 | 6.019 | 6.483 | 9.007 | 8.611 | 8.329 | 5.114 | 0.0054908 | holocytochrome c synthase |
| SPRYD4 | 5.982 | 4.047 | 4.033 | 6.846 | 6.413 | 6.388 | 5.115 | 0.0384905 | SPRY domain containing 4 |
| RPL9 | 13.044 | 13.083 | 13.458 | 15.461 | 15.813 | 15.201 | 5.116 | 0.0062222 | ribosomal protein L9 |
| MFSD11 | 7.298 | 4.747 | 5.467 | 7.853 | 7.490 | 7.822 | 5.117 | 0.0450589 | major facilitator superfamily domain containing 11 |
| POLA1 | 2.233 | 2.233 | 2.814 | 6.139 | 3.958 | 4.590 | 5.123 | 0.0165085 | polymerase (DNA directed), alpha 1, catalytic subunit |
| DUS3L | 6.732 | 5.891 | 7.892 | 9.299 | 9.881 | 8.249 | 5.126 | 0.0240440 | dihydrouridine synthase 3-like (S. cerevisiae) |
| GINS1 | 3.792 | 3.202 | 3.533 | 4.273 | 6.151 | 6.107 | 5.129 | 0.0295809 | GINS complex subunit 1 (Psf1 homolog) |
| DUS2L | 1.648 | 3.423 | 3.023 | 5.601 | 5.783 | 3.557 | 5.135 | 0.0311588 | dihydrouridine synthase 2-like, SMM1 homolog (S. cerevisiae) |
| AP1S1 | 6.392 | 4.435 | 4.529 | 8.272 | 7.128 | 6.798 | 5.143 | 0.0256087 | adaptor-related protein complex 1, sigma 1 subunit |
| ZNF335 | 6.472 | 6.168 | 7.567 | 8.835 | 9.036 | 8.781 | 5.145 | 0.0153778 | zinc finger protein 335 |
| XIRP1 | 4.086 | 5.451 | 5.902 | 5.651 | 7.815 | 8.329 | 5.147 | 0.0454610 | xin actin-binding repeat containing 1 |
| ERMP1 | 4.793 | 3.233 | 3.545 | 6.259 | 6.465 | 5.598 | 5.151 | 0.0168912 | endoplasmic reticulum metallopeptidase 1 |
| GPR133 | 4.539 | 4.510 | 5.553 | 7.918 | 6.485 | 7.399 | 5.152 | 0.0137958 | G protein-coupled receptor 133 |
| TMEM149 | 5.042 | 1.648 | 3.435 | 5.805 | 5.120 | 5.802 | 5.159 | 0.0420704 | transmembrane protein 149 |
| CEP192 | 3.860 | 1.387 | 3.043 | 5.256 | 5.411 | 5.606 | 5.160 | 0.0147442 | centrosomal protein 192 kDa |
| ZNF169 | 1.648 | 1.648 | 1.689 | 4.662 | 4.017 | 3.557 | 5.166 | 0.0072517 | zinc finger protein 169 |
| GP5 | 1.648 | 1.648 | 1.689 | 4.017 | 3.247 | 4.692 | 5.166 | 0.0112925 | glycoprotein V (platelet) |
| GRM2 | 1.648 | 1.648 | 1.978 | 4.017 | 2.739 | 4.830 | 5.166 | 0.0244815 | glutamate receptor, metabotropic 2 |
| HSPA1L | 1.648 | 2.601 | 3.841 | 4.931 | 4.017 | 7.633 | 5.166 | 0.0282679 | heat shock 70 kDa protein 1-like |
| RNF112 | 4.423 | 1.648 | 2.458 | 5.459 | 4.017 | 6.351 | 5.166 | 0.0340073 | ring finger protein 112 |
| FAM73B | 5.899 | 5.681 | 6.259 | 8.389 | 8.271 | 8.269 | 5.177 | 0.0044419 | family with sequence similarity 73, member B |
| C2orf15 | 7.533 | 6.811 | 7.285 | 9.375 | 9.658 | 9.858 | 5.179 | 0.0055789 | chromosome 2 open reading frame 15 |
| SRP72 | 8.037 | 7.503 | 6.290 | 10.411 | 8.922 | 9.039 | 5.184 | 0.0256315 | signal recognition particle 72 kDa |
| TIPRL | 6.834 | 6.896 | 6.290 | 9.329 | 8.758 | 8.665 | 5.187 | 0.0086166 | TIP41, TOR signaling pathway regulator-like (S. cerevisiae) |
| TAF10 | 8.832 | 7.280 | 8.270 | 10.645 | 10.863 | 10.596 | 5.188 | 0.0085896 | TAF10 RNA polymerase II, TATA box binding protein (TBP)-associated factor, 30 kDa |
| C9orf114 | 2.648 | 3.766 | 4.148 | 6.774 | 5.993 | 5.026 | 5.197 | 0.0179199 | chromosome 9 open reading frame 114 |

TABLE 4-continued

Differentially Expressed Genes in CD44+ Breast Epithelial Cells

| Gene Symbol | Nulliparous (NP) Samples | | Parous (P) Samples | | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| MRPL32 | 9.291 | 8.689 | 8.574 | 10.953 | 11.543 | 11.139 | 5.201 | 0.0070201 | mitochondrial ribosomal protein L32 |
| PELI3 | 5.235 | 4.092 | 4.926 | 7.779 | 6.766 | 6.472 | 5.205 | 0.0160745 | pellino homolog 3 (Drosophila) |
| FAAH | 3.422 | 3.209 | 4.453 | 5.731 | 6.086 | 5.802 | 5.207 | 0.0135906 | fatty acid amide hydrolase |
| RUNDC2C | 3.456 | 3.830 | 4.157 | 5.073 | 6.436 | 6.538 | 5.210 | 0.0169633 | RUN domain containing 2C |
| ADSSL1 | 5.452 | 3.209 | 2.601 | 5.102 | 5.591 | 7.566 | 5.215 | 0.0435560 | adenylosuccinate synthase like 1 |
| TEP1 | 5.789 | 5.445 | 6.146 | 8.332 | 8.529 | 7.667 | 5.217 | 0.0079366 | telomerase-associated protein 1 |
| LOC283314 | 5.594 | 5.031 | 5.301 | 7.419 | 7.715 | 7.804 | 5.234 | 0.0052780 | No description |
| RNF123 | 6.492 | 5.877 | 5.960 | 8.881 | 8.400 | 7.960 | 5.239 | 0.0089494 | ring finger protein 123 |
| CROP | 5.346 | 4.905 | 4.876 | 6.742 | 7.438 | 7.737 | 5.244 | 0.0098485 | CGRP receptor component |
| UTS2D | 2.233 | 3.047 | 3.983 | 5.773 | 4.624 | 5.842 | 5.245 | 0.0187407 | urotensin 2 domain containing |
| SLC10A7 | 4.525 | 2.233 | 2.524 | 5.167 | 4.624 | 5.279 | 5.245 | 0.0405438 | solute carrier family 10 (sodium/bile acid cotransporter family), member 7 |
| DOT1L | 9.224 | 8.417 | 10.187 | 11.615 | 11.692 | 11.379 | 5.246 | 0.0154173 | DOT1-like, histone H3 methyltransferase (S. cerevisiae) |
| TUBE1 | 4.620 | 5.243 | 5.352 | 8.111 | 7.636 | 6.612 | 5.253 | 0.0126603 | tubulin, epsilon 1 |
| HMX3 | 3.194 | 0.648 | 1.649 | 4.854 | 4.043 | 3.351 | 5.256 | 0.0305272 | H6 family homeobox 3 |
| CBLL1 | 6.690 | 6.086 | 6.285 | 8.679 | 8.723 | 8.482 | 5.260 | 0.0057667 | Cas-Br-M (murine) ecotropic retroviral transforming sequence-like 1 |
| ATP1B4 | 0.648 | 0.648 | 0.648 | 3.351 | 2.987 | 3.043 | 5.260 | 0.0025477 | ATPase, Na+/K+ transporting, beta 4 polypeptide |
| XKR6 | 0.648 | 0.648 | 0.648 | 3.351 | 2.987 | 3.043 | 5.260 | 0.0025477 | XK, Kell blood group complex subunit-related family, member 6 |
| DNAJB7 | 1.078 | 0.648 | 2.202 | 4.372 | 4.428 | 3.043 | 5.260 | 0.0125272 | DnaJ (Hsp40) homolog, subfamily B, member 7 |
| PKLR | 0.648 | 0.648 | 1.245 | 2.202 | 3.871 | 6.535 | 5.260 | 0.0175386 | pyruvate kinase, liver and RBC |
| CYP2R1 | 4.264 | 4.060 | 4.140 | 6.218 | 7.314 | 7.425 | 5.260 | 0.0060433 | cytochrome P450, family 2, subfamily R, polypeptide 1 |
| JRK | 4.871 | 4.988 | 4.727 | 7.271 | 7.110 | 11.795 | 5.277 | 0.0031761 | jerky homolog (mouse) |
| C1orf135 | 9.893 | 9.294 | 10.856 | 12.293 | 12.313 | 9.780 | 5.278 | 0.0180059 | chromosome 1 open reading frame 135 |
| CDK2AP2 | 7.912 | 6.944 | 8.556 | 11.173 | 9.345 | 8.382 | 5.278 | 0.0232565 | cyclin-dependent kinase 2 associated protein 2 |
| UTP6 | 5.982 | 6.439 | 5.474 | 8.241 | 8.733 | | 5.281 | 0.0061813 | UTP6, small subunit (SSU) processome component, homolog (yeast) |
| PPP1R16B | 5.936 | 3.456 | 3.859 | 5.857 | 5.858 | 8.633 | 5.284 | 0.0451726 | protein phosphatase 1, regulatory (inhibitor) subunit 16B |
| NFIC | 9.760 | 7.601 | 7.954 | 11.323 | 10.280 | 10.357 | 5.290 | 0.0264849 | nuclear factor I/C (CCAAT-binding transcription factor) |
| CCNJ | 3.233 | 4.087 | 4.138 | 6.541 | 5.970 | 5.927 | 5.291 | 0.0093986 | cyclin J |
| PPIF | 8.249 | 8.578 | 9.142 | 10.822 | 11.257 | 10.981 | 5.291 | 0.0071553 | peptidylprolyl isomerase F |
| DBF4B | 8.151 | 7.640 | 7.907 | 10.046 | 10.294 | 10.611 | 5.299 | 0.0048932 | DBF4 homolog B (S. cerevisiae) |
| C11orf53 | 0.648 | 3.336 | 3.873 | 6.103 | 5.742 | 5.158 | 5.299 | 0.0161244 | chromosome 11 open reading frame 53 |
| GATSL3 | 5.042 | 4.692 | 5.288 | 7.099 | 7.420 | 7.934 | 5.306 | 0.0059033 | GATS protein-like 3 |
| CARDIO | 6.340 | 4.285 | 4.830 | 6.910 | 9.220 | 6.693 | 5.307 | 0.0303532 | caspase recruitment domain family, member 10 |
| HAVCR2 | 4.525 | 2.233 | 3.686 | 6.098 | 4.889 | 6.707 | 5.322 | 0.0248024 | hepatitis A virus cellular receptor 2 |
| SHF | 6.713 | 5.167 | 6.258 | 8.436 | 8.570 | 9.128 | 5.333 | 0.0084815 | Src homology 2 domain containing F |
| ZNF321 | 7.068 | 6.892 | 7.874 | 9.310 | 9.635 | 9.947 | 5.344 | 0.0089064 | zinc finger protein 321 |
| SF3B2 | 8.186 | 8.042 | 8.130 | 10.796 | 10.549 | 9.833 | 5.346 | 0.0084371 | splicing factor 3b, subunit 2, 145 kDa |
| WFDC8 | 3.194 | 1.245 | 2.593 | 5.407 | 4.602 | 5.014 | 5.355 | 0.0114416 | WAP four-disulfide core domain 8 |
| ACSL4 | 6.317 | 6.394 | 6.678 | 9.096 | 8.876 | 8.739 | 5.357 | 0.0034139 | acyl-CoA synthetase long-chain family member 4 |
| PREX2 | 2.648 | 2.648 | 3.311 | 5.072 | 4.896 | 6.034 | 5.364 | 0.0090021 | phosphatidylinositol-3,4,5-trisphosphate-dependent Rac exchange factor 2 |
| SHOX2 | 7.265 | 6.667 | 6.672 | 9.095 | 8.204 | 9.797 | 5.365 | 0.0174756 | short stature homeobox 2 |
| TUBB2C | 10.754 | 11.200 | 11.438 | 12.578 | 13.676 | 13.862 | 5.368 | 0.0139282 | tubulin, beta 2C |

TABLE 4-continued

Differentially Expressed Genes in CD44+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD44+ N48 | CD44+ N58 | CD44+ N43 | CD44+ N37 | CD44+ N39 | CD44+ N40 | | | | |
| CESS | 2.970 | 3.712 | 3.111 | 4.754 | 5.889 | 6.140 | | 5.381 | 0.0132808 | carboxylesterase 3 |
| ZNF623 | 4.525 | 2.932 | 3.323 | 5.845 | 5.360 | 6.234 | | 5.381 | 0.0176329 | zinc finger protein 623 |
| TSG101 | 8.379 | 7.549 | 8.464 | 12.102 | 10.807 | 9.940 | | 5.383 | 0.0110083 | tumor susceptibility gene 101 |
| THUMPD3 | 2.233 | 2.814 | 2.233 | 4.722 | 5.244 | 3.054 | | 5.390 | 0.0370707 | THUMP domain containing 3 |
| TIMM13 | 8.389 | 7.927 | 9.322 | 10.820 | 11.640 | 10.454 | | 5.394 | 0.0132017 | translocase of inner mitochondrial membrane 13 homolog (yeast) |
| FAM166B | 0.648 | 0.648 | 0.648 | 3.081 | 2.987 | 3.351 | | 5.398 | 0.0024260 | family with sequence similarity 166, member B |
| TMCO2 | 0.648 | 0.648 | 0.648 | 3.081 | 2.987 | 4.748 | | 5.398 | 0.0066340 | transmembrane and coiled-coil domains 2 |
| RBM41 | 0.648 | 0.648 | 0.648 | 3.081 | 3.633 | 2.370 | | 5.398 | 0.0088260 | RNA binding motif protein 41 |
| CLDND2 | 0.648 | 0.648 | 1.962 | 3.081 | 3.633 | 3.966 | | 5.398 | 0.0114055 | claudin domain containing 2 |
| DYSFIP1 | 0.648 | 0.648 | 1.649 | 3.081 | 2.353 | 4.262 | | 5.398 | 0.0212419 | dysferlin interacting protein 1 |
| UBE2Q2P3 | 0.648 | 1.962 | 2.202 | 3.081 | 3.284 | 5.407 | | 5.398 | 0.0293522 | ubiquitin-conjugating enzyme E2Q family member 2 pseudogene 3 |
| INCA1 | 3.860 | 0.648 | 1.245 | 3.081 | 5.053 | 4.602 | | 5.398 | 0.0441279 | inhibitor of CDK, cyclin A1 interacting protein 1 |
| ADAT3 | 6.924 | 4.857 | 6.967 | 8.986 | 9.399 | 9.302 | | 5.400 | 0.0092593 | adenosine deaminase, tRNA-specific 3, TAD3 homolog (S. cerevisiae) |
| DGKQ | 5.664 | 2.970 | 4.070 | 6.504 | 7.003 | 6.188 | | 5.403 | 0.0256967 | diacylglycerol kinase, theta 110 kDa |
| C17orf63 | 6.676 | 6.658 | 7.042 | 9.328 | 9.476 | 8.361 | | 5.404 | 0.0109674 | chromosome 17 open reading frame 63 |
| MPPE1 | 4.619 | 3.615 | 5.355 | 6.463 | 7.054 | 7.135 | | 5.407 | 0.0148856 | metallophosphoesterase 1 |
| ALG13 | 1.648 | 3.023 | 4.174 | 5.459 | 6.219 | 4.975 | | 5.410 | 0.0182555 | asparagine-linked glycosylation 13 homolog (S. cerevisiae) |
| DGKE | 6.455 | 6.470 | 6.994 | 8.717 | 8.906 | 9.444 | | 5.412 | 0.0065979 | diacylglycerol kinase, epsilon 64 kDa |
| LOC400043 | 8.603 | 6.728 | 6.883 | 9.320 | 9.164 | 9.475 | | 5.413 | 0.0315380 | No description |
| ERIS | 7.988 | 6.517 | 7.764 | 10.458 | 9.969 | 8.953 | | 5.415 | 0.0174270 | ERI1 exoribonuclease family member 3 |
| INPP5D | 3.792 | 3.251 | 3.888 | 5.691 | 5.977 | 8.251 | | 5.427 | 0.0119851 | inositol polyphosphate-5-phosphatase, 145 kDa |
| LTB4R | 2.648 | 3.297 | 3.967 | 6.411 | 6.115 | 4.579 | | 5.438 | 0.0185314 | leukotriene B4 receptor |
| RNF208 | 2.233 | 3.508 | 3.029 | 5.952 | 5.416 | 4.955 | | 5.440 | 0.0097799 | ring finger protein 208 |
| CHST6 | 6.522 | 6.243 | 5.659 | 8.483 | 8.687 | 8.922 | | 5.441 | 0.0048274 | carbohydrate (N-acetylglucosamine 6-O) sulfotransferase 6 |
| SFH | 3.947 | 3.511 | 4.650 | 6.391 | 6.969 | 6.100 | | 5.443 | 0.0093113 | Sfi1 homolog, spindle assembly associated (yeast) |
| C8orf73 | 5.600 | 3.178 | 3.126 | 5.571 | 5.934 | 6.411 | | 5.444 | 0.0432510 | chromosome 8 open reading frame 73 |
| LOC100130776 | 3.422 | 4.051 | 4.926 | 6.666 | 6.534 | 5.869 | | 5.455 | 0.0159962 | No description |
| UNC13D | 3.648 | 4.800 | 5.761 | 6.978 | 7.236 | 8.211 | | 5.462 | 0.0128641 | unc-13 homolog D (C. elegans) |
| DPF2 | 6.196 | 5.399 | 6.864 | 8.648 | 8.566 | 8.731 | | 5.471 | 0.0088010 | D4, zinc and double PHD fingers family 2 |
| DDHD2 | 4.580 | 4.579 | 4.269 | 7.151 | 7.033 | 6.653 | | 5.479 | 0.0037348 | DDHD domain containing 2 |
| NT5DC3 | 7.493 | 7.525 | 6.442 | 8.509 | 10.635 | 9.947 | | 5.481 | 0.0163802 | 5'-nucleotidase domain containing 3 |
| CXCL1 | 7.367 | 8.304 | 8.644 | 10.120 | 10.908 | 10.758 | | 5.481 | 0.0096094 | chemokine (C-X-C motif) ligand 1 (melanoma growth stimulating activity, alpha) |
| DPP3 | 4.525 | 4.532 | 4.916 | 7.505 | 6.987 | 6.074 | | 5.481 | 0.0144177 | dipeptidyl-peptidase 3 |
| C9orf80 | 5.945 | 4.181 | 5.551 | 8.046 | 8.006 | 7.926 | | 5.482 | 0.0079726 | chromosome 9 open reading frame 80 |
| NSFL1C | 8.260 | 8.611 | 9.392 | 11.781 | 11.847 | 10.596 | | 5.483 | 0.0091920 | NSFL1 (p97) cofactor (p47) |
| PLCH2 | 1.648 | 1.648 | 1.648 | 3.326 | 5.405 | 4.104 | | 5.486 | 0.0115601 | phospholipase C, eta 2 |
| RBM44 | 1.648 | 3.475 | 1.648 | 4.721 | 5.120 | 4.104 | | 5.486 | 0.0184080 | RNA binding motif protein 44 |
| WDHD1 | 1.648 | 1.648 | 1.648 | 4.624 | 2.739 | 4.104 | | 5.486 | 0.0196572 | WD repeat and HMG-box DNA binding protein 1 |
| FLJ10213 | 1.648 | 1.648 | 1.648 | 4.154 | 2.739 | 4.104 | | 5.491 | 0.0200981 | No description |
| IKBKB | 5.640 | 6.072 | 6.393 | 8.456 | 8.529 | 8.809 | | 5.491 | 0.0040669 | inhibitor of kappa light polypeptide gene enhancer in B-cells, kinase beta |
| EFHC1 | 5.507 | 5.652 | 5.548 | 7.680 | 8.100 | 8.109 | | 5.492 | 0.0037168 | EF-hand domain (C-terminal) containing 1 |

TABLE 4-continued

Differentially Expressed Genes in CD44+ Breast Epithelial Cells

| | Nulliparous (NP) Samples | | | Parous (P) Samples | | | | Pseudo | | |
|---|---|---|---|---|---|---|---|---|---|---|
| Gene Symbol | CD44+ N48 | CD44+ N58 | CD44+ N43 | CD44+ N37 | CD44+ N39 | CD44+ N40 | fold change | P value | Gene description |
| MYO10 | 8.067 | 6.874 | 7.180 | 9.332 | 9.815 | 9.800 | 5.493 | 0.0113432 | myosin X |
| SLC2A8 | 5.587 | 3.202 | 4.432 | 6.891 | 7.266 | 6.835 | 5.496 | 0.0150832 | solute carrier family 2 (facilitated glucose transporter), member 8 |
| RHOF | 4.086 | 3.861 | 4.201 | 4.535 | 6.769 | 6.547 | 5.505 | 0.0400128 | ras homolog gene family, member F (in filopodia) |
| GIGYF1 | 7.565 | 7.333 | 8.150 | 10.137 | 9.982 | 10.027 | 5.510 | 0.0060295 | GRB10 interacting GYF protein 1 |
| VN1R2 | 2.233 | 2.461 | 2.570 | 4.869 | 5.078 | 4.697 | 5.515 | 0.0032621 | vomeronasal 1 receptor 2 |
| AVPI1 | 6.036 | 4.477 | 4.833 | 7.296 | 7.122 | 7.858 | 5.516 | 0.0149549 | arginine vasopressin-induced 1 |
| FUT5 | 4.142 | 2.702 | 2.822 | 5.167 | 5.458 | 6.290 | 5.521 | 0.0143705 | fucosyltransferase 5 (alpha (1,3) fucosyltransferase) |
| TNFRSF6B | 6.340 | 4.174 | 6.102 | 8.568 | 8.711 | 7.484 | 5.529 | 0.0152697 | tumor necrosis factor receptor superfamily, member 6b, decoy |
| USP54 | 5.235 | 4.675 | 5.561 | 7.702 | 7.763 | 7.256 | 5.532 | 0.0068343 | ubiquitin specific peptidase 54 |
| ACOT7 | 8.502 | 5.824 | 8.062 | 9.559 | 10.602 | 10.530 | 5.534 | 0.0173120 | acyl-CoA thioesterase 7 |
| NHEJ1 | 6.135 | 5.576 | 6.520 | 8.604 | 8.673 | 8.580 | 5.535 | 0.0047823 | nonhomologous end-joining factor 1 |
| HN1L | 8.515 | 7.920 | 8.543 | 10.389 | 11.133 | 10.662 | 5.536 | 0.0068614 | hematological and neurological expressed 1 -like |
| GTF2IRD1 | 5.945 | 6.047 | 6.952 | 8.608 | 9.024 | 8.416 | 5.544 | 0.0091026 | GTF2I repeat domain containing 1 |
| SLC23A2 | 6.427 | 5.127 | 5.238 | 7.711 | 7.935 | 7.602 | 5.549 | 0.0151234 | solute carrier family 23 (nucleobase transporters), member 2 |
| GFM1 | 5.899 | 5.836 | 5.465 | 8.308 | 8.486 | 7.309 | 5.549 | 0.0109404 | G elongation factor, mitochondrial 1 |
| KCNK6 | 3.233 | 3.714 | 3.924 | 5.708 | 5.816 | 6.499 | 5.560 | 0.0076260 | potassium channel, subfamily K, member 6 |
| TMEM53 | 6.189 | 4.110 | 6.621 | 8.666 | 8.923 | 8.460 | 5.568 | 0.0103463 | transmembrane protein 53 |
| POU2F2 | 3.818 | 5.285 | 4.794 | 7.366 | 5.382 | 7.762 | 5.569 | 0.0322631 | POU class 2 homeobox 2 |
| C1orf84 | 4.817 | 2.649 | 4.526 | 7.004 | 6.491 | 7.054 | 5.570 | 0.0108655 | chromosome 1 open reading frame 84 |
| TIE1 | 7.977 | 2.648 | 5.810 | 8.767 | 8.027 | 8.288 | 5.572 | 0.0397542 | tyrosine kinase with immunoglobulin-like and EGF-like domains 1 |
| DDTL | 2.233 | 3.870 | 5.064 | 6.297 | 7.199 | 6.349 | 5.574 | 0.0145328 | D-dopachrome tautomerase-like |
| OVGP1 | 3.422 | 2.894 | 2.601 | 4.017 | 5.903 | 5.770 | 5.583 | 0.0212010 | oviductal glycoprotein 1, 120 kDa |
| TECR | 9.400 | 7.745 | 8.252 | 10.740 | 10.883 | 10.712 | 5.607 | 0.0139636 | trans-2,3-enoyl-CoA reductase |
| SQLE | 3.619 | 3.589 | 3.902 | 6.578 | 5.879 | 6.109 | 5.621 | 0.0044239 | squalene epoxidase |
| CNTD2 | 6.227 | 3.696 | 5.310 | 6.131 | 7.801 | 9.169 | 5.621 | 0.0303899 | cyclin N-terminal domain containing 2 |
| OBSCN | 6.209 | 5.364 | 6.521 | 7.361 | 8.700 | 9.029 | 5.624 | 0.0176239 | obscurin, cytoskeletal calmodulin and titin-interacting RhoGEF |
| HIVEP3 | 6.987 | 6.767 | 7.062 | 7.920 | 9.482 | 9.963 | 5.638 | 0.0222825 | human immunodeficiency virus type I enhancer binding protein 3 |
| RNF26 | 6.912 | 5.751 | 6.810 | 9.408 | 9.018 | 8.823 | 5.639 | 0.0072156 | ring finger protein 26 |
| ANKMY1 | 4.008 | 3.059 | 3.544 | 6.619 | 6.040 | 4.376 | 5.642 | 0.0282977 | ankyrin repeat and MYND domain containing 1 |
| PRPSAP2 | 7.568 | 5.865 | 5.222 | 9.915 | 7.721 | 8.867 | 5.654 | 0.0228697 | phosphoribosyl pyrophosphate synthetase-associated protein 2 |
| LRP3 | 9.575 | 6.841 | 7.193 | 10.137 | 9.341 | 10.001 | 5.657 | 0.0496239 | low density lipoprotein receptor-related protein 3 |
| PEX16 | 6.103 | 6.051 | 6.695 | 9.195 | 8.697 | 7.836 | 5.657 | 0.0127428 | peroxisomal biogenesis factor 16 |
| SHISA4 | 6.398 | 4.174 | 4.631 | 7.356 | 6.675 | 7.187 | 5.659 | 0.0334049 | shisa homolog 4 (Xenopus laevis) |
| DPY19L2P2 | 4.657 | 2.814 | 2.778 | 5.610 | 5.561 | 5.279 | 5.662 | 0.0261750 | dpy-19-like 2 pseudogene 2 (C. elegans) |
| ZNF274 | 6.340 | 5.628 | 6.312 | 9.129 | 8.769 | 8.132 | 5.671 | 0.0063761 | zinc finger protein 274 |
| PPP1R3F | 6.714 | 5.154 | 5.703 | 8.882 | 7.842 | 8.209 | 5.680 | 0.0129584 | protein phosphatase 1, regulatory (inhibitor) subunit 3F |
| FGF5 | 5.173 | 4.492 | 5.310 | 7.455 | 7.039 | 7.816 | 5.680 | 0.0073286 | fibroblast growth factor 5 |
| PARD6A | 1.648 | 1.648 | 1.689 | 4.154 | 3.247 | 4.493 | 5.681 | 0.0104156 | par-6 partitioning defective 6 homolog alpha (C. elegans) |
| SULT2B1 | 1.648 | 1.648 | 1.689 | 4.154 | 7.200 | 2.752 | 5.681 | 0.0246853 | sulfotransferase family, cytosolic, 2B, member 1 |
| CNTN4 | 4.423 | 1.648 | 1.978 | 4.154 | 4.945 | 6.261 | 5.681 | 0.0338402 | contactin 4 |
| NEURL2 | 5.264 | 2.776 | 3.077 | 5.502 | 5.591 | 7.140 | 5.713 | 0.0302756 | neuralized homolog 2 (Drosophila) |

TABLE 4-continued

Differentially Expressed Genes in CD44+ Breast Epithelial Cells

| Gene Symbol | Nulliparous (NP) Samples | | | | Parous (P) Samples | | | | Pseudo fold change | P value | Gene description |
|---|---|---|---|---|---|---|---|---|---|---|---|
| | CD44+ N48 | CD44+ N58 | CD44+ N43 | | CD44+ N37 | CD44+ N39 | CD44+ N40 | | | | |
| CST7 | 6.490 | 6.655 | 4.734 | | 7.995 | 7.265 | 9.174 | | 5.733 | 0.0318270 | cystatin F (leukocystatin) |
| PLAU | 10.199 | 8.397 | 8.928 | | 12.719 | 11.986 | 10.247 | | 5.735 | 0.0250416 | plasminogen activator, urokinase |
| MHP | 6.418 | 4.700 | 3.904 | | 7.220 | 7.613 | 7.172 | | 5.737 | 0.0235747 | migration and invasion inhibitory protein |
| NXF1 | 10.852 | 10.034 | 10.767 | | 12.479 | 13.291 | 13.582 | | 5.754 | 0.0077321 | nuclear RNA export factor 1 |
| INSL3 | 1.648 | 1.648 | 1.978 | | 4.017 | 4.174 | 5.512 | | 5.758 | 0.0063581 | insulin-like 3 (Leydig cell) |
| ZNF845 | 1.648 | 1.648 | 2.064 | | 5.272 | 4.174 | 3.557 | | 5.758 | 0.0106825 | zinc finger protein 845 |
| CD79A | 1.648 | 1.648 | 2.121 | | 3.557 | 4.174 | 5.289 | | 5.758 | 0.0110617 | CD79a molecule, immunoglobulin-associated alpha |
| LOC100170939 | 3.422 | 1.648 | 1.834 | | 4.721 | 4.174 | 4.692 | | 5.758 | 0.0192912 | No description |
| TULP2 | 4.008 | 1.648 | 1.689 | | 5.196 | 4.174 | 6.394 | | 5.758 | 0.0201778 | tubby like protein 2 |
| WFIKKN1 | 2.233 | 3.073 | 2.932 | | 3.981 | 5.458 | 6.234 | | 5.758 | 0.0175296 | WAP, follistatin/kazal, immunoglobulin, kunitz and netrin domain containing 1 |
| CNTFR | 6.713 | 3.510 | 4.889 | | 7.416 | 6.851 | 7.904 | | 5.765 | 0.0324080 | ciliary neurotrophic factor receptor |
| ST20 | 0.648 | 0.648 | 1.245 | | 2.714 | 3.284 | 3.773 | | 5.765 | 0.0084281 | suppressor of tumorigenicity 20 |
| CHMP1A | 9.056 | 8.199 | 8.903 | | 11.504 | 11.431 | 10.807 | | 5.768 | 0.0063310 | chromatin modifying protein 1A |
| PHB2 | 11.122 | 9.677 | 11.602 | | 13.653 | 13.722 | 13.241 | | 5.778 | 0.0099116 | prohibitin 2 |
| TGFB2 | 7.261 | 7.356 | 7.414 | | 7.798 | 9.889 | 10.321 | | 5.785 | 0.0389050 | transforming growth factor, beta 2 |
| MAST2 | 8.232 | 7.217 | 9.054 | | 10.186 | 10.399 | 11.587 | | 5.788 | 0.0153029 | microtubule associated serine/threonine kinase 2 |
| MRPL12 | 7.693 | 7.320 | 7.201 | | 10.160 | 10.228 | 8.572 | | 5.794 | 0.0176149 | mitochondrial ribosomal protein L12 |
| HTR7P | 4.142 | 2.702 | 4.417 | | 6.952 | 6.654 | 6.293 | | 5.795 | 0.0073695 | No description |
| BAIAP2L1 | 7.362 | 6.084 | 7.107 | | 8.621 | 11.266 | 8.696 | | 5.804 | 0.0214291 | BAH-associated protein 2-like 1 |
| LRRC4B | 5.452 | 2.234 | 4.097 | | 7.446 | 5.060 | 6.634 | | 5.804 | 0.0382818 | leucine rich repeat containing 4B |
| SESN1 | 7.203 | 6.346 | 5.537 | | 9.324 | 8.077 | 9.352 | | 5.815 | 0.0138783 | sestrin 1 |
| GIT1 | 6.290 | 4.117 | 5.637 | | 8.034 | 8.178 | 8.233 | | 5.821 | 0.0102922 | G protein-coupled receptor kinase interacting ArfGAP 1 |
| KCNRG | 1.648 | 1.648 | 1.834 | | 4.376 | 3.805 | 4.376 | | 5.822 | 0.0039948 | potassium channel regulator |
| CDKN2A | 7.001 | 5.075 | 5.523 | | 8.814 | 7.769 | 8.066 | | 5.826 | 0.0187816 | cyclin-dependent kinase inhibitor 2A (melanoma, p16, inhibits CDK4) |
| SOX5 | 5.169 | 2.233 | 2.607 | | 5.696 | 4.777 | 7.389 | | 5.830 | 0.0328627 | SRY (sex determining region Y)-box 5 |
| FAM55C | 7.304 | 5.595 | 5.041 | | 7.949 | 8.140 | 8.575 | | 5.839 | 0.0240530 | family with sequence similarity 55, member C |
| RBM39 | 9.438 | 10.031 | 9.513 | | 12.113 | 11.192 | 12.578 | | 5.844 | 0.0126354 | RNA binding motif protein 39 |
| SHROOM1 | 5.849 | 3.982 | 4.953 | | 7.577 | 7.501 | 6.745 | | 5.848 | 0.0167068 | shroom family member 1 |
| SNRPA | 8.842 | 7.493 | 8.741 | | 11.397 | 10.536 | 10.938 | | 5.878 | 0.0093203 | small nuclear ribonucleoprotein polypeptide A |
| CHST9 | 2.233 | 2.391 | 2.570 | | 4.804 | 5.126 | 4.908 | | 5.883 | 0.0024711 | carbohydrate (N-acetylgalactosamine 4-0) sulfotransferase 9 |
| PI4K2A | 9.643 | 9.633 | 10.693 | | 12.113 | 12.543 | 13.251 | | 5.889 | 0.0081466 | phosphatidylinositol 4-kinase type 2 alpha |
| MZF1 | 5.552 | 5.555 | 6.338 | | 8.112 | 8.321 | 8.148 | | 5.898 | 0.0063400 | myeloid zinc finger 1 |
| PDE4C | 4.349 | 4.387 | 4.580 | | 6.949 | 6.344 | 7.261 | | 5.907 | 0.0062132 | phosphodiesterase 4C, cAMP-specific |
| APOA1 | 4.647 | 2.593 | 3.143 | | 4.748 | 6.666 | 7.209 | | 5.907 | 0.0200711 | apolipoprotein A-I |
| DMXL1 | 5.920 | 4.770 | 4.899 | | 8.314 | 7.333 | 7.474 | | 5.909 | 0.0100641 | Dmx-like 1 |
| WDR43 | 7.898 | 8.007 | 7.782 | | 9.862 | 10.967 | 10.461 | | 5.913 | 0.0058672 | WD repeat domain 43 |
| TTC32 | 5.104 | 3.934 | 4.250 | | 7.262 | 6.579 | 6.815 | | 5.917 | 0.0087581 | tetratricopeptide repeat domain 32 |
| C12orf10 | 8.314 | 7.730 | 7.649 | | 10.879 | 10.300 | 10.195 | | 5.917 | 0.0165917 | chromosome 12 open reading frame 10 |
| MCM5 | 7.876 | 5.466 | 6.717 | | 9.396 | 8.932 | 9.284 | | 5.927 | 0.0050790 | minichromosome maintenance complex component 5 |
| C2orf14 | 3.194 | 4.647 | 4.990 | | 6.811 | 7.215 | 7.380 | | 5.932 | 0.0078153 | chromosome 2 open reading frame 14 |
| C5orf56 | 2.233 | 2.360 | 2.233 | | 4.804 | 4.729 | 5.304 | | 5.941 | 0.0024621 | chromosome 5 open reading frame 56 |
| KRBA2 | 7.394 | 6.075 | 6.953 | | 9.507 | 9.526 | 9.546 | | 5.953 | 0.0053591 | KRAB-A domain containing 2 |
| UCKL1 | 7.949 | 6.414 | 7.805 | | 10.523 | 10.076 | 9.721 | | 5.955 | 0.0086832 | uridine-cytidine kinase 1-like 1 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| PSMD1 | 8.215 | 8.900 | 9.427 | 12.336 | 11.471 | 10.789 | 5.956 | 0.0099442 | proteasome (prosome, macropain) 26S subunit, non-ATPase, 1 |
| INPP5K | 4.214 | 5.296 | 4.875 | 7.452 | 6.595 | 8.152 | 5.967 | 0.0105764 | inositol polyphosphate-5-phosphatase K |
| MRPL48 | 5.870 | 3.256 | 4.381 | 7.261 | 6.966 | 6.006 | 5.999 | 0.0303712 | mitochondrial ribosomal protein L48 |
| MRPL14 | 8.726 | 8.124 | 7.274 | 10.711 | 11.196 | 10.599 | 6.008 | 0.0060114 | mitochondrial ribosomal protein L14 |
| ST6GALNAC4 | 8.204 | 5.889 | 7.513 | 10.793 | 9.636 | 8.886 | 6.015 | 0.0216482 | ST6 (alpha-N-acetyl-neuraminyl-2,3-beta-galactosyl-1,3)-N-acetylgalactosaminide alpha-2,6-sialyltransferase 4 |
| LAMP3 | 2.970 | 3.802 | 3.471 | 5.561 | 6.172 | 6.378 | 6.023 | 0.0054097 | lysosomal-associated membrane protein 3 |
| AES | 11.673 | 9.728 | 10.884 | 13.376 | 13.475 | 13.484 | 6.024 | 0.0098666 | amino-terminal enhancer of split |
| DDA1 | 9.278 | 8.660 | 9.334 | 11.737 | 12.015 | 11.251 | 6.024 | 0.0051740 | DET1 and DDB1 associated 1 |
| LOC100128675 | 2.648 | 2.768 | 3.937 | 5.762 | 5.240 | 5.709 | 6.027 | 0.0101002 | No description |
| FZD5 | 6.259 | 6.182 | 7.013 | 8.020 | 8.853 | 9.645 | 6.041 | 0.0145716 | frizzled homolog 5 (Drosophila) |
| FCGBP | 2.233 | 2.233 | 4.242 | 5.109 | 3.686 | 6.838 | 6.048 | 0.0437938 | Fc fragment of IgG binding protein |
| ALKBH4 | 8.856 | 6.574 | 7.826 | 10.610 | 10.359 | 10.423 | 6.048 | 0.0118693 | alkB, alkylation repair homolog 4 (E. coli) |
| NCRNA00115 | 1.648 | 2.234 | 2.894 | 4.830 | 2.739 | 6.165 | 6.049 | 0.0388045 | non-protein coding RNA 115 |
| MDM4 | 6.256 | 6.545 | 7.307 | 9.535 | 9.150 | 8.967 | 6.084 | 0.0068704 | Mdm4 p53 binding protein homolog (mouse) |
| LOC442421 | 2.648 | 2.648 | 2.822 | 5.929 | 4.713 | 5.255 | 6.091 | 0.0059123 | No description |
| TMEM63A | 5.178 | 4.384 | 4.935 | 7.788 | 7.517 | 7.461 | 6.105 | 0.0029307 | transmembrane protein 63A |
| PTBP1 | 10.547 | 7.741 | 8.385 | 10.997 | 11.093 | 10.995 | 6.113 | 0.0354769 | polypyrimidine tract binding protein 1 |
| C15orf61 | 6.756 | 4.734 | 6.056 | 8.626 | 8.769 | 8.671 | 6.128 | 0.0084052 | chromosome 15 open reading frame 61 |
| WWTR1 | 9.083 | 7.689 | 8.746 | 10.062 | 11.364 | 12.309 | 6.140 | 0.0144718 | WW domain containing transcription regulator 1 |
| BEGAIN | 5.482 | 5.815 | 5.909 | 7.074 | 8.623 | 8.434 | 6.143 | 0.0144024 | brain-enriched guanylate kinase-associated homolog (rat) |
| ITGB5 | 11.469 | 9.747 | 6.419 | 14.088 | 13.589 | 12.458 | 6.146 | 0.0143158 | integrin, beta 5 |
| WDR54 | 4.817 | 2.800 | 3.843 | 7.437 | 5.701 | 5.793 | 6.147 | 0.0210270 | WD repeat domain 54 |
| KCNH3 | 4.142 | 3.073 | 4.160 | 6.098 | 6.952 | 5.696 | 6.159 | 0.0119289 | potassium voltage-gated channel, subfamily H (eag-related), member 3 |
| PROCA1 | 0.648 | 0.648 | 1.245 | 3.871 | 2.987 | 3.773 | 6.170 | 0.0046853 | protein interacting with cyclin A1 |
| NONO | 8.444 | 8.711 | 8.853 | 11.153 | 11.774 | 11.073 | 6.184 | 0.0034409 | non-POU domain containing, octamer-binding |
| PCBD2 | 5.998 | 4.564 | 4.884 | 7.513 | 7.278 | 7.695 | 6.185 | 0.0119490 | pterin-4 alpha-carbinolamine dehydratase/dimerization cofactor of hepatocyte nuclear factor 1 alpha (TCF1) 2 |
| RHOD | 5.908 | 4.674 | 5.424 | 7.999 | 9.507 | 7.303 | 6.189 | 0.0107144 | ras homolog gene family, member D |
| SLC26A6 | 6.368 | 2.991 | 5.451 | 8.082 | 6.851 | 8.835 | 6.194 | 0.0211650 | solute carrier family 26, member 6 |
| FAM3A | 6.368 | 6.729 | 7.859 | 10.315 | 9.360 | 9.299 | 6.195 | 0.0098125 | family with sequence similarity 3, member A |
| USF1 | 2.233 | 2.233 | 3.118 | 5.253 | 4.818 | 5.752 | 6.207 | 0.0053140 | upstream transcription factor 1 |
| RDBP | 8.238 | 7.245 | 6.419 | 10.492 | 9.989 | 9.054 | 6.212 | 0.0151075 | RD RNA binding protein |
| SKA1 | 0.648 | 0.648 | 0.648 | 3.081 | 3.284 | 3.773 | 6.213 | 0.0022908 | spindle and kinetochore associated complex subunit 1 |
| CENPA | 0.648 | 0.648 | 0.999 | 3.662 | 3.284 | 3.043 | 6.213 | 0.0035844 | centromere protein A |
| KLRC3 | 0.648 | 0.648 | 1.719 | 2.202 | 3.284 | 5.407 | 6.213 | 0.0246402 | killer cell lectin-like receptor subfamily C, member 3 |
| LXN | 3.194 | 4.021 | 2.329 | 6.124 | 5.411 | 5.830 | 6.218 | 0.0101362 | latexin |
| POP4 | 3.619 | 2.233 | 2.987 | 6.471 | 5.626 | 4.777 | 6.230 | 0.0115109 | processing of precursor 4, ribonuclease P/MRP subunit (S. cerevisiae) |
| RPS6KB2 | 2.233 | 3.435 | 3.592 | 5.330 | 6.234 | 5.045 | 6.244 | 0.0134319 | ribosomal protein S6 kinase, 70 kDa, polypeptide 2 |
| DNAH12 | 3.422 | 3.557 | 3.645 | 6.065 | 6.340 | 6.091 | 6.247 | 0.0017071 | dynein, axonemal, heavy chain 12 |
| KAT5 | 5.982 | 5.883 | 3.696 | 8.625 | 7.290 | 6.905 | 6.249 | 0.0268690 | K(lysine) acetyltransferase 5 |
| DAXX | 9.165 | 7.966 | 9.083 | 11.415 | 11.809 | 11.438 | 6.254 | 0.0048094 | death-domain associated protein |
| NRBP1 | 8.644 | 8.738 | 8.507 | 11.870 | 11.290 | 11.138 | 6.259 | 0.0022305 | nuclear receptor binding protein 1 |

TABLE 4-continued

Differentially Expressed Genes in CD44+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD44+ N48 | CD44+ N58 | CD44+ N43 | CD44+ N37 | CD44+ N39 | CD44+ N40 | | | | |
| ACP1 | 6.062 | 5.239 | 6.471 | 8.709 | 9.351 | 7.416 | | 6.266 | 0.0146520 | acid phosphatase 1, soluble |
| GPR137 | 6.570 | 5.610 | 7.392 | 9.654 | 9.218 | 9.150 | | 6.266 | 0.0074998 | G protein-coupled receptor 137 |
| DGKZ | 5.973 | 5.489 | 5.902 | 7.877 | 8.550 | 8.766 | | 6.268 | 0.0047733 | diacylglycerol kinase, zeta |
| C21orf2 | 8.234 | 4.692 | 6.995 | 9.877 | 9.644 | 9.054 | | 6.272 | 0.0203179 | chromosome 21 open reading frame 2 |
| CCR7 | 3.233 | 5.306 | 4.835 | 7.485 | 5.768 | 9.409 | | 6.275 | 0.0207442 | chemokine (C-C motif) receptor 7 |
| RIPK1 | 8.020 | 6.117 | 6.060 | 9.536 | 9.163 | 8.710 | | 6.277 | 0.0184683 | receptor (TNFRSF)-interacting serine-threonine kinase 1 |
| FGFRL1 | 6.350 | 7.142 | 7.403 | 9.000 | 10.486 | 9.742 | | 6.277 | 0.0077972 | fibroblast growth factor receptor-like 1 |
| S100A3 | 5.264 | 3.247 | 3.423 | 6.308 | 7.915 | 5.398 | | 6.280 | 0.0253244 | S100 calcium binding protein A3 |
| DCFS | 6.232 | 2.625 | 4.839 | 7.890 | 7.493 | 6.634 | | 6.294 | 0.0246069 | decapping enzyme, scavenger |
| C4orf52 | 1.648 | 1.648 | 2.307 | 4.376 | 4.017 | 4.961 | | 6.295 | 0.0059213 | chromosome 4 open reading frame 52 |
| SLC13A3 | 2.648 | 3.520 | 2.744 | 5.385 | 5.733 | 5.400 | | 6.303 | 0.0053501 | solute carrier family 13 (sodium-dependent dicarboxylate transporter), members |
| NUDT16 | 4.264 | 4.280 | 3.574 | 7.404 | 6.234 | 6.388 | | 6.321 | 0.0072697 | nudix (nucleoside diphosphate linked moiety X)-type motif 16 |
| SRRT | 8.801 | 8.070 | 9.600 | 11.344 | 11.756 | 11.464 | | 6.335 | 0.0070742 | serrate RNA effector molecule homolog (Arabidopsis) |
| PCYOX1 | 7.113 | 4.762 | 4.280 | 7.817 | 7.427 | 7.309 | | 6.345 | 0.0378818 | prenylcysteine oxidase 1 |
| PLIN5 | 4.620 | 3.402 | 4.816 | 6.509 | 7.483 | 6.832 | | 6.350 | 0.0090846 | perilipin 5 |
| FST | 9.636 | 8.987 | 10.029 | 12.696 | 12.461 | 10.747 | | 6.352 | 0.0180815 | follistatin |
| SNRNP25 | 5.550 | 2.714 | 3.644 | 6.312 | 6.666 | 6.058 | | 6.358 | 0.0257397 | small nuclear ribonucleoprotein 25 kDa (U11/U12) |
| REL | 9.044 | 7.696 | 7.864 | 10.630 | 10.254 | 11.714 | | 6.362 | 0.0111477 | v-rel reticuloendotheliosis viral oncogene homolog (avian) |
| COPS7B | 3.422 | 2.926 | 3.423 | 6.136 | 4.692 | 6.091 | | 6.363 | 0.0127830 | COP9 constitutive photomorphogenic homolog subunit 7B (Arabidopsis) |
| THAP4 | 8.737 | 7.168 | 7.951 | 10.624 | 10.715 | 10.029 | | 6.375 | 0.0108045 | THAP domain containing 4 |
| MDK | 9.419 | 6.573 | 7.942 | 9.393 | 10.615 | 10.915 | | 6.378 | 0.0318180 | midkine (neurite growth-promoting factor 2) |
| LDLR | 11.145 | 9.238 | 10.343 | 13.139 | 13.351 | 11.911 | | 6.381 | 0.0158922 | low density lipoprotein receptor |
| CYP27C1 | 5.264 | 4.451 | 5.124 | 7.829 | 7.659 | 7.799 | | 6.385 | 0.0025702 | cytochrome P450, family 27, subfamily C, polypeptide 1 |
| STEAP1 | 6.202 | 5.166 | 5.748 | 9.886 | 8.423 | 7.786 | | 6.390 | 0.0086742 | six transmembrane epithelial antigen of the prostate 1 |
| B3GAT3 | 7.312 | 5.769 | 6.057 | 9.021 | 9.183 | 8.448 | | 6.404 | 0.0113251 | beta-1,3-glucuronyltransferase 3 (glucuronosyltransferase I) |
| DNAJC8 | 7.894 | 7.702 | 8.770 | 10.961 | 10.573 | 10.505 | | 6.404 | 0.0062901 | DnaJ (Hsp40) homolog, subfamily C, member 8 |
| C6orf145 | 10.253 | 9.976 | 11.077 | 13.185 | 12.581 | 13.758 | | 6.416 | 0.0069452 | chromosome 6 open reading frame 145 |
| HMOX2 | 8.521 | 6.826 | 8.220 | 10.903 | 11.025 | 10.098 | | 6.423 | 0.0086991 | heme oxygenase (decycling) 2 |
| DPH3B | 1.648 | 1.834 | 1.689 | 4.376 | 4.811 | 4.104 | | 6.437 | 0.0026367 | No description |
| NEDD4 | 2.648 | 2.908 | 3.405 | 5.599 | 5.682 | 5.336 | | 6.443 | 0.0041515 | neural precursor cell expressed, developmentally down-regulated 4 |
| ZBTB7C | 6.547 | 3.475 | 2.721 | 5.409 | 7.084 | 7.657 | | 6.446 | 0.0484676 | zinc finger and BTB domain containing 7C |
| WDR45 | 8.195 | 7.305 | 8.012 | 10.884 | 10.370 | 10.278 | | 6.448 | 0.0046672 | WD repeat domain 45 |
| KREMEN1 | 4.916 | 5.052 | 5.621 | 7.734 | 7.746 | 7.887 | | 6.468 | 0.0034874 | kringle containing transmembrane protein 1 |
| CARS | 8.256 | 7.492 | 8.359 | 11.053 | 10.980 | 9.389 | | 6.469 | 0.0151664 | cysteinyl-tRNA synthetase |
| GSC | 5.781 | 4.027 | 5.796 | 8.490 | 7.162 | 8.178 | | 6.472 | 0.0125813 | goosecoid homeobox |
| NXNL2 | 3.619 | 3.415 | 4.290 | 6.628 | 6.168 | 6.313 | | 6.472 | 0.0047192 | nucleoredoxin-like 2 |
| YPEL1 | 4.214 | 4.997 | 5.011 | 7.002 | 7.707 | 7.358 | | 6.480 | 0.0052600 | yippee-like 1 (Drosophila) |
| MAP3K7IP1 | 6.368 | 4.543 | 5.200 | 8.611 | 7.967 | 7.239 | | 6.480 | 0.0143435 | No description |
| UGGT2 | 4.565 | 3.752 | 5.288 | 7.985 | 7.353 | 5.802 | | 6.485 | 0.0193924 | UDP-glucose glycoprotein glucosyltransferase 2 |
| TOM1 | 7.660 | 7.549 | 5.875 | 10.358 | 8.711 | 8.977 | | 6.488 | 0.0242513 | target of myb1 (chicken) |
| KIAA0649 | 5.644 | 3.143 | 3.231 | 6.384 | 6.386 | 5.842 | | 6.494 | 0.0318360 | KIAA0649 |
| SNORA80B | 0.648 | 2.359 | 0.648 | 3.871 | 4.728 | 3.351 | | 6.508 | 0.0119581 | small nucleolar RNA, H/ACA box 80B |
| KRTAP2-4 | 0.648 | 0.648 | 0.648 | 2.202 | 4.602 | 3.351 | | 6.508 | 0.0122659 | keratin associated protein 2-4 |

TABLE 4-continued

Differentially Expressed Genes in CD44+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD44+ N48 | CD44+ N58 | CD44+ N43 | CD44+ N37 | CD44+ N39 | CD44+ N40 | | | | |
| DUSP9 | 3.194 | 0.648 | 0.648 | 3.351 | 4.043 | 3.773 | | 6.508 | 0.0323712 | dual specificity phosphatase 9 |
| PRDX6 | 10.697 | 10.443 | 10.454 | 13.734 | 12.822 | 13.162 | | 6.534 | 0.0035934 | peroxiredoxin 6 |
| S100A13 | 0.648 | 0.648 | 1.719 | 3.351 | 4.428 | 4.389 | | 6.540 | 0.0045827 | S100 calcium binding protein A13 |
| AHNAK2 | 5.322 | 3.737 | 3.982 | 5.462 | 6.785 | 8.036 | | 6.561 | 0.0262409 | AHNAK nucleoprotein 2 |
| PYCR1 | 8.229 | 5.885 | 7.535 | 10.249 | 10.373 | 8.817 | | 6.563 | 0.0198589 | pyrroline-5-carboxylate reductase 1 |
| YIF1B | 2.648 | 3.337 | 3.381 | 5.904 | 6.229 | 5.367 | | 6.581 | 0.0046312 | Yip interacting factor homolog B (*S. cerevisiae*) |
| CTRC | 5.109 | 2.233 | 3.008 | 4.953 | 6.218 | 5.811 | | 6.586 | 0.0368662 | chymotrypsin C (caldecrin) |
| ADRB3 | 4.972 | 4.986 | 4.665 | 7.695 | 7.380 | 7.786 | | 6.605 | 0.0017432 | adrenergic, beta-3-, receptor |
| IQCE | 5.453 | 3.951 | 4.219 | 6.943 | 7.048 | 6.937 | | 6.607 | 0.0108565 | IQ motif containing E |
| PIK3CG | 1.648 | 1.648 | 1.648 | 4.376 | 4.421 | 4.376 | | 6.623 | 0.0006645 | phosphoinositide-3-kinase, catalytic, gamma polypeptide |
| FADS6 | 1.648 | 1.648 | 1.834 | 4.376 | 4.529 | 4.493 | | 6.623 | 0.0009321 | fatty acid desaturase domain family, member 6 |
| ERP27 | 1.648 | 1.648 | 1.834 | 4.931 | 4.174 | 4.376 | | 6.623 | 0.0024801 | endoplasmic reticulum protein 27 |
| SIRPB1 | 4.423 | 1.648 | 1.834 | 4.376 | 5.120 | 5.289 | | 6.623 | 0.0331643 | signal-regulatory protein beta 1 |
| HNRNPU | 9.462 | 9.673 | 10.173 | 12.191 | 12.604 | 12.776 | | 6.628 | 0.0032080 | heterogeneous nuclear ribonucleoprotein U (scaffold attachment factor A) |
| ATP6V0B | 8.664 | 8.998 | 9.078 | 12.068 | 11.360 | 11.727 | | 6.634 | 0.0024530 | ATPase, H+ transporting, lysosomal 21 kDa, V0 subunit b |
| FANCC | 4.482 | 3.921 | 5.457 | 6.652 | 7.841 | 8.150 | | 6.639 | 0.0083241 | Fanconi anemia, complementation group C |
| SNX8 | 5.644 | 6.180 | 7.334 | 9.368 | 9.074 | 8.375 | | 6.643 | 0.0121487 | sorting nexin 8 |
| MMP17 | 2.970 | 3.682 | 5.146 | 6.742 | 6.169 | 6.414 | | 6.647 | 0.0154263 | matrix metallopeptidase 17 (membrane-inserted) |
| LOC100128640 | 2.648 | 3.314 | 3.891 | 6.049 | 5.682 | 6.251 | | 6.659 | 0.0055879 | No description |
| SCARF1 | 4.378 | 2.970 | 3.607 | 5.706 | 6.345 | 6.414 | | 6.661 | 0.0098395 | scavenger receptor class F, member 1 |
| REEP4 | 5.644 | 4.206 | 5.452 | 8.191 | 8.224 | 7.604 | | 6.678 | 0.0056198 | receptor accessory protein 4 |
| MMEL1 | 1.648 | 1.648 | 2.721 | 4.721 | 5.463 | 3.929 | | 6.689 | 0.0097120 | membrane metallo-endopeptidase-like 1 |
| NAP1L4 | 9.539 | 8.476 | 10.753 | 11.936 | 12.636 | 12.290 | | 6.732 | 0.0127199 | nucleosome assembly protein 1 -like 4 |
| SETDB1 | 3.947 | 4.681 | 5.606 | 7.499 | 7.434 | 6.857 | | 6.738 | 0.0110374 | SET domain, bifurcated 1 |
| TBRG4 | 7.002 | 7.572 | 8.748 | 10.736 | 10.847 | 9.756 | | 6.745 | 0.0113106 | transforming growth factor beta regulator 4 |
| C7orf43 | 5.690 | 6.907 | 6.059 | 8.601 | 8.817 | 8.925 | | 6.763 | 0.0066700 | chromosome 7 open reading frame 43 |
| PRRT1 | 5.861 | 2.648 | 3.533 | 6.131 | 6.291 | 6.955 | | 6.768 | 0.0296343 | proline-rich transmembrane protein 1 |
| ARL16 | 7.672 | 6.908 | 7.938 | 9.918 | 10.698 | 9.757 | | 6.770 | 0.0072426 | ADP-ribosylation factor-like 16 |
| TMEM212 | 6.190 | 5.826 | 6.188 | 8.496 | 8.947 | 9.601 | | 6.773 | 0.0030478 | transmembrane protein 212 |
| RRP7B | 3.792 | 3.630 | 3.953 | 5.420 | 6.951 | 6.553 | | 6.779 | 0.0096960 | ribosomal RNA processing 7 homolog B (*S. cerevisiae*) |
| SNX22 | 4.672 | 5.305 | 5.648 | 7.542 | 7.842 | 8.412 | | 6.793 | 0.0051969 | sorting nexin 22 |
| NLE1 | 7.085 | 5.988 | 6.730 | 8.941 | 9.911 | 8.752 | | 6.796 | 0.0087920 | notchless homolog 1 (*Drosophila*) |
| SFRS14 | 5.861 | 5.074 | 5.572 | 7.924 | 8.626 | 8.069 | | 6.799 | 0.0041244 | No description |
| PKP4 | 8.857 | 7.861 | 8.549 | 10.628 | 11.874 | 10.654 | | 6.810 | 0.0089244 | plakophilin 4 |
| DDX39 | 8.965 | 8.184 | 9.528 | 11.733 | 11.388 | 12.062 | | 6.811 | 0.0051879 | DEAD (Asp-Glu-Ala-Asp) box polypeptide 39 |
| RPS11 | 14.938 | 13.319 | 13.651 | 16.805 | 16.567 | 16.087 | | 6.813 | 0.0114645 | ribosomal protein S11 |
| SLC43A2 | 7.746 | 6.791 | 6.328 | 9.838 | 9.135 | 9.561 | | 6.819 | 0.0089154 | solute carrier family 43, member 2 |
| NHLRC1 | 2.233 | 2.233 | 2.565 | 5.003 | 5.183 | 5.279 | | 6.819 | 0.0012468 | NHL repeat containing 1 |
| ATP2A3 | 5.731 | 5.050 | 4.995 | 8.448 | 7.765 | 8.258 | | 6.822 | 0.0028517 | ATPase, Ca++ transporting, ubiquitous |
| TMEM229B | 1.648 | 1.648 | 1.648 | 5.102 | 4.421 | 3.294 | | 6.832 | 0.0096780 | transmembrane protein 229B |
| LOC344967 | 7.478 | 5.748 | 6.198 | 8.789 | 9.086 | 8.970 | | 6.833 | 0.0119199 | No description |
| PATE4 | 0.648 | 1.648 | 2.781 | 5.553 | 5.742 | 5.343 | | 6.835 | 0.0253334 | prostate and testis expressed 4 |
| KIAA1984 | 1.648 | 4.713 | 3.963 | 4.830 | 5.932 | 5.398 | | 6.837 | 0.0153480 | KIAA1984 |
| FLJ25006 | 2.233 | 2.625 | 3.323 | 5.821 | 5.167 | 6.074 | | 6.842 | 0.0051061 | No description |
| POLG | 8.151 | 3.047 | 8.700 | 10.906 | 10.926 | 11.497 | | 6.845 | 0.0029848 | polymerase (DNA directed), gamma |

TABLE 4-continued

Differentially Expressed Genes in CD44+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD44+ N48 | CD44+ N58 | CD44+ N43 | CD44+ N37 | CD44+ N39 | CD44+ N40 | | | | |
| TMEM222 | 8.159 | 7.523 | 7.573 | 10.934 | 10.769 | 10.196 | | 6.845 | 0.0028177 | transmembrane protein 222 |
| FKBPL | 5.452 | 3.294 | 3.077 | 5.853 | 6.401 | 6.962 | | 6.849 | 0.0223407 | FK506 binding protein like |
| APEH | 8.083 | 5.618 | 7.093 | 10.272 | 9.872 | 9.040 | | 6.861 | 0.0142818 | N-acylaminoacyl-peptide hydrolase |
| SLC35B1 | 7.886 | 7.192 | 8.196 | 11.478 | 10.665 | 9.658 | | 6.864 | 0.0085598 | solute carrier family 35, member B1 |
| APEX2 | 6.232 | 3.627 | 5.060 | 8.120 | 7.843 | 6.743 | | 6.882 | 0.0201300 | APEX nuclease (apurinic/apyrimidinic endonuclease) 2 |
| MUC16 | 3.233 | 3.848 | 3.233 | 5.157 | 7.664 | 6.016 | | 6.883 | 0.0124530 | mucin 16, cell surface associated |
| TMEM81 | 0.648 | 1.078 | 1.719 | 2.714 | 3.871 | 5.462 | | 6.931 | 0.0144898 | transmembrane protein 81 |
| NDUFV3 | 7.470 | 5.950 | 6.313 | 10.267 | 10.042 | 8.457 | | 6.947 | 0.0094257 | NADH dehydrogenase (ubiquinone) flavoprotein 3, 10 kDa |
| DDN | 1.648 | 1.648 | 2.177 | 3.326 | 4.529 | 4.975 | | 6.953 | 0.0122270 | dendrin |
| PSMB2 | 8.737 | 9.104 | 8.911 | 11.987 | 11.709 | 10.520 | | 6.953 | 0.0100371 | proteasome (prosome, macropain) subunit, beta type, 2 |
| SCFD2 | 2.970 | 3.984 | 3.111 | 5.859 | 5.910 | 6.111 | | 6.957 | 0.0052149 | sed family domain containing 2 |
| KIAA1949 | 12.647 | 9.975 | 9.867 | 12.774 | 12.769 | 14.106 | | 6.961 | 0.0329334 | KIAA1949 |
| B3GNT3 | 4.620 | 4.199 | 4.939 | 7.195 | 7.419 | 7.528 | | 6.963 | 0.0024170 | UDP-GlcNAc:betaGal beta-1,3-N-acetylglucosaminyltransferase 3 |
| STAT4 | 6.196 | 3.047 | 3.278 | 6.451 | 5.858 | 8.147 | | 7.016 | 0.0330562 | signal transducer and activator of transcription 4 |
| PSPH | 4.817 | 2.233 | 2.233 | 5.551 | 5.637 | 5.045 | | 7.022 | 0.0291553 | phosphoserine phosphatase |
| C18orf25 | 6.447 | 6.066 | 5.995 | 8.630 | 8.880 | 9.268 | | 7.034 | 0.0025868 | chromosome 18 open reading frame 25 |
| TRIP4 | 5.739 | 4.335 | 4.593 | 8.513 | 7.921 | 7.156 | | 7.066 | 0.0067213 | thyroid hormone receptor interactor 4 |
| CDH24 | 4.142 | 2.565 | 4.481 | 6.423 | 7.300 | 6.965 | | 7.077 | 0.0059754 | cadherin 24, type 2 |
| CD40 | 7.982 | 7.023 | 5.479 | 10.433 | 9.314 | 9.847 | | 7.081 | 0.0106402 | CD40 molecule, TNF receptor superfamily member 5 |
| KIAA0406 | 4.264 | 4.887 | 3.431 | 7.089 | 7.477 | 6.897 | | 7.086 | 0.0045147 | No description |
| APOL3 | 7.218 | 5.220 | 6.824 | 10.044 | 9.074 | 8.877 | | 7.087 | 0.0103102 | apolipoprotein L, 3 |
| METT11D1 | 7.715 | 6.688 | 7.373 | 10.253 | 10.378 | 9.514 | | 7.090 | 0.0050159 | methyltransferase 11 domain containing 1 |
| DHX38 | 7.942 | 6.174 | 5.515 | 9.761 | 8.342 | 10.121 | | 7.094 | 0.0158146 | DEAH (Asp-Glu-Ala-His) box polypeptide 38 |
| ADORA3 | 1.648 | 1.648 | 1.689 | 4.477 | 3.499 | 4.830 | | 7.106 | 0.0067664 | adenosine A3 receptor |
| FLJ14107 | 1.648 | 1.648 | 1.648 | 4.477 | 4.945 | 3.294 | | 7.106 | 0.0091740 | No description |
| PLD6 | 5.393 | 4.174 | 4.155 | 6.984 | 7.003 | 7.285 | | 7.107 | 0.0083782 | phospholipase D family, member 6 |
| CAPZB | 11.147 | 9.276 | 10.071 | 13.734 | 12.906 | 12.597 | | 7.131 | 0.0084974 | capping protein (actin filament) muscle Z-line, beta |
| YJEFN3 | 1.648 | 2.625 | 2.559 | 5.042 | 4.692 | 5.459 | | 7.132 | 0.0046763 | YjeF N-terminal domain containing 3 |
| KLC1 | 8.922 | 7.998 | 9.869 | 11.798 | 11.759 | 11.041 | | 7.145 | 0.0116440 | kinesin light chain 1 |
| DNHD1 | 5.455 | 4.625 | 5.180 | 8.293 | 7.574 | 7.738 | | 7.151 | 0.0037868 | dynein heavy chain domain 1 |
| PIK3R1 | 8.455 | 7.701 | 7.359 | 11.299 | 10.710 | 10.014 | | 7.178 | 0.0062672 | phosphoinositide-3-kinase, regulatory subunit 1 (alpha) |
| FAM70B | 4.972 | 0.648 | 2.401 | 5.870 | 5.246 | 4.748 | | 7.182 | 0.0377764 | family with sequence similarity 70, member B |
| CXCL17 | 1.648 | 4.006 | 3.879 | 5.908 | 6.914 | 4.493 | | 7.184 | 0.0267005 | chemokine (C-X-C motif) ligand 17 |
| TTC21A | 0.648 | 0.648 | 1.753 | 3.081 | 4.043 | 4.602 | | 7.201 | 0.0074818 | tetratricopeptide repeat domain 21A |
| LOC644669 | 0.648 | 3.043 | 4.647 | 5.813 | 5.894 | 6.847 | | 7.214 | 0.0149459 | No description |
| ERLIN1 | 8.037 | 5.870 | 8.277 | 10.934 | 10.519 | 10.889 | | 7.223 | 0.0063491 | ER lipid raft associated 1 |
| FAM41C | 5.264 | 4.386 | 6.217 | 7.786 | 8.549 | 8.125 | | 7.266 | 0.0076440 | family with sequence similarity 41, member C |
| MTERFD2 | 4.086 | 4.627 | 4.371 | 7.748 | 6.948 | 7.008 | | 7.269 | 0.0028426 | MTERF domain containing 2 |
| OSBPL7 | 5.350 | 3.607 | 4.872 | 7.068 | 6.966 | 8.217 | | 7.295 | 0.0104017 | oxysterol binding protein-like 7 |
| PAPL | 7.567 | 6.920 | 8.019 | 10.436 | 10.341 | 10.823 | | 7.304 | 0.0026548 | No description |
| SP9 | 3.194 | 1.477 | 3.431 | 4.854 | 4.602 | 6.304 | | 7.324 | 0.0193334 | Sp9 transcription factor homolog (mouse) |
| KCNE1L | 0.648 | 0.648 | 1.387 | 2.202 | 4.043 | 4.262 | | 7.338 | 0.0146374 | KCNE1-like |
| SPHK2 | 6.062 | 5.012 | 6.053 | 8.941 | 8.458 | 8.437 | | 7.356 | 0.0038458 | sphingosine kinase 2 |
| C6orf120 | 7.113 | 5.357 | 5.772 | 8.591 | 8.672 | 8.653 | | 7.364 | 0.0107594 | chromosome 6 open reading frame 120 |
| THPO | 1.648 | 2.121 | 2.934 | 5.314 | 4.529 | 5.220 | | 7.367 | 0.0058492 | thrombopoietin |

TABLE 4-continued

Differentially Expressed Genes in CD44+ Breast Epithelial Cells

| | Nulliparous (NP) Samples | | | Parous (P) Samples | | | Pseudo fold change | P value | Gene description |
|---|---|---|---|---|---|---|---|---|---|
| Gene Symbol | CD44+ N48 | CD44+ N58 | CD44+ N43 | CD44+ N37 | CD44+ N39 | CD44+ N40 | | | |
| TYMP | 9.517 | 9.168 | 9.502 | 14.060 | 12.216 | 12.052 | 7.378 | 0.0045466 | thymidine phosphorylase |
| GYS1 | 5.645 | 6.278 | 7.827 | 10.155 | 9.466 | 8.529 | 7.379 | 0.0141425 | glycogen synthase 1 (muscle) |
| METTL2A | 4.972 | 5.204 | 4.346 | 7.339 | 7.862 | 7.984 | 7.415 | 0.0031068 | methyltransferase like 2A |
| CKB | 9.440 | 8.053 | 9.757 | 11.045 | 12.336 | 12.605 | 7.443 | 0.0103192 | creatine kinase, brain |
| IL1B | 6.692 | 5.495 | 5.319 | 8.393 | 6.688 | 9.915 | 7.454 | 0.0294596 | interleukin 1, beta |
| HAX1 | 8.278 | 7.288 | 7.243 | 10.387 | 10.458 | 10.142 | 7.460 | 0.0046132 | HCLS1 associated protein X-1 |
| CTU2 | 5.814 | 5.405 | 6.103 | 8.593 | 9.006 | 8.388 | 7.477 | 0.0023539 | cytosolic thiouridylase subunit 2 homolog (*S. pombe*) |
| CROCCL1 | 5.552 | 5.406 | 3.427 | 8.457 | 7.365 | 8.208 | 7.492 | 0.0077140 | No description |
| GPRIN1 | 1.648 | 3.230 | 4.038 | 6.136 | 6.149 | 5.997 | 7.495 | 0.0075539 | G protein regulated inducer of neurite outgrowth 1 |
| ZEAND2B | 4.525 | 4.876 | 5.818 | 7.871 | 7.433 | 7.803 | 7.508 | 0.0067484 | zinc finger, AN1-type domain 2B |
| KCNG2 | 0.648 | 3.043 | 1.387 | 4.854 | 5.964 | 2.370 | 7.570 | 0.0333508 | potassium voltage-gated channel, subfamily G, member 2 |
| FAM153B | 4.008 | 4.536 | 4.275 | 7.078 | 7.385 | 7.198 | 7.581 | 0.0011130 | family with sequence similarity 153, member B |
| SNX5 | 7.631 | 6.632 | 7.519 | 10.177 | 10.555 | 10.412 | 7.585 | 0.0019983 | sorting nexin 5 |
| STX1A | 3.947 | 4.735 | 5.847 | 6.872 | 8.115 | 7.944 | 7.595 | 0.0108898 | syntaxin 1A (brain) |
| PLXNB1 | 6.814 | 6.921 | 7.470 | 9.847 | 10.753 | 9.132 | 7.600 | 0.0065619 | plexin B1 |
| ZBTB5 | 4.969 | 4.139 | 5.165 | 7.740 | 7.341 | 8.091 | 7.601 | 0.0033799 | zinc finger and BTB domain containing 5 |
| C9orf142 | 4.972 | 3.810 | 5.246 | 7.899 | 7.385 | 7.581 | 7.604 | 0.0032350 | chromosome 9 open reading frame 142 |
| C2orf52 | 0.648 | 2.758 | 3.143 | 5.764 | 5.687 | 4.748 | 7.612 | 0.0093362 | chromosome 2 open reading frame 52 |
| FLVCR1 | 2.970 | 4.397 | 3.247 | 5.899 | 6.988 | 6.973 | 7.615 | 0.0053917 | feline leukemia virus subgroup C cellular receptor 1 |
| C5orf44 | 3.619 | 3.467 | 4.530 | 6.868 | 6.398 | 7.389 | 7.624 | 0.0038728 | chromosome 5 open reading frame 44 |
| ANKRD36BL1 | 2.233 | 3.197 | 2.917 | 5.167 | 5.772 | 6.785 | 7.640 | 0.0047913 | No description |
| SLC37A1 | 5.499 | 4.230 | 6.012 | 8.366 | 8.795 | 8.433 | 7.641 | 0.0036898 | solute carrier family 37 (glycerol-3-phosphate transporter), member 1 |
| PPM1D | 5.731 | 4.688 | 4.092 | 7.233 | 7.036 | 8.780 | 7.697 | 0.0115269 | protein phosphatase, Mg2+/Mn2+ dependent, 1D |
| GFER | 6.532 | 5.316 | 5.634 | 8.974 | 8.262 | 8.598 | 7.703 | 0.0053231 | growth factor, augmenter of liver regeneration |
| SFRS8 | 7.087 | 7.993 | 7.126 | 10.072 | 10.057 | 10.128 | 7.706 | 0.0040128 | No description |
| TMOD1 | 5.087 | 5.019 | 5.577 | 9.015 | 8.034 | 6.676 | 7.711 | 0.0134693 | tropomodulin 1 |
| C17orf55 | 2.648 | 2.744 | 3.464 | 5.755 | 3.739 | 6.416 | 7.738 | 0.0262638 | chromosome 17 open reading frame 55 |
| LOC100288730 | 3.619 | 2.649 | 3.415 | 6.368 | 5.968 | 6.454 | 7.743 | 0.0022638 | No description |
| RAB3A | 6.777 | 4.033 | 7.445 | 6.368 | 6.987 | 8.578 | 7.746 | 0.0345411 | RAB3A, member RAS oncogene family |
| NES | 9.415 | 7.737 | 9.196 | 10.545 | 12.372 | 12.346 | 7.762 | 0.0114825 | nestin |
| HLA-DOB | 1.648 | 1.648 | 1.689 | 4.477 | 5.120 | 4.607 | 7.772 | 0.0009820 | major histocompatibility complex, class II, DO beta |
| ANKRD45 | 3.619 | 2.233 | 2.814 | 5.873 | 5.583 | 5.774 | 7.784 | 0.0045979 | ankyrin repeat domain 45 |
| RBBP9 | 4.008 | 3.420 | 4.975 | 6.981 | 7.625 | 6.818 | 7.853 | 0.0051289 | retinoblastoma binding protein 9 |
| NLRX1 | 5.264 | 1.648 | 2.281 | 5.997 | 5.256 | 4.975 | 7.864 | 0.0433314 | NLR family member X1 |
| LETM2 | 1.648 | 2.064 | 3.296 | 4.624 | 5.304 | 5.398 | 7.867 | 0.0081605 | leucine zipper-EF-hand containing transmembrane protein 2 |
| ABHD8 | 6.495 | 3.346 | 4.343 | 8.018 | 7.324 | 7.036 | 7.896 | 0.0209092 | abhydrolase domain containing 8 |
| FAM115A | 7.304 | 6.611 | 7.445 | 9.526 | 10.287 | 10.692 | 7.903 | 0.0035574 | family with sequence similarity 115, member A |
| IL2RA | 6.912 | 5.961 | 6.748 | 9.450 | 9.394 | 9.895 | 7.909 | 0.0022998 | interleukin 2 receptor, alpha |
| KIAA1919 | 4.734 | 1.978 | 3.814 | 6.619 | 6.934 | 6.798 | 7.910 | 0.0081043 | KIAA1919 |
| DNAI2 | 0.648 | 0.648 | 1.387 | 3.351 | 3.633 | 7.721 | 7.917 | 0.0120938 | dynein, axonemal, intermediate chain 2 |
| SDS | 0.648 | 3.644 | 2.781 | 4.748 | 3.633 | 7.410 | 7.917 | 0.0327518 | serine dehydratase |
| SLFN13 | 3.818 | 4.230 | 4.905 | 7.222 | 7.204 | 7.619 | 7.958 | 0.0025161 | schlafen family member 13 |
| WAS | 1.648 | 3.294 | 2.566 | 4.725 | 4.641 | 7.281 | 7.962 | 0.0150742 | Wiskott-Aldrich syndrome (eczema-thrombocytopenia) |
| ANKRD11 | 7.704 | 7.824 | 8.703 | 10.699 | 11.042 | 10.892 | 7.973 | 0.0037078 | ankyrin repeat domain 11 |
| CCDC61 | 2.233 | 2.461 | 3.291 | 6.288 | 5.513 | 4.777 | 7.983 | 0.0070381 | coiled-coil domain containing 61 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| GOLGA2L1 | 3.456 | 3.733 | 3.957 | 6.732 | 5.272 | 7.050 | 7.991 | 0.0105584 | No description |
| EEF1A2 | 2.970 | 3.866 | 5.042 | 7.698 | 8.042 | 5.847 | 7.999 | 0.0105854 | eukaryotic translation elongation factor 1 alpha 2 |
| C21orf88 | 6.791 | 6.388 | 6.747 | 9.443 | 9.571 | 9.798 | 8.040 | 0.0010270 | chromosome 21 open reading frame 88 |
| MRPL41 | 7.081 | 6.036 | 8.507 | 10.191 | 10.088 | 9.294 | 8.041 | 0.0158832 | mitochondrial ribosomal protein L41 |
| C14orf73 | 1.648 | 1.978 | 2.450 | 4.624 | 5.102 | 5.459 | 8.051 | 0.0023990 | chromosome 14 open reading frame 73 |
| LAMC3 | 7.714 | 6.902 | 7.620 | 9.912 | 10.480 | 11.681 | 8.052 | 0.0041785 | laminin, gamma 3 |
| LRRC27 | 6.541 | 5.659 | 6.734 | 9.093 | 9.552 | 9.694 | 8.061 | 0.0024350 | leucine rich repeat containing 27 |
| ZSCAN20 | 0.648 | 0.648 | 0.729 | 3.662 | 4.043 | 3.351 | 8.074 | 0.0011296 | zinc finger and SCAN domain containing 20 |
| INVS | 0.648 | 0.648 | 0.999 | 3.662 | 3.633 | 4.389 | 8.074 | 0.0013910 | inversin |
| DUOX2 | 0.648 | 1.753 | 1.564 | 3.662 | 6.202 | 4.389 | 8.074 | 0.0069750 | dual oxidase 2 |
| SMCR8 | 6.777 | 6.139 | 6.769 | 9.791 | 9.170 | 9.778 | 8.079 | 0.0020073 | Smith-Magenis syndrome chromosome region, candidate 8 |
| SETD8 | 8.182 | 7.579 | 8.961 | 10.750 | 11.199 | 11.345 | 8.095 | 0.0050250 | SET domain containing (lysine methyltransferase) 8 |
| C9orf41 | 5.076 | 3.397 | 5.123 | 7.189 | 7.492 | 8.146 | 8.129 | 0.0066790 | chromosome 9 open reading frame 41 |
| C6orf129 | 0.648 | 4.529 | 5.996 | 8.084 | 7.554 | 6.777 | 8.139 | 0.0196392 | chromosome 6 open reading frame 129 |
| TCP11L1 | 5.899 | 5.671 | 5.478 | 8.933 | 8.699 | 8.210 | 8.160 | 0.0018388 | t-complex 11 (mouse)-like 1 |
| ZFP41 | 4.525 | 2.951 | 3.815 | 7.076 | 6.851 | 6.613 | 8.201 | 0.0039359 | zinc finger protein 41 homolog (mouse) |
| DAK | 7.283 | 4.583 | 5.159 | 8.196 | 8.724 | 7.769 | 8.208 | 0.0213536 | dihydroxyacetone kinase 2 homolog (S. cerevisiae) |
| GGT8P | 3.860 | 0.648 | 1.564 | 4.972 | 3.871 | 4.602 | 8.213 | 0.0299712 | gamma-glutamyltransferase 8 pseudogene |
| ZWILCH | 3.422 | 1.648 | 2.177 | 6.340 | 4.692 | 5.416 | 8.245 | 0.0081834 | Zwilch, kinetochore associated, homolog (Drosophila) |
| GDH | 8.090 | 5.458 | 6.036 | 9.171 | 8.740 | 9.082 | 8.260 | 0.0215393 | GDP dissociation inhibitor 1 |
| MCOLN2 | 6.158 | 4.550 | 5.795 | 7.600 | 7.930 | 9.399 | 8.280 | 0.0123019 | mucolipin 2 |
| BRF1 | 6.753 | 4.951 | 6.415 | 9.468 | 9.306 | 9.615 | 8.297 | 0.0031851 | BRF1 homolog, subunit of RNA polymerase III transcription initiation factor IIIB (S. cerevisiae) |
| TIMM17B | 5.452 | 5.056 | 5.783 | 8.892 | 8.507 | 8.094 | 8.307 | 0.0019712 | translocase of inner mitochondrial membrane 17 homolog B (yeast) |
| TNFRSF1B | 9.518 | 7.432 | 9.619 | 12.188 | 12.396 | 12.674 | 8.308 | 0.0043650 | tumor necrosis factor receptor superfamily, member 1B |
| FGFR2 | 5.961 | 5.886 | 6.302 | 8.472 | 9.018 | 9.473 | 8.323 | 0.0026998 | fibroblast growth factor receptor 2 |
| PTPRCAP | 4.314 | 3.452 | 5.196 | 6.947 | 6.510 | 8.362 | 8.327 | 0.0106964 | protein tyrosine phosphatase, receptor type, C-associated protein |
| MYOM1 | 3.792 | 2.648 | 3.202 | 5.072 | 6.264 | 7.014 | 8.354 | 0.0089584 | myomesin 1, 185 kDa |
| G20orf425 | 6.741 | 4.904 | 5.334 | 8.399 | 8.346 | 8.736 | 8.365 | 0.0079137 | zinc finger protein 425 |
| G20orf4 | 2.233 | 6.023 | 5.771 | 8.836 | 8.958 | 8.289 | 8.367 | 0.0086076 | chromosome 20 open reading frame 4 |
| ZNF222 | 0.648 | 3.959 | 1.245 | 4.632 | 4.311 | 3.773 | 8.372 | 0.0398055 | zinc finger protein 222 |
| ANKFY1 | 7.155 | 5.147 | 5.861 | 9.208 | 8.931 | 8.746 | 8.397 | 0.0078291 | ankyrin repeat and FYVE domain containing 1 |
| NHLH1 | 1.648 | 2.304 | 2.625 | 4.721 | 5.730 | 5.220 | 8.411 | 0.0033709 | nescient helix loop helix 1 |
| C3orf42 | 2.648 | 3.659 | 5.385 | 5.982 | 6.731 | 6.955 | 8.412 | 0.0182250 | chromosome 3 open reading frame 42 |
| MAGI2 | 4.826 | 4.767 | 5.412 | 8.108 | 7.842 | 8.273 | 8.430 | 0.0012828 | membrane associated guanylate kinase, WW and PDZ domain containing 2 |
| KPTN | 6.232 | 4.529 | 6.036 | 8.246 | 9.047 | 9.310 | 8.442 | 0.0049203 | kaptin (actin binding protein) |
| LOC100216545 | 4.525 | 2.794 | 4.076 | 7.156 | 6.580 | 7.592 | 8.454 | 0.0041695 | No description |
| IRF3 | 5.849 | 4.352 | 4.842 | 7.922 | 7.805 | 7.986 | 8.456 | 0.0048752 | interferon regulatory factor 3 |
| GZF1 | 5.173 | 3.691 | 5.685 | 8.257 | 8.123 | 8.562 | 8.479 | 0.0035484 | GDNF-inducible zinc finger protein 1 |
| MAK | 2.648 | 2.648 | 2.822 | 5.929 | 5.733 | 5.558 | 8.485 | 0.0006825 | male germ cell-associated kinase |
| CLDN4 | 7.271 | 5.575 | 4.127 | 8.870 | 8.665 | 8.029 | 8.517 | 0.0168496 | claudin 4 |
| SCN4A | 4.872 | 4.214 | 7.282 | 7.966 | 7.961 | 8.549 | 8.539 | 0.0207962 | sodium channel, voltage-gated, type IV, alpha subunit |
| STEAP3 | 2.648 | 2.970 | 3.464 | 6.066 | 8.015 | 5.682 | 8.550 | 0.0048184 | STEAP family member 3 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| TCEA2 | 6.896 | 5.783 | 6.622 | 9.370 | 9.273 | 9.995 | 8.567 | 0.0028607 | transcription elongation factor A (SII), 2 |
| PARP10 | 7.070 | 4.346 | 6.639 | 9.474 | 9.291 | 10.176 | 8.610 | 0.0062312 | poly (ADP-ribose) polymerase family, member 10 |
| C11orf84 | 6.777 | 5.856 | 6.900 | 9.887 | 8.218 | 11.028 | 8.633 | 0.0104489 | chromosome 11 open reading frame 84 |
| ZNF554 | 4.708 | 4.194 | 5.145 | 7.837 | 7.680 | 7.822 | 8.660 | 0.0015629 | zinc finger protein 554 |
| RPS19BP1 | 6.340 | 4.529 | 4.477 | 8.800 | 8.921 | 7.592 | 8.664 | 0.0063671 | ribosomal protein S19 binding protein 1 |
| CCBP2 | 4.793 | 5.167 | 6.076 | 8.150 | 8.516 | 8.283 | 8.668 | 0.0035664 | chemokine binding protein 2 |
| SLC39A13 | 8.757 | 7.078 | 7.746 | 10.866 | 11.134 | 10.658 | 8.693 | 0.0048364 | solute carrier family 39 (zinc transporter), member 13 |
| INHA | 0.648 | 0.648 | 0.648 | 5.514 | 3.633 | 3.773 | 8.720 | 0.0024981 | inhibin, alpha |
| LOC729799 | 0.648 | 0.648 | 0.729 | 5.035 | 3.284 | 3.773 | 8.720 | 0.0030839 | No description |
| PAK6 | 0.648 | 2.941 | 3.046 | 5.256 | 7.339 | 3.773 | 8.720 | 0.0197452 | p21 protein (Cdc42/Rac)-activated kinase 6 |
| BIRC5 | 2.233 | 2.233 | 2.702 | 3.535 | 5.360 | 5.963 | 8.736 | 0.0168225 | baculoviral IAP repeat-containing 5 |
| DDX51 | 5.872 | 5.211 | 5.829 | 8.806 | 8.999 | 8.719 | 8.739 | 0.0008905 | DEAD (Asp-Glu-Ala-Asp) box polypeptide 51 |
| C20orf200 | 0.648 | 2.758 | 4.314 | 6.177 | 5.742 | 5.889 | 8.756 | 0.0124010 | chromosome 20 open reading frame 200 |
| USP45 | 5.289 | 4.323 | 4.492 | 7.626 | 7.575 | 8.418 | 8.773 | 0.0025341 | ubiquitin specific peptidase 45 |
| CHTF18 | 6.732 | 4.737 | 5.543 | 8.201 | 8.682 | 9.830 | 8.807 | 0.0074728 | CTF18, chromosome transmission fidelity factor 18 homolog (*S. cerevisiae*) |
| TAF1C | 5.264 | 5.956 | 7.390 | 9.099 | 9.039 | 9.249 | 8.834 | 0.0080863 | TATA box binding protein (TBP)-associated factor, RNA polymerase I, C, 110 kDa |
| LMAN2L | 7.001 | 4.760 | 6.052 | 9.002 | 9.259 | 9.195 | 8.835 | 0.0057397 | lectin, mannose-binding 2-like |
| RNF217 | 1.648 | 2.675 | 2.234 | 3.557 | 5.818 | 5.802 | 8.837 | 0.0131179 | ring finger protein 217 |
| HSPB1 | 6.756 | 4.351 | 8.610 | 8.659 | 9.355 | 11.755 | 8.846 | 0.0248863 | heat shock 27 kDa protein 1 |
| LRG1 | 5.781 | 2.894 | 5.736 | 5.781 | 8.928 | 8.889 | 8.863 | 0.0273480 | leucine-rich alpha-2-glycoprotein 1 |
| GPATCH3 | 4.525 | 4.616 | 6.703 | 8.229 | 8.067 | 7.677 | 8.889 | 0.0137778 | G patch domain containing 3 |
| NCOR2 | 7.864 | 7.048 | 6.689 | 10.378 | 9.842 | 10.740 | 8.893 | 0.0032260 | nuclear receptor corepressor 2 |
| MXD3 | 4.826 | 3.111 | 4.508 | 7.452 | 7.989 | 7.238 | 8.956 | 0.0033439 | MAX dimerization protein 3 |
| KIAA0562 | 6.457 | 5.507 | 6.000 | 9.174 | 9.235 | 8.823 | 9.027 | 0.0017730 | KIAA0562 |
| PPP4R1L | 1.648 | 1.648 | 1.648 | 5.272 | 4.811 | 4.830 | 9.075 | 0.0004614 | protein phosphatase 4, regulatory subunit 1 -like |
| CHMP6 | 5.598 | 3.643 | 5.167 | 8.647 | 8.351 | 7.198 | 9.092 | 0.0068884 | chromatin modifying protein 6 |
| PAPPA | 7.069 | 8.327 | 7.074 | 12.144 | 10.259 | 9.656 | 9.092 | 0.0100461 | pregnancy-associated plasma protein A, pappalysin 1 |
| MYLPF | 0.648 | 2.593 | 1.564 | 4.748 | 5.742 | 4.262 | 9.093 | 0.0058402 | myosin light chain, phosphorylatable, fast skeletal muscle |
| LRWD1 | 3.619 | 4.457 | 4.214 | 7.405 | 7.417 | 6.910 | 9.129 | 0.0015719 | leucine-rich repeats and WD repeat domain containing 1 |
| CIB2 | 7.101 | 3.107 | 5.624 | 8.818 | 8.641 | 9.442 | 9.150 | 0.0109764 | calcium and integrin binding family member 2 |
| CSNK2A1P | 7.568 | 6.006 | 7.283 | 10.480 | 10.663 | 10.240 | 9.169 | 0.0020343 | casein kinase 2, alpha 1 polypeptide pseudogene |
| DHX8 | 6.520 | 4.282 | 6.262 | 9.253 | 9.718 | 9.386 | 9.173 | 0.0032863 | DEAH (Asp-Glu-Ala-His) box polypeptide 8 |
| DCLRE1C | 5.482 | 4.472 | 4.501 | 8.172 | 7.670 | 8.184 | 9.179 | 0.0020932 | DNA cross-link repair 1C |
| PBX4 | 6.710 | 4.969 | 5.291 | 9.519 | 7.434 | 9.911 | 9.196 | 0.0104849 | pre-B-cell leukemia homeobox 4 |
| LOC146880 | 2.233 | 2.565 | 4.335 | 5.778 | 6.469 | 5.561 | 9.273 | 0.0105029 | No description |
| SDR39U1 | 7.893 | 7.755 | 8.570 | 11.201 | 10.968 | 11.469 | 9.276 | 0.0015130 | short chain dehydrogenase/reductase family 39U, member 1 |
| LOC401127 | 4.142 | 3.047 | 3.720 | 6.288 | 6.368 | 7.357 | 9.286 | 0.0041965 | No description |
| TAF3 | 7.298 | 5.721 | 5.444 | 8.956 | 8.676 | 8.936 | 9.287 | 0.0101633 | TAF3 RNA polymerase II, TATA box binding protein (TBP)-associated factor, 140 kDa |
| ZGPAT | 5.173 | 2.822 | 4.083 | 7.302 | 7.151 | 7.312 | 9.312 | 0.0061224 | zinc finger, CCCH-type with G patch domain |
| TGFB1I1 | 10.251 | 7.018 | 9.260 | 12.662 | 12.481 | 11.581 | 9.324 | 0.0108225 | transforming growth factor beta 1 induced transcript 1 |
| GMFG | 5.264 | 1.648 | 5.903 | 9.069 | 7.759 | 8.486 | 9.327 | 0.0095733 | glia maturation factor, gamma |
| HPVC1 | 0.648 | 0.648 | 0.729 | 3.871 | 3.871 | 4.262 | 9.332 | 0.0004163 | human papillomavirus (type 18) E5 central sequence-like 1 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| SLC16A13 | 0.648 | 0.648 | 0.648 | 3.871 | 4.311 | 3.351 | 9.332 | 0.0011837 | solute carrier family 16, member 13 (monocarboxylic acid transporter 13) |
| SPC25 | 0.648 | 0.648 | 0.729 | 3.871 | 3.284 | 4.602 | 9.332 | 0.0019622 | SPC25, NDC80 kinetochore complex component, homolog (S. cerevisiae) |
| CYP2D6 | 0.648 | 0.648 | 0.729 | 4.021 | 3.871 | 3.043 | 9.332 | 0.0023179 | cytochrome P450, family 2, subfamily D, polypeptide 6 |
| TDGF1 | 0.648 | 0.648 | 0.648 | 3.871 | 5.053 | 3.351 | 9.332 | 0.0023719 | teratocarcinoma-derived growth factor 1 |
| C19orf77 | 0.648 | 0.648 | 1.245 | 3.871 | 4.728 | 3.351 | 9.332 | 0.0033348 | chromosome 19 open reading frame 77 |
| RDH16 | 0.648 | 0.648 | 0.648 | 4.854 | 3.871 | 3.043 | 9.332 | 0.0034693 | retinol dehydrogenase 16 (all-trans) |
| SYNGR3 | 0.648 | 1.649 | 2.268 | 3.871 | 4.043 | 5.728 | 9.332 | 0.0099026 | synaptogyrin 3 |
| FERMT1 | 0.648 | 0.648 | 0.648 | 3.871 | 6.792 | 2.370 | 9.332 | 0.0130263 | fermitin family member 1 |
| ZBTB32 | 0.648 | 0.648 | 1.477 | 2.202 | 3.871 | 5.014 | 9.332 | 0.0162402 | zinc finger and BTB domain containing 32 |
| UGT2B10 | 0.648 | 0.648 | 0.648 | 4.021 | 3.871 | 0.648 | 9.332 | 0.0484032 | UDP glucuronosyltransferase 2 family, polypeptide B10 |
| CBS | 5.173 | 4.713 | 2.841 | 7.963 | 8.396 | 5.793 | 9.333 | 0.0156045 | cystathionine-beta-synthase |
| S100A7 | 0.648 | 4.043 | 5.396 | 7.272 | 8.119 | 6.684 | 9.377 | 0.0128551 | S100 calcium binding protein A7 |
| SULT1A4 | 4.972 | 6.308 | 6.711 | 8.484 | 9.543 | 9.678 | 9.416 | 0.0054818 | sulfotransferase family, cytosolic, 1A, phenol-preferring, member 4 |
| RASSF4 | 6.368 | 3.966 | 6.121 | 9.131 | 8.684 | 9.603 | 9.416 | 0.0048842 | Ras association (RalGDS/AF-6) domain family member 4 |
| PHB | 4.423 | 3.832 | 3.294 | 6.532 | 7.717 | 6.685 | 9.430 | 0.0039449 | prohibitin |
| PRRG2 | 1.648 | 3.247 | 4.429 | 5.502 | 6.934 | 6.486 | 9.439 | 0.0109993 | proline rich Gla (G-carboxyglutamic acid) 2 |
| SPPL2B | 7.572 | 5.453 | 7.312 | 10.267 | 10.562 | 10.734 | 9.516 | 0.0029667 | No description |
| FBXO27 | 6.003 | 4.242 | 5.287 | 8.163 | 8.540 | 8.622 | 9.533 | 0.0036357 | F-box protein 27 |
| VMO1 | 0.648 | 1.477 | 3.046 | 6.031 | 3.871 | 6.304 | 9.571 | 0.0083331 | vitelline membrane outer layer 1 homolog (chicken) |
| PANK4 | 6.818 | 6.439 | 8.490 | 9.851 | 10.120 | 10.084 | 9.619 | 0.0104399 | pantothenate kinase 4 |
| CYB5R2 | 5.377 | 5.206 | 6.429 | 9.436 | 9.682 | 8.478 | 9.659 | 0.0022976 | cytochrome b5 reductase 2 |
| KAT2A | 6.838 | 6.777 | 7.714 | 10.112 | 9.978 | 10.991 | 9.672 | 0.0025612 | K(lysine) acetyltransferase 2A |
| RBM19 | 6.067 | 5.591 | 6.470 | 9.341 | 9.672 | 8.961 | 9.676 | 0.0013549 | RNA binding motif protein 19 |
| B3GAT1 | 2.233 | 2.233 | 2.233 | 3.737 | 7.279 | 5.509 | 9.688 | 0.0124620 | beta-1,3-glucuronyltransferase 1 (glucuronosyltransferase P) |
| KDM5C | 7.234 | 5.985 | 6.462 | 9.747 | 9.813 | 9.729 | 9.747 | 0.0019532 | lysine (K)-specific demethylase 5C |
| HIP1R | 7.086 | 5.948 | 7.588 | 9.144 | 11.134 | 10.375 | 9.771 | 0.0063851 | huntingtin interacting protein 1 related |
| TMCO7 | 2.970 | 3.572 | 4.173 | 6.882 | 6.872 | 6.701 | 9.849 | 0.0016711 | transmembrane and coiled-coil domains 7 |
| AKNA | 8.629 | 6.813 | 9.566 | 11.545 | 11.930 | 12.585 | 9.856 | 0.0054638 | AT-hook transcription factor |
| SLC14A1 | 5.552 | 4.555 | 6.208 | 8.024 | 8.855 | 8.870 | 9.870 | 0.0047102 | solute carrier family 14 (urea transporter), member 1 (Kidd blood group) |
| C21orf99 | 0.648 | 0.648 | 0.999 | 4.021 | 4.311 | 3.351 | 9.932 | 0.0016891 | No description |
| MRPS18C | 1.648 | 5.203 | 3.517 | 7.353 | 6.831 | 6.394 | 9.946 | 0.0117362 | mitochondrial ribosomal protein S18C |
| C5orf60 | 0.648 | 0.648 | 0.729 | 5.133 | 3.871 | 3.966 | 9.973 | 0.0009640 | chromosome 5 open reading frame 60 |
| MTMR15 | 2.233 | 2.233 | 2.932 | 5.551 | 6.428 | 5.147 | 9.973 | 0.0026728 | No description |
| LRCH4 | 7.300 | 5.815 | 7.845 | 10.106 | 10.621 | 10.772 | 9.994 | 0.0036177 | leucine-rich repeats and calponin homology (CH) domain containing 4 |
| SLC25A1 | 7.796 | 6.246 | 6.749 | 10.487 | 10.212 | 9.570 | 10.008 | 0.0042700 | solute carrier family 25 (mitochondrial carrier; citrate transporter), member 1 |
| PTPN6 | 5.861 | 3.104 | 3.802 | 6.429 | 7.126 | 7.789 | 10.017 | 0.0161737 | protein tyrosine phosphatase, non-receptor type 6 |
| TMEM169 | 1.648 | 1.648 | 1.834 | 5.409 | 4.017 | 4.975 | 10.033 | 0.0031941 | transmembrane protein 169 |
| MPHOSPH6 | 4.525 | 5.812 | 5.717 | 8.400 | 9.149 | 8.002 | 10.102 | 0.0042520 | M-phase phosphoprotein 6 |
| KLC2 | 6.721 | 5.450 | 7.174 | 10.058 | 10.155 | 9.832 | 10.107 | 0.0020662 | kinesin light chain 2 |
| GATS | 6.569 | 2.970 | 3.410 | 7.952 | 6.313 | 7.546 | 10.147 | 0.0243061 | GATS, stromal antigen 3 opposite strand |

TABLE 4-continued

Differentially Expressed Genes in CD44+ Breast Epithelial Cells

| | Nulliparous (NP) Samples | | Parous (P) Samples | | | | Pseudo | | |
|---|---|---|---|---|---|---|---|---|---|
| Gene Symbol | CD44+ N48 | CD44+ N58 | CD44+ N43 | CD44+ N37 | CD44+ N39 | CD44+ N40 | fold change | P value | Gene description |
| CSF3R | 2.233 | 2.233 | 3.073 | 4.715 | 5.583 | 7.787 | 10.198 | 0.0083692 | colony stimulating factor 3 receptor (granulocyte) |
| ADC | 5.322 | 5.045 | 5.646 | 7.264 | 8.695 | 9.009 | 10.290 | 0.0062042 | arginine decarboxylase |
| IL1RL1 | 6.639 | 8.888 | 8.061 | 11.426 | 11.751 | 11.112 | 10.303 | 0.0037958 | interleukin 1 receptor-like 1 |
| MRTO4 | 6.575 | 6.703 | 7.788 | 10.312 | 10.971 | 9.944 | 10.330 | 0.0024891 | mRNA turnover 4 homolog (S. cerevisiae) |
| CCDC13 | 0.648 | 0.648 | 0.648 | 4.021 | 4.728 | 3.773 | 10.361 | 0.0006735 | coiled-coil domain containing 13 |
| NPB | 0.648 | 1.649 | 0.729 | 4.021 | 4.602 | 4.748 | 10.361 | 0.0013459 | neuropeptide B |
| OXT | 0.648 | 0.648 | 2.401 | 4.021 | 4.428 | 4.901 | 10.361 | 0.0054728 | oxytocin, prepropeptide |
| RASSF7 | 4.423 | 4.477 | 5.905 | 7.309 | 9.288 | 9.036 | 10.431 | 0.0049383 | Ras association (RalGDS/AF-6) domain family (N-terminal) member 7 |
| C19orf21 | 0.648 | 3.046 | 3.745 | 5.256 | 7.128 | 4.602 | 10.433 | 0.0182971 | chromosome 19 open reading frame 21 |
| HTR3B | 6.930 | 2.780 | 5.082 | 8.242 | 8.474 | 8.812 | 10.499 | 0.0125993 | 5-hydroxytryptamine (serotonin) receptor 3B |
| LEAP2 | 0.648 | 0.648 | 0.729 | 4.021 | 4.043 | 4.389 | 10.515 | 0.0002603 | liver expressed antimicrobial peptide 2 |
| ZSCAN5A | 0.648 | 0.648 | 1.719 | 5.133 | 4.043 | 3.966 | 10.515 | 0.0028967 | zinc finger and SCAN domain containing 5A |
| PLK1S1 | 0.648 | 2.202 | 0.729 | 4.632 | 5.060 | 5.230 | 10.515 | 0.0036447 | polo-like kinase 1 substrate 1 |
| TMEM213 | 5.503 | 4.557 | 4.169 | 7.751 | 7.952 | 8.465 | 10.516 | 0.0023809 | transmembrane protein 213 |
| SLC4A3 | 6.145 | 3.708 | 3.518 | 6.912 | 8.407 | 7.603 | 10.518 | 0.0121168 | solute carrier family 4, anion exchanger, member 3 |
| OSTF1 | 8.090 | 6.007 | 6.047 | 10.163 | 9.403 | 10.397 | 10.528 | 0.0070111 | osteoclast stimulating factor 1 |
| GPR83 | 2.233 | 2.565 | 3.415 | 5.963 | 5.911 | 6.681 | 10.543 | 0.0016621 | G protein-coupled receptor 83 |
| CYP8B1 | 0.648 | 2.268 | 2.359 | 5.213 | 4.990 | 5.761 | 10.573 | 0.0029127 | cytochrome P450, family 8, subfamily B, polypeptide 1 |
| HHIPL1 | 4.620 | 2.648 | 3.320 | 7.471 | 6.731 | 6.728 | 10.639 | 0.0038049 | HHIP-like 1 |
| RPAP2 | 2.648 | 3.297 | 2.999 | 6.476 | 6.709 | 5.137 | 10.639 | 0.0043920 | RNA polymerase II associated protein 2 |
| ZSCAN16 | 1.648 | 1.648 | 1.648 | 5.973 | 5.060 | 4.236 | 10.641 | 0.0023359 | zinc finger and SCAN domain containing 16 |
| POLR3E | 5.087 | 5.782 | 6.041 | 8.607 | 9.199 | 9.333 | 10.680 | 0.0012108 | polymerase (RNA) III (DNA directed) polypeptide E (80kD) |
| HIST1H1C | 3.194 | 0.648 | 0.729 | 6.612 | 5.687 | 2.370 | 10.688 | 0.0242423 | histone cluster 1, H1c |
| NASP | 7.297 | 7.602 | 8.422 | 10.949 | 11.022 | 11.573 | 10.700 | 0.0014811 | nuclear autoantigenic sperm protein (histone-binding) |
| RABL3 | 5.945 | 4.609 | 6.307 | 9.735 | 9.299 | 8.256 | 10.758 | 0.0042610 | RAB, member of RAS oncogene family-like 3 |
| FOXD2 | 0.648 | 1.245 | 2.401 | 5.355 | 3.633 | 5.830 | 10.768 | 0.0064302 | forkhead box D2 |
| MTHFR | 7.715 | 6.393 | 7.287 | 10.446 | 9.912 | 11.146 | 10.788 | 0.0030749 | methylenetetrahydrofolate reductase (NAD(P)H) |
| MFSD7 | 5.042 | 3.620 | 6.047 | 8.551 | 8.478 | 8.166 | 10.819 | 0.0046222 | major facilitator superfamily domain containing 7 |
| SBF1 | 4.736 | 5.374 | 6.886 | 8.357 | 8.810 | 8.811 | 10.819 | 0.0079546 | SET binding factor 1 |
| MFSD9 | 1.648 | 1.648 | 1.834 | 5.485 | 5.088 | 2.752 | 10.852 | 0.0167768 | major facilitator superfamily domain containing 9 |
| ST7L | 2.648 | 3.218 | 4.001 | 6.703 | 6.810 | 6.096 | 10.912 | 0.0027269 | suppression of tumorigenicity 7 like |
| ZBTB7B | 6.756 | 5.499 | 6.140 | 9.588 | 9.818 | 9.170 | 10.913 | 0.0016530 | zinc finger and BTB domain containing 7B |
| KIAA0664 | 6.660 | 7.575 | 5.365 | 9.713 | 10.587 | 10.110 | 10.925 | 0.0036808 | KIAA0664 |
| KIAA1161 | 2.970 | 3.942 | 5.189 | 7.107 | 7.396 | 7.659 | 10.957 | 0.0048004 | KIAA1161 |
| KIF1A | 1.648 | 4.218 | 4.139 | 5.102 | 8.171 | 6.091 | 10.960 | 0.0065834 | kinesin family member 1A |
| BTG3 | 5.936 | 3.695 | 4.226 | 8.147 | 7.680 | 7.642 | 10.960 | 0.0066159 | BTG family, member 3 |
| NFE2L1 | 9.660 | 7.368 | 9.100 | 13.114 | 11.536 | 11.109 | 10.961 | 0.0110707 | nuclear factor (erythroid-derived 2)-like 1 |
| SLC34A2 | 3.648 | 6.243 | 7.096 | 8.082 | 11.067 | 7.103 | 10.967 | 0.0328038 | solute carrier family 34 (sodium phosphate), member 2 |
| DEXI | 9.144 | 7.416 | 8.839 | 12.357 | 12.303 | 11.959 | 11.030 | 0.0016801 | Dexi homolog (mouse) |
| SIN3A | 8.510 | 7.806 | 7.949 | 11.414 | 11.014 | 12.108 | 11.041 | 0.0013730 | SIN3 homolog A, transcription regulator (yeast) |
| DDR2 | 6.950 | 4.869 | 5.169 | 9.869 | 8.929 | 8.338 | 11.073 | 0.0066250 | discoidin domain receptor tyrosine kinase 2 |
| TCHP | 4.969 | 3.475 | 4.394 | 7.733 | 7.933 | 7.865 | 11.085 | 0.0013820 | trichoplein, keratin filament binding |
| ATP6V1B1 | 4.008 | 2.625 | 3.499 | 6.308 | 7.483 | 6.333 | 11.119 | 0.0036267 | ATPase, H+ transporting, lysosomal 56/58 kDa, V1 subunit B1 |
| KLHDC9 | 0.648 | 0.648 | 1.753 | 3.351 | 4.990 | 5.230 | 11.132 | 0.0043331 | kelch domain containing 9 |
| PRC1 | 3.860 | 3.475 | 2.268 | 5.894 | 4.870 | 5.761 | 11.259 | 0.0119109 | protein regulator of cytokinesis 1 |

TABLE 4-continued

Differentially Expressed Genes in CD44+ Breast Epithelial Cells

| | Nulliparous (NP) Samples | | | Parous (P) Samples | | | | Pseudo | | |
|---|---|---|---|---|---|---|---|---|---|---|
| Gene Symbol | CD44+ N48 | CD44+ N58 | CD44+ N43 | CD44+ N37 | CD44+ N39 | CD44+ N40 | fold change | P value | Gene description |
| PRKDC | 7.197 | 6.631 | 7.920 | 11.110 | 10.790 | 10.134 | 11.333 | 0.0021023 | protein kinase, DNA-activated, catalytic polypeptide |
| NOC4L | 6.710 | 6.169 | 7.093 | 10.252 | 10.604 | 9.563 | 11.401 | 0.0013640 | nucleolar complex associated 4 homolog (S. cerevisiae) |
| ADCK5 | 5.042 | 1.648 | 3.904 | 7.793 | 6.969 | 7.423 | 11.461 | 0.0065078 | aarF domain containing kinase 5 |
| SGTA | 8.472 | 4.673 | 9.701 | 11.573 | 12.001 | 12.771 | 11.545 | 0.0094437 | small glutamine-rich tetratricopeptide repeat (TPR)-containing, alpha |
| SCRIB | 6.592 | 3.948 | 6.972 | 10.122 | 10.410 | 10.019 | 11.553 | 0.0031400 | scribbled homolog (Drosophila) |
| AATK | 0.648 | 0.999 | 2.401 | 4.529 | 5.053 | 4.262 | 11.556 | 0.0043241 | apoptosis-associated tyrosine kinase |
| NCAPD3 | 2.648 | 4.557 | 2.970 | 6.501 | 6.889 | 6.181 | 11.557 | 0.0059484 | non-SMC condensin II complex, subunit D3 |
| ZNF384 | 7.837 | 6.428 | 6.852 | 10.386 | 10.468 | 10.327 | 11.578 | 0.0018991 | zinc finger protein 384 |
| FBXW5 | 9.034 | 7.279 | 8.785 | 12.573 | 11.795 | 11.034 | 11.621 | 0.0049293 | F-box and WD repeat domain containing 5 |
| CASP8 | 5.377 | 4.848 | 5.514 | 8.226 | 8.916 | 9.061 | 11.625 | 0.0008815 | caspase 8, apoptosis-related cysteine peptidase |
| ANAPC2 | 5.768 | 4.577 | 4.007 | 8.416 | 7.549 | 8.419 | 11.654 | 0.0039719 | anaphase promoting complex subunit 2 |
| FAM83E | 5.452 | 3.814 | 5.304 | 8.512 | 8.621 | 9.009 | 11.770 | 0.0013279 | family with sequence similarity 83, member E |
| DOCK9 | 5.751 | 4.494 | 4.174 | 8.052 | 7.766 | 8.292 | 11.778 | 0.0034964 | dedicator of cytokinesis 9 |
| CCDC127 | 4.142 | 5.205 | 6.592 | 8.764 | 9.094 | 8.645 | 11.783 | 0.0045646 | coiled-coil domain containing 127 |
| REPIN1 | 8.839 | 6.352 | 6.959 | 10.657 | 10.701 | 9.922 | 11.877 | 0.0104246 | replication initiator 1 |
| BCL2L12 | 5.109 | 4.876 | 5.847 | 8.684 | 8.643 | 8.767 | 11.916 | 0.0008225 | BCL2-like 12 (proline rich) |
| RNASEH2C | 2.233 | 2.233 | 2.991 | 6.770 | 5.811 | 4.777 | 11.939 | 0.0047012 | ribonuclease H2, subunit C |
| SPSB3 | 8.515 | 6.780 | 3.891 | 10.359 | 10.000 | 11.095 | 11.948 | 0.0105258 | splA/ryanodine receptor domain and SOCS box containing 3 |
| TSEN54 | 5.644 | 4.457 | 5.551 | 8.461 | 9.240 | 8.654 | 12.092 | 0.0014361 | tRNA splicing endonuclease 54 homolog (S. cerevisiae) |
| XRCC6 | 10.802 | 10.443 | 11.398 | 14.405 | 14.473 | 14.080 | 12.158 | 0.0008406 | X-ray repair complementing defective repair in Chinese hamster cells 6 |
| LRRC10 | 0.648 | 0.648 | 0.729 | 3.871 | 4.728 | 4.262 | 12.245 | 0.0004794 | leucine rich repeat containing 10 |
| SLC22A9 | 0.648 | 0.648 | 0.648 | 2.202 | 4.428 | 4.262 | 12.245 | 0.0094347 | solute carrier family 22 (organic anion transporter), member 9 |
| SNORD34 | 0.648 | 1.962 | 3.351 | 4.262 | 5.865 | 5.961 | 12.245 | 0.0099983 | small nucleolar RNA, C/D box 34 |
| ACRBP | 0.648 | 0.648 | 0.648 | 4.529 | 0.648 | 4.262 | 12.245 | 0.0409719 | acrosin binding protein |
| ZNF767 | 4.525 | 2.814 | 4.876 | 8.122 | 8.400 | 8.140 | 12.251 | 0.0012288 | zinc finger family member 767 |
| TSPYL2 | 10.396 | 9.577 | 10.805 | 14.011 | 12.942 | 14.609 | 12.255 | 0.0028087 | TSPY-like 2 |
| CFP | 4.734 | 3.420 | 3.296 | 7.303 | 6.914 | 7.554 | 12.274 | 0.0022215 | complement factor properdin |
| SNORA57 | 3.194 | 2.593 | 0.648 | 4.748 | 5.246 | 6.823 | 12.373 | 0.0096510 | small nucleolar RNA, H/ACA box 57 |
| SECISBP2 | 7.068 | 5.153 | 6.509 | 10.596 | 10.142 | 9.735 | 12.403 | 0.0017251 | SECIS binding protein 2 |
| SURF2 | 0.648 | 0.648 | 0.999 | 4.632 | 4.311 | 3.043 | 12.409 | 0.0033889 | surfeit 2 |
| LOC283663 | 2.970 | 3.067 | 5.412 | 7.358 | 6.604 | 8.163 | 12.410 | 0.0073425 | No description |
| FBXO10 | 5.936 | 3.298 | 4.102 | 7.748 | 7.617 | 8.136 | 12.524 | 0.0067754 | F-box protein 10 |
| SCNM1 | 1.648 | 3.904 | 3.170 | 7.553 | 6.812 | 6.659 | 12.543 | 0.0019082 | sodium channel modifier 1 |
| PHKG1 | 1.648 | 1.648 | 1.648 | 4.017 | 5.304 | 5.398 | 12.603 | 0.0026277 | phosphorylase kinase, gamma 1 (muscle) |
| SHARPIN | 6.911 | 5.396 | 6.225 | 10.149 | 9.883 | 9.122 | 12.625 | 0.0021986 | SHANK-associated RH domain interactor |
| RAB34 | 9.747 | 8.006 | 8.931 | 13.319 | 12.592 | 12.196 | 12.650 | 0.0018721 | RAB34, member RAS oncogene family |
| C9orf45 | 0.648 | 0.648 | 0.729 | 3.871 | 4.311 | 5.961 | 12.664 | 0.0014901 | No description |
| PRDM11 | 0.648 | 0.648 | 0.729 | 3.081 | 4.311 | 4.901 | 12.664 | 0.0028877 | PR domain containing 11 |
| PVT1 | 7.214 | 6.483 | 6.496 | 9.054 | 12.090 | 10.160 | 12.671 | 0.0061452 | Pvt1 oncogene (non-protein coding) |
| HSD11B1 | 4.972 | 5.859 | 7.615 | 9.647 | 9.077 | 9.543 | 12.848 | 0.0078562 | hydroxysteroid (11-beta) dehydrogenase 1 |
| ACOX3 | 1.648 | 3.904 | 4.351 | 7.369 | 7.592 | 7.882 | 12.890 | 0.0021806 | acyl-CoA oxidase 3, pristanoyl |
| SNORD22 | 4.647 | 2.593 | 4.602 | 7.390 | 8.344 | 7.924 | 12.974 | 0.0065958 | small nucleolar RNA, C/D box 22 |
| FOXE3 | 0.648 | 0.648 | 0.729 | 4.372 | 4.428 | 0.648 | 12.986 | 0.0422596 | forkhead box E3 |
| C19orf76 | 5.552 | 4.667 | 5.989 | 7.636 | 9.252 | 9.704 | 12.993 | 0.0052059 | chromosome 19 open reading frame 76 |

TABLE 4-continued

Differentially Expressed Genes in CD44+ Breast Epithelial Cells

| | Nulliparous (NP) Samples | | | Parous (P) Samples | | | Pseudo fold change | P value | Gene description |
|---|---|---|---|---|---|---|---|---|---|
| Gene Symbol | CD44+ N48 | CD44+ N58 | CD44+ N43 | CD44+ N37 | CD44+ N39 | CD44+ N40 | | | |
| ZNF836 | 1.648 | 1.648 | 2.245 | 5.973 | 5.312 | 5.353 | 13.036 | 0.0005154 | zinc finger protein 836 |
| SGK269 | 7.191 | 6.789 | 8.039 | 9.615 | 11.249 | 11.744 | 13.041 | 0.0047553 | No description |
| FAM50B | 5.109 | 2.233 | 2.951 | 6.726 | 6.386 | 6.657 | 13.047 | 0.0107234 | family with sequence similarity 50, member B |
| ZNF53A | 3.233 | 3.714 | 4.101 | 7.016 | 7.837 | 6.942 | 13.074 | 0.0009549 | zinc finger protein 33A |
| NCRNA00105 | 3.947 | 3.151 | 4.132 | 4.754 | 7.659 | 7.841 | 13.078 | 0.0170277 | No description |
| DTPS | 5.690 | 6.424 | 5.052 | 9.401 | 9.546 | 8.967 | 13.099 | 0.0012648 | CTP synthase |
| WDR81 | 6.259 | 5.889 | 6.723 | 11.107 | 8.374 | 9.976 | 13.154 | 0.0060773 | WD repeat domain 81 |
| EPR1 | 5.264 | 1.978 | 4.692 | 5.997 | 8.411 | 8.872 | 13.172 | 0.0130173 | effector cell peptidase receptor 1 (non-protein coding) |
| CECR6 | 0.648 | 0.648 | 0.729 | 4.372 | 4.311 | 5.014 | 13.212 | 0.0002153 | cat eye syndrome chromosome region, candidate 6 |
| IGSF21 | 0.648 | 0.648 | 1.719 | 4.372 | 2.987 | 6.556 | 13.212 | 0.0099893 | immunoglobin superfamily, member 21 |
| GCHFR | 0.648 | 3.431 | 3.871 | 7.185 | 6.592 | 7.156 | 13.217 | 0.0038139 | GTP cyclohydrolase I feedback regulator |
| SNAI3 | 2.233 | 2.233 | 2.704 | 4.908 | 5.968 | 9.074 | 13.314 | 0.0070562 | snail homolog 3 (Drosophila) |
| LGSN | 0.648 | 0.648 | 1.245 | 3.871 | 4.990 | 4.389 | 13.369 | 0.0009910 | lengsin, lens protein with glutamine synthetase domain |
| BTN2A2 | 5.109 | 2.461 | 3.278 | 7.264 | 6.205 | 7.421 | 13.401 | 0.0084724 | butyrophilin, subfamily 2, member A2 |
| SLC23A3 | 1.648 | 1.648 | 1.648 | 4.878 | 5.405 | 7.777 | 13.521 | 0.0024080 | solute carrier family 23 (nucleobase transporters), member 3 |
| MRPL34 | 7.254 | 5.355 | 6.978 | 11.013 | 10.598 | 9.969 | 13.544 | 0.0017820 | mitochondrial ribosomal protein L34 |
| RFPL3S | 0.648 | 2.941 | 1.649 | 5.355 | 5.411 | 5.761 | 13.565 | 0.0027719 | RFPL3 antisense RNA (non-protein coding) |
| GPR37L1 | 4.142 | 3.510 | 4.713 | 7.317 | 7.914 | 8.253 | 13.665 | 0.0010409 | G protein-coupled receptor 37 like 1 |
| PJA1 | 7.413 | 3.861 | 4.442 | 8.466 | 8.121 | 8.214 | 13.669 | 0.0184170 | praja ring finger 1 |
| RINT1 | 4.314 | 3.256 | 4.602 | 8.375 | 7.921 | 7.305 | 13.673 | 0.0012198 | RAD50 interactor 1 |
| NRN1L | 3.194 | 0.648 | 2.359 | 6.398 | 5.411 | 6.133 | 13.682 | 0.0034319 | neuritin 1 -like |
| SNORD36C | 7.188 | 6.684 | 8.703 | 10.458 | 11.754 | 11.622 | 13.684 | 0.0034229 | small nucleolar RNA, C/D box 36C |
| LOC642313 | 3.194 | 0.648 | 1.962 | 5.606 | 5.742 | 6.202 | 13.733 | 0.0029938 | No description |
| PLAC8L1 | 0.648 | 0.648 | 0.999 | 4.262 | 4.428 | 5.014 | 13.734 | 0.0003234 | PLAC8-like 1 |
| SCT | 0.648 | 0.648 | 1.477 | 3.081 | 4.428 | 5.606 | 13.734 | 0.0059303 | secretin |
| LOC493754 | 8.585 | 7.733 | 8.893 | 11.782 | 12.181 | 12.679 | 13.788 | 0.0008135 | No description |
| GRID1 | 7.053 | 4.490 | 4.848 | 9.588 | 8.312 | 8.646 | 13.914 | 0.0084191 | glutamate receptor, ionotropic, delta 1 |
| ZNF570 | 1.648 | 1.648 | 2.177 | 5.459 | 4.945 | 6.040 | 14.032 | 0.0007775 | zinc finger protein 570 |
| ANAPC1 | 6.227 | 4.615 | 5.654 | 9.432 | 9.476 | 9.518 | 14.135 | 0.0007685 | anaphase promoting complex subunit 1 |
| RAGE | 4.008 | 4.376 | 5.037 | 7.974 | 8.283 | 8.202 | 14.183 | 0.0005875 | renal tumor antigen |
| NCF4 | 2.648 | 3.791 | 4.241 | 6.476 | 7.734 | 7.753 | 14.203 | 0.0023449 | neutrophil cytosolic factor 4, 40 kDa |
| RGS12 | 6.235 | 5.153 | 6.640 | 9.155 | 10.065 | 10.271 | 14.222 | 0.0015539 | regulator of G-protein signaling 12 |
| RECQL4 | 2.970 | 3.233 | 4.343 | 6.526 | 7.360 | 8.174 | 14.226 | 0.0020572 | RecQ protein-like 4 |
| BCAN | 4.423 | 2.601 | 4.505 | 7.996 | 7.558 | 8.343 | 14.296 | 0.0014631 | brevican |
| TNFRSF4 | 6.669 | 4.372 | 6.316 | 9.924 | 9.190 | 10.510 | 14.329 | 0.0027359 | tumor necrosis factor receptor superfamily, member 4 |
| SLC45A4 | 4.008 | 4.402 | 4.465 | 7.852 | 8.328 | 8.084 | 14.363 | 0.0002062 | solute carrier family 45, member 4 |
| IDO1 | 0.648 | 1.649 | 1.387 | 4.372 | 5.246 | 6.798 | 14.506 | 0.0018229 | Description |
| PRICKLES | 3.456 | 4.514 | 4.818 | 8.025 | 8.388 | 8.688 | 14.665 | 0.0005695 | prickle homolog 3 (Drosophila) |
| LOC284551 | 0.648 | 3.980 | 0.648 | 4.529 | 4.870 | 4.602 | 14.735 | 0.0214201 | No description |
| RMND5B | 5.688 | 4.492 | 4.883 | 9.585 | 9.071 | 8.280 | 14.890 | 0.0009459 | required for meiotic nuclear division 5 homolog B (S. cerevisiae) |
| EXTL3 | 6.870 | 5.070 | 6.362 | 11.076 | 10.080 | 8.971 | 14.940 | 0.0033619 | exostoses (multiple)-like 3 |
| C8orf86 | 5.400 | 5.119 | 6.628 | 9.455 | 9.958 | 9.023 | 14.967 | 0.0015359 | chromosome 8 open reading frame 86 |
| COX18 | 4.482 | 3.486 | 3.710 | 7.614 | 7.460 | 7.791 | 14.975 | 0.0005425 | COX18 cytochrome c oxidase assembly homolog (S. cerevisiae) |
| INTS12 | 4.647 | 4.262 | 3.980 | 8.181 | 8.551 | 7.847 | 14.977 | 0.0003144 | integrator complex subunit 12 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| MNAT1 | 5.726 | 3.013 | 4.481 | 8.953 | 8.422 | 7.204 | 15.356 | 0.0058263 | menage a trois homolog 1, cyclin H assembly factor (Xenopus laevis) |
| UCN | 0.648 | 3.046 | 0.999 | 5.894 | 5.411 | 4.602 | 15.490 | 0.0047373 | urocortin |
| G6PD | 7.905 | 7.528 | 9.221 | 12.805 | 12.079 | 11.482 | 15.498 | 0.0018811 | glucose-6-phosphate dehydrogenase |
| CD3E | 6.070 | 2.233 | 2.722 | 6.190 | 7.057 | 9.488 | 15.528 | 0.0155373 | CD3e molecule, epsilon (CD3-TCR complex) |
| KCNK3 | 2.233 | 3.170 | 2.722 | 8.049 | 6.639 | 6.196 | 15.594 | 0.0009231 | potassium channel, subfamily K, member 3 |
| SPEG | 3.792 | 2.648 | 2.871 | 6.240 | 8.218 | 6.838 | 15.633 | 0.0019442 | SPEG complex locus |
| ZNF692 | 5.377 | 4.273 | 5.235 | 8.826 | 8.972 | 9.346 | 15.655 | 0.0004253 | zinc finger protein 692 |
| SNORA21 | 0.648 | 0.648 | 1.477 | 4.632 | 4.990 | 5.230 | 15.822 | 0.0003324 | small nucleolar RNA, H/ACA box 21 |
| NUDT12 | 0.648 | 0.648 | 1.564 | 4.632 | 5.600 | 4.389 | 15.822 | 0.0008724 | nudix (nucleoside diphosphate linked moiety X)-type motif 12 |
| HOXC11 | 0.648 | 0.648 | 0.648 | 4.632 | 2.987 | 5.830 | 15.822 | 0.0040579 | homeobox C11 |
| TBC1D26 | 0.648 | 0.648 | 1.477 | 3.871 | 5.462 | 5.407 | 15.833 | 0.0012919 | TBC1 domain family, member 26 |
| CXorf15 | 2.233 | 2.649 | 4.221 | 6.239 | 6.710 | 7.624 | 16.059 | 0.0031158 | No description |
| PGS1 | 6.444 | 3.983 | 5.523 | 10.109 | 9.529 | 8.922 | 16.069 | 0.0021473 | phosphatidylglycerophosphate synthase 1 |
| MAP1S | 8.181 | 7.405 | 8.625 | 12.188 | 12.474 | 12.157 | 16.085 | 0.0003054 | microtubule-associated protein 1S |
| BCAM | 8.349 | 4.465 | 4.814 | 8.481 | 11.401 | 9.096 | 16.175 | 0.0164385 | basal cell adhesion molecule (Lutheran blood group) |
| CCT2 | 9.878 | 9.840 | 10.102 | 13.824 | 14.221 | 13.898 | 16.227 | 0.0001203 | chaperonin containing TCP1, subunit 2 (beta) |
| C17orf67 | 3.860 | 0.648 | 3.336 | 7.295 | 7.199 | 7.882 | 16.248 | 0.0018901 | chromosome 17 open reading frame 67 |
| SLED1 | 0.648 | 1.649 | 3.810 | 5.035 | 5.687 | 7.491 | 16.427 | 0.0076711 | No description |
| ZNF18 | 0.648 | 1.962 | 2.552 | 6.963 | 4.728 | 5.158 | 16.906 | 0.0044329 | zinc finger protein 18 |
| LOC654433 | 2.648 | 2.970 | 3.251 | 7.066 | 8.175 | 4.579 | 17.099 | 0.0093023 | No description |
| ABCB4 | 0.648 | 1.962 | 3.208 | 4.748 | 6.510 | 6.133 | 17.150 | 0.0049924 | ATP-binding cassette, sub-family B (MDR/TAP), member 4 |
| DECR2 | 3.947 | 4.983 | 6.306 | 8.447 | 9.153 | 9.094 | 17.277 | 0.0030569 | 2,4-dienoyl CoA reductase 2, peroxisomal |
| SMARCA4 | 6.554 | 7.264 | 8.534 | 11.374 | 11.986 | 11.026 | 17.278 | 0.0016080 | SWI/SNF related, matrix associated, actin dependent regulator of chromatin, subfamily a, member 4 |
| MESTIT1 | 4.620 | 3.659 | 4.621 | 8.136 | 7.836 | 8.742 | 17.398 | 0.0006464 | MEST intronic transcript 1 (non-protein coding) |
| LAT | 5.322 | 3.508 | 5.696 | 8.509 | 8.314 | 9.833 | 17.592 | 0.0031581 | linker for activation of T cells |
| C1orf51 | 4.423 | 5.256 | 6.187 | 8.726 | 9.400 | 9.418 | 17.680 | 0.0013369 | chromosome 1 open reading frame 51 |
| FBXL8 | 4.647 | 0.648 | 2.170 | 7.135 | 6.331 | 6.367 | 18.343 | 0.0071234 | F-box and leucine-rich repeat protein 8 |
| ZNF844 | 0.648 | 0.648 | 1.564 | 5.452 | 4.311 | 5.761 | 18.347 | 0.0007234 | zinc finger protein 844 |
| GPATCH2 | 2.648 | 3.621 | 3.896 | 6.852 | 7.826 | 7.868 | 18.428 | 0.0007144 | G patch domain containing 2 |
| RAB39 | 0.648 | 0.648 | 0.729 | 4.854 | 4.990 | 3.966 | 18.457 | 0.0004073 | RAB39, member RAS oncogene family |
| CACNB1 | 5.404 | 4.918 | 6.934 | 9.131 | 9.644 | 10.205 | 18.546 | 0.0021716 | calcium channel, voltage-dependent, beta 1 subunit |
| PUS7L | 0.648 | 0.648 | 0.648 | 4.372 | 4.870 | 5.014 | 18.660 | 0.0001293 | pseudouridylate synthase 7 homolog (S. cerevisiae)-like |
| ACTR5 | 4.264 | 5.186 | 5.611 | 9.415 | 9.520 | 9.044 | 18.757 | 0.0003504 | ARP5 actin-related protein 5 homolog (yeast) |
| SMURF1 | 8.266 | 6.625 | 8.664 | 12.432 | 12.705 | 12.497 | 18.776 | 0.0005244 | SMAD specific E3 ubiquitin protein ligase 1 |
| NPW | 0.648 | 1.962 | 3.336 | 5.688 | 7.185 | 6.202 | 18.895 | 0.0023629 | neuropeptide W |
| KRBA1 | 3.619 | 4.075 | 4.916 | 8.712 | 9.172 | 7.723 | 19.112 | 0.0007005 | KRAB-A domain containing 1 |
| MGC12982 | 1.648 | 1.648 | 2.206 | 6.517 | 4.017 | 6.487 | 19.846 | 0.0043151 | No description |
| TKTL1 | 0.648 | 1.962 | 3.959 | 6.279 | 5.246 | 6.944 | 19.929 | 0.0066069 | transketolase-like 1 |
| NSMCE1 | 4.647 | 0.648 | 3.351 | 7.681 | 7.681 | 6.367 | 20.124 | 0.0062582 | non-SMC element 1 homolog (S. cerevisiae) |
| LRRC37A3 | 4.972 | 0.648 | 2.329 | 6.552 | 6.666 | 7.441 | 20.201 | 0.0075990 | leucine rich repeat containing 37, member A3 |
| PECR | 0.648 | 0.648 | 1.719 | 5.813 | 4.990 | 5.606 | 20.282 | 0.0002783 | peroxisomal trans-2-enoyl-CoA reductase |
| ITGB7 | 4.647 | 2.268 | 2.987 | 5.764 | 7.494 | 8.995 | 20.368 | 0.0067983 | integrin, beta 7 |
| PRO0628 | 3.194 | 0.648 | 1.973 | 6.329 | 6.142 | 6.872 | 20.466 | 0.0011477 | No description |
| TBX2 | 9.232 | 6.609 | 4.244 | 11.368 | 9.502 | 10.966 | 20.481 | 0.0153196 | T-box 2 |

TABLE 4-continued

Differentially Expressed Genes in CD44+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD44+ N48 | CD44+ N58 | CD44+ N43 | CD44+ N37 | CD44+ N39 | CD44+ N40 | | | |
| CACNA1G | 7.881 | 5.986 | 7.549 | 10.415 | 10.363 | 13.188 | 20.775 | 0.0054007 | calcium channel, voltage-dependent, T type, alpha 1 G subunit |
| ZIK1 | 0.648 | 0.648 | 0.648 | 5.035 | 5.196 | 3.351 | 20.919 | 0.0015990 | zinc finger protein interacting with K protein 1 homolog (mouse) |
| MGC16384 | 0.648 | 2.552 | 0.729 | 5.035 | 5.246 | 5.462 | 20.919 | 0.0017341 | No description |
| PTPN23 | 7.691 | 6.872 | 8.243 | 12.222 | 12.142 | 11.267 | 21.037 | 0.0005515 | protein tyrosine phosphatase, non-receptor type 23 |
| QRSL1 | 5.431 | 4.501 | 5.485 | 9.400 | 9.941 | 9.513 | 21.950 | 0.0001653 | glutaminyl-tRNA synthase (glutamine-hydrolyzing)-like 1 |
| SLC1A5 | 10.089 | 9.315 | 12.001 | 14.578 | 14.943 | 14.478 | 22.450 | 0.0022395 | solute carrier family 1 (neutral amino acid transporter), member 5 |
| AIPL1 | 3.194 | 0.648 | 1.245 | 5.870 | 5.742 | 5.544 | 22.569 | 0.0026818 | aryl hydrocarbon receptor interacting protein-like 1 |
| C12orf59 | 3.194 | 0.648 | 1.245 | 5.355 | 5.742 | 6.006 | 22.569 | 0.0029217 | chromosome 12 open reading frame 59 |
| ANKRD34C | 0.648 | 0.648 | 1.973 | 5.213 | 6.052 | 5.158 | 22.772 | 0.0005334 | ankyrin repeat domain 340 |
| NOL6 | 4.580 | 3.779 | 5.382 | 8.297 | 9.972 | 9.096 | 22.912 | 0.0007594 | nucleolar protein family 6 (RNA-associated) |
| ZNF93 | 1.648 | 2.649 | 2.413 | 6.831 | 6.232 | 7.198 | 23.410 | 0.0002243 | zinc finger protein 93 |
| ACCN3 | 2.970 | 3.151 | 4.318 | 7.521 | 8.090 | 8.403 | 23.431 | 0.0003594 | amiloride-sensitive cation channel 3 |
| NME2P1 | 1.648 | 1.648 | 1.834 | 5.707 | 6.232 | 6.389 | 23.507 | 0.0001113 | non-metastatic cells 2, protein (NM23B) expressed in, pseudogene 1 |
| NOL7 | 1.648 | 1.648 | 1.648 | 6.634 | 6.204 | 3.294 | 23.519 | 0.0080295 | nucleolar protein 7, 27 kDa |
| UPK3B | 3.422 | 2.064 | 5.078 | 8.024 | 7.731 | 8.324 | 24.283 | 0.0019352 | uroplakin 3B |
| SS18L2 | 7.081 | 6.841 | 7.491 | 11.675 | 11.640 | 12.144 | 25.152 | 0.0000932 | synovial sarcoma translocation gene on chromosome 18-like 2 |
| RGPD1 | 2.233 | 2.951 | 2.233 | 7.147 | 7.451 | 6.906 | 25.508 | 0.0001023 | RANBP2-like and GRIP domain containing 1 |
| ZNF619 | 0.648 | 0.648 | 0.729 | 5.355 | 3.871 | 5.462 | 26.117 | 0.0006555 | zinc finger protein 619 |
| METTL2B | 0.648 | 0.648 | 1.719 | 5.452 | 6.052 | 5.407 | 27.064 | 0.0001834 | methyltransferase like2B |
| EVPL | 0.648 | 1.477 | 2.552 | 5.407 | 7.822 | 5.889 | 27.064 | 0.0014000 | envoplakin |
| DCXR | 6.617 | 6.701 | 8.147 | 11.804 | 12.259 | 11.408 | 27.672 | 0.0003893 | dicarbonyl/L-xylulose reductase |
| SPSB2 | 0.648 | 0.648 | 2.329 | 7.148 | 5.462 | 5.889 | 28.225 | 0.0006014 | splA/ryanodine receptor domain and SOCS box containing 2 |
| C15orf48 | 3.860 | 3.043 | 0.648 | 7.328 | 8.263 | 7.907 | 29.119 | 0.0009140 | chromosome 15 open reading frame 48 |
| FCER1G | 0.648 | 0.648 | 0.648 | 6.312 | 3.633 | 5.606 | 31.080 | 0.0013189 | Fc fragment of IgE, high affinity I, receptor for; gamma polypeptide |
| FANCB | 4.972 | 0.648 | 0.648 | 5.894 | 5.865 | 6.202 | 37.176 | 0.0135546 | Fanconi anemia, complementation group B |
| FSD1 | 0.648 | 0.648 | 0.648 | 5.870 | 0.648 | 6.006 | 37.314 | 0.0271508 | fibronectin type III and SPRY domain containing 1 |
| DRG1 | 1.648 | 2.926 | 5.319 | 8.440 | 8.179 | 7.484 | 38.122 | 0.0030298 | developmentally regulated GTP binding protein 1 |
| HPDL | 0.648 | 0.648 | 2.781 | 6.976 | 7.761 | 6.173 | 46.038 | 0.0003685 | 4-hydroxyphenylpyruvate dioxygenase-like |
| CD101 | 1.648 | 1.648 | 2.281 | 5.652 | 7.742 | 7.958 | 51.175 | 0.0004343 | CD101 molecule |
| SIRPB2 | 0.648 | 1.753 | 4.728 | 8.298 | 7.353 | 8.323 | 93.363 | 0.0015449 | signal-regulatory protein beta 2 |
| PLEKHM1P | 0.648 | 1.753 | 4.795 | 8.434 | 8.564 | 8.519 | 108.842 | 0.0007865 | pleckstrin homology domain containing, family M (with RUN domain) member 1 pseudogene |

TABLE 5

Differentially Expressed Genes in CD24+ Breast Epithelial Cells

| | Nulliparous (NP) Samples | | | Parous (P) Samples | | | | Pseudo fold change | P value | Gene description |
|---|---|---|---|---|---|---|---|---|---|---|
| | CD24+ N48 | CD24+ N58 | CD24+ N43 | CD24+ N37 | CD24+ N39 | CD24+ N40 | | | | |
| | | | | | | | | Higher Expression in Nulliparous | | |
| CIB1 | 1.559 | 10.620 | 10.983 | 1.559 | 1.559 | 1.559 | | 533.984 | 0.0337103 | calcium and integrin binding 1 (calmyrin) |
| TFF3 | 10.240 | 9.888 | 9.115 | 4.390 | 6.708 | 3.059 | | -45.167 | 0.0023684 | trefoil factor 3 (intestinal) |
| MTCYB | 13.943 | 8.170 | 12.290 | 7.242 | 7.324 | 7.214 | | -33.079 | 0.0206094 | No description |
| C7orf50 | 4.851 | 7.090 | 6.583 | 1.559 | 1.559 | 1.559 | | -32.538 | 0.0005825 | chromosome 7 open reading frame 50 |
| CCDC74A | 3.188 | 4.443 | 5.095 | -0.026 | -0.026 | -0.026 | | -22.144 | 0.0004559 | coiled-coil domain containing 74A |
| TFF1 | 11.621 | 11.941 | 10.851 | 6.961 | 7.801 | 6.437 | | -21.327 | 0.0003108 | trefoil factor 1 |
| SERPINA11 | 5.342 | 3.772 | 6.304 | 0.974 | 1.692 | 0.974 | | -20.636 | 0.0020169 | serpin peptidase inhibitor, clade A (alpha-1 antiproteinase, antitrypsin), member 11 |
| PVRL2 | 10.407 | 11.119 | 10.946 | 6.896 | 6.702 | 6.732 | | -18.559 | 0.0001028 | poliovirus receptor-related 2 (herpesvirus entry mediator B) |
| SUSD3 | 4.215 | 7.127 | 6.140 | 1.974 | 2.377 | 1.974 | | -17.947 | 0.0036823 | sushi domain containing 3 |
| EIF6 | 8.452 | 11.035 | 10.066 | 5.906 | 6.278 | 5.930 | | -17.574 | 0.0022003 | eukaryotic translation initiation factor 6 |
| C5orf38 | 4.605 | 3.974 | 4.944 | 0.845 | -0.026 | -0.026 | | -17.137 | 0.0002057 | chromosome 5 open reading frame 38 |
| AGR3 | 7.230 | 7.178 | 6.051 | 1.911 | 3.949 | 3.264 | | -15.080 | 0.0017874 | anterior gradient homolog 3 (Xenopus laevis) |
| ATHL1 | 10.501 | 10.990 | 9.529 | 6.235 | 7.175 | 6.449 | | -14.070 | 0.0006930 | ATH1, acid trehalase-like 1 (yeast) |
| MRPS11 | 3.188 | 5.147 | 4.857 | -0.026 | -0.026 | 1.348 | | -13.926 | 0.0018066 | mitochondrial ribosomal protein S11 |
| NDUFB4 | 7.373 | 8.506 | 6.918 | 3.176 | 4.239 | 3.825 | | -13.380 | 0.0007682 | NADH dehydrogenase (ubiquinone) 1 beta subcomplex, 4, 15 kDa |
| FAM86B2 | -0.026 | 4.592 | 3.693 | -0.026 | -0.026 | -0.026 | | -13.165 | 0.0481616 | family with sequence similarity 86, member B2 |
| AZGP1 | 10.381 | 12.099 | 9.970 | 6.678 | 7.118 | 6.482 | | -13.019 | 0.0010906 | alpha-2-glycoprotein 1, zinc-binding |
| LOC389033 | 3.649 | 3.288 | 5.348 | -0.026 | 1.169 | -0.026 | | -12.770 | 0.0023078 | No description |
| GPAA1 | 6.766 | 8.943 | 9.141 | 5.190 | 5.519 | 5.126 | | -12.319 | 0.0065104 | glycosylphosphatidylinositol anchor attachment protein 1 homolog (yeast) |
| COBRA1 | 6.106 | 8.803 | 8.403 | 4.892 | 5.309 | 4.150 | | -11.264 | 0.0107836 | cofactor of BRCA1 |
| PMPCA | 5.824 | 8.007 | 8.599 | 3.327 | 3.350 | 5.124 | | -11.119 | 0.0085541 | peptidase (mitochondrial processing) alpha |
| MRPL24 | 7.035 | 6.893 | 6.291 | 3.334 | 3.583 | 3.220 | | -10.941 | 0.0001842 | mitochondrial ribosomal protein L24 |
| MRPS33 | 5.605 | 5.240 | 4.954 | 1.474 | 4.016 | 1.819 | | -10.711 | 0.0099494 | mitochondrial ribosomal protein S33 |
| BMS1P5 | 5.492 | 5.644 | 4.208 | 0.845 | 1.169 | 3.335 | | -10.285 | 0.0070691 | BMS1 pseudogene 5 |
| CRB3 | 5.584 | 7.524 | 7.855 | 4.165 | 3.845 | 4.378 | | -10.263 | 0.0067038 | crumbs homolog 3 (Drosophila) |
| MTCO1 | 13.611 | 14.451 | 10.812 | 10.258 | 10.293 | 8.868 | | -10.214 | 0.0196493 | No description |
| PHGR1 | 7.919 | 5.175 | 8.219 | 4.568 | 4.706 | 3.591 | | -10.205 | 0.0191842 | proline/histidine/glycine-rich 1 |
| SCAND1 | 7.584 | 8.333 | 8.948 | 5.240 | 4.989 | 4.801 | | -10.149 | 0.0006431 | SCAN domain containing 1 |
| C9orf116 | 3.966 | 3.288 | 0.505 | -0.026 | -0.026 | -0.026 | | -9.939 | 0.0267529 | chromosome 9 open reading frame 116 |
| EREG | 6.353 | 7.355 | 4.883 | 4.050 | 2.559 | 2.559 | | -9.885 | 0.0082563 | epiregulin |
| ZNF467 | 4.851 | 5.416 | 5.049 | 2.826 | 1.559 | 1.559 | | -9.790 | 0.0010476 | zinc finger protein 467 |
| CCDC101 | 5.693 | 6.929 | 7.245 | 2.404 | 4.712 | 3.469 | | -9.775 | 0.0069839 | coiled-coil domain containing 101 |
| TPX2 | 5.086 | 4.235 | 5.066 | 1.474 | 3.324 | 0.974 | | -9.585 | 0.0080698 | TPX2, microtubule-associated, homolog (Xenopus laevis) |
| LOC646999 | 3.649 | 4.391 | 4.944 | -0.026 | 1.169 | 2.108 | | -9.331 | 0.0037813 | No description |
| VAV3 | 6.325 | 8.384 | 8.618 | 4.529 | 5.169 | 5.288 | | -9.284 | 0.0088933 | vav 3 guanine nucleotide exchange factor |
| C12orf70 | 3.188 | 3.616 | 4.158 | -0.026 | -0.026 | 1.348 | | -9.279 | 0.0015679 | chromosome 12 open reading frame 70 |
| ZNF669 | 4.851 | 6.383 | 5.942 | 3.169 | 2.648 | 2.173 | | -9.276 | 0.0019547 | zinc finger protein 669 |
| RNF126P1 | 8.036 | 7.646 | 8.207 | 4.857 | 4.906 | 4.857 | | -9.054 | 0.0001566 | ring finger protein 126 pseudogene 1 |
| RPL10A | 14.812 | 14.687 | 15.340 | 11.174 | 11.936 | 12.167 | | -9.020 | 0.0005150 | ribosomal protein L10a |
| MRPL54 | 6.771 | 6.849 | 7.016 | 3.013 | 4.222 | 3.704 | | -8.842 | 0.0004666 | mitochondrial ribosomal protein L54 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| SELENBP1 | 8.470 | 7.815 | 8.228 | 4.510 | 5.084 | 5.753 | −8.838 | 0.0008987 | selenium binding protein 1 |
| RTN2 | 4.054 | 5.749 | 7.379 | 2.610 | 3.496 | 2.404 | −8.808 | 0.0167337 | reticulon 2 |
| ENY2 | 4.277 | 4.107 | 2.247 | 0.974 | 0.974 | 0.974 | −8.768 | 0.0077767 | enhancer of yellow 2 homolog (Drosophila) |
| TMSB10 | 11.288 | 11.904 | 11.307 | 8.079 | 8.790 | 8.318 | −8.661 | 0.0003592 | thymosin beta 10 |
| HSP90AB1 | 12.327 | 13.551 | 12.840 | 8.810 | 9.765 | 10.447 | −8.598 | 0.0020706 | heat shock protein 90 kDa alpha (cytosolic), class B member 1 |
| SYTL1 | 6.465 | 6.431 | 7.194 | 3.327 | 3.772 | 3.650 | −8.595 | 0.0003216 | synaptotagmin-like 1 |
| CHCHD5 | 7.062 | 7.022 | 7.572 | 3.922 | 4.303 | 4.062 | −8.571 | 0.0001734 | coiled-coil-helix-coiled-coil-helix domain containing 5 |
| HMGCL | 4.054 | 4.457 | 4.083 | 0.974 | 1.692 | 0.974 | −8.453 | 0.0003699 | 3-hydroxymethyl-3-methylglutaryl-CoA lyase |
| CHMP2B | 6.820 | 6.172 | 5.046 | 3.108 | 3.090 | 3.376 | −8.368 | 0.0027260 | chromatin modifying protein 2B |
| RNF166 | 2.878 | 5.109 | 5.169 | 2.108 | 0.974 | 0.974 | −8.346 | 0.0085019 | ring finger protein 166 |
| ELF1 | 8.078 | 8.712 | 6.879 | 4.230 | 4.559 | 5.652 | −8.339 | 0.0041827 | E74-like factor 1 (ets domain transcription factor) |
| LILRB3 | 6.203 | 7.262 | 6.613 | 3.022 | 4.207 | 3.922 | −8.308 | 0.0015296 | leukocyte immunoglobulin-like receptor, subfamily B (with TM and ITIM domains), member 3 |
| IFRD2 | 6.087 | 8.625 | 8.764 | 4.412 | 5.653 | 5.586 | −8.220 | 0.0205986 | interferon-related developmental regulator 2 |
| PODXL2 | 7.074 | 6.172 | 7.483 | 4.050 | 4.367 | 3.787 | −8.133 | 0.0013454 | podocalyxin-like 2 |
| COX8A | 9.600 | 10.223 | 9.140 | 6.122 | 6.753 | 6.745 | −8.096 | 0.0006186 | cytochrome c oxidase subunit VIIIA (ubiquitous) |
| REEP5 | 7.493 | 9.006 | 8.503 | 5.700 | 5.475 | 5.508 | −7.970 | 0.0018173 | receptor accessory protein 5 |
| C19orf48 | 8.777 | 8.635 | 9.144 | 5.436 | 6.581 | 5.796 | −7.899 | 0.0003216 | chromosome 19 open reading frame 48 |
| LRRC41 | 6.651 | 10.165 | 8.862 | 5.425 | 5.894 | 6.471 | −7.824 | 0.0268918 | leucine rich repeat containing 41 |
| PTPRS | 6.297 | 6.643 | 6.542 | 3.578 | 3.772 | 2.899 | −7.801 | 0.0003377 | protein tyrosine phosphatase, receptor type, S |
| ITIH4 | 4.899 | 5.167 | 5.041 | 2.246 | 1.974 | 1.974 | −7.592 | 0.0001243 | inter-alpha (globulin) inhibitor H4 (plasma Kallikrein-sensitive glycoprotein) |
| C11orf10 | 9.678 | 9.947 | 9.006 | 6.203 | 6.586 | 7.055 | −7.422 | 0.0008365 | chromosome 11 open reading frame 10 |
| MGMT | 4.749 | 6.036 | 6.229 | 2.836 | 3.176 | 3.152 | −7.381 | 0.0029048 | O-6-methylguanine-DNA methyltransferase |
| FUZ | 4.851 | 5.667 | 5.277 | 2.404 | 2.648 | 2.173 | −7.325 | 0.0004021 | fuzzy homolog (Drosophila) |
| ARTN | 5.720 | 5.269 | 8.216 | 2.404 | 3.459 | 3.059 | −7.287 | 0.0079916 | artemin |
| ZNF232 | 1.913 | 3.335 | 2.835 | −0.026 | −0.026 | −0.026 | −7.263 | 0.0016063 | zinc finger protein 232 |
| EXOC3 | 6.184 | 8.234 | 7.461 | 4.616 | 4.444 | 4.951 | −7.186 | 0.0057836 | exocyst complex component 3 |
| CLCN7 | 7.526 | 9.222 | 9.226 | 6.079 | 6.384 | 5.873 | −7.173 | 0.0056470 | chloride channel 7 |
| LILRA5 | 3.758 | 3.922 | 3.799 | 0.974 | 0.974 | 0.974 | −7.082 | 0.0000921 | leukocyte immunoglobulin-like receptor, subfamily A (with TM domain), member 5 |
| DDX11 | 4.208 | 4.158 | 3.826 | 0.845 | 2.636 | 1.348 | −7.015 | 0.0054045 | DEAD/H (Asp-Glu-Ala-Asp/His) box polypeptide 11 |
| AHSA2 | 5.823 | 4.721 | 4.383 | 1.911 | 1.559 | 3.440 | −7.013 | 0.0088266 | AHA1, activator of heat shock 90 kDa protein ATPase homolog 2 (yeast) |
| HPX | 8.833 | 8.860 | 9.009 | 6.642 | 6.058 | 4.859 | −6.973 | 0.0018665 | hemopexin |
| PIN1 | 6.644 | 7.219 | 7.212 | 4.410 | 4.013 | 4.422 | −6.952 | 0.0003807 | peptidylprolyl cis/trans isomerase, NIMA-interacting 1 |
| VCL | 10.749 | 11.195 | 9.860 | 7.199 | 8.101 | 7.963 | −6.897 | 0.0019655 | vinculin |
| CBX8 | 3.758 | 3.997 | 4.619 | 1.845 | 0.974 | 0.974 | −6.885 | 0.0010261 | chromobox homolog 8 |
| GSDMD | 5.797 | 7.667 | 7.756 | 4.246 | 4.990 | 4.166 | −6.800 | 0.0086332 | gasdermin D |
| PGLS | 8.167 | 8.754 | 9.689 | 6.138 | 5.990 | 5.663 | −6.793 | 0.0015572 | 6-phosphogluconolactonase |
| MST1P2 | 5.577 | 4.930 | 5.421 | −0.026 | 3.345 | 2.671 | −6.729 | 0.0112041 | macrophage stimulating 1 (hepatocyte growth factor-like) pseudogene 2 |
| EPN1 | 6.666 | 8.478 | 8.825 | 5.840 | 5.728 | 5.600 | −6.728 | 0.0133837 | epsin 1 |
| YIF1A | 6.177 | 7.873 | 8.934 | 4.563 | 5.784 | 5.127 | −6.713 | 0.0186616 | Yip1 interacting factor homolog A (S. cerevisiae) |
| HYAL2 | 4.042 | 5.759 | 5.262 | 2.518 | 2.627 | 2.296 | −6.703 | 0.0041612 | hyaluronoglucosaminidase 2 |
| FUS | 8.547 | 9.376 | 8.624 | 5.823 | 6.132 | 6.353 | −6.610 | 0.0006823 | fused in sarcoma |
| ASCC2 | 4.126 | 5.838 | 5.924 | 3.043 | 3.204 | 2.899 | −6.587 | 0.0099125 | activating signal cointegrator 1 complex subunit 2 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| C12orf11 | 6.355 | 6.345 | 6.033 | 3.324 | 4.989 | 3.469 | −6.539 | 0.0069946 | chromosome 12 open reading frame 11 |
| PMAIP1 | 7.993 | 7.235 | 6.735 | 3.841 | 4.529 | 5.607 | −6.523 | 0.0058220 | phorbol-12-myristate-13-acetate-induced protein 1 |
| JOSD2 | 5.514 | 6.803 | 7.547 | 4.222 | 4.098 | 4.098 | −6.520 | 0.0067544 | Josephin domain containing 2 |
| VPS37D | 4.662 | 4.394 | 4.791 | 3.022 | 1.692 | 1.819 | −6.506 | 0.0031113 | vacuolar protein sorting 37 homolog D (*S. cerevisiae*) |
| RPS20 | 11.070 | 11.541 | 9.016 | 7.823 | 8.371 | 8.821 | −6.493 | 0.0250414 | ribosomal protein S20 |
| C1orf122 | 6.023 | 7.422 | 5.693 | 3.324 | 4.831 | 1.819 | −6.490 | 0.0139586 | chromosome 1 open reading frame 122 |
| FAM22A | 2.671 | 4.239 | 4.443 | −0.026 | −0.026 | 2.108 | −6.483 | 0.0093853 | family with sequence similarity 22, member A |
| RRP7A | 3.966 | 4.118 | 2.671 | 2.518 | −0.026 | 3.152 | −6.483 | 0.0370929 | ribosomal RNA processing 7 homolog A (*S. cerevisiae*) |
| PRINS | 4.797 | 5.638 | 5.214 | 2.518 | 2.296 | 2.695 | −6.482 | 0.0005257 | psoriasis associated RNA induced by stress (non-protein coding) |
| C19orf10 | 8.829 | 9.050 | 8.383 | 5.723 | 6.487 | 5.689 | −6.470 | 0.0007252 | chromosome 19 open reading frame 10 |
| ACTG1 | 14.586 | 15.068 | 13.525 | 11.545 | 11.805 | 12.398 | −6.361 | 0.0045533 | actin, gamma 1 |
| MARCKSL1 | 9.853 | 10.736 | 10.478 | 7.185 | 7.464 | 8.113 | −6.353 | 0.0011397 | MARCKS-like 1 |
| SNORD36A | 2.671 | 3.088 | 2.636 | −0.026 | −0.026 | 2.108 | −6.327 | 0.0206930 | small nucleolar RNA, C/D box 36A |
| FAM3D | 3.188 | 3.825 | 2.636 | −0.026 | −0.026 | 2.671 | −6.327 | 0.0302279 | family with sequence similarity 3, member D |
| JUP | 11.875 | 12.471 | 12.973 | 9.255 | 9.831 | 9.838 | −6.231 | 0.0010046 | junction plakoglobin |
| SERPINA1 | 8.496 | 8.443 | 5.886 | 5.106 | 5.858 | 4.752 | −6.226 | 0.0258212 | serpin peptidase inhibitor, clade A (alpha-1 antiproteinase, antitrypsin), member 1 |
| TACO1 | 3.649 | 6.286 | 6.229 | 2.836 | 3.649 | 2.671 | −6.219 | 0.0270595 | translational activator of mitochondrially encoded cytochrome c oxidase I |
| MGAT4B | 7.461 | 9.527 | 8.667 | 6.029 | 6.032 | 6.621 | −6.209 | 0.0102901 | mannosyl (alpha-1,3-)-glycoprotein beta-1,4-N-acetylglucosaminyltransferase, isozyme B |
| FAM160A2 | 4.708 | 7.223 | 7.273 | 3.821 | 4.390 | 4.643 | −6.191 | 0.0344911 | family with sequence similarity 160, member A2 |
| ARHGEF10L | 8.903 | 9.103 | 9.493 | 6.275 | 6.563 | 6.845 | −6.181 | 0.0004988 | Rho guanine nucleotide exchange factor (GEF) 10-like |
| SCUBE2 | 7.232 | 6.205 | 5.575 | 3.802 | 2.840 | 4.608 | −6.165 | 0.0091711 | signal peptide, CUB domain, EGF-like 2 |
| ACBD4 | 4.137 | 5.273 | 6.032 | 2.650 | 1.559 | 2.650 | −6.160 | 0.0048665 | acyl-CoA binding domain containing 4 |
| LASP1 | 7.207 | 8.076 | 6.702 | 4.675 | 4.484 | 4.585 | −6.158 | 0.0014329 | LIM and SH3 protein 1 |
| C17orf106 | 5.167 | 5.041 | 4.591 | 2.246 | 2.858 | 1.974 | −6.132 | 0.0009885 | chromosome 17 open reading frame 106 |
| TWF2 | 5.309 | 7.290 | 6.939 | 4.675 | 4.222 | 3.704 | −6.128 | 0.0124444 | twinfilin, actin-binding protein, homolog 2 (*Drosophila*) |
| DUSP10 | 6.104 | 4.771 | 4.013 | 2.404 | 2.075 | 2.173 | −6.054 | 0.0047782 | dual specificity phosphatase 10 |
| CD14 | 6.721 | 8.780 | 9.208 | 6.118 | 5.454 | 6.616 | −6.032 | 0.0271312 | CD14 molecule |
| RPL35 | 13.350 | 12.355 | 13.885 | 10.017 | 10.757 | 11.257 | −6.032 | 0.0056017 | ribosomal protein L35 |
| CCS | 4.042 | 5.633 | 6.023 | 3.404 | 2.627 | 3.043 | −6.021 | 0.0132180 | copper chaperone for superoxide dismutase |
| MTA1 | 8.119 | 9.199 | 8.140 | 5.412 | 6.611 | 6.247 | −6.017 | 0.0047644 | metastasis associated 1 |
| ALKBH7 | 8.798 | 8.202 | 9.437 | 5.616 | 5.823 | 6.875 | −6.002 | 0.0032617 | alkB, alkylation repair homolog 7 (*E. coli*) |
| ARVCF | 5.414 | 6.740 | 6.276 | 3.484 | 3.711 | 4.085 | −5.918 | 0.0031665 | armadillo repeat gene deleted in velocardiofacial syndrome |
| CSTF1 | 4.899 | 5.648 | 5.214 | 2.649 | 4.222 | 1.974 | −5.915 | 0.0139693 | cleavage stimulation factor, 3' pre-RNA, subunit 1, 50 kDa |
| C16orf89 | 4.215 | 5.410 | 5.313 | 1.974 | 2.858 | 1.974 | −5.864 | 0.0025265 | chromosome 16 open reading frame 89 |
| TCEAL4 | 5.376 | 5.661 | 5.125 | 2.826 | 1.559 | 4.144 | −5.858 | 0.0122072 | transcription elongation factor A (SII)-like 4 |
| ZNF775 | 1.913 | 2.525 | 4.240 | −0.026 | −0.026 | −0.026 | −5.857 | 0.0052418 | zinc finger protein 775 |
| FAM150B | 3.188 | 2.525 | 1.169 | −0.026 | −0.026 | −0.026 | −5.845 | 0.0089639 | family with sequence similarity 150, member B |
| MIER2 | 4.918 | 6.164 | 6.144 | 2.782 | 3.350 | 3.616 | −5.797 | 0.0034797 | mesoderm induction early response 1, family member 2 |
| TOMM34 | 6.319 | 7.250 | 6.565 | 3.907 | 4.030 | 4.590 | −5.796 | 0.0013922 | translocase of outer mitochondrial membrane 34 |
| LENG9 | 8.034 | 7.405 | 7.562 | 4.821 | 5.030 | 6.399 | −5.784 | 0.0075280 | leukocyte receptor cluster (LRC) member 9 |
| SNORD10 | 5.197 | 2.671 | 3.616 | 1.734 | −0.026 | 2.671 | −5.761 | 0.0396040 | small nucleolar RNA, C/D box 10 |
| OTUD5 | 7.134 | 8.489 | 8.724 | 5.426 | 6.012 | 5.972 | −5.727 | 0.0065679 | OTU domain containing 5 |
| LGMN | 7.074 | 7.780 | 7.146 | 4.839 | 4.565 | 5.010 | −5.692 | 0.0006715 | legumain |

TABLE 5-continued

Differentially Expressed Genes in CD24+ Breast Epithelial Cells

| | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| RAB11B | 8.150 | 9.341 | 8.247 | 5.884 | 5.667 | 5.747 | −5.658 | 0.0011121 | RAB11B, member RAS oncogene family |
| LRGUK | 3.758 | 3.659 | 3.469 | 0.974 | 1.692 | 0.974 | −5.635 | 0.0007897 | leucine-rich repeats and guanylate kinase domain containing |
| NCRNA00116 | 4.290 | 5.540 | 5.117 | 2.859 | 2.627 | 2.296 | −5.619 | 0.0027114 | non-protein coding RNA 116 |
| ARHGEF7 | 7.164 | 7.990 | 7.784 | 4.542 | 5.447 | 5.502 | −5.613 | 0.0021811 | Rho guanine nucleotide exchange factor (GEF) 7 |
| FTSJD2 | 6.501 | 7.938 | 8.083 | 4.960 | 5.608 | 5.101 | −5.562 | 0.0075173 | FtsJ methyltransferase domain containing 2 |
| RHOT2 | 6.868 | 8.612 | 9.093 | 6.143 | 6.172 | 5.895 | −5.539 | 0.0174167 | ras homolog gene family, member T2 |
| SSNA1 | 6.275 | 8.714 | 9.056 | 6.248 | 6.419 | 4.755 | −5.524 | 0.0434121 | Sjogren syndrome nuclear autoantigen 1 |
| PREB | 5.642 | 7.418 | 6.509 | 4.264 | 3.914 | 4.050 | −5.497 | 0.0048473 | prolactin regulatory element binding |
| SLC35A4 | 5.746 | 8.437 | 7.267 | 5.304 | 4.812 | 4.640 | −5.484 | 0.0221711 | solute carrier family 35, member A4 |
| MPST | 7.471 | 7.732 | 9.114 | 5.915 | 5.992 | 5.017 | −5.478 | 0.0071381 | mercaptopyruvate sulfurtransferase |
| ARAF | 4.892 | 7.380 | 6.366 | 3.913 | 4.786 | 3.296 | −5.477 | 0.0257690 | v-raf murine sarcoma 3611 viral oncogene homolog |
| RAB40B | 5.954 | 5.102 | 5.625 | 2.933 | 3.746 | 2.650 | −5.471 | 0.0025587 | RAB40B, member RAS oncogene family |
| TSPAN13 | 5.861 | 5.984 | 3.978 | 2.296 | 3.041 | 3.532 | −5.470 | 0.0157053 | tetraspanin 13 |
| C2orf81 | 4.662 | 3.482 | 3.426 | 0.974 | 0.974 | 2.348 | −5.469 | 0.0081873 | chromosome 2 open reading frame 81 |
| ZNF771 | 4.851 | 4.144 | 5.145 | 2.404 | 3.187 | 1.559 | −5.452 | 0.0073346 | zinc finger protein 771 |
| CXCL5 | 4.717 | 6.147 | 4.851 | 2.404 | 4.144 | 1.559 | −5.452 | 0.0184121 | chemokine (C-X-C motif) ligand 5 |
| GSTZ1 | 4.421 | 4.890 | 5.621 | 2.825 | 3.090 | 1.974 | −5.451 | 0.0047091 | glutathione transferase zeta 1 |
| CYP2D7P1 | 2.671 | 3.288 | 3.288 | 0.845 | −0.026 | 1.348 | −5.436 | 0.0038051 | cytochrome P450, family 2, subfamily D, polypeptide 7 pseudogene 1 |
| CD9 | 8.176 | 7.852 | 6.430 | 5.734 | 4.276 | 5.369 | −5.433 | 0.0125357 | CD9 molecule |
| PLEC1 | 9.927 | 11.395 | 10.461 | 7.493 | 8.697 | 8.957 | −5.404 | 0.0119279 | No description |
| PVRL4 | 9.260 | 9.804 | 8.735 | 6.762 | 6.923 | 6.830 | −5.389 | 0.0012740 | poliovirus receptor-related 4 |
| EEF1A1 | 8.856 | 9.090 | 8.279 | 5.806 | 6.434 | 7.394 | −5.362 | 0.0080315 | eukaryotic translation elongation factor 1 alpha 1 |
| PTHLH | 7.873 | 10.074 | 9.819 | 7.397 | 8.084 | 4.778 | −5.359 | 0.0460008 | parathyroid hormone-like hormone |
| CHRNE | 5.072 | 5.116 | 4.065 | 2.518 | 2.627 | 2.695 | −5.356 | 0.0030207 | cholinergic receptor, nicotinic, epsilon |
| PLA2G15 | 4.793 | 6.211 | 7.042 | 4.212 | 3.809 | 3.484 | −5.286 | 0.0161765 | phospholipase A2, group XV |
| MAD1L1 | 5.035 | 6.723 | 6.967 | 4.331 | 4.548 | 4.031 | −5.251 | 0.0194037 | MAD1 mitotic arrest deficient-like 1 (yeast) |
| DCTN3 | 6.544 | 7.483 | 7.496 | 4.154 | 5.034 | 5.306 | −5.244 | 0.0043546 | dynactin 3 (p22) |
| ZNF385B | 4.512 | 2.627 | 3.950 | 1.559 | 1.559 | 1.559 | −5.243 | 0.0103622 | zinc finger protein 385B |
| RPL13AP5 | 8.522 | 7.449 | 8.041 | 5.043 | 5.651 | 6.655 | −5.241 | 0.0091566 | ribosomal protein L13a pseudogene 5 |
| NUP188 | 6.263 | 8.311 | 7.613 | 5.236 | 5.035 | 5.365 | −5.194 | 0.0117790 | nucleoporin 188 kDa |
| PHC2 | 7.388 | 10.092 | 8.561 | 5.653 | 6.188 | 6.303 | −5.182 | 0.0126462 | polyhomeotic homolog 2 (Drosophila) |
| IL13RA1 | 6.340 | 8.884 | 8.245 | 5.871 | 5.915 | 5.339 | −5.182 | 0.0253070 | interleukin 13 receptor, alpha 1 |
| PRR23A | 10.022 | 8.374 | 7.524 | 4.906 | 6.001 | 7.729 | −5.182 | 0.0384405 | proline rich 23A |
| PCBP4 | 6.469 | 5.643 | 7.309 | 4.666 | 3.772 | 4.099 | −5.169 | 0.0075956 | poly(rC) binding protein 4 |
| CDK9 | 7.849 | 9.353 | 9.182 | 6.425 | 6.846 | 6.816 | −5.154 | 0.0083791 | cyclin-dependent kinase 9 |
| HINT2 | 6.023 | 6.288 | 6.613 | 4.801 | 3.922 | 3.304 | −5.154 | 0.0046316 | histidine triad nucleotide binding protein 2 |
| MGAT3 | 3.336 | 3.607 | 2.531 | 0.974 | 0.974 | 0.974 | −5.140 | 0.0022755 | mannosyl (beta-1,4-)-glycoprotein beta-1,4-N-acetylglucosaminyltransferase |
| SLC22A18 | 7.694 | 6.794 | 7.665 | 4.687 | 5.334 | 4.608 | −5.133 | 0.0017053 | solute carrier family 22, member 18 |
| SH3D20 | 4.605 | 4.592 | 5.191 | 2.836 | −0.026 | 2.671 | −5.116 | 0.0127245 | SH3 domain containing 20 |
| HOMER2 | 6.553 | 8.698 | 8.042 | 4.580 | 5.688 | 5.858 | −5.112 | 0.0145710 | homer homolog 2 (Drosophila) |
| KATNB1 | 6.516 | 7.186 | 7.722 | 5.362 | 5.113 | 4.166 | −5.100 | 0.0062740 | katanin p80 (WD repeat containing) subunit B 1 |
| CCNG1 | 6.194 | 5.874 | 4.134 | 3.469 | 3.343 | 3.846 | −5.090 | 0.0258826 | cyclin G1 |
| EEF1G | 13.037 | 12.050 | 11.621 | 9.275 | 10.042 | 10.562 | −5.085 | 0.0084375 | eukaryotic translation elongation factor 1 gamma |
| RPLP2 | 14.300 | 14.300 | 13.621 | 11.012 | 11.959 | 11.999 | −5.067 | 0.0024098 | ribosomal protein, large, P2 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| LRRC48 | 4.353 | 3.032 | 4.512 | 1.559 | 1.559 | 2.173 | −5.058 | 0.0074574 | leucine rich repeat containing 48 |
| SLC35B2 | 6.034 | 7.189 | 6.280 | 3.697 | 4.667 | 4.178 | −5.056 | 0.0041182 | solute carrier family 35, member B2 |
| TOP1MT | 4.028 | 3.854 | 1.692 | 1.474 | 1.692 | 0.974 | −5.049 | 0.0421915 | topoisomerase (DNA) I, mitochondrial |
| EIF3K | 9.513 | 8.330 | 8.745 | 5.626 | 6.491 | 7.183 | −5.031 | 0.0064229 | eukaryotic translation initiation factor 3, subunit K |
| LOC728640 | 5.043 | 5.095 | 3.176 | 0.845 | 2.636 | 3.335 | −5.030 | 0.0405940 | No description |
| FAM195B | 8.791 | 9.696 | 10.644 | 6.768 | 7.366 | 7.714 | −5.027 | 0.0079048 | family with sequence similarity 195, member B |
| RPL11 | 13.351 | 12.404 | 13.081 | 10.071 | 10.756 | 11.317 | −5.011 | 0.0049724 | ribosomal protein L11 |
| EIF3G | 8.241 | 9.149 | 8.893 | 5.918 | 6.620 | 6.756 | −5.006 | 0.0025073 | eukaryotic translation initiation factor 3, subunit G |
| DYNLRB1 | 5.410 | 8.161 | 6.980 | 4.527 | 4.661 | 4.973 | −4.989 | 0.0263070 | dynein, light chain, roadblock-type 1 |
| CNTROB | 5.684 | 5.982 | 7.015 | 3.649 | 4.266 | 3.672 | −4.956 | 0.0037490 | centrobin, centrosomal BRCA2 interacting protein |
| RPL37 | 12.750 | 10.540 | 10.627 | 8.232 | 9.584 | 9.813 | −4.952 | 0.0346639 | ribosomal protein L37 |
| GADD45B | 12.254 | 11.029 | 11.602 | 8.580 | 9.298 | 10.528 | −4.941 | 0.0155971 | growth arrest and DNA-damage-inducible, beta |
| DPM2 | 7.159 | 8.235 | 7.804 | 5.927 | 5.518 | 4.856 | −4.935 | 0.0040537 | dolichyl-phosphate mannosyltransferase polypeptide 2, regulatory subunit |
| EFCAB4A | 8.593 | 6.481 | 7.549 | 4.178 | 5.083 | 6.755 | −4.935 | 0.0381489 | EF-hand calcium binding domain 4A |
| HOXB2 | 4.605 | 3.649 | 2.108 | 1.734 | −0.026 | 1.348 | −4.930 | 0.0221604 | homeobox B2 |
| NCRNA00173 | 3.953 | 3.251 | 4.120 | 0.974 | 0.974 | 1.819 | −4.930 | 0.0018557 | non-protein coding RNA 173 |
| SEP4 | 5.410 | 3.583 | 6.255 | 1.974 | 2.858 | 3.954 | −4.928 | 0.0414444 | septin 4 |
| PLSCR3 | 6.485 | 8.356 | 7.465 | 5.164 | 4.885 | 5.325 | −4.927 | 0.0076754 | phospholipid scramblase 3 |
| KIAA1324 | 10.341 | 10.418 | 9.581 | 7.903 | 8.119 | 8.041 | −4.922 | 0.0018388 | KIAA1324 |
| ANXA3 | 6.734 | 7.606 | 7.271 | 5.873 | 4.977 | 4.092 | −4.905 | 0.0095088 | annexin A3 |
| CAPNS1 | 10.575 | 10.688 | 10.429 | 8.082 | 9.215 | 8.287 | −4.886 | 0.0039125 | calpain, small subunit 1 |
| KIF7 | 3.188 | 2.525 | 2.263 | −0.026 | −0.026 | 1.348 | −4.884 | 0.0081021 | kinesin family member 7 |
| RPS9 | 12.364 | 13.216 | 13.781 | 10.635 | 10.908 | 11.494 | −4.879 | 0.0077590 | ribosomal protein S9 |
| ARRDC1 | 7.744 | 9.437 | 9.128 | 6.841 | 7.156 | 6.618 | −4.860 | 0.0148350 | arrestin domain containing 1 |
| C1orf159 | 6.887 | 7.706 | 7.760 | 5.212 | 5.544 | 4.608 | −4.856 | 0.0028834 | chromosome 1 open reading frame 159 |
| RAB32 | 6.404 | 6.424 | 6.587 | 3.922 | 4.312 | 4.235 | −4.842 | 0.0002870 | RAB32, member RAS oncogene family |
| UROD | 5.475 | 5.993 | 6.206 | 3.205 | 4.201 | 3.496 | −4.823 | 0.0027575 | uroporphyrinogen decarboxylase |
| CTDSP1 | 6.973 | 9.606 | 8.201 | 6.553 | 5.933 | 5.796 | −4.814 | 0.0238350 | CTD (carboxy-terminal domain, RNA polymerase II, polypeptide A) small phosphatase 1 |
| SDHAF2 | 6.168 | 8.056 | 7.920 | 5.145 | 5.793 | 4.946 | −4.799 | 0.0169194 | succinate dehydrogenase complex assembly factor 2 |
| CENPH | 6.023 | 6.034 | 4.391 | 3.772 | 2.402 | 2.878 | −4.796 | 0.0099701 | centromere protein H |
| FAM82A2 | 5.045 | 6.853 | 6.222 | 3.854 | 4.327 | 3.963 | −4.789 | 0.0128941 | family with sequence similarity 82, member A2 |
| NAT14 | 4.715 | 5.383 | 6.299 | 3.746 | 3.781 | 2.457 | −4.783 | 0.0141312 | N-acetyltransferase 14 (GCN5-related, putative) |
| NPHP4 | 5.664 | 5.510 | 5.954 | 2.246 | 3.712 | 3.704 | −4.731 | 0.0042041 | nephronophthisis 4 |
| YBX1 | 6.059 | 7.708 | 6.264 | 2.194 | 5.466 | 4.679 | −4.728 | 0.0331788 | Y box binding protein 1 |
| EXOSC5 | 5.086 | 5.607 | 5.874 | 3.324 | 2.848 | 3.758 | −4.717 | 0.0026792 | exosome component 5 |
| H1FX | 10.383 | 8.882 | 8.843 | 7.653 | 7.048 | 6.608 | −4.711 | 0.0095403 | H1 histone family, member X |
| MTX1 | 7.647 | 8.717 | 7.995 | 5.977 | 6.286 | 5.412 | −4.707 | 0.0036309 | metaxin 1 |
| LMF2 | 7.028 | 8.812 | 8.731 | 6.202 | 6.263 | 6.578 | −4.705 | 0.0203124 | lipase maturation factor 2 |
| SYCE1 | 5.273 | 4.309 | 3.831 | 1.559 | 2.075 | 3.440 | −4.703 | 0.0191949 | synaptonemal complex central element protein 1 |
| KCNH6 | 6.677 | 7.036 | 5.536 | 4.448 | 2.169 | 5.482 | −4.689 | 0.0386416 | potassium voltage-gated channel, subfamily H (eag-related), member 6 |
| NDUFAB1 | 3.059 | 5.945 | 4.875 | 2.610 | 3.032 | 2.650 | −4.676 | 0.0477782 | NADH dehydrogenase (ubiquinone) 1, alpha/beta subcomplex, 1, 8 kDa |
| TSPAN1 | 5.440 | 6.253 | 5.455 | 4.032 | 3.343 | 2.296 | −4.662 | 0.0057943 | tetraspanin 1 |
| TSSC4 | 6.469 | 6.850 | 7.216 | 4.255 | 4.367 | 5.083 | −4.641 | 0.0021028 | tumor suppressing subtransferable candidate 4 |

TABLE 5-continued

Differentially Expressed Genes in CD24+ Breast Epithelial Cells

| | Nulliparous (NP) Samples | | | Parous (P) Samples | | | | | |
| --- | --- | --- | --- | --- | --- | --- | --- | --- | --- |
| | CD24+ N48 | CD24+ N58 | CD24+ N43 | CD24+ N37 | CD24+ N39 | CD24+ N40 | Pseudo fold change | P value | Gene description |
| KRT86 | 3.687 | 3.525 | 3.727 | 1.474 | 0.974 | 1.819 | −4.636 | 0.0011827 | keratin 86 |
| SPTBN1 | 8.181 | 9.945 | 8.352 | 6.143 | 6.083 | 6.726 | −4.622 | 0.0065380 | spectrin, beta, non-erythrocytic 1 |
| LOC728448 | 3.059 | 3.767 | 3.897 | 1.559 | 1.559 | 1.559 | −4.620 | 0.0019762 | No description |
| DEGS2 | 5.483 | 4.856 | 5.012 | 3.187 | 3.187 | 2.650 | −4.615 | 0.0015956 | degenerative spermatocyte homolog 2, lipid desaturase (Drosophila) |
| UGDH | 7.908 | 7.440 | 6.434 | 5.236 | 5.682 | 4.996 | −4.608 | 0.0098734 | UDP-glucose 6-dehydrogenase |
| FBXO21 | 5.801 | 8.108 | 6.644 | 4.441 | 4.673 | 4.213 | −4.607 | 0.0112256 | F-box protein 21 |
| LPCAT3 | 6.400 | 8.354 | 8.441 | 6.239 | 5.934 | 5.747 | −4.603 | 0.0336662 | lysophosphatidylcholine acyltransferase 3 |
| TCTN2 | 5.789 | 5.037 | 6.249 | 3.205 | 2.840 | 4.255 | −4.584 | 0.0083262 | tectonic family member 2 |
| POMP | 10.079 | 10.860 | 10.091 | 7.959 | 8.396 | 7.886 | −4.574 | 0.0016278 | proteasome maturation protein |
| PLXND1 | 5.678 | 7.229 | 7.184 | 5.038 | 4.719 | 4.148 | −4.568 | 0.0126355 | plexin D1 |
| PKIG | 6.658 | 7.293 | 6.205 | 5.076 | 5.102 | 3.565 | −4.567 | 0.0123377 | protein kinase (cAMP-dependent, catalytic) inhibitor gamma |
| CFDP1 | 5.103 | 4.883 | 5.195 | 2.610 | 2.913 | 4.315 | −4.563 | 0.0177866 | craniofacial development protein 1 |
| NDUFS3 | 7.350 | 7.514 | 6.842 | 4.693 | 4.989 | 5.325 | −4.559 | 0.0013645 | NADH dehydrogenase (ubiquinone) Fe-S protein 3, 30 kDa (NADH-coenzyme Q reductase) |
| TRIM52 | 8.375 | 9.719 | 8.362 | 6.175 | 6.342 | 6.642 | −4.553 | 0.0036930 | tripartite motif-containing 52 |
| VKORC1 | 4.952 | 4.574 | 3.743 | 1.559 | 3.032 | 1.559 | −4.542 | 0.0087130 | vitamin K epoxide reductase complex, subunit 1 |
| ZFP57 | 4.353 | 5.233 | 6.485 | 4.013 | 3.600 | 2.173 | −4.533 | 0.0019782 | zinc finger protein 57 homolog (mouse) |
| KRT18 | 5.369 | 5.253 | 5.783 | 3.088 | 4.301 | 3.077 | −4.518 | 0.0077237 | keratin 18 |
| EMID1 | 6.066 | 5.064 | 5.510 | 3.334 | 3.954 | 2.860 | −4.516 | 0.0047989 | EMI domain containing 1 |
| ASH2L | 4.290 | 6.379 | 5.209 | 3.343 | 3.041 | 2.296 | −4.491 | 0.0111481 | ash2 (absent, small, or homeotic)-like (Drosophila) |
| CDK10 | 3.364 | 5.410 | 6.100 | 2.859 | 3.248 | 3.293 | −4.476 | 0.0481389 | cyclin-dependent kinase 10 |
| SNRNP70 | 8.893 | 10.882 | 10.733 | 7.587 | 7.761 | 8.721 | −4.470 | 0.0199655 | small nuclear ribonucleoprotein 70 kDa (U1) |
| B4GALNT4 | 9.035 | 9.248 | 10.024 | 6.964 | 7.088 | 7.357 | −4.469 | 0.0017552 | beta-1,4-N-acetyl-galactosaminyl transferase 4 |
| C1orf77 | 6.066 | 6.066 | 4.134 | 2.860 | 1.974 | 4.098 | −4.467 | 0.0211335 | chromosome 1 open reading frame 77 |
| C17orf101 | 3.593 | 5.376 | 5.201 | 2.246 | 2.377 | 3.220 | −4.457 | 0.0153876 | chromosome 17 open reading frame 101 |
| AKIRIN1 | 8.664 | 8.221 | 7.784 | 5.632 | 5.632 | 6.996 | −4.444 | 0.0087843 | akirin 1 |
| PPP1CA | 5.799 | 6.549 | 6.074 | 4.422 | 3.648 | 3.907 | −4.440 | 0.0023292 | protein phosphatase 1, catalytic subunit, alpha isozyme |
| NDUFA11 | 8.300 | 9.744 | 8.755 | 6.986 | 7.194 | 6.154 | −4.426 | 0.0089355 | NADH dehydrogenase (ubiquinone) 1 alpha subcomplex, 11, 14.7 kDa |
| STARD10 | 4.851 | 4.316 | 4.976 | 2.610 | 3.032 | 2.173 | −4.417 | 0.0026370 | StAR-related lipid transfer (START) domain containing 10 |
| SPAG7 | 7.455 | 6.990 | 8.184 | 5.277 | 6.342 | 4.851 | −4.407 | 0.0122970 | sperm associated antigen 7 |
| ZAP70 | 1.913 | 2.108 | 2.108 | −0.026 | −0.026 | −0.026 | −4.387 | 0.0002272 | zeta-chain (TCR) associated protein kinase 70 kDa |
| GLTPD2 | 1.913 | 2.108 | 3.335 | −0.026 | −0.026 | −0.026 | −4.387 | 0.0030100 | glycolipid transfer protein domain containing 2 |
| GOLGA6L1 | 2.671 | 1.098 | 2.108 | −0.026 | −0.026 | −0.026 | −4.387 | 0.0086539 | golgin A6 family-like 1 |
| CPLX1 | 7.311 | 6.162 | 7.548 | 5.178 | 5.590 | 3.704 | −4.385 | 0.0177199 | complexin 1 |
| CES8 | 5.248 | 4.107 | 4.761 | 1.974 | 1.974 | 3.660 | −4.384 | 0.0144060 | No description |
| MAFK | 11.235 | 10.641 | 12.120 | 8.514 | 9.271 | 9.728 | −4.368 | 0.0097467 | v-maf musculoaponeurotic fibrosarcoma oncogene homolog K (avian) |
| STAP2 | 6.168 | 5.450 | 6.624 | 2.518 | 4.504 | 4.042 | −4.364 | 0.0117022 | signal transducing adaptor family member 2 |
| INPP5J | 4.153 | 5.199 | 5.806 | 3.205 | 2.782 | 3.077 | −4.354 | 0.0094152 | inositol polyphosphate-5-phosphatase J |
| CBLC | 6.082 | 6.120 | 5.634 | 3.351 | 3.960 | 4.327 | −4.352 | 0.0029992 | Cas-Br-M (murine) ecotropic retroviral transforming sequence c |
| COL9A2 | 5.352 | 6.025 | 6.615 | 3.907 | 3.604 | 4.286 | −4.341 | 0.0053592 | collagen, type IX, alpha 2 |
| PLCB4 | 5.642 | 4.674 | 4.255 | 3.043 | 2.559 | 2.559 | −4.332 | 0.0054413 | phospholipase C, beta 4 |
| WBSCR26 | 4.054 | 3.469 | 5.135 | 3.022 | 2.848 | 0.974 | −4.328 | 0.0377759 | Williams Beuren syndrome chromosome region 26 (non-protein coding) |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| SRP14 | 6.588 | 6.206 | 5.980 | 4.098 | 4.521 | 3.565 | −4.311 | 0.0022970 | signal recognition particle 14 kDa (homologous Alu RNA binding protein) |
| CUTA | 9.657 | 8.275 | 8.536 | 6.167 | 6.843 | 7.231 | −4.311 | 0.0099233 | cutA divalent cation tolerance homolog (*E. coli*) |
| R3HCC1 | 6.722 | 7.651 | 8.414 | 5.324 | 6.308 | 5.302 | −4.307 | 0.0163791 | R3H domain and coiled-coil containing 1 |
| GTPBP2 | 8.282 | 8.576 | 7.382 | 6.049 | 5.909 | 6.473 | −4.295 | 0.0064589 | GTP binding protein 2 |
| TNFRSF14 | 7.079 | 7.031 | 7.427 | 4.752 | 4.977 | 5.428 | −4.291 | 0.0012318 | tumor necrosis factor receptor superfamily, member 14 (herpesvirus entry mediator) |
| GSTA1 | 3.188 | 5.023 | 4.208 | −0.026 | 3.345 | 2.108 | −4.286 | 0.0457790 | glutathione S-transferase alpha 1 |
| RALGDS | 11.057 | 11.076 | 10.669 | 8.575 | 8.950 | 9.573 | −4.272 | 0.0041934 | ral guanine nucleotide dissociation stimulator |
| ZNF44 | 5.273 | 5.554 | 4.705 | 2.610 | 4.144 | 3.059 | −4.271 | 0.0131896 | zinc finger protein 44 |
| RPL27A | 10.238 | 7.636 | 8.238 | 6.012 | 6.151 | 7.550 | −4.247 | 0.0377652 | ribosomal protein L27a |
| BAI2 | 5.344 | 5.125 | 4.296 | 2.859 | 3.041 | 3.043 | −4.239 | 0.0038642 | brain-specific angiogenesis inhibitor 2 |
| TRAP1 | 8.713 | 8.729 | 8.617 | 6.052 | 6.915 | 6.631 | −4.236 | 0.0014137 | TNF receptor-associated protein 1 |
| RAE1 | 4.899 | 4.526 | 3.838 | 1.974 | 2.377 | 2.819 | −4.229 | 0.0050791 | RAE1 RNA export 1 homolog (*S. pombe*) |
| HES4 | 10.391 | 10.675 | 11.686 | 8.322 | 8.600 | 8.601 | −4.215 | 0.0026017 | hairy and enhancer of split 4 (*Drosophila*) |
| SDHAF1 | 3.954 | 5.325 | 5.270 | 2.860 | 3.196 | 3.220 | −4.210 | 0.0136209 | succinate dehydrogenase complex assembly factor 1 |
| PPME1 | 6.106 | 7.180 | 6.612 | 4.283 | 4.543 | 5.098 | −4.196 | 0.0054712 | protein phosphatase methylesterase 1 |
| CSRP1 | 13.321 | 12.373 | 13.440 | 10.100 | 11.253 | 11.548 | −4.193 | 0.0112794 | cysteine and glycine-rich protein 1 |
| XRN2 | 7.448 | 7.883 | 6.166 | 5.381 | 5.794 | 5.349 | −4.191 | 0.0230084 | 5′-3′ exoribonuclease 2 |
| ABHD14B | 7.805 | 7.225 | 8.018 | 4.670 | 5.740 | 6.005 | −4.183 | 0.0056631 | abhydrolase domain containing 14B |
| PXMP2 | 1.913 | 2.671 | 2.038 | −0.026 | −0.026 | −0.026 | −4.181 | 0.0009777 | peroxisomal membrane protein 2, 22 kDa |
| EGR4 | 2.671 | 1.169 | 2.038 | −0.026 | −0.026 | −0.026 | −4.181 | 0.0075472 | early growth response 4 |
| TMSB15A | 3.966 | 2.038 | 1.734 | −0.026 | −0.026 | −0.026 | −4.181 | 0.0088649 | thymosin beta 15a |
| MUSTN1 | 2.671 | 2.525 | 2.038 | −0.026 | −0.026 | 1.348 | −4.181 | 0.0103116 | musculoskeletal, embryonic nuclear protein 1 |
| POM121L1P | 4.749 | 1.098 | 2.038 | −0.026 | −0.026 | −0.026 | −4.181 | 0.0278657 | POM121 membrane glycoprotein-like 1, pseudogene |
| BTBD19 | 2.671 | 2.836 | 2.038 | −0.026 | −0.026 | 2.108 | −4.181 | 0.0373246 | BTB (POZ) domain containing 19 |
| ZDHHC4 | 7.345 | 6.359 | 6.090 | 4.296 | 5.545 | 3.809 | −4.177 | 0.0169409 | zinc finger, DHHC-type containing 4 |
| RANGRF | 4.137 | 3.885 | 3.032 | 1.559 | 2.075 | 1.559 | −4.175 | 0.0052909 | RAN guanine nucleotide release factor |
| DDX41 | 7.504 | 8.158 | 7.446 | 5.385 | 5.591 | 5.494 | −4.174 | 0.0010154 | DEAD (Asp-Glu-Ala-Asp) box polypeptide 41 |
| ARMC6 | 5.537 | 7.120 | 7.690 | 4.840 | 5.061 | 5.576 | −4.169 | 0.0435180 | armadillo repeat containing 6 |
| CHI3L2 | 9.895 | 11.472 | 10.081 | 8.785 | 8.393 | 7.843 | −4.146 | 0.0106815 | chitinase 3-like 2 |
| RPL10 | 15.252 | 14.909 | 14.712 | 12.304 | 13.087 | 13.201 | −4.145 | 0.0028197 | ribosomal protein L10 |
| COQ10A | 4.137 | 3.663 | 3.604 | 1.559 | 2.454 | 1.559 | −4.125 | 0.0043761 | coenzyme Q10 homolog A (*S. cerevisiae*) |
| SYNGR2 | 9.935 | 11.373 | 9.596 | 7.891 | 8.064 | 7.655 | −4.125 | 0.0060038 | synaptogyrin 2 |
| LRRC16B | 2.519 | 4.997 | 3.600 | 2.650 | 1.559 | 1.559 | −4.114 | 0.0477276 | leucine rich repeat containing 16B |
| HSD17B8 | 4.572 | 4.413 | 4.170 | 1.974 | 2.377 | 3.220 | −4.100 | 0.0071773 | hydroxysteroid (17-beta) dehydrogenases |
| GHDC | 3.810 | 5.509 | 5.106 | 2.559 | 3.476 | 2.899 | −4.091 | 0.0195848 | GH3 domain containing |
| CD2AP | 6.208 | 5.839 | 4.808 | 4.177 | 3.742 | 3.789 | −4.087 | 0.0132863 | CD2-associated protein |
| RPL13 | 14.215 | 13.942 | 14.098 | 11.644 | 12.067 | 12.646 | −4.086 | 0.0031220 | ribosomal protein L13 |
| ATP5F1 | 7.677 | 7.613 | 5.718 | 5.583 | 4.732 | 5.643 | −4.084 | 0.0422878 | ATP synthase, H+ transporting, mitochondrial Fo complex, subunit B1 |
| ZC3H11A | 5.954 | 7.876 | 6.820 | 5.036 | 4.459 | 4.792 | −4.078 | 0.0116807 | zinc finger CCCH-type containing 11A |
| MLPH | 6.304 | 5.748 | 4.930 | 4.277 | 3.519 | 3.557 | −4.075 | 0.0110046 | melanophilin |
| BRD9 | 6.599 | 7.619 | 7.882 | 4.608 | 5.768 | 5.593 | −4.073 | 0.0107943 | bromodomain containing 9 |
| COPB2 | 6.509 | 6.722 | 5.308 | 4.703 | 4.116 | 3.557 | −4.054 | 0.0115318 | coatomer protein complex, subunit beta 2 (beta prime) |
| RPN1 | 8.646 | 8.874 | 7.909 | 6.289 | 6.627 | 6.820 | −4.053 | 0.0044267 | ribophorin I |
| ZNF512B | 6.617 | 7.937 | 8.263 | 5.785 | 6.248 | 5.657 | −4.040 | 0.0207038 | zinc finger protein 512B |

TABLE 5-continued

Differentially Expressed Genes in CD24+ Breast Epithelial Cells

| | Nulliparous (NP) Samples | | Parous (P) Samples | | | | | |
|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| IMPDH2 | 8.405 | 8.352 | 7.345 | 5.350 | 6.317 | 6.392 | −4.038 | 0.0090115 | IMP (inosine 5′-monophosphate) dehydrogenase 2 |
| MRPS12 | 4.946 | 7.849 | 6.366 | 4.355 | 4.866 | 4.042 | −4.032 | 0.0423469 | mitochondrial ribosomal protein S12 |
| TACSTD2 | 12.015 | 11.922 | 11.277 | 9.911 | 9.917 | 9.897 | −4.030 | 0.0024589 | tumor-associated calcium signal transducer 2 |
| ARFRP1 | 4.554 | 7.410 | 5.977 | 3.973 | 3.747 | 4.561 | −4.012 | 0.0466815 | ADP-ribosylation factor related protein 1 |
| KRT10 | 3.966 | 6.003 | 4.675 | 2.108 | 2.836 | 2.671 | −4.011 | 0.0102302 | keratin 10 |
| TARSL2 | 2.747 | 4.514 | 3.976 | 1.974 | 1.974 | 1.974 | −4.003 | 0.0173868 | threonyl-tRNA synthetase-like 2 |
| ESRRA | 7.538 | 9.461 | 9.511 | 7.336 | 7.510 | 7.081 | −4.002 | 0.0497314 | estrogen-related receptor alpha |
| SIN3B | 8.127 | 9.670 | 8.823 | 6.823 | 7.224 | 6.681 | −4.001 | 0.0095510 | SIN3 homolog B, transcription regulator (yeast) |
| CLPP | 5.009 | 6.510 | 7.035 | 4.514 | 4.351 | 4.684 | −3.990 | 0.0314106 | ClpP caseinolytic peptidase, ATP-dependent, proteolytic subunit homolog (*E. coli*) |
| NME7 | 6.904 | 6.587 | 5.191 | 4.118 | 4.906 | 4.592 | −3.985 | 0.0254605 | non-metastatic cells 7, protein expressed in (nucleoside-diphosphate kinase) |
| GTF2H4 | 5.584 | 6.606 | 7.802 | 4.401 | 5.410 | 4.614 | −3.980 | 0.0309248 | general transcription factor IIH, polypeptide 4, 52 kDa |
| C14orf142 | 4.137 | 3.552 | 3.059 | 1.559 | 2.075 | 1.559 | −3.980 | 0.0058864 | chromosome 14 open reading frame 142 |
| DUSP16 | 4.899 | 3.966 | 2.973 | 2.860 | 1.974 | 1.974 | −3.976 | 0.0328235 | dual specificity phosphatase 16 |
| MAP3K11 | 6.664 | 8.405 | 8.386 | 6.418 | 5.857 | 5.439 | −3.964 | 0.0215372 | mitogen-activated protein kinase kinase kinase 11 |
| SFT2D1 | 5.453 | 5.381 | 4.901 | 3.396 | 4.479 | 2.602 | −3.960 | 0.0220253 | SFT2 domain containing 1 |
| G6PC | 4.353 | 5.378 | 5.998 | 3.872 | 4.013 | 1.559 | −3.960 | 0.0401942 | glucose-6-phosphatase, catalytic subunit |
| DULLARD | 5.500 | 6.633 | 5.444 | 3.462 | 4.049 | 4.085 | −3.952 | 0.0074344 | No description |
| ACAD8 | 5.344 | 5.756 | 4.076 | 3.043 | 3.697 | 3.364 | −3.944 | 0.0219478 | acyl-CoA dehydrogenase family, member 8 |
| BATF | 9.004 | 9.251 | 9.677 | 7.020 | 7.845 | 7.272 | −3.943 | 0.0036117 | basic leucine zipper transcription factor, ATF-like |
| COX5B | 5.690 | 6.396 | 5.382 | 4.035 | 4.421 | 3.293 | −3.931 | 0.0092241 | cytochrome c oxidase subunit Vb |
| PTP4A2 | 8.227 | 9.403 | 7.125 | 6.252 | 6.100 | 6.869 | −3.929 | 0.0302172 | protein tyrosine phosphatase type IVA, member 2 |
| DUSP4 | 7.614 | 7.248 | 6.394 | 5.217 | 5.275 | 5.413 | −3.926 | 0.0076915 | dual specificity phosphatase 4 |
| ZNF777 | 4.421 | 6.068 | 6.099 | 3.196 | 4.098 | 4.098 | −3.917 | 0.0292724 | zinc finger protein 777 |
| SEMA4B | 10.093 | 10.853 | 11.090 | 8.887 | 8.914 | 8.210 | −3.907 | 0.0048204 | sema domain, immunoglobulin domain (ig), transmembrane domain (TM) and short cytoplasmic domain, (semaphorin) 4B |
| NPDC1 | 10.084 | 9.870 | 9.747 | 7.204 | 7.905 | 8.209 | −3.907 | 0.0023891 | neural proliferation, differentiation and control, 1 |
| SEP2 | 7.885 | 8.586 | 7.119 | 5.452 | 5.922 | 6.196 | −3.899 | 0.0089248 | septin 2 |
| LUC7L2 | 5.456 | 7.309 | 7.087 | 4.686 | 5.348 | 5.016 | −3.892 | 0.0363622 | LUC7-like 2 (*S. cerevisiae*) |
| AP1AR | 4.870 | 5.350 | 4.534 | 2.911 | 3.277 | 2.899 | −3.888 | 0.0028941 | adaptor-related protein complex 1 associated regulatory protein |
| METRN | 6.589 | 7.969 | 7.650 | 6.012 | 5.548 | 5.152 | −3.883 | 0.0130522 | meteorin, glial cell differentiation regulator |
| BRMS1 | 4.353 | 4.765 | 3.388 | 2.404 | 1.559 | 2.650 | −3.863 | 0.0121750 | breast cancer metastasis suppressor 1 |
| MAPT | 7.919 | 6.694 | 6.616 | 5.325 | 5.094 | 4.670 | −3.852 | 0.0078780 | microtubule-associated protein tau |
| ANO9 | 5.159 | 7.026 | 6.867 | 4.428 | 4.419 | 5.082 | −3.847 | 0.0314635 | anoctamin 9 |
| ATG16L2 | 5.127 | 5.839 | 7.070 | 4.144 | 3.187 | 4.705 | −3.838 | 0.0244513 | ATG16 autophagy related 16-like 2 (*S. cerevisiae*) |
| ZNF598 | 9.693 | 11.012 | 10.132 | 8.192 | 8.034 | 8.414 | −3.837 | 0.0049939 | zinc finger protein 598 |
| DYNC2LI1 | 3.758 | 3.772 | 3.089 | 2.848 | 0.974 | 1.819 | −3.836 | 0.0286370 | dynein, cytoplasmic 2, light intermediate chain 1 |
| C6orf59 | 1.913 | 1.913 | 1.098 | −0.026 | −0.026 | −0.026 | −3.832 | 0.0049831 | No description |
| C6orf57 | 1.913 | 1.098 | 2.038 | −0.026 | −0.026 | −0.026 | −3.832 | 0.0053377 | chromosome 6 open reading frame 57 |
| SALL2 | 1.913 | 2.835 | 2.835 | 0.845 | 1.169 | −0.026 | −3.832 | 0.0113116 | sal-like 2 (*Drosophila*) |
| MCM9 | 1.913 | 2.108 | 2.038 | −0.026 | −0.026 | 1.348 | −3.832 | 0.0193292 | minichromosome maintenance complex component 9 |
| POP5 | 4.282 | 3.412 | 2.734 | 1.474 | 1.692 | 0.974 | −3.830 | 0.0084766 | processing of precursor 5, ribonuclease P/MRP subunit (*S. cerevisiae*) |

TABLE 5-continued

Differentially Expressed Genes in CD24+ Breast Epithelial Cells

| | Nulliparous (NP) Samples | | | Parous (P) Samples | | | | | |
| --- | --- | --- | --- | --- | --- | --- | --- | --- | --- |
| | CD24+ N48 | CD24+ N58 | CD24+ N43 | CD24+ N37 | CD24+ N39 | CD24+ N40 | Pseudo fold change | P value | Gene description |
| TRPC4AP | 9.521 | 10.055 | 10.220 | 7.656 | 8.284 | 8.026 | −3.828 | 0.0027682 | transient receptor potential cation channel, subfamily C, member 4 associated protein |
| SH3GL1 | 9.092 | 9.023 | 9.004 | 6.681 | 7.377 | 7.087 | −3.825 | 0.0012425 | SH3-domain GRB2-like 1 |
| SERPINA3 | 11.483 | 12.786 | 10.557 | 8.724 | 9.551 | 9.700 | −3.817 | 0.0150507 | serpin peptidase inhibitor, clade A (alpha-1 antiproteinase, antitrypsin), members |
| EIF3D | 9.096 | 10.765 | 9.920 | 7.966 | 7.989 | 8.621 | −3.811 | 0.0191374 | eukaryotic translation initiation factor 3, subunit D |
| ADRM1 | 8.325 | 9.953 | 9.590 | 7.661 | 7.950 | 7.525 | −3.807 | 0.0244728 | adhesion regulating molecule 1 |
| DAP | 6.441 | 5.916 | 5.219 | 3.988 | 4.296 | 3.717 | −3.804 | 0.0076362 | death-associated protein |
| ACAD11 | 7.275 | 6.185 | 7.174 | 5.348 | 5.076 | 4.899 | −3.802 | 0.0082671 | acyl-CoA dehydrogenase family, member 11 |
| ZFYVE28 | 3.810 | 4.484 | 4.750 | 2.559 | 2.559 | 2.559 | −3.797 | 0.0039286 | zinc finger, FYVE domain containing 28 |
| C17orf70 | 6.245 | 6.878 | 7.380 | 4.741 | 4.337 | 5.456 | −3.796 | 0.0086869 | chromosome 17 open reading frame 70 |
| TMEM199 | 3.475 | 4.187 | 3.447 | 1.559 | 1.559 | 1.559 | −3.772 | 0.0012533 | transmembrane protein 199 |
| SETD3 | 4.961 | 5.815 | 4.469 | 2.559 | 2.840 | 4.081 | −3.757 | 0.0188726 | SET domain containing 3 |
| PPP1R1B | 7.074 | 5.710 | 6.626 | 3.802 | 4.367 | 5.645 | −3.753 | 0.0267260 | protein phosphatase 1, regulatory (inhibitor) subunit 1B |
| RPS15A | 11.974 | 10.121 | 10.779 | 8.214 | 9.518 | 9.513 | −3.752 | 0.0280599 | ribosomal protein S15a |
| C19orf40 | 7.597 | 7.896 | 6.319 | 4.856 | 4.997 | 5.990 | −3.748 | 0.0158580 | chromosome 19 open reading frame 40 |
| NUDT16L1 | 2.878 | 2.878 | 3.063 | 0.974 | 0.974 | 0.974 | −3.741 | 0.0002594 | nudix (nucleoside diphosphate linked moiety X)-type motif 16-like 1 |
| NR2E3 | 2.878 | 3.469 | 3.246 | 0.974 | 0.974 | 1.819 | −3.741 | 0.0040645 | nuclear receptor subfamily 2, group E, member 3 |
| NTAN1 | 2.878 | 4.282 | 2.531 | 0.974 | 0.974 | 1.819 | −3.741 | 0.0165886 | N-terminal asparagine amidase |
| SMTN | 10.362 | 9.095 | 10.915 | 7.600 | 8.179 | 9.012 | −3.740 | 0.0270744 | smoothelin |
| P2RX4 | 7.702 | 7.563 | 8.912 | 5.662 | 6.654 | 6.851 | −3.734 | 0.0255180 | purinergic receptor P2X, ligand-gated ion channel, 4 |
| U2AF1L4 | 6.044 | 5.529 | 5.589 | 3.950 | 4.144 | 3.440 | −3.733 | 0.0029156 | U2 small nuclear RNA auxiliary factor 1-like 4 |
| TMEM88 | 6.757 | 5.918 | 6.697 | 3.022 | 4.989 | 4.801 | −3.723 | 0.0156178 | transmembrane protein 88 |
| DNAJC17 | 4.968 | 6.596 | 7.659 | 3.772 | 4.794 | 4.701 | −3.719 | 0.0382279 | DnaJ (Hsp40) homolog, subfamily C, member 17 |
| PLEKHG3 | 7.752 | 7.454 | 7.556 | 5.560 | 6.159 | 5.657 | −3.716 | 0.0020599 | pleckstrin homology domain containing, family G (with RhoGef domain) member 3 |
| PPP1CC | 6.329 | 8.017 | 6.906 | 4.442 | 5.158 | 5.345 | −3.699 | 0.0113484 | protein phosphatase 1, catalytic subunit, gamma isozyme |
| NUP88 | 7.306 | 7.323 | 5.874 | 5.113 | 5.435 | 5.238 | −3.699 | 0.0226163 | nucleoporin 88 kDa |
| RPL7 | 11.516 | 10.027 | 9.517 | 7.631 | 8.552 | 8.927 | −3.697 | 0.0245625 | ribosomal protein L7 |
| C1orf35 | 7.455 | 7.020 | 7.962 | 5.689 | 5.457 | 5.571 | −3.691 | 0.0030583 | chromosome 1 open reading frame 35 |
| C19orf20 | 4.685 | 5.429 | 5.499 | 3.032 | 3.617 | 3.307 | −3.687 | 0.0039394 | chromosome 19 open reading frame 20 |
| SLC37A4 | 3.364 | 4.638 | 4.178 | 2.518 | 2.296 | 2.296 | −3.686 | 0.0101044 | solute carrier family 37 (glucose-6-phosphate transporter), member 4 |
| ZNF689 | 3.336 | 4.282 | 3.089 | 1.474 | 2.402 | 0.974 | −3.681 | 0.0141504 | zinc finger protein 689 |
| H2AFX | 6.721 | 7.237 | 6.647 | 3.872 | 5.033 | 5.360 | −3.674 | 0.0079478 | H2A histone family, member X |
| DAZAP1 | 9.008 | 10.448 | 9.977 | 8.100 | 8.426 | 8.057 | −3.673 | 0.0161942 | DAZ associated protein 1 |
| C19orf63 | 8.378 | 10.164 | 10.087 | 8.289 | 8.069 | 7.992 | −3.667 | 0.0479325 | chromosome 19 open reading frame 63 |
| TTRAP | 3.758 | 3.922 | 2.848 | 2.404 | 0.974 | 1.819 | −3.664 | 0.0178603 | No description |
| ANKRD52 | 7.123 | 8.513 | 8.154 | 6.601 | 6.183 | 6.283 | −3.659 | 0.0175449 | ankyrin repeat domain 52 |
| SEMA3B | 11.533 | 11.512 | 12.860 | 9.643 | 10.872 | 10.044 | −3.652 | 0.0210944 | sema domain, immunoglobulin domain (ig), short basic domain, secreted, (semaphorin) 3B |
| MKRN2 | 4.205 | 5.867 | 4.943 | 2.782 | 3.026 | 3.999 | −3.651 | 0.0263830 | makorin ring finger protein 2 |
| SAE1 | 7.031 | 7.920 | 7.531 | 6.053 | 5.591 | 5.325 | −3.649 | 0.0051696 | SUMO1 activating enzyme subunit 1 |
| REEP6 | 6.863 | 7.174 | 6.920 | 5.293 | 5.309 | 4.222 | −3.642 | 0.0042924 | receptor accessory protein 6 |
| LIN7B | 3.336 | 4.712 | 5.240 | 2.848 | 2.848 | 2.878 | −3.641 | 0.0321251 | lin-7 homolog B (C. elegans) |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| GGA1 | 8.146 | 8.029 | 8.898 | 7.286 | 6.165 | 6.216 | | | golgi-associated, gamma adaptin ear containing, ARF binding protein 1 |
| ARRDC2 | 5.943 | 7.028 | 5.958 | 3.992 | 4.840 | 5.164 | -3.641 | 0.0119386 | arrestin domain containing 2 |
| IGFBP2 | 5.604 | 6.477 | 5.764 | 3.900 | 3.350 | 5.191 | -3.640 | 0.0204428 | insulin-like growth factor binding protein 2, 36 kDa |
| SFRS17A | 7.600 | 5.585 | 6.703 | 4.733 | 5.736 | 4.548 | -3.639 | 0.0232540 | No description |
| C10orf116 | 8.135 | 9.034 | 8.860 | 6.998 | 6.886 | 7.060 | -3.637 | 0.0449831 | chromosome 10 open reading frame 116 |
| PABPC1L | 6.672 | 5.753 | 5.818 | 3.343 | 4.594 | 4.810 | -3.636 | 0.0049363 | poly(A) binding protein, cytoplasmic 1-like |
| FLJ45079 | 5.483 | 4.952 | 4.512 | 2.650 | 4.382 | 3.059 | -3.635 | 0.0168880 | No description |
| MMP24 | 3.336 | 3.758 | 4.313 | 1.474 | 1.692 | 3.304 | -3.634 | 0.0321520 | matrix metallopeptidase 24 (membrane-inserted) |
| TMEM93 | 3.966 | 3.966 | 3.616 | -0.026 | 2.105 | 3.152 | -3.631 | 0.0366884 | transmembrane protein 93 |
| FAM40A | 4.784 | 5.707 | 4.305 | 2.296 | 3.847 | 3.680 | -3.630 | 0.0409662 | family with sequence similarity 40, member A |
| PSMA2 | 7.376 | 6.925 | 5.726 | 4.296 | 5.518 | 4.946 | -3.626 | 0.0355940 | proteasome (prosome, macropain) subunit, alpha type, 2 |
| LOC440957 | 6.216 | 6.364 | 6.349 | 4.282 | 4.507 | 4.493 | -3.621 | 0.0252686 | No description |
| CILP2 | 3.220 | 4.098 | 4.230 | 1.974 | 2.377 | 1.974 | -3.612 | 0.0004129 | cartilage intermediate layer protein 2 |
| SHCBP1 | 8.575 | 9.402 | 7.374 | 6.511 | 6.722 | 7.335 | -3.612 | 0.0073162 | SHC SH2-domain binding protein 1 |
| TEX10 | 6.408 | 7.026 | 6.849 | 4.396 | 5.204 | 4.996 | -3.611 | 0.0398803 | testis expressed 10 |
| DEF6 | 4.801 | 4.730 | 4.321 | 2.404 | 3.758 | 2.878 | -3.609 | 0.0036416 | differentially expressed in FDCP 6 homolog (mouse) |
| HSPB8 | 5.154 | 6.888 | 6.830 | 4.384 | 4.005 | 5.038 | -3.605 | 0.0154091 | heat shock 22 kDa protein 8 |
| GUK1 | 9.605 | 9.412 | 8.436 | 7.114 | 7.562 | 7.661 | -3.605 | 0.0260698 | guanylate kinase 1 |
| ZBTB48 | 5.138 | 6.974 | 6.411 | 4.241 | 4.562 | 4.697 | -3.603 | 0.0108350 | zinc finger and BTB domain containing 48 |
| MC1R | 3.810 | 5.724 | 4.685 | 2.746 | 2.840 | 3.496 | -3.593 | 0.0247506 | melanocortin 1 receptor (alpha melanocyte stimulating hormone receptor) |
| RPS15 | 7.013 | 5.864 | 7.246 | 4.899 | 5.404 | 5.002 | -3.584 | 0.0270990 | ribosomal protein S15 |
| EFEMP2 | 6.875 | 6.832 | 7.401 | 4.998 | 5.083 | 5.484 | -3.565 | 0.0178289 | EGF-containing fibulin-like extracellular matrix protein 2 |
| NUDT18 | 2.247 | 3.304 | 4.282 | 1.474 | 2.402 | 0.974 | -3.553 | 0.0024421 | nudix (nucleoside diphosphate linked moiety X)-type motif 18 |
| C22orf13 | 7.381 | 9.435 | 8.421 | 6.794 | 6.592 | 6.214 | -3.552 | 0.0464467 | chromosome 22 open reading frame 13 |
| VEZT | 6.196 | 7.467 | 5.446 | 3.983 | 4.572 | 4.368 | -3.551 | 0.0209071 | vezatin, adherens junctions transmembrane protein |
| PRKCZ | 5.747 | 6.831 | 7.313 | 5.008 | 5.435 | 4.899 | -3.538 | 0.0148243 | protein kinase C, zeta |
| TMEM134 | 6.993 | 7.361 | 8.609 | 5.614 | 6.145 | 5.171 | -3.536 | 0.0260269 | transmembrane protein 134 |
| TRIP6 | 8.946 | 9.571 | 10.211 | 7.751 | 7.952 | 7.466 | -3.532 | 0.0132755 | thyroid hormone receptor interactor 6 |
| HLA-F | 12.395 | 13.578 | 13.929 | 12.360 | 11.762 | 9.468 | -3.523 | 0.0077345 | major histocompatibility complex, class I, F |
| AGR2 | 4.126 | 7.026 | 4.375 | 2.559 | 3.204 | 2.559 | -3.520 | 0.0473147 | anterior gradient homolog 2 (Xenopus laevis) |
| PILRB | 5.908 | 7.514 | 7.077 | 4.615 | 5.264 | 5.495 | -3.515 | 0.0268619 | paired immunoglobin-like type 2 receptor beta |
| ATP1B1 | 8.445 | 8.506 | 7.054 | 6.695 | 6.405 | 6.219 | -3.510 | 0.0217498 | ATPase, Na+/K+ transporting, beta 1 polypeptide |
| ZNF580 | 6.259 | 6.256 | 5.921 | 4.900 | 4.446 | 3.922 | -3.506 | 0.0236792 | zinc finger protein 580 |
| U2AF2 | 9.118 | 9.357 | 10.284 | 7.310 | 8.130 | 7.984 | -3.503 | 0.0055503 | U2 small nuclear RNA auxiliary factor 2 |
| PROP | 3.364 | 5.185 | 4.435 | 3.343 | 2.627 | 2.296 | -3.501 | 0.0113223 | prolylcarboxypeptidase (angiotensinase C) |
| SPINT1 | 9.945 | 10.590 | 10.284 | 8.541 | 8.025 | 8.139 | -3.496 | 0.0379463 | serine peptidase inhibitor, Kunitz type 1 |
| POLR1E | 7.318 | 6.850 | 9.734 | 4.628 | 5.158 | 5.412 | -3.494 | 0.0039916 | polymerase (RNA) I polypeptide E, 53 kDa |
| RBM3 | 8.407 | 8.626 | 6.433 | 5.251 | 6.145 | 6.914 | -3.491 | 0.0062632 | RNA binding motif (RNP1, RRM) protein 3 |
| PKN3 | 5.642 | 6.088 | 7.582 | 4.997 | 6.603 | 7.466 | -3.490 | 0.0172379 | protein kinase N3 |
| NARFL | 3.728 | 5.583 | 5.943 | 3.117 | 4.140 | 3.173 | -3.488 | 0.0183538 | nuclear prelamin A recognition factor-like |
| UBAC2 | 4.360 | 4.414 | 4.777 | 2.559 | 2.974 | 2.974 | -3.484 | 0.0226685 | UBA domain containing 2 |
| ZFPL1 | 6.120 | 6.849 | 3.591 | 3.117 | 2.559 | 2.559 | -3.476 | 0.0064014 | zinc finger protein-like 1 |
| CCDC104 | 5.237 | 5.159 | 6.345 | 2.559 | 4.811 | 4.296 | -3.475 | 0.0058542 | coiled-coil domain containing 104 |
| RHOA | 11.818 | 12.120 | 11.800 | 9.937 | 10.323 | 10.172 | -3.475 | 0.0013024 | ras homolog gene family, member A |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| GDPD3 | 5.451 | 5.475 | 6.742 | 3.659 | 3.922 | 4.062 | −3.462 | 0.0074766 | glycerophosphodiester phosphodiesterase domain containing 3 |
| GRASP | 4.486 | 5.210 | 6.343 | 3.784 | 3.697 | 2.695 | −3.461 | 0.0200913 | GRP1 (general receptor for phosphoinositides 1)-associated scaffold protein |
| BAP1 | 7.391 | 8.891 | 8.436 | 6.654 | 6.969 | 6.560 | −3.441 | 0.0227744 | BRCA1 associated protein-1 (ubiquitin carboxy-terminal hydrolase) |
| DSC2 | 9.583 | 9.334 | 7.924 | 7.190 | 7.485 | 7.803 | −3.436 | 0.0380929 | desmocollin 2 |
| ZW10 | 4.360 | 5.899 | 5.475 | 3.591 | 3.476 | 4.126 | −3.417 | 0.0272809 | ZW10, kinetochore associated, homolog (Drosophila) |
| SUSD2 | 4.631 | 5.112 | 5.872 | 3.343 | 3.469 | 3.043 | −3.408 | 0.0060760 | sushi domain containing 2 |
| MYO9B | 7.816 | 7.124 | 7.900 | 5.760 | 6.132 | 6.010 | −3.405 | 0.0051320 | myosin IXB |
| TSTD1 | 7.446 | 8.051 | 7.504 | 5.806 | 6.286 | 5.627 | −3.399 | 0.0041719 | thiosulfate sulfurtransferase (rhodanese)-like domain containing 1 |
| APH1B | 5.604 | 6.520 | 6.455 | 4.757 | 4.415 | 4.179 | −3.394 | 0.0069731 | anterior pharynx defective 1 homolog B (C. elegans) |
| SEMA3G | 5.896 | 4.322 | 4.548 | 2.559 | 2.559 | 4.255 | −3.393 | 0.0390476 | sema domain, immunoglobulin domain (Ig), short basic domain, secreted, (semaphorin) 3G |
| UQCRQ | 6.840 | 7.017 | 6.240 | 4.478 | 5.607 | 4.998 | −3.393 | 0.0118634 | ubiquinol-cytochrome c reductase, complex III subunitVII, 9.5 kDa |
| PPP2R1A | 9.168 | 10.979 | 9.886 | 8.335 | 8.126 | 7.890 | −3.387 | 0.0148565 | protein phosphatase 2, regulatory subunit A, alpha |
| LOC729176 | 2.671 | 2.671 | 1.734 | −0.026 | 1.169 | −0.026 | −3.386 | 0.0106639 | No description |
| HAG HL | 2.944 | 4.054 | 4.187 | 2.296 | 2.296 | 2.296 | −3.381 | 0.0198442 | hydroxyacylglutathione hydrolase-like |
| DDOST | 5.346 | 7.436 | 5.473 | 4.111 | 3.591 | 4.368 | −3.375 | 0.0215157 | dolichyl-diphosphooligosaccharide-protein glycosyltransferase |
| TRIM45 | 3.758 | 2.531 | 3.922 | 0.974 | 2.169 | 0.974 | −3.371 | 0.0143845 | tripartite motif-containing 45 |
| CDC42BPB | 7.030 | 8.604 | 7.871 | 5.913 | 6.101 | 6.851 | −3.369 | 0.0298327 | CDC42 binding protein kinase beta (DMPK-like) |
| TP53TG1 | 5.772 | 5.577 | 5.348 | 4.118 | 3.825 | 2.108 | −3.369 | 0.0127705 | TP53 target 1 (non-protein coding) |
| DMAP1 | 6.796 | 7.406 | 8.211 | 6.461 | 5.557 | 5.484 | −3.363 | 0.0222625 | DNA methyltransferase 1 associated protein 1 |
| CAPN8 | 8.910 | 10.880 | 8.918 | 7.493 | 7.957 | 7.162 | −3.359 | 0.0211612 | calpain 8 |
| GYLTL1B | 4.042 | 3.468 | 4.875 | 2.296 | 2.296 | 2.695 | −3.354 | 0.0130008 | glycosyltransferase-like 1B |
| S100A14 | 12.917 | 13.609 | 13.796 | 11.646 | 12.054 | 11.190 | −3.346 | 0.0071167 | S100 calcium binding protein A14 |
| MTMR11 | 5.768 | 6.118 | 5.488 | 4.637 | 4.027 | 3.680 | −3.344 | 0.0080913 | myotubularin related protein 11 |
| RNASET2 | 8.650 | 8.533 | 10.916 | 6.793 | 7.668 | 7.889 | −3.340 | 0.0425295 | ribonuclease T2 |
| NUCB2 | 7.284 | 8.411 | 6.658 | 5.624 | 5.546 | 5.464 | −3.335 | 0.0129555 | nucleobindin 2 |
| EGFL8 | 4.360 | 4.577 | 5.475 | 2.746 | 2.840 | 3.205 | −3.333 | 0.0062057 | EGF-like-domain, multiples |
| STX3 | 7.520 | 7.227 | 6.186 | 5.336 | 5.440 | 5.784 | −3.331 | 0.0218772 | syntaxin 3 |
| C22orf28 | 7.241 | 6.234 | 5.394 | 4.290 | 4.990 | 4.498 | −3.331 | 0.0249731 | chromosome 22 open reading frame 28 |
| KCNAB3 | 4.421 | 5.510 | 5.070 | 3.334 | 4.448 | 2.457 | −3.330 | 0.0433784 | potassium voltage-gated channel, shaker-related subfamily, beta member 3 |
| MAGOH | 7.842 | 7.479 | 9.693 | 5.744 | 7.078 | 6.844 | −3.330 | 0.0469271 | mago-nashi homolog, proliferation-associated (Drosophila) |
| ZNF238 | 5.819 | 5.657 | 5.189 | 4.085 | 3.858 | 3.839 | −3.328 | 0.0031857 | zinc finger protein 238 |
| MOGS | 5.920 | 6.640 | 6.764 | 4.434 | 4.960 | 4.907 | −3.323 | 0.0067966 | mannosyl-oligosaccharide glucosidase |
| ATAD3B | 5.072 | 5.578 | 6.616 | 3.343 | 4.394 | 4.522 | −3.316 | 0.0281504 | ATPase family, AAA domain containing 3B |
| NFKBIL1 | 5.275 | 5.262 | 5.633 | 3.511 | 3.548 | 4.459 | −3.310 | 0.0105863 | nuclear factor of kappa light polypeptide gene enhancer in B-cells inhibitor-like 1 |
| HCFC1 | 7.083 | 8.841 | 8.171 | 6.450 | 6.192 | 6.650 | −3.298 | 0.0254213 | host cell factor C1 (VP16-accessory protein) |
| DBNDD1 | 6.520 | 8.441 | 8.257 | 6.721 | 6.037 | 5.484 | −3.295 | 0.0446777 | dysbindin (dystrobrevin binding protein 1) domain containing 1 |
| AMT | 6.643 | 5.533 | 6.546 | 4.054 | 3.817 | 5.829 | −3.287 | 0.0460829 | aminomethyltransferase |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24 N48 | CD24 N58 | CD24 N43 | CD24 N37 | CD24 N39 | CD24 N40 | Pseudo fold change | P value | Gene description |
| AQP3 | 6.223 | 9.404 | 7.127 | 5.069 | 5.412 | 5.844 | −3.284 | 0.0418580 | aquaporin 3 (Gill blood group) |
| WBP1 | 7.370 | 7.525 | 7.882 | 5.657 | 6.029 | 5.981 | −3.278 | 0.0022863 | WW domain binding protein 1 |
| SNRNP35 | 4.204 | 4.976 | 4.864 | 3.263 | 3.123 | 2.695 | −3.278 | 0.0062955 | small nuclear ribonucleoprotein 35 kDa (U11/U12) |
| LOC93622 | 4.042 | 5.560 | 5.299 | 3.848 | 3.248 | 3.043 | −3.278 | 0.0260061 | No description |
| MTATP6 | 12.461 | 13.249 | 11.341 | 10.448 | 10.749 | 10.880 | −3.276 | 0.0263998 | No description |
| SLC39A4 | 5.418 | 5.630 | 6.367 | 3.542 | 4.657 | 4.646 | −3.271 | 0.0229325 | solute carrier family 39 (zinc transporter), member 4 |
| KIAA0922 | 5.529 | 4.336 | 3.126 | 2.296 | 2.627 | 3.043 | −3.268 | 0.0459309 | KIAA0922 |
| LOC139201 | 5.418 | 4.857 | 4.382 | 2.108 | 3.825 | 3.152 | −3.260 | 0.0189816 | No description |
| NUP160 | 4.514 | 5.457 | 5.136 | 3.205 | 3.648 | 3.431 | −3.260 | 0.0079156 | nucleoporin 160 kDa |
| CCDC53 | 4.353 | 4.005 | 3.240 | 1.911 | 1.559 | 2.650 | −3.257 | 0.0116094 | coiled-coil domain containing 53 |
| PHF23 | 5.083 | 5.985 | 5.616 | 3.381 | 3.680 | 4.891 | −3.255 | 0.0268726 | PHD finger protein 23 |
| DTX2 | 6.906 | 7.902 | 7.101 | 5.168 | 6.249 | 5.400 | −3.252 | 0.0143108 | deltex homolog 2 (Drosophila) |
| MCAT | 6.098 | 7.146 | 7.575 | 5.776 | 5.445 | 5.164 | −3.250 | 0.0261190 | malonyl CoA:ACP acyltransferase (mitochondrial) |
| RILPL2 | 4.349 | 3.891 | 2.875 | 1.559 | 1.559 | 2.650 | −3.247 | 0.0205457 | Rab interacting lysosomal protein-like 2 |
| KHSRP | 7.942 | 7.734 | 7.277 | 6.036 | 6.034 | 6.218 | −3.245 | 0.0038956 | KH-type splicing regulatory protein |
| MMP14 | 4.987 | 6.276 | 5.817 | 4.400 | 4.121 | 3.831 | −3.241 | 0.0153661 | matrix metalloproteinase 14 (membrane-inserted) |
| ETNK2 | 6.978 | 5.258 | 4.423 | 3.643 | 3.565 | 3.443 | −3.233 | 0.0275526 | ethanolamine kinase 2 |
| TLCD1 | 3.470 | 3.604 | 2.453 | 1.911 | 1.559 | 1.559 | −3.233 | 0.0157160 | TLC domain containing 1 |
| CHKB | 6.001 | 6.835 | 6.286 | 3.664 | 4.593 | 5.462 | −3.232 | 0.0203653 | choline kinase beta |
| RPSAP58 | 12.692 | 12.206 | 11.701 | 9.495 | 10.631 | 11.001 | −3.230 | 0.0165127 | ribosomal protein SA pseudogene 58 |
| SBF1P1 | 10.300 | 9.473 | 9.980 | 7.647 | 8.620 | 8.291 | −3.224 | 0.0089747 | SET binding factor 1 pseudogene 1 |
| CEACAM19 | 6.203 | 7.654 | 8.265 | 4.926 | 5.998 | 5.965 | −3.223 | 0.0375180 | carcinoembryonic antigen-related cell adhesion molecule 19 |
| UBXN1 | 8.964 | 9.183 | 9.244 | 7.495 | 7.213 | 7.873 | −3.222 | 0.0034474 | UBX domain protein 1 |
| GPR108 | 7.417 | 8.575 | 8.837 | 6.888 | 7.022 | 6.694 | −3.221 | 0.0273615 | G protein-coupled receptor 108 |
| ALDH4A1 | 6.059 | 6.387 | 8.108 | 4.920 | 5.160 | 4.372 | −3.221 | 0.0199002 | aldehyde dehydrogenase 4 family, member A1 |
| CDK20 | 3.810 | 4.323 | 4.247 | 2.559 | 2.559 | 2.559 | −3.221 | 0.0024804 | cyclin-dependent kinase 20 |
| TBC1D10B | 5.924 | 6.312 | 6.510 | 4.237 | 5.281 | 4.462 | −3.219 | 0.0114052 | TBC1 domain family, member 10B |
| ZBTB22 | 4.964 | 5.735 | 5.802 | 3.585 | 4.116 | 3.888 | −3.218 | 0.0074981 | zinc finger and BTB domain containing 22 |
| NAPA | 8.693 | 10.011 | 8.597 | 7.280 | 7.170 | 6.916 | −3.206 | 0.0090844 | N-ethylmaleimide-sensitive factor attachment protein, alpha |
| UBR4 | 9.432 | 9.744 | 9.597 | 7.901 | 8.177 | 7.754 | −3.200 | 0.0017767 | ubiquitin protein ligase E3 component n-recognin 4 |
| PUF60 | 7.502 | 8.989 | 8.892 | 6.636 | 7.278 | 7.214 | −3.199 | 0.0375395 | poly-U binding splicing factor 60KDa |
| TICAM1 | 8.103 | 8.344 | 7.666 | 6.353 | 6.129 | 6.668 | −3.197 | 0.0044566 | toll-like receptor adaptor molecule 1 |
| CRIP2 | 9.331 | 9.214 | 8.990 | 6.680 | 7.677 | 7.538 | −3.195 | 0.0051489 | cysteine-rich protein 2 |
| INO80B | 6.289 | 5.144 | 6.371 | 3.469 | 4.821 | 4.246 | −3.193 | 0.0207859 | INO80 complex subunit B |
| CDK5RAP3 | 6.947 | 5.258 | 4.231 | 2.825 | 3.583 | 4.222 | −3.193 | 0.0466608 | CDK5 regulatory subunit associated protein 3 |
| FPGS | 6.547 | 7.094 | 6.929 | 5.213 | 5.269 | 5.258 | −3.184 | 0.0022218 | folylpolyglutamate synthase |
| SNX17 | 4.870 | 4.590 | 5.354 | 3.059 | 3.648 | 3.205 | −3.171 | 0.0061274 | sorting nexin 17 |
| C7orf53 | 4.870 | 4.255 | 3.914 | 2.559 | 2.559 | 2.559 | −3.170 | 0.0112901 | chromosome 7 open reading frame 53 |
| C11orf68 | 9.185 | 7.994 | 9.404 | 6.555 | 7.521 | 7.612 | −3.167 | 0.0262709 | chromosome 11 open reading frame 68 |
| FKBP11 | 8.150 | 9.389 | 9.594 | 7.754 | 7.625 | 7.726 | −3.154 | 0.0332893 | FK506 binding protein 11, 19 kDa |
| NUDT1 | 5.012 | 5.478 | 6.412 | 3.187 | 4.382 | 4.755 | −3.154 | 0.0441719 | nudix (nucleoside diphosphate linked moiety X)-type motif 1 |
| ZNF408 | 5.206 | 6.159 | 7.715 | 4.640 | 4.503 | 4.042 | −3.151 | 0.0294129 | zinc finger protein 408 |
| MIA | 6.514 | 6.488 | 7.236 | 3.825 | 5.581 | 5.352 | −3.150 | 0.0217283 | melanoma inhibitory activity |
| LRRFIP2 | 10.949 | 10.688 | 10.911 | 8.775 | 9.259 | 9.902 | −3.143 | 0.0111673 | leucine rich repeat (in FLII) interacting protein 2 |
| C11orf59 | 4.915 | 6.179 | 5.122 | 4.295 | 4.397 | 3.263 | −3.142 | 0.0389908 | chromosome 11 open reading frame 59 |
| IL17RD | 4.918 | 6.162 | 5.267 | 3.327 | 4.434 | 3.616 | −3.140 | 0.0196216 | interleukin 17 receptor D |

TABLE 5-continued

Differentially Expressed Genes in CD24+ Breast Epithelial Cells

| | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| SLC16A5 | 4.215 | 5.514 | 4.457 | 3.868 | 3.196 | 2.457 | -3.130 | 0.0335963 | solute carrier family 16, member 5 (monocarboxylic acid transporter 6) |
| ARL4A | 5.127 | 3.719 | 4.705 | 3.459 | 2.648 | 3.059 | -3.129 | 0.0279133 | ADP-ribosylation factor-like 4A |
| NIT2 | 7.239 | 7.932 | 7.559 | 5.441 | 6.287 | 6.087 | -3.127 | 0.0083154 | nitrilase family, member 2 |
| TXNDC11 | 5.121 | 5.223 | 3.802 | 3.578 | 2.840 | 2.899 | -3.126 | 0.0234198 | thioredoxin domain containing 11 |
| BARD1 | 3.475 | 3.203 | 2.404 | 1.559 | 1.559 | 1.559 | -3.125 | 0.0121366 | BRCA1 associated RING domain 1 |
| ITPA | 4.862 | 4.786 | 3.836 | 2.194 | 3.617 | 2.602 | -3.122 | 0.0216324 | inosine triphosphatase (nucleoside triphosphate pyrophosphatase) |
| PIK3R2 | 5.138 | 6.742 | 3.924 | 2.559 | 3.632 | 3.496 | -3.122 | 0.0386708 | phosphoinositide-3-kinase, regulatory subunit 2 (beta) |
| PAPSS1 | 5.664 | 6.398 | 4.665 | 4.758 | 3.712 | 3.954 | -3.117 | 0.0477889 | 3'-phosphoadenosine 5'-phosphosulfate synthase 1 |
| LIPH | 4.267 | 3.981 | 3.936 | 2.296 | 3.512 | 2.296 | -3.117 | 0.0267421 | lipase, member H |
| FAM65A | 7.948 | 9.749 | 8.833 | 7.121 | 7.196 | 7.281 | -3.110 | 0.0224697 | family with sequence similarity 65, member A |
| AMFR | 7.173 | 8.588 | 8.509 | 6.952 | 5.703 | 6.168 | -3.108 | 0.0208457 | autocrine motility factor receptor |
| GPX7 | 3.859 | 4.237 | 4.568 | 1.559 | 3.617 | 2.602 | -3.106 | 0.0360468 | glutathione peroxidase 7 |
| C19orf43 | 10.031 | 10.736 | 10.363 | 8.401 | 8.730 | 8.885 | -3.103 | 0.0038158 | chromosome 19 open reading frame 43 |
| ACAD10 | 5.443 | 5.206 | 5.613 | 3.809 | 3.343 | 4.042 | -3.103 | 0.0035434 | acyl-CoA dehydrogenase family, member 10 |
| CAPN1 | 8.999 | 10.888 | 9.513 | 8.342 | 7.880 | 7.544 | -3.102 | 0.0202947 | calpain 1, (mu/I) large subunit |
| RCVRN | 2.247 | 3.324 | 3.021 | 0.974 | 1.692 | 0.974 | -3.101 | 0.0124129 | recoverin |
| SF4 | 3.878 | 5.076 | 3.968 | 2.246 | 3.383 | 3.220 | -3.099 | 0.0435925 | No description |
| MAPKBP1 | 7.813 | 6.819 | 8.124 | 5.460 | 5.626 | 6.492 | -3.098 | 0.0177306 | mitogen-activated protein kinase binding protein 1 |
| PPP2R5C | 7.469 | 6.849 | 7.292 | 5.431 | 5.838 | 5.565 | -3.097 | 0.0040131 | protein phosphatase 2, regulatory subunit B'; gamma |
| TMED2 | 9.765 | 10.375 | 8.460 | 8.183 | 7.934 | 8.136 | -3.093 | 0.0423684 | transmembrane emp24 domain trafficking protein 2 |
| TAGLN2 | 10.227 | 10.345 | 9.741 | 8.717 | 8.563 | 8.425 | -3.092 | 0.0040752 | transgelin 2 |
| CYFIP2 | 4.353 | 3.187 | 2.404 | 1.559 | 2.075 | 1.559 | -3.089 | 0.0345556 | cytoplasmic FMR1 interacting protein 2 |
| E2F5 | 3.859 | 4.137 | 3.186 | 1.559 | 2.648 | 1.559 | -3.088 | 0.0121558 | E2F transcription factor 5, p130-binding |
| DDB1 | 8.015 | 8.884 | 8.882 | 6.935 | 7.249 | 7.258 | -3.087 | 0.0117183 | damage-specific DNA binding protein 1, 127 kDa |
| SF3B5 | 10.031 | 10.315 | 10.250 | 8.406 | 9.075 | 8.625 | -3.086 | 0.0049616 | splicing factor 3b, subunit 5, 10 kDa |
| CTBS | 6.060 | 6.339 | 6.470 | 4.846 | 4.503 | 4.650 | -3.083 | 0.0019870 | chitobiase, di-N-acetyl- |
| MAPK8IP3 | 8.376 | 9.226 | 9.773 | 7.603 | 7.431 | 7.948 | -3.081 | 0.0223937 | mitogen-activated protein kinase 8 interacting protein 3 |
| C8orf45 | 2.878 | 3.097 | 2.404 | 1.474 | 0.974 | 0.974 | -3.080 | 0.0048772 | chromosome 8 open reading frame 45 |
| NUMBL | 5.564 | 4.844 | 6.513 | 3.913 | 3.716 | 4.891 | -3.078 | 0.0464106 | numb homolog (Drosophila)-like |
| MKI67IP | 4.984 | 6.425 | 6.500 | 3.459 | 4.879 | 4.144 | -3.076 | 0.0261397 | MKI67 (FHA domain) interacting nucleolar phosphoprotein |
| COPE | 8.204 | 9.381 | 8.678 | 7.064 | 7.206 | 6.585 | -3.073 | 0.0085756 | coatomer protein complex, subunit epsilon |
| PNP | 9.193 | 8.805 | 8.913 | 7.185 | 7.294 | 7.969 | -3.072 | 0.0084482 | purine nucleoside phosphorylase |
| MIB2 | 7.936 | 7.427 | 9.656 | 6.318 | 6.157 | 6.318 | -3.070 | 0.0184451 | mindbomb homolog 2 (Drosophila) |
| ZNF32 | 4.382 | 5.775 | 5.577 | 3.542 | 3.345 | 4.158 | -3.067 | 0.0241474 | zinc finger protein 32 |
| TIMM10 | 6.694 | 6.670 | 6.262 | 4.938 | 5.197 | 4.646 | -3.065 | 0.0034367 | translocase of inner mitochondrial membrane 10 homolog (yeast) |
| NUMA1 | 9.200 | 9.814 | 9.188 | 7.728 | 7.573 | 8.099 | -3.064 | 0.0053484 | nuclear mitotic apparatus protein 1 |
| CUL7 | 5.390 | 6.419 | 6.232 | 4.357 | 4.618 | 4.618 | -3.061 | 0.0121857 | cullin 7 |
| KLHL17 | 4.843 | 4.756 | 6.261 | 3.605 | 3.144 | 4.066 | -3.056 | 0.0238864 | kelch-like 17 (Drosophila) |
| LNX2 | 4.350 | 5.893 | 4.962 | 3.598 | 3.026 | 3.351 | -3.054 | 0.0149624 | ligand of numb-protein X 2 |
| EIF2C2 | 7.151 | 7.497 | 7.540 | 5.540 | 5.695 | 6.372 | -3.054 | 0.0083369 | eukaryotic translation initiation factor 2C, 2 |
| BANF1 | 7.852 | 8.636 | 8.460 | 6.906 | 6.850 | 6.814 | -3.053 | 0.0069394 | barrier to autointegration factor 1 |
| PPP1R15A | 8.236 | 7.612 | 7.788 | 5.308 | 6.179 | 7.137 | -3.050 | 0.0250522 | protein phosphatase 1, regulatory (inhibitor) subunit 15A |
| TRPT1 | 4.215 | 3.593 | 3.583 | 2.649 | 1.974 | 1.974 | -3.049 | 0.0081980 | tRNA phosphotransferase 1 |
| STK36 | 4.741 | 4.959 | 3.999 | 2.943 | 3.026 | 3.351 | -3.047 | 0.0118526 | serine/threonine kinase 36 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| SFRS2 | 10.342 | 10.656 | 10.308 | 8.085 | 8.735 | 9.186 | −3.047 | 0.0064804 | No description |
| KDM1A | 6.760 | 7.091 | 5.441 | 5.165 | 5.183 | 4.901 | −3.020 | 0.0425833 | lysine (K)-specific demethylase 1A |
| MRPS30 | 5.418 | 5.998 | 5.197 | 3.664 | 3.825 | 4.283 | −3.016 | 0.0075748 | mitochondrial ribosomal protein S30 |
| CDK2 | 6.188 | 6.676 | 6.866 | 4.202 | 5.176 | 5.274 | −3.015 | 0.0111036 | cyclin-dependent kinase 2 |
| KIAA0427 | 7.060 | 8.296 | 8.845 | 6.536 | 6.871 | 6.705 | −3.013 | 0.0453799 | KIAA0427 |
| BUD31 | 4.572 | 5.587 | 4.449 | 2.860 | 3.196 | 3.565 | −3.010 | 0.0129900 | BUD31 homolog (S. cerevisiae) |
| NOP14 | 5.869 | 6.411 | 6.544 | 4.032 | 4.827 | 5.369 | −2.999 | 0.0196792 | NOP14 nucleolar protein homolog (yeast) |
| SIGLEC8 | 6.405 | 5.864 | 5.887 | 4.186 | 4.307 | 5.175 | −2.990 | 0.0140376 | sialic acid binding ig-like lectin 8 |
| LMNA | 13.446 | 13.289 | 13.361 | 11.788 | 11.525 | 12.909 | −2.974 | 0.0336416 | lamin A/C |
| ARGLU1 | 7.191 | 6.297 | 5.559 | 4.150 | 4.382 | 5.620 | −2.971 | 0.0393492 | arginine and glutamate rich 1 |
| DGCR2 | 5.915 | 7.696 | 7.048 | 5.478 | 5.619 | 5.085 | −2.969 | 0.0348020 | DiGeorge syndrome critical region gene 2 |
| DCAF11 | 6.837 | 6.151 | 6.406 | 5.267 | 4.822 | 4.730 | −2.968 | 0.0068181 | DDB1 and CUL4 associated factor 11 |
| EDF1 | 8.973 | 9.525 | 9.320 | 7.620 | 7.956 | 7.703 | −2.967 | 0.0038266 | endothelial differentiation-related factor 1 |
| ESRP1 | 5.930 | 5.003 | 5.012 | 3.728 | 3.738 | 3.434 | −2.967 | 0.0072778 | epithelial splicing regulatory protein 1 |
| RPS18 | 13.267 | 13.287 | 12.296 | 10.727 | 11.567 | 11.873 | −2.965 | 0.0215756 | ribosomal protein S18 |
| ABCE1 | 6.279 | 7.394 | 6.066 | 4.498 | 5.506 | 5.205 | −2.965 | 0.0286562 | ATP-binding cassette, sub-family E (OABP), member 1 |
| PHYHD1 | 6.039 | 6.042 | 6.513 | 4.520 | 4.421 | 4.946 | −2.963 | 0.0044459 | phytanoyl-CoA dioxygenase domain containing 1 |
| CUEDC1 | 4.126 | 5.516 | 3.649 | 2.559 | 3.204 | 2.559 | −2.962 | 0.0304305 | CUE domain containing 1 |
| PHRF1 | 8.019 | 8.604 | 9.115 | 7.038 | 7.277 | 6.975 | −2.960 | 0.0123078 | PHD and ring finger domains 1 |
| C1orf86 | 6.708 | 7.259 | 7.479 | 5.127 | 6.373 | 5.693 | −2.960 | 0.0241167 | chromosome 1 open reading frame 86 |
| B3GALNT1 | 3.475 | 3.844 | 2.703 | 1.911 | 2.075 | 1.559 | −2.956 | 0.0149455 | beta-1,3-N-acetylgalactosaminyltransferase 1 (globoside blood group) |
| ANO10 | 6.422 | 7.159 | 7.191 | 5.825 | 5.559 | 4.859 | −2.954 | 0.0153446 | anoctamin 10 |
| GGT7 | 6.056 | 6.860 | 7.207 | 4.367 | 5.443 | 5.645 | −2.953 | 0.0274114 | gamma-glutamyltransferase 7 |
| TMEM51 | 7.081 | 7.424 | 6.365 | 5.553 | 4.804 | 5.747 | −2.952 | 0.0158787 | transmembrane protein 51 |
| ATAD2 | 5.049 | 4.573 | 4.631 | 3.489 | 2.896 | 3.364 | −2.949 | 0.0058051 | ATPase family, AAA domain containing 2 |
| GLI4 | 4.448 | 3.699 | 4.716 | 1.474 | 3.022 | 3.156 | −2.948 | 0.0277306 | GLI family zinc finger 4 |
| PUM1 | 6.823 | 8.383 | 6.790 | 5.231 | 5.363 | 5.676 | −2.946 | 0.0144981 | pumilio homolog 1 (Drosophila) |
| AP2A1 | 3.831 | 5.167 | 4.937 | 3.496 | 3.337 | 3.379 | −2.944 | 0.0365211 | adaptor-related protein complex 2, alpha 1 subunit |
| GFOD1 | 6.372 | 5.290 | 4.997 | 3.872 | 3.859 | 3.440 | −2.942 | 0.0104981 | glucose-fructose oxidoreductase domain containing 1 |
| CHAD | 5.741 | 3.704 | 3.531 | 2.246 | 2.377 | 1.974 | −2.941 | 0.0198250 | chondroadherin |
| C9orf21 | 6.489 | 7.267 | 6.551 | 4.998 | 4.568 | 6.389 | −2.934 | 0.0478250 | chromosome 9 open reading frame 21 |
| BAD | 6.108 | 7.143 | 7.923 | 6.066 | 5.591 | 5.325 | −2.934 | 0.0472978 | BCL2-associated agonist of cell death |
| RPL29 | 7.233 | 5.932 | 6.457 | 4.905 | 5.041 | 4.686 | −2.933 | 0.0114751 | ribosomal protein L29 |
| TMEM160 | 5.908 | 6.858 | 7.780 | 5.693 | 5.306 | 4.801 | −2.932 | 0.0355833 | transmembrane protein 160 |
| UXT | 9.005 | 8.021 | 7.377 | 5.825 | 6.822 | 7.102 | −2.931 | 0.0395157 | ubiquitously-expressed transcript |
| SNRPD2 | 8.985 | 7.968 | 7.950 | 6.095 | 7.065 | 7.434 | −2.930 | 0.0367506 | small nuclear ribonucleoprotein D2 polypeptide 16.5 kDa |
| ELF2 | 5.128 | 5.891 | 4.690 | 3.271 | 3.144 | 4.351 | −2.920 | 0.0219685 | E74-like factor 2 (ets domain transcription factor) |
| ACADM | 5.607 | 5.535 | 6.144 | 4.730 | 3.922 | 4.062 | −2.918 | 0.0100683 | acyl-CoA dehydrogenase, C-4 to C-12 straight chain |
| HPCAL1 | 10.456 | 9.705 | 10.801 | 8.911 | 9.191 | 8.764 | −2.918 | 0.0180814 | hippocalcin-like 1 |
| RHPN1 | 7.516 | 7.334 | 8.170 | 5.824 | 6.278 | 5.972 | −2.917 | 0.0059079 | rhophilin, Rho GTPase binding protein 1 |
| FEZ2 | 6.793 | 7.518 | 7.168 | 5.099 | 6.065 | 5.626 | −2.912 | 0.0112464 | fasciculation and elongation protein zeta 2 (zygin II) |
| P4HB | 11.496 | 12.143 | 10.817 | 10.442 | 9.955 | 9.432 | −2.911 | 0.0232978 | prolyl 4-hydroxylase, beta polypeptide |
| MRPL42 | 7.786 | 8.213 | 6.931 | 6.605 | 6.246 | 6.115 | −2.909 | 0.0276163 | mitochondrial ribosomal protein L42 |
| LGALS3BP | 5.593 | 6.805 | 6.004 | 4.465 | 4.675 | 4.226 | −2.906 | 0.0103008 | lectin, galactoside-binding, soluble, 3 binding protein |
| RBM12 | 7.481 | 7.982 | 7.202 | 4.973 | 6.444 | 6.174 | −2.904 | 0.0190307 | RNA binding motif protein 12 |
| PBX2 | 8.125 | 8.698 | 8.764 | 7.227 | 6.817 | 7.097 | −2.902 | 0.0063438 | pre-B-cell leukemia homeobox 2 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| NDUFB7 | 6.529 | 7.105 | 7.060 | 5.523 | 5.927 | 4.736 | −2.901 | 0.0167636 | NADH dehydrogenase (ubiquinone) 1 beta subcomplex, 7, 18 kDa |
| HNRNPUL2 | 4.071 | 5.248 | 5.066 | 3.532 | 3.648 | 3.205 | −2.896 | 0.0247114 | heterogeneous nuclear ribonucleoprotein U-like2 |
| ZDHHC24 | 5.309 | 6.068 | 6.603 | 5.070 | 4.892 | 3.220 | −2.894 | 0.0487383 | zinc finger, DHHC-type containing 24 |
| UBE2A | 4.280 | 4.986 | 4.505 | 2.974 | 3.190 | 2.974 | −2.888 | 0.0045426 | ubiquitin-conjugating enzyme E2A(RAD6 homolog) |
| SMPDL3B | 3.336 | 4.167 | 3.932 | 3.022 | 2.402 | 0.974 | −2.888 | 0.0359010 | sphingomyelin phosphodiesterase, acid-like 3B |
| TMX2 | 5.537 | 7.083 | 5.013 | 4.190 | 4.266 | 3.484 | −2.887 | 0.0244835 | thioredoxin-related transmembrane protein 2 |
| RAP1GAP | 6.822 | 6.002 | 7.387 | 4.486 | 5.292 | 5.688 | −2.886 | 0.0272701 | RAP1 GTPase activating protein |
| CCND1 | 8.435 | 10.020 | 8.525 | 7.252 | 7.548 | 6.907 | −2.885 | 0.0197629 | cyclin D1 |
| TMEM101 | 6.458 | 7.445 | 7.219 | 4.957 | 5.917 | 5.016 | −2.884 | 0.0118104 | transmembrane protein 101 |
| GIPC1 | 8.995 | 9.865 | 8.513 | 6.987 | 7.876 | 7.494 | −2.878 | 0.0167851 | GIPC PDZ domain containing family, member 1 |
| ZNF688 | 4.215 | 5.258 | 5.810 | 3.966 | 2.692 | 4.098 | −2.875 | 0.0493507 | zinc finger protein 688 |
| ERCC2 | 5.140 | 4.455 | 5.031 | 3.617 | 3.296 | 3.296 | −2.874 | 0.0064454 | excision repair cross-complementing rodent repair deficiency, complementation group 2 |
| RAD9A | 6.738 | 7.195 | 6.138 | 4.678 | 5.215 | 5.643 | −2.873 | 0.0181090 | RAD9 homolog A (S. pombe) |
| ALOX15B | 9.153 | 7.845 | 8.800 | 7.630 | 6.579 | 7.149 | −2.873 | 0.0288127 | arachidonate 15-lipoxygenase, type B |
| CAD | 6.830 | 6.996 | 8.775 | 5.768 | 5.474 | 5.371 | −2.872 | 0.0179440 | carbamoyl-phosphate synthetase 2, aspartate transcarbamylase, and dihydroorotase |
| RRBP1 | 6.938 | 7.930 | 6.111 | 5.420 | 5.583 | 5.333 | −2.864 | 0.0288335 | ribosome binding protein 1 homolog 180 kDa (dog) |
| VARS2 | 6.907 | 8.281 | 8.179 | 6.492 | 6.765 | 6.547 | −2.859 | 0.0492617 | valyl-tRNA synthetase 2, mitochondrial (putative) |
| TMEM5 | 5.086 | 4.983 | 4.766 | 2.933 | 3.758 | 3.469 | −2.857 | 0.0061381 | transmembrane protein 5 |
| SFPQ | 7.654 | 9.586 | 8.607 | 6.610 | 7.094 | 7.295 | −2.855 | 0.0323998 | splicing factor proline/glutamine-rich |
| FAM76A | 4.218 | 4.195 | 3.809 | 2.518 | 2.896 | 2.296 | −2.854 | 0.0050576 | family with sequence similarity 76, member A |
| CCNK | 6.965 | 7.450 | 7.633 | 6.121 | 5.897 | 5.849 | −2.853 | 0.0070215 | cyclin K |
| CAPS | 4.126 | 5.386 | 4.715 | 3.205 | 2.840 | 3.496 | −2.848 | 0.0157790 | calcyphosine |
| ZNF581 | 5.954 | 6.074 | 6.133 | 4.098 | 4.627 | 4.584 | −2.842 | 0.0025480 | zinc finger protein 581 |
| GLT25D1 | 5.849 | 7.879 | 6.347 | 4.578 | 4.840 | 5.147 | −2.841 | 0.0239279 | glycosyltransferase 25 domain containing 1 |
| STOML2 | 7.074 | 9.621 | 7.616 | 6.110 | 5.896 | 6.749 | −2.840 | 0.0436662 | stomatin (EPB72)-like 2 |
| EPCAM | 6.839 | 5.966 | 6.399 | 4.083 | 5.333 | 5.263 | −2.840 | 0.0248757 | epithelial cell adhesion molecule |
| ACSF3 | 6.160 | 6.782 | 7.555 | 5.416 | 5.278 | 4.951 | −2.836 | 0.0151596 | acyl-CoA synthetase family member 3 |
| CMTM3 | 8.102 | 8.899 | 8.427 | 6.599 | 7.127 | 7.278 | −2.835 | 0.0110614 | CKLF-like MARVEL transmembrane domain containing 3 |
| WDR33 | 6.532 | 6.825 | 6.365 | 4.931 | 5.030 | 5.247 | −2.833 | 0.0030798 | WD repeat domain 33 |
| CHCHD2 | 11.669 | 12.241 | 13.517 | 10.739 | 11.188 | 10.656 | −2.832 | 0.0295395 | coiled-coil-helix-coiled-coil-helix domain containing 2 |
| MSRA | 4.421 | 6.280 | 5.523 | 4.421 | 4.022 | 3.443 | −2.831 | 0.0494371 | methionine sulfoxide reductase A |
| ORMDL1 | 6.056 | 6.066 | 6.133 | 4.241 | 4.565 | 4.367 | −2.830 | 0.0217836 | ORM1-like1 (S. cerevisiae) |
| ALKBH5 | 6.493 | 6.987 | 7.616 | 4.296 | 4.560 | 5.551 | −2.829 | 0.0227467 | alkB, alkylation repair homolog 5 (E. coli) |
| KIAA1683 | 4.126 | 3.637 | 5.796 | 4.083 | 4.560 | 5.263 | −2.828 | 0.0039601 | KIAA1683 |
| OR7E156P | 3.059 | 2.650 | 4.059 | 5.416 | 2.559 | 2.559 | −2.828 | 0.0393116 | olfactory receptor, family 7, subfamily E, member 156 pseudogene |
| GRTP1 | 4.968 | 3.922 | 5.225 | 1.559 | 2.075 | 1.559 | −2.826 | 0.0333952 | growth hormone regulated TBC protein 1 |
| STRC | 3.954 | 3.822 | 5.267 | 3.659 | 3.022 | 3.469 | −2.821 | 0.0195203 | stereocilin |
| PPFIBP2 | 5.055 | 5.010 | 2.860 | 1.974 | 1.974 | 2.457 | −2.818 | 0.0116646 | PTPRF interacting protein, binding protein 2 (liprin beta 2) |
| ILVBL | 6.061 | 5.072 | 4.353 | 3.319 | 2.858 | 3.704 | −2.816 | 0.0173154 | ilvB (bacterial acetolactate synthase)-like |
| GCAT | 3.059 | 3.051 | 5.084 | 3.578 | 4.347 | 3.787 | −2.812 | 0.0034259 | glycine C-acetyltransferase |
| ECHS1 | 5.747 | 5.402 | 2.650 | 1.559 | 1.559 | 1.559 | −2.811 | 0.0032402 | enoyl CoA hydratase, short chain, 1, mitochondrial |
| STBD1 | 5.604 | 6.118 | 5.851 | 3.963 | 4.360 | 3.954 | −2.810 | 0.0218519 | starch binding domain 1 |
| STX5 | 10.164 | 9.456 | 6.038 | 4.111 | 4.547 | 5.191 | −2.810 | 0.0201243 | syntaxin 5 |
| | | | 10.722 | 8.675 | 8.634 | 8.884 | −2.806 | | |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| KIAA0652 | 6.467 | 6.440 | 5.231 | 4.952 | 4.537 | 4.964 | −2.806 | 0.0403822 | No description |
| FBP1 | 6.747 | 6.473 | 6.027 | 5.602 | 4.985 | 4.367 | −2.805 | 0.0219071 | fructose-1,6-bisphosphatase 1 |
| PSPC1 | 4.428 | 5.686 | 3.774 | 2.943 | 3.026 | 2.782 | −2.798 | 0.0234091 | paraspeckle component 1 |
| PRSS22 | 8.961 | 9.960 | 10.401 | 7.838 | 8.478 | 8.859 | −2.794 | 0.0404137 | protease, serine, 22 |
| PRMT5 | 4.548 | 5.693 | 4.939 | 3.178 | 4.213 | 3.404 | −2.788 | 0.0255787 | protein arginine methyltransferase 5 |
| IMP3 | 5.575 | 7.155 | 5.386 | 4.548 | 4.485 | 3.907 | −2.788 | 0.0259954 | IMP3, U3 small nucleolar ribonucleoprotein, homolog (yeast) |
| LIG1 | 4.821 | 5.125 | 5.488 | 3.809 | 3.343 | 3.809 | −2.785 | 0.0068074 | ligase l, DNA, ATP-dependent |
| CEP290 | 3.954 | 3.724 | 3.724 | 2.246 | 2.692 | 1.974 | −2.785 | 0.0052801 | centrosomal protein 290 kDa |
| APOBEC3C | 4.801 | 4.801 | 4.693 | 3.324 | 3.022 | 3.758 | −2.782 | 0.0069286 | apolipoprotein B mRNA editing enzyme, catalytic polypeptide-like 3C |
| SH3BGRL | 6.314 | 6.256 | 4.989 | 3.992 | 4.840 | 4.498 | −2.779 | 0.0346316 | SH3 domain binding glutamic acid-rich protein like |
| CDK5RAP2 | 6.021 | 6.093 | 6.775 | 5.223 | 4.547 | 5.124 | −2.778 | 0.0168120 | CDK5 regulatory subunit associated protein 2 |
| ING5 | 5.349 | 5.694 | 5.655 | 3.848 | 4.820 | 4.183 | −2.776 | 0.0177091 | inhibitor of growth family, member 5 |
| ACSF2 | 6.639 | 6.999 | 7.227 | 5.527 | 5.722 | 5.226 | −2.774 | 0.0059509 | acyl-CoA synthetase family member 2 |
| PSME2 | 6.665 | 8.477 | 7.546 | 5.237 | 6.626 | 6.075 | −2.773 | 0.0442095 | proteasome (prosome, macropain) activator subunit 2 (PA28 beta) |
| WDR18 | 5.773 | 6.860 | 6.800 | 5.153 | 5.390 | 4.499 | −2.772 | 0.0232433 | WD repeat domain 18 |
| SCMH1 | 4.492 | 5.277 | 4.953 | 2.974 | 3.483 | 3.888 | −2.771 | 0.0145088 | sex comb on midleg homolog 1 (Drosophila) |
| ZFX | 5.035 | 5.647 | 4.066 | 3.565 | 4.032 | 2.782 | −2.771 | 0.0444421 | zinc finger protein, X-linked |
| EEF1D | 11.399 | 12.560 | 12.633 | 10.153 | 10.518 | 11.163 | −2.769 | 0.0227360 | eukaryotic translation elongation factor 1 delta (guanine nucleotide exchange protein) |
| BEND2 | 5.012 | 5.198 | 6.164 | 4.154 | 4.065 | 3.544 | −2.767 | 0.0162157 | BEN domain containing 2 |
| TMED3 | 7.873 | 8.104 | 7.627 | 6.581 | 6.336 | 6.408 | −2.761 | 0.0034689 | transmembrane emp24 protein transport domain containing 3 |
| ABCB9 | 4.408 | 4.384 | 3.616 | 2.943 | 2.782 | 2.782 | −2.760 | 0.0131374 | ATP-binding cassette, sub-family B (MDR/TAP), member 9 |
| EXOC7 | 7.761 | 8.737 | 9.649 | 7.274 | 7.629 | 6.919 | −2.758 | 0.0451857 | exocyst complex component 7 |
| C7orf63 | 5.745 | 5.495 | 4.412 | 4.116 | 3.519 | 4.031 | −2.758 | 0.0342087 | chromosome 7 open reading frame 63 |
| RNASEK | 10.642 | 11.328 | 11.639 | 9.865 | 9.900 | 9.420 | −2.757 | 0.0127813 | ribonuclease, RNase K |
| SMARCD2 | 6.309 | 7.195 | 7.181 | 5.732 | 5.457 | 4.980 | −2.757 | 0.0143323 | SWI/SNF related, matrix associated, actin dependent regulator of chromatin, subfamily d, member 2 |
| CHSY1 | 7.166 | 7.434 | 7.076 | 5.707 | 4.933 | 6.173 | −2.749 | 0.0116454 | chondroitin sulfate synthase 1 |
| MPG | 7.550 | 8.392 | 8.997 | 6.934 | 7.182 | 6.627 | −2.748 | 0.0283070 | N-methylpurine-DNA glycosylase |
| SF3A2 | 8.648 | 9.024 | 9.409 | 7.132 | 7.580 | 7.950 | −2.748 | 0.0120230 | splicing factor 3a, subunit 2, 66 kDa |
| GCN1L1 | 6.952 | 7.480 | 7.228 | 5.227 | 6.332 | 5.770 | −2.747 | 0.0153983 | GCN1 general control of amino-acid synthesis 1-like 1 (yeast) |
| NFRKB | 7.430 | 8.019 | 8.175 | 6.319 | 6.681 | 6.561 | −2.746 | 0.0101796 | nuclear factor related to kappaB binding protein |
| MRPS34 | 5.692 | 7.828 | 6.575 | 5.673 | 5.117 | 4.445 | −2.746 | 0.0491827 | mitochondrial ribosomal protein S34 |
| TNF | 11.469 | 10.461 | 11.873 | 9.639 | 10.227 | 10.012 | −2.745 | 0.0366278 | tumor necrosis factor |
| WDR59 | 6.213 | 6.439 | 5.483 | 4.263 | 4.866 | 4.758 | −2.741 | 0.0155157 | WD repeat domain 59 |
| ZNF783 | 4.717 | 4.922 | 4.575 | 3.396 | 3.187 | 3.264 | −2.738 | 0.0021320 | zinc finger family member 783 |
| TXNDC16 | 4.353 | 4.511 | 3.186 | 1.911 | 2.075 | 3.059 | −2.737 | 0.0240322 | thioredoxin domain containing 16 |
| ELMO2 | 4.292 | 4.613 | 4.565 | 2.911 | 2.840 | 3.205 | −2.736 | 0.0027007 | engulfment and cell motility 2 |
| NEDD4L | 10.390 | 10.001 | 9.915 | 8.063 | 8.683 | 8.938 | −2.736 | 0.0087475 | neural precursor cell expressed, developmentally down-regulated 4-like |
| FCGRT | 7.506 | 8.310 | 7.709 | 6.056 | 6.339 | 6.697 | −2.733 | 0.0106262 | Fc fragment of IgG, receptor, transporter, alpha |
| MFGE8 | 12.034 | 11.230 | 13.562 | 9.843 | 10.584 | 10.894 | −2.732 | 0.0370123 | milk fat globule-EGF factor 8 protein |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| TPD52 | 7.837 | 6.755 | 6.204 | 5.666 | 5.223 | 5.307 | −2.729 | 0.0258473 | tumor protein D52 |
| CTTN | 9.400 | 10.709 | 10.307 | 8.859 | 8.773 | 9.114 | −2.728 | 0.0355510 | cortactin |
| CD276 | 7.569 | 8.942 | 8.724 | 7.276 | 7.151 | 7.351 | −2.728 | 0.0496738 | CD276 molecule |
| TMC7 | 6.253 | 7.131 | 5.770 | 5.068 | 4.808 | 4.772 | −2.723 | 0.0179954 | transmembrane channel-like 7 |
| GRINA | 8.175 | 9.355 | 8.958 | 7.457 | 7.513 | 7.532 | −2.722 | 0.0200230 | glutamate receptor, ionotropic, N-methyl D-aspartate-associated protein 1 (glutamate binding) |
| PPP1R1A | 5.028 | 3.747 | 4.693 | 3.108 | 3.583 | 3.220 | −2.722 | 0.0409555 | protein phosphatase 1, regulatory (inhibitor) subunit 1A |
| ATAD1 | 6.837 | 6.422 | 5.932 | 4.906 | 5.225 | 4.978 | −2.722 | 0.0122655 | ATPase family, AAA domain containing 1 |
| KDM4B | 5.772 | 5.669 | 5.226 | 3.902 | 4.226 | 4.226 | −2.719 | 0.0050982 | lysine (K)-specific demethylase 4B |
| TNFAIP1 | 6.192 | 6.890 | 6.889 | 5.449 | 5.311 | 4.900 | −2.715 | 0.0103515 | tumor necrosis factor, alpha-induced protein 1 (endothelial) |
| VAMP8 | 8.553 | 10.523 | 8.303 | 7.078 | 7.112 | 7.281 | −2.715 | 0.0244620 | vesicle-associated membrane protein 8 (endobrevin) |
| B3GALT6 | 6.136 | 7.427 | 7.180 | 5.882 | 5.739 | 5.554 | −2.714 | 0.0401535 | UDP-Gal:betaGal beta 1,3-galactosyltransferase polypeptide 6 |
| SLC27A1 | 6.028 | 6.093 | 5.574 | 4.396 | 4.732 | 4.134 | −2.714 | 0.0064996 | solute carrier family 27 (fatty acid transporter), member 1 |
| ENSA | 7.270 | 7.060 | 6.778 | 5.339 | 5.630 | 5.690 | −2.711 | 0.0037383 | endosulfine alpha |
| ANKK1 | 7.705 | 7.572 | 6.644 | 6.087 | 6.110 | 6.266 | −2.710 | 0.0312840 | ankyrin repeat and kinase domain containing 1 |
| STK10 | 5.224 | 7.055 | 6.160 | 4.571 | 4.835 | 4.722 | −2.710 | 0.0377544 | serine/threonine kinase 10 |
| ABTI | 5.642 | 7.363 | 6.122 | 4.686 | 4.486 | 4.859 | −2.707 | 0.0201635 | activator of basal transcription 1 |
| TRAFD1 | 9.334 | 9.337 | 8.105 | 7.901 | 7.575 | 7.586 | −2.707 | 0.0381381 | TRAF-type zinc finger domain containing 1 |
| ZBTB47 | 4.419 | 6.026 | 5.506 | 4.070 | 4.148 | 3.509 | −2.706 | 0.0373438 | zinc finger and BTB domain containing 47 |
| NCAPH2 | 8.138 | 8.038 | 8.725 | 5.798 | 6.702 | 7.294 | −2.705 | 0.0167130 | non-SMC condensin II complex, subunit H2 |
| TMEM214 | 7.649 | 8.394 | 8.147 | 6.530 | 6.960 | 6.586 | −2.701 | 0.0102195 | transmembrane protein 214 |
| INPPL1 | 8.541 | 9.613 | 8.552 | 7.384 | 7.109 | 7.173 | −2.698 | 0.0094520 | inositol polyphosphate phosphatase-like 1 |
| PLA2G2D | 7.947 | 7.834 | 7.092 | 6.194 | 6.404 | 6.455 | −2.696 | 0.0154482 | phospholipase A2, group IID |
| LOC100233209 | 7.606 | 7.749 | 7.351 | 6.228 | 5.920 | 6.293 | −2.695 | 0.0038534 | No description |
| CDH1 | 11.665 | 11.560 | 10.986 | 9.795 | 10.187 | 10.130 | −2.695 | 0.0093745 | cadherin 1, type 1, E-cadherin (epithelial) |
| TSPAN4 | 5.309 | 5.651 | 6.938 | 4.165 | 4.222 | 4.758 | −2.693 | 0.0264375 | tetraspanin 4 |
| XRCC1 | 4.572 | 5.887 | 5.527 | 4.459 | 3.583 | 3.954 | −2.690 | 0.0367813 | X-ray repair complementing defective repair in Chinese hamster cells 1 |
| DDAH2 | 10.278 | 10.190 | 11.039 | 9.085 | 8.763 | 8.893 | −2.688 | 0.0070107 | dimethylarginine dimethylaminohydrolase 2 |
| PRDX2 | 7.848 | 7.891 | 7.240 | 6.026 | 6.465 | 5.875 | −2.687 | 0.0075579 | peroxiredoxin 2 |
| PDK2 | 4.793 | 5.019 | 5.305 | 3.880 | 3.638 | 3.236 | −2.685 | 0.0070959 | pyruvate dehydrogenase kinase, isozyme 2 |
| ELF3 | 10.236 | 9.851 | 9.027 | 8.051 | 8.237 | 8.814 | −2.680 | 0.0294021 | E74-like factor 3 (ets domain transcription factor, epithelial-specific) |
| GJC2 | 3.220 | 3.668 | 4.383 | 2.246 | 1.974 | 2.860 | −2.680 | 0.0256815 | gap junction protein, gamma 2, 47 kDa |
| PRDM2 | 7.555 | 7.658 | 6.965 | 5.927 | 6.135 | 6.219 | −2.676 | 0.0104774 | PR domain containing 2, with ZNF domain |
| ZNF250 | 6.682 | 6.005 | 5.958 | 4.540 | 4.547 | 5.673 | −2.673 | 0.0361351 | zinc finger protein 250 |
| SLC25A6 | 12.433 | 12.029 | 12.023 | 10.365 | 11.015 | 11.001 | −2.672 | 0.0100476 | solute carrier family 25 (mitochondrial carrier; adenine nucleotide translocator), member 6 |
| CYB561D2 | 5.097 | 6.528 | 5.187 | 4.486 | 4.594 | 3.680 | −2.670 | 0.0482671 | cytochrome b-561 domain containing 2 |
| FAM36A | 6.702 | 6.347 | 5.653 | 5.181 | 4.922 | 4.931 | −2.669 | 0.0226915 | family with sequence similarity 36, member A |
| KRH | 4.126 | 4.620 | 3.257 | 2.559 | 3.204 | 2.559 | −2.668 | 0.0448243 | KRH homolog 1 (Drosophila) |
| CBY1 | 6.204 | 7.413 | 6.824 | 5.747 | 5.410 | 5.394 | −2.665 | 0.0242180 | chibby homolog 1 (S. cerevisiae) |
| RPL27 | 9.780 | 9.760 | 8.555 | 7.533 | 7.639 | 8.366 | −2.664 | 0.0248258 | ribosomal protein L27 |
| CYB5RL | 7.092 | 6.868 | 6.282 | 5.454 | 5.135 | 5.651 | −2.664 | 0.0135994 | cytochrome b5 reductase-like |
| COMMD6 | 9.982 | 8.919 | 9.040 | 7.510 | 7.917 | 8.277 | −2.656 | 0.0216216 | COMM domain containing 6 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| ZNF204P | 3.706 | 4.074 | 3.387 | 2.296 | 2.296 | 2.296 | −2.656 | 0.0052525 | zinc finger protein 204, pseudogene |
| C8orf58 | 3.706 | 4.179 | 4.187 | 3.043 | 2.296 | 2.695 | −2.656 | 0.0117437 | chromosome 8 open reading frame 58 |
| IL11 | 3.706 | 3.798 | 4.749 | 3.013 | 2.296 | 3.043 | −2.656 | 0.0307107 | interleukin 11 |
| KIAA0895 | 4.631 | 5.225 | 5.571 | 2.709 | 3.817 | 4.445 | −2.654 | 0.0400223 | KIAA0895 |
| PLA2G2A | 2.878 | 2.878 | 1.643 | 1.474 | 0.974 | 0.974 | −2.646 | 0.0335065 | phospholipase A2, group IIA (platelets, synovial fluid) |
| LRPAP1 | 2.878 | 4.766 | 3.772 | 1.474 | 2.848 | 2.404 | −2.646 | 0.0490384 | low density lipoprotein receptor-related protein associated protein 1 |
| VEGFB | 6.204 | 6.044 | 5.355 | 4.907 | 3.469 | 4.641 | −2.644 | 0.0278849 | vascular endothelial growth factor B |
| POLR2G | 6.927 | 7.637 | 6.118 | 5.720 | 5.525 | 5.107 | −2.643 | 0.0287137 | polymerase (RNA) II (DNA directed) polypeptide G |
| DIS3L | 9.815 | 9.807 | 9.212 | 8.138 | 8.092 | 8.414 | −2.641 | 0.0074873 | DIS3 mitotic control homolog (S. cerevisiae)-like |
| ULK3 | 5.443 | 5.619 | 4.997 | 4.054 | 4.042 | 4.042 | −2.640 | 0.0069501 | unc-51-like kinase 3 (C. elegans) |
| SCARB2 | 6.571 | 5.922 | 4.927 | 4.835 | 4.210 | 4.525 | −2.634 | 0.0497598 | scavenger receptor class B, member 2 |
| PM20D2 | 5.109 | 5.892 | 4.977 | 4.107 | 3.877 | 3.581 | −2.631 | 0.0122341 | peptidase M20 domain containing 2 |
| C14orf1 | 3.470 | 4.585 | 2.875 | 2.610 | 2.075 | 1.559 | −2.630 | 0.0352264 | chromosome 14 open reading frame 1 |
| CLDN3 | 11.944 | 10.306 | 11.121 | 9.727 | 9.806 | 9.551 | −2.628 | 0.0303384 | claudin 3 |
| TRIM28 | 10.809 | 11.225 | 11.774 | 9.518 | 9.831 | 9.994 | −2.628 | 0.0108135 | tripartite motif-containing 28 |
| TSPAN9 | 4.607 | 4.642 | 5.608 | 4.215 | 3.704 | 3.077 | −2.626 | 0.0403715 | tetraspanin 9 |
| EIF4EBP1 | 8.458 | 9.158 | 8.062 | 7.474 | 7.066 | 6.722 | −2.624 | 0.0173569 | eukaryotic translation initiation factor 4E binding protein 1 |
| DCUN1D2 | 4.741 | 4.912 | 6.004 | 3.692 | 4.005 | 3.351 | −2.620 | 0.0193929 | DCN1, defective in cullin neddylation 1, domain containing 2 (S. cerevisiae) |
| GRK6 | 6.799 | 7.415 | 8.167 | 5.918 | 6.027 | 6.118 | −2.617 | 0.0200476 | G protein-coupled receptor kinase 6 |
| PTPRF | 9.737 | 10.180 | 10.451 | 8.793 | 8.178 | 9.201 | −2.615 | 0.0181366 | protein tyrosine phosphatase, receptor type, F |
| ICA1 | 8.614 | 8.797 | 9.800 | 7.505 | 8.159 | 7.229 | −2.612 | 0.0269808 | islet cell autoantigen 1,69 kDa |
| ABHD14A | 3.059 | 3.767 | 3.459 | 1.911 | 2.075 | 2.173 | −2.611 | 0.0077130 | abhydrolase domain containing 14A |
| ZNF667 | 4.042 | 3.680 | 3.364 | 2.296 | 2.627 | 2.296 | −2.610 | 0.0101389 | zinc finger protein 667 |
| ARL8A | 9.097 | 10.373 | 9.717 | 8.222 | 8.333 | 8.544 | −2.609 | 0.0218243 | ADP-ribosylation factor-like 8A |
| ENGASE | 6.178 | 7.262 | 8.371 | 5.056 | 5.900 | 5.879 | −2.609 | 0.0420706 | endo-beta-N-acetylglucosaminidase |
| HIGD2A | 7.281 | 6.431 | 7.542 | 5.861 | 5.482 | 6.160 | −2.607 | 0.0309355 | HIG1 hypoxia inducible domain family, member 2A |
| HNRNPAO | 7.663 | 9.014 | 7.607 | 6.225 | 6.701 | 7.043 | −2.607 | 0.0352371 | heterogeneous nuclear ribonucleoprotein AO |
| LOC1 002943 62 | 8.693 | 8.282 | 8.656 | 7.275 | 6.749 | 7.705 | −2.604 | 0.0168772 | No description |
| CBX6 | 4.585 | 5.018 | 4.455 | 3.205 | 3.960 | 2.782 | −2.603 | 0.0218350 | chromobox homolog 6 |
| SLC37A3 | 6.809 | 7.304 | 6.114 | 4.859 | 4.737 | 6.013 | −2.597 | 0.0297744 | solute carrier family 37 (glycerol-3-phosphate transporter), member 3 |
| ATP6AP1 | 7.260 | 7.831 | 7.843 | 5.955 | 6.466 | 5.962 | −2.597 | 0.0067859 | ATPase, H+ transporting, lysosomal accessory protein 1 |
| TNPO2 | 6.912 | 8.536 | 7.232 | 5.977 | 5.856 | 5.606 | −2.595 | 0.0170860 | transportin 2 |
| RPL36 | 15.870 | 15.207 | 15.070 | 13.740 | 13.833 | 14.164 | −2.591 | 0.0091405 | ribosomal protein L36 |
| THAP1 | 2.247 | 3.799 | 2.348 | 0.974 | 0.974 | 0.974 | −2.591 | 0.0142556 | THAP domain containing, apoptosis associated protein 1 |
| RECQL5 | 9.296 | 9.275 | 8.466 | 7.779 | 7.702 | 7.924 | −2.589 | 0.0186301 | RecQ protein-like 5 |
| MAGI1 | 7.339 | 6.251 | 6.337 | 5.564 | 4.879 | 5.793 | −2.588 | 0.0426608 | membrane associated guanylate kinase, WW and PDZ domain containing 1 |
| HDAC10 | 7.716 | 6.560 | 8.016 | 5.898 | 6.645 | 5.413 | −2.587 | 0.0426992 | histone deacetylase 10 |
| ACSL3 | 6.935 | 6.505 | 5.683 | 4.326 | 5.301 | 5.135 | −2.585 | 0.0279916 | acyl-CoA synthetase long-chain family member 3 |
| CLDND1 | 8.068 | 9.012 | 8.194 | 6.123 | 7.108 | 7.643 | −2.582 | 0.0354612 | claudin domain containing 1 |
| FLJ35220 | 3.728 | 5.094 | 4.557 | 2.974 | 2.974 | 3.728 | −2.578 | 0.0474171 | No description |
| LGALS1 | 8.272 | 7.357 | 7.070 | 6.121 | 5.720 | 5.991 | −2.578 | 0.0117997 | lectin, galactoside-binding, soluble, 1 |
| DCAF8 | 6.777 | 7.264 | 6.563 | 4.274 | 5.416 | 6.174 | −2.568 | 0.0345042 | DDB1 and CUL4 associated factor 8 |

TABLE 5-continued

Differentially Expressed Genes in CD24+ Breast Epithelial Cells

| | Nulliparous (NP) Samples | | | Parous (P) Samples | | | | | | |
|---|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| CRYZL1 | 3.220 | 4.665 | 3.334 | 1.974 | 1.974 | 1.974 | −2.566 | 0.0134873 | crystallin, zeta (quinone reductase)-like 1 |
| ZNF12 | 5.954 | 6.242 | 5.318 | 4.168 | 3.962 | 5.087 | −2.560 | 0.0250115 | zinc finger protein 12 |
| SPTAN1 | 6.820 | 7.268 | 7.155 | 5.800 | 5.400 | 6.258 | −2.559 | 0.0161097 | spectrin, alpha, non-erythrocytic 1 (alpha-fodrin) |
| CIAO1 | 7.742 | 7.700 | 6.943 | 5.864 | 5.674 | 6.387 | −2.559 | 0.0126930 | cytosolic iron-sulfur protein assembly 1 |
| CCDC106 | 3.593 | 5.309 | 5.167 | 2.860 | 2.377 | 3.954 | −2.558 | 0.0496447 | coiled-coil domain containing 106 |
| NRAS | 6.667 | 8.772 | 6.811 | 6.339 | 5.386 | 5.456 | −2.558 | 0.0471957 | neuroblastoma RAS viral (v-ras) oncogene homolog |
| RHOG | 8.266 | 8.767 | 8.172 | 6.817 | 7.413 | 7.136 | −2.557 | 0.0128327 | ras homolog gene family, member G (rho G) |
| GSTP1 | 10.005 | 11.863 | 10.764 | 9.412 | 9.486 | 9.061 | −2.553 | 0.0312663 | glutathione S-transferase pi 1 |
| HNRNPUL1 | 6.793 | 6.829 | 5.740 | 4.681 | 5.479 | 4.860 | −2.549 | 0.0229432 | heterogeneous nuclear ribonucleoprotein U-like 1 |
| SF3B14 | 6.655 | 7.471 | 6.354 | 5.020 | 5.306 | 5.635 | −2.547 | 0.0151704 | No description |
| PFKL | 10.207 | 10.387 | 10.923 | 8.859 | 9.065 | 9.125 | −2.546 | 0.0057452 | phosphofructokinase, liver |
| ACTR10 | 5.197 | 4.844 | 4.601 | 3.396 | 3.496 | 3.659 | −2.545 | 0.0059187 | actin-related protein 10 homolog (S. cerevisiae) |
| BMPS | 4.946 | 4.354 | 3.745 | 3.404 | 2.627 | 3.007 | −2.544 | 0.0278089 | bone morphogenetic protein 3 |
| EEPD1 | 4.910 | 3.531 | 4.457 | 2.246 | 2.377 | 3.565 | −2.539 | 0.0344774 | endonuclease/exonuclease/phosphatase family domain containing 1 |
| RING1 | 9.981 | 9.558 | 9.333 | 7.989 | 8.611 | 8.586 | −2.538 | 0.0174566 | ring finger protein 1 |
| C17orf28 | 8.631 | 8.961 | 9.258 | 7.877 | 7.920 | 7.267 | −2.527 | 0.0157682 | chromosome 17 open reading frame 28 |
| MTMR14 | 4.991 | 4.882 | 3.896 | 2.559 | 3.802 | 3.496 | −2.525 | 0.0470660 | myotubularin related protein 14 |
| THBS3 | 7.106 | 6.222 | 8.087 | 5.977 | 5.506 | 5.770 | −2.524 | 0.0461972 | thrombospondin 3 |
| ZHX1 | 5.052 | 5.225 | 4.744 | 3.717 | 3.716 | 3.509 | −2.524 | 0.0044075 | zinc fingers and homeoboxes 1 |
| B9D2 | 4.042 | 4.091 | 3.962 | 3.697 | 2.627 | 2.695 | −2.522 | 0.0484528 | B9 protein domain 2 |
| RAB1 7 | 6.906 | 7.980 | 8.257 | 7.185 | 5.645 | 5.571 | −2.522 | 0.0456339 | RAB17, member RAS oncogene family |
| PSMC4 | 6.422 | 7.995 | 6.236 | 4.902 | 5.661 | 5.356 | −2.521 | 0.0360683 | proteasome (prosome, macropain) 26S subunit, ATPase, 4 |
| PABPC4 | 7.460 | 9.108 | 7.751 | 6.126 | 6.808 | 6.924 | −2.521 | 0.0382471 | poly(A) binding protein, cytoplasmic 4 (inducible form) |
| NDUFB3 | 2.247 | 2.404 | 3.021 | 0.974 | 1.692 | 0.974 | −2.513 | 0.0179279 | NADH dehydrogenase (ubiquinone) 1 beta subcomplex, 3, 12 kDa |
| ZDHHC7 | 9.309 | 9.784 | 9.435 | 8.039 | 8.456 | 8.054 | −2.511 | 0.0073615 | zinc finger, DHHC-type containing 7 |
| REST | 3.706 | 5.296 | 3.624 | 3.043 | 2.296 | 2.695 | −2.510 | 0.0375794 | RE1-silencing transcription factor |
| UQCR11 | 8.828 | 8.252 | 10.342 | 7.457 | 7.918 | 7.500 | −2.509 | 0.0473354 | ubiquinol-cytochrome c reductase, complex III subunit XI |
| C1orf210 | 5.286 | 4.583 | 4.397 | 2.943 | 3.960 | 3.789 | −2.506 | 0.0413937 | chromosome 1 open reading frame 210 |
| PPM1G | 9.649 | 10.197 | 10.745 | 8.872 | 8.930 | 8.633 | −2.505 | 0.0154589 | protein phosphatase, Mg2+/Mn2+ dependent, 1G |
| METTL12 | 4.282 | 3.304 | 3.727 | 2.404 | 2.402 | 2.878 | −2.502 | 0.0242625 | methyltransferase like 12 |
| CTR9 | 6.135 | 6.822 | 5.464 | 4.675 | 4.812 | 5.191 | −2.502 | 0.0368726 | Ctr9, Paf1/RNA polymerase II complex component, homolog (S. cerevisiae) |
| USP7 | 8.300 | 9.666 | 9.538 | 7.269 | 7.677 | 8.346 | −2.496 | 0.0411888 | ubiquitin specific peptidase 7 (herpes virus-associated) |
| TIMM50 | 6.938 | 8.432 | 6.958 | 5.692 | 6.173 | 5.620 | −2.494 | 0.0240967 | translocase of inner mitochondrial membrane 50 homolog (S. cerevisiae) |
| TMEM184A | 7.266 | 7.131 | 8.352 | 5.975 | 5.947 | 5.872 | −2.494 | 0.0114896 | transmembrane protein 184A |
| ECH1 | 6.207 | 6.046 | 5.455 | 4.138 | 4.665 | 5.036 | −2.491 | 0.0220092 | enoyl CoA hydratase 1, peroxisomal |
| CUL4B | 4.710 | 4.670 | 3.875 | 2.559 | 3.591 | 3.205 | −2.490 | 0.0295602 | cullin 4B |
| CYBA | 6.748 | 7.527 | 7.916 | 6.211 | 6.551 | 5.829 | −2.490 | 0.0380437 | cytochrome b-245, alpha polypeptide |
| MAPK7 | 6.424 | 6.563 | 6.632 | 5.248 | 5.421 | 4.334 | −2.489 | 0.0115004 | mitogen-activated protein kinase 7 |
| ARHGEF5 | 8.593 | 8.717 | 9.838 | 7.282 | 7.482 | 8.301 | −2.482 | 0.0398296 | Rho guanine nucleotide exchange factor (GEF) 5 |
| PSMA6 | 8.072 | 9.248 | 7.884 | 6.572 | 6.866 | 6.873 | −2.482 | 0.0155756 | proteasome (prosome, macropain) subunit, alpha type, 6 |
| JOSD1 | 8.536 | 8.146 | 8.624 | 6.836 | 6.848 | 7.315 | −2.480 | 0.0059877 | Josephin domain containing 1 |
| C20orf54 | 3.496 | 4.914 | 4.513 | 2.559 | 3.204 | 3.205 | −2.478 | 0.0388120 | chromosome 20 open reading frame 54 |
| SCYL1 | 10.074 | 9.956 | 11.773 | 8.765 | 9.352 | 8.764 | −2.477 | 0.0339547 | SCY1-like1 (S. cerevisiae) |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| AUH | 4.028 | 3.711 | 3.754 | 2.848 | 2.402 | 2.404 | −2.477 | 0.0072026 | AU RNA binding protein/enoyl-CoA hydratase |
| UPF3A | 6.071 | 6.524 | 5.508 | 5.226 | 5.069 | 4.050 | −2.459 | 0.0454927 | UPF3 regulator of nonsense transcripts homolog A (yeast) |
| SENP3 | 4.964 | 5.732 | 6.140 | 4.402 | 4.436 | 4.716 | −2.456 | 0.0415695 | SUMO1/sentrin/SMT3 specific peptidase 3 |
| SAFE | 5.346 | 6.105 | 5.178 | 4.050 | 3.914 | 4.367 | −2.456 | 0.0127598 | scaffold attachment factor B |
| MYBBP1A | 6.075 | 7.773 | 6.967 | 4.992 | 5.675 | 5.722 | −2.449 | 0.0362164 | MYB binding protein (P160) 1a |
| FAM102A | 10.571 | 11.703 | 10.134 | 9.475 | 8.908 | 9.280 | −2.446 | 0.0228496 | family with sequence similarity 102, member A |
| LRP5 | 5.601 | 5.952 | 5.534 | 4.009 | 4.662 | 4.538 | −2.445 | 0.0111320 | low density lipoprotein receptor-related protein 5 |
| TMEM9 | 5.167 | 5.157 | 3.984 | 3.880 | 3.519 | 2.782 | −2.440 | 0.0391097 | transmembrane protein 9 |
| MAP1B | 8.121 | 9.302 | 8.359 | 7.654 | 7.659 | 6.836 | −2.437 | 0.0461005 | microtubule-associated protein 1B |
| EPB41L5 | 3.412 | 4.873 | 4.258 | 2.974 | 2.974 | 2.974 | −2.435 | 0.0413292 | erythrocyte membrane protein band 4.1 like 5 |
| CENPT | 9.137 | 9.940 | 10.105 | 8.658 | 8.644 | 8.716 | −2.431 | 0.0342540 | centromere protein T |
| SMAD3 | 9.248 | 10.481 | 10.007 | 8.193 | 8.726 | 8.736 | −2.429 | 0.0245012 | SMAD family member 3 |
| FLJ23867 | 5.697 | 6.270 | 5.774 | 4.991 | 4.607 | 4.396 | −2.426 | 0.0136884 | No description |
| ARSJ | 4.763 | 5.469 | 5.711 | 3.692 | 4.191 | 4.322 | −2.424 | 0.0243477 | arylsulfatase family, member J |
| THOC4 | 3.954 | 3.927 | 3.838 | 2.649 | 3.290 | 2.457 | −2.424 | 0.0213753 | THO complex 4 |
| PICK1 | 7.718 | 7.667 | 8.669 | 6.390 | 6.640 | 6.899 | −2.423 | 0.0187245 | protein interacting with PRKCA 1 |
| MLST8 | 4.821 | 5.572 | 6.014 | 4.570 | 4.276 | 4.298 | −2.419 | 0.0427183 | MTOR associated protein, LST8 homolog (S. cerevisiae) |
| ZNF703 | 6.128 | 5.809 | 6.760 | 5.486 | 5.175 | 3.859 | −2.418 | 0.0485065 | zinc finger protein 703 |
| HSD17B3 | 2.247 | 2.247 | 2.878 | 0.974 | 0.974 | 0.974 | −2.416 | 0.0049471 | hydroxysteroid (17-beta) dehydrogenases |
| MOSC1 | 2.247 | 2.072 | 2.878 | 0.974 | 0.974 | 0.974 | −2.416 | 0.0082840 | MOCO sulphurase C-terminal domain containing 1 |
| C14orf93 | 2.247 | 1.692 | 2.377 | 0.974 | 0.974 | 0.974 | −2.416 | 0.0146416 | chromosome 14 open reading frame 93 |
| CMPK2 | 3.470 | 4.513 | 4.133 | 2.826 | 3.240 | 2.650 | −2.416 | 0.0357659 | cytidine monophosphate (UMP-CMP) kinase 2, mitochondrial |
| C18orf26 | 3.671 | 4.246 | 3.440 | 2.933 | 2.402 | 2.348 | −2.410 | 0.0206646 | chromosome 18 open reading frame 26 |
| TCEB2 | 7.255 | 7.721 | 8.397 | 6.557 | 6.188 | 6.453 | −2.408 | 0.0171596 | transcription elongation factor B (SIII), polypeptide 2 (18 kDa, elongin B) |
| OSGEP | 3.793 | 4.454 | 4.202 | 3.187 | 1.559 | 2.970 | −2.408 | 0.0287736 | O-sialoglycoprotein endopeptidase |
| DOPEY2 | 7.426 | 8.448 | 6.813 | 5.777 | 6.231 | 6.159 | −2.408 | 0.0273507 | dopey family member 2 |
| SIGIRR | 6.707 | 8.282 | 7.555 | 6.246 | 6.290 | 6.353 | −2.404 | 0.0465733 | single immunoglobulin and toll-interleukin 1 receptor (TIR) domain |
| CSNK1G2 | 6.022 | 6.452 | 6.196 | 4.883 | 4.760 | 5.531 | −2.399 | 0.0199378 | casein kinase 1, gamma 2 |
| VSIG2 | 4.282 | 6.519 | 5.020 | 3.772 | 3.758 | 3.304 | −2.398 | 0.0395549 | V-set and immunoglobulin domain containing 2 |
| MPPED2 | 3.954 | 3.263 | 2.860 | 1.974 | 2.692 | 1.974 | −2.398 | 0.0437429 | metallophosphoesterase domain containing 2 |
| SLC25A14 | 3.593 | 3.236 | 2.860 | 1.974 | 1.974 | 1.974 | −2.397 | 0.0101688 | solute carrier family 25 (mitochondrial carrier, brain), member 14 |
| SPEN | 8.647 | 8.940 | 8.595 | 7.069 | 7.386 | 8.095 | −2.396 | 0.0238012 | spen homolog, transcriptional regulator (Drosophila) |
| RBM14 | 5.599 | 6.718 | 6.787 | 4.960 | 4.893 | 5.527 | −2.394 | 0.0395695 | RNA binding motif protein 14 |
| TSC22D4 | 6.547 | 7.618 | 7.184 | 6.359 | 5.177 | 5.971 | −2.394 | 0.0413484 | TSC22 domain family, member 4 |
| MAP2K2 | 9.747 | 10.354 | 10.123 | 8.864 | 9.157 | 8.470 | −2.393 | 0.0153553 | mitogen-activated protein kinase kinase 2 |
| FAM63B | 4.931 | 5.419 | 5.463 | 4.402 | 3.711 | 3.672 | −2.393 | 0.0139478 | family with sequence similarity 63, member B |
| FBXO34 | 4.607 | 5.059 | 4.638 | 3.598 | 3.598 | 3.351 | −2.388 | 0.0071274 | F-box protein 34 |
| TMEM66 | 7.487 | 6.233 | 5.676 | 4.421 | 5.064 | 5.346 | −2.387 | 0.0405833 | transmembrane protein 66 |
| AIMP1 | 7.081 | 7.555 | 6.963 | 5.364 | 6.015 | 6.301 | −2.386 | 0.0193822 | aminoacyl tRNA synthetase complex-interacting multifunctional protein 1 |
| ANKRD30A | 3.814 | 5.929 | 3.788 | 2.559 | 2.559 | 2.559 | −2.386 | 0.0258619 | ankyrin repeat domain 30A |
| CASP6 | 4.125 | 4.588 | 4.296 | 3.334 | 3.334 | 2.457 | −2.384 | 0.0189923 | caspase 6, apoptosis-related cysteine peptidase |
| EHBP1L1 | 5.944 | 6.905 | 6.793 | 5.655 | 5.279 | 5.157 | −2.378 | 0.0284328 | EH domain binding protein 1-like 1 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| DDR1 | 10.892 | 12.182 | 10.870 | 9.620 | 9.748 | 10.104 | −2.378 | 0.0234942 | discoidin domain receptor tyrosine kinase 1 |
| DVL1 | 6.559 | 5.928 | 6.802 | 4.760 | 5.171 | 5.553 | −2.378 | 0.0233500 | dishevelled, dsh homolog 1 (Drosophila) |
| FXYD3 | 11.426 | 11.190 | 11.624 | 10.375 | 10.056 | 10.160 | −2.377 | 0.0072510 | FXYD domain containing ion transport regulator 3 |
| HDAC11 | 4.687 | 4.859 | 4.452 | 4.026 | 3.204 | 3.205 | −2.376 | 0.0221903 | histone deacetylase 11 |
| PPIA | 8.404 | 7.762 | 7.490 | 6.855 | 6.398 | 6.514 | −2.374 | 0.0168281 | peptidylprolyl isomerase A (cyclophilin A) |
| FAH | 4.290 | 5.290 | 3.820 | 3.043 | 2.896 | 3.043 | −2.373 | 0.0222011 | fumarylacetoacetate hydrolase (fumarylacetoacetase) |
| BTBD1 | 5.035 | 6.053 | 5.238 | 4.190 | 4.629 | 3.789 | −2.371 | 0.0330445 | BTB (POZ) domain containing 1 |
| RASSF3 | 2.747 | 4.038 | 3.220 | 1.974 | 1.974 | 1.974 | −2.371 | 0.0215480 | Ras association (RalGDS/AF-6) domain family member 3 |
| SCPEP1 | 3.220 | 3.618 | 2.673 | 2.246 | 1.974 | 1.974 | −2.371 | 0.0267636 | serine carboxypeptidase 1 |
| GPLD1 | 3.220 | 4.164 | 2.905 | 2.649 | 1.974 | 1.974 | −2.371 | 0.0418473 | glycosylphosphatidylinositol specific phospholipase D1 |
| SPAG16 | 6.644 | 5.947 | 6.074 | 5.127 | 4.997 | 4.705 | −2.366 | 0.0125157 | sperm associated antigen 16 |
| PSMD2 | 8.407 | 9.623 | 9.243 | 8.113 | 8.001 | 7.792 | −2.365 | 0.0406516 | proteasome (prosome, macropain) 26S subunit, non-ATPase, 2 |
| STK32C | 5.206 | 6.097 | 6.796 | 4.486 | 4.866 | 4.856 | −2.364 | 0.0415464 | serine/threonine kinase 32C |
| NDUFV2 | 7.599 | 9.346 | 7.297 | 6.359 | 6.339 | 6.437 | −2.361 | 0.0323538 | NADH dehydrogenase (ubiquinone) flavoprotein 2, 24 kDa |
| XPOT | 6.278 | 6.854 | 6.319 | 5.443 | 5.615 | 4.859 | −2.361 | 0.0223377 | exportin, tRNA (nuclear export receptor for tRNAs) |
| MPHOSPH8 | 6.559 | 7.454 | 7.588 | 6.241 | 5.805 | 6.215 | −2.360 | 0.0380330 | M-phase phosphoprotein 8 |
| COQ4 | 8.170 | 8.854 | 8.934 | 7.138 | 7.696 | 7.607 | −2.359 | 0.0231343 | coenzyme Q4 homolog (S. cerevisiae) |
| WAPAL | 5.291 | 6.298 | 5.749 | 3.886 | 4.512 | 5.136 | −2.358 | 0.0422686 | wings apart-like homolog (Drosophila) |
| AKAP8L | 7.745 | 8.796 | 8.579 | 7.232 | 7.560 | 7.269 | −2.356 | 0.0466163 | A kinase (PRKA) anchor protein 8-like |
| LMX1B | 5.390 | 6.272 | 6.011 | 4.931 | 5.037 | 4.148 | −2.355 | 0.0363515 | LIM homeobox transcription factor 1, beta |
| CDK17 | 4.719 | 4.843 | 4.664 | 3.484 | 3.337 | 4.351 | −2.354 | 0.0429586 | cyclin-dependent kinase 17 |
| DTWD1 | 3.220 | 3.692 | 2.819 | 1.974 | 1.974 | 2.457 | −2.353 | 0.0285441 | DTW domain containing 1 |
| GAK | 9.884 | 10.314 | 10.592 | 8.700 | 9.358 | 9.077 | −2.351 | 0.0182049 | cyclin G associated kinase |
| DECR1 | 6.508 | 6.860 | 6.032 | 5.627 | 5.296 | 4.630 | −2.350 | 0.0268012 | 2,4-dienoyl CoA reductase 1, mitochondrial |
| BLOC1S3 | 4.597 | 5.059 | 4.450 | 3.583 | 3.712 | 3.220 | −2.346 | 0.0143952 | biogenesis of lysosomal organelles complex-1, subunit 3 |
| TP53 | 5.217 | 6.596 | 5.227 | 3.989 | 4.334 | 4.403 | −2.342 | 0.0291051 | tumor protein p53 |
| COX4NB | 6.973 | 7.383 | 7.478 | 6.046 | 6.217 | 6.156 | −2.340 | 0.0098381 | COX4 neighbor |
| CD3EAP | 5.696 | 6.551 | 6.855 | 4.729 | 5.411 | 5.325 | −2.338 | 0.0379816 | CD3e molecule, epsilon associated protein |
| F11R | 8.340 | 8.240 | 7.301 | 7.117 | 6.288 | 6.967 | −2.334 | 0.0446569 | F11 receptor |
| RRAGC | 8.238 | 7.965 | 7.857 | 6.742 | 6.407 | 7.016 | −2.334 | 0.0088757 | Ras-related GTP binding C |
| LYPLAL1 | 3.220 | 3.196 | 2.347 | 1.974 | 1.974 | 1.974 | −2.332 | 0.0452034 | lysophospholipase-like 1 |
| MAP2K4 | 5.454 | 5.334 | 5.091 | 3.872 | 4.144 | 4.230 | −2.328 | 0.0070407 | mitogen-activated protein kinase kinase 4 |
| CYTSA | 7.323 | 8.109 | 7.978 | 6.697 | 6.890 | 6.355 | −2.327 | 0.0230276 | No description |
| LATS2 | 7.418 | 7.512 | 6.490 | 5.271 | 5.958 | 6.469 | −2.326 | 0.0479048 | LATS, large tumor suppressor, homolog 2 (Drosophila) |
| NR3C2 | 4.554 | 4.882 | 4.042 | 3.271 | 3.337 | 3.605 | −2.324 | 0.0243991 | nuclear receptor subfamily 3, group C, member 2 |
| CEBPG | 6.168 | 6.652 | 5.929 | 4.791 | 5.048 | 4.952 | −2.323 | 0.0093638 | CCAAT/enhancer binding protein (C/EBP), gamma |
| HDAC2 | 6.617 | 6.264 | 6.523 | 4.879 | 5.308 | 5.519 | −2.322 | 0.0112149 | histone deacetylase 2 |
| RDH13 | 6.043 | 5.378 | 5.687 | 3.992 | 4.651 | 4.828 | −2.321 | 0.0232870 | retinol dehydrogenase 13 (all-trans/9-cis) |
| PLAT | 6.802 | 8.373 | 7.601 | 6.550 | 6.388 | 5.667 | −2.318 | 0.0409831 | plasminogen activator, tissue |
| C11orf60 | 4.126 | 4.255 | 3.222 | 3.043 | 2.559 | 2.559 | −2.317 | 0.0364935 | No description |
| RAD54L2 | 5.765 | 6.940 | 6.246 | 5.038 | 5.044 | 4.925 | −2.310 | 0.0202341 | RAD54-like 2 (S. cerevisiae) |
| MED22 | 5.291 | 6.089 | 6.055 | 4.121 | 4.881 | 4.520 | −2.310 | 0.0205756 | mediator complex subunit 22 |
| ZBTB8A | 10.008 | 9.432 | 9.509 | 7.928 | 8.303 | 8.903 | −2.306 | 0.0218135 | zinc finger and BTB domain containing 8A |
| PDRG1 | 5.410 | 5.624 | 5.556 | 3.583 | 4.353 | 4.806 | −2.302 | 0.0245518 | p53 and DNA-damage regulated 1 |
| C12orf45 | 6.630 | 5.874 | 6.696 | 3.855 | 5.494 | 5.447 | −2.300 | 0.0454582 | chromosome 12 open reading frame 45 |
| EID1 | 6.602 | 6.100 | 5.882 | 4.795 | 4.927 | 4.899 | −2.299 | 0.0088051 | EP300 interacting inhibitor of differentiation 1 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| PRKCD | 7.948 | 7.425 | 7.446 | 5.013 | 6.247 | 7.008 | −2.296 | 0.0417183 | protein kinase C, delta |
| RBM42 | 6.241 | 6.286 | 5.924 | 3.913 | 5.567 | 5.042 | −2.296 | 0.0447429 | RNA binding motif protein 42 |
| ALDH5A1 | 4.205 | 4.463 | 3.979 | 2.943 | 2.782 | 3.351 | −2.293 | 0.0131481 | aldehyde dehydrogenase 5 family, member A1 |
| KRTAP1-1 | 1.913 | 1.688 | 1.169 | 0.845 | −0.026 | −0.026 | −2.288 | 0.0220990 | keratin associated protein 1-1 |
| ARRB2 | 5.244 | 5.676 | 6.414 | 4.550 | 4.431 | 4.482 | −2.288 | 0.0215917 | arrestin, beta 2 |
| ZNHIT2 | 4.662 | 4.952 | 4.649 | 3.772 | 0.974 | 3.469 | −2.286 | 0.0411435 | zinc finger, HIT-type containing 2 |
| SLU7 | 6.704 | 7.339 | 6.671 | 5.479 | 5.877 | 5.630 | −2.285 | 0.0136101 | SLU7 splicing factor homolog (*S. cerevisiae*) |
| E2F1 | 3.470 | 3.613 | 3.841 | 1.911 | 2.648 | 2.650 | −2.284 | 0.0158112 | E2F transcription factor 1 |
| TSC2 | 6.930 | 7.776 | 7.574 | 6.398 | 6.383 | 6.284 | −2.283 | 0.0245411 | tuberous sclerosis 2 |
| ORMDL2 | 6.148 | 7.132 | 7.262 | 5.145 | 6.072 | 5.214 | −2.282 | 0.0323431 | ORM1-like 2 (*S. cerevisiae*) |
| EEF2 | 14.955 | 16.172 | 15.875 | 14.191 | 14.685 | 14.777 | −2.281 | 0.0498012 | eukaryotic translation elongation factor 2 |
| FGF13 | 4.192 | 3.436 | 3.786 | 2.246 | 3.196 | 2.457 | −2.281 | 0.0336769 | fibroblast growth factor 13 |
| ATP6V0E2 | 6.128 | 6.568 | 6.692 | 5.950 | 4.623 | 5.379 | −2.279 | 0.0485173 | ATPase, H+ transporting V0 subunit e2 |
| AR | 3.706 | 4.854 | 3.468 | 2.518 | 2.296 | 2.695 | −2.278 | 0.0211719 | androgen receptor |
| DHX29 | 4.473 | 4.672 | 4.091 | 3.246 | 2.974 | 3.484 | −2.278 | 0.0142341 | DEAH (Asp-Glu-Ala-His) box polypeptide 29 |
| C1orf126 | 5.489 | 5.912 | 4.969 | 4.534 | 4.279 | 4.302 | −2.277 | 0.0280384 | chromosome 1 open reading frame 126 |
| CFL1 | 12.836 | 13.123 | 12.737 | 11.649 | 12.373 | 11.452 | −2.277 | 0.0326408 | cofilin 1 (non-muscle) |
| SVOPL | 2.878 | 2.108 | 2.404 | 0.974 | 1.692 | 0.974 | −2.276 | 0.0221305 | SVOP-like |
| PLD2 | 5.972 | 6.416 | 6.555 | 5.157 | 4.787 | 5.459 | −2.273 | 0.0180399 | phospholipase D2 |
| FAM174A | 6.630 | 7.017 | 7.809 | 6.324 | 6.023 | 5.447 | −2.270 | 0.0414213 | family with sequence similarity 174, member A |
| NKRF | 4.678 | 4.944 | 4.196 | 3.802 | 2.840 | 3.496 | −2.269 | 0.0281213 | NFKB repressing factor |
| HMG20B | 8.123 | 8.161 | 7.901 | 6.942 | 6.491 | 7.373 | −2.266 | 0.0219985 | high-mobility group 20B |
| PEX1 | 4.664 | 5.323 | 4.793 | 3.809 | 3.934 | 3.484 | −2.266 | 0.0155863 | peroxisomal biogenesis factor 1 |
| SLC17A5 | 4.664 | 5.739 | 4.305 | 3.462 | 3.638 | 3.484 | −2.266 | 0.0279808 | solute carrier family 17 (anion/sugar transporter), member 5 |
| PPEF2 | 3.966 | 3.288 | 3.826 | 2.108 | 2.636 | 3.152 | −2.265 | 0.0475088 | protein phosphatase, EF-hand calcium binding domain 2 |
| RPL17 | 14.350 | 15.321 | 14.899 | 13.721 | 13.721 | 13.978 | −2.262 | 0.0333484 | ribosomal protein L17 |
| EBPL | 3.953 | 2.869 | 2.878 | 1.845 | 1.692 | 1.819 | −2.261 | 0.0159325 | emopamil binding protein-like |
| ROBOS | 6.773 | 7.015 | 7.611 | 5.600 | 6.106 | 6.437 | −2.256 | 0.0402809 | roundabout, axon guidance receptor, homolog 3 (*Drosophila*) |
| FANK1 | 3.597 | 4.283 | 4.033 | 2.860 | 3.196 | 1.974 | −2.255 | 0.0315979 | fibronectin type III and ankyrin repeat domains 1 |
| ZER1 | 8.113 | 8.619 | 9.010 | 7.447 | 7.595 | 7.110 | −2.253 | 0.0213070 | zer-1 homolog (C. elegans) |
| CHD2 | 11.739 | 11.416 | 11.378 | 9.707 | 10.247 | 10.975 | −2.248 | 0.0349870 | chromodomain helicase DNA binding protein 2 |
| ZSWIM4 | 5.930 | 6.149 | 5.368 | 4.404 | 4.612 | 4.980 | −2.248 | 0.0231059 | zinc finger, SWIM-type containing 4 |
| ARHGAP30 | 6.223 | 5.928 | 5.532 | 4.416 | 5.055 | 4.684 | −2.246 | 0.0196999 | Rho GTPase activating protein 30 |
| SLC38A10 | 5.846 | 6.796 | 6.167 | 5.511 | 5.001 | 4.851 | −2.244 | 0.0325641 | solute carrier family 38, member 10 |
| ENO1 | 10.548 | 11.155 | 10.574 | 9.854 | 9.957 | 9.385 | −2.240 | 0.0300522 | enolase 1, (alpha) |
| TCTN3 | 5.222 | 6.195 | 5.661 | 4.183 | 5.182 | 4.059 | −2.239 | 0.0460115 | tectonic family members |
| NCBP2 | 4.631 | 5.837 | 4.956 | 3.469 | 3.831 | 4.445 | −2.238 | 0.0462648 | nuclear cap binding protein subunit 2, 20 kDa |
| SND1 | 9.312 | 9.888 | 9.900 | 8.530 | 8.737 | 8.619 | −2.238 | 0.0168557 | staphylococcal nuclease and tudor domain containing 1 |
| SMG1 | 7.506 | 7.127 | 6.360 | 5.604 | 5.495 | 6.344 | −2.237 | 0.0455035 | SMG1 homolog, phosphatidylinositol 3-kinase-related kinase (C. elegans) |
| IPO5 | 8.368 | 7.632 | 7.318 | 6.373 | 6.471 | 6.837 | −2.236 | 0.0265948 | importin 5 |
| ADIPOR1 | 7.922 | 8.223 | 7.462 | 6.302 | 6.871 | 6.783 | −2.235 | 0.0185518 | adiponectin receptor 1 |
| MCL1 | 11.032 | 10.699 | 10.271 | 9.111 | 9.379 | 10.099 | −2.235 | 0.0383768 | myeloid cell leukemia sequence 1 (BCL2-related) |
| SH3GLB2 | 9.492 | 10.108 | 9.986 | 8.848 | 8.480 | 8.827 | −2.232 | 0.0154198 | SH3-domain GRB2-like endophilin B2 |
| C11orf66 | 3.954 | 4.492 | 5.386 | 3.334 | 3.334 | 2.860 | −2.231 | 0.0256040 | chromosome 11 open reading frame 66 |
| DHRS13 | 6.389 | 5.167 | 5.380 | 4.222 | 4.448 | 4.098 | −2.231 | 0.0215050 | dehydrogenase/reductase (SDR family) member 13 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| TINF2 | 3.709 | 4.575 | 3.674 | 2.518 | 2.627 | 2.695 | −2.229 | 0.0134574 | TERF1 (TRF1-interacting nuclear factor 2 |
| TNIP2 | 4.360 | 5.296 | 4.462 | 4.050 | 3.204 | 3.496 | −2.229 | 0.0438665 | TNFAIP3 interacting protein 2 |
| TTLL3 | 7.969 | 7.784 | 7.979 | 5.945 | 6.823 | 6.815 | −2.228 | 0.0130307 | tubulin tyrosine ligase-like family, member 3 |
| RIF1 | 5.396 | 6.295 | 5.221 | 4.066 | 4.537 | 4.302 | −2.228 | 0.0209877 | RAP1 interacting factor homolog (yeast) |
| SNRNP200 | 7.973 | 7.618 | 7.604 | 6.216 | 6.463 | 7.010 | −2.227 | 0.0190200 | small nuclear ribonucleoprotein 200 kDa (U5) |
| ING3 | 4.363 | 5.237 | 5.640 | 4.102 | 3.234 | 4.083 | −2.225 | 0.0435073 | inhibitor of growth family, member 3 |
| ATP5D | 9.246 | 10.106 | 10.075 | 8.988 | 8.846 | 8.092 | −2.225 | 0.0404712 | ATP synthase, H+ transporting, mitochondrial F1 complex, delta subunit |
| ATP1A1 | 10.473 | 11.507 | 10.011 | 9.321 | 8.952 | 9.783 | −2.222 | 0.0448511 | ATPase, Na+/K+ transporting, alpha 1 polypeptide |
| GMPPA | 6.610 | 5.957 | 7.468 | 5.727 | 5.556 | 4.806 | −2.220 | 0.0477521 | GDP-mannose pyrophosphorylase A |
| ACTN4 | 11.569 | 12.037 | 11.960 | 10.493 | 10.890 | 10.419 | −2.219 | 0.0096616 | actinin, alpha 4 |
| RBMX | 3.059 | 2.037 | 3.032 | 1.911 | 1.559 | 1.559 | −2.216 | 0.0493822 | RNA binding motif protein, X-linked |
| SNRPB | 11.046 | 12.159 | 11.143 | 9.898 | 10.032 | 10.426 | −2.215 | 0.0250837 | small nuclear ribonucleoprotein polypeptides B and B1 |
| VPS41 | 5.817 | 4.819 | 5.323 | 3.949 | 3.900 | 4.670 | −2.215 | 0.0397107 | vacuolar protein sorting 41 homolog (S. cerevisiae) |
| IRS1 | 5.418 | 5.276 | 5.408 | 4.271 | 4.244 | 4.144 | −2.215 | 0.0031005 | insulin receptor substrate 1 |
| ZNF124 | 3.059 | 2.948 | 2.703 | 1.559 | 2.075 | 1.559 | −2.209 | 0.0122180 | zinc finger protein 124 |
| FAF2 | 5.185 | 5.414 | 4.459 | 4.271 | 4.004 | 3.629 | −2.208 | 0.0435541 | Fas associated factor family member 2 |
| UQCRH | 11.100 | 11.143 | 10.638 | 9.790 | 9.634 | 10.000 | −2.207 | 0.0121965 | ubiquinol-cytochrome c reductase hinge protein |
| PYGB | 9.135 | 9.129 | 8.535 | 7.881 | 7.929 | 7.992 | −2.207 | 0.0213323 | phosphorylase, glycogen; brain |
| NAA25 | 8.010 | 7.421 | 7.505 | 6.282 | 6.655 | 6.781 | −2.202 | 0.0213484 | N(alpha)-acetyltransferase 25, NatB auxiliary subunit |
| PCBP1 | 8.278 | 7.400 | 6.702 | 5.876 | 6.274 | 6.262 | −2.199 | 0.0385602 | poly(rC) binding protein 1 |
| RASL10A | 6.177 | 4.810 | 6.118 | 3.809 | 3.817 | 5.041 | −2.198 | 0.0453392 | RAS-like, family 10, member A |
| ZNF625 | 4.851 | 5.416 | 5.070 | 3.767 | 4.282 | 3.859 | −2.195 | 0.0160123 | zinc finger protein 625 |
| MIDN | 10.614 | 10.965 | 10.756 | 9.623 | 9.321 | 10.073 | −2.194 | 0.0197421 | midnolin |
| OR2H1 | 2.878 | 2.108 | 1.692 | 0.974 | 0.974 | 0.974 | −2.193 | 0.0246654 | olfactory receptor, family 2, subfamily H, member 1 |
| LRRC29 | 2.247 | 1.505 | 2.108 | 0.974 | 0.974 | 0.974 | −2.193 | 0.0276577 | leucine rich repeat containing 29 |
| DUSP15 | 2.247 | 2.878 | 2.108 | 0.974 | 0.974 | 1.819 | −2.193 | 0.0366086 | dual specificity phosphatase 15 |
| HBXIP | 8.837 | 8.856 | 8.115 | 6.983 | 7.755 | 7.649 | −2.193 | 0.0334658 | hepatitis B virus x interacting protein |
| PXN | 6.730 | 6.252 | 6.159 | 5.015 | 5.378 | 5.601 | −2.189 | 0.0244206 | paxillin |
| PSMD8 | 8.274 | 9.281 | 8.620 | 7.543 | 7.364 | 7.492 | −2.187 | 0.0182893 | proteasome (prosome, macropain) 26S subunit, non-ATPase, 8 |
| FLJ36031 | 3.814 | 4.332 | 3.746 | 2.559 | 2.840 | 3.205 | −2.183 | 0.0235741 | No description |
| ABCC8 | 3.908 | 3.979 | 4.919 | 3.205 | 3.026 | 2.782 | −2.183 | 0.0237744 | ATP-binding cassette, sub-family C (CFTR/MRP), member 8 |
| VLDLR | 3.706 | 4.594 | 4.303 | 3.179 | 3.469 | 2.296 | −2.181 | 0.0428826 | very low density lipoprotein receptor |
| NOB1 | 4.741 | 4.953 | 5.408 | 3.943 | 4.062 | 3.616 | −2.180 | 0.0162333 | NIN1/RPN12 binding protein 1 homolog (S. cerevisiae) |
| LRRC8A | 9.392 | 9.528 | 9.904 | 8.407 | 8.030 | 8.894 | −2.175 | 0.0229701 | leucine rich repeat containing 8 family, member A |
| SLC39A6 | 6.383 | 7.667 | 6.534 | 5.391 | 5.415 | 5.887 | −2.171 | 0.0347913 | solute carrier family 39 (zinc transporter), member 6 |
| QRICH1 | 5.536 | 4.497 | 4.157 | 3.144 | 3.939 | 3.379 | −2.170 | 0.0478573 | glutamine-rich 1 |
| TOLLIP | 7.322 | 8.270 | 7.887 | 6.484 | 6.911 | 6.772 | −2.166 | 0.0295288 | toll interacting protein |
| URM1 | 4.687 | 5.386 | 4.915 | 3.837 | 3.802 | 3.787 | −2.164 | 0.0119693 | ubiquitin related modifier 1 |
| FTO | 6.178 | 5.649 | 5.498 | 5.065 | 4.516 | 4.489 | −2.163 | 0.0269348 | fat mass and obesity associated |
| THAP9 | 3.059 | 3.187 | 2.602 | 1.911 | 2.075 | 1.559 | −2.161 | 0.0191566 | THAP domain containing 9 |
| NQO1 | 5.435 | 5.943 | 5.382 | 4.577 | 4.836 | 4.165 | −2.154 | 0.0266577 | NAD(P)H dehydrogenase, quinone 1 |
| CTSB | 10.678 | 11.251 | 10.884 | 9.788 | 9.882 | 9.572 | −2.152 | 0.0105649 | cathepsin B |
| ATM | 5.090 | 5.219 | 4.842 | 3.992 | 3.638 | 4.115 | −2.149 | 0.0115879 | ataxia telangiectasia mutated |
| HSD11B1L | 5.410 | 5.201 | 5.753 | 4.457 | 4.098 | 4.378 | −2.148 | 0.0126654 | hydroxysteroid (11-beta) dehydrogenase 1-like |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| GGT5 | 4.770 | 5.325 | 5.748 | 4.527 | 4.222 | 3.704 | −2.147 | 0.0398020 | gamma-glutamyltransferase 5 |
| PSME1 | 9.531 | 9.260 | 8.584 | 8.159 | 8.161 | 8.241 | −2.142 | 0.0453607 | proteasome (prosoma, macropain) activator subunit 1 (PA28 alpha) |
| KCNMA1 | 6.408 | 6.950 | 6.912 | 5.814 | 5.968 | 5.013 | −2.140 | 0.0318181 | potassium large conductance calcium-activated channel, subfamily M, alpha member 1 |
| RPL26L1 | 5.514 | 5.850 | 5.584 | 3.966 | 5.041 | 4.486 | −2.140 | 0.0294712 | ribosomal protein L26-like 1 |
| KIAA0247 | 8.582 | 8.962 | 8.190 | 7.484 | 7.481 | 7.865 | −2.139 | 0.0350898 | KIAA0247 |
| MIF | 11.283 | 11.750 | 11.921 | 10.772 | 10.653 | 10.300 | −2.138 | 0.0211827 | macrophage migration inhibitory factor (glycosylation-inhibiting factor) |
| VCP | 8.109 | 8.753 | 9.094 | 7.884 | 7.657 | 7.249 | −2.138 | 0.0432517 | valosin-containing protein |
| RARA | 9.385 | 8.564 | 9.421 | 7.468 | 7.967 | 8.330 | −2.138 | 0.0331320 | retinoic acid receptor, alpha |
| TESK2 | 4.991 | 3.655 | 3.523 | 2.746 | 2.559 | 2.559 | −2.136 | 0.0290361 | testis-specific kinase 2 |
| CLIP1 | 7.184 | 6.979 | 6.201 | 5.459 | 5.898 | 5.886 | −2.134 | 0.0426416 | CAP-GLY domain containing linker protein 1 |
| CDT1 | 3.389 | 3.043 | 3.524 | 2.296 | 2.296 | 2.296 | −2.133 | 0.0125756 | chromatin licensing and DNA replication factor 1 |
| TMEM38A | 2.519 | 3.032 | 2.650 | 1.559 | 1.559 | 1.559 | −2.129 | 0.0083530 | transmembrane protein 38A |
| ZDHHC8P | 2.519 | 2.650 | 3.032 | 1.559 | 1.559 | 1.559 | −2.129 | 0.0083530 | No description |
| TTC18 | 3.059 | 3.059 | 2.650 | 1.559 | 2.075 | 1.559 | −2.129 | 0.0130952 | tetratricopeptide repeat domain 18 |
| ZNF506 | 3.059 | 2.650 | 2.802 | 1.559 | 2.075 | 1.559 | −2.129 | 0.0157575 | zinc finger protein 506 |
| DALRD3 | 7.792 | 8.755 | 7.553 | 6.704 | 6.524 | 6.855 | −2.127 | 0.0230829 | DALR anticodon binding domain containing 3 |
| GLIPR1 | 9.871 | 9.773 | 10.020 | 7.964 | 8.782 | 9.002 | −2.126 | 0.0185349 | GLI pathogenesis-related 1 |
| WDR13 | 8.029 | 8.218 | 8.639 | 6.989 | 7.132 | 7.352 | −2.123 | 0.0142809 | WD repeat domain 13 |
| PRAGMIN | 5.772 | 6.827 | 5.877 | 5.082 | 4.687 | 4.954 | −2.121 | 0.0258028 | No description |
| INTS1 | 8.956 | 8.769 | 9.699 | 7.686 | 8.486 | 7.878 | −2.118 | 0.0406132 | integrator complex subunit 1 |
| BMP7 | 8.048 | 7.381 | 8.232 | 7.054 | 6.588 | 6.967 | −2.116 | 0.0374359 | bone morphogenetic protein 7 |
| RAB15 | 6.625 | 7.025 | 7.051 | 5.544 | 5.653 | 6.034 | −2.115 | 0.0129233 | RAB15, member RAS oncogene family |
| CPEB1 | 2.671 | 3.188 | 4.208 | 2.108 | 2.105 | 2.108 | −2.115 | 0.0419325 | cytoplasmic polyadenylation element binding protein 1 |
| CCDC142 | 4.870 | 3.824 | 3.507 | 2.746 | 2.559 | 2.899 | −2.110 | 0.0297383 | coiled-coil domain containing 142 |
| CHRNB1 | 4.481 | 4.951 | 4.886 | 3.936 | 2.896 | 3.809 | −2.109 | 0.0282962 | cholinergic receptor, nicotinic, beta 1 (muscle) |
| UBA1 | 9.070 | 8.731 | 9.508 | 7.996 | 7.869 | 8.312 | −2.106 | 0.0275633 | ubiquitin-like modifier activating enzyme 1 |
| DYNC1LI2 | 9.782 | 10.109 | 9.411 | 8.906 | 8.524 | 8.711 | −2.101 | 0.0216025 | dynein, cytoplasmic 1, light intermediate chain 2 |
| CA13 | 6.138 | 6.163 | 5.996 | 4.866 | 5.068 | 5.558 | −2.100 | 0.0290760 | carbonic anhydrase XIII |
| C10orf57 | 3.364 | 3.468 | 3.043 | 2.296 | 2.296 | 2.296 | −2.097 | 0.0120038 | chromosome 10 open reading frame 57 |
| HOOK2 | 5.403 | 5.233 | 5.631 | 4.152 | 4.342 | 4.735 | −2.087 | 0.0211051 | hook homolog 2 (Drosophila) |
| LRSAM1 | 6.962 | 6.052 | 6.670 | 5.611 | 5.645 | 5.571 | −2.084 | 0.0397644 | leucine rich repeat and sterile alpha motif containing 1 |
| CCDC85C | 7.319 | 7.574 | 7.259 | 4.837 | 6.306 | 6.515 | −2.083 | 0.0332686 | coiled-coil domain containing 85C |
| MRPL55 | 8.397 | 8.148 | 9.120 | 7.220 | 7.753 | 7.339 | −2.082 | 0.0339939 | mitochondrial ribosomal protein L55 |
| PGAP2 | 5.659 | 4.686 | 4.555 | 3.821 | 3.594 | 3.629 | −2.080 | 0.0233776 | post-GPI attachment to proteins 2 |
| VAPA | 7.879 | 7.723 | 7.000 | 6.049 | 5.944 | 6.968 | −2.080 | 0.0405280 | VAMP (vesicle-associated membrane protein)-associated protein A, 33 kDa |
| ARL6IP4 | 7.447 | 8.245 | 7.471 | 6.712 | 6.392 | 6.454 | −2.078 | 0.0190975 | ADP-ribosylation-like factor 6 interacting protein 4 |
| TFE3 | 6.422 | 6.456 | 6.788 | 5.367 | 5.648 | 5.713 | −2.077 | 0.0163093 | transcription factor binding to IGHM enhancer 3 |
| NHS | 4.548 | 4.492 | 4.564 | 3.043 | 3.632 | 3.496 | −2.073 | 0.0111213 | Nance-Horan syndrome (congenital cataracts and dental anomalies) |
| FAM192A | 4.811 | 4.533 | 4.167 | 3.246 | 3.483 | 3.672 | −2.071 | 0.0219371 | family with sequence similarity 192, member A |
| TULP3 | 6.637 | 6.948 | 6.540 | 5.061 | 5.902 | 5.852 | −2.064 | 0.0289317 | tubby like protein 3 |
| PEX14 | 5.178 | 5.388 | 4.944 | 3.900 | 4.444 | 3.944 | −2.062 | 0.0184658 | peroxisomal biogenesis factor 14 |
| LRRC37B | 4.215 | 4.627 | 5.214 | 3.446 | 3.583 | 3.704 | −2.062 | 0.0285986 | leucine rich repeat containing 37B |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| LGALS8 | 6.581 | 6.274 | 6.530 | 5.414 | 5.537 | 5.251 | −2.061 | 0.0092686 | lectin, galactoside-binding, soluble, 8 |
| GAS2L1 | 5.799 | 6.180 | 5.909 | 4.866 | 4.347 | 5.460 | −2.061 | 0.0404436 | growth arrest-specific 2 like 1 |
| RELA | 9.484 | 9.155 | 8.633 | 8.076 | 7.943 | 8.443 | −2.057 | 0.0472433 | v-rel reticuloendotheliosis viral oncogene homolog A (avian) |
| ZNF117 | 4.428 | 4.269 | 3.820 | 3.462 | 3.026 | 2.782 | −2.054 | 0.0256922 | zinc finger protein 117 |
| C21orf49 | 6.387 | 6.175 | 6.406 | 5.351 | 5.462 | 4.857 | −2.051 | 0.0150806 | chromosome 21 open reading frame 49 |
| ITPR2 | 7.138 | 7.705 | 7.379 | 6.961 | 6.103 | 6.168 | −2.050 | 0.0460491 | inositol 1,4,5-triphosphate receptor, type 2 |
| WDFY2 | 6.065 | 5.693 | 6.105 | 4.933 | 5.070 | 5.010 | −2.049 | 0.0152893 | WD repeat and FYVE domain containing 2 |
| GTPBP6 | 7.239 | 7.117 | 7.062 | 6.084 | 5.891 | 6.327 | −2.046 | 0.0110929 | GTP binding protein 6 (putative) |
| MRPS24 | 9.495 | 10.190 | 9.758 | 8.727 | 8.725 | 9.103 | −2.044 | 0.0316170 | mitochondrial ribosomal protein S24 |
| KIAA0240 | 4.893 | 5.093 | 4.705 | 4.234 | 3.811 | 3.675 | −2.041 | 0.0221412 | KIAA0240 |
| PGR | 3.831 | 4.559 | 4.408 | 3.484 | 3.144 | 3.379 | −2.040 | 0.0368342 | progesterone receptor |
| TFEB | 3.954 | 4.529 | 4.362 | 3.013 | 3.334 | 3.404 | −2.038 | 0.0201742 | transcription factor EB |
| SUDS3 | 5.262 | 6.036 | 4.895 | 4.347 | 4.243 | 3.991 | −2.027 | 0.0290253 | suppressor of defective silencing 3 homolog (S. cerevisiae) |
| RNF149 | 7.698 | 7.193 | 6.995 | 5.988 | 6.175 | 6.427 | −2.026 | 0.0207966 | ring finger protein 149 |
| CCDC9 | 6.133 | 5.794 | 6.613 | 4.776 | 5.381 | 5.263 | −2.025 | 0.0361243 | coiled-coil domain containing 9 |
| IER2 | 12.147 | 12.120 | 12.727 | 11.299 | 11.106 | 11.580 | −2.020 | 0.0278196 | immediate early response 2 |
| LRRK1 | 5.214 | 5.486 | 5.361 | 3.782 | 4.350 | 4.490 | −2.014 | 0.0160867 | leucine-rich repeat kinase 1 |
| DHPS | 5.575 | 5.649 | 5.564 | 3.685 | 4.565 | 4.904 | −2.014 | 0.0304198 | deoxyhypusine synthase |
| FYTTD1 | 5.316 | 5.135 | 4.582 | 4.126 | 4.264 | 4.060 | −2.013 | 0.0043015 | forty-two-three domain containing 1 |
| TAF5L | 5.145 | 5.781 | 4.858 | 4.362 | 3.849 | 4.419 | −2.012 | 0.0400054 | TAF5-like RNA polymerase II, p300/CBP-associated factor (PCAF)-associated factor, 65 kDa |
| FAM116B | 6.107 | 6.446 | 7.425 | 5.443 | 5.704 | 5.288 | −2.005 | 0.0423262 | family with sequence similarity 116, member B |
| ENTPD4 | 3.709 | 4.327 | 3.299 | 2.709 | 2.896 | 2.296 | −2.004 | 0.0337667 | ectonucleoside triphosphate diphosphohydrolase 4 |
| MAP1LC3B | 9.117 | 8.080 | 8.085 | 7.479 | 7.090 | 7.081 | −1.999 | 0.0311757 | microtubule-associated protein 1 light chain 3 beta |
| CDK4 | 4.360 | 4.862 | 4.413 | 2.911 | 3.772 | 3.869 | −1.991 | 0.0469378 | cyclin-dependent kinase 4 |
| ADPRHL2 | 4.486 | 5.798 | 4.739 | 3.532 | 4.186 | 3.747 | −1.989 | 0.0484321 | ADP-ribosylhydrolase like 2 |
| RUSC2 | 5.304 | 5.059 | 5.470 | 4.004 | 4.551 | 4.316 | −1.983 | 0.0217176 | RUN and SH3 domain containing 2 |
| KCTD5 | 2.519 | 3.439 | 2.544 | 2.194 | 1.559 | 1.559 | −1.979 | 0.0480714 | potassium channel tetramerisation domain containing 5 |
| TMX1 | 4.931 | 6.199 | 4.828 | 4.064 | 3.844 | 4.085 | −1.978 | 0.0343860 | thioredoxin-related transmembrane protein 1 |
| C11orf31 | 8.280 | 8.133 | 8.086 | 7.243 | 7.300 | 7.040 | −1.973 | 0.0097675 | chromosome 11 open reading frame 31 |
| OBFC1 | 6.526 | 7.511 | 6.392 | 5.786 | 5.937 | 5.416 | −1.966 | 0.0469785 | oligonucleotide/oligosaccharide-binding fold containing 1 |
| MLH3 | 4.948 | 5.411 | 5.168 | 3.994 | 4.193 | 4.228 | −1.966 | 0.0127982 | mutL homolog 3 (E. coli) |
| NKIRAS2 | 6.339 | 7.219 | 6.120 | 5.708 | 5.148 | 5.365 | −1.965 | 0.0377145 | NFKB inhibitor interacting Ras-like 2 |
| ALOXE3 | 5.896 | 6.602 | 6.369 | 4.936 | 4.922 | 5.689 | −1.964 | 0.0340583 | arachidonate lipoxygenase 3 |
| UBE2R2 | 11.165 | 10.788 | 10.753 | 9.781 | 9.908 | 10.164 | −1.961 | 0.0206285 | ubiquitin-conjugating enzyme E2R 2 |
| GALNT3 | 6.079 | 5.576 | 5.200 | 4.607 | 4.412 | 4.759 | −1.958 | 0.0320422 | UDP-N-acetyl-alpha-D-galactosamine:polypeptide N-acetylgalactosaminyltransferase 3 (GalNAc-T3) |
| PSMD7 | 7.079 | 7.830 | 6.771 | 6.111 | 6.343 | 6.064 | −1.956 | 0.0393914 | proteasome (prosome, macropain) 26S subunit, non-ATPase, 7 |
| WDR6 | 6.914 | 7.031 | 6.852 | 5.225 | 5.947 | 6.469 | −1.954 | 0.0486731 | WD repeat domain 6 |
| FAM108C1 | 4.870 | 5.901 | 4.996 | 4.315 | 4.347 | 3.907 | −1.949 | 0.0441827 | family with sequence similarity 108, member C1 |
| CYP2J2 | 2.519 | 2.650 | 2.404 | 1.559 | 1.559 | 1.559 | −1.944 | 0.0077874 | cytochrome P450, family 2, subfamily J, polypeptide 2 |
| C1orf152 | 2.519 | 2.404 | 3.459 | 1.559 | 1.559 | 1.559 | −1.944 | 0.0239386 | chromosome 1 open reading frame 152 |
| LOC643763 | 3.519 | 4.033 | 3.324 | 2.746 | 2.559 | 2.559 | −1.944 | 0.0240054 | No description |
| CD1D | 2.519 | 2.602 | 2.037 | 1.559 | 1.559 | 1.559 | −1.944 | 0.0344114 | CD1d molecule |
| ZC3HC1 | 2.519 | 3.059 | 2.075 | 1.559 | 1.559 | 1.559 | −1.944 | 0.0382030 | zinc finger, C3HC-type containing 1 |
| TTC33 | 2.519 | 3.059 | 2.037 | 1.559 | 1.559 | 1.559 | −1.944 | 0.0423983 | tetratricopeptide repeat domain 33 |

TABLE 5-continued

Differentially Expressed Genes in CD24+ Breast Epithelial Cells

| | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| RAD51L3 | 3.814 | 3.574 | 3.516 | 2.559 | 2.559 | 3.205 | −1.941 | 0.0446462 | RAD51-like 3 (*S. cerevisiae*) |
| SEC14L2 | 7.988 | 8.479 | 8.232 | 7.554 | 7.276 | 5.957 | −1.941 | 0.0473461 | SEC14-like 2 (*S. cerevisiae*) |
| PFKFB3 | 8.608 | 7.714 | 7.345 | 6.763 | 6.551 | 6.772 | −1.933 | 0.0351543 | 6-phosphofructo-2-kinase/fructose-2,6-biphosphatase 3 |
| CHMP4B | 8.885 | 8.887 | 8.641 | 7.387 | 7.934 | 8.216 | −1.933 | 0.0362855 | chromatin modifying protein 4B |
| TMEM30A | 8.214 | 9.244 | 8.557 | 7.608 | 7.567 | 7.876 | −1.930 | 0.0466500 | transmembrane protein 30A |
| KIAA0831 | 6.716 | 6.614 | 5.943 | 5.380 | 5.285 | 5.770 | −1.926 | 0.0445464 | No description |
| PEBP1 | 10.120 | 11.108 | 10.106 | 9.212 | 9.562 | 9.161 | −1.925 | 0.0364827 | phosphatidylethanolamine binding protein 1 |
| B3GALNT2 | 5.539 | 6.990 | 5.984 | 4.957 | 5.039 | 5.040 | −1.925 | 0.0487276 | beta-1,3-N-acetylgalactosaminyltransferase 2 |
| TRMU | 6.420 | 6.687 | 7.009 | 6.064 | 5.341 | 5.823 | −1.924 | 0.0390737 | tRNA 5-methylaminomethyl-2-thiouridylate methyltransferase |
| UFC1 | 10.570 | 10.094 | 10.572 | 9.566 | 9.494 | 9.629 | −1.922 | 0.0283776 | ubiquitin-fold modifier conjugating enzyme 1 |
| TACC2 | 6.664 | 5.383 | 5.510 | 4.713 | 4.877 | 4.444 | −1.917 | 0.0459524 | transforming, acidic coiled-coil containing protein 2 |
| TRPM4 | 4.862 | 5.363 | 5.218 | 4.300 | 4.272 | 4.280 | −1.916 | 0.0236685 | transient receptor potential cation channel, subfamily M, member 4 |
| RNF126 | 5.292 | 5.747 | 6.308 | 4.882 | 4.811 | 4.407 | −1.913 | 0.0368511 | ring finger protein 126 |
| GART | 5.437 | 5.852 | 6.033 | 4.501 | 5.152 | 4.623 | −1.913 | 0.0316585 | phosphoribosylglycinamide formyltransferase, phosphoribosylglycinamide synthetase, phosphoribosylaminoimidazole synthetase |
| DAB2IP | 6.185 | 5.998 | 5.250 | 4.315 | 4.539 | 5.259 | −1.913 | 0.0499117 | DAB2 interacting protein |
| SCAMP4 | 5.680 | 6.338 | 5.932 | 5.042 | 4.998 | 4.810 | −1.911 | 0.0194896 | secretory carrier membrane protein 4 |
| BBS1 | 4.428 | 3.715 | 3.616 | 2.782 | 2.559 | 3.077 | −1.910 | 0.0305035 | Bardet-Biedl syndrome 1 |
| LHPP | 5.742 | 5.371 | 6.240 | 4.439 | 5.012 | 4.907 | −1.909 | 0.0425188 | phospholysine phosphohistidine inorganic pyrophosphate phosphatase |
| GFOD2 | 7.794 | 8.034 | 8.315 | 7.102 | 7.092 | 7.317 | −1.908 | 0.0260591 | glucose-fructose oxidoreductase domain containing 2 |
| C19orf60 | 6.182 | 6.468 | 7.284 | 5.551 | 5.537 | 5.335 | −1.906 | 0.0295979 | chromosome 19 open reading frame 60 |
| LOC100130872 | 2.747 | 2.953 | 2.905 | 1.974 | 1.974 | 1.974 | −1.906 | 0.0092418 | No description |
| MAP2K7 | 8.660 | 8.668 | 8.923 | 7.805 | 7.688 | 7.992 | −1.905 | 0.0151489 | mitogen-activated protein kinase kinase 7 |
| IMPDH1 | 8.028 | 8.541 | 9.312 | 7.317 | 7.614 | 7.662 | −1.902 | 0.0478358 | IMP (inosine 5′-monophosphate) dehydrogenase 1 |
| RBMXL1 | 3.810 | 3.487 | 3.074 | 2.559 | 2.559 | 2.559 | −1.901 | 0.0339225 | RNA binding motif protein, X-linked-like 1 |
| TIMM44 | 8.296 | 8.579 | 8.573 | 7.352 | 7.647 | 7.768 | −1.901 | 0.0219877 | translocase of inner mitochondrial membrane 44 homolog (yeast) |
| SFRS9 | 7.187 | 8.017 | 7.102 | 6.175 | 6.342 | 6.447 | −1.901 | 0.0285334 | No description |
| ARIH2 | 7.143 | 7.651 | 7.173 | 6.218 | 6.557 | 6.693 | −1.899 | 0.0443415 | ariadne homolog 2 (*Drosophila*) |
| FXN | 6.542 | 6.446 | 6.674 | 5.639 | 5.749 | 5.319 | −1.898 | 0.0144436 | frataxin |
| NAA50 | 5.999 | 6.454 | 6.198 | 5.135 | 5.106 | 5.530 | −1.897 | 0.0224996 | N(alpha)-acetyltransferase 50, NatE catalytic subunit |
| C17orf81 | 4.643 | 4.789 | 4.738 | 3.758 | 4.196 | 3.728 | −1.887 | 0.0291888 | chromosome 17 open reading frame 81 |
| CDC37 | 10.638 | 11.029 | 10.948 | 9.617 | 10.033 | 10.124 | −1.886 | 0.0247698 | cell division cycle 37 homolog (*S. cerevisiae*) |
| DUSP19 | 8.162 | 8.463 | 8.160 | 7.252 | 6.945 | 7.656 | −1.886 | 0.0280952 | dual specificity phosphatase 19 |
| TTC27 | 5.186 | 4.920 | 4.543 | 3.891 | 4.276 | 3.809 | −1.879 | 0.0401642 | tetratricopeptide repeat domain 27 |
| GPX4 | 12.474 | 12.058 | 12.785 | 11.128 | 11.734 | 11.635 | −1.878 | 0.0471220 | glutathione peroxidase 4 (phospholipid hydroperoxidase) |
| LRRC4 | 5.274 | 5.700 | 5.386 | 4.366 | 4.649 | 4.698 | −1.876 | 0.0249286 | leucine rich repeat containing 4 |
| TOM1L2 | 6.733 | 6.518 | 7.212 | 5.610 | 6.016 | 5.951 | −1.876 | 0.0322955 | target of myb1 like 2 (chicken) |
| NLRP8 | 8.646 | 8.522 | 8.027 | 7.623 | 7.186 | 7.693 | −1.864 | 0.0420499 | NLR family, pyrin domain containing 8 |
| STK38L | 5.192 | 4.836 | 4.496 | 3.865 | 4.197 | 3.937 | −1.864 | 0.0453500 | serine/threonine kinase 38 like |
| PITPNM1 | 6.123 | 6.228 | 6.276 | 5.102 | 5.335 | 5.446 | −1.857 | 0.0140184 | phosphatidylinositol transfer protein, membrane-associated 1 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| ALDH2 | 7.246 | 7.093 | 7.188 | 6.201 | 6.462 | 6.233 | −1.856 | 0.0138196 | aldehyde dehydrogenase 2 family (mitochondrial) |
| TRAPPC3 | 6.087 | 6.472 | 6.408 | 4.882 | 5.518 | 5.682 | −1.852 | 0.0390844 | trafficking protein particle complex 3 |
| SAPS2 | 6.764 | 7.209 | 7.836 | 5.926 | 6.326 | 6.320 | −1.852 | 0.0388672 | No description |
| TIA1 | 4.505 | 4.920 | 4.646 | 3.656 | 4.034 | 3.739 | −1.849 | 0.0256147 | TIA1 cytotoxic granule-associated RNA binding protein |
| PRKCI | 6.033 | 6.451 | 6.330 | 4.366 | 5.522 | 5.565 | −1.849 | 0.0499816 | protein kinase C, iota |
| FOXH1 | 2.747 | 2.860 | 3.922 | 1.974 | 1.974 | 1.974 | −1.847 | 0.0330652 | forkhead box H1 |
| PDGFB | 4.280 | 4.015 | 4.121 | 3.117 | 3.543 | 3.236 | −1.847 | 0.0260376 | platelet-derived growth factor beta polypeptide (simian sarcoma viral (v-sis) oncogene homolog) |
| COMMD9 | 6.844 | 6.474 | 6.661 | 5.806 | 5.968 | 5.274 | −1.836 | 0.0294336 | COMM domain containing 9 |
| MRPL45 | 7.565 | 8.075 | 7.705 | 6.832 | 7.194 | 6.734 | −1.832 | 0.0371458 | mitochondrial ribosomal protein L45 |
| TRAF3 | 4.687 | 5.599 | 4.921 | 4.050 | 3.914 | 4.378 | −1.829 | 0.0488051 | TNF receptor-associated factor 3 |
| ANXA4 | 6.148 | 7.091 | 5.986 | 5.240 | 5.379 | 5.285 | −1.820 | 0.0376416 | annexin A4 |
| SLC15A4 | 5.339 | 5.090 | 4.615 | 4.230 | 4.264 | 3.899 | −1.816 | 0.0430576 | solute carrier family 15, member 4 |
| UQCRC1 | 9.446 | 9.771 | 9.341 | 8.950 | 8.590 | 8.407 | −1.811 | 0.0356500 | ubiquinol-cytochrome c reductase core protein 1 |
| RICS | 8.263 | 7.376 | 7.197 | 6.386 | 6.541 | 6.522 | −1.807 | 0.0327544 | No description |
| SF1 | 10.054 | 10.489 | 10.075 | 9.033 | 9.437 | 9.637 | −1.805 | 0.0466922 | splicing factor 1 |
| CDIPT | 5.597 | 5.668 | 5.121 | 4.623 | 4.816 | 4.619 | −1.804 | 0.0444881 | CDP-diacylglycerol inositol 3-phosphatidyltransferase |
| CCDC90A | 3.364 | 3.126 | 4.166 | 2.518 | 2.296 | 2.695 | −1.799 | 0.0420084 | coiled-coil domain containing 90A |
| SLAMF8 | 4.899 | 3.704 | 3.966 | 3.196 | 3.196 | 2.860 | −1.796 | 0.0445196 | SLAM family member 8 |
| PLK1 | 3.220 | 3.966 | 3.220 | 2.649 | 2.377 | 2.457 | −1.793 | 0.0354259 | polo-like kinase 1 |
| C1QTNF6 | 4.167 | 4.344 | 4.242 | 3.296 | 3.471 | 3.509 | −1.783 | 0.0153768 | C1q and tumor necrosis factor related protein 6 |
| RETSAT | 7.537 | 7.329 | 7.512 | 6.512 | 6.705 | 6.595 | −1.780 | 0.0140591 | retinol saturase (all-trans-retinol 13,14-reductase) |
| C14orf101 | 3.728 | 3.949 | 4.094 | 3.117 | 2.974 | 3.236 | −1.772 | 0.0249624 | chromosome 14 open reading frame 101 |
| LMLN | 4.351 | 3.970 | 4.231 | 3.144 | 3.337 | 3.581 | −1.772 | 0.0322049 | leishmanolysin-like (metallopeptidase M8 family) |
| C12orf57 | 10.947 | 10.712 | 10.768 | 9.944 | 9.873 | 10.137 | −1.770 | 0.0192924 | chromosome 12 open reading frame 57 |
| NDEL1 | 4.652 | 4.643 | 4.777 | 4.146 | 3.815 | 3.831 | −1.767 | 0.0280491 | nudE nuclear distribution gene E homolog (A. nidulans)-like 1 |
| CSNK2B | 9.848 | 10.972 | 10.054 | 9.254 | 9.233 | 9.027 | −1.767 | 0.0374106 | casein kinase 2, beta polypeptide |
| FSD1L | 2.519 | 2.375 | 2.627 | 1.559 | 2.075 | 1.559 | −1.760 | 0.0456654 | fibronectin type III and SPRY domain containing 1-like |
| SUCLG1 | 9.105 | 8.634 | 8.550 | 7.737 | 7.991 | 8.107 | −1.756 | 0.0381596 | succinate-CoA ligase, alpha subunit |
| RPL41 | 17.551 | 16.677 | 16.677 | 15.865 | 15.865 | 15.865 | −1.756 | 0.0276055 | ribosomal protein L41 |
| PPL | 5.488 | 6.396 | 5.516 | 4.677 | 4.907 | 4.861 | −1.754 | 0.0442203 | periplakin |
| CWC25 | 5.371 | 4.973 | 4.665 | 4.327 | 3.900 | 4.163 | −1.753 | 0.0439870 | CWC25 spliceosome-associated protein homolog (S. cerevisiae) |
| DNTTIP2 | 6.810 | 6.702 | 6.851 | 5.983 | 6.263 | 5.894 | −1.751 | 0.0315380 | deoxynucleotidyltransferase, terminal, interacting protein 2 |
| ATN1 | 9.576 | 9.902 | 10.308 | 9.152 | 9.094 | 9.078 | −1.751 | 0.0453975 | atrophin 1 |
| LOC151162 | 5.052 | 5.392 | 4.763 | 4.243 | 4.248 | 4.419 | −1.746 | 0.0488373 | No description |
| NUCB1 | 7.571 | 7.104 | 7.266 | 6.139 | 6.772 | 6.471 | −1.740 | 0.0443062 | nucleobindin 1 |
| KLF13 | 7.873 | 7.671 | 7.282 | 6.895 | 6.879 | 6.624 | −1.732 | 0.0417690 | Kruppel-like factor 13 |
| NTRK3 | 2.747 | 2.976 | 3.091 | 1.974 | 1.974 | 2.457 | −1.708 | 0.0416953 | neurotrophic tyrosine kinase, receptor, type 3 |
| KCMF1 | 7.964 | 7.201 | 7.402 | 6.606 | 6.645 | 6.748 | −1.690 | 0.0448350 | potassium channel modulatory factor 1 |
| BNIP1 | 6.322 | 5.995 | 5.778 | 5.370 | 5.273 | 5.273 | −1.650 | 0.0469163 | BCL2/adenovirus E1B 19 kDa interacting protein 1 |
| OSCP1 | 5.554 | 5.478 | 5.277 | 4.746 | 4.844 | 4.705 | −1.636 | 0.0348695 | organic solute carrier partner 1 |
| SLC12A9 | 3.911 | 3.769 | 3.753 | 3.205 | 3.026 | 3.077 | −1.632 | 0.0238173 | solute carrier family 12 (potassium/chloride transporters), member 9 |
| FGFBP3 | 3.220 | 2.673 | 2.667 | 1.974 | 1.974 | 1.974 | −1.623 | 0.0291397 | fibroblast growth factor binding protein 3 |
| CTBP2 | 5.396 | 5.042 | 4.964 | 4.266 | 4.500 | 4.462 | −1.622 | 0.0440246 | C-terminal binding protein 2 |

TABLE 5-continued

Differentially Expressed Genes in CD24+ Breast Epithelial Cells

| | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| TMEM181 | 8.024 | 7.992 | 7.697 | 7.002 | 7.308 | 7.298 | −1.620 | 0.0463438 | transmembrane protein 181 |
| PFKFB2 | 3.944 | 4.234 | 3.927 | 3.296 | 3.296 | 3.296 | −1.566 | 0.0265272 | 6-phosphofructo-2-kinase/fructose-2,6-biphosphatase 2 |
| KIAA0090 | 3.999 | 4.102 | 3.943 | 3.462 | 3.377 | 2.974 | −1.559 | 0.0422479 | KIAA0090 |

Higher Expression in Parous

| LOC388692 | 6.190 | 6.225 | 6.353 | 6.958 | 6.717 | 6.890 | 1.521 | 0.0483277 | No description |
| PGBD2 | 1.559 | 1.559 | 1.559 | 2.404 | 2.075 | 2.173 | 1.530 | 0.0387978 | piggyBac transposable element derived 2 |
| TMEM185B | 2.559 | 2.585 | 2.585 | 3.205 | 3.075 | 3.496 | 1.537 | 0.0434965 | transmembrane protein 185B (pseudogene) |
| NIN | 5.461 | 5.391 | 5.473 | 6.712 | 6.027 | 6.092 | 1.553 | 0.0448880 | ninein (GSK3B interacting protein) |
| ZNF623 | 5.055 | 4.665 | 5.076 | 5.517 | 5.667 | 5.718 | 1.561 | 0.0469056 | zinc finger protein 623 |
| ZC3H12B | 1.974 | 1.974 | 1.974 | 2.649 | 2.858 | 2.457 | 1.597 | 0.0405556 | zinc finger CCCH-type containing 12B |
| SERPINB8 | 6.188 | 6.520 | 6.332 | 6.999 | 6.875 | 7.313 | 1.610 | 0.0495625 | serpin peptidase inhibitor, clade B (ovalbumin), member 8 |
| SOCS6 | 5.226 | 4.781 | 5.252 | 5.966 | 5.666 | 5.925 | 1.639 | 0.0452333 | suppressor of cytokine signaling 6 |
| N4BP1 | 7.299 | 7.806 | 7.555 | 8.386 | 8.284 | 8.181 | 1.658 | 0.0449271 | NEDD4 binding protein 1 |
| IDH | 8.143 | 7.875 | 8.242 | 8.877 | 8.780 | 8.913 | 1.663 | 0.0267744 | Description |
| LOC401093 | 4.360 | 4.237 | 4.606 | 5.117 | 4.973 | 5.226 | 1.666 | 0.0410568 | No description |
| LOC652276 | 4.304 | 4.282 | 3.868 | 4.825 | 5.047 | 4.856 | 1.673 | 0.0397913 | No description |
| LONRF2 | 4.331 | 3.944 | 3.912 | 5.022 | 4.841 | 4.667 | 1.688 | 0.0392264 | LON peptidase N-terminal domain and ring finger 2 |
| OXR1 | 6.439 | 6.600 | 6.553 | 7.065 | 7.309 | 7.938 | 1.689 | 0.0455249 | oxidation resistance 1 |
| L2HGDH | 7.244 | 6.733 | 7.035 | 7.768 | 7.643 | 8.002 | 1.691 | 0.0396577 | L-2-hydroxyglutarate dehydrogenase |
| HN1L | 9.635 | 10.345 | 10.255 | 11.105 | 10.762 | 11.019 | 1.698 | 0.0440714 | hematological and neurological expressed 1-like |
| EPB41L2 | 2.782 | 2.994 | 3.118 | 3.598 | 3.757 | 3.886 | 1.703 | 0.0288555 | erythrocyte membrane protein band 4.1-like 2 |
| C1orf27 | 6.526 | 6.700 | 6.503 | 7.300 | 7.796 | 7.201 | 1.710 | 0.0349509 | chromosome 1 open reading frame 27 |
| C14orf119 | 2.974 | 3.841 | 3.869 | 4.464 | 4.649 | 4.450 | 1.717 | 0.0466393 | chromosome 14 open reading frame 119 |
| PSMC6 | 8.916 | 8.961 | 8.143 | 9.631 | 9.741 | 9.603 | 1.717 | 0.0356692 | proteasome (prosome, macropain) 26S subunit, ATPase, 6 |
| CXorf36 | 3.539 | 3.214 | 3.497 | 4.514 | 3.907 | 4.286 | 1.728 | 0.0431965 | chromosome X open reading frame 36 |
| DGKA | 7.202 | 7.066 | 7.408 | 7.950 | 8.207 | 7.859 | 1.733 | 0.0326147 | diacylglycerol kinase, alpha 80 kDa |
| DPY19L3 | 4.234 | 4.263 | 3.546 | 4.902 | 4.887 | 5.066 | 1.744 | 0.0353300 | dpy-19-like 3 (C. elegans) |
| LOC643008 | 3.747 | 3.412 | 3.471 | 4.107 | 4.290 | 4.906 | 1.764 | 0.0474305 | No description |
| PREPL | 4.246 | 4.522 | 4.540 | 5.005 | 5.342 | 5.582 | 1.765 | 0.0321358 | prolyl endopeptidase-like |
| FAM120A | 8.136 | 8.400 | 7.513 | 8.955 | 9.199 | 8.919 | 1.765 | 0.0347176 | family with sequence similarity 120A |
| COX 10 | 3.144 | 3.539 | 3.963 | 4.360 | 4.351 | 4.559 | 1.767 | 0.0456546 | COX10 homolog, cytochrome c oxidase assembly protein, heme A: farnesyltransferase (yeast) |
| MRPS35 | 7.337 | 7.440 | 7.891 | 8.422 | 8.343 | 8.167 | 1.777 | 0.0496907 | mitochondrial ribosomal protein S35 |
| ZDHHC2 | 3.364 | 3.680 | 3.007 | 4.123 | 4.512 | 4.042 | 1.779 | 0.0446355 | zinc finger, DHHC-type containing 2 |
| IOCA1 | 2.974 | 2.994 | 2.974 | 3.484 | 3.809 | 4.280 | 1.783 | 0.0411543 | IQ motif containing with AAA domain 1 |
| SLFN13 | 5.626 | 4.999 | 5.484 | 6.219 | 6.464 | 6.287 | 1.787 | 0.0255004 | schlafen family member 13 |
| RAB14 | 10.094 | 10.845 | 10.747 | 11.684 | 11.339 | 11.410 | 1.789 | 0.0423576 | RAB14, member RAS oncogene family |
| CSPP1 | 5.109 | 5.002 | 4.964 | 5.537 | 6.075 | 5.843 | 1.791 | 0.0354152 | centrosome and spindle pole associated protein 1 |
| C20orf195 | 0.974 | 1.328 | 1.264 | 2.108 | 1.692 | 2.404 | 1.795 | 0.0413676 | chromosome 20 open reading frame 195 |
| USP8 | 5.613 | 6.690 | 5.854 | 7.562 | 7.377 | 6.696 | 2.118 | 0.0463078 | ubiquitin specific peptidase 8 |
| KDM2A | 9.849 | 9.619 | 9.543 | 11.120 | 10.703 | 10.398 | 2.121 | 0.0203400 | lysine (K)-specific demethylase 2A |
| ARHGAP23 | 6.238 | 7.206 | 6.902 | 8.158 | 7.626 | 7.988 | 2.123 | 0.0301174 | Rho GTPase activating protein 23 |
| YTHDF2 | 9.980 | 10.923 | 11.412 | 12.301 | 12.010 | 11.818 | 2.125 | 0.0381773 | YTH domain family, member 2 |
| NSL1 | 4.412 | 4.688 | 4.766 | 5.504 | 6.022 | 5.562 | 2.132 | 0.0158005 | NSL1, MIND kinetochore complex component, homolog (S. cerevisiae) |

TABLE 5-continued

Differentially Expressed Genes in CD24+ Breast Epithelial Cells

| | Nulliparous (NP) Samples | | | Parous (P) Samples | | | | | |
| --- | --- | --- | --- | --- | --- | --- | --- | --- | --- |
| | CD24+ N48 | CD24+ N58 | CD24+ N43 | CD24+ N37 | CD24+ N39 | CD24+ N40 | Pseudo fold change | P value | Gene description |
| POMGNT1 | 7.487 | 8.077 | 8.241 | 9.293 | 9.172 | 8.927 | 2.135 | 0.0162049 | protein O-linked mannose beta1,2-N-acetylglucosaminyltransferase |
| GCDH | 5.254 | 5.860 | 6.348 | 7.037 | 6.956 | 6.667 | 2.137 | 0.0400852 | glutaryl-CoA dehydrogenase |
| RTKN2 | 3.412 | 3.031 | 3.844 | 4.152 | 4.507 | 4.803 | 2.137 | 0.0339440 | rhotekin 2 |
| DAG LA | 4.548 | 5.102 | 4.255 | 6.030 | 5.443 | 5.645 | 2.139 | 0.0328342 | diacylglycerol lipase, alpha |
| C19orf12 | 5.847 | 6.570 | 5.598 | 6.830 | 7.225 | 6.945 | 2.139 | 0.0448074 | chromosome 19 open reading frame 12 |
| PCBD2 | 5.664 | 5.318 | 5.540 | 6.762 | 6.694 | 6.244 | 2.140 | 0.0160483 | pterin-4 alpha-carbinolamine dehydratase/dimerization cofactor of hepatocyte nuclear factor 1 alpha (TCF1) 2 |
| REC8 | 5.012 | 5.478 | 5.471 | 6.110 | 6.149 | 6.588 | 2.140 | 0.0274006 | REC8 homolog (yeast) |
| ZNF518B | 4.243 | 3.462 | 3.916 | 5.145 | 5.344 | 4.484 | 2.144 | 0.0362579 | zinc finger protein 518B |
| MGAT4A | 4.546 | 4.914 | 4.334 | 5.866 | 5.437 | 5.679 | 2.148 | 0.0183369 | mannosyl (alpha-1,3-)-glycoprotein beta-1,4-N-acetylglucosaminyltransferase, isozyme A |
| ARF1 | 12.915 | 13.572 | 13.433 | 14.679 | 14.486 | 14.060 | 2.154 | 0.0242817 | ADP-ribosylation factor 1 |
| FAM153B | 5.945 | 5.043 | 6.494 | 7.448 | 6.941 | 7.053 | 2.154 | 0.0349194 | family with sequence similarity 153, member B |
| ANKLE1 | 6.124 | 5.354 | 5.279 | 6.814 | 6.387 | 6.820 | 2.156 | 0.0317199 | ankyrin repeat and LEM domain containing 1 |
| PTGER2 | 2.296 | 2.448 | 2.675 | 3.784 | 3.751 | 3.043 | 2.157 | 0.0276470 | prostaglandin E receptor 2 (subtype EP2), 53 kDa |
| MRPS25 | 7.393 | 6.110 | 6.901 | 7.916 | 8.080 | 8.010 | 2.157 | 0.0335572 | mitochondrial ribosomal protein S25 |
| LOC285550 | 4.761 | 4.434 | 3.850 | 5.870 | 5.214 | 5.406 | 2.158 | 0.0301734 | No description |
| SFRS13A | 7.067 | 6.180 | 6.918 | 7.769 | 8.033 | 8.049 | 2.166 | 0.0185625 | No description |
| MTMR9 | 4.183 | 5.172 | 5.154 | 6.287 | 6.003 | 5.886 | 2.167 | 0.0266754 | myotubularin related protein 9 |
| SLC30A4 | 2.974 | 3.665 | 3.189 | 4.696 | 4.091 | 4.721 | 2.168 | 0.0189102 | solute carrier family 30 (zinc transporter), member 4 |
| SFRS2IP | 5.579 | 5.542 | 6.087 | 7.148 | 7.069 | 6.659 | 2.168 | 0.0130737 | No description |
| TNFSF10 | 9.032 | 8.641 | 9.174 | 10.507 | 9.976 | 9.761 | 2.173 | 0.0224589 | tumor necrosis factor (ligand) superfamily, member 10 |
| MTHFR | 8.533 | 8.257 | 8.834 | 9.991 | 9.652 | 9.103 | 2.178 | 0.0372694 | methylenetetrahydrofolate reductase (NAD(P)H |
| ATR | 4.777 | 5.173 | 5.618 | 6.741 | 6.187 | 5.921 | 2.179 | 0.0381880 | ataxia telangiectasia and Rad3 related |
| RSAD1 | 2.559 | 2.825 | 2.663 | 3.685 | 4.110 | 3.683 | 2.179 | 0.0096017 | radical S-adenosyl methionine domain containing 1 |
| FGF5 | 4.984 | 4.282 | 5.293 | 5.860 | 6.212 | 6.110 | 2.183 | 0.0233292 | fibroblast growth factor 5 |
| ATP5E | 0.974 | 0.974 | 0.974 | 2.108 | 1.692 | 2.878 | 2.193 | 0.0246654 | ATP synthase, H+ transporting, mitochondrial F1 complex, epsilon subunit |
| TAF1A | 0.974 | 1.328 | 3.927 | 2.108 | 2.848 | 1.819 | 2.193 | 0.0283530 | TATA box binding protein (TBP)-associated factor, RNA polymerase I, A, 48 kDa |
| SLC13A3 | 3.220 | 2.747 | 3.927 | 4.899 | 4.353 | 4.222 | 2.193 | 0.0384858 | solute carrier family 13 (sodium-dependent dicarboxylate transporter), member 3 |
| RNF160 | 5.793 | 5.206 | 4.870 | 6.360 | 6.003 | 6.469 | 2.194 | 0.0433208 | No description |
| AS3MT | 1.974 | 2.819 | 3.334 | 3.966 | 3.712 | 3.954 | 2.196 | 0.0420391 | arsenic (+3 oxidation state) methyltransferase |
| GGA2 | 6.106 | 5.609 | 5.881 | 7.354 | 6.746 | 6.997 | 2.199 | 0.0148672 | golgi-associated, gamma adaptin ear containing, ARF binding protein 2 |
| CCDC115 | 5.584 | 5.848 | 4.242 | 6.844 | 6.231 | 6.722 | 2.201 | 0.0432226 | coiled-coil domain containing 115 |
| CILP | 1.559 | 2.375 | 2.627 | 3.032 | 3.374 | 3.767 | 2.204 | 0.0348588 | cartilage intermediate layer protein, nucleotide pyrophosphohydrolase |
| NXF1 | 10.385 | 10.939 | 11.213 | 12.081 | 11.840 | 12.111 | 2.206 | 0.0184766 | nuclear RNA export factor 1 |
| NUFIP1 | 4.802 | 4.918 | 4.577 | 5.746 | 6.093 | 5.721 | 2.209 | 0.0110821 | nuclear fragile X mental retardation protein interacting protein 1 |
| ABL1 | 7.897 | 9.049 | 8.447 | 9.591 | 9.640 | 9.406 | 2.210 | 0.0391535 | c-abl oncogene 1, non-receptor tyrosine kinase |
| MDK | 9.878 | 8.916 | 10.464 | 10.848 | 11.022 | 11.187 | 2.210 | 0.0419670 | midkine (neurite growth-promoting factor 2) |
| GPR143 | 0.974 | 0.974 | 1.050 | 2.108 | 1.692 | 1.819 | 1.795 | 0.0186969 | G protein-coupled receptor 143 |
| FBN2 | 0.974 | 1.050 | 0.974 | 2.404 | 1.692 | 1.819 | 1.795 | 0.0269593 | fibrillin 2 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| RPL23AP82 | 1.559 | 1.559 | 1.759 | 2.404 | 2.075 | 2.650 | 1.795 | 0.0482003 | ribosomal protein L23a pseudogene 82 |
| CLCN5 | 2.974 | 3.206 | 2.994 | 3.825 | 3.934 | 4.033 | 1.804 | 0.0142916 | chloride channel 5 |
| LOC284232 | 7.744 | 7.871 | 7.936 | 8.723 | 8.573 | 8.860 | 1.805 | 0.0151297 | No description |
| COX 11 | 3.272 | 3.838 | 3.598 | 4.327 | 4.703 | 4.327 | 1.821 | 0.0342916 | COX11 cytochrome c oxidase assembly homolog (yeast) |
| MKLN1 | 8.236 | 7.011 | 8.324 | 8.907 | 9.078 | 9.193 | 1.826 | 0.0435468 | muskelin 1, intracellular mediator containing kelch motifs |
| CNGB1 | 2.944 | 2.880 | 2.296 | 3.469 | 3.817 | 3.680 | 1.831 | 0.0313530 | cyclic nucleotide gated channel beta 1 |
| ADAMTS1 | 3.764 | 3.448 | 3.448 | 4.263 | 4.321 | 5.028 | 1.831 | 0.0355403 | ADAM metallopeptidase with thrombospondin type 1 motif, 1 |
| MORF4L1 | 10.853 | 10.663 | 9.641 | 11.723 | 11.538 | 11.454 | 1.833 | 0.0365487 | mortality factor 4 like 1 |
| MRPL14 | 10.536 | 10.041 | 10.082 | 11.212 | 11.372 | 10.917 | 1.835 | 0.0267153 | mitochondrial ribosomal protein L14 |
| UBE2J1 | 9.593 | 9.063 | 9.474 | 10.749 | 10.313 | 9.946 | 1.844 | 0.0418688 | ubiquitin-conjugating enzyme E2, J1 (UBC6 homolog, yeast) |
| TCFL5 | 3.470 | 3.872 | 3.767 | 4.353 | 4.940 | 4.554 | 1.845 | 0.0311949 | transcription factor-like 5 (basic helix-loop-helix) |
| NSMCE4A | 1.974 | 1.974 | 2.013 | 3.319 | 2.858 | 2.457 | 1.845 | 0.0438104 | non-SMC element 4 homolog A (S. cerevisiae) |
| IKBKB | 7.860 | 7.701 | 7.608 | 8.585 | 8.375 | 8.953 | 1.846 | 0.0255457 | inhibitor of kappa light polypeptide gene enhancer in B-cells, kinase beta |
| TIMP4 | 1.974 | 1.974 | 1.974 | 4.168 | 2.858 | 2.860 | 1.847 | 0.0326616 | TIMP metallopeptidase inhibitor 4 |
| PAIP2B | 1.974 | 1.974 | 2.406 | 2.860 | 3.334 | 2.860 | 1.847 | 0.0339332 | poly(A) binding protein interacting protein 2B |
| PRIC285 | 3.865 | 4.126 | 4.522 | 5.012 | 5.016 | 4.980 | 1.848 | 0.0374574 | No description |
| WDR1 | 11.174 | 11.641 | 11.096 | 12.145 | 12.158 | 11.983 | 1.849 | 0.0403929 | WD repeat domain 1 |
| TROVE2 | 7.575 | 8.205 | 8.467 | 9.012 | 9.355 | 9.019 | 1.850 | 0.0325894 | TROVE domain family, member 2 |
| TRIT1 | 4.572 | 4.637 | 4.107 | 5.262 | 5.667 | 4.997 | 1.854 | 0.0494973 | tRNA isopentenyltransferase 1 |
| RAD18 | 4.819 | 5.492 | 5.691 | 6.218 | 6.584 | 6.177 | 1.856 | 0.0401834 | RAD18 homolog (S. cerevisiae) |
| SGK196 | 1.559 | 1.559 | 1.559 | 2.194 | 2.454 | 2.650 | 1.859 | 0.0198550 | No description |
| C20orf20 | 5.824 | 5.408 | 5.263 | 6.391 | 6.166 | 6.338 | 1.869 | 0.0396470 | chromosome 20 open reading frame 20 |
| DGKZ | 7.405 | 7.308 | 7.419 | 8.057 | 8.564 | 8.311 | 1.875 | 0.0182525 | diacylglycerol kinase, zeta |
| SORBS1 | 5.875 | 7.160 | 7.240 | 8.003 | 7.914 | 8.149 | 1.878 | 0.0396362 | sorbin and SH3 domain containing 1 |
| RNMTL1 | 5.584 | 6.625 | 6.511 | 7.461 | 7.093 | 7.421 | 1.880 | 0.0406992 | RNA methyltransferase like 1 |
| NARG2 | 2.782 | 2.974 | 3.419 | 4.133 | 3.704 | 3.886 | 1.881 | 0.0441151 | NMDA receptor regulated 2 |
| CBLL1 | 6.468 | 6.498 | 7.070 | 7.907 | 7.580 | 7.381 | 1.883 | 0.0363730 | Cas-Br-M (murine) ecotropic retroviral transforming sequence-like 1 |
| MYO19 | 6.846 | 6.789 | 6.516 | 7.431 | 7.622 | 7.805 | 1.886 | 0.0202064 | myosin XIX |
| CBARA1 | 6.747 | 6.299 | 6.513 | 7.651 | 7.607 | 7.217 | 1.890 | 0.0213645 | calcium binding atopy-related autoantigen 1 |
| PDE4D | 3.144 | 3.144 | 3.161 | 4.183 | 4.066 | 3.605 | 1.894 | 0.0381036 | phosphodiesterase 4D, cAMP-specific |
| PPP2CB | 11.603 | 11.058 | 11.557 | 11.870 | 12.479 | 12.719 | 1.895 | 0.0499470 | protein phosphatase 2, catalytic subunit, beta isozyme |
| NRM | 4.631 | 4.478 | 4.887 | 6.683 | 5.410 | 5.541 | 1.908 | 0.0402701 | nrim (nuclear envelope membrane protein) |
| PIK302B | 3.539 | 3.645 | 3.144 | 4.696 | 4.079 | 4.166 | 1.911 | 0.0463546 | phosphoinositide-3-kinase, class 2, beta polypeptide |
| CBX5 | 5.389 | 5.201 | 5.378 | 6.432 | 6.314 | 6.057 | 1.912 | 0.0142448 | chromobox homolog 5 |
| ZNF586 | 3.597 | 3.196 | 3.723 | 3.966 | 4.534 | 4.806 | 1.914 | 0.0498273 | zinc finger protein 586 |
| C6orf136 | 6.505 | 6.208 | 5.904 | 7.147 | 7.184 | 6.961 | 1.916 | 0.0285879 | chromosome 6 open reading frame 136 |
| HADHA | 9.823 | 10.058 | 10.347 | 11.083 | 10.851 | 11.000 | 1.921 | 0.0231949 | hydroxyacyl-CoA dehydrogenase/3-ketoacyl-CoA thiolase/enoyl-CoA hydratase (trifunctional protein), alpha subunit |
| LOC100133957 | 5.236 | 4.801 | 4.290 | 5.744 | 5.647 | 6.010 | 1.923 | 0.0363837 | No description |
| TPD52L2 | 9.569 | 10.358 | 10.302 | 11.249 | 11.152 | 11.256 | 1.928 | 0.0195311 | tumor protein D52-like 2 |
| ATP2A3 | 5.379 | 6.239 | 6.600 | 7.097 | 6.949 | 7.550 | 1.933 | 0.0474037 | ATPase, Ca++ transporting, ubiquitous |

TABLE 5-continued

Differentially Expressed Genes in CD24+ Breast Epithelial Cells

| | Nulliparous (NP) Samples | | | Parous (P) Samples | | | | | | |
|---|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| HBS1L | 4.747 | 5.484 | 5.522 | 6.239 | 6.119 | 6.478 | 1.939 | 0.0317652 | HBS1-like (*S. cerevisiae*) |
| ZNF828 | 2.651 | 2.944 | 2.859 | 4.054 | 3.817 | 3.364 | 1.942 | 0.0318849 | zinc finger protein 828 |
| SYNE2 | 7.390 | 6.453 | 6.471 | 8.202 | 7.411 | 8.072 | 1.943 | 0.0455418 | spectrin repeat containing, nuclear envelope 2 |
| TRIM26 | 9.483 | 9.248 | 9.956 | 10.298 | 10.835 | 10.443 | 1.945 | 0.0370015 | tripartite motif-containing 26 |
| MAFF | 6.503 | 8.507 | 8.445 | 9.215 | 9.363 | 9.468 | 1.947 | 0.0495518 | v-maf musculoaponeurotic fibrosarcoma oncogene homolog F (avian) |
| IPP | 3.679 | 3.908 | 4.408 | 5.369 | 5.084 | 4.570 | 1.947 | 0.0435434 | intracisternal A particle-promoted polypeptide |
| C10orf104 | 7.557 | 8.061 | 7.891 | 9.025 | 8.688 | 8.756 | 1.950 | 0.0191266 | No description |
| YTHDF3 | 7.183 | 7.305 | 6.185 | 8.185 | 7.657 | 8.149 | 1.954 | 0.0476285 | YTH domain family, member 3 |
| TRPM7 | 6.335 | 6.118 | 5.327 | 6.914 | 6.755 | 7.304 | 1.957 | 0.0427805 | transient receptor potential cation channel, subfamily M, member 7 |
| WNK1 | 7.803 | 7.432 | 7.725 | 8.696 | 8.403 | 8.875 | 1.960 | 0.0176009 | WNK lysine deficient protein kinase 1 |
| NCRNA00201 | 4.074 | 3.927 | 3.656 | 4.685 | 4.950 | 4.898 | 1.960 | 0.0159701 | non-protein coding RNA 201 |
| C6orf64 | 6.564 | 5.545 | 6.253 | 7.330 | 7.224 | 6.871 | 1.960 | 0.0452824 | chromosome 6 open reading frame 64 |
| TCEB3 | 8.241 | 7.218 | 8.230 | 9.213 | 8.979 | 9.055 | 1.961 | 0.0296470 | transcription elongation factor B (SIII), polypeptide 3 (110 kDa, elong in A) |
| SCAPER | 2.782 | 2.782 | 3.351 | 3.900 | 3.704 | 4.327 | 1.967 | 0.0323170 | S-phase cyclin A-associated protein in the ER |
| HTRA4 | 5.446 | 5.908 | 4.853 | 6.598 | 6.422 | 6.248 | 1.967 | 0.0428281 | HtrA serine peptidase 4 |
| HMGN4 | 7.579 | 7.103 | 6.748 | 8.081 | 8.268 | 7.951 | 1.970 | 0.0367398 | high mobility group nucleosomal binding domain 4 |
| TEAD4 | 7.536 | 6.906 | 7.783 | 8.205 | 8.440 | 8.768 | 1.980 | 0.0348427 | TEA domain family member 4 |
| LSS | 4.166 | 4.546 | 4.304 | 5.531 | 4.983 | 5.386 | 1.980 | 0.0237636 | lanosterol synthase (2,3-oxidosqualene-lanosterol cyclase) |
| KIAA2026 | 5.103 | 4.884 | 4.417 | 5.826 | 5.871 | 5.961 | 1.982 | 0.0164697 | KIAA2026 |
| NUDT21 | 7.236 | 7.626 | 6.885 | 8.614 | 8.188 | 8.017 | 1.983 | 0.0330338 | nudix (nucleoside diphosphate linked moiety X)-type motif 21 |
| METTL7A | 6.589 | 7.348 | 6.619 | 8.083 | 7.798 | 7.577 | 1.984 | 0.0422287 | methyltransferase like 7A |
| C12orf34 | 3.061 | 2.559 | 3.564 | 4.050 | 4.367 | 3.942 | 1.985 | 0.0371105 | chromosome 12 open reading frame 34 |
| SLC23A2 | 5.716 | 5.403 | 5.775 | 6.462 | 6.934 | 6.392 | 1.985 | 0.0249447 | solute carrier family 23 (nucleobase transporters), member 2 |
| CXCL12 | 3.483 | 2.782 | 3.026 | 4.049 | 4.018 | 3.963 | 1.989 | 0.0306539 | chemokine (C-X-C motif) ligand 12 |
| FBXL18 | 5.051 | 5.436 | 5.533 | 6.076 | 6.174 | 6.526 | 1.991 | 0.0284436 | F-box and leucine-rich repeat protein 18 |
| FNIP1 | 6.727 | 7.304 | 6.612 | 7.807 | 7.634 | 7.721 | 1.992 | 0.0440437 | folliculin interacting protein 1 |
| PIK3CA | 4.820 | 4.870 | 4.050 | 5.865 | 5.615 | 6.047 | 1.993 | 0.0444106 | phosphoinositide-3-kinase, catalytic, alpha polypeptide |
| GSN | 5.276 | 9.736 | 10.715 | 11.711 | 11.375 | 11.294 | 1.994 | 0.0291681 | gelsolin |
| RIT1 | 10.492 | 7.569 | 6.236 | 8.008 | 7.910 | 8.252 | 1.995 | 0.0473876 | Ras-like without CAAX 1 |
| SHISA9 | 2.804 | 3.117 | 2.610 | 3.907 | 3.802 | 3.787 | 1.998 | 0.0151190 | shisa homolog 9 (*Xenopus laevis*) |
| KANK2 | 3.006 | 2.782 | 2.782 | 3.999 | 4.005 | 3.616 | 1.998 | 0.0133269 | KN motif and ankyrin repeat domains 2 |
| ZXDC | 7.713 | 7.622 | 8.148 | 9.013 | 8.712 | 8.655 | 1.998 | 0.0231543 | ZXD family zinc finger C |
| C12orf5 | 4.820 | 5.036 | 5.365 | 6.094 | 6.035 | 5.986 | 1.999 | 0.0177575 | chromosome 12 open reading frame 5 |
| ABCF1 | 7.944 | 7.839 | 8.575 | 8.839 | 9.253 | 9.240 | 2.000 | 0.0345664 | ATP-binding cassette, sub-family F (GCN20), member 1 |
| STK25 | 6.738 | 6.176 | 6.554 | 7.391 | 7.617 | 7.554 | 2.000 | 0.0159540 | serine/threonine kinase 25 |
| GPATCH8 | 4.685 | 4.062 | 5.139 | 5.697 | 5.675 | 5.829 | 2.016 | 0.0320015 | G patch domain containing 8 |
| BTBD10 | 6.800 | 5.954 | 6.921 | 7.442 | 7.934 | 7.623 | 2.017 | 0.0355295 | BTB (POZ) domain containing 10 |
| COL4A3BP | 4.544 | 4.169 | 4.174 | 5.337 | 5.082 | 5.558 | 2.018 | 0.0169517 | collagen, type IV, alpha 3 (Goodpasture antigen) binding protein |
| C6orf48 | 8.706 | 9.544 | 9.011 | 9.791 | 9.945 | 10.559 | 2.021 | 0.0484635 | chromosome 6 open reading frame 48 |
| EXOSC7 | 4.666 | 4.548 | 4.608 | 5.623 | 5.362 | 5.832 | 2.021 | 0.0132072 | exosome component 7 |
| MDM4 | 6.924 | 7.005 | 7.670 | 8.548 | 8.332 | 7.943 | 2.026 | 0.0309954 | Mdm4 p53 binding protein homolog (mouse) |

TABLE 5-continued

Differentially Expressed Genes in CD24+ Breast Epithelial Cells

| | Nulliparous (NP) Samples | | Parous (P) Samples | | | | | |
|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| PSMA7 | 11.067 | 11.439 | 10.870 | 12.209 | 12.245 | 11.889 | 2.026 | 0.0221197 | proteasome (prosome, macropain) subunit, alpha type, 7 |
| SENP7 | 2.974 | 3.013 | 3.013 | 4.032 | 3.809 | 4.141 | 2.027 | 0.0091197 | SUMO1/sentrin specific peptidase 7 |
| C13orf1 | 5.171 | 5.128 | 4.645 | 6.477 | 5.667 | 5.937 | 2.031 | 0.0334766 | chromosome 13 open reading frame 1 |
| CCNL1 | 9.234 | 8.723 | 8.476 | 9.749 | 9.590 | 10.144 | 2.036 | 0.0338058 | cyclin L1 |
| ZSWIM7 | 4.475 | 4.642 | 4.623 | 5.649 | 5.778 | 5.171 | 2.037 | 0.0234305 | zinc finger, SWIM-type containing 7 |
| SIP1 | 4.054 | 4.998 | 4.576 | 6.025 | 5.451 | 5.386 | 2.038 | 0.0394298 | survival of motor neuron protein interacting protein 1 |
| CPNE2 | 6.996 | 8.955 | 9.071 | 9.975 | 10.099 | 9.864 | 2.040 | 0.0416339 | copine II |
| C16orf54 | 4.662 | 3.304 | 4.207 | 5.454 | 5.066 | 5.236 | 2.040 | 0.0410322 | chromosome 16 open reading frame 54 |
| GEN1 | 3.296 | 3.388 | 3.540 | 5.104 | 4.419 | 4.270 | 2.043 | 0.0180292 | Gen homolog 1, endonuclease (*Drosophila*) |
| KIAA0892 | 7.012 | 8.324 | 8.437 | 9.356 | 9.377 | 8.891 | 2.044 | 0.0443308 | No description |
| CEP170 | 2.559 | 2.635 | 2.559 | 3.673 | 3.591 | 3.205 | 2.045 | 0.0197107 | centrosomal protein 170 kDa |
| LMTK2 | 8.028 | 6.918 | 7.740 | 8.999 | 8.772 | 8.621 | 2.045 | 0.0261604 | lemur tyrosine kinase 2 |
| DCAF6 | 5.810 | 5.439 | 5.132 | 6.354 | 6.166 | 6.907 | 2.047 | 0.0378887 | DDB1 and CUL4 associated factor 6 |
| BST2 | 7.789 | 7.312 | 7.926 | 8.789 | 8.824 | 8.827 | 2.049 | 0.0120445 | bone marrow stromal cell antigen 2 |
| FRK | 1.974 | 2.228 | 2.161 | 2.825 | 3.196 | 3.376 | 2.049 | 0.0172939 | fyn-related kinase |
| PMS2L5 | 2.247 | 2.432 | 2.878 | 3.324 | 3.478 | 3.469 | 2.051 | 0.0286155 | No description |
| GTF2B | 7.320 | 7.475 | 7.761 | 8.790 | 8.690 | 8.356 | 2.051 | 0.0136639 | general transcription factor I IB |
| GLO1 | 11.439 | 11.459 | 11.984 | 13.022 | 12.985 | 12.270 | 2.053 | 0.0269701 | glyoxalase I |
| AP3S1 | 1.974 | 2.673 | 1.974 | 2.860 | 3.712 | 3.220 | 2.055 | 0.0421120 | adaptor-related protein complex 3, sigma 1 subunit |
| MST1R | 5.198 | 5.339 | 4.676 | 5.851 | 6.266 | 6.239 | 2.057 | 0.0239862 | macrophage stimulating 1 receptor (c-met-related tyrosine kinase) |
| LOC147804 | 3.117 | 3.205 | 3.948 | 4.991 | 4.651 | 4.126 | 2.060 | 0.0348235 | No description |
| GSTCD | 3.908 | 3.858 | 3.351 | 4.784 | 4.775 | 4.951 | 2.060 | 0.0124551 | glutathione S-transferase, C-terminal domain containing |
| NT5C2 | 7.515 | 7.235 | 6.500 | 8.279 | 8.192 | 8.452 | 2.061 | 0.0216938 | 5'-nucleotidase, cytosolic II |
| MRPS7 | 7.836 | 8.331 | 8.760 | 9.334 | 9.806 | 8.980 | 2.066 | 0.0454152 | mitochondrial ribosomal protein S7 |
| RBM23 | 7.989 | 8.236 | 8.531 | 9.309 | 9.411 | 9.037 | 2.068 | 0.0199547 | RNA binding motif protein 23 |
| ZNF516 | 5.189 | 4.917 | 4.343 | 5.959 | 6.038 | 5.969 | 2.074 | 0.0171404 | zinc finger protein 516 |
| MGC16384 | 4.605 | 3.616 | 3.966 | 4.938 | 5.023 | 5.462 | 2.080 | 0.0378097 | No description |
| PDE1C | 0.974 | 1.050 | 1.264 | 2.108 | 1.692 | 3.304 | 2.082 | 0.0469893 | phosphodiesterase 1C, calmodulin-dependent 70 kDa |
| FLVCR1 | 4.290 | 4.187 | 4.445 | 5.348 | 5.616 | 5.112 | 2.083 | 0.0134321 | feline leukemia virus subgroup C cellular receptor 1 |
| LOC344967 | 7.698 | 6.695 | 7.336 | 8.397 | 8.491 | 7.899 | 2.087 | 0.0489540 | No description |
| STARD3NL | 6.984 | 7.219 | 6.792 | 8.048 | 8.382 | 7.549 | 2.090 | 0.0351435 | STARD3 N-terminal like |
| POLH | 6.454 | 6.537 | 7.182 | 8.073 | 7.895 | 7.518 | 2.092 | 0.0259785 | polymerase (DNA directed), eta |
| CKB | 10.487 | 9.524 | 10.643 | 11.416 | 11.488 | 11.709 | 2.093 | 0.0222433 | creatine kinase, brain |
| HERC5 | 2.296 | 2.357 | 2.296 | 2.859 | 3.469 | 3.364 | 2.097 | 0.0265081 | hect domain and RLD 5 |
| DES | 1.974 | 3.247 | 2.953 | 3.525 | 4.022 | 4.106 | 2.097 | 0.0475641 | desmin |
| ABI2 | 4.419 | 4.304 | 4.614 | 6.071 | 5.487 | 5.289 | 2.100 | 0.0174275 | abl-interactor 2 |
| CRABP2 | 12.413 | 11.687 | 12.663 | 13.325 | 13.521 | 13.483 | 2.102 | 0.0222180 | cellular retinoic acid binding protein 2 |
| MRPL33 | 9.961 | 9.581 | 9.654 | 11.257 | 10.725 | 10.372 | 2.102 | 0.0308028 | mitochondrial ribosomal protein L33 |
| LAMB3 | 6.462 | 8.067 | 7.577 | 8.394 | 8.649 | 8.844 | 2.106 | 0.0487736 | laminin, beta 3 |
| TRPS1 | 7.517 | 7.435 | 7.600 | 8.796 | 8.592 | 8.057 | 2.114 | 0.0287521 | trichorhinophalangeal syndrome I |
| SEC31A | 10.791 | 9.850 | 10.470 | 11.212 | 11.494 | 11.489 | 2.116 | 0.0305710 | SEC31 homolog A (*S. cerevisiae*) |
| PPP3CC | 6.061 | 6.807 | 6.831 | 7.374 | 7.637 | 7.912 | 2.212 | 0.0313722 | protein phosphatase 3, catalytic subunit, gamma isozyme |
| SLC25A26 | 8.043 | 7.492 | 7.146 | 8.447 | 8.637 | 8.678 | 2.221 | 0.0311282 | solute carrier family 25, member 26 |
| FAM55C | 6.767 | 5.923 | 6.732 | 7.918 | 7.408 | 7.355 | 2.224 | 0.0364259 | family with sequence similarity 55, member C |
| TTL | 6.092 | 6.896 | 6.620 | 8.049 | 7.618 | 7.435 | 2.226 | 0.0236899 | tubulin tyrosine ligase |
| RAB6A | 3.687 | 5.634 | 5.336 | 6.642 | 6.490 | 6.310 | 2.226 | 0.0365318 | RAB6A, member RAS oncogene family |

TABLE 5-continued

Differentially Expressed Genes in CD24+ Breast Epithelial Cells

| | Nulliparous (NP) Samples | | | Parous (P) Samples | | | | | |
| --- | --- | --- | --- | --- | --- | --- | --- | --- | --- |
| | CD24+ N48 | CD24+ N58 | CD24+ N43 | CD24+ N37 | CD24+ N39 | CD24+ N40 | Pseudo fold change | P value | Gene description |
| CDH17 | 0.974 | 1.692 | 2.142 | 2.848 | 2.848 | 2.348 | 2.228 | 0.0481842 | cadherin 17, LI cadherin (liver-intestine) |
| UPP2 | 5.908 | 6.089 | 6.087 | 6.479 | 7.349 | 7.245 | 2.232 | 0.0368619 | uridine phosphorylase 2 |
| PABPN1 | 9.887 | 8.951 | 9.401 | 10.276 | 10.560 | 10.745 | 2.233 | 0.0286769 | poly(A) binding protein, nuclear 1 |
| ESRP2 | 6.109 | 6.698 | 6.422 | 7.352 | 7.809 | 7.583 | 2.237 | 0.0135372 | epithelial splicing regulatory protein 2 |
| HTATSF1 | 3.272 | 2.847 | 3.611 | 4.768 | 4.434 | 4.327 | 2.237 | 0.0137652 | HIV-1 Tat specific factor 1 |
| FAM3C | 4.169 | 5.097 | 5.153 | 5.982 | 6.317 | 6.201 | 2.241 | 0.0169854 | family with sequence similarity 3, member C |
| KCTD12 | 4.902 | 4.987 | 4.022 | 5.934 | 5.741 | 6.151 | 2.242 | 0.0193715 | potassium channel tetramerisation domain containing 12 |
| BID | 8.015 | 7.416 | 7.651 | 8.581 | 8.881 | 9.011 | 2.242 | 0.0152686 | BH3 interacting domain death agonist |
| CHMP4C | 6.450 | 6.122 | 6.151 | 8.128 | 7.316 | 7.048 | 2.242 | 0.0233983 | chromatin modifying protein 4C |
| PPP1R13L | 10.629 | 9.373 | 10.168 | 11.318 | 11.129 | 11.794 | 2.243 | 0.0266946 | protein phosphatase 1, regulatory (inhibitor) subunit 13 like |
| CCDC86 | 6.710 | 7.569 | 8.083 | 8.537 | 8.902 | 8.735 | 2.244 | 0.0333845 | coiled-coil domain containing 86 |
| CHST6 | 6.709 | 6.068 | 6.849 | 7.875 | 7.959 | 7.439 | 2.245 | 0.0194398 | carbohydrate (N-acetylglucosamine 6-O) sulfotransferase 6 |
| MAP | 3.656 | 3.485 | 3.781 | 5.042 | 4.259 | 4.823 | 2.245 | 0.0234835 | v-maf musculoaponeurotic fibrosarcoma oncogene homolog (avian) |
| LYN | 9.403 | 8.689 | 8.086 | 9.958 | 9.857 | 9.670 | 2.247 | 0.0472809 | v-yes-1 Yamaguchi sarcoma viral related oncogene homolog |
| RRAGA | 8.594 | 9.369 | 9.237 | 10.541 | 10.177 | 9.808 | 2.253 | 0.0323062 | Ras-related GTP binding A |
| PDZRN3 | 2.747 | 2.162 | 2.126 | 3.196 | 3.334 | 3.954 | 2.254 | 0.0262602 | PDZ domain containing ring finger 3 |
| DECR2 | 7.625 | 7.978 | 8.812 | 9.151 | 9.583 | 9.104 | 2.254 | 0.0410215 | 2,4-dienoyl CoA reductase 2, peroxisomal |
| ADO | 4.631 | 6.309 | 6.471 | 7.279 | 7.527 | 7.483 | 2.257 | 0.0314743 | 2-aminoethanethiol (cysteamine) dioxygenase |
| PARD6G | 4.215 | 4.376 | 4.417 | 5.344 | 5.553 | 5.677 | 2.262 | 0.0050261 | par-6 partitioning defective 6 homolog gamma (C. elegans) |
| SNTB2 | 6.533 | 6.599 | 6.998 | 7.778 | 7.755 | 8.174 | 2.265 | 0.0111896 | syntrophin, beta 2 (dystrophin-associated protein A1, 59 kDa, basic component 2) |
| UNC45A | 7.649 | 8.270 | 8.322 | 9.502 | 9.152 | 9.216 | 2.266 | 0.0144328 | unc-45 homolog A (C. elegans) |
| RAGE | 6.882 | 6.377 | 6.571 | 8.063 | 7.887 | 7.183 | 2.267 | 0.0305564 | renal tumor antigen |
| ADAMTS9 | 6.684 | 7.025 | 6.092 | 7.869 | 7.530 | 8.175 | 2.275 | 0.0219179 | ADAM metallopeptidase with thrombospondin type 1 motif, 9 |
| HCCS | 7.808 | 7.014 | 7.639 | 8.830 | 8.888 | 8.811 | 2.283 | 0.0095702 | holocytochrome c synthase |
| C9orf123 | 6.747 | 7.100 | 6.526 | 7.935 | 8.128 | 7.939 | 2.284 | 0.0090737 | chromosome 9 open reading frame 123 |
| TNRC6B | 6.101 | 6.342 | 6.068 | 7.701 | 7.294 | 6.778 | 2.287 | 0.0271205 | trinucleotide repeat containing 6B |
| POLR2A | 9.070 | 9.572 | 8.592 | 10.766 | 10.173 | 10.153 | 2.288 | 0.0223638 | polymerase (RNA) II (DNA directed) polypeptide A, 220 kDa |
| SLC37A1 | 7.654 | 8.854 | 8.704 | 10.048 | 9.786 | 9.340 | 2.288 | 0.0316378 | solute carrier family 37 (glycerol-3-phosphate transporter), member 1 |
| USP2 | 4.450 | 3.117 | 3.861 | 5.096 | 5.013 | 5.059 | 2.295 | 0.0309056 | ubiquitin specific peptidase 2 |
| JAGN1 | 6.809 | 8.074 | 8.044 | 9.273 | 8.892 | 8.478 | 2.296 | 0.0479862 | jagunal homolog 1 (Drosophila) |
| TRIM5 | 5.493 | 5.204 | 4.782 | 6.576 | 6.352 | 6.404 | 2.298 | 0.0096915 | tripartite motif-containing 5 |
| MAPRE2 | 3.764 | 3.766 | 4.220 | 5.181 | 4.968 | 5.295 | 2.303 | 0.0086055 | microtubule-associated protein, RP/EB family, member 2 |
| UTS2D | 1.559 | 3.077 | 3.552 | 4.705 | 4.282 | 4.144 | 2.305 | 0.0341550 | urotensin 2 domain containing |
| B4GALT6 | 1.974 | 3.051 | 2.377 | 3.263 | 3.583 | 3.637 | 2.306 | 0.0451750 | UDP-Gal:betaGlcNAc beta 1,4-galactosyltransferase, polypeptide 6 |
| GATS | 4.059 | 5.637 | 5.317 | 6.843 | 6.474 | 6.122 | 2.308 | 0.0332494 | GATS, stromal antigen 3 opposite strand |
| LOC254559 | 1.974 | 2.347 | 2.126 | 4.758 | 3.334 | 2.860 | 2.310 | 0.0391919 | No description |
| AASDHPPT | 5.232 | 5.616 | 4.543 | 6.049 | 6.713 | 6.441 | 2.312 | 0.0261796 | aminoadipate-semialdehyde dehydrogenase-phosphopantetheinyl transferase |
| GN AZ | 2.519 | 4.364 | 3.778 | 4.989 | 4.765 | 5.200 | 2.315 | 0.0421535 | guanine nucleotide binding protein (G protein), alpha z polypeptide |
| SLC25A43 | 6.140 | 6.738 | 6.433 | 7.353 | 7.959 | 7.367 | 2.317 | 0.0217391 | solute carrier family 25, member 43 |

TABLE 5-continued

Differentially Expressed Genes in CD24+ Breast Epithelial Cells

| | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| AVPH | 6.304 | 5.797 | 5.864 | 7.534 | 7.078 | 6.630 | 2.320 | 0.0311581 | arginine vasopressin-induced 1 |
| NDUFS2 | 3.117 | 2.881 | 3.360 | 4.422 | 4.344 | 4.099 | 2.325 | 0.0094259 | NADH dehydrogenase (ubiquinone) Fe-S protein 2, 49 kDa (NADH-coenzyme Q reductase) |
| AFTPH | 8.844 | 8.281 | 7.799 | 9.313 | 9.473 | 10.062 | 2.325 | 0.0250307 | aftiphilin |
| GGNBP2 | 8.968 | 8.406 | 8.194 | 9.604 | 9.627 | 9.938 | 2.331 | 0.0161305 | gametogenetin binding protein 2 |
| CARD10 | 7.059 | 7.253 | 7.671 | 8.280 | 8.513 | 8.785 | 2.331 | 0.0140883 | caspase recruitment domain family, member 10 |
| CLEC4E | 1.974 | 2.013 | 2.013 | 4.899 | 3.196 | 3.220 | 2.332 | 0.0207145 | C-type lectin domain family 4, member E |
| GPR115 | 1.974 | 1.974 | 1.974 | 3.196 | 3.196 | 2.457 | 2.332 | 0.0319010 | G protein-coupled receptor 115 |
| LOC349196 | 4.621 | 4.909 | 4.735 | 6.053 | 5.601 | 6.131 | 2.334 | 0.0106431 | No description |
| MAP3K4 | 4.719 | 4.772 | 4.738 | 5.964 | 5.672 | 6.373 | 2.338 | 0.0094045 | mitogen-activated protein kinase kinase kinase 4 |
| NONO | 10.191 | 8.872 | 10.369 | 11.478 | 11.417 | 10.905 | 2.339 | 0.0322157 | non-POU domain containing, octamer-binding |
| C11orf75 | 3.475 | 3.539 | 3.771 | 4.471 | 4.765 | 5.330 | 2.341 | 0.0148135 | chromosome 11 open reading frame 75 |
| CENPO | 1.974 | 4.388 | 4.547 | 5.758 | 5.615 | 5.136 | 2.341 | 0.0474658 | centromere protein O |
| PTAR1 | 6.474 | 6.290 | 5.577 | 7.265 | 7.701 | 7.213 | 2.342 | 0.0188457 | protein prenyltransferase alpha subunit repeat containing 1 |
| AKAP11 | 2.559 | 3.358 | 3.205 | 5.223 | 4.030 | 3.787 | 2.342 | 0.0461335 | A kinase (PRKA) anchor protein 11 |
| LCORL | 2.559 | 3.637 | 2.840 | 4.137 | 4.255 | 3.787 | 2.342 | 0.0462164 | ligand dependent nuclear receptor corepressor-like |
| MTA3 | 8.077 | 7.610 | 8.628 | 9.418 | 9.305 | 8.949 | 2.342 | 0.0324743 | metastasis associated 1 family, members |
| TAF11 | 6.967 | 7.249 | 6.861 | 8.197 | 8.135 | 8.341 | 2.346 | 0.0057560 | TAF11 RNA polymerase II, TATA box binding protein (TBP)-associated factor, 28 kDa |
| POLG | 9.646 | 9.452 | 10.300 | 10.829 | 11.124 | 10.878 | 2.348 | 0.0214106 | polymerase (DNA directed), gamma |
| ISOC2 | 6.066 | 7.113 | 7.209 | 8.347 | 8.417 | 7.732 | 2.352 | 0.0271811 | isochorismatase domain containing 2 |
| RAB36 | 3.706 | 3.343 | 3.126 | 4.683 | 4.939 | 4.296 | 2.352 | 0.0139800 | RAB36, member RAS oncogene family |
| CYP2R1 | 6.242 | 6.098 | 7.185 | 7.915 | 8.018 | 7.332 | 2.352 | 0.0336124 | cytochrome P450, family 2, subfamily R, polypeptide 1 |
| F12 | 6.339 | 5.171 | 5.761 | 7.109 | 7.293 | 6.406 | 2.354 | 0.0465625 | coagulation factor XII (Hageman factor) |
| AKAP5 | 1.974 | 2.162 | 2.406 | 3.643 | 2.858 | 3.565 | 2.357 | 0.0205564 | A kinase (PRKA) anchor protein 5 |
| C20orf4 | 5.470 | 5.341 | 6.779 | 7.965 | 7.558 | 6.578 | 2.357 | 0.0447659 | chromosome 20 open reading frame 4 |
| C11orf52 | 5.376 | 5.483 | 5.107 | 7.359 | 6.322 | 6.616 | 2.361 | 0.0134129 | chromosome 11 open reading frame 52 |
| MEIS3P1 | 3.709 | 4.554 | 3.875 | 5.128 | 4.950 | 5.399 | 2.364 | 0.0263177 | Meis homeobox 3 pseudogene 1 |
| ZBTB39 | 2.974 | 3.943 | 4.085 | 5.327 | 4.396 | 5.164 | 2.366 | 0.0374467 | zinc finger and BTB domain containing 39 |
| SLC14A1 | 7.489 | 6.415 | 7.857 | 8.398 | 8.618 | 9.101 | 2.369 | 0.0287245 | solute carrier family 14 (urea transporter), member 1 (Kidd blood group) |
| GPR56 | 2.782 | 3.188 | 3.616 | 4.133 | 4.706 | 4.434 | 2.371 | 0.0190660 | G protein-coupled receptor 56 |
| TMEM169 | 3.649 | 3.616 | 2.912 | 5.020 | 4.443 | 4.158 | 2.372 | 0.0338688 | transmembrane protein 169 |
| C19orf70 | 8.013 | 7.575 | 8.637 | 9.260 | 9.360 | 9.089 | 2.373 | 0.0270161 | chromosome 19 open reading frame 70 |
| DDHD2 | 4.804 | 5.028 | 5.207 | 6.275 | 6.495 | 5.839 | 2.374 | 0.0137099 | DDHD domain containing 2 |
| DFFB | 3.117 | 3.238 | 4.145 | 4.902 | 4.485 | 4.473 | 2.374 | 0.0375288 | DNA fragmentation factor, 40 kDa, beta polypeptide (caspase-activated DNase) |
| TMTC1 | 5.127 | 4.282 | 4.457 | 5.554 | 5.706 | 6.142 | 2.378 | 0.0247805 | transmembrane and tetratricopeptide repeat containing 1 |
| MYO10 | 7.878 | 8.053 | 7.966 | 9.304 | 9.253 | 9.033 | 2.380 | 0.0035150 | myosin X |
| KIAA0649 | 6.098 | 6.051 | 5.844 | 7.213 | 7.350 | 7.300 | 2.382 | 0.0026124 | KIAA0649 |
| DDA1 | 10.017 | 10.336 | 11.472 | 12.461 | 12.669 | 11.270 | 2.383 | 0.0434229 | DET1 and DDB1 associated 1 |
| TECR | 9.846 | 9.578 | 10.232 | 11.486 | 11.246 | 10.688 | 2.384 | 0.0189210 | trans-2,3-enoyl-CoA reductase |
| GBGT1 | 4.290 | 3.827 | 4.054 | 5.540 | 5.545 | 4.946 | 2.387 | 0.0113945 | globoside alpha-1,3-N-acetylgalactosaminyltransferase 1 |
| BCSIL | 1.974 | 2.162 | 2.126 | 4.020 | 3.383 | 3.141 | 2.389 | 0.0094766 | BCS1-like (S. cerevisiae) |
| VCAM1 | 1.559 | 3.059 | 2.602 | 3.187 | 3.859 | 4.144 | 2.390 | 0.0479432 | vascular cell adhesion molecule 1 |
| ZNF845 | 1.913 | 3.335 | 3.974 | 4.592 | 4.657 | 4.592 | 2.390 | 0.0402487 | zinc finger protein 845 |
| ARPC5 | 5.678 | 7.423 | 6.601 | 8.405 | 7.668 | 7.860 | 2.393 | 0.0427698 | actin related protein 2/3 complex, subunit 5, 16 kDa |

TABLE 5-continued

Differentially Expressed Genes in CD24+ Breast Epithelial Cells

| | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| FAM114A1 | 3.637 | 4.308 | 3.367 | 5.570 | 4.747 | 4.842 | 2.398 | 0.0273292 | family with sequence similarity 114, member A1 |
| SHE | 4.088 | 4.366 | 4.725 | 5.770 | 5.631 | 5.581 | 2.403 | 0.0085948 | Src homology 2 domain containing E |
| NHLRC1 | 3.220 | 3.578 | 3.571 | 4.572 | 5.214 | 4.486 | 2.406 | 0.0125917 | NHL repeat containing 1 |
| YY1AP1 | 7.712 | 7.733 | 7.207 | 8.475 | 8.547 | 9.501 | 2.408 | 0.0254021 | YY1 associated protein 1 |
| C11orf54 | 5.592 | 6.349 | 6.160 | 7.786 | 6.861 | 7.098 | 2.409 | 0.0291504 | chromosome 11 open reading frame 54 |
| ITGAL | 1.974 | 1.974 | 2.953 | 4.222 | 4.222 | 3.220 | 2.410 | 0.0198657 | integrin, alpha L (antigen CD11A (p180), lymphocyte function-associated antigen 1; alpha polypeptide) |
| SPR | 4.042 | 4.854 | 4.370 | 6.123 | 6.055 | 5.059 | 2.410 | 0.0293653 | sepiapterin reductase (7,8-dihydrobiopterin:NADP+ oxidoreductase) |
| CASP8 | 6.145 | 7.706 | 7.623 | 8.692 | 8.976 | 8.621 | 2.412 | 0.0240161 | caspase 8, apoptosis-related cysteine peptidase |
| LRRC47 | 3.272 | 5.520 | 5.664 | 6.934 | 6.693 | 6.174 | 2.413 | 0.0480606 | leucine rich repeat containing 47 |
| NFXL1 | 3.364 | 3.567 | 2.627 | 4.637 | 4.811 | 4.422 | 2.416 | 0.0118872 | nuclear transcription factor, X-box binding-like 1 |
| LOC100216545 | 4.984 | 3.389 | 5.427 | 6.427 | 6.111 | 6.260 | 2.423 | 0.0329916 | No description |
| PRRG1 | 5.201 | 5.605 | 5.891 | 6.885 | 6.787 | 6.953 | 2.427 | 0.0084873 | proline rich Gla (G-carboxyglutamic acid) 1 |
| MAPKSP1 | 8.097 | 7.025 | 7.473 | 8.921 | 8.561 | 8.753 | 2.428 | 0.0244098 | MAPK scaffold protein 1 |
| LOC641367 | 0.974 | 2.108 | 1.832 | 3.388 | 2.712 | 2.777 | 2.429 | 0.0275265 | No description |
| PLLP | 5.991 | 5.525 | 4.712 | 6.929 | 6.806 | 6.310 | 2.429 | 0.0341719 | plasmolipin |
| METTL11D1 | 8.582 | 8.836 | 9.678 | 10.192 | 10.062 | 10.117 | 2.431 | 0.0367229 | methyltransferase 11 domain containing 1 |
| TSPYL2 | 10.969 | 9.365 | 10.694 | 12.198 | 11.172 | 11.977 | 2.434 | 0.0458296 | TSPY-like 2 |
| ZBTB7C | 4.205 | 5.546 | 4.741 | 6.190 | 6.025 | 5.920 | 2.436 | 0.0360200 | zinc finger and BTB domain containing 7C |
| POM121 | 4.208 | 3.825 | 4.128 | 5.413 | 6.042 | 5.095 | 2.437 | 0.0107728 | POM121 membrane glycoprotein |
| CSF1 | 5.211 | 4.889 | 4.945 | 6.496 | 6.333 | 6.160 | 2.437 | 0.0042510 | colony stimulating factor 1 (macrophage) |
| SEC22B | 6.651 | 7.075 | 6.686 | 8.410 | 7.972 | 7.456 | 2.439 | 0.0268120 | SEC22 vesicle trafficking protein homolog B (S. cerevisiae) (gene/pseudogene) |
| NSFL1C | 10.111 | 9.868 | 11.340 | 12.348 | 12.166 | 11.155 | 2.440 | 0.0452717 | NSFL1 (p97) cofactor (p47) |
| PSD | 1.974 | 2.013 | 3.051 | 3.263 | 4.098 | 3.660 | 2.443 | 0.0306124 | pleckstrin and Sec7 domain containing |
| RIPK4 | 4.892 | 4.256 | 4.523 | 5.812 | 5.163 | 6.228 | 2.444 | 0.0329470 | receptor-interacting serine-threonine kinase 4 |
| C15orf17 | 6.961 | 7.137 | 7.435 | 7.966 | 8.450 | 8.726 | 2.446 | 0.0167744 | chromosome 15 open reading frame 17 |
| OAMK2D | 5.583 | 4.746 | 4.316 | 6.605 | 5.609 | 6.459 | 2.450 | 0.0383246 | calcium/calmodulin-dependent protein kinase II delta |
| C9orf5 | 5.539 | 6.048 | 6.943 | 7.649 | 7.342 | 7.062 | 2.451 | 0.0497099 | polymerase (DNA-directed), delta interacting protein 3 |
| ZBTB5 | 7.488 | 6.203 | 7.048 | 8.271 | 8.342 | 8.462 | 2.452 | 0.0178181 | chromosome 9 open reading frame 5 |
| TTLL4 | 9.505 | 8.568 | 8.396 | 10.449 | 10.024 | 9.694 | 2.458 | 0.0360576 | zinc finger and BTB domain containing 5 |
| JRK | 5.282 | 6.277 | 6.841 | 6.975 | 7.576 | 7.736 | 2.461 | 0.0482233 | tubulin tyrosine ligase-like family, member 4 |
| MLH1 | 3.859 | 5.068 | 4.340 | 5.640 | 5.454 | 5.908 | 2.463 | 0.0292164 | jerky homolog (mouse) |
| SMYD4 | 5.799 | 5.865 | 6.138 | 7.229 | 7.100 | 7.438 | 2.464 | 0.0043032 | mutL homolog 1, colon cancer, nonpolyposis type 2 (E. coli) |
| SLCO4A1 | 2.782 | 3.792 | 3.025 | 5.291 | 4.327 | 3.886 | 2.466 | 0.0481282 | SET and MYND domain containing 4 |
| POLDIP3 | 8.617 | 7.793 | 7.143 | 9.097 | 9.000 | 9.310 | 2.468 | 0.0359609 | solute carrier organic anion transporter family, member 4A1 |
| AATF | 5.040 | 6.282 | 5.618 | 6.871 | 6.921 | 6.985 | 2.468 | 0.0243883 | polymerase (DNA-directed), delta interacting protein 3 |
| RUNX3 | 5.909 | 6.592 | 6.563 | 7.714 | 7.896 | 7.714 | 2.469 | 0.0074022 | apoptosis antagonizing transcription factor |
| PIP4K2B | 4.085 | 4.420 | 4.196 | 5.724 | 5.194 | 5.699 | 2.470 | 0.0081236 | runt-related transcription factor 3 |
| YIPF4 | 6.100 | 6.407 | 5.317 | 7.265 | 7.510 | 7.405 | 2.471 | 0.0134682 | phosphatidylinositol-5-phosphate 4-kinase, type II, beta |
| REV1 | 5.724 | 5.873 | 6.713 | 7.341 | 7.444 | 7.030 | 2.472 | 0.0287629 | Yip1 domain family, member 4 |
| RANBP9 | 8.394 | 7.821 | 7.439 | 9.558 | 8.831 | 9.127 | 2.472 | 0.0224889 | REV1 homolog (S. cerevisiae) |
| ZNF521 | 2.559 | 3.061 | 2.559 | 4.622 | 3.648 | 3.869 | 2.478 | 0.0195503 | RAN binding protein 9 |
| EAPP | 6.405 | 7.567 | 6.653 | 8.171 | 7.991 | 7.715 | 2.479 | 0.0470153 | zinc finger protein 521 |
| | | | | | | | | | E2F-associated phosphoprotein |

TABLE 5-continued

Differentially Expressed Genes in CD24+ Breast Epithelial Cells

| | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| RRN3P3 | 9.906 | 9.937 | 9.889 | 11.500 | 11.216 | 10.649 | 2.479 | 0.0152579 | RNA polymerase I transcription factor homolog (S. cerevisiae) pseudogene 3 |
| REEP4 | 6.422 | 6.683 | 7.484 | 7.995 | 8.494 | 7.738 | 2.482 | 0.0346930 | receptor accessory protein 4 |
| CUL2 | 7.201 | 6.507 | 6.239 | 7.821 | 8.187 | 7.634 | 2.486 | 0.0235134 | cullin 2 |
| KCNH8 | 2.747 | 3.388 | 2.649 | 3.868 | 4.627 | 4.703 | 2.487 | 0.0144543 | potassium voltage-gated channel, subfamily H (eag-related), member 8 |
| GOLGB1 | 7.634 | 7.773 | 7.435 | 9.088 | 8.632 | 8.953 | 2.488 | 0.0064121 | golgin B1 |
| MIF4GD | 5.514 | 5.490 | 5.502 | 6.818 | 7.270 | 5.932 | 2.490 | 0.0393753 | MIF4G domain containing |
| TIPIN | 2.878 | 3.089 | 2.531 | 4.321 | 4.406 | 3.758 | 2.491 | 0.0116915 | TIMELESS interacting protein |
| DIAPH3 | 2.296 | 2.859 | 2.859 | 4.054 | 4.178 | 4.042 | 2.495 | 0.0050683 | diaphanous homolog 3 (Drosophila) |
| SLC28A3 | 4.153 | 3.758 | 3.900 | 5.475 | 5.383 | 4.717 | 2.499 | 0.0148457 | solute carrier family 28 (sodium-coupled nucleoside transporter), member 3 |
| GRPEL1 | 7.862 | 8.122 | 8.179 | 9.294 | 9.501 | 9.418 | 2.500 | 0.0029371 | GrpE-like 1, mitochondrial (E. coli) |
| CEBPB | 12.579 | 13.013 | 12.426 | 13.640 | 13.901 | 14.449 | 2.501 | 0.0149225 | CCAAT/enhancer binding protein (C/EBP), beta |
| CYP27C1 | 5.087 | 5.433 | 6.365 | 7.231 | 7.053 | 6.410 | 2.501 | 0.0406408 | cytochrome P450, family 27, subfamily C, polypeptide 1 |
| CTCF | 4.779 | 6.086 | 5.032 | 7.200 | 6.473 | 6.104 | 2.505 | 0.0490138 | CCCTC-binding factor (zinc finger protein) |
| RBM15B | 6.944 | 7.438 | 8.130 | 9.033 | 8.763 | 8.325 | 2.505 | 0.0376723 | RNA binding motif protein 15B |
| CETN2 | 8.366 | 8.051 | 7.147 | 9.384 | 9.378 | 8.898 | 2.508 | 0.0239655 | centrin, EF-hand protein, 2 |
| C9orf80 | 6.203 | 5.752 | 6.466 | 7.793 | 7.415 | 7.318 | 2.509 | 0.0100368 | chromosome 9 open reading frame 80 |
| RHEBL1 | 2.878 | 2.752 | 3.089 | 3.469 | 4.207 | 4.801 | 2.512 | 0.0323807 | Ras homolog enriched in brain like 1 |
| ZSCAN16 | 4.054 | 4.312 | 5.383 | 6.371 | 6.133 | 5.386 | 2.518 | 0.0379923 | zinc finger and SCAN domain containing 16 |
| RAB2B | 5.107 | 4.238 | 5.371 | 6.705 | 6.228 | 6.211 | 2.521 | 0.0162985 | RAB2B, member RAS oncogene family |
| ASCC1 | 6.485 | 6.707 | 6.454 | 8.605 | 7.820 | 7.320 | 2.522 | 0.0218880 | activating signal cointegrator 1 complex subunit 1 |
| ST3GAL5 | 1.913 | 2.038 | 2.636 | 3.974 | 3.825 | 3.152 | 2.528 | 0.0137398 | STS beta-galactoside alpha-2,3-sialyltransferase 5 |
| CBX7 | 4.821 | 5.488 | 4.848 | 7.024 | 6.188 | 6.151 | 2.531 | 0.0176546 | chromobox homolog 7 |
| PAR5 | 5.125 | 4.370 | 5.404 | 5.711 | 7.012 | 5.997 | 2.532 | 0.0489432 | No description |
| RAP1GDS1 | 2.559 | 4.550 | 4.314 | 5.476 | 5.895 | 4.939 | 2.539 | 0.0439447 | RAP1, GTP-GDP dissociation stimulator 1 |
| C9orf78 | 6.392 | 8.040 | 7.291 | 9.029 | 8.512 | 8.637 | 2.542 | 0.0293239 | chromosome 9 open reading frame 78 |
| PARG | 5.048 | 5.375 | 5.169 | 6.511 | 6.446 | 6.721 | 2.543 | 0.0032134 | poly (ADP-ribose) glycohydrolase |
| IDE | 5.944 | 6.890 | 6.385 | 7.915 | 8.238 | 7.136 | 2.545 | 0.0281972 | Description |
| C1orf21 | 8.690 | 7.456 | 7.727 | 8.805 | 9.136 | 9.274 | 2.548 | 0.0478465 | chromosome 1 open reading frame 21 |
| EFNB3 | 6.087 | 5.860 | 6.755 | 7.563 | 7.213 | 7.549 | 2.554 | 0.0201082 | ephrin-B3 |
| BRP44 | 0.974 | 1.050 | 1.050 | 2.404 | 1.692 | 3.304 | 2.557 | 0.0277038 | brain protein 44 |
| CCDC55 | 7.769 | 7.031 | 8.000 | 9.364 | 8.999 | 8.562 | 2.558 | 0.0208074 | coiled-coil domain containing 55 |
| SYNPO | 4.296 | 5.311 | 5.039 | 6.395 | 6.072 | 6.452 | 2.560 | 0.0138450 | synaptopodin |
| RNF145 | 9.825 | 8.940 | 8.623 | 10.297 | 10.060 | 10.362 | 2.562 | 0.0421282 | ring finger protein 145 |
| SLC25A22 | 4.793 | 4.313 | 4.398 | 6.037 | 6.150 | 5.273 | 2.562 | 0.0166938 | solute carrier family 25 (mitochondrial carrier: glutamate), member 22 |
| SF3B2 | 8.997 | 8.832 | 8.781 | 10.324 | 10.355 | 9.382 | 2.564 | 0.0293070 | splicing factor 3b, subunit 2, 145 kDa |
| SART1 | 8.474 | 7.721 | 8.977 | 9.835 | 10.041 | 9.729 | 2.568 | 0.0159432 | squamous cell carcinoma antigen recognized by T cells |
| SURF2 | 2.247 | 2.108 | 3.021 | 3.469 | 4.507 | 3.469 | 2.569 | 0.0313998 | surfeit 2 |
| TUSC1 | 7.051 | 8.043 | 7.108 | 8.698 | 8.414 | 8.481 | 2.572 | 0.0325365 | tumor suppressor candidate 1 |
| PSMD1 | 9.642 | 10.655 | 10.179 | 12.019 | 11.556 | 10.897 | 2.575 | 0.0318557 | proteasome (prosome, macropain) 26S subunit, non-ATPase, 1 |
| PPID | 3.247 | 3.090 | 3.724 | 4.612 | 4.436 | 5.403 | 2.575 | 0.0146094 | peptidylprolyl isomerase D |
| PIGS | 6.985 | 7.319 | 6.298 | 8.695 | 8.350 | 7.551 | 2.576 | 0.0344413 | phosphatidylinositol glycan anchor biosynthesis, class S |
| PAPL | 8.713 | 8.326 | 8.955 | 10.321 | 10.058 | 9.726 | 2.578 | 0.0097253 | No description |

TABLE 5-continued

Differentially Expressed Genes in CD24+ Breast Epithelial Cells

| | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| KRBA2 | 8.158 | 7.357 | 8.709 | 9.979 | 9.525 | 8.987 | 2.579 | 0.0319348 | KRAB-A domain containing 2 |
| NFYA | 7.953 | 7.703 | 8.413 | 9.165 | 9.320 | 9.568 | 2.580 | 0.0100875 | nuclear transcription factor Y, alpha |
| LOC84740 | 2.559 | 2.559 | 2.559 | 3.802 | 3.927 | 4.904 | 2.581 | 0.0091819 | No description |
| GLIPR1L2 | 3.247 | 2.901 | 3.335 | 4.707 | 4.038 | 4.683 | 2.588 | 0.0117682 | GLI pathogenesis-related 1 like 2 |
| RFXANK | 7.705 | 7.623 | 8.961 | 10.338 | 10.187 | 8.907 | 2.598 | 0.0299770 | regulatory factor X-associated ankyrin-containing protein |
| TSR1 | 4.566 | 4.395 | 3.988 | 6.003 | 5.773 | 4.944 | 2.598 | 0.0265618 | TSR1,20S rRNA accumulation, homolog (S. cerevisiae) |
| DPY30 | 5.171 | 6.115 | 5.163 | 6.707 | 6.665 | 6.542 | 2.600 | 0.0279025 | dpy-30 homolog (C. elegans) |
| C3orf1 | 7.255 | 6.208 | 6.001 | 7.967 | 7.828 | 7.379 | 2.600 | 0.0386815 | chromosome 3 open reading frame 1 |
| POU2F2 | 3.144 | 4.764 | 5.330 | 6.143 | 5.608 | 6.164 | 2.601 | 0.0495733 | POU class 2 homeobox 2 |
| SMC4 | 3.616 | 3.998 | 3.730 | 4.999 | 5.067 | 5.541 | 2.607 | 0.0056738 | structural maintenance of chromosomes 4 |
| MCM2 | 5.823 | 5.419 | 6.041 | 7.480 | 7.205 | 6.770 | 2.608 | 0.0109493 | minichromosome maintenance complex component 2 |
| CALU | 8.743 | 8.338 | 8.315 | 10.126 | 9.855 | 9.232 | 2.609 | 0.0175656 | calumenin |
| LOC729603 | 7.575 | 6.840 | 5.850 | 8.871 | 7.801 | 8.223 | 2.609 | 0.0370414 | No description |
| GMPS | 7.213 | 6.436 | 5.967 | 7.821 | 8.057 | 7.669 | 2.611 | 0.0251090 | guanine monphosphate synthetase |
| ATM IN | 5.569 | 6.587 | 6.101 | 7.810 | 7.487 | 7.209 | 2.613 | 0.0153338 | ATM interactor |
| PRDX6 | 10.103 | 10.212 | 10.096 | 11.872 | 11.495 | 11.351 | 2.625 | 0.0035257 | peroxiredoxin 6 |
| SYNGR1 | 6.635 | 5.880 | 7.383 | 8.503 | 8.028 | 7.579 | 2.626 | 0.0369117 | synaptogyrin 1 |
| INPP5A | 4.719 | 6.190 | 5.431 | 7.098 | 6.730 | 6.824 | 2.627 | 0.0243715 | inositol polyphosphate-5-phosphatase, 40 kDa |
| IGF1 | 4.450 | 5.091 | 6.018 | 6.893 | 6.487 | 6.436 | 2.630 | 0.0308565 | insulin-like growth factor 1 (somatomedin C) |
| RGMA | 6.160 | 6.709 | 5.992 | 7.812 | 8.037 | 7.389 | 2.634 | 0.0100077 | RGM domain family, member A |
| SERPINH1 | 6.604 | 7.734 | 7.382 | 8.177 | 8.357 | 9.132 | 2.636 | 0.0344221 | serpin peptidase inhibitor, clade H (heat shock protein 47), member 1, (collagen binding protein 1) |
| FAM126A | 2.559 | 3.205 | 2.840 | 3.752 | 4.367 | 4.604 | 2.638 | 0.0147122 | family with sequence similarity 126, member A |
| CLDN10 | 2.296 | 2.627 | 2.296 | 4.983 | 3.697 | 3.043 | 2.639 | 0.0392479 | claudin 10 |
| ASXL1 | 5.837 | 5.419 | 5.861 | 6.819 | 7.011 | 7.363 | 2.640 | 0.0078450 | additional sex combs like 1 (Drosophila) |
| MMAA | 3.412 | 4.371 | 3.206 | 5.062 | 4.607 | 5.745 | 2.640 | 0.0282410 | methylmalonic aciduria (cobalamin deficiency) cblA type |
| TGDS | 2.671 | 2.836 | 3.616 | 4.637 | 4.239 | 4.158 | 2.644 | 0.0190553 | TDP-glucose 4,6-dehydratase |
| PAGI | 4.126 | 3.571 | 3.886 | 6.029 | 5.290 | 4.368 | 2.647 | 0.0394674 | phosphoprotein associated with glycosphingolipid microdomains 1 |
| KIAA1919 | 3.706 | 5.049 | 4.296 | 5.821 | 5.776 | 5.112 | 2.650 | 0.0454758 | KIAA1919 |
| HSPG2 | 7.286 | 7.580 | 8.159 | 8.692 | 8.961 | 9.602 | 2.651 | 0.0185733 | heparan sulfate proteoglycan 2 |
| C4orf32 | 3.706 | 4.032 | 2.916 | 4.983 | 4.512 | 5.439 | 2.652 | 0.0235533 | chromosome 4 open reading frame 32 |
| SNHG10 | 3.810 | 3.173 | 3.173 | 4.580 | 4.227 | 5.571 | 2.686 | 0.0285602 | small nucleolar RNA host gene 10 (non-protein coding) |
| VAC14 | 3.117 | 3.410 | 4.315 | 4.838 | 4.821 | 4.665 | 2.659 | 0.0353492 | Vac14 homolog (S. cerevisiae) |
| NAA15 | 4.964 | 5.510 | 5.642 | 5.968 | 7.058 | 6.922 | 2.661 | 0.0307299 | N(alpha)-acetyltransferase 15, NatA auxiliary subunit |
| TMEM213 | 6.680 | 5.897 | 5.880 | 7.898 | 7.294 | 7.370 | 2.664 | 0.0157897 | transmembrane protein 213 |
| MCOLN2 | 4.991 | 5.253 | 5.988 | 6.746 | 6.407 | 6.752 | 2.669 | 0.0225725 | mucolipin 2 |
| PPP2R5B | 9.641 | 8.691 | 8.932 | 10.134 | 10.349 | 10.596 | 2.670 | 0.0193607 | protein phosphatase 2, regulatory subunit B'; beta |
| LIX1L | -0.026 | 2.108 | 1.734 | 3.335 | 2.636 | 3.152 | 2.672 | 0.0341343 | Lix1 homolog (mouse)-like |
| HLA-B | 13.780 | 14.160 | 14.258 | 15.724 | 15.548 | 15.205 | 2.686 | 0.0059294 | major histocompatibility complex, class I, B |
| UGP2 | 5.545 | 5.777 | 4.719 | 6.422 | 6.747 | 7.204 | 2.688 | 0.0192302 | UDP-glucose pyrophosphorylase 2 |
| DLL4 | 0.974 | 1.050 | 0.974 | 2.108 | 2.402 | 3.304 | 2.690 | 0.0109877 | delta-like 4 (Drosophila) |
| LSM11 | 0.974 | 1.050 | 1.050 | 2.404 | 3.022 | 2.404 | 2.694 | 0.0036009 | LSM11, U7 small nuclear RNA associated |
| COL2A1 | 0.974 | 0.974 | 1.264 | 2.848 | 2.402 | 2.404 | 2.694 | 0.0036608 | collagen, type II, alpha 1 |
| LOC1001339 20 | 0.974 | 0.974 | 0.974 | 2.404 | 2.848 | 1.819 | 2.694 | 0.0130414 | No description |
| ZNF484 | 0.974 | 1.328 | 0.974 | 2.848 | 1.692 | 2.404 | 2.694 | 0.0281781 | zinc finger protein 484 |

TABLE 5-continued

Differentially Expressed Genes in CD24+ Breast Epithelial Cells

| | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| psiTPTE22 | 0.974 | 1.050 | 2.432 | 3.772 | 3.022 | 2.404 | 2.694 | 0.0380821 | No description |
| CCDC3 | 0.974 | 2.546 | 1.692 | 2.404 | 3.887 | 3.922 | 2.694 | 0.0392371 | coiled-coil domain containing 3 |
| TOPORS | 4.946 | 5.608 | 4.047 | 6.376 | 6.096 | 6.618 | 2.695 | 0.0254712 | topoisomerase I binding, arginine/serine-rich, E3 ubiquitin protein ligase |
| SLC44A1 | 7.517 | 8.577 | 7.912 | 10.007 | 9.246 | 9.108 | 2.696 | 0.0211228 | solute carrier family 44, member 1 |
| NCBP1 | 5.975 | 4.813 | 4.725 | 6.155 | 6.815 | 6.672 | 2.696 | 0.0300798 | nuclear cap binding protein subunit 1,80 kDa |
| SNX5 | 8.871 | 7.731 | 8.382 | 9.813 | 9.973 | 9.463 | 2.696 | 0.0171773 | sorting nexin 5 |
| HIVEP3 | 6.813 | 7.903 | 8.321 | 8.546 | 9.250 | 9.752 | 2.697 | 0.0374682 | human immunodeficiency virus type I enhancer binding protein 3 |
| DNAJC8 | 8.362 | 8.208 | 8.860 | 9.767 | 9.852 | 9.797 | 2.703 | 0.0074129 | DnaJ (Hsp40) homolog, subfamily C, member 8 |
| ZFP41 | 4.290 | 4.179 | 5.210 | 6.404 | 5.760 | 5.616 | 2.708 | 0.0248649 | zinc finger protein 41 homolog (mouse) |
| MLXIPL | 3.616 | 4.824 | 5.281 | 6.718 | 5.827 | 5.744 | 2.709 | 0.0383139 | MLX interacting protein-like |
| NOLC1 | 5.513 | 5.585 | 5.436 | 6.339 | 7.002 | 7.023 | 2.709 | 0.0108243 | nucleolar and coiled-body phosphoprotein 1 |
| FRG1 | 5.086 | 5.678 | 5.514 | 7.164 | 6.953 | 6.056 | 2.710 | 0.0262180 | FSHD region gene 1 |
| DBF4B | 9.101 | 8.539 | 8.795 | 10.346 | 10.074 | 10.235 | 2.713 | 0.0047337 | DBF4 homolog B (*S. cerevisiae*) |
| C2orf60 | 4.377 | 4.991 | 5.256 | 6.562 | 6.433 | 5.828 | 2.716 | 0.0163384 | chromosome 2 open reading frame 60 |
| POLL | 6.787 | 6.104 | 6.407 | 7.852 | 7.738 | 7.949 | 2.722 | 0.0059616 | polymerase (DNA directed), lambda |
| AARSD1 | 5.435 | 4.514 | 4.585 | 6.511 | 6.343 | 5.959 | 2.722 | 0.0146608 | alanyl-tRNA synthetase domain containing 1 |
| CAPZB | 11.499 | 11.432 | 11.624 | 13.262 | 12.946 | 12.317 | 2.726 | 0.0138780 | capping protein (actin filament) muscle Z-line, beta |
| LOC150381 | 6.630 | 6.217 | 7.227 | 8.371 | 8.233 | 7.669 | 2.735 | 0.0181681 | No description |
| C10orf90 | 3.059 | 2.948 | 2.758 | 4.512 | 4.144 | 4.422 | 2.737 | 0.0029831 | chromosome 10 open reading frame 90 |
| MAP4K4 | 8.078 | 8.583 | 8.440 | 9.942 | 9.801 | 9.893 | 2.738 | 0.0028005 | mitogen-activated protein kinase kinase kinase kinase 4 |
| DCP1B | 1.974 | 4.222 | 3.712 | 5.167 | 5.556 | 4.378 | 2.741 | 0.0464674 | DCP1 decapping enzyme homolog B (*S. cerevisiae*) |
| SFXN1 | 4.350 | 5.214 | 5.258 | 6.713 | 6.081 | 6.226 | 2.741 | 0.0170668 | sideroflexin 1 |
| BAZ1B | 6.133 | 7.137 | 7.699 | 8.550 | 8.890 | 8.592 | 2.742 | 0.0160691 | bromodomain adjacent to zinc finger domain, 1B |
| DGKE | 6.600 | 6.520 | 7.100 | 8.056 | 8.131 | 8.013 | 2.742 | 0.0064697 | diacylglycerol kinase, epsilon 64 kDa |
| PDGFA | 4.125 | 5.890 | 4.979 | 6.120 | 6.434 | 7.315 | 2.742 | 0.0355188 | platelet-derived growth factor alpha polypeptide |
| LOC401127 | 3.892 | 4.192 | 4.375 | 5.989 | 5.648 | 5.309 | 2.743 | 0.0063822 | No description |
| MRPL32 | 8.752 | 8.928 | 8.479 | 10.190 | 10.384 | 10.205 | 2.744 | 0.0022540 | mitochondrial ribosomal protein L32 |
| DYNLL1 | 11.047 | 10.410 | 11.446 | 12.504 | 12.137 | 12.840 | 2.746 | 0.0134981 | dynein, light chain, LC8-type 1 |
| GPX3 | 3.434 | 5.312 | 5.544 | 5.989 | 5.648 | 5.756 | 2.746 | 0.0470952 | glutathione peroxidase 3 (plasma) |
| SDF4 | 8.896 | 9.905 | 9.449 | 11.363 | 10.939 | 10.263 | 2.749 | 0.0237299 | stromal cell derived factor 4 |
| ZNF692 | 8.405 | 7.000 | 8.488 | 9.769 | 9.636 | 9.947 | 2.752 | 0.0136992 | zinc finger protein 692 |
| CONC | 5.378 | 5.289 | 5.277 | 6.924 | 6.749 | 6.170 | 2.752 | 0.0102709 | cyclin O |
| GDAP1 | 3.908 | 4.014 | 3.616 | 5.475 | 5.475 | 4.570 | 2.752 | 0.0176332 | ganglioside-induced differentiation-associated protein 1 |
| INPP5K | 5.140 | 6.325 | 5.845 | 7.520 | 7.305 | 6.996 | 2.756 | 0.0150998 | inositol polyphosphate-5-phosphatase K |
| SIDT2 | 8.076 | 6.671 | 7.178 | 8.664 | 8.640 | 8.637 | 2.756 | 0.0273400 | SID1 transmembrane family, member 2 |
| SMG6 | 5.967 | 7.509 | 8.503 | 9.158 | 8.977 | 8.834 | 2.766 | 0.0496048 | Smg-6 homolog, nonsense mediated mRNA decay factor (*C. elegans*) |
| ADORA2A | 4.492 | 6.270 | 5.547 | 6.986 | 6.447 | 7.742 | 2.773 | 0.0377352 | adenosine A2a receptor |
| RUNDC2C | 3.296 | 3.374 | 3.913 | 4.772 | 5.427 | 4.820 | 2.781 | 0.0093530 | RUN domain containing 2C |
| GNG4 | 2.296 | 3.934 | 4.241 | 5.410 | 5.443 | 4.701 | 2.782 | 0.0342348 | guanine nucleotide binding protein (G protein), gamma 4 |
| MNAT1 | 6.674 | 6.863 | 7.537 | 9.014 | 8.747 | 8.064 | 2.783 | 0.0132502 | menage a trois homolog 1, cyclin H assembly factor (*Xenopus laevis*) |
| CD58 | 4.710 | 4.339 | 4.351 | 6.191 | 5.624 | 5.896 | 2.791 | 0.0053231 | CD58 molecule |
| ATP5J2 | 6.210 | 5.183 | 7.063 | 7.618 | 8.544 | 7.279 | 2.791 | 0.0379186 | ATP synthase, H+ transporting, mitochondrial Fo complex, subunit F2 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| C15orf24 | 6.140 | 6.611 | 5.373 | 7.640 | 7.622 | 6.911 | 2.793 | 0.0298005 | chromosome 15 open reading frame 24 |
| FGL2 | 4.126 | 2.861 | 3.642 | 5.223 | 5.125 | 4.978 | 2.795 | 0.0130844 | fibrinogen-like 2 |
| METTL2A | 7.173 | 5.723 | 6.084 | 7.794 | 7.571 | 7.348 | 2.803 | 0.0431857 | methyltransferase like 2A |
| TCEA2 | 7.424 | 6.190 | 8.087 | 8.912 | 8.919 | 8.582 | 2.805 | 0.0320599 | transcription elongation factor A (SII), 2 |
| TBC1D10A | 4.544 | 3.928 | 3.723 | 5.595 | 5.484 | 5.214 | 2.811 | 0.0113784 | TBC1 domain family, member 10A |
| PMS2 | 5.197 | 4.944 | 5.944 | 6.694 | 6.797 | 6.438 | 2.817 | 0.0193031 | PMS2 postmeiotic segregation increased 2 (S. cerevisiae) |
| NEK8 | 4.872 | 4.470 | 5.613 | 6.472 | 5.966 | 6.842 | 2.821 | 0.0220698 | NIMA (never in mitosis gene a)- related kinase 9 |
| SMCR8 | 6.199 | 7.656 | 7.715 | 9.211 | 8.553 | 8.609 | 2.821 | 0.0263553 | Smith-Magenis syndrome chromosome region, candidate 8 |
| RNASEH2C | 3.470 | 3.844 | 4.873 | 5.967 | 5.341 | 5.171 | 2.823 | 0.0308757 | ribonuclease H2, subunit C |
| MRTO4 | 6.711 | 7.659 | 8.709 | 9.157 | 9.990 | 8.857 | 2.824 | 0.0403546 | mRNA turnover 4 homolog (S. cerevisiae) |
| BTRC | 3.539 | 4.921 | 5.160 | 5.820 | 6.420 | 6.574 | 2.826 | 0.0215265 | beta-transducin repeat containing |
| VCAN | 1.559 | 1.759 | 1.559 | 4.705 | 2.454 | 3.059 | 2.828 | 0.0315718 | versican |
| ADI1 | 5.049 | 4.927 | 5.119 | 6.961 | 6.376 | 6.549 | 2.829 | 0.0028726 | acireductone dioxygenase 1 |
| UIMC1 | 5.309 | 5.317 | 4.764 | 6.437 | 6.536 | 6.820 | 2.834 | 0.0054305 | ubiquitin interaction motif containing 1 |
| ITCH | 5.186 | 4.795 | 5.093 | 6.547 | 6.694 | 6.545 | 2.844 | 0.0016493 | itchy E3 ubiquitin protein ligase homolog (mouse) |
| ABCD1 | 4.492 | 5.534 | 6.395 | 7.168 | 6.566 | 7.042 | 2.845 | 0.0436869 | ATP-binding cassette, sub-family D (ALD), member 1 |
| ACOX3 | 6.927 | 6.606 | 7.738 | 9.178 | 8.898 | 8.116 | 2.848 | 0.0173323 | acyl-CoA oxidase 3, pristanoyl |
| DCLRE1C | 5.254 | 5.009 | 6.172 | 7.683 | 7.577 | 6.439 | 2.849 | 0.0187951 | DNA cross-link repair 1C |
| C10orf35 | 6.858 | 6.089 | 7.754 | 8.962 | 8.851 | 7.601 | 2.851 | 0.0436262 | chromosome 10 open reading frame 35 |
| ZNF507 | 4.374 | 4.418 | 4.094 | 5.930 | 5.691 | 5.744 | 2.852 | 0.0020814 | zinc finger protein 507 |
| VPS25 | 8.394 | 8.969 | 8.806 | 11.110 | 10.319 | 9.535 | 2.854 | 0.0210345 | vacuolar protein sorting 25 homolog (S. cerevisiae) |
| ALOX12P2 | 2.296 | 3.376 | 2.875 | 5.154 | 4.042 | 3.809 | 2.854 | 0.0317091 | arachidonate 12-lipoxygenase pseudogene 2 |
| MIDI IPI | 6.296 | 6.692 | 6.115 | 7.809 | 7.648 | 7.828 | 2.854 | 0.0048987 | MIDI interacting protein 1 (gastrulation specific G12 homolog (zebrafish)) |
| SLC25A3 | 7.112 | 6.977 | 6.783 | 8.533 | 8.628 | 7.680 | 2.859 | 0.0168665 | solute carrier family 25 (mitochondrial carrier; phosphate carrier), member 3 |
| ZNF350 | 3.090 | 2.075 | 1.610 | 3.848 | 3.187 | 3.591 | 2.861 | 0.0431090 | zinc finger protein 350 |
| RINT1 | 5.720 | 6.093 | 4.825 | 7.272 | 7.237 | 6.471 | 2.861 | 0.0261903 | RAD50 interactor 1 |
| MX2 | 0.974 | 1.643 | 2.098 | 3.160 | 3.022 | 3.304 | 2.862 | 0.0097360 | myxovirus (influenza virus) resistance 2 (mouse) |
| RASD2 | 3.593 | 2.625 | 2.819 | 4.917 | 4.222 | 4.338 | 2.867 | 0.0150698 | RASD family, member 2 |
| CENPM | 2.519 | 3.187 | 4.390 | 4.952 | 4.706 | 4.705 | 2.867 | 0.0422095 | centromere protein M |
| JAM2 | 0.974 | 1.328 | 0.974 | 2.848 | 2.402 | 2.777 | 2.868 | 0.0029263 | junctional adhesion molecule 2 |
| VWDE | 2.296 | 2.296 | 2.327 | 4.486 | 3.817 | 3.043 | 2.868 | 0.0200652 | von Willebrand factor D and EGF domains |
| MUT | 2.296 | 2.838 | 3.809 | 4.537 | 3.817 | 4.740 | 2.868 | 0.0409210 | methylmalonyl CoA mutase |
| UBFD1 | 5.967 | 5.703 | 6.087 | 7.670 | 7.465 | 7.226 | 2.874 | 0.0030315 | ubiquitin family domain containing 1 |
| PPAPDC2 | 3.616 | 5.395 | 4.647 | 6.650 | 6.170 | 5.603 | 2.874 | 0.0349401 | phosphatidic acid phosphatase type 2 domain containing 2 |
| C2orf15 | 7.713 | 7.332 | 7.597 | 9.236 | 9.150 | 8.832 | 2.883 | 0.0029724 | chromosome 2 open reading frame 15 |
| PQLC1 | 8.469 | 9.177 | 9.887 | 10.705 | 10.647 | 10.863 | 2.888 | 0.0161466 | PQ loop repeat containing 1 |
| ZNF397OS | 5.167 | 4.844 | 4.572 | 6.697 | 6.455 | 6.068 | 2.888 | 0.0058757 | No description |
| LOC283314 | 5.497 | 4.846 | 6.423 | 7.742 | 7.664 | 6.376 | 2.891 | 0.0340913 | No description |
| NASP | 8.454 | 7.487 | 7.984 | 9.498 | 9.515 | 9.719 | 2.894 | 0.0068596 | nuclear autoantigenic sperm protein (histone-binding) |
| GPATCH3 | 5.954 | 5.667 | 6.293 | 7.842 | 7.487 | 6.999 | 2.900 | 0.0107183 | G patch domain containing 3 |
| DNM1L | 7.239 | 7.328 | 6.939 | 8.775 | 8.801 | 8.749 | 2.903 | 0.0013753 | dynamin 1-like |
| RPL12 | 14.890 | 13.395 | 14.196 | 15.217 | 15.932 | 15.733 | 2.903 | 0.0279363 | ribosomal protein L12 |
| HPS6 | 5.931 | 5.942 | 4.906 | 7.480 | 7.358 | 6.616 | 2.903 | 0.0182786 | Hermansky-Pudlak syndrome 6 |
| C11orf57 | 4.854 | 5.465 | 4.474 | 6.392 | 6.396 | 6.063 | 2.903 | 0.0149854 | chromosome 11 open reading frame 57 |
| C4orf52 | 3.220 | 2.860 | 4.223 | 4.572 | 4.759 | 4.842 | 2.907 | 0.0319823 | chromosome 4 open reading frame 52 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| TSHZ3 | 2.944 | 3.358 | 2.602 | 4.486 | 4.683 | 4.296 | 2.912 | 0.0060867 | teashirt zinc finger homeobox 3 |
| NPTN | 8.294 | 8.274 | 8.029 | 9.665 | 9.610 | 9.839 | 2.917 | 0.0016385 | neuroplastin |
| SHC1 | 5.064 | 6.148 | 5.487 | 7.407 | 7.032 | 6.797 | 2.918 | 0.0137843 | SHC (Src homology 2 domain containing) transforming protein 1 |
| TEX264 | 7.463 | 7.714 | 9.445 | 10.990 | 10.154 | 8.992 | 2.919 | 0.0494628 | testis expressed 264 |
| SLC39A13 | 7.894 | 8.786 | 9.234 | 10.333 | 10.575 | 10.331 | 2.922 | 0.0095196 | solute carrier family 39 (zinc transporter), member 13 |
| MUC16 | 6.136 | 8.166 | 8.865 | 9.716 | 9.593 | 9.900 | 2.927 | 0.0340046 | mucin 16, cell surface associated |
| SLC10A7 | 4.126 | 2.686 | 3.532 | 5.335 | 4.861 | 5.083 | 2.931 | 0.0152387 | solute carrier family 10 (sodium/bile acid cotransporter family), member 7 |
| OR7E91P | 2.878 | 2.108 | 2.348 | 3.659 | 4.406 | 4.235 | 2.931 | 0.0078089 | olfactory receptor, family 7, subfamily E, member 91 pseudogene |
| LOC400043 | 4.899 | 6.454 | 7.518 | 7.940 | 8.253 | 8.007 | 2.933 | 0.0430192 | No description |
| ROBO4 | 2.747 | 2.649 | 2.013 | 5.441 | 3.712 | 3.565 | 2.934 | 0.0286961 | roundabout homolog 4, magic roundabout (Drosophila) |
| PCBD1 | 5.516 | 4.164 | 5.050 | 6.781 | 6.660 | 5.719 | 2.938 | 0.0324935 | pterin-4 alpha-carbinolamine dehydratase/dimerization cofactor of hepatocyte nuclear factor 1 alpha |
| DHX8 | 7.154 | 7.328 | 8.181 | 9.503 | 9.527 | 8.710 | 2.939 | 0.0123269 | DEAH (Asp-Glu-Ala-His) box polypeptide 8 |
| PPM1H | 3.865 | 5.074 | 4.098 | 6.807 | 5.655 | 5.420 | 2.941 | 0.0289210 | protein phosphatase, Mg2+/Mn2+ dependent, 1H |
| C10orf118 | 5.258 | 5.123 | 5.414 | 6.972 | 6.850 | 6.603 | 2.945 | 0.0020491 | chromosome 10 open reading frame 118 |
| CD74 | 7.507 | 6.933 | 6.556 | 8.679 | 9.070 | 7.482 | 2.954 | 0.0429194 | CD74 molecule, major histocompatibility complex, class II invariant chain |
| LDLR | 11.958 | 11.786 | 13.234 | 13.521 | 13.489 | 13.567 | 2.956 | 0.0490798 | low density lipoprotein receptor |
| COL6A2 | 9.560 | 11.541 | 10.902 | 11.950 | 12.471 | 12.964 | 2.966 | 0.0281673 | collagen, type VI, alpha 2 |
| KLHL15 | 5.191 | 3.745 | 4.116 | 5.685 | 5.430 | 6.005 | 2.968 | 0.0341174 | kelch-like 15 (Drosophila) |
| GLG1 | 8.675 | 8.379 | 8.927 | 10.628 | 10.244 | 9.866 | 2.969 | 0.0062847 | golgi glycoprotein 1 |
| HSD11B2 | 5.410 | 4.098 | 4.428 | 5.313 | 6.194 | 6.980 | 2.970 | 0.0442855 | hydroxysteroid (11-beta) dehydrogenase 2 |
| METTL5 | 5.237 | 4.799 | 3.874 | 6.370 | 6.439 | 5.720 | 2.972 | 0.0214551 | methyltransferase like 5 |
| UBA5 | 6.945 | 6.903 | 6.690 | 8.476 | 8.913 | 7.621 | 2.974 | 0.0165318 | ubiquitin-like modifier activating enzyme 5 |
| KIAA0196 | 1.974 | 2.162 | 2.649 | 4.222 | 3.196 | 3.744 | 2.975 | 0.0152226 | KIAA0196 |
| UBLCP1 | 4.687 | 3.747 | 3.257 | 5.930 | 4.830 | 5.364 | 2.975 | 0.0333338 | ubiquitin-like domain containing CTD phosphatase 1 |
| FCHO2 | 3.616 | 3.744 | 4.150 | 5.317 | 4.547 | 6.034 | 2.975 | 0.0253338 | FCH domain only 2 |
| PRSS36 | 4.448 | 3.426 | 3.324 | 6.025 | 5.342 | 4.801 | 2.983 | 0.0201850 | protease, serine, 36 |
| PDE7B | 1.974 | 2.953 | 2.377 | 3.704 | 4.098 | 3.954 | 2.984 | 0.0105457 | phosphodiesterase 7B |
| SSBP3 | 4.003 | 3.533 | 3.927 | 5.112 | 5.345 | 5.887 | 2.987 | 0.0055741 | single stranded DNA binding protein 3 |
| PKP2 | 4.231 | 4.091 | 5.803 | 6.667 | 6.463 | 5.671 | 2.991 | 0.0412187 | plakophilin 2 |
| HEATR1 | 5.362 | 6.614 | 5.624 | 7.011 | 7.709 | 7.207 | 2.996 | 0.0236493 | HEAT repeat containing 1 |
| HSPB7 | 0.974 | 1.264 | 1.643 | 3.469 | 2.848 | 1.819 | 2.998 | 0.0371213 | heat shock 27 kDa protein family, member 7 (cardiovascular) |
| KLHL7 | 3.364 | 4.072 | 3.776 | 4.950 | 5.429 | 5.399 | 3.002 | 0.0067145 | kelch-like 7 (Drosophila) |
| TIMM17B | 8.253 | 7.073 | 7.757 | 9.420 | 9.345 | 8.900 | 3.005 | 0.0145280 | translocase of inner mitochondrial membrane 17 homolog B (yeast) |
| FGFBP1 | 7.571 | 9.276 | 9.494 | 9.672 | 10.736 | 11.084 | 3.013 | 0.0443607 | fibroblast growth factor binding protein 1 |
| H LA-DOB | 3.247 | 1.974 | 1.974 | 4.833 | 4.098 | 3.565 | 3.013 | 0.0206823 | major histocompatibility complex, class II, DO beta |
| SENP1 | 4.350 | 5.560 | 4.651 | 6.539 | 6.328 | 5.942 | 3.015 | 0.0214743 | SUMO1/sentrin specific peptidase 1 |
| EFNA1 | 10.382 | 9.552 | 9.204 | 10.991 | 11.180 | 11.144 | 3.016 | 0.0176439 | ephrin-A1 |
| FAM115A | 8.006 | 6.881 | 7.880 | 9.498 | 9.472 | 9.249 | 3.016 | 0.0069071 | family with sequence similarity 115, member A |
| TIPRL | 6.601 | 6.781 | 6.837 | 8.658 | 8.374 | 8.185 | 3.016 | 0.0016838 | TIP41, TOR signaling pathway regulator-like (S. cerevisiae) |
| LPCAT1 | 5.718 | 6.515 | 7.305 | 8.278 | 7.702 | 8.110 | 3.021 | 0.0256646 | lysophosphatidylcholine acyltransferase 1 |

TABLE 5-continued

Differentially Expressed Genes in CD24+ Breast Epithelial Cells

| | Nulliparous (NP) Samples | | Parous (P) Samples | | | | | |
|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| CTU2 | 6.021 | 6.238 | 7.360 | 7.719 | 8.016 | 7.833 | 3.022 | 0.0308864 | cytosolic thiouridylase subunit 2 homolog (S. pombe) |
| MPPE1 | 5.317 | 6.047 | 6.180 | 7.644 | 8.193 | 6.868 | 3.025 | 0.0149962 | metallophosphoesterase 1 |
| NT5DC3 | 6.867 | 6.787 | 6.342 | 7.940 | 8.196 | 9.934 | 3.027 | 0.0179655 | 5'-nucleotidase domain containing 3 |
| BTN2A2 | 7.104 | 6.234 | 5.558 | 8.605 | 7.156 | 7.884 | 3.027 | 0.0372970 | butyrophilin, subfamily 2, member A2 |
| ABCC13 | 4.054 | 2.752 | 3.262 | 4.507 | 5.797 | 4.354 | 3.035 | 0.0387598 | ATP-binding cassette, sub-family C (CFTR/MRP), member 13,pseudogene |
| AIP | 2.296 | 3.648 | 3.468 | 4.921 | 5.252 | 4.445 | 3.038 | 0.0156285 | aryl hydrocarbon receptor interacting protein |
| ZNF331 | 4.890 | 4.148 | 4.492 | 6.149 | 5.752 | 6.467 | 3.039 | 0.0072617 | zinc finger protein 331 |
| TUBB2B | 6.457 | 5.202 | 3.693 | 6.807 | 6.797 | 7.081 | 3.042 | 0.0482425 | tubulin, beta 2B |
| TMEM106A | 4.363 | 4.458 | 5.062 | 6.067 | 6.174 | 6.033 | 3.051 | 0.0058649 | transmembrane protein 106A |
| ZEB1 | 2.782 | 3.491 | 2.804 | 5.101 | 4.276 | 4.444 | 3.052 | 0.0104282 | zinc finger E-box binding homeobox 1 |
| FAM110A | 6.091 | 6.850 | 6.195 | 7.703 | 7.825 | 8.008 | 3.057 | 0.0078619 | family with sequence similarity 110, member A |
| CMTM1 | 0.974 | 1.691 | 2.134 | 3.746 | 2.402 | 3.304 | 3.057 | 0.0273185 | CKLF-like MARVEL transmembrane domain containing 1 |
| IFH 6 | 5.178 | 7.253 | 6.909 | 8.048 | 7.807 | 8.866 | 3.058 | 0.0357245 | interferon, gamma-inducible protein 16 |
| SFRS8 | 7.610 | 7.890 | 9.000 | 9.624 | 9.223 | 9.845 | 3.061 | 0.0302387 | No description |
| ZFAND2B | 6.882 | 6.773 | 6.549 | 8.164 | 8.218 | 8.574 | 3.064 | 0.0023576 | zinc finger, AN1-type domain 2B |
| KTELC1 | 4.408 | 5.239 | 5.580 | 7.196 | 6.985 | 5.764 | 3.066 | 0.0317406 | No description |
| C17orf63 | 8.367 | 7.481 | 7.967 | 9.537 | 9.600 | 9.590 | 3.079 | 0.0047675 | chromosome 17 open reading frame 63 |
| INHA | 4.215 | 2.860 | 1.974 | 5.556 | 4.353 | 4.486 | 3.088 | 0.0409102 | inhibin, alpha |
| GRK4 | 1.559 | 2.110 | 1.973 | 3.032 | 3.600 | 4.647 | 3.089 | 0.0128542 | G protein-coupled receptor kinase 4 |
| SH3PXD2A | 6.668 | 5.328 | 5.798 | 7.574 | 6.957 | 7.904 | 3.092 | 0.0230537 | SH3 and PX domains 2A |
| NEDD4 | 3.412 | 4.066 | 4.389 | 5.694 | 5.671 | 5.943 | 3.092 | 0.0043331 | neural precursor cell expressed, developmentally down-regulated 4 |
| C17orf77 | 1.974 | 2.013 | 2.086 | 3.643 | 3.583 | 4.969 | 3.096 | 0.0074236 | chromosome 17 open reading frame 77 |
| ATP6V1E1 | 5.578 | 6.054 | 7.180 | 7.687 | 8.454 | 7.316 | 3.100 | 0.0357836 | ATPase, H+ transporting, lysosomal 31 kDa, V1 subunit E1 |
| UCA1 | 2.559 | 2.861 | 2.710 | 4.727 | 4.344 | 3.173 | 3.104 | 0.0345449 | urothelial cancer associated 1 (non-protein coding) |
| MRVH | 0.974 | 0.974 | 0.974 | 2.610 | 3.324 | 1.819 | 3.108 | 0.0159808 | murine retrovirus integration site 1 homolog |
| GYS1 | 8.691 | 7.683 | 8.948 | 10.572 | 10.584 | 9.027 | 3.108 | 0.0386922 | glycogen synthase 1 (muscle) |
| LRRC1 | 4.512 | 5.553 | 5.955 | 7.591 | 6.866 | 6.964 | 3.109 | 0.0139908 | leucine rich repeat containing 1 |
| UTP6 | 6.770 | 6.437 | 5.825 | 7.447 | 8.082 | 8.539 | 3.127 | 0.0129793 | UTP6, small subunit (SSU) processome component, homolog (yeast) |
| HOXC11 | 1.974 | 2.038 | 2.038 | 2.836 | 3.649 | 3.335 | 3.131 | 0.0199271 | homeobox C11 |
| IMPA2 | 6.404 | 7.239 | 6.869 | 9.629 | 8.517 | 7.563 | 3.135 | 0.0308135 | inositol(myo)-1 (or 4)-monophosphatase 2 |
| RAB4A | 7.334 | 6.706 | 6.473 | 8.122 | 8.414 | 8.566 | 3.137 | 0.0085649 | RAB4A, member RAS oncogene family |
| BTG3 | 4.360 | 5.382 | 5.125 | 7.035 | 6.442 | 6.421 | 3.144 | 0.0096508 | BTG family, member 3 |
| NOC4L | 7.614 | 8.091 | 9.123 | 9.746 | 10.003 | 9.320 | 3.148 | 0.0328941 | nucleolar complex associated 4 homolog (S. cerevisiae) |
| SESN1 | 6.950 | 6.152 | 5.616 | 7.773 | 7.808 | 8.400 | 3.152 | 0.0121036 | sestrin 1 |
| LRCH1 | 8.295 | 8.256 | 9.254 | 9.937 | 9.953 | 10.459 | 3.154 | 0.0141919 | leucine-rich repeats and calponin homology (CH) domain containing 1 |
| FUT6 | 0.974 | 1.050 | 1.050 | 3.836 | 2.712 | 2.404 | 3.165 | 0.0080806 | fucosyltransferase 6 (alpha (1.3) fucosyltransferase) |
| APOL1 | 1.559 | 2.747 | 2.848 | 4.512 | 4.144 | 3.859 | 3.168 | 0.0123592 | apolipoprotein L, 1 |
| MAD2L1BP | 5.412 | 4.099 | 5.236 | 7.574 | 5.765 | 6.317 | 3.171 | 0.0416616 | MAD2L1 binding protein |
| PCYOX1 | 5.028 | 5.516 | 5.245 | 7.258 | 6.695 | 6.695 | 3.174 | 0.0042402 | prenylcysteine oxidase 1 |
| ITPRIP | 3.272 | 3.542 | 3.044 | 4.759 | 5.171 | 4.939 | 3.175 | 0.0024313 | inositol 1,4,5-triphosphate receptor interacting protein |
| PLB1 | 1.974 | 3.220 | 3.334 | 4.899 | 4.892 | 3.704 | 3.188 | 0.0290652 | phospholipase B1 |
| SERPINB6 | 8.545 | 9.062 | 9.855 | 11.350 | 10.816 | 10.218 | 3.190 | 0.0207437 | serpin peptidase inhibitor. clade B (ovalbumin), member 6 |
| C10orf54 | 3.272 | 3.440 | 4.486 | 5.826 | 5.114 | 5.035 | 3.191 | 0.0185050 | chromosome 10 open reading frame 54 |

TABLE 5-continued

Differentially Expressed Genes in CD24+ Breast Epithelial Cells

| | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| TM2D2 | 4.969 | 6.237 | 7.339 | 8.340 | 7.879 | 7.912 | 3.194 | 0.0295180 | TM2 domain containing 2 |
| FGFRL1 | 6.932 | 7.107 | 7.836 | 8.268 | 9.516 | 8.999 | 3.204 | 0.0167959 | fibroblast growth factor receptor-like 1 |
| NRN1 | 0.974 | 2.404 | 1.643 | 3.324 | 2.848 | 3.758 | 3.208 | 0.0197736 | neuritin 1 |
| FBXO10 | 3.272 | 4.741 | 6.061 | 6.391 | 6.427 | 6.580 | 3.217 | 0.0489325 | F-box protein 10 |
| PATL1 | 8.650 | 8.495 | 8.315 | 10.182 | 9.312 | 10.419 | 3.219 | 0.0137951 | protein associated with topoisomerase II homolog 1 (yeast) |
| SLC29A1 | 8.460 | 7.869 | 8.251 | 10.083 | 9.940 | 9.797 | 3.223 | 0.0020384 | solute carrier family 29 (nucleoside transporters), member 1 |
| NHEDC2 | 5.514 | 5.027 | 5.263 | 6.910 | 7.036 | 6.951 | 3.224 | 0.0014758 | Na+/H+ exchanger domain containing 2 |
| C8orf46 | 1.559 | 2.968 | 4.160 | 4.597 | 5.153 | 4.658 | 3.227 | 0.0348127 | chromosome 8 open reading frame 46 |
| PITPNB | 7.295 | 7.144 | 8.187 | 8.986 | 8.938 | 9.615 | 3.228 | 0.0122448 | phosphatidylinositol transfer protein, beta |
| IL17RA | 5.132 | 5.166 | 5.158 | 6.850 | 7.038 | 6.502 | 3.232 | 0.0018880 | interleukin 17 receptor A |
| TSEN54 | 6.013 | 6.821 | 6.815 | 8.343 | 8.514 | 7.821 | 3.234 | 0.0084114 | tRNA splicing endonuclease 54 homolog (S. cerevisiae) |
| ZBTB7B | 8.482 | 8.838 | 9.044 | 10.532 | 10.567 | 10.414 | 3.236 | 0.0017659 | zinc finger and BTB domain containing 7B |
| PHB2 | 11.919 | 11.411 | 13.211 | 13.613 | 13.944 | 13.207 | 3.237 | 0.0477030 | prohibitin 2 |
| AIDA | 4.870 | 6.197 | 6.017 | 7.893 | 7.235 | 7.165 | 3.241 | 0.0150230 | axin interactor, dorsalization associated |
| UBE2Q1 | 5.623 | 6.558 | 6.267 | 7.964 | 8.234 | 7.331 | 3.242 | 0.0103223 | ubiquitin-conjugating enzyme E2Q family member 1 |
| MAP3K7IP3 | 6.554 | 7.194 | 6.413 | 8.652 | 8.325 | 8.111 | 3.246 | 0.0060652 | No description |
| HSPB2 | 2.519 | 1.759 | 1.759 | 2.650 | 3.459 | 4.755 | 3.251 | 0.0423070 | heat shock 27 kDa protein 2 |
| PRKDC | 8.236 | 8.956 | 10.039 | 10.658 | 11.033 | 10.219 | 3.252 | 0.0339048 | protein kinase, DNA-activated, catalytic polypeptide |
| LDB2 | 2.519 | 2.650 | 2.037 | 4.353 | 4.013 | 4.144 | 3.257 | 0.0023185 | LIM domain binding 2 |
| SPSB3 | 10.098 | 9.233 | 7.344 | 10.997 | 10.658 | 10.939 | 3.263 | 0.0360890 | splA/ryanodine receptor domain and SOCS box containing 3 |
| C6orf120 | 7.217 | 6.376 | 7.602 | 8.272 | 9.309 | 8.304 | 3.265 | 0.0238603 | chromosome 6 open reading frame 120 |
| FXYD5 | 6.120 | 8.704 | 7.757 | 9.615 | 9.465 | 8.863 | 3.268 | 0.0452525 | FXYD domain containing ion transport regulator 5 |
| HTR3B | 6.505 | 5.506 | 6.652 | 8.361 | 8.158 | 7.541 | 3.268 | 0.0108457 | 5-hydroxytryptamine (serotonin) receptor 3B |
| REM1 | -0.026 | 1.913 | 2.263 | 3.335 | 3.176 | 3.974 | 3.275 | 0.0226270 | RAS (RAD and GEM)-like GTP-binding 1 |
| RAB4B | 2.878 | 3.772 | 2.348 | 5.240 | 4.952 | 4.062 | 3.280 | 0.0200123 | RAB4B, member RAS oncogene family |
| S100A8 | 0.974 | 3.747 | 3.796 | 5.513 | 5.074 | 5.236 | 3.286 | 0.0248964 | S100 calcium binding protein A8 |
| PRDX3 | 10.007 | 8.355 | 8.975 | 10.948 | 10.692 | 10.150 | 3.287 | 0.0343292 | peroxiredoxin 3 |
| MRPS6 | 3.793 | 4.280 | 4.900 | 6.493 | 5.999 | 5.614 | 3.291 | 0.0113008 | mitochondrial ribosomal protein S6 |
| MAST3 | 4.142 | 4.786 | 4.623 | 7.192 | 5.975 | 5.865 | 3.303 | 0.0120553 | microtubule associated serine/threonine kinase 3 |
| SHROOM2 | 4.631 | 4.968 | 4.486 | 7.156 | 6.357 | 6.034 | 3.308 | 0.0067437 | shroom family member 2 |
| FBXL8 | 2.878 | 4.983 | 5.512 | 6.715 | 6.976 | 5.797 | 3.322 | 0.0384628 | F-box and leucine-rich repeat protein 8 |
| PDE4C | 6.184 | 5.644 | 6.335 | 8.154 | 7.556 | 7.378 | 3.326 | 0.0077022 | phosphodiesterase 4C, cAMP-specific |
| PECR | 3.831 | 4.140 | 4.456 | 5.875 | 5.661 | 6.114 | 3.329 | 0.0028404 | peroxisomal trans-2-enoyl-CoA reductase |
| ATP10D | 3.188 | 1.913 | 3.664 | 5.810 | 4.780 | 3.649 | 3.332 | 0.0456109 | ATPase, class V, type 10D |
| SULT1A4 | 2.559 | 3.642 | 2.610 | 4.991 | 3.914 | 5.379 | 3.333 | 0.0185157 | sulfotransferase family, cytosolic, 1A, phenol-preferring, member 4 |
| | 6.790 | 7.681 | 8.280 | 8.956 | 9.419 | 9.841 | 3.335 | 0.0143738 | |
| FAM43A | 7.187 | 6.011 | 7.002 | 8.928 | 8.347 | 8.180 | 3.344 | 0.0115986 | family with sequence similarity 43, member A |
| PKP4 | 9.896 | 8.754 | 10.477 | 11.867 | 11.640 | 10.745 | 3.349 | 0.0284183 | plakophilin 4 |
| RNF26 | 6.520 | 7.445 | 8.156 | 9.394 | 9.189 | 8.481 | 3.349 | 0.0249908 | ring finger protein 26 |
| PAK6 | 3.220 | 4.759 | 4.922 | 6.798 | 6.505 | 4.899 | 3.353 | 0.0487943 | p21 protein (Cdc42/Rac)-activated kinase 6 |
| FGFR2 | 7.026 | 6.137 | 6.539 | 8.094 | 8.286 | 8.718 | 3.356 | 0.0050468 | fibroblast growth factor receptor 2 |
| ACBD6 | 2.519 | 3.475 | 2.217 | 5.225 | 4.765 | 3.591 | 3.365 | 0.0244693 | acyl-CoA binding domain containing 6 |
| C8orf37 | 4.851 | 4.165 | 4.512 | 7.826 | 6.264 | 5.027 | 3.370 | 0.0451427 | chromosome 8 open reading frame 37 |
| RBM27 | 5.246 | 6.217 | 5.645 | 7.628 | 7.669 | 7.000 | 3.371 | 0.0081765 | RNA binding motif protein 27 |
| FAM134B | 6.116 | 4.396 | 4.374 | 7.313 | 6.672 | 6.128 | 3.372 | 0.0334551 | family with sequence similarity 134, member B |

TABLE 5-continued

Differentially Expressed Genes in CD24+ Breast Epithelial Cells

| | Nulliparous (NP) Samples | | | Parous (P) Samples | | | | | | |
|---|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| ABLIM2 | 2.296 | 2.749 | 3.061 | 5.759 | 4.503 | 3.809 | 3.374 | 0.0166746 | actin binding LIM protein family, member 2 |
| ZC3H7B | 6.018 | 6.290 | 7.441 | 8.081 | 8.045 | 7.878 | 3.376 | 0.0259133 | zinc finger CCCH-type containing 7B |
| KREMEN1 | 4.102 | 5.439 | 5.626 | 7.160 | 7.382 | 6.953 | 3.379 | 0.0082456 | kringle containing transmembrane protein 1 |
| MAP1A | 0.974 | 1.264 | 1.264 | 3.022 | 2.402 | 3.922 | 3.382 | 0.0088158 | microtubule-associated protein 1A |
| GPATCH2 | 6.962 | 5.987 | 6.053 | 7.745 | 8.530 | 8.297 | 3.384 | 0.0076470 | G patch domain containing 2 |
| ACTR5 | 5.514 | 6.429 | 7.367 | 8.188 | 8.194 | 8.000 | 3.385 | 0.0218028 | ARP5 actin-related protein 5 homolog (yeast) |
| KLHL26 | 2.296 | 2.419 | 2.652 | 5.084 | 4.042 | 4.178 | 3.385 | 0.0041504 | kelch-like 26 (Drosophila) |
| TMEM100 | −0.026 | −0.026 | 0.121 | 1.734 | 1.169 | 2.108 | 3.386 | 0.0054904 | transmembrane protein 100 |
| XPO1 | 8.763 | 8.744 | 7.679 | 9.776 | 9.829 | 10.523 | 3.388 | 0.0145817 | exportin 1 (CRM1 homolog, yeast) |
| ANKRD49 | 3.059 | 4.015 | 2.703 | 4.464 | 5.392 | 5.444 | 3.390 | 0.0140483 | ankyrin repeat domain 49 |
| BRF1 | 7.292 | 6.701 | 7.191 | 8.645 | 8.953 | 8.982 | 3.391 | 0.0021704 | BRF1 homolog, subunit of RNA polymerase III transcription initiation factor IIIB (S. cerevisiae) |
| ST6GALNAC5 | 3.090 | 2.404 | 3.032 | 4.236 | 4.853 | 4.630 | 3.394 | 0.0046692 | ST6 (alpha-N-acetyl-neuraminyl-2,3-beta-galactosyl-1,3)-N-acetylgalactosaminide al pha-2,6-sialyltransferase 5 |
| METTL11A | 7.112 | 7.209 | 6.843 | 9.180 | 8.769 | 8.613 | 3.409 | 0.0019440 | methyltransferase like 11A |
| PRPSAP2 | 6.683 | 7.001 | 7.327 | 9.535 | 8.455 | 8.539 | 3.415 | 0.0081128 | phosphoribosyl pyrophosphate synthetase-associated protein 2 |
| IKZF2 | 3.999 | 4.520 | 3.366 | 6.073 | 5.774 | 5.164 | 3.422 | 0.0126761 | IKAROS family zinc finger 2 (Helios) |
| WWOX | 3.220 | 3.644 | 4.860 | 5.556 | 5.419 | 5.070 | 3.423 | 0.0343645 | WW domain containing oxidoreductase |
| WDR27 | 3.728 | 3.540 | 4.420 | 6.195 | 5.186 | 5.849 | 3.424 | 0.0082187 | WD repeat domain 27 |
| HUNK | 1.974 | 2.161 | 2.747 | 3.868 | 3.937 | 4.098 | 3.426 | 0.0038849 | hormonally up-regulated Neu-associated kinase |
| MTHFD2L | 3.831 | 4.686 | 5.124 | 5.543 | 6.464 | 6.993 | 3.428 | 0.0205226 | methylenetetrahydrofolate dehydrogenase (NADP+ dependent) 2-like |
| USH1G | 3.616 | 4.327 | 4.795 | 5.735 | 6.106 | 6.272 | 3.432 | 0.0081573 | Usher syndrome 1 G (autosomal recessive) |
| ADNP | 7.434 | 6.206 | 5.834 | 8.089 | 7.690 | 7.988 | 3.438 | 0.0330107 | activity-dependent neuroprotector homeobox |
| UPF3B | 6.204 | 5.516 | 5.538 | 7.421 | 7.301 | 7.510 | 3.446 | 0.0037598 | UPF3 regulator of nonsense transcripts homolog B (yeast) |
| SPARC | 4.017 | 4.282 | 3.967 | 6.549 | 5.424 | 5.805 | 3.452 | 0.0056293 | secreted protein, acidic, cysteine-rich (osteonectin) |
| ARPC3 | 3.059 | 3.246 | 4.841 | 5.964 | 5.898 | 4.851 | 3.462 | 0.0266285 | actin related protein 2/3 complex, subunit 3, 21 kDa |
| MLX | 7.736 | 8.003 | 8.354 | 10.170 | 9.768 | 9.528 | 3.463 | 0.0033615 | MAX-like protein X |
| DLAT | 4.795 | 6.653 | 5.913 | 7.866 | 7.706 | 6.755 | 3.464 | 0.0359401 | dihydrolipoamide S-acetyltransferase |
| KCNMB1 | 1.974 | 2.860 | 3.583 | 3.678 | 4.652 | 6.008 | 3.465 | 0.0361082 | potassium large conductance calcium-activated channel, subfamily M, beta member 1 |
| ZNF425 | 6.112 | 6.305 | 6.513 | 8.280 | 8.112 | 7.958 | 3.499 | 0.0011013 | zinc finger protein 425 |
| USP40 | 6.107 | 7.080 | 7.217 | 9.028 | 8.676 | 7.949 | 3.508 | 0.0144167 | ubiquitin specific peptidase 40 |
| COMT | 3.927 | 5.087 | 5.564 | 6.914 | 6.899 | 6.135 | 3.511 | 0.0188565 | catechol-O-methyltransferase |
| C6orf211 | 4.353 | 4.051 | 3.459 | 6.852 | 5.273 | 5.525 | 3.514 | 0.0147713 | chromosome 6 open reading frame 211 |
| ANGPTL2 | 0.974 | 2.247 | 1.738 | 4.062 | 2.848 | 3.469 | 3.517 | 0.0152118 | angiopoietin-like 2 |
| MGC12982 | 1.559 | 1.759 | 3.186 | 3.851 | 3.374 | 4.007 | 3.518 | 0.0289739 | No description |
| ENDOG | 6.404 | 6.246 | 7.088 | 8.904 | 8.375 | 6.976 | 3.522 | 0.0467429 | endonuclease G |
| ZNF844 | 4.512 | 2.519 | 3.032 | 4.851 | 4.765 | 5.027 | 3.527 | 0.0402594 | zinc finger protein 844 |
| RNH1 | 9.816 | 10.089 | 10.527 | 12.232 | 12.198 | 11.640 | 3.541 | 0.0032909 | ribonuclease/angiogenin inhibitor 1 |
| DCTN2 | 11.097 | 10.294 | 9.336 | 12.493 | 12.119 | 11.613 | 3.544 | 0.0188196 | dynactin 2 (p50) |
| RCN3 | 0.974 | 2.108 | 1.643 | 5.020 | 2.402 | 3.469 | 3.546 | 0.0321627 | reticulocalbin 3, EF-hand calcium binding domain |
| AKR1E2 | 0.974 | 1.050 | 1.050 | 2.848 | 2.848 | 2.878 | 3.551 | 0.0002379 | aldo-keto reductase family 1, member E2 |
| LCLAT1 | 5.138 | 6.522 | 5.792 | 8.324 | 7.622 | 7.226 | 3.557 | 0.0128434 | lysocardiolipin acyltransferase 1 |
| ITGB5 | 9.578 | 10.950 | 11.925 | 12.784 | 12.806 | 11.890 | 3.565 | 0.0485610 | integrin, beta 5 |
| KIAA1324L | 3.412 | 3.511 | 3.366 | 5.112 | 5.345 | 5.288 | 3.566 | 0.0004774 | KIAA1324-like |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| LOC100170939 | 2.878 | 1.738 | 3.089 | 4.379 | 4.062 | 4.926 | 3.573 | 0.0118419 | No description |
| GFER | 5.749 | 5.899 | 6.296 | 8.334 | 7.737 | 7.483 | 3.574 | 0.0038373 | growth factor, augmenter of liver regeneration |
| LOC440944 | 6.453 | 5.681 | 6.461 | 7.713 | 7.666 | 8.299 | 3.574 | 0.0073914 | No description |
| OSTF1 | 7.042 | 7.883 | 7.591 | 9.975 | 9.440 | 8.824 | 3.602 | 0.0079586 | osteoclast stimulating factor 1 |
| KCNH3 | 0.974 | 2.072 | 2.348 | 3.922 | 3.478 | 3.922 | 3.605 | 0.0081466 | potassium voltage-gated channel, subfamily H (eag-related), member 3 |
| FOXO1 | 6.631 | 7.341 | 7.147 | 9.039 | 8.487 | 9.046 | 3.619 | 0.0037038 | forkhead box O1 |
| CDKN2A | 4.851 | 5.021 | 4.512 | 6.708 | 7.024 | 5.691 | 3.624 | 0.0135480 | cyclin-dependent kinase inhibitor 2A (melanoma, p16, inhibits CDK4) |
| EYA2 | 7.471 | 6.541 | 7.835 | 9.539 | 9.330 | 9.017 | 3.628 | 0.0060438 | eyes absent homolog 2 (Drosophila) |
| TUBE1 | 5.827 | 5.186 | 5.217 | 7.327 | 7.687 | 5.895 | 3.631 | 0.0354367 | tubulin, epsilon 1 |
| POU3F1 | 3.090 | 2.075 | 2.674 | 4.144 | 4.382 | 4.952 | 3.636 | 0.0066086 | POU class 3 homeobox 1 |
| LZTS1 | 3.220 | 2.377 | 3.263 | 4.344 | 4.759 | 5.126 | 3.638 | 0.0076147 | leucine zipper, putative tumor suppressor 1 |
| RBM19 | 6.311 | 6.277 | 8.039 | 8.576 | 8.404 | 8.141 | 3.640 | 0.0417544 | RNA binding motif protein 19 |
| CHST9 | 2.944 | 2.327 | 3.218 | 4.823 | 4.601 | 4.809 | 3.644 | 0.0028511 | carbohydrate (N-acetylgalactosamine 4-0) sulfotransferase 9 |
| KDM5C | 8.291 | 7.035 | 7.193 | 9.334 | 9.148 | 8.901 | 3.644 | 0.0142111 | lysine (K)-specific demethylase 5C |
| CSF3R | 5.772 | 5.660 | 7.397 | 8.642 | 7.835 | 7.526 | 3.645 | 0.0324328 | colony stimulating factor 3 receptor (granulocyte) |
| HAX1 | 9.307 | 8.672 | 9.111 | 10.979 | 11.499 | 10.489 | 3.651 | 0.0043438 | HCLS1 associated protein X-1 |
| CNBP | 8.062 | 7.358 | 6.700 | 9.229 | 8.739 | 9.229 | 3.657 | 0.0129447 | CCHC-type zinc finger, nucleic acid binding protein |
| VHL | 7.708 | 9.118 | 8.280 | 10.235 | 10.152 | 9.614 | 3.658 | 0.0167529 | von Hippel-Lindau tumor suppressor |
| EGFLAM | 3.220 | 2.347 | 2.161 | 4.572 | 4.610 | 4.032 | 3.660 | 0.0073055 | EGF-like, fibronectin type III and laminin G domains |
| TAF3 | 3.706 | 5.861 | 5.460 | 7.734 | 6.883 | 7.263 | 3.663 | 0.0145925 | TAF3 RNA polymerase II, TATA box binding protein (TBP)-associated factor, 140 kDa |
| ANKRD45 | 2.519 | 2.893 | 3.388 | 4.859 | 5.002 | 4.393 | 3.666 | 0.0046585 | ankyrin repeat domain 45 |
| PLCB3 | 2.944 | 4.206 | 3.263 | 5.738 | 5.140 | 4.946 | 3.673 | 0.0114305 | phospholipase C, beta 3 (phosphatidylinositol-specific) |
| MMP2 | 2.782 | 2.782 | 3.567 | 6.552 | 4.623 | 4.662 | 3.680 | 0.0147606 | matrix metallopeptidase 2 (gelatinase A, 72 kDa gelatinase, 72 kDa type IV collagenase) |
| SLC34A2 | 8.952 | 11.335 | 11.869 | 13.261 | 13.224 | 12.168 | 3.704 | 0.0397352 | solute carrier family 34 (sodium phosphate), member 2 |
| C2orf68 | 4.507 | 6.886 | 7.160 | 9.052 | 8.684 | 8.129 | 3.711 | 0.0209486 | chromosome 2 open reading frame 68 |
| FBXW5 | 10.748 | 9.998 | 12.047 | 12.753 | 12.912 | 11.892 | 3.715 | 0.0464213 | F-box and WD repeat domain containing 5 |
| TMLHE | 3.999 | 3.848 | 4.989 | 5.945 | 6.148 | 5.743 | 3.718 | 0.0104390 | trimethyllysine hydroxylase, epsilon |
| LEAP2 | −0.026 | 2.038 | 2.263 | 3.176 | 3.176 | 4.158 | 3.720 | 0.0280092 | liver expressed antimicrobial peptide 2 |
| ARHGEF5L | 5.342 | 5.874 | 6.136 | 7.456 | 7.238 | 8.048 | 3.724 | 0.0058434 | No description |
| LOC642587 | 8.477 | 9.820 | 11.083 | 11.716 | 11.838 | 11.692 | 3.724 | 0.0298949 | No description |
| RAD52 | 1.559 | 3.059 | 2.075 | 3.459 | 4.013 | 4.705 | 3.732 | 0.0189317 | RAD52 homolog (S. cerevisiae) |
| CLEC17A | 1.559 | 1.559 | 2.037 | 2.404 | 3.459 | 4.705 | 3.732 | 0.0310146 | C-type lectin domain family 17, member A |
| FOXP3 | 0.974 | 1.326 | 2.518 | 3.437 | 4.113 | 2.878 | 3.741 | 0.0189424 | forkhead box P3 |
| NUDT16 | 4.003 | 4.607 | 4.351 | 6.571 | 6.258 | 5.862 | 3.750 | 0.0027897 | nudix (nucleoside diphosphate linked moiety X)-type motif 16 |
| CRTC2 | 6.129 | 5.896 | 7.447 | 8.388 | 8.462 | 7.804 | 3.754 | 0.0192817 | CREB regulated transcription coactivator 2 |
| SORBS2 | 5.066 | 6.168 | 4.588 | 8.077 | 7.380 | 6.314 | 3.757 | 0.0229593 | sorbin and SH3 domain containing 2 |
| SDK1 | 2.559 | 2.663 | 2.818 | 5.125 | 4.572 | 3.496 | 3.758 | 0.0161573 | sidekick homolog 1, cell adhesion molecule (chicken) |
| ELN | 1.559 | 1.610 | 1.803 | 2.650 | 3.524 | 4.875 | 3.768 | 0.0183062 | elastin |
| ADAMTS5 | 2.559 | 2.559 | 2.559 | 4.475 | 3.632 | 4.697 | 3.774 | 0.0068289 | ADAM metallopeptidase with thrombospondin type 1 motif, 5 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24 N48 | CD24 N58 | CD24 N43 | CD24 N37 | CD24 N39 | CD24 N40 | Pseudo fold change | P value | Gene description |
| PLD6 | 2.944 | 3.838 | 4.638 | 6.339 | 5.374 | 5.756 | 3.779 | 0.0131266 | phospholipase D family, member 6 |
| SNORD22 | 6.337 | 4.637 | 4.240 | 6.557 | 6.306 | 7.648 | 3.785 | 0.0435288 | small nucleolar RNA, C/D box 22 |
| CTPS | 6.900 | 8.059 | 7.042 | 8.910 | 9.069 | 8.962 | 3.785 | 0.0104068 | CTP synthase |
| ZNF33A | 6.568 | 6.685 | 6.342 | 8.491 | 9.017 | 7.685 | 3.790 | 0.0080422 | zinc finger protein 33A |
| VWF | 4.167 | 4.148 | 5.370 | 7.526 | 6.089 | 5.768 | 3.791 | 0.0250729 | von Willebrand factor |
| TMEM212 | 8.275 | 6.239 | 7.339 | 9.266 | 9.322 | 8.900 | 3.802 | 0.0197905 | transmembrane protein 212 |
| ERAL1 | 5.920 | 7.145 | 5.987 | 8.574 | 8.133 | 7.848 | 3.805 | 0.0108649 | Era G-protein-like 1 (*E. coli*) |
| WDR45 | 8.092 | 8.771 | 8.628 | 10.788 | 10.431 | 10.022 | 3.811 | 0.0034152 | WD repeat domain 45 |
| PRPS1 | 3.859 | 5.423 | 4.365 | 5.790 | 6.658 | 7.229 | 3.813 | 0.0166554 | phosphoribosyl pyrophosphate synthetase 1 |
| APPBP2 | 5.803 | 5.389 | 5.322 | 7.320 | 7.308 | 7.694 | 3.813 | 0.0013346 | amyloid beta precursor protein (cytoplasmic tail) binding protein 2 |
| ENC1 | 5.262 | 4.309 | 3.763 | 6.241 | 6.279 | 6.019 | 3.817 | 0.0130629 | ectodermal-neural cortex 1 (with BTB-like domain) |
| LOC493754 | 9.558 | 7.524 | 8.863 | 10.597 | 10.797 | 11.054 | 3.820 | 0.0123853 | No description |
| SPEG | 6.591 | 5.929 | 7.780 | 7.868 | 9.084 | 8.602 | 3.833 | 0.0300061 | SPEG complex locus |
| ZNF18 | 2.878 | 3.997 | 3.478 | 6.066 | 5.422 | 4.649 | 3.847 | 0.0128649 | zinc finger protein 18 |
| ZNF93 | 5.968 | 5.607 | 4.730 | 8.172 | 6.675 | 6.863 | 3.850 | 0.0223745 | zinc finger protein 93 |
| KRT71 | 2.878 | 1.264 | 2.108 | 2.848 | 4.062 | 5.386 | 3.875 | 0.0385779 | keratin 71 |
| FBXO27 | 5.611 | 5.116 | 5.499 | 7.942 | 7.075 | 7.304 | 3.889 | 0.0026900 | F-box protein 27 |
| IFITM3 | 7.795 | 8.507 | 8.708 | 10.765 | 10.330 | 9.757 | 3.896 | 0.0065487 | interferon induced transmembrane protein 3 (1-8U) |
| KIAA1949 | 10.133 | 10.009 | 10.680 | 12.098 | 11.902 | 12.751 | 3.903 | 0.0036715 | KIAA1949 |
| MRPS18C | 4.054 | 4.062 | 4.651 | 6.534 | 6.023 | 6.056 | 3.915 | 0.0022648 | mitochondrial ribosomal protein S18C |
| OLFM2 | 4.741 | 4.948 | 6.461 | 6.918 | 7.009 | 6.822 | 3.916 | 0.0317889 | olfactomedin 2 |
| C8orf33 | 6.968 | 6.619 | 6.754 | 8.939 | 8.420 | 8.854 | 3.920 | 0.0012103 | chromosome 8 open reading frame 33 |
| FTSJ3 | 2.974 | 5.767 | 4.751 | 6.916 | 6.204 | 6.725 | 3.929 | 0.0303208 | FtsJ homolog 3 (*E. coli*) |
| C14orf73 | 0.974 | 3.727 | 2.531 | 5.240 | 4.507 | 3.758 | 3.933 | 0.0379079 | chromosome 14 open reading frame 73 |
| C13orf34 | 1.559 | 3.024 | 2.404 | 4.829 | 4.382 | 4.266 | 3.939 | 0.0057053 | chromosome 13 open reading frame 34 |
| ZNF121 | 1.974 | 1.974 | 2.914 | 4.164 | 4.052 | 3.954 | 3.943 | 0.0055150 | zinc finger protein 121 |
| C1orf74 | 1.559 | 1.804 | 1.610 | 2.650 | 3.840 | 3.591 | 3.949 | 0.0092985 | chromosome 1 open reading frame 74 |
| GCHFR | 4.921 | 4.944 | 6.598 | 8.580 | 7.541 | 6.463 | 3.951 | 0.0327276 | GTP cyclohydrolase I feedback regulator |
| PLEKHF1 | 8.348 | 7.620 | 7.864 | 9.846 | 10.025 | 9.834 | 3.952 | 0.0016170 | pleckstrin homology domain containing, family F (with FYVE domain) member 1 |
| CCDC117 | 4.339 | 5.197 | 5.693 | 7.677 | 6.627 | 6.431 | 3.957 | 0.0175196 | coiled-coil domain containing 117 |
| SLC22A9 | −0.026 | 0.121 | −0.026 | 2.108 | 2.105 | 1.348 | 3.963 | 0.0030476 | solute carrier family 22 (organic anion transporter), member 9 |
| IL2RA | 6.697 | 7.058 | 7.671 | 9.254 | 9.045 | 8.791 | 3.963 | 0.0041397 | interleukin 2 receptor, alpha |
| SIN3A | 8.009 | 8.342 | 8.756 | 10.630 | 9.998 | 10.525 | 3.968 | 0.0025909 | SIN3 homolog A, transcription regulator (yeast) |
| HMOX1 | 6.760 | 9.598 | 9.758 | 10.433 | 10.640 | 11.754 | 3.989 | 0.0452141 | heme oxygenase (decycling) 1 |
| RGS5 | 2.974 | 3.052 | 2.994 | 5.830 | 4.840 | 4.996 | 4.007 | 0.0019041 | regulator of G-protein signaling 5 |
| SULT2B1 | 6.087 | 5.210 | 6.199 | 8.273 | 7.807 | 7.217 | 4.019 | 0.0085196 | sulfotransferase family, cytosolic, 2B, member 1 |
| IFITM1 | 5.908 | 7.350 | 5.527 | 9.056 | 7.919 | 7.551 | 4.032 | 0.0283262 | interferon induced transmembrane protein 1 (9-27) |
| C13orf27 | 1.559 | 4.422 | 3.600 | 5.616 | 5.376 | 5.823 | 4.046 | 0.0201957 | chromosome 13 open reading frame 27 |
| LOC440896 | 4.459 | 3.040 | 3.914 | 5.057 | 5.931 | 6.140 | 4.047 | 0.0138887 | No description |
| PLODS | 6.824 | 7.518 | 8.690 | 9.573 | 9.535 | 9.397 | 4.058 | 0.0174060 | procollagen-lysine, 2-oxoglutarate 5-dioxygenase 3 |
| SIRPB2 | 5.451 | 4.207 | 6.089 | 7.848 | 7.471 | 7.418 | 4.068 | 0.0080207 | signal-regulatory protein beta 2 |
| CP | 3.519 | 3.746 | 2.559 | 6.184 | 5.382 | 4.584 | 4.069 | 0.0124236 | ceruloplasmin (ferroxidase) |
| FLJ14107 | −0.026 | 0.611 | 1.734 | 3.542 | 2.636 | 2.108 | 4.068 | 0.0204037 | No description |
| TXN | 3.475 | 1.847 | 2.396 | 4.273 | 4.568 | 4.422 | 4.072 | 0.0127137 | thioredoxin |

TABLE 5-continued

Differentially Expressed Genes in CD24+ Breast Epithelial Cells

| | Nulliparous (NP) Samples | | | Parous (P) Samples | | | | | |
| --- | --- | --- | --- | --- | --- | --- | --- | --- | --- |
| | CD24+ N48 | CD24+ N58 | CD24+ N43 | CD24+ N37 | CD24+ N39 | CD24+ N40 | Pseudo fold change | P value | Gene description |
| UNC50 | 3.188 | 6.229 | 4.775 | 7.242 | 6.622 | 6.801 | 4.074 | 0.0334444 | unc-50 homolog (*C. elegans*) |
| CROCCL1 | 5.939 | 7.136 | 5.342 | 7.968 | 7.630 | 8.454 | 4.082 | 0.0178918 | No description |
| DRAM1 | 4.595 | 5.433 | 4.160 | 7.529 | 6.587 | 6.190 | 4.083 | 0.0115579 | DNA-damage regulated autophagy modulator 1 |
| EPB41L3 | 1.559 | 3.059 | 1.759 | 4.273 | 4.471 | 3.591 | 4.090 | 0.0126109 | erythrocyte membrane protein band 4.1-like 3 |
| CHRDL2 | 1.559 | 3.388 | 1.559 | 3.591 | 4.013 | 4.851 | 4.090 | 0.0246815 | chordin-like 2 |
| HNRNPU | 9.945 | 9.746 | 9.148 | 11.783 | 11.735 | 11.959 | 4.103 | 0.0011612 | heterogeneous nuclear ribonucleoprotein U (scaffold attachment factor A) |
| APOLD1 | 4.220 | 6.184 | 5.420 | 8.224 | 6.587 | 6.785 | 4.111 | 0.0334958 | apolipoprotein L domain containing 1 |
| FBXL14 | 1.559 | 3.059 | 1.759 | 4.013 | 3.600 | 3.859 | 4.114 | 0.0169624 | F-box and leucine-rich repeat protein 14 |
| TWIST1 | 1.559 | 1.559 | 1.559 | 4.568 | 3.600 | 2.173 | 4.114 | 0.0275825 | twist homolog 1 (*Drosophila*) |
| CRISPLD2 | 6.010 | 6.674 | 7.651 | 9.604 | 8.715 | 8.065 | 4.115 | 0.0186777 | cysteine-rich secretory protein LCCL domain containing 2 |
| DAZAP2 | 10.996 | 10.743 | 9.740 | 13.038 | 12.734 | 12.470 | 4.117 | 0.0037705 | DAZ associated protein 2 |
| ANKRD40 | 7.960 | 8.136 | 7.490 | 9.883 | 10.179 | 9.708 | 4.119 | 0.0014973 | ankyrin repeat domain 40 |
| THBD | 2.559 | 3.532 | 3.626 | 5.918 | 4.737 | 4.604 | 4.127 | 0.0159133 | thrombomodulin |
| TCF4 | 3.974 | 4.841 | 4.132 | 7.869 | 6.178 | 4.929 | 4.130 | 0.0416807 | transcription factor 4 |
| BCAN | 5.273 | 4.151 | 5.845 | 7.527 | 7.041 | 7.319 | 4.132 | 0.0076577 | brevican |
| CH25H | 0.974 | 0.974 | 1.264 | 2.404 | 3.022 | 3.848 | 4.134 | 0.0066347 | cholesterol 25-hydroxylase |
| BOC | 5.078 | 4.396 | 5.271 | 6.775 | 6.453 | 8.234 | 4.162 | 0.0107536 | Boc homolog (mouse) |
| OSGIN2 | 3.908 | 3.763 | 3.573 | 5.945 | 5.967 | 4.778 | 4.168 | 0.0089532 | oxidative stress induced growth inhibitor family member 2 |
| BCL2L11 | 7.969 | 8.008 | 8.364 | 11.356 | 10.070 | 9.820 | 4.175 | 0.0053016 | BCL2-like 11 (apoptosis facilitator) |
| BNIP2 | 6.553 | 5.306 | 5.328 | 7.779 | 7.473 | 7.371 | 4.184 | 0.0102494 | BCL2/adenovirus E1B 19 kDa interacting protein 2 |
| EFNB1 | 4.870 | 6.250 | 6.213 | 9.266 | 8.059 | 6.935 | 4.185 | 0.0201527 | ephrin-B1 |
| ALKBH4 | 9.183 | 7.891 | 7.986 | 10.612 | 10.282 | 9.957 | 4.186 | 0.0092878 | alkB, alkylation repair homolog 4 (*E. coli*) |
| DDX51 | 6.484 | 6.012 | 7.555 | 8.475 | 8.903 | 8.552 | 4.194 | 0.0096124 | DEAD (Asp-Glu-Ala-Asp) box polypeptide 51 |
| NHEJ1 | 6.196 | 6.193 | 6.859 | 8.262 | 8.453 | 8.418 | 4.195 | 0.0016600 | nonhomologous end-joining factor 1 |
| ZNF167 | 1.559 | 3.719 | 2.075 | 3.767 | 4.144 | 4.422 | 4.197 | 0.0401427 | zinc finger protein 167 |
| SLC16A13 | −0.026 | 3.693 | 4.322 | 6.306 | 5.772 | 4.428 | 4.224 | 0.0497490 | solute carrier family 16, member 13 (monocarboxylic acid transporter 13) |
| ZNF384 | 7.921 | 7.876 | 8.645 | 10.022 | 10.167 | 9.959 | 4.235 | 0.0025372 | zinc finger protein 384 |
| FAM83E | 5.127 | 5.297 | 7.556 | 8.272 | 8.163 | 7.212 | 4.243 | 0.0455672 | family with sequence similarity 83, member E |
| LRTOMT | 3.364 | 2.357 | 2.726 | 4.813 | 4.939 | 4.810 | 4.249 | 0.0025695 | leucine rich transmembrane and O-methyltransferase domain containing |
| C1GALT1C1 | 0.974 | 3.749 | 2.404 | 5.051 | 3.738 | 4.493 | 4.254 | 0.0384144 | C1 GALT 1-specific chaperone 1 |
| AHNAK2 | 4.607 | 5.185 | 5.935 | 7.275 | 7.143 | 7.459 | 4.256 | 0.0049094 | AHNAK nucleoprotein 2 |
| USP45 | 4.870 | 5.286 | 4.892 | 7.380 | 6.919 | 7.057 | 4.271 | 0.0008688 | ubiquitin specific peptidase 45 |
| EGR2 | 3.059 | 4.144 | 3.459 | 4.952 | 5.557 | 6.938 | 4.280 | 0.0131788 | early growth response 2 |
| TRIM16 | 9.698 | 9.795 | 11.478 | 12.839 | 12.732 | 11.796 | 4.281 | 0.0159977 | tripartite motif-containing 16 |
| ZNF836 | 2.519 | 2.432 | 3.778 | 4.712 | 5.159 | 4.533 | 4.288 | 0.0108987 | zinc finger protein 836 |
| PRRG2 | 5.720 | 5.825 | 7.159 | 8.670 | 8.123 | 7.823 | 4.294 | 0.0120338 | proline rich Gla (G-carboxyglutamic acid) 2 |
| SV2A | 2.296 | 2.559 | 3.218 | 4.809 | 4.149 | 5.320 | 4.295 | 0.0061865 | synaptic vesicle glycoprotein 2A |
| C13orf33 | 0.974 | 2.404 | 0.974 | 4.507 | 2.402 | 3.758 | 4.296 | 0.0251297 | chromosome 13 open reading frame 33 |
| SECISBP2 | 7.462 | 8.773 | 9.901 | 11.026 | 10.881 | 10.110 | 4.313 | 0.0303101 | SECIS binding protein 2 |
| CFP | 2.671 | 2.836 | 3.616 | 5.020 | 4.780 | 5.023 | 4.314 | 0.0035687 | complement factor properdin |
| C18orf25 | 6.378 | 5.876 | 5.699 | 8.151 | 7.812 | 8.399 | 4.326 | 0.0015848 | chromosome 18 open reading frame 25 |
| FUCA1 | 2.247 | 4.649 | 3.021 | 5.494 | 5.135 | 4.983 | 4.330 | 0.0299263 | fucosidase, alpha-L-1, tissue |
| RIPK1 | 4.473 | 5.974 | 5.891 | 8.099 | 7.740 | 6.588 | 4.331 | 0.0193500 | receptor (TNFRSF)-interacting serine-threonine kinase 1 |
| FLJ39653 | 2.296 | 2.327 | 2.447 | 4.412 | 4.421 | 4.856 | 4.335 | 0.0004451 | No description |

TABLE 5-continued

Differentially Expressed Genes in CD24+ Breast Epithelial Cells

| | Nulliparous (NP) Samples | | | Parous (P) Samples | | | | | |
| --- | --- | --- | --- | --- | --- | --- | --- | --- | --- |
| | CD24+ N48 | CD24+ N58 | CD24+ N43 | CD24+ N37 | CD24+ N39 | CD24+ N40 | Pseudo fold change | P value | Gene description |
| PODXL | 8.895 | 7.214 | 7.787 | 10.530 | 9.582 | 9.906 | 4.346 | 0.0127437 | podocalyxin-like |
| RRAGD | 5.678 | 6.731 | 5.726 | 8.058 | 7.798 | 8.180 | 4.348 | 0.0046984 | Ras-related GTP binding D |
| RPL9 | 14.258 | 13.647 | 14.065 | 16.381 | 16.166 | 16.166 | 4.356 | 0.0006078 | ribosomal protein L9 |
| SHROOM3 | 10.537 | 9.235 | 8.787 | 11.864 | 11.403 | 10.910 | 4.358 | 0.0192548 | shroom family member 3 |
| MAP1S | 10.790 | 9.402 | 11.252 | 13.111 | 12.914 | 12.265 | 4.360 | 0.0101581 | microtubule-associated protein 1S |
| RAB6C | −0.026 | 0.121 | −0.026 | 1.734 | 2.105 | 3.152 | 4.380 | 0.0035902 | RAB6C, member RAS oncogene family |
| LOC554202 | −0.026 | −0.026 | 0.121 | 1.734 | 2.105 | 4.428 | 4.380 | 0.0124697 | No description |
| PLK1S1 | −0.026 | 0.505 | 0.505 | 3.825 | 2.105 | 1.348 | 4.380 | 0.0176224 | polo-like kinase 1 substrate 1 |
| RFESD | −0.026 | −0.026 | −0.026 | 2.636 | 1.169 | 2.108 | 4.381 | 0.0120660 | Rieske (Fe-S) domain containing |
| FABP4 | 1.974 | 3.716 | 3.403 | 4.501 | 4.106 | 6.237 | 4.381 | 0.0426309 | fatty acid binding protein 4, adipocyte |
| UBQLNL | −0.026 | 0.121 | 0.121 | 2.108 | 3.176 | 2.108 | 4.387 | 0.0019332 | ubiquilin-like |
| PIWIL4 | −0.026 | −0.026 | 1.098 | 2.108 | 2.636 | 2.108 | 4.387 | 0.0072886 | piwi-like 4 (Drosophila) |
| KLF11 | 7.300 | 5.085 | 7.382 | 9.519 | 8.434 | 8.986 | 4.397 | 0.0179847 | Kruppel-like factor 11 |
| STEAP1 | 7.373 | 7.652 | 7.060 | 9.790 | 9.739 | 8.706 | 4.401 | 0.0048097 | six transmembrane epithelial antigen of the prostate 1 |
| DDTL | 4.899 | 3.212 | 4.699 | 5.775 | 7.037 | 5.712 | 4.402 | 0.0257191 | D-dopachrome tautomerase-like |
| KLF15 | 0.974 | 1.328 | 0.974 | 2.848 | 3.324 | 3.469 | 4.410 | 0.0010798 | Kruppel-like factor 15 |
| PSMB2 | 9.064 | 9.604 | 9.996 | 12.138 | 11.909 | 10.710 | 4.413 | 0.0104175 | proteasome (prosome, macropain) subunit, beta type, 2 |
| C4orf14 | 8.300 | 7.054 | 6.932 | 9.196 | 9.210 | 9.159 | 4.417 | 0.0118212 | chromosome 4 open reading frame 14 |
| EVPL | 7.424 | 6.814 | 8.832 | 9.470 | 9.742 | 9.568 | 4.420 | 0.0188833 | envoplakin |
| SLC45A4 | 3.954 | 4.587 | 5.699 | 7.065 | 6.860 | 6.101 | 4.431 | 0.0168987 | solute carrier family 45, member 4 |
| LAMC3 | 2.296 | 2.296 | 2.419 | 4.848 | 4.178 | 4.445 | 4.434 | 0.0008173 | laminin, gamma 3 |
| COPS7B | 4.605 | 3.176 | 3.345 | 5.948 | 5.462 | 5.496 | 4.441 | 0.0103814 | COP9 constitutive photomorphogenic homolog subunit 7B (Arabidopsis) |
| CSNK2A1P | 8.012 | 7.602 | 9.351 | 10.691 | 10.168 | 9.970 | 4.455 | 0.0150069 | casein kinase 2, alpha 1 polypeptide pseudogene |
| HEXA | 6.192 | 4.579 | 4.881 | 7.133 | 7.044 | 7.038 | 4.477 | 0.0131059 | hexosaminidase A (alpha polypeptide) |
| CACNB1 | 5.178 | 6.016 | 7.480 | 7.782 | 8.183 | 8.751 | 4.491 | 0.0247007 | calcium channel, voltage-dependent, beta 1 subunit |
| PLVAP | 1.974 | 2.649 | 2.880 | 5.884 | 4.817 | 3.954 | 4.491 | 0.0090522 | plasmalemma vesicle associated protein |
| GDI1 | 8.365 | 5.771 | 6.430 | 8.381 | 8.601 | 8.868 | 4.503 | 0.0476746 | GDP dissociation inhibitor 1 |
| TTC32 | 4.290 | 4.739 | 4.915 | 6.911 | 7.300 | 6.122 | 4.506 | 0.0042233 | chromosome 15 open reading frame 57 |
| C15orf57 | 5.298 | 4.139 | 4.187 | 6.967 | 6.977 | 6.315 | 4.520 | 0.0046048 | tetratricopeptide repeat domain 32 |
| CWF19L1 | 3.616 | 3.979 | 4.428 | 6.156 | 6.751 | 5.324 | 4.522 | 0.0080591 | CWF19-like 1, cell cycle control (S. pombe) |
| LRG1 | 5.273 | 7.375 | 8.531 | 9.560 | 9.616 | 9.335 | 4.548 | 0.0257084 | leucine-rich alpha-2-glycoprotein 1 |
| INTS12 | 6.566 | 6.292 | 7.556 | 8.702 | 8.901 | 8.751 | 4.549 | 0.0054520 | integrator complex subunit 12 |
| PLIN2 | 5.317 | 6.567 | 6.312 | 8.931 | 8.150 | 7.507 | 4.564 | 0.0105756 | perilipin 2 |
| C1R | 6.996 | 8.233 | 7.301 | 10.255 | 9.494 | 9.235 | 4.572 | 0.0068857 | complement component 1, r subcomponent |
| SIX5 | 6.439 | 5.872 | 5.438 | 8.222 | 8.065 | 7.672 | 4.572 | 0.0031451 | SIX homeobox 5 |
| NRBP1 | 9.452 | 9.012 | 8.869 | 11.274 | 11.228 | 11.065 | 4.582 | 0.0008795 | nuclear receptor binding protein 1 |
| DENND1A | 6.543 | 6.088 | 6.846 | 9.043 | 8.859 | 7.562 | 4.584 | 0.0109601 | DENN/MADD domain containing 1A |
| PPM1D | 6.104 | 4.872 | 3.831 | 7.261 | 6.724 | 7.074 | 4.599 | 0.0180706 | protein phosphatase, Mg2+/Mn2+ dependent, 1D |
| NPTX2 | 1.559 | 3.187 | 1.610 | 4.273 | 3.859 | 3.767 | 4.620 | 0.0173047 | neuronal pentraxin II |
| S100A3 | 3.336 | 5.236 | 5.924 | 7.684 | 7.445 | 6.025 | 4.623 | 0.0335173 | S100 calcium binding protein A3 |
| OPLAH | 7.418 | 6.665 | 8.218 | 9.568 | 9.723 | 9.629 | 4.629 | 0.0050154 | 5-oxoprolinase (ATP-hydrolysing) |
| C15orf61 | 6.473 | 6.131 | 6.033 | 8.248 | 8.501 | 8.401 | 4.643 | 0.0004881 | chromosome 15 open reading frame 61 |
| TNFRSF6B | 5.376 | 7.437 | 6.176 | 9.362 | 9.111 | 7.591 | 4.643 | 0.0190867 | tumor necrosis factor receptor superfamily, member 6b, decoy |
| KRT14 | 8.427 | 10.226 | 9.522 | 10.643 | 11.468 | 13.860 | 4.646 | 0.0302840 | keratin 14 |
| RTN4RL2 | 3.188 | 5.496 | 6.686 | 7.686 | 7.723 | 7.802 | 4.682 | 0.0246247 | reticulon 4 receptor-like 2 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| ACSL4 | 5.097 | 3.706 | 4.445 | 6.691 | 6.679 | 6.119 | 4.703 | 0.0063715 | acyl-CoA synthetase long-chain family member 4 |
| AP4S1 | 8.645 | 6.718 | 6.823 | 9.138 | 8.958 | 9.724 | 4.723 | 0.0252962 | adaptor-related protein complex 4, sigma 1 subunit |
| ABHD3 | 1.974 | 1.974 | 2.840 | 4.572 | 4.222 | 4.224 | 4.749 | 0.0026477 | abhydrolase domain containing 3 |
| C6orf145 | 9.746 | 9.469 | 10.953 | 12.198 | 11.721 | 12.171 | 4.762 | 0.0096401 | chromosome 6 open reading frame 145 |
| C14orf167 | 4.059 | 3.978 | 4.392 | 6.319 | 6.647 | 5.554 | 4.774 | 0.0037206 | chromosome 14 open reading frame 167 |
| TSG101 | 9.205 | 9.492 | 9.566 | 12.128 | 11.751 | 11.415 | 4.787 | 0.0007467 | tumor susceptibility gene 101 |
| REPIN1 | 8.862 | 9.184 | 9.326 | 12.007 | 11.452 | 11.036 | 4.814 | 0.0014543 | replication initiator 1 |
| SHKBP1 | 6.278 | 7.470 | 8.399 | 10.660 | 9.962 | 8.546 | 4.815 | 0.0233085 | SH3KBP1 binding protein 1 |
| PSCA | 3.593 | 3.927 | 3.447 | 6.085 | 6.197 | 5.633 | 4.824 | 0.0007145 | prostate stem cell antigen |
| PARP10 | 7.597 | 6.340 | 8.117 | 9.879 | 9.873 | 9.670 | 4.843 | 0.0050046 | poly (ADP-ribose) polymerase family, member 10 |
| CSGALNACT1 | 4.351 | 5.106 | 4.231 | 7.551 | 6.629 | 5.119 | 4.851 | 0.0357552 | chondroitin sulfate N-acetylgalactosaminyltransferase 1 |
| SHF | 4.042 | 4.895 | 5.156 | 7.439 | 7.109 | 6.755 | 4.867 | 0.0024206 | Src homology 2 domain containing F |
| CXorf15 | 2.247 | 3.469 | 3.089 | 5.063 | 5.066 | 5.752 | 4.869 | 0.0033400 | No description |
| ASAP3 | 3.539 | 3.178 | 3.322 | 6.046 | 4.811 | 5.606 | 4.869 | 0.0035794 | ArfGAP with SH3 domain, ankyrin repeat and PH domain 3 |
| SMARCA4 | 9.708 | 9.428 | 11.418 | 12.364 | 12.470 | 11.712 | 4.873 | 0.0202694 | SWI/SNF related, matrix associated, actin dependent regulator of chromatin, subfamily a, member 4 |
| SMURF1 | 10.045 | 9.779 | 11.914 | 12.707 | 12.604 | 12.065 | 4.876 | 0.0284981 | SMAD specific E3 ubiquitin protein ligase 1 |
| SLC25A1 | 7.758 | 7.810 | 8.241 | 10.446 | 10.217 | 10.046 | 4.881 | 0.0005610 | solute carrier family 25 (mitochondrial carrier; citrate transporter), member 1 |
| AES | 11.175 | 11.834 | 12.366 | 14.354 | 14.124 | 13.822 | 4.892 | 0.0026685 | amino-terminal enhancer of split |
| FAM50B | 3.220 | 4.759 | 5.313 | 7.128 | 7.051 | 5.804 | 4.896 | 0.0192709 | family with sequence similarity 50, member B |
| NFE2L1 | 9.214 | 9.721 | 9.958 | 12.644 | 12.015 | 10.778 | 4.901 | 0.0110153 | nuclear factor (erythroid-derived 2)-like 1 |
| SNAI2 | 2.747 | 2.162 | 2.013 | 4.457 | 3.196 | 5.662 | 4.906 | 0.0214213 | snail homolog 2 (Drosophila) |
| SPRY2 | 6.075 | 4.862 | 4.273 | 7.232 | 6.569 | 7.407 | 4.911 | 0.0148933 | sprouty homolog 2 (Drosophila) |
| KIAA0562 | 5.826 | 6.878 | 8.062 | 9.616 | 9.150 | 9.176 | 4.920 | 0.0105288 | KIAA0562 |
| GOS2 | 6.337 | 5.884 | 4.657 | 6.379 | 8.183 | 9.382 | 4.921 | 0.0336876 | G0/G1 switch 2 |
| AKNA | 7.803 | 8.030 | 10.357 | 10.932 | 10.968 | 10.104 | 4.927 | 0.0433423 | AT-hook transcription factor |
| RPS11 | 15.724 | 14.065 | 14.398 | 17.032 | 17.032 | 16.381 | 4.982 | 0.0109386 | ribosomal protein S11 |
| DOCK9 | 3.831 | 5.107 | 5.758 | 8.077 | 6.696 | 6.586 | 4.988 | 0.0183699 | dedicator of cytokinesis 9 |
| RACGAP1 | 4.605 | 3.176 | 4.240 | 6.666 | 6.559 | 6.229 | 4.989 | 0.0030691 | Rae GTPase activating protein 1 |
| MTERFD2 | 3.908 | 5.421 | 4.598 | 7.606 | 6.918 | 6.857 | 4.994 | 0.0040238 | MTERF domain containing 2 |
| SLC17A9 | 2.296 | 2.357 | 2.627 | 4.678 | 4.503 | 5.248 | 4.995 | 0.0080005 | solute carrier family 17, member 9 |
| GOLGA2L1 | 5.823 | 4.891 | 7.105 | 8.406 | 7.641 | 8.147 | 5.007 | 0.0171880 | No description |
| PIK3R1 | 5.535 | 7.277 | 6.524 | 9.340 | 8.850 | 8.479 | 5.014 | 0.0060545 | phosphoinositide-3-kinase, regulatory subunit 1 (alpha) |
| ZNF619 | 1.913 | 1.688 | 2.263 | 5.558 | 4.239 | 3.825 | 5.014 | 0.0043968 | zinc finger protein 619 |
| ODAM | 0.974 | 0.974 | 0.974 | 4.062 | 2.402 | 3.304 | 5.025 | 0.0051213 | odontogenic, ameloblast asssociated |
| FZD5 | 4.724 | 6.006 | 7.596 | 8.523 | 8.345 | 8.013 | 5.058 | 0.0271097 | frizzled homolog 5 (Drosophila) |
| MRPL34 | 7.990 | 7.283 | 9.531 | 11.428 | 11.088 | 9.629 | 5.085 | 0.0194505 | mitochondrial ribosomal protein L34 |
| ID3 | 5.720 | 5.790 | 6.038 | 8.813 | 7.994 | 8.136 | 5.085 | 0.0008580 | Description |
| HIRIP3 | 0.974 | 0.974 | 1.264 | 3.324 | 3.081 | 4.062 | 5.098 | 0.0012847 | HIRA interacting protein 3 |
| FADS6 | 0.974 | 1.328 | 1.643 | 3.324 | 4.207 | 3.469 | 5.098 | 0.0017375 | fatty acid desaturase domain family, member 6 |
| DSG2 | 9.885 | 9.940 | 9.402 | 12.013 | 11.772 | 12.402 | 5.170 | 0.0009563 | desmoglein 2 |
| TCHP | 5.848 | 5.513 | 6.699 | 8.143 | 8.482 | 8.223 | 5.191 | 0.0027368 | trichoplein, keratin filament binding |
| CYGB | 3.593 | 3.349 | 4.335 | 7.187 | 5.973 | 5.559 | 5.207 | 0.0058972 | cytoglobin |
| PPAP2B | 5.368 | 9.445 | 7.446 | 10.634 | 9.829 | 9.361 | 5.216 | 0.0459417 | phosphatidic acid phosphatase type 2B |
| SOBP | 2.296 | 2.627 | 2.296 | 4.486 | 4.683 | 6.119 | 5.229 | 0.0033292 | sine oculis binding protein homolog (Drosophila) |

TABLE 5-continued

Differentially Expressed Genes in CD24+ Breast Epithelial Cells

| | Nulliparous (NP) Samples | | | Parous (P) Samples | | | | | |
| --- | --- | --- | --- | --- | --- | --- | --- | --- | --- |
| | CD24+ N48 | CD24+ N58 | CD24+ N43 | CD24+ N37 | CD24+ N39 | CD24+ N40 | Pseudo fold change | P value | Gene description |
| RDH5 | 4.282 | 3.922 | 6.404 | 6.669 | 6.858 | 6.643 | 5.231 | 0.0385971 | retinol dehydrogenase 5(11-cis/9-cis) |
| ANAPC1 | 6.128 | 6.987 | 8.691 | 9.047 | 9.381 | 9.464 | 5.258 | 0.0271420 | anaphase promoting complex subunit 1 |
| ADRB3 | 4.448 | 5.344 | 4.801 | 7.750 | 7.534 | 6.056 | 5.301 | 0.0098841 | adrenergic, beta-3-, receptor |
| PCMT1 | 8.990 | 8.666 | 9.058 | 11.397 | 11.474 | 10.657 | 5.303 | 0.0014651 | protein-L-isoaspartate (D-aspartate) O-methyltransferase |
| XRCC6 | 11.845 | 11.961 | 12.547 | 14.755 | 14.954 | 14.198 | 5.304 | 0.0010691 | X-ray repair complementing defective repair in Chinese hamster cells 6 |
| CD34 | 2.747 | 3.334 | 3.704 | 7.288 | 5.750 | 4.806 | 5.335 | 0.0103960 | CD34 molecule |
| HOXC8 | 2.296 | 3.702 | 4.276 | 6.251 | 5.410 | 6.119 | 5.341 | 0.0084006 | homeobox C8 |
| CBR3 | 3.117 | 3.232 | 3.222 | 5.640 | 6.224 | 5.148 | 5.346 | 0.0011719 | carbonyl reductase 3 |
| PDPN | 0.974 | 1.643 | 0.974 | 3.922 | 3.022 | 4.062 | 5.348 | 0.0021596 | podoplanin |
| NME2P1 | 3.336 | 1.643 | 2.108 | 5.380 | 5.010 | 4.062 | 5.348 | 0.0087583 | non-metastatic cells 2, protein (NM23B) expressed in, pseudogene 1 |
| MESTIT1 | 5.523 | 3.659 | 5.357 | 7.712 | 7.948 | 7.639 | 5.370 | 0.0033952 | MEST intronic transcript 1 (non-protein coding) |
| POLR3E | 5.847 | 6.048 | 7.847 | 8.357 | 8.473 | 8.488 | 5.373 | 0.0233668 | polymerase (RNA) III (DNA directed) polypeptide E (80 kD) |
| RHOF | 2.747 | 2.770 | 5.071 | 5.501 | 5.832 | 5.177 | 5.388 | 0.0331213 | ras homolog gene family, member F (in filopodia) |
| C17orf103 | 5.420 | 5.603 | 5.389 | 8.736 | 7.852 | 6.923 | 5.400 | 0.0057283 | chromosome 17 open reading frame 103 |
| SMTNL2 | 0.974 | 0.974 | 3.021 | 5.454 | 3.922 | 2.878 | 5.400 | 0.0307698 | smoothelin-like 2 |
| TGFB2 | 7.040 | 6.197 | 6.958 | 8.907 | 9.316 | 9.479 | 5.422 | 0.0011504 | transforming growth factor, beta 2 |
| DDR2 | 4.137 | 2.948 | 3.552 | 6.806 | 5.993 | 5.107 | 5.430 | 0.0078235 | discoidin domain receptor tyrosine kinase 2 |
| SFRP4 | 1.974 | 2.162 | 2.347 | 5.262 | 3.712 | 4.614 | 5.470 | 0.0040023 | secreted frizzled-related protein 4 |
| KCNK3 | 1.559 | 1.559 | 1.759 | 4.851 | 4.013 | 4.013 | 5.476 | 0.0006539 | potassium channel, subfamily K, member 3 |
| SCRIB | 7.441 | 7.845 | 10.123 | 10.252 | 10.691 | 10.302 | 5.488 | 0.0405664 | scribbled homolog (Drosophila) |
| PAPPA | 3.296 | 4.931 | 4.357 | 7.515 | 6.817 | 5.147 | 5.500 | 0.0231167 | pregnancy-associated plasma protein A, pappalysin 1 |
| ACTL6A | 1.974 | 4.382 | 2.347 | 5.295 | 4.448 | 5.394 | 5.554 | 0.0257398 | actin-like 6A |
| FAIM2 | 2.296 | 2.448 | 2.327 | 5.696 | 4.811 | 2.695 | 5.594 | 0.0393008 | Fas apoptotic inhibitory molecule 2 |
| CIB2 | 6.066 | 4.168 | 6.409 | 8.904 | 8.530 | 7.683 | 5.639 | 0.0089854 | calcium and integrin binding family member 2 |
| DNAJC6 | 3.117 | 3.653 | 2.925 | 6.158 | 4.685 | 5.664 | 5.675 | 0.0053876 | DnaJ (Hsp40) homolog, subfamily C, member 6 |
| RABL3 | 6.044 | 6.623 | 7.917 | 9.529 | 9.827 | 8.549 | 5.676 | 0.0102602 | RAB, member of RAS oncogene family-like 3 |
| NRG1 | 3.144 | 4.592 | 5.195 | 5.756 | 7.097 | 7.487 | 5.678 | 0.0154305 | neuregulin 1 |
| GZF1 | 4.548 | 4.952 | 6.004 | 7.086 | 7.459 | 7.526 | 5.682 | 0.0053124 | GDNF-inducible zinc finger protein 1 |
| C6orf15 | 2.878 | 3.469 | 4.826 | 6.466 | 7.332 | 4.983 | 5.683 | 0.0188995 | chromosome 6 open reading frame 15 |
| FOXC2 | 1.559 | 3.247 | 4.313 | 5.758 | 6.734 | 5.720 | 5.700 | 0.0091090 | forkhead box C2 (MFH-1, mesenchyme forkhead 1) |
| NDUFV3 | 8.140 | 7.141 | 7.928 | 10.615 | 10.657 | 9.357 | 5.725 | 0.0046424 | NADH dehydrogenase (ubiquinone) flavoprotein 3, 10 kDa |
| SOX10 | 8.563 | 7.788 | 7.514 | 10.705 | 10.319 | 10.144 | 5.780 | 0.0017160 | SRY (sex determining region Y)-box 10 |
| SLC2A3 | 2.296 | 3.026 | 4.008 | 6.010 | 4.026 | 6.548 | 5.814 | 0.0234497 | solute carrier family 2 (facilitated glucose transporter), member 3 |
| PI4K2A | 7.661 | 8.128 | 8.892 | 10.898 | 10.668 | 10.302 | 5.815 | 0.0025802 | phosphatidylinositol 4-kinase type 2 alpha |
| HMGB1L1 | -0.026 | 1.098 | -0.026 | 2.108 | 2.636 | 3.649 | 5.862 | 0.0068964 | No description |
| USP54 | 9.254 | 6.849 | 6.335 | 9.623 | 8.892 | 10.393 | 5.885 | 0.0439340 | ubiquitin specific peptidase 54 |
| H1F0 | 9.432 | 8.005 | 7.107 | 12.675 | 9.666 | 9.735 | 5.891 | 0.0433315 | H1 histone family, member 0 |
| RASSF4 | 6.241 | 5.509 | 8.215 | 10.067 | 9.151 | 8.068 | 5.891 | 0.0286262 | Ras association (RalGDS/AF-6) domain family member 4 |
| FANCB | 3.966 | 0.611 | 2.636 | 5.270 | 5.197 | 4.428 | 5.903 | 0.0253684 | Fanconi anemia, complementation group B |
| SCNM1 | 2.878 | 3.492 | 5.993 | 7.141 | 6.953 | 5.447 | 5.934 | 0.0394405 | sodium channel modifier 1 |
| PJA1 | 5.637 | 4.921 | 6.041 | 8.208 | 8.256 | 8.009 | 5.943 | 0.0010368 | praja ring finger 1 |
| BMF | 2.782 | 5.194 | 3.730 | 7.769 | 6.853 | 5.373 | 6.024 | 0.0183170 | Bcl2 modifying factor |
| ST6GALNAC4 | 6.056 | 6.433 | 7.295 | 9.886 | 9.250 | 8.215 | 6.024 | 0.0067652 | ST6 (alpha-N-acetyl-neuraminyl-2,3-beta-galactosyl-1,3)-N-acetylgalactosaminide alpha-2,6-sialyltransferase 4 |

TABLE 5-continued

Differentially Expressed Genes in CD24+ Breast Epithelial Cells

| | Nulliparous (NP) Samples | | | Parous (P) Samples | | | | | |
| --- | --- | --- | --- | --- | --- | --- | --- | --- | --- |
| | CD24+ N48 | CD24+ N58 | CD24+ N43 | CD24+ N37 | CD24+ N39 | CD24+ N40 | Pseudo fold change | P value | Gene description |
| QRSL1 | 7.711 | 6.686 | 8.578 | 10.354 | 10.305 | 9.609 | 6.037 | 0.0076255 | glutaminyl-tRNA synthase (glutamine-hydrolyzing)-like 1 |
| CCND2 | 3.434 | 4.267 | 3.504 | 6.100 | 5.879 | 7.651 | 6.046 | 0.0043653 | cyclin D2 |
| SLC25A25 | 9.485 | 7.681 | 7.237 | 10.324 | 9.836 | 10.746 | 6.058 | 0.0196055 | solute carrier family 25 (mitochondrial carrier; phosphate carrier), member 25 |
| HSPA1L | 2.247 | 1.050 | 2.636 | 4.282 | 4.062 | 5.236 | 6.060 | 0.0060330 | heat shock 70 kDa protein 1-like |
| PGDN | 0.974 | 1.050 | 1.050 | 3.659 | 1.692 | 4.235 | 6.102 | 0.0217675 | podocan |
| SHISA4 | 1.559 | 4.957 | 4.997 | 7.615 | 6.521 | 5.525 | 6.136 | 0.0404244 | shisa homolog 4 (*Xenopus laevis*) |
| ZNF570 | −0.026 | 2.038 | 2.671 | 4.675 | 4.657 | 3.825 | 6.142 | 0.0115211 | zinc finger protein 570 |
| AIPL1 | 3.649 | 2.108 | 3.335 | 5.775 | 6.271 | 5.023 | 6.157 | 0.0048880 | aryl hydrocarbon receptor interacting protein-like 1 |
| NFIC | 8.833 | 8.498 | 8.611 | 11.564 | 11.237 | 10.572 | 6.175 | 0.0011228 | nuclear factor I/C (CCAAT-binding transcription factor) |
| CD40 | 4.054 | 5.253 | 3.827 | 7.889 | 6.690 | 6.032 | 6.216 | 0.0104605 | CD40 molecule, TNF receptor superfamily member 5 |
| SLC43A1 | 3.364 | 2.859 | 2.475 | 6.005 | 5.660 | 4.810 | 6.235 | 0.0023400 | solute carrier family 43, member 1 |
| NDUFA4L2 | 1.913 | 1.098 | 2.912 | 5.558 | 4.742 | 3.152 | 6.259 | 0.0186408 | NADH dehydrogenase (ubiquinone) 1 alpha subcomplex, 4-like 2 |
| LOC285375 | −0.026 | −0.026 | −0.026 | 3.664 | 2.636 | 2.108 | 6.327 | 0.0016946 | No description |
| ZNF691 | −0.026 | 0.121 | −0.026 | 1.734 | 2.636 | 3.152 | 6.327 | 0.0024966 | zinc finger protein 691 |
| KRTAP3-2 | −0.026 | −0.026 | −0.026 | 2.636 | 2.636 | 1.348 | 6.327 | 0.0042655 | keratin associated protein 3-2 |
| NDN | −0.026 | 0.611 | 1.734 | 3.974 | 2.636 | 3.335 | 6.327 | 0.0079263 | necdin homolog (mouse) |
| RAB34 | 7.698 | 8.519 | 9.167 | 11.615 | 11.262 | 10.365 | 6.350 | 0.0045042 | RAB34, member RAS oncogene family |
| LOC283174 | 2.559 | 2.585 | 2.663 | 3.961 | 5.256 | 5.379 | 6.368 | 0.0046209 | No description |
| PGS1 | 6.437 | 6.455 | 6.986 | 9.662 | 9.537 | 9.035 | 6.389 | 0.0004344 | phosphatidylglycerophosphate synthase 1 |
| TMEM81 | −0.026 | 1.913 | 0.505 | 3.176 | 2.836 | 4.592 | 6.404 | 0.0101988 | transmembrane protein 81 |
| OGN | −0.026 | −0.026 | −0.026 | 2.836 | 2.636 | 2.671 | 6.483 | 0.0001136 | osteoglycin |
| RDH16 | −0.026 | 1.688 | 0.505 | 4.208 | 3.345 | 2.671 | 6.483 | 0.0070514 | retinol dehydrogenase 16 (all-trans) |
| WFDC6 | −0.026 | −0.026 | −0.026 | 3.664 | 1.169 | 2.671 | 6.483 | 0.0109094 | WAP four-disulfide core domain 6 |
| ITGB7 | 3.059 | 3.883 | 6.051 | 5.825 | 6.588 | 7.233 | 6.525 | 0.0382809 | integrin, beta 7 |
| TLX3 | 0.974 | 1.050 | 1.050 | 4.197 | 3.231 | 3.758 | 6.535 | 0.0005718 | T-cell leukemia homeobox 3 |
| ATP8B2 | 2.974 | 4.616 | 3.071 | 6.083 | 5.690 | 6.968 | 6.569 | 0.0062525 | ATPase, class I, type 8B, member 2 |
| LOC93432 | 0.974 | 2.404 | 1.050 | 5.120 | 4.207 | 3.516 | 6.570 | 0.0051965 | No description |
| SP4 | 3.059 | 3.841 | 2.650 | 6.412 | 5.557 | 5.778 | 6.586 | 0.0017268 | Sp4 transcription factor |
| SERPINB7 | 1.974 | 4.103 | 2.973 | 5.695 | 5.999 | 5.493 | 6.599 | 0.0053699 | serpin peptidase inhibitor, clade B (ovalbumin), member 7 |
| PDE1B | 1.559 | 1.559 | 2.037 | 5.825 | 4.282 | 3.059 | 6.600 | 0.0123484 | phosphodiesterase 1B, calmodulin-dependent |
| SS18L2 | 9.202 | 7.465 | 8.341 | 11.072 | 11.499 | 10.566 | 6.638 | 0.0040345 | synovial sarcoma translocation gene on chromosome 18-like 2 |
| ANXA5 | 5.656 | 5.426 | 5.717 | 8.417 | 8.450 | 8.057 | 6.648 | 0.0001949 | annexin A5 |
| DRG1 | 4.208 | 5.162 | 6.825 | 7.921 | 7.964 | 6.941 | 6.651 | 0.0253231 | developmentally regulated GTP binding protein 1 |
| SCN4A | 2.782 | 2.804 | 3.322 | 6.557 | 5.507 | 5.546 | 6.692 | 0.0009670 | sodium channel, voltage-gated, type IV, alpha subunit |
| CCT2 | 11.076 | 11.298 | 11.816 | 14.041 | 14.159 | 13.978 | 6.696 | 0.0003914 | chaperonin containing TCP1, subunit 2 (beta) |
| ASF1A | 5.376 | 5.757 | 6.051 | 8.798 | 8.567 | 7.591 | 6.713 | 0.0020276 | ASF1 anti-silencing function 1 homolog A (*S. cerevisiae*) |
| SETD8 | 8.587 | 8.230 | 10.095 | 11.160 | 11.360 | 11.345 | 6.763 | 0.0083899 | SET domain containing (lysine methyltransferase) 8 |
| C1orf51 | 5.931 | 4.144 | 6.434 | 9.111 | 8.218 | 8.690 | 6.766 | 0.0044935 | chromosome 1 open reading frame 51 |
| FMNL3 | 4.210 | 4.541 | 5.829 | 7.613 | 6.969 | 7.662 | 6.772 | 0.0044674 | formin-like 3 |
| PRO0628 | 4.851 | 2.075 | 3.032 | 6.412 | 5.898 | 4.851 | 6.849 | 0.0256427 | No description |
| RAB3A | 5.167 | 2.377 | 3.388 | 6.166 | 6.625 | 6.013 | 6.859 | 0.0140015 | RAB3A, member RAS oncogene family |
| ERP27 | 0.974 | 1.050 | 3.659 | 4.062 | 4.312 | 3.758 | 6.885 | 0.0339655 | endoplasmic reticulum protein 27 |
| MHP | 5.236 | 4.507 | 4.514 | 8.025 | 7.919 | 7.141 | 6.911 | 0.0007790 | migration and invasion inhibitory protein |
| SOX11 | 2.559 | 3.688 | 3.037 | 5.838 | 6.091 | 5.356 | 6.946 | 0.0015188 | SRY (sex determining region Y)-box 11 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| ADC | 3.859 | 5.027 | 6.508 | 7.455 | 7.854 | 8.607 | 7.096 | 0.0104497 | arginine decarboxylase |
| C6orf41 | 3.188 | 4.322 | 3.345 | 6.068 | 6.173 | 6.387 | 7.101 | 0.0014436 | No description |
| EGFL7 | 0.974 | 3.758 | 5.446 | 7.838 | 6.596 | 6.479 | 7.153 | 0.0187536 | EGF-like-domain, multiple 7 |
| SRGAP2 | 4.576 | 5.167 | 5.126 | 8.540 | 7.895 | 7.430 | 7.231 | 0.0007360 | SLIT-ROBO Rho GTPase activating protein 2 |
| IL1B | -0.026 | -0.026 | 0.121 | 0.845 | 2.836 | 3.335 | 7.267 | 0.0169302 | interleukin 1, beta |
| SLC43A2 | 5.537 | 7.371 | 6.413 | 9.663 | 9.283 | 8.745 | 7.312 | 0.0039708 | solute carrier family 43, member 2 |
| RARRES2 | 0.974 | 1.691 | 1.050 | 3.855 | 4.207 | 4.493 | 7.367 | 0.0004236 | retinoic acid receptor responder (tazarotene induced) 2 |
| BRLIN1 | 7.385 | 7.825 | 8.613 | 10.403 | 10.716 | 10.706 | 7.369 | 0.0013131 | ER lipid raft associated 1 |
| LRRC37A3 | 2.247 | 3.246 | 5.386 | 6.089 | 6.373 | 6.134 | 7.404 | 0.0199163 | leucine rich repeat containing 37, member A3 |
| RMND5B | 6.374 | 6.170 | 7.334 | 9.674 | 9.492 | 9.059 | 7.406 | 0.0013239 | required for meiotic nuclear division 5 homolog B (S. cerevisiae) |
| FABP3 | 1.559 | 1.559 | 3.095 | 4.013 | 4.471 | 5.986 | 7.418 | 0.0098135 | fatty acid binding protein 3, muscle and heart (mammary-derived growth inhibitor) |
| LAT | 3.954 | 4.641 | 7.226 | 7.445 | 7.536 | 7.567 | 7.437 | 0.0385226 | linker for activation of T cells |
| C21orf91 | 4.544 | 6.908 | 5.162 | 8.060 | 8.046 | 8.444 | 7.456 | 0.0090629 | chromosome 21 open reading frame 91 |
| LHFP | 2.519 | 1.804 | 1.759 | 4.704 | 3.859 | 6.147 | 7.463 | 0.0060975 | lipoma HMGIC fusion partner |
| CCL4 | 0.974 | 2.826 | 1.050 | 4.197 | 3.887 | 5.219 | 7.529 | 0.0072134 | chemokine (C-C motif) ligand 4 |
| PPP1R3F | 2.296 | 3.507 | 5.048 | 6.828 | 6.424 | 6.151 | 7.553 | 0.0096807 | protein phosphatase 1, regulatory (inhibitor) subunit 3F |
| PLAU | 7.573 | 11.673 | 10.384 | 13.927 | 13.321 | 11.194 | 7.658 | 0.0445088 | plasminogen activator, urokinase |
| TMOD1 | 3.412 | 4.353 | 4.965 | 6.501 | 8.072 | 6.356 | 7.695 | 0.0078342 | tropomodulin 1 |
| VNN3 | 4.215 | 6.742 | 6.053 | 9.694 | 8.977 | 8.930 | 7.740 | 0.0034582 | vanin 3 |
| CNRIP1 | 0.974 | 2.531 | 1.643 | 5.084 | 4.605 | 4.191 | 7.793 | 0.0022325 | cannabinoid receptor interacting protein 1 |
| CD93 | 2.974 | 4.512 | 3.665 | 7.936 | 6.078 | 5.939 | 7.806 | 0.0077982 | CD93 molecule |
| TACC1 | 5.001 | 5.115 | 5.156 | 8.687 | 8.091 | 7.182 | 7.869 | 0.0014029 | transforming, acidic coiled-coil containing protein 1 |
| FOXF2 | 1.559 | 1.559 | 1.559 | 5.277 | 3.032 | 4.554 | 7.972 | 0.0061167 | forkhead box F2 |
| PUS7L | 1.974 | 2.926 | 2.860 | 5.517 | 5.921 | 5.136 | 7.973 | 0.0009094 | pseudouridylate synthase 7 homolog (S. cerevisiae)-like |
| GPIHBP1 | 0.974 | 2.878 | 4.712 | 6.844 | 5.874 | 5.236 | 7.976 | 0.0192195 | glycosylphosphatidylinositol anchored high density lipoprotein binding protein 1 |
| MMP3 | 2.559 | 3.591 | 3.591 | 8.119 | 6.587 | 5.285 | 7.977 | 0.0058327 | matrix metallopeptidase 3 (stromelysin 1, progelatinase) |
| INHBA | 2.296 | 5.376 | 3.820 | 6.845 | 7.069 | 6.431 | 8.138 | 0.0114160 | inhibin, beta A |
| FAM70B | -0.026 | 0.121 | 1.098 | 4.675 | 2.636 | 3.152 | 8.174 | 0.0043223 | family with sequence similarity 70, member B |
| CYB5R2 | 7.820 | 8.017 | 9.414 | 11.343 | 10.857 | 11.085 | 8.203 | 0.0033185 | cytochrome b5 reductase 2 |
| STEAP3 | 5.624 | 5.837 | 7.750 | 9.420 | 9.391 | 8.660 | 8.206 | 0.0079371 | STEAP family member 3 |
| INPP5D | 2.944 | 2.602 | 3.364 | 5.821 | 5.991 | 6.303 | 8.210 | 0.0002701 | inositol polyphosphate-5-phosphatase, 145 kDa |
| MMP12 | 0.974 | 3.848 | 2.933 | 6.888 | 5.949 | 5.597 | 8.226 | 0.0056846 | matrix metallopeptidase 12 (macrophage elastase) |
| HSD11B1 | 6.630 | 6.715 | 7.168 | 10.372 | 9.674 | 9.693 | 8.249 | 0.0003484 | hydroxysteroid (11-beta) dehydrogenase 1 |
| GMFG | 0.974 | 0.974 | 3.021 | 6.066 | 4.989 | 3.758 | 8.250 | 0.0089140 | glia maturation factor, gamma |
| TNFRSF1B | 7.518 | 9.057 | 10.612 | 12.261 | 12.108 | 10.841 | 8.287 | 0.0210752 | tumor necrosis factor receptor superfamily, member 1B |
| ABCB4 | -0.026 | 0.505 | 0.121 | 3.176 | 2.105 | 3.649 | 8.306 | 0.0022433 | ATP-binding cassette, sub-family B (MDR/TAP), member 4 |
| RPL23P8 | 1.913 | 0.121 | 0.121 | 3.176 | 3.176 | 3.335 | 8.306 | 0.0065787 | ribosomal protein L23 pseudogene 8 |
| ETV7 | 2.878 | 4.083 | 4.699 | 7.804 | 7.164 | 6.353 | 8.602 | 0.0032510 | ets variant 7 |
| HSPE1 | 2.519 | 2.183 | 4.869 | 5.341 | 7.135 | 5.624 | 8.608 | 0.0176117 | heat shock 10 kDa protein 1 (chaperonin 10) |
| DEXI | 7.926 | 8.742 | 10.539 | 11.854 | 11.950 | 11.379 | 8.645 | 0.0114413 | Dexi homolog (mouse) |
| ELTD1 | 2.296 | 5.344 | 4.017 | 8.470 | 7.135 | 7.063 | 8.728 | 0.0063131 | EGF, latrophilin and seven transmembrane domain containing 1 |

TABLE 5-continued

Differentially Expressed Genes in CD24+ Breast Epithelial Cells

| | Nulliparous (NP) Samples | | | Parous (P) Samples | | | | | | |
|---|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| IRX1 | 6.241 | 6.512 | 7.953 | 9.477 | 9.651 | 10.180 | 8.804 | 0.0032026 | iroquois homeobox 1 |
| PLEKHM1P | 4.921 | 4.337 | 7.964 | 8.068 | 8.331 | 7.893 | 8.857 | 0.0455142 | pleckstrin homology domain containing, family M (with RUN domain) member 1 pseudogene |
| TBX2 | 2.878 | 3.799 | 0.974 | 6.953 | 4.831 | 5.527 | 8.900 | 0.0122863 | T-box 2 |
| ADRA2C | 0.974 | 3.469 | 5.310 | 6.695 | 6.660 | 4.983 | 9.132 | 0.0407498 | adrenergic, alpha-2C-, receptor |
| TGFB1I1 | 5.507 | 7.424 | 9.982 | 10.717 | 10.618 | 9.786 | 9.151 | 0.0428933 | transforming growth factor beta 1 induced transcript 1 |
| SULT1B1 | −0.026 | 0.121 | −0.026 | 3.176 | 3.649 | 2.108 | 9.196 | 0.0014866 | sulfotransferase family, cytosolic, 1B, member 1 |
| TULP2 | −0.026 | −0.026 | −0.026 | 2.836 | 3.176 | 5.197 | 9.196 | 0.0020921 | tubby like protein 2 |
| CNTFR | −0.026 | −0.026 | 3.088 | 3.176 | 3.176 | 4.857 | 9.196 | 0.0314336 | ciliary neurotrophic factor receptor |
| ZEB2 | 1.559 | 1.559 | 1.610 | 5.057 | 4.774 | 2.650 | 9.286 | 0.0113592 | zinc finger E-box binding homeobox 2 |
| NSMCE1 | 4.821 | 5.122 | 8.108 | 8.658 | 8.444 | 8.073 | 9.530 | 0.0376830 | non-SMC element 1 homolog (S. cerevisiae) |
| DNER | 3.117 | 2.585 | 4.687 | 5.860 | 6.469 | 7.707 | 9.681 | 0.0062418 | delta/notch-like EGF repeat containing |
| FABP5 | 0.974 | 1.643 | 3.161 | 5.240 | 4.952 | 4.649 | 9.914 | 0.0041289 | fatty acid binding protein 5 (psoriasis-associated) |
| LOC642313 | −0.026 | 1.098 | 3.176 | 4.443 | 3.974 | 4.592 | 10.165 | 0.0137206 | No description |
| FBLN5 | 7.684 | 9.313 | 6.636 | 11.296 | 10.325 | 11.029 | 10.167 | 0.0084659 | fibulin 5 |
| TMEM204 | 2.247 | 2.348 | 4.448 | 7.009 | 6.049 | 5.605 | 10.252 | 0.0061673 | transmembrane protein 204 |
| SRPX | −0.026 | −0.026 | −0.026 | 4.592 | 3.345 | 2.108 | 10.341 | 0.0031558 | sushi-repeat-containing protein, X-linked |
| LALBA | −0.026 | −0.026 | 0.121 | 1.734 | 3.345 | 6.831 | 10.341 | 0.0173676 | lactalbumin, alpha- |
| ERMP1 | 4.777 | 4.990 | 5.818 | 9.411 | 8.406 | 6.478 | 10.671 | 0.0125649 | endoplasmic reticulum metallopeptidase 1 |
| LXN | 3.649 | 3.542 | 1.734 | 7.069 | 5.561 | 5.988 | 10.701 | 0.0045940 | latexin |
| LOX | 7.163 | 5.936 | 6.941 | 10.583 | 9.839 | 9.831 | 10.706 | 0.0007038 | lysyl oxidase |
| MEG3 | −0.026 | 4.443 | 3.966 | 5.492 | 5.735 | 7.868 | 10.738 | 0.0299056 | maternally expressed 3 (non-protein coding) |
| SNAI3 | 0.974 | 0.974 | 1.738 | 4.448 | 4.406 | 4.590 | 10.787 | 0.0002164 | snail homolog 3 (Drosophila) |
| PDGFRB | 1.559 | 2.037 | 3.388 | 7.069 | 5.002 | 5.027 | 10.870 | 0.0059401 | platelet-derived growth factor receptor, beta polypeptide |
| 00X18 | 4.280 | 4.805 | 4.521 | 8.461 | 7.982 | 6.548 | 11.016 | 0.0024697 | COX18 cytochrome c oxidase assembly homolog (S. cerevisiae) |
| PSPH | 1.974 | 2.649 | 4.042 | 6.497 | 6.283 | 5.511 | 11.600 | 0.0033016 | phosphoserine phosphatase |
| DUOX2 | 1.559 | 2.075 | 1.759 | 6.052 | 5.341 | 4.309 | 11.981 | 0.0010583 | dual oxidase 2 |
| GRID1 | 0.974 | 0.974 | 0.974 | 4.983 | 4.651 | 2.404 | 12.785 | 0.0073807 | glutamate receptor, ionotropic, delta 1 |
| PRDM1 | 5.135 | 4.989 | 5.174 | 9.340 | 8.541 | 8.816 | 12.829 | 0.0001351 | PR domain containing 1, with ZNF domain |
| IDO1 | 1.974 | 4.378 | 3.196 | 5.796 | 6.387 | 8.068 | 12.903 | 0.0066800 | Description |
| CST7 | 0.974 | 2.108 | 4.448 | 5.971 | 5.797 | 5.693 | 12.905 | 0.0106155 | cystatin F (leukocystatin) |
| MSC | −0.026 | 0.121 | 1.169 | 5.775 | 3.825 | 3.649 | 13.032 | 0.0018772 | musculin |
| NOL6 | 3.434 | 5.048 | 7.630 | 7.461 | 8.783 | 8.756 | 13.064 | 0.0307920 | nucleolar protein family 6 (RNA-associated) |
| CXCR7 | 0.974 | 4.507 | 4.753 | 8.517 | 7.426 | 5.736 | 13.589 | 0.0179547 | chemokine (C-X-C motif) receptor 7 |
| LAMA4 | 4.821 | 4.810 | 5.589 | 9.523 | 8.606 | 7.430 | 13.788 | 0.0021489 | laminin, alpha 4 |
| MYL1K | 4.660 | 4.850 | 3.527 | 7.898 | 7.350 | 9.620 | 14.150 | 0.0022111 | myosin light chain kinase |
| C15orf48 | 0.974 | 5.942 | 3.600 | 9.771 | 9.857 | 9.266 | 14.216 | 0.0035541 | chromosome 15 open reading frame 48 |
| BCAM | 6.870 | 6.838 | 8.114 | 11.563 | 11.740 | 10.671 | 14.247 | 0.0005503 | basal cell adhesion molecule (Lutheran blood group) |
| SLC1A5 | 9.190 | 9.949 | 11.409 | 14.121 | 14.013 | 13.037 | 14.392 | 0.0027790 | solute carrier family 1 (neutral amino acid transporter), member 5 |
| C17orf67 | 2.671 | 1.734 | 5.405 | 7.154 | 6.622 | 6.035 | 15.467 | 0.0143216 | chromosome 17 open reading frame 67 |
| LMAN2L | 5.344 | 5.547 | 7.322 | 9.551 | 9.611 | 9.418 | 16.041 | 0.0018281 | lectin, mannose-binding 2-like |
| IGFL1 | 1.559 | 5.636 | 4.952 | 9.663 | 8.916 | 6.340 | 16.303 | 0.0162817 | IGF-like family member 1 |
| TIE1 | 2.296 | 3.809 | 4.421 | 8.631 | 7.291 | 6.423 | 17.464 | 0.0033507 | tyrosine kinase with immunoglobulin-like and EGF-like domains 1 |
| FERMT1 | 3.220 | 2.050 | 2.264 | 6.429 | 7.536 | 4.997 | 17.937 | 0.0028619 | fermitin family member 1 |

TABLE 5-continued

Differentially Expressed Genes in CD24+ Breast Epithelial Cells

| | Nulliparous (NP) Samples | | | Parous (P) Samples | | | | | |
|---|---|---|---|---|---|---|---|---|---|
| | CD24+ N48 | CD24+ N58 | CD24+ N43 | CD24+ N37 | CD24+ N39 | CD24+ N40 | Pseudo fold change | P value | Gene description |
| EPR1 | 2.878 | 0.974 | 4.455 | 6.089 | 7.078 | 7.282 | 18.382 | 0.0052072 | effector cell peptidase receptor 1 (non-protein coding) |
| CXCL17 | 5.127 | 6.275 | 6.861 | 11.070 | 9.330 | 9.454 | 18.415 | 0.0020061 | chemokine (C-X-C motif) ligand 17 |
| LOC387763 | 5.584 | 6.095 | 7.544 | 11.641 | 10.420 | 10.089 | 20.036 | 0.0012210 | No description |
| B3GAT1 | 2.559 | 3.476 | 3.043 | 5.223 | 7.459 | 7.816 | 20.256 | 0.0032295 | beta-1,3-glucuronyltransferase 1 (glucuronosyltransferase P) |
| WFDC5 | −0.026 | 1.734 | 4.592 | 6.306 | 7.685 | 6.229 | 23.783 | 0.0082947 | WAP four-disulfide core domain 5 |
| TNFRSF4 | 1.913 | 0.121 | 4.675 | 7.896 | 7.019 | 4.857 | 26.648 | 0.0147329 | tumor necrosis factor receptor superfamily, member 4 |
| HSPA12B | −0.026 | −0.026 | 3.088 | 6.271 | 5.990 | 4.749 | 27.369 | 0.0035004 | heat shock 70 kD protein 12B |
| CSN1S1 | 1.974 | 1.974 | 2.013 | 6.455 | 6.862 | 10.189 | 29.601 | 0.0015081 | casein alpha s1 |
| CACNA1G | 0.974 | 0.974 | 1.692 | 6.707 | 5.527 | 6.511 | 32.342 | 0.0001458 | calcium channel, voltage-dependent, T type, alpha 1 G subunit |
| FST | 1.559 | 4.471 | 3.032 | 8.467 | 7.881 | 9.153 | 43.247 | 0.0007575 | follistatin |
| S100A7 | −0.026 | 5.581 | 8.514 | 11.885 | 11.071 | 8.586 | 44.950 | 0.0264919 | S100 calcium binding protein A7 |
| EDNRB | 2.747 | 2.466 | 3.917 | 10.515 | 9.214 | 8.289 | 88.494 | 0.0002487 | endothelin receptor type B |

TABLE 6

Differentially Expressed Genes in CD10+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD24+ N48 | CD24+ N58 | CD24+ N43 | CD24+ N37 | CD24+ N39 | CD24+ N40 | | | | |
| | | | | | | | | Higher Expression in Nulliparous | | |
| C1orf54 | 5.102 | 3.089 | 5.104 | -0.824 | -1.775 | 0.831 | | -29.107 | 0.0002869 | chromosome 1 open reading frame 54 |
| THSD4 | 6.561 | 9.441 | 8.353 | 4.283 | 4.081 | 3.953 | | -19.316 | 0.000508 | thrombospondin, type I, domain containing 4 |
| SNORD5 | -0.192 | 3.962 | 3.332 | -0.824 | -0.648 | -1.775 | | -17.826 | 0.0065107 | small nucleolar RNA, C/D box 5 |
| POSTN | 9.168 | 12.303 | 11.621 | 7.535 | 7.574 | 7.969 | | -16.525 | 0.0023939 | periostin, osteoblast specific factor |
| COL3A1 | 11.438 | 9.014 | 11.012 | 4.96 | 7.398 | 7.447 | | -15.897 | 0.0018316 | collagen, type III, alpha 1 |
| NINJ2 | 3.524 | 0.251 | 2.111 | -1.775 | -1.775 | -1.775 | | -14.779 | 0.0012771 | ninjurin 2 |
| ZFP57 | 6.093 | 3.677 | 0.631 | 0.173 | -0.264 | -0.206 | | -14.752 | 0.0103284 | zinc finger protein 57 homolog (mouse) |
| LRTM2 | 2.021 | 2.06 | 0.925 | -1.775 | -1.775 | -1.775 | | -13.887 | 0.0001538 | leucine-rich repeats and transmembrane domains 2 |
| DCN | 10.671 | 8.272 | 11.57 | 4.488 | 7.405 | 7.354 | | -13.772 | 0.00479 | decorin |
| PI16 | 8.33 | 4.395 | 8.715 | 2.101 | 4.938 | 4.422 | | -13.703 | 0.0158439 | peptidase inhibitor 16 |
| COL1A2 | 11.312 | 8.134 | 11.217 | 4.921 | 7.557 | 7.552 | | -12.682 | 0.0061 | collagen, type I, alpha 2 |
| RHOJ | 6.664 | 5.96 | 6.902 | 2.852 | 2.525 | 3.288 | | -12.245 | 0.0001324 | ras homolog gene family, member J |
| F10 | 6.906 | 2.442 | 7.022 | 2.36 | 3.43 | 3.093 | | -12.059 | 0.0391357 | coagulation factor X |
| SFRP2 | 5.944 | 6.005 | 7.791 | 2.36 | 3.565 | 3.768 | | -11.992 | 0.0009666 | secreted frizzled-related protein 2 |
| CD248 | 6.793 | 5.002 | 7.595 | 2.521 | 4.012 | 3.143 | | -11.985 | 0.0021056 | CD248 molecule, endosialin |
| PDGFRL | 5.035 | 4.423 | 5.684 | 1.459 | 1.387 | 1.576 | | -11.926 | 0.0001395 | platelet-derived growth factor receptor-like |
| CCL8 | 5.371 | 3.123 | 5.509 | 0.573 | 1.758 | 1.936 | | -11.896 | 0.0021199 | chemokine (C-C motif) ligand 8 |
| AGPHD1 | 2.021 | 1.783 | 1.247 | -1.775 | -1.775 | -1.775 | | -11.777 | 0.0000823 | aminoglycoside phosphotransferase domain containing 1 |
| COL15A1 | 7.943 | 5.164 | 8.626 | 3.506 | 4.729 | 4.439 | | -11.347 | 0.0066209 | collagen, type XV, alpha 1 |
| CREB3L1 | 6.259 | 2.891 | 6.607 | 1.797 | 2.946 | 2.758 | | -11.323 | 0.0144466 | cAMP responsive element binding protein 3-like 1 |
| SCARA5 | 7.209 | 3.9 | 7.207 | 2.238 | 3.715 | 3.427 | | -11.265 | 0.0087437 | scavenger receptor class A, member 5 (putative) |
| MFAP2 | 5.023 | 4.475 | 6.123 | 0.573 | 2.115 | 2.639 | | -11.184 | 0.001016 | microfibrillar-associated protein 2 |
| TMEM173 | 4.551 | 3.212 | 5.156 | 0.415 | -0.264 | 2.53 | | -11.127 | 0.0026508 | transmembrane protein 173 |
| SNORD27 | -1.775 | 1.699 | 2.26 | -1.775 | -1.775 | -1.775 | | -11.106 | 0.0229996 | small nucleolar RNA, C/D box 27 |
| TGFBI | 5.658 | 6.933 | 8.974 | 2.565 | 3.668 | 3.473 | | -11.003 | 0.0012556 | transforming growth factor, beta-induced, 68kDa |
| FBLN2 | 6.431 | 3.383 | 5.963 | 2.443 | 2.584 | 2.514 | | -10.919 | 0.0059827 | fibulin 2 |
| LOC572558 | 1.689 | 2.757 | 2.505 | -1.775 | -0.648 | -0.904 | | -10.617 | 0.0002297 | No description |
| SEPP1 | 8.128 | 7.649 | 8.746 | 4.267 | 4.944 | 4.804 | | -10.422 | 0.0001467 | selenoprotein P, plasma, 1 |
| ITM2A | 8.629 | 9.85 | 9.527 | 6.096 | 6.202 | 6.366 | | -10.024 | 0.0002168 | integral membrane protein 2A |
| NOXA1 | 2.391 | 3.579 | 4.019 | 0.173 | 0.695 | 0.162 | | -10.011 | 0.0005151 | NADPH oxidase activator 1 |
| MYOC | 5.977 | -0.046 | 3.484 | 0.173 | -0.264 | 1.075 | | -9.925 | 0.0429999 | myocilin, trabecular meshwork inducible glucocorticoid response |
| SRPX | 6.668 | 6.897 | 8.573 | 3.413 | 4.377 | 4.202 | | -9.549 | 0.0006024 | sushi-repeat-containing protein, X-linked |
| ST7OT2 | -0.904 | 2.884 | 3.31 | -0.311 | -0.887 | -0.362 | | -9.486 | 0.0413665 | ST7 overlapping transcript 2 (non-protein coding) |
| CPZ | 6.264 | 3.084 | 6.187 | 0.173 | 2.548 | 3.043 | | -9.321 | 0.0094055 | carboxypeptidase Z |
| OLFML1 | 4.902 | 1.54 | 4.336 | 1.121 | 0.814 | 1.436 | | -9.282 | 0.0140939 | olfactomedin-like 1 |
| LDB2 | 6.769 | 4.311 | 6.747 | 1.556 | 3.561 | 3.09 | | -9.235 | 0.0036811 | LIM domain binding 2 |
| ABCA8 | 5.494 | 2.727 | 7.114 | 2.238 | 3.119 | 2.311 | | -9.08 | 0.0236446 | ATP-binding cassette, sub-family A (ABC1), member 8 |
| LSP1 | 8.582 | 5.763 | 9.248 | 2.406 | 6.312 | 5.407 | | -9.03 | 0.0182636 | lymphocyte-specific protein 1 |
| TMEM132C | 4.274 | 1.241 | 4.013 | 0.86 | 0.848 | 0.886 | | -8.892 | 0.0146648 | transmembrane protein 132C |
| FIGF | 5.832 | 4.836 | 6.788 | 1.715 | 3.158 | 3.452 | | -8.695 | 0.0019174 | c-fos induced growth factor (vascular endothelial growth factor D) |
| CAT | 5.323 | 5.94 | 5.212 | 1.478 | 2.828 | 2.664 | | -8.645 | 0.0003356 | catalase |
| CTSK | 7.267 | 6.416 | 7.38 | 3.306 | 3.73 | 4.552 | | -8.63 | 0.0003212 | cathepsin K |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| DLK1 | 4.533 | 4.081 | 6.642 | 1.299 | 2.621 | 1.436 | −8.553 | 0.001999 | delta-like 1 homolog (Drosophila) |
| PENK | 1.541 | 3.971 | 5.292 | 1.757 | 0.515 | 0.886 | −8.485 | 0.016437 | proenkephalin |
| CMTM5 | 3.967 | 3.924 | 2.33 | −0.104 | 0.886 | 0.327 | −8.458 | 0.000845 | CKLF-like MARVEL transmembrane domain containing 5 |
| PTGDS | 8.456 | 6.809 | 10.25 | 3.743 | 6.499 | 6.516 | −8.379 | 0.0150662 | prostaglandin D2 synthase 21 kDa (brain) |
| ISLR | 5.665 | 3.479 | 5.466 | 2.101 | 2.402 | 2.488 | −8.362 | 0.0035966 | immunoglobulin superfamily containing leucine-rich repeat |
| FAM198B | 9.132 | 10.015 | 9.316 | 6.093 | 6.761 | 6.912 | −8.218 | 0.0002726 | family with sequence similarity 198, member B |
| OAF | 8.246 | 5.745 | 8.877 | 5.057 | 5.221 | 5.503 | −8.139 | 0.0130157 | OAF homolog (Drosophila) |
| OLFML3 | 7.383 | 4.852 | 7.283 | 1.854 | 4.11 | 4.501 | −7.989 | 0.0077091 | olfactomedin-like 3 |
| CSTA | 6.315 | 8.863 | 7.883 | 4.886 | 4.535 | 5.5 | −7.982 | 0.0037419 | cystatin A (stefin A) |
| DPT | 8.014 | 3.514 | 6.971 | 2.748 | 4.059 | 3.979 | −7.953 | 0.0301774 | dermatopontin |
| TNNT1 | 5.751 | 5.666 | 4.726 | 3.489 | 0.924 | 2.682 | −7.911 | 0.0023868 | troponin T type 1 (skeletal, slow) |
| CNRIP1 | 6.467 | 3.081 | 5.326 | 2.313 | 3.139 | 2.348 | −7.881 | 0.0160335 | cannabinoid receptor interacting protein 1 |
| PARVB | 6.455 | 2.539 | 4.339 | 1.299 | 1.362 | 1.928 | −7.873 | 0.008587 | parvin, beta |
| ELN | 6.422 | 4.033 | 6.521 | 1.065 | 3.701 | 3.353 | −7.826 | 0.0083423 | elastin |
| MCEE | 2.854 | 5.603 | 5.238 | 2.638 | 1.387 | 1.779 | −7.805 | 0.007053 | methylmalonyl CoA epimerase |
| OLFML2B | 5.402 | 4.001 | 5.188 | 2.335 | 1.758 | 2.226 | −7.791 | 0.0006382 | olfactomedin-like 2B |
| JAM2 | 5.895 | 5.363 | 5.074 | 2.124 | 3.218 | 2.195 | −7.729 | 0.000357 | junctional adhesion molecule 2 |
| TM4SF18 | 6.191 | 2.257 | 0.315 | −0.311 | −0.887 | −0.688 | −7.701 | 0.0147378 | transmembrane 4 L six family member 18 |
| HSPA12B | 5.06 | 2.669 | 5.254 | 1.556 | 2.324 | 2.074 | −7.62 | 0.0094591 | heat shock 70kD protein 12B |
| INS-IGF2 | 9.689 | 6.133 | 8.804 | 3.204 | 6.386 | 6.342 | −7.614 | 0.0215175 | No description |
| TNFRSF4 | 5.722 | 2.004 | 5.474 | 0.631 | 2.797 | 2.4 | −7.592 | 0.0322029 | tumor necrosis factor receptor superfamily, member 4 |
| CABP1 | 1.587 | 1.699 | 1.148 | −1.775 | −0.012 | −1.775 | −7.584 | 0.0017615 | calcium binding protein 1 |
| SSBP2 | 5.056 | 7.455 | 8.981 | 4.533 | 4.441 | 5.178 | −7.582 | 0.0198583 | single-stranded DNA binding protein 2 |
| C5orf13 | 5.225 | 7.535 | 6.988 | 4.068 | 4.276 | 3.885 | −7.569 | 0.0038048 | chromosome 5 open reading frame 13 |
| SDPR | 5.96 | 8.702 | 7.915 | 4.045 | 5.252 | 4.996 | −7.565 | 0.0048358 | serum deprivation response |
| PHLDA3 | 7.615 | 10.055 | 9.532 | 6.19 | 6.616 | 6.804 | −7.548 | 0.004531 | pleckstrin homology-like domain, family A, member 3 |
| LY96 | 4.804 | 1.114 | 2.602 | −0.311 | 1.49 | −0.362 | −7.534 | 0.0192144 | lymphocyte antigen 96 |
| CRISPLD1 | 5.01 | 8.092 | 7.816 | 4.661 | 4.884 | 5.192 | −7.465 | 0.0260192 | cysteine-rich secretory protein LCCL domain containing 1 |
| PTPRZ1 | 3.81 | 7.139 | 6.606 | 3.709 | 3.483 | 3.945 | −7.451 | 0.0250411 | protein tyrosine phosphatase, receptor-type, Z polypeptide 1 |
| TNFAIP3 | 7.863 | 11.202 | 10.946 | 7.399 | 8.313 | 8.054 | −7.406 | 0.0334221 | tumor necrosis factor, alpha-induced protein 3 |
| HNRPDL | 9.386 | 12.615 | 12.062 | 9.177 | 8.983 | 9.52 | −7.386 | 0.0232883 | heterogeneous nuclear ribonucleoprotein D-like |
| CRYM | 2.803 | 6.993 | 4.492 | 1.623 | 2.261 | 1.46 | −7.303 | 0.0100501 | crystallin, mu |
| MLLT11 | 3.708 | 4.372 | 4.832 | 1.513 | 1.948 | 1.471 | −7.251 | 0.0003999 | myeloid/lymphoid or mixed-lineage leukemia (trithorax homolog, Drosophila); translocated to, 11 |
| SNAP25 | 1.867 | 5.049 | 4.604 | 2.205 | 1.033 | 1.609 | −7.178 | 0.0217786 | synaptosomal-associated protein, 25kDa |
| HOXD3 | 3.014 | 1.715 | 3.239 | 0.173 | 0.283 | 0.162 | −7.166 | 0.0013572 | homeobox D3 |
| COL1A1 | 11.804 | 9.592 | 13.092 | 7.357 | 8.972 | 9.077 | −7.122 | 0.0074637 | collagen, type I, alpha 1 |
| SUMF1 | 3.663 | 5.562 | 6.011 | 2.269 | 3.016 | 2.735 | −7.098 | 0.005449 | sulfatase modifying factor 1 |
| CPE | 7.988 | 9.977 | 8.88 | 4.974 | 7.174 | 6.789 | −6.977 | 0.0059111 | carboxypeptidase E |
| LOXHD1 | 1.719 | 4.266 | 3.613 | −0.104 | 0.886 | 0.814 | −6.957 | 0.0045045 | lipoxygenase homology domains 1 |
| COL11A1 | 5.27 | 7.581 | 7.849 | 4.638 | 4.787 | 4.877 | −6.938 | 0.0126987 | collagen, type XI, alpha 1 |
| IFI44 | 3.953 | 3.678 | 2.821 | 1.065 | 0.848 | 0.886 | −6.926 | 0.0004572 | interferon-induced protein 44 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| NSMCE4A | 4.008 | 4.325 | 5.166 | 1.188 | 1.546 | 2.682 | −6.862 | 0.0013358 | non-SMC element 4 homolog A (S. cerevisiae) |
| MFAP5 | 5.807 | 2.506 | 4.877 | 1.698 | 2.101 | 2.342 | −6.849 | 0.0149832 | microfibrillar associated protein 5 |
| MEOX2 | 4.887 | 2.352 | 3.338 | 0.573 | 0.924 | 0.251 | −6.801 | 0.0021421 | mesenchyme homeobox 2 |
| SRBD1 | 1.871 | 2.776 | 2.97 | −0.104 | −0.887 | 1.408 | −6.763 | 0.0055785 | S1 RNA binding domain 1 |
| GAS1 | 5.686 | 7.409 | 8.211 | 4.66 | 4.482 | 5.362 | −6.724 | 0.0085405 | growth arrest-specific 1 |
| PLAC9 | 5.641 | 3.381 | 5.994 | 1.459 | 2.548 | 3.246 | −6.719 | 0.0085998 | placenta-specific 9 |
| IGFBP7 | 8.81 | 6.739 | 9.172 | 4.745 | 6.165 | 6.083 | −6.62 | 0.0065536 | insulin-like growth factor binding protein 7 |
| NPR1 | 5.142 | 1.835 | 4.238 | 1.366 | 1.513 | 1.609 | −6.612 | 0.0176991 | natriuretic peptide receptor A/guanylate cyclase A (atrionatriuretic peptide receptor A) |
| MAGED1 | 5.427 | 7.934 | 6.354 | 5.172 | 2.715 | 4.402 | −6.552 | 0.0128847 | melanoma antigen family D, 1 |
| OGN | 8.73 | 5.19 | 8.837 | 3.375 | 6.158 | 5.667 | −6.405 | 0.0363311 | osteoglycin |
| FMO1 | 4.039 | 4.435 | 4.937 | 1.366 | 2.107 | 1.948 | −6.38 | 0.0003499 | flavin containing monooxygenase 1 |
| FBN1 | 7.256 | 6.448 | 8.561 | 3.808 | 4.583 | 4.743 | −6.375 | 0.001227 | fibrillin 1 |
| VASH2 | 4.593 | 6.943 | 7.239 | 4.082 | 4.186 | 4.574 | −6.341 | 0.0196072 | vasohibin 2 |
| POTEE | 0.888 | 2.06 | 2.758 | −1.775 | −0.012 | −0.012 | −6.33 | 0.0055055 | POTE ankyrin domain family, member E |
| LMBR1L | 5.318 | 6.496 | 6.378 | 3.15 | 3.776 | 3.719 | −6.319 | 0.0008156 | limb region 1 homolog (mouse)-like |
| COLEC12 | 7.061 | 3.646 | 6.583 | 2.121 | 3.927 | 3.007 | −6.303 | 0.023417 | collectin sub-family member 12 |
| KCNMB4 | 3.198 | 2.812 | 4.689 | 1.818 | 1.099 | 0.162 | −6.275 | 0.0041962 | potassium large conductance calcium-activated channel, subfamily M, beta member 4 |
| CCDC152 | 7.213 | 6.032 | 7.58 | 3.806 | 4.935 | 4.418 | −6.254 | 0.0017887 | coiled-coil domain containing 152 |
| ADAMTS18 | 3.089 | 4.656 | 5.578 | 2.37 | 2.019 | 1.837 | −6.217 | 0.0056994 | ADAM metallopeptidase with thrombospondin type 1 motif, 18 |
| CD34 | 8.863 | 3.223 | 5.792 | 1.982 | 4.356 | 3.158 | −6.207 | 0.0422759 | CD34 molecule |
| EMILIN2 | 5.621 | 4.088 | 5.854 | 2.966 | 3.231 | 2.533 | −6.16 | 0.0037168 | elastin microfibril interfacer 2 |
| OR4E2 | 1.797 | 0.251 | 1.715 | −0.824 | −1.775 | −1.775 | −6.149 | 0.0015468 | olfactory receptor, family 4, subfamily E, member 2 |
| RCAN2 | 4.959 | 4.747 | 5.451 | 2.129 | 3.479 | 2.171 | −6.14 | 0.0014553 | regulator of calcineurin 2 |
| ACTA2 | 6.139 | 8.987 | 8.32 | 5.319 | 5.749 | 5.703 | −6.136 | 0.0123453 | actin, alpha 2, smooth muscle, aorta |
| CXCR4 | 5.908 | 5.696 | 3.497 | 1.525 | 2.795 | 3.297 | −6.108 | 0.0090985 | chemokine (C-X-C motif) receptor 4 |
| COL14A1 | 8.194 | 9.149 | 9.493 | 6.543 | 5.763 | 6.697 | −6.089 | 0.0009737 | collagen, type XIV, alpha 1 |
| TMEM55A | 3.174 | 4.774 | 4.45 | 1.846 | 1.82 | 1.999 | −6.082 | 0.0023167 | transmembrane protein 55A |
| FN1 | 6.972 | 4.777 | 7.377 | 3.927 | 4.774 | 4.001 | −6.075 | 0.0139536 | fibronectin 1 |
| KLHL22 | 2.643 | 4.542 | 4.48 | 1.679 | 1.944 | 1.72 | −6.052 | 0.006143 | kelch-like 22 (Drosophila) |
| C20orf46 | 1.689 | 2.526 | 1.494 | −1.775 | 0.988 | −0.904 | −6.033 | 0.0077857 | chromosome 20 open reading frame 46 |
| HTRA1 | 8.218 | 6.817 | 7.592 | 4.391 | 5 | 5.532 | −6.031 | 0.0013715 | HtrA serine peptidase 1 |
| ROBO1 | 5.017 | 7.233 | 7.08 | 4.613 | 3.944 | 4.351 | −6.02 | 0.0092509 | roundabout, axon guidance receptor, homolog 1 (Drosophila) |
| STC1 | 11.369 | 6.744 | 7.072 | 4.163 | 5.522 | 4.742 | −5.982 | 0.0090842 | stanniocalcin 1 |
| C9orf25 | 5.049 | 7.374 | 7.465 | 4.57 | 4.719 | 4.886 | −5.975 | 0.0191822 | chromosome 9 open reading frame 25 |
| COL6A6 | 5.493 | 3.608 | 6.676 | 2.799 | 3.378 | 2.921 | −5.947 | 0.014242 | collagen, type VI, alpha 6 |
| RSRC1 | 1.602 | 3.047 | 3.019 | 0.173 | 0.283 | 0.478 | −5.935 | 0.0022408 | arginine/serine-rich coiled-coil 1 |
| CALHM2 | 4.107 | 3.432 | 4.593 | 1.949 | 1.546 | 1.513 | −5.901 | 0.0007512 | calcium homeostasis modulator 2 |
| TNN | 7.528 | 5.3 | 7.485 | 3.498 | 4.975 | 4.706 | −5.871 | 0.0089719 | tenascin N |
| ST8SIA2 | 6.819 | 8.269 | 7.329 | 4.539 | 4.779 | 5.207 | −5.858 | 0.0008378 | ST8 alpha-N-acetyl-neuraminide alpha-2,8-sialyltransferase 2 |
| C7orf55 | 3.595 | 5.857 | 5.109 | 2.765 | 2.569 | 2.06 | −5.816 | 0.0045596 | chromosome 7 open reading frame 55 |
| PCOLCE | 8.195 | 6.361 | 9.153 | 4.442 | 5.656 | 5.939 | −5.815 | 0.0082114 | procollagen C-endopeptidase enhancer |
| S100A4 | 6.136 | 4.191 | 7.067 | 3.014 | 3.598 | 3.991 | −5.808 | 0.0123381 | S100 calcium binding protein A4 |
| SGCE | 7.219 | 9.297 | 8.943 | 6.287 | 6.414 | 6.526 | −5.773 | 0.0070802 | sarcoglycan, epsilon |
| TRPV6 | 1.888 | 5.075 | 3.751 | 1.228 | 0.695 | 1.779 | −5.748 | 0.0141518 | transient receptor potential cation channel, subfamily V, member 6 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| UBE2V1 | 0.609 | 1.699 | 3.102 | −0.824 | −0.012 | −1.775 | −5.745 | 0.0054346 | ubiquitin-conjugating enzyme E2 variant 1 |
| CD99 | 9.28 | 5.505 | 8.513 | 3.479 | 6.687 | 6 | −5.706 | 0.0485662 | CD99 molecule |
| TSC22D1 | 8.836 | 9.579 | 9.258 | 5.975 | 7.45 | 6.746 | −5.704 | 0.0012098 | TSC22 domain family, member 1 |
| TRIL | 4.539 | 6.374 | 6.051 | 2.841 | 3.674 | 3.542 | −5.691 | 0.0039214 | TLR4 interactor with leucine-rich repeats |
| BDKRB2 | 5.325 | 4.576 | 6.703 | 2.832 | 2.656 | 3.356 | −5.63 | 0.0025621 | bradykinin receptor B2 |
| MTRNR1 | 14.554 | 14.158 | 15.551 | 11.466 | 12.062 | 13.58 | −5.625 | 0.0057137 | No description |
| NTF3 | 5.626 | 8.418 | 8.063 | 5.836 | 5.386 | 5.578 | −5.598 | 0.0349381 | neurotrophin 3 |
| CPVL | 4.276 | 2.656 | 3.392 | 0.173 | 1.387 | 1.075 | −5.591 | 0.0020062 | carboxypeptidase, vitellogenic-like |
| C6orf15 | 2.461 | 4.636 | 4.254 | 1.773 | 1.176 | 2.042 | −5.581 | 0.0087959 | chromosome 6 open reading frame 115 |
| IL33 | 6.764 | 4.553 | 6.263 | 4.015 | 2.423 | 3.789 | −5.556 | 0.0068527 | interleukin 33 |
| HLA-DQB1 | 5.54 | 4.587 | 3.428 | 1.623 | 2.261 | 2.124 | −5.516 | 0.0027624 | major histocompatibility complex, class II, DQ beta 1 |
| MX2 | 5.186 | 2.845 | 4.983 | 2.669 | 2.521 | 2.169 | −5.51 | 0.0180167 | myxovirus (influenza virus) resistance 2 (mouse) |
| ST3GAL4 | 5.967 | 4.347 | 6.76 | 2.593 | 3.93 | 3.507 | −5.501 | 0.0078558 | ST3 beta-galactoside alpha-2,3-sialyltransferase 4 |
| LOC339568 | 1.797 | 2.06 | 3.476 | 1.029 | −1.775 | 0.429 | −5.454 | 0.0101681 | No description |
| RFX5 | 4.52 | 6.697 | 6.669 | 4.233 | 4.198 | 4.222 | −5.452 | 0.0214223 | regulatory factor X, 5 (influences HLA class II expression) |
| H3F3C | 8.303 | 10.66 | 8.956 | 6.55 | 5.923 | 6.513 | −5.437 | 0.0017329 | H3 histone, family 3C |
| UBQLNL | 1.091 | 2.978 | 1.753 | −0.311 | −0.887 | −0.688 | −5.43 | 0.001803 | ubiquilin-like |
| SIX5 | 4.715 | 6.541 | 6.443 | 3.638 | 4.102 | 3.925 | −5.424 | 0.0070122 | SIX homeobox 5 |
| SPON2 | 7.184 | 5.652 | 8.637 | 3.24 | 4.748 | 5.049 | −5.41 | 0.0069586 | spondin 2, extracellular matrix protein |
| ZNF630 | 0.644 | 1.893 | 2.33 | −0.104 | −0.887 | −0.688 | −5.404 | 0.0038263 | zinc finger protein 630 |
| TACC2 | 5.639 | 5.612 | 6.86 | 3.185 | 4.028 | 3.91 | −5.375 | 0.0019103 | transforming, acidic coiled-coil containing protein 2 |
| ENPP2 | 10.147 | 4.572 | 7.142 | 3.92 | 4.718 | 4.87 | −5.367 | 0.0336739 | ectonucleotide pyrophosphatase/phosphodiesterase 2 |
| CDH23 | 5.288 | 6.717 | 6.119 | 3.853 | 3.204 | 3.695 | −5.366 | 0.0012027 | cadherin-related 23 |
| GLT8D2 | 7.101 | 7.934 | 8.22 | 4.946 | 5.698 | 5.513 | −5.355 | 0.0010517 | glycosyltransferase 8 domain containing 2 |
| ITFG1 | 4.926 | 6.947 | 6.402 | 3.874 | 3.589 | 4.533 | −5.331 | 0.0074937 | integrin alpha FG-GAP repeat containing 1 |
| ODZ1 | 2.879 | 5.083 | 5.058 | 2.646 | 2.63 | 2.661 | −5.324 | 0.0250869 | odz, odd Oz/ten-m homolog 1 (Drosophila) |
| RIN2 | 5.406 | 7.715 | 6.79 | 4.387 | 4.383 | 4.518 | −5.289 | 0.0059469 | Ras and Rab interactor 2 |
| C14orf159 | 4.418 | 5.87 | 6.418 | 3.463 | 4.017 | 3.139 | −5.282 | 0.0081498 | chromosome 14 open reading frame 159 |
| C15orf32 | 3.499 | 2.567 | 2.943 | 0.573 | 0.17 | 0.552 | −5.266 | 0.0002941 | chromosome 15 open reading frame 32 |
| IFRD1 | 8.899 | 11.138 | 10.754 | 8.218 | 8.359 | 8.584 | −5.261 | 0.0144781 | interferon-related developmental regulator 1 |
| GPR124 | 6.905 | 5.121 | 8.362 | 3.17 | 4.583 | 4.511 | −5.254 | 0.0088517 | G protein-coupled receptor 124 |
| KATNAL2 | 1.855 | 3.15 | 3.313 | 0.762 | 0.924 | 0.552 | −5.235 | 0.0036396 | katanin p60 subunit A-like 2 |
| SLIT3 | 7.064 | 5.129 | 6.857 | 4.475 | 4.341 | 4.633 | −5.212 | 0.0106003 | slit homolog 3 (Drosophila) |
| CAPN6 | 4.869 | 6.308 | 7.831 | 3.409 | 4.038 | 3.928 | −5.206 | 0.0067303 | calpain 6 |
| PODN | 8.751 | 4.235 | 6.561 | 2.721 | 4.719 | 4.182 | −5.203 | 0.0275281 | podocan |
| ACOX2 | 2.16 | 3.454 | 4.774 | 0.415 | 1.616 | 1.075 | −5.202 | 0.0070731 | acyl-CoA oxidase 2, branched chain |
| SOSTDC1 | 5.669 | 7.193 | 5.447 | 3.794 | 4.017 | 4.381 | −5.199 | 0.00432 | sclerostin domain containing 1 |
| LMOD1 | 6.678 | 9.189 | 9.06 | 6.107 | 3.069 | 6.301 | −5.197 | 0.0225263 | leiomodin 1 (smooth muscle) |
| FAM184A | 4.925 | 7.544 | 7.02 | 4.495 | 6.812 | 4.645 | −5.185 | 0.0211211 | family with sequence similarity 184, member A |
| MEF2C | 6.151 | 6.243 | 4.93 | 3.338 | 4.731 | 3.869 | −5.184 | 0.0024426 | myocyte enhancer factor 2C |
| EPSTI1 | 3.708 | 1.388 | 3.015 | 1.267 | 3.732 | −0.012 | −5.164 | 0.012497 | epithelial stromal interaction 1 (breast) |
| SAMD11 | 2.005 | 3.595 | 2.891 | 1.228 | 0.647 | 0.162 | −5.157 | 0.0033691 | sterile alpha motif domain containing 11 |
| PDE1B | 4.475 | 2.184 | 4.334 | 1.969 | 0.283 | 2.048 | −5.154 | 0.0256622 | phosphodiesterase 1B, calmodulin-dependent |
| FUCA2 | 4.002 | 4.399 | 4.646 | 1.494 | 1.862 | 2.283 | −5.144 | 0.0004357 | fucosidase, alpha-L-2, plasma |
| IGFBP5 | 8.858 | 11.154 | 9.995 | 7.282 | 8.151 | 7.639 | −5.12 | 0.0154268 | insulin-like growth factor binding protein 5 |
| CXCL12 | 8.481 | 6.43 | 10.048 | 5.217 | 6.152 | 6.142 | −5.06 | 0.001491 | chemokine (C-X-C motif) ligand 12 |
| SPARC | 11.099 | 12.471 | 11.859 | 9.434 | 9.526 | 9.75 | −5.039 | 0.001491 | secreted protein, acidic, cysteine-rich (osteonectin) |

TABLE 6-continued

Differentially Expressed Genes in CD10+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD24+ N48 | CD24+ N58 | CD24+ N43 | CD24+ N37 | CD24+ N39 | CD24+ N40 | | | | |
| CHN1 | 3.529 | 2.572 | 3.637 | 0.762 | 1.305 | 0.552 | | −5.034 | 0.0010374 | chimerin (chimaerin) 1 |
| EMP1 | 10.735 | 7.104 | 9.657 | 6.459 | 7.548 | 7.326 | | −5.033 | 0.0371031 | epithelial membrane protein 1 |
| BMP5 | 5.501 | 6.837 | 5.976 | 4.507 | 1.82 | 3.851 | | −5.03 | 0.0053495 | bone morphogenetic protein 5 |
| PIGP | 4.307 | 4.363 | 3.975 | 1.672 | 2.994 | 1.645 | | −5.028 | 0.0026994 | phosphatidylinositol glycan anchor biosynthesis, class P |
| CTSD | 8.235 | 9.612 | 10.415 | 6.897 | 7.29 | 7.35 | | −4.999 | 0.0050719 | cathepsin D |
| PTPLAD2 | 2.888 | 1.126 | 3.759 | 0.573 | 0.17 | 1.277 | | −4.977 | 0.021539 | protein tyrosine phosphatase-like A domain containing 2 |
| CYYR1 | 4.245 | 3.175 | 0.945 | 0.86 | 0.515 | 0.886 | | −4.975 | 0.0260564 | cysteine/tyrosine-rich 1 |
| A2M | 10.21 | 11.185 | 10.085 | 8.256 | 7.775 | 8.455 | | −4.959 | 0.001124 | alpha-2-macroglobulin |
| OXTR | 9.258 | 11.522 | 11.028 | 8.719 | 8.512 | 8.793 | | −4.956 | 0.012258 | oxytocin receptor |
| SEMA3G | 8.578 | 5.278 | 6.183 | 3.543 | 3.95 | 3.875 | | −4.951 | 0.0054418 | sema domain, immunoglobulin domain (Ig), short basic domain, secreted, (semaphorin) 3G |
| EEPD1 | 6.508 | 6.351 | 5.769 | 4.046 | 4.267 | 3.202 | | −4.942 | 0.0009594 | endonuclease/exonuclease/phosphatase family domain containing 1 |
| IGF2AS | 2.546 | 0.623 | 1.942 | −0.311 | −0.887 | −0.362 | | −4.937 | 0.0041676 | insulin-like growth factor 2 antisense |
| MXRA5 | 5.979 | 7.043 | 8.098 | 4.573 | 4.956 | 4.744 | | −4.922 | 0.0041153 | matrix-remodelling associated 5 |
| TIMP2 | 10.148 | 9.257 | 10.371 | 6.869 | 8.079 | 7.984 | | −4.899 | 0.002414 | TIMP metallopeptidase inhibitor 2 |
| LUM | 9.048 | 7.399 | 9.517 | 4.192 | 7.022 | 7.227 | | −4.89 | 0.0182707 | lumican |
| MATN2 | 6.37 | 9.054 | 8.277 | 5.406 | 6.181 | 5.987 | | −4.889 | 0.0159877 | matrilin 2 |
| CEACAM1 | 6.148 | 9.01 | 7.627 | 5.3 | 5.343 | 5.718 | | −4.869 | 0.0132976 | carcinoembryonic antigen-related cell adhesion molecule 1 (biliary glycoprotein) |
| DYSF | 6.263 | 4.874 | 2.824 | 2.425 | 3.172 | 2.598 | | −4.843 | 0.0370208 | dysferlin, limb girdle muscular dystrophy 2B (autosomal recessive) |
| VSIG2 | 2.735 | 1.588 | −0.648 | −0.311 | −0.887 | −0.688 | | −4.841 | 0.0408829 | V-set and immunoglobulin domain containing 2 |
| PI15 | 6.039 | 7.951 | 8.63 | 5.303 | 5.899 | 5.681 | | −4.824 | 0.0188238 | peptidase inhibitor 15 |
| CHRDL1 | 6.044 | 3.319 | 6.29 | 1.797 | 4.023 | 3.633 | | −4.813 | 0.0406611 | chordin-like 1 |
| CPXM2 | 7.454 | 6.719 | 6.34 | 2.974 | 5.187 | 4.938 | | −4.812 | 0.0052272 | carboxypeptidase X (M14 family), member 2 |
| SRPX2 | 4.013 | 1.942 | 3.921 | 1.556 | 1.645 | 1.747 | | −4.81 | 0.0234993 | sushi-repeat-containing protein, X-linked 2 |
| C2 | 5.707 | 3.895 | 6.599 | 2.711 | 4.094 | 3.441 | | −4.809 | 0.0219196 | complement component 2 |
| SLC9A9 | 3.239 | 2.02 | 4.954 | 0.86 | 2.689 | 0.886 | | −4.806 | 0.0386592 | solute carrier family 9 (sodium/hydrogen exchanger), member 9 |
| TMEM144 | 3.579 | 5.656 | 4.887 | 2.624 | 1.408 | 2.832 | | −4.8 | 0.005328 | transmembrane protein 144 |
| ALPK2 | 3.12 | 5.183 | 3.207 | 0.86 | 2.206 | 2.06 | | −4.789 | 0.0117071 | alpha-kinase 2 |
| DHDH | 4.356 | 5.126 | 5.533 | 2.724 | 3.121 | 2.875 | | −4.761 | 0.0016184 | dihydrodiol dehydrogenase (dimeric) |
| KDELR3 | 3.324 | 1.966 | 3.149 | 0.173 | 0.283 | 1.075 | | −4.752 | 0.002268 | KDEL (Lys-Asp-Glu-Leu) endoplasmic reticulum protein retention receptor 3 |
| ECM2 | 4.607 | 2.847 | 5.11 | 1.366 | 2.53 | 2.358 | | −4.751 | 0.0114452 | extracellular matrix protein 2, female organ and adipocyte specific |
| LHFP | 7.357 | 8.726 | 8.838 | 6.479 | 6.344 | 6.553 | | −4.747 | 0.0056572 | lipoma HMGIC fusion partner |
| GPNMB | 10.06 | 10.578 | 9.963 | 7.886 | 7.719 | 8.18 | | −4.737 | 0.0003856 | glycoprotein (transmembrane) nmb |
| LYRM5 | 3.255 | 3.677 | 2.401 | 2.171 | 0.695 | 0.162 | | −4.72 | 0.0088374 | LYR motif containing 5 |
| HOXA2 | 3.298 | 3.521 | 3.25 | −0.311 | 2.692 | 1.059 | | −4.72 | 0.0129427 | homeobox A2 |
| GLB1 | 3.53 | 5.904 | 4.771 | 2.84 | 2.314 | 2.533 | | −4.711 | 0.0073056 | galactosidase, beta 1 |
| IGFBP3 | 12.05 | 11.696 | 10.87 | 9.46 | 9.13 | 9.497 | | −4.711 | 0.0013186 | insulin-like growth factor binding protein 3 |
| PIK3C2B | 6.308 | 8.495 | 5.841 | 3.653 | 4.073 | 4.292 | | −4.707 | 0.0033262 | phosphoinositide-3-kinase, class 2, beta polypeptide |
| EFEMP1 | 8.705 | 10.875 | 10.916 | 8.36 | 8.056 | 8.684 | | −4.699 | 0.0209759 | EGF-containing fibulin-like extracellular matrix protein 1 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| RASSF2 | 5.285 | 3.354 | 4.459 | 1.659 | 2.775 | 2.228 | −4.692 | 0.0060857 | Ras association (RalGDS/AF-6) domain family member 2 |
| ITM2B | 10.108 | 11.103 | 11.165 | 8.408 | 8.935 | 8.754 | −4.691 | 0.0016914 | integral membrane protein 2B |
| CYP1B1 | 8.524 | 8.017 | 9.48 | 5.798 | 6.88 | 6.644 | −4.655 | 0.0032046 | cytochrome P450, family 1, subfamily B, polypeptide 1 |
| ADAMTS14 | 0.871 | 2.391 | 4.04 | 0.173 | 0.283 | −0.206 | −4.652 | 0.0116713 | ADAM metallopeptidase with thrombospondin type 1 motif, 14 |
| PLAT | 8.741 | 11.05 | 8.947 | 6.734 | 6.687 | 7.058 | −4.637 | 0.0028125 | plasminogen activator, tissue |
| DFNA5 | 2.981 | 5.301 | 4.84 | 3.088 | 2.073 | 2.54 | −4.636 | 0.0216892 | deafness, autosomal dominant 5 |
| ITIH3 | 3.169 | 5.005 | 4.567 | 2.794 | 2.352 | 1.66 | −4.63 | 0.0090205 | inter-alpha (globulin) inhibitor H3 |
| PIM3 | 7.097 | 9.482 | 8.654 | 6.346 | 6.508 | 6.443 | −4.627 | 0.0113844 | pim-3 oncogene |
| DKK2 | 2.819 | 0.988 | 4.392 | 0.762 | 0.609 | 0.552 | −4.626 | 0.0233412 | dickkopf homolog 2 (Xenopus laevis) |
| BTN3A3 | 4.449 | 3.633 | 4.672 | 1.426 | 2.745 | 1.513 | −4.62 | 0.0022179 | butyrophilin, subfamily 3, member A3 |
| EPHX1 | 7.496 | 6.352 | 8.954 | 5.041 | 5.337 | 5.29 | −4.614 | 0.0059255 | epoxide hydrolase 1, microsomal (xenobiotic) |
| LMCD1 | 5.885 | 4.559 | 5.606 | 2.201 | 3.68 | 3.549 | −4.612 | 0.0047757 | LIM and cysteine-rich domains 1 |
| PTPRN | 1.896 | 1.998 | 2.976 | 0.415 | −0.264 | −0.206 | −4.61 | 0.0012413 | protein tyrosine phosphatase, receptor type, N |
| EDAR | 0.251 | 2.52 | 1.998 | 0.173 | −0.264 | −0.206 | −4.609 | 0.0227216 | ectodysplasin A receptor |
| ADAMTS4 | 10.316 | 9.462 | 10.936 | 7.259 | 8.472 | 8.169 | −4.601 | 0.0032461 | ADAM metallopeptidase with thrombospondin type 1 motif, 4 |
| LRRC4C | 3.772 | 5.158 | 5.26 | 2.908 | 3.059 | 2.575 | −4.597 | 0.0057652 | leucine rich repeat containing 4C |
| ST3GAL5 | 4.547 | 2.921 | 4.746 | 2.109 | 2.352 | 2.52 | −4.578 | 0.012781 | STS beta-galactoside alpha-2,3-sialyltransferase 5 |
| MBNL1 | 8.986 | 10.216 | 10.148 | 7.925 | 7.649 | 8.025 | −4.567 | 0.003475 | muscleblind-like (Drosophila) |
| AQP7P3 | 3.352 | 4.56 | 3.835 | 1.244 | 2.06 | 1.645 | −4.564 | 0.0015611 | aquaporin 7 pseudogene 3 |
| PLP1 | 2.887 | 4.511 | 3.556 | 1.366 | 1.033 | 1.609 | −4.562 | 0.0021128 | proteolipid protein 1 |
| TARBP1 | 3.286 | 5.46 | 5.848 | 2.887 | 3.275 | 3.274 | −4.552 | 0.0305996 | TAR (HIV-1) RNA binding protein 1 |
| RCVRN | 4.539 | 3.957 | 5.012 | 2.354 | 3.596 | 1.758 | −4.548 | 0.0090914 | recoverin |
| NEGR1 | 4.901 | 2.121 | 4.268 | 2.083 | 2.512 | 1.966 | −4.548 | 0.0499406 | neuronal growth regulator 1 |
| FAM83B | 3.847 | 6.33 | 5.991 | 3.809 | 3.316 | 3.81 | −4.538 | 0.0277599 | family with sequence similarity 83, member B |
| TRIM6 | 0.403 | 2.17 | 2.111 | −0.824 | −0.648 | −0.012 | −4.537 | 0.00698 | tripartite motif-containing 6 |
| MAPK12 | 4.966 | 0.862 | 2.809 | 0.631 | 0.415 | 0.814 | −4.526 | 0.0298054 | mitogen-activated protein kinase 12 |
| PCDHB3 | 2.073 | 3.738 | 2.33 | 0.967 | −0.104 | 1.107 | −4.522 | 0.0074193 | protocadherin beta 3 |
| GBP2 | 7.899 | 8.739 | 8.77 | 5.588 | 6.909 | 6.565 | −4.513 | 0.0031974 | guanylate binding protein 2, interferon-inducible |
| APOL4 | 6.368 | 4.95 | 3.326 | 3.436 | 2.777 | 2.409 | −4.51 | 0.0234578 | apolipoprotein L, 4 |
| SEMA6D | 4.489 | 6.479 | 5.744 | 3.573 | 3.397 | 4.07 | −4.504 | 0.0098233 | sema domain, transmembrane domain (TM), and cytoplasmic domain, (semaphorin) 6D |
| EPB41L3 | 4.187 | 3.827 | 5.136 | 1.698 | 2.706 | 2.016 | −4.501 | 0.0023095 | erythrocyte membrane protein band 4.1-like 3 |
| C8orf85 | 3.532 | 5.285 | 3.565 | 1.868 | 1.362 | 2.567 | −4.501 | 0.0062667 | chromosome 8 open reading frame 85 |
| MTUS1 | 6.921 | 6.272 | 7.408 | 4.148 | 4.753 | 5.154 | −4.493 | 0.0020276 | microtubule associated tumor suppressor 1 |
| CASP4 | 6.7 | 8.104 | 7.882 | 5.714 | 5.317 | 5.877 | −4.492 | 0.0044051 | caspase 4, apoptosis-related cysteine peptidase |
| PQLC3 | 2.812 | 2.579 | 2.574 | 0.415 | 0.283 | 1.779 | −4.482 | 0.0061143 | PQ loop repeat containing 3 |
| CASD1 | 4.675 | 6.423 | 6.337 | 3.675 | 3.443 | 4.261 | −4.477 | 0.0072412 | CAS1 domain containing 1 |
| GOLGA8B | 4.504 | 6.736 | 6.912 | 4.755 | 4.138 | 4.361 | −4.461 | 0.0363383 | golgin A8 family, member B |
| CA2 | 4.99 | 7.396 | 6.266 | 4.112 | 4.415 | 4.01 | −4.452 | 0.0100959 | carbonic anhydrase II |
| CMAH | 3.59 | 2.392 | 3.438 | 1.121 | 1.07 | 1.436 | −4.45 | 0.0030128 | cytidine monophosphate-N-acetylneuraminic acid hydroxylase (CMP-N-acetylneuraminate monooxygenase) pseudogene |
| CPXM1 | 8.32 | 8.212 | 8.809 | 6.059 | 6.638 | 6.55 | −4.447 | 0.0008307 | carboxypeptidase X (M14 family), member 1 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| TMEM176B | 6.098 | 4.261 | 7.562 | 2.109 | 4.715 | 4.081 | −4.445 | 0.0287308 | transmembrane protein 176B |
| FBXL7 | 6.395 | 5.072 | 6.414 | 4.109 | 4.102 | 4.263 | −4.444 | 0.0054146 | F-box and leucine-rich repeat protein 7 |
| NRBP2 | 5.752 | 8.804 | 8.237 | 5.335 | 6.093 | 6.086 | −4.443 | 0.0452436 | nuclear receptor binding protein 2 |
| TCN2 | 5.838 | 4.48 | 4.924 | 2.57 | 2.775 | 3.257 | −4.435 | 0.0019704 | transcobalamin II |
| OTOF | 2.596 | 4.562 | 3.847 | 1.698 | 1.408 | 2.19 | −4.434 | 0.0096745 | otoferlin |
| TCF4 | 10.509 | 7.186 | 8.39 | 5.056 | 6.695 | 6.249 | −4.413 | 0.0103155 | transcription factor 4 |
| SERPINF1 | 8.952 | 8.484 | 9.443 | 5.967 | 7.307 | 6.813 | −4.404 | 0.0021271 | serpin peptidase inhibitor, clade F (alpha-2 antiplasmin, pigment epithelium derived factor), member 1 |
| TSPAN3 | 5.512 | 7.033 | 7.079 | 4.94 | 3.639 | 4.214 | −4.403 | 0.0044545 | tetraspanin 3 |
| SKP2 | 2.196 | 5.213 | 3.618 | 1.606 | 0.848 | 1.486 | −4.385 | 0.010523 | S-phase kinase-associated protein 2 (p45) |
| NRP1 | 8.23 | 6.994 | 7.52 | 5.046 | 5.753 | 5.391 | −4.375 | 0.0016985 | neuropilin 1 |
| LOC100188947 | 2.221 | 4.533 | 1.865 | 1.641 | −0.264 | 0.713 | −4.374 | 0.0206511 | No description |
| ADAM12 | 4.417 | 5.669 | 6.037 | 3.119 | 3.562 | 3.55 | −4.345 | 0.0049632 | ADAM metallopeptidase domain 12 |
| SERPINI1 | 4.531 | 5.866 | 5.337 | 2.492 | 3.464 | 3.218 | −4.344 | 0.0025692 | serpin peptidase inhibitor, clade I (neuroserpin), member 1 |
| COL6A3 | 8.045 | 5.973 | 9.411 | 4.291 | 6.235 | 5.927 | −4.34 | 0.0248029 | collagen, type VI, alpha 3 |
| RASAL1 | 0.554 | 3.82 | 2.29 | 0.173 | 1.099 | 0.162 | −4.337 | 0.0495256 | RAS protein activator like 1 (GAP1 like) |
| FLCN | 6.52 | 8.294 | 8.427 | 6.11 | 6.187 | 6.18 | −4.329 | 0.0213858 | folliculin |
| PLSCR4 | 5.443 | 6.97 | 7.012 | 3.435 | 4.904 | 4.138 | −4.308 | 0.0046569 | phospholipid scramblase 4 |
| PCDHB14 | 2.457 | 4.212 | 3.684 | 1.121 | 1.07 | 2.107 | −4.3 | 0.0073127 | protocadherin beta 14 |
| C10orf11 | 3.112 | 3.302 | 2.409 | −0.104 | 1.198 | 1.059 | −4.299 | 0.0024548 | chromosome 10 open reading frame 11 |
| TRIP10 | 7.939 | 9.942 | 9.407 | 7.123 | 7.305 | 7.562 | −4.295 | 0.0133662 | thyroid hormone receptor interactor 10 |
| CERCAM | 7.344 | 6.666 | 7.925 | 5.113 | 5.687 | 5.244 | −4.288 | 0.0028511 | cerebral endothelial cell adhesion molecule |
| PTPRG | 4.405 | 5.999 | 6.32 | 4.189 | 3.563 | 3.899 | −4.288 | 0.0166402 | protein tyrosine phosphatase, receptor type, G |
| PLBD1 | 4.948 | 4.313 | 5.437 | 1.366 | 4.043 | 2.848 | −4.286 | 0.0132539 | phospholipase B domain containing 1 |
| LRP11 | 4.282 | 5.598 | 5.208 | 3.112 | 2.717 | 3.387 | −4.273 | 0.0035322 | low density lipoprotein receptor-related protein 11 |
| TMEM163 | 5.834 | 6.216 | 5.55 | 3.455 | 3.508 | 4.282 | −4.272 | 0.0011669 | transmembrane protein 163 |
| EMID1 | 2.98 | 2.879 | 3.404 | 1.407 | 0.515 | 0.886 | −4.269 | 0.0009022 | EMI domain containing 1 |
| MMP2 | 10.857 | 9.629 | 11.636 | 8.036 | 8.767 | 8.876 | −4.259 | 0.0059183 | matrix metallopeptidase 2 (gelatinase A, 72kDa gelatinase, 72kDa type IV collagenase) |
| ZNF711 | 5.208 | 7.3 | 7.226 | 4.481 | 5.212 | 4.714 | −4.253 | 0.0196752 | zinc finger protein 711 |
| SEC24D | 6.301 | 8.552 | 8.18 | 5.964 | 6.1 | 6.302 | −4.228 | 0.0323539 | SEC24 family, member D (S. cerevisiae) |
| FAIM2 | 3.27 | 2.163 | 3.914 | 1.366 | 1.033 | 1.201 | −4.198 | 0.005816 | Fas apoptotic inhibitory molecule 2 |
| DLC1 | 6.641 | 8.215 | 6.182 | 4.113 | 4.897 | 4.76 | −4.195 | 0.0037633 | deleted in liver cancer 1 |
| ECEL1 | 3.958 | 3.454 | 4.884 | 3.272 | 1.387 | 1.576 | −4.192 | 0.0116026 | endothelin converting enzyme-like 1 |
| KCTD18 | 1.703 | 4.072 | 3.211 | 1.407 | 1.145 | 1.138 | −4.188 | 0.0187587 | potassium channel tetramerisation domain containing 18 |
| TMEM189 | 5.992 | 8.531 | 7.116 | 5.567 | 4.402 | 5.057 | −4.169 | 0.010357 | transmembrane protein 189 |
| GNG11 | 7.926 | 4.155 | 5.347 | 2.396 | 3.588 | 3.29 | −4.162 | 0.0125435 | guanine nucleotide binding protein (G protein), gamma 11 |
| ASTN1 | 4.079 | 2.599 | 4.911 | 2.255 | 1.907 | 2.024 | −4.157 | 0.016324 | astrotactin 1 |
| GABARAPL1 | 5.318 | 7.035 | 7.332 | 4.781 | 5.142 | 4.98 | −4.157 | 0.0227717 | GABA(A) receptor-associated protein like 1 |
| SERPINA5 | 3.039 | 3.347 | 4.791 | 1.299 | 1.604 | 1.163 | −4.135 | 0.0024354 | serpin peptidase inhibitor, clade A (alpha-1 antiproteinase, antitrypsin), member 5 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| KCNJ2 | 3.886 | 6.906 | 5.403 | 3.323 | 3.587 | 3.357 | -4.13 | 0.0213093 | potassium inwardly-rectifying channel, subfamily J, member 2 |
| SLC17A7 | 4.943 | 2.849 | 4.809 | 2.466 | 2.899 | 2.667 | -4.125 | 0.0335086 | solute carrier family 17 (sodium-dependent inorganic phosphate cotransporter), member 7 |
| TMEM106B | 3.971 | 5.846 | 5.353 | 3.529 | 2.727 | 3.315 | -4.108 | 0.0102039 | transmembrane protein 106B |
| C20orf103 | 1.818 | 2.8 | 2.492 | 0.762 | 0.17 | 0.251 | -4.106 | 0.0018674 | chromosome 20 open reading frame 103 |
| PTH1R | 4.673 | 2.515 | 4.677 | 1.889 | 2.639 | 1.999 | -4.106 | 0.0223517 | parathyroid hormone 1 receptor |
| ST6GAL2 | 3.259 | 5.47 | 5.023 | 3.433 | 2.763 | 2.976 | -4.104 | 0.0349624 | ST6 beta-galactosamide alpha-2,6-sialyltranferase 2 |
| RNF122 | 4.682 | 3.799 | 4.634 | 1.715 | 2.601 | 2.663 | -4.091 | 0.0024791 | ring finger protein 122 |
| CCDC136 | 5.328 | 6.809 | 6.704 | 4.607 | 4.777 | 4.184 | -4.09 | 0.0084517 | coiled-coil domain containing 136 |
| HS1BP3 | 5.488 | 4.149 | 3.712 | 2.146 | 1.738 | 2.117 | -4.088 | 0.0020348 | HCLS1 binding protein 3 |
| ELMO1 | 6.094 | 5.362 | 6.321 | 4.064 | 4.099 | 4.029 | -4.087 | 0.0017543 | engulfment and cell motility 1 |
| ZEB1 | 6.955 | 4.923 | 6.444 | 4.195 | 4.691 | 4.415 | -4.082 | 0.0180311 | zinc finger E-box binding homeobox 1 |
| FZD7 | 7.053 | 9.213 | 9.303 | 6.619 | 7.188 | 7.242 | -4.069 | 0.0448158 | frizzled homolog 7 (Drosophila) |
| ADAM19 | 4.849 | 2.502 | 3.843 | 1.698 | 2.557 | 1.818 | -4.068 | 0.0242577 | ADAM metallopeptidase domain 19 |
| ECSCR | 6.553 | 1.846 | 3.45 | 1.426 | 1.305 | 1.715 | -4.068 | 0.0327474 | endothelial cell-specific chemotaxis regulator |
| MPV17 | 4.064 | 6.118 | 5.329 | 3.228 | 3.992 | 3.305 | -4.067 | 0.019844 | MpV17 mitochondrial inner membrane protein |
| PGCP | 5.674 | 6.409 | 6.094 | 3.54 | 4.389 | 4.176 | -4.057 | 0.0015898 | No description |
| KNDC1 | 3.025 | 0.924 | 2.647 | 0.86 | 0.515 | 0.631 | -4.045 | 0.0291858 | kinase non-catalytic C-lobe domain (KIND) containing 1 |
| CLIC2 | 7.177 | 5.471 | 6.842 | 4.097 | 5.014 | 4.838 | -4.011 | 0.0098805 | chloride intracellular channel 2 |
| NDRG3 | 3.966 | 4.282 | 3.839 | 1.837 | 2.728 | 1.837 | -4.005 | 0.0020841 | NDRG family member 3 |
| ADD3 | 6.214 | 6.258 | 7.682 | 4.212 | 5.178 | 5.298 | -4.005 | 0.0105445 | adducin 3 (gamma) |
| FMNL1 | 3.796 | 6.348 | 5.871 | 4.069 | 3.304 | 3.87 | -4.003 | 0.0429227 | formin-like 1 |
| RAB6C | 6.377 | 7.524 | 7.855 | 5.559 | 5.392 | 5.524 | -3.998 | 0.0061859 | RAB6C, member RAS oncogene family |
| AADAT | 2.242 | 2.822 | 3.187 | 1.188 | 0.609 | 0.552 | -3.996 | 0.001896 | aminoadipate aminotransferase |
| RWDD2A | 1.156 | 1.893 | 2.099 | -0.104 | -0.887 | 0.327 | -3.993 | 0.0040288 | RWD domain containing 2A |
| SCN1B | 2.911 | 5.637 | 4.321 | 2.323 | 2.486 | 2.111 | -3.993 | 0.0160671 | sodium channel, voltage-gated, type I, beta |
| TMEM185A | 5.328 | 5.719 | 4.834 | 3.332 | 3.561 | 3.271 | -3.987 | 0.0013859 | transmembrane protein 185A |
| HEPH | 6.017 | 7.928 | 8.153 | 5.515 | 5.983 | 5.934 | -3.982 | 0.0313866 | hephaestin |
| KIAA0182 | 5.196 | 6.892 | 6.845 | 4.902 | 4.558 | 4.37 | -3.973 | 0.0137318 | KIAA0182 |
| GNAI1 | 6.183 | 8.354 | 7.983 | 5.995 | 5.797 | 6.304 | -3.968 | 0.0378286 | guanine nucleotide binding protein (G protein), alpha inhibiting activity polypeptide 1 |
| ABLIM3 | 7.13 | 3.877 | 5.617 | 2.719 | 4.034 | 3.63 | -3.963 | 0.0263955 | actin binding LIM protein family, members |
| ITGA5 | 10.794 | 8.697 | 9.51 | 7.04 | 7.94 | 7.524 | -3.961 | 0.0063225 | integrin, alpha 5 (fibronectin receptor, alpha polypeptide) |
| HDGFRP2 | 4.226 | 6.181 | 5.603 | 2.767 | 3.827 | 3.618 | -3.961 | 0.0108857 | No description |
| AQP1 | 10.594 | 9.032 | 8.164 | 7.173 | 6.966 | 7.046 | -3.96 | 0.0071789 | aquaporin 1 (Colton blood group) |
| FHL1 | 5.786 | 5.487 | 5.426 | 3.629 | 3.503 | 3.478 | -3.956 | 0.0002654 | four and a half LIM domains 1 |
| CC2D1A | 6.116 | 8.142 | 8.03 | 5.676 | 6.161 | 5.977 | -3.95 | 0.034438 | coiled-coil and C2 domain containing 1A |
| IL1RAP | 6.973 | 8.785 | 8.882 | 6.893 | 6.652 | 6.805 | -3.944 | 0.0342277 | interleukin 1 receptor accessory protein |
| SHC4 | 3.71 | 6.207 | 4.953 | 2.852 | 3.176 | 2.977 | -3.936 | 0.0134092 | SHC (Src homology 2 domain containing) family, member 4 |
| LOXL2 | 6.909 | 8.636 | 8.001 | 6.219 | 5.431 | 6.025 | -3.935 | 0.0063848 | lysyl oxidase-like 2 |
| PCDHB13 | 2.258 | 2.074 | 2.039 | 0.173 | 0.283 | -0.206 | -3.932 | 0.0003785 | protocadherin beta 13 |
| IL11RA | 5.698 | 6.829 | 6.234 | 3.738 | 4.261 | 4.478 | -3.926 | 0.0018888 | interleukin 11 receptor, alpha |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| PALMD | 5.29 | 5.17 | 3.439 | 2.14 | 3.319 | 3.079 | -3.92 | 0.0178486 | palmdelphin |
| RETSAT | 6.892 | 7.932 | 7.751 | 5.637 | 5.457 | 5.964 | -3.913 | 0.0029985 | retinol saturase (all-trans-retinol 13,14-reductase) |
| SMPDL3A | 3.56 | 3.072 | 5.089 | 0.762 | 3.121 | 2.124 | -3.913 | 0.0281319 | sphingomyelin phosphodiesterase, acid-like SA |
| INPP5D | 5.35 | 4.946 | 5.194 | 3.232 | 4.07 | 2.981 | -3.897 | 0.0038191 | inositol polyphosphate-5-phosphatase, 145kDa |
| LYSMD4 | 2.711 | 5.178 | 4.899 | 2.33 | 2.578 | 3.217 | -3.895 | 0.0476869 | LysM, putative peptidoglycan-binding, domain containing 4 |
| NID2 | 3.4 | 2.111 | 3.776 | 1.121 | 1.82 | 0.935 | -3.879 | 0.0100787 | nidogen 2 (osteonidogen) |
| SOX11 | 6.201 | 7.296 | 6.3 | 5.185 | 4.247 | 4.815 | -3.876 | 0.0046856 | SRY (sex determining region Y)-box 11 |
| SYNM | 8.075 | 9.49 | 9.67 | 6.797 | 7.535 | 7.685 | -3.876 | 0.0119296 | synemin, intermediate filament protein |
| AGR3 | 2.715 | 3.918 | 1.66 | 0.762 | 1.546 | 0.552 | -3.872 | 0.0182421 | anterior gradient homolog 3 (Xenopus laevis) |
| OTUD1 | 5.905 | 6.561 | 5.462 | 4.172 | 3.957 | 3.865 | -3.858 | 0.0017185 | OTU domain containing 1 |
| SOCS2 | 5.858 | 6.167 | 6.548 | 3.911 | 4.504 | 4.306 | -3.855 | 0.0011455 | suppressor of cytokine signaling 2 |
| NBL1 | 8.422 | 8.421 | 10.308 | 7.619 | 6.477 | 7.816 | -3.847 | 0.0239315 | neuroblastoma, suppression of tumorigenicity 1 |
| MBNL2 | 8.685 | 11.438 | 10.333 | 7.527 | 8.394 | 8.425 | -3.834 | 0.0173707 | muscleblind-like 2 (Drosophila) |
| FABP7 | 1.571 | 4.038 | 0.788 | -0.311 | -0.887 | -0.362 | -3.818 | 0.0083745 | fatty acid binding protein 7, brain |
| IRX6 | 1.571 | -0.258 | 1.852 | -0.311 | -0.887 | -0.362 | -3.818 | 0.0291085 | iroquois homeobox 6 |
| GPR116 | 7.73 | 4.573 | 5.157 | 2.642 | 3.841 | 3.872 | -3.814 | 0.0166896 | G protein-coupled receptor 116 |
| BBS2 | 4.212 | 5.816 | 6.161 | 3.333 | 3.885 | 3.994 | -3.814 | 0.0191622 | Bardet-Biedl syndrome 2 |
| PCDH18 | 4.934 | 5.636 | 5.944 | 3.134 | 3.825 | 3.706 | -3.812 | 0.0023024 | protocadherin 18 |
| ETV1 | 6.254 | 8.288 | 7.115 | 4.325 | 5.62 | 5.264 | -3.809 | 0.00782 | ets variant 1 |
| SNX7 | 4.389 | 5.886 | 5.417 | 3.489 | 3.444 | 3.787 | -3.805 | 0.0085011 | sorting nexin 7 |
| CPS1 | 1.576 | 3.487 | 2.801 | 1.188 | 0.875 | 0.842 | -3.801 | 0.0150447 | carbamoyl-phosphate synthase 1, mitochondrial |
| TRO | 5.84 | 7.944 | 8.394 | 5.554 | 6.018 | 6.041 | -3.799 | 0.048632 | trophinin |
| CREB5 | 7.11 | 10.08 | 8.893 | 6.863 | 6.968 | 6.989 | -3.797 | 0.0336954 | cAMP responsive element binding protein 5 |
| C14orf132 | 3.869 | 6.034 | 6.055 | 4.13 | 3.968 | 3.481 | -3.797 | 0.0483959 | chromosome 14 open reading frame 132 |
| C8orf40 | 3.766 | 4.538 | 3.827 | 1.757 | 2.206 | 2.614 | -3.793 | 0.0027338 | chromosome 8 open reading frame 40 |
| CXCL13 | 1.714 | 1.75 | 1.674 | 0.173 | -0.264 | -0.206 | -3.784 | 0.0005509 | chemokine (C-X-C motif) ligand 13 |
| ZNF385D | 6.276 | 6.056 | 4.682 | 4.145 | 3.848 | 4.137 | -3.783 | 0.0119224 | zinc finger protein 385D |
| CDON | 4.156 | 4.334 | 4.386 | 2.238 | 2.794 | 2.311 | -3.78 | 0.000787 | Cdon homolog (mouse) |
| RBP5 | 2.884 | 0.522 | 2.14 | 0.967 | -0.104 | -0.688 | -3.777 | 0.0297324 | retinol binding protein 5, cellular |
| NTRK1 | 2.468 | 2.74 | 4.828 | 1.773 | 2.115 | 0.552 | -3.773 | 0.0279051 | neurotrophic tyrosine kinase, receptor, type 1 |
| FERMT2 | 8.877 | 10.445 | 10.316 | 8.254 | 8.359 | 8.532 | -3.767 | 0.0176497 | fermitin family member 2 |
| CCNG1 | 5.806 | 8.786 | 7.694 | 5.654 | 5.792 | 5.781 | -3.765 | 0.0403835 | cyclin G1 |
| FGL2 | 7.309 | 4.707 | 6.168 | 4.021 | 4.448 | 4.258 | -3.758 | 0.0207026 | fibrinogen-like 2 |
| C20orf199 | 9.8 | 11.308 | 10.845 | 8.937 | 8.615 | 9.297 | -3.755 | 0.0089096 | No description |
| C1S | 9.783 | 8.351 | 10.077 | 6.65 | 7.971 | 7.875 | -3.751 | 0.0124626 | complement component 1, s subcomponent |
| PPAP2A | 7.511 | 10.019 | 8.452 | 6.041 | 6.631 | 6.551 | -3.735 | 0.0075839 | phosphatidic acid phosphatase type 2A |
| VAT1 | 4.819 | 3.95 | 5.108 | 2.964 | 2.924 | 2.132 | -3.721 | 0.0037097 | vesicle amine transport protein 1 homolog (T. californica)-like |
| MGST2 | 5.537 | 2.526 | 1.247 | 1.029 | -0.648 | 0.831 | -3.718 | 0.0220577 | microsomal glutathione S-transferase 2 |
| ABCA6 | 4.316 | 2.432 | 4.733 | 2.423 | 2.32 | 2.466 | -3.715 | 0.0466473 | ATP-binding cassette, sub-family A (ABC1), member 6 |
| RPA3 | 2.607 | 4.26 | 3.196 | 0.924 | 2.332 | 1.305 | -3.709 | 0.0125506 | replication protein A3, 14kDa |
| SORCS2 | 3.765 | 5.887 | 5.432 | 3.339 | 3.542 | 3.767 | -3.705 | 0.0337326 | sortilin-related VPS10 domain containing receptor 2 |
| HVCN1 | 1.786 | -0.529 | 1.548 | -0.104 | -0.887 | -0.688 | -3.705 | 0.0473714 | hydrogen voltage-gated channel 1 |
| SEPN1 | 7.244 | 7.574 | 7.637 | 5.688 | 5.389 | 5.729 | -3.696 | 0.0005581 | selenoprotein N, 1 |
| GPR87 | 4.083 | 7.236 | 5.849 | 3.964 | 2.522 | 4.066 | -3.693 | 0.0219375 | G protein-coupled receptor 87 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| MAOB | 5.725 | 7.508 | 5.531 | 4.465 | 3.647 | 4.504 | −3.692 | 0.0091937 | monoamine oxidase B |
| PTN | 7.593 | 9.666 | 8.759 | 6.875 | 6.864 | 6.982 | −3.689 | 0.0126501 | pleiotrophin |
| NGFRAP1 | 8.008 | 9.794 | 9.7 | 6.564 | 7.725 | 7.913 | −3.681 | 0.0200336 | nerve growth factor receptor (TNFRSF16) associated protein 1 |
| C3orf59 | 5.204 | 4.493 | 4.294 | 3.324 | 2.56 | 2.585 | −3.68 | 0.0033119 | chromosome 3 open reading frame 59 |
| LCP1 | 10.817 | 8.26 | 8.661 | 7.29 | 6.381 | 6.91 | −3.68 | 0.0079309 | lymphocyte cytosolic protein 1 (L-plastin) |
| CCDC82 | 4.456 | 6.379 | 5.895 | 3.93 | 3.876 | 4.499 | −3.68 | 0.0286571 | coiled-coil domain containing 82 |
| POPDC2 | 6.424 | 7.197 | 7.817 | 4.546 | 5.884 | 5.518 | −3.675 | 0.0092438 | popeye domain containing 2 |
| ADAMTS9 | 9.439 | 8.795 | 8.12 | 7.072 | 6.558 | 6.918 | −3.673 | 0.0032389 | ADAM metallopeptidase with thrombospondin type 1 motif, 9 |
| HIBCH | 6.351 | 7.911 | 8.105 | 5.367 | 6.223 | 6.038 | −3.664 | 0.0216406 | 3-hydroxyisobutyryl-CoA hydrolase |
| THBS4 | 6.104 | 4.49 | 4.929 | 2.543 | 4.231 | 3.197 | −3.662 | 0.0147693 | thrombospondin 4 |
| KAZALD1 | 3.136 | 3.481 | 4.103 | 1.366 | 2.048 | 1.609 | −3.66 | 0.0023238 | Kazal-type serine peptidase inhibitor domain 1 |
| CFH | 7.197 | 5.063 | 6.622 | 4.75 | 4.639 | 4.839 | −3.659 | 0.0261766 | complement factor H |
| LY6E | 9.951 | 10.403 | 9.022 | 8.08 | 7.98 | 8.217 | −3.658 | 0.0059326 | lymphocyte antigen 6 complex, locus E |
| 7-Mar | 6.617 | 7.969 | 7.865 | 5.75 | 5.262 | 6.1 | −3.654 | 0.0075081 | membrane-associated ring finger (C3HC4) 7 |
| AGA | 2.419 | 3.953 | 2.802 | 0.762 | 2.115 | 0.552 | −3.649 | 0.0117336 | aspartylglucosaminidase |
| HOXB3 | 5.166 | 2.631 | 4.164 | 2.304 | 1.932 | 2.986 | −3.629 | 0.0418294 | homeobox B3 |
| PDS5B | 5.793 | 7.111 | 7.288 | 5.183 | 4.842 | 5.429 | −3.628 | 0.0135086 | PDS5, regulator of cohesion maintenance, homolog B (S. cerevisiae) |
| AFAP1 | 6.261 | 7.941 | 7.269 | 5.411 | 5.186 | 5.459 | −3.625 | 0.0068742 | actin filament associated protein 1 |
| CMC1 | 2.936 | 3.651 | 2.939 | 1.079 | 1.387 | 1.261 | −3.623 | 0.0011018 | COX assembly mitochondrial protein homolog (S. cerevisiae) |
| SSPN | 6.742 | 7.549 | 7.187 | 4.587 | 5.88 | 5.33 | −3.622 | 0.0042091 | sarcospan (Kras oncogene-associated gene) |
| PCDHB5 | 3.715 | 3.911 | 3.881 | 2.026 | 2.166 | 1.779 | −3.619 | 0.0004715 | protocadherin beta 5 |
| NAV1 | 6.65 | 7.441 | 6.002 | 5.126 | 4.425 | 4.8 | −3.606 | 0.0044273 | neuron navigator 1 |
| KLHL5 | 3.822 | 4.284 | 3.249 | 1.723 | 2.439 | 1.766 | −3.594 | 0.0037562 | kelch-like 5 (Drosophila) |
| GBP3 | 4.822 | 5.164 | 5.586 | 3.32 | 3.623 | 3.022 | −3.591 | 0.0016499 | guanylate binding protein 3 |
| DLEU1 | 2.488 | 4.643 | 3.968 | 1.623 | 2.623 | 2.124 | −3.59 | 0.0303069 | deleted in lymphocytic leukemia 1 (non-protein coding) |
| TST | 1.48 | 2.902 | 2.463 | 1.672 | −0.104 | −0.362 | −3.584 | 0.0183208 | thiosulfate sulfurtransferase (rhodanese) |
| EFR3A | 4.503 | 5.989 | 5.902 | 3.877 | 3.524 | 4.151 | −3.575 | 0.0129355 | EFR3 homolog A (S. cerevisiae) |
| FAT1 | 8.61 | 11.014 | 10.231 | 8.513 | 8.231 | 8.394 | −3.572 | 0.0319067 | FAT tumor suppressor homolog 1 (Drosophila) |
| F2RL1 | 4.219 | 6.695 | 5.334 | 3.842 | 3.498 | 3.261 | −3.57 | 0.0163519 | coagulation factor II (thrombin) receptor-like 1 |
| RBMS3 | 5.747 | 8.591 | 7.586 | 5.353 | 5.753 | 5.805 | −3.563 | 0.0385362 | RNA binding motif, single stranded interacting protein 3 |
| TMEM135 | 3.055 | 4.281 | 4.185 | 2.246 | 2.45 | 2.091 | −3.557 | 0.0082972 | transmembrane protein 135 |
| ZSCAN18 | 4.763 | 6.27 | 6.043 | 4.442 | 4.172 | 3.71 | −3.55 | 0.014194 | zinc finger and SCAN domain containing 18 |
| SARDH | 2.687 | 4.046 | 2.745 | 0.86 | 1.678 | 1.486 | −3.547 | 0.0070459 | sarcosine dehydrogenase |
| NCRNA00087 | 1.62 | 3.332 | 1.062 | 0.173 | −0.264 | −0.206 | −3.547 | 0.0083888 | non-protein coding RNA 87 |
| C7orf44 | 3.125 | 4.764 | 2.318 | 1.033 | 1.305 | 1.936 | −3.531 | 0.0148337 | chromosome 7 open reading frame 44 |
| CTSO | 6.535 | 6.192 | 6.386 | 4.209 | 5.068 | 4.573 | −3.513 | 0.0020913 | cathepsin O |
| RAP2A | 6.505 | 8.5 | 7.537 | 5.726 | 5.486 | 6.056 | −3.507 | 0.0128497 | RAP2A, member of RAS oncogene family |
| ANK2 | 5.426 | 3.609 | 4.918 | 2.727 | 2.882 | 3.619 | −3.499 | 0.0214574 | ankyrin 2, neuronal |
| FGF12 | 3.083 | 1.601 | 3.011 | 0.573 | 0.609 | 1.277 | −3.496 | 0.0098447 | fibroblast growth factor 12 |
| HS3ST1 | 3.827 | 6.975 | 4.987 | 3.182 | 3.643 | 2.643 | −3.495 | 0.0213272 | heparan sulfate (glucosamine) 3-O-sulfotransferase 1 |

TABLE 6-continued

Differentially Expressed Genes in CD10+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD24+ N48 | CD24+ N58 | CD24+ N43 | CD24+ N37 | CD24+ N39 | CD24+ N40 | | | | |
| LGALS3BP | 8.428 | 6.888 | 8.019 | 5.952 | 6.33 | 6.218 | -3.486 | 0.0106439 | lectin, galactoside-binding, soluble, 3 binding protein |
| ASPH | 7.776 | 8.964 | 8.404 | 6.589 | 6.604 | 6.642 | -3.483 | 0.003362 | aspartate beta-hydroxylase |
| PRSS23 | 6.451 | 6.84 | 6.046 | 4.127 | 4.661 | 5.041 | -3.479 | 0.0029634 | protease, serine, 23 |
| ID4 | 6.091 | 9.385 | 7.404 | 5.288 | 5.61 | 5.938 | -3.468 | 0.0267439 | Description |
| MST4 | 6.212 | 9.384 | 7.694 | 5.929 | 5.423 | 5.903 | -3.462 | 0.0233777 | No description |
| FAM43A | 7.006 | 7.363 | 5.864 | 4.983 | 5.216 | 5.326 | -3.457 | 0.0114309 | family with sequence similarity 43, member A |
| SH3BGRL | 7.653 | 9.124 | 8.936 | 6.553 | 7.232 | 7.148 | -3.454 | 0.01347 | SH3 domain binding glutamic acid-rich protein like |
| IL3RA | 5.049 | 3.928 | 2.281 | 1.525 | 2.291 | 2.141 | -3.451 | 0.0302304 | interleukin 3 receptor, alpha (low affinity) |
| LOC729156 | 3.443 | 2.882 | 4.095 | 2.309 | 0.924 | 1.827 | -3.45 | 0.0089647 | No description |
| C7orf60 | 3.621 | 5.725 | 5.177 | 3.391 | 3.363 | 3.489 | -3.45 | 0.0354053 | chromosome 7 open reading frame 60 |
| TRIM5 | 4.614 | 5.55 | 5.484 | 2.994 | 3.767 | 3.086 | -3.442 | 0.0027839 | tripartite motif-containing 5 |
| ARL6IP5 | 7.078 | 7.444 | 7.522 | 4.887 | 5.74 | 5.671 | -3.44 | 0.0017057 | ADP-ribosylation-like factor 6 interacting protein 5 |
| HOPX | 1.826 | 2.282 | 1.575 | 0.415 | 0.283 | -0.206 | -3.437 | 0.0024011 | HOP homeobox |
| F2R | 4.843 | 3.808 | 6.084 | 2.454 | 3.404 | 3.064 | -3.434 | 0.0132689 | coagulation factor II (thrombin) receptor |
| RAB15 | 7.285 | 8.959 | 8.932 | 7.179 | 6.205 | 6.602 | -3.433 | 0.015303 | RAB15, member RAS oncogene family |
| TMEM59L | 1.596 | 2.399 | 2.029 | 0.573 | 0.17 | 0.251 | -3.43 | 0.0024934 | transmembrane protein 59-like |
| AKR7A2 | 4.245 | 5.551 | 4.557 | 2.4 | 3.469 | 3.773 | -3.43 | 0.0189132 | aldo-keto reductase family 7, member A2 (aflatoxin aldehyde reductase) |
| GLYATL2 | 2.06 | 3.16 | 3.48 | 0.924 | 0.283 | 2.493 | -3.427 | 0.0321893 | glycine-N-acyltransferase-like 2 |
| LHFPL2 | 9.372 | 8.015 | 9.634 | 7.547 | 7.799 | 7.598 | -3.421 | 0.0264971 | lipoma HMGIC fusion partner-like 2 |
| ITGB1BP1 | 4.09 | 3.92 | 4.579 | 3.141 | 2.146 | 2.235 | -3.418 | 0.0049095 | integrin beta 1 binding protein 1 |
| FBLN5 | 6.866 | 6.049 | 8.513 | 4.276 | 5.66 | 5.675 | -3.418 | 0.022009 | fibulin 5 |
| ESM1 | 7.362 | 3.517 | 2.053 | 1.556 | 2.04 | 1.747 | -3.411 | 0.0448566 | endothelial cell-specific molecule 1 |
| PJA2 | 7.332 | 9.182 | 8.402 | 6.391 | 7.01 | 6.632 | -3.41 | 0.0157845 | praja ring finger 2 |
| IL15RA | 7.173 | 6.299 | 7.15 | 5.146 | 4.976 | 5.404 | -3.409 | 0.0034049 | interleukin 15 receptor, alpha |
| MTERFD3 | 3.915 | 4.231 | 4.751 | 3.71 | 2.42 | 2.146 | -3.407 | 0.0180024 | MTERF domain containing 3 |
| SH3KBP1 | 4.952 | 4.143 | 6.189 | 3.387 | 2.646 | 3.184 | -3.405 | 0.0077713 | SH3-domain kinase binding protein 1 |
| NCDN | 5.884 | 7.27 | 7.902 | 5.503 | 5.367 | 5.64 | -3.403 | 0.0246505 | neurochondrin |
| ANKMY2 | 5.867 | 6.335 | 6.446 | 4.1 | 5.789 | 4.555 | -3.403 | 0.026236 | ankyrin repeat and MYND domain containing 2 |
| PLEKHG1 | 6.172 | 5.092 | 5.049 | 3.283 | 3.875 | 3.636 | -3.399 | 0.0039358 | pleckstrin homology domain containing, family G (with RhoGef domain) member 1 |
| LOC389493 | 2.504 | 5.072 | 4.873 | 1.471 | 1.49 | 3.309 | -3.394 | 0.0280997 | No description |
| PLXDC1 | 7.133 | 6.109 | 9.023 | 4.975 | 5.838 | 5.372 | -3.39 | 0.0199735 | plexin domain containing 1 |
| DENND5A | 7.893 | 9.52 | 9.305 | 7.548 | 7.472 | 7.546 | -3.384 | 0.0248365 | DENN/MADD domain containing 5A |
| GIMAP2 | 2.618 | 0.978 | 3.244 | 0.86 | 0.515 | 1.244 | -3.381 | 0.0485075 | GTPase, IMAP family member 2 |
| OAS1 | 2.329 | 0.701 | 2.169 | 0.573 | 0.17 | 0.251 | -3.378 | 0.0259376 | 2',5'-oligoadenylate synthetase 1, 40/46 kDa |
| SECTM1 | 4.954 | 2.826 | 4.145 | 3.055 | 1.07 | 2.763 | -3.378 | 0.0416642 | secreted and transmembrane 1 |
| CHRNE | 5.606 | 6.828 | 6.215 | 4.485 | 4.068 | 4.459 | -3.376 | 0.003123 | cholinergic receptor, nicotinic, epsilon |
| ZNF280D | 3.495 | 4.161 | 4.299 | 2.406 | 2.406 | 2.167 | -3.375 | 0.0026365 | zinc finger protein 280D |
| GPRC5B | 4.826 | 3.823 | 2.909 | 1.999 | 2.298 | 2.071 | -3.368 | 0.0115955 | G protein-coupled receptor, family C, group 5, member B |
| LRRTM2 | 2.782 | 4.624 | 4.307 | 2.46 | 2.556 | 2.828 | -3.365 | 0.0435702 | leucine rich repeat transmembrane neuronal 2 |
| GALK2 | 2.841 | 4.967 | 4.573 | 2.301 | 2.592 | 3.217 | -3.365 | 0.0463926 | galactokinase 2 |

TABLE 6-continued

Differentially Expressed Genes in CD10+ Breast Epithelial Cells

| Gene Symbol | Nulliparous (NP) Samples | | Parous (P) Samples | | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| GXYLT2 | 2.584 | 4.104 | 4.292 | 2.354 | 2.497 | 1.486 | −3.363 | 0.0249073 | glucoside xylosyltransferase 2 |
| PPFIA1 | 8.163 | 10.483 | 9.912 | 8.166 | 7.784 | 8.179 | −3.356 | 0.0409094 | protein tyrosine phosphatase, receptor type, f polypeptide (PTPRF), interacting protein (liprin), alpha 1 |
| HEXA | 5.643 | 6.529 | 6.455 | 4.786 | 4.647 | 4.294 | −3.348 | 0.0042162 | hexosaminidase A (alpha polypeptide) |
| SUCLG2 | 4.033 | 5.341 | 4.321 | 2.293 | 3.051 | 3.175 | −3.34 | 0.0081205 | succinate-CoA ligase, GDP-forming, beta subunit |
| PAFAH1B3 | 3.044 | 4.517 | 2.917 | 1.623 | 1.305 | 1.277 | −3.338 | 0.003993 | platelet-activating factor acetylhydrolase 1b, catalytic subunit 3 (29kDa) |
| TMEM130 | 2.947 | 3.871 | 5.49 | 1.299 | 2.132 | 2.348 | −3.338 | 0.0111154 | transmembrane protein 130 |
| ANGPTL1 | 2.895 | 3.435 | 4.862 | 1.698 | 1.408 | 2.19 | −3.334 | 0.0086972 | angiopoietin-like 1 |
| TMEM109 | 6.722 | 8.29 | 7.974 | 6.237 | 6.002 | 6.32 | −3.332 | 0.0170502 | transmembrane protein 109 |
| VCAN | 6.771 | 5.693 | 8.444 | 4.626 | 5.331 | 5.041 | −3.317 | 0.0184453 | versican |
| SLC27A6 | 4.483 | 5.8 | 4.708 | 3.19 | 2.755 | 3.465 | −3.313 | 0.0048644 | solute carrier family 27 (fatty acid transporter), member 6 |
| DEPDC6 | 3.742 | 4.967 | 5.191 | 3.373 | 2.686 | 3.239 | −3.313 | 0.0151048 | No description |
| WASL | 7.532 | 9.111 | 9.223 | 7.185 | 7.384 | 7.383 | −3.313 | 0.0371711 | Wiskott-Aldrich syndrome-like |
| OLFM1 | 4.597 | 3.729 | 4.08 | 2.502 | 2.571 | 2.004 | −3.306 | 0.0025764 | olfactomedin 1 |
| CCDC153 | 2.118 | 2.616 | 1.408 | −0.311 | 1.198 | 0.327 | −3.293 | 0.0148265 | coiled-coil domain containing 153 |
| DCX | 2.697 | 4.361 | 5.478 | 2.642 | 2.377 | 2.824 | −3.293 | 0.0459605 | doublecortin |
| KCTD17 | 3.377 | 3.368 | 3.662 | 2.005 | 1.374 | 1.66 | −3.288 | 0.0011526 | potassium channel tetramerisation domain containing 17 |
| NEK7 | 6.453 | 7.858 | 7.698 | 5.862 | 5.643 | 6.144 | −3.28 | 0.01652 | NIMA (never in mitosis gene a)-related kinase 7 |
| EMB | 2.526 | 4.1 | 3.499 | 1.846 | 0.814 | 2.176 | −3.275 | 0.013641 | embigin |
| GP1BB | 2.021 | 1.699 | 1.148 | −0.824 | 0.647 | −0.012 | −3.272 | 0.0096888 | glycoprotein 1b (platelet), beta polypeptide |
| LOX | 4.809 | 4.147 | 5.062 | 2.995 | 3.352 | 3.002 | −3.27 | 0.0045811 | lysyl oxidase |
| TBC1D1 | 6.584 | 5.64 | 4.819 | 4.204 | 3.799 | 3.933 | −3.263 | 0.0105717 | TBC1 (tre-2/USP6, BUB2, cdc16) domain family, member 1 |
| NMI | 2.747 | 3.142 | 4.368 | 1.723 | 1.07 | 1.436 | −3.261 | 0.0047328 | N-myc (and STAT) interactor |
| LOC1001909 39 | 6.28 | 6.391 | 6.363 | 5.545 | 4.579 | 4.579 | −3.253 | 0.0078128 | No description |
| EGR2 | 7.96 | 9.783 | 9.427 | 6.509 | 7.917 | 7.727 | −3.247 | 0.0247349 | early growth response 2 |
| NXPH3 | 3.874 | 3.105 | 3.397 | 1.698 | 1.408 | 2.016 | −3.246 | 0.0023381 | neurexophilin 3 |
| ARMCX1 | 5.305 | 6.286 | 6.542 | 4.57 | 4.542 | 4.843 | −3.246 | 0.0135687 | armadillo repeat containing, X-linked 1 |
| LDHA | 10.756 | 12.752 | 12.285 | 10.588 | 10.148 | 10.617 | −3.244 | 0.0294863 | lactate dehydrogenase A |
| RBM7 | 6.056 | 7.82 | 7.372 | 5.48 | 5.675 | 5.803 | −3.241 | 0.0241067 | RNA binding motif protein 7 |
| TWSG1 | 6.707 | 8.285 | 8.382 | 6.007 | 6.586 | 6.686 | −3.24 | 0.0352071 | twisted gastrulation homolog 1 (Drosophila) |
| NR2F1 | 3.294 | 3.026 | 3.164 | 1.065 | 1.471 | 2.721 | −3.233 | 0.0233002 | nuclear receptor subfamily 2, group F, member 1 |
| SLC25A46 | 3.626 | 4.474 | 3.856 | 2.781 | 1.873 | 2.575 | −3.232 | 0.0068598 | solute carrier family 25, member 46 |
| DBI | 6.083 | 8.884 | 7.38 | 5.689 | 5.267 | 6.003 | −3.231 | 0.0281462 | diazepam binding inhibitor (GABA receptor modulator, acyl-CoA binding protein) |
| SPARCL1 | 10.765 | 11.159 | 11.134 | 9.083 | 9.242 | 9.534 | −3.207 | 0.0011311 | SPARC-like 1 (hevin) |
| CDKN1B | 6.105 | 7.994 | 7.463 | 4.981 | 6.07 | 5.782 | −3.206 | 0.0253087 | cyclin-dependent kinase inhibitor 1 B (p27, Kip1) |
| TP53INP1 | 4.239 | 4.329 | 4.601 | 2.565 | 2.56 | 3.214 | −3.202 | 0.002678 | tumor protein p53 inducible nuclear protein 1 |
| CCBL2 | 3.682 | 6.13 | 5.097 | 3.427 | 3.168 | 3.52 | −3.183 | 0.030538 | cysteine conjugate-beta lyase 2 |
| RFTN1 | 5.39 | 2.493 | 3.466 | 2.039 | 1.651 | 1.797 | −3.181 | 0.0211991 | raftlin, lipid raft linker 1 |
| IFITM1 | 9.662 | 7.706 | 8.718 | 6.354 | 7.279 | 7.053 | −3.171 | 0.0132139 | interferon induced transmembrane protein 1 (9-27) |
| C1orf61 | 5.306 | 6.926 | 5.741 | 4.076 | 4.271 | 4.062 | −3.17 | 0.0058303 | chromosome 1 open reading frame 61 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| CRYL1 | 2.785 | 1.931 | 3.254 | 1.121 | 0.814 | 1.334 | -3.169 | 0.0090062 | crystallin, lambda 1 |
| GNG2 | 2.454 | 3.239 | 4.378 | 1.698 | 1.575 | 1.568 | -3.168 | 0.0112327 | guanine nucleotide binding protein (G protein), gamma 2 |
| NUDT7 | 1.563 | 2.861 | 1.612 | -0.104 | 1.198 | 0.327 | -3.166 | 0.0204729 | nudix (nucleoside diphosphate linked moiety X)-type motif 7 |
| ZNF76 | 3.952 | 5.291 | 5.861 | 3.293 | 3.882 | 3.628 | -3.166 | 0.0299513 | zinc finger protein 76 (expressed in testis) |
| PIR | 3.319 | 2.853 | 3.483 | 0.86 | 2.008 | 1.66 | -3.158 | 0.005059 | pirin (iron-binding nuclear protein) |
| FNDC3B | 8.698 | 10.406 | 9.794 | 8.134 | 8.093 | 8.156 | -3.158 | 0.0165751 | fibronectin type III domain containing 3B |
| GUCY1B3 | 3.565 | 3.727 | 4.374 | 2.132 | 1.907 | 2.187 | -3.157 | 0.0016713 | guanylate cyclase 1, soluble, beta 3 |
| F8 | 4.532 | 3.478 | 2.36 | 1.478 | 1.82 | 1.999 | -3.156 | 0.0185033 | coagulation factor VIII, procoagulant component |
| VASN | 7.894 | 7.567 | 8.186 | 5.91 | 6.503 | 6.252 | -3.154 | 0.0023553 | vasorin |
| CFI | 6.01 | 6.904 | 6.183 | 4.132 | 5.248 | 4.785 | -3.152 | 0.0074437 | complement factor I |
| EGFL6 | 1.826 | 0.78 | 3.047 | 0.173 | 0.283 | -0.206 | -3.144 | 0.0156564 | EGF-like-domain, multiple 6 |
| TCF19 | 2.061 | 3.573 | 2.494 | 0.573 | 0.875 | 0.842 | -3.142 | 0.0040145 | transcription factor 19 |
| LOH3CR2A | 3.845 | 2.33 | 3.26 | 1.494 | 1.873 | 1.609 | -3.142 | 0.0141139 | loss of heterozygosity, 3, chromosomal region 2, gene A |
| TPT1 | 12.027 | 13.62 | 13.476 | 11.785 | 11.731 | 11.968 | -3.142 | 0.0428239 | tumor protein, translationally-controlled 1 |
| KLRAQ1 | 2.68 | 4.738 | 4.441 | 3.087 | 1.959 | 2.409 | -3.141 | 0.043304 | KLRAQ motif containing 1 |
| C1orf133 | 5.009 | 7.002 | 6.257 | 3.586 | 4.839 | 4.616 | -3.12 | 0.0197875 | chromosome 1 open reading frame 133 |
| C4orf33 | 2.564 | 3.097 | 3.184 | 0.762 | 2.444 | 1.456 | -3.119 | 0.0256479 | chromosome 4 open reading frame 33 |
| ERGIC1 | 6.572 | 7.146 | 6.583 | 5.205 | 4.899 | 5.505 | -3.117 | 0.0035601 | endoplasmic reticulum-golgi intermediate compartment (ERGIC) 1 |
| SFRP5 | 2.533 | 2.868 | 1.928 | 1.228 | 0.695 | 0.713 | -3.117 | 0.005371 | secreted frizzled-related protein 5 |
| TP53I3 | 4.724 | 5.697 | 5.452 | 4.056 | 3.646 | 3.125 | -3.117 | 0.0057065 | tumor protein p53 inducible protein 3 |
| JUN | 11.939 | 13.854 | 13.365 | 10.857 | 11.98 | 11.725 | -3.117 | 0.0303899 | jun proto-oncogene |
| MMP16 | 4.232 | 3.787 | 4.851 | 2.806 | 2.556 | 2.592 | -3.116 | 0.0041225 | matrix metallopeptidase 16 (membrane-inserted) |
| GPR137C | 3.31 | 4.069 | 3.518 | 2.358 | 1.575 | 2.43 | -3.116 | 0.0075295 | G protein-coupled receptor 137C |
| DMXL2 | 2.047 | 3.296 | 2.988 | 1.366 | 1.033 | 1.348 | -3.116 | 0.0088302 | Dmx-like 2 |
| ITM2C | 5.257 | 7.414 | 6.399 | 4.811 | 4.237 | 4.764 | -3.105 | 0.0160814 | integral membrane protein 2C |
| NEUROG2 | 2.667 | 4.901 | 3.345 | 1.033 | 2.612 | 2.026 | -3.104 | 0.0285262 | neurogenin 2 |
| ABCD3 | 6.751 | 8.53 | 8.045 | 6.312 | 6.412 | 6.51 | -3.103 | 0.0291357 | ATP-binding cassette, sub-family D (ALD), member 3 |
| C18orf1 | 3.37 | 5.439 | 4.743 | 3 | 3.109 | 3.264 | -3.103 | 0.0364434 | chromosome 18 open reading frame 1 |
| LRP1 | 11.001 | 9.368 | 10.866 | 8.241 | 9.294 | 8.737 | -3.092 | 0.022889 | low density lipoprotein receptor-related protein 1 |
| TSHZ1 | 6.317 | 5.338 | 6.214 | 4.32 | 4.69 | 4.358 | -3.089 | 0.006794 | teashirt zinc finger homeobox 1 |
| DAB2 | 9.061 | 8.834 | 9.345 | 7.186 | 7.723 | 7.504 | -3.079 | 0.0021893 | disabled homolog 2, mitogen-responsive phosphoprotein (Drosophila) |
| TMEM176A | 1.334 | 2.194 | 4.713 | 0.573 | 0.609 | 0.251 | -3.078 | 0.0184038 | transmembrane protein 176A |
| C1GALT1C1 | 1.467 | 2.546 | 2.459 | 0.573 | 0.924 | 0.552 | -3.077 | 0.0091343 | C1GALT1-specific chaperone 1 |
| ZNF92 | 2.983 | 4.632 | 3.099 | 2.999 | 1.362 | 1.999 | -3.077 | 0.0442405 | zinc finger protein 92 |
| PIM1 | 5.28 | 5.316 | 6.131 | 3.42 | 4.511 | 4.454 | -3.074 | 0.015635 | pim-1 oncogene |
| C20orf191 | 2.832 | 2.292 | 0.814 | 0.673 | -0.012 | 0.831 | -3.072 | 0.0333133 | chromosome 20 open reading frame 191 |
| HSPB2 | 5.194 | 6.896 | 6.067 | 4.448 | 4.716 | 4.446 | -3.071 | 0.0159948 | heat shock 27kDa protein 2 |
| KIAA0528 | 2.859 | 4.317 | 4.632 | 2.008 | 3.014 | 2.391 | -3.07 | 0.0305065 | KIAA0528 |
| CX3CL1 | 9.938 | 8.843 | 10.157 | 7.938 | 8.336 | 8.32 | -3.069 | 0.013852 | chemokine (C-X3-C motif) ligand 1 |
| C19orf62 | 4.666 | 6.137 | 5.991 | 4.519 | 3.925 | 4.199 | -3.069 | 0.0233906 | chromosome 19 open reading frame 62 |
| IGF1 | 7.7 | 6.852 | 8.763 | 5.628 | 6.31 | 6.083 | -3.068 | 0.0119153 | insulin-like growth factor 1 (somatomedin C) |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| ART5 | 2.118 | 1.66 | 1.942 | -0.104 | 0.886 | 0.327 | -3.063 | 0.0054561 | ADP-ribosyltransferase 5 |
| TMEM14C | 6.038 | 7.38 | 5.964 | 5.578 | 4.351 | 5.166 | -3.059 | 0.0295185 | transmembrane protein 14C |
| LPCAT4 | 4.698 | 6.047 | 6.298 | 4.435 | 4.567 | 4.33 | -3.058 | 0.0376712 | lysophosphatidylcholine acyltransferase 4 |
| MSX2P1 | 3.26 | 3.102 | 2.888 | 0.967 | 1.49 | 2.439 | -3.057 | 0.0149517 | msh homeobox 2 pseudogene 1 |
| KERA | 2.468 | 3.889 | 3.639 | 1.623 | 2.031 | 2.258 | -3.05 | 0.0227288 | keratocan |
| PIK3R2 | 5.915 | 7.473 | 7.071 | 5.238 | 5.464 | 5.726 | -3.048 | 0.023454 | phosphoinositide-3-kinase, regulatory subunit 2 (beta) |
| MLLT3 | 4.25 | 3.646 | 3.075 | 1.783 | 2.628 | 2.039 | -3.045 | 0.0111512 | myeloid/lymphoid or mixed-lineage leukemia (trithorax homolog, Drosophila); translocated to, 3 |
| HINT2 | 5.412 | 5.149 | 3.431 | 2.886 | 3.806 | 2.208 | -3.044 | 0.0289898 | histidine triad nucleotide binding protein 2 |
| LDLRAD2 | 5.555 | 5.896 | 5.358 | 4.152 | 3.95 | 3.905 | -3.043 | 0.0016427 | low density lipoprotein receptor class A domain containing 2 |
| GALC | 4.944 | 4.543 | 4.664 | 2.937 | 3.558 | 3.015 | -3.043 | 0.0030729 | galactosylceramidase |
| GNG5 | 7.681 | 9.097 | 9.072 | 7.491 | 6.921 | 7.2 | -3.043 | 0.021295 | guanine nucleotide binding protein (G protein), gamma 5 |
| ATPIF1 | 6.45 | 8.718 | 7.859 | 6.097 | 6.254 | 6.507 | -3.042 | 0.0453581 | ATPase inhibitory factor 1 |
| IGFBP4 | 10.82 | 10.293 | 10.443 | 8.689 | 9.083 | 9.132 | -3.041 | 0.0025263 | insulin-like growth factor binding protein 4 |
| VGLL4 | 7.647 | 8.15 | 7.754 | 6.441 | 6.094 | 6.216 | -3.039 | 0.0016041 | vestigial like 4 (Drosophila) |
| CDO1 | 3.77 | 4.41 | 4.55 | 2.593 | 2.242 | 2.947 | -3.039 | 0.0038928 | cysteine dioxygenase, type I |
| TRPS1 | 6.904 | 8.633 | 8.208 | 6.55 | 6.814 | 6.605 | -3.038 | 0.0389189 | trichorhinophalangeal syndrome I |
| RHOXF1 | 1.587 | 1.219 | 2.931 | -0.824 | 1.341 | -0.012 | -3.029 | 0.0300057 | Rhox homeobox family, member 1 |
| COG4 | 4.202 | 5.679 | 6.316 | 3.463 | 3.686 | 3.881 | -3.028 | 0.0198312 | component of oligomeric golgi complex 4 |
| SLC44A2 | 6.351 | 6.148 | 5.883 | 4.016 | 4.73 | 4.754 | -3.026 | 0.003319 | solute carrier family 44, member 2 |
| ALDH7A1 | 7.415 | 9.105 | 8.361 | 5.895 | 6.866 | 6.765 | -3.023 | 0.0108493 | aldehyde dehydrogenase 7 family, member A1 |
| MRGPRF | 5.586 | 4.738 | 4.654 | 3.523 | 3.99 | 3.016 | -3.023 | 0.0112885 | MAS-related GPR, member F |
| IFIT1 | 5.952 | 1.164 | 2.169 | 0.573 | 0.609 | 0.552 | -3.023 | 0.0351807 | interferon-induced protein with tetratricopeptide repeats 1 |
| CLTCL1 | 1.818 | 2.167 | 2.492 | 0.573 | 0.609 | 0.552 | -3.02 | 0.0020634 | clathrin, heavy chain-like 1 |
| LRRC17 | 1.826 | 1.753 | 3.757 | 0.924 | 0.695 | 0.162 | -3.012 | 0.015112 | leucine rich repeat containing 17 |
| HSD17B11 | 7.647 | 4.123 | 5.66 | 3.082 | 4.069 | 4.123 | -3.012 | 0.0325134 | hydroxysteroid (17-beta) dehydrogenase 11 |
| MAP3K12 | 3.211 | 4.579 | 5.232 | 2.853 | 3.221 | 2.99 | -3.008 | 0.0438957 | mitogen-activated protein kinase kinase kinase 12 |
| SCARA3 | 5.564 | 5.743 | 4.483 | 3.9 | 3.975 | 4.019 | -3.007 | 0.0189397 | scavenger receptor class A, member 3 |
| C4orf27 | 3.624 | 3.886 | 3.361 | 1.773 | 2.214 | 2.258 | -3.005 | 0.0027552 | chromosome 4 open reading frame 27 |
| FAM69A | 4.309 | 5.679 | 6.316 | 4.192 | 3.749 | 4.092 | -3.004 | 0.0326136 | family with sequence similarity 69, member A |
| IDH2 | 4.077 | 6.173 | 4.531 | 2.492 | 3.52 | 3.441 | -3 | 0.0195943 | Description |
| TSPAN6 | 5.589 | 4.818 | 5.326 | 3.743 | 3.427 | 3.869 | -2.995 | 0.0036181 | tetraspanin 6 |
| RSPO1 | 1.374 | 1.753 | 2.911 | 0.173 | 0.695 | -0.206 | -2.99 | 0.0085727 | R-spondin homolog (Xenopus laevis) |
| HMGCL | 2.691 | 3.24 | 3.633 | 1.471 | 1.66 | 1.878 | -2.989 | 0.0051685 | 3-hydroxymethyl-3-methylglutaryl-CoA lyase |
| PRKD1 | 2.539 | 4.102 | 4.243 | 2.667 | 1.709 | 2.295 | -2.982 | 0.0352694 | protein kinase D1 |
| TESC | 7.809 | 8.09 | 7.171 | 5.936 | 6.458 | 6.233 | -2.98 | 0.0063776 | tescalcin |
| ITGA11 | 5.869 | 7.503 | 6.477 | 4.759 | 5.045 | 4.902 | -2.98 | 0.008406 | integrin, alpha 11 |
| NDEL1 | 7.654 | 9.08 | 9.547 | 6.992 | 7.507 | 7.562 | -2.974 | 0.0330285 | nudE nuclear distribution gene E homolog (A. nidulans)-like 1 |
| KIAA0652 | 6.144 | 7.407 | 7.971 | 5.156 | 6.117 | 5.836 | -2.972 | 0.0289969 | No description |
| GOLM1 | 5.617 | 5.703 | 6.697 | 4.265 | 4.296 | 4.046 | -2.97 | 0.0032904 | golgi membrane protein 1 |
| LRRC6 | 1.275 | 1.742 | 1.865 | 0.173 | 0.283 | -0.206 | -2.967 | 0.0031902 | leucine rich repeat containing 6 |
| LRRC8C | 7.507 | 8.046 | 7.604 | 6.477 | 5.303 | 6.187 | -2.967 | 0.0048287 | leucine rich repeat containing 8 family, member C |

TABLE 6-continued

Differentially Expressed Genes in CD10+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD24+ N48 | CD24+ N58 | CD24+ N43 | CD24+ N37 | CD24+ N39 | CD24+ N40 | | | | |
| BRP44 | 5.815 | 8.137 | 6.68 | 5.09 | 5.111 | 5.49 | -2.967 | 0.0242842 | brain protein 44 |
| KIAA1755 | 4.804 | 5.854 | 6.379 | 4.171 | 4.81 | 4.253 | -2.967 | 0.0346949 | KIAA1755 |
| ADRA2A | 3.355 | 2.12 | 2.612 | 0.573 | 2.41 | 0.552 | -2.966 | 0.0369922 | adrenergic, alpha-2A-, receptor |
| LGALS3 | 8.713 | 10.243 | 9.889 | 8.332 | 7.577 | 8.323 | -2.962 | 0.0169028 | lectin, galactoside-binding, soluble, 3 |
| MORC3 | 6.39 | 6.909 | 7.509 | 5.344 | 5.339 | 5.768 | -2.959 | 0.0090699 | MORC family CW-type zinc finger 3 |
| TENC1 | 6.72 | 6.5 | 7.664 | 4.935 | 5.903 | 5.6 | -2.959 | 0.0144995 | tensin like C1 domain containing phosphatase (tensin 2) |
| SURF1 | 3.816 | 4.905 | 5.108 | 3.063 | 3.341 | 3.365 | -2.957 | 0.0172626 | surfeit 1 |
| LOC100271831 | 2.792 | 1.699 | 1.847 | -1.775 | 0.647 | 1.228 | -2.957 | 0.0236074 | No description |
| TBX5 | 2.136 | 0.817 | 2.827 | 0.573 | 0.609 | 0.251 | -2.955 | 0.0297396 | T-box 5 |
| MYOM2 | 1.976 | 3.111 | 3.548 | 0.415 | 1.616 | 1.576 | -2.951 | 0.016799 | myomesin (M-protein) 2, 165kDa |
| C20orf30 | 7.182 | 6.867 | 6.324 | 4.764 | 5.316 | 5.363 | -2.948 | 0.0040073 | chromosome 20 open reading frame 30 |
| TNFRSF19 | 3.017 | 4.248 | 2.993 | 1.659 | 1.434 | 1.886 | -2.947 | 0.00565 | tumor necrosis factor receptor superfamily, member 19 |
| CLEC12A | 2.132 | 2.899 | 3.039 | -0.824 | 1.341 | 1.908 | -2.944 | 0.0265651 | C-type lectin domain family 12, member A |
| INMT | 3.649 | 2.518 | 4.516 | 1.065 | 2.674 | 2.094 | -2.939 | 0.0319139 | indolethylamine N-methyltransferase |
| SENP7 | 3.968 | 4.882 | 5.052 | 2.414 | 2.731 | 3.698 | -2.937 | 0.0103999 | SUMO1/sentrin specific peptidase 7 |
| RARRES2 | 6.411 | 5.784 | 8.121 | 4.232 | 5.682 | 5.68 | -2.932 | 0.0490749 | retinoic acid receptor responder (tazarotene induced) 2 |
| TRMT5 | 8.091 | 8.792 | 8.15 | 6.335 | 6.998 | 7.24 | -2.931 | 0.0080597 | TRM5 tRNA methyltransferase 5 homolog (S. cerevisiae) |
| TBC1D5 | 6.35 | 6.626 | 6.353 | 4.073 | 5.212 | 4.804 | -2.925 | 0.0036467 | TBC1 domain family, members |
| RIPK2 | 6.737 | 8.191 | 8.227 | 6.008 | 6.679 | 6.428 | -2.925 | 0.0300379 | receptor-interacting serine-threonine kinase 2 |
| ATG7 | 6.759 | 6.798 | 6.659 | 5.25 | 4.665 | 5.229 | -2.924 | 0.0014767 | ATG7 autophagy related 7 homolog (S. cerevisiae) |
| BNIP3L | 6.039 | 8.947 | 7.243 | 5.584 | 5.695 | 5.854 | -2.924 | 0.0364163 | BCL2/adenovirus E1B 19kDa interacting protein 3-like |
| WIPF1 | 4.719 | 3.549 | 5.692 | 2.43 | 3.41 | 3.174 | -2.919 | 0.0237676 | WAS/WASL interacting protein family, member 1 |
| SCP2 | 5.287 | 6.495 | 4.931 | 3.743 | 4.191 | 3.671 | -2.916 | 0.0094126 | sterol carrier protein 2 |
| C3orf14 | 4.622 | 5.118 | 3.874 | 3.126 | 2.492 | 3.083 | -2.906 | 0.0072004 | chromosome 3 open reading frame 14 |
| SLC35E2 | 5.157 | 6.212 | 6.737 | 4.407 | 5.199 | 4.564 | -2.905 | 0.0326064 | solute carrier family 35, member E2 |
| SPHAR | 3.979 | 5.724 | 4.687 | 3.076 | 3.303 | 3.149 | -2.904 | 0.0123811 | S-phase response (cyclin related) |
| PCMTD2 | 4.385 | 5.725 | 5.875 | 3.986 | 4.337 | 3.952 | -2.903 | 0.0358961 | protein-L-isoaspartate (D-aspartate) O-methyltransferase domain containing 2 |
| ACTA1 | 2.461 | 3.613 | 3.169 | 0.924 | 1.332 | 2.735 | -2.903 | 0.0379488 | actin, alpha 1, skeletal muscle |
| TBC1D19 | 1.556 | 2.108 | 2.511 | 0.573 | 0.609 | 0.552 | -2.898 | 0.0051342 | TBC1 domain family, member 19 |
| OXCT1 | 4.291 | 5.981 | 5.258 | 4.039 | 2.755 | 3.901 | -2.897 | 0.0218731 | 3-oxoacid CoA transferase 1 |
| LCA5 | 5.033 | 7.46 | 6.268 | 4.144 | 4.764 | 4.733 | -2.897 | 0.024154 | Leber congenital amaurosis 5 |
| UTRN | 6.424 | 7.118 | 6.923 | 5.006 | 5.585 | 5.366 | -2.895 | 0.0044688 | utrophin |
| PITPNC1 | 6.058 | 4.281 | 5.017 | 3.597 | 3.484 | 2.856 | -2.893 | 0.0097174 | phosphatidylinositol transfer protein, cytoplasmic 1 |
| BAT5 | 4.74 | 5.995 | 5.406 | 3.875 | 3.617 | 3.993 | -2.89 | 0.0076562 | No description |
| FBXW4 | 5.338 | 6.896 | 6.701 | 4.921 | 5.17 | 5.177 | -2.889 | 0.0387823 | F-box and WD repeat domain containing 4 |
| FZD10 | 4.66 | 5.231 | 5.625 | 3.131 | 3.934 | 4.029 | -2.886 | 0.0109609 | frizzled homolog 10 (Drosophila) |
| NTRK2 | 8.592 | 9.51 | 8.308 | 6.997 | 7.08 | 7.064 | -2.885 | 0.0038857 | neurotrophic tyrosine kinase, receptor, type 2 |
| RHOBTB1 | 3.244 | 2.876 | 4.154 | 1.715 | 1.456 | 2.609 | -2.885 | 0.018235 | Rho-related BTB domain containing 1 |
| SIPA1L2 | 6.506 | 7.176 | 6.1 | 4.933 | 4.98 | 5.007 | -2.88 | 0.0042377 | signal-induced proliferation-associated 1 like 2 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| B3GNT1 | 5.124 | 6.349 | 6.028 | 3.71 | 4.824 | 4.352 | −2.879 | 0.0142491 | UDP-GlcNAc:betaGal beta-1,3-N-acetylglucosaminyltransferase 1 |
| GPC6 | 4.535 | 5.72 | 5.328 | 4.194 | 3.111 | 3.428 | −2.878 | 0.0105373 | glypican 6 |
| CXCL14 | 11.658 | 12.71 | 12.232 | 10.2 | 11.025 | 10.708 | −2.875 | 0.0079667 | chemokine (C-X-C motif) ligand 14 |
| ENTPD1 | 6.14 | 5.445 | 5.934 | 4.256 | 4.413 | 4.52 | −2.869 | 0.0039143 | ectonucleoside triphosphate diphosphohydrolase 1 |
| GCH1 | 7.381 | 8.752 | 9.121 | 6.795 | 7.233 | 7.494 | −2.866 | 0.0475746 | GTP cyclohydrolase 1 |
| SYNJ2 | 6.6 | 7.685 | 7.271 | 6.167 | 5.646 | 5.621 | −2.864 | 0.0122651 | synaptojanin 2 |
| GMNN | 3.095 | 5.915 | 4.441 | 1.949 | 2.928 | 3.311 | −2.854 | 0.0385433 | geminin, DNA replication inhibitor |
| MAF | 7.693 | 8.55 | 8.619 | 5.887 | 7.129 | 7.038 | −2.853 | 0.0121972 | v-maf musculoaponeurotic fibrosarcoma oncogene homolog (avian) |
| CREB3L2 | 7.3 | 8.051 | 8.276 | 6.541 | 6.471 | 6.577 | −2.849 | 0.0092295 | cAMP responsive element binding protein 3-like 2 |
| TMEM9 | 6.922 | 7.155 | 6.907 | 5.41 | 5.398 | 5.97 | −2.847 | 0.0040502 | transmembrane protein 9 |
| NCOA7 | 8.848 | 10.197 | 9.573 | 7.381 | 8.128 | 8.064 | −2.846 | 0.0080454 | nuclear receptor coactivator 7 |
| TPM1 | 10.137 | 12.285 | 10.993 | 9.485 | 9.319 | 9.815 | −2.845 | 0.0229491 | tropomyosin 1 (alpha) |
| HSDL2 | 4.61 | 4.055 | 5.452 | 3.944 | 2.687 | 3.086 | −2.844 | 0.0228962 | hydroxysteroid dehydrogenase like 2 |
| GAPDH | 10.2 | 11.614 | 11.388 | 9.865 | 9.881 | 10.011 | −2.842 | 0.0390499 | glyceraldehyde-3-phosphate dehydrogenase |
| LIPA | 6.686 | 6.268 | 5.92 | 5.193 | 4.417 | 4.697 | −2.834 | 0.0057337 | lipase A, lysosomal acid, cholesterol esterase |
| STX18 | 3.677 | 5.208 | 5.076 | 3.705 | 2.861 | 3.47 | −2.834 | 0.0367819 | syntaxin 18 |
| DNASE1L3 | 4.915 | 1.19 | 1.826 | −0.311 | 0.886 | 0.327 | −2.83 | 0.0262803 | deoxyribonuclease I-like 3 |
| PSAP | 10.913 | 11.179 | 11.459 | 9.643 | 9.679 | 9.72 | −2.827 | 0.0019847 | prosaposin |
| CGNL1 | 5.14 | 4.909 | 5.13 | 3.28 | 3.63 | 3.86 | −2.827 | 0.0027481 | cingulin-like 1 |
| GLCE | 2.311 | 4.446 | 2.709 | 2.546 | 0.814 | 1.334 | −2.822 | 0.0450705 | glucuronic acid epimerase |
| ZNF354B | 4.03 | 5.188 | 5.485 | 3.692 | 3.794 | 3.007 | −2.821 | 0.0230336 | zinc finger protein 354B |
| TAPT1 | 6.479 | 7.129 | 7.31 | 5.633 | 5.427 | 5.715 | −2.82 | 0.0066352 | transmembrane anterior posterior transformation 1 |
| PNPLA8 | 6.628 | 8.105 | 7.921 | 6.161 | 6.22 | 6.61 | −2.819 | 0.0372104 | patatin-like phospholipase domain containing 8 |
| STS | 4.162 | 3.243 | 4.508 | 2.875 | 2.344 | 2.669 | −2.814 | 0.0175839 | steroid sulfatase (microsomal), isozyme S |
| ITGA1 | 5.215 | 6.285 | 5.256 | 4.455 | 3.723 | 4.197 | −2.811 | 0.0120011 | integrin, alpha 1 |
| ANGPTL2 | 8.351 | 6.77 | 6.876 | 5.484 | 5.713 | 5.279 | −2.81 | 0.007327 | angiopoietin-like 2 |
| IMMP2L | 3.923 | 5.544 | 5.35 | 2.659 | 4.054 | 3.841 | −2.809 | 0.041501 | IMP2 inner mitochondrial membrane peptidase-like (S. cerevisiae) |
| UBA3 | 4.979 | 6.908 | 6.107 | 4.618 | 3.721 | 4.948 | −2.807 | 0.0277284 | ubiquitin-like modifier activating enzyme 3 |
| FAM43B | 4.295 | 2.593 | 2.763 | 1.672 | 1.49 | 1.107 | −2.801 | 0.0100715 | family with sequence similarity 43, member B |
| ZCCHC24 | 7.115 | 7.321 | 7.103 | 5.836 | 5.254 | 5.675 | −2.8 | 0.0018459 | zinc finger, CCHC domain containing 24 |
| ANGPT1 | 2.949 | 4.624 | 3.614 | 2.101 | 2.129 | 2.962 | −2.799 | 0.0360907 | angiopoietin 1 |
| PAPSS1 | 7.044 | 8.393 | 8.085 | 6.318 | 6.623 | 6.601 | −2.797 | 0.019492 | 3′-phosphoadenosine 5′-phosphosulfate synthase 1 |
| PNRC2 | 8.843 | 9.261 | 9.749 | 7.36 | 8.047 | 8.12 | −2.796 | 0.0095714 | proline-rich nuclear receptor coactivator 2 |
| IFFO2 | 10.409 | 12.327 | 11.687 | 10.164 | 10.252 | 10.205 | −2.794 | 0.0440567 | intermediate filament family orphan 2 |
| BTG2 | 8.408 | 9.517 | 9.645 | 7.249 | 8.164 | 7.704 | −2.792 | 0.0156278 | BTG family, member 2 |
| ACVR1 | 6.081 | 7.765 | 7.237 | 6.157 | 5.006 | 5.757 | −2.79 | 0.0353223 | activin A receptor, type I |
| SSC5D | 6.589 | 4.989 | 5.915 | 3.509 | 5.358 | 4.316 | −2.79 | 0.0451513 | No description |
| LIMCH1 | 6.693 | 6.778 | 6.825 | 4.903 | 5.646 | 5.3 | −2.786 | 0.0035036 | LIM and calponin homology domains 1 |
| MAD2L1 | 1.037 | 2.313 | 2.557 | 1.079 | 0.283 | 0.162 | −2.786 | 0.0234242 | MAD2 mitotic arrest deficient-like 1 (yeast) |
| UBAC1 | 4.531 | 6.143 | 5.344 | 4.245 | 3.867 | 3.493 | −2.785 | 0.0192774 | UBA domain containing 1 |
| LRRC32 | 7.736 | 3.703 | 4.676 | 2.226 | 3.483 | 3.318 | −2.783 | 0.0304994 | leucine rich repeat containing 32 |
| AUH | 3.905 | 4.424 | 4.433 | 2.949 | 2.289 | 3.195 | −2.778 | 0.0077506 | AU RNA binding protein/enoyl-CoA hydratase |
| FBXL4 | 2.165 | 3.755 | 3.736 | 1.864 | 1.269 | 2.283 | −2.773 | 0.0331251 | F-box and leucine-rich repeat protein 4 |
| C1R | 10.629 | 9.351 | 10.643 | 8.311 | 9.172 | 8.786 | −2.772 | 0.018969 | complement component 1, r subcomponent |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| TRAPPC2P1 | 4.33 | 5.041 | 4.71 | 3.571 | 3.196 | 3.119 | −2.771 | 0.0055377 | trafficking protein particle complex 2 pseudogene 1 |
| RHOB | 12.248 | 11.165 | 12.347 | 10.24 | 10.777 | 10.818 | −2.771 | 0.0208049 | ras homolog gene family, member B |
| BMPR1A | 4.93 | 6.228 | 6.262 | 4.531 | 4.357 | 4.792 | −2.771 | 0.0301109 | bone morphogenetic protein receptor, type IA |
| DIP2C | 5.682 | 6.917 | 6.555 | 5.085 | 5.298 | 4.956 | −2.77 | 0.019135 | DIP2 disco-interacting protein 2 homolog C (Drosophila) |
| ASTN2 | 5.565 | 7.144 | 6.526 | 5.057 | 4.983 | 5.062 | −2.77 | 0.0200537 | astrotactin 2 |
| PPP2R5B | 5.874 | 8.047 | 6.957 | 5.487 | 5.574 | 5.193 | −2.769 | 0.0266309 | protein phosphatase 2, regulatory subunit B, beta |
| SLC35A1 | 3.415 | 3.856 | 3.997 | 2.136 | 2.528 | 2.254 | −2.768 | 0.0036739 | solute carrier family 35 (CMP-sialic acid transporter), member A1 |
| STX12 | 6.774 | 8.097 | 7.658 | 6.189 | 5.466 | 6.278 | −2.767 | 0.0130607 | syntaxin 12 |
| UBC | 6.684 | 6.154 | 5.197 | 4.687 | 4.294 | 4.939 | −2.766 | 0.0217915 | ubiquitin C |
| IDH1 | 4.042 | 4.411 | 3.938 | 1.741 | 2.575 | 3.083 | −2.763 | 0.0067525 | Description |
| LPAR1 | 6.355 | 5.279 | 6.299 | 4.849 | 4.833 | 4.826 | −2.763 | 0.0260049 | lysophosphatidic acid receptor 1 |
| DENND3 | 5.547 | 3.715 | 4.678 | 2.986 | 3.286 | 3.212 | −2.761 | 0.0205201 | DENN/MADD domain containing 3 |
| LCP2 | 5.37 | 2.898 | 2.922 | 1.659 | 1.434 | 2.228 | −2.76 | 0.0206225 | lymphocyte cytosolic protein 2 (SH2 domain containing leukocyte protein of 76kDa) |
| CTSH | 6.3 | 5.993 | 4.971 | 4.07 | 4.532 | 4.808 | −2.752 | 0.0265901 | cathepsin H |
| SEP12 | 1.936 | 3.043 | 2.492 | 1.623 | 0.17 | 1.033 | −2.75 | 0.0166753 | septin 12 |
| PDE2A | 4.109 | 3.644 | 3.414 | 2.083 | 2.249 | 2.187 | −2.746 | 0.0025406 | phosphodiesterase 2A, cGMP-stimulated |
| RALGPS2 | 4.106 | 5.248 | 5.556 | 3.975 | 3.7 | 3.791 | −2.746 | 0.0404701 | Ral GEF with PH domain and SH3 binding motif 2 |
| POLD4 | 6.401 | 6.346 | 5.68 | 4.894 | 4.501 | 4.925 | −2.737 | 0.0070051 | polymerase (DNA-directed), delta 4 |
| ROPN1 | 1.44 | 3.763 | 1.715 | 0.323 | 0.988 | −0.012 | −2.735 | 0.0201223 | ropporin, rhophilin associated protein 1 |
| EXTL2 | 3.326 | 4.58 | 4.241 | 3.122 | 2.643 | 2.79 | −2.733 | 0.0273807 | exostoses (multiple)-like 2 |
| PLOD1 | 7.003 | 7.03 | 6.366 | 5.029 | 5.555 | 5.578 | −2.728 | 0.0065822 | procollagen-lysine 1, 2-oxoglutarate 5-dioxygenase 1 |
| FAM101A | 4.261 | 4.358 | 3.303 | 2.157 | 2.853 | 2.813 | −2.727 | 0.0160263 | family with sequence similarity 101, member A |
| IPO8 | 5.429 | 6.223 | 5.958 | 4.607 | 4.122 | 4.511 | −2.726 | 0.0054769 | importin 8 |
| LETMD1 | 4.677 | 5.986 | 6.755 | 3.516 | 4.54 | 4.539 | −2.725 | 0.0276626 | LETM1 domain containing 1 |
| BDH2 | 5.163 | 6.227 | 6.128 | 4.394 | 4.783 | 4.61 | −2.722 | 0.0187458 | 3-hydroxybutyrate dehydrogenase, type 2 |
| APBB2 | 6.475 | 5.415 | 6.089 | 4.645 | 4.854 | 4.464 | −2.721 | 0.0115175 | amyloid beta (A4) precursor protein-binding, family B, member 2 |
| CD46 | 7.677 | 8.754 | 8.966 | 6.846 | 7.312 | 7.349 | −2.717 | 0.0225821 | CD46 molecule, complement regulatory protein |
| UBA7 | 6.191 | 5.088 | 6.435 | 3.682 | 4.994 | 4.709 | −2.715 | 0.0273235 | ubiquitin-like modifier activating enzyme 7 |
| SFT2D2 | 2.657 | 2.875 | 1.721 | 1.121 | 0.814 | 1.436 | −2.712 | 0.0193217 | SFT2 domain containing 2 |
| HLA-DQA1 | 7.054 | 1.842 | 2.363 | 1.623 | 0.924 | 0.552 | −2.711 | 0.0405573 | major histocompatibility complex, class II, DQ alpha 1 |
| RTN1 | 4.447 | 5.393 | 4.511 | 3.315 | 3.217 | 3.009 | −2.71 | 0.0045382 | reticulon 1 |
| TSPAN13 | 7.535 | 7.78 | 7.152 | 5.715 | 5.919 | 6.457 | −2.709 | 0.0058017 | tetraspanin 13 |
| HIF1A | 8.234 | 7.913 | 7.107 | 6.682 | 6.446 | 6.475 | −2.709 | 0.0190284 | hypoxia inducible factor 1, alpha subunit (basic helix-loop-helix transcription factor) |
| TTC7B | 4.146 | 5.112 | 5.43 | 3.812 | 3.543 | 3.675 | −2.709 | 0.0244258 | tetratricopeptide repeat domain 7B |
| RCBTB2 | 3.487 | 4.702 | 4.732 | 3.294 | 2.932 | 3.254 | −2.709 | 0.0367024 | regulator of chromosome condensation (RCC1) and BTB (POZ) domain containing protein 2 |
| ALG5 | 4.392 | 4.24 | 3.462 | 2.955 | 2.304 | 2.434 | −2.707 | 0.0084797 | asparagine-linked glycosylation 5, dolichyl-phosphate beta-glucosyltransferase homolog (S. cerevisiae) |
| GHDC | 5.75 | 4.022 | 4.639 | 2.585 | 4.012 | 3.455 | −2.707 | 0.0358718 | GH3 domain containing |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| KDR | 7.26 | 3.682 | 3.604 | 2.246 | 3.536 | 2.242 | −2.705 | 0.0427967 | kinase insert domain receptor (a type III receptor tyrosine kinase) |
| TMEM44 | 4.725 | 4.108 | 5.04 | 3.074 | 3.605 | 3.204 | −2.704 | 0.0110639 | transmembrane protein 44 |
| TF | 5.411 | 6.071 | 7.299 | 3.977 | 5.41 | 5.033 | −2.702 | 0.0420298 | transferrin |
| PPIC | 5.162 | 5.095 | 4.518 | 3.528 | 3.586 | 3.728 | −2.701 | 0.0058897 | peptidylprolyl isomerase C (cyclophilin C) |
| ZNF516 | 5.769 | 7.161 | 6.8 | 5.368 | 5.346 | 5.536 | −2.698 | 0.0343221 | zinc finger protein 516 |
| ZNF577 | 3.238 | 3.938 | 4.713 | 3.176 | 2.509 | 2.406 | −2.694 | 0.032585 | zinc finger protein 577 |
| ZNF521 | 5.307 | 6.148 | 6.588 | 4.481 | 4.721 | 4.812 | −2.689 | 0.015851 | zinc finger protein 521 |
| FNDC1 | 5.132 | 4.555 | 4.589 | 3.802 | 2.721 | 3.168 | −2.678 | 0.0075767 | fibronectin type III domain containing 1 |
| RBKS | 2.504 | 2.528 | 1.033 | −0.104 | −0.104 | 1.107 | −2.678 | 0.0165822 | ribokinase |
| DEGS2 | 2.495 | 3.975 | 2.29 | 0.924 | 1.616 | 1.075 | −2.676 | 0.0126429 | degenerative spermatocyte homolog 2, lipid desaturase (Drosophila) |
| PICALM | 9.361 | 10.823 | 10.356 | 8.937 | 8.716 | 9.022 | −2.674 | 0.0242985 | phosphatidylinositol binding clathrin assembly protein |
| CCPG1 | 5.585 | 6.226 | 5.707 | 4.169 | 4.57 | 4.488 | −2.668 | 0.0044616 | cell cycle progression 1 |
| CDH1 | 10.24 | 11.49 | 10.715 | 9.129 | 9.299 | 9.351 | −2.668 | 0.0071546 | cadherin 1, type 1, E-cadherin (epithelial) |
| CTSF | 8.941 | 7.595 | 8.095 | 6.181 | 7.235 | 7.09 | −2.665 | 0.0258911 | cathepsin F |
| STAT3 | 9.039 | 9.912 | 10.024 | 8.511 | 8.452 | 8.499 | −2.663 | 0.0189569 | signal transducer and activator of transcription 3 (acute-phase response factor) |
| LOC644538 | 2.403 | 2.074 | 2.731 | 0.173 | 2.07 | 0.992 | −2.658 | 0.0395013 | No description |
| TCEAL3 | 2.975 | 3.779 | 4.313 | 1.898 | 2.142 | 2.904 | −2.655 | 0.0235165 | transcription elongation factor A (SII)-like 3 |
| AIP | 4.65 | 5.427 | 7.027 | 4.145 | 3.906 | 4.018 | −2.655 | 0.023548 | aryl hydrocarbon receptor interacting protein |
| PLA2G7 | 2.039 | 4.339 | 2.166 | 1.407 | 1.145 | 0.631 | −2.654 | 0.0236374 | phospholipase A2, group VII (platelet-activating factor acetylhydrolase, plasma) |
| CYB5R3 | 7.93 | 7.792 | 7.173 | 6.232 | 5.958 | 6.523 | −2.651 | 0.007126 | cytochrome b5 reductase 3 |
| VIPAR | 3.28 | 3.164 | 4.157 | 1.757 | 2.497 | 2.31 | −2.65 | 0.0154933 | VPS33B interacting protein, apical-basolateral polarity regulator |
| FAT3 | 2.111 | 2.972 | 3.157 | 1.698 | 1.408 | 1.568 | −2.647 | 0.0199392 | FAT tumor suppressor homolog 3 (Drosophila) |
| FAM188A | 3.34 | 4.385 | 4.808 | 3 | 1.936 | 3.25 | −2.646 | 0.0288753 | family with sequence similarity 188, member A |
| PIK3CA | 5.581 | 6.731 | 7.019 | 5.616 | 5.167 | 5.238 | −2.645 | 0.0492967 | phosphoinositide-3-kinase, catalytic, alpha polypeptide |
| DNAH1 | 3.246 | 4.628 | 3.713 | 2.163 | 2.311 | 2.916 | −2.644 | 0.0193983 | dynein, axonemal, heavy chain 1 |
| EPB41L4B | 3.428 | 5.511 | 4.234 | 2.832 | 2.7 | 3.247 | −2.642 | 0.0315218 | erythrocyte membrane protein band 4.1 like 4B |
| ABCA1 | 5.97 | 5.437 | 6.342 | 4.547 | 4.569 | 4.694 | −2.64 | 0.0085204 | ATP-binding cassette, sub-family A (ABC1), member 1 |
| AZIN1 | 8.145 | 9.04 | 8.82 | 7.481 | 7.31 | 7.419 | −2.639 | 0.0106561 | antizyme inhibitor 1 |
| SLC25A30 | 5.177 | 7.325 | 6.015 | 4.911 | 3.78 | 4.614 | −2.639 | 0.0210102 | solute carrier family 25, member 30 |
| PTGIS | 4.885 | 2.415 | 3.608 | 2.214 | 1.976 | 2.242 | −2.628 | 0.0403549 | prostaglandin I2 (prostacyclin) synthase |
| ADAMTS1 | 8.755 | 11.314 | 9.907 | 7.811 | 8.696 | 8.513 | −2.627 | 0.0337877 | ADAM metallopeptidase with thrombospondin type 1 motif, 1 |
| ITPR1 | 6.842 | 9.636 | 7.911 | 5.919 | 6.52 | 6.53 | −2.624 | 0.0276483 | inositol 1,4,5-triphosphate receptor, type 1 |
| BMP2K | 4.776 | 6.105 | 6.012 | 4.714 | 4.461 | 4.144 | −2.624 | 0.0365136 | BMP2 inducible kinase |
| KCNJ8 | 3.38 | 1.858 | 2.668 | 0.573 | 1.305 | 1.277 | −2.622 | 0.0132833 | potassium inwardly-rectifying channel, subfamily J, member 8 |
| ZNF792 | 4.2 | 0.82 | 1.674 | 0.173 | 0.283 | 0.478 | −2.622 | 0.0366416 | zinc finger protein 792 |
| NAGK | 5.856 | 7.386 | 6.864 | 5.808 | 5.342 | 5.474 | −2.621 | 0.0424984 | N-acetylglucosamine kinase |
| TBC1D4 | 9.008 | 10.004 | 10.538 | 7.974 | 9.015 | 8.614 | −2.619 | 0.034702 | TBC1 domain family, member 4 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| ASAH1 | 5.255 | 6.911 | 5.287 | 3.869 | 4.298 | 3.973 | −2.614 | 0.0104364 | N-acylsphingosine amidohydrolase (acid ceramidase) 1 |
| ARHGAP6 | 3.461 | 2.662 | 3.869 | 1.942 | 2.483 | 1.966 | −2.614 | 0.0266116 | Rho GTPase activating protein 6 |
| IGSF1 | 1.077 | 2.204 | 1.936 | 0.573 | 0.17 | 0.552 | −2.611 | 0.0157416 | immunoglobulin superfamily, member 1 |
| RHOQ | 8.689 | 9.507 | 9.698 | 7.884 | 8.19 | 8.123 | −2.61 | 0.0161651 | ras homolog gene family, member Q |
| SDCBP | 8.233 | 7.502 | 7.278 | 6.473 | 5.894 | 6.408 | −2.609 | 0.0096573 | syndecan binding protein (syntenin) |
| FAM8A1 | 6.676 | 6.973 | 6.258 | 4.874 | 5.484 | 5.585 | −2.609 | 0.0104507 | family with sequence similarity 8, member A1 |
| CNPY4 | 5.491 | 5.103 | 5.671 | 3.717 | 4.605 | 4.108 | −2.609 | 0.0123524 | canopy 4 homolog (zebrafish) |
| PLD1 | 5.361 | 5.919 | 5.905 | 3.883 | 5.269 | 4.521 | −2.609 | 0.0362395 | phospholipase D1, phosphatidylcholine-specific |
| CIC | 7.857 | 9.305 | 8.424 | 6.836 | 7.049 | 7.042 | −2.606 | 0.0099485 | capicua homolog (Drosophila) |
| SGK223 | 7.016 | 7.384 | 6.355 | 5.36 | 5.696 | 5.636 | −2.603 | 0.0102468 | No description |
| BASP1 | 9.616 | 9.332 | 8.695 | 7.248 | 8.631 | 7.951 | −2.603 | 0.0313458 | brain abundant, membrane attached signal protein 1 |
| FBXL5 | 4.152 | 5.618 | 5.169 | 4.17 | 3.55 | 3.791 | −2.599 | 0.0450047 | F-box and leucine-rich repeat protein 5 |
| GAN | 5.687 | 7.28 | 6.945 | 5.567 | 4.717 | 5.649 | −2.598 | 0.0376247 | gigaxonin |
| PPM1M | 5.293 | 4.663 | 5.394 | 3.287 | 4.396 | 3.77 | −2.597 | 0.0187794 | protein phosphatase, Mg2+/Mn2+ dependent, 1M |
| AMACR | 1.684 | 2.539 | 2.819 | 1.121 | 1.362 | 1.163 | −2.596 | 0.0268248 | alpha-methylacyl-CoA racemase |
| SCCPDH | 3.168 | 1.408 | 2.307 | 1.299 | 0.814 | 0.935 | −2.588 | 0.0370137 | saccharopine dehydrogenase (putative) |
| DOCK1 | 6.09 | 6.519 | 5.9 | 5.147 | 4.432 | 5.029 | −2.587 | 0.0102325 | dedicator of cytokinesis 1 |
| PDP1 | 5.901 | 6.759 | 7.341 | 5.253 | 5.677 | 5.389 | −2.586 | 0.0293647 | pyruvate dehydrogenase phosphatase catalytic subunit 1 |
| ALDH1A1 | 3.079 | 3.046 | 4.864 | 2.008 | 1.989 | 1.676 | −2.585 | 0.0129813 | aldehyde dehydrogenase 1 family, member A1 |
| NCEH1 | 5.32 | 7.494 | 6.433 | 5.229 | 4.785 | 5.063 | −2.585 | 0.0406876 | neutral cholesterol ester hydrolase 1 |
| NCAPG2 | 2.196 | 3.193 | 3.72 | 1.875 | 1.562 | 1.824 | −2.584 | 0.0269342 | non-SMC condensin II complex, subunit G2 |
| PFKFB2 | 7.349 | 9.472 | 8.384 | 6.702 | 7.225 | 7.015 | −2.582 | 0.0360979 | 6-phosphofructo-2-kinase/fructose-2,6-biphosphatase 2 |
| HMGN3 | 7.143 | 7.812 | 7.792 | 5.775 | 6.582 | 6.345 | −2.581 | 0.0108278 | high mobility group nucleosomal binding domain 3 |
| CYP27A1 | 5.94 | 7.54 | 6.166 | 4.649 | 4.801 | 5.032 | −2.576 | 0.0094784 | cytochrome P450, family 27, subfamily A, polypeptide 1 |
| LMBRD1 | 3.122 | 2.436 | 3.946 | 1.757 | 2.025 | 1.66 | −2.576 | 0.0205817 | LMBR1 domain containing 1 |
| EIF2S3 | 7.385 | 8.64 | 8.6 | 7.276 | 6.963 | 7.075 | −2.574 | 0.0419439 | eukaryotic translation initiation factor 2, subunit 3 gamma, 52kDa |
| SERPINE1 | 10.169 | 9.738 | 11.025 | 8.656 | 8.811 | 9.153 | −2.563 | 0.0126916 | serpin peptidase inhibitor, clade E (nexin, plasminogen activator inhibitor type 1), member 1 |
| MTIF3 | 3.336 | 3.693 | 3.973 | 2.219 | 3.066 | 1.98 | −2.56 | 0.020596 | mitochondrial translational initiation factor 3 |
| EFHC2 | 2.171 | 3.438 | 2.633 | 2.064 | 0.814 | 1.436 | −2.56 | 0.0319546 | EF-hand domain (C-terminal) containing 2 |
| TUBA1A | 9.844 | 10.547 | 9.199 | 7.926 | 8.489 | 8.671 | −2.558 | 0.0131359 | tubulin, alpha 1a |
| PLA2G4A | 3.568 | 5.356 | 3.896 | 2.488 | 2.543 | 2.546 | −2.556 | 0.0105516 | phospholipase A2, group IVA (cytosolic, calcium-dependent) |
| RUNX1T1 | 3.296 | 3.344 | 4.731 | 1.942 | 2.401 | 2.798 | −2.556 | 0.0250998 | runt-related transcription factor 1; translocated to, 1 (cyclin D-related) |
| PARVA | 7.062 | 8.142 | 7.833 | 6.479 | 6.475 | 6.48 | −2.555 | 0.0180096 | parvin, alpha |
| AGAP3 | 8.374 | 8.499 | 8.907 | 7.274 | 7.132 | 7.147 | −2.553 | 0.0030586 | ArfGAP with GTPase domain, ankyrin repeat and PH domain 3 |
| KLHL13 | 6.696 | 8.868 | 6.821 | 5.838 | 5.344 | 6.006 | −2.553 | 0.0228225 | kelch-like 13 (Drosophila) |
| HIBADH | 3.289 | 5.374 | 4.095 | 2.742 | 2.418 | 2.936 | −2.553 | 0.0243178 | 3-hydroxyisobutyrate dehydrogenase |
| HEPACAM | 3.107 | 2.491 | 1.589 | 1.407 | 0.515 | 1.138 | −2.553 | 0.0259784 | hepatocyte cell adhesion molecule |

TABLE 6-continued

Differentially Expressed Genes in CD10+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD24+ N48 | CD24+ N58 | CD24+ N43 | CD24+ N37 | CD24+ N39 | CD24+ N40 | | | | |
| SERPING1 | 9.026 | 9.284 | 9.092 | 7.49 | 7.934 | 7.759 | -2.549 | 0.0025835 | serpin peptidase inhibitor, clade G (C1 inhibitor), member 1 |
| LOC441204 | 0.726 | 1.923 | 1.88 | 0.573 | 0.17 | 0.251 | -2.549 | 0.0306876 | No description |
| C9orf46 | 3.899 | 4.896 | 4.191 | 3.695 | 2.313 | 2.841 | -2.548 | 0.023842 | chromosome 9 open reading frame 46 |
| BZW2 | 7.279 | 8.163 | 8.018 | 6.814 | 6.243 | 6.559 | -2.547 | 0.013402 | basic leucine zipper and W2 domains 2 |
| HEYL | 3.829 | 2.37 | 3.066 | 1.366 | 2.481 | 1.201 | -2.545 | 0.0312928 | hairy/enhancer-of-split related with YRPW motif-like |
| KRT14 | 16.031 | 16.031 | 15.235 | 14.495 | 14.684 | 14.684 | -2.544 | 0.0166609 | keratin 14 |
| C10orf32 | 6.702 | 5.905 | 6.774 | 5.318 | 5.304 | 5.427 | -2.544 | 0.0199199 | chromosome 10 open reading frame 32 |
| NTAN1 | 5.57 | 4.461 | 4.084 | 2.807 | 4.167 | 3.114 | -2.544 | 0.0413265 | N-terminal asparagine amidase |
| FSCN1 | 9.141 | 9.316 | 8.342 | 7.22 | 7.944 | 7.794 | -2.543 | 0.0179888 | fascin homolog 1, actin-bundling protein (Strongylocentrotus purpuratus) |
| DTX4 | 5.583 | 4.916 | 6.225 | 4.236 | 4.3 | 4.002 | -2.542 | 0.0133734 | deltex homolog 4 (Drosophila) |
| RORA | 7.021 | 6.846 | 7.328 | 5.467 | 6.108 | 5.676 | -2.541 | 0.0068012 | RAR-related orphan receptor A |
| C11orf74 | 1.774 | 2.857 | 1.976 | 1.407 | 0.515 | 0.631 | -2.54 | 0.0193146 | chromosome 11 open reading frame 74 |
| TMEM65 | 5.862 | 6.459 | 6.298 | 5.115 | 4.707 | 4.922 | -2.538 | 0.0064062 | transmembrane protein 65 |
| EXOC1 | 3.273 | 4.396 | 4.366 | 2.454 | 2.604 | 3.052 | -2.538 | 0.0197804 | exocyst complex component 1 |
| ENHO | 1.556 | 1.513 | 2.132 | 0.573 | 0.17 | 0.251 | -2.537 | 0.0049353 | energy homeostasis associated |
| CYB5D2 | 5.612 | 4.004 | 4.957 | 3.127 | 4.164 | 3.615 | -2.536 | 0.048416 | cytochrome b5 domain containing 2 |
| PGM2L1 | 5.955 | 7.117 | 7.207 | 5.429 | 5.869 | 5.424 | -2.528 | 0.0324748 | phosphoglucomutase 2-like 1 |
| ZMYM5 | 5.086 | 6.083 | 6.327 | 4.126 | 4.989 | 4.608 | -2.527 | 0.0287165 | zinc finger, MYM-type 5 |
| SLC22A4 | 5.006 | 5.723 | 4.619 | 4.155 | 4.021 | 3.282 | -2.526 | 0.021682 | solute carrier family 22 (organic cation/ergothioneine transporter), member 4 |
| RWDD3 | 2.078 | 3.906 | 2.97 | 1.44 | 1.633 | 1.878 | -2.526 | 0.0329427 | RWD domain containing 3 |
| GJA1 | 12.062 | 12.134 | 12.358 | 10.695 | 10.972 | 11.021 | -2.525 | 0.0036109 | gap junction protein, alpha 1, 43kDa |
| MAP6 | 2.028 | 2.769 | 3.341 | 1.299 | 1.82 | 1.436 | -2.52 | 0.0290806 | microtubule-associated protein 6 |
| NFIA | 7.748 | 9.127 | 8.041 | 6.415 | 6.891 | 7.149 | -2.519 | 0.0153681 | nuclear factor I/A |
| ABCG1 | 7.47 | 7.47 | 6.872 | 5.542 | 6.304 | 5.826 | -2.513 | 0.0082829 | ATP-binding cassette, sub-family G (WHITE), member 1 |
| SPATA7 | 2.601 | 3.254 | 3.441 | 1.121 | 2.242 | 1.928 | -2.507 | 0.0189912 | spermatogenesis associated 7 |
| PCDHB10 | 3.645 | 4.619 | 4.277 | 2.803 | 3.294 | 2.807 | -2.505 | 0.0180382 | protocadherin beta 10 |
| EPB41L2 | 6.463 | 7.397 | 7.547 | 5.786 | 6.11 | 6.072 | -2.505 | 0.0261551 | erythrocyte membrane protein band 4.1-like 2 |
| FNDC5 | 2.932 | 2.053 | 3.325 | 1.065 | 1.608 | 1.628 | -2.503 | 0.0188166 | fibronectin type III domain containing 5 |
| SLC2A12 | 4.482 | 6.594 | 5.383 | 3.605 | 4.07 | 4.059 | -2.503 | 0.0234507 | solute carrier family 2 (facilitated glucose transporter), member 12 |
| MTMR11 | 5.586 | 7.063 | 6.233 | 4.383 | 5.649 | 4.91 | -2.502 | 0.0381019 | myotubularin related protein 11 |
| PIGF | 4.182 | 4.952 | 4.859 | 3.537 | 3.548 | 3.423 | -2.501 | 0.0132396 | phosphatidylinositol glycan anchor biosynthesis, class F |
| LPAR6 | 6.05 | 8.59 | 7.193 | 5.525 | 5.87 | 5.881 | -2.501 | 0.0409301 | lysophosphatidic acid receptor 6 |
| MAGT1 | 6.478 | 7.697 | 6.583 | 5.703 | 5.156 | 5.689 | -2.499 | 0.0160957 | magnesium transporter 1 |
| WNT4 | 4.059 | 3.068 | 3.452 | 2.616 | 2.565 | 1.747 | -2.499 | 0.0260707 | wingless-type MMTV integration site family, member 4 |
| FAM149A | 2.654 | 1.489 | 1.658 | 0.762 | 0.17 | 0.552 | -2.494 | 0.0123596 | family with sequence similarity 149, member A |
| VIT | 4.248 | 3.813 | 5.789 | 2.495 | 3.618 | 3.368 | -2.494 | 0.0402132 | vitrin |
| RGL1 | 6.124 | 6.046 | 7.185 | 4.538 | 5.867 | 5.377 | -2.494 | 0.049545 | ral guanine nucleotide dissociation stimulator-like 1 |
| JUB | 6.272 | 7.384 | 7.151 | 5.834 | 6.01 | 5.6 | -2.492 | 0.0292151 | jub, ajuba homolog (Xenopus laevis) |
| MRC2 | 9.266 | 9.547 | 9.684 | 7.807 | 8.371 | 8.23 | -2.491 | 0.0047614 | mannose receptor, C type 2 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| CYBRD1 | 8.793 | 7.933 | 8.379 | 6.624 | 7.062 | 7.078 | −2.491 | 0.0061787 | cytochrome b reductase 1 |
| SIDT2 | 6.705 | 7.744 | 7.729 | 5.558 | 6.432 | 6.061 | −2.483 | 0.0172698 | SID1 transmembrane family, member 2 |
| ANXA6 | 7.259 | 7.453 | 7.136 | 5.658 | 6.141 | 6.136 | −2.482 | 0.0048859 | annexin A6 |
| SCARB2 | 7.507 | 8.462 | 7.893 | 6.581 | 6.523 | 6.733 | −2.482 | 0.0086242 | scavenger receptor class B, member 2 |
| GULP1 | 4.13 | 4.866 | 5.381 | 3.566 | 2.819 | 4.053 | −2.482 | 0.0308035 | GULP, engulfment adaptor PTB domain containing 1 |
| MPP5 | 6.519 | 7.041 | 7.742 | 5.73 | 5.708 | 5.836 | −2.481 | 0.0133462 | membrane protein, palmitoylated 5 (MAGUK p55 subfamily member 5) |
| GSTK1 | 7.713 | 8.635 | 8.032 | 6.402 | 7.179 | 6.943 | −2.481 | 0.0160406 | glutathione S-transferase kappa 1 |
| FAM162A | 6.397 | 7.754 | 7.01 | 5.699 | 5.658 | 5.969 | −2.481 | 0.0211619 | family with sequence similarity 162, member A |
| TNFSF13B | 2.005 | 2.097 | 1.978 | 0.924 | 0.695 | −0.206 | −2.479 | 0.0062524 | tumor necrosis factor (ligand) superfamily, member 13b |
| B2M | 13.204 | 12.625 | 13.58 | 11.859 | 11.894 | 11.962 | −2.479 | 0.0123954 | beta-2-microglobulin |
| SHISA5 | 7.564 | 7.488 | 6.739 | 6.172 | 5.703 | 6.254 | −2.479 | 0.0160886 | shisa homolog 5 (Xenopus laevis) |
| CSRP1 | 13.263 | 13.476 | 13.123 | 11.816 | 12.129 | 12.07 | −2.475 | 0.0038334 | cysteine and glycine-rich protein 1 |
| MEIS2 | 6.385 | 5.613 | 5.845 | 4.364 | 4.94 | 4.537 | −2.475 | 0.0089848 | Meis homeobox 2 |
| MAT1A | 1.513 | 2.812 | 2.548 | 0.692 | 1.506 | 1.075 | −2.473 | 0.0357874 | methionine adenosyltransferase I, alpha |
| SEP8 | 6.427 | 7.524 | 7.692 | 5.884 | 6.386 | 6.101 | −2.473 | 0.0440638 | septin 8 |
| HLCS | 2.958 | 3.967 | 3.675 | 2.661 | 2.225 | 2.203 | −2.471 | 0.0215461 | holocarboxylase synthetase (biotin-(propionyl-CoA-carboxylase (ATP-hydrolysing)) ligase) |
| RCAN1 | 11.185 | 10.02 | 9.741 | 8.436 | 9.256 | 9.43 | −2.471 | 0.0387336 | regulator of calcineurin 1 |
| RNF38 | 5.823 | 7.31 | 6.739 | 5.436 | 4.679 | 5.67 | −2.468 | 0.0283315 | ring finger protein 38 |
| SLCO2A1 | 5.967 | 7.888 | 6.89 | 5.728 | 5.196 | 5.588 | −2.466 | 0.0301989 | solute carrier organic anion transporter family, member 2A1 |
| CRLF1 | 4.818 | 5.754 | 3.618 | 3.517 | 3.581 | 2.717 | −2.464 | 0.0382979 | cytokine receptor-like factor 1 |
| ARMCX3 | 7.024 | 8.233 | 8.037 | 6.209 | 6.765 | 6.736 | −2.463 | 0.0299013 | armadillo repeat containing, X-linked 3 |
| FGF1 | 4.234 | 6.715 | 5.141 | 3.615 | 4.197 | 3.841 | −2.463 | 0.0453509 | fibroblast growth factor 1 (acidic) |
| ZNF304 | 5.072 | 5.822 | 5.619 | 4.512 | 4.218 | 4.32 | −2.461 | 0.0131216 | zinc finger protein 304 |
| FIGNL2 | 2.856 | 1.095 | 1.931 | 0.86 | 0.515 | 0.631 | −2.46 | 0.0340066 | fidgetin-like 2 |
| CCDC50 | 8.239 | 9.229 | 8.821 | 7.529 | 7.109 | 7.522 | −2.46 | 0.0095285 | coiled-coil domain containing 50 |
| TAC1 | 4.745 | 3.63 | 6.28 | 2.573 | 3.448 | 3.737 | −2.458 | 0.0422337 | tachykinin, precursor 1 |
| SPRED2 | 7.05 | 8.234 | 8.116 | 6.324 | 6.819 | 6.905 | −2.456 | 0.0391429 | sprouty-related, EVH1 domain containing 2 |
| CHST11 | 5.923 | 6.841 | 6.918 | 5.46 | 4.891 | 5.622 | −2.455 | 0.0225478 | carbohydrate (chondroitin 4) sulfotransferase 11 |
| TTC37 | 2.728 | 4.11 | 3.586 | 2.311 | 1.434 | 2.608 | −2.453 | 0.0299299 | tetratricopeptide repeat domain 37 |
| GPC4 | 3.219 | 4.574 | 4.341 | 3.046 | 2.685 | 3.115 | −2.453 | 0.0463855 | glypican 4 |
| PLAU | 8.166 | 8.351 | 8.744 | 7.087 | 7.056 | 6.896 | −2.452 | 0.0033763 | plasminogen activator, urokinase |
| EMILIN1 | 8.259 | 8.623 | 8.449 | 7.155 | 7.233 | 7.06 | −2.451 | 0.0030514 | elastin microfibril interfacer 1 |
| HOMER1 | 6.682 | 7.738 | 7.631 | 5.875 | 6.341 | 6.339 | −2.448 | 0.0263469 | homer homolog 1 (Drosophila) |
| ZNF331 | 6.938 | 7.991 | 7.527 | 5.305 | 6.7 | 6.277 | −2.447 | 0.0243936 | zinc finger protein 331 |
| CDH26 | 2.525 | 3.009 | 2.659 | 1.556 | 1.235 | 1.386 | −2.446 | 0.0039286 | cadherin 26 |
| ZNF642 | 1.46 | 1.766 | 2.606 | 1.033 | 0.17 | 0.842 | −2.446 | 0.0254969 | zinc finger protein 642 |
| JDP2 | 3.765 | 3.923 | 3.583 | 2.333 | 2.294 | 2.746 | −2.443 | 0.0046355 | Jun dimerization protein 2 |
| FZD1 | 8.781 | 8.943 | 9.61 | 7.494 | 8.173 | 7.715 | −2.44 | 0.0118738 | frizzled homolog 1 (Drosophila) |
| GBP1 | 7.472 | 8.359 | 9.002 | 6.408 | 7.328 | 7.072 | −2.44 | 0.0295113 | guanylate binding protein 1, interferon-inducible, 67kDa |
| RAP2B | 8.566 | 9.624 | 9.641 | 8.133 | 8.354 | 8.28 | −2.44 | 0.0430071 | RAP2B, member of RAS oncogene family |
| NUCB2 | 6.661 | 5.967 | 5.655 | 4.682 | 4.599 | 5.023 | −2.438 | 0.0116448 | nucleobindin 2 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24- N48 | CD24- N58 | CD24- N43 | CD24- N37 | CD24- N39 | CD24- N40 | Pseudo fold change | P value | Gene description |
| PLS3 | 7.967 | 9.147 | 8.123 | 7.114 | 6.681 | 7.346 | -2.438 | 0.0170859 | plastin 3 |
| MBD5 | 3.098 | 3.695 | 4.7 | 2.325 | 2.735 | 2.411 | -2.435 | 0.0251807 | methyl-CpG binding domain protein 5 |
| VPS8 | 2.591 | 4.704 | 3.554 | 2.339 | 2.136 | 2.274 | -2.428 | 0.0393804 | vacuolar protein sorting 8 homolog (S. cerevisiae) |
| PDK3 | 3.371 | 4.32 | 3.693 | 2.2 | 2.587 | 2.415 | -2.425 | 0.0079738 | pyruvate dehydrogenase kinase, isozyme 3 |
| FOXJ3 | 7.379 | 8.424 | 8.671 | 7.146 | 6.987 | 7.242 | -2.425 | 0.0494026 | forkhead box J3 |
| IFT88 | 2.422 | 2.16 | 3.289 | 1.065 | 1.145 | 1.864 | -2.424 | 0.0243421 | intraflagellar transport 88 homolog (Chlamydomonas) |
| EGLN1 | 7.099 | 6.481 | 7.269 | 5.435 | 5.785 | 5.992 | -2.423 | 0.014365 | egl nine homolog 1 (C. elegans) |
| ZNF410 | 5.373 | 6.614 | 5.392 | 4.931 | 4.097 | 4.741 | -2.422 | 0.0386807 | zinc finger protein 410 |
| TBC1D2B | 4.973 | 4.234 | 5.593 | 3.667 | 3.7 | 3.82 | -2.416 | 0.0262288 | TBC1 domain family, member 2B |
| PIK3C2G | 3.438 | 4.73 | 4.383 | 3.111 | 2.894 | 3.236 | -2.416 | 0.0378093 | phosphoinositide-3-kinase, class 2, gamma polypeptide |
| KIAA0922 | 6.393 | 7.538 | 7.501 | 5.92 | 5.818 | 6.266 | -2.415 | 0.0329606 | KIAA0922 |
| NBEAL1 | 2.337 | 3.355 | 2.797 | 1.494 | 2.048 | 1.525 | -2.414 | 0.0253516 | neurobeachin-like 1 |
| CCNDBP1 | 4.771 | 5.972 | 5.5 | 4.422 | 4.217 | 4.229 | -2.413 | 0.0283866 | cyclin D-type binding-protein 1 |
| ACP6 | 2.16 | 2.885 | 2.016 | 0.924 | 1.616 | 0.478 | -2.411 | 0.0188452 | acid phosphatase 6, lysophosphatidic |
| CEP170 | 6.059 | 7.848 | 6.773 | 5.27 | 5.503 | 5.543 | -2.411 | 0.0215318 | centrosomal protein 170kDa |
| C3orf64 | 7.24 | 8.398 | 8.051 | 6.783 | 6.77 | 6.791 | -2.408 | 0.0276311 | chromosome 3 open reading frame 64 |
| ANKRD36 | 1.424 | 2.952 | 2.674 | 0.692 | 0.283 | 1.685 | -2.406 | 0.0315561 | ankyrin repeat domain 36 |
| FAM115C | 1.818 | 3.14 | 3.176 | 2.09 | 1.305 | 0.552 | -2.405 | 0.0384646 | family with sequence similarity 115, member C |
| ROR2 | 3.91 | 4.274 | 4.624 | 2.258 | 3.359 | 3.076 | -2.404 | 0.0144924 | receptor tyrosine kinase-like orphan receptor 2 |
| KAT2B | 4.115 | 4.644 | 5.396 | 3.23 | 3.956 | 3.381 | -2.4 | 0.0318502 | K(lysine) acetyltransferase 2B |
| ZNF672 | 5.776 | 6.018 | 6.783 | 5.469 | 4.514 | 5.198 | -2.398 | 0.0369636 | zinc finger protein 672 |
| SYCE1 | 3.41 | 2.215 | 1.89 | 1.065 | 1.88 | 0.631 | -2.393 | 0.0421464 | synaptonemal complex central element protein 1 |
| PHF21A | 5.457 | 6.46 | 6.527 | 4.54 | 5.27 | 5.116 | -2.39 | 0.0313723 | PHD finger protein 21A |
| KIF21B | 3.125 | 4.336 | 4.009 | 2.752 | 2.879 | 2.585 | -2.39 | 0.0355985 | kinesin family member 21B |
| GPR146 | 5.18 | 1.998 | 1.538 | 0.924 | 0.283 | 1.305 | -2.387 | 0.0415211 | G protein-coupled receptor 146 |
| NDN | 6.387 | 6.224 | 6.651 | 5.705 | 5.134 | 4.897 | -2.384 | 0.0146841 | necdin homolog (mouse) |
| ITGBL1 | 4.471 | 6.374 | 4.077 | 2.884 | 3.356 | 3.219 | -2.382 | 0.0180625 | integrin, beta-like 1 (with EGF-like repeat domains) |
| MAN2B2 | 6.704 | 5.531 | 5.952 | 4.535 | 4.766 | 4.701 | -2.381 | 0.0107233 | mannosidase, alpha, class 2B, member 2 |
| ALKBH3 | 1.62 | 1.966 | 1.946 | 1.079 | 0.695 | 0.162 | -2.38 | 0.0150376 | alkB, alkylation repair homolog 3 (E. coli) |
| TBC1D23 | 6.405 | 7.417 | 7.596 | 6.187 | 5.714 | 6.166 | -2.38 | 0.0365672 | TBC1 domain family, member 23 |
| UBQLN2 | 7.488 | 9.051 | 8.546 | 7.296 | 6.92 | 7.316 | -2.379 | 0.040543 | ubiquilin 2 |
| C2orf28 | 5.333 | 6.476 | 5.669 | 4.036 | 4.431 | 5.226 | -2.377 | 0.0328318 | chromosome 2 open reading frame 28 |
| SLC27A3 | 6.379 | 6.227 | 6.164 | 5.131 | 4.701 | 4.978 | -2.376 | 0.0033834 | solute carrier family 27 (fatty acid transporter), member 3 |
| SIK3 | 8.627 | 9.391 | 9.519 | 8.149 | 8.143 | 8.113 | -2.376 | 0.0255656 | SIK family kinase 3 |
| GABARAP | 8.161 | 8.866 | 7.215 | 6.285 | 7.076 | 7.076 | -2.376 | 0.0331323 | GABA(A) receptor-associated protein |
| PDHB | 4.785 | 5.782 | 5.151 | 4.534 | 3.507 | 4.415 | -2.376 | 0.0469364 | pyruvate dehydrogenase (lipoamide) beta |
| PDLIM3 | 8.734 | 10.385 | 8.793 | 7.513 | 7.546 | 7.858 | -2.375 | 0.0134163 | PDZ and LIM domain 3 |
| ABLIM1 | 8.739 | 9.975 | 9.323 | 8.064 | 8.075 | 8.221 | -2.375 | 0.0202261 | actin binding LIM protein 1 |
| YAF2 | 8.189 | 10.196 | 9.306 | 8.062 | 7.271 | 8.215 | -2.369 | 0.0431681 | YY1 associated factor 2 |
| TIFA | 5.316 | 6.122 | 6.124 | 4.609 | 4.882 | 4.789 | -2.365 | 0.0212134 | TRAF-interacting protein with forkhead-associated domain |
| MOSC2 | 3.024 | 2.567 | 3.162 | 1.623 | 1.92 | 1.513 | -2.364 | 0.0082185 | MOCO sulphurase C-terminal domain containing 2 |
| PAPSS2 | 4.755 | 4.181 | 5.701 | 2.94 | 3.722 | 3.527 | -2.364 | 0.0178164 | 3'-phosphoadenosine 5'-phosphosulfate synthase 2 |
| TPM4 | 10.212 | 11.147 | 10.641 | 9.891 | 8.971 | 9.835 | -2.363 | 0.0386993 | tropomyosin 4 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
| --- | --- | --- | --- | --- | --- | --- | --- | --- | --- |
| | CD24+ N48 | CD24+ N58 | CD24+ N43 | CD24+ N37 | CD24+ N39 | CD24+ N40 | | | |
| CNTN3 | 2.463 | 4.33 | 3.5 | 2.539 | 1.587 | 2.26 | −2.362 | 0.0466402 | contactin 3 (plasmacytoma associated) |
| SH3BP5 | 7.925 | 9.783 | 8.074 | 6.686 | 7.58 | 7.426 | −2.36 | 0.0463633 | SH3-domain binding protein 5 (BTK-associated) |
| ARL15 | 3.483 | 4.611 | 3.986 | 2.749 | 2.339 | 3.157 | −2.358 | 0.0209337 | ADP-ribosylation factor-like 15 |
| SAMD9 | 3.375 | 1.275 | 2.17 | 1.121 | 0.814 | 0.935 | −2.354 | 0.0457323 | sterile alpha motif domain containing 9 |
| C3orf18 | 3.55 | 4.168 | 4.028 | 1.723 | 3.217 | 2.796 | −2.349 | 0.0253588 | chromosome 3 open reading frame 18 |
| TTYH3 | 5.438 | 7.724 | 6.307 | 5.108 | 4.485 | 5.074 | −2.349 | 0.0281391 | tweety homolog 3 (Drosophila) |
| TPST1 | 6.564 | 7.676 | 7.314 | 5.334 | 6.403 | 6.202 | −2.347 | 0.0356128 | tyrosylprotein sulfotransferase 1 |
| C14orf179 | 4.713 | 5.651 | 5.154 | 3.924 | 4.118 | 3.879 | −2.346 | 0.0142613 | chromosome 14 open reading frame 179 |
| CD74 | 9.6 | 8.856 | 8.016 | 7.094 | 7.67 | 7.627 | −2.345 | 0.0246984 | CD74 molecule, major histocompatibility complex, class II invariant chain |
| ST3GAL6 | 1.861 | 2.508 | 0.96 | 0.86 | 0.515 | 0.631 | −2.345 | 0.0484732 | ST3 beta-galactoside alpha-2,3-sialyltransferase 6 |
| RFXAP | 3.084 | 3.381 | 3.733 | 1.612 | 2.507 | 2.153 | −2.342 | 0.0119868 | regulatory factor X-associated protein |
| DOCK4 | 5.146 | 5.811 | 5.624 | 4.207 | 4.585 | 4.198 | −2.339 | 0.0106804 | dedicator of cytokinesis 4 |
| EXOC4 | 4.518 | 5.024 | 5.034 | 3.658 | 4.042 | 3.292 | −2.339 | 0.0140531 | exocyst complex component 4 |
| PIGK | 5.782 | 6.325 | 6.223 | 4.088 | 5.137 | 4.999 | −2.336 | 0.0131072 | phosphatidylinositol glycan anchor biosynthesis, class K |
| TPK1 | 1.896 | 0.96 | 1.747 | 0.173 | −0.264 | 0.713 | −2.336 | 0.0182278 | thiamin pyrophosphokinase 1 |
| WDFY3 | 6.495 | 7.209 | 7.657 | 6.054 | 5.978 | 5.987 | −2.333 | 0.0271568 | WD repeat and FYVE domain containing 3 |
| WLS | 7.594 | 9.338 | 8.521 | 7.299 | 7.419 | 7.096 | −2.333 | 0.0426608 | wntless homolog (Drosophila) |
| PNRC1 | 11.007 | 11.621 | 13.033 | 9.789 | 10.813 | 10.849 | −2.327 | 0.0468777 | proline-rich nuclear receptor coactivator 1 |
| FYN | 7.244 | 7.817 | 7.859 | 6.588 | 6.449 | 6.641 | −2.325 | 0.0141339 | FYN oncogene related to SRC, FGR, YES |
| ALX4 | 2.295 | 2.296 | 2.864 | 1.648 | 1.033 | 1.609 | −2.324 | 0.0236911 | ALX homeobox 4 |
| EPB41L4A | 4.168 | 5.041 | 4.572 | 3.277 | 2.954 | 3.834 | −2.321 | 0.0192631 | erythrocyte membrane protein band 4.1 like 4A |
| TRAPPC2L | 3.877 | 4.579 | 5.971 | 3.379 | 2.681 | 3.365 | −2.32 | 0.0203642 | trafficking protein particle complex 2-like |
| HNRNPD | 8.767 | 9.51 | 9.808 | 8.4 | 8.224 | 8.296 | −2.32 | 0.0298254 | heterogeneous nuclear ribonucleoprotein D (AU-rich element RNA binding protein 1,37kDa) |
| BMPR2 | 8.834 | 8.283 | 7.648 | 6.728 | 7.352 | 7.071 | −2.318 | 0.024941 | bone morphogenetic protein receptor, type II (serine/threonine kinase) |
| FBXO42 | 5.483 | 7.227 | 6.247 | 5.085 | 4.682 | 5.034 | −2.318 | 0.0259054 | F-box protein 42 |
| ARHGEF3 | 5.584 | 5.407 | 4.894 | 3.483 | 4.634 | 4.194 | −2.318 | 0.0271095 | Rho guanine nucleotide exchange factor (GEF) 3 |
| TGFBR3 | 8.42 | 8.618 | 9.619 | 7.207 | 7.95 | 7.924 | −2.317 | 0.0340631 | transforming growth factor, beta receptor III |
| GGN | 2.687 | 2.436 | 2.06 | 1.272 | 0.848 | 1.244 | −2.317 | 0.0075696 | gametogenetin |
| GSTZ1 | 4.179 | 5.216 | 4.357 | 2.967 | 3.351 | 3.513 | −2.315 | 0.0153288 | glutathione transferase zeta 1 |
| SKIV2L | 4.231 | 5.068 | 5.123 | 3.912 | 3.446 | 3.663 | −2.315 | 0.0224991 | superkiller viralicidic activity 2-like (S. cerevisiae) |
| C5 | 2.419 | 3.241 | 3.303 | 0.573 | 2.031 | 2.124 | −2.314 | 0.0301917 | complement component 5 |
| LPL | 3.986 | 3.794 | 4.286 | 3.058 | 3.076 | 1.948 | −2.313 | 0.017591 | lipoprotein lipase |
| SERPINB6 | 7.26 | 6.667 | 6.651 | 5.442 | 5.818 | 5.61 | −2.311 | 0.0087508 | serpin peptidase inhibitor, clade B (ovalbumin), member 6 |
| NUDT4P1 | 8.297 | 8.94 | 9.228 | 7.097 | 7.892 | 7.731 | −2.311 | 0.0193482 | nudix (nucleoside diphosphate linked moiety X)-type motif 4 pseudogene 1 |
| ST3GAL3 | 4.062 | 4.344 | 4.9 | 2.855 | 3.486 | 3.5 | −2.309 | 0.0215733 | ST3 beta-galactoside alpha-2,3-sialyltransferase 3 |
| FAM124A | 2.241 | 2.963 | 1.332 | 1.333 | 0.17 | 1.033 | −2.309 | 0.0391779 | family with sequence similarity 124A |
| CTSB | 10.174 | 9.535 | 8.81 | 8.028 | 8.547 | 8.329 | −2.308 | 0.0295886 | cathepsin B |
| CUL1 | 7.203 | 8.139 | 8.989 | 6.933 | 6.917 | 6.972 | −2.307 | 0.0493582 | cullin 1 |
| SPATA6 | 3.263 | 4.838 | 4.857 | 2.555 | 2.423 | 3.653 | −2.303 | 0.0372963 | spermatogenesis associated 6 |
| ANP32A | 5.144 | 5.584 | 4.99 | 3.935 | 4.193 | 3.941 | −2.302 | 0.0075438 | acidic (leucine-rich) nuclear phosphoprotein 32 family, member A |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| NRIP1 | 7.821 | 8.512 | 8.6 | 6.886 | 7.114 | 7.401 | −2.297 | 0.0161172 | nuclear receptor interacting protein 1 |
| COL4A2 | 10.156 | 11.255 | 9.757 | 9.172 | 8.749 | 8.957 | −2.295 | 0.0175367 | collagen, type IV, alpha 2 |
| ACP5 | 4.948 | 4.347 | 5.19 | 3.149 | 4.101 | 3.649 | −2.294 | 0.023719 | acid phosphatase 5, tartrate resistant |
| MEOX1 | 5.583 | 2.268 | 2.056 | 1.121 | 1.07 | 0.935 | −2.294 | 0.0263046 | mesenchyme homeobox 1 |
| HECW1 | 2.393 | 2.533 | 2.012 | 2.019 | 0.814 | 0.935 | −2.294 | 0.0476404 | HECT, C2 and WW domain containing E3 ubiquitin protein ligase 1 |
| SYNGR1 | 5.318 | 5.425 | 5.368 | 4.242 | 3.973 | 4.172 | −2.291 | 0.0027982 | synaptogyrin 1 |
| ATXN1 | 7.753 | 8.637 | 8.395 | 7.028 | 7.2 | 7.249 | −2.291 | 0.0194512 | ataxin 1 |
| FDXR | 2.693 | 3.084 | 3.743 | 1.818 | 2.548 | 1.779 | −2.29 | 0.0344645 | ferredoxin reductase |
| COL18A1 | 10.12 | 10.687 | 10.483 | 9.288 | 9.405 | 9.18 | −2.289 | 0.0090377 | collagen, type XVIII, alpha 1 |
| C17orf72 | 4.037 | 2.689 | 2.58 | 1.854 | 1.787 | 1.386 | −2.289 | 0.0199463 | chromosome 17 open reading frame 72 |
| TBC1D15 | 7.257 | 8.742 | 7.94 | 6.746 | 6.61 | 7.101 | −2.289 | 0.0394892 | TBC1 domain family, member 15 |
| PPT2 | 6.445 | 6.384 | 6.523 | 5.329 | 5.264 | 5.084 | −2.288 | 0.00302 | palmitoyl-protein thioesterase 2 |
| CPOX | 3.461 | 4.382 | 3.927 | 2.891 | 2.733 | 2.279 | −2.288 | 0.0132904 | coproporphyrinogen oxidase |
| UBR7 | 6.135 | 7.606 | 6.31 | 5.76 | 4.942 | 5.412 | −2.287 | 0.0321049 | ubiquitin protein ligase E3 component n-recognin 7 (putative) |
| KHDRBS1 | 9.3 | 9.863 | 9.859 | 8.695 | 8.096 | 8.669 | −2.282 | 0.0140316 | KH domain containing, RNA binding, signal transduction associated 1 |
| C7orf70 | 3.543 | 4.402 | 4.111 | 3.581 | 2.352 | 2.886 | −2.282 | 0.0484589 | chromosome 7 open reading frame 70 |
| DZIP1 | 4.865 | 6.258 | 5.93 | 4.744 | 4.769 | 4.229 | −2.276 | 0.0483237 | DAZ interacting protein 1 |
| LRRC16A | 6.03 | 6.219 | 6.454 | 5.053 | 5.033 | 5.004 | −2.274 | 0.0044759 | leucine rich repeat containing 16A |
| DCHS1 | 8.108 | 7.061 | 7.493 | 6.116 | 6.688 | 6.309 | −2.272 | 0.0219518 | dachsous 1 (Drosophila) |
| SCRN3 | 1.353 | 2.108 | 2.084 | 0.762 | 0.924 | 0.251 | −2.271 | 0.0177277 | secernin 3 |
| TPD52 | 4.933 | 6.196 | 5.583 | 4.4 | 4.593 | 4.388 | −2.271 | 0.0320906 | tumor protein D52 |
| CYB5R4 | 1.767 | 2.54 | 2.118 | 1.299 | 0.814 | 0.935 | −2.27 | 0.0173049 | cytochrome b5 reductase 4 |
| TDRD6 | 1.858 | 3.308 | 2.739 | 1.556 | 1.235 | 1.747 | −2.27 | 0.04391 | tudor domain containing 6 |
| SLC31A2 | 4.488 | 3.739 | 4.367 | 2.974 | 3.306 | 2.686 | −2.268 | 0.0149038 | solute carrier family 31 (copper transporters), member 2 |
| KDELC1 | 3.063 | 3.624 | 3.67 | 2.494 | 2.309 | 1.956 | −2.26 | 0.0117214 | KDEL (Lys-Asp-Glu-Leu) containing 1 |
| IFIT2 | 3.46 | 2.111 | 1.908 | 1.121 | 0.814 | 0.935 | −2.259 | 0.0148966 | interferon-induced protein with tetratricopeptide repeats 2 |
| 3-Mar | 4.878 | 5.49 | 4.938 | 4.099 | 3.703 | 4.09 | −2.258 | 0.0135544 | membrane-associated ring finger (C3HC4) 3 |
| LOC550643 | 6.403 | 6.504 | 5.797 | 5.31 | 5.125 | 5.229 | −2.258 | 0.0212757 | No description |
| TLE4 | 7.619 | 8.998 | 8.243 | 6.504 | 7.226 | 7.069 | −2.255 | 0.0212063 | transducin-like enhancer of split 4 (E(sp1) homolog, Drosophila) |
| PON2 | 5.557 | 7.364 | 6.245 | 5.074 | 5.048 | 5.176 | −2.251 | 0.0356271 | paraoxonase 2 |
| ATP11C | 5.917 | 6.508 | 6.604 | 5.436 | 4.854 | 5.289 | −2.247 | 0.016774 | ATPase, class VI, type 11C |
| STARD8 | 4.443 | 3.829 | 3.187 | 2.953 | 2.019 | 2.727 | −2.247 | 0.0298684 | StAR-related lipid transfer (START) domain containing 8 |
| AGXT2L2 | 5.601 | 5.424 | 6.447 | 4.632 | 4.434 | 4.43 | −2.246 | 0.0115561 | alanine-glyoxylate aminotransferase 2-like 2 |
| BDNFOS | 2.836 | 3.119 | 2.533 | 1.366 | 2.348 | 1.609 | −2.246 | 0.0340559 | No description |
| PNMA1 | 7.883 | 8.184 | 7.925 | 6.361 | 7.141 | 6.758 | −2.244 | 0.0094927 | paraneoplastic antigen MA1 |
| YPEL2 | 6.467 | 6.03 | 6.238 | 4.296 | 5.402 | 5.072 | −2.243 | 0.0139329 | yippee-like 2 (Drosophila) |
| TGM2 | 5.629 | 3.723 | 3.144 | 2.557 | 2.396 | 2.909 | −2.243 | 0.041242 | transglutaminase 2 (C polypeptide, protein-glutamine-gamma-glutamyltransferase) |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| RAPGEF2 | 8.084 | 8.845 | 9.044 | 7.68 | 7.526 | 7.746 | −2.242 | 0.0333348 | Rap guanine nucleotide exchange factor (GEF) 2 |
| HEY1 | 9.025 | 6.476 | 5.896 | 4.738 | 5.831 | 5.311 | −2.242 | 0.0426293 | hairy/enhancer-of-split related with YRPW motif 1 |
| TNIP1 | 7.27 | 7.897 | 8.466 | 6.565 | 6.733 | 6.87 | −2.241 | 0.0256064 | TNFAIP3 interacting protein 1 |
| PRTFDC1 | 4.249 | 4.478 | 5.095 | 2.876 | 4.037 | 3.315 | −2.239 | 0.0303756 | phosphoribosyl transferase domain containing 1 |
| CSNK1G3 | 5.966 | 6.859 | 6.68 | 5.51 | 5.54 | 5.519 | −2.235 | 0.0320977 | casein kinase 1, gamma 3 |
| ABHD14A | 4.808 | 4.323 | 5.042 | 3.421 | 3.883 | 3.613 | −2.232 | 0.0184181 | abhydrolase domain containing 14A |
| ADH5 | 6.736 | 7.902 | 7.398 | 5.96 | 6.24 | 6.368 | −2.232 | 0.0257523 | alcohol dehydrogenase 5 (class III), chi polypeptide |
| VPS45 | 2.722 | 3.404 | 3.896 | 2.409 | 2.245 | 1.818 | −2.232 | 0.0265043 | vacuolar protein sorting 45 homolog (S. cerevisiae) |
| LAMB1 | 7.839 | 7.244 | 9.301 | 6.193 | 7.242 | 6.68 | −2.232 | 0.0429527 | laminin, beta 1 |
| PIBF1 | 2.986 | 2.32 | 2.748 | 1.679 | 1.287 | 1.59 | −2.231 | 0.0114975 | progesterone immunomodulatory binding factor 1 |
| PECI | 5.832 | 7.246 | 6.289 | 5.245 | 4.689 | 5.133 | −2.229 | 0.016158 | peroxisomal D3,D2-enoyl-CoA isomerase |
| PGAP3 | 4.98 | 4.507 | 3.93 | 3.352 | 3.642 | 3.219 | −2.227 | 0.0304228 | post-GPI attachment to proteins 3 |
| SMARCA1 | 6.889 | 7.434 | 7.484 | 6.224 | 6.33 | 6.173 | −2.226 | 0.0165 | SWI/SNF related, matrix associated, actin dependent regulator of chromatin, subfamily a, member 1 |
| C1QTNF3 | 4.121 | 3.467 | 3.68 | 2.274 | 2.966 | 2.747 | −2.226 | 0.0212399 | C1q and tumor necrosis factor related protein 3 |
| SELE | 5.958 | 4.33 | 4.059 | 2.905 | 3.438 | 3.28 | −2.226 | 0.0220355 | selectin E |
| ZC4H2 | 2.805 | 3.354 | 3.453 | 1.494 | 2.449 | 2.2 | −2.226 | 0.024433 | zinc finger, C4H2 domain containing |
| ASMTL | 4.312 | 5.307 | 4.49 | 3.634 | 3.157 | 3.964 | −2.223 | 0.0337025 | acetylserotonin O-methyltransferase-like |
| DLG2 | 2.851 | 2.977 | 2.804 | 1.698 | 1.408 | 2.19 | −2.222 | 0.0149903 | discs, large homolog 2 (Drosophila) |
| SNTB1 | 3.449 | 3.131 | 3.243 | 2.351 | 1.85 | 2.091 | −2.222 | 0.0073485 | syntrophin, beta 1 (dystrophin-associated protein A1, 59kDa, basic component 1) |
| SEP6 | 5.267 | 4.854 | 5.105 | 3.702 | 4.241 | 3.921 | −2.222 | 0.0111784 | septin 6 |
| BCL2 | 5.817 | 6.544 | 6.566 | 5.045 | 5.415 | 5.374 | −2.22 | 0.0261623 | B-cell CLL/lymphoma 2 |
| RASSF1 | 8.07 | 8.316 | 8.756 | 7.356 | 7.058 | 7.167 | −2.218 | 0.0099006 | Ras association (RalGDS/AF-6) domain family member 1 |
| HAUS8 | 4.12 | 4.91 | 3.804 | 3.613 | 2.97 | 2.715 | −2.218 | 0.0325263 | HAUS augmin-like complex, subunit 8 |
| PCCA | 3.938 | 4.293 | 4.289 | 3.14 | 2.662 | 3.271 | −2.217 | 0.0115762 | propionyl CoA carboxylase, alpha polypeptide |
| NAALAD2 | 1.107 | 2.072 | 2.052 | 0.573 | 0.924 | 0.251 | −2.216 | 0.027214 | N-acetylated alpha-linked acidic dipeptidase 2 |
| WTAP | 9.619 | 9.497 | 9.69 | 8.375 | 8.349 | 8.751 | −2.215 | 0.0076075 | Wilms tumor 1 associated protein |
| SEMA6A | 5.611 | 5.313 | 6.391 | 4.464 | 4.924 | 4.417 | −2.214 | 0.0245103 | sema domain, transmembrane domain (TM), and cytoplasmic domain, (semaphorin) 6A |
| DDX42 | 7.271 | 8.158 | 8.177 | 6.644 | 6.88 | 7.033 | −2.21 | 0.035464 | DEAD (Asp-Glu-Ala-Asp) box polypeptide 42 |
| NIPSNAP1 | 4.452 | 5.476 | 4.638 | 3.308 | 3.809 | 3.908 | −2.21 | 0.0242699 | nipsnap homolog 1 (C. elegans) |
| CNIH3 | 2.821 | 1.944 | 2.657 | 0.86 | 1.678 | 0.886 | −2.208 | 0.0157344 | cornichon homolog 3 (Drosophila) |
| BAI2 | 4.824 | 5.435 | 5.06 | 4.434 | 3.917 | 3.651 | −2.208 | 0.0214395 | brain-specific angiogenesis inhibitor 2 |
| ABCD4 | 5.095 | 6.201 | 5.329 | 4.616 | 3.954 | 4.288 | −2.206 | 0.0208321 | ATP-binding cassette, sub-family D (ALD), member 4 |
| SKAP2 | 5.101 | 5.588 | 4.891 | 3.708 | 4.447 | 4.291 | −2.206 | 0.0295443 | src kinase associated phosphoprotein 2 |
| RAC2 | 3.081 | 3.66 | 2.657 | 1.606 | 1.88 | 2.52 | −2.204 | 0.0339994 | ras-related C3 botulinum toxin substrate 2 (rho family, small GTP binding protein Rac2) |
| C1orf226 | 5.627 | 6.864 | 6.644 | 5.022 | 5.725 | 5.169 | −2.202 | 0.0496129 | chromosome 1 open reading frame 226 |
| TTC31 | 2.356 | 1.982 | 2.844 | 1.757 | 0.848 | 0.886 | −2.196 | 0.0228647 | tetratricopeptide repeat domain 31 |
| CD180 | 0.871 | 1.715 | 1.747 | 0.924 | −0.264 | −0.206 | −2.196 | 0.028929 | CD180 molecule |
| RB1CC1 | 8.082 | 8.919 | 8.863 | 7.57 | 7.717 | 7.786 | −2.193 | 0.0404972 | RB1-inducible coiled-coil 1 |
| ARHGAP24 | 6.861 | 4.779 | 5.763 | 4.652 | 4.632 | 4.112 | −2.191 | 0.0451728 | Rho GTPase activating protein 24 |
| COMMD3 | 3.451 | 4.48 | 4.012 | 2.402 | 3.35 | 2.591 | −2.189 | 0.0290957 | COMM domain containing 3 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| ANK3 | 3.562 | 4.269 | 4.51 | 3.139 | 2.882 | 3.312 | −2.189 | 0.0359169 | ankyrin 3, node of Ranvier (ankyrin G) |
| GDF10 | 3.655 | 1.095 | 1.99 | 0.86 | 0.515 | 0.886 | −2.188 | 0.0458689 | growth differentiation factor 10 |
| ACTR8 | 4.431 | 4.826 | 4.872 | 3.557 | 3.744 | 3.351 | −2.186 | 0.0084303 | ARP8 actin-related protein 8 homolog (yeast) |
| ATXN10 | 5.32 | 6.64 | 5.95 | 5.239 | 4.191 | 5.033 | −2.186 | 0.0492101 | ataxin 10 |
| FAM19A5 | 4.829 | 5.296 | 5.82 | 4.693 | 4.017 | 4.126 | −2.183 | 0.0392123 | family with sequence similarity 19 (chemokine (C-C motif)-like), member A5 |
| KANK2 | 5.632 | 5.218 | 6.364 | 4.176 | 4.505 | 5.139 | −2.183 | 0.0411233 | KN motif and ankyrin repeat domains 2 |
| RBL2 | 5.109 | 5.291 | 5.141 | 4.1 | 4.165 | 3.967 | −2.182 | 0.0047113 | retinoblastoma-like 2 (p130) |
| PARP9 | 4.715 | 4.209 | 4.095 | 3.378 | 3.084 | 3.063 | −2.181 | 0.0106124 | poly (ADP-ribose) polymerase family, member 9 |
| ARL5B | 5.438 | 6.97 | 6.132 | 4.806 | 5.358 | 5.008 | −2.18 | 0.0482765 | ADP-ribosylation factor-like 5B |
| NAALADL1 | 3.036 | 4.125 | 3.538 | 2.026 | 2.414 | 2.735 | −2.179 | 0.0262732 | N-acetylated alpha-linked acidic dipeptidase-like 1 |
| ZNF136 | 4.065 | 5.469 | 4.463 | 3.792 | 2.941 | 3.603 | −2.179 | 0.0380053 | zinc finger protein 136 |
| GMPR2 | 5.416 | 6.605 | 5.506 | 4.293 | 5.013 | 4.952 | −2.179 | 0.0486785 | guanosine monophosphate reductase 2 |
| ASNSD1 | 6.17 | 5.863 | 5.63 | 4.891 | 4.74 | 4.704 | −2.178 | 0.0093618 | asparagine synthetase domain containing 1 |
| PPP1R2 | 6.466 | 6.953 | 6.426 | 5.831 | 5.266 | 5.797 | −2.176 | 0.0276697 | protein phosphatase 1, regulatory (inhibitor) subunit 2 |
| SSX2IP | 3.866 | 3.987 | 3.999 | 3.009 | 2.867 | 2.626 | −2.174 | 0.0061644 | synovial sarcoma, X breakpoint 2 interacting protein |
| TMCC2 | 3.745 | 4.31 | 2.895 | 3.19 | 1.787 | 1.943 | −2.174 | 0.0408972 | transmembrane and coiled-coil domain family 2 |
| ZNF433 | 4.764 | 4.688 | 4.431 | 3.302 | 3.57 | 3.73 | −2.17 | 0.00955 | zinc finger protein 433 |
| N4BP1 | 5.332 | 7.022 | 5.553 | 4.74 | 4.634 | 4.216 | −2.168 | 0.0253373 | NEDD4 binding protein 1 |
| SCN4B | 5.813 | 6.755 | 5.931 | 4.697 | 5.032 | 4.939 | −2.167 | 0.0129742 | sodium channel, voltage-gated, type IV, beta |
| CYR61 | 13.134 | 14.844 | 13.731 | 12.368 | 12.871 | 12.615 | −2.165 | 0.0352357 | cysteine-rich, angiogenic inducer, 61 |
| GRIA4 | 5.032 | 6.7 | 5.367 | 4.252 | 4.47 | 4.229 | −2.164 | 0.0254225 | glutamate receptor, ionotropic, AMPA4 |
| NEU1 | 6.338 | 7.076 | 7.24 | 5.526 | 5.885 | 6.126 | −2.163 | 0.0339171 | sialidase 1 (lysosomal sialidase) |
| SLC22A18 | 4.805 | 5.171 | 5.789 | 3.692 | 4.462 | 4.213 | −2.163 | 0.0290492 | solute carrier family 22, member 18 |
| LEPROT | 7.673 | 8.529 | 7.454 | 6.342 | 6.971 | 6.798 | −2.162 | 0.0260492 | leptin receptor overlapping transcript |
| CLU | 9.08 | 9.407 | 8.565 | 7.554 | 7.971 | 8.014 | −2.156 | 0.0163368 | clusterin |
| STK38L | 6.498 | 8.732 | 6.89 | 5.782 | 5.571 | 5.816 | −2.155 | 0.0243615 | serine/threonine kinase 38 like |
| AHR | 9.818 | 10.662 | 10.235 | 8.478 | 9.555 | 9.473 | −2.154 | 0.0474544 | aryl hydrocarbon receptor |
| MTCP1NB | 4.388 | 4.909 | 4.053 | 3.541 | 3.118 | 3.282 | −2.152 | 0.017742 | mature T-cell proliferation 1 neighbor |
| PDHX | 4.679 | 5.619 | 5.57 | 4.028 | 3.573 | 4.62 | −2.152 | 0.0297761 | pyruvate dehydrogenase complex, component X |
| TJP1 | 8.937 | 9.083 | 9.001 | 7.897 | 7.508 | 8.015 | −2.15 | 0.0059755 | tight junction protein 1 (zona occludens 1) |
| GAB1 | 7.107 | 7.245 | 6.863 | 5.285 | 6.251 | 6.005 | −2.147 | 0.0155835 | GRB2-associated binding protein 1 |
| C14orf145 | 1.515 | 2.224 | 2.946 | 1.121 | 1.07 | 1.163 | −2.147 | 0.0394698 | chromosome 14 open reading frame 145 |
| N4BP2L1 | 5.638 | 5.979 | 7.028 | 4.537 | 4.894 | 5.153 | −2.146 | 0.0211548 | NEDD4 binding protein 2-like 1 |
| RNASE4 | 6.708 | 6.059 | 6.535 | 4.817 | 5.607 | 5.588 | −2.145 | 0.0268448 | ribonuclease, RNase A family, 4 |
| TRAK1 | 8.387 | 8.693 | 8.733 | 7.251 | 7.668 | 7.593 | −2.144 | 0.0098519 | trafficking protein, kinesin binding 1 |
| NT5DC1 | 2.739 | 3.932 | 3.493 | 1.999 | 2.832 | 1.818 | −2.144 | 0.0406067 | 5′-nucleotidase domain containing 1 |
| FAM135A | 5.745 | 5.355 | 5.053 | 4.396 | 3.953 | 4.533 | −2.143 | 0.0197152 | family with sequence similarity 135, member A |
| SDK1 | 5.447 | 6.269 | 5.918 | 4.748 | 4.982 | 4.818 | −2.143 | 0.0226944 | sidekick homolog 1, cell adhesion molecule (chicken) |
| DNAJC12 | 2.574 | 3.312 | 3.349 | 2.283 | 2.214 | 1.033 | −2.141 | 0.0342563 | DnaJ (Hsp40) homolog, subfamily C, member 12 |
| CKAP4 | 9.47 | 9.574 | 8.976 | 8.511 | 7.744 | 8.373 | −2.14 | 0.0204658 | cytoskeleton-associated protein 4 |
| COPS8 | 5.374 | 5.328 | 5.398 | 4.187 | 4.279 | 4.501 | −2.136 | 0.0069092 | COP9 constitutive photomorphogenic homolog subunit 8 (Arabidopsis) |
| LRRC49 | 4.17 | 4.627 | 5.201 | 3.345 | 3.532 | 3.565 | −2.136 | 0.0174136 | leucine rich repeat containing 49 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| GLI2 | 2.513 | 2.608 | 5.891 | 1.494 | 1.513 | 1.948 | −2.136 | 0.0389504 | GLI family zinc finger 2 |
| PRDM6 | 2.128 | 2.974 | 2.636 | 2.205 | 1.033 | 1.201 | −2.136 | 0.04609 | PR domain containing 6 |
| RIN3 | 5.965 | 3.642 | 4.043 | 3.31 | 2.996 | 2.549 | −2.133 | 0.0340703 | Ras and Rab interactor 3 |
| DCAF6 | 7.88 | 8.614 | 8.504 | 7.415 | 7.409 | 7.516 | −2.128 | 0.037928 | DDB1 and CUL4 associated factor 6 |
| NRP2 | 8.895 | 9.138 | 8.979 | 8.049 | 7.575 | 7.957 | −2.127 | 0.0078 | neuropilin 2 |
| ALG6 | 4.024 | 3.162 | 3.9 | 2.935 | 1.513 | 2.909 | −2.127 | 0.0435308 | asparagine-linked glycosylation 6, alpha-1,3-glucosyltransferase homolog (S. cerevisiae) |
| SNTB2 | 9.237 | 10.285 | 9.865 | 8.342 | 9.038 | 8.779 | −2.124 | 0.0356729 | syntrophin, beta 2 (dystrophin-associated protein A1, 59kDa, basic component 2) |
| HS2ST1 | 6.453 | 7.17 | 6.954 | 6.085 | 5.345 | 5.958 | −2.122 | 0.0284668 | heparan sulfate 2-O-sulfotransferase 1 |
| FOXF1 | 3.378 | 3.806 | 4.588 | 2.682 | 2.72 | 3.111 | −2.122 | 0.0368026 | forkhead box F1 |
| OS9 | 7.464 | 7.844 | 7.922 | 6.629 | 6.837 | 6.749 | −2.121 | 0.0135301 | osteosarcoma amplified 9, endoplasmic reticulum lectin |
| SLC23A2 | 6.079 | 6.602 | 6.442 | 5.518 | 5.074 | 5.335 | −2.121 | 0.0145553 | solute carrier family 23 (nucleobase transporters), member 2 |
| TXNDC15 | 4.962 | 5.268 | 5.557 | 4.473 | 3.871 | 4.193 | −2.12 | 0.0178415 | thioredoxin domain containing 15 |
| PLS1 | 3.941 | 3.282 | 4.843 | 3.011 | 2.689 | 2.857 | −2.12 | 0.0398261 | plastin 1 |
| RET | 2.316 | 2.622 | 3.706 | 1.659 | 1.434 | 1.541 | −2.115 | 0.0195285 | ret proto-oncogene |
| FCRL6 | 1.923 | 2.829 | 1.66 | 1.188 | 0.609 | 0.842 | −2.115 | 0.0213544 | Fc receptor-like 6 |
| BMI1 | 5.261 | 6.049 | 6.319 | 4.254 | 4.97 | 4.99 | −2.113 | 0.03346 | BMI1 polycomb ring finger oncogene |
| SEP10 | 6.335 | 6.871 | 6.753 | 5.794 | 5.47 | 5.56 | −2.11 | 0.0146104 | septin 10 |
| SVEP1 | 4.89 | 4.507 | 5.425 | 3.956 | 3.744 | 3.813 | −2.109 | 0.0196466 | sushi, von Willebrand factor type A, EGF and pentraxin domain containing 1 |
| FZD8 | 7.939 | 9.902 | 8.203 | 7.127 | 7.101 | 7.356 | −2.108 | 0.0287572 | frizzled homolog 8 (Drosophila) |
| MXD3 | 4.435 | 4.55 | 4.466 | 3.798 | 3.263 | 3.393 | −2.105 | 0.0150519 | MAX dimerization protein 3 |
| SCN2A | 3.793 | 4.228 | 4.08 | 2.99 | 3.154 | 2.758 | −2.104 | 0.011657 | sodium channel, voltage-gated, type II, alpha subunit |
| CMAS | 4.475 | 5.194 | 4.854 | 3.741 | 3.592 | 4.121 | −2.104 | 0.025019 | cytidine monophosphate N-acetylneuraminic acid synthetase |
| FAM108B1 | 8.186 | 7.406 | 7.579 | 6.333 | 7.081 | 6.753 | −2.103 | 0.0379631 | family with sequence similarity 108, member B1 |
| CYC1 | 6.074 | 7.784 | 6.839 | 5.767 | 5.108 | 6.026 | −2.103 | 0.0443879 | cytochrome c-1 |
| JMJD1C | 8.166 | 8.976 | 8.627 | 7.266 | 7.897 | 7.556 | −2.101 | 0.0315289 | jumonji domain containing 1C |
| C1orf203 | 3.89 | 3.791 | 4.224 | 2.908 | 2.722 | 2.931 | −2.098 | 0.0078486 | No description |
| MAP4K3 | 5.697 | 6.698 | 6.767 | 5.112 | 5.097 | 5.699 | −2.096 | 0.0405173 | mitogen-activated protein kinase kinase kinase kinase 3 |
| CORO6 | 4.502 | 4.552 | 4.158 | 3.436 | 3.912 | 3.059 | −2.094 | 0.0393604 | coronin 6 |
| NGF | 3.355 | 6.98 | 4.021 | 3.023 | 2.289 | 3.04 | −2.093 | 0.0426365 | nerve growth factor (beta polypeptide) |
| LOC439994 | 1.587 | 1.388 | 2.008 | 0.323 | 0.988 | 0.429 | −2.092 | 0.0215983 | No description |
| TTLL3 | 6.979 | 7.844 | 8.03 | 6.065 | 6.791 | 6.779 | −2.092 | 0.0431373 | tubulin tyrosine ligase-like family, member 3 |
| PXDN | 8.039 | 7.302 | 7.262 | 6.47 | 6.481 | 6.198 | −2.09 | 0.0159562 | peroxidasin homolog (Drosophila) |
| TMEM195 | 2.977 | 2.224 | 1.784 | 1.299 | 1.07 | 1.163 | −2.087 | 0.0257909 | transmembrane protein 195 |
| CENPV | 3.075 | 3.942 | 3.595 | 2.09 | 2.261 | 2.882 | −2.085 | 0.0272333 | centromere protein V |
| CEP78 | 3.822 | 4.823 | 4.051 | 3.267 | 3.497 | 2.763 | −2.084 | 0.0395328 | centrosomal protein 78kDa |
| FLOT1 | 9.324 | 9.369 | 9.921 | 8.21 | 8.863 | 8.474 | −2.083 | 0.0265579 | flotillin 1 |
| BRI3 | 7.845 | 8.643 | 8.117 | 7.061 | 6.991 | 7.224 | −2.079 | 0.0160528 | brain protein I3 |
| SLC7A7 | 2.167 | 2.039 | 2.812 | 0.573 | 1.758 | 1.277 | −2.077 | 0.0368369 | solute carrier family 7 (cationic amino acid transporter, y+ system), member 7 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| CLSTN1 | 8.254 | 9.029 | 9.234 | 7.975 | 7.335 | 8.044 | −2.077 | 0.0402561 | calsyntenin 1 |
| ABLIM2 | 3.214 | 1.897 | 2.421 | 1.366 | 1.033 | 1.797 | −2.077 | 0.0445417 | actin binding LIM protein family, member 2 |
| LEO1 | 3.447 | 3.846 | 3.642 | 2.589 | 2.094 | 2.986 | −2.076 | 0.0218316 | Leo1, Paf1/RNA polymerase II complex component, homolog (S. cerevisiae) |
| ARF6 | 10.849 | 11.539 | 11.343 | 10.231 | 10.356 | 10.289 | −2.076 | 0.0246083 | ADP-ribosylation factor 6 |
| MXRA7 | 10.085 | 9.437 | 9.505 | 8.997 | 8.383 | 8.823 | −2.076 | 0.0380897 | matrix-remodelling associated 7 |
| LYPLAL1 | 3.41 | 3.937 | 3.483 | 2.109 | 2.689 | 2.886 | −2.073 | 0.0261408 | lysophospholipase-like 1 |
| GSTA4 | 4.536 | 4.943 | 4.62 | 2.946 | 3.904 | 3.572 | −2.067 | 0.0152672 | glutathione S-transferase alpha 4 |
| ANTXR1 | 7.417 | 7.951 | 8.058 | 6.498 | 7.011 | 6.616 | −2.067 | 0.017385 | anthrax toxin receptor 1 |
| ZNF100 | 2.274 | 2.95 | 3.016 | 1.969 | 1.434 | 1.386 | −2.067 | 0.0192488 | zinc finger protein 100 |
| IQCK | 3.719 | 3.85 | 3.748 | 2.432 | 2.804 | 2.793 | −2.064 | 0.0072984 | IQ motif containing K |
| AMIGO2 | 9.975 | 11.687 | 10.612 | 9.401 | 9.813 | 9.567 | −2.062 | 0.049756 | adhesion molecule with Ig-like domain 2 |
| SERPINB5 | 9.543 | 9.997 | 9.832 | 8.651 | 8.689 | 8.955 | −2.059 | 0.0132325 | serpin peptidase inhibitor, clade B (ovalbumin), member 5 |
| JHDM1D | 7.317 | 6.977 | 7.699 | 6.447 | 6.119 | 6.275 | −2.059 | 0.0185347 | jumonji C domain containing histone demethylase 1 homolog D (S. cerevisiae) |
| DENND4A | 6.283 | 6.942 | 7.257 | 5.901 | 5.813 | 5.918 | −2.057 | 0.0396351 | DENN/MADD domain containing 4A |
| FOXN3 | 8.114 | 8.813 | 7.907 | 6.867 | 7.361 | 7.302 | −2.057 | 0.0250726 | forkhead box N3 |
| NHLRC3 | 4.342 | 3.768 | 4.226 | 3.187 | 3.297 | 2.829 | −2.056 | 0.021486 | NHL repeat containing 3 |
| NEK6 | 4.38 | 4.71 | 4.889 | 4.074 | 3.37 | 3.34 | −2.056 | 0.0237884 | NIMA (never in mitosis gene a)-related kinase 6 |
| SMAD1 | 4.588 | 5.428 | 4.422 | 3.41 | 3.549 | 3.939 | −2.055 | 0.0223997 | SMAD family member 1 |
| PITPNM2 | 5.133 | 4.837 | 4.603 | 4.096 | 3.629 | 3.757 | −2.052 | 0.0174644 | phosphatidylinositol transfer protein, membrane-associated 2 |
| DNAJC18 | 4.205 | 4.259 | 4.512 | 3.761 | 3.122 | 3.223 | −2.05 | 0.0260635 | DnaJ (Hsp40) homolog, subfamily C, member 18 |
| FLYWCH1 | 7.015 | 7.575 | 7.989 | 6.539 | 6.773 | 6.506 | −2.05 | 0.0460249 | FLYWCH-type zinc finger 1 |
| CAMK2D | 6.865 | 7.607 | 7.908 | 5.864 | 6.874 | 6.213 | −2.047 | 0.0377255 | calcium/calmodulin-dependent protein kinase II delta |
| KANK1 | 7.685 | 8.564 | 8.142 | 7.117 | 6.795 | 7.11 | −2.046 | 0.0183795 | KN motif and ankyrin repeat domains 1 |
| RPGR | 5.567 | 4.765 | 5.422 | 4.519 | 3.878 | 4.395 | −2.038 | 0.0389433 | retinitis pigmentosa GTPase regulator |
| EEA1 | 6.183 | 6.981 | 6.907 | 5.956 | 5.256 | 5.84 | −2.035 | 0.0399392 | early endosome antigen 1 |
| ISOC1 | 5.451 | 6.642 | 5.654 | 4.443 | 4.63 | 4.934 | −2.033 | 0.0224247 | isochorismatase domain containing 1 |
| GAA | 7.578 | 8.311 | 7.888 | 6.56 | 7.287 | 6.76 | −2.033 | 0.0278837 | glucosidase, alpha; acid |
| TPBG | 7.804 | 8.991 | 8.29 | 7.417 | 7.181 | 7.267 | −2.032 | 0.0336274 | trophoblast glycoprotein |
| VIPR2 | 4.101 | 3.29 | 3.819 | 3.078 | 2.638 | 2.666 | −2.032 | 0.0382836 | vasoactive intestinal peptide receptor 2 |
| HOXC5 | 1.908 | 1.568 | 1.578 | 0.631 | 0.886 | 0.327 | −2.031 | 0.0138377 | homeobox C5 |
| APLP2 | 10.382 | 11.403 | 10.325 | 9.54 | 9.639 | 9.303 | −2.03 | 0.0218459 | amyloid beta (A4) precursor-like protein 2 |
| LGALS8 | 6.594 | 6.763 | 7.32 | 5.597 | 6.002 | 5.742 | −2.029 | 0.0164298 | lectin, galactoside-binding, soluble, 8 |
| BBS4 | 3.455 | 4.089 | 3.659 | 3.016 | 2.758 | 2.434 | −2.029 | 0.0263397 | Bardet-Biedl syndrome 4 |
| RFX2 | 7.057 | 7.475 | 8.582 | 6.174 | 6.633 | 6.454 | −2.029 | 0.0287987 | regulatory factor X, 2 (influences HLA class II expression) |
| MYEF2 | 3.071 | 4.258 | 2.818 | 1.797 | 2.156 | 2.19 | −2.028 | 0.0230987 | myelin expression factor 2 |
| YTHDF3 | 7.498 | 8.186 | 8.215 | 6.835 | 7.064 | 7.198 | −2.024 | 0.0356851 | YTH domain family, member 3 |
| EPHX2 | 5.183 | 5.734 | 5.048 | 2.657 | 4.718 | 4.173 | −2.023 | 0.0336517 | epoxide hydrolase 2, cytoplasmic |
| C4orf31 | 1.562 | 1.608 | 1.873 | 0.86 | 0.515 | 0.631 | −2.018 | 0.0116856 | chromosome 4 open reading frame 31 |
| TAF5 | 4.71 | 4.834 | 4.491 | 3.561 | 3.672 | 3.823 | −2.015 | 0.0114166 | TAF5 RNA polymerase II, TATA box binding protein (TBP)-associated factor, 100kDa |
| FBXL17 | 5.346 | 6.033 | 5.495 | 4.833 | 4.848 | 4.336 | −2.015 | 0.035024 | F-box and leucine-rich repeat protein 17 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24− N48 | CD24− N58 | CD24− N43 | CD24− N37 | CD24− N39 | CD24− N40 | Pseudo fold change | P value | Gene description |
| LPAR4 | 1.942 | 1.824 | 3.422 | 1.121 | 0.814 | 1.163 | −2.014 | 0.0281706 | lysophosphatidic acid receptor 4 |
| ACN9 | 2.548 | 3.705 | 2.724 | 2.233 | 1.538 | 1.741 | −2.014 | 0.0339243 | ACN9 homolog (S. cerevisiae) |
| XRCC6BP1 | 2.233 | 2.602 | 2.417 | 1.407 | 1.145 | 1.98 | −2.014 | 0.0426172 | XRCC6 binding protein 1 |
| BTN2A2 | 4.247 | 4.8 | 5.047 | 3.663 | 3.791 | 4.03 | −2.013 | 0.0475131 | butyrophilin, subfamily 2, member A2 |
| SMPD1 | 5.118 | 5.35 | 4.897 | 4.27 | 3.889 | 4.228 | −2.011 | 0.0168555 | sphingomyelin phosphodiesterase 1, acid lysosomal |
| C16orf62 | 4.869 | 4.432 | 4.794 | 3.318 | 3.975 | 3.786 | −2.011 | 0.0233269 | chromosome 16 open reading frame 62 |
| DOCK8 | 2.989 | 3.604 | 2.491 | 2.246 | 1.709 | 1.982 | −2.01 | 0.0379016 | dedicator of cytokinesis 8 |
| RNLS | 2.187 | 3.531 | 2.528 | 1.889 | 1.521 | 1.436 | −2.01 | 0.0384718 | renalase, FAD-dependent amine oxidase |
| FAM69B | 5.199 | 4.124 | 3.601 | 3.116 | 3.106 | 3.134 | −2.01 | 0.0386735 | family with sequence similarity 69, member B |
| ACP2 | 4.438 | 4.729 | 4.037 | 3.586 | 3.722 | 3.022 | −2.01 | 0.0391608 | acid phosphatase 2, lysosomal |
| HHAT | 4.582 | 4.267 | 4.121 | 3.052 | 3.713 | 3.261 | −2.009 | 0.0261 | hedgehog acyltransferase |
| MCF2L | 4.875 | 4.289 | 3.851 | 3.285 | 3.499 | 3.122 | −2.006 | 0.0322272 | MCF.2 cell line derived transforming sequence-like |
| TOX3 | 3.581 | 4.263 | 3.719 | 3.259 | 2.926 | 2.504 | −2.006 | 0.0410431 | TOX high mobility group box family member 3 |
| DPCD | 3.937 | 4.787 | 4.33 | 3.297 | 3.161 | 3.782 | −2.006 | 0.0461909 | deleted in primary ciliary dyskinesia homolog (mouse) |
| PCBP2 | 10.541 | 11.312 | 11.189 | 10.169 | 10.006 | 10.308 | −2.006 | 0.0497703 | poly(rC) binding protein 2 |
| PEX3 | 4.004 | 4.838 | 3.914 | 3.353 | 3.115 | 2.91 | −2.005 | 0.0234099 | peroxisomal biogenesis factor 3 |
| SRA1 | 5.645 | 6.254 | 6.592 | 5.25 | 4.845 | 5.296 | −2.005 | 0.0318573 | steroid receptor RNA activator 1 |
| SFXN3 | 6.768 | 6.93 | 6.144 | 5.685 | 5.765 | 5.849 | −2.005 | 0.0482307 | sideroflexin 3 |
| CDK5RAP2 | 6.479 | 5.856 | 6.323 | 5.07 | 5.477 | 4.979 | −2.003 | 0.0203935 | CDK5 regulatory subunit associated protein 2 |
| UBE2D1 | 6.513 | 7.058 | 6.91 | 5.961 | 5.887 | 5.913 | −1.996 | 0.0226236 | ubiquitin-conjugating enzyme E2D 1 (UBC4/5 homolog, yeast) |
| APIP | 4.551 | 5.085 | 5.259 | 4.092 | 3.608 | 4.088 | −1.996 | 0.0245518 | APAF1 interacting protein |
| CTPS2 | 4.726 | 5.25 | 5.554 | 4.224 | 4.04 | 4.558 | −1.995 | 0.0472297 | CTP synthase II |
| DOK1 | 3.616 | 2.673 | 2.312 | 1.679 | 1.944 | 1.652 | −1.991 | 0.0373306 | docking protein 1, 62kDa (downstream of tyrosine kinase 1) |
| BCAN | 4.29 | 3.92 | 3.501 | 3.013 | 2.809 | 2.928 | −1.989 | 0.025107 | brevican |
| MSH6 | 5.974 | 6.55 | 6.718 | 5.558 | 5.434 | 5.716 | −1.989 | 0.0477306 | mutS homolog 6 (E. coli) |
| NDUFV1 | 8.321 | 8.457 | 8.493 | 7.141 | 7.586 | 7.466 | −1.988 | 0.0112742 | NADH dehydrogenase (ubiquinone) flavoprotein 1, 51kDa |
| C1QTNF9 | 3.411 | 3.549 | 2.777 | 2.157 | 2.488 | 2.421 | −1.988 | 0.0432525 | C1q and tumor necrosis factor related protein 9 |
| TSHZ3 | 7.326 | 7.827 | 7.639 | 6.67 | 6.426 | 6.65 | −1.985 | 0.0140388 | teashirt zinc finger homeobox 3 |
| ELOVL5 | 9.261 | 9.505 | 9.973 | 8.21 | 8.989 | 8.552 | −1.977 | 0.0362467 | ELOVL family member 5, elongation of long chain fatty acids (FEN1/Elo2, SUR4/Elo3-like, yeast) |
| PCDHB4 | 1.959 | 3.545 | 2.5 | 1.121 | 1.521 | 1.59 | −1.972 | 0.0333419 | protocadherin beta 4 |
| SAMD9L | 2.269 | 1.793 | 1.935 | 1.121 | 0.814 | 1.163 | −1.971 | 0.0190084 | sterile alpha motif domain containing 9-like |
| FAM129B | 7.798 | 8.357 | 8.217 | 7.525 | 6.819 | 7.207 | −1.971 | 0.0361537 | family with sequence similarity 129, member B |
| GRAMD1C | 2.049 | 2.586 | 2.49 | 1.494 | 1.513 | 1.525 | −1.968 | 0.0279817 | GRAM domain containing 1C |
| CACHD1 | 7.483 | 7.916 | 8.509 | 6.654 | 7.075 | 6.94 | −1.967 | 0.0282085 | cache domain containing 1 |
| SUMF2 | 6.669 | 6.58 | 6.593 | 5.466 | 5.914 | 5.619 | −1.964 | 0.0152486 | sulfatase modifying factor 2 |
| PHF2 | 7.24 | 6.691 | 7.342 | 6.055 | 6.333 | 6.267 | −1.964 | 0.0375531 | PHD finger protein 2 |
| OAT | 8.36 | 8.97 | 9.02 | 7.977 | 7.743 | 8.047 | −1.963 | 0.0423954 | ornithine aminotransferase |
| CRY2 | 8.296 | 7.579 | 7.79 | 6.819 | 6.931 | 6.693 | −1.96 | 0.0162338 | cryptochrome 2 (photolyase-like) |
| LRRN3 | 2.556 | 3.592 | 3.61 | 1.773 | 1.758 | 2.639 | −1.96 | 0.0351735 | leucine rich repeat neuronal 3 |
| REV3L | 6.391 | 6.932 | 6.546 | 5.421 | 5.734 | 5.87 | −1.959 | 0.0251263 | REV3-like, catalytic subunit of DNA polymerase zeta (yeast) |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24- N48 | CD24- N58 | CD24- N43 | CD24- N37 | CD24- N39 | CD24- N40 | | | |
| RWDD2B | 3.456 | 3.548 | 3.094 | 2.49 | 1.818 | 2.614 | −1.954 | 0.0247056 | RWD domain containing 2B |
| LAMB2 | 9.981 | 10.127 | 10.151 | 8.972 | 9.161 | 9.232 | −1.953 | 0.0100064 | laminin, beta 2 (laminin S) |
| PDE4D | 4.961 | 4.533 | 5.066 | 3.785 | 4.062 | 3.995 | −1.953 | 0.0258983 | phosphodiesterase 4D, cAMP-specific |
| FKBP10 | 7.587 | 7.865 | 7.812 | 6.932 | 6.564 | 6.847 | −1.952 | 0.0140245 | FK506 binding protein 10, 65 kDa |
| PACSIN2 | 6.267 | 5.655 | 5.912 | 4.69 | 5.422 | 4.813 | −1.952 | 0.0362875 | protein kinase C and casein kinase substrate in neurons 2 |
| PTP RA | 6.812 | 7.072 | 7.548 | 6.48 | 6.108 | 5.855 | −1.95 | 0.0314552 | protein tyrosine phosphatase, receptor type, A |
| LOC96610 | 7.007 | 7.055 | 7.429 | 6.094 | 6.093 | 6.063 | −1.949 | 0.0081849 | No description |
| DAP | 7.398 | 7.184 | 6.745 | 6.437 | 5.746 | 6.32 | −1.948 | 0.0407155 | death-associated protein |
| USP13 | 5.622 | 5.675 | 5.204 | 4.661 | 4.093 | 4.777 | −1.947 | 0.0283559 | ubiquitin specific peptidase 13 (isopeptidase T-3) |
| QPRT | 4.496 | 4.305 | 4.969 | 3.537 | 3.538 | 3.387 | −1.945 | 0.012522 | quinolinate phosphoribosyltransferase |
| PAQR8 | 2.741 | 2.794 | 2.656 | 1.837 | 1.569 | 1.837 | −1.941 | 0.0095214 | progestin and adipoQ receptor family member VIII |
| BTBD2 | 6.98 | 6.706 | 6.657 | 5.599 | 6.283 | 5.749 | −1.94 | 0.0348344 | BTB (POZ) domain containing 2 |
| KCTD10 | 6.769 | 7.775 | 7.099 | 6.355 | 5.813 | 6.392 | −1.939 | 0.0396938 | potassium channel tetramerisation domain containing 10 |
| TAB3 | 7.222 | 7.489 | 7.819 | 6.526 | 6.535 | 6.594 | −1.937 | 0.0191028 | TGF-beta activated kinase 1/MAP3K7 binding protein 3 |
| ZHX3 | 6.196 | 5.663 | 6.518 | 5.564 | 4.824 | 5.048 | −1.937 | 0.0437304 | zinc fingers and homeoboxes 3 |
| UBTD2 | 8.766 | 8.454 | 8.623 | 7.447 | 7.893 | 7.672 | −1.933 | 0.0182493 | ubiquitin domain containing 2 |
| SOAT1 | 6.093 | 5.56 | 6.267 | 5.161 | 5.024 | 5.142 | −1.933 | 0.0338265 | sterol O-acyltransferase 1 |
| HERC5 | 4.121 | 3.227 | 3.852 | 2.281 | 2.902 | 2.966 | −1.932 | 0.0400286 | hect domain and RLD 5 |
| C5orf15 | 6.856 | 7.352 | 6.961 | 6.014 | 6.002 | 6.328 | −1.928 | 0.022072 | chromosome 5 open reading frame 15 |
| PBX1 | 7.546 | 7.779 | 7.212 | 6.032 | 6.949 | 6.6 | −1.926 | 0.0389647 | pre-B-cell leukemia homeobox 1 |
| XBP1 | 8.89 | 9.559 | 9.919 | 8.615 | 8.283 | 8.652 | −1.924 | 0.0490892 | X-box binding protein 1 |
| RECK | 6.333 | 6.499 | 7.046 | 5.532 | 5.558 | 5.67 | −1.92 | 0.018285 | reversion-inducing-cysteine-rich protein with kazal motifs |
| LRRC28 | 3.956 | 4.142 | 3.96 | 2.533 | 3.259 | 3.022 | −1.916 | 0.0156893 | leucine rich repeat containing 28 |
| ZBTB47 | 6.153 | 5.575 | 6.153 | 5.218 | 5.076 | 5.049 | −1.913 | 0.0377184 | zinc finger and BTB domain containing 47 |
| PGAP2 | 4.453 | 4.786 | 4.669 | 3.367 | 3.924 | 3.735 | −1.911 | 0.0210174 | post-GPI attachment to proteins 2 |
| B3GNT2 | 6.15 | 6.692 | 5.882 | 4.948 | 5.314 | 5.36 | −1.91 | 0.0255513 | UDP-GlcNAc:betaGal beta-1,3-N-acetylglucosaminyltransferase 2 |
| WWC3 | 6.875 | 7.551 | 7.077 | 6.282 | 5.943 | 6.57 | −1.908 | 0.0437941 | WWC family member 3 |
| PSMB8 | 7.598 | 6.732 | 6.464 | 5.533 | 5.993 | 6.012 | −1.906 | 0.0363597 | proteasome (prosome, macropain) subunit, beta type, 8 (large multifunctional peptidase 7) |
| EIF2C4 | 3.814 | 4.749 | 4.081 | 3.323 | 2.884 | 3.294 | −1.904 | 0.0303212 | eukaryotic translation initiation factor 2C, 4 |
| ZNF654 | 6.052 | 6.304 | 6.283 | 5.088 | 5.354 | 5.625 | −1.904 | 0.0306432 | zinc finger protein 654 |
| HDGFRP3 | 6.937 | 6.894 | 6.802 | 5.966 | 5.614 | 6.237 | −1.903 | 0.0223853 | No description |
| PHLPP1 | 7.448 | 8.298 | 7.888 | 6.756 | 7.061 | 6.96 | −1.903 | 0.0337197 | PH domain and leucine rich repeat protein phosphatase 1 |
| TMEM66 | 9.206 | 10.16 | 9.704 | 8.362 | 8.86 | 8.776 | −1.903 | 0.0338299 | transmembrane protein 66 |
| STK17A | 10.47 | 11.038 | 10.312 | 9.384 | 9.965 | 9.769 | −1.903 | 0.0461401 | serine/threonine kinase 17a |
| ARPC1B | 7.783 | 6.124 | 6.302 | 5.364 | 5.374 | 5.604 | −1.902 | 0.0362538 | actin related protein 2/3 complex, subunit 1B, 41kDa |
| FBXO31 | 8.203 | 7.968 | 7.896 | 7.276 | 6.953 | 7.236 | −1.9 | 0.0226744 | F-box protein 31 |
| PNKD | 6.235 | 6.945 | 6.241 | 5.39 | 5.816 | 5.309 | −1.9 | 0.0355677 | paroxysmal nonkinesigenic dyskinesia |
| TMEM170A | 4.902 | 5.351 | 4.615 | 4.366 | 3.946 | 3.978 | −1.898 | 0.0480439 | transmembrane protein 170A |
| CENPJ | 1.684 | 2.298 | 1.855 | 1.121 | 0.814 | 0.935 | −1.893 | 0.0203155 | centromere protein J |

TABLE 6-continued

Differentially Expressed Genes in CD10+ Breast Epithelial Cells

| Gene Symbol | Nulliparous (NP) Samples | | | Parous (P) Samples | | | | Pseudo fold change | P value | Gene description |
|---|---|---|---|---|---|---|---|---|---|---|
| | CD24+ N48 | CD24+ N58 | CD24+ N43 | CD24+ N37 | CD24+ N39 | CD24+ N40 | | | | |
| ARHGEF12 | 7.547 | 8.064 | 7.992 | 7.073 | 7.051 | 7.133 | | −1.891 | 0.0413594 | Rho guanine nucleotide exchange factor (GEF) 12 |
| CCDC85B | 8.221 | 9.793 | 8.37 | 7.303 | 7.633 | 7.612 | | −1.89 | 0.0345239 | coiled-coil domain containing 85B |
| EFNA3 | 4.067 | 5.021 | 5.075 | 3.21 | 4.157 | 3.418 | | −1.89 | 0.0412871 | ephrin-A3 |
| PLD3 | 8.563 | 8.821 | 8.912 | 8.12 | 7.646 | 7.646 | | −1.889 | 0.020812 | phospholipase D family, member 3 |
| HGSNAT | 6.968 | 7.196 | 7.474 | 6.278 | 6.457 | 6.174 | | −1.889 | 0.0228296 | heparan-alpha-glucosaminide N-acetyltransferase |
| PAM | 8.212 | 7.757 | 7.871 | 7.5 | 6.491 | 6.955 | | −1.887 | 0.0442656 | peptidylglycine alpha-amidating monooxygenase |
| PDZD11 | 3.821 | 4.508 | 3.801 | 3.144 | 3.128 | 2.886 | | −1.886 | 0.0264578 | PDZ domain containing 11 |
| RASA3 | 4.975 | 5.678 | 5.457 | 4.544 | 4.42 | 4.541 | | −1.886 | 0.036671 | RAS p21 protein activator 3 |
| DNAJC15 | 4.901 | 5.454 | 4.721 | 4.071 | 3.864 | 3.986 | | −1.885 | 0.0183967 | DnaJ (Hsp40) homolog, subfamily C, member 15 |
| C1orf21 | 9.795 | 10.108 | 10.069 | 8.851 | 9.324 | 9.155 | | −1.884 | 0.026706 | chromosome 1 open reading frame 21 |
| SATB1 | 4.072 | 4.687 | 3.951 | 3.29 | 3.039 | 3.262 | | −1.881 | 0.0207469 | SATB homeobox 1 |
| LIMK2 | 7.39 | 8.086 | 7.634 | 6.722 | 6.844 | 6.658 | | −1.881 | 0.0238635 | LIM domain kinase 2 |
| PCSK5 | 6.057 | 6.665 | 6.646 | 5.373 | 5.577 | 5.754 | | −1.88 | 0.0368606 | proprotein convertase subtilisin/kexin type 5 |
| IPW | 4.662 | 5.757 | 4.989 | 3.927 | 4.079 | 4.104 | | −1.879 | 0.0272834 | imprinted in Prader-Willi syndrome (non-protein coding) |
| BPHL | 4.172 | 5.069 | 4.172 | 3.267 | 3.786 | 3.286 | | −1.873 | 0.0388188 | biphenyl hydrolase-like (serine hydrolase) |
| APPL2 | 5.836 | 6.134 | 6.679 | 5.229 | 5.089 | 5.561 | | −1.873 | 0.0430844 | adaptor protein, phosphotyrosine interaction, PH domain and leucine zipper containing 2 |
| COL4A1 | 11.511 | 10.868 | 10.804 | 10.423 | 9.902 | 10.169 | | −1.869 | 0.0452579 | collagen, type IV, alpha 1 |
| ESD | 6.532 | 7.036 | 6.76 | 5.63 | 5.739 | 6.35 | | −1.869 | 0.0494362 | esterase D |
| ARID5A | 10.643 | 8.878 | 9.24 | 8.443 | 8.342 | 8.001 | | −1.864 | 0.0355491 | AT rich interactive domain 5A (MRF1-like) |
| SCRN1 | 3.806 | 5.412 | 3.967 | 3.148 | 2.909 | 3.225 | | −1.863 | 0.0331394 | secernin 1 |
| CREBL2 | 4.947 | 5.739 | 5.347 | 4.128 | 4.844 | 4.17 | | −1.86 | 0.0452293 | cAMP responsive element binding protein-like 2 |
| BTG1 | 9.78 | 10.114 | 9.662 | 8.28 | 9.219 | 9.025 | | −1.859 | 0.0358317 | B-cell translocation gene 1, anti-proliferative |
| FIS1 | 6.996 | 6.794 | 7.064 | 5.525 | 6.127 | 6.171 | | −1.857 | 0.021114 | fission 1 (mitochondrial outer membrane) homolog (S. cerevisiae) |
| PEX19 | 5.324 | 5.429 | 5.39 | 4.565 | 4.498 | 4.268 | | −1.855 | 0.0115633 | peroxisomal biogenesis factor 19 |
| ZNF622 | 6.962 | 7.582 | 6.792 | 6.071 | 6.306 | 6.071 | | −1.855 | 0.0306647 | zinc finger protein 622 |
| PCDHB16 | 4.326 | 4.819 | 4.317 | 3.435 | 3.937 | 2.998 | | −1.855 | 0.0333061 | protocadherin beta 16 |
| PSEN1 | 7.303 | 6.693 | 7.121 | 6.325 | 6.064 | 6.229 | | −1.855 | 0.0392559 | presenilin 1 |
| MLXIPL | 3.315 | 3.043 | 3.968 | 2.689 | 2.427 | 2.421 | | −1.852 | 0.0429928 | MLX interacting protein-like |
| HCFC2 | 3.821 | 4.058 | 4.145 | 3.39 | 3.172 | 2.479 | | −1.848 | 0.0335015 | host cell factor C2 |
| RAB8B | 6.612 | 6.855 | 7.729 | 6.194 | 5.822 | 5.969 | | −1.848 | 0.034765 | RAB8B, member RAS oncogene family |
| TMEM200A | 4.059 | 4.575 | 4.127 | 3.689 | 3.039 | 3.457 | | −1.848 | 0.0473142 | transmembrane protein 200A |
| SLC2A5 | 2.585 | 2.129 | 2.504 | 1.922 | 1.297 | 1.244 | | −1.847 | 0.0384789 | solute carrier family 2 (facilitated glucose/fructose transporter), member 5 |
| BLMH | 5.235 | 4.82 | 4.869 | 4.326 | 3.797 | 4.353 | | −1.844 | 0.0494856 | bleomycin hydrolase |
| ARAP3 | 6.819 | 6.536 | 6.918 | 6.16 | 5.626 | 5.937 | | −1.843 | 0.0354518 | ArfGAP with RhoGAP domain, ankyrin repeat and PH domain 3 |
| NBPF14 | 2.936 | 3.328 | 3.196 | 2.277 | 2.332 | 2.316 | | −1.84 | 0.0216677 | neuroblastoma breakpoint family, member 14 |
| THRA | 5.737 | 5.742 | 5.643 | 4.59 | 5.183 | 4.858 | | −1.839 | 0.0347263 | thyroid hormone receptor, alpha (erythroblastic leukemia viral (v-erb-a) oncogene homolog, avian) |
| RILP | 5.484 | 5.094 | 4.793 | 4.397 | 4.359 | 3.915 | | −1.838 | 0.0403191 | Rab interacting lysosomal protein |
| ARSA | 5.544 | 5.456 | 5.135 | 4.579 | 4.171 | 4.802 | | −1.837 | 0.0404822 | arylsulfatase A |
| NIN | 6.549 | 6.291 | 7.402 | 5.585 | 5.981 | 5.672 | | −1.837 | 0.0452951 | ninein (GSK3B interacting protein) |
| FRCP | 6.454 | 6.523 | 6.223 | 5.641 | 5.179 | 5.646 | | −1.836 | 0.0243865 | prolylcarboxypeptidase (angiotensinase C) |
| ALDH16A1 | 6.301 | 6.079 | 6.295 | 5.738 | 5.407 | 5.204 | | −1.834 | 0.0448737 | aldehyde dehydrogenase 16 family, member A1 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
| --- | --- | --- | --- | --- | --- | --- | --- | --- | --- |
| | CD24+ N48 | CD24+ N58 | CD24+ N43 | CD24+ N37 | CD24+ N39 | CD24+ N40 | | | |
| OLFM2 | 6.579 | 6.24 | 6.458 | 5.369 | 5.748 | 5.541 | −1.829 | 0.0235666 | olfactomedin 2 |
| PTPN12 | 7.777 | 8.563 | 8.109 | 7.24 | 7.217 | 7.366 | −1.826 | 0.0400558 | protein tyrosine phosphatase, non-receptor type 12 |
| ALAS1 | 5.525 | 4.921 | 4.777 | 4.098 | 4.187 | 3.909 | −1.824 | 0.0236982 | aminolevulinate, delta-, synthase 1 |
| TP53INP2 | 6.269 | 6.194 | 5.851 | 5.315 | 5.405 | 5.293 | −1.821 | 0.0364234 | tumor protein p53 inducible nuclear protein 2 |
| NCSTN | 7.226 | 7.245 | 6.816 | 6.307 | 6.361 | 6.38 | −1.821 | 0.0428568 | nicastrin |
| UBE2L6 | 6.67 | 6.296 | 7.033 | 5.471 | 5.84 | 5.808 | −1.817 | 0.0295371 | ubiquitin-conjugating enzyme E2L 6 |
| RAB1A | 9.587 | 10.632 | 9.977 | 8.97 | 9.116 | 9.214 | −1.817 | 0.0421342 | RAB1 A, member RAS oncogene family |
| DCP2 | 5.431 | 5.845 | 5.806 | 4.683 | 4.944 | 4.97 | −1.816 | 0.0320612 | DCP2 decapping enzyme homolog (S. cerevisiae) family |
| ATG2B | 4.749 | 5.633 | 5.108 | 4.247 | 4.306 | 4.177 | −1.816 | 0.0382908 | ATG2 autophagy related 2 homolog B (S. cerevisiae) |
| RFX7 | 4.815 | 5.979 | 5.024 | 4.364 | 4.337 | 3.956 | −1.814 | 0.0418924 | regulatory factor X, 7 |
| STARD3NL | 6.961 | 6.848 | 7.623 | 5.992 | 6.133 | 6.114 | −1.81 | 0.0192845 | STARD3 N-terminal like |
| ZNF185 | 5.936 | 7.256 | 5.959 | 5.08 | 5.193 | 5.452 | −1.809 | 0.041657 | zinc finger protein 185 (LIM domain) |
| C14orf37 | 2.144 | 3.173 | 2.09 | 1.659 | 1.235 | 1.386 | −1.809 | 0.042072 | chromosome 14 open reading frame 37 |
| C19orf71 | 2.108 | 1.513 | 1.885 | 1.033 | 0.609 | 1.277 | −1.804 | 0.0493954 | chromosome 19 open reading frame 71 |
| RDH10 | 5.358 | 5.313 | 5.571 | 4.507 | 4.869 | 4.463 | −1.802 | 0.0345739 | retinol dehydrogenase 10 (all-trans) |
| TUBGCP3 | 2.672 | 3.361 | 3.246 | 2.035 | 1.827 | 2.607 | −1.796 | 0.0478837 | tubulin, gamma complex associated protein 3 |
| CPA1 | 2.495 | 2.677 | 2.229 | 1.818 | 1.387 | 1.779 | −1.793 | 0.0431874 | carboxypeptidase A1 (pancreatic) |
| LSM2 | 5.896 | 6.862 | 6.005 | 5.167 | 5.338 | 5.141 | −1.787 | 0.0312671 | LSM2 homolog, U6 small nuclear RNA associated (S. cerevisiae) |
| KIAA1715 | 4.566 | 4.647 | 5.02 | 4.04 | 3.728 | 4.039 | −1.787 | 0.0385719 | KIAA1715 |
| HDAC11 | 5.146 | 4.885 | 4.85 | 3.929 | 4.247 | 4.31 | −1.784 | 0.0349238 | histone deacetylase 11 |
| PRPS2 | 5.036 | 4.875 | 5.136 | 4.202 | 3.928 | 4.442 | −1.783 | 0.0339679 | phosphoribosyl pyrophosphate synthetase 2 |
| FAM102B | 3.846 | 4.422 | 4.164 | 3.012 | 3.06 | 3.694 | −1.783 | 0.0475567 | family with sequence similarity 102, member B |
| TRAF3IP2 | 6.176 | 6.007 | 6.301 | 5.464 | 5.343 | 5.183 | −1.782 | 0.0233197 | TRAF3 interacting protein 2 |
| SLC44A1 | 6.318 | 6.669 | 6.553 | 5.12 | 5.72 | 5.901 | −1.782 | 0.0358188 | solute carrier family 44, member 1 |
| FAM131B | 3.463 | 2.983 | 3.089 | 2.261 | 2.284 | 2.171 | −1.776 | 0.0175703 | family with sequence similarity 131, member B |
| PLK3 | 8.736 | 9.086 | 8.615 | 7.787 | 8.042 | 7.952 | −1.775 | 0.0241947 | polo-like kinase 3 |
| CHMP5 | 6.415 | 6.698 | 6.278 | 5.355 | 5.896 | 5.588 | −1.775 | 0.0368749 | chromatin modifying protein 5 |
| CASKIN1 | 6.034 | 6.115 | 6.007 | 5.063 | 5.531 | 5.213 | −1.767 | 0.0354711 | CASK interacting protein 1 |
| TIMP3 | 10.062 | 10.19 | 10.06 | 8.779 | 9.51 | 9.244 | −1.764 | 0.0293153 | TIMP metallopeptidase inhibitors |
| SLC38A10 | 5.866 | 5.44 | 5.628 | 4.936 | 4.795 | 4.817 | −1.754 | 0.0310253 | solute carrier family 38, member 10 |
| SNX15 | 4.395 | 4.502 | 4.088 | 3.483 | 3.277 | 3.691 | −1.754 | 0.0319804 | sorting nexin 15 |
| C6orf89 | 4.834 | 5.108 | 4.835 | 4.299 | 3.678 | 4.234 | −1.752 | 0.0402061 | chromosome 6 open reading frame 89 |
| PDE8A | 5.131 | 5.016 | 5.251 | 4.443 | 4.344 | 4.171 | −1.751 | 0.0231409 | phosphodiesterase 8A |
| CBLN3 | 2.427 | 2.132 | 1.837 | 1.366 | 1.033 | 1.348 | −1.746 | 0.0321392 | cerebellin 3 precursor |
| WBP2 | 8.442 | 9.157 | 8.249 | 7.459 | 7.641 | 7.762 | −1.742 | 0.0330715 | WW domain binding protein 2 |
| AFF1 | 7.402 | 6.832 | 6.905 | 6.261 | 6.031 | 6.346 | −1.742 | 0.0407706 | AF4/FMR2 family, member 1 |
| ZMIZ1 | 7.884 | 8.805 | 8.106 | 7.084 | 7.546 | 7.373 | −1.74 | 0.047292 | zinc finger, MIZ-type containing 1 |
| PDSS2 | 2.442 | 2.957 | 2.442 | 2.008 | 1.645 | 1.747 | −1.737 | 0.0448494 | prenyl (decaprenyl) diphosphate synthase, subunit 2 |
| RPS3A | 13.092 | 12.979 | 13.175 | 12.205 | 12.185 | 12.426 | −1.733 | 0.0221693 | ribosomal protein S3A |
| RCN1 | 9.114 | 9.436 | 9.54 | 8.645 | 8.321 | 8.792 | −1.73 | 0.0490821 | reticulocalbin 1, EF-hand calcium binding domain |
| AKTIP | 3.407 | 3.791 | 3.513 | 3.002 | 2.432 | 2.802 | −1.728 | 0.0424605 | AKT interacting protein |
| PRC1 | 3.176 | 3.456 | 3.994 | 2.388 | 2.689 | 2.688 | −1.727 | 0.0332646 | protein regulator of cytokinesis 1 |
| BCAS2 | 4.823 | 4.777 | 5.952 | 3.989 | 4.137 | 4.329 | −1.726 | 0.0482571 | breast carcinoma amplified sequence 2 |
| BTBD3 | 5.275 | 5.89 | 5.901 | 5.114 | 4.639 | 4.58 | −1.725 | 0.0416785 | BTB (POZ) domain containing 3 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| BACE1 | 6.321 | 6.371 | 6.073 | 5.539 | 5.557 | 5.329 | −1.72 | 0.0305774 | beta-site APP-cleaving enzyme 1 |
| PPFIBP1 | 9.97 | 10.098 | 9.82 | 9.188 | 9.301 | 9.177 | −1.72 | 0.0307291 | PTPRF interacting protein, binding protein 1 (liprin beta 1) |
| CSRP2 | 7.912 | 8.043 | 8.274 | 7.174 | 7.518 | 7.485 | −1.714 | 0.0447643 | cysteine and glycine-rich protein 2 |
| DCTN2 | 6.81 | 8.043 | 7.1 | 6.323 | 6.411 | 6.113 | −1.714 | 0.0450118 | dynactin 2 (p50) |
| C12orf23 | 6.408 | 6.653 | 6.495 | 5.447 | 5.72 | 5.939 | −1.711 | 0.033802 | chromosome 12 open reading frame 23 |
| C6orf211 | 3.233 | 3.383 | 3.058 | 2.283 | 2.575 | 2.602 | −1.711 | 0.0440774 | chromosome 6 open reading frame 211 |
| ATP9A | 5.764 | 5.913 | 5.866 | 4.898 | 5.14 | 5.137 | −1.709 | 0.0238277 | ATPase, class II, type 9A |
| ZDHHC21 | 2.477 | 3.003 | 2.43 | 1.659 | 1.787 | 1.747 | −1.705 | 0.026691 | zinc finger, DHHC-type containing 21 |
| FEM1C | 7.569 | 7.45 | 8.013 | 6.741 | 6.804 | 7.004 | −1.7 | 0.0384145 | fem-1 homolog c (C. elegans) |
| RPL3 | 14.158 | 14.27 | 14.309 | 13.394 | 13.58 | 13.476 | −1.699 | 0.0233484 | ribosomal protein L3 |
| MYL5 | 3.147 | 3.453 | 3.741 | 2.794 | 2.551 | 2.688 | −1.699 | 0.0498118 | myosin, light chain 5, regulatory |
| PTGER | 2.302 | 2.112 | 3.379 | 1.556 | 1.434 | 1.541 | −1.695 | 0.0395621 | prostaglandin F receptor (FP) |
| MED29 | 6.927 | 6.258 | 6.351 | 5.826 | 5.497 | 5.611 | −1.695 | 0.0411963 | mediator complex subunit 29 |
| EIF4E | 8.675 | 8.976 | 8.845 | 7.917 | 8.085 | 8.182 | −1.694 | 0.0317007 | eukaryotic translation initiation factor 4E |
| ORAI3 | 3.41 | 4.007 | 3.185 | 2.759 | 2.429 | 2.695 | −1.69 | 0.0419911 | ORAI calcium release-activated calcium modulator 3 |
| KRTCAP2 | 7.038 | 6.953 | 6.587 | 5.905 | 6.283 | 6.079 | −1.688 | 0.0470816 | keratinocyte associated protein 2 |
| CD9 | 9.431 | 10.283 | 9.52 | 8.766 | 8.73 | 9.017 | −1.686 | 0.046349 | CD9 molecule |
| SLC25A12 | 5.854 | 6.393 | 5.814 | 5.084 | 5.106 | 5.392 | −1.68 | 0.0444022 | solute carrier family 25 (mitochondrial carrier, Aralar), member 12 |
| AP2M1 | 7.971 | 8.589 | 8.003 | 7.488 | 7.351 | 7.223 | −1.679 | 0.0439171 | adaptor-related protein complex 2, mu 1 subunit |
| RBMS1 | 9.889 | 9.586 | 10.14 | 9.181 | 9.02 | 9.149 | −1.671 | 0.0480582 | RNA binding motif, single stranded interacting protein 1 |
| CBLB | 8.667 | 8.365 | 8.155 | 7.625 | 7.73 | 7.447 | −1.67 | 0.0402633 | Cas-Br-M (murine) ecotropic retroviral transforming sequence b |
| KLF3 | 7.554 | 7.38 | 7.413 | 6.97 | 6.296 | 6.681 | −1.66 | 0.0476261 | Kruppel-like factor 3 (basic) |
| YWHAH | 9.163 | 9.848 | 9.242 | 8.458 | 8.518 | 8.727 | −1.651 | 0.0446805 | tyrosine 3-monooxygenase/tryptophan 5-monooxygenase activation protein, eta polypeptide |
| USP3 | 6.299 | 6.883 | 6.289 | 5.68 | 5.567 | 5.593 | −1.65 | 0.0325585 | ubiquitin specific peptidase 3 |
| BSN | 1.366 | 1.651 | 1.58 | 0.86 | 0.848 | 0.886 | −1.646 | 0.0453846 | bassoon (presynaptic cytomatrix protein) |
| LRTOMT | 3.917 | 3.586 | 3.569 | 2.963 | 3.048 | 2.864 | −1.631 | 0.0414696 | leucine rich transmembrane and 0-methyltransferase domain containing |
| LBR | 7.479 | 7.324 | 7.546 | 6.753 | 6.847 | 6.777 | −1.623 | 0.0433569 | lamin B receptor |
| FAM172A | 4.3 | 4.88 | 4.262 | 3.662 | 3.615 | 3.613 | −1.607 | 0.0373378 | family with sequence similarity 172, member A |
| FAM54B | 5.931 | 6.416 | 6.044 | 5.319 | 5.373 | 5.432 | −1.592 | 0.043123 | family with sequence similarity 54, member B |
| SH3GLB1 | 8.583 | 8.42 | 8.412 | 7.519 | 7.805 | 7.919 | −1.585 | 0.0451227 | SH3-domain GRB2-like endophilin B1 |
| SLC39A1 | 8.316 | 8.325 | 8.437 | 7.783 | 7.559 | 7.751 | −1.573 | 0.0448995 | solute carrier family 39 (zinc transporter), member 1 |
| LAMP1 | 8.84 | 9.256 | 8.907 | 8.333 | 8.21 | 8.274 | −1.551 | 0.0447006 | lysosomal-associated membrane protein 1 |
| SPRED1 | 8.537 | 8.551 | 9.018 | 7.944 | 7.96 | 7.944 | −1.524 | 0.0459176 | sprouty-related, EVH1 domain containing 1 |
| | | | | | | Higher Expression in Parous | | | |
| BPNT1 | 10.259 | 10.169 | 10.19 | 10.843 | 10.823 | 10.817 | 1.552 | 0.038358 | 3'(2'), 5'-bisphosphate nucleotidase 1 |
| CCDC124 | 6.993 | 7.012 | 6.866 | 7.891 | 7.507 | 7.619 | 1.56 | 0.0446433 | coiled-coil domain containing 124 |
| BCL2L2 | 7.758 | 7.328 | 7.727 | 8.26 | 8.408 | 8.308 | 1.569 | 0.0498641 | BCL2-like 2 |
| FDPSL2A | 4.21 | 4.018 | 4.326 | 4.807 | 4.948 | 4.862 | 1.571 | 0.0443743 | No description |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| WDR83 | 3.491 | 3.624 | 3.638 | 4.151 | 4.278 | 4.475 | 1.581 | 0.0391228 | WD repeat domain 83 |
| LOC339290 | 6.475 | 6.494 | 6.39 | 6.984 | 7.323 | 7.136 | 1.582 | 0.043817 | No description |
| RMND1 | 1.994 | 1.728 | 1.858 | 2.525 | 2.637 | 2.477 | 1.587 | 0.0420505 | required for meiotic nuclear division 1 homolog (S. cerevisiae) |
| TRDMT1 | 3.95 | 4.052 | 3.968 | 4.797 | 4.509 | 4.637 | 1.589 | 0.0488517 | tRNA aspartic acid methyltransferase 1 |
| BCKDHB | 5.685 | 5.641 | 5.49 | 6.46 | 6.159 | 6.315 | 1.595 | 0.0417142 | branched chain keto acid dehydrogenase E1, beta polypeptide |
| LOC389834 | 6.661 | 6.244 | 6.623 | 7.298 | 7.206 | 7.317 | 1.597 | 0.0379559 | No description |
| OR1J1 | 5.108 | 5.079 | 5.036 | 5.585 | 5.786 | 5.764 | 1.599 | 0.0470509 | olfactory receptor, family 1, subfamily J, member 1 |
| ZNF77 | 5.954 | 5.398 | 5.745 | 6.634 | 6.398 | 6.374 | 1.602 | 0.0488445 | zinc finger protein 77 |
| MAN1A2 | 4.472 | 4.381 | 4.03 | 4.916 | 5.063 | 5.113 | 1.603 | 0.0468119 | mannosidase, alpha, class 1A, member 2 |
| ZMYM4 | 6.09 | 5.738 | 5.737 | 6.616 | 6.677 | 6.42 | 1.605 | 0.0497353 | zinc finger, MYM-type 4 |
| CNN3 | 11.012 | 10.759 | 11.163 | 11.699 | 11.765 | 11.658 | 1.61 | 0.0449667 | calponin 3, acidic |
| ZNF345 | 3.518 | 3.381 | 3.267 | 3.957 | 4.183 | 4.08 | 1.613 | 0.0446119 | zinc finger protein 345 |
| PTPRF | 8.459 | 8.437 | 8.034 | 9.099 | 9.15 | 8.982 | 1.614 | 0.0399463 | protein tyrosine phosphatase, receptor type, F |
| TAT | 6.439 | 6.918 | 6.824 | 7.517 | 7.524 | 7.488 | 1.617 | 0.0368677 | tyrosine aminotransferase |
| ZFYVE27 | 6.791 | 6.062 | 6.697 | 7.305 | 7.397 | 7.439 | 1.624 | 0.0422952 | zinc finger, FYVE domain containing 27 |
| TMCO3 | 4.649 | 4.783 | 4.839 | 5.923 | 5.341 | 5.487 | 1.629 | 0.0375746 | transmembrane and coiled-coil domains 3 |
| TIMM44 | 8.207 | 8.067 | 8.179 | 8.998 | 8.779 | 8.814 | 1.638 | 0.0336589 | translocase of inner mitochondrial membrane 44 homolog (yeast) |
| GLE1 | 3.846 | 3.349 | 3.893 | 4.569 | 4.562 | 4.466 | 1.643 | 0.0343099 | GLE1 RNA export mediator homolog (yeast) |
| MAT2B | 4.773 | 4.912 | 4.695 | 5.409 | 5.633 | 5.541 | 1.648 | 0.0320004 | methionine adenosyltransferase II. beta |
| CCDC59 | 8.384 | 8.443 | 7.743 | 9.165 | 9.108 | 8.92 | 1.651 | 0.0411891 | coiled-coil domain containing 59 |
| C1orf35 | 7.142 | 7.386 | 7.082 | 7.865 | 8.338 | 7.769 | 1.651 | 0.0493511 | chromosome 1 open reading frame 35 |
| DKFZP586I14 20 | 3.202 | 3.536 | 3.743 | 4.158 | 4.21 | 4.47 | 1.654 | 0.0461716 | No description |
| ZNF514 | 1.525 | 2.122 | 2.359 | 2.829 | 2.849 | 2.959 | 1.655 | 0.0443436 | zinc finger protein 514 |
| THBS1 | 12.134 | 12.358 | 12.542 | 12.953 | 13.084 | 13.123 | 1.655 | 0.0479538 | thrombospondin 1 |
| MGAT4B | 8.367 | 8.388 | 8.462 | 9.191 | 9.118 | 8.941 | 1.658 | 0.0407083 | mannosyl (alpha-1,3-)-glycoprotein beta-1,4-N-acetylglucosaminyltransferase, isozyme B |
| NAA15 | 8.098 | 7.122 | 8.046 | 8.61 | 8.776 | 8.821 | 1.659 | 0.0417672 | N(alpha)-acetyltransferase 15, NatA auxiliary subunit |
| HCG18 | 7.283 | 6.661 | 7.057 | 7.883 | 7.774 | 7.79 | 1.662 | 0.0399943 | HLA complex group 18 |
| PAK2 | 5.954 | 5.769 | 4.932 | 6.506 | 6.654 | 6.455 | 1.666 | 0.0401331 | p21 protein (Cdc42/Rac)-activated kinase 2 |
| C11orf57 | 6.205 | 6.189 | 5.816 | 6.943 | 6.79 | 6.755 | 1.667 | 0.0395471 | chromosome 11 open reading frame 57 |
| TAF4 | 6.912 | 6.129 | 6.813 | 7.398 | 7.559 | 7.553 | 1.67 | 0.0426737 | TAF4 RNA polymerase II, TATA box binding protein (TBP)-associated factor, 135kDa |
| TNFRSF6B | 4.862 | 4.69 | 4.584 | 5.828 | 5.327 | 5.365 | 1.674 | 0.0429456 | tumor necrosis factor receptor superfamily, member 6b, decoy |
| ATAD3B | 9.926 | 8.893 | 9.743 | 10.671 | 10.435 | 10.343 | 1.675 | 0.0468999 | ATPase family, AAA domain containing 3B |
| DNAJC5 | 4.243 | 4.121 | 4.242 | 4.868 | 4.949 | 5.017 | 1.678 | 0.0238206 | DnaJ (Hsp40) homolog, subfamily C, member 5 |
| DNAL1 | 3.979 | 3.628 | 3.816 | 4.938 | 4.554 | 4.376 | 1.679 | 0.0424848 | dynein, axonemal, light chain 1 |
| FERMT1 | 2.056 | 2.946 | 2.944 | 3.613 | 3.696 | 3.414 | 1.682 | 0.0480311 | fermitin family member 1 |
| ZC3H6 | 8.078 | 7.644 | 8.024 | 8.714 | 8.831 | 8.524 | 1.685 | 0.0427796 | zinc finger CCCH-type containing 6 |
| CCDC120 | 8.5 | 8.21 | 8.787 | 9.134 | 9.253 | 9.53 | 1.685 | 0.0463998 | coiled-coil domain containing 120 |
| TYW3 | 6.517 | 6.45 | 5.686 | 7.274 | 7.067 | 7.022 | 1.691 | 0.0453252 | tRNA-yW synthesizing protein 3 homolog (S. cerevisiae) |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| FLJ25363 | 5.462 | 5.64 | 5.839 | 6.333 | 6.547 | 6.399 | 1.692 | 0.0324512 | No description |
| LAMP3 | 3.677 | 3.914 | 3.42 | 4.603 | 4.622 | 4.18 | 1.693 | 0.0480511 | lysosomal-associated membrane protein 3 |
| DUXA | 4.37 | 4.359 | 3.393 | 5.067 | 5.114 | 5.131 | 1.694 | 0.0304522 | double homeobox A |
| TMEM220 | 3.587 | 3.916 | 3.964 | 4.684 | 4.48 | 4.676 | 1.694 | 0.0327595 | transmembrane protein 220 |
| HNRNPH2 | 3.342 | 2.628 | 2.993 | 3.712 | 3.753 | 3.962 | 1.694 | 0.0475989 | heterogeneous nuclear ribonucleoprotein H2 (H') |
| MLL2 | 8.547 | 7.923 | 8.397 | 9.16 | 9.063 | 9.182 | 1.698 | 0.0359505 | myeloid/lymphoid or mixed-lineage leukemia 2 |
| LOC652276 | 5.117 | 4.979 | 4.966 | 5.881 | 5.568 | 5.794 | 1.698 | 0.0371639 | No description |
| TPD52L2 | 8.326 | 7.94 | 7.53 | 9.052 | 8.629 | 8.705 | 1.699 | 0.049985 | tumor protein D52-like 2 |
| CRAMP1L | 5.309 | 5.179 | 5.367 | 5.934 | 6.231 | 6.077 | 1.702 | 0.0252429 | Crm, cramped-like (Drosophila) |
| KDM5A | 7.326 | 7.506 | 7.046 | 8.274 | 7.902 | 8.034 | 1.703 | 0.0446577 | lysine (K)-specific demethylase 5A |
| GCK | 3.668 | 3.51 | 3.653 | 4.849 | 4.359 | 4.282 | 1.708 | 0.0285118 | glucokinase (hexokinase 4) |
| TNPO2 | 8.844 | 8.752 | 8.416 | 9.464 | 9.277 | 9.619 | 1.711 | 0.0411462 | transportin 2 |
| C2orf60 | 5.485 | 5.396 | 4.839 | 6.217 | 6.171 | 5.976 | 1.712 | 0.0352286 | chromosome 2 open reading frame 60 |
| LSM12 | 8.332 | 7.833 | 7.837 | 8.985 | 8.795 | 8.608 | 1.712 | 0.0474329 | LSM12 homolog (S. cerevisiae) |
| RBM12B | 3.02 | 3.441 | 3.29 | 4.224 | 4.062 | 4.061 | 1.72 | 0.0223252 | RNA binding motif protein 12B |
| C20orf20 | 4.852 | 4.43 | 4.509 | 5.614 | 5.37 | 5.213 | 1.72 | 0.0399149 | chromosome 20 open reading frame 20 |
| ZNF714 | 5.413 | 5.203 | 5.077 | 5.89 | 6.197 | 5.944 | 1.721 | 0.0349553 | zinc finger protein 714 |
| SAFB | 9.773 | 8.217 | 9.75 | 10.509 | 10.559 | 10.235 | 1.724 | 0.0483308 | scaffold attachment factor B |
| PIGW | 5.302 | 5.473 | 5.747 | 6.173 | 6.259 | 6.34 | 1.725 | 0.0412277 | phosphatidylinositol glycan anchor biosynthesis, class W |
| SLC2A11 | 6.22 | 6.096 | 5.941 | 6.802 | 7.041 | 6.728 | 1.726 | 0.0335215 | solute carrier family 2 (facilitated glucose transporter), member 11 |
| KRT8 | 6.994 | 6.545 | 6.955 | 7.743 | 8.791 | 7.323 | 1.727 | 0.0463418 | keratin 8 |
| BBS10 | 2.794 | 3.817 | 3.848 | 4.218 | 4.606 | 4.609 | 1.728 | 0.0498347 | Bardet-Biedl syndrome 10 |
| CNNM1 | 3.992 | 3.865 | 3.701 | 4.493 | 4.887 | 4.56 | 1.732 | 0.0350769 | cyclin M1 |
| PTPRU | 6.349 | 5.287 | 6.305 | 7.138 | 7.083 | 7.1 | 1.732 | 0.0271024 | protein tyrosine phosphatase, receptor type, U |
| ZNF578 | 6.69 | 6.803 | 6.476 | 7.419 | 7.652 | 7.271 | 1.735 | 0.0352429 | zinc finger protein 578 |
| PICK1 | 6.931 | 7.274 | 7.447 | 8.242 | 7.871 | 7.992 | 1.735 | 0.0399535 | protein interacting with PRKCA 1 |
| FAM20B | 5.521 | 5.55 | 5.574 | 6.171 | 6.347 | 6.422 | 1.737 | 0.0240874 | family with sequence similarity 20, member B |
| DNHD1 | 5.398 | 5.485 | 5.373 | 6.487 | 6.083 | 6.196 | 1.739 | 0.0239386 | dynein heavy chain domain 1 |
| MAPKAPK5 | 6.885 | 6.784 | 6.804 | 7.562 | 7.604 | 7.758 | 1.742 | 0.017023 | mitogen-activated protein kinase-activated protein kinase 5 |
| FAM127B | 3.656 | 3.61 | 3.236 | 4.417 | 4.205 | 4.412 | 1.744 | 0.0278436 | family with sequence similarity 127, member B |
| ZKSCAN1 | 5.029 | 4.588 | 4.75 | 5.509 | 5.604 | 5.554 | 1.746 | 0.0362131 | zinc finger with KRAB and SCAN domains 1 |
| GATAD2B | 8.028 | 7.51 | 7.654 | 8.314 | 8.669 | 8.673 | 1.746 | 0.0413837 | GATA zinc finger domain containing 2B |
| SULT1A4 | 7.342 | 7.625 | 7.108 | 7.995 | 8.288 | 8.146 | 1.746 | 0.0427345 | sulfotransferase family, cytosolic, 1A, phenol-preferring, member 4 |
| GCAT | 2.911 | 3.098 | 2.616 | 3.579 | 3.902 | 3.521 | 1.746 | 0.0443951 | glycine C-acetyltransferase |
| CHCHD3 | 6.281 | 6.265 | 6.061 | 7.071 | 6.653 | 7.137 | 1.748 | 0.0489154 | coiled-coil-helix-coiled-coil-helix domain containing 3 |
| PPM1J | 4.846 | 3.859 | 4.744 | 5.653 | 5.385 | 5.273 | 1.749 | 0.0484661 | protein phosphatase, Mg2+/Mn2+ dependent, 1J |
| OSBP2 | 4.917 | 4.194 | 4.607 | 5.464 | 5.414 | 5.274 | 1.749 | 0.0490062 | oxysterol binding protein 2 |
| FXN | 6.491 | 6.134 | 6.271 | 6.969 | 7.192 | 7.08 | 1.752 | 0.0313386 | frataxin |
| ZNF430 | 2.619 | 2.395 | 2.108 | 3.428 | 3.298 | 2.898 | 1.752 | 0.0444094 | zinc finger protein 430 |
| SF3B14 | 8.53 | 8.578 | 8.524 | 9.417 | 9.168 | 9.34 | 1.753 | 0.0241397 | No description |
| TEKT3 | 2.41 | 2.129 | 2.55 | 3.581 | 3.174 | 2.939 | 1.753 | 0.0396044 | tektin 3 |
| PPIA | 8.557 | 8.755 | 8.883 | 9.24 | 9.567 | 9.695 | 1.755 | 0.0444588 | peptidylprolyl isomerase A (cyclophilin A) |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| PRKDC | 7.35 | 7.404 | 7.078 | 8.321 | 7.993 | 7.891 | 1.757 | 0.0395256 | protein kinase, DNA-activated, catalytic polypeptide |
| EARS2 | 5.029 | 4.786 | 4.58 | 5.842 | 5.443 | 5.436 | 1.757 | 0.0488588 | glutamyl-tRNA synthetase 2, mitochondrial (putative) |
| SRRT | 10.565 | 9.813 | 10.27 | 11.087 | 11.092 | 10.952 | 1.762 | 0.0471074 | serrate RNA effector molecule homolog (Arabidopsis) |
| MRPL47 | 5.518 | 5.571 | 5.575 | 6.126 | 6.389 | 6.433 | 1.763 | 0.0292273 | mitochondrial ribosomal protein L47 |
| SERPINB9 | 9.638 | 9.456 | 9.181 | 10.174 | 10.457 | 10.27 | 1.764 | 0.0249267 | serpin peptidase inhibitor, clade B (ovalbumin), member 9 |
| NF2 | 8.531 | 8.653 | 8.183 | 9.357 | 9.289 | 9.354 | 1.768 | 0.0222659 | neurofibromin 2 (merlin) |
| DDX51 | 6.726 | 6.4 | 6.714 | 7.485 | 7.485 | 7.549 | 1.769 | 0.0161995 | DEAD (Asp-Glu-Ala-Asp) box polypeptide 51 |
| RFWD3 | 5.374 | 5.322 | 4.742 | 5.933 | 5.999 | 6.198 | 1.77 | 0.0332518 | ring finger and WD repeat domain 3 |
| STK16 | 5.398 | 5.493 | 5.144 | 6.222 | 6.422 | 5.95 | 1.771 | 0.0306575 | serine/threonine kinase 16 |
| ZNF493 | 7.172 | 6.958 | 7.411 | 7.999 | 8.116 | 7.997 | 1.775 | 0.0235408 | zinc finger protein 493 |
| RDH5 | 4.069 | 3.713 | 3.985 | 4.691 | 4.631 | 4.897 | 1.775 | 0.0284482 | retinol dehydrogenase 5 (11-cis/9-cis) |
| AP2B1 | 8.148 | 7.388 | 7.852 | 8.679 | 8.695 | 8.592 | 1.775 | 0.0408478 | adaptor-related protein complex 2, beta 1 subunit |
| AKT1 | 7.639 | 6.635 | 7.451 | 8.285 | 8.281 | 8.065 | 1.777 | 0.0425113 | v-akt murine thymoma viral oncogene homolog 1 |
| LOC344967 | 6.523 | 6.952 | 5.849 | 7.656 | 7.354 | 7.244 | 1.778 | 0.0467754 | No description |
| ASXL2 | 5.03 | 4.7 | 5.25 | 5.486 | 6.081 | 5.952 | 1.778 | 0.0477785 | additional sex combs like 2 (Drosophila) |
| TATDN3 | 4.528 | 3.673 | 4.039 | 5.158 | 4.857 | 4.871 | 1.779 | 0.0467203 | TatD DNase domain containing 3 |
| DICER1 | 7.907 | 7.596 | 8.199 | 8.943 | 8.737 | 8.739 | 1.781 | 0.0265508 | dicer 1, ribonuclease type III |
| MECR | 4.902 | 4.053 | 4.726 | 5.581 | 5.56 | 5.494 | 1.783 | 0.0292466 | mitochondrial trans-2-enoyl-CoA reductase |
| ADORA2B | 7.276 | 7.365 | 6.407 | 7.871 | 8.109 | 8.175 | 1.783 | 0.0328676 | adenosine A2b receptor |
| C10orf47 | 5.425 | 5.405 | 5.32 | 6.035 | 6.242 | 6.685 | 1.786 | 0.023885 | chromosome 10 open reading frame 47 |
| ACVR2B | 3.501 | 3.912 | 3.675 | 4.521 | 4.512 | 4.507 | 1.786 | 0.0255341 | activin A receptor, type I IB |
| TIRAP | 6.426 | 6.701 | 6.591 | 7.316 | 7.809 | 7.262 | 1.786 | 0.0293325 | toll-interleukin 1 receptor (TIR) domain containing adaptor protein |
| FAM115A | 6.244 | 6.427 | 6.265 | 6.89 | 7.657 | 7.102 | 1.786 | 0.0359677 | family with sequence similarity 115, member A |
| SMYD4 | 5.631 | 5.526 | 4.979 | 6.272 | 6.469 | 6.061 | 1.787 | 0.0379981 | SET and MYND domain containing 4 |
| PLA2G2D | 8.131 | 7.66 | 7.761 | 8.499 | 8.916 | 8.885 | 1.788 | 0.026867 | phospholipase A2, group HD |
| PDPK1 | 6.228 | 5.838 | 5.852 | 7.007 | 6.934 | 6.677 | 1.789 | 0.022942 | 3-phosphoinositide dependent protein kinase-1 |
| LDLR | 10.936 | 11.226 | 10.89 | 12.183 | 11.545 | 11.776 | 1.79 | 0.0468577 | low density lipoprotein receptor |
| SCAND2 | 5.853 | 5.906 | 5.988 | 6.693 | 6.997 | 6.719 | 1.791 | 0.0161294 | SCAN domain containing 2 pseudogene |
| FLJ25006 | 3.095 | 3.043 | 3.381 | 4.222 | 4.184 | 3.808 | 1.792 | 0.0241268 | No description |
| SBF1 | 6.391 | 5.542 | 6.277 | 6.999 | 7.236 | 6.917 | 1.797 | 0.0337676 | SET binding factor 1 |
| DFNB31 | 8.675 | 8.656 | 9.134 | 9.98 | 9.774 | 9.374 | 1.798 | 0.0388066 | deafness, autosomal recessive 31 |
| SIGLEC11 | 2.227 | 1.582 | 2.324 | 3.124 | 3.074 | 2.981 | 1.799 | 0.0223639 | sialic acid binding Ig-like lectin 11 |
| KIAA1967 | 6.316 | 5.912 | 6.155 | 6.838 | 7.003 | 7.108 | 1.8 | 0.0246577 | KIAA1967 |
| NELF | 7.934 | 7.62 | 7.794 | 8.979 | 8.468 | 8.57 | 1.8 | 0.0274115 | nasal embryonic LHRH factor |
| DECR2 | 5.873 | 5.777 | 5.23 | 6.303 | 6.722 | 6.447 | 1.801 | 0.042811 | 2,4-dienoyl CoA reductase 2, peroxisomal |
| SPTBN2 | 2.602 | 2.262 | 2.796 | 3.396 | 3.504 | 3.452 | 1.802 | 0.0227517 | spectrin, beta, non-erythrocytic 2 |
| NAIP | 5.517 | 5.293 | 5.37 | 6.221 | 6.541 | 5.983 | 1.804 | 0.030933 | NLR family, apoptosis inhibitory protein |
| LOC286135 | 2.275 | 2.235 | 2.655 | 3.508 | 3.488 | 3 | 1.806 | 0.0264334 | No description |
| HEBP2 | 4.188 | 4.146 | 3.909 | 4.761 | 5.177 | 4.864 | 1.806 | 0.0270172 | heme binding protein 2 |
| EPHA2 | 10.088 | 9.573 | 9.707 | 10.683 | 10.941 | 10.328 | 1.806 | 0.0434034 | EPH receptor A2 |
| C22orf27 | 2.775 | 3.231 | 3.003 | 4.059 | 4.088 | 3.587 | 1.811 | 0.0301467 | chromosome 22 open reading frame 27 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| SIGLEC10 | 3.46 | 3.69 | 3.428 | 4.179 | 4.37 | 4.548 | 1.812 | 0.0255269 | sialic acid binding Ig-like lectin 10 |
| TNFAIP8L1 | 7.647 | 7.401 | 7.785 | 8.412 | 8.733 | 8.259 | 1.813 | 0.0314481 | tumor necrosis factor, alpha-induced protein 8-like 1 |
| RNPC3 | 4.257 | 5.055 | 4.938 | 5.51 | 5.731 | 5.913 | 1.813 | 0.0340409 | RNA-binding region (RNP1, RRM) containing 3 |
| C19orf26 | 2.519 | 2.289 | 1.407 | 2.857 | 3.378 | 3.056 | 1.813 | 0.0444659 | chromosome 19 open reading frame 26 |
| ABCC9 | 5.326 | 5.457 | 5.601 | 6.298 | 6.185 | 6.934 | 1.814 | 0.0239837 | ATP-binding cassette, sub-family C (CFTR/MRP), member 9 |
| AGMAT | 9.172 | 8.309 | 8.874 | 9.734 | 9.981 | 9.67 | 1.815 | 0.0279745 | agmatine ureohydrolase (agmatinase) |
| NUDT3 | 6.108 | 6.42 | 6.385 | 7.223 | 7.28 | 7.03 | 1.816 | 0.0199664 | nudix (nucleoside diphosphate linked moiety X)-type motif 3 |
| MCM8 | 4.381 | 4.232 | 3.921 | 5.093 | 4.96 | 5.184 | 1.816 | 0.0211476 | minichromosome maintenance complex component 8 |
| C3orf74 | 2.988 | 2.711 | 2.926 | 3.714 | 3.572 | 4.065 | 1.816 | 0.0230722 | chromosome 3 open reading frame 74 |
| SEC16A | 8.821 | 8.021 | 8.575 | 9.681 | 9.147 | 9.371 | 1.816 | 0.0422158 | SEC16 homolog A (S. cerevisiae) |
| ANKS4B | 7.654 | 7.234 | 7.588 | 8.337 | 8.45 | 8.513 | 1.817 | 0.016246 | ankyrin repeat and sterile alpha motif domain containing 4B |
| POM121L8P | 4.16 | 4.273 | 3.775 | 4.895 | 5.238 | 4.636 | 1.817 | 0.0437376 | POM121 membrane glycoprotein-like 8 pseudogene |
| GEMIN5 | 4.673 | 4.726 | 4.172 | 5.652 | 5.036 | 5.498 | 1.819 | 0.0462961 | gem (nuclear organelle) associated protein 5 |
| TESK2 | 5.068 | 5.198 | 5.184 | 5.846 | 6.049 | 6.154 | 1.822 | 0.0170788 | testis-specific kinase 2 |
| GSDMA | 5.893 | 5.67 | 5.478 | 6.359 | 6.758 | 6.357 | 1.822 | 0.0393733 | gasdermin A |
| PCDHA9 | 4.59 | 4.629 | 4.824 | 5.496 | 5.842 | 5.375 | 1.824 | 0.0232604 | protocadherin alpha 9 |
| CHPF | 7.132 | 7.257 | 6.962 | 8.557 | 7.999 | 7.646 | 1.825 | 0.037498 | chondroitin polymerizing factor |
| C1orf84 | 3.535 | 3.563 | 2.327 | 4.379 | 4.027 | 4.431 | 1.825 | 0.0380246 | chromosome 1 open reading frame 84 |
| WFDC8 | 3.034 | 1.936 | 2.625 | 3.493 | 3.452 | 3.562 | 1.825 | 0.0431802 | WAP four-disulfide core domain 8 |
| NDUFAF4 | 8.469 | 7.346 | 8.14 | 8.927 | 9.008 | 9.225 | 1.826 | 0.0330786 | NADH dehydrogenase (ubiquinone) 1 alpha subcomplex, assembly factor 4 |
| POLR2F | 9.015 | 9.019 | 9.354 | 9.886 | 9.899 | 9.915 | 1.828 | 0.0309988 | polymerase (RNA) II (DNA directed) polypeptide F |
| LOC1001909 86 | 6.296 | 6.982 | 6.931 | 7.738 | 7.694 | 7.853 | 1.829 | 0.0200408 | No description |
| LOC400043 | 6.916 | 6.391 | 6.731 | 7.252 | 7.86 | 7.603 | 1.83 | 0.0375195 | No description |
| ZNF250 | 6.862 | 6.492 | 6.431 | 7.196 | 7.733 | 7.368 | 1.83 | 0.0413193 | zinc finger protein 250 |
| PPAN | 7.769 | 6.771 | 7.49 | 8.506 | 8.111 | 8.362 | 1.831 | 0.0404343 | peter pan homolog (Drosophila) |
| API5 | 8.124 | 7.756 | 7.733 | 8.86 | 8.39 | 9 | 1.835 | 0.0375603 | apoptosis inhibitor 5 |
| ZNF397OS | 2.787 | 3.339 | 3.359 | 3.888 | 4.075 | 4.235 | 1.836 | 0.0313071 | No description |
| CFLP1 | 4.722 | 4.749 | 5.067 | 5.575 | 5.628 | 6.114 | 1.839 | 0.0269929 | cofilin pseudogene 1 |
| WDR85 | 6.441 | 6.505 | 6.213 | 7.385 | 7.156 | 7.212 | 1.84 | 0.0190212 | WD repeat domain 85 |
| PRDM14 | 6.378 | 5.972 | 5.856 | 6.669 | 7.383 | 6.852 | 1.84 | 0.043681 | PR domain containing 14 |
| LOC1002893 41 | 5.77 | 5.923 | 5.64 | 6.65 | 6.739 | 6.564 | 1.841 | 0.01611 | No description |
| RNGTT | 5.187 | 5.025 | 5.037 | 6.422 | 5.793 | 5.921 | 1.845 | 0.0221421 | RNA guanylyltransferase and 5'-phosphatase |
| NCRNA00182 | 9.233 | 8.781 | 8.887 | 9.955 | 9.667 | 9.859 | 1.848 | 0.0276111 | non-protein coding RNA 182 |
| NRCAM | 3.018 | 3.483 | 3.065 | 4.369 | 3.778 | 4.225 | 1.849 | 0.0305509 | neuronal cell adhesion molecule |
| LIF | 11.346 | 11.043 | 11.551 | 11.93 | 12.594 | 12.129 | 1.849 | 0.0380776 | leukemia inhibitory factor (cholinergic differentiation factor) |
| CLOCK | 4.337 | 3.698 | 4.005 | 5.076 | 4.584 | 5.02 | 1.849 | 0.0414087 | clock homolog (mouse) |
| CNPY3 | 6.499 | 6.259 | 5.979 | 7.283 | 7.148 | 7.135 | 1.851 | 0.0183523 | canopy 3 homolog (zebrafish) |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24− N48 | CD24− N58 | CD24− N43 | CD24− N37 | CD24− N39 | CD24− N40 | | | |
| MRPS9 | 6.216 | 6.108 | 6.129 | 7.106 | 7.059 | 6.771 | 1.852 | 0.0224762 | mitochondrial ribosomal protein S9 |
| C10orf140 | 3.335 | 3.368 | 3.522 | 4.004 | 4.844 | 4.258 | 1.852 | 0.0315361 | chromosome 10 open reading frame 140 |
| HRAS | 9.004 | 8.529 | 8.242 | 9.616 | 9.378 | 9.425 | 1.86 | 0.0393389 | v-Ha-ras Harvey rat sarcoma viral oncogene homolog |
| RAI1 | 8.961 | 8.626 | 8.834 | 9.67 | 9.915 | 9.523 | 1.862 | 0.0216126 | retinoic acid induced 1 |
| CCDC86 | 9.485 | 8.426 | 9.144 | 10.381 | 10.029 | 9.94 | 1.862 | 0.0288503 | coiled-coil domain containing 86 |
| WNK3 | 4.501 | 4.415 | 5.086 | 5.575 | 5.312 | 5.873 | 1.862 | 0.0397775 | WNK lysine deficient protein kinase 3 |
| CACNG4 | 2.522 | 2.477 | 1.936 | 3.647 | 2.802 | 3.373 | 1.862 | 0.0423675 | calcium channel, voltage-dependent, gamma subunit 4 |
| MOCS3 | 4.21 | 3.687 | 3.849 | 4.676 | 4.673 | 5.108 | 1.863 | 0.0311941 | molybdenum cofactor synthesis 3 |
| DGKE | 7.427 | 6.967 | 7.233 | 8.07 | 8.136 | 8.131 | 1.864 | 0.0187143 | diacylglycerol kinase, epsilon 64kDa |
| PDGFC | 4.203 | 4.634 | 4.339 | 5.285 | 5.204 | 5.238 | 1.864 | 0.0231874 | platelet derived growth factor C |
| FLJ42627 | 6.348 | 5.627 | 6.151 | 7.049 | 6.938 | 7.081 | 1.864 | 0.0232389 | No description |
| IL10 | 6.141 | 6.003 | 6.326 | 7.04 | 7.763 | 6.68 | 1.864 | 0.0397625 | interleukin 10 |
| MGC57346 | 3.351 | 2.834 | 2.747 | 3.686 | 4.25 | 3.725 | 1.864 | 0.0407226 | No description |
| MSL2 | 6.087 | 6.443 | 5.984 | 6.884 | 7.031 | 7.146 | 1.865 | 0.0285541 | male-specific lethal 2 homolog (Drosophila) |
| C6orf97 | 2.91 | 3.481 | 3.57 | 4.468 | 4.38 | 3.992 | 1.865 | 0.0312478 | chromosome 6 open reading frame 97 |
| GPR113 | 1.563 | 1.8 | 1.714 | 2.498 | 2.51 | 2.7 | 1.866 | 0.0157917 | G protein-coupled receptor 113 |
| NAP1L4 | 9.959 | 9.288 | 9.264 | 10.662 | 10.703 | 10.164 | 1.866 | 0.0310718 | nucleosome assembly protein 1-like 4 |
| LASS4 | 4.983 | 3.986 | 4.928 | 5.884 | 5.37 | 5.608 | 1.868 | 0.0472476 | LAG1 homolog, ceramide synthase 4 |
| ZNF431 | 2.235 | 2.025 | 1.926 | 2.927 | 3.651 | 2.696 | 1.869 | 0.0307591 | zinc finger protein 431 |
| CTDP1 | 7.031 | 6.649 | 6.235 | 7.934 | 7.5 | 7.431 | 1.869 | 0.0326887 | CTD (carboxy-terminal domain, RNA polymerase II, polypeptide A) phosphatase, subunit 1 |
| RUVBL1 | 5.018 | 4.697 | 3.976 | 5.922 | 5.44 | 5.601 | 1.871 | 0.0296351 | RuvB-like 1 (E. coli) |
| ZNF767 | 4.631 | 4.892 | 4.855 | 5.76 | 5.874 | 5.223 | 1.872 | 0.0456199 | zinc finger family member 767 |
| ADSL | 6.007 | 5.808 | 4.716 | 6.912 | 6.206 | 6.695 | 1.873 | 0.0491164 | adenylosuccinate lyase |
| MLLT10 | 4.226 | 4.364 | 4.189 | 5.15 | 5.146 | 5.097 | 1.876 | 0.0115318 | myeloid/lymphoid or mixed-lineage leukemia (trithorax homolog, Drosophila); translocated to, 10 |
| GOT1 | 6.128 | 6.118 | 5.303 | 7.038 | 6.567 | 6.833 | 1.879 | 0.0410753 | glutamic-oxaloacetic transaminase 1, soluble (aspartate aminotransferase 1) |
| SIRT3 | 9.393 | 9.011 | 9.195 | 10.105 | 10.198 | 9.977 | 1.88 | 0.0186099 | sirtuin 3 |
| C19orf10 | 8.715 | 7.95 | 7.757 | 9.627 | 8.603 | 9.357 | 1.882 | 0.0498712 | chromosome 19 open reading frame 10 |
| CRX | 3.918 | 4.156 | 4.21 | 4.879 | 4.98 | 5.124 | 1.884 | 0.0163977 | cone-rod homeobox |
| MCPH1 | 4.556 | 4.522 | 4.261 | 5.716 | 5.174 | 5.358 | 1.884 | 0.0194384 | microcephalin 1 |
| RPUSD3 | 2.724 | 1.928 | 2.348 | 3.354 | 3.149 | 3.263 | 1.885 | 0.0335694 | RNA pseudouridylate synthase domain containing 3 |
| ZNF713 | 6.857 | 6.593 | 6.251 | 7.197 | 7.647 | 7.507 | 1.885 | 0.036007 | zinc finger protein 713 |
| SGPL1 | 5.855 | 5.92 | 5.464 | 6.837 | 6.244 | 6.774 | 1.887 | 0.041539 | sphingosine-1-phosphate lyase 1 |
| SLC19A3 | 3.297 | 2.781 | 2.919 | 3.901 | 3.697 | 4.12 | 1.888 | 0.0280017 | solute carrier family 19, member 3 |
| FHL2 | 10.843 | 11.028 | 10.787 | 11.705 | 11.93 | 11.897 | 1.889 | 0.011071 | four and a half LIM domains 2 |
| C1orf66 | 3.719 | 3.902 | 3.937 | 4.855 | 4.849 | 4.382 | 1.889 | 0.031921 | chromosome 1 open reading frame 66 |
| POLG2 | 4.408 | 4.846 | 4.453 | 5.47 | 5.527 | 5.326 | 1.89 | 0.024325 | polymerase (DNA directed), gamma 2, accessory subunit |
| MPHOSPH8 | 8.151 | 7.585 | 7.122 | 8.466 | 8.817 | 8.503 | 1.89 | 0.0413386 | M-phase phosphoprotein 8 |
| YDJC | 6.698 | 6.492 | 6.565 | 7.673 | 7.256 | 7.484 | 1.891 | 0.0202018 | YdjC homolog (bacterial) |
| ZNF202 | 3.079 | 2.919 | 2.03 | 3.697 | 4.001 | 3.772 | 1.894 | 0.0237261 | zinc finger protein 202 |
| RAGE | 5.002 | 4.595 | 5.286 | 6.212 | 5.733 | 5.845 | 1.899 | 0.0290234 | renal tumor antigen |

TABLE 6-continued

Differentially Expressed Genes in CD10+ Breast Epithelial Cells

| Gene Symbol | Nulliparous (NP) Samples | | | | Parous (P) Samples | | | | Pseudo fold change | P value | Gene description |
|---|---|---|---|---|---|---|---|---|---|---|---|
| | CD24+ N48 | CD24+ N58 | CD24+ N43 | CD24+ N37 | CD24+ N39 | CD24+ N40 | | | | | |
| KIAA0495 | 5.781 | 5.937 | 6.371 | 6.831 | 7.223 | 6.863 | | | 1.9 | 0.0271639 | KIAA0495 |
| MARVELD3 | 6.19 | 5.778 | 5.252 | 6.572 | 7.106 | 6.704 | | | 1.9 | 0.0301181 | MARVEL domain containing 3 |
| XPNPEP3 | 5.043 | 5.199 | 5.646 | 5.844 | 6.803 | 6.125 | | | 1.9 | 0.0481126 | X-prolyl aminopeptidase (aminopeptidase P) 3, putative |
| NACA | 3.63 | 3.298 | 3.327 | 4.956 | 4.254 | 3.98 | | | 1.901 | 0.0393318 | nascent polypeptide-associated complex alpha subunit |
| SFRS8 | 7.865 | 7.775 | 8.07 | 9.07 | 8.702 | 8.765 | | | 1.902 | 0.0165486 | No description |
| NUDT22 | 3.71 | 3.789 | 2.719 | 4.716 | 4.194 | 4.45 | | | 1.902 | 0.0416999 | nudix (nucleoside diphosphate linked moiety X)-type motif 22 |
| BRCC1 | 9.204 | 8.714 | 8.854 | 9.998 | 9.783 | 9.78 | | | 1.903 | 0.0201073 | excision repair cross-complementing rodent repair deficiency, complementation group 1 (includes overlapping antisense sequence) |
| ORAOV1 | 5.885 | 5.373 | 5.541 | 6.473 | 6.473 | 6.412 | | | 1.907 | 0.0269471 | oral cancer overexpressed 1 |
| HN1L | 8.928 | 7.892 | 8.765 | 9.846 | 9.697 | 9.574 | | | 1.908 | 0.020493 | hematological and neurological expressed 1 -like |
| EIF4E2 | 6.92 | 6.333 | 6.702 | 7.852 | 7.4 | 7.531 | | | 1.908 | 0.0272762 | eukaryotic translation initiation factor 4E family member 2 |
| ARHGEF18 | 4.821 | 4.178 | 4.048 | 5.541 | 4.981 | 5.525 | | | 1.91 | 0.0345167 | Rho/Rac guanine nucleotide exchange factor (GEF) 18 |
| DCLRE1C | 3.838 | 3.427 | 3.518 | 4.647 | 4.772 | 4.284 | | | 1.911 | 0.0201581 | DNA cross-link repair 1C |
| KLHL36 | 7.469 | 6.691 | 7.281 | 8.404 | 7.784 | 8.217 | | | 1.912 | 0.0355091 | kelch-like 36 (Drosophila) |
| PLCD3 | 9.191 | 9.006 | 9.473 | 10.127 | 10.007 | 10.267 | | | 1.913 | 0.0208686 | phospholipase C, delta 3 |
| ISLR2 | 4.079 | 3.766 | 3.587 | 4.716 | 4.765 | 4.523 | | | 1.913 | 0.0281069 | immunoglobulin superfamily containing leucine-rich repeat 2 |
| REPIN1 | 7.861 | 7.741 | 7.81 | 8.893 | 8.746 | 8.648 | | | 1.914 | 0.0091558 | replication initiator 1 |
| PPP1R9A | 2.724 | 2.146 | 2.367 | 3.548 | 3.083 | 3.548 | | | 1.914 | 0.0247836 | protein phosphatase 1, regulatory (inhibitor) subunit 9A |
| GYG2 | 1.143 | 0.464 | 0.251 | 1.188 | 1.758 | 1.827 | | | 1.915 | 0.0461072 | glycogenin 2 |
| C18orf25 | 6.441 | 6.646 | 7.099 | 7.425 | 7.591 | 7.584 | | | 1.916 | 0.0463562 | chromosome 18 open reading frame 25 |
| NLRP12 | 5.045 | 5.134 | 5.107 | 5.984 | 6.635 | 6.035 | | | 1.917 | 0.012019 | NLR family, pyrin domain containing 12 |
| RIOK1 | 7.066 | 7.132 | 6.766 | 8.144 | 7.92 | 7.706 | | | 1.918 | 0.0204393 | RIO kinase 1 (yeast) |
| CACYBP | 7.506 | 6.93 | 7.119 | 7.831 | 8.447 | 8.12 | | | 1.919 | 0.0314817 | calcyclin binding protein |
| FAM23A | 2.807 | 3.121 | 3.086 | 4.479 | 3.64 | 4.028 | | | 1.92 | 0.0230522 | family with sequence similarity 23, member A |
| GOLGA6C | 1.62 | 2.812 | 3.3 | 3.753 | 3.946 | 3.742 | | | 1.92 | 0.0380632 | golgin A6 family, member C |
| SNRPD2 | 10.029 | 9.649 | 9.402 | 10.352 | 10.59 | 10.687 | | | 1.92 | 0.0388739 | small nuclear ribonucleoprotein D2 polypeptide 16.5kDa |
| C21orf7 | 1.864 | 1.332 | 1.563 | 2.274 | 2.423 | 2.897 | | | 1.921 | 0.0313987 | chromosome 21 open reading frame 7 |
| ZNF485 | 3.525 | 4 | 3.667 | 4.467 | 5.13 | 4.529 | | | 1.922 | 0.0289705 | zinc finger protein 485 |
| SNHG4 | 3.654 | 3.413 | 3.026 | 4.356 | 3.968 | 4.624 | | | 1.923 | 0.034287 | small nucleolar RNA host gene 4 (non-protein coding) |
| NDNL2 | 6.501 | 6.353 | 6.072 | 7.447 | 7.245 | 7.246 | | | 1.926 | 0.0122823 | necdin-like 2 |
| LONP2 | 6.327 | 5.933 | 5.78 | 7.132 | 7.194 | 6.726 | | | 1.926 | 0.020983 | Ion peptidase 2, peroxisomal |
| HES2 | 3.721 | 3.428 | 2.914 | 4.332 | 4.638 | 4.375 | | | 1.927 | 0.0182779 | hairy and enhancer of split 2 (Drosophila) |
| LOC100130093 | 3.863 | 3.553 | 4.081 | 4.475 | 5.03 | 4.944 | | | 1.93 | 0.0245868 | No description |
| INTS12 | 5.097 | 4.444 | 4.576 | 5.769 | 5.525 | 5.462 | | | 1.93 | 0.0365915 | integrator complex subunit 12 |
| EN2 | 4.848 | 3.057 | 4.601 | 5.597 | 5.55 | 5.467 | | | 1.931 | 0.0318716 | engrailed homeobox 2 |
| TMEM186 | 4.382 | 3.57 | 3.944 | 5.332 | 4.504 | 4.997 | | | 1.932 | 0.0447914 | transmembrane protein 186 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| NXT2 | 4.042 | 4.065 | 3.503 | 5.016 | 4.526 | 4.827 | 1.934 | 0.0328747 | nuclear transport factor 2-like export factor 2 |
| COQ10B | 3.315 | 3.196 | 3.562 | 4.283 | 4.067 | 4.516 | 1.937 | 0.0207219 | coenzyme Q10 homolog B (S. cerevisiae) |
| ERBB3 | 3.908 | 4.098 | 3.46 | 4.444 | 4.863 | 4.92 | 1.939 | 0.0345468 | v-erb-b2 erythroblastic leukemia viral oncogene homolog 3 (avian) |
| HS3ST3A1 | 5.122 | 4.618 | 5.083 | 6.205 | 5.467 | 6.039 | 1.94 | 0.0349839 | heparan sulfate (glucosamine) 3-O-sulfotransferase 3A1 |
| NKX2-5 | 1.608 | 1.297 | 1.562 | 2.989 | 2.094 | 2.52 | 1.943 | 0.0250047 | NK2 transcription factor related, locus 5 (Drosophila) |
| LSM7 | 9.226 | 8.658 | 8.521 | 10.133 | 9.634 | 9.479 | 1.943 | 0.04089 | LSM7 homolog, U6 small nuclear RNA associated (S. cerevisiae) |
| RBM25 | 8.026 | 8.492 | 8.62 | 9.244 | 9.368 | 9.579 | 1.944 | 0.0182993 | RNA binding motif protein 25 |
| MACC1 | 4.614 | 4.138 | 4.253 | 5.168 | 5.562 | 5.212 | 1.944 | 0.0194241 | metastasis associated in colon cancer 1 |
| RHBDL1 | 5.402 | 5.466 | 5.334 | 6.362 | 6.618 | 6.226 | 1.945 | 0.0105931 | rhomboid, veinlet-like 1 (Drosophila) |
| CYHR1 | 5.824 | 5.136 | 5.123 | 6.472 | 6.784 | 5.893 | 1.945 | 0.0403763 | cysteine/histidine-rich 1 |
| ADIPOQ | 3.058 | 2.926 | 3.118 | 4.012 | 4.019 | 4.021 | 1.947 | 0.0065179 | adiponectin, C1Q and collagen domain containing |
| WDR92 | 4.107 | 3.684 | 3.953 | 5.001 | 5.062 | 4.645 | 1.947 | 0.0173921 | WD repeat domain 92 |
| C12orf43 | 4.851 | 4.338 | 3.448 | 5.806 | 5.015 | 5.299 | 1.947 | 0.0425542 | chromosome 12 open reading frame 43 |
| EFCAB5 | 1.065 | 1.075 | 1.164 | 2.039 | 2.228 | 1.948 | 1.95 | 0.0093346 | EF-hand calcium binding domain 5 |
| GPR75 | 2.789 | 2.546 | 2.423 | 3.376 | 3.753 | 3.683 | 1.95 | 0.0131287 | G protein-coupled receptor 75 |
| SLC14A1 | 6.465 | 6.365 | 6.196 | 7.16 | 7.547 | 7.191 | 1.95 | 0.015894 | solute carrier family 14 (urea transporter), member 1 (Kidd blood group) |
| NSUN5 | 6.908 | 7.471 | 7.029 | 8.167 | 7.909 | 7.993 | 1.95 | 0.0288968 | NOP2/Sun domain family, member 5 |
| CCDC141 | 0.871 | 1.044 | 1.301 | 2.417 | 1.616 | 2.008 | 1.95 | 0.0356199 | coiled-coil domain containing 141 |
| MBIP | 4.88 | 5.018 | 5.235 | 5.807 | 5.982 | 6.212 | 1.951 | 0.0170716 | MAP3K12 binding inhibitory protein 1 |
| ZNF321 | 6.88 | 6.166 | 6.765 | 7.442 | 7.846 | 7.308 | 1.952 | 0.0401259 | zinc finger protein 321 |
| UTP15 | 5.412 | 5.821 | 5.45 | 6.71 | 6.378 | 6.726 | 1.954 | 0.0130085 | UTP15, U3 small nucleolar ribonucleoprotein, homolog (S. cerevisiae) |
| RECQL4 | 5.018 | 3.751 | 5.163 | 5.588 | 6.129 | 5.738 | 1.954 | 0.0417271 | RecQ protein-like 4 |
| SEC61G | 7.429 | 7.862 | 8.103 | 9.041 | 8.599 | 8.83 | 1.956 | 0.0212685 | Sec61 gamma subunit |
| CD1D | 3.145 | 2.983 | 3.357 | 4.114 | 4.387 | 3.832 | 1.956 | 0.0226308 | CD1d molecule |
| CCDC71 | 5.165 | 3.195 | 4.69 | 6.133 | 5.592 | 5.554 | 1.956 | 0.0360213 | coiled-coil domain containing 71 |
| ZNF721 | 5.646 | 4.931 | 5.844 | 6.514 | 6.384 | 6.812 | 1.957 | 0.0239243 | zinc finger protein 721 |
| SETD1A | 8.391 | 7.337 | 7.909 | 9.267 | 8.877 | 8.745 | 1.957 | 0.0309108 | SET domain containing 1A |
| MTIF2 | 4.166 | 3.89 | 3.984 | 5.129 | 4.953 | 4.878 | 1.958 | 0.0109859 | mitochondrial translational initiation factor 2 |
| MDN1 | 5.221 | 4.986 | 5.174 | 6.391 | 5.955 | 6.045 | 1.958 | 0.0133319 | MDN1, midasin homolog (yeast) |
| DEAF1 | 7.636 | 6.893 | 7.309 | 8.279 | 8.531 | 8.151 | 1.958 | 0.0206825 | deformed epidermal autoregulatory factor 1 (Drosophila) |
| AATK | 4.689 | 4.173 | 3.567 | 5.142 | 5.322 | 4.915 | 1.958 | 0.0458618 | apoptosis-associated tyrosine kinase |
| BRI3BP | 2.073 | 2.257 | 1.126 | 3.227 | 2.994 | 2.439 | 1.958 | 0.0473213 | BRI3 binding protein |
| PLEKHJ1 | 6.438 | 6.283 | 6.473 | 7.456 | 7.408 | 7.086 | 1.959 | 0.0167811 | pleckstrin homology domain containing, family J member 1 |
| RBBP9 | 4.812 | 4.137 | 4.745 | 5.564 | 5.784 | 5.607 | 1.961 | 0.0156636 | retinoblastoma binding protein 9 |
| NPC1L1 | 4.029 | 4.466 | 4.42 | 5.088 | 5.438 | 5.311 | 1.961 | 0.017669 | NPC1 (Niemann-Pick disease, type C1, gene)-like 1 |
| TAF3 | 7.282 | 7.329 | 6.178 | 8.301 | 8.247 | 8.042 | 1.961 | 0.019819 | TAF3 RNA polymerase II, TATA box binding protein (TBP)-associated factor, 140kDa |
| PM20D2 | 5.041 | 5.535 | 5.655 | 6.626 | 6.233 | 6.271 | 1.961 | 0.0259855 | peptidase M20 domain containing 2 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| TIGD6 | 3.898 | 3.387 | 3.489 | 4.619 | 4.416 | 4.461 | 1.962 | 0.0229835 | tigger transposable element derived 6 |
| NHEJ1 | 5.031 | 3.903 | 4.656 | 5.629 | 5.862 | 5.527 | 1.963 | 0.0253445 | nonhomologous end-joining factor 1 |
| CDK16 | 9.634 | 8.997 | 9.315 | 10.371 | 10.289 | 10.078 | 1.964 | 0.0263325 | cyclin-dependent kinase 16 |
| POLG | 8.252 | 7.398 | 8.419 | 9.002 | 9.395 | 9.036 | 1.966 | 0.0266187 | polymerase (DNA directed), gamma |
| ACBD7 | 2.901 | 2.688 | 3.022 | 3.877 | 3.621 | 4.012 | 1.967 | 0.0157487 | acyl-CoA binding domain containing 7 |
| ZNF44 | 5.211 | 5.131 | 4.997 | 5.775 | 6.192 | 6.107 | 1.967 | 0.0188767 | zinc finger protein 44 |
| SNORA72 | 3.978 | 3.292 | 3.4 | 4.775 | 4.268 | 4.668 | 1.967 | 0.0264849 | small nucleolar RNA, H/ACA box 72 |
| LOC646851 | 5.964 | 5.601 | 5.616 | 6.623 | 6.771 | 6.578 | 1.968 | 0.0161437 | No description |
| F5 | 8.333 | 8.68 | 8.642 | 9.31 | 9.539 | 9.707 | 1.968 | 0.0166037 | coagulation factor V (proaccelerin, labile factor) |
| MAOA | 4.498 | 4.26 | 2.527 | 5.237 | 5.256 | 5.148 | 1.968 | 0.0317786 | monoamine oxidase A |
| CWC25 | 7.85 | 7.88 | 7.522 | 8.858 | 8.581 | 8.691 | 1.969 | 0.0150733 | CWC25 spliceosome-associated protein homolog (S. cerevisiae) |
| UCKL1 | 7.36 | 7.027 | 7.502 | 8.453 | 8.353 | 8.006 | 1.971 | 0.0203785 | uridine-cytidine kinase 1-like 1 |
| SFRS16 | 8.123 | 8.089 | 8.563 | 9.407 | 9.068 | 9.134 | 1.971 | 0.021853 | No description |
| IYD | 3.918 | 4.294 | 3.586 | 5.073 | 5.172 | 4.565 | 1.972 | 0.029937 | iodotyrosine deiodinase |
| BRD4 | 9.511 | 9.562 | 9.446 | 10.491 | 10.571 | 10.264 | 1.973 | 0.0118809 | bromodomain containing 4 |
| ZNF737 | 5.788 | 5.497 | 4.974 | 6.478 | 6.602 | 6.28 | 1.973 | 0.0231745 | zinc finger protein 737 |
| CDK20 | 5.184 | 4.509 | 4.432 | 5.717 | 5.413 | 5.796 | 1.974 | 0.0375338 | cyclin-dependent kinase 20 |
| CRELD2 | 5.576 | 5.085 | 4.649 | 6.288 | 5.797 | 6.066 | 1.974 | 0.0431445 | cysteine-rich with EGF-like domains 2 |
| TSTD1 | 5.59 | 5.75 | 3.89 | 6.717 | 6.507 | 6.572 | 1.975 | 0.0237812 | thiosulfate sulfurtransferase (rhodanese)-like domain containing 1 |
| ATP6V1D | 8.415 | 7.321 | 7.838 | 8.882 | 8.82 | 8.789 | 1.975 | 0.0418995 | ATPase, H+ transporting, lysosomal 34kDa, V1 subunit D |
| ZFP36L1 | 12.183 | 11.334 | 11.768 | 12.752 | 13.004 | 12.725 | 1.978 | 0.0210932 | zinc finger protein 36, C3H type-like 1 |
| FLJ39582 | 3.512 | 1.759 | 3.211 | 4.359 | 4.196 | 3.947 | 1.98 | 0.0339536 | No description |
| KCTD13 | 6.258 | 6.208 | 6.351 | 7.633 | 7.244 | 7.117 | 1.981 | 0.0111369 | potassium channel tetramerisation domain containing 13 |
| C20orf96 | 3.608 | 3.54 | 4.343 | 5.128 | 5.001 | 4.526 | 1.981 | 0.0301252 | chromosome 20 open reading frame 96 |
| ZNF192 | 3.758 | 3.908 | 3.953 | 4.532 | 5.124 | 4.895 | 1.982 | 0.0186392 | zinc finger protein 192 |
| UCKL1AS | 3.329 | 2.765 | 2.931 | 4.282 | 3.918 | 3.772 | 1.982 | 0.0238778 | No description |
| MPP6 | 6.728 | 6.382 | 6.584 | 7.752 | 7.37 | 7.437 | 1.983 | 0.0169643 | membrane protein, palmitoylated 6 (MAGUK p55 subfamily member 6) |
| CCDC113 | 1.837 | 2.059 | 2.235 | 3.116 | 3.222 | 2.453 | 1.983 | 0.0459376 | coiled-coil domain containing 113 |
| TRMU | 5.968 | 5.961 | 5.85 | 7.469 | 6.841 | 6.931 | 1.986 | 0.0099077 | tRNA 5-methylaminomethyl-2-thiouridylate methyltransferase |
| SUPT4H1 | 7.011 | 6.264 | 6.605 | 7.635 | 7.596 | 7.564 | 1.987 | 0.0236717 | suppressor of Ty 4 homolog 1 (S. cerevisiae) |
| LIAS | 4.897 | 4.328 | 4.699 | 5.102 | 6.023 | 5.689 | 1.987 | 0.0433691 | lipoic acid synthetase |
| E2F5 | 5.459 | 5.709 | 5.914 | 6.846 | 6.603 | 6.7 | 1.988 | 0.011901 | E2F transcription factor 5, p130-binding |
| ATF2 | 5.699 | 4.675 | 5.217 | 6.064 | 6.258 | 6.208 | 1.988 | 0.0375052 | activating transcription factor 2 |
| SHANK2 | 2.298 | 2.995 | 3.543 | 3.987 | 3.953 | 4.001 | 1.988 | 0.0406804 | SH3 and multiple ankyrin repeat domains 2 |
| STYXL1 | 3.763 | 3.169 | 2.187 | 4.115 | 4.16 | 4.27 | 1.988 | 0.0437712 | serine/threonine/tyrosine interacting-like 1 |
| ZNF91 | 1.228 | 2.008 | 2.466 | 2.999 | 3.434 | 2.593 | 1.988 | 0.0439028 | zinc finger protein 91 |
| SBNO2 | 9.873 | 9.232 | 9.773 | 10.868 | 10.585 | 10.293 | 1.993 | 0.0328604 | strawberry notch homolog 2 (Drosophila) |
| RNF166 | 4.176 | 3.326 | 4.883 | 5.489 | 5.091 | 5.172 | 1.993 | 0.047395 | ring finger protein 166 |
| PARD6G | 6.221 | 5.99 | 5.99 | 6.986 | 7.37 | 6.885 | 1.994 | 0.0142684 | par-6 partitioning defective 6 homolog gamma (C. elegans) |
| CCT2 | 10.422 | 9.653 | 10.006 | 11.193 | 10.89 | 11.001 | 1.994 | 0.0239908 | chaperonin containing TCP1, subunit 2 (beta) |

TABLE 6-continued

Differentially Expressed Genes in CD10+ Breast Epithelial Cells

| Gene Symbol | Nulliparous (NP) Samples | | Parous (P) Samples | | | Pseudo fold change | P value | Gene description |
|---|---|---|---|---|---|---|---|---|
| | CD24+ N48 | CD24+ N58 | CD24+ N43 | CD24+ N37 | CD24+ N39 | CD24+ N40 | | |
| RAD51L3 | 3.817 | 2.864 | 3.289 | 4.285 | 4.442 | 4.197 | 1.994 | 0.0336345 | RAD51-like 3 (S. cerevisiae) |
| ARHGEF33 | 1.748 | 2.048 | 1.818 | 3.209 | 2.8 | 2.745 | 1.996 | 0.0127738 | Rho guanine nucleotide exchange factor (GEF) 33 |
| NR2C2AP | 4.898 | 3.66 | 4.683 | 5.891 | 5.68 | 5.669 | 1.997 | 0.0163855 | nuclear receptor 2C2-associated protein |
| SCN11A | 5.51 | 5.097 | 4.982 | 5.98 | 6.298 | 6.112 | 1.997 | 0.0228819 | sodium channel, voltage-gated, type XI, alpha subunit |
| NCAPG | 0.589 | 1.126 | 1.421 | 2.157 | 1.92 | 2.124 | 1.997 | 0.0241754 | non-SMC condensin I complex, subunit G |
| YLPM1 | 5.552 | 5.118 | 5.146 | 6.16 | 6.117 | 6.396 | 1.998 | 0.0185276 | YLP motif containing 1 |
| NEURL4 | 6.201 | 5.35 | 5.613 | 6.493 | 6.612 | 6.811 | 1.999 | 0.0406482 | neuralized homolog 4 (Drosophila) |
| ABCF1 | 8.571 | 8.103 | 7.891 | 9.406 | 8.891 | 9.263 | 2 | 0.0265779 | ATP-binding cassette, sub-family F (GCN20), member 1 |
| UPP2 | 5.108 | 4.587 | 4.954 | 6.21 | 5.864 | 5.588 | 2.001 | 0.0234027 | uridine phosphorylase 2 |
| CTSC | 7.03 | 6.652 | 6.904 | 8.11 | 7.485 | 7.905 | 2.001 | 0.0234864 | cathepsin C |
| CEP192 | 4.34 | 4.409 | 4.456 | 5.411 | 6.146 | 4.856 | 2.003 | 0.0382063 | centrosomal protein 192kDa |
| POLE | 6.218 | 5.676 | 5.679 | 6.866 | 6.743 | 6.679 | 2.004 | 0.0268598 | polymerase (DNA directed), epsilon |
| CTU1 | 7.068 | 6.377 | 6.169 | 7.593 | 7.381 | 7.373 | 2.006 | 0.0447399 | cytosolic thiouridylase subunit 1 homolog (S. pombe) |
| LOC100292680 | 2.972 | 3.285 | 2.439 | 3.447 | 4.289 | 3.896 | 2.006 | 0.0469192 | No description |
| NAT10 | 8.556 | 7.438 | 8.027 | 9.562 | 8.789 | 8.902 | 2.008 | 0.0423303 | N-acetyltransferase 10 (GCN5-related) |
| DPP3 | 4.908 | 4.086 | 4.722 | 5.915 | 5.492 | 5.425 | 2.01 | 0.0281256 | dipeptidyl-peptidase 3 |
| LOC390595 | 5.916 | 5.154 | 5.429 | 6.408 | 6.777 | 6.437 | 2.011 | 0.0221213 | No description |
| C1orf162 | 2.241 | 2.357 | 1.44 | 3.365 | 2.812 | 3.022 | 2.011 | 0.0324247 | chromosome 1 open reading frame 162 |
| SPAG5 | 4.773 | 3.161 | 4.477 | 5.339 | 5.783 | 5.484 | 2.013 | 0.0237054 | sperm associated antigen 5 |
| RPL35 | 13.834 | 13.033 | 13.62 | 14.844 | 14.377 | 14.416 | 2.014 | 0.0254897 | ribosomal protein L35 |
| VAMP8 | 6.996 | 7.462 | 6.998 | 8.007 | 8.203 | 8.102 | 2.015 | 0.0185419 | vesicle-associated membrane protein 8 (endobrevin) |
| ZNF547 | 2.189 | 1.488 | 1.435 | 2.625 | 2.446 | 3.088 | 2.015 | 0.0338671 | zinc finger protein 547 |
| MBLAC1 | 4.051 | 3.743 | 3.809 | 4.758 | 5.022 | 4.952 | 2.021 | 0.008871 | metallo-beta-lactamase domain containing 1 |
| ZNF280C | 4.279 | 3.849 | 3.457 | 5.294 | 4.656 | 4.53 | 2.021 | 0.0468048 | zinc finger protein 280C |
| SFXN2 | 2.807 | 2.903 | 2.844 | 4.252 | 3.755 | 3.859 | 2.022 | 0.0086585 | sideroflexin 2 |
| TRIP13 | 4.181 | 4.158 | 4.068 | 5.35 | 5.174 | 4.793 | 2.022 | 0.0174351 | thyroid hormone receptor interactor 13 |
| C14orf176 | 3.418 | 2.766 | 3.331 | 4.526 | 3.762 | 4.346 | 2.022 | 0.0305309 | chromosome 14 open reading frame 176 |
| ZNF749 | 1.243 | 1.246 | 1.182 | 2.26 | 2.268 | 1.676 | 2.023 | 0.0375674 | zinc finger protein 749 |
| PCNXL3 | 7.225 | 6.713 | 6.737 | 7.856 | 7.73 | 8.036 | 2.025 | 0.0189011 | pecanex-like 3 (Drosophila) |
| LIME1 | 4.704 | 3.721 | 4.211 | 5.366 | 5.229 | 5.22 | 2.025 | 0.0252501 | Lek interacting transmembrane adaptor 1 |
| TRIM68 | 0.68 | 1.494 | 1.038 | 2.313 | 1.699 | 2.382 | 2.026 | 0.0301846 | tripartite motif-containing 68 |
| EXOC3 | 7.076 | 6.101 | 6.32 | 7.644 | 7.326 | 7.338 | 2.026 | 0.0471324 | exocyst complex component 3 |
| RCCD1 | 5.047 | 4.618 | 4.501 | 5.939 | 6.066 | 5.508 | 2.027 | 0.0150032 | RCC1 domain containing 1 |
| STRN4 | 8.858 | 7.477 | 8.484 | 9.521 | 9.503 | 9.161 | 2.027 | 0.0405645 | striatin, calmodulin binding protein 4 |
| GOLGA3 | 7.632 | 7.437 | 6.97 | 8.637 | 8.29 | 8.457 | 2.028 | 0.0135158 | golgin A3 |
| ASZ1 | 3.902 | 4.446 | 4.067 | 4.964 | 5.467 | 5.085 | 2.029 | 0.0188045 | ankyrin repeat, SAM and basic leucine zipper domain containing 1 |
| C10orf12 | 1.632 | 1.767 | 2.439 | 3.259 | 2.653 | 2.978 | 2.029 | 0.0327402 | chromosome 10 open reading frame 12 |
| STARD10 | 6.616 | 5.753 | 6.198 | 6.859 | 7.309 | 7.22 | 2.03 | 0.0404143 | StAR-related lipid transfer (START) domain containing 10 |
| RBBP5 | 4.76 | 4.222 | 3.366 | 4.95 | 5.244 | 5.666 | 2.031 | 0.0385576 | retinoblastoma binding protein 5 |
| C19orf46 | 5.618 | 5.708 | 5.289 | 6.962 | 6.606 | 6.312 | 2.032 | 0.0157273 | chromosome 19 open reading frame 46 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24- N48 | CD24- N58 | CD24- N43 | CD24- N37 | CD24- N39 | CD24- N40 | | | |
| CCR6 | 3.921 | 3.414 | 3.889 | 4.439 | 5.484 | 4.823 | 2.034 | 0.0225749 | chemokine (C-C motif) receptor 6 |
| FLJ45340 | 6.401 | 5.737 | 6.033 | 6.934 | 7.426 | 6.762 | 2.034 | 0.0321192 | No description |
| KDM4A | 6.481 | 5.689 | 5.707 | 7.129 | 7.033 | 6.715 | 2.036 | 0.0323217 | lysine (K)-specific demethylase 4A |
| RNF126P1 | 7.269 | 7.01 | 7.018 | 8.392 | 8.044 | 7.937 | 2.037 | 0.0129942 | ring finger protein 126 pseudogene 1 |
| RRAGO | 7.582 | 6.404 | 7.04 | 8.154 | 8.066 | 7.999 | 2.037 | 0.0333491 | Ras-related GTP binding C |
| HOMER3 | 5.319 | 5.839 | 4.955 | 6.346 | 6.178 | 6.416 | 2.037 | 0.0362753 | homer homolog 3 (Drosophila) |
| C15orf40 | 4.189 | 4.466 | 4.22 | 5.487 | 5.282 | 5.217 | 2.039 | 0.0089168 | chromosome 15 open reading frame 40 |
| SETD4 | 4.735 | 4.221 | 5.209 | 6.017 | 5.58 | 5.763 | 2.039 | 0.0283194 | SET domain containing 4 |
| SCARF2 | 5.198 | 4.924 | 4.283 | 5.953 | 5.997 | 6.138 | 2.04 | 0.0136875 | scavenger receptor class F, member 2 |
| CYP27B1 | 5.891 | 5.464 | 5.878 | 7.03 | 6.492 | 6.839 | 2.04 | 0.0169428 | cytochrome P450, family 27, subfamily B, polypeptide 1 |
| CELSR3 | 3.642 | 3.7 | 4.3 | 4.35 | 5.329 | 4.937 | 2.041 | 0.0463032 | cadherin, EGF LAG seven-pass G-type receptor 3 (flamingo homolog, Drosophila) |
| CLDN15 | 6.315 | 4.142 | 5.876 | 6.907 | 7.336 | 6.604 | 2.044 | 0.0362059 | claudin 15 |
| NOP2 | 7.033 | 7.76 | 7.419 | 8.052 | 8.793 | 8.608 | 2.046 | 0.026363 | NOP2 nucleolar protein homolog (yeast) |
| SAPS3 | 8.809 | 8.193 | 7.866 | 9.266 | 9.226 | 9.097 | 2.046 | 0.0455398 | No description |
| YJEFN3 | 2.658 | 2.743 | 2.949 | 3.983 | 3.613 | 3.806 | 2.048 | 0.0111927 | YjeF N-terminal domain containing 3 |
| TMEM216 | 4.046 | 4.112 | 4.689 | 5.153 | 5.132 | 5.147 | 2.048 | 0.0361937 | transmembrane protein 216 |
| CACNA1I | 1.03 | 1.408 | 0.912 | 2.064 | 2.258 | 1.975 | 2.049 | 0.0168627 | calcium channel, voltage-dependent, T type, alpha 1I subunit |
| TIMM13 | 8.745 | 7.721 | 8.187 | 9.555 | 9.223 | 9.001 | 2.05 | 0.035195 | translocase of inner mitochondrial membrane 13 homolog (yeast) |
| GGT7 | 7.584 | 7.051 | 7.612 | 8.843 | 8.186 | 8.087 | 2.05 | 0.0409165 | gamma-glutamyltransferase 7 |
| C10orf125 | 4.003 | 3.526 | 3.082 | 5.039 | 4.973 | 3.893 | 2.05 | 0.0495328 | chromosome 10 open reading frame 125 |
| LOC389765 | 1.037 | 0.162 | 0.498 | 0.924 | 2.073 | 2.008 | 2.051 | 0.0476798 | No description |
| KIAA1875 | 9.192 | 8.836 | 9.273 | 10.009 | 10.312 | 9.963 | 2.054 | 0.0162267 | KIAA1875 |
| EXOSC9 | 4.554 | 4.489 | 4.399 | 5.656 | 5.439 | 5.45 | 2.055 | 0.0065393 | exosome component 9 |
| PSMD5 | 4.889 | 4.911 | 4.382 | 5.514 | 5.95 | 5.766 | 2.055 | 0.0193761 | proteasome (prosome, macropain) 26S subunit, non-ATPase, 5 |
| PYCR1 | 6.547 | 6.334 | 6.159 | 7.665 | 7.199 | 7.347 | 2.057 | 0.0126644 | pyrroline-5-carboxylate reductase 1 |
| MPL | 4.562 | 3.154 | 3.724 | 5.155 | 4.737 | 4.765 | 2.058 | 0.0484331 | myeloproliferative leukemia virus oncogene |
| IDH3A | 7.52 | 7.045 | 7.007 | 8.438 | 8.168 | 8.05 | 2.059 | 0.0169836 | Description |
| C19orf44 | 4.502 | 3.247 | 4.206 | 5.544 | 5.236 | 5.128 | 2.059 | 0.0181491 | chromosome 19 open reading frame 44 |
| RFPL1S | 4.052 | 4.463 | 4.067 | 5.531 | 5.108 | 4.894 | 2.059 | 0.0245646 | RFPL1 antisense RNA (non-protein coding) |
| EIF2S2 | 9.717 | 9.743 | 9.079 | 10.785 | 10.333 | 10.439 | 2.06 | 0.0263254 | eukaryotic translation initiation factor 2, subunit 2 beta, 38kDa |
| MCRS1 | 4.501 | 4.148 | 4.467 | 6.002 | 5.407 | 5.193 | 2.062 | 0.0152057 | microspherule protein 1 |
| ANKRD13D | 6.652 | 6.065 | 5.949 | 7.11 | 7.318 | 7.035 | 2.064 | 0.0313207 | ankyrin repeat domain 13 family, member D |
| HIATL2 | 4.307 | 4.544 | 4.235 | 4.975 | 5.353 | 5.638 | 2.065 | 0.0244952 | hippocampus abundant transcript-like 2 |
| DDX18 | 9.02 | 8.306 | 8.653 | 10.068 | 9.421 | 9.689 | 2.067 | 0.0233126 | DEAD (Asp-Glu-Ala-Asp) box polypeptide 18 |
| GIGYF1 | 8.552 | 8.362 | 9.012 | 9.537 | 9.596 | 9.58 | 2.068 | 0.0242913 | GRB10 interacting GYF protein 1 |
| SPATA5 | 4.436 | 4.271 | 4.461 | 5.891 | 5.285 | 5.485 | 2.069 | 0.0087043 | spermatogenesis associated 5 |
| FCF1 | 7.437 | 7.306 | 7.069 | 8.17 | 8.487 | 8.316 | 2.07 | 0.0098304 | FCF1 small subunit (SSU) processome component homolog (S. cerevisiae) |
| HSCB | 6.938 | 6.246 | 6.54 | 7.416 | 7.988 | 7.431 | 2.072 | 0.0257301 | HscB iron-sulfur cluster co-chaperone homolog (E. coli) |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24- N48 | CD24- N58 | CD24- N43 | CD24- N37 | CD24- N39 | CD24- N40 | Pseudo fold change | P value | Gene description |
| LOC100216545 | 4.173 | 3.818 | 4.58 | 4.952 | 5.631 | 4.968 | 2.072 | 0.0378021 | No description |
| C21orf49 | 4.84 | 5.428 | 5.118 | 6.401 | 6.09 | 6.169 | 2.073 | 0.0121213 | chromosome 21 open reading frame 49 |
| DPH3B | 1.826 | 0.78 | 1.998 | 2.85 | 3.051 | 2.54 | 2.075 | 0.0215533 | No description |
| KRT80 | 5.063 | 4.184 | 4.288 | 5.306 | 5.856 | 5.341 | 2.075 | 0.041622 | keratin 80 |
| ELAVL3 | 3.144 | 3.059 | 2.984 | 3.598 | 4.266 | 4.113 | 2.077 | 0.0270001 | ELAV (embryonic lethal, abnormal vision, Drosophila)-like 3 (Hu antigen C) |
| AACS | 2.964 | 2.36 | 2.144 | 3.295 | 3.415 | 3.467 | 2.077 | 0.0392681 | acetoacetyl-CoA synthetase |
| RPL38 | 12.702 | 11.879 | 12.419 | 13.476 | 13.365 | 13.62 | 2.08 | 0.0142828 | ribosomal protein L38 |
| C3orf62 | 6.239 | 5.548 | 5.821 | 6.843 | 6.973 | 6.878 | 2.081 | 0.0172977 | chromosome 3 open reading frame 62 |
| ZBED4 | 5.975 | 5.593 | 5.609 | 7.033 | 6.231 | 6.714 | 2.081 | 0.037282 | zinc finger, BED-type containing 4 |
| ZNF274 | 7.134 | 6.233 | 7.085 | 7.971 | 8.191 | 8.128 | 2.082 | 0.0117894 | zinc finger protein 274 |
| GPC5 | 0.478 | 0.666 | 0.619 | 1.407 | 1.678 | 2.52 | 2.084 | 0.0151191 | glypican 5 |
| KDM6B | 11.711 | 10.082 | 11.001 | 12.062 | 12.285 | 11.93 | 2.086 | 0.0448229 | lysine (K)-specific demethylase 6B |
| TFAP4 | 4.048 | 4.452 | 4.176 | 5.898 | 5.216 | 5.11 | 2.088 | 0.0145832 | transcription factor AP-4 (activating enhancer binding protein 4) |
| ZNF181 | 3.252 | 2.774 | 2.724 | 3.787 | 4.227 | 3.857 | 2.089 | 0.0179116 | zinc finger protein 181 |
| USP37 | 5.66 | 4.95 | 4.681 | 6.012 | 6.483 | 5.864 | 2.089 | 0.0397353 | ubiquitin specific peptidase 37 |
| GINS1 | 3.856 | 2.548 | 3.259 | 4.868 | 4.322 | 4.277 | 2.09 | 0.0238084 | GINS complex subunit 1 (Psf1 homolog) |
| ACSS1 | 4.695 | 4.017 | 4.781 | 5.759 | 5.762 | 5.083 | 2.09 | 0.0347578 | acyl-CoA synthetase short-chain family member 1 |
| SRCIN1 | 3.259 | 3.358 | 3.432 | 4.792 | 4.422 | 4.142 | 2.091 | 0.011765 | SRC kinase signaling inhibitor 1 |
| B3GNT4 | 1.885 | 2.108 | 1.44 | 3.093 | 3.057 | 2.504 | 2.091 | 0.0220019 | UDP-GlcNAc:betaGal beta-1,3-N-acetylglucosaminyltransferase 4 |
| NANOS1 | 5.942 | 5.654 | 5.142 | 6.719 | 6.732 | 6.703 | 2.092 | 0.0134485 | nanos homolog 1 (Drosophila) |
| FBXO25 | 4.507 | 4.51 | 4.238 | 5.647 | 5.254 | 5.573 | 2.093 | 0.0097031 | F-box protein 25 |
| KLHL17 | 4.942 | 5.261 | 5.803 | 6.737 | 6.326 | 6.147 | 2.093 | 0.0270852 | kelch-like 17 (Drosophila) |
| MPHOSPH6 | 6.092 | 6.111 | 5.606 | 7.74 | 6.672 | 7.155 | 2.094 | 0.0174909 | M-phase phosphoprotein 6 |
| LOC728190 | 5.578 | 4.722 | 4.883 | 6.368 | 5.789 | 6.124 | 2.095 | 0.0318645 | No description |
| HSF2BP | 1.949 | 1.976 | 0.912 | 2.466 | 3.043 | 2.726 | 2.095 | 0.0322609 | heat shock transcription factor 2 binding protein |
| PHRF1 | 8.573 | 7.219 | 7.779 | 8.956 | 8.847 | 8.829 | 2.097 | 0.0498891 | PHD and ring finger domains 1 |
| ERICH1 | 5.957 | 5.849 | 5.266 | 7.024 | 6.807 | 6.918 | 2.098 | 0.0088445 | glutamate-rich 1 |
| ATP6VOD2 | 6.688 | 6.176 | 6.125 | 7.194 | 7.628 | 7.466 | 2.098 | 0.0142956 | ATPase, H+ transporting, lysosomal 38kDa, VO subunit d2 |
| PAQR5 | 3.016 | 3.717 | 2.735 | 4.281 | 4.219 | 3.805 | 2.099 | 0.0488302 | progestin and adipoQ receptor family member V |
| C1orf106 | 3.855 | 4.928 | 5.355 | 6.338 | 5.914 | 5.998 | 2.1 | 0.020895 | chromosome 1 open reading frame 106 |
| C17orf63 | 6.519 | 6.136 | 6.118 | 7.598 | 7.131 | 7.207 | 2.101 | 0.0146577 | chromosome 17 open reading frame 63 |
| FAM50B | 4.02 | 3.21 | 3.389 | 4.739 | 4.516 | 4.282 | 2.102 | 0.034194 | family with sequence similarity 50, member B |
| ATPAF1 | 5.58 | 4.551 | 4.923 | 6.522 | 5.995 | 5.755 | 2.102 | 0.0380704 | ATP synthase mitochondrial F1 complex assembly factor 1 |
| MRAP2 | 4.366 | 3.964 | 4.088 | 5.303 | 5.17 | 5.037 | 2.103 | 0.0108421 | melanocortin 2 receptor accessory protein 2 |
| PIGM | 4.256 | 3.893 | 3.567 | 5.328 | 4.442 | 5.24 | 2.103 | 0.0296938 | phosphatidylinositol glycan anchor biosynthesis, class M |
| PDDC1 | 4.081 | 4.473 | 4.967 | 5.548 | 5.75 | 5.199 | 2.106 | 0.035924 | Parkinson disease 7 domain containing 1 |
| MSH | 8.427 | 8.034 | 7.937 | 9.012 | 9.467 | 9.221 | 2.108 | 0.0121628 | musashi homolog 1 (Drosophila) |
| GOLIM4 | 4.797 | 4.222 | 4.74 | 5.492 | 5.299 | 6.043 | 2.11 | 0.02915 | golgi integral membrane protein 4 |
| RAVER2 | 3.808 | 4.375 | 4.274 | 4.902 | 5.453 | 5.303 | 2.112 | 0.0185204 | ribonucleoprotein, PTB-binding 2 |
| ZC3H4 | 5.826 | 5.978 | 5.44 | 6.709 | 7.008 | 6.905 | 2.113 | 0.0098376 | zinc finger CCCH-type containing 4 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| NCS1 | 8.41 | 7.988 | 8.618 | 9.672 | 9.49 | 9.417 | 2.114 | 0.0086778 | neuronal calcium sensor 1 |
| RARS2 | 4.689 | 3.928 | 3.847 | 5.151 | 4.928 | 5.287 | 2.115 | 0.036716 | arginyl-tRNA synthetase 2, mitochondrial |
| PPP1R3E | 3.722 | 3.314 | 3.698 | 4.395 | 4.812 | 4.498 | 2.116 | 0.0176232 | protein phosphatase 1, regulatory (inhibitor) subunit 3E |
| ZCCHC10 | 4.756 | 4.276 | 3.779 | 5.586 | 4.881 | 5.357 | 2.116 | 0.0435515 | zinc finger, COHO domain containing 10 |
| SF3B5 | 10.333 | 9.448 | 9.643 | 11.121 | 10.531 | 10.808 | 2.119 | 0.0358067 | splicing factor 3b, subunit 5, 10kDa |
| PRKCZ | 6.388 | 6.328 | 6.489 | 7.573 | 7.401 | 7.56 | 2.12 | 0.0042727 | protein kinase C, zeta |
| DAK | 6.032 | 6.131 | 5.726 | 7.216 | 6.711 | 7.148 | 2.121 | 0.0146247 | dihydroxyacetone kinase 2 homolog (S. cerevisiae) |
| RHEBL1 | 3.933 | 3.958 | 3.692 | 4.235 | 5.575 | 5.018 | 2.121 | 0.0407634 | Ras homolog enriched in brain like 1 |
| OTUD5 | 8.449 | 7.376 | 7.767 | 8.853 | 9.195 | 8.708 | 2.122 | 0.0349767 | OTU domain containing 5 |
| RNF20 | 4.364 | 3.484 | 3.305 | 5.403 | 4.7 | 4.39 | 2.122 | 0.0445797 | ring finger protein 20 |
| TMC4 | 3.661 | 3.532 | 2.957 | 4.043 | 5.214 | 4.565 | 2.123 | 0.0251878 | transmembrane channel-like 4 |
| EID3 | 5.729 | 5.545 | 5.411 | 6.374 | 6.704 | 6.816 | 2.124 | 0.0106632 | EP300 interacting inhibitor of differentiation 3 |
| STX10 | 1.334 | 1.513 | 0.888 | 1.949 | 3.121 | 2.421 | 2.124 | 0.0213021 | syntaxin 10 |
| PRICKLES | 3.678 | 3.475 | 4.154 | 5.448 | 4.75 | 4.562 | 2.124 | 0.0232124 | prickle homolog 3 (Drosophila) |
| MTPAP | 8.991 | 8.37 | 8.937 | 9.938 | 10.078 | 9.895 | 2.125 | 0.0084725 | mitochondrial poly(A) polymerase |
| MDFI | 7.121 | 7.083 | 7.719 | 8.537 | 8.171 | 8.443 | 2.125 | 0.0170645 | MyoD family inhibitor |
| ESRRA | 8.54 | 7.704 | 7.794 | 9.61 | 8.882 | 8.877 | 2.125 | 0.0305652 | estrogen-related receptor alpha |
| ABRA | 3.762 | 3.647 | 3.237 | 5.027 | 4.734 | 3.957 | 2.125 | 0.0416041 | actin-binding Rho activating protein |
| LYPD3 | 8.158 | 7.495 | 5.484 | 8.584 | 8.806 | 8.404 | 2.126 | 0.0464814 | LY6/PLAUR domain containing 3 |
| TRABD | 9.07 | 8.838 | 8.748 | 10.198 | 9.838 | 9.851 | 2.129 | 0.0096151 | TraB domain containing |
| FAM83A | 6.273 | 6.298 | 6.614 | 7.177 | 7.705 | 7.467 | 2.13 | 0.0138878 | family with sequence similarity 83, member A |
| C6orf145 | 10.308 | 9.415 | 10.016 | 10.91 | 11.314 | 11.107 | 2.131 | 0.0150104 | chromosome 6 open reading frame 145 |
| SSRP1 | 8.88 | 7.713 | 8.239 | 9.727 | 9.331 | 9.288 | 2.131 | 0.0252078 | structure specific recognition protein 1 |
| DUSP28 | 3.651 | 2.163 | 2.867 | 3.958 | 4.169 | 3.951 | 2.131 | 0.0403477 | dual specificity phosphatase 28 |
| KRBA2 | 6.382 | 5.533 | 6.244 | 7.1 | 7.474 | 7.12 | 2.132 | 0.0162195 | KRAB-A domain containing 2 |
| RNF185 | 6.18 | 6.073 | 6.409 | 7.473 | 7.167 | 7.418 | 2.134 | 0.0066609 | ring finger protein 185 |
| SNRPF | 8.774 | 8.427 | 8.411 | 9.868 | 9.465 | 9.725 | 2.135 | 0.0079452 | small nuclear ribonucleoprotein polypeptide F |
| RIN1 | 3.09 | 3.389 | 2.495 | 4.185 | 4.465 | 4.053 | 2.135 | 0.0127531 | Ras and Rab interactor 1 |
| LOC283914 | 4.157 | 3.606 | 3.564 | 4.659 | 4.855 | 5.191 | 2.136 | 0.015361 | No description |
| RPS15A | 10.403 | 10.303 | 10.91 | 11.398 | 11.719 | 11.649 | 2.136 | 0.0165966 | ribosomal protein S15a |
| CAMKK1 | 3.801 | 2.251 | 3.934 | 4.545 | 4.897 | 4.912 | 2.138 | 0.0238492 | calcium/calmodulin-dependent protein kinase kinase 1, alpha |
| ARL5A | 8.188 | 7.178 | 7.873 | 8.981 | 8.969 | 8.909 | 2.139 | 0.0155691 | ADP-ribosylation factor-like 5A |
| DHX35 | 0.986 | 1.037 | 1.386 | 3.157 | 2.126 | 2.083 | 2.139 | 0.0158239 | DEAH (Asp-Glu-Ala-His) box polypeptide 35 |
| SPEN | 10.39 | 9.61 | 9.879 | 10.773 | 11.189 | 10.977 | 2.14 | 0.0250118 | spen homolog, transcriptional regulator (Drosophila) |
| NOC4L | 7.791 | 6.65 | 7.391 | 8.89 | 8.174 | 8.34 | 2.142 | 0.0277864 | nucleolar complex associated 4 homolog (S. cerevisiae) |
| EI24 | 8.345 | 7.442 | 7.793 | 8.893 | 8.635 | 9.047 | 2.143 | 0.032444 | etoposide induced 2.4 mRNA |
| CECR7 | 3.207 | 3.112 | 2.824 | 3.539 | 4.212 | 4.322 | 2.144 | 0.031886 | cat eye syndrome chromosome region, candidate 7 (non-protein coding) |
| CENPL | 3.588 | 4.243 | 3.118 | 4.689 | 4.596 | 4.834 | 2.146 | 0.0326343 | centromere protein L |
| ZNF34 | 5.928 | 6.097 | 4.804 | 7.104 | 7.031 | 6.628 | 2.147 | 0.0217243 | zinc finger protein 34 |
| SDCCAG3 | 7.632 | 7.701 | 8.134 | 9.163 | 8.81 | 8.736 | 2.148 | 0.0140073 | serologically defined colon cancer antigen 3 |
| AARS | 6.473 | 5.958 | 5.646 | 7.136 | 6.958 | 7.061 | 2.148 | 0.0226873 | alanyl-tRNA synthetase |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| GRIN2A | 2.17 | 2.26 | 2.158 | 2.73 | 3.983 | 3.273 | 2.148 | 0.0287236 | glutamate receptor, ionotropic, N-methyl D-aspartate 2A |
| FUBP1 | 8.785 | 6.746 | 8.009 | 9.112 | 9.52 | 9.067 | 2.148 | 0.0369707 | far upstream element (FUSE) binding protein 1 |
| TECRL | 4.758 | 3.642 | 4.234 | 5.74 | 4.745 | 5.393 | 2.148 | 0.0478114 | trans-2,3-enoyl-CoA reductase-like |
| SUPT3H | 4.074 | 3.49 | 3.377 | 4.623 | 4.667 | 4.482 | 2.151 | 0.0279888 | suppressor of Ty 3 homolog (S. cerevisiae) |
| GIT1 | 6.113 | 5.509 | 5.564 | 6.943 | 6.614 | 7.087 | 2.152 | 0.01303 | G protein-coupled receptor kinase interacting ArGAP 1 |
| PWWP2A | 5.523 | 4.037 | 5.079 | 6.185 | 6.281 | 6.045 | 2.152 | 0.0248222 | PWWP domain containing 2A |
| ATAD3A | 8.453 | 7.672 | 7.875 | 9.057 | 8.995 | 8.778 | 2.152 | 0.032703 | ATPase family, AAA domain containing 3A |
| BCAM | 7.264 | 6.699 | 6.499 | 7.805 | 8.084 | 7.746 | 2.153 | 0.0205473 | basal cell adhesion molecule (Lutheran blood group) |
| XPO4 | 4.638 | 4.708 | 5.015 | 6.186 | 5.745 | 5.79 | 2.154 | 0.0099921 | exportin 4 |
| C2orf76 | 3.779 | 2.947 | 3.364 | 4.886 | 4.271 | 4.455 | 2.154 | 0.0177134 | chromosome 2 open reading frame 76 |
| PSMG3 | 6.954 | 6.615 | 6.333 | 7.724 | 8.12 | 7.228 | 2.158 | 0.0296222 | proteasome (prosome, macropain) assembly chaperone 3 |
| MSTO2P | 3.451 | 3.955 | 4.409 | 5.065 | 4.89 | 5.151 | 2.159 | 0.0217314 | misato homolog 2 pseudogene |
| SFXN1 | 3.047 | 3.352 | 3.434 | 4.475 | 4.545 | 4.012 | 2.16 | 0.0148558 | sideroflexin 1 |
| SAPS2 | 6.821 | 6.436 | 7.063 | 8.187 | 7.918 | 7.547 | 2.16 | 0.0176762 | No description |
| CNOT1 | 6.267 | 6.462 | 7.038 | 7.221 | 8.149 | 7.744 | 2.16 | 0.029193 | CCR4-NOT transcription complex, subunit 1 |
| IL12RB2 | 0.924 | 1.305 | 0.994 | 2.838 | 1.738 | 2.106 | 2.161 | 0.0238993 | interleukin 12 receptor, beta 2 |
| MOG | 1.847 | 1.241 | 0.543 | 2.913 | 2.352 | 1.864 | 2.161 | 0.0441812 | myelin oligodendrocyte glycoprotein |
| PDIA3 | 5.892 | 5.848 | 5.941 | 7.005 | 8.057 | 6.623 | 2.162 | 0.019927 | protein disulfide isomerase family A, member 3 |
| C7orf29 | 3.427 | 3.456 | 2.96 | 5.193 | 4.238 | 4.072 | 2.162 | 0.023274 | chromosome 7 open reading frame 29 |
| LOC100133957 | 3.999 | 3.595 | 3.812 | 4.708 | 5.362 | 4.871 | 2.163 | 0.0109788 | No description |
| DHX34 | 5.495 | 4.906 | 4.647 | 5.676 | 6.609 | 6.028 | 2.164 | 0.0348802 | DEAH (Asp-Glu-Ala-His) box polypeptide 34 |
| HSP90B1 | 7.909 | 9.464 | 8.909 | 9.981 | 10.038 | 10.024 | 2.165 | 0.0292946 | heat shock protein 90kDa beta (Grp94), member 1 |
| PANX2 | 3.994 | 4.614 | 4.315 | 5.431 | 5.564 | 5.237 | 2.166 | 0.0124025 | pannexin 2 |
| DDX31 | 5.384 | 6.407 | 5.927 | 6.829 | 7.093 | 7.042 | 2.167 | 0.0257158 | DEAD (Asp-Glu-Ala-Asp) box polypeptide 31 |
| KIAA1530 | 4.327 | 5.181 | 4.914 | 6.297 | 5.942 | 6.003 | 2.168 | 0.0103856 | KIAA1530 |
| SRCAP | 6.83 | 6.603 | 7.291 | 7.719 | 8.384 | 8.221 | 2.168 | 0.0145761 | Snf2-related CREBBP activator protein |
| CELF1 | 7.086 | 6.671 | 6.689 | 8.203 | 7.752 | 7.907 | 2.169 | 0.009799 | CUGBP, Elav-like family member 1 |
| ZNF625 | 5.086 | 5.14 | 4.828 | 6.162 | 6.3 | 5.946 | 2.17 | 0.0073557 | zinc finger protein 625 |
| LOC100294362 | 8.693 | 8.135 | 8.335 | 9.454 | 9.65 | 9.388 | 2.172 | 0.0103499 | No description |
| PCGF2 | 8.219 | 7.18 | 7.557 | 8.708 | 8.822 | 8.299 | 2.172 | 0.049902 | polycomb group ring finger 2 |
| TUBGCP4 | 3.95 | 3.303 | 3.329 | 4.829 | 4.423 | 4.641 | 2.174 | 0.0161923 | tubulin, gamma complex associated protein 4 |
| ALX3 | 2.956 | 2.861 | 1.315 | 4.076 | 3.556 | 3.601 | 2.174 | 0.0315969 | ALX homeobox 3 |
| METTL12 | 1.424 | 2.888 | 2.665 | 4.008 | 3.56 | 3.282 | 2.174 | 0.0317135 | methyltransferase like 12 |
| C4orf43 | 4.011 | 3.68 | 3.29 | 5.207 | 4.1 | 4.802 | 2.175 | 0.0442477 | chromosome 4 open reading frame 43 |
| TTF2 | 3.684 | 3.788 | 4.581 | 4.955 | 4.909 | 4.881 | 2.175 | 0.047976 | transcription termination factor, RNA polymerase II |
| LOC647979 | 7.522 | 7.205 | 7.547 | 8.643 | 8.289 | 8.872 | 2.176 | 0.0092366 | No description |
| ZNF780B | 2.891 | 3.251 | 3.694 | 4.483 | 4.373 | 4.227 | 2.176 | 0.017888 | zinc finger protein 780B |
| HS3ST2 | 3.601 | 4.459 | 1.429 | 5.378 | 4.631 | 4.722 | 2.176 | 0.0418051 | heparan sulfate (glucosamine) 3-O-sulfotransferase 2 |
| C20orf12 | 3.149 | 1.536 | 2.596 | 3.915 | 3.718 | 3.217 | 2.176 | 0.0465336 | chromosome 20 open reading frame 12 |
| C22orf30 | 4.992 | 4.244 | 4.551 | 6.114 | 5.378 | 5.458 | 2.177 | 0.0305137 | chromosome 22 open reading frame 30 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| KIAA0664 | 9.002 | 8.446 | 9.511 | 10.244 | 10.126 | 10.055 | 2.178 | 0.0201002 | KIAA0664 |
| PPHLN1 | 7.595 | 8.338 | 7.651 | 8.774 | 8.785 | 8.772 | 2.178 | 0.0347972 | periphilin 1 |
| CACNA1A | 3.059 | 3.149 | 2.524 | 3.647 | 4.334 | 3.684 | 2.178 | 0.0367439 | calcium channel, voltage-dependent, P/Q type, alpha 1A subunit |
| SAMD1 | 5.64 | 5.016 | 4.631 | 5.608 | 7.046 | 6.139 | 2.178 | 0.0489225 | sterile alpha motif domain containing 1 |
| MYL7 | 3.609 | 4.912 | 4.611 | 5.734 | 5.679 | 6.021 | 2.179 | 0.0130758 | myosin, light chain 7, regulatory |
| BRD9 | 7.865 | 7.024 | 7.74 | 8.989 | 8.726 | 8.626 | 2.18 | 0.0124827 | bromodomain containing 9 |
| DMWD | 7.048 | 6.29 | 6.462 | 7.714 | 7.665 | 7.415 | 2.18 | 0.0258153 | dystrophia myotonica, WD repeat containing |
| LOC26080 | 1.513 | 1.715 | 1.301 | 2.638 | 2.782 | 2.493 | 2.182 | 0.0072813 | No description |
| PPAPDC2 | 3.727 | 4.528 | 4.431 | 6.117 | 4.848 | 5.556 | 2.182 | 0.0259712 | phosphatidic acid phosphatase type 2 domain containing 2 |
| IL20RB | 1.66 | 2.142 | 1.075 | 2.515 | 3.269 | 2.777 | 2.183 | 0.0221492 | interleukin 20 receptor beta |
| EP300 | 8.06 | 7.573 | 8.197 | 8.7 | 9.274 | 9.279 | 2.184 | 0.016618 | E1A binding protein p300 |
| STMN1 | 8.863 | 7.929 | 8.786 | 9.056 | 10.015 | 9.657 | 2.184 | 0.047855 | stathmin 1 |
| KIAA1919 | 4.956 | 4.005 | 4.679 | 5.987 | 5.35 | 5.808 | 2.187 | 0.0222279 | KIAA1919 |
| LAT | 4.363 | 3.94 | 4.208 | 5.133 | 5.87 | 5.07 | 2.189 | 0.0153996 | linker for activation of T cells |
| PTPN23 | 7.908 | 7.259 | 7.594 | 9.264 | 8.505 | 8.39 | 2.189 | 0.0242362 | protein tyrosine phosphatase, non-receptor type 23 |
| HSF1 | 10.009 | 9.31 | 9.478 | 10.787 | 10.44 | 10.635 | 2.19 | 0.0213343 | heat shock transcription factor 1 |
| BET1L | 5.526 | 4.895 | 4.852 | 6.294 | 6.027 | 5.997 | 2.191 | 0.022512 | blocked early in transport 1 homolog (S. cerevisiae)-like |
| BHMT2 | 5.862 | 5.795 | 5.491 | 6.771 | 6.996 | 6.665 | 2.194 | 0.008758 | betaine homocysteine S-methyltransferase 2 |
| PLCB3 | 3.94 | 3.303 | 3.071 | 4.627 | 4.437 | 4.426 | 2.194 | 0.0225993 | phospholipase C, beta 3 (phosphatidylinositol-specific) |
| ZNF341 | 4.241 | 2.483 | 3.787 | 5.374 | 4.643 | 4.814 | 2.194 | 0.0271238 | zinc finger protein 341 |
| HOXA9 | 5.212 | 4.626 | 4.223 | 6.326 | 5.637 | 5.76 | 2.195 | 0.0201789 | homeobox A9 |
| TMEM120B | 5.301 | 5.65 | 6.467 | 7.421 | 6.68 | 6.785 | 2.196 | 0.0339465 | transmembrane protein 120B |
| LOC728606 | 4.446 | 4.539 | 4.132 | 5.296 | 5.675 | 5.297 | 2.197 | 0.0130014 | No description |
| KIAA0226 | 4.956 | 5.51 | 4.843 | 6.513 | 5.972 | 6.647 | 2.2 | 0.0114803 | KIAA0226 |
| NPM3 | 7.542 | 7.266 | 7.509 | 8.981 | 8.634 | 8.405 | 2.203 | 0.0065894 | nucleophosmin/nucleoplasmin 3 |
| ZNF692 | 5.125 | 5.739 | 5.653 | 6.513 | 6.878 | 6.635 | 2.203 | 0.010709 | zinc finger protein 692 |
| ZNF75A | 1.03 | 1.141 | 1.52 | 2.281 | 2.171 | 2.619 | 2.203 | 0.0111712 | zinc finger protein 75a |
| CPSF7 | 9.397 | 7.659 | 9.095 | 10.283 | 10.235 | 9.773 | 2.203 | 0.0309179 | cleavage and polyadenylation specific factor 7, 59kDa |
| CHI3L1 | 2.843 | 5.136 | 4.666 | 5.216 | 6.275 | 5.682 | 2.203 | 0.0446362 | chitinase 3-like 1 (cartilage glycoprotein-39) |
| MED10 | 6.502 | 5.776 | 6.217 | 7.642 | 7.097 | 7.256 | 2.204 | 0.0148193 | mediator complex subunit 10 |
| INO80E | 7.11 | 5.593 | 6.513 | 8.004 | 7.596 | 7.654 | 2.205 | 0.0221085 | INO80 complex subunit E |
| C2orf81 | 5.238 | 5.22 | 5.09 | 6.212 | 6.361 | 6.501 | 2.206 | 0.0039501 | chromosome 2 open reading frame 81 |
| C21orf88 | 6.171 | 5.605 | 6.126 | 6.954 | 7.404 | 6.747 | 2.207 | 0.0215103 | chromosome 21 open reading frame 88 |
| LOC645676 | 4.104 | 3.017 | 3.233 | 4.159 | 4.878 | 4.557 | 2.207 | 0.0399077 | No description |
| CCDC123 | 4.762 | 3.591 | 3.943 | 4.962 | 5.36 | 5.086 | 2.208 | 0.0414302 | coiled-coil domain containing 123 |
| ZNF558 | 4.403 | 4.257 | 4.882 | 5.547 | 5.627 | 5.476 | 2.21 | 0.0156822 | zinc finger protein 558 |
| INTS9 | 5.821 | 4.984 | 5.177 | 6.714 | 6.321 | 6.169 | 2.21 | 0.0257373 | integrator complex subunit 9 |
| ZSCAN22 | 3.012 | 1.504 | 2.337 | 3.331 | 3.48 | 3.869 | 2.21 | 0.028421 | zinc finger and SCAN domain containing 22 |
| ERCC4 | 2.594 | 2.511 | 2.966 | 3.415 | 4.266 | 3.739 | 2.211 | 0.0198855 | excision repair cross-complementing rodent repair deficiency, complementation group 4 |
| ZBTB48 | 5.726 | 4.925 | 4.925 | 6.364 | 6.475 | 6.07 | 2.211 | 0.0212828 | zinc finger and BTB domain containing 48 |
| LRRC10 | 2.111 | 1.466 | 1.824 | 2.417 | 3.28 | 2.97 | 2.213 | 0.0262045 | leucine rich repeat containing 10 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| GPS2 | 8.616 | 7.495 | 7.526 | 9.141 | 8.928 | 8.641 | 2.214 | 0.0495521 | G protein pathway suppressor 2 |
| PHAX | 5.097 | 4.97 | 5.3 | 6.245 | 6.137 | 6.304 | 2.215 | 0.0058088 | phosphorylated adaptor for RNA export |
| CDK5R1 | 5.094 | 5.52 | 4.926 | 6.241 | 6.241 | 6.427 | 2.215 | 0.0102819 | cyclin-dependent kinase 5, regulatory subunit 1 (p35) |
| CUL4A | 8.602 | 7.514 | 8.439 | 9.749 | 9.47 | 9.396 | 2.215 | 0.0127216 | cullin 4A |
| MAGOH | 10.216 | 8.466 | 9.31 | 10.862 | 10.325 | 10.457 | 2.215 | 0.0450834 | mago-nashi homolog, proliferation-associated (Drosophila) |
| NIP7 | 8.825 | 7.166 | 8.059 | 9.607 | 8.957 | 9.207 | 2.216 | 0.0394076 | nuclear import 7 homolog (S. cerevisiae) |
| DEGS1 | 6.007 | 5.802 | 6.144 | 6.938 | 7.516 | 7.155 | 2.217 | 0.0074122 | degenerative spermatocyte homolog 1, lipid desaturase (Drosophila) |
| SLC30A6 | 5.334 | 5.256 | 4.979 | 6.482 | 6.252 | 6.166 | 2.217 | 0.0077434 | solute carrier family 30 (zinc transporter), member 6 |
| UBE3B | 3.812 | 4.022 | 4.443 | 5.172 | 4.961 | 5.261 | 2.217 | 0.0166967 | ubiquitin protein ligase E3B |
| ARMC6 | 7.162 | 4.877 | 6.297 | 8.127 | 7.217 | 7.446 | 2.218 | 0.0414231 | armadillo repeat containing 6 |
| PERS | 4.322 | 4.468 | 4.441 | 5.345 | 5.59 | 5.648 | 2.218 | 0.0053567 | period homolog 3 (Drosophila) |
| SULT1A1 | 4.138 | 4.368 | 4.039 | 5.458 | 5.287 | 5.256 | 2.219 | 0.0051613 | sulfotransferase family, cytosolic, 1A, phenol-preferring, member 1 |
| ZCCHC4 | 5.422 | 5.358 | 5.575 | 6.58 | 6.725 | 6.273 | 2.219 | 0.0094198 | zinc finger, CCHC domain containing 4 |
| THG1L | 2.939 | 2.744 | 2.75 | 4.262 | 3.901 | 3.579 | 2.22 | 0.0129033 | tRNA-histidine guanylyltransferase 1-like (S. cerevisiae) |
| TSEN2 | 3.526 | 2.897 | 2.324 | 4.421 | 3.932 | 4.049 | 2.223 | 0.0226064 | tRNA splicing endonuclease 2 homolog (S. cerevisiae) |
| WDHD1 | 2.352 | 1.572 | 1.075 | 3.006 | 2.402 | 2.725 | 2.223 | 0.0489769 | WD repeat and HMG-box DNA binding protein 1 |
| PAQR7 | 7.553 | 6.937 | 7.442 | 8.599 | 8.669 | 8.297 | 2.23 | 0.0092151 | progestin and adipoQ receptor family member VII |
| RFPL3S | 3.862 | 4.103 | 4.056 | 5.213 | 5.494 | 4.5 | 2.23 | 0.0275567 | RFPL3 antisense RNA (non-protein coding) |
| GPR153 | 2.927 | 2.365 | 3.262 | 4.36 | 3.838 | 4.087 | 2.234 | 0.0138306 | G protein-coupled receptor 153 |
| RHOD | 4.01 | 4.689 | 3.998 | 5.839 | 5.396 | 5.16 | 2.236 | 0.0144652 | ras homolog gene family, member D |
| DUSP10 | 4.565 | 6.581 | 5.948 | 7.103 | 7.394 | 7.111 | 2.24 | 0.0256758 | dual specificity phosphatase 10 |
| OTX2OS1 | 3.03 | 3.812 | 3.409 | 3.999 | 4.975 | 4.738 | 2.24 | 0.0275982 | No description |
| C17orf73 | 5.24 | 4.149 | 4.884 | 5.981 | 6.342 | 6.048 | 2.241 | 0.0111641 | chromosome 17 open reading frame 73 |
| KLHL31 | 0.986 | 0.666 | 1.029 | 1.875 | 1.83 | 2.363 | 2.241 | 0.0114238 | kelch-like 31 (Drosophila) |
| LOC1001288 42 | 4.661 | 4.951 | 4.434 | 6.403 | 5.456 | 5.826 | 2.242 | 0.0164513 | No description |
| DHX32 | 6.735 | 6.014 | 5.728 | 7.904 | 6.869 | 7.723 | 2.248 | 0.0203356 | DEAH (Asp-Glu-Ala-His) box polypeptide 32 |
| PNPT1 | 6.721 | 6.737 | 6.953 | 8.2 | 7.49 | 7.907 | 2.249 | 0.0166109 | polyribonucleotide nucleotidyltransferase 1 |
| LOC441208 | 0.708 | 1.88 | 2.557 | 2.85 | 3.728 | 2.54 | 2.252 | 0.0497775 | No description |
| ZNF768 | 7.192 | 5.171 | 6.205 | 7.301 | 7.736 | 7.377 | 2.253 | 0.0475817 | zinc finger protein 768 |
| PIGR | 3.915 | 4.2 | 4.351 | 4.633 | 6.054 | 5.373 | 2.255 | 0.0313579 | polymeric immunoglobulin receptor |
| TMEM68 | 5.29 | 5.512 | 4.803 | 6.65 | 6.415 | 6.463 | 2.256 | 0.0063354 | transmembrane protein 68 |
| C16orf52 | 8.615 | 7.21 | 7.832 | 8.77 | 9.017 | 9.006 | 2.256 | 0.0496609 | chromosome 16 open reading frame 52 |
| HIPK3 | 4.61 | 3.46 | 4.553 | 5.786 | 5.245 | 5.325 | 2.258 | 0.0243736 | homeodomain interacting protein kinase 3 |
| TRAPPC6A | 3.315 | 2.311 | 2.592 | 4.567 | 3.496 | 3.486 | 2.258 | 0.0494727 | trafficking protein particle complex 6A |
| ZNF133 | 2.429 | 2.978 | 3.278 | 3.869 | 4.028 | 4.455 | 2.261 | 0.0151506 | zinc finger protein 133 |
| GCKR | 4.779 | 3.202 | 3.73 | 4.781 | 5.597 | 4.907 | 2.261 | 0.0482836 | glucokinase (hexokinase 4) regulator |
| MMP3 | 9.732 | 6.452 | 9.93 | 11.107 | 10.264 | 10.683 | 2.262 | 0.0456507 | matrix metallopeptidase 3 (stromelysin 1, progelatinase) |
| EID2 | 4.148 | 3.749 | 4.263 | 5.442 | 4.95 | 5.236 | 2.263 | 0.0106368 | EP300 interacting inhibitor of differentiation 2 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| CSTF1 | 5.364 | 4.677 | 4.73 | 6.22 | 6.172 | 5.857 | 2.265 | 0.013583 | cleavage stimulation factor, 3' pre-RNA, subunit 1, 50kDa |
| DGCR11 | 2.999 | 2.157 | 2.25 | 3.719 | 3.43 | 3.392 | 2.266 | 0.0266044 | DiGeorge syndrome critical region gene 11 |
| RRP15 | 6.051 | 5.372 | 5.429 | 6.861 | 6.65 | 6.553 | 2.267 | 0.0178558 | ribosomal RNA processing 15 homolog (S. cerevisiae) |
| PRRT3 | 3.246 | 4.227 | 3.658 | 4.86 | 4.84 | 4.595 | 2.268 | 0.0271761 | proline-rich transmembrane protein 3 |
| LOC100190940 | 2.021 | 1.388 | 1.715 | 3.204 | 3.14 | 2.556 | 2.271 | 0.0110002 | No description |
| MBP | 6.014 | 6.771 | 5.69 | 7.955 | 6.8 | 7.358 | 2.271 | 0.0345883 | myelin basic protein |
| COL22A1 | 1.065 | 1.44 | 1.513 | 2.254 | 2.648 | 2.663 | 2.279 | 0.0084446 | collagen, type XXII, alpha 1 |
| CARD10 | 7.241 | 7.632 | 7.717 | 8.957 | 8.429 | 8.587 | 2.279 | 0.012087 | caspase recruitment domain family, member 10 |
| SLC41A3 | 5.871 | 5.434 | 5.261 | 6.749 | 6.45 | 6.676 | 2.279 | 0.0124097 | solute carrier family 41, member 3 |
| NUP93 | 8.14 | 7.317 | 7.943 | 9.405 | 8.506 | 8.695 | 2.281 | 0.0373607 | nucleoporin 93kDa |
| FOXA1 | 2.602 | 3.195 | 2.482 | 4.582 | 3.318 | 3.793 | 2.283 | 0.0384074 | forkhead box A1 |
| FLJ16779 | 1.065 | 1.03 | 0.994 | 2.41 | 1.738 | 2.222 | 2.285 | 0.0128633 | No description |
| PDCD11 | 6.734 | 6.022 | 5.731 | 7.722 | 7.214 | 7.041 | 2.285 | 0.0253717 | programmed cell death 11 |
| FAM48A | 5.071 | 5.014 | 5.357 | 6.264 | 6.376 | 6.257 | 2.286 | 0.0050132 | family with sequence similarity 48, member A |
| ATP2A1 | 2.827 | 3.259 | 2.948 | 4.14 | 4.587 | 3.577 | 2.286 | 0.0267311 | ATPase, Ca++ transporting, cardiac muscle, fast twitch 1 |
| WDR5 | 5.668 | 5.336 | 5.203 | 6.937 | 6.294 | 6.53 | 2.287 | 0.0111011 | WD repeat domain 5 |
| WDR46 | 7.78 | 6.648 | 6.869 | 8.426 | 7.841 | 8.111 | 2.287 | 0.0467926 | WD repeat domain 46 |
| GALNS | 5.699 | 4.71 | 5.395 | 6.876 | 6.589 | 6.285 | 2.288 | 0.0133047 | galactosamine (N-acetyl)-6-sulfate sulfatase |
| LOC84740 | 1.936 | 1.067 | 0.929 | 2.724 | 2.488 | 2.124 | 2.289 | 0.0280854 | No description |
| S100A2 | 11.222 | 10.556 | 8.256 | 12.232 | 11.522 | 11.751 | 2.292 | 0.0343679 | S100 calcium binding protein A2 |
| MRPL4 | 7.891 | 7.264 | 7.389 | 8.82 | 8.586 | 8.493 | 2.293 | 0.0127388 | mitochondrial ribosomal protein L4 |
| C2orf14 | 4.669 | 4.802 | 4.459 | 5.656 | 6.3 | 5.84 | 2.293 | 0.006525 | chromosome 2 open reading frame 14 |
| MYLK3 | 4.886 | 4.265 | 4.261 | 5.458 | 5.538 | 5.515 | 2.293 | 0.0175152 | myosin light chain kinase 3 |
| PLEKHA6 | 5.923 | 5.367 | 4.825 | 6.464 | 6.605 | 6.564 | 2.293 | 0.019668 | pleckstrin homology domain containing, family A member 6 |
| C16orf93 | 2.886 | 2.993 | 3.757 | 4.892 | 4.121 | 4.19 | 2.293 | 0.0238563 | chromosome 16 open reading frame 93 |
| PHF5A | 7.218 | 6.414 | 6.482 | 7.959 | 7.623 | 7.68 | 2.293 | 0.0248508 | PHD finger protein 5A |
| ABCC13 | 2.891 | 2.726 | 2.927 | 4.089 | 4.281 | 3.764 | 2.295 | 0.0063054 | ATP-binding cassette, sub-family C (CFTR/MRP), member 13, pseudogene |
| SLC6A15 | 1.876 | 1.958 | 1.737 | 4.026 | 2.807 | 3.076 | 2.298 | 0.0104779 | solute carrier family 6 (neutral amino acid transporter), member 15 |
| ACER3 | 7.367 | 6.473 | 6.347 | 8.107 | 7.607 | 7.675 | 2.3 | 0.0353774 | alkaline ceramidase 3 |
| CYP8B1 | 2.359 | 2.868 | 1.747 | 3.814 | 3.984 | 2.949 | 2.301 | 0.0289633 | cytochrome P450, family 8, subfamily B, polypeptide 1 |
| C8orf41 | 3.703 | 2.888 | 2.628 | 4.662 | 4.091 | 3.871 | 2.302 | 0.0340338 | chromosome 8 open reading frame 41 |
| SMARCA4 | 8.464 | 7.874 | 8.528 | 9.732 | 9.109 | 9.244 | 2.303 | 0.0229763 | SWI/SNF related, matrix associated, actin dependent regulator of chromatin, subfamily a, member 4 |
| LOC100130015 | 0.708 | 0.283 | 0.88 | 1.911 | 1.773 | 2.084 | 2.305 | 0.0055448 | No description |
| SLC12A4 | 5.444 | 4.955 | 5.238 | 6.649 | 6.357 | 6.277 | 2.305 | 0.0067375 | solute carrier family 12 (potassium/chloride transporters), member 4 |
| CD209 | 2.061 | 1.314 | 2.2 | 3.228 | 3.288 | 3.269 | 2.309 | 0.0065322 | CD209 molecule |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| RNASEH1 | 4.353 | 4.798 | 4.302 | 5.975 | 5.736 | 5.509 | 2.309 | 0.0069514 | ribonuclease H1 |
| BAG4 | 4.471 | 3.927 | 2.898 | 5.134 | 5.303 | 5 | 2.309 | 0.0206954 | BCL2-associated athanogene 4 |
| PXN | 6.856 | 7.485 | 7.828 | 9.036 | 7.996 | 9.017 | 2.311 | 0.0245274 | paxillin |
| ZNF536 | 1.297 | 3.014 | 2.727 | 3.937 | 3.3 | 4.062 | 2.313 | 0.0299084 | zinc finger protein 536 |
| CWF19L1 | 3.171 | 2.478 | 2.295 | 4.403 | 3.474 | 3.69 | 2.317 | 0.0247178 | CWF19-like 1, cell cycle control (S. pombe) |
| BMS1P4 | 1.172 | 0.834 | 1.681 | 2.895 | 1.604 | 2.841 | 2.318 | 0.0380318 | BMS1 pseudogene 4 |
| ZMAT5 | 5.002 | 4.229 | 3.953 | 5.444 | 5.972 | 5.42 | 2.321 | 0.0209559 | zinc finger, matrin-type 5 |
| RPS6KB2 | 4.207 | 3.988 | 4.507 | 5.562 | 5.723 | 5.061 | 2.322 | 0.0109931 | ribosomal protein S6 kinase, 70kDa, polypeptide 2 |
| TTF1 | 5.201 | 4.815 | 3.762 | 6.417 | 5.525 | 5.909 | 2.322 | 0.0259977 | transcription termination factor, RNA polymerase I |
| LOC25845 | 5.6 | 4.712 | 4.826 | 6.295 | 6.041 | 5.96 | 2.322 | 0.0273163 | No description |
| RUNDC1 | 7.004 | 6.623 | 7.224 | 8.091 | 8.44 | 7.932 | 2.323 | 0.010103 | RUN domain containing 1 |
| PAR5 | 3.075 | 3.944 | 3.259 | 4.966 | 4.475 | 4.346 | 2.324 | 0.020357 | No description |
| CAPNS2 | 3.743 | 3.001 | 1.793 | 3.933 | 4.218 | 4.232 | 2.324 | 0.0442026 | calpain, small subunit 2 |
| TMEM170B | 3.706 | 4.223 | 4.234 | 4.869 | 5.611 | 5.44 | 2.325 | 0.0118423 | transmembrane protein 1706 |
| PMCHL2 | 2.758 | 2.004 | 2.624 | 3.227 | 3.66 | 3.976 | 2.326 | 0.0203713 | pro-melanin-concentrating hormone-like 2, pseudogene |
| KRT86 | 6.004 | 6.548 | 5.324 | 7.528 | 6.713 | 7.221 | 2.326 | 0.0311497 | keratin 86 |
| WDR62 | 3.218 | 3.211 | 3.528 | 4.466 | 4.747 | 4.138 | 2.327 | 0.0113408 | WD repeat domain 62 |
| KCTD15 | 7.158 | 5.96 | 6.966 | 8.37 | 7.925 | 8.185 | 2.328 | 0.0108614 | potassium channel tetramerisation domain containing 15 |
| NIF3L1 | 2.936 | 2.868 | 2.229 | 4.155 | 3.513 | 3.764 | 2.328 | 0.0195629 | NIF3 NGG1 interacting factor 3-like 1 (S. pombe) |
| BCL2L13 | 7.496 | 6.151 | 7.389 | 8.117 | 8.715 | 8.161 | 2.328 | 0.0256829 | BCL2-like 13 (apoptosis facilitator) |
| ACD | 4.292 | 3.17 | 2.967 | 4.814 | 4.895 | 4.185 | 2.328 | 0.0430572 | adrenocortical dysplasia homolog (mouse) |
| GGT6 | 3.106 | 3.528 | 3.69 | 4.558 | 4.91 | 4.74 | 2.329 | 0.0057409 | gamma-glutamyltransferase 6 |
| C16orf46 | 4.221 | 3.617 | 4.776 | 5.24 | 5.582 | 5.441 | 2.329 | 0.0196823 | chromosome 16 open reading frame 46 |
| INTS7 | 8.944 | 8.408 | 8.474 | 9.629 | 10.285 | 9.643 | 2.33 | 0.011539 | integrator complex subunit 7 |
| MITD1 | 2.14 | 1.907 | 2.497 | 3.313 | 3.49 | 3.361 | 2.331 | 0.0068284 | MIT, microtubule interacting and transport, domain containing 1 |
| SLC15A2 | 3.222 | 3.093 | 3.918 | 5.026 | 4.314 | 4.663 | 2.331 | 0.0154461 | solute carrier family 15 (H+/peptide transporter), member 2 |
| WDR20 | 6.103 | 4.719 | 5.366 | 6.577 | 6.587 | 6.646 | 2.331 | 0.0265114 | WD repeat domain 20 |
| FLJ45445 | 8.371 | 8.583 | 8.925 | 10.148 | 9.643 | 9.653 | 2.335 | 0.0108206 | No description |
| WDR89 | 4.293 | 2.807 | 3.516 | 4.656 | 4.739 | 4.909 | 2.335 | 0.0289561 | WD repeat domain 89 |
| NDUFAB1 | 7.914 | 7.11 | 6.692 | 8.482 | 7.916 | 8.53 | 2.336 | 0.0445868 | NADH dehydrogenase (ubiquinone) 1, alpha/beta subcomplex, 1, 8kDa |
| CCNA2 | 2.993 | 1.66 | 2.339 | 3.746 | 3.564 | 3.117 | 2.338 | 0.0373678 | cyclin A2 |
| WDR90 | 3.129 | 2.735 | 3.059 | 4.751 | 3.958 | 4.285 | 2.339 | 0.0069235 | WD repeat domain 90 |
| SCT | 1.571 | 2.004 | 0.842 | 2.189 | 2.797 | 2.889 | 2.339 | 0.0324104 | secretin |
| GCN1L1 | 7.563 | 7.124 | 7.401 | 8.789 | 8.394 | 8.618 | 2.34 | 0.0056786 | GCN1 general control of amino-acid synthesis 1-like 1 (yeast) |
| YPEL1 | 5.357 | 4.933 | 5.535 | 6.761 | 6.464 | 6.417 | 2.34 | 0.0065751 | yippee-like 1 (Drosophila) |
| RNF157 | 3.297 | 3.365 | 2.532 | 4.551 | 4.525 | 4.232 | 2.341 | 0.0078965 | ring finger protein 157 |
| PFDN6 | 7.175 | 5.247 | 6.242 | 7.85 | 7.358 | 7.469 | 2.341 | 0.0373163 | prefoldin subunit 6 |
| NCOA6 | 6.056 | 4.902 | 5.633 | 7.035 | 6.862 | 6.626 | 2.344 | 0.0149689 | nuclear receptor coactivator 6 |
| PPIL6 | 4.859 | 4.07 | 3.955 | 5.184 | 5.455 | 5.313 | 2.344 | 0.0304851 | peptidylprolyl isomerase (cyclophilin)-like 6 |
| DUSP7 | 10.617 | 9.421 | 9.942 | 11.324 | 10.862 | 11.171 | 2.345 | 0.0306182 | dual specificity phosphatase 7 |
| HIPK2 | 8.821 | 8.118 | 8.408 | 10.156 | 9.155 | 9.638 | 2.346 | 0.0213737 | homeodomain interacting protein kinase 2 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| LOC285456 | 2.651 | 2.812 | 2.358 | 3.963 | 4.042 | 2.933 | 2.346 | 0.0441311 | No description |
| RC3H2 | 5.185 | 4.105 | 4.67 | 6.09 | 5.817 | 5.901 | 2.347 | 0.0135616 | ring finger and CCCH-type domains 2 |
| WNT6 | 3.423 | 4.068 | 4.03 | 4.654 | 5.487 | 5.164 | 2.347 | 0.0144151 | wingless-type MMTV integration site family, member 6 |
| ZNF232 | 5.316 | 4.817 | 5.147 | 6.547 | 5.738 | 6.386 | 2.347 | 0.0191751 | zinc finger protein 232 |
| SNORA78 | 5.526 | 5.4 | 5.72 | 5.929 | 6.983 | 6.756 | 2.347 | 0.0394448 | small nucleolar RNA, H/ACA box 78 |
| XKRX | 1.037 | 2.533 | 2.014 | 3.643 | 2.548 | 3.246 | 2.348 | 0.0383652 | XK, Kell blood group complex subunit-related, X-linked |
| SIRPB2 | 2.6 | 2.677 | 1.062 | 2.798 | 3.909 | 3.562 | 2.348 | 0.0472777 | signal-regulatory protein beta 2 |
| P2RX7 | 4.112 | 3.778 | 4.203 | 4.604 | 5.435 | 5.358 | 2.349 | 0.0222931 | purinergic receptor P2X, ligand-gated ion channel, 7 |
| ARHGAP22 | 2.97 | 2.795 | 2.6 | 4.229 | 3.655 | 4.028 | 2.351 | 0.008803 | Rho GTPase activating protein 22 |
| TOP1 | 7.946 | 6.727 | 7.301 | 8.391 | 8.851 | 8.536 | 2.353 | 0.0191279 | topoisomerase (DNA) I |
| ELP2P | 2.669 | 1.075 | 1.762 | 3.632 | 2.601 | 2.996 | 2.353 | 0.045215 | No description |
| SLC7A5P2 | 6.739 | 6.039 | 4.373 | 7.035 | 7.818 | 7.274 | 2.354 | 0.0282614 | solute carrier family 7 (cationic amino acid transporter, y+ system), member 5 pseudogene 2 |
| WHSC1 | 6.655 | 6.355 | 6.486 | 7.879 | 7.695 | 7.723 | 2.357 | 0.0030443 | Wolf-Hirschhorn syndrome candidate 1 |
| MUC1 | 5.183 | 3.648 | 4.424 | 5.422 | 6.146 | 5.661 | 2.357 | 0.0274286 | mucin 1, cell surface associated |
| SFRS14 | 6.582 | 5.807 | 6.73 | 7.522 | 7.967 | 7.608 | 2.358 | 0.0111855 | No description |
| RPS12 | 12.823 | 11.989 | 12.05 | 13.704 | 13.287 | 13.263 | 2.358 | 0.0209687 | ribosomal protein S12 |
| CSNK2A2 | 7.261 | 6.675 | 6.528 | 7.913 | 8.016 | 7.823 | 2.358 | 0.0156493 | casein kinase 2, alpha prime polypeptide |
| QPCTL | 2.609 | 3.112 | 2.336 | 4.402 | 3.762 | 3.574 | 2.359 | 0.0180239 | glutaminyl-peptide cyclotransferase-like |
| C16orf55 | 1.651 | 1.241 | 1.589 | 2.827 | 2.91 | 2.06 | 2.359 | 0.0224569 | chromosome 16 open reading frame 55 |
| NAF1 | 7.012 | 6.435 | 7.298 | 8.163 | 8.528 | 8.251 | 2.36 | 0.0066874 | nuclear assembly factor 1 homolog (S. cerevisiae) |
| PPTC7 | 5.601 | 5.716 | 6.221 | 6.812 | 7.46 | 7.34 | 2.36 | 0.0076876 | PTC7 protein phosphatase homolog (S. cerevisiae) |
| DCLRE1A | 2.248 | 2.722 | 1.72 | 3.487 | 3.114 | 3.721 | 2.36 | 0.0190356 | DNA cross-link repair 1A |
| ESRP2 | 6.27 | 5.608 | 6.485 | 7.649 | 6.846 | 7.513 | 2.36 | 0.0212277 | epithelial splicing regulatory protein 2 |
| C9orf102 | 1.748 | 2.028 | 2.18 | 3.269 | 3.233 | 3.333 | 2.363 | 0.003412 | chromosome 9 open reading frame 102 |
| OGFRL1 | 6.813 | 6.762 | 7.73 | 8.003 | 8.964 | 8.309 | 2.364 | 0.0200057 | opioid growth factor receptor-like 1 |
| FGF5 | 3.653 | 3.601 | 3.514 | 4.985 | 4.366 | 4.843 | 2.365 | 0.0098061 | fibroblast growth factor 5 |
| CLTB | 11.248 | 9.465 | 10.177 | 11.739 | 11.419 | 11.346 | 2.365 | 0.047058 | clathrin, light chain B |
| C4orf10 | 5.447 | 5.023 | 5.158 | 6.54 | 6.265 | 6.441 | 2.366 | 0.0053853 | chromosome 4 open reading frame 10 |
| KLK14 | 2.382 | 2.931 | 2.671 | 4.048 | 3.96 | 3.624 | 2.366 | 0.0079953 | kallikrein-related peptidase 14 |
| ZNF709 | 3.308 | 2.691 | 2.688 | 3.93 | 4.252 | 4.14 | 2.366 | 0.0095142 | zinc finger protein 709 |
| AMN | 2.956 | 2.004 | 2.724 | 4.728 | 3.247 | 3.672 | 2.367 | 0.0318294 | amnionless homolog (mouse) |
| NR5A1 | 0.817 | 1.629 | 0.757 | 2.946 | 1.678 | 2.06 | 2.368 | 0.0423811 | nuclear receptor subfamily 5, group A, member 1 |
| CCDC144A | 4.378 | 3.837 | 4.11 | 5.573 | 5.354 | 5.216 | 2.369 | 0.0056142 | coiled-coil domain containing 144A |
| SECISBP2 | 5.753 | 4.648 | 4.915 | 6.179 | 6.16 | 5.924 | 2.37 | 0.0455827 | SECIS binding protein 2 |
| SMURF1 | 8.016 | 6.622 | 7.808 | 9.186 | 9.053 | 8.267 | 2.371 | 0.0283487 | SMAD specific E3 ubiquitin protein ligase 1 |
| SFRS15 | 7.65 | 6.159 | 7.216 | 8.294 | 8.882 | 8.462 | 2.372 | 0.0134843 | No description |
| TNFRSF9 | 2.976 | 3.635 | 2.284 | 3.855 | 4.223 | 4.314 | 2.373 | 0.0325778 | tumor necrosis factor receptor superfamily, member 9 |
| LMTK3 | 4.894 | 3.808 | 3.753 | 5.118 | 6.07 | 5.001 | 2.376 | 0.0369171 | lemur tyrosine kinase 3 |
| C19orf28 | 8.353 | 8.026 | 7.678 | 9.603 | 8.937 | 9.025 | 2.377 | 0.0164585 | chromosome 19 open reading frame 28 |
| EIF5B | 9.476 | 8.984 | 9.054 | 10.562 | 10.233 | 10.33 | 2.378 | 0.0070323 | eukaryotic translation initiation factor 5B |
| LOC220729 | 4.918 | 3.945 | 5.588 | 6.168 | 6.833 | 6.101 | 2.378 | 0.0167332 | No description |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| LOC1001305 81 | 7.628 | 6.543 | 6.556 | 7.793 | 7.947 | 8.137 | 2.378 | 0.0408163 | No description |
| C12orf48 | 0.825 | 1.15 | 2.282 | 2.97 | 2.317 | 2.4 | 2.378 | 0.0480761 | chromosome 12 open reading frame 48 |
| ZBTB3 | 1.767 | 1.494 | 1.52 | 3.125 | 2.372 | 2.771 | 2.379 | 0.0120541 | zinc finger and BTB domain containing 3 |
| FANCA | 4.017 | 4.035 | 4.27 | 4.817 | 5.521 | 5.433 | 2.38 | 0.012957 | Fanconi anemia, complementation group A |
| BCL7A | 5.69 | 6.298 | 6.07 | 7.617 | 6.615 | 7.322 | 2.382 | 0.0231552 | B-cell CLL/lymphoma 7A |
| SLC2A10 | 4.783 | 3.578 | 4.463 | 6.036 | 4.959 | 5.64 | 2.383 | 0.0307412 | solute carrier family 2 (facilitated glucose transporter), member 10 |
| LOC1002722 17 | 1.077 | 1.464 | 1.611 | 2.843 | 2.488 | 2.717 | 2.384 | 0.00522 | No description |
| ZNF611 | 4.827 | 4.5 | 5.072 | 6.063 | 6.389 | 5.753 | 2.385 | 0.0088231 | zinc finger protein 611 |
| ZNF260 | 2.8 | 2.756 | 3.015 | 3.559 | 4.055 | 4.343 | 2.386 | 0.0148122 | zinc finger protein 260 |
| LOC1001348 68 | 2.628 | 2.707 | 2.779 | 3.962 | 4.435 | 3.799 | 2.387 | 0.0043836 | No description |
| SLC25A10 | 3.508 | 2.588 | 2.526 | 4.622 | 4.764 | 3.181 | 2.388 | 0.0430715 | solute carrier family 25 (mitochondrial carrier; dicarboxylate transporter), member 10 |
| ALG13 | 3.001 | 2.677 | 1.747 | 4.258 | 3.774 | 3.879 | 2.389 | 0.0104851 | asparagine-linked glycosylation 13 homolog (S. cerevisiae) |
| EP400 | 7.305 | 6.566 | 7.274 | 8.562 | 8.276 | 8.212 | 2.39 | 0.0087365 | E1A binding protein p400 |
| REXO1 | 8.168 | 7.12 | 7.131 | 8.377 | 8.872 | 8.646 | 2.39 | 0.0277935 | REX1, RNA exonuclease 1 homolog (S. cerevisiae) |
| BAG2 | 3.622 | 3.258 | 2.885 | 4.646 | 4.516 | 4.146 | 2.392 | 0.0135015 | BCL2-associated athanogene 2 |
| SEMA3B | 7.431 | 7.024 | 6.951 | 8.283 | 8.736 | 8.158 | 2.393 | 0.0082042 | sema domain, immunoglobulin domain (ig), short basic domain, secreted, (semaphorin) 3B |
| MRPS36 | 7.91 | 7.21 | 7.272 | 8.531 | 8.543 | 8.499 | 2.393 | 0.0171718 | mitochondrial ribosomal protein S36 |
| MGC3771 | 2.266 | 1.99 | 1.611 | 2.967 | 3.249 | 3.342 | 2.394 | 0.0084868 | No description |
| EFTUD1 | 6.101 | 5.972 | 6.045 | 7.73 | 6.619 | 7.304 | 2.394 | 0.0198784 | elongation factor Tu GTP binding domain containing 1 |
| CCDC110 | 1.408 | 1.471 | 0.251 | 1.949 | 2.731 | 2.6 | 2.396 | 0.0201452 | coiled-coil domain containing 110 |
| EBNA1BP2 | 7.093 | 7.477 | 7.07 | 8.738 | 7.844 | 8.484 | 2.397 | 0.0193339 | EBNA1 binding protein 2 |
| C17orf55 | 4.014 | 3.41 | 4.184 | 4.212 | 5.615 | 5.275 | 2.397 | 0.0442835 | chromosome 17 open reading frame 55 |
| NKRF | 6.268 | 5.524 | 5.724 | 6.832 | 7.235 | 6.988 | 2.402 | 0.0126844 | NFKB repressing factor |
| SYNGR3 | 1.888 | −0.046 | 1.538 | 2.803 | 2.999 | 2.735 | 2.403 | 0.0143307 | synaptogyrin 3 |
| C1orf135 | 9.672 | 8.847 | 9.089 | 10.599 | 10.496 | 10.112 | 2.404 | 0.0147521 | chromosome 1 open reading frame 135 |
| FAM86B2 | 4.123 | 3.704 | 4.368 | 5.377 | 4.969 | 5.788 | 2.404 | 0.0108786 | family with sequence similarity 86, member B2 |
| NKAP | 5.226 | 4.993 | 4.958 | 6.452 | 6.367 | 6.224 | 2.405 | 0.0028053 | NFKB activating protein |
| ABCB5 | 1.875 | 1.44 | 1.762 | 3.316 | 2.835 | 2.708 | 2.408 | 0.0078844 | ATP-binding cassette, sub-family B (MDR/TAP), member 5 |
| ARFGAP1 | 4.329 | 4.699 | 3.964 | 5.672 | 5.47 | 5.597 | 2.408 | 0.0079037 | ADP-ribosylation factor GTPase activating protein 1 |
| PRMT1 | 10.708 | 10.007 | 10.649 | 12.15 | 11.275 | 11.416 | 2.408 | 0.0244881 | protein arginine methyltransferase 1 |
| ZRSR2 | 4.568 | 4.634 | 3.843 | 5.755 | 5.788 | 5.905 | 2.413 | 0.0046713 | zinc finger (CCCH type), RNA-binding motif and serine/arginine rich 2 |
| LMTK2 | 7.25 | 7.894 | 7.608 | 9.006 | 8.646 | 8.88 | 2.415 | 0.0071861 | lemur tyrosine kinase 2 |
| CAPN2 | 7.525 | 8.619 | 7.533 | 8.798 | 9.02 | 8.968 | 2.416 | 0.042165 | calpain 2, (m/ll) large subunit |
| C5orf35 | 4.056 | 3.787 | 4.464 | 5.245 | 5.331 | 5.693 | 2.42 | 0.006867 | chromosome 5 open reading frame 35 |
| ZNF70 | 2.791 | 2.623 | 2.712 | 3.616 | 4.068 | 3.991 | 2.424 | 0.0058654 | zinc finger protein 70 |
| PILRA | 2.982 | 4.098 | 3.311 | 4.588 | 4.499 | 5.079 | 2.424 | 0.0196952 | paired immunoglobin-like type 2 receptor alpha |
| EIF4G2 | 10.177 | 10.936 | 11.007 | 11.804 | 12.15 | 12.285 | 2.425 | 0.0086413 | eukaryotic translation initiation factor 4 gamma, 2 |

TABLE 6-continued

Differentially Expressed Genes in CD10+ Breast Epithelial Cells

| | Nulliparous (NP) Samples | | | Parous (P) Samples | | | | | | |
|---|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| KIAA0895 | 4.005 | 3.399 | 3.009 | 4.955 | 4.674 | 4.677 | 2.425 | 0.0114381 | KIAA0895 |
| DHX30 | 8.723 | 7.521 | 7.499 | 9.511 | 8.777 | 8.922 | 2.425 | 0.0418573 | DEAH (Asp-Glu-Ala-His) box polypeptide 30 |
| GLDC | 0.478 | 0.588 | 0.543 | 1.757 | 3.046 | 1.77 | 2.428 | 0.0074265 | glycine dehydrogenase (decarboxylating) |
| WDR31 | 1.19 | 0.819 | 1.47 | 2.4 | 2.751 | 2.115 | 2.429 | 0.0100429 | WD repeat domain 31 |
| MARS | 9.352 | 9.31 | 8.813 | 11.017 | 10.094 | 10.094 | 2.43 | 0.0172233 | methionyl-tRNA synthetase |
| NDUFB10 | 4.101 | 4.536 | 3.38 | 4.661 | 5.387 | 5.786 | 2.43 | 0.0296423 | NADH dehydrogenase (ubiquinone) 1 beta subcomplex, 10, 22kDa |
| TRIP4 | 3.5 | 2.361 | 2.648 | 4.432 | 4.424 | 3.644 | 2.432 | 0.0202755 | thyroid hormone receptor interactor 4 |
| BOK | 6.57 | 6.334 | 5.459 | 7.853 | 7.289 | 7.375 | 2.433 | 0.0133247 | BCL2-related ovarian killer |
| FBXO2 | 7.603 | 7.224 | 6.945 | 8.536 | 8.508 | 8.288 | 2.435 | 0.0091128 | F-box protein 2 |
| C9orf91 | 5.367 | 5.299 | 5.211 | 6.652 | 6.528 | 6.53 | 2.436 | 0.001853 | chromosome 9 open reading frame 91 |
| GTF2H2 | 4.898 | 3.818 | 4.34 | 5.109 | 6.182 | 5.139 | 2.436 | 0.0478908 | general transcription factor IIH, polypeptide 2, 44kDa |
| SLC4A2 | 7.906 | 6.651 | 6.806 | 8.44 | 8.463 | 7.937 | 2.439 | 0.0359898 | solute carrier family 4, anion exchanger, member 2 (erythrocyte membrane protein band 3-like 1) |
| RPL14 | 11.414 | 10.612 | 10.941 | 11.989 | 12.341 | 12.232 | 2.446 | 0.0119489 | ribosomal protein L14 |
| RPL32P3 | 4.128 | 3.378 | 3.085 | 4.852 | 4.684 | 4.376 | 2.447 | 0.028021 | ribosomal protein L32 pseudogene 3 |
| ZNF594 | 2.418 | 1.314 | 2.211 | 3.713 | 3.321 | 3.031 | 2.453 | 0.0146441 | zinc finger protein 594 |
| TMEM53 | 5.806 | 4.826 | 5.172 | 6.466 | 6.746 | 6.192 | 2.453 | 0.018695 | transmembrane protein 53 |
| C1orf83 | 6.994 | 6.342 | 6.653 | 7.798 | 8.158 | 7.948 | 2.454 | 0.0061072 | chromosome 1 open reading frame 83 |
| WDR81 | 5.044 | 4.436 | 5.193 | 6.41 | 6.34 | 5.846 | 2.456 | 0.0102397 | WD repeat domain 81 |
| ZNF566 | 3.931 | 3.273 | 4.018 | 5.228 | 5.27 | 4.816 | 2.457 | 0.0075367 | zinc finger protein 566 |
| LOC100131496 | 6.765 | 5.852 | 6.176 | 7.673 | 7.395 | 7.472 | 2.457 | 0.0116999 | No description |
| ODF2 | 6.848 | 5.687 | 6.049 | 8.05 | 6.985 | 7.59 | 2.458 | 0.0222208 | outer dense fiber of sperm tails 2 |
| HSPB8 | 9.41 | 9.475 | 7.962 | 10.259 | 10.773 | 10.641 | 2.459 | 0.0133806 | heat shock 22kDa protein 8 |
| DNAJC11 | 6.207 | 5.632 | 5.742 | 8.023 | 6.522 | 7.041 | 2.46 | 0.0244473 | DnaJ (Hsp40) homolog, subfamily C, member 11 |
| PLOD3 | 7.898 | 6.792 | 6.822 | 8.224 | 8.286 | 8.091 | 2.46 | 0.0431037 | procollagen-lysine, 2-oxoglutarate 5-dioxygenase 3 |
| SCAP | 7.254 | 6.446 | 6.858 | 8.18 | 8.115 | 8.158 | 2.462 | 0.0071618 | SREBF chaperone |
| OSR1 | 7.137 | 6.381 | 6.947 | 7.799 | 8.366 | 8.247 | 2.462 | 0.0095428 | odd-skipped related 1 (Drosophila) |
| ADAT1 | 1.77 | 2.737 | 2.406 | 3.057 | 3.706 | 4.216 | 2.462 | 0.0196144 | adenosine deaminase, tRNA-specific 1 |
| SMOC1 | 3.662 | 5 | 3.75 | 5.513 | 5.737 | 4.962 | 2.462 | 0.0325921 | SPARC related modular calcium binding 1 |
| FXR2 | 7.616 | 6.899 | 7.189 | 8.916 | 8.385 | 8.335 | 2.463 | 0.0093275 | fragile X mental retardation, autosomal homolog 2 |
| ANKRD42 | 3.534 | 1.611 | 3.273 | 4.688 | 4.444 | 4.573 | 2.463 | 0.013143 | ankyrin repeat domain 42 |
| HSPBP1 | 7.389 | 6.301 | 6.403 | 8.369 | 7.842 | 7.602 | 2.464 | 0.0252694 | HSPA (heat shock 70kDa) binding protein, cytoplasmic cochaperone 1 |
| MRPL28 | 7.447 | 5.513 | 6.15 | 8.203 | 7.448 | 7.452 | 2.465 | 0.0450905 | mitochondrial ribosomal protein L28 |
| FAM179A | 0.162 | 1.067 | 2.168 | 2.882 | 2.053 | 2.37 | 2.467 | 0.0497181 | family with sequence similarity 179, member A |
| CSPG5 | 2.828 | 2.621 | 2.652 | 4.335 | 3.843 | 3.956 | 2.469 | 0.0037025 | chondroitin sulfate proteoglycan 5 (neuroglycan C) |
| JAG1 | 8.075 | 8.903 | 8.292 | 9.6 | 9.596 | 9.59 | 2.469 | 0.0128196 | jagged 1 |
| DHDDS | 4.339 | 3.539 | 2.925 | 5.526 | 4.233 | 5.276 | 2.476 | 0.0293575 | dehydrodolichyl diphosphate synthase |
| GPLD1 | 3.235 | 3.31 | 3.72 | 5.029 | 4.403 | 4.722 | 2.478 | 0.0072612 | glycosylphosphatidylinositol specific phospholipase D1 |
| EPRS | 4.172 | 4.017 | 3.192 | 5.851 | 4.501 | 4.921 | 2.479 | 0.0312013 | glutamyl-prolyl-tRNA synthetase |
| GBP6 | 2.056 | 2.724 | 2.902 | 3.852 | 4.212 | 3.775 | 2.48 | 0.0076948 | guanylate binding protein family, member 6 |

TABLE 6-continued

Differentially Expressed Genes in CD10+ Breast Epithelial Cells

| | Nulliparous (NP) Samples | | | | Parous (P) Samples | | | | | |
|---|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| YARS | 9.105 | 8.401 | 8.7 | 10.343 | 9.712 | 10.068 | 2.481 | 0.0092008 | tyrosyl-tRNA synthetase |
| PBLD | 1.645 | 2.787 | 1.936 | 3.248 | 3.445 | 3.181 | 2.482 | 0.0235737 | phenazine biosynthesis-like protein domain containing |
| ACCN1 | 4.222 | 4.302 | 2.83 | 5.614 | 5.225 | 5.055 | 2.484 | 0.0165894 | amiloride-sensitive cation channel 1, neuronal |
| GAL3ST4 | 1.065 | 1.269 | 1.859 | 2.841 | 2.787 | 2.379 | 2.487 | 0.0107555 | galactose-3-O-sulfotransferase 4 |
| KRBA1 | 5.49 | 5.892 | 6.445 | 7.759 | 6.99 | 7.052 | 2.487 | 0.0154139 | KRAB-A domain containing 1 |
| CSNK1E | 11.746 | 10.735 | 9.844 | 12.05 | 12.101 | 12.041 | 2.487 | 0.038881 | casein kinase 1, epsilon |
| MGC12916 | 2.419 | 3.064 | 3.757 | 4.213 | 4.379 | 4.391 | 2.489 | 0.0218602 | No description |
| PLXNB3 | 2.33 | 3.503 | 2.661 | 3.646 | 4.424 | 4.49 | 2.49 | 0.0197467 | plexin B3 |
| FZD3 | 6.241 | 5.937 | 4.275 | 7.446 | 7.253 | 7.158 | 2.491 | 0.0122508 | frizzled homolog 3 (Drosophila) |
| POP1 | 5.189 | 4.13 | 4.375 | 6.094 | 5.448 | 5.889 | 2.492 | 0.020093 | processing of precursor 1, ribonuclease P/MRP subunit (S. cerevisiae) |
| OVOL2 | 4.911 | 4.855 | 4.561 | 5.88 | 6.273 | 6.018 | 2.495 | 0.0043979 | ovo-like 2 (Drosophila) |
| HOOK2 | 5.854 | 6.528 | 6.465 | 7.847 | 7.647 | 7.639 | 2.496 | 0.0043056 | hook homolog 2 (Drosophila) |
| MLL4 | 8.59 | 7.33 | 7.892 | 9.3 | 9.192 | 9.215 | 2.502 | 0.0163061 | No description |
| SLC5A1 | 2.532 | 2.022 | 2.244 | 3.413 | 4.376 | 3.346 | 2.503 | 0.0098591 | solute carrier family 5 (sodium/glucose cotransporter), member 1 |
| C2orf42 | 3.51 | 3.222 | 1.607 | 4.105 | 4.833 | 4.164 | 2.503 | 0.0231337 | chromosome 2 open reading frame 42 |
| C1orf51 | 6.472 | 6.375 | 6.283 | 7.474 | 8.009 | 7.699 | 2.504 | 0.0036596 | chromosome 1 open reading frame 51 |
| ZG16B | 1.714 | 1.998 | 0.422 | 3.038 | 2.751 | 3.128 | 2.504 | 0.0125971 | zymogen granule protein 16 homolog B (rat) |
| TLE1 | 7.877 | 7.031 | 8.468 | 9.202 | 9.685 | 9.164 | 2.505 | 0.0110074 | transducin-like enhancer of split 1 (E(sp1) homolog, Drosophila) |
| MORC2 | 7.826 | 6.373 | 7.051 | 8.182 | 8.53 | 8.376 | 2.505 | 0.0239594 | MORC family CW-type zinc finger 2 |
| KAT5 | 6.718 | 6.079 | 5.979 | 7.603 | 7.494 | 7.304 | 2.507 | 0.0111297 | K(lysine) acetyltransferase 5 |
| PTRH1 | 5.658 | 4.095 | 5.021 | 6.893 | 6.333 | 6.347 | 2.507 | 0.0118938 | peptidyl-tRNA hydrolase 1 homolog (S. cerevisiae) |
| CASP8 | 5.276 | 5.095 | 4.503 | 6.376 | 6.603 | 5.9 | 2.508 | 0.0105302 | caspase 8, apoptosis-related cysteine peptidase |
| ZNF565 | 1.48 | 0.862 | 1.894 | 2.189 | 2.885 | 3.013 | 2.509 | 0.0197539 | zinc finger protein 565 |
| PTRH2 | 3.851 | 3.548 | 2.471 | 4.453 | 4.59 | 5.18 | 2.512 | 0.0172111 | peptidyl-tRNA hydrolase 2 |
| SUMO1 | 2.417 | 1.287 | 1.219 | 2.87 | 2.548 | 3.149 | 2.512 | 0.0290663 | SMT3 suppressor of mif two 3 homolog 1 (S. cerevisiae) |
| KHDRBS3 | 9.445 | 8.038 | 8.59 | 9.606 | 8.53 | 10.015 | 2.512 | 0.0358467 | KH domain containing, RNA binding, signal transduction associated 3 |
| RCE1 | 6.843 | 5.693 | 6.052 | 7.346 | 7.618 | 7.381 | 2.513 | 0.017551 | RCE1 homolog, prenyl protein peptidase (S. cerevisiae) |
| ZNF394 | 3.66 | 2.946 | 3.077 | 4.37 | 4.623 | 4.413 | 2.525 | 0.008924 | zinc finger protein 394 |
| PDCD7 | 7.816 | 7.425 | 7.368 | 8.553 | 9.154 | 8.882 | 2.528 | 0.0060042 | programmed cell death 7 |
| CBX8 | 5.109 | 5.15 | 5.727 | 7.065 | 6.611 | 6.134 | 2.528 | 0.014976 | chromobox homolog 8 |
| NCOR2 | 7.415 | 6.374 | 5.783 | 8.258 | 8.278 | 7.122 | 2.53 | 0.0395972 | nuclear receptor corepressor 2 |
| ZDHHC13 | 5.7 | 4.915 | 5.137 | 6.85 | 6.308 | 6.478 | 2.533 | 0.0101438 | zinc finger, DHHC-type containing 13 |
| DAZAP1 | 9.555 | 8.277 | 9.141 | 10.734 | 10.483 | 10.371 | 2.534 | 0.0085798 | DAZ associated protein 1 |
| OST4 | 8.878 | 8.219 | 8.344 | 9.753 | 9.676 | 9.686 | 2.535 | 0.0076433 | oligosaccharyltransferase 4 homolog (S. cerevisiae) |
| TRMT1 | 8.643 | 8.178 | 8.021 | 9.747 | 9.367 | 9.682 | 2.542 | 0.0060643 | TRM1 tRNA methyltransferase 1 homolog (S. cerevisiae) |
| MURC | 3.289 | 2.782 | 3.071 | 4.322 | 4.7 | 4.13 | 2.546 | 0.0057208 | muscle-related coiled-coil protein |
| TRIM56 | 4.637 | 4.001 | 4.081 | 5.557 | 5.539 | 5.349 | 2.547 | 0.0075224 | tripartite motif-containing 56 |
| ZNF347 | 2.966 | 1.305 | 1.928 | 4.134 | 3.277 | 3.139 | 2.547 | 0.0268842 | zinc finger protein 347 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| FAM83E | 5.147 | 4.075 | 4.535 | 5.885 | 6.148 | 5.526 | 2.549 | 0.0174279 | family with sequence similarity 83, member E |
| SNORD23 | 2.908 | 1.783 | 2.758 | 4.203 | 3.874 | 4.109 | 2.551 | 0.0064985 | small nucleolar RNA, C/D box 23 |
| TNFRSF12A | 10.483 | 10.047 | 9.631 | 11.962 | 10.913 | 11.398 | 2.552 | 0.0146176 | tumor necrosis factor receptor superfamily, member 12A |
| TMC5 | 5.798 | 4.92 | 5.738 | 6.981 | 7.151 | 6.987 | 2.554 | 0.0043908 | transmembrane channel-like 5 |
| MTHFD2L | 3.481 | 4.237 | 3.543 | 5.651 | 4.749 | 4.897 | 2.557 | 0.0142212 | methylenetetrahydrofolate dehydrogenase (NADP+ dependent) 2-like |
| NCBP2 | 8.413 | 6.943 | 7.746 | 9.135 | 8.945 | 9.101 | 2.558 | 0.0184575 | nuclear cap binding protein subunit 2, 20kDa |
| CEACAM19 | 6.781 | 5.733 | 5.382 | 8.086 | 7.088 | 6.883 | 2.558 | 0.0303284 | carcinoembryonic antigen-related cell adhesion molecule 19 |
| LOC152225 | 6.866 | 6.252 | 6.346 | 7.61 | 7.885 | 7.711 | 2.563 | 0.0071933 | No description |
| RBM19 | 6.562 | 5.687 | 6.486 | 7.92 | 7.094 | 7.401 | 2.563 | 0.0211283 | RNA binding motif protein 19 |
| CDK7 | 3.98 | 5.392 | 3.901 | 6.169 | 5.26 | 5.869 | 2.564 | 0.033681 | cyclin-dependent kinase 7 |
| BMS1P1 | 3.514 | 3.323 | 3.089 | 4.501 | 4.873 | 4.455 | 2.566 | 0.0047972 | BMS1 pseudogene 1 |
| IL12RB1 | 3.368 | 3.427 | 2.775 | 4.863 | 4.087 | 4.729 | 2.568 | 0.0096501 | interleukin 12 receptor, beta 1 |
| EIF4ENIF1 | 6.277 | 5.176 | 5.519 | 6.879 | 7.05 | 6.692 | 2.568 | 0.0189204 | eukaryotic translation initiation factor 4E nuclear import factor 1 |
| PHC2 | 9.771 | 8.986 | 9.063 | 11.021 | 10.35 | 10.538 | 2.573 | 0.0099993 | polyhomeotic homolog 2 (Drosophila) |
| C17orf96 | 10.804 | 8.687 | 9.754 | 10.864 | 11.324 | 11.118 | 2.574 | 0.0426994 | chromosome 17 open reading frame 96 |
| VPS72 | 5.364 | 4.332 | 4.179 | 5.905 | 5.728 | 5.544 | 2.575 | 0.0361122 | vacuolar protein sorting 72 homolog (S. cerevisiae) |
| GRK6 | 5.767 | 6.036 | 5.441 | 7.614 | 6.925 | 6.807 | 2.576 | 0.0090134 | G protein-coupled receptor kinase 6 |
| HOXC13 | 0.838 | 1.758 | 0.871 | 2.718 | 2.36 | 2.204 | 2.577 | 0.0153753 | homeobox C13 |
| MGAT1 | 10.283 | 8.869 | 9.05 | 10.415 | 10.319 | 10.813 | 2.577 | 0.0490534 | mannosyl (alpha-1,3-)-glycoprotein beta-1,2-N-acetylglucosaminyltransferase |
| CDHR1 | 1.182 | 1.864 | 1.075 | 2.715 | 2.442 | 2.854 | 2.578 | 0.0096008 | cadherin-related family member 1 |
| MOBKL1B | 6.91 | 5.316 | 6.272 | 7.373 | 8.277 | 7.639 | 2.579 | 0.0150805 | MOB1, Mps One Binder kinase activator-like 1B (yeast) |
| C17orf89 | 7.562 | 6.396 | 6.707 | 8.739 | 7.899 | 8.074 | 2.579 | 0.0192559 | chromosome 17 open reading frame 89 |
| PTBP1 | 11.017 | 9.001 | 10.15 | 12.129 | 11.518 | 11.226 | 2.58 | 0.0250798 | polypyrimidine tract binding protein 1 |
| CDCP1 | 6.3 | 7.608 | 6.666 | 8.55 | 7.667 | 8.155 | 2.58 | 0.0295714 | CUB domain containing protein 1 |
| SLC23A3 | 2.352 | 2.319 | 2.922 | 3.687 | 3.847 | 4.085 | 2.581 | 0.0057945 | solute carrier family 23 (nucleobase transporters), member 3 |
| IL18 | 5.496 | 5.078 | 6.424 | 7.121 | 6.865 | 6.794 | 2.582 | 0.0230207 | interleukin 18 (interferon-gamma-inducing factor) |
| TMEM161B | 3.93 | 3.118 | 3.886 | 5.256 | 4.8 | 5.269 | 2.584 | 0.0064914 | transmembrane protein 161B |
| LOC339047 | 3.675 | 4.166 | 4.398 | 5.557 | 5.516 | 5.537 | 2.586 | 0.0036882 | No description |
| THOP1 | 7.293 | 6.672 | 6.577 | 8.684 | 7.68 | 8.043 | 2.586 | 0.0170988 | thimet oligopeptidase 1 |
| TMED2 | 10.578 | 9.834 | 9.386 | 11.207 | 10.936 | 11.285 | 2.589 | 0.0216606 | transmembrane emp24 domain trafficking protein 2 |
| ABTB2 | 6.749 | 2.851 | 5.678 | 6.885 | 7.447 | 7.051 | 2.589 | 0.0432646 | ankyrin repeat and BTB (POZ) domain containing 2 |
| TMEM55B | 3.726 | 3.315 | 3.306 | 4.288 | 5.256 | 4.69 | 2.594 | 0.0120262 | transmembrane protein 55B |
| VAC14 | 2.443 | 2.819 | 2.815 | 4.644 | 3.818 | 3.819 | 2.595 | 0.0078629 | Vac14 homolog (S. cerevisiae) |
| ARHGDIA | 11.02 | 9.266 | 9.793 | 11.934 | 11.082 | 11.169 | 2.596 | 0.0352765 | Rho GDP dissociation inhibitor (GDI) alpha |
| PLCH2 | 4.742 | 5.722 | 5.039 | 6.467 | 6.516 | 6.119 | 2.598 | 0.0174208 | phospholipase C, eta 2 |
| MAPK8 | 3.672 | 3.247 | 3.329 | 5.521 | 3.987 | 4.706 | 2.598 | 0.0240602 | mitogen-activated protein kinase 8 |
| SBNO1 | 6.577 | 6.674 | 6.47 | 7.567 | 8.187 | 7.955 | 2.599 | 0.0046641 | strawberry notch homolog 1 (Drosophila) |
| SLC27A5 | 5.367 | 4.597 | 3.83 | 5.976 | 6.076 | 5.838 | 2.6 | 0.0198068 | solute carrier family 27 (fatty acid transporter), member 5 |
| CDK4 | 9.075 | 7.825 | 8.274 | 10.165 | 9.204 | 10.032 | 2.601 | 0.0193911 | cyclin-dependent kinase 4 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
| --- | --- | --- | --- | --- | --- | --- | --- | --- | --- |
| | CD24+ N48 | CD24+ N58 | CD24+ N43 | CD24+ N37 | CD24+ N39 | CD24+ N40 | | | |
| ROMO1 | 4.505 | 4.344 | 5.942 | 5.723 | 6.437 | 6.368 | 2.601 | 0.0456028 | reactive oxygen species modulator 1 |
| RPS15 | 7.447 | 7.42 | 6.731 | 8.236 | 8.826 | 8.541 | 2.602 | 0.0091808 | ribosomal protein S15 |
| HES7 | 4.961 | 6.091 | 6 | 6.855 | 7.472 | 6.913 | 2.604 | 0.0152343 | hairy and enhancer of split 7 (Drosophila) |
| FAM173A | 5.026 | 4.459 | 4.856 | 6.238 | 6.405 | 5.954 | 2.607 | 0.0040867 | family with sequence similarity 173, member A |
| C3orf33 | 2.539 | 2.882 | 2.344 | 4.582 | 3.803 | 3.727 | 2.608 | 0.0072147 | chromosome 3 open reading frame 33 |
| SMARCE1 | 5.791 | 5.234 | 5.207 | 7.175 | 6.167 | 6.801 | 2.61 | 0.0147449 | SWI/SNF related, matrix associated, actin dependent regulator of chromatin, subfamily e, member 1 |
| TMEM208 | 7.103 | 5.569 | 6.145 | 7.877 | 7.007 | 7.529 | 2.61 | 0.044946 | transmembrane protein 208 |
| TMEM180 | 3.834 | 3.245 | 3.109 | 5.183 | 5.144 | 4.493 | 2.611 | 0.0053352 | transmembrane protein 180 |
| S100A16 | 9.921 | 8.374 | 8.701 | 10.808 | 9.763 | 10.415 | 2.618 | 0.0358789 | S100 calcium binding protein A16 |
| LOC730668 | 3.111 | 2.97 | 2.996 | 4.455 | 4.386 | 4.375 | 2.62 | 0.0010732 | No description |
| DLL3 | 1.275 | 1.715 | 1.471 | 3.742 | 2.863 | 2.54 | 2.624 | 0.0075152 | delta-like 3 (Drosophila) |
| HSPA1L | 2.541 | 0.588 | 0.96 | 1.757 | 3.933 | 3.502 | 2.624 | 0.0418366 | heat shock 70kDa protein 1-like |
| LILRA5 | 3.73 | 3.559 | 2.521 | 5.123 | 4.6 | 4.232 | 2.625 | 0.0196537 | leukocyte immunoglobulin-like receptor, subfamily A (with TM domain), member 5 |
| PITPNM3 | 2.646 | 1.49 | 2.246 | 3.671 | 3.336 | 3.64 | 2.627 | 0.010151 | PITPNM family member 3 |
| STK32C | 4.618 | 4.228 | 5.343 | 6.357 | 5.743 | 6.012 | 2.628 | 0.0162918 | serine/threonine kinase 32C |
| CCNB1 | 4.326 | 3.44 | 3.948 | 5.058 | 5.757 | 4.835 | 2.63 | 0.0165679 | cyclin B1 |
| MS4A7 | 5.849 | 5.274 | 4.616 | 6.742 | 6.669 | 6.245 | 2.63 | 0.017971 | membrane-spanning 4-domains, subfamily A, member 7 |
| PTPN6 | 3.792 | 3.42 | 3.768 | 4.927 | 5.635 | 4.817 | 2.634 | 0.005552 | protein tyrosine phosphatase, non-receptor type 6 |
| TXLNG | 4.676 | 3.776 | 4.858 | 5.937 | 6.255 | 5.51 | 2.634 | 0.0112814 | taxilin gamma |
| MCCC2 | 4.814 | 4.249 | 4.214 | 6.091 | 6.001 | 5.614 | 2.637 | 0.004189 | methylcrotonoyl-CoA carboxylase 2 (beta) |
| TMEM147 | 7.228 | 6.265 | 5.859 | 8.282 | 7.664 | 7.57 | 2.637 | 0.019761 | transmembrane protein 147 |
| RPS6 | 14.08 | 12.935 | 13.834 | 15.235 | 15.038 | 15.235 | 2.641 | 0.0065608 | ribosomal protein S6 |
| FZD5 | 5.665 | 4.275 | 4.748 | 6.238 | 6.15 | 6.134 | 2.642 | 0.0216255 | frizzled homolog 5 (Drosophila) |
| CAPN10 | 1.362 | 2.474 | 1.075 | 3.163 | 2.763 | 2.575 | 2.642 | 0.0361608 | calpain 10 |
| AEBP1 | 6.061 | 5.48 | 5.558 | 6.883 | 7.388 | 7.214 | 2.645 | 0.004101 | AE binding protein 1 |
| NCRNA00114 | 2.986 | 2.682 | 2.638 | 4.089 | 3.998 | 4.391 | 2.648 | 0.0031158 | non-protein coding RNA 114 |
| TECPR2 | 8.714 | 7.859 | 8.389 | 8.631 | 10.368 | 9.794 | 2.648 | 0.0434178 | tectonin beta-propeller repeat containing 2 |
| KIAA1704 | 2.219 | 2.17 | 2.758 | 4.215 | 3.624 | 3.336 | 2.649 | 0.0107484 | KIAA1704 |
| CYP24A1 | 1.994 | 2.821 | 3.582 | 4.227 | 4.11 | 4.346 | 2.649 | 0.0175295 | cytochrome P450, family 24, subfamily A, polypeptide 1 |
| SNRNP25 | 6.534 | 5.087 | 5.96 | 7.352 | 7.94 | 7.193 | 2.65 | 0.0102111 | small nuclear ribonucleoprotein 25kDa (U11/U12) |
| KRT7 | 12.594 | 12.05 | 12.125 | 14.221 | 12.979 | 13.531 | 2.65 | 0.0178736 | keratin 7 |
| BCL2L1 | 8.661 | 6.186 | 8.087 | 10.067 | 8.783 | 9.155 | 2.65 | 0.0363526 | BCL2-like 1 |
| C14orf104 | 7.407 | 6.124 | 6.094 | 7.501 | 7.811 | 7.579 | 2.651 | 0.0481799 | chromosome 14 open reading frame 104 |
| AEN | 6.674 | 5.683 | 6.622 | 8.081 | 7.867 | 7.779 | 2.652 | 0.0053066 | apoptosis enhancing nuclease |
| CITED4 | 8.717 | 8.807 | 9.331 | 10.777 | 9.512 | 10.215 | 2.652 | 0.0272691 | Cbp/p300-interacting transactivator, with Glu/Asp-rich carboxy-terminal domain, 4 |
| CLCN2 | 6.867 | 5.309 | 6.253 | 6.956 | 8.274 | 7.351 | 2.652 | 0.0353009 | chloride channel 2 |
| PRR15 | 1.709 | 1.108 | 1.893 | 3.764 | 2.519 | 2.745 | 2.658 | 0.0159412 | proline rich 15 |
| FAM166A | 6.888 | 6.739 | 6.515 | 8.067 | 8.151 | 8.171 | 2.66 | 0.0017958 | family with sequence similarity 166, member A |
| WDR66 | 3.116 | 2.431 | 2.997 | 4.279 | 4.493 | 4.408 | 2.66 | 0.0028339 | WD repeat domain 66 |
| ZNHIT1 | 3.7 | 2.828 | 1.818 | 4.38 | 3.817 | 4.24 | 2.66 | 0.0336202 | zinc finger, HIT-type containing 1 |
| DPY19L2P2 | 3.167 | 2.6 | 3.287 | 4.666 | 4.409 | 4.58 | 2.663 | 0.0031087 | dpy-19-like 2 pseudogene 2 (C. elegans) |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| C5orf38 | 4.84 | 4.5 | 4.284 | 6.122 | 5.991 | 5.697 | 2.663 | 0.0041747 | chromosome 5 open reading frame 38 |
| MRPL52 | 8.39 | 8.174 | 7.506 | 9.802 | 9.058 | 9.257 | 2.663 | 0.0121335 | mitochondrial ribosomal protein L52 |
| CLIP2 | 8.475 | 7.019 | 7.541 | 8.955 | 9.042 | 8.449 | 2.663 | 0.0449975 | CAP-GLY domain containing linker protein 2 |
| HLA-J | 2.028 | 2.354 | 3.063 | 3.625 | 3.962 | 3.768 | 2.665 | 0.0122437 | major histocompatibility complex, class I, J (pseudogene) |
| SMCR7L | 7.789 | 6.676 | 6.966 | 8.689 | 8.092 | 8.511 | 2.668 | 0.0180554 | Smith-Magenis syndrome chromosome region, candidate 7-like |
| PRRG4 | 4.653 | 4.682 | 3.602 | 5.743 | 6.098 | 6.03 | 2.669 | 0.0054983 | proline rich Gla (G-carboxyglutamic acid) 4 (transmembrane) |
| SLC27A4 | 4.403 | 2.905 | 3.259 | 5.455 | 4.323 | 4.807 | 2.672 | 0.0345596 | solute carrier family 27 (fatty acid transporter), member 4 |
| CECR5 | 5.225 | 4.835 | 5.869 | 7.198 | 6.513 | 6.644 | 2.673 | 0.0091415 | cat eye syndrome chromosome region, candidate 5 |
| RRS1 | 6.983 | 5.881 | 5.915 | 7.765 | 7.3 | 7.74 | 2.674 | 0.0161508 | RRS1 ribosome biogenesis regulator homolog (S. cerevisiae) |
| MRFAP1L1 | 7.659 | 6.114 | 6.734 | 7.943 | 8.155 | 8.186 | 2.677 | 0.0287644 | Morf4 family associated protein 1-like 1 |
| PYGO1 | 2.651 | 1.044 | 2.414 | 2.957 | 4.072 | 3.128 | 2.677 | 0.040855 | pygopus homolog 1 (Drosophila) |
| C17orf80 | 4.813 | 3.353 | 3.768 | 5.097 | 6.028 | 5.19 | 2.679 | 0.0210517 | chromosome 17 open reading frame 80 |
| C8orf86 | 6.703 | 6.277 | 6.073 | 8.081 | 7.703 | 7.495 | 2.68 | 0.0054912 | chromosome 8 open reading frame 86 |
| LDLRAD3 | 5.296 | 5.267 | 6.53 | 7.102 | 6.689 | 6.758 | 2.68 | 0.037664 | low density lipoprotein receptor class A domain containing 3 |
| SEPHS2 | 7.5 | 6.214 | 6.101 | 7.756 | 7.912 | 7.527 | 2.687 | 0.0459984 | selenophosphate synthetase 2 |
| MEP1B | 1.077 | 1.685 | 0.585 | 2.504 | 2.261 | 3.022 | 2.689 | 0.0101753 | meprin A, beta |
| S100A11 | 10.783 | 9.619 | 10.052 | 11.973 | 11.479 | 11.362 | 2.689 | 0.0109537 | S100 calcium binding protein A11 |
| UBE3C | 8.369 | 7.135 | 7.642 | 9.705 | 8.925 | 9.07 | 2.69 | 0.0113551 | ubiquitin protein ligase E3C |
| AHSA1 | 9.491 | 8.16 | 8.374 | 9.59 | 10.114 | 9.926 | 2.695 | 0.0324175 | AHA1, activator of heat shock 90kDa protein ATPase homolog 1 (yeast) |
| GNA15 | 2.717 | 2.761 | 1.793 | 4.193 | 3.793 | 4.006 | 2.697 | 0.0055184 | guanine nucleotide binding protein (G protein), alpha 15 (Gq class) |
| CRYAB | 10.972 | 11.11 | 11.719 | 12.426 | 12.598 | 12.542 | 2.698 | 0.0085333 | crystallin, alpha B |
| FAM153B | 4.791 | 4.884 | 4.428 | 5.86 | 6.62 | 5.993 | 2.699 | 0.0053638 | family with sequence similarity 153, member B |
| CBX6 | 7.526 | 6.593 | 5.899 | 8.027 | 8.266 | 7.93 | 2.702 | 0.0205595 | chromobox homolog 6 |
| WNK2 | 4.916 | 5.495 | 6.013 | 6.349 | 7.597 | 6.471 | 2.702 | 0.0288431 | WNK lysine deficient protein kinase 2 |
| EIF4G1 | 8.521 | 7.937 | 7.802 | 9.877 | 9.237 | 9.475 | 2.704 | 0.0062739 | eukaryotic translation initiation factor 4 gamma, 1 |
| RAB31 | 7.39 | 6.903 | 5.981 | 8.686 | 7.448 | 8.338 | 2.705 | 0.0284138 | RAB31, member RAS oncogene family |
| TCEB2 | 9.405 | 8.716 | 8.529 | 10.316 | 10.153 | 10.133 | 2.707 | 0.0087172 | transcription elongation factor B (SIII), polypeptide 2 (18kDa, elongin B) |
| NUBP1 | 5.536 | 4.278 | 4.377 | 6.485 | 5.759 | 5.814 | 2.707 | 0.027493 | nucleotide binding protein 1 (MinD homolog, E. coli) |
| HIF1AN | 6.048 | 4.447 | 4.785 | 6.372 | 6.143 | 6.222 | 2.707 | 0.0475438 | hypoxia inducible factor 1, alpha subunit inhibitor |
| DSCR3 | 4.437 | 5.174 | 3.308 | 5.416 | 6.005 | 5.874 | 2.708 | 0.0257981 | Down syndrome critical region gene 3 |
| TRIAP1 | 7.095 | 6.415 | 5.935 | 7.855 | 7.686 | 8.103 | 2.713 | 0.0110782 | TP53 regulated inhibitor of apoptosis 1 |
| ACADM | 5.308 | 4.068 | 4.392 | 6.038 | 5.922 | 5.509 | 2.715 | 0.024594 | acyl-CoA dehydrogenase, C-4 to C-12 straight chain |
| IFRD2 | 10.183 | 8.603 | 9.387 | 11.308 | 10.673 | 10.828 | 2.716 | 0.0143936 | interferon-related developmental regulator 2 |
| MID1IP1 | 5.567 | 5.029 | 5.322 | 6.14 | 7.186 | 6.763 | 2.717 | 0.0103427 | MID1 interacting protein 1 (gastrulation specific G12 homolog (zebrafish)) |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| LOC100129550 | 4.236 | 4.369 | 3.519 | 5.811 | 5.28 | 5.539 | 2.718 | 0.0056858 | No description |
| HOXC8 | 5.711 | 3.825 | 4.445 | 5.887 | 6.37 | 5.739 | 2.718 | 0.0386664 | homeobox C8 |
| PRDM2 | 7.424 | 6.069 | 6.853 | 8.092 | 8.785 | 8.296 | 2.719 | 0.0092223 | PR domain containing 2, with ZNF domain |
| MLLT1 | 9.268 | 7.603 | 8.589 | 10.297 | 10.032 | 9.985 | 2.719 | 0.0115103 | myeloid/lymphoid or mixed-lineage leukemia (trithorax homolog, Drosophila); translocated to, 1 |
| IRAK1 | 8.77 | 7.74 | 8.773 | 10.218 | 9.38 | 9.31 | 2.721 | 0.0332818 | interleukin-1 receptor-associated kinase 1 |
| IGSF22 | 0.545 | 0.817 | 1.083 | 4.12 | 2.261 | 1.936 | 2.722 | 0.0117457 | immunoglobulin superfamily, member 22 |
| CHERP | 9.24 | 7.885 | 8.485 | 10.112 | 9.93 | 9.907 | 2.722 | 0.0117772 | calcium homeostasis endoplasmic reticulum protein |
| RGS12 | 7.648 | 7.39 | 8.712 | 9.248 | 9.263 | 8.835 | 2.723 | 0.0310575 | regulator ofG-protein signaling 12 |
| TFCP2L1 | 2.963 | 3.33 | 3.107 | 4.944 | 4.329 | 4.553 | 2.724 | 0.0033476 | transcription factor CP2-like 1 |
| CSTF3 | 4.855 | 5.356 | 5.113 | 6.351 | 6.649 | 6.561 | 2.727 | 0.0030801 | cleavage stimulation factor; 3' pre-RNA, subunit 3, 77kDa |
| C7orf13 | 3.372 | 2.39 | 2.486 | 3.636 | 4.82 | 3.966 | 2.728 | 0.0203026 | chromosome 7 open reading frame 13 |
| COL17A1 | 7.955 | 9.716 | 8.783 | 9.72 | 10.24 | 10.233 | 2.731 | 0.0422558 | collagen, type XVII, alpha 1 |
| RPL24 | 12.191 | 11.057 | 10.605 | 12.594 | 12.316 | 12.507 | 2.732 | 0.0402704 | ribosomal protein L24 |
| HOMEZ | 7.961 | 6.871 | 6.997 | 8.505 | 8.627 | 8.322 | 2.735 | 0.0208757 | homeobox and leucine zipper encoding |
| WDR76 | 4.266 | 3.022 | 2.859 | 4.395 | 4.475 | 4.55 | 2.738 | 0.0485419 | WD repeat domain 76 |
| C19orf24 | 4.632 | 4.111 | 3.95 | 6.532 | 4.876 | 5.564 | 2.739 | 0.0228504 | chromosome 19 open reading frame 24 |
| OSGEPL1 | 1.83 | 1.03 | 2.509 | 3.069 | 3.521 | 3.286 | 2.743 | 0.0128704 | O-sialoglycoprotein endopeptidase-like 1 |
| LOC283050 | 0.589 | 0.464 | 0.888 | 2.689 | 1.92 | 1.936 | 2.744 | 0.0044902 | No description |
| PDRG1 | 6.796 | 5.014 | 5.807 | 7.046 | 7.263 | 7.32 | 2.744 | 0.0300866 | p53 and DNA-damage regulated 1 |
| FAM174A | 5.842 | 5.044 | 4.023 | 7.206 | 6.463 | 6.501 | 2.747 | 0.0117965 | family with sequence similarity 174, member A |
| SCAMP2 | 4.881 | 3.723 | 3.532 | 6.095 | 4.991 | 5.764 | 2.748 | 0.015934 | secretory carrier membrane protein 2 |
| POLR2L | 9.667 | 8.566 | 8.206 | 10.525 | 9.977 | 10.027 | 2.753 | 0.022273 | polymerase (RNA) II (DNA directed) polypeptide L, 7.6kDa |
| C22orf26 | 0.323 | 0.464 | 1.042 | 2.073 | 1.546 | 2.504 | 2.755 | 0.0097381 | chromosome 22 open reading frame 26 |
| KCNJ11 | 2.621 | 2.392 | 3.219 | 4.735 | 3.855 | 3.974 | 2.756 | 0.0102611 | potassium inwardly-rectifying channel, subfamily J, member 11 |
| NFKBIB | 9.434 | 7.866 | 8.107 | 10.019 | 9.448 | 9.569 | 2.756 | 0.0439679 | nuclear factor of kappa light polypeptide gene enhancer in B-cells inhibitor; beta |
| TBCCD1 | 3.884 | 3.08 | 3.207 | 5.393 | 4.671 | 4.333 | 2.757 | 0.0136267 | TBCC domain containing 1 |
| ZNF500 | 3.598 | 2.393 | 2.567 | 4.29 | 4.026 | 4.031 | 2.758 | 0.0202826 | zinc finger protein 500 |
| SNORD95 | -0.152 | -0.177 | 0.925 | 1.267 | 2.39 | 1.908 | 2.76 | 0.0099213 | small nucleolar RNA, C/D box 95 |
| SRC | 6.854 | 5.689 | 5.637 | 7.317 | 7.362 | 7.102 | 2.76 | 0.027767 | v-src sarcoma (Schmidt-Ruppin A-2) viral oncogene homolog (avian) |
| MVK | 4.924 | 3.469 | 3.769 | 5.107 | 5.491 | 5.234 | 2.761 | 0.0326472 | mevalonate kinase |
| POLN | 1.684 | 1.747 | 2.6 | 3.212 | 3.29 | 3.163 | 2.761 | 0.0151914 | polymerase (DNA directed) nu |
| LTA | 0.554 | 1.936 | 2.048 | 3.156 | 3.513 | 2.316 | 2.761 | 0.0267132 | lymphotoxin alpha (TNF superfamily, member 1) |
| ZC3HAV1L | 1.407 | 0.903 | 1.52 | 2.987 | 2.518 | 2.415 | 2.763 | 0.0067232 | zinc finger CCCH-type, antiviral 1-like |
| SHQ1 | 6.286 | 4.58 | 5.068 | 6.545 | 6.513 | 6.536 | 2.765 | 0.0408407 | SHQ1 homolog (S. cerevisiae) |
| ZNF646 | 4.352 | 2.807 | 2.876 | 4.604 | 4.678 | 4.274 | 2.765 | 0.0492681 | zinc finger protein 646 |
| KIAA1244 | 5.052 | 4.16 | 4.077 | 5.696 | 6.172 | 5.546 | 2.767 | 0.0123882 | KIAA1244 |
| SDR42E1 | 2.323 | 1.176 | 1.767 | 3.791 | 2.324 | 3.389 | 2.767 | 0.0268033 | short chain dehydrogenase/reductase family 42E, member 1 |
| C16orf88 | 3.586 | 3.209 | 1.886 | 5.022 | 4.438 | 4.679 | 2.77 | 0.0084589 | chromosome 16 open reading frame 88 |
| TNPO3 | 5.913 | 5.113 | 5.397 | 6.869 | 7.063 | 6.776 | 2.773 | 0.0050061 | transportin 3 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| MAK16 | 7.695 | 6.694 | 7.056 | 8.746 | 8.324 | 8.528 | 2.774 | 0.0091629 | MAK16 homolog (S. cerevisiae) |
| CPNE9 | 0.162 | 0.701 | 1.793 | 2.78 | 2.819 | 1.635 | 2.775 | 0.0256407 | copine family member IX |
| PPP1R14B | 1.374 | 2.52 | 1.334 | 3.868 | 2.807 | 3.444 | 2.777 | 0.0113479 | protein phosphatase 1, regulatory (inhibitor) subunit 14B |
| HARS | 7.886 | 6.631 | 6.587 | 8.635 | 8.06 | 8.33 | 2.778 | 0.0247764 | histidyl-tRNA synthetase |
| PDE6G | 2.59 | 1.568 | 1.637 | 2.508 | 4.063 | 3.172 | 2.778 | 0.0370781 | phosphodiesterase 6G, cGMP-specific, rod, gamma |
| C8orf38 | 1.992 | 1.318 | 0.327 | 3.469 | 2.342 | 2.528 | 2.782 | 0.0209265 | chromosome 8 open reading frame 38 |
| CLDN3 | 3.932 | 4.939 | 3.112 | 4.615 | 6.415 | 5.331 | 2.782 | 0.0474472 | claudin 3 |
| TRIM16L | 3.514 | 3.721 | 2.888 | 4.776 | 5.059 | 4.993 | 2.788 | 0.0036954 | tripartite motif-containing 16-like |
| ST14 | 5.637 | 5.78 | 5.167 | 6.648 | 7.401 | 6.998 | 2.79 | 0.0052629 | suppression of tumorigenicity 14 (colon carcinoma) |
| CHRNB1 | 5.842 | 5.701 | 4.473 | 6.845 | 7.325 | 6.836 | 2.795 | 0.0087293 | cholinergic receptor, nicotinic, beta 1 (muscle) |
| GYLTL1B | 6.107 | 6.499 | 7.441 | 8.402 | 7.978 | 7.982 | 2.795 | 0.0137741 | glycosyltransferase-like 1 B |
| SMCR8 | 6.654 | 4.96 | 5.674 | 7.159 | 7.212 | 7.046 | 2.799 | 0.0234364 | Smith-Magenis syndrome chromosome region, candidate 8 |
| FLAD1 | 6.883 | 5.559 | 5.442 | 7.632 | 7.043 | 7.015 | 2.799 | 0.034375 | FAD1 flavin adenine dinucleotide synthetase homolog (S. cerevisiae) |
| NAGS | 3.767 | 3.229 | 3.293 | 5.862 | 4.208 | 4.779 | 2.8 | 0.0168384 | N-acetylglutamate synthase |
| ITGB1BP2 | 1.936 | 2.326 | 2.132 | 3.537 | 4.156 | 3.423 | 2.801 | 0.0033548 | integrin beta 1 binding protein (melusin) 2 |
| USP51 | 5.101 | 5.108 | 3.879 | 6.594 | 6.357 | 5.754 | 2.801 | 0.0136195 | ubiquitin specific peptidase 51 |
| THOC6 | 7.401 | 8.133 | 7.177 | 8.664 | 9.149 | 8.904 | 2.803 | 0.0111226 | THO complex 6 homolog (Drosophila) |
| HPX | 3.885 | 3.43 | 4.694 | 5.372 | 5.539 | 5.268 | 2.803 | 0.0127602 | hemopexin |
| STK39 | 4.537 | 6.013 | 5.279 | 7.5 | 6.301 | 6.23 | 2.804 | 0.0329949 | serine threonine kinase 39 |
| PDCD5 | 8.423 | 7.577 | 8.365 | 9.911 | 9.183 | 9.55 | 2.805 | 0.009369 | programmed cell death 5 |
| PPM1G | 10.585 | 9.225 | 9.415 | 11.725 | 10.715 | 10.903 | 2.805 | 0.0274787 | protein phosphatase, Mg2+/Mn2+ dependent, 1G |
| FUNDC2 | 4.701 | 2.75 | 3.481 | 5.117 | 4.97 | 4.749 | 2.808 | 0.041984 | FUN14 domain containing 2 |
| LOC1001328 32 | 4.244 | 2.854 | 2.548 | 4.698 | 4.347 | 4.252 | 2.814 | 0.0465264 | No description |
| TRPM8 | 4.6 | 3.492 | 4.594 | 5.719 | 5.863 | 6.097 | 2.822 | 0.0055928 | transient receptor potential cation channel, subfamily M, member 8 |
| HSPB1 | 6.041 | 5.568 | 4.73 | 5.829 | 7.676 | 7.065 | 2.822 | 0.041926 | heat shock 27kDa protein 1 |
| PRPSAP2 | 5.335 | 4.573 | 4.565 | 6.606 | 6.282 | 6.062 | 2.823 | 0.0056715 | phosphoribosyl pyrophosphate synthetase-associated protein 2 |
| CFDP1 | 6.553 | 6.018 | 6.263 | 7.916 | 7.436 | 8.051 | 2.825 | 0.0035895 | craniofacial development protein 1 |
| ZNF384 | 7.053 | 6.069 | 6.296 | 7.774 | 7.831 | 7.794 | 2.825 | 0.0093861 | zinc finger protein 384 |
| NAT14 | 5.066 | 3.968 | 3.794 | 5.863 | 5.951 | 5.293 | 2.828 | 0.0164442 | N-acetyltransferase 14 (GCN5-related, putative) |
| QTRTD1 | 5.698 | 6.002 | 5.268 | 7.163 | 7.199 | 7.383 | 2.829 | 0.0024283 | queuine tRNA-ribosyltransferase domain containing 1 |
| JRKL | 3.188 | 2.701 | 2.262 | 4.102 | 4.689 | 3.8 | 2.829 | 0.0093418 | jerky homolog-like (mouse) |
| MGAM | 0.825 | 1.568 | 1.126 | 2.886 | 1.894 | 3.068 | 2.829 | 0.0138592 | maltase-glucoamylase (alpha-glucosidase) |
| EPCAM | 4.442 | 5.824 | 4.899 | 6.4 | 6.444 | 6.283 | 2.83 | 0.0188696 | epithelial cell adhesion molecule |
| CCNB1IP1 | 3.799 | 3.886 | 4.176 | 5.437 | 5.3 | 5.394 | 2.831 | 0.0018745 | cyclin B1 interacting protein 1 |
| WNT5B | 3.434 | 3.375 | 2.928 | 5.805 | 4.394 | 4.876 | 2.831 | 0.0056214 | wingless-type MMTV integration site family, member 5B |
| OR8D1 | 4.05 | 3.38 | 3.476 | 5.136 | 4.911 | 4.981 | 2.837 | 0.0049224 | olfactory receptor, family 8, subfamily D, member 1 |
| GPR135 | 2.073 | 0.554 | −0.648 | 3.329 | 2.06 | 1.878 | 2.84 | 0.0379416 | G protein-coupled receptor 135 |
| C17orf69 | 3.516 | 3.693 | 3.322 | 5.235 | 5.013 | 4.828 | 2.841 | 0.0019031 | chromosome 17 open reading frame 69 |
| DAXX | 9.502 | 8.252 | 8.152 | 9.764 | 9.938 | 9.659 | 2.841 | 0.0387694 | death-domain associated protein |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| ZNF587 | 4.919 | 4.395 | 5.013 | 6.052 | 6.519 | 6.196 | 2.842 | 0.0039 | zinc finger protein 587 |
| FAM185A | 3.076 | 2.601 | 2.299 | 4.579 | 4.294 | 3.806 | 2.842 | 0.0050862 | family with sequence similarity 185, member A |
| S100A14 | 9.75 | 8.56 | 7.104 | 9.871 | 10.2 | 10.067 | 2.842 | 0.0387265 | S100 calcium binding protein A14 |
| FLJ10038 | 5.667 | 5.154 | 6.117 | 7.369 | 7.175 | 7.095 | 2.843 | 0.0042656 | No description |
| FAM40B | 2.222 | 2.463 | 3.076 | 3.972 | 3.789 | 4.237 | 2.845 | 0.0067869 | family with sequence similarity 40, member B |
| GNA11 | 8.814 | 7.668 | 7.296 | 9.153 | 9.419 | 9.178 | 2.848 | 0.0241683 | guanine nucleotide binding protein (G protein), alpha 11 (Gq class) |
| ZNF273 | 3.163 | 2.885 | 3.606 | 4.675 | 4.894 | 4.652 | 2.851 | 0.0032117 | zinc finger protein 273 |
| SLC37A2 | 2.439 | 2.427 | 2.263 | 3.939 | 4.082 | 3.593 | 2.852 | 0.0019775 | solute carrier family 37 (glycerol-3-phosphate transporter), member 2 |
| CILP2 | 5.703 | 4.167 | 4.663 | 6.17 | 6.755 | 6.176 | 2.853 | 0.0153159 | cartilage intermediate layer protein 2 |
| FITM1 | 3.242 | 1.471 | 2.318 | 3.933 | 3.832 | 3.457 | 2.856 | 0.0262116 | fat storage-inducing transmembrane protein 1 |
| LOC1001286 75 | 4.603 | 4.25 | 3.911 | 6.012 | 5.767 | 5.576 | 2.861 | 0.0033977 | No description |
| HSP90AA1 | 12.851 | 11.785 | 11.099 | 13.123 | 13.379 | 13.303 | 2.863 | 0.0275639 | heat shock protein 90kDa alpha (cytosolic), class A member 1 |
| SUN3 | 4.142 | 2.343 | 3.039 | 4.557 | 4.239 | 4.82 | 2.864 | 0.0310939 | Sad1 and UNC84 domain containing 3 |
| COL2A1 | 3.847 | 4.718 | 4.644 | 5.671 | 6.238 | 5.853 | 2.868 | 0.0061358 | collagen, type II, alpha 1 |
| DGAT2 | 0.554 | 0.886 | 2.277 | 3.521 | 2.829 | 2.076 | 2.872 | 0.0280353 | diacylglycerol O-acyltransferase 2 |
| TRNT1 | 5.078 | 4.851 | 5.32 | 6.615 | 6.376 | 6.614 | 2.877 | 0.0022952 | tRNA nucleotidyl transferase, CCA-adding, 1 |
| ZMAT3 | 7.365 | 7.163 | 8.139 | 9.241 | 8.966 | 8.69 | 2.883 | 0.0094663 | zinc finger, matrin-type 3 |
| LOC678655 | 7.014 | 7.144 | 8.394 | 8.657 | 8.672 | 8.989 | 2.884 | 0.0287916 | No description |
| MYBBP1A | 9.135 | 9.017 | 9.09 | 10.87 | 10.085 | 10.619 | 2.886 | 0.0043522 | MYB binding protein (P160) 1a |
| SAMD10 | 0.924 | 1.075 | 1.46 | 2.903 | 2.99 | 1.92 | 2.888 | 0.0104436 | sterile alpha motif domain containing 10 |
| FBXL15 | 6.469 | 5.23 | 5.59 | 7.12 | 7.235 | 7.07 | 2.888 | 0.0127459 | F-box and leucine-rich repeat protein 15 |
| CDKN2B | 4.43 | 2.832 | 3.865 | 4.905 | 5.467 | 5.396 | 2.889 | 0.0147235 | cyclin-dependent kinase inhibitor 2B (p15, inhibits CDK4) |
| UPK3B | 5.297 | 4.072 | 3.544 | 5.474 | 5.806 | 5.607 | 2.897 | 0.031843 | uroplakin 3B |
| BYSL | 8.552 | 7.094 | 7.363 | 8.898 | 8.708 | 8.907 | 2.897 | 0.0383509 | bystin-like |
| PADI3 | -0.264 | 0.78 | 0.422 | 1.459 | 1.773 | 2.316 | 2.899 | 0.0088588 | peptidyl arginine deiminase, type III |
| PEG3AS | 5.315 | 4.046 | 4.778 | 5.983 | 6.796 | 6.317 | 2.906 | 0.0078415 | No description |
| RPP21 | 8.536 | 7.556 | 7.411 | 9.476 | 9.178 | 8.95 | 2.906 | 0.014345 | ribonuclease P/MRP 21 kDa subunit |
| VWA5B1 | 1.44 | 1.219 | -1.775 | 2.981 | 2.725 | 2.651 | 2.911 | 0.0129498 | von Willebrand factor A domain containing 5B1 |
| PYY2 | 3.161 | 3.102 | 1.408 | 4.703 | 3.998 | 4.557 | 2.913 | 0.0104071 | peptide YY, 2 (seminalplasmin) |
| NCRNA00183 | 4.47 | 3.569 | 3.812 | 5.306 | 5.82 | 5.356 | 2.915 | 0.0053424 | non-protein coding RNA 183 |
| MTFMT | 3.842 | 3.754 | 3.747 | 5.298 | 5.412 | 5.195 | 2.916 | 0.0007441 | mitochondrial methionyl-tRNA formyltransferase |
| LASS2 | 8.466 | 6.609 | 7.291 | 8.974 | 8.837 | 8.754 | 2.92 | 0.0275424 | LAG1 homolog, ceramide synthase 2 |
| LOC644669 | 3.219 | 2.343 | 2.706 | 4.347 | 4.556 | 3.891 | 2.923 | 0.006198 | No description |
| DLG5 | 6.883 | 6.081 | 8.477 | 8.872 | 8.431 | 8.426 | 2.923 | 0.0476061 | discs, large homolog 5 (Drosophila) |
| NDUFA8 | 6.907 | 5.954 | 5.797 | 7.395 | 7.812 | 7.502 | 2.924 | 0.0139257 | NADH dehydrogenase (ubiquinone) 1 alpha subcomplex, 8, 19kDa |
| DKFZp686O2 4166 | 3.964 | 3.134 | 4.197 | 5.808 | 4.683 | 5.318 | 2.925 | 0.0136553 | No description |
| ZC3H3 | 6.908 | 5.008 | 5.62 | 7.692 | 7.168 | 7.116 | 2.925 | 0.0261193 | zinc finger CCCH-type containing 3 |
| MGC16384 | 2.028 | 1.54 | 2.056 | 3.267 | 3.608 | 3.147 | 2.931 | 0.0036667 | No description |
| CSF1 | 5.265 | 4.29 | 5.23 | 6.176 | 6.819 | 6.441 | 2.935 | 0.0072483 | colony stimulating factor 1 (macrophage) |
| ANKRD11 | 9.798 | 8.726 | 8.887 | 10.611 | 10.82 | 10.283 | 2.941 | 0.0104708 | ankyrin repeat domain 11 |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| G10orf10 | 6.885 | 7.684 | 7.004 | 8.442 | 9.065 | 8.807 | 2.943 | 0.0045525 | chromosome 10 open reading frame 10 |
| CROCCL2 | 2.817 | 2.317 | 3.599 | 4.089 | 4.501 | 4.377 | 2.948 | 0.0129162 | No description |
| VPS4A | 7.236 | 5.875 | 5.96 | 8.234 | 7.434 | 7.643 | 2.948 | 0.0216749 | vacuolar protein sorting 4 homolog A (S. cerevisiae) |
| NCRNA00116 | 7.127 | 6.196 | 6.285 | 8.687 | 7.449 | 8.02 | 2.949 | 0.0136124 | non-protein coding RNA 116 |
| FTL | 13.854 | 11.894 | 12.248 | 14.27 | 13.808 | 13.808 | 2.949 | 0.049507 | ferritin, light polypeptide |
| RASAL2 | 6.976 | 7.241 | 7.499 | 9.06 | 8.388 | 8.971 | 2.951 | 0.0035458 | RAS protein activator like 2 |
| TRIM44 | 6.009 | 5.238 | 5.583 | 7.078 | 7.146 | 7.168 | 2.956 | 0.0032317 | tripartite motif-containing 44 |
| EPS8L1 | 4.081 | 4.508 | 4.339 | 5.923 | 5.905 | 5.658 | 2.961 | 0.00174 | EPS8-like 1 |
| ANAPC1 | 5.919 | 5.515 | 4.984 | 6.864 | 7.485 | 6.892 | 2.961 | 0.0050447 | anaphase promoting complex subunit 1 |
| C17orf67 | 2.118 | 1.374 | 1.033 | 3.684 | 2.06 | 3.035 | 2.961 | 0.0287379 | chromosome 17 open reading frame 67 |
| C14orf21 | 4.002 | 2.224 | 2.616 | 4.844 | 4.182 | 3.968 | 2.962 | 0.0355913 | chromosome 14 open reading frame 21 |
| LOH12CR2 | 4.214 | 3.713 | 3.192 | 4.917 | 5.425 | 5.28 | 2.963 | 0.0067668 | loss of heterozygosity, 12, chromosomal region 2 |
| RPL13P5 | 4.202 | 3.677 | 3.122 | 5.305 | 4.689 | 5.483 | 2.963 | 0.0100286 | ribosomal protein L13 pseudogene 5 |
| WDR8 | 4.648 | 4.493 | 3.652 | 6.215 | 5.496 | 5.368 | 2.963 | 0.0132468 | WD repeat domain 8 |
| SDC4 | 10.655 | 11.007 | 10.398 | 12.316 | 11.968 | 12.385 | 2.969 | 0.0029491 | syndecan 4 |
| SEC1 | 4.131 | 2.74 | 3.444 | 4.935 | 5.105 | 5.015 | 2.97 | 0.0081427 | No description |
| FAM22A | 3.615 | 0.93 | 2.621 | 4.487 | 4.1 | 4.192 | 2.971 | 0.0203427 | family with sequence similarity 22, member A |
| C1orf103 | 3.294 | 2.731 | 2.998 | 4.488 | 4.785 | 4.57 | 2.972 | 0.0017257 | chromosome 1 open reading frame 103 |
| ATRIP | 5.917 | 4.437 | 4.579 | 6.399 | 6.305 | 6.011 | 2.976 | 0.0326959 | ATR interacting protein |
| ARHGAP39 | 3.908 | 3.802 | 4.183 | 5.578 | 5.444 | 5.483 | 2.979 | 0.0012628 | Rho GTPase activating protein 39 |
| SCNN1A | 3.809 | 4.901 | 3.222 | 5.02 | 6.394 | 5.385 | 2.981 | 0.0215661 | sodium channel, nonvoltage-gated 1 alpha |
| PRKAG1 | 5.494 | 4.803 | 4.093 | 6.661 | 6.233 | 6.38 | 2.983 | 0.0078343 | protein kinase, AMP-activated, gamma 1 non-catalytic subunit |
| SPTBN5 | 7.158 | 6.411 | 6.686 | 7.656 | 8.906 | 8.265 | 2.987 | 0.0105788 | spectrin, beta, non-erythrocytic 5 |
| BCL9L | 10.68 | 9.129 | 9.564 | 11.143 | 11.349 | 11.071 | 2.988 | 0.0197732 | B-cell CLL/lymphoma 9-like |
| MRPS27 | 3.264 | 2.833 | 2.449 | 5.059 | 4.278 | 4.03 | 2.993 | 0.0068083 | mitochondrial ribosomal protein S27 |
| NTNG2 | 0.478 | 1.455 | 0.757 | 3.581 | 2.206 | 2.06 | 2.995 | 0.0120798 | netrin G2 |
| DHX33 | 5.6 | 5.726 | 4.64 | 7.309 | 6.405 | 7.021 | 2.997 | 0.0092931 | DEAH (Asp-Glu-Ala-His) box polypeptide 33 |
| RPS17 | 12.979 | 12.598 | 12.027 | 14.554 | 14.158 | 14.183 | 3 | 0.0026043 | ribosomal protein S17 |
| PTGES2 | 2.045 | 1.134 | 2.006 | 3.63 | 3.19 | 3.052 | 3 | 0.0060428 | prostaglandin E synthase 2 |
| PPP1R3C | 4.376 | 5.096 | 5.333 | 7.286 | 5.532 | 6.683 | 3.003 | 0.0204464 | protein phosphatase 1, regulatory (inhibitor) subunit 3C |
| ANKRD13B | 6.793 | 6.004 | 6.96 | 8.381 | 8.401 | 8.232 | 3.005 | 0.0025971 | ankyrin repeat domain 13B |
| SCRIB | 6.335 | 5.609 | 5.862 | 7.437 | 7.923 | 7.434 | 3.005 | 0.0027266 | scribbled homolog (Drosophila) |
| TBC1D26 | 0.251 | 0.96 | 1.301 | 3.021 | 2.548 | 1.305 | 3.005 | 0.028949 | TBC1 domain family, member 26 |
| LOC100128164 | -0.104 | 0.522 | 0.842 | 2.548 | 1.49 | 2.031 | 3.018 | 0.0079524 | No description |
| GUCA1B | 3.425 | 4.181 | 2.313 | 5.775 | 4.951 | 4.733 | 3.018 | 0.0115833 | guanylate cyclase activator 1B (retina) |
| TMEM5 | 4.96 | 4.039 | 3.474 | 6.143 | 5.3 | 5.633 | 3.018 | 0.0151649 | transmembrane protein 5 |
| CRABP2 | 10.399 | 8.422 | 9.233 | 10.828 | 10.928 | 10.671 | 3.02 | 0.0266559 | cellular retinoic acid binding protein 2 |
| TBCA | 9.022 | 9.354 | 8.078 | 10.95 | 10.295 | 10.404 | 3.022 | 0.0060714 | tubulin folding cofactor A |
| PES1 | 9.234 | 7.499 | 7.511 | 9.991 | 9.095 | 9.186 | 3.023 | 0.0466617 | pescadillo homolog 1, containing BRCT domain (zebrafish) |
| TIMM16 | 5.379 | 5.448 | 3.84 | 7.045 | 5.946 | 6.452 | 3.024 | 0.021031 | No description |
| ELK1 | 8.365 | 6.888 | 7.244 | 8.909 | 8.566 | 8.842 | 3.027 | 0.0277034 | ELK1, member of ETS oncogene family |
| SCAMP3 | 8.081 | 6.818 | 7.101 | 8.748 | 8.684 | 8.7 | 3.029 | 0.0137984 | secretory carrier membrane protein 3 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| MEX3D | 7.716 | 6.122 | 7.47 | 8.486 | 9.317 | 8.893 | 3.034 | 0.0093203 | mex-3 homolog D (C. elegans) |
| TRAF2 | 6.82 | 5.329 | 5.07 | 7.053 | 6.93 | 6.898 | 3.034 | 0.0474401 | TNF receptor-associated factor 2 |
| GPATCH4 | 9.497 | 7.956 | 9.395 | 11.099 | 10.404 | 10.804 | 3.037 | 0.008192 | G patch domain containing 4 |
| WDR4 | 6.025 | 4.134 | 4.677 | 6.382 | 6.28 | 6.159 | 3.037 | 0.0367568 | WD repeat domain 4 |
| BTF3 | 5.381 | 5.229 | 5.64 | 7.015 | 6.833 | 7.171 | 3.04 | 0.0014352 | basic transcription factor 3 |
| RPPH1 | 3.036 | 3.044 | 2.229 | 3.669 | 4.855 | 4.642 | 3.043 | 0.0094341 | ribonuclease P RNA component H1 |
| TMEM39B | 6.607 | 4.873 | 5.557 | 7.216 | 7.165 | 6.767 | 3.047 | 0.0274415 | transmembrane protein 39B |
| UCN | 1.908 | 1.893 | 2.099 | 4.53 | 3.467 | 3.517 | 3.049 | 0.0026436 | urocortin |
| HYLS1 | 4.423 | 3.431 | 3.064 | 4.673 | 5.924 | 5.997 | 3.051 | 0.0087651 | hydrolethalus syndrome 1 |
| CLIC3 | 2.968 | 1.715 | 1.219 | 3.158 | 4.578 | 3.128 | 3.053 | 0.0255584 | chloride intracellular channel 3 |
| NME1 | 9.562 | 8.047 | 8.566 | 10.653 | 10.132 | 10.177 | 3.056 | 0.0112599 | non-metastatic cells 1, protein (NM23A) expressed in |
| LSR | 8.487 | 7.254 | 6.429 | 9.689 | 8.866 | 8.635 | 3.056 | 0.0217987 | lipolysis stimulated lipoprotein receptor |
| FOXP3 | 1.783 | 0.283 | -0.104 | 2.629 | 1.556 | 1.898 | 3.063 | 0.0451155 | forkhead box P3 |
| UBE2I2 | 9.409 | 7.746 | 8.329 | 10.275 | 9.944 | 9.627 | 3.064 | 0.0211004 | ubiquitin-conjugating enzyme E2, I2 (UBC6 homolog, yeast) |
| TMEM169 | 2.248 | 1.366 | 1.589 | 3.222 | 2.983 | 3.535 | 3.069 | 0.0056357 | transmembrane protein 169 |
| CCNT1 | 4.461 | 3.124 | 3.348 | 4.884 | 4.967 | 5.135 | 3.071 | 0.0181563 | cyclin T1 |
| CCDC127 | 5.397 | 4.282 | 3.86 | 6.312 | 5.902 | 5.86 | 3.072 | 0.0149281 | coiled-coil domain containing 127 |
| C9orf114 | 5.36 | 4.111 | 3.922 | 6.646 | 5.541 | 6.137 | 3.073 | 0.0142141 | chromosome 9 open reading frame 114 |
| TNFSF11 | 0.251 | -0.046 | 0.422 | 2.026 | 2.003 | 1.576 | 3.078 | 0.0016642 | tumor necrosis factor (ligand) superfamily, member 11 |
| BANF1 | 8.324 | 7.147 | 7.021 | 9.294 | 8.893 | 8.645 | 3.081 | 0.0160192 | barrier to autointegration factor 1 |
| TLR9 | 3.3 | 1.741 | 1.613 | 4.029 | 3.363 | 3.372 | 3.097 | 0.0351062 | toll-like receptor 9 |
| IER3 | 11.255 | 11.384 | 11.193 | 12.886 | 13.092 | 12.823 | 3.098 | 0.000631 | immediate early response 3 |
| KCNMA1 | 8.107 | 9.191 | 7.992 | 10.467 | 9.624 | 9.975 | 3.1 | 0.0101889 | potassium large conductance calcium-activated channel, subfamily M, alpha member 1 |
| PTDSS2 | 6.874 | 5.323 | 5.935 | 7.746 | 7.572 | 7.279 | 3.111 | 0.0152887 | phosphatidylserine synthase 2 |
| FAM160A1 | 5.248 | 5.742 | 6.391 | 7.335 | 7.465 | 7.38 | 3.113 | 0.0049918 | family with sequence similarity 160, member A1 |
| BNIP1 | 5.95 | 4.991 | 4.624 | 6.703 | 6.283 | 6.631 | 3.116 | 0.0177349 | BCL2/adenovirus E1B 19kDa interacting protein 1 |
| HAGHL | 3.521 | 5.04 | 5.009 | 6.234 | 6.682 | 6.143 | 3.12 | 0.0076218 | hydroxyacylglutathione hydrolase-like |
| ZNF419 | 3.464 | 2.908 | 3.233 | 5.238 | 4.479 | 4.875 | 3.122 | 0.0028583 | zinc finger protein 419 |
| SNORA80 | 2.219 | 1.783 | 1.715 | 3.863 | 3.025 | 3.661 | 3.127 | 0.0039071 | small nucleolar RNA, H/ACA box 80 |
| TTC22 | 1.303 | 0.924 | 1.388 | 3.477 | 2.569 | 2.614 | 3.129 | 0.0038785 | tetratricopeptide repeat domain 22 |
| LOC100303728 | 2.602 | 1.44 | 1.762 | 4.248 | 2.835 | 4.24 | 3.13 | 0.0097102 | No description |
| ADRBK1 | 7.599 | 5.825 | 6.278 | 8.07 | 8.053 | 7.472 | 3.131 | 0.0406682 | adrenergic, beta, receptor kinase 1 |
| TSN | 6.631 | 5.431 | 4.87 | 7.459 | 6.595 | 7.078 | 3.132 | 0.0310324 | translin |
| C17orf100 | 1.911 | 2.701 | 2.114 | 3.762 | 4.018 | 3.73 | 3.133 | 0.0031545 | chromosome 17 open reading frame 100 |
| GSR | 2.722 | 1.741 | 2.821 | 3.702 | 4.469 | 4.162 | 3.133 | 0.0061573 | glutathione reductase |
| LOC100272216 | -0.104 | 0.994 | 0.589 | 2.949 | 2.236 | 0.814 | 3.133 | 0.0370065 | No description |
| SPNS2 | 7.69 | 6.432 | 5.745 | 8.39 | 7.952 | 8.08 | 3.134 | 0.0227588 | spinster homolog 2 (Drosophila) |
| MYLPF | 3.175 | 2.17 | 2.674 | 4.824 | 4.495 | 3.336 | 3.138 | 0.017312 | myosin light chain, phosphorylatable, fast skeletal muscle |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| C21orf56 | 2.949 | 3.333 | 3.531 | 5.025 | 5.184 | 4.345 | 3.145 | 0.0045883 | chromosome 21 open reading frame 56 |
| LOC100128003 | 4.179 | 3.338 | 4.294 | 5.948 | 5.699 | 5.54 | 3.147 | 0.0027195 | No description |
| NMUR1 | 3.573 | 2.798 | 4.833 | 5.49 | 5.227 | 4.983 | 3.147 | 0.0268985 | neuromedin U receptor 1 |
| SMPD4 | 0.323 | 0.701 | 0.251 | 1.908 | 2.053 | 2.02 | 3.153 | 0.0014281 | sphingomyelin phosphodiesterase 4, neutral membrane (neutral sphingomyelinase-3) |
| SUSD5 | 4.283 | 4.111 | 4.174 | 5.834 | 6.227 | 5.732 | 3.16 | 0.0008879 | sushi domain containing 5 |
| FAM200A | 3.52 | 3.088 | 4.369 | 5.18 | 5.198 | 4.753 | 3.16 | 0.0150304 | family with sequence similarity 200, member A |
| GEMIN6 | 3.512 | 1.797 | 2.27 | 3.931 | 3.909 | 4.207 | 3.163 | 0.0189762 | gem (nuclear organelle) associated protein 6 |
| PLD6 | 4.242 | 3.277 | 4.962 | 5.904 | 5.637 | 6.047 | 3.164 | 0.0095357 | phospholipase D family, member 6 |
| IRX1 | 10.297 | 9.258 | 9.024 | 10.726 | 11.143 | 10.921 | 3.166 | 0.0145267 | iroquois homeobox 1 |
| UGT2B10 | 1.037 | 0.78 | 1.062 | 3.156 | 2.414 | 2.704 | 3.174 | 0.0014073 | UDP glucuronosyltransferase 2 family, polypeptide B10 |
| HCST | 2.956 | 2.202 | 1.126 | 3.869 | 4.211 | 3.702 | 3.177 | 0.0085133 | hematopoietic cell signal transducer |
| METTL2B | 3.645 | 3.017 | 3.181 | 5.061 | 5.158 | 4.686 | 3.179 | 0.0020133 | methyltransferase like2B |
| MLNR | 1.091 | 0.224 | -0.648 | 2.548 | 1.894 | 1.408 | 3.181 | 0.0140459 | motilin receptor |
| APOA1 | 4.512 | 3.856 | 3.924 | 5.594 | 6.377 | 5.443 | 3.182 | 0.0042584 | apolipoprotein A-I |
| PDZK1IP1 | 3.645 | 2.497 | 3.076 | 4.008 | 6.225 | 4.747 | 3.185 | 0.0147163 | PDZK1 interacting protein 1 |
| GMEB1 | 5.747 | 3.952 | 4.356 | 6.527 | 5.803 | 6.032 | 3.195 | 0.0288574 | glucocorticoid modulatory element binding protein 1 |
| AIM1L | 3.152 | 2.268 | 2.487 | 4.783 | 4.164 | 4.088 | 3.197 | 0.0039429 | absent in melanoma 1-like |
| PHB | 5.874 | 4.139 | 5.159 | 6.952 | 6.836 | 6.547 | 3.198 | 0.0097582 | prohibitin |
| XCR1 | 0.609 | -0.887 | 0.925 | 2.217 | 2.39 | 2.288 | 3.202 | 0.0047829 | chemokine (C motif) receptor 1 |
| TOMM6 | 8.269 | 7.187 | 7.163 | 9.662 | 8.843 | 8.979 | 3.203 | 0.0089576 | translocase of outer mitochondrial membrane 6 homolog (yeast) |
| ZNF765 | 6.178 | 4.983 | 5.184 | 7.292 | 6.752 | 6.87 | 3.218 | 0.0096816 | zinc finger protein 765 |
| LCN2 | 0.162 | 0.323 | 1.239 | 2.157 | 2.928 | 1.846 | 3.225 | 0.0070874 | lipocalin 2 |
| NUPL2 | 3.486 | 2.861 | 2.339 | 5.123 | 4.553 | 4.248 | 3.23 | 0.0054075 | nucleoporin like 2 |
| ZNF836 | 3.564 | 3.415 | 3.286 | 4.474 | 5.171 | 5.256 | 3.232 | 0.0037848 | zinc finger protein 836 |
| DLGAP3 | 2.064 | 0.93 | 1.239 | 3.026 | 2.623 | 3.187 | 3.233 | 0.0080811 | discs, large (Drosophila) homolog-associated protein 3 |
| CNTFR | 4.55 | 3.228 | 3.297 | 4.981 | 6.014 | 4.991 | 3.235 | 0.0143378 | ciliary neurotrophic factor receptor |
| MGRN1 | 6.93 | 5.514 | 5.961 | 8.039 | 7.219 | 7.658 | 3.242 | 0.0152815 | mahogunin, ring finger 1 |
| C8orf73 | 5.452 | 4.769 | 3.966 | 6.896 | 6.467 | 6.463 | 3.243 | 0.0045739 | chromosome 8 open reading frame 73 |
| FBLL1 | 2.546 | 3.287 | 2.602 | 4.244 | 4.654 | 4.623 | 3.244 | 0.0025335 | fibrillarin-like 1 |
| BCL7C | 6.181 | 4.094 | 5.07 | 6.794 | 6.772 | 6.624 | 3.254 | 0.01911 | B-cell CLL/lymphoma 7C |
| ATP6V0B | 10.114 | 8.912 | 9 | 10.903 | 10.69 | 10.703 | 3.256 | 0.0123081 | ATPase, H+ transporting, lysosomal 21kDa, V0 subunit b |
| C17orf91 | 3.791 | 3.614 | 2.976 | 4.211 | 5.684 | 5.317 | 3.257 | 0.0125292 | chromosome 17 open reading frame 91 |
| CORO7 | 6.456 | 5.177 | 5.257 | 7.77 | 7.495 | 6.881 | 3.259 | 0.0077928 | coronin 7 |
| FBXO10 | 3.472 | 3.384 | 3.2 | 5.513 | 4.906 | 4.985 | 3.263 | 0.0011955 | F-box protein 10 |
| MGC70857 | 5.478 | 3.893 | 4.409 | 6.628 | 5.92 | 6.118 | 3.269 | 0.0121142 | No description |
| C9orf142 | 4.872 | 5.162 | 4.342 | 6.872 | 6.242 | 6.453 | 3.272 | 0.0029291 | chromosome 9 open reading frame 142 |
| HINT1 | 6.002 | 5.987 | 6.063 | 7.65 | 7.928 | 7.713 | 3.274 | 0.0004214 | histidine triad nucleotide binding protein 1 |
| TMPRSS11BNL | 0.825 | 0.623 | 0.478 | 2.189 | 2.236 | 3.068 | 3.274 | 0.0019632 | TMPRSS11B N terminal-like |
| CCNA1 | 3.46 | 3.598 | 3.445 | 5.31 | 5.191 | 5.156 | 3.276 | 0.0003928 | cyclin A1 |
| PTAFR | 3.212 | 1.958 | 2.249 | 4.578 | 3.672 | 3.998 | 3.281 | 0.0101295 | platelet-activating factor receptor |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| LOC1001339 91 | 3.156 | 3.454 | 3.095 | 4.755 | 5.432 | 4.871 | 3.284 | 0.0015683 | No description |
| MKI67IP | 7.045 | 6.42 | 6.508 | 8.696 | 8.137 | 8.421 | 3.287 | 0.0018173 | MKI67 (FHA domain) interacting nucleolar phosphoprotein |
| HIST1H2BG | 0.525 | 0.552 | -0.104 | 1.641 | 2.269 | 2.153 | 3.287 | 0.0029219 | histone cluster 1, H2bg |
| NDUFA10 | 3.747 | 2.893 | 1.605 | 4.942 | 4.613 | 4.434 | 3.295 | 0.010289 | NADH dehydrogenase (ubiquinone) 1 alpha subcomplex, 10, 42kDa |
| SPTBN4 | 4.537 | 4.288 | 4.141 | 6.092 | 5.891 | 6.009 | 3.296 | 0.0007942 | spectrin, beta, non-erythrocytic 4 |
| SLC39A3 | 6.624 | 4.766 | 4.915 | 7.083 | 6.68 | 6.488 | 3.298 | 0.0468191 | solute carrier family 39 (zinc transporter), member 3 |
| LOC1001255 56 | -0.264 | 0.162 | 0.825 | 1.459 | 2.166 | 2.008 | 3.3 | 0.0060213 | No description |
| ZNF528 | 4.053 | 3.297 | 2.605 | 5.105 | 4.565 | 5.02 | 3.3 | 0.0104143 | zinc finger protein 528 |
| TAF1A | 1.587 | 2.292 | 0.814 | 3.511 | 2.539 | 3.622 | 3.304 | 0.0134306 | TATA box binding protein (TBP)-associated factor, RNA polymerase I, A, 48kDa |
| ASNA1 | 8.086 | 6.467 | 6.889 | 9.124 | 8.613 | 8.583 | 3.305 | 0.0125041 | arsA arsenite transporter, ATP-binding, homolog 1 (bacterial) |
| PVT1 | 8.276 | 9.216 | 10.759 | 11.334 | 10.399 | 10.941 | 3.305 | 0.0499549 | Pvt1 oncogene (non-protein coding) |
| AMZ1 | 5.023 | 3.981 | 4.909 | 6.265 | 6.748 | 6.281 | 3.306 | 0.0036038 | archaelysin family metallopeptidase 1 |
| E4F1 | 2.849 | 1.645 | 1.801 | 3.846 | 3.68 | 3.371 | 3.308 | 0.0092781 | E4F transcription factor 1 |
| EIF4EBP1 | 6.754 | 6.923 | 5.563 | 8.649 | 7.291 | 8.031 | 3.31 | 0.019155 | eukaryotic translation initiation factor 4E binding protein 1 |
| GRIN1 | -0.104 | -0.529 | 1.033 | 2.048 | 1.198 | 2.484 | 3.311 | 0.012107 | glutamate receptor, ionotropic, N-methyl D-aspartate 1 |
| LOC286467 | 4.422 | 3.582 | 4.031 | 5.759 | 5.871 | 5.595 | 3.313 | 0.0020419 | No description |
| ARRDC5 | 4.307 | 3.906 | 3.613 | 5.341 | 5.652 | 5.663 | 3.313 | 0.0023796 | arrestin domain containing 5 |
| L1CAM | 1.456 | 1.269 | 1.297 | 4.091 | 3.001 | 3.017 | 3.32 | 0.0018602 | L1 cell adhesion molecule |
| ZNF324 | 2.333 | 1.748 | 1.618 | 3.336 | 3.812 | 4.065 | 3.322 | 0.002165 | zinc finger protein 324 |
| CHD5 | 2.385 | 2.429 | 2.269 | 4.161 | 4.118 | 4.043 | 3.323 | 0.0003012 | chromodomain helicase DNA binding protein 5 |
| RNF216L | 0.986 | 1.297 | 0.96 | 2.722 | 3.205 | 2.132 | 3.33 | 0.0048043 | ring finger protein 216-like |
| FCN3 | 4.008 | 2.36 | 2.717 | 4.697 | 5.03 | 4.096 | 3.332 | 0.0183137 | ficolin (collagen/fibrinogen domain containing) 3 (Hakata antigen) |
| PRF1 | 3.934 | 3.287 | 4.668 | 5.671 | 6.026 | 5.544 | 3.336 | 0.0049989 | perforin 1 (pore forming protein) |
| MARVELD2 | 1.506 | 1.963 | 1.844 | 3.701 | 3.564 | 3.329 | 3.336 | 0.0009523 | MARVEL domain containing 2 |
| TMEM80 | 5.84 | 4.817 | 6.06 | 6.558 | 7.982 | 7.197 | 3.343 | 0.0137247 | transmembrane protein 80 |
| LLPH | 7.352 | 5.763 | 5.786 | 8.216 | 7.804 | 7.506 | 3.348 | 0.0197224 | LLP homolog, long-term synaptic facilitation (Aplysia) |
| C1orf13 | 2.721 | 1.858 | 2.323 | 3.727 | 4.402 | 4.068 | 3.352 | 0.0028196 | chromosome 1 open reading frame 113 |
| FAM171A2 | 3.609 | 2.397 | 2.64 | 4.386 | 5.184 | 4.218 | 3.355 | 0.008074 | family with sequence similarity 171, member A2 |
| PRSS22 | 9.112 | 7.761 | 5.282 | 10.565 | 9.507 | 9.189 | 3.355 | 0.0246712 | protease, serine, 22 |
| SLC38A7 | 3.664 | 1.951 | 2.358 | 4.106 | 4.004 | 4.655 | 3.358 | 0.0162724 | solute carrier family 38, member 7 |
| MOSC1 | 3.365 | 1.709 | 1.908 | 4.397 | 3.459 | 4.166 | 3.365 | 0.0155234 | MOCO sulphurase C-terminal domain containing 1 |
| ENTPD2 | 4.904 | 6.009 | 4.247 | 7.019 | 6.659 | 6.567 | 3.375 | 0.011247 | ectonucleoside triphosphate diphosphohydrolase 2 |
| TBL2 | 5.208 | 3.629 | 3.24 | 5.675 | 4.996 | 5.825 | 3.378 | 0.0338148 | transducin (beta)-like 2 |
| ALDH1A3 | 4.034 | 3.134 | 5.001 | 5.983 | 5.078 | 5.791 | 3.38 | 0.0220841 | aldehyde dehydrogenase 1 family, member A3 |
| TOP2A | 2.572 | 3.933 | 3.19 | 5.414 | 4.333 | 5.076 | 3.388 | 0.0095643 | topoisomerase (DNA) II alpha 170kDa |
| GAL3ST1 | 3.942 | 3.233 | 2.756 | 4.995 | 5.441 | 4.873 | 3.392 | 0.0039787 | galactose-3-O-sulfotransferase 1 |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24-N48 | CD24-N58 | CD24-N43 | CD24-N37 | CD24-N39 | CD24-N40 | Pseudo fold change | P value | Gene description |
| TTC27 | 5.13 | 3.221 | 4.002 | 6.093 | 5.515 | 5.765 | 3.392 | 0.0147907 | tetratricopeptide repeat domain 27 |
| DEPDC7 | 2.607 | 2.597 | 1.998 | 3.493 | 4.45 | 4.361 | 3.396 | 0.0045453 | DEP domain containing 7 |
| MT1L | 3.484 | 1.547 | 4.607 | 4.998 | 6.346 | 5.249 | 3.397 | 0.0151985 | metallothionein 1L (gene/pseudogene) |
| LDHAL6A | 0.162 | 0.464 | 0.17 | 0.762 | 2.261 | 1.936 | 3.401 | 0.0200265 | lactate dehydrogenase A-like 6A |
| UGCG | 7.001 | 6.612 | 6.435 | 8.378 | 8.41 | 8.377 | 3.402 | 0.001066 | UDP-glucose ceramide glucosyltransferase |
| WNT7B | 3.752 | 2.146 | 1.679 | 3.69 | 4.29 | 3.913 | 3.403 | 0.0369779 | wingless-type MMTV integration site family, member 7B |
| RGP1 | 2.296 | 2.494 | 1.793 | 4.307 | 3.829 | 3.56 | 3.404 | 0.0031402 | RGP1 retrograde golgi transport homolog (S. cerevisiae) |
| SAAL1 | 3.611 | 2.657 | 3.033 | 5.382 | 3.938 | 5.089 | 3.414 | 0.0103713 | serum amyloid A-like 1 |
| CBFB | 8.194 | 6.062 | 7.04 | 8.53 | 8.929 | 8.811 | 3.415 | 0.0187072 | core-binding factor, beta subunit |
| SNW1 | 5.232 | 4.389 | 4.314 | 6.449 | 6.14 | 6.165 | 3.425 | 0.0043271 | SNW domain containing 1 |
| LOC645332 | 2.798 | 1.828 | 1.315 | 4.156 | 3.093 | 3.668 | 3.429 | 0.0122895 | No description |
| RGPD1 | 0.625 | 1.818 | 2.489 | 4.679 | 2.008 | 3.597 | 3.43 | 0.0404021 | RANBP2-like and GRIP domain containing 1 |
| RHD | 6.252 | 5.438 | 5.465 | 7.346 | 7.383 | 7.219 | 3.436 | 0.0035179 | Rh blood group, D antigen |
| B4GALT2 | 8.296 | 6.962 | 7.454 | 9.736 | 8.895 | 9.236 | 3.441 | 0.0072741 | UDP-Gal:betaGlcNAc beta 1,4-galactosyltransferase, polypeptide 2 |
| ZSCAN1 | 1.374 | 0.78 | 0.631 | 2.601 | 2.414 | 2.798 | 3.442 | 0.002331 | zinc finger and SCAN domain containing 1 |
| ARRDC1 | 5.694 | 4.113 | 5.184 | 7.477 | 6.759 | 6.031 | 3.443 | 0.0143722 | arrestin domain containing 1 |
| ARHGAP11A | 4.517 | 3.425 | 3.036 | 4.916 | 5.208 | 5.25 | 3.443 | 0.0152272 | Rho GTPase activating protein 11A |
| FLJ36777 | 0.838 | 0.967 | 1.082 | 2.868 | 2.408 | 2.763 | 3.448 | 0.0009237 | No description |
| NFAM1 | 2.677 | 1.709 | 1.631 | 3.677 | 3.422 | 3.507 | 3.462 | 0.0066538 | NFAT activating protein with ITAM motif 1 |
| CKM | 0.478 | 1.366 | 0.543 | 3.222 | 1.145 | 2.336 | 3.465 | 0.0388259 | creatine kinase, muscle |
| RAB36 | 3.2 | 2.685 | 2.432 | 4.848 | 4.227 | 4.584 | 3.47 | 0.0022108 | RAB36, member RAS oncogene family |
| NUP62 | 8.223 | 6.079 | 6.698 | 8.493 | 8.558 | 8.431 | 3.47 | 0.0302375 | nucleoporin 62kDa |
| SCIN | 2.087 | 1.966 | 1.5 | 3.762 | 3.859 | 3.297 | 3.473 | 0.001657 | scinderin |
| CCL17 | 2.118 | 0.862 | 2.202 | 3.684 | 3.998 | 3.309 | 3.474 | 0.0045189 | chemokine (C-C motif) ligand 17 |
| GCNT1 | 4.594 | 5.602 | 4.934 | 6.732 | 6.771 | 6.547 | 3.477 | 0.0037705 | glucosaminyl (N-acetyl) transferase 1, core 2 |
| DHCR7 | 6.216 | 5.375 | 4.163 | 7.159 | 7.636 | 7.175 | 3.483 | 0.0063426 | 7-dehydrocholesterol reductase |
| DOHH | 6.326 | 5.404 | 4.912 | 8.173 | 5.944 | 7.205 | 3.485 | 0.0397059 | deoxyhypusine hydroxylase/monooxygenase |
| LOC285696 | 2.795 | 1.951 | 2.634 | 4.378 | 4.244 | 4.597 | 3.487 | 0.0013043 | No description |
| MRPL12 | 7.596 | 6.278 | 6.074 | 8.882 | 7.876 | 8.292 | 3.488 | 0.0124168 | mitochondrial ribosomal protein L12 |
| ZFP28 | 4.734 | 2.416 | 3.441 | 4.679 | 5.436 | 5.247 | 3.495 | 0.0302569 | zinc finger protein 28 homolog (mouse) |
| ACSBG2 | 0.924 | 1.03 | 1.164 | 3.074 | 2.835 | 2.708 | 3.496 | 0.0004786 | acyl-CoA synthetase bubblegum family member 2 |
| HIRA | 8.011 | 6.824 | 6.847 | 8.921 | 8.829 | 8.63 | 3.496 | 0.0083101 | HIR histone cell cycle regulation defective homolog A (S. cerevisiae) |
| MTMR1 | 3.088 | 3.295 | 3.073 | 3.97 | 5.103 | 4.928 | 3.502 | 0.007629 | myotubularin related protein 1 |
| AKNAD1 | 1.896 | 1.228 | 1.47 | 3.038 | 3.946 | 3.128 | 3.505 | 0.0028268 | AKNA domain containing 1 |
| KLF16 | 10.58 | 8.675 | 8.898 | 10.708 | 10.789 | 10.626 | 3.508 | 0.0430214 | Kruppel-like factor 16 |
| DDX46 | 6.794 | 7.095 | 6.975 | 8.907 | 8.131 | 8.853 | 3.511 | 0.0025549 | DEAD (Asp-Glu-Ala-Asp) box polypeptide 46 |
| NUDC | 10.024 | 8.815 | 8.844 | 11.163 | 10.662 | 10.629 | 3.516 | 0.0092652 | nuclear distribution gene C homolog (A. nidulans) |
| PCID2 | 3.823 | 5.238 | 3.71 | 5.634 | 5.64 | 5.658 | 3.523 | 0.0225334 | PCI domain containing 2 |
| DOK7 | 3.169 | 2.722 | 1.911 | 5.069 | 3.444 | 4.539 | 3.524 | 0.0134628 | docking protein 7 |
| LOC100133091 | 7.145 | 5.046 | 5.473 | 7.299 | 7.222 | 7.292 | 3.529 | 0.0415819 | No description |
| ZNF69 | 1.037 | 0.96 | 1.287 | 3.106 | 2.493 | 3.108 | 3.532 | 0.0013114 | zinc finger protein 69 |
| G6PD | 7.489 | 5.803 | 6.118 | 8.785 | 7.902 | 7.939 | 3.532 | 0.0131845 | glucose-6-phosphate dehydrogenase |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| MTND1 | 13.394 | 11.844 | 11.268 | 13.444 | 13.665 | 14.023 | 3.533 | 0.0284281 | No description |
| MIF4GD | 5.038 | 3.677 | 3.559 | 5.61 | 5.584 | 5.383 | 3.54 | 0.018627 | MIF4G domain containing |
| RABEPK | 7.178 | 5.402 | 5.229 | 7.391 | 7.053 | 7.582 | 3.54 | 0.0389576 | Rab9 effector protein with kelch motifs |
| LY6K | 8.351 | 9.503 | 8.635 | 10.502 | 10.463 | 10.399 | 3.55 | 0.0050791 | lymphocyte antigen 6 complex, locus K |
| GLB1L2 | 5.107 | 4.342 | 4.198 | 6.641 | 6.032 | 6.171 | 3.553 | 0.0035823 | galactosidase, beta 1-like 2 |
| ANKS3 | 6.042 | 5.444 | 6.243 | 8.073 | 7.282 | 7.342 | 3.555 | 0.0046984 | ankyrin repeat and sterile alpha motif domain containing 3 |
| U2AF2 | 9.729 | 8.441 | 9.127 | 10.958 | 11.028 | 10.718 | 3.558 | 0.0038714 | U2 small nuclear RNA auxiliary factor 2 |
| DNAJC9 | 5.199 | 4.376 | 3.626 | 5.658 | 6.364 | 6.209 | 3.562 | 0.0102182 | DnaJ (Hsp40) homolog, subfamily C, member 9 |
| NFKBIL2 | 0.625 | 1.733 | 0.543 | 3.406 | 2.376 | 2.618 | 3.563 | 0.0063991 | No description |
| KBTBD7 | 1.709 | 1.342 | 1.747 | 2.171 | 3.623 | 3.543 | 3.565 | 0.0154862 | kelch repeat and BTB (POZ) domain containing 7 |
| C16orf67 | 4.428 | 5.225 | 5.824 | 7.269 | 6.98 | 7.061 | 3.568 | 0.0032246 | No description |
| CD82 | 2.612 | 3.77 | 2.419 | 4.808 | 4.258 | 4.475 | 3.577 | 0.0103928 | CD82 molecule |
| LOC100128788 | 0.708 | 0.552 | 0.886 | 2.391 | 2.548 | 3.108 | 3.579 | 0.0008807 | No description |
| CD22 | 0.825 | 1.893 | 1.126 | 2.886 | 3.194 | 2.968 | 3.585 | 0.0034678 | CD22 molecule |
| RANBP1 | 8.727 | 6.9 | 7.71 | 9.97 | 9.235 | 9.553 | 3.587 | 0.0098734 | RAN binding protein 1 |
| PRSS21 | 4.527 | 5.398 | 3.043 | 7.472 | 4.886 | 6.092 | 3.59 | 0.044106 | protease, serine, 21 (testisin) |
| ZNF286A | 1.492 | 1.366 | 0.543 | 2.388 | 3.581 | 2.548 | 3.592 | 0.0083351 | zinc finger protein 286A |
| AOYP1 | 4.208 | 2.588 | 2.41 | 4.503 | 4.419 | 4.435 | 3.598 | 0.0319346 | acylphosphatase 1, erythrocyte (common) type |
| SNRNP40 | 5.577 | 4.405 | 4.394 | 6.689 | 6.57 | 6.242 | 3.601 | 0.0058375 | small nuclear ribonucleoprotein 40kDa (U5) |
| SNORD10 | 4.393 | 2.934 | 3.689 | 5.546 | 5.357 | 5.821 | 3.622 | 0.0041082 | small nucleolar RNA, C/D box 10 |
| LETM2 | 3.392 | 3.23 | 3.178 | 5.25 | 4.733 | 5.153 | 3.624 | 0.0008736 | leucine zipper-EF-hand containing transmembrane protein 2 |
| IL11 | 6.137 | 5.087 | 4.875 | 6.796 | 7.052 | 6.946 | 3.626 | 0.0081677 | interleukin 11 |
| MAP1LC3C | 1.719 | -0.529 | 0.797 | 1.471 | 2.797 | 2.656 | 3.627 | 0.0329806 | microtubule-associated protein 1 light chain 3 gamma |
| PDCD2 | 6.157 | 4.941 | 5.137 | 7.242 | 7.021 | 6.802 | 3.633 | 0.0070659 | programmed cell death 2 |
| NGEF | 1.714 | -0.046 | -0.104 | 1.818 | 3.341 | 1.779 | 3.641 | 0.0240402 | neuronal guanine nucleotide exchange factor |
| PRKAA2 | 3.89 | 3.954 | 3.296 | 5.819 | 5.199 | 5.409 | 3.642 | 0.0021721 | protein kinase, AMP-activated, alpha 2 catalytic subunit |
| TUBA1C | 11.595 | 9.855 | 9.431 | 12.125 | 11.658 | 11.719 | 3.642 | 0.0308764 | tubulin, alpha 1c |
| PMS2L1 | 1.908 | 1.262 | 2.457 | 3.774 | 4.518 | 3.068 | 3.644 | 0.006628 | No description |
| PNLDC1 | 1.714 | 1.715 | 1.219 | 3.588 | 3.513 | 3.156 | 3.662 | 0.000938 | poly(A)-specific ribonuclease (PARN)-like domain containing 1 |
| ZGLP1 | 3.51 | 2.896 | 2.973 | 4.77 | 5.193 | 4.942 | 3.665 | 0.0011884 | zinc finger, GATA-like protein 1 |
| REXO4 | 7.631 | 5.467 | 5.697 | 8.192 | 7.34 | 7.635 | 3.665 | 0.0458289 | REX4, RNA exonuclease 4 homolog (S. cerevisiae) |
| H2AFX | 10.094 | 8.448 | 7.599 | 9.855 | 10.323 | 10.333 | 3.667 | 0.0486113 | H2A histone family, member X |
| GPR97 | 3.026 | 2.544 | 1.368 | 4.902 | 3.755 | 4.256 | 3.669 | 0.0068885 | G protein-coupled receptor 97 |
| PGM5P2 | 3.234 | 3.568 | 2.767 | 5.17 | 5.11 | 5.009 | 3.671 | 0.0010446 | phosphoglucomutase 5 pseudogene 2 |
| ALG3 | 7.413 | 6.003 | 5.447 | 8.5 | 7.885 | 7.71 | 3.686 | 0.0154339 | asparagine-linked glycosylation 3, alpha-1,3-mannosyltransferase homolog (S. cerevisiae) |
| KRT16P2 | 1.571 | 1.736 | 1.033 | 2.735 | 5.665 | 3.454 | 3.689 | 0.0081355 | keratin 16 pseudogene 2 |
| EXOSC5 | 5.746 | 4.784 | 5.234 | 7.265 | 7.119 | 6.784 | 3.693 | 0.0024211 | exosome component 5 |
| DCST1 | 0.403 | -0.887 | 1.847 | 1.743 | 2.39 | 2.288 | 3.694 | 0.0339608 | DC-STAMP domain containing 1 |
| PPP1R14C | 3.74 | 5.541 | 5.134 | 7.164 | 6.387 | 7.019 | 3.695 | 0.0060285 | protein phosphatase 1, regulatory (inhibitor) subunit 14C |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| C11orf83 | 3.315 | 3.149 | 3.861 | 5.459 | 5.043 | 5.204 | 3.702 | 0.0016255 | chromosome 11 open reading frame 83 |
| RPL18 | 12.725 | 11.636 | 11.962 | 13.854 | 13.958 | 13.854 | 3.713 | 0.0028905 | ribosomal protein L18 |
| C11orf71 | 3.356 | 2.838 | 4.09 | 4.582 | 5.984 | 5.411 | 3.716 | 0.0069729 | chromosome 11 open reading frame 71 |
| PI4KAP1 | 3.248 | 4.049 | 3.596 | 4.032 | 5.974 | 5.49 | 3.717 | 0.0261265 | phosphatidylinositol 4-kinase, catalytic, alpha pseudogene 1 |
| GPR35 | 4.684 | 4.194 | 3.902 | 6.148 | 6.089 | 6.018 | 3.719 | 0.0012914 | G protein-coupled receptor 35 |
| SLC19A1 | 4.663 | 3.654 | 3.778 | 5.96 | 5.678 | 5.671 | 3.732 | 0.0034321 | solute carrier family 19 (folate transporter), member 1 |
| LOC643763 | 3.475 | 2.504 | 2.616 | 4.511 | 4.674 | 4.517 | 3.733 | 0.0033405 | No description |
| GPR37L1 | 4.761 | 4.865 | 4.023 | 6.277 | 6.767 | 6.491 | 3.737 | 0.0014839 | G protein-coupled receptor 37 like 1 |
| STK35 | 5.723 | 5.263 | 6.335 | 6.935 | 8.237 | 7.686 | 3.737 | 0.0059684 | serine/threonine kinase 35 |
| ISG20L2 | 9.643 | 7.905 | 7.545 | 9.832 | 9.707 | 9.808 | 3.741 | 0.0385905 | interferon stimulated exonuclease gene 20kDa-like 2 |
| HCG4 | 2.84 | 2.039 | 1.66 | 2.489 | 4.745 | 4.037 | 3.745 | 0.0361408 | HLA complex group 4 |
| C12orf65 | 5.478 | 4.639 | 4.419 | 6.364 | 6.863 | 6.546 | 3.751 | 0.003812 | chromosome 12 open reading frame 65 |
| KCNK3 | 2.637 | 4.659 | 3.125 | 5.032 | 5.483 | 4.639 | 3.753 | 0.0258582 | potassium channel, subfamily K, member 3 |
| SLC12A3 | -0.012 | 1.604 | 0.422 | 2.293 | 2.332 | 2.735 | 3.759 | 0.0076361 | solute carrier family 12 (sodium/chloride transporters), member 3 |
| POU2F2 | 5.042 | 4.443 | 3.679 | 6.357 | 6.813 | 6.294 | 3.77 | 0.0022609 | POU class 2 homeobox 2 |
| UNC93B1 | 5.124 | 2.988 | 3.784 | 6.003 | 5.69 | 5.702 | 3.78 | 0.011994 | unc-93 homolog B1 (C. elegans) |
| MGAT5B | 0.838 | 0.834 | 1.277 | 3.212 | 2.758 | 2.04 | 3.782 | 0.0048716 | mannosyl (alpha-1,6-)-glycoprotein beta-1,6-N-acetyl-glucosaminyltransferase, isozyme B |
| TNFRSF10A | 2.847 | 2.807 | 2.021 | 5.087 | 3.74 | 4.729 | 3.789 | 0.0044344 | tumor necrosis factor receptor superfamily, member 10a |
| LYSMD2 | 6.494 | 4.261 | 4.611 | 7.082 | 6.394 | 6.532 | 3.789 | 0.0355319 | LysM, putative peptidoglycan-binding, domain containing 2 |
| KIAA1826 | 4.497 | 2.629 | 3.067 | 5.463 | 4.857 | 4.989 | 3.79 | 0.0144323 | KIAA1826 |
| MRPL53 | 3.474 | 1.604 | 2.792 | 4.894 | 4.596 | 4.715 | 3.791 | 0.0043765 | mitochondrial ribosomal protein L53 |
| BIRC5 | 2.493 | 1.298 | 1.896 | 3.464 | 3.822 | 3.835 | 3.8 | 0.0034464 | baculoviral IAP repeat-containing 5 |
| ABCC3 | 4.901 | 5.814 | 5.323 | 7.779 | 6.438 | 7.255 | 3.815 | 0.0059898 | ATP-binding cassette, sub-family C (CFTR/MRP), member 3 |
| GPR109A | -0.648 | 1.219 | -0.904 | 1.029 | 2.938 | 2.288 | 3.817 | 0.0134235 | G protein-coupled receptor 109A |
| ACCN4 | 0.589 | 0.323 | 0.251 | 1.623 | 2.623 | 2.258 | 3.824 | 0.0025478 | amiloride-sensitive cation channel 4, pituitary |
| HSD17B10 | 7.995 | 6.601 | 6.274 | 8.618 | 8.537 | 8.426 | 3.828 | 0.015831 | hydroxysteroid (17-beta) dehydrogenase 10 |
| SOLH | 8.845 | 6.976 | 7.355 | 9.912 | 9.18 | 9.293 | 3.83 | 0.0145339 | small optic lobes homolog (Drosophila) |
| DNASE1L2 | 1.44 | -1.775 | 0.599 | 1.898 | 2.539 | 2.556 | 3.837 | 0.0174837 | deoxyribonuclease I-like 2 |
| GLB1L3 | 1.433 | 1.988 | 2.884 | 3.861 | 4.149 | 3.929 | 3.838 | 0.0041368 | galactosidase, beta 1-like 3 |
| MRPS30 | 6.457 | 4.515 | 4.626 | 6.712 | 6.538 | 6.572 | 3.852 | 0.0375267 | mitochondrial ribosomal protein S30 |
| RPS16 | 11.739 | 10.233 | 10.578 | 13.149 | 12.523 | 12.396 | 3.853 | 0.0068212 | ribosomal protein S16 |
| SBSN | 1.742 | 1.199 | 2.215 | 3.679 | 4.085 | 3.689 | 3.856 | 0.0011741 | suprabasin |
| SERPINA1 | 6.131 | 5.128 | 5.249 | 7.076 | 7.534 | 7.465 | 3.858 | 0.0026579 | serpin peptidase inhibitor, clade A (alpha-1 antiproteinase, antitrypsin), member 1 |
| AREG | 5.088 | 6.893 | 5.023 | 7.495 | 6.97 | 7.351 | 3.858 | 0.0219446 | amphiregulin |
| CLDN1 | 2.834 | 3.832 | 3.834 | 4.285 | 6.41 | 5.784 | 3.868 | 0.0115246 | claudin 1 |
| PYGM | 4.844 | 4.582 | 4.697 | 7.172 | 6.565 | 6.535 | 3.871 | 0.0005652 | phosphorylase, glycogen, muscle |
| SSU72 | 9.825 | 8.412 | 8.52 | 10.823 | 10.371 | 10.475 | 3.877 | 0.0098877 | SSU72 RNA polymerase II CTD phosphatase homolog (S. cerevisiae) |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| DCAF4 | 7.238 | 5.311 | 5.473 | 7.728 | 7.266 | 7.454 | 3.878 | 0.0309845 | DDB1 and CUL4 associated factor 4 |
| ADNP2 | 6.358 | 6.032 | 5.364 | 7.525 | 8.082 | 7.989 | 3.882 | 0.0019561 | ADNP homeobox2 |
| QRICH2 | 6.097 | 4.13 | 5.304 | 7.47 | 7.261 | 6.655 | 3.882 | 0.008685 | glutamine rich 2 |
| WRAP53 | 5.651 | 3.397 | 3.91 | 6.196 | 5.867 | 5.817 | 3.887 | 0.0250261 | WD repeat containing, antisense to TP53 |
| C9orf152 | 2.315 | 2.797 | 1.993 | 4.214 | 4.274 | 4.285 | 3.887 | 0.0010589 | chromosome 9 open reading frame 152 |
| ASB16 | 2.994 | 2.14 | 2.677 | 4.636 | 4.437 | 4.668 | 3.889 | 0.0010024 | ankyrin repeat and SOCS box-containing 16 |
| CCBP2 | 5.932 | 5.086 | 6.822 | 8.141 | 7.892 | 7.668 | 3.891 | 0.0053137 | chemokine binding protein 2 |
| FERMT3 | 5.215 | 4.32 | 4.796 | 6.164 | 7.176 | 6.846 | 3.892 | 0.0027409 | fermitin family member 3 |
| SLC22A9 | 0.162 | 0.464 | 0.17 | 2.396 | 2.427 | 1.715 | 3.898 | 0.0011598 | solute carrier family 22 (organic anion transporter), member 9 |
| CNTD2 | 4.824 | 4.719 | 5.307 | 6.79 | 7.32 | 6.641 | 3.907 | 0.0011812 | cyclin N-terminal domain containing 2 |
| TRMT6 | 6.404 | 5.306 | 4.952 | 8.254 | 6.919 | 7.818 | 3.909 | 0.005107 | tRNA methyltransferase 6 homolog (S. cerevisiae) |
| JAGN1 | 6.92 | 5.027 | 5.058 | 7.502 | 6.994 | 7.059 | 3.909 | 0.0292395 | jagunal homolog 1 (Drosophila) |
| CSF3R | 1.818 | 1.386 | 0.251 | 3.489 | 2.221 | 3.52 | 3.918 | 0.0097918 | colony stimulating factor 3 receptor (granulocyte) |
| SLC39A4 | 4.873 | 3.851 | 3.431 | 6.594 | 5.403 | 5.84 | 3.925 | 0.0072076 | solute carrier family 39 (zinc transporter), member 4 |
| VPS11 | 7.112 | 5.413 | 5.489 | 7.733 | 7.465 | 7.449 | 3.934 | 0.0193074 | vacuolar protein sorting 11 homolog (S. cerevisiae) |
| MRPS15 | 6.838 | 4.964 | 5.532 | 7.958 | 7.257 | 7.512 | 3.945 | 0.0112256 | mitochondrial ribosomal protein S15 |
| SPDYA | 0.208 | 1.847 | 0.886 | 2.63 | 3.373 | 2.872 | 3.96 | 0.005127 | speedy homolog A (Xenopus laevis) |
| SNTA1 | 4.969 | 2.549 | 3.126 | 5.198 | 5.115 | 5.044 | 3.968 | 0.0342205 | syntrophin, alpha 1 (dystrophin-associated protein A1,59kDa, acidic component) |
| NOG | 7.095 | 5.447 | 6.201 | 8.276 | 7.829 | 8.191 | 3.97 | 0.0061286 | noggin |
| C19orf25 | 5.676 | 3.841 | 4.146 | 6.856 | 6.137 | 6.115 | 3.975 | 0.0119081 | chromosome 19 open reading frame 25 |
| C11orf84 | 6.608 | 4.821 | 4.788 | 7.546 | 8.054 | 6.782 | 3.982 | 0.0097453 | chromosome 11 open reading frame 84 |
| C15orf48 | 2.429 | 2.004 | 1.826 | 4.408 | 3.998 | 3.918 | 3.985 | 0.0007012 | chromosome 15 open reading frame 48 |
| SGSM1 | 3.331 | 3.371 | 2.42 | 5.355 | 5.261 | 5.326 | 3.986 | 0.0006582 | small G protein signaling modulator 1 |
| LOC1002868 44 | 2.32 | 1.908 | 2.025 | 3.953 | 4.158 | 4.02 | 3.988 | 0.0003713 | No description |
| MRPL41 | 7.476 | 5.877 | 6.41 | 9.157 | 8.406 | 8.345 | 3.989 | 0.0046283 | mitochondrial ribosomal protein L41 |
| S100A9 | 4.281 | 2.419 | 3.707 | 5.66 | 6.28 | 5.626 | 3.998 | 0.0029076 | S100 calcium binding protein A9 |
| CCK | 2.546 | 2.257 | 2.339 | 5.05 | 4.14 | 4.339 | 4.001 | 0.0008085 | cholecystokinin |
| HDX | 4.167 | 1.885 | 2.549 | 4.757 | 4.553 | 4.28 | 4.01 | 0.023465 | highly divergent homeobox |
| COMTD1 | 3.303 | 2.964 | 3.133 | 5.766 | 4.969 | 5.059 | 4.014 | 0.000694 | catechol-O-methyltransferase domain containing 1 |
| MARCKSL1 | 10.077 | 8.475 | 8.657 | 10.571 | 10.772 | 10.662 | 4.015 | 0.0132761 | MARCKS-like 1 |
| GAL | 5.185 | 4.456 | 4.141 | 6.798 | 6.34 | 6.465 | 4.025 | 0.0019918 | galanin prepropeptide |
| NCAPD3 | 3.576 | 2.6 | 3.032 | 5.588 | 4.998 | 4.9 | 4.035 | 0.001554 | non-SMC condensin II complex, subunit D3 |
| FBXL6 | 6.755 | 5.424 | 6.114 | 8.033 | 8.334 | 8.127 | 4.035 | 0.0020491 | F-box and leucine-rich repeat protein 6 |
| LOC728323 | 1.037 | 2.497 | 0.162 | 2.638 | 3.051 | 3.498 | 4.038 | 0.0177205 | No description |
| GNL1 | 6.507 | 5.059 | 5.067 | 7.541 | 7.712 | 7.074 | 4.04 | 0.0060571 | guanine nucleotide binding protein-like 1 |
| PHLDB3 | 6.691 | 5.051 | 4.978 | 7.126 | 7.065 | 6.997 | 4.04 | 0.022444 | pleckstrin homology-like domain, family B, member 3 |
| FAHD1 | 4.917 | 3.63 | 2.534 | 6.503 | 4.549 | 6.026 | 4.042 | 0.0222587 | fumarylacetoacetate hydrolase domain containing 1 |
| TKT | 8.956 | 7.873 | 7.22 | 10.453 | 9.851 | 9.893 | 4.056 | 0.0047185 | transketolase |
| AKT1S1 | 6.428 | 4.691 | 5.328 | 7.351 | 7.734 | 7.028 | 4.063 | 0.0071332 | AKT1 substrate 1 (proline-rich) |
| RNMTL1 | 7.241 | 3.99 | 5.136 | 7.454 | 7.158 | 7.115 | 4.063 | 0.0412492 | RNA methyltransferase like 1 |
| BAD | 7.439 | 5.076 | 6.06 | 8.087 | 8.113 | 7.897 | 4.078 | 0.0152128 | BCL2-associated agonist of cell death |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| PITPNM1 | 7.127 | 7.181 | 6.69 | 8.722 | 9.464 | 9.044 | 4.09 | 0.0007655 | phosphatidylinositol transfer protein, membrane-associated 1 |
| EXOSC6 | 6.658 | 5.634 | 5.641 | 7.723 | 7.83 | 7.668 | 4.094 | 0.0034535 | exosome component 6 |
| C1orf163 | 5.715 | 2.831 | 4.159 | 6.203 | 6.003 | 6.239 | 4.124 | 0.0215246 | chromosome 1 open reading frame 163 |
| LOC285847 | 1.228 | 1.075 | 2.453 | 1.825 | 4.498 | 3.614 | 4.125 | 0.0398784 | No description |
| L3MBTL2 | 5.923 | 4.104 | 4.799 | 7.161 | 6.65 | 6.848 | 4.138 | 0.0063705 | l(3)mbt-like 2 (Drosophila) |
| TRPM2 | 2.41 | 0.924 | 1.09 | 4.156 | 2.983 | 3.237 | 4.169 | 0.0069021 | transient receptor potential cation channel, subfamily M, member 2 |
| PCYT1A | 1.703 | 0.666 | 1.778 | 4.426 | 1.88 | 3.763 | 4.171 | 0.0192273 | phosphate cytidylyltransferase 1, choline, alpha |
| COX7A2L | 5.105 | 3.459 | 3.932 | 5.993 | 6.29 | 5.65 | 4.173 | 0.0078271 | cytochrome c oxidase subunit VIIa polypeptide 2 like |
| SCO1 | 6.066 | 4.076 | 4.901 | 7.833 | 6.702 | 6.964 | 4.178 | 0.0067089 | SCO cytochrome oxidase deficient homolog 1 (yeast) |
| TSG1 | 2.539 | 4.266 | 3.091 | 4.495 | 6.329 | 5.815 | 4.179 | 0.0074565 | No description |
| CCDC72 | 8.846 | 7.787 | 8.612 | 10.913 | 10.403 | 10.451 | 4.19 | 0.0012699 | coiled-coil domain containing 72 |
| CYP2B6 | 3.353 | 3.296 | 2.689 | 5.312 | 5.426 | 5.196 | 4.208 | 0.0004143 | cytochrome P450, family 2, subfamily B, polypeptide 6 |
| CHCHD2 | 10.609 | 8.887 | 10.041 | 12.625 | 12.115 | 11.859 | 4.21 | 0.0025191 | coiled-coil-helix-coiled-coil-helix domain containing 2 |
| KLC2 | 7.25 | 5.649 | 6.333 | 8.521 | 8.395 | 8.41 | 4.22 | 0.0034607 | kinesin light chain 2 |
| C19orf77 | 2.167 | 2.194 | 1.959 | 5.57 | 3.538 | 4.246 | 4.224 | 0.0033333 | chromosome 19 open reading frame 77 |
| PABPC4 | 10.428 | 8.035 | 8.997 | 11.128 | 10.683 | 11.082 | 4.242 | 0.0175581 | poly(A) binding protein, cytoplasmic 4 (inducible form) |
| CST9 | -0.904 | 0.814 | 0.315 | 2.548 | 2.06 | 2.4 | 4.244 | 0.0027767 | cystatin 9 (testatin) |
| STEAP3 | 4.036 | 2.506 | 3.004 | 5.019 | 5.092 | 5.17 | 4.25 | 0.0042513 | STEAP family member 3 |
| AP1S1 | 3.715 | 3.274 | 2.695 | 5.439 | 5.362 | 4.81 | 4.251 | 0.0020205 | adaptor-related protein complex 1, sigma 1 subunit |
| LGALS12 | 1.424 | 0.499 | 0.825 | 3.493 | 3.513 | 2.54 | 4.254 | 0.0015397 | lectin, galactoside-binding, soluble, 12 |
| EDARADD | 4.623 | 2.742 | 2.232 | 5.19 | 4.852 | 4.325 | 4.265 | 0.0371439 | EDAR-associated death domain |
| ITGAM | 0.625 | 0.588 | 1.234 | 3.581 | 2.569 | 2.721 | 4.274 | 0.0015969 | integrin, alpha M (complement component 3 receptor 3 subunit) |
| SUV39H1 | 3.56 | 1.562 | 1.234 | 4.405 | 3.331 | 3.936 | 4.277 | 0.0256901 | suppressor of variegation 3-9 homolog 1 (Drosophila) |
| C21orf99 | 1.161 | -0.258 | 1.894 | 3.258 | 1.894 | 3.601 | 4.279 | 0.0173635 | No description |
| SCGB3A1 | 2.623 | 2.46 | 1.645 | 4.347 | 4.636 | 4.562 | 4.294 | 0.0006725 | secretoglobin, family 3A, member 1 |
| NLE1 | 6.503 | 4.705 | 5.127 | 7.712 | 7.101 | 7.229 | 4.295 | 0.0079109 | notchless homolog 1 (Drosophila) |
| RPS9 | 13.004 | 11.407 | 12.007 | 14.113 | 14.113 | 13.731 | 4.303 | 0.0057802 | ribosomal protein S9 |
| FST | 10.28 | 9.041 | 7.553 | 11.635 | 10.617 | 11.147 | 4.306 | 0.0123667 | follistatin |
| CD3EAP | 8.757 | 8.254 | 7.955 | 10.475 | 10.361 | 10.224 | 4.309 | 0.0007369 | CD3e molecule, epsilon associated protein |
| RASD2 | 2.776 | 3.267 | 2.145 | 5.368 | 4.575 | 4.886 | 4.317 | 0.0015111 | RASD family, member 2 |
| TUSC2 | 7.274 | 5.862 | 5.955 | 8.569 | 8.067 | 8.061 | 4.323 | 0.0055591 | tumor suppressor candidate 2 |
| PDZD9 | 2.118 | 2.152 | 1.942 | 4.428 | 3.869 | 4.231 | 4.326 | 0.0003427 | PDZ domain containing 9 |
| SNORD66 | 0.609 | -0.887 | 0.224 | 2.056 | 2.725 | 2.099 | 4.335 | 0.0020985 | small nucleolar RNA, C/D box 66 |
| MFNG | 6.578 | 5.117 | 4.912 | 7.03 | 7.537 | 7.414 | 4.342 | 0.0092581 | MFNG O-fucosylpeptide 3-beta-N-acetylglucosaminyltransferase |
| NFATC3 | 7.503 | 5.451 | 5.51 | 7.575 | 7.955 | 7.888 | 4.359 | 0.0235337 | nuclear factor of activated T-cells, cytoplasmic, calcineurin-dependent 3 |
| SNORA80B | -0.192 | -0.177 | -1.775 | 0.673 | 1.948 | 1.908 | 4.362 | 0.0057874 | small nucleolar RNA, H/ACA box 80B |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| CDKN2A | 3.997 | 2.388 | 3.88 | 5.967 | 6.122 | 5.616 | 4.364 | 0.0017815 | cyclin-dependent kinase inhibitor 2A (melanoma, p16, inhibits CDK4) |
| MAP7D2 | 2.175 | 1.471 | 2.078 | 4.16 | 4.3 | 3.785 | 4.365 | 0.0006096 | MAP7 domain containing 2 |
| TSEN34 | 3.369 | 2.423 | 2.93 | 4.542 | 5.495 | 5.087 | 4.365 | 0.0016785 | tRNA splicing endonuclease 34 homolog (S. cerevisiae) |
| C12orf61 | 2.359 | 0.499 | 1.219 | 4 | 3.56 | 2.628 | 4.373 | 0.0089991 | chromosome 12 open reading frame 61 |
| PPP1R16A | 4.051 | 4.065 | 3.764 | 5.896 | 6.297 | 5.99 | 4.383 | 0.0002797 | protein phosphatase 1, regulatory (inhibitor) subunit 16A |
| SCARNA13 | -0.192 | 2.17 | 2.834 | 3.906 | 4.327 | 4.305 | 4.393 | 0.0076147 | small Cajal body-specific RNA 13 |
| MYO1G | 3.86 | 2.784 | 4.142 | 5.997 | 5.895 | 6.229 | 4.397 | 0.0009809 | myosin IG |
| KRTCAP3 | 2.592 | 2.004 | 0.315 | 4.199 | 4.14 | 3.634 | 4.397 | 0.0050304 | keratinocyte associated protein 3 |
| CYP4F11 | 7.316 | 6.229 | 6.585 | 9.746 | 7.39 | 8.723 | 4.402 | 0.0163783 | cytochrome P450, family 4, subfamily F, polypeptide 11 |
| KRT18 | 3.256 | 2.112 | 1.573 | 3.932 | 5.303 | 4.253 | 4.41 | 0.0055999 | keratin 18 |
| COQ3 | 2.556 | 2.657 | 2.363 | 5.213 | 4.253 | 4.698 | 4.412 | 0.0006868 | coenzyme Q3 homolog, methyltransferase (S. cerevisiae) |
| CSNK2A1P | 7.227 | 5.222 | 5.672 | 8.089 | 7.816 | 7.647 | 4.419 | 0.01217 | casein kinase 2, alpha 1 polypeptide pseudogene |
| OXT | 2.908 | -0.887 | 2.111 | 3.841 | 4.397 | 4.256 | 4.423 | 0.0112184 | oxytocin, prepropeptide |
| NCF4 | 3.988 | 1.547 | 2.976 | 5.085 | 5.688 | 5.121 | 4.424 | 0.0046026 | neutrophil cytosolic factor 4, 40kDa |
| COX6B2 | 2.447 | 1.677 | 2.028 | 4.056 | 4.598 | 4.149 | 4.441 | 0.0005781 | cytochrome c oxidase subunit VIb polypeptide 2 (testis) |
| RRP9 | 9.54 | 6.49 | 8.062 | 10.874 | 10.216 | 10.006 | 4.448 | 0.0117142 | ribosomal RNA processing 9, small subunit (SSU) processome component, homolog (yeast) |
| AUP1 | 6.266 | 5.966 | 6.725 | 8.15 | 8.865 | 8.422 | 4.458 | 0.0008664 | ancient ubiquitous protein 1 |
| COLEC11 | 4.775 | 2.89 | 3.418 | 4.508 | 6.936 | 6.059 | 4.474 | 0.0166681 | collectin sub-family member 11 |
| GPR25 | 0.888 | -0.887 | -0.064 | 1.898 | 2.142 | 2.099 | 4.481 | 0.0040431 | G protein-coupled receptor 25 |
| CDH16 | 1.03 | 0.903 | 0.978 | 2.064 | 3.462 | 3.147 | 4.496 | 0.0036324 | cadherin 16, KSP-cadherin |
| PCNA | 7.72 | 6.162 | 6.606 | 8.776 | 8.786 | 8.716 | 4.499 | 0.0043128 | proliferating cell nuclear antigen |
| KRT16 | 11.189 | 11.579 | 9.689 | 11.894 | 13.756 | 12.909 | 4.522 | 0.0140674 | keratin 16 |
| TXNIP | 7.046 | 6.237 | 8.025 | 8.677 | 9.629 | 9.223 | 4.523 | 0.0054633 | thioredoxin interacting protein |
| LMAN2L | 5.638 | 3.781 | 3.603 | 6.154 | 6.42 | 5.782 | 4.529 | 0.0167597 | lectin, mannose-binding 2-like |
| TUBA4A | 4.511 | 2.57 | 2.981 | 5.165 | 5.881 | 5.056 | 4.542 | 0.0082901 | tubulin, alpha 4a |
| MRPL13 | 5.845 | 3.919 | 4.544 | 7.341 | 6.388 | 6.731 | 4.552 | 0.0071017 | mitochondrial ribosomal protein L13 |
| LRRC56 | 5.059 | 3.43 | 3.807 | 6.085 | 6.319 | 5.621 | 4.565 | 0.0063919 | leucine rich repeat containing 56 |
| ARRB2 | 4.349 | 4.09 | 4.386 | 6.283 | 6.742 | 6.415 | 4.573 | 0.0002583 | arrestin, beta 2 |
| RPRM | 1.719 | 2.593 | -0.274 | 4.001 | 3.915 | 3.874 | 4.583 | 0.0056071 | reprimo, TP53 dependent G2 arrest mediator candidate |
| C19orf55 | 3.046 | 2.316 | 2.119 | 4.52 | 4.317 | 4.534 | 4.588 | 0.0013429 | chromosome 19 open reading frame 55 |
| ZC3H13 | 5.441 | 6.072 | 4.754 | 7.761 | 7.213 | 7.645 | 4.607 | 0.0020562 | zinc finger CCCH-type containing 13 |
| ERP27 | 2.683 | 0.862 | 0.315 | 2.886 | 3.832 | 3.068 | 4.613 | 0.0152415 | endoplasmic reticulum protein 27 |
| LAT2 | 4.198 | 2.639 | 2.709 | 4.901 | 4.917 | 5.077 | 4.622 | 0.007981 | linker for activation of T cells family, member 2 |
| KCNN4 | 7.941 | 5.941 | 5.76 | 8.168 | 8.155 | 7.994 | 4.64 | 0.0317858 | potassium intermediate/small conductance calcium-activated channel, subfamily N, member 4 |
| NKX3-1 | 6.227 | 4.673 | 4.038 | 6.772 | 6.892 | 7.04 | 4.656 | 0.0107849 | NK3 homeobox 1 |
| AURKAIP1 | 7.984 | 6.061 | 6.611 | 9.458 | 8.832 | 8.672 | 4.661 | 0.005997 | aurora kinase A interacting protein 1 |
| SH2D2A | 0.162 | 0.464 | 0.888 | 2.157 | 3.111 | 2.813 | 4.67 | 0.0011383 | SH2 domain containing 2A |
| HOMER2 | 4.035 | 2.588 | 2.783 | 5.379 | 5.007 | 4.917 | 4.673 | 0.0041819 | homer homolog 2 (Drosophila) |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| C17orf56 | 2.952 | 2.605 | 1.473 | 4.543 | 5.183 | 4.613 | 4.694 | 0.0015755 | chromosome 17 open reading frame 56 |
| CPNE7 | 1.949 | 1.709 | 2.205 | 4.193 | 4.571 | 3.662 | 4.739 | 0.0007584 | copine VII |
| TMEM97 | 6.486 | 4.346 | 4.282 | 6.904 | 6.597 | 6.529 | 4.745 | 0.0291572 | transmembrane protein 97 |
| ACTR5 | 6.194 | 5.235 | 4.79 | 7.646 | 7.483 | 7.189 | 4.749 | 0.0029148 | ARP5 actin-related protein 5 homolog (yeast) |
| S100A6 | 11.768 | 9.001 | 10.197 | 13.263 | 12.445 | 12.265 | 4.749 | 0.0095071 | S100 calcium binding protein A6 |
| GJB3 | 1.077 | 0.323 | 0.68 | 3.874 | 2.928 | 2.459 | 4.751 | 0.0015325 | gap junction protein, beta 3, 31 kDa |
| RASL10B | 3.642 | 1.15 | 0.884 | 4.677 | 3.134 | 3.443 | 4.757 | 0.0391007 | RAS-like, family 10, member B |
| POPDC3 | 0.723 | 0.992 | −0.104 | 3.246 | 2.332 | 2.261 | 4.77 | 0.0030057 | popeye domain containing 3 |
| KRT13 | −0.376 | 1.828 | −0.778 | 1.672 | 2.317 | 1.878 | 4.77 | 0.032112 | keratin 13 |
| TMEM199 | 4.989 | 3.24 | 3.662 | 6.335 | 5.917 | 5.832 | 4.772 | 0.0047256 | transmembrane protein 199 |
| NKAPL | −0.012 | 0.78 | −0.104 | 2.417 | 2.548 | 2.153 | 4.779 | 0.000895 | NFKB activating protein-like |
| FAM83G | 4.144 | 3.539 | 2.735 | 5.797 | 5.966 | 5.521 | 4.785 | 0.0015254 | family with sequence similarity 83, member G |
| SPI1 | 1.62 | 0.162 | 2.401 | 4.463 | 3.294 | 3.879 | 4.787 | 0.0044831 | spleen focus forming virus (SFFV) proviral integration oncogene spH |
| KRT19 | 4.436 | 4.34 | 4.104 | 6.089 | 7.521 | 6.602 | 4.796 | 0.0010231 | keratin 19 |
| PMEPA1 | 9.046 | 7.127 | 7.526 | 10.578 | 9.787 | 9.791 | 4.806 | 0.0058582 | prostate transmembrane protein, androgen induced 1 |
| ZNF98 | 2.132 | 1.783 | 2.111 | 4.121 | 4.397 | 4.109 | 4.807 | 0.0002368 | zinc finger protein 98 |
| FOXL1 | 2.031 | 1.432 | 1.342 | 3.612 | 4.204 | 3.743 | 4.823 | 0.0005294 | forkhead box L1 |
| SNORD19 | 3.073 | 2.526 | 2.986 | 5.259 | 4.875 | 5.324 | 4.832 | 0.0003141 | small nucleolar RNA, C/D box 19 |
| MT2A | 13.756 | 13.204 | 14.736 | 16.031 | 15.551 | 16.031 | 4.84 | 0.0041296 | metallothionein 2A |
| TFR2 | 1.379 | 0.224 | 1.724 | 3.66 | 3.657 | 3.541 | 4.851 | 0.0010303 | transferrin receptor 2 |
| E2F4 | 5.133 | 3.458 | 3.76 | 6.371 | 6.172 | 5.737 | 4.854 | 0.005758 | E2F transcription factor 4, p107/p130-binding |
| ANKRD1 | 4.076 | 4.809 | 6.863 | 7.681 | 6.355 | 7.332 | 4.855 | 0.0309401 | ankyrin repeat domain 1 (cardiac muscle) |
| AATF | 7.494 | 5.434 | 5.546 | 8.204 | 7.761 | 7.838 | 4.897 | 0.0171532 | apoptosis antagonizing transcription factor |
| RNASE6 | 1.571 | −0.258 | 0.589 | 2.735 | 2.994 | 2.889 | 4.927 | 0.0030658 | ribonuclease, RNase A family, k6 |
| B3GAT1 | 2.628 | 4.114 | 2.69 | 5.857 | 4.93 | 5.58 | 4.931 | 0.0029363 | beta-1,3-glucuronyltransferase 1 (glucuronosyltransferase P) |
| HIST1H1C | 1.44 | 1.033 | 2.392 | 3.395 | 5.173 | 3.336 | 4.935 | 0.0055305 | histone cluster 1, H1c |
| POMZP3 | 3.517 | 0.391 | 1.148 | 3.451 | 2.938 | 4.256 | 4.935 | 0.0411533 | POM121 and ZP3 fusion |
| ADCK2 | 6.498 | 3.642 | 4.42 | 6.73 | 6.903 | 6.485 | 4.961 | 0.0267511 | aarF domain containing kinase 2 |
| UHRF2 | 4.149 | 4.375 | 5.346 | 6.1 | 7.659 | 7.461 | 4.97 | 0.0027696 | ubiquitin-like with PHD and ring finger domains 2 |
| HMGA2 | 4.978 | 4.598 | 5.928 | 8.258 | 5.952 | 7.292 | 4.971 | 0.0146033 | high mobility group AT-hook 2 |
| NPB | 1.44 | −1.775 | 0.224 | 2.652 | 2.539 | 0.831 | 4.974 | 0.0360142 | neuropeptide B |
| RPL7L1 | 2.4 | 2.521 | 1.33 | 4.838 | 3.922 | 3.924 | 4.983 | 0.0029706 | ribosomal protein L7-like 1 |
| LRRC69 | 1.091 | −0.258 | −0.274 | 2.048 | 2.46 | 2.208 | 5.002 | 0.0032976 | leucine rich repeat containing 69 |
| MICALCL | 4.864 | 6.268 | 4.689 | 8.592 | 5.685 | 7.48 | 5.007 | 0.0294419 | MICAL C-terminal like |
| TMEM52 | 3.322 | 0.162 | 1.747 | 4.266 | 4.072 | 3.444 | 5.011 | 0.0172905 | transmembrane protein 52 |
| SLC7A5 | 11.505 | 9.988 | 9.514 | 13.092 | 12.191 | 12.316 | 5.019 | 0.0058231 | solute carrier family 7 (cationic amino acid transporter, y+ system), member 5 |
| HMHA1 | 3.661 | 1.944 | 3.452 | 5.998 | 5.292 | 4.931 | 5.052 | 0.0034192 | histocompatibility (minor) HA-1 |
| FKBP5 | 6.359 | 4.534 | 7.267 | 8.791 | 8.64 | 8.697 | 5.054 | 0.0042305 | FK506 binding protein 5 |
| DLST | 5.486 | 5.479 | 7.178 | 7.82 | 8.321 | 8.344 | 5.067 | 0.0051198 | dihydrolipoamide S-succinyltransferase (E2 component of 2-oxo-glutarate complex) |
| SFRS7 | 7.95 | 6.614 | 6.878 | 9.221 | 9.351 | 9.008 | 5.071 | 0.0024862 | No description |
| PGAM5 | 1.297 | 0.623 | −0.274 | 3.645 | 3.229 | 1.265 | 5.089 | 0.0138807 | phosphoglycerate mutase family member 5 |
| MRPS18C | 5.03 | 2.607 | 4.016 | 6.642 | 6.369 | 6.122 | 5.108 | 0.0040359 | mitochondrial ribosomal protein S18C |

TABLE 6-continued

Differentially Expressed Genes in CD10+ Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | CD24+ N48 | CD24+ N58 | CD24+ N43 | CD24+ N37 | CD24+ N39 | CD24+ N40 | | | |
| LRFN4 | 6.903 | 4.772 | 5.125 | 8.13 | 7.485 | 7.245 | 5.132 | 0.0107162 | leucine rich repeat and fibronectin type III domain containing 4 |
| FCRLB | 0.609 | 1.033 | 1.148 | 3.279 | 3.517 | 3.119 | 5.165 | 0.000244 | Fc receptor-like B |
| S100A3 | 2.798 | 0.623 | −0.648 | 3.744 | 2.994 | 1.878 | 5.171 | 0.0472848 | S100 calcium binding protein A3 |
| PHKG1 | 2.111 | 2.877 | 1.809 | 4.44 | 4.784 | 4.495 | 5.22 | 0.0007155 | phosphorylase kinase, gamma 1 (muscle) |
| UBE2M | 4.586 | 3.783 | 3.619 | 6.005 | 6.817 | 6.31 | 5.224 | 0.0008593 | ubiquitin-conjugating enzyme E2M (UBC12 homolog, yeast) |
| PSD4 | 4.159 | 3.091 | 3.773 | 6.547 | 5.925 | 5.856 | 5.233 | 0.0007226 | pleckstrin and Sec7 domain containing 4 |
| KIAA0406 | 4.741 | 2.649 | 3.163 | 5.552 | 5.689 | 5.358 | 5.237 | 0.0079595 | No description |
| TMED10 | 2.946 | 3.692 | 2.716 | 5.108 | 5.851 | 5.779 | 5.251 | 0.0006654 | transmembrane emp24-like trafficking protein 10 (yeast) |
| LOC645851 | 0.162 | 0.323 | 0.68 | 2.72 | 2.053 | 3.125 | 5.268 | 0.0009451 | No description |
| RASGEF1A | 1.219 | 1.46 | 1.271 | 3.865 | 3.764 | 3.022 | 5.294 | 0.0005366 | RasGEF domain family, member 1A |
| UHRF1 | 2.7 | 1.911 | 1.575 | 4.021 | 4.565 | 4.33 | 5.348 | 0.001109 | ubiquitin-like with PHD and ring finger domains 1 |
| SPAG4 | −0.648 | 0.251 | 0.599 | 2.437 | 3.025 | 2.651 | 5.373 | 0.0005438 | sperm associated antigen 4 |
| HESRG | 5.267 | 4.245 | 4.07 | 6.682 | 6.59 | 7.053 | 5.413 | 0.0013501 | No description |
| FOXC2 | 1.82 | 1.651 | 0.817 | 4.262 | 4.037 | 3.774 | 5.434 | 0.0004071 | forkhead box C2 (MFH-1, mesenchyme forkhead 1) |
| TLR2 | 3.159 | 2.968 | 2.549 | 4.696 | 6.253 | 5.425 | 5.491 | 0.0010875 | toll-like receptor 2 |
| GNL2 | 7.876 | 5.882 | 6.454 | 8.967 | 8.687 | 8.912 | 5.495 | 0.0052415 | guanine nucleotide binding protein-like 2 (nucleolar) |
| BANP | 7.132 | 4.889 | 5.115 | 7.388 | 7.857 | 7.576 | 5.507 | 0.0154067 | BTG3 associated nuclear protein |
| SPEM1 | 2.118 | −0.529 | 0.315 | 2.776 | 2.797 | 2.208 | 5.507 | 0.0174766 | spermatid maturation 1 |
| ACOT7 | 8.143 | 6.403 | 6.119 | 8.935 | 8.869 | 8.629 | 5.527 | 0.0100572 | acyl-CoA thioesterase 7 |
| TMEM177 | 3.081 | 1.651 | 1.99 | 4.463 | 4.478 | 4.383 | 5.553 | 0.0018387 | transmembrane protein 177 |
| C20orf165 | 0.525 | 0.162 | 0.162 | 2.638 | 2.999 | 2.008 | 5.555 | 0.0006797 | chromosome 20 open reading frame 165 |
| UBIAD1 | 9.212 | 5.604 | 6.88 | 9.47 | 9.312 | 9.367 | 5.604 | 0.0256972 | UbiA prenyltransferase domain containing 1 |
| BLOC1S3 | 6.369 | 3.35 | 3.695 | 6.736 | 6.13 | 6.194 | 5.651 | 0.0350311 | biogenesis of lysosomal organelles complex-1, subunit 3 |
| RPL26L1 | 6.58 | 4.996 | 4.165 | 7.503 | 7.516 | 7.199 | 5.686 | 0.0080196 | ribosomal protein L26-like 1 |
| PSPN | 4.022 | 2.257 | 1.315 | 5.302 | 4.347 | 4.766 | 5.69 | 0.0101152 | persephin |
| IMP4 | 3.308 | 3.291 | 2.847 | 5.702 | 5.544 | 5.819 | 5.699 | 0.000171 | IMP4, U3 small nucleolar ribonucleoprotein, homolog (yeast) |
| XDH | 4.776 | 5.707 | 3.555 | 7.592 | 6.39 | 7.288 | 5.704 | 0.0047471 | xanthine dehydrogenase |
| NEFM | 6.452 | 7.098 | 6.474 | 8.983 | 9.556 | 9.29 | 5.778 | 0.0002511 | neurofilament, medium polypeptide |
| ZSCAN29 | 5.93 | 4.207 | 4.316 | 6.741 | 6.885 | 6.967 | 5.79 | 0.0052064 | zinc finger and SCAN domain containing 29 |
| C19orf38 | 2.289 | 0.623 | −0.648 | 2.548 | 3.194 | 3.172 | 5.853 | 0.0129234 | chromosome 19 open reading frame 38 |
| HUS1B | 2.073 | 0.224 | 0.842 | 3.684 | 2.797 | 3.394 | 5.862 | 0.0040939 | HUS1 checkpoint homolog b (S. pombe) |
| FGFBP1 | 0.786 | 1.199 | 0.17 | 2.724 | 3.806 | 3.29 | 5.873 | 0.0007727 | fibroblast growth factor binding protein 1 |
| TCTEX1D4 | 0.224 | −0.529 | −0.778 | 1.88 | 2.06 | 2.031 | 5.896 | 0.0005008 | Tctex1 domain containing 4 |
| RAMP1 | 4.009 | 1.675 | 4.06 | 6.025 | 6.627 | 5.981 | 5.924 | 0.0025005 | receptor (G protein-coupled) activity modifying protein 1 |
| SRCRB4D | 2.211 | 0.522 | −0.778 | 4.076 | 3.093 | 3.068 | 5.939 | 0.0054275 | scavenger receptor cysteine rich domain containing, group B (4 domains) |
| FAM195A | 5.781 | 3.888 | 4.405 | 7.572 | 6.877 | 6.98 | 5.959 | 0.0026651 | family with sequence similarity 195, member A |
| GJB5 | 3.546 | 1.126 | 1.079 | 4.329 | 3.661 | 4.037 | 5.99 | 0.0147764 | gap junction protein, beta 5, 31.1kDa |
| SCAF1 | 4.924 | 3.826 | 3.823 | 6.034 | 7.509 | 6.892 | 6.001 | 0.0015826 | SR-related CTD-associated factor 1 |
| SIRT7 | 6.055 | 5.188 | 4.939 | 8.103 | 7.81 | 7.733 | 6.157 | 0.0005223 | sirtuin 7 |

TABLE 6-continued

Differentially Expressed Genes in CD10+ Breast Epithelial Cells

| | Nulliparous (NP) Samples | | | Parous (P) Samples | | | | | | |
|---|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| TPST2 | 7.187 | 5.353 | 5.226 | 8.704 | 8.232 | 7.853 | 6.177 | 0.0046426 | tyrosylprotein sulfotransferase 2 |
| TIGD3 | 2.359 | 0.886 | 0.162 | 2.957 | 4.213 | 3.514 | 6.182 | 0.0050376 | tigger transposable element derived 3 |
| IL19 | 1.885 | 1.625 | 1.947 | 5.344 | 4.537 | 3.893 | 6.283 | 0.0004858 | interleukin 19 |
| TDRD10 | −0.904 | −0.258 | 0.315 | 2.97 | −0.104 | 2.4 | 6.3 | 0.0278908 | tudor domain containing 10 |
| TGFB2 | 5.857 | 7.839 | 6.069 | 8.805 | 8.523 | 8.833 | 6.346 | 0.0060356 | transforming growth factor, beta 2 |
| ZNF48 | 4.656 | 2.091 | 1.042 | 5.757 | 4.759 | 4.453 | 6.355 | 0.0205273 | zinc finger protein 48 |
| MPZL3 | 1.703 | 1.982 | 0.757 | 3.855 | 4.652 | 3.821 | 6.363 | 0.0007799 | myelin protein zero-like 3 |
| TNFRSF18 | 5.884 | 3.456 | 3.229 | 6.608 | 6.179 | 5.915 | 6.434 | 0.0183723 | tumor necrosis factor receptor superfamily, member 18 |
| ASCL2 | 1.091 | −0.529 | −0.274 | 3.59 | 3.485 | 2.159 | 6.446 | 0.001393 | achaete-scute complex homolog 2 (Drosophila) |
| NOL7 | 3.498 | 2.647 | 3.727 | 6.419 | 5.706 | 5.559 | 6.464 | 0.0006511 | nucleolar protein 7, 27kDa |
| GAST | 2.149 | −0.258 | 1.196 | 3.949 | 3.258 | 3.902 | 6.527 | 0.0031688 | gastrin |
| LLGL2 | 5.229 | 4.307 | 3.785 | 7.072 | 6.962 | 7.013 | 6.528 | 0.0007083 | lethal giant larvae homolog 2 (Drosophila) |
| C12orf52 | 3.365 | 1.54 | 1.273 | 4.796 | 4.27 | 4.212 | 6.635 | 0.0044974 | chromosome 12 open reading frame 52 |
| KRTDAP | 4.639 | 2.542 | 3.112 | 5.858 | 5.858 | 5.907 | 6.711 | 0.0030951 | keratinocyte differentiation-associated protein |
| IFNA2 | −0.264 | 0.162 | −0.21 | 3.272 | 1.387 | 2.54 | 6.725 | 0.0019489 | interferon, alpha 2 |
| CXCL5 | 2.812 | 0.283 | 3.082 | 5.567 | 5.058 | 5.689 | 6.747 | 0.0018817 | chemokine (C-X-C motif) ligand 5 |
| CCDC11 | 0.323 | 1.301 | 1.199 | 3.818 | 4.062 | 3.886 | 6.779 | 0.0001925 | coiled-coil domain containing 11 |
| CTRL | 5.44 | 3.159 | 3.435 | 6.782 | 6.26 | 5.954 | 6.943 | 0.0066731 | chymotrypsin-like |
| SCGB1D2 | −1.775 | 1.783 | −1.775 | 1.029 | 2.725 | 2.819 | 6.982 | 0.017043 | secretoglobin, family 1D, member 2 |
| VNN1 | 0.162 | 1.685 | 0.585 | 3.041 | 3.389 | 3.457 | 6.983 | 0.0012342 | vanin 1 |
| PEX11B | 5.092 | 2.76 | 3.348 | 5.833 | 6.435 | 6.159 | 7.018 | 0.0048115 | peroxisomal biogenesis factor 11 beta |
| PIK3R5 | −1.155 | −1.775 | −0.376 | 2.437 | −0.648 | 1.908 | 7.027 | 0.0169307 | phosphoinositide-3-kinase, regulatory subunit 5 |
| NPW | 5.041 | 2.838 | 2.931 | 6.414 | 5.657 | 5.75 | 7.056 | 0.0064499 | neuropeptide W |
| ZNF628 | 4.382 | 2.41 | 2.883 | 5.707 | 5.722 | 5.337 | 7.079 | 0.0033047 | zinc finger protein 628 |
| RPL29 | 6.492 | 6.685 | 6.762 | 8.103 | 10.009 | 9.51 | 7.084 | 0.0018244 | ribosomal protein L29 |
| SLC25A38 | 6.205 | 3.999 | 4.209 | 7.411 | 6.912 | 7.058 | 7.208 | 0.0056285 | solute carrier family 25, member 38 |
| SLC34A2 | 1.916 | 1.305 | 1.818 | 3.748 | 5.428 | 4.677 | 7.253 | 0.0005953 | solute carrier family 34 (sodium phosphate), member 2 |
| RPS19BP1 | 5.607 | 4.22 | 4.064 | 7.776 | 7.444 | 7.036 | 7.849 | 0.0009094 | ribosomal protein S19 binding protein 1 |
| NOP16 | 5.385 | 3.98 | 4.13 | 7.004 | 7.367 | 7.353 | 8.131 | 0.0006239 | NOP16 nucleolar protein homolog (yeast) |
| CRB3 | 3.672 | 3.166 | 1.959 | 6.701 | 5.891 | 5.532 | 8.163 | 0.0007298 | crumbs homolog 3 (Drosophila) |
| DES | 2.687 | 0.814 | 0.924 | 4.693 | 3.852 | 4.584 | 8.214 | 0.0014696 | desmin |
| C9orf140 | 3.738 | 1.801 | 1.44 | 5.159 | 4.859 | 4.697 | 8.323 | 0.0036252 | chromosome 9 open reading frame 140 |
| SCFD2 | 2.68 | 2.189 | 2.795 | 5.841 | 5.609 | 5.758 | 8.445 | 0.0001037 | sed family domain containing 2 |
| SLPI | 3.645 | 1.547 | 0.162 | 4.018 | 5.164 | 4.648 | 8.579 | 0.0077234 | secretory leukocyte peptidase inhibitor |
| C2orf82 | 0.403 | 0.607 | 1.715 | 3.511 | 4.355 | 4.186 | 8.62 | 0.0003642 | chromosome 2 open reading frame 82 |
| PAX4 | −0.104 | −0.258 | −0.012 | 3.045 | 3.247 | 2.73 | 8.868 | 0.0000894 | paired box4 |
| C4orf40 | −0.904 | −0.529 | 0.16 | 2.048 | 2.987 | 3.309 | 8.871 | 0.0003284 | chromosome 4 open reading frame 40 |
| SRL | 3.686 | 1.228 | 1.674 | 5.842 | 4.874 | 4.763 | 9.188 | 0.0026923 | sarcalumenin |
| GOLGA6L1 | −0.648 | −0.177 | 2.241 | 2.901 | 3.025 | 3.412 | 9.202 | 0.0062982 | golgin A6 family-like 1 |
| MIR886 | 2.132 | 2.102 | 0.224 | 3.948 | 5.195 | 5.342 | 9.251 | 0.0010947 | No description |
| CTSL2 | 4.54 | 4.616 | 4.838 | 5.317 | 8.233 | 7.837 | 9.321 | 0.0091057 | cathepsin L2 |
| PHLDA2 | 8.598 | 7.122 | 6.049 | 10.47 | 10.352 | 10.321 | 9.382 | 0.0014002 | pleckstrin homology-like domain, family A, member 2 |
| KISS1 | −0.192 | −0.887 | −1.775 | 3.081 | 2.142 | 1.908 | 9.666 | 0.0004286 | KiSS-1 metastasis-suppressor |
| MMP7 | 0.625 | 4.235 | 1.618 | 3.941 | 5.521 | 5.246 | 9.957 | 0.0124483 | matrix metallopeptidase 7 (matrilysin, uterine) |

TABLE 6-continued

Differentially Expressed Genes in CD10+ Breast Epithelial Cells

| | Nulliparous (NP) Samples | | | Parous (P) Samples | | | | | |
|---|---|---|---|---|---|---|---|---|---|
| Gene Symbol | CD24+ N48 | CD24+ N58 | CD24+ N43 | CD24+ N37 | CD24+ N39 | CD24+ N40 | Pseudo fold change | P value | Gene description |
| SAA4 | 1.275 | 0.886 | 2.817 | 4.593 | 5.075 | 4.474 | 9.975 | 0.0008521 | serum amyloid A4, constitutive |
| HIST1H4L | 3.248 | 0.251 | 1.247 | 3.644 | 5.016 | 4.675 | 10.505 | 0.0053209 | histone cluster 1, H4l |
| GABRP | 1.763 | 1.762 | 2.073 | 3.791 | 5.876 | 5.188 | 10.738 | 0.0008013 | gamma-aminobutyric acid (GABA) A receptor, pi |
| SERPINC1 | 2.495 | −0.046 | 0.422 | 3.379 | 4.542 | 3.904 | 10.743 | 0.0028654 | serpin peptidase inhibitor, clade C (antithrombin), member 1 |
| OLFM4 | 1.388 | 2.061 | 1.483 | 3.182 | 5.508 | 5.288 | 10.906 | 0.0019418 | olfactomedin 4 |
| PINX1 | 2.398 | 3.094 | 2.348 | 6.625 | 5.779 | 6.329 | 11.557 | 0.0001252 | PIN2/TERF1 interacting, telomerase inhibitor 1 |
| PITX1 | 1.386 | 1.72 | 1.602 | 5.299 | 5.148 | 4.505 | 11.68 | 0.0001109 | paired-like homeodomain 1 |
| EFNA2 | 1.341 | −1.775 | −0.904 | 2.704 | 2.142 | 2.651 | 11.753 | 0.0042856 | ephrin-A2 |
| CCL20 | 1.714 | 2.455 | 3.84 | 6.084 | 6.09 | 6.143 | 12.42 | 0.0004429 | chemokine (C-C motif) ligand 20 |
| ST20 | 2.945 | −0.177 | 1.148 | 4.824 | 4.999 | 4.713 | 12.783 | 0.0015039 | suppressor of tumorigenicity 20 |
| DEFB1 | −1.775 | −1.775 | −0.904 | 2.437 | 1.527 | 2.819 | 13.204 | 0.0001782 | defensin, beta 1 |
| SAA1 | 10.069 | 7.303 | 10.989 | 13.808 | 13.834 | 13.704 | 13.351 | 0.0009952 | serum amyloid A1 |
| WFDC2 | 6.61 | 4.66 | 5.087 | 9.038 | 8.968 | 8.517 | 14.491 | 0.0004643 | WAP four-disulfide core domain 2 |
| HPDL | 3.114 | −0.887 | 1.494 | 5.908 | 5.566 | 5.088 | 16.818 | 0.0014424 | 4-hydroxyphenylpyruvate dioxygenase-like |
| BCL11B | 1.806 | 2.141 | 1.879 | 3.619 | 6.354 | 5.988 | 17.253 | 0.0016112 | B-cell CLL/lymphoma 11B (zinc finger protein) |
| IQCF1 | −0.648 | 0.251 | −1.493 | 3.204 | 4.397 | 3.336 | 17.708 | 0.0001853 | IQ motif containing F1 |
| C21orf121 | −1.775 | −1.775 | 2.834 | 4.198 | 2.39 | 4.155 | 17.937 | 0.008607 | chromosome 21 open reading frame 121 |
| EPR1 | 4.224 | 2.102 | −1.775 | 6.277 | 6.395 | 5.49 | 18.057 | 0.0049846 | effector cell peptidase receptor 1 (non-protein coding) |
| PI3 | 1.275 | 1.044 | 1.219 | 5.305 | 6.038 | 5.364 | 19.165 | 0.0000751 | peptidase inhibitor 3, skin-derived |
| LTF | 1.939 | 2.431 | 1.342 | 4.314 | 7.062 | 6.408 | 22.146 | 0.0006167 | lactotransferrin |
| SAA2 | 4.018 | 2.008 | 3.561 | 6.978 | 8.546 | 7.98 | 23.067 | 0.0002096 | serum amyloid A2 |
| HIST1H2BK | 1.874 | 1.959 | 0.978 | 5.718 | 7.257 | 6.486 | 26.716 | 0.0000966 | histone cluster 1, H2bk |
| IGLL1 | −0.904 | −0.258 | −0.274 | −0.311 | 5.475 | 4.623 | 29.796 | 0.0136481 | immunoglobulin lambda-like polypeptide 1 |
| GSTT1 | 0.68 | 0.834 | 5.638 | 6.459 | 5.979 | 6.367 | 39.354 | 0.0077163 | glutathione S-transferase theta 1 |
| ESR2 | −0.264 | −0.046 | 4.539 | 6.365 | 5.571 | 8.985 | 57.055 | 0.002248 | estrogen receptor 2 (ER beta) |
| RBP4 | 2.439 | −1.775 | −0.904 | 4.939 | 5.016 | 4.562 | 57.368 | 0.0009165 | retinol binding protein 4, plasma |
| KRTAP2-4 | 4.991 | 2.17 | 3.451 | 9.151 | 10.712 | 10 | 93.615 | 0.0001181 | keratin associated protein 2-4 |

TABLE 7

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| Higher Expression in Nulliparous | | | | | | | | | |
| CIB1 | 8.918 | 0.751 | 7.453 | 0.751 | 0.751 | 0.751 | −104.129 | 0.0263699 | calcium and integrin binding 1 (calmyrin) |
| RELL2 | 4.528 | 4.664 | 4.128 | 3.848 | −0.834 | −0.834 | −31.160 | 0.0174792 | RELT-like 2 |
| COL1A1 | 13.613 | 10.721 | 10.752 | 5.932 | 7.368 | 6.175 | −27.644 | 0.0005223 | collagen, type I, alpha 1 |
| CACNA1D | 6.820 | 7.844 | 6.850 | 2.166 | 2.166 | 6.722 | −25.177 | 0.0223877 | calcium channel, voltage-dependent, L type, alpha 1D subunit |
| FAM43B | 6.144 | 6.144 | 4.173 | 1.588 | 0.951 | 0.166 | −23.522 | 0.0002856 | family with sequence similarity 43, member B |
| C15orf48 | 5.915 | 6.941 | 4.306 | 5.421 | 0.166 | 0.166 | −17.626 | 0.0311312 | chromosome 15 open reading frame 48 |
| WFIKKN1 | 4.894 | 4.917 | 4.820 | 4.226 | 0.751 | 0.751 | −16.783 | 0.0171827 | WAP, follistatin/kazal, immunoglobulin, kunitz and netrin domain containing 1 |
| PI16 | 10.217 | 10.615 | 11.238 | 6.113 | 7.173 | 6.622 | −16.742 | 0.0001532 | peptidase inhibitor 16 |
| FREM1 | 8.554 | 5.952 | 6.788 | 2.488 | 4.581 | 2.488 | −15.700 | 0.0023521 | FRAS1 related extracellular matrix 1 |
| LIPC | 3.293 | 5.446 | 2.969 | −0.834 | 1.493 | −0.834 | −15.495 | 0.0027757 | lipase, hepatic |
| LEPREL2 | 9.489 | 9.413 | 7.569 | 6.776 | 5.483 | 3.556 | −15.242 | 0.0061184 | leprecan-like 2 |
| COL1A2 | 12.960 | 11.062 | 12.216 | 7.421 | 9.076 | 7.523 | −14.763 | 0.0006199 | collagen, type I, alpha 2 |
| CCDC74A | 2.837 | 3.050 | 3.281 | −0.834 | −0.834 | −0.834 | −14.760 | 0.0000889 | coiled-coil domain containing 74A |
| HAS1 | 7.726 | 9.916 | 9.883 | 5.326 | 6.063 | 5.345 | −14.447 | 0.0013325 | hyaluronan synthase 1 |
| SPSB4 | 5.062 | 4.607 | 4.519 | 0.751 | 1.318 | 0.751 | −13.624 | 0.0001116 | splA/ryanodine receptor domain and SOCS box containing 4 |
| FIGF | 8.629 | 6.223 | 5.755 | 2.471 | 2.166 | 3.072 | −13.476 | 0.0010201 | c-fos induced growth factor (vascular endothelial growth factor D) |
| RCC2 | 11.023 | 9.918 | 9.399 | 6.241 | 7.904 | 5.453 | −12.791 | 0.0019573 | regulator of chromosome condensation 2 |
| LASS1 | 5.538 | 3.727 | 3.179 | 1.290 | 1.888 | −0.834 | −12.550 | 0.0072008 | LAG1 homolog, ceramide synthase 1 |
| CCL26 | 3.782 | 4.890 | 6.463 | 0.166 | 3.944 | 0.166 | −12.262 | 0.0160079 | chemokine (C-C motif) ligand 26 |
| ARHGEF10L | 7.126 | 9.060 | 8.778 | 4.560 | 6.872 | 3.558 | −11.858 | 0.0094300 | Rho guanine nucleotide exchange factor (GEF) 10-like |
| HIC1 | 8.486 | 9.372 | 8.899 | 5.354 | 6.766 | 4.968 | −11.453 | 0.0011229 | hypermethylated in cancer 1 |
| EN1 | 4.282 | 5.068 | 5.775 | 1.588 | 3.098 | 0.166 | −11.161 | 0.0037266 | engrailed homeobox 1 |
| GPRC5A | 9.571 | 11.352 | 10.095 | 8.432 | 6.646 | 5.332 | −10.916 | 0.0046290 | G protein-coupled receptor, family C, group 5, member A |
| MATK | 0.456 | 2.614 | 3.736 | −0.834 | −0.834 | −0.834 | −10.913 | 0.0069936 | megakaryocyte-associated tyrosine kinase |
| LOC390595 | 4.176 | 4.185 | 4.348 | 0.751 | 3.995 | 0.751 | −10.737 | 0.0342742 | No description |
| CPZ | 9.019 | 8.062 | 8.273 | 5.363 | 5.628 | 4.071 | −10.488 | 0.0005745 | carboxypeptidase Z |
| TIMP1 | 11.217 | 10.873 | 12.597 | 11.095 | 7.732 | 7.533 | −10.129 | 0.0306380 | TIMP metallopeptidase inhibitor 1 |
| CYP2E1 | 3.179 | 2.837 | 2.503 | 0.692 | −0.834 | −0.834 | −10.104 | 0.0009210 | cytochrome P450, family 2, subfamily E, polypeptide 1 |
| RTN2 | 3.793 | 5.236 | 4.414 | 1.122 | 3.782 | 0.166 | −9.795 | 0.0226464 | reticulon 2 |
| RCVRN | 6.714 | 5.727 | 5.194 | 2.817 | 1.951 | 2.625 | −9.468 | 0.0004731 | recoverin |
| ECEL1 | 9.036 | 4.888 | 5.727 | 2.488 | 3.950 | 2.488 | −9.442 | 0.0120427 | endothelin converting enzyme-like 1 |
| PROK2 | 4.718 | 2.722 | 5.067 | 1.835 | 0.751 | 0.751 | −9.397 | 0.0040427 | prokineticin 2 |
| PITX3 | 5.566 | 5.660 | 4.145 | 2.335 | 3.098 | 0.166 | −9.391 | 0.0063741 | paired-like homeodomain 3 |
| UTP18 | 5.391 | 7.936 | 7.825 | 5.861 | 4.611 | 2.166 | −9.278 | 0.0348007 | UTP18, small subunit (SSU) processome component, homolog (yeast) |
| DPP4 | 6.285 | 6.959 | 7.005 | 5.620 | 3.627 | 3.072 | −9.270 | 0.0088567 | dipeptidyl-peptidase 4 |
| C15orf59 | 6.065 | 5.863 | 5.729 | 2.656 | 4.217 | 1.751 | −9.231 | 0.0027530 | chromosome 15 open reading frame 59 |
| COL14A1 | 9.737 | 7.810 | 8.634 | 6.310 | 5.432 | 5.259 | −9.198 | 0.0017417 | collagen, type XIV, alpha 1 |
| MFAP5 | 6.962 | 7.391 | 9.341 | 3.030 | 6.147 | 4.683 | −9.155 | 0.0103793 | microfibrillar associated protein 5 |
| CPXM1 | 12.482 | 11.393 | 10.357 | 9.266 | 8.214 | 8.136 | −9.052 | 0.0035246 | carboxypeptidase X (M14 family), member 1 |
| NAPSB | 0.951 | 3.330 | 3.851 | 0.166 | 0.166 | 0.166 | −8.963 | 0.0151486 | napsin B aspartic peptidase pseudogene |
| BAI2 | 8.195 | 5.627 | 4.428 | 2.488 | 3.380 | 2.488 | −8.809 | 0.0097901 | brain-specific angiogenesis inhibitor 2 |
| THBS3 | 7.590 | 9.026 | 8.068 | 4.323 | 6.679 | 4.952 | −8.668 | 0.0055344 | thrombospondin 3 |

TABLE 7-continued

Differentially Exprssed Genes in Stromal Breast Epithelial Cells

| | Nulliparous (NP) Samples | | | Parous (P) Samples | | | Pseudo | | |
| --- | --- | --- | --- | --- | --- | --- | --- | --- | --- |
| Gene Symbol | Stroma N33 | Stroma N35 | Stroma N58 | Stroma N37 | Stroma N39 | Stroma N40 | fold change | P value | Gene description |
| MYOC | 2.764 | 5.590 | 7.336 | 2.487 | 2.857 | 0.751 | −8.593 | 0.0274240 | myocilin, trabecular meshwork inducible glucocorticoid response |
| FAM159A | 4.573 | 2.567 | 3.266 | 1.122 | 0.166 | 0.166 | −8.570 | 0.0022213 | family with sequence similarity 159, member A |
| ABTB2 | 8.322 | 9.212 | 9.342 | 6.250 | 6.134 | 4.146 | −8.527 | 0.0015473 | ankyrin repeat and BTB (POZ) domain containing 2 |
| DNM1 | 9.521 | 8.760 | 7.786 | 4.697 | 7.313 | 5.028 | −8.506 | 0.0083188 | dynamin 1 |
| FZD1 | 7.300 | 5.233 | 5.578 | 3.368 | 4.184 | 2.166 | −8.381 | 0.0084376 | frizzled homolog 1 (Drosophila) |
| CFD | 13.706 | 18.067 | 16.205 | 12.861 | 13.235 | 13.143 | −8.347 | 0.0249210 | complement factor D (adipsin) |
| CMA1 | 1.355 | 2.222 | 3.075 | −0.834 | −0.834 | −0.834 | −8.317 | 0.0008302 | chymase 1, mast cell |
| CD300A | 0.456 | 2.222 | 2.837 | −0.834 | −0.834 | −0.834 | −8.317 | 0.0054315 | CD300a molecule |
| CXXC5 | 9.732 | 9.471 | 6.781 | 6.432 | 6.158 | 6.656 | −8.218 | 0.0317568 | CXXC finger protein 5 |
| LOC389634 | 4.528 | 4.975 | 2.723 | −0.834 | 1.493 | 2.165 | −8.202 | 0.0122719 | No description |
| HPSE2 | 8.267 | 6.618 | 5.653 | 4.282 | 3.583 | 3.253 | −8.198 | 0.0035132 | heparanase 2 |
| ARTN | 4.354 | 5.631 | 3.455 | 2.609 | 2.092 | 0.166 | −8.121 | 0.0112129 | artemin |
| PTK7 | 10.583 | 9.568 | 7.665 | 7.394 | 6.232 | 6.548 | −8.113 | 0.0167530 | PTK7 protein tyrosine kinase 7 |
| LMNA | 13.507 | 13.627 | 13.216 | 10.488 | 9.100 | 11.615 | −8.102 | 0.0027001 | lamin A/C |
| C16orf93 | 3.168 | 3.389 | 2.861 | 0.166 | 0.166 | 0.166 | −8.011 | 0.0001229 | chromosome 16 open reading frame 93 |
| SOX5 | 6.113 | 6.794 | 4.424 | 3.111 | 2.928 | 3.333 | −8.009 | 0.0056933 | SRY (sex determining region Y)-box 5 |
| ECM1 | 10.046 | 10.838 | 10.912 | 9.039 | 7.467 | 7.048 | −7.986 | 0.0035548 | extracellular matrix protein 1 |
| FNDC1 | 8.211 | 7.114 | 5.939 | 4.142 | 4.120 | 4.071 | −7.968 | 0.0020526 | fibronectin type III domain containing 1 |
| ADORA2B | 3.903 | 3.144 | 3.164 | 0.166 | 2.092 | 0.166 | −7.880 | 0.0056592 | adenosine A2b receptor |
| EMILIN1 | 8.546 | 7.575 | 7.185 | 6.035 | 4.616 | 3.623 | −7.779 | 0.0043400 | elastin microfibril interfacer 1 |
| GADD45G | 6.611 | 7.312 | 7.747 | 4.850 | 3.661 | 3.960 | −7.728 | 0.0007266 | growth arrest and DNA-damage-inducible, gamma |
| CXCL14 | 6.966 | 9.492 | 10.357 | 4.101 | 7.369 | 6.559 | −7.636 | 0.0340541 | chemokine (C-X-C motif) ligand 14 |
| MEG3 | 13.477 | 13.408 | 14.632 | 11.318 | 11.709 | 10.177 | −7.582 | 0.0024013 | maternally expressed 3 (non-protein coding) |
| WNT6 | 5.964 | 3.795 | 3.069 | 1.122 | 2.946 | 0.166 | −7.480 | 0.0220359 | wingless-type MMTV integration site family, member 6 |
| MRC2 | 10.029 | 10.282 | 10.299 | 7.617 | 7.380 | 7.053 | −7.477 | 0.0001834 | mannose receptor, C type 2 |
| XPNPEP2 | 4.059 | 4.873 | 6.008 | 1.974 | 2.821 | 1.974 | −7.460 | 0.0030458 | X-prolyl aminopeptidase (aminopeptidase P) 2, membrane-bound |
| ARC | 10.064 | 11.106 | 12.064 | 8.135 | 8.213 | 8.393 | −7.426 | 0.0018635 | activity-regulated cytoskeleton-associated protein |
| CNN1 | 8.806 | 7.865 | 7.619 | 5.160 | 5.920 | 4.404 | −7.393 | 0.0014648 | calponin 1, basic, smooth muscle |
| WNT2 | 7.669 | 5.577 | 4.858 | 3.680 | 2.821 | 1.974 | −7.385 | 0.0061486 | wingless-type MMTV integration site family member 2 |
| TMEM98 | 9.727 | 7.936 | 7.091 | 5.219 | 4.217 | 5.448 | −7.328 | 0.0031978 | transmembrane protein 98 |
| IFT172 | 5.845 | 5.843 | 5.560 | 2.973 | 2.244 | 4.843 | −7.310 | 0.0131554 | intraflagellar transport 172 homolog (Chlamydomonas) |
| ELN | 12.244 | 10.753 | 9.930 | 7.460 | 7.382 | 9.382 | −7.267 | 0.0092871 | elastin |
| DACT3 | 8.467 | 7.539 | 6.111 | 5.618 | 5.061 | 1.751 | −7.203 | 0.0212137 | dapper, antagonist of beta-catenin, homolog 3 (Xenopus laevis) |
| CERCAM | 11.232 | 9.912 | 7.728 | 7.230 | 7.073 | 6.948 | −7.154 | 0.0232197 | cerebral endothelial cell adhesion molecule |
| TMEM88 | 7.608 | 8.493 | 8.419 | 4.614 | 7.948 | 5.580 | −7.154 | 0.0476108 | transmembrane protein 88 |
| BLK | 3.179 | 1.983 | 2.113 | 2.165 | −0.834 | −0.834 | −7.045 | 0.0418181 | B lymphoid tyrosine kinase |
| NAPSA | 2.745 | 3.965 | 0.692 | −0.834 | 1.161 | −0.834 | −6.981 | 0.0290382 | napsin A aspartic peptidase |
| HMX1 | 2.946 | 4.483 | 3.795 | 2.946 | 0.951 | 0.166 | −6.869 | 0.0234497 | H6 family homeobox 1 |
| COL3A1 | 11.385 | 10.918 | 9.981 | 5.875 | 8.644 | 8.597 | −6.686 | 0.0088983 | collagen, type III, alpha 1 |
| C1QTNF4 | 5.283 | 3.858 | 3.636 | 1.122 | 3.362 | 0.166 | −6.663 | 0.0203113 | C1q and tumor necrosis factor related protein 4 |
| ITIH4 | 4.569 | 4.065 | 4.683 | 1.835 | 1.977 | 0.751 | −6.657 | 0.0006570 | inter-alpha (globulin) inhibitor H4 (plasma Kallikrein-sensitive glycoprotein) |
| SEMA4A | 10.502 | 11.179 | 10.454 | 7.729 | 7.732 | 9.218 | −6.610 | 0.0032969 | sema domain, immunoglobulin domain (Ig), transmembrane domain (TM) and short cytoplasmic domain, (semaphorin) 4A |
| FLNC | 8.741 | 8.647 | 8.304 | 6.043 | 5.922 | 4.557 | −6.608 | 0.0007886 | filamin C, gamma |
| MST1 | 3.941 | 2.969 | 1.888 | −0.834 | −0.834 | 2.165 | −6.597 | 0.0236055 | macrophage stimulating 1 (hepatocyte growth factor-like) |
| FGD1 | 7.389 | 7.322 | 5.800 | 5.763 | 2.488 | 4.601 | −6.592 | 0.0271554 | FYVE, RhoGEF and PH domain containing 1 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| MFGE8 | 10.788 | 10.952 | 10.969 | 8.235 | 10.194 | 7.883 | −6.573 | 0.0181940 | milk fat globule-EGF factor 8 protein |
| HSP90AB1 | 12.181 | 12.296 | 14.984 | 9.581 | 12.701 | 8.810 | −6.567 | 0.0485178 | heat shock protein 90 kDa alpha (cytosolic), class B member 1 |
| SFRP2 | 7.304 | 6.039 | 6.797 | 4.102 | 5.163 | 2.626 | −6.476 | 0.0075927 | secreted frizzled-related protein 2 |
| WISP2 | 5.901 | 8.146 | 9.030 | 3.874 | 6.338 | 5.125 | −6.462 | 0.0324081 | WNT1 inducible signaling pathway protein 2 |
| MMP2 | 12.299 | 11.743 | 11.503 | 11.614 | 9.064 | 6.737 | −6.404 | 0.0468453 | matrix metal lopeptidase 2 (gelatinase A, 72 kDa gelatinase, 72 kDa type IV collagenase) |
| USP2 | 6.132 | 5.982 | 6.696 | 5.275 | 3.460 | 3.253 | −6.374 | 0.0109270 | ubiquitin specific peptidase 2 |
| VCAN | 9.685 | 9.702 | 10.671 | 9.606 | 7.031 | 6.441 | −6.372 | 0.0334444 | versican |
| BDKRB1 | 7.902 | 8.921 | 8.284 | 7.429 | 5.617 | 3.069 | −6.350 | 0.0237984 | bradykinin receptor B1 |
| PRKCG | 3.699 | 4.833 | 6.248 | 2.672 | 2.166 | 2.166 | −6.349 | 0.0078733 | protein kinase C, gamma |
| RAP1GAP | 7.490 | 5.053 | 3.315 | 2.392 | 3.315 | 1.751 | −6.325 | 0.0313306 | RAP1 GTPase activating protein |
| ZFPM1 | 7.532 | 8.620 | 6.500 | 6.709 | 4.571 | 3.842 | −6.312 | 0.0265291 | zinc finger protein, multitype 1 |
| COL16A1 | 10.454 | 9.136 | 9.973 | 7.317 | 6.996 | 7.424 | −6.306 | 0.0011418 | collagen, type XVI, alpha 1 |
| CILP | 10.250 | 11.238 | 11.023 | 8.641 | 7.738 | 7.597 | −6.289 | 0.0008869 | cartilage intermediate layer protein, nucleotide pyrophosphohydrolase |
| SEMA5B | 4.968 | 4.917 | 3.832 | 2.270 | 3.048 | 0.751 | −6.265 | 0.0090980 | sema domain, seven thrombospondin repeats (type 1 and type 1-like), transmembrane domain (TM) and short cytoplasmic domain, (semaphorin) 5B |
| CCDC80 | 11.647 | 12.727 | 12.687 | 9.445 | 11.000 | 9.008 | −6.228 | 0.0067916 | coiled-coil domain containing 80 |
| ERF | 10.371 | 10.555 | 8.974 | 7.442 | 7.091 | 7.928 | −6.179 | 0.0035019 | Ets2 repressor factor |
| PCOLCE | 8.738 | 7.363 | 7.122 | 5.819 | 5.226 | 4.497 | −6.169 | 0.0046403 | procollagen C-endopeptidase enhancer |
| COL5A1 | 11.329 | 8.614 | 8.102 | 5.479 | 6.630 | 6.150 | −6.158 | 0.0075095 | collagen, type V, alpha 1 |
| FSTL1 | 13.159 | 11.426 | 12.792 | 9.806 | 10.538 | 9.295 | −6.150 | 0.0045972 | follistatin-like 1 |
| MAPKAPK2 | 13.745 | 13.653 | 11.924 | 10.918 | 11.016 | 11.137 | −6.096 | 0.0115216 | mitogen-activated protein kinase-activated protein kinase 2 |
| HTRA3 | 5.938 | 7.304 | 5.967 | 4.000 | 3.447 | 3.336 | −6.073 | 0.0012765 | HtrA serine peptidase 3 |
| ACP5 | 7.749 | 7.731 | 7.559 | 4.999 | 5.122 | 6.968 | −5.898 | 0.0182129 | acid phosphatase 5, tartrate resistant |
| BICD1 | 4.304 | 3.069 | 2.946 | 1.588 | 1.755 | 0.166 | −5.854 | 0.0102674 | bicaudal D homolog 1 (Drosophila) |
| RAET1G | 3.709 | 3.736 | 2.414 | 2.165 | 1.161 | −0.834 | −5.848 | 0.0237666 | retinoic acid early transcript 1G |
| FAM180B | 5.482 | 7.637 | 5.711 | 2.946 | 3.168 | 3.456 | −5.826 | 0.0020866 | family with sequence similarity 180, member B |
| SOX8 | 7.577 | 7.608 | 7.511 | 5.044 | 4.805 | 5.577 | −5.786 | 0.0004353 | SRY (sex determining region Y)-box 8 |
| BGN | 10.733 | 10.661 | 10.861 | 7.913 | 8.674 | 8.203 | −5.776 | 0.0003340 | biglycan |
| LTBP3 | 12.203 | 11.997 | 10.665 | 9.190 | 9.383 | 9.677 | −5.760 | 0.0052039 | latent transforming growth factor beta binding protein 3 |
| OSR1 | 7.786 | 8.105 | 7.910 | 7.751 | 5.390 | 3.852 | −5.735 | 0.0484172 | odd-skipped related 1 (Drosophila) |
| SFRP4 | 12.765 | 12.325 | 11.074 | 10.941 | 9.482 | 8.588 | −5.602 | 0.0177334 | secreted frizzled-related protein 4 |
| PCDH7 | 6.088 | 4.819 | 4.073 | 3.576 | 2.334 | 1.751 | −5.598 | 0.0127682 | protocadherin 7 |
| CLEC11A | 5.894 | 5.966 | 5.606 | 3.412 | 3.757 | 1.488 | −5.586 | 0.0030193 | C-type lectin domain family 11, member A |
| ZNF574 | 5.608 | 5.970 | 5.566 | 4.337 | 3.126 | 1.974 | −5.585 | 0.0062197 | zinc finger protein 574 |
| BHLHE40 | 13.832 | 14.127 | 12.890 | 11.649 | 10.762 | 10.966 | −5.569 | 0.0018892 | basic helix-loop-helix family, member e40 |
| HBB | 8.833 | 9.189 | 13.402 | 6.357 | 8.229 | 7.760 | −5.566 | 0.0408075 | hemoglobin, beta |
| COL9A3 | 8.069 | 4.616 | 4.978 | 2.144 | 3.315 | 2.866 | −5.545 | 0.0132190 | collagen, type IX, alpha 3 |
| SLC25A44 | 9.088 | 9.707 | 10.072 | 6.637 | 8.712 | 6.618 | −5.541 | 0.0143045 | solute carrier family 25, member 44 |
| ZNF503 | 6.661 | 6.833 | 8.813 | 5.902 | 6.023 | 4.199 | −5.508 | 0.0384452 | zinc finger protein 503 |
| SCO2 | 7.667 | 8.821 | 8.979 | 6.568 | 4.907 | 6.361 | −5.503 | 0.0056819 | SCO cytochrome oxidase deficient homolog 2 (yeast) |
| LPHN1 | 10.172 | 9.646 | 7.710 | 7.187 | 6.550 | 7.561 | −5.498 | 0.0272598 | latrophilin 1 |
| SULF1 | 7.078 | 7.125 | 8.336 | 4.420 | 5.883 | 5.350 | −5.475 | 0.0068491 | sulfatase 1 |
| CD276 | 10.934 | 9.392 | 10.543 | 8.489 | 8.353 | 5.664 | −5.447 | 0.0156169 | CD276 molecule |
| RELT | 6.300 | 7.620 | 6.272 | 5.178 | 4.541 | 2.336 | −5.435 | 0.0144308 | RELT tumor necrosis factor receptor |
| CBX8 | 5.137 | 4.711 | 4.678 | 2.698 | 2.487 | 0.751 | −5.425 | 0.0023151 | chromobox homolog 8 |
| MARCKSL1 | 8.607 | 8.635 | 8.585 | 6.168 | 6.502 | 4.666 | −5.422 | 0.0017530 | MARCKS-like 1 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| MXRA8 | 10.621 | 11.069 | 10.886 | 6.260 | 9.562 | 8.451 | −5.410 | 0.0135594 | matrix-remodelling associated 8 |
| CTHRC1 | 7.154 | 7.569 | 8.036 | 5.237 | 5.607 | 3.528 | −5.384 | 0.0036418 | collagen triple helix repeat containing 1 |
| SH3GL3 | 4.401 | 4.380 | 2.270 | 1.453 | 1.977 | 0.751 | −5.368 | 0.0170760 | SH3-domain GRB2-like 3 |
| SELP | 7.786 | 9.421 | 8.837 | 5.999 | 5.362 | 8.089 | −5.368 | 0.0342629 | selectin P (granule membrane protein 140 kDa, antigen CD62) |
| APOE | 14.930 | 14.604 | 13.036 | 11.108 | 12.186 | 12.268 | −5.346 | 0.0101449 | apolipoprotein E |
| BST1 | 4.248 | 5.153 | 5.916 | 1.835 | 4.726 | 2.487 | −5.329 | 0.0468680 | bone marrow stromal cell antigen 1 |
| SELE | 4.163 | 5.887 | 6.860 | 4.276 | 3.480 | 3.254 | −5.304 | 0.0386774 | selectin E |
| PTPRN | 7.450 | 4.379 | 4.151 | 2.539 | 1.974 | 1.974 | −5.299 | 0.0095443 | protein tyrosine phosphatase, receptor type, N |
| COL18A1 | 9.870 | 9.350 | 9.512 | 8.350 | 6.292 | 7.112 | −5.279 | 0.0072515 | collagen, type XVIII, alpha 1 |
| CPSF7 | 8.886 | 8.924 | 9.494 | 7.726 | 6.368 | 6.529 | −5.262 | 0.0039694 | cleavage and polyadenylation specific factor 7, 59 kDa |
| SNORD10 | 3.075 | 2.745 | 4.264 | 0.692 | 3.075 | −0.834 | −5.216 | 0.0494784 | small nucleolar RNA, C/D box 10 |
| LCNL1 | 1.880 | 3.352 | 3.134 | 0.751 | 0.751 | 0.751 | −5.216 | 0.0062477 | lipocalin-like 1 |
| RASL10A | 6.272 | 5.248 | 3.669 | 2.702 | 2.866 | 3.411 | −5.214 | 0.0259747 | RAS-like, family 10, member A |
| FBLN1 | 12.263 | 12.006 | 12.396 | 10.835 | 9.883 | 8.808 | −5.207 | 0.0057538 | fibulin 1 |
| BCL9L | 11.205 | 10.928 | 8.987 | 8.856 | 8.142 | 7.853 | −5.096 | 0.0227939 | B-cell CLL/lymphoma 9-like |
| MICALL2 | 5.742 | 6.452 | 5.902 | 3.966 | 4.108 | 2.751 | −5.076 | 0.0025049 | MICAL-like 2 |
| UCN2 | 5.381 | 3.972 | 4.292 | 1.949 | 3.357 | 1.488 | −5.074 | 0.0120163 | urocortin 2 |
| PODN | 11.171 | 11.247 | 10.419 | 8.892 | 8.733 | 8.829 | −5.068 | 0.0012992 | podocan |
| AHDC1 | 8.736 | 9.196 | 7.039 | 6.795 | 6.400 | 5.502 | −5.049 | 0.0227598 | AT hook, DNA binding motif, containing 1 |
| CHKB | 6.144 | 6.118 | 6.812 | 4.069 | 3.782 | 4.072 | −5.049 | 0.0005337 | choline kinase beta |
| CHRD | 8.599 | 9.242 | 8.286 | 6.266 | 6.965 | 5.662 | −5.037 | 0.0023824 | chordin |
| NTN5 | 5.472 | 4.853 | 3.250 | 1.722 | 3.142 | 1.166 | −5.028 | 0.0156479 | netrin 5 |
| PITPNM3 | 6.751 | 5.196 | 3.440 | 3.061 | 2.702 | 2.866 | −5.027 | 0.0319996 | PITPNM family member 3 |
| SLC26A10 | 6.765 | 5.359 | 5.076 | 4.203 | 3.030 | 2.866 | −5.024 | 0.0086244 | solute carrier family 26, member 10 |
| WDR52 | 8.249 | 7.333 | 6.939 | 5.109 | 4.365 | 5.923 | −5.012 | 0.0057387 | WD repeat domain 52 |
| FAM46A | 9.929 | 8.424 | 10.218 | 8.616 | 7.606 | 5.418 | −5.004 | 0.0409754 | family with sequence similarity 46, member A |
| CSF1 | 8.358 | 8.450 | 7.618 | 7.024 | 5.362 | 5.296 | −5.000 | 0.0090110 | colony stimulating factor 1 (macrophage) |
| ABCA6 | 4.023 | 5.075 | 6.111 | 2.931 | 2.753 | 2.166 | −4.999 | 0.0063098 | ATP-binding cassette, sub-family A (ABC1), member 6 |
| GALNTL1 | 7.377 | 6.100 | 4.230 | 3.784 | 3.784 | 3.485 | −4.981 | 0.0299573 | UDP-N-acetyl-alpha-D-galactosamine:polypeptide N-acetylgalactosaminyltransferase-like 1 |
| GPNMB | 9.337 | 10.647 | 10.157 | 8.339 | 7.832 | 7.059 | −4.954 | 0.0049512 | glycoprotein (transmembrane) nmb |
| EMP3 | 9.508 | 10.637 | 10.771 | 9.041 | 8.330 | 6.899 | −4.950 | 0.0168468 | epithelial membrane protein 3 |
| AEBP1 | 6.653 | 7.033 | 5.897 | 4.825 | 4.353 | 3.336 | −4.924 | 0.0048196 | AE binding protein 1 |
| DYRK2 | 6.957 | 6.628 | 6.740 | 6.004 | 4.442 | 3.919 | −4.918 | 0.0175662 | dual-s pecificity tyrosine-(Y)-phosphorylation regulated kinase 2 |
| SLC7A3 | 5.963 | 3.048 | 3.048 | 0.751 | 1.318 | 0.751 | −4.913 | 0.0081199 | solute carrier family 7 (cationic amino acid transporter, y+ system), member 3 |
| C11orf9 | 4.522 | 4.057 | 3.145 | 2.229 | 1.488 | 1.488 | −4.899 | 0.0047878 | chromosome 11 open reading frame 9 |
| HSPB8 | 6.654 | 6.913 | 8.729 | 4.526 | 6.301 | 4.624 | −4.884 | 0.0229013 | heat shock 22 kDa protein 8 |
| TMEM63B | 9.852 | 10.514 | 9.074 | 7.716 | 7.564 | 6.976 | −4.884 | 0.0025390 | transmembrane protein 63B |
| APOC1 | 11.023 | 11.789 | 10.004 | 7.600 | 8.743 | 9.825 | −4.856 | 0.0222402 | apolipoprotein C-I |
| SGMS2 | 5.393 | 5.647 | 7.345 | 4.146 | 5.066 | 2.974 | −4.851 | 0.0336207 | sphingomyelin synthase 2 |
| CREB3L1 | 7.095 | 6.860 | 6.455 | 5.245 | 4.588 | 2.867 | −4.830 | 0.0073975 | cAMP responsive element binding protein 3-like 1 |
| SLC38A5 | 6.547 | 5.023 | 6.447 | 3.652 | 4.392 | 2.751 | −4.828 | 0.0084225 | solute carrier family 38, member 5 |
| WDR86 | 7.421 | 7.427 | 4.581 | 2.911 | 5.158 | 4.119 | −4.820 | 0.0394769 | WD repeat domain 86 |
| NGFR | 7.023 | 7.135 | 6.762 | 3.920 | 5.195 | 4.755 | −4.819 | 0.0017114 | nerve growth factor receptor |
| AKAP13 | 8.933 | 9.648 | 10.569 | 8.549 | 7.193 | 6.668 | −4.806 | 0.0149686 | A kinase (PRKA) anchor protein 13 |
| PVRL1 | 8.826 | 9.526 | 8.196 | 7.266 | 6.525 | 6.386 | −4.792 | 0.0053151 | poliovirus receptor-related 1 (herpesvirus entry mediator C) |
| MYO15B | 9.286 | 8.727 | 7.944 | 5.433 | 6.963 | 7.025 | −4.792 | 0.0118831 | myosin XVB pseudogene |
| ETV5 | 6.412 | 5.000 | 5.733 | 3.107 | 4.745 | 2.751 | −4.752 | 0.0174565 | ets variant 5 |
| CLCN7 | 7.313 | 8.217 | 8.684 | 5.971 | 7.529 | 3.751 | −4.743 | 0.0478741 | chloride channel 7 |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| LOXL1 | 8.421 | 6.301 | 7.060 | 5.701 | 4.140 | 4.817 | −4.735 | 0.0130654 | lysyl oxidase-like 1 |
| MUSTN1 | 5.070 | 5.842 | 5.312 | 2.799 | 4.695 | 3.069 | −4.734 | 0.0221494 | musculoskeletal, embryonic nuclear protein 1 |
| UBASH3B | 8.060 | 8.264 | 8.413 | 6.024 | 6.323 | 3.751 | −4.726 | 0.0058612 | ubiquitin associated and SH3 domain containing B |
| SMO | 5.899 | 4.380 | 4.862 | 2.626 | 3.219 | 2.626 | −4.711 | 0.0046176 | smoothened homolog (Drosophila) |
| GLT25D2 | 5.161 | 4.580 | 4.943 | 2.928 | 2.750 | 1.488 | −4.703 | 0.0020753 | glycosyltransferase 25 domain containing 2 |
| HMOX1 | 13.282 | 15.360 | 14.604 | 11.923 | 13.128 | 12.011 | −4.697 | 0.0207697 | heme oxygenase (decycling) 1 |
| FNIP2 | 7.887 | 8.790 | 9.738 | 7.396 | 6.454 | 6.563 | −4.683 | 0.0154852 | folliculin interacting protein 2 |
| ATP10A | 5.921 | 6.141 | 7.046 | 4.385 | 4.827 | 3.166 | −4.655 | 0.0082924 | ATPase, class V, type 10A |
| IER3 | 13.332 | 14.070 | 12.999 | 12.699 | 11.114 | 9.490 | −4.653 | 0.0272485 | immediate early response 3 |
| NECAB2 | 3.913 | 3.409 | 2.968 | 2.487 | 0.751 | 0.751 | −4.649 | 0.0137954 | N-terminal EF-hand calcium binding protein 2 |
| CACNA2D2 | 3.777 | 4.276 | 3.705 | 1.488 | 3.416 | 1.488 | −4.649 | 0.0315390 | calcium channel, voltage-dependent, alpha 2/delta subunit 2 |
| REEP5 | 7.971 | 7.863 | 9.110 | 5.756 | 7.692 | 4.865 | −4.642 | 0.0311199 | receptor accessory protein 5 |
| OLFML3 | 6.578 | 4.770 | 5.564 | 3.404 | 4.364 | 2.488 | −4.641 | 0.0171214 | olfactomedin-like 3 |
| STMN3 | 8.981 | 9.216 | 8.535 | 6.941 | 6.332 | 6.768 | −4.637 | 0.0010654 | stathmin-like 3 |
| PYGO1 | 4.190 | 4.323 | 3.256 | 2.911 | 1.977 | 0.751 | −4.636 | 0.0207167 | pygopus homolog 1 (Drosophila) |
| SPON2 | 10.831 | 10.397 | 10.225 | 9.689 | 8.014 | 8.080 | −4.631 | 0.0172160 | spondin 2, extracellular matrix protein |
| RABGEF1 | 10.561 | 9.926 | 9.736 | 8.362 | 7.824 | 6.705 | −4.592 | 0.0036812 | RAB guanine nucleotide exchange factor (GEF) 1 |
| CPEB1 | 5.919 | 6.994 | 5.361 | 4.801 | 4.217 | 1.751 | −4.571 | 0.0265140 | cytoplasmic polyadenylation element binding protein 1 |
| COL5A2 | 9.041 | 7.943 | 7.971 | 5.753 | 6.500 | 6.148 | −4.562 | 0.0031025 | collagen, type V, alpha 2 |
| RAP1GAP2 | 7.210 | 5.805 | 5.355 | 4.003 | 5.018 | 3.166 | −4.561 | 0.0253990 | RAP1 GTPase activating protein 2 |
| PI4KAP1 | 1.355 | 1.888 | 1.663 | 0.692 | −0.834 | −0.834 | −4.560 | 0.0113446 | phosphatidylinositol 4-kinase, catalytic, alpha pseudogene 1 |
| VGF | 2.067 | 2.424 | 1.355 | −0.834 | 1.161 | −0.834 | −4.560 | 0.0194656 | VGF nerve growth factor inducible |
| ZNF775 | 2.424 | 3.247 | 1.355 | −0.834 | 1.493 | −0.834 | −4.560 | 0.0236282 | zinc finger protein 775 |
| SUSD2 | 5.861 | 4.990 | 4.350 | 3.072 | 3.627 | 2.166 | −4.544 | 0.0115662 | sushi domain containing 2 |
| BMP1 | 9.427 | 8.410 | 8.265 | 7.245 | 6.802 | 4.892 | −4.539 | 0.0150382 | bone morphogenetic protein 1 |
| SPAG7 | 8.035 | 8.789 | 9.325 | 6.607 | 7.524 | 5.251 | −4.539 | 0.0162969 | sperm associated antigen 7 |
| GGT5 | 8.459 | 8.148 | 7.904 | 5.241 | 6.476 | 5.972 | −4.518 | 0.0019868 | gamma-glutamyltransferase 5 |
| C17orf96 | 6.982 | 5.509 | 5.716 | 4.283 | 4.718 | 3.335 | −4.511 | 0.0174247 | chromosome 17 open reading frame 96 |
| NR2E3 | 3.144 | 2.174 | 2.335 | 0.166 | 0.166 | 0.166 | −4.497 | 0.0008983 | nuclear receptor subfamily 2, group E, member 3 |
| C1QL1 | 2.639 | 2.335 | 0.420 | 0.166 | 0.166 | 0.166 | −4.497 | 0.0486827 | complement component 1, q subcomponent-like 1 |
| GATAD2A | 10.421 | 10.363 | 10.052 | 9.091 | 8.197 | 7.876 | −4.488 | 0.0056706 | GATA zinc finger domain containing 2A |
| NT5E | 7.901 | 8.117 | 8.220 | 7.024 | 5.952 | 5.108 | −4.485 | 0.0105306 | 5'-nucleotidase, ecto (CD73) |
| TNFRSF18 | 7.799 | 8.266 | 6.147 | 5.925 | 5.057 | 5.634 | −4.484 | 0.0288952 | tumor necrosis factor receptor superfamily, member 18 |
| AGPAT4 | 7.983 | 8.139 | 7.851 | 6.972 | 5.824 | 5.409 | −4.466 | 0.0093287 | 1-acylglycerol-3-phosphate O-acyltransferase 4 (lysophosphatidic acid acyltransferase, delta) |
| SFRS15 | 7.447 | 7.134 | 7.564 | 6.094 | 5.288 | 4.155 | −4.465 | 0.0079240 | No description |
| APOL4 | 6.238 | 5.639 | 4.610 | 3.394 | 3.752 | 3.485 | −4.448 | 0.0092530 | apolipoprotein L, 4 |
| ZNF408 | 6.983 | 7.160 | 6.937 | 4.833 | 5.965 | 3.558 | −4.440 | 0.0129966 | zinc finger protein 408 |
| ST5 | 7.999 | 8.149 | 8.186 | 5.369 | 7.245 | 5.999 | −4.439 | 0.0148249 | suppression of tumorigenicity 5 |
| PGAM1 | 6.888 | 6.757 | 6.193 | 5.907 | 4.607 | 3.163 | −4.437 | 0.0303597 | phosphoglycerate mutase 1 (brain) |
| RFX2 | 7.649 | 8.190 | 7.556 | 6.046 | 5.913 | 4.899 | −4.421 | 0.0029648 | regulatory factor X, 2 (influences HLA class II expression) |
| SOD3 | 9.931 | 9.849 | 9.058 | 7.709 | 4.199 | 8.776 | −4.408 | 0.0448400 | superoxide dismutase 3, extracellular |
| COL6A2 | 14.769 | 14.954 | 14.199 | 13.232 | 12.451 | 12.060 | −4.405 | 0.0043514 | collagen, type VI, alpha 2 |
| TICAM1 | 6.481 | 7.080 | 7.363 | 4.344 | 5.409 | 4.634 | −4.399 | 0.0029089 | toll-like receptor adaptor molecule 1 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| LTBP1 | 8.799 | 8.538 | 7.900 | 8.053 | 5.765 | 5.968 | −4.394 | 0.0426244 | latent transforming growth factor beta binding protein 1 |
| IL2RB | 1.641 | 3.179 | 4.467 | 2.335 | 0.166 | 0.166 | −4.382 | 0.0481184 | interleukin 2 receptor, beta |
| ITGA11 | 6.090 | 8.113 | 5.954 | 3.608 | 4.357 | 5.987 | −4.366 | 0.0476312 | integrin, alpha 11 |
| SAFB | 5.744 | 5.580 | 7.130 | 5.006 | 4.165 | 3.072 | −4.359 | 0.0226237 | scaffold attachment factor B |
| FAT1 | 8.181 | 8.466 | 8.452 | 6.329 | 6.834 | 5.095 | −4.356 | 0.0049792 | FAT tumor suppressor homolog 1 (Drosophila) |
| HDX | 3.168 | 2.639 | 2.289 | 0.166 | 2.092 | 0.166 | −4.354 | 0.0270995 | highly divergent homeobox |
| ADAM33 | 6.448 | 6.081 | 5.000 | 3.550 | 3.961 | 4.164 | −4.347 | 0.0084633 | ADAM metallopeptidase domain 33 |
| MINPP1 | 3.828 | 2.857 | 3.163 | 2.911 | 0.751 | 0.751 | −4.304 | 0.0426895 | multiple inositol-polyphosphate phosphatase 1 |
| KCNAB3 | 4.190 | 3.527 | 3.852 | 2.270 | 1.748 | 0.751 | −4.300 | 0.0038642 | potassium voltage-gated channel, shaker-related subfamily, beta member 3 |
| DFNB31 | 7.305 | 6.566 | 6.050 | 5.546 | 4.029 | 3.951 | −4.285 | 0.0123567 | deafness, autosomal recessive 31 |
| ARL4D | 4.270 | 5.696 | 5.804 | 2.821 | 3.710 | 3.596 | −4.272 | 0.0169225 | ADP-ribosylation factor-like 4D |
| UGCG | 6.268 | 6.823 | 7.694 | 6.146 | 4.731 | 3.724 | −4.265 | 0.0293498 | UDP-glucose ceramide glucosyltransferase |
| HSD17B14 | 5.622 | 5.472 | 4.539 | 3.379 | 4.020 | −0.834 | −4.264 | 0.0401207 | hydroxysteroid (17-beta) dehydrogenase 14 |
| THY1 | 9.375 | 7.949 | 8.165 | 5.479 | 6.391 | 7.286 | −4.256 | 0.0164777 | Thy-1 cell surface antigen |
| FLJ45445 | 9.124 | 9.025 | 7.699 | 7.213 | 2.092 | 6.936 | −4.255 | 0.0436668 | No description |
| CLDN11 | 7.130 | 6.922 | 6.255 | 5.131 | 4.035 | 4.837 | −4.242 | 0.0040034 | claudin 11 |
| UBE2Q2P3 | 4.072 | 3.069 | 3.565 | 2.567 | 1.484 | 0.166 | −4.230 | 0.0189747 | ubiquitin-conjugating enzyme E2Q family member 2 pseudogene 3 |
| EGFL8 | 5.709 | 6.427 | 6.171 | 4.091 | 5.161 | 1.751 | −4.228 | 0.0279966 | EGF-like-domain, multiple 8 |
| SLC22A16 | 3.913 | 3.048 | 2.764 | 1.835 | 0.751 | 0.751 | −4.224 | 0.0062666 | solute carrier family 22 (organic cation/carnitine transporter), member 16 |
| MEIS2 | 5.802 | 6.482 | 7.144 | 4.358 | 5.068 | 3.919 | −4.218 | 0.0086471 | Meis homeobox 2 |
| TNC | 7.702 | 5.973 | 5.147 | 4.688 | 4.755 | 3.073 | −4.211 | 0.0382856 | tenascin C |
| KIFC2 | 7.376 | 7.900 | 6.139 | 5.302 | 5.748 | 4.899 | −4.210 | 0.0200337 | kinesin family member C2 |
| MEIS3 | 8.571 | 8.176 | 7.482 | 6.385 | 6.503 | 5.184 | −4.194 | 0.0088756 | Meis homeobox 3 |
| PDE4DIP | 7.563 | 7.239 | 7.589 | 5.497 | 6.282 | 4.676 | −4.189 | 0.0081086 | phosphodiesterase 4D interacting protein |
| CDK3 | 6.904 | 6.808 | 8.188 | 4.151 | 6.171 | 4.843 | −4.171 | 0.0155132 | cyclin-dependent kinase 3 |
| RRBP1 | 6.586 | 6.352 | 7.693 | 5.262 | 5.641 | 4.191 | −4.147 | 0.0209278 | ribosome binding protein 1 homolog 180 kDa (dog) |
| TRIM3 | 8.523 | 9.254 | 7.691 | 6.556 | 6.475 | 6.324 | −4.136 | 0.0061297 | tripartite motif-containing 3 |
| LRP1 | 12.017 | 11.130 | 11.262 | 9.693 | 9.969 | 8.793 | −4.135 | 0.0067349 | low density lipoprotein receptor-related protein 1 |
| PLTP | 10.539 | 10.702 | 10.852 | 8.791 | 8.592 | 8.656 | −4.130 | 0.0003635 | phospholipid transfer protein |
| PALM3 | 2.952 | 2.986 | 1.122 | 0.166 | 0.951 | 0.166 | −4.100 | 0.0231638 | paralemmin 3 |
| UST | 6.227 | 5.911 | 5.432 | 4.788 | 3.877 | 2.867 | −4.097 | 0.0142190 | uronyl-2-sulfotransferase |
| CNTN4 | 4.365 | 4.269 | 3.024 | 1.751 | 2.334 | 1.751 | −4.088 | 0.0087780 | contactin 4 |
| SDHA | 3.815 | 3.865 | 2.317 | 1.835 | 1.318 | 0.751 | −4.087 | 0.0133922 | succinate dehydrogenase complex, subunit A, flavoprotein (Fp) |
| LRP5L | 6.408 | 6.216 | 5.694 | 5.282 | 4.185 | 1.974 | −4.085 | 0.0328037 | low density lipoprotein receptor-related protein 5-like |
| SOLH | 8.101 | 8.793 | 9.374 | 7.522 | 6.765 | 5.190 | −4.079 | 0.0172772 | small optic lobes homolog (Drosophila) |
| MRAP2 | 4.848 | 4.192 | 4.468 | 2.821 | 2.821 | 1.974 | −4.076 | 0.0033249 | melanocortin 2 receptor accessory protein 2 |
| GTF3C1 | 8.723 | 7.940 | 6.592 | 6.073 | 5.925 | 5.486 | −4.043 | 0.0211797 | general transcription factor IIIC, polypeptide 1, alpha 220 kDa |
| FOXK2 | 9.620 | 9.864 | 8.865 | 8.867 | 7.605 | 6.824 | −4.039 | 0.0394149 | forkhead box K2 |
| MEF2D | 10.416 | 10.515 | 8.992 | 8.502 | 8.140 | 7.797 | −4.035 | 0.0163967 | myocyte enhancer factor 2D |
| MAP1A | 8.635 | 9.393 | 8.284 | 7.384 | 6.803 | 5.874 | −4.024 | 0.0091524 | microtubule-associated protein 1A |
| KCNE1L | 2.249 | 2.174 | 2.639 | 0.166 | 1.484 | 0.166 | −4.023 | 0.0141123 | KCNE1-like |
| HYLS1 | 4.573 | 4.282 | 4.603 | 3.275 | 2.567 | 0.166 | −4.018 | 0.0198741 | hydrolethalus syndrome 1 |
| AFAP1L2 | 4.278 | 3.604 | 2.242 | 2.045 | 1.611 | 1.166 | −3.979 | 0.0311653 | actin filament associated protein 1-like 2 |
| APOD | 17.920 | 16.308 | 15.955 | 16.180 | 13.059 | 14.316 | −3.977 | 0.0477697 | apolipoprotein D |
| SPSB1 | 10.760 | 11.556 | 10.295 | 10.192 | 8.310 | 8.343 | −3.960 | 0.0284626 | splA/ryanodine receptor domain and SOCS box containing 1 |
| PPTC7 | 4.735 | 4.890 | 5.343 | 4.329 | 2.751 | 2.751 | −3.957 | 0.0243423 | PTC7 protein phosphatase homolog (S. cerevisiae) |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| NBLA00301 | 4.072 | 4.796 | 3.144 | 3.164 | 2.092 | 0.166 | −3.945 | 0.0386887 | No description |
| MAPKBP1 | 6.004 | 6.709 | 6.158 | 4.184 | 5.761 | 3.625 | −3.927 | 0.0338733 | mitogen-activated protein kinase binding protein 1 |
| SSC5D | 9.833 | 9.447 | 8.304 | 7.801 | 6.331 | 7.788 | −3.926 | 0.0252334 | No description |
| GGT7 | 6.050 | 6.077 | 6.170 | 4.104 | 5.285 | 3.556 | −3.926 | 0.0166078 | gamma-glutamyltransferase 7 |
| TAF1D | 9.993 | 10.144 | 10.365 | 9.115 | 8.172 | 7.011 | −3.921 | 0.0135367 | TATA box binding protein (TBP)-associated factor, RNA polymerase I, D, 41 kDa |
| C1orf92 | 3.709 | 2.424 | 0.995 | 0.692 | 0.456 | −0.834 | −3.911 | 0.0268635 | chromosome 1 open reading frame 92 |
| H2AFX | 7.242 | 7.347 | 8.044 | 5.380 | 6.635 | 3.784 | −3.910 | 0.0224436 | H2A histone family, member X |
| FAM18A | 4.537 | 3.629 | 2.572 | 2.572 | 1.488 | 1.488 | −3.905 | 0.0364531 | family with sequence similarity 18, member A |
| ZC3H12A | 5.038 | 5.605 | 4.768 | 4.348 | 3.076 | 1.974 | −3.895 | 0.0244974 | zinc finger CCCH-type containing 12A |
| TMEM132C | 4.762 | 4.566 | 4.377 | 2.610 | 3.874 | 2.336 | −3.882 | 0.0220836 | transmembrane protein 132C |
| SLCO5A1 | 3.712 | 3.445 | 4.296 | 2.928 | 1.488 | 1.488 | −3.881 | 0.0162704 | solute carrier organic anion transporter family, member 5A1 |
| ALPL | 8.915 | 7.617 | 6.959 | 4.536 | 5.865 | 6.963 | −3.868 | 0.0398650 | alkaline phosphatase, liver/bone/kidney |
| TBC1D26 | 4.072 | 3.069 | 1.862 | 1.122 | 1.755 | 0.166 | −3.856 | 0.0313544 | TBC1 domain family, member 26 |
| PRRG3 | 2.698 | 2.968 | 1.748 | 0.751 | 0.751 | 0.751 | −3.854 | 0.0088453 | proline rich Gla (G-carboxyglutamic acid) 3 (transmembrane) |
| WDR62 | 4.792 | 3.852 | 2.698 | 2.487 | 1.977 | 0.751 | −3.854 | 0.0284308 | WD repeat domain 62 |
| SHC3 | 2.698 | 4.271 | 2.949 | 2.270 | 1.748 | 0.751 | −3.854 | 0.0358695 | SHC (Src homology 2 domain containing) transforming protein 3 |
| CPXM2 | 8.840 | 8.668 | 8.663 | 5.885 | 6.726 | 6.970 | −3.844 | 0.0016774 | carboxypeptidase X (M14 family), member 2 |
| HS6ST1 | 8.735 | 8.975 | 8.567 | 7.033 | 6.919 | 5.103 | −3.843 | 0.0066222 | heparan sulfate 6-O-sulfotransferase 1 |
| GZMB | 2.565 | 3.108 | 4.516 | 1.166 | 1.166 | 1.166 | −3.842 | 0.0075397 | granzyme B (granzyme 2, cytotoxic T-lymphocyte-associated serine esterase 1) |
| PLXDC1 | 9.292 | 8.368 | 9.285 | 6.301 | 8.171 | 7.344 | −3.839 | 0.0319520 | plexin domain containing 1 |
| IL6R | 7.879 | 8.152 | 9.447 | 7.506 | 6.594 | 5.449 | −3.838 | 0.0296554 | interleukin 6 receptor |
| NUDT11 | 3.221 | 3.256 | 3.578 | 2.793 | 1.318 | 0.751 | −3.830 | 0.0299762 | nudix (nucleoside diphosphate linked moiety X)-type motif 11 |
| WNK4 | 6.249 | 4.171 | 3.993 | 2.392 | 2.062 | 2.866 | −3.812 | 0.0129505 | WNK lysine deficient protein kinase 4 |
| UPF1 | 10.273 | 9.083 | 9.729 | 8.102 | 7.798 | 7.233 | −3.812 | 0.0059671 | UPF1 regulator of nonsense transcripts homolog (yeast) |
| CCNK | 7.396 | 7.041 | 8.167 | 6.172 | 6.239 | 4.567 | −3.804 | 0.0231751 | cyclin K |
| CD7 | 5.682 | 6.311 | 7.163 | 5.236 | 3.302 | 4.492 | −3.804 | 0.0206380 | CD7 molecule |
| COL6A1 | 9.763 | 9.951 | 10.041 | 8.025 | 9.390 | 6.750 | −3.801 | 0.0371282 | collagen, type VI, alpha 1 |
| PTGIS | 4.569 | 6.130 | 4.762 | 4.204 | 3.596 | 2.488 | −3.800 | 0.0406638 | prostaglandin I2 (prostacyclin) synthase |
| MKI67IP | 5.621 | 6.920 | 7.136 | 5.211 | 5.074 | 3.250 | −3.799 | 0.0274913 | MKI67 (FHA domain) interacting nucleolar phosphoprotein |
| COL2A1 | 1.862 | 2.092 | 2.174 | 0.166 | 0.166 | 0.166 | −3.798 | 0.0005110 | collagen, type II, alpha 1 |
| SLC6A1 | 2.092 | 3.248 | 1.484 | 0.166 | 0.166 | 0.166 | −3.798 | 0.0072213 | solute carrier family 6 (neurotransmitter transporter, GABA), member 1 |
| HPCA | 2.092 | 2.152 | 0.759 | 0.166 | 0.166 | 0.166 | −3.798 | 0.0269051 | hippocalcin |
| F10 | 6.052 | 6.267 | 5.730 | 4.250 | 4.343 | 1.751 | −3.797 | 0.0128370 | coagulation factor X |
| KDM6B | 14.307 | 13.889 | 13.038 | 12.482 | 11.122 | 11.719 | −3.776 | 0.0117439 | lysine (K)-specific demethylase 6B |
| SLIT3 | 6.145 | 6.252 | 7.272 | 4.593 | 5.357 | 3.810 | −3.769 | 0.0138544 | slit homolog 3 (Drosophila) |
| COL7A1 | 5.448 | 4.230 | 5.716 | 2.853 | 3.811 | 2.626 | −3.744 | 0.0122833 | collagen, type VII, alpha 1 |
| PELI2 | 6.282 | 5.365 | 6.003 | 4.379 | 4.177 | 3.336 | −3.739 | 0.0066857 | pel lino homolog 2 (Drosophila) |
| OMD | 3.068 | 3.907 | 4.723 | 2.045 | 2.817 | 1.166 | −3.737 | 0.0256078 | osteomodulin |
| SYN1 | 3.637 | 3.483 | 3.512 | 2.817 | 1.611 | 1.166 | −3.734 | 0.0198627 | synapsin I |
| PRRT2 | 4.863 | 5.688 | 4.442 | 2.429 | 2.965 | 4.002 | −3.727 | 0.0190420 | proline-rich transmembrane protein 2 |
| MIB2 | 8.044 | 9.177 | 8.446 | 6.273 | 7.779 | 6.149 | −3.720 | 0.0242092 | mindbomb homolog 2 (Drosophila) |
| EGLN3 | 4.620 | 3.646 | 4.873 | 2.702 | 3.254 | 1.751 | −3.718 | 0.0205624 | egl nine homolog 3 (C. elegans) |
| CD14 | 6.344 | 8.239 | 7.930 | 5.047 | 6.352 | 5.666 | −3.699 | 0.0328801 | CD14 molecule |
| IGHMBP2 | 4.632 | 4.932 | 6.206 | 3.250 | 4.333 | 2.166 | −3.664 | 0.0300526 | immunoglobulin mu binding protein 2 |
| SGSM2 | 8.979 | 8.849 | 8.608 | 6.848 | 7.986 | 6.741 | −3.648 | 0.0157190 | small G protein signaling modulator 2 |
| FAP | 7.340 | 7.177 | 7.701 | 5.785 | 5.311 | 5.614 | −3.647 | 0.0017228 | fibroblast activation protein, alpha |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| HPX | 5.637 | 5.129 | 5.272 | 4.203 | 3.158 | 3.411 | −3.632 | 0.0068710 | hemopexin |
| CACNA1C | 6.597 | 5.753 | 4.934 | 4.272 | 4.097 | 3.073 | −3.632 | 0.0173075 | calcium channel, voltage-dependent, L type, alpha 1C subunit |
| C16orf72 | 7.977 | 7.223 | 7.814 | 5.197 | 6.616 | 5.954 | −3.631 | 0.0147099 | chromosome 16 open reading frame 72 |
| LRRC37B | 5.045 | 5.107 | 5.180 | 3.015 | 4.128 | 3.250 | −3.621 | 0.0092349 | leucine rich repeat containing 37B |
| KDM4A | 5.768 | 5.265 | 4.941 | 4.761 | 2.318 | 3.411 | −3.614 | 0.0375223 | lysine (K)-specific demethylase 4A |
| ERGIC3 | 8.251 | 7.520 | 8.641 | 6.398 | 4.119 | 6.972 | −3.612 | 0.0262666 | ERGIC and golgi 3 |
| LRRN4CL | 4.188 | 4.481 | 5.387 | 2.610 | 3.692 | 2.336 | −3.610 | 0.0186214 | LRRN4 C-terminal like |
| PLXNA4 | 8.119 | 6.470 | 5.960 | 4.262 | 4.628 | 5.571 | −3.586 | 0.0256849 | plexin A4 |
| C16orf65 | 2.165 | 3.727 | 2.424 | 0.692 | 1.888 | −0.834 | −3.577 | 0.0321494 | No description |
| WDR47 | 4.710 | 5.114 | 3.806 | 3.759 | 2.821 | 1.974 | −3.562 | 0.0357908 | WD repeat domain 47 |
| NAT10 | 8.105 | 8.416 | 7.950 | 7.199 | 5.509 | 6.273 | −3.560 | 0.0142931 | N-acetyltransferase 10 (GCN5-related) |
| PRDM2 | 7.392 | 7.236 | 8.207 | 7.023 | 5.563 | 5.252 | −3.555 | 0.0352719 | PR domain containing 2, with ZNF domain |
| RHPN1 | 5.576 | 5.590 | 4.473 | 3.517 | 3.761 | 3.687 | −3.554 | 0.0153771 | rhophilin, Rho GTPase binding protein 1 |
| SLC35E4 | 6.920 | 7.081 | 5.901 | 5.928 | 5.094 | 3.411 | −3.547 | 0.0485405 | solute carrier family 35, member E4 |
| TRH | 2.092 | 2.946 | 1.641 | 1.122 | 0.166 | 0.166 | −3.541 | 0.0173521 | thyrotropin-releasing hormone |
| RAB17 | 4.263 | 3.569 | 3.981 | 2.165 | 3.075 | −0.834 | −3.520 | 0.0406282 | RAB17, member RAS oncogene family |
| GAS7 | 8.947 | 8.558 | 8.642 | 6.411 | 7.106 | 7.132 | −3.520 | 0.0026683 | growth arrest-specific 7 |
| MFAP2 | 4.790 | 4.382 | 2.776 | 1.722 | 2.974 | 1.166 | −3.519 | 0.0314255 | microfibrillar-associated protein 2 |
| CHSY3 | 2.817 | 2.981 | 4.260 | 1.166 | 1.611 | 1.166 | −3.519 | 0.0069822 | chondroitin sulfate synthase 3 |
| MC1R | 4.094 | 4.944 | 6.795 | 3.441 | 3.129 | 2.488 | −3.518 | 0.0220004 | melanocortin 1 receptor (alpha melanocyte stimulating hormone receptor) |
| FGFR3 | 7.573 | 7.669 | 5.322 | 4.659 | 3.771 | 5.855 | −3.517 | 0.0439346 | fibroblast growth factor receptor 3 |
| DCHS1 | 8.122 | 7.596 | 8.133 | 6.495 | 6.308 | 5.466 | −3.515 | 0.0054724 | dachsous 1 (Drosophila) |
| EP400 | 8.425 | 8.523 | 7.175 | 7.184 | 5.362 | 5.800 | −3.515 | 0.0258498 | E1A binding protein p400 |
| LILRA5 | 3.048 | 3.110 | 3.266 | 1.453 | 1.318 | 0.751 | −3.514 | 0.0014126 | leukocyte immunoglobulin-like receptor, subfamily A (with TM domain), member 5 |
| SMOC2 | 6.314 | 6.459 | 5.721 | 4.621 | 4.502 | 4.191 | −3.512 | 0.0037840 | SPARC related modular calcium binding 2 |
| MAB21L1 | 2.609 | 1.974 | 1.752 | 0.166 | 0.166 | 0.166 | −3.502 | 0.0017999 | mab-21-like 1 (C. elegans) |
| TMEM41B | 6.893 | 5.065 | 6.599 | 5.085 | 4.631 | 4.011 | −3.502 | 0.0437273 | transmembrane protein 41B |
| PKD2 | 8.458 | 8.635 | 8.406 | 7.294 | 6.652 | 6.591 | −3.497 | 0.0039414 | polycystic kidney disease 2 (autosomal dominant) |
| TOP1 | 8.815 | 8.265 | 8.658 | 7.837 | 6.089 | 6.852 | −3.497 | 0.0252787 | topoisomerase (DNA) I |
| IGFN1 | 6.606 | 5.481 | 5.161 | 3.682 | 4.388 | 3.559 | −3.480 | 0.0127311 | immunoglobulin-like and fibronectin type III domain containing 1 |
| FN1 | 9.513 | 8.609 | 8.874 | 7.717 | 7.558 | 5.681 | −3.473 | 0.0221607 | fibronectin 1 |
| CNPY4 | 7.355 | 6.216 | 5.298 | 4.159 | 4.941 | 4.424 | −3.465 | 0.0285571 | canopy 4 homolog (zebrafish) |
| TRAF3 | 4.958 | 5.558 | 6.507 | 4.619 | 4.342 | 3.166 | −3.463 | 0.0396532 | TNF receptor-associated factor 3 |
| PTPRU | 6.672 | 6.752 | 6.380 | 5.152 | 4.888 | 4.071 | −3.445 | 0.0043135 | protein tyrosine phosphatase, receptor type, U |
| EFHD2 | 10.926 | 12.094 | 11.617 | 10.309 | 10.030 | 9.065 | −3.445 | 0.0180488 | EF-hand domain family, member D2 |
| GCNT4 | 3.256 | 3.163 | 2.533 | 0.751 | 1.748 | 0.751 | −3.439 | 0.0064073 | glucosaminyl (N-acetyl) transferase 4, core 2 |
| DUSP8 | 8.043 | 8.055 | 7.216 | 6.276 | 6.120 | 5.917 | −3.431 | 0.0063514 | dual specificity phosphatase 8 |
| LRRC41 | 7.124 | 7.231 | 8.551 | 5.348 | 6.999 | 5.356 | −3.426 | 0.0415480 | leucine rich repeat containing 41 |
| MAST2 | 12.070 | 10.506 | 9.596 | 9.082 | 8.470 | 8.731 | −3.423 | 0.0280685 | microtubule associated serine/threonine kinase 2 |
| FRAT2 | 4.892 | 4.357 | 4.847 | 3.412 | 3.074 | 1.488 | −3.418 | 0.0143196 | frequently rearranged in advanced T-cell lymphomas 2 |
| CRY1 | 8.855 | 8.905 | 9.507 | 7.734 | 7.445 | 5.560 | −3.418 | 0.0160669 | cryptochrome 1 (photolyase-like) |
| KLHL21 | 8.818 | 8.756 | 10.183 | 7.052 | 8.414 | 5.209 | −3.410 | 0.0327356 | kelch-like 21 (Drosophila) |
| DYSFIP1 | 3.858 | 4.066 | 2.559 | 2.567 | 2.092 | 0.166 | −3.403 | 0.0487394 | dysferlin interacting protein 1 |
| RAB3IL1 | 7.544 | 8.672 | 8.074 | 6.308 | 7.334 | 4.528 | −3.401 | 0.0373135 | RAB3A interacting protein (rabin3)-like 1 |
| FAM63A | 5.351 | 5.262 | 3.874 | 3.586 | 2.804 | 3.336 | −3.399 | 0.0299232 | family with sequence similarity 63, member A |
| RABEP1 | 8.148 | 8.078 | 7.287 | 6.316 | 6.996 | 5.501 | −3.393 | 0.0292561 | rabaptin, RAB GTPase binding effector protein 1 |
| MAN1C1 | 4.439 | 4.154 | 3.618 | 2.392 | 2.867 | 1.751 | −3.391 | 0.0103453 | mannosidase, alpha, class 1C, member 1 |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| DKFZp686O24166 | 3.730 | 4.178 | 6.377 | 2.973 | 3.394 | 1.974 | −3.379 | 0.0464020 | No description |
| TRIO | 9.350 | 9.039 | 10.193 | 8.439 | 8.050 | 6.409 | −3.373 | 0.0291010 | triple functional domain (PTPRF interacting) |
| PDGFRL | 3.996 | 3.364 | 2.375 | 1.166 | 2.242 | 1.166 | −3.372 | 0.0275261 | platelet-derived growth factor receptor-like |
| AUTS2 | 7.662 | 6.666 | 7.097 | 6.185 | 5.315 | 4.913 | −3.371 | 0.0184489 | autism susceptibility candidate 2 |
| SPOCK1 | 4.918 | 4.176 | 5.413 | 3.444 | 3.071 | 3.166 | −3.369 | 0.0130836 | sparc/osteonectin, cwcv and kazal-like domains proteoglycan (testican) 1 |
| NPEPPS | 7.767 | 8.079 | 8.521 | 7.254 | 6.331 | 5.976 | −3.359 | 0.0187621 | aminopeptidase puromycin sensitive |
| XIRP1 | 6.975 | 6.571 | 7.274 | 6.202 | 4.351 | 5.228 | −3.357 | 0.0280284 | xin actin-binding repeat containing 1 |
| KLF16 | 7.217 | 7.148 | 6.279 | 5.472 | 5.276 | 4.846 | −3.352 | 0.0089512 | Kruppel-like factor 16 |
| WDFY2 | 6.527 | 7.078 | 7.321 | 5.881 | 5.334 | 4.760 | −3.349 | 0.0132530 | WD repeat and FYVE domain containing 2 |
| LOC100130581 | 6.073 | 5.754 | 5.584 | 5.218 | 4.010 | 3.687 | −3.349 | 0.0316184 | No description |
| FCHO1 | 3.416 | 3.231 | 3.416 | 1.488 | 2.750 | 1.488 | −3.348 | 0.0273453 | FCH domain only 1 |
| HES7 | 3.454 | 3.782 | 2.625 | 2.045 | 1.611 | 1.166 | −3.334 | 0.0142379 | hairy and enhancer of split 7 (Drosophila) |
| RFPL3S | 5.345 | 4.546 | 4.072 | 4.016 | 2.567 | 2.335 | −3.332 | 0.0367092 | RFPL3 antisense RNA (non-protein coding) |
| FRMD4B | 1.748 | 2.487 | 3.183 | 0.751 | 0.751 | 0.751 | −3.331 | 0.0114739 | FERM domain containing 4B |
| IPMK | 1.453 | 2.698 | 2.487 | 0.751 | 0.751 | 0.751 | −3.331 | 0.0212364 | inositol polyphosphate multikinase |
| RAD9A | 5.896 | 5.878 | 6.982 | 5.247 | 4.764 | 3.072 | −3.328 | 0.0339157 | RAD9 homolog A (S. pombe) |
| ENGASE | 6.672 | 6.794 | 7.346 | 5.064 | 6.322 | 4.326 | −3.317 | 0.0322341 | endo-beta-N-acetylglucosaminidase |
| RNF152 | 3.830 | 5.107 | 5.160 | 3.433 | 2.817 | 3.250 | −3.310 | 0.0266728 | ring finger protein 152 |
| EEF2 | 15.291 | 15.548 | 15.543 | 14.090 | 13.817 | 13.502 | −3.307 | 0.0025276 | eukaryotic translation elongation factor 2 |
| MAPK13 | 4.597 | 4.086 | 4.581 | 3.048 | 2.857 | 0.751 | −3.303 | 0.0178158 | mitogen-activated protein kinase 13 |
| SFMBT1 | 3.430 | 3.250 | 4.735 | 3.015 | 2.169 | 1.166 | −3.295 | 0.0452712 | Scm-like with four mbt domains 1 |
| TNXB | 5.554 | 6.390 | 5.987 | 4.269 | 4.249 | 4.624 | −3.290 | 0.0065261 | tenascin XB |
| NFKB2 | 11.222 | 11.701 | 10.625 | 10.459 | 8.913 | 9.265 | −3.277 | 0.0300374 | nuclear factor of kappa light polypeptide gene enhancer in B-cells 2 (p49/p100) |
| C14orf169 | 6.984 | 7.763 | 6.084 | 6.168 | 3.841 | 5.272 | −3.277 | 0.0467931 | chromosome 14 open reading frame 169 |
| PCSK9 | 6.193 | 2.878 | 2.587 | 1.166 | 1.166 | 1.166 | −3.276 | 0.0249951 | proprotein convertase subtilisin/kexin type 9 |
| ARID5A | 11.705 | 10.682 | 9.919 | 9.485 | 8.208 | 9.695 | −3.275 | 0.0480390 | AT rich interactive domain 5A (MRF1-like) |
| ZNF787 | 6.581 | 7.606 | 6.498 | 6.131 | 3.399 | 4.872 | −3.268 | 0.0323325 | zinc finger protein 787 |
| LRRC4 | 4.009 | 4.613 | 4.825 | 2.906 | 3.017 | 2.488 | −3.266 | 0.0059179 | leucine rich repeat containing 4 |
| HMHA1 | 2.485 | 4.393 | 4.335 | 2.687 | 1.166 | 1.166 | −3.264 | 0.0280836 | histocompatibility (minor) HA-1 |
| SMG1 | 6.766 | 6.589 | 7.769 | 5.818 | 6.065 | 4.295 | −3.257 | 0.0425707 | SMG1 homolog, phosphatidylinositol 3-kinase-related kinase (C. elegans) |
| MSI1 | 6.144 | 5.604 | 4.771 | 4.700 | 3.719 | 3.072 | −3.245 | 0.0340957 | musashi homolog 1 (Drosophila) |
| RPL13AP20 | 1.484 | 1.862 | 1.974 | 0.166 | 0.166 | 0.166 | −3.239 | 0.0020246 | ribosomal protein L13a pseudogene 20 |
| ZFP57 | 1.862 | 3.858 | 1.484 | 0.166 | 0.166 | 0.166 | −3.239 | 0.0155480 | zinc finger protein 57 homolog (mouse) |
| MAP3K15 | 3.707 | 1.862 | 0.759 | 0.166 | 0.166 | 0.166 | −3.239 | 0.0421486 | mitogen-activated protein kinase kinase kinase 15 |
| SKI | 10.954 | 10.779 | 9.099 | 9.261 | 7.723 | 8.358 | −3.234 | 0.0367515 | v-ski sarcoma viral oncogene homolog (avian) |
| C22orf9 | 8.868 | 9.083 | 9.814 | 7.824 | 8.121 | 6.630 | −3.234 | 0.0213710 | chromosome 22 open reading frame 9 |
| METAP2 | 7.314 | 7.002 | 7.535 | 6.261 | 3.413 | 5.621 | −3.233 | 0.0277863 | methionyl aminopeptidase 2 |
| POLR2D | 6.310 | 6.415 | 6.682 | 6.033 | 4.724 | 3.897 | −3.229 | 0.0441161 | polymerase (RNA) II (DNA directed) polypeptide D |
| ELF4 | 7.122 | 8.592 | 8.615 | 6.927 | 6.803 | 5.537 | −3.222 | 0.0387523 | E74-like factor 4 (ets domain transcription factor) |
| TEX10 | 6.905 | 6.725 | 7.819 | 5.217 | 6.273 | 3.662 | −3.222 | 0.0285299 | testis expressed 10 |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| C14orf176 | 3.391 | 3.201 | 2.854 | 1.166 | 2.484 | 1.166 | −3.222 | 0.0253128 | chromosome 14 open reading frame 176 |
| GLIPR1 | 6.724 | 6.780 | 6.559 | 5.037 | 6.041 | 4.451 | −3.219 | 0.0278317 | GLI pathogenesis-related 1 |
| FBLN2 | 6.727 | 7.384 | 6.694 | 4.277 | 5.040 | 6.231 | −3.218 | 0.0275465 | fibulin 2 |
| RNF24 | 8.399 | 7.553 | 8.147 | 7.499 | 5.920 | 5.871 | −3.209 | 0.0363809 | ring finger protein 24 |
| FAM22A | 3.450 | 3.515 | 4.043 | 1.835 | 2.487 | 0.751 | −3.204 | 0.0113135 | family with sequence similarity 22, member A |
| ZNRF3 | 5.653 | 5.444 | 5.562 | 3.884 | 4.116 | 3.558 | −3.199 | 0.0019005 | zinc and ring finger 3 |
| KIAA1407 | 4.993 | 4.559 | 3.594 | 2.702 | 3.315 | 2.866 | −3.199 | 0.0334066 | KIAA1407 |
| BCAR1 | 10.571 | 10.567 | 9.571 | 8.473 | 8.896 | 8.550 | −3.194 | 0.0118476 | breast cancer anti-estrogen resistance 1 |
| GSN | 14.460 | 14.862 | 14.463 | 12.944 | 12.276 | 13.187 | −3.193 | 0.0044300 | gelsolin |
| BRD2 | 9.916 | 9.984 | 10.114 | 9.468 | 7.940 | 8.310 | −3.191 | 0.0339883 | bromodomain containing 2 |
| ARL13B | 8.118 | 7.627 | 8.174 | 6.998 | 6.232 | 5.955 | −3.188 | 0.0126320 | ADP-ribosylation factor-like 13B |
| RCOR1 | 7.020 | 6.483 | 6.798 | 5.130 | 5.506 | 3.971 | −3.176 | 0.0105533 | REST corepressor 1 |
| C5orf42 | 6.603 | 5.996 | 5.280 | 4.178 | 4.330 | 4.479 | −3.172 | 0.0134376 | chromosome 5 open reading frame 42 |
| AMN | 1.641 | 2.787 | 2.174 | 1.122 | 0.166 | 0.166 | −3.170 | 0.0153105 | amnionless homolog (mouse) |
| MAFK | 9.691 | 11.650 | 11.494 | 8.089 | 9.988 | 8.423 | −3.164 | 0.0305420 | v-maf musculoaponeurotic fibrosarcoma oncogene homolog K (avian) |
| ICAM5 | 2.734 | 3.230 | 3.145 | 1.488 | 1.488 | 1.488 | −3.154 | 0.0026494 | intercellular adhesion molecule 5, telencephalin |
| KNDC1 | 4.893 | 3.407 | 3.083 | 1.751 | 1.751 | 1.751 | −3.150 | 0.0104444 | kinase non-catalytic C-lobe domain (KIND) containing 1 |
| MAFA | 7.581 | 6.993 | 7.337 | 5.843 | 5.927 | 3.795 | −3.147 | 0.0184716 | v-maf musculoaponeurotic fibrosarcoma oncogene homolog A (avian) |
| C17orf56 | 3.861 | 3.775 | 3.107 | 2.122 | 2.429 | 1.166 | −3.145 | 0.0162439 | chromosome 17 open reading frame 56 |
| TUBBS | 8.254 | 8.255 | 8.982 | 6.358 | 7.330 | 6.733 | −3.143 | 0.0098317 | tubulin, beta 3 |
| CDK17 | 6.072 | 5.556 | 6.939 | 4.121 | 5.291 | 4.285 | −3.133 | 0.0289399 | cyclin-dependent kinase 17 |
| ANGPTL4 | 12.527 | 12.023 | 13.089 | 11.442 | 10.927 | 9.977 | −3.132 | 0.0187235 | angiopoietin-like 4 |
| MTA2 | 5.349 | 5.600 | 5.575 | 4.748 | 3.930 | 3.336 | −3.128 | 0.0223423 | metastasis associated 1 family, member 2 |
| HIC2 | 5.576 | 5.470 | 6.343 | 4.676 | 4.699 | 3.414 | −3.126 | 0.0311842 | hypermethylated in cancer 2 |
| PENK | 6.491 | 2.969 | 3.498 | 1.949 | 1.854 | 1.488 | −3.126 | 0.0283400 | proenkephalin |
| CTGF | 11.616 | 11.043 | 12.859 | 9.859 | 9.975 | 10.133 | −3.120 | 0.0162107 | connective tissue growth factor |
| ZFP36L1 | 10.453 | 10.604 | 12.985 | 9.491 | 9.464 | 8.812 | −3.118 | 0.0309769 | zinc finger protein 36, C3H type-like 1 |
| INTS7 | 7.220 | 7.088 | 8.955 | 5.448 | 6.589 | 6.349 | −3.117 | 0.0493536 | integrator complex subunit 7 |
| ACAN | 2.817 | 3.250 | 2.429 | 1.166 | 1.611 | 1.166 | −3.115 | 0.0092644 | aggrecan |
| CNTD2 | 7.806 | 6.865 | 5.778 | 5.566 | 5.230 | 4.985 | −3.106 | 0.0437160 | cyclin N-terminal domain containing 2 |
| FADD | 6.318 | 6.329 | 6.085 | 4.908 | 4.374 | 4.683 | −3.105 | 0.0027871 | Fas (TNFRSF6)-associated via death domain |
| SCARA5 | 4.960 | 6.201 | 7.777 | 4.567 | 4.857 | 3.558 | −3.104 | 0.0442379 | scavenger receptor class A, member 5 (putative) |
| IRF1 | 7.724 | 8.419 | 8.541 | 6.911 | 6.866 | 5.711 | −3.094 | 0.0153219 | interferon regulatory factor 1 |
| MFHAS1 | 5.266 | 4.795 | 6.117 | 4.507 | 3.519 | 3.166 | −3.092 | 0.0275972 | malignant fibrous histiocytoma amplified sequence 1 |
| TRIM45 | 2.965 | 3.348 | 3.512 | 1.722 | 2.429 | 1.166 | −3.086 | 0.0202871 | tripartite motif-containing 45 |
| RARA | 9.856 | 10.334 | 8.949 | 8.145 | 8.246 | 8.234 | −3.077 | 0.0209731 | retinoic acid receptor, alpha |
| LOC284578 | 6.098 | 7.065 | 6.169 | 5.447 | 3.724 | 4.815 | −3.070 | 0.0237780 | No description |
| CMYA5 | 3.685 | 3.445 | 3.101 | 1.488 | 2.339 | 1.488 | −3.060 | 0.0087273 | cardiomyopathy associated 5 |
| TSC22D2 | 6.310 | 6.713 | 7.882 | 5.101 | 5.978 | 4.819 | −3.056 | 0.0307727 | TSC22 domain family, member 2 |
| ZNF512B | 6.023 | 5.569 | 4.538 | 3.961 | 4.272 | 3.919 | −3.047 | 0.0436365 | zinc finger protein 512B |
| OLFML1 | 3.708 | 3.580 | 3.737 | 1.974 | 2.805 | 1.974 | −3.044 | 0.0130079 | olfactomedin-like 1 |
| PTPN7 | 1.748 | 2.698 | 3.439 | 1.835 | 0.751 | 0.751 | −3.041 | 0.0478627 | protein tyrosine phosphatase, non-receptor type 7 |
| C2orf89 | 4.072 | 4.170 | 4.218 | 2.567 | 0.166 | 3.456 | −3.038 | 0.0450957 | chromosome 2 open reading frame 89 |
| VASN | 6.993 | 6.180 | 6.005 | 5.786 | 4.577 | 4.199 | −3.037 | 0.0389429 | vasorin |
| LPCAT3 | 6.928 | 8.506 | 7.248 | 4.860 | 6.932 | 5.649 | −3.031 | 0.0482394 | lysophosphatidylcholine acyltransferase 3 |
| TGIF2 | 7.101 | 6.956 | 7.498 | 4.396 | 6.373 | 5.502 | −3.031 | 0.0251623 | TGFB-induced factor homeobox 2 |
| MAPK8IP1 | 2.040 | 3.048 | 2.350 | 0.751 | 0.751 | 0.751 | −3.030 | 0.0052356 | mitogen-activated protein kinase 8 interacting protein 1 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| PBX2 | 8.073 | 8.758 | 7.847 | 6.187 | 7.172 | 6.697 | −3.002 | 0.0179595 | pre-B-cell leukemia homeobox 2 |
| LOC1001296 37 | 3.319 | 4.068 | 3.975 | 2.144 | 2.490 | 1.751 | −2.985 | 0.0074981 | No description |
| ADAM12 | 7.243 | 5.180 | 5.831 | 4.390 | 4.261 | 3.810 | −2.969 | 0.0196797 | ADAM metallopeptidase domain 12 |
| SCYL1 | 10.170 | 11.145 | 10.026 | 9.003 | 9.578 | 7.976 | −2.962 | 0.0364815 | SCY1-like 1 (S. cerevisiae) |
| FBLN7 | 5.824 | 5.418 | 5.297 | 3.852 | 4.333 | 2.166 | −2.961 | 0.0176025 | fibulin 7 |
| SIX2 | 4.216 | 4.316 | 4.905 | 2.750 | 4.021 | 1.488 | −2.959 | 0.0489595 | SIX homeobox 2 |
| C14orf132 | 5.050 | 5.160 | 4.467 | 3.542 | 3.487 | 3.254 | −2.954 | 0.0077674 | chromosome 14 open reading frame 132 |
| MLL4 | 8.455 | 8.207 | 7.985 | 7.698 | 6.424 | 6.580 | −2.951 | 0.0394883 | No description |
| MECP2 | 9.341 | 8.720 | 7.943 | 7.783 | 7.346 | 6.013 | −2.943 | 0.0460677 | methyl CpG binding protein 2 (Rett syndrome) |
| MTMR3 | 6.300 | 6.709 | 6.595 | 5.687 | 5.041 | 4.550 | −2.936 | 0.0188090 | myotubularin related protein 3 |
| MMP14 | 7.207 | 6.952 | 7.712 | 6.166 | 5.957 | 2.974 | −2.920 | 0.0403567 | matrix metallopeptidase 14 (membrane-inserted) |
| PLD3 | 10.265 | 9.404 | 9.285 | 7.747 | 8.358 | 8.722 | −2.903 | 0.0328151 | phospholipase D family, member 3 |
| GPR124 | 6.945 | 5.347 | 5.389 | 4.087 | 4.765 | 3.810 | −2.902 | 0.0317341 | G protein-coupled receptor 124 |
| JAMS | 7.420 | 6.554 | 7.689 | 6.154 | 5.981 | 3.414 | −2.898 | 0.0453166 | junctional adhesion molecule 3 |
| TMC5 | 6.471 | 5.169 | 5.625 | 5.056 | 4.090 | 2.488 | −2.898 | 0.0454247 | transmembrane channel-like 5 |
| CTBP2 | 5.007 | 4.974 | 4.033 | 3.441 | 3.492 | 2.336 | −2.895 | 0.0257455 | C-terminal binding protein 2 |
| FAM181B | 0.692 | 2.165 | 2.222 | 0.692 | −0.834 | −0.834 | −2.888 | 0.0225102 | family with sequence similarity 181, member B |
| BDKRB2 | 4.434 | 4.280 | 4.683 | 3.814 | 2.751 | 2.751 | −2.886 | 0.0272001 | bradykinin receptor B2 |
| FBXL14 | 4.860 | 4.861 | 3.231 | 2.229 | 2.572 | 3.333 | −2.883 | 0.0421131 | F-box and leucine-rich repeat protein 14 |
| ACE | 4.550 | 6.689 | 5.811 | 3.107 | 4.485 | 4.285 | −2.881 | 0.0481070 | angiotensin I converting enzyme (peptidyl-dipeptidase A) 1 |
| NDRG1 | 10.753 | 11.448 | 11.702 | 9.230 | 10.262 | 9.268 | −2.873 | 0.0138430 | N-myc downstream regulated 1 |
| UBIAD1 | 8.156 | 8.535 | 7.699 | 7.190 | 5.728 | 6.635 | −2.870 | 0.0234194 | UbiA prenyltransferase domain containing 1 |
| KCNJ12 | 4.177 | 3.926 | 3.813 | 2.166 | 2.406 | 3.556 | −2.869 | 0.0496834 | potassium inwardly-rectifying channel, subfamily J, member 12 |
| EVC | 4.528 | 4.444 | 3.341 | 3.010 | 2.804 | 2.626 | −2.865 | 0.0377992 | Ellis van Creveld syndrome |
| NAF1 | 6.452 | 6.490 | 5.331 | 5.216 | 3.815 | 4.697 | −2.859 | 0.0399762 | nuclear assembly factor 1 homolog (S. cerevisiae) |
| SAMD4A | 9.210 | 9.294 | 8.593 | 7.399 | 7.785 | 7.295 | −2.846 | 0.0077296 | sterile alpha motif domain containing 4A |
| C5orf45 | 7.352 | 7.304 | 7.389 | 5.152 | 5.844 | 6.451 | −2.844 | 0.0165329 | chromosome 5 open reading frame 45 |
| SLC22A17 | 8.012 | 7.762 | 7.438 | 6.256 | 6.592 | 4.899 | −2.841 | 0.0174996 | solute carrier family 22, member 17 |
| MTSS1L | 6.788 | 7.094 | 6.277 | 5.527 | 5.591 | 4.366 | −2.835 | 0.0240412 | metastasis suppressor 1-like |
| PRKCZ | 3.438 | 4.414 | 4.298 | 2.799 | 3.098 | 0.166 | −2.826 | 0.0497644 | protein kinase C, zeta |
| TNKS1BP1 | 10.097 | 9.456 | 9.377 | 7.962 | 8.707 | 7.469 | −2.817 | 0.0179391 | tankyrase 1 binding protein 1, 182 kDa |
| ZFAND2A | 11.032 | 10.507 | 9.941 | 9.561 | 8.176 | 9.013 | −2.816 | 0.0283778 | zinc finger, AN1-type domain 2A |
| PDCD7 | 6.558 | 5.859 | 6.257 | 4.690 | 5.455 | 4.365 | −2.816 | 0.0260919 | programmed cell death 7 |
| TRIM28 | 11.497 | 11.320 | 11.303 | 9.829 | 10.615 | 8.810 | −2.810 | 0.0267636 | tripartite motif-containing 28 |
| TTC7A | 7.326 | 8.001 | 7.678 | 6.061 | 6.510 | 5.877 | −2.810 | 0.0086131 | tetratricopeptide repeat domain 7A |
| ADAMTS14 | 3.826 | 3.897 | 3.760 | 2.336 | 2.336 | 2.336 | −2.810 | 0.0011025 | ADAM metallopeptidase with thrombospondin type 1 motif, 14 |
| PHF23 | 5.722 | 5.467 | 5.422 | 3.978 | 4.577 | 2.866 | −2.807 | 0.0188203 | PHD finger protein 23 |
| CDR2 | 7.675 | 7.724 | 7.972 | 6.783 | 6.238 | 5.767 | −2.800 | 0.0107061 | cerebellar degeneration-related protein 2, 62 kDa |
| COL13A1 | 3.986 | 4.256 | 3.649 | 2.931 | 2.406 | 2.166 | −2.795 | 0.0116154 | collagen, type XIII, alpha 1 |
| SLC7A1 | 7.146 | 7.376 | 7.628 | 6.477 | 5.895 | 3.810 | −2.793 | 0.0344709 | solute carrier family 7 (cationic amino acid transporter, y+ system), member 1 |
| IER5 | 9.911 | 10.295 | 10.642 | 8.814 | 9.471 | 8.262 | −2.791 | 0.0259936 | immediate early response 5 |
| MTMR11 | 4.710 | 4.936 | 5.427 | 3.456 | 3.681 | 3.250 | −2.790 | 0.0060980 | myotubularin related protein 11 |
| LOC619207 | 2.968 | 3.287 | 1.949 | 1.488 | 1.488 | 1.488 | −2.789 | 0.0444807 | No description |

TABLE 7-continued

Differentially Exprssed Genes in Stromal Breast Epithelial Cells

| | Nulliparous (NP) Samples | | | Parous (P) Samples | | | Pseudo fold change | P value | Gene description |
|---|---|---|---|---|---|---|---|---|---|
| Gene Symbol | Stroma N33 | Stroma N35 | Stroma N58 | Stroma N37 | Stroma N39 | Stroma N40 | | | |
| RUNX1T1 | 3.452 | 2.527 | 4.379 | 1.974 | 1.974 | 1.974 | −2.787 | 0.0399164 | runt-related transcription factor 1; translocated to, 1 (cyclin D-related) |
| VTN | 1.641 | 2.386 | 1.588 | 0.166 | 0.166 | 0.166 | −2.780 | 0.0040314 | vitronectin |
| GNG8 | 2.249 | 2.946 | 1.641 | 1.588 | 0.166 | 0.166 | −2.780 | 0.0352122 | guanine nucleotide binding protein (G protein), gamma 8 |
| EHD1 | 9.288 | 9.409 | 9.591 | 7.953 | 8.117 | 7.786 | −2.778 | 0.0027644 | EH-domain containing 1 |
| NEFM | 1.620 | 1.888 | 2.165 | 0.692 | 0.456 | −0.834 | −2.776 | 0.0155942 | neurofilament, medium polypeptide |
| PRSSL1 | 0.456 | 2.165 | 1.663 | 0.692 | −0.834 | −0.834 | −2.776 | 0.0401902 | protease, serine-like 1 |
| TLE1 | 8.608 | 7.883 | 8.825 | 6.829 | 7.353 | 6.491 | −2.775 | 0.0161146 | transducin-like enhancer of split 1 (E(sp1) homolog, Drosophila) |
| SPEN | 7.884 | 8.523 | 8.791 | 7.184 | 7.319 | 4.887 | −2.774 | 0.0395034 | spen homolog, transcriptional regulator (Drosophila) |
| CHERP | 8.099 | 8.300 | 8.875 | 6.890 | 7.405 | 4.893 | −2.770 | 0.0298022 | calcium homeostasis endoplasmic reticulum protein |
| CDK5RAP2 | 5.792 | 6.534 | 6.385 | 4.703 | 5.067 | 4.815 | −2.764 | 0.0123060 | CDK5 regulatory subunit associated protein 2 |
| USP7 | 8.768 | 8.918 | 9.745 | 7.451 | 8.308 | 5.908 | −2.763 | 0.0331101 | ubiquitin specific peptidase 7 (herpes virus-associated) |
| PDLIM4 | 12.113 | 12.321 | 11.862 | 11.401 | 10.650 | 9.720 | −2.756 | 0.0329399 | PDZ and LIM domain 4 |
| MYH11 | 4.876 | 4.735 | 5.058 | 3.274 | 3.781 | 3.414 | −2.754 | 0.0063400 | myosin, heavy chain 11, smooth muscle |
| FOXL1 | 2.817 | 2.625 | 2.085 | 1.166 | 1.166 | 1.166 | −2.748 | 0.0109830 | forkhead box L1 |
| ARL8A | 8.701 | 9.283 | 10.091 | 7.686 | 8.482 | 7.825 | −2.746 | 0.0428733 | ADP-ribosylation factor-like 8A |
| CRY2 | 8.867 | 9.000 | 9.917 | 7.671 | 8.046 | 7.410 | −2.745 | 0.0158007 | cryptochrome 2 (photolyase-like) |
| MAN2C1 | 6.411 | 7.206 | 7.636 | 5.235 | 6.184 | 5.422 | −2.736 | 0.0303854 | mannosidase, alpha, class 2C, member 1 |
| SQSTM1 | 13.426 | 13.022 | 13.739 | 12.613 | 11.978 | 11.523 | −2.729 | 0.0282954 | sequestosome 1 |
| ARFGAP3 | 10.145 | 10.364 | 9.371 | 9.020 | 8.697 | 6.758 | −2.728 | 0.0426471 | ADP-ribosylation factor GTPase activating protein 3 |
| NCOA1 | 7.072 | 6.954 | 7.576 | 5.728 | 6.113 | 5.507 | −2.726 | 0.0112523 | nuclear receptor coactivator 1 |
| PIK3R6 | 3.256 | 2.764 | 3.048 | 1.453 | 1.318 | 2.487 | −2.723 | 0.0399520 | phosphoinositide-3-kinase, regulatory subunit 6 |
| SNX16 | 4.607 | 4.043 | 4.683 | 2.270 | 3.646 | 3.163 | −2.722 | 0.0335042 | sorting nexin 16 |
| GPR176 | 3.914 | 4.758 | 3.933 | 3.576 | 2.490 | 1.751 | −2.719 | 0.0379225 | G protein-coupled receptor 176 |
| HOXC4 | 3.748 | 3.871 | 2.965 | 2.429 | 2.408 | 1.166 | −2.718 | 0.0315957 | homeobox C4 |
| SERPINH1 | 11.390 | 11.409 | 10.855 | 10.340 | 9.413 | 9.871 | −2.717 | 0.0221025 | serpin peptidase inhibitor, clade H (heat shock protein 47), member 1, (collagen binding protein 1) |
| TTYH2 | 4.280 | 3.713 | 3.193 | 1.751 | 3.158 | 1.751 | −2.716 | 0.0416101 | tweety homolog 2 (Drosophila) |
| ACOT9 | 8.041 | 8.381 | 9.151 | 7.291 | 7.710 | 6.514 | −2.715 | 0.0452144 | acyl-CoA thioesterase 9 |
| AMT | 7.592 | 7.457 | 6.994 | 4.040 | 6.105 | 6.154 | −2.710 | 0.0286713 | aminomethyltransferase |
| RPL28 | 12.286 | 12.159 | 13.653 | 10.848 | 10.745 | 11.031 | −2.709 | 0.0129852 | ribosomal protein L28 |
| SLC17A7 | 6.150 | 5.372 | 4.846 | 4.593 | 4.059 | 3.411 | −2.703 | 0.0407144 | solute carrier family 17 (sodium-dependent inorganic phosphate cotransporter), member 7 |
| BCORL1 | 5.611 | 5.508 | 4.787 | 4.075 | 4.254 | 3.336 | −2.700 | 0.0244104 | BCL6 corepressor-like 1 |
| BLOC1S3 | 5.456 | 5.279 | 6.102 | 4.675 | 4.024 | 1.166 | −2.697 | 0.0411940 | biogenesis of lysosomal organelles complex-1, subunit 3 |
| STK35 | 5.457 | 5.519 | 4.918 | 4.185 | 3.715 | 3.488 | −2.696 | 0.0096902 | serine/threonine kinase 35 |
| RRP7B | 5.864 | 5.813 | 4.557 | 4.435 | 3.770 | 3.333 | −2.692 | 0.0322190 | ribosomal RNA processing 7 homolog B (S. cerevisiae) |
| ANKH | 8.942 | 8.882 | 8.522 | 7.593 | 7.094 | 7.226 | −2.691 | 0.0055760 | ankylosis, progressive homolog (mouse) |
| CCDC59 | 8.794 | 9.004 | 8.643 | 8.283 | 6.620 | 7.366 | −2.689 | 0.0428846 | coiled-coil domain containing 59 |
| RPS16 | 14.251 | 13.656 | 13.118 | 12.827 | 12.487 | 11.399 | −2.683 | 0.0456479 | ribosomal protein S16 |
| NLGN2 | 9.493 | 8.658 | 8.950 | 8.070 | 7.854 | 7.002 | −2.683 | 0.0295216 | neuroligin 2 |
| CAMSAP1 | 6.709 | 6.388 | 6.624 | 5.902 | 5.058 | 4.968 | −2.676 | 0.0268249 | calmodulin regulated spectrin-associated protein 1 |
| LUC7L3 | 9.348 | 9.871 | 9.261 | 8.163 | 6.082 | 8.451 | −2.676 | 0.0331865 | LUC7-like 3 (S. cerevisiae) |
| MXRA5 | 6.744 | 5.593 | 5.792 | 4.375 | 4.722 | 4.335 | −2.671 | 0.0149013 | matrix-remodelling associated 5 |
| FAM198A | 3.458 | 4.100 | 3.234 | 2.144 | 2.685 | 1.751 | −2.668 | 0.0241131 | family with sequence similarity 198, member A |
| TFAP2E | 3.935 | 3.346 | 3.158 | 2.866 | 1.751 | 1.751 | −2.652 | 0.0374762 | transcription factor AP-2 epsilon (activating enhancer binding protein 2 epsilon) |
| EXOSC6 | 5.635 | 6.718 | 5.986 | 5.326 | 4.579 | 3.411 | −2.651 | 0.0370110 | exosome component 6 |
| OSBPL3 | 5.329 | 6.235 | 7.046 | 4.829 | 4.885 | 4.243 | −2.651 | 0.0337303 | oxysterol binding protein-like 3 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| GPR84 | 2.167 | 1.748 | 2.857 | 1.453 | 0.751 | 0.751 | −2.646 | 0.0401698 | G protein-coupled receptor 84 |
| MMP16 | 5.531 | 4.561 | 4.664 | 4.129 | 3.302 | 2.336 | −2.643 | 0.0331290 | matrix metal lopeptidase 16 (membrane-inserted) |
| CSDA | 3.018 | 4.265 | 4.227 | 2.144 | 1.751 | 2.866 | −2.638 | 0.0294020 | cold shock domain protein A |
| TNRC6A | 7.436 | 8.000 | 7.347 | 6.515 | 5.178 | 6.603 | −2.633 | 0.0340843 | trinucleotide repeat containing 6A |
| SNX29 | 7.151 | 7.300 | 5.927 | 5.906 | 5.061 | 5.154 | −2.628 | 0.0427583 | sorting nexin 29 |
| ZFC3H1 | 8.035 | 7.796 | 7.746 | 6.847 | 6.404 | 5.857 | −2.626 | 0.0115851 | zinc finger, C3H1-type containing |
| CAMK2A | 3.635 | 4.224 | 2.943 | 2.317 | 2.244 | 1.974 | −2.622 | 0.0240004 | calcium/calmodulin-dependent protein kinase II alpha |
| ANGPTL2 | 7.695 | 8.225 | 8.775 | 6.835 | 7.085 | 6.579 | −2.622 | 0.0205269 | angiopoietin-like 2 |
| ZCCHC14 | 6.680 | 6.520 | 6.012 | 5.291 | 5.190 | 4.335 | −2.617 | 0.0188544 | zinc finger, CCHC domain containing 14 |
| LMF2 | 8.300 | 7.490 | 7.959 | 6.272 | 6.913 | 6.503 | −2.615 | 0.0185896 | lipase maturation factor 2 |
| KIF1B | 8.089 | 8.085 | 8.568 | 6.698 | 6.981 | 7.083 | −2.615 | 0.0098642 | kinesin family member 1B |
| CHD2 | 10.537 | 10.348 | 10.587 | 9.150 | 9.263 | 7.348 | −2.614 | 0.0202477 | chromodomain helicase DNA binding protein 2 |
| SNCAIP | 4.518 | 4.796 | 4.585 | 2.144 | 3.315 | 3.411 | −2.611 | 0.0134792 | synuclein, alpha interacting protein |
| FERMT3 | 3.239 | 3.785 | 4.007 | 2.166 | 2.624 | 2.166 | −2.608 | 0.0157727 | fermitin family member 3 |
| KDELC2 | 6.353 | 5.925 | 5.974 | 4.593 | 5.099 | 3.411 | −2.603 | 0.0201146 | KDEL (Lys-Asp-Glu-Leu) containing 2 |
| PI4KB | 8.511 | 8.896 | 8.570 | 7.772 | 7.145 | 7.131 | −2.603 | 0.0150753 | phosphatidylinositol 4-kinase, catalytic, beta |
| ABCC1 | 6.082 | 5.129 | 7.168 | 4.775 | 4.831 | 3.751 | −2.600 | 0.0431002 | ATP-binding cassette, sub-family C (CFTR/MRP), member 1 |
| DOCK7 | 6.337 | 6.092 | 5.242 | 4.592 | 4.805 | 4.714 | −2.598 | 0.0393234 | dedicator of cytokinesis 7 |
| CBFA2T2 | 7.247 | 7.043 | 6.378 | 5.581 | 5.873 | 5.290 | −2.591 | 0.0232598 | core-binding factor, runt domain, alpha subunit 2; translocated to, 2 |
| LOC221710 | 6.710 | 6.143 | 6.513 | 5.751 | 4.920 | 4.779 | −2.574 | 0.0281623 | No description |
| MAD2L2 | 6.556 | 6.554 | 6.312 | 5.903 | 4.996 | 4.949 | −2.572 | 0.0356131 | MAD2 mitotic arrest deficient-like 2 (yeast) |
| KIAA1026 | 10.055 | 9.720 | 8.667 | 8.693 | 7.507 | 7.555 | −2.572 | 0.0371010 | No description |
| LOC642361 | 3.474 | 4.148 | 3.986 | 1.166 | 2.965 | 2.625 | −2.568 | 0.0348620 | No description |
| RBM44 | 2.946 | 2.174 | 2.619 | 1.588 | 1.484 | 0.166 | −2.565 | 0.0343635 | RNA binding motif protein 44 |
| SCARF2 | 4.677 | 4.329 | 4.018 | 3.482 | 2.971 | 2.166 | −2.563 | 0.0258385 | scavenger receptor class F, member 2 |
| GFRA2 | 4.465 | 4.057 | 3.729 | 3.111 | 3.065 | 1.488 | −2.555 | 0.0409641 | GDNF family receptor alpha 2 |
| TLE3 | 7.850 | 7.585 | 7.572 | 6.497 | 4.664 | 6.352 | −2.554 | 0.0212939 | transducin-like enhancer of split 3 (E(sp1) homolog, Drosophila) |
| SGCD | 5.959 | 5.301 | 5.392 | 2.867 | 4.397 | 4.610 | −2.548 | 0.0366668 | sarcoglycan, delta (35 kDa dystrophin-associated glycoprotein) |
| ZNF703 | 7.624 | 6.466 | 5.908 | 5.132 | 4.567 | 5.208 | −2.534 | 0.0239459 | zinc finger protein 703 |
| SERPING1 | 6.878 | 7.589 | 7.705 | 6.248 | 6.504 | 5.138 | −2.532 | 0.0386585 | serpin peptidase inhibitor, clade G (C1 inhibitor), member 1 |
| MAP2K3 | 10.177 | 10.304 | 11.181 | 8.347 | 9.993 | 8.965 | −2.531 | 0.0495503 | mitogen-activated protein kinase 3 |
| SUN1 | 8.333 | 8.169 | 8.080 | 6.832 | 7.102 | 6.384 | −2.525 | 0.0084747 | Sad1 and UNC84 domain containing 1 |
| HSP90AA1 | 11.104 | 10.685 | 13.080 | 9.599 | 10.190 | 9.771 | −2.519 | 0.0443423 | heat shock protein 90 kDa alpha (cytosolic), class A member 1 |
| GTF3C4 | 4.204 | 3.761 | 3.117 | 2.453 | 2.871 | 1.751 | −2.518 | 0.0427008 | general transcription factor IIIC, polypeptide 4, 90 kDa |
| TRAF5 | 3.750 | 4.008 | 4.683 | 3.022 | 3.352 | 1.974 | −2.516 | 0.0472349 | TNF receptor-associated factor 5 |
| DCTN1 | 6.229 | 6.905 | 7.240 | 6.101 | 4.900 | 5.095 | −2.514 | 0.0363922 | dynactin 1 |
| C19orf28 | 7.268 | 7.589 | 7.638 | 6.330 | 6.260 | 4.954 | −2.512 | 0.0185049 | chromosome 19 open reading frame 28 |
| LOC349114 | 5.735 | 5.662 | 5.599 | 4.706 | 4.121 | 4.335 | −2.509 | 0.0099104 | No description |
| VTI1A | 4.259 | 5.050 | 4.874 | 3.922 | 3.552 | 2.166 | −2.501 | 0.0444013 | vesicle transport through interaction with t-SNAREs homolog 1A (yeast) |
| SFT2D3 | 4.145 | 4.434 | 4.254 | 3.334 | 2.933 | 1.166 | −2.499 | 0.0312046 | SFT2 domain containing 3 |
| CDK9 | 7.987 | 8.718 | 8.940 | 6.692 | 7.619 | 6.854 | −2.498 | 0.0215934 | cyclin-dependent kinase 9 |
| SHROOM4 | 7.765 | 6.814 | 7.629 | 6.311 | 6.325 | 5.910 | −2.494 | 0.0336320 | shroom family member 4 |
| SNX32 | 2.567 | 2.335 | 1.484 | 1.588 | 0.166 | 0.166 | −2.493 | 0.0458892 | sorting nexin 32 |
| HHIP | 1.318 | 2.343 | 2.069 | 0.751 | 0.751 | 0.751 | −2.493 | 0.0368408 | hedgehog interacting protein |

TABLE 7-continued

Differentially Exprssed Genes in Stromal Breast Epithelial Cells

| | Nulliparous (NP) Samples | | | Parous (P) Samples | | | Pseudo | | |
| --- | --- | --- | --- | --- | --- | --- | --- | --- | --- |
| Gene Symbol | Stroma N33 | Stroma N35 | Stroma N58 | Stroma N37 | Stroma N39 | Stroma N40 | fold change | P value | Gene description |
| MIR155HG | 2.069 | 2.666 | 1.615 | 0.751 | 1.318 | 0.751 | −2.493 | 0.0448907 | MIR155 host gene (non-protein coding) |
| CALML6 | 3.256 | 2.069 | 1.318 | 0.751 | 0.751 | 0.751 | −2.493 | 0.0465382 | calmodulin-like 6 |
| LRRFIP2 | 8.531 | 9.304 | 9.616 | 8.008 | 8.033 | 7.220 | −2.481 | 0.0307946 | leucine rich repeat (in FLU) interacting protein 2 |
| PHRF1 | 8.193 | 7.858 | 7.895 | 6.648 | 6.886 | 5.648 | −2.475 | 0.0154663 | PHD and ring finger domains 1 |
| ZBTB7A | 9.188 | 8.873 | 8.533 | 7.693 | 7.566 | 7.230 | −2.473 | 0.0111282 | zinc finger and BTB domain containing 7A |
| LSP1 | 10.022 | 10.396 | 10.259 | 7.969 | 9.277 | 8.958 | −2.464 | 0.0222160 | lymphocyte-specific protein 1 |
| FAIM2 | 5.835 | 3.788 | 3.643 | 2.392 | 2.490 | 2.866 | −2.459 | 0.0340155 | Fas apoptotic inhibitory molecule 2 |
| LRRC8A | 9.458 | 9.524 | 9.029 | 8.445 | 8.164 | 7.218 | −2.451 | 0.0284928 | leucine rich repeat containing 8 family, member A |
| LTBP4 | 8.784 | 9.304 | 8.231 | 7.739 | 7.490 | 7.048 | −2.451 | 0.0278846 | latent transforming growth factor beta binding protein 4 |
| NUPL2 | 3.179 | 3.050 | 2.969 | 1.888 | 1.888 | −0.834 | −2.447 | 0.0370299 | nucleoporin like 2 |
| JUND | 12.973 | 13.841 | 12.417 | 11.969 | 11.889 | 11.127 | −2.444 | 0.0401585 | jun D proto-oncogene |
| ISG20L2 | 7.674 | 7.736 | 7.936 | 6.654 | 6.458 | 5.954 | −2.432 | 0.0083302 | interferon stimulated exonuclease gene 20 kDa-like 2 |
| DEF6 | 3.661 | 4.209 | 5.581 | 3.231 | 2.928 | 2.750 | −2.431 | 0.0447825 | differentially expressed in FDCP 6 homolog (mouse) |
| PLD1 | 6.633 | 6.627 | 6.107 | 5.009 | 4.829 | 5.392 | −2.426 | 0.0112727 | phospholipase D1, phosphatidylcholine-specific |
| FAM53C | 8.240 | 8.395 | 7.986 | 7.605 | 6.708 | 6.790 | −2.424 | 0.0358211 | family with sequence similarity 53, member C |
| ZNF513 | 6.837 | 6.297 | 5.799 | 4.792 | 5.020 | 5.098 | −2.423 | 0.0208347 | zinc finger protein 513 |
| FLNA | 12.785 | 12.838 | 11.689 | 11.562 | 11.057 | 10.491 | −2.422 | 0.0403453 | filamin A, alpha |
| DNAJB1 | 13.206 | 13.130 | 13.466 | 9.889 | 12.190 | 12.041 | −2.422 | 0.0333340 | DnaJ (Hsp40) homolog, subfamily B, member 1 |
| AMFR | 8.129 | 7.659 | 7.353 | 6.081 | 6.819 | 6.510 | −2.416 | 0.0285836 | autocrine motility factor receptor |
| ANK2 | 4.894 | 6.411 | 5.439 | 4.412 | 4.529 | 3.626 | −2.409 | 0.0484868 | ankyrin 2, neuronal |
| HAS2 | 3.320 | 3.749 | 4.136 | 2.488 | 2.865 | 2.488 | −2.397 | 0.0341146 | hyaluronan synthase 2 |
| SCARF1 | 5.511 | 5.172 | 5.189 | 4.151 | 4.250 | 3.724 | −2.397 | 0.0133809 | scavenger receptor class F, member 1 |
| COL15A1 | 6.317 | 6.286 | 6.755 | 5.282 | 5.497 | 4.611 | −2.392 | 0.0214247 | collagen, type XV, alpha 1 |
| GJC1 | 8.881 | 8.682 | 8.242 | 7.628 | 7.542 | 6.851 | −2.383 | 0.0267220 | gap junction protein, gamma 1, 45 kDa |
| TRABD | 9.528 | 9.897 | 9.228 | 8.674 | 7.343 | 8.276 | −2.381 | 0.0286902 | TraB domain containing |
| FKBP11 | 8.817 | 8.739 | 9.395 | 7.787 | 8.145 | 5.947 | −2.378 | 0.0452825 | FK506 binding protein 11, 19 kDa |
| UBB | 9.790 | 9.528 | 8.976 | 8.259 | 8.279 | 8.497 | −2.376 | 0.0353877 | ubiquitin B |
| SLIT2 | 4.175 | 4.050 | 4.169 | 2.931 | 2.931 | 2.166 | −2.368 | 0.0097492 | slit homolog 2 (Drosophila) |
| TBX19 | 7.172 | 6.634 | 6.774 | 5.756 | 5.731 | 5.391 | −2.367 | 0.0146131 | T-box 19 |
| BAG3 | 7.396 | 7.441 | 7.255 | 6.188 | 6.198 | 5.786 | −2.367 | 0.0069142 | BCL2-associated athanogene 3 |
| ESRRA | 7.829 | 8.162 | 8.415 | 6.924 | 7.355 | 6.535 | −2.359 | 0.0300079 | estrogen-related receptor alpha |
| CD99 | 10.034 | 10.215 | 10.808 | 8.602 | 9.185 | 9.576 | −2.349 | 0.0393627 | CD99 molecule |
| RYBP | 10.297 | 10.207 | 10.977 | 9.154 | 9.024 | 9.065 | −2.348 | 0.0103340 | RING1 and YY1 binding protein |
| CSNK2A2 | 4.589 | 4.779 | 4.751 | 3.359 | 4.173 | 3.487 | −2.346 | 0.0447492 | casein kinase 2, alpha prime polypeptide |
| ABHD5 | 7.293 | 8.260 | 7.676 | 6.153 | 6.063 | 7.044 | −2.345 | 0.0380601 | abhydrolase domain containing 5 |
| IP6K2 | 9.037 | 8.149 | 8.758 | 7.582 | 7.529 | 7.207 | −2.344 | 0.0281365 | inositol hexakisphosphate kinase 2 |
| KIAA0247 | 7.683 | 7.645 | 8.244 | 7.092 | 6.465 | 4.865 | −2.327 | 0.0397250 | KIAA0247 |
| ZSWIM6 | 5.968 | 5.774 | 7.433 | 4.844 | 5.208 | 4.557 | −2.325 | 0.0389278 | zinc finger, SWIM-type containing 6 |
| RYK | 6.612 | 6.506 | 5.829 | 5.294 | 5.369 | 4.775 | −2.317 | 0.0358393 | RYK receptor-like tyrosine kinase |
| RAPGEF4 | 4.785 | 5.346 | 5.165 | 4.135 | 3.638 | 3.623 | −2.315 | 0.0147863 | Rap guanine nucleotide exchange factor (GEF) 4 |
| AXIN2 | 5.770 | 5.530 | 5.699 | 4.492 | 4.927 | 3.919 | −2.309 | 0.0292092 | axin 2 |
| MED15 | 10.023 | 10.304 | 10.451 | 9.536 | 9.098 | 8.531 | −2.307 | 0.0336660 | mediator complex subunit 15 |
| COLEC12 | 3.901 | 3.541 | 4.793 | 2.793 | 3.166 | 2.336 | −2.305 | 0.0433975 | collectin sub-family member 12 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| SAP30BP | 7.459 | 7.756 | 8.341 | 6.623 | 6.599 | 6.256 | −2.303 | 0.0167417 | SAP30 binding protein |
| RASSF5 | 3.596 | 4.055 | 4.358 | 2.853 | 2.972 | 2.626 | −2.300 | 0.0236169 | Ras association (RalGDS/AF-6) domain family member 5 |
| DCX | 6.289 | 3.687 | 3.674 | 2.488 | 2.488 | 2.488 | −2.296 | 0.0346222 | doublecortin |
| STX1A | 7.367 | 6.835 | 6.470 | 6.170 | 5.685 | 4.413 | −2.292 | 0.0495390 | syntaxin 1A (brain) |
| OSBPL5 | 6.645 | 6.302 | 6.646 | 5.450 | 5.865 | 4.479 | −2.289 | 0.0463045 | oxysterol binding protein-like 5 |
| TSHZ2 | 5.115 | 5.240 | 5.687 | 3.423 | 4.565 | 4.052 | −2.279 | 0.0296744 | teashirt zinc finger homeobox 2 |
| STAC | 3.249 | 3.693 | 2.702 | 2.392 | 2.062 | 1.751 | −2.277 | 0.0457061 | SH3 and cysteine rich domain |
| ZNFX1 | 9.262 | 9.251 | 10.138 | 8.368 | 8.070 | 8.712 | −2.268 | 0.0440427 | zinc finger, NFX1-type containing 1 |
| LIME1 | 6.238 | 6.844 | 6.220 | 5.135 | 5.671 | 4.619 | −2.254 | 0.0325775 | Lek interacting transmembrane adaptor 1 |
| SLC16A4 | 1.923 | 2.167 | 1.304 | 0.751 | 0.751 | 0.751 | −2.253 | 0.0419036 | solute carrier family 16, member 4 (monocarboxylic acid transporter 5) |
| PLXNA1 | 8.094 | 8.433 | 7.885 | 7.380 | 6.930 | 5.954 | −2.241 | 0.0366554 | plexin A1 |
| SBF1P1 | 8.887 | 8.499 | 8.528 | 7.417 | 7.726 | 5.915 | −2.237 | 0.0328377 | SET binding factor 1 pseudogene 1 |
| RAB11FIP3 | 5.665 | 5.709 | 6.499 | 4.552 | 5.338 | 4.071 | −2.236 | 0.0472129 | RAB11 family interacting protein 3 (class II) |
| HNRNPF | 5.400 | 4.777 | 4.949 | 3.789 | 4.386 | 3.414 | −2.235 | 0.0404134 | heterogeneous nuclear ribonucleoprotein F |
| C3orf19 | 5.018 | 5.221 | 5.520 | 4.181 | 4.364 | 3.556 | −2.229 | 0.0266615 | chromosome 3 open reading frame 19 |
| TMEM176B | 8.091 | 6.910 | 7.407 | 6.314 | 6.344 | 5.756 | −2.226 | 0.0328264 | transmembrane protein 176B |
| TUSC4 | 6.686 | 6.169 | 6.455 | 5.302 | 4.465 | 5.756 | −2.224 | 0.0430200 | No description |
| MAP3K14 | 3.769 | 4.161 | 4.437 | 3.010 | 3.416 | 2.626 | −2.209 | 0.0427697 | mitogen-activated protein kinase kinase kinase 14 |
| SIRT2 | 2.914 | 3.504 | 2.632 | 1.949 | 2.146 | 1.488 | −2.209 | 0.0403188 | sirtuin 2 |
| DZIP1L | 5.769 | 6.442 | 6.296 | 5.299 | 4.852 | 4.978 | −2.208 | 0.0293831 | DAZ interacting protein 1-like |
| GRN | 9.756 | 9.812 | 9.355 | 8.575 | 8.427 | 8.674 | −2.201 | 0.0198256 | granulin |
| MLXIP | 7.878 | 8.190 | 7.713 | 7.050 | 7.060 | 6.442 | −2.188 | 0.0358098 | MLX interacting protein |
| SLC4A8 | 1.880 | 2.069 | 1.726 | 0.751 | 0.751 | 0.751 | −2.187 | 0.0092076 | solute carrier family 4, sodium bicarbonate cotransporter, member 8 |
| PVRIG | 1.748 | 1.880 | 2.857 | 0.751 | 0.751 | 0.751 | −2.187 | 0.0204368 | poliovirus receptor related immunoglobulin domain containing |
| KIF2C | 2.410 | 1.880 | 1.880 | 0.751 | 1.318 | 0.751 | −2.187 | 0.0332092 | kinesin family member 2C |
| DPYS | 3.048 | 1.880 | 1.835 | 0.751 | 1.318 | 0.751 | −2.187 | 0.0427266 | dihydropyrimidinase |
| C1orf35 | 7.076 | 7.355 | 6.929 | 5.270 | 6.238 | 5.948 | −2.186 | 0.0238703 | chromosome 1 open reading frame 35 |
| C14orf73 | 3.455 | 3.144 | 3.565 | 2.567 | 1.484 | 2.335 | −2.173 | 0.0338249 | chromosome 14 open reading frame 73 |
| SLK | 7.996 | 7.315 | 7.602 | 6.997 | 6.484 | 6.063 | −2.170 | 0.0476895 | STE20-like kinase |
| C5orf4 | 2.801 | 2.665 | 2.602 | 1.488 | 1.854 | 1.488 | −2.165 | 0.0168355 | chromosome 5 open reading frame 4 |
| JMJD6 | 9.022 | 8.683 | 9.089 | 7.980 | 7.917 | 7.846 | −2.151 | 0.0210904 | jumonji domain containing 6 |
| GNB5 | 6.073 | 5.580 | 5.413 | 4.310 | 4.666 | 4.837 | −2.149 | 0.0354535 | guanine nucleotide binding protein (G protein), beta 5 |
| NCK2 | 8.782 | 8.681 | 9.058 | 7.680 | 6.178 | 8.096 | −2.146 | 0.0447379 | NCK adaptor protein 2 |
| DENND5B | 5.406 | 5.754 | 5.410 | 4.653 | 4.343 | 4.024 | −2.145 | 0.0195299 | DENN/MADD domain containing 5B |
| ABCA9 | 4.514 | 5.269 | 4.878 | 3.787 | 4.160 | 3.414 | −2.143 | 0.0450420 | ATP-binding cassette, sub-family A (ABC1), member 9 |
| OGFR | 9.328 | 9.409 | 8.973 | 8.310 | 8.086 | 7.928 | −2.141 | 0.0183302 | opioid growth factor receptor |
| RUNX1 | 9.188 | 9.435 | 9.640 | 8.340 | 8.677 | 6.843 | −2.136 | 0.0484285 | runt-related transcription factor 1 |
| PLINS | 7.999 | 8.381 | 8.441 | 7.291 | 7.539 | 6.666 | −2.129 | 0.0410049 | perilipin 3 |
| HELLS | 1.438 | 1.880 | 1.835 | 0.751 | 0.751 | 0.751 | −2.119 | 0.0281176 | helicase, lymphoid-specific |
| PAR-SN | 2.750 | 2.264 | 2.930 | 1.488 | 1.854 | 1.488 | −2.108 | 0.0379452 | No description |
| NEO1 | 5.976 | 4.639 | 4.234 | 3.803 | 3.590 | 3.166 | −2.097 | 0.0494936 | neogenin 1 |
| LOC646999 | 4.011 | 3.929 | 4.340 | 2.880 | 3.490 | 2.866 | −2.090 | 0.0432689 | No description |
| SLC22A4 | 3.818 | 3.379 | 3.395 | 2.888 | 1.755 | 2.335 | −2.085 | 0.0407530 | solute carrier family 22 (organic cation/ergothioneine transporter), member 4 |
| CAPN11 | 2.225 | 1.951 | 2.537 | 1.166 | 1.166 | 1.166 | −2.083 | 0.0223536 | calpain 11 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| FAM102A | 7.972 | 7.989 | 8.539 | 6.941 | 7.480 | 5.822 | −2.083 | 0.0446554 | family with sequence similarity 102, member A |
| FBXL6 | 5.771 | 5.140 | 5.539 | 4.221 | 4.492 | 4.651 | −2.065 | 0.0370783 | F-box and leucine-rich repeat protein 6 |
| CENPT | 9.005 | 9.097 | 8.894 | 8.028 | 8.052 | 7.844 | −2.062 | 0.0143612 | centromere protein T |
| IFI16 | 9.758 | 10.377 | 10.448 | 9.592 | 8.714 | 8.821 | −2.061 | 0.0473574 | interferon, gamma-inducible protein 16 |
| TRMU | 6.406 | 5.891 | 5.525 | 4.853 | 4.863 | 4.756 | −2.053 | 0.0329618 | tRNA 5-methylaminomethyl-2-thiouridylate methyltransferase |
| GJC2 | 5.055 | 4.352 | 4.123 | 3.315 | 3.158 | 3.411 | −2.052 | 0.0278960 | gap junction protein, gamma 2, 47 kDa |
| RASL12 | 4.759 | 3.499 | 3.737 | 2.702 | 2.702 | 2.866 | −2.049 | 0.0425821 | RAS-like, family 12 |
| CHD6 | 4.286 | 4.088 | 3.909 | 3.073 | 3.206 | 3.073 | −2.021 | 0.0227296 | chromodomain helicase DNA binding protein 6 |
| RBM9 | 8.618 | 8.225 | 8.433 | 7.687 | 7.419 | 7.046 | −2.021 | 0.0344595 | No description |
| CNOT1 | 5.331 | 5.742 | 5.163 | 4.676 | 4.377 | 4.164 | −1.999 | 0.0413476 | CCR4-NOT transcription complex, subunit 1 |
| TMEM35 | 1.748 | 2.270 | 1.639 | 0.751 | 0.751 | 0.751 | −1.996 | 0.0205042 | transmembrane protein 35 |
| KCNN3 | 1.318 | 1.748 | 1.838 | 0.751 | 0.751 | 0.751 | −1.996 | 0.0455378 | potassium intermediate/small conductance calcium-activated channel, subfamily N, member 3 |
| UBE2R2 | 10.856 | 11.462 | 11.330 | 10.414 | 10.333 | 10.118 | −1.995 | 0.0490057 | ubiquitin-conjugating enzyme E2R 2 |
| ZNF385A | 10.370 | 9.921 | 10.280 | 8.926 | 9.114 | 9.442 | −1.992 | 0.0331978 | zinc finger protein 385A |
| CYTH1 | 9.275 | 9.615 | 9.639 | 8.804 | 8.587 | 8.286 | −1.984 | 0.0415057 | cytohesin 1 |
| CCDC113 | 2.928 | 2.789 | 2.264 | 1.949 | 1.488 | 1.488 | −1.971 | 0.0458332 | coiled-coil domain containing 113 |
| ARHGAP20 | 3.711 | 3.679 | 3.220 | 2.737 | 2.488 | 2.488 | −1.965 | 0.0363430 | Rho GTPase activating protein 20 |
| CAMK1D | 6.840 | 6.588 | 6.725 | 5.871 | 4.524 | 5.825 | −1.957 | 0.0444474 | calcium/calmodulin-dependent protein kinase ID |
| GTF2F1 | 6.626 | 6.797 | 6.899 | 5.837 | 6.035 | 5.365 | −1.945 | 0.0352439 | general transcription factor HF, polypeptide 1, 74 kDa |
| CDON | 4.009 | 3.898 | 4.200 | 2.974 | 3.244 | 2.974 | −1.939 | 0.0248551 | Cdon homolog (mouse) |
| KIAA0240 | 4.837 | 4.692 | 4.855 | 3.891 | 4.140 | 3.166 | −1.927 | 0.0487243 | KIAA0240 |
| SHB | 7.307 | 7.487 | 8.084 | 6.470 | 6.823 | 6.546 | −1.920 | 0.0477508 | Src homology 2 domain containing adaptor protein B |
| STX5 | 9.327 | 9.722 | 9.402 | 8.747 | 8.466 | 8.431 | −1.914 | 0.0356872 | syntaxin 5 |
| KCNAB2 | 3.472 | 3.472 | 2.804 | 2.539 | 1.974 | 1.974 | −1.910 | 0.0436479 | potassium voltage-gated channel, shaker-related subfamily, beta member 2 |
| EMILIN2 | 5.748 | 5.613 | 5.428 | 4.682 | 4.869 | 3.749 | −1.906 | 0.0469111 | elastin microfibril interfacer 2 |
| PARP14 | 6.239 | 6.312 | 6.507 | 5.298 | 5.579 | 5.531 | −1.904 | 0.0346108 | poly (ADP-ribose) polymerase family, member 14 |
| INTS6 | 6.593 | 6.475 | 6.500 | 5.571 | 5.734 | 5.539 | −1.903 | 0.0211456 | integrator complex subunit 6 |
| REC8 | 6.773 | 6.465 | 7.041 | 5.655 | 5.877 | 5.997 | −1.861 | 0.0484754 | REC8 homolog (yeast) |
| SCIN | 2.686 | 2.750 | 2.264 | 1.488 | 1.854 | 1.488 | −1.861 | 0.0416933 | scinderin |
| RBMX | 1.748 | 1.438 | 1.639 | 0.751 | 0.751 | 0.751 | −1.851 | 0.0320942 | RNA binding motif protein, X-linked |
| IL11 | 3.636 | 3.895 | 3.809 | 2.944 | 2.821 | 2.973 | −1.822 | 0.0301827 | interleukin 11 |
| MEGF6 | 5.205 | 5.838 | 5.389 | 4.616 | 4.580 | 4.515 | −1.753 | 0.0491176 | multiple EGF-like-domains 6 |
| C12orf57 | 11.466 | 11.673 | 11.501 | 10.429 | 10.718 | 10.903 | −1.721 | 0.0470261 | chromosome 12 open reading frame 57 |
| Higher Expression in Parous | | | | | | | | | |
| WDR48 | 2.683 | 2.543 | 2.683 | 3.264 | 3.482 | 3.687 | 1.740 | 0.0453703 | WD repeat domain 48 |
| GRSF1 | 5.968 | 5.312 | 6.117 | 6.743 | 6.951 | 6.720 | 1.782 | 0.0489240 | G-rich RNA sequence binding factor 1 |
| COPS4 | 5.324 | 5.409 | 5.064 | 6.264 | 6.051 | 6.010 | 1.809 | 0.0449096 | COP9 constitutive photomorphogenic homolog subunit 4 (Arabidopsis) |
| SEL1L3 | 2.486 | 2.735 | 2.618 | 4.214 | 3.365 | 3.485 | 1.838 | 0.0417114 | sel-1 suppressor of lin-12-like 3 (C. elegans) |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| GOT2 | 6.305 | 6.283 | 6.226 | 7.742 | 7.191 | 7.031 | 1.876 | 0.0331751 | glutamic-oxaloacetic transaminase 2, mitochondrial (aspartate aminotransferase 2) |
| FAM98B | 1.710 | 1.813 | 2.048 | 2.687 | 3.253 | 2.625 | 1.886 | 0.0417924 | family with sequence similarity 98, member B |
| GNB1 | 5.525 | 5.891 | 5.833 | 6.897 | 6.441 | 6.659 | 1.887 | 0.0432803 | guanine nucleotide binding protein (G protein), beta polypeptide 1 |
| ADPRHL1 | 3.113 | 3.378 | 3.004 | 4.029 | 3.891 | 4.434 | 1.887 | 0.0427810 | ADP-ribosylhydrolase like 1 |
| SIGMAR1 | 6.764 | 6.348 | 6.464 | 7.694 | 7.271 | 7.576 | 1.905 | 0.0329210 | sigma non-opioid intracellular receptor 1 |
| GEN1 | 3.294 | 3.019 | 2.989 | 4.185 | 4.014 | 3.920 | 1.907 | 0.0282243 | Gen homolog 1, endonuclease (Drosophila) |
| FAM104A | 5.801 | 5.931 | 6.059 | 6.886 | 6.680 | 7.000 | 1.921 | 0.0290269 | family with sequence similarity 104, member A |
| SLC35A1 | 3.555 | 3.411 | 3.732 | 4.497 | 4.515 | 4.441 | 1.921 | 0.0250132 | solute carrier family 35 (CMP-sialic acid transporter), member A1 |
| FAM122A | 3.416 | 3.333 | 3.941 | 4.276 | 4.852 | 4.651 | 1.922 | 0.0440821 | family with sequence similarity 122A |
| CLTA | 8.046 | 7.773 | 7.936 | 8.716 | 9.002 | 8.805 | 1.922 | 0.0286433 | clathrin, light chain A |
| ZC3H13 | 4.664 | 4.785 | 4.940 | 5.486 | 5.732 | 5.884 | 1.924 | 0.0367810 | zinc finger CCCH-type containing 13 |
| ERI3 | 8.894 | 8.546 | 7.959 | 9.513 | 9.489 | 9.769 | 1.955 | 0.0375019 | ERH exoribonuclease family member 3 |
| TBCA | 8.997 | 9.091 | 8.998 | 9.965 | 10.533 | 9.733 | 1.955 | 0.0377266 | tubulin folding cofactor A |
| FBXO28 | 4.934 | 4.550 | 4.937 | 6.342 | 5.807 | 5.521 | 1.960 | 0.0400269 | F-box protein 28 |
| SLC39A3 | 5.921 | 6.303 | 5.902 | 7.092 | 6.866 | 7.274 | 1.960 | 0.0269610 | solute carrier family 39 (zinc transporter), member 3 |
| SUMO2 | 9.100 | 9.857 | 9.407 | 10.676 | 10.381 | 10.361 | 1.964 | 0.0430405 | SMT3 suppressor of mif two 3 homolog 2 (S. cerevisiae) |
| N4BP1 | 5.594 | 5.562 | 5.368 | 6.542 | 6.285 | 6.741 | 1.972 | 0.0245586 | NEDD4 binding protein 1 |
| CAMK1 | 5.949 | 6.261 | 6.037 | 6.995 | 7.734 | 6.939 | 1.986 | 0.0329096 | calcium/calmodulin-dependent protein kinase I |
| PDCL | 4.864 | 5.458 | 4.872 | 6.123 | 5.866 | 6.345 | 2.003 | 0.0382742 | phosducin-like |
| PDE1A | 1.166 | 1.166 | 1.166 | 1.722 | 2.169 | 2.625 | 2.004 | 0.0495125 | phosphodiesterase 1A, calmodulin-dependent |
| RPL12 | 13.182 | 13.313 | 12.857 | 14.194 | 13.740 | 14.675 | 2.016 | 0.0462818 | ribosomal protein L12 |
| WSB2 | 4.780 | 5.366 | 4.876 | 5.706 | 6.103 | 6.378 | 2.018 | 0.0429331 | WD repeat and SOCS box-containing 2 |
| ANGEL2 | 2.593 | 2.244 | 2.479 | 3.493 | 3.115 | 3.919 | 2.020 | 0.0377470 | angel homolog 2 (Drosophila) |
| CTBP1 | 6.613 | 6.867 | 7.273 | 8.178 | 8.049 | 7.639 | 2.037 | 0.0420329 | C-terminal binding protein 1 |
| MPDZ | 5.294 | 5.957 | 6.206 | 7.024 | 6.788 | 6.985 | 2.040 | 0.0376660 | multiple PDZ domain protein |
| SLC26A2 | 2.737 | 2.488 | 2.543 | 3.517 | 3.583 | 3.750 | 2.040 | 0.0161865 | solute carrier family 26 (sulfate transporter), member 2 |
| TMEM133 | 1.318 | 1.453 | 0.751 | 2.270 | 2.316 | 2.487 | 2.048 | 0.0209096 | transmembrane protein 133 |
| PTAR1 | 6.229 | 5.974 | 6.203 | 7.242 | 6.798 | 7.858 | 2.054 | 0.0383672 | protein prenyltransferase alpha subunit repeat containing 1 |
| DCAF6 | 5.576 | 5.417 | 5.161 | 6.615 | 6.608 | 5.977 | 2.054 | 0.0437961 | DDB1 and CUL4 associated factor 6 |
| NDUFA13 | 10.345 | 10.842 | 10.280 | 11.500 | 11.318 | 11.677 | 2.054 | 0.0359240 | NADH dehydrogenase (ubiquinone) 1 alpha subcomplex, 13 |
| MRPS35 | 5.720 | 6.020 | 6.260 | 7.259 | 7.062 | 6.994 | 2.058 | 0.0201577 | mitochondrial ribosomal protein S35 |
| FAM48A | 4.737 | 4.999 | 4.961 | 5.780 | 5.800 | 6.067 | 2.060 | 0.0231456 | family with sequence similarity 48, member A |
| RBM18 | 2.901 | 2.541 | 2.169 | 3.759 | 3.606 | 3.558 | 2.093 | 0.0273567 | RNA binding motif protein 18 |
| LPAR6 | 4.392 | 4.532 | 4.201 | 5.273 | 5.415 | 6.389 | 2.103 | 0.0297704 | lysophosphatidic acid receptor 6 |
| ZEB1 | 6.054 | 6.213 | 6.676 | 7.286 | 7.091 | 8.221 | 2.104 | 0.0465601 | zinc finger E-box binding homeobox 1 |
| AQP11 | 0.925 | 0.751 | 1.172 | 1.835 | 1.977 | 2.487 | 2.119 | 0.0250768 | aquaporin 11 |
| TMEM111 | 1.488 | 1.938 | 1.854 | 2.572 | 3.467 | 2.750 | 2.119 | 0.0355420 | transmembrane protein 111 |
| UNC119 | 6.356 | 6.348 | 6.526 | 7.102 | 7.469 | 7.611 | 2.121 | 0.0304974 | unc-119 homolog (C. elegans) |
| RAB9A | 1.122 | 2.411 | 2.081 | 3.180 | 3.168 | 3.069 | 2.125 | 0.0386471 | RAB9A, member RAS oncogene family |
| MTM1 | 2.817 | 2.920 | 2.929 | 4.008 | 4.420 | 3.596 | 2.126 | 0.0295034 | myotubularin 1 |

TABLE 7-continued

Differentially Exprssed Genes in Stromal Breast Epithelial Cells

| | Nulliparous (NP) Samples | | | Parous (P) Samples | | | Pseudo fold change | P value | Gene description |
|---|---|---|---|---|---|---|---|---|---|
| Gene Symbol | Stroma N33 | Stroma N35 | Stroma N58 | Stroma N37 | Stroma N39 | Stroma N40 | | | |
| STAT1 | 5.009 | 4.672 | 5.497 | 6.270 | 6.388 | 5.762 | 2.128 | 0.0480957 | signal transducer and activator of transcription 1, 91 kDa |
| EPM2AIP1 | 5.469 | 4.772 | 4.933 | 6.558 | 5.614 | 6.473 | 2.128 | 0.0497455 | EPM2A (laforin) interacting protein 1 |
| LYRM2 | 3.881 | 3.805 | 3.938 | 5.140 | 4.895 | 4.971 | 2.129 | 0.0082697 | LYR motif containing 2 |
| PTPRM | 2.797 | 2.961 | 3.072 | 3.814 | 4.477 | 4.052 | 2.130 | 0.0197281 | protein tyrosine phosphatase, receptor type, M |
| FMR1 | 3.238 | 2.751 | 3.197 | 3.845 | 4.434 | 3.866 | 2.135 | 0.0496948 | fragile X mental retardation 1 |
| DCAF17 | 2.821 | 2.309 | 2.237 | 3.162 | 3.879 | 3.919 | 2.140 | 0.0326502 | DDB1 and CUL4 associated factor 17 |
| CHP | 6.539 | 6.233 | 6.705 | 7.253 | 7.641 | 7.957 | 2.146 | 0.0299875 | No description |
| RAP2A | 3.034 | 3.563 | 3.642 | 4.230 | 4.748 | 4.616 | 2.152 | 0.0307243 | RAP2A, member of RAS oncogene family |
| UBE2L6 | 5.656 | 5.557 | 5.385 | 6.610 | 7.339 | 6.495 | 2.159 | 0.0202682 | ubiquitin-conjugating enzyme E2L 6 |
| RNF187 | 6.950 | 7.175 | 7.229 | 8.020 | 8.286 | 8.728 | 2.160 | 0.0179020 | ring finger protein 187 |
| THSD1P | 1.453 | 2.069 | 1.639 | 2.270 | 3.183 | 3.163 | 2.164 | 0.0471925 | No description |
| FAM13A | 4.208 | 4.728 | 4.386 | 5.501 | 5.990 | 5.062 | 2.166 | 0.0490495 | family with sequence similarity 13, member A |
| NSF | 5.623 | 5.687 | 5.837 | 7.623 | 6.439 | 6.804 | 2.170 | 0.0364036 | N-ethylmalelmide-sensitive factor |
| KCNJ8 | 3.635 | 3.893 | 3.788 | 4.433 | 5.787 | 4.908 | 2.174 | 0.0412765 | potassium inwardly-rectifying channel, subfamily J, member 8 |
| BOP1 | 5.854 | 5.970 | 6.305 | 7.624 | 6.837 | 7.096 | 2.183 | 0.0319293 | block of proliferation 1 |
| RNF125 | 5.317 | 4.848 | 4.590 | 6.443 | 5.641 | 6.195 | 2.183 | 0.0370896 | ring finger protein 125 |
| DDIT4 | 2.685 | 2.485 | 2.504 | 3.142 | 3.819 | 3.748 | 2.194 | 0.0397023 | DNA-damage-inducible transcript 4 |
| ZNF84 | 2.896 | 3.239 | 3.105 | 4.143 | 4.233 | 4.373 | 2.194 | 0.0097341 | zinc finger protein 84 |
| ACAP2 | 4.403 | 4.031 | 4.027 | 5.538 | 5.315 | 4.759 | 2.197 | 0.0429217 | ArfGAP with coiled-coil, ankyrin repeat and PH domains 2 |
| KIAA2026 | 4.277 | 4.146 | 4.682 | 5.552 | 5.290 | 5.686 | 2.210 | 0.0205738 | KIAA2026 |
| ATR | 3.879 | 4.430 | 4.195 | 5.645 | 5.118 | 5.031 | 2.223 | 0.0338060 | ataxia telangiectasia and Rad3 related |
| KIAA1429 | 4.561 | 4.798 | 5.170 | 6.040 | 6.000 | 5.713 | 2.223 | 0.0278090 | KIAA1429 |
| PPM1H | 2.264 | 1.595 | 1.595 | 3.111 | 3.074 | 2.750 | 2.227 | 0.0269384 | protein phosphatase, Mg2+/Mn2+ dependent, 1H |
| TTC39A | 1.788 | 1.595 | 1.488 | 2.522 | 3.917 | 2.750 | 2.227 | 0.0301101 | tetratricopeptide repeat domain 39A |
| GDE1 | 7.460 | 7.322 | 7.380 | 8.535 | 7.975 | 8.798 | 2.228 | 0.0390927 | glycerophosphodiester phosphodiesterase 1 |
| SNRPC | 4.324 | 4.540 | 4.844 | 5.697 | 7.072 | 5.394 | 2.230 | 0.0398234 | small nuclear ribonucleoprotein polypeptide C |
| TGDS | 1.318 | 2.487 | 2.764 | 3.251 | 3.646 | 3.852 | 2.233 | 0.0397137 | TDP-glucose 4,6-dehydratase |
| ACO1 | 6.398 | 7.017 | 6.992 | 7.559 | 8.807 | 7.882 | 2.236 | 0.0441426 | aconitase 1, soluble |
| RPRD1A | 4.860 | 4.975 | 4.717 | 6.476 | 5.610 | 6.022 | 2.238 | 0.0261645 | regulation of nuclear pre-mRNA domain containing 1A |
| TTC9 | 4.757 | 4.617 | 4.137 | 5.299 | 6.201 | 5.552 | 2.239 | 0.0380488 | tetratricopeptide repeat domain 9 |
| MYCBP | 1.949 | 2.027 | 3.023 | 3.111 | 3.757 | 3.960 | 2.239 | 0.0456237 | c-myc binding protein |
| FTO | 4.474 | 4.423 | 3.991 | 5.240 | 5.637 | 5.485 | 2.239 | 0.0185344 | fat mass and obesity associated |
| SMPD2 | 3.526 | 4.479 | 4.209 | 5.645 | 5.158 | 5.272 | 2.244 | 0.0258196 | sphingomyelin phosphodiesterase 2, neutral membrane (neutral sphingomyelinase) |
| HLCS | 0.925 | 1.318 | 1.318 | 1.835 | 2.487 | 2.487 | 2.248 | 0.0363173 | holocarboxylase synthetase (biotin-(proprionyl-CoA-carboxylase (ATP-hydrolysing)) ligase) |
| CCDC50 | 5.922 | 6.898 | 7.014 | 7.848 | 8.183 | 7.843 | 2.249 | 0.0270843 | coiled-coil domain containing 50 |
| PHF17 | 4.483 | 4.773 | 5.268 | 5.653 | 6.016 | 5.972 | 2.251 | 0.0430594 | PHD finger protein 17 |
| IFIT3 | 2.244 | 2.472 | 2.378 | 3.022 | 3.554 | 4.485 | 2.259 | 0.0402674 | interferon-induced protein with tetratricopeptide repeats 3 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| AGFG1 | 6.922 | 7.565 | 7.628 | 8.793 | 7.970 | 8.806 | 2.263 | 0.0481721 | ArfGAP with FG repeats 1 |
| C18orf45 | 3.742 | 4.025 | 3.497 | 4.921 | 4.571 | 5.609 | 2.264 | 0.0299005 | chromosome 18 open reading frame 45 |
| RAB1B | 6.449 | 6.942 | 6.749 | 7.659 | 8.470 | 7.628 | 2.265 | 0.0324308 | RAB1B, member RAS oncogene family |
| RHBDD2 | 5.475 | 5.666 | 5.601 | 6.782 | 7.481 | 6.374 | 2.267 | 0.0261456 | rhomboid domain containing 2 |
| ARCN1 | 7.135 | 6.859 | 7.750 | 8.700 | 8.353 | 8.041 | 2.269 | 0.0465269 | archain 1 |
| FAM172A | 3.616 | 3.254 | 3.226 | 4.080 | 4.590 | 4.801 | 2.275 | 0.0302999 | family with sequence similarity 172, member A |
| NLRX1 | 4.907 | 4.379 | 3.872 | 5.554 | 5.570 | 6.047 | 2.282 | 0.0247031 | NLR family member X1 |
| DBF4B | 8.778 | 8.168 | 8.436 | 9.185 | 9.629 | 10.654 | 2.287 | 0.0420904 | DBF4 homolog B (S. cerevisiae) |
| EIF2B2 | 3.591 | 4.647 | 5.037 | 6.232 | 5.666 | 5.813 | 2.291 | 0.0299119 | eukaryotic translation initiation factor 2B, subunit 2 beta, 39 kDa |
| THOC2 | 3.339 | 3.276 | 3.864 | 5.042 | 4.768 | 4.472 | 2.291 | 0.0182281 | THO complex 2 |
| KRTCAP2 | 8.442 | 8.457 | 8.133 | 9.329 | 9.634 | 10.796 | 2.291 | 0.0224550 | keratinocyte associated protein 2 |
| RGS19 | 1.949 | 2.750 | 2.921 | 3.956 | 4.010 | 3.333 | 2.306 | 0.0404709 | regulator of G-protein signaling 19 |
| KIAA1671 | 4.418 | 4.761 | 4.595 | 5.653 | 5.629 | 7.058 | 2.315 | 0.0288620 | KIAA1671 |
| ARMC7 | 1.641 | 1.122 | 1.588 | 2.335 | 2.335 | 3.069 | 2.318 | 0.0382969 | armadillo repeat containing 7 |
| NHLRC1 | 2.429 | 2.250 | 2.817 | 3.433 | 3.649 | 5.198 | 2.330 | 0.0356502 | NHL repeat containing 1 |
| PDE2A | 3.253 | 3.088 | 3.013 | 3.899 | 4.313 | 5.742 | 2.337 | 0.0387258 | phosphodiesterase 2A, cGMP-stimulated |
| NAGK | 6.056 | 5.892 | 6.446 | 6.949 | 7.281 | 7.863 | 2.338 | 0.0300730 | N-acetylglucosamine kinase |
| FAM120A | 7.883 | 7.420 | 7.563 | 9.227 | 8.212 | 8.790 | 2.341 | 0.0458219 | family with sequence similarity 120A |
| UBE2F | 4.170 | 4.981 | 4.434 | 5.606 | 6.121 | 5.662 | 2.343 | 0.0233022 | ubiquitin-conjugating enzyme E2F (putative) |
| CORO1B | 8.130 | 7.887 | 7.508 | 9.359 | 8.470 | 9.321 | 2.343 | 0.0374459 | coronin, actin binding protein, 1B |
| NDFIP2 | 3.516 | 3.677 | 4.432 | 5.620 | 5.075 | 4.745 | 2.344 | 0.0369883 | Nedd4 family interacting protein 2 |
| SIKE1 | 2.406 | 2.406 | 2.797 | 3.253 | 4.027 | 3.842 | 2.346 | 0.0286244 | suppressor of IKBKE 1 |
| CORO2A | 2.194 | 2.244 | 2.528 | 3.759 | 2.853 | 3.485 | 2.347 | 0.0496063 | coronin, actin binding protein, 2A |
| RNF160 | 4.209 | 3.580 | 3.905 | 6.425 | 4.815 | 5.084 | 2.354 | 0.0334557 | No description |
| MRPS21 | 4.834 | 4.269 | 4.363 | 5.239 | 6.070 | 5.798 | 2.354 | 0.0298816 | mitochondrial ribosomal protein S21 |
| COPS5 | 4.994 | 5.741 | 6.394 | 6.922 | 7.070 | 6.981 | 2.362 | 0.0404315 | COP9 constitutive photomorphogenic homolog subunit 5 (Arabidopsis) |
| HSD17B13 | 2.821 | 2.244 | 2.568 | 3.680 | 5.970 | 3.485 | 2.364 | 0.0460193 | hydroxysteroid (17-beta) dehydrogenase 13 |
| LCORL | 2.686 | 2.789 | 2.164 | 3.412 | 3.757 | 5.060 | 2.375 | 0.0355042 | ligand dependent nuclear receptor corepressor-like |
| C7orf27 | 6.319 | 5.522 | 5.845 | 7.314 | 6.770 | 7.190 | 2.377 | 0.0288839 | chromosome 7 open reading frame 27 |
| RGAG4 | 5.058 | 5.650 | 4.217 | 6.309 | 6.029 | 6.378 | 2.380 | 0.0470450 | retrotransposon gag domain containing 4 |
| PCMTD2 | 3.339 | 3.218 | 3.987 | 4.407 | 5.964 | 4.591 | 2.383 | 0.0424898 | protein-L-isoaspartate (D-aspartate) O-methyltransferase domain containing 2 |
| ESYT1 | 8.029 | 7.385 | 6.278 | 8.611 | 8.638 | 9.135 | 2.384 | 0.0328983 | extended synaptotagmin-like protein 1 |
| AFAP1L1 | 6.681 | 6.483 | 6.338 | 7.736 | 7.620 | 7.817 | 2.384 | 0.0073151 | actin filament associated protein 1-like 1 |
| UBE2Q1 | 6.105 | 6.418 | 5.593 | 7.773 | 7.041 | 6.848 | 2.387 | 0.0466161 | ubiquitin-conjugating enzyme E2Q family member 1 |
| SHC1 | 6.547 | 6.042 | 5.935 | 7.298 | 7.259 | 7.470 | 2.388 | 0.0188393 | SHC (Src homology 2 domain containing) transforming protein 1 |
| POLDIP2 | 7.039 | 6.833 | 6.896 | 7.856 | 8.153 | 8.796 | 2.390 | 0.0174020 | polymerase (DNA-directed), delta interacting protein 2 |
| ACOT13 | 2.299 | 2.166 | 2.668 | 3.250 | 4.687 | 3.556 | 2.390 | 0.0319406 | acyl-CoA thioesterase 13 |
| C1orf25 | 2.299 | 2.406 | 3.064 | 3.600 | 4.496 | 3.556 | 2.390 | 0.0358506 | chromosome 1 open reading frame 25 |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| FAM83D | 2.750 | 2.789 | 3.333 | 4.465 | 4.010 | 4.209 | 2.394 | 0.0158846 | family with sequence similarity 83, member D |
| ACBD5 | 4.967 | 4.588 | 4.276 | 5.340 | 5.849 | 6.381 | 2.397 | 0.0365148 | acyl-CoA binding domain containing 5 |
| SMAD1 | 3.482 | 3.562 | 3.281 | 5.136 | 4.744 | 3.951 | 2.398 | 0.0461547 | SMAD family member 1 |
| NIF3L1 | 2.968 | 2.857 | 3.957 | 4.581 | 4.917 | 4.119 | 2.398 | 0.0433030 | NIF3 NGG1 interacting factor 3-like 1 (S. pombe) |
| DHDDS | 2.854 | 2.488 | 2.855 | 3.944 | 5.542 | 3.750 | 2.399 | 0.0291411 | dehydrodolichyl diphosphate synthase |
| KLHL7 | 3.841 | 3.521 | 3.425 | 5.676 | 4.295 | 4.786 | 2.403 | 0.0385155 | kelch-like 7 (Drosophila) |
| GRLF1 | 5.307 | 6.098 | 4.696 | 6.765 | 6.572 | 6.449 | 2.403 | 0.0493869 | glucocorticoid receptor DNA binding factor 1 |
| CYTSB | 1.751 | 1.841 | 1.751 | 2.702 | 3.018 | 3.724 | 2.406 | 0.0182765 | No description |
| PARM1 | 6.260 | 6.401 | 5.768 | 7.401 | 7.035 | 7.846 | 2.407 | 0.0238287 | prostate androgen-regulated mucin-like protein 1 |
| PIP4K2B | 4.212 | 3.941 | 3.962 | 5.340 | 4.959 | 5.486 | 2.417 | 0.0130949 | phosphatidylinositol-5-phosphate 4-kinase, type II, beta |
| JKAMP | 3.855 | 4.113 | 4.153 | 6.063 | 5.322 | 5.131 | 2.422 | 0.0126078 | JNK1/MAPK8-associated membrane protein |
| ST7 | 2.463 | 3.029 | 3.059 | 3.926 | 4.339 | 3.842 | 2.427 | 0.0241600 | suppression of tumorigenicity 7 |
| GPD2 | 4.021 | 3.599 | 4.584 | 5.864 | 4.784 | 5.643 | 2.428 | 0.0365473 | glycerol-3-phosphate dehydrogenase 2 (mitochondrial) |
| ANP32E | 3.351 | 3.542 | 3.679 | 4.825 | 4.072 | 4.994 | 2.432 | 0.0424557 | acidic (leucine-rich) nuclear phosphoprotein 32 family, member E |
| GALNT1 | 4.040 | 3.969 | 4.885 | 5.253 | 6.099 | 5.391 | 2.435 | 0.0379565 | UDP-N-acetyl-alpha-D-galactosamine:polypeptide N-acetylgalactosaminyltransferase 1 (GalNAc-T1) |
| NHP2L1 | 6.800 | 7.462 | 7.929 | 8.748 | 8.982 | 8.259 | 2.438 | 0.0394565 | NHP2 non-histone chromosome protein 2-like 1 (S. cerevisiae) |
| FXC1 | 5.087 | 5.117 | 4.889 | 6.413 | 6.377 | 5.649 | 2.445 | 0.0333612 | fracture callus 1 homolog (rat) |
| SORT1 | 3.380 | 4.031 | 3.808 | 4.335 | 5.653 | 5.102 | 2.452 | 0.0433710 | sortilin 1 |
| EXOSC7 | 4.214 | 3.184 | 3.687 | 4.478 | 4.935 | 5.974 | 2.452 | 0.0448135 | exosome component 7 |
| THTPA | 4.354 | 4.326 | 3.512 | 4.736 | 5.620 | 6.445 | 2.453 | 0.0388188 | thiamine triphosphatase |
| TCEA1 | 7.677 | 7.601 | 7.976 | 9.728 | 8.838 | 8.975 | 2.460 | 0.0143725 | transcription elongation factor A (SII), 1 |
| C11orf54 | 4.332 | 4.846 | 4.979 | 5.632 | 6.071 | 6.770 | 2.462 | 0.0230299 | chromosome 11 open reading frame 54 |
| MRPS9 | 4.299 | 5.227 | 4.672 | 5.972 | 6.320 | 5.666 | 2.462 | 0.0306494 | mitochondrial ribosomal protein S9 |
| THUMPD3 | 2.556 | 2.423 | 2.920 | 4.210 | 3.955 | 3.724 | 2.464 | 0.0102243 | THUMP domain containing 3 |
| TANK | 2.423 | 2.318 | 2.658 | 4.475 | 3.513 | 3.724 | 2.464 | 0.0149126 | TRAF family member-associated NFKB activator |
| PECR | 4.338 | 3.723 | 3.439 | 5.025 | 4.963 | 5.634 | 2.465 | 0.0221721 | peroxisomal trans-2-enoyl-CoA reductase |
| GFM1 | 4.989 | 5.770 | 6.414 | 7.621 | 6.895 | 7.071 | 2.465 | 0.0310321 | G elongation factor, mitochondrial 1 |
| SLC30A5 | 5.027 | 5.356 | 5.494 | 5.898 | 7.353 | 6.660 | 2.468 | 0.0394262 | solute carrier family 30 (zinc transporter), member 5 |
| CLTCL1 | 1.971 | 1.971 | 2.085 | 3.305 | 3.276 | 3.335 | 2.470 | 0.0022704 | clathrin, heavy chain-like 1 |
| CNPY2 | 5.469 | 5.590 | 5.793 | 6.947 | 6.778 | 6.911 | 2.477 | 0.0058083 | canopy 2 homolog (zebrafish) |
| C4orf32 | 5.033 | 5.636 | 5.216 | 6.223 | 6.526 | 7.184 | 2.480 | 0.0231275 | chromosome 4 open reading frame 32 |
| YWHAB | 8.875 | 9.129 | 9.921 | 10.945 | 10.374 | 10.440 | 2.480 | 0.0336812 | tyrosine 3-monooxygenase/tryptophan 5-monooxygenase activation protein, beta polypeptide |
| MGAT4A | 3.294 | 2.909 | 3.708 | 5.021 | 4.106 | 4.889 | 2.485 | 0.0257144 | mannosyl (alpha-1,3-)-glycoprotein beta-1,4-N-acetylglucosaminyltransferase, isozyme A |
| SH3BGRL2 | 2.603 | 2.999 | 2.708 | 3.332 | 4.333 | 4.022 | 2.485 | 0.0438226 | SH3 domain binding glutamic acid-rich protein like 2 |
| HIF1AN | 3.248 | 3.522 | 3.376 | 4.705 | 4.192 | 4.837 | 2.487 | 0.0184043 | hypoxia inducible factor 1, alpha subunit inhibitor |
| OSTM1 | 2.749 | 2.608 | 3.458 | 4.573 | 4.774 | 3.487 | 2.489 | 0.0464754 | osteopetrosis associated transmembrane protein 1 |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| DIXDC1 | 4.024 | 3.711 | 3.986 | 5.031 | 5.222 | 6.083 | 2.496 | 0.0128166 | DIX domain containing 1 |
| SNX6 | 5.739 | 6.422 | 6.881 | 7.140 | 7.965 | 7.744 | 2.500 | 0.0434436 | sorting nexin 6 |
| STX17 | 2.961 | 2.841 | 3.039 | 4.130 | 4.477 | 4.285 | 2.503 | 0.0042409 | syntaxin 17 |
| PPP2R5A | 6.204 | 6.287 | 6.400 | 7.120 | 7.614 | 9.405 | 2.508 | 0.0376547 | protein phosphatase 2, regulatory subunit B', alpha |
| MED20 | 1.751 | 1.841 | 2.395 | 3.315 | 3.724 | 2.866 | 2.512 | 0.0243574 | mediator complex subunit 20 |
| CCM2 | 3.966 | 4.435 | 3.006 | 5.295 | 5.666 | 4.801 | 2.513 | 0.0357515 | cerebral cavernous malformation 2 |
| RAB8A | 5.064 | 4.899 | 5.067 | 6.556 | 5.894 | 6.393 | 2.513 | 0.0133491 | RAB8A, member RAS oncogene family |
| MRPL33 | 8.986 | 9.280 | 9.159 | 10.375 | 10.317 | 11.132 | 2.517 | 0.0105790 | mitochondrial ribosomal protein L33 |
| UBQLNL | 1.122 | 1.122 | 0.420 | 2.799 | 1.755 | 2.335 | 2.522 | 0.0248022 | ubiquilin-like |
| C21orf63 | 5.540 | 6.015 | 6.823 | 7.266 | 7.027 | 8.164 | 2.533 | 0.0496554 | chromosome 21 open reading frame 63 |
| EIF2AK1 | 7.827 | 7.998 | 7.140 | 9.323 | 8.562 | 9.173 | 2.541 | 0.0239573 | eukaryotic translation initiation factor 2-alpha kinase 1 |
| PPID | 2.808 | 3.029 | 3.012 | 4.359 | 4.906 | 4.118 | 2.544 | 0.0071486 | peptidylprolyl isomerase D |
| FBXL17 | 4.880 | 4.629 | 4.493 | 5.315 | 5.980 | 6.826 | 2.550 | 0.0377840 | F-box and leucine-rich repeat protein 17 |
| GBP3 | 3.163 | 2.764 | 3.836 | 5.173 | 4.581 | 4.119 | 2.559 | 0.0357795 | guanylate binding protein 3 |
| C14orf119 | 2.289 | 2.289 | 2.960 | 3.647 | 3.849 | 4.285 | 2.564 | 0.0144913 | chromosome 14 open reading frame 119 |
| COX4I1 | 4.999 | 4.822 | 4.827 | 5.940 | 7.928 | 6.191 | 2.573 | 0.0259338 | cytochrome c oxidase subunit IV isoform 1 |
| IMMP1L | 2.092 | 2.741 | 3.168 | 3.455 | 4.032 | 5.546 | 2.573 | 0.0445382 | IMP1 inner mitochondrial membrane peptidase-like (S. cerevisiae) |
| TSLP | 0.925 | 0.925 | 1.880 | 2.270 | 3.256 | 2.487 | 2.595 | 0.0306191 | thymic stromal lymphopoietin |
| NRD1 | 2.821 | 3.426 | 3.651 | 4.259 | 5.061 | 4.199 | 2.599 | 0.0435359 | nardilysin (N-arginine dibasic convertase) |
| DDRGK1 | 6.460 | 6.785 | 6.216 | 7.595 | 7.688 | 9.004 | 2.602 | 0.0230185 | DDRGK domain containing 1 |
| ZFAND2B | 5.927 | 6.412 | 6.038 | 7.107 | 7.421 | 8.310 | 2.607 | 0.0200806 | zinc finger, AN1-type domain 2B |
| C6orf114 | 0.951 | 0.166 | 1.353 | 2.567 | 2.092 | 2.335 | 2.611 | 0.0176539 | chromosome 6 open reading frame 114 |
| C19orf70 | 7.743 | 7.653 | 6.903 | 8.109 | 9.038 | 10.256 | 2.611 | 0.0391297 | chromosome 19 open reading frame 70 |
| MUS81 | 6.178 | 6.045 | 5.966 | 7.432 | 6.558 | 7.711 | 2.615 | 0.0446123 | MUS81 endonuclease homolog (S. cerevisiae) |
| RPL39 | 11.104 | 10.768 | 11.561 | 12.491 | 12.678 | 12.476 | 2.616 | 0.0100685 | ribosomal protein L39 |
| SFRS3 | 7.557 | 7.910 | 8.281 | 9.303 | 9.653 | 9.216 | 2.626 | 0.0085382 | No description |
| NEDD4 | 3.686 | 4.151 | 3.264 | 5.546 | 4.497 | 5.465 | 2.629 | 0.0254217 | neural precursor cell expressed, developmentally down-regulated 4 |
| ATP5A1 | 5.235 | 4.357 | 3.809 | 5.205 | 6.455 | 6.349 | 2.632 | 0.0405405 | ATP synthase, H+ transporting, mitochondrial F1 complex, alpha subunit 1, cardiac muscle |
| CNRIP1 | 6.788 | 7.154 | 7.677 | 8.551 | 7.867 | 9.293 | 2.634 | 0.0448604 | cannabinoid receptor interacting protein 1 |
| UQCR10 | 3.566 | 4.446 | 4.282 | 4.785 | 7.467 | 5.679 | 2.634 | 0.0443128 | ubiquinol-cytochrome c reductase, complex III subunit X |
| TNS1 | 7.980 | 7.733 | 7.794 | 9.131 | 9.631 | 9.161 | 2.636 | 0.0048476 | tensin 1 |
| SYNJ2BP | 4.019 | 3.707 | 4.140 | 4.718 | 5.431 | 5.540 | 2.639 | 0.0226668 | synaptojanin 2 binding protein |
| C2orf18 | 3.978 | 3.750 | 4.210 | 5.610 | 5.418 | 4.902 | 2.639 | 0.0145420 | chromosome 2 open reading frame 18 |
| C19orf77 | 0.751 | 0.925 | 1.081 | 2.487 | 1.977 | 2.487 | 2.651 | 0.0073733 | chromosome 19 open reading frame 77 |
| SPRY2 | 6.646 | 5.861 | 6.723 | 9.575 | 7.666 | 7.271 | 2.657 | 0.0457213 | sprouty homolog 2 (Drosophila) |
| POP7 | 4.091 | 4.853 | 4.823 | 6.460 | 5.501 | 5.580 | 2.658 | 0.0414119 | processing of precursor 7, ribonuclease P/MRP subunit (S. cerevisiae) |
| CLTC | 6.621 | 6.763 | 6.866 | 8.174 | 7.739 | 8.282 | 2.659 | 0.0090753 | clathrin, heavy chain (Hc) |
| RFC5 | 1.949 | 3.236 | 2.750 | 4.647 | 4.229 | 3.333 | 2.659 | 0.0468884 | replication factor C (activator 1) 5, 36.5 kDa |
| KCTD10 | 3.103 | 2.834 | 2.909 | 3.450 | 4.321 | 4.808 | 2.661 | 0.0451176 | potassium channel tetramerisation domain containing 10 |
| ZDHHC6 | 3.425 | 4.486 | 4.846 | 5.700 | 5.898 | 5.941 | 2.662 | 0.0186101 | zinc finger, DHHC-type containing 6 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
| --- | --- | --- | --- | --- | --- | --- | --- | --- | --- |
| | Stroma N33 | Stroma N35 | Stroma N58 | Stroma N37 | Stroma N39 | Stroma N40 | | | |
| KIAA0391 | 3.407 | 3.282 | 4.052 | 4.813 | 4.819 | 5.364 | 2.662 | 0.0151244 | KIAA0391 |
| PODXL | 6.131 | 5.476 | 6.142 | 8.467 | 6.890 | 6.961 | 2.665 | 0.0392727 | podocalyxin-like |
| PARL | 7.663 | 8.179 | 8.035 | 9.001 | 9.783 | 9.452 | 2.671 | 0.0109588 | presenilin associated, rhomboid-like |
| RNASEH2A | 3.256 | 3.163 | 2.343 | 3.957 | 4.581 | 4.586 | 2.672 | 0.0187772 | ribonuclease H2, subunit A |
| GIMAP2 | 1.318 | 2.243 | 2.698 | 3.356 | 4.117 | 3.528 | 2.674 | 0.0229436 | GTPase, IMAP family member 2 |
| SNF8 | 7.756 | 8.458 | 7.788 | 9.177 | 9.742 | 9.592 | 2.677 | 0.0099520 | SNF8, ESCRT-II complex subunit, homolog (S. cerevisiae) |
| RXRA | 5.333 | 5.136 | 4.354 | 5.775 | 6.310 | 7.234 | 2.678 | 0.0359051 | retinoid X receptor, alpha |
| PREPL | 3.325 | 3.494 | 3.380 | 4.147 | 4.803 | 5.125 | 2.683 | 0.0217523 | prolyl endopeptidase-like |
| TOMM22 | 4.222 | 4.604 | 5.457 | 6.028 | 6.786 | 5.741 | 2.684 | 0.0370488 | translocase of outer mitochondrial membrane 22 homolog (yeast) |
| CHPT1 | 2.998 | 2.194 | 2.528 | 3.953 | 5.298 | 3.485 | 2.686 | 0.0311085 | choline phosphotransferase 1 |
| GABBR1 | 6.527 | 7.137 | 6.342 | 8.562 | 7.290 | 8.167 | 2.686 | 0.0407871 | gamma-aminobutyric acid (GABA) B receptor, 1 |
| AKT1 | 8.870 | 9.312 | 8.019 | 10.441 | 9.445 | 10.426 | 2.687 | 0.0468998 | v-akt murine thymoma viral oncogene homolog 1 |
| ESRP2 | 2.815 | 2.977 | 2.682 | 3.626 | 4.242 | 4.853 | 2.689 | 0.0221267 | epithelial splicing regulatory protein 2 |
| RAB4A | 6.675 | 7.033 | 6.460 | 7.888 | 8.103 | 8.797 | 2.691 | 0.0113022 | RAB4A. member RAS |
| F8A1 | 4.876 | 5.164 | 4.637 | 6.605 | 6.066 | 6.214 | 2.693 | 0.0089921 | oncogene family coagulation factor VIII-associated (intronic transcript) 1 |
| TMEM184C | 3.059 | 3.103 | 3.282 | 5.024 | 4.360 | 4.533 | 2.693 | 0.0059293 | transmembrane protein 184C |
| DARS | 6.766 | 5.965 | 6.667 | 7.755 | 8.101 | 8.118 | 2.702 | 0.0089323 | aspartyl-tRNA synthetase |
| HSD17B10 | 8.062 | 8.200 | 7.609 | 9.574 | 9.360 | 9.498 | 2.706 | 0.0044073 | hydroxysteroid (17-beta) dehydrogenase 10 |
| ITGA1 | 2.299 | 2.166 | 3.010 | 4.016 | 4.448 | 3.556 | 2.710 | 0.0166350 | integrin, alpha 1 |
| HSBP1 | 5.642 | 6.073 | 6.573 | 7.517 | 7.735 | 7.080 | 2.710 | 0.0227107 | heat shock factor binding protein 1 |
| SERINC2 | 5.110 | 4.601 | 5.084 | 6.040 | 7.253 | 6.354 | 2.712 | 0.0145533 | serine incorporator 2 |
| CALCOCO2 | 6.021 | 6.050 | 7.429 | 7.462 | 8.544 | 7.885 | 2.715 | 0.0461275 | calcium binding and coiled-coil domain 2 |
| MRPL30 | 4.699 | 4.878 | 4.539 | 6.030 | 5.980 | 7.086 | 2.716 | 0.0107780 | mitochondrial ribosomal protein L30 |
| UTP14A | 3.266 | 4.215 | 3.542 | 5.879 | 4.986 | 4.586 | 2.722 | 0.0317863 | UTP14, U3 small nucleolar ribonucleoprotein, homolog A (yeast) |
| USH1G | 2.244 | 3.077 | 2.541 | 4.222 | 3.481 | 4.522 | 2.722 | 0.0229550 | Usher syndrome 1G (autosomal recessive) |
| CALM2 | 8.538 | 8.558 | 9.526 | 9.611 | 10.974 | 10.153 | 2.728 | 0.0486713 | calmodulin 2 (phosphorylase kinase, delta) |
| PACSIN3 | 3.472 | 3.176 | 2.422 | 4.129 | 3.872 | 4.975 | 2.731 | 0.0472704 | protein kinase C and casein kinase substrate in neurons 3 |
| ADI1 | 7.355 | 6.585 | 5.936 | 7.664 | 7.908 | 8.806 | 2.734 | 0.0382296 | acireductone dioxygenase 1 |
| TMEM9B | 4.943 | 4.749 | 6.135 | 7.209 | 6.774 | 6.202 | 2.736 | 0.0407031 | TMEM9 domain family, member B |
| PSMB8 | 5.699 | 6.350 | 7.039 | 7.072 | 8.129 | 8.491 | 2.736 | 0.0404429 | proteasome (prosome, macropain) subunit, beta type, 8 (large multifunctional peptidase 7) |
| C13orf31 | 1.751 | 2.379 | 2.135 | 3.834 | 3.810 | 2.866 | 2.742 | 0.0225359 | chromosome 13 open reading frame 31 |
| RUVBL1 | 2.866 | 3.517 | 3.713 | 4.973 | 5.577 | 4.252 | 2.743 | 0.0229996 | RuvB-like 1 (E. coli) |
| SUB1 | 4.194 | 3.916 | 4.525 | 5.373 | 7.697 | 5.646 | 2.744 | 0.0254845 | SUB1 homolog (S. cerevisiae) |
| BRCC3 | 2.611 | 2.406 | 2.624 | 3.656 | 4.070 | 4.335 | 2.748 | 0.0062984 | BRCA1/BRCA2-containing complex, subunit 3 |
| PCYOX1 | 5.798 | 5.632 | 5.114 | 7.092 | 6.040 | 8.100 | 2.751 | 0.0460564 | prenylcysteine oxidase 1 |
| SDF2 | 3.895 | 4.488 | 4.416 | 6.375 | 5.356 | 5.409 | 2.752 | 0.0217825 | stromal cell-derived factor 2 |
| CLEC17A | 1.166 | 1.722 | 1.952 | 3.142 | 2.631 | 3.907 | 2.760 | 0.0182508 | C-type lectin domain family 17, member A |
| MCCC2 | 6.942 | 6.111 | 5.894 | 7.607 | 7.097 | 8.407 | 2.761 | 0.0439610 | methylcrotonoyl-CoA carboxylase 2 (beta) |
| PIGY | 5.608 | 6.214 | 5.548 | 7.013 | 7.521 | 7.362 | 2.761 | 0.0082583 | phosphatidylinositol glycan anchor biosynthesis, class Y |

TABLE 7-continued

Differentially Exprssed Genes in Stromal Breast Epithelial Cells

| | Nulliparous (NP) Samples | | | Parous (P) Samples | | | Pseudo fold change | P value | Gene description |
|---|---|---|---|---|---|---|---|---|---|
| Gene Symbol | Stroma N33 | Stroma N35 | Stroma N58 | Stroma N37 | Stroma N39 | Stroma N40 | | | |
| ZMAT2 | 3.207 | 4.120 | 4.811 | 5.586 | 6.219 | 5.119 | 2.763 | 0.0335594 | zinc finger, matrin-type 2 |
| C7orf70 | 1.620 | 1.983 | 2.424 | 3.495 | 3.890 | 2.969 | 2.764 | 0.0190049 | chromosome 7 open reading frame 70 |
| APOM | 2.424 | 2.424 | 1.888 | 2.678 | 3.890 | 4.264 | 2.764 | 0.0491630 | apolipoprotein M |
| ARMC1 | 2.607 | 3.338 | 3.986 | 4.074 | 5.360 | 4.816 | 2.765 | 0.0462114 | armadillo repeat containing 1 |
| C6orf70 | 4.050 | 4.170 | 3.858 | 5.292 | 5.518 | 5.837 | 2.766 | 0.0040541 | chromosome 6 open reading frame 70 |
| PLVAP | 6.904 | 7.917 | 6.715 | 8.876 | 8.186 | 9.100 | 2.771 | 0.0250654 | plasmalemma vesicle associated protein |
| CNOT7 | 5.390 | 5.349 | 6.372 | 7.498 | 6.635 | 7.846 | 2.777 | 0.0229731 | CCR4-NOT transcription complex, subunit 7 |
| ZSCAN2 | 2.802 | 3.790 | 3.776 | 4.278 | 5.128 | 5.331 | 2.781 | 0.0314141 | zinc finger and SCAN domain containing 2 |
| CHKB-CPT1B | 1.592 | 1.579 | 0.420 | 2.335 | 2.493 | 3.069 | 2.785 | 0.0316070 | No description |
| SEP7 | 3.072 | 2.429 | 3.536 | 4.730 | 4.983 | 3.907 | 2.787 | 0.0251812 | septin 7 |
| CBR4 | 1.595 | 1.854 | 2.232 | 2.572 | 4.010 | 3.333 | 2.787 | 0.0346464 | carbonyl reductase 4 |
| CCDC115 | 5.260 | 4.836 | 4.607 | 6.044 | 6.315 | 8.068 | 2.788 | 0.0235564 | coiled-coil domain containing 115 |
| C14orf167 | 4.497 | 4.212 | 3.786 | 5.382 | 5.267 | 7.252 | 2.791 | 0.0315579 | chromosome 14 open reading frame 167 |
| DTWD1 | 2.871 | 2.556 | 2.877 | 3.315 | 4.354 | 4.522 | 2.795 | 0.0363695 | DTW domain containing 1 |
| COPZ1 | 6.733 | 6.648 | 6.190 | 8.338 | 7.677 | 7.697 | 2.803 | 0.0145117 | coatomer protein complex, subunit zeta 1 |
| INPP5A | 5.911 | 5.027 | 5.458 | 7.356 | 6.595 | 6.947 | 2.806 | 0.0143915 | inositol polyphosphate-5-phosphatase, 40 kDa |
| TMEM123 | 3.175 | 3.805 | 3.466 | 5.062 | 4.956 | 4.666 | 2.807 | 0.0084111 | transmembrane protein 123 |
| SAP5OL | 4.628 | 4.847 | 4.662 | 7.077 | 5.867 | 6.154 | 2.814 | 0.0109043 | SAP30-like |
| ATP6V1G1 | 5.468 | 5.577 | 4.820 | 7.078 | 6.423 | 6.403 | 2.830 | 0.0219739 | ATPase, H+ transporting, lysosomal 13 kDa, V1 subunit G1 |
| MAPK14 | 5.026 | 4.441 | 5.094 | 7.055 | 5.946 | 6.087 | 2.838 | 0.0204860 | mitogen-activated protein kinase 14 |
| FASN | 7.665 | 7.067 | 6.361 | 8.322 | 8.581 | 8.934 | 2.857 | 0.0178415 | fatty acid synthase |
| SIVA1 | 5.636 | 5.529 | 4.451 | 6.631 | 7.151 | 6.564 | 2.858 | 0.0184603 | SIVA1, apoptosis-inducing factor |
| TPRKB | 6.257 | 6.835 | 6.488 | 8.299 | 8.040 | 7.773 | 2.860 | 0.0063211 | TP53RK binding protein |
| SEC22B | 6.823 | 6.472 | 6.562 | 8.339 | 7.503 | 8.215 | 2.861 | 0.0140246 | SEC22 vesicle trafficking protein homolog B (S. cerevisiae) (gene/pseudogene) |
| MRPS10 | 3.554 | 4.577 | 4.161 | 6.094 | 5.257 | 5.560 | 2.861 | 0.0170064 | mitochondrial ribosomal protein S10 |
| IRGM | 0.751 | 0.751 | 0.751 | 2.270 | 1.318 | 2.487 | 2.866 | 0.0333135 | immunity-related GTPase family, M |
| ELAC1 | 1.299 | 1.166 | 1.166 | 2.687 | 2.484 | 3.596 | 2.869 | 0.0076456 | elaC homolog 1 (E. coli) |
| EXOC5 | 5.239 | 5.360 | 6.399 | 6.929 | 6.882 | 6.808 | 2.872 | 0.0431547 | exocyst complex component 5 |
| PDHX | 1.166 | 1.813 | 1.493 | 3.015 | 3.581 | 2.625 | 2.872 | 0.0106880 | pyruvate dehydrogenase complex, component X |
| NUDCD2 | 5.553 | 5.525 | 5.459 | 6.983 | 7.033 | 8.287 | 2.875 | 0.0070420 | NudC domain containing 2 |
| C9orf78 | 7.366 | 7.321 | 7.192 | 9.014 | 8.167 | 8.848 | 2.881 | 0.0133695 | chromosome 9 open reading frame 78 |
| WRB | 5.895 | 5.816 | 5.418 | 7.347 | 6.855 | 8.369 | 2.890 | 0.0120987 | tryptophan rich basic protein |
| ZDHHC2 | 1.611 | 2.674 | 2.810 | 3.142 | 4.511 | 4.165 | 2.891 | 0.0347235 | zinc finger, DHHC-type containing 2 |
| TUBG1 | 4.519 | 5.676 | 5.790 | 6.658 | 7.211 | 7.217 | 2.898 | 0.0148809 | tubulin, gamma 1 |
| NAA10 | 8.558 | 8.438 | 8.101 | 9.641 | 9.924 | 10.096 | 2.905 | 0.0044414 | N(alpha)-acetyltransferase 10, NatA catalytic subunit |
| LOC147804 | 2.404 | 2.833 | 2.758 | 5.258 | 4.302 | 3.333 | 2.915 | 0.0316615 | No description |
| PUS7L | 2.411 | 2.411 | 1.595 | 3.956 | 3.065 | 5.060 | 2.917 | 0.0223763 | pseudouridylate synthase 7 homolog (S. cerevisiae)-like |
| SLC25A3 | 6.238 | 6.542 | 6.309 | 7.856 | 7.256 | 8.221 | 2.922 | 0.0148362 | solute carrier family 25 (mitochondrial carrier; phosphate carrier), member 3 |
| SEPX1 | 6.405 | 6.138 | 5.166 | 7.114 | 7.760 | 7.686 | 2.925 | 0.0171025 | selenoprotein X, 1 |
| DTYMK | 5.100 | 4.345 | 4.896 | 5.827 | 7.162 | 6.445 | 2.926 | 0.0150639 | deoxythymidylate kinase (thymidylate kinase) |
| HIST2H2BE | 4.292 | 4.451 | 4.508 | 6.984 | 5.007 | 6.001 | 2.928 | 0.0360321 | histone cluster 2, H2be |
| NECAP2 | 7.297 | 6.959 | 6.849 | 8.515 | 8.327 | 8.848 | 2.929 | 0.0049308 | NECAP endocytosis associated 2 |
| MPI | 2.625 | 3.068 | 2.250 | 3.334 | 4.385 | 4.619 | 2.930 | 0.0307356 | mannose phosphate isomerase |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| CXorf36 | 4.035 | 4.350 | 3.992 | 5.028 | 5.587 | 6.076 | 2.932 | 0.0163741 | chromosome X open reading frame 36 |
| WDR61 | 3.231 | 2.756 | 4.566 | 4.772 | 5.684 | 4.786 | 2.938 | 0.0446010 | WD repeat domain 61 |
| CAPN12 | 7.314 | 7.445 | 6.975 | 8.690 | 8.533 | 9.477 | 2.944 | 0.0079845 | calpain 12 |
| FLJ35776 | 2.270 | 3.653 | 2.461 | 3.828 | 5.031 | 4.199 | 2.945 | 0.0361108 | No description |
| FAM136A | 4.376 | 5.043 | 4.562 | 6.349 | 6.121 | 5.934 | 2.945 | 0.0074626 | family with sequence similarity 136, member A |
| STAM2 | 3.190 | 3.899 | 4.034 | 5.149 | 5.047 | 5.593 | 2.946 | 0.0099898 | signal transducing adaptor molecule (SH3 domain and ITAM motif) 2 |
| HCLS1 | 2.735 | 2.954 | 4.269 | 4.294 | 4.802 | 5.313 | 2.946 | 0.0440132 | hematopoietic cell-specific Lyn substrate 1 |
| FUNDC1 | 0.751 | 1.081 | 0.925 | 1.453 | 2.698 | 2.487 | 2.952 | 0.0372137 | FUN14 domain containing 1 |
| SYDE1 | 5.140 | 5.765 | 5.354 | 7.411 | 6.704 | 6.900 | 2.955 | 0.0072818 | synapse defective 1, Rho GTPase, homolog 1 (C. elegans) |
| NCRNA00081 | 1.788 | 1.854 | 1.854 | 2.297 | 3.426 | 4.209 | 2.973 | 0.0434550 | No description |
| BLOC1S1 | 9.552 | 10.261 | 8.760 | 10.332 | 10.979 | 12.107 | 2.973 | 0.0476781 | biogenesis of lysosomal organelles complex-1, subunit 1 |
| NIPAL3 | 3.446 | 2.937 | 3.715 | 5.329 | 4.033 | 5.019 | 2.975 | 0.0327780 | NIPA-like domain containing 3 |
| SPR | 4.452 | 4.638 | 3.524 | 5.778 | 6.589 | 5.097 | 2.975 | 0.0304414 | sepiapterin reductase (7,8-dihydrobiopterin:NADP+ oxidoreductase) |
| MGC14436 | 1.484 | 0.166 | 0.759 | 1.588 | 2.335 | 3.165 | 2.982 | 0.0408188 | No description |
| STK25 | 5.504 | 5.301 | 5.674 | 7.082 | 6.316 | 7.833 | 2.987 | 0.0208143 | serine/threonine kinase 25 |
| GHITM | 3.556 | 3.205 | 4.223 | 5.189 | 5.803 | 4.285 | 2.990 | 0.0450238 | growth hormone inducible transmembrane protein |
| LDHB | 9.284 | 8.535 | 9.660 | 10.101 | 11.005 | 11.243 | 2.996 | 0.0216138 | lactate dehydrogenase B |
| DCTD | 5.132 | 4.546 | 5.044 | 6.341 | 6.271 | 6.717 | 3.001 | 0.0058831 | dOMP deaminase |
| RPAP2 | 3.969 | 4.126 | 3.992 | 4.947 | 5.712 | 5.666 | 3.003 | 0.0109157 | RNA polymerase II associated protein 2 |
| ABHD4 | 4.841 | 4.515 | 5.291 | 6.240 | 6.731 | 6.428 | 3.004 | 0.0066108 | abhydrolase domain containing 4 |
| LARP7 | 3.828 | 3.801 | 5.475 | 5.390 | 5.866 | 6.722 | 3.009 | 0.0467523 | La ribonucleoprotein domain family, member 7 |
| ENDOD1 | 2.051 | 2.317 | 3.382 | 3.432 | 3.970 | 4.975 | 3.016 | 0.0449905 | endonuclease domain containing 1 |
| CARD8 | 4.900 | 5.965 | 5.007 | 6.495 | 6.521 | 7.669 | 3.022 | 0.0265571 | caspase recruitment domain family, member 8 |
| LSM2 | 4.080 | 5.208 | 5.547 | 5.655 | 7.053 | 7.142 | 3.022 | 0.0388544 | LSM2 homolog, U6 small nuclear RNA associated (S. cerevisiae) |
| PIK3R1 | 7.920 | 7.207 | 7.637 | 10.409 | 8.071 | 9.234 | 3.023 | 0.0485851 | phosphoinositide-3-kinase, regulatory subunit 1 (alpha) |
| MUT | 2.264 | 2.632 | 2.750 | 3.861 | 3.991 | 4.786 | 3.026 | 0.0077182 | methylmalonyl CoA mutase |
| POLD2 | 4.950 | 5.614 | 6.267 | 7.212 | 7.044 | 7.545 | 3.028 | 0.0136154 | polymerase (DNA directed), delta 2, regulatory subunit 50 kDa |
| GOLGA5 | 4.012 | 3.921 | 4.038 | 5.926 | 4.933 | 5.611 | 3.030 | 0.0108377 | golgin A5 |
| ZNF512 | 4.322 | 4.270 | 4.173 | 5.869 | 5.639 | 6.666 | 3.031 | 0.0046736 | zinc finger protein 512 |
| NAALADL1 | 3.877 | 3.400 | 3.049 | 4.999 | 4.137 | 6.141 | 3.031 | 0.0371396 | N-acetylated alpha-linked acidic dipeptidase-like 1 |
| SNRPD1 | 0.751 | 1.563 | 1.962 | 3.387 | 3.128 | 3.163 | 3.032 | 0.0066744 | small nuclear ribonucleoprotein D1 polypeptide 16 kDa |
| C6orf120 | 6.054 | 6.884 | 5.583 | 8.486 | 6.769 | 8.203 | 3.036 | 0.0411827 | chromosome 6 open reading frame 120 |
| DYNC1I2 | 3.284 | 4.040 | 3.987 | 4.898 | 5.985 | 5.004 | 3.060 | 0.0214716 | dynein, cytoplasmic 1, intermediate chain 2 |
| COX16 | 4.198 | 4.065 | 3.781 | 5.065 | 5.683 | 6.065 | 3.068 | 0.0093794 | COX16 cytochrome c oxidase assembly homolog (S. cerevisiae) |
| CLDN7 | 3.425 | 3.621 | 4.428 | 5.239 | 6.685 | 4.896 | 3.069 | 0.0273831 | claudin 7 |
| ATP5S | 3.239 | 3.536 | 2.625 | 4.372 | 4.248 | 5.409 | 3.080 | 0.0240526 | ATP synthase, H+ transporting, mitochondrial Fo complex, subunit s (factor B) |
| ZSCAN21 | 3.841 | 2.833 | 3.841 | 5.467 | 4.678 | 4.651 | 3.086 | 0.0295571 | zinc finger and SCAN domain containing 21 |
| MBNL3 | 1.166 | 1.166 | 1.710 | 2.817 | 1.971 | 3.335 | 3.086 | 0.0368219 | muscleblind-like 3 (Drosophila) |
| ROBO4 | 4.662 | 4.921 | 4.331 | 5.919 | 6.290 | 7.140 | 3.091 | 0.0081539 | roundabout homolog 4, magic roundabout (Drosophila) |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| SLC14A1 | 6.688 | 6.583 | 5.833 | 7.466 | 7.669 | 8.883 | 3.101 | 0.0248907 | solute carrier family 14 (urea transporter), member 1 (Kidd blood group) |
| MFSD6 | 3.832 | 3.649 | 3.913 | 4.796 | 5.474 | 6.393 | 3.120 | 0.0143498 | major facilitator superfamily domain containing 6 |
| TMEM126B | 2.410 | 2.270 | 2.403 | 3.221 | 4.051 | 5.010 | 3.132 | 0.0192863 | transmembrane protein 126B |
| DBNL | 8.012 | 7.963 | 6.879 | 8.533 | 9.545 | 10.060 | 3.145 | 0.0239308 | drebrin-like |
| ALG3 | 7.055 | 7.257 | 6.799 | 8.911 | 8.098 | 8.781 | 3.147 | 0.0083037 | asparagine-linked glycosylation 3, alpha-1,3-mannosyltransferase homolog (S. cerevisiae) |
| C5orf22 | 1.420 | 1.166 | 1.710 | 2.429 | 3.075 | 3.748 | 3.149 | 0.0140859 | chromosome 5 open reading frame 22 |
| CDH13 | 3.949 | 5.217 | 5.411 | 6.150 | 6.819 | 7.067 | 3.150 | 0.0168998 | cadherin 13, H-cadherin (heart) |
| C1D | 5.147 | 5.682 | 5.393 | 8.144 | 6.803 | 6.807 | 3.151 | 0.0112840 | C1D nuclear receptor corepressor |
| ADK | 1.971 | 2.085 | 3.504 | 3.349 | 4.926 | 5.161 | 3.155 | 0.0292712 | adenosine kinase |
| RSU1 | 4.324 | 4.344 | 4.540 | 4.933 | 6.751 | 6.003 | 3.157 | 0.0381010 | Ras suppressor protein 1 |
| KIAA0649 | 4.454 | 4.479 | 3.231 | 5.750 | 4.892 | 6.627 | 3.161 | 0.0355722 | KIAA0649 |
| AKTIP | 2.135 | 2.062 | 1.925 | 3.724 | 5.278 | 3.411 | 3.163 | 0.0103226 | AKT interacting protein |
| RNF7 | 6.089 | 6.611 | 6.712 | 8.138 | 7.893 | 8.374 | 3.165 | 0.0038529 | ring finger protein 7 |
| SH3GLB1 | 5.834 | 5.589 | 5.907 | 7.177 | 7.496 | 7.983 | 3.165 | 0.0029535 | SH3-domain GRB2-like endophilin B1 |
| FAM127B | 2.409 | 2.926 | 2.343 | 3.678 | 5.118 | 4.072 | 3.166 | 0.0154036 | family with sequence similarity 127, member B |
| INHBB | 4.093 | 5.539 | 5.737 | 6.142 | 6.750 | 7.401 | 3.168 | 0.0386101 | inhibin, beta B |
| PROSC | 5.361 | 4.993 | 4.732 | 6.477 | 7.259 | 6.397 | 3.173 | 0.0075662 | proline synthetase co-transcribed homolog (bacterial) |
| CCDC58 | 1.692 | 1.484 | 2.980 | 3.002 | 4.646 | 3.456 | 3.175 | 0.0443824 | coiled-coil domain containing 58 |
| C5orf55 | 3.449 | 4.247 | 2.085 | 4.307 | 5.004 | 5.914 | 3.176 | 0.0436252 | chromosome 5 open reading frame 55 |
| RBX1 | 7.355 | 7.005 | 7.714 | 8.392 | 9.372 | 9.381 | 3.176 | 0.0106297 | ring-box 1, E3 ubiquitin protein ligase |
| FRMD3 | 1.974 | 1.974 | 1.974 | 3.642 | 4.098 | 2.973 | 3.179 | 0.0097084 | FERM domain containing 3 |
| RAB6A | 5.056 | 5.117 | 4.657 | 6.728 | 5.405 | 7.498 | 3.185 | 0.0419149 | RAB6A, member RAS oncogene family |
| FAM24B | 0.166 | 0.420 | 0.951 | 2.092 | 2.092 | 2.335 | 3.185 | 0.0042523 | family with sequence similarity 24, member B |
| PMS2L5 | 0.951 | 0.420 | 0.420 | 2.092 | 2.092 | 3.795 | 3.185 | 0.0120806 | No description |
| NUDT4 | 8.726 | 8.521 | 8.160 | 9.652 | 10.192 | 11.509 | 3.186 | 0.0136433 | nudix (nucleoside diphosphate linked moiety X)-type motif 4 |
| C8orf41 | 3.676 | 4.221 | 4.138 | 6.153 | 4.710 | 5.813 | 3.193 | 0.0251033 | chromosome 8 open reading frame 41 |
| DMRTA1 | 1.161 | 1.161 | −0.834 | 2.837 | 2.837 | 2.165 | 3.195 | 0.0173869 | DMRT-like family A1 |
| RAB5C | 6.178 | 6.822 | 6.557 | 8.234 | 8.664 | 7.766 | 3.197 | 0.0066335 | RAB5C, member RAS oncogene family |
| DHCR7 | 4.715 | 4.909 | 4.340 | 7.087 | 6.017 | 6.143 | 3.198 | 0.0082129 | 7-dehydrocholesterol reductase |
| NUCKS1 | 9.526 | 9.521 | 9.568 | 11.248 | 10.321 | 11.212 | 3.206 | 0.0169951 | nuclear casein kinase and cyclin-dependent kinase substrate 1 |
| SRI | 4.551 | 5.291 | 4.275 | 5.956 | 6.476 | 6.504 | 3.207 | 0.0110662 | sorcin |
| LHFP | 7.308 | 6.751 | 7.082 | 8.170 | 8.764 | 8.991 | 3.208 | 0.0078506 | lipoma HMGIC fusion partner |
| AGTPBP1 | 2.735 | 3.161 | 3.962 | 4.895 | 4.754 | 4.843 | 3.209 | 0.0146524 | ATP/GTP binding protein 1 |
| C7orf30 | 2.424 | 3.727 | 4.735 | 4.766 | 6.418 | 5.185 | 3.211 | 0.0488234 | chromosome 7 open reading frame 30 |
| PRDX6 | 11.906 | 10.973 | 10.915 | 12.793 | 12.231 | 13.592 | 3.217 | 0.0256963 | peroxiredoxin 6 |
| PRKAB1 | 4.571 | 4.640 | 5.137 | 5.790 | 6.375 | 6.824 | 3.220 | 0.0134036 | protein kinase, AMP-activated, beta 1 non-catalytic subunit |
| NFYB | 3.519 | 3.486 | 4.739 | 5.174 | 6.250 | 5.206 | 3.221 | 0.0283514 | nuclear transcription factor Y, beta |
| TSSC1 | 3.348 | 4.079 | 3.068 | 5.236 | 4.791 | 5.035 | 3.221 | 0.0125321 | tumor suppressing subtransferable candidate 1 |
| LOC147727 | 4.853 | 4.827 | 4.416 | 6.323 | 6.105 | 7.225 | 3.223 | 0.0060095 | No description |
| STARD3NL | 6.602 | 7.250 | 6.972 | 8.660 | 7.871 | 9.060 | 3.223 | 0.0157394 | STARD3 N-terminal like |
| LANCL1 | 3.176 | 3.332 | 3.784 | 4.485 | 5.021 | 6.522 | 3.224 | 0.0207810 | LanC lantibiotic synthetase component C-like 1 (bacterial) |
| TMEM62 | 3.718 | 3.719 | 4.285 | 5.385 | 5.409 | 6.911 | 3.226 | 0.0108559 | transmembrane protein 62 |
| PSMG2 | 5.879 | 5.764 | 6.553 | 8.117 | 7.455 | 8.218 | 3.228 | 0.0047765 | proteasome (prosome, macropain) assembly chaperone 2 |
| C9orf95 | 4.665 | 5.121 | 5.552 | 5.857 | 6.812 | 7.474 | 3.229 | 0.0293294 | chromosome 9 open reading frame 95 |
| ANKMY1 | 4.134 | 2.702 | 3.234 | 5.633 | 4.059 | 5.827 | 3.232 | 0.0330087 | ankyrin repeat and MYND domain containing 1 |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| DDAH1 | 3.610 | 4.294 | 3.405 | 5.305 | 6.168 | 5.050 | 3.238 | 0.0121721 | dimethylarginine dimethylaminohydrolase 1 |
| LOC647979 | 6.930 | 6.847 | 6.499 | 8.951 | 8.543 | 8.111 | 3.242 | 0.0036698 | No description |
| MAPK3 | 8.663 | 8.203 | 6.597 | 8.796 | 9.613 | 10.361 | 3.243 | 0.0462500 | mitogen-activated protein kinase 3 |
| UQCRFS1 | 8.020 | 8.490 | 9.211 | 9.719 | 10.294 | 10.252 | 3.247 | 0.0189202 | ubiquinol-cytochrome c reductase, Rieske iron-sulfur polypeptide 1 |
| PEX14 | 2.973 | 2.901 | 3.361 | 4.673 | 5.462 | 3.919 | 3.250 | 0.0213483 | peroxisomal biogenesis factor 14 |
| LPGAT1 | 4.407 | 4.423 | 4.751 | 6.124 | 6.657 | 5.856 | 3.252 | 0.0044905 | lysophosphatidylglycerol acyltransferase 1 |
| NXNL2 | 3.859 | 3.596 | 4.465 | 5.743 | 5.299 | 5.670 | 3.255 | 0.0076154 | nucleoredoxin-like 2 |
| ISOC1 | 4.471 | 4.559 | 4.601 | 6.263 | 5.983 | 6.453 | 3.257 | 0.0015359 | isochorismatase domain containing 1 |
| ATOX1 | 9.713 | 8.951 | 8.201 | 9.905 | 10.375 | 11.743 | 3.259 | 0.0412387 | ATX1 antioxidant protein 1 homolog (yeast) |
| FBXO27 | 5.953 | 5.690 | 5.637 | 7.396 | 6.724 | 8.951 | 3.261 | 0.0228294 | F-box protein 27 |
| PEX7 | 3.458 | 1.862 | 2.741 | 3.439 | 4.546 | 5.167 | 3.269 | 0.0405874 | peroxisomal biogenesis factor 7 |
| TIGD2 | 0.692 | 1.161 | 0.456 | 3.070 | 2.165 | 2.165 | 3.270 | 0.0092984 | tigger transposable element derived 2 |
| APOBEC3B | 0.692 | 0.456 | 1.161 | 2.165 | 4.310 | 2.165 | 3.270 | 0.0204671 | apolipoprotein B mRNA editing enzyme, catalytic polypeptide-like 3B |
| DNASE1L1 | 2.551 | 2.795 | 2.455 | 3.444 | 4.372 | 4.508 | 3.277 | 0.0152583 | deoxyribonuclease 1-like 1 |
| TMEM14B | 4.554 | 4.771 | 6.299 | 6.056 | 7.713 | 8.012 | 3.279 | 0.0302772 | transmembrane protein 14B |
| OGFRL1 | 4.345 | 4.686 | 4.666 | 6.154 | 6.848 | 6.064 | 3.291 | 0.0033438 | opioid growth factor receptor-like 1 |
| LTF | 1.751 | 2.144 | 2.832 | 3.030 | 6.694 | 3.864 | 3.294 | 0.0487636 | lactotransferrin |
| KLHL5 | 2.567 | 2.051 | 2.051 | 2.821 | 3.771 | 4.714 | 3.295 | 0.0390473 | kelch-like 5 (Drosophila) |
| PPIL5 | 3.168 | 3.778 | 4.066 | 5.239 | 4.890 | 6.040 | 3.299 | 0.0129126 | peptidylproly isomerase (cyclophilin)-like 5 |
| AP3S1 | 2.494 | 1.453 | 2.101 | 4.051 | 4.218 | 3.163 | 3.302 | 0.0111865 | adaptor-related protein complex 3, sigma 1 subunit |
| TTC38 | 3.660 | 2.973 | 2.983 | 4.710 | 4.136 | 6.100 | 3.310 | 0.0274724 | tetratricopeptide repeat domain 38 |
| HS3ST1 | 1.438 | 1.318 | 0.751 | 3.048 | 1.977 | 4.119 | 3.316 | 0.0243158 | heparan sulfate (glucosamine) 3-O-sulfotransferase 1 |
| NAGPA | 1.318 | 2.542 | 1.748 | 4.811 | 3.048 | 3.253 | 3.316 | 0.0276607 | N-acetylglucosamine-1-phosphodiester alpha-N-acetylglucosaminidase |
| Magmas | 6.436 | 6.430 | 5.930 | 7.863 | 7.661 | 8.462 | 3.320 | 0.0050617 | No description |
| DLG3 | 2.973 | 2.735 | 2.051 | 3.890 | 3.784 | 4.714 | 3.324 | 0.0185163 | discs, large homolog 3 (Drosophila) |
| TMEM205 | 4.059 | 4.257 | 4.326 | 6.132 | 5.992 | 5.384 | 3.329 | 0.0049043 | transmembrane protein 205 |
| RPE | 1.453 | 0.751 | 1.172 | 2.487 | 3.982 | 2.487 | 3.331 | 0.0155685 | ribulose-5-phosphate-3-epimerase |
| C18orf18 | 0.925 | 2.040 | 0.751 | 3.048 | 3.256 | 2.487 | 3.331 | 0.0167984 | chromosome 18 open reading frame 18 |
| C7orf68 | 0.751 | 0.751 | 0.751 | 1.453 | 3.752 | 2.487 | 3.331 | 0.0294285 | chromosome 7 open reading frame 68 |
| C19orf52 | 3.256 | 4.065 | 4.119 | 5.857 | 4.795 | 5.851 | 3.336 | 0.0158234 | chromosome 19 open reading frame 52 |
| DGUOK | 6.055 | 5.944 | 6.461 | 8.200 | 7.516 | 8.093 | 3.338 | 0.0031865 | deoxyguanosine kinase |
| LYN | 3.413 | 5.851 | 5.358 | 7.183 | 6.543 | 7.097 | 3.339 | 0.0249020 | v-yes-1 Yamaguchi sarcoma viral related oncogene homolog |
| BLCAP | 7.418 | 6.824 | 6.094 | 7.430 | 8.565 | 9.686 | 3.342 | 0.0428037 | bladder cancer associated protein |
| CCDC107 | 4.665 | 4.997 | 5.026 | 6.111 | 6.739 | 7.737 | 3.344 | 0.0089134 | coiled-coil domain containing 107 |
| LOC100286844 | 2.027 | 2.264 | 1.595 | 2.928 | 3.770 | 4.861 | 3.347 | 0.0183778 | No description |
| NAA20 | 5.706 | 5.449 | 6.291 | 8.035 | 7.376 | 7.237 | 3.350 | 0.0074194 | N(alpha)-acetyltransferase 20, NatB catalytic subunit |
| MRPL12 | 7.827 | 9.107 | 7.575 | 9.861 | 9.629 | 9.323 | 3.359 | 0.0389974 | mitochondrial ribosomal protein L12 |
| NDRG2 | 7.037 | 7.528 | 6.782 | 7.988 | 9.279 | 8.843 | 3.366 | 0.0192356 | NDRG family member 2 |
| DDT | 6.886 | 7.724 | 8.060 | 8.264 | 9.476 | 9.948 | 3.367 | 0.0334179 | D-dopachrome tautomerase |
| LOC440944 | 5.347 | 6.109 | 5.007 | 7.250 | 6.085 | 7.862 | 3.371 | 0.0421017 | No description |
| IDE | 4.404 | 5.674 | 4.696 | 7.428 | 6.112 | 7.030 | 3.374 | 0.0134489 | Description |
| HOXA4 | 2.315 | 2.314 | 1.493 | 3.349 | 3.330 | 4.069 | 3.374 | 0.0152061 | homeobox A4 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| NCKIPSD | 3.653 | 3.275 | 2.797 | 4.552 | 5.822 | 4.742 | 3.375 | 0.0125057 | NCK interacting protein with SH3 domain |
| RAP1GDS1 | 4.501 | 4.181 | 2.617 | 5.859 | 4.689 | 6.258 | 3.381 | 0.0371955 | RAP1, GTP-GDP dissociation stimulator 1 |
| BTF3L4 | 4.221 | 4.941 | 5.948 | 6.586 | 6.740 | 6.699 | 3.382 | 0.0232311 | basic transcription factor 3-like 4 |
| HSPBAP1 | 3.717 | 4.208 | 3.939 | 5.708 | 4.649 | 5.968 | 3.386 | 0.0246918 | HSPB (heat shock 27 kDa) associated protein 1 |
| MRPL19 | 3.780 | 4.363 | 4.172 | 5.632 | 6.124 | 5.925 | 3.389 | 0.0022402 | mitochondrial ribosomal protein L19 |
| C7orf49 | 3.960 | 4.036 | 4.057 | 5.797 | 5.431 | 5.879 | 3.390 | 0.0015586 | chromosome 7 open reading frame 49 |
| POP4 | 4.088 | 4.377 | 4.444 | 5.854 | 5.892 | 6.699 | 3.400 | 0.0034376 | processing of precursor 4, ribonuclease P/MRP subunit (S. cerevisiae) |
| MIF4GD | 4.668 | 5.550 | 4.363 | 6.438 | 6.422 | 7.025 | 3.409 | 0.0095964 | MIF4G domain containing |
| GNGT2 | 0.925 | 2.494 | 1.318 | 2.698 | 3.248 | 3.852 | 3.416 | 0.0282523 | guanine nucleotide binding protein (G protein), gamma transducing activity polypeptide 2 |
| PARP1 | 5.650 | 5.613 | 5.563 | 7.387 | 6.941 | 7.898 | 3.420 | 0.0034036 | poly (ADP-ribose) polymerase 1 |
| SACM1L | 3.257 | 3.410 | 2.947 | 5.122 | 5.187 | 3.687 | 3.428 | 0.0376229 | SAC1 suppressor of actin mutations 1-like (yeast) |
| HMGN1 | 5.407 | 4.718 | 6.135 | 7.646 | 6.719 | 7.192 | 3.447 | 0.0156055 | high-mobility group nucleosome binding domain 1 |
| CCDC25 | 4.558 | 4.481 | 5.302 | 6.266 | 6.942 | 6.538 | 3.448 | 0.0051441 | coiled-coil domain containing 25 |
| NDUFA8 | 6.734 | 7.265 | 6.361 | 7.978 | 9.055 | 8.975 | 3.457 | 0.0082470 | NADH dehydrogenase (ubiquinone) 1 alpha subcomplex, 8, 19 kDa |
| GCDH | 4.818 | 5.771 | 4.659 | 6.452 | 6.577 | 8.469 | 3.465 | 0.0213597 | glutaryl-CoA dehydrogenase |
| OSGIN2 | 4.134 | 4.330 | 3.474 | 5.927 | 5.179 | 7.286 | 3.466 | 0.0139641 | oxidative stress induced growth inhibitor family member 2 |
| MEIS3P1 | 2.821 | 3.612 | 3.363 | 5.408 | 4.752 | 4.843 | 3.473 | 0.0055647 | Meis homeobox 3 pseudogene 1 |
| PRKRA | 4.356 | 4.022 | 3.994 | 5.870 | 5.794 | 5.828 | 3.482 | 0.0012220 | protein kinase, interferon-inducible double stranded RNA dependent activator |
| MPDU1 | 2.242 | 2.156 | 2.029 | 3.015 | 4.045 | 4.002 | 3.490 | 0.0128937 | mannose-P-dolichol utilization defect 1 |
| MAPKAPK3 | 3.652 | 4.276 | 4.587 | 6.082 | 5.177 | 6.631 | 3.496 | 0.0158120 | mitogen-activated protein kinase-activated protein kinase 3 |
| VDAC3 | 3.949 | 4.470 | 4.715 | 6.297 | 6.448 | 5.756 | 3.497 | 0.0046925 | voltage-dependent anion channel 3 |
| FDFT1 | 5.926 | 5.470 | 5.903 | 7.914 | 7.614 | 7.276 | 3.497 | 0.0021176 | farnesyl-diphosphate farnesyltransferase 1 |
| DHRSX | 4.324 | 4.381 | 4.940 | 6.381 | 6.188 | 6.146 | 3.501 | 0.0026797 | dehydrogenase/reductase (SDR family) X-linked |
| USHBP1 | 2.395 | 3.669 | 2.917 | 4.031 | 4.731 | 5.968 | 3.515 | 0.0243688 | Usher syndrome 1C binding protein 1 |
| EXD2 | 5.243 | 4.153 | 3.653 | 6.044 | 5.471 | 6.260 | 3.525 | 0.0302016 | exonuclease 3'-5' domain containing 2 |
| GABARAPL2 | 3.347 | 3.809 | 3.570 | 4.489 | 6.358 | 5.390 | 3.530 | 0.0178831 | GABA(A) receptor-associated protein-like 2 |
| SLC29A2 | 1.938 | 2.164 | 1.595 | 3.506 | 3.416 | 4.317 | 3.532 | 0.0045768 | solute carrier family 29 (nucleoside transporters), member 2 |
| TYMS | 3.338 | 2.485 | 1.493 | 4.742 | 3.074 | 5.161 | 3.539 | 0.0433597 | thymidylate synthetase |
| ARPC5 | 6.262 | 4.627 | 5.972 | 6.838 | 6.802 | 8.087 | 3.543 | 0.0441048 | actin related protein 2/3 complex, subunit 5, 16 kDa |
| C17orf37 | 5.112 | 5.446 | 6.094 | 6.939 | 7.802 | 7.347 | 3.549 | 0.0071751 | chromosome 17 open reading frame 37 |
| SERPINB6 | 8.629 | 9.321 | 8.273 | 10.101 | 10.594 | 11.064 | 3.551 | 0.0080934 | serpin peptidase inhibitor, clade B (ovalbumin), member 6 |
| IFI44 | 2.270 | 3.723 | 3.410 | 4.555 | 5.552 | 5.139 | 3.553 | 0.0115329 | interferon-induced protein 44 |
| FARS2 | 5.404 | 5.096 | 4.076 | 5.960 | 5.906 | 7.671 | 3.556 | 0.0480276 | phenylalanyl-tRNA synthetase 2, mitochondrial |
| ASMTL | 4.448 | 4.365 | 4.056 | 6.213 | 5.568 | 6.279 | 3.559 | 0.0035957 | acetylserotonin O-methyltransferase-like |
| CASKIN2 | 4.917 | 4.965 | 3.108 | 5.175 | 6.797 | 6.727 | 3.560 | 0.0390624 | CASK interacting protein 2 |
| RUNDC2A | 1.081 | 1.081 | 1.880 | 2.915 | 3.439 | 3.687 | 3.566 | 0.0031751 | RUN domain containing 2A |
| C14orf156 | 4.777 | 5.412 | 6.033 | 6.848 | 7.867 | 6.992 | 3.566 | 0.0125208 | chromosome 14 open reading frame 156 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| GLRX | 5.895 | 6.755 | 7.699 | 7.949 | 9.117 | 8.595 | 3.580 | 0.0272969 | glutaredoxin (thioltransferase) |
| LNX1 | 3.656 | 3.249 | 4.217 | 4.538 | 5.603 | 6.058 | 3.583 | 0.0229126 | ligand of numb-protein X 1 |
| NSMCE4A | 1.488 | 1.949 | 2.155 | 3.647 | 4.565 | 3.333 | 3.592 | 0.0055533 | non-SMC element 4 homolog A (S. cerevisiae) |
| MPHOSPH6 | 6.606 | 6.101 | 6.087 | 8.007 | 7.256 | 8.451 | 3.593 | 0.0125889 | M-phase phosphoprotein 6 |
| ELTD1 | 7.018 | 9.386 | 8.541 | 10.556 | 9.891 | 10.387 | 3.596 | 0.0257878 | EGF, latrophilin and seven transmembrane domain containing 1 |
| TREX1 | 5.203 | 5.761 | 4.880 | 7.051 | 6.590 | 7.994 | 3.600 | 0.0096449 | three prime repair exonuclease 1 |
| CHCHD8 | 3.526 | 4.995 | 5.426 | 6.586 | 7.275 | 6.230 | 3.602 | 0.0165216 | coiled-coil-helix-coiled-coil-helix domain containing 8 |
| VPS25 | 7.548 | 6.352 | 5.701 | 8.784 | 7.481 | 9.397 | 3.602 | 0.0284512 | vacuolar protein sorting 25 homolog (S. cerevisiae) |
| C10orf35 | 2.745 | 2.165 | 1.888 | 4.020 | 3.722 | 5.185 | 3.618 | 0.0083922 | chromosome 10 open reading frame 35 |
| FAM89A | 2.489 | 3.264 | 3.412 | 4.050 | 5.120 | 5.988 | 3.620 | 0.0168098 | family with sequence similarity 89, member A |
| PECAM1 | 5.642 | 5.553 | 6.757 | 7.517 | 7.409 | 7.526 | 3.621 | 0.0192659 | platelet/endothelial cell adhesion molecule |
| MORF4L1 | 9.630 | 10.185 | 10.430 | 12.465 | 11.094 | 12.043 | 3.625 | 0.0132795 | mortality factor 4 like 1 |
| COMMD8 | 1.299 | 1.299 | 1.493 | 3.159 | 4.724 | 2.625 | 3.630 | 0.0120616 | COMM domain containing 8 |
| C3orf1 | 6.263 | 5.617 | 6.146 | 7.781 | 7.479 | 8.705 | 3.634 | 0.0056131 | chromosome 3 open reading frame 1 |
| FKBP3 | 2.067 | 1.983 | 3.569 | 3.848 | 4.838 | 4.264 | 3.644 | 0.0238400 | FK506 binding protein 3, 25 kDa |
| OXCT1 | 1.751 | 2.144 | 2.144 | 2.392 | 4.582 | 4.011 | 3.648 | 0.0432371 | 3-oxoacid CoA transferase 1 |
| SCCPDH | 2.144 | 2.702 | 4.063 | 4.013 | 6.299 | 4.461 | 3.653 | 0.0464300 | saccharopine dehydrogenase (putative) |
| NEK9 | 4.072 | 5.078 | 4.068 | 6.139 | 6.127 | 5.939 | 3.657 | 0.0088264 | NIMA (never in mitosis gene a)-related kinase 9 |
| HDHD2 | 3.012 | 2.244 | 2.539 | 3.557 | 4.411 | 5.698 | 3.660 | 0.0207432 | haloacid dehalogenase-like hydrolase domain containing 2 |
| ANXA6 | 8.952 | 8.503 | 7.636 | 9.112 | 10.379 | 11.064 | 3.671 | 0.0317682 | annexin A6 |
| SNAP29 | 4.215 | 4.068 | 4.731 | 6.049 | 6.255 | 6.091 | 3.672 | 0.0019346 | synaptosomal-associated protein, 29 kDa |
| C21orf59 | 2.135 | 3.128 | 2.213 | 4.650 | 4.017 | 4.683 | 3.686 | 0.0048854 | chromosome 21 open reading frame 59 |
| GLRX3 | 3.624 | 4.041 | 4.445 | 5.934 | 6.330 | 4.966 | 3.693 | 0.0165775 | glutaredoxin 3 |
| KLF15 | 3.640 | 2.480 | 4.180 | 5.894 | 5.525 | 4.699 | 3.693 | 0.0180730 | Kruppel-like factor 15 |
| SCP2 | 2.675 | 2.804 | 2.853 | 3.514 | 6.545 | 4.693 | 3.706 | 0.0313952 | sterol carrier protein 2 |
| DCTN2 | 9.483 | 8.349 | 8.070 | 10.875 | 9.722 | 11.376 | 3.712 | 0.0175110 | dynactin 2 (p50) |
| ARHGEF16 | 3.142 | 2.085 | 1.611 | 2.817 | 4.385 | 5.035 | 3.714 | 0.0468340 | Rho guanine nucleotide exchange factor (GEF) 16 |
| H3F3C | 4.804 | 5.125 | 5.118 | 7.012 | 8.091 | 5.351 | 3.717 | 0.0473983 | H3 histone, family 3C |
| C4orf27 | 1.611 | 3.462 | 3.454 | 3.696 | 5.356 | 5.251 | 3.717 | 0.0383173 | chromosome 4 open reading frame 27 |
| LOC148413 | 4.039 | 4.689 | 4.233 | 6.141 | 6.189 | 6.064 | 3.753 | 0.0016660 | No description |
| PECI | 5.619 | 4.546 | 6.162 | 7.307 | 7.763 | 7.528 | 3.755 | 0.0065692 | peroxisomal D3,D2-enoyl-CoA isomerase |
| MYLK | 6.970 | 7.804 | 6.564 | 9.336 | 8.223 | 9.713 | 3.756 | 0.0138067 | myosin light chain kinase |
| ADH5 | 5.157 | 4.484 | 6.771 | 6.399 | 8.161 | 7.409 | 3.769 | 0.0488014 | alcohol dehydrogenase 5 (class III), chi polypeptide |
| psITPTE22 | 0.420 | 1.738 | 0.420 | 2.567 | 2.335 | 3.456 | 3.771 | 0.0142492 | No description |
| APOO | 3.256 | 2.968 | 1.172 | 5.173 | 4.081 | 3.852 | 3.778 | 0.0346827 | apolipoprotein O |
| MMEL1 | 3.069 | 3.069 | 1.353 | 3.275 | 4.695 | 6.135 | 3.789 | 0.0387780 | membrane metallo-endopeptidase-like 1 |
| AK3 | 4.894 | 4.153 | 4.505 | 5.686 | 6.429 | 7.010 | 3.795 | 0.0090548 | adenylate kinase 3 |
| HDDC2 | 3.783 | 3.368 | 4.027 | 4.428 | 7.665 | 5.710 | 3.803 | 0.0344981 | HD domain containing 2 |
| MRPL16 | 6.375 | 5.623 | 5.652 | 7.583 | 7.151 | 8.449 | 3.814 | 0.0101335 | mitochondrial ribosomal protein L16 |
| MAGOHB | 3.338 | 3.892 | 3.425 | 5.827 | 4.921 | 5.741 | 3.824 | 0.0034187 | mago-nashi homolog B (Drosophila) |
| AP1M1 | 8.809 | 8.197 | 7.532 | 10.171 | 9.168 | 10.747 | 3.831 | 0.0198143 | adaptor-related protein complex 1, mu 1 subunit |
| COMMD7 | 7.016 | 6.693 | 6.310 | 7.862 | 8.631 | 9.793 | 3.832 | 0.0114384 | COMM domain containing 7 |
| KIAA0494 | 5.754 | 5.612 | 6.722 | 7.551 | 7.916 | 7.716 | 3.833 | 0.0091320 | KIAA0494 |
| DSTN | 4.689 | 4.850 | 5.422 | 6.811 | 7.361 | 6.548 | 3.833 | 0.0034792 | destrin (actin depolymerizing factor) |
| CLNS1A | 6.044 | 5.390 | 6.368 | 7.329 | 8.182 | 8.053 | 3.835 | 0.0055874 | chloride channel, nucleotide-sensitive, 1A |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| MYL12A | 8.168 | 7.118 | 8.751 | 9.420 | 10.691 | 9.623 | 3.837 | 0.0199716 | myosin, light chain 12A, regulatory, non-sarcomeric |
| ALG5 | 4.080 | 4.104 | 4.896 | 5.660 | 6.837 | 6.108 | 3.841 | 0.0093098 | asparagine-linked glycosylation 5, dolichyl-phosphate beta-glucosyltransferase homolog (S. cerevisiae) |
| C6orf64 | 4.740 | 4.465 | 4.537 | 6.483 | 5.813 | 7.631 | 3.853 | 0.0091131 | chromosome 6 open reading frame 64 |
| C9orf119 | 2.069 | 1.748 | 0.751 | 2.698 | 4.190 | 3.528 | 3.854 | 0.0156592 | chromosome 9 open reading frame 119 |
| PIGS | 6.280 | 6.845 | 5.888 | 8.654 | 6.691 | 8.795 | 3.863 | 0.0465934 | phosphatidylinositol glycan anchor biosynthesis, class S |
| PPAP2C | 3.029 | 5.412 | 4.880 | 5.521 | 6.936 | 6.831 | 3.866 | 0.0377727 | phosphatidic acid phosphatase type 2C |
| EIF4EBP1 | 4.753 | 4.182 | 5.927 | 6.479 | 7.882 | 6.252 | 3.879 | 0.0289285 | eukaryotic translation initiation factor 4E binding protein 1 |
| FAM50B | 5.077 | 4.257 | 3.317 | 5.763 | 5.273 | 8.409 | 3.879 | 0.0446910 | family with sequence similarity 50, member B |
| TPD52L1 | 3.841 | 5.024 | 5.321 | 5.350 | 9.026 | 6.983 | 3.888 | 0.0416668 | tumor protein D52-like 1 |
| PHYH | 1.813 | 2.742 | 2.495 | 2.853 | 6.330 | 4.456 | 3.894 | 0.0435851 | phytanoyl-CoA 2-hydroxylase |
| CDKN2AIPNL | 2.676 | 2.908 | 2.757 | 3.197 | 5.366 | 4.719 | 3.896 | 0.0399875 | CDKN2A interacting protein N-terminal like |
| ARL2BP | 3.486 | 3.739 | 5.477 | 5.452 | 6.004 | 6.224 | 3.906 | 0.0417568 | ADP-ribosylation factor-like 2 binding protein |
| TNFRSF11B | 0.166 | 0.166 | 1.122 | 1.122 | 3.091 | 2.335 | 3.913 | 0.0368691 | tumor necrosis factor receptor superfamily, member 11b |
| XRCC5 | 5.648 | 6.132 | 6.339 | 8.307 | 8.134 | 7.572 | 3.914 | 0.0024278 | X-ray repair complementing defective repair in Chinese hamster cells 5 (double-strand-break rejoining) |
| NHP2 | 5.365 | 5.907 | 5.746 | 7.870 | 7.803 | 7.337 | 3.923 | 0.0013937 | NHP2 ribonucleoprotein homolog (yeast) |
| PCBP3 | 1.751 | 1.751 | 3.471 | 3.787 | 4.815 | 3.724 | 3.926 | 0.0324194 | poly(rC) binding protein 3 |
| FUT1 | 1.751 | 3.173 | 2.213 | 3.030 | 4.235 | 5.152 | 3.941 | 0.0431358 | fucosyltransferase 1 (galactoside 2-alpha-L-fucosyltransferase, H blood group) |
| BNIP2 | 4.965 | 5.431 | 5.165 | 7.389 | 6.404 | 7.410 | 3.943 | 0.0050957 | BCL2/adenovirus E1B 19 kDa interacting protein 2 |
| EIF4EBP2 | 6.736 | 6.479 | 6.738 | 7.518 | 8.717 | 8.958 | 3.946 | 0.0135927 | eukaryotic translation initiation factor 4E binding protein 2 |
| UBL7 | 6.703 | 6.728 | 5.586 | 7.577 | 7.623 | 8.711 | 3.954 | 0.0263287 | ubiquitin-like 7 (bone marrow stromal cell-derived) |
| TOM1L1 | 2.787 | 0.951 | 2.567 | 3.180 | 4.603 | 4.551 | 3.957 | 0.0253529 | target of myb1 (chicken)-like 1 |
| MLF2 | 6.541 | 6.309 | 6.587 | 8.380 | 8.296 | 8.789 | 3.965 | 0.0008075 | myeloid leukemia factor 2 |
| RPS19BP1 | 6.952 | 6.773 | 4.977 | 8.237 | 7.829 | 8.942 | 3.971 | 0.0183930 | ribosomal protein S19 binding protein 1 |
| PDHA1 | 7.876 | 7.757 | 6.516 | 8.507 | 8.590 | 9.866 | 3.972 | 0.0400155 | pyruvate dehydrogenase (lipoamide) alpha 1 |
| TAL1 | 2.480 | 4.648 | 3.490 | 5.732 | 4.471 | 5.778 | 3.974 | 0.0426653 | T-cell acute lymphocytic leukemia 1 |
| PDCD10 | 1.318 | 2.698 | 1.172 | 4.065 | 4.581 | 3.163 | 3.975 | 0.0105117 | programmed cell death 10 |
| FLJ33630 | 1.488 | 2.623 | 2.027 | 2.928 | 4.616 | 4.117 | 3.981 | 0.0210790 | No description |
| GPT2 | 6.153 | 3.913 | 3.945 | 5.906 | 7.230 | 7.790 | 3.982 | 0.0261872 | glutamic pyruvate transaminase (alanine aminotransferase) 2 |
| PARG | 3.681 | 2.646 | 3.246 | 5.144 | 4.639 | 5.947 | 3.983 | 0.0069331 | poly (ADP-ribose) glycohydrolase |
| APOLD1 | 7.998 | 7.643 | 9.597 | 9.639 | 11.569 | 11.240 | 3.988 | 0.0167795 | apolipoprotein L domain containing 1 |
| MAGEF1 | 3.797 | 4.328 | 3.578 | 6.524 | 5.204 | 5.798 | 4.004 | 0.0072666 | melanoma antigen family F, 1 |
| MMADHC | 5.323 | 5.701 | 6.106 | 7.710 | 7.738 | 7.694 | 4.026 | 0.0012878 | methylmalonic aciduria (cobalamin deficiency) cblD type, with homocystinuria |
| GALK2 | 1.949 | 1.488 | 1.595 | 3.115 | 3.626 | 3.960 | 4.032 | 0.0026048 | galactokinase 2 |
| CRADD | 3.919 | 1.923 | 1.919 | 3.931 | 4.654 | 5.139 | 4.034 | 0.0274353 | CASP2 and RIPK1 domain containing adaptor with death domain |
| CFL2 | 2.794 | 2.658 | 3.468 | 3.500 | 5.836 | 4.815 | 4.060 | 0.0414800 | cofilin 2 (muscle) |
| RAB4B | 2.467 | 3.464 | 2.899 | 5.025 | 4.117 | 5.490 | 4.071 | 0.0100367 | RAB4B, member RAS oncogene family |
| C19orf12 | 6.238 | 6.426 | 6.714 | 7.372 | 8.620 | 8.740 | 4.072 | 0.0123937 | chromosome 19 open reading frame 12 |
| TNS3 | 3.456 | 4.377 | 4.692 | 4.649 | 6.778 | 6.403 | 4.073 | 0.0437697 | tensin 3 |

TABLE 7-continued

Differentially Exprssed Genes in Stromal Breast Epithelial Cells

| | Nulliparous (NP) Samples | | | Parous (P) Samples | | | Pseudo | | |
|---|---|---|---|---|---|---|---|---|---|
| Gene Symbol | Stroma N33 | Stroma N35 | Stroma N58 | Stroma N37 | Stroma N39 | Stroma N40 | fold change | P value | Gene description |
| ACVRL1 | 6.396 | 6.664 | 6.360 | 8.424 | 7.496 | 8.780 | 4.079 | 0.0091676 | activin A receptor type II-like 1 |
| PIGP | 6.131 | 6.264 | 5.607 | 6.829 | 8.160 | 9.720 | 4.083 | 0.0239822 | phosphatidylinositol glycan anchor biosynthesis, class P |
| ALDH9A1 | 6.576 | 5.922 | 5.860 | 7.546 | 7.953 | 9.811 | 4.089 | 0.0126615 | aldehyde dehydrogenase 9 family, member A1 |
| CDK2AP1 | 6.109 | 5.452 | 6.538 | 7.484 | 8.682 | 7.483 | 4.089 | 0.0137107 | cyclin-dependent kinase 2 associated protein 1 |
| MAD2L1BP | 5.037 | 3.603 | 3.179 | 6.504 | 4.981 | 7.072 | 4.100 | 0.0221380 | MAD2L1 binding protein |
| ROBLD3 | 7.169 | 7.193 | 6.464 | 7.334 | 9.205 | 9.669 | 4.100 | 0.0412273 | roadblock domain containing 3 |
| PAFAH1B3 | 3.643 | 2.503 | 2.165 | 4.539 | 3.495 | 6.550 | 4.101 | 0.0470866 | platelet-activating factor acetylhydrolase 1b, catalytic subunit 3 (29 kDa) |
| TMEM204 | 8.429 | 8.374 | 6.995 | 9.558 | 9.268 | 10.467 | 4.107 | 0.0209542 | transmembrane protein 204 |
| C6orf211 | 3.450 | 1.453 | 3.048 | 4.190 | 4.444 | 5.490 | 4.113 | 0.0216986 | chromosome 6 open reading frame 211 |
| C15orf24 | 5.416 | 5.811 | 5.486 | 8.010 | 7.240 | 7.528 | 4.118 | 0.0015246 | chromosome 15 open reading frame 24 |
| PFN2 | 4.855 | 3.093 | 4.261 | 5.242 | 6.306 | 6.601 | 4.126 | 0.0197394 | profilin 2 |
| NME2P1 | 1.122 | 1.641 | 1.862 | 3.424 | 3.168 | 4.189 | 4.130 | 0.0033551 | non-metastatic cells 2, protein (NM23B) expressed in, pseudogene 1 |
| SAMM50 | 8.468 | 7.856 | 6.788 | 8.399 | 9.909 | 10.564 | 4.150 | 0.0375904 | sorting and assembly machinery component 50 homolog (*S. cerevisiae*) |
| MRPL10 | 5.278 | 4.250 | 4.863 | 6.775 | 6.310 | 7.707 | 4.172 | 0.0064187 | mitochondrial ribosomal protein L10 |
| HOXB8 | 0.751 | 2.926 | 1.453 | 2.746 | 4.190 | 4.996 | 4.199 | 0.0271812 | homeobox B8 |
| ABLIM3 | 6.407 | 7.289 | 7.382 | 8.315 | 9.362 | 11.097 | 4.207 | 0.0133022 | actin binding LIM protein family, member 3 |
| TB01D13 | 3.083 | 3.213 | 2.054 | 4.502 | 4.128 | 5.571 | 4.211 | 0.0140745 | TBC1 domain family, member 13 |
| MCCC1 | 2.928 | 3.333 | 3.145 | 3.938 | 5.617 | 5.220 | 4.214 | 0.0170344 | methylcrotonoyl-CoA carboxylase 1 (alpha) |
| RAD21 | 5.319 | 5.288 | 5.484 | 7.563 | 7.545 | 6.768 | 4.223 | 0.0020639 | RAD21 homolog (*S. pombe*) |
| CD320 | 6.831 | 6.886 | 6.227 | 8.307 | 8.915 | 9.359 | 4.239 | 0.0019981 | CD320 molecule |
| DCAKD | 1.611 | 1.166 | 1.299 | 2.045 | 3.696 | 3.596 | 4.241 | 0.0212023 | dephospho-CoA kinase domain containing |
| ISOC2 | 8.130 | 7.379 | 5.931 | 8.800 | 8.659 | 10.215 | 4.241 | 0.0282750 | isochorismatase domain containing 2 |
| METTL11A | 6.955 | 6.761 | 6.666 | 8.846 | 7.672 | 9.085 | 4.242 | 0.0131849 | methyltransferase like 11A |
| CWF19L2 | 4.254 | 5.130 | 5.256 | 6.346 | 6.570 | 7.776 | 4.261 | 0.0104331 | CWF19-like 2, cell cycle control (*S. pombe*) |
| TRIM21 | 1.748 | 2.968 | 2.968 | 3.957 | 3.840 | 5.490 | 4.263 | 0.0263400 | tripartite motif-containing 21 |
| APIP | 4.215 | 4.390 | 5.173 | 6.021 | 6.485 | 7.884 | 4.273 | 0.0102787 | APAF1 interacting protein |
| NAT6 | 2.092 | 2.567 | 2.946 | 4.016 | 4.672 | 5.208 | 4.301 | 0.0042107 | N-acetyltransferase 6 (GCN5-related) |
| FUCA1 | 2.745 | 1.880 | 2.857 | 4.853 | 3.840 | 5.883 | 4.310 | 0.0085117 | fucosidase, alpha-L-1, tissue |
| IER3IP1 | 3.692 | 3.149 | 3.671 | 5.802 | 5.258 | 5.410 | 4.314 | 0.0014762 | immediate early response 3 interacting protein 1 |
| PHGDH | 4.652 | 4.158 | 5.747 | 5.573 | 8.146 | 6.764 | 4.322 | 0.0418703 | phosphoglycerate dehydrogenase |
| SULT2B1 | 2.069 | 0.751 | 0.751 | 3.048 | 2.864 | 3.687 | 4.327 | 0.0086918 | sulfotransferase family, cytosolic, 2B, member 1 |
| USP30 | 2.871 | 2.807 | 2.670 | 5.174 | 4.921 | 4.688 | 4.328 | 0.0004240 | ubiquitin specific peptidase 30 |
| KRT17 | 7.951 | 7.653 | 8.812 | 9.767 | 11.048 | 9.935 | 4.328 | 0.0077485 | keratin 17 |
| AASDHPPT | 3.109 | 4.359 | 4.710 | 6.711 | 6.299 | 6.474 | 4.333 | 0.0027114 | aminoadipate-semialdehyde dehydrogenase-phosphopantetheinyl transferase |
| AIDA | 5.736 | 5.729 | 5.244 | 7.845 | 7.000 | 7.959 | 4.336 | 0.0027228 | axin interactor, dorsalization associated |
| SEP10 | 4.817 | 5.128 | 6.942 | 6.934 | 7.809 | 8.749 | 4.339 | 0.0245178 | septin 10 |
| ATP5J2 | 4.972 | 6.202 | 4.371 | 7.471 | 6.492 | 7.144 | 4.349 | 0.0215707 | ATP synthase, H+ transporting, mitochondrial Fo complex, subunit F2 |
| FAM69B | 2.999 | 2.676 | 2.144 | 3.486 | 5.029 | 5.122 | 4.355 | 0.0159875 | family with sequence similarity 69, member B |
| ORC4L | 2.572 | 2.994 | 2.716 | 4.840 | 3.693 | 5.428 | 4.359 | 0.0132644 | No description |
| ZSCAN16 | 2.741 | 3.131 | 1.898 | 4.866 | 3.168 | 5.546 | 4.363 | 0.0351562 | zinc finger and SCAN domain containing 16 |
| HOXA10 | 2.871 | 2.917 | 2.958 | 3.617 | 5.045 | 5.448 | 4.370 | 0.0198476 | homeobox A10 |
| CENPBD1 | 1.453 | 1.880 | 2.069 | 4.202 | 2.698 | 4.119 | 4.385 | 0.0137258 | CENPB DNA-binding domains containing 1 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| NUDT16 | 4.084 | 5.175 | 3.896 | 6.219 | 5.878 | 8.398 | 4.392 | 0.0175775 | nudix (nucleoside diphosphate linked moiety X)-type motif 16 |
| C11orf52 | 0.420 | 2.386 | 1.862 | 2.567 | 3.168 | 6.040 | 4.429 | 0.0499815 | chromosome 11 open reading frame 52 |
| ARHGEF5L | 2.745 | 2.614 | 2.424 | 4.766 | 4.128 | 5.901 | 4.445 | 0.0042636 | No description |
| AGL | 3.110 | 3.885 | 3.210 | 5.364 | 5.081 | 6.047 | 4.452 | 0.0028846 | amylo-alpha-1, 6-glucosidase, 4-alpha-glucanotransferase |
| ALG8 | 0.456 | −0.364 | −0.364 | 0.692 | 2.614 | 2.165 | 4.464 | 0.0211910 | asparagine-linked glycosylation 8, alpha-1,3-glucosyltransferase homolog (S. cerevisiae) |
| LSM4 | 7.752 | 7.298 | 6.886 | 8.320 | 9.458 | 10.604 | 4.470 | 0.0164890 | LSM4 homolog, U6 small nuclear RNA associated (S. cerevisiae) |
| MEF2C | 3.854 | 5.130 | 3.755 | 4.724 | 6.514 | 7.294 | 4.480 | 0.0458483 | myocyte enhancer factor 2C |
| CDC26 | 4.215 | 4.738 | 6.319 | 6.670 | 7.787 | 6.904 | 4.488 | 0.0222651 | cell division cycle 26 homolog (S. cerevisiae) |
| GRHPR | 7.027 | 6.588 | 6.179 | 7.695 | 8.756 | 9.559 | 4.494 | 0.0117213 | glyoxylate reductase/hydroxypyruvate reductase |
| SCGN | 0.166 | 0.166 | 0.166 | 1.588 | 5.623 | 2.335 | 4.497 | 0.0196554 | secretagogin, EF-hand calcium binding protein |
| GPR180 | 4.169 | 3.332 | 3.121 | 5.654 | 5.300 | 6.267 | 4.531 | 0.0030912 | G protein-coupled receptor 180 |
| SCOC | 1.595 | 1.488 | 1.755 | 3.777 | 4.672 | 3.662 | 4.536 | 0.0010011 | short coiled-coil protein |
| EXOSC1 | 2.542 | 1.453 | 3.455 | 4.065 | 4.835 | 4.726 | 4.545 | 0.0143309 | exosome component 1 |
| POLR2I | 6.026 | 6.342 | 5.051 | 7.237 | 7.653 | 8.671 | 4.553 | 0.0114232 | polymerase (RNA) II (DNA directed) polypeptide I, 14.5 kDa |
| DCXR | 10.494 | 10.219 | 7.366 | 12.123 | 10.728 | 12.684 | 4.563 | 0.0359467 | dicarbonyl/L-xylulose reductase |
| MRPL34 | 9.722 | 9.101 | 6.939 | 10.975 | 10.233 | 11.912 | 4.565 | 0.0231123 | mitochondrial ribosomal protein L34 |
| UIMC1 | 4.145 | 4.037 | 5.097 | 7.060 | 6.336 | 6.298 | 4.568 | 0.0035359 | ubiquitin interaction motif containing 1 |
| MTHFD2L | 2.608 | 2.387 | 2.326 | 5.423 | 4.582 | 4.099 | 4.577 | 0.0021615 | methylenetetrahydrofolate dehydrogenase (NADP+ dependent) 2-like |
| USMG5 | 3.458 | 4.390 | 5.290 | 6.587 | 9.261 | 5.634 | 4.588 | 0.0258082 | up-regulated during skeletal muscle growth 5 homolog (mouse) |
| CTF1 | 2.625 | 3.317 | 1.878 | 3.142 | 4.823 | 6.675 | 4.591 | 0.0442795 | cardiotrophin 1 |
| C15orf61 | 6.616 | 6.741 | 6.198 | 8.930 | 7.159 | 8.940 | 4.594 | 0.0235450 | chromosome 15 open reading frame 61 |
| ANKRD40 | 7.327 | 8.486 | 7.597 | 10.257 | 9.532 | 10.635 | 4.610 | 0.0030079 | ankyrin repeat domain 40 |
| PNPLA2 | 8.061 | 9.772 | 8.683 | 9.690 | 11.545 | 11.978 | 4.615 | 0.0244497 | patatin-like phospholipase domain containing 2 |
| RCSD1 | 1.318 | 2.060 | 2.445 | 3.527 | 4.148 | 5.050 | 4.623 | 0.0054111 | RCSD domain containing 1 |
| TKT | 6.051 | 6.223 | 5.847 | 7.428 | 8.260 | 8.849 | 4.623 | 0.0037379 | transketolase |
| ALKBH3 | 0.951 | 2.092 | 1.641 | 2.799 | 3.851 | 4.306 | 4.626 | 0.0093551 | alkB, alkylation repair homolog 3 (E. coli) |
| SCN4A | 5.747 | 7.271 | 4.567 | 8.088 | 6.778 | 9.065 | 4.632 | 0.0479648 | sodium channel, voltage-gated, type IV, alpha subunit |
| ADCK4 | 2.480 | 2.395 | 3.030 | 3.815 | 5.786 | 4.697 | 4.650 | 0.0106411 | aarF domain containing kinase 4 |
| DDIT4L | 1.938 | 2.901 | 3.065 | 5.120 | 3.357 | 5.879 | 4.656 | 0.0252939 | DNA-damage-inducible transcript 4-like |
| COX7A2 | 2.741 | 2.567 | 4.217 | 4.182 | 6.438 | 6.040 | 4.664 | 0.0189051 | cytochrome c oxidase subunit VIIa polypeptide 2 (liver) |
| MNAT1 | 6.335 | 6.047 | 5.176 | 7.588 | 7.422 | 8.565 | 4.691 | 0.0085496 | menage a trois homolog 1, cyclin H assembly factor (Xenopus laevis) |
| HEBP2 | 5.777 | 6.263 | 4.558 | 6.797 | 7.678 | 9.362 | 4.720 | 0.0199338 | heme binding protein 2 |
| SGK1 | 3.691 | 4.861 | 5.079 | 6.505 | 7.783 | 5.933 | 4.730 | 0.0142076 | serum/glucocorticoid regulated kinase 1 |
| PJA1 | 6.427 | 6.154 | 4.547 | 8.399 | 6.583 | 8.897 | 4.739 | 0.0278203 | praja ring finger 1 |
| MPV17 | 2.844 | 2.919 | 2.722 | 3.512 | 5.092 | 5.171 | 4.750 | 0.0199603 | MpV17 mitochondrial inner membrane protein |
| C7orf41 | 6.387 | 7.171 | 6.769 | 7.229 | 9.070 | 9.423 | 4.762 | 0.0364399 | chromosome 7 open reading frame 41 |
| SNORD95 | 0.692 | −0.364 | −0.364 | 1.888 | 1.161 | 4.812 | 4.763 | 0.0297039 | small nucleolar RNA, C/D box 95 |
| C20orf27 | 7.122 | 7.019 | 5.786 | 8.041 | 9.047 | 10.056 | 4.772 | 0.0099331 | chromosome 20 open reading frame 27 |
| TSPAN3 | 5.348 | 5.558 | 4.473 | 6.716 | 8.005 | 7.604 | 4.777 | 0.0038945 | tetraspanin 3 |
| ETFA | 2.734 | 4.155 | 5.486 | 5.867 | 7.171 | 6.412 | 4.780 | 0.0202069 | electron-transfer-flavoprotein, alpha polypeptide |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| FRY | 5.480 | 6.184 | 5.312 | 7.570 | 7.700 | 8.936 | 4.784 | 0.0031290 | furry homolog (Drosophila) |
| SNX15 | 5.034 | 5.069 | 5.040 | 6.020 | 7.330 | 7.325 | 4.791 | 0.0092757 | sorting nexin 15 |
| GPI | 3.073 | 3.550 | 3.120 | 4.702 | 5.386 | 6.273 | 4.811 | 0.0045208 | glucose-6-phosphate isomerase |
| PPP2R1B | 3.798 | 4.967 | 4.385 | 5.106 | 7.994 | 6.652 | 4.814 | 0.0292205 | protein phosphatase 2, regulatory subunit A, beta |
| TMEM141 | 6.080 | 5.696 | 4.547 | 6.202 | 8.237 | 8.348 | 4.814 | 0.0258907 | transmembrane protein 141 |
| MANEAL | 1.166 | 1.420 | 1.611 | 2.429 | 3.689 | 3.907 | 4.820 | 0.0090223 | mannosidase, endo-alpha-like |
| MCAM | 6.625 | 6.902 | 7.270 | 9.372 | 8.896 | 9.252 | 4.827 | 0.0007114 | melanoma cell adhesion molecule |
| UNC50 | 4.573 | 4.066 | 5.088 | 6.512 | 6.338 | 7.565 | 4.828 | 0.0043718 | unc-50 homolog (C. elegans) |
| UBE2V2 | 1.488 | 1.938 | 2.264 | 4.099 | 4.538 | 3.960 | 4.837 | 0.0009679 | ubiquitin-conjugating enzyme E2 variant 2 |
| HNRNPD | 7.054 | 8.188 | 6.985 | 10.059 | 9.466 | 9.262 | 4.848 | 0.0041176 | heterogeneous nuclear ribonucleoprotein D (AU-rich element RNA binding protein 1, 37 kDa) |
| C4orf3 | 6.933 | 7.219 | 7.224 | 7.720 | 9.497 | 9.567 | 4.850 | 0.0246222 | chromosome 4 open reading frame 3 |
| FAM107A | 3.739 | 3.294 | 5.791 | 4.783 | 8.069 | 7.236 | 4.852 | 0.0492235 | family with sequence similarity 107, member A |
| MRPS7 | 6.717 | 8.347 | 6.917 | 9.197 | 9.104 | 9.500 | 4.858 | 0.0117326 | mitochondrial ribosomal protein S7 |
| RPS6KA2 | 5.148 | 5.303 | 5.074 | 7.439 | 6.312 | 7.583 | 4.858 | 0.0059784 | ribosomal protein S6 kinase, 90 kDa, polypeptide 2 |
| CHMP4A | 6.608 | 7.038 | 6.468 | 7.379 | 9.108 | 9.319 | 4.860 | 0.0218272 | chromatin modifying protein 4A |
| NDUFS5 | 6.816 | 6.611 | 8.081 | 8.126 | 10.363 | 9.174 | 4.862 | 0.0276176 | NADH dehydrogenase (ubiquinone) Fe-S protein 5, 15 kDa (NADH-coenzyme Q reductase) |
| AOC3 | 4.535 | 5.319 | 4.665 | 5.262 | 7.605 | 7.416 | 4.878 | 0.0355306 | amine oxidase, copper containing 3 (vascular adhesion protein 1) |
| MTERFD2 | 4.317 | 4.446 | 3.942 | 6.610 | 5.383 | 8.262 | 4.903 | 0.0134603 | MTERF domain containing 2 |
| KRT16 | −0.834 | 1.355 | 2.222 | 2.165 | 3.281 | 4.516 | 4.905 | 0.0385541 | keratin 16 |
| FERMT1 | 0.751 | 0.751 | 0.751 | 3.048 | 1.748 | 4.726 | 4.913 | 0.0170533 | fermitin family member 1 |
| PNMAL2 | 1.420 | 1.299 | 1.166 | 2.045 | 4.481 | 3.596 | 4.916 | 0.0195488 | PNMA-like2 |
| SAP18 | 4.876 | 5.000 | 5.527 | 6.275 | 7.368 | 7.826 | 4.919 | 0.0083506 | Sin3A-associated protein, 18 kDa |
| ASCC1 | 5.805 | 5.570 | 5.911 | 8.186 | 6.248 | 8.216 | 4.940 | 0.0305306 | activating signal cointegrator 1 complex subunit 1 |
| PFDN4 | 3.333 | 3.416 | 5.017 | 5.885 | 5.763 | 5.666 | 5.039 | 0.0169837 | prefoldin subunit 4 |
| LOC284551 | 0.420 | 0.420 | 1.122 | 3.164 | 0.951 | 3.456 | 5.041 | 0.0440541 | No description |
| IDO1 | 0.166 | 2.946 | 3.472 | 4.453 | 5.286 | 5.617 | 5.063 | 0.0146335 | Description |
| BNIP3L | 5.287 | 5.093 | 4.645 | 7.477 | 7.440 | 7.416 | 5.087 | 0.0002636 | BCL2/adenovirus E1B 19 kDa interacting protein 3-like |
| BAALC | 2.796 | 4.289 | 3.231 | 5.148 | 6.129 | 6.355 | 5.107 | 0.0045465 | brain and acute leukemia, cytoplasmic |
| CCDC12 | 4.067 | 5.576 | 4.992 | 7.344 | 7.350 | 6.911 | 5.108 | 0.0028249 | coiled-coil domain containing 12 |
| PROM1 | 2.878 | 3.966 | 3.642 | 4.233 | 6.310 | 6.319 | 5.109 | 0.0215223 | prominin 1 |
| ESAM | 4.815 | 5.615 | 4.476 | 6.829 | 7.190 | 7.796 | 5.110 | 0.0025896 | endothelial cell adhesion molecule |
| FADS2 | 7.237 | 6.921 | 5.070 | 9.338 | 7.429 | 9.585 | 5.133 | 0.0254626 | fatty acid desaturase 2 |
| GCOM1 | 2.264 | 1.595 | 1.595 | 3.412 | 6.303 | 3.960 | 5.152 | 0.0110775 | GRINL1A complex locus |
| ZBTB8OS | 2.698 | 3.913 | 4.820 | 5.907 | 6.058 | 7.189 | 5.166 | 0.0074384 | zinc finger and BTB domain containing 8 opposite strand |
| GNG11 | 4.390 | 5.303 | 4.820 | 6.517 | 9.782 | 7.189 | 5.166 | 0.0107515 | guanine nucleotide binding protein (G protein), gamma 11 |
| TMEM18 | 3.367 | 3.931 | 4.030 | 5.085 | 6.418 | 6.303 | 5.176 | 0.0050132 | transmembrane protein 18 |
| DUSP22 | 1.166 | 1.420 | 2.304 | 2.374 | 4.679 | 3.907 | 5.187 | 0.0261759 | dual specificity phosphatase 22 |
| RABL3 | 7.043 | 6.904 | 5.331 | 9.456 | 7.541 | 9.296 | 5.248 | 0.0174679 | RAB, member of RAS oncogene family-like 3 |
| CCDC124 | 6.504 | 6.610 | 6.167 | 8.593 | 8.613 | 9.006 | 5.264 | 0.0003748 | coiled-coil domain containing 124 |
| FADS6 | 1.122 | 1.122 | 0.166 | 3.164 | 2.567 | 5.617 | 5.281 | 0.0094414 | fatty acid desaturase domain family, member 6 |
| C10orf111 | 0.166 | 0.166 | 0.166 | 2.567 | 0.951 | 3.069 | 5.281 | 0.0163589 | chromosome 10 open reading frame 111 |
| FAM70B | 4.098 | 6.019 | 4.264 | 6.697 | 6.598 | 6.668 | 5.290 | 0.0216532 | family with sequence similarity 70, member B |
| PEX19 | 3.125 | 2.603 | 3.423 | 4.318 | 6.176 | 5.534 | 5.313 | 0.0070125 | peroxisomal biogenesis factor 19 |
| TTRAP | 0.751 | 0.925 | 3.544 | 3.957 | 4.683 | 3.163 | 5.320 | 0.0395185 | No description |
| SLC48A1 | 5.937 | 5.912 | 4.394 | 6.811 | 7.315 | 8.960 | 5.339 | 0.0193945 | solute carrier family 48 (heme transporter), member 1 |
| TSPAN15 | 2.696 | 3.782 | 2.932 | 5.147 | 5.113 | 6.547 | 5.342 | 0.0041789 | tetraspanin 15 |
| ANXA7 | 3.847 | 4.363 | 4.845 | 6.894 | 7.267 | 5.741 | 5.357 | 0.0053688 | annexin A7 |
| PSAT1 | 2.085 | 1.166 | 4.614 | 6.375 | 6.070 | 3.596 | 5.389 | 0.0395374 | phosphoserine aminotransferase 1 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| MYH14 | 4.741 | 4.428 | 3.673 | 5.224 | 6.858 | 7.829 | 5.391 | 0.0169111 | myosin, heavy chain 14, non-muscle |
| ZCCHC9 | 2.429 | 3.068 | 3.730 | 5.370 | 5.462 | 6.164 | 5.406 | 0.0015132 | zinc finger, CCHC domain containing 9 |
| DPY30 | 3.513 | 3.289 | 4.145 | 5.727 | 6.406 | 6.477 | 5.417 | 0.0008756 | dpy-30 homolog (C. elegans) |
| TMEM212 | 7.760 | 8.480 | 6.458 | 8.896 | 9.099 | 11.344 | 5.422 | 0.0360208 | transmembrane protein 212 |
| ECHDC1 | 4.724 | 4.358 | 5.314 | 6.412 | 7.752 | 7.410 | 5.422 | 0.0028060 | enoyl CoA hydratase domain containing 1 |
| EIF4E3 | 3.503 | 3.679 | 2.896 | 3.586 | 6.365 | 5.943 | 5.425 | 0.0471275 | eukaryotic translation initiation factor 4E family member 3 |
| TIPIN | 1.862 | 1.738 | 2.386 | 4.999 | 2.946 | 4.306 | 5.441 | 0.0138733 | TIMELESS interacting protein |
| DLAT | 4.641 | 4.627 | 5.099 | 7.089 | 6.439 | 7.591 | 5.455 | 0.0018226 | dihydrolipoamide S-acetyltransferase |
| MECR | 6.320 | 6.526 | 5.000 | 6.543 | 8.772 | 9.203 | 5.472 | 0.0327129 | mitochondrial trans-2-enoyl-CoA reductase |
| ACBD6 | 3.266 | 2.764 | 2.421 | 5.217 | 3.806 | 5.928 | 5.477 | 0.0136040 | acyl-CoA binding domain containing 6 |
| GNG2 | 3.810 | 4.051 | 4.822 | 4.851 | 7.276 | 6.776 | 5.481 | 0.0270616 | guanine nucleotide binding protein (G protein), gamma 2 |
| C9orf46 | 1.962 | 1.438 | 2.185 | 2.698 | 4.419 | 5.010 | 5.489 | 0.0168884 | chromosome 9 open reading frame 46 |
| STEAP1 | 8.158 | 7.560 | 7.122 | 10.824 | 8.057 | 10.019 | 5.495 | 0.0378642 | six transmembrane epithelial antigen of the prostate 1 |
| CIDECP | 1.484 | 0.420 | 0.166 | 1.122 | 3.944 | 3.795 | 5.500 | 0.0349754 | cell death-inducing DFFA-like effector c pseudogene |
| ASPH | 6.920 | 7.903 | 7.906 | 9.017 | 10.372 | 10.806 | 5.538 | 0.0053574 | aspartate beta-hydroxylase |
| HIST1H4C | 1.888 | 0.692 | 1.620 | 4.098 | 3.000 | 7.933 | 5.571 | 0.0184157 | histone cluster 1, H4c |
| MTND6 | 10.305 | 9.937 | 11.250 | 11.159 | 12.785 | 13.954 | 5.580 | 0.0330427 | No description |
| TRIB3 | 2.734 | 3.445 | 1.595 | 7.271 | 5.221 | 3.960 | 5.609 | 0.0165662 | tribbles homolog 3 (Drosophila) |
| NDUFS8 | 6.262 | 6.432 | 6.672 | 6.823 | 9.621 | 8.926 | 5.631 | 0.0365662 | NADH dehydrogenase (ubiquinone) Fe-S protein 8, 23 kDa (NADH-coenzyme Q reductase) |
| KCTD18 | 3.144 | 3.455 | 3.506 | 5.639 | 5.843 | 6.402 | 5.635 | 0.0003226 | potassium channel tetramerisation domain containing 18 |
| NEIL2 | 3.193 | 2.423 | 2.967 | 3.842 | 5.689 | 5.484 | 5.641 | 0.0116494 | nei endonuclease VIII-like 2 (E. coli) |
| PDE6D | 2.392 | 1.724 | 1.748 | 3.828 | 4.250 | 5.010 | 5.663 | 0.0016887 | phosphodiesterase 6D, cGMP-specific, rod, delta |
| SNAP23 | 3.542 | 3.928 | 5.504 | 6.430 | 6.329 | 6.522 | 5.665 | 0.0113635 | synaptosomal-associated protein, 23 kDa |
| PCK2 | 3.822 | 3.888 | 3.809 | 4.862 | 6.330 | 6.959 | 5.689 | 0.0096267 | phosphoenolpyruvate carboxykinase 2 (mitochondrial) |
| EFCAB3 | −0.364 | −0.364 | 0.456 | 2.424 | 0.456 | 2.969 | 5.710 | 0.0300877 | EF-hand calcium binding domain 3 |
| FBXO25 | 4.861 | 4.190 | 4.416 | 5.583 | 7.042 | 7.401 | 5.816 | 0.0087477 | F-box protein 25 |
| PNPLA4 | 2.990 | 3.328 | 2.969 | 4.034 | 5.914 | 5.530 | 5.817 | 0.0114989 | patatin-like phospholipase domain containing 4 |
| NDUFB10 | 3.315 | 3.346 | 3.460 | 4.878 | 5.887 | 6.635 | 5.819 | 0.0029928 | NADH dehydrogenase (ubiquinone) 1 beta subcomplex, 10, 22 kDa |
| TXNDC17 | 2.942 | 3.513 | 3.274 | 5.668 | 6.191 | 5.497 | 5.877 | 0.0004580 | thioredoxin domain containing 17 |
| MTND1 | 12.503 | 11.813 | 12.779 | 13.008 | 16.013 | 15.062 | 5.893 | 0.0254104 | No description |
| MIIP | 4.825 | 4.782 | 3.266 | 7.319 | 5.835 | 8.198 | 5.935 | 0.0076645 | migration and invasion inhibitory protein |
| KRT5 | 6.326 | 6.556 | 8.156 | 8.904 | 9.676 | 9.295 | 5.970 | 0.0081312 | keratin 5 |
| RPUSD3 | 0.951 | 2.092 | 2.092 | 3.531 | 5.927 | 4.072 | 5.983 | 0.0068030 | RNA pseudouridylate synthase domain containing 3 |
| NQO2 | 1.103 | 1.484 | 0.951 | 2.411 | 3.829 | 4.072 | 6.010 | 0.0057160 | NAD(P)H dehydrogenase, quinone 2 |
| ZIK1 | 0.692 | 2.837 | 0.995 | 4.511 | 3.281 | 3.736 | 6.018 | 0.0137765 | zinc finger protein interacting with K protein 1 homolog (mouse) |
| CCDC69 | 3.719 | 3.752 | 3.840 | 4.358 | 7.019 | 6.354 | 6.070 | 0.0238135 | coiled-coil domain containing 69 |
| SYNPO | 5.049 | 6.122 | 5.007 | 7.666 | 7.650 | 7.624 | 6.071 | 0.0017810 | synaptopodin |
| FLJ45244 | 0.925 | 0.925 | 0.925 | 2.270 | 3.632 | 3.528 | 6.073 | 0.0032167 | No description |
| NME4 | 7.103 | 7.103 | 5.968 | 8.421 | 9.715 | 10.442 | 6.111 | 0.0038302 | non-metastatic cells 4, protein expressed in |
| C9orf123 | 5.603 | 5.553 | 5.313 | 6.159 | 8.166 | 9.193 | 6.118 | 0.0218007 | chromosome 9 open reading frame 123 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| TRIM5 | 3.334 | 3.448 | 3.898 | 6.066 | 4.374 | 7.156 | 6.141 | 0.0187508 | tripartite motif-containing 5 |
| PKP1 | 1.751 | 1.841 | 1.751 | 3.474 | 4.374 | 4.522 | 6.160 | 0.0012334 | plakophilin 1 (ectodermal dysplasia/skin fragility syndrome) |
| SOX10 | 3.783 | 3.072 | 1.493 | 4.120 | 4.146 | 6.561 | 6.179 | 0.0477394 | SRY (sex determining region Y)-box 10 |
| GYS1 | 6.665 | 7.067 | 5.503 | 9.364 | 8.180 | 9.296 | 6.195 | 0.0041993 | glycogen synthase 1 (muscle) |
| CYB5R3 | 8.103 | 7.814 | 7.105 | 8.903 | 10.446 | 11.254 | 6.197 | 0.0087591 | cytochrome b5 reductase 3 |
| ST6GALNAC3 | 2.397 | 3.170 | 2.551 | 5.184 | 5.016 | 5.869 | 6.205 | 0.0006683 | ST6 (alpha-N-acetyl-neuraminyl-2,3-beta-galactosyl-1,3)-N-acetylgalactosaminide alpha-2,6-sialyltransferase 3 |
| RNASEH2B | 2.624 | 2.505 | 3.121 | 4.619 | 5.263 | 5.773 | 6.227 | 0.0013211 | ribonuclease H2, subunit B |
| POLR3GL | 3.269 | 2.817 | 3.452 | 3.874 | 5.929 | 6.521 | 6.318 | 0.0200919 | polymerase (RNA) III (DNA directed) polypeptide G (32kD)-like |
| MLX | 6.659 | 6.993 | 6.203 | 8.864 | 9.075 | 9.857 | 6.327 | 0.0008642 | MAX-like protein X |
| MTND5 | 5.454 | 6.035 | 7.384 | 7.274 | 11.890 | 8.697 | 6.330 | 0.0353650 | No description |
| ZNF619 | 1.620 | 1.983 | −0.834 | 4.648 | 1.888 | 3.736 | 6.343 | 0.0389709 | zinc finger protein 619 |
| PIGC | 0.951 | 1.122 | 0.420 | 3.790 | 3.716 | 2.335 | 6.354 | 0.0029421 | phosphatidylinositol glycan anchor biosynthesis, class C |
| TUBE1 | 5.027 | 4.867 | 4.479 | 8.039 | 5.659 | 7.538 | 6.365 | 0.0141570 | tubulin, epsilon 1 |
| C10orf104 | 6.683 | 7.035 | 6.822 | 7.691 | 9.705 | 9.672 | 6.366 | 0.0135480 | No description |
| ALAD | 4.192 | 3.997 | 3.636 | 4.459 | 7.162 | 6.668 | 6.371 | 0.0269497 | aminolevulinate dehydratase |
| LOC100133920 | 2.166 | 2.234 | 2.299 | 4.589 | 6.126 | 4.927 | 6.465 | 0.0007682 | No description |
| ALKBH4 | 7.771 | 8.380 | 7.667 | 10.698 | 8.419 | 11.073 | 6.466 | 0.0297818 | alkB, alkylation repair homolog 4 (E. coli) |
| C20orf108 | 4.404 | 4.695 | 4.645 | 5.929 | 7.340 | 8.232 | 6.474 | 0.0054467 | chromosome 20 open reading frame 108 |
| NDUFAF2 | 2.915 | 4.534 | 4.028 | 7.046 | 6.750 | 5.621 | 6.524 | 0.0040654 | NADH dehydrogenase (ubiquinone) 1 alpha subcomplex, assembly factor 2 |
| CXCL17 | 0.751 | 1.453 | 0.925 | 3.632 | 2.332 | 4.346 | 6.527 | 0.0064618 | chemokine (C-X-C motif) ligand 17 |
| ACAA2 | 4.465 | 4.032 | 5.187 | 5.681 | 7.874 | 7.898 | 6.549 | 0.0098204 | acetyl-CoA acyltransferase 2 |
| CETN2 | 6.936 | 5.514 | 5.607 | 8.324 | 8.124 | 9.715 | 6.572 | 0.0042946 | centrin, EF-hand protein, 2 |
| IGJ | 3.919 | 7.537 | 6.277 | 9.045 | 8.654 | 8.995 | 6.579 | 0.0123680 | immunoglobulin J polypeptide, linker protein for immunoglobulin alpha and mu polypeptides |
| PSMG1 | 0.456 | −0.834 | 0.456 | 1.888 | 3.653 | 2.165 | 6.597 | 0.0065995 | proteasome (prosome, macropain) assembly chaperone 1 |
| THYN1 | 3.632 | 3.163 | 4.065 | 3.847 | 6.516 | 6.790 | 6.610 | 0.0434157 | thymocyte nuclear protein 1 |
| ACSL1 | 4.181 | 4.306 | 5.211 | 5.146 | 7.942 | 7.479 | 6.638 | 0.0265685 | acyl-CoA synthetase long-chain family member 1 |
| TIMM8B | 1.592 | 3.861 | 4.459 | 4.633 | 7.191 | 5.472 | 6.641 | 0.0369996 | translocase of inner mitochondrial membrane 8 homolog B (yeast) |
| MGC72080 | 1.161 | 2.837 | 2.222 | 4.020 | 5.008 | 4.959 | 6.667 | 0.0032356 | No description |
| SLC25A46 | 2.878 | 2.495 | 3.425 | 5.239 | 5.246 | 6.421 | 6.699 | 0.0014240 | solute carrier family 25, member 46 |
| RPS6KL1 | 2.756 | 2.789 | 1.949 | 5.538 | 3.581 | 5.525 | 6.725 | 0.0096713 | ribosomal protein S6 kinase-like 1 |
| NDUFA1 | 6.817 | 7.697 | 7.319 | 9.750 | 10.168 | 10.070 | 6.731 | 0.0003045 | NADH dehydrogenase (ubiquinone) 1 alpha subcomplex, 1, 7.5 kDa |
| ANAPC13 | 4.127 | 4.046 | 5.345 | 5.523 | 8.394 | 6.888 | 6.780 | 0.0208793 | anaphase promoting complex subunit 13 |
| TSG101 | 7.826 | 8.501 | 7.724 | 11.262 | 9.473 | 10.674 | 6.781 | 0.0044792 | tumor susceptibility gene 101 |
| BNIP3 | 4.170 | 3.970 | 4.254 | 6.406 | 7.192 | 6.935 | 6.798 | 0.0002205 | BCL2/adenovirus E1B 19 kDa interacting protein 3 |
| AVEN | 1.945 | 1.641 | 1.484 | 4.423 | 3.915 | 5.837 | 6.878 | 0.0014353 | apoptosis, caspase activation inhibitor |
| CHURC1 | 3.852 | 3.303 | 3.335 | 4.484 | 6.127 | 6.926 | 6.928 | 0.0121403 | churchill domain containing 1 |
| RMND5B | 6.467 | 5.985 | 4.772 | 9.006 | 6.335 | 9.264 | 6.947 | 0.0296207 | required for meiotic nuclear division 5 homolog B (S. cerevisiae) |
| NEURL3 | 1.318 | 1.880 | 1.318 | 4.117 | 3.189 | 5.010 | 6.956 | 0.0026275 | neuralized homolog 3 (Drosophila) pseudogene |
| NUDT7 | 1.122 | 2.567 | 1.588 | 2.946 | 4.848 | 5.390 | 7.077 | 0.0107893 | nudix (nucleoside diphosphate linked moiety X)-type motif 7 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| MCF2L | 5.413 | 6.212 | 5.541 | 9.038 | 6.880 | 8.797 | 7.093 | 0.0080609 | MCF.2 cell line derived transforming sequence-like |
| SPHAR | 1.880 | 0.925 | 1.318 | 2.487 | 4.148 | 5.563 | 7.110 | 0.0131297 | S-phase response (cyclin related) |
| NIPSNAP3A | 2.062 | 2.062 | 2.608 | 3.202 | 5.465 | 5.206 | 7.246 | 0.0112243 | nipsnap homolog 3A (C. elegans) |
| HADH | 3.552 | 3.885 | 4.240 | 4.080 | 8.227 | 6.743 | 7.250 | 0.0445601 | hydroxyacyl-CoA dehydrogenase |
| CCL13 | 1.318 | 3.323 | 1.748 | 4.607 | 3.646 | 6.361 | 7.255 | 0.0153884 | chemokine (C-C motif) ligand 13 |
| RNF14 | 2.567 | 2.541 | 3.245 | 4.783 | 6.106 | 5.673 | 7.264 | 0.0011797 | ring finger protein 14 |
| TTC1 | 4.576 | 5.390 | 5.655 | 7.148 | 8.257 | 8.839 | 7.294 | 0.0018113 | tetratricopeptide repeat domain 1 |
| FABP5 | 4.711 | 5.863 | 5.725 | 6.547 | 9.078 | 8.603 | 7.353 | 0.0107402 | fatty acid binding protein 5 (psoriasis-associated) |
| BOLA3 | 2.741 | 2.174 | 2.841 | 3.164 | 5.639 | 5.915 | 7.454 | 0.0233287 | bolA homolog 3 (E. coli) |
| HSD17B1 | 3.928 | 3.409 | 3.584 | 4.163 | 6.483 | 7.405 | 7.459 | 0.0265949 | hydroxysteroid (17-beta) dehydrogenase 1 |
| SLC9A3R2 | 4.099 | 4.407 | 2.964 | 5.440 | 9.603 | 7.012 | 7.534 | 0.0106055 | solute carrier family 9 (sodium/hydrogen exchanger), member 3 regulator 2 |
| MRP63 | 3.468 | 3.854 | 4.084 | 6.026 | 6.768 | 8.035 | 7.537 | 0.0013438 | mitochondrial ribosomal protein 63 |
| PPARG | 7.031 | 7.402 | 8.342 | 7.925 | 10.828 | 11.256 | 7.540 | 0.0367364 | peroxisome proliferator-activated receptor gamma |
| SUCLG2 | 3.450 | 4.452 | 3.921 | 4.065 | 6.837 | 7.481 | 7.551 | 0.0492931 | succinate-CoA ligase, GDP-forming, beta subunit |
| ATP5G3 | 7.285 | 7.239 | 7.397 | 9.932 | 10.361 | 10.208 | 7.584 | 0.0001343 | ATP synthase, H+ transporting, mitochondrial Fo complex, subunit C3 (subunit 9) |
| C2orf28 | 4.728 | 4.276 | 4.744 | 5.716 | 7.660 | 7.740 | 7.632 | 0.0073582 | chromosome 2 open reading frame 28 |
| DSG2 | 4.028 | 4.227 | 4.584 | 6.114 | 7.183 | 8.945 | 7.763 | 0.0038794 | desmoglein 2 |
| LOC644538 | 3.978 | 4.421 | 3.591 | 4.700 | 6.944 | 7.882 | 7.814 | 0.0206963 | No description |
| FAIM | −0.834 | −0.834 | 1.290 | 1.290 | 4.264 | 2.165 | 7.861 | 0.0240998 | Fas apoptotic inhibitory molecule |
| GPN3 | 1.453 | 1.748 | 0.925 | 4.489 | 3.723 | 4.726 | 7.879 | 0.0004921 | GPN-loop GTPase 3 |
| PCYT2 | 2.756 | 2.796 | 2.083 | 3.495 | 5.736 | 6.830 | 7.887 | 0.0139104 | phosphate cytidylyltransferase 2, ethanolamine |
| UBLCP1 | 2.682 | 2.626 | 2.410 | 5.609 | 5.371 | 6.124 | 7.907 | 0.0001645 | ubiquitin-like domain containing CTD phosphatase 1 |
| HINT3 | 3.162 | 3.988 | 3.498 | 5.797 | 6.482 | 7.507 | 7.911 | 0.0011683 | histidine triad nucleotide binding protein 3 |
| MTCO3 | 14.380 | 13.260 | 14.195 | 14.444 | 17.366 | 17.355 | 7.927 | 0.0277674 | No description |
| MTCO2 | 11.738 | 11.539 | 11.619 | 12.533 | 16.071 | 14.607 | 7.937 | 0.0159535 | No description |
| ANP32A | 0.951 | 2.174 | 1.484 | 2.799 | 4.482 | 6.198 | 7.987 | 0.0119489 | acidic (leucine-rich) nuclear phosphoprotein 32 family, member A |
| PRDX3 | 8.261 | 7.309 | 6.921 | 10.588 | 9.688 | 11.261 | 7.998 | 0.0015700 | peroxiredoxin 3 |
| COX7B | 3.828 | 4.190 | 4.879 | 6.767 | 7.886 | 7.268 | 8.039 | 0.0005934 | cytochrome c oxidase subunit VIIb |
| GMFG | 6.858 | 8.027 | 6.202 | 9.211 | 9.611 | 11.172 | 8.047 | 0.0045579 | glia maturation factor, gamma |
| LPL | 5.285 | 4.967 | 6.190 | 6.031 | 10.673 | 8.295 | 8.055 | 0.0356615 | lipoprotein lipase |
| HRCT1 | 2.069 | 2.343 | 2.333 | 2.698 | 5.348 | 7.908 | 8.083 | 0.0343211 | histidine rich carboxyl terminus 1 |
| PIR | 1.318 | 0.925 | 1.318 | 2.746 | 4.365 | 4.346 | 8.156 | 0.0023673 | pirin (iron-binding nuclear protein) |
| NAT1 | 0.166 | 0.420 | 0.420 | 3.455 | 3.230 | 3.456 | 8.201 | 0.0001002 | N-acetyltransferase 1 (arylamine N-acetyltransferase) |
| C2orf55 | 0.951 | 0.420 | 0.166 | 1.588 | 3.472 | 4.840 | 8.292 | 0.0125624 | chromosome 2 open reading frame 55 |
| PGM1 | 4.564 | 3.728 | 4.192 | 4.277 | 7.977 | 7.253 | 8.345 | 0.0453816 | phosphoglucomutase 1 |
| PET112L | 4.057 | 4.728 | 3.676 | 4.881 | 7.119 | 8.204 | 8.347 | 0.0216252 | PET112-like (yeast) |
| LAIR1 | 1.299 | 2.742 | 3.611 | 3.477 | 5.805 | 7.120 | 8.354 | 0.0242750 | leukocyte-associated immunoglobulin-like receptor 1 |
| SLC7A10 | 1.751 | 1.751 | 1.751 | 2.144 | 5.415 | 4.815 | 8.362 | 0.0291902 | solute carrier family 7, (neutral amino acid transporter, y+ system) member 10 |
| ECHS1 | 3.555 | 3.290 | 3.780 | 3.860 | 9.867 | 6.629 | 8.422 | 0.0428529 | enoyl CoA hydratase, short chain, 1, mitochondrial |
| TUSC5 | 2.336 | 2.336 | 2.336 | 2.336 | 5.414 | 7.021 | 8.442 | 0.0498797 | tumor suppressor candidate 5 |
| TM4SF18 | 5.999 | 6.679 | 4.795 | 9.095 | 6.485 | 10.183 | 8.549 | 0.0280170 | transmembrane 4 L six family member 18 |
| NDUFA7 | 5.866 | 3.632 | 4.061 | 4.665 | 8.299 | 8.970 | 8.597 | 0.0484399 | NADH dehydrogenase (ubiquinone) 1 alpha subcomplex, 7, 14.5 kDa |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| KRT14 | 4.159 | 6.511 | 7.371 | 8.828 | 8.913 | 10.479 | 8.621 | 0.0071093 | keratin 14 |
| CCDC85A | 3.416 | 3.162 | 3.972 | 3.661 | 7.075 | 7.091 | 8.684 | 0.0402561 | coiled-coil domain containing 85A |
| TST | 1.710 | 1.166 | 3.334 | 3.696 | 6.460 | 6.460 | 8.729 | 0.0069709 | thiosulfate sulfurtransferase (rhodanese) |
| C10orf108 | 2.411 | 2.632 | 2.083 | 5.570 | 4.517 | 5.879 | 8.931 | 0.0006887 | chromosome 10 open reading frame 108 |
| TMEM42 | 1.748 | 1.453 | 1.880 | 2.270 | 4.986 | 5.050 | 9.002 | 0.0214361 | transmembrane protein 42 |
| GPIHBP1 | 7.800 | 8.849 | 5.199 | 8.393 | 10.809 | 12.542 | 9.154 | 0.0323030 | glycosylphosphatidylinositol anchored high density lipoprotein binding protein 1 |
| GNAZ | 4.710 | 6.105 | 5.040 | 7.095 | 8.237 | 10.044 | 9.168 | 0.0060828 | guanine nucleotide binding protein (G protein), alpha z polypeptide |
| HIRIP3 | 1.456 | 0.636 | 0.951 | 2.335 | 4.173 | 5.568 | 9.336 | 0.0083620 | HIRA interacting protein 3 |
| SLC22A12 | −0.834 | −0.834 | −0.834 | −0.834 | 2.424 | 2.969 | 9.562 | 0.0475295 | solute carrier family 22 (organic anion/urate transporter), member 12 |
| MDH1 | 7.805 | 8.401 | 7.884 | 10.620 | 11.144 | 12.069 | 9.578 | 0.0004467 | malate dehydrogenase 1, NAD (soluble) |
| ATP5J | 5.853 | 6.360 | 7.170 | 8.066 | 10.430 | 9.695 | 9.582 | 0.0047992 | ATP synthase, H+ transporting, mitochondrial Fo complex, subunit F6 |
| IDH1 | 2.423 | 2.702 | 4.343 | 4.007 | 7.624 | 6.440 | 9.722 | 0.0236759 | Description |
| ACADS | 5.652 | 6.452 | 5.495 | 6.858 | 9.452 | 9.737 | 9.751 | 0.0115964 | acyl-CoA dehydrogenase, C-2 to C-3 short chain |
| TXNDC9 | 0.166 | 0.166 | 0.420 | 3.455 | 5.036 | 3.069 | 9.773 | 0.0005450 | thioredoxin domain containing 9 |
| CPA1 | 0.166 | 0.166 | 0.166 | 0.166 | 3.802 | 3.456 | 9.779 | 0.0477905 | carboxypeptidase A1 (pancreatic) |
| MTND4 | 16.057 | 14.989 | 14.554 | 18.075 | 18.279 | 19.121 | 9.783 | 0.0007001 | No description |
| PLLP | 1.318 | 3.464 | 3.439 | 4.711 | 5.440 | 6.756 | 9.795 | 0.0089626 | plasmolipin |
| C6orf203 | 0.420 | 0.951 | 2.861 | 3.770 | 5.843 | 5.617 | 10.196 | 0.0028657 | chromosome 6 open reading frame 203 |
| XRCCGBP1 | 0.166 | 0.951 | 1.122 | 2.092 | 4.306 | 5.548 | 10.234 | 0.0078045 | XRCC6 binding protein 1 |
| VTI1B | 4.570 | 5.189 | 6.197 | 7.934 | 9.324 | 9.233 | 10.300 | 0.0009096 | vesicle transport through interaction with t-SNAREs homolog 1B (yeast) |
| METTL5 | 1.748 | 2.343 | 2.940 | 5.057 | 6.279 | 6.309 | 10.333 | 0.0004126 | methyltransferase like 5 |
| MUCL1 | 0.420 | 1.122 | 4.497 | 4.796 | 5.001 | 3.795 | 10.375 | 0.0486267 | mucin-like 1 |
| LSM3 | 2.752 | 0.951 | 1.353 | 4.145 | 6.891 | 4.775 | 10.715 | 0.0033922 | LSM3 homolog, U6 small nuclear RNA associated (S. cerevisiae) |
| GIMAP7 | 2.734 | 3.396 | 3.101 | 3.938 | 6.544 | 8.396 | 10.873 | 0.0178529 | GTPase, IMAP family member 7 |
| GPT | 1.611 | 1.299 | 1.611 | 2.045 | 5.081 | 5.790 | 11.078 | 0.0219164 | glutamic-pyruvate transaminase (alanine aminotransferase) |
| RDH5 | 6.999 | 6.252 | 4.986 | 6.768 | 9.727 | 11.298 | 11.126 | 0.0261176 | retinol dehydrogenase 5(11-cis/9-cis) |
| NDUFV3 | 6.444 | 6.958 | 6.180 | 9.937 | 9.240 | 11.256 | 11.256 | 0.0006312 | NADH dehydrogenase (ubiquinone) flavoprotein 3, 10 kDa |
| GDF5 | −0.834 | 0.456 | 0.177 | 2.678 | 3.379 | 4.516 | 11.403 | 0.0008415 | growth differentiation factor 5 |
| NAT8L | 2.919 | 2.603 | 2.610 | 2.793 | 6.140 | 7.701 | 11.550 | 0.0415594 | N-acetyltransferase 8-like (GCN5-related, putative) |
| C2orf84 | 0.166 | 1.738 | 0.636 | 2.620 | 4.173 | 5.711 | 11.611 | 0.0057046 | chromosome 2 open reading frame 84 |
| DBI | 3.142 | 2.667 | 4.728 | 5.420 | 9.044 | 6.691 | 11.704 | 0.0088151 | diazepam binding inhibitor (GABA receptor modulator, acyl-CoA binding protein) |
| LOC285550 | 3.252 | 3.614 | 4.017 | 4.496 | 7.590 | 7.168 | 11.746 | 0.0136993 | No description |
| MGST2 | 2.067 | 4.210 | 2.222 | 5.622 | 6.401 | 6.124 | 11.753 | 0.0019232 | microsomal glutathione S-transferase 2 |
| SGK2 | 1.166 | 1.166 | 1.299 | 1.166 | 4.758 | 5.865 | 12.054 | 0.0455859 | serum/glucocorticoid regulated kinase 2 |
| SNAPIN | 3.256 | 3.801 | 3.957 | 4.949 | 7.552 | 7.454 | 12.090 | 0.0062780 | SNAP-associated protein |
| HRASLS5 | 1.166 | 1.166 | 1.299 | 1.166 | 4.765 | 6.311 | 12.113 | 0.0457871 | HRAS-like suppressor family, member 5 |
| GCSH | 2.069 | 2.700 | 3.700 | 5.630 | 7.301 | 6.611 | 12.141 | 0.0007379 | glycine cleavage system protein H (aminomethyl carrier) |
| SLC25A10 | 4.721 | 3.729 | 2.921 | 3.757 | 7.654 | 8.348 | 12.355 | 0.0498438 | solute carrier family 25 (mitochondrial carrier; dicarboxylate transporter), member 10 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| SLC25A1 | 7.337 | 7.477 | 6.078 | 9.713 | 10.580 | 11.736 | 12.425 | 0.0009898 | solute carrier family 25 (mitochondrial carrier: citrate transporter), member 1 |
| LBP | −0.834 | −0.364 | 2.222 | 3.709 | 2.837 | 5.754 | 12.738 | 0.0075208 | lipopolysaccharide binding protein |
| EXOC3L | −0.834 | −0.834 | −0.834 | −0.834 | 2.837 | 2.969 | 12.738 | 0.0438956 | exocyst complex component 3-like |
| MTND2 | 10.503 | 10.437 | 12.690 | 11.970 | 16.371 | 14.616 | 12.828 | 0.0308060 | No description |
| HOXA7 | 0.420 | 1.862 | 0.420 | 3.790 | 5.033 | 5.546 | 12.854 | 0.0006048 | homeobox A7 |
| HIGD1B | 2.487 | 3.163 | 1.880 | 2.487 | 6.200 | 7.401 | 13.111 | 0.0466910 | HIG1 hypoxia inducible domain family, member 1B |
| GCHFR | 5.030 | 5.919 | 4.489 | 7.117 | 8.751 | 10.299 | 13.183 | 0.0037039 | GTP cyclohydrolase I feedback regulator |
| NQO1 | 2.593 | 3.800 | 4.317 | 5.708 | 8.626 | 7.670 | 14.619 | 0.0025503 | NAD(P)H dehydrogenase, quinone 1 |
| PALMD | 2.234 | 3.330 | 3.799 | 3.742 | 8.087 | 7.211 | 14.735 | 0.0223234 | palmdelphin |
| SCD | 6.163 | 6.195 | 5.317 | 8.368 | 10.520 | 10.060 | 14.895 | 0.0008188 | stearoyl-CoA desaturase (delta-9-desaturase) |
| AGPAT2 | 7.767 | 7.626 | 6.470 | 7.455 | 11.576 | 12.195 | 15.455 | 0.0345669 | 1-acylglycerol-3-phosphate O-acyltransferase 2 (lysophosphatidic acid acyltransferase, beta) |
| C10orf58 | 3.245 | 4.783 | 5.619 | 5.722 | 9.992 | 8.751 | 15.648 | 0.0149391 | chromosome 10 open reading frame 58 |
| RGS5 | 4.580 | 6.104 | 6.001 | 6.606 | 10.046 | 10.075 | 15.683 | 0.0124686 | regulator of G-protein signaling 5 |
| HOXB7 | 2.069 | 3.085 | 2.487 | 3.847 | 6.872 | 7.167 | 16.939 | 0.0068899 | homeobox B7 |
| TM7SF2 | 4.883 | 4.838 | 4.382 | 4.734 | 8.950 | 9.971 | 17.297 | 0.0362818 | transmembrane 7 superfamily member 2 |
| LXN | 2.614 | 4.023 | 2.503 | 7.453 | 6.297 | 8.170 | 17.723 | 0.0004013 | latexin |
| LDHD | 1.166 | 1.166 | 1.166 | 2.045 | 5.334 | 5.410 | 17.975 | 0.0117999 | lactate dehydrogenase D |
| G0S2 | 3.770 | 6.727 | 7.866 | 8.417 | 10.468 | 12.054 | 18.229 | 0.0104557 | G0/G1 switch 2 |
| GPR109A | −0.834 | −0.834 | 0.456 | 0.692 | 3.379 | 4.959 | 18.546 | 0.0137576 | G protein-coupled receptor 109A |
| NDUFA12 | 0.166 | 2.494 | 0.636 | 4.658 | 6.492 | 4.889 | 19.067 | 0.0010541 | NADH dehydrogenase (ubiquinone) 1 alpha subcomplex, 12 |
| MAOA | 3.422 | 3.280 | 4.081 | 4.276 | 8.465 | 7.730 | 19.811 | 0.0178642 | monoamine oxidase A |
| ITGB1BP1 | 2.973 | 2.735 | 2.687 | 3.898 | 7.414 | 7.050 | 19.900 | 0.0085942 | integrin beta 1 binding protein 1 |
| CSN1S1 | 0.166 | 0.166 | 0.166 | 1.122 | 4.695 | 7.524 | 23.086 | 0.0166781 | casein alpha s1 |
| AQP7 | 1.949 | 3.162 | 2.789 | 3.412 | 8.905 | 7.343 | 23.499 | 0.0171675 | aquaporin 7 |
| HEPACAM | 1.166 | 1.166 | 1.299 | 1.166 | 5.802 | 6.730 | 24.856 | 0.0362553 | hepatocyte cell adhesion molecule |
| AQP7P3 | 1.122 | 0.166 | 1.588 | 3.903 | 6.766 | 5.769 | 25.046 | 0.0007568 | aquaporin 7 pseudogene 3 |
| TPRG1 | 0.751 | 0.751 | 0.751 | 0.751 | 5.442 | 6.309 | 25.824 | 0.0342345 | tumor protein p63 regulated 1 |
| HSPB7 | 4.595 | 6.218 | 4.595 | 6.259 | 10.579 | 11.065 | 28.782 | 0.0110548 | heat shock 27 kDa protein family, member 7 (cardiovascular) |
| LIPE | 3.932 | 5.260 | 5.385 | 4.724 | 11.661 | 10.199 | 30.681 | 0.0373990 | lipase, hormone-sensitive |
| ALDOC | 3.661 | 4.861 | 3.676 | 6.909 | 8.652 | 9.882 | 31.479 | 0.0009489 | aldolase C, fructose-bisphosphate |
| GPAM | 3.126 | 3.126 | 3.620 | 4.565 | 8.586 | 8.993 | 41.443 | 0.0072326 | glycerol-3-phosphate acyltransferase, mitochondrial |
| GPR34 | 0.166 | 0.166 | 0.166 | 0.166 | 5.629 | 7.281 | 44.104 | 0.0309561 | G protein-coupled receptor 34 |
| KCNIP2 | 2.973 | 3.246 | 4.269 | 3.126 | 9.783 | 9.470 | 45.679 | 0.0414232 | Kv channel interacting protein 2 |
| TIMP4 | 5.285 | 5.375 | 4.314 | 6.834 | 10.900 | 11.673 | 48.997 | 0.0040806 | TIMP metallopeptidase inhibitor 4 |
| CIDEC | 1.166 | 1.166 | 2.810 | 1.722 | 8.950 | 7.069 | 59.834 | 0.0346713 | cell death-inducing DFFA-like effector c |
| GYG2 | 4.351 | 3.586 | 3.557 | 3.394 | 10.429 | 10.392 | 67.535 | 0.0393030 | glycogenin 2 |
| PLIN1 | 2.751 | 2.797 | 3.934 | 2.751 | 10.428 | 8.887 | 68.114 | 0.0423862 | perilipin 1 |
| BPIL1 | −0.834 | −0.834 | −0.834 | 0.692 | 5.446 | 5.351 | 72.733 | 0.0053370 | bactericidal/permeability-increasing protein-like 1 |
| SAA1 | 5.835 | 5.597 | 9.372 | 8.690 | 15.271 | 15.700 | 80.310 | 0.0094603 | serum amyloid A1 |
| SAA2 | 1.488 | 1.488 | 1.595 | 1.488 | 9.062 | 7.851 | 82.297 | 0.0282054 | serum amyloid A2 |
| CIDEA | 1.974 | 1.974 | 2.973 | 1.974 | 9.464 | 8.753 | 89.950 | 0.0361918 | cell death-inducing DFFA-like effector a |
| PFKFB1 | 0.692 | −0.834 | −0.834 | −0.834 | 6.902 | 7.207 | 91.418 | 0.0388714 | 6-phosphofructo-2-kinase/fructose-2,6-biphosphatase 1 |
| ALDH1L1 | 0.751 | 0.751 | 1.318 | 0.751 | 7.646 | 8.378 | 119.008 | 0.0310511 | aldehyde dehydrogenase 1 family, member L1 |

TABLE 7-continued

Differentially Exprssed Genes in Stromal Breast Epithelial Cells

| Gene Symbol | Nulliparous (NP) Samples | | | Parous (P) Samples | | | Pseudo fold change | P value | Gene description |
|---|---|---|---|---|---|---|---|---|---|
| | Stroma N33 | Stroma N35 | Stroma N58 | Stroma N37 | Stroma N39 | Stroma N40 | | | |
| GPD1 | 2.853 | 2.626 | 4.079 | 2.626 | 11.086 | 10.658 | 128.615 | 0.0382144 | glycerol-3-phosphate dehydrogenase 1 (soluble) |
| S100B | 2.423 | 2.334 | 3.158 | 2.392 | 9.741 | 10.449 | 156.537 | 0.0312636 | S100 calcium binding protein B |

Figure 6:
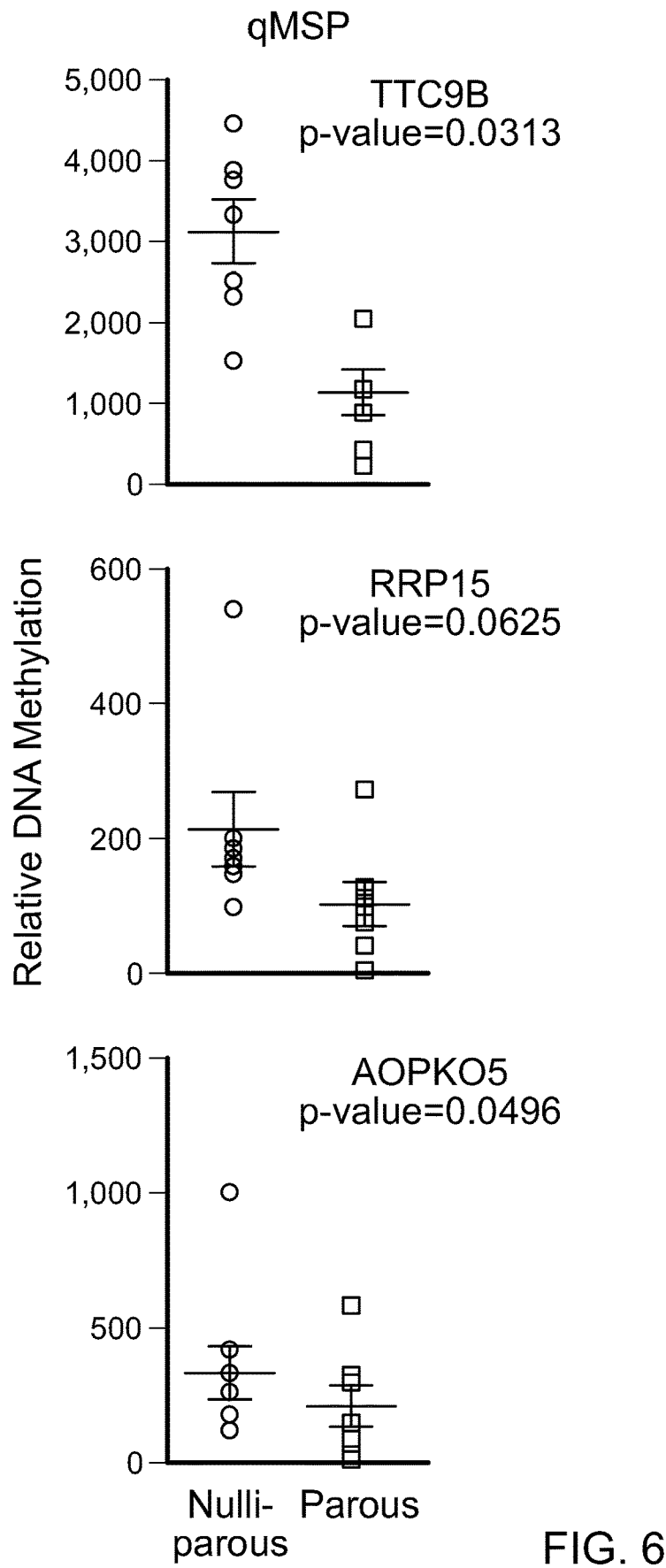
FIG. 6 contains dot plots showing the relative DNA methylation, as determined by qMSP analysis (left panel), and the expression, as determined by qRT-PCR (right panel), of the indicated genes (left panel: TTC9B, RRP15, and AOPKO5; right panel: CDKN1B, PTGS2, COL1A1 and COL3A1) in CD44+, CD24− breast epithelial cells and CD24− breast epithelial cells isolated from multiple nulliparous and parous women, respectively. Relative methylation and expression levels normalized to ACTB and RPL19, respectively, are indicated on the y-axis. The bars mark the median and p-values indicate the statistical significance of the observed differences.
Figure 6:
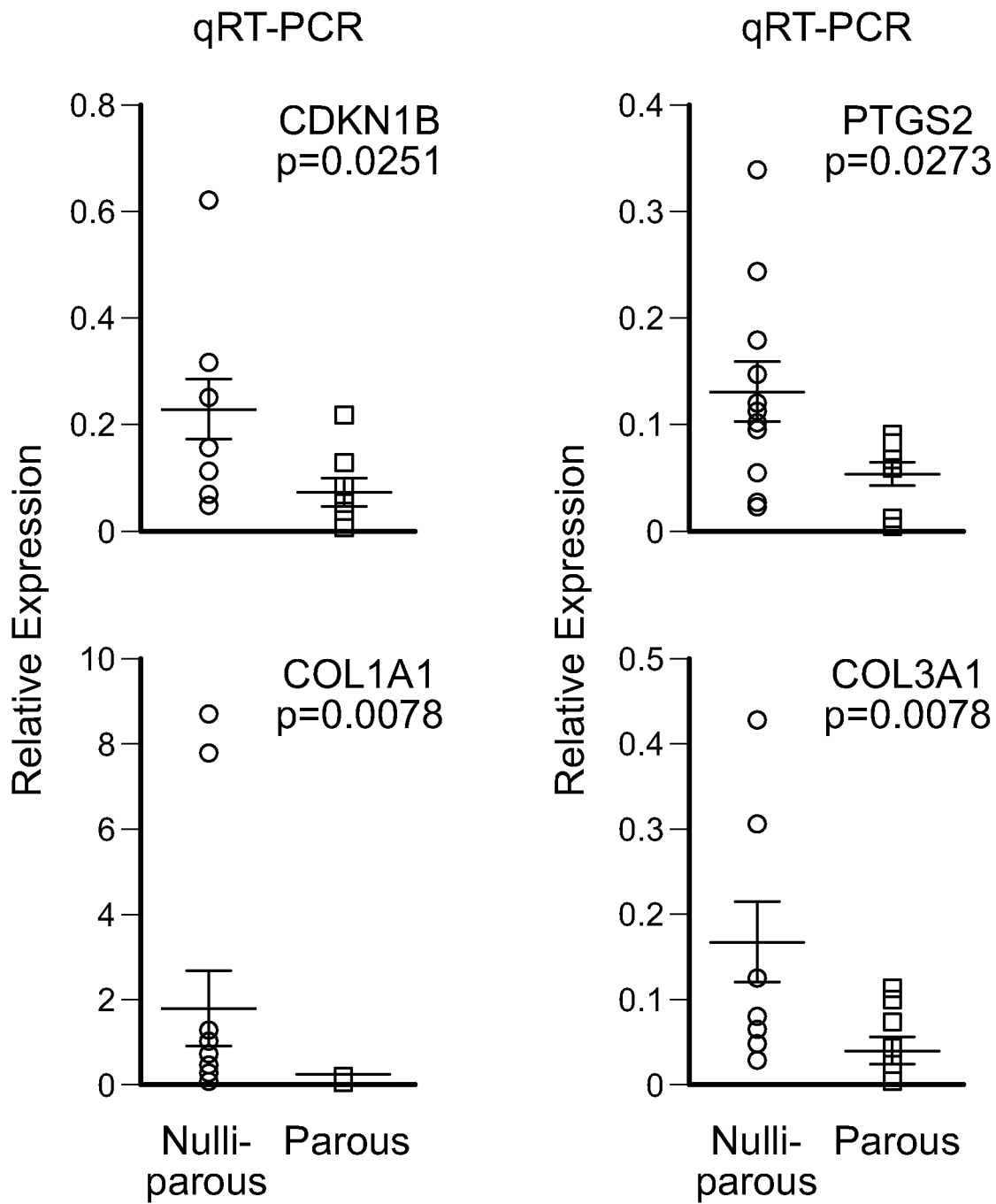

To validate differences in gene expression in additional samples and by other methods, quantitative RT-PCR (qRT-PCR) analyses of selected genes were performed using CD44+ cells from multiple nulliparous and parous cases. Despite some interpersonal variability, statistically significant differences between nulliparous and parous groups were detected that overall correlated with SAGEseq data (FIG. 6).

Figure 7:
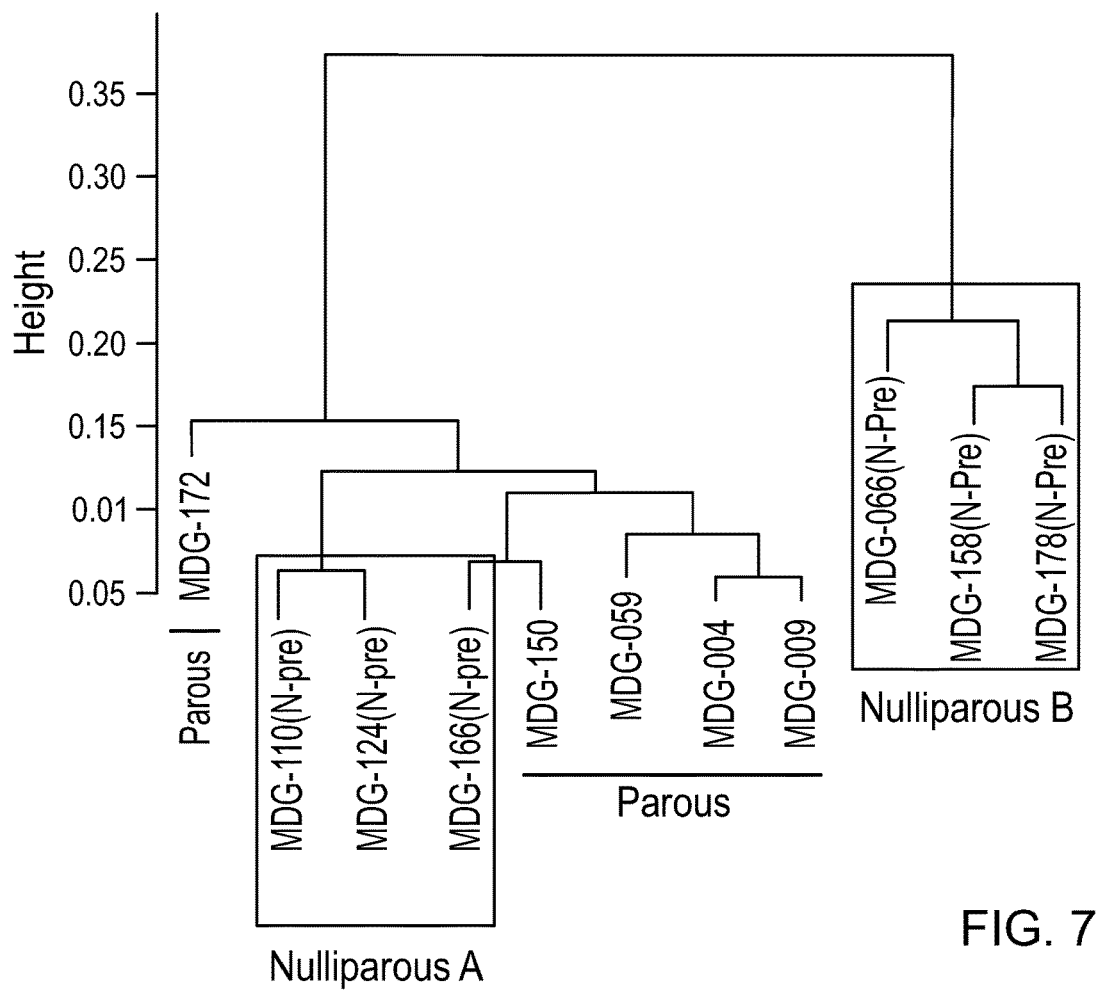
FIG. 7 is a dendrogram showing the hierarchical clustering of Norwegian cohort (GSE18672) based on Pearson correlation using genes differentially expressed in CD44+ cells. Individual patient samples from the cohort are shown (MDG-110, MDG124, etc.); "N-pre" means premenopausal. Clustering analysis using the differentially expressed gene sets divided these samples into two groups, a mixed parous/nulliparous (Nulliparous A) group, and a distinct, nulliparous (Nulliparous B) group.
Figure 8:
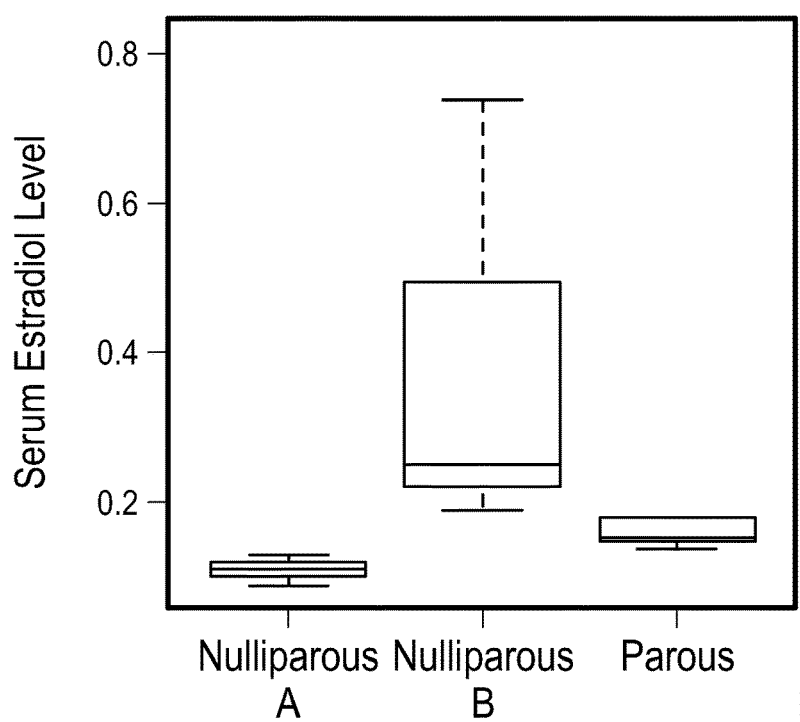
FIG. 8 is a bar plot of the scrum estradiol levels in picograms per milliliter for the samples corresponding to FIG. 7 (Nulliparous A, Nulliparous B and Parous groups).

To validate the parity-related gene expression differences in an independent cohort, the levels of the differentially expressed genes (in all cell types or only in CD44+ cells) were analyzed in gene expression data from breast biopsies of a cohort of Norwegian women matched to the nulliparous and parous samples for age (<40) and parity (P2). Clustering analysis using the differentially expressed gene sets divided these samples into a distinct nulliparous (Nulliparous B) and a mixed parous/nulliparous (Nulliparous A) group (FIG. 7). Using genes differentially expressed in all four cell types (i.e., CD24+, CD10+, CD44+ cells, and fibroblasts), combined, or only in CD44+ cells, gave identical results, supporting the hypothesis that changes in CD44+ cells are the most significant and physiologically relevant. Interestingly, the nulliparous samples that formed a distinct cluster (Nulliparous B), or were closer to parous cases (Nulliparous A), displayed significant differences in serum estradiol levels (SEL), with the samples more similar to parous cases having low SEL; all parous samples also had low SEL (FIG. 8). Because these were all premenopausal women and SEL is known to be higher in the luteal phase of the menstrual cycle, when breast epithelial cell proliferation is also higher, these findings implied that breast tissues of nulliparous and parous women may be more distinct in the luteal phase potentially due to differences in the activity of signaling pathways driving cell proliferation or the number of cells that respond to these stimuli.

Figure 9A:
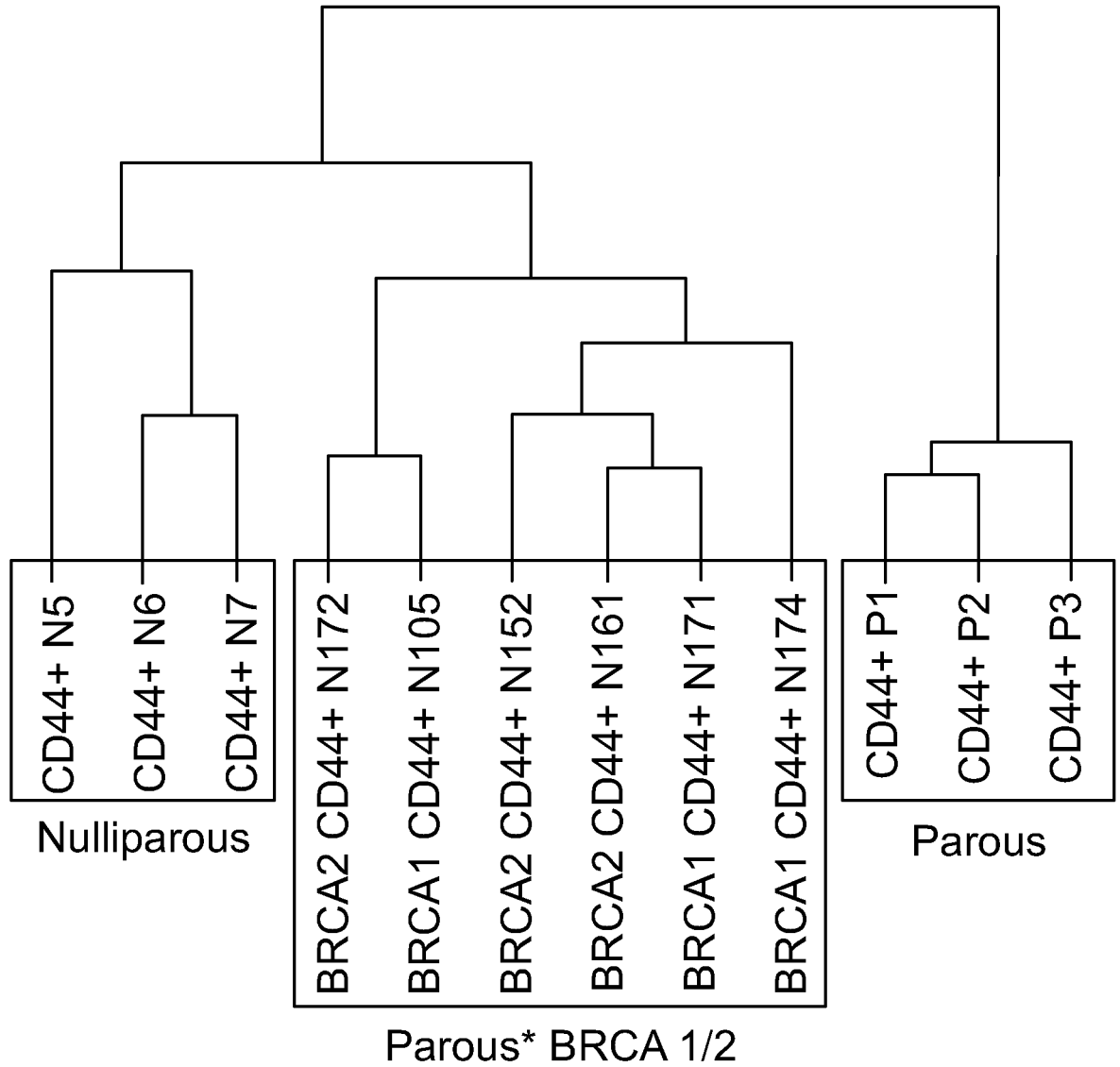
FIG. 9A is a dendrogram showing the hierarchical clustering of CD44+ cells from parous and nulliparous control women and parous BRCA1 mutation carriers.

To strengthen the hypothesis that the parity-associated differences detected in CD44+ cells might be related to subsequent breast cancer risk, the gene expression profiles of CD44+ cells from parous BRCA1 and BRCA2 mutation carriers, whose risk is not decreased by parity, were analyzed. CD44+ cells from parous BRCA1/2 mutation carriers clustered with CD44+ cells from nulliparous controls (FIG. 9A), thereby demonstrating that parity-associated changes observed in control parous women may not occur in these high risk women. The gene expression data in CD10-, CD24-, CD44+ breast epithelial cells from BRCA1 and BRCA2 mutation carriers is shown in Tables 8 and 9, below. Tables 8 and 9 show, from left column to right column, the t-value (t-score), the q-value, which is the smallest FDR (false discovery rate) at which a particular gene would just stay on the list of positives, the p-value, which is the smallest false positive rate (FPR) at which the gene appears positive, and the gene expression in P1, P2, and P3 (samples from three control tissues (CD10-, CD24-, CD44+ breast epithelial cells from parous subjects)), and in BRCA1-N105, BRCA1-N171 and BRCA1-N174 (samples from three BRCA1 mutation carriers) in Table 8 or in BRCA2-N151, BRCA2-N161 and BRCA2-N172 (samples from three BRCA2 mutation carriers). The statistical values t, p, and q are described at http://discover.nci.nih.gov/microarrayAnalysis/Statistical.Tests.jsp.

TABLE 8

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| HSPA1A | 2.19567994 | 0.043453389 | 0.000119088 | 1663.164892 | 2.993831 | 4.736586 | 7.997641 | 15.436302 | 17.228905 | 14.991147 |
| HNRNPA1 | 2.118243596 | 0.043453389 | 0.000173528 | 672.2332477 | 3.024504 | 2.023048 | 2.165421 | 12.868252 | 11.558239 | 9.620989 |
| LOC642361 | 1.969434006 | 0.043453389 | 0.000261994 | 578.5332207 | 1.874444 | 2.023048 | 2.995681 | 12.171937 | 11.778929 | 8.745549 |
| ID2B | 2.198930945 | 0.043453389 | 0.000112283 | 509.5369524 | 1.874444 | 2.023048 | 2.165421 | 11.549452 | 11.016091 | 9.303041 |
| RPS29 | 1.84392888 | 0.043453389 | 0.00044573 | 427.4999894 | 4.309025 | 5.362142 | 6.282905 | 15.630577 | 14.101923 | 11.48514 |
| MAGEB10 | 2.429149475 | 0.043453389 | 7.15E−05 | 422.777762 | 3.024504 | 2.023048 | 2.165421 | 10.746803 | 11.544714 | 11.312574 |
| CENPH | 2.165594943 | 0.043453389 | 0.000139503 | 419.9055175 | 4.743564 | 3.770995 | 2.165421 | 11.697868 | 12.808177 | 12.484916 |
| KRT18 | 1.696996829 | 0.043453389 | 0.000779177 | 363.1762985 | 1.874444 | 3.872014 | 2.165421 | 12.37654 | 10.68376 | 8.213534 |
| RPL27A | 2.223955537 | 0.043453389 | 0.000105478 | 317.7835144 | 5.779429 | 5.148082 | 6.670675 | 14.585927 | 14.09133 | 13.791736 |
| RAD21-AS1 | 2.318523081 | 0.043453389 | 9.87E−05 | 301.3830562 | 1.874444 | 2.406905 | 2.165421 | 10.093095 | 11.437977 | 10.400875 |
| RPLP1 | 2.183840284 | 0.043453389 | 0.000125893 | 301.1534971 | 6.52121 | 6.072636 | 6.527811 | 15.605413 | 14.755565 | 13.685741 |
| USP33 | 1.918655981 | 0.043453389 | 0.000323239 | 290.8179694 | 5.982974 | 3.360637 | 3.764125 | 11.54461 | 12.544527 | 12.777496 |
| AKR1D1 | 2.034393168 | 0.043453389 | 0.000227969 | 281.8516744 | 2.993831 | 3.770995 | 3.935222 | 10.369894 | 11.909787 | 12.782289 |
| FAM83A | 2.059799803 | 0.043453389 | 0.000243359 | 265.2498231 | 1.874444 | 2.023048 | 2.165421 | 8.723321 | 10.074256 | 10.27958 |
| BMP3 | 2.291911149 | 0.043453389 | 9.19E−05 | 262.4866963 | 3.350997 | 3.360637 | 3.764125 | 11.047646 | 11.800225 | 11.713056 |
| ATPIF1 | 1.958064245 | 0.043453389 | 0.000289214 | 253.5595079 | 3.024504 | 2.023048 | 2.379345 | 11.378567 | 10.365525 | 9.018932 |
| APEX1 | 2.100883422 | 0.043453389 | 0.000200749 | 251.0765437 | 2.201691 | 2.023048 | 2.165421 | 10.608241 | 10.137404 | 9.008063 |
| NDUFB9 | 2.220381039 | 0.043453389 | 0.000105478 | 242.6979432 | 3.024504 | 2.406905 | 2.165421 | 10.632786 | 10.329923 | 10.117111 |
| EEF1B2 | 1.93003145 | 0.043453389 | 0.000302824 | 238.8353675 | 5.658609 | 3.872014 | 4.508334 | 13.773392 | 12.408206 | 11.469377 |
| COX6A1 | 2.12160288 | 0.043453389 | 0.000166723 | 228.6747402 | 2.201691 | 2.023048 | 2.165421 | 11.38219 | 10.002574 | 9.363984 |
| AZGP1 | 1.618309973 | 0.043453389 | 0.001044573 | 225.9865268 | 3.024504 | 5.43468 | 2.165421 | 13.636724 | 9.985514 | 10.157018 |
| NGFRAP1 | 1.985894212 | 0.043453389 | 0.000248384 | 224.8691195 | 2.201691 | 2.809601 | 2.165421 | 10.283397 | 10.622543 | 8.894619 |
| RPL5 | 1.961424091 | 0.043453389 | 0.000275604 | 219.8114179 | 4.682076 | 4.911517 | 6.450701 | 13.291304 | 12.849623 | 12.462199 |
| F5 | 2.169345983 | 0.043453389 | 0.000132698 | 217.5426617 | 4.743564 | 4.389936 | 5.389265 | 12.155091 | 13.106596 | 13.021304 |
| TRMT5 | 1.959177502 | 0.043453389 | 0.000282409 | 214.0595634 | 2.993831 | 2.406905 | 3.324375 | 11.841672 | 10.735699 | 9.462817 |
| IFNG | 1.839643425 | 0.043453389 | 0.000452535 | 210.0206014 | 1.874444 | 2.023048 | 2.165421 | 9.904384 | 7.870158 | 9.737435 |
| MRFAP1 | 1.628363209 | 0.043453389 | 0.001003743 | 205.9092748 | 1.874444 | 2.023048 | 2.165421 | 11.655074 | 9.708913 | 7.03218 |
| NDUFB4 | 1.602438669 | 0.043453389 | 0.001105818 | 202.805178 | 5.304463 | 4.389936 | 5.389265 | 10.207812 | 9.979782 | 10.070856 |
| RPS15AP10 | 2.107597589 | 0.043453389 | 0.000187138 | 198.9640087 | 1.874444 | 2.406905 | 2.165421 | 10.522177 | 9.179013 | 9.801784 |
| TMEM66 | 2.021922072 | 0.043453389 | 0.000234774 | 195.3421233 | 3.819732 | 3.770995 | 4.508334 | 12.465486 | 11.429592 | 10.913082 |
| CRIP1 | 2.140409416 | 0.043453389 | 0.000153113 | 183.3012252 | 1.874444 | 2.023048 | 2.165421 | 9.513069 | 9.392516 | 10.769222 |
| VKORC1 | 2.135818569 | 0.043453389 | 0.000159918 | 170.4303269 | 2.201691 | 2.023048 | 2.165421 | 9.212855 | 9.578459 | 10.233665 |
| ANP32A-IT1 | 1.865657143 | 0.043453389 | 0.000411705 | 168.643307 | 2.993831 | 2.023048 | 2.165421 | 10.088666 | 10.391662 | 8.488368 |
| GADD45A | 1.931996026 | 0.043453389 | 0.000296019 | 160.2363742 | 2.201691 | 4.413323 | 3.324375 | 11.590755 | 10.573912 | 10.648433 |
| TPT1 | 1.708125641 | 0.043453389 | 0.000735927 | 155.053927 | 7.317579 | 7.598177 | 8.345336 | 15.666962 | 14.875403 | 13.24435 |
| COX6C | 1.761022932 | 0.043453389 | 0.000636271 | 154.2260542 | 1.874444 | 2.023048 | 4.449894 | 11.326854 | 10.479583 | 9.143346 |
| ORC4 | 1.966892101 | 0.043453389 | 0.000268799 | 153.869353 | 5.658609 | 6.270596 | 4.724406 | 12.49758 | 13.536158 | 12.87419 |
| ATP5C1 | 1.852589825 | 0.043453389 | 0.000438925 | 153.8305556 | 2.201691 | 3.872014 | 2.165421 | 10.413045 | 9.847551 | 9.430619 |
| RPL23AP32 | 1.809158235 | 0.043453389 | 0.00052772 | 153.6520772 | 3.819732 | 5.43468 | 5.544653 | 13.203909 | 12.609999 | 11.083256 |
| PLAC9 | 2.10842088 | 0.043453389 | 0.000180333 | 150.8812505 | 1.874444 | 2.406905 | 2.165421 | 9.111713 | 9.570854 | 9.540302 |
| LECT2 | 2.102414855 | 0.043453389 | 0.000193944 | 148.9165857 | 1.874444 | 2.023048 | 2.165421 | 9.137671 | 9.866312 | 9.092804 |
| FOS | 1.885638086 | 0.043453389 | 0.000377679 | 143.7517704 | 7.906175 | 8.359538 | 9.485302 | 15.43434 | 15.772014 | 15.526973 |
| SHFM1 | 2.043479395 | 0.043453389 | 0.000221164 | 141.4833514 | 1.874444 | 2.406905 | 2.165421 | 10.061802 | 9.294336 | 9.018932 |
| ERH | 1.8936896 | 0.043453389 | 0.000357264 | 140.8997425 | 2.993831 | 2.023048 | 2.165421 | 10.132356 | 9.615895 | 8.705744 |
| GAS5 | 1.923211748 | 0.043453389 | 0.000316434 | 140.7527401 | 5.263699 | 4.830496 | 5.723602 | 13.152318 | 12.400718 | 11.714728 |
| SEC61B | 1.892002869 | 0.043453389 | 0.000364069 | 139.6464222 | 1.874444 | 2.023048 | 2.165421 | 9.359771 | 9.148683 | 8.11568 |
| SH3BGRL | 1.913051187 | 0.043453389 | 0.000330044 | 139.3348421 | 2.993831 | 3.770995 | 3.90836 | 12.125128 | 10.893407 | 10.033825 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| RPL22L1 | 1.508761265 | 0.043453389 | 0.001534536 | 137.5242179 | 3.024504 | 2.023048 | 2.165421 | 10.128046 | 9.303543 | 6.942983 |
| COX5B | 1.705369901 | 0.043453389 | 0.000751956 | 134.1276716 | 4.209882 | 2.406905 | 2.379345 | 9.615142 | 9.563208 | 9.446808 |
| KLHDC2 | 2.065680981 | 0.043453389 | 0.000207554 | 133.7125125 | 1.874444 | 2.023048 | 2.165421 | 9.299725 | 9.086038 | 8.771488 |
| MAGED1 | 1.222033132 | 0.043453389 | 0.005155495 | 132.7235295 | 1.874444 | 2.023048 | 2.165421 | 9.698891 | 9.075328 | 4.790662 |
| PNN | 1.557414287 | 0.043453389 | 0.001269139 | 131.9970759 | 3.024504 | 2.023048 | 3.764125 | 10.906311 | 10.068866 | 7.825039 |
| LOC100506023 | 1.740666913 | 0.043453389 | 0.000663491 | 131.9005109 | 5.753024 | 5.487673 | 5.544653 | 11.096994 | 12.920903 | 12.58796 |
| NSA2 | 1.91147922 | 0.043453389 | 0.000336849 | 129.8697361 | 3.024504 | 4.389936 | 4.285996 | 11.410858 | 11.142043 | 10.561895 |
| DKFZP586I1420 | 1.811855658 | 0.043453389 | 0.000051378 | 129.7565838 | 1.874444 | 2.023048 | 2.165421 | 9.4931 | 9.042712 | 7.825039 |
| ALS2CR11 | 1.876227772 | 0.043453389 | 0.000398095 | 129.5512648 | 2.201691 | 2.023048 | 2.165421 | 8.190235 | 10.019435 | 9.040427 |
| SYTL2 | 1.815733438 | 0.043453389 | 0.00050017 | 126.4505035 | 4.263463 | 2.406905 | 2.995681 | 10.384422 | 8.564762 | 9.389334 |
| NPM1 | 1.807635518 | 0.043453389 | 0.000534195 | 126.21798599 | 4.263463 | 5.297868 | 5.571599 | 13.009671 | 12.277642 | 11.085843 |
| HNRPDL | 1.641044066 | 0.043453389 | 0.000969718 | 123.9718851 | 5.335413 | 5.661685 | 5.723602 | 13.207998 | 12.615554 | 10.648433 |
| NUDT4P1 | 1.644886848 | 0.043453389 | 0.000956108 | 123.4313424 | 1.874444 | 2.023048 | 3.90836 | 9.102956 | 9.075328 | 8.822008 |
| GBP4 | 1.755743811 | 0.043453389 | 0.000643076 | 122.4065158 | 2.993831 | 4.389936 | 3.90836 | 9.929368 | 11.33847 | 10.176565 |
| EIF4E | 1.830671756 | 0.043453389 | 0.000479755 | 122.177064 | 5.779429 | 6.184248 | 6.072169 | 11.889562 | 13.117078 | 13.048081 |
| CCDC53 | 1.901119239 | 0.043453389 | 0.000350459 | 119.3551415 | 2.201691 | 2.023048 | 2.165421 | 8.254097 | 9.064538 | 9.211256 |
| REXO1L1 | 1.607322078 | 0.043453389 | 0.001078598 | 116.8998888 | 1.874444 | 2.023048 | 2.379345 | 6.954147 | 8.892178 | 9.220702 |
| HSPA2 | 1.890116728 | 0.043453389 | 0.000370874 | 116.6670084 | 2.201691 | 2.023048 | 5.217616 | 8.222933 | 9.031674 | 9.276113 |
| HSPA1B | 1.447420164 | 0.043453389 | 0.001956448 | 115.393179 | 6.054828 | 7.476899 | 10.290431 | 12.905242 | 16.251649 | 15.72644 |
| S100A4 | 1.923729909 | 0.043453389 | 0.000309629 | 114.2240591 | 2.993831 | 2.023048 | 2.165421 | 9.81605 | 9.540026 | 8.858771 |
| HSP90AB2P | 1.713727119 | 0.043453389 | 0.000711126 | 112.5574067 | 5.865559 | 3.872014 | 4.285996 | 10.686531 | 11.745539 | 11.813235 |
| ODF2L | 2.009494261 | 0.043453389 | 0.000241579 | 112.2550355 | 2.201691 | 2.406905 | 2.379345 | 9.012327 | 9.20872 | 8.79697 |
| ALPK1 | 1.839164445 | 0.043453389 | 0.00045934 | 111.5506182 | 4.263463 | 3.872014 | 5.217616 | 10.955788 | 11.905258 | 11.065018 |
| HTRA1 | 1.429785882 | 0.043453389 | 0.002153794 | 110.6174257 | 2.993831 | 2.809601 | 3.90836 | 7.36523 | 10.697795 | 10.166824 |
| SCP2 | 1.459462552 | 0.043453389 | 0.001820347 | 110.3947184 | 1.874444 | 3.770995 | 2.165421 | 11.063531 | 8.951948 | 7.327219 |
| RNF130 | 1.731917012 | 0.043453389 | 0.000683906 | 109.097839 | 2.993831 | 2.406905 | 4.285996 | 9.645614 | 9.76331 | 9.984774 |
| RGS2 | 1.630971596 | 0.043453389 | 0.000833328 | 108.8304071 | 3.024504 | 2.406905 | 4.754917 | 11.332484 | 10.084974 | 9.172843 |
| NANS | 1.785611204 | 0.043453389 | 0.000581831 | 108.7541616 | 1.874444 | 2.809601 | 2.165421 | 10.564256 | 8.63937 | 8.66481 |
| C2orf40 | 1.507074711 | 0.043453389 | 0.001541341 | 102.9875918 | 4.209882 | 6.466258 | 4.285996 | 10.896209 | 11.076418 | 10.871709 |
| NUDT16P1 | 1.713972761 | 0.043453389 | 0.000704321 | 102.0659385 | 2.201691 | 2.406905 | 4.285996 | 8.875048 | 8.655275 | 10.42967 |
| ID2 | 1.855985231 | 0.043453389 | 0.000425315 | 101.7708428 | 1.874444 | 2.023048 | 2.165421 | 9.565008 | 8.140553 | 8.692228 |
| WBP5 | 1.701778978 | 0.043453389 | 0.000765567 | 101.1067993 | 2.993831 | 4.750708 | 3.935222 | 9.832037 | 10.666023 | 10.594958 |
| SCGB2A2 | 1.295621129 | 0.043453389 | 0.003998639 | 100.5383317 | 1.874444 | 3.32135 | 2.165421 | 15.276814 | 8.817023 | 6.32627 |
| FAM111B | 1.641725993 | 0.043453389 | 0.000962913 | 99.44021447 | 3.839948 | 2.023048 | 2.165421 | 8.801178 | 9.944904 | 8.678584 |
| TSPAN6 | 1.577243253 | 0.043453389 | 0.001214699 | 98.92829493 | 3.819732 | 2.406905 | 2.165421 | 10.448044 | 9.500541 | 7.849596 |
| MTRNR2L5 | 1.875961939 | 0.043453389 | 0.0004049 | 96.13170883 | 1.874444 | 2.023048 | 2.165421 | 8.105092 | 8.609988 | 8.870819 |
| FRA10AC1 | 1.815597976 | 0.043453389 | 0.000506975 | 95.7508315 | 3.024504 | 2.023048 | 2.165421 | 8.604261 | 9.031674 | 9.040427 |
| TIMELESS | 1.820527248 | 0.043453389 | 0.000493365 | 95.51583958 | 7.497182 | 8.595375 | 8.735088 | 8.779359 | 8.71031 | 10.18624 |
| GBAS | 1.708761447 | 0.043453389 | 0.000738346 | 95.16216427 | 2.201691 | 2.809601 | 3.764125 | 9.519665 | 8.737737 | 7.582913 |
| NEIL1 | 1.794248436 | 0.043453389 | 0.00056822 | 94.92711748 | 1.874444 | 2.023048 | 2.165421 | 8.591796 | 8.055928 | 10.070856 |
| COX17 | 1.807086789 | 0.043453389 | 0.000541 | 94.26613985 | 1.874444 | 2.406905 | 2.165421 | 9.154721 | 8.724089 | 8.03232 |
| VPS29 | 1.879831614 | 0.043453389 | 0.000391129 | 93.27969155 | 1.874444 | 2.023048 | 2.165421 | 8.566539 | 9.075328 | 8.175185 |
| BRD7P3 | 1.779594439 | 0.043453389 | 0.000588636 | 92.72338294 | 1.874444 | 2.406905 | 2.165421 | 8.700282 | 9.148683 | 7.920856 |
| SPTSSA | 1.881210649 | 0.043453389 | 0.000384485 | 92.2481629 | 6.008206 | 6.311907 | 6.450701 | 12.416848 | 13.163326 | 12.839356 |
| SSBP2 | 1.653705956 | 0.043453389 | 0.000928887 | 92.09088911 | 2.201691 | 2.023048 | 2.379345 | 8.768324 | 8.904331 | 7.395512 |
| RPL37 | 1.713115805 | 0.043453389 | 0.000717931 | 89.83259212 | 7.497182 | 8.595375 | 8.735088 | 15.940876 | 15.026399 | 13.986349 |
| PRINS | 1.703343767 | 0.043453389 | 0.000758761 | 89.39815136 | 3.024504 | 4.413323 | 3.764125 | 9.388882 | 10.50375 | 10.895496 |
| LAMB1 | 1.300864559 | 0.043453389 | 0.003930589 | 89.33361805 | 5.658609 | 4.750708 | 5.225216 | 8.688623 | 12.418836 | 11.706348 |
| ASTN2 | 1.778701368 | 0.043453389 | 0.000595441 | 88.9410239 | 5.263699 | 6.060401 | 5.544653 | 11.538127 | 12.603491 | 12.019431 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| SCGB1D2 | 1.289303444 | 0.043453389 | 0.004059884 | 88.89001699 | 1.874444 | 3.872014 | 2.165421 | 14.671711 | 8.63937 | 6.69026 |
| SPARCL1 | 1.547325881 | 0.043453389 | 0.001309969 | 87.74998484 | 5.897292 | 4.911517 | 5.217616 | 10.088666 | 12.274133 | 12.352619 |
| ABCC9 | 1.751429087 | 0.043453389 | 0.000649881 | 87.54727253 | 3.819732 | 4.830496 | 4.754917 | 10.271723 | 11.577343 | 11.173574 |
| LINC00311 | 1.710463899 | 0.043453389 | 0.000724736 | 87.32826877 | 1.874444 | 3.32135 | 2.379345 | 9.111713 | 9.652384 | 8.32282 |
| ZNF638 | 1.663370591 | 0.043453389 | 0.000867642 | 87.09798586 | 2.201691 | 2.023048 | 2.165421 | 8.757204 | 8.609988 | 7.36177 |
| NNMT | 1.546620081 | 0.043453389 | 0.001330384 | 86.64286536 | 4.639409 | 5.43468 | 3.764125 | 9.651632 | 11.076418 | 12.388682 |
| CSDA | 1.564885589 | 0.043453389 | 0.001241919 | 86.50388582 | 4.263463 | 2.406905 | 3.935222 | 10.967897 | 10.369915 | 8.650903 |
| FLJ30679 | 1.809168563 | 0.043453389 | 0.000520585 | 86.26644468 | 1.874444 | 2.023048 | 2.165421 | 8.447068 | 10.232059 | 8.305171 |
| KIFAP3 | 1.695183285 | 0.043453389 | 0.000785982 | 86.2019723 | 1.874444 | 2.023048 | 2.165421 | 7.394225 | 8.59507 | 8.503924 |
| GOLGA8A | 1.685234499 | 0.043453389 | 0.000813202 | 86.17042702 | 3.839948 | 3.360637 | 2.165421 | 10.263887 | 9.789758 | 8.882768 |
| ZCRB1 | 1.630753387 | 0.043453389 | 0.000990133 | 85.25338234 | 1.874444 | 2.023048 | 2.379345 | 8.993498 | 8.436733 | 7.255535 |
| LINC00550 | 1.597891195 | 0.043453389 | 0.001119428 | 85.00576375 | 4.639409 | 3.32135 | 2.379345 | 9.179923 | 10.970576 | 9.730839 |
| FAM156A | 1.859916134 | 0.043453389 | 0.00041851 | 83.57033195 | 1.874444 | 2.023048 | 2.165421 | 8.105092 | 8.829823 | 8.407967 |
| LTV1 | 1.295780792 | 0.043453389 | 0.003991834 | 83.4826698 | 1.874444 | 2.406905 | 2.165421 | 8.79031 | 8.579995 | 5.634184 |
| XCL2 | 1.406450137 | 0.043453389 | 0.00235182 | 83.2755294 | 1.874444 | 2.023048 | 2.165421 | 10.26781 | 8.402869 | 6.106561 |
| PCNP | 1.522140822 | 0.043453389 | 0.00147329 | 82.74568936 | 2.201691 | 2.023048 | 3.324375 | 8.895478 | 9.694987 | 7.352555 |
| METTL3 | 1.697356632 | 0.043453389 | 0.000772372 | 82.43731548 | 3.350997 | 2.023048 | 2.995681 | 9.716222 | 8.94019 | 8.705744 |
| TAF1A | 1.76331782 | 0.043453389 | 0.000629466 | 80.7900104 | 5.982974 | 4.911517 | 4.944468 | 11.247622 | 11.978942 | 11.938737 |
| BUD31 | 1.659059754 | 0.043453389 | 0.000901667 | 80.5667882 | 2.201691 | 3.360637 | 3.324375 | 9.252991 | 8.533804 | 9.928242 |
| SNRPE | 1.44655248 | 0.043453389 | 0.001963253 | 80.01631261 | 3.839948 | 2.023048 | 2.165421 | 10.162171 | 8.59507 | 7.492252 |
| SMA4 | 1.854393939 | 0.043453389 | 0.00043212 | 79.2767086 | 1.874444 | 2.023048 | 2.165421 | 8.331873 | 8.486085 | 8.053616 |
| SEPP1 | 1.594210951 | 0.043453389 | 0.001139843 | 78.3774597 | 4.263463 | 4.750708 | 5.217616 | 11.043074 | 12.04356 | 9.869404 |
| DAP | 1.426831249 | 0.043453389 | 0.002167404 | 77.25511038 | 4.815804 | 2.023048 | 2.379345 | 9.929368 | 8.63937 | 8.650903 |
| LOC100507577 | 1.777731736 | 0.043453389 | 0.000602246 | 77.24192131 | 2.201691 | 2.023048 | 2.165421 | 8.711848 | 8.436733 | 7.849596 |
| SRD5A3 | 1.538238892 | 0.043453389 | 0.00139163 | 77.24192131 | 3.839948 | 2.023048 | 2.165421 | 8.39062 | 8.436733 | 8.894619 |
| RCN2 | 1.786163442 | 0.043453389 | 0.000575026 | 76.80562542 | 1.874444 | 2.023048 | 2.165421 | 8.286188 | 9.540026 | 8.053616 |
| PENK | 0.914976213 | 0.044110923 | 0.015605308 | 76.80562542 | 1.874444 | 2.023048 | 2.165421 | 8.286188 | 8.97518 | 2.921909 |
| PGM5P2 | 1.635560543 | 0.043453389 | 0.000976523 | 76.58492221 | 1.874444 | 2.023048 | 2.165421 | 7.167419 | 8.36819 | 8.424409 |
| MYEOV2 | 1.693775148 | 0.043453389 | 0.000792787 | 76.35512295 | 1.874444 | 2.023048 | 2.165421 | 9.633502 | 8.277663 | 7.611911 |
| MARCH7 | 1.465747937 | 0.043453389 | 0.001765907 | 76.35512295 | 1.874444 | 2.023048 | 2.995681 | 9.552198 | 8.277663 | 6.931222 |
| PLEKHG4B | 1.691246176 | 0.043453389 | 0.002644437 | 76.34592584 | 1.874444 | 2.023048 | 2.165421 | 7.656039 | 8.4199 | 9.329475 |
| CTSK | 1.657867832 | 0.043453389 | 0.000908472 | 75.793297 | 2.993831 | 2.406905 | 2.165421 | 8.286188 | 10.840623 | 8.650903 |
| B3GNT6 | 1.835463685 | 0.043453389 | 0.00047295 | 74.94925286 | 1.874444 | 2.023048 | 2.165421 | 8.051486 | 8.71031 | 8.25089 |
| RAB6C | 1.441137748 | 0.043453389 | 0.002024498 | 73.65572695 | 1.874444 | 2.809601 | 2.165421 | 9.012327 | 8.453372 | 6.649696 |
| HAT1 | 1.825900902 | 0.043453389 | 0.00048656 | 73.51086639 | 1.874444 | 2.023048 | 2.165421 | 8.222933 | 8.737737 | 8.03232 |
| MRPL51 | 1.739162714 | 0.043453389 | 0.000670296 | 73.38641922 | 1.874444 | 2.023048 | 2.165421 | 9.07636 | 8.220489 | 7.722406 |
| LETMD1 | 1.662786021 | 0.043453389 | 0.000881252 | 73.38641922 | 1.874444 | 2.023048 | 2.165421 | 9.381659 | 8.220489 | 7.428484 |
| AGR2 | 1.102299491 | 0.04349335 | 0.008119769 | 73.14253387 | 3.350997 | 2.023048 | 2.165421 | 10.686531 | 8.220489 | 4.146207 |
| HMGB1 | 1.716566958 | 0.043453389 | 0.000697516 | 72.76196462 | 2.201691 | 2.023048 | 3.90836 | 9.963633 | 10.132246 | 9.230086 |
| SH3YL1 | 1.385568479 | 0.043453389 | 0.002644437 | 72.70291986 | 2.201691 | 2.023048 | 2.165421 | 9.424465 | 8.350533 | 6.106561 |
| SSBP1 | 1.488885082 | 0.043453389 | 0.001602586 | 72.39752441 | 1.874444 | 2.809601 | 2.165421 | 9.33006 | 8.385634 | 7.020304 |
| N4BP2 | 1.769713911 | 0.043453389 | 0.000618856 | 72.12258695 | 4.209882 | 2.406905 | 2.165421 | 7.748771 | 8.200916 | 8.503924 |
| ADD3 | 1.446031008 | 0.043453389 | 0.001983668 | 71.22139426 | 5.753024 | 3.770995 | 3.935222 | 8.993498 | 10.558612 | 8.579284 |
| SLC25A34 | 1.54063354 | 0.043453389 | 0.001371215 | 70.47474434 | 2.201691 | 2.406905 | 4.944468 | 10.153715 | 11.224335 | 11.098707 |
| GPR124 | 1.401742654 | 0.043453389 | 0.002433481 | 70.40654115 | 2.993831 | 3.32135 | 4.285996 | 7.074163 | 10.074256 | 9.454835 |
| TCEAL4 | 1.673515508 | 0.043453389 | 0.000840422 | 70.33945248 | 3.350997 | 2.023048 | 2.165421 | 10.423634 | 10.356707 | 9.02972 |
| BBS5 | 1.770316472 | 0.043453389 | 0.000609051 | 69.92017279 | 5.491121 | 2.406905 | 2.379345 | 8.139755 | 9.321782 | 8.010706 |
| TMEM231 | 1.217252978 | 0.043453389 | 0.005264376 | 69.77123215 | 5.491121 | 2.406905 | 2.379345 | 8.527804 | 8.791075 | 8.534542 |
| MLF1 | 1.578356542 | 0.043453389 | 0.001207894 | 69.77123215 | 2.993831 | 2.023048 | 2.379345 | 7.607339 | 9.540026 | 8.503924 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| NUBPL | 1.458889222 | 0.043453389 | 0.001833957 | 69.20197918 | 1.874444 | 2.023048 | 3.90836 | 8.069577 | 8.751258 | 8.135789 |
| SNHG4 | 1.432548484 | 0.043453389 | 0.002112964 | 69.17804025 | 1.874444 | 2.023048 | 2.165421 | 6.283686 | 8.277663 | 8.213534 |
| CXCL14 | 0.96220209 | 0.043778104 | 0.013275944 | 69.07376332 | 4.309025 | 6.092406 | 5.592916 | 6.651882 | 12.418836 | 11.702982 |
| SDHD | 1.334042198 | 0.043453389 | 0.003318135 | 68.91673571 | 1.874444 | 2.809601 | 2.165421 | 8.361545 | 8.916384 | 6.106561 |
| SEC61G | 1.709367061 | 0.043453389 | 0.000731541 | 68.14216959 | 1.874444 | 2.023048 | 2.379345 | 8.604261 | 8.469821 | 8.374509 |
| PON2 | 1.691338951 | 0.043453389 | 0.000799592 | 68.14216959 | 1.874444 | 2.406905 | 2.379345 | 10.119387 | 8.469821 | 7.920856 |
| HBP1 | 1.679649016 | 0.043453389 | 0.000820007 | 67.76725294 | 3.839948 | 3.32135 | 4.285996 | 10.298817 | 9.409671 | 9.922465 |
| BHMT2 | 1.398157011 | 0.043453389 | 0.002460701 | 67.38609368 | 2.993831 | 2.023048 | 2.165421 | 6.651882 | 8.2398 | 9.211256 |
| PPIA | 1.661242799 | 0.043453389 | 0.000894862 | 67.13840789 | 6.554045 | 6.762934 | 6.326717 | 11.869047 | 12.859021 | 12.623111 |
| ACTG2 | 1.247105706 | 0.043453389 | 0.004760363 | 66.49012465 | 1.874444 | 2.406905 | 2.165421 | 8.895478 | 8.220489 | 5.426231 |
| PPWD1 | 1.542531026 | 0.043453389 | 0.0013508 | 66.46423302 | 1.874444 | 2.023048 | 2.379345 | 8.65307 | 8.077554 | 6.931222 |
| TATDN1 | 1.435006348 | 0.043453389 | 0.002092548 | 66.46423302 | 1.874444 | 2.023048 | 2.165421 | 9.344992 | 8.077554 | 6.32627 |
| COX4I1 | 1.663688649 | 0.043453389 | 0.000860837 | 66.05695683 | 5.316227 | 4.80797 | 5.723602 | 12.255316 | 11.30448 | 10.853609 |
| MUCL1 | 1.361022676 | 0.043453389 | 0.002957469 | 66.01609304 | 4.209882 | 5.148082 | 2.995681 | 13.474327 | 9.375155 | 9.040427 |
| CCDC148 | 1.666417704 | 0.043453389 | 0.000854032 | 65.85659481 | 1.874444 | 2.406905 | 2.165421 | 8.206677 | 8.518072 | 7.523109 |
| LOC100507584 | 1.378889104 | 0.043453389 | 0.002746512 | 64.6344836 | 2.993831 | 2.023048 | 2.165421 | 6.498222 | 8.402869 | 9.008063 |
| CLU | 1.480628323 | 0.043453389 | 0.001670636 | 64.44572806 | 4.309025 | 6.044198 | 4.724406 | 12.054211 | 11.175024 | 9.857343 |
| TOP2B | 1.620680744 | 0.043453389 | 0.001017353 | 64.191368 | 3.350997 | 3.32135 | 2.995681 | 9.513069 | 9.321782 | 8.357484 |
| AGR3 | 1.190971261 | 0.043453389 | 0.005957809 | 63.80223603 | 3.024509 | 3.32135 | 2.023048 | 9.973276 | 8.160956 | 5.446557 |
| C8orf59 | 1.579039887 | 0.043453389 | 0.001194284 | 63.61700766 | 3.839948 | 3.770995 | 2.165421 | 9.577706 | 9.312691 | 8.519314 |
| SYNPO2 | 1.348636836 | 0.043453389 | 0.003107179 | 63.52197144 | 6.099991 | 1.874444 | 3.935222 | 9.924405 | 9.841243 | 10.166824 |
| ANKRA2 | 1.299220119 | 0.043453389 | 0.003944199 | 63.49764466 | 1.874444 | 2.023048 | 2.165421 | 8.346785 | 8.011679 | 5.634184 |
| METTL9 | 1.482599976 | 0.043453389 | 0.001663831 | 63.4548232 | 4.263463 | 2.406905 | 2.165421 | 8.745998 | 9.348715 | 8.010706 |
| TRIM58 | 1.656609465 | 0.043453389 | 0.000922082 | 63.44208563 | 1.874444 | 2.809601 | 2.165421 | 9.179923 | 8.518072 | 8.79697 |
| PLK2 | 1.430182539 | 0.043453389 | 0.002146989 | 63.39053395 | 2.993831 | 3.360637 | 5.018694 | 9.137671 | 9.44338 | 9.346832 |
| CHMP2B | 1.448769749 | 0.043453389 | 0.001922423 | 62.90718247 | 1.874444 | 2.809601 | 4.285996 | 10.240121 | 9.198885 | 7.849596 |
| CD48 | 1.672049138 | 0.043453389 | 0.000847227 | 61.81627289 | 3.024509 | 2.023048 | 2.995681 | 8.974419 | 8.332658 | 8.858771 |
| C14orf2 | 1.601642733 | 0.043453389 | 0.001112623 | 61.76640587 | 4.682076 | 4.351315 | 2.379345 | 10.145209 | 9.796295 | 10.630827 |
| TMEM50A | 1.769806 | 0.043453389 | 0.000625723 | 61.69181251 | 4.639409 | 2.023048 | 2.165421 | 10.586416 | 9.064538 | 6.106561 |
| AP1S | 1.247261419 | 0.043453389 | 0.004699558 | 60.75654758 | 1.874444 | 2.406905 | 4.754917 | 8.331873 | 8.36819 | 7.800057 |
| CD2 | 1.618406033 | 0.043453389 | 0.001031768 | 60.58129954 | 1.874444 | 2.023048 | 2.165421 | 8.915622 | 7.25505 | 7.943848 |
| UG0898H09 | 1.441054827 | 0.043453389 | 0.002031303 | 60.49735265 | 4.743564 | 2.023048 | 3.935222 | 8.745998 | 9.492512 | 10.662364 |
| GPLD1 | 1.379815947 | 0.043453389 | 0.002726097 | 60.48688242 | 4.682076 | 3.872014 | 3.90836 | 7.792994 | 9.075328 | 9.973643 |
| PPT1 | 1.523784225 | 0.043453389 | 0.001452875 | 60.21843259 | 3.350997 | 2.023048 | 2.165421 | 8.206677 | 8.077554 | 7.96648 |
| LUM | 1.4691771 | 0.043453389 | 0.001738687 | 60.21559926 | 4.815804 | 4.389936 | 5.974145 | 10.402378 | 12.532831 | 10.302002 |
| TOP1P1 | 1.516181741 | 0.043453389 | 0.00151412 | 59.3643455 | 2.993831 | 3.32135 | 3.90836 | 9.799885 | 9.615895 | 8.155622 |
| PITRM1 | 1.589520795 | 0.043453389 | 0.001173869 | 59.32962928 | 2.201691 | 2.809601 | 2.165421 | 8.700282 | 8.36819 | 7.492252 |
| GNG11 | 1.157979692 | 0.043453389 | 0.006665532 | 59.27383745 | 5.700376 | 2.406905 | 2.165421 | 8.239009 | 8.296229 | 9.008063 |
| NUDT9 | 1.591693272 | 0.043453389 | 0.00116706 | 59.14136941 | 4.743564 | 4.413323 | 3.90836 | 9.794456 | 10.765988 | 9.832914 |
| DLC1 | 1.436271223 | 0.043453389 | 0.002072133 | 58.9993446 | 1.874444 | 2.809601 | 4.285996 | 8.239009 | 9.20872 | 8.692228 |
| GNPTG | 1.251006579 | 0.043453389 | 0.004617897 | 58.88495099 | 3.024509 | 2.023048 | 2.379345 | 8.875048 | 8.904331 | 6.106561 |
| OR11A1 | 1.430393383 | 0.043453389 | 0.002140184 | 58.66564075 | 1.874444 | 2.023048 | 2.165421 | 6.339437 | 8.077554 | 7.897492 |
| GTF3A | 1.519092461 | 0.043453389 | 0.0014869 | 58.55343516 | 3.350997 | 2.023048 | 2.165421 | 9.733347 | 7.89473 | 6.924055 |
| MSH3 | 1.461677519 | 0.043453389 | 0.001806737 | 58.09168605 | 3.819732 | 2.406905 | 2.165421 | 7.210813 | 8.751258 | 9.211256 |
| THUMPD1 | 1.417095149 | 0.043453389 | 0.002215039 | 57.86115524 | 1.874444 | 2.023048 | 2.165421 | 7.877571 | 8.258856 | 8.095288 |
| AREG | 0.832883218 | 0.044797567 | 0.019843484 | 57.77096022 | 1.874444 | 3.770995 | 3.935222 | 12.218289 | 9.623267 | 2.921909 |
| BCO2 | 1.652383994 | 0.043453389 | 0.000935692 | 57.70781913 | 1.874444 | 2.023048 | 2.165421 | 7.42265 | 8.751258 | 7.873743 |
| DDHD1 | 1.556078511 | 0.043453389 | 0.001289554 | 57.6532377 | 4.309025 | 2.406905 | 3.935222 | 9.212855 | 10.157854 | 9.389334 |
| LOC401074 | 1.611799847 | 0.043453389 | 0.001058183 | 57.59860672 | 1.874444 | 2.406905 | 2.165421 | 7.814607 | 9.652384 | 7.722406 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| STXBP3 | 1.541650609 | 0.043453389 | 0.00136441 | 57.56461128 | 1.874444 | 2.023048 | 2.165421 | 9.030914 | 7.870158 | 6.931222 |
| EFCAB4A | 1.426180066 | 0.043453389 | 0.002174209 | 56.97599942 | 2.201691 | 2.023048 | 2.995681 | 9.4931 | 8.033973 | 6.931222 |
| TMEM17 | 1.732072961 | 0.043453389 | 0.000677101 | 56.90132997 | 1.874444 | 2.023048 | 2.165421 | 7.995811 | 7.819723 | 8.579284 |
| ITPR1 | 1.661592255 | 0.043453389 | 0.000888057 | 56.57579413 | 1.874444 | 2.023048 | 2.165421 | 8.033165 | 7.845161 | 7.36177 |
| RPL23P8 | 1.418889418 | 0.043453389 | 0.002208234 | 56.57094654 | 8.224469 | 8.407985 | 8.710484 | 14.854834 | 14.229975 | 12.740216 |
| USMG5 | 1.279768138 | 0.043453389 | 0.00418918 | 56.30308342 | 4.682076 | 5.297868 | 2.379345 | 11.349244 | 10.11666 | 8.194487 |
| DYNC2LI1 | 1.492102969 | 0.043453389 | 0.001561756 | 56.13765012 | 1.874444 | 2.023048 | 3.324375 | 7.937902 | 7.68534 | 8.232333 |
| TUBA1A | 1.589065557 | 0.043453389 | 0.001180674 | 56.06002393 | 4.963444 | 5.809601 | 4.944468 | 11.18883 | 11.618502 | 10.437793 |
| TRIP13 | 1.478101842 | 0.043453389 | 0.001684246 | 55.6753434 | 1.874444 | 2.406905 | 3.324375 | 7.679787 | 7.870158 | 9.123341 |
| QARS | 1.493715001 | 0.043453389 | 0.001554951 | 55.28257456 | 3.819732 | 3.872014 | 3.324375 | 10.544987 | 9.608485 | 8.32282 |
| NDUFAB1 | 1.603960178 | 0.043453389 | 0.001099013 | 54.55432044 | 1.874444 | 2.809601 | 2.165421 | 8.579223 | 8.033973 | 7.640338 |
| ACTA2 | 1.084132897 | 0.043516135 | 0.008805036 | 54.41355806 | 1.874444 | 6.060401 | 2.165421 | 9.615142 | 8.140553 | 7.640338 |
| IGFBP7 | 1.533128851 | 0.043453389 | 0.00141885 | 54.35845954 | 7.392123 | 5.195784 | 6.704285 | 13.156556 | 12.408206 | 11.964266 |
| IKBKAP | 1.629863814 | 0.043453389 | 0.000996938 | 54.23709835 | 2.201691 | 2.023048 | 2.379345 | 7.42265 | 8.140553 | 8.03232 |
| ASB4 | 1.245046811 | 0.043453389 | 0.004753998 | 53.94510074 | 3.024504 | 2.023048 | 5.018694 | 7.995811 | 8.777924 | 8.784285 |
| FAM192A | 1.62042571 | 0.043453389 | 0.001024158 | 53.87659078 | 2.201691 | 2.201691 | 3.324375 | 8.591796 | 8.453372 | 7.774634 |
| TMEM9 | 1.475841785 | 0.043453389 | 0.001697856 | 53.52562077 | 1.874444 | 2.406905 | 3.324375 | 9.23707 | 8.332658 | 7.943848 |
| SNHG5 | 1.614652598 | 0.043453389 | 0.001051378 | 53.3518941 | 1.874444 | 2.023048 | 2.379345 | 9.196483 | 7.96603 | 7.611911 |
| PCF11 | 1.388454947 | 0.043453389 | 0.002589997 | 53.3518941 | 1.874444 | 2.023048 | 3.90836 | 8.122528 | 8.4199 | 7.611911 |
| TRIM59 | 1.457570981 | 0.043453389 | 0.001847567 | 53.18306912 | 1.874444 | 2.023048 | 3.764125 | 7.607339 | 8.777924 | 8.456743 |
| PSIP1 | 1.486005217 | 0.043453389 | 0.001629806 | 53.17005402 | 1.874444 | 3.32135 | 2.165421 | 7.897963 | 8.055928 | 7.800057 |
| LMOD1 | 1.593751306 | 0.043453389 | 0.001146649 | 53.15269239 | 2.201691 | 3.360637 | 2.165421 | 9.040118 | 8.71031 | 7.897492 |
| LGALS3 | 1.655847023 | 0.043453389 | 0.000915277 | 53.07275475 | 4.963444 | 4.911517 | 5.723602 | 11.400174 | 11.419041 | 10.641416 |
| FASTKD2 | 1.663093547 | 0.043453389 | 0.000874447 | 53.05103103 | 1.874444 | 2.406905 | 2.165421 | 8.051486 | 7.89473 | 7.611911 |
| NUP133 | 1.592058655 | 0.043453389 | 0.001160259 | 53.05103103 | 2.201691 | 2.023048 | 2.165421 | 7.177844 | 7.89473 | 8.095288 |
| KLHL7-AS1 | 1.605178652 | 0.043453389 | 0.001092208 | 52.91933604 | 3.024504 | 2.023048 | 2.165421 | 7.748771 | 8.71031 | 8.32282 |
| BRP44L | 1.574914581 | 0.043453389 | 0.001228309 | 52.62060003 | 1.874444 | 2.023048 | 2.379345 | 8.316805 | 7.740604 | 7.180104 |
| FAM200A | 1.490969843 | 0.043453389 | 0.001582171 | 52.62060003 | 1.874444 | 2.023048 | 2.165421 | 6.664985 | 7.740604 | 8.440667 |
| C16orf80 | 1.486472 | 0.043453389 | 0.001623001 | 52.62060003 | 1.874444 | 2.023048 | 2.165421 | 9.229044 | 7.740604 | 6.73963 |
| BPHL | 1.133394708 | 0.043453389 | 0.007257571 | 52.62060003 | 1.874444 | 2.023048 | 2.165421 | 4.739845 | 7.740604 | 8.407967 |
| CD69 | 1.314100946 | 0.043453389 | 0.003644777 | 51.81823228 | 3.024504 | 2.023048 | 4.508334 | 10.203722 | 7.107836 | 9.710869 |
| FBXW4 | 1.311814589 | 0.043453389 | 0.003699217 | 51.75598181 | 2.993831 | 3.360637 | 2.165421 | 9.049264 | 8.696398 | 6.69026 |
| LOC100859930 | 1.556766111 | 0.043453389 | 0.001282749 | 51.53009294 | 3.024504 | 2.023048 | 2.995681 | 8.711848 | 8.055928 | 8.758577 |
| FGFR1OP2 | 1.455211655 | 0.043453389 | 0.001854372 | 51.50604618 | 1.874444 | 2.023048 | 2.995681 | 7.856887 | 8.682351 | 7.033813 |
| LOC283104 | 1.5573986 | 0.043453389 | 0.00127594 | 51.41707166 | 2.201691 | 3.32135 | 2.165421 | 8.376156 | 8.609988 | 7.849596 |
| FOXM1 | 1.450908287 | 0.043453389 | 0.001881592 | 51.41707166 | 3.350997 | 3.360637 | 2.165421 | 8.331873 | 9.555522 | 7.849596 |
| DDOST | 1.395716358 | 0.043453389 | 0.002481116 | 51.11806947 | 4.639409 | 3.770995 | 6.282905 | 8.488001 | 9.321782 | 8.997112 |
| HSPA6 | 1.206110167 | 0.043453389 | 0.005475332 | 50.82479756 | 1.874444 | 2.023048 | 2.165421 | 9.438455 | 10.666023 | 8.60836 |
| TRAPPC2L | 1.559059581 | 0.043453389 | 0.001262334 | 50.64305361 | 1.874444 | 2.023048 | 2.165421 | 8.501391 | 7.68534 | 7.020304 |
| SRGN | 1.303216971 | 0.043453389 | 0.003855733 | 50.61192066 | 6.58615 | 2.023048 | 5.225216 | 11.092577 | 9.944904 | 10.886622 |
| GRAMD3 | 1.31245776 | 0.043453389 | 0.003685607 | 50.34684703 | 2.993831 | 3.32135 | 2.995681 | 8.65307 | 8.97518 | 6.931222 |
| CMKLR1 | 1.439974974 | 0.043453389 | 0.002038108 | 50.21710565 | 4.639409 | 3.360637 | 4.754917 | 10.329172 | 8.867558 | 10.405024 |
| OR1J1 | 1.462635218 | 0.043453389 | 0.001793127 | 49.69678306 | 3.819732 | 2.023048 | 4.449894 | 8.566539 | 10.084974 | 9.446808 |
| SDHB | 1.5573986 | 0.043453389 | 0.00127594 | 49.65429477 | 1.874444 | 2.023048 | 2.165421 | 9.794456 | 7.656894 | 5.634184 |
| MTRNR2L8 | 1.279968458 | 0.043453389 | 0.004182375 | 49.64604431 | 8.984007 | 11.971005 | 12.360493 | 17.9941 | 15.136436 | 16.001611 |
| FMO1 | 1.14853349 | 0.043581008 | 0.006896904 | 49.57929852 | 1.874444 | 2.023048 | 3.90836 | 4.894482 | 9.540026 | 7.825039 |
| ARPC2 | 1.017504819 | 0.043453389 | 0.01115073 | 49.25842145 | 5.263699 | 3.872014 | 3.324375 | 9.040118 | 9.540026 | 9.494312 |
| C13orf15 | 1.359692536 | 0.043453389 | 0.002977884 | 49.23190156 | 3.839948 | 3.770995 | 2.379345 | 11.017672 | 9.392516 | 8.809543 |
| CRIM1 | 1.559100619 | 0.043453389 | 0.001255529 | 49.04918518 | 2.993831 | 4.351315 | 2.379345 | 9.621288 | 8.609988 | 8.155622 |
| (CRIM1) | 1.404335344 | 0.043453389 | 0.002385846 | | | | | | | |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| TRAPPC12 | 1.542077607 | 0.043453389 | 0.001357605 | 48.82980598 | 3.024504 | 2.023048 | 2.379345 | 8.316805 | 7.989035 | 7.668215 |
| RERG | 1.355380167 | 0.043453389 | 0.003045934 | 48.68655809 | 3.839948 | 2.023048 | 2.995681 | 9.4454 | 7.713236 | 7.897492 |
| NDUFA12 | 1.349872936 | 0.043453389 | 0.003086764 | 48.66554626 | 1.874444 | 2.023048 | 2.165421 | 10.170577 | 7.627877 | 6.129407 |
| CCDC142 | 1.247830974 | 0.043453389 | 0.004679143 | 48.54459561 | 2.993831 | 2.023048 | 4.754917 | 7.748771 | 8.59507 | 8.719135 |
| AHSA2 | 1.523550347 | 0.043453389 | 0.001466485 | 48.53492918 | 3.350997 | 2.023048 | 3.935222 | 9.102956 | 8.951948 | 8.66481 |
| NUP54 | 1.64565965 | 0.043453389 | 0.000949302 | 48.46566641 | 1.874444 | 2.023048 | 2.165421 | 7.531061 | 7.473335 | 8.155622 |
| PPCS | 1.093083876 | 0.04349335 | 0.008487241 | 48.23933414 | 2.201691 | 2.406905 | 2.165421 | 8.553743 | 7.793829 | 4.790662 |
| RIOK1 | 1.554499834 | 0.043453389 | 0.001303164 | 48.07234315 | 1.874444 | 2.406905 | 2.379345 | 8.433162 | 7.191402 | 7.96648 |
| MYH11 | 1.400384219 | 0.043453389 | 0.00244709 | 48.04000683 | 2.993831 | 4.389936 | 2.165421 | 8.801178 | 8.579995 | 8.488368 |
| C14orf166 | 1.110429163 | 0.043485739 | 0.007901327 | 47.98515005 | 3.839948 | 2.023048 | 2.165421 | 9.424465 | 8.314558 | 5.446557 |
| SDPR | 1.528826607 | 0.043453389 | 0.001425655 | 47.94638146 | 2.201691 | 2.023048 | 2.165421 | 7.748771 | 7.094385 | 9.153246 |
| LINC00116 | 1.435184958 | 0.043453389 | 0.002085743 | 47.94638146 | 3.024504 | 3.32135 | 2.165421 | 7.91889 | 7.91889 | 9.018932 |
| ANKRD30A | 0.964015512 | 0.043778104 | 0.013194284 | 47.6768087 | 1.874444 | 2.023048 | 2.165421 | 8.286188 | 7.598264 | 3.676349 |
| TRIM4 | 1.517903873 | 0.043453389 | 0.00150051 | 47.74376348 | 1.874444 | 3.872014 | 3.90836 | 9.322536 | 9.47632 | 8.771488 |
| TAF7 | 1.45084417 | 0.043453389 | 0.001888397 | 47.4126254 | 4.682076 | 3.770995 | 2.165421 | 8.822673 | 10.095614 | 9.33818 |
| TSPAN13 | 1.19113304 | 0.043453389 | 0.005944199 | 47.36570059 | 2.201691 | 2.809601 | 2.165421 | 9.220972 | 7.767462 | 5.580533 |
| NCRUPAR | 1.184335036 | 0.043453389 | 0.006073494 | 47.33736239 | 4.743564 | 4.389936 | 4.724406 | 5.579836 | 7.819723 | 8.374509 |
| TXN | 1.37895339 | 0.043453389 | 0.002739707 | 47.32022999 | 1.874444 | 2.023048 | 2.165421 | 11.393008 | 10.288791 | 8.745549 |
| TTC23 | 1.575782543 | 0.043453389 | 0.001221504 | 47.17221773 | 1.874444 | 4.830496 | 5.217616 | 7.074163 | 8.011679 | 7.582913 |
| LOC494558 | 1.346818519 | 0.043453389 | 0.003134399 | 47.12945204 | 4.743564 | 3.360637 | 2.379345 | 7.937902 | 9.339793 | 9.875397 |
| UQCRQ | 1.38307657 | 0.043453389 | 0.002692072 | 47.10625677 | 5.865559 | 4.351315 | 3.764125 | 10.701112 | 9.909162 | 9.656224 |
| TRA2B | 1.515886798 | 0.043453389 | 0.001520925 | 46.91340918 | 5.744513 | 4.736586 | 5.018694 | 10.570622 | 10.320883 | 10.791579 |
| OLFML3 | 1.331512079 | 0.043453389 | 0.003358966 | 46.79253506 | 1.874444 | 2.406905 | 4.449894 | 7.42265 | 9.834907 | 8.564524 |
| PSMD10 | 1.251820898 | 0.043453389 | 0.004597482 | 46.77985834 | 2.201691 | 2.023048 | 2.165421 | 8.540832 | 7.713236 | 5.580533 |
| C7orf55 | 1.467418008 | 0.043453389 | 0.001759102 | 46.68808276 | 7.427999 | 5.661685 | 4.285996 | 8.014609 | 7.56803 | 6.587378 |
| CTSC | 1.342591047 | 0.043453389 | 0.00320245 | 46.47540701 | 3.819732 | 4.389936 | 4.285996 | 10.998912 | 12.082858 | 11.200081 |
| WDR91 | 1.387972805 | 0.043453389 | 0.002617217 | 46.4578361 | 2.201691 | 4.389936 | 3.324375 | 8.222933 | 9.357582 | 9.478651 |
| OSGEP | 1.465263983 | 0.043453389 | 0.001772712 | 46.2144858 | 1.874444 | 2.023048 | 3.324375 | 8.239009 | 7.942653 | 7.553321 |
| UROD | 1.222650641 | 0.043453389 | 0.00514869 | 46.05448993 | 5.263699 | 3.32135 | 2.379345 | 8.286188 | 8.867558 | 8.84662 |
| CPPED1 | 1.193727842 | 0.043453389 | 0.005842123 | 46.0350933 | 3.024504 | 3.360637 | 5.596986 | 8.885299 | 8.916384 | 8.650903 |
| EFHA1 | 1.461384558 | 0.043453389 | 0.001813542 | 45.92057625 | 1.874444 | 3.360637 | 2.165421 | 8.801178 | 8.033973 | 7.395512 |
| GSTK1 | 1.511118558 | 0.043453389 | 0.001527731 | 45.54988718 | 3.024504 | 4.830496 | 5.217616 | 10.726991 | 10.106175 | 10.086439 |
| CDKN1B | 1.412085189 | 0.043453389 | 0.002276965 | 45.54748689 | 1.874444 | 3.360637 | 3.324375 | 10.580119 | 8.533804 | 7.553321 |
| WDR61 | 1.362437942 | 0.043453389 | 0.002930248 | 45.54023245 | 4.263463 | 3.360637 | 3.324375 | 9.772533 | 8.928336 | 7.943848 |
| DDX26B | 1.48532569 | 0.043453389 | 0.001636611 | 45.50688735 | 1.874444 | 2.023048 | 2.165421 | 7.531061 | 8.140553 | 6.69026 |
| CPE | 1.339294032 | 0.043453389 | 0.00326589 | 45.44430871 | 5.658609 | 4.351315 | 6.031658 | 10.444582 | 11.821211 | 9.857343 |
| ARMCX2 | 1.516230905 | 0.043453389 | 0.001507315 | 45.41059124 | 3.024504 | 2.809601 | 2.165421 | 7.33564 | 8.314558 | 7.695565 |
| C1orf43 | 1.324423029 | 0.043453389 | 0.003508676 | 45.41059124 | 4.263463 | 2.809601 | 2.379345 | 8.641022 | 8.314558 | 7.774634 |
| LOC100286844 | 1.607849608 | 0.043453389 | 0.001071793 | 45.06308174 | 2.201691 | 2.023048 | 2.165421 | 7.42265 | 7.96603 | 7.695565 |
| ESD | 1.47935505 | 0.043453389 | 0.001677441 | 45.02909103 | 2.993831 | 2.023048 | 3.764125 | 8.361545 | 9.25691 | 8.175185 |
| FAM13A-AS1 | 1.34622041 | 0.043453389 | 0.000314801 | 44.96673738 | 1.874444 | 2.023048 | 3.935222 | 7.36623 | 8.564762 | 7.96648 |
| C6orf125 | 1.609002638 | 0.043453389 | 0.001064988 | 44.8590162 | 1.874444 | 2.023048 | 2.165421 | 8.301578 | 7.473335 | 7.36177 |
| LCMT1 | 1.347650621 | 0.043453389 | 0.003120789 | 44.71066871 | 1.874444 | 2.406905 | 2.165421 | 7.656039 | 7.505595 | 6.051818 |
| MFF | 1.413350928 | 0.043453389 | 0.002249064 | 44.55954665 | 3.024504 | 2.023048 | 3.324375 | 8.955085 | 8.502167 | 7.291822 |
| CCNG1 | 1.2914608 | 0.043453389 | 0.001677441 | 44.44482313 | 2.201691 | 4.750708 | 2.165421 | 9.755869 | 8.332658 | 7.640338 |
| DKK3 | 1.403636687 | 0.043453389 | 0.002392651 | 44.29851721 | 1.874444 | 3.360637 | 2.379345 | 8.801178 | 8.829823 | 6.942983 |
| SMARCD3 | 1.321852303 | 0.043453389 | 0.003556312 | 44.21529072 | 3.839948 | 2.023048 | 2.165421 | 7.631894 | 7.56803 | 8.010706 |
| LOC100507377 | 1.44605423 | 0.043453389 | 0.001976863 | 43.72198226 | 1.874444 | 2.023048 | 2.165421 | 6.544171 | 7.473335 | 8.374509 |
| DCTN6 | 1.032970004 | 0.043577906 | 0.01047363 | 43.72198226 | 1.874444 | 2.023048 | 2.165421 | 8.604261 | 7.473335 | 4.146207 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| IMMT | 1.465211561 | 0.043453389 | 0.001779517 | 43.6907014 | 3.839948 | 2.809601 | 3.324375 | 8.514658 | 8.258856 | 9.414247 |
| DZIP3 | 1.487817212 | 0.043453389 | 0.001616196 | 43.34135597 | 2.201691 | 2.023048 | 2.995681 | 7.918071 | 7.713236 | 7.46072 |
| MSMO1 | 1.022115956 | 0.043577906 | 0.010954066 | 43.30365941 | 5.316227 | 4.736586 | 2.379345 | 11.702223 | 10.173004 | 6.195186 |
| RAB13 | 1.217060254 | 0.043453389 | 0.005277986 | 43.07348259 | 5.491121 | 3.32135 | 2.995681 | 9.396069 | 8.817023 | 8.424409 |
| HCG18 | 1.528499119 | 0.043453389 | 0.001439265 | 42.93417375 | 5.316227 | 4.750708 | 5.225216 | 10.174762 | 11.041076 | 10.341502 |
| FAM166A | 1.436612261 | 0.043453389 | 0.002058523 | 42.75676716 | 1.874444 | 2.023048 | 3.324375 | 8.206677 | 7.292524 | 7.943848 |
| TSTD1 | 1.238113063 | 0.043453389 | 0.004842463 | 42.75676716 | 1.874444 | 4.80797 | 2.165421 | 9.171571 | 7.292524 | 8.391335 |
| GPR132 | 1.584706913 | 0.043453389 | 0.001187479 | 42.73933339 | 1.874444 | 2.406905 | 2.165421 | 7.394225 | 7.627877 | 7.582913 |
| PAPSS1 | 1.469113279 | 0.043453389 | 0.001745492 | 42.73933339 | 3.350997 | 2.809601 | 2.165421 | 8.361545 | 8.751258 | 7.582913 |
| C12orf36 | 1.431417987 | 0.043453389 | 0.002133379 | 42.73933339 | 1.874444 | 3.32135 | 2.165421 | 7.477873 | 8.71031 | 7.582913 |
| RBM34 | 1.4166217 | 0.043453389 | 0.002221844 | 42.73331073 | 1.874444 | 2.023048 | 2.165421 | 7.771052 | 7.440337 | 6.385515 |
| GTF3C6 | 1.411474328 | 0.043453389 | 0.000228377 | 42.73331073 | 1.874444 | 2.023048 | 2.165421 | 8.40494 | 7.440337 | 6.385515 |
| UBE2Q2 | 1.385312403 | 0.043453389 | 0.002651242 | 42.73331073 | 1.874444 | 2.023048 | 2.165421 | 9.16317 | 7.440337 | 6.32627 |
| C8orf40 | 1.363947141 | 0.043453389 | 0.002903028 | 42.73331073 | 1.874444 | 2.023048 | 2.165421 | 7.995811 | 7.440337 | 6.129407 |
| SURF1 | 1.313444203 | 0.043453389 | 0.003665192 | 42.73331073 | 1.874444 | 2.023048 | 2.165421 | 8.604261 | 7.440337 | 5.874974 |
| TMEM218 | 1.428905497 | 0.043453389 | 0.002160599 | 42.65029818 | 3.024504 | 2.023048 | 2.379345 | 7.109557 | 7.793829 | 8.622681 |
| HNRNPR | 1.366854964 | 0.043453389 | 0.002869003 | 42.44290195 | 3.839948 | 3.360637 | 3.90836 | 10.698207 | 9.2474 | 7.849596 |
| SUMO1P3 | 1.384841881 | 0.043453389 | 0.002664852 | 42.43513285 | 3.024504 | 2.023048 | 2.995681 | 8.964784 | 8.402869 | 6.942983 |
| ERGIC2 | 1.405748318 | 0.043453389 | 0.002372235 | 42.38367042 | 1.874444 | 2.023048 | 2.165421 | 6.339437 | 7.713236 | 7.428484 |
| LHX6 | 1.200882398 | 0.043453389 | 0.005631848 | 42.38367042 | 1.874444 | 2.023048 | 2.165421 | 7.631894 | 5.317867 | 7.428484 |
| ACAT1 | 1.340431433 | 0.043453389 | 0.000324328 | 42.256482 | 3.819732 | 2.023048 | 2.995681 | 7.450526 | 8.098861 | 9.220702 |
| RBM41 | 1.594819382 | 0.043453389 | 0.001133038 | 42.15946375 | 2.993831 | 2.023048 | 2.995681 | 8.254907 | 8.65384 | 8.719135 |
| PPIH | 1.595217589 | 0.043453389 | 0.001126233 | 41.96278636 | 1.874444 | 2.023048 | 2.165421 | 7.814607 | 7.414086 | 7.218312 |
| TRAPPC2 | 1.546635447 | 0.043453389 | 0.001323579 | 41.96278636 | 1.874444 | 2.023048 | 2.185421 | 8.033165 | 7.417086 | 7.020304 |
| MTRNR2L2 | 1.385174447 | 0.043453389 | 0.002658047 | 41.96278636 | 1.874444 | 2.023048 | 11.205289 | 8.885299 | 7.414086 | 6.69026 |
| PA2G4 | 1.267816237 | 0.043453389 | 0.004318476 | 41.96278636 | 1.874444 | 2.023048 | 2.165421 | 8.885299 | 7.414086 | 5.634184 |
| NMNAT1 | 1.328071996 | 0.043453389 | 0.003427016 | 41.87788429 | 2.993831 | 2.023048 | 2.379345 | 6.544171 | 7.767462 | 9.103055 |
| RAB32 | 1.561236212 | 0.043453389 | 0.001248724 | 41.87160178 | 1.874444 | 2.406329 | 2.165421 | 7.957464 | 7.25505 | 7.553321 |
| WHAMMP3 | 1.374727452 | 0.043453389 | 0.002780538 | 41.87160178 | 2.993831 | 2.023048 | 2.165421 | 6.814118 | 8.502167 | 7.553321 |
| ZNF518A | 1.413564365 | 0.043453389 | 0.002242259 | 41.74465515 | 1.874444 | 2.023048 | 2.165421 | 8.051486 | 7.406567 | 6.385515 |
| THADA | 1.306835109 | 0.043453389 | 0.003774073 | 41.74465515 | 1.874444 | 2.023048 | 2.165421 | 7.556937 | 7.406567 | 5.882028 |
| GOLGA8B | 1.163736681 | 0.043453389 | 0.006529432 | 41.74465515 | 1.874444 | 2.023048 | 2.165421 | 7.70315 | 7.406567 | 5.106393 |
| DFNA5 | 1.005193684 | 0.043588662 | 0.011640014 | 41.74465515 | 1.874444 | 2.023048 | 2.165421 | 7.679787 | 7.406567 | 4.146207 |
| ZNF277 | 1.20070631 | 0.043453389 | 0.005652263 | 41.67824488 | 2.201691 | 4.750708 | 2.995681 | 8.433162 | 8.469821 | 7.582913 |
| CYC1 | 1.391859779 | 0.043453389 | 0.002528751 | 41.6744441 | 1.874444 | 3.360637 | 2.995681 | 9.914429 | 8.277663 | 7.255535 |
| CIR1 | 1.523715219 | 0.043453389 | 0.00145968 | 41.44401553 | 3.350997 | 3.32135 | 3.764125 | 9.171571 | 8.724089 | 8.456743 |
| PSMA5 | 1.314131429 | 0.043453389 | 0.003637972 | 41.42599842 | 4.263463 | 1.42599842 | 2.165421 | 9.171571 | 8.119857 | 7.395512 |
| RAD50 | 1.308659323 | 0.043453389 | 0.003746853 | 41.42599842 | 3.839948 | 2.023048 | 2.379345 | 7.995811 | 7.819723 | 7.395512 |
| NDUFA5 | 1.381709522 | 0.043453389 | 0.002705682 | 41.40489187 | 2.201691 | 1.40489187 | 2.165421 | 7.856887 | 7.53715 | 6.32627 |
| ID4 | 1.338933687 | 0.043453389 | 0.003263695 | 41.40489187 | 2.993831 | 2.023048 | 2.165421 | 8.628872 | 7.53715 | 6.618407 |
| ANO7 | 1.555812959 | 0.043453389 | 0.001296359 | 41.36091126 | 5.056948 | 5.297868 | 5.544653 | 10.427146 | 10.98209 | 10.576683 |
| POTEM | 1.257244921 | 0.043453389 | 0.004515822 | 41.33842066 | 1.874444 | 2.406905 | 2.379345 | 5.743334 | 8.682351 | 7.748756 |
| TMEM14C | 1.442674436 | 0.043453389 | 0.001997278 | 41.29025674 | 3.839948 | 2.406905 | 2.995681 | 9.120418 | 8.855089 | 7.774634 |
| LPHN2 | 1.546166302 | 0.043453389 | 0.001327196 | 41.23049802 | 2.201691 | 2.809601 | 2.165421 | 7.531061 | 7.942653 | 7.800057 |
| TARBP1 | 1.368079503 | 0.043453389 | 0.002855393 | 41.1461104 | 3.350997 | 3.360637 | 2.165421 | 8.723321 | 7.819723 | 7.020304 |
| FKBP3 | 1.360010375 | 0.043453389 | 0.002971079 | 41.00387972 | 3.350997 | 3.872014 | 2.165421 | 9.506443 | 8.65384 | 6.32627 |
| RPS8 | 1.313242754 | 0.043453389 | 0.003671997 | 40.86067925 | 3.839948 | 8.170275 | 8.525393 | 15.13044 | 13.522916 | 6.618407 |
| EFEMP1 | 1.345181954 | 0.043453389 | 0.003168425 | 40.79152379 | 3.839948 | 4.413323 | 4.508334 | 8.286188 | 10.554762 | 11.967075 |
| EIF3E | 1.450038836 | 0.043453389 | 0.001908813 | 40.70453366 | 4.815804 | 4.911517 | 3.935222 | 11.480129 | 10.162922 | 9.220702 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| ISCU | 1.431579404 | 0.043453389 | 0.002126574 | 40.56713041 | 4.963444 | 3.770995 | 4.508334 | 10.115039 | 9.853832 | 9.113234 |
| CCPG1 | 1.528731479 | 0.043453389 | 0.000143246 | 40.56551863 | 1.874444 | 2.023048 | 2.165421 | 7.36523 | 8.402869 | 7.033813 |
| THSD7A | 1.488964105 | 0.043453389 | 0.001595781 | 40.56551863 | 1.874444 | 2.023048 | 2.379345 | 7.36523 | 8.160956 | 6.924055 |
| SP110 | 1.447744901 | 0.043453389 | 0.001942838 | 40.4683409 | 1.874444 | 2.023048 | 2.165421 | 6.550689 | 7.68534 | 7.36177 |
| WBP4 | 1.413152326 | 0.043453389 | 0.002255869 | 40.4683409 | 1.874444 | 2.023048 | 2.165421 | 6.395481 | 7.56803 | 7.36177 |
| RPL7 | 1.355704319 | 0.043453389 | 0.00030225519 | 40.28674451 | 7.730559 | 8.07747 | 8.13956 | 14.422425 | 13.409703 | 12.068646 |
| POF1B | 1.523838928 | 0.043453389 | 0.00144607 | 40.21069629 | 1.874444 | 2.023048 | 2.165421 | 6.954147 | 8.098861 | 7.352555 |
| CDO1 | 1.36920719 | 0.043453389 | 0.002841783 | 40.21069629 | 1.874444 | 2.023048 | 2.165421 | 6.183122 | 7.819723 | 7.352555 |
| PDGFD | 1.160482073 | 0.043453389 | 0.006611092 | 40.21069629 | 1.874444 | 2.023048 | 2.165421 | 5.026959 | 8.453372 | 7.352555 |
| PSMA3 | 1.335577999 | 0.043453389 | 0.003290915 | 40.20952181 | 4.263463 | 2.023048 | 3.324375 | 9.466036 | 8.65384 | 7.722406 |
| BDH2 | 1.403601523 | 0.043453389 | 0.002399456 | 40.11694283 | 4.682076 | 2.406905 | 3.90836 | 8.745998 | 10.008216 | 9.072081 |
| STARD10 | 1.250422197 | 0.043453389 | 0.004631507 | 39.97769849 | 2.201691 | 2.023048 | 2.995681 | 8.316805 | 7.53715 | 6.129407 |
| OBFC2B | 1.453744377 | 0.043453389 | 0.001861177 | 39.89178909 | 4.209882 | 3.32135 | 3.324375 | 8.801178 | 8.63937 | 8.809543 |
| PLBD1 | 1.462346937 | 0.043453389 | 0.001799932 | 39.74198427 | 1.874444 | 2.023048 | 2.165421 | 7.33564 | 8.533804 | 6.722123 |
| C7orf50 | 1.32994999 | 0.043453389 | 0.002394456 | 39.73813364 | 3.819732 | 2.023048 | 2.165421 | 7.477873 | 7.473335 | 9.061607 |
| CRNDE | 1.447735123 | 0.043453389 | 0.001949643 | 39.70751324 | 2.993831 | 3.770995 | 3.764125 | 10.052735 | 8.737737 | 8.305171 |
| DIMT1 | 1.309418202 | 0.043453389 | 0.003740048 | 39.56068284 | 1.874444 | 3.360637 | 2.379345 | 8.993498 | 7.68534 | 6.722123 |
| GOLGA4 | 1.237573436 | 0.043453389 | 0.004856073 | 39.51069887 | 2.993831 | 2.023048 | 4.449894 | 8.94532 | 8.332658 | 7.327219 |
| WHAMMP2 | 1.223517522 | 0.043453389 | 0.005114665 | 39.51069887 | 1.874444 | 2.023048 | 2.165421 | 5.448591 | 7.767462 | 7.327219 |
| LOC100287015 | 1.209760998 | 0.043453389 | 0.005441307 | 39.48959045 | 1.874444 | 2.809601 | 4.508334 | 7.177844 | 8.63937 | 8.32282 |
| CCDC125 | 1.346385086 | 0.043453389 | 0.003141204 | 39.47920976 | 2.201691 | 3.872014 | 2.995681 | 7.504712 | 8.579995 | 8.391335 |
| CD6 | 1.400324753 | 0.043453389 | 0.002453896 | 39.40219283 | 1.874444 | 2.023048 | 3.764125 | 8.843852 | 7.174648 | 8.549611 |
| INPP4B | 1.341667752 | 0.043453389 | 0.00321606 | 39.26846672 | 1.874444 | 2.406905 | 2.165421 | 8.122528 | 6.205902 | 7.46072 |
| PLN | 1.447955565 | 0.043453389 | 0.001936033 | 39.25656159 | 1.874444 | 2.023048 | 2.165421 | 6.664985 | 7.31791 | 8.593895 |
| TAZ | 1.364268243 | 0.043453389 | 0.002889418 | 39.25656159 | 1.874444 | 2.023048 | 2.165421 | 6.183122 | 7.31791 | 7.492252 |
| CA2 | 1.100125961 | 0.043516135 | 0.008221844 | 39.25656159 | 1.874444 | 2.023048 | 2.165421 | 11.13615 | 7.31791 | 4.562324 |
| HERC4 | 1.302668709 | 0.04349335 | 0.003869343 | 39.18845706 | 2.993831 | 2.023048 | 2.165421 | 8.286188 | 7.767462 | 6.32627 |
| SRP9 | 1.315831463 | 0.043453389 | 0.003617557 | 39.12890373 | 6.008206 | 4.351315 | 4.724406 | 11.298369 | 10.865703 | 9.040427 |
| PRMT10 | 1.406410991 | 0.043453389 | 0.002358625 | 38.99196047 | 1.874444 | 2.023048 | 2.165421 | 7.450526 | 6.373501 | 7.36177 |
| TTC37 | 1.468192955 | 0.043453389 | 0.001752297 | 38.79705492 | 3.350997 | 3.32135 | 2.379345 | 8.628872 | 8.518072 | 7.873743 |
| SNORD36A | 1.381553079 | 0.043453389 | 0.002712487 | 38.79399871 | 1.874444 | 2.023048 | 3.324375 | 7.877571 | 7.68534 | 7.152205 |
| ESR1 | 1.413593415 | 0.043453389 | 0.002253454 | 38.68038585 | 3.024504 | 2.023048 | 2.995681 | 8.566539 | 7.174648 | 8.269212 |
| PPIP5K2 | 1.436480191 | 0.043453389 | 0.002065328 | 38.63199311 | 3.024504 | 2.023048 | 2.379345 | 8.139755 | 8.296229 | 7.033813 |
| LAPTM5 | 1.305262789 | 0.043453389 | 0.003794488 | 38.57185413 | 2.993831 | 2.023048 | 4.285996 | 8.925589 | 7.292524 | 9.192178 |
| ARL5B | 1.128916867 | 0.043453389 | 0.007359646 | 38.57185413 | 1.874444 | 2.023048 | 4.724406 | 8.316805 | 7.292524 | 7.291822 |
| SETD7 | 1.126551442 | 0.043453389 | 0.007448112 | 38.55507345 | 4.963444 | 2.023048 | 2.165421 | 7.937902 | 8.181074 | 7.291822 |
| TIMM23 | 1.398014149 | 0.043453389 | 0.002467506 | 38.40077714 | 2.201691 | 3.32135 | 2.165421 | 8.41912 | 7.473335 | 7.428484 |
| SERPINA3 | 1.090161231 | 0.043516135 | 0.008600885 | 38.30238585 | 4.963444 | 8.158996 | 5.596986 | 13.673048 | 10.856349 | 9.737435 |
| RAB9A | 1.384299959 | 0.043453389 | 0.002678462 | 38.29254369 | 3.350997 | 2.406905 | 2.165421 | 8.447068 | 8.609988 | 6.942983 |
| SEPT2 | 1.187339094 | 0.043453389 | 0.006012249 | 38.2838813 | 6.765086 | 4.736586 | 4.508334 | 9.767 | 10.284148 | 10.070856 |
| UBE2NL | 1.261437949 | 0.043453389 | 0.00444771 | 38.25366027 | 1.874444 | 2.023048 | 3.764125 | 9.02165 | 7.292524 | 7.774634 |
| APOF | 1.304627375 | 0.043453389 | 0.003835318 | 38.09494312 | 1.874444 | 2.023048 | 2.165421 | 7.274575 | 7.942653 | 5.882028 |
| NAA40 | 1.433897504 | 0.043453389 | 0.002099354 | 38.04861649 | 6.45321 | 6.092406 | 5.702912 | 10.62363 | 11.52517 | 11.702982 |
| CMC1 | 1.11846103 | 0.043485739 | 0.007629126 | 37.96245679 | 1.874444 | 2.023048 | 2.165421 | 8.553743 | 7.269549 | 4.790662 |
| SNX17 | 1.453689637 | 0.043453389 | 0.001867982 | 37.95786248 | 3.839948 | 2.809601 | 2.995681 | 8.501391 | 8.055928 | 8.96375 |
| GPRASP1 | 1.299712561 | 0.043453389 | 0.003937394 | 37.8998065 | 1.874444 | 2.023048 | 2.165421 | 6.244586 | 8.2398 | 7.695565 |
| MRPS31 | 1.257910811 | 0.043453389 | 0.00450917 | 37.8127138 | 3.350997 | 2.023048 | 2.165421 | 8.591796 | 7.767462 | 6.32627 |
| LOC375190 | 1.448955474 | 0.043453389 | 0.001915618 | 37.70965681 | 1.874444 | 2.023048 | 2.165421 | 7.25991 | 7.656894 | 6.587378 |
| SPATA6 | 1.241297889 | 0.043453389 | 0.004794828 | 37.70965681 | 1.874444 | 2.023048 | 2.165421 | 7.25991 | 7.56803 | 5.580533 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| TXNIP | 1.188615764 | 0.043453389 | 0.005991834 | 37.65317973 | 6.707871 | 4.750708 | 6.564874 | 10.398804 | 11.94257 | 10.18624 |
| MRPL15 | 1.334379529 | 0.043453389 | 0.00331133 | 37.58283222 | 1.874444 | 2.023048 | 2.165421 | 7.531061 | 7.25505 | 6.051818 |
| RAB25 | 1.115733348 | 0.043485739 | 0.007724396 | 37.58283222 | 1.874444 | 2.023048 | 2.165421 | 8.40404 | 7.25505 | 4.790662 |
| P2RY6 | 1.374554258 | 0.043453389 | 0.002787343 | 37.567624 | 4.309025 | 2.406905 | 4.285996 | 8.361545 | 9.540026 | 9.446808 |
| MATN2 | 1.390500842 | 0.043453389 | 0.002549166 | 37.4785643 | 1.874444 | 3.360637 | 2.379345 | 7.607339 | 8.453372 | 7.327219 |
| HMGB2 | 1.370593472 | 0.043453389 | 0.002821368 | 37.43681167 | 3.024504 | 2.023048 | 4.285996 | 8.122528 | 9.418172 | 8.25089 |
| LOC155060 | 1.349375887 | 0.043453389 | 0.003093569 | 37.40064496 | 4.209882 | 2.406905 | 3.324375 | 8.087444 | 8.549366 | 8.579284 |
| HEPH | 1.520376076 | 0.043453389 | 0.001480095 | 37.27143751 | 1.874444 | 2.023048 | 2.165421 | 7.243046 | 7.627877 | 6.924055 |
| DDX59 | 1.215720273 | 0.043453389 | 0.005298401 | 37.27143751 | 1.874444 | 2.023048 | 2.165421 | 7.243046 | 7.598264 | 5.446557 |
| TUBA1B | 1.392465316 | 0.043453389 | 0.002515141 | 37.17455237 | 5.897292 | 6.03611 | 5.592916 | 11.987974 | 11.113535 | 10.171703 |
| FAM162A | 1.396701727 | 0.043453389 | 0.002474311 | 37.15013347 | 3.024504 | 2.023048 | 7.450526 | 7.450526 | 8.2398 | 7.03218 |
| C1orf52 | 1.36529979 | 0.043453389 | 0.002882613 | 37.13673373 | 5.056948 | 4.80797 | 6.175931 | 10.271723 | 10.655275 | 10.166824 |
| CKS1B | 1.296113072 | 0.043453389 | 0.003978224 | 37.12907239 | 3.024504 | 2.023048 | 3.324375 | 8.239009 | 8.916384 | 6.722123 |
| CCDC120 | 1.401883397 | 0.043453389 | 0.002426676 | 37.1209054 | 1.874444 | 6.670655 | 5.609945 | 10.752415 | 11.73537 | 12.047569 |
| TC2N | 0.983133573 | 0.043626235 | 0.012476033 | 36.93931612 | 2.993831 | 2.406905 | 3.324375 | 9.417418 | 8.200016 | 4.790662 |
| PLRG1 | 1.255175754 | 0.043453389 | 0.004549847 | 36.84570388 | 2.201691 | 3.770995 | 2.379345 | 8.974419 | 7.89473 | 6.722123 |
| GUCY1A3 | 1.388682006 | 0.043453389 | 0.002576387 | 36.78649874 | 3.839948 | 2.809601 | 2.165421 | 8.885299 | 7.819723 | 8.010706 |
| FAM92A3 | 1.47064828 | 0.043453389 | 0.001725077 | 36.75348136 | 1.874444 | 2.406905 | 2.165421 | 7.36523 | 8.2398 | 6.924055 |
| HPS3 | 1.33182711 | 0.043453389 | 0.003345356 | 36.75348136 | 1.874444 | 2.023048 | 2.165421 | 7.36523 | 7.269549 | 6.051818 |
| MFN1 | 1.544560552 | 0.043453389 | 0.001343995 | 36.75191175 | 1.874444 | 2.023048 | 2.165421 | 7.074163 | 7.56803 | 7.180104 |
| ROBO1 | 1.450324623 | 0.043453389 | 0.001902007 | 36.63787738 | 3.024504 | 2.023048 | 2.379345 | 7.897963 | 8.055928 | 7.218312 |
| CYFIP2 | 0.95368102 | 0.043857532 | 0.01372916 | 36.54786367 | 1.874444 | 2.023048 | 5.389265 | 7.394225 | 7.066159 | 7.36177 |
| LINC00346 | 1.442118755 | 0.043453389 | 0.002010888 | 36.47119008 | 1.874444 | 2.023048 | 2.165421 | 6.664985 | 7.56803 | 7.36177 |
| CD1D | 1.211502008 | 0.043453389 | 0.005400476 | 36.44794275 | 4.639409 | 2.023048 | 2.379345 | 7.210813 | 8.181074 | 8.809543 |
| AKR1B1 | 1.070898828 | 0.043516135 | 0.009210616 | 36.38805819 | 5.263699 | 2.809601 | 2.995681 | 7.274575 | 8.181074 | 8.503924 |
| DARC | 1.073310749 | 0.043516135 | 0.009149371 | 36.2571758 | 1.874444 | 3.360637 | 5.723602 | 8.540832 | 6.861783 | 12.084253 |
| MTDH | 1.388662989 | 0.043453389 | 0.003283192 | 36.07183693 | 5.304463 | 5.148082 | 3.935222 | 10.45838 | 10.320883 | 9.363984 |
| CD9 | 1.38801567 | 0.043453389 | 0.002603607 | 35.98181115 | 3.819732 | 3.770995 | 3.324375 | 9.761445 | 8.94019 | 7.943848 |
| TMBIM4 | 1.439837927 | 0.043453389 | 0.002044913 | 35.96083631 | 2.993831 | 2.023048 | 2.165421 | 7.656039 | 7.191402 | 7.825039 |
| IFT80 | 1.302221671 | 0.043453389 | 0.003896563 | 35.96083631 | 1.874444 | 2.023048 | 2.165421 | 7.74877 | 7.191402 | 5.900694 |
| HSPA14 | 1.402645435 | 0.043453389 | 0.002413066 | 35.85464659 | 1.874444 | 2.023048 | 2.165421 | 6.396698 | 7.187136 | 7.65565 |
| LOC728758 | 1.388281227 | 0.043453389 | 0.002596802 | 35.85646659 | 1.874444 | 2.023048 | 2.165421 | 7.631894 | 7.187136 | 6.32627 |
| AGXT2L2 | 1.424490989 | 0.043453389 | 0.002187819 | 35.73757686 | 4.639409 | 2.023048 | 2.165421 | 7.556937 | 7.414086 | 7.033813 |
| RBMXL1 | 1.240727835 | 0.043453389 | 0.004815243 | 35.72902629 | 4.963444 | 2.406905 | 3.90836 | 9.067384 | 9.847551 | 7.873743 |
| MTERFD3 | 1.214900368 | 0.043453389 | 0.005318816 | 35.69713784 | 1.874444 | 2.023048 | 3.935222 | 7.631894 | 7.440337 | 7.03218 |
| KIAA0125 | 1.160531396 | 0.043453389 | 0.006604287 | 35.62445955 | 1.874444 | 2.023048 | 2.165421 | 7.177844 | 8.220489 | 5.106393 |
| MRPL18 | 1.4076362 | 0.043453389 | 0.002331405 | 35.62231572 | 4.263463 | 4.80797 | 2.995681 | 9.067384 | 9.418172 | 9.570168 |
| OS9 | 1.40470259 | 0.043453389 | 0.00237904 | 35.61838256 | 4.309025 | 5.148082 | 5.217616 | 10.508978 | 10.302633 | 9.380933 |
| LAGE3 | 1.197476388 | 0.043453389 | 0.005754338 | 35.56753009 | 2.201691 | 2.023048 | 2.165421 | 7.856887 | 7.31791 | 5.446557 |
| EBAG9 | 1.181688504 | 0.043453389 | 0.00613474 | 35.56753009 | 2.201691 | 2.023048 | 2.165421 | 7.36523 | 7.31791 | 5.426231 |
| EMCN | 1.490643802 | 0.043453389 | 0.001588976 | 35.54561617 | 1.874444 | 2.023048 | 2.165421 | 6.814118 | 7.174648 | 7.611911 |
| MRPL36 | 1.290651561 | 0.043453389 | 0.004046274 | 35.54561617 | 1.874444 | 2.023048 | 2.165421 | 7.33564 | 7.174648 | 5.874974 |
| ANGPT1 | 1.198238124 | 0.043453389 | 0.005733923 | 35.54561617 | 1.874444 | 2.023048 | 2.165421 | 5.320955 | 7.174648 | 8.636861 |
| RNF103 | 1.338680588 | 0.043453389 | 0.0032705 | 35.5380192 | 3.819732 | 3.32135 | 5.018694 | 9.81605 | 9.418172 | 8.472642 |
| AP3M1 | 1.253406043 | 0.043453389 | 0.004563457 | 35.49321071 | 7.445608 | 6.42919 | 7.481604 | 10.828761 | 12.59508 | 12.699415 |
| CAMLG | 1.303984004 | 0.043453389 | 0.003848928 | 35.45367093 | 1.874444 | 2.809601 | 3.764125 | 7.957464 | 8.63937 | 7.180104 |
| EBAG9 | 1.235053693 | 0.043453389 | 0.004903709 | 35.481279 | 1.874444 | 2.406905 | 2.165421 | 5.705318 | 7.440337 | 7.553321 |
| POMT1 | 1.406329771 | 0.043453389 | 0.00236543 | 35.40449285 | 1.874444 | 2.023048 | 2.995681 | 7.70315 | 7.505595 | 7.020304 |
| ATP1B1 | 1.101418348 | 0.04349335 | 0.008167404 | 35.40449285 | 1.874444 | 4.351315 | 4.449894 | 9.704692 | 8.402869 | 7.020304 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| COL6A6 | 1.027393674 | 0.043577906 | 0.010654644 | 35.3908917 | 1.874444 | 2.023048 | 3.90836 | 5.095353 | 9.053666 | 7.722406 |
| LOC285768 | 1.24747431 | 0.043453389 | 0.004685948 | 35.36795892 | 1.874444 | 2.023048 | 2.165421 | 7.167419 | 7.598264 | 5.634184 |
| GK5 | 1.327377235 | 0.043453389 | 0.003474651 | 35.32740941 | 8.351337 | 7.786385 | 8.418052 | 12.214229 | 13.494054 | 13.790943 |
| RPS20 | 1.450603522 | 0.043453389 | 0.001895202 | 35.27945205 | 8.294165 | 8.544272 | 8.448127 | 13.709563 | 13.588884 | 13.019276 |
| ZNF695 | 1.302496366 | 0.043453389 | 0.003882953 | 35.12611544 | 4.815804 | 4.413323 | 2.379345 | 8.286188 | 9.547795 | 9.910841 |
| FLJ12825 | 1.375548086 | 0.043453389 | 0.002766928 | 34.9969504 | 3.350997 | 2.023048 | 2.165421 | 7.631894 | 8.277663 | 7.152205 |
| CCDC76 | 1.355625514 | 0.043453389 | 0.003032324 | 34.9969504 | 1.874444 | 2.023048 | 2.165421 | 6.183122 | 7.473335 | 7.152205 |
| PDGFRL | 1.181369617 | 0.043453389 | 0.006155155 | 34.9969504 | 1.874444 | 2.023048 | 3.764125 | 6.396698 | 9.687973 | 7.152205 |
| LOC100129480 | 1.237623153 | 0.043453389 | 0.004849268 | 34.97654884 | 5.056948 | 4.351315 | 6.410545 | 9.479631 | 10.475516 | 10.388357 |
| HPS5 | 1.049527651 | 0.043568903 | 0.009936033 | 34.9471662 | 1.874444 | 2.023048 | 2.165421 | 7.210813 | 7.292524 | 4.562324 |
| SRP54 | 1.322374142 | 0.043453389 | 0.003542702 | 34.92649946 | 1.874444 | 2.406905 | 2.379345 | 8.361545 | 7.505595 | 6.195186 |
| SCOC | 1.022960332 | 0.043577906 | 0.010920041 | 34.92649946 | 2.201691 | 2.023048 | 2.379345 | 8.376156 | 7.505595 | 4.562324 |
| LOC401397 | 1.225307567 | 0.043453389 | 0.005073835 | 34.89228003 | 3.839948 | 2.023048 | 2.165421 | 8.964784 | 8.055928 | 6.385515 |
| OBFC2A | 1.41910191 | 0.043453389 | 0.002201429 | 34.82012411 | 2.993831 | 3.872014 | 3.324375 | 8.488001 | 8.579995 | 8.11568 |
| COL6A4P2 | 1.295847045 | 0.043453389 | 0.003985029 | 34.8151922 | 3.350997 | 3.872014 | 2.165421 | 7.33564 | 8.682351 | 8.472642 |
| ZMAT1 | 1.491876506 | 0.043453389 | 0.001568561 | 34.80098872 | 1.874444 | 2.023048 | 2.165421 | 7.144104 | 7.406567 | 7.020304 |
| TSG1 | 1.474748257 | 0.043453389 | 0.001704661 | 34.80098872 | 1.874444 | 2.023048 | 2.165421 | 7.144104 | 6.794431 | 7.897492 |
| NQO2 | 1.203078015 | 0.043453389 | 0.005543382 | 34.80098872 | 1.874444 | 2.023048 | 2.165421 | 7.144104 | 7.414086 | 5.426231 |
| LOC100129917 | 1.318969079 | 0.043453389 | 0.003576727 | 34.76422937 | 6.186289 | 5.297868 | 4.724406 | 9.868664 | 10.589051 | 10.4174 |
| CYB5R1 | 1.483421527 | 0.043453389 | 0.001657026 | 34.68414378 | 1.874444 | 2.406905 | 2.165421 | 7.037879 | 7.191402 | 7.523109 |
| AARS2 | 1.174641158 | 0.043453389 | 0.006291256 | 34.67758039 | 4.209882 | 2.023048 | 2.379345 | 7.631894 | 7.138979 | 7.553321 |
| C7orf23 | 1.088246078 | 0.043516135 | 0.008668935 | 34.67758039 | 1.874444 | 2.023048 | 2.379345 | 7.394225 | 7.138979 | 4.790662 |
| SCARA5 | 1.107340416 | 0.043453389 | 0.007997278 | 34.67524504 | 4.743564 | 3.32135 | 3.935222 | 6.960054 | 9.991223 | 9.051056 |
| LRIG1 | 1.077989902 | 0.043516135 | 0.00902688 | 34.66439245 | 2.201691 | 3.32135 | 5.018694 | 10.388031 | 8.436733 | 6.587378 |
| JTB | 1.393284287 | 0.043453389 | 0.002508336 | 34.63221867 | 4.815804 | 3.872014 | 3.935222 | 9.049264 | 9.392516 | 9.040427 |
| PHF20L1 | 1.344948274 | 0.043453389 | 0.00318203 | 34.53159608 | 3.350997 | 4.389936 | 2.379345 | 8.460842 | 8.737737 | 8.340256 |
| RCOR3 | 1.459138408 | 0.043453389 | 0.001828186 | 34.51828186 | 2.993831 | 2.809601 | 2.379345 | 7.450526 | 7.91889 | 8.519314 |
| ATF3 | 1.038416009 | 0.043577906 | 0.007997278 | 34.43362266 | 4.743564 | 5.789702 | 6.410545 | 11.761857 | 9.586024 | 8.456743 |
| C15orf2 | 1.432012016 | 0.043453389 | 0.002119769 | 34.39503536 | 4.815804 | 2.023048 | 2.165421 | 6.544171 | 7.269549 | 7.152205 |
| UBAC1 | 1.424572918 | 0.043453389 | 0.002181014 | 34.39503536 | 2.201691 | 2.023048 | 2.165421 | 7.897963 | 7.269549 | 6.618407 |
| GSG1 | 1.415867287 | 0.043453389 | 0.002228649 | 34.37241972 | 1.874444 | 2.023048 | 2.995681 | 7.631894 | 8.098861 | 6.942983 |
| IRX3 | 1.018536847 | 0.043577906 | 0.011117387 | 34.37241972 | 1.874444 | 2.023048 | 2.995681 | 10.034429 | 8.098861 | 4.790662 |
| SNX3 | 1.373035243 | 0.043453389 | 0.002807758 | 34.28193988 | 4.815804 | 3.360637 | 3.764125 | 9.744652 | 9.915181 | 8.32282 |
| DDX1 | 1.202456456 | 0.043453389 | 0.005563797 | 34.26229035 | 4.815804 | 3.32135 | 2.165421 | 9.002943 | 8.4199 | 7.640338 |
| ULBP1 | 1.327665772 | 0.043453389 | 0.003454236 | 34.21251151 | 1.874444 | 3.770995 | 3.935222 | 8.488001 | 9.031674 | 7.873743 |
| IMMP1L | 1.123339567 | 0.043453389 | 0.007475332 | 34.07953365 | 2.201691 | 2.023048 | 2.379345 | 8.376156 | 7.292524 | 5.091834 |
| HSD17B4 | 1.408109059 | 0.043453389 | 0.0023246 | 34.05108501 | 1.874444 | 2.023048 | 2.165421 | 9.08528 | 7.25505 | 6.722123 |
| POPDC2 | 1.310879857 | 0.043453389 | 0.003726438 | 34.05108501 | 2.201691 | 2.023048 | 2.165421 | 6.063041 | 7.25505 | 7.774634 |
| ZC2HC1A | 1.484712077 | 0.043453389 | 0.001650221 | 33.97753111 | 1.874444 | 2.023048 | 2.165421 | 7.109557 | 6.794431 | 7.352555 |
| ACBD7 | 1.383101718 | 0.043453389 | 0.002685267 | 33.97753111 | 1.874444 | 2.023048 | 2.165421 | 7.109557 | 7.53715 | 6.32627 |
| TXLNG2P | 1.326574143 | 0.043453389 | 0.003499066 | 33.95708335 | 3.839948 | 2.023048 | 2.165421 | 8.925589 | 7.627877 | 6.051818 |
| MED30 | 1.069320708 | 0.043516135 | 0.009285471 | 33.95636401 | 1.874444 | 2.023048 | 2.165421 | 6.960054 | 7.845161 | 5.426231 |
| TTTY15 | 1.409807012 | 0.043453389 | 0.002304185 | 33.937026 | 1.874444 | 2.809601 | 2.379345 | 8.087444 | 7.68534 | 7.327219 |
| ENPP1 | 1.192839633 | 0.043453389 | 0.005882953 | 33.937026 | 1.874444 | 2.023048 | 2.165421 | 8.361545 | 7.107836 | 5.446557 |
| SYBU | 1.159363995 | 0.043453389 | 0.006631507 | 33.937026 | 1.874444 | 2.023048 | 2.165421 | 9.137671 | 7.107836 | 5.106393 |
| BOLA1 | 1.148524892 | 0.043453389 | 0.006903709 | 33.72497065 | 3.819732 | 2.023048 | 2.379345 | 7.814607 | 7.942653 | 5.091834 |
| DCTN4 | 1.129596454 | 0.043453389 | 0.007352841 | 33.69251979 | 3.024504 | 2.023048 | 2.165421 | 8.895478 | 8.098861 | 5.874974 |
| TTC14 | 1.389413666 | 0.043453389 | 0.002562776 | 33.62674462 | 1.874444 | 2.406905 | 2.165421 | 7.037879 | 8.098861 | 7.582913 |
| CWC15 | 1.208383591 | 0.043453389 | 0.005454917 | 33.62674462 | 1.874444 | 2.023048 | 2.165421 | 8.955085 | 7.094585 | 5.426231 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| MAP3K1 | 1.189837508 | 0.043453389 | 0.005985029 | 33.62674462 | 1.874444 | 2.023048 | 2.379345 | 8.822673 | 7.094585 | 5.426231 |
| RAET1E | 1.102071727 | 0.04349335 | 0.008140184 | 33.62674462 | 1.874444 | 2.023048 | 2.379345 | 4.894482 | 7.094585 | 7.327219 |
| EIF3M | 1.102076061 | 0.043453389 | 0.008133379 | 33.55694331 | 1.874444 | 4.830496 | 2.379345 | 8.156778 | 7.91889 | 6.942983 |
| CUL4B | 1.379250948 | 0.043453389 | 0.002732902 | 33.54726746 | 3.350997 | 2.023048 | 2.379345 | 8.41912 | 8.033973 | 7.03218 |
| VEZT | 1.487961556 | 0.043453389 | 0.001609391 | 33.48787281 | 3.819732 | 3.32135 | 3.324375 | 8.885299 | 8.609988 | 8.374509 |
| SFRP2 | 1.199631142 | 0.043453389 | 0.005699898 | 33.4548031 | 3.839948 | 2.809601 | 4.724406 | 8.206677 | 10.99919 | 7.873743 |
| C12orf65 | 1.1612775 | 0.043453389 | 0.006577067 | 33.40156651 | 6.924263 | 6.311907 | 7.401896 | 10.084223 | 11.986107 | 12.946423 |
| SCARB2 | 1.36621899 | 0.043453389 | 0.002875808 | 33.39925127 | 4.963444 | 4.413323 | 4.508334 | 10.025188 | 9.853832 | 8.870819 |
| DCTN3 | 1.177209706 | 0.043453389 | 0.006250425 | 33.36461308 | 4.309025 | 5.340619 | 2.995681 | 8.925589 | 8.055928 | 10.788406 |
| PTPRC | 0.96059629 | 0.043778104 | 0.01333719 | 33.33183655 | 2.993831 | 3.770995 | 7.295639 | 9.939241 | 8.829823 | 8.593895 |
| FBXL5 | 1.230566457 | 0.043453389 | 0.004964954 | 33.30472878 | 2.993831 | 2.023048 | 2.165421 | 8.051486 | 7.989035 | 5.900694 |
| TRO | 1.241195316 | 0.043453389 | 0.004801633 | 33.28891815 | 3.350997 | 2.023048 | 2.165421 | 6.063041 | 8.385634 | 8.407967 |
| FREM2 | 1.391757549 | 0.043453389 | 0.002535556 | 33.2844889 | 1.874444 | 2.023048 | 2.995681 | 7.394225 | 8.033973 | 6.931222 |
| NGRN | 1.158756095 | 0.043453389 | 0.006645117 | 33.17148844 | 3.350997 | 3.872014 | 2.995681 | 9.873821 | 8.402869 | 6.587378 |
| C12orf75 | 1.209762247 | 0.043453389 | 0.005434502 | 33.15408767 | 1.874444 | 2.023048 | 2.165421 | 7.074163 | 7.845161 | 5.446557 |
| ATP5F1 | 1.275750943 | 0.043453389 | 0.00423001 | 33.28891815 | 3.350997 | 2.023048 | 3.935222 | 8.98399 | 8.867558 | 8.407967 |
| CXCR2P1 | 1.23926553 | 0.043453389 | 0.004835658 | 33.02284377 | 1.874444 | 2.023048 | 2.165421 | 7.210813 | 8.033973 | 5.634184 |
| SNRNP27 | 1.356756624 | 0.043453389 | 0.002991494 | 33.02188826 | 3.839948 | 3.872014 | 2.165421 | 8.885299 | 8.296229 | 7.722406 |
| C6orf97 | 1.446216131 | 0.043453389 | 0.001970058 | 32.99792332 | 3.024504 | 3.360637 | 2.379345 | 8.40494 | 7.870158 | 7.943848 |
| PPP2R3C | 1.387584727 | 0.043453389 | 0.002624022 | 32.97066079 | 1.874444 | 2.023048 | 2.165421 | 7.856887 | 7.066159 | 6.385515 |
| FYB | 1.363601988 | 0.043453389 | 0.002909833 | 32.97066079 | 3.024504 | 2.023048 | 2.165421 | 8.801178 | 7.066159 | 7.180104 |
| CLK2 | 1.334545291 | 0.043453389 | 0.003304525 | 32.97066079 | 1.874444 | 2.023048 | 2.165421 | 7.631894 | 7.066159 | 6.106561 |
| TMEM216 | 1.06054035 | 0.04354029 | 0.009532494 | 32.97066079 | 1.874444 | 2.023048 | 2.165421 | 7.937902 | 7.066159 | 4.562324 |
| MEA1 | 1.345578521 | 0.043453389 | 0.00316162 | 32.86071323 | 3.350997 | 2.809601 | 2.995681 | 8.553743 | 8.033973 | 7.255535 |
| PPIL4 | 1.323820648 | 0.043453389 | 0.003515481 | 32.58551088 | 3.024504 | 2.406905 | 3.324375 | 8.139755 | 8.350533 | 7.033813 |
| MYOF | 1.052019993 | 0.043568903 | 0.009867982 | 32.54092707 | 4.639409 | 3.32135 | 2.165421 | 9.663593 | 8.36819 | 6.195186 |
| MLKL | 1.402090617 | 0.043453389 | 0.002419871 | 32.48530105 | 1.874444 | 2.406905 | 2.165421 | 6.651882 | 7.187136 | 8.175185 |
| ARL3 | 1.201090601 | 0.043453389 | 0.005611432 | 32.48530105 | 3.819732 | 2.023048 | 2.165421 | 7.36525 | 7.187136 | 7.180104 |
| PRKAR2B | 1.152292124 | 0.043453389 | 0.006794828 | 32.42260326 | 4.815804 | 4.413323 | 2.995681 | 8.014609 | 7.740604 | 8.095288 |
| GPR112 | 1.201497747 | 0.043453389 | 0.005591017 | 32.37079998 | 2.201691 | 2.023048 | 3.935222 | 7.897963 | 7.066159 | 7.218312 |
| VAV3 | 1.381178359 | 0.043453389 | 0.002719292 | 32.23968258 | 1.874444 | 2.023048 | 2.165421 | 9.058353 | 6.551443 | 7.033813 |
| NDUFB3 | 1.304711993 | 0.043453389 | 0.003828513 | 32.21071544 | 3.024504 | 2.023048 | 2.165421 | 6.395481 | 8.033973 | 7.748756 |
| ASNSD1 | 1.359241318 | 0.043453389 | 0.002984689 | 32.20531095 | 2.201691 | 2.023048 | 2.165421 | 7.504712 | 7.174648 | 6.32627 |
| TRAPPC6B | 1.116486033 | 0.043485739 | 0.00790371 | 32.20531095 | 1.874444 | 2.406905 | 2.165421 | 7.33564 | 7.174648 | 5.106393 |
| ZNF165 | 0.973849717 | 0.043681142 | 0.01278394 | 32.20531095 | 1.874444 | 2.023048 | 2.165421 | 8.033165 | 7.174648 | 4.146207 |
| CHTOP | 1.110911107 | 0.043485739 | 0.007880912 | 32.20320163 | 4.815804 | 2.023048 | 2.995681 | 8.628872 | 8.077554 | 7.03218 |
| CCDC84 | 1.326710028 | 0.043453389 | 0.003481456 | 32.18606305 | 4.639409 | 3.770995 | 3.324375 | 8.779359 | 8.564762 | 8.809543 |
| TFG | 1.100762898 | 0.04349335 | 0.008208234 | 32.17972436 | 4.743564 | 4.80797 | 2.379345 | 9.8105 | 8.055928 | 8.010706 |
| SSPN | 1.310003663 | 0.043453389 | 0.003733243 | 32.14832954 | 3.839948 | 2.406905 | 4.508334 | 8.105092 | 9.275744 | 8.84662 |
| SRP14 | 1.211610124 | 0.043453389 | 0.005386866 | 32.13004187 | 5.263699 | 2.406905 | 3.935222 | 9.094145 | 8.402869 | 8.941073 |
| LOC285696 | 1.491817839 | 0.043453389 | 0.001575366 | 32.04434856 | 2.201691 | 2.023048 | 2.165421 | 7.167419 | 7.269549 | 6.924055 |
| EPHX1 | 1.27375849 | 0.043453389 | 0.00424362 | 32.02049957 | 4.209882 | 4.413323 | 4.944468 | 8.433162 | 9.962448 | 9.414247 |
| TSPYL4 | 1.356029306 | 0.043453389 | 0.003018714 | 31.93919991 | 3.024504 | 2.023048 | 2.995681 | 8.895478 | 7.845161 | 7.020304 |
| FAM149B1 | 1.320857343 | 0.043453389 | 0.003563117 | 31.93919991 | 1.874444 | 2.023048 | 2.165421 | 6.063041 | 7.269549 | 7.020304 |
| PART1 | 1.368688849 | 0.043453389 | 0.002848588 | 31.89391753 | 6.008206 | 5.362142 | 6.175931 | 10.187245 | 11.395554 | 11.003415 |
| SLC50A1 | 1.382840452 | 0.043453389 | 0.002698877 | 31.87912041 | 4.815804 | 3.32135 | 4.944468 | 9.359771 | 9.939008 | 9.462817 |
| KARS | 1.282930243 | 0.043453389 | 0.00445155 | 31.78127145 | 3.839948 | 2.023048 | 3.935222 | 8.014609 | 8.2398 | 7.46072 |
| AKAP9 | 1.214905317 | 0.043453389 | 0.005312011 | 31.77620768 | 3.839948 | 3.360637 | 5.389265 | 9.179923 | 8.829823 | 8.650903 |
| CLDN12 | 1.196098343 | 0.043453389 | 0.005778683 | 31.71553571 | 1.874444 | 2.023048 | 3.90836 | 8.895478 | 7.107435 | 6.73963 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| METTL15 | 1.187012909 | 0.043453389 | 0.006032664 | 31.70820459 | 3.819732 | 2.023048 | 2.165421 | 7.037879 | 7.406567 | 7.152205 |
| DNAJC15 | 1.191990207 | 0.043453389 | 0.005910174 | 31.65206094 | 3.819732 | 2.809601 | 2.165421 | 8.925589 | 7.793829 | 6.587378 |
| C1orf123 | 1.328508052 | 0.043453389 | 0.003420211 | 31.62369838 | 2.993831 | 2.406905 | 3.935222 | 7.976765 | 8.4199 | 7.748756 |
| CNKSR3 | 1.448262341 | 0.043453389 | 0.001929228 | 31.61880125 | 1.874444 | 2.406905 | 2.165421 | 6.857154 | 7.187136 | 7.352555 |
| HSDL2 | 1.069268156 | 0.043516135 | 0.009292276 | 31.61253292 | 4.639409 | 2.023048 | 2.379345 | 7.656039 | 7.066159 | 7.36177 |
| CFL1P1 | 1.220170687 | 0.043453389 | 0.00518952 | 31.56735444 | 4.639409 | 2.406905 | 4.285996 | 7.726141 | 9.266358 | 9.346832 |
| NDUFA4 | 1.361403149 | 0.043453389 | 0.002943858 | 31.53288055 | 4.263463 | 4.830496 | 4.944468 | 11.275169 | 9.809281 | 8.997112 |
| MGC23370 | 1.330889548 | 0.043453389 | 0.003392991 | 31.53065789 | 3.350997 | 2.406905 | 2.165421 | 7.144104 | 7.713236 | 7.553321 |
| CACNB2 | 1.215211839 | 0.043453389 | 0.005305206 | 31.46256022 | 4.963444 | 5.297868 | 3.324375 | 8.376156 | 9.939008 | 9.984774 |
| SF3B1 | 1.273743468 | 0.043453389 | 0.004250425 | 31.42949639 | 5.982974 | 4.389936 | 5.609945 | 11.138295 | 10.527518 | 9.363984 |
| GNE | 1.21272124 | 0.043453389 | 0.005359646 | 31.4199118 | 4.263463 | 3.770995 | 2.165421 | 9.23707 | 7.406567 | 8.305171 |
| HDAC1 | 1.214654734 | 0.043453389 | 0.005325621 | 31.41884653 | 2.201691 | 2.023048 | 2.165421 | 7.394225 | 7.138979 | 5.634184 |
| IARS2 | 1.205076227 | 0.043453389 | 0.005495747 | 31.41884653 | 3.024504 | 2.023048 | 2.165421 | 8.316805 | 7.138979 | 6.051818 |
| YBX1 | 1.37527445 | 0.043453389 | 0.002773733 | 31.29942083 | 5.056948 | 4.750708 | 5.389265 | 10.561063 | 10.025012 | 9.454835 |
| RILPL2 | 1.313962622 | 0.043453389 | 0.003658387 | 31.26954414 | 3.839948 | 2.023048 | 3.90836 | 8.875048 | 8.200916 | 8.053616 |
| RAB33B | 1.133148507 | 0.043453389 | 0.007271181 | 31.22285776 | 3.024504 | 3.360637 | 2.995681 | 8.925589 | 7.989035 | 6.195186 |
| MEN2 | 1.264116174 | 0.043453389 | 0.004379721 | 31.15626786 | 3.819732 | 2.809601 | 2.165421 | 7.771052 | 8.140553 | 7.218312 |
| DBI | 1.056131079 | 0.043540291 | 0.00972984 | 31.09862275 | 4.743564 | 4.389936 | 4.285996 | 10.650924 | 9.348715 | 7.03218 |
| BEND2 | 1.152357621 | 0.043453389 | 0.006788023 | 31.08883941 | 2.993831 | 2.406905 | 4.944468 | 7.36523 | 8.258856 | 8.997112 |
| UHRF2 | 1.334885608 | 0.043453389 | 0.00329772 | 30.99408886 | 1.874444 | 3.360637 | 3.764125 | 7.726141 | 8.314558 | 8.32282 |
| NTRK2 | 1.150755415 | 0.043453389 | 0.006849268 | 30.92098567 | 2.201691 | 4.750708 | 2.995681 | 9.252991 | 8.033973 | 7.152205 |
| LOC100131257 | 1.38664099 | 0.043453389 | 0.002630827 | 30.918754 | 7.067614 | 6.821329 | 7.593473 | 11.725233 | 12.639383 | 12.018077 |
| FUCA2 | 1.126130656 | 0.043453389 | 0.007434502 | 30.82988526 | 2.201691 | 2.023048 | 3.324375 | 8.270632 | 8.200916 | 5.580533 |
| SELE | 1.046294498 | 0.043577906 | 0.010100034 | 30.78458253 | 1.874444 | 3.360637 | 2.165421 | 7.109557 | 5.165949 | 9.103055 |
| NBAS | 1.244369869 | 0.043453389 | 0.004774413 | 30.74788378 | 1.874444 | 2.023048 | 2.165421 | 5.705318 | 7.107836 | 7.033813 |
| FRZB | 1.127406931 | 0.043453389 | 0.007407281 | 30.74788378 | 1.874444 | 2.023048 | 2.165421 | 5.095353 | 7.107836 | 5.634184 |
| ZNF189 | 1.235415384 | 0.043453389 | 0.004890099 | 30.63280987 | 1.874444 | 2.023048 | 2.165421 | 6.960054 | 7.656894 | 7.825039 |
| ARHGEF6 | 1.195695111 | 0.043453389 | 0.005801293 | 30.63280987 | 2.201691 | 2.023048 | 3.90836 | 6.960054 | 7.269549 | 7.492252 |
| RICTOR | 1.263380463 | 0.043453389 | 0.00400136 | 30.61865727 | 4.209882 | 3.360637 | 2.995681 | 9.146221 | 8.436733 | 4.146207 |
| TMEM198B | 0.867447711 | 0.044369384 | 0.018025859 | 30.579245565 | 2.201691 | 2.809601 | 3.324375 | 7.835902 | 8.258856 | 7.033813 |
| NOL10 | 1.484870677 | 0.043453389 | 0.001643416 | 30.50765727 | 2.201691 | 2.023048 | 2.165421 | 6.954147 | 7.25505 | 7.428484 |
| KIF22 | 1.345811504 | 0.043453389 | 0.003154815 | 30.50560287 | 1.874444 | 2.809601 | 2.165421 | 6.544171 | 7.740604 | 3.676349 |
| PQLC3 | 1.263380463 | 0.044203301 | 0.016808438 | 30.46676027 | 1.874444 | 2.406905 | 2.165421 | 6.960054 | 7.094585 | 3.676349 |
| C1orf140 | 0.894136718 | 0.044066162 | 0.02397278 | 30.46676027 | 2.201691 | 2.023048 | 2.165421 | 2.820813 | 7.094585 | 7.352555 |
| MRPS11 | 0.771554363 | 0.043453389 | 0.003821708 | 30.27358514 | 1.874444 | 3.360637 | 2.165421 | 7.814607 | 6.794431 | 7.582913 |
| MZT2B | 1.304815336 | 0.043453389 | 0.00705342 | 30.27358514 | 1.874444 | 3.770995 | 3.324375 | 9.367104 | 6.794431 | 7.218312 |
| ZNF674 | 1.440991678 | 0.043453389 | 0.003916979 | 30.1480339 | 4.309025 | 4.80797 | 5.571599 | 8.955085 | 10.183015 | 10.485591 |
| COQ5 | 1.301934657 | 0.043453389 | 0.002078938 | 30.08567326 | 2.993831 | 2.406905 | 2.379345 | 8.316805 | 7.31791 | 6.32627 |
| MYLK4 | 1.23175442 | 0.043453389 | 0.002078938 | 30.07069338 | 1.874444 | 2.023048 | 2.165421 | 7.210813 | 6.78473 | 7.020304 |
| SKAP2 | 1.435288397 | 0.043453389 | 0.00705342 | 30.07069338 | 1.874444 | 2.023048 | 4.285996 | 8.270632 | 6.78473 | 7.255535 |
| TSFM | 1.141876001 | 0.043453389 | 0.007196325 | 30.0646308 | 1.874444 | 3.360637 | 2.165421 | 7.094585 | 7.094585 | 5.874974 |
| DLK1 | 0.9225467 | 0.044091888 | 0.015218782 | 30.03852001 | 4.682076 | 2.406905 | 2.165421 | 9.590293 | 8.867558 | 3.676349 |
| CAT | 1.195492807 | 0.043453389 | 0.00808098 | 30.02758475 | 1.874444 | 2.809601 | 3.935222 | 9.884081 | 9.198885 | 7.36177 |
| RPSAP9 | 1.251028246 | 0.043453389 | 0.004604287 | 30.02669603 | 1.874444 | 2.023048 | 2.165421 | 5.728038 | 7.656894 | 6.931222 |
| BTN2A1 | 1.200475895 | 0.043453389 | 0.005672678 | 30.02669603 | 1.874444 | 2.023048 | 2.165421 | 7.814607 | 7.174648 | 6.931222 |
| IRX5 | 1.219657742 | 0.043453389 | 0.005209935 | 30.02014287 | 3.024504 | 4.413323 | 3.324375 | 7.897963 | 8.258856 | 7.582913 |
| PRKAA1 | 1.288206241 | 0.043453389 | 0.004114325 | 29.90431184 | 1.874444 | 2.023048 | 2.995681 | 6.063041 | 8.220489 | 6.649696 |
| KLHDC1 | 1.314816514 | 0.043453389 | 0.003624362 | 29.87790531 | 1.874444 | 2.023048 | 2.165421 | 6.063041 | 7.627877 | 6.924055 |
| GTF2H1 | 1.211573024 | 0.043453389 | 0.005393671 | 29.87790531 | 3.839948 | 2.023048 | 2.165421 | 8.206677 | 7.187136 | 6.924055 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| DUSP10 | 1.181364273 | 0.043453389 | 0.00616196 | 29.87233018 | 2.201691 | 2.023048 | 2.165421 | 8.822673 | 7.066159 | 5.426231 |
| KLHL2 | 1.01285523 | 0.043581008 | 0.011361688 | 29.87233018 | 2.201691 | 2.023048 | 2.165421 | 7.167419 | 7.066159 | 4.562324 |
| HNF1A-AS1 | 1.452617105 | 0.043453389 | 0.001874787 | 29.86186912 | 1.874444 | 2.023048 | 2.165421 | 6.857154 | 6.774676 | 7.291822 |
| ITFG1 | 1.194757594 | 0.043453389 | 0.005828513 | 29.8113244 | 3.839948 | 2.023048 | 2.165421 | 7.210813 | 8.737737 | 6.69026 |
| OXA1L | 1.360793121 | 0.043453389 | 0.002964274 | 29.79857409 | 3.350997 | 3.770995 | 3.935222 | 9.755869 | 8.668166 | 8.010706 |
| KDM5B | 1.126061068 | 0.043453389 | 0.007441307 | 29.74872027 | 3.839948 | 2.023048 | 2.165421 | 8.734704 | 7.187136 | 6.195186 |
| C9orf16 | 1.26485903 | 0.043453389 | 0.004372916 | 29.72420265 | 3.024504 | 4.750708 | 3.324375 | 7.918071 | 8.94019 | 8.870819 |
| ZNF252 | 1.326603647 | 0.043453389 | 0.003488261 | 29.56092315 | 2.201691 | 2.406905 | 2.165421 | 6.339437 | 7.292524 | 7.291822 |
| OXCT1 | 1.014578067 | 0.04358l008 | 0.011280027 | 29.52243909 | 2.993831 | 2.023048 | 2.165421 | 7.877571 | 7.406567 | 4.790662 |
| ZNF669 | 1.327488278 | 0.043453389 | 0.003467846 | 29.44516018 | 4.309025 | 4.413323 | 4.285996 | 8.460642 | 9.188984 | 10.028457 |
| MAL2 | 1.114360625 | 0.043485739 | 0.007778836 | 29.35846873 | 2.201691 | 3.770995 | 2.379345 | 9.627408 | 7.25505 | 6.106561 |
| PSMD5 | 1.388001581 | 0.043453389 | 0.002610412 | 29.24717514 | 3.024504 | 2.406905 | 3.324375 | 7.582358 | 7.89473 | 7.943848 |
| MED28 | 1.090203204 | 0.043516135 | 0.00859408 | 29.13069048 | 2.201691 | 2.406905 | 2.165421 | 7.814607 | 7.066159 | 5.106393 |
| AHNAK | 1.305297342 | 0.043453389 | 0.003787683 | 29.08342561 | 6.554045 | 7.303362 | 6.282905 | 11.41617 | 12.322489 | 10.992428 |
| COL3A1 | 1.067263884 | 0.043516135 | 0.009333106 | 28.9900444 | 5.700376 | 7.197097 | 8.234655 | 10.557862 | 13.454821 | 11.141608 |
| PDCD6 | 1.311659275 | 0.043453389 | 0.003706022 | 28.93779811 | 2.201691 | 3.872014 | 2.165421 | 8.579223 | 8.2398 | 7.020304 |
| MRPL11 | 1.258241709 | 0.043453389 | 0.004481797 | 28.93779811 | 1.874444 | 2.406905 | 2.165421 | 7.897963 | 5.936219 | 7.020304 |
| C8orf44 | 1.283268884 | 0.043453389 | 0.00416196 | 28.91838598 | 2.201691 | 2.023048 | 2.995681 | 6.395481 | 7.414086 | 7.849596 |
| CPNE3 | 1.22296601 | 0.043453389 | 0.005141885 | 28.86615951 | 4.309025 | 3.872014 | 2.165421 | 8.723321 | 8.777924 | 7.523109 |
| LOC494127 | 1.178201462 | 0.043453389 | 0.006209595 | 28.80295076 | 4.263463 | 2.406905 | 2.165421 | 7.177844 | 7.25505 | 8.84662 |
| TRIM39 | 1.441349613 | 0.043453389 | 0.002017693 | 28.79366669 | 1.874444 | 2.023048 | 2.165421 | 6.814118 | 7.094585 | 6.722123 |
| TOP1MT | 1.34212424 | 0.043453389 | 0.003209255 | 28.79366669 | 1.874444 | 2.023048 | 2.165421 | 7.144104 | 7.292524 | 6.722123 |
| FOLR1 | 1.158283711 | 0.043453389 | 0.006651922 | 28.79366669 | 1.874444 | 2.809601 | 2.165421 | 9.29204 | 6.774676 | 6.722123 |
| C1orf126 | 1.327742062 | 0.043453389 | 0.003447431 | 28.70445443 | 5.304463 | 4.830496 | 3.935222 | 9.171571 | 10.147665 | 9.570168 |
| PAIP1 | 1.058249399 | 0.043540291 | 0.009593739 | 28.62083171 | 3.350997 | 3.770995 | 2.995681 | 8.222933 | 8.609988 | 6.106561 |
| LOC100131176 | 1.32954682 | 0.043453389 | 0.003413406 | 28.61570033 | 1.874444 | 2.023048 | 2.165421 | 7.937902 | 6.861783 | 6.195186 |
| C4orf33 | 1.039027569 | 0.043577906 | 0.010330725 | 28.61570033 | 1.874444 | 2.023048 | 2.165421 | 8.173604 | 6.861783 | 4.476242 |
| SUCLA2 | 1.30692967 | 0.043453389 | 0.003767268 | 28.52404123 | 1.874444 | 3.872014 | 2.165421 | 6.857154 | 7.094585 | 6.051818 |
| FAM76A | 1.201224353 | 0.043453389 | 0.005604627 | 28.52404123 | 3.839948 | 4.830496 | 3.935222 | 6.857154 | 10.147665 | 8.135789 |
| CEP290 | 1.162996485 | 0.043453389 | 0.006536237 | 28.52404123 | 1.874444 | 2.023048 | 2.165421 | 6.857154 | 7.598264 | 7.020304 |
| FGG | 0.803230397 | 0.045338539 | 0.021842123 | 28.52404123 | 3.839948 | 2.023048 | 2.165421 | 6.857154 | 9.950776 | 2.921909 |
| ZNF280D | 1.344961563 | 0.043453389 | 0.00317523 | 28.48484659 | 2.201691 | 2.406905 | 3.324375 | 7.70315 | 10.12707 | 7.033813 |
| TTF1 | 1.191744079 | 0.043453389 | 0.005930589 | 28.46679443 | 2.993831 | 4.413323 | 2.165421 | 7.748771 | 8.098861 | 7.825039 |
| MBOAT1 | 1.22317861 | 0.043453389 | 0.005128275 | 28.45749028 | 1.874444 | 2.809601 | 4.449894 | 8.854326 | 7.89473 | 7.640338 |
| HSP90AA1 | 1.292334802 | 0.043453389 | 0.004025859 | 28.36550061 | 8.313476 | 8.544272 | 9.431116 | 13.483213 | 7.627877 | 13.003629 |
| LOC100129316 | 1.340554031 | 0.043453389 | 0.003236475 | 28.32574051 | 1.874444 | 2.023048 | 2.995681 | 7.531061 | 14.257181 | 6.587378 |
| LOC100507043 | 1.258204983 | 0.043453389 | 0.004488602 | 28.32574051 | 1.874444 | 2.023048 | 2.379345 | 6.954147 | 7.819723 | 7.033813 |
| SMAGP | 1.154754322 | 0.043453389 | 0.006740388 | 28.29142686 | 5.700376 | 6.139057 | 2.165421 | 7.631894 | 7.187136 | 5.580533 |
| POLR1D | 1.247452902 | 0.043453389 | 0.004692753 | 28.27757202 | 5.700376 | 6.139057 | 4.724406 | 10.960644 | 7.598264 | 9.808064 |
| SELENBP1 | 1.302155205 | 0.043453389 | 0.003910174 | 28.24420953 | 4.639409 | 4.736586 | 6.031658 | 9.45919 | 9.950776 | 10.637895 |
| EID1 | 1.302217304 | 0.043453389 | 0.003903368 | 28.1563887 | 5.744513 | 3.872014 | 6.012527 | 9.81605 | 10.12707 | 10.473789 |
| NOP2 | 1.224208852 | 0.043453389 | 0.00510786 | 28.14801618 | 1.874444 | 2.023048 | 3.90836 | 8.723321 | 10.827917 | 6.587378 |
| INTS4 | 1.025871953 | 0.043577906 | 0.010736305 | 28.09141903 | 1.874444 | 2.809601 | 2.379345 | 4.894482 | 7.656894 | 7.695565 |
| CDK11A | 1.385874106 | 0.043453389 | 0.002637632 | 28.05059022 | 3.350997 | 3.360637 | 3.324375 | 9.344992 | 7.191402 | 7.849596 |
| C6orf147 | 1.389243899 | 0.043453389 | 0.002569581 | 28.00846712 | 1.874444 | 2.023048 | 2.379345 | 6.544171 | 8.160956 | 7.020304 |
| UBE2A | 1.336013022 | 0.043453389 | 0.00328411 | 27.92504731 | 2.201691 | 3.32135 | 3.90636 | 8.711848 | 7.187136 | 7.920656 |
| LOC145216 | 1.295275515 | 0.043453389 | 0.004005444 | 27.89537618 | 5.491121 | 4.911517 | 5.702912 | 9.403221 | 7.989035 | 10.293075 |
| AP3S1 | 1.185039382 | 0.043453389 | 0.006059884 | 27.84645718 | 3.839948 | 2.406905 | 2.379345 | 7.856667 | 10.732294 | 6.455366 |
| C8orf83 | 1.266030782 | 0.043453389 | 0.004359306 | 27.8286526 | 1.874444 | 2.023048 | 2.379345 | 7.177844 | 8.63937 | 5.900694 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| TERF1 | 1.318635193 | 0.043453389 | 0.003597142 | 27.81396266 | 3.819732 | 2.809601 | 3.324375 | 7.607339 | 8.533804 | 8.155622 |
| CUL1 | 1.336475973 | 0.043453389 | 0.003277305 | 27.7705281 | 1.874444 | 2.809601 | 3.324375 | 7.33564 | 8.119657 | 7.46072 |
| NEXN | 1.19780668 | 0.043453389 | 0.005740728 | 27.75417262 | 1.874444 | 2.809601 | 2.165421 | 6.960054 | 7.819723 | 5.900694 |
| UBE2V2 | 1.016211074 | 0.043581008 | 0.011205172 | 27.75417262 | 2.201691 | 2.023048 | 2.165421 | 6.960054 | 7.414086 | 4.562324 |
| CHMP5 | 1.262148716 | 0.043453389 | 0.004440966 | 27.70487106 | 4.639409 | 3.32135 | 4.449894 | 9.431477 | 8.668166 | 8.456743 |
| HIBCH | 1.408205581 | 0.043453389 | 0.002311795 | 27.67558528 | 1.874444 | 2.023048 | 2.165421 | 6.664965 | 7.473335 | 6.722123 |
| LOC151475 | 1.288672205 | 0.043453389 | 0.004127935 | 27.67558528 | 1.874444 | 3.360637 | 2.165421 | 6.664965 | 7.942653 | 7.523109 |
| KIAA0922 | 1.200724007 | 0.043453389 | 0.005645458 | 27.67558528 | 1.874444 | 2.023048 | 3.764125 | 6.664965 | 7.440337 | 7.611911 |
| CACYBP | 1.31956748 | 0.043453389 | 0.003569922 | 27.64478389 | 6.45321 | 6.572071 | 6.83141 | 10.70401 | 11.620345 | 11.57626 |
| PHLDA3 | 1.205863977 | 0.043453389 | 0.005482137 | 27.6407809 | 2.201691 | 2.023048 | 2.165421 | 6.954147 | 7.473335 | 5.634184 |
| PCDHB9 | 1.410768292 | 0.043453389 | 0.002290575 | 27.63248235 | 1.874444 | 2.023048 | 2.165421 | 6.811341 | 6.640994 | 7.668215 |
| ALG6 | 1.394775296 | 0.043453389 | 0.002494726 | 27.63248235 | 1.874444 | 2.023048 | 2.379345 | 6.811341 | 7.066159 | 6.69026 |
| SMARCAD1 | 1.304513855 | 0.043453389 | 0.003842123 | 27.63248235 | 1.874444 | 2.023048 | 2.165421 | 6.811341 | 7.138979 | 6.051818 |
| MCEE | 1.184678753 | 0.043453389 | 0.006066689 | 27.63248235 | 1.874444 | 2.023048 | 2.165421 | 6.811341 | 7.414066 | 5.426231 |
| GULP1 | 0.781133439 | 0.045799831 | 0.023259612 | 27.63248235 | 1.874444 | 2.023048 | 2.379345 | 6.811341 | 7.440337 | 5.921909 |
| DYNC1I2 | 1.327615653 | 0.043453389 | 0.003461041 | 27.58807888 | 5.658609 | 5.297868 | 4.754917 | 10.444562 | 10.006216 | 9.570168 |
| PHAX | 1.243471647 | 0.043453389 | 0.004781218 | 27.54026237 | 5.316227 | 4.911517 | 3.935222 | 8.723321 | 9.694987 | 9.769968 |
| CAGE1 | 1.20359799 | 0.043453389 | 0.005522967 | 27.52617776 | 3.839948 | 2.406905 | 2.165421 | 6.252746 | 8.609988 | 8.622681 |
| ADH4 | 1.389436138 | 0.043453389 | 0.002555971 | 27.42236243 | 1.874444 | 2.023048 | 2.165421 | 6.651882 | 8.055928 | 6.73963 |
| COX5A | 1.203328515 | 0.043453389 | 0.005529772 | 27.41727934 | 4.309025 | 3.872014 | 4.724406 | 10.91884 | 9.086038 | 7.873743 |
| TMEM131 | 1.316177849 | 0.043453389 | 0.003610752 | 27.3838058 | 1.874444 | 2.023048 | 3.324375 | 7.976765 | 7.793829 | 6.649696 |
| CHD1L | 1.395319453 | 0.043453389 | 0.002487921 | 27.34488431 | 1.874444 | 2.406905 | 2.379345 | 6.960054 | 6.861783 | 7.180104 |
| KCNS3 | 1.333010474 | 0.043453389 | 0.003331745 | 27.31049112 | 1.874444 | 2.023048 | 2.379345 | 7.144104 | 6.794431 | 6.195186 |
| VPS37A | 1.331793484 | 0.043453389 | 0.003352161 | 27.31049112 | 1.874444 | 2.023048 | 2.165421 | 7.36523 | 6.794431 | 6.195186 |
| ITPKB | 1.267570998 | 0.043453389 | 0.004325281 | 27.31049112 | 2.993831 | 2.023048 | 2.995681 | 8.156778 | 6.794431 | 7.291822 |
| TP53INP1 | 1.212479915 | 0.043453389 | 0.005366451 | 27.31049112 | 2.993831 | 2.023048 | 3.764125 | 8.069577 | 6.794431 | 8.053616 |
| C3orf75 | 1.185333178 | 0.043453389 | 0.005862538 | 27.31049112 | 1.874444 | 2.023048 | 2.165421 | 7.607339 | 6.794431 | 5.426231 |
| PTH1R | 1.048036445 | 0.043577906 | 0.010018374 | 27.31049112 | 1.874444 | 2.023048 | 2.165421 | 4.718672 | 6.794431 | 7.020304 |
| CD2AP | 1.292672349 | 0.043453389 | 0.004019054 | 27.27154382 | 3.024504 | 2.406905 | 3.324375 | 9.704692 | 7.793829 | 7.033813 |
| C7orf53 | 1.186350694 | 0.043453389 | 0.006039469 | 27.21916211 | 1.874444 | 2.406905 | 4.508334 | 8.757204 | 6.640994 | 8.650903 |
| CYB5RL | 1.302765953 | 0.043453389 | 0.003862538 | 27.21082387 | 4.963444 | 4.351315 | 3.935222 | 8.540832 | 9.729553 | 9.414247 |
| SEPT1 | 1.392275523 | 0.043453389 | 0.002521946 | 27.20501672 | 2.201691 | 2.023048 | 2.165421 | 7.70315 | 6.613395 | 6.931222 |
| TENC1 | 1.318863278 | 0.043453389 | 0.003583532 | 27.18396073 | 3.350997 | 2.406905 | 3.935222 | 7.771052 | 8.564762 | 8.11568 |
| BCAS2 | 1.412430196 | 0.043453389 | 0.002262674 | 27.12745785 | 1.874444 | 2.023048 | 2.165421 | 7.36523 | 6.78473 | 6.618407 |
| SLC25A20 | 1.302507789 | 0.043453389 | 0.003876148 | 27.12745785 | 1.874444 | 2.023048 | 2.165421 | 7.109557 | 6.78473 | 6.51818 |
| C2orf67 | 1.288782249 | 0.043453389 | 0.004073444 | 27.12745785 | 3.024504 | 2.023048 | 2.165421 | 6.960054 | 6.78473 | 7.291822 |
| CGNL1 | 1.239415644 | 0.043453389 | 0.004828853 | 27.12745785 | 1.874444 | 2.023048 | 2.995681 | 8.801178 | 6.78473 | 6.385515 |
| MRPL9 | 1.221641844 | 0.043453389 | 0.005169105 | 27.12745785 | 1.874444 | 2.023048 | 2.165421 | 7.394225 | 6.78473 | 5.634184 |
| CAPZA2 | 1.251008609 | 0.043453389 | 0.004611092 | 27.11795784 | 3.350997 | 4.736586 | 3.935222 | 9.220972 | 8.696398 | 8.135789 |
| C15orf29 | 1.267254291 | 0.043453389 | 0.004138891 | 27.08898184 | 1.874444 | 2.406905 | 2.379345 | 8.301578 | 7.138979 | 6.051818 |
| D2HGDH | 1.236465647 | 0.043453389 | 0.004862879 | 27.08898184 | 1.874444 | 2.406905 | 2.379345 | 7.531061 | 7.138979 | 5.900694 |
| TIA1 | 1.246571093 | 0.043453389 | 0.004719973 | 27.07231286 | 3.839948 | 4.389936 | 3.935222 | 9.137671 | 9.148683 | 7.774634 |
| MRPS33 | 1.324974146 | 0.043453389 | 0.003501871 | 27.07020821 | 1.874444 | 2.406905 | 2.165421 | 6.339437 | 7.187136 | 6.924055 |
| ARAF | 1.20305 | 0.043453389 | 0.005550889 | 27.00097964 | 2.993831 | 3.872014 | 2.165421 | 7.748771 | 7.094585 | 7.800057 |
| NEK5 | 1.279086825 | 0.043453389 | 0.004195985 | 26.9930149 | 5.491121 | 4.351315 | 5.018694 | 9.102956 | 10.779249 | 9.649245 |
| GFM2 | 1.312923887 | 0.043453389 | 0.003678802 | 26.93907272 | 1.874444 | 2.023048 | 2.165421 | 7.074163 | 6.774676 | 6.106561 |
| MYO9A | 1.304878008 | 0.043453389 | 0.003814903 | 26.93907272 | 1.874444 | 2.023048 | 2.165421 | 6.067497 | 6.774676 | 7.352555 |
| PIGB | 1.268381405 | 0.043453389 | 0.004304866 | 26.93907272 | 1.874444 | 2.023048 | 2.165421 | 7.30543 | 6.774676 | 5.882028 |
| ENOPH1 | 0.908376858 | 0.044173537 | 0.015981626 | 26.93907272 | 1.874444 | 2.023048 | 2.165421 | 8.033165 | 6.774676 | 3.630092 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| EFNA4 | 0.879435185 | 0.044278935 | 0.017476693 | 26.93907272 | 1.874444 | 2.023048 | 2.165421 | 7.109557 | 6.774676 | 3.630092 |
| SYPL1 | 1.198475456 | 0.043453389 | 0.005720313 | 26.86521477 | 5.700376 | 4.389936 | 4.449894 | 10.448044 | 9.266358 | 8.784285 |
| CHPT1 | 1.210262053 | 0.043453389 | 0.005420891 | 26.85520033 | 4.209882 | 3.360637 | 3.935222 | 10.746803 | 8.682351 | 7.428484 |
| LOC100128292 | 1.322332238 | 0.043453389 | 0.003549507 | 26.83698597 | 4.963444 | 3.360637 | 4.944468 | 8.993498 | 9.694987 | 9.690619 |
| KLHL20 | 1.33934312 | 0.043453389 | 0.003250085 | 26.7963288 | 1.874444 | 2.023048 | 2.379345 | 8.270632 | 6.640994 | 6.618407 |
| GLB1 | 1.258683321 | 0.043453389 | 0.0004474991 | 26.7776453 | 3.024504 | 2.023048 | 2.165421 | 7.726141 | 7.767462 | 6.195186 |
| CAPN6 | 1.104637166 | 0.0043349335 | 0.008058523 | 26.74675975 | 2.201691 | 2.023048 | 3.324375 | 5.728038 | 9.749902 | 6.942983 |
| PCBP1 | 1.158269909 | 0.043453389 | 0.006658727 | 26.71527101 | 6.099991 | 5.487673 | 6.056062 | 11.549452 | 10.795655 | 9.113234 |
| LRRC70 | 1.143404665 | 0.043453389 | 0.007019394 | 26.7034022 | 1.874444 | 2.023048 | 3.764125 | 7.274575 | 6.613395 | 7.033813 |
| PPL | 1.187302315 | 0.043453389 | 0.000619054 | 26.62256564 | 1.874444 | 3.32135 | 3.324375 | 8.087444 | 8.055928 | 6.455366 |
| SRBD1 | 1.410076224 | 0.044464174 | 0.000229738 | 26.60421067 | 1.874444 | 2.023048 | 2.165421 | 7.144104 | 6.608026 | 6.73963 |
| BCL11B | 0.853806804 | 0.043453389 | 0.018663491 | 26.60421067 | 1.874444 | 2.406905 | 5.702912 | 7.167419 | 6.608026 | 7.640338 |
| MPPED2 | 1.288231932 | 0.043453389 | 0.00410752 | 26.42959835 | 2.201691 | 2.406905 | 2.165421 | 6.252746 | 7.596264 | 6.931222 |
| NDUFAF4 | 1.225280207 | 0.043453389 | 0.00508064 | 26.43270033 | 3.024504 | 3.770995 | 2.165421 | 7.037879 | 8.098861 | 7.748756 |
| TCP1 | 1.294560006 | 0.043453389 | 0.004012249 | 26.35673733 | 6.054828 | 6.184248 | 6.891005 | 10.998912 | 11.611105 | 10.591321 |
| IFI27L1 | 1.344183329 | 0.043453389 | 0.000318884 | 26.29255667 | 1.874444 | 2.023048 | 2.165421 | 6.339437 | 7.819723 | 6.73963 |
| ZNF204P | 1.190536984 | 0.043453389 | 0.005971419 | 26.281036 | 1.874444 | 2.023048 | 2.379345 | 5.579836 | 7.094585 | 6.931222 |
| DUSP16 | 0.808288261 | 0.045257569 | 0.021494386 | 26.281036 | 4.263463 | 2.023048 | 2.379345 | 9.171571 | 7.094585 | 4.146207 |
| SUB1 | 1.169061275 | 0.043453389 | 0.006545476 | 26.26664559 | 5.700376 | 5.487673 | 3.90836 | 11.207333 | 10.202833 | 8.456743 |
| TPM1 | 1.191107633 | 0.043453389 | 0.005951004 | 26.25449514 | 5.263699 | 6.184248 | 3.324375 | 10.898741 | 9.834907 | 9.113234 |
| FANCD2 | 1.297734103 | 0.043453389 | 0.003971419 | 26.24490192 | 3.839948 | 3.360637 | 2.165421 | 7.556937 | 8.533804 | 8.074602 |
| TMEM200B | 1.0933647 | 0.0434933335 | 0.00847363 | 26.22615433 | 1.874444 | 2.023048 | 3.90836 | 7.274575 | 6.78473 | 6.587378 |
| GBP2 | 1.355447985 | 0.043453389 | 0.003039129 | 26.19997746 | 4.263463 | 3.360637 | 4.754917 | 9.381659 | 8.916384 | 8.974957 |
| F10 | 1.122974473 | 0.043480953 | 0.007514801 | 26.16558154 | 2.201691 | 4.351315 | 3.324375 | 6.664985 | 8.033973 | 9.584871 |
| NRBP2 | 1.043836521 | 0.043577906 | 0.010215039 | 26.16230076 | 3.839948 | 2.406905 | 5.225216 | 8.628872 | 8.549366 | 7.291822 |
| C3orf58 | 1.130842011 | 0.043453389 | 0.0073725621 | 26.08107487 | 3.350997 | 2.406905 | 2.995681 | 7.835902 | 8.055928 | 6.106561 |
| CXCL2 | 1.06489746 | 0.043516135 | 0.009394352 | 26.03931406 | 3.350997 | 5.297868 | 5.225216 | 11.153218 | 8.63937 | 8.053616 |
| PTRHD1 | 1.201607749 | 0.043453389 | 0.005577407 | 26.02333161 | 2.993831 | 2.809601 | 4.449894 | 8.98399 | 7.656894 | 7.695565 |
| CEP85L | 1.166244188 | 0.043453389 | 0.006488602 | 25.97542296 | 1.874444 | 2.023048 | 3.935222 | 7.33564 | 7.793829 | 6.722123 |
| SLC25A12 | 1.276421753 | 0.043453389 | 0.004223205 | 25.9266156 | 2.993831 | 2.023048 | 2.165421 | 6.664985 | 6.861783 | 7.695565 |
| BCL11A | 1.252313386 | 0.043453389 | 0.004538872 | 25.9266156 | 2.201691 | 2.023048 | 2.165421 | 9.388882 | 6.861783 | 6.051818 |
| C14orf45 | 1.245184011 | 0.043453389 | 0.004740388 | 25.9266156 | 2.201691 | 2.023048 | 2.165421 | 7.33564 | 6.861783 | 5.874974 |
| AK5 | 1.235847176 | 0.043453389 | 0.004883294 | 25.9266156 | 2.201691 | 2.406905 | 2.165421 | 8.270632 | 6.861783 | 5.900694 |
| DUSP12 | 0.887282254 | 0.044203301 | 0.01714869 | 25.90081669 | 1.874444 | 3.32135 | 2.165421 | 8.579223 | 6.861783 | 4.146207 |
| RB1CC1 | 1.228300107 | 0.043453389 | 0.005019394 | 25.84356993 | 3.819732 | 4.413323 | 2.379345 | 8.514658 | 8.668166 | 7.774634 |
| TRPT1 | 1.27393932 | 0.043453389 | 0.004356815 | 25.84356993 | 2.201691 | 3.32135 | 2.165421 | 6.857154 | 7.138979 | 7.943848 |
| CDC123 | 1.002153052 | 0.043588662 | 0.011776114 | 25.84356993 | 1.874444 | 4.80797 | 2.165421 | 6.857154 | 7.767462 | 7.020304 |
| SKP1 | 1.221824281 | 0.043453389 | 0.005352841 | 25.74697466 | 4.682076 | 2.023048 | 3.324375 | 10.224057 | 9.228189 | 8.010706 |
| SATB1 | 1.092761889 | 0.0434349335 | 0.005360851 | 25.69536742 | 1.874444 | 2.023048 | 3.324375 | 8.591796 | 7.138979 | 6.722123 |
| LOC439990 | 1.040800583 | 0.043577906 | 0.010276284 | 25.65778815 | 3.350997 | 2.406905 | 5.018694 | 7.177844 | 8.2398 | 8.03232 |
| SP100 | 1.311890328 | 0.043453389 | 0.003692412 | 25.59872008 | 5.328526 | 4.389936 | 4.508334 | 10.006526 | 9.81573 | 8.894619 |
| TAGAP | 1.377341913 | 0.043453389 | 0.002753317 | 25.5809718 | 1.874444 | 2.023048 | 2.165421 | 7.70315 | 6.551443 | 6.69026 |
| WDR11 | 1.373235057 | 0.043453389 | 0.002800953 | 25.5809718 | 1.874444 | 2.023048 | 2.165421 | 7.835902 | 6.551443 | 6.69026 |
| ICOS | 1.091663323 | 0.0435113 | 0.008552569 | 25.5809718 | 1.874444 | 2.023048 | 4.285996 | 7.748771 | 6.551443 | 7.255535 |
| MAPKAPK5 | 1.262296109 | 0.043453389 | 0.000434161 | 25.56761687 | 1.874444 | 2.023048 | 3.324375 | 6.550689 | 7.56803 | 7.46072 |
| NUDT2 | 1.391350895 | 0.043453389 | 0.002542361 | 25.55468098 | 1.874444 | 2.406905 | 2.165421 | 6.651882 | 6.549959 | 6.942983 |
| LOC440704 | 1.14382507 | 0.0043577906 | 0.007005784 | 25.45236756 | 1.874444 | 2.023048 | 2.165421 | 6.544171 | 8.258856 | 8.03232 |
| INO80B | 1.269804049 | 0.043453389 | 0.004277645 | 25.40802313 | 2.993831 | 2.023048 | 2.165421 | 7.995811 | 6.774676 | 6.69026 |
| COL21A1 | 1.060703985 | 0.043540291 | 0.009518884 | 25.40802313 | 1.874444 | 2.023048 | 2.165421 | 4.739845 | 7.627877 | 6.69026 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| GUCY1A2 | 1.342706111 | 0.043453389 | 0.003195645 | 25.34683046 | 3.350997 | 2.809601 | 3.324375 | 7.976765 | 7.473335 | 8.074602 |
| GTF2A2 | 1.178175253 | 0.043453389 | 0.0062164 | 25.34470702 | 3.350997 | 4.389936 | 2.379345 | 8.014609 | 8.436733 | 7.395512 |
| KDM3B | 0.993371271 | 0.043626235 | 0.012109561 | 25.33506092 | 2.993831 | 2.809601 | 3.324375 | 8.156778 | 7.656894 | 5.446557 |
| SNHG13 | 1.054233315 | 0.043568903 | 0.009786322 | 25.28293607 | 2.201691 | 2.023048 | 3.324375 | 8.688623 | 6.861783 | 5.446557 |
| EXOC1 | 1.269905002 | 0.043453389 | 0.00427084 | 25.26824784 | 1.874444 | 2.406905 | 2.995681 | 7.177844 | 7.066159 | 6.69026 |
| PLA2G16 | 1.252695268 | 0.043453389 | 0.004577067 | 25.18457649 | 3.024504 | 3.32135 | 2.379345 | 8.616619 | 7.31791 | 7.033813 |
| CTSF | 1.195993532 | 0.043453389 | 0.005794488 | 25.13083076 | 3.350997 | 5.297868 | 5.018694 | 8.447068 | 9.81573 | 9.67008 |
| FTO | 1.057854852 | 0.043540291 | 0.009963457 | 25.12617097 | 5.335413 | 2.809601 | 2.995681 | 8.757204 | 8.011679 | 7.46072 |
| IFT43 | 1.154193206 | 0.043453389 | 0.006753998 | 25.12483103 | 4.639409 | 3.360637 | 2.379345 | 8.361545 | 8.011679 | 7.582913 |
| C4orf43 | 1.400491226 | 0.043453389 | 0.002440286 | 25.08403735 | 2.201691 | 2.023048 | 2.165421 | 6.814118 | 7.138979 | 6.649696 |
| ABCB7 | 1.225878698 | 0.043453389 | 0.005046614 | 25.08403735 | 1.874444 | 2.406905 | 6.165421 | 6.814118 | 7.066159 | 5.882028 |
| HIST1H2BD | 1.173051353 | 0.043453389 | 0.006318476 | 25.08403735 | 1.874444 | 2.023048 | 2.165421 | 8.811966 | 6.774676 | 5.446557 |
| LARS | 1.261372601 | 0.043453389 | 0.004454576 | 25.05974983 | 4.743564 | 3.872014 | 2.995681 | 8.616619 | 8.453372 | 8.519314 |
| BBNA1BP2 | 1.182228211 | 0.043453389 | 0.00612113 | 24.96189192 | 3.350997 | 2.023048 | 2.379345 | 9.16317 | 7.96603 | 6.32627 |
| OXSR1 | 1.172615583 | 0.043453389 | 0.006132086 | 24.94924674 | 2.993831 | 2.809601 | 2.379345 | 7.450526 | 8.098861 | 6.129407 |
| BAG1 | 1.152218936 | 0.043453389 | 0.006801633 | 24.79874847 | 3.360637 | 2.995681 | 2.995681 | 8.514658 | 7.627877 | 6.195186 |
| NDUFB6 | 1.273549571 | 0.043453389 | 0.00425723 | 24.79322335 | 3.839948 | 3.770995 | 3.324375 | 8.723321 | 8.402869 | 7.582913 |
| SLC9A3R2 | 1.258137486 | 0.043453389 | 0.004495407 | 24.78739546 | 3.024504 | 3.770995 | 2.379345 | 7.656039 | 7.870158 | 7.428484 |
| NCDN | 1.268437083 | 0.043453389 | 0.004298061 | 24.74405998 | 1.874444 | 2.023048 | 2.165421 | 7.074163 | 6.794431 | 6.106561 |
| LACTB2 | 1.193060818 | 0.043453389 | 0.005869343 | 24.74405998 | 2.201691 | 2.023048 | 2.165421 | 7.25991 | 6.794431 | 5.634184 |
| LSM6 | 1.101421926 | 0.04349335 | 0.008160599 | 24.74405998 | 1.874444 | 2.406905 | 2.165421 | 8.376156 | 6.794431 | 5.106393 |
| C3orf14 | 1.098911998 | 0.04349335 | 0.008235454 | 24.74405998 | 1.874444 | 2.406905 | 2.165421 | 8.033165 | 6.794431 | 5.106393 |
| KRCC1 | 1.35182118 | 0.043453389 | 0.00309544 | 24.7410445 | 1.874444 | 2.023048 | 2.379345 | 6.651882 | 6.551443 | 6.931222 |
| ZNF639 | 1.288369293 | 0.043453389 | 0.004093609 | 24.7410445 | 2.201691 | 2.023048 | 2.995681 | 6.651882 | 7.187136 | 7.218312 |
| BTN3A1 | 1.149993582 | 0.043453389 | 0.006862879 | 24.71535693 | 2.201691 | 2.406905 | 4.724406 | 6.651882 | 8.668166 | 8.519314 |
| NADKD1 | 1.204650513 | 0.043453389 | 0.005502552 | 24.70357767 | 3.819732 | 2.406905 | 2.379345 | 8.447068 | 7.292524 | 6.924055 |
| LZTFL1 | 1.322482116 | 0.043453389 | 0.004298092 | 24.70357767 | 1.874444 | 2.023048 | 2.165421 | 8.433162 | 6.373501 | 6.649696 |
| GLUD2 | 1.318825257 | 0.043453389 | 0.003590337 | 24.70357767 | 1.874444 | 2.023048 | 2.165421 | 7.394225 | 6.205902 | 6.649696 |
| PLXDC2 | 1.26491987 | 0.043453389 | 0.004366111 | 24.70357767 | 1.874444 | 2.023048 | 2.165421 | 7.42265 | 5.920411 | 6.649696 |
| KBTBD6 | 1.028182814 | 0.043577906 | 0.010627424 | 24.61500587 | 4.682076 | 2.023048 | 2.165421 | 7.771052 | 7.25505 | 6.106393 |
| JPX | 1.000944502 | 0.043588662 | 0.01182375 | 24.6122067 | 4.682076 | 4.830496 | 4.285996 | 7.037879 | 9.303543 | 9.676959 |
| ANKHD1 | 1.092120533 | 0.0435113 | 0.008532154 | 24.59580057 | 1.874444 | 3.32135 | 3.935222 | 9.276547 | 7.942653 | 6.106561 |
| IGSF10 | 1.088869818 | 0.043516135 | 0.008641715 | 24.57822677 | 2.201691 | 3.770995 | 3.90836 | 6.063041 | 9.809281 | 8.391335 |
| SMYD3 | 1.370998938 | 0.043453389 | 0.002814563 | 24.57822677 | 1.874444 | 2.023048 | 2.165421 | 6.550689 | 6.78473 | 7.395512 |
| KIAA1598 | 1.229811105 | 0.043453389 | 0.004978564 | 24.57822677 | 1.874444 | 2.809601 | 2.165421 | 7.582358 | 6.78473 | 6.195186 |
| CC2D2B | 1.225940584 | 0.043453389 | 0.005039809 | 24.57822677 | 1.874444 | 2.023048 | 2.165421 | 5.728038 | 6.78473 | 6.722123 |
| PAN2 | 1.113940659 | 0.043485739 | 0.007785641 | 24.57822677 | 1.874444 | 2.023048 | 2.165421 | 8.579223 | 6.78473 | 5.446557 |
| FGF5 | 1.046443307 | 0.043577906 | 0.010079619 | 24.57822677 | 1.874444 | 2.023048 | 2.165421 | 5.095353 | 6.78473 | 7.523109 |
| ZNF511 | 0.730238727 | 0.047384624 | 0.027087445 | 24.5606664 | 2.993831 | 2.023048 | 2.165421 | 7.937902 | 6.78473 | 2.921909 |
| RBL2 | 1.011402059 | 0.043581008 | 0.011395713 | 24.5606664 | 5.744513 | 3.770995 | 3.324375 | 8.474485 | 7.942653 | 8.549611 |
| ZDHHC1 | 1.347018693 | 0.043453389 | 0.003127594 | 24.5550265 | 1.874444 | 2.023048 | 2.165421 | 6.811341 | 6.640994 | 6.32627 |
| RSBN1L | 1.252956716 | 0.043453389 | 0.004570262 | 24.5550265 | 1.874444 | 2.023048 | 2.165421 | 6.814118 | 6.640994 | 5.874974 |
| FTSJ1 | 1.234877871 | 0.043453389 | 0.004910514 | 24.5550265 | 1.874444 | 2.023048 | 2.165421 | 7.167419 | 6.640994 | 5.900694 |
| CXorf56 | 1.20881455 | 0.043453389 | 0.005448112 | 24.5550265 | 1.874444 | 2.023048 | 2.165421 | 7.074163 | 6.640994 | 5.634184 |
| GRHL1 | 0.893151154 | 0.044203301 | 0.016856073 | 24.5550265 | 1.874444 | 2.023048 | 2.165421 | 7.748771 | 6.640994 | 3.630092 |
| SNX1 | 1.156859925 | 0.043453389 | 0.006692753 | 24.54898272 | 3.819732 | 4.413323 | 2.379345 | 9.030914 | 8.011679 | 7.428484 |
| ZNF511 | 0.964307712 | 0.043778104 | 0.01318748 | 24.53129473 | 1.874444 | 3.32135 | 2.165421 | 7.937902 | 7.53715 | 4.562324 |
| SKIL | 0.884512322 | 0.044203301 | 0.017237155 | 24.52866177 | 4.209882 | 4.750708 | 7.794136 | 9.367104 | 9.687973 | 9.248674 |
| ECHDC2 | 1.226139953 | 0.043453389 | 0.005033004 | 24.50006535 | 2.993831 | 4.911517 | 6.012527 | 9.52623 | 9.275744 | 10.531856 |

TABLE 8-continued

Differentially Expressed Genes in CD10–, CD24–, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| DNAJC1 | 1.22334731 | 0.043453389 | 0.00512147 | 24.44821815 | 1.874444 | 2.406905 | 2.995681 | 7.607339 | 7.505595 | 6.129407 |
| LRRCC1 | 1.314195332 | 0.043453389 | 0.000631167 | 24.40754464 | 2.201691 | 2.023048 | 2.165421 | 6.252746 | 6.774676 | 6.924055 |
| PPP1R21 | 1.194302362 | 0.043453389 | 0.005835318 | 24.40754464 | 2.201691 | 2.023048 | 2.165421 | 7.771052 | 6.774676 | 5.634184 |
| SEPT7 | 1.135413648 | 0.043453389 | 0.00723035 | 24.34669689 | 6.344798 | 4.830496 | 4.724406 | 9.33006 | 9.532216 | 9.910841 |
| FAM84A | 0.988776416 | 0.043626235 | 0.012232052 | 24.32697642 | 2.201691 | 2.809601 | 4.944468 | 7.450526 | 7.414086 | 7.152205 |
| IL7R | 1.117427596 | 0.044853389 | 0.007656346 | 24.27757762 | 1.874444 | 4.911517 | 4.449894 | 9.513069 | 7.656894 | 8.549611 |
| PARP3 | 1.245668254 | 0.043453389 | 0.004733583 | 24.21014158 | 2.201691 | 3.32135 | 2.995681 | 7.243046 | 7.91889 | 7.020304 |
| CLUAP1 | 1.159695681 | 0.043453389 | 0.006624702 | 24.20051978 | 1.874444 | 2.809601 | 2.165421 | 5.705318 | 7.406567 | 7.395512 |
| EIF2B1 | 1.33114887 | 0.043453389 | 0.003379381 | 24.17357893 | 1.874444 | 2.023048 | 2.165421 | 6.283686 | 7.31791 | 6.618407 |
| MUC22 | 1.327998933 | 0.043453389 | 0.003433821 | 24.17357893 | 1.874444 | 2.023048 | 2.165421 | 6.244586 | 6.774676 | 6.618407 |
| CSTA | 1.283373611 | 0.043485739 | 0.00414835 | 24.17357893 | 1.874444 | 2.023048 | 2.165421 | 6.063041 | 7.740604 | 6.618407 |
| C3orf72 | 1.228707434 | 0.043453389 | 0.004992174 | 24.17357893 | 2.201691 | 2.023048 | 3.764125 | 7.748771 | 8.200916 | 6.618407 |
| ALDH5A1 | 1.183001358 | 0.043453389 | 0.006100715 | 24.17357893 | 1.874444 | 2.023048 | 3.324375 | 6.498222 | 7.656894 | 6.618407 |
| OTUD1 | 1.089180811 | 0.043516135 | 0.008628105 | 24.17357893 | 3.350997 | 2.023048 | 4.285996 | 8.270632 | 8.055928 | 6.618407 |
| SLC15A2 | 1.113022627 | 0.043485739 | 0.007819667 | 24.11160572 | 3.350997 | 2.809601 | 5.018694 | 7.856887 | 7.942653 | 8.472642 |
| LINC00173 | 1.330363199 | 0.043453389 | 0.003399796 | 24.08974772 | 1.874444 | 2.023048 | 2.185421 | 6.283686 | 6.613395 | 7.327219 |
| LOC338799 | 1.131234123 | 0.043453389 | 0.007312011 | 24.08974772 | 4.209882 | 2.023048 | 2.379345 | 7.582358 | 6.613395 | 8.11568 |
| LOC100506783 | 1.06676176 | 0.043516135 | 0.009353522 | 24.08974772 | 1.874444 | 2.023048 | 2.165421 | 4.894482 | 10.573912 | 6.931222 |
| KLHL5 | 1.161614437 | 0.043453389 | 0.006563457 | 24.06893827 | 6.417969 | 4.750708 | 5.225216 | 9.3744 | 7.942653 | 9.814317 |
| RECQL | 1.213446908 | 0.043453389 | 0.005346036 | 24.05937003 | 2.993831 | 3.32135 | 2.379345 | 7.582358 | 7.094585 | 6.649696 |
| CCDC82 | 1.196942975 | 0.043453389 | 0.005774073 | 24.05937003 | 4.209882 | 2.023048 | 4.285996 | 9.120418 | 9.294336 | 6.051818 |
| SARNP | 1.351167297 | 0.043453389 | 0.003073154 | 24.03537901 | 1.874444 | 4.736586 | 4.285996 | 7.531061 | 6.608026 | 8.79697 |
| C1orf133 | 1.174488081 | 0.043485739 | 0.006304866 | 24.00026479 | 1.874444 | 2.023048 | 2.165421 | 8.676869 | 6.608026 | 5.446557 |
| HSPB11 | 1.027331267 | 0.043577906 | 0.01067506 | 24.00026479 | 4.209882 | 3.360637 | 2.16421 | 6.550689 | 7.656894 | 4.476242 |
| CDKN2AIPNL | 1.262796542 | 0.043453389 | 0.00442051 | 23.97088779 | 2.201691 | 2.406905 | 2.165421 | 8.239009 | 6.78473 | 7.943848 |
| HEXB | 1.200598886 | 0.043453389 | 0.005659068 | 23.96802366 | 2.201691 | 2.023048 | 2.165421 | 7.109557 | 7.870158 | 5.874974 |
| SIKE1 | 1.224561602 | 0.043453389 | 0.005101055 | 23.93288639 | 1.874444 | 3.32135 | 2.165421 | 7.167419 | 6.861783 | 6.455366 |
| RBM15 | 1.104539406 | 0.04349335 | 0.008065328 | 23.93288639 | 1.874444 | 2.023048 | 3.764125 | 7.36523 | 7.138979 | 6.455366 |
| ZNF10 | 0.94699911 | 0.043900827 | 0.01404219 | 23.93288639 | 1.874444 | 2.023048 | 4.944468 | 6.960054 | 6.794431 | 4.790662 |
| TTC33 | 1.057372085 | 0.043577906 | 0.010371555 | 23.92934054 | 1.874444 | 2.023048 | 2.379345 | 9.99237 | 12.049044 | 11.065018 |
| KCNQ1OT1 | 1.188493591 | 0.043453389 | 0.005998639 | 23.87464806 | 6.48761 | 6.049721 | 6.800663 | 9.188227 | 9.392516 | 8.974957 |
| KLRD1 | 1.333603849 | 0.043453389 | 0.00332494 | 23.861422 | 4.815804 | 4.351315 | 4.724406 | 8.331873 | 10.167971 | 11.441372 |
| SERPING1 | 1.077117872 | 0.043516135 | 0.009047295 | 23.83575652 | 5.316227 | 5.661685 | 5.592916 | 7.631894 | 6.774676 | 5.874974 |
| C5orf56 | 1.156360275 | 0.043453389 | 0.006706363 | 23.80157906 | 2.201691 | 2.809601 | 2.165421 | 7.109557 | 7.56803 | 7.352555 |
| KIAA1109 | 1.369557355 | 0.043453389 | 0.004665532 | 23.7910824 | 3.819732 | 2.023048 | 2.995681 | 5.891233 | 7.845161 | 8.053616 |
| SYNE1 | 1.142927948 | 0.043453389 | 0.007033004 | 23.75822255 | 3.819732 | 2.023048 | 3.324375 | 6.664985 | 7.174648 | 6.587378 |
| LOC100233209 | 1.288443668 | 0.043453389 | 0.004087104 | 23.74413357 | 6.792865 | 6.391145 | 7.462086 | 10.960644 | 11.961598 | 11.981038 |
| METTL21A | 1.217985065 | 0.043453389 | 0.005243961 | 23.68699744 | 4.309025 | 5.487673 | 4.724406 | 8.875048 | 9.451686 | 9.430619 |
| MRPL13 | 1.356059366 | 0.043453389 | 0.003011909 | 23.65921155 | 1.874444 | 2.023048 | 2.165421 | 6.396608 | 6.78473 | 6.587378 |
| PAAF1 | 1.289259813 | 0.043453389 | 0.004066689 | 23.65921155 | 1.874444 | 2.023048 | 2.165421 | 6.067497 | 6.794431 | 6.587378 |
| TBC1D7 | 1.280406093 | 0.043453389 | 0.00417557 | 23.65921155 | 3.024504 | 2.023048 | 2.165421 | 7.504712 | 6.043524 | 6.587378 |
| TRIM66 | 1.268142789 | 0.043453389 | 0.004311671 | 23.65921155 | 3.024504 | 2.023048 | 2.165421 | 7.109557 | 7.191402 | 6.587378 |
| GPR89A | 1.248674399 | 0.043453389 | 0.004665532 | 23.65921155 | 1.874444 | 2.023048 | 2.165421 | 5.891233 | 7.845161 | 6.587378 |
| HDAC11 | 1.179513077 | 0.043453389 | 0.006193335 | 23.65921155 | 3.350997 | 2.023048 | 2.165421 | 6.811341 | 7.174648 | 6.587378 |
| CRIPT | 1.171066747 | 0.043453389 | 0.006393331 | 23.62953761 | 2.993831 | 2.023048 | 3.324375 | 8.206677 | 7.066159 | 6.587378 |
| GPR155 | 1.281341803 | 0.043453389 | 0.004168765 | 23.60885295 | 3.839948 | 4.389936 | 3.90836 | 8.139755 | 8.579995 | 8.952456 |
| MED18 | 1.151729621 | 0.043453389 | 0.006828853 | 23.56230868 | 1.874444 | 2.023048 | 2.995681 | 7.556937 | 5.936219 | 6.587378 |
| GLT8D2 | 0.957806402 | 0.043835088 | 0.013535216 | 23.54320638 | 3.024504 | 2.809601 | 3.90836 | 5.448591 | 9.44338 | 7.582913 |
| TMSB10 | 1.263616916 | 0.043453389 | 0.004386526 | 23.54320638 | 7.730559 | 8.526827 | 8.589765 | 12.223349 | 13.084066 | 13.815308 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| CEP120 | 1.231317893 | 0.043453389 | 0.004958149 | 23.53445132 | 2.993831 | 2.023048 | 2.165421 | 6.664985 | 6.861783 | 6.722123 |
| GUSBP3 | 1.095976136 | 0.044349335 | 0.00836475 | 23.53445132 | 1.874444 | 2.023048 | 2.165421 | 5.095353 | 6.608026 | 6.722123 |
| LOC649395 | 0.889163887 | 0.044203301 | 0.01705342 | 23.52035554 | 6.736762 | 7.440099 | 6.737132 | 12.140187 | 11.292969 | 8.822008 |
| PLOD2 | 1.263438737 | 0.043453389 | 0.004393331 | 23.4558644 | 3.024504 | 3.32135 | 2.379345 | 8.270632 | 7.56803 | 6.931222 |
| KCNJ5 | 0.904184544 | 0.044173537 | 0.016219803 | 23.4558644 | 1.874444 | 2.023048 | 2.379345 | 4.013424 | 6.640994 | 6.931222 |
| SPG11 | 1.021646357 | 0.043577906 | 0.010960871 | 23.40601888 | 3.819732 | 3.32135 | 2.995681 | 8.433162 | 7.870158 | 6.051818 |
| KIF20B | 1.087081501 | 0.043516135 | 0.008709765 | 23.39534754 | 3.839948 | 2.023048 | 4.449894 | 6.811341 | 8.998044 | 8.194487 |
| LOC646999 | 1.152033513 | 0.043453389 | 0.006822048 | 23.36181394 | 4.263463 | 2.809601 | 2.995681 | 6.814118 | 8.181074 | 8.809543 |
| MTIF2 | 1.145688081 | 0.043453389 | 0.006951344 | 23.171432 | 2.993831 | 4.351315 | 2.165421 | 7.792994 | 7.53715 | 7.492252 |
| PSMA2 | 1.126665995 | 0.043453389 | 0.007427696 | 23.2475319 | 5.700376 | 4.736586 | 5.217616 | 10.325413 | 9.756621 | 8.519314 |
| KTN1 | 1.097868094 | 0.04349335 | 0.008269479 | 23.23771193 | 5.856559 | 4.389936 | 3.90836 | 10.515592 | 8.928336 | 8.269212 |
| H6PD | 0.816997509 | 0.045162628 | 0.020899626 | 23.21289741 | 6.58615 | 3.360637 | 2.379345 | 7.30543 | 8.220489 | 7.897492 |
| DPCD | 1.224892697 | 0.043453389 | 0.005087445 | 23.1891746B | 1.874444 | 2.023048 | 2.995681 | 7.531061 | 7.094585 | 6.129407 |
| LOC100507463 | 1.268755891 | 0.043453389 | 0.004291256 | 23.16947987 | 4.743564 | 4.736586 | 5.592916 | 9.220972 | 10.12707 | 9.50208 |
| DFNB59 | 1.248884911 | 0.043453389 | 0.004658727 | 23.07717768 | 1.874444 | 2.023048 | 2.165421 | 6.811341 | 6.551443 | 5.882028 |
| ALAS1 | 1.171121886 | 0.043453389 | 0.006386526 | 23.07717768 | 3.819732 | 2.023048 | 2.379345 | 7.976765 | 6.551443 | 7.46072 |
| WDR76 | 1.141200772 | 0.043453389 | 0.00709425 | 23.07717768 | 1.874444 | 2.023048 | 2.995681 | 5.320955 | 6.551443 | 6.942983 |
| VTCN1 | 1.035607373 | 0.043577906 | 0.010398775 | 23.07717768 | 3.819732 | 2.023048 | 2.165421 | 8.723321 | 6.551443 | 4.562324 |
| ATP13A5 | 0.949172623 | 0.043900827 | 0.013919701 | 23.07717768 | 1.874444 | 2.023048 | 2.165421 | 7.243046 | 6.551443 | 4.146207 |
| GCNT2 | 0.902248155 | 0.044190907 | 0.016357945 | 23.07717768 | 1.874444 | 2.023048 | 2.165421 | 8.069577 | 6.551443 | 3.676249 |
| MAP7D3 | 1.140714523 | 0.043453389 | 0.00712147 | 23.06512989 | 3.819732 | 2.023048 | 2.995681 | 6.550689 | 7.53715 | 8.25089 |
| PDE5A | 1.302298759 | 0.043453389 | 0.003889758 | 23.06171826 | 3.350997 | 2.023048 | 2.995681 | 7.450526 | 7.56803 | 7.523109 |
| CNTLN | 1.521129 | 0.043453389 | 0.006815243 | 23.06171826 | 3.024504 | 2.809601 | 2.995681 | 6.283686 | 7.845161 | 7.523109 |
| PDIA5 | 1.18414961 | 0.043453389 | 0.000680299 | 23.05346013 | 1.874444 | 2.023048 | 2.165421 | 8.768324 | 6.549959 | 5.580533 |
| TMEM156 | 1.140719187 | 0.043453389 | 0.007114665 | 23.05346013 | 1.874444 | 2.023048 | 2.165421 | 5.320955 | 6.549959 | 6.924055 |
| MTRNR2L6 | 1.113511115 | 0.043485739 | 0.007799251 | 23.05346013 | 1.874444 | 2.023048 | 2.165421 | 9.002943 | 6.549959 | 5.106393 |
| PTPN22 | 1.110853583 | 0.043485739 | 0.007887717 | 23.05346013 | 1.874444 | 2.023048 | 2.165421 | 7.877571 | 6.549959 | 5.091834 |
| RNF141 | 1.107560434 | 0.043485739 | 0.007976182 | 23.05346013 | 1.874444 | 2.023048 | 2.165421 | 7.450526 | 6.549959 | 5.091834 |
| C14orf133 | 0.939895687 | 0.043955231 | 0.014385846 | 23.05346013 | 1.874444 | 2.023048 | 2.165421 | 6.954147 | 6.549959 | 4.146207 |
| TCEAL3 | 0.783262576 | 0.045695042 | 0.023084723 | 23.05346013 | 1.874444 | 2.023048 | 2.165421 | 7.42265 | 6.549959 | 2.921909 |
| DHX29 | 1.209878241 | 0.043453389 | 0.005427696 | 23.02037138 | 3.819732 | 2.406905 | 2.165421 | 7.957464 | 7.845161 | 6.69026 |
| CMAHP | 1.193224533 | 0.043453389 | 0.005862538 | 23.02037138 | 2.201691 | 3.32135 | 2.165421 | 7.30543 | 7.845161 | 6.69026 |
| PCDHA9 | 1.250634511 | 0.043453389 | 0.004624702 | 23.00396157 | 2.993831 | 2.023048 | 2.995681 | 6.954147 | 7.845161 | 7.774634 |
| PPP1CA | 1.014377122 | 0.043581008 | 0.011293637 | 22.96869421 | 3.839948 | 2.023048 | 2.165421 | 8.361545 | 7.174648 | 5.446557 |
| C1QTNF3 | 1.279008286 | 0.043453389 | 0.004022279 | 22.96116086 | 1.874444 | 2.023048 | 2.379345 | 6.544171 | 6.189775 | 7.020304 |
| RIOK2 | 1.247866237 | 0.043485739 | 0.004672338 | 22.96116086 | 1.874444 | 2.023048 | 2.165421 | 6.544171 | 6.774676 | 5.882028 |
| CETN3 | 1.19302659 | 0.043453389 | 0.005876148 | 22.95978186 | 1.874444 | 2.023048 | 2.165421 | 6.395481 | 7.406567 | 8.784285 |
| C12orf35 | 1.179090721 | 0.043453389 | 0.00618918 | 22.95636454 | 4.263463 | 3.770995 | 2.379345 | 7.957464 | 7.31791 | 6.924055 |
| MTERFD1 | 1.161402762 | 0.043453389 | 0.006570262 | 22.950162 | 2.201691 | 2.023048 | 2.379345 | 7.144104 | 6.794431 | 5.446557 |
| TMEM55A | 0.950170014 | 0.043900827 | 0.01389248 | 22.80859486 | 6.186289 | 5.340619 | 5.225216 | 9.466036 | 10.697795 | 4.146207 |
| YEATS4 | 0.757736983 | 0.046414887 | 0.025004423 | 22.80173059 | 1.874444 | 2.023048 | 3.90836 | 6.651882 | 7.094585 | 2.921909 |
| LOC572558 | 1.353469445 | 0.043453389 | 0.003052739 | 22.78344152 | 1.874444 | 2.023048 | 2.995681 | 5.579836 | 7.505595 | 6.618407 |
| LOC729987 | 1.252239637 | 0.043453389 | 0.004590677 | 22.73764785 | 6.008206 | 6.42919 | 5.609945 | 9.188227 | 10.558612 | 8.784285 |
| OXNAD1 | 1.219809578 | 0.043453389 | 0.005196325 | 22.69516974 | 2.201691 | 4.80797 | 4.285996 | 8.79031 | 9.25691 | 6.722123 |
| FBXL13 | 1.25711159 | 0.043453389 | 0.004522627 | 22.80859486 | 6.186289 | 5.340619 | 5.225216 | 9.466036 | 10.697795 | 10.683012 |
| ZMYM5 | 1.049337581 | 0.043568903 | 0.009949643 | 22.80173059 | 1.874444 | 2.023048 | 3.90836 | 6.651882 | 7.094585 | 6.385515 |
| ATG3 | 1.145909948 | 0.043453389 | 0.006944539 | 22.78344152 | 1.874444 | 2.023048 | 2.995681 | 5.579836 | 7.505595 | 7.352555 |
| ANKK1 | 1.105381766 | 0.04349335 | 0.008038108 | 22.73764785 | 6.008206 | 6.42919 | 5.609945 | 9.188227 | 10.558612 | 10.936201 |
| MYSM1 | 1.254087593 | 0.043453389 | 0.004556652 | 22.69516974 | 2.201691 | 4.80797 | 4.285996 | 8.79031 | 9.25691 | 8.503924 |

TABLE 8-continued

Differentially Expressed Genes in CD10−, CD24−, CD44− Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| HES1 | 1.151707567 | 0.043453389 | 0.006835658 | 22.64704292 | 6.898923 | 4.80797 | 5.225216 | 11.400174 | 10.701282 | 9.163078 |
| H3F3C | 1.11487893 | 0.043485739 | 0.007744811 | 22.61524911 | 7.546975 | 6.044198 | 6.800663 | 12.522423 | 11.299887 | 10.112044 |
| ROR1 | 1.204467799 | 0.043453389 | 0.005509357 | 22.5945777 | 7.218633 | 6.502398 | 7.227914 | 10.67476 | 11.716537 | 11.789629 |
| POLR2B | 1.301024382 | 0.043453389 | 0.003923784 | 22.55572722 | 5.304463 | 4.830496 | 4.508334 | 9.799885 | 9.294336 | 9.276113 |
| CHCHD5 | 1.285369228 | 0.043453389 | 0.00413474 | 22.55457658 | 4.263463 | 3.360637 | 3.324375 | 8.41912 | 7.819723 | 8.732403 |
| ZNF117 | 1.057989887 | 0.043540291 | 0.009614154 | 22.52970593 | 3.350997 | 2.023048 | 4.754917 | 6.396698 | 8.402869 | 9.248674 |
| ELF3 | 0.931051292 | 0.044025007 | 0.014771011 | 22.50469941 | 4.263463 | 6.849665 | 3.90836 | 11.341819 | 9.158864 | 7.553321 |
| ZNF84 | 1.115063625 | 0.043485739 | 0.007738006 | 22.47087019 | 4.209882 | 4.389936 | 3.324375 | 7.210813 | 8.87992 | 8.732403 |
| COL7A1 | 1.246126711 | 0.043453389 | 0.004726778 | 22.45491538 | 1.874444 | 3.360637 | 2.165421 | 6.339437 | 7.793829 | 7.849596 |
| TECRL | 1.131394847 | 0.043453389 | 0.007305206 | 22.41607031 | 4.309025 | 2.406905 | 2.165421 | 6.651882 | 8.332658 | 7.695565 |
| FMO5 | 1.161055278 | 0.043453389 | 0.006697482 | 22.38212433 | 2.201691 | 3.872014 | 2.165421 | 7.477873 | 7.56803 | 6.649696 |
| LOC100130093 | 1.083397887 | 0.043516135 | 0.008829534 | 22.36116014 | 1.874444 | 2.809601 | 4.449894 | 7.243046 | 7.292524 | 7.640338 |
| PIM2 | 1.185715223 | 0.043453389 | 0.006046274 | 22.30822306 | 2.993831 | 3.360637 | 4.754917 | 9.137671 | 7.473335 | 8.564524 |
| PPP1R3B | 1.130144755 | 0.043453389 | 0.007346036 | 22.30822306 | 2.993831 | 4.413323 | 2.379345 | 8.447068 | 7.473335 | 7.218312 |
| NDUFS4 | 0.948026902 | 0.043900827 | 0.01398751 | 22.29643679 | 4.209882 | 2.023048 | 2.165421 | 8.688623 | 7.406567 | 5.091834 |
| APPL2 | 1.025993921 | 0.043577906 | 0.0107295 | 22.29283571 | 3.839948 | 4.351315 | 2.165421 | 6.283686 | 8.829823 | 8.32282 |
| MYOM2 | 1.00784184 | 0.043581008 | 0.011525009 | 22.27963156 | 1.874444 | 2.023048 | 2.995681 | 6.498222 | 7.167419 | 4.790662 |
| TCEAL8 | 1.330900548 | 0.043453389 | 0.003386186 | 22.24753286 | 1.874444 | 2.023048 | 5.018694 | 8.65307 | 9.532215 | 6.587378 |
| CMBL | 1.263152586 | 0.043453389 | 0.004406941 | 22.29643679 | 4.209882 | 2.023048 | 2.165421 | 8.239009 | 7.598264 | 6.129407 |
| FKBP14 | 1.165173956 | 0.043453389 | 0.006509017 | 22.24753286 | 2.201691 | 2.809601 | 2.165421 | 8.087444 | 6.640994 | 5.900694 |
| TTC13 | 1.304945821 | 0.043581008 | 0.011525009 | 22.24137525 | 1.874444 | 2.023048 | 2.995681 | 7.33564 | 6.640994 | 7.020304 |
| CDKAL1 | 1.153339676 | 0.043453389 | 0.006677413 | 22.13476986 | 4.743564 | 3.872014 | 5.018694 | 6.498222 | 7.473335 | 8.340256 |
| GORASP1 | 1.19006641 | 0.043453389 | 0.005978224 | 22.13126956 | 4.263463 | 3.770995 | 2.165421 | 8.239009 | 7.598264 | 8.287303 |
| C2orf42 | 1.245053909 | 0.043453389 | 0.004747193 | 22.0856739 | 1.874444 | 2.406421 | 2.995681 | 7.394225 | 6.319269 | 7.46072 |
| LOC444009 | 1.340949485 | 0.043453389 | 0.003222865 | 22.08498467 | 2.084984 | 2.023048 | 2.165421 | 6.339437 | 6.613395 | 6.587378 |
| ARHGAP10 | 1.298241949 | 0.043453389 | 0.003964614 | 22.08498467 | 2.084984 | 2.023048 | 2.165421 | 6.339437 | 6.373501 | 7.695565 |
| TRNAU1AP | 1.030477019 | 0.043577906 | 0.010562096 | 22.08498467 | 1.874444 | 2.023048 | 3.764125 | 6.339437 | 6.551443 | 6.649696 |
| FAM63B | 1.10606033 | 0.043493335 | 0.008024498 | 22.08468177 | 3.819732 | 2.809601 | 4.754917 | 7.274575 | 8.469827 | 8.745549 |
| SYNJ2BP | 1.217673594 | 0.043453389 | 0.005257571 | 22.04628173 | 4.309025 | 3.360637 | 3.324375 | 7.394225 | 8.59507 | 8.771488 |
| OSBPL8 | 1.0094965 | 0.043581008 | 0.011443348 | 22.03641419 | 5.316227 | 4.351315 | 4.449894 | 9.778045 | 8.97518 | 7.428484 |
| SFT2D1 | 1.046800881 | 0.043577906 | 0.010038789 | 21.98250773 | 4.209882 | 2.809601 | 2.165421 | 7.792994 | 8.668166 | 6.051818 |
| ABHD16A | 1.128444419 | 0.043453389 | 0.007373256 | 21.91687869 | 1.874444 | 3.360637 | 2.379345 | 7.814607 | 7.31791 | 5.874974 |
| PMPCA | 1.090664614 | 0.043516135 | 0.008587275 | 21.91687869 | 5.056948 | 2.023048 | 2.379345 | 7.814607 | 7.440337 | 9.220702 |
| RAB11FIP2 | 1.25564049 | 0.043453389 | 0.004534042 | 21.90773924 | 3.024504 | 2.023048 | 2.379345 | 7.477873 | 7.269549 | 6.455366 |
| MRPL24 | 1.103071753 | 0.043453389 | 0.008106159 | 21.90645386 | 4.682076 | 3.32135 | 2.165421 | 8.033165 | 7.505595 | 7.774634 |
| SCAMP1 | 1.107884556 | 0.043485739 | 0.0079557719 | 21.8843391 | 1.874444 | 2.406419 | 3.935222 | 8.105092 | 7.187136 | 6.32627 |
| TPD52 | 0.936912684 | 0.043994974 | 0.014494046 | 21.8843391 | 4.309025 | 3.770995 | 4.449894 | 9.847848 | 6.78473 | 6.32627 |
| LYPLAL1 | 1.322376639 | 0.043453389 | 0.003535897 | 21.85954701 | 2.201691 | 2.406905 | 2.165421 | 6.651882 | 8.97518 | 6.587378 |
| SH3KBP1 | 1.062286614 | 0.043453389 | 0.009454859 | 21.85212054 | 1.878736275 | 2.809601 | 3.764125 | 7.771052 | 8.696398 | 8.374509 |
| GBP6 | 1.073147113 | 0.043516135 | 0.009169786 | 21.82597742 | 2.201691 | 2.023048 | 2.165421 | 5.026959 | 6.613395 | 7.395512 |
| IL17RB | 0.852596969 | 0.044464174 | 0.018724736 | 21.82597742 | 1.874444 | 2.023048 | 2.165421 | 6.498222 | 6.613395 | 3.676349 |
| CSRP2 | 0.912965448 | 0.044110923 | 0.015714188 | 21.80377418 | 1.803774184 | 2.023048 | 2.165421 | 4.341916 | 7.440337 | 7.03218 |
| GUCY1B3 | 1.04705003 | 0.043577906 | 0.010031984 | 21.7997463 | 3.839948 | 2.406421 | 2.165421 | 8.286188 | 7.406567 | 5.580533 |
| FAM36A | 1.183445161 | 0.043453389 | 0.006087104 | 21.78736275 | 4.743564 | 5.297868 | 4.508334 | 10.344114 | 9.188984 | 8.534542 |
| PLAT | 1.08313585 | 0.043516135 | 0.008849949 | 21.76011776 | 5.263699 | 3.770995 | 4.508334 | 10.671802 | 8.951948 | 7.611911 |
| LOC100288198 | 1.276806347 | 0.043453389 | 0.004209595 | 21.74490341 | 1.874444 | 2.023048 | 2.165421 | 6.498222 | 6.608026 | 6.051818 |
| MLPH | 0.863856913 | 0.043377262 | 0.018178292 | 21.67698395 | 6.275577 | 3.770995 | 4.285996 | 10.780147 | 8.724089 | 6.73963 |
| B3GALNT1 | 1.249034959 | 0.043453389 | 0.004651922 | 21.62717945 | 2.201691 | 2.406905 | 2.379345 | 6.814118 | 7.292524 | 6.195186 |
| LIMA1 | 0.932357659 | 0.044025007 | 0.014709765 | 21.62717945 | 1.874444 | 5.487673 | 2.379345 | 6.814118 | 8.998044 | 6.73963 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| MAGI2-AS3 | 1.149391051 | 0.043453389 | 0.006876489 | 21.59666179 | 4.963444 | 4.389936 | 6.012527 | 8.822673 | 9.789758 | 9.910841 |
| KIAA0907 | 1.143342564 | 0.043453389 | 0.007026199 | 21.59098171 | 1.874444 | 3.360637 | 2.379345 | 7.792994 | 7.56803 | 5.882028 |
| LOC550643 | 1.048553766 | 0.043577906 | 0.009991153 | 21.59040227 | 4.263463 | 2.023048 | 2.165421 | 7.30543 | 7.292524 | 6.455366 |
| DHFR | 1.140539091 | 0.043453389 | 0.007141885 | 21.51224679 | 3.350997 | 4.389936 | 4.944468 | 7.856887 | 8.817023 | 9.123341 |
| ZBED5 | 1.094317809 | 0.04349335 | 0.0084328 | 21.47217083 | 4.639409 | 2.406905 | 3.324375 | 7.748771 | 8.2398 | 7.291822 |
| STS | 1.220772879 | 0.043453389 | 0.005182715 | 21.43589975 | 1.874444 | 2.809601 | 2.165421 | 6.395481 | 6.78473 | 6.587378 |
| TAF6 | 0.95119662 | 0.043900827 | 0.013855165 | 21.43589975 | 5.263699 | 2.809601 | 2.165421 | 7.835902 | 8.011679 | 6.587378 |
| DNAJB4 | 1.10081803 | 0.04349335 | 0.008201429 | 21.41104943 | 3.839948 | 3.360637 | 5.217616 | 9.23707 | 9.637899 | 7.255535 |
| NPHP3 | 1.200838175 | 0.043453389 | 0.005638653 | 21.41063031 | 2.993831 | 2.023048 | 2.165421 | 6.664985 | 7.414086 | 6.32627 |
| PROS1 | 0.970877493 | 0.043709154 | 0.012956108 | 21.41063031 | 2.993831 | 2.406905 | 3.935222 | 5.579836 | 7.414086 | 8.650903 |
| FBXL3 | 1.004374061 | 0.043588662 | 0.0116877649 | 21.35817204 | 2.201691 | 2.406905 | 5.018694 | 7.477873 | 8.402869 | 6.618407 |
| HIBADH | 1.213528619 | 0.043453389 | 0.005339231 | 21.34509478 | 3.024504 | 3.32135 | 2.379345 | 8.014609 | 7.440337 | 6.722123 |
| SCAPER | 1.053208768 | 0.043568903 | 0.009820347 | 21.33405473 | 4.263463 | 2.023048 | 2.379345 | 7.814607 | 6.794431 | 6.722123 |
| PVRL4 | 0.882367895 | 0.044229452 | 0.017338551 | 21.33405473 | 1.874444 | 4.413323 | 2.379345 | 8.885299 | 6.794431 | 5.091834 |
| CSRNP2 | 1.128364492 | 0.043453389 | 0.007386866 | 21.27285194 | 3.839948 | 2.406905 | 4.508334 | 7.36523 | 8.453372 | 8.25089 |
| BRP44 | 1.25909785 | 0.043453389 | 0.004468186 | 21.26659501 | 5.056948 | 4.80797 | 2.995681 | 9.252991 | 9.218487 | 9.051056 |
| DPYD | 1.076566114 | 0.043516135 | 0.009060905 | 21.24781347 | 1.874444 | 2.023048 | 4.449894 | 6.283686 | 8.486085 | 7.395512 |
| ZNF26 | 1.179547641 | 0.043453389 | 0.00617557 | 21.23998086 | 2.993831 | 2.809601 | 2.379345 | 6.283686 | 7.414086 | 7.21312 |
| SLC24A4 | 1.255898831 | 0.043540291 | 0.004536237 | 21.17714343 | 2.993831 | 2.406905 | 2.165421 | 6.811341 | 6.78473 | 7.180104 |
| KCTD3 | 1.022241988 | 0.043577906 | 0.010947261 | 21.15034203 | 2.201691 | 3.770995 | 2.165421 | 8.173604 | 7.107836 | 5.580533 |
| MFAP1 | 1.017234996 | 0.043581008 | 0.011157537 | 21.13798314 | 2.201691 | 2.023048 | 3.324375 | 7.726141 | 7.406567 | 5.091834 |
| LOC100506710 | 1.03147008 | 0.043577906 | 0.010528071 | 21.10965547 | 5.304463 | 3.360637 | 2.995681 | 8.79031 | 8.011679 | 7.395512 |
| CNNM2 | 1.182598819 | 0.043516135 | 0.00610752 | 21.07156548 | 7.198002 | 7.197097 | 7.107458 | 10.752415 | 11.594323 | 11.64277 |
| KRT8 | 1.029676591 | 0.043577906 | 0.010568901 | 21.02626007 | 3.350997 | 5.809601 | 3.324375 | 10.203722 | 8.402869 | 7.428484 |
| RAB42 | 1.19698114 | 0.043453389 | 0.005767268 | 21.02202167 | 4.963444 | 6.466258 | 6.056062 | 9.847848 | 10.589051 | 10.449891 |
| GBA2 | 1.162542767 | 0.043453389 | 0.006556652 | 20.96022135 | 3.024504 | 3.872014 | 2.165421 | 8.014609 | 7.414086 | 6.931222 |
| AKAP7 | 1.061857776 | 0.043540291 | 0.009491664 | 20.93037391 | 1.874444 | 2.406905 | 2.165421 | 6.651882 | 6.794431 | 5.091834 |
| ABHD14A | 1.28832932 | 0.043453389 | 0.004100715 | 20.90856097 | 2.201691 | 2.023048 | 2.165421 | 6.252746 | 6.551443 | 7.352555 |
| CXorf26 | 0.977493102 | 0.043661316 | 0.012646478 | 20.90856097 | 2.201691 | 2.023048 | 2.165421 | 6.544171 | 6.551443 | 4.476242 |
| LEO1 | 0.75724389 | 0.046424242 | 0.025024158 | 20.90856097 | 1.874444 | 2.809601 | 2.165421 | 8.447068 | 6.551443 | 2.921909 |
| CKLF | 1.081303605 | 0.043516135 | 0.008904389 | 20.90371112 | 2.201691 | 2.023048 | 3.90836 | 7.877571 | 6.551443 | 6.587378 |
| IPO11 | 1.119005761 | 0.043485739 | 0.007615515 | 20.89764534 | 2.201691 | 2.023048 | 2.165421 | 6.660689 | 6.363925 | 3.961222 |
| TADA3 | 1.101278571 | 0.04349335 | 0.008174209 | 20.89764534 | 3.839948 | 3.872014 | 2.165421 | 6.550689 | 7.989035 | 9.008063 |
| APTX | 1.24183747 | 0.043453389 | 0.004788023 | 20.88707221 | 2.201691 | 2.023048 | 2.165421 | 7.976765 | 6.549959 | 6.051818 |
| RNLS | 1.13918867 | 0.043453389 | 0.007182715 | 20.88707221 | 2.201691 | 2.023048 | 2.165421 | 7.856887 | 6.549959 | 5.426231 |
| SVIP | 1.121333981 | 0.043480953 | 0.007569241 | 20.88707221 | 3.024504 | 2.406905 | 2.165421 | 8.974419 | 6.549959 | 5.882028 |
| ASH2L | 1.09321024 | 0.04349335 | 0.008480436 | 20.88707221 | 2.201691 | 2.809601 | 2.165421 | 5.252045 | 6.549959 | 6.69026 |
| NSMCE4A | 1.127984451 | 0.043453389 | 0.007393671 | 20.80344652 | 1.874444 | 3.32135 | 4.944468 | 6.544171 | 7.107836 | 6.32627 |
| CXorf23 | 1.007593043 | 0.043581008 | 0.011538619 | 20.80344652 | 2.201691 | 2.023048 | 6.282905 | 10.852466 | 6.640994 | 4.790662 |
| LRIG3 | 0.963881502 | 0.043778104 | 0.013214269 | 20.80344652 | 1.874444 | 2.406905 | 5.018694 | 8.156778 | 7.138979 | 4.476242 |
| IDH2 | 1.072214024 | 0.043516135 | 0.009197006 | 20.79785347 | 5.316227 | 4.750708 | 4.724406 | 10.302647 | 7.740604 | 6.385515 |
| ANKS1B | 1.012247532 | 0.043581008 | 0.011375298 | 20.77592572 | 6.186289 | 3.872014 | 4.944468 | 9.693068 | 9.409671 | 7.395512 |
| RAB1A | 1.054081527 | 0.043568903 | 0.009799932 | 20.7661745 | 5.056948 | 6.049721 | 6.282905 | 10.852466 | 10.562453 | 9.072081 |
| CTBS | 1.016957613 | 0.043581008 | 0.011171147 | 20.73033449 | 2.201691 | 3.32135 | 5.018694 | 8.156778 | 7.91889 | 9.430619 |
| RP9P | 1.019143444 | 0.043577906 | 0.011090167 | 20.73002377 | 1.874444 | 2.023048 | 3.935222 | 6.396698 | 7.174648 | 6.32627 |
| GATA3 | 1.115838352 | 0.043485739 | 0.007710786 | 20.729099 | 3.839948 | 5.362142 | 4.724406 | 10.302647 | 8.777924 | 8.213534 |
| SIRT5 | 1.284826826 | 0.043453389 | 0.004141545 | 20.71254249 | 1.874444 | 2.023048 | 2.165421 | 6.395481 | 6.613395 | 6.129407 |
| P4HA2 | 1.148177474 | 0.043453389 | 0.006910514 | 20.71254249 | 1.874444 | 2.023048 | 2.165421 | 6.395481 | 6.78473 | 5.426231 |
| LPHN3 | 1.139875825 | 0.043453389 | 0.00717591 | 20.71254249 | 1.874444 | 2.023048 | 2.165421 | 6.395481 | 5.353925 | 7.291822 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| DNM1P35 | 1.132212428 | 0.043453389 | 0.007284791 | 20.71254249 | 3.350997 | 2.023048 | 2.165421 | 6.395481 | 6.640994 | 7.033813 |
| LRTM2 | 1.096873569 | 0.04349335 | 0.008330725 | 20.71254249 | 1.874444 | 2.023048 | 2.165421 | 6.395481 | 7.292524 | 5.106393 |
| RARB | 1.080631367 | 0.043516135 | 0.008945219 | 20.68485257 | 3.839948 | 2.809601 | 2.165421 | 6.244586 | 8.518072 | 7.180104 |
| TMEM237 | 1.199436956 | 0.043453389 | 0.005706703 | 20.67969012 | 1.874444 | 2.809601 | 2.165421 | 6.244586 | 7.269549 | 6.455366 |
| KIT | 1.022370647 | 0.043577906 | 0.010940456 | 20.67927292 | 4.209882 | 4.351315 | 3.324375 | 10.321643 | 8.579995 | 6.455366 |
| NFYC | 1.195031766 | 0.043453389 | 0.005814903 | 20.67692246 | 3.024504 | 2.406905 | 3.935222 | 7.30543 | 7.31791 | 8.305171 |
| ZNF622 | 1.110659104 | 0.043485739 | 0.007894522 | 20.66820086 | 4.209882 | 2.406905 | 3.764125 | 8.579223 | 7.870158 | 7.03218 |
| SRA1 | 0.985128705 | 0.043626235 | 0.012361347 | 20.66820086 | 4.209882 | 2.023048 | 2.165421 | 8.579223 | 6.640994 | 5.882028 |
| ATF6 | 1.000114757 | 0.043588662 | 0.011844165 | 20.62567356 | 5.779429 | 4.736586 | 2.379345 | 9.102956 | 9.1177 | 7.695565 |
| MMAB | 1.027196216 | 0.043577906 | 0.010681865 | 20.59504363 | 6.898923 | 4.389936 | 6.282905 | 9.252991 | 9.956624 | 11.263149 |
| EPCAM | 0.956974648 | 0.043835088 | 0.015576046 | 20.59168372 | 3.819732 | 3.32135 | 2.165421 | 10.492308 | 7.68534 | 5.091834 |
| ACYP2 | 1.092819971 | 0.04349335 | 0.008494046 | 20.57773238 | 1.874444 | 2.406905 | 3.764125 | 7.877571 | 6.237456 | 6.931222 |
| NREP | 1.188300114 | 0.043453389 | 0.006005444 | 20.56996084 | 3.839948 | 2.023048 | 2.165421 | 7.856887 | 8.140553 | 6.385515 |
| TF | 1.131628078 | 0.043453389 | 0.007298401 | 20.56996084 | 1.874444 | 2.023048 | 2.165421 | 7.631894 | 5.306419 | 6.385515 |
| CCDC23 | 1.060574149 | 0.043540291 | 0.009525689 | 20.56996084 | 4.209882 | 2.023048 | 2.165421 | 7.167419 | 7.656894 | 6.385515 |
| MOV10 | 0.987570112 | 0.043626235 | 0.012272882 | 20.53887792 | 2.201691 | 2.406905 | 2.379345 | 4.802615 | 7.191402 | 6.73963 |
| RFC2 | 1.182203662 | 0.043453389 | 0.006127935 | 20.50377435 | 1.874444 | 2.809601 | 3.324375 | 7.167419 | 6.640994 | 7.327219 |
| IL23R | 0.97524481 | 0.043661316 | 0.012734944 | 20.50377435 | 5.335413 | 2.809601 | 5.596986 | 7.167419 | 9.563208 | 10.214881 |
| MRPL3 | 1.149278427 | 0.043453389 | 0.006883294 | 20.43692117 | 4.743564 | 4.389936 | 2.379345 | 8.286188 | 9.09667 | 8.03232 |
| SUMF1 | 1.169405213 | 0.043453389 | 0.000640966 | 20.4297469 | 1.874444 | 3.360637 | 2.165421 | 7.037879 | 7.713236 | 6.195186 |
| MIR4454 | 1.197697024 | 0.043453389 | 0.005747533 | 20.3993743 | 1.874444 | 2.023048 | 2.165421 | 5.705318 | 6.373501 | 6.587378 |
| FANCM | 1.155981546 | 0.043453389 | 0.006719973 | 20.3993743 | 1.874444 | 2.023048 | 2.995681 | 6.664985 | 6.373501 | 6.32627 |
| RPA3 | 1.149755588 | 0.043453389 | 0.006869684 | 20.3993743 | 1.874444 | 2.023048 | 2.165421 | 7.877571 | 6.373501 | 5.426231 |
| OPRM1 | 1.069158738 | 0.043516135 | 0.009299081 | 20.3993743 | 2.201691 | 2.406905 | 2.165421 | 5.026939 | 6.373501 | 6.649696 |
| IQCF3 | 0.960220128 | 0.043802358 | 0.013379381 | 20.38946458 | 2.201691 | 2.406905 | 2.165421 | 4.341916 | 6.373501 | 6.924055 |
| PIGX | 1.229453629 | 0.043453389 | 0.004985369 | 20.38631556 | 5.304463 | 2.406905 | 2.165421 | 7.33564 | 6.551443 | 6.129407 |
| MYO6 | 1.015479636 | 0.043581008 | 0.011218782 | 20.38631556 | 4.682076 | 5.661685 | 3.324375 | 10.011214 | 8.119857 | 8.175185 |
| TFCP2L1 | 1.219575506 | 0.043453389 | 0.00521674 | 20.37881995 | 2.201691 | 2.406905 | 3.324375 | 6.550689 | 7.292524 | 7.611911 |
| OLFML2A | 0.822433615 | 0.045030324 | 0.020587955 | 20.37881995 | 2.201691 | 3.770995 | 5.544653 | 6.550689 | 9.99691 | 6.618407 |
| MYD88 | 1.219677889 | 0.043453389 | 0.00520313 | 20.36850932 | 2.201691 | 2.023048 | 2.379345 | 8.069577 | 6.549959 | 6.051818 |
| DPH3 | 1.093824775 | 0.04349335 | 0.008453215 | 20.35577471 | 4.815804 | 3.770995 | 2.995681 | 9.16317 | 8.200916 | 7.291822 |
| GEM | 0.99698263 | 0.043626235 | 0.011938074 | 20.3529917 | 5.304463 | 6.139057 | 7.809663 | 9.651632 | 10.905551 | 10.880675 |
| SCUBE2 | 0.939618499 | 0.043955231 | 0.014392651 | 20.34870405 | 1.874444 | 3.32135 | 6.355801 | 9.388882 | 7.656894 | 7.668215 |
| C1QTNF2 | 0.71652796 | 0.047853797 | 0.028232732 | 20.29114353 | 1.874444 | 2.023048 | 2.379345 | 2.820813 | 6.373501 | 6.722123 |
| PLCG2 | 1.049089858 | 0.043568903 | 0.009956448 | 20.2869598 | 1.874444 | 2.406905 | 2.165421 | 6.544171 | 5.165949 | 6.924055 |
| HTR2A | 1.167811651 | 0.043453389 | 0.006325281 | 20.12013724 | 6.417969 | 5.340619 | 6.054038 | 10.174762 | 11.162428 | 9.676959 |
| SACM1L | 1.040558281 | 0.043577906 | 0.008276284 | 20.06641628 | 6.099991 | 8.819674 | 7.462086 | 7.835902 | 7.656894 | 6.618407 |
| IL33 | 1.023219628 | 0.043577906 | 0.010906431 | 20.18965012 | 4.309025 | 2.023048 | 3.324375 | 6.244586 | 7.656894 | 8.705744 |
| ENY2 | 1.079167605 | 0.043516135 | 0.008992855 | 20.13543034 | 4.682076 | 2.023048 | 3.324375 | 7.656039 | 7.76462 | 7.553321 |
| TMEM14A | 1.194985779 | 0.043453389 | 0.005837108 | 20.1336666 | 1.874444 | 3.770995 | 2.995681 | 7.274575 | 7.627877 | 7.327219 |
| CRTAM | 1.108430436 | 0.043485739 | 0.007948962 | 20.12089333 | 1.874444 | 3.32135 | 4.285996 | 8.616619 | 7.191402 | 7.218312 |
| C15orf34 | 1.172909757 | 0.043453389 | 0.006325281 | 20.12013724 | 4.209882 | 5.148082 | 5.702912 | 9.058353 | 9.500541 | 9.478651 |
| ANXA1 | 1.097821099 | 0.04349335 | 0.008276284 | 20.06641628 | 6.099991 | 8.819674 | 7.462086 | 12.826968 | 11.788797 | 11.358224 |
| METTL10 | 1.086679873 | 0.043516135 | 0.008723375 | 20.02983597 | 2.993831 | 2.023048 | 3.324375 | 8.301578 | 7.31791 | 5.874974 |
| SERPINA1 | 0.888229908 | 0.044203301 | 0.017114665 | 20.02863005 | 3.839948 | 4.911517 | 4.285996 | 11.771561 | 8.609988 | 5.874974 |
| GNG5 | 1.057261832 | 0.043540291 | 0.009668595 | 19.99626604 | 5.982974 | 4.830496 | 5.544653 | 10.834062 | 9.866312 | 8.391335 |
| RFXAP | 1.288768809 | 0.043453389 | 0.000480299 | 19.9835652 | 1.874444 | 2.023048 | 2.165421 | 6.544171 | 6.319269 | 6.195186 |
| GGH | 1.263037625 | 0.043453389 | 0.004413746 | 19.9835652 | 1.874444 | 2.023048 | 2.165421 | 7.42265 | 6.237456 | 6.195186 |
| PYROXD2 | 1.240993728 | 0.043453389 | 0.004808438 | 19.9835652 | 1.874444 | 2.023048 | 2.379345 | 6.283686 | 7.598264 | 6.195186 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| KIAA0528 | 1.231548362 | 0.043453389 | 0.004951344 | 19.9835652 | 1.874444 | 2.406905 | 2.165421 | 6.339437 | 7.68534 | 6.195486 |
| HSPE1 | 0.956380122 | 0.043840967 | 0.013607349 | 19.98349795 | 6.678389 | 7.939256 | 7.575421 | 12.581933 | 11.896158 | 9.697401 |
| SMC5 | 1.190954715 | 0.043453389 | 0.005964614 | 19.96893779 | 4.639409 | 3.770995 | 3.935222 | 8.254907 | 8.65384 | 8.095288 |
| SNRPG | 0.83044419 | 0.044867325 | 0.020059884 | 19.93289759 | 5.056948 | 4.736586 | 4.449894 | 10.191381 | 9.053666 | 6.106561 |
| PTER | 1.171711187 | 0.043453389 | 0.006372916 | 19.92336801 | 1.874444 | 2.023048 | 2.165421 | 6.339437 | 6.640994 | 5.580533 |
| RNASE6 | 0.980367976 | 0.043626235 | 0.012558693 | 19.92336801 | 1.874444 | 2.023048 | 2.165421 | 6.339437 | 6.205902 | 6.73963 |
| C9orf3 | 0.921826003 | 0.044110923 | 0.015268459 | 19.91756292 | 4.309025 | 5.297868 | 4.285996 | 6.814118 | 8.892178 | 9.613837 |
| LYRM7 | 1.050342722 | 0.043568903 | 0.009922423 | 19.91753306 | 4.682076 | 2.809601 | 5.018694 | 7.33564 | 8.998044 | 9.211256 |
| GPX7 | 1.082214597 | 0.043516135 | 0.008870364 | 19.90719656 | 4.309025 | 2.406905 | 2.995681 | 7.835902 | 7.819723 | 6.722123 |
| CD46 | 1.153439298 | 0.043453389 | 0.008760803 | 19.88226484 | 6.186289 | 3.03611 | 4.944468 | 10.862879 | 10.343377 | 9.257878 |
| ANKRD26 | 1.097397861 | 0.043453389 | 0.008303505 | 19.84790949 | 3.350997 | 2.023048 | 2.379345 | 7.726141 | 6.043524 | 6.69026 |
| ESYT2 | 1.200309661 | 0.043453389 | 0.005686288 | 19.79837935 | 3.350997 | 3.770995 | 4.449894 | 8.757204 | 8.624754 | 7.582913 |
| LINC00221 | 0.98072241 | 0.043626235 | 0.012545083 | 19.78762072 | 1.874444 | 3.32135 | 2.165421 | 4.802615 | 7.627877 | 7.395512 |
| LOC100507600 | 1.266177522 | 0.043453389 | 0.004352501 | 19.74236107 | 1.874444 | 2.023048 | 2.165421 | 6.067497 | 6.08026 | 6.32627 |
| GIMAP4 | 1.231743293 | 0.043453389 | 0.004944539 | 19.74236107 | 1.874444 | 2.023048 | 2.165421 | 5.891233 | 6.608026 | 6.32627 |
| CAP2 | 1.212193906 | 0.043453389 | 0.005373256 | 19.74236107 | 1.874444 | 2.023048 | 2.165421 | 8.566539 | 5.920411 | 6.32627 |
| ATP6AP2 | 1.011380456 | 0.043581008 | 0.011402518 | 19.74236107 | 4.682076 | 2.023048 | 3.76125 | 9.60897 | 8.055928 | 6.323627 |
| N4BP2L1 | 1.112490718 | 0.043485739 | 0.007826472 | 19.73651413 | 3.819732 | 3.32135 | 2.165421 | 8.122528 | 7.094585 | 6.924055 |
| RASA1 | 1.028919422 | 0.043577906 | 0.010613814 | 19.72002953 | 5.328526 | 3.872014 | 2.995681 | 8.173604 | 8.277663 | 7.849596 |
| SULT1A1 | 1.136237798 | 0.043453389 | 0.007223545 | 19.69770527 | 3.839948 | 2.809601 | 3.935222 | 7.109557 | 7.767462 | 8.758577 |
| TRERF1 | 1.00488519 | 0.043588662 | 0.011660429 | 19.69770527 | 2.993831 | 2.809601 | 4.724406 | 7.109557 | 7.713236 | 7.352555 |
| LAMTOR1 | 1.072966029 | 0.043516135 | 0.009176591 | 19.69268718 | 5.856559 | 4.351315 | 2.379345 | 8.616619 | 8.97518 | 8.650903 |
| COPB2 | 0.971682926 | 0.043681142 | 0.012920041 | 19.65890821 | 6.306772 | 4.830496 | 3.935222 | 9.322536 | 9.179013 | 8.232333 |
| KIAA0564 | 1.262501049 | 0.043453389 | 0.004427356 | 19.6467864 | 1.874444 | 2.023048 | 2.165421 | 7.504712 | 6.319269 | 6.129407 |
| CD247 | 1.200428549 | 0.043453389 | 0.005679483 | 19.6467864 | 1.874444 | 2.023048 | 2.165421 | 5.728038 | 6.319269 | 6.931222 |
| ZNF138 | 1.182505218 | 0.043453389 | 0.006114325 | 19.6467864 | 1.874444 | 2.023048 | 2.165421 | 5.728038 | 6.319269 | 6.931222 |
| HPRT1 | 1.144861288 | 0.043453389 | 0.006985369 | 19.6467864 | 1.874444 | 2.023048 | 2.165421 | 7.748771 | 6.319269 | 5.426231 |
| SNORA78 | 1.141656924 | 0.043453389 | 0.00706703 | 19.6467864 | 1.874444 | 2.023048 | 2.995681 | 6.063041 | 6.319269 | 7.553321 |
| SNTB1 | 1.09377877 | 0.04349335 | 0.00846002 | 19.6467864 | 1.874444 | 2.023048 | 2.165421 | 8.361545 | 6.319269 | 5.106393 |
| ABCA13 | 0.840786271 | 0.044709815 | 0.019450834 | 19.6467864 | 1.874444 | 2.023048 | 2.165421 | 6.544171 | 6.319269 | 3.676349 |
| LOC646214 | 1.134958042 | 0.043453389 | 0.007237155 | 19.60392616 | 8.55164 | 8.491292 | 8.693844 | 11.982016 | 13.005848 | 12.844711 |
| FAM102B | 0.78253485 | 0.045701235 | 0.023138482 | 19.5560358 | 4.263463 | 2.023048 | 3.324375 | 8.553743 | 8.119857 | 4.146207 |
| ITIH4 | 1.236080159 | 0.043453389 | 0.004869684 | 19.56150134 | 1.874444 | 2.023048 | 2.165421 | 6.339437 | 5.920411 | 6.455366 |
| TDP1 | 1.211473047 | 0.043453389 | 0.005407281 | 19.56150134 | 2.201691 | 2.023048 | 2.165421 | 5.891233 | 7.473335 | 6.455366 |
| PIGM | 1.169458941 | 0.043453389 | 0.006427356 | 19.56150134 | 2.201691 | 3.360637 | 2.165421 | 6.811341 | 7.627877 | 6.453666 |
| ATG5 | 0.912189522 | 0.044142622 | 0.015754338 | 19.56150134 | 5.056948 | 2.406905 | 2.165421 | 7.177844 | 7.505595 | 6.455366 |
| LOC100500773 | 1.234168281 | 0.043453389 | 0.004924124 | 19.54991374 | 8.051258 | 7.458616 | 7.913913 | 12.203003 | 12.218027 | 11.795962 |
| KIAA0040 | 1.154245989 | 0.043453389 | 0.006747193 | 19.5210601 | 2.993831 | 4.413323 | 5.225216 | 8.700282 | 8.469821 | 8.952456 |
| IFT172 | 1.008842476 | 0.043588662 | 0.011667234 | 19.50792269 | 2.201691 | 3.32135 | 5.217616 | 7.607339 | 7.269549 | 8.456743 |
| SLC19A3 | 1.066391205 | 0.043516135 | 0.009367132 | 19.49434474 | 4.263463 | 2.809601 | 3.90836 | 6.283686 | 7.094585 | 8.010706 |
| FLJ30838 | 0.99232907 | 0.043626235 | 0.012116366 | 19.49434474 | 1.874444 | 2.809601 | 3.324375 | 5.252045 | 7.094585 | 7.327219 |
| C14orf101 | 1.083321605 | 0.043516135 | 0.008843144 | 19.38559577 | 4.309025 | 3.32135 | 2.165421 | 6.814118 | 7.598261 | 8.357484 |
| MMRN2 | 1.221133942 | 0.043453389 | 0.00517591 | 19.34471928 | 5.056948 | 4.750708 | 5.571599 | 9.196483 | 9.330816 | 9.750536 |
| PSMB1 | 1.170873288 | 0.043453389 | 0.006406941 | 19.33721294 | 6.648293 | 4.911517 | 5.723602 | 9.978073 | 9.99691 | 10.520428 |
| LRIF1 | 1.249543553 | 0.043453389 | 0.004645117 | 19.29761994 | 1.874444 | 2.023048 | 2.379345 | 6.063041 | 6.549959 | 6.649696 |
| BIVM | 1.141320636 | 0.043453389 | 0.00708064 | 19.29761994 | 2.993831 | 2.023048 | 2.379345 | 6.067497 | 7.269549 | 6.649696 |
| LRP11 | 1.006391205 | 0.044592081 | 0.019004423 | 19.24056029 | 2.993831 | 2.809601 | 2.165421 | 7.25991 | 7.656894 | 4.476242 |
| LMO7 | 0.872670666 | 0.044299467 | 0.017744811 | 19.22033256 | 1.874444 | 2.809601 | 2.165421 | 7.074163 | 6.551443 | 4.146207 |
| LOC283585 | 1.096332721 | 0.04349335 | 0.00835114 | 19.21590049 | 1.874444 | 2.023048 | 2.995681 | 7.25991 | 6.551443 | 5.634184 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA-N171 | BRCA1-N174 |
|---|---|---|---|---|---|---|---|---|---|---|
| MINOS1 | 1.150081551 | 0.043453389 | 0.006856073 | 19.20986307 | 5.056948 | 3.872014 | 4.449894 | 9.98762 | 8.63937 | 8.135789 |
| OAF | 0.870981499 | 0.044325295 | 0.017831916 | 19.20160099 | 4.309025 | 5.297868 | 4.508334 | 6.544171 | 9.985514 | 8.771488 |
| NCBP2 | 1.030836164 | 0.043577906 | 0.010541681 | 19.19034259 | 4.639409 | 4.830496 | 2.379345 | 7.36523 | 8.258856 | 9.092804 |
| HOXD8 | 1.057943224 | 0.043540291 | 0.009627765 | 19.18157667 | 1.874444 | 2.023048 | 2.379345 | 5.026959 | 6.640994 | 6.618407 |
| UQCRC2 | 1.217839329 | 0.043453389 | 0.005250766 | 19.17901973 | 5.335413 | 4.736586 | 4.508334 | 9.45919 | 8.998044 | 8.986077 |
| PTPN21 | 1.191306876 | 0.043453389 | 0.005937394 | 19.17585071 | 2.993831 | 2.023048 | 2.165421 | 6.814118 | 7.25505 | 6.195186 |
| IPO8 | 1.2595572 | 0.043453389 | 0.004461381 | 19.16813679 | 1.874444 | 2.023048 | 2.165421 | 6.283686 | 7.414086 | 6.129407 |
| KIAA1009 | 1.082366215 | 0.043516135 | 0.008863559 | 19.16813679 | 2.993831 | 2.023048 | 4.449894 | 6.283686 | 8.486085 | 8.488368 |
| SNRPF | 1.123147798 | 0.043453389 | 0.007495747 | 19.15771161 | 3.839948 | 4.389936 | 2.995681 | 8.460842 | 8.2398 | 7.255535 |
| HSF2 | 1.097998315 | 0.04349335 | 0.008249064 | 19.15127384 | 3.024504 | 2.023048 | 2.995681 | 7.556937 | 7.25505 | 5.882028 |
| LIN28A | 0.910420501 | 0.044159136 | 0.015189248 | 19.15127384 | 4.815804 | 2.023048 | 2.995681 | 6.339437 | 7.25505 | 7.492252 |
| WDR33 | 1.227821619 | 0.043453389 | 0.005026199 | 19.14204453 | 4.743564 | 4.351315 | 4.944468 | 9.452312 | 8.609988 | 8.974957 |
| MAGI1 | 1.055590879 | 0.043540291 | 0.009750255 | 19.09786014 | 3.839948 | 3.770995 | 2.379345 | 6.857154 | 7.174648 | 8.095288 |
| ZNF184 | 1.26741054 | 0.043453389 | 0.004332086 | 19.09289409 | 1.874444 | 2.023048 | 2.165421 | 6.498222 | 6.237456 | 6.129407 |
| UNC13B | 1.113073689 | 0.043485739 | 0.007812862 | 19.09289409 | 1.874444 | 2.023048 | 2.165421 | 6.664985 | 7.094585 | 6.129407 |
| SRPK2 | 0.953574578 | 0.043857532 | 0.013735965 | 19.09289409 | 1.874444 | 3.32135 | 2.379345 | 7.33564 | 7.598264 | 6.129407 |
| CCNI | 1.175410757 | 0.043453389 | 0.006277645 | 19.07312948 | 7.259029 | 5.148082 | 6.489771 | 11.099197 | 10.666023 | 10.74324 |
| DNAJC24 | 1.170835072 | 0.043453389 | 0.006413746 | 19.03370769 | 4.309025 | 2.809601 | 3.764125 | 8.014609 | 8.220489 | 7.640338 |
| LOC100131564 | 1.119389173 | 0.043485739 | 0.00760871 | 19.0053109 | 4.209882 | 6.060401 | 5.018694 | 9.058353 | 9.722706 | 9.267025 |
| PARK7 | 1.064398047 | 0.043516135 | 0.009407962 | 18.96510715 | 4.963444 | 4.389936 | 2.379345 | 7.976765 | 9.20872 | 7.748756 |
| TNFRSF10D | 1.140156922 | 0.043453389 | 0.0071623 | 18.96118638 | 3.350997 | 2.406905 | 2.995681 | 6.651882 | 6.861783 | 8.678584 |
| PM20D2 | 1.083395294 | 0.043516135 | 0.008836339 | 18.88360241 | 1.874444 | 2.023048 | 2.379345 | 7.814607 | 6.549959 | 6.618407 |
| ADAM22 | 0.929254982 | 0.043485739 | 0.014854712 | 18.81862481 | 1.874444 | 2.406905 | 4.449894 | 7.243046 | 6.640994 | 6.195186 |
| OR2H1 | 1.192612573 | 0.043453389 | 0.005889758 | 18.81811624 | 1.874444 | 2.406905 | 2.379345 | 5.891233 | 6.613395 | 7.180104 |
| ANAPC4 | 1.256476775 | 0.043453389 | 0.004529432 | 18.792918 | 1.874444 | 2.023048 | 2.165421 | 6.252746 | 7.174648 | 6.106561 |
| PGCP | 1.097967478 | 0.04349335 | 0.008255869 | 18.792918 | 1.874444 | 2.023048 | 3.324375 | 6.252746 | 8.098861 | 6.106561 |
| SLC25A27 | 1.044256776 | 0.043577906 | 0.010194624 | 18.792918 | 1.874444 | 2.406905 | 3.90836 | 7.33564 | 7.107836 | 6.106561 |
| FUT8 | 1.156828145 | 0.043453389 | 0.006699558 | 18.78197464 | 2.201691 | 2.023048 | 2.165421 | 6.396698 | 8.077554 | 5.634184 |
| PMVK | 1.224828626 | 0.043453389 | 0.00509425 | 18.76613612 | 1.874444 | 2.406905 | 2.165421 | 6.395481 | 6.549959 | 6.106561 |
| MRPL21 | 1.164105335 | 0.043453389 | 0.006515822 | 18.76613612 | 2.993831 | 2.023048 | 2.165421 | 6.395481 | 7.107836 | 6.32627 |
| AGMO | 1.104090868 | 0.04349335 | 0.007800078938 | 18.76613612 | 3.350997 | 2.809601 | 2.165421 | 6.395481 | 6.373501 | 7.033813 |
| PFDN1 | 0.912789636 | 0.044110923 | 0.015720994 | 18.76143219 | 1.874444 | 6.072636 | 4.449894 | 6.252746 | 9.897049 | 9.832914 |
| TRIAP1 | 0.981542702 | 0.043626235 | 0.012524668 | 18.74290867 | 1.874444 | 2.023048 | 2.165421 | 6.244586 | 7.819723 | 6.051818 |
| RDH11 | 0.8192624 | 0.045111103 | 0.020777816 | 18.70995721 | 6.973646 | 4.351315 | 3.935222 | 7.037879 | 7.406567 | 5.091834 |
| RGL1 | 1.145033141 | 0.043453389 | 0.006971759 | 18.70713686 | 4.309025 | 3.770995 | 2.995681 | 8.811966 | 8.160956 | 8.60836 |
| VAMP8 | 1.048849678 | 0.043577906 | 0.009970738 | 18.692517 | 5.056948 | 5.340619 | 2.165421 | 7.177844 | 8.453372 | 8.534542 |
| SRP19 | 1.058655016 | 0.043540291 | 0.009573324 | 18.69022689 | 3.350997 | 2.809601 | 2.165421 | 9.565008 | 8.2398 | 8.374509 |
| GIT2 | 1.024567702 | 0.043577906 | 0.010831575 | 18.69022689 | 1.874444 | 2.023048 | 4.285996 | 9.410337 | 7.094585 | 7.033813 |
| PPP1CC | 1.161138791 | 0.043453389 | 0.006613872 | 18.67413032 | 5.056948 | 6.072636 | 5.609945 | 6.252746 | 7.269549 | 9.832914 |
| EBPL | 1.234283596 | 0.043453389 | 0.004917319 | 18.65561977 | 1.874444 | 2.023048 | 2.165421 | 9.410337 | 7.819723 | 6.051818 |
| PRPF18 | 1.225478172 | 0.043453389 | 0.00506703 | 18.65561977 | 1.874444 | 2.023048 | 2.165421 | 6.244586 | 6.794431 | 5.900694 |
| PCA3 | 1.219247194 | 0.043453389 | 0.005223545 | 18.65561977 | 1.874444 | 2.023048 | 2.165421 | 6.244586 | 5.936219 | 7.668215 |
| LOC283856 | 0.976568056 | 0.043661316 | 0.012660088 | 18.61044216 | 2.993831 | 3.770995 | 5.544653 | 7.42265 | 7.989035 | 8.906373 |
| BAG3 | 1.120467153 | 0.043485739 | 0.007588149 | 18.60437624 | 5.744513 | 6.931478 | 7.663508 | 10.780147 | 11.194951 | 11.149048 |
| FLJ41200 | 1.203136819 | 0.043453389 | 0.005536577 | 18.59745833 | 3.350997 | 2.406905 | 3.764125 | 7.274575 | 7.56803 | 7.943848 |
| THNSL2 | 0.8622511 | 0.044379352 | 0.018285812 | 18.59745833 | 4.963444 | 2.809601 | 2.165421 | 7.36523 | 7.56803 | 4.476242 |
| C10orf32 | 1.045039813 | 0.043577906 | 0.010167404 | 18.57287155 | 1.874444 | 2.406905 | 4.449894 | 8.665019 | 8.668166 | 7.395512 |
| KLRB1 | 1.221913282 | 0.043453389 | 0.00051623 | 18.56364137 | 1.874444 | 2.023048 | 2.165421 | 6.651882 | 6.237456 | 5.882028 |
| SCG3 | 1.191887689 | 0.043453389 | 0.005923784 | 18.56364137 | 1.874444 | 2.023048 | 2.165421 | 5.728038 | 6.237456 | 7.020304 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| C7orf44 | 1.162911025 | 0.043453389 | 0.006543042 | 18.56364137 | 1.874444 | 2.023048 | 2.165421 | 6.544171 | 6.237456 | 5.580533 |
| CD8B | 1.080789907 | 0.043516135 | 0.008924804 | 18.56364137 | 1.874444 | 2.023048 | 2.165421 | 7.177844 | 6.237456 | 5.091834 |
| TNFSF15 | 1.043879803 | 0.043577906 | 0.010208234 | 18.56364137 | 1.874444 | 2.023048 | 2.165421 | 4.894482 | 6.237456 | 6.942983 |
| ABCB5 | 1.006664853 | 0.043588662 | 0.011605988 | 18.56364137 | 1.874444 | 2.023048 | 2.165421 | 4.718672 | 6.237456 | 6.649696 |
| RPP38 | 1.004825809 | 0.043588662 | 0.011680844 | 18.56364137 | 1.874444 | 2.023048 | 2.165421 | 7.995811 | 6.237456 | 4.562324 |
| GGTA1P | 0.902660572 | 0.044190907 | 0.016303505 | 18.56364137 | 1.874444 | 2.023048 | 2.379345 | 6.954147 | 6.237456 | 4.146207 |
| TMEM72-AS1 | 0.903237077 | 0.044190907 | 0.01633753 | 18.56364137 | 1.874444 | 2.023048 | 2.165421 | 6.395481 | 6.237456 | 4.146207 |
| MNS1 | 0.828487216 | 0.044930476 | 0.020236815 | 18.56364137 | 1.874444 | 2.023048 | 2.379345 | 6.814118 | 6.237456 | 3.676349 |
| ZBTB11 | 0.849521549 | 0.044521554 | 0.018911194 | 18.5605534 | 1.874444 | 2.023048 | 3.90836 | 8.122528 | 7.269549 | 4.146207 |
| KCTD10 | 1.097778152 | 0.04349335 | 0.008283089 | 18.52674722 | 3.839948 | 3.770995 | 2.379345 | 8.051486 | 7.406567 | 7.020304 |
| FOXP2 | 1.119992628 | 0.043485739 | 0.0075951 | 18.52628879 | 1.874444 | 2.023048 | 3.324375 | 6.339437 | 7.107836 | 6.618407 |
| AMPD2 | 1.070724754 | 0.043516135 | 0.009231031 | 18.51071886 | 4.309025 | 2.406905 | 4.285996 | 7.918071 | 7.269549 | 8.519314 |
| GAR1 | 1.1204971 | 0.043485739 | 0.007840082 | 18.5032964 | 1.874444 | 3.32135 | 2.165421 | 7.531061 | 6.861783 | 5.900694 |
| FLJ25363 | 1.093505943 | 0.04349335 | 0.008466825 | 18.49025955 | 4.815804 | 4.351315 | 4.754917 | 7.771052 | 8.963611 | 9.613837 |
| PTPN4 | 1.205839119 | 0.043453389 | 0.005488942 | 18.48239708 | 2.201691 | 2.023048 | 2.165421 | 6.960054 | 6.373501 | 5.882028 |
| ACN9 | 1.095626718 | 0.04349335 | 0.008371155 | 18.48239708 | 3.024504 | 2.023048 | 2.165421 | 7.25991 | 6.373501 | 5.874974 |
| ARL6IP6 | 0.957485579 | 0.043835088 | 0.013548826 | 18.48239708 | 1.874444 | 2.406905 | 2.165421 | 6.814118 | 6.373501 | 4.562324 |
| FAF1 | 1.070471075 | 0.043516135 | 0.009237836 | 18.48179558 | 4.209882 | 2.023048 | 2.379345 | 7.144104 | 7.96603 | 6.587378 |
| RAPGEF6 | 1.121615148 | 0.043480953 | 0.007555631 | 18.47360161 | 4.309025 | 3.360637 | 3.324375 | 7.556937 | 7.56803 | 7.873743 |
| OXTR | 1.000590668 | 0.043588662 | 0.01183055 | 18.47360161 | 2.201691 | 3.360637 | 2.165421 | 5.448591 | 7.56803 | 6.587378 |
| SMAD5 | 1.225632816 | 0.043453389 | 0.005060225 | 18.47267198 | 4.309025 | 4.413323 | 3.90836 | 8.604261 | 8.609988 | 8.11568 |
| RRAS2 | 1.008119222 | 0.043581008 | 0.011511398 | 18.44988872 | 2.201691 | 3.872014 | 4.508334 | 8.993498 | 8.077554 | 6.385515 |
| ZG16 | 1.114684319 | 0.043485739 | 0.007758421 | 18.42712866 | 6.58615 | 6.228068 | 7.250844 | 10.153715 | 11.454603 | 10.862687 |
| LOC100130451 | 0.926075252 | 0.04406867 | 0.0150541 | 18.31603729 | 1.874444 | 3.770995 | 3.935222 | 5.448591 | 7.96603 | 8.194487 |
| IGSF9B | 0.948769591 | 0.043900827 | 0.01394016 | 18.31430117 | 4.309025 | 4.351315 | 2.995681 | 6.252746 | 8.624754 | 8.503924 |
| PLSCR4 | 0.836290021 | 0.044768725 | 0.019682205 | 18.28225372 | 3.839948 | 4.351315 | 2.995681 | 5.252045 | 10.142544 | 8.03232 |
| C10orf116 | 1.100867431 | 0.04349335 | 0.008194624 | 18.27011835 | 6.008206 | 7.197097 | 6.919905 | 6.954147 | 10.690795 | 12.407415 |
| LOC254128 | 0.852905659 | 0.044464174 | 0.018704321 | 18.24559808 | 3.024504 | 3.360637 | 4.449894 | 5.252045 | 8.63937 | 8.11568 |
| GVINP1 | 1.121677954 | 0.043480953 | 0.007548826 | 18.23632159 | 4.682076 | 4.389936 | 5.217616 | 9.590293 | 8.2398 | 8.870819 |
| BCDIN3D | 1.128446657 | 0.043453389 | 0.00738061 | 18.2344872 | 1.874444 | 2.023048 | 2.995681 | 6.063041 | 6.189775 | 8.213534 |
| STXBP5 | 1.124573853 | 0.043453389 | 0.007461722 | 18.2344872 | 1.874444 | 2.406905 | 2.995681 | 6.063041 | 7.292524 | 6.455366 |
| LOC100506085 | 1.178089764 | 0.043453389 | 0.006223205 | 18.21816902 | 4.743564 | 4.413323 | 3.935222 | 8.122528 | 8.59507 | 9.02972 |
| ZDHHC23 | 1.216336801 | 0.043453389 | 0.005284791 | 18.16203854 | 1.874444 | 2.023048 | 2.165421 | 6.814118 | 6.205902 | 5.874974 |
| MST1P2 | 1.192595927 | 0.043453389 | 0.005896563 | 18.16203854 | 1.874444 | 2.023048 | 2.165421 | 5.743334 | 6.205902 | 6.649696 |
| FLJ44635 | 1.168690434 | 0.043453389 | 0.00646138 | 18.16203854 | 2.993831 | 2.023048 | 2.165421 | 6.954147 | 6.205902 | 6.649696 |
| C9orf82 | 1.146649422 | 0.043453389 | 0.006930929 | 18.16203854 | 1.874444 | 2.023048 | 2.379345 | 7.177844 | 6.205902 | 5.634184 |
| NCAPG2 | 1.136541966 | 0.043453389 | 0.007209935 | 18.16203854 | 1.874444 | 2.023048 | 2.165421 | 6.664985 | 6.205902 | 5.446557 |
| CES4A | 1.127486816 | 0.043453389 | 0.007400476 | 18.16203854 | 1.874444 | 2.023048 | 2.165421 | 6.395481 | 6.205902 | 5.426231 |
| MED21 | 1.080989067 | 0.043516135 | 0.008917999 | 18.16203854 | 1.874444 | 2.023048 | 2.379345 | 7.792994 | 6.205902 | 5.091834 |
| VRK1 | 1.079327258 | 0.043516135 | 0.008898605 | 18.16203854 | 1.874444 | 2.023048 | 2.165421 | 7.33564 | 6.205902 | 5.091834 |
| C4orf34 | 0.972469599 | 0.043681142 | 0.012879211 | 18.16203854 | 2.993831 | 2.023048 | 2.165421 | 6.960054 | 6.205902 | 4.476242 |
| ACSL5 | 0.881982872 | 0.044229452 | 0.017352161 | 18.16203854 | 4.743564 | 2.023048 | 2.165421 | 6.960054 | 6.205902 | 6.722123 |
| POC1B | 0.864316456 | 0.044377262 | 0.018137462 | 18.16203854 | 1.874444 | 2.023048 | 2.165421 | 7.42265 | 6.205902 | 3.676349 |
| LOC100216479 | 0.848590249 | 0.044592081 | 0.018984008 | 18.16203854 | 1.874444 | 2.023048 | 2.165421 | 7.109557 | 6.205902 | 3.630092 |
| TMEM45A | 0.755093585 | 0.046508764 | 0.025261654 | 18.16203854 | 1.874444 | 2.023048 | 2.165421 | 7.167419 | 6.205902 | 2.921909 |
| GLMN | 0.741421875 | 0.046993264 | 0.026259952 | 18.16203854 | 1.874444 | 2.023048 | 2.379345 | 6.811341 | 6.205902 | 2.921909 |
| KDM4C | 1.117443201 | 0.04348573 | 0.007649541 | 18.13640401 | 2.993831 | 2.023048 | 2.165421 | 6.395481 | 7.174648 | 5.091834 |
| ZNF438 | 1.244865244 | 0.043453389 | 0.00476080 | 18.09318541 | 1.874444 | 2.023048 | 2.165421 | 6.183122 | 6.774676 | 6.051818 |
| ECHS1 | 1.062558941 | 0.043516135 | 0.009462402 | 18.08208224 | 4.263463 | 4.351315 | 2.165421 | 8.527804 | 7.713236 | 7.36177 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| FTSJ2 | 0.81921377 | 0.045111103 | 0.020784621 | 18.05112222 | 1.874444 | 2.023048 | 2.165421 | 6.339437 | 6.205902 | 3.630092 |
| SPP1 | 0.749329358 | 0.046728791 | 0.025692412 | 18.05112222 | 1.874444 | 3.770995 | 2.165421 | 6.339437 | 8.402869 | 3.676349 |
| PNRC1 | 1.216199662 | 0.043453389 | 0.005291596 | 18.03795748 | 8.161926 | 6.139057 | 8.037751 | 12.00996 | 12.33489 | 12.198613 |
| PPP1R2P9 | 1.201419866 | 0.043453389 | 0.005559782 | 18.02762962 | 1.874444 | 2.023048 | 2.165421 | 8.239009 | 5.920411 | 6.195186 |
| GALT | 1.116380998 | 0.043485739 | 0.007697176 | 18.02762962 | 1.874444 | 2.023048 | 2.165421 | 5.320955 | 7.25505 | 6.195186 |
| ZBTB24 | 1.091583046 | 0.0435113 | 0.008559374 | 18.02762962 | 3.350997 | 2.023048 | 2.165421 | 6.811341 | 6.608026 | 6.195186 |
| MFSD4 | 1.081306041 | 0.043516135 | 0.008897584 | 18.02762962 | 1.874444 | 2.023048 | 2.165421 | 6.550689 | 5.165949 | 6.195186 |
| POLK | 1.009916836 | 0.043581008 | 0.011436543 | 18.02762962 | 3.024504 | 2.023048 | 3.935222 | 7.30543 | 7.269549 | 6.195186 |
| NDUFS1 | 0.998047964 | 0.043626235 | 0.011917659 | 18.02762962 | 4.209882 | 2.023048 | 2.165421 | 7.835902 | 6.613395 | 6.195186 |
| ITGA4 | 0.946653766 | 0.043900827 | 0.014069411 | 18.02712992 | 1.874444 | 2.023048 | 2.379345 | 6.339437 | 6.551443 | 4.476242 |
| SLC16A2 | 1.088035473 | 0.043516135 | 0.008682545 | 18.023535 | 2.201691 | 3.360637 | 2.165421 | 6.339437 | 6.373501 | 7.03218 |
| SMEK1 | 1.131643294 | 0.043453389 | 0.007291596 | 18.02163406 | 4.263463 | 3.770995 | 2.995681 | 8.222933 | 7.942633 | 7.352555 |
| LOC653566 | 1.235259126 | 0.043453389 | 0.004896904 | 17.99088536 | 3.819732 | 2.023048 | 3.90836 | 7.976765 | 8.077554 | 7.943848 |
| MT1F | 1.228662523 | 0.043453389 | 0.004998979 | 17.98946004 | 1.874444 | 2.023048 | 2.165421 | 7.210813 | 6.043524 | 6.129407 |
| LTB | 1.228599552 | 0.043453389 | 0.005005784 | 17.98946004 | 1.874444 | 2.023048 | 2.165421 | 6.063041 | 6.043524 | 6.618407 |
| COG5 | 0.955579004 | 0.043840967 | 0.01366179 | 17.98946004 | 4.263463 | 3.872014 | 3.764125 | 8.665019 | 6.043524 | 6.942983 |
| ANXA3 | 1.167640125 | 0.043453389 | 0.006474991 | 17.96015231 | 1.874444 | 2.023048 | 2.165421 | 5.743334 | 6.189775 | 8.84662 |
| IL20RA | 1.157010759 | 0.043453389 | 0.006685948 | 17.96015231 | 1.874444 | 2.023048 | 2.165421 | 7.631894 | 6.189775 | 5.580533 |
| MTCP1NB | 1.133345532 | 0.043453389 | 0.007264376 | 17.96015231 | 1.874444 | 2.023048 | 2.165421 | 7.394225 | 6.189775 | 5.426231 |
| CYP7B1 | 1.006149944 | 0.043588662 | 0.011612793 | 17.96015231 | 1.874444 | 2.023048 | 2.165421 | 6.063041 | 6.189775 | 6.73963 |
| UCP2 | 0.955579004 | 0.043840967 | 0.01366179 | 17.96015231 | 4.263463 | 3.872014 | 3.764125 | 4.718672 | 6.189775 | 6.924055 |
| ANAPC10 | 0.969580348 | 0.043726704 | 0.013009867 | 17.96015231 | 1.874444 | 2.023048 | 2.165421 | 6.960054 | 6.189775 | 3.630092 |
| GTF2H2D | 0.881413949 | 0.044251488 | 0.017374617 | 17.96015231 | 1.874444 | 2.023048 | 2.165421 | 8.527804 | 6.189775 | 3.630092 |
| KIAA1143 | 0.852207565 | 0.044480228 | 0.018753317 | 17.96015231 | 1.874444 | 2.023048 | 2.165421 | 7.25991 | 6.189775 | 7.825039 |
| TMCO1 | 1.14499078 | 0.043588662 | 0.006978564 | 17.91806264 | 4.639409 | 4.351315 | 2.379345 | 8.514658 | 8.737737 | 8.232333 |
| AIFM2 | 1.01542368 | 0.043581008 | 0.011225587 | 17.91806264 | 5.700376 | 4.351315 | 2.995681 | 8.514658 | 8.533804 | 12.420795 |
| EPHB3 | 1.020833448 | 0.043577906 | 0.011008506 | 17.91785111 | 9.354026 | 8.25747 | 6.636262 | 11.70801 | 12.556129 | 5.634184 |
| LOC100506757 | 1.076052742 | 0.043516135 | 0.00906771 | 17.90923325 | 3.024504 | 2.023048 | 2.379345 | 8.139755 | 7.187136 | 6.32627 |
| PIN4 | 1.123150886 | 0.043453389 | 0.007488942 | 17.88712493 | 4.263463 | 2.406905 | 2.165421 | 5.252045 | 8.36819 | 6.32627 |
| SYTL1 | 1.097114387 | 0.04349335 | 0.00832392 | 17.88712493 | 1.874444 | 2.023048 | 2.165421 | 6.544171 | 6.319269 | 6.32627 |
| MGC16142 | 1.051754884 | 0.043568903 | 0.009881592 | 17.88712493 | 3.350997 | 3.360637 | 2.165421 | 6.183122 | 6.489775 | 5.882028 |
| C9orf53 | 1.211624664 | 0.043453389 | 0.00580061 | 17.87751803 | 1.874444 | 2.023048 | 2.165421 | 6.183122 | 7.094585 | 5.106393 |
| LOC286177 | 1.080691902 | 0.043516135 | 0.008931609 | 17.87751803 | 1.874444 | 2.023048 | 2.165421 | 7.56803 | 7.56803 | 6.385515 |
| CCBL2 | 1.002061546 | 0.043588662 | 0.011782919 | 17.87751803 | 2.201691 | 2.023048 | 2.165421 | 6.183122 | 7.406567 | 4.476242 |
| MRPL1 | 0.977513586 | 0.043661316 | 0.012639673 | 17.87751803 | 1.874444 | 2.023048 | 2.165421 | 6.183122 | 7.269549 | 4.146207 |
| DYNLT3 | 0.905579442 | 0.044173537 | 0.016138142 | 17.87751803 | 1.874444 | 2.023048 | 2.165421 | 6.183122 | 6.549959 | 7.920856 |
| OSBPL9 | 0.972505431 | 0.043681142 | 0.012872406 | 17.83614132 | 5.856559 | 3.872014 | 3.764125 | 9.058353 | 8.160956 | 7.033813 |
| PSMB10 | 1.038860997 | 0.043577906 | 0.010033753 | 17.83250093 | 4.263463 | 4.413323 | 3.764125 | 8.895478 | 8.4199 | 5.634184 |
| ALG8 | 1.141078847 | 0.043453389 | 0.007101055 | 17.80053164 | 1.874444 | 2.023048 | 2.165421 | 6.954147 | 6.319269 | 2.921909 |
| PION | 0.763861162 | 0.046215863 | 0.024567754 | 17.80053164 | 2.201691 | 2.023048 | 2.165421 | 7.937902 | 6.319269 | 5.091834 |
| LOC401324 | 0.969723309 | 0.043726704 | 0.012996257 | 17.79425588 | 3.024504 | 2.023048 | 2.379345 | 7.177844 | 6.319269 | 7.800057 |
| GOLPH3L | 0.957645687 | 0.043835088 | 0.013542021 | 17.79048138 | 5.744513 | 3.32135 | 3.935222 | 8.087444 | 8.579995 | 4.476242 |
| CASP10 | 0.864788918 | 0.044377262 | 0.018119769 | 17.75867877 | 2.993831 | 2.809601 | 2.165421 | 6.960054 | 7.31791 | 7.033813 |
| CEP63 | 1.026874994 | 0.043577906 | 0.01068867 | 17.564735 | 2.993831 | 2.023048 | 4.724406 | 7.144104 | 8.200916 | 8.175185 |
| ZNF33B | 1.130735036 | 0.043453389 | 0.007332426 | 17.71716601 | 4.682076 | 3.770995 | 3.90836 | 7.918071 | 8.2398 | 5.426231 |
| ARHGEF25 | 1.045905599 | 0.043577906 | 0.010134059 | 17.69117584 | 1.874444 | 3.360637 | 2.165421 | 7.037879 | 7.505595 | 7.748756 |
| ACTR6 | 1.138403637 | 0.043453389 | 0.00718952 | 17.68612438 | 2.993831 | 2.809601 | 3.90836 | 6.954147 | 7.440337 | 5.091834 |
| ZNF410 | 0.965744339 | 0.043778104 | 0.013153454 | 17.6680224 | 4.963444 | 4.830496 | 4.449894 | 8.974419 | 9.179013 | 8.25089 |
| ALG9 | 1.141867693 | 0.043453389 | 0.007060225 | 17.67849429 | 4.743564 | 2.406905 | 2.165421 | 6.550689 | 6.549959 | 5.091834 |
| | 0.916485713 | 0.044110923 | 0.015496427 | 17.67678914 | | | | | | 7.523109 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| NSDHL | 1.098643214 | 0.04349335 | 0.008242259 | 17.6678456 | 2.993831 | 2.406905 | 2.165421 | 8.361545 | 6.549959 | 5.874974 |
| CHCHD7 | 1.095211142 | 0.04349335 | 0.008412385 | 17.6678456 | 3.024504 | 2.406905 | 2.165421 | 7.856887 | 6.549959 | 5.882028 |
| DKFZP564C196 | 1.045705848 | 0.043577906 | 0.010140864 | 17.661246 | 6.52121 | 4.736586 | 5.974145 | 9.012327 | 10.11666 | 10.32408 |
| ZSCAN29 | 1.152921992 | 0.043453389 | 0.006781218 | 17.59710875 | 3.024504 | 2.406905 | 2.379345 | 6.544171 | 6.373501 | 7.180104 |
| NUP160 | 1.170373965 | 0.043453389 | 0.006420551 | 17.58601318 | 4.743564 | 4.80797 | 4.449894 | 8.286188 | 8.87992 | 9.143346 |
| LOC400950 | 1.103771933 | 0.04349335 | 0.008085743 | 17.58587823 | 4.209882 | 2.023048 | 3.324375 | 6.960054 | 8.296229 | 7.46072 |
| ZNF3 | 1.201516935 | 0.043453389 | 0.005584212 | 17.54978763 | 2.201691 | 2.809601 | 2.165421 | 6.283686 | 6.608026 | 6.942983 |
| HDGFRP3 | 0.982123427 | 0.043626235 | 0.012504253 | 17.54978763 | 4.639409 | 2.809601 | 2.379345 | 7.877571 | 6.794431 | 6.942983 |
| FCF1 | 1.073693847 | 0.043516135 | 0.009128955 | 17.54440726 | 7.427999 | 6.228068 | 7.317525 | 10.039027 | 11.450464 | 12.464189 |
| PRKCDBP | 1.01493821 | 0.043581008 | 0.011273222 | 17.51604504 | 4.263463 | 3.360637 | 3.764125 | 6.664985 | 7.89473 | 8.456743 |
| SUPV3L1 | 1.115154826 | 0.043485739 | 0.007731201 | 17.4808179 | 3.024504 | 2.379345 | 2.379345 | 7.074163 | 7.31791 | 7.152205 |
| STOX2 | 0.984635598 | 0.043626235 | 0.012381763 | 17.4808179 | 3.024504 | 2.406905 | 2.165421 | 5.252045 | 6.551443 | 7.152205 |
| C7orf73 | 1.072078285 | 0.043516135 | 0.009203811 | 17.45554299 | 4.682076 | 4.80797 | 3.90836 | 9.030914 | 8.033973 | 8.095288 |
| RAB10 | 0.974640124 | 0.043661316 | 0.012755359 | 17.44816265 | 5.304463 | 4.389936 | 4.754917 | 9.615142 | 8.87992 | 7.428484 |
| NUTF2 | 0.962056609 | 0.043778104 | 0.013289554 | 17.42365096 | 5.056948 | 3.360637 | 2.379345 | 9.179923 | 7.793829 | 6.385515 |
| MIER1 | 1.004274033 | 0.043588662 | 0.011701259 | 17.3755482 | 2.993831 | 3.32135 | 3.324375 | 7.835902 | 7.440337 | 5.900694 |
| HEMK1 | 1.176306876 | 0.043453389 | 0.006264035 | 17.36686186 | 1.874444 | 2.406905 | 2.165421 | 6.283686 | 6.551443 | 5.882028 |
| RBBP5 | 1.121452265 | 0.043480953 | 0.007562436 | 17.36686186 | 2.201691 | 2.023048 | 2.165421 | 6.283686 | 5.509998 | 6.455366 |
| EGF | 1.061661786 | 0.043540291 | 0.009498469 | 17.36686186 | 1.874444 | 2.023048 | 2.165421 | 6.283686 | 6.189775 | 5.106393 |
| LMOD3 | 1.057670449 | 0.043540291 | 0.009641375 | 17.36686186 | 1.874444 | 2.809601 | 2.165421 | 6.283686 | 7.174648 | 5.446557 |
| RPAP3 | 1.029402941 | 0.043577906 | 0.010582511 | 17.36686186 | 3.350997 | 2.023048 | 2.165421 | 6.283686 | 6.205902 | 6.32627 |
| TMEM8B | 1.003944085 | 0.043588662 | 0.011708064 | 17.36686186 | 1.874444 | 4.389936 | 4.754917 | 6.283686 | 6.189775 | 4.790662 |
| BOLA3 | 1.122661383 | 0.043480953 | 0.007521606 | 17.35784487 | 3.839948 | 3.770995 | 2.165421 | 7.957464 | 7.191402 | 7.492252 |
| TXNDC11 | 1.032257244 | 0.043577906 | 0.010500851 | 17.33916214 | 4.682076 | 2.023048 | 3.324375 | 7.70315 | 7.440337 | 7.291822 |
| ALDH1A1 | 1.018152868 | 0.043453389 | 0.011137802 | 17.32129403 | 3.024504 | 2.023048 | 2.379345 | 5.252.45 | 7.138979 | 6.931222 |
| C14orf28 | 0.985293726 | 0.043626235 | 0.01234737 | 17.32103992 | 2.201691 | 2.809601 | 2.165421 | 5.026959 | 6.613395 | 6.924055 |
| PON3 | 1.054290233 | 0.043568903 | 0.009779517 | 17.30895205 | 1.874444 | 2.023048 | 3.764125 | 7.877571 | 6.774676 | 5.874974 |
| GALNT7 | 0.977794966 | 0.043661316 | 0.012619258 | 17.29991328 | 4.263463 | 3.32135 | 2.165421 | 8.376156 | 6.861783 | 6.455366 |
| KIAA1279 | 0.776328525 | 0.045884853 | 0.023623682 | 17.29346193 | 1.874444 | 2.023048 | 2.995681 | 6.244586 | 7.107836 | 3.630092 |
| AFF3 | 0.975830326 | 0.043661316 | 0.012700919 | 17.27215586 | 3.024504 | 2.023048 | 5.018694 | 9.12907 | 7.094585 | 6.69026 |
| COMMD3 | 1.178041021 | 0.043453389 | 0.006023001 | 17.22413491 | 1.874444 | 2.023048 | 2.165421 | 5.705318 | 6.640994 | 6.129407 |
| LOC653061 | 1.177635024 | 0.043453389 | 0.006236815 | 17.22413491 | 1.874444 | 2.023048 | 2.165421 | 5.728038 | 7.25505 | 6.129407 |
| METTL20 | 1.174550244 | 0.043453389 | 0.000298061 | 17.22413491 | 1.874444 | 2.023048 | 2.165421 | 5.705318 | 7.191402 | 6.129407 |
| FAM82B | 1.088006657 | 0.043516135 | 0.008668935 | 17.22413491 | 1.874444 | 2.023048 | 2.995681 | 7.243046 | 5.857745 | 6.129407 |
| PGAP2 | 1.013167333 | 0.043581008 | 0.011341273 | 17.22413491 | 2.201691 | 2.023048 | 3.764125 | 6.954147 | 6.549959 | 6.129407 |
| RHOH | 0.996939492 | 0.043626235 | 0.011951606 | 17.22413491 | 1.874444 | 2.023048 | 2.165421 | 7.450526 | 4.608763 | 6.129407 |
| OLAH | 0.966608624 | 0.043778104 | 0.013126233 | 17.22413491 | 1.874444 | 2.023048 | 2.165421 | 6.550689 | 4.539173 | 6.129407 |
| KRT1 | 0.736819334 | 0.047171086 | 0.026613134 | 17.22413491 | 4.209882 | 2.023048 | 2.165421 | 2.820813 | 7.138979 | 6.129407 |
| CNTN1 | 0.916069568 | 0.044110923 | 0.015537258 | 17.2128895 | 1.874444 | 2.023048 | 4.724406 | 6.954147 | 8.829823 | 5.426231 |
| SLC25A15 | 1.169440615 | 0.043453389 | 0.008425995 | 17.1972946 | 4.209882 | 3.360637 | 3.324375 | 7.877571 | 8.200916 | 7.428484 |
| CXorf21 | 1.094500154 | 0.04349335 | 0.008425995 | 17.19423849 | 3.819732 | 3.32135 | 3.324375 | 7.177844 | 8.696398 | 8.858771 |
| SNHG12 | 1.023249774 | 0.043577906 | 0.010892821 | 17.17283706 | 3.819732 | 4.351315 | 5.389265 | 10.140938 | 8.453372 | 7.582913 |
| IFT81 | 1.095415832 | 0.04349335 | 0.008398775 | 17.12788729 | 3.819732 | 2.023048 | 3.324375 | 7.42265 | 7.870158 | 6.618407 |
| CENPN | 1.08065566 | 0.043516135 | 0.008938414 | 17.0998926 | 4.309025 | 5.43468 | 4.449894 | 8.40494 | 8.904331 | 8.593895 |
| XKR5 | 0.990197007 | 0.043626235 | 0.012177611 | 17.09909288 | 4.682076 | 3.360637 | 5.596986 | 7.582358 | 8.777924 | 9.33818 |
| CEP68 | 1.026780782 | 0.043577906 | 0.01070228 | 17.06801449 | 5.304463 | 3.32135 | 4.508334 | 7.74871 | 8.258856 | 9.397686 |
| IQCC | 1.157917212 | 0.043453389 | 0.006672338 | 17.04075834 | 5.316227 | 5.661685 | 6.355801 | 9.403221 | 10.446718 | 10.233665 |
| ITM2A | 0.953404398 | 0.043857532 | 0.013749575 | 17.01258392 | 5.056948 | 5.195784 | 6.769247 | 9.284314 | 11.103027 | 8.549611 |
| MITD1 | 1.21708174 | 0.043453389 | 0.005271181 | 16.99837624 | 1.874444 | 2.023048 | 2.165421 | 6.252746 | 6.205902 | 5.900694 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| NAA16 | 1.092329265 | 0.04349335 | 0.008521266 | 16.99837624 | 2.993831 | 2.023048 | 2.165421 | 6.252746 | 7.96603 | 5.874974 |
| SNUPN | 1.044975227 | 0.043577906 | 0.010174209 | 16.99837624 | 1.874444 | 2.406905 | 2.165421 | 6.252746 | 7.174648 | 5.091834 |
| FAM82A2 | 0.876854231 | 0.044280042 | 0.017576046 | 16.99837624 | 2.201691 | 4.80797 | 2.165421 | 6.252746 | 6.861783 | 6.924055 |
| FBXW7 | 1.077479668 | 0.043516135 | 0.00904049 | 16.98150388 | 3.024504 | 3.770995 | 2.995681 | 7.856887 | 7.505595 | 6.455366 |
| CFDP1 | 1.033511375 | 0.043577906 | 0.01044641 | 16.97355658 | 3.024504 | 3.32135 | 2.165421 | 5.743334 | 7.406567 | 7.395512 |
| LOC400550 | 1.175153213 | 0.043453389 | 0.00628445 | 16.95351964 | 1.874444 | 2.023048 | 2.165421 | 5.705318 | 6.794431 | 6.106561 |
| SEPT14 | 1.10788162 | 0.043485739 | 0.007962572 | 16.95351964 | 1.874444 | 2.023048 | 2.165421 | 5.320955 | 7.174648 | 6.106561 |
| LOC100130691 | 1.104692709 | 0.04349335 | 0.008051718 | 16.95351964 | 1.874444 | 2.023048 | 2.165421 | 5.320955 | 6.613395 | 6.106561 |
| LOC375295 | 1.077042002 | 0.043516135 | 0.0090541 | 16.93801234 | 1.874444 | 2.023048 | 3.324375 | 5.448591 | 7.406567 | 7.36177 |
| SERPINB1 | 1.088341873 | 0.043516135 | 0.00866213 | 16.93569515 | 2.201691 | 3.360637 | 2.165421 | 6.283686 | 6.237456 | 8.60836 |
| TMCO4 | 1.172353068 | 0.043453389 | 0.006345696 | 16.90877224 | 3.350997 | 3.360637 | 2.165421 | 7.36523 | 7.440337 | 6.931222 |
| C3orf27 | 1.152170919 | 0.043453389 | 0.000808438 | 16.90250726 | 1.874444 | 2.023048 | 2.165421 | 6.244586 | 6.189775 | 5.580533 |
| NMI | 1.147514463 | 0.043453389 | 0.006917319 | 16.90260726 | 2.201691 | 2.023048 | 2.165421 | 6.244586 | 6.861783 | 5.634184 |
| SHROOM4 | 1.01876127 | 0.043577906 | 0.01111582 | 16.88604281 | 3.819732 | 3.360637 | 2.165421 | 6.063041 | 7.53715 | 7.897492 |
| STL | 1.108916413 | 0.043485739 | 0.007935352 | 16.85141865 | 5.304463 | 4.80797 | 4.724406 | 8.39062 | 10.132246 | 8.882768 |
| CCL21 | 1.007211727 | 0.043588662 | 0.011578768 | 16.84770994 | 5.263699 | 3.32135 | 3.764125 | 7.976765 | 7.31791 | 9.33818 |
| COA5 | 1.144095047 | 0.043453389 | 0.006992174 | 16.81917229 | 2.201691 | 2.023048 | 2.165421 | 7.531061 | 6.237456 | 5.634184 |
| CDC14B | 1.099903227 | 0.04349335 | 0.008228649 | 16.81917229 | 1.874444 | 2.406905 | 2.165421 | 6.857154 | 6.237456 | 5.446557 |
| PTGFR | 1.08773024 | 0.043485739 | 0.00870296 | 16.81917229 | 1.874444 | 2.023048 | 2.165421 | 5.252045 | 6.237456 | 6.195186 |
| MCART6 | 1.039699887 | 0.043577906 | 0.01031031 | 16.81917229 | 1.874444 | 2.023048 | 2.165421 | 6.395481 | 6.237456 | 5.106393 |
| PTCHD1 | 0.999938973 | 0.043603337 | 0.011855053 | 16.81917229 | 1.874444 | 2.809601 | 2.165421 | 7.25991 | 6.237456 | 5.091834 |
| ROPN1 | 0.71461311 | 0.047877006 | 0.028352501 | 16.81917229 | 1.874444 | 2.023048 | 2.165421 | 6.183122 | 6.237456 | 2.921909 |
| AIM1 | 0.925773265 | 0.04407613 | 0.015088125 | 16.81617232 | 2.993831 | 2.406905 | 3.764125 | 7.135902 | 7.138979 | 5.426231 |
| SETDB2 | 1.02538999 | 0.043577906 | 0.01077033 | 16.80290348 | 3.839948 | 3.872014 | 3.935222 | 6.814118 | 7.942653 | 8.03232 |
| LRRC58 | 1.107321989 | 0.04349335 | 0.008004083 | 16.76993027 | 5.335413 | 4.351315 | 4.449894 | 8.41912 | 9.042712 | 8.60836 |
| UBR3 | 1.169193907 | 0.043453389 | 0.006447771 | 16.76965563 | 4.209882 | 3.770995 | 2.165421 | 7.771052 | 8.277663 | 7.695565 |
| MDP1 | 1.203877633 | 0.043453389 | 0.006168765 | 16.69999651 | 1.874444 | 1.874444 | 2.165421 | 6.063041 | 5.936219 | 7.152205 |
| NBN | 1.161123687 | 0.043453389 | 0.006590977 | 16.51799894 | 4.963044 | 3.32135 | 3.764125 | 7.99581 | 7.713236 | 7.825039 |
| ALG10B | 1.027375254 | 0.043577906 | 0.010668255 | 16.69002952 | 4.963044 | 3.32135 | 3.764125 | 7.99581 | 7.713236 | 7.825039 |
| DTWD2 | 1.16731277 | 0.043453389 | 0.000481797 | 16.68813024 | 4.209882 | 4.830496 | 4.449894 | 8.270632 | 9.053666 | 8.503924 |
| MEX3B | 1.163860821 | 0.043453389 | 0.006522627 | 16.62832223 | 3.350997 | 3.872014 | 3.935222 | 8.087444 | 7.406567 | 7.897492 |
| TRIM72 | 1.023989483 | 0.043577906 | 0.010865601 | 16.58930513 | 3.024504 | 2.809601 | 2.165421 | 7.167419 | 6.861783 | 5.580533 |
| LOC100132526 | 1.080190174 | 0.043516135 | 0.008965635 | 16.57030064 | 3.839948 | 4.830496 | 5.225216 | 8.190235 | 9.275744 | 8.579284 |
| ZNF483 | 1.064051433 | 0.043516135 | 0.009421572 | 16.5526081 | 6.846868 | 6.537655 | 7.107458 | 9.978073 | 10.932507 | 11.15645 |
| NT5DC1 | 1.202798468 | 0.043453389 | 0.005556992 | 16.51799894 | 1.874444 | 2.023048 | 2.165421 | 6.960054 | 5.920411 | 6.051818 |
| DMRT2 | 1.179700715 | 0.043453389 | 0.006168765 | 16.51799894 | 1.874444 | 2.023048 | 2.165421 | 8.488001 | 5.920411 | 6.051818 |
| FGF13 | 1.101245769 | 0.04349335 | 0.008181014 | 16.51799894 | 1.874444 | 2.406905 | 2.165421 | 6.067497 | 5.920411 | 6.649696 |
| ATP8A1 | 1.050056505 | 0.043568903 | 0.009929228 | 16.51799894 | 4.209882 | 2.023048 | 2.165421 | 6.954147 | 9.053666 | 6.051818 |
| BBS9 | 1.199031935 | 0.043453389 | 0.005713508 | 16.50063556 | 1.874444 | 2.023048 | 3.764125 | 7.037879 | 7.406567 | 7.152205 |
| POSTN | 1.117202388 | 0.043485739 | 0.007663151 | 16.50063556 | 1.874444 | 2.023048 | 2.165421 | 7.167419 | 6.861783 | 5.580533 |
| KNTC1 | 0.957429356 | 0.043835088 | 0.013555631 | 16.50063556 | 1.874444 | 2.023048 | 2.165421 | 6.067497 | 10.589051 | 6.32627 |
| FAM110B | 0.903908649 | 0.044173537 | 0.016240218 | 16.50063556 | 4.209882 | 2.023048 | 2.165421 | 6.067497 | 4.539173 | 6.385515 |
| LINC00339 | 0.820275383 | 0.045095391 | 0.020711807 | 16.50063556 | 1.874444 | 2.023048 | 2.165421 | 6.067497 | 6.373501 | 6.69026 |
| LOC100506776 | 0.64300694 | 0.05194815 | 0.036164682 | 16.50063556 | 1.874444 | 2.023048 | 5.609945 | 6.067497 | 6.373501 | 3.676349 |
| SKIV2L2 | 0.96795695 | 0.043738451 | 0.013061586 | 16.46869544 | 3.024504 | 2.023048 | 2.165421 | 7.582358 | 7.066159 | 6.455366 |
| SUGT1 | 1.057495826 | 0.043540291 | 0.009654985 | 16.45957435 | 2.993831 | 2.809601 | 3.324375 | 7.36523 | 7.269549 | 6.106561 |
| SHPRH | 1.147351929 | 0.043453389 | 0.009624124 | 16.45530902 | 1.874444 | 2.023048 | 2.165421 | 5.579836 | 5.857745 | 6.129407 |
| SLC30A6 | 1.117848363 | 0.043485739 | 0.007642736 | 16.45530902 | 1.874444 | 2.406905 | 2.165421 | 6.651882 | 6.205902 | 5.580533 |
| CPEB3 | 1.106679069 | 0.04349335 | 0.008010888 | 16.45530902 | 2.201691 | 2.023048 | 2.165421 | 6.954147 | 6.205902 | 5.426231 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| MRPL35 | 1.206455171 | 0.043453389 | 0.005468527 | 16.44974648 | 1.874444 | 2.023048 | 2.165421 | 6.063041 | 5.936219 | 6.106561 |
| GSTM4 | 1.196896227 | 0.043453389 | 0.005780878 | 16.44974648 | 1.874444 | 2.023048 | 2.165421 | 6.063041 | 5.857745 | 6.73963 |
| LOC100506409 | 1.004361262 | 0.043588662 | 0.011694454 | 16.44974648 | 4.263463 | 2.023048 | 2.165421 | 6.063041 | 7.713236 | 7.020304 |
| PTPN13 | 0.876132814 | 0.044280042 | 0.017610071 | 16.4310072 | 2.993831 | 4.80797 | 2.165421 | 6.252746 | 7.406567 | 7.03218 |
| VSIG1 | 1.141241209 | 0.043453389 | 0.007087445 | 16.42853806 | 2.201691 | 2.406905 | 2.995681 | 6.183122 | 6.613395 | 7.033813 |
| ADSS | 0.950415548 | 0.043900827 | 0.013885675 | 16.4174094 | 3.819732 | 2.023048 | 3.764125 | 7.856887 | 7.066159 | 6.106561 |
| NFIL3 | 1.091773068 | 0.0435113 | 0.008538959 | 16.37365648 | 6.678389 | 5.362142 | 7.401896 | 10.409498 | 10.711694 | 10.910165 |
| CPN2 | 1.063794065 | 0.043516135 | 0.009428377 | 16.35045117 | 1.874444 | 4.80797 | 3.935222 | 7.679787 | 8.077554 | 7.96648 |
| TGFBI | 1.091375482 | 0.0435113 | 0.008572984 | 16.3502397 | 6.381847 | 5.148082 | 6.769247 | 10.59581 | 10.413087 | 9.697401 |
| MYO5C | 1.109000745 | 0.043485739 | 0.007908132 | 16.33353083 | 2.993831 | 2.809601 | 2.165421 | 8.460842 | 6.551443 | 6.195186 |
| HDHD3 | 1.102868053 | 0.04349335 | 0.008112964 | 16.33353083 | 2.993831 | 2.023048 | 2.165421 | 7.144104 | 6.043524 | 6.195186 |
| COQ9 | 1.058205558 | 0.043540291 | 0.009600544 | 16.33353083 | 2.993831 | 3.32135 | 2.165421 | 6.651882 | 7.56803 | 6.195186 |
| VAMP7 | 1.024554446 | 0.043577906 | 0.01083838 | 16.33353083 | 3.819732 | 3.360637 | 2.165421 | 8.676869 | 7.094585 | 6.195186 |
| NOL8 | 1.003790483 | 0.043588662 | 0.011714869 | 16.33353083 | 2.993831 | 2.023048 | 2.165421 | 7.679787 | 5.306419 | 6.195186 |
| LPP-AS2 | 0.949875454 | 0.043900827 | 0.013899285 | 16.33899285 | 1.874444 | 2.023048 | 2.165421 | 6.063041 | 4.539173 | 6.195186 |
| GAPT | 1.173295554 | 0.043453389 | 0.006311671 | 16.32227493 | 1.874444 | 2.023048 | 2.165421 | 5.728038 | 6.319269 | 6.051818 |
| RP11-165H20.1 | 1.165541036 | 0.043453389 | 0.006502212 | 16.32227493 | 1.874444 | 2.023048 | 2.165421 | 5.705318 | 7.174648 | 6.051818 |
| STAR | 1.15766408 | 0.043453389 | 0.006679143 | 16.32227493 | 1.874444 | 2.023048 | 2.379345 | 6.063041 | 5.920411 | 6.051818 |
| IKZF1 | 1.042565168 | 0.043577906 | 0.010242259 | 16.29379656 | 1.874444 | 2.406905 | 2.995681 | 7.477873 | 5.920411 | 5.900694 |
| MARC2 | 0.906765906 | 0.044173537 | 0.010063287 | 16.29379656 | 1.874444 | 2.023048 | 4.285996 | 6.252746 | 7.174648 | 5.900694 |
| STAM | 0.781616303 | 0.04575418 | 0.023207894 | 16.29379656 | 1.874444 | 2.023048 | 5.389265 | 6.664985 | 7.107836 | 5.900694 |
| C2orf69 | 1.056540168 | 0.043540291 | 0.00968901 | 16.27239452 | 1.874444 | 2.023048 | 2.165421 | 8.139755 | 6.189775 | 5.446557 |
| AMD1 | 0.955436986 | 0.043840967 | 0.013568595 | 16.2646502 | 4.682076 | 5.340619 | 6.769247 | 9.968463 | 9.426624 | 8.705744 |
| MAOA | 0.824368702 | 0.044949653 | 0.020444369 | 16.25930205 | 6.054828 | 4.351315 | 2.165421 | 8.935488 | 6.551443 | 8.374509 |
| FBLN7 | 0.876668223 | 0.044280042 | 0.017589656 | 16.25525417 | 3.024504 | 3.770995 | 2.995681 | 5.252045 | 7.793829 | 7.428484 |
| PLEKHH1 | 1.20095235 | 0.043453389 | 0.006625043 | 16.22870191 | 1.874444 | 2.023048 | 2.165421 | 6.396698 | 6.043524 | 5.882028 |
| BLZF1 | 1.200025992 | 0.043453389 | 0.005693093 | 16.22870191 | 1.874444 | 2.023048 | 2.165421 | 6.252746 | 6.043524 | 5.882028 |
| ABCB10 | 1.19196571 | 0.043453389 | 0.005916979 | 16.22870191 | 1.874444 | 2.023048 | 2.165421 | 7.210813 | 6.043524 | 5.882028 |
| CD84 | 1.172599763 | 0.043453389 | 0.006338891 | 16.22870191 | 1.874444 | 2.023048 | 2.165421 | 5.728038 | 6.043524 | 6.32627 |
| LOC100129518 | 1.145188445 | 0.043453389 | 0.006964954 | 16.22870191 | 1.874444 | 2.023048 | 2.165421 | 5.579836 | 6.043524 | 6.385515 |
| TMEM144 | 1.123125975 | 0.043453389 | 0.0075022552 | 16.22870191 | 1.874444 | 2.023048 | 2.165421 | 5.448591 | 6.043524 | 6.722123 |
| OCIAD2 | 1.111782801 | 0.043485739 | 0.007853692 | 16.22870191 | 1.874444 | 2.023048 | 2.165421 | 8.811966 | 6.043524 | 5.446557 |
| SHANK2 | 1.067789003 | 0.043516135 | 0.009319496 | 16.22870191 | 1.874444 | 2.023048 | 2.165421 | 7.877571 | 6.043524 | 5.106393 |
| F8 | 1.062852533 | 0.043516135 | 0.009455597 | 16.19752558 | 2.201691 | 2.023048 | 2.165421 | 5.095353 | 6.043524 | 6.931222 |
| C11orf1 | 1.022686914 | 0.043577906 | 0.010290846 | 16.19752558 | 1.874444 | 2.023048 | 2.165421 | 8.222933 | 6.043524 | 4.790662 |
| UNG | 1.015231021 | 0.043581008 | 0.011246002 | 16.19752558 | 1.874444 | 2.023048 | 2.165421 | 4.802615 | 6.043524 | 7.033813 |
| C12orf26 | 0.98898028 | 0.043626235 | 0.012218442 | 16.19752558 | 1.874444 | 2.023048 | 2.165421 | 6.339437 | 6.043524 | 6.455366 |
| C5 | 0.943766096 | 0.043921714 | 0.014197346 | 16.22870191 | 1.874444 | 2.023048 | 2.165421 | 6.857154 | 6.043524 | 4.476242 |
| HSD17B2 | 0.907039354 | 0.044173537 | 0.010649677 | 16.22870191 | 1.874444 | 2.023048 | 2.379345 | 6.339437 | 6.043524 | 4.146207 |
| HEBP1 | 0.742134994 | 0.046946487 | 0.02618986 | 16.22870191 | 1.874444 | 2.023048 | 2.165421 | 7.556937 | 6.043524 | 2.921909 |
| TPTE2P6 | 1.201064883 | 0.043453389 | 0.005618237 | 16.19752558 | 1.874444 | 2.023048 | 2.379345 | 6.183122 | 5.857745 | 6.129407 |
| WDR70 | 1.10347609 | 0.04349335 | 0.008092548 | 16.19752558 | 2.201691 | 2.023048 | 2.165421 | 6.183122 | 6.774676 | 5.426231 |
| GNAI1 | 1.046293932 | 0.043577906 | 0.010106839 | 16.19752558 | 1.874444 | 2.023048 | 2.165421 | 6.183122 | 6.794431 | 5.106393 |
| UQCRB | 0.918388332 | 0.044110923 | 0.013568595 | 16.19752558 | 3.819732 | 2.023048 | 2.165421 | 6.183122 | 6.205902 | 6.106561 |
| MKRN2 | 1.183024864 | 0.043453389 | 0.006093909 | 16.19361071 | 2.201691 | 2.406905 | 2.379345 | 6.396698 | 6.794431 | 6.051818 |
| KLF10 | 1.106381225 | 0.04349335 | 0.008017693 | 16.1895139 | 5.335413 | 6.311907 | 5.974145 | 9.352401 | 10.463244 | 9.951121 |
| TIAL1 | 1.023983311 | 0.043577906 | 0.010872406 | 16.18762743 | 5.328526 | 4.911517 | 3.90836 | 9.352401 | 8.928336 | 7.748756 |
| GTF2F2 | 0.822099892 | 0.045048325 | 0.020604287 | 16.1872899 | 1.874444 | 4.750708 | 2.379345 | 5.891233 | 6.774676 | 6.587378 |
| C1orf210 | 1.105557384 | 0.04349335 | 0.008031303 | 16.17995492 | 1.874444 | 2.023048 | 2.379345 | 6.395481 | 6.237456 | 5.446557 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| SDAD1 | 0.91352748 | 0.044110923 | 0.015686968 | 16.17995492 | 2.993831 | 2.023048 | 2.379345 | 6.395481 | 7.066159 | 4.790662 |
| ARL1 | 0.988134533 | 0.043626235 | 0.012252467 | 16.11698423 | 5.753024 | 4.80797 | 3.764125 | 9.314972 | 9.009341 | 7.774634 |
| CLDN3 | 0.793855018 | 0.04542938 | 0.022433481 | 16.11698423 | 5.304463 | 7.598777 | 3.764125 | 10.492308 | 9.339793 | 7.774634 |
| FAM13C | 1.042909218 | 0.043577906 | 0.010221844 | 16.10357514 | 3.024504 | 2.406905 | 4.285996 | 8.254907 | 6.774676 | 7.033813 |
| LOC100506844 | 1.178589353 | 0.043453389 | 0.00620279 | 16.08433297 | 1.874444 | 2.023048 | 2.165421 | 5.891233 | 6.613395 | 5.882028 |
| IFIT2 | 1.17744273 | 0.043453389 | 0.00624362 | 16.08433297 | 1.874444 | 2.023048 | 2.165421 | 7.037879 | 5.920411 | 5.882028 |
| GLRX2 | 1.084152457 | 0.043516135 | 0.008798231 | 16.08433297 | 1.874444 | 2.023048 | 2.165421 | 6.252746 | 6.189775 | 5.882028 |
| ZNF720 | 1.024183313 | 0.043577906 | 0.010858796 | 16.08433297 | 1.874444 | 2.023048 | 3.324375 | 6.244586 | 6.551443 | 5.882028 |
| STK36 | 1.015306467 | 0.043581008 | 0.011239197 | 16.08433297 | 1.874444 | 2.023048 | 3.935222 | 6.960054 | 7.191402 | 5.882028 |
| EZH2 | 0.942225446 | 0.043921714 | 0.014285812 | 16.08433297 | 1.874444 | 3.32135 | 4.449894 | 7.877571 | 7.819723 | 5.882028 |
| FAM65B | 1.096605198 | 0.04349335 | 0.008344335 | 16.08262456 | 3.839948 | 2.023048 | 3.935222 | 6.960054 | 7.942653 | 7.800057 |
| MGC34034 | 1.108719884 | 0.043485739 | 0.007942157 | 16.06522034 | 2.201691 | 3.32135 | 2.165421 | 6.067497 | 6.78473 | 7.327219 |
| ICK | 0.974907063 | 0.043661316 | 0.012748554 | 16.05101743 | 1.874444 | 3.360637 | 2.165421 | 7.36523 | 6.78473 | 5.091834 |
| SUSD3 | 1.070154257 | 0.043516135 | 0.009244641 | 16.04677342 | 2.201691 | 2.406905 | 2.165421 | 5.448591 | 6.205902 | 6.587378 |
| HMGN2 | 1.11339629 | 0.043485739 | 0.007806056 | 16.01930674 | 2.201691 | 2.809601 | 2.165421 | 6.811341 | 5.857745 | 6.455366 |
| COL4A5 | 0.680958882 | 0.049464555 | 0.031548146 | 16.01930674 | 1.874444 | 2.406905 | 2.379345 | 6.811341 | 6.549959 | 2.921909 |
| MCTP2 | 1.159091449 | 0.043453389 | 0.006638312 | 16.01729401 | 3.350997 | 3.770995 | 3.324375 | 7.995811 | 7.269549 | 7.352555 |
| PRKG1 | 1.142078156 | 0.043453389 | 0.007046614 | 16.00588013 | 1.874444 | 2.023048 | 2.995681 | 6.954147 | 6.794431 | 5.874974 |
| CSRNP3 | 1.130917009 | 0.043453389 | 0.007318816 | 16.00588013 | 1.874444 | 2.406905 | 2.165421 | 5.891233 | 6.608026 | 5.874974 |
| TIFA | 1.113770163 | 0.043485739 | 0.007792446 | 16.00588013 | 1.874444 | 2.406905 | 2.379345 | 6.664985 | 5.936219 | 5.874974 |
| MARVELD2 | 1.078696107 | 0.043516135 | 0.00901327 | 16.00588013 | 8.234634 | 2.023048 | 3.324375 | 6.811341 | 6.774676 | 5.874974 |
| H1FX | 0.842492791 | 0.044657496 | 0.019273903 | 15.97792757 | 1.874444 | 5.43468 | 6.369239 | 9.60897 | 10.404555 | 10.367248 |
| LINC00476 | 1.061625485 | 0.043540291 | 0.009505274 | 15.95235121 | 5.263699 | 4.389936 | 2.995681 | 8.105092 | 8.385634 | 8.593895 |
| NME7 | 1.059726218 | 0.043540291 | 0.009539299 | 15.94326401 | 3.819732 | 2.406905 | 2.995681 | 7.814607 | 7.713236 | 6.129407 |
| BVES | 1.018186264 | 0.043577906 | 0.01130997 | 15.93531826 | 1.874444 | 2.406905 | 2.379345 | 5.026959 | 6.373501 | 6.924055 |
| LINC00092 | 1.114797282 | 0.043485739 | 0.007751616 | 15.87379945 | 1.874444 | 2.406905 | 2.165421 | 6.395481 | 7.598264 | 6.106561 |
| HELQ | 1.084701096 | 0.043516135 | 0.007844621 | 15.87379945 | 3.350997 | 2.406905 | 2.165421 | 6.395481 | 6.373501 | 7.033813 |
| RPS6KA1 | 1.027802355 | 0.043577906 | 0.010634229 | 15.86840013 | 2.201691 | 2.809601 | 2.165421 | 7.42265 | 6.189775 | 5.426231 |
| PDZD9 | 0.915332976 | 0.044110923 | 0.015564478 | 15.86840013 | 1.874444 | 2.023048 | 3.324375 | 5.026959 | 6.189775 | 7.36177 |
| SAR1B | 1.018526872 | 0.043577906 | 0.011124192 | 15.85871066 | 4.309025 | 4.750708 | 3.90836 | 9.307369 | 8.296229 | 7.218312 |
| CIZ1 | 0.914353585 | 0.044110923 | 0.015625723 | 15.84954932 | 4.209882 | 3.360637 | 3.90836 | 8.553743 | 7.89473 | 6.051818 |
| SGCE | 1.032146207 | 0.043577906 | 0.010507656 | 15.83861524 | 4.815804 | 4.911517 | 6.601009 | 8.801178 | 10.369915 | 9.438736 |
| CRYL1 | 0.779930703 | 0.045824482 | 0.023329704 | 15.83263961 | 1.874444 | 2.809601 | 2.165421 | 6.396698 | 6.794431 | 3.630092 |
| PPP1R1A | 1.103246763 | 0.04349335 | 0.008099354 | 15.83059 | 3.350997 | 2.023048 | 2.165421 | 7.33564 | 5.920411 | 6.942983 |
| LOC729678 | 1.171160778 | 0.043453389 | 0.00637972 | 15.82441302 | 3.024504 | 2.406905 | 3.324375 | 7.30543 | 7.414086 | 6.924055 |
| UVRAG | 0.91858925 | 0.044110923 | 0.015390249 | 15.81587015 | 1.874444 | 4.351315 | 2.995681 | 7.177844 | 5.857745 | 7.492252 |
| CP | 0.911082034 | 0.044159136 | 0.01583804 | 15.81587015 | 5.316227 | 3.360637 | 3.935222 | 8.875048 | 5.857745 | 6.32627 |
| TLN1 | 0.916199807 | 0.044110923 | 0.015516842 | 15.81092502 | 2.201691 | 5.362142 | 5.571599 | 9.344992 | 9.687973 | 7.748756 |
| B4GALT4 | 0.678088573 | 0.049604445 | 0.031832596 | 15.79538996 | 2.993831 | 2.406905 | 2.165421 | 6.183122 | 6.613395 | 2.921909 |
| MRPS14 | 0.828545961 | 0.044930476 | 0.020223205 | 15.79127519 | 2.993831 | 2.809601 | 3.324375 | 7.30543 | 7.094585 | 4.790662 |
| UVRAG | 0.890298043 | 0.044203301 | 0.016985369 | 15.77725776 | 3.839948 | 4.911517 | 4.754917 | 8.122528 | 7.819723 | 6.051818 |
| MRPL22 | 1.109694033 | 0.043485739 | 0.007928547 | 15.76452689 | 3.024504 | 2.406905 | 3.324375 | 6.954147 | 5.857745 | 6.385515 |
| KATNA1 | 1.088737307 | 0.043516135 | 0.00864852 | 15.75799488 | 4.743564 | 4.413323 | 5.544653 | 9.260886 | 8.97518 | 8.391335 |
| KCTD9 | 0.998794091 | 0.043626235 | 0.011876829 | 15.7535303 | 5.056498 | 3.872014 | 2.379345 | 7.36523 | 8.200916 | 7.849596 |
| DHTKD1 | 0.942772995 | 0.043921714 | 0.014265396 | 15.74112592 | 4.682076 | 2.023048 | 3.764125 | 6.283686 | 7.740604 | 8.407967 |
| ABTB1 | 1.007251376 | 0.043588662 | 0.011565158 | 15.72516028 | 3.350997 | 3.360637 | 2.165421 | 7.33564 | 6.205902 | 6.649696 |
| ARHGEF26 | 1.023509858 | 0.043577906 | 0.010886016 | 15.70619277 | 3.819732 | 2.023048 | 2.165421 | 7.792994 | 7.138979 | 5.634184 |
| EHD4 | 0.808664443 | 0.045247607 | 0.021461722 | 15.69113752 | 6.924263 | 9.104741 | 5.596986 | 13.076619 | 11.071037 | 9.061607 |
| CD24 | 1.059645933 | 0.043540291 | 0.009552909 | 15.68581543 | 5.328526 | 4.80797 | 3.764125 | 8.779359 | 9.218487 | 8.010706 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| SPTLC1 | 0.777757634 | 0.045844227 | 0.023471249 | 15.68368311 | 4.209882 | 2.809601 | 2.165421 | 6.811341 | 8.181074 | 4.562324 |
| DDX50 | 0.67203473 | 0.049993148 | 0.032517183 | 15.63379178 | 2.201691 | 2.406905 | 2.165421 | 6.283686 | 6.373501 | 2.921909 |
| MRPL50 | 0.94340021 | 0.043921714 | 0.014224566 | 15.61731819 | 1.874444 | 2.809601 | 2.165421 | 6.283686 | 6.774676 | 4.790662 |
| CORO1C | 1.128621809 | 0.044453389 | 0.007366451 | 15.61535602 | 2.201691 | 4.389936 | 4.285996 | 7.748771 | 8.296229 | 8.25089 |
| NGDN | 1.094045272 | 0.04349335 | 0.008439605 | 15.60902004 | 4.639409 | 4.389936 | 4.508334 | 7.814607 | 8.986657 | 8.472642 |
| ADH1B | 0.99339247 | 0.043626235 | 0.012068731 | 15.60447739 | 4.743564 | 3.872014 | 6.072169 | 7.835902 | 9.188984 | 9.922465 |
| CA5B | 0.995051845 | 0.043626235 | 0.012034706 | 15.58823665 | 6.186289 | 4.736586 | 6.450701 | 8.734704 | 10.413087 | 10.070856 |
| LOC100128071 | 0.995972401 | 0.043626235 | 0.011993875 | 15.58601781 | 4.743564 | 2.406905 | 4.285996 | 7.70315 | 7.191402 | 8.705744 |
| EBP | 1.100867876 | 0.04349335 | 0.008187819 | 15.54594117 | 1.874444 | 2.809601 | 2.995681 | 6.954147 | 6.549959 | 6.195186 |
| FBXL19-AS1 | 1.063135817 | 0.043516135 | 0.009435182 | 15.53774345 | 8.129608 | 7.786385 | 7.884888 | 11.107978 | 12.316817 | 11.842593 |
| PFDN5 | 1.010186089 | 0.043581008 | 0.011429738 | 15.47039008 | 6.617556 | 6.42919 | 7.156853 | 10.706903 | 11.108291 | 9.649245 |
| GPR172A | 0.855713734 | 0.044416666 | 0.018571623 | 15.42208119 | 5.304463 | 3.770995 | 2.379345 | 8.033165 | 7.989035 | 6.32627 |
| ACADSB | 1.12379237 | 0.044453389 | 0.007468527 | 15.40392692 | 5.866559 | 5.362142 | 3.764125 | 9.307369 | 9.266358 | 9.430619 |
| RNF31 | 0.916275239 | 0.044110923 | 0.015510037 | 15.37209431 | 3.024504 | 3.770995 | 4.449894 | 6.063041 | 7.713236 | 8.822008 |
| DBT | 1.12233991 | 0.043480953 | 0.007528411 | 15.36463959 | 4.209882 | 5.297868 | 5.592916 | 8.811966 | 9.484439 | 9.23941 |
| DYNLT1 | 0.995517476 | 0.043626235 | 0.012014291 | 15.36035749 | 3.024504 | 4.389936 | 2.165421 | 7.679787 | 8.077554 | 6.106561 |
| XPA | 0.986050683 | 0.04349335 | 0.012334127 | 15.36035749 | 2.201691 | 2.023048 | 2.165421 | 6.894482 | 6.189775 | 6.106561 |
| ACAT2 | 1.10226965 | 0.043626235 | 0.008126574 | 15.34742142 | 2.993831 | 2.023048 | 2.379345 | 6.814118 | 6.319269 | 6.106561 |
| TMEM110 | 1.042187686 | 0.043577906 | 0.010249064 | 15.34742142 | 4.963444 | 5.362142 | 2.379345 | 6.664985 | 6.319269 | 6.106561 |
| ERI2 | 0.922509057 | 0.044091888 | 0.015225587 | 15.34742142 | 6.008206 | 6.391145 | 6.282905 | 6.067497 | 6.319269 | 4.476242 |
| LMBRD1 | 0.863932642 | 0.044377262 | 0.018164682 | 15.34742142 | 1.874444 | 2.809601 | 2.379345 | 7.814607 | 6.319269 | 4.146207 |
| IL2 | 0.926206997 | 0.04406867 | 0.01504049 | 15.30080031 | 1.874444 | 2.023048 | 3.324375 | 7.25991 | 6.551443 | 4.790662 |
| DHX16 | 0.891621106 | 0.044203301 | 0.016924124 | 15.28134145 | 5.056948 | 3.32135 | 3.324375 | 6.857154 | 7.25505 | 7.428484 |
| EEF1E1 | 0.672534904 | 0.049933984 | 0.032419871 | 15.28134145 | 1.874444 | 3.32135 | 2.165421 | 6.550689 | 7.25505 | 2.921909 |
| ARGLU1 | 0.968033541 | 0.043738451 | 0.013047976 | 15.27527206 | 5.700376 | 5.43468 | 6.031658 | 9.633502 | 10.24167 | 8.357484 |
| LOC100132352 | 1.073780256 | 0.043516135 | 0.00912215 | 15.2689873 | 2.993831 | 2.406905 | 2.165421 | 6.339437 | 7.138979 | 5.900694 |
| ACPP | 1.097258815 | 0.043577906 | 0.008317115 | 15.2637082 | 4.963444 | 5.362142 | 6.012527 | 8.895478 | 9.749902 | 9.67008 |
| C11orf63 | 1.109861953 | 0.043485739 | 0.007914937 | 15.26310806 | 6.008206 | 6.391145 | 6.282905 | 9.621288 | 10.72546 | 10.214881 |
| MPL | 1.075897604 | 0.043516135 | 0.009074515 | 15.26216166 | 4.263463 | 3.360637 | 3.324375 | 7.243046 | 7.292524 | 8.440667 |
| AP3B1 | 0.988363424 | 0.043626235 | 0.012245662 | 15.26216166 | 3.839948 | 3.360637 | 2.165421 | 8.346785 | 7.292524 | 5.882028 |
| LYPLA1 | 0.930621252 | 0.043485739 | 0.016784621 | 15.26216166 | 4.309025 | 3.360637 | 2.379345 | 8.566539 | 7.292524 | 5.874974 |
| P2RY8 | 1.046390045 | 0.043577906 | 0.010093229 | 15.25473049 | 1.874444 | 3.360637 | 2.995681 | 6.550689 | 6.237456 | 7.291822 |
| LOC100130872 | 1.081678059 | 0.043516135 | 0.008877169 | 15.24934087 | 3.024504 | 2.023048 | 3.324375 | 6.814118 | 7.25505 | 6.32627 |
| KIAA1324 | 0.876947813 | 0.04428042 | 0.017569241 | 15.2409551 | 2.993831 | 6.228068 | 5.389265 | 10.157949 | 8.855089 | 7.395512 |
| ARHGEF7 | 1.041393143 | 0.043577906 | 0.010262674 | 15.24035342 | 6.099991 | 6.139057 | 6.031658 | 10.029816 | 9.075328 | 10.924687 |
| GABARAPL2 | 1.093851028 | 0.04349335 | 0.00844644 | 15.23974469 | 5.328526 | 4.80797 | 2.995681 | 9.102956 | 8.737737 | 8.32282 |
| CDON | 0.993158488 | 0.043626235 | 0.012089146 | 15.21810394 | 2.201691 | 2.023048 | 2.379345 | 4.894482 | 7.25505 | 6.129407 |
| BBS1 | 1.100753942 | 0.04349335 | 0.008215039 | 15.15472702 | 2.201691 | 3.32135 | 2.995681 | 7.243046 | 6.549959 | 6.69026 |
| CLEC2D | 0.845499903 | 0.044641179 | 0.019145968 | 15.15219467 | 4.743564 | 3.32135 | 6.450701 | 8.665019 | 9.608485 | 7.291822 |
| EPB41L5 | 0.891191139 | 0.044203301 | 0.016944539 | 15.13026614 | 3.024504 | 2.406905 | 4.754917 | 8.711848 | 6.549959 | 6.32627 |
| CNOT2 | 0.907307763 | 0.044173537 | 0.016036067 | 15.11027913 | 2.993831 | 4.750708 | 6.012527 | 9.171571 | 8.668166 | 7.46072 |
| CYP27C1 | 0.933420351 | 0.044025007 | 0.01467574 | 15.08371432 | 3.839948 | 4.413323 | 4.285996 | 6.550689 | 8.200916 | 8.732403 |
| MRPS28 | 1.140216094 | 0.044453389 | 0.007155495 | 15.06544747 | 1.874444 | 2.023048 | 2.165421 | 7.167419 | 5.936219 | 5.634184 |
| NEK3 | 1.116947249 | 0.043485739 | 0.007683566 | 15.06544747 | 1.874444 | 2.023048 | 2.379345 | 6.857154 | 5.936219 | 5.634184 |
| MRPS17 | 1.056231906 | 0.04354029 | 0.009723035 | 15.06544747 | 1.874444 | 2.023048 | 2.165421 | 7.177844 | 5.936219 | 5.106393 |
| SPTSSB | 1.054192823 | 0.043568903 | 0.009793127 | 15.06544747 | 1.874444 | 2.023048 | 2.165421 | 6.814118 | 5.936219 | 5.106393 |
| INE1 | 0.989526311 | 0.043626235 | 0.012191222 | 15.06544747 | 1.874444 | 2.023048 | 2.165421 | 6.283686 | 5.936219 | 4.790662 |
| FNBP1L | 0.957201121 | 0.043835088 | 0.013562436 | 15.06544747 | 1.874444 | 2.023048 | 2.165421 | 7.177844 | 5.936219 | 4.476242 |
| NEK10 | 0.906074446 | 0.044173537 | 0.016097312 | 15.06544747 | 1.874444 | 2.023048 | 2.165421 | 4.341916 | 5.936219 | 6.106561 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| ATP5EP2 | 0.869137359 | 0.044335719 | 0.017915618 | 15.06544747 | 1.874444 | 2.023048 | 2.165421 | 8.540832 | 5.936219 | 3.676349 |
| LOC389493 | 0.800678786 | 0.045343936 | 0.021938755 | 15.06544747 | 1.874444 | 2.023048 | 2.165421 | 6.244586 | 5.936219 | 3.630092 |
| RNF39 | 0.749384944 | 0.044671806 | 0.025669956 | 15.06544747 | 1.874444 | 2.023048 | 2.165421 | 7.477873 | 5.936219 | 2.921909 |
| ZNF92 | 0.747630928 | 0.046678073 | 0.025801973 | 15.06544747 | 1.874444 | 2.023048 | 2.165421 | 7.42265 | 5.936219 | 2.921909 |
| L1TD1 | 0.702022973 | 0.048553714 | 0.029645458 | 15.06544747 | 1.874444 | 2.023048 | 2.165421 | 6.244586 | 5.936219 | 2.921909 |
| CBX3 | 1.066499318 | 0.043516135 | 0.009360327 | 15.06348089 | 5.491121 | 6.044198 | 5.702912 | 10.351527 | 9.615895 | 8.974957 |
| GREB1 | 0.953590882 | 0.044025007 | 0.01464852 | 15.05866404 | 2.201691 | 2.809601 | 4.285996 | 6.814118 | 6.551443 | 6.722123 |
| ATF7IP2 | 0.712023892 | 0.0479972 | 0.028583192 | 15.05866404 | 3.024504 | 2.809601 | 6.054038 | 7.25991 | 7.066159 | 6.722123 |
| KIAA1797 | 1.084708438 | 0.043516135 | 0.008777816 | 15.05701907 | 2.993831 | 2.406905 | 2.165421 | 6.550689 | 6.319269 | 6.106561 |
| PCOLCE | 0.909519107 | 0.044173036 | 0.015939435 | 15.05480822 | 4.209882 | 5.43468 | 6.601009 | 8.173604 | 9.860086 | 9.346832 |
| PHKB | 1.145669497 | 0.043453389 | 0.006958149 | 15.04055951 | 4.815804 | 4.80797 | 4.508334 | 8.41912 | 8.97518 | 8.519314 |
| ZNF22 | 0.948332618 | 0.043900827 | 0.013974141 | 15.02944361 | 4.682076 | 2.809601 | 2.995681 | 8.591796 | 8.119857 | 5.882028 |
| MAP3K8 | 1.097546007 | 0.04349335 | 0.008289895 | 15.02103452 | 3.819732 | 3.360637 | 3.935222 | 8.864724 | 7.269549 | 7.395512 |
| GNPNAT1 | 0.971790749 | 0.043681142 | 0.012906431 | 15.01978267 | 1.874444 | 2.023048 | 2.379345 | 7.679787 | 5.936219 | 6.129407 |
| SLIT3 | 1.069585236 | 0.043516135 | 0.009271861 | 15.0145002 | 4.815804 | 4.351315 | 5.225216 | 8.173604 | 8.724289 | 8.784285 |
| TMEM25 | 1.09245722 | 0.04349335 | 0.008507656 | 15.02944361 | 5.056948 | 3.32135 | 5.702912 | 9.252991 | 8.963611 | 8.70819 |
| GPR116 | 0.962137188 | 0.043778104 | 0.013282749 | 14.9993165 | 5.328526 | 3.360637 | 6.355801 | 7.814607 | 7.138979 | 9.899123 |
| PPM1K | 1.122244487 | 0.043480953 | 0.007535216 | 14.97900623 | 2.201691 | 2.023048 | 2.379345 | 5.705318 | 6.613395 | 6.106561 |
| C1orf122 | 0.889558756 | 0.044203301 | 0.017019394 | 14.97900623 | 4.815804 | 4.351315 | 4.754917 | 8.895478 | 7.96603 | 6.106561 |
| CES1P1 | 0.913785341 | 0.044110923 | 0.015673358 | 14.97555838 | 3.350997 | 2.406905 | 5.225216 | 8.173604 | 8.724289 | 7.255535 |
| LINC00294 | 0.982376304 | 0.043626235 | 0.012490643 | 14.97449355 | 5.856559 | 4.736586 | 6.355801 | 8.641022 | 9.809281 | 9.894518 |
| FAM179B | 0.98371443 | 0.043622635 | 0.012415788 | 14.97052598 | 3.350997 | 2.023048 | 2.165421 | 5.252045 | 7.25505 | 6.722123 |
| DTWD1 | 0.969813435 | 0.043726704 | 0.012989452 | 14.92378811 | 3.024504 | 2.406905 | 4.508334 | 6.550689 | 8.160956 | 6.924055 |
| PLS3 | 1.089569628 | 0.043516135 | 0.00860769 | 14.91857584 | 2.201691 | 3.872014 | 2.379345 | 7.771052 | 7.713236 | 6.051818 |
| CHM | 1.079454559 | 0.04349335 | 0.008979245 | 14.90976367 | 5.897292 | 4.389936 | 4.724406 | 8.254907 | 9.563208 | 9.795477 |
| LOC440028 | 1.091750436 | 0.0435113 | 0.008545764 | 14.90392508 | 2.201691 | 2.023048 | 2.165421 | 6.063041 | 7.656894 | 5.426231 |
| CABP4 | 1.021166109 | 0.043577906 | 0.010981286 | 14.90392508 | 1.874444 | 2.023048 | 2.165421 | 6.063041 | 6.043524 | 6.618407 |
| CD200 | 1.008071429 | 0.043581008 | 0.011518203 | 14.90392508 | 2.201691 | 3.360637 | 2.165421 | 6.063041 | 6.319269 | 6.32627 |
| TSLP | 0.681896925 | 0.049428793 | 0.031493025 | 14.90392508 | 2.201691 | 2.023048 | 2.165421 | 6.063041 | 6.205902 | 2.921909 |
| ATG10 | 1.133527843 | 0.043453389 | 0.007250766 | 14.9012633 | 1.874444 | 2.023048 | 2.165421 | 6.395481 | 5.920411 | 5.580533 |
| COX7A2L | 1.105200863 | 0.04349335 | 0.008044913 | 14.9012633 | 1.874444 | 2.023048 | 2.165421 | 5.448591 | 5.920411 | 6.106561 |
| C2orf77 | 1.070094806 | 0.043516135 | 0.009251446 | 14.9012633 | 1.874444 | 2.023048 | 2.165421 | 5.252045 | 5.920411 | 6.195186 |
| EYS | 1.051232855 | 0.043568903 | 0.009895202 | 14.9012633 | 1.874444 | 2.023048 | 2.165421 | 6.651882 | 5.920411 | 5.106393 |
| IGSF1 | 1.008254721 | 0.043581008 | 0.011484178 | 14.9012633 | 2.201691 | 2.023048 | 2.165421 | 7.607339 | 5.920411 | 4.790662 |
| ESRP1 | 1.007343243 | 0.043588662 | 0.011551548 | 14.9012633 | 1.874444 | 2.023048 | 2.165421 | 7.477873 | 5.920411 | 4.790662 |
| HMGCS2 | 0.944793283 | 0.043921714 | 0.014149711 | 14.9012633 | 1.874444 | 2.023048 | 2.165421 | 10.70979 | 5.920411 | 4.146207 |
| RAMP3 | 0.929852912 | 0.044037172 | 0.014820687 | 14.9012633 | 1.874444 | 2.023048 | 3.935222 | 5.579836 | 5.920411 | 8.534542 |
| LZIC | 0.906097767 | 0.044173537 | 0.016090507 | 14.9012633 | 1.874444 | 2.023048 | 2.165421 | 6.395481 | 5.920411 | 4.146207 |
| CD40LG | 0.880465417 | 0.044278935 | 0.017429058 | 14.9012633 | 1.874444 | 2.023048 | 2.165421 | 6.283686 | 5.920411 | 4.146207 |
| LOC100505718 | 0.738165652 | 0.047140798 | 0.026539639 | 14.9012633 | 1.874444 | 2.023048 | 2.165421 | 7.167419 | 5.920411 | 2.921909 |
| COQ3 | 0.705498815 | 0.048378239 | 0.029294998 | 14.9012633 | 4.209882 | 3.32135 | 3.324375 | 6.339437 | 5.920411 | 2.921909 |
| LOC645212 | 1.084083159 | 0.043516135 | 0.008811841 | 14.89711874 | 5.304463 | 3.360637 | 2.165421 | 7.877571 | 7.414086 | 7.218312 |
| TMEM208 | 0.840841224 | 0.044701668 | 0.019433141 | 14.87582306 | 2.201691 | 3.360637 | 2.165421 | 7.607339 | 6.549959 | 7.255535 |
| SPOPL | 0.952030919 | 0.043900827 | 0.013817625 | 14.87082418 | 1.874444 | 3.360637 | 4.944468 | 8.40494 | 7.25505 | 6.73963 |
| C8orf45 | 0.946777657 | 0.04349335 | 0.014055801 | 14.87082418 | 4.639409 | 3.360637 | 2.165421 | 6.857154 | 7.25505 | 7.291822 |
| NAMPT | 1.095043344 | 0.04349335 | 0.00841919 | 14.84932626 | 7.641685 | 6.270596 | 6.450701 | 11.483507 | 10.162922 | 11.276797 |
| C14orf159 | 1.107740283 | 0.043485739 | 0.007969377 | 14.84648683 | 3.350997 | 2.406905 | 3.324375 | 7.243046 | 7.174648 | 6.618407 |
| C14orf23 | 0.960177616 | 0.043802358 | 0.01339299 | 14.82074755 | 5.263699 | 3.360637 | 4.508334 | 7.177844 | 8.402869 | 9.153246 |
| FERMT3 | 0.888585195 | 0.044203301 | 0.017073835 | 14.81707367 | 4.209882 | 2.023048 | 4.285996 | 5.743334 | 8.119857 | 8.175185 |

TABLE 8-continued

Differentially Expressed Genes in CD10-, CD24-, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| SPATA7 | 1.080032193 | 0.043516135 | 0.00897244 | 14.78843233 | 1.874444 | 2.023048 | 2.165421 | 5.320955 | 5.936219 | 6.051818 |
| RWDD3 | 1.019658474 | 0.043577906 | 0.011056142 | 14.78843233 | 2.201691 | 2.023048 | 2.165421 | 5.026959 | 6.640994 | 6.051818 |
| PEX19 | 0.765904251 | 0.046178907 | 0.024413066 | 14.78843233 | 5.700376 | 3.32135 | 2.165421 | 7.30543 | 7.96603 | 6.051818 |
| TPTE2P1 | 1.008448006 | 0.043581008 | 0.011463763 | 14.74759853 | 7.392123 | 7.106065 | 7.250844 | 10.174762 | 11.149721 | 11.274531 |
| A2M | 0.953829485 | 0.043857532 | 0.01371555 | 14.73474231 | 6.554045 | 6.228068 | 6.919905 | 9.196483 | 10.450867 | 10.801055 |
| DEF6 | 1.042854013 | 0.043577906 | 0.010228649 | 14.72972682 | 3.839948 | 2.809601 | 2.379345 | 7.582358 | 6.549959 | 6.69026 |
| F11R | 1.005529275 | 0.043588662 | 0.011633209 | 14.71116825 | 5.304463 | 6.060401 | 3.324375 | 9.939241 | 8.764653 | 8.519314 |
| SFMBT2 | 1.039530845 | 0.043577906 | 0.010317115 | 14.70365259 | 2.201691 | 2.023048 | 2.165421 | 7.995811 | 6.043524 | 5.091834 |
| FAM107A | 1.007288843 | 0.043588662 | 0.011558353 | 14.70365259 | 3.350997 | 3.32135 | 2.165421 | 6.498222 | 6.043524 | 10.265959 |
| FH | 0.965384678 | 0.043778104 | 0.013180674 | 14.70365259 | 2.201691 | 2.023048 | 2.165421 | 8.190235 | 6.043524 | 4.562324 |
| MPEG1 | 0.786950329 | 0.045564387 | 0.022815924 | 14.70365259 | 2.201691 | 2.023048 | 2.165421 | 6.244586 | 6.043524 | 3.676349 |
| FAT3 | 1.171925002 | 0.043453389 | 0.006366111 | 14.69900523 | 1.874444 | 2.023048 | 2.165421 | 5.891233 | 5.920411 | 5.900694 |
| ATP1A2 | 1.127206025 | 0.043453389 | 0.007414086 | 14.69900523 | 1.874444 | 2.023048 | 2.379345 | 5.728038 | 6.794431 | 5.900694 |
| UBAC2 | 1.127089011 | 0.043453389 | 0.007420891 | 14.69900523 | 1.874444 | 2.023048 | 2.379345 | 5.728038 | 6.608026 | 5.900694 |
| REP15 | 1.086761093 | 0.043516135 | 0.00871657 | 14.69900523 | 1.874444 | 2.023048 | 2.165421 | 5.320955 | 7.174648 | 5.900694 |
| THEMIS | 1.084339722 | 0.043516135 | 0.008791426 | 14.69900523 | 1.874444 | 2.023048 | 2.379345 | 7.771052 | 5.317867 | 5.900694 |
| RBMX | 1.062869837 | 0.043516135 | 0.009448792 | 14.69900523 | 1.874444 | 2.023048 | 2.379345 | 6.954147 | 5.317867 | 5.900694 |
| SLC35F3 | 1.058130996 | 0.043540291 | 0.009607349 | 14.69900523 | 1.874444 | 2.023048 | 2.165421 | 6.498222 | 5.165949 | 5.900694 |
| ZNF821 | 0.968907424 | 0.043738451 | 0.013043365 | 14.69900523 | 3.839948 | 2.023048 | 2.165421 | 6.244586 | 7.440337 | 5.900694 |
| TTC18 | 0.910744523 | 0.044159136 | 0.015851665 | 14.69900523 | 2.201691 | 2.023048 | 3.764125 | 6.244586 | 6.205902 | 5.900694 |
| MUC21 | 0.855239925 | 0.044416666 | 0.018585233 | 14.69900523 | 1.874444 | 2.023048 | 2.165421 | 4.013424 | 6.205902 | 5.900694 |
| DYRK4 | 0.787842675 | 0.045562713 | 0.0227574 | 14.69018878 | 4.639409 | 2.023048 | 2.165421 | 6.067497 | 6.551443 | 5.106393 |
| TMPRSS13 | 1.021230132 | 0.043577906 | 0.010974481 | 14.69018878 | 1.874444 | 2.406905 | 2.165421 | 6.283686 | 6.205902 | 9.192178 |
| DST | 1.002367366 | 0.043588662 | 0.011762504 | 14.68173311 | 5.316227 | 7.197097 | 5.571599 | 10.110676 | 10.701282 | 9.103055 |
| ACTB | 0.883471677 | 0.044229452 | 0.017304525 | 14.68146335 | 5.982974 | 6.762934 | 4.449894 | 10.638857 | 8.486085 | 9.446808 |
| RUNX1T1 | 0.724769831 | 0.047575442 | 0.027518884 | 14.67419411 | 5.056948 | 3.770995 | 5.571599 | 5.705318 | 9.1177 | 7.640338 |
| HCG22 | 1.023243968 | 0.043577906 | 0.010899626 | 14.61464827 | 2.201691 | 3.770995 | 2.165421 | 5.579836 | 7.406567 | 7.640338 |
| LCOR | 0.981570763 | 0.043626235 | 0.012517863 | 14.61464827 | 3.350997 | 3.770995 | 4.944468 | 8.222933 | 7.31791 | 5.882028 |
| KIAA1731 | 1.155743353 | 0.043453389 | 0.006726778 | 14.61006678 | 1.874444 | 2.023048 | 2.165421 | 5.743334 | 6.613395 | 6.106561 |
| LOC100132987 | 1.153432242 | 0.043453389 | 0.006767608 | 14.61006678 | 1.874444 | 2.023048 | 2.165421 | 5.743334 | 5.857745 | 6.051818 |
| POP5 | 1.002247453 | 0.043588662 | 0.011769309 | 14.61006678 | 1.874444 | 3.32135 | 2.165421 | 5.743334 | 7.066159 | 8.472642 |
| C10orf58 | 0.882850966 | 0.044229452 | 0.01732494 | 14.6070175 | 6.054828 | 3.872014 | 4.285996 | 8.433162 | 7.740604 | 6.931222 |
| IF146 | 1.13054837 | 0.043453389 | 0.007339231 | 14.60292315 | 2.201691 | 2.023048 | 2.379345 | 5.891233 | 5.936219 | 6.69026 |
| NCKAP5 | 1.08518875 | 0.043516135 | 0.008750595 | 14.60292315 | 1.874444 | 2.023048 | 2.165421 | 5.891233 | 5.317867 | 6.106561 |
| LY86-AS1 | 1.055465856 | 0.043540291 | 0.00975706 | 14.60292315 | 1.874444 | 2.023048 | 2.995681 | 5.891233 | 6.608026 | 6.106561 |
| TRMT11 | 1.039317854 | 0.043577906 | 0.01032392 | 14.60292315 | 2.201691 | 2.023048 | 2.165421 | 5.891233 | 6.237456 | 5.091834 |
| VCPIP1 | 0.945616065 | 0.043921714 | 0.014115686 | 14.60292315 | 1.874444 | 2.023048 | 2.165421 | 5.891233 | 6.237456 | 4.562324 |
| LEKR1 | 0.795967407 | 0.045374706 | 0.022247703 | 14.60056002 | 1.874444 | 2.023048 | 2.165421 | 6.244586 | 6.043524 | 3.676349 |
| CMAS | 0.87828841 | 0.044280042 | 0.017521606 | 14.59745244 | 2.993897 | 5.195784 | 5.389265 | 8.875048 | 6.861783 | 4.562324 |
| CLSTN1 | 1.065102349 | 0.043516135 | 0.009387547 | 14.5818471 | 5.982974 | 2.406905 | 4.285996 | 8.433162 | 9.25691 | 10.421501 |
| TCEAL1 | 0.901285671 | 0.044203301 | 0.016394012 | 14.57886787 | 2.201691 | 4.750708 | 2.995681 | 6.814118 | 6.861783 | 4.562324 |
| CCDC163P | 0.764010394 | 0.046193441 | 0.024534195 | 14.57725795 | 10.655041 | 10.67631 | 11.046193 | 14.200262 | 6.043524 | 6.385515 |
| RPL11 | 1.084852853 | 0.043516135 | 0.00887574 | 14.55529887 | 5.335413 | 2.023048 | 4.944468 | 8.501391 | 14.541958 | 15.032296 |
| N4BP2L2 | 1.08901281 | 0.043516135 | 0.00863491 | 14.55295244 | 2.993831 | 3.872014 | 3.90836 | 7.771052 | 9.198885 | 8.636861 |
| SCAF8 | 1.11436828 | 0.043485739 | 0.007772031 | 14.54742582 | 4.263463 | 2.023048 | 2.995681 | 6.857154 | 7.406567 | 7.46072 |
| ZHX1 | 0.91762084 | 0.044110923 | 0.015441987 | 14.53513991 | 3.819732 | 2.406905 | 5.018694 | 7.679787 | 7.31791 | 6.051818 |
| GNG2 | 0.958424642 | 0.043826549 | 0.013483498 | 14.52085298 | 5.856559 | 4.750708 | 4.285996 | 10.641884 | 8.385634 | 3.676349 |
| HMGCS1 | 0.816660399 | 0.045162628 | 0.020920041 | 14.5130688 | 1.874444 | 2.023048 | 2.165421 | 6.498222 | 8.609988 | 6.942983 |
| LOC643770 | 1.117096804 | 0.043485739 | 0.007676761 | 14.51004335 | 1.874444 | 2.023048 | 2.165421 | 6.498222 | 5.509998 | 6.618407 |

TABLE 8-continued

Differentially Expressed Genes in CD10–, CD24–, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| DPP8 | 1.104099415 | 0.04349335 | 0.008072133 | 14.51004335 | 1.874444 | 2.023048 | 2.165421 | 5.448591 | 6.205902 | 5.882028 |
| LINC00488 | 1.05238887 | 0.043568903 | 0.009861177 | 14.51004335 | 1.874444 | 2.023048 | 2.165421 | 6.244586 | 5.165949 | 5.882028 |
| RIMKLB | 1.046530557 | 0.043577906 | 0.010072814 | 14.51004335 | 2.993831 | 2.023048 | 2.995681 | 6.664985 | 7.138979 | 5.882028 |
| PARP11 | 0.983663847 | 0.043626235 | 0.012422593 | 14.51004335 | 3.839948 | 2.023048 | 2.165421 | 6.544171 | 7.174648 | 5.882028 |
| C1GALT1 | 0.74650288 | 0.046800775 | 0.025893161 | 14.50130425 | 3.024504 | 2.023048 | 2.379345 | 7.177844 | 6.237456 | 3.676349 |
| INPP5E | 1.02264443 | 0.043577906 | 0.010933651 | 14.49692321 | 2.201691 | 3.360637 | 2.165421 | 6.183122 | 5.936219 | 7.218312 |
| HES2 | 0.952232611 | 0.043900827 | 0.01379789 | 14.49692321 | 1.874444 | 3.360637 | 3.324375 | 6.063041 | 6.237456 | 7.218312 |
| KCNJ8 | 0.786835204 | 0.045564387 | 0.022822729 | 14.47392391 | 5.779429 | 2.809601 | 3.324375 | 6.664985 | 6.551443 | 8.010706 |
| IKZF5 | 1.02091215 | 0.043577906 | 0.011001701 | 14.46131325 | 1.874444 | 3.872014 | 3.764125 | 7.726141 | 7.107836 | 6.73963 |
| MCM3 | 1.056412263 | 0.043540291 | 0.009709425 | 14.45597623 | 1.874444 | 3.32135 | 2.165421 | 5.728038 | 6.78473 | 6.924055 |
| SFR1 | 1.04609294 | 0.043577906 | 0.010120449 | 14.45597623 | 1.874444 | 2.809601 | 3.764125 | 5.728038 | 7.406567 | 7.180104 |
| LOC157273 | 0.899555091 | 0.044203301 | 0.016514461 | 14.45597623 | 1.874444 | 2.809601 | 3.935222 | 7.726141 | 7.870158 | 6.129407 |
| E2F5 | 1.082808963 | 0.043516135 | 0.008856754 | 14.43926926 | 1.874444 | 2.023048 | 2.165421 | 6.067497 | 5.353925 | 5.874974 |
| MBLAC2 | 1.077862218 | 0.043516135 | 0.010235454 | 14.43926926 | 1.874444 | 2.023048 | 2.165421 | 6.252746 | 5.306419 | 5.874974 |
| SLC35B3 | 1.042809801 | 0.043577906 | 0.010235454 | 14.43926926 | 2.993831 | 2.023048 | 2.165421 | 5.891233 | 7.107836 | 5.874974 |
| NGLY1 | 1.031533 | 0.043577906 | 0.010521266 | 14.43926926 | 3.350997 | 2.023048 | 2.995681 | 9.067384 | 6.640994 | 5.874974 |
| HTATIP2 | 1.025522546 | 0.043577906 | 0.010749915 | 14.43926926 | 1.874444 | 2.023048 | 2.165421 | 5.026959 | 6.205902 | 5.874974 |
| TDRD6 | 0.995138223 | 0.043626235 | 0.012027901 | 14.43926926 | 1.874444 | 2.023048 | 2.165421 | 6.664985 | 4.797798 | 5.874974 |
| UBA3 | 0.974612548 | 0.043661316 | 0.012762164 | 14.43926926 | 3.819732 | 2.023048 | 2.995681 | 6.664985 | 8.385634 | 5.874974 |
| GAS1 | 0.957906342 | 0.043835088 | 0.013521606 | 14.43926926 | 3.839948 | 2.023048 | 2.165421 | 7.243046 | 6.237456 | 5.874974 |
| ORC3 | 0.948191649 | 0.043900827 | 0.013980946 | 14.43926926 | 1.874444 | 2.023048 | 3.324375 | 7.25991 | 5.353925 | 5.874974 |
| AURKAPS1 | 0.853096372 | 0.044464174 | 0.018690711 | 14.43926926 | 1.874444 | 2.023048 | 2.165421 | 4.013424 | 6.189775 | 5.874974 |
| SERPINI1 | 1.088511877 | 0.043516135 | 0.008655325 | 14.42331974 | 4.743564 | 4.413323 | 4.754917 | 8.779359 | 7.96603 | 8.593895 |
| CTSH | 0.779294556 | 0.045829476 | 0.023356244 | 14.42331974 | 4.743564 | 4.389936 | 6.054038 | 6.651882 | 10.11666 | 8.593895 |
| SMOC2 | 0.981399472 | 0.043626235 | 0.012531473 | 14.41074015 | 4.263463 | 4.389936 | 2.379345 | 8.239009 | 7.89473 | 6.73963 |
| SNX2 | 1.118059859 | 0.043485739 | 0.007635931 | 14.40639168 | 5.056948 | 5.43468 | 4.508334 | 8.905585 | 8.842512 | 8.997112 |
| SAMD8 | 1.016826341 | 0.043581008 | 0.01184757 | 14.40593795 | 4.639409 | 3.32135 | 2.995681 | 8.488001 | 8.402869 | 6.455366 |
| RPS24 | 1.020996618 | 0.043577906 | 0.010988091 | 14.38182469 | 8.313476 | 7.885522 | 8.616497 | 12.64513 | 12.15965 | 11.283573 |
| DMTF1 | 1.067655726 | 0.043516135 | 0.009326301 | 14.34306104 | 2.993831 | 2.809601 | 2.165421 | 6.651882 | 7.440337 | 5.874974 |
| EEF1G | 1.107502832 | 0.043485739 | 0.007982987 | 14.33573698 | 9.127293 | 9.647142 | 9.369586 | 13.488686 | 12.910395 | 13.21983 |
| LOC256880 | 1.097410022 | 0.0082967 | 0.013357605 | 14.32134049 | 4.309025 | 3.872014 | 4.508334 | 8.190235 | 7.713236 | 8.25089 |
| ZBTB38 | 0.960462082 | 0.043778104 | 0.016317115 | 14.31879496 | 4.743564 | 2.809601 | 2.995681 | 7.243046 | 8.119857 | 6.649696 |
| ZDHHC2 | 0.902605957 | 0.044190907 | 0.014997618 | 14.29740298 | 3.839948 | 2.406905 | 2.165421 | 7.679787 | 6.319269 | 5.426231 |
| CR1 | 0.926698613 | 0.044037172 | 0.011924464 | 14.29329005 | 4.815804 | 2.406905 | 3.324375 | 6.244586 | 7.56803 | 8.053616 |
| LRPPRC | 0.997623938 | 0.043778104 | 0.016317115 | 14.28599 | 4.351315 | 4.285996 | 3.90836 | 8.65307 | 8.314558 | 7.033813 |
| LOC644961 | 1.069548309 | 0.043516135 | 0.009278666 | 14.2860105 | 3.839948 | 4.351315 | 4.285996 | 8.122528 | 6.857154 | 10.161929 |
| C1QTNF9 | 0.805768824 | 0.045315307 | 0.021657707 | 14.27710635 | 5.304463 | 4.80797 | 5.018694 | 8.854326 | 7.31791 | 6.73963 |
| C1orf50 | 1.102002758 | 0.04349335 | 0.008146989 | 14.26785693 | 1.874444 | 2.023048 | 2.165421 | 6.244586 | 9.266358 | 5.446557 |
| CDC14A | 1.048785385 | 0.043577906 | 0.009977543 | 14.26785693 | 1.874444 | 2.023048 | 2.165421 | 7.33564 | 5.857745 | 5.106393 |
| TBCK | 1.044737712 | 0.043577906 | 0.010181014 | 14.26785693 | 1.874444 | 2.023048 | 2.165421 | 6.857154 | 5.857745 | 5.091834 |
| PDSS2 | 1.019411027 | 0.043577906 | 0.011069752 | 14.26785693 | 1.874444 | 2.023048 | 2.379345 | 6.664985 | 5.857745 | 5.091834 |
| EREG | 0.990539027 | 0.043626235 | 0.012170806 | 14.26785693 | 2.201691 | 2.023048 | 3.324375 | 7.177844 | 5.857745 | 5.882028 |
| PRPH | 0.989756962 | 0.043626235 | 0.012184416 | 14.26785693 | 1.874444 | 2.023048 | 2.165421 | 4.718672 | 5.857745 | 7.352555 |
| FAM82A1 | 0.983404192 | 0.043626235 | 0.012249813 | 14.26785693 | 1.874444 | 2.023048 | 2.165421 | 6.252746 | 5.857745 | 4.790662 |
| ESRRG | 0.983169318 | 0.043626235 | 0.012470228 | 14.26785693 | 1.874444 | 2.023048 | 2.165421 | 6.244586 | 5.857745 | 4.790662 |
| ANG | 0.975676969 | 0.043661316 | 0.012714529 | 14.26785693 | 1.874444 | 2.023048 | 2.165421 | 8.433162 | 5.857745 | 4.562324 |
| OMA1 | 0.944294196 | 0.043921714 | 0.014163321 | 14.26785693 | 1.874444 | 2.023048 | 2.165421 | 6.811341 | 5.857745 | 4.476242 |
| HARS2 | 0.851463723 | 0.044490827 | 0.018793467 | 14.26785693 | 1.874444 | 2.023048 | 2.165421 | 7.897963 | 5.857745 | 3.676349 |
| CKAP2 | 0.842228435 | 0.044657496 | 0.019307928 | 14.26785693 | 1.874444 | 2.023048 | 2.165421 | 7.748771 | 5.857745 | 3.630092 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| LOC221442 | 0.793585031 | 0.04542938 | 0.022440286 | 14.26785693 | 1.874444 | 2.023048 | 2.165421 | 6.183122 | 5.857745 | 3.630092 |
| NOXA1 | 0.742666896 | 0.046946487 | 0.026169445 | 14.26785693 | 1.874444 | 2.023048 | 2.165421 | 7.42265 | 5.857745 | 2.921909 |
| C8orf76 | 0.720622928 | 0.047703746 | 0.027855733 | 14.26785693 | 1.874444 | 2.023048 | 2.379345 | 7.25991 | 5.857745 | 2.921909 |
| APBB1IP | 0.686783046 | 0.04920934 | 0.030940456 | 14.26785693 | 1.874444 | 2.023048 | 2.379345 | 6.395481 | 5.857745 | 2.921909 |
| TMEM111 | 1.059624928 | 0.043540291 | 0.009559714 | 14.23522131 | 3.024504 | 2.809601 | 2.379345 | 7.726141 | 6.640994 | 5.900694 |
| KIAA0146 | 0.89273251 | 0.044203301 | 0.016876489 | 14.23522131 | 2.993831 | 2.809601 | 2.165421 | 8.628872 | 6.640994 | 4.562324 |
| SLC4A1AP | 1.143834603 | 0.043453389 | 0.006998979 | 14.23010699 | 1.874444 | 2.023048 | 2.165421 | 5.705318 | 5.936219 | 5.874974 |
| KLLN | 1.140594156 | 0.043453389 | 0.00713508 | 14.23010699 | 1.874444 | 2.023048 | 2.165421 | 5.705318 | 5.857745 | 5.900694 |
| LOC139201 | 1.121744558 | 0.043480953 | 0.007542021 | 14.23010699 | 1.874444 | 2.023048 | 2.379345 | 5.705318 | 5.936219 | 6.195186 |
| NSUN6 | 1.055981561 | 0.043540291 | 0.009736645 | 14.23010699 | 1.874444 | 2.023048 | 2.995681 | 5.705318 | 6.774676 | 6.129407 |
| FLJ43663 | 1.057027623 | 0.043540291 | 0.0096754 | 14.22903071 | 1.874444 | 3.360637 | 3.764125 | 7.394225 | 7.191402 | 6.618407 |
| MKL2 | 0.901228005 | 0.044203301 | 0.016400817 | 14.22691204 | 3.819732 | 2.406905 | 3.90836 | 8.591796 | 6.237456 | 6.455366 |
| ZFYVE9 | 0.99590569 | 0.043626235 | 0.012000681 | 14.21268621 | 3.350997 | 2.023048 | 2.165421 | 5.320955 | 6.794431 | 7.180104 |
| TMSB4X | 1.043907148 | 0.043577906 | 0.010201429 | 14.21237819 | 8.996009 | 8.644729 | 9.426087 | 12.513364 | 13.255163 | 12.475083 |
| INSIG1 | 0.981084043 | 0.043626235 | 0.012538278 | 14.20980575 | 5.856559 | 4.80797 | 6.450701 | 10.279516 | 9.847551 | 8.564524 |
| RRM2B | 0.900310527 | 0.044203301 | 0.016441647 | 14.15903323 | 3.350997 | 2.023048 | 3.935222 | 7.897963 | 7.174648 | 5.446357 |
| PABPC1 | 1.123186538 | 0.043453389 | 0.007482137 | 14.12956085 | 8.313476 | 8.299167 | 8.291057 | 12.838225 | 12.119812 | 11.833387 |
| ITGB1BP1 | 0.802070401 | 0.04534393 | 0.021887036 | 14.12606251 | 2.993831 | 2.023048 | 5.217616 | 6.814118 | 7.53715 | 6.129407 |
| ECM2 | 0.709198475 | 0.04824159 | 0.028872406 | 14.11803152 | 3.024504 | 2.023048 | 6.564874 | 7.074163 | 8.055928 | 7.180104 |
| RRAD | 1.011008732 | 0.043581008 | 0.011409323 | 14.10466763 | 5.056948 | 2.809601 | 4.724406 | 8.875048 | 7.713236 | 8.155622 |
| DAPK2 | 0.946377089 | 0.043900827 | 0.014083021 | 14.10005355 | 2.993831 | 3.32135 | 4.508334 | 8.665019 | 7.138979 | 6.455366 |
| LOC220906 | 1.140709197 | 0.043453389 | 0.007128275 | 14.08829911 | 4.682076 | 4.911517 | 4.724406 | 8.540832 | 9.064538 | 8.456743 |
| SHQ1 | 0.978733216 | 0.043661316 | 0.012592038 | 14.08258955 | 1.874444 | 2.023048 | 2.379345 | 4.802615 | 6.189775 | 6.195186 |
| CXCL3 | 0.749465998 | 0.046704093 | 0.025647499 | 14.07352354 | 4.263463 | 4.413323 | 6.670675 | 10.485586 | 9.962448 | 5.874974 |
| AAA1 | 1.018919503 | 0.043577906 | 0.011096972 | 14.07052669 | 2.201691 | 2.406905 | 3.324375 | 5.705318 | 7.138979 | 6.618407 |
| BSN-AS2 | 0.8385434 | 0.044732882 | 0.01958149 | 14.06473587 | 3.350997 | 3.360637 | 4.285996 | 5.728038 | 7.174648 | 8.155622 |
| DSP | 0.793880673 | 0.04542938 | 0.022426676 | 14.06009743 | 4.682076 | 7.631788 | 3.935222 | 10.548217 | 8.951948 | 7.748756 |
| PDLIM3 | 1.050566712 | 0.043568903 | 0.009915618 | 14.02742823 | 4.743564 | 4.413323 | 4.754917 | 8.553743 | 7.740604 | 9.040427 |
| MAP3K9 | 0.814221447 | 0.045212649 | 0.021144607 | 14.01408571 | 1.874444 | 2.809601 | 4.754917 | 6.063041 | 6.78473 | 6.618407 |
| PTPN18 | 0.973814798 | 0.043681142 | 0.012804355 | 14.00766253 | 3.819732 | 4.736586 | 3.764125 | 9.154721 | 7.627877 | 7.033813 |
| SBF2 | 0.970981042 | 0.043709154 | 0.012935692 | 13.99444021 | 4.309025 | 3.360637 | 2.165421 | 7.167419 | 7.713236 | 6.455366 |
| NDUFS3 | 1.110983164 | 0.043485739 | 0.007874107 | 13.99129137 | 5.335413 | 4.413323 | 5.225216 | 9.111713 | 9.031674 | 8.66481 |
| EHF | 0.7549496 | 0.046508764 | 0.025275264 | 13.97511937 | 5.304463 | 6.670655 | 2.379345 | 10.475444 | 9.188984 | 6.106561 |
| IMPA1 | 1.04772849 | 0.043577906 | 0.010025179 | 13.96656846 | 3.839948 | 2.023048 | 3.764125 | 7.607339 | 7.56803 | 6.69026 |
| SLC22A5 | 0.993512731 | 0.043626235 | 0.012055121 | 13.96532733 | 3.350997 | 3.360637 | 2.379345 | 6.183122 | 7.174648 | 6.649696 |
| PHYHD1 | 0.949445559 | 0.043900827 | 0.013912896 | 13.94617002 | 4.209882 | 3.360637 | 5.723602 | 8.553743 | 8.011679 | 7.96648 |
| FAM49A | 1.035537679 | 0.043577906 | 0.01040558 | 13.9191293 | 1.874444 | 2.406905 | 3.324375 | 6.954147 | 6.205902 | 6.051818 |
| RPS6KA6 | 1.008301876 | 0.043581008 | 0.011470568 | 13.9191293 | 1.874444 | 2.406905 | 2.995681 | 7.25991 | 6.205902 | 5.446357 |
| LOC100506207 | 0.926981767 | 0.044037172 | 0.014977203 | 13.9191293 | 1.874444 | 2.406905 | 3.764125 | 6.283686 | 6.205902 | 6.106561 |
| MGMT | 0.99141493 | 0.043626235 | 0.01215039 | 13.91361075 | 3.024504 | 2.809601 | 2.165421 | 5.448591 | 6.608026 | 7.395512 |
| KIAA1407 | 0.787533324 | 0.045564387 | 0.022788704 | 13.91361075 | 2.201691 | 2.809601 | 5.389265 | 6.283686 | 6.608026 | 7.640338 |
| PRMT5 | 1.017221766 | 0.043581008 | 0.011164342 | 13.90908257 | 5.753024 | 4.736586 | 4.508334 | 9.146221 | 8.502167 | 8.534542 |
| PATE4 | 1.097913468 | 0.04349335 | 0.008262674 | 13.9067527 | 5.491121 | 5.195784 | 5.571599 | 8.993498 | 9.722706 | 9.040427 |
| GNAI3 | 0.979191052 | 0.043656588 | 0.01258115 | 13.87348654 | 5.263699 | 4.830496 | 4.285996 | 9.276547 | 8.624754 | 7.611911 |
| ZNF621 | 1.033115094 | 0.043577906 | 0.01046002 | 13.86397202 | 4.209882 | 3.872014 | 4.944468 | 8.051486 | 8.737737 | 7.640338 |
| CCP110 | 0.902824777 | 0.044190907 | 0.0162967 | 13.85625192 | 4.263463 | 2.023048 | 4.754917 | 6.252746 | 8.055928 | 8.374509 |
| USPL1 | 1.024608342 | 0.043577906 | 0.010817965 | 13.84140973 | 4.309025 | 3.935222 | 3.935222 | 7.726141 | 8.436733 | 6.931222 |
| GTF2H2B | 1.087919069 | 0.043516135 | 0.008696155 | 13.84121555 | 2.993831 | 2.406905 | 2.995681 | 7.531061 | 6.78473 | 6.106561 |
| KIAA0586 | 0.913355773 | 0.04410923 | 0.015693773 | 13.82489366 | 4.815804 | 2.023048 | 3.764125 | 7.70315 | 6.613395 | 7.553321 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| WDR48 | 0.996653353 | 0.043626235 | 0.01197346 | 13.82347586 | 4.263463 | 3.360637 | 2.995681 | 8.122528 | 6.78473 | 7.033813 |
| ARHGAP15 | 0.884482085 | 0.044203301 | 0.017243961 | 13.81541049 | 1.874444 | 3.32135 | 4.754917 | 7.109557 | 6.189775 | 7.722406 |
| GALNT11 | 1.096665775 | 0.04349335 | 0.00833753 | 13.80562198 | 4.263463 | 4.351315 | 3.935222 | 8.222933 | 7.870158 | 7.722406 |
| LARP4 | 0.958079125 | 0.043835088 | 0.013507996 | 13.79894094 | 3.839948 | 3.32135 | 2.165421 | 7.109557 | 7.107836 | 6.106561 |
| SNAPC1 | 0.958065909 | 0.043626235 | 0.011910854 | 13.79697838 | 8.388231 | 7.08238 | 8.12722 | 10.880921 | 11.885468 | 12.174512 |
| EIF3H | 1.052757427 | 0.043568903 | 0.009840762 | 13.78898303 | 6.648293 | 7.26179 | 7.462086 | 11.610972 | 10.859474 | 10.433737 |
| CTTNBP2NL | 1.023614469 | 0.043577906 | 0.010879211 | 13.78647971 | 3.024504 | 2.406905 | 3.324375 | 7.109557 | 6.373501 | 6.32627 |
| RBM3 | 1.111044175 | 0.043485739 | 0.007867302 | 13.77507509 | 6.736762 | 6.537655 | 5.018694 | 10.321643 | 10.202833 | 10.345825 |
| DDX60L | 0.992112054 | 0.043626235 | 0.012129976 | 13.77004465 | 1.874444 | 2.406905 | 3.324375 | 5.448591 | 7.107836 | 6.587378 |
| EPS8 | 1.038325377 | 0.043577906 | 0.010357945 | 13.74532532 | 6.820119 | 6.03611 | 6.054038 | 9.663593 | 9.834907 | 11.049199 |
| DNAJC12 | 0.867949044 | 0.044335719 | 0.018566227 | 13.745096 | 2.993831 | 4.413323 | 2.379345 | 9.4454 | 6.774676 | 5.426231 |
| SGTB | 1.013718375 | 0.043581008 | 0.011314052 | 13.7289854 | 4.209882 | 3.360637 | 3.764125 | 7.835902 | 7.989035 | 6.73963 |
| NAV3 | 0.893739147 | 0.044203301 | 0.016835658 | 13.7274795 | 2.201691 | 2.023048 | 2.995681 | 6.063041 | 6.774676 | 4.790662 |
| SART3 | 0.962279841 | 0.043778104 | 0.013269139 | 13.72644992 | 3.350997 | 4.389936 | 4.754917 | 8.190235 | 8.533804 | 6.942983 |
| PIGR | 0.941813219 | 0.043921714 | 0.014306227 | 13.69663959 | 4.743564 | 6.983552 | 4.754917 | 10.653925 | 9.188984 | 8.519314 |
| PPM1B | 1.075272138 | 0.043516135 | 0.009088125 | 13.68950702 | 8.947392 | 8.203594 | 8.75928 | 11.971229 | 12.722391 | 12.710353 |
| SF3B14 | 0.997377571 | 0.043626235 | 0.011931269 | 13.6646932 | 4.639409 | 5.487673 | 5.018694 | 9.789006 | 8.791075 | 7.96648 |
| KIF14 | 0.935197228 | 0.044003812 | 0.014575706 | 13.6497119 | 1.874444 | 2.406905 | 2.165421 | 7.144104 | 5.936219 | 4.562324 |
| CCDC58 | 0.91218818 | 0.044142622 | 0.015761143 | 13.6497119 | 1.874444 | 3.770995 | 4.754917 | 6.544171 | 5.936219 | 5.882028 |
| MTOR | 0.829413633 | 0.044930476 | 0.020167404 | 13.6497119 | 1.874444 | 2.809601 | 2.165421 | 6.960054 | 5.936219 | 4.146207 |
| GPN1 | 0.825741854 | 0.044949653 | 0.020383124 | 13.63173987 | 2.993831 | 2.023048 | 5.018694 | 7.856887 | 5.936219 | 4.146204 |
| MON1B | 0.771851268 | 0.04405792 | 0.023944199 | 13.6282566 | 6.099991 | 2.809601 | 4.285996 | 7.835902 | 6.613395 | 7.988762 |
| ELF5 | 0.731102124 | 0.047384624 | 0.027039809 | 13.6497119 | 1.874444 | 2.406905 | 2.165421 | 6.544171 | 5.936219 | 2.921909 |
| HAUS3 | 1.114454922 | 0.043485739 | 0.007765226 | 13.63320281 | 5.316227 | 5.487673 | 5.225216 | 9.08528 | 8.892178 | 9.49312 |
| ZC3H11A | 1.019394149 | 0.044949653 | 0.011076557 | 13.63173987 | 6.736762 | 4.911517 | 5.018694 | 10.50566 | 10.074256 | 8.534542 |
| DECR1 | 1.112053053 | 0.043485739 | 0.007833277 | 13.62825669 | 4.309025 | 3.32135 | 4.285996 | 7.771052 | 8.077554 | 7.96648 |
| MGP | 0.775047768 | 0.045974332 | 0.023755699 | 13.62804816 | 8.341965 | 10.719181 | 9.197307 | 15.205994 | 12.965814 | 10.904315 |
| SMARCA5 | 1.057535333 | 0.043540291 | 0.00964818 | 13.62258063 | 4.682076 | 4.351315 | 3.935222 | 7.70315 | 8.518072 | 8.010706 |
| WDR92 | 0.921537088 | 0.044110923 | 0.015275264 | 13.58215181 | 3.024504 | 3.872014 | 4.449894 | 6.252746 | 7.819723 | 8.213534 |
| FAM8A1 | 0.992323431 | 0.043626235 | 0.01212317 | 13.56369603 | 4.743564 | 4.351315 | 4.724406 | 8.665019 | 8.486085 | 7.46072 |
| PDHX | 0.933782907 | 0.044025007 | 0.014641715 | 13.55311089 | 4.309025 | 3.872014 | 2.165421 | 8.069577 | 6.78473 | 6.73963 |
| EGFL6 | 1.11998904 | 0.043485739 | 0.007601905 | 13.54548907 | 1.874444 | 2.023048 | 2.165421 | 5.743394 | 6.613395 | 5.634184 |
| GLCCI1 | 0.919809554 | 0.044110923 | 0.015349439 | 13.54548907 | 1.874444 | 4.351315 | 4.285996 | 7.607339 | 7.187136 | 5.634184 |
| CRIPAK | 0.895084284 | 0.044203301 | 0.016753998 | 13.54548907 | 1.874444 | 4.351315 | 2.379345 | 7.166419 | 6.861783 | 5.634184 |
| AGK | 0.883590092 | 0.044229452 | 0.01729772 | 13.54548907 | 1.874444 | 3.770995 | 2.165421 | 6.067497 | 6.319269 | 5.634184 |
| LOC100281811 | 0.778542863 | 0.045844227 | 0.02430419 | 13.54548907 | 1.874444 | 2.023048 | 4.285996 | 5.891233 | 6.043524 | 12.965814 |
| AVPR1A | 0.827524069 | 0.044930476 | 0.020025723 | 13.53839483 | 3.024504 | 3.872014 | 4.449894 | 6.252746 | 7.819723 | 7.523109 |
| STEAP2 | 0.928552837 | 0.044037172 | 0.014888738 | 13.53481323 | 4.743564 | 4.413323 | 4.724406 | 7.037879 | 8.502167 | 7.523109 |
| ANKRD6 | 0.998330914 | 0.043626235 | 0.011904049 | 13.53211211 | 3.839948 | 2.809601 | 2.165421 | 5.705318 | 7.598264 | 7.553321 |
| TLK1 | 0.987114554 | 0.043626235 | 0.01230102 | 13.51827682 | 3.350997 | 2.023048 | 2.379345 | 5.579836 | 7.107836 | 6.385515 |
| FHDC1 | 1.095417327 | 0.04349335 | 0.00839197 | 13.50702375 | 5.658609 | 5.195784 | 5.544653 | 8.905585 | 9.409671 | 9.414247 |
| FANCL | 1.031298948 | 0.043577906 | 0.010534876 | 13.50095651 | 1.874444 | 2.023048 | 2.165421 | 5.891233 | 5.920411 | 5.106393 |
| ACSL6 | 0.995871176 | 0.043626235 | 0.012007486 | 13.50095651 | 1.874444 | 2.809601 | 2.165421 | 5.320955 | 5.920411 | 6.722123 |
| ANO9 | 0.96057342 | 0.043778104 | 0.0133028 | 13.50095651 | 1.874444 | 3.360637 | 2.165421 | 6.814118 | 5.920411 | 5.634184 |
| ERV3-1 | 0.947611968 | 0.043900827 | 0.014028581 | 13.50095651 | 2.993831 | 2.023048 | 2.165421 | 7.556937 | 5.920411 | 5.106393 |
| DIRC2 | 0.667139886 | 0.050335207 | 0.033083362 | 13.50095651 | 2.201691 | 2.023048 | 2.165421 | 6.063041 | 5.920411 | 2.921909 |
| UGP2 | 0.944249416 | 0.043921714 | 0.014170126 | 13.47046923 | 5.658609 | 4.736586 | 4.508334 | 9.410337 | 8.829823 | 7.611911 |
| CMTM7 | 0.804113829 | 0.045327183 | 0.021178156 | 13.45454007 | 1.874444 | 4.389936 | 3.935222 | 9.094145 | 7.68534 | 4.790662 |
| BOD1 | 1.001742819 | 0.043588662 | 0.011796529 | 13.45492599 | 3.350997 | 2.809601 | 2.379345 | 7.582358 | 6.189775 | 6.129407 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| TAPT1 | 0.879554746 | 0.044278935 | 0.017456278 | 13.45492599 | 3.839948 | 4.830496 | 2.379345 | 8.79031 | 7.414086 | 6.129407 |
| BOLA3-AS1 | 1.002821442 | 0.043588662 | 0.011755699 | 13.4523652 | 3.350997 | 4.389936 | 3.324375 | 7.074163 | 7.174648 | 7.774634 |
| TRIP12 | 1.074870198 | 0.043516135 | 0.00910854 | 13.44966268 | 4.309025 | 4.736586 | 5.018694 | 8.711848 | 8.486085 | 8.135789 |
| BRD7 | 0.975155564 | 0.043661316 | 0.012741749 | 13.44068357 | 3.819732 | 3.360637 | 3.90836 | 6.498222 | 7.656894 | 7.582913 |
| TLR7 | 0.986328177 | 0.043626235 | 0.012320517 | 13.43228908 | 4.263463 | 4.413323 | 4.944468 | 7.504712 | 8.160956 | 8.705744 |
| CLCN6 | 1.049345748 | 0.043568903 | 0.009942838 | 13.42865379 | 4.263463 | 2.406905 | 3.764125 | 7.109557 | 7.414086 | 8.010706 |
| MEIS1 | 0.830335198 | 0.044867325 | 0.020073494 | 13.41522476 | 2.993831 | 2.023048 | 3.935222 | 4.894482 | 7.989035 | 6.73963 |
| IRF2 | 0.867011268 | 0.044369384 | 0.018053079 | 13.39803104 | 4.743564 | 4.736586 | 2.995681 | 8.811966 | 7.505595 | 6.73963 |
| MRPS18B | 0.98608769 | 0.043626235 | 0.012372322 | 13.38300836 | 6.008206 | 5.809601 | 4.944468 | 8.447068 | 9.708913 | 9.750536 |
| AUH | 1.007218577 | 0.043588662 | 0.011571963 | 13.37847188 | 1.874444 | 2.809601 | 3.90836 | 7.450526 | 6.551443 | 6.385515 |
| DPH5 | 1.059697576 | 0.043540291 | 0.009546104 | 13.37793922 | 2.201691 | 3.872014 | 3.324375 | 7.144104 | 7.066159 | 7.020304 |
| TUBA1C | 0.927936308 | 0.044037172 | 0.014929568 | 13.33791063 | 5.658609 | 6.638536 | 4.754917 | 9.396069 | 8.751258 | 9.555312 |
| LEPR | 0.911732464 | 0.044142622 | 0.015795168 | 13.33191166 | 9.227402 | 9.276362 | 9.869299 | 11.967616 | 13.740642 | 13.013174 |
| RYR2 | 1.05630484 | 0.043540291 | 0.00971623 | 13.3177051 | 1.874444 | 2.023048 | 2.165421 | 5.252045 | 5.857745 | 5.900694 |
| CWC27 | 0.955907864 | 0.043840967 | 0.013641375 | 13.3177051 | 3.350997 | 3.360637 | 2.165421 | 7.177844 | 6.613395 | 5.900694 |
| LOC389765 | 0.952497365 | 0.043882243 | 0.013778156 | 13.3177051 | 2.201691 | 2.023048 | 2.165421 | 6.067497 | 4.797798 | 5.900694 |
| XXYLT1 | 0.944859702 | 0.043921714 | 0.014142906 | 13.3177051 | 1.874444 | 2.023048 | 2.165421 | 5.026959 | 6.551443 | 5.900694 |
| C16orf74 | 0.907503097 | 0.044173537 | 0.016022457 | 13.3177051 | 2.201691 | 2.023048 | 2.165421 | 6.067497 | 4.539173 | 5.900694 |
| MDM1 | 0.872420424 | 0.044299467 | 0.01776526 | 13.3177051 | 3.024504 | 2.023048 | 2.165421 | 4.718672 | 6.861783 | 5.900694 |
| DNAJC19 | 0.781046631 | 0.045805247 | 0.023277305 | 13.3177051 | 5.328526 | 3.32135 | 2.165421 | 7.835902 | 7.187136 | 5.900694 |
| GPR183 | 1.012672647 | 0.043581008 | 0.011368493 | 13.3108308 | 2.201691 | 2.023048 | 2.379345 | 8.105092 | 5.936219 | 5.106393 |
| TINF2 | 0.939211476 | 0.043986717 | 0.014431439 | 13.30547426 | 4.263463 | 3.360637 | 2.379345 | 6.339437 | 7.094585 | 7.46072 |
| NUCB2 | 0.860242611 | 0.044379352 | 0.018394692 | 13.25189934 | 2.993831 | 3.770995 | 3.764125 | 9.111713 | 8.385624 | 7.492252 |
| IAPP | 1.025506518 | 0.043577906 | 0.01075672 | 13.23065208 | 6.48761 | 3.77099 | 2.165421 | 5.891233 | 5.857745 | 5.091834 |
| RPE | 1.008255147 | 0.043581008 | 0.01147373 | 13.23065208 | 1.874444 | 2.406905 | 2.165421 | 5.891233 | 6.608026 | 5.106393 |
| RCBTB2 | 0.939993697 | 0.043921714 | 0.014367472 | 13.23065208 | 2.201691 | 2.023048 | 2.165421 | 5.891233 | 7.174648 | 4.562324 |
| MGAT2 | 0.909912382 | 0.044159136 | 0.015906091 | 13.23065208 | 1.874444 | 2.023048 | 2.165421 | 5.891233 | 6.613395 | 6.455366 |
| SKIV2L | 0.907950146 | 0.044173537 | 0.016002042 | 13.23065208 | 2.993831 | 2.809601 | 2.165421 | 5.891233 | 6.551443 | 4.790662 |
| MZT1 | 1.035730746 | 0.043577906 | 0.010385165 | 13.23065208 | 1.874444 | 2.023048 | 2.165421 | 5.743334 | 6.861783 | 5.106393 |
| LOC100130000 | 0.973497609 | 0.043681142 | 0.01282477 | 13.23065208 | 3.350997 | 2.023048 | 2.165421 | 5.743334 | 6.189775 | 6.385515 |
| CLSTN2 | 0.942030873 | 0.043921714 | 0.012822617 | 13.23065208 | 1.874444 | 2.023048 | 2.165421 | 5.743334 | 4.539173 | 6.649696 |
| SIX4 | 0.935684973 | 0.043994974 | 0.014534876 | 13.23065208 | 3.024504 | 2.023048 | 3.935222 | 5.743334 | 7.505595 | 6.924055 |
| GIMAP1 | 0.772583258 | 0.046036363 | 0.023882953 | 13.20033324 | 2.993831 | 2.023048 | 3.764125 | 7.607339 | 6.373501 | 6.129407 |
| BOD1L | 1.052687501 | 0.043568903 | 0.009847567 | 13.20033324 | 4.639409 | 2.406905 | 2.165421 | 6.063041 | 6.189775 | 6.129407 |
| GTF2H5 | 1.116087126 | 0.043485739 | 0.00703981 | 13.1876666 | 5.328526 | 5.789702 | 6.175931 | 9.565008 | 9.897049 | 7.722406 |
| PRSS35 | 1.051079108 | 0.043568903 | 0.009902007 | 13.18007422 | 2.201691 | 2.023048 | 2.165421 | 5.743334 | 7.53715 | 5.874974 |
| NUP35 | 1.046288019 | 0.043577906 | 0.01011364 | 13.18007422 | 1.874444 | 2.406905 | 2.165421 | 5.743334 | 5.353925 | 6.722123 |
| UGT2B10 | 1.038587589 | 0.043577906 | 0.010344335 | 13.18007422 | 2.993831 | 2.023048 | 2.165421 | 5.743334 | 6.373501 | 5.106393 |
| ARHGEF37 | 0.918348441 | 0.044110923 | 0.01541084 | 13.18007422 | 3.350997 | 2.023048 | 2.165421 | 5.743334 | 6.861783 | 6.385515 |
| BRMS1L | 0.905774021 | 0.044173537 | 0.016117727 | 13.18007422 | 1.874444 | 2.023048 | 2.165421 | 5.743334 | 4.539173 | 6.649696 |
| C9orf46 | 0.878595308 | 0.044280042 | 0.017514801 | 13.18007422 | 3.024504 | 2.023048 | 3.935222 | 5.743334 | 7.505595 | 6.924055 |
| MBNL2 | 0.834966314 | 0.044793607 | 0.019722355 | 13.1876666 | 5.328526 | 5.789702 | 6.175931 | 9.565008 | 9.897049 | 7.722406 |
| PARP4 | 1.117161292 | 0.043485739 | 0.007669956 | 13.18007422 | 2.201691 | 2.023048 | 2.165421 | 5.743334 | 7.53715 | 5.874974 |
| ZNF300 | 1.075239313 | 0.043516135 | 0.00909493 | 13.18007422 | 1.874444 | 2.406905 | 2.165421 | 5.743334 | 5.353925 | 6.722123 |
| LOC100505989 | 1.052826099 | 0.043568903 | 0.009833957 | 13.18007422 | 2.993831 | 2.023048 | 2.165421 | 5.743334 | 6.373501 | 5.106393 |
| AASDH | 0.892343309 | 0.044203301 | 0.016883294 | 13.23065208 | 1.874444 | 2.406905 | 2.165421 | 5.891233 | 6.205902 | 4.476242 |
| ZNF860 | 0.686280596 | 0.049293152 | 0.031014631 | 13.23065208 | 1.874444 | 2.406905 | 2.165421 | 5.891233 | 6.640994 | 2.921909 |
| CAB39L | 0.952083378 | 0.043900827 | 0.01381082 | 13.20033324 | 2.993831 | 2.023048 | 3.764125 | 7.607339 | 6.373501 | 6.129407 |
| DNMT3A | 0.760899973 | 0.046345577 | 0.024798911 | 13.20033324 | 4.639409 | 2.406905 | 2.165421 | 6.063041 | 6.189775 | 6.129407 |
| BOD1L | 1.052687501 | 0.043568903 | 0.009847567 | 13.16714224 | 4.682076 | 4.830496 | 4.285996 | 8.460842 | 8.549366 | 7.849596 |
| GTF2H5 | 1.116087126 | 0.043485739 | 0.00703981 | 13.15881989 | 5.335413 | 3.32135 | 5.389265 | 9.012327 | 9.107223 | 9.018932 |
| PRSS35 | 1.051079108 | 0.043568903 | 0.009902007 | 13.14650042 | 1.874444 | 2.406905 | 2.165421 | 6.960054 | 5.353925 | 5.882028 |
| NUP35 | 1.046288019 | 0.043577906 | 0.01011364 | 13.14650042 | 2.201691 | 2.809601 | 2.165421 | 6.067497 | 6.043524 | 5.882028 |
| UGT2B10 | 1.038587589 | 0.043577906 | 0.010344335 | 13.14650042 | 2.201691 | 2.023048 | 2.165421 | 5.252045 | 6.205902 | 5.882028 |
| ARHGEF37 | 0.918348441 | 0.044110923 | 0.01541084 | 13.14650042 | 2.201691 | 2.023048 | 2.165421 | 6.067497 | 4.608763 | 6.924055 |
| BRMS1L | 0.905774021 | 0.044173537 | 0.016117727 | 13.14650042 | 2.993831 | 2.023048 | 2.165421 | 4.894482 | 7.094585 | 5.882028 |
| C9orf46 | 0.878595308 | 0.044280042 | 0.017514801 | 13.14650042 | 4.209882 | 3.872014 | 2.165421 | 9.16317 | 6.78473 | 5.882028 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| LIN7C | 0.700514603 | 0.04869904 | 0.029825791 | 13.14650042 | 6.227577 | 2.809601 | 2.165421 | 7.748771 | 7.25505 | 5.882028 |
| FAM190A | 1.044609719 | 0.043577906 | 0.010187819 | 13.13301274 | 3.024504 | 2.023048 | 2.165421 | 5.728038 | 6.205902 | 6.73963 |
| CMYA5 | 1.013627102 | 0.043581008 | 0.011327662 | 13.13301274 | 3.024504 | 3.32135 | 2.165421 | 6.067497 | 6.794431 | 6.73963 |
| SLC35E3 | 1.015724372 | 0.043581008 | 0.011211977 | 13.09663538 | 4.639409 | 3.360637 | 4.449894 | 7.477873 | 8.350533 | 7.897492 |
| FLNB | 0.960306262 | 0.043778104 | 0.01336441 | 13.09607079 | 3.819732 | 5.195784 | 4.449894 | 9.466036 | 8.160956 | 7.291822 |
| METTL21D | 0.956439729 | 0.043840967 | 0.013600544 | 13.08955464 | 3.024504 | 3.872014 | 2.379345 | 7.582358 | 6.608026 | 6.106561 |
| HCN1 | 0.935154639 | 0.044003812 | 0.014582511 | 13.08237714 | 2.201691 | 2.023048 | 2.165421 | 4.739845 | 5.936219 | 5.874974 |
| SENP2 | 0.868608189 | 0.044335719 | 0.017936033 | 13.08237714 | 4.639409 | 2.809601 | 2.165421 | 7.210813 | 7.191402 | 5.874974 |
| SEMA3C | 0.764909652 | 0.046181862 | 0.024498809 | 13.08237714 | 2.201691 | 4.750708 | 2.165421 | 6.067497 | 6.613395 | 5.874974 |
| FLI1 | 1.041810741 | 0.043577906 | 0.010255869 | 13.08134273 | 3.024504 | 2.406905 | 3.324375 | 6.283686 | 6.613395 | 7.033813 |
| TRPM8 | 0.863251995 | 0.044377262 | 0.018232732 | 13.08134273 | 1.874444 | 4.80797 | 3.324375 | 6.244586 | 7.473335 | 7.033813 |
| BCKDHB | 1.046439605 | 0.043577906 | 0.010086424 | 13.07927039 | 4.309025 | 4.413323 | 3.764125 | 8.239009 | 7.473335 | 7.849596 |
| HSPA7 | 0.695394114 | 0.048858998 | 0.030266757 | 13.0513108 | 5.335413 | 6.139057 | 9.749619 | 9.29204 | 12.218027 | 9.84518 |
| TCTEX1D2 | 0.983058134 | 0.043626235 | 0.012483838 | 13.05101308 | 1.874444 | 3.360637 | 2.165421 | 6.252746 | 6.774676 | 5.580533 |
| ARNTL | 0.946802221 | 0.043900827 | 0.014048996 | 13.05101308 | 1.874444 | 2.406905 | 3.324375 | 6.396698 | 6.189775 | 5.580533 |
| ILKAP | 1.070054726 | 0.043516135 | 0.009258251 | 13.04470248 | 1.874444 | 2.023048 | 2.379345 | 5.579836 | 7.187136 | 5.634184 |
| FAM58A | 1.007836257 | 0.043581008 | 0.011531814 | 13.04470248 | 1.874444 | 2.023048 | 2.995681 | 5.579836 | 6.613395 | 5.874974 |
| LEPREL1 | 0.880598153 | 0.044278935 | 0.017415447 | 13.04470248 | 1.874444 | 4.911517 | 2.995681 | 5.579836 | 7.870158 | 7.988762 |
| ISCA2 | 1.086064959 | 0.043516135 | 0.008736985 | 13.04106563 | 1.874444 | 2.023048 | 2.165421 | 5.728038 | 7.174648 | 5.446557 |
| CCDC126 | 1.084803539 | 0.043516135 | 0.008771011 | 13.04106563 | 1.874444 | 2.023048 | 2.165421 | 5.728038 | 6.189775 | 5.426231 |
| BDNF-AS1 | 1.073452982 | 0.043516135 | 0.009142565 | 13.04106563 | 1.874444 | 2.023048 | 2.165421 | 5.728038 | 5.353925 | 6.73963 |
| SENP8 | 1.065863922 | 0.043516135 | 0.009373937 | 13.04106563 | 1.874444 | 2.023048 | 2.165421 | 5.728038 | 5.306419 | 6.722123 |
| FMO4 | 1.032779289 | 0.043577906 | 0.010487241 | 13.04106563 | 1.874444 | 2.023048 | 2.165421 | 5.728038 | 7.174648 | 5.091834 |
| LINC00547 | 1.030678725 | 0.043577906 | 0.010555291 | 13.04106563 | 3.024504 | 2.023048 | 2.165421 | 5.728038 | 6.613395 | 6.106561 |
| FIGNL1 | 1.018897029 | 0.043577906 | 0.01110377 | 13.04106563 | 1.874444 | 2.023048 | 2.165421 | 5.728038 | 5.920411 | 5.091834 |
| C14orf126 | 0.976429387 | 0.043661316 | 0.012673699 | 13.04106563 | 2.993831 | 2.023048 | 2.165421 | 5.728038 | 5.936219 | 5.882028 |
| LOC100505648 | 0.938608641 | 0.043986717 | 0.014438244 | 13.04106563 | 1.874444 | 2.023048 | 2.165421 | 5.728038 | 4.608763 | 6.106561 |
| TMEM200A | 0.893808062 | 0.044203301 | 0.016828853 | 13.04106563 | 1.874444 | 2.023048 | 2.995681 | 5.728038 | 4.797798 | 6.931222 |
| CHEK2P2 | 0.876769665 | 0.044280042 | 0.01758285 | 13.04106563 | 1.874444 | 2.023048 | 2.165421 | 5.728038 | 6.551443 | 4.146207 |
| COQ10A | 0.736220688 | 0.047233845 | 0.026663491 | 13.04106563 | 4.743564 | 2.023048 | 2.379345 | 5.728038 | 6.373501 | 6.106561 |
| ZNF485 | 0.999751667 | 0.043626235 | 0.01187024 | 13.02812046 | 4.682076 | 2.023048 | 5.018694 | 7.556937 | 8.385634 | 8.593895 |
| ANKRD36BP1 | 0.948516997 | 0.043900827 | 0.013967336 | 13.0175637 | 5.328526 | 5.43468 | 7.003286 | 9.030914 | 10.173004 | 9.555312 |
| PRSS23 | 0.880794027 | 0.044278935 | 0.017408642 | 13.0175637 | 5.328526 | 2.809601 | 3.90836 | 9.030914 | 8.314558 | 6.195186 |
| MCCC1 | 0.888695309 | 0.044203301 | 0.01706703 | 13.01713567 | 5.491121 | 3.770995 | 2.995681 | 8.087444 | 7.473335 | 7.36177 |
| FILIP1L | 1.003769199 | 0.043588662 | 0.011721674 | 13.00581703 | 5.263699 | 3.32135 | 4.449894 | 8.964784 | 7.740604 | 8.074602 |
| CHRNA5 | 0.973688171 | 0.043681142 | 0.012811116 | 12.99331557 | 6.227577 | 5.809601 | 5.974145 | 8.768324 | 9.673843 | 10.524247 |
| ZFYVE19 | 1.005168799 | 0.043588662 | 0.011646819 | 12.97460589 | 2.201691 | 3.360637 | 2.165421 | 7.582358 | 6.608026 | 5.900694 |
| GPR75-ASB3 | 0.939506889 | 0.043955231 | 0.014406261 | 12.98706672 | 2.201691 | 2.406905 | 2.165421 | 4.802615 | 6.861783 | 5.900694 |
| NIPSNAP3A | 0.925740635 | 0.04407613 | 0.015049493 | 12.98706672 | 2.201691 | 2.023048 | 2.995681 | 7.037879 | 5.936219 | 5.900694 |
| HPSE | 0.905532708 | 0.044173537 | 0.01614947 | 12.98706672 | 2.201691 | 2.809601 | 2.165421 | 4.894482 | 6.640994 | 5.900694 |
| DRAM2 | 0.992702757 | 0.043626235 | 0.012102756 | 12.98661625 | 4.743564 | 3.32135 | 3.324375 | 8.41912 | 7.440337 | 7.020304 |
| NUDT5 | 0.95948838 | 0.043826549 | 0.013429058 | 12.98661625 | 4.682076 | 3.32135 | 2.165421 | 7.995811 | 6.794431 | 7.020304 |
| SNHG6 | 1.012942415 | 0.043581008 | 0.011354883 | 12.97747945 | 7.198002 | 7.152299 | 7.628916 | 11.326854 | 11.018888 | 10.396714 |
| CPSF6 | 0.901304404 | 0.044203301 | 0.016387207 | 12.97460589 | 3.024504 | 3.770995 | 5.389265 | 8.301578 | 8.2398 | 6.722123 |
| IAH1 | 0.895650913 | 0.044203301 | 0.016713168 | 12.97460589 | 3.024504 | 4.351315 | 2.165421 | 6.183122 | 7.191402 | 6.722123 |
| LONRF1 | 0.798796476 | 0.045355733 | 0.022082341 | 12.97315853 | 6.143785 | 5.661685 | 6.175931 | 7.556987 | 9.841243 | 10.489503 |
| RAB3B | 0.929557121 | 0.044037172 | 0.014841102 | 12.9639101 | 2.993831 | 2.023048 | 2.165421 | 4.802615 | 6.608026 | 6.69026 |
| NCSTN | 0.876014478 | 0.044285705 | 0.01762096 | 12.94729481 | 4.263463 | 2.023048 | 2.995681 | 5.579836 | 8.011679 | 6.69026 |
| RTCD1 | 0.823032559 | 0.045019115 | 0.020541681 | 12.94729481 | 4.639409 | 4.413323 | 2.995681 | 8.40494 | 6.794431 | 6.69026 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| PHKG2 | 0.956949091 | 0.043840967 | 0.013586934 | 12.93451072 | 3.819732 | 4.351315 | 5.018694 | 8.711848 | 7.68534 | 7.523109 |
| ARHGAP25 | 0.962375098 | 0.043778104 | 0.013262334 | 12.92707283 | 1.874444 | 2.023048 | 2.023048 | 5.743334 | 5.857745 | 4.790662 |
| RIC3 | 0.915056776 | 0.044110923 | 0.015584893 | 12.92707283 | 1.874444 | 3.360637 | 2.165421 | 6.067497 | 5.857745 | 5.634184 |
| PKIB | 0.743055806 | 0.046915454 | 0.02612181 | 12.92707283 | 1.874444 | 2.809601 | 2.165421 | 9.657624 | 5.857745 | 2.921909 |
| TMEM42 | 0.705574031 | 0.048360255 | 0.029273903 | 12.92707283 | 3.350997 | 2.023048 | 2.165421 | 7.177844 | 5.857745 | 3.676349 |
| FAM120B | 0.917067225 | 0.044110923 | 0.015455597 | 12.91622318 | 3.839948 | 3.32135 | 2.165421 | 7.531061 | 7.138979 | 5.634184 |
| AHI1 | 1.036240011 | 0.043577906 | 0.01037836 | 12.91467332 | 5.779429 | 5.809601 | 5.974145 | 9.030914 | 9.500541 | 9.757043 |
| GPR82 | 0.898393736 | 0.044230301 | 0.016566179 | 12.90217497 | 2.201691 | 2.023048 | 2.165421 | 5.891233 | 4.539173 | 5.882028 |
| RPGR | 0.851242427 | 0.044490827 | 0.01880272 | 12.89393432 | 4.743564 | 2.809601 | 2.379345 | 6.498222 | 7.174648 | 6.455366 |
| C15orf40 | 0.938171393 | 0.043986717 | 0.014458659 | 12.88497394 | 5.744513 | 4.389936 | 5.544653 | 9.727662 | 8.077554 | 8.758577 |
| PPFIBP1 | 1.095498972 | 0.04349335 | 0.008378484 | 12.87109469 | 5.263699 | 5.487673 | 5.389265 | 8.843852 | 9.075328 | 9.50208 |
| ZNF140 | 0.983580619 | 0.043626235 | 0.012436203 | 12.86930913 | 3.819732 | 3.360637 | 2.379345 | 6.550689 | 7.505595 | 6.587378 |
| PPP1R2 | 1.00176233 | 0.043588662 | 0.011789724 | 12.86684943 | 4.815804 | 4.736586 | 3.764125 | 8.501391 | 7.656894 | 8.11568 |
| TPCN1 | 1.024569533 | 0.043577906 | 0.01082477 | 12.84075276 | 4.309025 | 4.351315 | 4.724406 | 8.501391 | 8.033973 | 7.640338 |
| CD28 | 1.095383167 | 0.04349335 | 0.008730384 | 12.83730384 | 1.874444 | 2.023048 | 2.165421 | 5.705318 | 5.509998 | 6.69026 |
| RNF212 | 1.085781213 | 0.043516135 | 0.00874379 | 12.83730384 | 1.874444 | 2.023048 | 2.165421 | 5.705318 | 6.608026 | 5.446557 |
| ABCB6 | 1.070750359 | 0.043516135 | 0.009224226 | 12.83730384 | 1.874444 | 2.023048 | 2.165421 | 5.705318 | 5.353925 | 6.385515 |
| VEGFC | 1.064677912 | 0.043516135 | 0.009401157 | 12.83730384 | 1.874444 | 2.023048 | 2.165421 | 5.705318 | 5.317867 | 6.385515 |
| CDYL | 0.932063488 | 0.044025007 | 0.014723375 | 12.82873632 | 5.304463 | 3.872014 | 2.995681 | 7.477873 | 8.140553 | 7.553321 |
| EHBP1 | 0.857716308 | 0.044387761 | 0.018475672 | 12.817417 | 3.024504 | 3.770995 | 4.285996 | 5.743334 | 7.96603 | 7.722406 |
| CHRDL1 | 0.902567775 | 0.044190907 | 0.01632392 | 12.77680226 | 5.056948 | 3.32135 | 6.527811 | 8.40494 | 9.075328 | 8.732403 |
| MTX3 | 0.924460444 | 0.044086036 | 0.015139843 | 12.77409406 | 4.639409 | 3.360637 | 3.935222 | 6.396698 | 8.314558 | 8.175185 |
| WBSCR22 | 0.95996168 | 0.04419907 | 0.01340660 | 12.76390771 | 4.743564 | 4.736586 | 3.90836 | 7.582358 | 7.740604 | 8.519314 |
| ANKRD44 | 1.014077323 | 0.043581008 | 0.011307247 | 12.75758124 | 2.201691 | 2.023048 | 2.995681 | 6.339437 | 5.857745 | 5.874974 |
| CTH | 0.989125746 | 0.043626235 | 0.012204832 | 12.75758124 | 4.682076 | 2.406905 | 3.324375 | 8.139755 | 5.936219 | 6.587378 |
| ACPL2 | 0.919184342 | 0.044110923 | 0.015356244 | 12.75758124 | 2.201691 | 2.023048 | 3.324375 | 7.144104 | 5.306419 | 14.148553 |
| MTHFD1 | 0.895336418 | 0.043626235 | 0.016726778 | 12.75758124 | 2.201691 | 2.023048 | 3.324375 | 7.835902 | 7.31791 | 7.020304 |
| COX8A | 1.032589058 | 0.043577906 | 0.010494046 | 12.75456761 | 7.218633 | 6.35207 | 6.670675 | 10.632786 | 8.140553 | 7.695565 |
| SLA | 0.771698267 | 0.046066162 | 0.02395917 | 12.74220491 | 1.874444 | 3.360637 | 5.609945 | 7.631894 | 10.025012 | 10.573 |
| PRF1 | 0.841524278 | 0.044701668 | 0.019371895 | 12.72892144 | 3.350997 | 5.43468 | 5.596986 | 7.42265 | 6.319269 | 7.03218 |
| GGCT | 0.902290194 | 0.04419907 | 0.01635114 | 12.72278325 | 1.874444 | 3.770995 | 2.165421 | 8.119857 | 9.267025 | 9.267025 |
| HYAL2 | 0.915002802 | 0.044110923 | 0.015598503 | 12.72247443 | 3.350997 | 2.023048 | 2.165421 | 7.074163 | 7.440337 | 4.790662 |
| TSEN15 | 0.860416238 | 0.044379352 | 0.018381082 | 12.72244641 | 4.682076 | 2.023048 | 9.203198 | 5.095353 | 6.205902 | 7.020304 |
| RPS18 | 1.067036784 | 0.043516135 | 0.009346717 | 12.71370293 | 10.48024 | 11.04134 | 10.756834 | 14.660003 | 6.794431 | 6.587378 |
| ARID4A | 1.006140008 | 0.043588662 | 0.011619599 | 12.70866207 | 4.309025 | 2.406905 | 3.90836 | 7.976765 | 14.518428 | 14.148553 |
| HECTD1 | 0.994906277 | 0.043626235 | 0.012041511 | 12.69662826 | 5.056948 | 2.406905 | 4.724406 | 8.723321 | 7.31791 | 7.020304 |
| BRMS1 | 0.956525242 | 0.043840967 | 0.013593739 | 12.69119225 | 3.024504 | 3.32135 | 2.165421 | 7.531061 | 8.140553 | 7.695565 |
| CRAMP1L | 1.004840221 | 0.043588662 | 0.011674039 | 12.64950863 | 5.744513 | 5.487673 | 5.225216 | 8.514658 | 5.509998 | 6.69026 |
| AOX1 | 1.074716038 | 0.043516135 | 0.009115345 | 12.64585358 | 1.874444 | 2.406905 | 2.165421 | 6.067497 | 9.148683 | 9.525135 |
| PSMA4 | 0.933581517 | 0.044025007 | 0.014655325 | 12.64150737 | 5.779429 | 5.661685 | 3.764125 | 9.33006 | 5.509998 | 6.051818 |
| RNF6 | 0.829055687 | 0.044930476 | 0.020194624 | 12.62359827 | 2.993831 | 2.023048 | 2.165421 | 6.651882 | 9.321782 | 7.873743 |
| LMCH1 | 0.875488467 | 0.044285705 | 0.01766179 | 12.61868652 | 2.201691 | 3.770995 | 5.544653 | 7.995811 | 7.187136 | 4.146207 |
| CCNDBP1 | 0.769300124 | 0.046082352 | 0.024102756 | 12.61868652 | 6.381847 | 2.406905 | 3.90836 | 7.748771 | 8.402869 | 7.428484 |
| GOLGA8IP | 1.056494403 | 0.043540291 | 0.009695815 | 12.61037063 | 8.971905 | 8.783406 | 9.203198 | 12.307705 | 12.991677 | 12.628444 |
| ZFP90 | 0.885867603 | 0.044203301 | 0.01718952 | 12.60685291 | 3.819732 | 2.406905 | 3.90836 | 6.063041 | 6.78473 | 7.640338 |
| PRPS2 | 0.913024725 | 0.044285705 | 0.015707383 | 12.60613267 | 2.201691 | 2.406905 | 2.165421 | 4.739845 | 5.857745 | 6.32627 |
| DUSP19 | 0.948708747 | 0.043900827 | 0.013946921 | 12.58949229 | 8.485078 | 7.631788 | 8.685452 | 10.965483 | 12.139226 | 12.489807 |
| OLA1 | 0.937081433 | 0.043994974 | 0.014487241 | 12.57340381 | 3.839948 | 5.362142 | 4.944468 | 10.048181 | 8.181074 | 7.492252 |
| FAM214A | 0.945422529 | 0.043921714 | 0.014122491 | 12.57216282 | 4.815804 | 4.750708 | 6.072169 | 9.506443 | 8.402869 | 8.472642 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| ENSA | 1.03205867 | 0.043577906 | 0.010514461 | 12.56538264 | 6.227577 | 4.911517 | 5.592916 | 9.87896 | 9.09667 | 9.163078 |
| LRP12 | 0.87957494 | 0.044278935 | 0.017449473 | 12.55301339 | 1.874444 | 2.023048 | 3.764125 | 6.067497 | 7.414086 | 5.091834 |
| MLH3 | 0.801599728 | 0.045343936 | 0.021904729 | 12.54436002 | 3.839948 | 2.809601 | 4.449894 | 5.252045 | 8.098861 | 8.053616 |
| FAM200B | 0.967250065 | 0.043778104 | 0.013099013 | 12.5365444 | 4.743564 | 5.195784 | 3.764125 | 8.843852 | 8.314558 | 7.553321 |
| RUNX2 | 0.670323386 | 0.050073072 | 0.032698197 | 12.52868649 | 2.993831 | 2.023048 | 5.596986 | 6.814118 | 6.640994 | 5.874974 |
| EMI4 | 0.952658484 | 0.043882243 | 0.013771351 | 12.52426057 | 5.328526 | 4.750708 | 6.012527 | 9.909415 | 8.97518 | 8.194487 |
| LOC100131067 | 1.024626663 | 0.043577906 | 0.01081116 | 12.51654746 | 3.024504 | 2.809601 | 2.165421 | 5.743334 | 7.406567 | 6.455366 |
| NAAA | 0.983954015 | 0.043626235 | 0.012402178 | 12.50916052 | 3.350997 | 2.406905 | 2.995681 | 6.339437 | 7.187136 | 6.051818 |
| SEC22C | 1.037677767 | 0.043577906 | 0.01036475 | 12.49548073 | 5.056948 | 4.80797 | 4.285996 | 8.700282 | 8.696398 | 7.897492 |
| GCFC2 | 0.804246691 | 0.045327183 | 0.021750936 | 12.49337873 | 4.639409 | 3.770995 | 2.379345 | 8.301578 | 7.414086 | 5.446557 |
| C1orf63 | 1.065498536 | 0.043516135 | 0.009380742 | 12.48621817 | 6.707871 | 6.732825 | 7.156853 | 10.420113 | 10.779249 | 10.350135 |
| LINC00260 | 0.799435579 | 0.045343942 | 0.022044913 | 12.45543243 | 5.335413 | 3.32135 | 5.609945 | 6.960054 | 7.767462 | 10.191053 |
| GSDMD | 0.907617969 | 0.044135537 | 0.016015652 | 12.45155452 | 4.639409 | 6.060401 | 3.764125 | 7.897963 | 8.277663 | 9.172843 |
| SLC25A30 | 0.973254286 | 0.043681142 | 0.01283838 | 12.43744748 | 3.024504 | 2.406905 | 2.165421 | 7.274575 | 6.043524 | 5.446557 |
| FUNDC1 | 0.849557077 | 0.044521554 | 0.018904389 | 12.43744748 | 2.993831 | 2.406905 | 2.165421 | 7.30543 | 6.043524 | 4.562324 |
| PDZRN3 | 0.81441062 | 0.045212649 | 0.021137802 | 12.429554 | 4.963444 | 3.32135 | 4.754917 | 8.39062 | 8.609988 | 6.195186 |
| NADSYN1 | 1.080299071 | 0.043516135 | 0.00895883 | 12.42827745 | 1.874444 | 2.023048 | 2.165421 | 7.679787 | 5.509998 | 5.634184 |
| ZC3H12B | 1.078996504 | 0.043516135 | 0.00899966 | 12.42827745 | 1.874444 | 2.023048 | 2.165421 | 5.891233 | 5.509998 | 5.580533 |
| TTC9C | 1.072643204 | 0.043516135 | 0.009190201 | 12.42827745 | 1.874444 | 2.023048 | 2.165421 | 7.835902 | 5.509998 | 5.580533 |
| ZC4H2 | 1.055026165 | 0.043540291 | 0.009763865 | 12.42827745 | 1.874444 | 2.406905 | 2.165421 | 5.891233 | 5.509998 | 5.900694 |
| NRXN3 | 1.053820818 | 0.043568903 | 0.009806737 | 12.42827745 | 1.874444 | 2.406905 | 2.165421 | 5.891233 | 5.509998 | 5.882028 |
| WRN | 0.975824963 | 0.043661316 | 0.012707724 | 12.42827745 | 1.874444 | 2.023048 | 2.379345 | 6.544171 | 5.509998 | 6.587378 |
| PRKCB | 0.973545341 | 0.043681142 | 0.01281769 | 12.42827745 | 1.874444 | 2.023048 | 2.995681 | 5.891233 | 5.509998 | 6.051818 |
| MYBL1 | 0.97173629 | 0.043681142 | 0.012913236 | 12.42827745 | 1.874444 | 2.406905 | 3.324375 | 6.664985 | 5.509998 | 6.455366 |
| ZNF711 | 0.800604577 | 0.045343936 | 0.02194556 | 12.42590411 | 4.209882 | 2.023048 | 3.935222 | 6.183122 | 7.845161 | 6.051818 |
| WDR17 | 0.995350607 | 0.043626235 | 0.012021096 | 12.40464627 | 3.024504 | 3.360637 | 3.935222 | 6.396698 | 7.56803 | 7.327219 |
| ISG15 | 0.852817719 | 0.044464174 | 0.018711126 | 12.39243525 | 4.682076 | 4.830496 | 3.764125 | 7.897963 | 5.936219 | 7.395512 |
| SLC16A4 | 1.040741441 | 0.043577906 | 0.010283089 | 12.33932494 | 3.024504 | 2.023048 | 2.995681 | 6.252746 | 6.319269 | 6.649696 |
| DTX3L | 0.976148907 | 0.043661316 | 0.012680504 | 12.3131789 | 6.054828 | 6.270596 | 6.012527 | 8.98399 | 10.157854 | 9.676959 |
| GLRX3 | 0.799158265 | 0.045355733 | 0.022075536 | 12.3098614 | 6.143785 | 4.389936 | 3.324375 | 8.361545 | 8.011679 | 7.327219 |
| VPS41 | 0.970953796 | 0.043709154 | 0.012942497 | 12.30963202 | 4.815804 | 4.830496 | 3.935222 | 7.556987 | 8.011679 | 8.745549 |
| POLR2C | 0.899552608 | 0.044203301 | 0.016521266 | 12.30963202 | 5.056948 | 3.360637 | 3.935222 | 7.556937 | 7.793829 | 7.152205 |
| PBLD | 1.055802609 | 0.043540291 | 0.00974345 | 12.30892212 | 3.350997 | 3.32135 | 3.764125 | 7.109557 | 7.094585 | 6.942983 |
| CALCOCO1 | 0.890663262 | 0.044203301 | 0.016964954 | 12.30892212 | 5.316227 | 3.32135 | 4.285996 | 8.239009 | 8.314558 | 6.942983 |
| EIF4E3 | 0.816133188 | 0.045165524 | 0.020854954 | 12.30892212 | 3.024504 | 3.32135 | 3.764125 | 7.556987 | 7.627877 | 6.942983 |
| ZC3H12A | 0.915421403 | 0.044135537 | 0.015557673 | 12.30054642 | 3.350997 | 4.413323 | 5.018694 | 11.307926 | 8.033973 | 6.455366 |
| MED4 | 0.965487649 | 0.043778104 | 0.013173869 | 12.29750485 | 3.350997 | 4.750708 | 4.944468 | 7.504712 | 8.564762 | 8.03232 |
| ZNF124 | 0.900528571 | 0.04420330l | 0.016434842 | 12.29547398 | 2.993831 | 3.770995 | 4.944468 | 6.396698 | 7.767462 | 8.564524 |
| CDS1 | 0.863340849 | 0.044377262 | 0.018225927 | 12.29366246 | 1.874444 | 4.413323 | 2.165421 | 8.033165 | 6.237456 | 5.426231 |
| MGST2 | 0.904329641 | 0.044173537 | 0.016212777 | 12.29128777 | 2.993831 | 2.809601 | 4.285996 | 8.270632 | 6.613395 | 6.129407 |
| FAM206A | 0.782334216 | 0.045701235 | 0.023165703 | 12.29128777 | 2.993831 | 3.770995 | 2.165421 | 8.139755 | 6.613395 | 4.476242 |
| CAPN7 | 1.000278902 | 0.043588662 | 0.01183736 | 12.29074996 | 4.682076 | 4.351315 | 3.935222 | 8.301578 | 7.989035 | 7.395512 |
| PAIP2 | 0.963487812 | 0.043778104 | 0.013235114 | 12.28408127 | 7.112399 | 6.060401 | 6.326717 | 10.052735 | 9.776594 | 9.945435 |
| MGC14436 | 0.976038768 | 0.043661316 | 0.012687309 | 12.27553455 | 1.874444 | 3.770995 | 2.995681 | 6.396698 | 6.613395 | 6.722123 |
| LOC100132891 | 0.807268839 | 0.045278798 | 0.021547465 | 12.27553455 | 3.024504 | 2.406905 | 2.995681 | 7.243046 | 6.613395 | 4.476242 |
| GNL3 | 0.905979797 | 0.044173537 | 0.016104117 | 12.2626138 | 6.52121 | 6.957749 | 6.031658 | 11.019999 | 10.137404 | 8.929599 |
| EFR3A | 0.86246451 | 0.043588662 | 0.018279006 | 12.25669528 | 4.639409 | 3.770995 | 2.379345 | 8.254907 | 7.505595 | 5.874974 |
| NAE1 | 1.027632369 | 0.043577906 | 0.010641034 | 12.253864 | 4.209882 | 4.351315 | 2.165421 | 7.33564 | 7.627877 | 7.96648 |
| LOC339803 | 1.04505476 | 0.043577906 | 0.010160599 | 12.25379949 | 4.209882 | 3.872014 | 4.285996 | 7.30543 | 8.668166 | 7.825039 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| PPP6C | 0.892212902 | 0.044203301 | 0.016903709 | 12.2503371 | 5.328526 | 4.911517 | 3.90836 | 8.955085 | 7.91889 | 7.523109 |
| LOC100130890 | 0.909235331 | 0.044173036 | 0.01595985 | 12.2426966 | 8.424205 | 7.547799 | 8.859664 | 10.70401 | 12.038054 | 12.989194 |
| MERTK | 0.958681654 | 0.043826549 | 0.013465083 | 12.22993628 | 3.024504 | 2.406905 | 2.995681 | 7.36523 | 6.608026 | 5.446557 |
| ALOX5 | 0.729237285 | 0.047411805 | 0.02716162 | 12.21969441 | 1.874444 | 2.023048 | 2.165421 | 6.651882 | 3.134528 | 5.634184 |
| DCN | 0.901177275 | 0.044203301 | 0.016407622 | 12.21165883 | 8.691047 | 8.181467 | 9.374815 | 11.112348 | 14.059416 | 12.301234 |
| ORMDL1 | 0.960888006 | 0.043778104 | 0.013323579 | 12.16974349 | 4.682076 | 5.43468 | 4.285996 | 7.976765 | 8.518072 | 8.287303 |
| PPP2R2D | 0.92966909 | 0.044037172 | 0.014834297 | 12.13683918 | 4.743564 | 3.872014 | 4.754917 | 8.40494 | 7.473335 | 7.640338 |
| TMX2 | 1.020171365 | 0.043577906 | 0.011042531 | 12.13681501 | 4.963444 | 4.389936 | 4.754917 | 8.069577 | 8.564762 | 8.074602 |
| SNX24 | 0.957946362 | 0.043835088 | 0.013514801 | 12.1230449 | 2.201691 | 4.389936 | 3.324375 | 7.25991 | 6.861783 | 6.924055 |
| ERCC3 | 0.90777916 | 0.044173537 | 0.016008847 | 12.11192565 | 5.779429 | 4.413323 | 4.449894 | 8.173604 | 8.011679 | 8.549611 |
| RPL31 | 1.013673873 | 0.043581008 | 0.011320857 | 12.10998464 | 9.461799 | 10.227521 | 9.996864 | 13.615329 | 13.594989 | 13.134325 |
| STEAP4 | 0.98781763 | 0.043626235 | 0.012259272 | 12.10266693 | 6.554045 | 6.931478 | 7.317525 | 10.528731 | 9.822151 | 12.309004 |
| SLBP | 0.924727384 | 0.044086036 | 0.015133038 | 12.1051707 | 1.874444 | 3.872014 | 3.90836 | 7.167419 | 7.505595 | 6.129407 |
| ASB11 | 0.973907833 | 0.043681142 | 0.012777135 | 12.07437843 | 9.761558 | 9.007473 | 9.757647 | 12.248383 | 13.351524 | 14.081766 |
| PHF14 | 0.990993273 | 0.043626235 | 0.01206201189 | 12.06201189 | 3.350997 | 3.770995 | 4.724406 | 8.316805 | 7.89473 | 6.942983 |
| GPHN | 1.062426074 | 0.043516135 | 0.009469207 | 12.04434321 | 4.209882 | 3.770995 | 3.764125 | 7.33564 | 7.53715 | 7.800057 |
| ASPN | 0.896865911 | 0.044203301 | 0.016658727 | 12.03642974 | 1.874444 | 4.389936 | 4.944468 | 6.814118 | 8.533804 | 7.428484 |
| LHPP | 0.987648693 | 0.043626235 | 0.012266077 | 12.03271966 | 3.024504 | 3.360637 | 3.764125 | 7.607339 | 6.613395 | 6.649696 |
| METTL6 | 0.966681685 | 0.043778104 | 0.013119428 | 12.03271966 | 3.024504 | 2.023048 | 4.724406 | 5.891233 | 6.613395 | 5.426231 |
| HERC1 | 0.977570578 | 0.043661316 | 0.012632868 | 12.02888209 | 3.839948 | 2.809601 | 3.764125 | 7.856887 | 6.319269 | 7.352555 |
| MAN1B1 | 0.911807656 | 0.044142622 | 0.015788363 | 12.02888209 | 2.201691 | 2.809601 | 3.935222 | 5.579836 | 6.549959 | 7.352555 |
| MRPS21 | 0.91607175 | 0.044110923 | 0.015530453 | 12.02435655 | 4.963444 | 3.360637 | 3.935222 | 8.051486 | 7.066159 | 7.523109 |
| STAM2 | 0.877361844 | 0.044280042 | 0.017555631 | 12.02435655 | 5.779429 | 4.389936 | 3.935222 | 8.139755 | 8.624754 | 7.523109 |
| TOMM70A | 0.755076599 | 0.046508764 | 0.025268459 | 12.0174967 | 4.815804 | 4.736586 | 5.225216 | 9.268737 | 8.402869 | 6.385515 |
| TRA2A | 0.925940018 | 0.04408867 | 0.015060905 | 12.00687014 | 6.792865 | 6.311907 | 7.132367 | 10.849852 | 10.378653 | 9.363984 |
| GLIPR1L2 | 1.048079436 | 0.043577906 | 0.010004764 | 12.00502808 | 4.209882 | 4.830496 | 5.018694 | 8.604261 | 8.200916 | 8.269212 |
| GPNMB | 0.86828546 | 0.044335719 | 0.017970058 | 12.00256867 | 6.008206 | 7.458616 | 7.69729 | 9.344992 | 11.290656 | 11.043888 |
| KIAA1377 | 0.972797339 | 0.043681142 | 0.01285199 | 11.99109912 | 4.682076 | 3.32135 | 3.90836 | 7.556937 | 7.440337 | 7.492252 |
| GAB1 | 0.993466638 | 0.043626235 | 0.012061926 | 11.98802334 | 3.024504 | 2.023048 | 2.379345 | 5.728038 | 6.608026 | 5.900694 |
| ZFYVE21 | 1.058441604 | 0.043540291 | 0.009586934 | 11.94151162 | 2.201691 | 2.023048 | 2.165421 | 5.743334 | 6.549959 | 5.426231 |
| TFAP2E | 0.969628504 | 0.043726704 | 0.013003062 | 11.94151162 | 1.874444 | 2.809601 | 2.165421 | 5.743334 | 5.306419 | 6.455366 |
| ARHGAP11A | 0.818924497 | 0.045111103 | 0.020798231 | 11.94151162 | 3.350997 | 3.770995 | 2.165421 | 5.743334 | 5.857745 | 7.36177 |
| C8orf4 | 0.861362665 | 0.044379352 | 0.018340252 | 11.91179602 | 6.792865 | 6.092406 | 7.970268 | 12.987836 | 9.666725 | 9.717557 |
| PARK2 | 1.069592179 | 0.043516135 | 0.009265056 | 11.91038053 | 4.209882 | 2.023048 | 2.165421 | 5.448591 | 5.920411 | 5.580533 |
| TESK2 | 1.034321401 | 0.043577906 | 0.01041919 | 11.91038053 | 1.874444 | 2.023048 | 2.379345 | 5.448591 | 5.509998 | 6.385515 |
| PTPRJ | 0.896551962 | 0.043568903 | 0.014682545 | 11.89360016 | 1.874444 | 3.360637 | 2.165421 | 5.448591 | 5.857745 | 6.106561 |
| IGIP | 0.863347943 | 0.045374706 | 0.022254508 | 11.89360016 | 1.874444 | 2.023048 | 4.449894 | 6.544171 | 6.205902 | 6.051818 |
| LOC100289211 | 1.052576344 | 0.043568903 | 0.009854372 | 11.89360016 | 1.874444 | 2.023048 | 2.165421 | 5.448591 | 6.319269 | 5.446557 |
| FAM86B2 | 1.05192565 | 0.043568903 | 0.009874787 | 11.89360016 | 1.874444 | 2.023048 | 2.165421 | 5.448591 | 5.936219 | 5.446557 |
| C4orf21 | 1.051284078 | 0.043568903 | 0.009883397 | 11.89051703 | 5.897292 | 6.931478 | 6.049721 | 9.179923 | 9.608485 | 9.704151 |
| TMEM164 | 0.795954361 | 0.045374706 | 0.022254508 | 11.81556599 | 6.227577 | 6.049721 | 4.754917 | 9.794456 | 8.986657 | 8.834367 |
| IMPDH2 | 0.932369312 | 0.044022007 | 0.01470296 | 11.81556599 | 1.874444 | 2.023048 | 2.165421 | 5.728038 | 5.509998 | 5.446557 |
| ATRX | 0.875866815 | 0.044285705 | 0.014761818 | 11.89115544 | 5.744513 | 6.228068 | 6.031658 | 9.799885 | 9.637899 | 8.66481 |
| REEP5 | 0.915281186 | 0.044110923 | 0.015571283 | 11.87751933 | 6.898923 | 5.297868 | 5.592916 | 9.094145 | 9.321782 | 9.163078 |
| RHOC | 0.933141974 | 0.044025007 | 0.014682545 | 11.87600552 | 5.897292 | 6.931478 | 5.609945 | 9.179923 | 9.608485 | 9.704151 |
| C12orf47 | 1.057290766 | 0.043540291 | 0.00966179 | 11.81556599 | 1.874444 | 2.023048 | 2.165421 | 5.728038 | 5.509998 | 5.446557 |
| KLHL13 | 0.929241299 | 0.044037172 | 0.014611518 | 11.81556599 | 2.201691 | 2.023048 | 2.165421 | 6.544171 | 7.414086 | 4.562324 |
| ARAP1 | 0.895471955 | 0.044203301 | 0.016719973 | 11.80079328 | 3.819732 | 3.360637 | 4.449894 | 6.339437 | 7.53715 | 8.010706 |
| LOC285965 | 0.80438775 | 0.045327183 | 0.021737326 | 11.79595259 | 4.263463 | 4.80797 | 4.449894 | 6.339437 | 8.36819 | 8.232333 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| NR3C1 | 1.053621751 | 0.043568903 | 0.009813542 | 11.77838249 | 6.227577 | 4.736586 | 5.974145 | 9.499787 | 9.532215 | 9.570168 |
| USP28 | 0.829720088 | 0.044930476 | 0.020153794 | 11.77464517 | 2.993831 | 2.023048 | 2.165421 | 5.728038 | 6.551443 | 4.562324 |
| SEPHS1 | 1.003402787 | 0.043588662 | 0.011735284 | 11.7743835 | 4.209882 | 2.406905 | 3.935222 | 7.42265 | 7.767462 | 6.924055 |
| CPOX | 1.048065682 | 0.043577906 | 0.010011569 | 11.77361635 | 1.874444 | 2.023048 | 2.165421 | 5.320955 | 5.920411 | 5.580533 |
| FBX038 | 1.02667235 | 0.043577906 | 0.010071589 | 11.77361635 | 1.874444 | 2.023048 | 2.379345 | 5.320955 | 6.774676 | 5.580533 |
| LATS1 | 1.025197695 | 0.043577906 | 0.010790745 | 11.77361635 | 1.874444 | 2.023048 | 2.165421 | 6.283686 | 5.165949 | 5.580533 |
| F2RL1 | 0.975673109 | 0.043661316 | 0.012721334 | 11.77361635 | 1.874444 | 2.023048 | 2.165421 | 7.477873 | 4.797798 | 5.580533 |
| ACAD8 | 0.96391037 | 0.043778104 | 0.013207894 | 11.77361635 | 1.874444 | 2.023048 | 2.379345 | 4.894482 | 6.861783 | 5.580533 |
| PHOSPHO2 | 0.922248271 | 0.044110923 | 0.015254849 | 11.77361635 | 1.874444 | 2.023048 | 2.165421 | 6.339437 | 4.539173 | 5.580533 |
| CDKN2B-AS1 | 0.915044201 | 0.044110923 | 0.015591698 | 11.77361635 | 1.874444 | 2.023048 | 2.165421 | 6.063041 | 4.539173 | 5.580533 |
| CYP4Z1 | 0.904852468 | 0.044173537 | 0.016199388 | 11.77361635 | 3.024504 | 2.023048 | 2.995681 | 5.705318 | 7.174648 | 5.580533 |
| EXOSC4 | 0.897254279 | 0.044203301 | 0.016627424 | 11.77361635 | 1.874444 | 2.023048 | 2.165421 | 8.553743 | 4.131418 | 5.106393 |
| POU5F1 | 0.896451688 | 0.044203301 | 0.016672338 | 11.76863057 | 3.350997 | 2.023048 | 2.379345 | 7.748771 | 5.936219 | 5.874974 |
| BRDT | 1.052986083 | 0.043568903 | 0.009827152 | 11.76792341 | 1.874444 | 2.023048 | 2.165421 | 5.579836 | 5.353925 | 5.874974 |
| RAD51 | 1.048139689 | 0.043577906 | 0.009979683 | 11.76792341 | 1.874444 | 2.023048 | 2.165421 | 5.579836 | 5.306419 | 6.924055 |
| LOC100505678 | 1.046727287 | 0.043577906 | 0.010045594 | 11.76792341 | 1.874444 | 2.023048 | 2.165421 | 5.579836 | 5.317867 | 5.874974 |
| RFC3 | 1.015144236 | 0.043581008 | 0.011259612 | 11.76792341 | 1.874444 | 2.023048 | 2.165421 | 5.579836 | 6.640994 | 5.091834 |
| SMAD9 | 0.914326436 | 0.044110923 | 0.015632528 | 11.76792341 | 1.874444 | 2.023048 | 2.165421 | 5.579836 | 5.920411 | 4.562324 |
| C9orf66 | 0.913778613 | 0.044110923 | 0.015666553 | 11.76792341 | 1.874444 | 2.023048 | 2.995681 | 5.579836 | 6.613395 | 5.106393 |
| FMO3 | 0.911891068 | 0.044142622 | 0.015774753 | 11.76792341 | 1.874444 | 2.023048 | 2.379345 | 5.579836 | 4.608763 | 6.385515 |
| FGFBP2 | 0.848019143 | 0.044599879 | 0.019028921 | 11.76792341 | 1.874444 | 2.023048 | 2.165421 | 5.579836 | 4.131418 | 6.051818 |
| LOC100652846 | 0.777873576 | 0.045844227 | 0.023457639 | 11.76792341 | 1.874444 | 2.023048 | 2.165421 | 5.579836 | 6.043524 | 3.676349 |
| PCDHB4 | 0.755261751 | 0.046505334 | 0.025237155 | 11.76792341 | 1.874444 | 2.023048 | 2.165421 | 5.579836 | 3.571326 | 5.882028 |
| DPAGT1 | 0.66651124 | 0.050336605 | 0.033154815 | 11.76792341 | 1.874444 | 2.023048 | 2.165421 | 5.579836 | 5.920411 | 2.921909 |
| HMGCL | 0.933466077 | 0.044025007 | 0.01466213 | 11.76254379 | 2.993831 | 3.770995 | 2.165421 | 6.811341 | 6.549959 | 6.051818 |
| A2ML1 | 0.842164271 | 0.044677344 | 0.019235579 | 11.76254379 | 3.024504 | 2.809601 | 2.995681 | 5.891233 | 6.549959 | 4.562324 |
| ZNF451 | 0.888565127 | 0.043986717 | 0.015632528 | 11.73936481 | 3.839948 | 7.218985 | 7.481604 | 7.074163 | 11.236404 | 5.634184 |
| NHLRC3 | 0.820008709 | 0.045095391 | 0.020664171 | 11.75955411 | 3.839948 | 4.413323 | 5.592916 | 6.183122 | 6.551443 | 4.146207 |
| WAPAL | 0.87596015 | 0.044285705 | 0.01763457 | 11.75447288 | 4.209882 | 4.830496 | 6.031658 | 7.976765 | 8.385634 | 8.705744 |
| DDIT4 | 1.003656098 | 0.043588662 | 0.011728479 | 11.74746824 | 3.024504 | 2.809601 | 2.995681 | 7.679787 | 6.549959 | 5.900694 |
| NEU1 | 0.937711558 | 0.043986717 | 0.014936373 | 11.73936481 | 4.743564 | 7.218985 | 7.481604 | 7.450526 | 11.236404 | 11.353938 |
| AICDA | 0.943152023 | 0.043921714 | 0.014251786 | 11.73834788 | 5.700376 | 2.023048 | 2.379345 | 9.934313 | 8.928336 | 7.96648 |
| RG9MTD1 | 1.057955858 | 0.043540291 | 0.00962096 | 11.72720348 | 1.874444 | 2.023048 | 2.165421 | 6.063041 | 5.509998 | 5.426231 |
| KIAA1432 | 0.830974122 | 0.044867325 | 0.019991834 | 11.72720348 | 1.874444 | 4.750708 | 2.165421 | 6.960054 | 7.094585 | 5.426231 |
| NAALADL2 | 0.996187511 | 0.043626235 | 0.011980265 | 11.71785132 | 4.963444 | 3.872014 | 3.90836 | 7.42265 | 7.89473 | 8.488368 |
| KIAA0240 | 1.006755671 | 0.043588662 | 0.011599218 | 11.71545003 | 2.993831 | 2.406905 | 2.165421 | 6.544171 | 6.237456 | 5.634184 |
| BLOC1S2 | 0.848789137 | 0.044567264 | 0.018955883 | 11.71545003 | 2.993831 | 4.911517 | 2.995681 | 6.544171 | 6.861783 | 7.492252 |
| NDNL2 | 1.045995957 | 0.043577906 | 0.010127254 | 11.71474695 | 4.309025 | 4.80797 | 4.754917 | 9.171571 | 7.845161 | 8.305171 |
| CAND2 | 0.927823987 | 0.044037172 | 0.014936373 | 11.64925523 | 4.743564 | 3.360637 | 3.90836 | 7.450526 | 7.793829 | 7.03218 |
| PPP2R2A | 0.831433626 | 0.044867325 | 0.019978224 | 11.64821739 | 3.819732 | 2.023048 | 2.379345 | 6.811341 | 4.608763 | 7.36177 |
| EARP2 | 0.7860966 | 0.045579058 | 0.022866962 | 11.6475378 | 4.815804 | 5.195784 | 5.389265 | 9.914429 | 8.737737 | 6.649696 |
| WDR73 | 0.998719712 | 0.043626235 | 0.011883634 | 11.64503997 | 2.201691 | 2.406905 | 2.165421 | 5.743334 | 5.317867 | 6.106561 |
| BTN3A2 | 1.026588524 | 0.043577906 | 0.010722695 | 11.64037532 | 1.874444 | 4.750708 | 2.379345 | 6.063041 | 5.920411 | 5.874974 |
| PLEKHF2 | 0.930011726 | 0.044037172 | 0.01480707 | 11.635267 | 3.839948 | 3.32135 | 2.165421 | 6.063041 | 6.861783 | 7.020304 |
| C1AO1 | 0.898751962 | 0.044203301 | 0.016552569 | 11.635267 | 4.309025 | 3.32135 | 2.379345 | 8.474485 | 6.861783 | 5.900694 |
| RBM45 | 1.025591798 | 0.043577906 | 0.01074311 | 11.63412807 | 7.463005 | 6.270596 | 6.175931 | 9.716222 | 10.987812 | 10.950464 |
| PMS1 | 1.033699882 | 0.043577906 | 0.0104328 | 11.63095218 | 2.201691 | 2.023048 | 2.165421 | 5.705318 | 5.317867 | 6.106561 |
| LRRC40 | 0.934221799 | 0.044402131 | 0.014609051 | 11.63095218 | 2.201691 | 2.023048 | 2.165421 | 5.705318 | 5.936219 | 4.790662 |
| | 0.865451489 | 0.044377262 | 0.018205512 | 11.63095218 | 2.993831 | 2.023048 | 2.165421 | 5.705318 | 6.640994 | 4.790662 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| LDB3 | 0.747189045 | 0.046789913 | 0.025828513 | 11.63095218 | 3.024504 | 5.297868 | 2.165421 | 5.705318 | 6.78473 | 7.695565 |
| CNOT6L | 0.863404213 | 0.044377262 | 0.018212317 | 11.62148856 | 4.963444 | 4.413323 | 6.450701 | 9.68135 | 8.502167 | 8.03232 |
| AQP3 | 0.843739594 | 0.044645837 | 0.019218101 | 11.61657734 | 1.874444 | 5.487673 | 3.935222 | 7.477873 | 7.473335 | 7.180104 |
| BMPR2 | 0.93241384 | 0.044025007 | 0.01468935 | 11.59480409 | 5.335413 | 4.750708 | 3.935222 | 7.531061 | 8.220489 | 8.870819 |
| ZMYM6 | 0.920155549 | 0.044110923 | 0.015322218 | 11.57371071 | 2.993831 | 2.023048 | 3.324375 | 6.857154 | 6.551443 | 5.446557 |
| DCAF11 | 0.842390772 | 0.044657496 | 0.019294318 | 11.5672755 | 5.700376 | 4.389936 | 3.90836 | 8.254907 | 7.440337 | 7.943848 |
| CCDC6 | 1.078985181 | 0.043516135 | 0.009006465 | 11.55443607 | 5.658609 | 5.195784 | 5.702912 | 9.154721 | 9.188984 | 9.192178 |
| UBXN4 | 1.0243232 | 0.043577906 | 0.01085199 | 11.55443607 | 5.658609 | 3.770995 | 6.072169 | 9.452312 | 9.188984 | 8.997112 |
| SEC22A | 0.873465326 | 0.044299467 | 0.017717591 | 11.55012205 | 1.874444 | 2.809601 | 2.165421 | 6.339437 | 6.237456 | 4.476242 |
| ZNF680 | 1.024881301 | 0.043577906 | 0.01079755 | 11.54594574 | 1.874444 | 2.406905 | 2.165421 | 5.448591 | 5.936219 | 5.634184 |
| CSNK2A2 | 0.893502984 | 0.044203301 | 0.016842463 | 11.54594574 | 3.819732 | 2.406905 | 3.90836 | 7.450526 | 5.936219 | 7.218312 |
| RPPH1 | 0.815855258 | 0.045173526 | 0.020991494 | 11.54594574 | 3.350997 | 2.406905 | 2.165421 | 4.739845 | 5.936219 | 6.942983 |
| LOC100129269 | 0.897025715 | 0.044203301 | 0.016645117 | 11.53862847 | 4.639409 | 2.809601 | 3.764125 | 6.252746 | 7.292524 | 8.809543 |
| LOC731275 | 0.922615043 | 0.044091888 | 0.015172 | 11.52694552 | 3.024504 | 2.406905 | 2.165421 | 5.095353 | 6.551443 | 6.32627 |
| SNAPC3 | 0.924732264 | 0.044086036 | 0.015126233 | 11.52222119 | 2.201691 | 2.406905 | 3.90836 | 5.728038 | 6.549959 | 7.020304 |
| KCNJ11 | 0.863169997 | 0.044377262 | 0.018239537 | 11.522222119 | 1.874444 | 2.406905 | 2.165421 | 5.728038 | 4.539173 | 6.106561 |
| AKAP5 | 0.771395749 | 0.046066162 | 0.02398639 | 11.52092771 | 3.024504 | 2.023048 | 5.225216 | 6.550689 | 6.189775 | 7.327219 |
| SMARCA2 | 0.965661259 | 0.043778104 | 0.013160259 | 11.49949418 | 4.263463 | 3.872014 | 4.724406 | 7.531061 | 8.609988 | 7.395512 |
| PSPC1 | 0.910989368 | 0.044159136 | 0.015844845 | 11.48318318 | 4.209882 | 4.736586 | 5.723602 | 9.245052 | 8.502167 | 7.553321 |
| IWS1 | 0.925811382 | 0.04407613 | 0.01508132 | 11.48237798 | 2.993831 | 3.770995 | 2.379345 | 6.544171 | 7.191402 | 5.900694 |
| MRE11A | 0.872538992 | 0.044299467 | 0.017758421 | 11.48237798 | 3.839948 | 3.32135 | 2.379345 | 7.771052 | 6.205902 | 5.900694 |
| RPL26L1 | 0.768852671 | 0.046108296 | 0.024143586 | 11.47630214 | 5.263699 | 4.80797 | 2.379345 | 7.074163 | 6.608026 | 8.784285 |
| SH3BGRL2 | 0.646218277 | 0.051798486 | 0.035717591 | 11.46899565 | 3.024504 | 2.023048 | 2.165421 | 6.544171 | 6.373501 | 2.921909 |
| HRH1 | 0.718586344 | 0.047781016 | 0.028061245 | 11.44096074 | 3.350997 | 3.360637 | 4.449894 | 5.026959 | 7.96603 | 3.676349 |
| ZYG11B | 0.944232361 | 0.043921714 | 0.014176931 | 11.42451014 | 5.316227 | 4.830496 | 4.285996 | 7.726141 | 8.011679 | 8.758577 |
| ALMS1 | 0.95052539 | 0.043900827 | 0.01387887 | 11.42011732 | 1.874444 | 2.406905 | 2.165421 | 4.894482 | 5.920411 | 6.722123 |
| FOXA1 | 0.764062786 | 0.046193441 | 0.024520585 | 11.42011732 | 3.024504 | 2.406905 | 2.165421 | 9.196483 | 5.920411 | 5.900694 |
| C1S | 0.765808082 | 0.046178907 | 0.02441987 | 11.41980247 | 6.949166 | 7.0583 | 8.26876 | 9.102956 | 11.782226 | 3.630092 |
| PCCA | 0.890071925 | 0.044203301 | 0.016992174 | 11.41300488 | 3.839948 | 2.023048 | 2.165421 | 5.320955 | 6.189775 | 10.859668 |
| NARS2 | 0.935677479 | 0.043994974 | 0.014541681 | 11.40732183 | 1.874444 | 2.809601 | 2.379345 | 5.891233 | 6.549959 | 7.352555 |
| MTCH2 | 0.902618509 | 0.044190907 | 0.01631031 | 11.38978011 | 1.874444 | 2.809601 | 2.165421 | 4.718672 | 6.319269 | 5.091834 |
| TTC3P1 | 0.73673459 | 0.047188004 | 0.026630146 | 11.38978011 | 4.682076 | 2.023048 | 2.995681 | 7.36523 | 6.319269 | 6.106561 |
| INPP5B | 0.910728101 | 0.044159136 | 0.015858455 | 11.38460674 | 4.963444 | 4.830496 | 5.544653 | 7.656039 | 9.053666 | 3.676349 |
| PPP1R8 | 0.944893961 | 0.043921714 | 0.01425859 | 11.35870594 | 4.209882 | 3.770995 | 3.90836 | 7.976765 | 7.414086 | 8.758577 |
| TMEM203 | 0.953761419 | 0.043857532 | 0.013722355 | 11.3563295 | 3.024504 | 2.809601 | 3.764125 | 7.177844 | 7.269549 | 6.722123 |
| PLEKHH2 | 0.953940044 | 0.043857532 | 0.013708744 | 11.34974248 | 5.328526 | 6.03611 | 5.723602 | 9.968463 | 9.228189 | 5.900694 |
| PILRB | 0.998576253 | 0.043626235 | 0.011897244 | 11.34903893 | 5.658609 | 5.195784 | 4.508334 | 8.700282 | 8.385634 | 8.488368 |
| LOH12CR1 | 0.840129193 | 0.044722631 | 0.01947329 | 11.3347672 | 1.874444 | 2.023048 | 2.379345 | 5.705318 | 6.205902 | 9.153246 |
| ETAA1 | 0.641134626 | 0.052118775 | 0.036824443 | 11.33365004 | 3.024504 | 2.406905 | 2.995681 | 6.498222 | 5.920411 | 5.882028 |
| COPS7A | 0.913850137 | 0.044110923 | 0.015659748 | 11.32269771 | 3.819732 | 2.406905 | 3.764125 | 8.033165 | 6.861783 | 2.921909 |
| STK17A | 0.855649851 | 0.044416666 | 0.018578428 | 11.31510372 | 6.267718 | 6.42919 | 4.724406 | 9.929368 | 8.97518 | 5.634184 |
| BBS7 | 0.666321665 | 0.050341041 | 0.033165703 | 11.27948081 | 5.328526 | 2.406905 | 2.379345 | 6.063041 | 6.640994 | 8.549611 |
| TMOD2 | 0.803226477 | 0.045338539 | 0.028148928 | 11.26510959 | 1.874444 | 2.406905 | 2.165421 | 4.013424 | 5.857745 | 5.874974 |
| EIF2C4 | 0.711128735 | 0.048057698 | 0.028664852 | 11.26510959 | 4.682076 | 2.406905 | 2.165421 | 5.743334 | 6.237456 | 5.900694 |
| ZBTB8A | 0.958485289 | 0.043826549 | 0.013476693 | 11.26401148 | 9.132739 | 8.75372 | 9.124675 | 11.760466 | 12.618324 | 13.098908 |
| TMED3 | 0.778396473 | 0.045844227 | 0.023444029 | 11.2609987 | 6.344798 | 4.389936 | 3.935222 | 8.604261 | 8.077554 | 7.428484 |
| RNF139 | 0.889186622 | 0.044203301 | 0.017039809 | 11.26056386 | 5.316227 | 5.297868 | 6.410545 | 8.854326 | 8.791075 | 8.986077 |
| ARHGEF9 | 0.927232038 | 0.044037172 | 0.014956788 | 11.25713732 | 1.874444 | 3.32135 | 3.935222 | 6.814118 | 5.936219 | 7.033813 |
| ARHGEF11 | 0.870617246 | 0.044325295 | 0.017845526 | 11.25713732 | 4.815804 | 3.32135 | 4.508334 | 6.814118 | 8.469821 | 7.523109 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| CORO1A | 0.983330653 | 0.043626235 | 0.012456618 | 11.2465455 | 1.874444 | 2.023048 | 3.764125 | 7.243046 | 5.306419 | 7.255535 |
| RPS27 | 0.970090329 | 0.043726704 | 0.012982647 | 11.2264398 | 11.434209 | 11.615306 | 12.321759 | 15.338386 | 14.923037 | 15.410824 |
| ADHFE1 | 0.914415019 | 0.044110923 | 0.015612113 | 11.21340538 | 3.839948 | 2.023048 | 3.90836 | 6.339437 | 6.78473 | 7.395512 |
| CD52 | 1.04069327 | 0.043577906 | 0.010289895 | 11.21183234 | 1.874444 | 2.023048 | 2.165421 | 5.320955 | 5.509998 | 7.327219 |
| SID T1 | 1.010994828 | 0.043581008 | 0.011416128 | 11.21183234 | 1.874444 | 2.023048 | 2.165421 | 7.33564 | 5.509998 | 5.106393 |
| FEM1B | 1.010819556 | 0.043581008 | 0.011422933 | 11.21183234 | 1.874444 | 2.023048 | 2.165421 | 7.177844 | 5.509998 | 5.106393 |
| FGFR1OP | 1.009234095 | 0.043581008 | 0.011456958 | 11.21183234 | 1.874444 | 2.023048 | 2.165421 | 7.631894 | 5.509998 | 5.091834 |
| DDX60 | 1.008160778 | 0.043581008 | 0.011504593 | 11.21183234 | 1.874444 | 2.023048 | 2.165421 | 6.339437 | 5.509998 | 5.106393 |
| LOC157381 | 0.976998501 | 0.043661316 | 0.012653283 | 11.21183234 | 1.874444 | 2.023048 | 2.165421 | 4.894482 | 5.509998 | 6.649696 |
| SLC30A1 | 0.940058283 | 0.043921714 | 0.01436067 | 11.21183234 | 1.874444 | 2.023048 | 2.165421 | 7.976765 | 5.509998 | 4.562324 |
| THAP1 | 0.935538795 | 0.043994974 | 0.014555291 | 11.21183234 | 1.874444 | 2.023048 | 2.165421 | 7.450526 | 5.509998 | 4.562324 |
| GPR171 | 0.930880176 | 0.044025007 | 0.014777816 | 11.21183234 | 1.874444 | 2.023048 | 2.165421 | 8.222933 | 5.509998 | 4.476242 |
| CCT6P1 | 0.911766829 | 0.044110923 | 0.015727799 | 11.21183234 | 1.874444 | 2.023048 | 2.165421 | 6.664985 | 5.509998 | 4.476242 |
| SIAE | 0.854483098 | 0.044464174 | 0.018629466 | 11.21183234 | 1.874444 | 2.023048 | 2.379345 | 7.177844 | 5.509998 | 4.146207 |
| CYP4V2 | 0.822966138 | 0.045019115 | 0.020548486 | 11.21183234 | 1.874444 | 2.023048 | 2.995681 | 6.664985 | 5.509998 | 4.476242 |
| MYBPC1 | 0.771370906 | 0.044066162 | 0.024 | 11.21183234 | 1.874444 | 2.023048 | 2.379345 | 9.621288 | 5.509998 | 2.921909 |
| CTNND2 | 0.715005996 | 0.047877006 | 0.028311671 | 11.21183234 | 1.874444 | 2.023048 | 2.165421 | 7.274575 | 5.509998 | 2.921909 |
| FAM113B | 0.694595008 | 0.048864786 | 0.030299422 | 11.21183234 | 1.874444 | 2.023048 | 2.379345 | 2.820813 | 5.509998 | 7.03218 |
| BEX5 | 0.656398353 | 0.050987756 | 0.03420074 9 | 11.21183234 | 1.874444 | 2.023048 | 2.995681 | 6.664985 | 5.509998 | 2.921909 |
| FLJ26245 | 0.653636626 | 0.051180942 | 0.034561415 | 11.21183234 | 1.874444 | 2.023048 | 2.379345 | 6.183122 | 5.509998 | 2.921909 |
| NALCN | 0.648182042 | 0.05162501 | 0.035343314 | 11.21183234 | 1.874444 | 2.023048 | 2.165421 | 5.743334 | 5.509998 | 5.900694 |
| TMEM159 | 0.629012622 | 0.053255542 | 0.038219122 | 11.21183234 | 1.874444 | 2.023048 | 2.995681 | 2.820813 | 5.509998 | 2.921909 |
| RASGRP1 | 0.819946491 | 0.045095391 | 0.021497788 | 11.2034071 | 1.874444 | 3.872014 | 3.90836 | 6.811341 | 6.319269 | 5.874974 |
| ZNF192 | 0.966920903 | 0.043778104 | 0.013112623 | 11.19023993 | 4.639409 | 4.413323 | 2.165421 | 7.394225 | 8.011679 | 7.897492 |
| HNMT | 0.966984728 | 0.043778104 | 0.013105818 | 11.18941401 | 3.819732 | 4.830496 | 4.754917 | 7.109557 | 8.314558 | 7.611911 |
| ANP32A | 0.878834176 | 0.04428042 | 0.017501191 | 11.18935604 | 3.839948 | 3.770995 | 2.995681 | 7.957464 | 7.25505 | 5.874974 |
| FTSJD1 | 0.630364753 | 0.053156193 | 0.038025179 | 11.18868799 | 4.309025 | 3.360637 | 2.995681 | 7.504712 | 7.066159 | 4.146207 |
| ZDHHC4 | 0.949818602 | 0.043900827 | 0.013906091 | 11.16928622 | 5.056948 | 2.406905 | 4.285996 | 7.792994 | 7.767462 | 7.395512 |
| LMLN | 0.967255712 | 0.043778104 | 0.013092208 | 11.16213696 | 2.201691 | 3.872014 | 4.754917 | 8.105092 | 7.793829 | 7.352555 |
| CUL3 | 0.951220022 | 0.043900827 | 0.013844845 | 11.16141718 | 4.639409 | 5.195784 | 2.379345 | 7.274575 | 8.119857 | 7.640338 |
| CREG2 | 0.629012622 | 0.053255542 | 0.038219122 | 11.15393926 | 1.874444 | 3.360637 | 4.724406 | 8.173604 | 5.353925 | 2.921909 |
| PDE8B | 1.008189306 | 0.043581008 | 0.011497788 | 11.15393926 | 1.874444 | 2.406905 | 2.165421 | 6.067497 | 5.353925 | 5.580533 |
| NCL | 0.878195452 | 0.04428042 | 0.017535216 | 11.15393926 | 5.056948 | 4.389936 | 8.011136 | 8.527804 | 6.319269 | 5.874974 |
| PIP | 1.016445978 | 0.043581008 | 0.011198367 | 11.07456727 | 7.968408 | 8.041069 | 8.011136 | 11.510248 | 11.483245 | 10.816712 |
| ATL3 | 0.873630311 | 0.044299467 | 0.01770398 1 | 11.07138096 | 1.874444 | 2.023048 | 2.165421 | 10.987062 | 5.306419 | 5.900694 |
| DNMBP-AS1 | 0.943646061 | 0.043921714 | 0.014210956 | 11.14557916 | 1.874444 | 2.023048 | 2.379345 | 4.894482 | 7.505595 | 5.580533 |
| SPATA13 | 0.926989618 | 0.044037172 | 0.014970398 | 11.14219276 | 3.839948 | 4.736586 | 4.285996 | 8.376156 | 5.857745 | 7.352555 |
| AP1G1 | 0.926568136 | 0.043968867 | 0.014015992 | 11.13785785 | 6.143785 | 4.413323 | 4.449894 | 9.621288 | 7.31791 | 7.668215 |
| FABP4 | 0.820657 08 | 0.045095391 | 0.020677782 | 11.13426505 | 6.267718 | 7.512784 | 7.593473 | 9.744652 | 8.94019 | 11.713056 |
| ZNF273 | 0.967298321 | 0.043767668 | 0.013077237 | 11.13099124 | 5.304463 | 3.360637 | 4.724406 | 8.206677 | 9.783191 | 8.03232 |
| SRPRB | 0.914286587 | 0.044110923 | 0.015639333 | 11.08745656 | 5.056948 | 4.389936 | 3.90836 | 8.527804 | 8.200916 | 7.523109 |
| NCL | 0.943988068 | 0.043921714 | 0.014183736 | 11.07456727 | 7.968408 | 8.041069 | 8.011136 | 11.510248 | 7.473335 | 11.483245 |
| PIP | 1.016445978 | 0.043581008 | 0.011198367 | 11.07138096 | 1.874444 | 2.406905 | 2.165421 | 10.987062 | 5.306419 | 10.816712 |
| B3GNT1 | 0.846234275 | 0.044641179 | 0.019132358 | 11.07138096 | 1.874444 | 2.809601 | 2.379345 | 4.341916 | 7.505595 | 5.634184 |
| MZT2A | 0.795748551 | 0.045395954 | 0.022306907 | 11.07138096 | 1.874444 | 2.406905 | 2.379345 | 8.087444 | 3.571326 | 5.634184 |
| AKR7L | 0.766217379 | 0.046178907 | 0.023923651 | 11.07138096 | 1.874444 | 2.809601 | 2.165421 | 4.013424 | 6.319269 | 5.634184 |
| DLD | 0.851494518 | 0.04449082 7 | 0.018786662 | 11.06865296 | 5.779429 | 4.351315 | 3.90836 | 7.771052 | 7.819723 | 8.175185 |
| ARMC10 | 0.977986502 | 0.043661316 | 0.012605648 | 11.06605162 | 3.024504 | 2.406905 | 2.379345 | 5.728038 | 7.094585 | 5.874974 |
| LOC100134229 | 0.897470529 | 0.044203301 | 0.016593399 | 11.06605162 | 4.815804 | 2.406905 | 2.995681 | 7.748771 | 7.91889 | 7.523109 |
| CCDC71L | 0.922001551 | 0.044110923 | 0.015261654 | 11.02551715 | 4.815804 | 5.297868 | 4.285996 | 7.748771 | 7.870158 | 9.346832 |
| ZMYM6NB | 0.850220115 | 0.044510429 | 0.018858115 | 11.02477713 | 4.263463 | 2.023048 | 2.165421 | 7.726141 | 6.551443 | 5.091834 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| STX7 | 0.776823167 | 0.045858868 | 0.023559034 | 11.01980527 | 4.309025 | 3.770995 | 2.995681 | 7.771052 | 7.292524 | 5.426231 |
| PIAS1 | 0.95614524 | 0.043840967 | 0.01362096 | 11.01604925 | 2.993831 | 3.360637 | 3.90836 | 7.177844 | 6.861783 | 6.455366 |
| ZBTB33 | 0.768143371 | 0.046157531 | 0.024253147 | 11.00704303 | 3.350997 | 2.809601 | 3.324375 | 7.037879 | 6.78473 | 4.790662 |
| RBP1 | 0.928882195 | 0.044037172 | 0.014875128 | 11.00193045 | 4.309025 | 3.360637 | 2.995681 | 6.664985 | 9.418172 | 6.455366 |
| ARID4B | 0.920109223 | 0.044110923 | 0.015342634 | 10.98688406 | 5.056948 | 4.911517 | 6.054038 | 8.514658 | 9.237827 | 8.407967 |
| DDX47 | 1.002884624 | 0.043588662 | 0.011742089 | 10.97895094 | 4.639409 | 4.750708 | 4.724406 | 9.154721 | 8.181074 | 7.748756 |
| GIMAP8 | 0.751036617 | 0.046646446 | 0.025542021 | 10.96008643 | 3.024504 | 2.023048 | 3.764125 | 4.341916 | 6.861783 | 7.218312 |
| LPCAT4 | 0.928018107 | 0.044037172 | 0.014922763 | 10.953543 | 1.874444 | 3.32135 | 2.379345 | 5.095353 | 6.774676 | 6.587378 |
| PDZD11 | 0.846700263 | 0.044634679 | 0.01909425 | 10.953543 | 2.201691 | 3.32135 | 4.754917 | 7.42265 | 6.774676 | 6.32627 |
| PAR-SN | 0.961199325 | 0.043778104 | 0.013316774 | 10.93365673 | 2.993831 | 3.360637 | 2.165421 | 6.811341 | 6.189775 | 6.051818 |
| IFNGR1 | 0.928374143 | 0.044037172 | 0.013857516 | 10.90801917 | 5.700376 | 3.770995 | 4.285996 | 9.137671 | 8.668166 | 7.218312 |
| RSAD2 | 0.617758663 | 0.054216311 | 0.039804695 | 10.90461125 | 4.743564 | 4.389936 | 4.944468 | 5.320955 | 8.220489 | 8.391335 |
| RBM22 | 0.865998941 | 0.044377262 | 0.018092548 | 10.89925185 | 4.209882 | 4.351315 | 2.995681 | 7.656039 | 8.119857 | 6.106561 |
| ADPGK | 0.805179508 | 0.045318476 | 0.021682205 | 10.89925185 | 4.209882 | 3.32135 | 2.379345 | 7.656039 | 6.043524 | 5.882028 |
| TRDMT1 | 0.932378568 | 0.044025007 | 0.014696155 | 10.89232761 | 5.335413 | 5.43468 | 3.935222 | 7.897963 | 8.87992 | 8.534542 |
| FGD3 | 0.796761073 | 0.045374042 | 0.02220279 | 10.88444106 | 3.024504 | 2.023048 | 3.90836 | 7.210813 | 4.608763 | 7.352555 |
| RSRC1 | 1.032910817 | 0.043577906 | 0.010480436 | 10.87861515 | 1.874444 | 2.023048 | 2.165421 | 6.063041 | 5.317867 | 5.446557 |
| CASP3 | 1.030768928 | 0.043577906 | 0.010548486 | 10.87861515 | 1.874444 | 2.023048 | 2.165421 | 6.283686 | 5.317867 | 5.426231 |
| LRAT | 0.918557887 | 0.044110923 | 0.015397074 | 10.87861515 | 1.874444 | 3.32135 | 2.165421 | 6.664985 | 5.317867 | 5.900694 |
| C11orf51 | 0.861007243 | 0.044379352 | 0.01836067 | 10.87861515 | 1.874444 | 3.770995 | 2.165421 | 5.320955 | 5.317867 | 6.32627 |
| LOC728218 | 0.878639427 | 0.044280042 | 0.017507996 | 10.85703452 | 6.45321 | 2.023048 | 5.389265 | 8.051486 | 8.829823 | 9.113234 |
| NARG2 | 0.938377207 | 0.043986717 | 0.014451854 | 10.85147085 | 4.639409 | 3.770995 | 2.379345 | 7.210813 | 7.713236 | 7.352555 |
| OCLN | 0.706349851 | 0.044309794 | 0.029167744 | 10.83888895 | 4.639409 | 6.044198 | 3.935222 | 8.757204 | 8.077554 | 5.882028 |
| IMP3 | 0.858024092 | 0.044387761 | 0.018462062 | 10.81914598 | 5.700376 | 4.389936 | 4.508334 | 8.139755 | 7.91889 | 7.943848 |
| DAD1 | 0.983634974 | 0.043626235 | 0.012429398 | 10.81517367 | 2.201691 | 2.809601 | 2.165421 | 6.244586 | 5.936219 | 5.446557 |
| UFSP2 | 0.859346492 | 0.044387761 | 0.018428037 | 10.80625082 | 4.815804 | 3.360637 | 2.379345 | 7.210813 | 6.794431 | 6.73963 |
| ZNF449 | 1.025423213 | 0.043577906 | 0.010763525 | 10.79263902 | 1.874444 | 2.023048 | 2.165421 | 5.728038 | 5.306419 | 5.426231 |
| GPR146 | 1.015138545 | 0.043581008 | 0.011266417 | 10.79263902 | 1.874444 | 2.023048 | 2.165421 | 5.320955 | 5.306419 | 6.587378 |
| ZNF696 | 0.991721452 | 0.043626235 | 0.01213678 | 10.79263902 | 1.874444 | 2.406905 | 2.165421 | 7.177844 | 5.306419 | 5.426231 |
| MET | 0.724924194 | 0.047570884 | 0.02750119 | 10.79263902 | 1.874444 | 5.362142 | 2.165421 | 8.447068 | 5.306419 | 5.882028 |
| MUC20 | 0.920486671 | 0.044110923 | 0.015302484 | 10.78966854 | 4.309025 | 3.360637 | 4.449894 | 8.39062 | 7.740604 | 6.618407 |
| ZSCAN12P1 | 0.884972008 | 0.044203301 | 0.017223545 | 10.78127489 | 4.209882 | 4.389936 | 5.592916 | 8.014609 | 8.402869 | 7.640338 |
| ABHD14B | 0.903713425 | 0.044173537 | 0.016253828 | 10.76248877 | 5.304463 | 3.32135 | 5.225216 | 7.726141 | 8.077554 | 8.732403 |
| C14orf93 | 0.943579603 | 0.043921714 | 0.01421776 | 10.74462573 | 1.874444 | 2.023048 | 2.165421 | 5.448591 | 4.797798 | 5.874974 |
| CCDC90B | 0.787857436 | 0.045562713 | 0.022750595 | 10.74462573 | 4.815804 | 2.023048 | 2.165421 | 5.448591 | 7.187136 | 6.455366 |
| SPAM1 | 0.774974332 | 0.045974332 | 0.023762654 | 10.74462573 | 1.874444 | 2.023048 | 2.165421 | 5.448591 | 6.189775 | 3.676349 |
| RSPO1 | 0.761279466 | 0.046345577 | 0.024778496 | 10.74462573 | 4.263463 | 2.023048 | 2.165421 | 4.739845 | 6.205902 | 5.900694 |
| KIAA0825 | 0.955729095 | 0.043840967 | 0.013654985 | 10.73201389 | 2.993831 | 3.360637 | 4.449894 | 6.396698 | 7.598264 | 7.873743 |
| HHAT | 1.023123237 | 0.044203301 | 0.010913236 | 10.72948777 | 1.874444 | 2.023048 | 2.165421 | 5.448591 | 5.353925 | 5.446557 |
| SIX1 | 0.987365168 | 0.043626235 | 0.01228492 | 10.72948777 | 1.874444 | 2.023048 | 2.165421 | 5.026959 | 5.205902 | 5.446557 |
| ACVR1C | 0.963508596 | 0.043778104 | 0.013228309 | 10.72948777 | 5.304463 | 2.023048 | 2.379345 | 5.448591 | 6.319269 | 5.446557 |
| LOC154822 | 0.963393158 | 0.043778104 | 0.013241919 | 10.72948777 | 1.874444 | 2.023048 | 2.165421 | 4.894482 | 6.043524 | 5.446557 |
| ATP2B3 | 0.935013005 | 0.044003812 | 0.014589316 | 10.72948777 | 1.874444 | 2.023048 | 2.165421 | 4.739845 | 5.936219 | 5.446557 |
| PLGLA | 0.790578421 | 0.045525452 | 0.022638312 | 10.72948777 | 3.819732 | 2.023048 | 2.165421 | 5.705318 | 5.92041 | 5.446557 |
| ZNF467 | 0.682775806 | 0.049399307 | 0.031390269 | 10.72948777 | 1.874444 | 2.023048 | 2.379345 | 6.244586 | 3.134528 | 5.446557 |
| PPA2 | 0.89690072 | 0.044203301 | 0.016651922 | 10.72492834 | 6.054828 | 4.750708 | 5.723602 | 8.173604 | 9.303543 | 9.163078 |
| PDE7B | 0.684367741 | 0.049360973 | 0.031255529 | 10.71189147 | 3.819732 | 4.911517 | 4.508334 | 5.448591 | 8.332658 | 8.095288 |
| ZNF32 | 0.943698595 | 0.043921714 | 0.01204151 | 10.70199538 | 4.639409 | 3.872014 | 2.165421 | 6.954147 | 7.740604 | 7.291822 |
| PTX3 | 0.720388741 | 0.047703746 | 0.027903368 | 10.70199538 | 2.993831 | 3.872014 | 5.974145 | 7.33564 | 7.107836 | 7.291822 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| DAB2IP | 0.863624095 | 0.044377262 | 0.018185097 | 10.70146591 | 2.993831 | 4.351315 | 3.935222 | 7.771052 | 6.608026 | 6.69026 |
| HIGD2A | 0.99130026 | 0.043626235 | 0.012157196 | 10.69672051 | 5.856559 | 4.80797 | 5.544653 | 8.98399 | 8.804107 | 8.96375 |
| LOC100507217 | 0.889166409 | 0.044203301 | 0.017046614 | 10.68790096 | 7.530567 | 7.033812 | 6.489771 | 10.948474 | 10.467346 | 9.584871 |
| SEC13 | 0.846717512 | 0.044634679 | 0.019087445 | 10.68365704 | 5.744513 | 4.351315 | 3.935222 | 8.346785 | 8.119857 | 7.352555 |
| PPA1 | 0.85309444 | 0.044464174 | 0.018697516 | 10.67911006 | 5.658609 | 5.362142 | 6.355801 | 11.105787 | 9.075328 | 7.943848 |
| SUCLG2 | 0.782725706 | 0.045701235 | 0.023131677 | 10.67762591 | 4.639409 | 4.389936 | 3.90836 | 7.856887 | 8.055928 | 6.129407 |
| E2F6 | 0.833391017 | 0.044797567 | 0.019816264 | 10.67486761 | 3.350997 | 4.351315 | 5.723602 | 7.631894 | 7.767462 | 7.825039 |
| CCDC34 | 0.918173429 | 0.044110923 | 0.015417489 | 10.67483163 | 3.350997 | 3.770995 | 4.508334 | 7.937902 | 7.187136 | 6.73963 |
| RGS1 | 0.701247734 | 0.048630415 | 0.029739367 | 10.6738375 | 6.736762 | 6.849665 | 9.532856 | 11.317421 | 10.152769 | 10.497297 |
| FAM96A | 1.01943571 | 0.043577906 | 0.011062947 | 10.6672219 | 2.201691 | 2.023048 | 2.165421 | 7.897963 | 5.306419 | 5.580533 |
| CCDC51 | 1.015350863 | 0.043581008 | 0.011232392 | 10.6672219 | 1.874444 | 2.023048 | 2.165421 | 5.320955 | 5.353925 | 5.580533 |
| INE2 | 0.975977483 | 0.043661316 | 0.012694114 | 10.6672219 | 2.201691 | 2.023048 | 2.165421 | 5.026959 | 6.549959 | 5.580533 |
| C14orf132 | 0.954925294 | 0.043840967 | 0.013695815 | 10.6672219 | 2.201691 | 2.023048 | 2.165421 | 4.894482 | 6.551443 | 5.580533 |
| ST8SIA1 | 0.816022511 | 0.045165524 | 0.020971759 | 10.6672219 | 3.819732 | 2.023048 | 2.165421 | 6.396698 | 5.509998 | 5.580533 |
| AGPAT9 | 0.800141265 | 0.045434942 | 0.022004083 | 10.6672219 | 2.201691 | 4.389936 | 2.165421 | 6.498222 | 6.319269 | 5.580533 |
| TDP2 | 0.797733127 | 0.045355733 | 0.022129976 | 10.6672219 | 4.309025 | 2.406905 | 2.165421 | 6.063041 | 6.794431 | 5.580533 |
| MCM10 | 0.893885177 | 0.044203301 | 0.016822048 | 10.66206395 | 2.201691 | 2.023048 | 2.165421 | 5.579836 | 6.794431 | 4.476242 |
| ENOX2 | 0.841389625 | 0.044701668 | 0.019385505 | 10.66206395 | 3.839948 | 2.809601 | 2.165421 | 5.579836 | 6.237456 | 6.587378 |
| DPY19L2P3 | 0.825937784 | 0.044948812 | 0.020351182 | 10.66206395 | 1.874444 | 2.023048 | 2.165421 | 5.579836 | 5.317867 | 5.580533 |
| GRIA3 | 0.763755974 | 0.046221625 | 0.024585233 | 10.66206395 | 2.201691 | 2.023048 | 2.165421 | 5.579836 | 6.549959 | 3.630092 |
| PHYH | 0.857572809 | 0.044387761 | 0.018482477 | 10.65692621 | 1.874444 | 2.023048 | 3.764125 | 7.177844 | 6.861783 | 4.562324 |
| HADH | 0.877630451 | 0.044280042 | 0.017548826 | 10.65319674 | 4.743564 | 2.023048 | 3.90836 | 8.156778 | 8.098861 | 6.051818 |
| MBTPS1 | 0.862072188 | 0.044379352 | 0.018292617 | 10.62630663 | 6.054828 | 4.750708 | 4.285996 | 9.388882 | 8.2398 | 7.695565 |
| AQR | 0.926734837 | 0.044037172 | 0.014984008 | 10.60034028 | 4.309025 | 5.487673 | 4.754917 | 8.768324 | 8.160956 | 7.825039 |
| DNAL1 | 0.972558852 | 0.043681142 | 0.012865601 | 10.59186492 | 6.792865 | 6.702075 | 6.601009 | 9.687221 | 10.227229 | 10.106959 |
| PRCP | 0.951029594 | 0.043900827 | 0.013858455 | 10.58458229 | 4.309025 | 4.389936 | 3.324375 | 7.582358 | 7.793829 | 7.03218 |
| C2orf74 | 1.021297856 | 0.043577906 | 0.010967676 | 10.57937753 | 1.874444 | 2.023048 | 2.165421 | 5.252045 | 6.861783 | 5.426231 |
| PLXNC1 | 1.02074957 | 0.043577906 | 0.011022116 | 10.57937753 | 1.874444 | 2.023048 | 2.165421 | 5.252045 | 6.237456 | 5.426231 |
| FLVCR1-AS1 | 1.001630305 | 0.043588662 | 0.011803334 | 10.57937753 | 1.874444 | 2.023048 | 2.165421 | 5.705318 | 5.165949 | 5.426231 |
| LOC152024 | 0.988989346 | 0.043626235 | 0.012211637 | 10.57937753 | 2.201691 | 2.023048 | 2.165421 | 5.026959 | 6.861783 | 5.426231 |
| RPGRIP1L | 0.959230227 | 0.043826549 | 0.013442668 | 10.57937753 | 1.874444 | 2.023048 | 2.165421 | 4.894482 | 5.920411 | 5.426231 |
| DCDC2 | 0.946164804 | 0.043900827 | 0.014096632 | 10.57937753 | 3.024504 | 2.023048 | 2.379345 | 6.396698 | 5.920411 | 5.426231 |
| TSC22D1-AS1 | 0.937640342 | 0.043986717 | 0.014472269 | 10.57937753 | 1.874444 | 2.023048 | 2.165421 | 5.728038 | 4.797798 | 5.426231 |
| ALDH6A1 | 0.935806978 | 0.043994974 | 0.014521266 | 10.57937753 | 1.874444 | 2.023048 | 2.165421 | 4.718672 | 6.237456 | 5.426231 |
| SEPSECS | 0.911173577 | 0.044159136 | 0.01582443 | 10.57937753 | 1.874444 | 2.023048 | 2.379345 | 4.718672 | 6.189775 | 5.426231 |
| MOSPD2 | 0.892813325 | 0.044203301 | 0.016682879 | 10.57937753 | 1.874444 | 2.023048 | 2.165421 | 5.728038 | 4.539173 | 5.426231 |
| BTNL8 | 0.891969836 | 0.044203301 | 0.016910514 | 10.57937753 | 1.874444 | 2.023048 | 2.165421 | 5.705318 | 4.539173 | 5.426231 |
| REPS2 | 0.806840211 | 0.045297753 | 0.021586254 | 10.57937753 | 2.201691 | 2.023048 | 4.449894 | 6.183122 | 7.107836 | 5.426231 |
| HSD17B7P2 | 0.658489659 | 0.050764584 | 0.031393936033 | 10.57937753 | 1.874444 | 2.023048 | 2.165421 | 2.820813 | 6.237456 | 5.426231 |
| TBPL1 | 0.868745927 | 0.044335719 | 0.017929228 | 10.57482242 | 5.328526 | 3.872014 | 2.379345 | 7.274575 | 7.819723 | 7.180104 |
| ERRFI1 | 0.76950338 | 0.046076407 | 0.024085063 | 10.56465753 | 8.129608 | 7.218985 | 9.395543 | 12.831614 | 10.911585 | 10.62016 |
| CSTF2T | 0.652979968 | 0.051221132 | 0.034669616 | 10.56350303 | 3.024504 | 2.406905 | 2.995681 | 6.396698 | 6.549959 | 3.676349 |
| RPIA | 0.950713298 | 0.043900827 | 0.013872065 | 10.55912404 | 4.639409 | 4.351315 | 3.935222 | 7.33564 | 7.53715 | 8.232333 |
| IPO9 | 0.90217415 | 0.044190907 | 0.01636475 | 10.55548897 | 6.45321 | 5.661685 | 5.217616 | 8.65307 | 9.570854 | 9.061607 |
| AFAP1L2 | 0.739403307 | 0.047109709 | 0.026429398 | 10.554595 | 2.993831 | 3.360637 | 2.995681 | 6.395481 | 7.440337 | 4.562324 |
| PHF17 | 0.948661669 | 0.043900827 | 0.013953726 | 10.54159207 | 6.648293 | 4.911517 | 6.282905 | 9.204692 | 9.680925 | 9.724213 |
| PRKCH | 0.815060744 | 0.045182971 | 0.021058864 | 10.53752674 | 2.993831 | 3.32135 | 5.225216 | 6.183122 | 7.066159 | 8.622681 |
| TMEM106C | 0.928314981 | 0.044037172 | 0.014902348 | 10.53747095 | 4.209882 | 4.911517 | 3.90836 | 7.607339 | 8.055928 | 7.36177 |
| MCFD2 | 1.016733182 | 0.043581008 | 0.011191562 | 10.53499494 | 5.491121 | 5.340619 | 5.018694 | 8.745998 | 8.737737 | 8.650903 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| HSD17B8 | 0.931853363 | 0.044025007 | 0.01473018 | 10.52903112 | 1.874444 | 2.809601 | 2.165421 | 5.743334 | 6.205902 | 5.106393 |
| YARS2 | 0.92969913 | 0.044037172 | 0.014827492 | 10.52903112 | 3.024504 | 2.809601 | 2.165421 | 6.544171 | 6.205902 | 5.426231 |
| GSTZ1 | 0.91699256 | 0.044110923 | 0.015469207 | 10.52903112 | 2.201691 | 2.809601 | 3.764125 | 6.651882 | 6.205902 | 6.129407 |
| PHC3 | 0.98879688 | 0.043626235 | 0.012225247 | 10.50600765 | 6.707871 | 6.762934 | 6.891005 | 9.858293 | 10.284148 | 10.224304 |
| CNNM1 | 0.913095647 | 0.044110923 | 0.015700578 | 10.50151677 | 4.682076 | 3.770995 | 5.018694 | 7.274575 | 8.296229 | 8.074602 |
| CPZ | 0.803800452 | 0.045338539 | 0.021808098 | 10.49767338 | 2.993831 | 2.809601 | 3.935222 | 5.252045 | 6.640994 | 7.327219 |
| LOC643401 | 0.947817387 | 0.043900827 | 0.014021776 | 10.49719397 | 6.765086 | 6.311907 | 6.636262 | 9.403221 | 10.137404 | 10.157018 |
| MAB21L1 | 0.794537024 | 0.04542938 | 0.022381763 | 10.48193895 | 2.201691 | 3.32135 | 2.995681 | 4.739845 | 6.774676 | 6.385515 |
| KBTBD7 | 0.90314733 | 0.044190907 | 0.016283089 | 10.47322353 | 3.350997 | 2.023048 | 2.165421 | 5.095353 | 6.189775 | 6.73963 |
| LOC286437 | 0.792635642 | 0.045439604 | 0.02248656 | 10.46692373 | 5.304463 | 5.195784 | 5.974145 | 7.450526 | 9.601037 | 8.692228 |
| TPP2 | 0.822731902 | 0.045019115 | 0.020568901 | 10.45111058 | 4.815804 | 2.809601 | 3.935222 | 7.42265 | 7.767462 | 6.195186 |
| GHITM | 0.805150151 | 0.045318476 | 0.021695815 | 10.44058169 | 5.982974 | 3.360637 | 4.724406 | 9.367104 | 7.942653 | 7.020304 |
| HLA-DPA1 | 0.782456045 | 0.045701235 | 0.023145288 | 10.43911481 | 5.491121 | 4.750708 | 6.410545 | 8.875048 | 7.473335 | 9.863386 |
| FGD5-AS1 | 0.920767918 | 0.044110923 | 0.015295679 | 10.43676358 | 6.820119 | 6.072636 | 6.175931 | 10.203722 | 9.722706 | 9.133378 |
| XRN1 | 1.01310111 | 0.043581008 | 0.011348078 | 10.43579992 | 5.304463 | 5.340119 | 4.449894 | 8.553743 | 8.724089 | 8.534542 |
| BAZ2B | 0.928759132 | 0.044037172 | 0.014881933 | 10.43487513 | 4.963444 | 2.023048 | 5.389265 | 8.346785 | 8.453372 | 7.611911 |
| FKTN | 0.911125649 | 0.044159136 | 0.015831235 | 10.43344278 | 5.491121 | 2.406905 | 5.225216 | 7.504712 | 8.737737 | 8.60836 |
| C15orf44 | 0.979700032 | 0.043626235 | 0.012565498 | 10.43266492 | 4.309025 | 3.872014 | 2.379345 | 7.167419 | 7.25505 | 7.352555 |
| ERICH1 | 0.87889079 | 0.04428042 | 0.017494386 | 10.41438808 | 1.874444 | 4.413323 | 2.995681 | 5.252045 | 7.793829 | 7.668215 |
| CD3D | 0.708057305 | 0.048268527 | 0.029001021 | 10.41199214 | 2.993831 | 2.809601 | 5.702912 | 7.607339 | 6.189775 | 6.73963 |
| CSF2RA | 0.839644975 | 0.044722631 | 0.019520925 | 10.40835225 | 2.993831 | 2.023048 | 3.764125 | 6.664985 | 6.373501 | 5.446557 |
| LOC286135 | 0.817273762 | 0.045152347 | 0.020886696 | 10.40835225 | 2.993831 | 2.406905 | 4.449894 | 6.067497 | 6.373501 | 6.942983 |
| ANTXR1 | 0.869725818 | 0.044335719 | 0.017895202 | 10.40325953 | 4.743564 | 5.195784 | 6.175931 | 8.122528 | 8.892178 | 8.79697 |
| ELMOD2 | 0.927065287 | 0.044037172 | 0.014963593 | 10.40238701 | 2.201691 | 2.406905 | 2.165421 | 5.026959 | 5.857745 | 5.580533 |
| KIF2A | 0.798579852 | 0.045355733 | 0.022089146 | 10.40238701 | 3.024504 | 3.872014 | 4.285996 | 8.39062 | 6.613395 | 5.580533 |
| TCEAL7 | 0.837435238 | 0.044763248 | 0.01963048 | 10.39735712 | 2.201691 | 2.406905 | 5.389265 | 5.579836 | 8.296229 | 7.523109 |
| CRYZ | 0.830077804 | 0.044900952 | 0.020109561 | 10.3950123 | 4.309025 | 2.406905 | 2.995681 | 7.144104 | 6.373501 | 5.900694 |
| MID1 | 0.814576698 | 0.045212649 | 0.021130997 | 10.3950123 | 1.874444 | 4.389936 | 2.995681 | 7.25991 | 6.373501 | 5.634184 |
| GPM6A | 0.94915183 | 0.043900827 | 0.013933311 | 10.39343918 | 1.874444 | 2.023048 | 2.995681 | 5.252045 | 5.920411 | 6.195186 |
| BTBD1 | 0.852520272 | 0.044480228 | 0.018739707 | 10.38037581 | 6.143785 | 4.911517 | 2.165421 | 8.447068 | 7.793829 | 8.287303 |
| WDR6 | 0.972198325 | 0.043681142 | 0.01289282 | 10.36620726 | 5.779429 | 5.195784 | 6.355801 | 9.52623 | 9.1177 | 9.153246 |
| RNF113B | 0.951406849 | 0.043900827 | 0.013831235 | 10.36408679 | 3.024504 | 2.809601 | 4.508334 | 6.183122 | 7.819723 | 7.695565 |
| ATIC | 0.613358763 | 0.054636493 | 0.040396734 | 10.35455279 | 3.024504 | 2.023048 | 2.379345 | 6.396698 | 6.189775 | 2.921909 |
| CCT4 | 0.980402673 | 0.043626235 | 0.012551888 | 10.35170267 | 6.054828 | 6.391145 | 5.702912 | 9.252991 | 9.426624 | 9.635186 |
| HSP90B1 | 0.843906228 | 0.044645837 | 0.019211296 | 10.35122978 | 6.820119 | 4.80797 | 5.544653 | 10.857682 | 8.916384 | 8.11568 |
| SFMBT1 | 0.814038065 | 0.045212649 | 0.019678085 | 10.34689834 | 3.350997 | 2.023048 | 4.724406 | 6.395481 | 6.794431 | 6.722123 |
| SEMA3D | 0.602506556 | 0.05597852 | 0.042301463 | 10.34582098 | 3.024504 | 2.406905 | 2.165421 | 6.395481 | 6.205902 | 2.921909 |
| MEAF6 | 0.78612346 | 0.045579058 | 0.022853351 | 10.33347257 | 5.779429 | 6.35207 | 5.596986 | 10.21189 | 9.148683 | 7.748756 |
| ARGFX | 0.92642488 | 0.04406867 | 0.01502688 | 10.31431089 | 6.186289 | 5.148082 | 5.225216 | 8.514658 | 8.951948 | 9.123341 |
| RPL13AP20 | 0.970688207 | 0.043709154 | 0.012962913 | 10.30759026 | 11.4075 | 11.947432 | 11.784204 | 14.999282 | 14.844591 | 15.313067 |
| SOX17 | 0.596059306 | 0.056713306 | 0.043476012 | 10.29583919 | 2.993831 | 2.023048 | 2.379345 | 5.743334 | 2.265287 | 8.357484 |
| TCTA | 0.947887109 | 0.043900827 | 0.01401497 | 10.29379662 | 5.304463 | 4.389936 | 4.944468 | 7.995811 | 8.668166 | 8.11568 |
| CUTA | 1.019714214 | 0.04357790 6 | 0.011049337 | 10.28877632 | 6.898923 | 6.849665 | 6.769247 | 10.834062 | 10.132246 | 10.147144 |
| GDI2 | 0.893232498 | 0.044203301 | 0.016849268 | 10.2884409 | 5.056948 | 3.872014 | 4.754917 | 7.918071 | 8.4199 | 7.291822 |
| MAEA | 0.819769302 | 0.045111103 | 0.0207574 | 10.28435845 | 5.335413 | 7.197097 | 5.217616 | 8.955085 | 8.579995 | 10.086439 |
| POLR1E | 0.829554173 | 0.044930476 | 0.020160599 | 10.28287953 | 5.056948 | 6.03611 | 3.764125 | 8.41912 | 7.740604 | 8.472642 |
| UBA7 | 0.90473174 | 0.044173537 | 0.016206193 | 10.28039902 | 3.024504 | 2.809601 | 4.508334 | 5.891233 | 7.870158 | 7.553321 |
| PUM1 | 0.9334459 | 0.044025007 | 0.014668935 | 10.27885202 | 6.008206 | 5.362142 | 5.217616 | 8.579223 | 8.829823 | 8.974957 |
| PPP4R2 | 0.99695544 | 0.043626235 | 0.011944879 | 10.27460209 | 3.024504 | 2.809601 | 2.165421 | 6.067497 | 6.043524 | 6.385515 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| MUTYH | 0.767642677 | 0.046164489 | 0.024315754 | 10.26889971 | 5.753024 | 3.360637 | 3.935222 | 6.396698 | 7.440337 | 9.113234 |
| TMEM176B | 0.927628533 | 0.044037172 | 0.014943178 | 10.22279952 | 5.658609 | 5.340619 | 6.355801 | 9.012327 | 10.12707 | 8.678584 |
| NEO1 | 0.772140631 | 0.046057921 | 0.023923784 | 10.20744665 | 4.209882 | 3.32135 | 3.90836 | 7.25991 | 7.68534 | 5.580533 |
| PRKY | 0.884401139 | 0.044203301 | 0.017250766 | 10.20120189 | 3.819732 | 4.389936 | 3.324375 | 6.252746 | 7.740604 | 7.611911 |
| NOTCH2NL | 0.754295995 | 0.04655221 | 0.025314733 | 10.18939489 | 3.024504 | 2.406905 | 2.165421 | 6.063041 | 6.373501 | 4.146207 |
| PPIG | 0.895218516 | 0.044203301 | 0.016747193 | 10.18806548 | 5.779429 | 4.80797 | 4.508334 | 8.156778 | 8.609988 | 8.11568 |
| LOC100131434 | 0.634307403 | 0.052781704 | 0.037421572 | 10.18725026 | 1.874444 | 2.023048 | 2.379345 | 5.728038 | 5.509998 | 2.921909 |
| TRAPPC3 | 0.945153478 | 0.043921714 | 0.014136101 | 10.18230792 | 5.056948 | 4.351315 | 2.165421 | 8.40494 | 7.269549 | 7.695565 |
| CORIN | 0.850855369 | 0.044490827 | 0.018827492 | 10.17653684 | 3.024504 | 2.023048 | 3.90836 | 5.728038 | 6.043524 | 7.255535 |
| RBM17 | 1.009356937 | 0.043581008 | 0.011450153 | 10.17301144 | 6.45321 | 6.35207 | 6.489771 | 9.799885 | 9.623267 | 10.01223 |
| KIAA1522 | 0.810096653 | 0.045243682 | 0.021380742 | 10.16769607 | 5.056948 | 5.809601 | 4.508334 | 10.252053 | 8.402869 | 7.020304 |
| VWA5A | 0.941416419 | 0.043921714 | 0.014319837 | 10.16548004 | 2.993831 | 3.32135 | 2.379345 | 6.339437 | 6.551443 | 5.882028 |
| SPDEF | 0.931468004 | 0.044025007 | 0.01474379 | 10.16227764 | 4.815804 | 4.830496 | 3.764125 | 10.106301 | 8.160956 | 6.931222 |
| C3orf15 | 0.947972362 | 0.043900827 | 0.013944556 | 10.15823006 | 1.874444 | 2.023048 | 2.165421 | 4.894482 | 5.509998 | 5.446557 |
| OSBPL6 | 0.884143586 | 0.045366463 | 0.017280027 | 10.15823006 | 1.874444 | 3.32135 | 2.165421 | 6.395481 | 5.509998 | 5.446557 |
| GHR | 0.861078518 | 0.044379352 | 0.018353862 | 10.15823006 | 1.874444 | 2.023048 | 2.165421 | 5.252045 | 5.509998 | 6.385515 |
| MST4 | 0.845448845 | 0.044641179 | 0.019159578 | 10.15823006 | 1.874444 | 2.809601 | 2.165421 | 6.651882 | 5.509998 | 4.562324 |
| NUP210 | 0.820150713 | 0.045095391 | 0.020732222 | 10.15823006 | 3.024504 | 2.023048 | 2.165421 | 7.450526 | 5.509998 | 4.476242 |
| GPCRLTM7 | 0.797090029 | 0.045366463 | 0.022178292 | 10.15823006 | 1.874444 | 2.023048 | 2.165421 | 4.013424 | 5.509998 | 5.446557 |
| GMNN | 0.782729057 | 0.045701235 | 0.023124872 | 10.15823006 | 2.993831 | 2.809601 | 2.379345 | 9.154721 | 5.509998 | 3.630092 |
| NSMCE2 | 0.744853358 | 0.046867572 | 0.02602654 | 10.15823006 | 1.874444 | 2.023048 | 2.165421 | 5.448591 | 5.509998 | 3.676349 |
| RFX3 | 0.737897012 | 0.047140798 | 0.026560054 | 10.15823006 | 1.874444 | 2.023048 | 2.165421 | 5.448591 | 5.509998 | 3.630092 |
| CEP57L1 | 0.668672579 | 0.050217419 | 0.032869684 | 10.15823006 | 2.201691 | 2.023048 | 2.165421 | 6.651882 | 5.509998 | 2.921909 |
| RNF128 | 0.637784294 | 0.052501106 | 0.036957469 | 10.15823006 | 1.874444 | 2.023048 | 2.165421 | 5.448591 | 5.509998 | 2.921909 |
| ANXA7 | 0.767689863 | 0.04616149 | 0.024304866 | 10.14115681 | 6.846868 | 5.487673 | 3.935222 | 9.506443 | 8.829823 | 7.668215 |
| GAGE1 | 0.84753216 | 0.044619412 | 0.019051378 | 10.12865214 | 3.839948 | 3.872014 | 4.754917 | 6.283686 | 7.96603 | 8.095288 |
| UPF3A | 0.928195837 | 0.044037172 | 0.014909153 | 10.12208726 | 5.658609 | 5.148082 | 5.217616 | 8.122528 | 8.998044 | 8.745549 |
| ASB8 | 0.902902451 | 0.044190907 | 0.016289895 | 10.12165593 | 3.819732 | 4.911517 | 4.754917 | 7.477873 | 7.627877 | 8.25089 |
| AMIGO2 | 0.825190613 | 0.044949653 | 0.020417149 | 10.11203933 | 4.682076 | 5.148082 | 2.165421 | 6.814118 | 8.486085 | 7.291822 |
| GPM6B | 0.85601454 | 0.044416666 | 0.018551208 | 10.10931153 | 5.316227 | 4.351315 | 3.764125 | 8.254907 | 8.65384 | 6.722123 |
| SIPA1L2 | 0.888364018 | 0.044203301 | 0.01710786 | 10.10751265 | 4.639409 | 2.023048 | 4.449894 | 7.976765 | 7.56803 | 6.649696 |
| PSMA6 | 0.804211207 | 0.045327183 | 0.021764546 | 10.10063104 | 7.445608 | 6.03611 | 5.217616 | 9.539272 | 9.168974 | 9.372483 |
| HNRNPUL2 | 0.850359676 | 0.044510429 | 0.01885131 | 10.08891485 | 3.839948 | 2.809601 | 2.379345 | 5.095353 | 7.174648 | 7.033813 |
| LOC100128338 | 0.80888284 | 0.045247607 | 0.021448112 | 10.08891485 | 3.839948 | 4.911517 | 3.324375 | 7.25991 | 7.174648 | 6.69026 |
| ATAD3B | 0.750271393 | 0.04666281 | 0.0255808 | 10.08891485 | 3.839948 | 6.060401 | 3.90836 | 7.42265 | 7.174648 | 8.287303 |
| CRYAB | 0.850048872 | 0.044510429 | 0.021055208 | 10.08667674 | 7.579257 | 9.026217 | 7.107458 | 11.304111 | 12.126312 | 10.441837 |
| KIAA1244 | 0.740999421 | 0.047036111 | 0.026299422 | 10.06334753 | 4.743564 | 6.605686 | 4.944468 | 8.433162 | 8.296229 | 8.074602 |
| PALMD | 0.992772384 | 0.043626235 | 0.012095951 | 10.06222282 | 1.874444 | 2.023048 | 2.165421 | 7.30543 | 5.353925 | 5.106393 |
| MAP4K3 | 0.991703648 | 0.043626235 | 0.012143586 | 10.06222282 | 1.874444 | 2.023048 | 2.165421 | 6.811341 | 5.353925 | 5.106393 |
| C2orf76 | 0.989217712 | 0.043626235 | 0.012198027 | 10.06222282 | 1.874444 | 2.023048 | 2.165421 | 6.183121 | 5.353925 | 5.106393 |
| ANKRD32 | 0.987569112 | 0.043626235 | 0.012279687 | 10.06222282 | 1.874444 | 2.023048 | 2.379345 | 6.283686 | 5.353925 | 5.091834 |
| CEP152 | 0.986564853 | 0.043626235 | 0.01231371 | 10.06222282 | 1.874444 | 2.023048 | 2.165421 | 5.095353 | 5.353925 | 6.051818 |
| DOCK8 | 0.961441007 | 0.043778104 | 0.01330969 | 10.06222282 | 1.874444 | 2.023048 | 2.165421 | 6.063041 | 5.353925 | 5.106393 |
| LRRC8D | 0.956122582 | 0.043840967 | 0.013627765 | 10.06222282 | 1.874444 | 2.023048 | 2.379345 | 4.894482 | 5.353925 | 6.195186 |
| FAM213B | 0.951491466 | 0.043900827 | 0.01382443 | 10.06222282 | 1.874444 | 2.023048 | 2.165421 | 6.544171 | 5.353925 | 5.874974 |
| CISH | 0.943845056 | 0.043921714 | 0.01419054 | 10.06222282 | 1.874444 | 2.023048 | 2.165421 | 6.498222 | 5.353925 | 4.790662 |
| DYNC1I1 | 0.943364003 | 0.043921714 | 0.014231371 | 10.06222282 | 1.874444 | 2.023048 | 2.165421 | 4.739845 | 5.353925 | 4.790662 |
| STRADB | 0.931553385 | 0.044025007 | 0.014736985 | 10.06222282 | 1.874444 | 2.023048 | 2.165421 | 6.195186 | 5.353925 | 6.195186 |
| CCDC112 | 0.925893834 | 0.04406867 | 0.015071113 | 10.06222282 | 1.874444 | 2.023048 | 2.165421 | 5.579836 | 5.353925 | 4.790662 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| TUBGCP3 | 0.925893834 | 0.04406867 | 0.015071113 | 10.06222282 | 1.874444 | 2.023048 | 2.165421 | 5.579836 | 5.353925 | 4.790662 |
| LINC00336 | 0.92256132 | 0.044091888 | 0.015211977 | 10.06222282 | 1.874444 | 2.023048 | 2.165421 | 4.718672 | 5.353925 | 5.900694 |
| C7orf10 | 0.916984882 | 0.044110923 | 0.015476012 | 10.06222282 | 1.874444 | 2.023048 | 2.165421 | 4.739845 | 5.353925 | 5.580533 |
| TPK1 | 0.891613522 | 0.044203301 | 0.016930929 | 10.06222282 | 1.874444 | 2.023048 | 2.165421 | 6.283686 | 5.353925 | 4.476242 |
| DPP4 | 0.867734706 | 0.044335719 | 0.017997278 | 10.06222282 | 3.350997 | 2.023048 | 2.165421 | 6.252746 | 5.353925 | 5.634184 |
| LOC729852 | 0.840876863 | 0.044701668 | 0.019426335 | 10.06222282 | 1.874444 | 2.023048 | 2.165421 | 6.283686 | 5.353925 | 4.146207 |
| CD5 | 0.800057773 | 0.045343942 | 0.022017693 | 10.06222282 | 1.874444 | 2.023048 | 2.165421 | 7.582358 | 5.353925 | 3.630092 |
| ZNF385B | 0.794563604 | 0.04542938 | 0.022374957 | 10.06222282 | 1.874444 | 2.023048 | 2.165421 | 7.33564 | 5.353925 | 3.630092 |
| RBM20 | 0.742858391 | 0.046915454 | 0.02614225 | 10.06222282 | 1.874444 | 2.023048 | 2.165421 | 5.579836 | 5.353925 | 3.676349 |
| ZWINT | 0.667171033 | 0.050335207 | 0.030076557 | 10.06222282 | 1.874444 | 2.023048 | 2.165421 | 6.244586 | 5.353925 | 2.921909 |
| ADAMTS18 | 0.649185151 | 0.05155431 | 0.035183396 | 10.06222282 | 1.874444 | 2.023048 | 2.165421 | 2.820813 | 5.353925 | 6.129407 |
| SAC3D1 | 0.643611146 | 0.051940048 | 0.036085063 | 10.06222282 | 1.874444 | 2.023048 | 2.165421 | 5.728038 | 5.353925 | 6.129407 |
| GLCE | 0.6303342 | 0.052995535 | 0.037682205 | 10.06222282 | 1.874444 | 2.023048 | 2.379345 | 5.891233 | 5.353925 | 2.921909 |
| RNF14 | 0.828518624 | 0.044930476 | 0.02023001 | 10.06021475 | 4.309025 | 3.872014 | 2.995681 | 6.498222 | 8.033973 | 6.32627 |
| GTF3C3 | 0.798490048 | 0.045355733 | 0.022095951 | 10.05931713 | 3.350997 | 2.809601 | 3.764125 | 5.320955 | 7.094585 | 6.69026 |
| INTS6 | 0.608821132 | 0.055250119 | 0.041289554 | 10.05670647 | 4.682076 | 5.362142 | 8.487278 | 8.222933 | 9.809281 | 8.692228 |
| ATP6V1C2 | 0.841593969 | 0.044701668 | 0.019358285 | 10.0534798 | 4.639409 | 3.360637 | 2.165421 | 7.144104 | 6.373501 | 6.69026 |
| FGD6 | 0.9694963 | 0.043726704 | 0.01302347 | 10.05060281 | 4.309025 | 4.80797 | 4.724406 | 8.376156 | 7.598264 | 8.053616 |
| SENP7 | 0.826233551 | 0.044936643 | 0.020332086 | 10.0465569 | 4.682076 | 3.872014 | 6.072169 | 7.679787 | 8.696398 | 8.010706 |
| HMGCR | 0.863597718 | 0.044377262 | 0.018191902 | 10.03902107 | 5.335413 | 5.340619 | 3.935222 | 8.65307 | 8.668166 | 7.327219 |
| TMEM135 | 0.935774819 | 0.043994974 | 0.014528071 | 10.03874905 | 4.963444 | 3.360637 | 3.324375 | 6.651882 | 8.200916 | 7.873743 |
| LOC728537 | 0.816318555 | 0.045165524 | 0.020951344 | 10.03874905 | 1.874444 | 2.023048 | 3.324375 | 6.651882 | 4.797798 | 5.426231 |
| CHN1 | 0.829189089 | 0.044930476 | 0.020187819 | 10.03708367 | 4.209882 | 2.023048 | 2.165421 | 5.026959 | 7.53715 | 6.385515 |
| KLF12 | 0.693083397 | 0.048944238 | 0.030407622 | 10.02807827 | 2.993831 | 2.023048 | 2.379345 | 5.705318 | 6.640994 | 3.676349 |
| EXOSC3 | 0.858338174 | 0.044387761 | 0.018455257 | 10.01151229 | 1.874444 | 2.023048 | 2.995681 | 4.739845 | 6.319269 | 5.634184 |
| LOC100507178 | 0.898151722 | 0.044203301 | 0.016577984 | 9.986541747 | 4.815804 | 4.389936 | 2.165421 | 6.811341 | 7.56803 | 8.135789 |
| GNB4 | 0.960589767 | 0.043778104 | 0.013343995 | 9.985302696 | 3.350997 | 2.809601 | 2.995681 | 7.607339 | 6.189775 | 6.129407 |
| STK38L | 0.856044801 | 0.044416666 | 0.018544403 | 9.985302696 | 4.263463 | 2.809601 | 3.90836 | 7.42265 | 7.25505 | 6.129407 |
| TP53BP1 | 0.744150043 | 0.046883977 | 0.026051718 | 9.985302696 | 5.700376 | 2.809601 | 2.995681 | 7.748771 | 7.174648 | 6.129407 |
| PEX1 | 0.764993661 | 0.046181862 | 0.024485199 | 9.984179535 | 5.335413 | 3.32135 | 2.165421 | 6.498222 | 6.640994 | 7.291822 |
| KAT2B | 0.905515337 | 0.044173537 | 0.016151752 | 9.982413069 | 2.993831 | 3.872014 | 3.90836 | 7.504712 | 7.191402 | 6.195186 |
| MEMO1 | 0.791124827 | 0.045499568 | 0.022595441 | 9.981432053 | 3.819732 | 2.023048 | 4.449894 | 8.801178 | 7.138979 | 5.091834 |
| ZNF197 | 0.816666542 | 0.045162628 | 0.020913236 | 9.978698709 | 4.309025 | 2.406905 | 2.165421 | 4.739845 | 7.627877 | 7.180104 |
| TM7SF3 | 0.900591868 | 0.044203301 | 0.016428037 | 9.969775757 | 5.056948 | 4.736586 | 4.724406 | 7.504712 | 8.119857 | 8.374509 |
| TOMM20 | 0.797013061 | 0.045366463 | 0.022183097 | 9.969504474 | 6.736762 | 5.789702 | 4.508334 | 10.437633 | 9.107223 | 7.668215 |
| AGPS | 0.810482052 | 0.045237293 | 0.021363049 | 9.952935733 | 5.263699 | 3.872014 | 2.165421 | 7.918071 | 7.187136 | 6.455366 |
| GALNT3 | 0.597106192 | 0.05661225 | 0.043335829 | 9.937051943 | 1.874444 | 2.023048 | 2.165421 | 7.726141 | 6.551443 | 2.921909 |
| HLA-DQB1 | 0.839968333 | 0.044722631 | 0.01950051 | 9.933187 | 3.839948 | 2.023048 | 4.724406 | 7.33564 | 6.373501 | 7.152205 |
| FOXJ3 | 0.758638442 | 0.044395081 | 0.024928207 | 9.930643744 | 6.554045 | 4.80797 | 4.508334 | 8.854326 | 8.119857 | 7.849596 |
| EIF2AK3 | 0.857464483 | 0.044387761 | 0.018489282 | 9.92346474 | 5.328526 | 4.351315 | 6.012527 | 9.102956 | 8.63937 | 7.825039 |
| BCL2A1 | 0.906945791 | 0.044173537 | 0.016056482 | 9.917923541 | 2.201691 | 2.023048 | 3.764125 | 7.074163 | 5.306419 | 6.455366 |
| DEPTOR | 0.609281096 | 0.055148494 | 0.041082681 | 9.917923541 | 1.874444 | 2.406905 | 3.764125 | 7.074163 | 6.549959 | 2.921909 |
| FAS | 0.957845691 | 0.043835088 | 0.013528411 | 9.917331798 | 4.309025 | 4.413323 | 3.90836 | 7.477873 | 8.033973 | 7.218312 |
| SUPT7L | 0.843134104 | 0.044657496 | 0.019239878 | 9.914685652 | 5.700376 | 3.770995 | 4.724406 | 8.591796 | 8.033973 | 7.395512 |
| NKRF | 0.878010959 | 0.044280042 | 0.017542021 | 9.911359138 | 3.839948 | 4.413323 | 5.225216 | 7.144104 | 8.737737 | 7.722406 |
| RCBTB1 | 0.818691232 | 0.045111103 | 0.020811841 | 9.906031905 | 2.201691 | 3.32135 | 2.165421 | 7.556937 | 5.509998 | 4.790662 |
| LOC100506874 | 0.858530621 | 0.044387761 | 0.018448452 | 9.9045413 | 3.024504 | 4.80797 | 4.724406 | 6.814118 | 7.25505 | 7.180104 |
| HNRNPA0 | 0.91784539 | 0.044110923 | 0.015424294 | 9.901062618 | 7.880509 | 7.0089 | 7.825025 | 10.611332 | 10.722031 | 11.188093 |
| CASP6 | 0.899669973 | 0.044203301 | 0.016507656 | 9.893210764 | 6.381847 | 5.195784 | 5.609945 | 8.616619 | 8.916384 | 9.584871 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| IL16 | 0.854285251 | 0.044464174 | 0.018649881 | 9.885360647 | 3.819732 | 4.830496 | 3.324375 | 6.396698 | 7.440337 | 8.135789 |
| LAMA2 | 0.871603074 | 0.044318262 | 0.017800612 | 9.877567183 | 3.839948 | 4.736586 | 5.544653 | 7.144104 | 8.564762 | 8.678584 |
| DOCK10 | 0.833718956 | 0.044797567 | 0.019768629 | 9.871322676 | 4.639409 | 2.809601 | 3.90836 | 6.339437 | 7.942653 | 6.924055 |
| H1FX-AS1 | 0.874769867 | 0.044285705 | 0.0176754 | 9.869404161 | 5.658609 | 3.770995 | 5.389265 | 7.656039 | 8.751258 | 8.692228 |
| GLUL | 0.849453112 | 0.044521554 | 0.018917999 | 9.862635138 | 8.074081 | 7.0089 | 8.234655 | 11.853468 | 10.890355 | 10.310874 |
| ATP7A | 0.938603807 | 0.043986717 | 0.014445049 | 9.861219758 | 3.024504 | 2.809601 | 3.324375 | 5.891233 | 7.174648 | 6.32627 |
| ORC1 | 0.752640716 | 0.046595104 | 0.025427696 | 9.861219758 | 3.024504 | 3.770995 | 2.995681 | 5.095353 | 7.094585 | 6.32627 |
| ZNF107 | 0.818464532 | 0.045111103 | 0.020839061 | 9.840278913 | 3.350997 | 2.023048 | 4.508334 | 7.36523 | 5.857745 | 6.649696 |
| COPG2 | 1.002842091 | 0.043588662 | 0.011748894 | 9.834877721 | 2.201691 | 2.023048 | 2.165421 | 5.320955 | 6.861783 | 5.426231 |
| YY2 | 0.960029096 | 0.043802358 | 0.013399796 | 9.834877721 | 2.993831 | 2.023048 | 2.165421 | 5.320955 | 6.237456 | 6.129407 |
| ST3GAL3 | 0.93402239 | 0.044025007 | 0.014628105 | 9.834877721 | 1.874444 | 2.023048 | 2.165421 | 5.320955 | 6.043524 | 4.790662 |
| ALKBH2 | 0.889272106 | 0.044203301 | 0.017026199 | 9.834877721 | 3.839948 | 2.023048 | 2.165421 | 5.320955 | 4.539173 | 5.874974 |
| SERGEF | 0.867155383 | 0.044369384 | 0.018039469 | 9.834877721 | 3.839948 | 2.023048 | 2.165421 | 5.320955 | 6.794431 | 6.195186 |
| SELL | 0.827353131 | 0.043930476 | 0.020264035 | 9.834877721 | 1.874444 | 2.023048 | 2.165421 | 5.320955 | 5.920411 | 4.146207 |
| LOC641364 | 0.797583876 | 0.045366463 | 0.022157877 | 9.834877721 | 2.201691 | 3.770995 | 3.764125 | 5.320955 | 5.920411 | 5.874974 |
| RASL12 | 0.77137254 | 0.045111103 | 0.023993195 | 9.834877721 | 1.874444 | 2.023048 | 4.508334 | 5.320955 | 7.269549 | 6.931222 |
| KLHL25 | 0.664710494 | 0.050400851 | 0.033303164 | 9.834877721 | 1.874444 | 2.023048 | 2.165421 | 5.320955 | 6.237456 | 2.921909 |
| KCNA1 | 0.662709358 | 0.050529771 | 0.033531133 | 9.834877721 | 1.874444 | 2.023048 | 2.165421 | 5.320955 | 6.189775 | 2.921909 |
| IL1RAP | 0.638478293 | 0.052444079 | 0.036826810 | 9.834877721 | 1.874444 | 2.023048 | 3.764125 | 5.320955 | 7.174648 | 3.630092 |
| FHL5 | 0.871655697 | 0.044318262 | 0.017793807 | 9.828419614 | 3.819732 | 2.809601 | 3.324375 | 7.30543 | 6.237456 | 6.106561 |
| ARID1B | 0.820831137 | 0.045095391 | 0.020670977 | 9.828222483 | 5.779429 | 5.43468 | 5.217616 | 9.07636 | 8.764653 | 7.668215 |
| LOC100507173 | 0.79613624 | 0.045374706 | 0.022240898 | 9.826053304 | 4.743564 | 5.487673 | 3.90836 | 6.664985 | 8.277663 | 8.784285 |
| NFX1 | 0.876652948 | 0.044280042 | 0.017596461 | 9.818598525 | 8.193536 | 8.041069 | 8.651386 | 10.852466 | 12.098811 | 11.489054 |
| FOXN2 | 0.594696083 | 0.056878376 | 0.043676761 | 9.8178355 | 3.839948 | 3.872014 | 3.935222 | 7.167419 | 7.25505 | 4.562324 |
| LINC00487 | 0.996168025 | 0.043626235 | 0.01198707 | 9.813846659 | 1.874444 | 2.023048 | 2.165421 | 5.252045 | 5.317867 | 5.446557 |
| ARL15 | 0.985891601 | 0.043626235 | 0.012340932 | 9.813846659 | 1.874444 | 2.023048 | 2.165421 | 6.395481 | 5.317867 | 5.106393 |
| C6orf162 | 0.98521865 | 0.043626235 | 0.012354542 | 9.813846659 | 1.874444 | 2.023048 | 2.165421 | 6.252746 | 5.317867 | 5.106393 |
| C2orf63 | 0.984835411 | 0.043626235 | 0.012374697 | 9.813846659 | 1.874444 | 2.023048 | 2.165421 | 6.183122 | 5.317867 | 5.106393 |
| ELL3 | 0.977770816 | 0.043661316 | 0.012626063 | 9.813846659 | 1.874444 | 2.023048 | 2.165421 | 5.705318 | 5.317867 | 5.091834 |
| NAALAD2 | 0.94790344 | 0.043900827 | 0.014001361 | 9.813846659 | 1.874444 | 2.023048 | 2.165421 | 4.894482 | 5.317867 | 5.874974 |
| PCDH9 | 0.941234975 | 0.043921714 | 0.014333447 | 9.813846659 | 1.874444 | 2.023048 | 2.165421 | 4.894482 | 5.317867 | 5.580533 |
| SKP1P2 | 0.934023951 | 0.044025007 | 0.0146213 | 9.813846659 | 1.874444 | 2.023048 | 2.165421 | 6.063041 | 5.317867 | 4.790662 |
| ACP6 | 0.897316154 | 0.044203301 | 0.016613814 | 9.813846659 | 1.874444 | 2.023048 | 2.165421 | 6.063041 | 12.098811 | 4.562324 |
| LYZ | 0.897169481 | 0.044203301 | 0.016638312 | 9.813846659 | 1.874444 | 2.023048 | 2.165421 | 6.811341 | 5.317867 | 4.476242 |
| FBXO5 | 0.89499506 | 0.044203301 | 0.016767608 | 9.813846659 | 1.874444 | 2.023048 | 2.165421 | 6.664985 | 5.317867 | 4.476242 |
| GLYATL2 | 0.874171492 | 0.044299467 | 0.017690371 | 9.813846659 | 1.874444 | 2.023048 | 2.165421 | 5.728038 | 5.317867 | 4.476242 |
| RAB23 | 0.83710216 | 0.044763248 | 0.019644097 | 9.813846659 | 1.874444 | 2.023048 | 2.165421 | 6.252746 | 5.317867 | 4.146207 |
| LRMP | 0.820153681 | 0.045095391 | 0.020725417 | 9.813846659 | 1.874444 | 2.023048 | 2.165421 | 5.728038 | 5.317867 | 4.146207 |
| GPR98 | 0.811718241 | 0.045218796 | 0.021269139 | 9.813846659 | 1.874444 | 2.023048 | 3.324375 | 6.857154 | 5.317867 | 4.790662 |
| CARD16 | 0.775795021 | 0.045911642 | 0.023680163 | 9.813846659 | 1.874444 | 2.023048 | 2.165421 | 6.498222 | 5.317867 | 3.676349 |
| HMGN5 | 0.766109793 | 0.046178907 | 0.024406261 | 9.813846659 | 1.874444 | 2.023048 | 2.165421 | 6.396698 | 5.317867 | 3.630092 |
| PROL1 | 0.762818226 | 0.046304892 | 0.024695475 | 9.813846659 | 1.874444 | 2.023048 | 2.165421 | 9.904384 | 5.317867 | 2.921909 |
| LOC100507062 | 0.761300757 | 0.046345155 | 0.024768289 | 9.813846659 | 1.874444 | 2.023048 | 2.165421 | 6.067497 | 5.317867 | 3.676349 |
| GNRH1 | 0.761300757 | 0.046345155 | 0.024768289 | 9.813846659 | 1.874444 | 2.023048 | 2.165421 | 6.067497 | 5.317867 | 3.676349 |
| LOC100506963 | 0.746486231 | 0.046811314 | 0.025908813 | 9.813846659 | 1.874444 | 2.023048 | 2.165421 | 5.705318 | 5.317867 | 3.676349 |
| GK | 0.740631282 | 0.047048421 | 0.026328003 | 9.813846659 | 1.874444 | 2.023048 | 3.324375 | 5.579836 | 5.317867 | 3.676349 |
| MLF1IP | 0.733703947 | 0.047307334 | 0.026809119 | 9.813846659 | 1.874444 | 2.023048 | 2.165421 | 5.579836 | 5.317867 | 3.630092 |
| GLRA3 | 0.691483849 | 0.048955004 | 0.030565498 | 9.813846659 | 1.874444 | 2.023048 | 2.165421 | 6.960054 | 5.317867 | 2.921909 |
| MAD2L1 | 0.676922509 | 0.049712169 | 0.031972099 | 9.813846659 | 1.874444 | 2.023048 | 2.165421 | 6.550689 | 5.317867 | 2.921909 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| CXCR6 | 0.674925916 | 0.049831488 | 0.032191222 | 9.813846659 | 1.874444 | 2.023048 | 2.165421 | 6.498222 | 5.317867 | 2.921909 |
| ABHD10 | 0.670922019 | 0.050055202 | 0.032652603 | 9.813846659 | 1.874444 | 2.023048 | 2.165421 | 6.395481 | 5.317867 | 2.921909 |
| TMEM206 | 0.670922019 | 0.050055202 | 0.032652603 | 9.813846659 | 1.874444 | 2.023048 | 2.165421 | 6.395481 | 5.317867 | 2.921909 |
| DNAH14 | 0.670922019 | 0.050055202 | 0.032652603 | 9.813846659 | 1.874444 | 2.023048 | 2.165421 | 6.395481 | 5.317867 | 2.921909 |
| LOC100507331 | 0.649243735 | 0.051527347 | 0.035154134 | 9.813846659 | 1.874444 | 2.023048 | 2.165421 | 5.891233 | 5.317867 | 2.921909 |
| DHRS7 | 0.901580499 | 0.044203301 | 0.016380401 | 9.813480648 | 3.024504 | 3.770995 | 2.379345 | 6.651882 | 6.319269 | 6.106561 |
| TACSTD2 | 0.688647036 | 0.049115877 | 0.030775774 | 9.80963878 | 5.753024 | 8.936581 | 5.702912 | 11.495267 | 9.312691 | 8.997112 |
| MSTO1 | 0.840805747 | 0.044709815 | 0.019444029 | 9.79499518 | 1.874444 | 3.32135 | 2.165421 | 6.283686 | 6.613395 | 4.562324 |
| CDKL2 | 0.993360304 | 0.043626235 | 0.012082341 | 9.791337483 | 1.874444 | 2.023048 | 2.165421 | 5.448591 | 5.165949 | 5.446557 |
| STARD13 | 0.857418713 | 0.044387761 | 0.018496087 | 9.787161977 | 5.753024 | 4.80797 | 3.90836 | 7.748771 | 8.098861 | 8.374509 |
| LUC7L2 | 0.839621195 | 0.044722631 | 0.019527731 | 9.780720723 | 6.45321 | 6.466258 | 6.326717 | 8.641022 | 9.74315 | 10.117111 |
| THUMPD2 | 0.899802187 | 0.044203301 | 0.016489282 | 9.780139171 | 2.993831 | 2.023048 | 2.995681 | 6.283686 | 7.25505 | 5.091834 |
| GBP1 | 0.80033406 | 0.045343942 | 0.021983668 | 9.776299082 | 4.815804 | 6.03611 | 6.369239 | 8.105092 | 9.99691 | 8.636861 |
| LYRM2 | 0.963839153 | 0.043778104 | 0.013221504 | 9.77272607 | 5.263699 | 5.362142 | 5.018694 | 8.206677 | 8.63937 | 8.650903 |
| PHTF2 | 0.780423963 | 0.045824482 | 0.023309289 | 9.768274352 | 3.819732 | 2.023048 | 3.955222 | 8.206677 | 7.107836 | 4.790662 |
| MOAP1 | 0.793443674 | 0.04542938 | 0.022460701 | 9.767604383 | 1.874444 | 2.023048 | 2.995681 | 6.283686 | 5.317867 | 4.476242 |
| SPIN4 | 0.593097125 | 0.057042958 | 0.043954406 | 9.767604383 | 1.874444 | 2.023048 | 2.995681 | 6.283686 | 5.317867 | 2.921909 |
| PRTG | 0.983423935 | 0.043626235 | 0.012443008 | 9.736285637 | 1.874444 | 2.023048 | 2.165421 | 6.183122 | 5.306419 | 5.106393 |
| MAB21L3 | 0.936573225 | 0.043994974 | 0.01450085 | 9.736285637 | 1.874444 | 2.023048 | 2.165421 | 6.339437 | 5.306419 | 4.790662 |
| LYRM5 | 0.926719544 | 0.044037172 | 0.014990813 | 9.736285637 | 1.874444 | 2.023048 | 2.165421 | 5.743334 | 5.306419 | 4.790662 |
| LOC440288 | 0.923476732 | 0.044091888 | 0.015191562 | 9.736285637 | 1.874444 | 2.023048 | 2.165421 | 4.718672 | 5.306419 | 6.195186 |
| POLR3K | 0.908990215 | 0.044173036 | 0.015966655 | 9.736285637 | 1.874444 | 2.023048 | 2.165421 | 6.857154 | 5.306419 | 4.562324 |
| MORN2 | 0.9082417 | 0.044173537 | 0.015995236 | 9.736285637 | 1.874444 | 2.023048 | 2.165421 | 4.802615 | 5.306419 | 4.476242 |
| TRUB1 | 0.892265141 | 0.044203301 | 0.016896904 | 9.736285637 | 1.874444 | 2.023048 | 2.165421 | 4.341916 | 5.306419 | 6.129407 |
| VPS8 | 0.887695059 | 0.044203301 | 0.017128275 | 9.736285637 | 4.815804 | 2.023048 | 2.379345 | 7.748771 | 5.306419 | 7.352555 |
| BAHD1 | 0.868390782 | 0.044335719 | 0.017956448 | 9.736285637 | 1.874444 | 2.023048 | 3.324375 | 5.728038 | 5.306419 | 5.874974 |
| IMPG2 | 0.864477889 | 0.044377262 | 0.018126574 | 9.736285637 | 1.874444 | 2.023048 | 2.995681 | 7.792994 | 5.306419 | 5.091834 |
| ERVFRD-1 | 0.862997577 | 0.044377262 | 0.018253147 | 9.736285637 | 1.874444 | 2.023048 | 2.165421 | 4.802615 | 5.306419 | 7.46072 |
| ERAP2 | 0.861717153 | 0.044379352 | 0.018306227 | 9.736285637 | 4.309025 | 2.023048 | 2.165421 | 4.341916 | 5.306419 | 6.129407 |
| FAM177B | 0.855920837 | 0.044416666 | 0.018558013 | 9.736285637 | 1.874444 | 2.023048 | 2.165421 | 4.341916 | 5.306419 | 7.352555 |
| LYRM1 | 0.793382177 | 0.04368142 | 0.018311575 | 9.734927954 | 1.874444 | 2.023048 | 2.165421 | 7.274575 | 5.306419 | 5.874974 |
| CSN3 | 0.92738906 | 0.044529634 | 0.014949983 | 9.734927954 | 1.874444 | 2.023048 | 2.165421 | 9.68135 | 5.306419 | 3.630092 |
| USP6NL | 0.757936957 | 0.046414887 | 0.024970398 | 9.736285637 | 1.874444 | 2.023048 | 2.165421 | 6.339437 | 5.306419 | 2.921909 |
| ECT2 | 0.743872 | 0.046889341 | 0.026084382 | 9.736285637 | 1.874444 | 2.023048 | 2.379345 | 7.167419 | 5.306419 | 3.630092 |
| GNA14 | 0.721530519 | 0.047677157 | 0.027796529 | 9.736285637 | 3.819732 | 2.023048 | 3.324375 | 5.743334 | 5.306419 | 5.426231 |
| SDHC | 0.687648317 | 0.049147961 | 0.03085131 | 9.736285637 | 4.263463 | 2.023048 | 2.165421 | 5.743334 | 5.306419 | 5.580533 |
| FHIT | 0.672722794 | 0.049933984 | 0.032392651 | 9.736285637 | 4.309025 | 2.023048 | 2.165421 | 5.579836 | 5.306419 | 5.634184 |
| TFB2M | 0.652266136 | 0.051304265 | 0.034786662 | 9.736285637 | 1.874444 | 2.023048 | 2.379345 | 6.395481 | 5.306419 | 2.921909 |
| ZCWPW1 | 0.633200358 | 0.052977658 | 0.037647499 | 9.734927954 | 1.874444 | 2.023048 | 2.165421 | 5.579836 | 5.306419 | 2.921909 |
| ZMYM1 | 0.973382177 | 0.043681142 | 0.012831575 | 9.734927954 | 1.874444 | 2.023048 | 2.165421 | 4.341916 | 5.317867 | 5.106393 |
| GZMB | 0.917315023 | 0.044110923 | 0.015448792 | 9.734927954 | 1.874444 | 2.023048 | 2.165421 | 5.448591 | 4.797798 | 5.446557 |
| LIN28B | 0.88049863 | 0.044278935 | 0.017422252 | 9.734927954 | 1.874444 | 2.023048 | 2.165421 | 5.448591 | 5.306419 | 4.790662 |
| ATG4A | 0.869448938 | 0.044335719 | 0.017902007 | 9.734927954 | 3.024504 | 3.32135 | 2.165421 | 5.448591 | 4.539173 | 5.426231 |
| PPIP5K1 | 0.797855442 | 0.045355733 | 0.022116366 | 9.734927954 | 1.874444 | 4.736586 | 2.165421 | 5.448591 | 7.174648 | 6.455366 |
| PRUNE | 0.717835429 | 0.047825499 | 0.028111603 | 9.734927954 | 1.874444 | 2.809601 | 2.165421 | 5.448591 | 6.608026 | 7.352555 |
| ZNF200 | 0.97042204 | 0.043726704 | 0.012975842 | 9.721212549 | 2.201691 | 2.023048 | 2.165421 | 5.095353 | 5.306419 | 3.676849 |
| TP53TG1 | 0.906570934 | 0.044173537 | 0.016070092 | 9.721212549 | 2.201691 | 3.360637 | 2.165421 | 6.283686 | 6.043524 | 5.446557 |
| PPFIA2 | 0.905115432 | 0.044173537 | 0.016185777 | 9.721212549 | 1.874444 | 2.023048 | 2.165421 | 4.718672 | 6.043524 | 5.446557 |
| MYEF2 | 0.865948946 | 0.044377262 | 0.018099354 | 9.721212549 | 3.839948 | 3.32135 | 2.165421 | 8.087444 | 6.549959 | 5.446557 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| CCNE2 | 0.85004373 | 0.044510429 | 0.018885335 | 9.721212549 | 3.024504 | 2.023048 | 2.165421 | 5.448591 | 5.353925 | 5.446557 |
| SULT1C2P1 | 0.839355283 | 0.044722631 | 0.019541341 | 9.721212549 | 1.874444 | 2.406905 | 2.165421 | 4.341916 | 6.205902 | 5.446557 |
| PI15 | 0.721212383 | 0.047696784 | 0.027816264 | 9.721212549 | 4.263463 | 3.872014 | 2.165421 | 7.937902 | 6.043524 | 5.446557 |
| KIAA1430 | 0.649830844 | 0.051486266 | 0.035069071 | 9.71596498 | 5.700376 | 3.360637 | 2.165421 | 6.814118 | 6.640994 | 6.129407 |
| SVEP1 | 0.899997074 | 0.044203301 | 0.016462062 | 9.714846786 | 3.839948 | 3.872014 | 4.724406 | 7.074163 | 8.140553 | 7.152205 |
| LIN52 | 0.866546926 | 0.044377262 | 0.018085743 | 9.697601849 | 8.379096 | 7.815412 | 7.762571 | 10.427146 | 11.656724 | 11.358224 |
| ACAD9 | 0.809452115 | 0.045247607 | 0.021427696 | 9.683528031 | 5.304463 | 4.736586 | 3.324375 | 7.177844 | 8.579995 | 7.255535 |
| SNRPD2P2 | 0.947059405 | 0.043900827 | 0.014035386 | 9.682225174 | 7.238972 | 6.35207 | 6.355801 | 9.627408 | 10.378653 | 10.166824 |
| DIEXF | 0.861349135 | 0.044379352 | 0.018347057 | 9.678964415 | 3.819732 | 3.32135 | 2.165421 | 6.252746 | 7.094585 | 5.874974 |
| ADAT1 | 0.884199603 | 0.044223984 | 0.017273222 | 9.671598011 | 2.201691 | 4.389936 | 3.764125 | 7.037879 | 7.269549 | 6.455366 |
| TRAF5 | 0.92370064 | 0.044091888 | 0.015177952 | 9.657434613 | 4.815804 | 4.389936 | 4.944468 | 8.087444 | 7.505595 | 8.32282 |
| TMEM109 | 0.932206584 | 0.044025007 | 0.01471657 | 9.652755559 | 4.639409 | 3.770995 | 4.285996 | 7.556937 | 7.713236 | 7.255535 |
| VPS35 | 0.826417753 | 0.044930476 | 0.020311671 | 9.652755559 | 5.658609 | 4.736586 | 4.285996 | 7.556937 | 8.963611 | 7.668215 |
| IPW | 0.867782866 | 0.044335719 | 0.017990473 | 9.635537548 | 3.024504 | 4.830496 | 4.508334 | 7.177844 | 8.098861 | 7.152205 |
| HTRA4 | 0.882186688 | 0.044229452 | 0.017345356 | 9.628786419 | 6.554045 | 6.092406 | 7.339085 | 9.821399 | 10.183015 | 9.592168 |
| ANTXR2 | 0.833553373 | 0.044797567 | 0.019795849 | 9.625651874 | 4.639409 | 3.770995 | 5.596986 | 7.037879 | 9.47632 | 7.800057 |
| F2R | 0.710179697 | 0.048157645 | 0.02877101 | 9.625651874 | 3.839948 | 3.770995 | 6.527811 | 7.037879 | 8.928336 | 7.352555 |
| ZNF786 | 0.832395202 | 0.04483949 | 0.019876829 | 9.621672836 | 4.263463 | 2.406905 | 3.90836 | 5.891233 | 7.174648 | 7.428484 |
| HERPUD1 | 0.899847697 | 0.044203301 | 0.016475672 | 9.608276134 | 7.155835 | 6.139057 | 6.072169 | 10.420113 | 10.008216 | 9.08248 |
| SPIN1 | 0.911994826 | 0.044142622 | 0.015767948 | 9.605772857 | 6.054828 | 4.750708 | 5.225216 | 8.014609 | 9.20872 | 9.123341 |
| CDIPT | 0.863469387 | 0.04437262 | 0.018198707 | 9.605128152 | 6.267718 | 3.872014 | 5.389265 | 8.65307 | 8.97518 | 8.175185 |
| PDSS5B | 0.815278848 | 0.045173526 | 0.021032324 | 9.587704469 | 5.316227 | 3.770995 | 4.754917 | 7.531061 | 8.986657 | 7.03218 |
| C8orf58 | 0.958867918 | 0.044326549 | 0.01345628 | 9.585208521 | 1.874444 | 2.023048 | 2.165421 | 5.026959 | 5.317867 | 5.426231 |
| MOSPD1 | 0.905387624 | 0.044173537 | 0.016158557 | 9.585208521 | 2.201691 | 2.023048 | 2.165421 | 7.25991 | 4.608763 | 5.426231 |
| LOC100289178 | 0.899914037 | 0.044203301 | 0.016468867 | 9.585208521 | 1.874444 | 2.406905 | 2.165421 | 5.891233 | 4.797798 | 5.426231 |
| TXNDC16 | 0.897450994 | 0.044203301 | 0.01600204 | 9.585208521 | 3.024504 | 2.809601 | 2.165421 | 6.498222 | 5.857745 | 5.426231 |
| HEATR5B | 0.881113588 | 0.044271261 | 0.017396393 | 9.585208521 | 3.024504 | 3.360637 | 2.165421 | 6.244586 | 6.861783 | 5.426231 |
| RNF214 | 0.870006405 | 0.044335719 | 0.017867982 | 9.585208521 | 1.874444 | 2.406905 | 2.165421 | 6.283686 | 4.539173 | 5.426231 |
| CWC22 | 0.837181983 | 0.044763248 | 0.019637292 | 9.585208521 | 1.874444 | 3.360637 | 2.165421 | 6.063041 | 5.306419 | 5.426231 |
| ENPP4 | 0.808617938 | 0.045247607 | 0.021468527 | 9.585208521 | 3.350997 | 2.023048 | 2.165421 | 7.109557 | 4.797798 | 5.426231 |
| GMCL1P1 | 0.795633277 | 0.04540117 | 0.022317795 | 9.585208521 | 3.839948 | 2.023048 | 2.165421 | 6.811341 | 5.306419 | 5.426231 |
| KIAA0317 | 0.726474512 | 0.047532676 | 0.027403879 | 9.585208521 | 2.993831 | 4.830496 | 2.165421 | 6.954147 | 6.640994 | 5.426231 |
| TRIM7 | 0.654723789 | 0.051064299 | 0.034427356 | 9.585208521 | 1.874444 | 2.023048 | 2.165421 | 5.320955 | 3.134528 | 5.426231 |
| TMC7 | 0.838074609 | 0.044745607 | 0.019601225 | 9.574490581 | 9.354026 | 8.07747 | 7.180931 | 11.036191 | 12.15075 | 11.336666 |
| SNX7 | 0.973833177 | 0.04368142 | 0.01279074 | 9.574397339 | 3.024504 | 3.32135 | 2.379345 | 6.283686 | 6.549959 | 6.195186 |
| ACSL3 | 0.816843554 | 0.045162628 | 0.020906431 | 9.572986163 | 4.309025 | 6.060401 | 5.018694 | 9.4454 | 8.277663 | 7.46072 |
| KIF3A | 0.842455419 | 0.044657496 | 0.019287513 | 9.572626689 | 2.993831 | 3.360637 | 4.944468 | 6.252746 | 7.292524 | 7.825039 |
| INSIG2 | 0.630615361 | 0.053156193 | 0.037966655 | 9.565033307 | 5.753024 | 3.360637 | 2.379345 | 6.252746 | 6.640994 | 6.618407 |
| ETNK2 | 0.896344059 | 0.044203301 | 0.016679143 | 9.560125365 | 2.993831 | 3.32135 | 2.379345 | 6.244586 | 6.608026 | 5.900694 |
| MAP1LC3C | 0.726242372 | 0.047543032 | 0.02741953 | 9.554503585 | 2.993831 | 3.360637 | 3.935222 | 4.802615 | 7.191402 | 7.152205 |
| SLC30A8 | 0.881230913 | 0.044271261 | 0.017389588 | 9.554494328 | 1.874444 | 2.406905 | 3.764125 | 5.095353 | 6.613395 | 7.020304 |
| LNX2 | 0.896223803 | 0.04483949 | 0.016692753 | 9.545622161 | 3.350997 | 3.360637 | 2.379345 | 6.954147 | 6.551443 | 5.634184 |
| EDC3 | 0.832364969 | 0.044235717 | 0.018990439 | 9.545622161 | 2.993831 | 3.360637 | 2.379345 | 6.954147 | 7.191402 | 5.634184 |
| PRCC | 0.755454341 | 0.046505334 | 0.02520313 | 9.545622161 | 3.839948 | 3.872014 | 2.379345 | 6.067497 | 7.292524 | 5.634184 |
| TMEM106B | 0.765043724 | 0.04617890707 | 0.024467506 | 9.526289835 | 4.743564 | 4.830496 | 3.935222 | 8.105092 | 7.187136 | 6.129407 |
| SRSF8 | 0.905270347 | 0.044173537 | 0.016172167 | 9.525246799 | 6.186289 | 2.809601 | 5.389265 | 8.641022 | 8.332658 | 8.997112 |
| TAC1 | 0.822497754 | 0.045019115 | 0.020575706 | 9.518638124 | 2.993831 | 2.406905 | 3.935222 | 6.244586 | 8.904331 | 5.106393 |
| BRWD3 | 0.815048871 | 0.045182971 | 0.021065669 | 9.509104506 | 2.993831 | 3.770995 | 3.935222 | 5.579836 | 7.656894 | 7.020304 |
| C14orf129 | 0.93107695 | 0.044025007 | 0.014764206 | 9.50643849 | 2.201691 | 2.406905 | 2.995681 | 6.244586 | 5.857745 | 5.446557 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| TUT1 | 0.856500495 | 0.044407381 | 0.018532154 | 9.496456142 | 3.839948 | 3.360637 | 2.165421 | 5.705318 | 6.608026 | 6.942983 |
| SCCPDH | 0.788738046 | 0.045550411 | 0.022722014 | 9.496456142 | 4.815804 | 3.360637 | 2.379345 | 7.477873 | 6.608026 | 6.051818 |
| BCL10 | 0.752473999 | 0.046595104 | 0.025441307 | 9.496456142 | 5.982974 | 3.360637 | 2.379345 | 9.179923 | 6.608026 | 6.385515 |
| PEX3 | 0.923709358 | 0.044091888 | 0.015171147 | 9.493239106 | 2.201691 | 3.360637 | 2.379345 | 5.448591 | 6.373501 | 6.385515 |
| TMTC4 | 0.883980315 | 0.044223984 | 0.017286832 | 9.493239106 | 2.201691 | 2.406905 | 3.324375 | 5.448591 | 5.936219 | 6.195186 |
| ZDHHC11 | 0.739411847 | 0.047109709 | 0.026422593 | 9.49008989 | 6.186289 | 4.736586 | 5.544653 | 7.144104 | 8.791075 | 9.50208 |
| ZNF593 | 0.850988388 | 0.044490827 | 0.018820687 | 9.485152665 | 5.056948 | 5.43468 | 4.449894 | 9.229044 | 7.740604 | 7.695565 |
| LOC441666 | 0.97562023 | 0.043661316 | 0.012728139 | 9.479864214 | 2.201691 | 2.023048 | 2.379345 | 5.252045 | 7.066159 | 5.446557 |
| NCK1 | 0.864860262 | 0.044377262 | 0.018112964 | 9.479864214 | 2.201691 | 2.809601 | 3.764125 | 6.664985 | 6.608026 | 5.446557 |
| AZIN1 | 0.910682111 | 0.044159136 | 0.015872065 | 9.478210162 | 6.143785 | 6.049721 | 5.571599 | 9.863488 | 9.294336 | 8.564524 |
| EXOG | 0.776869037 | 0.045858868 | 0.023545424 | 9.473157121 | 5.304463 | 3.32135 | 3.90836 | 6.664985 | 7.819723 | 7.152205 |
| HERC3 | 0.910576228 | 0.044159136 | 0.015885675 | 9.459568595 | 2.993831 | 3.32135 | 2.995681 | 6.857154 | 6.237456 | 5.874974 |
| SLC37A2 | 0.771108571 | 0.04607418 | 0.02402654 | 9.459568595 | 2.993831 | 3.360637 | 2.995681 | 4.894482 | 6.237456 | 7.36177 |
| PDGFC | 0.568154693 | 0.060662455 | 0.049376659 | 9.459568595 | 2.993831 | 3.872014 | 2.995681 | 7.504712 | 6.237456 | 3.630092 |
| SAA2 | 0.87573713 | 0.044285705 | 0.017654985 | 9.448753911 | 4.815804 | 4.351315 | 3.90836 | 7.679787 | 8.055928 | 6.931222 |
| VBP1 | 0.759208297 | 0.046382879 | 0.024899626 | 9.436994364 | 4.263463 | 4.750708 | 5.389265 | 8.864724 | 7.989035 | 6.587378 |
| DEM1 | 0.895866201 | 0.044203301 | 0.016706363 | 9.424272208 | 3.350997 | 2.406905 | 2.165421 | 5.252045 | 6.205902 | 6.587378 |
| PRPF39 | 0.846324796 | 0.044634679 | 0.01912147 | 9.423837309 | 2.993831 | 3.32135 | 5.596986 | 8.833301 | 8.579995 | 5.874974 |
| PANK1 | 0.856876757 | 0.044387761 | 0.018502892 | 9.420784716 | 7.595107 | 6.270596 | 7.381261 | 9.506443 | 10.535355 | 11.106371 |
| GCC2 | 0.918854585 | 0.044110923 | 0.015369854 | 9.420113192 | 3.839948 | 2.023048 | 3.90836 | 7.144104 | 6.640994 | 6.649696 |
| OPHN1 | 0.940384211 | 0.043921714 | 0.014347057 | 9.408222924 | 3.024504 | 2.406905 | 2.379345 | 5.705318 | 6.043524 | 6.195186 |
| NCKAP1L | 0.909563941 | 0.044173036 | 0.015593263 | 9.395368165 | 1.874444 | 2.406905 | 2.379345 | 5.743334 | 5.317867 | 5.106393 |
| LRRC28 | 0.895000367 | 0.044203301 | 0.016760803 | 9.395368165 | 1.874444 | 2.809601 | 2.165421 | 6.252746 | 5.335925 | 5.106393 |
| C9orf103 | 0.868352765 | 0.044335719 | 0.017963253 | 9.395368165 | 1.874444 | 2.023048 | 2.165421 | 6.960054 | 6.373501 | 5.106393 |
| ANK3 | 0.830502516 | 0.044867325 | 0.020032664 | 9.395368165 | 1.874444 | 2.406905 | 2.165421 | 6.183122 | 6.319269 | 5.106393 |
| PGBD2 | 0.818323631 | 0.045123634 | 0.02085199 | 9.395368165 | 1.874444 | 2.406905 | 3.324375 | 5.705318 | 5.920411 | 5.106393 |
| ZNF853 | 0.809455894 | 0.045247607 | 0.021420891 | 9.395368165 | 1.874444 | 2.406905 | 3.764125 | 6.544171 | 5.936219 | 5.106393 |
| XDH | 0.722780918 | 0.04762218 | 0.027667234 | 9.395368165 | 1.874444 | 4.351315 | 2.379345 | 6.39481 | 5.936219 | 5.106393 |
| NDUFC2 | 0.890802577 | 0.044203301 | 0.016958149 | 9.380428912 | 6.143785 | 5.362142 | 6.072169 | 8.591796 | 9.138429 | 9.397686 |
| ENTPD1 | 0.723807981 | 0.047585406 | 0.027571283 | 9.376899158 | 5.335413 | 5.297868 | 5.544653 | 6.960054 | 9.042712 | 8.564524 |
| DKFZp686K1684 | 0.976441613 | 0.043661316 | 0.012666894 | 9.376158358 | 1.874444 | 2.023048 | 2.165421 | 5.252045 | 6.608026 | 5.091834 |
| DNAH8 | 0.972720601 | 0.043681142 | 0.012858796 | 9.376158358 | 1.874444 | 2.023048 | 2.165421 | 5.252045 | 5.936219 | 5.091834 |
| HLTF | 0.931103178 | 0.044025007 | 0.0147574 | 9.376158358 | 1.874444 | 2.023048 | 2.165421 | 5.252045 | 6.319269 | 4.790662 |
| GLDN | 0.903950697 | 0.044173537 | 0.016233413 | 9.376158358 | 1.874444 | 2.023048 | 2.165421 | 5.252045 | 4.608763 | 6.385515 |
| PDZD2 | 0.902453037 | 0.044190907 | 0.016330725 | 9.376158358 | 1.874444 | 2.023048 | 2.165421 | 5.252045 | 6.774676 | 4.562324 |
| RHOBTB2 | 0.888507122 | 0.044203301 | 0.017094425 | 9.376158358 | 1.874444 | 2.023048 | 2.165421 | 5.252045 | 5.936219 | 4.562324 |
| TRDN | 0.887342981 | 0.044203301 | 0.017141885 | 9.376158358 | 1.874444 | 2.023048 | 2.165421 | 5.252045 | 4.539173 | 6.051818 |
| C15orf38 | 0.801224952 | 0.045343936 | 0.02193195 | 9.376158358 | 1.874444 | 2.023048 | 2.165421 | 5.252045 | 4.131418 | 5.446557 |
| ODZ1 | 0.767738664 | 0.04616149 | 0.02428445 | 9.376158358 | 1.874444 | 2.023048 | 2.165421 | 5.252045 | 6.613395 | 3.630092 |
| LOC729176 | 0.723392766 | 0.04762218 | 0.027626404 | 9.376158358 | 1.874444 | 2.023048 | 2.165421 | 5.252045 | 3.571326 | 5.634184 |
| LRRIQ1 | 0.651726569 | 0.051344565 | 0.034858796 | 9.376158358 | 1.874444 | 2.023048 | 2.165421 | 5.252045 | 3.134528 | 5.446557 |
| ENPP5 | 0.646385108 | 0.051758104 | 0.035680163 | 9.376158358 | 1.874444 | 2.023048 | 2.165421 | 5.252045 | 5.920411 | 2.921909 |
| AADAT | 0.687584579 | 0.049147961 | 0.030858115 | 9.36150775 | 3.839948 | 3.360637 | 2.165421 | 4.341916 | 7.138979 | 6.587378 |
| EIF3J | 0.869232158 | 0.044335719 | 0.017908813 | 9.359758546 | 8.17254 | 6.931478 | 7.538623 | 10.157949 | 10.850079 | 11.356082 |
| UAP1 | 0.873399131 | 0.044299467 | 0.017724396 | 9.357023515 | 5.897292 | 5.362142 | 6.670675 | 8.935488 | 9.383862 | 9.123341 |
| LOC729176 | 0.900215093 | 0.044203301 | 0.016448452 | 9.354444804 | 7.410173 | 6.702075 | 6.450701 | 10.635825 | 9.884832 | 9.814317 |
| C11orf10 | 0.90951017 | 0.044173036 | 0.01594624 | 9.336106901 | 3.819732 | 3.32135 | 3.764125 | 6.544171 | 7.473335 | 6.618407 |
| ALDH8A1 | 0.897748399 | 0.044203301 | 0.016579789 | 9.331026833 | 4.309025 | 2.809601 | 3.764125 | 7.531061 | 6.861783 | 6.587378 |
| KAT8 | | | | | | | | | | |
| TRMT112 | 0.903638141 | 0.044173537 | 0.016260633 | 9.329124799 | 6.898923 | 6.184248 | 5.592916 | 9.204692 | 10.058027 | 9.40599 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| LDHA | 0.7850247 | 0.045655746 | 0.022978564 | 9.327175138 | 8.224469 | 8.124619 | 7.082111 | 11.445909 | 10.430001 | 10.354432 |
| LOC285758 | 0.958240786 | 0.043826549 | 0.013497108 | 9.323744973 | 1.874444 | 2.023048 | 2.165421 | 5.095353 | 6.608026 | 5.106393 |
| FMO2 | 0.849129284 | 0.044539625 | 0.018939775 | 9.323744973 | 1.874444 | 2.023048 | 4.754917 | 5.095353 | 7.656894 | 7.255535 |
| CLIC5 | 0.814651902 | 0.045212649 | 0.021124192 | 9.323744973 | 1.874444 | 2.406905 | 3.935222 | 5.095353 | 6.189775 | 6.73963 |
| MAMDC2 | 0.767188288 | 0.04617033 | 0.024353862 | 9.323744973 | 1.874444 | 3.32135 | 4.449894 | 5.095353 | 7.292524 | 7.03218 |
| HAS2 | 0.695563313 | 0.048858998 | 0.030246342 | 9.323744973 | 1.874444 | 2.809601 | 5.018694 | 5.095353 | 6.613395 | 7.03218 |
| C6orf130 | 0.659554816 | 0.050730781 | 0.03385165 | 9.323744973 | 1.874444 | 2.023048 | 4.449894 | 5.095353 | 5.936219 | 5.426231 |
| ODZ2 | 0.63058346 | 0.053156193 | 0.037984348 | 9.323744973 | 1.874444 | 4.736586 | 2.165421 | 5.095353 | 6.189775 | 5.426231 |
| C16orf87 | 0.846783268 | 0.044634679 | 0.01908064 | 9.3183741 | 3.024504 | 2.023048 | 2.165421 | 6.244586 | 6.237456 | 4.562324 |
| CELSR2 | 0.82306347 | 0.045019115 | 0.020534876 | 9.316556204 | 2.993831 | 2.406905 | 3.324375 | 6.544171 | 6.373501 | 5.091834 |
| GTF2H2C | 0.74921211 | 0.046728791 | 0.025712827 | 9.316556204 | 4.309025 | 3.32135 | 3.324375 | 6.544171 | 5.509998 | 7.849596 |
| RSU1 | 0.94616863 | 0.043900827 | 0.014089826 | 9.312944397 | 5.744513 | 6.072636 | 4.508334 | 8.745998 | 9.179013 | 8.96375 |
| RPLP2 | 0.93637201 | 0.043994974 | 0.01451461 | 9.311680707 | 11.957438 | 12.145455 | 12.163832 | 15.364497 | 14.963896 | 15.494123 |
| ASZ1 | 0.7581796270 | 0.046410533 | 0.024957469 | 9.309957171 | 5.982974 | 5.148082 | 5.571599 | 7.36623 | 8.87992 | 9.201749 |
| HCP5 | 0.967961818 | 0.043738451 | 0.013054781 | 9.301029682 | 1.874444 | 2.023048 | 2.165421 | 7.25991 | 5.165949 | 5.091834 |
| TMEM56 | 0.96650004 | 0.043778104 | 0.013133038 | 9.301029682 | 1.874444 | 2.406905 | 2.165421 | 5.320955 | 5.353925 | 5.091834 |
| GATM | 0.96634556 | 0.043778104 | 0.01313943 | 9.301029682 | 1.874444 | 2.023048 | 2.165421 | 6.811341 | 5.165949 | 5.091834 |
| KIAA1841 | 0.963340515 | 0.043778104 | 0.013248724 | 9.301029682 | 1.874444 | 2.023048 | 2.165421 | 6.183122 | 5.165949 | 5.091834 |
| APLF | 0.943921714 | 0.043921714 | 0.014326642 | 9.301029682 | 1.874444 | 2.406905 | 2.165421 | 5.320955 | 6.205902 | 5.091834 |
| RFK | 0.863101924 | 0.044377262 | 0.018246342 | 9.301029682 | 1.874444 | 1.874444 | 2.165421 | 8.014609 | 5.306419 | 5.091834 |
| LOC286189 | 0.846946602 | 0.044634679 | 0.019073835 | 9.301029682 | 1.874444 | 2.023048 | 2.995681 | 5.448591 | 5.509998 | 5.091834 |
| HHLA3 | 0.802955265 | 0.045338539 | 0.021862538 | 9.301029682 | 1.874444 | 2.023048 | 3.90836 | 6.396698 | 5.920411 | 9.201749 |
| NUDT16L1 | 0.779996533 | 0.045824482 | 0.023322899 | 9.301029682 | 1.874444 | 2.406905 | 3.935222 | 7.33564 | 5.509998 | 5.091834 |
| NOS1AP | 0.699884747 | 0.048716465 | 0.029867302 | 9.301029682 | 1.874444 | 2.406905 | 4.285996 | 5.728038 | 6.205902 | 5.091834 |
| ARFGEF1 | 0.918679425 | 0.044110923 | 0.015383464 | 9.296676091 | 3.839948 | 4.351315 | 3.935222 | 7.177844 | 7.56803 | 6.942983 |
| ATG13 | 0.757486548 | 0.046414887 | 0.024997618 | 9.295211201 | 6.554045 | 3.32135 | 4.944468 | 7.792994 | 8.160956 | 8.357484 |
| MGEA5 | 0.935566485 | 0.043994974 | 0.014548486 | 9.289062291 | 6.417969 | 4.389936 | 6.704285 | 9.633502 | 9.853832 | 9.201749 |
| RB1 | 0.880285647 | 0.044278935 | 0.017435863 | 9.266798674 | 2.993831 | 2.023048 | 2.165421 | 5.579836 | 6.205902 | 5.091834 |
| CRIP2 | 0.897537899 | 0.044203301 | 0.016586594 | 9.261728195 | 6.48761 | 6.821329 | 6.410545 | 9.698891 | 9.198885 | 11.006149 |
| BCCIP | 0.640164642 | 0.052240009 | 0.036551208 | 9.260646112 | 4.639409 | 5.43468 | 4.754917 | 9.012327 | 7.96603 | 5.882028 |
| MIOS | 0.729896664 | 0.047394039 | 0.0271228310 | 9.254529613 | 4.963444 | 4.389936 | 3.90836 | 8.173604 | 7.656894 | 6.051818 |
| KLHL18 | 0.897376279 | 0.044203301 | 0.016607009 | 9.246341455 | 3.350997 | 3.770995 | 3.935222 | 7.144104 | 6.613395 | 6.649696 |
| CTSL2 | 0.841410508 | 0.044701668 | 0.0193787 | 9.246341455 | 1.874444 | 4.736586 | 4.285996 | 7.144104 | 6.551443 | 7.218312 |
| FBLIM1 | 0.888553471 | 0.044203301 | 0.017087445 | 9.214815232 | 5.700376 | 6.228068 | 5.609945 | 8.822673 | 8.904331 | 8.941073 |
| WDSUB1 | 0.800227728 | 0.045343942 | 0.021990473 | 9.198219341 | 2.993831 | 2.023048 | 2.165421 | 5.448591 | 4.608763 | 6.195186 |
| KANSL2 | 0.911360788 | 0.044142622 | 0.015801973 | 9.197215391 | 2.201691 | 4.413323 | 3.90836 | 7.109557 | 7.406567 | 6.73963 |
| ZNF827 | 0.926309187 | 0.044406867 | 0.015035685 | 9.197160696 | 1.874444 | 4.736586 | 2.379345 | 5.095353 | 5.165949 | 5.580533 |
| PPCDC | 0.91181476 | 0.044142622 | 0.015781558 | 9.197160696 | 1.874444 | 4.389936 | 2.379345 | 4.894482 | 5.317867 | 5.580533 |
| C8orf77 | 0.771528202 | 0.046066162 | 0.023979585 | 9.19322946 | 3.819732 | 3.872014 | 2.379345 | 5.026959 | 7.440337 | 7.020304 |
| ST20 | 0.845473246 | 0.044641179 | 0.019152773 | 9.192713565 | 1.874444 | 3.360637 | 2.379345 | 5.579836 | 5.317867 | 6.195186 |
| LOC100129250 | 0.614352157 | 0.054545342 | 0.040267438 | 9.192713565 | 3.350997 | 2.023048 | 2.379345 | 5.579836 | 5.306419 | 2.921909 |
| NXT2 | 0.807721254 | 0.045265409 | 0.021512079 | 9.192428236 | 3.350997 | 3.770995 | 2.165421 | 5.448591 | 6.551443 | 6.587378 |
| LRBA | 0.795682203 | 0.04540117 | 0.0223246 | 9.192428236 | 3.350997 | 2.406905 | 2.379345 | 4.739845 | 6.551443 | 6.051818 |
| PIGC | 0.649384165 | 0.051527347 | 0.035133719 | 9.192428236 | 3.350997 | 3.360637 | 2.165421 | 7.177844 | 7.107836 | 3.676349 |
| ZFYVE28 | 0.582195638 | 0.05842099 | 0.046208915 | 9.186251256 | 2.201691 | 3.360637 | 3.90836 | 2.820813 | 7.942653 | 6.385515 |
| FAF2 | 0.855808527 | 0.044416666 | 0.018564818 | 9.183783341 | 4.743564 | 3.360637 | 2.995681 | 7.243046 | 5.317867 | 6.129407 |
| KLHL12 | 0.866573272 | 0.044377262 | 0.018078938 | 9.182980724 | 3.350997 | 2.023048 | 2.165421 | 4.894482 | 7.440337 | 6.195186 |
| FAH | 0.754377791 | 0.04655221 | 0.025307928 | 9.182980724 | 3.350997 | 3.360637 | 2.165421 | 7.243046 | 6.549959 | 4.476242 |
| TMEM192 | 0.670947347 | 0.050055202 | 0.032638993 | 9.17934421 | 5.335413 | 4.389936 | 4.508334 | 5.728038 | 8.533804 | 8.407967 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| SCN3B | 0.867006862 | 0.044369384 | 0.018059884 | 9.16379046 | 2.993831 | 2.023048 | 2.165421 | 5.095353 | 6.189775 | 5.446557 |
| MAML2 | 0.842487463 | 0.044657496 | 0.019280708 | 9.16379046 | 2.993831 | 2.023048 | 2.995681 | 4.894482 | 6.189775 | 6.649696 |
| C7orf25 | 0.830688539 | 0.044867325 | 0.020019054 | 9.16379046 | 2.993831 | 2.023048 | 3.324375 | 6.544171 | 6.189775 | 5.106393 |
| SMARCA1 | 0.934715878 | 0.044402131 | 0.014602246 | 9.162154918 | 4.309025 | 4.413323 | 4.754917 | 7.504712 | 8.502167 | 7.523109 |
| SLC35B2 | 0.86431263 | 0.044377262 | 0.018144267 | 9.159611284 | 4.209882 | 3.770995 | 4.944468 | 8.139755 | 7.505595 | 6.924055 |
| SLC12A6 | 0.894592532 | 0.044299467 | 0.016801633 | 9.156625193 | 5.316227 | 3.770995 | 4.508334 | 7.70315 | 7.627877 | 8.232333 |
| ZNF281 | 0.872608268 | 0.044299467 | 0.017751616 | 9.155591896 | 4.743564 | 2.809601 | 3.764125 | 7.937902 | 6.861783 | 6.73963 |
| SAMD9L | 0.903736525 | 0.044417353 | 0.016247023 | 9.15204562 | 1.874444 | 2.809601 | 2.995681 | 5.728038 | 6.189775 | 5.580533 |
| MXRA5 | 0.890361021 | 0.044203301 | 0.016978564 | 9.126440744 | 3.839948 | 3.360637 | 4.724406 | 6.550689 | 10.329923 | 7.020304 |
| TRAK2 | 0.749359631 | 0.046728791 | 0.025685607 | 9.126440744 | 5.304463 | 3.360637 | 2.995681 | 6.550689 | 7.793829 | 6.455366 |
| SEC62 | 0.905812398 | 0.044173537 | 0.016110922 | 9.122733769 | 7.759008 | 6.877454 | 6.861515 | 10.948474 | 9.968249 | 10.469833 |
| ZNF839 | 0.961888108 | 0.043778104 | 0.013296359 | 9.116652051 | 2.201691 | 2.023048 | 2.165421 | 6.857154 | 5.353925 | 5.091834 |
| ERBB4 | 0.791671426 | 0.045499568 | 0.022575026 | 9.116652051 | 1.874444 | 3.32135 | 2.165421 | 7.748771 | 5.353925 | 4.476242 |
| CYP2U1 | 0.755413416 | 0.046505334 | 0.025209935 | 9.116652051 | 3.024504 | 3.770995 | 2.165421 | 7.25991 | 5.353925 | 5.426231 |
| GABRB2 | 0.617802715 | 0.054209095 | 0.039789044 | 9.116652051 | 1.874444 | 2.023048 | 2.165421 | 5.252045 | 5.353925 | 2.921909 |
| PLA2G2D | 0.872688847 | 0.044299467 | 0.017738006 | 9.109287856 | 5.263699 | 2.406905 | 4.285996 | 7.42265 | 7.473335 | 7.722406 |
| C16orf48 | 0.759390888 | 0.046382879 | 0.024886016 | 9.108611025 | 3.819732 | 2.406905 | 4.508334 | 6.339437 | 5.920411 | 7.695565 |
| ATAD1 | 0.734743702 | 0.04729774 | 0.026744471 | 9.108611025 | 6.52121 | 4.830496 | 4.508334 | 8.616619 | 8.160956 | 7.695565 |
| BTG2 | 0.928118321 | 0.044037172 | 0.014915958 | 9.104185558 | 8.062715 | 7.631788 | 8.223105 | 12.3874 | 10.818314 | 11.126612 |
| AP1AR | 0.85480432 | 0.044445393 | 0.018604287 | 9.082898197 | 3.839948 | 3.770995 | 4.724406 | 6.954147 | 7.269549 | 7.218312 |
| KRBOX1 | 0.818567324 | 0.045111103 | 0.020832256 | 9.082898197 | 2.201691 | 2.023048 | 2.165421 | 6.954147 | 5.857745 | 5.106393 |
| GTF2H2 | 0.807513546 | 0.045272487 | 0.021522967 | 9.061379311 | 3.024504 | 5.661685 | 6.031658 | 8.173604 | 9.237827 | 9.486503 |
| PLA2G2D | 0.830735558 | 0.044867325 | 0.020012249 | 9.050462554 | 9.504433 | 9.168002 | 9.143179 | 11.58762 | 12.480008 | 12.682424 |
| ABI3BP | 0.833037273 | 0.044867325 | 0.020066689 | 9.043438974 | 4.682076 | 2.406905 | 4.285996 | 6.498222 | 8.453372 | 7.640338 |
| ZFAND1 | 0.831590798 | 0.044687325 | 0.019964614 | 9.032956932 | 4.639409 | 3.872014 | 3.324375 | 7.814607 | 7.187136 | 6.32627 |
| HECTD3 | 0.889990273 | 0.044203301 | 0.016998979 | 9.023132952 | 3.024504 | 2.406905 | 2.379345 | 5.448591 | 6.319269 | 5.580533 |
| CCDC88C | 0.638459655 | 0.052444079 | 0.036833617 | 9.023132952 | 2.993831 | 2.406905 | 2.165421 | 6.183122 | 3.571326 | 5.580533 |
| CCNT2 | 0.694763209 | 0.048858998 | 0.030280367 | 9.019230124 | 4.309325 | 4.389936 | 5.217616 | 8.39062 | 8.160956 | 5.874974 |
| SLC35A3 | 0.830125225 | 0.044892504 | 0.020098673 | 9.01876997 | 1.874444 | 2.406905 | 2.165421 | 5.579836 | 5.353925 | 4.476242 |
| PPP1R9A | 0.892281855 | 0.044203301 | 0.016890099 | 9.016793543 | 4.682076 | 4.389936 | 3.935222 | 7.631894 | 7.107836 | 7.668215 |
| TMEM183B | 0.860443755 | 0.044379352 | 0.018374277 | 9.016793543 | 3.350997 | 4.351315 | 3.935222 | 6.544171 | 7.107836 | 7.255535 |
| TGOLN2 | 0.888395767 | 0.044203301 | 0.017101055 | 9.012880998 | 3.350997 | 3.770995 | 4.285996 | 6.651882 | 7.292524 | 6.942983 |
| LOC100302401 | 0.783831946 | 0.045695042 | 0.023050698 | 9.011667533 | 6.054828 | 4.351315 | 5.596986 | 9.438455 | 8.402869 | 7.523109 |
| TCEB2 | 0.816346166 | 0.045165524 | 0.020944539 | 9.004719181 | 3.024504 | 2.023048 | 3.324375 | 4.802615 | 7.292524 | 6.195186 |
| VIPR1 | 0.912481384 | 0.044142622 | 0.015747533 | 8.997870117 | 6.792865 | 6.572071 | 4.724406 | 9.16317 | 9.962448 | 9.710869 |
| ZC3H7A | 0.702777863 | 0.048528882 | 0.029591017 | 8.994451756 | 1.874444 | 4.413323 | 3.764125 | 7.582358 | 5.936219 | 5.446557 |
| PNPT1 | 0.83647507 | 0.044768725 | 0.019668595 | 8.989135901 | 4.639409 | 4.750708 | 2.165421 | 6.960054 | 7.91889 | 7.033813 |
| PGR | 0.756468996 | 0.046650467 | 0.025104457 | 8.982980273 | 5.304463 | 6.762934 | 5.544653 | 8.711848 | 8.764653 | 8.503924 |
| ST13P4 | 0.868567126 | 0.044335719 | 0.017942838 | 8.975030465 | 7.392123 | 6.983552 | 6.861515 | 10.149468 | 10.739097 | 9.67008 |
| SNX14 | 0.868446922 | 0.044335719 | 0.017949643 | 8.97101457 | 3.024506 | 2.023048 | 2.165421 | 6.067497 | 6.189775 | 4.790662 |
| MLLT10 | 0.787733481 | 0.045562713 | 0.022764206 | 8.9494534 | 5.335413 | 3.872014 | 3.90836 | 7.957464 | 7.094585 | 7.033813 |
| FDPSL2A | 0.728303007 | 0.047454185 | 0.027253488 | 8.94071197 | 5.304463 | 5.43468 | 4.449894 | 6.664985 | 8.59507 | 8.519314 |
| LOC145820 | 0.820398817 | 0.045095391 | 0.020691392 | 8.939703918 | 2.201691 | 3.770995 | 3.90836 | 7.877571 | 5.306419 | 6.931222 |
| STIL | 0.790244186 | 0.045525452 | 0.022651922 | 8.939703918 | 2.993831 | 3.770995 | 2.165421 | 5.095353 | 6.237456 | 6.931222 |
| DDX19B | 0.952674875 | 0.043882243 | 0.013764546 | 8.91067111 | 1.874444 | 2.023048 | 2.165421 | 5.320955 | 5.165949 | 5.106393 |
| ZNF862 | 0.892767201 | 0.044203301 | 0.016869684 | 8.91067111 | 3.024504 | 2.809601 | 2.165421 | 5.320955 | 6.794431 | 5.874974 |
| ATG7 | 0.780363381 | 0.045824482 | 0.023316094 | 8.91067111 | 4.209882 | 2.809601 | 2.165421 | 5.320955 | 6.861783 | 6.32627 |
| LOC283914 | 0.683028088 | 0.049394421 | 0.031348078 | 8.903302375 | 4.309025 | 3.872014 | 4.285996 | 5.448591 | 7.440337 | 7.668215 |
| TTC17 | 0.871808297 | 0.044318262 | 0.017778002 | 8.900755449 | 4.743564 | 4.413323 | 3.764125 | 6.814118 | 7.845161 | 7.897492 |

TABLE 8-continued

Differentially Expressed Genes in CD10−, CD24−, CD44− Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| ACOT2 | 0.935387147 | 0.043994974 | 0.014565498 | 8.892043921 | 1.874444 | 2.023048 | 2.165421 | 5.026959 | 5.353925 | 5.106393 |
| FASTKD3 | 0.935387147 | 0.043994974 | 0.014565498 | 8.892043921 | 1.874444 | 2.023048 | 2.165421 | 5.026959 | 5.353925 | 5.106393 |
| GNPAT | 0.842973479 | 0.044657496 | 0.019246683 | 8.892043921 | 1.874444 | 3.32135 | 2.379345 | 5.026959 | 6.237456 | 5.882028 |
| TDRD3 | 0.811981162 | 0.045218796 | 0.021235114 | 8.892043921 | 1.874444 | 3.770995 | 2.379345 | 5.026959 | 6.205902 | 6.385515 |
| MB21D1 | 0.752793235 | 0.046592834 | 0.025416808 | 8.892043921 | 1.874444 | 2.023048 | 3.764125 | 5.026959 | 5.353925 | 6.129407 |
| RPL23AP64 | 0.960632025 | 0.043778104 | 0.013330384 | 8.891616387 | 1.874444 | 2.023048 | 2.165421 | 7.109557 | 5.317867 | 5.106393 |
| ADAMTS6 | 0.919056794 | 0.044110923 | 0.015363049 | 8.891616387 | 1.874444 | 2.406905 | 2.165421 | 5.095353 | 5.317867 | 5.446557 |
| SCRN3 | 0.872302172 | 0.044299467 | 0.017772031 | 8.891616387 | 3.024504 | 2.406905 | 2.165421 | 6.395481 | 5.317867 | 5.446557 |
| RFTN1 | 0.826832431 | 0.044930476 | 0.020291256 | 8.891616387 | 3.350997 | 2.023048 | 2.165421 | 5.728038 | 5.317867 | 5.874974 |
| LOC145663 | 0.723145969 | 0.04762218 | 0.027640014 | 8.891616387 | 1.874444 | 2.023048 | 2.165421 | 5.252045 | 5.317867 | 3.676349 |
| ZRANB2-AS1 | 0.716166872 | 0.04786157 | 0.028245662 | 8.891616387 | 1.874444 | 2.023048 | 2.165421 | 5.252045 | 5.317867 | 3.630092 |
| EPB41L4B | 0.619721719 | 0.054008689 | 0.039501871 | 8.891616387 | 3.024504 | 2.406905 | 2.165421 | 7.504712 | 5.317867 | 2.921909 |
| MDGA2 | 0.614045652 | 0.054587228 | 0.040317115 | 8.891616387 | 2.201691 | 2.023048 | 2.165421 | 5.705318 | 5.317867 | 2.921909 |
| PRSS16 | 0.607696045 | 0.05527432 | 0.041349439 | 8.891616387 | 1.874444 | 2.406905 | 2.165421 | 5.705318 | 5.317867 | 2.921909 |
| LOC729013 | 0.600355523 | 0.056340121 | 0.042788704 | 8.891616387 | 2.201691 | 2.023048 | 2.165421 | 5.448591 | 5.317867 | 2.921909 |
| STAU2 | 0.800036913 | 0.045343942 | 0.022024498 | 8.890131126 | 2.201691 | 2.406905 | 3.935222 | 6.651882 | 5.353925 | 5.882028 |
| PPPDE1 | 0.871203173 | 0.044325295 | 0.017818306 | 8.880392409 | 4.263463 | 3.360637 | 3.324375 | 7.144104 | 7.414086 | 6.129407 |
| GNAI2 | 0.906370477 | 0.044173537 | 0.016083702 | 8.868460971 | 7.427999 | 6.270596 | 7.180931 | 10.240121 | 9.927144 | 10.576683 |
| NR2C1 | 0.824034027 | 0.044786157 | 0.028245662 | 8.859499576 | 3.350997 | 4.351315 | 4.508334 | 6.498222 | 7.870158 | 7.152205 |
| C1APIN1 | 0.720561139 | 0.047703746 | 0.027869343 | 8.859499576 | 3.024504 | 2.023048 | 3.324375 | 6.498222 | 7.174648 | 5.106393 |
| EEF1A1 | 0.923960992 | 0.044091888 | 0.015164342 | 8.859041915 | 12.260147 | 11.991816 | 12.5153 | 15.659795 | 15.662451 | 15.077998 |
| DIS3 | 0.823425764 | 0.045005314 | 0.020512419 | 8.853633233 | 5.056948 | 4.830496 | 6.031658 | 7.976765 | 8.63937 | 8.305171 |
| PDK4 | 0.713517357 | 0.044910176 | 0.028412385 | 8.851123148 | 8.965816 | 6.732825 | 6.737132 | 10.9362 | 9.878685 | 10.256805 |
| ELK4 | 0.916072017 | 0.044110923 | 0.015523647 | 8.843301973 | 7.09018 | 6.605686 | 6.769247 | 9.750272 | 10.539257 | 9.83906 |
| CDH16 | 0.945321789 | 0.043921714 | 0.014129296 | 8.832988699 | 1.874444 | 2.023048 | 2.165421 | 4.894482 | 5.165949 | 7.774634 |
| ARV1 | 0.920116207 | 0.044110923 | 0.015335829 | 8.832988699 | 1.874444 | 2.023048 | 2.165421 | 6.244586 | 5.165949 | 4.790662 |
| LDHAL6A | 0.91072405 | 0.044159136 | 0.01586526 | 8.832988699 | 1.874444 | 2.406905 | 2.379345 | 5.252045 | 5.165949 | 5.106393 |
| LINC00410 | 0.850522752 | 0.044504737 | 0.018840422 | 8.832988699 | 1.874444 | 2.406905 | 2.165421 | 4.341916 | 5.165949 | 6.129407 |
| LINC00340 | 0.826277834 | 0.044930476 | 0.020321878 | 8.832988699 | 1.874444 | 2.023048 | 2.165421 | 6.339437 | 5.165949 | 4.146207 |
| PCCB | 0.826277834 | 0.044930476 | 0.020321878 | 8.832988699 | 1.874444 | 2.023048 | 2.165421 | 6.339437 | 5.165949 | 4.146207 |
| DENND2D | 0.815702996 | 0.045173526 | 0.021011909 | 8.832988699 | 1.874444 | 2.023048 | 2.995681 | 7.70315 | 5.165949 | 4.476242 |
| ADAM28 | 0.781131312 | 0.045799831 | 0.023266417 | 8.832988699 | 1.874444 | 2.023048 | 2.379345 | 7.976765 | 5.165949 | 3.676349 |
| CCDC99 | 0.757356082 | 0.046414887 | 0.025011228 | 8.832988699 | 1.874444 | 2.023048 | 2.165421 | 6.283686 | 5.165949 | 3.630092 |
| PPIL1 | 0.736960252 | 0.047171086 | 0.026606329 | 8.832988699 | 1.874444 | 2.023048 | 2.165421 | 5.891233 | 5.165949 | 3.630092 |
| KIF27 | 0.723865581 | 0.047585406 | 0.027564478 | 8.832988699 | 1.874444 | 2.023048 | 2.165421 | 5.579836 | 5.165949 | 2.921909 |
| C8orf85 | 0.652044561 | 0.051316368 | 0.034823409 | 8.832988699 | 1.874444 | 2.023048 | 2.165421 | 6.183122 | 5.165949 | 5.882028 |
| ARHGAP36 | 0.647187024 | 0.05166843 | 0.035522967 | 8.832988699 | 4.639409 | 2.023048 | 4.285996 | 6.067497 | 5.165949 | 7.428484 |
| C11orf74 | 0.64699619 | 0.05169609 | 0.035571963 | 8.830456312 | 5.263699 | 2.023048 | 2.165421 | 6.063041 | 7.793829 | 5.106393 |
| SPA17 | 0.954944142 | 0.043840967 | 0.01368901 | 8.821343956 | 2.201691 | 2.809601 | 2.165421 | 6.252746 | 5.306419 | 8.758577 |
| BATF3 | 0.900046151 | 0.044203301 | 0.016455257 | 8.821343956 | 1.874444 | 2.023048 | 2.165421 | 4.894482 | 5.306419 | 5.874977 |
| TRUB2 | 0.879447847 | 0.044278935 | 0.017469888 | 8.821343956 | 1.874444 | 2.406905 | 2.165421 | 4.739845 | 5.306419 | 5.874974 |
| GINS2 | 0.831970289 | 0.044855041 | 0.019911535 | 8.821343956 | 1.874444 | 2.023048 | 2.165421 | 5.705318 | 5.306419 | 4.476242 |
| SULT1E1 | 0.824556675 | 0.044949653 | 0.020430759 | 8.821343956 | 3.024504 | 2.023048 | 4.285996 | 5.252045 | 7.793829 | 5.426231 |
| ZNF23 | 0.795839139 | 0.045374706 | 0.022274923 | 8.821343956 | 2.993831 | 2.809601 | 2.165421 | 4.894482 | 5.306419 | 4.562324 |
| CASQ2 | 0.763890936 | 0.046215863 | 0.024560735 | 8.821343956 | 3.819732 | 2.406905 | 2.165421 | 6.651882 | 5.306419 | 7.020304 |
| CCDC88B | 0.676254139 | 0.049726364 | 0.032036747 | 8.821343956 | 2.201691 | 2.023048 | 2.165421 | 5.026959 | 5.306419 | 2.921909 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| C7orf46 | 0.626663461 | 0.053489675 | 0.038566859 | 8.821343956 | 2.993831 | 2.023048 | 2.165421 | 7.656039 | 5.306419 | 2.921909 |
| UTP15 | 0.860246619 | 0.044379352 | 0.018387887 | 8.808773156 | 3.839948 | 2.809601 | 3.935222 | 7.074163 | 6.794431 | 6.195186 |
| RPS27L | 0.759054746 | 0.046382879 | 0.024906431 | 8.801809402 | 8.085359 | 6.537655 | 6.054038 | 9.675455 | 10.347834 | 9.517491 |
| LOC100216546 | 0.909823847 | 0.044159136 | 0.015912896 | 8.800496432 | 1.874444 | 3.360637 | 3.324375 | 6.498222 | 6.205902 | 6.051818 |
| VSIG10 | 0.835023256 | 0.044793607 | 0.01971555 | 8.788253044 | 2.993831 | 2.809601 | 2.995681 | 5.252045 | 6.373501 | 6.129407 |
| TSC22D2 | 0.913599984 | 0.044110923 | 0.015680163 | 8.772096566 | 5.316227 | 5.789702 | 6.056062 | 8.864724 | 9.188984 | 8.678584 |
| CTPS2 | 0.929534814 | 0.044037172 | 0.014847907 | 8.769315211 | 4.639409 | 4.80797 | 4.449894 | 7.582358 | 8.63937 | 7.668215 |
| ALS2CR8 | 0.702824226 | 0.04852027 | 0.029578088 | 8.758315564 | 3.350997 | 4.750708 | 2.379345 | 6.544171 | 5.509998 | 6.942983 |
| ZMYM2 | 0.819543147 | 0.045111103 | 0.02077011 | 8.746364803 | 5.335413 | 4.80797 | 5.571599 | 8.700282 | 8.624754 | 7.46072 |
| C1orf131 | 0.657940159 | 0.050866557 | 0.03405376 | 8.733852469 | 3.350997 | 2.809601 | 2.165421 | 7.25991 | 5.936219 | 3.676349 |
| ZNF37BP | 0.840152947 | 0.044722631 | 0.019466485 | 8.725933753 | 5.856559 | 6.792427 | 7.204614 | 9.111713 | 10.329923 | 9.899123 |
| USP46 | 0.859986057 | 0.044379352 | 0.018401497 | 8.716974692 | 4.209882 | 4.413323 | 2.165421 | 6.544171 | 7.53715 | 7.03218 |
| SPTY2D1 | 0.903991892 | 0.044173537 | 0.016226608 | 8.70925824 | 5.753024 | 5.148082 | 5.596986 | 8.270632 | 8.63937 | 9.294121 |
| AQP1 | 0.834495589 | 0.044793607 | 0.019749575 | 8.698428211 | 3.819732 | 5.661685 | 4.724406 | 6.814118 | 7.845161 | 11.2096 |
| FGL2 | 0.891629786 | 0.044203301 | 0.01694173 | 8.689765039 | 5.658609 | 4.830496 | 4.944468 | 7.835902 | 8.777924 | 8.472642 |
| ETV1 | 0.940220965 | 0.043921714 | 0.014353862 | 8.689446069 | 2.201691 | 2.023048 | 2.379345 | 5.320955 | 7.269549 | 5.091834 |
| TSPAN7 | 0.727993136 | 0.047463619 | 0.027266417 | 8.689446069 | 2.201691 | 3.872014 | 5.018694 | 5.320955 | 6.613395 | 9.372483 |
| NECAB1 | 0.727040953 | 0.047516329 | 0.027371895 | 8.689446069 | 2.201691 | 2.406905 | 2.165421 | 5.320955 | 6.78473 | 3.676349 |
| WDR66 | 0.876372325 | 0.044280042 | 0.017603266 | 8.670864417 | 2.201691 | 2.023048 | 2.379345 | 4.739845 | 5.317867 | 6.129407 |
| TMPRSS11BNL | 0.83696069 | 0.044768725 | 0.019654985 | 8.670864417 | 2.201691 | 2.809601 | 2.165421 | 4.802615 | 5.317867 | 6.618407 |
| MSRB3 | 0.909700309 | 0.044159136 | 0.015919701 | 8.66191416 | 5.263699 | 5.43468 | 4.285996 | 8.331873 | 8.549366 | 7.988762 |
| IFIT4 | 0.848575892 | 0.044592081 | 0.018990813 | 8.658990602 | 3.839948 | 2.023048 | 2.165421 | 6.954147 | 6.205902 | 5.106393 |
| SLC38A6 | 0.83797027 | 0.044745607 | 0.01960803 | 8.658990602 | 3.839948 | 2.809601 | 3.90836 | 6.954147 | 7.138979 | 5.900694 |
| VCL | 0.910069355 | 0.044159136 | 0.015899285 | 8.656953078 | 7.744853 | 7.899144 | 7.295639 | 10.409498 | 10.840623 | 11.508465 |
| UCHL5 | 0.755981081 | 0.046488705 | 0.025146649 | 8.655547354 | 4.309025 | 2.023048 | 3.764125 | 7.42265 | 6.613395 | 5.426231 |
| FBX032 | 0.690675452 | 0.048985317 | 0.030614495 | 8.654781361 | 6.099991 | 6.502398 | 4.449894 | 8.105092 | 9.615895 | 7.774634 |
| LOC100499177 | 0.920983025 | 0.044110923 | 0.015288874 | 8.653934669 | 5.335413 | 6.049721 | 6.369239 | 9.094145 | 9.275744 | 9.163078 |
| RCHY1 | 0.802212448 | 0.04534393 | 0.021880231 | 8.652637758 | 5.491121 | 4.80797 | 4.508334 | 8.604261 | 8.502167 | 6.942983 |
| SLC22A18 | 0.820285527 | 0.045095391 | 0.020705002 | 8.651857506 | 3.819732 | 4.736586 | 2.995681 | 7.835902 | 5.857745 | 7.849596 |
| ARRDC4 | 0.869845965 | 0.044335719 | 0.017881592 | 8.650177287 | 2.993831 | 3.360637 | 4.285996 | 7.144104 | 7.174648 | 6.106561 |
| PTK2B | 0.851872764 | 0.044480228 | 0.018760122 | 8.650177287 | 2.993831 | 3.360637 | 3.90836 | 7.477873 | 6.237456 | 6.106561 |
| C6orf62 | 0.843535631 | 0.044654714 | 0.019228989 | 8.645917924 | 7.155835 | 5.362142 | 6.326717 | 9.102956 | 9.915181 | 9.438736 |
| PPME1 | 0.86740201 | 0.044369384 | 0.018032664 | 8.634426507 | 5.056948 | 4.80797 | 4.449894 | 7.918071 | 7.25505 | 8.784285 |
| LAP3 | 0.79142201 | 0.045499568 | 0.022588636 | 8.606724079 | 6.58615 | 6.638536 | 5.225216 | 8.566539 | 9.168974 | 9.744001 |
| SCN11A | 0.815387344 | 0.045173526 | 0.021025519 | 8.604122393 | 6.008206 | 4.736586 | 4.724406 | 7.394225 | 8.469821 | 9.113234 |
| CLIP1 | 0.797114981 | 0.045366463 | 0.022171487 | 8.599160299 | 3.819732 | 4.911517 | 5.217616 | 8.993498 | 7.53715 | 6.924055 |
| RNF144B | 0.70437448 | 0.048408779 | 0.029387547 | 8.592589642 | 3.819732 | 2.406905 | 3.90836 | 7.70315 | 5.509998 | 5.580533 |
| NCOA7 | 0.925703204 | 0.04407613 | 0.015101735 | 8.591368156 | 7.218633 | 6.983552 | 7.273415 | 10.617494 | 10.24167 | 10.086439 |
| KHDRBS3 | 0.790694128 | 0.045520454 | 0.022620619 | 8.569370112 | 2.201691 | 4.911517 | 6.054038 | 8.014609 | 5.857745 | 8.010706 |
| LRIG2 | 0.765385115 | 0.046178907 | 0.024440286 | 8.565823114 | 3.024504 | 2.023048 | 3.935222 | 5.252045 | 7.53715 | 7.033813 |
| ATG14 | 0.889741842 | 0.044203301 | 0.017005784 | 8.564724264 | 5.700376 | 4.830496 | 5.723602 | 8.768324 | 8.220489 | 8.822008 |
| MCTS1 | 0.900922875 | 0.044203301 | 0.016414427 | 8.562385284 | 6.792865 | 6.139057 | 6.175931 | 9.23707 | 9.492512 | 9.857343 |
| PRRG4 | 0.899179892 | 0.04654641 | 0.016538959 | 8.549259441 | 5.491121 | 5.789702 | 5.609945 | 9.29204 | 8.36819 | 8.705744 |
| RGPD3 | 0.79530244 | 0.04540117 | 0.02233821 | 8.54640041 | 4.263463 | 3.360637 | 4.724406 | 6.252746 | 7.819723 | 7.46072 |
| SGCD | 0.875124847 | 0.044285705 | 0.017668595 | 8.528833974 | 1.874444 | 4.413323 | 4.944468 | 6.954147 | 7.505595 | 7.825039 |
| SPTBN1 | 0.813170398 | 0.045218796 | 0.021187479 | 8.523943798 | 7.893399 | 6.572071 | 7.132367 | 9.663593 | 10.589051 | 10.37995 |
| C7orf59 | 0.882585744 | 0.044229452 | 0.017331745 | 8.517495099 | 6.008206 | 6.092406 | 6.012527 | 9.102956 | 9.228189 | 8.732403 |
| FAM168B | 0.85327035 | 0.044464174 | 0.018677101 | 8.516149859 | 5.753024 | 4.736586 | 4.724406 | 7.814607 | 8.2398 | 8.407967 |
| DFFA | 0.805456022 | 0.045318476 | 0.0216754 | 8.515900772 | 7.497182 | 7.458616 | 6.056062 | 9.146221 | 10.178018 | 11.489054 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| SPATS2L | 0.936397596 | 0.043994974 | 0.014507656 | 8.500688673 | 6.099991 | 6.092406 | 6.355801 | 9.410337 | 9.44338 | 9.133378 |
| NFYB | 0.754270234 | 0.046655221 | 0.025328343 | 8.495161589 | 5.316227 | 4.830496 | 4.285996 | 6.651882 | 8.402869 | 8.074602 |
| NKAPP1 | 0.940579679 | 0.043921714 | 0.014340252 | 8.495058686 | 2.201691 | 2.023048 | 2.165421 | 5.252045 | 5.509998 | 5.106393 |
| SOX6 | 0.940878961 | 0.044325295 | 0.017838721 | 8.495058686 | 2.201691 | 3.32135 | 2.165421 | 5.252045 | 6.205902 | 5.900694 |
| ARSE | 0.858670798 | 0.044387761 | 0.018441647 | 8.495058686 | 1.874444 | 2.023048 | 2.165421 | 5.252045 | 5.165949 | 4.562324 |
| QRICH1 | 0.805160045 | 0.045318476 | 0.02168901 | 8.495058686 | 2.201691 | 4.389936 | 2.165421 | 5.252045 | 6.861783 | 6.587378 |
| ACYP1 | 0.791887166 | 0.045479433 | 0.022546444 | 8.495058686 | 3.839948 | 2.406905 | 2.165421 | 5.252045 | 6.205902 | 6.051834 |
| URM1 | 0.686865305 | 0.049176261 | 0.030911875 | 8.495058686 | 4.815804 | 2.406905 | 2.165421 | 5.252045 | 6.237456 | 6.455366 |
| PIGQ | 0.674364361 | 0.049848381 | 0.032234774 | 8.495058686 | 4.209882 | 2.023048 | 2.165421 | 5.252045 | 5.165949 | 6.051818 |
| CCDC30 | 0.606960698 | 0.055426536 | 0.041489622 | 8.495058686 | 1.874444 | 2.023048 | 2.165421 | 5.252045 | 5.165949 | 2.921909 |
| CCDC15 | 0.606960698 | 0.055426536 | 0.041489622 | 8.495058686 | 1.874444 | 2.023048 | 2.165421 | 5.252045 | 5.165949 | 2.921909 |
| ANO1 | 0.761899797 | 0.046345155 | 0.024739027 | 8.487023421 | 6.143785 | 7.08238 | 5.217616 | 9.229044 | 9.468155 | 8.519314 |
| CTNNAL1 | 0.811742609 | 0.045218796 | 0.021262334 | 8.480248056 | 3.839948 | 5.789702 | 4.285996 | 8.447068 | 8.258856 | 6.924055 |
| LOC100506421 | 0.924934963 | 0.044407613 | 0.01510854 | 8.475775753 | 1.874444 | 2.023048 | 2.165421 | 4.894482 | 5.920411 | 5.106393 |
| LINC00052 | 0.924182515 | 0.044091888 | 0.015150732 | 8.475775753 | 1.874444 | 2.023048 | 2.165421 | 4.894482 | 5.857745 | 5.106393 |
| ECHDC3 | 0.907319187 | 0.044173537 | 0.016029262 | 8.475775753 | 1.874444 | 2.023048 | 2.165421 | 4.718672 | 6.640994 | 5.106393 |
| CEP41 | 0.885377915 | 0.044203301 | 0.01721674 | 8.475775753 | 1.874444 | 2.023048 | 2.165421 | 4.718672 | 5.353925 | 5.106393 |
| AIF1 | 0.86999921 | 0.044335719 | 0.017874787 | 8.475775753 | 1.874444 | 2.023048 | 2.165421 | 5.448591 | 4.608763 | 5.106393 |
| RBM12B | 0.847625931 | 0.044619412 | 0.019044573 | 8.475775753 | 2.993831 | 2.023048 | 2.995681 | 6.498222 | 5.936219 | 5.106393 |
| EHHADH | 0.833549952 | 0.044797567 | 0.019802654 | 8.475775753 | 1.874444 | 2.023048 | 2.165421 | 7.074163 | 4.131418 | 5.106393 |
| LCA5 | 0.820181613 | 0.045095391 | 0.020718612 | 8.475775753 | 1.874444 | 2.023048 | 2.165421 | 4.341916 | 5.317867 | 5.106393 |
| SNX25 | 0.814986711 | 0.045198955 | 0.021088125 | 8.475775753 | 1.874444 | 2.023048 | 2.165421 | 6.183122 | 4.131418 | 5.106393 |
| POC5 | 0.73885259 | 0.044712834 | 0.015150732 | 8.475775753 | 3.839948 | 2.023048 | 2.165421 | 6.283686 | 5.317867 | 5.106393 |
| STAMBP | 0.698314907 | 0.048744753 | 0.03002654 | 8.475775753 | 4.263463 | 2.023048 | 2.165421 | 5.448591 | 6.373501 | 5.106393 |
| EPHA7 | 0.64932755 | 0.051527347 | 0.035147329 | 8.471647074 | 1.874444 | 2.023048 | 2.165421 | 5.579836 | 3.134528 | 5.106393 |
| ZNHIT6 | 0.856650747 | 0.044407381 | 0.018525349 | 8.468658349 | 4.209882 | 2.023048 | 2.165421 | 6.339437 | 7.292524 | 6.69026 |
| HMCN1 | 0.85270708 | 0.044464174 | 0.018717931 | 8.468206122 | 2.201691 | 3.872014 | 4.754917 | 6.954147 | 7.440337 | 6.69026 |
| PCDHB11 | 0.800513531 | 0.045343936 | 0.021965975 | 8.468206122 | 3.02454 | 2.023048 | 2.165421 | 5.252045 | 4.797798 | 6.106561 |
| TAS2R20 | 0.768022626 | 0.046157531 | 0.024266757 | 8.465714455 | 3.819732 | 2.809601 | 2.379345 | 5.891233 | 7.174648 | 5.091834 |
| PRG4 | 0.579992784 | 0.058796241 | 0.046738346 | 8.465714455 | 1.874444 | 2.809601 | 2.165421 | 5.891233 | 5.306419 | 2.921909 |
| ACTL6A | 0.720605455 | 0.047703746 | 0.027862538 | 8.45712153 | 7.336579 | 2.406905 | 5.018694 | 7.835902 | 8.098861 | 8.974957 |
| LOC400027 | 0.785532131 | 0.045624536 | 0.02293229 | 8.451652171 | 4.743564 | 2.023048 | 4.285996 | 7.36523 | 7.414086 | 6.106561 |
| PICALM | 0.861424022 | 0.044379352 | 0.018333447 | 8.432858648 | 6.949166 | 6.931478 | 5.974145 | 10.025188 | 9.59355 | 9.509806 |
| HSP90AB1 | 0.815025156 | 0.045182971 | 0.021072474 | 8.425136669 | 10.2590065 | 10.745814 | 10.670173 | 12.660133 | 13.744873 | 14.561793 |
| NOTCH4 | 0.803454625 | 0.045338539 | 0.021821708 | 8.419102698 | 2.993831 | 2.023048 | 4.285996 | 6.067497 | 6.043524 | 6.618407 |
| GPAA1 | 0.797839987 | 0.045355733 | 0.022123171 | 8.415447663 | 5.856559 | 4.351315 | 4.724406 | 7.177844 | 8.181074 | 8.929599 |
| MITF | 0.617721156 | 0.054216311 | 0.039811501 | 8.411751433 | 4.682076 | 3.360637 | 5.609945 | 5.252045 | 8.682351 | 7.988762 |
| HSPH1 | 0.733633924 | 0.047307334 | 0.026815924 | 8.411542483 | 7.943836 | 9.255331 | 11.023067 | 11.732348 | 13.563241 | 12.327702 |
| KRT8P41 | 0.916388001 | 0.044110923 | 0.015503232 | 8.411162839 | 2.201691 | 2.023048 | 2.165421 | 5.095353 | 5.306419 | 5.106393 |
| PCDHB14 | 0.905670924 | 0.044135537 | 0.016131337 | 8.411162839 | 1.874444 | 2.023048 | 2.379345 | 5.095353 | 5.317867 | 5.091834 |
| LOC344595 | 0.900761685 | 0.044203301 | 0.016421232 | 8.411162839 | 1.874444 | 2.023048 | 2.165421 | 5.095353 | 5.509998 | 4.790662 |
| NANOG | 0.899815359 | 0.044203301 | 0.016482477 | 8.411162839 | 1.874444 | 2.023048 | 2.165421 | 5.095353 | 4.797798 | 5.426231 |
| CCDC18 | 0.894869372 | 0.044203301 | 0.016784621 | 8.411162839 | 1.874444 | 2.023048 | 2.165421 | 5.095353 | 5.306419 | 4.790662 |
| CCDC121 | 0.894869372 | 0.044203301 | 0.016784621 | 8.411162839 | 1.874444 | 2.023048 | 2.165421 | 5.095353 | 5.306419 | 4.790662 |
| AGBL2 | 0.879491627 | 0.044278935 | 0.017463083 | 8.411162839 | 1.874444 | 2.023048 | 2.165421 | 5.095353 | 4.608763 | 5.882028 |
| KIAA1467 | 0.829259088 | 0.044930476 | 0.020181014 | 8.411162839 | 2.993831 | 2.023048 | 2.165421 | 5.095353 | 5.509998 | 5.426231 |
| BET1 | 0.812567073 | 0.045218796 | 0.021214699 | 8.411162839 | 1.874444 | 2.023048 | 2.165421 | 5.095353 | 6.043524 | 4.146207 |
| AGA | 0.787156603 | 0.045564387 | 0.022802314 | 8.411162839 | 1.874444 | 2.023048 | 2.165421 | 5.095353 | 5.317867 | 4.146207 |
| C3orf18 | 0.787049067 | 0.045564387 | 0.022809119 | 8.411162839 | 1.874444 | 2.023048 | 2.379345 | 5.095353 | 5.920411 | 4.146207 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| DNAJB14 | 0.78234296 | 0.045701235 | 0.023158898 | 8.411162839 | 1.874444 | 2.023048 | 2.995681 | 5.095353 | 6.237456 | 4.562324 |
| EED | 0.777273761 | 0.045858846 | 0.02351412 | 8.411162839 | 2.993831 | 2.023048 | 4.285996 | 5.095353 | 7.094585 | 6.73963 |
| MBTPS2 | 0.771276234 | 0.046066162 | 0.024006805 | 8.411162839 | 1.874444 | 2.023048 | 2.995681 | 5.095353 | 6.237456 | 4.476242 |
| KLHL3 | 0.765761688 | 0.046178907 | 0.024426676 | 8.411162839 | 3.350997 | 2.023048 | 3.90836 | 5.095353 | 7.414086 | 6.195186 |
| RGR | 0.740868363 | 0.047048421 | 0.026321198 | 8.411162839 | 1.874444 | 2.023048 | 2.379345 | 5.095353 | 6.774676 | 3.630092 |
| HES5 | 0.727637047 | 0.047495226 | 0.027323579 | 8.411162839 | 1.874444 | 2.023048 | 2.379345 | 5.095353 | 3.571326 | 6.587378 |
| NSUN7 | 0.708362428 | 0.048245878 | 0.028952705 | 8.411162839 | 1.874444 | 2.023048 | 2.165421 | 5.095353 | 5.353925 | 3.630092 |
| C6orf168 | 0.705939209 | 0.048351237 | 0.029237836 | 8.411162839 | 1.874444 | 2.023048 | 2.165421 | 5.095353 | 5.306419 | 3.630092 |
| TEX15 | 0.705939209 | 0.048351237 | 0.029237836 | 8.411162839 | 1.874444 | 2.023048 | 2.165421 | 5.095353 | 5.306419 | 3.630092 |
| MYOZ3 | 0.62923349 | 0.053255542 | 0.038197346 | 8.411162839 | 1.874444 | 2.023048 | 2.379345 | 5.095353 | 6.189775 | 2.921909 |
| RANBP6 | 0.605708464 | 0.0555885 | 0.041744811 | 8.411162839 | 1.874444 | 2.023048 | 2.165421 | 5.095353 | 5.306419 | 2.921909 |
| SCRG1 | 0.671080899 | 0.05005437 | 0.032605648 | 8.408312292 | 1.874444 | 2.406905 | 2.995681 | 6.067497 | 3.571326 | 5.882028 |
| TSIX | 0.910581538 | 0.044159136 | 0.01587887 | 8.40768589 | 7.480194 | 7.800972 | 7.611303 | 10.475444 | 11.180031 | 10.683012 |
| C3orf52 | 0.683984347 | 0.049369649 | 0.031292276 | 8.405506515 | 1.874444 | 4.351315 | 3.324375 | 7.42265 | 5.353925 | 5.426231 |
| RNF170 | 0.915990274 | 0.044110923 | 0.022051463 | 8.404172917 | 3.819732 | 2.023048 | 3.324375 | 6.395481 | 6.861783 | 6.32627 |
| COL14A1 | 0.814695923 | 0.045198955 | 0.02110854 | 8.4016411006 | 5.856559 | 6.092406 | 6.326717 | 8.376156 | 9.516465 | 9.163078 |
| KLF4 | 0.795919922 | 0.045374706 | 0.022261313 | 8.399742495 | 6.381847 | 6.931478 | 7.809663 | 10.001823 | 10.311787 | 9.620989 |
| NET1 | 0.811044598 | 0.045237293 | 0.021315413 | 8.392620156 | 5.491121 | 3.360637 | 6.175931 | 9.245052 | 8.350533 | 7.640338 |
| MFAP2 | 0.917027054 | 0.044110923 | 0.015462402 | 8.390670857 | 1.874444 | 2.023048 | 2.165421 | 4.739845 | 7.627877 | 5.091834 |
| GIPC2 | 0.916772773 | 0.044110923 | 0.015489622 | 8.390670857 | 1.874444 | 2.023048 | 2.165421 | 6.664985 | 4.797798 | 5.091834 |
| SNX12 | 0.898524281 | 0.044203301 | 0.016559374 | 8.390670857 | 1.874444 | 2.023048 | 2.165421 | 4.718672 | 6.043524 | 5.091834 |
| ANO5 | 0.896255715 | 0.044203301 | 0.016685948 | 8.390670857 | 1.874444 | 2.023048 | 2.165421 | 5.320955 | 4.797798 | 5.091834 |
| SH2D1A | 0.891069296 | 0.044203301 | 0.016951344 | 8.390670857 | 1.874444 | 2.023048 | 2.165421 | 7.531061 | 4.539173 | 5.091834 |
| PRORSD1P | 0.889194701 | 0.044203301 | 0.017033004 | 8.390670857 | 1.874444 | 2.023048 | 2.379345 | 6.244586 | 4.797798 | 5.091834 |
| SW15 | 0.839169406 | 0.044732882 | 0.019561075 | 8.390670857 | 3.350997 | 2.023048 | 3.324375 | 7.33564 | 6.373501 | 5.091834 |
| KANK4 | 0.805646801 | 0.045318476 | 0.021668595 | 8.390670857 | 1.874444 | 2.023048 | 2.165421 | 4.013424 | 6.549959 | 5.091834 |
| PRADC1 | 0.804164743 | 0.045327183 | 0.021771351 | 8.390670857 | 3.350997 | 2.023048 | 2.165421 | 6.244586 | 5.317867 | 5.091834 |
| GORAB | 0.788810345 | 0.045550411 | 0.022715209 | 8.390670857 | 2.201691 | 2.023048 | 4.944468 | 7.144104 | 5.857745 | 5.091834 |
| PRKACB | 0.785292521 | 0.045643174 | 0.022962913 | 8.390670857 | 3.839948 | 2.023048 | 2.379345 | 5.320955 | 7.989035 | 5.091834 |
| HILPDA | 0.765708206 | 0.046178907 | 0.02443481 | 8.390670857 | 4.209882 | 2.023048 | 2.165421 | 5.705318 | 7.174648 | 5.091834 |
| FCHSD2 | 0.755739016 | 0.046493188 | 0.025164342 | 8.390670857 | 3.350997 | 2.023048 | 2.165421 | 5.252045 | 5.509998 | 5.091834 |
| FAM150B | 0.74501266 | 0.04685274 | 0.026040083 | 8.390670857 | 1.874444 | 2.023048 | 2.165421 | 6.544171 | 3.571326 | 5.091834 |
| ACP2 | 0.741932736 | 0.046959999 | 0.026211637 | 8.390670857 | 3.839948 | 2.023048 | 2.165421 | 6.396698 | 5.306419 | 5.091834 |
| GSTA1 | 0.738730603 | 0.04712834 | 0.026506975 | 8.386108414 | 9.099752 | 8.089403 | 8.050877 | 11.118879 | 11.527136 | 11.5836 |
| TXLNB | 0.738730603 | 0.04712834 | 0.026506975 | 8.382936672 | 5.335413 | 2.023048 | 5.723602 | 7.450526 | 8.402869 | 8.745549 |
| HOXA4 | 0.859699373 | 0.044379352 | 0.019929228 | 8.382280489 | 3.839948 | 2.406905 | 2.995681 | 6.063041 | 6.861783 | 5.580533 |
| EMB | 0.815087239 | 0.045182971 | 0.021052059 | 8.381521898 | 4.815804 | 4.911517 | 2.379345 | 6.814118 | 5.353925 | 5.446557 |
| IL18RAP | 0.66235715 | 0.050569223 | 0.035573324 | 8.367552933 | 6.344798 | 4.754917 | 8.915622 | 7.819723 | 7.988762 |
| NDST3 | 0.756540616 | 0.046450467 | 0.025090847 | 8.366901741 | 4.209882 | 4.413323 | 5.544658 | 7.274575 | 7.819723 | 8.074602 |
| OSTM1 | 0.809463467 | 0.045247607 | 0.021414086 | 8.363834676 | 5.897292 | 3.32135 | 3.324375 | 8.069577 | 7.191402 | 6.385515 |
| TMEM33 | 0.719861441 | 0.047724223 | 0.027952365 | 8.352738314 | 6.186289 | 5.340619 | 3.764125 | 8.316805 | 8.402869 | 8.456743 |
| TAP1 | 0.836337932 | 0.044768725 | 0.0196754 | 8.343133038 | 6.099991 | 4.389936 | 6.072169 | 7.450526 | 8.668166 | 9.922465 |
| C8orf84 | 0.667962326 | 0.050279153 | 0.032963593 | 8.343133038 | 1.874444 | 4.389936 | 2.165421 | 7.450526 | 6.640994 | 3.630092 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| CXorf69 | 0.796652623 | 0.045374706 | 0.022213678 | 8.339795926 | 5.700376 | 4.413323 | 3.324375 | 7.897963 | 7.473335 | 7.46072 |
| ZRANB2 | 0.786040139 | 0.045579058 | 0.022873767 | 8.329587462 | 5.491121 | 5.340619 | 5.592916 | 9.299725 | 8.549366 | 7.46072 |
| STX17 | 0.829346688 | 0.044930476 | 0.020174209 | 8.323800179 | 5.779429 | 4.736586 | 2.165421 | 7.995811 | 7.793829 | 7.611911 |
| ASCC3 | 0.830902165 | 0.044867325 | 0.019998639 | 8.317424162 | 2.993831 | 3.770995 | 2.995681 | 5.705318 | 7.767462 | 6.051818 |
| PFKFB2 | 0.77657627 | 0.045873421 | 0.023601905 | 8.317424162 | 4.209882 | 2.023048 | 2.995681 | 5.448591 | 7.107836 | 6.051818 |
| C14orf119 | 0.867040806 | 0.044369384 | 0.018046274 | 8.312325426 | 4.815804 | 4.351315 | 3.764125 | 7.477873 | 7.406567 | 7.255535 |
| LOC285074 | 0.833969096 | 0.044797567 | 0.019761824 | 8.31066274 | 4.309025 | 4.911517 | 5.596986 | 8.604261 | 7.53715 | 7.96648 |
| CYP20A1 | 0.788385705 | 0.045562713 | 0.02274379 | 8.297871814 | 7.931391 | 6.762934 | 6.919905 | 9.23707 | 10.543149 | 10.984132 |
| C9orf40 | 0.90508547 | 0.044173537 | 0.016192583 | 8.284152046 | 2.201691 | 2.023048 | 2.379345 | 5.252045 | 5.353925 | 5.106393 |
| KLHL9 | 0.698657454 | 0.044763723 | 0.029996597 | 8.282084617 | 3.819732 | 3.32135 | 3.764125 | 6.814118 | 7.138979 | 5.091834 |
| FHL1 | 0.830267909 | 0.044867325 | 0.020080299 | 8.27999419 | 6.381847 | 3.360637 | 6.355801 | 9.431477 | 8.777924 | 8.519314 |
| LINC00514 | 0.826187333 | 0.044936643 | 0.020338891 | 8.277855658 | 9.344671 | 9.026217 | 9.161448 | 11.570252 | 12.210705 | 12.438107 |
| AIMP1 | 0.87587406 | 0.044285705 | 0.017641375 | 8.275906832 | 5.744513 | 5.297868 | 4.944468 | 8.346785 | 8.314558 | 8.424409 |
| ZNF81 | 0.819113782 | 0.045111103 | 0.020791426 | 8.271467391 | 1.874444 | 2.809601 | 2.165421 | 5.728038 | 5.857745 | 4.476242 |
| ELMOD3 | 0.801382326 | 0.045343936 | 0.021911535 | 8.269741685 | 2.993831 | 2.023048 | 2.995681 | 5.252045 | 6.043524 | 5.446557 |
| IQCK | 0.797621918 | 0.045355733 | 0.022143586 | 8.269741685 | 1.874444 | 2.023048 | 2.995681 | 4.739845 | 6.043524 | 5.091834 |
| ANKRD10 | 0.848716249 | 0.044567264 | 0.018965635 | 8.258194188 | 6.58615 | 4.750708 | 6.012527 | 9.058353 | 8.777924 | 9.143346 |
| LSM1 | 0.786471974 | 0.045579058 | 0.022846546 | 8.257971836 | 1.874444 | 3.872014 | 3.90836 | 6.954147 | 6.861783 | 5.426231 |
| ACOT13 | 0.841084169 | 0.044701668 | 0.019412725 | 8.257476648 | 3.350997 | 3.872014 | 3.324375 | 6.396698 | 7.25505 | 6.051818 |
| DIS3L | 0.767968368 | 0.046157531 | 0.024273562 | 8.253886563 | 9.440001 | 9.542523 | 9.288789 | 11.362146 | 12.485075 | 12.978097 |
| ZFR | 0.704911433 | 0.048378239 | 0.029308608 | 8.250271702 | 6.143785 | 5.43468 | 5.702912 | 9.188227 | 8.817023 | 7.36177 |
| PRKAA2 | 0.814068963 | 0.045212649 | 0.021158217 | 8.248873508 | 4.815804 | 4.351315 | 3.935222 | 8.361545 | 6.613395 | 7.395512 |
| CRYM-AS1 | 0.743901277 | 0.046889341 | 0.026077577 | 8.242739537 | 4.209882 | 3.770995 | 5.702912 | 6.814118 | 8.098861 | 7.523109 |
| ICA1L | 0.753220592 | 0.04658639 | 0.02539231 | 8.23675328 | 7.497182 | 7.323707 | 7.557139 | 9.307369 | 10.539257 | 10.958955 |
| DNTTIP2 | 0.81571606 | 0.045173526 | 0.021005104 | 8.216100517 | 6.949166 | 6.957749 | 6.326717 | 9.9762 | 8.963611 | 10.293075 |
| NUP107 | 0.861700491 | 0.044379352 | 0.018313032 | 8.215451758 | 5.056948 | 5.487673 | 4.449894 | 7.937902 | 8.098861 | 8.095288 |
| DENND4C | 0.772015685 | 0.046057921 | 0.023930589 | 8.21022621 | 3.819732 | 6.044198 | 5.018694 | 6.857154 | 8.65384 | 8.986077 |
| FAM115C | 0.756659987 | 0.046450467 | 0.025084042 | 8.202927315 | 6.648293 | 6.391261 | 7.381261 | 8.864729 | 9.687973 | 10.4174 |
| MAGI3 | 0.7599391 | 0.046382879 | 0.024854712 | 8.2024829 | 3.024504 | 3.360637 | 2.995681 | 6.396698 | 6.189775 | 5.106393 |
| RBM48 | 0.832177105 | 0.044855041 | 0.019904729 | 8.195565886 | 3.024504 | 3.360637 | 2.165421 | 6.395481 | 5.920411 | 5.426231 |
| TAGLN | 0.747804758 | 0.046782073 | 0.025788363 | 8.186836992 | 8.8383 | 10.996101 | 9.542181 | 12.3874 | 11.871606 | 14.895969 |
| CHML | 0.737368706 | 0.047155325 | 0.026589316 | 8.186032839 | 4.209882 | 4.351315 | 5.702912 | 7.243046 | 7.819723 | 7.46072 |
| ABLIM1 | 0.870126147 | 0.044335719 | 0.017861177 | 8.183836997 | 5.335413 | 6.03611 | 3.324375 | 8.122528 | 8.36819 | 8.822008 |
| RYK | 0.823278166 | 0.045019115 | 0.020528071 | 8.181309969 | 5.897292 | 4.911517 | 5.217616 | 8.433162 | 8.453372 | 7.943848 |
| BIRC3 | 0.71487156 | 0.047877006 | 0.028318476 | 8.175256072 | 6.48761 | 6.670655 | 7.180931 | 10.698207 | 9.701967 | 8.374509 |
| SEMA3G | 0.776862426 | 0.045858868 | 0.023552229 | 8.169833097 | 2.201691 | 2.023048 | 3.764125 | 4.739845 | 6.794431 | 8.593895 |
| C16orf88 | 0.748312739 | 0.046757859 | 0.025758421 | 8.158810472 | 4.263463 | 2.406905 | 2.995681 | 4.894482 | 6.774676 | 7.291822 |
| ACTR10 | 0.723802268 | 0.047585406 | 0.027578088 | 8.158810472 | 4.263463 | 2.023048 | 3.764125 | 4.341916 | 7.187136 | 7.291822 |
| CXCL12 | 0.702380903 | 0.048544976 | 0.029616196 | 8.141142202 | 7.497182 | 7.26179 | 9.310781 | 9.832037 | 12.336012 | 10.76277 |
| CCDC66 | 0.730451266 | 0.047384624 | 0.027073835 | 8.139148993 | 4.815804 | 3.360637 | 2.379345 | 6.183122 | 6.640994 | 6.385515 |
| MDC1 | 0.691360492 | 0.048955004 | 0.030572304 | 8.138890021 | 5.856559 | 3.32135 | 3.935222 | 6.960054 | 6.640994 | 8.010706 |
| NMNAT2 | 0.707338859 | 0.048274546 | 0.029047976 | 8.135043224 | 1.874444 | 4.389936 | 3.324375 | 5.026959 | 7.414086 | 6.129407 |
| IRS1 | 0.733165225 | 0.047307334 | 0.026877169 | 8.131021282 | 5.328526 | 3.770995 | 3.324375 | 8.628872 | 6.794431 | 6.195186 |
| RBMY2FP | 0.80341301 | 0.045338539 | 0.021828513 | 8.123966263 | 5.700376 | 4.351315 | 5.217616 | 7.582358 | 8.2398 | 8.340256 |
| STAG2 | 0.640962114 | 0.052128403 | 0.036397414 | 8.122283953 | 3.819732 | 3.872014 | 5.544653 | 8.566539 | 8.160956 | 5.091834 |
| LOC100505876 | 0.756782151 | 0.046448971 | 0.025066349 | 8.115403758 | 7.931391 | 7.581983 | 7.884888 | 9.727662 | 10.905551 | 11.101266 |
| DPY19L4 | 0.730394791 | 0.047384624 | 0.02708064 | 8.115079366 | 3.350997 | 2.406905 | 3.764125 | 5.448591 | 6.78473 | 5.634184 |
| BBX | 0.885780763 | 0.04420301 | 0.017196325 | 8.114778375 | 6.48761 | 5.148082 | 6.175931 | 9.196483 | 9.401119 | 8.929599 |
| XPNPEP1 | 0.761489127 | 0.046345155 | 0.024758081 | 8.112226742 | 4.815804 | 2.406905 | 2.165421 | 7.835902 | 7.406567 | 4.562324 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| CLYBL | 0.841110018 | 0.044701668 | 0.01940592 | 8.111893222 | 1.874444 | 2.809601 | 2.379345 | 4.894482 | 5.353925 | 6.051818 |
| LOC100129662 | 0.83150444 | 0.044867325 | 0.019971419 | 8.111893222 | 1.874444 | 2.023048 | 2.995681 | 4.894482 | 5.306419 | 5.874974 |
| YIPF5 | 0.883354043 | 0.044229452 | 0.01731113 | 8.10960927 | 5.335413 | 4.750708 | 5.596986 | 8.616619 | 8.277663 | 8.11568 |
| SPN | 0.840004869 | 0.044722631 | 0.019493705 | 8.109557158 | 6.48761 | 6.670655 | 7.360327 | 9.23707 | 10.142544 | 10.37995 |
| NIPA1 | 0.78539925 | 0.045643174 | 0.022956108 | 8.107885225 | 2.201691 | 2.406905 | 2.995681 | 7.109557 | 4.539173 | 5.426231 |
| DUS4L | 0.767707236 | 0.04616149 | 0.02429806 | 8.107885225 | 2.993831 | 2.406905 | 2.165421 | 6.396698 | 4.539173 | 5.426231 |
| JAZF1 | 0.772657085 | 0.046036363 | 0.023876148 | 8.100927246 | 1.874444 | 3.32135 | 4.285996 | 6.339437 | 7.174648 | 5.446557 |
| TM2D1 | 0.693421241 | 0.048932925 | 0.030380401 | 8.092755593 | 5.856559 | 4.389936 | 3.90836 | 7.109557 | 7.406567 | 7.611911 |
| BCL2L2 | 0.716777767 | 0.047841399 | 0.028196666 | 8.087507289 | 5.056948 | 2.809601 | 3.90836 | 6.183122 | 7.138979 | 6.924055 |
| MTMR12 | 0.86149738 | 0.044379352 | 0.018326642 | 8.084518213 | 4.682076 | 4.413323 | 4.285996 | 8.65307 | 6.794431 | 7.428484 |
| C5orf43 | 0.705216871 | 0.048378239 | 0.029301803 | 8.061858448 | 4.263463 | 3.32135 | 2.995681 | 7.274575 | 6.608026 | 5.106393 |
| SYNCRIP | 0.841649364 | 0.044701668 | 0.01935148 | 8.056726703 | 6.186289 | 6.311907 | 6.831141 | 9.196483 | 9.418172 | 9.397686 |
| C6orf108 | 0.79740571 | 0.045366463 | 0.022164682 | 8.051889558 | 4.815804 | 4.413323 | 3.324375 | 7.42265 | 7.440337 | 6.649696 |
| SEMA5A | 0.768706767 | 0.046113847 | 0.024177611 | 8.047138432 | 6.054828 | 4.830496 | 6.056062 | 7.976765 | 9.064538 | 8.534542 |
| ZNF322 | 0.864149847 | 0.044377262 | 0.018151072 | 8.046882208 | 4.209882 | 3.360637 | 3.324375 | 6.954147 | 6.189775 | 7.218312 |
| SLC39A8 | 0.886429459 | 0.044203301 | 0.017115495 | 8.038537485 | 5.263699 | 3.32135 | 4.724406 | 8.270632 | 7.598264 | 7.668215 |
| COL1A2 | 0.768155168 | 0.046157531 | 0.024246342 | 8.036755239 | 8.646058 | 7.458616 | 8.80648 | 10.46523 | 13.508557 | 10.8042 |
| PIGF | 0.708344426 | 0.048268527 | 0.029014631 | 8.033820973 | 4.263463 | 2.406905 | 3.324375 | 7.243046 | 7.269549 | 4.562324 |
| NFU1 | 0.782851117 | 0.045695042 | 0.023105138 | 8.03236783 | 4.963444 | 3.32135 | 4.285996 | 6.651882 | 7.473335 | 7.291822 |
| PAQR5 | 0.795777729 | 0.04542938 | 0.022447091 | 8.022306766 | 5.316227 | 4.736586 | 3.90836 | 6.814118 | 7.740604 | 8.732403 |
| LOC158696 | 0.903523105 | 0.044173537 | 0.016267438 | 8.021715481 | 1.874444 | 2.023048 | 2.165421 | 5.026959 | 6.205902 | 4.790662 |
| SNORA72 | 0.895871497 | 0.044203301 | 0.016699558 | 8.021715481 | 1.874444 | 2.023048 | 2.165421 | 5.026959 | 4.797798 | 5.580533 |
| ZNF354A | 0.783865535 | 0.045695042 | 0.023043892 | 8.021715481 | 1.874444 | 2.023048 | 2.165421 | 5.026959 | 5.353925 | 4.146207 |
| KATNAL1 | 0.771121005 | 0.04607418 | 0.024019735 | 8.021715481 | 4.309025 | 2.023048 | 2.379345 | 5.026959 | 6.608026 | 6.587378 |
| C7orf61 | 0.728671444 | 0.047423411 | 0.027207894 | 8.021715481 | 1.874444 | 2.023048 | 2.379345 | 5.026959 | 6.551443 | 3.630092 |
| FAM104B | 0.708408573 | 0.04824159 | 0.028942497 | 8.021715481 | 1.874444 | 2.023048 | 2.165421 | 5.026959 | 5.306419 | 3.676349 |
| ELP4 | 0.708408573 | 0.04824159 | 0.028942497 | 8.021715481 | 1.874444 | 2.023048 | 2.165421 | 5.026959 | 5.306419 | 3.676349 |
| RPSA | 0.697298053 | 0.04880813 | 0.030102076 | 8.021715481 | 1.874444 | 2.023048 | 2.379345 | 5.026959 | 3.571326 | 5.874974 |
| TSR2 | 0.678608028 | 0.049556832 | 0.03177067 | 8.021715481 | 4.263463 | 2.023048 | 2.165421 | 5.026959 | 5.936219 | 5.634184 |
| CRISPLD1 | 0.656360069 | 0.050987756 | 0.034207554 | 8.021715481 | 1.874444 | 2.023048 | 2.165421 | 5.026959 | 6.549959 | 2.921909 |
| PTTG1 | 0.637509215 | 0.052501106 | 0.036991494 | 8.021715481 | 1.874444 | 2.023048 | 2.165421 | 5.026959 | 8.791075 | 5.446557 |
| PTGES3 | 0.842914284 | 0.044657496 | 0.019253488 | 8.015380943 | 8.203921 | 7.756763 | 8.487278 | 11.094787 | 3.134528 | 4.562324 |
| NOB1 | 0.702049597 | 0.048553714 | 0.029638653 | 8.01435311 | 4.963444 | 5.661685 | 3.90836 | 9.87896 | 11.548591 | 10.759534 |
| CUTC | 0.746733284 | 0.046800775 | 0.025865941 | 8.01051905 | 4.263463 | 2.023048 | 3.324375 | 5.252045 | 7.96603 | 6.051818 |
| PCBD1 | 0.660483276 | 0.050683546 | 0.033752297 | 8.007619935 | 5.982974 | 5.789702 | 4.944468 | 10.048181 | 7.187136 | 6.32627 |
| JAK2 | 0.851136583 | 0.044490827 | 0.018813882 | 8.002931958 | 1.874444 | 2.406905 | 2.165421 | 6.396698 | 8.791075 | 6.45366 |
| LOC729513 | 0.821723408 | 0.045048325 | 0.020617897 | 8.002931958 | 3.350997 | 2.809601 | 3.324375 | 5.728038 | 5.165949 | 4.562324 |
| RNF180 | 0.701707396 | 0.048571998 | 0.029678802 | 8.002931958 | 2.201691 | 2.023048 | 2.165421 | 5.705318 | 5.165949 | 6.924055 |
| PCDHB3 | 0.701101694 | 0.048630415 | 0.029746172 | 8.002931958 | 1.874444 | 2.023048 | 2.165421 | 5.026959 | 5.165949 | 3.630092 |
| ATP13A4 | 0.694116093 | 0.048919234 | 0.030347737 | 8.002931958 | 1.874444 | 2.023048 | 2.165421 | 5.026959 | 5.165949 | 3.676349 |
| GBE1 | 0.678242629 | 0.049589172 | 0.031799251 | 8.002931958 | 4.309025 | 2.809601 | 2.165421 | 6.063041 | 5.165949 | 3.630092 |
| ZAN | 0.593619814 | 0.057018726 | 0.043874787 | 8.002931958 | 1.874444 | 2.023048 | 2.165421 | 5.026959 | 5.165949 | 6.051818 |
| CGN | 0.592891033 | 0.057080847 | 0.044019735 | 8.002931958 | 3.024504 | 2.023048 | 2.165421 | 7.074163 | 5.165949 | 2.921909 |
| ADM | 0.83990164 | 0.044722631 | 0.019507315 | 8.000088991 | 6.143785 | 5.148082 | 6.031658 | 8.331873 | 9.031674 | 9.103055 |
| LIAS | 0.782427778 | 0.045701235 | 0.023152093 | 7.991764305 | 5.491121 | 6.044198 | 6.769247 | 8.700282 | 9.042172 | 9.051056 |
| NEMF | 0.818859621 | 0.045111103 | 0.020805036 | 7.990913815 | 6.186289 | 5.297868 | 2.165421 | 8.628872 | 8.296229 | 7.722406 |
| SLU7 | 0.921227883 | 0.044110923 | 0.015282069 | 7.989260489 | 5.982974 | 5.297868 | 6.031658 | 8.964784 | 8.904331 | 9.02972 |
| ZNF250 | 0.818586679 | 0.045111103 | 0.020818646 | 7.987277482 | 7.595107 | 7.664061 | 7.250844 | 9.698891 | 10.592811 | 11.383675 |
| DCAF8 | 0.869769911 | 0.044335719 | 0.017888397 | 7.984017169 | 5.304463 | 3.360637 | 6.072169 | 8.301578 | 8.71031 | 8.287303 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| LRP5 | 0.854560097 | 0.044464174 | 0.018622661 | 7.98032207 | 4.263463 | 4.830496 | 3.764125 | 7.25991 | 7.473335 | 7.28312 |
| CDC37L1 | 0.759454112 | 0.046382879 | 0.024879211 | 7.98032207 | 4.263463 | 3.360637 | 3.324375 | 7.25991 | 7.138979 | 5.426231 |
| VIM | 0.646751746 | 0.051710823 | 0.035614835 | 7.973984909 | 11.358374 | 11.213413 | 12.538201 | 13.036939 | 14.425289 | 15.533502 |
| RHOJ | 0.574086263 | 0.059729834 | 0.048034025 | 7.973600661 | 5.658609 | 5.487673 | 4.449894 | 5.728038 | 8.65384 | 8.549611 |
| COL5A2 | 0.727501921 | 0.047495226 | 0.027330384 | 7.972845827 | 6.306772 | 5.195784 | 7.422239 | 8.301578 | 10.417334 | 9.192178 |
| MFSD1 | 0.840091587 | 0.044722631 | 0.019480095 | 7.969800186 | 5.263699 | 4.830496 | 5.544653 | 8.895478 | 8.033973 | 7.825039 |
| HNRNPA2B1 | 0.718101819 | 0.047790154 | 0.028074175 | 7.95411622 | 8.493568 | 8.464054 | 9.054723 | 12.564496 | 11.48527 | 10.354432 |
| MYO3B | 0.71105044 | 0.048062795 | 0.02869071 | 7.949617131 | 7.841135 | 7.726519 | 8.011136 | 9.552198 | 11.002021 | 10.936201 |
| PHF11 | 0.839534414 | 0.044722631 | 0.019534536 | 7.938317978 | 4.682076 | 4.413323 | 3.935222 | 7.556937 | 7.414086 | 6.924055 |
| ETFA | 0.886266549 | 0.044203301 | 0.017169105 | 7.925194216 | 4.743564 | 4.911517 | 2.165421 | 7.897963 | 7.713236 | 7.218312 |
| BACE1 | 0.779368694 | 0.045829476 | 0.023349439 | 7.918023917 | 5.328526 | 3.872014 | 4.449894 | 6.857154 | 8.033973 | 7.582913 |
| DENND5B | 0.807007538 | 0.045297753 | 0.021572644 | 7.911318143 | 5.700376 | 2.809601 | 4.508334 | 7.33564 | 8.119857 | 7.492252 |
| USP48 | 0.830738579 | 0.044867325 | 0.020005444 | 7.909022718 | 4.309025 | 3.770995 | 4.944468 | 7.210813 | 7.292524 | 7.428484 |
| IRF2BP2 | 0.768794731 | 0.046108296 | 0.024157196 | 7.899537998 | 7.513971 | 7.197097 | 8.114773 | 11.235653 | 10.495739 | 9.724213 |
| COMMD6 | 0.889647616 | 0.044203301 | 0.017012589 | 7.89545727 | 6.648293 | 8.278469 | 8.735088 | 11.259492 | 11.175024 | 11.56518 |
| PAM | 0.755462062 | 0.046650334 | 0.025196325 | 7.895091721 | 6.267718 | 4.830496 | 4.944468 | 7.42265 | 8.277663 | 9.248674 |
| DUSP6 | 0.846693477 | 0.044634679 | 0.019101055 | 7.888082159 | 6.186289 | 6.092406 | 5.596986 | 8.41912 | 9.524361 | 9.072081 |
| REV3L | 0.708649131 | 0.04824159 | 0.02891868 | 7.883529254 | 4.743564 | 2.406905 | 4.944468 | 5.705318 | 7.793829 | 7.722406 |
| RBBP7 | 0.762911834 | 0.046294386 | 0.02467574 | 7.873611376 | 5.056948 | 4.389936 | 5.571599 | 8.843852 | 8.033973 | 7.180104 |
| WDR59 | 0.753027729 | 0.04658639 | 0.02540592 | 7.867493112 | 4.682076 | 4.351315 | 5.592916 | 7.748771 | 7.740604 | 7.327219 |
| CHFR | 0.779084376 | 0.045829476 | 0.023369854 | 7.864056854 | 3.350997 | 4.736586 | 2.379345 | 7.25991 | 6.205902 | 6.32627 |
| CDC42EP3 | 0.716672042 | 0.047841399 | 0.028210276 | 7.861572572 | 4.682076 | 6.502398 | 5.217616 | 8.676869 | 7.656894 | 8.340256 |
| STRBP | 0.619899834 | 0.054008689 | 0.039490983 | 7.860276525 | 4.743564 | 4.389936 | 2.379345 | 8.222933 | 5.353925 | 6.051818 |
| GAL3ST4 | 0.824814408 | 0.044949653 | 0.020423954 | 7.858042956 | 3.839948 | 4.351315 | 2.995681 | 6.814118 | 6.549959 | 6.931222 |
| PSMD4 | 0.73408097 | 0.047307334 | 0.026781899 | 7.856783944 | 6.765086 | 5.340619 | 5.225216 | 9.067384 | 8.314558 | 8.287303 |
| CAPZA1 | 0.777823648 | 0.045844227 | 0.023464444 | 7.852992711 | 6.678389 | 6.35207 | 5.389265 | 9.651632 | 8.751258 | 8.705744 |
| FAM20B | 0.823358103 | 0.045005314 | 0.020492004 | 7.83721444 | 5.263699 | 4.351315 | 5.018694 | 7.36523 | 7.989035 | 8.155622 |
| RUFY3 | 0.83260516 | 0.04483949 | 0.019870024 | 7.835636934 | 4.743564 | 6.139057 | 5.609945 | 8.316805 | 8.579995 | 8.719135 |
| MREG | 0.769300725 | 0.04608352 | 0.024095951 | 7.830222225 | 3.819732 | 4.80797 | 4.285996 | 10.384422 | 7.25505 | 5.874974 |
| ZNF292 | 0.813779885 | 0.045218796 | 0.021180674 | 7.827906858 | 4.815804 | 4.80797 | 5.723602 | 7.814607 | 7.767462 | 8.692228 |
| DISC2 | 0.763795549 | 0.046221625 | 0.024578428 | 7.808259511 | 1.874444 | 2.406905 | 4.508334 | 4.718672 | 7.473335 | 6.618407 |
| AKD1 | 0.859955472 | 0.044379352 | 0.018408302 | 7.804243338 | 2.201691 | 2.406905 | 2.165421 | 4.894482 | 5.165949 | 5.634184 |
| TSC22D1 | 0.684803491 | 0.049311103 | 0.031183396 | 7.802114119 | 8.55164 | 8.359538 | 9.485302 | 12.449167 | 11.795338 | 10.284093 |
| ZNF704 | 0.819630825 | 0.045111103 | 0.020764206 | 7.799917319 | 4.639409 | 2.809601 | 5.217616 | 7.36523 | 8.181074 | 7.03218 |
| NR2F2 | 0.647631905 | 0.051640811 | 0.035444029 | 7.797351636 | 9.060289 | 4.830496 | 6.976024 | 9.552198 | 9.939008 | 10.039174 |
| OGT | 0.74781431 | 0.046782073 | 0.025808778 | 7.792875096 | 7.04469 | 7.664091 | 8.037751 | 11.024644 | 10.626217 | 9.532738 |
| DGKB | 0.74755534 | 0.046268527 | 0.028980606 | 7.777525921 | 1.874444 | 2.023048 | 3.324375 | 6.283686 | 4.608763 | 5.091834 |
| CCDC91 | 0.708096674 | 0.048763723 | 0.029989792 | 7.713311298 | 4.263463 | 2.023048 | 3.764125 | 7.450526 | 7.767462 | 7.695565 |
| ATAD2B | 0.883253265 | 0.044229452 | 0.017318155 | 7.713234896 | 4.639409 | 5.297868 | 5.018694 | 7.918071 | 7.767462 | 8.175185 |
| ETV6 | 0.86912487 | 0.044335719 | 0.017922423 | 7.773866125 | 3.350997 | 3.360637 | 2.165421 | 6.183122 | 6.319269 | 6.618407 |
| MAP3K5 | 0.760159006 | 0.046360115 | 0.024239537 | 7.767875877 | 4.815804 | 6.270596 | 5.389265 | 8.346785 | 8.469821 | 8.03232 |
| SMARCD1 | 0.727223008 | 0.047508117 | 0.02734978 | 7.758931336 | 6.45321 | 5.661685 | 5.225216 | 8.801178 | 8.502167 | 7.640338 |
| CNIH | 0.802230384 | 0.04534393 | 0.021873426 | 7.740283892 | 3.024504 | 3.32135 | 4.508334 | 5.579836 | 8.181074 | 7.46072 |
| TANC1 | 0.698760437 | 0.048763723 | 0.021873426 | 7.713311298 | 4.263463 | 2.023048 | 3.324375 | 7.210813 | 7.440337 | 6.385515 |
| CAB39 | 0.768183294 | 0.046157531 | 0.024239537 | 7.713234896 | 4.639409 | 5.297868 | 5.018694 | 7.918071 | 4.797798 | 8.175185 |
| C7orf60 | 0.653334383 | 0.051215566 | 0.034617217 | 7.711545169 | 3.839948 | 5.661685 | 3.764125 | 8.566539 | 7.96603 | 7.03218 |
| TRIM33 | 0.730215695 | 0.047384624 | 0.027101055 | 7.70881774 | 2.201691 | 2.406905 | 3.764125 | 7.177844 | 5.353925 | 4.146207 |
| CCNYL1 | 0.899000976 | 0.044203301 | 0.016545764 | 7.695263555 | 5.328526 | 5.195784 | 5.225216 | 9.196483 | 8.502167 | 7.255535 |
| NIT1 | 0.853213811 | 0.044464174 | 0.018683906 | 7.689967805 | 5.263699 | 5.340619 | 5.723602 | 8.206677 | 8.160956 | 8.440667 |
|  |  |  |  |  |  |  |  |  | 8.453372 | 8.340256 |

TABLE 8-continued

Differentially Expressed Genes in CD10−, CD24−, CD44−, Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| TRIM78P | 0.835956809 | 0.044768725 | 0.01968901 | 7.682682037 | 1.874444 | 2.023048 | 2.379345 | 5.320955 | 4.608763 | 5.091834 |
| LOC146336 | 0.842295274 | 0.044657496 | 0.019301123 | 7.679287153 | 1.874444 | 2.023048 | 2.165421 | 5.095353 | 4.539173 | 5.106393 |
| UBXN2B | 0.812255916 | 0.045218796 | 0.021228309 | 7.679287153 | 2.993831 | 2.406905 | 2.165421 | 6.244586 | 5.165949 | 5.106393 |
| ATPAF1 | 0.778898268 | 0.045829476 | 0.023383464 | 7.679287153 | 1.874444 | 3.360637 | 2.165421 | 5.026959 | 6.189775 | 5.106393 |
| BARD1 | 0.753106087 | 0.04658639 | 0.025399115 | 7.679287153 | 2.201691 | 2.023048 | 2.165421 | 5.252045 | 4.131418 | 5.106393 |
| FAIM | 0.7375199 | 0.047140798 | 0.026573665 | 7.679287153 | 3.819732 | 2.809601 | 2.165421 | 6.063041 | 6.043524 | 5.106393 |
| WDR37 | 0.718924396 | 0.047781016 | 0.028047635 | 7.679287153 | 2.993831 | 3.360637 | 2.165421 | 6.396698 | 5.165949 | 5.106393 |
| BCAR3 | 0.665266692 | 0.050389557 | 0.033253488 | 7.679287153 | 3.350997 | 4.750708 | 2.165421 | 7.210813 | 6.319269 | 5.106393 |
| CAPN3 | 0.619152689 | 0.054069926 | 0.039584212 | 7.679287153 | 1.874444 | 2.023048 | 2.165421 | 5.026959 | 3.134528 | 5.106393 |
| GLTPD1 | 0.606919951 | 0.055428454 | 0.04149983 | 7.679287153 | 4.743564 | 2.406905 | 2.165421 | 6.395481 | 5.353925 | 5.106393 |
| ASNS | 0.833047644 | 0.044797567 | 0.019836679 | 7.678295396 | 5.304463 | 4.80797 | 2.995681 | 8.122528 | 7.187136 | 7.748756 |
| ORAI1 | 0.620212169 | 0.054006231 | 0.039448792 | 7.676976239 | 5.753024 | 2.406905 | 2.995681 | 7.504712 | 5.936219 | 5.882028 |
| ELF1 | 0.872703848 | 0.044299467 | 0.017731201 | 7.676299171 | 5.865559 | 2.406905 | 6.410545 | 9.049264 | 8.579995 | 8.79697 |
| UACA | 0.712347221 | 0.047984994 | 0.02854032 | 7.671109411 | 6.924263 | 5.362142 | 7.422239 | 8.301578 | 9.974027 | 10.166824 |
| TAF9B | 0.793984412 | 0.04542938 | 0.022419871 | 7.666253266 | 3.024504 | 2.809601 | 2.379345 | 5.448591 | 5.317867 | 5.091834 |
| ARHGEF38 | 0.688544636 | 0.049115877 | 0.030796189 | 7.666253266 | 3.024504 | 2.023048 | 2.379345 | 7.42265 | 5.317867 | 3.676349 |
| KCNMA1 | 0.58747444 | 0.05763794 | 0.045051378 | 7.666253266 | 3.024504 | 5.661685 | 2.379345 | 7.274575 | 5.317867 | 6.195186 |
| SYF2 | 0.81126663 | 0.045231055 | 0.021302484 | 7.664387248 | 7.278811 | 6.03611 | 6.410545 | 10.115039 | 9.348715 | 9.23941 |
| ARID5B | 0.740984576 | 0.047036111 | 0.026306227 | 7.658259979 | 7.497182 | 6.184248 | 8.525393 | 9.958788 | 10.434198 | 10.550703 |
| NUP153 | 0.73876637 | 0.04712834 | 0.026489963 | 7.642632392 | 7.0583 | 7.0583 | 8.355951 | 9.99237 | 10.550902 | 9.956785 |
| RARS | 0.834614926 | 0.044793607 | 0.019735965 | 7.640945632 | 5.865559 | 5.809601 | 3.764125 | 8.79031 | 8.453372 | 8.074602 |
| TMEM126B | 0.715902201 | 0.047867182 | 0.028263355 | 7.640849969 | 4.639409 | 2.809601 | 2.165421 | 5.743334 | 7.138979 | 5.580533 |
| CXCR3 | 0.680210983 | 0.049490097 | 0.031604627 | 7.640849969 | 3.024504 | 2.809601 | 4.724406 | 5.448591 | 6.613395 | 6.129407 |
| FLJ42709 | 0.676861777 | 0.049712169 | 0.031992514 | 7.640849969 | 4.209882 | 2.809601 | 5.609945 | 5.743334 | 7.793829 | 7.800057 |
| SLC25A36 | 0.81733983 | 0.045152347 | 0.020879891 | 7.632138706 | 5.056948 | 4.911517 | 5.609945 | 9.651632 | 7.989035 | 7.523109 |
| SELK | 0.722501424 | 0.047570884 | 0.027494386 | 7.627713864 | 7.854379 | 7.240547 | 7.381261 | 10.78563 | 10.417334 | 9.329475 |
| CCDC149 | 0.800129287 | 0.045343942 | 0.022010888 | 7.620746067 | 2.993831 | 3.32135 | 8.525393 | 5.095353 | 5.857745 | 6.618407 |
| LOC100129716 | 0.750525992 | 0.046662281 | 0.025574005 | 7.620746067 | 1.874444 | 7.0583 | 2.165421 | 5.095353 | 6.774676 | 4.562324 |
| LINC00473 | 0.70292959 | 0.048515004 | 0.029560395 | 7.620746067 | 3.024504 | 2.023048 | 2.379345 | 5.095353 | 6.189775 | 4.146207 |
| LOC387723 | 0.57943649 | 0.058820115 | 0.046834297 | 7.620746067 | 2.201691 | 4.389936 | 2.165421 | 5.095353 | 5.317867 | 2.921909 |
| ZDHHC21 | 0.571781645 | 0.060073766 | 0.048504934 | 7.620746067 | 2.993831 | 2.809601 | 2.165421 | 5.095353 | 6.613395 | 2.921909 |
| ERO1L | 0.803940431 | 0.045338539 | 0.021801293 | 7.616336552 | 4.209882 | 4.389936 | 4.724406 | 7.70315 | 7.138979 | 6.195186 |
| NTAN1 | 0.791974089 | 0.045479433 | 0.022539639 | 7.616336552 | 4.209882 | 4.389936 | 3.324375 | 5.728038 | 7.138979 | 5.874974 |
| SNX13 | 0.820390988 | 0.045095391 | 0.020698197 | 7.613825378 | 4.639409 | 4.389936 | 2.379345 | 7.274575 | 7.56803 | 6.455366 |
| ATPBD4 | 0.825347764 | 0.044949653 | 0.020403539 | 7.611452577 | 1.874444 | 2.809601 | 2.165421 | 4.802615 | 5.317867 | 5.634184 |
| CEP78 | 0.811511838 | 0.045218796 | 0.021228509 | 7.611452577 | 1.874444 | 2.809601 | 2.165421 | 4.802615 | 5.165949 | 5.634184 |
| FREM1 | 0.659892932 | 0.050684199 | 0.033776795 | 7.611452577 | 3.024504 | 4.750708 | 4.724406 | 4.802615 | 8.332658 | 7.428484 |
| PRIM2 | 0.768273111 | 0.04614639 | 0.024223886 | 7.605665154 | 2.201691 | 3.32135 | 2.379345 | 6.550689 | 5.306419 | 5.426231 |
| NCOA2 | 0.885945538 | 0.044203301 | 0.017182715 | 7.602179765 | 1.874444 | 2.023048 | 2.165421 | 6.396698 | 4.797798 | 5.091834 |
| STX18 | 0.871168165 | 0.044325295 | 0.017825111 | 7.602179765 | 1.874444 | 2.406905 | 2.165421 | 4.718672 | 6.78473 | 5.091834 |
| GRIN2A | 0.80972385 | 0.045243682 | 0.021394352 | 7.602179765 | 2.201691 | 2.809601 | 2.165421 | 4.894482 | 5.509998 | 5.091834 |
| WDR12 | 0.782840697 | 0.045695042 | 0.023111943 | 7.602179765 | 1.874444 | 3.360637 | 2.165421 | 6.067497 | 5.306419 | 5.091834 |
| SYDE2 | 0.76873736 | 0.046108296 | 0.024167404 | 7.602179765 | 1.874444 | 2.023048 | 2.165421 | 5.026959 | 4.131418 | 5.091834 |
| ARMC12 | 0.768273111 | 0.04620301 | 0.024167404 | 7.602179765 | 1.874444 | 2.023048 | 2.165421 | 5.026959 | 4.718672 | 5.091834 |
| MCF2L-AS1 | 0.751697786 | 0.044325295 | 0.01782511 | 7.602179765 | 3.024504 | 2.023048 | 2.165421 | 5.891233 | 6.774676 | 5.091834 |
| ALDH18A1 | 0.699356305 | 0.045243682 | 0.021394352 | 7.602179765 | 1.874444 | 2.406905 | 2.165421 | 7.274575 | 6.549959 | 5.091834 |
| C8orf55 | 0.659410532 | 0.050730781 | 0.033858455 | 7.600716786 | 4.263463 | 3.872014 | 3.764125 | 8.033165 | 8.453372 | 6.69026 |
| NDUFAF3 | 0.768462664 | 0.04614639 | 0.024210276 | 7.591502453 | 6.099991 | 4.911517 | 3.324375 | 7.835902 | 6.549959 | 7.46072 |
| RAB9B | 0.862924433 | 0.044377262 | 0.018259952 | 7.586081293 | 1.874444 | 2.023048 | 2.379345 | 5.252045 | 4.797798 | 5.106393 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| RPL7A | 0.75235937 | 0.046595104 | 0.025454917 | 7.586081293 | 1.874444 | 2.023048 | 3.324375 | 5.252045 | 4.797798 | 5.634184 |
| MRS2P2 | 0.724795006 | 0.047575442 | 0.027512079 | 7.586081293 | 1.874444 | 2.023048 | 3.324375 | 5.095353 | 4.797798 | 5.426231 |
| C5orf64 | 0.709365174 | 0.04824159 | 0.028865601 | 7.586081293 | 1.874444 | 2.406905 | 3.90836 | 6.183122 | 4.797798 | 5.634184 |
| CTLA4 | 0.60942205 | 0.055130486 | 0.04104117 | 7.586081293 | 1.874444 | 2.023048 | 4.285996 | 5.705318 | 4.797798 | 5.091834 |
| PRITFDC1 | 0.839756876 | 0.044722631 | 0.01951412 | 7.583455348 | 3.839948 | 3.32135 | 3.764125 | 6.244586 | 7.187136 | 6.455366 |
| CEPT1 | 0.776237403 | 0.045884853 | 0.023630487 | 7.580626984 | 4.263463 | 4.413323 | 2.165421 | 7.33564 | 7.107836 | 5.900694 |
| GNB2L1 | 0.687492571 | 0.049147961 | 0.03086492 | 7.578134819 | 10.078965 | 9.9999 | 10.148051 | 13.069894 | 13.026151 | 11.713056 |
| FYN | 0.810814514 | 0.045237293 | 0.021329023 | 7.578131912 | 6.054828 | 4.80797 | 5.702912 | 8.935488 | 8.624754 | 7.988762 |
| BYSL | 0.755534842 | 0.046493188 | 0.025171147 | 7.56026288 | 2.993831 | 2.809601 | 3.90836 | 5.728038 | 5.936219 | 6.195186 |
| CD8A | 0.696922996 | 0.04882091 | 0.030140864 | 7.559203239 | 3.819732 | 4.351315 | 6.072169 | 9.417418 | 7.269549 | 6.587378 |
| ANKRD1 | 0.863867337 | 0.044377262 | 0.018171487 | 7.548648983 | 1.874444 | 2.023048 | 2.165421 | 5.448591 | 4.797798 | 4.790662 |
| LIPH | 0.816140328 | 0.045165524 | 0.020958149 | 7.548648983 | 1.874444 | 2.809601 | 2.165421 | 7.394225 | 4.797798 | 4.790662 |
| NDUFAF1 | 0.756518884 | 0.04645067 | 0.025097652 | 7.548648983 | 1.874444 | 3.32135 | 2.165421 | 4.894482 | 6.78473 | 4.790662 |
| MARK1 | 0.716157814 | 0.04786157 | 0.028252467 | 7.548648983 | 1.874444 | 2.023048 | 3.764125 | 4.894482 | 6.861783 | 4.790662 |
| PKP1 | 0.630558238 | 0.053156193 | 0.037991153 | 7.548648983 | 1.874444 | 4.750708 | 2.165421 | 6.063041 | 5.936219 | 4.790662 |
| LOC100189589 | 0.801323981 | 0.045343936 | 0.021925145 | 7.548056537 | 2.993831 | 3.32135 | 3.935222 | 6.244586 | 6.237456 | 6.195186 |
| ANKRD65 | 0.761061875 | 0.046345577 | 0.024792106 | 7.548056537 | 1.874444 | 4.351315 | 2.379345 | 4.341916 | 6.237456 | 6.051818 |
| PIK3R4 | 0.739944303 | 0.047086482 | 0.026380401 | 7.548056537 | 3.350997 | 3.32135 | 2.995681 | 6.498222 | 6.237456 | 5.091834 |
| RAD51B | 0.728440372 | 0.047423411 | 0.027228309 | 7.548056537 | 1.874444 | 3.32135 | 4.449894 | 5.705318 | 6.237456 | 6.618407 |
| PDS5A | 0.775735294 | 0.045911642 | 0.023693773 | 7.547148664 | 5.753024 | 4.351315 | 4.724406 | 7.450526 | 8.469821 | 7.640338 |
| CSMD2 | 0.707289022 | 0.048274546 | 0.029061586 | 7.537311106 | 3.024504 | 2.406905 | 2.165421 | 5.320955 | 6.551443 | 4.146207 |
| LOC100507117 | 0.585867443 | 0.05791529 | 0.04543141 | 7.537311106 | 1.874444 | 2.406905 | 2.165421 | 5.320955 | 5.306419 | 2.921909 |
| PYROXD1 | 0.851839574 | 0.044480228 | 0.018766928 | 7.523926732 | 5.263699 | 5.148082 | 2.379345 | 7.631894 | 7.68534 | 8.175185 |
| LOC678655 | 0.810736494 | 0.045237293 | 0.021342602 | 7.522934812 | 6.267718 | 7.0089 | 5.974145 | 9.744652 | 9.179013 | 9.08248 |
| MUT | 0.636248922 | 0.052582167 | 0.037130316 | 7.494086699 | 5.897292 | 2.023048 | 4.508334 | 7.726141 | 7.414086 | 5.874974 |
| TRIM56 | 0.848477092 | 0.044592081 | 0.018997618 | 7.483610316 | 4.209882 | 4.351315 | 4.944468 | 7.074163 | 7.25505 | 9.303041 |
| TMEM60 | 0.693023078 | 0.044480228 | 0.03044114427 | 7.479704487 | 1.874444 | 2.023048 | 3.90836 | 6.811341 | 6.613395 | 3.630092 |
| ARSK | 0.684783355 | 0.049319443 | 0.031190207 | 7.47317937 | 3.350997 | 2.023048 | 2.165421 | 6.252746 | 6.189775 | 3.676349 |
| FANCI | 0.846377795 | 0.044634679 | 0.019114665 | 7.468719401 | 3.839948 | 6.060401 | 3.764125 | 6.664985 | 6.043524 | 6.722123 |
| GMEB1 | 0.739213087 | 0.04712834 | 0.026450493 | 7.467550723 | 7.067614 | 6.060401 | 6.031658 | 8.122528 | 9.968249 | 9.717557 |
| SPRY1 | 0.804374029 | 0.045327183 | 0.021744131 | 7.466978217 | 6.227577 | 3.360637 | 6.031658 | 8.665019 | 9.128102 | 7.988762 |
| HYMAI | 0.623997089 | 0.053689061 | 0.038863559 | 7.461751528 | 5.744513 | 2.406905 | 4.285996 | 8.641022 | 7.870158 | 5.426231 |
| ZZZ3 | 0.769935166 | 0.046076407 | 0.024064648 | 7.453686465 | 4.209882 | 4.389936 | 3.90836 | 8.051486 | 7.107836 | 6.129407 |
| GPR65 | 0.666988573 | 0.050336605 | 0.033120789 | 7.450365372 | 4.815804 | 2.406905 | 5.225216 | 8.122528 | 6.551443 | 6.32627 |
| C3orf23 | 0.82284677 | 0.045019115 | 0.020562096 | 7.449371236 | 6.143785 | 4.351315 | 6.369239 | 8.676869 | 9.266358 | 9.67008 |
| RNF220 | 0.679568449 | 0.049531477 | 0.031666553 | 7.446224102 | 5.744513 | 4.351315 | 4.508334 | 8.641022 | 7.870158 | 6.051818 |
| EARS2 | 0.727710084 | 0.047495226 | 0.027309969 | 7.441285383 | 4.263463 | 2.406905 | 2.995681 | 5.891233 | 6.613395 | 5.580533 |
| GINS4 | 0.617267407 | 0.054254364 | 0.039901327 | 7.441285383 | 5.491121 | 3.360637 | 3.324375 | 5.891233 | 6.551443 | 6.931222 |
| GPX8 | 0.702481029 | 0.048544976 | 0.029609391 | 7.433238314 | 5.304463 | 3.770995 | 2.165421 | 6.664985 | 7.656894 | 6.385515 |
| SORT1 | 0.63711194 | 0.052546395 | 0.037071793 | 7.433238314 | 5.856559 | 3.770995 | 2.379345 | 6.664985 | 6.189775 | 7.36177 |
| TMEM134 | 0.601738393 | 0.056105963 | 0.04248656 | 7.433238314 | 6.58615 | 3.770995 | 2.379345 | 6.664985 | 7.138979 | 8.11568 |
| FBXO3 | 0.864091616 | 0.044377262 | 0.018157877 | 7.431545968 | 2.201691 | 2.023048 | 2.379345 | 5.095353 | 6.373501 | 4.790662 |
| HMGB3 | 0.750700989 | 0.04666281 | 0.025560395 | 7.431545968 | 2.201691 | 2.406905 | 3.90836 | 5.095353 | 5.920411 | 6.195186 |
| BTBD6 | 0.699409776 | 0.048734593 | 0.029919701 | 7.431545968 | 2.201691 | 4.389936 | 2.379345 | 5.095353 | 7.269549 | 5.426231 |
| SERAC1 | 0.583069196 | 0.058825755 | 0.045978224 | 7.431545968 | 4.263463 | 2.809601 | 4.754917 | 5.095353 | 5.857745 | 5.882028 |
| PSD4 | 0.861682759 | 0.044379352 | 0.018319837 | 7.42354801 | 3.350997 | 3.360637 | 2.165421 | 6.252746 | 5.920411 | 6.106561 |
| C10orf81 | 0.587198117 | 0.057666624 | 0.045099013 | 7.421604432 | 3.819732 | 4.351315 | 2.165421 | 7.243046 | 5.353925 | 5.091834 |
| RPL32 | 0.845319379 | 0.044645837 | 0.019177271 | 7.415445118 | 11.786594 | 12.076687 | 12.425557 | 14.96722 | 15.017334 | 14.963458 |
| CDHR3 | 0.651010356 | 0.05143697 | 0.034962232 | 7.41344061 | 2.201691 | 2.406905 | 4.449894 | 5.579836 | 6.237456 | 5.091834 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| RCL1 | 0.697474483 | 0.04880813 | 0.030088465 | 7.40577698 | 2.201691 | 5.297868 | 4.285996 | 7.70315 | 7.174648 | 5.882028 |
| C10orf28 | 0.643107866 | 0.05194815 | 0.036151072 | 7.40577698 | 3.839948 | 4.389936 | 4.285996 | 7.33564 | 7.174648 | 5.446557 |
| THOC2 | 0.878200836 | 0.044280042 | 0.017528411 | 7.399896104 | 5.056948 | 3.360637 | 4.724406 | 7.856887 | 7.56803 | 7.611911 |
| LAPTM4B | 0.795775867 | 0.045395954 | 0.022300102 | 7.399751791 | 6.008206 | 4.413323 | 5.217616 | 8.105092 | 8.277663 | 8.074602 |
| BCL6 | 0.809263681 | 0.045247607 | 0.021434502 | 7.396110562 | 7.530567 | 6.877454 | 8.175959 | 10.991813 | 10.417334 | 10.117111 |
| CD99P1 | 0.810552597 | 0.045237293 | 0.021356244 | 7.393956156 | 2.201691 | 2.023048 | 2.995681 | 5.448591 | 4.797798 | 5.882028 |
| HINT2 | 0.752423287 | 0.046595104 | 0.025448112 | 7.392546222 | 4.682076 | 3.770995 | 3.90836 | 6.811341 | 6.794431 | 6.69026 |
| BZW2 | 0.726567383 | 0.047532676 | 0.027397074 | 7.392546222 | 3.839948 | 4.413323 | 3.90836 | 8.875048 | 6.794431 | 5.634184 |
| FAM193A | 0.891201709 | 0.044203301 | 0.016937734 | 7.390879324 | 4.309025 | 3.360637 | 4.449894 | 7.33564 | 7.191402 | 7.152205 |
| FAM160A2 | 0.884733169 | 0.044203301 | 0.01723035 | 7.385538475 | 4.209882 | 4.413323 | 4.449894 | 7.274575 | 7.094585 | 8.232333 |
| SCML1 | 0.764023022 | 0.046193441 | 0.02452739 | 7.384763095 | 2.201691 | 3.32135 | 2.165421 | 5.026959 | 6.205902 | 5.091834 |
| C1orf109 | 0.746450881 | 0.046811314 | 0.025915618 | 7.375499797 | 4.263463 | 4.830496 | 4.285996 | 6.544171 | 7.713236 | 7.218312 |
| ATF1 | 0.808372501 | 0.045247607 | 0.021482137 | 7.373642718 | 4.309025 | 3.360637 | 2.995681 | 5.743334 | 7.191402 | 7.020304 |
| LRRC49 | 0.589553641 | 0.057478449 | 0.044708404 | 7.372606205 | 3.839948 | 2.809601 | 2.809601 | 4.013424 | 6.189775 | 6.722123 |
| USP1 | 0.720403854 | 0.047703746 | 0.027896453 | 7.367333842 | 2.993831 | 4.351315 | 5.225216 | 7.726141 | 7.942653 | 5.874974 |
| BEX4 | 0.717780734 | 0.047825499 | 0.028118408 | 7.364139895 | 5.491121 | 5.487673 | 5.018694 | 9.049264 | 8.36819 | 6.924055 |
| SNX19 | 0.626957483 | 0.05346854 | 0.038500851 | 7.354877469 | 5.865559 | 3.770995 | 2.995681 | 6.550689 | 7.138979 | 6.649696 |
| C3orf17 | 0.777095221 | 0.045858868 | 0.023538619 | 7.348094196 | 5.263699 | 4.80797 | 3.935222 | 8.79031 | 7.68534 | 6.722123 |
| FLJ31813 | 0.712371829 | 0.047984994 | 0.028533515 | 7.346562137 | 5.148082 | 5.148082 | 6.891005 | 8.286188 | 8.36819 | 9.018932 |
| ANKRD36B | 0.806244406 | 0.045315307 | 0.021637292 | 7.343001821 | 2.993831 | 2.809601 | 3.90836 | 6.252746 | 6.78473 | 5.634184 |
| CEP70 | 0.812900991 | 0.045218796 | 0.021207894 | 7.342086404 | 3.024504 | 3.360637 | 3.764125 | 6.183122 | 5.857745 | 5.900694 |
| HABP4 | 0.832386787 | 0.04483949 | 0.019883634 | 7.341727244 | 3.839948 | 2.809601 | 3.935222 | 6.811341 | 6.640994 | 6.129407 |
| SDC2 | 0.758994848 | 0.046382879 | 0.024913236 | 7.340912228 | 5.744513 | 4.351315 | 6.282905 | 9.07636 | 9.158864 | 8.074602 |
| TRIL | 0.793570611 | 0.04542938 | 0.022453896 | 7.330111849 | 1.874444 | 3.32135 | 4.508334 | 6.063041 | 7.107836 | 6.195186 |
| CARS2 | 0.829727223 | 0.044930476 | 0.020146989 | 7.325663398 | 4.963444 | 2.809601 | 4.754917 | 6.960054 | 7.627877 | 7.800057 |
| IFT88 | 0.857804811 | 0.044387761 | 0.018468867 | 7.317923755 | 1.874444 | 2.023048 | 2.165421 | 4.894482 | 6.319269 | 4.562324 |
| PKIA | 0.847326835 | 0.044634679 | 0.01906703 | 7.317923755 | 1.874444 | 2.023048 | 2.165421 | 4.894482 | 4.539173 | 5.874974 |
| NOX4 | 0.842608936 | 0.044657496 | 0.019267098 | 7.317923755 | 1.874444 | 2.023048 | 2.165421 | 4.894482 | 4.539173 | 5.634184 |
| SUGT1P3 | 0.836675021 | 0.044768725 | 0.01966179 | 7.317923755 | 1.874444 | 2.023048 | 2.379345 | 4.894482 | 5.165949 | 4.790662 |
| VPRBP | 0.794666744 | 0.04542938 | 0.022368152 | 7.317923755 | 2.993831 | 2.023048 | 2.379345 | 4.894482 | 5.165949 | 6.195186 |
| HTR1D | 0.760520712 | 0.046360115 | 0.024828173 | 7.317923755 | 1.874444 | 2.023048 | 2.165421 | 4.894482 | 4.131418 | 5.106393 |
| ZNF187 | 0.717025436 | 0.047840971 | 0.028172167 | 7.317923755 | 1.874444 | 2.023048 | 2.165421 | 4.894482 | 5.920411 | 3.630092 |
| SLC9A7P1 | 0.714817592 | 0.047877006 | 0.028332086 | 7.317923755 | 1.874444 | 2.023048 | 2.165421 | 4.894482 | 5.857745 | 3.630092 |
| TBCE | 0.685331006 | 0.049314432 | 0.031141204 | 7.317923755 | 1.874444 | 2.023048 | 3.935222 | 4.894482 | 6.613395 | 4.790662 |
| ETV3L | 0.672706232 | 0.049933984 | 0.032399456 | 7.317923755 | 1.874444 | 2.023048 | 2.165421 | 4.894482 | 3.571326 | 5.091834 |
| BEND5 | 0.634875537 | 0.05273953 | 0.03735148 | 7.317923755 | 1.874444 | 2.023048 | 2.165421 | 4.894482 | 6.237456 | 2.921909 |
| C5orf54 | 0.593422432 | 0.057025989 | 0.043914257 | 7.317923755 | 1.874444 | 2.023048 | 2.165421 | 4.894482 | 5.317867 | 2.921909 |
| COL11A1 | 0.592821047 | 0.057082126 | 0.044038789 | 7.317923755 | 1.874444 | 2.023048 | 2.165421 | 4.894482 | 6.613395 | 4.790662 |
| ZNF789 | 0.592821047 | 0.057082126 | 0.044038789 | 7.317923755 | 1.874444 | 2.023048 | 2.165421 | 4.894482 | 5.306419 | 2.921909 |
| LOC100133612 | 0.5852326 | 0.057986105 | 0.045571283 | 7.314510097 | 1.874444 | 2.023048 | 2.165421 | 4.894482 | 5.165949 | 2.921909 |
| PLSCR1 | 0.790667624 | 0.045520454 | 0.022627424 | 7.302675283 | 6.054828 | 4.736586 | 7.056312 | 8.925589 | 8.842512 | 9.380933 |
| WNK3 | 0.768420939 | 0.04614639 | 0.02421708 | 7.302281111 | 2.993831 | 3.32135 | 2.995681 | 6.339437 | 6.189775 | 5.874974 |
| ENDOD1 | 0.755497831 | 0.046505334 | 0.02518952 | 7.298583355 | 4.743564 | 5.661685 | 3.935222 | 7.897963 | 7.066159 | 7.611911 |
| ZNF7 | 0.706304347 | 0.048309794 | 0.029174549 | 7.297868 | 4.963444 | 3.872014 | 3.324375 | 6.244586 | 7.191402 | 6.73963 |
| SYK | 0.684507067 | 0.049344803 | 0.031236475 | 7.297372046 | 6.186289 | 5.297868 | 5.571599 | 7.243046 | 9.053666 | 8.636861 |
| ZBTB48 | 0.785622555 | 0.045624536 | 0.022925485 | 7.295447971 | 4.815804 | 4.351315 | 3.935222 | 6.811341 | 7.414086 | 7.218312 |
| ASUN | 0.768667555 | 0.046141453 | 0.024199388 | 7.295447971 | 3.819732 | 4.351315 | 2.995681 | 5.728038 | 7.094585 | 7.218312 |
| RPP30 | 0.776648409 | 0.045873421 | 0.0235951 | 7.291349816 | 4.639409 | 5.43468 | 3.935222 | 7.656039 | 7.505595 | 7.395512 |
| PTPRZ1 | 0.816546844 | 0.045165524 | 0.020937734 | 7.287388383 | 1.874444 | 2.809601 | 2.165421 | 4.739845 | 5.317867 | 5.634184 |

TABLE 8-continued

Differentially Expressed Genes in CD10−, CD24−, CD44− Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| CNTN3 | 0.756675501 | 0.046450467 | 0.025077237 | 7.287388383 | 1.874444 | 3.32135 | 2.995681 | 4.739845 | 6.861783 | 5.634184 |
| IL21R | 0.707062274 | 0.04829046 | 0.02909493 | 7.287382786 | 2.201691 | 2.023048 | 3.324375 | 4.013424 | 6.189775 | 5.874974 |
| CLCC1 | 0.742946112 | 0.046915454 | 0.02613542 | 7.285708041 | 5.779429 | 4.830496 | 4.944468 | 7.918071 | 7.819723 | 7.695565 |
| GCLC | 0.692727978 | 0.048944238 | 0.030428037 | 7.281727472 | 4.209882 | 3.360637 | 5.544653 | 7.074163 | 7.414086 | 6.722123 |
| CDCA7L | 0.643124834 | 0.051942518 | 0.036129296 | 7.270543995 | 1.874444 | 4.413323 | 2.995681 | 4.802615 | 5.857745 | 6.587378 |
| PI4K2B | 0.588550452 | 0.057530341 | 0.044860837 | 7.270543995 | 1.874444 | 2.023048 | 2.995681 | 5.579836 | 5.857745 | 2.921909 |
| PDSS1 | 0.672508695 | 0.049933984 | 0.032440286 | 7.267895994 | 2.201691 | 4.80797 | 2.165421 | 5.026959 | 6.043524 | 6.618407 |
| GPR56 | 0.781467311 | 0.04575418 | 0.023221504 | 7.257814679 | 3.350997 | 4.911517 | 3.935222 | 7.771052 | 6.640994 | 6.722123 |
| COPS4 | 0.809545727 | 0.045247607 | 0.021407281 | 7.252655774 | 5.897292 | 6.03611 | 5.217616 | 8.331873 | 8.502167 | 8.894619 |
| RABGAP1L | 0.815486188 | 0.045173526 | 0.021018714 | 7.252075299 | 4.309025 | 2.406905 | 4.754917 | 7.167419 | 7.292524 | 6.722123 |
| PRKCI | 0.812963765 | 0.045218796 | 0.021201089 | 7.248244414 | 5.335413 | 6.060401 | 5.592916 | 8.190235 | 8.486085 | 8.918033 |
| FMR1 | 0.71355444 | 0.047910176 | 0.02840558 | 7.241451953 | 4.963444 | 3.360637 | 3.935222 | 7.037879 | 7.819723 | 5.882028 |
| UBE3A | 0.733196316 | 0.047307334 | 0.026870364 | 7.240391762 | 5.856559 | 6.03611 | 7.003286 | 8.833301 | 8.892178 | 9.072081 |
| SLC31A1 | 0.730237723 | 0.047384624 | 0.02709425 | 7.237665664 | 6.58615 | 5.487673 | 6.282905 | 8.014609 | 9.138429 | 9.486503 |
| ARFIP1 | 0.712872602 | 0.047938332 | 0.028472269 | 7.235404488 | 4.682076 | 4.389936 | 3.324375 | 7.25991 | 7.53715 | 5.900694 |
| WWC3 | 0.844920873 | 0.044645837 | 0.019184076 | 7.234256233 | 5.316227 | 4.830496 | 3.764125 | 8.139755 | 7.68534 | 7.523109 |
| APBB2 | 0.776122793 | 0.045884853 | 0.023650902 | 7.23081806 | 6.45321 | 6.092406 | 6.054038 | 9.307369 | 8.486085 | 8.952456 |
| CIRH1A | 0.706179329 | 0.048342199 | 0.029201769 | 7.224925441 | 4.309025 | 3.32135 | 4.285996 | 7.877571 | 7.138979 | 5.426231 |
| KIAA0196 | 0.73762439 | 0.047140798 | 0.026566859 | 7.207546316 | 4.963444 | 3.360637 | 3.935222 | 7.037879 | 6.78473 | 6.649696 |
| ANGPTL1 | 0.676907287 | 0.049712169 | 0.031978904 | 7.207546316 | 5.328526 | 2.023048 | 3.935222 | 7.726141 | 6.78473 | 5.634184 |
| FAM73A | 0.785494721 | 0.045624536 | 0.022939095 | 7.204929585 | 4.682076 | 4.911517 | 5.723602 | 7.531061 | 8.296229 | 8.010706 |
| PUS1 | 0.56991987 | 0.06033194 | 0.048923443 | 7.186879148 | 1.874444 | 3.360637 | 2.165421 | 5.705318 | 6.205902 | 2.921909 |
| BMP4 | 0.788940003 | 0.045529634 | 0.022696836 | 7.186319743 | 3.819732 | 3.872014 | 5.609945 | 6.664985 | 7.740604 | 8.357484 |
| LITAF | 0.709557734 | 0.048237753 | 0.028848588 | 7.18266255 | 7.09018 | 6.931478 | 6.976024 | 10.351527 | 8.724089 | 9.820543 |
| HEATR5A | 0.806635887 | 0.045297753 | 0.021606669 | 7.18193748 | 4.263463 | 2.023048 | 3.935222 | 6.396698 | 7.107836 | 6.32627 |
| NHEG1 | 0.846553239 | 0.044634679 | 0.01910786 | 7.181219266 | 1.874444 | 2.023048 | 2.165421 | 4.718672 | 5.165949 | 4.790662 |
| CEP85 | 0.701970133 | 0.048553714 | 0.029652263 | 7.181219266 | 1.874444 | 3.770995 | 2.165421 | 4.718672 | 5.165949 | 6.32627 |
| MED12L | 0.691188968 | 0.04881728 | 0.030129976 | 7.181219266 | 1.874444 | 2.023048 | 3.90836 | 4.718672 | 5.509998 | 5.874974 |
| NPFF | 0.681036284 | 0.04946136 | 0.031537258 | 7.181219266 | 1.874444 | 2.406905 | 3.935222 | 4.718672 | 6.205902 | 5.426231 |
| TYW1B | 0.645111299 | 0.051836922 | 0.035906771 | 7.181219266 | 1.874444 | 2.023048 | 3.764125 | 4.718672 | 5.306419 | 5.106393 |
| ATP1B4 | 0.810298486 | 0.045237293 | 0.021020739 | 7.181020739 | 3.350997 | 2.406905 | 2.995681 | 5.728038 | 5.509998 | 6.195186 |
| IGBP1 | 0.726040359 | 0.047543032 | 0.027426335 | 7.179138163 | 5.700376 | 6.03611 | 6.527811 | 9.466036 | 8.87992 | 8.010706 |
| PGM2 | 0.671798735 | 0.050003999 | 0.032532154 | 7.172124828 | 4.963444 | 3.770995 | 3.935222 | 7.074163 | 6.613395 | 5.580533 |
| PAPLN | 0.685945955 | 0.049293152 | 0.031045934 | 7.171187046 | 2.201691 | 4.413323 | 5.225216 | 5.728038 | 7.740604 | 7.255535 |
| MEF2C | 0.733196664 | 0.047307334 | 0.026849949 | 7.165328586 | 4.682076 | 4.413323 | 3.935222 | 7.394225 | 6.237456 | 7.523109 |
| RPL15 | 0.854358563 | 0.044464174 | 0.018643076 | 7.162720388 | 10.414694 | 10.079831 | 10.175278 | 13.255201 | 13.246238 | 12.862923 |
| SPRED2 | 0.638236089 | 0.052467325 | 0.03687785 | 7.154217959 | 4.743564 | 4.750708 | 3.90836 | 7.582358 | 7.91889 | 5.580533 |
| RNF113A | 0.78477747 | 0.045655746 | 0.022992174 | 7.149201367 | 5.056948 | 5.297868 | 4.724406 | 7.25991 | 7.89473 | 8.391335 |
| TRMT1L | 0.713028886 | 0.047932772 | 0.028461381 | 7.145483504 | 2.201691 | 3.770995 | 3.324375 | 5.320955 | 6.608026 | 5.580533 |
| PPP1R11 | 0.619635141 | 0.054008689 | 0.039508676 | 7.145483504 | 5.744513 | 3.770995 | 2.379345 | 6.954147 | 6.608026 | 6.195186 |
| CTSO | 0.753340003 | 0.04658639 | 0.025385505 | 7.14421314 | 5.328526 | 6.311907 | 5.018694 | 7.631894 | 9.148683 | 8.503924 |
| CAMK2N1 | 0.830457955 | 0.044867325 | 0.020053079 | 7.13622682 | 5.263699 | 3.360637 | 5.571599 | 8.376156 | 8.098861 | 7.582913 |
| COL15A1 | 0.701088052 | 0.048630415 | 0.029752977 | 7.136156204 | 6.381847 | 5.487673 | 4.449894 | 6.954147 | 10.058027 | 8.32282 |
| PCDHB10 | 0.853942577 | 0.044464174 | 0.018656686 | 7.133196051 | 1.874444 | 3.360637 | 3.764125 | 6.183122 | 6.373501 | 6.195186 |
| ATF2 | 0.810653571 | 0.045237293 | 0.021349439 | 7.130724499 | 5.982974 | 4.80797 | 6.450701 | 9.204692 | 8.817023 | 8.391335 |
| CCDC132 | 0.763297192 | 0.046274022 | 0.024642395 | 7.126729785 | 3.024504 | 3.32135 | 2.165421 | 6.811341 | 5.857745 | 4.790662 |
| IL18 | 0.605683685 | 0.0555885 | 0.041751616 | 7.126729785 | 3.024504 | 3.770995 | 5.571599 | 7.33564 | 5.857745 | 6.618407 |
| DROSHA | 0.73382511 | 0.047307334 | 0.026795509 | 7.117861104 | 5.328526 | 4.736586 | 2.165421 | 8.156778 | 7.56803 | 6.129407 |
| TCEANC2 | 0.699705494 | 0.048673855 | 0.029902007 | 7.115538594 | 6.707871 | 6.702075 | 7.77844 | 8.864724 | 9.789758 | 10.609413 |

TABLE 8-continued

Differentially Expressed Genes in CD10−, CD24−, CD44− Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| GGCX | 0.755328602 | 0.046505334 | 0.025223545 | 7.111431336 | 6.227577 | 6.702075 | 6.83141 | 8.641022 | 9.532215 | 9.801784 |
| CHD9 | 0.766457585 | 0.046178907 | 0.024381763 | 7.10477409 | 5.491121 | 4.351315 | 4.508334 | 7.33564 | 8.549366 | 7.180104 |
| P2RX7 | 0.629798503 | 0.053216585 | 0.038108881 | 7.104488334 | 5.328526 | 5.487673 | 6.054038 | 6.664985 | 8.87992 | 8.882768 |
| SECISBP2L | 0.748557452 | 0.046757859 | 0.025744811 | 7.102733926 | 5.491121 | 4.389936 | 4.449894 | 7.36523 | 7.942653 | 7.218312 |
| PPP3R1 | 0.854419221 | 0.044464174 | 0.018636271 | 7.100875566 | 4.209882 | 4.389936 | 3.935222 | 7.037879 | 8.332658 | 6.73963 |
| SGMS1 | 0.760721059 | 0.046345577 | 0.024805716 | 7.098138576 | 4.743564 | 2.809601 | 4.754917 | 7.582358 | 7.414086 | 6.385515 |
| ENPP6 | 0.690086034 | 0.048987301 | 0.030645798 | 7.09003385 | 5.856559 | 5.43468 | 4.724406 | 6.954147 | 8.682351 | 8.357484 |
| DBF4 | 0.712101991 | 0.0479972 | 0.028576387 | 7.086321933 | 3.839948 | 4.830496 | 5.389265 | 6.664985 | 7.819723 | 7.722406 |
| EXOSC10 | 0.871225053 | 0.044325295 | 0.017811501 | 7.077566226 | 3.839948 | 3.872014 | 3.764125 | 7.243046 | 6.640994 | 6.587378 |
| MICB | 0.710568707 | 0.048127555 | 0.028736985 | 7.077566226 | 5.328526 | 2.023048 | 3.764125 | 6.339437 | 7.174648 | 6.587378 |
| DLG1 | 0.778406374 | 0.045844227 | 0.023437224 | 7.076290445 | 5.328526 | 4.389936 | 4.944468 | 7.918071 | 7.767462 | 7.291822 |
| NIPAL1 | 0.825890386 | 0.044948812 | 0.020358625 | 7.075462227 | 4.743564 | 4.750708 | 5.974145 | 7.477873 | 8.63937 | 8.79697 |
| RNF219 | 0.71482041 | 0.047877006 | 0.028325281 | 7.073799703 | 2.201691 | 3.360637 | 2.165421 | 6.183122 | 5.936219 | 4.146207 |
| PPP1R12A | 0.805071325 | 0.045318476 | 0.02170262 | 7.059099505 | 7.021395 | 6.42919 | 6.527811 | 9.410337 | 9.637899 | 9.248674 |
| NOS1 | 0.581518722 | 0.058540518 | 0.046349779 | 7.053750931 | 6.417969 | 6.537655 | 6.737132 | 7.531061 | 9.555522 | 9.380933 |
| CCRN4L | 0.762988137 | 0.04628868 | 0.024664852 | 7.053044594 | 4.639409 | 3.872014 | 3.324375 | 8.190235 | 6.043524 | 6.69026 |
| NBEA | 0.681070433 | 0.04946136 | 0.031530453 | 7.053044594 | 5.982974 | 3.872014 | 3.935222 | 7.33564 | 7.96603 | 6.69026 |
| ANK2 | 0.748735756 | 0.046735137 | 0.025723716 | 7.042577861 | 3.819732 | 4.351315 | 5.389265 | 7.167419 | 7.107836 | 7.640338 |
| KDELC2 | 0.633497261 | 0.052935473 | 0.037605988 | 6.992847126 | 4.963444 | 3.872014 | 5.544653 | 5.728038 | 8.350533 | 8.340256 |
| KANSL3 | 0.785913456 | 0.045579058 | 0.022887377 | 6.989656732 | 5.304463 | 4.413323 | 5.389265 | 8.190235 | 7.89473 | 8.194487 |
| RCAN2 | 0.633995267 | 0.052606547 | 0.037158898 | 6.989057445 | 5.744513 | 2.406905 | 4.724406 | 6.183122 | 6.640994 | 8.549611 |
| ANKIB1 | 0.704780862 | 0.048386088 | 0.02933719 | 6.988741637 | 5.491121 | 4.351315 | 3.324375 | 8.254907 | 7.473335 | 6.129407 |
| IL19 | 0.700450997 | 0.048706455 | 0.02983804 | 6.988741637 | 1.874444 | 2.809601 | 3.324375 | 4.739845 | 5.165949 | 6.129407 |
| ATG16L1 | 0.766117383 | 0.046178907 | 0.024399456 | 6.98853082 | 5.328526 | 4.413323 | 3.764125 | 7.074163 | 7.793829 | 7.218312 |
| RSL24D1 | 0.743761236 | 0.046889341 | 0.026091187 | 6.978466666 | 6.973646 | 6.572071 | 5.571599 | 10.106301 | 9.294336 | 8.374509 |
| JAK1 | 0.694554329 | 0.048864786 | 0.030306227 | 6.975193152 | 5.658609 | 4.750708 | 6.919905 | 8.460842 | 8.963611 | 8.053616 |
| TPR | 0.604944554 | 0.055644091 | 0.041846206 | 6.966972979 | 4.309025 | 6.03611 | 3.764125 | 7.109557 | 7.53715 | 6.649696 |
| RPL13 | 0.834558464 | 0.044793607 | 0.01974277 | 6.9658023 | 12.312017 | 12.382127 | 12.452391 | 15.182416 | 14.855391 | 16.262357 |
| USP42 | 0.703637877 | 0.048490179 | 0.029475332 | 6.961765959 | 5.316227 | 5.195784 | 6.489771 | 8.553743 | 8.077554 | 8.11568 |
| TIGD1 | 0.769040285 | 0.046096091 | 0.024124532 | 6.960231769 | 6.381847 | 5.340619 | 6.012527 | 8.139755 | 9.508524 | 8.692228 |
| COQ6 | 0.676023832 | 0.049752474 | 0.032071453 | 6.952301537 | 5.744513 | 4.413323 | 3.764125 | 7.210813 | 7.187136 | 7.255535 |
| DNPEP | 0.73273744 | 0.047310912 | 0.026909833 | 6.940206389 | 9.292103 | 9.410824 | 9.465832 | 11.385805 | 12.205803 | 12.340755 |
| LOC100287846 | 0.793906389 | 0.04542938 | 0.022413066 | 6.937762426 | 5.700376 | 6.060401 | 5.723602 | 8.222933 | 8.518072 | 9.123341 |
| SCAI | 0.756851866 | 0.046433585 | 0.025050698 | 6.933495421 | 6.792865 | 6.228068 | 7.339085 | 9.02165 | 9.687973 | 9.939727 |
| BZW1 | 0.856705442 | 0.044407381 | 0.018518544 | 6.932859883 | 7.355332 | 7.615377 | 7.360327 | 10.391631 | 10.408827 | 10.142182 |
| FLJ31662 | 0.76712426 | 0.04617033 | 0.024360667 | 6.930558334 | 3.839948 | 3.872014 | 4.508334 | 6.664985 | 6.861783 | 6.649696 |
| STUB1 | 0.80439964 | 0.045327183 | 0.021730521 | 6.910860268 | 5.316227 | 4.80797 | 5.018694 | 8.105092 | 7.53715 | 7.825039 |
| ZNF394 | 0.734361412 | 0.047307334 | 0.026766247 | 6.907737242 | 5.056948 | 4.351315 | 4.724406 | 7.607339 | 7.845161 | 6.69026 |
| PPAP2A | 0.765241038 | 0.046178907 | 0.024453896 | 6.906274427 | 5.658609 | 5.340619 | 6.012527 | 7.177844 | 8.098861 | 8.010706 |
| ZKSCAN1 | 0.772812667 | 0.046036363 | 0.023869343 | 6.902980997 | 6.186289 | 4.413323 | 5.544653 | 8.331873 | 9.218487 | 8.503924 |
| DOCK11 | 0.690527769 | 0.048985317 | 0.0306213 | 6.901459957 | 2.201691 | 2.023048 | 3.935222 | 5.320955 | 4.608763 | 6.722123 |
| CASP4 | 0.778736139 | 0.045829476 | 0.023390269 | 6.899848881 | 1.874444 | 2.023048 | 3.764125 | 6.550689 | 4.539173 | 6.129407 |
| ZFAND6 | 0.682436794 | 0.04941326 | 0.031437224 | 6.899848881 | 2.993831 | 2.023048 | 3.764125 | 6.550689 | 5.165949 | 5.091834 |
| LOC285972 | 0.708701085 | 0.04824159 | 0.028911875 | 6.893930444 | 4.963444 | 6.391145 | 5.974145 | 7.748771 | 8.314558 | 9.60665 |
| SEC24B | 0.707301819 | 0.048274546 | 0.029054781 | 6.890989591 | 3.839948 | 4.389936 | 4.508334 | 6.664985 | 7.174648 | 6.649696 |
| SGK1 | 0.793395313 | 0.04542938 | 0.022467506 | 6.890391966 | 6.45321 | 6.537655 | 6.175931 | 8.676869 | 9.237827 | 7.825039 |
| CROCCP3 | 0.739952749 | 0.047086482 | 0.026373596 | 6.888503936 | 4.209882 | 4.830496 | 4.508334 | 6.339437 | 7.292524 | 8.472642 |
| GUK1 | 0.684513781 | 0.049344803 | 0.03122967 | 6.883850407 | 7.513971 | 7.631788 | 7.825025 | 10.608241 | 9.357582 | 8.579284 |
| CCNG2 | 0.568127385 | 0.060662455 | 0.049383464 | 6.881073303 | 5.316227 | 4.389936 | 6.704285 | 9.687221 | 8.098861 | 6.195186 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| BAAT | 0.72717691 | 0.047508117 | 0.027359646 | 6.87757626 | 2.993831 | 2.406905 | 3.90836 | 4.739845 | 6.608026 | 6.69026 |
| NDUFS2 | 0.719490934 | 0.047752902 | 0.027991834 | 6.875265914 | 6.099991 | 4.830496 | 2.995681 | 8.122528 | 7.191402 | 7.611911 |
| KCTD6 | 0.724043748 | 0.047585406 | 0.027544063 | 6.870657215 | 4.263463 | 3.770995 | 2.995681 | 7.074163 | 6.551443 | 5.634184 |
| IPO7 | 0.648457328 | 0.051584246 | 0.03528411 | 6.870552983 | 5.700376 | 6.391145 | 5.609945 | 9.171571 | 8.609988 | 7.352555 |
| SLC17A5 | 0.741043196 | 0.047036111 | 0.026292617 | 6.868746927 | 4.963444 | 4.351315 | 3.764125 | 6.544171 | 8.011679 | 6.942983 |
| CYP3A4 | 0.709782224 | 0.04819475 | 0.028808438 | 6.867897172 | 5.335413 | 3.872014 | 5.225216 | 6.651882 | 8.200916 | 7.873743 |
| NLRC3 | 0.790929545 | 0.045520454 | 0.022613814 | 6.866464843 | 2.201691 | 2.023048 | 3.90836 | 4.802615 | 6.551443 | 6.385515 |
| PHYHIPL | 0.753340396 | 0.04658639 | 0.0253787 | 6.866464843 | 1.874444 | 2.023048 | 2.995681 | 4.802615 | 4.608763 | 6.106561 |
| TRPM1 | 0.713670454 | 0.047910176 | 0.028398775 | 6.866464843 | 1.874444 | 2.023048 | 2.165421 | 4.802615 | 5.857745 | 3.676349 |
| C5orf63 | 0.672477559 | 0.049933984 | 0.032447091 | 6.866464843 | 4.263463 | 2.023048 | 2.165421 | 4.802615 | 6.205902 | 5.634184 |
| CYS1 | 0.567105836 | 0.060808506 | 0.049521606 | 6.866464843 | 1.874444 | 2.023048 | 2.379345 | 4.802615 | 5.306429 | 2.921909 |
| CROCC | 0.67232718 | 0.049970781 | 0.032487921 | 6.866359717 | 4.743564 | 3.32135 | 4.508334 | 5.705318 | 7.31791 | 7.523109 |
| CFLAR | 0.81304772 | 0.045218796 | 0.021194284 | 6.849277396 | 10.610849 | 9.990385 | 10.399636 | 12.72221 | 13.98053 | 13.175588 |
| C14orf109 | 0.828962535 | 0.044930476 | 0.020201429 | 6.84357683 | 1.874444 | 2.023048 | 2.379345 | 6.550689 | 4.797798 | 4.562324 |
| GKAP1 | 0.821677832 | 0.045048325 | 0.020624702 | 6.84357683 | 1.874444 | 2.023048 | 2.165421 | 5.095353 | 4.797798 | 4.562324 |
| MUC15 | 0.815112827 | 0.04518297 | 0.021045253 | 6.84357683 | 1.874444 | 2.023048 | 2.165421 | 5.320955 | 4.797798 | 4.476242 |
| NME5 | 0.800585288 | 0.045343936 | 0.021952365 | 6.84357683 | 1.874444 | 2.023048 | 3.764125 | 6.811341 | 4.797798 | 4.146207 |
| SWT1 | 0.794489417 | 0.04542938 | 0.022388568 | 6.84357683 | 1.874444 | 2.023048 | 2.165421 | 6.498222 | 4.797798 | 4.146207 |
| SLC25A16 | 0.766653308 | 0.046178907 | 0.024174957 | 6.84357683 | 1.874444 | 2.023048 | 2.379345 | 6.183122 | 4.797798 | 4.146207 |
| C3orf71 | 0.761848503 | 0.046345155 | 0.024751276 | 6.84357683 | 2.993831 | 2.023048 | 2.165421 | 5.026959 | 4.797798 | 5.634184 |
| NAT1 | 0.732633772 | 0.047319258 | 0.026931608 | 6.84357683 | 1.874444 | 2.023048 | 2.165421 | 6.498222 | 4.797798 | 3.676349 |
| NRG4 | 0.722097878 | 0.047646206 | 0.027733243 | 6.84357683 | 1.874444 | 2.023048 | 2.165421 | 6.339437 | 4.797798 | 3.630092 |
| DHX57 | 0.720454539 | 0.047703746 | 0.027882953 | 6.84357683 | 3.839948 | 2.023048 | 2.165421 | 6.395481 | 4.797798 | 5.426231 |
| RPP40 | 0.720093979 | 0.047711776 | 0.027922423 | 6.84357683 | 1.874444 | 2.023048 | 2.165421 | 6.067497 | 4.797798 | 3.676349 |
| MIR567 | 0.698021359 | 0.04880344 | 0.03005376 | 6.84357683 | 1.874444 | 2.023048 | 2.165421 | 5.448591 | 4.797798 | 3.676349 |
| C3orf43 | 0.682646231 | 0.049399307 | 0.031397074 | 6.84357683 | 1.874444 | 2.023048 | 2.165421 | 5.252045 | 4.797798 | 3.630092 |
| RAB30 | 0.681954283 | 0.049428793 | 0.03148622 | 6.84357683 | 1.874444 | 2.023048 | 2.379345 | 5.095353 | 4.797798 | 3.676349 |
| RTP4 | 0.672321344 | 0.049970781 | 0.032494726 | 6.84357683 | 1.874444 | 2.023048 | 2.165421 | 7.607339 | 4.797798 | 3.676349 |
| CTAGE5 | 0.671451522 | 0.050012479 | 0.03255461 | 6.84357683 | 1.874444 | 2.023048 | 2.165421 | 6.283686 | 4.797798 | 3.630092 |
| CIDEC | 0.657691512 | 0.05087892 | 0.034083702 | 6.84357683 | 1.874444 | 2.023048 | 2.165421 | 5.448591 | 4.797798 | 2.921909 |
| C4BPA | 0.633586811 | 0.052918525 | 0.037585573 | 6.84357683 | 1.874444 | 2.023048 | 2.165421 | 5.252045 | 4.797798 | 2.921909 |
| GPR18 | 0.633586811 | 0.052918525 | 0.037585573 | 6.84357683 | 1.874444 | 2.023048 | 2.165421 | 6.395481 | 4.797798 | 3.676349 |
| ABCG5 | 0.629404622 | 0.053243865 | 0.038178972 | 6.84357683 | 1.874444 | 2.023048 | 2.165421 | 6.395481 | 4.797798 | 2.921909 |
| TMEM125 | 0.621233243 | 0.053905072 | 0.039309969 | 6.84357683 | 1.874444 | 2.023048 | 2.165421 | 6.283686 | 4.797798 | 3.630092 |
| MSH5 | 0.610755906 | 0.054914277 | 0.040784621 | 6.84357683 | 1.874444 | 2.023048 | 2.379345 | 6.544171 | 4.797798 | 2.921909 |
| FAM83B | 0.59343521 | 0.057025989 | 0.043907452 | 6.84357683 | 2.201691 | 2.023048 | 4.449894 | 5.891233 | 4.797798 | 5.446557 |
| PCDH17 | 0.579470453 | 0.058820115 | 0.046827492 | 6.84357683 | 3.839948 | 2.023048 | 2.165421 | 5.448591 | 4.797798 | 7.327219 |
| LOC100129858 | 0.574964563 | 0.059590623 | 0.047831916 | 6.84357683 | 1.874444 | 2.023048 | 2.165421 | 5.026959 | 4.797798 | 2.921909 |
| GRHL2 | 0.574964563 | 0.059590623 | 0.047831916 | 6.84357683 | 1.874444 | 2.023048 | 2.165421 | 5.095353 | 4.797798 | 2.921909 |
| RGS6 | 0.574301071 | 0.05968693 | 0.047956448 | 6.84357683 | 5.982974 | 2.023048 | 2.165421 | 6.811341 | 4.797798 | 6.618407 |
| LOC145474 | 0.571102763 | 0.060240587 | 0.048706363 | 6.84357683 | 1.874444 | 2.023048 | 2.165421 | 5.026959 | 4.797798 | 2.921909 |
| FAM90A1 | 0.571102763 | 0.060240587 | 0.048706363 | 6.84357683 | 1.874444 | 2.023048 | 2.165421 | 5.026959 | 4.797798 | 2.921909 |
| FRMPD4 | 0.571102763 | 0.060240587 | 0.048706363 | 6.84357683 | 1.874444 | 2.023048 | 2.165421 | 5.026959 | 4.797798 | 2.921909 |
| H2AFX | 0.586387877 | 0.057789468 | 0.045252127 | 6.842157888 | 5.897292 | 5.789702 | 6.072169 | 6.954147 | 8.724089 | 8.84662 |
| STK10 | 0.778693091 | 0.045838382 | 0.023402518 | 6.841989478 | 4.263463 | 4.80797 | 3.935222 | 7.037879 | 6.608026 | 8.095288 |
| TMEM67 | 0.785938447 | 0.045579058 | 0.022880572 | 6.841856282 | 1.874444 | 4.80797 | 4.944468 | 7.582358 | 9.064538 | 8.549611 |
| CHN2 | 0.759611025 | 0.04638287 | 0.024872406 | 6.836116085 | 6.306772 | 3.770995 | 2.165421 | 6.544171 | 4.608763 | 5.882028 |
| ACSS3 | 0.584539044 | 0.058094288 | 0.045711466 | 6.83179936 | 5.700376 | 4.389936 | 5.018694 | 8.220489 | 8.220489 | 8.472642 |
| C5orf22 | 0.674560796 | 0.04983446 | 0.032208915 | 6.82548782 | 4.263463 | 2.809601 | 3.764125 | 7.144104 | 5.936219 | 5.580533 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| ATP6V1H | 0.605840477 | 0.055562083 | 0.041714188 | 6.824898254 | 6.648293 | 5.148082 | 3.764125 | 8.105092 | 7.91889 | 7.033813 |
| DFFB | 0.645325588 | 0.051831344 | 0.035840082 | 6.822187473 | 4.682076 | 2.809601 | 4.944468 | 5.579836 | 7.187136 | 7.722406 |
| MPP7 | 0.733355119 | 0.047307334 | 0.028063559 | 6.821022268 | 4.263463 | 5.148082 | 2.379345 | 7.918071 | 6.319269 | 6.73963 |
| GATAD1 | 0.80421962 | 0.045327183 | 0.021157741 | 6.811921071 | 6.707871 | 6.184248 | 6.670675 | 8.905585 | 9.708913 | 9.438736 |
| F3 | 0.666917081 | 0.050336605 | 0.033134399 | 6.810534237 | 4.309025 | 4.830496 | 3.324375 | 6.244586 | 7.598264 | 6.32627 |
| C6orf15 | 0.849969076 | 0.044510429 | 0.01889214 | 6.809808289 | 1.874444 | 2.023048 | 2.165421 | 6.183122 | 4.608763 | 4.790662 |
| WDR78 | 0.838771668 | 0.044732882 | 0.019574685 | 6.809808289 | 1.874444 | 2.023048 | 2.165421 | 6.067497 | 4.539173 | 4.790662 |
| BCMO1 | 0.831112204 | 0.044867325 | 0.019985029 | 6.809808289 | 1.874444 | 2.023048 | 2.165421 | 4.739845 | 4.797798 | 4.790662 |
| ABCG2 | 0.827007715 | 0.044930476 | 0.020277645 | 6.809808289 | 1.874444 | 2.023048 | 2.165421 | 5.448591 | 4.539173 | 4.790662 |
| SH2D3C | 0.826899676 | 0.044930476 | 0.02028445 | 6.809808289 | 2.201691 | 2.023048 | 2.165421 | 5.095353 | 4.797798 | 4.790662 |
| BBIP1 | 0.730748004 | 0.047384624 | 0.027060225 | 6.809808289 | 3.350997 | 2.023048 | 2.995681 | 5.320955 | 7.094585 | 4.790662 |
| TMEM69 | 0.703897431 | 0.048451596 | 0.029436543 | 6.809808289 | 4.815804 | 2.023048 | 2.165421 | 7.109557 | 6.319269 | 4.790662 |
| LOC731424 | 0.691837333 | 0.048955004 | 0.030524668 | 6.809808289 | 3.024504 | 2.023048 | 2.995681 | 6.550689 | 4.797798 | 4.790662 |
| NCAM1 | 0.686022455 | 0.049293152 | 0.031035046 | 6.809808289 | 3.350997 | 2.023048 | 2.379345 | 5.320955 | 5.165949 | 4.790662 |
| ILDR1 | 0.665776484 | 0.050365391 | 0.033197686 | 6.809808289 | 1.874444 | 2.023048 | 2.165421 | 5.095353 | 3.571326 | 4.790662 |
| OXGR1 | 0.662186006 | 0.050577128 | 0.033595781 | 6.809808289 | 1.874444 | 2.023048 | 2.165421 | 5.026959 | 3.571326 | 4.790662 |
| OD24 | 0.651954127 | 0.051325457 | 0.0348377 | 6.809808289 | 3.819732 | 2.023048 | 2.165421 | 5.579836 | 5.165949 | 4.790662 |
| DNAJC14 | 0.644724495 | 0.051844669 | 0.035928547 | 6.809808289 | 3.839948 | 2.023048 | 2.995681 | 5.095353 | 6.794431 | 9.776388 |
| TMEM223 | 0.608770855 | 0.055170585 | 0.041167064 | 6.809808289 | 4.639409 | 2.023048 | 2.165421 | 5.579836 | 6.043524 | 6.129407 |
| ATP6V1E2 | 0.600504806 | 0.056318704 | 0.042763525 | 6.809808289 | 1.874444 | 2.023048 | 3.90836 | 4.739845 | 5.317867 | 4.790662 |
| EXOSC1 | 0.815820419 | 0.045173526 | 0.020098299 | 6.805878528 | 4.743564 | 4.413323 | 3.764125 | 7.210813 | 7.138979 | 7.180104 |
| AFF4 | 0.792169513 | 0.045455125 | 0.022515822 | 6.787369723 | 7.530567 | 7.152299 | 7.557139 | 10.395222 | 10.29342 | 9.776388 |
| DAAM1 | 0.701480993 | 0.048577236 | 0.029689758 | 6.780186296 | 5.304463 | 2.023048 | 2.995681 | 8.033165 | 7.174648 | 6.129407 |
| PWP1 | 0.606274027 | 0.055476612 | 0.041610071 | 6.779672353 | 3.819732 | 6.03611 | 4.508334 | 6.651882 | 7.269549 | 7.611911 |
| TBL1XR1 | 0.685258175 | 0.049314432 | 0.03114801 | 6.776529125 | 6.143785 | 5.340619 | 6.369239 | 9.146221 | 8.904331 | 7.611911 |
| CMPK1 | 0.742103002 | 0.046946487 | 0.024196666 | 6.772494116 | 7.641685 | 6.732825 | 5.609945 | 10.123723 | 9.492512 | 9.040427 |
| FMNL2 | 0.76368763 | 0.046237294 | 0.024600885 | 6.772386219 | 5.328526 | 5.789702 | 5.544653 | 7.771052 | 8.549366 | 8.357484 |
| C1orf55 | 0.756424277 | 0.046454067 | 0.025111262 | 6.716237063 | 4.963444 | 4.351315 | 5.217616 | 7.976765 | 7.440337 | 7.218312 |
| UBE2L6 | 0.669230773 | 0.050138385 | 0.032794148 | 6.757111557 | 6.417969 | 4.351315 | 4.944468 | 7.109557 | 8.609988 | 7.988762 |
| LOC100505854 | 0.772574981 | 0.046036363 | 0.023889758 | 6.758137251 | 3.819732 | 2.023048 | 3.90836 | 6.664985 | 6.205902 | 5.882028 |
| C7orf30 | 0.806785494 | 0.045297753 | 0.021593059 | 6.738454453 | 5.304463 | 4.830496 | 2.995681 | 7.394225 | 7.68534 | 7.582913 |
| FBXO21 | 0.690164554 | 0.048987301 | 0.030638993 | 6.735575466 | 5.856559 | 5.43468 | 4.754917 | 7.037879 | 8.277663 | 8.60836 |
| ZAK | 0.68577198 | 0.049293152 | 0.031086764 | 6.731244415 | 8.096549 | 7.197097 | 7.401896 | 9.284314 | 10.152769 | 11.136626 |
| PLAGL1 | 0.604625764 | 0.055684088 | 0.041911535 | 6.716481984 | 3.819732 | 4.750708 | 6.601009 | 7.177844 | 9.348715 | 6.618407 |
| TCF19 | 0.722740151 | 0.04762218 | 0.027674039 | 6.716237063 | 1.874444 | 2.023048 | 2.995681 | 5.743334 | 4.797798 | 4.476242 |
| TRIM36 | 0.654977526 | 0.051064299 | 0.034393331 | 6.716237063 | 1.874444 | 2.023048 | 2.995681 | 5.743334 | 5.306419 | 3.630092 |
| TPD52L1 | 0.752045018 | 0.0466011 | 0.025481456 | 6.711764035 | 5.700376 | 6.537655 | 3.935222 | 8.447068 | 8.564762 | 8.194487 |
| GNRHR2 | 0.714752821 | 0.047877006 | 0.028345696 | 6.71044272 | 4.682076 | 4.351315 | 3.935222 | 6.244586 | 7.107836 | 7.428484 |
| CYFIP1 | 0.758405425 | 0.046395081 | 0.024935012 | 6.709399216 | 5.856559 | 4.413323 | 4.285996 | 8.540832 | 7.845161 | 7.03218 |
| CCDC152 | 0.708058857 | 0.048268527 | 0.028994216 | 6.702081699 | 6.267718 | 6.270596 | 7.913913 | 9.012327 | 10.463244 | 9.329475 |
| GFRA1 | 0.700760693 | 0.048679397 | 0.029799251 | 6.694378691 | 6.344798 | 5.362142 | 7.003286 | 8.105092 | 8.892178 | 10.060372 |
| CSAD | 0.696788 | 0.048824537 | 0.030158557 | 6.690442644 | 5.263699 | 5.362142 | 6.175931 | 7.144104 | 8.842512 | 8.918033 |
| HOPX | 0.765004983 | 0.046181862 | 0.024478394 | 6.688537771 | 6.143785 | 4.413323 | 5.018694 | 6.063041 | 7.25505 | 7.395512 |
| SYT11 | 0.664619722 | 0.050400851 | 0.033316774 | 6.686557525 | 6.143785 | 4.413323 | 5.225216 | 7.274575 | 8.098861 | 7.96648 |
| UBR5 | 0.753972134 | 0.046571395 | 0.025346717 | 6.686317861 | 5.491121 | 4.750708 | 6.012527 | 7.771052 | 8.518072 | 8.232333 |
| TRIM14 | 0.769526997 | 0.046076407 | 0.024071453 | 6.676269236 | 6.792865 | 7.174872 | 7.401896 | 10.140938 | 9.991223 | 9.372483 |
| RHOBTB1 | 0.762006604 | 0.046345155 | 0.024732222 | 6.674531336 | 3.819732 | 3.872014 | 3.324375 | 6.063041 | 6.78473 | 6.195186 |
| MTX1 | 0.719108997 | 0.047781016 | 0.028034025 | 6.66652432 | 6.736762 | 5.340619 | 6.054038 | 9.252991 | 8.077554 | 8.918033 |
| TMF1 | 0.703583454 | 0.048494719 | 0.029497788 | 6.663963635 | 6.554045 | 6.702075 | 5.018694 | 9.43455 | 8.963611 | 8.095288 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| EYA3 | 0.746296781 | 0.046811314 | 0.025936033 | 6.663656769 | 2.993831 | 3.872014 | 4.724406 | 6.550689 | 6.205902 | 7.46072 |
| NEBL | 0.570113424 | 0.06033194 | 0.048894862 | 6.662263214 | 3.350997 | 3.872014 | 5.217616 | 7.976765 | 6.608026 | 5.091834 |
| C14orf142 | 0.807154464 | 0.045278798 | 0.02155427 | 6.654452133 | 1.874444 | 2.406905 | 2.165421 | 5.095353 | 4.608763 | 5.106393 |
| PTPN7 | 0.773130477 | 0.046036363 | 0.023848928 | 6.654452133 | 1.874444 | 2.023048 | 3.90836 | 6.395481 | 4.608763 | 6.32627 |
| PUS3 | 0.692493612 | 0.048955004 | 0.030463423 | 6.654452133 | 1.874444 | 3.770995 | 2.165421 | 5.705318 | 4.608763 | 5.634184 |
| PBOV1 | 0.611091007 | 0.054867364 | 0.040706363 | 6.654452133 | 1.874444 | 2.023048 | 3.764125 | 5.026959 | 4.608763 | 5.091834 |
| ADRB2 | 0.589571262 | 0.057478449 | 0.044701599 | 6.654452133 | 1.874444 | 4.750708 | 2.165421 | 5.579836 | 4.608763 | 6.106561 |
| RSRC2 | 0.783008898 | 0.045695042 | 0.023098333 | 6.654315806 | 7.259029 | 7.174872 | 7.056312 | 10.686531 | 9.909162 | 9.380933 |
| OBFC1 | 0.746450009 | 0.046811314 | 0.025922423 | 6.653425707 | 4.682076 | 4.80797 | 3.764125 | 6.498222 | 7.269549 | 7.873743 |
| TADA1 | 0.671507456 | 0.050012479 | 0.032547805 | 6.653425707 | 3.350997 | 2.023048 | 3.764125 | 6.498222 | 6.189775 | 4.562324 |
| SYNM | 0.839253106 | 0.044732882 | 0.01955427 | 6.648832442 | 4.209882 | 4.351315 | 2.995681 | 7.074163 | 6.774676 | 6.942983 |
| TPMT | 0.803600089 | 0.045338539 | 0.021814903 | 6.64540175 | 3.350997 | 2.406905 | 2.995681 | 5.728038 | 5.857745 | 5.634184 |
| FYCO1 | 0.806175784 | 0.045315307 | 0.021644097 | 6.642426559 | 3.819732 | 3.872014 | 3.324375 | 7.748771 | 6.551443 | 5.900694 |
| ERGIC1 | 0.678168983 | 0.049604445 | 0.031818986 | 6.640369465 | 6.143785 | 4.389936 | 3.90836 | 8.875048 | 8.220489 | 6.106561 |
| LRRN4CL | 0.698804692 | 0.048763723 | 0.029982987 | 6.63895878 | 3.819732 | 4.413323 | 6.054038 | 6.550689 | 8.737787 | 7.695565 |
| HOXC10 | 0.599161745 | 0.056396398 | 0.042994216 | 6.63895878 | 3.819732 | 2.809601 | 3.90836 | 6.550689 | 6.774676 | 4.476242 |
| RPL35 | 0.801358162 | 0.045343936 | 0.02191834 | 6.638338764 | 10.960825 | 11.292965 | 10.774746 | 13.509545 | 13.505568 | 15.114718 |
| CCNJL | 0.796271953 | 0.045374706 | 0.022227288 | 6.636707286 | 3.819732 | 3.32135 | 3.935222 | 6.960054 | 6.549959 | 6.051818 |
| EFHA2 | 0.608478707 | 0.055189127 | 0.041198367 | 6.636707286 | 5.897292 | 3.32135 | 3.324375 | 6.811341 | 7.269549 | 6.051818 |
| WWP1 | 0.796244121 | 0.045374706 | 0.022234093 | 6.634429739 | 5.744513 | 5.148082 | 4.285996 | 8.474485 | 7.793829 | 7.774634 |
| KLRG1 | 0.775319686 | 0.045964297 | 0.02374277 | 6.630241233 | 2.993831 | 2.406905 | 2.165421 | 4.894482 | 5.306419 | 5.634184 |
| TTLL7 | 0.742195156 | 0.046946487 | 0.026183055 | 6.630241233 | 1.874444 | 2.023048 | 2.165421 | 4.894482 | 4.131418 | 4.790662 |
| MIPOL1 | 0.730948555 | 0.047384624 | 0.027046614 | 6.630241233 | 3.024504 | 3.32135 | 2.165421 | 4.894482 | 5.857745 | 5.882028 |
| C1orf180 | 0.671071474 | 0.05005437 | 0.032612453 | 6.630241233 | 1.874444 | 2.023048 | 2.165421 | 4.894482 | 4.797798 | 3.676349 |
| CDYL2 | 0.654781832 | 0.051064299 | 0.034413746 | 6.630241233 | 1.874444 | 2.023048 | 2.165421 | 4.894482 | 3.571326 | 4.790662 |
| MAGEA10 | 0.64791903 | 0.051631895 | 0.03539163 | 6.630241233 | 1.874444 | 2.406905 | 2.165421 | 4.894482 | 5.165949 | 3.630092 |
| MESP1 | 0.624040881 | 0.053689061 | 0.038856754 | 6.630241233 | 2.993831 | 2.023048 | 2.165421 | 4.894482 | 6.205902 | 3.630092 |
| DVL1 | 0.612310586 | 0.054772558 | 0.040558601 | 6.630241233 | 4.263483 | 4.413323 | 2.165421 | 4.894482 | 6.043524 | 7.943848 |
| TFDP1 | 0.614187236 | 0.054577731 | 0.04030146 | 6.628593599 | 5.304463 | 2.406905 | 4.508334 | 8.033165 | 6.794431 | 5.446557 |
| HDAC8 | 0.79229189 | 0.04545525 | 0.02250907 | 6.62099641 | 1.874444 | 2.809601 | 2.379345 | 4.894482 | 5.509998 | 5.106393 |
| TLR4 | 0.64058893 | 0.052201656 | 0.036498129 | 6.61461189 | 3.024504 | 4.413323 | 5.723602 | 7.144104 | 7.138979 | 6.618407 |
| MTUS1 | 0.65319224 | 0.051218943 | 0.034651922 | 6.598724016 | 5.856559 | 6.638536 | 7.180931 | 7.897963 | 9.903118 | 9.649245 |
| LOC100506994 | 0.744997695 | 0.04685274 | 0.026010888 | 6.586995484 | 5.304463 | 4.389936 | 2.165421 | 7.109557 | 6.78473 | 7.291822 |
| S100A10 | 0.659217236 | 0.050733231 | 0.033882953 | 6.585482971 | 7.786906 | 9.622716 | 8.114773 | 10.834062 | 10.785834 | 11.496849 |
| EML1 | 0.804996697 | 0.045318476 | 0.021709425 | 6.58484187 | 3.024504 | 2.023048 | 3.324375 | 5.743334 | 6.043524 | 5.426231 |
| RNF34 | 0.656276645 | 0.050987756 | 0.034221164 | 6.581504775 | 3.350997 | 2.809601 | 3.324375 | 6.395481 | 6.043524 | 4.562324 |
| FAM95B1 | 0.602013037 | 0.056043118 | 0.042421232 | 6.579143031 | 1.874444 | 4.389936 | 4.754917 | 6.339437 | 7.473335 | 5.091834 |
| SHMT2 | 0.616307176 | 0.054355679 | 0.040042872 | 6.574119148 | 6.008206 | 4.389936 | 3.764125 | 7.33564 | 7.107836 | 6.942983 |
| FAM133B | 0.833702616 | 0.044797567 | 0.019775434 | 6.574119148 | 1.874444 | 2.023048 | 2.165421 | 4.739845 | 5.936219 | 4.562324 |
| OR9Q1 | 0.833432603 | 0.044797567 | 0.019809459 | 6.574119148 | 1.874444 | 2.023048 | 2.165421 | 4.739845 | 5.92041 | 4.562324 |
| UPRT | 0.825766128 | 0.044949653 | 0.020376318 | 6.574119148 | 1.874444 | 2.023048 | 2.165421 | 4.739845 | 5.509998 | 4.562324 |
| FABP2 | 0.820609147 | 0.045095391 | 0.020684587 | 6.574119148 | 2.201691 | 2.023048 | 2.165421 | 4.739845 | 5.165949 | 4.790662 |
| RS1 | 0.81231687 | 0.045218796 | 0.021221504 | 6.574119148 | 1.874444 | 2.023048 | 2.165421 | 4.739845 | 4.539173 | 5.106393 |
| PTH2R | 0.811855987 | 0.045218796 | 0.021248724 | 6.574119148 | 1.874444 | 2.023048 | 2.165421 | 4.739845 | 4.539173 | 5.091834 |
| C1orf49 | 0.80845907 | 0.045247607 | 0.021475332 | 6.574119148 | 1.874444 | 2.023048 | 2.165421 | 4.739845 | 5.306419 | 4.476242 |
| FASTKD1 | 0.772305866 | 0.046057921 | 0.023916979 | 6.574119148 | 3.024504 | 2.023048 | 2.379345 | 4.739845 | 5.509998 | 5.580533 |
| KAL1 | 0.72974547 | 0.047394039 | 0.02713644 | 6.574119148 | 1.874444 | 2.023048 | 3.324375 | 4.739845 | 7.269549 | 4.476242 |
| SPEF2 | 0.719176809 | 0.047780505 | 0.028023137 | 6.574119148 | 1.874444 | 2.023048 | 2.165421 | 4.739845 | 6.205902 | 3.676349 |
| HEATR3 | 0.662680439 | 0.050529771 | 0.033537938 | 6.574119148 | 1.874444 | 2.023048 | 2.165421 | 4.739845 | 3.571326 | 5.106393 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| FAM176A | 0.621384502 | 0.053905072 | 0.039296359 | 6.574119148 | 1.874444 | 2.023048 | 2.165421 | 4.739845 | 6.189775 | 2.921909 |
| PTGR2 | 0.607910815 | 0.055264045 | 0.041317455 | 6.574119148 | 1.874444 | 2.023048 | 2.165421 | 4.739845 | 5.857745 | 2.921909 |
| CADM2 | 0.582837549 | 0.058309181 | 0.046037428 | 6.574119148 | 1.874444 | 2.023048 | 2.165421 | 4.739845 | 5.317867 | 2.921909 |
| PKD1L3 | 0.574911917 | 0.059591591 | 0.047842123 | 6.574119148 | 1.874444 | 2.023048 | 2.165421 | 4.739845 | 5.165949 | 2.921909 |
| SMC2 | 0.699747928 | 0.048730157 | 0.029891119 | 6.57276684 | 3.350997 | 2.809601 | 2.165421 | 6.067497 | 4.608763 | 5.580533 |
| IPCEF1 | 0.791576015 | 0.045499568 | 0.022581831 | 6.570522938 | 1.874444 | 2.023048 | 2.379345 | 5.095353 | 4.797798 | 4.562324 |
| SNRNP200 | 0.772553931 | 0.046036363 | 0.023896563 | 6.565925263 | 7.259029 | 7.0089 | 6.175931 | 9.388882 | 9.974027 | 9.438736 |
| ADPRHL2 | 0.679921625 | 0.049515112 | 0.031642055 | 6.554515277 | 3.350997 | 4.351315 | 2.379345 | 6.339437 | 6.794431 | 5.091834 |
| FLJ23867 | 0.650574964 | 0.05147219 | 0.035014631 | 6.554515277 | 3.839948 | 4.80797 | 2.379345 | 7.274575 | 6.861783 | 5.091834 |
| PCID2 | 0.761260126 | 0.046345577 | 0.024783501 | 6.549997035 | 3.839948 | 2.809601 | 3.90836 | 7.531061 | 6.551443 | 5.446557 |
| HDAC9 | 0.816007434 | 0.045165524 | 0.020978564 | 6.549964635 | 2.993831 | 3.32135 | 3.324375 | 5.705318 | 5.920411 | 6.722123 |
| ZNF326 | 0.647828733 | 0.051631895 | 0.035398435 | 6.543117209 | 6.267718 | 5.340619 | 4.508334 | 8.156778 | 8.181074 | 7.218312 |
| RBM24 | 0.659841458 | 0.050686676 | 0.033787683 | 6.501719706 | 3.350997 | 3.32135 | 2.165421 | 4.894482 | 5.306419 | 6.051818 |
| ANKRD50 | 0.682945167 | 0.049399307 | 0.031376659 | 6.500068692 | 3.024504 | 3.32135 | 5.217616 | 7.918071 | 7.414086 | 4.476242 |
| PREB | 0.592609126 | 0.057088939 | 0.044053079 | 6.499806249 | 4.743564 | 2.809601 | 2.165421 | 5.448591 | 5.509998 | 5.900694 |
| LGALS12 | 0.74150387 | 0.046993264 | 0.026246342 | 6.495714591 | 1.874444 | 2.406905 | 2.995681 | 4.802615 | 5.353925 | 5.106393 |
| COL12A1 | 0.717458629 | 0.047840971 | 0.028151752 | 6.48336025 | 5.316227 | 4.80797 | 6.704285 | 7.504712 | 9.053666 | 8.822008 |
| FXN | 0.739926373 | 0.047086482 | 0.026387207 | 6.481368213 | 5.316227 | 4.351315 | 5.723602 | 7.30543 | 8.4199 | 7.988762 |
| VPS45 | 0.838165312 | 0.044732882 | 0.019588295 | 6.478341568 | 1.874444 | 2.023048 | 2.165421 | 4.718672 | 6.373501 | 4.562324 |
| C6orf170 | 0.829863001 | 0.044925422 | 0.02013474 | 6.478341568 | 1.874444 | 2.023048 | 2.379345 | 4.718672 | 6.549959 | 4.476242 |
| NUDT6 | 0.8214516 | 0.045095391 | 0.020657366 | 6.478341568 | 1.874444 | 2.023048 | 2.165421 | 4.718672 | 6.043524 | 4.476242 |
| LOC28602 | 0.818579599 | 0.045111103 | 0.020825451 | 6.478341568 | 1.874444 | 2.023048 | 2.165421 | 4.718672 | 4.539173 | 5.446557 |
| IL18BP | 0.763993352 | 0.046193441 | 0.024541 | 6.478341568 | 1.874444 | 2.023048 | 2.165421 | 4.718672 | 4.131418 | 5.634184 |
| LRP1B | 0.7459248 | 0.046831501 | 0.025976863 | 6.478341568 | 1.874444 | 2.023048 | 2.165421 | 4.718672 | 4.131418 | 5.091834 |
| GMCL1 | 0.7459248 | 0.046831501 | 0.025976863 | 6.478341568 | 1.874444 | 2.023048 | 2.165421 | 4.718672 | 4.131418 | 5.091834 |
| UTP14C | 0.706412629 | 0.048309794 | 0.029154134 | 6.478341568 | 1.874444 | 2.023048 | 2.165421 | 4.718672 | 5.857745 | 3.676349 |
| BCS1L | 0.687965602 | 0.049127354 | 0.03081116 | 6.478341568 | 4.309025 | 2.023048 | 2.379345 | 4.718672 | 6.613395 | 5.900694 |
| ZNF185 | 0.687390901 | 0.049147961 | 0.03087853 | 6.478341568 | 1.874444 | 2.023048 | 2.165421 | 4.718672 | 5.509998 | 3.630092 |
| LRRTM2 | 0.679494508 | 0.049531477 | 0.031686968 | 6.478341568 | 1.874444 | 2.023048 | 2.379345 | 4.718672 | 5.165949 | 3.676349 |
| MFSD8 | 0.646729425 | 0.051721663 | 0.035630487 | 6.478341568 | 3.839948 | 3.770995 | 2.379345 | 4.718672 | 6.613395 | 4.790662 |
| GZMK | 0.573453137 | 0.049795609 | 0.048176255 | 6.478341568 | 1.874444 | 2.023048 | 2.165421 | 4.718672 | 5.165949 | 2.921909 |
| POLD3 | 0.653196282 | 0.051218943 | 0.034645117 | 6.465632376 | 2.201691 | 2.023048 | 2.379345 | 4.894482 | 5.509998 | 3.630092 |
| ZFPL1 | 0.662817535 | 0.050504642 | 0.033505274 | 6.464835878 | 6.054828 | 4.830496 | 3.764125 | 7.144104 | 7.767462 | 7.523109 |
| AKIP1 | 0.721877647 | 0.047650501 | 0.027745492 | 6.464446376 | 3.350997 | 3.770995 | 3.324375 | 5.448591 | 6.043524 | 6.931222 |
| FAM175A | 0.658468956 | 0.050764584 | 0.033942838 | 6.464446376 | 3.350997 | 2.023048 | 3.764125 | 4.718672 | 6.043524 | 6.129407 |
| RDH10 | 0.609457543 | 0.055130486 | 0.04102756 | 6.464446376 | 3.350997 | 2.023048 | 5.723602 | 7.167419 | 6.043524 | 5.900694 |
| NUPL1 | 0.692517596 | 0.048944238 | 0.030448452 | 6.461629205 | 5.753024 | 4.736586 | 3.935222 | 7.177844 | 7.656894 | 7.428484 |
| FAM49B | 0.735325858 | 0.047271239 | 0.026670743 | 6.460579268 | 4.815804 | 5.195784 | 6.031658 | 8.723321 | 7.845161 | 7.668215 |
| TRAP1 | 0.708952753 | 0.04824159 | 0.028844655 | 6.460440824 | 6.58615 | 6.35207 | 5.609945 | 8.301578 | 8.63937 | 9.414247 |
| SERF2 | 0.73235542 | 0.047319258 | 0.026952024 | 6.458501571 | 7.595107 | 6.957749 | 7.401896 | 10.093095 | 10.558612 | 9.303041 |
| LOC55103 | 0.652495679 | 0.051266842 | 0.034739027 | 6.458419077 | 2.201691 | 3.360637 | 4.724406 | 5.705318 | 6.319269 | 6.051818 |
| TRAM1 | 0.6179319 | 0.05418054 | 0.039750936 | 6.454930432 | 8.502009 | 7.033812 | 6.326717 | 9.33006 | 10.041614 | 9.724213 |
| EPHX2 | 0.69784744 | 0.04880344 | 0.030060565 | 6.451704131 | 3.350997 | 3.770995 | 4.724406 | 5.448591 | 7.414086 | 6.385515 |
| TIGD6 | 0.688904041 | 0.049056873 | 0.030728139 | 6.451476692 | 5.328526 | 4.750708 | 3.764125 | 6.498222 | 7.440337 | 7.825039 |
| CTDSPL | 0.801857075 | 0.04534393 | 0.021893841 | 6.448250934 | 4.815804 | 4.736586 | 3.935222 | 7.504712 | 7.31791 | 7.152205 |
| ZBTB2 | 0.640824842 | 0.052144602 | 0.036426676 | 6.445484384 | 4.815804 | 4.750708 | 5.389265 | 7.897963 | 8.077554 | 6.32627 |
| LINC00467 | 0.831652972 | 0.044860922 | 0.019949643 | 6.443660661 | 1.874444 | 2.023048 | 2.165421 | 6.811341 | 4.608763 | 4.562324 |
| PLG | 0.825333299 | 0.044949653 | 0.020410344 | 6.443660661 | 1.874444 | 2.023048 | 2.165421 | 6.395481 | 4.608763 | 4.562324 |
| C11orf82 | 0.824438303 | 0.044949653 | 0.020437564 | 6.443660661 | 1.874444 | 2.023048 | 2.165421 | 6.339437 | 4.608763 | 4.562324 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| SULT1C2 | 0.800502124 | 0.045343936 | 0.02197278 | 6.443660661 | 1.874444 | 2.023048 | 2.165421 | 4.718672 | 4.797798 | 4.562324 |
| SLC16A9 | 0.793300266 | 0.04542938 | 0.022474311 | 6.443660661 | 1.874444 | 2.023048 | 2.165421 | 4.894482 | 4.608763 | 4.562324 |
| PACRGL | 0.770609706 | 0.046076407 | 0.024051038 | 6.443660661 | 1.874444 | 2.023048 | 2.379345 | 5.095353 | 4.608763 | 4.562324 |
| AMPH | 0.767546252 | 0.046164489 | 0.024322559 | 6.443660661 | 1.874444 | 2.023048 | 2.995681 | 5.448591 | 5.353925 | 4.562324 |
| C2orf47 | 0.753529883 | 0.046580354 | 0.025365771 | 6.443660661 | 1.874444 | 2.809601 | 2.165421 | 6.664985 | 4.608763 | 4.562324 |
| KIAA1586 | 0.750529313 | 0.046662281 | 0.0255672 | 6.443660661 | 1.874444 | 2.023048 | 2.995681 | 5.095353 | 5.509998 | 4.562324 |
| PMP2 | 0.732387434 | 0.047319258 | 0.026945219 | 6.443660661 | 1.874444 | 2.023048 | 2.995681 | 5.026959 | 5.306419 | 4.562324 |
| RGPD2 | 0.703458338 | 0.048494719 | 0.029518203 | 6.443660661 | 1.874444 | 2.406905 | 3.324375 | 6.811341 | 4.797798 | 4.562324 |
| TAF5 | 0.697840522 | 0.04880344 | 0.03006737 | 6.443660661 | 1.874444 | 2.406905 | 2.995681 | 5.095353 | 5.165949 | 4.562324 |
| LOC440300 | 0.697478812 | 0.04880813 | 0.03008166 | 6.443660661 | 1.874444 | 2.023048 | 3.324375 | 5.026959 | 5.509998 | 4.562324 |
| TMEM154 | 0.674484583 | 0.049848381 | 0.032227969 | 6.443660661 | 1.874444 | 3.32135 | 2.165421 | 6.063041 | 4.608763 | 4.562324 |
| LOC283070 | 0.59965454 | 0.053361464 | 0.042903028 | 6.443660661 | 1.874444 | 3.360637 | 2.995681 | 6.067497 | 4.608763 | 4.562324 |
| SVIL | 0.779152955 | 0.045829476 | 0.023363049 | 6.429842921 | 3.350997 | 5.789702 | 6.326717 | 8.474485 | 8.998044 | 7.825039 |
| CXorf36 | 0.696448727 | 0.048851278 | 0.030190541 | 6.423717227 | 4.963444 | 4.351315 | 4.944468 | 6.183122 | 7.627877 | 8.870819 |
| ALAD | 0.749700277 | 0.046680047 | 0.026531848 | 6.418166844 | 5.304463 | 2.809601 | 4.724406 | 6.814118 | 7.406567 | 7.668215 |
| PFDN2 | 0.811878551 | 0.045218796 | 0.021241919 | 6.41010187 | 3.839948 | 5.43468 | 5.217616 | 7.897963 | 7.740604 | 7.943848 |
| CPEB2 | 0.715200732 | 0.047877006 | 0.028291256 | 6.407196 | 4.682076 | 4.80797 | 6.636362 | 8.700282 | 8.63937 | 7.36177 |
| LOC150622 | 0.717627912 | 0.047839239 | 0.028140864 | 6.405749748 | 6.099991 | 6.03611 | 5.225216 | 8.779359 | 8.098861 | 8.194487 |
| FAM198B | 0.809894509 | 0.045243682 | 0.021387547 | 6.404666456 | 6.381847 | 6.044198 | 6.636262 | 8.723321 | 10.843782 | 9.008063 |
| GOLGA7 | 0.647396377 | 0.051665552 | 0.035478734 | 6.404198818 | 5.328526 | 5.487673 | 3.90836 | 8.254907 | 7.505595 | 6.587378 |
| LINC00485 | 0.63730912 | 0.052514975 | 0.037026199 | 6.404198818 | 1.874444 | 2.809601 | 3.90836 | 4.341916 | 5.509998 | 6.587378 |
| MAGEH1 | 0.618203421 | 0.054162167 | 0.039706703 | 6.403910875 | 5.263699 | 4.389936 | 3.935222 | 5.448591 | 7.942653 | 6.051818 |
| STOML2 | 0.608674123 | 0.055179858 | 0.041182715 | 6.39949832 | 5.304463 | 5.195784 | 5.217616 | 8.331873 | 8.181074 | 7.873743 |
| IQCB1 | 0.721798843 | 0.047650501 | 0.027759102 | 6.397463061 | 5.491121 | 4.736586 | 4.754917 | 7.477873 | 7.414086 | 7.640338 |
| PARD3 | 0.786109028 | 0.045579058 | 0.02286017 | 6.391891713 | 5.856559 | 5.195784 | 5.609945 | 8.286188 | 8.033973 | 8.519314 |
| RWDD4 | 0.670758881 | 0.050060495 | 0.032666213 | 6.391800305 | 5.897292 | 4.389936 | 2.165421 | 6.857154 | 7.066159 | 7.218312 |
| SERINC1 | 0.604313082 | 0.055729438 | 0.041974141 | 6.378789812 | 5.982974 | 5.487673 | 5.217616 | 9.645614 | 8.160956 | 6.455366 |
| RRN3 | 0.698964767 | 0.048753782 | 0.029960531 | 6.372106251 | 6.143785 | 5.148082 | 4.508334 | 8.540832 | 8.160956 | 7.180104 |
| ARL6IP5 | 0.773147811 | 0.046036363 | 0.023842123 | 6.370082256 | 6.846868 | 7.0583 | 7.519866 | 10.191381 | 9.694987 | 9.642233 |
| RBM8A | 0.798449919 | 0.045355733 | 0.022102756 | 6.369318925 | 7.880509 | 8.170275 | 7.762571 | 10.43065 | 10.68376 | 10.841414 |
| PCGF3 | 0.675805492 | 0.049779748 | 0.032118408 | 6.369173936 | 6.186289 | 5.43468 | 4.724406 | 8.190235 | 8.350533 | 7.395512 |
| SEPN1 | 0.717131738 | 0.047840971 | 0.028158557 | 6.365120559 | 6.099991 | 5.661685 | 4.508334 | 8.331873 | 8.436733 | 7.611911 |
| PDCD6IP | 0.746645602 | 0.046800775 | 0.025872746 | 6.354708396 | 7.427999 | 6.849665 | 6.072169 | 9.352401 | 9.608485 | 9.517491 |
| CHURC1 | 0.777390157 | 0.045858846 | 0.02350051 | 6.349587244 | 5.700376 | 4.389936 | 5.389265 | 8.173604 | 8.055928 | 7.748756 |
| C6orf89 | 0.576182123 | 0.059351075 | 0.047470568 | 6.349587244 | 6.099991 | 4.911517 | 5.389265 | 8.811966 | 8.055928 | 6.455366 |
| RPL39L | 0.823650169 | 0.045005314 | 0.020498809 | 6.341084581 | 1.874444 | 2.023048 | 2.165421 | 6.811341 | 4.539173 | 4.562324 |
| CEP97 | 0.804479862 | 0.045327183 | 0.021723716 | 6.341084581 | 1.874444 | 2.023048 | 2.165421 | 5.705318 | 4.539173 | 4.790622 |
| PIP5K1B | 0.798401458 | 0.045355733 | 0.022109561 | 6.341084581 | 1.874444 | 2.023048 | 2.165421 | 4.739845 | 4.539173 | 4.790662 |
| WNT4 | 0.741790999 | 0.046966189 | 0.026222525 | 6.341084581 | 1.874444 | 2.809601 | 2.165421 | 5.705318 | 4.539173 | 4.790662 |
| NOSTRIN | 0.659765358 | 0.050686676 | 0.033794488 | 6.341084581 | 1.874444 | 3.360637 | 3.764125 | 6.067497 | 4.539173 | 6.385515 |
| LOC100509894 | 0.645735625 | 0.051818705 | 0.035799932 | 6.341084581 | 1.874444 | 2.406905 | 3.90836 | 5.705318 | 4.539173 | 5.580533 |
| ARHGAP9 | 0.57368366 | 0.059795609 | 0.048128615 | 6.341084581 | 1.874444 | 2.023048 | 4.449894 | 5.743334 | 4.539173 | 5.900694 |
| WNT5A | 0.566836366 | 0.060088212 | 0.049629806 | 6.341084581 | 1.874444 | 2.023048 | 5.225216 | 6.544171 | 4.539173 | 5.634184 |
| EVI5 | 0.729239139 | 0.047411805 | 0.027154815 | 6.329201007 | 6.648293 | 3.872014 | 5.544653 | 8.206677 | 8.077554 | 8.650903 |
| PNPLA4 | 0.648912942 | 0.051556323 | 0.035214699 | 6.322924346 | 4.263463 | 4.351315 | 5.974145 | 6.498222 | 7.138979 | 6.924055 |
| VDR | 0.678128041 | 0.049604445 | 0.031825791 | 6.312771171 | 3.839948 | 4.911517 | 5.571599 | 6.063041 | 8.160956 | 7.668215 |
| ZFHX4 | 0.637630221 | 0.052501106 | 0.036971079 | 6.311461597 | 5.744513 | 3.770995 | 5.592916 | 7.167419 | 9.075328 | 8.25089 |
| ERAP1 | 0.692048724 | 0.048955004 | 0.030493365 | 6.286061303 | 4.309025 | 5.148082 | 3.935222 | 7.191402 | 7.191402 | 6.587378 |
| ANP32B | 0.706956099 | 0.04829046 | 0.029101735 | 6.279094921 | 7.626325 | 7.106065 | 6.636262 | 9.805293 | 9.756621 | 9.33818 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| SERP1 | 0.676438867 | 0.049712169 | 0.032019735 | 6.277966306 | 7.04469 | 6.391145 | 7.381261 | 11.733767 | 9.694987 | 8.135789 |
| KLF9 | 0.63876887 | 0.05242235 | 0.036773052 | 6.270893872 | 9.955336 | 8.170275 | 8.844667 | 10.98468 | 11.493339 | 11.770461 |
| BATF | 0.720638274 | 0.047703746 | 0.027848928 | 6.26859894 | 5.335413 | 5.340619 | 5.592916 | 9.268737 | 7.269549 | 7.988762 |
| VANGL1 | 0.663655344 | 0.050460138 | 0.033397074 | 6.266299509 | 4.209882 | 2.809601 | 2.379345 | 5.026959 | 6.205902 | 5.900694 |
| LOC285593 | 0.579011342 | 0.058845512 | 0.046898945 | 6.266299509 | 1.874444 | 2.023048 | 2.379345 | 5.026959 | 3.134528 | 4.790662 |
| MTG1 | 0.589399659 | 0.05748724 | 0.044736305 | 6.254110872 | 6.306772 | 4.750708 | 3.935222 | 8.105092 | 6.640994 | 7.395512 |
| DICER1 | 0.776695265 | 0.045858868 | 0.023579449 | 6.2531581 | 6.765086 | 6.092406 | 6.072169 | 9.049264 | 9.409671 | 8.705744 |
| THEM4 | 0.667022298 | 0.050336605 | 0.033103096 | 6.25007546 | 6.873131 | 5.195784 | 5.702912 | 8.346785 | 8.71031 | 8.213534 |
| CARKD | 0.707235261 | 0.048286461 | 0.029077237 | 6.248534478 | 5.779429 | 4.750708 | 4.944468 | 7.394225 | 7.845161 | 7.825039 |
| PRMT7 | 0.756997911 | 0.046433585 | 0.025043892 | 6.245595399 | 3.819732 | 4.830496 | 5.389265 | 7.394225 | 7.473335 | 7.553321 |
| FAM3C | 0.668091983 | 0.050279153 | 0.032952705 | 6.233492416 | 6.52121 | 6.311707 | 5.723602 | 9.4454 | 8.951948 | 7.748756 |
| ASTE1 | 0.667604696 | 0.050323626 | 0.033043892 | 6.226851464 | 4.263463 | 2.809601 | 2.995681 | 6.498222 | 5.509998 | 5.634184 |
| AASS | 0.672534726 | 0.049933984 | 0.032426676 | 6.226410414 | 7.021395 | 6.35207 | 6.601009 | 8.331873 | 9.933088 | 9.23941 |
| FGD5 | 0.576082364 | 0.059369107 | 0.047494386 | 6.221935787 | 4.682076 | 2.023048 | 4.724406 | 6.183122 | 5.317867 | 7.36177 |
| GYLTL1B | 0.781499405 | 0.04575418 | 0.023214699 | 6.221206979 | 2.201691 | 2.023048 | 2.165421 | 4.802615 | 5.165949 | 4.476242 |
| MAP4K2 | 0.68660571 | 0.049239157 | 0.030966996 | 6.221206979 | 3.350997 | 2.023048 | 2.165421 | 4.802615 | 4.608763 | 6.051818 |
| FAM69B | 0.605091915 | 0.055639512 | 0.041833957 | 6.221206979 | 2.993831 | 4.413323 | 2.165421 | 4.802615 | 5.165949 | 7.327219 |
| PABPC1P2 | 0.630421597 | 0.053156193 | 0.038004764 | 6.220177893 | 1.874444 | 2.809601 | 4.285996 | 5.026959 | 6.043524 | 5.446557 |
| NOP10 | 0.746207029 | 0.046831501 | 0.02595985 | 6.210492173 | 6.267718 | 5.789702 | 5.702912 | 9.212855 | 8.160956 | 8.424409 |
| PGM1 | 0.599237274 | 0.05639214 | 0.042979925 | 6.205034262 | 5.304463 | 4.351315 | 3.764125 | 7.937902 | 7.107836 | 5.634184 |
| GPD1L | 0.810753051 | 0.045237293 | 0.021335829 | 6.200469805 | 1.874444 | 2.406905 | 2.165421 | 6.960054 | 4.797798 | 4.476242 |
| LOC100507632 | 0.789061705 | 0.045529634 | 0.022690031 | 6.200469805 | 1.874444 | 2.023048 | 2.165421 | 4.739845 | 4.797798 | 4.476242 |
| MMS22L | 0.734010545 | 0.047307334 | 0.026788704 | 6.200469805 | 2.201691 | 2.023048 | 2.165421 | 4.013424 | 4.797798 | 5.900694 |
| THAP10 | 0.725477305 | 0.047551011 | 0.027461041 | 6.200469805 | 1.874444 | 2.023048 | 2.165421 | 5.095353 | 4.797798 | 4.146207 |
| PHGR1 | 0.679287337 | 0.049531477 | 0.031707383 | 6.200469805 | 1.874444 | 2.023048 | 2.165421 | 7.243046 | 4.797798 | 3.630092 |
| COMMD10 | 0.631234294 | 0.053124771 | 0.0378918 | 6.200469805 | 1.874444 | 2.809601 | 2.165421 | 8.239009 | 4.797798 | 2.921909 |
| LOC100306975 | 0.628967889 | 0.053255542 | 0.038225927 | 6.200469805 | 2.993831 | 2.023048 | 2.165421 | 6.395481 | 4.797798 | 3.676349 |
| RAB20 | 0.623340081 | 0.053779735 | 0.038988772 | 6.200469805 | 2.201691 | 2.023048 | 2.165421 | 6.811341 | 4.797798 | 2.921909 |
| SAMD12 | 0.622886223 | 0.053781042 | 0.039050698 | 6.200469805 | 1.874444 | 2.406905 | 2.165421 | 6.960054 | 4.797798 | 2.921909 |
| YME1L1 | 0.707759655 | 0.048268527 | 0.029028241 | 6.200217736 | 8.183076 | 7.0583 | 7.519866 | 10.538507 | 10.260704 | 9.690619 |
| C12orf23 | 0.586249836 | 0.05781824 | 0.045292957 | 6.197431708 | 5.491121 | 4.389936 | 5.225216 | 7.856887 | 8.533804 | 5.900694 |
| KIAA0430 | 0.799977127 | 0.045434942 | 0.022038108 | 6.194682883 | 5.263699 | 2.809601 | 5.217616 | 7.42265 | 7.89473 | 7.695565 |
| NR4A3 | 0.671300675 | 0.05002854 | 0.032579789 | 6.192430988 | 6.973646 | 6.391145 | 7.746525 | 9.02165 | 9.198885 | 10.75629 |
| KAT6B | 0.67240424 | 0.049938578 | 0.032457979 | 6.191837919 | 5.744513 | 4.389936 | 5.592916 | 8.711848 | 7.819723 | 7.020304 |
| SH3BP5 | 0.739196023 | 0.04712834 | 0.026457298 | 6.182635673 | 6.678389 | 6.060401 | 6.704285 | 8.688623 | 9.500541 | 9.1113234 |
| PSME4 | 0.723918014 | 0.047585406 | 0.027557673 | 6.176140084 | 6.58615 | 6.03611 | 5.592916 | 9.212855 | 8.486085 | 8.374509 |
| C10orf137 | 0.771626799 | 0.046066162 | 0.023965975 | 6.171850359 | 2.201691 | 3.770995 | 3.764125 | 6.396698 | 6.189775 | 5.882028 |
| SLC38A9 | 0.803247556 | 0.045338539 | 0.021835318 | 6.169874574 | 2.201691 | 2.023048 | 2.165421 | 5.705318 | 4.539173 | 4.790662 |
| LY75 | 0.746199097 | 0.046831501 | 0.021835318 | 6.169874574 | 1.874444 | 2.809601 | 2.165421 | 4.718672 | 5.317867 | 4.790662 |
| ST3GAL6 | 0.732745297 | 0.047310912 | 0.026930028 | 6.169874574 | 1.874444 | 2.023048 | 2.165421 | 4.739845 | 4.131418 | 4.790662 |
| SORCS1 | 0.731293144 | 0.047384624 | 0.027029602 | 6.169874574 | 1.874444 | 2.023048 | 2.165421 | 4.718672 | 4.131418 | 4.790662 |
| ATP6V1G2 | 0.731293144 | 0.047384624 | 0.027029602 | 6.169874574 | 1.874444 | 2.023048 | 2.165421 | 4.718672 | 4.131418 | 4.790662 |
| ZCCHC7 | 0.689604371 | 0.048997321 | 0.030667574 | 6.169874574 | 4.209882 | 2.023048 | 2.165421 | 6.395481 | 5.936219 | 4.790662 |
| LOXL4 | 0.643914313 | 0.05192151 | 0.036039469 | 6.169874574 | 1.874444 | 2.023048 | 2.165421 | 4.718672 | 3.571326 | 4.790662 |
| PDCD10 | 0.622790976 | 0.053781042 | 0.039076557 | 6.169874574 | 2.201691 | 4.80797 | 2.165421 | 6.063041 | 6.189775 | 4.790662 |
| LRP2 | 0.613359747 | 0.054636493 | 0.040389929 | 6.169874574 | 3.024504 | 5.809601 | 2.165421 | 8.033165 | 6.78473 | 4.790662 |
| CEP128 | 0.580950678 | 0.058713636 | 0.046551888 | 6.169874574 | 1.874444 | 2.023048 | 2.165421 | 4.718672 | 3.134528 | 4.790662 |
| SLITRK2 | 0.580950678 | 0.058713636 | 0.046551888 | 6.169874574 | 1.874444 | 2.023048 | 2.165421 | 4.718672 | 3.134528 | 4.790662 |
| PRR15 | 0.580950678 | 0.058713636 | 0.046551888 | 6.169874574 | 1.874444 | 2.023048 | 2.165421 | 4.718672 | 3.134528 | 4.790662 |

TABLE 8-continued

Differentially Expressed Genes in CD10–, CD24–, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| MS4A10 | 0.566973128 | 0.060860764 | 0.049593059 | 6.169874574 | 1.874444 | 3.770995 | 2.165421 | 4.718672 | 4.797798 | 4.790662 |
| HAUS7 | 0.704638232 | 0.048398142 | 0.029365771 | 6.166945962 | 1.874444 | 4.413323 | 3.935222 | 7.037879 | 5.936219 | 5.900694 |
| UBE2E2 | 0.644630089 | 0.051758104 | 0.035673358 | 6.165717833 | 6.099991 | 4.80797 | 4.449894 | 7.074163 | 8.011679 | 7.640338 |
| FBXO42 | 0.672918528 | 0.049933984 | 0.03237904 | 6.153428226 | 5.056948 | 4.389936 | 3.764125 | 7.074163 | 7.174648 | 6.385515 |
| GREM2 | 0.746388815 | 0.046811314 | 0.025929228 | 6.147729224 | 1.874444 | 2.406905 | 2.995681 | 5.026959 | 6.608026 | 4.476242 |
| TRAPPC4 | 0.712375839 | 0.047984994 | 0.0285267 | 6.147729224 | 3.024504 | 2.406905 | 2.165421 | 5.026959 | 5.920411 | 4.562324 |
| TRIM35 | 0.699310759 | 0.048734593 | 0.029933311 | 6.144287498 | 6.949166 | 5.661685 | 6.031658 | 8.527804 | 9.128102 | 8.650903 |
| RAP2A | 0.592278803 | 0.057117807 | 0.044140864 | 6.138671976 | 5.856559 | 3.32135 | 5.544653 | 8.474485 | 7.767462 | 6.106561 |
| HSD17B7 | 0.758373148 | 0.046395081 | 0.024941817 | 6.133154875 | 2.201691 | 2.809601 | 2.379345 | 5.095353 | 4.797798 | 5.426231 |
| PRPF38B | 0.722189064 | 0.047646206 | 0.027719633 | 6.130013613 | 6.417969 | 6.732825 | 7.030042 | 9.733347 | 9.348715 | 8.79697 |
| ULK3 | 0.749737816 | 0.046675232 | 0.025610071 | 6.128218609 | 4.815804 | 2.406905 | 3.935222 | 6.550689 | 6.549959 | 6.931222 |
| UBE2D3 | 0.713478308 | 0.047910176 | 0.02841919 | 6.122541332 | 8.028068 | 7.547799 | 8.659978 | 11.633951 | 10.523584 | 10.161929 |
| SAAL1 | 0.576950706 | 0.059162429 | 0.047291596 | 6.112848079 | 4.309025 | 2.809601 | 3.324375 | 6.954147 | 5.936219 | 4.562324 |
| CLPTM1L | 0.72293872 | 0.04762218 | 0.027653624 | 6.110404087 | 5.056948 | 5.789702 | 3.764125 | 7.976765 | 7.31791 | 7.668215 |
| NEDD1 | 0.63932846 | 0.052350016 | 0.036669616 | 6.102397887 | 3.024504 | 2.809601 | 3.764125 | 6.063041 | 6.373501 | 4.562324 |
| MIR3654 | 0.569651195 | 0.060367121 | 0.048971079 | 6.102397887 | 3.839948 | 6.03611 | 3.764125 | 7.42265 | 6.373501 | 6.73963 |
| GSPT1 | 0.641873024 | 0.052014843 | 0.03627016 | 6.101961302 | 6.227577 | 6.983552 | 6.282905 | 11.101397 | 8.892178 | 7.695565 |
| USP53 | 0.73272147 | 0.047310912 | 0.026916638 | 6.100229584 | 5.491121 | 6.638536 | 5.571599 | 9.08528 | 9.2474 | 7.774634 |
| SBNO2 | 0.68502202 | 0.04931773 | 0.031172508 | 6.096581054 | 5.856559 | 5.43468 | 5.592916 | 8.579223 | 8.200916 | 7.46072 |
| HSPB8 | 0.707660141 | 0.048268527 | 0.029035046 | 6.094578281 | 3.839948 | 5.661685 | 6.072169 | 7.450526 | 8.277663 | 8.269212 |
| MATR3 | 0.738742593 | 0.04712834 | 0.026496768 | 6.094130153 | 7.463005 | 7.0089 | 7.884888 | 10.492308 | 10.471437 | 9.478651 |
| CHD1 | 0.64011702 | 0.052240009 | 0.036558013 | 6.09238336 | 6.267718 | 7.440099 | 8.775186 | 9.794456 | 10.047106 | 10.256805 |
| SETD3 | 0.722273843 | 0.047646206 | 0.027706022 | 6.092276597 | 4.209882 | 4.413323 | 6.395481 | 6.814118 | 6.043524 | 7.020304 |
| CXorf38 | 0.686245117 | 0.049293152 | 0.031028241 | 6.080696513 | 4.209882 | 4.80797 | 5.571599 | 8.2398 | 6.373501 | 7.36177 |
| C16orf42 | 0.726677653 | 0.047532676 | 0.027390269 | 6.073407682 | 4.639409 | 3.770995 | 3.764125 | 6.339437 | 6.373501 | 7.611911 |
| PPP1R3E | 0.621803794 | 0.05388098 | 0.039241239 | 6.073407682 | 4.682076 | 3.770995 | 5.702912 | 7.582358 | 7.819723 | 7.492252 |
| XPO6 | 0.64679371 | 0.051706895 | 0.035359742 | 6.071729159 | 6.648293 | 5.466258 | 5.217616 | 8.665019 | 7.819723 | 9.329475 |
| MYB | 0.799367566 | 0.045351572 | 0.022062606 | 6.070427587 | 2.406905 | 2.406905 | 2.379345 | 8.553743 | 4.608763 | 4.476242 |
| MS4A1 | 0.794188762 | 0.04542938 | 0.022395373 | 6.070427587 | 1.874444 | 2.023048 | 2.165421 | 5.743334 | 4.539173 | 4.476242 |
| LOC100507651 | 0.791877862 | 0.045479433 | 0.022556652 | 6.070427587 | 1.874444 | 2.023048 | 2.165421 | 5.252045 | 4.608763 | 4.476242 |
| PKHD1 | 0.791877862 | 0.045479433 | 0.022556652 | 6.070427587 | 1.874444 | 2.023048 | 2.165421 | 5.252045 | 4.608763 | 4.476242 |
| TMEM117 | 0.785648524 | 0.045624536 | 0.02291868 | 6.070427587 | 1.874444 | 2.023048 | 2.165421 | 5.026959 | 4.608763 | 4.476242 |
| TTC8 | 0.784940642 | 0.045655746 | 0.022985369 | 6.070427587 | 1.874444 | 2.023048 | 2.165421 | 5.320955 | 4.539173 | 4.476242 |
| LOC100130231 | 0.783263733 | 0.045695042 | 0.023077918 | 6.070427587 | 1.874444 | 2.023048 | 2.165421 | 5.252045 | 4.539173 | 4.476242 |
| LOC148824 | 0.772954975 | 0.046036363 | 0.023855733 | 6.070427587 | 1.874444 | 2.023048 | 2.165421 | 4.894482 | 4.539173 | 4.476242 |
| SERPINA5 | 0.767359794 | 0.046164489 | 0.024336169 | 6.070427587 | 1.874444 | 2.023048 | 2.165421 | 6.244586 | 4.539173 | 4.476242 |
| LOC399708 | 0.716773255 | 0.047841399 | 0.028203471 | 6.070427587 | 1.874444 | 3.32135 | 2.165421 | 5.252045 | 5.857745 | 4.476242 |
| PLCE1 | 0.700930208 | 0.04866899 | 0.02978428 | 6.070427587 | 1.874444 | 2.023048 | 3.935222 | 5.705318 | 6.205902 | 4.476242 |
| LOC730102 | 0.648580539 | 0.051579258 | 0.035263015 | 6.070427587 | 1.874444 | 2.023048 | 4.285996 | 5.320955 | 6.608026 | 4.476242 |
| CREG1 | 0.622962184 | 0.053781042 | 0.039021436 | 6.06973273 | 7.6108 | 5.789702 | 6.410545 | 9.388882 | 9.218487 | 8.391335 |
| RNF111 | 0.606547346 | 0.055460008 | 0.041578088 | 6.058809683 | 4.263463 | 3.770995 | 4.508334 | 5.320955 | 6.861783 | 7.46072 |
| PHF3 | 0.711095397 | 0.048062795 | 0.028677101 | 6.050338806 | 6.820119 | 5.362142 | 6.282905 | 8.514658 | 8.87992 | 8.906373 |
| CROT | 0.721799242 | 0.047650501 | 0.027752297 | 6.049691902 | 5.056948 | 5.297868 | 4.508334 | 7.177844 | 7.89473 | 7.46072 |
| NSD1 | 0.685638365 | 0.049314432 | 0.031113984 | 6.049691902 | 5.263509 | 5.297868 | 3.90836 | 7.074163 | 7.89473 | 7.218312 |
| MTFMT | 0.644864473 | 0.051844669 | 0.035921742 | 6.047784881 | 6.099991 | 6.184248 | 5.389265 | 7.25991 | 8.696398 | 9.182543 |
| LOC100507547 | 0.717768269 | 0.047825499 | 0.028125213 | 6.046530874 | 2.993831 | 2.406905 | 2.165421 | 5.891233 | 4.797798 | 4.146207 |
| AMMECR1 | 0.712692645 | 0.047957459 | 0.031113984 | 6.046229889 | 4.815804 | 4.413323 | 3.324375 | 4.802615 | 5.920411 | 5.874974 |
| RFC5 | 0.651676868 | 0.051348633 | 0.034869684 | 6.046229889 | 2.201691 | 2.406905 | 3.324375 | 7.450526 | 5.920411 | 6.722123 |
| TWISTNB | 0.720680766 | 0.047703746 | 0.027842123 | 6.039824233 | 5.856559 | 5.195784 | 5.225216 | 8.665019 | 7.819723 | 7.611911 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| FAM208B | 0.698379335 | 0.048774753 | 0.030019735 | 6.034305046 | 5.263699 | 5.195784 | 5.702912 | 7.856887 | 8.332658 | 7.395512 |
| RBM7 | 0.602306335 | 0.055983853 | 0.042340932 | 6.029656857 | 4.743564 | 2.809601 | 6.282905 | 7.33564 | 7.56803 | 6.649696 |
| RNF19B | 0.743501271 | 0.046889341 | 0.026097993 | 6.019084747 | 5.328826 | 5.789702 | 5.592916 | 7.918071 | 7.96603 | 8.60836 |
| LOC728743 | 0.72890928 | 0.047423411 | 0.027201089 | 6.007240436 | 2.993831 | 2.406905 | 2.379345 | 5.448591 | 4.608763 | 5.580533 |
| TTC39B | 0.793923005 | 0.04542938 | 0.022406261 | 6.003132932 | 1.874444 | 2.023048 | 2.165421 | 4.341916 | 4.608763 | 6.195186 |
| FGF14 | 0.782165744 | 0.045708444 | 0.023176591 | 6.003132932 | 1.874444 | 2.023048 | 2.165421 | 4.341916 | 4.608763 | 5.634184 |
| G6PC2 | 0.77718423 | 0.045858868 | 0.023525009 | 6.003132932 | 1.874444 | 2.023048 | 2.165421 | 4.341916 | 4.608763 | 5.426231 |
| RMND1 | 0.774093763 | 0.046000938 | 0.023805376 | 6.003132932 | 1.874444 | 2.023048 | 2.165421 | 4.739845 | 4.608763 | 4.476242 |
| LRRC34 | 0.774093763 | 0.046000938 | 0.023805376 | 6.003132932 | 1.874444 | 2.023048 | 2.165421 | 4.739845 | 4.608763 | 4.476242 |
| KBTBD3 | 0.735795927 | 0.047251954 | 0.022668867 | 6.003132932 | 1.874444 | 2.023048 | 2.165421 | 5.026959 | 4.608763 | 4.146207 |
| AMY2B | 0.706730325 | 0.048309794 | 0.029122831 | 6.003132932 | 1.874444 | 2.023048 | 2.165421 | 6.396698 | 4.608763 | 3.630092 |
| DPY19L2P1 | 0.706696085 | 0.048309794 | 0.029129636 | 6.003132932 | 1.874444 | 2.023048 | 2.165421 | 6.395481 | 4.608763 | 3.630092 |
| BBOX1 | 0.703502776 | 0.048494719 | 0.029504593 | 6.003132932 | 1.874444 | 2.023048 | 2.165421 | 6.283686 | 4.608763 | 3.630092 |
| TOR3A | 0.6871121 | 0.04915291 | 0.030889418 | 6.003132932 | 1.874444 | 2.023048 | 2.165421 | 5.579836 | 4.608763 | 3.676349 |
| RALGPS1 | 0.685158463 | 0.049314432 | 0.031154815 | 6.003132932 | 1.874444 | 2.023048 | 2.165421 | 5.705318 | 4.608763 | 3.630092 |
| FER | 0.674172074 | 0.049879314 | 0.032269479 | 6.003132932 | 3.350997 | 2.023048 | 2.165421 | 6.395481 | 4.608763 | 5.091834 |
| TMEM155 | 0.657802063 | 0.050866557 | 0.03406737 | 6.003132932 | 1.874444 | 2.023048 | 2.165421 | 4.894482 | 4.608763 | 3.676349 |
| FER1L6 | 0.657549253 | 0.050890262 | 0.034099354 | 6.003132932 | 1.874444 | 2.023048 | 2.165421 | 5.026959 | 4.608763 | 3.630092 |
| SLC35D2 | 0.648662627 | 0.051564319 | 0.035237836 | 6.003132932 | 1.874444 | 2.023048 | 2.165421 | 7.30543 | 4.608763 | 2.921909 |
| IL12A | 0.646078574 | 0.051811216 | 0.03574277 | 6.003132932 | 1.874444 | 2.023048 | 3.324375 | 5.320955 | 4.608763 | 4.562324 |
| MSTO2P | 0.645893653 | 0.05181797 | 0.035778836 | 6.003132932 | 1.874444 | 2.023048 | 2.165421 | 4.802615 | 4.608763 | 3.630092 |
| HSP90AB4P | 0.645893653 | 0.05181797 | 0.035778836 | 6.003132932 | 1.874444 | 2.023048 | 2.165421 | 4.802615 | 4.608763 | 3.630092 |
| NMNAT3 | 0.613271733 | 0.054662138 | 0.040434842 | 6.003132932 | 1.874444 | 2.023048 | 2.165421 | 6.244586 | 4.608763 | 2.921909 |
| GRTP1 | 0.611635505 | 0.054824023 | 0.040630827 | 6.003132932 | 4.815804 | 2.023048 | 2.165421 | 6.339437 | 4.608763 | 5.900694 |
| LYPD6 | 0.610938485 | 0.054913436 | 0.040749234 | 6.003132932 | 1.874444 | 2.023048 | 2.165421 | 6.183122 | 4.608763 | 2.921909 |
| C1orf168 | 0.606446728 | 0.055460008 | 0.041584893 | 6.003132932 | 1.874444 | 2.023048 | 2.165421 | 6.067497 | 4.608763 | 2.921909 |
| DYX1C1 | 0.599324182 | 0.056384204 | 0.042964954 | 6.003132932 | 1.874444 | 2.023048 | 2.165421 | 5.891233 | 4.608763 | 2.921909 |
| HS6ST2 | 0.596655057 | 0.056634604 | 0.043390949 | 6.003132932 | 1.874444 | 2.023048 | 2.165421 | 6.283686 | 4.608763 | 2.921909 |
| C15orf41 | 0.593068783 | 0.057053082 | 0.04397346 | 6.003132932 | 1.874444 | 2.023048 | 2.379345 | 5.743334 | 4.608763 | 2.921909 |
| NEK11 | 0.591416681 | 0.057236297 | 0.044338891 | 6.003132932 | 1.874444 | 2.023048 | 2.165421 | 5.705318 | 4.608763 | 2.921909 |
| UGT2B15 | 0.591416681 | 0.057236297 | 0.044338891 | 6.003132932 | 1.874444 | 2.023048 | 2.165421 | 5.705318 | 4.608763 | 2.921909 |
| RGS22 | 0.586043541 | 0.057869242 | 0.045371895 | 6.003132932 | 1.874444 | 2.023048 | 2.165421 | 6.283686 | 4.608763 | 5.874974 |
| GPR137C | 0.585826717 | 0.057927026 | 0.045451514 | 6.003132932 | 1.874444 | 2.023048 | 2.165421 | 5.579836 | 4.608763 | 2.921909 |
| TEX11 | 0.579740941 | 0.058818437 | 0.046805036 | 6.003132932 | 1.874444 | 2.023048 | 2.165421 | 5.448591 | 4.608763 | 2.921909 |
| ZNF174 | 0.573567715 | 0.059795609 | 0.048145628 | 6.003132932 | 1.874444 | 2.023048 | 2.165421 | 5.320955 | 4.608763 | 2.921909 |
| STX19 | 0.573567715 | 0.059795609 | 0.048145628 | 6.003132932 | 1.874444 | 2.023048 | 2.165421 | 5.320955 | 4.608763 | 2.921909 |
| JAKMIP3 | 0.570122628 | 0.06033194 | 0.048881252 | 6.003132932 | 1.874444 | 2.023048 | 2.165421 | 5.252045 | 4.608763 | 2.921909 |
| MORN4 | 0.716966686 | 0.047841399 | 0.028183055 | 6.001082393 | 3.350997 | 2.023048 | 2.379345 | 4.718672 | 5.936219 | 5.874974 |
| SCMH1 | 0.682122182 | 0.049418096 | 0.028613457 | 6.001082393 | 3.350997 | 2.809601 | 2.165421 | 5.705318 | 5.936219 | 5.634184 |
| IDH1 | 0.628930644 | 0.053255542 | 0.038239537 | 6.001082393 | 3.350997 | 3.32135 | 4.754917 | 2.820813 | 4.608763 | 5.426231 |
| PSRC1 | 0.594989078 | 0.056818692 | 0.043610752 | 5.999541211 | 1.874444 | 2.023048 | 2.995681 | 7.074163 | 5.936219 | 5.580533 |
| MYCL1 | 0.570018369 | 0.06033194 | 0.048916638 | 5.999541211 | 1.874444 | 3.32135 | 2.995681 | 4.718672 | 3.571326 | 5.580533 |
| CALM1 | 0.725328255 | 0.047551011 | 0.027474651 | 5.997499245 | 8.705736 | 8.288855 | 9.015087 | 10.873216 | 11.373865 | 11.373125 |
| GYPC | 0.565125401 | 0.061148989 | 0.049953726 | 5.992474504 | 7.218633 | 4.830496 | 5.544653 | 7.556937 | 7.473335 | 9.801784 |
| SRSF3 | 0.695567999 | 0.048858998 | 0.030239537 | 5.992052519 | 9.071674 | 8.288855 | 8.089553 | 11.341819 | 10.871906 | 10.713441 |
| SLC19A2 | 0.713100849 | 0.047923769 | 0.028448452 | 5.98572237 | 7.04469 | 6.184248 | 7.462086 | 10.043611 | 9.1177 | 9.430619 |
| RDX | 0.714447662 | 0.047789236 | 0.028369513 | 5.983644174 | 6.008206 | 4.830496 | 4.724406 | 7.30543 | 7.91889 | 8.357484 |
| LOC100129361 | 0.784601478 | 0.045655746 | 0.022998979 | 5.979009001 | 4.682076 | 4.351315 | 2.995681 | 7.167419 | 6.774676 | 6.931222 |
| IGSF8 | 0.691075165 | 0.048955004 | 0.030579109 | 5.976678835 | 4.963444 | 3.32135 | 3.764125 | 6.960054 | 7.191402 | 5.900694 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| HDDC3 | 0.624785838 | 0.053620377 | 0.03879687 | 5.976678835 | 4.815804 | 3.32135 | 2.379345 | 7.25991 | 5.165949 | 5.900694 |
| PLA2G15 | 0.61080131 | 0.054914277 | 0.040771011 | 5.976678835 | 4.209882 | 3.32135 | 2.379345 | 5.095353 | 5.920411 | 5.900694 |
| AP4B1 | 0.728947163 | 0.047423411 | 0.027187479 | 5.971353843 | 5.753024 | 5.148082 | 5.609945 | 7.726141 | 7.989035 | 8.488368 |
| CLK1 | 0.67499159 | 0.04982684 | 0.032180333 | 5.969034457 | 8.467946 | 8.407985 | 9.44112 | 11.922288 | 12.018618 | 10.256805 |
| RAB27A | 0.747093406 | 0.046789913 | 0.025835318 | 5.966471036 | 6.099991 | 5.340619 | 5.609945 | 8.676869 | 8.140553 | 8.11568 |
| NSUN4 | 0.685861268 | 0.049293152 | 0.031066349 | 5.96495681 | 5.700376 | 4.750708 | 4.449894 | 7.30543 | 7.740604 | 7.327219 |
| SNAP47 | 0.697199462 | 0.04881728 | 0.030123171 | 5.9641631 | 3.024504 | 2.023048 | 3.324375 | 4.894482 | 5.353925 | 5.900694 |
| ARHGAP12 | 0.675983849 | 0.049752474 | 0.032085063 | 5.961115945 | 3.819732 | 3.360637 | 2.165421 | 7.531061 | 5.936219 | 4.476242 |
| AJUBA | 0.699902104 | 0.048716465 | 0.029860497 | 5.960002356 | 3.024504 | 3.872014 | 3.764125 | 6.339437 | 6.613395 | 5.426231 |
| LSG1 | 0.693405707 | 0.048932925 | 0.030387207 | 5.959425446 | 6.099991 | 6.732825 | 7.003286 | 8.875048 | 9.578459 | 8.84662 |
| C5orf38 | 0.738526765 | 0.047133227 | 0.026517183 | 5.956333696 | 3.024504 | 2.406905 | 2.165421 | 4.739845 | 5.306419 | 5.446557 |
| WDR65 | 0.698410727 | 0.048774753 | 0.03001293 | 5.956333696 | 2.201691 | 2.023048 | 2.165421 | 4.739845 | 6.613395 | 3.630092 |
| LGR6 | 0.67787504 | 0.049640889 | 0.031879551 | 5.956333696 | 1.874444 | 2.809601 | 2.165421 | 4.739845 | 5.509998 | 4.146207 |
| TAF12 | 0.677000267 | 0.049712169 | 0.031965294 | 5.956333696 | 4.209882 | 3.360637 | 2.165421 | 4.739845 | 6.608026 | 6.722123 |
| AQP7P1 | 0.65932558 | 0.050730781 | 0.033872065 | 5.956333696 | 2.201691 | 2.023048 | 2.165421 | 4.739845 | 5.317867 | 3.676349 |
| EIF2S1 | 0.767368281 | 0.046164489 | 0.024329364 | 5.95344287 | 5.658609 | 6.03611 | 4.724406 | 8.014609 | 8.579995 | 8.232333 |
| CPSF1 | 0.689489128 | 0.049009935 | 0.030683226 | 5.952291484 | 6.054828 | 6.792427 | 6.410545 | 8.98399 | 8.200916 | 9.808064 |
| LSM3 | 0.697295217 | 0.04880813 | 0.030108881 | 5.950901869 | 5.304463 | 2.809601 | 3.324375 | 7.877571 | 7.656894 | 5.106393 |
| CLASP2 | 0.665584368 | 0.050369816 | 0.033208574 | 5.945003372 | 4.815804 | 5.195784 | 5.225216 | 6.814118 | 7.767462 | 7.800057 |
| PDP1 | 0.771021059 | 0.04607418 | 0.024033345 | 5.942861897 | 3.839948 | 4.389936 | 4.285996 | 6.857154 | 6.640094 | 6.924055 |
| LOC253039 | 0.638100126 | 0.05248745 | 0.036913916 | 5.938510303 | 6.381847 | 5.340619 | 5.571599 | 7.33564 | 8.951948 | 8.269212 |
| SLC37A4 | 0.673725749 | 0.049906853 | 0.03231099 | 5.937611447 | 3.024504 | 3.32135 | 2.165421 | 5.891233 | 5.306419 | 4.790662 |
| C5orf35 | 0.604699334 | 0.055669574 | 0.04181918 | 5.937611447 | 3.350997 | 3.32135 | 5.389265 | 5.891233 | 6.774676 | 6.587378 |
| MCTP1 | 0.603258657 | 0.055835227 | 0.042122491 | 5.937611447 | 1.874444 | 3.32135 | 3.935222 | 5.891233 | 4.131418 | 6.722123 |
| DDX20 | 0.654901491 | 0.051064299 | 0.034406941 | 5.935682232 | 3.350997 | 4.351315 | 2.995681 | 6.396698 | 5.920411 | 5.634184 |
| PADI2 | 0.629013999 | 0.053255542 | 0.038212317 | 5.926589534 | 4.263463 | 4.750708 | 4.944468 | 7.556937 | 7.31791 | 6.106561 |
| NOV | 0.757520231 | 0.046414887 | 0.024990813 | 5.925177523 | 2.993831 | 3.360637 | 5.225216 | 5.891233 | 5.306419 | 6.931222 |
| LTF | 0.590651369 | 0.057323276 | 0.044460701 | 5.920761027 | 3.819732 | 8.028729 | 3.90836 | 10.170577 | 8.055928 | 6.385515 |
| TRIM68 | 0.678975193 | 0.049548437 | 0.031733923 | 5.914231015 | 5.491121 | 3.770995 | 5.571599 | 7.167419 | 7.440337 | 8.135789 |
| MSH6 | 0.676849013 | 0.049712169 | 0.031999319 | 5.905854793 | 4.263463 | 2.809601 | 3.764125 | 5.320955 | 7.107836 | 6.32627 |
| ARSD | 0.703348717 | 0.048494719 | 0.029525009 | 5.904513307 | 6.186289 | 4.911517 | 3.90836 | 8.676869 | 7.473335 | 7.327219 |
| APOM | 0.727491772 | 0.047495226 | 0.02733719 | 5.899846122 | 2.993831 | 3.32135 | 2.379345 | 5.448591 | 5.165949 | 5.882028 |
| MAGT1 | 0.63896869 | 0.052399012 | 0.036735624 | 5.892189698 | 6.648293 | 5.661685 | 5.018694 | 8.376156 | 8.220489 | 7.873743 |
| USP9X | 0.77674678 | 0.045858868 | 0.023557644 | 5.887554248 | 6.554045 | 6.605686 | 6.800663 | 9.111713 | 9.158864 | 9.656224 |
| TIMM8B | 0.696031416 | 0.048858998 | 0.030210276 | 5.887491283 | 3.819732 | 4.389936 | 3.324375 | 6.283686 | 7.094585 | 5.882028 |
| SAP 18 | 0.703615866 | 0.048494719 | 0.029490983 | 5.879949428 | 7.6108 | 6.702075 | 7.295639 | 10.388031 | 9.673843 | 9.257878 |
| LOC100289019 | 0.589964562 | 0.057478449 | 0.044694794 | 5.878842455 | 3.839948 | 2.809601 | 2.165421 | 6.395481 | 4.131418 | 5.446557 |
| SLC16A1 | 0.632110702 | 0.05307838 | 0.037811501 | 5.87802434 | 3.024504 | 2.023048 | 4.754917 | 5.579836 | 6.549959 | 5.446557 |
| ZNF721 | 0.600240025 | 0.056344664 | 0.042805716 | 5.87802434 | 3.024504 | 4.389936 | 3.90836 | 5.579836 | 7.174648 | 5.580533 |
| SLC4A5 | 0.677629479 | 0.04967045 | 0.031914257 | 5.876079703 | 7.427999 | 7.174872 | 7.360327 | 8.915622 | 9.915181 | 10.8322 |
| GTDC1 | 0.655353963 | 0.051064299 | 0.034350459 | 5.871660196 | 3.819732 | 2.023048 | 2.379345 | 5.743334 | 6.373501 | 4.146207 |
| LOC285540 | 0.682575999 | 0.04941326 | 0.031423613 | 5.869556561 | 1.874444 | 2.406905 | 2.165421 | 4.718672 | 6.373501 | 3.630092 |
| IRAK4 | 0.659207363 | 0.050733231 | 0.033889758 | 5.869556561 | 3.350997 | 3.32135 | 2.165421 | 4.718672 | 6.205902 | 5.446557 |
| GOLGA7B | 0.648040779 | 0.051631895 | 0.035365771 | 5.869556561 | 1.874444 | 2.023048 | 2.165421 | 4.718672 | 4.608763 | 3.676349 |
| PHF19 | 0.730920509 | 0.047384624 | 0.02705342 | 5.858744494 | 3.819732 | 2.023048 | 3.324375 | 5.448591 | 6.189775 | 5.874974 |
| PDE3B | 0.717854869 | 0.0478155 | 0.028096632 | 5.858744494 | 1.874444 | 2.023048 | 4.754917 | 5.728038 | 4.131418 | 5.874974 |
| MPV17 | 0.644316027 | 0.051909408 | 0.035981626 | 5.858744494 | 5.328526 | 4.413323 | 3.324375 | 7.814607 | 7.191402 | 5.580533 |
| MYO5A | 0.635568338 | 0.05262489 | 0.037211977 | 5.858744494 | 4.682076 | 4.750708 | 3.324375 | 7.835902 | 6.608026 | 5.874974 |
| PDLIM5 | 0.641856744 | 0.052014843 | 0.036276965 | 5.856813917 | 7.530567 | 6.904719 | 6.369239 | 10.09751 | 8.549366 | 9.454835 |

TABLE 8-continued

Differentially Expressed Genes in CD10–, CD24–, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| YAP1 | 0.579821576 | 0.05881361 | 0.046782579 | 5.856245611 | 7.021395 | 6.572071 | 6.800663 | 9.571371 | 9.47632 | 7.920856 |
| PDK3 | 0.658664765 | 0.050764584 | 0.033929228 | 5.852465898 | 5.328526 | 3.770995 | 5.225216 | 7.877571 | 6.78473 | 7.218312 |
| SLC25A32 | 0.598012329 | 0.056497546 | 0.043185437 | 5.852124624 | 4.743564 | 4.413323 | 2.165421 | 5.026959 | 7.292524 | 6.69026 |
| MICAL1 | 0.777688262 | 0.045844227 | 0.023484859 | 5.849343305 | 3.819732 | 3.770995 | 3.764125 | 6.067497 | 6.319269 | 7.640338 |
| EEPD1 | 0.59251198 | 0.057110241 | 0.044089826 | 5.849343305 | 3.839948 | 3.770995 | 3.764125 | 5.026959 | 6.319269 | 6.649696 |
| C14orf105 | 0.732192824 | 0.047339553 | 0.026977884 | 5.844202729 | 4.209882 | 3.32135 | 3.90836 | 6.498222 | 6.189775 | 6.455366 |
| PBRM1 | 0.630499357 | 0.053156193 | 0.037997958 | 5.844202729 | 5.316227 | 3.32135 | 3.90836 | 6.252746 | 7.187136 | 6.455366 |
| IFI44L | 0.654697141 | 0.051064299 | 0.034434161 | 5.838819305 | 5.316227 | 4.389936 | 5.609945 | 7.274575 | 7.174648 | 8.155622 |
| NUAK1 | 0.775659009 | 0.045918659 | 0.023704661 | 5.838702945 | 6.846868 | 2.023048 | 7.519866 | 9.466036 | 9.392516 | 9.08248 |
| TBC1D23 | 0.683988787 | 0.049364239 | 0.031280027 | 5.838252633 | 6.008206 | 4.80797 | 4.724406 | 8.553743 | 7.656894 | 7.152205 |
| ANP32E | 0.673464155 | 0.049917775 | 0.032325961 | 5.828821825 | 5.753028 | 4.830496 | 6.175931 | 8.301578 | 8.296229 | 7.611911 |
| SAP30 | 0.634836195 | 0.05273953 | 0.037358285 | 5.823218787 | 3.350997 | 4.750708 | 6.072169 | 8.566539 | 7.292524 | 6.385515 |
| TDG | 0.71506089 | 0.047877006 | 0.028298061 | 5.821197424 | 5.056948 | 5.661685 | 4.754917 | 8.688623 | 7.598264 | 7.218312 |
| BBS10 | 0.626933241 | 0.053471909 | 0.038511739 | 5.816843156 | 3.350997 | 4.413323 | 2.379345 | 5.891233 | 6.613395 | 5.091834 |
| KLHL17 | 0.662920968 | 0.050504642 | 0.033471249 | 5.816121601 | 2.993831 | 3.360637 | 2.165421 | 5.579836 | 4.539173 | 5.900694 |
| TROAP | 0.768799847 | 0.046108296 | 0.024150391 | 5.81297314 | 1.874444 | 2.023048 | 2.165421 | 4.341916 | 5.306419 | 4.562324 |
| SAMD7 | 0.764944169 | 0.046181862 | 0.024492004 | 5.81297314 | 1.874444 | 2.023048 | 2.165421 | 4.341916 | 5.165949 | 4.562324 |
| CLEC4A | 0.76265668 | 0.046311565 | 0.024706363 | 5.81297314 | 1.874444 | 2.023048 | 2.165421 | 6.244586 | 4.131418 | 4.562324 |
| GRIA4 | 0.746521389 | 0.046800775 | 0.025886356 | 5.81297314 | 1.874444 | 2.023048 | 2.165421 | 4.013424 | 6.205902 | 4.562324 |
| ABCC8 | 0.719357866 | 0.047758583 | 0.028002722 | 5.81297314 | 1.874444 | 2.023048 | 2.165421 | 7.33564 | 3.571326 | 4.562324 |
| MED7 | 0.716660504 | 0.047853797 | 0.028225927 | 5.81297314 | 3.024504 | 2.023048 | 2.379345 | 4.739845 | 4.131418 | 4.562324 |
| MS4A6A | 0.685401815 | 0.049314432 | 0.031127594 | 5.81297314 | 1.874444 | 2.023048 | 2.165421 | 5.579836 | 4.797798 | 4.562324 |
| TAG | 0.679408784 | 0.049531477 | 0.031693773 | 5.81297314 | 1.874444 | 2.023048 | 2.165421 | 5.891233 | 3.571326 | 4.562324 |
| CGA | 0.676103313 | 0.049736329 | 0.032051038 | 5.81297314 | 2.993831 | 2.023048 | 2.165421 | 4.718672 | 5.165949 | 4.562324 |
| MED7 | 0.652242397 | 0.051304265 | 0.034800272 | 5.81297314 | 3.024504 | 2.023048 | 2.165421 | 4.802615 | 4.797798 | 4.562324 |
| PGF | 0.64601953 | 0.05181797 | 0.035768629 | 5.81297314 | 1.874444 | 2.023048 | 2.165421 | 5.252045 | 6.794431 | 4.562324 |
| ZNF707 | 0.645285504 | 0.051831344 | 0.035846887 | 5.81297314 | 1.874444 | 2.023048 | 2.165421 | 5.026959 | 3.571326 | 4.562324 |
| AIMP2 | 0.638675212 | 0.052436705 | 0.036811841 | 5.81297314 | 1.874444 | 2.023048 | 2.165421 | 4.894482 | 3.571326 | 4.562324 |
| ENO4 | 0.633763146 | 0.052882301 | 0.037512759 | 5.81297314 | 1.874444 | 2.023048 | 2.165421 | 4.802615 | 3.571326 | 4.562324 |
| EXTL2 | 0.617259269 | 0.054254364 | 0.039908132 | 5.81297314 | 1.874444 | 2.023048 | 2.165421 | 2.820813 | 6.794431 | 4.562324 |
| PDE6B | 0.604054866 | 0.055744926 | 0.042027901 | 5.81297314 | 1.874444 | 2.023048 | 2.165421 | 5.448591 | 3.134528 | 4.562324 |
| PDCD1LG2 | 0.595270371 | 0.056763192 | 0.043550187 | 5.81297314 | 1.874444 | 2.023048 | 2.165421 | 2.820813 | 6.189775 | 4.562324 |
| CASC1 | 0.587139369 | 0.057666624 | 0.045112623 | 5.81297314 | 1.874444 | 2.023048 | 2.165421 | 5.095353 | 3.134528 | 4.562324 |
| ZNF385D | 0.662126017 | 0.050577128 | 0.033602586 | 5.808455927 | 2.201691 | 2.406905 | 3.90836 | 4.739845 | 5.353925 | 6.195186 |
| CENPC1 | 0.617023127 | 0.054286282 | 0.039965975 | 5.797792991 | 3.819732 | 3.872014 | 4.724406 | 5.026959 | 6.608026 | 5.580533 |
| PRPF4B | 0.682997823 | 0.049394421 | 0.031354485 | 5.794615067 | 6.678389 | 6.311907 | 7.7303 | 9.739011 | 9.834907 | 8.84662 |
| NUP43 | 0.597896082 | 0.056511538 | 0.043214018 | 5.794270306 | 4.682076 | 3.872014 | 5.018694 | 5.728038 | 7.269549 | 7.553321 |
| C7orf70 | 0.646792008 | 0.051706895 | 0.035603947 | 5.789955904 | 3.839948 | 2.023048 | 2.995681 | 5.320955 | 6.373501 | 4.790662 |
| PSME1 | 0.579136251 | 0.058839456 | 0.046875128 | 5.778354991 | 8.977969 | 7.530398 | 7.295639 | 10.207812 | 9.828543 | 10.328455 |
| GPSM3 | 0.756359649 | 0.0464784 | 0.025133719 | 5.778103718 | 3.819732 | 3.360637 | 3.764125 | 5.891233 | 6.189775 | 7.03218 |
| LOC100628307 | 0.599759933 | 0.056344664 | 0.042872406 | 5.774356979 | 4.209882 | 4.413323 | 4.724406 | 5.728038 | 7.440337 | 6.942983 |
| CLEC4E | 0.608261984 | 0.055202948 | 0.041217421 | 5.769454624 | 6.554045 | 4.351315 | 8.199725 | 8.433162 | 9.608485 | 9.08248 |
| KCTD7 | 0.74996402 | 0.046675232 | 0.025616876 | 5.763485537 | 5.658609 | 5.43468 | 5.592916 | 7.748771 | 8.119857 | 8.771488 |
| BDP1 | 0.621328735 | 0.053905072 | 0.039303164 | 5.759666814 | 4.743564 | 4.736586 | 5.702912 | 8.41912 | 7.269549 | 6.649696 |
| MTMR11 | 0.749396644 | 0.04671806 | 0.025663151 | 5.75764856 | 4.743564 | 2.406905 | 4.508334 | 6.396698 | 7.25505 | 7.033813 |
| SLC22A15 | 0.703130467 | 0.048515004 | 0.02953359 | 5.751654222 | 3.350997 | 2.406905 | 2.165421 | 5.448591 | 4.539173 | 5.874974 |
| OTX2OS1 | 0.613854736 | 0.054598842 | 0.040342974 | 5.750506093 | 4.682076 | 4.830496 | 5.571599 | 6.395481 | 7.598264 | 8.095288 |
| GNPTAB | 0.61754354 | 0.054225734 | 0.039830555 | 5.749911688 | 6.381847 | 4.80797 | 5.225216 | 7.70315 | 7.819723 | 7.748756 |
| SPTAN1 | 0.635954497 | 0.052606547 | 0.037165703 | 5.744015408 | 5.779429 | 4.830496 | 6.355801 | 8.974419 | 8.033973 | 7.352555 |

TABLE 8-continued

Differentially Expressed Genes in CD10−, CD24−, CD44− Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| ATG4C | 0.648594687 | 0.051564319 | 0.035244641 | 5.741352919 | 4.682076 | 3.360637 | 3.764125 | 6.811341 | 6.319269 | 5.882028 |
| SSH3 | 0.696766505 | 0.048824537 | 0.030165362 | 5.736395398 | 1.874444 | 3.770995 | 3.935222 | 5.448591 | 5.936219 | 6.455366 |
| RSF1 | 0.648542826 | 0.051584246 | 0.035277305 | 5.731640456 | 6.008206 | 4.736586 | 5.225216 | 7.995811 | 7.845161 | 7.255535 |
| LOC100506123 | 0.680184513 | 0.049490097 | 0.031611432 | 5.731532735 | 5.658609 | 7.581983 | 6.601009 | 8.700282 | 10.100904 | 9.051056 |
| UBE2B | 0.693641309 | 0.048932925 | 0.030373596 | 5.730329324 | 8.096549 | 7.726519 | 8.448127 | 11.282943 | 10.615167 | 9.984774 |
| INTU | 0.623653848 | 0.053749228 | 0.038941136 | 5.729036137 | 2.993831 | 5.789702 | 6.489771 | 6.811341 | 7.819723 | 9.008063 |
| NPC2 | 0.711182688 | 0.048009392 | 0.028598843 | 5.728018429 | 6.554045 | 6.904719 | 7.204614 | 9.252991 | 9.909162 | 9.072081 |
| TRIM2 | 0.615372178 | 0.05441792 | 0.040123171 | 5.727474014 | 5.982974 | 4.413323 | 4.449894 | 7.631894 | 7.269549 | 6.931222 |
| AEBP2 | 0.61314741 | 0.054662138 | 0.040441647 | 5.726717113 | 5.056948 | 6.537655 | 6.031658 | 9.252991 | 8.549366 | 7.152205 |
| TBC1D9 | 0.733603476 | 0.047307334 | 0.026822729 | 5.725701724 | 5.779429 | 5.195784 | 5.723602 | 9.012327 | 7.713236 | 8.03232 |
| MANSC4 | 0.628223788 | 0.053354225 | 0.038362708 | 5.723833206 | 2.201691 | 2.023048 | 2.379345 | 4.718672 | 3.571326 | 5.446557 |
| C7orf31 | 0.617147803 | 0.054283162 | 0.039955087 | 5.723833206 | 2.201691 | 2.023048 | 3.324375 | 4.718672 | 4.131418 | 5.900694 |
| APBA2 | 0.622468819 | 0.053781042 | 0.039117387 | 5.720601948 | 2.993831 | 2.023048 | 3.935222 | 7.33564 | 5.509998 | 4.146207 |
| TACR1 | 0.720431747 | 0.047703746 | 0.027889758 | 5.720436921 | 1.874444 | 2.023048 | 2.165421 | 6.954147 | 4.539173 | 3.676349 |
| RXFP1 | 0.717039206 | 0.047840971 | 0.028165362 | 5.720436921 | 1.874444 | 2.023048 | 2.165421 | 4.739845 | 4.539173 | 4.146207 |
| GTPBP8 | 0.695921817 | 0.048858998 | 0.030225927 | 5.720436921 | 1.874444 | 2.023048 | 2.165421 | 6.244586 | 4.539173 | 3.630092 |
| ZEB1-AS1 | 0.685925214 | 0.049293152 | 0.031052739 | 5.720436921 | 1.874444 | 2.023048 | 2.165421 | 5.728038 | 4.539173 | 3.676349 |
| CEP170P1 | 0.669646167 | 0.050087347 | 0.03273018 | 5.720436921 | 1.874444 | 2.023048 | 2.165421 | 5.448591 | 4.539173 | 3.630092 |
| GPR160 | 0.664700217 | 0.050400851 | 0.033309969 | 5.720436921 | 1.874444 | 2.023048 | 2.165421 | 8.087444 | 4.539173 | 2.921909 |
| ITGA8 | 0.658150718 | 0.050826016 | 0.034 | 5.720436921 | 1.874444 | 2.023048 | 2.379345 | 5.705318 | 4.539173 | 3.630092 |
| LOC653786 | 0.65341886 | 0.051215566 | 0.034603607 | 5.720436921 | 1.874444 | 2.023048 | 2.379345 | 5.579836 | 4.539173 | 3.630092 |
| FIGN | 0.652448255 | 0.051266842 | 0.034749234 | 5.720436921 | 1.874444 | 2.023048 | 2.165421 | 4.894482 | 4.539173 | 3.676349 |
| SCLT1 | 0.652448255 | 0.051266842 | 0.034749234 | 5.720436921 | 1.874444 | 2.023048 | 2.165421 | 4.894482 | 4.539173 | 3.676349 |
| WFDC1 | 0.645575962 | 0.051818705 | 0.035820347 | 5.720436921 | 1.874444 | 2.023048 | 2.165421 | 4.894482 | 4.539173 | 3.630092 |
| PMS2P5 | 0.643975023 | 0.05192151 | 0.036032664 | 5.720436921 | 3.350997 | 2.023048 | 2.165421 | 5.026959 | 4.539173 | 5.091834 |
| LOC100128822 | 0.64078097 | 0.052144602 | 0.036433481 | 5.720436921 | 1.874444 | 2.023048 | 2.165421 | 4.802615 | 4.539173 | 3.630092 |
| HRASLS5 | 0.60918499 | 0.055155203 | 0.041111943 | 5.720436921 | 1.874444 | 2.023048 | 2.165421 | 6.283686 | 4.539173 | 2.921909 |
| C10orf90 | 0.607727238 | 0.05527432 | 0.041342634 | 5.720436921 | 1.874444 | 2.023048 | 2.165421 | 6.244586 | 4.539173 | 2.921909 |
| EIF2C3 | 0.60540701 | 0.055614955 | 0.04179789 | 5.720436921 | 1.874444 | 2.023048 | 2.165421 | 6.183122 | 4.539173 | 2.921909 |
| UBE2T | 0.600943485 | 0.05625006 | 0.042666894 | 5.720436921 | 1.874444 | 2.023048 | 2.165421 | 6.067497 | 4.539173 | 2.921909 |
| MAGEB3 | 0.593874258 | 0.056998407 | 0.043829874 | 5.720436921 | 1.874444 | 2.023048 | 2.165421 | 5.891233 | 4.539173 | 2.921909 |
| CDT1 | 0.58767426 | 0.057633938 | 0.045032324 | 5.720436921 | 1.874444 | 2.023048 | 2.165421 | 5.743334 | 4.539173 | 2.921909 |
| FLJ39080 | 0.586038106 | 0.057869242 | 0.0453787 | 5.720436921 | 1.874444 | 2.023048 | 2.165421 | 5.705318 | 4.539173 | 2.921909 |
| RRM2 | 0.568394348 | 0.060588284 | 0.049294318 | 5.716520029 | 4.743564 | 2.809601 | 2.995681 | 5.320955 | 4.539173 | 7.033813 |
| MIR137HG | 0.564995203 | 0.061169439 | 0.049989792 | 5.713270096 | 3.350997 | 4.750708 | 2.995681 | 5.252045 | 5.353925 | 6.051818 |
| CDH6 | 0.582697999 | 0.058324851 | 0.046095211 | 5.713270096 | 3.839948 | 3.872014 | 5.389265 | 4.894482 | 5.509998 | 5.634184 |
| CMTM8 | 0.64714969 | 0.05168843 | 0.035529772 | 5.710040895 | 5.744513 | 3.872014 | 2.995681 | 7.243046 | 5.509998 | 6.385515 |
| NEK4 | 0.63296368 | 0.052996828 | 0.037693093 | 5.709164592 | 8.224469 | 8.379112 | 8.26876 | 6.498222 | 7.627877 | 10.78204 |
| DNAJB9 | 0.638223427 | 0.052467325 | 0.036884655 | 5.708924963 | 6.054828 | 5.809601 | 4.944468 | 8.98399 | 10.487684 | 8.32282 |
| SLC25A5 | 0.741498962 | 0.046993264 | 0.026253147 | 5.701547947 | 1.874444 | 2.809601 | 4.724406 | 11.374934 | 8.764653 | 7.218312 |
| KCNE3 | 0.61041224 | 0.055028265 | 0.040886696 | 5.700992657 | 4.263463 | 3.872014 | 2.165421 | 6.857154 | 5.317867 | 5.634184 |
| NAB2 | 0.658024396 | 0.050865657 | 0.034046955 | 5.694030585 | 10.746681 | 11.243094 | 10.991078 | 5.320955 | 6.774676 | 13.534412 |
| SLC12A9 | 0.704407672 | 0.050866577 | 0.029380742 | 5.69385347 | 6.949166 | 6.184248 | 6.489771 | 6.244586 | 12.804939 | 8.858771 |
| RPL13AP3 | 0.667818478 | 0.05027915 | 0.032990813 | 5.68938534 | 6.267718 | 6.391145 | 6.489771 | 13.752544 | 8.998044 | 8.952456 |
| HDAC2 | 0.728960958 | 0.047423411 | 0.02780674 | 5.689385347 | 1.874444 | 2.809601 | 3.324375 | 9.452312 | 8.998044 | 4.476242 |
| NIPBL | 0.713814769 | 0.047910176 | 0.028839197 | 5.689355664 | 3.350997 | 2.023048 | 2.995681 | 8.488001 | 5.317867 | 5.106393 |
| NDUFB1 | 0.660656657 | 0.050667775 | 0.033725757 | 5.683374834 | 1.874444 | 2.809601 | 2.995681 | 5.728038 | 5.857745 | 8.579284 |
| TTC31 | 0.670700714 | 0.050060495 | 0.032673018 | 5.682983595 | 6.554045 | 6.072636 | 6.564874 | 4.894482 | 5.857745 | 5.106393 |
| PTPN12 | 0.723992986 | 0.047585406 | 0.027550868 | 5.682983595 | 6.554045 | 6.072636 | 6.564874 | 9.47285 | 8.829823 | 8.579284 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| AKIRIN1 | 0.695555547 | 0.048858998 | 0.030259952 | 5.682969265 | 6.58615 | 6.702075 | 6.800663 | 8.566539 | 9.20872 | 9.814317 |
| CSNK1G1 | 0.711384891 | 0.048031846 | 0.028627424 | 5.676861469 | 4.309025 | 2.809601 | 5.217616 | 6.814118 | 7.414086 | 6.587378 |
| GPBP1 | 0.732958879 | 0.047310912 | 0.026896223 | 5.667534511 | 7.355332 | 7.383076 | 8.114773 | 10.617494 | 10.329923 | 9.776388 |
| RNF8 | 0.684755574 | 0.049319443 | 0.031197006 | 5.665116747 | 4.815804 | 5.43468 | 4.285996 | 7.210813 | 7.31791 | 7.327219 |
| TFCP2 | 0.738047111 | 0.047140798 | 0.026546444 | 5.662687565 | 4.639409 | 3.872014 | 2.165421 | 6.954147 | 6.373501 | 6.195186 |
| NT2 | 0.732584071 | 0.047319258 | 0.026938414 | 5.660354322 | 5.316227 | 6.270596 | 6.031658 | 8.270632 | 8.385634 | 8.771488 |
| RARS2 | 0.644139643 | 0.05192151 | 0.036019054 | 5.655038827 | 3.819732 | 2.023048 | 3.764125 | 4.894482 | 6.319269 | 6.051818 |
| MARCH9 | 0.635884078 | 0.052606547 | 0.037172508 | 5.651889726 | 3.350997 | 5.340619 | 4.285996 | 6.252746 | 6.78473 | 7.352555 |
| NXNL2 | 0.691951187 | 0.048955004 | 0.030511058 | 5.651565974 | 7.177073 | 6.184248 | 6.83141 | 9.33006 | 10.29342 | 8.503924 |
| DNAJC16 | 0.748481951 | 0.046757859 | 0.025751616 | 5.64690479 | 4.639409 | 4.80797 | 2.995681 | 7.30543 | 7.107836 | 6.649696 |
| APAF1 | 0.662945673 | 0.050504642 | 0.033464444 | 5.64690479 | 5.335413 | 4.80797 | 5.596986 | 7.30543 | 7.406767 | 8.155622 |
| ANKRD28 | 0.679511578 | 0.049531477 | 0.031680163 | 5.643671184 | 5.304463 | 6.044198 | 4.944468 | 8.540832 | 8.033973 | 7.291822 |
| ZDHHC3 | 0.645166544 | 0.051833045 | 0.035875468 | 5.629821346 | 5.856559 | 4.830496 | 4.449894 | 7.918071 | 7.505595 | 6.942983 |
| ZCCHC8 | 0.640335197 | 0.052233632 | 0.036528751 | 5.615311659 | 5.304463 | 4.736586 | 4.944468 | 7.531061 | 7.793829 | 6.618407 |
| APC | 0.617971238 | 0.054171819 | 0.039735965 | 5.612640492 | 5.328526 | 3.872014 | 4.285996 | 6.814118 | 6.774676 | 6.69026 |
| CD53 | 0.711335106 | 0.048031846 | 0.028634229 | 5.611984491 | 4.743564 | 2.023048 | 5.544653 | 8.033165 | 7.187136 | 6.455366 |
| SCD5 | 0.670428918 | 0.050060495 | 0.032679823 | 5.610499142 | 5.328526 | 5.43468 | 4.754917 | 7.243046 | 8.277663 | 7.291822 |
| ING1 | 0.633169979 | 0.052977658 | 0.037654304 | 5.60839943 | 6.898923 | 6.092406 | 6.054038 | 8.069577 | 8.579995 | 9.462817 |
| KLHDC5 | 0.755305796 | 0.046505334 | 0.02523035 | 5.607719226 | 5.304463 | 4.830496 | 2.165421 | 7.33564 | 7.31791 | 7.180104 |
| DMAP1 | 0.606246624 | 0.055476612 | 0.041616876 | 5.607456519 | 6.48761 | 6.072636 | 2.995681 | 7.274575 | 7.414086 | 8.974957 |
| FBXO9 | 0.695826786 | 0.048858998 | 0.030232732 | 5.606612853 | 7.021395 | 7.34377 | 6.769247 | 9.058353 | 9.508524 | 9.945435 |
| TAGLN2 | 0.661080494 | 0.050645852 | 0.036695134 | 5.60037725 | 9.110831 | 8.436292 | 8.37695 | 10.557862 | 10.935471 | 11.596355 |
| C9orf156 | 0.638714067 | 0.05242235 | 0.036786662 | 5.599919931 | 4.309025 | 2.023048 | 3.935222 | 5.026959 | 6.794431 | 6.32627 |
| RALGAPA1 | 0.663460377 | 0.05046582 | 0.033416808 | 5.596939773 | 4.263463 | 5.195784 | 5.592916 | 7.36523 | 8.077554 | 7.03218 |
| ADH5 | 0.571992204 | 0.060047609 | 0.048474311 | 5.582745586 | 7.701538 | 5.789702 | 4.285996 | 8.270632 | 9.168974 | 7.722406 |
| XIAP | 0.757223896 | 0.060424242 | 0.025030963 | 5.578845229 | 6.765086 | 6.670655 | 5.609945 | 9.245052 | 9.086038 | 8.918033 |
| CTBP2 | 0.600035518 | 0.056344664 | 0.042830214 | 5.575509776 | 5.304463 | 5.340619 | 5.544658 | 8.527804 | 7.819723 | 6.649696 |
| SSR4 | 0.643796313 | 0.05192151 | 0.036057162 | 5.572491024 | 8.646058 | 7.494953 | 6.919905 | 9.973276 | 9.956624 | 10.384159 |
| SEPT8 | 0.626325172 | 0.053550098 | 0.038628785 | 5.569312009 | 6.52121 | 4.830496 | 5.609945 | 8.087444 | 7.767462 | 8.11568 |
| DNAJC10 | 0.628946276 | 0.053255542 | 0.038232732 | 5.566485664 | 5.316227 | 6.670655 | 4.724406 | 7.792994 | 7.56803 | 6.455366 |
| KRR1 | 0.623434717 | 0.053779735 | 0.038975162 | 5.564173424 | 4.263463 | 5.661685 | 5.544653 | 8.447068 | 7.56803 | 6.73963 |
| MRPS27 | 0.667757184 | 0.050304351 | 0.033022116 | 5.562389604 | 4.309025 | 5.297868 | 2.379345 | 6.283686 | 6.78473 | 7.180104 |
| BTF3 | 0.626472148 | 0.053550098 | 0.038597482 | 5.556441045 | 3.024504 | 3.360637 | 4.449894 | 5.320955 | 5.857745 | 6.924055 |
| ELF2 | 0.704909472 | 0.048378239 | 0.029315413 | 5.556256441 | 5.056948 | 4.750708 | 5.544653 | 7.531061 | 7.870158 | 7.36177 |
| MRPL47 | 0.708855224 | 0.048241159 | 0.028898265 | 5.554248025 | 4.263463 | 3.770995 | 3.324375 | 6.244586 | 6.373501 | 6.195186 |
| VPS13A | 0.675577189 | 0.049794345 | 0.032136781 | 5.547533404 | 3.024504 | 4.389936 | 3.324375 | 6.183122 | 6.861783 | 5.426231 |
| OSBP | 0.718653653 | 0.047781016 | 0.028055444 | 5.531311159 | 5.335413 | 3.872014 | 5.389265 | 7.856887 | 7.627877 | 7.218312 |
| USP49 | 0.643827528 | 0.05192151 | 0.036050357 | 5.531245015 | 5.982974 | 4.750708 | 3.324375 | 6.857154 | 7.793829 | 7.218312 |
| C8orf37 | 0.786698111 | 0.045564387 | 0.022829534 | 5.530741745 | 1.874444 | 2.023048 | 2.165421 | 4.341916 | 6.613395 | 4.476242 |
| CREBL2 | 0.633131893 | 0.052977658 | 0.037661109 | 5.529884629 | 4.743564 | 4.413323 | 5.974574 | 7.210813 | 8.36819 | 7.03218 |
| DENND1B | 0.649160617 | 0.047781016 | 0.035190201 | 5.528914934 | 5.335413 | 5.487673 | 5.389265 | 6.857154 | 7.191402 | 7.46072 |
| RBMS2 | 0.627368315 | 0.053451936 | 0.038480436 | 5.527416111 | 5.982974 | 4.80797 | 3.324375 | 7.274575 | 8.350533 | 8.858771 |
| MDH2 | 0.679327644 | 0.049531477 | 0.031700578 | 5.524372636 | 7.992569 | 7.711156 | 6.861515 | 10.45838 | 9.601037 | 9.945435 |
| MLLT3 | 0.636669322 | 0.052568146 | 0.037103777 | 5.523761898 | 4.309025 | 3.32135 | 5.389265 | 6.814118 | 6.774676 | 6.73963 |
| CCDC88A | 0.69268385 | 0.048944238 | 0.030434842 | 5.515128831 | 3.024504 | 4.750708 | 4.754917 | 6.244586 | 7.138979 | 7.218312 |
| AHCYL1 | 0.712229372 | 0.047984994 | 0.028547125 | 5.513438848 | 7.6108 | 6.184248 | 7.611303 | 9.5623 | 10.074256 | 9.776388 |
| FOXO3 | 0.644279538 | 0.051978194 | 0.036210276 | 5.512563395 | 7.744853 | 6.670655 | 8.024505 | 9.98762 | 10.735699 | 9.133378 |
| DCAF16 | 0.699860663 | 0.048730157 | 0.029884314 | 5.51204557 | 5.658609 | 6.060401 | 5.974145 | 7.70315 | 8.436733 | 9.389334 |
| PRKD3 | 0.639457533 | 0.052350016 | 0.03666281 | 5.511224544 | 4.815804 | 5.43468 | 6.072169 | 6.811341 | 8.453372 | 8.534542 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| LOC100289495 | 0.672661232 | 0.049933984 | 0.032406261 | 5.50983934 | 4.963444 | 4.830496 | 6.056062 | 7.109557 | 8.518072 | 7.873743 |
| PPIL3 | 0.723276503 | 0.04762218 | 0.027633209 | 5.509061175 | 5.658609 | 6.270596 | 5.702912 | 8.566539 | 7.989035 | 8.732403 |
| TACC2 | 0.658064146 | 0.050858744 | 0.034029942 | 5.508192901 | 5.056948 | 4.80797 | 4.285996 | 8.885299 | 7.269549 | 6.051818 |
| PARP8 | 0.705630956 | 0.048360255 | 0.029267098 | 5.504286553 | 5.744513 | 6.228068 | 6.527811 | 8.688623 | 8.36819 | 8.84662 |
| CCDC90A | 0.746900968 | 0.046798828 | 0.025855053 | 5.502639651 | 5.056948 | 2.809601 | 5.225216 | 7.167419 | 7.68534 | 7.255535 |
| IRF1 | 0.597495528 | 0.056551179 | 0.043264376 | 5.495128386 | 6.997718 | 7.87177 | 8.960487 | 10.362575 | 10.329923 | 9.968046 |
| MTR | 0.740357688 | 0.047053425 | 0.026345696 | 5.494089614 | 6.306772 | 3.32135 | 6.175931 | 8.239009 | 8.764653 | 8.175185 |
| QDPR | 0.720472503 | 0.047703746 | 0.027876148 | 5.48243198 | 4.309025 | 4.736586 | 4.944468 | 8.173604 | 7.191402 | 6.649696 |
| C2orf28 | 0.643115734 | 0.051942518 | 0.036136101 | 5.482271165 | 6.227577 | 5.362142 | 3.90836 | 7.477873 | 8.682351 | 7.152205 |
| MKI67IP | 0.649636931 | 0.0515003 | 0.03509493 | 5.47824303 | 5.491121 | 4.911517 | 4.508334 | 7.36523 | 7.406567 | 7.033813 |
| ZNF148 | 0.664336323 | 0.050408343 | 0.033297704 | 5.47794164 | 4.963444 | 3.872014 | 4.285996 | 6.067497 | 8.098861 | 6.73963 |
| PAX8 | 0.751976242 | 0.0466011 | 0.025495066 | 5.476271078 | 1.874444 | 2.023048 | 2.165421 | 6.183122 | 4.131418 | 4.476242 |
| SASS6 | 0.749312681 | 0.046728791 | 0.025699217 | 5.476271078 | 1.874444 | 2.023048 | 2.165421 | 6.067497 | 4.131418 | 4.476242 |
| LOC646471 | 0.733555618 | 0.047307334 | 0.026839741 | 5.476271078 | 1.874444 | 2.023048 | 2.165421 | 5.448591 | 4.131418 | 4.476242 |
| MDH1B | 0.733555618 | 0.047307334 | 0.026839741 | 5.476271078 | 1.874444 | 2.023048 | 2.165421 | 5.448591 | 4.131418 | 4.476242 |
| CLDN19 | 0.733386172 | 0.047307334 | 0.026856754 | 5.476271078 | 2.201691 | 2.023048 | 2.379345 | 5.095353 | 4.608763 | 4.476242 |
| UCP3 | 0.708091975 | 0.048268527 | 0.02898741 | 5.476271078 | 1.874444 | 2.023048 | 2.165421 | 4.013424 | 5.165949 | 4.476242 |
| SNORD81 | 0.685408689 | 0.049314432 | 0.031120789 | 5.476271078 | 1.874444 | 2.023048 | 2.165421 | 6.339437 | 3.571326 | 4.476242 |
| GLYATL1 | 0.655916457 | 0.050993826 | 0.033268118 | 5.476271078 | 1.874444 | 2.023048 | 2.165421 | 5.448591 | 3.571326 | 4.476242 |
| CRISP1 | 0.648118744 | 0.051631895 | 0.033358966 | 5.476271078 | 1.874444 | 2.023048 | 2.165421 | 5.252045 | 3.571326 | 4.476242 |
| CD1A | 0.638302053 | 0.052467325 | 0.036871045 | 5.476271078 | 1.874444 | 2.023048 | 2.165421 | 5.026959 | 3.571326 | 4.476242 |
| CDKL3 | 0.622732848 | 0.053781042 | 0.039083362 | 5.476271078 | 1.874444 | 2.023048 | 2.165421 | 4.718672 | 3.571326 | 4.476242 |
| ACOX2 | 0.615061766 | 0.054502508 | 0.040195985 | 5.476271078 | 2.201691 | 2.023048 | 4.724406 | 5.448591 | 7.138979 | 4.476242 |
| WDR5B | 0.61120033 | 0.054867364 | 0.040692753 | 5.476271078 | 4.209882 | 2.023048 | 3.324375 | 6.244586 | 6.373501 | 4.476242 |
| WNT10B | 0.608060098 | 0.055244379 | 0.041274583 | 5.476271078 | 1.874444 | 2.023048 | 2.165421 | 5.705318 | 3.134528 | 4.476242 |
| IFIH1 | 0.59370435 | 0.057040543 | 0.043936713 | 5.476271078 | 5.335413 | 2.023048 | 2.165421 | 7.109557 | 6.043524 | 4.476242 |
| C1orf204 | 0.565043745 | 0.061157134 | 0.049970058 | 5.476271078 | 1.874444 | 2.023048 | 2.165421 | 4.802615 | 3.134528 | 4.476242 |
| BMP8A | 0.638179804 | 0.052467325 | 0.03689146 | 5.475193258 | 1.874444 | 2.809601 | 2.995681 | 5.448591 | 4.797798 | 4.476242 |
| FBP1 | 0.68308866 | 0.049394421 | 0.031341273 | 5.474495763 | 2.993831 | 4.413323 | 3.764125 | 7.771052 | 6.205902 | 5.446557 |
| ZNF706 | 0.751989504 | 0.0466011 | 0.025488261 | 5.469676437 | 7.04469 | 7.0583 | 6.769247 | 9.4454 | 10.173004 | 9.220702 |
| LOC282980 | 0.589875248 | 0.057439458 | 0.044641715 | 5.467479334 | 1.874444 | 2.023048 | 2.995681 | 4.739845 | 3.571326 | 5.446557 |
| PEX13 | 0.71175857 | 0.048009392 | 0.028605648 | 5.465027325 | 4.209882 | 5.487673 | 4.285996 | 7.937902 | 7.53715 | 6.618407 |
| TAF1 | 0.721745384 | 0.047650501 | 0.027765907 | 5.455980803 | 4.743564 | 4.830496 | 4.449894 | 6.811341 | 7.191402 | 7.523109 |
| ANKZF1 | 0.742985759 | 0.046915454 | 0.026128615 | 5.45377576 | 4.309025 | 3.872014 | 3.90836 | 6.664985 | 6.319269 | 6.722123 |
| SCRN1 | 0.752102871 | 0.0466011 | 0.025474651 | 5.441882825 | 4.815804 | 4.80797 | 2.379345 | 7.25991 | 7.174648 | 6.722123 |
| FUS | 0.73358453 | 0.047307334 | 0.026829534 | 5.439262975 | 7.716122 | 7.0089 | 7.422239 | 9.452312 | 9.809281 | 11.35179 |
| ANKRD39 | 0.691873917 | 0.048955004 | 0.030517863 | 5.439004399 | 2.201691 | 2.023048 | 2.165421 | 4.718672 | 4.608763 | 4.146207 |
| C7orf65 | 0.68410552 | 0.049364239 | 0.031273222 | 5.439004399 | 1.874444 | 2.023048 | 2.165421 | 4.013424 | 4.608763 | 4.476242 |
| NDUFA2 | 0.6688089 | 0.048009392 | 0.028628879 | 5.439004399 | 1.874444 | 2.406905 | 2.165421 | 6.252746 | 4.608763 | 3.630092 |
| MPV17L | 0.625880611 | 0.0535411 | 0.03868867 | 5.439004399 | 3.024504 | 3.32135 | 2.165421 | 4.894482 | 4.608763 | 6.195186 |
| GLRB | 0.587496583 | 0.057633938 | 0.045039129 | 5.439004399 | 1.874444 | 2.406905 | 2.165421 | 6.395481 | 4.608763 | 2.921909 |
| KPNA7 | 0.565501659 | 0.060923671 | 0.049682885 | 5.439004399 | 2.201691 | 2.023048 | 2.165421 | 5.743334 | 4.608763 | 2.921909 |
| PSMC2 | 0.638697976 | 0.05242235 | 0.036793467 | 5.434043624 | 5.018694 | 6.072636 | 5.018694 | 9.212855 | 8.011679 | 7.46072 |
| CTR9 | 0.645131098 | 0.051833045 | 0.035882273 | 5.430404433 | 5.779429 | 5.661685 | 6.056062 | 7.477873 | 8.220489 | 8.84662 |
| DCP2 | 0.699304832 | 0.048734593 | 0.029940116 | 5.430325412 | 5.335413 | 4.911517 | 5.723602 | 8.069577 | 8.011679 | 7.352555 |
| THAP5 | 0.669462105 | 0.050101245 | 0.032753998 | 5.425403919 | 4.815804 | 4.750708 | 2.165421 | 6.063041 | 6.78473 | 7.255535 |
| RNF146 | 0.680974304 | 0.049464555 | 0.031554951 | 5.422892722 | 5.056948 | 5.43468 | 5.596986 | 7.074163 | 8.817023 | 7.873743 |
| ITGA1 | 0.682092936 | 0.049418096 | 0.031463763 | 5.419948891 | 4.209882 | 3.360637 | 3.935222 | 6.498222 | 6.373501 | 5.882028 |
| TNRC6A | 0.703719964 | 0.048482651 | 0.029463083 | 5.418322648 | 7.177073 | 6.139057 | 7.422239 | 9.146221 | 9.860086 | 9.486503 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| TCERG1 | 0.747739273 | 0.046782073 | 0.025795168 | 5.41524012 | 6.45321 | 6.605686 | 4.754917 | 8.65307 | 9.042712 | 8.719135 |
| TUFT1 | 0.664958259 | 0.050400851 | 0.033289554 | 5.411868189 | 5.263699 | 5.809601 | 4.285996 | 8.964784 | 7.68534 | 6.722123 |
| MAT2B | 0.652231687 | 0.051304265 | 0.034807077 | 5.410038995 | 5.335413 | 4.351315 | 3.935222 | 7.771052 | 7.292524 | 6.129407 |
| BRCC3 | 0.62880659 | 0.053282651 | 0.038274243 | 5.410038995 | 5.335413 | 3.770995 | 3.764125 | 7.771052 | 7.191402 | 5.580533 |
| PIGK | 0.640254582 | 0.052240009 | 0.036544403 | 5.406328669 | 4.263463 | 5.297868 | 4.508334 | 6.396698 | 8.033973 | 6.942983 |
| NHS | 0.700747645 | 0.048679397 | 0.029806056 | 5.404945696 | 4.743564 | 4.413323 | 5.389265 | 7.177844 | 7.138979 | 7.748756 |
| DNASE1L1 | 0.630351144 | 0.053156193 | 0.038031984 | 5.400202623 | 3.819732 | 2.406905 | 2.379345 | 6.252746 | 5.306419 | 4.476242 |
| NVL | 0.65290511 | 0.051234373 | 0.034687989 | 5.397905165 | 2.993831 | 2.023048 | 2.165421 | 4.894482 | 4.131418 | 5.426231 |
| ZNF876P | 0.676450865 | 0.049712169 | 0.03201293 | 5.395907064 | 5.263699 | 4.736586 | 4.724406 | 6.960054 | 7.191402 | 7.695565 |
| ZNF436 | 0.575826438 | 0.049377251 | 0.044529092 | 5.395820187 | 5.316227 | 5.43468 | 6.737132 | 6.811341 | 9.168974 | 8.534542 |
| CENPL | 0.635086857 | 0.052702802 | 0.037307423 | 5.392983573 | 4.743564 | 4.911517 | 4.285996 | 6.283686 | 7.174648 | 7.36177 |
| SEL1L3 | 0.633904612 | 0.052866846 | 0.037490303 | 5.392899178 | 1.874444 | 3.32135 | 3.764125 | 4.894482 | 5.317867 | 6.195186 |
| STK32B | 0.689269968 | 0.04903993 | 0.030709765 | 5.3909869 | 1.874444 | 2.023048 | 2.995681 | 4.013424 | 5.317867 | 5.426231 |
| PRMT3 | 0.637058356 | 0.05255004 | 0.037082681 | 5.3909869 | 5.744513 | 3.32135 | 2.995681 | 7.748771 | 7.187136 | 5.426231 |
| C12orf32 | 0.620400385 | 0.053994857 | 0.039418769 | 5.3909869 | 2.201691 | 3.770995 | 2.995681 | 5.743334 | 4.797798 | 5.426231 |
| TMED7 | 0.602522059 | 0.055597852 | 0.042294658 | 5.388189638 | 6.707871 | 4.80797 | 5.571599 | 9.137671 | 7.89473 | 7.291822 |
| PSME2 | 0.677877156 | 0.049640889 | 0.031872746 | 5.37925091 | 6.949166 | 6.821329 | 6.282905 | 9.049264 | 8.71031 | 9.470756 |
| FLJ45340 | 0.631700439 | 0.0530981 | 0.037847567 | 5.368742372 | 8.074081 | 7.34377 | 7.69729 | 9.179923 | 10.121874 | 11.011601 |
| PTPMT1 | 0.667228644 | 0.050335207 | 0.033069752 | 5.366029401 | 4.743564 | 4.389936 | 2.995681 | 7.167419 | 6.551443 | 6.106561 |
| METAP1 | 0.577527987 | 0.059116451 | 0.047217421 | 5.364191855 | 5.491121 | 4.351315 | 2.379345 | 7.477873 | 6.774676 | 5.446557 |
| SLC39A10 | 0.574384903 | 0.059641821 | 0.047901327 | 5.364191855 | 1.874444 | 4.351315 | 3.935222 | 4.739845 | 6.774676 | 5.874974 |
| ST7 | 0.719739421 | 0.04773847 | 0.027968016 | 5.35933045 | 3.024504 | 3.32135 | 3.324375 | 5.448591 | 6.613395 | 5.446557 |
| DCUN1D1 | 0.674132989 | 0.049888566 | 0.03228445 | 5.359074947 | 3.819732 | 3.32135 | 2.379345 | 5.743334 | 7.138979 | 4.790662 |
| NPDC1 | 0.669323397 | 0.050130746 | 0.032781218 | 5.354088768 | 6.554045 | 6.931478 | 6.601009 | 9.02165 | 8.502167 | 9.899123 |
| SUMF2 | 0.744029647 | 0.046883977 | 0.026058523 | 5.349043493 | 4.309025 | 6.184248 | 6.326717 | 8.745998 | 8.350533 | 8.407967 |
| LINC00263 | 0.656693027 | 0.050983118 | 0.034185777 | 5.347852534 | 2.993831 | 2.023048 | 3.324375 | 5.743334 | 4.797798 | 5.106393 |
| PIK3AP1 | 0.613960409 | 0.054598842 | 0.040336169 | 5.347852534 | 1.874444 | 2.023048 | 3.324375 | 5.743334 | 5.165949 | 3.676349 |
| TYW5 | 0.695556872 | 0.048858998 | 0.030253147 | 5.345864671 | 7.259029 | 6.35207 | 6.056062 | 8.474485 | 9.366395 | 9.60665 |
| GRPEL2 | 0.655177167 | 0.051064299 | 0.034364069 | 5.343965295 | 5.056948 | 4.750708 | 3.90836 | 7.394225 | 7.292524 | 6.32627 |
| PNPLA8 | 0.617501645 | 0.054225734 | 0.039844165 | 5.337363296 | 6.973646 | 5.195784 | 6.031658 | 9.33006 | 8.564762 | 7.611911 |
| LAX1 | 0.579823276 | 0.05881361 | 0.046775774 | 5.334979339 | 8.543486 | 7.885522 | 8.83711 | 9.633502 | 10.958969 | 11.301489 |
| ARL2BP | 0.769511775 | 0.046076407 | 0.024078258 | 5.323003772 | 6.054828 | 6.060401 | 3.324375 | 8.105092 | 8.436733 | 8.472642 |
| SNAPC5 | 0.704724796 | 0.048386088 | 0.0293508 | 5.31959759 | 1.874444 | 2.406905 | 2.379345 | 5.448591 | 4.131418 | 4.790662 |
| ACADM | 0.647149603 | 0.05166843 | 0.035536577 | 5.30973996 | 4.743564 | 4.80797 | 4.285996 | 6.244586 | 7.505595 | 7.152205 |
| EPC2 | 0.704294481 | 0.048419405 | 0.029402518 | 5.30931255 | 4.209882 | 4.830496 | 4.449894 | 8.270632 | 6.640994 | 6.618407 |
| HOTAIRM1 | 0.677913097 | 0.049626141 | 0.031854372 | 5.296849907 | 6.143785 | 6.35207 | 6.861515 | 8.757204 | 9.275744 | 8.519314 |
| CASD1 | 0.614624799 | 0.054543342 | 0.040260633 | 5.293477868 | 5.491121 | 2.406905 | 3.935222 | 6.339437 | 7.406567 | 5.882028 |
| C5orf60 | 0.617272994 | 0.054254364 | 0.039894522 | 5.291449402 | 5.335413 | 3.770995 | 3.324375 | 5.728038 | 6.640994 | 7.523109 |
| TMEM5 | 0.719961409 | 0.04771980 | 0.027934672 | 5.290900462 | 4.209882 | 4.389936 | 3.324375 | 6.395481 | 6.613395 | 6.618407 |
| CACNB4 | 0.644108311 | 0.05192151 | 0.036025859 | 5.290900462 | 4.209882 | 2.809601 | 4.944468 | 7.109557 | 5.874974 | 5.874974 |
| CTNNA1 | 0.613093042 | 0.054675277 | 0.04046002 | 5.284902414 | 6.48761 | 7.033812 | 6.919905 | 10.377176 | 9.321782 | 7.988762 |
| CKAP5 | 0.662870885 | 0.050504642 | 0.033484859 | 5.284569027 | 4.963444 | 4.736586 | 2.379345 | 7.36523 | 6.189775 | 6.722123 |
| PRDM14 | 0.663653889 | 0.050460138 | 0.033403879 | 5.27239722 | 7.09018 | 6.270596 | 7.156853 | 8.700282 | 9.47632 | 9.555312 |
| TMEM136 | 0.655981539 | 0.050993826 | 0.034247703 | 5.270787183 | 4.815804 | 4.413323 | 3.90836 | 6.811341 | 6.319269 | 7.020304 |
| TRADD | 0.599879064 | 0.056344664 | 0.042858796 | 5.268919693 | 3.839948 | 3.770995 | 2.165421 | 6.183122 | 6.237456 | 6.618407 |
| STAG3L4 | 0.722229218 | 0.047646206 | 0.027712827 | 5.266714371 | 2.201691 | 2.023048 | 2.165421 | 5.743334 | 4.131418 | 5.874974 |
| ABAT | 0.62661217 | 0.053505098 | 0.038590677 | 5.266714371 | 3.819732 | 2.406905 | 2.165421 | 5.705318 | 5.353925 | 4.562324 |
| ANKRD23 | 0.610791094 | 0.054914277 | 0.040077816 | 5.266714371 | 1.874444 | 2.406905 | 2.165421 | 5.095353 | 3.571326 | 4.562324 |
| ZRSR2 | 0.599617513 | 0.05636405 | 0.042913916 | 5.266714371 | 2.201691 | 2.023048 | 2.165421 | 4.718672 | 3.571326 | 4.562324 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| PCGF6 | 0.595699514 | 0.056728942 | 0.043505954 | 5.266714371 | 3.024504 | 3.770995 | 2.165421 | 5.095353 | 6.319269 | 4.562324 |
| POGZ | 0.656715837 | 0.050983118 | 0.034178972 | 5.264351144 | 6.099991 | 5.148082 | 5.723602 | 8.39062 | 8.119857 | 7.553321 |
| LINC00312 | 0.601268992 | 0.056215269 | 0.042613814 | 5.261285118 | 4.743564 | 4.413323 | 3.935222 | 5.743334 | 7.138979 | 6.924055 |
| CCDC109B | 0.624840447 | 0.053610471 | 0.038781218 | 5.257599817 | 4.639409 | 5.195784 | 5.389265 | 5.743334 | 7.066159 | 7.033813 |
| MIR17HG | 0.677384083 | 0.049687867 | 0.031933311 | 5.252595862 | 4.309025 | 6.044198 | 6.054038 | 7.814607 | 7.819723 | 7.943848 |
| PHF7 | 0.602179909 | 0.056019794 | 0.042385846 | 5.250073823 | 3.350997 | 2.023048 | 3.324375 | 8.447068 | 5.353925 | 4.476242 |
| LOC100287314 | 0.733064369 | 0.047310912 | 0.026889418 | 5.245385786 | 2.201691 | 4.389936 | 3.935222 | 5.743334 | 6.237456 | 6.32627 |
| MYO1B | 0.647015547 | 0.051681274 | 0.035555359 | 5.244049302 | 6.707871 | 6.537655 | 6.355801 | 6.544171 | 8.928336 | 9.103055 |
| ECT2L | 0.637580165 | 0.052501106 | 0.036984689 | 5.237790537 | 9.869873 | 9.382008 | 9.920257 | 8.331873 | 12.258832 | 13.230974 |
| CDK2 | 0.652609609 | 0.051258571 | 0.034719292 | 5.230727802 | 5.263699 | 6.049721 | 5.609945 | 11.088146 | 8.436733 | 8.340256 |
| TNFRSF14 | 0.692856278 | 0.048944238 | 0.030421232 | 5.230659092 | 5.335413 | 4.80797 | 5.217616 | 7.30543 | 7.25505 | 7.722406 |
| BFCAB2 | 0.719554043 | 0.047747218 | 0.027980946 | 5.229578497 | 5.335413 | 4.911517 | 5.225216 | 7.531061 | 7.473335 | 7.611911 |
| TXNDC9 | 0.588536782 | 0.057530341 | 0.044871725 | 5.227675967 | 3.819732 | 2.023048 | 2.165421 | 7.656039 | 6.205902 | 3.630092 |
| ANKRD20A9P | 0.645122742 | 0.051833045 | 0.035895883 | 5.22049219 | 9.663383 | 9.529443 | 9.976372 | 11.387609 | 12.829846 | 12.047569 |
| SFT2D3 | 0.618870382 | 0.054111443 | 0.039642055 | 5.219703032 | 4.309025 | 3.32135 | 2.165421 | 5.705318 | 5.165949 | 6.195186 |
| ESRG | 0.638326106 | 0.052467325 | 0.03686424 | 5.216873863 | 6.267718 | 5.809601 | 5.225216 | 7.856887 | 7.767462 | 8.650903 |
| PUM2 | 0.69181226 | 0.048955004 | 0.030538278 | 5.215392864 | 5.491121 | 6.42919 | 6.704285 | 8.811966 | 8.842512 | 8.472642 |
| GM2A | 0.659594803 | 0.050730781 | 0.033844845 | 5.213030191 | 6.099991 | 5.661685 | 5.225216 | 7.607339 | 8.140553 | 8.269212 |
| EEF2K | 0.59856252 | 0.056432998 | 0.043090167 | 5.211801323 | 6.617556 | 6.849665 | 7.481604 | 8.346785 | 9.47632 | 9.863386 |
| STYX | 0.632790307 | 0.052998119 | 0.037710786 | 5.208597546 | 4.639409 | 3.360637 | 4.944468 | 7.144104 | 6.043524 | 7.020304 |
| LOC100019986 | 0.680212205 | 0.049490097 | 0.031597822 | 5.199359546 | 6.054828 | 6.502398 | 7.156853 | 8.433162 | 9.366395 | 9.430619 |
| LOC282997 | 0.639291084 | 0.052350016 | 0.036676421 | 5.188531272 | 4.743564 | 4.80797 | 3.90836 | 6.283686 | 6.78473 | 7.428484 |
| PRUNE2 | 0.727712374 | 0.047495226 | 0.027303164 | 5.182873998 | 1.874444 | 2.406905 | 2.165421 | 6.283686 | 4.539173 | 4.146207 |
| LOC401052 | 0.712165839 | 0.047984994 | 0.028560735 | 5.182873998 | 1.874444 | 2.406905 | 2.165421 | 5.728038 | 4.539173 | 4.146207 |
| LOC100288069 | 0.673330451 | 0.049922388 | 0.032336849 | 5.182873998 | 2.993831 | 2.023048 | 2.165421 | 4.341916 | 4.539173 | 6.106561 |
| ZNF2 | 0.667921893 | 0.050279153 | 0.032977203 | 5.182873998 | 1.874444 | 2.406905 | 2.165421 | 6.244586 | 4.539173 | 3.676349 |
| NLGN4X | 0.662823842 | 0.050504642 | 0.033498469 | 5.182873998 | 2.201691 | 3.770995 | 2.165421 | 5.728038 | 4.539173 | 5.580533 |
| FAM105A | 0.634519149 | 0.052771408 | 0.037399115 | 5.182873998 | 3.350997 | 2.023048 | 2.165421 | 8.433162 | 4.539173 | 3.630092 |
| LOC338817 | 0.626378203 | 0.053505098 | 0.03860837 | 5.182873998 | 2.201691 | 3.360637 | 2.165421 | 5.320955 | 4.539173 | 4.790662 |
| AP3B2 | 0.62616071 | 0.053522686 | 0.038660088 | 5.182873998 | 2.201691 | 2.023048 | 2.165421 | 5.095353 | 4.539173 | 3.630092 |
| C1orf15 | 0.589210155 | 0.05748724 | 0.044760803 | 5.182873998 | 3.024504 | 2.023048 | 2.165421 | 6.183122 | 4.539173 | 3.630092 |
| C2orf43 | 0.585674929 | 0.057930543 | 0.04547261 | 5.182873998 | 2.201691 | 2.023048 | 2.165421 | 6.339437 | 4.539173 | 2.921909 |
| CXADRP2 | 0.572374046 | 0.060003659 | 0.048410344 | 5.182873998 | 5.328526 | 3.32135 | 2.165421 | 7.656039 | 4.539173 | 6.385515 |
| DHFRL1 | 0.583890327 | 0.058126643 | 0.045782919 | 5.178636586 | 5.335413 | 3.872014 | 5.702912 | 6.244586 | 7.713236 | 7.96648 |
| NR1D2 | 0.604799916 | 0.055661385 | 0.041870024 | 5.174186189 | 4.815804 | 4.830496 | 5.974145 | 7.30543 | 7.187136 | 7.748756 |
| CDK14 | 0.690195041 | 0.048987301 | 0.030632188 | 5.169565981 | 3.819732 | 2.406905 | 3.324375 | 5.579836 | 6.189775 | 5.446557 |
| ZBTB41 | 0.616713666 | 0.054320822 | 0.04 | 5.169565981 | 3.819732 | 3.872014 | 2.995681 | 7.631894 | 6.189775 | 4.562324 |
| GMPPA | 0.589390158 | 0.05748724 | 0.04474311 | 5.16895933 | 6.227577 | 4.80797 | 3.324375 | 7.177844 | 6.861783 | 7.553321 |
| C12orf43 | 0.662863053 | 0.050504642 | 0.033491664 | 5.160975513 | 6.973646 | 6.228068 | 7.030042 | 8.79031 | 9.086038 | 9.397686 |
| GOPC | 0.689644536 | 0.048997321 | 0.030660769 | 5.160673696 | 5.982974 | 4.911517 | 5.018694 | 8.014609 | 8.350533 | 7.218312 |
| TMEM161B | 0.654088719 | 0.051134477 | 0.034515141 | 5.160105894 | 4.743564 | 3.360637 | 3.764125 | 5.728038 | 6.608026 | 6.942983 |
| ARL4A | 0.653210101 | 0.051218943 | 0.034638312 | 5.160105894 | 4.309025 | 3.360637 | 3.935222 | 5.728038 | 6.549959 | 6.385515 |
| SDHAF2 | 0.603041842 | 0.055919113 | 0.042194624 | 5.158947283 | 6.924263 | 5.789702 | 5.225216 | 8.156778 | 7.68534 | 9.123341 |
| CEBPZ | 0.755776339 | 0.046493188 | 0.025157537 | 5.157810389 | 5.856559 | 6.03611 | 2.165421 | 7.937902 | 8.402869 | 7.920856 |
| PDE6D | 0.632935334 | 0.052996828 | 0.037699898 | 5.157519487 | 3.819732 | 4.80797 | 2.406905 | 5.448591 | 7.174648 | 6.051818 |
| PLEKHG3 | 0.60477696 | 0.055661385 | 0.041876829 | 5.157519487 | 4.815804 | 4.80797 | 4.754917 | 6.339437 | 7.174648 | 7.255535 |
| COG6 | 0.649330656 | 0.051527347 | 0.035140524 | 5.155073589 | 4.743564 | 2.809601 | 2.379345 | 7.109557 | 6.78473 | 4.476242 |
| ITM2B | 0.660601263 | 0.05067924 | 0.033741409 | 5.151145124 | 9.782496 | 9.342669 | 9.765631 | 12.130524 | 12.487096 | 11.379464 |
| ACAA1 | 0.723436509 | 0.047612321 | 0.02760803 | 5.135957766 | 2.201691 | 2.023048 | 2.379345 | 6.550689 | 4.131418 | 4.562324 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| KIAA1524 | 0.610679563 | 0.054959374 | 0.040826812 | 5.135485008 | 1.874444 | 3.360637 | 2.379345 | 4.739845 | 4.539173 | 5.106393 |
| PRKCQ | 0.682628202 | 0.049399307 | 0.031403879 | 5.134037834 | 2.993831 | 3.32135 | 2.379345 | 5.026959 | 5.353925 | 5.580533 |
| ATHL1 | 0.568815705 | 0.060479768 | 0.049167744 | 5.125966006 | 6.846868 | 6.904719 | 6.737132 | 9.204692 | 7.89473 | 9.910841 |
| TRPC6 | 0.618099005 | 0.054162167 | 0.039720313 | 5.120725443 | 4.263463 | 2.809601 | 3.324375 | 6.067497 | 5.165949 | 6.129407 |
| FLOT1 | 0.647565337 | 0.051665552 | 0.035471929 | 5.120291279 | 7.671922 | 7.152299 | 6.919905 | 9.08528 | 9.508524 | 10.176565 |
| MGC21881 | 0.642153618 | 0.052008291 | 0.036247703 | 5.119491911 | 5.658609 | 2.809601 | 4.449894 | 8.014609 | 6.608026 | 6.385515 |
| NR2C2 | 0.573183225 | 0.059824474 | 0.048218442 | 5.116783437 | 3.839948 | 4.389936 | 5.571599 | 6.811341 | 7.414086 | 6.195186 |
| PRKRA | 0.584572402 | 0.05794619 | 0.045503232 | 5.108348839 | 6.381847 | 4.736586 | 5.723602 | 8.734704 | 8.098861 | 6.931222 |
| LOC100289341 | 0.630820136 | 0.053142215 | 0.037921062 | 5.107876878 | 6.820119 | 6.092406 | 6.737132 | 8.190235 | 9.148683 | 9.172843 |
| C1orf220 | 0.616408846 | 0.054342412 | 0.040024498 | 5.098608444 | 4.682076 | 4.736586 | 5.723602 | 7.33564 | 7.406567 | 7.03218 |
| EDA2R | 0.585405813 | 0.05795448 | 0.045537258 | 5.098003049 | 4.263463 | 2.023048 | 3.324375 | 4.718672 | 6.613395 | 5.446557 |
| SH3TC2 | 0.568261888 | 0.060062468 | 0.049333106 | 5.097631347 | 3.839948 | 3.32135 | 2.165421 | 4.013424 | 6.189775 | 6.106561 |
| ARHGEF3 | 0.612470045 | 0.054769559 | 0.040547125 | 5.094076361 | 4.309025 | 2.809601 | 4.508334 | 6.857154 | 6.319269 | 5.580533 |
| LOC100128640 | 0.613642586 | 0.054633981 | 0.040370194 | 5.083406092 | 6.707871 | 5.148082 | 7.003286 | 7.897963 | 9.053666 | 9.143346 |
| METAP2 | 0.718963592 | 0.047781016 | 0.02804083 | 5.079134345 | 6.143785 | 4.413323 | 6.636262 | 8.801178 | 8.350533 | 8.488368 |
| POLR1B | 0.647223324 | 0.051168843 | 0.035516162 | 5.079066186 | 4.263463 | 4.911517 | 3.90836 | 6.396698 | 6.608026 | 7.020304 |
| TECPR1 | 0.685778284 | 0.049293152 | 0.031079959 | 5.078303514 | 8.379096 | 7.843866 | 8.234655 | 10.178935 | 10.687282 | 10.723442 |
| LOC100506548 | 0.580372581 | 0.058778844 | 0.046680504 | 5.075488405 | 6.554045 | 5.297868 | 7.003286 | 7.33564 | 9.237827 | 9.346832 |
| CCDC14 | 0.598344109 | 0.056462942 | 0.043150051 | 5.071701192 | 5.658609 | 5.297868 | 6.601009 | 8.087444 | 8.436733 | 7.640338 |
| C11orf73 | 0.704276825 | 0.048419405 | 0.029409323 | 5.071831124 | 4.209882 | 4.389936 | 3.764125 | 6.544171 | 7.473335 | 6.106561 |
| RAB2A | 0.651060775 | 0.05143697 | 0.034948622 | 5.062420553 | 6.997718 | 6.072636 | 5.596986 | 9.337546 | 9.107223 | 7.774634 |
| PRLR | 0.59133023 | 0.057248319 | 0.044357264 | 5.061860622 | 4.743564 | 4.911517 | 4.754917 | 8.514658 | 7.094585 | 5.882028 |
| NDRG4 | 0.599381794 | 0.056379839 | 0.042952705 | 5.060666722 | 1.874444 | 3.770995 | 5.018694 | 8.087444 | 3.571326 | 4.476242 |
| TMEM123 | 0.611495917 | 0.054837105 | 0.0406492 | 5.055485034 | 5.897292 | 6.466258 | 6.670675 | 10.548217 | 8.804107 | 7.352555 |
| CDK5RAP2 | 0.651850253 | 0.05481369 | 0.040600885 | 5.049800489 | 6.008206 | 4.413323 | 5.596986 | 6.244586 | 8.119857 | 7.428484 |
| SMAP2 | 0.617233549 | 0.054273567 | 0.039993263 | 5.048114459 | 6.846868 | 5.487673 | 4.754917 | 9.778045 | 8.486085 | 8.784285 |
| LYST | 0.627679769 | 0.053394669 | 0.048430759 | 5.034921624 | 4.743564 | 6.42919 | 5.217616 | 8.206677 | 6.640994 | 8.269212 |
| C7orf29 | 0.592244706 | 0.057117807 | 0.044147669 | 5.034621719 | 6.58615 | 6.072636 | 5.609945 | 7.274575 | 8.904331 | 8.918033 |
| SPARC | 0.634783997 | 0.052753682 | 0.037376659 | 5.027323625 | 6.617556 | 5.148082 | 5.389265 | 7.477873 | 8.296229 | 8.60836 |
| PDE7A | 0.594147666 | 0.056928919 | 0.043758421 | 5.026034632 | 3.024504 | 2.023048 | 2.379345 | 5.252045 | 5.353925 | 3.676349 |
| ZNF37A | 0.589042755 | 0.05748724 | 0.044712218 | 5.02313918 | 6.617556 | 5.789702 | 6.601009 | 7.607339 | 9.158864 | 8.929599 |
| VEGFB | 0.609929413 | 0.055085743 | 0.040964274 | 5.018039775 | 2.993831 | 2.023048 | 2.165421 | 5.320955 | 5.306419 | 3.630092 |
| MTRF1 | 0.579874462 | 0.05881361 | 0.046768969 | 5.011608367 | 1.874444 | 2.023048 | 2.995681 | 5.320955 | 4.608763 | 3.630092 |
| RP1-177G6.2 | 0.685096409 | 0.04931773 | 0.031165703 | 5.009343851 | 7.530567 | 7.152299 | 7.056312 | 9.794456 | 9.586024 | 9.380933 |
| ZMYND19 | 0.611783253 | 0.05481369 | 0.030614495 | 5.006890649 | 4.263463 | 2.023048 | 3.764125 | 5.320955 | 5.509998 | 6.587378 |
| IFT140 | 0.584855955 | 0.058042825 | 0.045643416 | 5.004323696 | 4.815804 | 3.360637 | 3.324375 | 5.026959 | 7.138979 | 6.385515 |
| SREK1 | 0.603579672 | 0.055577445 | 0.042061245 | 5.004312023 | 4.815804 | 3.872014 | 4.754917 | 6.664985 | 7.187136 | 6.195186 |
| NACAD | 0.615811811 | 0.05440747 | 0.040106839 | 5.003678354 | 7.09018 | 6.092406 | 6.369239 | 8.604261 | 8.777924 | 8.692228 |
| C14orf102 | 0.653217871 | 0.051218943 | 0.034631507 | 5.000891462 | 2.993831 | 2.023048 | 2.995681 | 5.252045 | 5.317867 | 4.562324 |
| ZNF263 | 0.609322441 | 0.055142692 | 0.04106771 | 5.000891462 | 3.024509 | 2.023048 | 2.995681 | 5.448591 | 5.317867 | 4.146207 |
| LSM5 | 0.595721078 | 0.056728942 | 0.043499149 | 5.000352438 | 1.874444 | 3.872014 | 4.285996 | 4.894482 | 6.608026 | 5.900694 |
| PHF6 | 0.606741943 | 0.055431478 | 0.041521606 | 4.997075608 | 3.350997 | 4.413323 | 5.596986 | 7.918071 | 7.414086 | 5.634184 |
| GCC1 | 0.70841444 | 0.048241 59 | 0.02893229 | 4.98940818 | 1.874444 | 2.023048 | 2.165421 | 4.341916 | 4.131418 | 5.106393 |
| ADAM19 | 0.647991241 | 0.051631895 | 0.035384825 | 4.98940818 | 1.874444 | 2.023048 | 2.165421 | 4.341916 | 5.353925 | 3.630092 |
| RRM1 | 0.643521736 | 0.051940717 | 0.036104798 | 4.98940818 | 1.874444 | 2.023048 | 2.165421 | 4.341916 | 3.571326 | 5.446557 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| PLAC8 | 0.640739001 | 0.052197898 | 0.036480436 | 4.98940818 | 1.874444 | 2.023048 | 2.165421 | 4.341916 | 5.165949 | 3.630092 |
| MTRNR2L10 | 0.62951332 | 0.053240793 | 0.038159918 | 4.98940818 | 1.874444 | 2.023048 | 2.165421 | 4.341916 | 3.571326 | 5.091834 |
| MED6 | 0.620173776 | 0.054006231 | 0.039462402 | 4.970029894 | 5.982974 | 5.195784 | 6.737132 | 8.579223 | 8.296229 | 7.943848 |
| HSD3BP4 | 0.696278507 | 0.048851278 | 0.030197346 | 4.964909299 | 3.350997 | 2.406905 | 3.324375 | 4.718672 | 5.509998 | 7.352555 |
| PYCR2 | 0.599691149 | 0.056357089 | 0.042890779 | 4.961652994 | 3.819732 | 2.809601 | 2.165421 | 5.728038 | 5.509998 | 4.476242 |
| HRH2 | 0.598561441 | 0.056432998 | 0.043100374 | 4.961652994 | 1.874444 | 2.023048 | 2.165421 | 4.341916 | 3.571326 | 4.476242 |
| KBTBD12 | 0.598561441 | 0.056432998 | 0.043100374 | 4.961652994 | 1.874444 | 2.023048 | 2.165421 | 4.341916 | 3.571326 | 4.476242 |
| EFCAB11 | 0.590776635 | 0.05748724 | 0.044774413 | 4.961652994 | 1.874444 | 2.809601 | 2.165421 | 5.705318 | 3.571326 | 4.476242 |
| PDCD4 | 0.687746537 | 0.049134487 | 0.030823409 | 4.956839287 | 7.021395 | 5.340619 | 7.680498 | 9.633502 | 9.330816 | 9.201749 |
| LMO4 | 0.651048417 | 0.05143697 | 0.034955427 | 4.955527682 | 7.410173 | 5.43468 | 7.956385 | 9.54575 | 10.265423 | 8.96375 |
| DMD | 0.685399662 | 0.049314432 | 0.031134399 | 4.941064812 | 5.056948 | 5.487673 | 4.285996 | 7.70315 | 7.191402 | 7.36177 |
| POLR2G | 0.631878658 | 0.05307838 | 0.037825111 | 4.93875207 | 6.898923 | 6.03611 | 5.225216 | 8.553743 | 8.314558 | 8.340256 |
| MRVI1 | 0.59217015 | 0.057129881 | 0.044166043 | 4.936965583 | 5.897292 | 4.736586 | 6.737132 | 7.274575 | 8.200916 | 8.986077 |
| PHLDB2 | 0.633722901 | 0.052882301 | 0.037519564 | 4.932209488 | 4.309025 | 4.830496 | 3.935222 | 6.396698 | 6.237456 | 7.46072 |
| FIS1 | 0.699549026 | 0.048733855 | 0.029908813 | 4.925617809 | 7.463005 | 7.421341 | 7.082111 | 9.698891 | 9.76331 | 9.562759 |
| CASP2 | 0.637503754 | 0.052501106 | 0.036698299 | 4.919662898 | 5.982974 | 5.43468 | 5.571599 | 7.877571 | 7.870158 | 7.492252 |
| LYPLA2 | 0.622935626 | 0.053781042 | 0.039028241 | 4.919053136 | 4.209882 | 4.351315 | 5.217616 | 7.792994 | 6.373501 | 6.649696 |
| LOC100128164 | 0.7221269 | 0.047646206 | 0.027726438 | 4.916195348 | 1.874444 | 3.770995 | 3.90836 | 5.743334 | 6.205902 | 6.051818 |
| TP53I3 | 0.667530282 | 0.050323626 | 0.033050698 | 4.916195348 | 1.874444 | 4.80797 | 3.90836 | 6.498222 | 6.205902 | 6.106561 |
| MYCBP2 | 0.70479151 | 0.048386088 | 0.029330384 | 4.91463052 | 5.700376 | 6.060401 | 6.072169 | 7.918071 | 9.25691 | 8.357484 |
| CMPK2 | 0.601508874 | 0.056113873 | 0.042528071 | 4.912654932 | 3.839948 | 3.770995 | 3.324375 | 6.067497 | 4.608763 | 7.748756 |
| PPP2R5C | 0.626342797 | 0.053505098 | 0.038615175 | 4.912630893 | 5.753024 | 5.809601 | 6.054038 | 7.582358 | 8.350533 | 8.232333 |
| LOC338651 | 0.601083764 | 0.056247441 | 0.042656005 | 4.912476789 | 3.024504 | 4.944468 | 5.320955 | 6.774676 | 6.931222 | |
| CFL2 | 0.641416334 | 0.052107192 | 0.036366111 | 4.910594455 | 5.779429 | 5.43468 | 4.724406 | 8.433162 | 7.68534 | 7.020304 |
| SEPT7P2 | 0.706100317 | 0.048351237 | 0.029220823 | 4.90948268 | 6.186289 | 4.351315 | 6.369239 | 7.937902 | 6.613395 | 8.66481 |
| DPYSL2 | 0.723793799 | 0.047585406 | 0.027584893 | 4.905210095 | 4.743564 | 3.770995 | 4.449894 | 7.037879 | 6.587378 | |
| LCP2 | 0.598356033 | 0.053255542 | 0.043143246 | 4.901971869 | 3.024504 | 2.023048 | 2.165421 | 5.095353 | 5.317867 | 3.676349 |
| C15orf23 | 0.657504014 | 0.050903629 | 0.034116366 | 4.879821557 | 3.819732 | 4.736586 | 2.165421 | 5.891233 | 6.640994 | 6.106561 |
| DIP2B | 0.593764493 | 0.057012338 | 0.043849609 | 4.87981284 | 4.263463 | 3.32135 | 3.90836 | 5.095353 | 7.094585 | 6.195186 |
| LIN54 | 0.583364397 | 0.058208993 | 0.045893841 | 4.874324244 | 5.744513 | 6.670655 | 7.273415 | 9.558617 | 9.158864 | 7.825039 |
| YY1 | 0.59248399 | 0.057110241 | 0.044096632 | 4.870248403 | 7.918838 | 6.03611 | 7.204614 | 8.139755 | 10.202833 | 10.096736 |
| CTSL1P2 | 0.582786783 | 0.058317693 | 0.046062606 | 4.867468606 | 6.381847 | 7.679931 | 7.156853 | 8.665019 | 9.009341 | 10.265959 |
| EHMT1 | 0.582734302 | 0.058324851 | 0.046082341 | 4.864571601 | 6.417969 | 5.195784 | 3.935222 | 8.700282 | 7.473335 | 6.649696 |
| PLA2G4A | 0.625586482 | 0.053562842 | 0.038721334 | 4.86323049 | 3.024504 | 2.023048 | 2.995681 | 5.095353 | 5.306419 | 4.476242 |
| NRD1 | 0.647733242 | 0.051631895 | 0.035429738 | 4.855441047 | 4.963444 | 3.770995 | 5.217616 | 7.243046 | 6.608026 | 7.352555 |
| PRKD1 | 0.706536691 | 0.048309794 | 0.029147329 | 4.854756561 | 1.874444 | 3.32135 | 3.764125 | 5.448591 | 6.043524 | 5.580533 |
| EPT1 | 0.648958272 | 0.051556323 | 0.035207894 | 4.84851789 | 6.45321 | 6.877454 | 6.326717 | 8.604261 | 8.842512 | 8.858771 |
| PPP3CA | 0.599918036 | 0.056344664 | 0.04285199 | 4.838756121 | 6.099991 | 6.466258 | 5.217616 | 8.190235 | 8.904331 | 7.492252 |
| P2RY14 | 0.628903623 | 0.053255542 | 0.038246342 | 4.838470141 | 2.201691 | 2.406905 | 2.165421 | 6.396698 | 3.571326 | 4.476242 |
| TUBGCP4 | 0.592296984 | 0.057117807 | 0.044134059 | 4.838470141 | 2.201691 | 3.360637 | 2.165421 | 6.183122 | 4.131418 | 4.476242 |
| ZFX | 0.582020154 | 0.058454033 | 0.046244301 | 4.836098269 | 5.779429 | 4.750708 | 4.944468 | 8.700282 | 7.269549 | 7.218312 |
| DNAJB6 | 0.646183047 | 0.051798486 | 0.035724396 | 4.835844007 | 8.877752 | 9.104741 | 9.696318 | 11.534875 | 11.874698 | 11.151519 |
| TMEM175 | 0.632058571 | 0.05307838 | 0.037818306 | 4.834857348 | 2.993831 | 5.362142 | 6.012527 | 8.286188 | 7.191402 | 6.924055 |
| ATF7IP | 0.688548406 | 0.049115877 | 0.030782579 | 4.830624127 | 4.743564 | 4.750708 | 5.723602 | 7.995811 | 7.942653 | 6.931222 |
| C9orf68 | 0.601231615 | 0.056227768 | 0.042632188 | 4.829132256 | 2.201691 | 3.360637 | 2.995681 | 6.183122 | 4.539173 | 4.146207 |
| EZR | 0.669200368 | 0.05015850 | 0.044250425 | 4.816536816 | 7.278811 | 7.926009 | 9.696318 | 11.328733 | 10.030567 | 9.329475 |
| MIS18BP1 | 0.591874444 | 0.057215069 | 0.044250425 | 4.812457552 | 5.897292 | 5.362142 | 5.389265 | 7.656039 | 7.713236 | 6.73963 |
| CHCHD1 | 0.568846404 | 0.060479768 | 0.049154134 | 4.810968868 | 6.143785 | 4.911517 | 3.935222 | 7.177844 | 7.505595 | 6.942983 |
| YAF2 | 0.606184496 | 0.055489397 | 0.041642055 | 4.809587016 | 7.943836 | 7.033812 | 5.974145 | 9.299725 | 9.426624 | 9.143346 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| AP1S3 | 0.626727115 | 0.053474985 | 0.038547805 | 4.807833173 | 4.639409 | 4.351315 | 4.754917 | 6.954147 | 6.319269 | 7.020304 |
| DHX36 | 0.706360824 | 0.048309794 | 0.029160939 | 4.793999137 | 6.873131 | 6.572071 | 5.217616 | 8.833301 | 9.086038 | 8.692228 |
| BBS2 | 0.592897292 | 0.057080847 | 0.04401293 | 4.793512098 | 6.417969 | 5.487673 | 4.724406 | 7.170315 | 7.793829 | 7.748756 |
| FLJ35390 | 0.682433052 | 0.04941326 | 0.031444029 | 4.789116491 | 4.263463 | 4.389936 | 3.935222 | 6.498222 | 6.373501 | 6.649696 |
| L3MBTL3 | 0.608009189 | 0.055250119 | 0.041296359 | 4.787203117 | 2.993831 | 3.32135 | 3.764125 | 4.894482 | 6.373501 | 5.580533 |
| EXOC4 | 0.588633498 | 0.057508969 | 0.044825451 | 4.787203117 | 4.309025 | 3.32135 | 2.379345 | 5.252045 | 5.920411 | 5.580533 |
| COL2A1 | 0.585421787 | 0.057795448 | 0.045530453 | 4.783987856 | 2.993831 | 2.023048 | 2.379345 | 5.252045 | 5.165949 | 3.676349 |
| PARP2 | 0.610222281 | 0.055039622 | 0.040912555 | 4.783859583 | 5.304463 | 3.872014 | 4.285996 | 6.544171 | 7.292524 | 6.455366 |
| ASPM | 0.691608132 | 0.048955004 | 0.030551888 | 4.779881377 | 1.874444 | 2.023048 | 2.165421 | 5.320955 | 4.131418 | 4.146207 |
| FAM169A | 0.691518888 | 0.048955004 | 0.030558693 | 4.779881377 | 1.874444 | 2.023048 | 2.379345 | 6.067497 | 4.131418 | 4.146207 |
| TRIM69 | 0.679536444 | 0.049531477 | 0.031673358 | 4.779881377 | 1.874444 | 2.023048 | 2.995681 | 5.252045 | 4.131418 | 5.106393 |
| RPUSD2 | 0.672656516 | 0.049933984 | 0.032413066 | 4.779881377 | 1.874444 | 2.023048 | 2.165421 | 4.739845 | 4.131418 | 4.146207 |
| CD27 | 0.650183578 | 0.05147219 | 0.035021436 | 4.779881377 | 1.874444 | 2.023048 | 3.324375 | 5.026959 | 4.131418 | 5.580533 |
| AKR1E2 | 0.626436431 | 0.053505098 | 0.03862198 | 4.779881377 | 1.874444 | 3.32135 | 2.165421 | 5.252045 | 4.131418 | 5.106393 |
| NUF2 | 0.606579002 | 0.055458006 | 0.041565839 | 4.779881377 | 1.874444 | 3.360637 | 2.379345 | 6.183122 | 4.131418 | 4.562324 |
| GPRC5B | 0.604211424 | 0.055732254 | 0.042002722 | 4.779881377 | 1.874444 | 2.023048 | 2.995681 | 5.252045 | 4.131418 | 5.106393 |
| GEMIN8P4 | 0.593461676 | 0.057025989 | 0.043900646 | 4.779881377 | 1.874444 | 2.406905 | 3.324375 | 6.396698 | 4.131418 | 4.790662 |
| SDC3 | 0.610281783 | 0.055039622 | 0.04090575 | 4.777856422 | 4.309025 | 3.770995 | 2.995681 | 4.802615 | 8.181074 | 5.426231 |
| GANC | 0.599150193 | 0.056396398 | 0.043001021 | 4.777856422 | 3.350997 | 3.360637 | 2.379345 | 5.252045 | 5.306419 | 4.476242 |
| TMEM167A | 0.652254763 | 0.051304265 | 0.034793467 | 4.757034401 | 6.554045 | 5.809601 | 5.596986 | 8.527804 | 8.804107 | 7.774634 |
| FAM13A | 0.668516292 | 0.050253093 | 0.032900987 | 4.754714923 | 5.982974 | 6.35207 | 6.489771 | 8.501391 | 9.2474 | 8.232333 |
| NCEH1 | 0.630411636 | 0.053156193 | 0.038011569 | 4.749912062 | 2.993831 | 2.809601 | 3.935222 | 6.183122 | 4.797798 | 5.900694 |
| WARS2 | 0.628430812 | 0.053328786 | 0.038332766 | 4.749912062 | 4.815804 | 3.360637 | 3.935222 | 6.183122 | 6.774676 | 6.129407 |
| UBC | 0.667125321 | 0.050335207 | 0.033090167 | 4.749465528 | 3.819732 | 4.750708 | 2.165421 | 6.067497 | 6.640994 | 6.051818 |
| LACTB | 0.634483165 | 0.052771408 | 0.03740592 | 4.749465528 | 3.819732 | 2.809601 | 3.324375 | 6.067497 | 5.317867 | 5.426231 |
| HNRNPU-AS1 | 0.583168111 | 0.058250261 | 0.045963253 | 4.748361894 | 5.304463 | 5.148082 | 7.132367 | 8.822673 | 8.350533 | 7.395512 |
| CAMK1D | 0.58093219 | 0.058719081 | 0.046566498 | 4.748162376 | 4.963444 | 6.537655 | 6.072169 | 7.210813 | 8.486085 | 8.636861 |
| EIF2S3 | 0.66830737 | 0.050279153 | 0.032939095 | 4.740249064 | 7.021395 | 7.033812 | 6.369239 | 10.21189 | 9.266358 | 8.503924 |
| CCDC104 | 0.645129397 | 0.051833045 | 0.035889078 | 4.738801666 | 5.744513 | 4.351315 | 5.018694 | 7.167419 | 7.989035 | 7.152205 |
| TJP1 | 0.629425389 | 0.053243865 | 0.038172167 | 4.73375864 | 5.982974 | 6.184248 | 5.592916 | 7.835902 | 8.564762 | 7.988762 |
| ADARB2 | 0.597089754 | 0.056614769 | 0.043346717 | 4.731893934 | 4.309025 | 4.413323 | 2.995681 | 4.894482 | 6.551443 | 7.748756 |
| IL13RA1 | 0.591686543 | 0.057222443 | 0.044291936 | 4.730182156 | 5.263699 | 6.092406 | 4.944468 | 7.243406 | 7.505595 | 8.010706 |
| EFHC1 | 0.675107981 | 0.049822189 | 0.032169445 | 4.727950373 | 6.617556 | 6.049721 | 7.030042 | 8.854326 | 9.128102 | 8.858771 |
| NEK7 | 0.59747759 | 0.056551179 | 0.043271181 | 4.713640765 | 6.143785 | 6.044198 | 6.527811 | 8.616619 | 8.764653 | 7.748756 |
| HBXIP | 0.676883207 | 0.049712169 | 0.031985709 | 4.70866159 | 7.445608 | 7.615377 | 7.360327 | 10.236122 | 9.680925 | 9.525135 |
| CYBA | 0.626875294 | 0.053474985 | 0.03852793 | 4.702329925 | 5.897292 | 6.03611 | 4.944468 | 7.177844 | 8.011679 | 8.894619 |
| DDX41 | 0.647822651 | 0.051631895 | 0.03540524 | 4.698660797 | 5.779429 | 5.809601 | 5.018694 | 7.109557 | 8.011679 | 8.870819 |
| VPS26A | 0.696918857 | 0.04882091 | 0.03014769 | 4.69812704 | 3.819732 | 3.32135 | 3.90836 | 7.607339 | 5.509998 | 6.051818 |
| PSAP | 0.635309129 | 0.052679972 | 0.037282749 | 4.69315026 | 9.316235 | 8.445606 | 9.048192 | 11.223584 | 11.897679 | 10.676162 |
| GNPDA2 | 0.638895026 | 0.052413388 | 0.036753998 | 4.689449412 | 2.993831 | 2.023048 | 2.379345 | 5.026959 | 4.608763 | 4.562324 |
| PAPOLG | 0.681468807 | 0.049458162 | 0.031519564 | 4.688522063 | 5.335413 | 6.139057 | 6.355801 | 8.376156 | 8.36819 | 8.32282 |
| TMEM87B | 0.584445053 | 0.057952709 | 0.045517523 | 4.686369198 | 5.304463 | 4.389936 | 2.165421 | 6.664985 | 5.936219 | 6.618407 |
| LTBR | 0.581543854 | 0.058540518 | 0.046342974 | 4.684705832 | 4.963444 | 4.413323 | 3.935222 | 6.183122 | 7.191402 | 6.32627 |
| B3GNT7 | 0.588477237 | 0.057530341 | 0.04488853 | 4.683348549 | 3.024509 | 4.413323 | 3.324375 | 5.252045 | 6.237456 | 5.874974 |
| LOC339788 | 0.635330128 | 0.052679972 | 0.037275944 | 4.681160123 | 5.491121 | 5.195784 | 4.724406 | 7.42265 | 7.107836 | 7.523109 |
| DSTYK | 0.630597135 | 0.053156193 | 0.037977543 | 4.660749298 | 7.730559 | 6.572071 | 6.769247 | 8.591796 | 9.673843 | 9.951121 |
| UHMK1 | 0.57003732 | 0.06003194 | 0.048909833 | 4.658599905 | 5.335413 | 3.360637 | 3.935222 | 7.274575 | 6.608026 | 5.580533 |
| RMI1 | 0.678104383 | 0.049763477 | 0.032100034 | 4.652769951 | 4.682076 | 4.389936 | 3.90836 | 6.811341 | 6.608026 | 6.587378 |
| LOC100507501 | 0.667943435 | 0.050279153 | 0.032970398 | 4.651279958 | 5.056948 | 5.340619 | 5.544653 | 7.274575 | 7.505595 | 8.340256 |

TABLE 8-continued

Differentially Expressed Genes in CD10−, CD24−, CD44− Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| PJA2 | 0.606837943 | 0.05543128 | 0.041510718 | 4.641433488 | 7.317579 | 6.060401 | 6.056062 | 8.270632 | 9.468155 | 8.579284 |
| ORC6 | 0.574084374 | 0.059729834 | 0.04804083 | 4.632632095 | 7.744853 | 6.42919 | 7.082111 | 8.641022 | 9.492512 | 9.50208 |
| YPEL3 | 0.674347123 | 0.049848381 | 0.032241579 | 4.620798576 | 6.417969 | 4.736586 | 6.031658 | 8.087444 | 8.2398 | 8.440667 |
| MARCH6 | 0.64352197 | 0.051940717 | 0.036097993 | 4.6202491 | 7.04469 | 6.983552 | 7.003286 | 9.919426 | 8.777924 | 9.211256 |
| RAPGEF2 | 0.589760204 | 0.057461905 | 0.044668255 | 4.619472198 | 5.744513 | 6.139057 | 5.571599 | 8.346785 | 8.055928 | 7.36177 |
| ING3 | 0.618159422 | 0.054162167 | 0.039713508 | 4.618368323 | 5.335413 | 4.830496 | 3.90836 | 7.037879 | 7.107836 | 6.722123 |
| EIF4G2 | 0.70334423 | 0.048494719 | 0.029531814 | 4.612257841 | 8.151234 | 8.101237 | 8.151795 | 11.235653 | 10.356707 | 10.275054 |
| LOC338739 | 0.581441763 | 0.058561473 | 0.046375638 | 4.607878853 | 3.839948 | 4.389936 | 5.544653 | 6.283686 | 6.551443 | 7.748756 |
| MRPL46 | 0.622243042 | 0.053817472 | 0.039177952 | 4.606193653 | 3.839948 | 2.023048 | 2.165421 | 4.013424 | 6.043524 | 5.580533 |
| CDK13 | 0.626764006 | 0.053474985 | 0.038541 | 4.604582504 | 6.186289 | 5.340619 | 5.596986 | 7.42265 | 8.963611 | 7.800057 |
| SMG1 | 0.572186896 | 0.060021442 | 0.043561826 | 4.603568119 | 6.099991 | 6.311907 | 7.481604 | 8.514658 | 9.275744 | 8.503924 |
| LOC400084 | 0.631452828 | 0.053106978 | 0.037870704 | 4.600716125 | 3.024504 | 2.406905 | 2.165421 | 4.013424 | 4.608763 | 6.722123 |
| ST8SIA4 | 0.580597455 | 0.058752276 | 0.046631507 | 4.600716125 | 3.024504 | 2.406905 | 3.90836 | 7.210813 | 4.608763 | 4.790662 |
| PCM1 | 0.654778509 | 0.051064299 | 0.034420551 | 4.588190724 | 6.52121 | 6.849665 | 6.800663 | 9.23707 | 8.916384 | 8.719135 |
| LGMN | 0.604129724 | 0.055732254 | 0.042009527 | 4.571223597 | 6.846868 | 5.809601 | 6.489771 | 7.937902 | 8.682351 | 9.267025 |
| MLL5 | 0.565601392 | 0.061091369 | 0.049854372 | 4.569436364 | 7.278811 | 6.311907 | 7.156853 | 9.704692 | 8.817023 | 8.503924 |
| RPL14 | 0.646855426 | 0.051704967 | 0.035586254 | 4.567449791 | 10.288639 | 10.341668 | 10.357997 | 12.533057 | 12.852763 | 12.223493 |
| SREK1IP1 | 0.618667464 | 0.054133185 | 0.039673358 | 4.563890635 | 7.067614 | 6.311907 | 5.225216 | 8.447068 | 8.077554 | 9.257878 |
| SCIN | 0.594343739 | 0.056918505 | 0.043734604 | 4.558779321 | 1.874444 | 3.32135 | 3.935222 | 4.739845 | 5.509998 | 5.882028 |
| RGS10 | 0.590742688 | 0.057311568 | 0.044433481 | 4.555775177 | 5.335413 | 6.270596 | 6.072169 | 9.12907 | 7.767462 | 7.523109 |
| RNF20 | 0.58989068 | 0.057439458 | 0.04463491 | 4.540902856 | 4.309025 | 2.809601 | 2.379345 | 6.067497 | 5.920411 | 4.562324 |
| UBR7 | 0.605281751 | 0.055617731 | 0.041808778 | 4.53061323 | 4.682076 | 3.770995 | 3.935222 | 6.244586 | 6.861783 | 5.874974 |
| LOC401320 | 0.655895222 | 0.050993826 | 0.034274923 | 4.528824992 | 4.209882 | 5.148082 | 5.571599 | 7.144104 | 7.656894 | 7.327219 |
| ATXN3 | 0.598892344 | 0.056423848 | 0.043039809 | 4.521019299 | 7.513971 | 7.129367 | 7.030042 | 8.935488 | 9.321782 | 9.690619 |
| ANKRD26P1 | 0.654941727 | 0.051064299 | 0.034400136 | 4.520541748 | 1.874444 | 2.023048 | 2.165421 | 4.341916 | 4.131418 | 4.146207 |
| APTTD1 | 0.611103378 | 0.054867364 | 0.040699558 | 4.520541748 | 1.874444 | 2.406905 | 2.165421 | 4.341916 | 5.353925 | 3.630092 |
| SLC9A4 | 0.600589129 | 0.056308034 | 0.042746512 | 4.520541748 | 2.201691 | 2.023048 | 2.165421 | 4.341916 | 3.571326 | 5.091834 |
| NRAS | 0.663336995 | 0.05046582 | 0.033425613 | 4.520430032 | 6.898923 | 6.311907 | 4.508334 | 8.801178 | 8.314558 | 8.488368 |
| PPFIBP2 | 0.642438185 | 0.051967533 | 0.036194624 | 4.512901426 | 4.263463 | 4.413323 | 2.165421 | 5.891233 | 6.043524 | 6.587378 |
| HMBS | 0.566532954 | 0.060923671 | 0.04967608 | 4.506846946 | 2.993831 | 2.023048 | 2.165421 | 4.739845 | 5.165949 | 3.676349 |
| LONP2 | 0.605566255 | 0.055588631 | 0.041769309 | 4.505359624 | 7.177073 | 7.08238 | 7.92821 | 9.204692 | 9.348715 | 10.284093 |
| NCALD | 0.60898809 | 0.055156748 | 0.04114801 | 4.504413157 | 2.993831 | 4.830496 | 3.935222 | 6.664985 | 5.936219 | 6.106561 |
| KIAA1715 | 0.62850987 | 0.053328876 | 0.038325961 | 4.499553673 | 5.700376 | 5.43468 | 4.285996 | 7.36523 | 7.870158 | 7.180104 |
| NECAP1 | 0.660380834 | 0.055133391 | 0.041052059 | 4.497544857 | 4.963444 | 6.03611 | 4.754917 | 8.087444 | 7.598264 | 6.924055 |
| RBBP4 | 0.66840825 | 0.050269006 | 0.03291936 | 4.496666752 | 7.373845 | 7.240547 | 7.317525 | 9.486381 | 9.809281 | 9.380933 |
| NCOA4 | 0.575569102 | 0.059298663 | 0.047625723 | 4.495829863 | 7.317759 | 7.323707 | 6.527811 | 9.744652 | 8.696398 | 9.008063 |
| PAN3 | 0.587154536 | 0.057666624 | 0.045165818 | 4.486167914 | 6.898923 | 6.702075 | 6.369239 | 9.220972 | 8.867558 | 8.175185 |
| TRIM41 | 0.629716505 | 0.053228219 | 0.038127254 | 4.480008275 | 3.350997 | 4.413323 | 4.449894 | 6.396698 | 6.613395 | 6.051818 |
| HERPUD2 | 0.619939035 | 0.054048689 | 0.039480095 | 4.477992615 | 6.267718 | 5.297868 | 5.544653 | 8.239009 | 8.119857 | 7.46072 |
| DYNC1LI1 | 0.610915674 | 0.054914277 | 0.040760122 | 4.469656416 | 5.658609 | 6.049721 | 6.072169 | 7.976765 | 7.819723 | 8.232333 |
| ARMC9 | 0.619494096 | 0.054008689 | 0.039522286 | 4.468616614 | 2.993831 | 2.406905 | 2.379345 | 5.252045 | 4.539173 | 4.562324 |
| ZNF778 | 0.593045604 | 0.057053082 | 0.043980265 | 4.468616614 | 1.874444 | 2.406905 | 2.379345 | 5.026959 | 4.539173 | 3.630092 |
| JMJD7 | 0.580564425 | 0.058752276 | 0.046638312 | 4.468616614 | 1.874444 | 4.750708 | 3.90836 | 6.811341 | 6.549959 | 2.921909 |
| QTRTD1 | 0.606242536 | 0.055476612 | 0.041623682 | 4.466478121 | 4.963444 | 5.297868 | 5.544653 | 6.067497 | 7.740604 | 5.446557 |
| GTF3C2 | 0.592542252 | 0.057105447 | 0.044074855 | 4.464492619 | 5.049177 | 6.092406 | 6.072169 | 7.70315 | 7.107836 | 7.492252 |
| NMD3 | 0.645279256 | 0.051831344 | 0.035853692 | 4.460197426 | 5.316227 | 5.195784 | 5.723602 | 8.65307 | 7.473335 | 7.255535 |
| APOA1BP | 0.599828664 | 0.056344664 | 0.041623682 | 4.45770112 | 5.304463 | 4.413323 | 4.449894 | 6.244586 | 6.549959 | 5.446557 |
| PCSK5 | 0.632511246 | 0.053040507 | 0.037764546 | 4.451200429 | 5.897292 | 6.092406 | 6.326717 | 8.051486 | 8.502167 | 8.232333 |
| EMX2OS | 0.59865878 | 0.056432998 | 0.043076557 | 4.45018608 | 5.056948 | 6.060401 | 4.754917 | 7.210813 | 7.191402 | 8.194487 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| INTS3 | 0.583594776 | 0.058194436 | 0.045845526 | 4.447364981 | 5.744513 | 5.789702 | 6.072169 | 7.477873 | 7.942653 | 8.287303 |
| RAD23B | 0.62012434 | 0.054006231 | 0.039469207 | 4.446652462 | 7.6108 | 7.87177 | 7.462086 | 10.149468 | 9.468155 | 9.76352 |
| CHORDC1 | 0.577611187 | 0.059114532 | 0.047206533 | 4.442949661 | 5.700376 | 6.605686 | 6.861515 | 8.757204 | 9.540026 | 7.611911 |
| ARPC5L | 0.588623185 | 0.057508969 | 0.044832256 | 4.435879596 | 5.700376 | 4.736586 | 6.056062 | 8.190235 | 7.066159 | 7.849596 |
| DCUN1D4 | 0.599133078 | 0.05640611 | 0.043017353 | 4.420622621 | 4.815804 | 4.911517 | 6.012527 | 6.960054 | 7.767462 | 7.640338 |
| DNAJC13 | 0.584295739 | 0.058106817 | 0.045730521 | 4.418475241 | 5.897292 | 4.736586 | 4.508334 | 6.651882 | 7.767462 | 7.327219 |
| UHRF1BP1 | 0.577854374 | 0.059077666 | 0.047167744 | 4.418475241 | 5.491121 | 4.389926 | 4.508334 | 6.651882 | 6.640994 | 7.46072 |
| PHF16 | 0.649901625 | 0.051478217 | 0.035047295 | 4.412037769 | 3.024504 | 3.32135 | 2.379345 | 5.320955 | 5.165949 | 5.091834 |
| SGPP1 | 0.5825627 | 0.058351052 | 0.046125893 | 4.412037769 | 3.024504 | 2.023048 | 2.995681 | 4.718672 | 5.165949 | 4.476242 |
| ZNF346 | 0.631557526 | 0.053106978 | 0.037863899 | 4.409870064 | 7.671922 | 8.016282 | 8.102218 | 9.693068 | 10.626217 | 10.157018 |
| PAK3 | 0.665397621 | 0.050389557 | 0.033233072 | 4.408310355 | 2.201691 | 2.023048 | 2.379345 | 4.341916 | 5.306419 | 4.146207 |
| FBXL4 | 0.630640513 | 0.053156193 | 0.037955767 | 4.408310355 | 2.201691 | 2.023048 | 2.995681 | 4.341916 | 6.205902 | 4.146207 |
| LOC441204 | 0.676775503 | 0.049712169 | 0.032006125 | 4.404505427 | 1.874444 | 2.023048 | 2.165421 | 4.013424 | 5.317867 | 4.146207 |
| FGF7 | 0.667814352 | 0.050279153 | 0.032997618 | 4.404505427 | 1.874444 | 2.023048 | 2.165421 | 4.013424 | 4.131418 | 5.091834 |
| CLEC4C | 0.659342336 | 0.050730781 | 0.03386526 | 4.404505427 | 1.874444 | 2.023048 | 2.165421 | 4.013424 | 4.797798 | 4.146207 |
| KIF6 | 0.649081697 | 0.05155431 | 0.035197006 | 4.404505427 | 1.874444 | 2.023048 | 2.165421 | 4.013424 | 4.539173 | 4.146207 |
| TFDP2 | 0.602911049 | 0.055929015 | 0.042215039 | 4.402755746 | 6.792865 | 6.670655 | 7.401896 | 8.553743 | 9.28507 | 9.540302 |
| KIAA0090 | 0.613344067 | 0.054649646 | 0.040415107 | 4.397153419 | 4.209882 | 3.360637 | 3.764125 | 5.891233 | 5.936219 | 5.900694 |
| SGOL2 | 0.608078561 | 0.055241507 | 0.04125689 | 4.397153419 | 4.209882 | 2.023048 | 2.379345 | 5.320955 | 5.936219 | 5.900694 |
| RPS6KA3 | 0.665245947 | 0.050393971 | 0.033264376 | 4.395032475 | 5.897292 | 5.148082 | 6.012527 | 8.033165 | 8.098861 | 7.920856 |
| RNF207 | 0.590999749 | 0.057296054 | 0.044412385 | 4.392869701 | 3.819732 | 4.413323 | 3.90836 | 6.954147 | 6.043524 | 5.634184 |
| RPL30 | 0.627841934 | 0.053359515 | 0.038388568 | 4.38930984 | 12.434528 | 12.527359 | 12.674306 | 14.402267 | 14.661354 | 15.012718 |
| NEB | 0.600909688 | 0.05625806 | 0.042681865 | 4.384061903 | 3.819732 | 2.406905 | 3.324375 | 6.814118 | 4.539173 | 5.426231 |
| LOC648740 | 0.598432765 | 0.056461394 | 0.043130997 | 4.384061903 | 2.993831 | 2.406905 | 2.995681 | 6.063041 | 4.539173 | 4.562324 |
| MANSC1 | 0.620990997 | 0.053929257 | 0.03933787 | 4.375833998 | 5.328526 | 4.830496 | 4.449894 | 6.960054 | 6.551443 | 8.095288 |
| LARP7 | 0.621388224 | 0.053905072 | 0.039289554 | 4.374608916 | 5.897292 | 5.43468 | 5.596986 | 7.726141 | 7.819723 | 7.668215 |
| ARNTL2 | 0.665305814 | 0.050389557 | 0.033246683 | 4.363982547 | 5.744513 | 6.139057 | 3.324375 | 7.531061 | 7.870158 | 8.03232 |
| CYB561D2 | 0.582833203 | 0.058317693 | 0.046055801 | 4.362655941 | 3.839948 | 3.32135 | 2.379345 | 4.802615 | 5.857745 | 5.446557 |
| RFC1 | 0.586053788 | 0.057869242 | 0.04536509 | 4.361371767 | 4.815804 | 5.297868 | 3.764125 | 7.42265 | 6.373501 | 6.722123 |
| MAP3K12 | 0.577304935 | 0.05913221 | 0.047248724 | 4.357685141 | 4.682076 | 2.023048 | 5.544653 | 5.705318 | 6.551443 | 7.668215 |
| NTM | 0.633597422 | 0.052918525 | 0.037575366 | 4.35647027 | 1.874444 | 2.023048 | 2.165421 | 5.705318 | 3.571326 | 4.146207 |
| 1/2-SBSRNA4 | 0.617330403 | 0.054248673 | 0.03987819 | 4.35647027 | 1.874444 | 2.023048 | 2.165421 | 5.252045 | 3.571326 | 4.146207 |
| FAAH2 | 0.611203161 | 0.054867364 | 0.040681865 | 4.35647027 | 1.874444 | 2.023048 | 2.165421 | 5.095353 | 3.571326 | 4.146207 |
| LRRC6 | 0.602850516 | 0.055929015 | 0.042221844 | 4.35647027 | 1.874444 | 2.023048 | 2.165421 | 4.894482 | 3.571326 | 4.146207 |
| SEMA4G | 0.602846132 | 0.055929015 | 0.042228649 | 4.35647027 | 1.874444 | 2.023048 | 2.165421 | 6.339437 | 3.134528 | 4.146207 |
| MED20 | 0.600837653 | 0.056271437 | 0.042709971 | 4.35647027 | 4.309628 | 2.023048 | 2.165421 | 6.067497 | 6.205902 | 4.146207 |
| TIGD3 | 0.575196242 | 0.059557774 | 0.047758421 | 4.35647027 | 1.874444 | 2.023048 | 2.165421 | 4.341916 | 3.571326 | 4.146207 |
| NHLRC1 | 0.59406393 | 0.056941984 | 0.043777475 | 4.333154296 | 4.815804 | 5.148082 | 5.225216 | 6.960054 | 7.406567 | 6.931222 |
| ADAMTS9-AS2 | 0.570575458 | 0.060307793 | 0.048817965 | 4.324586544 | 2.993831 | 2.023048 | 3.764125 | 5.579836 | 4.608763 | 5.106393 |
| FABP5 | 0.56713409 | 0.060808506 | 0.049514801 | 4.323801552 | 5.700376 | 6.049721 | 5.723602 | 7.835902 | 7.25505 | 8.534542 |
| ILDR2 | 0.575983323 | 0.059372673 | 0.047506635 | 4.319043905 | 1.874444 | 4.351315 | 2.995681 | 6.395481 | 4.797798 | 5.106393 |
| C1orf64 | 0.692028347 | 0.048955004 | 0.03050017 | 4.312039929 | 1.874444 | 2.023048 | 2.165421 | 7.607339 | 4.131418 | 3.630092 |
| LINC00277 | 0.660698794 | 0.050657328 | 0.033710786 | 4.312039929 | 1.874444 | 2.023048 | 2.165421 | 6.396698 | 4.131418 | 3.630092 |
| DNAH7 | 0.650932948 | 0.051450055 | 0.034987411 | 4.312039929 | 1.874444 | 2.023048 | 2.165421 | 6.067497 | 4.131418 | 3.630092 |
| KIF11 | 0.650837653 | 0.051450055 | 0.03498741 | 4.312039929 | 1.874444 | 2.023048 | 2.165421 | 5.705318 | 4.131418 | 3.630092 |
| MKI67 | 0.640654816 | 0.052197898 | 0.036487241 | 4.312039929 | 1.874444 | 2.023048 | 2.165421 | 5.743334 | 4.131418 | 3.630092 |
| LOC375196 | 0.623702521 | 0.055740303 | 0.038926165 | 4.312039929 | 1.874444 | 2.023048 | 2.165421 | 5.095353 | 4.131418 | 3.676349 |
| TDRD5 | 0.604277789 | 0.055729438 | 0.041980946 | 4.312039929 | 1.874444 | 2.023048 | 2.165421 | 7.144104 | 4.131418 | 2.921909 |
| JPH4 | 0.588345849 | 0.057537859 | 0.044900306 | 4.312039929 | 3.024504 | 2.023048 | 2.165421 | 4.894482 | 4.131418 | 4.562324 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA-N171 | BRCA1-N174 |
|---|---|---|---|---|---|---|---|---|---|---|
| RASGRF2 | 0.580676767 | 0.058750841 | 0.046618578 | 4.312039929 | 3.024504 | 2.023048 | 2.995681 | 4.718672 | 4.131418 | 5.882028 |
| FSIP2 | 0.574018552 | 0.059729834 | 0.048047635 | 4.312039929 | 1.874444 | 2.023048 | 2.165421 | 6.252746 | 4.131418 | 2.921909 |
| SP140 | 0.567041929 | 0.060850034 | 0.049574685 | 4.312039929 | 1.874444 | 2.023048 | 2.165421 | 6.067497 | 4.131418 | 2.921909 |
| DCP1A | 0.644330759 | 0.051940717 | 0.036118408 | 4.311712995 | 5.897292 | 5.789702 | 6.056062 | 7.897963 | 8.453372 | 7.988762 |
| STON1 | 0.601969269 | 0.056056571 | 0.042440286 | 4.311682298 | 4.815804 | 3.32135 | 3.90836 | 5.320955 | 6.861783 | 6.924055 |
| CUL5 | 0.619522207 | 0.054008689 | 0.039515481 | 4.304293337 | 6.008206 | 5.661685 | 4.449894 | 7.274575 | 7.767462 | 8.053616 |
| CREM | 0.583423937 | 0.058208993 | 0.045887036 | 4.302217502 | 6.227577 | 6.502398 | 7.69729 | 9.767 | 8.332658 | 9.051056 |
| UTRN | 0.590048615 | 0.057439458 | 0.0446213 | 4.297110305 | 5.897292 | 6.537655 | 7.156853 | 8.641022 | 8.385634 | 8.997112 |
| SNHG8 | 0.629688342 | 0.053228219 | 0.038134059 | 4.292861342 | 4.309025 | 6.184248 | 5.609945 | 8.286188 | 7.406567 | 7.668215 |
| DHDDS | 0.680833229 | 0.049467746 | 0.031572644 | 4.292612468 | 3.350997 | 2.023048 | 3.324375 | 5.448591 | 5.317867 | 5.426231 |
| TMEM170B | 0.601604758 | 0.056112677 | 0.042508336 | 4.291699032 | 4.209882 | 3.872014 | 4.449894 | 5.891233 | 6.551443 | 6.385515 |
| TCF7 | 0.596947402 | 0.056619804 | 0.043361688 | 4.287968018 | 3.350997 | 4.389936 | 5.217616 | 6.244586 | 7.31791 | 6.32627 |
| EPRS | 0.594473707 | 0.056874578 | 0.04293297 | 4.275676573 | 3.350997 | 2.406905 | 2.995681 | 4.739845 | 5.306419 | 5.091834 |
| RPP14 | 0.574120156 | 0.059716764 | 0.047999319 | 4.272972883 | 6.227577 | 5.487673 | 5.974145 | 7.835902 | 8.385634 | 7.582913 |
| ZYG11A | 0.59170848 | 0.057222443 | 0.044285131 | 4.2679743 | 3.024504 | 4.830496 | 4.754917 | 6.651882 | 5.936219 | 6.924055 |
| TCEA3 | 0.643795519 | 0.05192151 | 0.036063967 | 4.257722988 | 5.328526 | 4.736586 | 5.702912 | 7.792994 | 7.414086 | 7.395512 |
| RREB1 | 0.588636771 | 0.057508969 | 0.044818646 | 4.257579181 | 5.316227 | 6.049721 | 5.723602 | 8.139755 | 7.406567 | 7.774634 |
| KCNMB3 | 0.569024334 | 0.06047758 | 0.04910854 | 4.251447552 | 4.263463 | 3.360637 | 2.165421 | 5.448591 | 5.317867 | 5.580533 |
| LOC283888 | 0.571453164 | 0.060151333 | 0.048596121 | 4.245457746 | 1.874444 | 3.360637 | 4.449894 | 5.095353 | 6.043324 | 5.446557 |
| MEGF9 | 0.585911991 | 0.05791529 | 0.045426235 | 4.242978847 | 6.924263 | 7.08238 | 6.769247 | 8.460842 | 9.009341 | 9.562759 |
| WDR67 | 0.583491483 | 0.058208993 | 0.045880231 | 4.242400805 | 3.350997 | 2.809601 | 2.379345 | 4.894482 | 4.539173 | 5.426231 |
| PSMD7 | 0.593606544 | 0.057018726 | 0.043881592 | 4.232149161 | 7.09018 | 6.466258 | 4.449894 | 9.171571 | 8.258856 | 7.897492 |
| TTC27 | 0.655403665 | 0.051058737 | 0.034333447 | 4.230892705 | 3.819732 | 3.872014 | 3.90836 | 6.550689 | 5.920411 | 5.900694 |
| ZNF620 | 0.597294271 | 0.056603505 | 0.043320177 | 4.230892705 | 3.819732 | 2.023048 | 2.165421 | 4.013424 | 5.317867 | 5.900694 |
| LNX1 | 0.579383195 | 0.058820115 | 0.046841102 | 4.229426657 | 3.839948 | 4.389936 | 2.995681 | 7.814607 | 5.920411 | 4.790662 |
| OBSL1 | 0.56542101 | 0.061091369 | 0.049867982 | 4.2268141 | 6.267718 | 6.03611 | 5.571599 | 7.274575 | 8.777924 | 8.11568 |
| NUDT15 | 0.623783793 | 0.053718218 | 0.038901667 | 4.225271913 | 3.350997 | 4.80797 | 4.508334 | 6.811341 | 6.205902 | 6.587378 |
| ASL | 0.620433217 | 0.053986985 | 0.039403879 | 4.222334823 | 5.328526 | 5.297868 | 5.571599 | 7.109557 | 7.406567 | 8.488368 |
| PARP6 | 0.585563116 | 0.057934468 | 0.045484859 | 4.213203065 | 7.355332 | 6.311907 | 6.012527 | 8.087444 | 8.928336 | 9.285145 |
| EIF3A | 0.602378608 | 0.055983853 | 0.042334127 | 4.195996346 | 7.956174 | 7.829709 | 7.98402 | 10.025188 | 10.307217 | 9.635186 |
| SUV39H2 | 0.590450289 | 0.057353094 | 0.044511058 | 4.18606193 | 1.874444 | 3.360637 | 3.90836 | 4.739845 | 5.936219 | 5.426231 |
| LPAR6 | 0.570398128 | 0.060316154 | 0.048843824 | 4.181467599 | 5.491121 | 6.044198 | 6.601009 | 8.665019 | 8.033973 | 7.695565 |
| FRAT2 | 0.591896615 | 0.05748724 | 0.044767608 | 4.180049374 | 5.263699 | 2.406905 | 5.225216 | 6.857154 | 6.189775 | 7.327219 |
| G2E3 | 0.5788261 | 0.058868113 | 0.046944539 | 4.162798874 | 4.682076 | 3.872014 | 5.592916 | 6.498222 | 7.53715 | 6.73963 |
| SPAG16 | 0.683202521 | 0.049394421 | 0.031334468 | 4.160797452 | 4.963444 | 2.023048 | 5.389265 | 6.960054 | 7.187136 | 7.020304 |
| REPS1 | 0.646438144 | 0.051758104 | 0.036666553 | 4.143549777 | 4.743564 | 4.351315 | 2.379345 | 6.283686 | 6.794331 | 6.129407 |
| TNFAIP8L3 | 0.568560215 | 0.060550782 | 0.049244641 | 4.127826737 | 5.328526 | 4.351315 | 2.379345 | 6.396698 | 7.292524 | 5.580533 |
| MACC1 | 0.590659894 | 0.057323276 | 0.044453896 | 4.119000641 | 5.056948 | 5.661685 | 5.217616 | 6.067497 | 7.25505 | 7.492252 |
| NBPF3 | 0.61179168 | 0.05481369 | 0.04060769 | 4.098298853 | 3.839948 | 3.770995 | 4.449894 | 5.705318 | 7.56803 | 5.874974 |
| NRN1 | 0.635366342 | 0.052679972 | 0.037269139 | 4.097356656 | 5.263699 | 4.351315 | 5.225216 | 7.25991 | 6.237456 | 9.311906 |
| ARHGAP5 | 0.602091357 | 0.056022466 | 0.042396734 | 4.091461253 | 6.054828 | 6.072636 | 5.723602 | 8.087444 | 8.564762 | 7.582913 |
| PLCL1 | 0.587073877 | 0.057666624 | 0.045119428 | 4.091343135 | 3.350997 | 3.32135 | 4.449894 | 6.396698 | 5.353925 | 5.900694 |
| DNAJI1 | 0.571517723 | 0.060119309 | 0.048560735 | 4.077185857 | 4.209882 | 2.023048 | 2.379345 | 6.067497 | 6.237456 | 3.676349 |
| C12orf51 | 0.60944289 | 0.055130486 | 0.041034365 | 4.074262825 | 5.744513 | 4.413323 | 6.282905 | 7.771052 | 7.440337 | 8.232333 |
| GEN1 | 0.662288615 | 0.050569223 | 0.033580129 | 4.067179921 | 5.328526 | 2.809601 | 6.072169 | 7.25991 | 8.033973 | 7.352555 |
| ALG13 | 0.570587741 | 0.060307793 | 0.04881116 | 4.063509413 | 6.054828 | 7.106065 | 5.018694 | 8.051486 | 8.077554 | 8.66481 |
| CLSPN | 0.600166288 | 0.056344664 | 0.042812521 | 4.057634517 | 6.736762 | 6.466258 | 6.012527 | 8.033165 | 8.486085 | 9.257878 |
| SORBS2 | 0.603416045 | 0.055822582 | 0.042104117 | 4.05595508 | 6.48761 | 5.297868 | 3.324375 | 8.447068 | 7.31791 | 7.033813 |
| PCBP4 | 0.604603375 | 0.055688845 | 0.041922423 | 4.05516005 | 4.639409 | 4.911517 | 4.754917 | 6.395481 | 6.774676 | 7.722406 |

TABLE 8-continued

Differentially Expressed Genes in CD10−, CD24−, CD44− Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| PIGA | 0.572746041 | 0.059889668 | 0.048299422 | 4.047397101 | 7.410173 | 6.605686 | 5.389265 | 8.955085 | 8.4199 | 8.622681 |
| RPS14 | 0.573602117 | 0.059795609 | 0.044813542 | 4.041384257 | 6.417969 | 7.0089 | 6.704285 | 9.410337 | 8.220489 | 8.719135 |
| RAB6B | 0.685857125 | 0.049293152 | 0.031073154 | 4.034732995 | 4.639409 | 4.80797 | 2.165421 | 6.651882 | 6.640994 | 6.722123 |
| FKBP1B | 0.567081452 | 0.060825097 | 0.049544743 | 4.033551695 | 4.639409 | 4.413323 | 3.90836 | 6.339437 | 5.920411 | 6.739863 |
| KLHDC10 | 0.63026408 | 0.053186878 | 0.038063967 | 4.028162114 | 5.779429 | 5.809601 | 4.724406 | 7.70315 | 7.819723 | 7.582913 |
| FEZ2 | 0.635772622 | 0.052614987 | 0.037186798 | 4.018146841 | 6.143785 | 5.661685 | 2.995681 | 7.477873 | 7.68534 | 7.668215 |
| DDX58 | 0.577883006 | 0.059377251 | 0.047522286 | 4.004046935 | 5.779429 | 6.092406 | 6.704285 | 7.631894 | 8.564762 | 8.705744 |
| SLC37A3 | 0.590114799 | 0.059485925 | 0.044597482 | 3.999629121 | 5.753024 | 5.809601 | 6.056062 | 7.582358 | 8.055928 | 8.010706 |
| TFAP2B | 0.573492814 | 0.059483925 | 0.047656346 | 3.990352321 | 3.819732 | 3.32135 | 2.165421 | 5.743334 | 5.317867 | 4.790662 |
| ZNHIT2 | 0.574115961 | 0.059723631 | 0.048014291 | 3.990352321 | 3.350997 | 3.32135 | 2.379345 | 6.395481 | 5.317867 | 4.146207 |
| RALGPS2 | 0.61903513 | 0.054100449 | 0.039623682 | 3.981996143 | 3.350997 | 2.809601 | 3.324375 | 7.243046 | 5.317867 | 4.476242 |
| INADL | 0.58608689 | 0.057856068 | 0.045331745 | 3.973071129 | 5.700376 | 5.362142 | 3.324375 | 7.450526 | 6.640994 | 7.352555 |
| LOC100652768 | 0.648439971 | 0.051584246 | 0.035290915 | 3.973404729 | 1.874444 | 2.023048 | 2.165421 | 4.013424 | 6.205902 | 3.676349 |
| C14orf1 | 0.64776718 | 0.051631895 | 0.035422933 | 3.973404729 | 2.201691 | 2.023048 | 2.165421 | 4.013424 | 5.317867 | 4.146207 |
| COL6A5 | 0.591458225 | 0.057236297 | 0.045321878 | 3.973404729 | 1.874444 | 2.023048 | 2.165421 | 4.013424 | 4.608763 | 3.676349 |
| SHISA2 | 0.586265489 | 0.05781824 | 0.045286152 | 3.973404729 | 1.874444 | 2.023048 | 2.379345 | 4.013424 | 5.165949 | 3.630092 |
| LYSMD3 | 0.608071352 | 0.055241507 | 0.041263695 | 3.968523126 | 5.856559 | 2.809601 | 4.944468 | 6.857154 | 7.845161 | 6.587378 |
| NHSL1 | 0.600633724 | 0.056295567 | 0.042728139 | 3.947082503 | 3.024504 | 2.809601 | 2.165421 | 4.739845 | 6.043524 | 4.146207 |
| FRMD6-AS1 | 0.622087085 | 0.053826336 | 0.039192923 | 3.918249241 | 6.054828 | 5.661685 | 6.012527 | 7.631894 | 7.96603 | 8.906373 |
| RSBN1 | 0.620213272 | 0.054006231 | 0.039441987 | 3.916354682 | 6.306772 | 3.360637 | 6.326717 | 8.139755 | 8.296229 | 7.46072 |
| GMPR2 | 0.606714338 | 0.055431478 | 0.041528411 | 3.915893432 | 5.779429 | 5.195784 | 6.054038 | 7.748771 | 7.942653 | 7.695565 |
| ITGBL1 | 0.612987097 | 0.054692088 | 0.040481116 | 3.906827387 | 2.201691 | 2.023048 | 2.165421 | 5.743334 | 4.131418 | 3.630092 |
| WAC | 0.6092432 | 0.055148494 | 0.041089486 | 3.900125105 | 6.736762 | 5.362142 | 7.030042 | 8.700282 | 8.777924 | 8.503924 |
| PHACTR2 | 0.572131382 | 0.060021442 | 0.048843688 | 3.89375811 | 7.563198 | 6.092406 | 6.737132 | 8.033165 | 9.524361 | 9.494312 |
| ARMC1 | 0.653370237 | 0.051215566 | 0.034610412 | 3.892864931 | 5.779429 | 5.43468 | 3.324375 | 7.70315 | 7.292524 | 7.395512 |
| RELN | 0.587735386 | 0.057632378 | 0.045010548 | 3.891477272 | 3.024504 | 3.360637 | 4.285996 | 5.320955 | 9.237827 | 4.476242 |
| CFB | 0.566846512 | 0.06087149 | 0.049611432 | 3.891100309 | 6.736762 | 4.413323 | 4.754917 | 8.087444 | 6.373501 | 8.622681 |
| GPANK1 | 0.615000146 | 0.054502508 | 0.04020279 | 3.850211746 | 6.417969 | 4.750708 | 6.012527 | 7.957464 | 7.89473 | 8.232333 |
| KCMF1 | 0.57516633 | 0.059559002 | 0.047774073 | 3.839185479 | 6.846868 | 7.152299 | 7.056312 | 9.02165 | 8.804107 | 8.997112 |
| MGAT4A | 0.579004903 | 0.058854512 | 0.04690575 | 3.825427973 | 4.682076 | 4.351315 | 6.054038 | 7.957464 | 5.857745 | 6.385515 |
| SERPINB9 | 0.585685893 | 0.057930543 | 0.045465805 | 3.821381246 | 10.604984 | 10.20576 | 10.772767 | 12.38198 | 12.706861 | 12.50728 |
| TLL2 | 0.590011284 | 0.057439458 | 0.044628105 | 3.809832667 | 2.201691 | 2.809601 | 2.165421 | 4.013424 | 4.131418 | 5.874974 |
| LRRC8C | 0.591835555 | 0.057215069 | 0.044261313 | 3.783982989 | 4.263463 | 4.750708 | 4.285996 | 7.582358 | 6.205902 | 6.129407 |
| CYB5R1 | 0.572590947 | 0.059927693 | 0.048339571 | 3.768903211 | 5.263699 | 6.03611 | 3.324375 | 7.177844 | 7.473335 | 6.931222 |
| SNRPC | 0.590231225 | 0.057400709 | 0.044566179 | 3.701602063 | 6.678389 | 6.228068 | 3.764125 | 8.566539 | 7.989035 | 7.523109 |
| GALC | 0.617867746 | 0.054205948 | 0.039778106 | 3.673026868 | 6.344798 | 2.023048 | 5.217616 | 6.960054 | 7.094585 | 7.988762 |
| CCDC101 | 0.595230882 | 0.056765675 | 0.043561075 | 3.649965238 | 4.682076 | 2.023048 | 5.225216 | 6.664985 | 6.549959 | 8.340256 |
| ZCCHC4 | 0.5692702 | 0.060422443 | 0.049025519 | 3.561712927 | 8.096549 | 8.203594 | 7.580498 | 9.513069 | 9.872512 | 10.838349 |
| NID2 | 0.573558554 | 0.059548053 | 0.047722355 | 3.557804272 | 4.963444 | 2.023048 | 3.764125 | 5.579836 | 6.794431 | 7.580533 |
| TUSC3 | 0.587760847 | 0.057632378 | 0.045003743 | 3.521519007 | 5.263699 | 5.661685 | 5.217616 | 7.074163 | 8.764653 | 7.033813 |
| GTF3C5 | 0.58399387 | 0.058125809 | 0.045763865 | 3.479414259 | 6.054828 | 6.139057 | 4.754917 | 7.937902 | 7.167462 | 7.695565 |
| PIGG | 0.573525978 | 0.059795609 | 0.04816264 | 3.452363084 | 6.924263 | 6.311907 | 4.508334 | 8.711848 | 7.989035 | 7.920856 |
| RPL10A | 0.581875712 | 0.058472442 | 0.046268118 | 3.411624816 | 11.664076 | 12.12893 | 12.102905 | 13.796321 | 13.434535 | 15.373863 |
| FAM122C | 0.568777241 | 0.060487245 | 0.049183396 | 3.376191033 | 3.350997 | 2.023048 | 3.764125 | 5.095353 | 5.353925 | 5.106393 |
| CDCA4 | 0.57971865 | 0.058818437 | 0.046811841 | 3.307690635 | 4.263463 | 2.023048 | 3.90836 | 5.891233 | 5.509998 | 5.634184 |
| CYP4Z2P | 0.607836375 | 0.055264045 | 0.04132426 | 3.24199663 | 1.874444 | 2.023048 | 2.165421 | 6.396698 | 3.571326 | 3.676349 |
| CENPK | 0.599416654 | 0.056374578 | 0.042939775 | 3.24199663 | 1.874444 | 2.023048 | 2.165421 | 6.283686 | 3.571326 | 3.630092 |
| PKD1L2 | 0.592339152 | 0.057117807 | 0.044123171 | 3.24199663 | 1.874444 | 2.406905 | 2.165421 | 7.037879 | 3.571326 | 3.630092 |
| HNF4G | 0.580986915 | 0.058713636 | 0.04652671 | 3.24199663 | 1.874444 | 2.023048 | 2.165421 | 5.743334 | 3.571326 | 3.630092 |

TABLE 8-continued

Differentially Expressed Genes in CD10–, CD24–, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| CENPE | 0.580439718 | 0.058778844 | 0.046669616 | 3.24199663 | 1.874444 | 2.023048 | 2.165421 | 5.728038 | 3.571326 | 3.630092 |
| CLCA4 | 0.580086959 | 0.058796241 | 0.046731541 | 3.24199663 | 1.874444 | 2.023048 | 2.165421 | 5.579836 | 3.571326 | 3.676349 |
| C5orf27 | 0.575242321 | 0.059556798 | 0.047748214 | 3.24199663 | 1.874444 | 2.023048 | 2.165421 | 5.448591 | 3.571326 | 3.676349 |
| EFNA3 | 0.575242321 | 0.059556798 | 0.047748214 | 3.24199663 | 1.874444 | 2.023048 | 2.165421 | 5.448591 | 3.571326 | 3.676349 |
| TLR3 | 0.565308078 | 0.061121202 | 0.049902007 | 3.24199663 | 1.874444 | 2.023048 | 2.165421 | 5.320955 | 3.571326 | 3.630092 |
| NUB1 | 0.580812511 | 0.058735678 | 0.046587955 | 3.138230176 | 4.963444 | 2.406905 | 5.389265 | 6.395481 | 6.613395 | 7.03218 |
| SERPINA6 | 0.577062955 | 0.059160521 | 0.047280708 | 2.160672033 | 1.874444 | 2.023048 | 2.165421 | 9.111713 | 3.134528 | 2.921909 |
| FGFR3 | 0.576789682 | 0.059216257 | 0.047343995 | 0.163236674 | 6.186289 | 7.197097 | 9.451056 | 6.396698 | 3.571326 | 5.091834 |
| PBX3 | -0.599921695 | 0.056344664 | 0.042845185 | 0.119069371 | 5.335413 | 6.877454 | 7.422239 | 6.183122 | 2.265287 | 2.921909 |
| GAL | -0.727832119 | 0.047482522 | 0.027284791 | 0.007044643 | 2.201691 | 10.779349 | 11.920956 | 2.820813 | 4.608763 | 3.630092 |
| TMEM80 | 0.672786463 | 0.049933984 | 0.032385846 | -0.026302331 | 1.874444 | 2.023048 | 2.165421 | 1.661149 | 7.414086 | 7.36177 |
| LRRC17 | 0.64985539 | 0.051486266 | 0.035062266 | -0.029490783 | 3.024504 | 3.770995 | 3.324375 | 2.820813 | 9.075328 | 8.407967 |
| LGALSL | 0.665988758 | 0.050345474 | 0.033176591 | -0.029738234 | 1.874444 | 2.023048 | 2.379345 | 1.661149 | 7.094585 | 7.897492 |
| NPR2 | 0.641775885 | 0.05203621 | 0.036300102 | -0.031497751 | 1.874444 | 2.406905 | 2.165421 | 1.661149 | 7.25505 | 7.395512 |
| WIF1 | 0.589244536 | 0.05748724 | 0.044749915 | -0.034273582 | 1.874444 | 3.872014 | 2.165421 | 1.661149 | 8.928336 | 7.03218 |
| C16orf89 | 0.636463843 | 0.052578532 | 0.037119428 | -0.036863019 | 1.874444 | 2.023048 | 2.165421 | 1.661149 | 6.78473 | 7.180104 |
| CALN1 | 0.620957766 | 0.053929257 | 0.039344675 | -0.041666207 | 1.874444 | 2.023048 | 2.165421 | 1.661149 | 6.608026 | 7.020304 |
| IFITD1 | 0.609022918 | 0.055156748 | 0.041134399 | -0.042490899 | 1.874444 | 2.406905 | 2.165421 | 1.661149 | 6.640994 | 6.722123 |
| SULT1A2 | 0.628163313 | 0.053354225 | 0.038376318 | -0.043377436 | 1.874444 | 3.872014 | 2.165421 | 1.661149 | 6.549959 | 7.255535 |
| RASL11A | 0.623353924 | 0.053779735 | 0.038881967 | -0.046316877 | 1.874444 | 2.023048 | 2.165421 | 1.661149 | 6.549959 | 6.106561 |
| VTRNA2-1 | 0.629909118 | 0.053198883 | 0.038087785 | -0.047876504 | 1.874444 | 2.809601 | 2.165421 | 2.820813 | 6.549959 | 6.455366 |
| YAE1D1 | 0.588212226 | 0.057572401 | 0.044936373 | -0.050652503 | 1.874444 | 2.023048 | 2.165421 | 1.661149 | 6.608026 | 8.719135 |
| FLJ37453 | 0.622690765 | 0.053781042 | 0.039090167 | -0.053868742 | 1.874444 | 2.023048 | 2.165421 | 1.661149 | 6.237456 | 6.32627 |
| CFI | 0.596638643 | 0.056634604 | 0.043397754 | -0.055059899 | 1.874444 | 2.023048 | 2.165421 | 1.661149 | 6.205902 | 7.523109 |
| TTC12 | 0.581098682 | 0.058657474 | 0.046470228 | -0.055059899 | 1.874444 | 2.023048 | 2.165421 | 1.661149 | 6.205902 | 6.931222 |
| WDR53 | 0.581098682 | 0.058657474 | 0.046470228 | -0.055059899 | 1.874444 | 2.023048 | 2.165421 | 1.661149 | 6.205902 | 6.587378 |
| GSTM5 | 0.642211142 | 0.052001547 | 0.036234774 | -0.0554741 | 1.874444 | 3.872014 | 2.165421 | 1.661149 | 8.119857 | 6.587378 |
| LINC00518 | 0.574174081 | 0.059709894 | 0.047984348 | -0.058984802 | 1.874444 | 2.023048 | 2.165421 | 1.661149 | 6.549959 | 6.195186 |
| LOC91948 | 0.592357428 | 0.057117807 | 0.044116366 | -0.061619223 | 1.874444 | 2.023048 | 2.995681 | 1.661149 | 6.043524 | 6.106561 |
| SPAST | 0.648382924 | 0.051597178 | 0.035309289 | -0.066674675 | 3.024504 | 2.406905 | 2.165421 | 2.820813 | 6.794431 | 7.033813 |
| OLFML1 | 0.575704501 | 0.059399513 | 0.047556312 | -0.069255582 | 1.874444 | 2.023048 | 2.165421 | 1.661149 | 6.861783 | 6.931222 |
| TGFBR3 | 0.570629624 | 0.060307793 | 0.048979755 | -0.092706724 | 9.869873 | 5.297868 | 6.670675 | 9.030914 | 10.697795 | 5.874974 |
| ZNF688 | 0.736142769 | 0.047245915 | 0.026677782 | -0.106653489 | 5.316227 | 2.023048 | 2.165421 | 5.252045 | 6.373501 | 10.101857 |
| FOPNL | 0.622816817 | 0.053781042 | 0.039069752 | -0.110577208 | 4.263463 | 3.872014 | 2.165421 | 4.013424 | 7.440337 | 7.943848 |
| FAM110D | 0.586513181 | 0.057769858 | 0.045227628 | -0.124954205 | 1.874444 | 2.406905 | 8.553333 | 1.661149 | 5.165949 | 7.291822 |
| KLHL8 | 0.578405248 | 0.05896564 | 0.047031643 | -0.129992093 | 4.639409 | 2.809601 | 2.995681 | 4.013424 | 6.549959 | 9.08248 |
| YIF1A | 0.639174717 | 0.05236413 | 0.036694794 | -0.130537464 | 6.417969 | 4.750708 | 8.407885 | 6.063041 | 7.56803 | 7.582913 |
| EIF2B3 | 0.655860976 | 0.050993826 | 0.034281728 | -0.14994268 | 4.815804 | 3.32135 | 8.355951 | 4.739845 | 7.269549 | 9.355434 |
| C1RL | 0.684544018 | 0.049333995 | 0.031214018 | -0.170370622 | 8.653654 | 7.530398 | 8.257481 | 4.718672 | 6.794431 | 7.553321 |
| FAM214B | 0.570629624 | 0.060479768 | 0.04912147 | -2.723567075 | 8.653654 | 7.530398 | 8.553333 | 9.030914 | 7.107836 | 7.03218 |
| EPB41 | -0.570984743 | 0.060259921 | 0.048741068 | -2.743862666 | 6.949166 | 7.829709 | 6.976024 | 1.661149 | 6.373501 | 7.255535 |
| RAB3IL1 | -0.565166666 | 0.061148989 | 0.049946921 | -2.789317281 | 8.129608 | 7.77165 | 8.407885 | 7.440337 | 7.440337 | 5.634184 |
| CHRD | -0.577500921 | 0.05912348 | 0.047232392 | -3.10182488 | 8.183076 | 7.815412 | 8.355951 | 1.661149 | 6.549959 | 6.649696 |
| SLC6A6 | -0.66170494 | 0.050579662 | 0.033627084 | -3.137150692 | 8.264707 | 8.214531 | 8.257481 | 1.661149 | 6.608026 | 7.428484 |
| ELOVL6 | -0.622646088 | 0.053781042 | 0.039096972 | -3.349002317 | 6.344730 | 6.270596 | 6.282905 | 1.661149 | 4.539173 | 6.73963 |
| CTSL1 | -0.568872007 | 0.060479768 | 0.049147329 | -3.442360216 | 11.56685 | 12.044102 | 12.220114 | 8.173604 | 10.260704 | 4.790662 |
| NDOR1 | -0.584765016 | 0.058064889 | 0.045669956 | -3.473764818 | 8.653654 | 8.136169 | 8.407885 | 6.857154 | 4.797798 | 10.561895 |
| USP40 | -0.57011814 | 0.06033194 | 0.048888057 | -3.487642935 | 8.831618 | 8.586982 | 8.477589 | 5.320955 | 6.78473 | 6.69026 |
| MOB2 | -0.566602255 | 0.061004458 | 0.049758421 | -3.489675192 | 9.242593 | 9.342669 | 9.721163 | 7.918071 | 6.189775 | 7.748756 |

TABLE 8-continued

Differentially Expressed Genes in CD10−, CD24−, CD44− Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| B3GALT4 | −0.580161257 | 0.058796241 | 0.046724736 | −3.534864559 | 4.743564 | 4.911517 | 4.508334 | 1.661149 | 3.134528 | 2.921909 |
| FRMD6 | −0.602425223 | 0.055983853 | 0.042327322 | −3.536195015 | 10.70342 | 11.09115 | 10.815695 | 8.993498 | 9.749902 | 5.882028 |
| DPP7 | −0.602451938 | 0.055981204 | 0.042312351 | −3.544312275 | 9.566109 | 9.281572 | 9.353784 | 6.063041 | 7.740604 | 7.582913 |
| RPP25 | −0.565434701 | 0.061091369 | 0.049861177 | −3.555533586 | 5.316227 | 5.195784 | 6.369239 | 1.661149 | 4.539173 | 3.630092 |
| LINC00341 | −0.584662694 | 0.058076564 | 0.045688329 | −3.632620804 | 8.996009 | 8.509169 | 9.583416 | 4.894482 | 7.191402 | 7.722406 |
| LOC100130776 | −0.569041988 | 0.060471767 | 0.049094425 | −3.67753789 | 7.04469 | 6.391145 | 5.702912 | 1.661149 | 5.165949 | 4.790662 |
| REXO2 | −0.565212718 | 0.061131857 | 0.049920381 | −3.690709425 | 10.991122 | 10.797649 | 10.616004 | 8.94532 | 9.107223 | 8.534542 |
| DISP1 | −0.667001664 | 0.050336605 | 0.033113984 | −3.72278708 | 7.530567 | 7.631788 | 7.273415 | 1.661149 | 5.920411 | 5.634184 |
| ALDH1A2 | −0.607221087 | 0.055354487 | 0.041418169 | −3.762813805 | 8.214232 | 8.561508 | 10.172278 | 1.661149 | 8.764653 | 6.649696 |
| SLC7A8 | −0.571389136 | 0.060168186 | 0.048619258 | −3.762877996 | 9.372557 | 7.218985 | 8.66852 | 1.661149 | 7.187136 | 7.46072 |
| FBXL19 | −0.609188432 | 0.055115203 | 0.041105138 | −3.783691236 | 5.491121 | 5.789702 | 5.389265 | 1.661149 | 3.571326 | 4.146207 |
| QRSL1 | −0.57304166 | 0.059837281 | 0.048247703 | −3.797579367 | 10.112425 | 10.575983 | 10.1175278 | 7.679787 | 8.4199 | 8.650903 |
| RASA4P | −0.582242473 | 0.058409447 | 0.046190541 | −3.799598273 | 8.720278 | 7.800972 | 9.708794 | 1.661149 | 6.794431 | 8.440667 |
| NCAPD3 | −0.596272099 | 0.056676183 | 0.043438585 | −3.803739422 | 6.765086 | 7.033812 | 5.974145 | 4.894482 | 2.265287 | 5.106393 |
| DPF2 | −0.61906709 | 0.054100449 | 0.039616876 | −3.804643769 | 9.4134 | 9.104741 | 9.197307 | 5.579836 | 7.269549 | 7.668215 |
| EN2 | −0.569051152 | 0.060471767 | 0.049087445 | −3.823401085 | 6.306772 | 7.033812 | 7.855267 | 1.661149 | 5.920411 | 5.634184 |
| TEP1 | −0.570590603 | 0.060307793 | 0.048804355 | −3.880658028 | 8.69841 | 8.988481 | 8.063885 | 5.252045 | 6.861783 | 7.03218 |
| RPLP0 | −0.602681381 | 0.055954239 | 0.04225655 | −3.900372297 | 16.262427 | 15.918147 | 15.946254 | 14.042609 | 13.451719 | 14.298816 |
| POLL | −0.628527804 | 0.053328876 | 0.038319156 | −3.933651071 | 7.800655 | 7.197097 | 7.227914 | 5.252045 | 5.920411 | 3.630092 |
| ANPEP | −0.609512784 | 0.055120848 | 0.041007826 | −3.943214556 | 10.757297 | 10.094707 | 9.930946 | 6.664985 | 8.777924 | 8.194487 |
| SPRY2 | −0.573270705 | 0.059824474 | 0.048211637 | −3.951334389 | 11.113223 | 9.410824 | 10.06638 | 8.173604 | 8.436733 | 7.428484 |
| ATAT1 | −0.661768665 | 0.050579662 | 0.033620279 | −3.952900832 | 8.096549 | 7.857885 | 7.295639 | 1.661149 | 6.319269 | 5.874974 |
| RBM23 | −0.591067961 | 0.05728668 | 0.044396053 | −3.958050799 | 10.499337 | 9.905188 | 9.68794 | 7.70315 | 8.160956 | 8.010706 |
| CPSF3L | −0.609092228 | 0.055156748 | 0.041127594 | −4.03794869 | 10.047596 | 9.401283 | 8.829514 | 4.894482 | 8.033973 | 7.553321 |
| RNF208 | −0.594325927 | 0.056918505 | 0.043741409 | −4.066606802 | 6.58615 | 6.060401 | 5.225216 | 1.661149 | 4.131418 | 4.562324 |
| SGIP1 | −0.605577374 | 0.055588631 | 0.041762504 | −4.074903319 | 7.278811 | 6.060401 | 6.282905 | 5.252045 | 2.265287 | 4.476242 |
| TEKT4 | −0.628908733 | 0.060497768 | 0.038319156 | −4.184566636 | 9.159663 | 9.013748 | 7.557139 | 6.395481 | 7.094585 | 5.580533 |
| EHD1 | −0.597544631 | 0.056527426 | 0.043235114 | −4.1920442 | 10.300784 | 10.821096 | 10.459924 | 6.498222 | 8.331873 | 8.194487 |
| ATP6V0E1 | −0.622274721 | 0.053817472 | 0.039171147 | −4.21009182 | 11.026657 | 10.885817 | 10.774746 | 8.811966 | 9.086038 | 8.32282 |
| PDCD11 | −0.574360779 | 0.059672428 | 0.047935352 | −4.223792773 | 7.956174 | 8.464054 | 7.519866 | 6.283686 | 4.608763 | 6.385515 |
| MANF | −0.587026465 | 0.057671126 | 0.045141204 | −4.223855652 | 11.239738 | 9.867571 | 9.431116 | 8.331873 | 8.077554 | 7.352555 |
| KHNYN | −0.578119083 | 0.059023503 | 0.047105818 | −4.228937815 | 10.300784 | 10.821096 | 10.459924 | 8.331873 | 8.220489 | 8.952456 |
| FNIP1 | −0.579344147 | 0.058828079 | 0.046856754 | −4.233806643 | 9.60972 | 8.731048 | 9.619106 | 6.811341 | 7.53715 | 7.36177 |
| MLXIP | −0.602275451 | 0.056009923 | 0.042369513 | −4.259749299 | 8.183076 | 9.271133 | 9.455998 | 7.36523 | 6.613395 | 6.129407 |
| CHCHD2 | −0.571697263 | 0.060090644 | 0.048528071 | −4.301434465 | 11.901113 | 12.110017 | 10.885132 | 8.447068 | 9.796295 | 10.044503 |
| SLC2A1 | −0.582026996 | 0.058778844 | 0.046687309 | −4.302967122 | 9.470427 | 8.867571 | 8.387335 | 6.814118 | 6.78473 | 7.428484 |
| ASB1 | −0.583175169 | 0.058250261 | 0.045956448 | −4.310066694 | 8.151234 | 7.458616 | 7.519866 | 5.320955 | 6.043524 | 5.580533 |
| SYNGR3 | −0.604215777 | 0.055732254 | 0.041995917 | −4.316452007 | 4.309025 | 3.770995 | 6.012527 | 1.661149 | 2.265287 | 2.921909 |
| NOC2L | −0.575657175 | 0.059408169 | 0.047572644 | −4.328544045 | 8.351337 | 9.162364 | 7.422239 | 6.544171 | 6.237456 | 5.580533 |
| CCDC167 | −0.584934938 | 0.058034601 | 0.045627765 | −4.335165004 | 8.583805 | 7.991061 | 7.381261 | 5.743334 | 6.043524 | 5.874974 |
| GNL2 | −0.595383637 | 0.056763192 | 0.043543382 | −4.348124552 | 7.730559 | 9.239354 | 8.187891 | 6.067497 | 6.551443 | 5.900694 |
| LRFN4 | −0.5735611 | 0.059795609 | 0.048155835 | −4.355784173 | 5.753024 | 7.174872 | 6.056062 | 4.739845 | 4.131418 | 3.630092 |
| ANKRD13D | −0.621531015 | 0.05903339 | 0.039267778 | −4.367534819 | 8.450608 | 8.278469 | 7.870154 | 5.743334 | 5.857745 | 6.455366 |
| FIBP | −0.57100888 | 0.060259921 | 0.048734263 | −4.375087473 | 10.095792 | 9.568332 | 9.149294 | 6.396698 | 7.91889 | 7.96648 |
| RNF123 | −0.582948922 | 0.058281216 | 0.046006125 | −4.379052629 | 9.545842 | 8.738645 | 8.257481 | 6.244586 | 6.608026 | 7.218312 |
| TRIM11 | −0.702114965 | 0.048553714 | 0.029631848 | −4.384570123 | 8.214232 | 7.991061 | 8.175959 | 1.661149 | 6.043524 | 6.587378 |
| C15orf57 | −0.591444124 | 0.057236297 | 0.044328683 | −4.384950817 | 7.716122 | 8.016282 | 7.227914 | 5.095353 | 5.353925 | 6.106561 |
| CRTC3 | −0.781400954 | 0.045776109 | 0.023239878 | −4.394512506 | 10.336619 | 10.219399 | 10.479473 | 1.661149 | 8.200916 | 8.407967 |
| AGAP3 | −0.64570215 | 0.051818705 | 0.035806737 | −4.396126486 | 9.991752 | 9.327635 | 8.896486 | 7.918071 | 7.191402 | 5.106393 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| CYBASC3 | −0.65972574 | 0.050702199 | 0.033812862 | −4.40160937 | 9.533343 | 8.731048 | 8.677011 | 5.026959 | 6.640994 | 7.395512 |
| PRDM1 | −0.675997116 | 0.049752474 | 0.032078258 | −4.40440939 | 10.139728 | 9.931942 | 12.60146 | 7.792994 | 8.220489 | 8.340256 |
| CXXC1P1 | −0.568830644 | 0.060479768 | 0.049160939 | −4.421238185 | 7.298325 | 6.311907 | 7.250844 | 1.661149 | 6.189775 | 5.106393 |
| PDGFA | −0.577969844 | 0.059048459 | 0.04713508 | −4.439705556 | 9.201724 | 7.912639 | 7.7303 | 5.579836 | 6.774676 | 5.874974 |
| PRDM11 | −0.583195594 | 0.058250261 | 0.045949643 | −4.46476327 | 3.819732 | 4.413323 | 5.217616 | 1.661149 | 2.265287 | 2.921909 |
| C9orf114 | −0.647329836 | 0.05166843 | 0.035498469 | −4.468758627 | 8.415295 | 8.34965 | 8.211462 | 5.743334 | 6.189775 | 6.385515 |
| PPP3CB | −0.697299524 | 0.04880813 | 0.030095271 | −4.47636582 | 7.480194 | 7.512784 | 6.800663 | 1.661149 | 5.317867 | 5.426231 |
| PTGES | −0.645600071 | 0.051818705 | 0.035813542 | −4.491032974 | 11.951287 | 8.833929 | 8.562528 | 6.395481 | 7.473335 | 7.033813 |
| RXRB | −0.583919886 | 0.058126643 | 0.045776114 | −4.50190949 | 9.558037 | 9.2447 | 9.692135 | 7.074163 | 7.269549 | 7.96648 |
| CRAT | −0.655960057 | 0.050993826 | 0.034261313 | −4.502039668 | 10.643643 | 8.124619 | 7.913913 | 5.743334 | 6.205902 | 6.587378 |
| C15orf61 | −0.604377794 | 0.055717618 | 0.041954406 | −4.506861268 | 9.206890 | 9.327635 | 9.316227 | 7.144104 | 7.89473 | 5.900694 |
| FAM173A | −0.594917911 | 0.056842436 | 0.043637972 | −4.512025364 | 7.480194 | 7.218985 | 7.746525 | 1.661149 | 5.306419 | 6.924055 |
| MEN1 | −0.585027669 | 0.058022045 | 0.04560871 | −4.537939495 | 8.69841 | 7.129367 | 7.762571 | 5.579836 | 5.936219 | 5.580533 |
| FOXP4 | −0.575135251 | 0.059555002 | 0.047787683 | −4.541195121 | 7.497182 | 8.436292 | 8.246113 | 6.063041 | 5.936219 | 6.106561 |
| DEGS1 | −0.69182375 | 0.048955004 | 0.030531473 | −4.543057025 | 6.792865 | 6.792427 | 6.704285 | 1.661149 | 4.608763 | 5.091834 |
| LOC100127983 | −0.652882114 | 0.051234373 | 0.034694794 | −4.567929706 | 7.701538 | 8.089403 | 8.994854 | 6.067497 | 5.509998 | 6.051818 |
| ZNF668 | −0.716835922 | 0.047841399 | 0.02818986 | −4.569168271 | 7.298325 | 7.152299 | 7.401896 | 1.661149 | 5.509998 | 5.106393 |
| ACO1 | −0.574424911 | 0.059635779 | 0.047887036 | −4.609342261 | 8.756004 | 7.174872 | 7.317525 | 5.743334 | 6.551443 | 3.676349 |
| MXD3 | −0.666897298 | 0.050336605 | 0.033141204 | −4.616983956 | 7.841135 | 8.101237 | 7.250844 | 6.067497 | 3.134528 | 5.634184 |
| CUL4A | −0.644291042 | 0.051917117 | 0.035996597 | −4.632245334 | 10.169176 | 10.563205 | 10.538909 | 7.957464 | 8.098861 | 8.549611 |
| TFRC | −0.661127619 | 0.050645852 | 0.033688329 | −4.636853604 | 9.952259 | 10.919629 | 10.245467 | 8.156778 | 7.942653 | 8.03232 |
| CAPN2 | −0.623115156 | 0.053781042 | 0.039007826 | −4.670548012 | 8.831618 | 9.302226 | 8.011136 | 4.894482 | 6.608026 | 7.152205 |
| SPSB2 | −0.593755822 | 0.057016532 | 0.043861858 | −4.67310745 | 7.317579 | 5.661685 | 6.355801 | 1.661149 | 4.131418 | 5.580533 |
| SRCRB4D | −0.606109987 | 0.055492203 | 0.041652943 | −4.678913342 | 3.819732 | 5.148082 | 4.724406 | 1.661149 | 2.265287 | 2.921909 |
| FAM176B | −0.570211662 | 0.06033194 | 0.048866962 | −4.679309221 | 11.496784 | 10.775662 | 10.352707 | 7.70315 | 8.549366 | 9.704151 |
| ANKH | −0.575143685 | 0.059559002 | 0.047780878 | −4.693670452 | 8.661211 | 9.659201 | 10.496363 | 7.394225 | 7.505595 | 7.428484 |
| MAPK8IP3 | −0.671400608 | 0.050012479 | 0.032561415 | −4.704546717 | 9.099752 | 8.170275 | 9.041632 | 6.067497 | 5.936219 | 6.931222 |
| MLXIPL | −0.711055131 | 0.048062795 | 0.028683906 | −4.710934525 | 6.48761 | 7.033812 | 7.339085 | 1.661149 | 4.797798 | 5.106393 |
| RAB6A | −0.637829568 | 0.052501106 | 0.036950663 | −4.720057872 | 8.096549 | 6.762934 | 6.564874 | 6.811341 | 5.857745 | 5.091834 |
| SYN1 | −0.625239843 | 0.053566177 | 0.038732222 | −4.733957223 | 4.682076 | 4.413323 | 4.508334 | 1.661149 | 2.265287 | 2.921909 |
| GLYCTK | −0.65534822 | 0.051064299 | 0.034357264 | −4.747642027 | 6.792865 | 4.389936 | 3.90836 | 1.661149 | 2.265287 | 2.921909 |
| PLCH2 | −0.578241219 | 0.05899939 | 0.047077237 | −4.747642027 | 4.263463 | 5.195784 | 3.90836 | 1.661149 | 3.134528 | 2.921909 |
| PRAF2 | −0.569125298 | 0.060463488 | 0.049068391 | −4.747642027 | 5.658609 | 4.830496 | 3.90836 | 1.661149 | 3.134528 | 2.921909 |
| RIC8A | −0.587053667 | 0.057668875 | 0.045130316 | −4.77003192 | 9.823483 | 8.862025 | 8.12722 | 6.067497 | 6.608026 | 7.36177 |
| MTMR10 | −0.648227273 | 0.051597178 | 0.035316094 | −4.77197455 | 9.689484 | 8.805276 | 9.321653 | 6.550689 | 7.505595 | 6.722123 |
| UCN | −0.623038965 | 0.053817472 | 0.039164342 | −4.772474169 | 6.554045 | 5.195784 | 5.389265 | 1.661149 | 3.134528 | 4.562324 |
| ITGB7 | −0.583045539 | 0.058208993 | 0.045873426 | −4.790156046 | 6.227577 | 7.965391 | 9.729351 | 5.705318 | 4.131418 | 6.32627 |
| GALNT2 | −0.800559348 | 0.045343936 | 0.02195917 | −4.806416557 | 9.483274 | 9.327635 | 9.431116 | 1.661149 | 7.174648 | 7.218312 |
| SF3B2 | −0.618939844 | 0.054401265 | 0.040085063 | −4.831939486 | 11.625003 | 11.283907 | 10.529562 | 9.352401 | 8.842512 | 8.534542 |
| LOC401164 | −0.614643103 | 0.054543342 | 0.040253828 | −4.836867155 | 4.309025 | 5.809601 | 3.935222 | 1.661149 | 2.265287 | 2.921909 |
| TCHP | −0.59182425 | 0.057215069 | 0.044268118 | −4.857941559 | 8.085359 | 8.454859 | 8.323869 | 6.811341 | 6.043524 | 5.634184 |
| YRDC | −0.64282037 | 0.05195198 | 0.03617557 | −4.865336645 | 8.535285 | 8.124619 | 7.746525 | 6.252746 | 6.205902 | 4.562324 |
| SLC43A1 | −0.60262496 | 0.055959634 | 0.042269479 | −4.870270968 | 7.730559 | 6.957749 | 8.246113 | 5.743334 | 5.165949 | 5.446557 |
| PRRT1 | −0.634982267 | 0.052738117 | 0.037340592 | −4.878883462 | 6.417969 | 6.228068 | 6.891005 | 1.661149 | 4.131418 | 5.900694 |
| JAGN1 | −0.593237853 | 0.057040543 | 0.043435318 | −4.918509885 | 10.006659 | 8.988481 | 8.175959 | 6.664985 | 7.094585 | 6.69026 |
| SLC22A23 | −0.653433031 | 0.051215566 | 0.034596802 | −4.928850497 | 10.223779 | 8.158996 | 8.279951 | 6.954147 | 5.857745 | 6.051818 |
| ABCF1 | −0.639012375 | 0.052378804 | 0.036713168 | −4.969612481 | 10.452202 | 10.7211 | 9.733427 | 7.631894 | 7.96603 | 8.407967 |
| KAT6A | −0.639563375 | 0.052338861 | 0.036636951 | −4.977947379 | 10.969981 | 11.183109 | 11.570693 | 8.566539 | 8.867558 | 9.478651 |
| GNB2 | −0.641549436 | 0.052091702 | 0.036347057 | −4.988655315 | 12.794595 | 12.085651 | 11.915585 | 9.767 | 9.540026 | 10.508909 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| C15orf17 | −0.650095297 | 0.05147219 | 0.035028241 | −4.990603984 | 9.444387 | 9.538176 | 9.537526 | 7.70315 | 6.774676 | 7.218312 |
| IDUA | −0.578980687 | 0.058855047 | 0.04691868 | −5.031229045 | 8.971905 | 9.614482 | 10.75483 | 7.531061 | 6.640994 | 8.32282 |
| MAFK | −0.630933521 | 0.053142215 | 0.037914257 | −5.034554561 | 9.722364 | 10.106499 | 11.138237 | 8.433162 | 7.740604 | 7.774634 |
| C12orf10 | −0.598826989 | 0.056432998 | 0.043061586 | −5.040235359 | 11.638464 | 10.986561 | 10.809916 | 8.65307 | 8.140553 | 9.832914 |
| FBLN5 | −0.598635997 | 0.056432998 | 0.043083362 | −5.045942424 | 11.343187 | 10.71726 | 12.377524 | 7.36523 | 10.446718 | 9.008063 |
| UBE4B | −0.672514052 | 0.049933984 | 0.032433481 | −5.072413739 | 10.922037 | 11.33617 | 11.042912 | 8.993498 | 8.564762 | 8.870819 |
| UGGT2 | −0.575483844 | 0.059485925 | 0.047663151 | −5.08670682 | 8.57583 | 7.598777 | 6.012527 | 5.252045 | 4.539173 | 5.446557 |
| INTS12 | −0.673096786 | 0.049933984 | 0.03236475 | −5.087321842 | 8.831618 | 9.06903 | 8.163928 | 5.095353 | 6.549959 | 6.722123 |
| MCM2 | −0.647374555 | 0.051665552 | 0.035485539 | −5.094660747 | 7.943836 | 6.957749 | 6.410545 | 5.026959 | 4.608763 | 4.476242 |
| UPK3B | −0.580180648 | 0.05878341 | 0.046700238 | −5.112909273 | 8.824905 | 8.23616 | 8.598731 | 6.244586 | 5.306419 | 7.395512 |
| PLXNA1 | −0.662109739 | 0.050577128 | 0.033609391 | −5.12000005 | 8.424205 | 9.239354 | 9.68794 | 6.067497 | 7.53715 | 6.129407 |
| AAMP | −0.678631703 | 0.049556832 | 0.031763865 | −5.122872886 | 9.3863 | 9.511817 | 9.431116 | 7.074163 | 7.505595 | 6.69026 |
| RCC2 | −0.623918296 | 0.053698943 | 0.038879211 | −5.132570673 | 7.410173 | 11.863059 | 8.234655 | 5.579836 | 7.269549 | 5.874974 |
| PHF1 | −0.594649638 | 0.056878376 | 0.043683566 | −5.135863496 | 11.844989 | 10.407489 | 12.472651 | 8.206677 | 9.179013 | 10.112044 |
| PTK7 | −0.73893081 | 0.04712834 | 0.026470908 | −5.138013217 | 8.535285 | 8.969237 | 8.642743 | 4.718672 | 6.608026 | 6.32627 |
| PPP3CC | −0.638739155 | 0.05242235 | 0.036779857 | −5.145941818 | 10.177104 | 9.457608 | 9.028421 | 6.664985 | 7.25505 | 7.695565 |
| ANKRD9 | −0.694702932 | 0.048858998 | 0.030287173 | −5.148142055 | 9.301804 | 9.013748 | 8.448127 | 6.954147 | 5.165949 | 6.649696 |
| DGKZ | −0.621476081 | 0.053903339 | 0.039274583 | −5.156807651 | 8.638422 | 9.007473 | 9.209064 | 7.504712 | 6.640994 | 5.634184 |
| RNF145 | −0.649575969 | 0.051507311 | 0.03510786 | −5.158148094 | 10.54906 | 10.550312 | 11.118111 | 7.748771 | 8.751258 | 8.692228 |
| ZBTB39 | −0.687394781 | 0.049147961 | 0.030871725 | −5.172921877 | 6.648293 | 6.502398 | 5.702912 | 1.661149 | 4.131418 | 4.476242 |
| ADCYAP1R1 | −0.618855407 | 0.054111443 | 0.03964886 | −5.196471994 | 9.316235 | 8.445606 | 10.144994 | 4.894482 | 7.767462 | 7.352555 |
| CCND2 | −0.606613004 | 0.05543975 | 0.041543382 | −5.19730322 | 10.969981 | 10.58444 | 11.75943 | 8.206677 | 9.74315 | 8.407967 |
| IL32 | −0.668178778 | 0.050279153 | 0.0329459 | −5.200125752 | 10.024346 | 9.96146 | 9.343153 | 7.918071 | 6.237456 | 7.582913 |
| LDLRAP1 | −0.629531067 | 0.053240793 | 0.038153113 | −5.200833296 | 7.786906 | 8.299167 | 6.056062 | 1.661149 | 5.920411 | 5.580533 |
| CYHR1 | −0.653986962 | 0.051134477 | 0.034521946 | −5.209849475 | 8.43306 | 7.615377 | 8.089553 | 5.026959 | 5.936219 | 6.051818 |
| LDB1 | −0.720286737 | 0.047703746 | 0.027910174 | −5.210458242 | 8.535285 | 8.595375 | 9.556058 | 1.661149 | 7.174648 | 6.924055 |
| ACTR1A | −0.651311251 | 0.051429843 | 0.03493297 | −5.210581399 | 9.946086 | 8.99484 | 8.598731 | 5.728038 | 6.613395 | 7.582913 |
| LOC401588 | −0.648011013 | 0.051631895 | 0.03537802 | −5.220007999 | 7.773024 | 6.060401 | 7.611303 | 5.743334 | 4.131418 | 3.676349 |
| WIPI2 | −0.667909389 | 0.050279153 | 0.032984008 | −5.24693146 | 10.392166 | 9.974387 | 10.003631 | 7.976765 | 7.96603 | 7.582913 |
| SAMD4A | −0.630396584 | 0.053156193 | 0.038018374 | −5.256154244 | 8.720278 | 9.821812 | 10.568875 | 7.582358 | 7.767462 | 6.32627 |
| ADAMTS7 | −0.660122936 | 0.050684199 | 0.033762185 | −5.25728583 | 5.316227 | 4.351315 | 4.508334 | 1.661149 | 2.265287 | 2.921909 |
| QSOX1 | −0.655050998 | 0.051064299 | 0.034379721 | −5.258507599 | 10.174466 | 10.896044 | 9.945076 | 8.501391 | 8.258856 | 6.618407 |
| ASF1A | −0.727695934 | 0.047495226 | 0.027313467 | −5.271343058 | 9.170294 | 8.896392 | 9.112206 | 6.498222 | 6.78473 | 6.587378 |
| COPS7B | −0.57668063 | 0.059225813 | 0.047361007 | −5.288355045 | 6.417969 | 3.872014 | 5.974145 | 1.661149 | 3.571326 | 3.676349 |
| AKIRIN2 | −0.669995807 | 0.05007307 | 0.032711807 | −5.298768867 | 11.244777 | 11.22833 | 11.79692 | 8.822673 | 9.158864 | 9.320717 |
| TUBB2B | −0.622545257 | 0.053781042 | 0.039110781 | −5.29887631 | 8.254752 | 9.145317 | 8.355951 | 5.448591 | 6.608026 | 6.73963 |
| LOC283174 | −0.610159044 | 0.055042551 | 0.040923443 | −5.32766668 | 5.335413 | 7.197097 | 5.702912 | 4.013424 | 4.131418 | 2.921909 |
| RANBP9 | −0.622580417 | 0.053781042 | 0.039103777 | −5.340668765 | 10.649353 | 9.905188 | 10.939077 | 8.222933 | 8.4199 | 8.232333 |
| CALU | −0.633613062 | 0.052913654 | 0.037556992 | −5.346445143 | 12.926253 | 11.521536 | 11.990733 | 9.102956 | 9.866312 | 10.302002 |
| LOC100216545 | −0.581635178 | 0.058531256 | 0.04632392 | −5.355484142 | 7.579241 | 6.762934 | 7.825025 | 4.341916 | 4.539173 | 6.385515 |
| BAZ1B | −0.739889804 | 0.047086482 | 0.026394012 | −5.361777882 | 10.266516 | 10.456685 | 10.736668 | 7.877571 | 8.033973 | 8.053616 |
| FCHO2 | −0.620173798 | 0.054006231 | 0.039455597 | −5.366123891 | 5.982974 | 6.049721 | 7.7303 | 1.661149 | 5.306419 | 4.476242 |
| PHPT1 | −0.584243738 | 0.058116747 | 0.04747533 | −5.375688476 | 11.356048 | 11.126325 | 10.088827 | 8.65307 | 8.624754 | 8.929599 |
| SOBP | −0.803184742 | 0.045338539 | 0.021855733 | −5.3835207 | 9.553983 | 9.466786 | 10.298708 | 1.661149 | 7.870158 | 7.218312 |
| HEATR7A | −0.665381641 | 0.050389557 | 0.033239878 | −5.389365281 | 7.671922 | 8.388801 | 7.227914 | 5.728038 | 4.797798 | 5.446557 |
| YTHDC1 | −0.620821895 | 0.053957661 | 0.039373937 | −5.392162439 | 12.142253 | 11.711095 | 12.738081 | 10.174762 | 10.307217 | 9.276113 |
| SEC31A | −0.710515588 | 0.048141008 | 0.028752637 | −5.39911954 | 12.964166 | 12.567371 | 12.463477 | 9.778045 | 10.531442 | 10.233665 |
| AMOTL1 | −0.705928655 | 0.048355462 | 0.029248044 | −5.4111228 | 9.562079 | 9.767145 | 10.309671 | 5.026959 | 7.845161 | 7.873743 |
| DENND5A | −0.707841206 | 0.048268527 | 0.029021436 | −5.41641842 | 10.874072 | 10.609516 | 11.314569 | 9.058353 | 8.436733 | 7.218312 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| G3BP1 | −0.714814255 | 0.047877006 | 0.028338891 | −5.429613022 | 10.668227 | 10.711481 | 11.38104 | 8.361545 | 8.94019 | 7.523109 |
| CENPO | −0.67016014 | 0.050073072 | 0.032705002 | −5.435393982 | 8.415295 | 7.952383 | 7.4423 | 5.252045 | 5.509998 | 5.882028 |
| PQBP1 | −0.715057074 | 0.047877006 | 0.028304866 | −5.438554222 | 10.861007 | 10.682232 | 10.371139 | 8.239009 | 8.140553 | 8.287303 |
| TUSC1 | −0.68768578 | 0.049147961 | 0.030844505 | −5.4682029 | 11.023729 | 10.082818 | 10.440106 | 6.252746 | 7.989035 | 8.929599 |
| PGRMC1 | −0.656238279 | 0.050993826 | 0.034236815 | −5.471894209 | 11.344361 | 12.34279 | 12.202577 | 8.745998 | 10.047106 | 9.750536 |
| STEAP1 | −0.662901348 | 0.050504642 | 0.033478054 | −5.48499336 | 10.707075 | 8.841005 | 8.163928 | 6.244586 | 7.066159 | 6.385515 |
| METTL17 | −0.700188684 | 0.048716465 | 0.029853692 | −5.486180102 | 10.963884 | 11.082221 | 10.32596 | 8.361545 | 7.870158 | 8.66481 |
| OTUD7B | −0.725543864 | 0.047551011 | 0.027454236 | −5.500903441 | 8.493568 | 8.23616 | 8.334642 | 5.320955 | 6.237456 | 5.874974 |
| TMEM204 | −0.644228499 | 0.051917117 | 0.036003403 | −5.5125791185 | 11.072716 | 8.949732 | 9.374815 | 1.661149 | 8.609988 | 8.32282 |
| SLC44A1 | −0.643459532 | 0.051940717 | 0.036111603 | −5.525143657 | 11.210423 | 9.659201 | 10.40986 | 7.835902 | 8.350533 | 7.943848 |
| CNIH4 | −0.587354383 | 0.057642811 | 0.045064308 | −5.530294582 | 6.099991 | 4.911517 | 5.389265 | 1.661149 | 4.539173 | 2.921909 |
| CAPN5 | −0.637235706 | 0.052514975 | 0.037033004 | −5.348106696 | 7.336579 | 6.311907 | 6.948237 | 1.661149 | 5.857745 | 4.476242 |
| FAM89B | −0.617512672 | 0.054225734 | 0.03983736 | −5.563615815 | 9.099752 | 9.686953 | 9.542181 | 6.550689 | 7.066159 | 7.920856 |
| ATP8B2 | −0.622840508 | 0.053781042 | 0.039062947 | −5.591518861 | 9.927407 | 8.101237 | 9.1735 | 5.728038 | 7.406567 | 6.69026 |
| CMIP | −0.659950267 | 0.050684199 | 0.03376899 | −5.617591086 | 10.499357 | 12.374223 | 10.432604 | 8.768324 | 7.942653 | 8.822008 |
| ABU | −0.580726003 | 0.058750841 | 0.046611773 | −5.620163214 | 10.643643 | 11.152155 | 10.992779 | 9.716222 | 8.502167 | 8.03232 |
| ZNF592 | −0.633699863 | 0.052882301 | 0.03752637 | −5.6439882 | 9.663383 | 9.104741 | 9.66678 | 7.918071 | 6.608026 | 6.942983 |
| LRR1 | −0.635673348 | 0.05262489 | 0.037218782 | −5.646686927 | 6.973646 | 6.42919 | 7.4423 | 1.661149 | 6.043524 | 4.476242 |
| NENF | −0.648810972 | 0.051560318 | 0.035225587 | −5.687911995 | 6.344798 | 6.184248 | 5.389265 | 1.661149 | 4.539173 | 3.676349 |
| CDK2AP2 | −0.619232567 | 0.054043498 | 0.039556312 | −5.695895386 | 11.225792 | 11.174733 | 10.613794 | 7.748771 | 9.563208 | 8.66481 |
| SLC41A1 | −0.655978784 | 0.050993826 | 0.034254508 | −5.705594812 | 11.989307 | 9.781927 | 10.520155 | 8.270632 | 7.269549 | 8.834367 |
| TAPBP | −0.683629873 | 0.049394421 | 0.031323579 | −5.712085204 | 10.073312 | 9.9999 | 11.136698 | 5.891233 | 8.181074 | 8.622681 |
| MMP19 | −0.670970149 | 0.050055202 | 0.032628105 | −5.727261606 | 11.25105 | 10.658398 | 10.427581 | 7.792994 | 8.140553 | 9.018932 |
| TRIM26 | −0.59453525 | 0.056882604 | 0.043695815 | −5.736091038 | 8.947392 | 8.225386 | 10.315121 | 5.705318 | 6.373501 | 8.010706 |
| ANKRD33B | −0.701262867 | 0.048630415 | 0.029732562 | −5.753796151 | 10.681293 | 10.996101 | 11.130529 | 8.156778 | 8.36819 | 8.929599 |
| PARP1 | −0.63567357 | 0.05262489 | 0.037205172 | −5.775491806 | 7.956174 | 6.821329 | 8.66852 | 5.320955 | 5.509998 | 5.426231 |
| SHISA5 | −0.586053813 | 0.057869242 | 0.045358285 | −5.80921866 | 9.11634 | 9.228604 | 7.7303 | 6.283686 | 6.551443 | 6.69026 |
| TAF3 | −0.665021558 | 0.050400851 | 0.033282749 | −5.81908058 | 11.305107 | 9.935252 | 9.494939 | 6.954147 | 8.36819 | 7.611911 |
| BCL9L | −0.719891668 | 0.047724223 | 0.02794556 | −5.824117325 | 9.648253 | 9.162364 | 9.636624 | 5.026959 | 7.094585 | 7.611911 |
| PNLDC1 | −0.737998639 | 0.047140798 | 0.026553249 | −5.831655264 | 10.484506 | 10.53294 | 10.868547 | 7.556937 | 7.989035 | 8.519314 |
| RHBDL1 | −0.57890274 | 0.058863581 | 0.046931609 | −5.83947779 | 6.227577 | 4.736586 | 6.175931 | 1.661149 | 4.539173 | 3.630092 |
| IDO1 | −0.706030827 | 0.048351237 | 0.029227628 | −5.85120299 | 4.209882 | 4.80797 | 6.056062 | 1.661149 | 2.265287 | 2.921909 |
| NEURL3 | −0.569865599 | 0.06033611 | 0.048936373 | −5.85120299 | 4.209882 | 5.789702 | 6.976024 | 1.661149 | 4.797798 | 2.921909 |
| LY6K | −0.685884181 | 0.049293152 | 0.031059544 | −5.858441778 | 4.815804 | 6.502398 | 3.90836 | 1.661149 | 2.265287 | 2.921909 |
| NPM3 | −0.596903477 | 0.056619804 | 0.044368493 | −5.866673135 | 8.369902 | 9.770854 | 7.519866 | 4.718672 | 6.189775 | 7.218312 |
| ALG3 | −0.666742144 | 0.050336605 | 0.03314801 | −5.868917913 | 10.184989 | 10.45438 | 9.569802 | 7.631894 | 6.794431 | 8.305171 |
| THAP3 | −0.661252638 | 0.050645852 | 0.033681524 | −5.876019123 | 10.793848 | 10.601206 | 9.226523 | 8.239009 | 5.936219 | 8.232333 |
| DPYSL4 | −0.712652267 | 0.047957459 | 0.028498809 | −5.877637703 | 9.301804 | 8.841005 | 8.874506 | 7.037879 | 6.319269 | 6.051818 |
| ATAD3A | −0.678658873 | 0.049556832 | 0.03175706 | −5.879264025 | 7.445608 | 8.136169 | 8.13956 | 4.802615 | 5.936219 | 5.580533 |
| DYNLL1 | −0.590293302 | 0.057400709 | 0.044555937 | −5.885294589 | 8.313476 | 8.535576 | 7.663508 | 7.037879 | 5.509998 | 5.106393 |
| SDK1 | −0.703486747 | 0.048494719 | 0.029511398 | −5.902963212 | 12.686273 | 13.376538 | 14.094171 | 10.580119 | 10.815098 | 11.043888 |
| UCN2 | −0.588136115 | 0.057577292 | 0.044949302 | −5.911469437 | 10.009622 | 7.303362 | 7.628916 | 4.739845 | 6.774676 | 5.900694 |
| PLCD4 | −0.688546416 | 0.049115877 | 0.030789384 | −5.918405557 | 4.209882 | 4.830496 | 5.596986 | 1.661149 | 2.265287 | 2.921909 |
| SLC20A2 | −0.637201839 | 0.052523453 | 0.037047295 | −5.918405557 | 4.815804 | 4.830496 | 5.225216 | 1.661149 | 2.265287 | 3.630092 |
| HES6 | −0.582710102 | 0.058324851 | 0.046089146 | −5.939296851 | 9.830202 | 10.999267 | 8.555333 | 7.25991 | 7.174648 | 7.988762 |
| ASB6 | −0.699391995 | 0.048734593 | 0.029926506 | −5.944987954 | 8.0045 | 6.849665 | 7.663508 | 5.728038 | 3.134528 | 5.091834 |
| ACOX3 | −0.746715559 | 0.046800775 | 0.02587951 | −5.949214733 | 9.186094 | 9.789261 | 9.048192 | 6.550689 | 6.613395 | 7.020304 |
| COL4A1 | −0.658170362 | 0.050826016 | 0.033993195 | −5.984695075 | 7.867504 | 7.899144 | 8.366488 | 6.664985 | 5.317867 | 4.476242 |
| | −0.628216583 | 0.053354225 | 0.038369513 | −5.993564323 | 13.2 | 11.517125 | 11.709604 | 8.344785 | 9.776594 | 10.616586 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| MVK | −0.725430667 | 0.047551011 | 0.027467846 | −6.022175436 | 8.224469 | 7.303362 | 6.450701 | 1.661149 | 4.797798 | 5.634184 |
| CLSTN3 | −0.582365366 | 0.058378104 | 0.046156516 | −6.059927337 | 9.496006 | 7.991061 | 9.460924 | 4.739845 | 6.861783 | 7.873743 |
| PLSCR2 | −0.637718941 | 0.052501106 | 0.036964274 | −6.082249516 | 4.815804 | 4.736586 | 6.175931 | 1.661149 | 3.571326 | 2.921909 |
| MESDC1 | −0.76805643 | 0.046157531 | 0.024259952 | −6.120787725 | 8.720278 | 8.34965 | 9.093298 | 5.891233 | 6.189775 | 6.106561 |
| MAMLD1 | −0.653010131 | 0.051221132 | 0.03446281 | −6.126074355 | 6.186289 | 6.228068 | 7.381261 | 4.739845 | 3.571326 | 4.146207 |
| SLC16A7 | −0.568540828 | 0.060558243 | 0.049260293 | −6.159206453 | 5.753024 | 4.830496 | 5.544653 | 1.661149 | 4.539173 | 2.921909 |
| RPS6KB2 | −0.65630138 | 0.050987756 | 0.034214359 | −6.161819254 | 6.099991 | 6.537655 | 4.285996 | 1.661149 | 2.265287 | 4.476242 |
| PAK6 | −0.597910353 | 0.056511538 | 0.043207213 | −6.161819254 | 5.316227 | 7.631788 | 4.285996 | 1.661149 | 4.539173 | 2.921909 |
| NOL7 | −0.565942528 | 0.061013478 | 0.049775434 | −6.161819254 | 6.973646 | 6.821329 | 4.285996 | 1.661149 | 3.134528 | 5.426231 |
| PPP1R3F | −0.645798961 | 0.051818705 | 0.035789044 | −6.173852491 | 9.632963 | 8.136169 | 8.767255 | 6.067497 | 5.509998 | 7.352555 |
| INHBA | −0.743983806 | 0.046883977 | 0.026065328 | −6.21077408 | 7.906175 | 7.197097 | 7.107458 | 1.661149 | 5.920411 | 4.562324 |
| REC8 | −0.654372642 | 0.051128995 | 0.03448588 | −6.211188386 | 6.648293 | 7.912639 | 8.932392 | 4.013424 | 4.539173 | 6.587378 |
| HS6ST1 | −0.811798301 | 0.045218796 | 0.021255529 | −6.214967094 | 8.224469 | 8.595375 | 9.243773 | 1.661149 | 6.608026 | 6.051818 |
| SLC3A2 | −0.770754927 | 0.04607418 | 0.02404015 | −6.222570977 | 12.31447 | 11.868263 | 11.933413 | 9.337546 | 9.158864 | 9.676959 |
| UBTD1 | −0.708048713 | 0.048268527 | 0.029007826 | −6.233207508 | 9.247621 | 9.434406 | 9.66678 | 6.252746 | 6.794431 | 7.582913 |
| MAP3K6 | −0.646038166 | 0.051811216 | 0.035749575 | −6.251857735 | 7.067614 | 8.278469 | 9.099629 | 5.026959 | 6.205902 | 5.634184 |
| C14orf176 | −0.630776355 | 0.053145686 | 0.03793195 | −6.260290154 | 3.350997 | 4.911517 | 6.601009 | 1.661149 | 2.265287 | 2.921909 |
| DHX37 | −0.649742472 | 0.051496281 | 0.035084042 | −6.265496617 | 8.294165 | 8.988481 | 7.899474 | 5.252045 | 5.306419 | 7.03218 |
| GFM1 | −0.617366115 | 0.054239984 | 0.039863219 | −6.275649048 | 8.84495 | 8.916627 | 7.4423 | 6.252746 | 5.857745 | 6.195186 |
| REL | −0.77035407 | 0.046076407 | 0.024057843 | −6.288132133 | 11.464756 | 11.038265 | 12.534117 | 8.895478 | 8.385634 | 9.143346 |
| PEX10 | −0.61195855 | 0.054273567 | 0.039939435 | −6.289823517 | 7.744853 | 7.615377 | 6.031658 | 4.718672 | 4.539173 | 5.091834 |
| GFER | −0.722844951 | 0.04762218 | 0.027660429 | −6.316630267 | 9.83355 | 8.595375 | 8.925282 | 6.339437 | 5.936219 | 7.020304 |
| ULK1 | −0.728553698 | 0.047423411 | 0.027214699 | −6.336831217 | 9.277427 | 8.603718 | 9.955583 | 4.894482 | 6.78473 | 7.291822 |
| PLAC8L1 | −0.752486578 | 0.046595104 | 0.025434502 | −6.386730266 | 4.815804 | 4.750788 | 5.596986 | 1.661149 | 2.265287 | 2.921909 |
| IRF7 | −0.630020793 | 0.053186878 | 0.038070772 | −6.390636271 | 9.227402 | 9.626816 | 9.902263 | 8.173604 | 6.551443 | 6.931222 |
| E4F1 | −0.778344452 | 0.045844227 | 0.023423613 | −6.404922988 | 5.491121 | 4.911517 | 4.944468 | 1.661149 | 2.265287 | 2.921909 |
| C8orf73 | −0.744516681 | 0.046883977 | 0.026044913 | −6.431708718 | 6.099991 | 6.139057 | 6.83141 | 1.661149 | 4.131418 | 4.146207 |
| LEPREL1 | −0.640950745 | 0.05213413 | 0.036409663 | −6.435879381 | 5.316227 | 4.351315 | 5.389265 | 7.037879 | 2.265287 | 3.630092 |
| HLX | −0.573475064 | 0.059795609 | 0.048169445 | −6.435879381 | 6.52121 | 4.351315 | 5.702912 | 1.661149 | 4.608763 | 2.921909 |
| ILK | −0.731855259 | 0.047353867 | 0.026993535 | −6.455088136 | 12.117061 | 12.072184 | 12.305422 | 9.08528 | 9.426624 | 10.171703 |
| PACS1 | −0.767247636 | 0.046164489 | 0.024342974 | −6.464290503 | 9.065993 | 8.509169 | 8.345336 | 4.739845 | 6.373501 | 6.106561 |
| SRGAP1 | −0.728915344 | 0.047423411 | 0.027194284 | −6.488745223 | 10.166524 | 10.926298 | 11.422028 | 7.037879 | 8.724089 | 8.32282 |
| ADO | −0.728523362 | 0.047423411 | 0.027221504 | −6.496926702 | 8.804578 | 8.147628 | 8.767255 | 6.067497 | 6.613395 | 4.562324 |
| CCDC86 | −0.808952879 | 0.045247607 | 0.021441307 | −6.497686323 | 10.033108 | 11.065705 | 9.969475 | 7.607339 | 7.269549 | 7.46072 |
| KIAA0368 | −0.751219483 | 0.046631339 | 0.02552637 | −6.515005865 | 11.299065 | 11.518229 | 12.061349 | 8.94532 | 9.357582 | 8.579284 |
| GANAB | −0.759027971 | 0.04712834 | 0.026464103 | −6.517918164 | 11.422029 | 10.227521 | 9.369586 | 7.274575 | 7.713236 | 7.523109 |
| SERPINB6 | −0.704762756 | 0.048386088 | 0.029343995 | −6.521375886 | 11.284461 | 10.414621 | 10.508308 | 7.631894 | 8.332658 | 8.579284 |
| CHTF18 | −0.666944265 | 0.050336605 | 0.033127594 | −6.548513661 | 8.691047 | 9.145317 | 10.459924 | 6.664985 | 5.920411 | 7.748756 |
| DNER | −0.800027807 | 0.045343942 | 0.022031303 | −6.572701764 | 7.278811 | 6.732825 | 6.355801 | 1.661149 | 4.131418 | 4.562324 |
| MIR205HG | −0.777286105 | 0.045858846 | 0.023507315 | −6.605553343 | 9.761558 | 12.403193 | 9.272072 | 7.037879 | 7.167462 | 6.722123 |
| SDS | −0.690986891 | 0.048967655 | 0.03059476 | −6.628983794 | 5.056948 | 4.389936 | 7.942366 | 1.661149 | 3.571326 | 2.921909 |
| LHFPL2 | −0.590604418 | 0.05733088 | 0.044475672 | −6.675087649 | 10.509839 | 10.015619 | 10.548196 | 7.771052 | 9.357582 | 6.924055 |
| CLN6 | −0.753587937 | 0.046571395 | 0.025535522 | −6.681745529 | 7.906175 | 8.692451 | 7.663508 | 6.063041 | 5.165949 | 4.476242 |
| RAB14 | −0.823445693 | 0.045005314 | 0.020505614 | −6.688665342 | 12.216577 | 11.995784 | 12.002604 | 9.260886 | 9.492512 | 9.201749 |
| PKM2 | −0.713312871 | 0.047910176 | 0.028425995 | −6.69713948 | 12.705129 | 11.923468 | 11.142841 | 9.179923 | 9.128102 | 9.547827 |
| BOP1 | −0.705631933 | 0.048360255 | 0.029260293 | −6.736594165 | 8.107653 | 9.391678 | 8.634047 | 7.037879 | 4.797798 | 5.882028 |
| FTX | −0.734915262 | 0.047277268 | 0.026717931 | −6.736949755 | 11.37685 | 11.502697 | 10.748801 | 8.616619 | 8.624754 | 8.745549 |
| C1QB | −0.654980874 | 0.051064299 | 0.034386526 | −6.737316104 | 6.48761 | 4.413323 | 8.151795 | 1.661149 | 2.265287 | 5.580533 |
| E2F3 | −0.776480516 | 0.045873421 | 0.02360871 | −6.770394439 | 8.254752 | 8.544272 | 8.487278 | 5.728038 | 6.237456 | 4.790662 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| WDR45 | −0.851215296 | 0.044490827 | 0.018807077 | −6.80048145 | 11.631749 | 11.067214 | 10.965312 | 8.301578 | 8.220489 | 8.357484 |
| CLTB | −0.787568327 | 0.045564387 | 0.022781899 | −6.806256017 | 10.452202 | 11.32738 | 10.365897 | 6.550689 | 7.68534 | 8.66481 |
| TCIRG1 | −0.755218454 | 0.046505334 | 0.025243961 | −6.809129204 | 10.956225 | 9.853646 | 10.1327 | 7.36523 | 7.187136 | 8.095288 |
| MT2A | −0.583221464 | 0.058250261 | 0.045942838 | −6.825889039 | 16.589026 | 16.588349 | 15.299176 | 12.528159 | 13.23365 | 15.384407 |
| FAM3A | −0.732351939 | 0.047319258 | 0.02695883 | −6.833413098 | 11.05991 | 10.052661 | 9.955583 | 6.811341 | 7.656894 | 8.287303 |
| UBN1 | −0.783419109 | 0.045695042 | 0.023071113 | −6.835279089 | 8.630745 | 8.041069 | 8.063885 | 4.718672 | 5.857745 | 5.634184 |
| DIO3 | −0.757564004 | 0.046414887 | 0.024984008 | −6.873299715 | 4.815804 | 4.750708 | 5.702912 | 1.661149 | 2.265287 | 2.921909 |
| SLC25A38 | −0.625092429 | 0.053581742 | 0.038751956 | −6.884540775 | 9.558037 | 9.568332 | 9.283238 | 6.252746 | 6.774676 | 8.213534 |
| UNC45A | −0.707208261 | 0.048286461 | 0.029084042 | −6.889717456 | 10.991122 | 9.807436 | 9.854403 | 8.206677 | 7.656894 | 6.69026 |
| ATG4B | −0.817377487 | 0.045152347 | 0.020873086 | −6.909282283 | 10.228873 | 9.778245 | 10.284887 | 4.894482 | 7.440337 | 7.774634 |
| MYLPF | −0.691757806 | 0.048955004 | 0.030545083 | −6.910284693 | 5.304463 | 6.044198 | 4.449894 | 1.661149 | 2.265287 | 3.630092 |
| ANKMY1 | −0.674662752 | 0.04983446 | 0.03220211 | −6.910284693 | 6.898923 | 5.195784 | 4.449894 | 1.661149 | 3.571326 | 2.921909 |
| FBXO18 | −0.702920534 | 0.048515004 | 0.0295672 | −6.912562631 | 11.784865 | 10.539479 | 10.239746 | 7.450526 | 8.181074 | 8.822008 |
| LTBP3 | −0.725943931 | 0.047543032 | 0.027439946 | −6.915055221 | 9.799716 | 10.815719 | 11.383636 | 6.252746 | 8.2398 | 8.593895 |
| NRXN2 | −0.570411423 | 0.060316154 | 0.048837019 | −6.931329527 | 4.682076 | 4.750708 | 7.401896 | 1.661149 | 4.608763 | 2.921909 |
| ADCK5 | −0.740465724 | 0.047053425 | 0.026338891 | −6.933443315 | 8.5104 | 7.402335 | 7.794136 | 4.894482 | 4.608763 | 5.900694 |
| CYP1A1 | −0.795787918 | 0.045395954 | 0.022293297 | −6.941746079 | 7.513971 | 6.792427 | 6.601009 | 4.718672 | 4.131418 | 2.921909 |
| SCT | −0.609808088 | 0.0551042214 | 0.04098673 | −6.972580711 | 3.350997 | 5.148082 | 5.723602 | 1.661149 | 2.265287 | 2.921909 |
| ZNF703 | −0.69264847 | 0.048944238 | 0.030441647 | −6.984324236 | 5.658609 | 7.197097 | 7.899474 | 5.095353 | 4.131418 | 2.921909 |
| CLCF1 | −0.746989541 | 0.046798828 | 0.025848248 | −6.998171017 | 7.579241 | 8.329668 | 8.743197 | 5.728038 | 5.936219 | 4.476242 |
| CRTC2 | −0.806427756 | 0.045297753 | 0.021613474 | −7.006635641 | 9.358681 | 8.868964 | 9.7854 | 6.550689 | 6.549959 | 6.455366 |
| AGPAT6 | −0.841889051 | 0.044695604 | 0.019338551 | −7.010405138 | 10.52234 | 10.346648 | 10.309671 | 7.792994 | 7.53715 | 7.291822 |
| KRT5 | −0.772872808 | 0.046036363 | 0.023862538 | −7.016388947 | 12.45478 | 15.685283 | 11.439601 | 8.628872 | 10.167971 | 10.106959 |
| FAM131A | −0.654351102 | 0.051134477 | 0.034501531 | −7.017626845 | 8.668728 | 7.34377 | 6.175931 | 4.013424 | 5.857745 | 4.146207 |
| FAM50B | −0.779463329 | 0.045829476 | 0.023342634 | −7.020345328 | 6.973646 | 6.957749 | 6.489771 | 1.661149 | 4.797798 | 4.146207 |
| SEC16A | −0.814901589 | 0.045198955 | 0.021101735 | −7.056830439 | 10.412457 | 10.760815 | 9.996864 | 7.177844 | 7.627877 | 7.774634 |
| NUDT4 | −0.588394916 | 0.057530341 | 0.044885335 | −7.070634371 | 12.289089 | 11.431828 | 10.190185 | 7.243046 | 8.609988 | 10.413286 |
| NFYA | −0.774681697 | 0.046000938 | 0.02378428 | −7.074457873 | 10.226328 | 9.511817 | 10.295954 | 7.037879 | 7.473335 | 7.36177 |
| GABBR1 | −0.726034179 | 0.047543032 | 0.027433141 | −7.099804308 | 10.432466 | 9.781927 | 10.559721 | 6.954147 | 8.296229 | 7.492252 |
| MGC12982 | −0.663891751 | 0.050428178 | 0.0333508 | −7.109836982 | 6.648293 | 4.389936 | 6.976024 | 1.661149 | 3.571326 | 4.146207 |
| HLA-C | −0.777917909 | 0.045844227 | 0.023450834 | −7.109901294 | 14.565223 | 14.24246 | 14.570289 | 11.412631 | 12.186026 | 11.653272 |
| SRGAP2 | −0.622993791 | 0.053781042 | 0.039014631 | −7.141197354 | 7.641685 | 8.509169 | 10.336718 | 5.743334 | 7.505595 | 6.649696 |
| MIR3682 | −0.734434678 | 0.047307334 | 0.026759442 | −7.163505134 | 8.69841 | 6.821329 | 9.255159 | 5.705318 | 5.857745 | 5.882028 |
| GPR137 | −0.722993726 | 0.04762218 | 0.027646819 | −7.117449004 | 6.820119 | 7.679931 | 8.279951 | 5.448591 | 5.165949 | 3.630092 |
| C1orf216 | −0.825702351 | 0.044949653 | 0.020389929 | −7.121901626 | 10.454378 | 9.898421 | 9.816476 | 5.705318 | 7.066159 | 7.800057 |
| DUSP4 | −0.789983711 | 0.045525452 | 0.022658727 | −7.128194378 | 7.716122 | 7.26179 | 7.4423 | 5.448591 | 4.608763 | 2.921909 |
| KAZN | −0.69228366 | 0.048955004 | 0.030479755 | −7.129613805 | 10.403474 | 13.158825 | 11.763423 | 9.584013 | 8.277663 | 8.929599 |
| ABCA2 | −0.713190736 | 0.047910176 | 0.0284328 | −7.133128022 | 10.52855 | 10.664394 | 9.696318 | 8.628872 | 6.861783 | 7.152205 |
| NUDT22 | −0.669642476 | 0.050087347 | 0.032736985 | −7.140756662 | 7.730559 | 8.436292 | 9.490128 | 1.661149 | 6.373501 | 6.455366 |
| SLC26A6 | −0.615844857 | 0.054404356 | 0.040095951 | −7.195500884 | 9.170294 | 11.432999 | 10.640089 | 7.792994 | 8.140553 | 5.649696 |
| IP6K1 | −0.7892139913 | 0.045529634 | 0.022683226 | −7.170773077 | 9.3863 | 9.520657 | 10.036997 | 6.544171 | 5.857745 | 7.020304 |
| METTL1 | −0.674089829 | 0.049888566 | 0.032291256 | −7.179599117 | 7.686806 | 7.383076 | 5.723602 | 1.661149 | 4.539173 | 5.446557 |
| HIPK2 | −0.722346377 | 0.047646206 | 0.027699217 | −7.192137635 | 11.585835 | 10.428779 | 9.310781 | 7.582358 | 7.56803 | 7.748756 |
| SCFD2 | −0.807485972 | 0.045272487 | 0.021529772 | −7.193247514 | 6.417969 | 6.044198 | 6.601009 | 1.661149 | 3.571326 | 4.146207 |
| NT5DC3 | −0.647772701 | 0.051631895 | 0.035416128 | −7.195500884 | 9.170294 | 11.432999 | 10.640089 | 7.792994 | 8.140553 | 7.722406 |
| PARP16 | −0.795899369 | 0.045374706 | 0.022268118 | −7.226627157 | 6.417969 | 6.03611 | 7.462086 | 1.661149 | 4.608763 | 3.630092 |
| DHX38 | −0.601623285 | 0.056111267 | 0.042501531 | −7.241003583 | 10.518185 | 8.561508 | 10.730562 | 5.705318 | 7.440337 | 7.020304 |
| RRAGA | −0.77195692 | 0.046057921 | 0.023937394 | −7.242751562 | 12.257657 | 11.356063 | 11.196982 | 7.856887 | 9.401119 | 8.784285 |
| THPO | −0.797000919 | 0.045366463 | 0.022191902 | −7.247685686 | 5.779429 | 5.43468 | 6.072169 | 1.661149 | 3.571326 | 2.921909 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| CD101 | −0.637988809 | 0.052496924 | 0.036928887 | −7.262730803 | 5.744513 | 8.181467 | 8.458015 | 5.320955 | 2.265287 | 5.900694 |
| VANGL2 | −0.708447426 | 0.04824159 | 0.028925485 | −7.266727449 | 7.445608 | 6.537655 | 8.54408 | 4.802615 | 5.509998 | 3.676349 |
| PWWP2B | −0.643105923 | 0.05194815 | 0.036157877 | −7.276084409 | 6.846868 | 7.402335 | 7.855267 | 6.396698 | 4.539173 | 2.921909 |
| DNAJC8 | −0.848420041 | 0.044599879 | 0.019015311 | −7.296850735 | 11.66877 | 11.352354 | 11.224758 | 8.688623 | 8.564762 | 8.357484 |
| ITFG3 | −0.637419733 | 0.052514975 | 0.037019394 | −7.302072329 | 9.902119 | 8.407985 | 7.7303 | 4.718672 | 6.319269 | 7.033813 |
| NONO | −0.783818675 | 0.045695042 | 0.023057503 | −7.305648867 | 11.935794 | 12.567904 | 11.872799 | 9.698891 | 9.451686 | 8.834367 |
| TUBB4B | −0.67555335 | 0.049794345 | 0.032143586 | −7.310908571 | 13.313745 | 14.69107 | 14.743622 | 11.849546 | 11.567822 | 11.821019 |
| RAB33A | −0.701754769 | 0.048571998 | 0.029671997 | −7.351296306 | 6.554045 | 5.362142 | 6.012527 | 1.661149 | 3.134528 | 4.476242 |
| NASP | −0.833088605 | 0.044797567 | 0.019829874 | −7.353070822 | 11.753395 | 11.774369 | 12.393714 | 8.875048 | 8.951948 | 9.372483 |
| SV2A | −0.708764122 | 0.04824159 | 0.02890507 | −7.372390938 | 9.689484 | 7.679931 | 6.601009 | 5.743334 | 4.797798 | 4.476242 |
| ZSCAN16 | −0.622379472 | 0.053792728 | 0.039134399 | −7.375779037 | 6.417969 | 5.148082 | 4.724406 | 1.661149 | 2.265287 | 4.476242 |
| TIPRL | −0.82755683 | 0.044930476 | 0.020250425 | −7.400189864 | 10.078965 | 9.168002 | 9.149294 | 6.396698 | 7.191402 | 5.091834 |
| TRIP4 | −0.786658035 | 0.04555041 | 0.022728819 | −7.400521501 | 9.206896 | 8.278469 | 7.360327 | 1.661149 | 6.319269 | 5.580533 |
| CALCA | −0.775356807 | 0.045942803 | 0.023724396 | −7.40085677 | 4.743564 | 5.809601 | 4.944468 | 1.661149 | 2.265287 | 2.921909 |
| C15orf48 | −0.58770507 | 0.057633938 | 0.045025519 | −7.406055343 | 7.980539 | 8.660813 | 8.366488 | 7.504712 | 5.317867 | 5.091834 |
| LAMB2 | −0.777110997 | 0.045858868 | 0.023531814 | −7.424694627 | 12.063179 | 12.135419 | 12.701612 | 9.049264 | 9.809281 | 9.769968 |
| ZNF395 | −0.650032917 | 0.05147219 | 0.035035046 | −7.455800752 | 12.222335 | 10.405104 | 10.234003 | 7.33564 | 8.696398 | 8.952456 |
| PPP2CB | −0.814928785 | 0.045198955 | 0.02109493 | −7.458084416 | 13.268699 | 13.616544 | 14.099313 | 10.369894 | 10.769315 | 11.146572 |
| PRDX6 | −0.82578989 | 0.044949653 | 0.020369513 | −7.494335789 | 14.518145 | 13.702332 | 14.113068 | 10.873216 | 11.207267 | 11.512316 |
| ASCC1 | −0.765379888 | 0.046178907 | 0.024447091 | −7.523695748 | 10.098578 | 7.843866 | 8.702188 | 1.661149 | 7.187136 | 6.195186 |
| MTHFD2L | −0.664716652 | 0.05040851 | 0.033296359 | −7.570034815 | 6.054828 | 7.129367 | 5.389265 | 1.661149 | 3.134528 | 5.106393 |
| POU3F1 | −0.626828337 | 0.053474985 | 0.038534195 | −7.570034815 | 6.054828 | 6.311907 | 8.525393 | 4.718672 | 3.134528 | 5.106393 |
| S100A9 | −0.625688072 | 0.053562842 | 0.038714529 | −7.570034815 | 6.054828 | 8.628465 | 5.389265 | 1.661149 | 3.134528 | 6.129407 |
| IL23A | −0.639514586 | 0.052338861 | 0.036643756 | −7.575844619 | 7.067614 | 5.195784 | 7.180931 | 4.894482 | 2.265287 | 4.146207 |
| PCMT1 | −0.831868027 | 0.044860922 | 0.019922423 | −7.582887957 | 12.028542 | 11.73977 | 11.504251 | 9.260886 | 8.817023 | 8.424409 |
| SH3PXD2A | −0.784249598 | 0.045655746 | 0.023012589 | −7.585348973 | 10.671972 | 10.20576 | 11.2175 | 7.037879 | 8.502167 | 7.748756 |
| WFIKKN1 | −0.706615224 | 0.048309794 | 0.029140524 | −7.623729122 | 3.839948 | 5.195784 | 6.410545 | 1.661149 | 2.265287 | 2.921909 |
| SLED1 | −0.637627755 | 0.052501106 | 0.036977884 | −7.623729122 | 5.263699 | 5.195784 | 5.389265 | 4.718672 | 3.134528 | 6.129407 |
| IRX1 | −0.830498767 | 0.044867325 | 0.020039469 | −7.627233895 | 8.85157 | 11.519332 | 8.011136 | 6.283686 | 5.920411 | 5.426231 |
| ELF4 | −0.905277707 | 0.044173537 | 0.016165362 | −7.63546089 | 8.028068 | 7.912639 | 8.024505 | 5.095353 | 4.131418 | 5.091834 |
| FAM189B | −0.729910375 | 0.047394039 | 0.027116026 | −7.657934818 | 10.577293 | 12.256783 | 10.644425 | 9.154721 | 8.055928 | 5.634184 |
| HMGA1 | −0.849137033 | 0.044539625 | 0.01893297 | −7.751345264 | 8.890666 | 8.147628 | 7.997641 | 1.661149 | 5.936219 | 5.446557 |
| AGPAT2 | −0.890737718 | 0.044203301 | 0.016971759 | −7.759185469 | 8.051258 | 8.889534 | 8.26876 | 5.095353 | 5.317867 | 6.129407 |
| MVP | −0.789558511 | 0.045529634 | 0.022669616 | −7.740124088 | 10.620572 | 9.396488 | 9.028421 | 6.244586 | 6.640994 | 7.668215 |
| JMJD8 | −0.694843851 | 0.048858998 | 0.030073562 | −7.747993073 | 10.655041 | 10.381035 | 9.504512 | 6.550689 | 10.511716 | 8.60836 |
| SNORD22 | −0.762876577 | 0.046294386 | 0.024682545 | −7.763926618 | 10.056219 | 9.201373 | 10.282106 | 1.661149 | 5.317867 | 5.446557 |
| RASSF4 | −0.840983962 | 0.044701668 | 0.01941953 | −7.766460499 | 12.975954 | 13.437325 | 13.701247 | 6.244586 | 6.640994 | 7.897492 |
| HNRNPU | −0.844181678 | 0.044645837 | 0.019204491 | −7.811794785 | 11.017855 | 10.055705 | 11.088182 | 10.74399 | 10.511716 | 9.851274 |
| OSTF1 | −0.730641943 | 0.047384624 | 0.02706703 | −7.814991529 | 9.750974 | 8.445606 | 8.428147 | 8.122528 | 7.56803 | 7.218312 |
| UBL4A | −0.759292758 | 0.046382879 | 0.024892821 | −7.835235608 | 8.84495 | 6.983552 | 7.056312 | 5.320955 | 6.78473 | 6.106561 |
| RNASEH1 | −0.712205346 | 0.047984994 | 0.02855393 | −7.856603559 | 10.914153 | 12.234791 | 13.174964 | 9.260886 | 4.797798 | 5.874974 |
| WWTR1 | −0.632169178 | 0.05307838 | 0.037804695 | −7.880354138 | 4.639409 | 6.049721 | 8.102218 | 1.661149 | 9.64516 | 9.072081 |
| SLC23A3 | −0.724044292 | 0.047585406 | 0.027537258 | −7.902791099 | 7.773024 | 5.297868 | 6.056062 | 1.661149 | 4.797798 | 3.630092 |
| PORCN | −0.773677971 | 0.046006594 | 0.023815584 | −7.917186749 | 8.713026 | 8.158996 | 8.735088 | 5.728038 | 3.134528 | 4.790662 |
| RC3H2 | −0.80736439 | 0.045278798 | 0.02154066 | −7.936730826 | 12.676518 | 11.783579 | 11.727086 | 9.002943 | 5.165949 | 6.32627 |
| SSR2 | −0.797680187 | 0.045355733 | 0.022136781 | −7.969225848 | 9.625257 | 11.312186 | 9.948587 | 6.954147 | 9.687973 | 8.60836 |
| SLC25A37 | −0.84804937 | 0.044599879 | 0.019022116 | −7.972366897 | 9.648253 | 9.184784 | 8.607641 | 6.067497 | 6.78473 | 7.920856 |
| HCCS | −0.797680187 | 0.04458868 | 0.019022116 | −7.972366897 | 9.648253 | 9.184784 | 8.607641 | 6.067497 | 6.189775 | 6.195186 |
| BLOC1S1 | −0.763008009 | 0.04628868 | 0.024658047 | −7.997576706 | 11.610439 | 10.845928 | 10.242609 | 7.243046 | 7.31791 | 9.092804 |

TABLE 8-continued

Differentially Expressed Genes in CD10−, CD24−, CD44− Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| PPIF | −0.780944698 | 0.045805247 | 0.02328411 | −8.023150935 | 11.643242 | 12.044868 | 11.755426 | 9.81605 | 8.751258 | 8.11568 |
| PDLIM7 | −0.806679401 | 0.045297753 | 0.021599864 | −8.033212252 | 11.459349 | 11.804542 | 11.210206 | 7.42265 | 8.453372 | 9.363984 |
| LAT | −0.783124361 | 0.045695042 | 0.023091528 | −8.124475148 | 9.21205 | 8.841005 | 10.39192 | 6.183122 | 6.189775 | 7.152205 |
| GLS | −0.738297443 | 0.047140798 | 0.026532834 | −8.128310697 | 9.936777 | 10.794007 | 11.830609 | 7.771052 | 8.724089 | 7.428484 |
| PLOD3 | −0.840077898 | 0.044722631 | 0.0194869 | −8.155236142 | 10.163866 | 10.135563 | 9.400679 | 5.026959 | 7.107836 | 7.428484 |
| GPC1 | −0.663765178 | 0.050437995 | 0.033373256 | −8.17454591 | 9.09418 | 10.046553 | 7.227914 | 6.063041 | 5.317867 | 6.722123 |
| GMPS | −0.764905926 | 0.046181862 | 0.024505614 | −8.174607461 | 9.105302 | 9.081032 | 7.593473 | 6.550689 | 5.509998 | 4.562324 |
| RABL3 | −0.755134568 | 0.046508764 | 0.025254849 | −8.220449372 | 10.587244 | 9.96146 | 8.767255 | 5.728038 | 7.25505 | 7.327219 |
| ECM1 | −0.860989871 | 0.044379352 | 0.01836747 | −8.247641658 | 10.869187 | 10.23291 | 10.484319 | 5.252045 | 7.440337 | 8.213534 |
| SLC18A2 | −0.844741392 | 0.044645837 | 0.019197686 | −8.260502478 | 6.617556 | 7.383076 | 6.175931 | 1.661149 | 3.571326 | 4.476242 |
| LRRC20 | −0.579815073 | 0.05881361 | 0.046789384 | −8.280514429 | 4.815804 | 6.184248 | 7.462086 | 1.661149 | 3.134528 | 5.634184 |
| DGKD | −0.905722119 | 0.044173537 | 0.016124532 | −8.296655574 | 8.36065 | 9.778245 | 8.562528 | 5.743334 | 5.509998 | 5.446557 |
| SNHG15 | −0.84553808 | 0.044645837 | 0.019170466 | −8.308653721 | 11.183126 | 11.461972 | 11.350843 | 6.651882 | 8.296229 | 9.051056 |
| IL1RL1 | −0.866653723 | 0.044377262 | 0.018072133 | −8.324540446 | 12.185473 | 12.502474 | 11.753421 | 8.122528 | 9.128102 | 9.555312 |
| FCER1G | −0.654102238 | 0.051134477 | 0.034508336 | −8.345884991 | 5.982974 | 6.184248 | 5.596986 | 1.661149 | 2.265287 | 2.921909 |
| TUBGCP2 | −0.682996378 | 0.049394421 | 0.031361688 | −8.356548197 | 10.748456 | 9.332664 | 8.642743 | 5.579836 | 7.56803 | 7.180104 |
| SP9 | −0.787330732 | 0.045564387 | 0.022795509 | −8.358472793 | 5.328526 | 4.351315 | 6.489771 | 1.661149 | 2.265287 | 2.921909 |
| PPAP2B | −0.806277462 | 0.045315307 | 0.021630487 | −8.421171228 | 14.571377 | 12.857663 | 12.843677 | 6.252746 | 11.497356 | 10.565606 |
| ARHGAP39 | −0.852380327 | 0.044480228 | 0.018746512 | −8.428829214 | 5.491121 | 5.340619 | 5.225216 | 1.661149 | 2.265287 | 2.921909 |
| ZFAT | −0.682791216 | 0.049399307 | 0.031383464 | −8.429446045 | 4.736586 | 4.736586 | 6.054038 | 1.661149 | 4.131418 | 2.921909 |
| NPTX2 | −0.673185212 | 0.0499291 | 0.032349098 | −8.429446045 | 8.763044 | 4.736586 | 7.056312 | 1.661149 | 2.265287 | 6.32627 |
| UBE3C | −0.774376467 | 0.046000938 | 0.023791085 | −8.447539069 | 10.898254 | 11.067214 | 9.757647 | 5.891233 | 7.819723 | 8.472642 |
| LRCH1 | −0.799245244 | 0.045343942 | 0.022051718 | −8.480062502 | 10.832846 | 10.868609 | 11.67399 | 7.748771 | 8.4199 | 8.564524 |
| TUBBP5 | −0.747515272 | 0.046789913 | 0.025821708 | −8.531355643 | 7.701538 | 8.319573 | 7.519866 | 2.820813 | 4.608763 | 6.455366 |
| KCNQ4 | −0.680923186 | 0.049467746 | 0.031565839 | −8.5329723 | 6.227577 | 6.792427 | 5.609945 | 1.661149 | 3.134528 | 5.091834 |
| STK39 | −0.82388972 | 0.044990161 | 0.020477033 | −8.556950093 | 8.720278 | 9.679079 | 8.418052 | 5.320955 | 5.920411 | 6.385515 |
| GRID1 | −0.839057005 | 0.044732882 | 0.01956788 | −8.574123645 | 10.497228 | 8.805276 | 9.167487 | 6.067497 | 3.571326 | 7.523109 |
| APEH | −0.754272665 | 0.04655221 | 0.025321538 | −8.593488103 | 11.115975 | 10.638232 | 9.653933 | 6.550689 | 7.440337 | 8.503924 |
| MAP2K1 | −0.911252149 | 0.044159136 | 0.015817625 | −8.595705298 | 12.344701 | 11.573437 | 12.291665 | 8.579223 | 8.469821 | 9.329475 |
| NRM | −0.850189273 | 0.044510429 | 0.018871725 | −8.60178564 | 7.701538 | 6.270596 | 7.250844 | 1.661149 | 4.608763 | 4.146207 |
| FADS3 | −0.862559101 | 0.044437262 | 0.018264757 | −8.648292961 | 11.06988 | 10.208498 | 10.91953 | 7.957464 | 6.78473 | 7.897492 |
| BAK1 | −0.739431397 | 0.047109709 | 0.026415788 | −8.650726573 | 7.259029 | 8.473191 | 6.948237 | 6.067497 | 3.134528 | 4.146207 |
| UBE2I1 | −0.775954349 | 0.045911642 | 0.023673358 | −8.663216582 | 12.155021 | 11.116154 | 11.028054 | 9.040118 | 7.767462 | 8.745549 |
| PDGFRB | −0.721682286 | 0.047677157 | 0.027789724 | −8.672663054 | 12.834827 | 10.887527 | 12.05077 | 7.771052 | 9.673843 | 9.532738 |
| SQSTM1 | −0.922359369 | 0.044110923 | 0.015241239 | −8.686796628 | 13.688951 | 13.715385 | 13.806091 | 10.541751 | 10.596561 | 10.853609 |
| GLG1 | −0.790357992 | 0.045525452 | 0.022289132 | −8.689426722 | 12.528932 | 11.155977 | 11.93164 | 7.792994 | 9.409671 | 9.220702 |
| ZNF496 | −0.853409752 | 0.044464174 | 0.018670296 | −8.704706925 | 7.730559 | 7.512784 | 7.997641 | 1.661149 | 4.608763 | 5.634184 |
| FAM171B | −0.827327042 | 0.044930476 | 0.02027084 | −8.707682082 | 4.639409 | 6.044198 | 7.227914 | 1.661149 | 3.134528 | 2.921909 |
| MTHFR | −0.828775193 | 0.044930476 | 0.020208234 | −8.715420287 | 11.183126 | 10.393119 | 11.824889 | 7.504712 | 7.269549 | 8.941073 |
| LRWD1 | −0.808112394 | 0.045257569 | 0.021501191 | −8.723384602 | 7.956174 | 7.664061 | 7.204614 | 5.448591 | 4.539173 | 3.630092 |
| THTPA | −0.759874813 | 0.046382879 | 0.024865601 | −8.741084651 | 7.410173 | 6.049721 | 6.891005 | 4.894482 | 3.571326 | 2.921909 |
| PACSIN3 | −0.682045731 | 0.049418096 | 0.031470568 | −8.767275637 | 6.417969 | 6.762934 | 6.054038 | 5.095353 | 3.134528 | 2.921909 |
| ZDHHC9 | −0.757708199 | 0.046414887 | 0.024972035 | −8.776888283 | 11.202676 | 10.7664 | 10.207872 | 7.074163 | 7.187136 | 9.008063 |
| CHPF | −0.760658727 | 0.046345577 | 0.024812521 | −8.795458469 | 10.744904 | 9.634981 | 8.418052 | 6.498222 | 7.174648 | 6.051818 |
| IRF5 | −0.8939899 | 0.044203301 | 0.016815243 | −8.802834196 | 9.037244 | 9.019996 | 8.775186 | 6.244586 | 5.165949 | 5.882028 |
| REEP4 | −0.816551838 | 0.045155524 | 0.020930929 | −8.832484053 | 8.804578 | 8.723411 | 8.063885 | 6.189775 | 6.189775 | 5.580533 |
| CBLL1 | −0.918716606 | 0.044110923 | 0.015376659 | −8.856956289 | 9.349356 | 9.190335 | 8.903739 | 6.283686 | 6.043524 | 5.426231 |
| AGER | −0.588970503 | 0.05748724 | 0.044788023 | −8.857020985 | 6.344798 | 4.80797 | 5.596986 | 1.661149 | 2.265287 | 5.091834 |
| TARBP2 | −0.721147201 | 0.047696784 | 0.027823069 | −8.881028124 | 7.278811 | 6.072636 | 6.072169 | 1.661149 | 5.353925 | 2.921909 |

TABLE 8-continued

Differentially Expressed Genes in CD10-, CD24-, CD44- Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| SDR39U1 | -0.755368897 | 0.046505334 | 0.02521674 | -8.890527039 | 12.032189 | 11.748263 | 12.248164 | 8.173604 | 8.87992 | 10.242966 |
| ACVR1B | -0.826772934 | 0.044930476 | 0.020304866 | -8.922320379 | 9.562079 | 9.352605 | 9.749619 | 7.25991 | 6.319269 | 6.195186 |
| YKT6 | -0.894968224 | 0.044203301 | 0.016774413 | -8.973397163 | 10.626374 | 10.238279 | 9.671037 | 5.095353 | 7.174648 | 7.46072 |
| CHPF2 | -0.62615087 | 0.053522686 | 0.038666894 | -8.996682069 | 6.58615 | 5.43468 | 2.995681 | 1.661149 | 2.265287 | 2.921909 |
| RBM19 | -0.886272888 | 0.044203301 | 0.0171623 | -9.028585084 | 9.949176 | 10.339172 | 9.431116 | 7.109557 | 6.774676 | 6.32627 |
| C13orf33 | -0.865605462 | 0.044377262 | 0.018106159 | -9.041434449 | 9.740312 | 8.595375 | 8.88187 | 5.705318 | 6.794431 | 4.146207 |
| PVT1 | -0.822965869 | 0.045019115 | 0.020555291 | -9.08210941 | 9.789409 | 12.918293 | 10.823365 | 8.501391 | 6.861783 | 7.640338 |
| YARS | -0.780860706 | 0.045805247 | 0.023290915 | -9.105581266 | 10.373887 | 10.484061 | 9.226523 | 7.210813 | 7.187136 | 7.180104 |
| GPN2 | -0.663820017 | 0.050437995 | 0.033366451 | -9.136954894 | 6.52121 | 6.391145 | 6.012527 | 2.820813 | 3.134528 | 5.091834 |
| PTMS | -0.930005374 | 0.044037172 | 0.014813882 | -9.159799465 | 12.719677 | 12.547504 | 12.836114 | 8.331873 | 9.524361 | 9.899123 |
| DAAM2 | -0.875988795 | 0.044285705 | 0.017627765 | -9.192810828 | 10.673841 | 10.484061 | 11.337515 | 1.661149 | 7.473335 | 8.974957 |
| HLA-B | -0.890314281 | 0.044190907 | 0.016344335 | -9.23062158 | 16.466846 | 16.263629 | 15.995935 | 13.054079 | 12.325882 | 13.564862 |
| WDR43 | -0.800144549 | 0.045343942 | 0.021997278 | -9.259256622 | 10.647452 | 11.766958 | 11.199931 | 7.243046 | 7.989035 | 9.113234 |
| PATH | -0.887419322 | 0.044203301 | 0.01713508 | -9.278797097 | 11.115975 | 9.931942 | 11.267554 | 6.954147 | 7.292524 | 8.053616 |
| KLC1 | -0.930230507 | 0.044025007 | 0.014791426 | -9.294454255 | 12.648279 | 12.464036 | 11.669742 | 8.65307 | 8.453372 | 9.462817 |
| PTRH1 | -0.752206336 | 0.0466011 | 0.025467846 | -9.295542761 | 9.61362 | 9.710324 | 7.956385 | 4.739845 | 5.857745 | 7.291822 |
| HBA2 | -0.951403686 | 0.043900827 | 0.01383804 | -9.30742812 | 10.755533 | 10.889234 | 10.414946 | 1.661149 | 7.53715 | 7.873743 |
| MFSD5 | -0.917671402 | 0.044110923 | 0.015435182 | -9.311913641 | 9.262601 | 8.595375 | 8.076776 | 1.661149 | 6.043524 | 5.446557 |
| EXOC3L4 | -0.841331228 | 0.044701668 | 0.01939231 | -9.333292622 | 4.682076 | 5.487673 | 6.355801 | 1.661149 | 2.265287 | 2.921909 |
| WDR5 | -0.763520152 | 0.046268297 | 0.024624702 | -9.34318169 | 7.355332 | 7.476899 | 6.450701 | 1.661149 | 4.131418 | 5.446557 |
| APEX2 | -0.835171682 | 0.044793607 | 0.019708744 | -9.34402914 | 8.804578 | 8.359538 | 6.800663 | 5.448591 | 5.165949 | 5.580533 |
| LOX | -0.804037633 | 0.045334912 | 0.021789044 | -9.352297424 | 10.412457 | 9.737119 | 8.279951 | 5.448591 | 7.187136 | 6.051818 |
| ABHD2 | -0.776144043 | 0.045884853 | 0.023644097 | -9.38607801 | 10.334258 | 10.009352 | 8.257481 | 5.026959 | 7.174648 | 6.73963 |
| SOLH | -0.885595922 | 0.044203301 | 0.01720313 | -9.44624761 | 9.121827 | 9.20686 | 9.015087 | 6.550689 | 5.509998 | 5.882028 |
| CORO1B | -0.711158742 | 0.048057698 | 0.028658047 | -9.447026393 | 10.822774 | 9.239354 | 8.313014 | 4.718672 | 6.78473 | 7.582913 |
| NHEJ1 | -0.834626565 | 0.044793607 | 0.01972916 | -9.465030148 | 9.26756 | 9.13384 | 9.008374 | 5.891233 | 5.317867 | 6.924055 |
| PRR7 | -0.749289358 | 0.046728791 | 0.025706022 | -9.499912701 | 6.924263 | 7.282726 | 6.175931 | 1.661149 | 5.306419 | 3.676349 |
| FAU | -0.808739538 | 0.045247607 | 0.021454917 | -9.51088753 | 15.808595 | 16.331419 | 15.781741 | 12.468898 | 12.559015 | 13.877468 |
| WBSCR16 | -0.709993708 | 0.048157645 | 0.028777816 | -9.556497976 | 8.890666 | 8.016282 | 6.072169 | 1.661149 | 5.509998 | 5.634184 |
| PDPK1 | -0.65781501 | 0.050866557 | 0.034060565 | -9.560892278 | 8.705736 | 8.016282 | 8.726933 | 5.448591 | 4.608763 | 7.352555 |
| BAG6 | -0.914120641 | 0.044110923 | 0.015646138 | -9.585705604 | 12.922328 | 12.444485 | 11.900255 | 8.768324 | 8.63937 | 9.750536 |
| KIAA1984 | -0.888800286 | 0.044203301 | 0.017060225 | -9.595375997 | 5.316227 | 6.184248 | 5.225216 | 1.661149 | 2.265287 | 2.921909 |
| ESYT1 | -0.833671381 | 0.044797567 | 0.019782239 | -9.65572573 | 11.026657 | 10.251615 | 9.769607 | 6.498222 | 7.627877 | 7.553321 |
| PLEKHM2 | -0.627767824 | 0.055380879 | 0.038412385 | -9.683590785 | 6.846868 | 7.0089 | 5.225216 | 1.661149 | 3.571326 | 5.446557 |
| CHI3L1 | -0.831735815 | 0.044860922 | 0.019942838 | -9.68778531 | 8.959701 | 9.471353 | 7.593473 | 5.743334 | 3.571326 | 6.195186 |
| MEF2D | -0.796478819 | 0.045374706 | 0.022220483 | -9.709688414 | 10.392166 | 10.091744 | 11.958009 | 6.498222 | 7.505595 | 8.678584 |
| MRPL32 | -0.953418697 | 0.043857532 | 0.01374277 | -9.737647816 | 11.704864 | 12.282348 | 12.007662 | 8.65307 | 8.724089 | 8.870819 |
| FOXK1 | -0.97296996 | 0.043681142 | 0.012845185 | -9.770371508 | 9.605809 | 9.901809 | 10.295954 | 6.395481 | 6.613395 | 6.722123 |
| METTL11A | -0.961775474 | 0.043778104 | 0.01330164 | -9.825423702 | 10.256573 | 9.725696 | 9.725263 | 6.960054 | 6.608026 | 5.091834 |
| IL1B | -0.614720956 | 0.054543342 | 0.040247023 | -9.886624606 | 9.048812 | 6.702075 | 10.587011 | 5.743334 | 5.317867 | 7.03218 |
| LOC440896 | -0.578268742 | 0.05899939 | 0.047070432 | -9.891289606 | 8.085359 | 6.228068 | 5.609945 | 1.661149 | 6.774676 | 2.921909 |
| FAM70B | -0.844849088 | 0.044645837 | 0.019190881 | -9.892338198 | 6.417969 | 5.487673 | 5.571599 | 1.661149 | 2.265287 | 3.676349 |
| TRMT61A | -0.776150303 | 0.045884853 | 0.023637292 | -9.921385699 | 9.895728 | 6.605686 | 5.571599 | 4.341916 | 2.265287 | 2.921909 |
| SEC22B | -0.783741595 | 0.045695042 | 0.023064308 | -9.954512035 | 11.776192 | 9.038579 | 8.598731 | 5.728038 | 7.31791 | 5.106393 |
| CARS | -0.850201162 | 0.044510429 | 0.01886492 | -9.962353829 | 8.763044 | 12.05022 | 10.023743 | 8.460842 | 7.713236 | 7.492252 |
| SDC1 | -0.745878107 | 0.04683654 | 0.02598707 | -10.0080276 | 9.525286 | 8.454859 | 8.677011 | 7.210813 | 7.191402 | 5.446557 |
| TIE1 | -0.729749424 | 0.047394039 | 0.027129636 | -10.01085039 | 8.77005 | 8.158996 | 9.310781 | 1.661149 | 5.353925 | 8.305171 |
| MESTIT1 | -0.814204241 | 0.045212649 | 0.021151412 | -10.03149741 | 9.927407 | 10.594942 | 9.934491 | 4.718672 | 6.613395 | 5.446557 |
| TXNRD1 | -0.793454507 | 0.045455125 | 0.022502212 | | | | | 8.206677 | 6.608026 | 6.587378 |

TABLE 8-continued

Differentially Expressed Genes in CD10−, CD24−, CD44− Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| RGPD1 | −0.776814587 | 0.045858868 | 0.023565839 | −10.03659603 | 7.530567 | 7.458616 | 7.082111 | 1.661149 | 4.131418 | 5.882028 |
| NCKAP5L | −0.939611467 | 0.043955231 | 0.014399456 | −10.00383492 | 8.583805 | 8.776041 | 9.765631 | 5.448591 | 5.306419 | 6.051818 |
| SBF1P1 | −0.906556652 | 0.044173537 | 0.016076897 | −10.09698092 | 9.541754 | 9.789261 | 9.179489 | 4.013424 | 6.205902 | 7.020304 |
| GLRA4 | −0.806007175 | 0.045315307 | 0.021650902 | −10.15879849 | 5.744513 | 5.43468 | 5.609945 | 1.661149 | 2.265287 | 3.630092 |
| MPHOSPH10 | −0.787656452 | 0.045562713 | 0.022771011 | −10.1703371 | 9.967577 | 9.964703 | 9.197307 | 5.728038 | 7.68534 | 6.618407 |
| H2AFZ | −0.946587478 | 0.043900827 | 0.014076216 | −10.18956731 | 13.044008 | 14.116738 | 14.556262 | 9.739011 | 9.694987 | 11.2096 |
| NECAP2 | −0.845935978 | 0.044641179 | 0.019139163 | −10.20795393 | 9.426762 | 9.291936 | 8.458015 | 5.448591 | 6.861783 | 5.106393 |
| SH3RF2 | −0.879658918 | 0.044278935 | 0.017442668 | −10.2499531 | 5.335413 | 6.638536 | 5.018694 | 1.661149 | 2.265287 | 2.921909 |
| ERMP1 | −0.678869851 | 0.049555317 | 0.031746172 | −10.2499531 | 6.52121 | 6.537655 | 5.018694 | 1.661149 | 4.797798 | 2.921909 |
| MRPL41 | −0.888129066 | 0.044203301 | 0.01712147 | −10.32240169 | 11.054181 | 10.790357 | 10.000252 | 7.42265 | 7.292524 | 7.640338 |
| TNFAIP2 | −0.83178287 | 0.044860922 | 0.019936033 | −10.37206772 | 12.492332 | 13.015697 | 12.411632 | 8.723321 | 9.1177 | 10.554443 |
| DCPS | −0.733749154 | 0.047307334 | 0.026802314 | −10.41928433 | 8.476537 | 8.028729 | 6.056062 | 5.095353 | 4.131418 | 4.476242 |
| NHLH1 | −0.811631155 | 0.045218796 | 0.021275944 | −10.50731094 | 5.658609 | 6.184248 | 5.225216 | 1.661149 | 2.265287 | 3.676349 |
| RNH1 | −0.984476281 | 0.043626235 | 0.012388568 | −10.50807554 | 13.619617 | 12.861582 | 12.27568 | 8.993498 | 9.468155 | 9.509806 |
| OTUD4 | −0.928997003 | 0.044037172 | 0.014863323 | −10.51136662 | 11.536537 | 12.264698 | 12.727901 | 9.137671 | 8.36819 | 8.870819 |
| STX1A | −0.775790664 | 0.045911642 | 0.023686968 | −10.56476017 | 7.177073 | 8.586982 | 8.428147 | 5.026959 | 3.134528 | 6.195186 |
| TTLL4 | −0.955232088 | 0.043840967 | 0.013682205 | −10.57578211 | 9.60972 | 9.967938 | 9.277666 | 5.891233 | 6.794431 | 5.874974 |
| NOC4L | −0.920139133 | 0.044110923 | 0.015329023 | −10.62443854 | 11.041209 | 11.273484 | 10.117184 | 7.631894 | 6.861783 | 7.774634 |
| SMG5 | −0.841578697 | 0.044701668 | 0.01936509 | −10.68664256 | 9.72957 | 9.655192 | 8.607641 | 6.960054 | 6.237456 | 4.790662 |
| POLG | −0.916955677 | 0.044110923 | 0.015482817 | −10.70025486 | 11.800648 | 11.730275 | 12.326489 | 8.270632 | 8.181074 | 9.220702 |
| CNPPD1 | −0.886024718 | 0.044203301 | 0.01717591 | −10.71327407 | 10.518185 | 9.357547 | 8.702188 | 5.705318 | 5.936219 | 6.722123 |
| CFP | −0.894698365 | 0.044203301 | 0.016794828 | −10.77736692 | 7.906175 | 7.34377 | 7.98402 | 5.320955 | 2.265287 | 4.476242 |
| CREB3 | −0.941686039 | 0.043921714 | 0.014313032 | −10.82470977 | 10.126141 | 9.891622 | 9.214907 | 5.579836 | 6.794431 | 6.455366 |
| KLHL36 | −0.626279448 | 0.053518816 | 0.038647159 | −10.82921574 | 7.867504 | 8.417483 | 8.234655 | 4.341916 | 4.797798 | 7.46072 |
| B3GAT1 | −0.767738053 | 0.04616149 | 0.024291256 | −10.8349816 | 4.309025 | 7.648015 | 5.702912 | 1.661149 | 2.265287 | 3.676349 |
| APOA1 | −0.784817536 | 0.045655746 | 0.023005784 | −10.90763179 | 5.316227 | 7.174872 | 7.593473 | 1.661149 | 4.131418 | 4.146207 |
| LAMA4 | −1.011960811 | 0.043581008 | 0.011382103 | −10.9413837 | 13.510376 | 13.124805 | 13.51518 | 7.771052 | 10.063457 | 10.18624 |
| TMEM39B | −0.830478048 | 0.044867325 | 0.020046274 | −10.95872455 | 8.016332 | 8.417483 | 8.448127 | 4.718672 | 6.205902 | 4.562324 |
| HIVEP2 | −0.924168713 | 0.044091888 | 0.015157537 | −10.9829661 | 10.36466 | 11.113235 | 11.47655 | 7.656039 | 7.942653 | 7.395512 |
| C11orf53 | −0.765235387 | 0.046178907 | 0.024460701 | −10.99148689 | 6.48761 | 5.195784 | 5.723602 | 1.661149 | 2.265287 | 4.146207 |
| PEX16 | −0.830671139 | 0.044867325 | 0.020025859 | −11.02186796 | 9.964527 | 9.190335 | 8.024505 | 5.728038 | 5.317867 | 6.455366 |
| MLEC | −0.958245591 | 0.043826549 | 0.01349303 | −11.11331989 | 11.173911 | 10.828234 | 11.330804 | 8.864724 | 9.218487 | 9.133378 |
| VPS72 | −0.881873883 | 0.044229452 | 0.017358966 | −11.02727643 | 12.877747 | 12.609931 | 11.662277 | 7.36523 | 8.098861 | 7.96648 |
| MRPS2 | −0.973826011 | 0.043681142 | 0.01279755 | −11.04290522 | 10.497228 | 10.319043 | 8.88187 | 6.252746 | 6.373501 | 7.03218 |
| TEX264 | −0.794936082 | 0.045408694 | 0.022349098 | −11.08292067 | 10.244048 | 10.578102 | 7.746525 | 6.283686 | 7.107836 | 6.32627 |
| PSMB2 | −0.955258347 | 0.04411923 | 0.0136754 | −11.10719774 | 10.563246 | 9.663198 | 10.007003 | 6.339437 | 6.189775 | 7.492252 |
| CTRC | −0.742293667 | 0.046946487 | 0.02617625 | −11.12170539 | 5.148082 | 5.190335 | 8.024505 | 5.728038 | 9.218487 | 9.133378 |
| VNN3 | −0.97787971 | 0.043661316 | 0.012612453 | −11.21795033 | 5.753024 | 6.139057 | 5.596986 | 1.661149 | 2.265287 | 2.921909 |
| TIGD5 | −0.907141942 | 0.044173537 | 0.016042872 | −11.21833093 | 8.502009 | 7.829709 | 7.762571 | 4.341916 | 3.571326 | 5.634184 |
| RHCG | −1.001066401 | 0.043588662 | 0.011816945 | −11.22400596 | 9.725971 | 9.996735 | 9.485302 | 1.661149 | 6.237456 | 6.73963 |
| WDR90 | −0.899950073 | 0.044203301 | 0.016528071 | −11.23199169 | 10.929879 | 9.921968 | 10.228237 | 6.396698 | 7.440337 | 7.327219 |
| SLC9B2 | −0.959934812 | 0.043802358 | 0.013413406 | −11.26016638 | 10.929879 | 10.440472 | 9.560654 | 6.067497 | 6.373501 | 7.492252 |
| RPS6KA4 | −0.987147795 | 0.043626235 | 0.01229297 | −11.33344954 | 10.864285 | 10.082818 | 10.365897 | 6.814118 | 6.640994 | 7.36177 |
| EFNB1 | −0.942353766 | 0.043921714 | 0.012479006 | −11.33870594 | 11.410866 | 11.971811 | 12.651867 | 7.531061 | 9.148683 | 8.549611 |
| SHARPIN | −1.0455639 | 0.043577906 | 0.010153794 | −11.35789927 | 11.427578 | 12.620763 | 11.341526 | 7.835902 | 8.077554 | 8.03232 |
| JHDM1D | −0.983202613 | 0.043626235 | 0.012463423 | −11.37073219 | 9.621388 | 10.115279 | 10.7688 | 6.339437 | 6.608026 | 6.931222 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| CPNE2 | −0.91400021 | 0.044110923 | 0.015653943 | −11.39931261 | 11.103549 | 10.91293 | 10.770785 | 7.25991 | 7.292524 | 8.357484 |
| POLR3D | −0.811536249 | 0.045218796 | 0.021282749 | −11.42515884 | 5.779429 | 5.195784 | 6.072169 | 1.661149 | 2.265287 | 3.676349 |
| RGMA | −0.841203105 | 0.044701668 | 0.019399115 | −11.45484611 | 9.399914 | 8.25747 | 9.532856 | 1.661149 | 7.174648 | 5.882028 |
| LOC400043 | −1.033653913 | 0.043577906 | 0.010439605 | −11.45666243 | 10.126141 | 9.748452 | 10.151102 | 5.891233 | 6.608026 | 6.649696 |
| HOXC8 | −0.70977819 | 0.04819475 | 0.028815243 | −11.47229801 | 10.213536 | 6.931478 | 9.839352 | 1.661149 | 6.319269 | 7.668215 |
| LCLAT1 | −0.645177416 | 0.051833045 | 0.035868663 | −11.52553162 | 9.988753 | 7.857885 | 7.156853 | 6.339437 | 6.373501 | 3.630092 |
| CAPG | −1.033301159 | 0.043577906 | 0.010453215 | −11.54875532 | 10.213536 | 10.073837 | 10.414946 | 6.544171 | 6.551443 | 7.020304 |
| HSPB7 | −0.960209952 | 0.043802358 | 0.013386186 | −11.58860705 | 6.344798 | 5.195784 | 6.054038 | 1.661149 | 2.265287 | 2.921909 |
| LAMC3 | −0.810884673 | 0.045237293 | 0.021322218 | −11.60409971 | 10.701589 | 11.225629 | 12.489019 | 5.891233 | 8.928336 | 8.952456 |
| DAZAP2 | −0.920197693 | 0.044110923 | 0.015315413 | −11.60999858 | 13.870218 | 13.016869 | 12.862876 | 10.332922 | 10.074256 | 9.02972 |
| MRPL14 | −0.998615009 | 0.043626235 | 0.011890439 | −11.62363013 | 11.550668 | 12.016244 | 11.252009 | 8.514658 | 8.011679 | 7.553321 |
| TWIST2 | −0.93949615 | 0.043986717 | 0.014224634 | −11.66661578 | 4.963444 | 5.809601 | 7.575421 | 1.661149 | 2.265287 | 2.921909 |
| ANKRD34C | −0.93393653 | 0.044025007 | 0.01463491 | −11.66689528 | 5.263699 | 6.466258 | 5.596986 | 1.661149 | 2.265287 | 2.921909 |
| TPRN | −0.682445718 | 0.04941326 | 0.031430419 | −11.66689528 | 7.259029 | 6.466258 | 6.072169 | 1.661149 | 5.920411 | 3.630092 |
| TCEB3 | −1.014566892 | 0.043581008 | 0.011286828 | −11.68174688 | 10.595155 | 11.365907 | 10.914153 | 7.42265 | 7.819723 | 5.874974 |
| TRIM29 | −0.677666219 | 0.04967045 | 0.031907452 | −11.68820206 | 7.177073 | 9.367381 | 5.592916 | 1.661149 | 6.608026 | 3.630092 |
| CASKIN1 | −0.923579765 | 0.044091888 | 0.015184757 | −11.72147892 | 8.947392 | 8.25747 | 7.69729 | 5.095353 | 5.306419 | 4.146207 |
| GPAT2 | −0.867718749 | 0.044335719 | 0.018004083 | −11.76530593 | 8.397309 | 6.638536 | 5.217616 | 1.661149 | 3.571326 | 3.676349 |
| DCTPP1 | −0.959389468 | 0.043826549 | 0.01345863 | −11.77479945 | 9.138164 | 9.291936 | 8.967426 | 1.661149 | 6.551443 | 5.580533 |
| TNRC18 | −0.873660024 | 0.044299467 | 0.017697176 | −11.78001292 | 10.827818 | 9.352605 | 9.831767 | 5.579836 | 7.269549 | 6.931222 |
| SEMA4A | −0.734871863 | 0.04729774 | 0.026737666 | −11.82502362 | 7.931391 | 10.819306 | 13.346454 | 6.395481 | 7.767462 | 7.255535 |
| NRG1 | −0.647329085 | 0.05166843 | 0.035505274 | −11.8274553 | 5.753024 | 10.308872 | 5.225216 | 1.661149 | 4.131418 | 5.426231 |
| CDC42EP2 | −0.943333341 | 0.043921714 | 0.014238176 | −11.87717713 | 7.701538 | 6.391145 | 6.861515 | 1.661149 | 4.131418 | 3.630092 |
| KDM5C | −0.750093793 | 0.046662281 | 0.025587615 | −11.93153419 | 10.36466 | 10.461284 | 10.371139 | 9.094145 | 6.794431 | 5.900694 |
| BASP1 | −0.868052485 | 0.044335719 | 0.017976863 | −11.94669494 | 12.530995 | 10.601206 | 13.170085 | 7.582358 | 9.009341 | 8.952456 |
| GPR25 | −1.00510973 | 0.043588662 | 0.011653624 | −11.96284627 | 5.856559 | 6.502398 | 6.670675 | 1.661149 | 3.134528 | 5.091834 |
| GHRLOS2 | −0.821991541 | 0.045048325 | 0.020611092 | −12.36684512 | 6.306772 | 6.762934 | 7.339085 | 1.661149 | 3.134528 | 6.455366 |
| FGFBP1 | −0.600154281 | 0.056344664 | 0.042819326 | −12.38424163 | 6.381847 | 8.454859 | 6.012527 | 4.739845 | 2.265287 | 6.924055 |
| SF3B4 | −0.926180292 | 0.04406867 | 0.015047295 | −12.43372566 | 11.756044 | 11.05205 | 10.707953 | 8.105092 | 8.119857 | 6.924055 |
| MAP4K4 | −1.056430273 | 0.043540291 | 0.00970262 | −12.45466341 | 12.193312 | 12.09973 | 12.554998 | 6.550689 | 8.916384 | 8.705744 |
| CNPY3 | −0.931431291 | 0.044025007 | 0.014750595 | −12.46099728 | 11.072716 | 10.582331 | 9.640971 | 5.705318 | 7.414086 | 6.942983 |
| C7orf43 | −0.877188968 | 0.044280042 | 0.017562436 | −12.46103997 | 9.344671 | 10.2447 | 9.421041 | 5.728038 | 5.509998 | 7.03218 |
| YY1AP1 | −0.955856313 | 0.043840967 | 0.01364818 | −12.47792987 | 9.967577 | 9.740906 | 10.602695 | 8.604261 | 7.406567 | 6.32627 |
| EIF3J | −0.947888626 | 0.043900827 | 0.014008166 | −12.54518237 | 10.925179 | 12.226035 | 11.918273 | 8.331873 | 8.160956 | 8.269212 |
| SRRT | −1.020650926 | 0.043577906 | 0.011028921 | −12.56768236 | 12.068161 | 12.530645 | 12.261635 | 7.210813 | 8.609988 | 9.257878 |
| SLC1A3 | −0.769165749 | 0.046096091 | 0.024117727 | −12.67749036 | 6.45321 | 8.454859 | 9.067696 | 4.718672 | 5.165949 | 4.790662 |
| LRRC56 | −0.969518722 | 0.043726704 | 0.01310672 | −12.70546935 | 5.328526 | 5.789702 | 6.704285 | 1.661149 | 2.265287 | 2.921909 |
| TKTL1 | −0.986582687 | 0.043626235 | 0.012306907 | −12.81241608 | 7.238972 | 5.340619 | 7.003286 | 8.105092 | 8.119857 | 2.921909 |
| LRP8 | −0.885440498 | 0.044203301 | 0.017209935 | −12.85072154 | 6.45321 | 6.605686 | 4.449894 | 1.661149 | 2.265287 | 3.630092 |
| MAF1 | −1.026815045 | 0.043577906 | 0.010695475 | −12.89396502 | 12.070291 | 10.899437 | 11.34019 | 7.210813 | 7.740604 | 2.921909 |
| DECR2 | −1.056860541 | 0.043540291 | 0.009682205 | −12.9116065 | 9.186094 | 9.626816 | 9.773571 | 1.661149 | 5.936219 | 8.095288 |
| CCDC127 | −1.019245899 | 0.043577906 | 0.011083362 | −12.97457427 | 9.594014 | 9.572589 | 9.203198 | 1.661149 | 6.373501 | 6.106561 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| ZNRF1 | −0.965993219 | 0.043778104 | 0.013146649 | −12.97469283 | 10.249071 | 9.173617 | 10.627001 | 5.252045 | 6.551443 | 6.942983 |
| TGFB2 | −0.915168616 | 0.044110923 | 0.015578088 | −12.99833211 | 8.323035 | 10.586546 | 10.992779 | 5.320955 | 7.292524 | 5.580533 |
| CCNJ | −0.922852723 | 0.044091888 | 0.015198367 | −13.00499235 | 7.134281 | 5.362142 | 6.072169 | 1.661149 | 3.134528 | 2.921909 |
| SECISBP2 | −1.028574022 | 0.043577906 | 0.010620619 | −13.03291582 | 11.478722 | 10.821096 | 10.467286 | 5.891233 | 7.191402 | 7.774634 |
| ZDHHC14 | −0.842888254 | 0.044657496 | 0.019260293 | −13.06360376 | 9.44876 | 9.821812 | 9.627892 | 4.341916 | 5.920411 | 7.873743 |
| GTF2IRD1 | −0.981673862 | 0.043626235 | 0.012511058 | −13.07334317 | 9.377152 | 9.502922 | 8.874506 | 6.339437 | 5.165949 | 5.580533 |
| UBE2J2 | −1.011487011 | 0.043581008 | 0.011388908 | −13.09284144 | 10.410216 | 10.324102 | 9.972928 | 1.661149 | 6.613395 | 7.255535 |
| RHOD | −0.833349241 | 0.044797567 | 0.019823069 | −13.26212076 | 8.527038 | 10.227521 | 7.519866 | 6.396698 | 4.797798 | 4.562324 |
| PPP2R5B | −0.964014386 | 0.043778104 | 0.013201089 | −13.28472356 | 9.914819 | 9.377149 | 8.467835 | 6.183122 | 5.353925 | 5.446557 |
| PEA15 | −1.073181109 | 0.043516135 | 0.009162981 | −13.28795009 | 12.40389 | 12.918293 | 12.772165 | 9.040118 | 9.275744 | 8.456743 |
| ERI3 | −0.909441273 | 0.044173036 | 0.015953045 | −13.30211683 | 11.286905 | 10.783028 | 9.556058 | 5.705318 | 7.414086 | 7.553321 |
| ZNF692 | −1.073278176 | 0.043516135 | 0.009156176 | −13.30372337 | 9.61362 | 9.439076 | 9.986654 | 5.705318 | 6.043524 | 6.195186 |
| TSPYL2 | −0.968532823 | 0.043738451 | 0.01304117 | −13.30543365 | 14.743536 | 13.80924 | 15.607453 | 10.075297 | 10.570102 | 11.927244 |
| ABCD1 | −0.993376032 | 0.043626235 | 0.012075536 | −13.31905803 | 8.274593 | 7.34377 | 8.751261 | 4.894482 | 4.539173 | 3.676349 |
| DCTN2 | −1.006856732 | 0.043588662 | 0.011592378 | −13.32448975 | 12.319851 | 11.813562 | 10.991078 | 8.270632 | 8.077554 | 7.774634 |
| DGKQ | −0.94675307 | 0.043900827 | 0.014062606 | −13.34847138 | 6.873131 | 6.931478 | 6.410545 | 1.661149 | 3.134528 | 4.146207 |
| RPS6 | −0.825668069 | 0.044949653 | 0.020396734 | −13.37289001 | 17.351942 | 18.282063 | 17.649163 | 13.610703 | 13.848762 | 15.900822 |
| GRPEL1 | −1.059283312 | 0.043540291 | 0.009566519 | −13.43796723 | 10.145127 | 10.742039 | 10.672298 | 7.109557 | 6.189775 | 6.924055 |
| SLC27A4 | −0.658574018 | 0.050764584 | 0.039922423 | −13.44265457 | 7.198002 | 6.670655 | 2.995681 | 1.661149 | 3.134528 | 2.921909 |
| AKNA | −1.024486824 | 0.043577906 | 0.010845185 | −13.46698742 | 12.286038 | 12.688032 | 13.435161 | 9.012327 | 7.819723 | 9.683805 |
| CD276 | −0.956046878 | 0.043840967 | 0.01363457 | −13.50636388 | 9.961469 | 8.586982 | 9.243773 | 4.718672 | 6.205902 | 5.882028 |
| RARG | −0.82992103 | 0.044925422 | 0.020127935 | −13.55075859 | 7.410173 | 8.491292 | 8.102218 | 4.341916 | 6.043524 | 3.630092 |
| RMND5B | −0.922277371 | 0.044091888 | 0.015248044 | −13.57246476 | 10.412457 | 9.683021 | 8.589765 | 6.550689 | 5.920411 | 5.634184 |
| SH2B2 | −1.029033121 | 0.043577906 | 0.010600204 | −13.57522269 | 7.278811 | 7.664063 | 8.302077 | 1.661149 | 4.539173 | 4.146207 |
| FOXF2 | −0.96550394 | 0.043778104 | 0.013167064 | −13.62109619 | 10.376185 | 8.868964 | 10.947875 | 13.610703 | 6.613395 | 7.180104 |
| BEGAIN | −0.95074642 | 0.043900827 | 0.01386526 | −13.7170218 | 7.530567 | 9.09885 | 9.035041 | 5.320955 | 5.317867 | 3.676349 |
| TIMM17A | −1.084837505 | 0.043516135 | 0.008764206 | −13.75513926 | 12.16834 | 12.206308 | 11.321356 | 7.877571 | 7.713236 | 8.424409 |
| PRKDC | −1.027481881 | 0.043577906 | 0.010647839 | −13.77375556 | 11.916191 | 11.577679 | 10.834794 | 7.36523 | 7.793829 | 8.053616 |
| ACHE | −0.826813189 | 0.044930476 | 0.020298061 | −13.82819362 | 6.054828 | 6.502398 | 6.012527 | 1.661149 | 2.265287 | 4.476242 |
| PLXNB1 | −1.007108262 | 0.043588662 | 0.011585573 | −13.99273059 | 10.581282 | 11.450453 | 9.725263 | 6.651882 | 6.774676 | 7.03218 |
| GPIHBP1 | −0.698926541 | 0.048753782 | 0.030935886 | −14.06179919 | 7.656883 | 6.904719 | 6.948237 | 1.661149 | 3.134528 | 6.73963 |
| NOTCH2 | −0.944446097 | 0.043921714 | 0.014156516 | −14.17400232 | 10.785229 | 12.016244 | 12.296494 | 6.960054 | 9.02055 | 7.825039 |
| AEN | −0.914378592 | 0.044110923 | 0.015618918 | −14.34805458 | 9.700528 | 9.891622 | 9.155384 | 4.802615 | 5.857745 | 7.218312 |
| CCDC71 | −0.908254349 | 0.044173537 | 0.015988431 | −14.35350285 | 8.638422 | 8.319573 | 7.4423 | 1.661149 | 5.920411 | 4.476242 |
| MAPKAPK2 | −0.851837925 | 0.044480228 | 0.018773733 | −14.37563566 | 12.910092 | 12.532285 | 13.428261 | 7.877571 | 9.064538 | 11.146572 |
| MAP1LC3B2 | −1.013609747 | 0.043516135 | 0.011334468 | −14.39637365 | 7.814275 | 7.87177 | 8.939468 | 1.661149 | 4.608763 | 5.091834 |
| RPL9 | −1.073454789 | 0.043516135 | 0.000913576 | −14.483567 | 16.388277 | 17.351906 | 16.857923 | 12.897666 | 13.495561 | 12.534993 |
| BCKDK | −1.048729508 | 0.043577906 | 0.009984348 | −14.51018605 | 13.648655 | 12.771872 | 13.628963 | 8.033165 | 9.956624 | 9.769968 |
| GIGYF1 | −1.068745814 | 0.043516135 | 0.009305886 | −14.55433223 | 11.614337 | 10.762679 | 10.236878 | 7.037879 | 6.373501 | 7.291822 |
| IRX4 | −1.062952004 | 0.043516135 | 0.009441987 | −14.58828895 | 10.844508 | 10.684201 | 10.728522 | 4.739845 | 6.861783 | 7.611911 |
| FMNL3 | −0.87895133 | 0.044278935 | 0.017483498 | −14.74875362 | 7.09018 | 8.028729 | 5.225216 | 1.661149 | 3.134528 | 4.146207 |
| EIF5AL1 | −0.982157595 | 0.043626235 | 0.012497448 | −14.78047187 | 10.416927 | 9.128067 | 11.065724 | 5.891233 | 5.936219 | 7.180104 |
| GLO1 | −1.081402142 | 0.043516135 | 0.008890779 | −14.79727798 | 14.320856 | 15.05024 | 14.224426 | 11.040784 | 10.669588 | 10.337166 |
| PRRC2B | −0.972089196 | 0.043681142 | 0.008896937 | −14.89806937 | 13.235233 | 13.037804 | 11.663346 | 8.801178 | 8.855089 | 9.33818 |
| TULP4 | −1.080495755 | 0.043516135 | 0.008952024 | −14.97943202 | 12.419569 | 12.572694 | 12.705768 | 8.514658 | 8.65384 | 9.267025 |
| CDKN2A | −0.952405847 | 0.043900827 | 0.013791085 | −15.01706419 | 7.298325 | 8.065438 | 7.538623 | 1.661149 | 5.306419 | 3.630092 |
| ENDOG | −1.072779627 | 0.043516135 | 0.009183396 | −15.09123057 | 9.048812 | 9.007473 | 8.477589 | 1.661149 | 7.174648 | 4.562324 |
| EFHD2 | −1.046638338 | 0.043577906 | 0.010066009 | −15.09954913 | 11.422029 | 12.292707 | 12.593633 | 8.069577 | 7.505595 | 8.906373 |

TABLE 8-continued

Differentially Expressed Genes in CD10−, CD24−, CD44− Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| RASSF7 | −0.943233062 | 0.043921714 | 0.014244981 | −15.2198587 | 7.854379 | 9.864102 | 9.537526 | 4.739845 | 5.936219 | 5.426231 |
| CKB | −1.0151566 | 0.043581008 | 0.011252807 | −15.22458362 | 11.905096 | 13.183736 | 13.589027 | 7.976765 | 8.36819 | 10.033825 |
| STX4 | −1.075011215 | 0.043516135 | 0.009101735 | −15.23038947 | 11.60163 | 11.210685 | 12.069434 | 6.550689 | 8.140553 | 7.96648 |
| C10orf35 | −0.692128138 | 0.048955004 | 0.03048656 | −15.36143612 | 7.134281 | 8.417483 | 3.764125 | 1.661149 | 3.134528 | 4.476242 |
| TNFRSF18 | −0.749980379 | 0.046675232 | 0.025603266 | −15.36212782 | 5.263699 | 8.889584 | 8.659978 | 4.718672 | 3.134528 | 4.790662 |
| NES | −1.070790332 | 0.043516135 | 0.009217421 | −15.50672082 | 11.349047 | 13.189984 | 13.185046 | 7.394225 | 8.098861 | 9.23941 |
| MAZ | −1.028964463 | 0.043577906 | 0.010607009 | −15.51030385 | 12.214011 | 11.325396 | 12.539366 | 7.36523 | 8.258856 | 8.784285 |
| TMEM63B | −0.994582774 | 0.043626235 | 0.012048316 | −15.60673845 | 9.191323 | 9.737119 | 9.692135 | 5.728038 | 4.797798 | 6.722123 |
| THAP4 | −1.136729434 | 0.043453389 | 0.00720313 | −15.70473206 | 11.478722 | 11.476811 | 10.648749 | 7.037879 | 7.505595 | 6.931222 |
| SPSB1 | −1.046681961 | 0.043577906 | 0.010052399 | −15.75890155 | 10.767835 | 10.95593 | 12.151699 | 8.173604 | 7.191402 | 5.882028 |
| PJA1 | −0.942363982 | 0.043921714 | 0.014272201 | −15.76461021 | 9.071674 | 8.454859 | 8.345336 | 1.661149 | 6.549959 | 4.476242 |
| DDR2 | −0.985088969 | 0.043626235 | 0.012368152 | −15.77402551 | 10.622509 | 9.489477 | 8.534767 | 1.661149 | 5.509998 | 6.942983 |
| RBM15B | −1.162640786 | 0.043453389 | 0.006549847 | −15.77800333 | 10.398961 | 10.012489 | 9.86187 | 6.252746 | 6.189775 | 5.882028 |
| EIF4G1 | −1.096020408 | 0.043495335 | 0.008357945 | −15.80072094 | 10.177104 | 10.293481 | 9.390389 | 5.743334 | 6.237456 | 6.195186 |
| HIP1R | −1.03372532 | 0.043577906 | 0.010425995 | −15.82965244 | 9.886086 | 11.882049 | 11.102436 | 6.395481 | 6.043524 | 7.897492 |
| ZNF219 | −1.001427809 | 0.043588662 | 0.01181014 | −15.85743752 | 9.296962 | 9.555485 | 8.726933 | 4.739845 | 6.373501 | 5.106393 |
| ACSL4 | −1.156094605 | 0.043453389 | 0.006713168 | −15.90256621 | 9.927407 | 9.555485 | 9.405796 | 5.579836 | 5.936219 | 3.630092 |
| GPATCH3 | −1.020827228 | 0.043577906 | 0.011015311 | −15.9601516 | 8.831618 | 8.535576 | 8.050877 | 1.661149 | 4.539173 | 5.634184 |
| MFSD10 | −1.064358609 | 0.043516135 | 0.009414767 | −16.07428577 | 11.641333 | 11.904174 | 10.813772 | 7.450526 | 7.56803 | 7.897492 |
| RAI14 | −1.025216616 | 0.043577906 | 0.01078394 | −16.08080906 | 10.380769 | 10.59075 | 9.155384 | 4.894482 | 6.373501 | 6.722123 |
| MRTO4 | −1.14156161 | 0.043453389 | 0.007073835 | −16.08299318 | 11.057048 | 11.705291 | 10.557423 | 7.210813 | 6.549959 | 7.152205 |
| ANKRD11 | −1.020984919 | 0.043577906 | 0.010994896 | −16.15549982 | 12.126645 | 12.491837 | 12.328512 | 7.607339 | 8.314558 | 9.454835 |
| UBASH3B | −0.873508987 | 0.044299467 | 0.017710786 | −16.18672861 | 7.595107 | 9.874484 | 10.629191 | 5.026959 | 5.857745 | 6.195186 |
| KDM2A | −1.109797134 | 0.043485739 | 0.007921742 | −16.30309268 | 12.44003 | 11.907548 | 12.304737 | 7.631894 | 8.277663 | 8.771488 |
| REXO4 | −0.641884838 | 0.052014843 | 0.036263355 | −16.41415912 | 8.183076 | 8.288855 | 6.012527 | 1.661149 | 7.107836 | 4.146207 |
| TSG101 | −1.040524424 | 0.043577906 | 0.01030505 | −16.42813514 | 12.904531 | 11.620455 | 10.577971 | 7.582358 | 7.91889 | 7.36177 |
| DAXX | −1.192434448 | 0.043453389 | 0.005903368 | −16.42748781 | 12.180223 | 12.596406 | 12.270078 | 8.139755 | 8.140553 | 8.549611 |
| CTPS | −0.959060726 | 0.043826549 | 0.013449473 | −16.5571654 | 10.112425 | 10.235597 | 9.421041 | 6.063041 | 5.306419 | 7.291822 |
| PIEZO1 | −1.115733968 | 0.043485739 | 0.007717591 | −16.56325923 | 10.264036 | 10.701797 | 10.804114 | 6.651882 | 7.094585 | 6.129407 |
| C1orf51 | −1.01690307 | 0.043581008 | 0.01117952 | −16.69247905 | 9.4134 | 10.124007 | 10.10465 | 4.894482 | 6.043524 | 6.924055 |
| RIPK1 | −1.095481392 | 0.043495335 | 0.008385165 | −16.77404198 | 10.305614 | 9.564062 | 9.118454 | 4.718672 | 6.237456 | 5.580533 |
| ANAPC1 | −1.0672441 | 0.043516135 | 0.009339912 | −16.77781072 | 10.145127 | 10.094707 | 10.120301 | 4.894482 | 7.066159 | 6.051818 |
| RRP9 | −1.142206242 | 0.043453389 | 0.007039809 | −16.9311492 | 8.884223 | 10.046553 | 8.685452 | 4.802615 | 4.608763 | 5.446557 |
| MID1IP1 | −1.146362147 | 0.043453389 | 0.006937734 | −16.93907577 | 8.691047 | 8.473191 | 9.061224 | 1.661149 | 4.608763 | 5.106393 |
| SLC29A1 | −1.092361129 | 0.043495335 | 0.008514461 | −16.94405603 | 11.453921 | 11.803637 | 10.857383 | 7.976765 | 6.774676 | 7.327219 |
| B4GALT2 | −1.089244207 | 0.043516135 | 0.0086213 | −16.98860911 | 9.961469 | 10.243628 | 9.485302 | 4.718672 | 6.608026 | 5.874974 |
| SAP25 | −0.988406832 | 0.043626235 | 0.012238857 | −16.99845029 | 7.968408 | 8.147628 | 9.945076 | 1.661149 | 5.857745 | 4.790662 |
| FBXO10 | −1.081182402 | 0.043516135 | 0.008911194 | −17.06596987 | 8.224469 | 7.952383 | 8.571664 | 1.661149 | 4.131418 | 5.106393 |
| TRAF7 | −1.060864469 | 0.043540291 | 0.009512079 | −17.25905194 | 11.503105 | 11.300684 | 10.459924 | 6.183122 | 7.191402 | 7.800057 |
| LOC729603 | −1.139475577 | 0.043453389 | 0.007169105 | −17.27713913 | 9.217186 | 8.417483 | 8.467835 | 1.661149 | 4.539173 | 5.106393 |
| ATP6V0B | −1.111691559 | 0.043485739 | 0.007860497 | −17.29715697 | 12.871118 | 12.069927 | 12.61754 | 7.957464 | 8.296229 | 9.133378 |
| CIB2 | −1.101744465 | 0.043495335 | 0.008153794 | −17.34565645 | 9.470427 | 9.173617 | 10.166259 | 1.661149 | 5.353925 | 6.32627 |
| GPRIN1 | −1.00821412 | 0.043581008 | 0.01149083 | −17.34634806 | 6.381847 | 6.792427 | 6.031658 | 1.661149 | 2.265287 | 3.630092 |
| ALDOA | −1.201834655 | 0.043453389 | 0.005570602 | −17.36183889 | 14.676022 | 14.551526 | 13.910595 | 9.799885 | 9.939008 | 10.558174 |
| FAM180A | −0.884246506 | 0.044223984 | 0.017266417 | −17.36704887 | 5.779429 | 6.502398 | 7.4423 | 1.661149 | 2.265287 | 4.562324 |
| SOX8 | −0.833637233 | 0.044797567 | 0.019789044 | −17.36704887 | 5.779429 | 6.391145 | 8.981205 | 1.661149 | 4.539173 | 3.630092 |
| CRISPLD2 | −0.895320384 | 0.044203301 | 0.016733583 | −17.3987106 | 14.783358 | 14.269426 | 14.861804 | 7.394225 | 10.66245 | 12.877926 |
| HSD17B10 | −1.035669627 | 0.043577906 | 0.01039197 | −17.51235631 | 11.219408 | 10.964054 | 9.578892 | 5.448591 | 6.774676 | 7.218312 |
| AP1S1 | −0.941857198 | 0.043921714 | 0.014299422 | −17.53047974 | 8.922456 | 7.726519 | 6.861515 | 1.661149 | 4.608763 | 4.790662 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| TCP11L1 | -1.124927939 | 0.043453389 | 0.007454917 | -17.58504269 | 9.640629 | 9.302226 | 8.562528 | 5.252045 | 5.165949 | 5.106393 |
| SLC4A3 | -1.046659297 | 0.043577906 | 0.010059204 | -17.73682739 | 6.924263 | 8.943172 | 7.825025 | 2.820813 | 4.608763 | 3.676349 |
| DENND1A | -0.95622193 | 0.043840967 | 0.013614154 | -17.74931675 | 10.475962 | 8.790733 | 8.458015 | 1.661149 | 5.857745 | 6.32627 |
| FZD5 | -1.029052288 | 0.043577906 | 0.010593399 | -17.87868598 | 8.518743 | 9.480443 | 10.355354 | 4.341916 | 5.509998 | 6.195186 |
| KCNH3 | -0.958595483 | 0.043826549 | 0.013469888 | -17.88243156 | 7.155835 | 7.08238 | 6.054038 | 1.661149 | 4.131418 | 2.921909 |
| UCK2 | -1.02738692 | 0.043577906 | 0.010661449 | -18.10087642 | 6.973646 | 8.309406 | 6.83141 | 1.661149 | 4.131418 | 3.630092 |
| SLC25A25 | -1.078167348 | 0.043516135 | 0.009020075 | -18.2077769 | 11.325462 | 11.233716 | 12.341256 | 6.396698 | 7.138979 | 8.564524 |
| NXF1 | -0.984411763 | 0.043626235 | 0.012395373 | -18.26795942 | 13.187953 | 14.286857 | 14.48989 | 8.616619 | 10.095614 | 11.202466 |
| KIF1A | -1.083501194 | 0.043516135 | 0.008822729 | -18.32079214 | 5.856559 | 8.676719 | 6.012527 | 1.661149 | 2.265287 | 2.921909 |
| HIVEP3 | -0.949154065 | 0.043900827 | 0.013926506 | -18.4444431 | 8.351337 | 10.311422 | 10.726478 | 7.243046 | 5.509998 | 4.146207 |
| SS18L2 | -1.218312091 | 0.043453389 | 0.005237155 | -18.45254373 | 12.426237 | 12.431408 | 12.913159 | 8.616619 | 8.220489 | 8.407967 |
| BRF1 | -1.24466661 | 0.043453389 | 0.004767608 | -18.4713131 | 10.266516 | 9.935252 | 10.334036 | 5.728038 | 6.189775 | 5.874974 |
| BCL2L11 | -1.166125577 | 0.043453389 | 0.006495407 | -18.52011489 | 11.636671 | 11.248425 | 12.191507 | 7.42265 | 8.011679 | 6.73963 |
| FLNA | -1.086523174 | 0.043516135 | 0.00873018 | -18.57989161 | 13.080394 | 13.7137 | 13.244097 | 8.864724 | 8.998044 | 10.166824 |
| ELTD1 | -0.794273379 | 0.04540117 | 0.022331405 | -18.63973708 | 10.150506 | 9.538176 | 10.295954 | 5.320955 | 5.317867 | 8.809543 |
| SAA1 | -1.006095589 | 0.043588662 | 0.011626404 | -18.6799756 | 11.637507 | 13.081773 | 9.887706 | 7.918071 | 7.414086 | 6.455366 |
| ACCN3 | -1.120093471 | 0.043485739 | 0.007588295 | -18.8598055 | 7.980539 | 8.398425 | 9.035041 | 1.661149 | 4.797798 | 4.562324 |
| TMUB1 | -1.081510223 | 0.043516135 | 0.008883974 | -18.96214266 | 10.857723 | 10.351611 | 9.996864 | 7.25991 | 5.509998 | 6.106561 |
| HSPG2 | -1.050837409 | 0.043568903 | 0.009908813 | -19.00163023 | 10.856078 | 10.762679 | 11.299525 | 5.448591 | 6.608026 | 8.155622 |
| FANCB | -0.837544399 | 0.044763248 | 0.019623682 | -19.10558612 | 6.52121 | 6.03611 | 6.737132 | 1.661149 | 2.265287 | 4.790662 |
| FADS1 | -0.680143431 | 0.049490097 | 0.031618237 | -19.10635158 | 11.896318 | 7.843866 | 6.976024 | 1.661149 | 6.043524 | 7.640338 |
| TBRG4 | -1.133698065 | 0.043453389 | 0.007277986 | -19.11332195 | 11.567836 | 11.667979 | 10.493962 | 6.954147 | 6.237456 | 7.668215 |
| REPIN1 | -1.198428402 | 0.043453389 | 0.005727118 | -19.59828051 | 11.479791 | 11.452764 | 10.703803 | 7.074163 | 7.187136 | 6.722123 |
| PDPN | -0.948648322 | 0.043900827 | 0.013960531 | -19.6204415 | 9.840223 | 9.337675 | 9.400679 | 1.661149 | 7.656894 | 5.106393 |
| NPW | -1.181567785 | 0.043453389 | 0.006141545 | -19.69267187 | 6.186289 | 7.218985 | 6.564874 | 1.661149 | 2.265287 | 2.921909 |
| ZBTB7B | -1.222990056 | 0.043453389 | 0.00513508 | -19.76735252 | 10.254077 | 10.445123 | 9.753639 | 5.448591 | 6.189775 | 5.874974 |
| CRABP2 | -0.962688698 | 0.043778104 | 0.013255529 | -19.89380202 | 11.527082 | 14.393872 | 14.306583 | 8.566539 | 10.079625 | 9.257878 |
| HSD11B1 | -1.097383211 | 0.043493355 | 0.00831031 | -20.12272642 | 10.414694 | 9.542523 | 10.251164 | 1.661149 | 5.920411 | 6.73963 |
| PEAK1 | -1.025388024 | 0.043577906 | 0.010777135 | -20.20403416 | 10.288639 | 11.992611 | 12.57558 | 7.656039 | 7.68534 | 7.46072 |
| XIRP1 | -0.972220384 | 0.043681142 | 0.012886016 | -20.27198211 | 5.658609 | 7.965391 | 8.903739 | 2.820813 | 2.265287 | 4.562324 |
| MARS | -1.026758202 | 0.043577906 | 0.010709085 | -20.57109723 | 12.507608 | 12.018586 | 10.394496 | 7.656039 | 7.53715 | 7.800057 |
| LRCH4 | -1.088113716 | 0.043516135 | 0.00867574 | -21.12023628 | 10.870817 | 11.257708 | 11.353494 | 6.857154 | 6.373501 | 8.03232 |
| NRN1L | -0.77868838 | 0.045838382 | 0.023409323 | -21.28089657 | 6.949166 | 6.072636 | 6.704285 | 1.661149 | 2.265287 | 5.446557 |
| CXorf65 | -1.140229962 | 0.043453389 | 0.00714869 | -21.2879603 | 11.739185 | 10.936243 | 10.279321 | 5.095353 | 6.774676 | 7.327219 |
| LDLRAD2 | -0.895309444 | 0.044203301 | 0.016740388 | -21.30473308 | 12.507608 | 12.018586 | 7.156853 | 1.661149 | 2.265287 | 4.790662 |
| FGFRL1 | -1.211118333 | 0.043453389 | 0.005414086 | -21.38367043 | 9.659616 | 11.021236 | 10.309671 | 5.891233 | 6.189775 | 5.634184 |
| PPARD | -1.091552864 | 0.0435113 | 0.008566179 | -21.52092138 | 10.690553 | 11.500464 | 10.979111 | 1.661149 | 6.551443 | 8.03232 |
| ST7-AS1 | -1.154802289 | 0.043453389 | 0.006733583 | -21.53587326 | 7.563198 | 6.702075 | 6.564874 | 1.661149 | 3.134528 | 2.921909 |
| C11orf91 | -0.827858518 | 0.044930476 | 0.02024362 | -21.71146222 | 7.238972 | 8.916627 | 8.974332 | 6.814118 | 2.265287 | 4.476242 |
| NSMCE1 | -0.996898812 | 0.043626235 | 0.011966655 | -21.96907954 | 8.294165 | 8.028729 | 6.891005 | 1.661149 | 3.571326 | 5.091834 |
| SCAP | -1.058649799 | 0.043540291 | 0.009580129 | -21.97318011 | 9.792853 | 9.019996 | 8.467835 | 1.661149 | 6.319269 | 4.562324 |
| IER3 | -1.178994645 | 0.043453389 | 0.006195985 | -21.99339825 | 13.331022 | 14.646838 | 14.300241 | 8.711848 | 9.841243 | 10.19585 |
| GPR133 | -1.067957459 | 0.043516135 | 0.009312691 | -22.28357469 | 8.332531 | 6.139057 | 7.580498 | 1.661149 | 4.131418 | 2.921909 |
| C11orf96 | -1.04112008 | 0.043577906 | 0.010269479 | -22.29903859 | 16.640765 | 14.974649 | 16.285645 | 10.771883 | 10.495739 | 13.322651 |
| CDK16 | -1.350035981 | 0.043453389 | 0.003079959 | -22.64426987 | 12.430665 | 12.496885 | 12.174366 | 7.995811 | 7.767462 | 7.748756 |
| FBXW5 | -1.214274742 | 0.043453389 | 0.005332426 | -22.70790464 | 13.284993 | 12.573225 | 11.899348 | 7.394225 | 7.440337 | 8.870819 |
| FAM41C | -1.172089952 | 0.043453389 | 0.006359306 | -22.81593236 | 8.284413 | 8.949732 | 8.525393 | 4.013424 | 3.571326 | 5.091834 |
| SEMA3B | -0.897269661 | 0.044203301 | 0.016620619 | -23.29325466 | 7.595107 | 11.129218 | 10.265311 | 5.320955 | 5.306419 | 6.587378 |
| RGS12 | -1.111885411 | 0.043485739 | 0.007846887 | -23.49858062 | 9.806546 | 10.634165 | 10.881463 | 5.252045 | 5.317867 | 7.395512 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| ZNF384 | −1.331186761 | 0.043453389 | 0.003372576 | −23.740022157 | 11.156639 | 11.236402 | 11.108726 | 5.026959 | 6.774676 | 6.587378 |
| FHL3 | −1.218555443 | 0.043453389 | 0.0052035 | −23.81693238 | 10.145127 | 10.521976 | 10.47461 | 1.661149 | 6.319269 | 5.900694 |
| FBXL8 | −1.239645557 | 0.043453389 | 0.004822048 | −23.83934302 | 7.497182 | 6.572071 | 6.564874 | 1.661149 | 2.265287 | 2.921909 |
| SKI | −1.136238445 | 0.043453389 | 0.00721674 | −23.8401672 | 10.632154 | 10.695955 | 11.755426 | 4.718672 | 7.138979 | 7.180104 |
| FOXC2 | −1.020499187 | 0.043577906 | 0.011035726 | −23.86175684 | 8.0045 | 7.711156 | 6.369239 | 1.661149 | 3.134528 | 4.476242 |
| ADC | −1.014326805 | 0.043581008 | 0.011300442 | −23.94364826 | 7.730559 | 9.190335 | 9.619106 | 1.661149 | 4.608763 | 6.106561 |
| NOL6 | −1.089511108 | 0.043516135 | 0.008614495 | −23.94579735 | 8.934978 | 10.640261 | 9.509275 | 1.661149 | 5.857745 | 6.051818 |
| HHIPL1 | −0.970941699 | 0.043709154 | 0.012949302 | −24.18814023 | 7.980539 | 6.849665 | 6.861515 | 1.661149 | 2.265287 | 5.091834 |
| RAB11FIP5 | −1.26668748 | 0.043453389 | 0.004345696 | −24.45398266 | 7.355332 | 6.877454 | 7.746525 | 1.661149 | 3.134528 | 2.921909 |
| SLC43A3 | −1.118954647 | 0.043453389 | 0.0076222321 | −24.46831038 | 13.900662 | 12.612518 | 11.918273 | 7.30543 | 7.440337 | 9.642233 |
| SHOX2 | −0.978590593 | 0.043661316 | 0.012598843 | −24.5047815 | 9.700528 | 8.761199 | 10.43761 | 4.894482 | 7.269549 | 4.146207 |
| ABLIM2 | −0.983947884 | 0.043626235 | 0.012408983 | −24.72747266 | 8.459303 | 7.303362 | 7.762571 | 1.661149 | 3.134528 | 5.634184 |
| TMEM222 | −1.285803674 | 0.043453389 | 0.00412113 | −24.87311261 | 11.735611 | 11.421245 | 10.782636 | 6.651882 | 6.78473 | 6.924055 |
| PLA2G2A | −0.632746025 | 0.052998119 | 0.037717591 | −24.92344671 | 1.874444 | 6.904719 | 7.746525 | 1.661149 | 2.265287 | 2.921909 |
| HMOX2 | −1.187150649 | 0.043453389 | 0.006023859 | −24.98353047 | 11.750741 | 12.02403 | 10.825276 | 5.252045 | 7.107836 | 7.668215 |
| YTHDF2 | −1.393479198 | 0.043453389 | 0.002501531 | −25.0046254 | 12.815486 | 12.972053 | 12.867057 | 8.222933 | 8.385634 | 7.825039 |
| ZFP41 | −1.174561264 | 0.043453389 | 0.00627084 | −25.39003807 | 7.730559 | 6.931478 | 6.636262 | 1.661149 | 2.265287 | 3.630092 |
| S100A3 | −1.075714839 | 0.043516135 | 0.00908132 | −25.80324952 | 7.238972 | 8.319573 | 5.592916 | 1.661149 | 2.265287 | 3.630092 |
| HSF1 | −1.290214015 | 0.043453389 | 0.004051079 | −25.83329037 | 11.465836 | 12.206993 | 11.055992 | 6.396698 | 6.774676 | 7.36177 |
| EXT1 | −1.318299792 | 0.043453389 | 0.003603947 | −25.9066643 | 11.772709 | 12.592743 | 12.054033 | 7.25991 | 7.187136 | 7.897492 |
| PHB2 | −1.307973855 | 0.043453389 | 0.003753658 | −26.24230271 | 14.446432 | 14.778544 | 14.188872 | 9.002943 | 9.722706 | 10.350135 |
| TMBIM1 | −1.348326147 | 0.043453389 | 0.003113984 | −27.25902992 | 13.336931 | 12.66579 | 12.425557 | 8.087444 | 7.656894 | 8.287303 |
| CXCR7 | −1.1813783 | 0.043453389 | 0.000614835 | −27.2651573 | 12.246398 | 12.024036 | 10.910557 | 1.661149 | 7.25505 | 7.748756 |
| ATP6V0C | −1.384655155 | 0.043453389 | 0.002671657 | −28.10583583 | 13.775701 | 14.458412 | 14.410962 | 9.645614 | 9.375155 | 9.051056 |
| SETD8 | −1.298601103 | 0.043453389 | 0.003957809 | −28.54854148 | 11.569865 | 12.022481 | 12.134846 | 6.498222 | 7.187136 | 7.825039 |
| SNORD36C | −1.31106347 | 0.043453389 | 0.003719633 | −28.59802369 | 11.305107 | 12.608895 | 12.474479 | 7.771052 | 7.066159 | 6.924055 |
| ELK1 | −1.032984883 | 0.043577906 | 0.010466825 | −28.83483774 | 8.89708 | 7.77165 | 7.250844 | 1.661149 | 5.509998 | 2.921909 |
| PANK4 | −1.193406119 | 0.043453389 | 0.005855733 | −28.8469234 | 10.685004 | 10.852945 | 10.786565 | 1.661149 | 5.936219 | 7.180104 |
| PRRX2 | −1.235962298 | 0.043453389 | 0.004876489 | −28.91781073 | 11.472293 | 10.914608 | 12.199633 | 5.095353 | 7.740604 | 6.618407 |
| CAPZB | −1.364032662 | 0.043453389 | 0.002896223 | −29.1339417 | 14.504558 | 13.770854 | 13.621833 | 8.757204 | 9.218487 | 9.363984 |
| EXTL3 | −1.270357757 | 0.043453389 | 0.004264035 | −29.54570421 | 11.92955 | 10.821096 | 9.658228 | 5.252045 | 5.936219 | 6.195186 |
| ZFPM1 | −1.200479042 | 0.043453389 | 0.005665873 | −29.66208903 | 7.155835 | 7.965391 | 6.601009 | 1.661149 | 2.265287 | 3.630092 |
| POLR3E | −1.225860926 | 0.043453389 | 0.00505342 | −29.78040556 | 9.26756 | 9.686953 | 9.913086 | 1.661149 | 5.857745 | 4.790662 |
| SHF | −1.324459126 | 0.043453389 | 0.003338551 | −29.99913145 | 9.164988 | 9.038579 | 9.704647 | 1.661149 | 4.797798 | 4.476242 |
| MIIP | −1.034773197 | 0.043577906 | 0.010412385 | −30.2576043 | 7.841135 | 7.843866 | 7.646315 | 1.661149 | 5.353925 | 2.921909 |
| BCAR1 | −1.159990054 | 0.043453389 | 0.006617897 | −30.50092012 | 10.266516 | 11.130663 | 10.788525 | 4.802615 | 5.857745 | 7.46072 |
| OGFOD2 | −1.193521761 | 0.043453389 | 0.005848928 | −30.52268767 | 7.513971 | 7.197097 | 6.670675 | 1.661149 | 2.265287 | 3.630092 |
| HDGF | −1.133928581 | 0.043453389 | 0.007243961 | −30.57849285 | 10.117927 | 9.276362 | 9.532856 | 4.341916 | 6.549959 | 4.476242 |
| SEC61A1 | −1.363308609 | 0.043453389 | 0.002916638 | −30.7493823 | 13.931844 | 13.098107 | 12.46409 | 7.631894 | 8.486085 | 8.155622 |
| HAPLN3 | −1.230310392 | 0.043453389 | 0.004971759 | −31.2273392 | 11.071298 | 12.143311 | 12.243884 | 7.957464 | 7.066159 | 6.106561 |
| SLC45A4 | −1.170566648 | 0.043453389 | 0.006400136 | −31.5663239 | 8.55164 | 8.841005 | 8.487278 | 1.661149 | 3.571326 | 5.446557 |
| AKT1 | −1.363188046 | 0.043453389 | 0.002923443 | −31.91557789 | 12.030002 | 11.492623 | 11.352169 | 4.718672 | 6.794431 | 7.033813 |
| CXCL1 | −1.208205327 | 0.043453389 | 0.005461722 | −32.00179074 | 10.920464 | 11.648955 | 11.55004 | 7.792994 | 6.549959 | 5.874974 |
| NRBP1 | −1.307401639 | 0.043453389 | 0.003760463 | −32.29750587 | 12.648754 | 12.047164 | 11.901161 | 8.190235 | 6.794431 | 7.033813 |
| PAPPA | −1.151081904 | 0.043453389 | 0.006842463 | −32.79983607 | 12.906519 | 10.931279 | 10.287661 | 5.252045 | 6.373501 | 7.695565 |
| HPDL | −1.291325831 | 0.043453389 | 0.004039469 | −32.97913878 | 7.513971 | 7.965391 | 6.282905 | 1.661149 | 2.265287 | 2.921909 |
| POM121 | −1.269466165 | 0.043453389 | 0.0028445 | −33.32239888 | 7.278811 | 7.323707 | 7.481604 | 1.661149 | 2.265287 | 3.630092 |
| ST14 | −1.232366679 | 0.043453389 | 0.004930929 | −33.40774621 | 8.638422 | 11.11031 | 7.98402 | 4.341916 | 4.539173 | 2.921909 |
| CSF1 | −1.473909726 | 0.043453389 | 0.001711466 | −33.98864293 | 13.012599 | 12.359516 | 13.053461 | 7.30543 | 7.56803 | 7.96648 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA1-N171 | BRCA1-N174 |
|---|---|---|---|---|---|---|---|---|---|---|
| ZNF385A | −1.299184197 | 0.043453389 | 0.003951004 | −34.43309341 | 10.734196 | 10.132682 | 11.229095 | 5.026959 | 5.353925 | 6.73963 |
| SLC7A5 | −1.305999732 | 0.043453389 | 0.003780878 | −35.08488101 | 12.236315 | 13.12154 | 11.865388 | 7.74871 | 6.237456 | 7.988762 |
| ZC3H18 | −0.905115471 | 0.044173537 | 0.016178972 | −35.30928419 | 8.183076 | 7.756763 | 8.063885 | 1.661149 | 6.608026 | 2.921909 |
| SIN3A | −1.322824336 | 0.043453389 | 0.003522286 | −35.68378214 | 12.222974 | 11.787247 | 12.905953 | 6.244586 | 7.740604 | 7.748756 |
| SLC39A13 | −1.327805815 | 0.043453389 | 0.003440626 | −35.71742924 | 11.708516 | 11.855218 | 11.378439 | 1.661149 | 6.549959 | 7.020304 |
| NCOR2 | −1.27663494 | 0.043453389 | 0.0042164 | −35.77252063 | 11.08119 | 10.368847 | 11.361418 | 4.739845 | 5.920411 | 7.020304 |
| TNFRSF12A | −1.304907735 | 0.043453389 | 0.003808098 | −36.69515947 | 11.133737 | 13.199649 | 12.063779 | 8.087444 | 5.936219 | 6.195186 |
| CNTFR | −1.361643045 | 0.043453389 | 0.002937053 | −36.76125981 | 7.893399 | 7.08238 | 8.334642 | 1.661149 | 3.134528 | 2.921909 |
| PVRL1 | −1.148962222 | 0.043453389 | 0.006890099 | −36.88137962 | 8.129608 | 9.767145 | 10.27653 | 1.661149 | 5.936219 | 4.562324 |
| SDF4 | −1.433115184 | 0.043453389 | 0.002106159 | −37.50406544 | 12.606325 | 12.242159 | 11.568413 | 6.339437 | 7.138979 | 7.255535 |
| ERLIN1 | −1.311211592 | 0.043453389 | 0.003712827 | −38.04139106 | 11.704864 | 11.23506 | 11.748393 | 1.661149 | 7.094585 | 6.455366 |
| CCT2 | −1.538505871 | 0.043453389 | 0.001384825 | −38.08422211 | 14.53752 | 15.45363 | 14.74438 | 9.4931 | 9.666725 | 9.303041 |
| PPP1R14B | −1.407572375 | 0.043453389 | 0.0023382l | −38.5002184 | 13.46846 | 13.959023 | 12.774145 | 8.139755 | 8.055928 | 8.692228 |
| MAP7D1 | −1.349231338 | 0.043453389 | 0.003100374 | −38.67748926 | 13.436616 | 14.192165 | 13.634968 | 8.361545 | 8.033973 | 9.628105 |
| TNFRSF4 | −1.40968292 | 0.043453389 | 0.00231099 | −39.28100822 | 10.70342 | 9.803819 | 11.231079 | 4.739845 | 5.936219 | 5.091834 |
| PRRC2A | −1.442498163 | 0.043453389 | 0.002004083 | −39.56084343 | 11.946657 | 12.217905 | 12.080677 | 4.718672 | 6.774676 | 7.327219 |
| CTU2 | −1.423300168 | 0.043453389 | 0.002194624 | −40.08971128 | 9.272502 | 9.291936 | 8.896486 | 4.739845 | 3.571326 | 3.676349 |
| ANAPC2 | −1.172340152 | 0.043453389 | 0.006352501 | −40.21352716 | 8.959701 | 7.87177 | 8.967426 | 5.252045 | 2.265287 | 3.630092 |
| MFSD7 | −1.331296213 | 0.043453389 | 0.003365771 | −40.25576082 | 9.296962 | 9.007473 | 8.506461 | 1.661149 | 4.797798 | 3.676349 |
| CSNK2A1P | −1.361038187 | 0.043453389 | 0.002950663 | −40.59144864 | 11.263514 | 11.477946 | 10.994478 | 1.661149 | 5.920411 | 6.618407 |
| CYB5R2 | −1.22853843 | 0.043453389 | 0.005012589 | −40.6566729 | 10.192831 | 10.465868 | 9.021769 | 4.739845 | 6.205902 | 3.676349 |
| ACOT7 | −1.24677747 | 0.043453389 | 0.004713168 | −41.98246996 | 10.286197 | 11.331154 | 11.252009 | 4.894482 | 5.509998 | 7.352555 |
| OPLAH | −1.340798956 | 0.043453389 | 0.00322967 | −42.18604746 | 9.344671 | 9.075043 | 8.767255 | 5.026959 | 3.134528 | 3.676349 |
| FOSL1 | −1.578582579 | 0.043453389 | 0.001201089 | −42.5594008 | 11.796921 | 12.737687 | 11.624364 | 6.550689 | 6.237456 | 6.385515 |
| C11orf84 | −1.249683431 | 0.043453389 | 0.004638312 | −42.64502612 | 10.66635 | 8.644729 | 11.819147 | 5.252045 | 4.797798 | 5.426231 |
| RECQL4 | −1.403093335 | 0.043453389 | 0.002406261 | −44.05494592 | 6.792865 | 7.726519 | 8.553333 | 1.661149 | 2.265287 | 2.921909 |
| CSK | −1.314023 | 0.043453389 | 0.003651582 | −45.73401893 | 11.025194 | 11.073236 | 10.452524 | 1.661149 | 5.509998 | 6.649696 |
| FST | −1.445737051 | 0.043453389 | 0.001990473 | −45.96670366 | 13.420009 | 13.268836 | 11.534938 | 6.339437 | 6.640994 | 7.897492 |
| NAP1L4 | −1.373536741 | 0.043453389 | 0.002794148 | −48.01070264 | 12.722389 | 13.45184 | 13.090879 | 6.857154 | 7.505595 | 8.929599 |
| GSC | −1.351460142 | 0.043453389 | 0.003066349 | −48.75422278 | 9.237547 | 7.494953 | 8.553333 | 1.661149 | 3.571326 | 3.630092 |
| PRICKLE3 | −1.5466463l | 0.043453389 | 0.001316774 | −49.935035 | 8.705736 | 8.962765 | 9.272072 | 1.661149 | 3.571326 | 3.630092 |
| ARF1 | −1.605830256 | 0.043453389 | 0.001085403 | −50.91201485 | 16.051263 | 15.850516 | 15.232693 | 9.873821 | 10.434198 | 9.562759 |
| ABL1 | −1.506656192 | 0.043453389 | 0.001548146 | −50.92899856 | 13.422234 | 12.980487 | 13.207566 | 6.244586 | 7.53715 | 8.374509 |
| TMEM150A | −1.540384415 | 0.043453389 | 0.00137802 | −52.03248383 | 10.581282 | 10.064799 | 10.420013 | 4.718672 | 4.131418 | 5.426231 |
| EDNRB | −1.369859472 | 0.043453389 | 0.002828173 | −52.63071575 | 16.024278 | 14.320468 | 14.511564 | 7.918071 | 9.680925 | 10.306444 |
| ZC3H3 | −1.458519677 | 0.043453389 | 0.001840762 | −53.19539178 | 9.363321 | 9.538176 | 8.874506 | 1.661149 | 4.539173 | 3.630092 |
| S100A7 | −1.535053407 | 0.043453389 | 0.00140524 | −54.293114ó5 | 7.918838 | 8.684606 | 7.462086 | 1.661149 | 2.265287 | 2.921909 |
| SLC34A2 | −1.258017636 | 0.043453389 | 0.004502212 | −54.99206125 | 8.5104 | 11.827879 | 7.4423 | 6.857154 | 3.571326 | 4.476242 |
| PDLIM4 | −1.463502373 | 0.043453389 | 0.001786322 | −56.56801751 | 12.788139 | 14.182623 | 12.679069 | 9.415978 | 7.56803 | 8.269212 |
| RNF26 | −1.376047641 | 0.043453389 | 0.002760122 | −57.46658578 | 10.268991 | 9.634981 | 9.415978 | 5.705318 | 3.571326 | 3.630092 |
| SMURF1 | −1.518408267 | 0.043453389 | 0.001493705 | −58.24779733 | 13.205502 | 13.492287 | 13.395192 | 7.531061 | 7.25505 | 8.636861 |
| ADRA2C | −1.143524541 | 0.043453389 | 0.007012589 | −59.15827153 | 11.941236 | 8.848046 | 8.151795 | 4.341916 | 2.265287 | 5.882028 |
| ITGB5 | −1.366904937 | 0.043453389 | 0.002862198 | −60.002217 | 14.842401 | 14.590751 | 13.301169 | 7.394225 | 8.436733 | 9.995819 |
| TNFRSF1B | −1.472508512 | 0.043453389 | 0.001718272 | −60.18446343 | 12.961491 | 13.21675 | 13.609133 | 7.30543 | 6.373501 | 8.719135 |
| MSC | −1.356099743 | 0.043453389 | 0.003005104 | −62.23007221 | 11.353718 | 9.342669 | 10.301457 | 4.341916 | 3.134528 | 6.129407 |
| BCAN | −1.646719651 | 0.043453389 | 0.000942497 | −67.67595767 | 8.683645 | 7.74172 | 8.859664 | 1.661149 | 2.265287 | 2.921909 |
| PARP10 | −1.407416702 | 0.043453389 | 0.002345015 | −68.37146334 | 10.24153 | 9.67116 | 10.862976 | 1.661149 | 5.920411 | 4.146207 |
| TGFB1I1 | −1.437336263 | 0.043453389 | 0.002051718 | −68.60337821 | 13.445669 | 9.29161 | 12.446285 | 4.802615 | 7.191402 | 8.456743 |
| PLAU | −1.356315118 | 0.043453389 | 0.002998299 | −70.03420822 | 13.422512 | 12.862886 | 11.047831 | 1.661149 | 7.292524 | 7.152205 |

TABLE 8-continued

Differentially Expressed Genes in CD10−, CD24−, CD44+ Breast Epithelial cells of BRCA1 Mutation Carriers

| ID | t-value | q-value | p-value | Fold change | P1 | P2 | P3 | BRCA1-N105 | BRCA-N171 | BRCA1-N174 |
|---|---|---|---|---|---|---|---|---|---|---|
| NELF | −1.533219697 | 0.043453389 | 0.001412045 | −72.96003906 | 11.295428 | 11.542304 | 10.817617 | 1.661149 | 5.936219 | 5.106393 |
| LOC493754 | −1.592726357 | 0.043453389 | 0.001153454 | −73.2929511 | 12.591076 | 13.027374 | 13.636057 | 6.395481 | 7.989035 | 6.69026 |
| ST6GALNAC4 | −1.477261866 | 0.043453389 | 0.001691051 | −77.24943366 | 11.577872 | 10.256915 | 9.499733 | 1.661149 | 5.306419 | 4.476242 |
| PTPN23 | −1.625433235 | 0.043453389 | 0.001010548 | −83.90736359 | 12.940685 | 13.016869 | 12.113109 | 5.252045 | 6.549959 | 7.291822 |
| DEXI | −1.676603098 | 0.043453389 | 0.000833617 | −88.18520104 | 13.103459 | 13.16024 | 12.764217 | 5.728038 | 6.640994 | 7.611911 |
| PPP1R18 | −1.535851454 | 0.043453389 | 0.001398435 | −92.43491901 | 13.531403 | 13.587389 | 15.153047 | 6.544171 | 8.350533 | 8.622681 |
| G6PD | −1.618934407 | 0.043453389 | 0.001030963 | −94.50029597 | 13.572807 | 12.935748 | 12.358515 | 4.894482 | 6.373501 | 7.668215 |
| KRBA1 | −1.718073711 | 0.043453389 | 0.000690711 | −97.23318603 | 9.525286 | 9.686953 | 8.355951 | 1.661149 | 3.134528 | 2.921909 |
| RTN4RL2 | −1.796707132 | 0.043453389 | 0.000561415 | −102.4987363 | 8.78396 | 8.509169 | 9.601371 | 1.661149 | 2.265287 | 2.921909 |
| SNX8 | −1.469750014 | 0.043453389 | 0.001731882 | −111.131302 | 10.205806 | 9.71803 | 8.889197 | 1.661149 | 5.165949 | 3.630092 |
| C8orf82 | −1.765416053 | 0.043453389 | 0.000622661 | −130.174528 | 10.177104 | 9.651173 | 8.685452 | 1.661149 | 2.265287 | 3.630092 |
| TEAD4 | −1.565151516 | 0.043453389 | 0.001235114 | −133.3551204 | 8.720278 | 9.663198 | 9.410896 | 1.661149 | 2.265287 | 4.476242 |
| TRIM8 | −1.837758629 | 0.043453389 | 0.000466145 | −134.1110566 | 12.178907 | 11.176132 | 12.577282 | 5.095353 | 5.509998 | 5.106393 |
| KLC2 | −1.80152759 | 0.043453389 | 0.000547805 | −137.5778808 | 10.734196 | 10.78119 | 10.402199 | 1.661149 | 4.539173 | 3.630092 |
| PXDC1 | −1.97287208 | 0.043453389 | 0.000255189 | −181.3785395 | 13.835783 | 13.389565 | 14.655065 | 5.579836 | 6.549959 | 7.152205 |
| PI4K2A | −1.909491761 | 0.043453389 | 0.000343654 | −181.6360591 | 12.905327 | 13.400383 | 14.195167 | 5.320955 | 6.640994 | 6.69026 |
| NCS1 | −2.158869699 | 0.043453389 | 0.000146308 | −204.8049473 | 11.897918 | 12.105617 | 11.809525 | 4.894482 | 4.131418 | 4.146207 |
| SCRIB | −1.801281324 | 0.043453389 | 0.00055461 | −224.0705541 | 10.942337 | 11.150732 | 10.697557 | 1.661149 | 3.134528 | 5.106393 |
| MMP1 | −1.679174554 | 0.043453389 | 0.000826812 | −241.3496561 | 15.939572 | 12.046399 | 9.4756 | 1.661149 | 4.131418 | 4.790662 |
| MMP3 | −1.746023977 | 0.043453389 | 0.000656686 | −465.624075 | 14.466518 | 12.539371 | 11.057619 | 1.661149 | 6.640994 | 3.676349 |
| MMP12 | −2.408034216 | 0.043453389 | 7.83E−05 | −586.6006309 | 12.34294 | 11.169121 | 10.857383 | 1.661149 | 2.265287 | 2.921909 |

TABLE 9

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| HSPA1A | 2.011561712 | 0.04958755 | 0.000389152 | 2489.16994 | 2.993831 | 4.7365865 | 7.9976413 | 16.0180355 | 17.2726998 | 14.8795479 |
| LOC642361 | 2.198386219 | 0.04958755 | 0.000172511 | 2137.354775 | 1.8744435 | 2.0230478 | 2.9956812 | 10.9516464 | 13.1605909 | 14.0572919 |
| RPS29 | 2.280347449 | 0.04958755 | 0.000148439 | 1128.6294 | 4.309025 | 5.3621423 | 6.2829045 | 14.7874254 | 15.5024984 | 15.6669952 |
| HNRNPA1 | 2.349268832 | 0.04958755 | 0.000124368 | 858.800101 | 3.0245043 | 2.0230478 | 2.1654208 | 11.7692264 | 12.0704905 | 12.5017958 |
| MTRNR2L2 | 1.945683642 | 0.04958755 | 0.000493461 | 685.9243605 | 1.8744435 | 2.0230478 | 2.1654208 | 9.4518602 | 11.4449535 | 12.8355435 |
| RPL23AP32 | 2.091154616 | 0.04958755 | 0.000284843 | 647.8613061 | 3.8197323 | 5.4346801 | 5.5446534 | 13.4958827 | 14.2869369 | 14.8841946 |
| RPL27A | 2.112261591 | 0.04958755 | 0.000268796 | 548.9609052 | 5.7794294 | 5.1480825 | 6.6706745 | 14.2486421 | 15.5219953 | 15.4572907 |
| ERH | 2.042512894 | 0.04958755 | 0.000349033 | 536.2523097 | 2.993831 | 2.0230478 | 2.1654208 | 11.3198595 | 10.5362848 | 12.0605992 |
| COX6A1 | 1.966234652 | 0.04958755 | 0.000453342 | 533.4692445 | 2.2016907 | 2.0230478 | 2.1654208 | 9.5311029 | 11.2246821 | 11.7648175 |
| COX6C | 1.8119455 | 0.04958755 | 0.000846506 | 476.7862499 | 1.8744435 | 2.0230478 | 4.4498938 | 10.7716423 | 10.9430782 | 12.193477 |
| RPLP1 | 2.095830752 | 0.04958755 | 0.000276819 | 435.5638137 | 6.5212096 | 6.0726357 | 6.5278107 | 14.3822043 | 15.7350278 | 15.2879499 |
| PLAC9 | 2.087657395 | 0.04958755 | 0.000292867 | 417.2461993 | 1.8744435 | 2.406905 | 2.1654208 | 10.8701759 | 10.1377987 | 11.3236165 |
| S100A4 | 1.898294036 | 0.04958755 | 0.000581722 | 403.7127825 | 2.993831 | 2.0230478 | 2.1654208 | 9.6949272 | 10.8915463 | 11.6510165 |
| CRIP1 | 1.94320544 | 0.04958755 | 0.000509508 | 331.8700773 | 1.8744435 | 2.0230478 | 2.1654208 | 10.2489183 | 10.3046864 | 13.3062766 |
| TRMT5 | 2.00878041 | 0.04958755 | 0.000397176 | 313.6729166 | 2.993831 | 5.4346805 | 3.3243747 | 11.6174919 | 10.9138572 | 10.9475666 |
| RPL5 | 1.820629375 | 0.04958755 | 0.000806387 | 312.0508774 | 4.6820765 | 4.9115166 | 6.4507011 | 12.9677139 | 13.2606973 | 13.4534914 |
| GPR124 | 1.854126236 | 0.04958755 | 0.000726149 | 303.5484281 | 2.993831 | 2.406905 | 3.9352215 | 11.488177 | 10.474736 | 10.964382 |
| MRFAP1 | 1.925871803 | 0.04958755 | 0.000525556 | 297.7890169 | 1.8744435 | 2.0230478 | 2.1654208 | 10.2950545 | 9.9586202 | 10.3835676 |
| NGFRAP1 | 2.016446906 | 0.04958755 | 0.000381128 | 275.0852243 | 2.2016907 | 2.8096013 | 2.1654208 | 8.1554584 | 10.0147482 | 10.9133361 |
| EEF1B2 | 1.821363767 | 0.04958755 | 0.000798363 | 256.1184813 | 5.6586086 | 3.8720139 | 4.5083337 | 11.8726814 | 13.4982434 | 13.049964 |
| ID2B | 2.05796395 | 0.04958755 | 0.000332986 | 254.1750195 | 1.8744435 | 2.0230478 | 2.1654208 | 10.1550993 | 9.9150431 | 9.9011097 |
| ID4 | 1.897124133 | 0.04958755 | 0.000589746 | 252.5713197 | 2.993831 | 2.406905 | 2.1654208 | 9.921389 | 10.1587087 | 10.974378 |
| CSN1S2AP | 1.766559238 | 0.04958755 | 0.001006981 | 244.8191184 | 1.8744435 | 2.0230478 | 2.1654208 | 8.7595777 | 9.9586202 | 11.5499195 |
| NDUFA12 | 1.679843789 | 0.04958755 | 0.001327931 | 221.5800857 | 1.8744435 | 2.0230478 | 2.1654208 | 8.1554584 | 10.0147482 | 9.8147322 |
| TPT1 | 1.872361385 | 0.04958755 | 0.000669983 | 218.8064975 | 7.3175786 | 7.5987767 | 8.3453359 | 15.3722884 | 15.9356836 | 15.1839282 |
| FOS | 1.759686731 | 0.04958755 | 0.001023028 | 212.2571788 | 7.9061745 | 8.3595375 | 9.4853018 | 16.6082294 | 16.2213996 | 15.635844 |
| IGFBP7 | 1.65560679 | 0.04958755 | 0.001424216 | 209.3287664 | 7.3921232 | 5.1957839 | 6.7042855 | 12.9054307 | 14.6094119 | 14.8693167 |
| NDUFB4 | 1.493463501 | 0.04958755 | 0.002281152 | 208.7156419 | 5.3044627 | 3.7709946 | 2.1654208 | 10.0513961 | 10.1122999 | 11.5764126 |
| TMEM50A | 1.520345167 | 0.04958755 | 0.002112653 | 201.0725579 | 4.6394091 | 2.0230478 | 2.1654208 | 10.3937635 | 9.8802157 | 9.6746202 |
| BRP44L | 1.814686728 | 0.04958755 | 0.000834482 | 196.9348643 | 1.8744435 | 2.0230478 | 2.3793449 | 8.9446225 | 10.0009196 | 9.6498858 |
| ATP5C1 | 1.66930315 | 0.04958755 | 0.001360026 | 193.2139252 | 2.2016907 | 3.8720139 | 2.1654208 | 9.8991573 | 9.7594761 | 10.3326709 |
| C1orf54 | 1.847285377 | 0.04958755 | 0.000734173 | 187.3542647 | 1.8744435 | 2.0230478 | 2.1654208 | 8.9732809 | 9.5726728 | 9.9011097 |
| SCP2 | 1.647703974 | 0.04958755 | 0.001464334 | 186.263745 | 1.8744435 | 3.7709946 | 2.1654208 | 9.7946438 | 10.4061014 | 9.4156466 |
| LMOD1 | 1.6465569 | 0.04958755 | 0.001472358 | 182.7950339 | 2.2016907 | 3.360637 | 2.1654208 | 8.6922175 | 10.6322453 | 10.8747201 |
| VKORC1 | 1.81935768 | 0.04958755 | 0.000814411 | 180.0144181 | 2.2016907 | 2.0230478 | 2.3793449 | 10.515675 | 9.6573895 | 9.0502468 |
| COX5B | 1.577302487 | 0.04958755 | 0.001807751 | 178.3216194 | 4.2098819 | 2.406905 | 2.379449 | 9.4920255 | 9.8852428 | 11.7298405 |
| NEXN | 1.628041721 | 0.04958755 | 0.001560619 | 171.2147535 | 1.8744435 | 2.8096013 | 2.1654208 | 8.5941417 | 9.585084 | 11.7376868 |
| CAMLG | 1.584433083 | 0.04958755 | 0.001767632 | 170.8974041 | 1.8744435 | 2.8096013 | 3.7641245 | 9.6378909 | 9.2914302 | 11.346887 |
| ZCRB1 | 0.730109439 | 0.12232325 | 0.048180213 | 170.479371 | 1.8744435 | 2.0230478 | 2.3793449 | 9.4365051 | 1.2054667 | 10.1565715 |
| NSA2 | 1.665392749 | 0.04958755 | 0.001368049 | 170.1783538 | 3.0245043 | 4.3899364 | 4.2859964 | 10.6789908 | 10.8013455 | 11.8008401 |
| FRZB | 1.680291136 | 0.04958755 | 0.001319907 | 164.6148715 | 1.8744435 | 4.3899364 | 2.1654208 | 8.3206874 | 10.5364387 | 9.3859987 |
| LUM | 1.325246537 | 0.04958755 | 0.003685309 | 162.8753855 | 4.815804 | 2.0230478 | 5.9741452 | 14.898528 | 12.1634288 | 9.5102912 |
| NUDT4P1 | 1.50881325 | 0.04958755 | 0.002184867 | 161.4407011 | 1.8744435 | 2.0230478 | 3.9083598 | 8.4987997 | 9.6515005 | 11.2432203 |
| FAM83A | 1.087975532 | 0.051099543 | 0.007900185 | 157.7790835 | 4.2098819 | 2.0230478 | 2.1654208 | 4.5400907 | 10.2036711 | 9.32481 |
| GAS5 | 1.65829574 | 0.04958755 | 0.001384097 | 154.2221872 | 5.2636993 | 4.8304956 | 5.7236017 | 11.5103468 | 13.0980966 | 12.5325658 |
| SH3BGRL | 1.687732365 | 0.04958755 | 0.001287812 | 153.3767099 | 2.993831 | 3.7709946 | 3.9083598 | 10.2547666 | 10.4095948 | 11.5742234 |
| HTRA1 | 1.68985596 | 0.04958755 | 0.001271764 | 153.1310862 | 2.993831 | 2.8096013 | 3.9083598 | 11.1669832 | 9.7758097 | 10.4708877 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| EIF3E | 1.729612843 | 0.04958755 | 0.001111289 | 152.7662557 | 4.815804 | 4.9115166 | 3.9352215 | 12.166987 | 11.3390176 | 11.6777725 |
| HMGB1 | 1.786208332 | 0.04958755 | 0.000926743 | 151.9266336 | 3.3509967 | 3.7709946 | 3.9083598 | 10.4458174 | 11.0182256 | 11.209764 |
| NDUFB9 | 1.724643617 | 0.04958755 | 0.001135361 | 150.4087851 | 3.0245043 | 2.406905 | 2.1654208 | 9.2961016 | 9.63965 | 10.8240285 |
| ID2 | 1.858037615 | 0.04958755 | 0.000718126 | 147.0157127 | 1.8744435 | 2.0230478 | 2.1654208 | 9.1086088 | 9.3652474 | 9.1594204 |
| RPS8 | 1.672940289 | 0.04958755 | 0.001352002 | 143.9921462 | 7.3553323 | 8.1702751 | 8.5253933 | 14.4062143 | 15.6952396 | 15.4187663 |
| NPM1 | 1.697940181 | 0.04958755 | 0.001231646 | 135.1248514 | 4.2634629 | 5.297868 | 5.5715986 | 12.0878069 | 12.6497478 | 11.8702944 |
| APEX1 | 1.724583928 | 0.04958755 | 0.001143384 | 130.4360676 | 2.2016907 | 2.0230478 | 2.1654208 | 9.0559909 | 10.8890459 | 9.0502468 |
| RPL23P8 | 1.762733974 | 0.04958755 | 0.001015004 | 130.2506523 | 8.2244688 | 8.4079855 | 8.7104835 | 15.2496156 | 15.3777432 | 15.9830695 |
| SNX3 | 1.588710112 | 0.04958755 | 0.001751585 | 128.5751992 | 4.815804 | 3.360637 | 3.761245 | 10.7777775 | 10.367105 | 10.892401 |
| HSPA1B | 1.349532351 | 0.04958755 | 0.003436572 | 127.4012481 | 6.0548278 | 7.4768994 | 10.290431 | 14.470135 | 15.6075614 | 14.2615737 |
| HSPA6 | 1.257105041 | 0.04958755 | 0.004503731 | 124.381701 | 1.8744435 | 3.7709946 | 6.289045 | 11.2673077 | 12.0130894 | 8.833074 |
| GADD45A | 1.482436267 | 0.04958755 | 0.002377437 | 122.9810319 | 2.2016907 | 4.4133226 | 3.3243747 | 10.3175808 | 10.2666667 | 9.2717591 |
| SPARCL1 | 1.695383389 | 0.04958755 | 0.001247693 | 122.6627149 | 5.8972917 | 4.9115166 | 5.2176156 | 12.3396908 | 12.1561685 | 12.1441484 |
| SHFM1 | 1.623557334 | 0.04958755 | 0.001568643 | 121.4047016 | 1.8744435 | 2.406905 | 2.1654208 | 9.0891013 | 8.492491 | 11.1135456 |
| SDHD | 1.553693036 | 0.04958755 | 0.001924556 | 118.9246556 | 1.8744435 | 2.8096013 | 2.1654208 | 9.7035053 | 8.0663803 | 9.1710561 |
| TRIAP1 | 1.363652009 | 0.04958755 | 0.003300168 | 118.9385984 | 1.8744435 | 2.8096013 | 2.9956812 | 10.3007191 | 7.1932904 | 9.6827716 |
| CYC1 | 1.556023812 | 0.04958755 | 0.001936131 | 115.8145008 | 1.8744435 | 3.360637 | 2.9956812 | 8.7346847 | 9.9297155 | 9.8513533 |
| RPL37 | 1.623480945 | 0.04958755 | 0.001592714 | 113.8051711 | 7.4971815 | 8.5953745 | 8.7350882 | 14.5925156 | 15.5655105 | 15.3421906 |
| CSDA | 1.653217538 | 0.04958755 | 0.001432239 | 113.1484488 | 4.2634629 | 2.406905 | 3.9352215 | 10.7572945 | 10.4975743 | 10.8604176 |
| C3orf58 | 0.773325102 | 0.102731018 | 0.036751184 | 111.3829314 | 3.3509967 | 6.4662577 | 2.9956812 | 9.8991573 | 10.150381 | 2.9963609 |
| RPL22L1 | 1.542645885 | 0.04958755 | 0.002008345 | 110.5620909 | 3.0245043 | 2.0230478 | 2.1654208 | 9.4969685 | 9.8132173 | 8.1057709 |
| CRIM1 | 1.452682565 | 0.04958755 | 0.002594078 | 110.0472041 | 2.993831 | 4.3513152 | 2.3793449 | 8.9446225 | 9.7758097 | 11.2349287 |
| TSPYL4 | 1.612298222 | 0.04958755 | 0.001640857 | 109.7535432 | 3.0245043 | 2.0230478 | 2.9956812 | 9.1717924 | 9.802628 | 9.1358635 |
| ESD | 1.628935008 | 0.04958755 | 0.001544572 | 108.3953599 | 2.993831 | 2.0230478 | 3.761245 | 9.6644958 | 9.7539902 | 10.4708877 |
| FAM162A | 1.534570789 | 0.04958755 | 0.002024392 | 107.2637724 | 3.0245043 | 2.0230478 | 2.1654208 | 9.1021356 | 8.1852726 | 9.7695234 |
| VPS29 | 1.210057074 | 0.04969927 | 0.00521945 | 107.242504 | 1.8744435 | 2.0230478 | 2.1654208 | 8.7677808 | 5.6724615 | 9.6079656 |
| LMBRD1 | 1.588188941 | 0.04958755 | 0.001759608 | 102.988435 | 1.8744435 | 2.8096013 | 2.3793449 | 9.0559909 | 8.3971729 | 9.62472 |
| C2orf40 | 1.25502942 | 0.04958755 | 0.004551874 | 100.0050568 | 4.2098819 | 6.4662577 | 3.9083598 | 9.042531 | 12.0792909 | 13.1101869 |
| SNCA | 1.514903647 | 0.04958755 | 0.002136725 | 99.91921443 | 1.8744435 | 3.3213504 | 2.1654208 | 8.8081111 | 8.5186068 | 9.5194229 |
| HSPA2 | 1.624362497 | 0.04958755 | 0.001584691 | 98.81739776 | 2.2016907 | 2.0230478 | 2.1654208 | 8.792114 | 9.3866756 | 8.1996456 |
| RCN2 | 1.570698655 | 0.04958755 | 0.001855893 | 98.53634008 | 1.8744435 | 2.0230478 | 2.1654208 | 9.7865924 | 7.9173057 | 8.6456318 |
| MARCH7 | 1.573906313 | 0.04958755 | 0.001831822 | 96.59859584 | 1.8744435 | 2.0230478 | 2.9956812 | 9.0221027 | 8.9985279 | 8.4683738 |
| PDE5A | 1.392211273 | 0.04958755 | 0.00306748 | 96.29592213 | 3.3509967 | 2.0230478 | 2.9956812 | 7.7378191 | 9.585084 | 10.7866977 |
| GAS1 | 1.425320668 | 0.04958755 | 0.002842815 | 92.84004774 | 3.8197323 | 2.0230478 | 2.1654208 | 11.211266 | 9.1975554 | 8.5597232 |
| CENPH | 1.479198037 | 0.04958755 | 0.002433603 | 90.806377 | 4.7435639 | 3.7709946 | 2.1654208 | 9.8342407 | 11.2482856 | 10.1089703 |
| TMEM66 | 1.577099619 | 0.04958755 | 0.001815775 | 90.27049693 | 3.8197323 | 3.7709946 | 4.5083337 | 11.4273358 | 10.2743512 | 10.2906199 |
| LETMD1 | 1.607427252 | 0.04958755 | 0.001664928 | 90.23148577 | 1.8744435 | 2.0230478 | 2.1654208 | 8.0915413 | 8.5186068 | 9.2717591 |
| LOC572558 | 1.257774329 | 0.04958755 | 0.004495707 | 90.23148577 | 1.8744435 | 2.0230478 | 2.1654208 | 6.0805901 | 11.2715091 | 9.32481 |
| LGALS3 | 1.549891724 | 0.04958755 | 0.001968226 | 90.16385704 | 4.963444 | 4.9115166 | 5.7236017 | 12.5593915 | 11.2715091 | 11.4579213 |
| ARL5B | 1.390198804 | 0.04958755 | 0.003083527 | 89.53147488 | 1.8744435 | 2.0230478 | 4.7244061 | 10.0680992 | 11.2087291 | 8.2662493 |
| C9orf16 | 1.460560392 | 0.04958755 | 0.002529888 | 89.4839902 | 3.0245043 | 4.7507076 | 3.3243747 | 11.0954589 | 9.8079324 | 9.6989376 |
| TXN | 1.657574944 | 0.04958755 | 0.001400144 | 89.10525649 | 4.7435639 | 4.3899364 | 4.7244061 | 11.0440392 | 10.950811 | 11.2210025 |
| KLHL20 | 1.458277395 | 0.04958755 | 0.001863917 | 88.28304195 | 1.8744435 | 2.0230478 | 2.3793449 | 9.8264078 | 7.4590463 | 8.4871122 |
| SSBP2 | 1.567587513 | 0.04958755 | 0.001863917 | 86.87340126 | 2.2016907 | 2.0230478 | 2.3793449 | 8.2046286 | 8.6425333 | 9.9957527 |
| OTUD1 | 1.387472669 | 0.04958755 | 0.003107598 | 86.31581609 | 3.3509967 | 2.0230478 | 4.2859964 | 9.7825497 | 8.6306088 | 10.2852763 |
| FRA10AC1 | 1.529397684 | 0.04958755 | 0.002064511 | 86.18477383 | 3.0245043 | 2.0230478 | 2.1654208 | 8.5848861 | 8.4524089 | 9.5991074 |
| CPE | 1.411164363 | 0.04958755 | 0.002963171 | 86.13910109 | 5.6586086 | 4.3513152 | 6.0316576 | 13.1100097 | 10.799116 | 11.6447709 |
| NDUFS4 | 1.32764682 | 0.04958755 | 0.003637166 | 86.00454975 | 4.2098819 | 2.0230478 | 2.1654208 | 8.8473445 | 8.9320699 | 8.4493889 |
| RHOBTB2 | 1.299050496 | 0.04958755 | 0.003934045 | 86.00454975 | 1.8744435 | 2.0230478 | 2.1654208 | 6.3362802 | 9.1975554 | 8.4493889 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| HOXD8 | 1.256597584 | 0.04958755 | 0.004519779 | 86.00454975 | 1.8744435 | 2.0230478 | 2.3793449 | 6.2304884 | 8.9609276 | 8.4493889 |
| ATPIF1 | 1.520079762 | 0.04958755 | 0.002120677 | 85.457625 | 3.0245043 | 2.0230478 | 2.3793449 | 9.4416416 | 8.2645713 | 8.8905079 |
| EXTL2 | 1.657927005 | 0.04958755 | 0.001392121 | 85.17722749 | 1.8744435 | 2.0230478 | 2.1654208 | 8.2868394 | 8.5694617 | 8.4683738 |
| TGFBI | 1.431778936 | 0.04958755 | 0.002794672 | 84.5847424 | 6.3818471 | 5.1480825 | 6.7692467 | 11.5888403 | 12.5511867 | 13.1715722 |
| C8orf59 | 1.527350527 | 0.04958755 | 0.002088582 | 81.75696807 | 3.8399484 | 3.3213504 | 2.1654208 | 9.2789856 | 10.0819703 | 9.6746202 |
| DDOST | 1.359787432 | 0.04958755 | 0.003348311 | 81.75222065 | 4.6394091 | 3.3213504 | 2.1654208 | 10.5278012 | 8.5186068 | 10.2959438 |
| CPNE3 | 1.269435444 | 0.04958755 | 0.004311161 | 81.17688147 | 4.309025 | 3.8720139 | 2.1654208 | 8.6661239 | 8.8104958 | 10.652022 |
| LDB3 | 1.222646743 | 0.049622329 | 0.005025275 | 81.05015516 | 3.0245043 | 5.297868 | 2.1654208 | 8.7093547 | 9.3652474 | 9.8072951 |
| IKBIP | 1.306551712 | 0.04958755 | 0.003869855 | 80.2856462 | 4.309025 | 2.0230478 | 2.1654208 | 8.3860905 | 8.492491 | 9.62472 |
| PA2G4 | 1.560754558 | 0.04958755 | 0.00191206 | 78.66443444 | 1.8744435 | 2.0230478 | 2.1654208 | 8.3206874 | 7.89754 | 9.0502468 |
| NNMT | 1.272026986 | 0.04958755 | 0.004263019 | 77.61720445 | 4.6394091 | 5.4346801 | 3.7641245 | 11.7129846 | 9.0169669 | 11.0329417 |
| RAB13 | 1.263967871 | 0.04958755 | 0.004407446 | 77.58775101 | 5.4911209 | 3.3213504 | 2.9956812 | 10.2893675 | 9.3214118 | 9.5991074 |
| COX4I1 | 1.534205737 | 0.04958755 | 0.002048463 | 77.5690528 | 5.3162271 | 4.8079702 | 5.7236017 | 11.2157704 | 11.5936364 | 11.7298405 |
| MFF | 1.543301563 | 0.04958755 | 0.002000321 | 77.33312988 | 3.0245043 | 2.0230478 | 3.3243747 | 8.90798 | 9.5973894 | 9.2932141 |
| ARID4A | 1.357625431 | 0.04958755 | 0.003372382 | 77.21562241 | 4.309025 | 2.406905 | 3.9083598 | 10.6459942 | 8.6777266 | 9.9150162 |
| TSPAN8 | 1.592514075 | 0.04958755 | 0.001727513 | 76.69548921 | 1.8744435 | 2.0230478 | 8.1428995 | 9.1428995 | 8.1355133 | 8.6948242 |
| NFYC | 1.18893642 | 0.049809046 | 0.005525957 | 76.64975075 | 3.0245043 | 2.406905 | 3.9352215 | 9.2847135 | 6.9843361 | 10.4614424 |
| PSMA5 | 1.318513484 | 0.04958755 | 0.003741475 | 76.47272106 | 4.2634629 | 2.0230478 | 2.1654208 | 9.2499997 | 8.2799211 | 8.8476482 |
| PDGFD | 1.594099673 | 0.04958755 | 0.00171949 | 75.74114718 | 1.8744435 | 2.0230478 | 2.1654208 | 8.1174489 | 8.618585 | 8.1534715 |
| RPL7 | 1.3766417 | 0.04958755 | 0.00319586 | 75.71781413 | 7.7305591 | 8.0774702 | 8.1395596 | 12.8629666 | 14.320031 | 14.4021203 |
| GUCY1A3 | 1.204465435 | 0.049809046 | 0.005317339 | 75.23008478 | 3.8399484 | 2.8096013 | 2.1654208 | 6.7105675 | 10.0731862 | 9.449072 |
| TUBA1B | 1.495452473 | 0.04958755 | 0.002257081 | 74.96786098 | 5.8972917 | 6.0361098 | 5.5929159 | 11.3651676 | 12.2643101 | 12.1278212 |
| FBXL5 | 1.492505724 | 0.04958755 | 0.002289176 | 74.82594796 | 2.993831 | 2.0230478 | 2.1654208 | 9.1779611 | 12.2799211 | 8.3908876 |
| WBP5 | 1.479710635 | 0.04958755 | 0.002409532 | 74.31002586 | 2.993831 | 4.7507076 | 3.9352215 | 10.3777739 | 10.1036991 | 10.1507065 |
| NCSTN | 1.287900928 | 0.04958755 | 0.004054401 | 74.01416522 | 4.2634629 | 2.0230478 | 2.1654208 | 10.6548673 | 7.89754 | 9.2054107 |
| CDKN1B | 1.258808243 | 0.04958755 | 0.004487684 | 73.91627559 | 3.0245043 | 2.8096013 | 3.3243747 | 9.2323245 | 9.63965 | 7.277042 |
| EIF2B1 | 1.619324424 | 0.04958755 | 0.001608762 | 73.79376795 | 1.8744435 | 2.0230478 | 2.1654208 | 8.2166637 | 8.2014848 | 8.3708479 |
| CSRP2 | 1.277513525 | 0.04958755 | 0.004150686 | 73.52784755 | 2.993831 | 2.0230478 | 2.1654208 | 6.7770801 | 8.6306088 | 9.1940499 |
| MYEOV2 | 1.59222937 | 0.04958755 | 0.001735537 | 73.47300304 | 1.8744435 | 2.0230478 | 2.1654208 | 8.4486569 | 8.0305306 | 8.2221901 |
| MDP1 | 1.353328829 | 0.04958755 | 0.003412501 | 73.47300304 | 1.8744435 | 2.0230478 | 2.1654208 | 6.7770801 | 8.5186068 | 8.2221901 |
| AKR1D1 | 1.451592365 | 0.04958755 | 0.002626173 | 73.33292309 | 2.993831 | 3.7709946 | 3.9352215 | 9.1902202 | 10.5332397 | 9.5011013 |
| SUMO1P3 | 1.509272512 | 0.04958755 | 0.00216882 | 73.3088369 | 3.0245043 | 2.0230478 | 2.9956812 | 9.2204195 | 8.7233541 | 8.7577092 |
| OSGEP | 1.181992672 | 0.049897122 | 0.005702479 | 71.42190958 | 2.2016907 | 2.0230478 | 3.3243747 | 6.4501951 | 9.4826695 | 8.3908876 |
| RAB6C | 1.356873329 | 0.04958755 | 0.003380406 | 71.33648369 | 1.8744435 | 2.8096013 | 1.6154208 | 8.9661695 | 8.9609276 | 7.0438915 |
| TUBA1A | 1.527741496 | 0.04958755 | 0.002080463 | 70.82043701 | 4.963444 | 5.8096013 | 4.9444683 | 11.0905621 | 11.9316049 | 11.5610175 |
| ZMYM6NB | 1.27444784 | 0.04958755 | 0.004206852 | 70.7599515 | 4.2634629 | 2.0230478 | 2.1654208 | 8.167909 | 8.492491 | 9.1119156 |
| SEPP1 | 1.438843966 | 0.049897122 | 0.002770601 | 69.7076022 | 2.2016907 | 4.7507076 | 5.2176156 | 12.5605724 | 10.8739517 | 10.2307226 |
| SRP9 | 1.340519984 | 0.04958755 | 0.003508786 | 68.75018272 | 6.0082059 | 4.3513152 | 4.7244061 | 10.4886329 | 10.8276977 | 10.964382 |
| TMEM173 | 1.410807276 | 0.04958755 | 0.002971195 | 67.89101196 | 2.2016907 | 3.3213504 | 2.3793449 | 8.2868394 | 8.3543123 | 10.2582573 |
| SMARCD3 | 1.366321237 | 0.04958755 | 0.003268073 | 67.67969473 | 3.8399484 | 2.0230478 | 2.1654208 | 8.7093547 | 9.5411694 | 8.1057709 |
| TMEM14C | 1.440060555 | 0.04958755 | 0.002738506 | 67.42583117 | 3.8399484 | 2.406905 | 2.9956812 | 8.9873994 | 9.0709107 | 9.2278676 |
| HNRPDL | 1.143832093 | 0.050004604 | 0.006502447 | 67.09977963 | 5.3354128 | 5.6616851 | 5.7236017 | 11.7298786 | 12.0073369 | 9.0875635 |
| DKK3 | 1.021508686 | 0.053385633 | 0.009912541 | 66.06024177 | 2.2016907 | 3.360637 | 2.3793449 | 5.3405168 | 8.4250552 | 10.0784017 |
| LSM6 | 1.474758131 | 0.04958755 | 0.002449651 | 65.53641157 | 1.8744435 | 2.406905 | 2.1654208 | 7.7210195 | 9.2539552 | 8.1996456 |
| UBE2NL | 1.300373059 | 0.04958755 | 0.003917997 | 65.24682953 | 1.8744435 | 3.3213504 | 3.7641245 | 8.3094927 | 9.7919604 | 8.4106527 |
| SNX17 | 1.37096864 | 0.04958755 | 0.003244002 | 65.18289308 | 3.8399484 | 2.8096013 | 2.9956812 | 9.0221027 | 8.4111814 | 10.3785579 |
| SYNPO2 | 1.088683463 | 0.051099543 | 0.007887613 | 65.04402637 | 6.09999914 | 3.7709946 | 3.9352215 | 8.0517861 | 10.4677231 | 12.123336 |
| EIF3M | 1.167538131 | 0.04991757 | 0.006054722 | 65.02830438 | 1.8744435 | 4.8304956 | 2.3793449 | 8.5376958 | 9.2989842 | 7.8974394 |
| ARPC2 | 1.338497886 | 0.04958755 | 0.003524834 | 64.94385735 | 5.2636993 | 3.8720139 | 3.3243747 | 10.3091746 | 10.7192716 | 9.3454959 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| MAGEB10 | 1.468276533 | 0.04958755 | 0.002497793 | 64.67962353 | 3.0245043 | 2.0230478 | 2.1654208 | 8.0382872 | 8.6892694 | 8.7108559 |
| LOC401397 | 1.288154681 | 0.04958755 | 0.004046377 | 64.67962353 | 3.8399484 | 2.0230478 | 2.1654208 | 8.0382872 | 8.2951094 | 8.5238744 |
| SFRP2 | 1.102664421 | 0.050647945 | 0.007502207 | 64.43314203 | 3.8399484 | 2.8096013 | 4.7244061 | 11.9249666 | 9.8496795 | 7.0438915 |
| CCNI | 1.412509957 | 0.04958755 | 0.0029391 | 64.1749969 | 7.2590288 | 5.1480825 | 6.4897707 | 13.2138577 | 12.0715935 | 12.4937102 |
| CPZ | 1.374128252 | 0.04958755 | 0.003219931 | 63.71532184 | 2.993831 | 2.8096013 | 3.9352215 | 9.3407758 | 8.3397377 | 9.92879 |
| F10 | 1.26110697 | 0.04958755 | 0.004439541 | 63.21189527 | 2.2016907 | 4.3513152 | 3.3243747 | 7.8958605 | 9.3064989 | 11.1344986 |
| PPP1CA | 1.297655189 | 0.04958755 | 0.003950092 | 62.71417303 | 3.8399484 | 2.0230478 | 2.1654208 | 8.3317959 | 7.9937674 | 8.7423946 |
| C4orf43 | 1.471272756 | 0.04958755 | 0.002473722 | 62.6869192 | 2.2016907 | 2.0230478 | 2.1654208 | 7.6158948 | 8.1355133 | 8.9725869 |
| PLRG1 | 1.349951005 | 0.04958755 | 0.003428549 | 62.56072818 | 2.2016907 | 3.7709946 | 2.3793449 | 8.6033384 | 8.1688761 | 9.0375903 |
| PTP4A3 | 1.04157703 | 0.052218844 | 0.009273851 | 62.25169979 | 4.2098819 | 5.4346801 | 3.9083598 | 7.333969 | 11.3947214 | 10.7522537 |
| BPHL | 1.447922215 | 0.04958755 | 0.002650245 | 62.2475057 | 1.8744435 | 2.0230478 | 2.1654208 | 7.9829919 | 9.9869572 | 7.6203219 |
| RNF130 | 1.247274884 | 0.04958755 | 0.004648159 | 62.06909417 | 2.993831 | 2.406905 | 4.2859964 | 10.1425368 | 7.4040744 | 10.2417996 |
| C10orf116 | 1.107755293 | 0.050567091 | 0.007332103 | 61.81852322 | 6.0082059 | 7.1970971 | 6.9199049 | 9.906606 | 12.8698722 | 14.2454979 |
| PABPC1 | 1.497341339 | 0.04958755 | 0.002224986 | 61.79922223 | 8.3134756 | 8.2991672 | 8.2910567 | 13.8826068 | 14.248684 | 14.6961651 |
| YBX1 | 1.439984097 | 0.04958755 | 0.0274653 | 61.71215431 | 5.0569476 | 4.7507076 | 5.3892653 | 10.4560066 | 11.0044304 | 11.671642 |
| TMEM200B | 1.243826297 | 0.04958755 | 0.004688277 | 61.4443822 | 1.8744435 | 2.0230478 | 3.9083598 | 8.0109044 | 7.8156527 | 8.577319 |
| SCARB2 | 1.271590944 | 0.04958755 | 0.004271042 | 61.13940004 | 4.963444 | 4.4133226 | 4.5083337 | 11.1145241 | 9.0531526 | 10.4423642 |
| COMMD3 | 1.256251288 | 0.04958755 | 0.004527802 | 61.09554124 | 1.8744435 | 2.0230478 | 2.1654208 | 6.2771857 | 7.956043 | 6.6948242 |
| TTC37 | 1.413153818 | 0.04958755 | 0.002923052 | 61.08895858 | 3.3509967 | 3.3213504 | 2.3793449 | 9.1779611 | 9.2883364 | 8.350526 |
| LOC100130992 | 0.954763991 | 0.058459296 | 0.013046618 | 60.66146213 | 1.8744435 | 2.0230478 | 2.9956812 | 4.5400907 | 8.2014848 | 8.9183896 |
| GTF3A | 1.494946165 | 0.04958755 | 0.002265105 | 60.48710739 | 1.8744435 | 2.0230478 | 2.1654208 | 7.5790795 | 8.0839766 | 8.0813159 |
| C13orf15 | 1.302997066 | 0.04958755 | 0.003877879 | 59.80779534 | 3.8399484 | 3.7709946 | 3.3243747 | 9.6732562 | 9.7812134 | 8.2221901 |
| NUP133 | 1.354719271 | 0.04958755 | 0.0338843 | 59.75383871 | 2.2016907 | 2.0230478 | 2.1654208 | 6.9599943 | 8.0663803 | 8.6456318 |
| DLC1 | 1.239666427 | 0.04958755 | 0.004720372 | 59.10560221 | 1.8744435 | 2.8096013 | 4.2859964 | 11.1164882 | 7.7062919 | 8.6948242 |
| KAZALD1 | 1.164353572 | 0.04991757 | 0.006102864 | 58.89126673 | 1.8744435 | 2.0230478 | 4.7549172 | 7.7544253 | 8.5314896 | 8.985824 |
| AGR2 | 1.3674802 | 0.04958755 | 0.003284121 | 57.99132181 | 1.8744435 | 2.0230478 | 2.1654208 | 7.8808129 | 6.9463683 | 8.6118796 |
| PPIG | 1.086854253 | 0.051099543 | 0.007948327 | 57.9386355 | 5.7794294 | 4.8079702 | 4.5083337 | 11.6764143 | 8.3971729 | 10.664424 |
| PDGFRL | 1.273968839 | 0.04958755 | 0.0042229 | 57.9105084 | 1.8744435 | 2.0230478 | 3.7641245 | 9.6198778 | 7.7288372 | 7.925186 |
| SUMF1 | 1.338681832 | 0.04958755 | 0.00351681 | 57.55403893 | 1.8744435 | 3.360637 | 2.1654208 | 9.0289443 | 8.0122661 | 7.8108476 |
| MYH11 | 1.228827781 | 0.049622329 | 0.004920966 | 57.27924846 | 2.993831 | 4.3899364 | 2.1654208 | 8.5472581 | 10.7471516 | 8.0053615 |
| CHTOP | 1.238000448 | 0.04958755 | 0.004752467 | 57.11515586 | 4.815804 | 2.0230478 | 2.9956812 | 8.4281014 | 8.831483 | 10.0722095 |
| APOF | 1.154242557 | 0.04991757 | 0.006335553 | 56.38520863 | 1.8744435 | 2.0230478 | 2.1654208 | 5.7241063 | 8.1688761 | 7.8402926 |
| DNAJC1 | 1.208497727 | 0.04976927 | 0.005259568 | 56.09338511 | 3.3509967 | 2.8096013 | 2.9956812 | 8.2166637 | 6.6504789 | 8.9592273 |
| RAB9A | 1.146298538 | 0.049952273 | 0.006446281 | 56.09338511 | 3.3509967 | 2.0230478 | 2.1654208 | 8.2166637 | 6.4455364 | 9.2609108 |
| TMEM9 | 1.336139445 | 0.04958755 | 0.003556929 | 55.96704725 | 2.2016907 | 3.3213504 | 3.3243747 | 9.1278561 | 7.7728978 | 10.652022 |
| ISCU | 1.121704249 | 0.050341156 | 0.00693252 | 55.74772078 | 4.963444 | 3.7709946 | 4.5083337 | 10.3091746 | 7.9173057 | 11.016911 |
| CIR1 | 1.391702504 | 0.04958755 | 0.003075503 | 55.60823767 | 3.3509967 | 3.3213504 | 3.7641245 | 9.9648504 | 9.1482234 | 8.6786124 |
| PCBP1 | 1.469786481 | 0.04958755 | 0.002481746 | 55.45771505 | 6.0999914 | 5.4876732 | 6.0560619 | 11.5237292 | 11.7765588 | 11.8933076 |
| SCOC | 1.187092333 | 0.049875978 | 0.005582123 | 55.16140473 | 2.2016907 | 2.406905 | 2.3793449 | 8.1924923 | 6.2722716 | 8.1767432 |
| SERPINB1 | 1.363712477 | 0.04958755 | 0.003292145 | 54.12838797 | 1.8744435 | 2.0230478 | 2.1654208 | 8.2404369 | 8.9609276 | 7.925186 |
| ANGPT1 | 1.272721237 | 0.04958755 | 0.004246971 | 54.10692909 | 5.0569476 | 2.0230478 | 4.2404061 | 6.4501951 | 9.0260988 | 7.7807893 |
| RRAD | 1.182597163 | 0.049897122 | 0.005670384 | 53.9419662 | 5.0569476 | 2.8096013 | 4.7244061 | 8.2046286 | 10.4777423 | 11.4507791 |
| TXNIP | 1.272637775 | 0.04958755 | 0.004254995 | 52.94693365 | 6.7078705 | 4.7507076 | 6.564874 | 12.3547449 | 10.8013455 | 12.2913492 |
| RPS20 | 1.373057483 | 0.04958755 | 0.003235978 | 52.86393774 | 8.2941654 | 8.5442716 | 8.4481275 | 13.4266559 | 14.1723395 | 14.6373499 |
| FTO | 1.213656157 | 0.049622329 | 0.005153655 | 51.24389687 | 5.3354128 | 2.8096013 | 2.9956812 | 8.4889095 | 10.1711108 | 9.6162329 |
| TAF7 | 1.185041995 | 0.049897122 | 0.005614218 | 51.20170184 | 4.6820765 | 3.7709946 | 2.1654208 | 9.6107862 | 9.4491144 | 8.0564393 |
| JPH4 | 1.300400867 | 0.04958755 | 0.003909974 | 51.1341912 | 3.0245043 | 2.0230478 | 2.1654208 | 7.7070287 | 8.7007207 | 8.3908876 |
| SDPR | 1.188535221 | 0.049809046 | 0.005533981 | 51.08655784 | 2.2016907 | 2.0230478 | 2.1654208 | 6.0269554 | 9.0351732 | 7.8402926 |
| MINOS1 | 1.28631585 | 0.04958755 | 0.004070449 | 50.69951751 | 5.0569476 | 3.8720139 | 4.4498938 | 9.535914 | 9.5973894 | 10.8129303 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| ZNF32 | 1.141081302 | 0.050038461 | 0.006558613 | 50.65987046 | 4.6394091 | 3.8720139 | 2.1654208 | 7.4827092 | 9.5347853 | 10.3735309 |
| PCOLCE | 1.235550224 | 0.04958755 | 0.004808634 | 50.64708585 | 4.2098819 | 5.4346801 | 6.6010094 | 11.0970874 | 10.3562848 | 11.595968 |
| PLS3 | 1.24253936 | 0.04958755 | 0.004696301 | 50.40470395 | 2.2016907 | 3.8720139 | 2.3793449 | 7.9107527 | 7.8571772 | 10.7050105 |
| LSM3 | 1.112589744 | 0.050440463 | 0.007214956 | 50.40432222 | 5.3044627 | 2.8096013 | 3.3243747 | 8.5183788 | 8.9978503 | 9.0752315 |
| NGRN | 1.213165485 | 0.049622329 | 0.005169702 | 50.36193654 | 3.3509967 | 3.8720139 | 2.9956812 | 9.5262757 | 7.4857665 | 9.5011013 |
| ZFP2 | 1.230649539 | 0.04958755 | 0.004880847 | 49.76630678 | 1.8744435 | 2.0230478 | 2.1654208 | 6.2304884 | 7.6601162 | 8.5056104 |
| PFDN5 | 1.283686576 | 0.04958755 | 0.004102544 | 49.11269646 | 6.6175557 | 6.4291807 | 7.1568531 | 11.3932764 | 12.2604461 | 12.7748773 |
| PSMA3 | 1.226333944 | 0.049622329 | 0.004961085 | 49.09072991 | 4.2634629 | 2.0230478 | 3.3243747 | 7.9254928 | 8.9417534 | 9.473175 |
| NFIA | 1.144851825 | 0.049952273 | 0.006478376 | 48.59003034 | 8.2039211 | 5.3406193 | 7.3175252 | 13.8065095 | 11.7340016 | 11.9107637 |
| CC2D2B | 1.390073999 | 0.04958755 | 0.003091551 | 48.26304389 | 1.8744435 | 2.0230478 | 2.1654208 | 7.6158948 | 7.2567201 | 8.7267115 |
| HSDL2 | 0.972842488 | 0.056901344 | 0.012062104 | 48.02597265 | 4.6394091 | 2.0230478 | 2.3793449 | 5.5826351 | 8.872563 | 10.2252152 |
| LPCAT4 | 1.179623371 | 0.049897122 | 0.005806788 | 47.87739864 | 1.8744435 | 3.3213504 | 2.3793449 | 6.5294995 | 8.9026233 | 8.3908876 |
| ITFG1 | 1.223162307 | 0.049622329 | 0.005009227 | 47.69275331 | 3.8399484 | 2.0230478 | 2.1654208 | 8.5848861 | 7.0925914 | 9.4156466 |
| MMGT1 | 1.192755838 | 0.049800046 | 0.005477814 | 47.34622678 | 4.6820765 | 3.7709946 | 2.1654208 | 9.7373165 | 9.3361721 | 8.1298183 |
| MEA1 | 1.320226275 | 0.04958755 | 0.003717404 | 44.98683606 | 4.2098819 | 4.4133226 | 4.9444683 | 9.9719683 | 8.9026233 | 11.2432203 |
| EPHX1 | 1.235368241 | 0.04958755 | 0.004816657 | 47.13234991 | 4.2098819 | 4.4133226 | 4.9444683 | 9.9719683 | 8.9026233 | 11.2432203 |
| PNRC1 | 1.223343852 | 0.049622329 | 0.005001204 | 46.9937726 | 8.1619262 | 6.1390574 | 8.0377511 | 12.9334843 | 13.7163239 | 12.3019721 |
| CCNG1 | 1.179877657 | 0.049897122 | 0.005790741 | 46.95821723 | 2.2016907 | 4.7507076 | 2.1654208 | 9.0152285 | 9.0884529 | 7.7187266 |
| ATP5F1 | 1.239248843 | 0.04958755 | 0.004728396 | 46.94223549 | 3.0245043 | 2.8096013 | 3.9352215 | 9.9612782 | 7.8365643 | 8.577319 |
| TOP1P1 | 1.331001422 | 0.04958755 | 0.003605071 | 46.20712428 | 2.993831 | 2.0230478 | 3.9083598 | 8.8855392 | 9.0351732 | 8.5238744 |
| H6PD | 1.064669082 | 0.051378258 | 0.008807582 | 45.82600305 | 6.5861495 | 3.360637 | 2.3793449 | 11.0098654 | 10.507389 | 7.8974394 |
| RCAN2 | 1.080495704 | 0.051255379 | 0.008116023 | 45.5828459 | 5.7445127 | 2.406905 | 4.7244061 | 8.6124767 | 11.261781 | 9.2825265 |
| PROS1 | 1.251466364 | 0.04958755 | 0.004591992 | 45.04456776 | 2.993831 | 2.406905 | 3.9352215 | 8.1045532 | 8.6064601 | 8.4871122 |
| CKS1B | 1.275690462 | 0.04958755 | 0.004166734 | 44.90963177 | 3.0245043 | 2.0230478 | 3.3243747 | 9.1902202 | 7.5120008 | 8.4301508 |
| UQCRQ | 1.17123908 | 0.04991757 | 0.005966461 | 44.424703 | 5.8565586 | 4.3513152 | 3.7641245 | 9.6600956 | 9.2374148 | 11.9518161 |
| RBMXL1 | 1.238370018 | 0.04958755 | 0.004744444 | 44.36064291 | 4.963444 | 2.406905 | 3.9083598 | 9.8991573 | 9.3795682 | 8.9045161 |
| ETV1 | 1.395577091 | 0.04958755 | 0.003027361 | 43.85511891 | 2.2016907 | 2.0230478 | 2.3793449 | 7.6339561 | 8.0663803 | 7.4777211 |
| GEM | 1.12529579 | 0.050330336 | 0.006876354 | 43.52923052 | 5.3044627 | 6.1390574 | 7.8096632 | 11.9585009 | 12.0988978 | 10.7483753 |
| HAS2 | 1.053335045 | 0.051900312 | 0.00892241 | 43.50277077 | 1.8744435 | 2.8096013 | 5.018694 | 8.7759375 | 7.3174789 | 8.8034763 |
| TRA2B | 1.254309489 | 0.04958755 | 0.004567921 | 43.49411589 | 5.7445127 | 4.7365865 | 5.018694 | 9.8342407 | 11.1925978 | 10.461424 |
| BAG3 | 1.16868153 | 0.04991757 | 0.006014603 | 43.44352174 | 5.7445127 | 6.9314777 | 7.6635078 | 11.4757116 | 13.104577 | 11.6067187 |
| ITPKB | 1.251400122 | 0.04958755 | 0.004600016 | 43.24542336 | 2.993831 | 2.0230478 | 2.9956812 | 7.7694413 | 7.5879581 | 8.4301508 |
| FILIP1L | 1.210814628 | 0.049694878 | 0.005201797 | 43.11079458 | 5.2636993 | 3.3213504 | 4.4498938 | 8.7513276 | 10.3885066 | 10.3785579 |
| PLSCR4 | 1.173276782 | 0.04991757 | 0.005918818 | 42.84224996 | 3.8399484 | 3.3213504 | 4.5083337 | 10.9695379 | 7.956043 | 9.2609108 |
| DPYD | 1.13183715 | 0.050131358 | 0.006714784 | 42.60573396 | 1.8744435 | 2.0230478 | 4.4498938 | 8.4072489 | 7.2874192 | 8.5419101 |
| USMG5 | 1.117965601 | 0.050341156 | 0.0070609 | 42.34928863 | 4.6820765 | 5.2978680 | 2.3793449 | 8.1428995 | 10.0863423 | 10.6353184 |
| SNRNP27 | 1.205939776 | 0.04976927 | 0.005299687 | 41.87462177 | 3.8399484 | 3.3213504 | 2.1654208 | 8.7093547 | 7.5879581 | 8.9725869 |
| CCDC7L | 1.207572491 | 0.04976927 | 0.005283641 | 41.84107785 | 4.815804 | 5.297868 | 4.2859964 | 10.7838279 | 9.0971447 | 10.2026521 |
| PHF17 | 1.19477139 | 0.04958755 | 0.005437696 | 41.76391558 | 6.6482929 | 4.9115166 | 6.2829045 | 10.2193155 | 12.032478 | 11.8541443 |
| JTB | 1.277581166 | 0.04958755 | 0.004142662 | 41.60696211 | 4.815804 | 3.8720139 | 3.9352215 | 9.21443 | 9.3139746 | 11.0424753 |
| STXBP3 | 1.314375881 | 0.065320795 | 0.003781594 | 41.57502364 | 1.8744435 | 2.0230478 | 2.1654208 | 7.400693 | 8.5314896 | 6.8834842 |
| MCM3 | 0.90652013 | 0.049800046 | 0.016626013 | 41.42259025 | 1.8744435 | 3.3213504 | 2.1654208 | 4.5400907 | 7.5377667 | 9.8294924 |
| KRT18 | 1.188466971 | 0.04991757 | 0.005542004 | 41.36811838 | 1.8744435 | 3.8720139 | 2.1654208 | 7.244891 | 8.7675828 | 8.0053615 |
| NDUFAB1 | 1.134749868 | 0.049800046 | 0.006670946 | 41.04899075 | 4.309025 | 2.8096013 | 4.7244061 | 6.0269554 | 8.1688761 | 7.925186 |
| CLU | 1.220192652 | 0.049622329 | 0.005049346 | 41.0003459 | 1.8744435 | 6.0441977 | 2.1654208 | 9.9896111 | 10.0819703 | 11.0007002 |
| RP40 | 0.793104195 | 0.094990031 | 0.03240873 | 40.86330087 | 1.8744435 | 2.0230478 | 2.1654208 | 3.1012538 | 7.3757827 | 8.3708479 |
| PARK7 | 1.183245174 | 0.049897122 | 0.005654337 | 40.73945076 | 4.963444 | 4.3899364 | 2.3793449 | 9.5691497 | 8.5186068 | 10.3117986 |
| TMEM14A | 1.154126905 | 0.04991757 | 0.006351601 | 39.51249258 | 1.8744435 | 3.7709946 | 2.9956812 | 7.6339561 | 7.5120008 | 9.0752315 |
| NTRK2 | 1.093741072 | 0.050952718 | 0.007725267 | 39.38100766 | 2.2016907 | 4.7507076 | 2.9956812 | 7.335969 | 8.2951094 | 11.0265508 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| EIF4E | 1.293115393 | 0.04958755 | 0.003998235 | 39.1691643 | 5.7794294 | 6.1842483 | 6.0721689 | 11.3638154 | 11.7087024 | 10.7327567 |
| CXCL14 | 1.127760708 | 0.050237584 | 0.006829816 | 39.15476934 | 4.309025 | 6.0924064 | 5.5929159 | 12.3140128 | 10.884032 | 9.1119156 |
| DIMT1 | 1.116399801 | 0.050341156 | 0.007092995 | 38.70718979 | 1.8744435 | 3.360637 | 2.3793449 | 6.4088472 | 9.2056159 | 7.6538745 |
| LOC100129316 | 0.891568891 | 0.067647212 | 0.018014122 | 38.60104563 | 1.8744435 | 2.0230478 | 2.9956812 | 4.1976103 | 8.1852726 | 8.2662493 |
| PFDN1 | 1.105638493 | 0.050608213 | 0.007429993 | 38.53508315 | 1.8744435 | 2.0230478 | 2.1654208 | 7.2911484 | 5.5764175 | 8.3090028 |
| SYBU | 1.249210792 | 0.04958755 | 0.004624087 | 38.43560364 | 1.8744435 | 2.0230478 | 2.1654208 | 6.6046733 | 7.2874192 | 9.3454959 |
| TMEM159 | 1.043832883 | 0.052218844 | 0.009209661 | 38.43560364 | 1.8744435 | 2.0230478 | 2.9956812 | 5.5826351 | 7.2874192 | 9.4918525 |
| SDHB | 0.975021932 | 0.056617715 | 0.011955388 | 38.30294505 | 1.8744435 | 2.0230478 | 2.1654208 | 4.8170878 | 7.2874192 | 7.4397554 |
| PM20D2 | 1.093785567 | 0.050952718 | 0.007717243 | 37.86890311 | 3.8197323 | 3.8720139 | 2.3793449 | 6.6408414 | 9.1313973 | 7.7500915 |
| TSPAN6 | 1.209016548 | 0.04976927 | 0.005235497 | 37.25049072 | 1.8744435 | 2.0230478 | 2.1654208 | 9.062674 | 6.9073747 | 8.9457427 |
| CHMP2B | 1.061990898 | 0.051493437 | 0.008611891 | 37.22365586 | 3.8197323 | 2.8096013 | 4.2859964 | 9.7205099 | 7.5377667 | 7.093473 |
| RFK | 1.244846221 | 0.04958755 | 0.004680254 | 36.92006254 | 1.8744435 | 3.3213504 | 2.1654208 | 8.4987997 | 7.0925914 | 8.0564393 |
| MTDH | 1.152706596 | 0.04991757 | 0.006359624 | 36.84905737 | 5.3044627 | 5.1480825 | 3.9352215 | 10.5107958 | 9.2530552 | 9.5904678 |
| ARHGEF25 | 1.053500437 | 0.051888429 | 0.008899141 | 36.75071144 | 2.993831 | 2.8096013 | 3.9083598 | 8.2521782 | 6.6948447 | 9.1119156 |
| CHPT1 | 1.2568292 | 0.04958755 | 0.004511755 | 36.7507144 | 4.2098819 | 3.360637 | 3.9352215 | 8.9732809 | 9.7262434 | 8.5597232 |
| PRKG1 | 1.232993795 | 0.04958755 | 0.004824681 | 36.6500659 | 1.8744435 | 2.0230478 | 2.9956812 | 7.0702087 | 7.5120008 | 7.6538745 |
| RERG | 1.08336884 | 0.051255379 | 0.00804381 | 36.63688122 | 3.8399484 | 2.0230478 | 2.9956812 | 6.4903918 | 9.0351732 | 8.6118796 |
| CCL21 | 0.903857128 | 0.065688432 | 0.016833026 | 36.19275114 | 5.2636993 | 3.3213504 | 3.7641245 | 6.2771857 | 8.9417534 | 12.2913492 |
| CAT | 1.110357196 | 0.050482841 | 0.0072703 | 36.08658372 | 4.6820765 | 2.8096013 | 3.9352215 | 7.9829919 | 8.65436 | 9.9080797 |
| DDX1 | 1.09502981 | 0.050952718 | 0.007669101 | 35.8962651 | 4.815804 | 3.3213504 | 2.1654208 | 7.7708426 | 9.2762025 | 8.4871122 |
| SRP14 | 1.070121757 | 0.051378258 | 0.008356736 | 35.60183646 | 5.2636993 | 2.406905 | 3.9352215 | 9.0891013 | 8.0122661 | 9.6076956 |
| METTL9 | 1.045489091 | 0.052154186 | 0.00915189 | 35.46470088 | 4.2634629 | 2.0230478 | 2.1654208 | 7.3137327 | 6.8260777 | 9.6162329 |
| C14orf2 | 1.167914156 | 0.04991757 | 0.006038674 | 35.27071303 | 4.6820765 | 3.3213504 | 2.3793449 | 9.8224753 | 8.3687411 | 9.3038231 |
| SRGN | 0.878735799 | 0.069997503 | 0.019411859 | 35.24933404 | 6.5861495 | 4.3513152 | 5.2252164 | 11.7256736 | 8.734539 | 7.9524091 |
| SNRPE | 1.217994037 | 0.049622329 | 0.005073417 | 35.19871284 | 3.8399484 | 2.0230478 | 2.1654208 | 8.6748743 | 7.1604986 | 8.8733587 |
| VEZT | 0.946679859 | 0.059314973 | 0.01353045 | 35.05722834 | 3.8197323 | 3.3213504 | 3.3243747 | 8.5183788 | 8.9513724 | 6.1659595 |
| THOC7 | 1.190097301 | 0.049800046 | 0.005509909 | 34.90370026 | 4.2098819 | 3.3213504 | 2.1654208 | 7.9107527 | 8.4387969 | 9.33519 |
| CDC14B | 1.250934032 | 0.04958755 | 0.004616064 | 34.6288712 | 1.8744435 | 2.406905 | 2.1654208 | 6.988347 | 8.7456379 | 7.0438915 |
| SACM1L | 1.108018963 | 0.050567091 | 0.007324079 | 34.58421951 | 2.2016907 | 3.3213504 | 4.2859964 | 7.3137327 | 8.6425333 | 8.932131 |
| HES1 | 1.14131182 | 0.050390282 | 0.007149162 | 34.4407878 | 6.8989234 | 4.8079702 | 5.2252164 | 9.9140164 | 11.5859378 | 10.6603018 |
| TCEAL4 | 1.031032678 | 0.052917554 | 0.009632512 | 34.38493745 | 2.993831 | 3.3213504 | 4.2859964 | 10.2547666 | 8.4250552 | 6.8257955 |
| NDUFA4 | 1.236006231 | 0.04958755 | 0.00480061 | 34.01899484 | 4.2634629 | 4.8304956 | 4.9444683 | 9.3517316 | 9.7703857 | 12.0792452 |
| ADH1B | 1.104534829 | 0.050647945 | 0.007478135 | 33.82051586 | 4.7435639 | 3.8720139 | 6.0721689 | 8.9518406 | 10.150381 | 10.8092119 |
| IF746 | 1.136970343 | 0.050038461 | 0.006662803 | 33.50987303 | 2.2016907 | 2.0230478 | 2.3793449 | 7.268205 | 8.2799211 | 6.069928 |
| TTF1 | 1.049775849 | 0.051934328 | 0.009000067 | 33.35735192 | 2.993831 | 4.4133226 | 2.1654208 | 8.2166637 | 7.2253537 | 8.2877844 |
| TPM1 | 1.066630038 | 0.051378258 | 0.008443392 | 33.17904161 | 5.2636993 | 6.1842483 | 3.3243747 | 8.8160436 | 10.3158996 | 11.1014343 |
| SEPT7 | 1.06062609 | 0.051535817 | 0.00865201 | 33.12205037 | 6.3447976 | 4.8304956 | 4.7244061 | 9.1593751 | 9.8802157 | 11.924578 |
| FAM110B | 1.097027787 | 0.050892627 | 0.007630587 | 33.06334689 | 4.2098819 | 2.0230478 | 2.1654208 | 7.0702087 | 8.7007207 | 7.7807893 |
| TMSB4X | 1.259227779 | 0.049227554 | 0.004471636 | 32.83570884 | 8.9960085 | 8.6447292 | 9.4260873 | 14.3968235 | 14.0332022 | 13.8620403 |
| GBP2 | 1.116751851 | 0.050341156 | 0.007084972 | 32.71044977 | 4.2634629 | 3.360637 | 4.7549172 | 8.6484622 | 9.7865969 | 8.4683738 |
| ASNSD1 | 1.284977565 | 0.04958755 | 0.004086496 | 32.45539202 | 4.7435639 | 2.0230478 | 6.0721689 | 7.0434341 | 7.1604986 | 8.5947028 |
| ATF6 | 1.056318328 | 0.051814299 | 0.008835754 | 32.14158087 | 5.7794294 | 4.7365865 | 2.3793449 | 9.7539295 | 9.7429554 | 8.6786124 |
| RBM3 | 1.203181806 | 0.049809046 | 0.005325363 | 31.96968146 | 6.7367617 | 6.537655 | 5.018694 | 10.8947292 | 11.7353942 | 11.3621946 |
| RPS24 | 1.218459898 | 0.049622329 | 0.005065394 | 31.81215456 | 8.3134756 | 7.885522 | 8.6164969 | 12.7649469 | 13.3049818 | 13.87898999 |
| TRAPPC6B | 1.222360087 | 0.049622329 | 0.005033299 | 31.60879706 | 2.2016907 | 2.0230478 | 2.1654208 | 7.147675 | 6.6504789 | 7.8104476 |
| SKP1 | 1.225665084 | 0.049622329 | 0.004977132 | 31.48910377 | 4.6820765 | 4.8079702 | 3.3243747 | 9.4313502 | 9.2452562 | 9.784751 |
| OS9 | 1.113179533 | 0.050444063 | 0.007190885 | 31.40162226 | 4.309025 | 5.1480825 | 5.2176156 | 11.0304667 | 10.120849 | 8.6118796 |
| AKAP9 | 1.079168649 | 0.051291304 | 0.008149723 | 31.32574214 | 3.8399484 | 3.360637 | 5.3892653 | 8.8081111 | 10.5835916 | 8.3299138 |
| BOLA3 | 1.08392778 | 0.051255379 | 0.008011715 | 30.87780167 | 3.8399484 | 3.7709946 | 2.1654208 | 8.2404369 | 7.2567201 | 8.7884466 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| RHOB | 1.19389932 | 0.049809046 | 0.005461767 | 30.81942645 | 9.0997518 | 8.0894025 | 8.050877 | 13.6197313 | 12.9966452 | 13.4747732 |
| ZFYVE28 | 1.083584421 | 0.051255379 | 0.008035786 | 30.68131477 | 2.2016907 | 2.0230478 | 3.9083598 | 6.7105675 | 7.5879581 | 8.8476482 |
| PPP3R1 | 1.179286695 | 0.049897122 | 0.005830859 | 30.66118368 | 4.2098819 | 4.3899364 | 3.9352215 | 9.4416416 | 9.1482234 | 8.4106527 |
| HSP90AA1 | 1.111956607 | 0.050440463 | 0.007239028 | 30.00976133 | 8.3134756 | 8.5442716 | 9.4311157 | 13.6455578 | 14.3384757 | 12.7440469 |
| SOD3 | 0.8413111 | 0.078969245 | 0.023810479 | 29.97106828 | 6.8201191 | 4.3513152 | 8.6427428 | 9.4820885 | 11.7726177 | 11.7513159 |
| SMOC2 | 1.011459622 | 0.054106764 | 0.01032095 | 29.86282523 | 4.7435639 | 4.3899364 | 6.0540376 | 10.1106434 | 8.3250145 | 10.9543163 |
| CHMP5 | 1.068286689 | 0.051378258 | 0.008387226 | 29.11967163 | 4.6394091 | 3.3213504 | 4.4498938 | 8.4588258 | 8.1852726 | 10.3378421 |
| BUD31 | 1.135809126 | 0.050038461 | 0.006646875 | 29.05869226 | 2.2016907 | 3.360637 | 3.3243747 | 6.9310735 | 8.1852726 | 8.9592273 |
| ATF1 | 1.171785545 | 0.04991757 | 0.005950413 | 28.93126406 | 4.309025 | 3.360637 | 2.2956812 | 7.8502387 | 9.1229101 | 8.818351 |
| KIAA0040 | 1.11379844 | 0.050440463 | 0.007174838 | 28.7898761 | 2.993831 | 4.4133226 | 5.2252164 | 8.5661948 | 9.2608123 | 9.8657454 |
| UROD | 1.019126456 | 0.053436225 | 0.009984755 | 28.76033974 | 5.2636993 | 3.3213504 | 2.3793449 | 8.7513276 | 7.2253537 | 10.0968205 |
| OXA1L | 1.196354418 | 0.049809046 | 0.005405601 | 28.67050844 | 3.3509967 | 3.7709946 | 3.9352215 | 8.1924923 | 8.4250552 | 8.833074 |
| CHCHD5 | 1.017902709 | 0.053512074 | 0.010066597 | 28.62112774 | 4.2634629 | 3.360637 | 3.3243747 | 7.7022087 | 9.4147603 | 8.1996456 |
| TADA3 | 1.118860945 | 0.050341156 | 0.007020782 | 28.61782399 | 3.8399484 | 3.8720139 | 2.1654208 | 8.0246608 | 7.8365643 | 8.7108559 |
| ADCY3 | 1.005622578 | 0.054519995 | 0.01062505 | 28.47134779 | 6.0548278 | 4.9115166 | 4.5083337 | 8.5848861 | 9.7429554 | 11.0007002 |
| BOD1L | 1.251495541 | 0.04958755 | 0.004583969 | 28.4354758 | 4.6820765 | 4.8304956 | 4.2859964 | 9.5116965 | 9.4286003 | 9.5904678 |
| RSF1 | 1.103321921 | 0.050647945 | 0.007494183 | 28.09592371 | 6.0082059 | 4.7365865 | 5.2252164 | 10.9371717 | 10.0375054 | 9.3658894 |
| NUTF2 | 1.044201536 | 0.052196569 | 0.009192008 | 27.9983901 | 5.0569476 | 3.360637 | 2.3793449 | 8.167909 | 8.9798503 | 8.0311264 |
| KDM3B | 1.157265402 | 0.04991757 | 0.006255316 | 27.96292869 | 2.993831 | 2.8096013 | 3.3243747 | 8.0915413 | 7.1604986 | 8.1298183 |
| ZNF22 | 1.135202924 | 0.050038461 | 0.006654898 | 27.91198177 | 4.6820765 | 2.8096013 | 2.9956812 | 9.3894343 | 7.6124139 | 9.0119393 |
| PRSS23 | 0.858015062 | 0.07443975 | 0.021530129 | 27.90585885 | 5.3285264 | 2.8096013 | 3.9083598 | 10.2518454 | 6.2722716 | 8.7108559 |
| MTRNR2L8 | 0.883344973 | 0.06911283 | 0.018893525 | 27.88554783 | 8.9840072 | 11.9710046 | 12.360928 | 13.7854529 | 16.0492172 | 17.4110649 |
| MAT2B | 1.062231312 | 0.051494337 | 0.008603867 | 27.75067801 | 5.3354128 | 4.3513152 | 3.9352215 | 10.1298639 | 8.3543123 | 9.2054107 |
| PHF20L1 | 1.020552807 | 0.053420513 | 0.009944636 | 27.72767982 | 3.3509967 | 4.3899364 | 2.3793449 | 7.1725999 | 8.1522912 | 8.4106527 |
| GRIP2 | 1.118420778 | 0.050341156 | 0.007044853 | 27.62692888 | 2.993831 | 2.8096013 | 2.3793449 | 7.5976045 | 6.6002221 | 8.8763623 |
| ANAPC4 | 1.207263617 | 0.04967927 | 0.005291663 | 27.59191082 | 1.8744435 | 2.0230478 | 2.1654208 | 6.8092213 | 6.6483084 | 9.1594204 |
| CAMK2N1 | 1.108563382 | 0.050567091 | 0.007316056 | 27.41976823 | 5.2636993 | 3.360637 | 5.5715986 | 10.1519689 | 9.062059 | 10.0408434 |
| CKLF | 0.877062992 | 0.070409075 | 0.019676643 | 27.28909407 | 2.2016907 | 2.0230478 | 3.9083598 | 4.9379926 | 7.7510357 | 8.6786124 |
| CCDC23 | 0.979973225 | 0.056452334 | 0.011848672 | 27.14670171 | 4.2098819 | 4.2098819 | 2.1654208 | 7.5790795 | 6.0753543 | 8.9725869 |
| RGL1 | 1.08762558 | 0.051099543 | 0.007908208 | 27.0409702 | 4.309025 | 4.3899364 | 2.2956812 | 8.5280696 | 9.3580333 | 7.550782 |
| MAGEH1 | 1.100456639 | 0.050801344 | 0.007550349 | 26.98429144 | 5.2636993 | 2.0230478 | 4.5083337 | 9.6556819 | 8.6892694 | 8.577319 |
| ABHD14B | 0.988655221 | 0.055891005 | 0.0113512 | 26.92308403 | 5.3044627 | 2.406905 | 3.9352215 | 7.8031272 | 10.1669886 | 9.9759882 |
| MGC23270 | 1.100364081 | 0.050801344 | 0.007558373 | 26.65141881 | 3.3509967 | 2.406905 | 3.9352215 | 6.9015613 | 7.0213307 | 8.2662493 |
| DBI | 1.05073765 | 0.051900312 | 0.0089866 | 26.56643051 | 4.7435639 | 4.3899364 | 4.2859964 | 9.1214689 | 8.0305306 | 9.7307362 |
| SEPT2 | 1.066092671 | 0.051378258 | 0.008467464 | 26.52132722 | 6.7650859 | 4.7365865 | 4.5083337 | 10.0924701 | 9.2374148 | 10.6561678 |
| TENC1 | 1.052735588 | 0.051905221 | 0.008938403 | 26.49070248 | 3.3509967 | 2.406905 | 3.9352215 | 8.0784109 | 9.9248413 | 6.7657063 |
| DCN | 1.095932971 | 0.050930656 | 0.007653053 | 26.32546136 | 8.6910467 | 8.181467 | 9.3748148 | 15.5515758 | 13.4094336 | 12.6823704 |
| FKBP3 | 1.158907362 | 0.04991757 | 0.006223221 | 26.27071633 | 3.3509967 | 3.8720139 | 2.1654208 | 8.3206874 | 8.0063803 | 7.8691489 |
| PPP1CC | 1.006896922 | 0.054519995 | 0.010592955 | 26.23121993 | 5.0569476 | 6.0726357 | 5.6099449 | 10.3231579 | 8.8210275 | 11.2569347 |
| DNAJC19 | 0.99815007 | 0.055641947 | 0.011190725 | 26.2149345 | 5.3285264 | 3.3213504 | 2.1654208 | 7.7378191 | 7.7728978 | 10.0408434 |
| H3F3C | 1.101892388 | 0.05069779 | 0.007518254 | 26.20779302 | 7.5469748 | 6.0441977 | 6.8006628 | 12.0121399 | 12.0392592 | 10.7561217 |
| SMARCA5 | 1.15158858 | 0.04991757 | 0.006383696 | 26.1801923 | 4.6820765 | 4.3513152 | 3.9352215 | 9.0956332 | 9.1143726 | 8.6456318 |
| CSTF2T | 1.128249261 | 0.050237584 | 0.006821793 | 26.14278261 | 3.0245043 | 2.406905 | 2.2956812 | 7.704022 | 6.7836452 | 8.2443879 |
| OSBPL8 | 0.911676464 | 0.064396246 | 0.016130948 | 26.11251738 | 5.3162271 | 4.3513152 | 4.4498938 | 10.0412806 | 9.1565634 | 7.4397554 |
| NR2F1 | 1.114643822 | 0.050390282 | 0.007133114 | 26.0355434 | 4.7435639 | 2.8096013 | 3.3243747 | 9.4209849 | 7.5120008 | 9.3454959 |
| SSPN | 0.965854952 | 0.057385588 | 0.012525074 | 26.02744303 | 3.8399484 | 2.406905 | 4.5083337 | 9.4157741 | 6.6483084 | 8.5419101 |
| AP1S | 0.997656928 | 0.055362341 | 0.011026238 | 25.86863709 | 1.8744435 | 2.406905 | 4.7549172 | 6.5675757 | 8.0305306 | 9.1358635 |
| TRMT112 | 1.069532789 | 0.051378258 | 0.008372783 | 25.8642226 | 6.8989234 | 6.1842483 | 5.5929159 | 10.5682844 | 10.2858018 | 11.7532525 |
| APPL2 | 1.141669697 | 0.050038461 | 0.00655059 | 25.60636104 | 3.8399484 | 4.3513152 | 2.1654208 | 8.5183788 | 8.3101394 | 8.6786124 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| MRPL24 | 0.976133088 | 0.056551597 | 0.011916072 | 25.49985287 | 4.6820765 | 3.3213504 | 2.1654208 | 7.3794393 | 7.9937674 | 8.0053615 |
| ESYT2 | 1.127210629 | 0.050237584 | 0.00683784 | 25.41170312 | 3.3509967 | 3.7709946 | 4.4499838 | 8.4384157 | 8.5314896 | 8.3908876 |
| HSP90B1 | 1.047493482 | 0.052136699 | 0.009113376 | 25.12136303 | 6.8201191 | 4.8079702 | 5.5446534 | 10.8490686 | 10.1955997 | 9.9559492 |
| NUCB2 | 0.857158159 | 0.07471249 | 0.021641659 | 25.04634492 | 6.4876101 | 3.7709946 | 3.7641245 | 9.2499997 | 8.4524089 | 8.4106527 |
| UBAC1 | 1.133065064 | 0.050083269 | 0.006701436 | 24.99903401 | 2.2016907 | 2.0230478 | 2.1654208 | 6.8092213 | 7.5630806 | 6.1659595 |
| TAF1A | 0.989629606 | 0.055830986 | 0.011302255 | 24.92788342 | 5.982974 | 4.9115166 | 4.9444683 | 9.6334087 | 8.6892694 | 10.6226625 |
| ALPK1 | 1.054759492 | 0.051852306 | 0.008867849 | 24.8747231 | 4.2634629 | 3.8720139 | 5.2176156 | 8.5086224 | 8.9798503 | 9.14769 |
| SLIT3 | 0.972251656 | 0.056976583 | 0.012110246 | 24.73397869 | 4.815804 | 3.3213504 | 5.2252164 | 9.8536389 | 7.6124139 | 9.482544 |
| AP3B1 | 1.121219722 | 0.050341156 | 0.006956592 | 24.49459452 | 3.8399484 | 3.360637 | 2.1654208 | 7.7378191 | 7.9750285 | 7.9791282 |
| LOC649395 | 1.107263721 | 0.050608213 | 0.007357779 | 24.4656859 | 4.4656859 | 7.440099 | 6.7371315 | 11.4529988 | 11.3698308 | 11.3494495 |
| PPAP2A | 1.051192411 | 0.051900312 | 0.008970553 | 24.32673452 | 5.6586086 | 4.3899364 | 4.7244061 | 8.9944071 | 9.1057844 | 10.2745294 |
| EID1 | 0.878311349 | 0.070189649 | 0.019511354 | 24.14880415 | 5.7445127 | 3.8720139 | 6.0125266 | 11.0490962 | 8.4658937 | 8.7884466 |
| MSX1 | 0.966291352 | 0.057324142 | 0.012483351 | 23.99322086 | 5.7794294 | 6.7629335 | 8.0377511 | 11.3474884 | 11.3929577 | 10.7209308 |
| A2M | 1.083873977 | 0.051255379 | 0.008019738 | 23.95820173 | 6.5540448 | 6.2280676 | 6.9199049 | 10.3990542 | 11.2848856 | 11.5023526 |
| ACTA2 | 0.776075962 | 0.101300404 | 0.036012196 | 23.84726009 | 1.8744435 | 6.0604012 | 2.1654208 | 6.4501951 | 7.3469252 | 8.4683738 |
| RAB1A | 1.034098858 | 0.052871735 | 0.009545856 | 23.78310968 | 6.186289 | 6.0497213 | 6.2829045 | 11.157649 | 10.7581544 | 9.6581778 |
| KAT8 | 1.002544307 | 0.054695215 | 0.010766268 | 23.74971006 | 4.309025 | 2.8096013 | 3.7641245 | 7.3794393 | 7.7728978 | 8.985824 |
| ANKRD10 | 0.986272516 | 0.056015811 | 0.011451496 | 23.6877588 | 6.5861495 | 4.7507076 | 6.0125266 | 9.6198778 | 9.8289569 | 11.1522193 |
| TRPT1 | 0.911731758 | 0.064396246 | 0.016122924 | 23.65405426 | 2.2016907 | 3.3213504 | 2.1654208 | 5.4258059 | 8.1688761 | 6.7657063 |
| COX5A | 1.112669548 | 0.050440463 | 0.007206933 | 23.47497516 | 4.309025 | 3.8720139 | 4.7244061 | 8.4072489 | 9.5475254 | 8.8620767 |
| COX8A | 1.098023629 | 0.050846008 | 0.007598492 | 23.45824348 | 7.2186326 | 6.3520696 | 6.6706745 | 10.8118669 | 11.2226976 | 11.9635729 |
| EIF3H | 1.138433463 | 0.050038461 | 0.006398732 | 23.43898524 | 6.6482929 | 7.2617905 | 7.4620859 | 11.8164541 | 11.8126287 | 11.4838112 |
| DYNLT3 | 0.944532411 | 0.059600929 | 0.013713392 | 23.36075252 | 5.8565586 | 3.8720139 | 3.7641245 | 8.6305817 | 8.3101394 | 9.2825265 |
| SYTL2 | 1.106061098 | 0.050608213 | 0.007421969 | 23.23514746 | 2.2016907 | 2.406905 | 2.9956812 | 6.9915613 | 6.7399276 | 9.6076956 |
| ARHGAP15 | 0.895945684 | 0.066907118 | 0.017552756 | 23.17349422 | 1.8744435 | 3.3213504 | 4.7549172 | 6.4088472 | 7.4318221 | 9.5375148 |
| RGMB | 1.06704067 | 0.051378258 | 0.008419321 | 23.0855306 | 4.2098819 | 4.8079702 | 5.2252164 | 9.001381 | 8.8210275 | 9.7541334 |
| DNAJC14 | 1.077450578 | 0.051291304 | 0.008403274 | 22.77973184 | 5.3285264 | 6.3119075 | 5.018694 | 10.4610743 | 9.5283729 | 10.3984929 |
| HSPA7 | 1.115607564 | 0.064737869 | 0.007109043 | 22.73469649 | 3.0245043 | 2.8096013 | 2.9956812 | 8.1174489 | 7.1604986 | 6.9389568 |
| SELENBP1 | 1.033273507 | 0.052897282 | 0.009561903 | 22.63478525 | 1.8744435 | 6.1390574 | 9.7496192 | 12.948898 | 13.5238541 | 8.5056104 |
| CTSO | 1.001229982 | 0.054963463 | 0.010875391 | 22.83243116 | 4.6394091 | 4.7365865 | 6.0316576 | 9.1531261 | 9.3214118 | 10.4519348 |
| DDIT4 | 1.077450578 | 0.051291304 | 0.008181818 | 22.77973184 | 6.9736463 | 6.5720715 | 5.5715986 | 10.0846112 | 11.608209 | 10.54877 |
| ADAM22 | 0.945001049 | 0.059600929 | 0.013697344 | 22.63478525 | 1.8744435 | 2.8096013 | 4.4498938 | 7.5025051 | 8.0839766 | 6.9389568 |
| TMEM176B | 0.961176425 | 0.057805981 | 0.012712028 | 22.61260454 | 5.6586086 | 5.3406193 | 6.3558005 | 10.8548558 | 8.8104958 | 10.5443033 |
| SPRY1 | 0.802939311 | 0.0911622 | 0.030322555 | 22.57321793 | 6.2275774 | 3.360637 | 6.0316576 | 11.2202607 | 7.8571772 | 8.8620767 |
| FHL1 | 0.973697036 | 0.056754796 | 0.012004333 | 22.5159121 | 6.3818471 | 3.360637 | 6.3558005 | 10.515675 | 9.0351732 | 10.8747201 |
| HNMT | 1.025699356 | 0.05313101 | 0.009769718 | 22.4774594 | 3.8197323 | 4.8304956 | 4.7549172 | 8.5280696 | 8.3101394 | 10.3274811 |
| SCRN1 | 0.891362841 | 0.067695766 | 0.018038193 | 22.44028499 | 4.815804 | 4.8079702 | 2.3793449 | 7.8190025 | 7.5377667 | 9.3038231 |
| TUBA1C | 0.922344888 | 0.062363889 | 0.015244323 | 22.2228063 | 5.6586086 | 6.6385363 | 4.7549172 | 8.5941417 | 11.4483541 | 10.1329672 |
| PHYHD1 | 0.931379512 | 0.06125755 | 0.014628902 | 22.12286754 | 4.2098819 | 3.360637 | 5.7236017 | 7.8347051 | 8.6777266 | 9.7463764 |
| LOC100506710 | 0.947114485 | 0.059314973 | 0.013514403 | 22.06006448 | 5.3044627 | 2.9956812 | 2.9956812 | 8.2753779 | 7.4590463 | 8.985824 |
| SARNP | 0.94549733 | 0.059597087 | 0.013633154 | 22.00320019 | 4.2098819 | 4.7365865 | 4.2859964 | 7.3578678 | 8.7456379 | 9.9693394 |
| RRAS2 | 1.041137027 | 0.052218844 | 0.009281874 | 21.97665491 | 2.2016907 | 3.8720139 | 4.5083337 | 8.3860905 | 7.8156527 | 8.3299138 |
| TBL1XR1 | 0.824889773 | 0.08448824 | 0.02661478 | 21.86482197 | 6.1437849 | 5.3406193 | 6.3692392 | 10.8197789 | 7.9937674 | 10.7676638 |
| PEX19 | 0.900027743 | 0.066348129 | 0.017133114 | 21.8489524 | 5.7003762 | 3.3213504 | 2.1654208 | 7.7708426 | 7.2567201 | 9.8072951 |
| TMEM223 | 0.905246977 | 0.065436968 | 0.016725508 | 21.82870119 | 4.6394091 | 2.0230478 | 2.1654208 | 5.7241063 | 7.7288372 | 9.0875635 |
| MBNL2 | 0.877773417 | 0.070285138 | 0.019618872 | 21.46901007 | 1.8489524 | 5.7897017 | 6.1759311 | 10.6636862 | 7.4590463 | 10.2139459 |
| FOXJ2 | 0.905385776 | 0.065436968 | 0.016717484 | 21.40455473 | 3.3509967 | 2.8096013 | 4.9444683 | 7.7708426 | 9.3724255 | 6.8257955 |
| LMO4 | 1.029960252 | 0.05293768 | 0.009671026 | 21.34954394 | 7.4101728 | 5.4346801 | 7.9563845 | 11.8263061 | 11.903876 | 11.1522193 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| HDGFRP3 | 0.932125716 | 0.06110322 | 0.014571933 | 21.34390766 | 4.6394091 | 2.8096013 | 2.3793449 | 7.147675 | 7.2253537 | 8.0564393 |
| STEAP4 | 1.000010753 | 0.055166136 | 0.010942791 | 21.30360368 | 6.5540448 | 6.9314777 | 7.3175252 | 10.1829712 | 11.3445033 | 13.8917924 |
| SPTSSA | 1.110892866 | 0.050482841 | 0.007262296 | 21.18629628 | 6.0082059 | 6.3119075 | 6.4507011 | 10.6190426 | 10.8739517 | 10.4132654 |
| CNTLN | 0.779291101 | 0.100174631 | 0.035364679 | 21.18559501 | 3.0245043 | 2.8096013 | 2.9956812 | 7.400693 | 4.8088443 | 7.4397554 |
| C8orf84 | 0.941363386 | 0.060058355 | 0.013929231 | 21.15229292 | 1.8744435 | 4.3899364 | 2.1654208 | 6.2771857 | 8.7784313 | 7.0438915 |
| ZFP90 | 0.963704308 | 0.057515704 | 0.012627778 | 21.14604998 | 3.8197323 | 2.406905 | 3.9083598 | 6.8092213 | 7.6364622 | 8.5947028 |
| ARID4B | 0.856200545 | 0.074899345 | 0.021782075 | 21.09662862 | 5.0569476 | 4.9115166 | 6.0540376 | 10.5326233 | 9.4558882 | 7.8691489 |
| PDCD6 | 0.870486295 | 0.071737566 | 0.020284041 | 21.09064583 | 2.2016907 | 3.8720139 | 2.1654208 | 5.5826351 | 6.6002221 | 8.6118796 |
| EFR3A | 0.908557594 | 0.065051314 | 0.01646634 | 20.91348244 | 4.6394091 | 3.7709946 | 2.3793449 | 7.5413002 | 9.7262434 | 6.7657063 |
| OLA1 | 0.9418973 | 0.059948356 | 0.013872262 | 20.91318791 | 3.8399484 | 5.3621423 | 4.944683 | 7.7210195 | 9.7484834 | 9.5011013 |
| USPL1 | 1.027712499 | 0.053094283 | 0.009277995 | 20.90533531 | 4.309025 | 3.3213504 | 3.9352215 | 7.4827092 | 8.3971729 | 8.6948242 |
| EFHA1 | 1.011052628 | 0.054161962 | 0.010035465 | 20.84409197 | 1.8744435 | 3.360637 | 2.1654208 | 6.988347 | 7.1604986 | 6.2560101 |
| EEF1G | 1.053201682 | 0.051900312 | 0.008930434 | 20.75732369 | 9.127293 | 9.6471417 | 9.3695859 | 13.1140369 | 14.0226902 | 13.8812053 |
| ITGA7 | 0.897019636 | 0.066827455 | 0.017446843 | 20.69311928 | 6.0999914 | 4.9115166 | 6.3558005 | 8.4588258 | 10.4710706 | 10.8888821 |
| PDP1 | 1.087167846 | 0.051099543 | 0.007940303 | 20.64861088 | 3.8399484 | 4.3899364 | 4.2859964 | 8.2285993 | 8.5186068 | 8.7579092 |
| MRPL18 | 0.955885588 | 0.058365313 | 0.012977614 | 20.60623361 | 4.2634629 | 4.8079702 | 2.9956812 | 8.2285993 | 9.8237295 | 7.3606902 |
| UQCRC2 | 1.059299864 | 0.051695193 | 0.008737864 | 20.58504727 | 5.3354128 | 4.7365865 | 4.5083337 | 8.7677808 | 9.2056159 | 9.6989376 |
| ARFIP1 | 0.858203205 | 0.07443975 | 0.021506058 | 20.55462698 | 4.6820765 | 4.3899364 | 3.3243747 | 8.7513276 | 6.4455364 | 9.4156466 |
| DNAJB9 | 0.982707351 | 0.056301234 | 0.011656904 | 20.52323742 | 5.7445127 | 3.8720139 | 5.3892653 | 9.4518602 | 10.1036991 | 8.6288544 |
| ZFAND1 | 1.003702266 | 0.054558959 | 0.010712509 | 20.52227622 | 4.6394091 | 3.8720139 | 3.3243747 | 7.2911484 | 8.9985279 | 8.8620767 |
| GNAI2 | 0.985472847 | 0.056096089 | 0.011506058 | 20.42260955 | 7.4279993 | 6.270596 | 7.1809309 | 11.7682045 | 10.250627 | 11.7800947 |
| PTPN18 | 1.012778724 | 0.054044749 | 0.010258365 | 20.38087076 | 3.8197323 | 4.7365865 | 3.7641245 | 7.8808129 | 8.168761 | 9.33519 |
| TLN1 | 1.058853562 | 0.051725293 | 0.0087611935 | 20.35333457 | 5.3162271 | 5.3621423 | 5.5715986 | 9.2263843 | 9.7093356 | 10.0022812 |
| RAB10 | 1.075372865 | 0.051291304 | 0.008205889 | 20.18465892 | 5.3044627 | 4.3899364 | 4.7549172 | 9.5549994 | 9.63965 | 8.6786124 |
| NR2F2 | 0.95581188 | 0.058394261 | 0.012993661 | 20.05485407 | 9.0602887 | 4.8049956 | 6.976024 | 11.1435335 | 11.3019035 | 13.1437919 |
| GMPR | 1.036515929 | 0.05264149 | 0.00946963 | 20.04222754 | 3.3509967 | 2.8096013 | 2.1654208 | 6.4903918 | 7.0925914 | 9.0119393 |
| MSH6 | 0.906915941 | 0.065226749 | 0.016858594 | 19.97124046 | 4.2634629 | 2.8096013 | 3.7641245 | 6.4501951 | 8.0839766 | 8.6622163 |
| PDLIM3 | 0.870842761 | 0.071737566 | 0.020076017 | 19.95246522 | 4.7435639 | 4.4133226 | 4.7549172 | 7.0434341 | 9.062059 | 9.7695234 |
| RNF103 | 0.947644285 | 0.059309685 | 0.013475889 | 19.83650498 | 3.8197323 | 3.3213504 | 5.018694 | 7.7708426 | 8.4792536 | 8.1298183 |
| H1FX | 0.910275693 | 0.064737869 | 0.016336356 | 19.68868936 | 8.234634 | 5.4346801 | 6.3692392 | 10.481169 | 11.5704161 | 10.6685344 |
| TBC1D15 | 0.947903505 | 0.059309685 | 0.013451817 | 19.64787657 | 6.6175557 | 6.270596 | 6.0560619 | 10.6482176 | 10.9138572 | 9.4350787 |
| FAM102B | 0.911657173 | 0.064417984 | 0.016146995 | 19.53567509 | 4.2634629 | 2.2030478 | 3.3243747 | 6.4501951 | 7.6124139 | 8.0053615 |
| SNRPD2P2 | 0.982350109 | 0.05631807 | 0.011688197 | 19.41918907 | 7.2389721 | 6.3520696 | 6.3558005 | 10.1890925 | 10.7360641 | 11.5183831 |
| TINF2 | 0.947284605 | 0.059309685 | 0.01349996 | 19.27906972 | 4.2634629 | 3.360637 | 2.3793449 | 7.4827092 | 6.6483084 | 9.1239392 |
| CD9 | 1.02651993 | 0.053094283 | 0.009744042 | 19.2567535 | 3.8197323 | 3.7709946 | 3.3243747 | 8.0382872 | 9.1648555 | 7.141714 |
| FAM36A | 0.997051405 | 0.055405156 | 0.011051914 | 19.24443227 | 4.7435639 | 5.297868 | 4.5083337 | 9.3017621 | 8.2799211 | 9.5642342 |
| ENY2 | 0.986572336 | 0.056015811 | 0.011427425 | 19.18086683 | 4.6820765 | 2.2030478 | 3.3243747 | 8.6748743 | 7.4318221 | 7.5859707 |
| CYB561D2 | 0.940667677 | 0.060104489 | 0.013967745 | 19.17995452 | 3.8399484 | 3.3213504 | 2.3793449 | 6.6408414 | 8.3250145 | 7.0438915 |
| MUT | 0.819358001 | 0.086050848 | 0.027531894 | 19.14968888 | 5.8972917 | 2.0230478 | 4.5083337 | 7.0434341 | 8.7675828 | 9.0248218 |
| WAC | 0.891139399 | 0.067798428 | 0.018076707 | 19.12960958 | 6.7367617 | 5.3621423 | 7.0300422 | 9.6198778 | 9.7758097 | 13.1124517 |
| ZMAT2 | 0.893293167 | 0.067248681 | 0.017778224 | 19.02171579 | 6.1437849 | 4.2098819 | 4.5083337 | 8.5755707 | 8.922321 | 8.7579092 |
| C1S | 0.985498012 | 0.056096089 | 0.011498034 | 18.94088318 | 6.9491661 | 7.0583001 | 8.26876 | 11.7538223 | 11.1925978 | 11.8101721 |
| C11orf73 | 1.000992882 | 0.054963463 | 0.010883415 | 18.88171674 | 4.2098819 | 4.3899364 | 3.7641245 | 7.5976045 | 8.5569151 | 8.6288544 |
| HSD17B11 | 0.971245962 | 0.057076743 | 0.012174436 | 18.81569836 | 4.7435639 | 4.8304956 | 5.6099449 | 9.8727797 | 8.9892193 | 10.4614424 |
| ANKS1B | 0.94148941 | 0.060032865 | 0.013911578 | 18.78225317 | 6.2275774 | 3.8720139 | 4.944683 | 8.1428995 | 9.5475254 | 8.7267115 |
| SNHG6 | 1.023424431 | 0.05332335 | 0.009855572 | 18.71829485 | 5.3162271 | 7.1522986 | 7.6289155 | 11.0029324 | 11.424795 | 13.1460046 |
| PDK4 | 0.866897983 | 0.072230876 | 0.020542406 | 18.66699306 | 7.1980024 | 6.7328249 | 6.7371315 | 10.6955425 | 12.4048378 | 11.1135456 |
| ZMAT2 | 0.886860184 | 0.068365464 | 0.01849314 | 18.57349372 | 8.9658158 | 5.3621423 | 3.7641245 | 8.5755707 | 8.4250552 | 9.6989376 |
| CADM1 | 0.914652188 | 0.063667641 | 0.015854128 | 18.56709887 | 6.1437849 | 10.9961008 | 9.5421815 | 12.5235071 | 14.8358001 | 15.2107773 |
| TAGLN | | | | | 8.8382996 | | | | | |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| AMD1 | 0.908125705 | 0.065125118 | 0.016506459 | 18.30652211 | 4.6820765 | 5.3406193 | 6.7692467 | 10.575312 | 9.7149936 | 8.8763623 |
| TFG | 0.963965378 | 0.057515704 | 0.012619754 | 18.25927754 | 4.7435639 | 4.8079702 | 2.3793449 | 8.2521782 | 8.9985279 | 8.0053615 |
| RPS18 | 0.935240153 | 0.060873607 | 0.014336837 | 18.11094714 | 10.4802403 | 11.0413399 | 10.7568342 | 13.8496561 | 15.3851924 | 14.9356243 |
| AIMP1 | 1.030541317 | 0.05293768 | 0.009646955 | 18.08849656 | 5.7445127 | 5.297868 | 4.9444683 | 9.1214689 | 9.7262434 | 9.6827716 |
| COL12A1 | 0.894287853 | 0.067193151 | 0.017705207 | 17.99713286 | 5.3162271 | 4.8079702 | 6.702855 | 10.8739807 | 9.7093356 | 8.6288544 |
| SEPN1 | 0.917366135 | 0.063325847 | 0.015680013 | 17.97359722 | 6.0999914 | 5.6616851 | 4.5083337 | 10.3147842 | 8.4658937 | 9.8294924 |
| ADM | 0.999143484 | 0.055166136 | 0.010958838 | 17.94256552 | 6.1437849 | 5.1480825 | 6.0316576 | 9.261664 | 10.6908421 | 10.1969719 |
| HSD17B12 | 0.965308956 | 0.057395438 | 0.012555564 | 17.93139787 | 5.4911209 | 3.3213504 | 3.9083598 | 9.3571784 | 7.4857665 | 9.3557287 |
| PRINS | 0.900498166 | 0.066280364 | 0.017093798 | 17.79230067 | 3.3025043 | 4.4133226 | 3.764124 | 6.6046733 | 7.9173057 | 8.9592273 |
| RPL31 | 1.021311537 | 0.053385633 | 0.009928589 | 17.7338341 | 9.4617995 | 10.2275206 | 9.9968644 | 13.6106387 | 14.2235993 | 14.3361442 |
| TMSB10 | 0.889019108 | 0.068085662 | 0.018298965 | 17.71732251 | 7.7305591 | 8.5268269 | 8.5897647 | 13.1027323 | 12.6739156 | 10.9710537 |
| SPARC | 1.051950508 | 0.051900312 | 0.008954505 | 17.67233245 | 9.1860944 | 8.6924512 | 9.1794888 | 14.13433 | 12.8358717 | 13.251156 |
| NR1D2 | 0.96009316 | 0.057945377 | 0.012769799 | 17.58211353 | 4.815804 | 4.8304956 | 5.9741452 | 8.9518406 | 9.1565634 | 9.5375148 |
| RGS4 | 0.914472915 | 0.0369643 | 0.01587178 | 17.54652348 | 2.993831 | 3.360637 | 4.9444683 | 8.7513276 | 7.1269443 | 7.8108476 |
| PSMA2 | 0.991486891 | 0.055698998 | 0.011230843 | 17.37369867 | 5.7003762 | 4.7365865 | 5.2176156 | 10.013954 | 9.361721 | 8.8034763 |
| KHDRBS3 | 0.789226734 | 0.096254372 | 0.033117227 | 17.30725824 | 2.2016907 | 4.9115166 | 6.0540376 | 6.988347 | 9.2374148 | 9.0248218 |
| PRMT3 | 0.821794565 | 0.085361525 | 0.027114659 | 17.1116875 | 5.7445127 | 3.3213504 | 2.9956812 | 7.704022 | 7.0925914 | 9.1239392 |
| AHNAK | 0.810769582 | 0.088793079 | 0.028993822 | 17.10714203 | 6.6540448 | 7.3033622 | 6.2829045 | 11.399889 | 8.7675828 | 11.3443198 |
| GHITM | 0.897948926 | 0.066685485 | 0.017308032 | 17.04926294 | 5.982974 | 3.360637 | 4.7244061 | 8.8160436 | 8.8418632 | 8.577319 |
| DNAJC24 | 0.82869478 | 0.082955513 | 0.025913504 | 17.00807471 | 4.300025 | 2.8096013 | 3.764124 | 5.8529567 | 8.3971729 | 8.3090028 |
| TMEM183B | 0.93445083 | 0.061000896 | 0.014477253 | 16.98492089 | 3.3509967 | 3.7709946 | 4.2859364 | 6.9599943 | 7.8571772 | 8.7108559 |
| MRPL3 | 0.986593546 | 0.056015811 | 0.01419401 | 16.89398154 | 4.7435639 | 4.3899364 | 2.3793449 | 7.7708426 | 8.7233541 | 8.4683738 |
| CASQ2 | 0.830920851 | 0.082259709 | 0.025578111 | 16.88543107 | 3.8197323 | 2.0230478 | 2.1654026 | 6.8406623 | 5.1121088 | 7.8974394 |
| PPP1R12A | 0.964224668 | 0.057492262 | 0.012603707 | 16.73452716 | 7.021395 | 6.4291897 | 6.5278107 | 10.0846112 | 10.6618412 | 11.0861509 |
| ABCC9 | 0.982279682 | 0.056350705 | 0.011704245 | 16.69195001 | 3.8197323 | 4.8304956 | 4.7549172 | 7.8808129 | 8.65436 | 9.9759882 |
| GPM6B | 0.948805259 | 0.059219172 | 0.013375592 | 16.63555852 | 5.3162271 | 4.3513152 | 3.764124 | 7.7210195 | 9.3724255 | 8.932131 |
| SERPING1 | 0.913991292 | 0.063950039 | 0.015944797 | 16.51027049 | 3.8394484 | 3.8720139 | 3.9352215 | 6.8092213 | 7.9173057 | 8.7884466 |
| FOXN2 | 0.982650155 | 0.05631807 | 0.01167215 | 16.4832761 | 1.8744435 | 4.4389364 | 4.9449938 | 8.9873994 | 7.89754 | 8.3299138 |
| ASPN | 0.871058768 | 0.071735945 | 0.02025997 | 16.40786315 | 4.815804 | 2.0230478 | 3.3243747 | 7.244891 | 7.4857665 | 7.3606902 |
| C9orf167 | 0.979250363 | 0.05641197 | 0.0180053 | 16.40146769 | 8.0512583 | 7.4586165 | 7.9139132 | 11.4943695 | 12.1603217 | 11.602428 |
| LOC100500773 | 0.888377151 | 0.068136485 | 0.018323839 | 16.35708965 | 4.815804 | 3.7709946 | 2.3793449 | 7.147675 | 7.3469252 | 8.8476482 |
| IMMP2L | 0.764521413 | 0.106201322 | 0.038838161 | 16.34027114 | 5.7003762 | 4.3899364 | 4.4498938 | 9.3787623 | 6.5504789 | 9.7307362 |
| SYPL1 | 0.927113657 | 0.061709548 | 0.014960282 | 16.232529 | 8.5678121 | 8.181467 | 7.7625708 | 12.588628 | 11.3536 | 12.2189249 |
| PPP1CB | 0.818569992 | 0.086383601 | 0.027723662 | 16.19136378 | 5.2636993 | 4.8304956 | 4.2859964 | 9.6289125 | 7.0925914 | 8.8476482 |
| GNAI3 | 0.831375906 | 0.082162426 | 0.02550349 | 16.16475463 | 5.3162271 | 5.6616851 | 5.5929159 | 10.4960584 | 7.8156527 | 9.6076956 |
| SERPING1 | 0.784356581 | 0.098241201 | 0.034279066 | 16.03432866 | 8.3513375 | 5.6616851 | 6.3558005 | 10.3588926 | 10.9113951 | 9.9424335 |
| ZBTB16 | 0.860338778 | 0.073930333 | 0.021220412 | 16.01423883 | 7.2186326 | 4.8304956 | 5.5446534 | 8.8317789 | 10.2743512 | 10.4278881 |
| GYPC | 0.855825571 | 0.075059941 | 0.021853486 | 15.89461259 | 6.7367617 | 5.7897017 | 4.5083337 | 8.4987997 | 10.995159 | 9.6664224 |
| TOMM20 | 0.917255853 | 0.063325847 | 0.015688037 | 15.87934642 | 4.7435639 | 4.7365865 | 3.9083598 | 8.0109044 | 9.1565634 | 7.8974394 |
| WBSCR22 | 0.908372026 | 0.065072401 | 0.016482388 | 15.7440435 | 1.8744435 | 3.7709946 | 2.3793449 | 5.8529567 | 7.2253537 | 7.141714 |
| GNPNAT1 | 0.748541404 | 0.113371792 | 0.042915831 | 15.72938845 | 4.2098819 | 3.360637 | 2.1654208 | 5.0495858 | 8.1852726 | 7.4397554 |
| TAF12 | 0.969565439 | 0.057171148 | 0.01232769 | 15.71850025 | 5.7003762 | 6.0361098 | 6.5278107 | 10.0105015 | 11.1618566 | 9.5642342 |
| IGBP1 | 0.889399583 | 0.068037763 | 0.018242799 | 15.42702692 | 5.5686086 | 5.297868 | 4.7549172 | 7.7469252 | 9.2452562 | 8.1767432 |
| DYNC1I2 | 0.855107761 | 0.075373255 | 0.021987483 | 15.41332547 | 5.7445127 | 6.0726357 | 4.5083337 | 9.690619 | 8.0839766 | 10.2473064 |
| RSU1 | 0.902145045 | 0.066071176 | 0.016985477 | 15.39138307 | 4.7435639 | 5.1957839 | 6.1759311 | 9.2732348 | 9.1398349 | 9.0248218 |
| ANTXR1 | 0.756545048 | 0.109706101 | 0.040787932 | 15.37237905 | 6.0082059 | 4.7507076 | 4.7549172 | 9.9505082 | 9.469341 | 6.9389568 |
| PTEN | 0.921934745 | 0.062446634 | 0.015282837 | 15.23068926 | 11.4342087 | 11.6153056 | 12.3217587 | 15.1118134 | 15.5442149 | 16.3577483 |
| RPS27 | 0.930611735 | 0.061334604 | 0.01470941 | 15.17974807 | 5.7794294 | 5.4346801 | 5.2176156 | 9.7035053 | 8.734539 | 9.3959492 |
| ARID1B | 0.836600005 | 0.080460501 | 0.024644147 | 15.17601432 | 8.062715 | 7.6317881 | 8.2231054 | 12.5021549 | 11.986436 | 10.4566964 |
| BTG2 | | | | | | | | | | |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| AP3M1 | 0.902261075 | 0.065963593 | 0.016938939 | 15.12580138 | 7.4456083 | 6.4291897 | 7.481604 | 10.9133361 | 11.6285305 | 10.3481293 |
| LRRC41 | 0.818474757 | 0.086394299 | 0.027741314 | 15.11369233 | 7.0676142 | 7.1970971 | 6.4105447 | 11.1148814 | 9.3139746 | 11.0233447 |
| ACTB | 0.890474441 | 0.067913831 | 0.01815534 | 15.044116213 | 5.982974 | 6.7629335 | 4.4498938 | 10.5517522 | 8.9704199 | 9.8941059 |
| TMEM106B | 0.807355054 | 0.089824887 | 0.029508144 | 14.98109425 | 4.7435639 | 3.8720139 | 3.9352215 | 9.042531 | 6.6002221 | 7.8402926 |
| RAB2A | 0.915125416 | 0.063632534 | 0.01582444 | 14.97498509 | 6.9977182 | 6.0726357 | 5.5969865 | 10.9022008 | 9.3795682 | 10.3583437 |
| LITAF | 0.987545534 | 0.056015811 | 0.011388911 | 14.959361 | 7.0901803 | 6.9314777 | 6.976024 | 12.2706547 | 10.8790006 | 10.5443033 |
| CTDSP1 | 0.8142444 | 0.087587599 | 0.028355131 | 14.91926147 | 8.1619262 | 6.3520696 | 6.7371315 | 10.6459942 | 10.2511738 | 10.9610346 |
| FAM8A1 | 0.89368479 | 0.067225527 | 0.017744931 | 14.89908179 | 4.7435639 | 4.3513152 | 4.7244061 | 8.6215576 | 7.4040744 | 9.5904678 |
| RPL11 | 0.917420527 | 0.063325847 | 0.015671989 | 14.81956399 | 10.6550412 | 10.6763105 | 11.0461932 | 14.0123343 | 14.5823892 | 14.935643 |
| EIF2S3 | 0.935533137 | 0.060847991 | 0.014312766 | 14.7496231 | 7.021395 | 7.0338116 | 6.3692392 | 10.2518454 | 11.8086651 | 10.4181561 |
| PFDN2 | 0.96628903 | 0.057324142 | 0.012491374 | 14.74521914 | 3.8399484 | 5.4346801 | 5.2176156 | 8.6033384 | 9.2216029 | 9.0997909 |
| NUP160 | 0.766079018 | 0.105517102 | 0.038440985 | 14.73626778 | 4.7435639 | 4.8079702 | 4.4498938 | 6.7770801 | 8.6892694 | 8.6288544 |
| COL14A1 | 0.940714393 | 0.060104489 | 0.013959721 | 14.6794039 | 5.8565586 | 6.0924064 | 6.3267171 | 11.1731726 | 9.9681278 | 9.3143547 |
| GTF2A2 | 0.861236018 | 0.073634891 | 0.021099254 | 14.66835217 | 3.3509967 | 4.3899364 | 2.3793449 | 6.7105675 | 8.2645713 | 6.8257955 |
| MEF2C | 0.972453265 | 0.056976583 | 0.012102223 | 14.60009264 | 4.6820765 | 4.4133226 | 3.9352215 | 7.8031272 | 8.2175169 | 10.3835676 |
| NFIL3 | 0.893071786 | 0.067286289 | 0.017810319 | 14.59704312 | 6.6783891 | 5.3621423 | 7.4018955 | 11.2644118 | 10.5459934 | 9.6989376 |
| HTR2A | 0.880871193 | 0.06957449 | 0.019134237 | 14.59403557 | 6.4179694 | 5.3406193 | 6.0540376 | 8.8001347 | 10.1587087 | 10.2852763 |
| MFN2 | 0.7874173336 | 0.097112287 | 0.033612292 | 14.58611914 | 3.8197323 | 2.8096013 | 2.1654208 | 6.6761254 | 5.2428646 | 7.8691489 |
| MDGA2 | 0.92651987 | 0.061745969 | 0.014991575 | 14.53576003 | 2.2016907 | 2.0230478 | 2.1654208 | 6.0269554 | 5.1121088 | 8.5419101 |
| ANXA1 | 0.86503442 | 0.072750432 | 0.020714114 | 14.50515735 | 6.0999914 | 8.8196737 | 7.4620859 | 11.9404711 | 11.3205799 | 11.0201315 |
| C11orf10 | 0.826621276 | 0.083744193 | 0.026311482 | 14.47669177 | 7.4101728 | 6.7020747 | 6.4507011 | 11.2658605 | 9.4147603 | 10.7327567 |
| NAMPT | 0.899404137 | 0.066432398 | 0.017187676 | 14.44686593 | 7.6416849 | 6.270596 | 6.4507011 | 11.4943695 | 10.5300335 | 10.0845675 |
| GBP4 | 0.885000359 | 0.068624233 | 0.018680895 | 14.38836994 | 2.993831 | 4.3899364 | 3.9083598 | 6.8406623 | 7.4040744 | 9.1825988 |
| ZC3H11A | 0.898652074 | 0.066663913 | 0.017269518 | 14.37146758 | 6.7367617 | 4.9115166 | 5.018694 | 10.0547522 | 8.756652 | 9.9219195 |
| CHURC1 | 0.854047038 | 0.07547923 | 0.022074942 | 14.29183243 | 5.7003762 | 5.3406193 | 5.3892653 | 9.2263843 | 7.6601162 | 10.6395124 |
| METRN | 0.800389393 | 0.092403668 | 0.030948407 | 14.21615392 | 6.186289 | 4.4899364 | 5.3083598 | 7.7378191 | 8.4111814 | 10.1210186 |
| RGS5 | 0.875131616 | 0.070754858 | 0.019831501 | 14.15551048 | 10.1124251 | 8.214531 | 8.54408 | 11.7722875 | 13.935717 | 13.3023141 |
| SNHG12 | 0.860824133 | 0.073804927 | 0.02117227 | 14.06681488 | 3.8197323 | 4.3513152 | 5.3892653 | 7.6339701 | 9.2838364 | 8.0813159 |
| ANP32B | 0.89043607 | 0.067913831 | 0.018163364 | 14.04322846 | 7.6263253 | 7.1060646 | 6.6362622 | 10.2012578 | 11.438128 | 10.9908856 |
| YAP1 | 0.726124291 | 0.124034522 | 0.049366124 | 14.01822561 | 7.021395 | 6.5720715 | 6.8006628 | 11.1078071 | 8.5819002 | 10.6098946 |
| SEC22C | 0.88811537 | 0.068142722 | 0.018362353 | 13.96660489 | 5.0569476 | 4.8079702 | 4.2859964 | 8.8855392 | 7.7510357 | 8.6118796 |
| CHRDL1 | 0.832537837 | 0.081828571 | 0.025265185 | 13.96431152 | 5.0569476 | 3.3213504 | 6.5278107 | 10.3314833 | 8.0305306 | 8.7884466 |
| UBE2E2 | 0.828750202 | 0.082955513 | 0.025890235 | 13.88416192 | 6.0999914 | 4.8079702 | 4.4498938 | 8.6033384 | 8.0122661 | 10.0028812 |
| ATAD1 | 0.820422617 | 0.085658176 | 0.027321672 | 13.84278208 | 6.5212096 | 4.3804956 | 4.5083337 | 8.6215576 | 8.5694617 | 9.6908773 |
| PAIP2 | 0.89769947 | 0.06670795 | 0.017349755 | 13.77234114 | 7.1123989 | 6.0604012 | 6.3267171 | 10.1829712 | 10.6352324 | 9.8441031 |
| RPL15 | 0.911255945 | 0.064460843 | 0.016215999 | 13.68783107 | 10.4146938 | 10.0798327 | 10.1752278 | 13.3603592 | 14.1894599 | 14.1865251 |
| GTF2H5 | 0.793331984 | 0.094918088 | 0.032337318 | 13.653898 | 5.3354128 | 3.3213504 | 5.3892653 | 8.4177128 | 7.0925914 | 10.1029082 |
| PSMA4 | 0.845247147 | 0.07794672 | 0.023224745 | 13.62416608 | 5.7794294 | 5.6616851 | 3.7641245 | 8.6215576 | 9.5475254 | 8.4301508 |
| LOC100129480 | 0.821054607 | 0.084573525 | 0.027220573 | 13.56111025 | 5.0569476 | 4.3513152 | 6.4105447 | 8.3967085 | 9.5601539 | 8.818351 |
| MSRB3 | 0.884465914 | 0.0867652 | 0.018729038 | 13.55847085 | 5.2636993 | 5.4346801 | 4.2859964 | 8.0382872 | 9.2680123 | 9.0248218 |
| EPS8 | 0.756418019 | 0.10976326 | 0.040827249 | 13.49071421 | 6.8201191 | 6.0361098 | 6.0540376 | 8.3317959 | 9.8079324 | 11.3596546 |
| XLAP | 0.94272791 | 0.059848162 | 0.013809677 | 13.44324316 | 6.7650859 | 6.6706551 | 5.6099449 | 10.4174205 | 10.5138952 | 9.9080797 |
| PCBP4 | 0.90225861 | 0.065963593 | 0.016946963 | 13.30588266 | 4.6394091 | 4.9115166 | 4.7549172 | 8.4889095 | 7.8365643 | 9.3454959 |
| TMEM109 | 0.896518772 | 0.066891468 | 0.017504614 | 13.23484742 | 4.6394091 | 3.7709946 | 4.2859964 | 8.4384157 | 8.0122661 | 7.4007641 |
| RPL13AP20 | 0.877873407 | 0.070255881 | 0.019875579 | 13.18153468 | 11.4075 | 11.9474319 | 11.7842038 | 14.668965 | 15.6678784 | 15.6610764 |
| ARHGAP6 | 0.754587312 | 0.110509614 | 0.041307069 | 13.17146169 | 7.0446897 | 3.360637 | 5.3892653 | 9.1086088 | 8.3250145 | 9.3759791 |
| BRP44 | 0.952738879 | 0.058717048 | 0.013155741 | 13.14009898 | 5.0569476 | 4.8079702 | 2.9956812 | 8.3537595 | 8.5819002 | 8.5238744 |
| TMEM64 | 0.839898422 | 0.079307362 | 0.024056006 | 12.99663839 | 6.3818471 | 5.8096013 | 7.4018955 | 11.1019621 | 9.4216969 | 10.225152 |
| IGFBP3 | 0.85596607 | 0.075059941 | 0.021845463 | 12.99561165 | 6.7650859 | 5.3621423 | 6.0540376 | 10.575312 | 9.7539902 | 9.0375903 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| GFRA1 | 0.848370253 | 0.077303306 | 0.022846827 | 12.95239124 | 6.3447976 | 5.3621423 | 7.0032858 | 10.6984324 | 9.2295305 | 9.6626598 |
| OBFC1 | 0.833824268 | 0.08138461 | 0.025022065 | 12.87646451 | 4.6820765 | 4.8079702 | 3.7641245 | 6.7442069 | 8.3687411 | 10.0784017 |
| C6orf62 | 0.806529204 | 0.090187602 | 0.029671829 | 12.77674175 | 7.1158353 | 5.3621423 | 6.3267171 | 10.4174205 | 10.0819703 | 9.0375903 |
| PSPC1 | 0.848312388 | 0.077303306 | 0.02285485 | 12.76451011 | 4.2098819 | 4.7365865 | 5.7236017 | 8.2638247 | 8.734539 | 8.4106527 |
| PPP2R2A | 0.919897851 | 0.06299636 | 0.015502688 | 12.69878235 | 4.815804 | 5.1957839 | 5.3892653 | 8.4281014 | 8.8624022 | 9.32481 |
| CEP68 | 0.805182069 | 0.090395406 | 0.029844339 | 12.6668481 | 5.3044627 | 3.3213504 | 4.5083337 | 8.7008115 | 6.9843361 | 8.4106527 |
| NEMF | 0.886849834 | 0.068365464 | 0.018509187 | 12.58795995 | 6.186289 | 5.297868 | 2.1654208 | 8.9518406 | 9.1057844 | 8.833074 |
| ATL1 | 0.88032251 | 0.069612081 | 0.019190404 | 12.53921637 | 4.6394091 | 3.7709946 | 3.3243747 | 7.9545288 | 6.9073747 | 8.2877844 |
| CXCL12 | 0.848861391 | 0.077198422 | 0.022781032 | 12.53209292 | 7.4971815 | 7.2617905 | 9.3107812 | 12.9583367 | 10.5459934 | 12.671147 |
| FGD5-AS1 | 0.828839559 | 0.082955513 | 0.02588221 | 12.48870381 | 6.8201191 | 6.0726357 | 6.1759311 | 10.6962851 | 9.818483 | 9.14769 |
| ARPC3 | 0.811201413 | 0.088696263 | 0.028906363 | 12.44812129 | 6.3447976 | 4.8304956 | 3.9083598 | 9.5165726 | 8.21751692 | 8.4683738 |
| FAM200B | 0.812901739 | 0.088144268 | 0.028607879 | 12.44323818 | 4.7435639 | 5.1957839 | 3.7641245 | 7.4827092 | 7.956043 | 8.833074 |
| ARMC1 | 0.831038389 | 0.082217411 | 0.025547621 | 12.4263524 | 5.7794294 | 5.4346801 | 3.3243747 | 8.6124767 | 9.4147603 | 8.0311264 |
| NARFL | 0.852386776 | 0.075877883 | 0.022228998 | 12.39814856 | 3.8197323 | 2.0230478 | 2.1654208 | 5.6551006 | 7.4318221 | 6.496723 |
| ETFA | 0.874096683 | 0.070954628 | 0.019934205 | 12.38389714 | 4.7435639 | 4.9115166 | 2.1654208 | 7.3794393 | 8.2490564 | 8.5419101 |
| HDDC2 | 0.790933841 | 0.095718911 | 0.032783439 | 12.35546194 | 5.6586086 | 5.3621423 | 5.2176156 | 7.8190025 | 8.9892193 | 9.6415459 |
| PCBD1 | 0.81978204 | 0.08595687 | 0.027445238 | 12.25462899 | 5.982974 | 5.7897017 | 4.9444683 | 9.7035053 | 8.8418632 | 8.5597232 |
| GLUL | 0.938475604 | 0.060337931 | 0.01411137 | 12.23713573 | 8.0740814 | 7.0089004 | 8.2346552 | 11.776359 | 11.6872754 | 11.5274641 |
| GCFC2 | 0.846975683 | 0.077594277 | 0.022987242 | 12.16765085 | 4.6394091 | 3.7709946 | 2.3793449 | 7.244891 | 6.8260777 | 8.2443879 |
| TCP1 | 0.821839578 | 0.085361525 | 0.027106636 | 12.12563722 | 6.0548278 | 6.1842483 | 6.8910052 | 10.3147842 | 10.4909939 | 8.9457427 |
| SF3B1 | 0.893056562 | 0.067286289 | 0.017813342 | 12.04916889 | 5.982974 | 4.3899364 | 5.6099449 | 9.5738357 | 8.8926726 | 8.985824 |
| NR3C1 | 0.870071476 | 0.071776816 | 0.020330579 | 12.04450485 | 6.2275774 | 4.7365865 | 5.9741452 | 9.5644483 | 8.8926726 | 9.6331575 |
| C10orf26 | 0.728929501 | 0.12296607 | 0.048493942 | 12.01722991 | 6.6175557 | 3.8720139 | 3.9352215 | 8.5086224 | 7.4590463 | 8.8476482 |
| MAP7D3 | 0.763281078 | 0.106685386 | 0.039156704 | 11.99484074 | 3.8197323 | 2.0230478 | 2.9956812 | 5.8529567 | 7.4040744 | 5.8563328 |
| HNRNPA0 | 0.855576216 | 0.075140343 | 0.021901629 | 11.99027384 | 7.8805094 | 7.0089004 | 7.8250252 | 11.8679196 | 11.0874723 | 10.5926931 |
| ANK2 | 0.804168668 | 0.090775559 | 0.030104309 | 11.87419279 | 3.8197323 | 4.3513152 | 5.3892653 | 8.9590228 | 7.1604986 | 8.1767432 |
| PPIA | 0.873594632 | 0.07101993 | 0.019975929 | 11.75274209 | 6.5544048 | 6.7629335 | 6.3267171 | 9.5262757 | 11.0874723 | 10.1089703 |
| TRIM4 | 0.892260879 | 0.067567176 | 0.017948327 | 11.74747067 | 1.8744435 | 3.8720139 | 3.9083598 | 7.4626381 | 6.8672984 | 7.2333272 |
| UBE2L6 | 0.7673978 | 0.104951556 | 0.038123245 | 11.65311685 | 6.4179694 | 4.3513152 | 4.9444683 | 9.7205099 | 7.9937674 | 8.48711222 |
| SAP18 | 0.856343613 | 0.074882017 | 0.021752387 | 11.63961466 | 7.6108005 | 6.7020747 | 7.2956386 | 10.2430461 | 9.9454868 | 10.9908856 |
| IRS2 | 0.784635392 | 0.098241201 | 0.034238947 | 11.62981855 | 7.9805393 | 7.6153768 | 8.685452 | 12.2252087 | 11.6800618 | 10.575284 |
| STAG1 | 0.766157825 | 0.10551702 | 0.02971275 | 11.59669944 | 2.993831 | 3.7709946 | 8.8079702 | 6.5294995 | 7.5630806 | 7.8402926 |
| ADCY6 | 0.861887475 | 0.073515148 | 0.021020621 | 11.56158826 | 4.309025 | 4.8079702 | 2.9956812 | 7.400693 | 8.0663803 | 7.8402926 |
| DPYSL2 | 0.806313842 | 0.090221715 | 0.02897173 | 11.5539731 | 7.9188379 | 6.0361098 | 7.2046135 | 11.4247442 | 9.5664269 | 11.1898834 |
| RPLP2 | 0.811964359 | 0.088607313 | 0.028816497 | 11.53303828 | 11.9574379 | 12.1454554 | 12.1638325 | 14.7428672 | 15.6731561 | 15.8474469 |
| XRN1 | 0.762923418 | 0.106946495 | 0.039286669 | 11.4231475 | 5.3044627 | 5.3406193 | 4.4498938 | 7.0964955 | 9.585084 | 8.818351 |
| SPRED2 | 0.816394046 | 0.086958113 | 0.028017331 | 11.35686286 | 4.7435639 | 4.7507076 | 3.9083598 | 9.0891013 | 8.2490564 | 6.9389568 |
| ITM2A | 0.827219202 | 0.083495213 | 0.026178288 | 11.35248957 | 5.0569476 | 5.1957839 | 6.7692467 | 12.7556967 | 8.7007207 | 8.5597232 |
| BZW1 | 0.743063913 | 0.116342943 | 0.044223494 | 11.3465869 | 7.3553323 | 7.6153768 | 7.3603269 | 10.9371717 | 9.6749135 | 11.1195633 |
| MSMO1 | 0.895471257 | 0.067048563 | 0.017600899 | 11.25024034 | 5.3162271 | 4.7365865 | 2.3793449 | 8.8081111 | 8.0305306 | 8.1767432 |
| IRF2BP2 | 0.85567373 | 0.075127708 | 0.02188581 | 11.23445061 | 7.5139709 | 7.1970971 | 8.114773 | 11.5655021 | 10.8013455 | 11.003957 |
| F5 | 0.809705695 | 0.089166903 | 0.029159913 | 11.23407095 | 4.7435639 | 4.3899364 | 5.3892653 | 7.8808129 | 8.2333728 | 8.3090028 |
| C1orf55 | 0.826119237 | 0.083959567 | 0.026420605 | 11.22750064 | 4.963444 | 4.3513152 | 5.2176156 | 10.3425096 | 8.4524089 | 7.3194719 |
| ARID5B | 0.838880462 | 0.079552776 | 0.024242419 | 11.20842419 | 7.4971815 | 6.1842483 | 8.5253933 | 10.9836931 | 11.7214074 | 10.7979987 |
| BAZ2B | 0.851873338 | 0.076086629 | 0.022232769 | 11.19833906 | 4.963444 | 2.0230478 | 5.3892653 | 8.4486569 | 8.6892694 | 7.6538745 |
| GLT8D1 | 0.756167544 | 0.109799836 | 0.040876996 | 11.18069702 | 5.3354128 | 4.7365865 | 4.2859964 | 8.2521782 | 7.1269443 | 8.818351 |
| COPB2 | 0.780413175 | 0.099833202 | 0.035079836 | 11.15019582 | 6.3067721 | 4.3513152 | 5.9352215 | 8.3094927 | 8.0122661 | 9.4637448 |
| EPAS1 | 0.795185177 | 0.094440529 | 0.032065313 | 11.11704826 | 9.417868 | 8.5529154 | 7.9423658 | 11.5513158 | 12.0302104 | 12.5017958 |
| MLL5 | 0.861482611 | 0.075811947 | 0.021071973 | 11.09848594 | 7.2788106 | 6.3119075 | 7.1568531 | 10.7511015 | 10.3121715 | 10.2691257 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| CUTA | 0.878573558 | 0.070068758 | 0.019443152 | 11.08631047 | 6.8989234 | 6.8496647 | 6.7692467 | 10.3203721 | 9.9822728 | 10.575284 |
| KDELR2 | 0.725237177 | 0.124340802 | 0.049626093 | 11.05074583 | 9.0885863 | 7.7567626 | 7.8848881 | 12.5546582 | 10.059091 | 12.2203256 |
| POLR2C | 0.780455965 | 0.099816017 | 0.03505737 | 11.04375185 | 5.0569476 | 3.360637 | 3.9352215 | 8.3753938 | 7.5120008 | 6.8257955 |
| MAP9 | 0.793472674 | 0.094918088 | 0.032322073 | 10.88186968 | 6.8989234 | 4.4133226 | 4.5083337 | 9.8727797 | 7.8571772 | 9.4542526 |
| STOML2 | 0.825359025 | 0.084246978 | 0.026524914 | 10.88119993 | 6.9736463 | 5.1957839 | 5.2176156 | 8.6394596 | 9.7093356 | 10.1797958 |
| PPFIBP1 | 0.900382913 | 0.066297168 | 0.017109043 | 10.83045106 | 5.2263993 | 5.4876732 | 5.3892653 | 10.2489183 | 8.7007207 | 8.7267115 |
| FABP4 | 0.795096253 | 0.094440529 | 0.032081361 | 10.7891167 | 6.2677178 | 5.7127845 | 5.5934735 | 9.6992226 | 10.7332789 | 11.5183831 |
| CCDC152 | 0.771249521 | 0.103361885 | 0.037221375 | 10.73287898 | 6.2677178 | 6.270596 | 7.9139132 | 11.3378784 | 10.2236543 | 9.3959492 |
| PSMB1 | 0.820919126 | 0.085550248 | 0.027259087 | 10.67551065 | 6.6482929 | 4.9115166 | 5.7236017 | 8.9446225 | 9.1398349 | 9.8585673 |
| LACTB | 0.74997367 | 0.112655516 | 0.042459279 | 10.67047795 | 3.8197323 | 2.8096013 | 3.3243747 | 5.4258059 | 6.7399276 | 8.0813159 |
| THY1 | 0.790197086 | 0.095932777 | 0.032919843 | 10.65897244 | 5.7003762 | 6.7328249 | 6.7042855 | 10.8891001 | 9.1143726 | 9.5375148 |
| TNFRSF10B | 0.823626154 | 0.084832597 | 0.026812966 | 10.65530237 | 6.4876101 | 6.3520696 | 7.2508437 | 10.4610743 | 9.8496795 | 9.9011097 |
| RPS27L | 0.743906468 | 0.115861858 | 0.044163524 | 10.56179378 | 8.085359 | 6.537655 | 6.0540376 | 10.2807948 | 9.2685279 | 11.486142 |
| RDX | 0.806764669 | 0.090105859 | 0.029630105 | 10.4205879 | 6.0082059 | 4.8304956 | 4.7244061 | 9.1902202 | 8.6064601 | 8.1057709 |
| AP1G1 | 0.739016742 | 0.118062901 | 0.045865163 | 10.41875502 | 6.1437849 | 4.4133226 | 4.4498938 | 8.5472581 | 7.7944336 | 8.350526 |
| MPHOSPH8 | 0.80426854 | 0.090718963 | 0.030070609 | 10.33872951 | 8.234634 | 7.282726 | 7.5571389 | 11.3705641 | 10.6764145 | 10.9271259 |
| BBX | 0.845222161 | 0.07794672 | 0.023332769 | 10.24247886 | 6.4876101 | 5.1480825 | 6.1759311 | 9.4969685 | 9.1398349 | 9.8441031 |
| RWDD1 | 0.795884361 | 0.094227095 | 0.029630105 | 10.23174627 | 7.373845 | 7.9523826 | 7.056316 | 10.1921435 | 11.5719758 | 10.7288255 |
| COMMD6 | 0.735226165 | 0.11955052 | 0.046612373 | 10.209609 | 6.6482929 | 8.2784691 | 8.7350882 | 10.3831235 | 11.2242208 | 12.0869439 |
| ARL6IP4 | 0.753531554 | 0.111173921 | 0.041626414 | 10.11038492 | 7.7015384 | 6.6385363 | 6.0560619 | 9.4569424 | 9.9101189 | 11.0393044 |
| CIZ1 | 0.824390792 | 0.084691716 | 0.026720693 | 10.08547882 | 4.2098819 | 3.360637 | 3.9083598 | 7.0161533 | 6.6948447 | 8.7423946 |
| NGDN | 0.806379437 | 0.090221715 | 0.029704726 | 10.04378133 | 4.6394091 | 4.3899364 | 4.5083337 | 7.147675 | 7.8365643 | 8.833074 |
| PRPF38B | 0.814006316 | 0.087666999 | 0.028401669 | 10.03580366 | 6.4179694 | 6.7328249 | 7.0300422 | 9.4416416 | 10.059091 | 11.1225628 |
| DTYMK | 0.7343269 | 0.120303656 | 0.046965418 | 9.973951109 | 6.5212096 | 5.6616851 | 3.9083598 | 8.0651989 | 8.9798503 | 9.1710561 |
| KLF4 | 0.802408973 | 0.091256582 | 0.030414026 | 9.9575909 | 6.3818471 | 6.9314777 | 7.8096632 | 10.8872188 | 10.2472744 | 10.1682304 |
| ARF6 | 0.826941548 | 0.083599382 | 0.026230442 | 9.900203577 | 7.786906 | 8.3195726 | 8.5625279 | 12.4238576 | 11.6270308 | 11.0644784 |
| CLSTN1 | 0.824145345 | 0.084705069 | 0.026744765 | 9.803034952 | 5.982974 | 5.1957839 | 5.3892653 | 8.930077 | 9.2762025 | 8.4683738 |
| SF3B14 | 0.732678491 | 0.121002258 | 0.047323277 | 9.790926277 | 4.6394091 | 5.4876732 | 5.018694 | 7.1223122 | 8.3101394 | 9.6746202 |
| FBXO32 | 0.742217933 | 0.116885203 | 0.04466902 | 9.777346435 | 6.0999914 | 6.5023977 | 4.4498938 | 9.3894343 | 9.4216969 | 8.2443879 |
| GNB2L1 | 0.856705399 | 0.074812109 | 0.021707454 | 9.730049602 | 10.0789648 | 9.9998997 | 10.0148512 | 13.3614119 | 13.2194954 | 13.6080838 |
| SERF2 | 0.816085647 | 0.086958113 | 0.028063474 | 9.715628863 | 7.5951068 | 6.9577495 | 7.4018955 | 10.9534456 | 10.6822029 | 10.2139459 |
| TTC17 | 0.789448888 | 0.0961872 | 0.033054642 | 9.711989783 | 4.7435639 | 4.4133226 | 3.7641245 | 7.268205 | 9.4216969 | 7.0438915 |
| ANO7 | 0.7514334644 | 0.112148902 | 0.042120677 | 9.59215601 | 5.0569476 | 5.297868 | 5.5446534 | 7.4827092 | 9.9869572 | 8.5597232 |
| HSPE1 | 0.741951881 | 0.117013269 | 0.044756479 | 9.580184638 | 6.6783891 | 7.939256 | 7.5754206 | 10.835474 | 11.5082338 | 9.6664224 |
| CD4 | 0.731944187 | 0.121372077 | 0.047542325 | 9.571507262 | 4.963444 | 3.8720139 | 6.0721689 | 8.7784313 | 8.7784313 | 8.2221901 |
| ZCCHC9 | 0.822130593 | 0.085361525 | 0.027082564 | 9.516284116 | 5.8972917 | 5.297868 | 3.3243747 | 8.3094927 | 8.3543123 | 9.14769 |
| PRKD3 | 0.779991955 | 0.099902938 | 0.035178528 | 9.508665498 | 9.508865498 | 5.4346801 | 6.0721689 | 9.1531261 | 9.3214118 | 7.9524091 |
| SLU7 | 0.772266119 | 0.103092658 | 0.036988687 | 9.490976356 | 5.982974 | 5.297868 | 6.0316576 | 8.0517861 | 9.2295305 | 10.3835676 |
| TRA2A | 0.79776008 | 0.093697465 | 0.031659312 | 9.483417779 | 6.7928648 | 6.3119075 | 7.1323668 | 10.3777739 | 10.2589411 | 9.4731175 |
| TINAGL1 | 0.763896816 | 0.106557388 | 0.038995426 | 9.414495775 | 6.2275774 | 8.0894025 | 6.8910052 | 9.2382403 | 11.3242864 | 11.2542022 |
| NRN1 | 0.792012044 | 0.095431107 | 0.032653454 | 9.368150281 | 5.2263993 | 4.3531152 | 5.2252164 | 7.5790795 | 9.2989842 | 8.2662493 |
| TAP1 | 0.771449011 | 0.103268709 | 0.037170826 | 9.231131614 | 6.0999914 | 4.3899364 | 6.0721689 | 8.9005384 | 9.3064989 | 8.4683738 |
| GOLTIB | 0.758119283 | 0.109295557 | 0.040473401 | 9.185277219 | 7.0446897 | 6.3911446 | 5.5929159 | 9.7703533 | 9.2295305 | 9.5904678 |
| EEF1A1 | 0.804961547 | 0.090458328 | 0.029894889 | 9.118221008 | 12.2601471 | 11.9918161 | 12.5153 | 15.4488994 | 15.8390843 | 15.1507049 |
| FOXO3 | 0.739397768 | 0.1180144 | 0.045522747 | 9.077014441 | 7.7448535 | 6.6706551 | 8.0245047 | 10.1170787 | 11.2067226 | 10.5970127 |
| SPTAN1 | 0.778798295 | 0.100470987 | 0.035485838 | 9.060517648 | 5.7794294 | 4.8304956 | 6.3558005 | 8.9590228 | 8.6660906 | 9.2166829 |
| PTPN12 | 0.7986597 | 0.0936714 | 0.031421809 | 9.046527085 | 6.6540448 | 6.0726357 | 6.564874 | 9.2499997 | 9.7812134 | 9.7149245 |
| IGFBP6 | 0.798794549 | 0.093160485 | 0.031347188 | 9.029994426 | 6.7367617 | 6.2280676 | 6.4897707 | 9.6644958 | 9.802628 | 9.4253954 |
| EXOSC1 | 0.746844264 | 0.114273666 | 0.043407687 | 9.029433269 | 4.7435639 | 4.4133226 | 3.761245 | 6.6761254 | 7.5879581 | 8.3090028 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| AKT3 | 0.731883481 | 0.121384784 | 0.047572816 | 9.017307225 | 7.1342805 | 5.3621423 | 6.3358005 | 8.8855392 | 10.0193285 | 9.5284972 |
| C2orf28 | 0.745362914 | 0.115114708 | 0.043784001 | 8.996396945 | 6.2275774 | 5.3621423 | 3.9083598 | 9.001381 | 8.5314896 | 8.0053615 |
| MALAT1 | 0.771461089 | 0.103268709 | 0.037162802 | 8.909143621 | 10.7555327 | 10.4027151 | 11.5361053 | 14.3258503 | 14.5371937 | 13.5580019 |
| ITPRIPL2 | 0.731552532 | 0.121504123 | 0.047714034 | 8.879622299 | 7.0446897 | 6.3911446 | 5.9741452 | 10.195188 | 8.922321 | 9.5904678 |
| NDUFAF2 | 0.794539832 | 0.094647408 | 0.032167215 | 8.740510082 | 6.8731305 | 6.1842483 | 6.0316576 | 9.1593751 | 9.7703857 | 9.9492072 |
| SOWAHC | 0.752162632 | 0.111864532 | 0.041961005 | 8.612717825 | 5.2663993 | 5.4876732 | 5.4876732 | 8.5941417 | 8.5569151 | 8.6622163 |
| KTN1 | 0.727540118 | 0.123575599 | 0.048696975 | 8.600192586 | 5.8565586 | 4.3899364 | 3.9083598 | 8.7008115 | 8.9609276 | 6.7030085 |
| DNAJC27 | 0.798691215 | 0.093241241 | 0.031397737 | 8.594323591 | 5.3354128 | 4.8079702 | 4.9444683 | 7.9107527 | 8.4387969 | 8.2662493 |
| PLEKHH2 | 0.771739161 | 0.10322713 | 0.037106636 | 8.583847152 | 5.3285264 | 6.0361098 | 5.7236017 | 10.013954 | 8.5942324 | 8.4301508 |
| HIGD2A | 0.724166466 | 0.12474266 | 0.049914146 | 8.5025188 | 5.8565586 | 4.8079702 | 5.5446534 | 7.8958605 | 8.3543123 | 9.1710561 |
| IMPDH2 | 0.785690282 | 0.097887794 | 0.033977373 | 8.497198131 | 5.7445127 | 6.2280676 | 6.0316576 | 9.4720826 | 8.831483 | 9.0997909 |
| PTGES3 | 0.759187807 | 0.108650799 | 0.04014523 | 8.479227622 | 8.2039211 | 7.7567626 | 8.4872775 | 11.4436698 | 10.8406955 | 11.369788 |
| PRRC2C | 0.727843513 | 0.123293242 | 0.048863035 | 8.446888491 | 8.9473922 | 9.0199958 | 8.1639276 | 12.0984158 | 11.6987427 | 11.3105244 |
| VEGFB | 0.737366924 | 0.118603779 | 0.04606756 | 8.38947916 | 6.6175557 | 5.1480825 | 5.3892653 | 8.2166637 | 8.9798503 | 9.6076956 |
| GGCX | 0.808858608 | 0.089366489 | 0.029298724 | 8.363983186 | 6.2275774 | 6.7020747 | 6.8314096 | 9.7662649 | 9.8802157 | 9.6908773 |
| NAA40 | 0.777390992 | 0.100997357 | 0.035771484 | 8.270024433 | 6.4532097 | 6.0924064 | 5.7029118 | 9.062674 | 9.0531526 | 9.5011013 |
| LOC100505806 | 0.750958224 | 0.112223511 | 0.042222579 | 8.238156309 | 5.3285264 | 4.8079702 | 5.3892653 | 7.7210195 | 8.6306088 | 8.3708479 |
| NMD3 | 0.751117871 | 0.112223511 | 0.042184065 | 8.21400123 | 5.3162271 | 5.1957839 | 5.7236017 | 7.8190025 | 8.3543123 | 10.1565715 |
| PSMD6 | 0.751067056 | 0.112223511 | 0.042192089 | 7.930604712 | 5.7445127 | 5.1480825 | 5.018694 | 7.9254928 | 8.1355133 | 9.5991074 |
| PSAP | 0.727966231 | 0.123245219 | 0.048815694 | 7.930336744 | 9.3162351 | 8.4456055 | 9.0481921 | 12.8172612 | 11.4329877 | 11.8212914 |
| PTPN14 | 0.745990948 | 0.114727673 | 0.043617909 | 7.861074951 | 5.3354128 | 6.0441977 | 2.9556812 | 7.704022 | 8.3101394 | 8.985824 |
| RNF146 | 0.743577286 | 0.116083282 | 0.0442670 | 7.792187433 | 5.0569476 | 5.4346801 | 5.5969865 | 8.3967085 | 8.65436 | 7.9791282 |
| RSBN1 | 0.731873193 | 0.121384784 | 0.047587258 | 7.70079791 | 6.3067721 | 3.3606472 | 6.3267171 | 8.0784109 | 9.2136315 | 9.2717591 |
| METAP2 | 0.746981866 | 0.114203645 | 0.043343497 | 7.628749906 | 6.1437849 | 4.4133226 | 6.6362622 | 9.1963108 | 8.8624022 | 9.0752315 |
| PPP1R2 | 0.755372689 | 0.110198518 | 0.04110808 | 7.54336207 | 4.815804 | 4.7365865 | 3.7641245 | 7.6517941 | 6.6483084 | 9.6989376 |
| TMEM51 | 0.762670859 | 0.106981687 | 0.039334831 | 7.480659068 | 5.3162271 | 6.0726357 | 6.0560619 | 8.7093547 | 8.9704199 | 8.9592273 |
| RPL13 | 0.736262615 | 0.119102493 | 0.046378881 | 7.3459284 | 12.3120719 | 12.3821266 | 12.4523907 | 14.907489 | 15.2590714 | 15.9687652 |
| TSPAN3 | 0.724995864 | 0.124466391 | 0.049696702 | 7.228570825 | 7.9561744 | 7.4213407 | 6.3358005 | 10.2750512 | 10.1669886 | 10.5034676 |
| LARP7 | 0.724530127 | 0.12468513 | 0.049810639 | 7.222019893 | 5.8972917 | 5.4346801 | 5.5969865 | 8.0651599 | 9.6632545 | 8.4493889 |
| PEAR1 | 0.789096967 | 0.096303907 | 0.033158148 | 7.173081778 | 5.3354128 | 2.0230478 | 5.7236017 | 8.5661948 | 8.1522912 | 8.0564393 |
| PSMD7 | 0.727750668 | 0.123353368 | 0.048907165 | 6.881426431 | 7.0901803 | 6.4662577 | 4.4498938 | 9.2084155 | 8.9609276 | 9.8728879 |
| NUAK1 | 0.755537417 | 0.110198518 | 0.041100056 | 6.386668583 | 6.8468682 | 4.4133226 | 7.5198657 | 9.2961016 | 9.5219318 | 10.0344875 |
| TNFRSF18 | -0.867019435 | 0.072221888 | 0.020527963 | 0.039506385 | 5.2663993 | 8.8895842 | 8.6599785 | 5.9133149 | 6.6483084 | 6.6019289 |
| RGS14 | -0.768464034 | 0.1046949 | 0.037908208 | 0.038093846 | 5.3162271 | 7.7863852 | 7.7663078 | 5.9712523 | 8.9704199 | 6.6019289 |
| GAL | -0.727426869 | 0.123381232 | 0.048999438 | 0.030832695 | 2.2016907 | 10.7793494 | 11.9209565 | 6.9015613 | 15.2590714 | 6.6019289 |
| AIF1L | -0.840537939 | 0.079141153 | 0.02393244 | 0.028309227 | 5.7445127 | 9.0508366 | 8.9812053 | 6.8092213 | 8.9609276 | 6.6019289 |
| CD101 | -0.796285688 | 0.094083369 | 0.031867127 | 0.028309227 | 5.7445127 | 8.181467 | 8.458015 | 6.6046733 | 9.5219318 | 6.6019289 |
| CD3E | -0.805206584 | 0.090395406 | 0.029836315 | 0.020842034 | 6.186289 | 7.282726 | 10.117184 | 7.0161533 | 8.1522912 | 6.6019289 |
| AXIN1 | -0.762244952 | 0.107082149 | 0.039389393 | 0.018673437 | 6.3447976 | 7.885522 | 8.6252987 | 6.7442069 | 8.9609276 | 6.6019289 |
| STAT4 | -0.724193033 | 0.12474266 | 0.049898098 | 0.018083082 | 7.4456083 | 6.3911446 | 8.6252987 | 7.5025051 | 9.5219318 | 6.6019289 |
| ACVR2A | -0.728607126 | 0.123036393 | 0.048578994 | 0.01774996 | 6.4179694 | 7.1522986 | 7.7625708 | 6.8714329 | 7.5025051 | 6.6019289 |
| THOC6 | -0.72710556 | 0.123566409 | 0.049093316 | 0.016666186 | 7.1123989 | 7.0338116 | 8.1639276 | 7.4626381 | 7.5025051 | 6.6019289 |
| RLIM | -0.736510971 | 0.119030883 | 0.046292225 | 0.01603187 | 8.3699022 | 8.5002579 | 8.9535147 | 8.6627439 | 7.4626381 | 6.6019289 |
| ALS2CL | -0.809500504 | 0.089247119 | 0.029230834 | 0.01294733 | 6.8731305 | 9.4804432 | 7.6804979 | 7.4626381 | 2.5373444 | 6.6019289 |
| TNF | -0.757233013 | 0.109484618 | 0.040651129 | 0.012472543 | 7.5305672 | 9.4155716 | 7.2046135 | 8.1174489 | 1.2054667 | 6.6019289 |
| SLC4A7 | -0.731769694 | 0.121411587 | 0.047617749 | 0.011426949 | 7.6568826 | 7.6153768 | 8.0111355 | 8.0109044 | 1.2054667 | 6.6019289 |
| EXOSC2 | -0.767700479 | 0.104951556 | 0.038035786 | 0.011124148 | 7.4801945 | 7.6156281 | 8.8701536 | 7.5025051 | 1.2054667 | 6.6019289 |
| SLC7A6 | -0.78451864 | 0.098241201 | 0.034246971 | 0.010487801 | 7.1770729 | 7.9653908 | 8.1759589 | 7.4626381 | 1.2054667 | 6.6019289 |
| SKP2 | -0.740635906 | 0.11768042 | 0.045139212 | 0.009570616 | 7.9925691 | 7.9126391 | 7.6113033 | 8.0517861 | 1.2054667 | 6.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| LIMD1 | −0.740129831 | 0.117838959 | 0.045289256 | 0.009286124 | 7.9561744 | 7.6317881 | 8.0111355 | 8.1045532 | 1.2054667 | 0.6019289 |
| LRRFIP2 | −0.801591152 | 0.091706201 | 0.030624248 | 0.009284772 | 7.943836 | 8.8758705 | 7.9563845 | 8.1045532 | 1.2054667 | 0.6019289 |
| ISG20L2 | −0.773253949 | 0.102731018 | 0.036767231 | 0.008980224 | 8.0044995 | 7.926009 | 8.2799514 | 8.1045532 | 1.2054667 | 0.6019289 |
| RNF149 | −0.749616412 | 0.112869889 | 0.042577229 | 0.008906872 | 8.016332 | 8.3984252 | 7.9976413 | 8.4689236 | 1.2054667 | 0.6019289 |
| SIK3 | −0.750578967 | 0.112470747 | 0.042334109 | 0.008834709 | 8.0280683 | 7.939256 | 8.9181369 | 8.7093547 | 1.2054667 | 0.6019289 |
| SORBS1 | −0.823563365 | 0.084832597 | 0.02682099 | 0.008400829 | 7.4971815 | 8.8963925 | 9.0932984 | 8.2285993 | 1.2054667 | 0.6019289 |
| MAN1A1 | −0.759865974 | 0.108225602 | 0.039970312 | 0.008234283 | 8.1296079 | 7.5987767 | 8.3873354 | 8.180253 | 1.2054667 | 0.6019289 |
| EP400 | −0.773589899 | 0.102608214 | 0.036679772 | 0.007992855 | 8.1725401 | 8.1476275 | 8.5625279 | 8.4789512 | 1.2054667 | 0.6019289 |
| SUN1 | −0.763245699 | 0.10685404 | 0.03918238 | 0.007591562 | 7.7448535 | 8.246842 | 8.4281467 | 8.3206874 | 1.2054667 | 0.6019289 |
| CLIC2 | −0.778371509 | 0.100596765 | 0.035546819 | 0.006713412 | 8.4242047 | 7.8717699 | 9.8393517 | 9.0559909 | 1.2054667 | 0.6019289 |
| SLC39A14 | −0.740179162 | 0.117838919 | 0.045273209 | 0.006408378 | 8.7418194 | 8.4912918 | 7.9423658 | 9.001381 | 1.2054667 | 0.6019289 |
| ALDH1A2 | −0.889153515 | 0.068037763 | 0.01826687 | 0.00610395 | 8.2142315 | 8.5615078 | 10.172278 | 8.3206874 | 1.2054667 | 0.6019289 |
| HS6ST1 | −0.762719163 | 0.106964099 | 0.03931076 | 0.005962331 | 8.2244688 | 8.5953745 | 9.243773 | 9.2499997 | 1.2054667 | 0.6019289 |
| ENPP2 | −0.784959192 | 0.098230159 | 0.03416111 | 0.005861952 | 8.016332 | 8.9031688 | 10.3867524 | 9.6153392 | 1.2054667 | 0.6019289 |
| VCAN | −0.751810338 | 0.112027084 | 0.042056487 | 0.005157503 | 8.8045782 | 8.2784691 | 10.36852 | 10.1041793 | 1.2054667 | 0.6019289 |
| ITGA5 | −0.809190402 | 0.089304414 | 0.029248977 | 0.005148384 | 9.3114408 | 8.2035936 | 9.7576474 | 9.3841082 | 1.2054667 | 0.6019289 |
| IL1R1 | −0.730474898 | 0.12218185 | 0.04806467 | 0.004814919 | 9.1702939 | 8.7907325 | 8.9037393 | 10.097686 | 1.2054667 | 0.6019289 |
| CXCR4 | −0.930425312 | 0.061359395 | 0.01473401 | 0.004445723 | 8.4152951 | 9.0988503 | 11.4433385 | 8.8395827 | 1.2054667 | 0.6019289 |
| HTRA3 | −0.74927297 | 0.113077513 | 0.04269271 | 0.004240561 | 8.6910467 | 9.0869958 | 9.4260873 | 10.064774 | 1.2054667 | 0.6019289 |
| PFKFB3 | −0.7434702 | 0.116136259 | 0.044306347 | 0.00420586 | 8.9960085 | 9.0988503 | 9.7853995 | 10.5181084 | 1.2054667 | 0.6019289 |
| RALGDS | −0.880007525 | 0.069702623 | 0.01924977 | 0.004138105 | 8.518743 | 9.4060615 | 9.3324431 | 8.6573201 | 1.2054667 | 0.6019289 |
| PLN | 0.800820775 | 0.09214206 | 0.030830458 | −0.002312924 | 1.8744435 | 2.0230478 | 2.1654208 | 1.0866873 | 11.124081 | 10.7791142 |
| G1GYF1 | −0.735915558 | 0.119192232 | 0.04643343 | −4.98595154 | 10.8445084 | 10.6842005 | 10.7285216 | 8.8703825 | 1.2054667 | 8.4106527 |
| LRRC27 | −0.757810776 | 0.109635365 | 0.040519939 | −5.636335447 | 9.7650691 | 10.0738369 | 10.3367183 | 7.5790795 | 7.9937674 | 0.6019289 |
| BAZ1B | −0.778109877 | 0.100704268 | 0.03560138 | −5.783886136 | 10.2665157 | 10.4566846 | 10.7366678 | 8.2046286 | 8.0305306 | 0.6019289 |
| HSPA9 | −0.754789861 | 0.110502458 | 0.041247693 | −5.839258562 | 10.2540769 | 10.0678182 | 9.9832349 | 7.522033 | 8.1852726 | 0.6019289 |
| DDX19A | −0.729250965 | 0.122818874 | 0.04839204 | −6.648574266 | 3.8197323 | 3.3213504 | 5.3892653 | 1.0866873 | 1.2054667 | 0.6019289 |
| C1orf16 | −0.748784302 | 0.12325619 | 0.04282672 | −6.742394852 | 3.8399484 | 3.3213504 | 6.1842483 | 1.0866873 | 1.2054667 | 0.6019289 |
| C3orf45 | −0.726813934 | 0.123667925 | 0.049174356 | −6.742394852 | 3.8399484 | 3.3213504 | 5.2176156 | 1.0866873 | 8.2799211 | 0.6019289 |
| EXOSC10 | −0.725663986 | 0.124142562 | 0.049485678 | −6.742394852 | 3.8399484 | 3.8720139 | 3.7641245 | 1.0866873 | 7.0574008 | 0.6019289 |
| C14orf80 | −0.725663986 | 0.124142562 | 0.049485678 | −6.742394852 | 3.8399484 | 3.8720139 | 3.7641245 | 6.4501951 | 1.2054667 | 0.6019289 |
| PNPLA2 | −0.798814577 | 0.093160485 | 0.031323116 | −6.743481091 | 11.0670382 | 11.5584909 | 11.1181107 | 9.1902202 | 1.2054667 | 9.2711591 |
| IGF2-AS1 | −0.750010672 | 0.112640836 | 0.042435208 | −6.767899146 | 3.8399484 | 3.360637 | 6.0540376 | 8.8703825 | 9.2056159 | 0.6019289 |
| AP3M2 | −0.739119149 | 0.118017692 | 0.045626254 | −6.767899146 | 3.8399484 | 3.360637 | 5.5446534 | 1.0866873 | 1.2054667 | 0.6019289 |
| EIF2B5 | −0.756284617 | 0.1097794 | 0.04085132 | −6.801867543 | 10.0533501 | 10.4704377 | 9.3903888 | 8.0784109 | 7.2874192 | 0.6019289 |
| ZNF219 | −0.748675552 | 0.11328963 | 0.042866084 | −6.809091159 | 9.2969617 | 9.5554851 | 8.7269332 | 6.5294995 | 1.2054667 | 7.141714 |
| ID1 | −0.739338591 | 0.1180144 | 0.045554842 | −6.851800368 | 10.1234083 | 9.0569264 | 10.2848865 | 7.9107527 | 7.3469252 | 0.6019289 |
| TTC27 | −0.736331318 | 0.119080705 | 0.046350798 | −6.893929505 | 3.8197323 | 3.8720139 | 3.9083598 | 1.0866873 | 1.2054667 | 0.6019289 |
| EXOC6B | −0.736331318 | 0.119080705 | 0.046350798 | −6.893929505 | 3.8197323 | 3.8720139 | 3.9083598 | 1.0866873 | 1.2054667 | 0.6019289 |
| BRSK2 | −0.732825648 | 0.120980991 | 0.047289577 | −6.893929505 | 5.3285264 | 3.8720139 | 3.3243747 | 1.0866873 | 1.2054667 | 0.6019289 |
| HMX3 | −0.732825648 | 0.120980991 | 0.047289577 | −6.893929505 | 5.3285264 | 3.8720139 | 3.3243747 | 1.0866873 | 1.2054667 | 0.6019289 |
| PYG01 | −0.731610332 | 0.121504123 | 0.047697986 | −6.893929505 | 3.045043 | 3.8720139 | 6.7371315 | 1.0866873 | 1.2054667 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| RNF4 | −0.746849112 | 0.114273666 | 0.043399663 | −6.917140287 | 10.0155294 | 9.6751249 | 10.148051 | 8.2285993 | 7.2253537 | 0.6019289 |
| C16orf86 | −0.728635031 | 0.123036393 | 0.04857097 | −7.06981506 | 5.0569476 | 3.3213504 | 3.9083598 | 1.0866873 | 1.2054667 | 0.6019289 |
| CCK | −0.728059626 | 0.123245219 | 0.048790018 | −7.06981506 | 3.3509967 | 4.9115166 | 3.9083598 | 1.0866873 | 1.2054667 | 0.6019289 |
| TOR1AIP1 | −0.740044453 | 0.117838959 | 0.04532777 | −7.160851517 | 9.3305229 | 9.1792112 | 9.4997334 | 6.4903918 | 7.7062919 | 0.6019289 |
| REXO2 | −0.747909667 | 0.113710993 | 0.043100377 | −7.168174054 | 10.9911217 | 10.7976487 | 10.616036 | 9.3352666 | 7.956043 | 0.6019289 |
| CNKSR1 | −0.752078898 | 0.111864532 | 0.041977052 | −7.202682103 | 3.3509967 | 5.7897017 | 3.9352215 | 1.0866873 | 1.2054667 | 0.6019289 |
| LOC283553 | −0.737485942 | 0.118571391 | 0.046035465 | −7.202682103 | 5.3044627 | 3.3213504 | 3.9352215 | 1.0866873 | 1.2054667 | 0.6019289 |
| TAL1 | −0.728332919 | 0.123091778 | 0.048645591 | −7.202682103 | 4.963444 | 3.3213504 | 3.9352215 | 1.0866873 | 1.2054667 | 0.6019289 |
| C8orf75 | −0.725502838 | 0.124199978 | 0.049529006 | −7.202682103 | 3.3509967 | 4.7507076 | 3.9352215 | 1.0866873 | 1.2054667 | 0.6019289 |
| NCAPH | −0.724468606 | 0.12468513 | 0.049825082 | −7.202682103 | 4.6820765 | 3.360637 | 3.9352215 | 1.0866873 | 1.2054667 | 0.6019289 |
| MTHFR | −0.776164694 | 0.101257001 | 0.035980101 | −7.253714166 | 11.1831257 | 10.3931195 | 11.8248894 | 8.9661695 | 1.2054667 | 8.5419101 |
| RRAGA | −0.787612446 | 0.097014689 | 0.033562545 | −7.498873168 | 12.2576569 | 11.3560627 | 11.1969823 | 9.8879116 | 1.2054667 | 8.4493889 |
| KDM5C | −0.760571865 | 0.107869852 | 0.039788975 | −7.508375245 | 10.36466 | 10.4612835 | 10.3711388 | 7.4626381 | 1.2054667 | 8.6786124 |
| IL32 | −0.771855276 | 0.103179141 | 0.037053679 | −7.555715522 | 10.0243457 | 9.9614598 | 9.3431532 | 7.6158948 | 1.2054667 | 7.0438915 |
| TNKS1BP1 | −0.749573581 | 0.112884449 | 0.042613 | −7.775239005 | 9.4044234 | 8.8620252 | 9.6366244 | 7.5413002 | 6.4455364 | 0.6019289 |
| DHX9 | −0.779507923 | 0.100080374 | 0.035306908 | −7.793367414 | 10.503547 | 10.1752932 | 10.6357397 | 7.5413002 | 1.2054667 | 8.4493889 |
| XPO1 | −0.745018917 | 0.115280747 | 0.0438851 | −7.877838079 | 10.7341965 | 9.7819266 | 10.637916 | 8.7513276 | 7.6601162 | 0.6019289 |
| RAB14 | −0.859602606 | 0.074257601 | 0.021363235 | −7.97136647 | 12.2165773 | 11.5957841 | 12.002604 | 9.4820885 | 9.0077769 | 2.9963609 |
| MAF1 | −0.827690658 | 0.083401623 | 0.026094038 | −7.972651837 | 12.0702912 | 10.8994373 | 11.3401902 | 8.3967085 | 1.2054667 | 9.0752315 |
| SIRT3 | −0.802328843 | 0.091317418 | 0.03044933 | −8.301227813 | 12.7304926 | 12.8797325 | 12.5081797 | 9.8264078 | 9.7484834 | 8.2221901 |
| PRRX2 | −0.739429303 | 0.1180144 | 0.045481024 | −8.324886536 | 11.4722934 | 10.9146078 | 12.1996331 | 8.4689236 | 7.8571772 | 8.8763623 |
| SRGAP1 | −0.830811354 | 0.082259709 | 0.02560138 | −8.384447916 | 10.1665236 | 10.9262977 | 11.4220281 | 7.8808129 | 8.3543123 | 0.6019289 |
| LRCH1 | −0.738456709 | 0.118223679 | 0.045842093 | −8.422075134 | 10.8328458 | 10.8686094 | 11.6739901 | 5.9133149 | 7.7944336 | 9.1710561 |
| TM4SF1 | −0.743323608 | 0.116287998 | 0.044383375 | −8.453549844 | 13.8777375 | 15.0481396 | 13.513107 | 8.7430302 | 10.9881675 | 11.9685824 |
| FOXQ1 | −0.725855612 | 0.124120257 | 0.04943593 | −8.45924995 | 4.2634629 | 3.3213504 | 4.2859964 | 1.0866873 | 1.2054667 | 0.6019289 |
| ALPP | −0.731089651 | 0.121739156 | 0.047826266 | −8.497462516 | 10.976053 | 11.5659833 | 11.7544238 | 8.4789512 | 9.9394149 | 2.9963609 |
| KHNYN | −0.736988199 | 0.118760034 | 0.046147797 | −8.586415137 | 10.3007843 | 10.8210959 | 10.4599237 | 7.3578678 | 9.4216969 | 0.6019289 |
| SQSTM1 | −0.739446201 | 0.1180144 | 0.045473 | −8.690718017 | 13.6889506 | 13.7153851 | 13.8060905 | 11.4643999 | 10.5959097 | 9.6642224 |
| BTN3A3 | −0.803174961 | 0.091042429 | 0.030252748 | −8.713151242 | 4.2098819 | 3.3213504 | 7.2508437 | 1.0866873 | 1.2054667 | 0.6019289 |
| BMP2K | −0.777172382 | 0.1010258 | 0.035814812 | −8.713151242 | 4.2098819 | 3.3213504 | 6.0125266 | 1.0866873 | 1.2054667 | 0.6019289 |
| KIT | −0.726517285 | 0.123806361 | 0.049249779 | −8.713151242 | 4.2098819 | 4.3513152 | 3.3243747 | 1.0866873 | 1.2054667 | 0.6019289 |
| MCM7 | −0.730604819 | 0.122080069 | 0.048000481 | −8.715781982 | 9.5580365 | 10.2409561 | 10.992779 | 4.8170878 | 7.5630806 | 7.8691489 |
| MYO10 | −0.749778324 | 0.112789349 | 0.042528284 | −8.805157925 | 12.2829797 | 12.0107639 | 12.2259124 | 8.7595777 | 9.6277013 | 9.0875635 |
| PRKAA2 | −0.769263962 | 0.104318244 | 0.03768595 | −8.851049717 | 4.815804 | 4.3513152 | 3.9352215 | 1.6938929 | 1.2054667 | 0.6019289 |
| C1orf106 | −0.798503734 | 0.093373222 | 0.031491615 | −8.951910626 | 3.8399484 | 6.4291897 | 3.7641245 | 1.0866873 | 1.2054667 | 0.6019289 |
| MIR3654 | −0.792079027 | 0.095429111 | 0.032621359 | −8.951910626 | 3.8399484 | 4.7507076 | 3.7641245 | 1.0866873 | 1.2054667 | 0.6019289 |
| GALK2 | −0.782128639 | 0.098981747 | 0.034666613 | −8.951910626 | 5.3285264 | 3.8720139 | 3.7641245 | 1.0866873 | 1.2054667 | 0.6019289 |
| MTHFSD | −0.767221412 | 0.10498791 | 0.038169783 | −8.951910626 | 3.8197323 | 4.9115166 | 3.7641245 | 1.0866873 | 1.2054667 | 0.6019289 |
| ATP2A1 | −0.766509233 | 0.105276608 | 0.038309396 | −8.951910626 | 4.6820765 | 3.8720139 | 3.7641245 | 1.0866873 | 1.2054667 | 0.6019289 |
| SLC6A7 | −0.765130438 | 0.105922473 | 0.038666453 | −8.951910626 | 3.8399484 | 4.7507076 | 3.7641245 | 1.0866873 | 1.2054667 | 0.6019289 |
| PRSS36 | −0.763012467 | 0.106907023 | 0.039254594 | −8.951910626 | 3.8197323 | 4.7507076 | 3.7641245 | 1.0866873 | 1.2054667 | 0.6019289 |
| NUDCD1 | −0.792600071 | 0.09520032 | 0.032527481 | −8.994640793 | 5.4911209 | 3.7709946 | 3.9352215 | 1.0866873 | 1.2054667 | 0.6019289 |
| LRRC14 | −0.788009239 | 0.096821537 | 0.033455829 | −8.994640793 | 5.2636993 | 3.7709946 | 3.9083598 | 1.0866873 | 1.2054667 | 0.6019289 |
| KCNQ3 | −0.786617204 | 0.097552701 | 0.033796839 | −8.994640793 | 5.3285264 | 3.7709946 | 3.9083598 | 1.0866873 | 1.2054667 | 0.6019289 |
| NCKIPSD | −0.78526516 | 0.098120682 | 0.034090508 | −8.994640793 | 5.2636993 | 3.7709946 | 3.7641245 | 1.0866873 | 1.2054667 | 0.6019289 |
| LOC729987 | −0.784664614 | 0.098241201 | 0.034230924 | −8.994640793 | 4.2634629 | 3.7709946 | 4.2859964 | 1.0866873 | 1.2054667 | 0.6019289 |
| FAM186B | −0.763037456 | 0.106907023 | 0.03924657 | −8.994640793 | 3.8197323 | 3.7709946 | 4.7244061 | 1.0866873 | 1.2054667 | 0.6019289 |
| PTCH2 | −0.758577042 | 0.109048772 | 0.040328171 | −8.994640793 | 3.8399484 | 3.7709946 | 4.5083337 | 1.0866873 | 1.2054667 | 0.6019289 |
| NEK1 | −0.754491245 | 0.110509614 | 0.041323116 | −8.994640793 | 3.8197323 | 3.7709946 | 4.4498938 | 1.0866873 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| GPR176 | −0.833023803 | 0.081679166 | 0.025192169 | −9.042838045 | 4.2634629 | 3.7709946 | 5.9741452 | 1.0866873 | 1.2054667 | 0.6019289 |
| R3HDM1 | −0.820485766 | 0.085658176 | 0.027313648 | −9.042838045 | 4.2634629 | 5.3406193 | 3.7641245 | 1.0866873 | 1.2054667 | 0.6019289 |
| TMEM30B | −0.804682097 | 0.090664228 | 0.029984755 | −9.042838045 | 4.2634629 | 7.3033622 | 3.3243747 | 1.0866873 | 1.2054667 | 0.6019289 |
| TMED10P1 | −0.797312014 | 0.093829277 | 0.031734735 | −9.042838045 | 4.2634629 | 3.8720139 | 4.2859964 | 1.0866873 | 1.2054667 | 0.6019289 |
| TOX3 | −0.790781372 | 0.09572616 | 0.032833186 | −9.042838045 | 4.2634629 | 4.4133226 | 3.7641245 | 1.0866873 | 1.2054667 | 0.6019289 |
| PTPDC1 | −0.790781372 | 0.09572616 | 0.032833186 | −9.042838045 | 4.2634629 | 4.4133226 | 3.7641245 | 1.0866873 | 1.2054667 | 0.6019289 |
| GRM2 | −0.767055183 | 0.105041879 | 0.038206692 | −9.042838045 | 4.2634629 | 3.3213504 | 5.3892653 | 1.0866873 | 1.2054667 | 0.6019289 |
| LACC1 | −0.739397345 | 0.1180144 | 0.045530771 | −9.042838045 | 4.2634629 | 3.360637 | 4.4498938 | 1.0866873 | 1.2054667 | 0.6019289 |
| SPC25 | −0.734212844 | 0.120413206 | 0.047028003 | −9.042838045 | 4.2634629 | 3.3213504 | 4.4498938 | 1.0866873 | 1.2054667 | 0.6019289 |
| KDM2A | −0.87790267 | 0.070255881 | 0.019579555 | −9.068082933 | 12.4400298 | 11.9075484 | 12.3047368 | 9.3626047 | 1.2054667 | 9.1239392 |
| TTC21A | −0.811166838 | 0.088696254 | 0.028918398 | −9.091193323 | 4.2634629 | 4.3899364 | 3.9352215 | 1.0866873 | 1.2054667 | 0.6019289 |
| SURF2 | −0.811166838 | 0.088696214 | 0.028918398 | −9.091193323 | 4.2634629 | 4.3899364 | 3.9352215 | 1.0866873 | 1.2054667 | 0.6019289 |
| PIEZO1 | −0.874186213 | 0.070954628 | 0.019926181 | −9.136868614 | 10.260365 | 10.701797 | 10.8041137 | 7.5790795 | 7.6124139 | 0.6019289 |
| EIF5AL1 | −0.728314847 | 0.123091778 | 0.048653615 | −9.162475801 | 14.3208565 | 15.0502399 | 14.2244262 | 11.8545024 | 10.653026 | 11.8432763 |
| ATXN7L2 | −0.831389503 | 0.082162426 | 0.025495467 | −9.185187146 | 5.7530242 | 3.7709946 | 4.2859964 | 1.0866873 | 1.2054667 | 0.6019289 |
| C9orf7 | −0.831239237 | 0.082167973 | 0.025518735 | −9.185187146 | 5.7445127 | 3.7709946 | 4.2859964 | 1.0866873 | 1.2054667 | 0.6019289 |
| BROX | −0.816627968 | 0.086956079 | 0.02799326 | −9.185187146 | 5.0569476 | 3.7709946 | 4.2859964 | 1.0866873 | 1.2054667 | 0.6019289 |
| C10orf28 | −0.800843559 | 0.092139422 | 0.030814411 | −9.185187146 | 3.8399484 | 3.8399484 | 4.2859964 | 1.0866873 | 1.2054667 | 0.6019289 |
| LOC283914 | −0.800210963 | 0.092461329 | 0.030998155 | −9.185187146 | 4.309025 | 3.8720139 | 4.2859964 | 1.0866873 | 1.2054667 | 0.6019289 |
| AGTPBP1 | −0.772064763 | 0.103179141 | 0.037038434 | −9.185187146 | 5.3285264 | 3.3213504 | 4.2859964 | 1.0866873 | 1.2054667 | 0.6019289 |
| NAT6 | −0.748260606 | 0.113494139 | 0.042980823 | −9.185187146 | 4.7435639 | 3.3213504 | 10.6277014 | 8.2982105 | 1.2054667 | 7.0438915 |
| ZNRF1 | −0.75223209 | 0.111864532 | 0.041944957 | −9.222639568 | 10.2490712 | 9.1736173 | 10.9653115 | 6.8092213 | 8.4250552 | 8.0813159 |
| WDR45 | −0.804439806 | 0.090692834 | 0.030032095 | −9.232325976 | 11.6317494 | 11.0672144 | 4.2859964 | 1.0866873 | 1.2054667 | 0.6019289 |
| ZNF771 | −0.8507148 | 0.07656248 | 0.022555564 | −9.239763602 | 4.2634629 | 4.4133226 | 4.2859964 | 1.0866873 | 1.2054667 | 0.6019289 |
| C11orf83 | −0.8507148 | 0.07656248 | 0.022555564 | −9.239763602 | 3.8399484 | 4.4133226 | 4.2859964 | 1.0866873 | 1.2054667 | 0.6019289 |
| CYP27C1 | −0.802090153 | 0.091443132 | 0.030506299 | −9.239763602 | 3.8399484 | 4.4133226 | 4.2859964 | 1.0866873 | 1.2054667 | 0.6019289 |
| LIN9 | −0.799498689 | 0.092882057 | 0.031188317 | −9.239763602 | 3.8197323 | 4.4133226 | 4.2859964 | 1.0866873 | 1.2054667 | 0.6019289 |
| LOC100129931 | −0.799498689 | 0.092882057 | 0.031188317 | −9.239763602 | 3.8197323 | 4.4133226 | 4.2859964 | 1.0866873 | 1.2054667 | 0.6019289 |
| PCSK7 | −0.793828215 | 0.094750565 | 0.032249057 | −9.239763602 | 4.309025 | 4.4133226 | 3.7641245 | 1.0866873 | 1.2054667 | 0.6019289 |
| LOC100506085 | −0.770675867 | 0.103610875 | 0.037328091 | −9.239763602 | 4.7435639 | 4.4133226 | 3.9352215 | 1.6938929 | 1.2054667 | 0.6019289 |
| RNF207 | −0.767532302 | 0.104951556 | 0.03809115 | −9.239763602 | 3.8197323 | 4.4133226 | 3.9083598 | 1.0866873 | 1.2054667 | 0.6019289 |
| TAF10 | −0.879195745 | 0.069835403 | 0.019316676 | −9.251870263 | 11.485123 | 11.6255857 | 11.3159291 | 8.2753779 | 8.7707207 | 0.6019289 |
| LMTK2 | −0.784148926 | 0.098241201 | 0.034302335 | −9.257801408 | 9.6520508 | 9.7782453 | 9.8655896 | 6.5675757 | 7.9750285 | 9.6989376 |
| MAPKAPK2 | −0.73941682 | 0.1180144 | 0.045489048 | −9.260909792 | 12.9100916 | 12.5322853 | 13.4282613 | 10.6746346 | 8.8826529 | 9.6989376 |
| G3BP1 | −0.815129278 | 0.087351733 | 0.02825002 | −9.27360905 | 10.6682266 | 10.7114808 | 11.3810399 | 8.167909 | 6.7399276 | 7.5147138 |
| LTC4S | −0.797878154 | 0.093671851 | 0.03163524 | −9.303692426 | 3.8197323 | 5.4876732 | 3.9352215 | 1.0866873 | 1.2054667 | 0.6019289 |
| MYEOV | −0.796860401 | 0.093970965 | 0.031798122 | −9.303692426 | 3.8197323 | 5.4346801 | 3.9352215 | 1.0866873 | 1.2054667 | 0.6019289 |
| FER1L6-AS1 | −0.792917894 | 0.095066463 | 0.032450453 | −9.303692426 | 3.8197323 | 3.8720139 | 5.5715986 | 1.0866873 | 1.2054667 | 0.6019289 |
| TSPAN15 | −0.782665528 | 0.098744651 | 0.034551071 | −9.303692426 | 3.8197323 | 4.9115166 | 3.9083598 | 1.0866873 | 1.2054667 | 0.6019289 |
| SNORA80B | −0.780040099 | 0.099902938 | 0.035170505 | −9.303692426 | 3.8197323 | 4.8079702 | 3.9083598 | 1.0866873 | 1.2054667 | 0.6019289 |
| CENPC1 | −0.773908381 | 0.10250508 | 0.036609163 | −9.303692426 | 3.8197323 | 3.8720139 | 4.7244061 | 1.0866873 | 1.2054667 | 0.6019289 |
| LOC283731 | −0.73447351 | 0.120231025 | 0.046917275 | −9.303692426 | 4.7435639 | 4.8079702 | 5.5715986 | 2.5373444 | 1.2054667 | 0.6019289 |
| HNRNPH3 | −0.834327813 | 0.110612279 | 0.04138085 | −9.31923649 | 11.7356106 | 10.4817994 | 12.9194344 | 9.6992226 | 9.4007863 | 0.6019289 |
| SYNGR3 | −0.837865016 | 0.079970163 | 0.024401829 | −9.33297891 | 4.309025 | 3.7709946 | 6.0125266 | 1.0866873 | 1.2054667 | 0.6019289 |
| USP48 | −0.815471908 | 0.087217212 | 0.028169783 | −9.33297891 | 4.309025 | 3.360637 | 4.9444683 | 1.0866873 | 1.2054667 | 0.6019289 |
| FOXD1 | −0.790833907 | 0.09572616 | 0.032806708 | −9.33297891 | 4.309025 | 3.360637 | 6.0560619 | 1.0866873 | 1.2054667 | 0.6019289 |
| SRGAP3 | −0.775491546 | 0.101477705 | 0.036125331 | −9.33297891 | 4.309025 | 3.3213504 | 5.3892653 | 1.0866873 | 1.2054667 | 0.6019289 |
| MLLT3 | −0.77062067 | 0.103668192 | 0.037365803 | −9.33297891 | 4.309025 | 3.3213504 | 5.3892653 | 1.0866873 | 1.2054667 | 0.6019289 |
| LOC100616668 | −0.766030864 | 0.105517102 | 0.038449009 | −9.33297891 | 4.309025 | 3.3213504 | 5.2252164 | 1.0866873 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| INVS | −0.739762121 | 0.1179053 | 0.045388751 | −9.33297891 | 4.309025 | 3.3213504 | 4.5083337 | 1.0866873 | 1.2054667 | 0.6019289 |
| COMTD1 | −0.72911852 | 0.122887691 | 0.048439381 | −9.33297891 | 4.309025 | 5.3406193 | 2.2956812 | 1.0866873 | 1.2054667 | 0.6019289 |
| PPARD | −0.881850378 | 0.069778792 | 0.019034743 | −9.350778557 | 10.6905534 | 11.5004644 | 10.9791106 | 8.2753779 | 7.7728978 | 0.6019289 |
| SECISBP2 | −0.791727626 | 0.095488356 | 0.032688759 | −9.403108955 | 11.4787224 | 10.8210959 | 10.4672856 | 1.0866873 | 7.5879581 | 9.2278676 |
| SERPINA1 | −0.821407486 | 0.085414368 | 0.027171628 | −9.434980403 | 3.8399484 | 4.9115166 | 4.2859964 | 1.0866873 | 1.2054667 | 0.6019289 |
| COL11A2 | −0.78805069 | 0.096788354 | 0.033420525 | −9.434980403 | 3.8399484 | 3.8720139 | 5.2176156 | 1.0866873 | 1.2054667 | 0.6019289 |
| GAGE1 | −0.776976992 | 0.101087509 | 0.035853326 | −9.434980403 | 3.8399484 | 3.8720139 | 4.7549172 | 1.0866873 | 1.2054667 | 0.6019289 |
| SLC36A2 | −0.769455295 | 0.104268882 | 0.037633796 | −9.434980403 | 3.8399484 | 3.8720139 | 4.5083337 | 1.0866873 | 1.2054667 | 0.6019289 |
| FLJ31662 | −0.769455295 | 0.104268882 | 0.037633796 | −9.434980403 | 3.8399484 | 3.8720139 | 4.5083337 | 1.0866873 | 1.2054667 | 0.6019289 |
| MLLT11 | −0.767397147 | 0.104951556 | 0.038131269 | −9.434980403 | 3.8399484 | 3.8720139 | 4.4498938 | 1.0866873 | 1.2054667 | 0.6019289 |
| B3GAT3 | −0.852203623 | 0.075942035 | 0.02226029 | −9.47805185 | 9.8828584 | 9.6947857 | 9.1431787 | 6.4501951 | 6.8672984 | 0.6019289 |
| PARP10 | −0.746564495 | 0.11442898 | 0.043485517 | −9.517364112 | 10.2415299 | 9.6711603 | 10.862976 | 6.0805901 | 7.6124139 | 7.3606902 |
| TUBB4B | −0.740204167 | 0.117838959 | 0.045265185 | −9.540072622 | 13.3137451 | 14.69107 | 14.7436225 | 10.1009363 | 12.3033305 | 10.0597448 |
| TAF1L | −0.863423848 | 0.07316741 | 0.020881008 | −9.610609518 | 4.309025 | 4.3513152 | 4.4498938 | 1.0866873 | 1.2054667 | 0.6019289 |
| TRNT1 | −0.827914627 | 0.083196626 | 0.026016208 | −9.610609518 | 3.8399484 | 4.3513152 | 4.9444683 | 1.0866873 | 1.2054667 | 0.6019289 |
| E2F6 | −0.785925601 | 0.097841721 | 0.033945278 | −9.610609518 | 3.3509967 | 4.3513152 | 5.7236017 | 1.0866873 | 1.2054667 | 0.6019289 |
| WDR3 | −0.772568008 | 0.102979156 | 0.036914066 | −9.610609518 | 5.3285264 | 4.3513152 | 3.3243747 | 1.0866873 | 1.2054667 | 0.6019289 |
| RASA2 | −0.756979468 | 0.109559231 | 0.040697264 | −9.610609518 | 3.3509967 | 4.3513152 | 4.7549172 | 1.0866873 | 1.2054667 | 0.6019289 |
| FANCG | −0.728137258 | 0.123231261 | 0.048737062 | −9.610609518 | 2.993831 | 4.3513152 | 5.2252164 | 1.0866873 | 1.2054667 | 0.6019289 |
| KLHL6 | −0.845095305 | 0.077962917 | 0.023263259 | −9.647030648 | 4.2098819 | 3.8720139 | 6.3692392 | 1.0866873 | 1.2054667 | 0.6019289 |
| UBE2Q2P3 | −0.844914243 | 0.07804894 | 0.023301773 | −9.647030648 | 4.2098819 | 3.8720139 | 6.3558005 | 1.0866873 | 1.2054667 | 0.6019289 |
| PARP2 | −0.835041567 | 0.080094735 | 0.024866405 | −9.647030648 | 5.3044627 | 3.8720139 | 4.2859964 | 1.0866873 | 1.2054667 | 0.6019289 |
| TMEM198 | −0.832250094 | 0.082026528 | 0.025339806 | −9.647030648 | 7.4456083 | 3.8720139 | 4.9352215 | 1.0866873 | 1.2054667 | 0.6019289 |
| MED27 | −0.829383499 | 0.082893908 | 0.025826045 | −9.647030648 | 5.0569476 | 3.8720139 | 4.2859964 | 1.0866873 | 1.2054667 | 0.6019289 |
| KIAA1432 | −0.789716433 | 0.096100137 | 0.033008906 | −9.647030648 | 4.963444 | 3.8720139 | 3.9083598 | 1.0866873 | 1.2054667 | 0.6019289 |
| ARID3B | −0.785124582 | 0.098161941 | 0.034120998 | −9.647030648 | 4.6820765 | 3.8720139 | 3.9352215 | 1.0866873 | 1.2054667 | 0.6019289 |
| PRRC2A | −0.898664265 | 0.066663913 | 0.017261494 | −9.647676821 | 11.9466566 | 12.2179049 | 12.0806774 | 9.1655971 | 8.8104958 | 0.6019289 |
| IL10 | −0.810799926 | 0.088793079 | 0.028985798 | −9.740486084 | 6.7078705 | 6.537655 | 7.481604 | 4.1976103 | 3.9031434 | 0.6019289 |
| ESYT1 | −0.846231458 | 0.077708686 | 0.023072294 | −9.77324712 | 11.0266571 | 10.2516151 | 9.7696066 | 7.7378191 | 7.2567201 | 0.6019289 |
| ISM2 | −0.815470463 | 0.087217212 | 0.028177806 | −9.868747668 | 3.8399484 | 4.4133226 | 4.5083337 | 1.0866873 | 1.2054667 | 0.6019289 |
| FANCA | −0.851312069 | 0.076234421 | 0.02240873 | −9.871361236 | 3.8197323 | 4.3899364 | 6.0316576 | 1.0866873 | 1.2054667 | 0.6019289 |
| NR2C2 | −0.845934009 | 0.077792812 | 0.023135682 | −9.871361236 | 3.8399484 | 4.3899364 | 5.5715986 | 1.0866873 | 1.2054667 | 0.6019289 |
| PPEF2 | −0.839746665 | 0.079317736 | 0.024080077 | −9.871361236 | 3.8197323 | 4.3899364 | 5.3892653 | 1.0866873 | 1.2054667 | 0.6019289 |
| TMEM229B | −0.831520299 | 0.082162426 | 0.025448126 | −9.871361236 | 5.3354128 | 4.3899364 | 3.7641245 | 1.0866873 | 1.2054667 | 0.6019289 |
| BEND7 | −0.822024598 | 0.085361525 | 0.027098612 | −9.871361236 | 3.8197323 | 4.3899364 | 4.7549172 | 1.0866873 | 1.2054667 | 0.6019289 |
| NIF3L1 | −0.800318964 | 0.092410962 | 0.030096606 | −9.871361236 | 6.4179694 | 4.3899364 | 3.3243747 | 1.0866873 | 1.2054667 | 0.6019289 |
| BNC1 | −0.795394566 | 0.094440529 | 0.032049266 | −9.871361236 | 3.3509967 | 4.3899364 | 6.0125266 | 1.0866873 | 1.2054667 | 0.6019289 |
| TCF7 | −0.775597441 | 0.101475033 | 0.036107679 | −9.871361236 | 3.0245043 | 4.3899364 | 5.2176156 | 1.0866873 | 1.2054667 | 0.6019289 |
| WNT1 | −0.765288866 | 0.105844907 | 0.038620717 | −9.871361236 | 4.7435639 | 4.3899364 | 6.3692392 | 1.0866873 | 1.2054667 | 0.6019289 |
| MAPK13 | −0.755515067 | 0.110198518 | 0.041050309 | −9.871361236 | 4.6820765 | 4.3899364 | 3.3243747 | 1.0866873 | 1.2054667 | 0.6019289 |
| TSPAN18 | −0.752933419 | 0.111491357 | 0.041176362 | −9.871361236 | 6.7928648 | 4.3899364 | 3.3243747 | 1.0866873 | 1.2054667 | 0.6019289 |
| GLYCTK | −0.871376681 | 0.071618584 | 0.020215037 | −9.893156366 | 6.7928648 | 4.3899364 | 3.9083598 | 1.0866873 | 1.2054667 | 0.6019289 |
| TMEM38B | −0.859759036 | 0.074257601 | 0.021339164 | −9.893156366 | 5.8972917 | 4.3899364 | 3.9083598 | 1.0866873 | 1.2054667 | 0.6019289 |
| ZDHHC24 | −0.852874223 | 0.075772552 | 0.02218567 | −9.893156366 | 5.4911209 | 4.3899364 | 3.9083598 | 1.0866873 | 1.2054667 | 0.6019289 |
| PLCH2 | −0.835056527 | 0.080094735 | 0.024850357 | −9.893156366 | 4.2634629 | 4.3899364 | 3.9083598 | 1.0866873 | 1.2054667 | 0.6019289 |
| ZBTB25 | −0.826240556 | 0.083957582 | 0.026406162 | −9.893156366 | 4.6394091 | 5.1957839 | 3.9083598 | 1.0866873 | 1.2054667 | 0.6019289 |
| MRTO4 | −0.84869977 | 0.077242351 | 0.022806708 | −9.904732109 | 11.0570484 | 4.3513152 | 10.5574232 | 8.180253 | 8.3971729 | 0.6019289 |
| ERLIN1 | −0.783442968 | 0.098499754 | 0.03444917 | −9.914684253 | 11.7048641 | 11.2350596 | 11.7483934 | 7.9254928 | 8.8624022 | 8.3299138 |
| CSF1 | −0.824689172 | 0.084515403 | 0.026637246 | −9.959991289 | 13.0125994 | 12.3595162 | 13.0534609 | 9.7373165 | 9.7206295 | 8.577319 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| TMEM136 | −0.837776017 | 0.080029549 | 0.024433122 | −10.03268119 | 4.815804 | 4.4133226 | 3.9083598 | 1.0866873 | 1.2054667 | 0.6019289 |
| CPSF3 | −0.831802362 | 0.082115651 | 0.025394367 | −10.03268119 | 5.2636993 | 4.4133226 | 3.7641245 | 1.0866873 | 1.2054667 | 0.6019289 |
| FKBP1B | −0.830817699 | 0.082259709 | 0.025593356 | −10.03268119 | 4.6394091 | 4.4133226 | 3.9083598 | 1.0866873 | 1.2054667 | 0.6019289 |
| DOCK4 | −0.787739558 | 0.096975009 | 0.033532857 | −10.03268119 | 3.3509967 | 4.4133226 | 5.5969865 | 1.0866873 | 1.2054667 | 0.6019289 |
| FGF17 | −0.7773037 | 0.1010258 | 0.035798764 | −10.03268119 | 3.3509967 | 4.4133226 | 5.2176156 | 1.0866873 | 1.2054667 | 0.6019289 |
| LMNB1 | −0.743999802 | 0.115827669 | 0.044131429 | −10.03268119 | 2.993831 | 4.4133226 | 5.5969865 | 1.0866873 | 1.2054667 | 0.6019289 |
| TOMM40L | −0.741090637 | 0.11759359 | 0.045036508 | −10.03268119 | 5.4911209 | 4.4133226 | 2.9956812 | 1.0866873 | 1.2054667 | 0.6019289 |
| KAZN | −0.838725782 | 0.07961428 | 0.02426703 | −10.06621054 | 10.5285503 | 10.6643939 | 9.6963177 | 7.1971015 | 7.7944336 | 0.6019289 |
| WASF3 | −0.871844424 | 0.071557972 | 0.020178127 | −10.07908406 | 6.8998234 | 4.3513152 | 3.9352215 | 1.0866873 | 1.2054667 | 0.6019289 |
| OSGIN1 | −0.855121163 | 0.075307325 | 0.021979459 | −10.07908406 | 5.3285264 | 4.4133226 | 3.9352215 | 1.0866873 | 1.2054667 | 0.6019289 |
| LOC401164 | −0.853867831 | 0.075520715 | 0.022099815 | −10.07908406 | 4.309025 | 5.8096013 | 3.9352215 | 1.0866873 | 1.2054667 | 0.6019289 |
| MMEL1 | −0.841739307 | 0.078901035 | 0.023755918 | −10.07908406 | 4.2634629 | 5.3621423 | 3.9352215 | 1.0866873 | 1.2054667 | 0.6019289 |
| IMP4 | −0.833112659 | 0.081670717 | 0.025176121 | −10.07908406 | 4.309025 | 4.8304956 | 3.9352215 | 1.0866873 | 1.2054667 | 0.6019289 |
| KCNRG | −0.831442613 | 0.082162426 | 0.025475407 | −10.07908406 | 4.6820765 | 4.3513152 | 3.9352215 | 1.0866873 | 1.2054667 | 0.6019289 |
| GNRHR2 | −0.831442613 | 0.082162426 | 0.025475407 | −10.07908406 | 4.6820765 | 4.3513152 | 3.9352215 | 1.0866873 | 1.2054667 | 0.6019289 |
| FAM212A | −0.831412674 | 0.082162426 | 0.025487443 | −10.07908406 | 4.2634629 | 4.9115166 | 3.9352215 | 1.0866873 | 1.2054667 | 0.6019289 |
| FOXP3 | −0.830494188 | 0.08237599 | 0.025651127 | −10.07908406 | 4.309025 | 4.7507076 | 3.9352215 | 1.0866873 | 1.2054667 | 0.6019289 |
| IL17RC | −0.829072426 | 0.08292734 | 0.025850116 | −10.07908406 | 4.2634629 | 4.8304956 | 3.9352215 | 1.0866873 | 1.2054667 | 0.6019289 |
| SLC16A12 | −0.826552827 | 0.083748845 | 0.026326727 | −10.07908406 | 4.2634629 | 4.7507076 | 3.9352215 | 1.0866873 | 1.2054667 | 0.6019289 |
| XRCC3 | −0.824141777 | 0.084705069 | 0.026752788 | −10.07908406 | 4.2098819 | 4.8304956 | 3.9352215 | 1.0866873 | 1.2054667 | 0.6019289 |
| RPP30 | −0.727957261 | 0.123245219 | 0.048823718 | −10.07908406 | 4.6394091 | 5.4346801 | 3.9352215 | 1.0866873 | 2.5373444 | 0.6019289 |
| FAM3A | −0.834979721 | 0.080994735 | 0.024874428 | −10.14075402 | 11.0599097 | 10.0526605 | 9.9555834 | 6.7105675 | 8.3687411 | 2.9636609 |
| PAWR | −0.728330719 | 0.123091778 | 0.048661638 | −10.24215848 | 7.7590076 | 10.2030168 | 9.0805542 | 5.7241063 | 7.6601162 | 0.6019289 |
| MAP4K4 | −0.79879715 | 0.093160485 | 0.031339164 | −10.28043139 | 12.1933119 | 12.0997301 | 12.5549798 | 9.6644958 | 8.831483 | 8.4106527 |
| GMDS | −0.856826964 | 0.074799231 | 0.021691407 | −10.29025241 | 3.8197323 | 6.0361098 | 4.4498938 | 1.0866873 | 1.2054667 | 0.6019289 |
| TMEM169 | −0.808651446 | 0.089424388 | 0.029324244 | −10.29025241 | 6.3818471 | 3.360637 | 4.4498938 | 1.0866873 | 1.2054667 | 0.6019289 |
| PIK3C2B | −0.772692948 | 0.109243446 | 0.036877156 | −10.29025241 | 4.963444 | 3.360637 | 4.4498938 | 1.0866873 | 1.2054667 | 0.6019289 |
| ST3GAL1 | −0.824654588 | 0.084680705 | 0.026671748 | −10.3055564 | 11.4108658 | 11.9718106 | 12.618667 | 10.1582229 | 8.6064601 | 0.6019289 |
| DAZAP2 | −0.855274416 | 0.075282272 | 0.021955388 | −10.36456829 | 13.870218 | 13.016869 | 12.862876 | 9.8765776 | 9.4892879 | 9.8799953 |
| AKIRIN2 | −0.89622438 | 0.066907118 | 0.017544732 | −10.46571833 | 11.2447766 | 11.22833 | 11.79692 | 8.5848861 | 7.8571772 | 2.9636609 |
| HIVEP2 | −0.856950919 | 0.074758653 | 0.021667335 | −10.60698699 | 10.36466 | 11.1132349 | 11.4765505 | 8.4889095 | 7.7062919 | 0.6019289 |
| PRSS21 | −0.893989691 | 0.067225527 | 0.017730883 | −10.71564202 | 3.8399484 | 8.9099134 | 4.5083337 | 1.0866873 | 1.2054667 | 0.6019289 |
| RHPN1 | −0.837017112 | 0.080350378 | 0.024573945 | −10.71564202 | 4.7435639 | 3.8720139 | 4.5083337 | 1.0866873 | 1.2054667 | 0.6019289 |
| NUDT15 | −0.769089119 | 0.1044167 | 0.037782235 | −10.71564202 | 3.3509967 | 4.8079702 | 4.5083337 | 1.0866873 | 1.2054667 | 0.6019289 |
| MPHOSPH9 | −0.767619169 | 0.104951556 | 0.038067079 | −10.71564202 | 4.7435639 | 3.360637 | 4.5083337 | 1.0866873 | 1.2054667 | 0.6019289 |
| ELMO1 | −0.76485949 | 0.106046107 | 0.038729038 | −10.71564202 | 4.6820765 | 3.360637 | 4.5083337 | 1.0866873 | 1.2054667 | 0.6019289 |
| ANKRD11 | −0.779956837 | 0.099902938 | 0.035186552 | −10.74746309 | 12.1266449 | 12.4918369 | 12.3285117 | 9.7825497 | 8.7007207 | 8.8476482 |
| LOC339524 | −0.894728733 | 0.067157603 | 0.017662682 | −10.8073613 | 4.6394091 | 4.4133226 | 4.4498938 | 1.0866873 | 1.2054667 | 0.6019289 |
| SUV39H1 | −0.894728733 | 0.067157603 | 0.017662682 | −10.8073613 | 4.6394091 | 4.4133226 | 4.4498938 | 1.0866873 | 1.2054667 | 0.6019289 |
| SYN1 | −0.902520879 | 0.065854333 | 0.016897216 | −11.13175989 | 4.6820765 | 4.4133226 | 4.5083337 | 1.0866873 | 1.2054667 | 0.6019289 |
| NES | −0.758396098 | 0.109168569 | 0.040408409 | −11.18458928 | 11.3490472 | 13.189984 | 13.1850455 | 7.8656068 | 9.1398349 | 10.1329672 |
| MRPL32 | −0.8823 8114 | 0.069332647 | 0.019010672 | −11.22155263 | 11.7048641 | 12.2823483 | 12.0076619 | 8.2166637 | 8.3397377 | 8.833074 |
| PDIA3 | −0.775006043 | 0.101834075 | 0.036268956 | −11.25375614 | 7.4279993 | 6.270596 | 6.0125266 | 4.5400907 | 1.2054667 | 2.7782613 |
| ECM1 | −0.918277657 | 0.063260715 | 0.015627858 | −11.28230098 | 10.8691867 | 10.2329098 | 10.4843186 | 6.988347 | 7.5120008 | 0.6019289 |
| HLA-B | −0.886920836 | 0.068365464 | 0.018485116 | −11.36234947 | 16.466846 | 16.263629 | 15.5959348 | 12.1313726 | 12.8596921 | 12.9606567 |
| UBE2I1 | −0.891892727 | 0.067604226 | 0.017980422 | −11.43569008 | 12.1550212 | 11.1161542 | 11.1280543 | 8.6395496 | 8.0305306 | 0.6019289 |
| LOC100628307 | −0.872785081 | 0.071297709 | 0.020065795 | −11.46321176 | 4.2098819 | 4.4133226 | 4.7244061 | 1.0866873 | 1.2054667 | 0.6019289 |
| PSMB2 | −0.864922686 | 0.072798529 | 0.02073979 | −11.49048458 | 12.837747 | 12.6099312 | 11.3308037 | 9.5924293 | 1.2054667 | 9.0875635 |
| WHSC2 | −0.876489201 | 0.070539978 | 0.019748054 | −11.56040292 | 4.2098819 | 4.7365865 | 4.4498938 | 1.0866873 | 1.2054667 | 0.6019289 |

TABLE 9-continued

Differentially Expressed Genes in CD10-, CD24-, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| PAQR5 | -0.816320908 | 0.086958113 | 0.028041403 | -11.56040292 | 5.3162271 | 4.7365865 | 3.9083598 | 1.6938929 | 1.2054667 | 0.6019289 |
| RGS12 | -0.85632049 | 0.074889306 | 0.02176683 | -11.61300118 | 9.8065464 | 4.6341645 | 10.8814627 | 7.0964955 | 7.956043 | 0.6019289 |
| CENPL | -0.844281161 | 0.078284823 | 0.023423734 | -11.61644899 | 4.7435639 | 4.9115166 | 4.2859964 | 1.6938929 | 1.2054667 | 0.6019289 |
| METTL11A | -0.740936492 | 0.117655882 | 0.045099093 | -11.65975483 | 10.2565732 | 9.7256961 | 9.7252629 | 6.1822306 | 1.2054667 | 8.932131 |
| LOC388588 | -0.843083808 | 0.078689412 | 0.023640376 | -11.6741118 | 3.8197323 | 4.7507076 | 4.7244061 | 1.0866873 | 1.2054667 | 0.6019289 |
| NOL9 | -0.836326587 | 0.080597949 | 0.024699511 | -11.6741118 | 4.7435639 | 4.7507076 | 3.7641245 | 1.0866873 | 1.2054667 | 0.6019289 |
| HIPK2 | -0.806974555 | 0.090048446 | 0.029596405 | -11.69279133 | 11.5858346 | 10.4287786 | 9.3107812 | 8.0382872 | 7.5630806 | 0.6019289 |
| HYAL4 | -0.844676871 | 0.078078462 | 0.023323437 | -11.70822562 | 3.8197323 | 4.7507076 | 4.7549172 | 1.0866873 | 1.2054667 | 0.6019289 |
| LOC284551 | -0.843940366 | 0.078442556 | 0.02349675 | -11.70822562 | 3.8197323 | 4.7365865 | 4.7549172 | 1.0866873 | 1.2054667 | 0.6019289 |
| DUSP11 | -0.837499289 | 0.080180061 | 0.024494103 | -11.70822562 | 4.7435639 | 3.7709946 | 4.7549172 | 1.0866873 | 1.2054667 | 0.6019289 |
| C12orf59 | -0.912981555 | 0.064158575 | 0.016018615 | -11.73480352 | 4.6394091 | 4.3899364 | 4.7244061 | 1.0866873 | 1.2054667 | 0.6019289 |
| AP1S3 | -0.909991271 | 0.064756039 | 0.016359624 | -11.73480352 | 4.6394091 | 4.3513152 | 4.7549172 | 1.0866873 | 1.2054667 | 0.6019289 |
| TMEM108 | -0.869893387 | 0.071778384 | 0.020346626 | -11.73480352 | 4.6394091 | 5.297868 | 3.9083598 | 1.0866873 | 1.2054667 | 0.6019289 |
| TMCO6 | -0.858233419 | 0.07443975 | 0.021498034 | -11.73480352 | 4.6394091 | 3.7709946 | 5.5715986 | 1.0866873 | 1.2054667 | 0.6019289 |
| BARX2 | -0.85163589 | 0.076222506 | 0.022384659 | -11.73480352 | 4.6394091 | 5.3406193 | 3.7641245 | 1.0866873 | 1.2054667 | 0.6019289 |
| ADORA3 | -0.805634209 | 0.090331212 | 0.029778544 | -11.73480352 | 4.6394091 | 3.360637 | 5.5969865 | 1.0866873 | 1.2054667 | 0.6019289 |
| PLEKHN1 | -0.774750635 | 0.101915392 | 0.036314691 | -11.73480352 | 4.6394091 | 6.1390574 | 2.9956812 | 1.0866873 | 1.2054667 | 0.6019289 |
| ARHGEF16 | -0.730806987 | 0.122051571 | 0.047969189 | -11.73480352 | 4.6394091 | 4.8304956 | 2.9956812 | 1.0866873 | 1.2054667 | 0.6019289 |
| NOTCH2 | -0.8151801 | 0.087291954 | 0.02821632 | -12.00940689 | 10.7852289 | 12.0162438 | 12.2964944 | 9.7077753 | 1.2054667 | 8.4301508 |
| GLO1 | -0.890477608 | 0.067913831 | 0.018147316 | -12.0679301 | 13.2352334 | 13.0378039 | 11.663346 | 9.690619 | 1.2054667 | 9.4446975 |
| DSP | -0.908220827 | 0.065023856 | 0.016448688 | -12.08704063 | 4.6820765 | 7.6317881 | 3.9352215 | 1.0866873 | 1.2054667 | 0.6019289 |
| SENP7 | -0.884133097 | 0.068843868 | 0.018786007 | -12.08704063 | 4.6820765 | 3.8720139 | 6.0721689 | 1.0866873 | 1.2054667 | 0.6019289 |
| PUS7 | -0.809142718 | 0.08931343 | 0.029266629 | -12.08704063 | 4.6820765 | 5.7897017 | 3.3243747 | 1.0866873 | 1.2054667 | 0.6019289 |
| IGSF21 | -0.773209859 | 0.102731018 | 0.036775255 | -12.08704063 | 4.6820765 | 2.8096013 | 6.861515 | 1.0866873 | 1.2054667 | 0.6019289 |
| LOC285965 | -0.885841557 | 0.068486123 | 0.018609484 | -12.14679241 | 4.2634629 | 4.8079702 | 4.4498938 | 1.0866873 | 1.2054667 | 0.6019289 |
| LEAP2 | -0.885841557 | 0.068486123 | 0.018609484 | -12.14679241 | 4.2634629 | 4.8079702 | 4.4498938 | 1.0866873 | 1.2054667 | 0.6019289 |
| KIAA0391 | -0.839162193 | 0.079358501 | 0.024149884 | -12.14679241 | 4.7435639 | 4.8079702 | 3.7641245 | 1.0866873 | 1.2054667 | 0.6019289 |
| PKP2 | -0.920126875 | 0.062956501 | 0.01548022 | -12.19276133 | 4.2098819 | 7.3437697 | 4.5083337 | 1.0866873 | 1.2054667 | 0.6019289 |
| LRRC1 | -0.912519193 | 0.064224388 | 0.016058734 | -12.19276133 | 4.2098819 | 6.3911446 | 4.5083337 | 1.0866873 | 1.2054667 | 0.6019289 |
| HLA-DOB | -0.897978406 | 0.066685485 | 0.017300008 | -12.19276133 | 4.2098819 | 4.7365865 | 4.7549172 | 1.0866873 | 1.2054667 | 0.6019289 |
| CIDEB | -0.897026531 | 0.066827455 | 0.017438819 | -12.19276133 | 4.2098819 | 4.7507076 | 4.7244061 | 1.6938929 | 1.2054667 | 0.6019289 |
| ZSCAN12P1 | -0.891088835 | 0.067801994 | 0.018091952 | -12.19276133 | 4.2098819 | 4.3899364 | 5.5929159 | 1.0866873 | 1.2054667 | 0.6019289 |
| RAD52 | -0.88039878 | 0.069612081 | 0.01918238 | -12.19276133 | 4.2098819 | 4.4133226 | 4.9444683 | 1.0866873 | 1.2054667 | 0.6019289 |
| C10orf6 | -0.880133946 | 0.069663629 | 0.01921608 | -12.19276133 | 4.2098819 | 4.8304956 | 4.4498938 | 1.0866873 | 1.2054667 | 0.6019289 |
| PEX13 | -0.87845895 | 0.070105249 | 0.019464816 | -12.19276133 | 4.2098819 | 5.4876732 | 4.2859964 | 1.0866873 | 1.2054667 | 0.6019289 |
| PANK3 | -0.878124667 | 0.070226005 | 0.019533018 | -12.19276133 | 4.2098819 | 4.3899364 | 4.9444683 | 1.0866873 | 1.2054667 | 0.6019289 |
| CNGB1 | -0.906468901 | 0.065320795 | 0.01664206 | -12.21292904 | 4.815804 | 4.7435639 | 4.5083337 | 1.0866873 | 1.2054667 | 0.6019289 |
| CPLX1 | -0.860132739 | 0.073977368 | 0.021246088 | -12.21292904 | 4.815804 | 4.7507076 | 3.9083598 | 1.0866873 | 1.2054667 | 0.6019289 |
| JRKL | -0.77765297 | 0.100926453 | 0.035705689 | -12.21292904 | 4.815804 | 3.3213504 | 4.7244061 | 1.0866873 | 1.2054667 | 0.6019289 |
| NFATC2IP | -0.826832706 | 0.083627111 | 0.026260932 | -12.31491054 | 5.3162271 | 4.3513152 | 4.2859964 | 1.6938929 | 1.2054667 | 0.6019289 |
| BPGM | -0.936238501 | 0.0607352 | 0.014274252 | -12.33793384 | 4.6820765 | 4.8304956 | 4.5083337 | 1.0866873 | 1.2054667 | 0.6019289 |
| SPDEF | -0.844040402 | 0.078399915 | 0.023471074 | -12.33793384 | 4.7435639 | 4.8304956 | 3.7641245 | 1.0866873 | 1.2054667 | 0.6019289 |
| CDK7 | -0.840233259 | 0.079229335 | 0.024006259 | -12.33793384 | 4.7435639 | 4.3899364 | 3.7641245 | 1.0866873 | 1.2054667 | 0.6019289 |
| ZYG11A | -0.740624937 | 0.117680421 | 0.045147236 | -12.33793384 | 3.0245043 | 4.8304956 | 4.7549172 | 1.0866873 | 1.2054667 | 0.6019289 |
| PSORS1C3 | -0.739937177 | 0.117838959 | 0.045343818 | -12.33793384 | 4.815804 | 4.8304956 | 2.9956812 | 1.0866873 | 1.2054667 | 0.6019289 |
| OSCP1 | -0.948693574 | 0.059219172 | 0.013383616 | -12.4469363 | 4.6394091 | 4.7507076 | 4.7244061 | 1.0866873 | 1.2054667 | 0.6019289 |
| KLRD1 | -0.919274002 | 0.0631711 | 0.01555083 | -12.4469363 | 4.815804 | 4.3513152 | 4.7244061 | 1.6938929 | 1.2054667 | 0.6019289 |
| GGT8P | -0.889099657 | 0.069560685 | 0.019118992 | -12.4469363 | 5.7003762 | 3.8720139 | 4.7244061 | 1.0866873 | 1.2054667 | 0.6019289 |
| SRCRB4D | -0.859480022 | 0.074270892 | 0.021379283 | -12.4469363 | 3.8197323 | 5.1480825 | 4.7244061 | 1.0866873 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| TMEM180 | −0.758472976 | 0.109154239 | 0.04038514 | −12.4469363 | 3.045043 | 5.297868 | 4.7244061 | 1.0866873 | 1.2054667 | 0.6019289 |
| LMAN2L | −0.78123052 | 0.099549317 | 0.034906523 | −12.52486855 | 9.7790278 | 9.6947857 | 9.8655896 | 6.1323043 | 1.2054667 | 8.2877844 |
| ZNF395 | −0.880010734 | 0.069702623 | 0.019241756 | −12.5252262 | 12.2223355 | 10.4051041 | 10.2340031 | 8.5755707 | 7.0925914 | 0.6019289 |
| MIR600HG | −0.934993454 | 0.060960411 | 0.014375351 | −12.552468 | 4.2098819 | 4.7365865 | 6.4105447 | 1.0866873 | 1.2054667 | 0.6019289 |
| LOC100287036 | −0.798413914 | 0.093373222 | 0.031503651 | −12.552468 | 5.3044627 | 4.7365865 | 3.3243747 | 1.0866873 | 1.2054667 | 0.6019289 |
| ACAD9 | −0.798413914 | 0.093373222 | 0.031503651 | −12.552468 | 5.3044627 | 4.7365865 | 3.3243747 | 1.0866873 | 1.2054667 | 0.6019289 |
| ASB7 | −0.785341092 | 0.098120682 | 0.03407446 | −12.552468 | 4.963444 | 4.7365865 | 3.3243747 | 1.0866873 | 1.2054667 | 0.6019289 |
| GRK4 | −0.782157826 | 0.098981747 | 0.034658589 | −12.552468 | 2.993831 | 4.7365865 | 6.1759311 | 1.0866873 | 1.2054667 | 0.6019289 |
| C4orf48 | −0.769100631 | 0.1044167 | 0.037774212 | −12.552468 | 5.7003762 | 4.7365865 | 2.9956812 | 1.0866873 | 1.2054667 | 0.6019289 |
| C9orf69 | −0.959604504 | 0.058066829 | 0.012826767 | −12.6133237 | 4.7435639 | 4.7365865 | 4.7549172 | 1.0866873 | 1.2054667 | 0.6019289 |
| KRTCAP3 | −0.896768841 | 0.066883613 | 0.017480542 | −12.6133237 | 4.7435639 | 6.036109 | 3.9352215 | 1.0866873 | 1.2054667 | 0.6019289 |
| KCNK1 | −0.857882763 | 0.074452862 | 0.0215542 | −12.6133237 | 4.7435639 | 5.297868 | 3.7641245 | 1.0866873 | 7.5879581 | 0.6019289 |
| FAM189A2 | −0.843312966 | 0.078689412 | 0.023609885 | −12.6133237 | 4.7435639 | 7.3237074 | 3.3243747 | 1.0866873 | 1.2054667 | 0.6019289 |
| DCP1B | −0.806172723 | 0.090230223 | 0.029730402 | −12.6133237 | 4.7435639 | 3.3213504 | 5.5446534 | 1.0866873 | 1.2054667 | 0.6019289 |
| PRDX6 | −0.831630078 | 0.082162426 | 0.025440103 | −12.62026134 | 14.5181455 | 13.702332 | 14.1130677 | 11.5079002 | 10.4542551 | 9.32481 |
| DCK | −0.91038203 | 0.064737869 | 0.016320308 | −12.65410906 | 4.2634629 | 4.8304956 | 4.7549172 | 1.0866873 | 1.2054667 | 0.6019289 |
| LOC285456 | −0.886537401 | 0.068460049 | 0.01855733 | −12.65410906 | 4.2634629 | 4.3899364 | 5.018694 | 1.0866873 | 1.2054667 | 0.6019289 |
| GPC2 | −0.883677564 | 0.068960631 | 0.018840568 | −12.65410906 | 4.2634629 | 5.4346801 | 4.2859964 | 1.0866873 | 1.2054667 | 0.6019289 |
| POLR2H | −0.854594887 | 0.075433888 | 0.022041242 | −12.65848286 | 9.892521 | 10.0708307 | 9.5788924 | 6.2304884 | 7.5879581 | 0.6019289 |
| C9orf9 | −0.939304704 | 0.060301826 | 0.014063227 | −12.6759349 | 4.2634629 | 4.7507076 | 6.0540376 | 1.0866873 | 1.2054667 | 0.6019289 |
| GDPD3 | −0.927752976 | 0.061660694 | 0.014897697 | −12.6759349 | 4.2098819 | 4.7507076 | 5.7029118 | 1.0866873 | 1.2054667 | 0.6019289 |
| HLA-DOA | −0.925044742 | 0.061862376 | 0.015068603 | −12.6759349 | 4.7435639 | 4.7507076 | 5.2252164 | 1.0866873 | 1.2054667 | 0.6019289 |
| NRON | −0.915440474 | 0.063593959 | 0.015804381 | −12.6759349 | 4.2634629 | 4.7507076 | 4.9444683 | 1.0866873 | 1.2054667 | 0.6019289 |
| PADI2 | −0.915440474 | 0.063593959 | 0.015804381 | −12.6759349 | 4.2634629 | 4.7507076 | 4.9444683 | 1.0866873 | 1.2054667 | 0.6019289 |
| FAM120C | −0.897628097 | 0.066707952 | 0.01735777 | −12.6759349 | 3.8399484 | 4.7507076 | 6.9482372 | 1.0866873 | 1.2054667 | 0.6019289 |
| LOC650368 | −0.891607202 | 0.067647212 | 0.018006098 | −12.6759349 | 5.8972917 | 4.7507076 | 3.9083598 | 1.0866873 | 1.2054667 | 0.6019289 |
| GRPEL2 | −0.870351383 | 0.071746883 | 0.020298484 | −12.6759349 | 5.0569476 | 4.7507076 | 3.9083598 | 1.0866873 | 1.2054667 | 0.6019289 |
| PIK3CG | −0.771773186 | 0.1031674 | 0.037084169 | −12.6759349 | 4.309025 | 4.7507076 | 5.3892653 | 1.0866873 | 2.5373444 | 0.6019289 |
| LOC100506746 | −0.888404792 | 0.068142722 | 0.018354329 | −12.71297622 | 6.8201191 | 3.7709946 | 4.7549172 | 1.0866873 | 1.2054667 | 0.6019289 |
| HBA1 | −0.795136179 | 0.094440529 | 0.032073337 | −12.71297622 | 5.0569476 | 3.360637 | 4.7549172 | 1.0866873 | 6.9463683 | 9.5284972 |
| DUOX2 | −0.779733164 | 0.099997455 | 0.035236299 | −12.71297622 | 2.993831 | 6.0361098 | 4.7549172 | 1.0866873 | 1.2054667 | 0.6019289 |
| BSPRY | −0.763131727 | 0.106854219 | 0.039200032 | −12.71297622 | 2.993831 | 5.4867322 | 4.7549172 | 1.0866873 | 1.2054667 | 0.6019289 |
| C3orf70 | −0.734549997 | 0.120170675 | 0.046873947 | −12.71297622 | 5.3354128 | 2.8096013 | 4.7549172 | 1.0866873 | 1.2054667 | 0.6019289 |
| ABL1 | −0.858010142 | 0.07443975 | 0.021538153 | −12.80884394 | 13.4222343 | 12.9804873 | 13.2075656 | 10.6370662 | 6.8092213 | 9.5284972 |
| C1orf130 | −0.942275574 | 0.059921626 | 0.013856214 | −12.85330548 | 4.6820765 | 6.8774542 | 4.2859964 | 1.0866873 | 1.2054667 | 0.6019289 |
| KIAA0226L | −0.934761475 | 0.060960411 | 0.014391399 | −12.85330548 | 4.6394091 | 6.4291897 | 4.2859964 | 1.0866873 | 1.2054667 | 0.6019289 |
| LOC728342 | −0.929508507 | 0.061440918 | 0.014763701 | −12.85330548 | 5.3285264 | 4.7365865 | 4.2859964 | 1.0866873 | 1.2054667 | 0.6019289 |
| ANO6 | −0.871677277 | 0.071557972 | 0.020186151 | −12.90661826 | 9.0659928 | 9.4437316 | 9.2664566 | 6.8092213 | 5.5764175 | 0.6019289 |
| KIAA0368 | −0.930883897 | 0.061288269 | 0.014686673 | −12.92961805 | 11.2990651 | 11.5182291 | 12.0613488 | 8.2285993 | 8.3687411 | 0.6019289 |
| RPL9 | −0.878805649 | 0.069923269 | 0.01937174 | −12.93422083 | 16.3882771 | 17.3519057 | 16.8579231 | 12.69515559 | 13.5064231 | 13.481798 |
| BCAR1 | −0.833396415 | 0.081552171 | 0.025112734 | −12.95946304 | 10.2665157 | 11.1306625 | 10.7885254 | 6.2304884 | 7.0925914 | 8.0311264 |
| PRLR | −0.972502034 | 0.056976583 | 0.012094199 | −13.05065106 | 4.7435639 | 4.9115166 | 4.7549172 | 1.0866873 | 1.2054667 | 0.6019289 |
| B3GALT4 | −0.945420587 | 0.059597087 | 0.013641178 | −13.05065106 | 4.7435639 | 4.9115166 | 4.5083337 | 1.0866873 | 1.2054667 | 0.6019289 |
| AKR7A3 | −0.940283633 | 0.060114874 | 0.013991816 | −13.05065106 | 4.6820765 | 4.9115166 | 4.5083337 | 1.0866873 | 1.2054667 | 0.6019289 |
| ITK | −0.954988566 | 0.05844483 | 0.013024151 | −13.06011811 | 4.309025 | 4.7507076 | 7.5008617 | 1.0866873 | 1.2054667 | 0.6019289 |
| S100A13 | −0.936482812 | 0.060682102 | 0.014243762 | −13.06011811 | 4.309025 | 5.4346801 | 4.7549172 | 1.0866873 | 1.2054667 | 0.6019289 |
| QDPR | −0.920616954 | 0.062815622 | 0.015416834 | −13.06011811 | 4.309025 | 4.7365865 | 4.9444683 | 1.0866873 | 1.2054667 | 0.6019289 |
| NKX3-1 | −0.918694632 | 0.063231386 | 0.015602182 | −13.06011811 | 4.309025 | 6.5023977 | 4.4499388 | 1.0866873 | 1.2054667 | 0.6019289 |
| PDE12 | −0.911163958 | 0.06461959 | 0.016232047 | −13.06011811 | 4.309025 | 5.3406193 | 4.5083337 | 1.0866873 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| LOC286184 | −0.907179176 | 0.065205844 | 0.016569847 | −13.06011811 | 4.309025 | 5.1480825 | 4.5083337 | 1.0866873 | 1.2054667 | 0.6019289 |
| SERPINC1 | −0.894316682 | 0.067193151 | 0.017697184 | −13.06011811 | 4.309025 | 4.4133226 | 5.018694 | 1.0866873 | 1.2054667 | 0.6019289 |
| TRAF7 | −0.926313084 | 0.061745969 | 0.014999599 | −13.11118079 | 11.503105 | 11.3006838 | 10.4599237 | 7.9400838 | 7.5879581 | 0.6019289 |
| SMAD6 | −0.938047619 | 0.060391495 | 0.014133836 | −13.18917896 | 4.2634629 | 4.8079702 | 5.5929159 | 1.0866873 | 1.2054667 | 0.6019289 |
| RHBDL1 | −0.937823607 | 0.060554615 | 0.014181979 | −13.18917896 | 4.2098819 | 4.8079702 | 6.0560619 | 1.0866873 | 1.2054667 | 0.6019289 |
| RAB17 | −0.933771022 | 0.061000896 | 0.014469229 | −13.18917896 | 5.2639993 | 4.8079702 | 4.2859964 | 1.0866873 | 1.2054667 | 0.6019289 |
| TNIK | −0.930914053 | 0.061288269 | 0.014678649 | −13.18917896 | 4.2098819 | 4.8079702 | 5.5969865 | 1.0866873 | 1.2054667 | 0.6019289 |
| WDR46 | −0.897053947 | 0.066827455 | 0.017423574 | −13.18917896 | 5.7530242 | 4.8079702 | 3.9352215 | 1.0866873 | 1.2054667 | 0.6019289 |
| SNX4 | −0.896883849 | 0.066827455 | 0.017454866 | −13.18917896 | 5.7445127 | 4.8079702 | 3.9352215 | 1.0866873 | 1.2054667 | 0.6019289 |
| KIAA1737 | −0.886856725 | 0.068363464 | 0.018501163 | −13.18917896 | 5.3285264 | 4.8079702 | 3.9352215 | 1.0866873 | 1.2054667 | 0.6019289 |
| C3orf17 | −0.884909513 | 0.068629673 | 0.018696943 | −13.18917896 | 5.2639993 | 4.8079702 | 3.9352215 | 1.0866873 | 1.2054667 | 0.6019289 |
| CCM2 | −0.88241271 | 0.069332647 | 0.019002648 | −13.18917896 | 5.3044627 | 4.8079702 | 3.9083598 | 1.0866873 | 1.2054667 | 0.6019289 |
| SLC45A1 | −0.876539684 | 0.070539978 | 0.0197400 | −13.18917896 | 5.8565586 | 4.9115166 | 3.7641245 | 1.0866873 | 1.2054667 | 0.6019289 |
| LOC646329 | −0.859628068 | 0.074257601 | 0.021355211 | −13.18917896 | 3.8399484 | 5.4876732 | 4.9444683 | 1.0866873 | 1.2054667 | 0.6019289 |
| MFSD9 | −0.827594489 | 0.08341132 | 0.026116505 | −13.18917896 | 6.186289 | 4.8079702 | 3.3243747 | 1.0866873 | 1.2054667 | 0.6019289 |
| LOC100507034 | −0.789210257 | 0.096254372 | 0.033125251 | −13.18917896 | 4.963444 | 4.8079702 | 5.5929159 | 1.0866873 | 1.2054667 | 0.6019289 |
| DNAJC6 | −0.761086301 | 0.107598348 | 0.039667817 | −13.18917896 | 5.3354128 | 4.8079702 | 2.9956812 | 1.0866873 | 1.2054667 | 0.6019289 |
| MCART1 | −0.76036557 | 0.107936957 | 0.039845944 | −13.18917896 | 5.3162271 | 4.8079702 | 2.9956812 | 1.0866873 | 1.2054667 | 0.6019289 |
| DUSP4 | −0.802811444 | 0.091192269 | 0.030362674 | −13.19865944 | 10.4034739 | 13.1588246 | 11.763422 | 9.4365051 | 9.0441909 | 0.6019289 |
| HMOX2 | −0.9074809 | 0.065205844 | 0.016561823 | −13.25790347 | 11.7507415 | 11.7826607 | 10.8252763 | 7.0964955 | 8.1355133 | 7.7187266 |
| SLC24A2 | −0.979159915 | 0.056444275 | 0.011816577 | −13.26099116 | 4.815804 | 4.9115166 | 4.7549172 | 1.0866873 | 1.2054667 | 0.6019289 |
| SHROOM2 | −0.93973829 | 0.060175708 | 0.014023911 | −13.26099116 | 4.815804 | 5.4876732 | 4.2859964 | 1.0866873 | 1.2054667 | 0.6019289 |
| NEURL3 | −0.906087156 | 0.065387484 | 0.016680575 | −13.26099116 | 4.815804 | 6.5023977 | 3.9083598 | 1.0866873 | 1.2054667 | 0.6019289 |
| ANO2 | −0.885674921 | 0.068524346 | 0.018631148 | −13.26099116 | 4.815804 | 3.8720139 | 5.5929159 | 1.0866873 | 1.2054667 | 0.6019289 |
| PQLC2 | −0.88274984 | 0.069240191 | 0.018954505 | −13.26099116 | 4.815804 | 5.297868 | 4.2859964 | 1.0866873 | 1.2054667 | 0.6019289 |
| TP63 | −0.877819293 | 0.070271956 | 0.019603627 | −13.26099116 | 4.815804 | 5.1480825 | 3.9083598 | 1.0866873 | 1.2054667 | 0.6019289 |
| TTBK2 | −0.816821327 | 0.086878366 | 0.0279459 | −13.26099116 | 4.815804 | 3.360637 | 5.5715986 | 1.0866873 | 1.2054667 | 0.6019289 |
| C15orf39 | −0.803013528 | 0.09115906 | 0.030306507 | −13.26099116 | 4.815804 | 5.297868 | 3.3243747 | 1.0866873 | 1.2054667 | 0.6019289 |
| CCDC85C | −0.986505402 | 0.056015811 | 0.011435449 | −13.35216307 | 5.8972917 | 4.8079702 | 4.9444683 | 1.0866873 | 1.2054667 | 0.6019289 |
| ZNF740 | −0.94772421 | 0.059309685 | 0.013467865 | −13.39672335 | 4.2098819 | 4.8304956 | 5.5969865 | 1.0866873 | 1.2054667 | 0.6019289 |
| UCN2 | −0.932809134 | 0.06110322 | 0.014531814 | −13.39672335 | 4.2098819 | 4.8304956 | 5.5969865 | 1.0866873 | 1.2054667 | 0.6019289 |
| TAF5L | −0.923553707 | 0.062190894 | 0.015179331 | −13.39672335 | 4.2098819 | 4.8304956 | 5.2176156 | 1.0866873 | 1.2054667 | 0.6019289 |
| ZNF785 | −0.897280299 | 0.066820774 | 0.017409131 | −13.39672335 | 5.8565586 | 4.8304956 | 3.9083598 | 1.0866873 | 1.2054667 | 0.6019289 |
| PRAF2 | −0.893201673 | 0.067248681 | 0.017786247 | −13.39672335 | 6.6586086 | 4.8304956 | 3.9083598 | 1.0866873 | 1.2054667 | 0.6019289 |
| FLNC | −0.827529887 | 0.08341132 | 0.026124529 | −13.39672335 | 3.3509967 | 4.8304956 | 5.9741452 | 1.0866873 | 1.2054667 | 0.6019289 |
| GTF3C4 | −0.804546629 | 0.090667629 | 0.030008826 | −13.39672335 | 5.3162271 | 4.8304956 | 3.3243747 | 1.0866873 | 1.2054667 | 0.6019289 |
| PNPLA7 | −0.801698683 | 0.091676899 | 0.030599374 | −13.39672335 | 2.993831 | 4.8304956 | 6.7371315 | 1.0866873 | 1.2054667 | 0.6019289 |
| HDX | −0.794466501 | 0.094648791 | 0.032183262 | −13.39672335 | 5.0569476 | 4.8304956 | 3.3243747 | 1.0866873 | 1.2054667 | 0.6019289 |
| SH3GL3 | −0.786747415 | 0.097501748 | 0.033763139 | −13.39672335 | 3.0245043 | 4.8304956 | 5.9741452 | 1.0866873 | 1.2054667 | 0.6019289 |
| SLC2A1 | −0.807932462 | 0.089586442 | 0.029415069 | −13.4200783 | 9.4704275 | 9.5338162 | 8.3873354 | 5.7241063 | 7.0925914 | 0.6019289 |
| CCDC17 | −0.938985547 | 0.060319904 | 0.014079275 | −13.44862092 | 4.6394091 | 4.3513152 | 6.0316576 | 1.0866873 | 1.2054667 | 0.6019289 |
| LCORL | −0.931215669 | 0.061288269 | 0.014646554 | −13.52894396 | 4.963444 | 4.3899364 | 4.7244061 | 1.0866873 | 1.2054667 | 0.6019289 |
| SDR39U1 | −0.967280061 | 0.057324142 | 0.012467303 | −13.62670378 | 12.0321894 | 11.7482626 | 12.2481644 | 8.2638247 | 8.2799211 | 8.1534715 |
| PUS7L | −0.95072848 | 0.058798663 | 0.013211105 | −13.81350423 | 4.7435639 | 4.3899364 | 5.7236017 | 1.0866873 | 1.2054667 | 0.6019289 |
| SMYD5 | −0.949556833 | 0.059058759 | 0.01328733 | −13.81350423 | 5.7794294 | 4.3899364 | 4.7244061 | 1.0866873 | 1.2054667 | 0.6019289 |
| LOC399715 | −0.948531938 | 0.059271835 | 0.013413303 | −13.81350423 | 4.7435639 | 4.3899364 | 5.5715986 | 1.0866873 | 1.2054667 | 0.6019289 |
| ZCCHC6 | −0.93864086 | 0.060337931 | 0.014103346 | −13.81350423 | 4.6394091 | 4.3899364 | 5.5969865 | 1.0866873 | 1.2054667 | 0.6019289 |
| ANKRD49 | −0.924168861 | 0.06209712 | 0.015136003 | −13.81350423 | 6.0999914 | 4.3899364 | 4.4498938 | 1.0866873 | 1.2054667 | 0.6019289 |
| C15orf40 | −0.769196988 | 0.104415043 | 0.037738105 | −13.81350423 | 5.7445127 | 4.3899364 | 5.5446534 | 1.6938929 | 2.9023413 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| IFI44L | −0.755362469 | 0.110198518 | 0.041116104 | −13.81350423 | 5.3162271 | 4.3899364 | 5.6099449 | 3.1012538 | 1.2054667 | 0.6019289 |
| MPHOSPH6 | −0.730394597 | 0.122181851 | 0.048080719 | −13.85391663 | 9.1327388 | 9.8744841 | 8.4281467 | 5.3405168 | 8.2799211 | 0.6019289 |
| SDF4 | −0.910345458 | 0.064473869 | 0.016328332 | −13.85918352 | 12.606325 | 12.2241592 | 11.5684125 | 9.3947409 | 1.2054667 | 8.4493889 |
| HNRNPU | −0.928092542 | 0.061611794 | 0.014865602 | −13.96666639 | 12.9759544 | 13.4373245 | 13.701247 | 9.6334087 | 8.618585 | 10.0722095 |
| RIPK1 | −0.888433847 | 0.068142722 | 0.018346305 | −14.01491523 | 10.3056141 | 9.5640624 | 9.1184541 | 6.4903918 | 1.2054667 | 6.496723 |
| HOXC5 | −0.957917723 | 0.058190948 | 0.012890957 | −14.03924755 | 4.815804 | 4.4133226 | 5.5446534 | 1.0868873 | 1.2054667 | 0.6019289 |
| SNX18 | −0.956511083 | 0.058267533 | 0.012936693 | −14.03924755 | 6.186289 | 4.4133226 | 4.7244061 | 1.0868873 | 1.2054667 | 0.6019289 |
| FIG4 | −0.947519062 | 0.059309685 | 0.013483912 | −14.03924755 | 5.3044627 | 4.4133226 | 4.7549172 | 1.0868873 | 1.2054667 | 0.6019289 |
| HIST2H2BF | −0.938921486 | 0.060319904 | 0.014087298 | −14.03924755 | 4.6820765 | 4.4133226 | 5.2252164 | 1.0868873 | 1.2054667 | 0.6019289 |
| PPFIA4 | −0.917217777 | 0.063325847 | 0.01569606 | −14.03924755 | 5.3354128 | 4.4133226 | 4.4498938 | 1.0868873 | 1.2054667 | 0.6019289 |
| BSCL2 | −0.75731644 | 0.109468311 | 0.040627457 | −14.05710257 | 3.0245043 | 4.9115166 | 5.018694 | 1.0868873 | 1.2054667 | 0.6019289 |
| TIMM8A | −0.995568387 | 0.055453935 | 0.011107278 | −14.17060296 | 4.815804 | 4.9115166 | 4.9444683 | 1.0868873 | 1.2054667 | 0.6019289 |
| LOC285074 | −0.953083847 | 0.058645827 | 0.013126855 | −14.17060296 | 4.309025 | 4.9115166 | 5.5969865 | 1.0868873 | 1.2054667 | 0.6019289 |
| PREX2 | −0.946677917 | 0.059349536 | 0.013548102 | −14.17060296 | 4.2098819 | 4.9115166 | 6.0316576 | 1.0868873 | 1.2054667 | 0.6019289 |
| RNF121 | −0.890044132 | 0.067956016 | 0.01818583 | −14.17060296 | 5.3285264 | 4.9115166 | 3.9083598 | 1.0868873 | 1.2054667 | 0.6019289 |
| C14orf176 | −0.846874852 | 0.077605332 | 0.02300329 | −14.17060296 | 3.3509967 | 4.9115166 | 6.6010094 | 1.0868873 | 1.2054667 | 0.6019289 |
| ITGAL | −0.840347968 | 0.079182309 | 0.023978978 | −14.17060296 | 3.3509967 | 4.9115166 | 6.2829045 | 1.0868873 | 1.2054667 | 0.6019289 |
| PKI55 | −0.886016594 | 0.068486123 | 0.018581401 | −14.1822691 | 6.4532097 | 6.0604012 | 4.2859964 | 2.6271932 | 1.2054667 | 0.6019289 |
| PPIF | −0.979337463 | 0.0564197 | 0.011792506 | −14.32277854 | 11.6432418 | 12.0448681 | 11.7554265 | 8.2046286 | 8.1688761 | 0.6019289 |
| AKR1C2 | −0.986909742 | 0.056015811 | 0.011411378 | −14.39968022 | 7.8277675 | 8.2468542 | 4.4498938 | 1.0868873 | 1.2054667 | 0.6019289 |
| ITGA2 | −0.972015183 | 0.056976583 | 0.012126294 | −14.39968022 | 4.7435639 | 7.5649923 | 4.4498938 | 1.0868873 | 1.2054667 | 0.6019289 |
| GJC3 | −0.969905803 | 0.057171148 | 0.012279547 | −14.39968022 | 4.7435639 | 5.4346801 | 4.5083337 | 1.0868873 | 1.2054667 | 0.6019289 |
| LOC100292680 | −0.96071379 | 0.057915811 | 0.012753751 | −14.39968022 | 4.815804 | 5.4346801 | 4.4498938 | 1.0868873 | 1.2054667 | 0.6019289 |
| E2F2 | −0.952472929 | 0.058717048 | 0.013171788 | −14.39968022 | 5.3285264 | 4.7507076 | 4.4498938 | 1.0868873 | 1.2054667 | 0.6019289 |
| HOOK1 | −0.952066377 | 0.058745484 | 0.013187836 | −14.39968022 | 4.6394091 | 6.1842483 | 4.4498938 | 1.0868873 | 1.2054667 | 0.6019289 |
| PPME1 | −0.949361138 | 0.059079344 | 0.013303378 | −14.39968022 | 5.0569476 | 4.8079702 | 4.4498938 | 1.0868873 | 1.2054667 | 0.6019289 |
| KIDINS220 | −0.942843974 | 0.059848162 | 0.013801653 | −14.39968022 | 4.6820765 | 5.1957839 | 4.4498938 | 1.0868873 | 1.2054667 | 0.6019289 |
| FDPSL2A | −0.928367818 | 0.061590622 | 0.014842333 | −14.39968022 | 5.3044627 | 5.4346801 | 4.4498938 | 1.6938929 | 1.2054667 | 0.6019289 |
| GOLGA5 | −0.732634546 | 0.121002258 | 0.04733772 | −14.39968022 | 7.2186326 | 5.297868 | 4.4498938 | 3.9905627 | 1.2054667 | 0.6019289 |
| NASP | −0.975778307 | 0.056551597 | 0.011932119 | −14.41456301 | 11.7533953 | 11.7743687 | 12.3937135 | 8.180253 | 8.5442583 | 0.6019289 |
| PCDHB19P | −0.976195217 | 0.056551597 | 0.011908048 | −14.43481723 | 5.0569476 | 4.7365865 | 4.7244061 | 1.0868873 | 1.2054667 | 0.6019289 |
| CCNB1IP1 | −0.958825268 | 0.058132446 | 0.013801653 | −14.43481723 | 5.0569476 | 4.4804956 | 4.5083337 | 1.0868873 | 1.2054667 | 0.6019289 |
| MAST2 | −0.94025906 | 0.060114874 | 0.01399984 | −14.4908788 | 11.0339514 | 11.1277725 | 12.3558728 | 8.4987997 | 7.6601162 | 9.4058315 |
| NETO2 | −0.959824261 | 0.057974898 | 0.012785846 | −14.46073544 | 4.2643629 | 6.3119075 | 4.9444683 | 7.1971015 | 1.2054667 | 0.6019289 |
| OIP5-AS1 | −0.954421279 | 0.058488069 | 0.013062665 | −14.44798945 | 5.3044627 | 4.3513152 | 4.9444683 | 1.0868873 | 1.2054667 | 0.6019289 |
| KLHDC9 | −0.928801674 | 0.061490252 | 0.014795796 | −14.44798945 | 4.2098819 | 5.1480825 | 4.9444683 | 1.0868873 | 1.2054667 | 0.6019289 |
| POLA1 | −0.894940416 | 0.067128739 | 0.017632994 | −14.44798945 | 6.2275774 | 3.7709946 | 4.9444683 | 1.0868873 | 1.2054667 | 0.6019289 |
| FAM169B | −0.886995155 | 0.068365464 | 0.018462649 | −14.44798945 | 5.3285264 | 3.8720139 | 4.9444683 | 1.0868873 | 1.2054667 | 0.6019289 |
| DMBX1 | −0.813967286 | 0.087666999 | 0.028409693 | −14.44798945 | 5.265993 | 3.360637 | 4.9444683 | 1.0868873 | 1.2054667 | 0.6019289 |
| LYSMD3 | −0.763882262 | 0.106557388 | 0.03900345 | −14.44798945 | 5.8565586 | 2.8096013 | 4.9444683 | 1.0868873 | 1.2054667 | 0.6019289 |
| MDK | −0.805066433 | 0.090425668 | 0.029869213 | −14.52989826 | 10.1665236 | 11.3436619 | 11.7403133 | 7.4827092 | 7.6601162 | 0.6019289 |
| FMNL3 | −0.862499446 | 0.073380796 | 0.02096606 | −14.60735401 | 10.4169274 | 9.1280672 | 11.0657244 | 7.1971015 | 1.2054667 | 7.141714 |
| PPP1R16A | −0.995699659 | 0.055419354 | 0.01109123 | −14.68994094 | 4.963444 | 4.7365865 | 5.018694 | 1.0868873 | 1.2054667 | 0.6019289 |
| CCDC136 | −0.970852506 | 0.057122382 | 0.012213753 | −14.68994094 | 4.963444 | 4.3899364 | 5.7236017 | 1.0868873 | 1.2054667 | 0.6019289 |
| C3orf74 | −0.950228548 | 0.058798663 | 0.013219129 | −14.68994094 | 4.963444 | 5.4346801 | 4.2859964 | 1.0868873 | 1.2054667 | 0.6019289 |
| C2CD4A | −0.92224424 | 0.062363889 | 0.015252347 | −14.68994094 | 4.963444 | 6.8213295 | 3.9083598 | 1.0868873 | 1.2054667 | 0.6019289 |
| PCDHB15 | −0.8994577 | 0.066433398 | 0.017179652 | −14.68994094 | 4.963444 | 3.8720139 | 5.7236017 | 1.0868873 | 1.2054667 | 0.6019289 |
| CHI3L2 | −0.861580236 | 0.073534549 | 0.021046297 | −14.68994094 | 4.963444 | 7.440099 | 3.3243747 | 1.0868873 | 1.2054667 | 0.6019289 |
| VIPR2 | −0.724139645 | 0.12474266 | 0.049930193 | −14.68994094 | 4.963444 | 2.406905 | 6.0721689 | 1.0868873 | 1.2054667 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| SLC3A2 | -0.849534926 | 0.07698033 | 0.022704004 | -14.69215517 | 12.31447 | 11.8688263 | 11.9334135 | 9.44676 | 7.5630806 | 8.0564393 |
| URGCP | -0.728833633 | 0.12296007 | 0.048508385 | -14.73532721 | 8.062715 | 7.8717699 | 7.8250252 | 3.9905627 | 6.9463683 | 0.6019289 |
| EIF3J | -0.936587926 | 0.060682102 | 0.014235738 | -14.9390924 | 10.9251791 | 12.2260351 | 11.9182731 | 1.0866873 | 8.3250145 | 8.2262493 |
| TMBIM1 | -0.925542759 | 0.06185043 | 0.015045334 | -14.94364839 | 13.3369313 | 12.6657897 | 12.4255567 | 8.3206874 | 9.4354708 | 9.0627933 |
| KLF15 | -0.971136783 | 0.057101475 | 0.012190484 | -14.94949482 | 6.4876101 | 4.7365865 | 4.5083337 | 1.0866873 | 1.2054667 | 0.6019289 |
| RBM43 | -0.968228825 | 0.057313185 | 0.012427184 | -14.94949482 | 6.0548278 | 4.7365865 | 4.5083337 | 1.0866873 | 1.2054667 | 0.6019289 |
| TSPAN17 | -0.965319394 | 0.057395438 | 0.012547541 | -14.99494982 | 5.7530242 | 4.7365865 | 4.5083337 | 1.0866873 | 1.2054667 | 0.6019289 |
| PPP1R3A | -0.969801358 | 0.057171148 | 0.012295595 | -15.12876689 | 11.6026113 | 10.3241015 | 10.8759415 | 6.9599943 | 7.6833888 | 0.6019289 |
| QRSL1 | -0.932186978 | 0.0611032 | 0.014563909 | -15.12924244 | 10.1124251 | 10.5759834 | 10.175278 | 7.5025051 | 1.2054667 | 6.2560101 |
| CALU | -0.773206571 | 0.102731018 | 0.036791302 | -15.1826568 | 12.9262534 | 11.5215357 | 11.9907327 | 11.5237292 | 8.0663803 | 0.6019289 |
| ATM | -0.981437281 | 0.056391645 | 0.011752387 | -15.2634239 | 5.8972917 | 4.4133226 | 5.018694 | 1.0866873 | 1.2054667 | 0.6019289 |
| TRIML2 | -0.888091599 | 0.068142722 | 0.018370376 | -15.2634239 | 3.8399484 | 5.3621423 | 5.018694 | 1.0866873 | 1.2054667 | 0.6019289 |
| RELL2 | -0.839223046 | 0.079358501 | 0.02414186 | -15.2634239 | 5.8972917 | 3.360637 | 5.018694 | 1.0866873 | 1.2054667 | 0.6019289 |
| DDX10 | -1.016733339 | 0.053584658 | 0.01009789 | -15.37607941 | 4.815804 | 5.1480825 | 5.018694 | 1.0866873 | 1.2054667 | 0.6019289 |
| C1orf46 | -0.846654646 | 0.077638018 | 0.023025756 | -15.40021146 | 6.0082059 | 6.5720715 | 3.9352215 | 2.6271932 | 1.2054667 | 0.6019289 |
| PRRC2B | -0.927119866 | 0.061709548 | 0.014952259 | -15.57126168 | 12.419569 | 12.5726936 | 12.7057679 | 9.8891573 | 1.2054667 | 8.6118796 |
| HSF1 | -0.978029137 | 0.056452334 | 0.018406648 | -15.59060532 | 11.4658356 | 12.2069929 | 11.0559919 | 7.5976045 | 1.2054667 | 8.2443879 |
| SEC61A1 | -0.958224345 | 0.058154469 | 0.012873305 | -15.63502711 | 13.9318442 | 13.0981071 | 12.464905 | 9.5068039 | 9.1313973 | 8.6456318 |
| SDS | -0.994094449 | 0.055573321 | 0.01115863 | -15.67355243 | 5.0569476 | 4.3899364 | 7.9423658 | 1.0866873 | 1.2054667 | 0.6019289 |
| CROT | -0.984491465 | 0.056097909 | 0.011544572 | -15.67355243 | 5.0569476 | 5.297868 | 4.5083337 | 1.0866873 | 1.2054667 | 0.6019289 |
| NUP107 | -0.981882031 | 0.056371224 | 0.01173634 | -15.67355243 | 5.0569476 | 5.4876732 | 4.4498938 | 1.0866873 | 1.2054667 | 0.6019289 |
| PPP1R14C | -0.91253866 | 0.064224288 | 0.01605071 | -15.67355243 | 5.0569476 | 5.7897017 | 3.9083598 | 1.0866873 | 1.2054667 | 0.6019289 |
| ADPRHL1 | -0.889348037 | 0.068037763 | 0.018258846 | -15.67355243 | 5.0569476 | 3.8720139 | 5.2176156 | 8.6215576 | 8.8926726 | 8.6948242 |
| ENTPD2 | -0.727588729 | 0.123357599 | 0.048961727 | -15.67355243 | 6.9047187 | 14.7785443 | 14.188872 | 10.6258278 | 10.365077 | 10.4519348 |
| CKB | -0.912486407 | 0.064224388 | 0.016066758 | -15.77538473 | 11.9050961 | 13.1837362 | 13.5890269 | 7.9254928 | 9.9051779 | 14.160494 |
| NXF1 | -0.921624763 | 0.062559106 | 0.01533098 | -15.84700527 | 13.1897532 | 14.2868575 | 14.4898903 | 10.3007191 | 9.5347853 | 10.3984929 |
| AKNA | -0.991626336 | 0.055698998 | 0.01122282 | -15.92484719 | 12.2860376 | 12.6880319 | 13.4351605 | 8.6215576 | 8.8926726 | 8.6948242 |
| PHB2 | -1.012380119 | 0.054044749 | 0.010282436 | -15.99908648 | 14.4464319 | 14.7785443 | 14.188872 | 10.6258278 | 10.365077 | 10.4519348 |
| RPS6 | -0.934828642 | 0.060960411 | 0.014383375 | -15.98285773 | 17.3519419 | 18.2820626 | 17.6491629 | 12.6330859 | 14.2836091 | 14.160494 |
| IL12B | -1.012968249 | 0.054044749 | 0.010242317 | -16.1355043 | 5.0569476 | 4.7365865 | 5.2176156 | 1.0866873 | 1.2054667 | 0.6019289 |
| PLCD4 | -0.819614943 | 0.085991355 | 0.027484554 | -16.22053786 | 5.2636993 | 4.8304956 | 5.2252164 | 1.0866873 | 1.2054667 | 9.62472 |
| CAPN10 | -0.991626336 | 0.05293768 | 0.009654979 | -16.69654979 | 4.815804 | 5.1480825 | 5.2252164 | 1.0866873 | 1.2054667 | 0.6019289 |
| MURC | -1.004920568 | 0.054532631 | 0.010664367 | -16.421115 | 5.8565586 | 5.1480825 | 4.5083337 | 1.0866873 | 1.2054667 | 0.6019289 |
| CAPZB | -0.869863337 | 0.071778384 | 0.02035465 | -16.421115 | 4.6394091 | 5.4346801 | 6.0560619 | 2.6271932 | 9.9101189 | 0.6019289 |
| RPUSD3 | -1.042678019 | 0.052218844 | 0.00924977 | -16.51979571 | 14.5045577 | 13.7708539 | 13.621832 | 9.72473 | 1.2054667 | 0.6019289 |
| NHLRC1 | -0.819614943 | 0.085991355 | 0.027484554 | -16.65903114 | 5.2636993 | 5.1480825 | 3.3243747 | 1.0866873 | 1.2054667 | 0.6019289 |
| ROGDI | -1.030233833 | 0.05293768 | 0.009654979 | -16.69654979 | 4.815804 | 5.1480825 | 5.2252164 | 1.0866873 | 1.2054667 | 0.6019289 |
| BMP6 | -1.004920568 | 0.054532631 | 0.010664367 | -16.69558977 | 5.8565586 | 5.1480825 | 4.5083337 | 1.0866873 | 1.2054667 | 0.6019289 |
| NLRX1 | -0.983055676 | 0.056243388 | 0.011626414 | -16.69558977 | 4.309025 | 5.1480825 | 6.2829045 | 1.0866873 | 1.2054667 | 0.6019289 |
| SPCS2 | -0.982168494 | 0.056371224 | 0.011720292 | -16.69558977 | 6.4876101 | 5.1480825 | 4.2859964 | 1.0866873 | 1.2054667 | 0.6019289 |
| C9orf152 | -0.982070357 | 0.056371224 | 0.011728316 | -16.69558977 | 5.3044627 | 5.1480825 | 4.4498938 | 1.0866873 | 1.2054667 | 0.6019289 |
| MCM9 | -0.975870736 | 0.056551597 | 0.011924095 | -16.69558977 | 4.2098819 | 5.1480825 | 6.8910052 | 1.0866873 | 1.2054667 | 0.6019289 |
| SCT | -0.932245242 | 0.0611032 | 0.014555885 | -16.69558977 | 6.2677178 | 5.1480825 | 3.9352215 | 1.0866873 | 1.2054667 | 0.6019289 |
| LOC442459 | -0.840503323 | 0.079141153 | 0.023940464 | -16.69558977 | 3.3509967 | 5.1480825 | 5.7236017 | 1.0866873 | 1.2054667 | 0.6019289 |
| RNH1 | -0.798793615 | 0.093160485 | 0.031355211 | -16.69558977 | 5.8565586 | 5.1480825 | 2.956812 | 1.0866873 | 1.2054667 | 0.6019289 |
| SRRT | -0.948124939 | 0.059309685 | 0.01343577 | -16.69619213 | 13.619617 | 12.8615819 | 12.27568 | 8.8001347 | 14.2836091 | 10.1029082 |
| RHEBL1 | -0.99083686 | 0.055727384 | 0.011254915 | -16.70246805 | 12.0681612 | 12.5306452 | 12.261635 | 6.0269554 | 8.8826529 | 8.1996456 |
| GCNT1 | -1.010885495 | 0.054161962 | 0.010378721 | -16.91401854 | 4.6820765 | 4.9115166 | 6.7371315 | 1.0866873 | 1.2054667 | 0.6019289 |
| C1orf220 | -1.002311307 | 0.054766682 | 0.010798363 | -16.91401854 | 4.6820765 | 4.9115166 | 5.5446534 | 1.0866873 | 1.2054667 | 0.6019289 |
| | -0.986090906 | 0.056015811 | 0.01145952 | -16.91401854 | 4.6820765 | 4.7365865 | 5.7236017 | 1.0866873 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| HLA-L | −0.985782589 | 0.056084432 | 0.011482789 | −16.91401854 | 4.6820765 | 4.7507076 | 5.5715986 | 1.0866873 | 1.2054667 | 0.6019289 |
| SYN2 | −0.984009846 | 0.056097909 | 0.011568643 | −16.91401854 | 4.6820765 | 5.6616851 | 4.7244061 | 1.0866873 | 1.2054667 | 0.6019289 |
| GPR110 | −0.982707654 | 0.056201234 | 0.011648881 | −16.91401854 | 4.6820765 | 4.7507076 | 5.3892653 | 1.0866873 | 1.2054667 | 0.6019289 |
| DLST | −0.927886582 | 0.061636261 | 0.01488165 | −16.91401854 | 4.6820765 | 6.0497213 | 6.3558005 | 2.6271932 | 1.2054667 | 0.6019289 |
| UBQLN4 | −0.872161462 | 0.071512479 | 0.020138009 | −17.05829267 | 5.3162271 | 5.297868 | 5.2176156 | 2.6271932 | 1.2054667 | 0.6019289 |
| C15orf52 | −0.889458921 | 0.068025256 | 0.018226751 | −17.1364458 | 5.3044627 | 5.297868 | 3.7641245 | 1.0866873 | 1.2054667 | 0.6019289 |
| HN1L | −1.02519858 | 0.05313101 | 0.009785766 | −17.12195244 | 11.387139 | 12.0578318 | 11.6813945 | 7.2911484 | 7.4857665 | 7.924091 |
| LOC220729 | −1.038967719 | 0.052564289 | 0.009379764 | −17.25684206 | 4.6820765 | 5.1957839 | 6.5278107 | 1.0866873 | 1.2054667 | 0.6019289 |
| HACL1 | −1.010725945 | 0.054161962 | 0.010386745 | −17.25684206 | 5.982974 | 5.1957839 | 4.508333 | 1.0866873 | 1.2054667 | 0.6019289 |
| ANKMY1 | −1.010546879 | 0.054161962 | 0.010394769 | −17.25684206 | 6.8989234 | 5.1957839 | 4.4498938 | 1.0866873 | 1.2054667 | 0.6019289 |
| SLC13A4 | −0.984037104 | 0.056097909 | 0.011560619 | −17.25684206 | 4.309025 | 5.1957839 | 6.0721689 | 1.0866873 | 1.2054667 | 0.6019289 |
| WFIKKN1 | −0.925711587 | 0.06185043 | 0.01503731 | −17.25684206 | 3.8399484 | 5.1957839 | 6.4105447 | 1.0866873 | 1.2054667 | 0.6019289 |
| EPHB2 | −1.06062186 | 0.051416052 | 0.008539677 | −17.27675605 | 5.3162271 | 5.1957839 | 5.018694 | 1.0866873 | 1.2054667 | 0.6019289 |
| PLEKHG5 | −0.739305473 | 0.1180144 | 0.045586135 | −17.27675605 | 5.3162271 | 4.7365865 | 5.5446534 | 3.4605153 | 1.2054667 | 9.482544 |
| IER3 | −0.901012889 | 0.066271613 | 0.017061703 | −17.34672646 | 13.3310215 | 14.646838 | 14.3002414 | 9.21443 | 11.3371844 | 9.482544 |
| TSPYL2 | −0.954249863 | 0.058516799 | 0.013078713 | −17.41463728 | 14.7435364 | 13.8092403 | 15.6074533 | 10.6213079 | 11.8708107 | 0.6019289 |
| ZSCAN16 | −1.039429149 | 0.052533354 | 0.009363717 | −17.41763908 | 6.4179694 | 5.1480825 | 4.7244061 | 1.0866873 | 1.2054667 | 0.6019289 |
| HAS3 | −1.021979615 | 0.053385633 | 0.009896494 | −17.41763908 | 4.963444 | 8.0533052 | 4.7244061 | 1.0866873 | 1.2054667 | 0.6019289 |
| RAB15 | −0.996570735 | 0.054849354 | 0.011067159 | −17.41763908 | 4.7435639 | 6.4291897 | 4.7244061 | 1.0866873 | 1.2054667 | 0.6019289 |
| ASL | −1.036739808 | 0.052603935 | 0.009445559 | −17.42467348 | 5.3285264 | 5.297868 | 5.5715986 | 1.0866873 | 1.2054667 | 0.6019289 |
| TET3 | −0.99628127 | 0.055419354 | 0.011083206 | −17.50804512 | 5.3354128 | 4.8079702 | 4.7549172 | 1.6938929 | 1.2054667 | 0.6019289 |
| FGD2 | −1.080312244 | 0.051255379 | 0.008124047 | −17.51996815 | 5.3162271 | 5.1480825 | 5.2176156 | 1.0866873 | 1.2054667 | 0.6019289 |
| DYNC1H1 | −1.038734459 | 0.052564289 | 0.009387788 | −17.51996815 | 5.2645993 | 4.8304956 | 5.2176156 | 1.0866873 | 1.2054667 | 0.6019289 |
| POLR3C | −0.994465392 | 0.055530925 | 0.01140977 | −17.51996815 | 5.7445127 | 4.4133226 | 5.2176156 | 1.0866873 | 1.2054667 | 0.6019289 |
| ICA1 | −0.990414455 | 0.055727384 | 0.011262938 | −17.51996815 | 4.309025 | 6.4291897 | 5.2176156 | 1.0866873 | 1.2054667 | 0.6019289 |
| RBMY2FP | −0.984391482 | 0.056097909 | 0.011552596 | −17.51996815 | 5.7003762 | 4.3513152 | 5.2176156 | 1.0866873 | 1.2054667 | 0.6019289 |
| PPTC7 | −1.01448761 | 0.053847872 | 0.010168694 | −17.56531502 | 4.963444 | 4.7365865 | 5.5446534 | 1.0866873 | 1.2054667 | 0.6019289 |
| PLSCR2 | −1.004932597 | 0.054532652 | 0.010656343 | −17.56531502 | 4.815804 | 4.7365865 | 6.1759311 | 1.0866873 | 1.2054667 | 0.6019289 |
| CTBP2 | −1.036800341 | 0.052603935 | 0.009437535 | −17.57134353 | 5.3044627 | 5.3406193 | 5.5446534 | 1.6938929 | 1.2054667 | 0.6019289 |
| CCNYL1 | −1.086573831 | 0.051099543 | 0.007956351 | −17.61251609 | 5.3285264 | 5.1957839 | 5.2252164 | 1.0866873 | 1.2054667 | 0.6019289 |
| DCLRE1B | −0.989225859 | 0.055849348 | 0.0113175 | −17.61251609 | 5.8972917 | 4.3513152 | 5.2176156 | 1.0866873 | 1.2054667 | 0.6019289 |
| LOC286359 | −0.984590815 | 0.056097909 | 0.015365648 | −17.61251609 | 5.4911209 | 4.3899364 | 5.2252164 | 1.0866873 | 1.2054667 | 0.6019289 |
| MRP5 | −0.812526249 | 0.088296719 | 0.028700955 | −17.61251609 | 6.9491661 | 6.6056864 | 5.9741452 | 1.6938929 | 1.2054667 | 4.3970308 |
| TGM5 | −0.726075807 | 0.124034522 | 0.049381369 | −17.61251609 | 1.8744435 | 7.6317881 | 8.2799514 | 5.8529567 | 4.1872998 | 0.6019289 |
| ITGB8 | −1.044907943 | 0.051974546 | 0.009034743 | −17.65047354 | 4.7435639 | 7.8154118 | 5.2176156 | 1.0866873 | 1.2054667 | 0.6019289 |
| CALCA | −1.017152669 | 0.053550528 | 0.010082645 | −17.65047354 | 4.7435639 | 5.8096013 | 4.9444683 | 1.0866873 | 1.2054667 | 0.6019289 |
| NIPAL1 | −0.933866668 | 0.060990824 | 0.014454786 | −17.65047354 | 4.7435639 | 6.7924268 | 5.9741452 | 1.0866873 | 1.2054667 | 0.6019289 |
| SP140L | −0.86832499 | 0.07203996 | 0.02045254 | −17.65944717 | 8.8382996 | 8.3296681 | 8.2799514 | 1.0866873 | 1.2054667 | 4.0446258 |
| MED10 | −1.026604158 | 0.053094283 | 0.009736019 | −17.73808861 | 5.8972917 | 4.7507076 | 5.018694 | 1.0866873 | 1.2054667 | 0.6019289 |
| DIO3 | −1.002914562 | 0.054659392 | 0.010750221 | −17.73808861 | 4.815804 | 4.7507076 | 5.7029118 | 1.0866873 | 1.2054667 | 0.6019289 |
| PLAC8L1 | −1.001561609 | 0.054889674 | 0.010849715 | −17.73808861 | 5.0569476 | 6.7924268 | 5.5969865 | 1.0866873 | 1.2054667 | 0.6019289 |
| LGSN | −1.034904764 | 0.052782082 | 0.009520982 | −17.78992245 | 4.815804 | 7.8717699 | 4.7549172 | 1.0866873 | 1.2054667 | 0.6019289 |
| CDH3 | −1.010269768 | 0.054185592 | 0.010426061 | −17.78992245 | 4.815804 | 7.8717699 | 4.7549172 | 1.0866873 | 1.2054667 | 0.6019289 |
| HYOU1 | −0.843021754 | 0.078689412 | 0.023648399 | −17.78992245 | 8.5352855 | 6.7020747 | 4.7549172 | 4.5400907 | 1.2054667 | 0.6019289 |
| CCDC41 | −1.061808472 | 0.051493437 | 0.008627939 | −17.83544858 | 4.963444 | 5.3621423 | 5.2252164 | 1.0866873 | 1.2054667 | 0.6019289 |
| NAP1L4 | −0.920246948 | 0.062900898 | 0.01545615 | −18.0696402 | 12.7223886 | 13.4518404 | 13.0908792 | 8.9153833 | 4.1872998 | 10.7090071 |
| LYRM2 | −1.071715123 | 0.051355105 | 0.00833429 | −18.08863901 | 5.2645993 | 5.3621423 | 5.018694 | 1.0866873 | 1.2054667 | 0.6019289 |
| CADPS2 | −1.06806104 | 0.051378258 | 0.00839525 | −18.08863901 | 5.2645993 | 5.297868 | 5.018694 | 1.0866873 | 1.2054667 | 0.6019289 |
| CCDC154 | −1.046078406 | 0.052154186 | 0.009143866 | −18.08863901 | 5.2645993 | 4.7507076 | 5.7029118 | 1.0866873 | 1.2054667 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| TMEM8A | -0.905538953 | 0.065433337 | 0.016703041 | -18.08863901 | 5.2663993 | 5.7897017 | 3.7641245 | 1.0866873 | 1.2054667 | 0.6019289 |
| CHMP4C | -0.747487226 | 0.11383441 | 0.043184626 | -18.08863901 | 5.2663993 | 7.1970971 | 2.1654208 | 1.0866873 | 1.2054667 | 0.6019289 |
| FLJ16341 | -1.039807551 | 0.052533354 | 0.009355693 | -18.17393109 | 4.7435639 | 5.3406193 | 5.3892653 | 1.0866873 | 1.2054667 | 0.6019289 |
| DAGLB | -0.980982056 | 0.056391645 | 0.011768435 | -18.17393109 | 5.3354128 | 4.3513152 | 5.3892653 | 1.0866873 | 1.2054667 | 0.6019289 |
| LEPRE1 | -0.980036899 | 0.05641197 | 0.011784482 | -18.17393109 | 5.3162271 | 4.3513152 | 5.3892653 | 1.0866873 | 1.2054667 | 0.6019289 |
| DDN | -0.788527044 | 0.096601594 | 0.03332424 | -18.17393109 | 2.993831 | 5.297868 | 5.3892653 | 1.0866873 | 1.2054667 | 0.6019289 |
| CXorf65 | -0.96484037 | 0.0574622 | 0.012587659 | -18.39725212 | 11.7391851 | 10.9362428 | 10.2793206 | 7.268205 | 7.5377667 | 0.6019289 |
| PCGF1 | -1.058944549 | 0.051725293 | 0.008755912 | -18.52216349 | 6.7650859 | 5.297868 | 4.7549172 | 1.0866873 | 1.2054667 | 0.6019289 |
| ALG1 | -1.053480386 | 0.051888429 | 0.008907165 | -18.52216349 | 4.7435639 | 5.297868 | 6.0540376 | 1.0866873 | 1.2054667 | 0.6019289 |
| CES3 | -0.983299566 | 0.056243388 | 0.01161839 | -18.52216349 | 4.2634629 | 5.297868 | 5.9741452 | 1.0866873 | 1.2054667 | 0.6019289 |
| SLC33A1 | -0.868729768 | 0.07202519 | 0.020436492 | -18.52216349 | 6.5540448 | 5.297868 | 3.3243747 | 1.0866873 | 1.2054667 | 0.6019289 |
| ITGA11 | -0.844617366 | 0.07808379 | 0.02333788 | -18.52216349 | 3.0245043 | 5.297868 | 7.1323668 | 1.0866873 | 1.2054667 | 0.6019289 |
| LOC100129617 | -0.813311595 | 0.087899593 | 0.028514001 | -18.52216349 | 2.993831 | 5.297868 | 6.0540376 | 1.0866873 | 1.2054667 | 0.6019289 |
| IL24 | -0.754050432 | 0.110813327 | 0.041473161 | -18.52216349 | 6.5212096 | 5.297868 | 2.3793449 | 1.0866873 | 1.2054667 | 0.6019289 |
| PIGZ | -1.056819349 | 0.051814299 | 0.00882773 | -18.55678797 | 4.815804 | 6.0361098 | 5.2252164 | 1.0866873 | 1.2054667 | 0.6019289 |
| MRAP2 | -1.050326209 | 0.051900312 | 0.008994624 | -18.55678797 | 4.815804 | 5.3406193 | 5.3892653 | 1.0866873 | 1.2054667 | 0.6019289 |
| ANKRD16 | -1.066376798 | 0.051378258 | 0.008451416 | -18.60702339 | 5.3044627 | 4.8079702 | 6.6706745 | 1.0866873 | 1.2054667 | 0.6019289 |
| MYLPF | -1.011868486 | 0.054077708 | 0.010298484 | -18.60702339 | 5.3044627 | 6.0441977 | 4.4498938 | 1.0866873 | 1.2054667 | 0.6019289 |
| C11orf61 | -1.00640301 | 0.054519995 | 0.010600979 | -18.60702339 | 5.3044627 | 4.4133226 | 6.0316576 | 1.0866873 | 1.2054667 | 0.6019289 |
| ZNF768 | -0.985307509 | 0.056096089 | 0.011514082 | -18.60702339 | 5.3044627 | 4.3513152 | 5.5446534 | 1.0866873 | 1.2054667 | 0.6019289 |
| CMTM4 | -0.915707643 | 0.063435834 | 0.015744203 | -18.60702339 | 5.3044627 | 6.0726357 | 3.7641245 | 1.0866873 | 1.2054667 | 0.6019289 |
| MSR1 | -0.882838258 | 0.069229646 | 0.018936853 | -18.60702339 | 5.3044627 | 3.360637 | 7.0032858 | 1.0866873 | 1.2054667 | 0.6019289 |
| LOC401321 | -1.051746214 | 0.051900312 | 0.008962529 | -18.74672502 | 5.3285264 | 4.8304956 | 5.3892653 | 1.0866873 | 1.2054667 | 0.6019289 |
| LRRC8B | -1.036843982 | 0.052603935 | 0.00942911 | -18.74672502 | 5.0569476 | 4.8304956 | 5.5969865 | 1.0866873 | 1.2054667 | 0.6019289 |
| LOC100289495 | -1.032005546 | 0.052917554 | 0.009616465 | -18.74672502 | 4.963444 | 4.804956 | 6.0560619 | 1.0866873 | 1.2054667 | 0.6019289 |
| PAK6 | -1.00394672 | 0.054558959 | 0.010704485 | -18.75937447 | 5.3162271 | 7.6317881 | 4.2859964 | 1.0866873 | 1.2054667 | 0.6019289 |
| CTF1 | -0.779568344 | 0.100080374 | 0.035291663 | -18.75937447 | 5.3162271 | 2.8096013 | 5.7236017 | 1.0866873 | 1.2054667 | 0.6019289 |
| BCL2L11 | -0.972877471 | 0.056901344 | 0.01205408 | -18.80321009 | 11.6336712 | 11.248424 | 12.1915069 | 8.6661239 | 2.5373444 | 7.4007641 |
| LOC100129550 | -1.080030009 | 0.051255379 | 0.008132071 | -18.91998555 | 5.3285264 | 5.4346801 | 5.018694 | 1.0866873 | 1.2054667 | 0.6019289 |
| ANKS1A | -1.065282036 | 0.051378258 | 0.008499559 | -18.91998555 | 5.3285264 | 4.8079702 | 6.0540376 | 1.0866873 | 1.2054667 | 0.6019289 |
| DAPP1 | -1.031537473 | 0.052917554 | 0.009624488 | -18.91998555 | 5.3285264 | 7.4023354 | 4.5083337 | 1.0866873 | 1.2054667 | 0.6019289 |
| MICALL2 | -1.011861957 | 0.053847872 | 0.010182942 | -18.91998555 | 5.3285264 | 5.6616851 | 4.5083337 | 1.0866873 | 1.2054667 | 0.6019289 |
| SP9 | -1.005756306 | 0.054519995 | 0.010617026 | -18.91998555 | 5.3285264 | 4.3513152 | 6.6497707 | 1.0866873 | 1.2054667 | 0.6019289 |
| USF1 | -1.004791737 | 0.054532631 | 0.01067239 | -18.91998555 | 5.3285264 | 4.3899364 | 6.0316576 | 1.0866873 | 1.2054667 | 0.6019289 |
| EPC1 | -0.84068558 | 0.079132386 | 0.02389874 | -18.91998555 | 5.3285264 | 3.3213504 | 5.5715986 | 1.0866873 | 1.2054667 | 0.6019289 |
| POU2F3 | -0.732063433 | 0.121322681 | 0.047503009 | -18.91998555 | 5.3285264 | 6.537655 | 2.1654208 | 1.0866873 | 1.2054667 | 0.6019289 |
| BEND3 | -1.067853566 | 0.051378258 | 0.008411297 | -19.0105118 | 5.3354128 | 4.8079702 | 6.2829045 | 1.0866873 | 1.2054667 | 0.6019289 |
| SELP | -1.058480372 | 0.051725293 | 0.008777983 | -19.0105118 | 5.3354128 | 6.7629335 | 4.724061 | 1.0866873 | 1.2054667 | 0.6019289 |
| LAYN | -1.058089052 | 0.051725293 | 0.00879403 | -19.0105118 | 5.3354128 | 6.0361098 | 4.7549172 | 1.0866873 | 1.2054667 | 0.6019289 |
| MYCT1 | -1.056160909 | 0.051814299 | 0.008843778 | -19.0105118 | 5.3354128 | 4.8079702 | 5.5715986 | 1.0866873 | 1.2054667 | 0.6019289 |
| TNFSF10 | -1.059661739 | 0.051660967 | 0.008706571 | -19.07924221 | 4.7435639 | 5.3406193 | 6.3267171 | 1.0866873 | 1.2054667 | 0.6019289 |
| TSSC1 | -0.92167222 | 0.062529069 | 0.015313327 | -19.07924221 | 6.2275774 | 5.3406193 | 3.7641245 | 1.0866873 | 1.2054667 | 0.6019289 |
| MAZ | -0.926606407 | 0.061733832 | 0.01497633 | -19.24211565 | 12.2140107 | 11.3235963 | 12.539366 | 8.9590228 | 7.0574008 | 7.7807893 |
| ABCC10 | -0.989171293 | 0.055849348 | 0.011325524 | -19.36601165 | 5.8972917 | 5.3621624 | 4.2859964 | 1.0866873 | 1.2054667 | 0.6019289 |
| NOP14 | -1.048653562 | 0.051974546 | 0.009058814 | -19.456853 | 5.0569476 | 5.4876732 | 4.9444683 | 1.0866873 | 1.2054667 | 0.6019289 |
| ARHGAP39 | -1.109443785 | 0.050523319 | 0.007292787 | -19.50340646 | 5.4911209 | 5.3406193 | 5.2252164 | 1.0866873 | 1.2054667 | 0.6019289 |
| E4F1 | -1.033043144 | 0.052897282 | 0.009593998 | -19.50340646 | 5.4911209 | 4.9115166 | 4.9444683 | 1.0866873 | 1.2054667 | 0.6019289 |
| GEMIN8 | -0.845637154 | 0.077914269 | 0.023184626 | -19.50340646 | 5.4911209 | 3.360637 | 5.3892653 | 1.0866873 | 1.2054667 | 0.6019289 |
| INTS10 | -0.788588211 | 0.096601594 | 0.033316216 | -19.56952071 | 9.9053047 | 9.4437316 | 8.9109561 | 5.1531951 | 8.2951094 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| RTKN | -1.058692464 | 0.051725293 | 0.008769959 | -19.73354129 | 4.6820765 | 7.5477987 | 5.3892653 | 1.0866873 | 1.2054667 | 0.6019289 |
| LOC100126784 | -1.052153113 | 0.051900312 | 0.008946482 | -19.73354129 | 4.6394091 | 6.7924268 | 5.3892653 | 1.0866873 | 1.2054667 | 0.6019289 |
| AGT | -1.001601344 | 0.054889674 | 0.010841691 | -19.73354129 | 4.309025 | 6.270596 | 5.3892653 | 1.0866873 | 1.2054667 | 0.6019289 |
| RAVER2 | -1.000919056 | 0.054963463 | 0.010891439 | -19.73354129 | 4.309025 | 6.2280676 | 5.3892653 | 1.0866873 | 1.2054667 | 0.6019289 |
| EDN2 | -0.889144176 | 0.068037763 | 0.018274894 | -19.73354129 | 3.3509967 | 7.1060646 | 5.3892653 | 1.0866873 | 1.2054667 | 0.6019289 |
| CNIH4 | -1.058839165 | 0.051099543 | 0.007964375 | -19.82965461 | 6.0999914 | 4.9115166 | 5.3892653 | 1.0866873 | 1.2054667 | 0.6019289 |
| PARP9 | -1.065601862 | 0.051378258 | 0.008483511 | -19.82965461 | 5.7445127 | 4.9115166 | 5.2176156 | 1.0866873 | 1.2054667 | 0.6019289 |
| SLC7A11 | -0.983498366 | 0.056177581 | 0.011594319 | -20.04859947 | 6.8468682 | 7.2617905 | 4.9444683 | 1.0866873 | 1.2054667 | 2.9363609 |
| LETM2 | -1.120873605 | 0.050341156 | 0.006964615 | -20.24069278 | 5.3044627 | 5.3406193 | 5.5446534 | 1.0866873 | 1.2054667 | 0.6019289 |
| LOC100507501 | -1.090800347 | 0.050995256 | 0.007780631 | -20.24069278 | 5.0569476 | 5.3406193 | 5.5446534 | 1.0866873 | 1.2054667 | 0.6019289 |
| CLDN1 | -0.771626601 | 0.10322713 | 0.037121881 | -20.24069278 | 5.3285264 | 6.537655 | 5.5446534 | 4.1976103 | 1.2054667 | 0.6019289 |
| RNASEH2C | -1.090060905 | 0.051027823 | 0.007819947 | -20.2877834 | 6.6783891 | 5.3621423 | 4.9444683 | 1.0866873 | 1.2054667 | 0.6019289 |
| SCN8A | -1.087257029 | 0.051099543 | 0.00793228 | -20.2877834 | 6.3067721 | 5.3406193 | 4.9444683 | 1.0866873 | 1.2054667 | 0.6019289 |
| TOPBP1 | -1.082039442 | 0.051255379 | 0.008067881 | -20.2877834 | 5.4911209 | 5.4876732 | 4.9444683 | 1.0866873 | 1.2054667 | 0.6019289 |
| INF2 | -0.745173385 | 0.115164025 | 0.043821712 | -20.2877834 | 6.7078705 | 7.0338116 | 4.9444683 | 5.0495858 | 1.2054667 | 0.6019289 |
| ZNF384 | -0.920584832 | 0.062815622 | 0.015424858 | -20.35650695 | 11.1566394 | 11.2364018 | 11.1087264 | 6.8092213 | 8.8624022 | 0.6019289 |
| LOC284950 | -1.074705028 | 0.051291304 | 0.008229961 | -20.36461672 | 4.815804 | 5.4346801 | 6.0125266 | 1.0866873 | 1.2054667 | 0.6019289 |
| RNPC3 | -1.054180159 | 0.051852306 | 0.008883896 | -20.36461672 | 5.7003762 | 5.4346801 | 4.7244061 | 1.0866873 | 1.2054667 | 0.6019289 |
| PYGM | -1.04785195 | 0.052136699 | 0.009097328 | -20.36461672 | 4.6820765 | 5.4346801 | 5.7029118 | 1.0866873 | 1.2054667 | 0.6019289 |
| WAS | -1.015335487 | 0.05365276 | 0.010119554 | -20.36461672 | 4.309025 | 5.4346801 | 7.3390847 | 1.0866873 | 1.2054667 | 0.6019289 |
| WRAP73 | -1.007119811 | 0.054507998 | 0.010576908 | -20.36461672 | 6.6783891 | 5.4346801 | 4.2859964 | 1.0866873 | 1.2054667 | 0.6019289 |
| CHPF2 | -0.836740211 | 0.080425127 | 0.024620075 | -20.36461672 | 6.5861495 | 5.4346801 | 2.2995812 | 1.0866873 | 1.2054667 | 0.6019289 |
| ASZ1 | -1.059823672 | 0.051660967 | 0.008690524 | -20.62227961 | 5.982974 | 5.1480825 | 5.5715986 | 1.6938929 | 1.2054667 | 0.6019289 |
| TRIM68 | -0.910649926 | 0.064737869 | 0.016288213 | -20.62227961 | 5.4911209 | 3.7709946 | 5.5715986 | 1.0866873 | 1.2054667 | 0.6019289 |
| PATL1 | -1.0218647 | 0.053385633 | 0.009904517 | -20.70300639 | 11.1159753 | 9.9319425 | 11.267554 | 6.7442069 | 6.9463683 | 0.6019289 |
| PRKDC | -0.956038323 | 0.058865313 | 0.01296959 | -20.88490167 | 11.9161912 | 11.5776788 | 10.834794 | 8.6215576 | 7.1932904 | 0.6019289 |
| WIPF3 | -1.118533324 | 0.050341156 | 0.007028805 | -20.92925666 | 5.2635993 | 5.3406193 | 5.5929159 | 1.0866873 | 1.2054667 | 0.6019289 |
| NELF | -0.933909534 | 0.060990824 | 0.014446762 | -20.93802018 | 11.2954278 | 11.5423038 | 10.8176167 | 4.9379926 | 6.9073747 | 8.4106527 |
| PLIN2 | -0.839739876 | 0.079317736 | 0.024088101 | -21.03041133 | 13.0985972 | 10.6959553 | 11.8801716 | 10.5278012 | 7.4857665 | 0.6019289 |
| SMPD3 | -1.007494581 | 0.054397005 | 0.010538394 | -21.12655816 | 4.2098819 | 5.4876732 | 7.4222392 | 1.0866873 | 1.2054667 | 0.6019289 |
| SPTBN5 | -0.810466905 | 0.088930093 | 0.029053197 | -21.12655816 | 2.993831 | 5.4876732 | 5.7029118 | 1.0866873 | 1.2054667 | 0.6019289 |
| LOC389641 | -1.009603326 | 0.054296381 | 0.010474204 | -21.17710664 | 5.4911209 | 6.537655 | 4.2859964 | 1.0866873 | 1.2054667 | 0.6019289 |
| LOC100289230 | -0.927185635 | 0.061709548 | 0.014944235 | -21.17710664 | 5.4911209 | 3.7709946 | 6.0540376 | 1.0866873 | 1.2054667 | 0.6019289 |
| ZNF513 | -1.126405547 | 0.050294669 | 0.006853888 | -21.17776189 | 5.3285264 | 5.3406193 | 5.6099449 | 1.0866873 | 1.2054667 | 0.6019289 |
| GPC1 | -0.850274044 | 0.076767438 | 0.022628581 | -21.2441842 | 9.0941798 | 10.0465526 | 7.2279137 | 4.6851838 | 6.5504789 | 0.6019289 |
| USP2 | -1.112343074 | 0.050440463 | 0.00722298 | -21.35889525 | 6.7928648 | 5.4876732 | 5.018694 | 1.0866873 | 1.2054667 | 0.6019289 |
| SH3RF2 | -1.097066153 | 0.050892627 | 0.007622563 | -21.35889525 | 5.3354128 | 6.6385363 | 5.018694 | 1.0866873 | 1.2054667 | 0.6019289 |
| NEDD4 | -1.089534581 | 0.051027823 | 0.007844018 | -21.35889525 | 5.8565586 | 5.297868 | 5.018694 | 1.0866873 | 1.2054667 | 0.6019289 |
| C10orf111 | -1.088815903 | 0.051099543 | 0.007884137 | -21.35889525 | 5.2635993 | 6.0497213 | 5.018694 | 1.0866873 | 1.2054667 | 0.6019289 |
| ESRP2 | -1.088103421 | 0.051291304 | 0.007892161 | -21.35889525 | 5.3162271 | 8.464054 | 5.018694 | 1.0866873 | 1.2054667 | 0.6019289 |
| AGFG2 | -1.07206747 | 0.051291304 | 0.008298163 | -21.35889525 | 5.7003762 | 5.1480825 | 5.018694 | 1.0866873 | 1.2054667 | 0.6019289 |
| NRIP3 | -1.07206747 | 0.051291304 | 0.008298163 | -21.35889525 | 5.7003762 | 5.1480825 | 5.018694 | 1.0866873 | 1.2054667 | 0.6019289 |
| ZNF34 | -0.83719034 | 0.08030325 | 0.024543047 | -21.35889525 | 6.5540448 | 6.0924064 | 5.018694 | 3.7493131 | 1.2054667 | 0.6019289 |
| PSMC2 | -0.741828316 | 0.117105527 | 0.044811041 | -21.35889525 | 6.186289 | 6.0726357 | 5.018694 | 4.3788962 | 1.2054667 | 0.6019289 |
| TMEM68 | -0.732064959 | 0.121322681 | 0.047494985 | -21.35889525 | 5.7445127 | 6.7328249 | 5.018694 | 4.5400907 | 1.2054667 | 0.6019289 |
| DNM1L | -0.945244166 | 0.059597087 | 0.013657225 | -21.52985331 | 10.1206704 | 9.9018086 | 9.6667798 | 7.2911484 | 5.473542 | 0.6019289 |
| UPF3A | -1.094464181 | 0.050952718 | 0.007685148 | -21.90429601 | 6.6586086 | 5.1480825 | 5.2176156 | 1.0866873 | 1.2054667 | 0.6019289 |
| CCDC146 | -1.010294501 | 0.054185592 | 0.010418037 | -21.90429601 | 5.6586086 | 4.3899364 | 5.5969865 | 1.0866873 | 1.2054667 | 0.6019289 |
| TAP2 | -1.10726228 | 0.050608213 | 0.007365803 | -21.93280923 | 5.0569476 | 6.270596 | 5.3892653 | 1.0866873 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| IRF8 | −1.098614716 | 0.050846008 | 0.007582444 | −21.93280923 | 5.0569476 | 5.3406193 | 7.7138893 | 1.0866873 | 1.2054667 | 0.6019289 |
| LAMC2 | −0.858147586 | 0.07443975 | 0.021514082 | −21.93280923 | 5.0569476 | 8.3396934 | 6.976024 | 1.0866873 | 4.8088443 | 0.6019289 |
| ALDOA | −1.043740778 | 0.052218844 | 0.009217684 | −21.96444367 | 14.6760218 | 14.5515264 | 13.9105947 | 10.0944284 | 9.1731002 | 10.6056134 |
| SLC16A7 | −1.078675722 | 0.051291304 | 0.008165771 | −21.97766377 | 5.7530242 | 4.804956 | 5.5446534 | 1.0866873 | 1.2054667 | 0.6019289 |
| LOC389906 | −1.023854055 | 0.053244867 | 0.009832304 | −21.97766377 | 4.309025 | 7.282726 | 5.5446534 | 1.0866873 | 1.2054667 | 0.6019289 |
| SLC29A1 | −0.956998844 | 0.058245659 | 0.01292225 | −22.09386148 | 11.4539207 | 11.8036371 | 10.8573834 | 6.988347 | 1.2054667 | 8.6288544 |
| ALG13 | −0.994850358 | 0.055484459 | 0.011123325 | −22.2844786 | 6.0548278 | 7.1060646 | 5.018694 | 2.6271932 | 1.2054667 | 0.6019289 |
| LOC442421 | −1.104466196 | 0.050647945 | 0.007486159 | −22.39199677 | 6.4532097 | 4.9115166 | 5.5715986 | 1.0866873 | 1.2054667 | 0.6019289 |
| ZWILCH | −1.081430513 | 0.051255379 | 0.008083928 | −22.39199677 | 6.4876101 | 4.7507076 | 5.5715986 | 1.0866873 | 1.2054667 | 0.6019289 |
| DHODH | −1.009753746 | 0.054264218 | 0.010458156 | −22.39199677 | 7.1158353 | 6.0726357 | 5.5715986 | 1.0866873 | 1.2054667 | 0.6019289 |
| LOC148413 | −0.902946945 | 0.0658276 | 0.016879564 | −22.39199677 | 4.309025 | 3.360637 | 5.5715986 | 1.0866873 | 1.2054667 | 0.6019289 |
| TMEM45B | −0.947082387 | 0.059314973 | 0.013522426 | −22.54771722 | 5.7003762 | 5.6616851 | 3.9352215 | 1.0866873 | 1.2054667 | 0.6019289 |
| TMEM120B | −1.01043802 | 0.054161962 | 0.010402792 | −22.5873818 | 6.4179694 | 5.6616851 | 5.7029118 | 2.6271932 | 1.2054667 | 0.6019289 |
| ZNF385A | −0.878330612 | 0.070167691 | 0.019493701 | −22.68564918 | 10.7341965 | 10.1326825 | 11.2290953 | 6.2304884 | 4.1872998 | 8.818351 |
| ITPR2 | −1.093345617 | 0.050952718 | 0.007741314 | −22.7253173 | 6.8989234 | 4.8079702 | 5.5929159 | 1.0866873 | 1.2054667 | 0.6019289 |
| SNORD100 | −0.947874013 | 0.051291304 | 0.008221937 | −22.7253173 | 4.6820765 | 6.7020747 | 5.5929159 | 1.0866873 | 1.2054667 | 0.6019289 |
| UTS2D | −1.024967758 | 0.0531310 | 0.00979379 | −22.7253173 | 6.0082059 | 4.4133226 | 5.5929159 | 1.0866873 | 1.2054667 | 0.6019289 |
| PIK3R3 | −1.008582845 | 0.054397005 | 0.010522346 | −22.73029278 | 7.6263253 | 7.2405467 | 8.6938442 | 3.7493131 | 1.2054667 | 0.6019289 |
| PEAK1 | −0.906413224 | 0.065373045 | 0.016666132 | −22.73501634 | 10.2886388 | 11.9926106 | 12.5755803 | 9.1841037 | 7.4857665 | 0.6019289 |
| RAD9A | −1.16391281 | 0.04991757 | 0.006126936 | −22.78952839 | 5.6586086 | 5.4346801 | 5.5969865 | 1.0866873 | 1.2054667 | 0.6019289 |
| PRPF40B | −1.106827621 | 0.050608213 | 0.00738987 | −22.78952839 | 6.4876101 | 4.9115166 | 5.5969865 | 1.0866873 | 1.2054667 | 0.6019289 |
| SH3D21 | −1.063807516 | 0.051416052 | 0.008638749 | −22.78952839 | 4.6394091 | 6.2280676 | 5.5969865 | 1.0866873 | 1.2054667 | 0.6019289 |
| FCER1G | −0.874306636 | 0.070926344 | 0.019902913 | −22.78952839 | 5.982974 | 3.360637 | 5.5969865 | 1.0866873 | 1.2054667 | 0.6019289 |
| LOC652276 | −1.1313409 | 0.050131358 | 0.006733531 | −22.91364401 | 5.3162271 | 5.3621423 | 5.7236017 | 1.0866873 | 1.2054667 | 0.6019289 |
| SLC9A5 | −1.070382999 | 0.051355105 | 0.008342293 | −22.91364401 | 6.4876101 | 5.6616851 | 5.7236017 | 1.0866873 | 1.2054667 | 0.6019289 |
| OGDH | −1.041913546 | 0.052218844 | 0.009257803 | −23.13183402 | 10.7782963 | 10.4451226 | 9.5092748 | 5.9133149 | 6.4989608 | 0.6019289 |
| CUL4A | −1.049025571 | 0.051974546 | 0.009042767 | −23.1934646 | 10.169176 | 10.5632048 | 10.5389092 | 6.7442069 | 6.0032628 | 0.6019289 |
| GLRA4 | −1.169609548 | 0.04991757 | 0.005990532 | −23.24818277 | 5.7445127 | 5.4346801 | 5.6699448 | 1.0866873 | 1.2054667 | 0.6019289 |
| MAP2K1 | −1.004934549 | 0.054532631 | 0.010648319 | −23.27370247 | 12.3447011 | 11.5734369 | 12.2916645 | 8.7595777 | 7.7510357 | 6.6374655 |
| DPYSL5 | −1.105100662 | 0.050647945 | 0.007454064 | −23.36299872 | 5.2636993 | 5.1480825 | 6.0721689 | 1.0866873 | 1.2054667 | 0.6019289 |
| LOC284578 | −1.081223012 | 0.051255379 | 0.008108 | −23.36299872 | 7.3175786 | 5.1480825 | 5.5929159 | 1.6938929 | 1.2054667 | 0.6019289 |
| KIAA0284 | −0.73788623 | 0.118499692 | 0.045980101 | −23.38574598 | 5.7530242 | 6.3119075 | 5.2176156 | 4.6851838 | 1.2054667 | 0.6019289 |
| MRPL14 | −1.101698193 | 0.05069779 | 0.007526278 | −23.54252971 | 11.1506678 | 12.0162438 | 11.2520092 | 7.2211194 | 7.4590463 | 6.6374655 |
| PAXIP1 | −1.128353669 | 0.050237584 | 0.006813769 | −23.78403042 | 5.6586086 | 6.6706551 | 5.018694 | 1.0866873 | 1.2054667 | 0.6019289 |
| PSPH | −1.112033431 | 0.050400463 | 0.007231004 | −23.78403042 | 5.6586086 | 6.0924064 | 4.9444683 | 1.0866873 | 1.2054667 | 0.6019289 |
| KIAA0664L3 | −1.087279832 | 0.051099543 | 0.007924256 | −23.78403042 | 5.6586086 | 6.3520696 | 4.7549172 | 1.0866873 | 1.2054667 | 0.6019289 |
| VAMP1 | −1.033105705 | 0.052897282 | 0.009577951 | −23.78403042 | 5.6586086 | 4.3899364 | 6.3558005 | 1.0866873 | 1.2054667 | 0.6019289 |
| NFXL1 | −0.955465442 | 0.058423167 | 0.013009709 | −23.78403042 | 5.6586086 | 6.0497213 | 3.9083598 | 1.0866873 | 1.2054667 | 0.6019289 |
| ABCB8 | −1.144103261 | 0.050004604 | 0.006494423 | −23.83480311 | 6.4098488 | 5.6616851 | 5.2176156 | 1.0866873 | 1.2054667 | 0.6019289 |
| C8orf42 | −1.019681473 | 0.053434625 | 0.009968707 | −23.83480311 | 4.2098488 | 5.6616851 | 7.273415 | 1.0866873 | 1.2054667 | 0.6019289 |
| WWOX | −1.019283571 | 0.053434625 | 0.009976731 | −23.83480311 | 6.4179694 | 5.6616851 | 4.2859964 | 1.0866873 | 1.2054667 | 0.6019289 |
| RRN3P1 | −0.960986378 | 0.057805981 | 0.01272051 | −23.83480311 | 6.0999914 | 5.6616851 | 3.9352215 | 1.0866873 | 1.2054667 | 0.6019289 |
| FBXL19 | −1.155206384 | 0.04991757 | 0.006303458 | −23.98790096 | 5.4911209 | 5.7897017 | 5.3892653 | 4.5400907 | 6.6948447 | 0.6019289 |
| ALPK3 | −0.776731462 | 0.101203431 | 0.035911097 | −23.98790096 | 6.5212096 | 11.3659071 | 5.7029118 | 4.5400907 | 1.2054667 | 0.6019289 |
| TCEB3 | −1.078344861 | 0.051291304 | 0.008173794 | −24.06437463 | 10.5915154 | 10.3659071 | 10.9141534 | 6.7770801 | 1.2054667 | 0.6019289 |
| UCN | −1.125887673 | 0.050330336 | 0.00686833 | −24.14838796 | 6.5540448 | 5.1957839 | 5.3892653 | 1.0866873 | 1.2054667 | 0.6019289 |
| RPP25 | −1.117890001 | 0.050341156 | 0.007068924 | −24.14838796 | 5.3162271 | 5.1957839 | 6.3692392 | 4.5400907 | 1.2054667 | 0.6019289 |
| KIAA0513 | −1.110972773 | 0.050482841 | 0.007254273 | −24.14838796 | 5.2636993 | 5.1957839 | 6.0560619 | 1.0866873 | 1.2054667 | 0.6019289 |
| SLED1 | −1.06097181 | 0.050608213 | 0.007413945 | −24.14838796 | 5.2636993 | 5.1957839 | 7.7625708 | 1.0866873 | 1.2054667 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| CHST5 | −0.812688426 | 0.088274767 | 0.028679291 | −24.44449668 | 7.5951068 | 7.5477987 | 7.4018955 | 5.5826351 | 2.5373444 | 2.9363609 |
| PRSS22 | −1.12301005 | 0.050330336 | 0.006900425 | −24.48266733 | 5.7003762 | 8.8620252 | 5.018694 | 1.0866873 | 1.2054667 | 0.6019289 |
| CYP8B1 | −1.084420154 | 0.051255379 | 0.008035691 | −24.48266733 | 5.7003762 | 4.7507076 | 6.0721689 | 1.0866873 | 1.2054667 | 0.6019289 |
| TPD52L1 | −0.974181295 | 0.056729293 | 0.011988285 | −24.48266733 | 5.7003762 | 6.537655 | 3.9352215 | 1.0866873 | 1.2054667 | 0.6019289 |
| PPP1R35 | −1.120632432 | 0.050341156 | 0.006972639 | −24.51659385 | 5.3162271 | 6.3520696 | 5.2176156 | 1.0866873 | 1.2054667 | 0.6019289 |
| NLRC5 | −1.119605807 | 0.050341156 | 0.006988687 | −24.51659385 | 5.3162271 | 6.0497213 | 5.2176156 | 1.0866873 | 1.2054667 | 0.6019289 |
| SLC35F2 | −1.114471503 | 0.050390282 | 0.007141138 | −24.51659385 | 5.2636993 | 6.270596 | 5.2176156 | 1.0866873 | 1.2054667 | 0.6019289 |
| GPAT2 | −0.736905429 | 0.118810891 | 0.046187114 | −24.51659385 | 8.3973089 | 6.6385363 | 5.2176156 | 5.9133149 | 1.2054667 | 0.6019289 |
| B3GAT1 | −1.038281538 | 0.052564289 | 0.009395812 | −24.52573578 | 4.309025 | 7.6480149 | 5.7029118 | 1.0866873 | 1.2054667 | 0.6019289 |
| SYNGAP1 | −0.833729585 | 0.08138461 | 0.025039718 | −24.52573578 | 6.7650859 | 2.8096013 | 5.7029118 | 1.0866873 | 1.2054667 | 0.6019289 |
| NHLH1 | −1.15576946 | 0.04991757 | 0.006295434 | −24.64610095 | 5.6586086 | 6.1842483 | 5.2252164 | 1.0866873 | 1.2054667 | 0.6019289 |
| KIAA1984 | −1.121279851 | 0.050341156 | 0.006940544 | −24.64610095 | 5.3162271 | 6.1842483 | 5.2252164 | 1.0866873 | 1.2054667 | 0.6019289 |
| ZNF687 | −1.119417901 | 0.050341156 | 0.007004734 | −24.64610095 | 6.4532097 | 5.297868 | 5.2252164 | 1.0866873 | 1.2054667 | 0.6019289 |
| FEZ1 | −1.116882676 | 0.050341156 | 0.007076948 | −24.64610095 | 7.1342805 | 5.297868 | 5.2252164 | 1.0866873 | 1.2054667 | 0.6019289 |
| TTC9 | −0.786206215 | 0.097781854 | 0.033892321 | −24.64610095 | 7.3365789 | 8.8895842 | 5.2252164 | 6.0269554 | 1.2054667 | 0.6019289 |
| CTSS | −0.784110909 | 0.098241201 | 0.034310359 | −24.64610095 | 6.6175557 | 6.0924064 | 5.2252164 | 4.3788962 | 1.2054667 | 0.6019289 |
| SIN3A | −1.091762716 | 0.050952718 | 0.007765386 | −24.69302643 | 12.2229738 | 11.7872468 | 12.9059529 | 7.0161533 | 8.2799211 | 7.7187266 |
| C11orf53 | −1.159338942 | 0.04991757 | 0.006215197 | −24.87999641 | 6.4876101 | 5.1957839 | 5.7236017 | 1.0866873 | 1.2054667 | 0.6019289 |
| LAD1 | −1.13021942 | 0.050131358 | 0.006757603 | −24.87999641 | 5.0569476 | 8.7686392 | 5.7236017 | 1.0866873 | 1.2054667 | 0.6019289 |
| VTA1 | −0.755390234 | 0.110198518 | 0.041092032 | −25.12570076 | 5.8565586 | 5.8096013 | 2.3793449 | 1.0866873 | 1.2054667 | 0.6019289 |
| ATP6V0C | −1.059937427 | 0.051695193 | 0.00872984 | −25.22581055 | 13.7757009 | 14.4584116 | 14.4109621 | 10.4960584 | 8.21751 69 | 9.7541334 |
| PTPN3 | −1.164269615 | 0.04991757 | 0.006110888 | −25.24324388 | 5.7445127 | 7.1748717 | 5.2252164 | 1.0866873 | 1.2054667 | 0.6019289 |
| C6orf132 | −1.161215018 | 0.04991757 | 0.006183102 | −25.24324388 | 5.7445127 | 7.6317881 | 5.2252164 | 1.0866873 | 1.2054667 | 0.6019289 |
| VNN3 | −0.989079617 | 0.055849948 | 0.011333547 | −25.24324388 | 5.7445127 | 7.5477987 | 3.9083598 | 1.0866873 | 1.2054667 | 0.6019289 |
| DUS2L | −0.846442617 | 0.077676075 | 0.023049827 | −25.24324388 | 5.7445127 | 6.3520696 | 2.956812 | 1.0866873 | 1.2054667 | 0.6019289 |
| MRPL41 | −0.942306481 | 0.059221626 | 0.013848191 | −25.24721803 | 11.0541814 | 10.7903568 | 10.0002517 | 6.1323043 | 1.2054667 | 8.0564393 |
| NONO | −1.090272933 | 0.051027823 | 0.0078029 | −25.25946532 | 11.9357942 | 12.5679039 | 11.8727987 | 8.3206874 | 1.2054667 | 7.277042 |
| ANKRD34C | −1.157038511 | 0.04991757 | 0.006271363 | −25.31236428 | 5.2636993 | 6.4662577 | 5.5969865 | 1.0866873 | 1.2054667 | 0.6019289 |
| C5orf42 | −0.773989939 | 0.10250289 | 0.036591511 | −25.31236428 | 5.2636993 | 6.3520696 | 7.273415 | 4.9379926 | 1.2054667 | 0.6019289 |
| PTHLH | −0.769551426 | 0.104268882 | 0.037600899 | −25.31236428 | 5.2636993 | 7.9877767 | 6.4105447 | 5.1531951 | 1.2054667 | 0.6019289 |
| NRG1 | −1.139781827 | 0.050038461 | 0.006574661 | −25.39261219 | 5.7530242 | 10.3088724 | 5.2252164 | 1.0866873 | 1.2054667 | 0.6019289 |
| CCHCR1 | −1.107130629 | 0.050608213 | 0.00738185 | −25.39261219 | 5.7530242 | 4.8304956 | 6.4897707 | 1.0866873 | 1.2054667 | 0.6019289 |
| ZNF318 | −0.941341464 | 0.060058355 | 0.013937254 | −25.39261219 | 5.7530242 | 3.7709946 | 6.0721689 | 1.0866873 | 1.2054667 | 0.6019289 |
| PEBP4 | −1.182241366 | 0.049897122 | 0.005686432 | −25.84520947 | 5.8972917 | 5.4876732 | 5.6099449 | 5.4258059 | 1.2054667 | 0.6019289 |
| C4orf42 | −1.116176396 | 0.050341156 | 0.007101019 | −25.84520947 | 5.8972917 | 5.3406193 | 6.1759311 | 1.6938929 | 1.2054667 | 0.6019289 |
| GMPR2 | −1.158234865 | 0.04991757 | 0.006239268 | −25.8616311 | 5.7794294 | 5.1957839 | 6.0540376 | 1.0866873 | 1.2054667 | 0.6019289 |
| FAM83H | −1.152062794 | 0.04991757 | 0.006375672 | −25.8616311 | 5.7794294 | 9.0262169 | 5.2176156 | 1.0866873 | 1.2054667 | 0.6019289 |
| RAPGEF3 | −1.093737902 | 0.050952718 | 0.007733291 | −25.8616311 | 5.7794294 | 4.7365865 | 6.4105447 | 1.0866873 | 1.2054667 | 0.6019289 |
| ANKRD45 | −0.769551426 | 0.04991757 | 0.005982508 | −25.91901741 | 6.0548278 | 5.297868 | 6.0316576 | 1.0866873 | 1.2054667 | 0.6019289 |
| C8orf46 | −1.1681595 | 0.04991757 | 0.006022627 | −25.91901741 | 5.297868 | 5.297868 | 5.7029118 | 1.0866873 | 1.2054667 | 0.6019289 |
| HDAC4 | −1.1704403 | 0.04991757 | 0.006062746 | −25.91901741 | 5.7003762 | 5.297868 | 6.0125266 | 1.0866873 | 1.2054667 | 0.6019289 |
| RASL11B | −0.738524773 | 0.118195214 | 0.045803579 | −25.91901741 | 5.982974 | 6.1390574 | 8.1272196 | 5.4258059 | 1.2054667 | 0.6019289 |
| CHIC1 | −1.158675747 | 0.04991757 | 0.006231244 | −26.03776623 | 5.3044627 | 6.3067721 | 5.5715986 | 1.0866873 | 1.2054667 | 0.6019289 |
| KIF9 | −1.167966933 | 0.04991757 | 0.006030651 | −26.04644157 | 6.3067721 | 5.7897017 | 5.2252164 | 1.0866873 | 1.2054667 | 0.6019289 |
| IDO1 | −1.025530753 | 0.05313101 | 0.009777742 | −26.04644157 | 4.2098819 | 5.7897017 | 6.976024 | 1.0866873 | 1.2054667 | 0.6019289 |
| TSG101 | −0.96503207 | 0.057395438 | 0.012563588 | −26.0802458 | 12.9045312 | 11.6204548 | 10.5779713 | 7.9254928 | 1.2054667 | 8.1996456 |
| ATP6V0B | −1.059389265 | 0.051695193 | 0.008721817 | −26.11464535 | 12.8711183 | 12.0699274 | 12.6175399 | 7.9107527 | 1.2054667 | 8.833074 |
| ARF1 | −1.142396882 | 0.050004604 | 0.006534542 | −26.17442195 | 16.0512629 | 15.8501555 | 15.2326933 | 11.3959251 | 10.4200244 | 11.1404298 |
| FHL3 | −0.843210483 | 0.078689412 | 0.023625933 | −26.2107535 | 10.145127 | 10.521976 | 10.4746101 | 1.0866873 | 5.7625232 | 8.985824 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| ADAMTSL4 | −1.17262456 | 0.04991757 | 0.005926342 | −26.25095895 | 5.3162271 | 6.0604012 | 5.7236017 | 1.0866873 | 1.2054667 | 0.6019289 |
| POLR2J4 | −1.166617304 | 0.04991757 | 0.006078793 | −26.25095895 | 5.3162271 | 5.6616851 | 6.0125266 | 1.0866873 | 1.2054667 | 0.6019289 |
| TCF24 | −1.157153144 | 0.04991757 | 0.006263339 | −26.25095895 | 5.3162271 | 6.0924064 | 5.5446534 | 1.0866873 | 1.2054667 | 0.6019289 |
| ESRG | −1.169004788 | 0.04991757 | 0.005998556 | −26.24081977 | 6.2677178 | 5.8096013 | 5.2252164 | 1.0866873 | 1.2054667 | 0.6019289 |
| TWIST2 | −1.13317049 | 0.050083269 | 0.006693413 | −26.24081977 | 4.963444 | 5.8096013 | 7.5754206 | 1.0866873 | 1.2054667 | 0.6019289 |
| ZDHHC6 | −1.094536014 | 0.050952718 | 0.007677124 | −26.24081977 | 6.4532097 | 5.8096013 | 4.7244061 | 1.0866873 | 1.2054667 | 0.6019289 |
| RPS6KL1 | −1.083832915 | 0.051255379 | 0.008027762 | −26.24081977 | 5.982974 | 5.8096013 | 4.7244061 | 1.0866873 | 1.2054667 | 0.6019289 |
| BICD1 | −1.022620994 | 0.053385633 | 0.009880446 | −26.24081977 | 4.309025 | 5.8096013 | 6.0721689 | 1.0866873 | 1.2054667 | 0.6019289 |
| MPP6 | −1.022052076 | 0.053385633 | 0.00988847 | −26.24081977 | 4.309025 | 5.8096013 | 6.0540376 | 1.0866873 | 1.2054667 | 0.6019289 |
| LRRC56 | −1.185017396 | 0.049897122 | 0.005622242 | −26.47571031 | 5.3285264 | 5.7897017 | 6.7042855 | 1.0866873 | 1.2054667 | 0.6019289 |
| C2orf82 | −1.150781629 | 0.04991757 | 0.006391719 | −26.47571031 | 5.3285264 | 8.6924512 | 5.6099449 | 1.0866873 | 1.2054667 | 0.6019289 |
| POP1 | −1.179510103 | 0.04991757 | 0.005814812 | −26.60238835 | 5.3354128 | 6.4291897 | 5.7236017 | 1.0866873 | 1.2054667 | 0.6019289 |
| LOC283174 | −1.174702071 | 0.04991757 | 0.005910294 | −26.60238835 | 5.3354128 | 7.1970971 | 5.7029118 | 1.0866873 | 1.2054667 | 0.6019289 |
| ATAD2 | −1.164065348 | 0.04991757 | 0.006118912 | −26.60238835 | 5.3354128 | 6.0604012 | 5.5929159 | 1.0866873 | 1.2054667 | 0.6019289 |
| CSF3R | −1.160517669 | 0.04991757 | 0.006191126 | −26.60238835 | 5.3354128 | 5.6616851 | 8.3020771 | 1.0866873 | 1.2054667 | 0.6019289 |
| TBX19 | −0.822405285 | 0.083361525 | 0.027042446 | −26.64346093 | 7.5139709 | 6.8213295 | 7.8701536 | 5.6551006 | 1.2054667 | 2.7782613 |
| PEX11B | −1.176714772 | 0.04991757 | 0.005894247 | −26.69856636 | 5.7445127 | 5.3406193 | 6.0125266 | 1.0866873 | 1.2054667 | 0.6019289 |
| MAK | −1.163704296 | 0.04991757 | 0.006142983 | −26.69856636 | 6.1437849 | 5.3406193 | 5.5715986 | 1.0866873 | 1.2054667 | 0.6019289 |
| ADCY4 | −1.1303484 | 0.050004604 | 0.006526518 | −26.69856636 | 6.8201191 | 5.3406193 | 5.3892653 | 1.0866873 | 1.2054667 | 0.6019289 |
| TIGD1 | −0.796735326 | 0.094012974 | 0.03182781 | −26.69856636 | 6.3818471 | 5.3406193 | 6.0125266 | 4.1976103 | 1.2054667 | 0.6019289 |
| SMPD2 | −1.145402148 | 0.049952273 | 0.006462328 | −27.0998576 | 6.0082059 | 5.3621423 | 5.3892653 | 1.0866873 | 1.2054667 | 0.6019289 |
| IL10RA | −0.822770866 | 0.083310984 | 0.026986279 | −27.0998576 | 6.6540448 | 5.3621423 | 7.5934735 | 4.8170878 | 1.2054667 | 0.6019289 |
| GLE1 | −0.780281415 | 0.099852653 | 0.035103105 | −27.0998576 | 7.373845 | 5.3621423 | 6.0540376 | 4.8170878 | 1.2054667 | 0.6019289 |
| BDH1 | −0.816808778 | 0.086378366 | 0.027953944 | −27.28188256 | 5.8565586 | 2.8096013 | 6.0316576 | 1.0866873 | 1.2054667 | 6.2560101 |
| APEH | −0.880438908 | 0.069612081 | 0.019167937 | −27.57473528 | 11.1159753 | 10.6382319 | 9.6539332 | 5.8529567 | 8.6064601 | 0.6019289 |
| LARS2 | −1.182259354 | 0.049897122 | 0.005678408 | −27.61416076 | 5.7003762 | 7.1060646 | 5.3892653 | 7.9107527 | 8.1013608 | 0.6019289 |
| BCOR | −1.155856283 | 0.04991757 | 0.006287411 | −27.61416076 | 6.3818471 | 5.3621423 | 5.3892653 | 5.2498839 | 1.2054667 | 0.6019289 |
| SF3B4 | −1.036548528 | 0.05264149 | 0.009461606 | −27.78126148 | 11.7560442 | 11.0520503 | 10.7079526 | 7.9829919 | 1.2054667 | 6.2560101 |
| DCTN2 | −1.010937276 | 0.054161962 | 0.010370697 | −28.07863429 | 12.3198511 | 11.8135625 | 10.0910775 | 7.0161533 | 8.6064601 | 0.6019289 |
| PAPPA | −0.919794449 | 0.06299636 | 0.015510712 | −27.95740662 | 12.9065195 | 10.9312788 | 10.2876614 | 7.9107527 | 8.1013608 | 0.6019289 |
| KCTD18 | −0.73851497 | 0.118195214 | 0.045811602 | −27.99427461 | 7.0676142 | 5.6616851 | 6.0125266 | 5.2498839 | 1.2054667 | 0.6019289 |
| FLJ40852 | −1.199394461 | 0.049809046 | 0.005389553 | −28.06313647 | 5.8972917 | 5.3621423 | 6.2829045 | 1.0866873 | 1.2054667 | 0.6019289 |
| C3orf78 | −1.094220702 | 0.050952718 | 0.007693172 | −28.06313647 | 5.8972917 | 6.1842483 | 4.7244061 | 1.0866873 | 1.2054667 | 0.6019289 |
| SLC29A2 | −1.073859749 | 0.051291304 | 0.008237984 | −28.06313647 | 5.8972917 | 6.874542 | 4.5083337 | 1.0866873 | 1.2054667 | 0.6019289 |
| EIF1AD | −0.970656228 | 0.057154457 | 0.012239429 | −28.06313647 | 5.8972917 | 6.0441977 | 5.5715986 | 1.0866873 | 2.8554202 | 0.6019289 |
| GJB2 | −0.843672168 | 0.078621688 | 0.023563348 | −28.06313647 | 5.8972917 | 6.0726357 | 2.9956812 | 1.0866873 | 1.2054667 | 0.6019289 |
| PHF1 | −1.044979745 | 0.052154186 | 0.009175961 | −28.31821818 | 11.8449893 | 10.4074891 | 12.472651 | 7.8808129 | 7.0213307 | 0.6019289 |
| RNF217 | −1.08136684 | 0.051255379 | 0.008091952 | −28.45564751 | 4.6394091 | 6.0361098 | 6.0125266 | 1.0866873 | 1.2054667 | 0.6019289 |
| ADIPOQ | −0.969902939 | 0.057171148 | 0.012287571 | −28.45564751 | 5.982974 | 6.0361098 | 3.9083598 | 1.0866873 | 1.2054667 | 0.6019289 |
| THPO | −1.194692655 | 0.049809046 | 0.005453743 | −28.49725711 | 5.7794294 | 5.4346801 | 6.0721689 | 1.0866873 | 1.2054667 | 0.6019289 |
| PPIL6 | −1.180807392 | 0.049897122 | 0.005774693 | −28.49725711 | 6.7367617 | 5.4346801 | 5.6099449 | 1.0866873 | 1.2054667 | 0.6019289 |
| LOC100132774 | −1.172016814 | 0.04991757 | 0.005942389 | −28.49725711 | 7.3175786 | 5.4346801 | 5.5715986 | 1.0866873 | 1.2054667 | 0.6019289 |
| SNHG10 | −0.780277773 | 0.099902938 | 0.035148038 | −28.49725711 | 6.0548278 | 5.4346801 | 7.1074578 | 4.8088443 | 1.2054667 | 0.6019289 |
| CCDC24 | −1.061041584 | 0.051493437 | 0.008635962 | −28.6156210 | 6.0082059 | 6.0441977 | 4.5083337 | 1.0866873 | 1.2054667 | 0.6019289 |
| ZNF408 | −1.195166668 | 0.049809046 | 0.005429672 | −28.81146038 | 5.5354128 | 6.0497213 | 6.0540376 | 1.0866873 | 1.2054667 | 0.6019289 |
| ZNF670 | −1.19463811 | 0.049809046 | 0.005469791 | −28.81146038 | 5.3285264 | 6.0361098 | 6.0540376 | 1.0866873 | 1.2054667 | 0.6019289 |
| NRBF2 | −0.800642897 | 0.092266937 | 0.030887427 | −28.85723281 | 12.16834 | 12.2063081 | 11.3213559 | 4.9379926 | 7.3174789 | 0.6019289 |
| TIMM17A | −1.072733126 | 0.051291304 | 0.008270079 | −28.93862603 | 5.982974 | 6.0604012 | 3.9083598 | 8.0246608 | 1.2054667 | 0.6019289 |
| APBA1 | −0.970822845 | 0.057122382 | 0.012221776 | −28.93882603 | 5.982974 | 6.0604012 | 3.9083598 | 1.0866873 | 1.2054667 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| CNO | −0.816352453 | 0.086958113 | 0.028033379 | −28.93882603 | 5.8565586 | 6.0604012 | 6.3358005 | 4.3788962 | 1.2054667 | 0.6019289 |
| LXN | −0.762186333 | 0.107099669 | 0.039413464 | −28.93882603 | 6.8989234 | 6.0604012 | 5.5929159 | 4.9379926 | 7.8156527 | 0.6019289 |
| BAG6 | −1.114100391 | 0.050390282 | 0.007157185 | −28.98366791 | 12.9223282 | 12.4484855 | 11.900255 | 8.0651599 | 8.0651599 | 0.6019289 |
| EFHD2 | −0.923575336 | 0.062190894 | 0.015171307 | −29.05843049 | 11.4220286 | 12.292707 | 12.5936325 | 10.0242622 | 7.4318221 | 0.6019289 |
| YTHDF2 | −1.138011177 | 0.050038461 | 0.006606756 | −29.07475291 | 12.8154861 | 12.972526 | 12.8670565 | 7.244891 | 8.922321 | 8.0053615 |
| SNORA8 | −1.196404616 | 0.049809046 | 0.005397577 | −29.17583876 | 5.3354128 | 6.0604012 | 6.0721689 | 1.0866873 | 1.2054667 | 0.6019289 |
| DCAF12 | −1.191433089 | 0.049809046 | 0.005501886 | −29.17583876 | 5.3044627 | 6.0604012 | 6.0721689 | 1.0866873 | 1.2054667 | 0.6019289 |
| CCNF | −1.219574122 | 0.049622329 | 0.00505737 | −29.1852795 | 5.6586086 | 6.0726357 | 5.7236017 | 5.0495858 | 1.2054667 | 0.6019289 |
| TNPO3 | −0.728074845 | 0.123245219 | 0.048775576 | −29.1852795 | 5.7003762 | 6.0726357 | 6.3358005 | 1.0866873 | 1.2054667 | 0.6019289 |
| FAM70B | −1.184302644 | 0.049897122 | 0.005638289 | −29.56348102 | 6.4179694 | 5.4876732 | 5.5715986 | 1.0866873 | 1.2054667 | 0.6019289 |
| CTRC | −1.213925515 | 0.049622329 | 0.005145631 | −29.58798768 | 5.7445127 | 6.0924064 | 5.5929159 | 1.0866873 | 1.2054667 | 0.6019289 |
| RPP14 | −1.22080848 | 0.049622329 | 0.005041322 | −29.59861642 | 6.2275774 | 5.4876732 | 5.9741452 | 1.0866873 | 1.2054667 | 0.6019289 |
| CD58 | −1.107238322 | 0.050608213 | 0.007373827 | −29.59861642 | 6.4876101 | 4.7365865 | 5.9741452 | 1.0866873 | 1.2054667 | 0.6019289 |
| COPS7B | −0.977041821 | 0.056452334 | 0.01186472 | −29.59861642 | 6.4179694 | 3.8720139 | 5.9741452 | 1.0866873 | 1.2054667 | 0.6019289 |
| WDR27 | −0.892178862 | 0.067585712 | 0.017964375 | −29.59861642 | 6.1437849 | 3.3213504 | 5.9741452 | 1.0866873 | 1.2054667 | 0.6019289 |
| TMPRSS11B | −1.177279086 | 0.04991757 | 0.005870176 | −29.78030621 | 5.982974 | 5.1957839 | 6.3267171 | 1.0866873 | 1.2054667 | 0.6019289 |
| RAB33A | −1.208860195 | 0.04976927 | 0.005243521 | −30.39662533 | 6.6540448 | 5.3621423 | 6.0125266 | 1.0866873 | 1.2054667 | 0.6019289 |
| TRIM44 | −1.181352553 | 0.049897122 | 0.005734574 | −30.39662533 | 6.4532097 | 5.1957839 | 6.0125266 | 1.0866873 | 1.2054667 | 0.6019289 |
| CRABP2 | −0.838843328 | 0.079557207 | 0.02423654 | −30.41814631 | 11.5270824 | 14.3938721 | 14.3065826 | 11.1003391 | 6.6002221 | 9.9375903 |
| WDR90 | −1.216307855 | 0.049622329 | 0.005097489 | −30.56038327 | 5.7530242 | 6.1390574 | 5.5969865 | 1.0866873 | 1.2054667 | 0.6019289 |
| PRICKLE1 | −1.035842696 | 0.052824698 | 0.009485678 | −30.56038327 | 4.309025 | 6.1390574 | 6.3692392 | 1.0866873 | 1.2054667 | 0.6019289 |
| CYTH3 | −0.731745138 | 0.121426098 | 0.047643425 | −30.56038327 | 6.1437849 | 6.1390574 | 7.2279137 | 5.1531951 | 1.2054667 | 0.6019289 |
| COX15 | −1.25591041 | 0.049622329 | 0.005113536 | −30.75447693 | 6.4876101 | 5.7897017 | 5.5446534 | 1.0866873 | 1.2054667 | 0.6019289 |
| ZNF251 | −1.171109561 | 0.04991757 | 0.005974484 | −30.8023879 | 6.2677178 | 5.1480825 | 6.0316576 | 1.0866873 | 1.2054667 | 0.6019289 |
| RLF | −1.192296511 | 0.049809046 | 0.005485838 | −30.89759131 | 5.2635993 | 6.0361098 | 6.3692392 | 1.0866873 | 1.2054667 | 0.6019289 |
| FAM171B | −1.106165494 | 0.050608213 | 0.007405922 | −31.07129311 | 4.6394091 | 6.0441977 | 5.5715986 | 1.0866873 | 1.2054667 | 0.6019289 |
| ARF5 | −1.071804786 | 0.051355105 | 0.008326246 | −31.07129311 | 6.7078705 | 6.0441977 | 4.4498938 | 1.0866873 | 1.2054667 | 0.6019289 |
| SORD | −0.971769164 | 0.056976683 | 0.012134318 | −31.07129311 | 6.6482929 | 6.0441977 | 3.761245 | 1.0866873 | 1.2054667 | 0.6019289 |
| ADSSL1 | −1.197792314 | 0.049809046 | 0.005373506 | −31.19048223 | 5.3044627 | 6.0497213 | 8.0377511 | 1.0866873 | 1.2054667 | 0.6019289 |
| SLC23A3 | −1.109306172 | 0.050523319 | 0.00730081 | −31.19048223 | 4.6394091 | 6.0497213 | 8.1022182 | 1.0866873 | 1.2054667 | 0.6019289 |
| ZFAT | −1.107369817 | 0.050608213 | 0.007349755 | −31.28393853 | 6.3067721 | 4.7365865 | 6.0040376 | 1.0866873 | 1.2054667 | 0.6019289 |
| MTHFD2L | −1.2170735 | 0.049622329 | 0.005089465 | −31.30107976 | 6.0548278 | 7.1293668 | 5.3892653 | 1.0866873 | 1.2054667 | 0.6019289 |
| TECPR2 | −1.18709002 | 0.049875978 | 0.005590147 | −31.30107976 | 6.0548278 | 5.1957839 | 6.7042855 | 1.0866873 | 1.2054667 | 0.6019289 |
| FBXL6 | −1.18119933 | 0.049897122 | 0.005758646 | −31.30107976 | 6.0548278 | 6.1842483 | 5.2176156 | 1.0866873 | 1.2054667 | 0.6019289 |
| ITGA6 | −1.181023415 | 0.049897122 | 0.005766669 | −31.30107976 | 6.0548278 | 8.7980224 | 5.2252164 | 1.0866873 | 1.2054667 | 0.6019289 |
| MCM4 | −1.148160295 | 0.049952273 | 0.006430233 | −31.30107976 | 6.0548278 | 6.7328249 | 4.9444683 | 1.0866873 | 1.2054667 | 0.6019289 |
| B3GALTL | −1.19857482 | 0.049809046 | 0.005365482 | −31.32786522 | 5.3162271 | 6.2280676 | 6.0560619 | 5.6551006 | 1.2054667 | 0.6019289 |
| IPP | −1.182022258 | 0.049897122 | 0.005694456 | −31.32786522 | 6.3447976 | 5.1957839 | 6.0560619 | 1.0866873 | 1.2054667 | 0.6019289 |
| RHCG | −1.177059128 | 0.04991757 | 0.005878199 | −31.32786522 | 6.4876101 | 6.0604012 | 6.0560619 | 1.0866873 | 1.2054667 | 0.6019289 |
| MTSS1 | −1.14578992 | 0.049952273 | 0.006454305 | −31.32786522 | 7.0446837 | 5.1480825 | 6.0560619 | 1.0866873 | 1.2054667 | 0.6019289 |
| PRSS50 | −0.738943623 | 0.118078127 | 0.045694456 | −31.32786522 | 1.8744435 | 4.9115166 | 6.0560619 | 1.0866873 | 1.2054667 | 0.6019289 |
| TRMT61A | −1.042839667 | 0.052218844 | 0.009233732 | −31.33427445 | 6.4876101 | 6.6385363 | 6.0560619 | 1.0866873 | 2.8554202 | 0.6019289 |
| PRMT6 | −0.79735604 | 0.098329277 | 0.031726711 | −31.33427445 | 7.5792405 | 6.6056864 | 5.5715986 | 5.6551006 | 1.2054667 | 0.6019289 |
| EDC4 | −1.259207151 | 0.04958755 | 0.004958755 | −31.33427445 | 6.1437849 | 7.4023354 | 5.5715986 | 1.0866873 | 1.2054667 | 0.6019289 |
| TPCN2 | −0.779496397 | 0.100080374 | 0.004958755 | −31.42223417 | 6.186289 | 6.0604012 | 5.7236017 | 5.6551006 | 1.2054667 | 0.6019289 |
| LOC100507032 | −1.202740978 | 0.049809046 | 0.035314932 | −31.42223417 | 5.3162271 | 6.1842483 | 2.3793449 | 1.0866873 | 1.2054667 | 0.6019289 |
| C3orf62 | −1.105580696 | 0.050608213 | 0.005333387 | −31.53280526 | 4.7435639 | 6.1842483 | 6.1759311 | 1.0866873 | 1.2054667 | 0.6019289 |
| UBR1 | −1.225656217 | 0.049622329 | 0.007438017 | −31.57743994 | 6.186289 | 5.4876732 | 6.0721689 | 1.0866873 | 1.2054667 | 0.6019289 |
| RETSAT | −1.136774466 | 0.050038461 | 0.004969109 | −31.57743994 | 6.186289 | 4.9115166 | 6.1759311 | 1.0866873 | 1.2054667 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| CLCN5 | -1.237209001 | 0.04958755 | 0.004776539 | -31.68983724 | 6.2677178 | 6.0726357 | 5.5446534 | 1.0866873 | 1.2054667 | 0.6019289 |
| TARP | -1.063942599 | 0.051416052 | 0.008555725 | -31.68983724 | 4.2634629 | 6.0726357 | 8.5897647 | 1.0866873 | 1.2054667 | 0.6019289 |
| HIST1H1C | -0.883810095 | 0.068843426 | 0.018824521 | -31.68983724 | 7.0676142 | 6.0726357 | 2.9956812 | 1.0866873 | 1.2054667 | 0.6019289 |
| ARHGEF35 | -1.221577656 | 0.049622329 | 0.005081441 | -31.80070703 | 5.7794294 | 7.1293668 | 5.5929159 | 1.0866873 | 1.2054667 | 0.6019289 |
| SEPX1 | -0.79324218 | 0.094987603 | 0.032376635 | -31.80070703 | 8.3699022 | 7.3237074 | 5.5929159 | 1.0866873 | 6.0753543 | 0.6019289 |
| FBXO25 | -1.224927673 | 0.049622329 | 0.004985156 | -31.89056092 | 6.3818471 | 5.8096013 | 5.5969865 | 1.0866873 | 1.2054667 | 0.6019289 |
| ACVR2B | -1.208399188 | 0.04976927 | 0.005267592 | -31.89056092 | 6.3067721 | 5.6616851 | 5.5969865 | 1.0866873 | 1.2054667 | 0.6019289 |
| H2AFZ | -0.910542856 | 0.064737869 | 0.016312284 | -32.0373946 | 13.0440078 | 14.1167381 | 14.5562622 | 9.1150532 | 11.4398374 | 7.6538745 |
| GMPPB | -0.785968482 | 0.097841721 | 0.033930835 | -32.17829531 | 8.9779688 | 7.3237074 | 5.6099449 | 6.3662802 | 1.2054667 | 0.6019289 |
| PPARGC1B | -1.212919925 | 0.049694878 | 0.00518575 | -32.29645787 | 6.0999914 | 5.3406193 | 6.6706745 | 1.0866873 | 1.2054667 | 0.6019289 |
| RPS6KB2 | -1.046583191 | 0.052154186 | 0.009135842 | -32.29645787 | 6.0999914 | 6.537655 | 4.2859964 | 1.0866873 | 1.2054667 | 0.6019289 |
| DNAJC9 | -1.261701619 | 0.049622329 | 0.004423494 | -32.49420971 | 6.2275774 | 6.0497213 | 5.7236017 | 1.0866873 | 1.2054667 | 0.6019289 |
| PNLDC1 | -1.110250676 | 0.050482841 | 0.007278344 | -32.49420971 | 6.2275774 | 4.7365865 | 6.1759311 | 1.0866873 | 1.2054667 | 0.6019289 |
| TRIT1 | -1.280524846 | 0.04958755 | 0.004118591 | -32.50525139 | 5.8565586 | 6.2280676 | 6.0540376 | 1.0866873 | 1.2054667 | 0.6019289 |
| SNAI3 | -1.184676183 | 0.049897122 | 0.005630266 | -33.18294662 | 5.2636993 | 6.1390574 | 9.6879398 | 1.0866873 | 1.2054667 | 0.6019289 |
| MTO1 | -1.228329408 | 0.049622329 | 0.004945037 | -33.28221884 | 5.6586086 | 5.7897017 | 7.0300422 | 1.0866873 | 1.2054667 | 0.6019289 |
| C12orf76 | -1.237429114 | 0.04958755 | 0.004760491 | -33.29185955 | 6.1437849 | 5.4876732 | 6.4897707 | 1.0866873 | 1.2054667 | 0.6019289 |
| SOX7 | -1.259545707 | 0.04958755 | 0.004463612 | -33.35326768 | 6.4876101 | 5.6616851 | 6.0721689 | 1.0866873 | 1.2054667 | 0.6019289 |
| CPEB1 | -1.223136817 | 0.049622329 | 0.005017251 | -33.35326768 | 5.7445127 | 5.6616851 | 7.0563116 | 1.0866873 | 1.2054667 | 0.6019289 |
| VPS13B | -0.763277617 | 0.10685386 | 0.039164728 | -33.35326768 | 6.5212096 | 5.6616851 | 6.9199049 | 1.0866873 | 1.2054667 | 0.6019289 |
| APBB3 | -0.933940862 | 0.060990824 | 0.014438739 | -33.47771963 | 6.2677178 | 6.270596 | 7.2279137 | 5.2498839 | 4.1976103 | 0.6019289 |
| GALM | -0.804296008 | 0.090718963 | 0.030062585 | -33.47771963 | 5.7003762 | 6.270596 | 8.0638846 | 5.2498839 | 1.2054667 | 0.6019289 |
| EXT1 | -1.04765316 | 0.052136699 | 0.009105352 | -33.49064808 | 11.7727085 | 12.5927431 | 12.0365324 | 6.983347 | 1.2054667 | 9.0248218 |
| IYD | -1.266906035 | 0.04958755 | 0.004359304 | -33.76455956 | 6.2677178 | 5.6616851 | 6.2829045 | 1.0866873 | 1.2054667 | 0.6019289 |
| RASSF6 | -0.933318064 | 0.061078464 | 0.014507743 | -34.03579391 | 7.6263253 | 7.7863852 | 7.5934735 | 5.4258059 | 2.5373444 | 0.6019289 |
| WDPCP | -1.260253752 | 0.04958755 | 0.004447565 | -34.23881777 | 7.0446897 | 6.1842483 | 5.5969865 | 1.0866873 | 1.2054667 | 0.6019289 |
| PFN1P2 | -1.260215045 | 0.04958755 | 0.004455589 | -34.23881777 | 6.7078705 | 6.1842483 | 5.5969865 | 1.0866873 | 1.2054667 | 0.6019289 |
| MRPS22 | -1.2277063 | 0.049622329 | 0.004953061 | -34.23881777 | 7.2788106 | 6.1842483 | 5.3892653 | 5.2498839 | 1.2054667 | 0.6019289 |
| MOSPD3 | -1.201089531 | 0.049809046 | 0.005349434 | -34.23881777 | 6.8989234 | 6.1842483 | 5.2176156 | 1.0866873 | 1.2054667 | 0.6019289 |
| LTB4R | -1.128416792 | 0.050237584 | 0.006805745 | -34.23881777 | 6.8468682 | 6.1842483 | 4.7549172 | 1.0866873 | 1.2054667 | 0.6019289 |
| NQO1 | -1.01812465 | 0.053512074 | 0.010042526 | -34.23881777 | 7.373845 | 6.1842483 | 3.9352215 | 1.0866873 | 1.2054667 | 0.6019289 |
| ASAP3 | -1.08124665 | 0.051255379 | 0.008099976 | -34.28728281 | 6.186289 | 4.4133226 | 7.1074578 | 1.0866873 | 1.2054667 | 0.6019289 |
| KCNIP3 | -1.274145011 | 0.04958755 | 0.004214876 | -34.32012535 | 7.2983248 | 6.1842483 | 5.7029118 | 1.0866873 | 1.2054667 | 0.6019289 |
| LMO2 | -1.267546241 | 0.04958755 | 0.00435128 | -34.32012535 | 7.021395 | 6.0924064 | 5.7029118 | 1.0866873 | 1.2054667 | 0.6019289 |
| MAPKBP1 | -1.232379554 | 0.04958755 | 0.004832705 | -34.32012535 | 5.7530242 | 6.7020747 | 5.7029118 | 1.0866873 | 1.2054667 | 0.6019289 |
| NDST2 | -0.822231852 | 0.085361525 | 0.027074541 | -34.32012535 | 7.4279993 | 7.0089004 | 5.7029118 | 5.2498839 | 1.2054667 | 0.6019289 |
| ANKRD13C | -1.27341299 | 0.049809046 | 0.004230924 | -34.80566947 | 5.7794294 | 6.0604012 | 6.3267171 | 1.0866873 | 1.2054667 | 0.6019289 |
| RPL36A | -1.269310645 | 0.04958755 | 0.004319185 | -34.80566947 | 5.7445127 | 6.0726357 | 6.3267171 | 1.0866873 | 1.2054667 | 0.6019289 |
| ZNF623 | -1.214978782 | 0.049897122 | 0.005137607 | -35.2827259 | 6.2275774 | 5.3406193 | 6.3558005 | 1.0866873 | 1.2054667 | 0.6019289 |
| DPY19L2P2 | -1.183217577 | 0.049897122 | 0.005562361 | -35.2827259 | 6.2275774 | 5.1480825 | 6.3558005 | 1.0866873 | 1.2054667 | 0.6019289 |
| LOC440896 | -1.255516058 | 0.04958755 | 0.004454385 | -35.29471513 | 8.085359 | 6.2280676 | 5.6099449 | 1.0866873 | 1.2054667 | 0.6019289 |
| BNIP1 | -1.23138098 | 0.04958755 | 0.004856776 | -35.29471513 | 6.8989234 | 6.2280676 | 5.3892653 | 1.0866873 | 1.2054667 | 0.6019289 |
| BTNL9 | -1.06045766 | 0.051535817 | 0.008660034 | -35.29471513 | 4.309025 | 6.2280676 | 6.7042855 | 1.0866873 | 1.2054667 | 0.6019289 |
| ZNF502 | -1.01282874 | 0.054044749 | 0.010250341 | -35.29471513 | 6.9736463 | 6.2280676 | 3.9352215 | 1.0866873 | 1.2054667 | 0.6019289 |
| THBS3 | -1.264919754 | 0.04958755 | 0.004375351 | -35.32417139 | 5.7445127 | 6.0361098 | 7.273415 | 1.0866873 | 1.2054667 | 0.6019289 |
| SERPINB6 | -0.971103796 | 0.057101475 | 0.012198508 | -35.39604594 | 11.2844606 | 10.4146205 | 10.5083079 | 8.5376958 | 5.3627916 | 0.6019289 |
| TMEM62 | -0.793120439 | 0.094990031 | 0.03240076 | -35.51444079 | 7.1123989 | 6.0726357 | 6.3558005 | 5.2498839 | 1.2054667 | 0.6019289 |
| DOCK7 | -1.272727649 | 0.04958755 | 0.004238947 | -35.53319016 | 5.7530242 | 6.7328249 | 6.0560619 | 1.0866873 | 1.2054667 | 0.6019289 |
| LRFN4 | -1.26943836 | 0.04958755 | 0.004303137 | -35.53319016 | 5.7530242 | 7.1748717 | 6.0560619 | 1.0866873 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| SRL | −1.268528049 | 0.04958755 | 0.004343256 | −36.35063649 | 8.518743 | 6.270596 | 5.7236017 | 1.0866873 | 1.2054667 | 0.6019289 |
| ZSCAN21 | −1.175037579 | 0.04991757 | 0.005902271 | −36.35063649 | 6.8731305 | 6.270596 | 5.018694 | 1.0866873 | 1.2054667 | 0.6019289 |
| SYNJ2 | −1.112777237 | 0.050440463 | 0.007198909 | −36.35063649 | 4.6820765 | 6.270596 | 6.4507011 | 1.0866873 | 1.2054667 | 0.6019289 |
| PCK2 | −1.230799732 | 0.04958755 | 0.004872824 | −36.39523994 | 6.3818471 | 6.3911446 | 5.3892653 | 1.0866873 | 1.2054667 | 0.6019289 |
| ZHX1-C8ORF76 | −1.261405628 | 0.04958755 | 0.004431517 | −36.44812728 | 5.982974 | 5.7897017 | 7.5386226 | 1.0866873 | 1.2054667 | 0.6019289 |
| B4GALNT4 | −1.275059723 | 0.04958755 | 0.004174757 | −36.66209183 | 5.6586086 | 7.4949535 | 6.2829045 | 1.0866873 | 1.2054667 | 0.6019289 |
| CLDN15 | −1.329566658 | 0.04958755 | 0.003613095 | −36.88795755 | 6.0999914 | 6.1842483 | 6.4105447 | 1.0866873 | 1.2054667 | 0.6019289 |
| CHEK1 | −0.901713374 | 0.066175504 | 0.017023189 | −36.88795755 | 6.3818471 | 7.08238 | 6.4105447 | 4.5400907 | 1.2054667 | 0.6019289 |
| FAM178A | −0.788886416 | 0.096395323 | 0.033205488 | −36.88795755 | 6.8201191 | 6.0361098 | 6.4105447 | 5.1531951 | 1.2054667 | 0.6019289 |
| JRK | −0.832007614 | 0.082058134 | 0.025363075 | −36.9740458 | 8.1076531 | 7.1293668 | 8.0638846 | 6.2771857 | 2.8554202 | 0.6019289 |
| PARP16 | −0.877918856 | 0.070255881 | 0.019571532 | −37.07828671 | 6.4179694 | 6.0361098 | 7.4620859 | 4.6851838 | 1.2054667 | 0.6019289 |
| SPATA5 | −1.255842775 | 0.04958755 | 0.004535826 | −37.27366545 | 6.3067721 | 6.4662577 | 5.5446534 | 1.0866873 | 1.2054667 | 0.6019289 |
| COLQ | −1.231269334 | 0.04958755 | 0.0048648 | −37.27366545 | 6.3067721 | 5.3621423 | 6.7692467 | 1.0866873 | 1.2054667 | 0.6019289 |
| ZNF710 | −1.128926595 | 0.050187311 | 0.006789698 | −37.27366545 | 6.3067721 | 6.7629335 | 4.7244061 | 1.0866873 | 1.2054667 | 0.6019289 |
| C1orf212 | −0.897611169 | 0.066733582 | 0.017375431 | −37.37678042 | 7.0676142 | 6.4291897 | 6.0540376 | 4.3788962 | 1.2054667 | 0.6019289 |
| SCYL2 | −1.284354792 | 0.04958755 | 0.00409452 | −37.40657992 | 6.5540448 | 6.3119075 | 5.7029118 | 1.0866873 | 1.2054667 | 0.6019289 |
| STK11IP | −1.270738335 | 0.04958755 | 0.0042870 | −37.40657992 | 6.8731305 | 6.3119075 | 5.5969865 | 1.0866873 | 1.2054667 | 0.6019289 |
| HSF4 | −1.065861929 | 0.051378258 | 0.008475487 | −37.40657992 | 4.2098819 | 6.3119075 | 7.5571389 | 1.0866873 | 1.2054667 | 0.6019289 |
| NPAS2 | −1.007449898 | 0.054397005 | 0.010546417 | −37.40657992 | 6.6175557 | 6.3119075 | 3.9352215 | 1.0866873 | 1.2054667 | 0.6019289 |
| FAM59B | −1.231743915 | 0.04958755 | 0.004840729 | −37.7925454 | 7.2186326 | 5.3406193 | 6.3267171 | 1.0866873 | 1.2054667 | 0.6019289 |
| KIF1A | −1.254995019 | 0.04958755 | 0.004559897 | −38.1769435 | 5.8565586 | 8.6767186 | 6.0125266 | 1.0866873 | 1.2054667 | 0.6019289 |
| SAMD5 | −0.999252242 | 0.055166136 | 0.010950814 | −38.1769435 | 5.8565586 | 7.1060646 | 6.976024 | 3.7493131 | 1.2054667 | 0.6019289 |
| NPHP4 | −1.302686423 | 0.04958755 | 0.003885902 | −38.26915924 | 6.3447976 | 5.7897017 | 6.6706745 | 1.0866873 | 1.2054667 | 0.6019289 |
| C9orf89 | −0.841722311 | 0.078901035 | 0.023763941 | −38.29158551 | 10.2314132 | 9.9743873 | 10.0760433 | 4.8170878 | 1.2054667 | 9.0502468 |
| GUF1 | −0.767488199 | 0.104915156 | 0.038107197 | −38.34033568 | 7.0676142 | 6.4662577 | 6.2829045 | 5.6551006 | 1.2054667 | 0.6019289 |
| ABCB4 | −1.179716366 | 0.049897122 | 0.005798764 | −38.46254365 | 5.0569476 | 6.3520696 | 6.564874 | 1.0866873 | 1.2054667 | 0.6019289 |
| RHOF | −1.062277841 | 0.051458876 | 0.00858782 | −38.46254365 | 4.309025 | 6.3520696 | 6.564874 | 1.0866873 | 1.2054667 | 0.6019289 |
| PRC1 | −1.161495204 | 0.04991757 | 0.006167054 | −38.56214049 | 6.7928648 | 4.9115166 | 6.3558005 | 1.0866873 | 1.2054667 | 0.6019289 |
| TNFRSF12A | −1.137824052 | 0.050038461 | 0.00661478 | −38.70541355 | 11.1337373 | 13.1996494 | 12.0637791 | 1.0866873 | 6.9843361 | 7.925186 |
| BHLHE22 | −1.310318837 | 0.04958755 | 0.003821712 | −39.26466745 | 6.3818471 | 5.8096013 | 7.1104578 | 1.0866873 | 1.2054667 | 0.6019289 |
| SLC25A22 | −1.271236738 | 0.04958755 | 0.004279066 | −39.26466745 | 6.3818471 | 6.6056864 | 5.5929159 | 1.0866873 | 1.2054667 | 0.6019289 |
| PROM1 | −1.231696113 | 0.04958755 | 0.004848752 | −39.26466745 | 6.3818471 | 8.7907325 | 5.3892653 | 1.0866873 | 1.2054667 | 0.6019289 |
| SUV420H1 | −0.802865156 | 0.091189447 | 0.030346626 | −39.27019233 | 5.8972917 | 6.8213295 | 6.8006628 | 5.1531951 | 1.2054667 | 0.6019289 |
| ACHE | −1.307305838 | 0.04958755 | 0.003853807 | −39.31290468 | 6.6048278 | 6.5023977 | 6.0125266 | 1.0866873 | 1.2054667 | 0.6019289 |
| FLJ32224 | −1.163716343 | 0.049897122 | 0.006134959 | −39.51852612 | 6.5861495 | 6.3911446 | 4.9444683 | 1.0866873 | 1.2054667 | 0.6019289 |
| ZNF500 | −0.828724094 | 0.082955513 | 0.02590548 | −39.82888789 | 6.5212096 | 6.8774542 | 6.2829045 | 5.0495858 | 1.2054667 | 0.6019289 |
| GDNF | −0.757422237 | 0.109447664 | 0.040601781 | −39.82888789 | 6.5212096 | 6.0924064 | 7.0563116 | 5.6551006 | 2.5373444 | 0.6019289 |
| ITGB5 | −1.196102237 | 0.049809046 | 0.005413624 | −39.97341997 | 14.4842014 | 14.590751 | 13.3011693 | 9.5214323 | 8.5186068 | 9.2054107 |
| PIKFYVE | −1.302147289 | 0.04958755 | 0.003893926 | −40.05352667 | 5.7794294 | 8.0963775 | 6.4105447 | 1.0866873 | 1.2054667 | 0.6019289 |
| PCMT1 | −1.135012583 | 0.050038461 | 0.006662922 | −40.25016683 | 12.0285424 | 11.7397701 | 11.5042513 | 6.4088472 | 1.2054667 | 7.925186 |
| SETMAR | −1.215484752 | 0.049622329 | 0.005129584 | −40.26018907 | 6.4179694 | 6.7924268 | 5.2252164 | 1.0866873 | 1.2054667 | 0.6019289 |
| PSAT1 | −0.812862157 | 0.088193489 | 0.02863837 | −40.26018907 | 6.4179694 | 7.4213407 | 2.1654208 | 1.0866873 | 1.2054667 | 0.6019289 |
| ERMP1 | −1.179438344 | 0.049897122 | 0.005822836 | −40.28548644 | 6.5212096 | 6.4291897 | 5.018694 | 1.0866873 | 1.2054667 | 0.6019289 |
| G0S2 | −0.840819309 | 0.079098445 | 0.023875471 | −40.30282763 | 7.7590076 | 8.0530528 | 7.8701536 | 6.6046733 | 2.5373444 | 0.6019289 |
| XPO4 | −1.274663474 | 0.04958755 | 0.004198829 | −40.57452592 | 6.6175557 | 6.4291897 | 5.5969865 | 1.0866873 | 1.2054667 | 0.6019289 |
| NRP2 | −1.187535678 | 0.049875978 | 0.005574099 | −40.57452592 | 7.1342805 | 6.4291897 | 7.0563116 | 1.0866873 | 1.2054667 | 0.6019289 |
| ASRGL1 | −1.3620059 | 0.04958755 | 0.00332424 | −40.74576236 | 6.5540448 | 6.1842483 | 5.018694 | 1.0866873 | 1.2054667 | 0.6019289 |
| ANKAR | −1.315309508 | 0.04958755 | 0.00377357 | −40.74576236 | 6.5540448 | 6.0726357 | 6.0560619 | 1.0866873 | 1.2054667 | 0.6019289 |
| PAN3-AS1 | −0.87914413 | 0.069835403 | 0.019332424 | −40.74576236 | 6.5540448 | 6.0924064 | 6.8910052 | 4.5400907 | 1.2054667 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| CDH13 | −1.310142409 | 0.04958755 | 0.003829736 | −41.05275997 | 6.4532097 | 5.8096013 | 6.564874 | 1.0866873 | 1.2054667 | 0.6019289 |
| RPS6KA5 | −0.82227276 | 0.085361525 | 0.027066517 | −41.05275997 | 6.2275774 | 6.5720715 | 6.564874 | 4.9379926 | 1.2054667 | 0.6019289 |
| SLAMF1 | −1.145061522 | 0.049952273 | 0.006470352 | −41.25572316 | 6.4532097 | 4.7365865 | 7.1323668 | 1.0866873 | 1.2054667 | 0.6019289 |
| LRP8 | −1.088987639 | 0.051077531 | 0.007860066 | −41.25572316 | 6.4532097 | 6.6056864 | 4.4498938 | 1.0866873 | 1.2054667 | 0.6019289 |
| CCDC22 | −0.82134412 | 0.085414368 | 0.027187676 | −41.25808009 | 7.6416849 | 6.5720715 | 6.4105447 | 5.5826351 | 1.2054667 | 0.6019289 |
| XRRA1 | −0.819898981 | 0.085792514 | 0.027378641 | −41.25808009 | 6.5861495 | 6.5720715 | 6.1759311 | 4.9379926 | 1.2054667 | 0.6019289 |
| SCAND2 | −0.727611054 | 0.123575599 | 0.048946482 | −41.32802826 | 8.2244688 | 8.3396934 | 8.313014 | 7.522033 | 2.8545202 | 2.9363609 |
| REPIN1 | −1.010947882 | 0.054161962 | 0.010362674 | −41.41765033 | 11.4797912 | 11.4527639 | 10.7038034 | 6.0805901 | 8.4493889 | 0.6019289 |
| CACNA1H | −1.278012966 | 0.04958755 | 0.004134639 | −41.63054178 | 7.463005 | 6.4662577 | 5.5715986 | 1.0866873 | 1.2054667 | 0.6019289 |
| SCFD2 | −1.346879903 | 0.03468667 | 0.009403835 | −42.09399983 | 6.4179694 | 6.0441977 | 6.6010094 | 1.0866873 | 1.2054667 | 0.6019289 |
| STC2 | −1.038058792 | 0.052564289 | 0.013102784 | −42.25126886 | 6.4876101 | 7.5649923 | 3.9352215 | 1.0866873 | 1.2054667 | 0.6019289 |
| NR5A2 | −0.953561114 | 0.058581361 | 0.00441547 | −42.25126886 | 6.4876101 | 6.270596 | 6.5278107 | 1.0866873 | 3.9031434 | 0.6019289 |
| LOC100133091 | −1.261717222 | 0.04958755 | 0.003942069 | −42.31459405 | 5.4911209 | 7.0207471 | 6.4897707 | 1.0866873 | 1.2054667 | 0.6019289 |
| INPP5D | −1.298416296 | 0.04958755 | 0.015710503 | −42.40836537 | 6.0082059 | 6.270596 | 8.8671038 | 5.7241063 | 1.2054667 | 0.6019289 |
| REXO4 | −0.916377462 | 0.063342057 | 0.041839044 | −42.53556349 | 8.1830764 | 8.2888552 | 6.0125266 | 1.0866873 | 1.2054667 | 0.6019289 |
| SLC35C1 | −0.752574811 | 0.111643653 | 0.003749499 | −42.53556349 | 6.9242634 | 7.4586165 | 6.0125266 | 5.5826351 | 1.2054667 | 0.6019289 |
| NSMAF | −1.318446245 | 0.04958755 | 0.00396614 | −42.57955515 | 6.6175557 | 5.8096013 | 6.6010094 | 1.0866873 | 1.2054667 | 0.6019289 |
| ZBTB39 | −1.296949779 | 0.04991757 | 0.005958437 | −42.68657254 | 6.6482929 | 6.5023977 | 5.7029118 | 1.0866873 | 1.2054667 | 0.6019289 |
| CWF19L1 | −1.171736265 | 0.04991757 | 0.005958437 | −42.68657254 | 6.7078705 | 6.5023977 | 4.9444683 | 1.0866873 | 1.2054667 | 0.6019289 |
| EIF4EBP1 | −1.009282897 | 0.054296381 | 0.010482227 | −42.68657254 | 7.2590288 | 6.5023977 | 3.7641245 | 1.0866873 | 1.2054667 | 0.6019289 |
| GPRIN1 | −1.34524293 | 0.04958755 | 0.003492739 | −43.10336796 | 6.3818471 | 6.7924268 | 6.0316576 | 1.0866873 | 1.2054667 | 0.6019289 |
| ISLR2 | −0.765630944 | 0.105690271 | 0.038530851 | −43.13525319 | 7.2389721 | 6.0726357 | 6.6326622 | 5.7241063 | 1.2054667 | 0.6019289 |
| DAGLA | −1.321482684 | 0.04958755 | 0.003701356 | −43.24682539 | 6.5212096 | 5.8096013 | 7.1809309 | 1.0866873 | 1.2054667 | 0.6019289 |
| LOC401127 | −1.318003394 | 0.04958755 | 0.003757522 | −43.24682539 | 6.5212096 | 5.8096013 | 7.6463154 | 1.0866873 | 1.2054667 | 0.6019289 |
| ZNF589 | −1.154505115 | 0.04991757 | 0.006327529 | −43.24682539 | 6.5212096 | 4.8079702 | 6.861515 | 1.0866873 | 1.2054667 | 0.6019289 |
| FAM115C | −0.935446678 | 0.060847991 | 0.01432079 | −43.49646331 | 6.6482929 | 6.3911446 | 7.3812609 | 4.5400907 | 1.2054667 | 0.6019289 |
| RSPRY1 | −1.32103371 | 0.04958755 | 0.00370938 | −43.64644834 | 6.1437849 | 6.0497213 | 7.1074578 | 1.0866873 | 1.2054667 | 0.6019289 |
| SFXN1 | −1.346500584 | 0.04958755 | 0.003484715 | −43.77722656 | 8.2039211 | 6.537655 | 6.0540376 | 1.0866873 | 1.2054667 | 0.6019289 |
| POLR1C | −1.334331058 | 0.04958755 | 0.003581 | −43.77722656 | 6.2677178 | 7.2405467 | 6.0540376 | 1.0866873 | 1.2054667 | 0.6019289 |
| POU3F1 | −1.315525305 | 0.04958755 | 0.003765546 | −43.80121316 | 6.0548278 | 6.3119075 | 8.5253933 | 5.6675757 | 1.2054667 | 0.6019289 |
| C16orf54 | −0.742108103 | 0.116965003 | 0.044718768 | −43.80121316 | 6.0548278 | 6.7328249 | 6.976024 | 5.8529567 | 1.2054667 | 0.6019289 |
| FAM122B | −1.344170962 | 0.04958755 | 0.003500762 | −43.83869544 | 7.2186326 | 6.3520696 | 6.0560619 | 1.0866873 | 1.2054667 | 0.6019289 |
| AGTRAP | −0.74263594 | 0.116661419 | 0.044546257 | −43.83869544 | 8.6836453 | 8.2035936 | 6.0560619 | 7.522033 | 1.2054667 | 0.6019289 |
| ATP6V0A2 | −1.360198297 | 0.04958755 | 0.045727353 | −43.83869544 | 7.7015384 | 7.282726 | 7.3812609 | 6.5675757 | 1.2054667 | 6.7657063 |
| SGIP1 | −1.336401969 | 0.04958755 | 0.003548905 | −43.97075077 | 7.2788106 | 6.0604012 | 6.2829045 | 1.0866873 | 1.2054667 | 0.6019289 |
| CLEC4E | −1.106224223 | 0.050608213 | 0.007397898 | −44.24239204 | 6.5540448 | 4.3513152 | 8.1197247 | 5.5826351 | 1.2054667 | 0.6019289 |
| TARBP2 | −1.312720057 | 0.04958755 | 0.003805665 | −44.33087692 | 7.2788106 | 6.0726357 | 6.0721689 | 5.2498839 | 1.2054667 | 0.6019289 |
| SLC7A5 | −1.0737793 | 0.051291304 | 0.008246008 | −44.34220984 | 12.236315 | 13.1215399 | 11.8653879 | 9.3352666 | 1.2054667 | 0.6019289 |
| BRAP | −1.360198297 | 0.04958755 | 0.003340287 | −44.34522153 | 7.2590288 | 6.0726357 | 6.4897707 | 1.0866873 | 1.2054667 | 0.6019289 |
| HGF | −0.845168108 | 0.077954823 | 0.023248014 | −44.34522153 | 8.234634 | 6.0726357 | 6.8910052 | 5.5826351 | 1.2054667 | 0.6019289 |
| QPRT | −0.819629312 | 0.085991355 | 0.027476531 | −44.34522153 | 6.8989234 | 6.0726357 | 6.976024 | 5.2498839 | 1.2054667 | 0.6019289 |
| PDE4B | −1.216104931 | 0.049622329 | 0.005105512 | −44.41337869 | 6.6783891 | 5.1957839 | 6.6010094 | 1.0866873 | 1.2054667 | 0.6019289 |
| DDIT4L | −0.940386813 | 0.060114874 | 0.013983792 | −44.57573489 | 6.8201191 | 3.3213504 | 6.564874 | 1.0866873 | 1.2054667 | 0.6019289 |
| LOC440944 | −0.863501351 | 0.07316741 | 0.020872984 | −44.81437991 | 8.3882311 | 8.101237 | 8.4180516 | 6.9015613 | 2.9023413 | 0.6019289 |
| C8orf73 | −1.329536207 | 0.04958755 | 0.003621119 | −45.19409703 | 6.0999914 | 6.1390574 | 6.8314096 | 1.0866873 | 1.2054667 | 0.6019289 |
| CAMSAP1 | −0.780687291 | 0.099766818 | 0.03502367 | −45.21779682 | 6.2275774 | 7.6317881 | 6.7042855 | 5.9133149 | 1.2054667 | 0.6019289 |
| FCHSD1 | −1.148806111 | 0.049952273 | 0.00642221 | −45.23796818 | 6.5861495 | 4.7365865 | 6.976024 | 1.0866873 | 1.2054667 | 0.6019289 |
| MMP10 | −1.274777825 | 0.04958755 | 0.004190805 | −45.70632956 | 7.4971815 | 5.4876732 | 6.6010094 | 1.0866873 | 1.2054667 | 0.6019289 |
| GNL3L | −0.819243207 | 0.08612692 | 0.027570408 | −45.75827541 | 8.2647067 | 8.0533052 | 7.8402254 | 7.070287 | 2.5373444 | 0.6019289 |

TABLE 9-continued

Differentially Expressed Genes in CD10-, CD24-, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| TNFRSF25 | -0.967924895 | 0.057313185 | 0.012451256 | -46.12120124 | 6.4452097 | 6.7328249 | 9.0869404 | 4.9379926 | 1.2054667 | 0.6019289 |
| IQSEC2 | -1.368007005 | 0.04958755 | 0.00326005 | -46.2335532 | 6.6175557 | 6.0497213 | 7.273415 | 1.0866873 | 1.2054667 | 0.6019289 |
| KIAA0415 | -0.821941638 | 0.086019863 | 0.027507823 | -46.29908547 | 6.5861495 | 8.0037262 | 6.7371315 | 5.9712523 | 1.2054667 | 0.6019289 |
| KDM2B | -0.789394032 | 0.096229838 | 0.033085132 | -46.58701386 | 6.1437849 | 6.8496647 | 7.481604 | 5.7899671 | 1.2054667 | 0.6019289 |
| C8orf86 | -1.180045145 | 0.049897122 | 0.005782717 | -47.11544113 | 10.3669723 | 10.806712 | 10.1109305 | 6.4088472 | 4.8088443 | 0.6019289 |
| DTNB | -1.347770316 | 0.04958755 | 0.003444596 | -47.22914655 | 6.6482929 | 8.1129752 | 5.9741452 | 1.0866873 | 1.2054667 | 0.6019289 |
| PRSS53 | -1.290519788 | 0.04958755 | 0.004022306 | -47.22914655 | 6.6482929 | 7.1522986 | 5.5715986 | 1.0866873 | 1.2054667 | 0.6019289 |
| MGC12982 | -1.098430029 | 0.050846008 | 0.007590468 | -47.22914655 | 6.6482929 | 4.3899364 | 6.976024 | 1.0866873 | 1.2054667 | 0.6019289 |
| BFAR | -0.730330556 | 0.122185801 | 0.048102383 | -47.30038439 | 6.5861495 | 6.8213295 | 6.7692467 | 6.2304884 | 1.2054667 | 0.6019289 |
| SLC18A2 | -1.387209714 | 0.04958755 | 0.003115622 | -47.63672085 | 6.6175557 | 7.3830764 | 6.1759311 | 1.0866873 | 1.2054667 | 0.6019289 |
| MID2 | -1.393121706 | 0.04958755 | 0.003059456 | -47.96691659 | 7.2590288 | 6.6706551 | 6.1759311 | 1.0866873 | 1.2054667 | 0.6019289 |
| SLC27A4 | -0.915008348 | 0.063651711 | 0.015839685 | -47.96691659 | 7.1980024 | 6.6706551 | 2.9956812 | 1.0866873 | 1.2054667 | 0.6019289 |
| DZIP1L | -1.3142787 | 0.04958755 | 0.003789617 | -47.96756191 | 5.7003762 | 7.3437697 | 6.6706745 | 1.0866873 | 1.2054667 | 0.6019289 |
| MADD | -1.307318272 | 0.04958755 | 0.003845784 | -47.96756191 | 7.1980024 | 5.6616851 | 6.6706745 | 1.0866873 | 1.2054667 | 0.6019289 |
| NPW | -1.385451107 | 0.04958755 | 0.003139693 | -47.97996091 | 6.186289 | 7.2189854 | 6.564874 | 1.0866873 | 1.2054667 | 0.6019289 |
| FGFR3 | -0.989652067 | 0.055830986 | 0.011294231 | -47.97996091 | 6.186289 | 7.1970971 | 9.451056 | 4.9379926 | 1.2054667 | 0.6019289 |
| ABCA1 | -0.7378705 | 0.118499692 | 0.045988125 | -47.97996091 | 6.186289 | 6.8774542 | 7.8402254 | 1.0866873 | 6.6504789 | 0.6019289 |
| PDZK1IP1 | -1.246212416 | 0.04958755 | 0.004664206 | -48.08110433 | 6.7928648 | 8.225386 | 5.5969865 | 1.6938929 | 1.2054667 | 0.6019289 |
| LOC349196 | -0.776405308 | 0.101218075 | 0.035949611 | -48.08110433 | 6.7928648 | 6.6056864 | 8.7909179 | 6.7770801 | 1.2054667 | 0.6019289 |
| LYSMD2 | -1.296386231 | 0.04958755 | 0.003974164 | -48.22474775 | 6.6783891 | 7.2189854 | 5.5929159 | 1.0866873 | 1.2054667 | 0.6019289 |
| LMBR1L | -1.388247678 | 0.067567176 | 0.017940303 | -48.99805002 | 6.8201191 | 6.5023977 | 7.6113033 | 5.1531951 | 1.2054667 | 0.6019289 |
| TFAP2A | -0.801269748 | 0.091903585 | 0.030705288 | -48.99805002 | 6.8201191 | 8.2784691 | 6.8910052 | 5.7241063 | 1.2054667 | 0.6019289 |
| EXD2 | -1.363416853 | 0.04958755 | 0.003308192 | -49.02301788 | 6.6082059 | 6.7020747 | 6.8314096 | 1.0866873 | 1.2054667 | 0.6019289 |
| HHIPL1 | -1.376997207 | 0.04958755 | 0.003187836 | -49.09819765 | 6.9491661 | 6.0726357 | 6.7042855 | 6.4903918 | 1.2054667 | 0.6019289 |
| NRM | -0.945047362 | 0.059600929 | 0.01368932 | -49.3729357 | 6.2275774 | 7.9653908 | 9.729351 | 5.9133149 | 1.2054667 | 0.6019289 |
| SCNN1D | -1.188371026 | 0.049809046 | 0.005550028 | -49.38301053 | 4.963444 | 7.7629335 | 6.8314096 | 1.0866873 | 1.2054667 | 0.6019289 |
| MLLT4 | -0.740979105 | 0.117645691 | 0.045075824 | -49.38301053 | 6.5212096 | 7.2617905 | 6.8314096 | 6.3662802 | 1.2054667 | 0.6019289 |
| PI4K2A | -1.236807626 | 0.04958755 | 0.004784562 | -50.14064835 | 12.9053268 | 13.4403826 | 14.1951669 | 8.5472581 | 7.8774997 | 0.6019289 |
| LOC286467 | -1.388247678 | 0.04958755 | 0.003099575 | -50.21597183 | 6.7367617 | 6.1390574 | 6.861515 | 1.0866873 | 1.2054667 | 0.6019289 |
| TFAP2A | -1.139489964 | 0.050038461 | 0.006582685 | -50.21597183 | 6.7367617 | 8.2784691 | 4.5083337 | 1.0866873 | 5.7625232 | 0.6019289 |
| EXD2 | -0.77576077 | 0.101475033 | 0.036091631 | -50.22884531 | 8.1296079 | 7.4949535 | 6.7371315 | 1.0866873 | 1.2054667 | 0.6019289 |
| HHIPL1 | -0.788475009 | 0.096602025 | 0.033340287 | -50.24336677 | 7.9805393 | 6.8496647 | 6.861515 | 1.0866873 | 1.2054667 | 0.6019289 |
| CDC42EP2 | -0.757540682 | 0.109414016 | 0.040571291 | -50.4243366 | 7.7015384 | 6.3911446 | 7.2508437 | 6.4903918 | 1.2054667 | 0.6019289 |
| VAMP3 | -0.740246657 | 0.117838959 | 0.045241916 | -50.4243366 | 8.1830764 | 6.3520696 | 6.564874 | 6.3662802 | 6.7399276 | 0.6019289 |
| TMEM222 | -1.082457507 | 0.051255379 | 0.008059857 | -50.5178631 | 5.1211593 | 10.4212449 | 10.7826361 | 6.7442069 | 1.2054667 | 0.6019289 |
| DNAJB13 | -1.374263704 | 0.04958755 | 0.003211907 | -50.76593604 | 11.7356106 | 6.3520696 | 6.3558005 | 8.1174489 | 5.7625232 | 0.6019289 |
| MEX3A | -0.889466152 | 0.068025256 | 0.018218727 | -50.76593604 | 6.2677178 | 7.2405467 | 6.3558005 | 1.0866873 | 1.2054667 | 7.6538745 |
| PPP1R13B | -1.346693475 | 0.04958755 | 0.003476691 | -50.867318 | 6.2677178 | 7.5987767 | 7.7784397 | 5.5063453 | 10.3453823 | 0.6019289 |
| NRM | -0.739167854 | 0.118017692 | 0.045611811 | -50.867318 | 6.3067721 | 6.270596 | 8.313014 | 1.0866873 | 1.2054667 | 6.5688072 |
| RABEPK | -0.777610808 | 0.100926453 | 0.03572976 | -50.98452513 | 7.1770729 | 6.270596 | 7.2508437 | 8.2753779 | 5.3627916 | 0.6019289 |
| NCAPD3 | -1.364776213 | 0.04958755 | 0.003276097 | -51.2115939 | 6.7650859 | 6.8774542 | 6.564874 | 6.0269554 | 1.2054667 | 6.5688072 |
| EDNRB | -1.161692014 | 0.04991757 | 0.006159031 | -51.22922893 | 16.0242776 | 14.3204681 | 14.5115642 | 10.195188 | 6.7399276 | 0.6019289 |
| KCNC4 | -1.282841303 | 0.04991757 | 0.004110567 | -51.35950412 | 5.4911209 | 7.1060646 | 7.7692467 | 1.0866873 | 1.2054667 | 0.6019289 |
| OTUD4 | -1.165494096 | 0.04991757 | 0.006086817 | -51.8362882 | 11.5363574 | 12.2646977 | 12.727901 | 8.2753779 | 5.3627916 | 6.5688072 |
| GHRLOS2 | -1.421911546 | 0.04958755 | 0.002866886 | -52.15895996 | 6.3067721 | 6.7629335 | 7.3390847 | 1.0866873 | 1.2054667 | 0.6019289 |
| ABTB2 | -0.85833366 | 0.07443975 | 0.021473963 | -52.15895996 | 6.3067721 | 7.7111563 | 8.1272196 | 6.0269554 | 6.7399276 | 0.6019289 |
| FLVCR1 | -0.822668496 | 0.085317325 | 0.027002327 | -52.3449401 | 6.3067721 | 7.1060646 | 7.0300422 | 6.4903918 | 1.2054667 | 0.6019289 |
| VILL | -1.415130664 | 0.04958755 | 0.002907005 | -52.3449401 | 6.6783891 | 6.3119075 | 7.3175252 | 5.5063453 | 1.2054667 | 0.6019289 |
| EIF2B2 | -1.411559831 | 0.04958755 | 0.002955147 | -52.3449401 | 7.2590288 | 6.3119075 | 6.6362622 | 1.0866873 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| CXXC1P1 | −0.795326087 | 0.094440529 | 0.03205729 | −52.3449401 | 7.2983248 | 6.3119075 | 7.2508437 | 5.9712523 | 1.2054667 | 0.6019289 |
| KIFC2 | −1.394743823 | 0.04958755 | 0.003035385 | −52.50701226 | 6.1437849 | 6.8213295 | 6.9199049 | 1.0866873 | 1.2054667 | 0.6019289 |
| C9orf72 | −0.854566499 | 0.075433888 | 0.022049266 | −52.50701226 | 7.1980024 | 6.7924268 | 6.9199049 | 5.5063453 | 1.2054667 | 0.6019289 |
| SAA1 | −1.139465631 | 0.050038461 | 0.006590708 | −52.86321164 | 11.637507 | 13.0817734 | 9.8877056 | 5.9133149 | 1.2054667 | 7.4777211 |
| STK16 | −1.386577772 | 0.04958755 | 0.003123646 | −52.8850554 | 7.2389721 | 6.3911446 | 6.3267171 | 1.0866873 | 1.2054667 | 0.6019289 |
| MRPL48 | −1.192094794 | 0.049809046 | 0.005493862 | −52.8850554 | 7.7305591 | 7.3635569 | 6.3267171 | 3.1012538 | 1.2054667 | 0.6019289 |
| RRAGD | −0.784928469 | 0.098230159 | 0.034177164 | −52.8850554 | 8.254752 | 7.9523826 | 6.3267171 | 6.9310735 | 1.2054667 | 0.6019289 |
| SEMA3F | −1.404816045 | 0.04958755 | 0.002987242 | −53.20285626 | 6.8201191 | 7.3033622 | 6.1759311 | 1.0866873 | 1.2054667 | 0.6019289 |
| NOL7 | −1.089665965 | 0.051027823 | 0.007835995 | −53.24751041 | 6.9736463 | 6.8213295 | 4.2859964 | 1.0866873 | 1.2054667 | 0.6019289 |
| SHISA4 | −0.758589669 | 0.109048772 | 0.040320148 | −53.82261845 | 7.7448535 | 6.3520696 | 7.3812609 | 6.6948447 | 1.2054667 | 0.6019289 |
| DNER | −1.427505584 | 0.04958755 | 0.002834791 | −53.96198945 | 7.2788106 | 6.7328249 | 6.3358005 | 1.0866873 | 1.2054667 | 0.6019289 |
| CTNNBIP1 | −0.914190684 | 0.063789541 | 0.01590348 | −54.46699285 | 7.3365789 | 7.5987767 | 6.3692392 | 5.1531951 | 1.2054667 | 0.6019289 |
| NKD2 | −1.004673177 | 0.054532631 | 0.010680414 | −54.49982243 | 6.9736463 | 6.3911446 | 7.9139132 | 4.3788962 | 1.2054667 | 0.6019289 |
| GPKOW | −0.918172687 | 0.063283514 | 0.015643906 | −54.58971634 | 8.7700497 | 6.6706551 | 6.976024 | 5.5826351 | 1.2054667 | 0.6019289 |
| OSBPL3 | −1.20153285 | 0.049809046 | 0.005341411 | −54.75154075 | 4.963444 | 7.1970971 | 6.861515 | 1.0866873 | 1.2054667 | 0.6019289 |
| PXDC1 | −1.287367142 | 0.04958755 | 0.004062425 | −54.89880206 | 13.8357827 | 13.3895655 | 14.6550651 | 8.7677808 | 1.2054667 | 8.8763623 |
| TAF1D | −0.93106596 | 0.061288269 | 0.014662601 | −55.12681398 | 10.324773 | 10.208492 | 10.6313772 | 4.5400907 | 8.8624022 | 0.6019289 |
| ARHGAP32 | −1.497182857 | 0.04958755 | 0.002241033 | −55.19414079 | 6.8731305 | 6.9314777 | 6.8006628 | 1.0866873 | 1.2054667 | 0.6019289 |
| CCNC | −1.017993933 | 0.053512074 | 0.010058873 | −55.19414079 | 6.8731305 | 7.0089004 | 3.7641245 | 1.0866873 | 1.2054667 | 0.6019289 |
| TRIP11 | −0.839932745 | 0.079307362 | 0.024047982 | −55.30030911 | 7.2983248 | 6.3911446 | 7.1809309 | 5.5826351 | 1.2054667 | 0.6019289 |
| RAB24 | −1.382539596 | 0.04958755 | 0.003155741 | −55.3359823 | 7.1558353 | 6.8774542 | 6.0316576 | 1.0866873 | 1.2054667 | 0.6019289 |
| PBX3 | −1.266414594 | 0.04958755 | 0.004367327 | −55.3359823 | 5.3354128 | 6.9314777 | 7.4222392 | 6.32242 | 1.2054667 | 0.6019289 |
| ORAOV1 | −1.44175751 | 0.04958755 | 0.002722458 | −55.84800011 | 6.8201191 | 7.0089004 | 6.4105447 | 1.0866873 | 1.2054667 | 0.6019289 |
| C14orf169 | −1.445476277 | 0.04958755 | 0.002698387 | −56.04896295 | 6.5048086 | 6.8496647 | 6.4105447 | 1.0866873 | 1.2054667 | 0.6019289 |
| TMC5 | −1.420661147 | 0.04958755 | 0.00287491 | −56.33815629 | 6.4179694 | 7.1522986 | 6.564874 | 6.8714329 | 1.2054667 | 0.6019289 |
| PLA2G2A | −0.811796465 | 0.088696214 | 0.028875873 | −56.4159582 | 1.8744435 | 6.9047187 | 7.7465254 | 6.3662802 | 1.2054667 | 0.6019289 |
| KAT6A | −1.181643125 | 0.049897122 | 0.005718527 | −56.50543402 | 10.9699811 | 11.1831093 | 11.5706927 | 7.335969 | 5.3627916 | 0.6019289 |
| UMPS | −0.725297124 | 0.124297571 | 0.049588382 | −56.67244581 | 6.6783891 | 7.0331116 | 7.0300422 | 6.6046733 | 1.2054667 | 0.6019289 |
| AHCTF1 | −1.444807895 | 0.04958755 | 0.002706411 | −56.77802403 | 7.373845 | 6.4291897 | 6.8006628 | 1.0866873 | 1.2054667 | 0.6019289 |
| GDAP2 | −1.446555092 | 0.04958755 | 0.00268234 | −56.8207099 | 6.6175557 | 7.0338116 | 6.564874 | 1.0866873 | 7.8365643 | 0.6019289 |
| RACGAP1 | −0.816909459 | 0.086958113 | 0.02805745 | −56.8207099 | 6.6482929 | 7.0338116 | 8.2346552 | 6.32242 | 1.2054667 | 0.6019289 |
| FBXO31 | −0.80824163 | 0.089516458 | 0.029377357 | −56.8207099 | 6.8989234 | 7.0338116 | 6.7371315 | 1.6938929 | 1.2054667 | 0.6019289 |
| SUFU | −0.760523148 | 0.107869852 | 0.039803418 | −57.25076191 | 7.0446897 | 6.8213295 | 8.0111355 | 6.0805901 | 1.2054667 | 0.6019289 |
| CCL20 | −0.969796366 | 0.057171148 | 0.012303619 | −57.7630963 | 9.949176 | 8.8052757 | 6.4507011 | 6.3662802 | 7.4318221 | 6.5680 72 |
| NMUR1 | −0.839507414 | 0.079317736 | 0.02411137 | −57.71381923 | 7.0901803 | 6.7924268 | 7.0563116 | 5.6551006 | 2.5373444 | 0.6019289 |
| MCC | −1.456664958 | 0.04958755 | 0.002570007 | −57.73125842 | 6.4532097 | 6.9047187 | 7.1123668 | 1.0866873 | 1.2054667 | 0.6019289 |
| SLC1A3 | −0.774466937 | 0.102109423 | 0.036434245 | −57.73125842 | 6.8468682 | 8.4548593 | 9.0676963 | 6.6046733 | 1.2054667 | 0.6019289 |
| RILPL1 | −1.491652502 | 0.04958755 | 0.002305223 | −57.79342406 | 6.7367617 | 7.0338116 | 6.8314096 | 1.0866873 | 7.8365643 | 0.6019289 |
| CASK | −1.416773443 | 0.04958755 | 0.002899981 | −57.79342406 | 7.0901803 | 7.0583001 | 6.7371315 | 1.6938929 | 1.2054667 | 0.6019289 |
| KIF21B | −1.319295837 | 0.04958755 | 0.003725427 | −57.79342406 | 5.6586086 | 7.0583001 | 6.976024 | 1.0866873 | 1.2054667 | 0.6019289 |
| WRNIP1 | −0.968662676 | 0.057313185 | 0.01241117 | −57.79342406 | 6.8731305 | 7.0583001 | 7.4620859 | 4.8170878 | 2.8554202 | 0.6019289 |
| TGFB1I1 | −1.38402487 | 0.04958755 | 0.003147717 | −58.07269421 | 13.445669 | 13.2916102 | 12.4468155 | 7.6868219 | 1.2054667 | 0.6019289 |
| IQCE | −1.274955253 | 0.04958755 | 0.004068781 | −58.1436557 | 7.2389721 | 6.7020747 | 9.0482372 | 5.1531951 | 1.2054667 | 0.6019289 |
| SHE | −0.897868689 | 0.066669982 | 0.017333708 | −58.16774841 | 7.0676142 | 6.6706551 | 7.2046135 | 1.0866873 | 1.2054667 | 0.6019289 |
| GPT2 | −1.37316698 | 0.04958755 | 0.003227955 | −58.18110428 | 6.9491661 | 8.7234108 | 6.0316576 | 1.0866873 | 1.2054667 | 0.6019289 |
| SEC31B | −1.45215489 | 0.04958755 | 0.002610126 | −58.25576141 | 6.8468682 | 6.4662577 | 7.6113033 | 1.0866873 | 1.2054667 | 0.6019289 |
| PDDC1 | −1.213226433 | 0.049622329 | 0.005161679 | −58.25576141 | 6.9736463 | 6.4662577 | 7.481604 | 1.0866873 | 2.8554202 | 0.6019289 |
| FAM50B | −1.461235411 | 0.04958755 | 0.002521865 | −58.52828813 | 6.9736463 | 6.9577495 | 6.4897707 | 1.0866873 | 1.2054667 | 0.6019289 |
| MCM2 | −1.447989742 | 0.04958755 | 0.002642221 | −58.52828813 | 7.943836 | 6.9577495 | 6.4105447 | 1.0866873 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| MCRS1 | -1.379018401 | 0.04958755 | 0.003171788 | -58.52828813 | 8.2647067 | 6.9577495 | 6.0125266 | 1.0866873 | 1.2054667 | 0.6019289 |
| CCT2 | -1.376265498 | 0.04958755 | 0.003203883 | -58.54185582 | 14.5375205 | 15.4536305 | 14.7443802 | 8.6661239 | 9.8496795 | 8.7884466 |
| BMPR1A | -0.75467612 | 0.110509614 | 0.041291021 | -58.75519803 | 7.7448835 | 7.0089004 | 7.0821113 | 6.9310735 | 1.2054667 | 0.6019289 |
| PSD | -1.459126615 | 0.04958755 | 0.002245936 | -59.167676 | 6.9736463 | 6.4291897 | 7.4423001 | 1.0866873 | 1.2054667 | 0.6019289 |
| WDR85 | -1.250937065 | 0.04958755 | 0.00460804 | -59.167676 | 6.9736463 | 7.3033622 | 5.2252164 | 1.0866873 | 1.2054667 | 0.6019289 |
| TMCO7 | -1.453392299 | 0.04958755 | 0.002286055 | -59.21299099 | 7.3921232 | 6.7924268 | 6.4897707 | 1.0866873 | 1.2054667 | 0.6019289 |
| CHD7 | -0.835488129 | 0.080837307 | 0.024786167 | -59.21299099 | 7.1170729 | 7.3830764 | 6.4897707 | 5.7241063 | 1.2054667 | 0.6019289 |
| POU6F1 | -0.813669388 | 0.087770982 | 0.028457835 | -59.79658195 | 8.0044995 | 6.8496647 | 7.1074578 | 6.4088472 | 1.2054667 | 0.6019289 |
| POLE | -0.748784251 | 0.1132519 | 0.042834791 | -60.00173053 | 7.1123989 | 7.3237074 | 7.0032858 | 6.7770801 | 1.2054667 | 0.6019289 |
| TKTL1 | -1.270060388 | 0.04958755 | 0.004295114 | -60.40510285 | 7.2389721 | 5.3406193 | 7.0032858 | 1.0866873 | 1.2054667 | 0.6019289 |
| TIGD5 | -1.458785999 | 0.04958755 | 0.00255396 | -60.51751032 | 6.5212096 | 7.6317881 | 6.8314096 | 1.0866873 | 1.2054667 | 0.6019289 |
| HPS6 | -1.460325415 | 0.04958755 | 0.002537912 | -60.79504453 | 8.2039211 | 6.9577495 | 6.5278107 | 1.0866873 | 1.2054667 | 0.6019289 |
| AP1G2 | -1.456046175 | 0.04958755 | 0.002578031 | -60.79504453 | 6.7650859 | 7.4213407 | 6.5278107 | 1.0866873 | 1.2054667 | 0.6019289 |
| MGRN1 | -1.021505515 | 0.053385633 | 0.009920565 | -60.79504453 | 8.2844125 | 7.6480149 | 6.5278107 | 4.81708878 | 1.2054667 | 0.6019289 |
| DDR1 | -0.84237993 | 0.078811783 | 0.023698147 | -60.79504453 | 8.0512583 | 9.1453174 | 6.5278107 | 6.9959943 | 1.2054667 | 0.6019289 |
| LOC100132077 | -1.446697233 | 0.04958755 | 0.002666292 | -61.21129731 | 6.7078705 | 6.537655 | 7.6635078 | 1.0866873 | 1.2054667 | 0.6019289 |
| BTN2A2 | -0.870170973 | 0.071778816 | 0.020322555 | -61.21129731 | 7.8411348 | 6.537655 | 7.8448881 | 6.0269554 | 1.2054667 | 0.6019289 |
| ATG2B | -1.481823504 | 0.04958755 | 0.02401508 | -61.53583637 | 7.4801945 | 7.3033622 | 7.0300422 | 1.0866873 | 1.2054667 | 0.6019289 |
| DDHD2 | -0.784845532 | 0.099230159 | 0.034193212 | -61.68432032 | 7.5951068 | 7.1522986 | 6.8910052 | 6.5294995 | 1.2054667 | 0.6019289 |
| KCNH3 | -1.395593779 | 0.04958755 | 0.003019337 | -61.83572393 | 7.1558353 | 7.08238 | 6.0540376 | 1.0866873 | 1.2054667 | 0.6019289 |
| ZCCHC14 | -0.858047636 | 0.07443975 | 0.021522105 | -61.83572393 | 7.1558353 | 6.9314777 | 8.3453359 | 6.2304884 | 1.2054667 | 0.6019289 |
| C6orf228 | -0.768128087 | 0.104791398 | 0.037960363 | -61.87936411 | 6.6783891 | 7.3033622 | 7.168531 | 6.4088472 | 1.2054667 | 0.6019289 |
| PWWP2A | -1.418967161 | 0.04958755 | 0.002890957 | -62.2378112 | 7.0446897 | 6.1842483 | 7.2279137 | 1.0866873 | 1.2054667 | 0.6019289 |
| ST7-AS1 | -1.451955685 | 0.04958755 | 0.00261815 | -62.37712183 | 7.5631978 | 6.7020747 | 6.564874 | 1.0866873 | 1.2054667 | 0.6019289 |
| TREX1 | -1.440363594 | 0.04958755 | 0.002730482 | -62.37712183 | 8.4506083 | 6.7924268 | 6.564874 | 1.0866873 | 1.2054667 | 0.6019289 |
| FBXL8 | -1.436943373 | 0.04958755 | 0.002786648 | -62.37712183 | 7.4971815 | 6.5720715 | 6.564874 | 1.0866873 | 1.2054667 | 0.6019289 |
| WWC1 | -0.834101668 | 0.081251647 | 0.024966701 | -62.37712183 | 7.7305591 | 10.3491315 | 6.564874 | 7.3578678 | 1.2054667 | 0.6019289 |
| DYRK2 | -0.761661609 | 0.107291504 | 0.039519377 | -62.68909303 | 7.2590288 | 6.5720715 | 7.7784397 | 6.7105675 | 1.2054667 | 0.6019289 |
| IL23A | -1.246891748 | 0.04958755 | 0.004656182 | -62.92076189 | 7.0676142 | 5.1957839 | 7.1809309 | 1.0866873 | 1.2054667 | 0.6019289 |
| SMURF1 | -1.245079199 | 0.04958755 | 0.00467223 | -63.75645085 | 13.205502 | 13.4922866 | 13.3951924 | 7.400693 | 8.6892694 | 8.4493889 |
| CYP1A1 | -1.468628309 | 0.04958755 | 0.00248977 | -63.9592212 | 7.5139709 | 6.7924268 | 6.6010094 | 1.0866873 | 1.2054667 | 0.6019289 |
| HTR7P1 | -0.767367365 | 0.104951556 | 0.038139292 | -63.9592212 | 7.6416849 | 7.2617905 | 6.6010094 | 6.6046733 | 1.2054667 | 0.6019289 |
| IRX4 | -1.264737812 | 0.04958755 | 0.004391399 | -64.15514131 | 7.0901803 | 8.0287286 | 5.2252164 | 1.0866873 | 1.2054667 | 0.6019289 |
| LOC100506835 | -1.47233144 | 0.04958755 | 0.002465698 | -64.1690561 | 6.8201191 | 6.6056864 | 7.5198657 | 1.0866873 | 1.2054667 | 0.6019289 |
| G6PD | -1.240306547 | 0.04958755 | 0.004712349 | -64.20769258 | 13.5728075 | 12.9357477 | 12.3585146 | 6.9310735 | 1.2054667 | 8.4493889 |
| SYT8 | -0.877332097 | 0.070335652 | 0.019644548 | -64.9280771 | 2.2016907 | 8.5442716 | 7.1074578 | 1.0866873 | 1.2054667 | 0.6019289 |
| SPTLC2 | -0.833721532 | 0.08138461 | 0.025047741 | -65.00356981 | 7.5469748 | 6.9577495 | 7.2279137 | 6.1323043 | 1.2054667 | 0.6019289 |
| CLK4 | -0.792014303 | 0.095431107 | 0.03264543 | -65.00356981 | 7.2590288 | 7.038116 | 7.2279137 | 6.4088472 | 1.2054667 | 0.6019289 |
| ATP6V1B1 | -1.498372831 | 0.04958755 | 0.002216962 | -65.54134109 | 7.0676142 | 7.77165 | 6.6362622 | 1.0866873 | 1.2054667 | 0.6019289 |
| ZFP41 | -1.485343071 | 0.04958755 | 0.002337318 | -65.54134109 | 7.7305591 | 6.9314777 | 6.6362622 | 1.0866873 | 1.2054667 | 0.6019289 |
| OPA1 | -0.723957315 | 0.12484568 | 0.049991976 | -65.54134109 | 8.0740814 | 7.5649923 | 6.6362622 | 7.4626381 | 1.2054667 | 0.6019289 |
| GRK6 | -1.402816972 | 0.04958755 | 0.003011313 | -65.92160364 | 7.4277993 | 7.1293668 | 6.0560619 | 1.0866873 | 1.2054667 | 0.6019289 |
| MARK3 | -0.748823873 | 0.11325619 | 0.042818743 | -66.04497956 | 7.2788106 | 7.1748717 | 7.0208437 | 6.9310735 | 1.2054667 | 0.6019289 |
| MPDZ | -0.781693536 | 0.099294469 | 0.034792586 | -66.05882908 | 7.9313911 | 7.1293668 | 7.1323668 | 1.0866873 | 1.2054667 | 0.6019289 |
| REC8 | -1.001899297 | 0.054859251 | 0.010825644 | -66.09017745 | 6.6482929 | 7.9126391 | 8.9323923 | 1.0866873 | 6.9073747 | 0.6019289 |
| C10orf35 | -1.061945922 | 0.051493437 | 0.008619915 | -66.14651431 | 7.1342805 | 8.4174829 | 3.7641245 | 5.4258059 | 1.2054667 | 0.6019289 |
| NUP205 | -1.464959087 | 0.04958755 | 0.002513841 | -66.42075071 | 7.2590288 | 7.1522986 | 6.4105447 | 1.0866873 | 1.2054667 | 0.6019289 |
| SENP1 | -1.472731922 | 0.04958755 | 0.002457675 | -66.99780884 | 7.893399 | 7.1522986 | 6.4570011 | 1.0866873 | 1.2054667 | 0.6019289 |
| TBC1D25 | -0.846164576 | 0.077719653 | 0.023088341 | -67.08639294 | 7.7448535 | 7.1060646 | 7.273415 | 6.2304884 | 1.2054667 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| DHCR7 | -0.900805814 | 0.066271613 | 0.017069726 | -67.12348009 | 8.7346746 | 8.3791124 | 6.6706745 | 6.4903918 | 1.2054667 | 0.6019289 |
| ZFPM1 | -1.497208629 | 0.04958755 | 0.00223301 | -67.14220526 | 7.1158353 | 7.9653908 | 6.6010094 | 1.0866873 | 1.2054667 | 0.6019289 |
| MUC1 | -1.333349257 | 0.04958755 | 0.003589024 | -67.14220526 | 7.1158353 | 9.3073441 | 5.7029118 | 1.0866873 | 1.2054667 | 0.6019289 |
| PPP1R18 | -1.264339428 | 0.04958755 | 0.004399422 | -67.87854833 | 13.5314028 | 13.5873889 | 15.1530469 | 7.5025051 | 9.5024342 | 0.6019289 |
| APOA1 | -1.279466814 | 0.04958755 | 0.004126615 | -68.03401776 | 5.3162271 | 7.1748717 | 7.5934735 | 1.0866873 | 1.2054667 | 0.6019289 |
| TRIM29 | -1.318614771 | 0.04958755 | 0.003733451 | -68.13789901 | 7.1770729 | 9.3673812 | 5.5929159 | 1.0866873 | 1.2054667 | 0.6019289 |
| PLCD1 | -1.49212559 | 0.04958755 | 0.0022972 | -68.25477669 | 7.2983248 | 6.8496647 | 6.7042855 | 1.0866873 | 1.2054667 | 0.6019289 |
| BET1L | -1.490769282 | 0.04958755 | 0.002321271 | -68.60043399 | 8.0044995 | 6.7020747 | 6.9482372 | 7.1477675 | 1.2054667 | 0.6019289 |
| IL1B | -0.88488578 | 0.068629673 | 0.018704967 | -68.60043399 | 9.0488124 | 6.7020747 | 10.5870107 | 7.0964955 | 1.2054667 | 0.6019289 |
| PDK1 | -0.817044141 | 0.086745168 | 0.027882532 | -68.70563693 | 7.7161217 | 7.4213407 | 7.7042855 | 6.32242 | 1.2054667 | 0.6019289 |
| C9orf91 | -0.724351556 | 0.124712075 | 0.049856375 | -69.16922996 | 7.8543794 | 7.3033622 | 7.3175252 | 7.6158948 | 1.2054667 | 0.6019289 |
| GCLM | -0.750048713 | 0.112640836 | 0.042419161 | -69.17179262 | 7.3175786 | 7.4768994 | 7.1323668 | 7.0434341 | 1.2054667 | 0.6019289 |
| TTC32 | -1.511943235 | 0.04958755 | 0.002160796 | -69.45112731 | 7.5305672 | 6.6385363 | 7.2046135 | 1.0866873 | 1.2054667 | 0.6019289 |
| MCF2L | -1.512578538 | 0.04958755 | 0.002152772 | -70.0783039 | 8.1296079 | 6.7328249 | 7.1323668 | 1.0866873 | 1.2054667 | 0.6019289 |
| GABARAPL1 | -0.754590412 | 0.110509614 | 0.041299045 | -70.0783039 | 7.4101728 | 6.7328249 | 8.1272196 | 7.147675 | 1.2054667 | 0.6019289 |
| LBR | -0.740086584 | 0.117838959 | 0.045312525 | -70.0783039 | 7.6108005 | 6.7328249 | 7.5386226 | 7.0964955 | 1.2054667 | 0.6019289 |
| BANP | -0.847000038 | 0.077594277 | 0.022979218 | -70.08881039 | 7.3365789 | 7.1293668 | 7.6635078 | 6.2304884 | 1.2054667 | 0.6019289 |
| CHD8 | -1.393122433 | 0.04958755 | 0.003051432 | -70.14644612 | 7.4971815 | 7.2189854 | 5.9741452 | 1.0866873 | 1.2054667 | 0.6019289 |
| LOC100133957 | -0.769027696 | 0.1044167 | 0.037790259 | -70.21065329 | 7.893399 | 7.0089004 | 7.3390847 | 7.0161533 | 1.2054667 | 0.6019289 |
| SCAMP3 | -0.799918713 | 0.092705411 | 0.031095242 | -70.28781043 | 7.5139709 | 7.8154118 | 6.7371315 | 6.6046733 | 1.2054667 | 0.6019289 |
| GCHFR | -1.482189174 | 0.04958755 | 0.002385461 | -70.58190233 | 7.4801945 | 6.4662577 | 7.2279137 | 1.0866873 | 1.2054667 | 0.6019289 |
| SPEG | -1.479590603 | 0.04958755 | 0.000242558 | -70.58190233 | 6.6540448 | 8.6767186 | 7.2279137 | 1.0866873 | 1.2054667 | 0.6019289 |
| BAIAP2L1 | -1.154170686 | 0.04991757 | 0.006343577 | -70.72720119 | 9.2068962 | 12.0654034 | 9.0805542 | 5.6551006 | 4.4251522 | 2.9363609 |
| S100A3 | -1.332050336 | 0.04958755 | 0.003597047 | -71.12499591 | 7.2389721 | 8.3195726 | 5.5929159 | 1.0866873 | 1.2054667 | 0.6019289 |
| TET2 | -0.803877945 | 0.09087079 | 0.030150847 | -71.12499591 | 7.2389721 | 7.0089004 | 8.3976469 | 1.0866873 | 1.2054667 | 0.6019289 |
| PPP4C | -1.130796382 | 0.050131358 | 0.006741555 | -71.41178272 | 7.943836 | 7.3635569 | 7.273415 | 4.1976103 | 1.2054667 | 0.6019289 |
| PPARG | -1.007762246 | 0.054397005 | 0.0105037 | -71.41178272 | 10.2590653 | 7.3635569 | 7.2279137 | 5.8529567 | 1.2054667 | 0.6019289 |
| ANKS3 | -0.79394253 | 0.094750565 | 0.032241033 | -71.41178272 | 6.6416849 | 7.3635569 | 6.861515 | 6.5675757 | 1.2054667 | 0.6019289 |
| ABLIM3 | -0.89353122 | 0.067244392 | 0.017762978 | -71.55618601 | 8.234634 | 6.7629335 | 7.5386226 | 5.9712523 | 1.2054667 | 0.6019289 |
| DKC1 | -1.496754126 | 0.04958755 | 0.002249057 | -71.86999955 | 6.9491661 | 8.1476275 | 6.7692467 | 1.0866873 | 1.2054667 | 0.6019289 |
| DPP3 | -1.477407095 | 0.04958755 | 0.002441627 | -72.2588875 | 8.1619262 | 7.2617905 | 6.4507011 | 1.0866873 | 1.2054667 | 0.6019289 |
| SLC2A8 | -0.790027729 | 0.095977935 | 0.032951135 | -72.29350892 | 7.0676142 | 7.4586165 | 7.3812609 | 6.6408414 | 1.2054667 | 0.6019289 |
| LOC158435 | -0.927265603 | 0.061709548 | 0.014936211 | -73.03407959 | 7.5951068 | 6.7924268 | 7.5754206 | 5.4258059 | 1.2054667 | 0.6019289 |
| DFNB31 | -1.534925226 | 0.04958755 | 0.002016368 | -73.05625505 | 6.7928648 | 7.2617905 | 8.151795 | 1.0866873 | 1.2054667 | 0.6019289 |
| PWWP2B | -1.01121709 | 0.054161962 | 0.010346626 | -73.3573053 | 6.8468682 | 7.4023354 | 7.8552671 | 4.8170878 | 1.2054667 | 0.6019289 |
| WDR13 | -0.841676272 | 0.078911195 | 0.023799493 | -73.3573053 | 7.5469748 | 7.4023354 | 6.6199049 | 6.1323043 | 1.2054667 | 0.6019289 |
| SHROOM1 | -1.064598297 | 0.051378258 | 0.008515606 | -73.45220328 | 8.1296079 | 7.8154118 | 6.8006628 | 4.6851838 | 1.2054667 | 0.6019289 |
| ZNF668 | -1.598622483 | 0.04958755 | 0.001697023 | -74.1121141 | 7.2983248 | 7.1522986 | 7.4018955 | 1.0866873 | 1.2054667 | 0.6019289 |
| CDH1 | -1.481949348 | 0.04958755 | 0.002393485 | -74.1121141 | 7.2983248 | 9.1047412 | 6.6010094 | 1.0866873 | 1.2054667 | 0.6019289 |
| CRCP | -1.328977546 | 0.04958755 | 0.003629142 | -74.1121141 | 7.2983248 | 7.4213407 | 8.0245047 | 1.0866873 | 1.2054667 | 0.6019289 |
| MVK | -1.479685689 | 0.04958755 | 0.002417556 | -74.37134082 | 8.2244688 | 6.8213295 | 6.4507011 | 1.0866873 | 1.2054667 | 0.6019289 |
| ANKRD33B | -0.757790562 | 0.109363019 | 0.040534382 | -74.51198399 | 7.9561744 | 6.8213295 | 8.8685197 | 7.7544253 | 1.2054667 | 2.9363609 |
| FBXL18 | -1.019029046 | 0.053434625 | 0.010000802 | -74.67392472 | 7.4277993 | 9.2711329 | 7.3390847 | 5.5826351 | 1.2054667 | 0.6019289 |
| UCK2 | -1.503785059 | 0.04958755 | 0.002192891 | -75.03442075 | 6.9736463 | 8.309406 | 6.8314096 | 1.0866873 | 1.2054667 | 0.6019289 |
| LOC440335 | -1.446313563 | 0.04958755 | 0.002690363 | -75.03442075 | 7.0676142 | 10.5175668 | 6.8314096 | 1.0866873 | 1.2054667 | 0.6019289 |
| VTI1B | -0.947296514 | 0.059309685 | 0.013491936 | -75.03442075 | 8.1404613 | 7.6799309 | 6.8314096 | 5.5826351 | 1.2054667 | 0.6019289 |
| SETDB1 | -0.929131247 | 0.061465602 | 0.014779748 | -75.03442075 | 7.9061745 | 7.5819833 | 6.6199049 | 6.1323043 | 1.2054667 | 0.6019289 |
| SCGB3A1 | -1.403479681 | 0.04958755 | 0.002995266 | -75.1050418 | 6.5861495 | 12.0456339 | 7.3175252 | 1.0866873 | 1.2054667 | 0.6019289 |
| SETD8 | -1.338134765 | 0.04958755 | 0.003532857 | -75.1923537 | 11.5698646 | 12.0224811 | 12.1348465 | 5.7899671 | 6.6483084 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| C1orf216 | −0.792649967 | 0.09519921 | 0.032511434 | −75.41781298 | 7.7161217 | 7.2617905 | 7.4423001 | 6.9015613 | 1.2054667 | 0.6019289 |
| ELP3 | −1.512987677 | 0.04958755 | 0.002144748 | −75.42757164 | 7.6416849 | 7.3237074 | 6.6010094 | 1.0866873 | 1.2054667 | 0.6019289 |
| RECK | −0.784078996 | 0.098241201 | 0.034318382 | −75.9998986 | 8.5996216 | 6.8496647 | 7.7625708 | 7.3578678 | 1.2054667 | 0.6019289 |
| TMCO3 | −0.787985178 | 0.096821537 | 0.033463853 | −76.27560445 | 8.6984102 | 7.4586165 | 6.861515 | 7.1971015 | 1.2054667 | 0.6019289 |
| PTPN6 | −1.529250327 | 0.04958755 | 0.002072535 | −76.4838051 | 6.7078705 | 7.3437697 | 8.1022182 | 1.0866873 | 1.2054667 | 0.6019289 |
| AP1S1 | −0.874595489 | 0.070910747 | 0.019886865 | −76.61665111 | 8.9224556 | 7.7265191 | 6.861515 | 6.6046733 | 1.2054667 | 0.6019289 |
| CREB5 | −0.781181471 | 0.099949317 | 0.034914547 | −76.61665111 | 8.2244688 | 7.5127845 | 6.861515 | 7.0702087 | 1.2054667 | 0.6019289 |
| WDR5 | −1.485089658 | 0.04958755 | 0.002345342 | −77.09925115 | 7.3553323 | 7.4768994 | 6.4507011 | 1.0866873 | 1.2054667 | 0.6019289 |
| LMBR1 | −0.907892186 | 0.065167114 | 0.016538554 | −77.24837461 | 7.373845 | 7.4768994 | 7.5571389 | 5.8529567 | 1.2054667 | 0.6019289 |
| FUT4 | −1.526606869 | 0.04958755 | 0.002096606 | −77.36663297 | 7.5305672 | 6.6706551 | 7.3603269 | 1.0866873 | 1.2054667 | 0.6019289 |
| RAB11FIP5 | −1.564383851 | 0.04958755 | 0.001887988 | −77.47482283 | 7.3553323 | 6.8774542 | 7.7465254 | 1.0866873 | 1.2054667 | 0.6019289 |
| POM121 | −1.619674349 | 0.04958755 | 0.001600738 | −77.50069481 | 7.2788106 | 7.3237074 | 7.481604 | 1.0866873 | 1.2054667 | 0.6019289 |
| MTERFD2 | −0.850886516 | 0.076483673 | 0.022494584 | −77.50069481 | 8.2745933 | 7.7083001 | 7.481604 | 6.5294995 | 1.2054667 | 0.6019289 |
| PLEKHG4 | −1.413178236 | 0.04958755 | 0.002915028 | −77.54004108 | 7.8675036 | 7.3635569 | 6.0316576 | 1.0866873 | 1.2054667 | 0.6019289 |
| CHCHD6 | −0.875459502 | 0.070710498 | 0.01980743 | −78.19889362 | 8.3038528 | 7.926009 | 6.8910052 | 6.8910052 | 1.2054667 | 0.6019289 |
| FAM160B2 | −0.846092007 | 0.077730608 | 0.023104389 | −78.19889362 | 8.9287302 | 8.4079855 | 6.8910052 | 6.4501951 | 1.2054667 | 0.6019289 |
| ZBTB17 | −0.756630664 | 0.109655369 | 0.040751023 | −78.22114654 | 8.3699022 | 7.4949535 | 7.4620859 | 7.268205 | 1.2054667 | 0.6019289 |
| DCTN5 | −0.941606189 | 0.060032865 | 0.013903555 | −78.34204321 | 7.4971815 | 7.2617905 | 7.9840197 | 7.7544253 | 1.2054667 | 0.6019289 |
| METTL1 | −1.35841738 | 0.04958755 | 0.003364359 | −78.59627948 | 7.6868062 | 7.3830764 | 5.7236017 | 5.7241063 | 1.2054667 | 0.6019289 |
| GPIHBP1 | −1.52816644 | 0.04958755 | 0.002080558 | −78.94575618 | 7.6568826 | 6.9047187 | 6.9482372 | 1.0866873 | 1.2054667 | 0.6019289 |
| LOC283663 | −1.079098437 | 0.051291304 | 0.008157747 | −78.94575618 | 7.8411348 | 6.9047187 | 8.5716641 | 4.8170878 | 1.2054667 | 0.6019289 |
| ASB1 | −0.76200063 | 0.107152042 | 0.039450373 | −79.58358573 | 8.1512337 | 7.4586165 | 7.5198657 | 7.5976045 | 1.2054667 | 0.6019289 |
| SLC4A3 | −0.949358564 | 0.059079344 | 0.013311402 | −80.02253901 | 6.9242634 | 8.9431715 | 7.8250252 | 6.0269554 | 1.2054667 | 0.6019289 |
| PCBD2 | −1.394115092 | 0.04958755 | 0.003043408 | −80.086405 | 7.4101728 | 7.3035622 | 7.6972902 | 1.0866873 | 2.5373444 | 0.6019289 |
| VARS2 | −1.55714433 | 0.04958755 | 0.001920083 | −80.1761103 | 7.5305672 | 7.0089004 | 7.7063116 | 1.0866873 | 1.2054667 | 0.6019289 |
| KIAA1161 | −0.784061636 | 0.098241201 | 0.034326406 | −80.1761103 | 7.5305672 | 7.4586165 | 7.7138893 | 7.147675 | 1.2054667 | 0.6019289 |
| LOC388692 | −0.797962539 | 0.093669983 | 0.031619193 | −80.43269814 | 7.6108005 | 6.9314777 | 7.8994736 | 6.8406623 | 1.2054667 | 0.6019289 |
| TULP4 | −0.877030927 | 0.070425023 | 0.01969269 | −80.62503437 | 7.2983248 | 8.0654383 | 7.5386226 | 6.3662802 | 1.2054667 | 0.6019289 |
| KIAA1530 | −0.726840915 | 0.123667925 | 0.049156704 | −80.70876318 | 7.463005 | 7.4213407 | 7.0821113 | 1.0866873 | 7.3469252 | 0.6019289 |
| WDR44 | −0.945566274 | 0.059597087 | 0.01362513 | −81.09314574 | 7.5469748 | 7.5303978 | 8.2114624 | 5.9712523 | 1.2054667 | 0.6019289 |
| DPH2 | −1.580392082 | 0.04958755 | 0.001791703 | −81.41581601 | 6.9491661 | 7.7265191 | 7.4018955 | 6.7770801 | 1.2054667 | 0.6019289 |
| EPB41 | −1.534209702 | 0.04958755 | 0.00204044 | −81.41581601 | 6.9491661 | 8.7297091 | 6.976024 | 1.0866873 | 1.2054667 | 0.6019289 |
| XPO5 | −0.850734045 | 0.07656248 | 0.022543529 | −81.88985198 | 8.8906661 | 8.731048 | 7.4423001 | 6.0805901 | 1.2054667 | 0.6019289 |
| TRAF3 | −0.748220565 | 0.11350837 | 0.043004894 | −82.01018229 | 7.5631978 | 7.5819833 | 7.0300422 | 7.1971015 | 1.2054667 | 7.5859707 |
| DUSP8 | −0.74622734 | 0.106099876 | 0.038783599 | −82.11225072 | 8.4242047 | 7.5649923 | 7.5386226 | 7.7870752 | 1.2054667 | 0.6019289 |
| RGPD1 | −1.603753769 | 0.04958755 | 0.001680976 | −82.82125551 | 7.5305672 | 7.4586165 | 7.0821113 | 1.0866873 | 1.2054667 | 0.6019289 |
| ECI1 | −1.562951081 | 0.04958755 | 0.001896012 | −82.82125551 | 8.234634 | 7.4586165 | 6.861515 | 1.0866873 | 1.2054667 | 0.6019289 |
| HEBP2 | −1.090137131 | 0.051027823 | 0.007811923 | −82.94568721 | 8.5996216 | 8.1589958 | 6.976024 | 4.9379926 | 1.2054667 | 0.6019289 |
| SLC5A6 | −0.969653314 | 0.057171148 | 0.012319666 | −82.94568721 | 9.1649884 | 9.5381761 | 6.976024 | 6.7770801 | 1.2054667 | 0.6019289 |
| CYP4F30P | −0.959501561 | 0.058066829 | 0.012863791 | −83.0850306 | 7.2186326 | 7.5819833 | 7.9563845 | 5.5826351 | 1.2054667 | 0.6019289 |
| ARHGEF40 | −0.896457 | 0.066607118 | 0.017520661 | −83.84425872 | 7.5951068 | 7.6153768 | 7.4423001 | 6.0805901 | 1.2054667 | 0.6019289 |
| MECR | −1.603389592 | 0.04958755 | 0.001688999 | −84.76129852 | 7.6108005 | 7.3237074 | 7.1323668 | 1.0866873 | 1.2054667 | 0.6019289 |
| HPDL | −1.465928616 | 0.04958755 | 0.002505817 | −86.06075619 | 7.5139709 | 7.9653908 | 6.2829045 | 1.0866873 | 1.2054667 | 0.6019289 |
| GABRP | −1.420407921 | 0.04958755 | 0.002882933 | −86.4131138 | 6.4876101 | 11.6418129 | 7.5198657 | 1.0866873 | 1.2054667 | 0.6019289 |
| ADCY2 | −0.945201282 | 0.059597087 | 0.013665249 | −86.59538116 | 7.6416849 | 7.2189854 | 8.4969013 | 5.9712523 | 1.2054667 | 0.6019289 |
| KAT5 | −0.978358618 | 0.056452334 | 0.011832625 | −86.87376615 | 9.3725567 | 7.4768994 | 7.6463154 | 6.1822306 | 1.2054667 | 0.6019289 |
| DGUOK | −0.788873062 | 0.096395853 | 0.033221536 | −86.97616394 | 9.625257 | 7.6480149 | 7.1323668 | 7.8958605 | 1.2054667 | 0.6019289 |
| DISP1 | −1.641610762 | 0.04958755 | 0.001488406 | −87.05648639 | 7.5305672 | 7.6317881 | 7.273415 | 1.0866873 | 1.2054667 | 0.6019289 |
| RAB35 | −0.761371213 | 0.107520115 | 0.039621279 | −87.91522748 | 8.062715 | 7.2617905 | 7.6635078 | 7.522033 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| CDH24 | −1.584225542 | 0.04958755 | 0.001775656 | −87.9489505 | 7.1770729 | 7.6640611 | 7.1074578 | 1.0866873 | 1.2054667 | 0.6019289 |
| LRWD1 | −1.121241482 | 0.050341156 | 0.006948568 | −87.9489505 | 7.9561744 | 7.6640611 | 7.2046135 | 4.3788962 | 1.2054667 | 0.6019289 |
| SH2B2 | −1.054710393 | 0.051852306 | 0.008875873 | −87.9489505 | 7.2788106 | 7.6640611 | 8.3020771 | 5.0495858 | 1.2054667 | 0.6019289 |
| MAP3K6 | −0.933178137 | 0.061078464 | 0.014515767 | −88.38228495 | 7.0676142 | 8.2784691 | 9.0996286 | 6.5675757 | 1.2054667 | 0.6019289 |
| HEATR7A | −0.998030885 | 0.055362341 | 0.011018214 | −88.42946762 | 7.671922 | 8.3888011 | 7.2279137 | 5.5063453 | 1.2054667 | 0.6019289 |
| DTNBP1 | −0.943387389 | 0.059848162 | 0.013793629 | −88.42946762 | 7.671922 | 7.1522986 | 7.9563845 | 5.7241063 | 1.2054667 | 0.6019289 |
| SP4 | −0.776469077 | 0.101218075 | 0.035935563 | −88.42946762 | 7.671922 | 7.1522986 | 8.3664885 | 7.4626381 | 1.2054667 | 0.6019289 |
| SZT2 | −0.763728008 | 0.10657523 | 0.039027521 | −88.92173827 | 8.1296079 | 7.6799309 | 7.4423001 | 7.6517941 | 1.2054667 | 0.6019289 |
| PYCRL | −0.819098469 | 0.086243773 | 0.027636203 | −88.95669037 | 7.2389721 | 7.8578854 | 7.6804979 | 6.8406623 | 1.2054667 | 0.6019289 |
| C6orf136 | −1.607515823 | 0.04958755 | 0.001655690 | −89.29150746 | 7.7015384 | 7.08238 | 7.4620859 | 1.0866873 | 1.2054667 | 0.6019289 |
| PMS2 | −1.616417665 | 0.04958755 | 0.001624809 | −89.34651221 | 7.6868062 | 7.3437697 | 7.2046135 | 1.0866873 | 1.2054667 | 0.6019289 |
| LOC387646 | −1.012391504 | 0.054044749 | 0.010274412 | −89.34651221 | 7.6868062 | 7.1522986 | 7.9139132 | 5.1531951 | 1.2054667 | 0.6019289 |
| ATXN2 | −0.819126464 | 0.086237986 | 0.027620156 | −89.89452721 | 7.5951068 | 6.9956281 | 8.1759589 | 7.221194 | 1.2054667 | 0.6019289 |
| FAM105B | −0.780864829 | 0.099749586 | 0.035001204 | −89.99815478 | 7.786906 | 7.4213407 | 7.6972902 | 7.2911484 | 1.2054667 | 0.6019289 |
| ZDHHC13 | −1.161474288 | 0.04991757 | 0.006175078 | −90.04368463 | 7.5792405 | 7.7265191 | 4.4449938 | 1.0866873 | 1.2054667 | 0.6019289 |
| TUBBP5 | −1.194741205 | 0.049809046 | 0.005445719 | −90.26355767 | 7.7015384 | 8.3195726 | 7.5198657 | 4.1976103 | 1.2054667 | 0.6019289 |
| SURF6 | −0.986425466 | 0.056015811 | 0.011443473 | −90.85719646 | 8.0965491 | 7.7111563 | 7.1074578 | 5.4258059 | 1.2054667 | 0.6019289 |
| NIP7 | −1.656555176 | 0.04958755 | 0.001408168 | −90.86731728 | 7.4971815 | 7.7111563 | 7.3812609 | 1.0866873 | 1.2054667 | 0.6019289 |
| FLJ31485 | −1.335190989 | 0.04958755 | 0.003572976 | −90.93641216 | 8.8113858 | 5.4876732 | 7.5934735 | 1.0866873 | 1.2054667 | 0.6019289 |
| LOC401588 | −1.427715926 | 0.04958755 | 0.002826767 | −92.06724184 | 7.7730243 | 6.0604012 | 7.6113033 | 1.0866873 | 1.2054667 | 0.6019289 |
| ZNF496 | −1.129082857 | 0.050187311 | 0.006781674 | −92.09765111 | 7.7305591 | 7.5127845 | 7.7976413 | 4.5400907 | 1.2054667 | 0.6019289 |
| PAG1 | −0.827229665 | 0.083495213 | 0.026170264 | −92.24749547 | 10.322392 | 7.1293668 | 8.2231054 | 1.0866873 | 8.1688761 | 0.6019289 |
| IL1RL1 | −1.446586269 | 0.04958755 | 0.002674316 | −92.43530004 | 12.1854726 | 12.5024742 | 11.7534205 | 5.6551006 | 6.1440192 | 0.6019289 |
| FBRSL1 | −0.810997289 | 0.087112957 | 0.028934858 | −92.43952209 | 7.9061745 | 8.6608125 | 7.1323668 | 7.3794393 | 1.2054667 | 0.6019289 |
| BIRC2 | −1.012483014 | 0.054044749 | 0.010266389 | −92.62053515 | 9.4356014 | 9.846632 | 9.3107812 | 7.5025051 | 2.9023413 | 0.6019289 |
| TMEM165 | −0.739323773 | 0.1180144 | 0.0455708 9 | −92.81290068 | 8.7130255 | 7.7417201 | 7.6972902 | 8.4072489 | 1.2054667 | 0.6019289 |
| FAM173A | −1.631709047 | 0.04958755 | 0.001528524 | −93.12255655 | 7.4801945 | 7.2189854 | 7.7465254 | 1.0866873 | 1.2054667 | 0.6019289 |
| FZD5 | −1.152147834 | 0.04991757 | 0.006367648 | −93.31792243 | 8.518743 | 9.4804432 | 10.3553544 | 6.0269554 | 1.2054667 | 2.9363609 |
| LCLAT1 | −1.228448043 | 0.049622329 | 0.004937014 | −94.02185473 | 9.9887526 | 7.8578854 | 7.1568531 | 4.1976103 | 1.2054667 | 0.6019289 |
| GON4L | −0.947912754 | 0.059309685 | 0.013443794 | −94.02185473 | 8.7560036 | 8.225386 | 7.1568531 | 6.32242 | 1.2054667 | 0.6019289 |
| ATRIP | −0.856463294 | 0.074869193 | 0.02173634 | −94.02185473 | 7.9061745 | 8.0410693 | 7.1568531 | 1.0866873 | 6.6948447 | 0.6019289 |
| RHD | −0.954938167 | 0.058459296 | 0.013038594 | −94.1402651 | 8.2844125 | 7.6956281 | 7.7625708 | 6.1323043 | 1.2054667 | 0.6019289 |
| GATS | −1.437570115 | 0.04958755 | 0.002778625 | −94.3289068 | 8.6074655 | 6.0924064 | 7.6463154 | 1.0866873 | 1.2054667 | 0.6019289 |
| MKNK1 | −0.921044084 | 0.062677445 | 0.015370296 | −94.84879717 | 7.7730243 | 7.3635569 | 8.257481 | 6.2304884 | 1.2054667 | 0.6019289 |
| TBC1D8 | −1.543889611 | 0.04958755 | 0.001992297 | −95.02237149 | 7.6568826 | 7.8717699 | 6.6706745 | 1.0866873 | 1.2054667 | 0.6019289 |
| MIR3682 | −0.887065659 | 0.068365464 | 0.018446602 | −95.20350534 | 7.893399 | 7.1748717 | 8.1022182 | 6.4088472 | 1.2054667 | 0.6019289 |
| RIN3 | −0.871861884 | 0.071556137 | 0.02016208 | −95.20350534 | 8.0044995 | 7.1748717 | 9.232296 | 7.1223122 | 1.2054667 | 0.6019289 |
| MAP1A | −1.070095654 | 0.051378258 | 0.00836476 | −95.34887174 | 7.1770729 | 8.5869821 | 8.4281467 | 5.3405168 | 1.2054667 | 0.6019289 |
| STX1A | −1.57850311 | 0.04958755 | 0.001799727 | −95.45974195 | 8.0044995 | 6.8496647 | 7.6635078 | 1.0866873 | 1.2054667 | 0.6019289 |
| HES6 | −1.57494503 | 0.04958755 | 0.001823798 | −95.45974195 | 6.9736463 | 9.1395902 | 7.6635078 | 1.0866873 | 1.2054667 | 0.6019289 |
| KRT80 | −1.076350836 | 0.051291304 | 0.008189842 | −95.83078903 | 11.2635145 | 11.4779465 | 10.9944785 | 8.7093547 | 1.2054667 | 4.6810971 |
| CSNK2A1P | −1.597132956 | 0.04958755 | 0.001705047 | −96.01811201 | 7.671922 | 8.0774702 | 6.9482372 | 1.0866873 | 1.2054667 | 0.6019289 |
| ZNF33A | −0.887065659 | 0.068365464 | 0.00184787 | −96.55262725 | 6.8201191 | 7.8717699 | 8.2799514 | 1.0866873 | 1.2054667 | 0.6019289 |
| MIR3682 | −1.571922698 | 0.04958755 | 0.002200915 | −96.55262725 | 9.6894845 | 7.6799309 | 6.6010094 | 1.0866873 | 1.2054667 | 0.6019289 |
| SV2A | −1.501682231 | 0.04958755 | 0.001648881 | −96.5905788 | 7.9805393 | 7.7089004 | 7.6804979 | 1.0866873 | 1.2054667 | 0.6019289 |
| ZNF512 | −1.609270458 | 0.04958755 | 0.002634197 | −96.5905788 | 8.3325307 | 6.1390574 | 7.6635078 | 5.3405168 | 1.2054667 | 0.6019289 |
| GPR133 | −1.448796509 | 0.04958755 | 0.001799727 | −97.18653973 | 8.5434862 | 8.3369 34 | 7.6804979 | 1.0866873 | 1.2054667 | 0.6019289 |
| HRAS | −0.800975915 | 0.09207197 | 0.030776699 | −97.18653973 | 8.3882311 | 9.0869958 | 7.2046135 | 7.704022 | 8.3250145 | 0.6019289 |
| HPCAL1 | −0.774515452 | 0.102109423 | 0.036410976 | −97.72141729 | 4.2098819 | 8.5002579 | 7.6972902 | 1.0866873 | 1.2054667 | 0.6019289 |
| CRABP1 | −1.148146775 | 0.049952273 | 0.006438257 | −97.72141729 | 4.2098819 | 8.5002579 | 7.6972902 | 1.0866873 | 1.2054667 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| SLC7A8 | -0.74755663 | 0.11383441 | 0.043168579 | -98.15953515 | 9.3725567 | 7.2189854 | 8.6685197 | 8.8855392 | 1.2054667 | 0.6019289 |
| SLCO2B | -0.861646901 | 0.073515148 | 0.021028645 | -98.64967465 | 8.5020086 | 7.8297091 | 7.7625708 | 7.147675 | 1.2054667 | 0.6019289 |
| FOXC2 | -1.490800072 | 0.04958755 | 0.002313247 | -98.66516766 | 8.0044995 | 7.7111563 | 6.3692392 | 1.0866873 | 1.2054667 | 0.6019289 |
| AVPI1 | -1.642058323 | 0.04958755 | 0.001480382 | -99.0053393 | 7.7161217 | 7.1748717 | 8.0377511 | 1.0866873 | 1.2054667 | 0.6019289 |
| LOC100506730 | -0.894587493 | 0.067185728 | 0.017681136 | -99.04249435 | 8.4418607 | 8.8991443 | 8.3238686 | 1.6938929 | 6.9843361 | 0.6019289 |
| MXD3 | -1.237265891 | 0.04958755 | 0.004768515 | -99.43405496 | 7.8411348 | 8.101237 | 7.2508437 | 3.7493131 | 1.2054667 | 0.6019289 |
| MIIP | -0.877983737 | 0.070255881 | 0.019563508 | -99.43405496 | 7.8411348 | 7.843866 | 7.6463154 | 6.6046733 | 1.2054667 | 0.6019289 |
| C11orf91 | -1.018032408 | 0.053512074 | 0.01005055 | -99.52887028 | 7.2389721 | 8.9166266 | 8.9743323 | 6.1822306 | 1.2054667 | 0.6019289 |
| ALDH9A1 | -0.911140092 | 0.06461959 | 0.016240071 | -99.63755699 | 8.9779688 | 7.2405467 | 7.8552671 | 6.6046733 | 1.2054667 | 0.6019289 |
| RECQL4 | -1.565773327 | 0.04958755 | 0.001879965 | -99.72143967 | 6.7928648 | 7.7265191 | 8.5533334 | 1.0866873 | 1.2054667 | 0.6019289 |
| TERF2 | -0.896274379 | 0.066907118 | 0.017536709 | -100.3511085 | 7.8543794 | 7.6153768 | 8.0377511 | 6.5294995 | 1.2054667 | 0.6019289 |
| ST3GAL5 | -0.803526046 | 0.090941756 | 0.030189361 | -100.9222099 | 7.2590288 | 7.8991443 | 7.9563845 | 7.1725999 | 1.2054667 | 0.6019289 |
| DBN1 | -0.738852144 | 0.118078127 | 0.045719329 | -101.1155832 | 9.4487599 | 7.2617905 | 8.2461133 | 8.8081111 | 1.2054667 | 0.6019289 |
| TBCC | -1.223850645 | 0.049622329 | 0.00499318 | -101.5680736 | 9.2823359 | 8.8717699 | 7.8096632 | 4.5400907 | 1.2054667 | 0.6019289 |
| WDR34 | -1.529456393 | 0.04958755 | 0.002056487 | -101.8339871 | 8.0512583 | 7.7567626 | 6.564874 | 1.0866873 | 1.2054667 | 0.6019289 |
| MEN1 | -1.624573861 | 0.04958755 | 0.001576667 | -102.2447866 | 8.6984102 | 7.1293668 | 7.7625708 | 1.0866873 | 1.2054667 | 0.6019289 |
| DKFZp761E198 | -0.928406191 | 0.06157485 | 0.014826286 | -102.7263479 | 10.9981205 | 9.6309041 | 9.4609238 | 8.5086224 | 2.9023413 | 2.782613 |
| SELRC1 | -1.700155281 | 0.04958755 | 0.001223622 | -103.5136769 | 7.7590076 | 7.8991443 | 7.5008617 | 1.0866873 | 1.2054667 | 0.6019289 |
| BTBD10 | -0.893691618 | 0.067225527 | 0.017738907 | -103.5136769 | 8.0044995 | 7.8991443 | 7.6972902 | 6.6046733 | 1.2054667 | 0.6019289 |
| IDH3A | -1.651366521 | 0.04958755 | 0.001448287 | -103.5159803 | 7.9805393 | 7.5649923 | 7.2956386 | 1.0866873 | 1.2054667 | 0.6019289 |
| IARS | -0.892544622 | 0.067503575 | 0.01789858 | -103.5159803 | 8.518743 | 8.1129752 | 7.2956386 | 6.7442069 | 1.2054667 | 0.6019289 |
| NEDD9 | -0.75098096 | 0.112223511 | 0.042208136 | -103.5159803 | 8.559749 | 9.9647026 | 7.2956386 | 5.9133149 | 9.1731002 | 0.6019289 |
| N4BP1 | -1.581234598 | 0.04958755 | 0.00178368 | -103.9465389 | 8.1935364 | 7.7863852 | 6.8314096 | 6.4903918 | 1.2054667 | 0.6019289 |
| LDLRAP1 | -1.439187606 | 0.04958755 | 0.002762577 | -103.9840689 | 7.786906 | 8.2991672 | 6.0560619 | 6.9015613 | 1.2054667 | 0.6019289 |
| CFP | -0.863006793 | 0.073206726 | 0.020904277 | -104.0193286 | 7.9061745 | 7.3437697 | 7.9840197 | 7.7544253 | 1.2054667 | 0.6019289 |
| ABLIM2 | -1.66185065 | 0.04958755 | 0.001376073 | -104.0716479 | 8.4593032 | 7.3033622 | 8.7512612 | 6.4903918 | 1.2054667 | 0.6019289 |
| CX3CL1 | -1.138600456 | 0.050038461 | 0.006638851 | -105.0983536 | 8.3038528 | 7.8297091 | 7.0821113 | 1.0866873 | 2.8554202 | 0.6019289 |
| LOC152217 | -0.804666039 | 0.090664228 | 0.029992779 | -105.4592832 | 7.9925691 | 9.1047412 | 7.5754206 | 5.0495858 | 1.2054667 | 0.6019289 |
| SERINC2 | -1.431606119 | 0.04958755 | 0.002802696 | -105.9755664 | 7.8142752 | 7.926009 | 7.7138893 | 7.4626381 | 1.2054667 | 0.6019289 |
| ZFYVE1 | -1.042998888 | 0.052218844 | 0.009225708 | -106.4320874 | 7.8142752 | 9.2500252 | 6.0316576 | 1.0866873 | 1.2054667 | 0.6019289 |
| TMOD1 | -0.985105936 | 0.056090689 | 0.011522105 | -106.6807318 | 9.5741372 | 7.939256 | 9.1308694 | 5.9133149 | 1.2054667 | 0.6019289 |
| BRAT1 | -0.885930455 | 0.068486123 | 0.018589425 | -106.6807318 | 8.8581604 | 8.3296681 | 7.3390847 | 6.4903918 | 1.2054667 | 0.6019289 |
| PGAM5 | -0.772531831 | 0.102996779 | 0.036937335 | -106.7704996 | 7.943836 | 8.2574696 | 7.4018955 | 6.9015613 | 1.2054667 | 0.6019289 |
| ABCD1 | -0.944800461 | 0.059600929 | 0.013705368 | -107.027728 | 8.2745933 | 7.3437697 | 8.7512612 | 7.7544253 | 1.2054667 | 0.6019289 |
| TMEM63A | -1.628461023 | 0.04958755 | 0.001552596 | -107.1153742 | 8.4152951 | 7.8297091 | 7.0821113 | 6.4903918 | 1.2054667 | 0.6019289 |
| MTAP | -1.403634178 | 0.04958755 | 0.00300329 | -107.1153742 | 7.8543794 | 7.8297091 | 7.5754206 | 1.0866873 | 2.8554202 | 0.6019289 |
| PRRG1 | -0.936403251 | 0.060082102 | 0.014251785 | -107.4048923 | 8.559749 | 7.9523826 | 7.7784397 | 6.5675757 | 1.2054667 | 0.6019289 |
| CENPO | -0.911417367 | 0.064529265 | 0.016185509 | -107.4048923 | 8.4152951 | 7.9523826 | 7.4423001 | 6.5294995 | 1.2054667 | 0.6019289 |
| MICU1 | -0.904709839 | 0.065548582 | 0.016764824 | -107.7032389 | 8.4418607 | 7.5649923 | 7.9563845 | 6.6761254 | 1.2054667 | 0.6019289 |
| FLT4 | -0.77762629 | 0.100926453 | 0.035721736 | -107.8889534 | 7.3553323 | 8.0410693 | 9.6058253 | 1.0866873 | 1.2054667 | 0.6019289 |
| ZFAND2B | -1.042998888 | 0.086352882 | 0.027699591 | -108.1716545 | 8.5020086 | 7.843866 | 8.2910567 | 1.0866873 | 8.4387969 | 7.7187266 |
| TRIP4 | -1.066136222 | 0.051378258 | 0.00845944 | -108.2631145 | 9.2068962 | 8.2784691 | 7.3603269 | 5.6551006 | 1.2054667 | 0.6019289 |
| PARN | -0.840559145 | 0.079141153 | 0.023916393 | -108.3776979 | 9.545842 | 7.9653908 | 7.4222392 | 7.704022 | 1.2054667 | 0.6019289 |
| ADRB3 | -1.692806226 | 0.04958755 | 0.001263741 | -109.0298814 | 7.9061745 | 7.4213407 | 7.8552671 | 1.0866873 | 1.2054667 | 0.6019289 |
| SLC4A2 | -0.803232363 | 0.091042429 | 0.030244724 | -109.0298814 | 8.8382996 | 7.843866 | 7.8552671 | 1.0866873 | 1.2054667 | 0.6019289 |
| MIB2 | -0.937045989 | 0.060673 | 0.01421969 | -109.3505041 | 7.5951068 | 7.9782827 | 8.050877 | 6.2304884 | 7.9937674 | 0.6019289 |
| GET4 | -0.851348292 | 0.076222506 | 0.022392682 | -109.7862091 | 7.6108005 | 8.4079855 | 7.9840197 | 7.1971015 | 1.2054667 | 0.6019289 |
| THRAP3 | -0.765566314 | 0.105690271 | 0.038546899 | -109.7862091 | 8.7560036 | 7.926009 | 7.9840197 | 8.4281014 | 1.2054667 | 0.6019289 |
| TMEM53 | -0.94368197 | 0.059774283 | 0.013763139 | -109.8119015 | 9.3162351 | 9.3276089 | 8.9674264 | 7.7708426 | 2.5373444 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| TM4SF18 | −1.686526041 | 0.04958755 | 0.001295836 | −109.8455017 | 8.2039211 | 7.8297091 | 7.3812609 | 1.0866873 | 1.2054667 | 0.6019289 |
| CCDC167 | −0.982586278 | 0.05631807 | 0.011680173 | −109.8455017 | 8.5838045 | 7.9910605 | 7.3812609 | 5.9712523 | 1.2054667 | 0.6019289 |
| SRCAP | −1.652071958 | 0.04958755 | 0.001440263 | −109.9838222 | 7.5139709 | 7.3830764 | 8.313014 | 1.0866873 | 1.2054667 | 0.6019289 |
| TLE4 | −0.873886546 | 0.071004424 | 0.019959881 | −110.323311 | 7.5139709 | 7.9910605 | 8.8671038 | 7.147675 | 1.2054667 | 0.6019289 |
| ADCK5 | −1.68060118 | 0.04958755 | 0.001311883 | −111.4618743 | 8.5104001 | 7.4023354 | 7.7941359 | 1.0866873 | 1.2054667 | 0.6019289 |
| CSPP1 | −1.501080745 | 0.04958755 | 0.002208938 | −111.8691825 | 6.3818471 | 7.9523826 | 8.0111355 | 1.0866873 | 1.2054667 | 0.6019289 |
| CNTFR | −1.633825233 | 0.04958755 | 0.001520501 | −111.9500755 | 7.893399 | 7.08238 | 8.3346422 | 1.0866873 | 1.2054667 | 0.6019289 |
| UNC50 | −0.821592775 | 0.085414368 | 0.027145952 | −112.4224448 | 8.7130255 | 7.6956281 | 7.8994736 | 7.6833888 | 1.2054667 | 0.6019289 |
| CUL9 | −1.648265224 | 0.04958755 | 0.001456311 | −112.9399295 | 7.4971815 | 7.4213407 | 8.5253933 | 1.0866873 | 1.2054667 | 0.6019289 |
| FBXW2 | −0.925072897 | 0.061862376 | 0.015060579 | −113.0102885 | 9.1218267 | 8.5953745 | 7.4222392 | 7.0434341 | 1.2054667 | 0.6019289 |
| CREB1 | −0.8179622 | 0.086474917 | 0.027781433 | −113.4530692 | 7.8411348 | 7.9126391 | 8.5897647 | 7.5102577 | 1.2054667 | 0.6019289 |
| CITED4 | −1.549867771 | 0.04958755 | 0.00197625 | −113.9415836 | 7.9188379 | 9.4576082 | 6.7371315 | 1.0866873 | 1.2054667 | 0.6019289 |
| ITGA10 | −1.688102437 | 0.04958755 | 0.001279788 | −114.4179877 | 7.7448535 | 7.440099 | 8.2799514 | 1.0866873 | 1.2054667 | 0.6019289 |
| CCDC71 | −1.494359426 | 0.04958755 | 0.002273128 | −114.5926879 | 8.6384218 | 8.3195726 | 7.4423001 | 2.6271932 | 1.2054667 | 0.6019289 |
| GFM1 | −0.900747633 | 0.066280364 | 0.017085774 | −114.5926879 | 8.8449503 | 8.9166266 | 7.4423001 | 7.3137327 | 1.2054667 | 0.6019289 |
| USP54 | −0.898399296 | 0.066677304 | 0.017283961 | −114.5926879 | 8.3134756 | 8.1702751 | 7.4423001 | 6.7105675 | 1.2054667 | 0.6019289 |
| TNK2 | −0.968614125 | 0.057313185 | 0.012419161 | −114.8557622 | 7.4456083 | 8.8827436 | 8.5347669 | 6.5294995 | 1.2054667 | 0.6019289 |
| RAD21 | −0.863633724 | 0.073142123 | 0.020849715 | −115.0240391 | 8.0512583 | 8.0654383 | 8.0245047 | 7.1725999 | 1.2054667 | 0.6019289 |
| CLK3 | −0.934301045 | 0.060990824 | 0.014430715 | −115.1873542 | 7.9188379 | 8.0533052 | 8.3976469 | 6.6408414 | 1.2054667 | 0.6019289 |
| ZNF195 | −0.833328386 | 0.081558088 | 0.025127979 | −115.1873542 | 8.0965491 | 8.0533052 | 7.6463154 | 7.268205 | 1.2054667 | 0.6019289 |
| ITPK1 | −0.878801921 | 0.069923269 | 0.019379764 | −115.9411012 | 8.062715 | 8.214531 | 8.0377511 | 7.1223122 | 1.2054667 | 0.6019289 |
| ZC3H18 | −0.965572928 | 0.057385588 | 0.012533098 | −116.0351384 | 8.1830764 | 7.7576626 | 8.0638846 | 6.1822306 | 1.2054667 | 0.6019289 |
| S100A7 | −1.697906723 | 0.04958755 | 0.001239669 | −116.1750909 | 7.9188379 | 8.8846063 | 7.4620859 | 1.0866873 | 1.2054667 | 0.6019289 |
| KRT7 | −0.910265331 | 0.064737869 | 0.016344379 | −116.1750909 | 8.7418194 | 11.8243128 | 7.4620859 | 1.0866873 | 8.3687411 | 0.6019289 |
| UBE2Q1 | −0.82138717 | 0.085414368 | 0.027179652 | −116.1750909 | 8.9960085 | 8.8760413 | 7.4620859 | 8.1174489 | 1.2054667 | 0.6019289 |
| LYN | −1.681654987 | 0.04958755 | 0.001303859 | −116.2491308 | 7.463005 | 8.9099134 | 7.8402254 | 1.0866873 | 1.2054667 | 0.6019289 |
| KIAA1549 | −0.944478843 | 0.060960411 | 0.01440744 | −116.9458772 | 7.5792405 | 8.2991672 | 7.9563845 | 6.5675757 | 6.3900594 | 0.6019289 |
| RUSC1 | −0.945182934 | 0.059597087 | 0.013673273 | −117.3741127 | 8.4850778 | 7.4468994 | 8.2799514 | 6.4501951 | 1.2054667 | 0.6019289 |
| XIRP1 | −1.381740013 | 0.04958755 | 0.003163765 | −117.6782154 | 5.6586086 | 7.9653908 | 8.9037393 | 1.0866873 | 1.2054667 | 0.6019289 |
| KIFC3 | −0.968105352 | 0.057313185 | 0.012435208 | −117.7574976 | 8.7839604 | 8.5468566 | 7.481604 | 6.9599943 | 1.2054667 | 0.6019289 |
| PROSER1 | −1.673022607 | 0.04958755 | 0.001343978 | −117.7752267 | 8.085359 | 8.0654383 | 7.2508437 | 1.0866873 | 1.2054667 | 0.6019289 |
| DNHD1 | −1.066843604 | 0.051378258 | 0.008435369 | −118.1181206 | 8.7839604 | 7.6640611 | 8.0895532 | 5.5826351 | 1.2054667 | 0.6019289 |
| CYHR1 | −0.904079679 | 0.065667985 | 0.016816978 | −118.1181206 | 8.4330597 | 7.6153768 | 8.0895532 | 6.7770801 | 1.2054667 | 0.6019289 |
| SLC25A43 | −1.714560415 | 0.04958755 | 0.001159432 | −118.69229 | 8.0965491 | 7.926009 | 7.5008617 | 1.0866873 | 1.2054667 | 0.6019289 |
| NUP214 | −0.773763104 | 0.102561162 | 0.036646072 | −119.1596127 | 8.2844125 | 7.8578854 | 8.1022182 | 8.1174489 | 1.2054667 | 0.6019289 |
| TBP | −1.710400436 | 0.04958755 | 0.001191527 | −119.7907928 | 8.4418607 | 7.9910605 | 7.4620859 | 1.0866873 | 1.2054667 | 0.6019289 |
| MATL2963 | −1.452171834 | 0.04958755 | 0.002602102 | −119.7907928 | 7.8142752 | 7.9910605 | 8.1022182 | 2.8554202 | 1.2054667 | 0.6019289 |
| SSFA2 | −0.948970074 | 0.059206517 | 0.013359544 | −120.051411 | 7.893399 | 8.1129752 | 8.4775892 | 6.5675757 | 1.2054667 | 0.6019289 |
| MAP3K4 | −1.711613147 | 0.04958755 | 0.001175479 | −120.3384614 | 8.1725401 | 7.4586165 | 7.9976413 | 1.0866873 | 1.2054667 | 0.6019289 |
| PDCD11 | −1.717671633 | 0.04958755 | 0.001151408 | −120.9223211 | 7.9561744 | 8.464054 | 7.5198657 | 1.0866873 | 1.2054667 | 0.6019289 |
| LY6K | −1.033216317 | 0.052897282 | 0.009569927 | −120.9223211 | 8.3699022 | 9.7708544 | 7.5198657 | 6.2771857 | 1.2054667 | 0.6019289 |
| RHOD | −0.949075258 | 0.059206517 | 0.013351521 | −120.9223211 | 8.5270379 | 10.2275206 | 7.5198657 | 7.2911484 | 1.2054667 | 0.6019289 |
| YRDC | −0.909435869 | 0.064939231 | 0.016416593 | −121.0242239 | 8.5352855 | 8.1246187 | 7.7465254 | 6.8714329 | 1.2054667 | 0.6019289 |
| BEGAIN | −0.970096616 | 0.057171148 | 0.0122635 | −121.8226255 | 7.5305672 | 9.0988503 | 9.0350412 | 6.9015613 | 1.2054667 | 0.6019289 |
| SEC23A | −0.769334871 | 0.104294685 | 0.037660274 | −121.9970372 | 11.082598 | 7.9126391 | 7.9563845 | 9.6016369 | 1.2054667 | 0.6019289 |
| DPYSL4 | −1.714051698 | 0.04958755 | 0.001167456 | −122.2840926 | 7.4456083 | 8.136169 | 8.1395596 | 1.0866873 | 1.2054667 | 0.6019289 |
| ELF4 | −1.781203872 | 0.04958755 | 0.000942791 | −122.6001885 | 8.0280683 | 8.136169 | 8.0245047 | 1.0866873 | 1.2054667 | 0.6019289 |
| USP4 | −1.753437705 | 0.04958755 | 0.001039076 | −122.9596638 | 8.0740814 | 8.0287286 | 7.6972902 | 1.0866873 | 1.2054667 | 0.6019289 |
| NSMCE1 | −1.603874523 | 0.04958755 | 0.001672952 | −122.9596638 | 8.2941654 | 8.0287286 | 6.8910052 | 1.0866873 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| SAP25 | -1.020514947 | 0.053420513 | 0.00995266 | -122.969851 | 7.9684083 | 8.1476275 | 9.9450759 | 6.6046733 | 1.2054667 | 0.6019289 |
| RIC8B | -1.637264245 | 0.04958755 | 0.001504453 | -123.3413253 | 7.9061745 | 7.5819833 | 8.6427428 | 1.6938929 | 1.2054667 | 0.6019289 |
| CASP9 | -0.918951128 | 0.063218173 | 0.015586135 | -124.0159555 | 7.6868062 | 8.0410693 | 8.7104835 | 1.0866873 | 6.8260777 | 0.6019289 |
| TEKT4 | -0.970642644 | 0.057154457 | 0.012247452 | -124.2871574 | 9.1596632 | 9.0137478 | 7.5571389 | 6.9310735 | 1.2054667 | 0.6019289 |
| PDE6A | -1.777079975 | 0.04958755 | 0.000958838 | -124.3670823 | 8.0044995 | 7.843866 | 8.1639276 | 1.0866873 | 1.2054667 | 0.6019289 |
| C6orf1 | -0.845486138 | 0.077930488 | 0.023202279 | -124.9154799 | 8.7908658 | 8.1702751 | 7.5754206 | 7.522033 | 1.2054667 | 0.6019289 |
| UBA1 | -0.774500595 | 0.102109423 | 0.036419 | -124.9154799 | 9.031425 | 8.1702751 | 7.928209 | 8.5848861 | 1.2054667 | 0.6019289 |
| ANAPC7 | -0.836934433 | 0.080350378 | 0.024583969 | -125.022477 | 8.1404613 | 8.0533052 | 7.5754206 | 1.0866873 | 7.2567201 | 0.6019289 |
| TRIM11 | -0.906514543 | 0.065320795 | 0.016634037 | -125.4085779 | 8.2142315 | 7.9910605 | 8.1759589 | 6.9015613 | 1.2054667 | 0.6019289 |
| PAK1 | -1.738444973 | 0.04958755 | 0.001063147 | -125.888295 | 7.6568826 | 8.181467 | 7.8848881 | 1.0866873 | 1.2054667 | 0.6019289 |
| COX18 | -1.693540988 | 0.04958755 | 0.001255717 | -125.8906781 | 8.062715 | 7.3437697 | 8.3238686 | 1.0866873 | 1.2054667 | 0.6019289 |
| MEG3 | -0.968059287 | 0.057313185 | 0.012443232 | -125.9806114 | 11.3183106 | 12.7395811 | 13.6991642 | 11.2973689 | 5.7625232 | 0.6019289 |
| CHRD | -0.840425429 | 0.079172346 | 0.02396293 | -126.0288094 | 8.1830764 | 7.8154118 | 8.355951 | 7.5025051 | 1.2054667 | 0.6019289 |
| DGKA | -1.02915944 | 0.053066061 | 0.009703924 | -126.8611105 | 7.786906 | 8.1925727 | 8.4281467 | 5.8529567 | 1.2054667 | 0.6019289 |
| ASMTL-AS1 | -1.3265779 | 0.04958755 | 0.003661237 | -127.1848339 | 5.3162271 | 8.0774702 | 8.4281467 | 1.0866873 | 1.2054667 | 0.6019289 |
| HLA-DRB1 | -0.907934297 | 0.065167114 | 0.01653053 | -127.1848339 | 8.4418607 | 8.0774702 | 2.1654208 | 1.0866873 | 8.4524089 | 0.6019289 |
| SEMA3B | -1.293203471 | 0.04958755 | 0.003990211 | -127.3961494 | 7.5951068 | 11.1292182 | 10.2653112 | 5.4258059 | 1.2054667 | 0.6019289 |
| UBASH3B | -1.166914886 | 0.04991757 | 0.006070769 | -127.3961494 | 7.5951068 | 9.8744841 | 10.6291909 | 6.1822306 | 1.2054667 | 0.6019289 |
| MAP7D1 | -1.276723003 | 0.04958755 | 0.00415871 | -127.7785741 | 13.436616 | 14.1921646 | 13.6349676 | 9.5924293 | 1.2054667 | 6.6374655 |
| SYT15 | -1.018883332 | 0.053434625 | 0.01001685 | -127.8629426 | 8.2039211 | 8.181467 | 8.5987306 | 6.2304884 | 1.2054667 | 0.6019289 |
| RINT1 | -1.081430833 | 0.051255379 | 0.008075905 | -128.8067428 | 8.9349778 | 8.214531 | 7.7784397 | 5.6551006 | 1.2054667 | 0.6019289 |
| RARG | -1.707528008 | 0.04958755 | 0.001215598 | -129.3853887 | 7.4101728 | 8.4912918 | 8.1022182 | 1.0866873 | 1.2054667 | 0.6019289 |
| NUDCD3 | -0.811280509 | 0.086963443 | 0.02889192 | -129.3853887 | 9.4443871 | 8.4174829 | 8.2346552 | 1.0866873 | 8.4524089 | 0.6019289 |
| GGA2 | -0.961568439 | 0.05775016 | 0.012688759 | -129.6970769 | 8.2244688 | 7.6640611 | 8.076776 | 6.4501951 | 1.2054667 | 0.6019289 |
| BOP1 | -0.841008568 | 0.079024571 | 0.023840167 | -129.8737246 | 8.1076531 | 9.3916776 | 8.6340471 | 1.0866873 | 1.2054667 | 8.2877844 |
| MCOLN2 | -1.082842865 | 0.051255379 | 0.008051833 | -130.6141445 | 8.234634 | 7.885522 | 9.9798073 | 6.0805901 | 1.2054667 | 0.6019289 |
| KLHL36 | -0.886923443 | 0.068365464 | 0.018477092 | -130.6160642 | 7.8675036 | 8.4174829 | 8.2346552 | 7.147675 | 1.2054667 | 0.6019289 |
| TMEM115 | -0.84830834 | 0.077303306 | 0.022862874 | -130.7523766 | 8.5838045 | 8.0162816 | 8.1022182 | 7.7210195 | 8.4524089 | 0.6019289 |
| RNF216 | -0.818882516 | 0.086352882 | 0.027691567 | -130.7523766 | 8.4242047 | 7.6416849 | 7.8552671 | 7.8031272 | 1.2054667 | 0.6019289 |
| C9orf41 | -1.737871523 | 0.04958755 | 0.001079194 | -131.5763092 | 7.6416849 | 8.0162816 | 8.7187318 | 1.0866873 | 1.2054667 | 0.6019289 |
| EDN1 | -1.547333597 | 0.04958755 | 0.001984273 | -131.8652503 | 8.1296079 | 9.212327 | 6.6010094 | 6.0805901 | 1.2054667 | 0.6019289 |
| CASKIN1 | -0.80252372 | 0.091248678 | 0.030396373 | -132.6980119 | 8.9473922 | 8.2574696 | 7.6972902 | 8.1554584 | 1.2054667 | 0.6019289 |
| NBEAL2 | -1.178789266 | 0.049897122 | 0.005838883 | -132.9696988 | 7.6568826 | 8.7980224 | 9.0547229 | 5.1531951 | 1.2054667 | 0.6019289 |
| USP31 | -0.945273203 | 0.059597087 | 0.013649202 | -133.365349 | 8.2647067 | 9.5029224 | 7.9139132 | 7.147675 | 1.2054667 | 0.6019289 |
| PRDM2 | -0.814438287 | 0.08753544 | 0.028323839 | -133.365349 | 8.2647067 | 7.7417201 | 8.313014 | 7.7378191 | 1.2054667 | 0.6019289 |
| CLN6 | -1.730463411 | 0.04958755 | 0.001103266 | -133.5817338 | 7.9061745 | 8.6924512 | 7.6635078 | 1.0866873 | 1.2054667 | 0.6019289 |
| ARFIP2 | -0.998090167 | 0.0553384 | 0.011002166 | -133.5817338 | 9.1808468 | 8.3693581 | 7.6635078 | 6.4501951 | 1.2054667 | 0.6019289 |
| ATAD3A | -0.851977218 | 0.076025266 | 0.022972 | -133.7405618 | 8.3134756 | 8.5355756 | 8.26876 | 7.4626381 | 1.2054667 | 0.6019289 |
| SENP5 | -1.808464908 | 0.04958755 | 0.000862553 | -133.7405618 | 8.1404613 | 7.9653908 | 8.26876 | 1.0866873 | 1.2054667 | 0.6019289 |
| SNORD22 | -0.977607843 | 0.056452334 | 0.018156696 | -133.7405618 | 8.0512583 | 8.8895842 | 7.6635078 | 6.6761254 | 1.2054667 | 0.6019289 |
| RHOG | -0.79945818 | 0.092882057 | 0.031200353 | -134.6436487 | 8.6836453 | 8.2784691 | 8.0111355 | 8.2521782 | 1.2054667 | 0.6019289 |
| ZBTB5 | -1.709658146 | 0.04958755 | 0.001207574 | -135.0397414 | 8.3325307 | 7.4023354 | 8.1639276 | 1.0866873 | 1.2054667 | 0.6019289 |
| WDR77 | -0.892391203 | 0.067567176 | 0.01793228 | -135.1994867 | 8.2844125 | 9.4060615 | 7.9423658 | 7.6339561 | 1.2054667 | 0.6019289 |
| RUFY1 | -1.072668419 | 0.051291304 | 0.008278103 | -135.6164675 | 8.5352855 | 8.2888552 | 7.8848881 | 5.6551006 | 1.2054667 | 0.6019289 |
| DHX37 | -1.058119957 | 0.051725293 | 0.008786007 | -136.1165559 | 8.2941654 | 8.9884813 | 7.8994736 | 5.9712523 | 1.2054667 | 0.6019289 |
| ZDHHC14 | -1.230390684 | 0.04958755 | 0.004888871 | -136.2910611 | 9.4487599 | 9.8218125 | 9.6278916 | 6.0269554 | 2.5373444 | 0.6019289 |
| LCP1 | -0.882681535 | 0.069240191 | 0.018962529 | -136.589157 | 9.3018043 | 7.6956281 | 9.4756 | 8.1428995 | 1.2054667 | 0.6019289 |
| APRT | -1.059727634 | 0.051660967 | 0.008698548 | -136.7466126 | 9.4960062 | 9.6062 | 7.6972902 | 6.6408414 | 1.2054667 | 0.6019289 |
| PIAS3 | -1.168916415 | 0.04991757 | 0.006005679 | -136.8650636 | 9.2921029 | 8.2574696 | 8.3020771 | 5.4258059 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| C1orf27 | −0.810423663 | 0.088976142 | 0.029082885 | −137.0336254 | 8.3308528 | 8.3693581 | 8.1022182 | 8.0382872 | 1.2054667 | 0.6019289 |
| GNL2 | −0.837940573 | 0.07993439 | 0.024377758 | −137.3014868 | 7.7305591 | 9.2393544 | 8.1873908 | 1.0866873 | 7.956043 | 0.6019289 |
| ABCF3 | −0.885182575 | 0.068624233 | 0.018672872 | −137.5621063 | 8.3882311 | 8.309406 | 8.2910567 | 7.4216382 | 1.2054667 | 0.6019289 |
| LTBP2 | −1.055657991 | 0.051814299 | 0.008851801 | −138.5432709 | 7.7161217 | 9.9582098 | 8.7830733 | 6.4903918 | 1.2054667 | 0.6019289 |
| NIN | −0.858288265 | 0.07443975 | 0.02149001 | −139.7848352 | 8.3325307 | 8.2035936 | 9.3590709 | 8.1302303 | 1.2054667 | 0.6019289 |
| EIF4E2 | −1.092219531 | 0.050952718 | 0.007749338 | −139.9115003 | 9.7078433 | 8.5180248 | 7.7302997 | 5.9712523 | 1.2054667 | 0.6019289 |
| GFPT1 | −1.00333721 | 0.054590844 | 0.010727754 | −139.9895691 | 9.6097199 | 8.0894025 | 8.3346422 | 6.8092213 | 1.2054667 | 0.6019289 |
| EIF5B | −0.896694096 | 0.066891468 | 0.01749659 | −140.7019057 | 8.3419647 | 8.715733 | 8.076776 | 7.3794393 | 1.2054667 | 0.6019289 |
| BCAN | −0.932558572 | 0.0611032 | 0.014547862 | −141.0234444 | 8.6836453 | 7.7417201 | 8.8596637 | 7.0964955 | 1.2054667 | 0.6019289 |
| DCLRE1C | −1.041626265 | 0.052218844 | 0.009265827 | −141.0310718 | 8.6307448 | 7.885522 | 8.3453359 | 5.9712523 | 1.2054667 | 0.6019289 |
| TAB3 | −0.991773349 | 0.055676176 | 0.011206772 | −142.5015434 | 8.5270379 | 7.7567626 | 8.6513864 | 6.4088472 | 1.2054667 | 0.6019289 |
| ACOX3 | −1.769947548 | 0.04958755 | 0.000990933 | −143.1140782 | 7.8675036 | 7.8991443 | 8.3664885 | 1.0866873 | 1.2054667 | 0.6019289 |
| RNF123 | −0.839677133 | 0.079317736 | 0.024103346 | −144.0867366 | 9.545842 | 8.738645 | 8.257481 | 1.0866873 | 1.2054667 | 8.5238744 |
| ACCN3 | −1.122190853 | 0.050341156 | 0.006924497 | −146.317496 | 7.9805393 | 8.3984252 | 9.0350412 | 5.5826351 | 1.2054667 | 0.6019289 |
| ENDOG | −0.858546474 | 0.07443975 | 0.021457915 | −146.3484907 | 9.0488124 | 9.0074725 | 8.2799514 | 1.0866873 | 1.2054667 | 8.2443879 |
| RASA4P | −0.866514478 | 0.0723611 | 0.02059135 | −146.9358494 | 8.720278 | 7.8009715 | 9.708794 | 8.180253 | 1.2054667 | 0.6019289 |
| UPF3B | −0.93047712 | 0.061334604 | 0.014717965 | −147.1214047 | 8.40633 | 8.5442716 | 8.2231054 | 7.0964955 | 1.2054667 | 0.6019289 |
| PHRF1 | −0.923044751 | 0.062250826 | 0.015204204 | −147.1214047 | 8.40633 | 8.5180248 | 7.9282096 | 6.988347 | 1.2054667 | 0.6019289 |
| TRIM3 | −1.1152029 | 0.050341156 | 0.007117067 | −147.2800955 | 8.5516405 | 8.101237 | 8.4078853 | 5.5063453 | 1.2054667 | 0.6019289 |
| HEATR1 | −1.770087533 | 0.04958755 | 0.000982909 | −149.4062111 | 8.085359 | 8.8963925 | 7.8250252 | 1.0866873 | 1.2054667 | 0.6019289 |
| C9orf142 | −1.268615334 | 0.04958755 | 0.004327209 | −149.4062111 | 8.5678121 | 8.6527933 | 7.8250252 | 4.3788962 | 1.2054667 | 0.6019289 |
| CARHSP1 | −1.797501719 | 0.050341156 | 0.000910696 | −151.0838776 | 7.8411348 | 8.3984252 | 8.2346552 | 1.0866873 | 1.2054667 | 0.6019289 |
| UBL4A | −1.361078988 | 0.04958755 | 0.001816109 | −151.1816109 | 9.7509741 | 8.4456055 | 8.4281467 | 4.3788962 | 1.2054667 | 0.6019289 |
| GLRX | −0.828147293 | 0.083137747 | 0.025984113 | −151.4461182 | 8.4593032 | 8.3595375 | 8.4481275 | 4.1976103 | 1.2054667 | 0.6019289 |
| TPP1 | −0.930932127 | 0.061288269 | 0.014670625 | −151.7067672 | 8.4506083 | 8.2574696 | 8.9109561 | 7.8656068 | 1.2054667 | 0.6019289 |
| TCHP | −1.84525382 | 0.04958755 | 0.000742197 | −152.1544347 | 8.085359 | 8.4548593 | 8.3238686 | 8.7262907 | 1.2054667 | 0.6019289 |
| PSMG4 | −1.807936788 | 0.04958755 | 0.000878601 | −152.4876246 | 8.8675036 | 8.3296681 | 8.458015 | 1.0866873 | 1.2054667 | 0.6019289 |
| FNDC4 | −0.860854484 | 0.073757739 | 0.021146594 | −153.1272587 | 9.031425 | 8.464054 | 8.1639276 | 8.1924923 | 1.2054667 | 0.6019289 |
| LOC729603 | −0.843530888 | 0.0786267 | 0.02357779 | −153.5291314 | 9.2171857 | 8.4174829 | 8.4678353 | 7.5976045 | 1.2054667 | 8.2662493 |
| MRPS35 | −1.447577306 | 0.04958755 | 0.002658268 | −153.5409135 | 8.467946 | 8.4362921 | 5.9741452 | 7.0434341 | 1.2054667 | 0.6019289 |
| C9orf114 | −1.863989936 | 0.059219172 | 0.000702078 | −153.5923215 | 8.4152951 | 8.3496496 | 8.2114624 | 1.0866873 | 1.2054667 | 0.6019289 |
| CDKN2A | −1.347283072 | 0.04958755 | 0.003460644 | −154.5706385 | 9.5335435 | 8.0162816 | 8.4775892 | 7.9423658 | 1.2054667 | 0.6019289 |
| CHKA | −0.927505586 | 0.061709548 | 0.014920164 | −155.0729073 | 8.467946 | 8.4822695 | 9.7536389 | 7.9400838 | 1.2054667 | 0.6019289 |
| ERLEC1 | −0.832845493 | 0.081776009 | 0.025235497 | −155.0729073 | 10.3104277 | 8.4822695 | 7.8994736 | 3.4605153 | 1.2054667 | 0.6019289 |
| OTUD7B | −1.869000125 | 0.04958755 | 0.000678007 | −156.2921342 | 8.493568 | 8.23616 | 8.3346422 | 6.0269554 | 1.2054667 | 0.6019289 |
| MAGI2 | −0.82686788 | 0.083599382 | 0.026238466 | −159.0433565 | 8.518743 | 8.2035936 | 8.6427428 | 1.0866873 | 1.2054667 | 0.6019289 |
| ADIPOR2 | −0.879146254 | 0.069835403 | 0.0193244 | −160.8775054 | 8.5352855 | 7.9782827 | 8.7269332 | 7.5976045 | 1.2054667 | 0.6019289 |
| GPATCH3 | −0.948649699 | 0.059219172 | 0.013391639 | −160.9098586 | 8.8316181 | 8.5355756 | 8.050877 | 7.0434341 | 1.2054667 | 0.6019289 |
| TMEM39B | −1.838788308 | 0.04958755 | 0.000766268 | −160.9864594 | 8.016332 | 8.4174829 | 8.4481275 | 7.9963845 | 1.2054667 | 0.6019289 |
| RAB11FIP1 | −0.899579378 | 0.066432398 | 0.017171628 | −162.0659195 | 8.6687278 | 9.7782453 | 7.9423658 | 5.3405168 | 9.3795682 | 0.6019289 |
| SLC45A4 | −1.483476478 | 0.04958755 | 0.002353366 | −162.711655 | 8.5516405 | 8.4410048 | 8.4872775 | 4.6851838 | 1.2054667 | 0.6019289 |
| LOC646214 | −1.090455887 | 0.050995256 | 0.007788654 | −162.711655 | 8.2244688 | 8.4912918 | 8.6938442 | 6.0269554 | 1.2054667 | 0.6019289 |
| FBXO10 | −1.81572425 | 0.04958755 | 0.000822434 | −163.1950704 | 10.2288728 | 7.9523826 | 8.5716641 | 1.0866873 | 1.2054667 | 0.6019289 |
| SCD | −1.710166439 | 0.04958755 | 0.001199551 | −163.6483896 | 9.6136199 | 7.9653908 | 7.9563845 | 5.0495858 | 1.2054667 | 0.6019289 |
| PTRH1 | −1.294375343 | 0.04958755 | 0.003982187 | −163.6483896 | 9.247621 | 9.7103237 | 7.9563845 | 5.3405168 | 1.2054667 | 0.6019289 |
| METTL22 | −1.185531397 | 0.049897122 | 0.005606194 | −164.5041865 | 8.7611989 | 12.0471643 | 11.9011612 | 5.3405168 | 1.2054667 | 0.6019289 |
| NRBP1 | −1.160150061 | 0.04991757 | 0.006207173 | −164.5458051 | 8.5678121 | 8.6846063 | 8.1022182 | 4.6851838 | 1.2054667 | 0.6019289 |
| PRPF3 | −1.018911031 | 0.053434625 | 0.010008826 | −164.7256029 | 8.4506083 | 8.7980224 | 6.5278107 | 6.4088472 | 1.2054667 | 0.6019289 |
| NT5C2 | −1.552180589 | 0.04958755 | 0.001960202 | −164.7256029 | 8.4506083 | 8.7980224 | 6.5278107 | 1.0866873 | 1.2054667 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| USP13 | −1.886083484 | 0.04958755 | 0.000621841 | −165.7213753 | 8.4593032 | 8.4912918 | 8.2910567 | 1.0866873 | 1.2054667 | 0.6019289 |
| HADHB | −1.732147353 | 0.04958755 | 0.001095242 | −166.2679949 | 9.9179761 | 8.464054 | 7.6289155 | 1.0866873 | 1.2054667 | 0.6019289 |
| C15orf48 | −1.831484384 | 0.04958755 | 0.000790339 | −166.4113908 | 7.9805393 | 8.6608125 | 8.3664885 | 6.9599943 | 1.2054667 | 0.6019289 |
| C9orf80 | −0.969701651 | 0.057171148 | 0.012311642 | −166.7468171 | 8.7560036 | 8.5869821 | 8.257481 | 1.0866873 | 1.2054667 | 0.6019289 |
| FAM189B | −1.805915755 | 0.04958755 | 0.000894648 | −168.3958074 | 8.8906661 | 8.1476275 | 7.7976413 | 1.0866873 | 1.2054667 | 0.6019289 |
| CAPN2 | −0.972188703 | 0.056976683 | 0.01211827 | −169.9782824 | 8.8316181 | 9.3022264 | 8.0111355 | 1.0866873 | 1.2054667 | 0.6019289 |
| LARP4B | −1.00590607 | 0.054519995 | 0.010609003 | −170.0482589 | 8.6152671 | 9.0011699 | 8.5533334 | 6.9310735 | 1.2054667 | 0.6019289 |
| PDPK1 | −1.028509852 | 0.053066061 | 0.009711947 | −170.5856686 | 8.7057364 | 8.0162816 | 8.7269332 | 6.3662802 | 1.2054667 | 0.6019289 |
| NAT10 | −1.120056376 | 0.050341156 | 0.006980663 | −170.965335 | 8.6230267 | 9.0262169 | 8.3664885 | 5.9133149 | 1.2054667 | 0.6019289 |
| SLC34A2 | −1.630410002 | 0.04958755 | 0.001536548 | −171.6960137 | 8.5104001 | 11.8278786 | 7.4423001 | 1.0866873 | 1.2054667 | 0.6019289 |
| FBXL15 | −1.815165712 | 0.04958755 | 0.000830458 | −172.063791 | 9.625257 | 8.0287286 | 8.4678353 | 1.0866873 | 1.2054667 | 0.6019289 |
| DNAJA2 | −0.952611676 | 0.058717048 | 0.013163765 | −172.2762996 | 8.3790957 | 9.0324114 | 8.6340471 | 7.335969 | 1.2054667 | 0.6019289 |
| NDOR1 | −1.862220108 | 0.04958755 | 0.000710102 | −174.6336406 | 8.6536544 | 8.136169 | 8.4078853 | 1.0866873 | 1.2054667 | 0.6019289 |
| FAM214B | −1.750957202 | 0.04958755 | 0.001055123 | −174.6336406 | 8.6536544 | 7.5303978 | 8.5533334 | 1.0866873 | 1.2054667 | 0.6019289 |
| S100A16 | −1.00864516 | 0.054374712 | 0.010506299 | −174.7257144 | 9.6633833 | 11.33617 | 8.050877 | 8.0784109 | 1.2054667 | 0.6019289 |
| DEAF1 | −1.808014479 | 0.04958755 | 0.000870577 | −175.7747745 | 8.720278 | 8.5442716 | 7.8096632 | 1.0866873 | 1.2054667 | 0.6019289 |
| TEP1 | −0.934959598 | 0.060960411 | 0.014399422 | −176.308194 | 8.6984102 | 8.9984813 | 8.0638846 | 7.335969 | 1.2054667 | 0.6019289 |
| GSC | −1.738117957 | 0.04958755 | 0.00107171 | −176.8823292 | 9.237547 | 7.4949535 | 8.5533334 | 1.0866873 | 1.2054667 | 0.6019289 |
| ADRBK1 | −0.968704049 | 0.057313185 | 0.01240313 | −177.4479242 | 8.6536544 | 8.6767186 | 8.7987201 | 7.244891 | 1.2054667 | 0.6019289 |
| PRSS8 | −1.655758772 | 0.04958755 | 0.001416192 | −177.7706583 | 8.559749 | 11.5049261 | 7.508617 | 1.0866873 | 1.2054667 | 0.6019289 |
| CROCCP2 | −1.737347339 | 0.04958755 | 0.001087218 | −178.0132167 | 9.1327388 | 7.478994 | 8.5625279 | 6.7442069 | 1.2054667 | 0.6019289 |
| TCP11L1 | −1.087355091 | 0.051099543 | 0.007916232 | −178.0132167 | 9.6406286 | 9.3022264 | 8.5625279 | 1.0866873 | 1.2054667 | 6.7657063 |
| NCKAP5L | −0.842203504 | 0.078867347 | 0.023727834 | −180.6579828 | 8.5838045 | 8.7760413 | 8.1639276 | 1.0866873 | 1.2054667 | 8.818351 |
| RC3H2 | −1.049708942 | 0.051974546 | 0.009026719 | −181.9702575 | 8.7130255 | 8.1589958 | 8.7350882 | 1.0866873 | 1.2054667 | 0.6019289 |
| DOCK9 | −1.840029634 | 0.04958755 | 0.000758244 | −184.7214906 | 8.7346746 | 7.9523826 | 8.6252987 | 6.2771857 | 1.2054667 | 8.7423946 |
| SEMA6A | −0.809221506 | 0.089275781 | 0.029924906 | −186.8450595 | 9.7650691 | 8.1476275 | 9.1122062 | 9.244132 | 1.2054667 | 0.6019289 |
| PRPS1 | −0.897868827 | 0.06669982 | 0.017325684 | −186.8574797 | 8.8249055 | 8.5953745 | 8.7512612 | 7.9524928 | 1.2054667 | 0.6019289 |
| ADRA2C | −1.241808339 | 0.04958755 | 0.004704325 | −187.3855785 | 11.9412356 | 8.8480457 | 8.151795 | 5.7241063 | 1.2054667 | 0.6019289 |
| ST14 | −1.752477485 | 0.051291304 | 0.001047099 | −187.6284116 | 8.6384218 | 11.1103098 | 7.9840197 | 1.0866873 | 1.2054667 | 0.6019289 |
| ENTPD4 | −1.073368374 | 0.04958755 | 0.008262056 | −187.8989939 | 9.5169807 | 8.715733 | 8.7592802 | 6.7442069 | 1.2054667 | 0.6019289 |
| SLC22A23 | −1.780900655 | 0.04958755 | 0.000950814 | −188.3231904 | 10.2237788 | 8.1589958 | 8.2799514 | 1.0866873 | 1.2054667 | 0.6019289 |
| SHROOM3 | −1.798755562 | 0.04958755 | 0.000902672 | −188.9680657 | 8.559749 | 10.5653425 | 8.1639276 | 1.0866873 | 1.2054667 | 0.6019289 |
| USP39 | −0.84736959 | 0.077498921 | 0.022933483 | −190.4529957 | 9.4400009 | 8.9431715 | 8.6599785 | 1.0866873 | 2.8554202 | 8.7423946 |
| JAGN1 | −1.291021385 | 0.04958755 | 0.004014282 | −190.5505537 | 10.0066589 | 8.9984813 | 8.1759589 | 5.0495858 | 1.2054667 | 0.6019289 |
| PDE4D | −0.892584353 | 0.067480686 | 0.017880928 | −191.2794541 | 9.1108314 | 8.181467 | 9.1492942 | 8.0915413 | 1.2054667 | 0.6019289 |
| SCARB1 | −1.236087204 | 0.04958755 | 0.004752586 | −192.2863826 | 8.1935364 | 8.8895842 | 9.2090644 | 5.1531951 | 1.2054667 | 0.6019289 |
| TPRG1L | −0.992402994 | 0.055641947 | 0.011182701 | −193.8718297 | 11.359536 | 10.4543796 | 10.2078722 | 9.4311502 | 1.2054667 | 0.6019289 |
| REEP4 | −1.866626073 | 0.04958755 | 0.000686031 | −193.8922739 | 8.8045782 | 8.7234108 | 8.0638846 | 5.0495858 | 1.2054667 | 0.6019289 |
| SLC26A6 | −1.615837809 | 0.04958755 | 0.001632833 | −195.5946241 | 8.6984102 | 6.8213295 | 9.2551594 | 1.0866873 | 1.2054667 | 0.6019289 |
| MOK | −0.890946565 | 0.067801994 | 0.018099976 | −196.1074499 | 8.4242047 | 8.7980224 | 8.7021879 | 1.0866873 | 7.89754 | 0.6019289 |
| FNBP4 | −0.969143352 | 0.057284566 | 0.012371018 | −196.5904012 | 8.7057364 | 8.5615078 | 8.8891965 | 1.0866873 | 7.2874192 | 0.6019289 |
| UPK3B | −1.89395178 | 0.04958755 | 0.000597769 | −196.6435107 | 8.249055 | 8.23616 | 8.5987306 | 1.0866873 | 1.2054667 | 0.6019289 |
| MMP19 | −0.967039148 | 0.057324142 | 0.012475327 | −197.1919891 | 8.9473922 | 8.225386 | 10.3151209 | 7.8347051 | 1.2054667 | 0.6019289 |
| USP40 | −1.932792181 | 0.04958755 | 0.000517532 | −197.5605898 | 8.8316181 | 8.5869821 | 8.4775892 | 1.0866873 | 1.2054667 | 0.6019289 |
| TACR2 | −1.883823606 | 0.04958755 | 0.000629864 | −201.1262655 | 8.1512337 | 8.738645 | 9.0869404 | 1.0866873 | 1.2054667 | 0.6019289 |
| CCBP2 | −0.942508549 | 0.059875002 | 0.013825724 | −201.5692884 | 8.7418194 | 9.1106081 | 8.7350882 | 1.0866873 | 7.7510357 | 0.6019289 |
| THAP3 | −0.881810206 | 0.069395654 | 0.01905079 | −203.5217256 | 9.3018043 | 8.8410048 | 8.7451057 | 1.0866873 | 1.2054667 | 8.3908876 |
| C13orf33 | −0.886617333 | 0.068383167 | 0.018525235 | −204.5632422 | 9.7403116 | 8.5953745 | 8.8818698 | 8.5567575 | 1.2054667 | 0.6019289 |
| LOX | −1.01904388 | 0.053434625 | 0.009992779 | −204.7929812 | 10.4124568 | 9.7371189 | 8.2799514 | 7.8190025 | 1.2054667 | 0.6019289 |

TABLE 9-continued

Differentially Expressed Genes in CD10-, CD24-, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| RRP9 | -1.638655462 | 0.04958755 | 0.001496429 | -204.8972254 | 8.8842233 | 10.0465526 | 8.685452 | 3.1012538 | 1.2054667 | 0.6019289 |
| MTA3 | -1.075537391 | 0.051291304 | 0.008197866 | -204.8972254 | 8.8842233 | 8.8124926 | 9.0676963 | 6.6408414 | 1.2054667 | 0.6019289 |
| PPP1R3F | -1.864704058 | 0.04958755 | 0.000694054 | -205.1545868 | 9.6329633 | 8.136169 | 8.7672549 | 1.0866873 | 1.2054667 | 0.6019289 |
| PAM16 | -1.555059152 | 0.04958755 | 0.001944155 | -205.351523 | 8.9161535 | 8.7686392 | 6.4897707 | 1.0866873 | 1.2054667 | 0.6019289 |
| MESTIT1 | -1.881839333 | 0.04958755 | 0.000637888 | -205.5524001 | 8.7700497 | 8.1589958 | 9.3107812 | 1.0866873 | 1.2054667 | 0.6019289 |
| FAM73B | -0.959679933 | 0.058006829 | 0.012818743 | -207.4163729 | 8.9287302 | 8.5091687 | 8.7830733 | 8.7759375 | 7.4040744 | 0.6019289 |
| INO80 | -0.997498753 | 0.055362341 | 0.011034261 | -208.5204676 | 9.6018881 | 8.7907325 | 8.7104835 | 8.3453359 | 7.4857665 | 0.6019289 |
| ZNF767 | -1.956547657 | 0.04958755 | 0.000469389 | -208.539735 | 8.7908658 | 8.9031688 | 8.5159583 | 1.0866873 | 1.2054667 | 0.6019289 |
| CLDN4 | -1.482706099 | 0.04958755 | 0.0236139 | -209.5404697 | 9.5979562 | 9.2711329 | 8.313014 | 7.0964955 | 3.9031434 | 0.6019289 |
| FAM50A | -0.881296819 | 0.06950889 | 0.019093316 | -209.6781596 | 9.625257 | 8.5615078 | 8.7987201 | 1.0866873 | 8.5314896 | 0.6019289 |
| HTT | -1.944746855 | 0.04958755 | 0.000501484 | -210.8123442 | 8.6307448 | 8.5268269 | 9.2528282 | 1.0866873 | 1.2054667 | 0.6019289 |
| TGFB2 | -1.16038771 | 0.04991757 | 0.006191149 | -211.0009536 | 8.3230346 | 10.5865465 | 10.992779 | 7.1725999 | 1.2054667 | 0.6019289 |
| TAOK2 | -1.902682465 | 0.04958755 | 0.000573698 | -212.4698427 | 8.3973089 | 8.936581 | 8.4381717 | 1.0866873 | 1.2054667 | 0.6019289 |
| TLE1 | -0.868164597 | 0.072080134 | 0.020475808 | -212.4698427 | 9.4400009 | 8.936581 | 8.8521851 | 8.7759375 | 1.2054667 | 7.8974394 |
| PJA1 | -1.892735881 | 0.04958755 | 0.000605793 | -214.2879639 | 9.0716745 | 8.4548593 | 8.3453359 | 1.0866873 | 1.2054667 | 0.6019289 |
| EPS8L2 | -1.833104284 | 0.04958755 | 0.000782316 | -215.1812484 | 8.3513375 | 9.9998997 | 8.3664885 | 1.0866873 | 1.2054667 | 0.6019289 |
| OFD1 | -1.013957102 | 0.053847872 | 0.010174918 | -215.1812484 | 8.3513375 | 9.1680015 | 9.161448 | 7.0964955 | 1.2054667 | 0.6019289 |
| DGKD | -1.874089809 | 0.04958755 | 0.000661959 | -216.5746807 | 8.3606497 | 9.7782453 | 8.5625279 | 1.0866873 | 1.2054667 | 0.6019289 |
| ANAPC2 | -1.834056877 | 0.04958755 | 0.000774292 | -217.0614504 | 8.9597007 | 7.8717699 | 8.9674264 | 1.0866873 | 1.2054667 | 0.6019289 |
| IRX1 | -1.759617278 | 0.04958755 | 0.001031052 | -217.5017447 | 8.8515705 | 11.5193322 | 8.0111355 | 1.0866873 | 1.2054667 | 0.6019289 |
| SDC1 | -1.073663186 | 0.051291304 | 0.008254032 | -218.1029684 | 8.7630437 | 12.0502202 | 8.9743323 | 7.7544253 | 1.2054667 | 0.6019289 |
| GTF2IRD1 | -0.973612754 | 0.056754796 | 0.012012357 | -220.9871027 | 9.3771524 | 9.5029224 | 8.7450757 | 1.0866873 | 1.2054667 | 0.6019289 |
| PARL | -1.14328116 | 0.050038461 | 0.00667897 | -222.2004657 | 10.5098386 | 9.4576082 | 8.3976469 | 6.7770801 | 1.2054667 | 0.6019289 |
| MFSD7 | -1.184039425 | 0.049897122 | 0.005646313 | -223.1710103 | 9.2969617 | 9.0074725 | 8.5064613 | 5.7899671 | 1.2054667 | 0.6019289 |
| ANKRD9 | -1.048868371 | 0.051974546 | 0.00905079 | -224.1438442 | 9.3018043 | 9.0137478 | 8.4481275 | 6.8406623 | 1.2054667 | 0.6019289 |
| STK39 | -1.908965524 | 0.04958755 | 0.000565674 | -225.3654702 | 8.720278 | 9.6790785 | 8.4180516 | 1.0866873 | 1.2054667 | 0.6019289 |
| CHPF | -1.190029972 | 0.049809046 | 0.005517933 | -225.3654702 | 10.744904 | 9.6349807 | 8.4180516 | 6.4903918 | 1.2054667 | 0.6019289 |
| LAS1L | -1.149041935 | 0.049952273 | 0.006414186 | -225.9900776 | 9.0255823 | 9.1047412 | 8.7987201 | 6.1323043 | 1.2054667 | 0.6019289 |
| ANKS4B | -1.118435442 | 0.050341156 | 0.007036829 | -226.3091709 | 10.6775714 | 10.7994659 | 10.0951772 | 8.0651599 | 2.8554202 | 0.6019289 |
| ATG9A | -1.886631915 | 0.04958755 | 0.000613817 | -226.4778407 | 10.061939 | 8.9099134 | 8.2910567 | 1.0866873 | 1.2054667 | 0.6019289 |
| AGPAT2 | -1.794157386 | 0.04958755 | 0.000918719 | -229.6467922 | 9.0773338 | 8.9299601 | 7.6804979 | 1.0866873 | 1.2054667 | 0.6019289 |
| ADCYAP1R1 | -0.971289785 | 0.057045525 | 0.012158389 | -229.7110784 | 9.3162351 | 8.4456055 | 10.144994 | 8.0517861 | 1.2054667 | 0.6019289 |
| PECR | -0.957010345 | 0.058245659 | 0.012914226 | -231.1651637 | 8.7839604 | 8.9884813 | 8.9394675 | 7.6833888 | 1.2054667 | 0.6019289 |
| TIE1 | -1.91812866 | 0.04958755 | 0.000541603 | -231.1892237 | 9.5252859 | 8.7907325 | 8.6770107 | 1.0866873 | 1.2054667 | 0.6019289 |
| DENND1A | -1.87849402 | 0.04958755 | 0.000645912 | -231.6934852 | 10.475962 | 8.4548593 | 8.458015 | 1.0866873 | 1.2054667 | 0.6019289 |
| CHI3L1 | -1.774527036 | 0.04958755 | 0.000966602 | -234.4300037 | 8.9597007 | 9.4713525 | 7.5934735 | 1.0866873 | 1.2054667 | 0.6019289 |
| S100A14 | -1.771989246 | 0.04958755 | 0.000974886 | -237.4173458 | 8.9779688 | 10.8686094 | 7.8250252 | 1.0866873 | 1.2054667 | 0.6019289 |
| SRGAP2 | -1.104682351 | 0.050647945 | 0.007470112 | -240.0581031 | 9.8065464 | 8.5091687 | 10.3367183 | 7.1971015 | 1.2054667 | 0.6019289 |
| NHEJ1 | -0.918672036 | 0.063231386 | 0.015610206 | -242.474132 | 9.2675602 | 9.1338402 | 9.0083744 | 1.0866873 | 1.2054667 | 8.2443879 |
| UPP1 | -1.917793944 | 0.04958755 | 0.000549627 | -242.7730291 | 9.7997158 | 8.7002536 | 8.5253933 | 1.0866873 | 1.2054667 | 0.6019289 |
| LDB1 | -1.918673102 | 0.04958755 | 0.000533579 | -244.4433886 | 8.5352855 | 8.5953745 | 9.5560578 | 1.0866873 | 1.2054667 | 0.6019289 |
| CHTF18 | -1.06684701 | 0.051378258 | 0.008427345 | -245.5462076 | 8.6910467 | 9.1453174 | 10.4599237 | 7.3578678 | 1.2054667 | 0.6019289 |
| SELS | -1.024302775 | 0.053170593 | 0.009809837 | -245.9380453 | 9.9645265 | 9.167041 | 8.54408 | 7.4626381 | 1.2054667 | 0.6019289 |
| SLC20A2 | -1.248126382 | 0.04958755 | 0.004632111 | -247.5205541 | 9.8302021 | 10.9992667 | 8.5533334 | 6.2771857 | 1.2054667 | 0.6019289 |
| DHX38 | -1.252482902 | 0.04958755 | 0.004575945 | -248.926994 | 10.5181848 | 8.5615078 | 10.7305624 | 6.4501951 | 1.2054667 | 0.6019289 |
| CBLL1 | -1.11931977 | 0.050341156 | 0.007012758 | -253.3288924 | 9.349356 | 9.1903345 | 8.9037393 | 6.6046733 | 1.2054667 | 0.6019289 |
| MCCC2 | -1.911762651 | 0.04958755 | 0.000557651 | -253.9421132 | 9.5900602 | 9.0750432 | 8.2461133 | 1.0866873 | 1.2054667 | 0.6019289 |
| GFER | -1.955966526 | 0.04958755 | 0.000477413 | -254.8395939 | 9.83355 | 8.5953745 | 8.9252822 | 1.0866873 | 1.2054667 | 0.6019289 |
| NFATC4 | -1.013099465 | 0.05402997 | 0.01022627 | -258.7222436 | 10.7643305 | 9.0810319 | 9.220727 | 8.2285993 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| PFKP | −1.187960106 | 0.049809046 | 0.005558052 | −260.8052864 | 9.2171857 | 10.2542676 | 9.232296 | 6.6046733 | 1.2054667 | 0.6019289 |
| SLC25A26 | −1.040815694 | 0.052341914 | 0.009312365 | −262.8883295 | 9.0430399 | 9.5725889 | 9.243773 | 7.4626381 | 1.2054667 | 0.6019289 |
| OBSCN | −1.729177598 | 0.04958755 | 0.001127337 | −263.4489889 | 7.3365789 | 9.1280672 | 9.4559984 | 1.0866873 | 1.2054667 | 0.6019289 |
| PRICKLE3 | −2.003108115 | 0.04958755 | 0.000413223 | −268.0959382 | 8.7057364 | 8.9627645 | 9.2720722 | 1.0866873 | 1.2054667 | 0.6019289 |
| C11orf84 | −1.673769995 | 0.04958755 | 0.001335954 | −268.6965228 | 10.6663503 | 8.6447292 | 11.8191469 | 3.7493131 | 1.2054667 | 0.6019289 |
| EIF2B4 | −1.18183145 | 0.049897122 | 0.005710503 | −270.8399451 | 9.6406286 | 9.2867634 | 8.8064803 | 6.2304884 | 1.2054667 | 0.6019289 |
| HCCS | −1.991827919 | 0.04958755 | 0.000437246 | −274.0121903 | 9.6482555 | 9.1873836 | 8.6076411 | 1.0866873 | 1.2054667 | 0.6019289 |
| ADC | −1.809969915 | 0.04958755 | 0.000854529 | −275.0685108 | 7.7305591 | 9.1903345 | 9.6191055 | 1.0866873 | 1.2054667 | 0.6019289 |
| DPF2 | −0.931796365 | 0.061198931 | 0.01460483 | −276.401096 | 9.4134004 | 9.1047412 | 9.1973068 | 1.0866873 | 8.4387969 | 0.6019289 |
| C15orf61 | −0.969075173 | 0.057284566 | 0.012379042 | −276.428115 | 9.2068962 | 9.3276354 | 9.3162272 | 8.1174489 | 1.2054667 | 0.6019289 |
| MTMR10 | −1.335672777 | 0.04958755 | 0.003564952 | −277.4696374 | 9.6894845 | 8.8052757 | 9.3216528 | 5.1531951 | 1.2054667 | 0.6019289 |
| SAMD4A | −1.181244457 | 0.049897122 | 0.005750622 | −277.8859592 | 8.720278 | 9.8218125 | 10.568875 | 6.7770801 | 1.2054667 | 0.6019289 |
| TEAD4 | −1.004156302 | 0.054558959 | 0.010696462 | −277.8859592 | 8.720278 | 9.6631985 | 9.410896 | 1.0866873 | 7.7728978 | 0.6019289 |
| STX5 | −0.928270665 | 0.061590622 | 0.014850357 | −278.6226398 | 9.9553358 | 9.3276354 | 9.0547229 | 8.7430302 | 1.2054667 | 0.6019289 |
| CASP8 | −1.969325796 | 0.04958755 | 0.000445318 | −278.6628962 | 8.467946 | 9.3326639 | 9.2090644 | 1.0866873 | 1.2054667 | 0.6019289 |
| CREB3 | −0.991361133 | 0.055698998 | 0.011238867 | −279.7937964 | 10.1261411 | 8.8916225 | 9.2149075 | 1.0866873 | 1.2054667 | 8.4683738 |
| ACBD3 | −0.844565126 | 0.078118626 | 0.023361149 | −280.5942047 | 10.2665157 | 9.3276354 | 9.3378081 | 9.9323777 | 1.2054667 | 0.6019289 |
| MOB2 | −0.976739125 | 0.056484456 | 0.011880767 | −281.541151 | 9.2245928 | 9.3426687 | 9.7211633 | 1.0866873 | 1.2054667 | 8.1534715 |
| OPLAH | −2.022592217 | 0.04958755 | 0.000365081 | −281.9321151 | 9.3446707 | 9.0750432 | 8.7672549 | 6.8714329 | 1.2054667 | 0.6019289 |
| C7orf43 | −1.158133585 | 0.04991757 | 0.006247292 | −281.9321151 | 9.3446707 | 9.2446997 | 9.4210413 | 6.5675757 | 1.2054667 | 0.6019289 |
| TAT | −1.03050114 | 0.05293768 | 0.009663002 | −284.7602952 | 9.3633211 | 8.9031688 | 9.3590709 | 7.4422837 | 1.2054667 | 0.6019289 |
| ZC3H3 | −1.104871962 | 0.050647945 | 0.007462088 | −285.60045 | 9.3633211 | 9.5381761 | 8.745057 | 6.8714329 | 1.2054667 | 0.6019289 |
| RABL3 | −1.181603954 | 0.049897122 | 0.005726551 | −287.0833804 | 10.5872439 | 9.9614598 | 8.7672549 | 6.8714329 | 1.2054667 | 0.6019289 |
| CTU2 | −2.057615598 | 0.04958755 | 0.000341009 | −291.1895863 | 9.2725023 | 9.291936 | 8.8964862 | 1.0866873 | 1.2054667 | 0.6019289 |
| PDPN | −0.966171861 | 0.057361825 | 0.012509027 | −293.0924785 | 9.8402226 | 9.337675 | 9.4006788 | 8.5086224 | 1.2054667 | 0.6019289 |
| UBTD1 | −1.124886453 | 0.050330336 | 0.006884378 | −300.0250627 | 9.247621 | 9.4344059 | 9.6667798 | 6.988347 | 1.2054667 | 0.6019289 |
| ISCA1 | −1.089004787 | 0.051027823 | 0.007827971 | −300.0250627 | 9.2526317 | 9.4344059 | 9.5328559 | 7.221194 | 1.2054667 | 0.6019289 |
| ZBTB40 | −1.045224098 | 0.052154186 | 0.009167937 | −300.9979004 | 9.1163395 | 9.4390763 | 10.1203006 | 7.8031272 | 1.2054667 | 0.6019289 |
| LAT | −2.000471888 | 0.04958755 | 0.000421247 | −302.1405275 | 9.2120501 | 8.8410048 | 10.3919196 | 1.0866873 | 1.2054667 | 0.6019289 |
| IRF6 | −1.876038469 | 0.04958755 | 0.000653936 | −302.9679493 | 8.8449503 | 12.1800439 | 9.1112062 | 1.0866873 | 1.2054667 | 0.6019289 |
| PPP3CC | −1.099484575 | 0.050846008 | 0.00757442 | −304.4892519 | 10.1771041 | 9.4576082 | 9.0284206 | 7.3137327 | 1.2054667 | 0.6019289 |
| CIB2 | −1.314098684 | 0.04958755 | 0.003797641 | −307.610468 | 9.4704275 | 9.1736173 | 10.1662594 | 5.7241063 | 1.2054667 | 0.6019289 |
| APBB1 | −0.880690685 | 0.069591194 | 0.019150285 | −310.9834366 | 9.9614695 | 9.3673812 | 9.3107812 | 1.0866873 | 9.4354708 | 0.6019289 |
| C16orf61 | −0.96953519 | 0.057171148 | 0.012335714 | −313.6447944 | 9.2774274 | 9.4984545 | 9.5514472 | 8.3537595 | 1.2054667 | 0.6019289 |
| SSRP1 | −1.096073289 | 0.050930656 | 0.007643029 | −315.5687158 | 10.281302 | 9.7634255 | 8.9037393 | 7.4626381 | 1.2054667 | 0.6019289 |
| NOL6 | −1.121541297 | 0.049694878 | 0.005109962 | −316.0059962 | 8.9349778 | 10.6402613 | 9.5092748 | 6.5294995 | 1.2054667 | 0.6019289 |
| ELN | −1.3107077 | 0.04958755 | 0.003813689 | −317.3213699 | 4.7435639 | 9.3964882 | 10.4500491 | 1.0866873 | 1.2054667 | 0.6019289 |
| C15orf17 | −1.045359173 | 0.052154186 | 0.009159913 | −322.2551404 | 9.4443871 | 9.5381761 | 9.5375262 | 7.7544253 | 1.2054667 | 0.6019289 |
| SBF1P1 | −1.18129826 | 0.049897122 | 0.005742598 | −323.2009053 | 9.5417541 | 9.789261 | 9.1794888 | 6.6046733 | 1.2054667 | 0.6019289 |
| ZNF692 | −1.033090662 | 0.052897282 | 0.009585974 | −326.8282723 | 9.6136199 | 9.4390763 | 9.9866543 | 1.0866873 | 1.2054667 | 8.0053615 |
| MDM4 | −0.9042061 | 0.06561616 | 0.01679907 | −328.2373702 | 10.221225 | 9.5640624 | 9.2998271 | 9.3787623 | 9.4354708 | 0.6019289 |
| CCDC127 | −1.229027469 | 0.04958755 | 0.004904919 | −330.1830474 | 9.5940136 | 9.5725889 | 9.2031976 | 6.1822306 | 1.2054667 | 0.6019289 |
| IDUA | −1.118108804 | 0.050341156 | 0.007052877 | −330.8368735 | 8.9719051 | 9.6144818 | 10.7548302 | 7.4216382 | 1.2054667 | 0.6019289 |
| AGFG1 | −2.122985576 | 0.04958755 | 0.000252748 | −332.1098859 | 9.5661093 | 9.4622042 | 9.1735003 | 1.0866873 | 1.2054667 | 0.6019289 |
| CENPT | −1.011796623 | 0.054077708 | 0.010306507 | −334.2059233 | 9.5900602 | 9.9582098 | 9.0805542 | 8.0915413 | 1.2054667 | 0.6019289 |
| KLHDC3 | −1.032141646 | 0.052917554 | 0.009608441 | −338.9385959 | 10.7234089 | 9.6103468 | 9.220727 | 8.3206874 | 1.2054667 | 0.6019289 |
| CYB5R2 | −0.98695882 | 0.056015811 | 0.011403354 | −342.4715885 | 10.1928307 | 10.4658679 | 9.0217694 | 1.0866873 | 8.8521692 | 0.6019289 |
| IRF7 | −1.124787095 | 0.050330336 | 0.006892402 | −342.8299514 | 9.2274023 | 9.626816 | 9.9022635 | 7.1725999 | 1.2054667 | 0.6019289 |
| RNF26 | −1.072597284 | 0.051291304 | 0.008286127 | −344.7756292 | 10.2689906 | 9.6349807 | 9.4159775 | 7.8808129 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| SHF | -2.068944649 | 0.04958755 | 0.000308914 | -346.4853095 | 9.1649884 | 9.0385793 | 9.7046472 | 1.0866873 | 1.2054667 | 0.6019289 |
| KRBA1 | -1.952241559 | 0.04958755 | 0.000485437 | -346.9535054 | 9.5252859 | 9.6869535 | 8.355951 | 1.0866873 | 1.2054667 | 0.6019289 |
| GDI1 | -1.065545116 | 0.051178258 | 0.004891535 | -348.2932537 | 9.8731306 | 9.3124437 | 9.6496254 | 7.7210195 | 1.2054667 | 0.6019289 |
| ASB6 | -2.069392577 | 0.04958755 | 0.000300891 | -348.8016827 | 9.1860944 | 9.789261 | 9.0481921 | 1.0866873 | 1.2054667 | 0.6019289 |
| RASSF7 | -1.843825426 | 0.04958755 | 0.000750221 | -349.909191 | 7.7843794 | 9.8641025 | 9.5375262 | 9.4920255 | 1.2054667 | 0.6019289 |
| ATP13A3 | -0.879850994 | 0.069719181 | 0.019265827 | -350.3763035 | 9.667141 | 9.4576082 | 9.6582281 | 5.8529567 | 1.2054667 | 0.6019289 |
| TAF1C | -1.325813209 | 0.04958755 | 0.003677285 | -351.63054 | 9.6638333 | 9.659201 | 9.87669 | 6.7770801 | 1.2054667 | 0.6019289 |
| ZNF592 | -1.154931649 | 0.04991757 | 0.006311482 | -351.63054 | 9.6638333 | 9.1047412 | 9.6667798 | 8.6395496 | 1.2054667 | 0.6019289 |
| JARID2 | -1.01023974 | 0.054185592 | 0.010434085 | -353.5008785 | 10.4673671 | 9.5683319 | 9.6710367 | 8.3250145 | 8.3250145 | 0.6019289 |
| ACSL4 | -1.005248462 | 0.054519995 | 0.010633074 | -354.2926717 | 9.9274071 | 9.5554851 | 9.4057964 | 1.0866873 | 1.2054667 | 0.6019289 |
| SRP72 | -1.130324879 | 0.050131358 | 0.006749579 | -356.6254536 | 11.2026761 | 9.3722734 | 9.6837325 | 7.7378191 | 1.2054667 | 0.6019289 |
| PPFIA1 | -0.996526487 | 0.054193354 | 0.011075183 | -359.8793528 | 9.7615582 | 9.7295138 | 9.0932984 | 8.2166637 | 1.2054667 | 0.6019289 |
| DECR2 | -1.04691939 | 0.052136699 | 0.009121399 | -372.2501736 | 9.1860944 | 9.626816 | 9.7735711 | 1.0866873 | 7.7944336 | 0.6019289 |
| RA114 | -1.336629914 | 0.04958755 | 0.003540881 | -375.7046063 | 10.3807689 | 10.5907502 | 9.1553839 | 6.0805901 | 1.2054667 | 0.6019289 |
| AMOTL1 | -1.208284077 | 0.04976927 | 0.005275616 | -377.8521646 | 9.5620786 | 9.7671448 | 10.3096707 | 6.9015613 | 1.2054667 | 0.6019289 |
| C8orf82 | -2.019365041 | 0.04958755 | 0.000373104 | -378.5881171 | 10.1771041 | 9.6511726 | 8.685452 | 1.0866873 | 1.2054667 | 0.6019289 |
| NT5DC3 | -1.17835977 | 0.04991757 | 0.005854128 | -379.6075768 | 9.1702939 | 11.432999 | 10.640089 | 8.1045532 | 7.7728978 | 0.6019289 |
| FGFRL1 | -1.035641328 | 0.052732335 | 0.00950333 | -380.810206 | 9.6596157 | 10.1012355 | 10.3096707 | 6.2771857 | 1.2054667 | 8.9045161 |
| TMEM63B | -2.139009203 | 0.04958755 | 0.000228677 | -385.181377 | 9.1913231 | 9.7371189 | 9.6921348 | 9.2265231 | 1.2054667 | 0.6019289 |
| RMND5B | -1.992047471 | 0.04958755 | 0.000429271 | -387.0387096 | 10.4124568 | 9.6830214 | 8.5897647 | 1.0866873 | 1.2054667 | 0.6019289 |
| AEN | -2.131847591 | 0.04958755 | 0.000244724 | -391.7638487 | 9.7005278 | 9.8916225 | 9.1553839 | 1.0866873 | 1.2054667 | 0.6019289 |
| CPSF4 | -1.04270456 | 0.052218844 | 0.009241756 | -392.3083547 | 10.1397279 | 9.2177732 | 9.87669 | 8.1045532 | 1.2054667 | 0.6019289 |
| YARS | -1.309803 | 0.04958755 | 0.00383776 | -394.694925 | 10.3738871 | 10.484061 | 9.2265231 | 6.2771857 | 1.2054667 | 0.6019289 |
| SNX8 | -2.066344568 | 0.04958755 | 0.000324962 | -396.5456278 | 10.2058065 | 9.7180304 | 8.8891965 | 1.0866873 | 1.2054667 | 0.6019289 |
| PLXNB1 | -1.050757239 | 0.051900312 | 0.008978577 | -398.5385928 | 10.5812817 | 11.4504526 | 9.7252629 | 6.2771857 | 1.2054667 | 9.1119156 |
| POLR3E | -2.154194175 | 0.04958755 | 0.000196582 | -406.0831357 | 9.2675602 | 9.6869535 | 9.9485869 | 1.0866873 | 1.2054667 | 0.6019289 |
| MIR205HG | -2.005277086 | 0.04958755 | 0.000405199 | -408.6922091 | 9.7615582 | 12.4031935 | 9.9130863 | 1.0866873 | 1.2054667 | 0.6019289 |
| TTLL4 | -2.149222233 | 0.04958755 | 0.000212629 | -408.9376732 | 9.6097199 | 9.6830214 | 9.2720722 | 1.0866873 | 1.2054667 | 0.6019289 |
| RBM23 | -1.385841948 | 0.04958755 | 0.000244724 | -415.7929187 | 10.4993373 | 9.8480074 | 9.2776661 | 1.0866873 | 1.2054667 | 0.6019289 |
| CEP104 | -1.143556892 | 0.050004604 | 0.006510471 | -417.738599 | 9.9211266 | 9.9051881 | 9.6879398 | 5.7899671 | 1.2054667 | 0.6019289 |
| MSC | -1.176853531 | 0.04991757 | 0.005886223 | -427.784312 | 11.3537183 | 9.9119233 | 9.4006788 | 7.244891 | 7.7062919 | 0.6019289 |
| SLC25A37 | -1.264855103 | 0.04958755 | 0.004383375 | -428.4907328 | 10.5624580 | 9.3426687 | 10.3014565 | 6.2771857 | 1.2054667 | 0.6019289 |
| TNRC18 | -2.13855213 | 0.04958755 | 0.000236701 | -430.7406434 | 10.8278185 | 11.3121855 | 9.9485869 | 1.0866873 | 1.2054667 | 0.6019289 |
| B4GALT2 | -1.200331177 | 0.049809046 | 0.005357458 | -432.3340874 | 9.9614695 | 10.2436282 | 9.8317667 | 6.9310735 | 1.2054667 | 0.6019289 |
| MPHOSPH10 | -2.14835658 | 0.04958755 | 0.000220653 | -434.1682598 | 9.9675771 | 9.9647026 | 9.4853018 | 6.988347 | 1.2054667 | 0.6019289 |
| GAK | -1.057736319 | 0.051778996 | 0.000410845 | -439.1410845 | 10.3104277 | 9.9840074 | 9.1973068 | 8.2404369 | 1.2054667 | 0.6019289 |
| EIF4G1 | -1.150402457 | 0.049952273 | 0.006406162 | -442.1707781 | 10.1771041 | 10.2934808 | 9.4853018 | 7.4626381 | 1.2054667 | 0.6019289 |
| RPS6KA4 | -2.197651511 | 0.04958755 | 0.000180534 | -443.032446 | 9.7259714 | 9.9967352 | 9.3903888 | 1.0866873 | 1.2054667 | 0.6019289 |
| TEX264 | -1.506556711 | 0.04958755 | 0.002176843 | -446.1966831 | 10.5624580 | 9.6631985 | 9.4853018 | 5.0495858 | 7.7062919 | 0.6019289 |
| RBM15B | -1.036998998 | 0.052603935 | 0.009214888 | -447.8966482 | 10.3989614 | 10.0124887 | 9.8618705 | 8.6835719 | 1.2054667 | 0.6019289 |
| C1orf51 | -1.21586143 | 0.049622329 | 0.005122156 | -449.2801383 | 9.4134004 | 10.1240072 | 10.1046498 | 1.0866873 | 6.8672984 | 0.6019289 |
| CTPS | -1.091998447 | 0.050952718 | 0.007757362 | -451.6659568 | 10.1124251 | 10.2355969 | 9.4210413 | 1.0866873 | 7.956043 | 0.6019289 |
| DUSP2 | -1.071981094 | 0.051313496 | 0.008310198 | -456.2474005 | 9.4356014 | 11.6916565 | 11.6177631 | 9.4157741 | 1.2054667 | 0.6019289 |
| RBM19 | -2.19370782 | 0.04958755 | 0.000185558 | -465.4520309 | 9.949176 | 10.3391716 | 9.4311157 | 1.0866873 | 1.2054667 | 0.6019289 |
| HLA-DRB5 | -1.06249744 | 0.051458876 | 0.008579796 | -466.3929082 | 11.4275778 | 2.406905 | 9.9520894 | 8.6835719 | 1.2054667 | 0.6019289 |
| YY1AP1 | -1.140015964 | 0.050038461 | 0.006566637 | -471.4267509 | 9.9675771 | 9.7409065 | 10.6026947 | 1.0866873 | 7.7944336 | 0.6019289 |
| PPP6R3 | -1.351378153 | 0.04958755 | 0.003420525 | -476.3542331 | 10.1013577 | 9.6227163 | 10.637916 | 6.1323043 | 1.2054667 | 0.6019289 |
| ST6GALNAC4 | -1.285113497 | 0.04958755 | 0.004078472 | -476.986444 | 11.5778717 | 10.2569152 | 9.4997334 | 6.9310735 | 1.2054667 | 0.6019289 |
| HIAT1 | -1.322400605 | 0.04958755 | 0.003693332 | -479.52554 | 10.688706 | 10.0373419 | 10.1109305 | 6.5675757 | 1.2054667 | 0.6019289 |

TABLE 9-continued

Differentially Expressed Genes in CD10−, CD24−, CD44+ Breast Epithelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| TCIRG1 | -1.155969856 | 0.04991757 | 0.006279387 | -486.8162289 | 10.9562254 | 9.8536456 | 10.1137001 | 7.9107527 | 1.2054667 | 0.6019289 |
| PRDM1 | -1.064407776 | 0.051378258 | 0.008852363 | -489.1934451 | 10.1397279 | 9.9319425 | 12.6014599 | 9.4052958 | 1.2054667 | 0.6019289 |
| ELTD1 | -1.172245787 | 0.04991757 | 0.005934366 | -489.8673135 | 10.150506 | 9.5381761 | 10.2959543 | 1.0866873 | 7.3757827 | 0.6019289 |
| ARHGAP21 | -1.097391256 | 0.050892627 | 0.007614539 | -491.6744774 | 9.7331593 | 10.1470263 | 11.354818 | 8.5280696 | 1.2054667 | 0.6019289 |
| ERI3 | -1.131503515 | 0.050131358 | 0.006725508 | -495.9768187 | 11.286905 | 10.7830279 | 9.5560578 | 8.3967085 | 1.2054667 | 0.6019289 |
| SHARPIN | -1.197014776 | 0.049809046 | 0.005381529 | -497.7593503 | 10.9298789 | 10.4404718 | 9.5606537 | 7.5413002 | 1.2054667 | 0.6019289 |
| NPM3 | -1.209047034 | 0.04976927 | 0.005227473 | -500.7244135 | 10.1894988 | 10.4543796 | 9.5698019 | 7.147675 | 1.2054667 | 0.6019289 |
| RASSF4 | -2.149457138 | 0.04958755 | 0.000204606 | -501.3003551 | 10.0562188 | 9.2013727 | 10.2821063 | 1.0866873 | 1.2054667 | 0.6019289 |
| ATG4B | -1.30720084 | 0.04958755 | 0.003861831 | -520.3743927 | 10.2288728 | 9.7782453 | 10.2848865 | 6.4501951 | 1.2054667 | 0.6019289 |
| RDBP | -1.292042051 | 0.04958755 | 0.004006259 | -522.8798613 | 11.201381 | 10.6032881 | 9.6322646 | 6.988347 | 1.2054667 | 0.6019289 |
| ANAPC1 | -2.3237163 | 0.04958755 | 0.000140416 | -524.069121 | 10.145127 | 10.094707 | 10.1203006 | 1.0866873 | 1.2054667 | 0.6019289 |
| CNPY3 | -1.326627967 | 0.04958755 | 0.00364519 | -526.0449259 | 11.0727157 | 10.5823306 | 9.6409711 | 6.6761254 | 1.2054667 | 0.6019289 |
| TFRC | -1.113336621 | 0.050440463 | 0.007182861 | -526.3942621 | 9.9522592 | 10.9196294 | 10.2454666 | 8.3753938 | 1.2054667 | 0.6019289 |
| EXTL3 | -1.4299608 | 0.04958755 | 0.002818743 | -532.3750557 | 11.9295502 | 10.8210959 | 9.6582281 | 6.2771857 | 1.2054667 | 0.6019289 |
| PDXDC2P | -1.143231837 | 0.05004604 | 0.006518495 | -547.8181585 | 10.1638663 | 10.4451226 | 10.1842406 | 1.0866873 | 8.0122661 | 0.6019289 |
| ABCF1 | -1.208532092 | 0.04976927 | 0.005251545 | -560.8606471 | 10.4522017 | 10.7211001 | 9.7334275 | 7.4626381 | 1.2054667 | 0.6019289 |
| AGPAT6 | -1.093955674 | 0.050952718 | 0.007709219 | -564.6375571 | 10.52234 | 10.346648 | 10.3096707 | 8.6033384 | 1.2054667 | 0.6019289 |
| TMUB1 | -1.353502195 | 0.04958755 | 0.003404477 | -566.5832397 | 10.8577227 | 10.3516108 | 9.9968644 | 6.4903918 | 1.2054667 | 0.6019289 |
| UBE3C | -1.325855596 | 0.04958755 | 0.003669261 | -570.3558468 | 10.8982541 | 11.0672144 | 9.7576474 | 6.8714329 | 1.2054667 | 0.6019289 |
| JHDM1D | -1.297089546 | 0.04958755 | 0.003958116 | -572.2214721 | 10.8642847 | 10.0828183 | 10.3658965 | 6.9599943 | 1.2054667 | 0.6019289 |
| HSD11B1 | -2.231594237 | 0.04958755 | 0.000164487 | -573.8290139 | 10.4116938 | 9.5425229 | 10.2511644 | 1.0866873 | 1.2054667 | 0.6019289 |
| ZBTB7B | -2.278605468 | 0.04958755 | 0.000156463 | -574.9886042 | 10.2340769 | 10.4451226 | 9.7536389 | 1.0866873 | 8.5942324 | 0.6019289 |
| BRF1 | -1.06401508 | 0.051416052 | 0.008547701 | -579.967541 | 10.2665157 | 9.9352522 | 10.3340363 | 7.522033 | 1.2054667 | 0.6019289 |
| GABBR1 | -1.195187312 | 0.04958755 | 0.005421648 | -580.0355996 | 10.4324661 | 9.7819266 | 10.5597209 | 6.6046733 | 1.2054667 | 0.6019289 |
| TNFRSF4 | -1.362226553 | 0.053094283 | 0.009752066 | -588.9046168 | 10.7034196 | 9.8038191 | 11.2319795 | 9.6688827 | 1.2054667 | 0.6019289 |
| CAPG | -2.338244164 | 0.04958755 | 0.000132392 | -592.0104983 | 10.2135363 | 10.0738369 | 10.4149456 | 1.0866873 | 7.9173057 | 0.6019289 |
| TMEM150A | -1.377574605 | 0.04958755 | 0.003179812 | -594.0935538 | 10.5812817 | 10.0647994 | 10.420013 | 6.2771857 | 1.2054667 | 0.6019289 |
| HIVEP3 | -1.958203811 | 0.04958755 | 0.000461366 | -598.3038045 | 8.3513375 | 10.3114217 | 10.4021988 | 6.1822306 | 1.2054667 | 0.6019289 |
| HIP1R | -1.413085767 | 0.04958755 | 0.002931076 | -623.4618933 | 9.8860865 | 11.8820494 | 10.7264778 | 1.0866873 | 1.2054667 | 0.6019289 |
| FOXF2 | -2.06728355 | 0.04958755 | 0.000316938 | -625.7737647 | 10.3761847 | 8.8689644 | 11.102436 | 6.6408414 | 8.0663803 | 0.6019289 |
| BCL9L | -1.122875356 | 0.050330336 | 0.006908449 | -642.4648719 | 10.484506 | 10.5329404 | 10.9478749 | 1.0866873 | 1.2054667 | 0.6019289 |
| CARS | -1.301826243 | 0.04958755 | 0.00390195 | -685.8808531 | 11.7761924 | 11.7650993 | 10.8685469 | 8.6748743 | 1.2054667 | 0.6019289 |
| OSTF1 | -1.24743225 | 0.04958755 | 0.004440135 | -701.2455606 | 11.0178349 | 10.0557048 | 10.0237431 | 7.8031272 | 1.2054667 | 0.6019289 |
| SH3PXD2A | -1.026389057 | 0.053094283 | 0.009752066 | -707.4601654 | 10.6719718 | 10.2057601 | 11.217504 | 7.704022 | 1.2054667 | 0.6019289 |
| NOC4L | -1.238616511 | 0.04958755 | 0.004473642 | -731.7743792 | 11.041209 | 11.2734843 | 10.117184 | 9.6688827 | 1.2054667 | 0.6019289 |
| KLC2 | -1.443114232 | 0.04958755 | 0.002714435 | -738.6411371 | 10.7341965 | 10.7811898 | 10.4021988 | 6.1822306 | 7.9173057 | 0.6019289 |
| BCKDK | -1.347561777 | 0.04958755 | 0.00345262 | -753.36883 | 11.6143372 | 10.7626792 | 10.2368775 | 7.0964955 | 1.2054667 | 0.6019289 |
| ACOT7 | -1.228589032 | 0.049622329 | 0.00492899 | -753.8409114 | 10.2861973 | 11.3311537 | 11.1252092 | 1.6938929 | 8.0663803 | 0.6019289 |
| SPSB3 | -1.09414793 | 0.050952718 | 0.007701196 | -782.1046505 | 11.2257922 | 10.6979052 | 11.9588801 | 1.0866873 | 1.2054667 | 0.6019289 |
| PVT1 | -2.117228858 | 0.04958755 | 0.000260772 | -785.7347293 | 9.7894089 | 12.9182925 | 10.8233652 | 1.6938929 | 1.2054667 | 9.7618489 |
| SETD5 | -1.119427798 | 0.050341156 | 0.00699671 | -786.9794931 | 9.9684592 | 10.2221111 | 10.8869629 | 8.7840484 | 1.2054667 | 0.6019289 |
| DENND5A | -1.164886351 | 0.04991757 | 0.006094841 | -813.8423114 | 10.8740722 | 10.6095165 | 11.3145693 | 8.7178475 | 1.2054667 | 0.6019289 |
| HBA2 | -2.438275777 | 0.04958755 | 0.000108321 | -822.2406076 | 10.7555327 | 10.8892344 | 10.4149456 | 1.0866873 | 1.2054667 | 0.6019289 |
| PANK4 | -2.486263498 | 0.04958755 | 9.23E-05 | -831.6759225 | 10.685004 | 10.8529448 | 10.786565 | 1.0866873 | 1.2054667 | 0.6019289 |
| METTL17 | -1.482528902 | 0.04958755 | 0.002369413 | -845.7169775 | 10.9638836 | 11.0822207 | 10.32596 | 6.0805901 | 1.2054667 | 0.6019289 |
| SCRIB | -1.519020197 | 0.04958755 | 0.002128701 | -853.2770769 | 10.9423372 | 11.1507321 | 10.6975571 | 6.0269554 | 1.2054667 | 0.6019289 |
| SPSB1 | -1.129664342 | 0.050131358 | 0.006765626 | -861.3542886 | 10.7678347 | 10.9559296 | 12.1151698 | 9.5018945 | 1.2054667 | 0.6019289 |
| NCOR2 | -1.154796082 | 0.04991757 | 0.006319506 | -871.2352855 | 11.0811904 | 10.3688475 | 11.3614183 | 8.8001347 | 1.2054667 | 0.6019289 |
| MARS | -1.807733194 | 0.04958755 | 0.000886624 | -886.8629295 | 12.5076077 | 12.0185859 | 10.3944962 | 4.8170878 | 1.2054667 | 0.6019289 |

TABLE 9-continued

Differentially Expressed Genes in CD10−, CD24−, CD44+ Breast Epthelial cells of BRCA2 Mutation Carriers

| ID | t-value | q-value | p-value | Fold change | P1 | P2 | P3 | BRCA2-N151 | BRCA2-N161 | BRCA2-N172 |
|---|---|---|---|---|---|---|---|---|---|---|
| TBRG4 | -1.635451967 | 0.04958755 | 0.001512477 | -950.164405 | 11.5678559 | 11.6679794 | 10.4939623 | 5.5826351 | 1.2054667 | 0.6019289 |
| LAMC3 | -1.162042867 | 0.04991757 | 0.006151007 | -1038.411561 | 10.7015886 | 11.2256293 | 12.4890185 | 9.4261769 | 1.2054667 | 0.6019289 |
| WDR43 | -1.289690541 | 0.04958755 | 0.00403033 | -1056.826885 | 10.6474523 | 11.7669579 | 11.1999314 | 1.0866873 | 8.0305306 | 0.6019289 |
| THAP4 | -1.230088278 | 0.04958755 | 0.004896895 | -1057.776938 | 11.4787224 | 11.4768113 | 10.6487486 | 8.5086224 | 1.2054667 | 0.6019289 |
| LRCH4 | -1.300096053 | 0.04958755 | 0.003926021 | -1061.759775 | 10.8708171 | 11.2577084 | 11.3534943 | 7.8958605 | 1.2054667 | 0.6019289 |
| PKP4 | -1.409205026 | 0.04958755 | 0.002979218 | -1194.433713 | 11.4275778 | 12.6207635 | 11.3415261 | 7.8031272 | 1.2054667 | 0.6019289 |
| MMP12 | -2.472561968 | 0.04958755 | 0.000100297 | -1222.360855 | 12.3429402 | 11.1691215 | 10.8573834 | 1.0866873 | 1.2054667 | 0.6019289 |
| AKT1 | -1.268544805 | 0.04958755 | 0.004335232 | -1249.518342 | 12.0300023 | 11.492623 | 11.3521694 | 8.7595777 | 1.2054667 | 0.6019289 |
| CXCR7 | -1.56648185 | 0.04958755 | 0.001871941 | -1268.254454 | 12.2463976 | 12.0240363 | 10.9105574 | 1.0866873 | 6.6002221 | 0.6019289 |
| CXCL1 | -1.57288326 | 0.04958755 | 0.001839846 | -1276.993173 | 10.920464 | 11.6489554 | 11.5500399 | 6.1822306 | 1.2054667 | 0.6019289 |
| PLAU | -1.32661482 | 0.04958755 | 0.003653214 | -1394.857498 | 13.4225123 | 12.862886 | 11.0478309 | 9.1963108 | 1.2054667 | 0.6019289 |
| MMP3 | -1.782634668 | 0.04958755 | 0.000934767 | -1404.352727 | 14.4665178 | 12.539371 | 11.05761485 | 5.8529567 | 1.2054667 | 0.6019289 |
| HAPLN3 | -1.425218988 | 0.04958755 | 0.002850838 | -1417.732406 | 11.0712985 | 12.1433106 | 12.2438842 | 7.7210195 | 1.2054667 | 0.6019289 |
| SLC39A13 | -1.534554747 | 0.04958755 | 0.002032416 | -1451.218318 | 11.7085155 | 11.8552182 | 11.378439 | 6.7770801 | 1.2054667 | 0.6019289 |
| POLG | -1.289672695 | 0.04958755 | 0.004038354 | -1473.272096 | 11.6006476 | 11.7302749 | 12.3264891 | 8.9227488 | 1.2054667 | 0.6019289 |
| TRIM8 | -1.430480932 | 0.04958755 | 0.00281072 | -1524.587701 | 12.1789072 | 11.1761323 | 12.5772823 | 7.8656068 | 1.2054667 | 0.6019289 |
| FOSL1 | -1.4246527 | 0.04958755 | 0.002858862 | -1542.92711 | 11.7969209 | 12.7376868 | 11.6243638 | 8.0246608 | 1.2054667 | 0.6019289 |
| NCS1 | -1.354139155 | 0.04958755 | 0.003396454 | -1796.820819 | 11.8979182 | 12.1056174 | 11.8095251 | 1.0866873 | 8.492491 | 0.6019289 |
| YTHDC1 | -1.178215458 | 0.04991757 | 0.005862152 | -1960.202132 | 12.1422534 | 11.7110949 | 12.7380809 | 10.3342478 | 1.2054667 | 0.6019289 |
| MMP1 | -2.041983191 | 0.04958755 | 0.000357057 | -1991.599689 | 15.9395716 | 12.0463993 | 9.4756 | 1.0866873 | 1.2054667 | 0.6019289 |
| DAXX | -1.729329332 | 0.04958755 | 0.001119313 | -2141.805429 | 12.1802227 | 12.964062 | 12.270784 | 6.32242 | 1.2054667 | 0.6019289 |
| KLC1 | -1.368185449 | 0.04958755 | 0.003252026 | -2146.563279 | 12.6482792 | 12.4640362 | 11.6697419 | 8.7430302 | 1.2054667 | 0.6019289 |
| CDK16 | -1.41163952 | 0.04958755 | 0.002947123 | -2393.984757 | 12.4306649 | 12.4968854 | 12.1743664 | 8.5567575 | 1.2054667 | 0.6019289 |
| FBXW5 | -1.766773527 | 0.04958755 | 0.000998957 | -2516.87735 | 13.2849926 | 12.5732248 | 11.8993481 | 6.2771857 | 1.2054667 | 0.6019289 |
| SS18L2 | -1.562850336 | 0.04958755 | 0.001904036 | -2600.044501 | 12.4262368 | 12.4310079 | 12.9131587 | 1.0866873 | 7.7062919 | 0.6019289 |
| KRT5 | -2.422419242 | 0.04958755 | 0.000116344 | -2643.241145 | 12.4547797 | 15.685283 | 11.4396006 | 1.0866873 | 1.2054667 | 0.6019289 |
| SNORD36C | -2.653171098 | 0.04958755 | 8.42E-05 | -2679.560608 | 11.305107 | 12.6088953 | 12.4744788 | 1.0866873 | 1.2054667 | 0.6019289 |
| PTPN23 | -1.617863825 | 0.04958755 | 0.001616786 | -2918.84222 | 12.9406847 | 13.016896 | 12.1131094 | 7.400693 | 1.2054667 | 0.6019289 |
| PDLIM4 | -1.556766622 | 0.04958755 | 0.001928107 | -3067.127371 | 12.788139 | 14.1826228 | 12.679069 | 8.3967085 | 1.2054667 | 0.6019289 |
| LOC493754 | -1.710741767 | 0.04958755 | 0.001183503 | -3620.335642 | 12.5910761 | 13.0273744 | 13.6360568 | 7.221194 | 1.2054667 | 0.6019289 |
| DEXI | -1.439654924 | 0.04958755 | 0.002754553 | -3816.388306 | 13.1034589 | 13.1602396 | 12.7642174 | 9.1278561 | 1.2054667 | 0.6019289 |
| TNFRSF1B | -1.588927616 | 0.04958755 | 0.001743561 | -4128.15949 | 12.9614908 | 13.2167497 | 13.6091329 | 8.2863934 | 1.2054667 | 0.6019289 |
| PPP1R14B | -1.486868809 | 0.04958755 | 0.002329295 | -4615.324 | 13.4684599 | 13.959023 | 13.6091329 | 9.1963108 | 1.2054667 | 0.6019289 |
| LAMA4 | -1.359775376 | 0.04958755 | 0.003336335 | -5076.834781 | 13.6103758 | 13.1248048 | 13.5151803 | 10.3063616 | 1.2054667 | 0.6019289 |

Figure 9B:
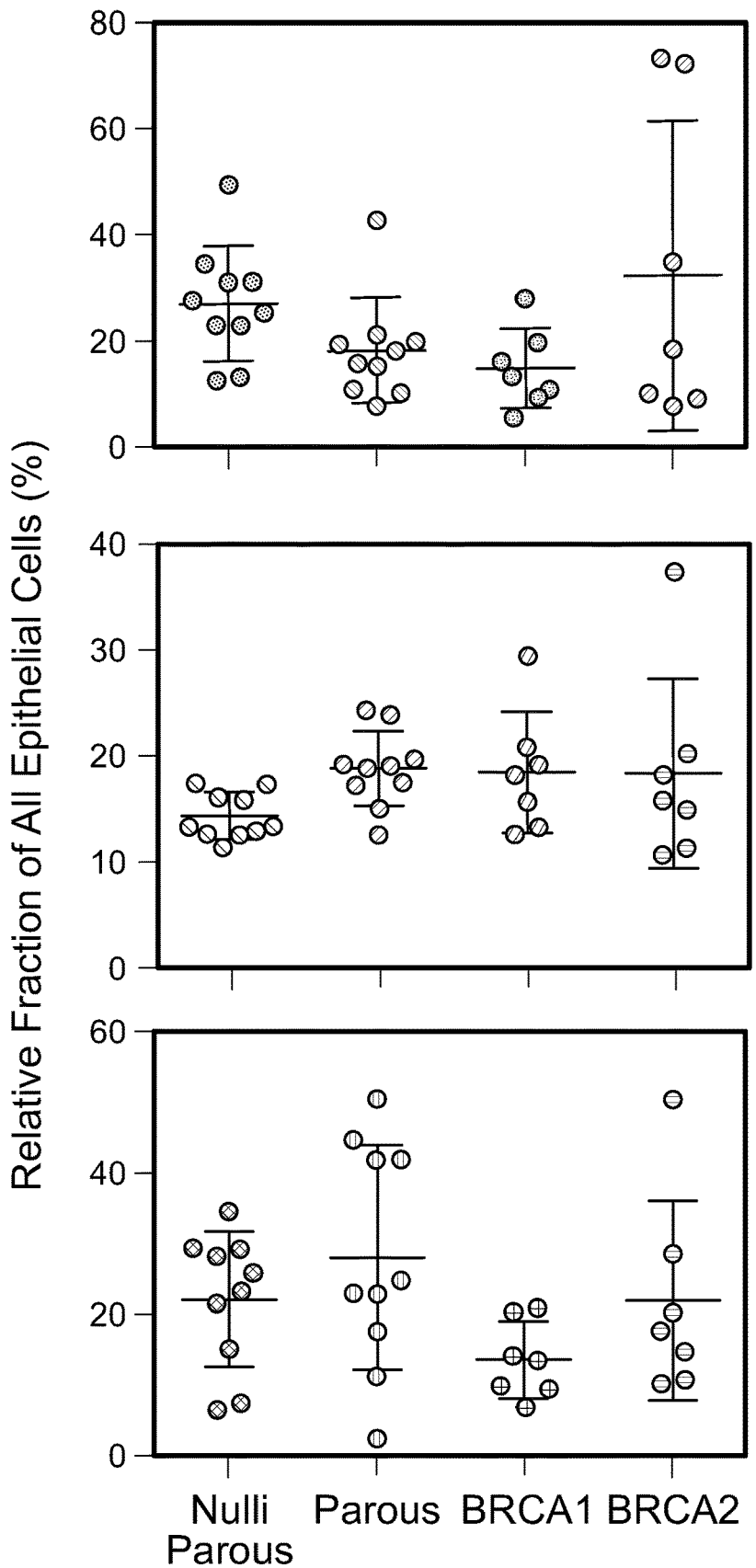
FIG. 9B is a dot plot showing the relative frequency of $CD44^+$, $CD24^+$, and $CD10^+$ cells among all breast epithelial cells in samples from nulliparous and parous groups from control and BRCA1/2 mutation carriers. The error bars mark the mean±standard error of the mean (SEM).

To determine if the lack of parity-associated changes in CD44+ cells from BRCA1/2 women could be due to differences in the cell populations identified by the three cell surface markers, FACS analysis of multiple tissue samples from control and BRCA1/2 women was performed. The relative frequency of CD44+ was slightly higher in control and BRCA1/2 parous compared to nulliparous control samples, which was associated with a slight decrease in the frequency of CD24+ cells, whereas the relative frequency of CD10+ cells was about the same in all groups (FIG. 9B). The increase in the relative frequency of CD44+ to CD24+ cells in parous samples could potentially be due to the increased number of lobulo-alveolar relative to ductal structures observed in parous women (FIG. 1), or due to the loss of CD24+ cells during involution, or may also reflect the presence of parity-induced stem cells described in murine mammary glands.

Example 3: Biological Pathways and Networks Affected by Parity-Related Gene Expression Changes This example identifies biological pathways that are activated or repressed by parity.

It was investigated which signaling pathways might be affected by parity-related molecular changes. Early pregnancy specifically decreases the risk of ER+ breast tumors. Differentially expressed genes (Table 4, supra) were explored in CD44+ cells for candidate mediators of this effect. Several genes were identified that can change the response of breast tissue to steroid hormones by altering metabolism (e.g., HSD17B11, HSD17B12, and HSD17B14) or by modulating nuclear receptors (e.g., NCOR1, NCOR2, NCOA4, and NCOA7). Interestingly, androgen receptor (AR) and one of its key targets PSA (KLK3) were highly expressed in nulliparous CD44+ cells, implying active androgen signaling pathway that is decreased following pregnancy. Among genes highly expressed in parous CD44+ cells were a number of known tumor suppressors, such as Hakai/CBLL1, CASP8, SCRIB and LLGL2, and DNA repair-related genes (e.g., PRKDC, FANCB), suggesting that these cells may be more resistant to transformation in parous women.

Figure 10:
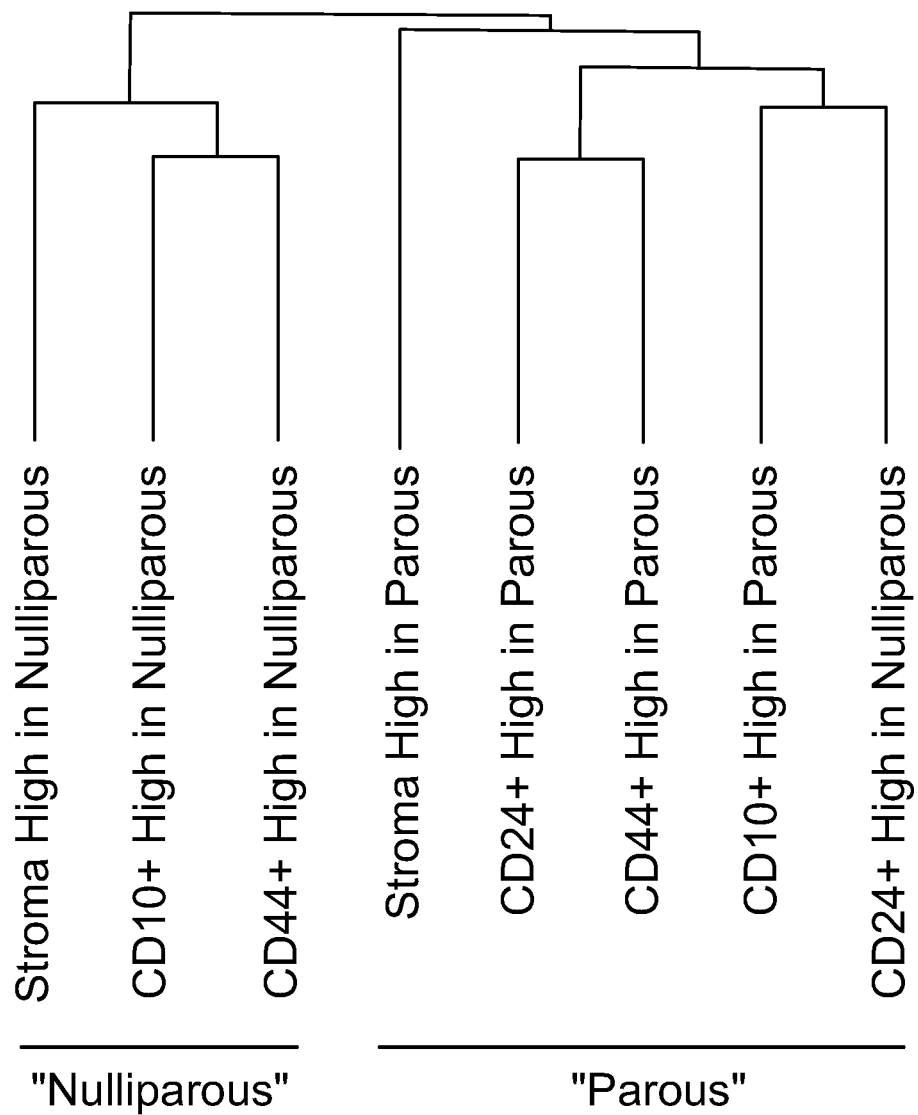
FIG. 10 is a dendrogram depicting hierarchical clustering of signaling pathways significantly high in parous or nulliparous samples in any of the four cell types (stromal fibroblasts ("stroma"), CD10+, CD44+ and CD24+ breast epithelial cells) analyzed.

In order to determine overall activation of specific biological functions due to parity in the cell types analyzed, pathway enrichment, network, and protein interactome analyses were performed using the MetaCore platform. The analyses are summarized in Table 10, below, which contains a full list of enriched GeneGo pathway maps in four different cell types (CD24+, CD44+, CD10+ and stromal fibroblasts) from human breast epithelium from nulliparous and parous subjects. Table 10 contains canonical pathway maps with p-values (<0.05) indicating significance of enrichment for differentially expressed genes upregulated in individual cell types (CD44+, CD24+, CD10+ and stroma) isolated from nulliparous and parous breast tissue, pathway maps, and p-value of enrichment in differentially expressed gene sets from the indicated human cell types from nulliparous and parous women. Table 10 also includes pathways enriched in genes highly expressed in virgin compared to publicly available datasets for parous rats [Blakely et al., supra]. It was found that parity had similar global effects on three of the four cell types analyzed, as pathways built on expression patterns in CD10+ and CD44+ cells and stroma cluster together for parous and nulliparous states (FIG. 10).

TABLE 10

List of Enriched GeneGo Pathway Maps in Four Different Breast Epithelial Cell Types

| Pathway maps | p-values in Nulliparous | | | | | p-values in Parous | | | |
| --- | --- | --- | --- | --- | --- | --- | --- | --- | --- |
| | CD44+ | CD24+ | CD10+ | Stroma | rat | CD44+ | CD24+ | CD10+ | Stroma |
| Cytoskeleton remodeling_Cytoskeleton remodeling | 1.05E−09 | 1.79E−04 | 3.27E−06 | 9.10E−05 | 3.77E−04 | 3.49E−03 | | 0.0256 | 1.17E−04 |
| Cytoskeleton remodeling_Regulation of actin cytoskeleton by Rho GTPases | 1.34E−09 | 1.17E−02 | 2.73E−02 | | 9.98E−07 | 0.00412 | | | 7.52E−04 |
| Cytoskeleton remodeling_TGF, WNT and cytoskeletal remodeling | 1.88E−09 | 5.71E−08 | 1.46E−07 | 8.12E−04 | 2.69E−03 | 6.92E−03 | 1.92E−02 | 7.29E−03 | 2.63E−04 |
| Cell adhesion_Chemokines and adhesion | 2.69E−07 | 3.55E−05 | 1.03E−05 | 3.54E−04 | 3.88E−03 | 0.0217 | 2.84E−02 | | 4.53E−02 |
| Cytoskeleton remodeling_Role of PKA in cytoskeleton re-organisation | 6.44E−07 | 1.40E−04 | | | 9.01E−05 | | | | 0.00934 |
| Development_MAG-dependent inhibition of neurite outgrowth | 1.54E−06 | 1.45E−02 | 3.82E−02 | 1.71E−02 | 1.12E−02 | | | | 0.0318 |
| Role of DNA methylation in progression of multiple myeloma | 2.40E−06 | 7.26E−03 | 1.50E−03 | 6.35E−03 | | | 0.00478 | 4.82E−03 | |
| Cell adhesion_Histamine H1 receptor signaling in the interruption of cell barrier integrity | 3.24E−06 | 7.62E−06 | | | 6.00E−03 | | | 0.0205 | 0.00325 |
| Cell adhesion_Alpha-4 integrins in cell migration and adhesion | 3.71E−06 | 1.02E−02 | 6.75E−03 | | 7.85E−03 | 0.0221 | 0.0334 | | |
| Stem cells_Response to hypoxia in glioblastoma stem cells | 4.22E−06 | | 3.68E−03 | | | | | | |
| Development_WNT signaling pathway. Part 2 | 5.42E−06 | 4.58E−03 | 5.02E−03 | 1.38E−02 | | | 0.00283 | 6.24E−06 | |
| Development_Slit-Robo signaling | 6.19E−06 | 1.32E−04 | 3.54E−03 | 8.20E−03 | 4.54E−03 | | | | |
| Cytoskeleton remodeling_Fibronectin-binding integrins in cell motility | 8.94E−06 | 1.17E−03 | 7.71E−04 | | 8.39E−04 | | | | |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Oxidative phosphorylation | 9.31E−06 | 1.25E−07 | | | 5.50E−03 | | | | 2.34E−13 |
| Cell adhesion_Role of tetraspanins in the integrin-mediated cell adhesion | 1.02E−05 | 5.25E−04 | | | 4.99E−05 | | | | |
| Cell cycle_Role of Nek in cell cycle regulation | 1.27E−05 | 7.84E−03 | 9.44E−04 | | 1.60E−05 | | 5.46E−03 | | 0.0196 |
| Signal transduction_PKA signaling | 1.64E−05 | 1.47E−02 | | | 2.59E−03 | 3.46E−02 | | 0.0356 | |
| Blood coagulation_Blood coagulation | 1.86E−05 | | 6.50E−04 | | 2.90E−03 | | | | |
| Cell adhesion_ECM remodeling | 2.09E−05 | | 2.54E−08 | 1.01E−06 | 2.90E−03 | | 0.0000897 | | |
| Inhibitory action of Lipoxin A4 on PDGF, EGF and LTD4 signaling | 2.45E−05 | 4.38E−02 | 6.75E−03 | | 3.60E−02 | | 0.00123 | | |
| Stem cells_WNT/Beta-catenin and NOTCH in induction of osteogenesis | 2.48E−05 | | | 4.20E−03 | | | | 0.0118 | |
| HIF-1 in gastric cancer | 3.00E−05 | | 9.13E−03 | | 1.60E−03 | | 2.68E−02 | | 0.0181 |
| Cell adhesion_Plasmin signaling | 3.33E−05 | | 7.32E−07 | 1.41E−02 | | | 0.00805 | | |
| Development_Lipoxin inhibitory action on PDGF, EGF and LTD4 signaling | 3.33E−05 | 4.80E−02 | 7.80E−03 | | 3.95E−02 | | 0.00144 | | |
| Cell adhesion_Integrin-mediated cell adhesion and migration | 3.84E−05 | 1.11E−02 | 1.02E−02 | 9.18E−03 | 1.81E−03 | | | | 0.000871 |
| Cytoskeleton remodeling_Reverse signaling by ephrin B | 5.92E−05 | | 4.20E−03 | | 5.25E−03 | | | | |
| Immune response_IL-1 signaling pathway | 7.06E−05 | | 1.50E−03 | 6.35E−03 | | | | | |
| Cell adhesion_Endothelial cell contacts by junctional mechanisms | 7.46E−05 | 4.30E−04 | | | 2.36E−03 | | | | |
| Signal transduction_cAMP signaling | 7.78E−05 | | | 1.87E−02 | 2.53E−03 | | | | 0.00751 |
| Regulation of CFTR activity (norm and CF) | 7.82E−05 | | | 1.98E−02 | 2.57E−04 | 3.91E−04 | 1.08E−03 | 2.12E−02 | 1.13E−02 |
| Development_TGF-beta-dependent induction of EMT via RhoA, PI3K and ILK. | 1.13E−04 | 3.86E−04 | 4.37E−04 | | 2.52E−04 | 1.40E−03 | 0.00597 | 6.19E−03 | |
| Role of stellate cells in progression of pancreatic cancer | 1.16E−04 | 9.06E−03 | 7.55E−06 | 1.92E−04 | 1.57E−03 | | 0.00135 | | |
| Cell cycle_Influence of Ras and Rho proteins on G1/S Transition | 1.18E−04 | 3.51E−05 | 1.73E−02 | | 3.23E−03 | 4.07E−02 | | 0.000894 | 2.90E−02 |
| Stem cells_NOTCH1-induced self-renewal of glioblastoma stem cells | 1.30E−04 | | | | | | | | |
| Stem cells_Pancreatic cancer stem cells in tumor metastasis | 1.30E−04 | | 3.68E−03 | | 1.36E−06 | | | | 0.000276 |
| Tumor-stroma interactions in pancreatic cancer | 1.44E−04 | | 5.38E−05 | 8.16E−04 | | | | | |
| Stem cells_Regulation of lung epithelial progenitor cell differentiation | 1.66E−04 | | 2.88E−05 | 2.41E−02 | | | | | |
| LKB1 signaling pathway in lung cancer cells | 1.66E−04 | | 9.23E−04 | 1.33E−02 | 6.90E−04 | | 6.32E−04 | | 0.000598 |
| Immune response_CCR3 signaling in eosinophils | 1.68E−04 | 3.21E−03 | 4.15E−02 | 1.76E−02 | 1.17E−04 | | | | 0.000191 |
| Non-genomic signaling of ESR2 (membrane) in lung cancer cells | 1.76E−04 | 4.00E−02 | | | 1.81E−03 | | | | 0.00451 |
| Blood coagulation_GPCRs in platelet aggregation | 2.20E−04 | | 2.73E−02 | | 1.18E−03 | | | | 0.0283 |
| Cytoskeleton remodeling_Role of PDGFs in cell migration | 2.55E−04 | | | | 1.10E−02 | | 0.00146 | | |
| Stem cells_Role of BMP signaling in embryonic stem cell neural differentiation | 2.59E−04 | | 3.54E−03 | | | | | | |
| Development_Hedgehog and PTH signaling pathways in bone and cartilage development | 3.07E−04 | | | 1.71E−02 | 4.70E−02 | | | 0.0316 | |
| Stem cells_Endothelial differentiation during embryonic development | 3.25E−04 | | 3.98E−05 | | | 3.46E−02 | 0.0365 | 3.56E−02 | |
| Stem cells_Hedgehog, BMP and Parathyroid hormone in osteogenesis | 3.25E−04 | 5.00E−02 | 1.41E−02 | | | | | | |

TABLE 10-continued

List of Enriched GeneGo Pathway Maps in Four Different Breast Epithelial Cell Types

| | p-values in Nulliparous | | | | | p-values in Parous | | | |
|---|---|---|---|---|---|---|---|---|---|
| Pathway maps | CD44+ | CD24+ | CD10+ | Stroma | rat | CD44+ | CD24+ | CD10+ | Stroma |
| Dual role of BMP signaling in gastric cancer | 3.50E−04 | 1.57E−02 | 1.31E−03 | | | 2.99E−02 | | 0.0306 | 4.69E−02 |
| IGF signaling in HCC | 3.94E−04 | 1.61E−02 | 1.11E−03 | 1.21E−02 | 1.08E−04 | | | 0.0269 | 0.0108 |
| Development_EGFR signaling via small GTPases | 4.43E−04 | 3.61E−02 | | | | | | | |
| Development_FGF2-dependent induction of EMT | 4.46E−04 | | 3.56E−04 | | 5.64E−03 | 0.0139 | 0.034 | | |
| Cell adhesion_Cadherin-mediated cell adhesion | 4.72E−04 | 4.30E−04 | 4.09E−02 | | 3.07E−04 | | | | |
| Stem cells_Differentiation of white adipocytes | 4.75E−04 | | | 6.82E−04 | | | | | 6.78E−06 |
| Apoptosis and survival_Endoplasmic reticulum stress response pathway | 4.75E−04 | 1.76E−02 | | | | | | 0.0419 | |
| Development_BMP signaling | 5.69E−04 | | 2.45E−02 | 1.15E−02 | | | | 0.0202 | |
| Development_TGF-beta-dependent induction of EMT via MAPK | 6.02E−04 | 3.70E−02 | 2.33E−03 | 3.74E−02 | 7.44E−03 | | | 0.00698 | |
| Transcription_ChREBP regulation pathway | 6.25E−04 | | | | 6.76E−03 | 0.0165 | 6.22E−03 | | 4.33E−03 |
| Translation_Regulation of translation initiation | 6.27E−04 | 2.05E−02 | | | | 3.85E−02 | | 0.00155 | |
| PGE2 pathways in cancer | 6.80E−04 | | | | | | | | 0.0333 |
| Immune response_Antigen presentation by MHC class I | 8.21E−04 | 2.32E−02 | | | 3.32E−03 | | | | |
| Muscle contraction_Regulation of eNOS activity in endothelial cells | 8.47E−04 | | 1.36E−03 | 2.89E−02 | 2.39E−03 | | | 0.0343 | |
| HBV-dependent NF-kB and PI3K/AKT pathways leading to HCC | 8.76E−04 | 1.70E−05 | | | 3.43E−02 | 8.47E−03 | 0.00814 | 2.99E−02 | |
| IL-6 signaling in multiple myeloma | 8.76E−04 | 1.08E−04 | 3.71E−02 | | 9.11E−03 | 0.0291 | 8.14E−03 | | 5.00E−03 |
| Development_Melanocyte development and pigmentation | 8.76E−04 | | | | | | | | |
| Stem cells_Extraembryonic differentiation of embryonic stem cells | 9.09E−04 | | 1.65E−03 | | | | | | |
| Stem cells_Astrocyte differentiation from adult stem cells | 9.09E−04 | | 3.09E−02 | | 3.95E−02 | | | | |
| Apoptosis and survival_BAD phosphorylation | 9.18E−04 | 5.76E−03 | | | 8.02E−04 | 3.55E−03 | 3.77E−03 | 7.83E−04 | 3.78E−04 |
| Apoptosis and survival_Apoptotic TNF-family pathways | 9.18E−04 | | | 2.61E−02 | | 3.55E−03 | 0.00377 | 1.49E−02 | |
| Stem cells_Auditory hair cell differentiation in embryogenesis | 1.06E−03 | | | | | | | | |
| Effect of H. pylori infection on gastric epithelial cells motility | 1.12E−03 | 2.38E−04 | 5.57E−03 | | | | | | |
| Development_S1P3 receptor signaling pathway | 1.12E−03 | | | 4.78E−03 | | 1.89E−02 | | 0.0126 | |
| Development_Role of IL-8 in angiogenesis | 1.12E−03 | 1.88E−03 | | 2.00E−02 | | | | 0.0212 | |
| Immune response_IL-9 signaling pathway | 1.13E−03 | 1.29E−02 | 3.44E−02 | | 4.32E−02 | | | | 0.0291 |
| Transcription_CREB pathway | 1.35E−03 | 2.88E−02 | | 1.07E−03 | | 0.00464 | 4.78E−03 | | 5.07E−04 |
| Apoptosis and survival_Granzyme A signaling | 1.35E−03 | 2.92E−02 | | 6.98E−04 | | 1.33E−02 | | 0.0136 | 2.64E−03 |
| Cell adhesion_Gap junctions | 1.35E−03 | | 1.67E−02 | 4.63E−02 | 6.98E−04 | | | | |
| DNA damage_Brca1 as a transcription regulator | 1.35E−03 | 2.92E−02 | | | | | | | |
| Stem cells_Early embryonal hypaxial myogenesis | 1.40E−03 | | | 1.71E−02 | | | | | |
| Immune response_Oncostatin M signaling via MAPK in human cells | 1.40E−03 | | | 1.12E−02 | | | 4.37E−02 | 3.16E−02 | 0.00115 |
| Stem cells_Beta adrenergic receptors in brown adipocyte differentiation | 1.40E−03 | | | 2.20E−03 | | | 1.02E−02 | | 0.0000202 |
| ENaC regulation in airways (normal and CF) | 1.48E−03 | | 3.27E−03 | 4.28E−02 | | | | | |
| EGFR family signaling in pancreatic cancer | 1.49E−03 | 7.40E−06 | 4.97E−03 | | 1.91E−03 | | | 0.00101 | |

TABLE 10-continued

List of Enriched GeneGo Pathway Maps in Four Different Breast Epithelial Cell Types

| Pathway maps | p-values in Nulliparous | | | | | p-values in Parous | | | |
| --- | --- | --- | --- | --- | --- | --- | --- | --- | --- |
| | CD44+ | CD24+ | CD10+ | Stroma | rat | CD44+ | CD24+ | CD10+ | Stroma |
| Cell adhesion_Endothelial cell contacts by non-junctional mechanisms | 1.52E−03 | 1.36E−02 | | 2.59E−02 | | | | | 0.0423 |
| Immune response_Inhibitory action of Lipoxins on pro-inflammatory TNF-alpha signaling | 1.62E−03 | 3.14E−02 | 7.19E−03 | | | 4.18E−05 | 0.000182 | 5.47E−03 | |
| Neurophysiological process_Glutamate regulation of Dopamine D1A receptor signaling | 1.62E−03 | 8.10E−03 | | | 6.00E−03 | | | | |
| Neurophysiological process_Receptor-mediated axon growth repulsion | 1.62E−03 | 8.10E−03 | 2.56E−02 | | 2.15E−04 | | | | |
| Role of cell adhesion molecules in progression of pancreatic cancer | 1.62E−03 | | 7.19E−03 | | | | | | |
| Immune response_Fc gamma R-mediated phagocytosis in macrophages | 1.62E−03 | 8.10E−03 | | | 2.48E−02 | | | | |
| Neurophysiological process_ACM regulation of nerve impulse | 1.93E−03 | | | 3.50E−02 | 2.52E−04 | | | 0.0226 | |
| Transcription_Transcription regulation of aminoacid metabolism | 1.98E−03 | | | | | | | | |
| G-protein signaling_Regulation of p 38 and JNK signaling mediated by G-proteins | 2.08E−03 | | 4.65E−02 | | 1.40E−02 | | | 0.0105 | 0.0377 |
| Stem cells_Role of GSK3 beta in cardioprotection against myocardial infarction | 2.12E−03 | | 2.17E−02 | | 6.03E−03 | | | | 0.0196 |
| Development_NOTCH-induced EMT | 2.12E−03 | | | | | | | | |
| HCV-dependent transcription regulation leading to HCC | 2.12E−03 | 6.90E−04 | | | 3.16E−02 | | | | |
| Regulation of lipid metabolism_Insulin signaling:generic cascades | 2.29E−03 | 7.67E−05 | | | 2.94E−04 | 6.73E−03 | | 0.00698 | 7.65E−04 |
| Development_PDGF signaling via MAPK cascades | 2.29E−03 | 3.70E−02 | | | | | 0.00664 | | |
| Transport Clathrin-coated vesicle cycle | 2.30E−03 | | 8.53E−04 | 1.21E−02 | | | | | 0.00213 |
| Stem cells_Stimulation of differentiation of mouse embryonic fibroblasts into adipocytes by extracellular factors | 2.30E−03 | | 3.02E−03 | | 4.60E−03 | | 2.20E−04 | | 0.0000954 |
| Immune response_MIF in innate immunity response | 2.50E−03 | 4.50E−03 | | | | | | 0.0425 | |
| Development_S1P2 and S1P3 receptors in cell proliferation and differentiation | 2.54E−03 | 1.80E−02 | | | 1.46E−02 | | | | |
| Reproduction_GnRH signaling | 2.61E−03 | 2.32E−02 | | | | | | 0.0225 | |
| Regulation of lipid metabolism_Stimulation of Arachidonic acid production by ACM receptors | 2.61E−03 | | 2.94E−02 | 4.48E−02 | 3.00E−04 | | | | |
| Regulation of lipid metabolism_Insulin regulation of glycogen metabolism | 2.76E−03 | 2.25E−02 | | | 1.95E−04 | 1.72E−02 | | 0.0178 | 2.20E−03 |
| Immune response_Oncostatin M signaling via JAK-Stat in human cells | 2.84E−03 | | | | 3.62E−02 | | | | |
| Development_WNT signaling pathway. Part 1. Degradation of beta-catenin in the absence WNT signaling | 2.84E−03 | | 3.70E−05 | 1.79E−03 | 3.62E−02 | | 0.0006 | | |
| Development_VEGF-family signaling | 3.00E−03 | | 2.88E−05 | | | | | | 0.0441 |
| Hypoxia-induced EMT in cancer and fibrosis | 3.01E−03 | | 6.83E−04 | | | | 0.0398 | | |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Cell adhesion_Role of CDK5 in cell adhesion | 3.01E-03 | | | | | | | | |
| Immune response_IL-2 activation and signaling pathway | 3.17E-03 | 1.22E-02 | | | 3.43E-02 | 2.91E-02 | 0.0314 | 2.99E-02 | |
| Mechanisms of drug resistance in multiple myeloma | 3.17E-03 | 1.22E-02 | | 4.27E-02 | | | | 0.0299 | |
| Activation of TGF-beta signaling in pancreatic cancer | 3.20E-03 | | | | | | | | |
| Development_NOTCH1-mediated pathway for NF-KB activity modulation | 3.20E-03 | | | | | | | 0.00103 | |
| Regulation of VEGF signaling in pancreatic cancer | 3.20E-03 | | 2.01E-03 | | | | | | |
| Possible pathway of TGF-beta 1-dependent inhibition of CFTR expression | 3.20E-03 | | | | | | | | |
| Signal transduction_Erk Interactions: Inhibition of Erk | 3.20E-03 | 1.02E-02 | | | 1.40E-03 | | | 0.0227 | |
| Muscle contraction_ GPCRs in the regulation of smooth muscle tone | 3.51E-03 | | | | 2.31E-04 | | | | |
| Stem cells_NOTCH in inhibition of WNT/Beta-catenin-induced osteogenesis | 3.56E-03 | | | 1.16E-04 | | | | | |
| Apoptosis and survival_Inhibition of ROS-induced apoptosis by 17beta-estradiol | 3.56E-03 | | | | | | | | |
| Development_TGF-beta receptor signaling | 3.70E-03 | 1.34E-02 | | 4.55E-02 | | | | | |
| TGF-beta 1-induced trans-activation of membrane receptors signaling in HCC | 3.70E-03 | 3.28E-03 | 1.27E-02 | | 2.30E-03 | | 0.000388 | | |
| Beta-2 adrenergic-dependent CFTR expression | 3.87E-03 | | | | | | | | |
| Immune response_Oncostatin M signaling via MAPK in mouse cells | 3.88E-03 | | | | 8.88E-03 | | 3.66E-02 | | 0.000851 |
| Role of osteoblasts in bone lesions formation in multiple myeloma | 3.88E-03 | | 3.09E-02 | 2.31E-03 | | | | | |
| Mechanisms of CAM–DR in multiple myeloma | 3.88E-03 | 4.80E-02 | | | 3.95E-02 | | 0.0366 | | |
| Development_TGF-beta-dependent induction of EMT via SMADs | 3.88E-03 | | 7.80E-03 | | | | 0.000216 | 2.55E-02 | |
| Stem cells_WNT and Notch signaling in early cardiac myogenesis | 3.88E-03 | | 7.80E-03 | 2.55E-02 | | | | | |
| PI3K signaling in gastric cancer | 4.30E-03 | 3.68E-03 | 9.62E-04 | | 5.23E-04 | 6.36E-04 | 0.00226 | 2.49E-05 | |
| Some pathways of EMT in cancer cells | 4.30E-03 | 7.92E-04 | | | | | 7.66E-05 | 3.56E-02 | 0.025 |
| Membrane-bound ESR1: interaction with G-proteins signaling | 4.30E-03 | | | 1.18E-02 | 1.10E-02 | | | | |
| Cell adhesion_Tight junctions | 4.66E-03 | | | 2.63E-03 | 1.00E-02 | | | | |
| Cytoskeleton remodeling_Keratin filaments | 4.66E-03 | 1.29E-02 | | | 1.90E-03 | | 9.08E-03 | 5.23E-06 | 0.000138 |
| IGF-1 signaling in pancreatic cancer | 4.66E-03 | 2.61E-03 | 8.97E-03 | | 4.32E-02 | | 9.08E-03 | | 0.0291 |
| Stem cells_Dopamine-induced expression of CNTF in adult neurogenesis | 4.79E-03 | | | | 4.63E-02 | | | | |
| Cell cycle_Role of 14-3-3 proteins in cell cycle regulation | 4.79E-03 | | | | 1.07E-03 | | | | 0.00516 |
| Development_Thrombopoetin signaling via JAK-STAT pathway | 4.79E-03 | | | | | | | | |
| Immune response_IL-17 signaling pathways | 4.82E-03 | 3.05E-02 | | | | | 0.00571 | 7.94E-03 | |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Suppression of TGF-beta signaling in pancreatic cancer | 4.93E-03 | | | 7.26E-03 | | | | | |
| G-protein signaling_G-Protein alpha-12 signaling pathway | 5.57E-03 | | | | 1.12E-02 | | | | 0.0067 |
| Translation _Regulation of EIF4F activity | 5.72E-03 | 1.03E-03 | | | 6.82E-04 | 1.81E-04 | | 0.000894 | 1.59E-03 |
| G-protein signaling_Regulation of cAMP levels by ACM | 5.78E-03 | | | | | | | | |
| Cell adhesion_Ephrin signaling | 5.78E-03 | | | 2.52E-04 | 2.48E-02 | | | | |
| G-protein signaling_Crosstalk between Ras-family GTPases | 6.08E-03 | | | | 9.44E-03 | | | | |
| Proteolysis_Putative ubiquitin pathway | 6.08E-03 | | 8.14E-04 | | | | | | |
| Stem cells_Aberrant Wnt signaling in medulloblastoma stem cells | 6.08E-03 | | 2.73E-02 | 3.07E-03 | | | | 0.000622 | |
| Putative role of Estrogen receptor and Androgen receptor signaling in progression of lung cancer | 6.56E-03 | 5.08E-03 | | | | | | | 0.00806 |
| ERBB family and HGF signaling in gastric cancer | 6.56E-03 | 1.91E-02 | 1.47E-03 | | 3.60E-03 | | 4.51E-02 | 4.53E-02 | 0.00806 |
| Stem cells_Noncanonical WNT signaling in cardiac myogenesis | 6.59E-03 | 9.53E-05 | | | | | | 0.00921 | |
| K-RAS signaling in lung cancer | 6.72E-03 | 9.01E-03 | 8.12E-03 | | | 2.20E-02 | 2.46E-02 | 2.26E-02 | 1.66E-02 |
| G-protein signaling_Rap2A regulation pathway | 7.03E-03 | | | | | | | | |
| Transport_Macropinocytosis regulation by growth factors | 7.05E-03 | | | | | | 2.60E-02 | | 0.000969 |
| Development_EGFR signaling pathway | 7.05E-03 | 7.64E-04 | | | 4.84E-04 | | | 0.0106 | |
| Dual role of TGF-beta 1 in HCC | 7.59E-03 | 1.36E-02 | | | | | | | |
| Immune response_IFN alpha/beta signaling pathway | 7.59E-03 | | | | | | | | |
| Development_Glucocorticoid receptor signaling | 7.59E-03 | | | 2.59E-02 | | | | 0.00515 | |
| Cell adhesion_PLAU signaling | 7.76E-03 | | 3.17E-03 | | 2.90E-03 | | | 0.0386 | 0.00839 |
| Transcription_P53 signaling pathway | 7.76E-03 | 7.33E-04 | | 1.05E-02 | 1.40E-02 | | 0.0377 | | |
| Stem cells_BMP7 in brown adipocyte differentiation | 7.76E-03 | 3.96E-03 | | | | | | | 0.0000304 |
| Development_Beta-adrenergic receptors regulation of ERK | 7.77E-03 | | | | 2.93E-02 | | | | |
| Role and regulation of Prostaglandin E2 in gastric cancer | 7.77E-03 | | | | | | | 0.0249 | |
| Development_Leptin signaling via PI3K-dependent pathway | 7.77E-03 | 3.70E-02 | | | 7.44E-03 | | | 0.0249 | |
| Transport_Alpha-2 adrenergic receptor regulation of ion channels | 7.77E-03 | | 3.10E-02 | 3.74E-02 | 2.93E-02 | | | | |
| Influence of bone marrow cell environment on progression of multiple myeloma | 7.77E-03 | | 2.33E-03 | | 1.60E-03 | | 0.00664 | | |
| Immune response_CD40 signaling | 7.95E-03 | 4.01E-02 | 4.85E-03 | 1.61E-03 | | | 0.0278 | 3.47E-03 | |
| Muscle contraction_ACM regulation of smooth muscle contraction | 8.52E-03 | | | | 9.93E-04 | | | | |
| Stem cells_H3K4 demethylases in stem cell maintenance | 8.73E-03 | | 2.17E-02 | | | | | | |
| Development_PDGF signaling via STATs and NF-kB | 8.73E-03 | 1.39E-03 | | | 2.96E-02 | | 8.83E-04 | | 0.00354 |
| Muscle contraction_Relaxin signaling pathway | 8.94E-03 | | | 4.00E-02 | | 0.0265 | 2.90E-02 | | 1.97E-02 |
| Transition of HCC cells to invasive and migratory phenotype | 9.07E-03 | | | | 1.55E-02 | | 0.0141 | 4.25E-02 | |

TABLE 10-continued

List of Enriched GeneGo Pathway Maps in Four Different Breast Epithelial Cell Types

| | p-values in Nulliparous | | | | | p-values in Parous | | | |
|---|---|---|---|---|---|---|---|---|---|
| Pathway maps | CD44+ | CD24+ | CD10+ | Stroma | rat | CD44+ | CD24+ | CD10+ | Stroma |
| WNT signaling in HCC | 9.07E-03 | 4.50E-03 | 1.42E-04 | 4.20E-03 | | | 0.0141 | 1.18E-02 | |
| Development_Neurotrophin family signaling | 9.07E-03 | | 1.42E-04 | | | | | | 0.00934 |
| Ubiquinone metabolism | 9.10E-03 | 8.55E-03 | | | | | | | 9.27E-08 |
| Immune response_Oncostatin M signaling via JAK-Stat in mouse cells | 9.13E-03 | | | | 2.73E-02 | | | | |
| Androgen signaling in HCC | 9.13E-03 | 4.73E-03 | | | | | | | |
| Cell cycle_Initiation of mitosis | 9.37E-03 | | | | | 2.99E-02 | | 0.0306 | 4.69E-02 |
| Development_Leptin signaling via JAK/STAT and MAPK cascades | 9.37E-03 | | 3.60E-02 | | | | | | |
| Transport_Macropinocytosis | 9.84E-03 | | | | | 0.0176 | | | |
| Transport_RAB1A regulation pathway | 9.84E-03 | | | | | | | | |
| Cytoskeleton remodel_Integrin outside-in signaling | 1.02E-02 | 1.22E-02 | 1.14E-02 | 3.14E-04 | | | | | |
| Influence of multiple myeloma cells on bone marrow stromal cells | 1.04E-02 | 3.98E-02 | | 3.27E-02 | | 0.0196 | 0.00624 | | |
| Role of metalloproteases and heparanase in progression of pancreatic cancer | 1.04E-02 | | 2.45E-02 | | | | | | |
| Cytoskeleton remodeling_Thyroliberin in cytoskeleton remodeling | 1.04E-02 | | | | | | | | |
| Transport_ACM3 in salivary glands | 1.06E-02 | | | 1.71E-02 | | | | 0.0465 | |
| Transport_Intracellular cholesterol transport in norm | 1.10E-02 | | 2.85E-02 | | | | | | |
| Muscle contraction_Delta type opioid receptor in smooth muscle contraction | 1.14E-02 | | | 2.36E-03 | | | | | |
| G-protein signaling_Ras family GTPases in kinase cascades (scheme) | 1.14E-02 | | | | | | | 0.0348 | |
| Development_Alpha-1 adrenergic receptors signaling via cAMP | 1.16E-02 | | | | | | | | |
| HCV-mediated liver damage and predisposition to HCC progression via p 53 | 1.16E-02 | 5.81E-03 | | | | | | 0.0118 | |
| wtCFTR and delta508 traffic/Clathrin coated vesicles formation (norm and CF) | 1.16E-02 | 3.71E-02 | 2.16E-03 | | | | | | 0.0228 |
| Apoptosis and survival_HTR1A signaling | 1.17E-02 | 4.65E-02 | | | 1.00E-02 | 3.17E-02 | | 0.0327 | 2.93E-05 |
| Immune response_Histamine signaling in dendritic cells | 1.17E-02 | 4.65E-02 | | | | | | | |
| Development_GM-CSF signaling | 1.17E-02 | 6.92E-04 | 4.04E-02 | | | | 3.39E-02 | 3.27E-02 | 0.00553 |
| Development_A2B receptor: action via G-protein alpha s | 1.17E-02 | 4.65E-02 | | 4.55E-02 | | | 0.00897 | 3.27E-02 | |
| Angiogenesis in HCC | 1.17E-02 | | 8.29E-04 | | | | | | |
| Pro-inflammatory action of Gastrin in gastric cancer | 1.17E-02 | 3.28E-03 | | | | | 3.39E-02 | 2.54E-03 | 0.0231 |
| Chemoresistance pathways mediated by constitutive activation of PI3K pathway and BCL-2 in small cell lung cancer | 1.22E-02 | 2.41E-02 | 1.09E-03 | 8.02E-04 | | 2.20E-05 | 1.72E-02 | 7.83E-04 | 1.15E-02 |
| Oxidative stress_Role of ASK1 under oxidative stress | 1.22E-02 | | | | | | | 0.00528 | |
| Stem cells_BMP signaling in cardiac myogenesis | 1.22E-02 | | 1.38E-03 | | | | | | |
| Transcription_Role of VDR in regulation of genes involved in osteoporosis | 1.23E-02 | | | | | | | | |
| Stem cells_TNF-alpha, IL-1 alpha and WNT5A-dependent regulation of osteogenesis and adipogenesis in mesenchymal stem cells | 1.33E-02 | 1.47E-02 | | 4.83E-02 | 2.59E-03 | | | 0.0356 | 0.025 |

TABLE 10-continued

List of Enriched GeneGo Pathway Maps in Four Different Breast Epithelial Cell Types

| | p-values in Nulliparous | | | | | p-values in Parous | | | |
|---|---|---|---|---|---|---|---|---|---|
| Pathway maps | CD44+ | CD24+ | CD10+ | Stroma | rat | CD44+ | CD24+ | CD10+ | Stroma |
| Transcription_Role of Akt in hypoxia induced HIF1 activation | 1.38E−02 | | | 5.59E−03 | 2.81E−03 | 1.49E−03 | | 0.00869 | |
| Mitochondrial ketone bodies biosynthesis and metabolism | 1.38E−02 | | | | 4.26E−05 | | | | |
| Signal transduction_AKT signaling | 1.40E−02 | 4.91E−06 | | | 1.54E−04 | 2.74E−05 | 0.00425 | 1.75E−04 | |
| Regulation of beta-adrenergic receptors signaling in pancreatic cancer | 1.40E−02 | | | | | | | | |
| Development_Notch Signaling Pathway | 1.40E−02 | | | | | | | 0.00422 | |
| Development_A2A receptor signaling | 1.40E−02 | 1.34E−03 | | | 2.07E−02 | | | 0.0000291 | |
| Development_VEGF signaling and activation | 1.40E−02 | 2.64E−02 | 2.08E−02 | | | | | | |
| Apoptosis and survival_Anti-apoptotic action of Gastrin | 1.40E−02 | 1.34E−03 | | | 4.78E−03 | | | 0.000175 | |
| Neurophysiological process_Melatonin signaling | 1.40E−02 | | | | | | | | |
| Neurophysiological process_EphB receptors in dendritic spine morphogenesis and synaptogenesis | 1.43E−02 | | | | 3.95E−02 | | | | |
| Stem cells_Putative pathways of telomerase regulation in glioblastoma stem cells | 1.46E−02 | | | | 6.24E−05 | 0.000261 | | | |
| Cytoskeleton remodeling_Role of Activin A in cytoskeleton remodeling | 1.46E−02 | 8.91E−04 | | | | | | | |
| Stem cells_H3K36 demethylation in stem cell maintenance | 1.46E−02 | 4.24E−02 | | | | | | 0.0142 | |
| Development_Beta-adrenergic receptors signaling via cAMP | 1.50E−02 | | | | 1.08E−04 | 0.0117 | | | 6.71E−03 |
| Effect of H. pylori infection on inflammation in gastric epithelial cells | 1.54E−02 | 3.27E−02 | | | | | | 0.000141 | |
| K-RAS signaling in pancreatic cancer | 1.60E−02 | | | | | 0.0179 | | | |
| Development_S1P1 signaling pathway | 1.60E−02 | | | | 5.36E−03 | | | | 0.0139 |
| Development_Ligand-independent activation of ESR1 and ESR2 | 1.60E−02 | 2.88E−02 | | | | | 4.78E−03 | 1.85E−02 | 0.0139 |
| CFTR-dependent regulation of ion channels in Airway Epithelium (norm and CF) | 1.60E−02 | | | | | | | | |
| Mechanisms of resistance to EGFR inhibitors in lung cancer | 1.60E−02 | 2.81E−04 | 2.31E−02 | 2.11E−04 | 1.82E−04 | | 0.0179 | 5.07E−04 | |
| Development_Regulation of CDK5 in CNS | 1.64E−02 | | | | | | | | |
| HGF signaling in pancreatic cancer | 1.64E−02 | | 6.21E−06 | | 3.32E−03 | | 0.003 | 4.42E−02 | |
| E-cadherin signaling and its regulation in gastric cancer | 1.67E−02 | 4.41E−04 | 1.96E−03 | | 1.90E−03 | | 0.000034 | | |
| HBV signaling via protein kinases leading to HCC | 1.67E−02 | 2.61E−03 | | | | | | 0.0285 | |
| Development_Endothelin-1/EDNRA signaling | 1.69E−02 | 1.76E−02 | | | 1.32E−02 | | 2.83E−03 | 1.34E−02 | 0.00159 |
| Development_VEGF signaling via VEGFR2-generic cascades | 1.82E−02 | 3.14E−02 | 2.56E−02 | | | | | | |
| Immune response_IL-13 signaling via JAK-STAT | 1.82E−02 | | | | | | | | |
| Signal transduction_Calcium signaling | 1.82E−02 | | | | 6.00E−03 | | | | |
| Cytoskeleton remodeling_ACM3 and ACM4 in keratinocyte migration | 1.92E−02 | | | | 1.12E−02 | | | | |
| Stem cells_Role of Neuregulin 1 and Thymosin beta-4 in myocardium regeneration after infarction | 1.94E−02 | | 7.11E−05 | | 3.90E−03 | 0.0484 | | | |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Cholesterol and Sphingolipids transport/Distribution to the intracellular membrane compartments (normal and CF) | 1.94E−02 | | | | | | | | 0.014 |
| Stem cells_Notch signaling in medulloblastoma stem cells | 1.94E−02 | | | | | | | | |
| Proteolysis_Putative SUMO-1 pathway | 1.94E−02 | 5.10E−03 | | | | | | 0.0494 | |
| FGF signaling in pancreatic cancer | 2.07E−02 | 2.01E−03 | 8.12E−03 | | 2.70E−02 | 0.022 | 1.22E−03 | | 1.66E−02 |
| Cytoskeleton remodeling_CDC42 in cellular processes | 2.18E−02 | 9.99E−03 | | | | 0.0194 | | | |
| Transcription_Role of heterochromatin protein 1 (HP1) family in transcriptional silencing | 2.18E−02 | 9.99E−03 | 4.30E−03 | 2.59E−03 | | | 4.36E−02 | | 0.000604 |
| Immune response_MIF-mediated glucocorticoid regulation | 2.18E−02 | 9.99E−03 | | | | | | | |
| Apoptosis and survival_Ceramides signaling pathway | 2.21E−02 | 1.61E−02 | 1.17E−02 | | | 1.96E−03 | 3.69E−04 | 9.21E−03 | 7.51E−03 |
| Cell adhesion_Cell-matrix glycoconjugates | 2.21E−02 | | 9.29E−05 | 6.14E−06 | | | 0.0475 | | |
| Role of histone modificators in progression of multiple myeloma | 2.28E−02 | 5.92E−03 | | | | 1.33E−02 | | 0.00275 | |
| Cytoskeleton remodeling_RalA regulation pathway | 2.28E−02 | 2.92E−02 | | | | | | | |
| Muscle contraction_S1P2 receptor-mediated smooth muscle contraction | 2.28E−02 | | | 2.39E−02 | | | | | 0.0158 |
| EGFR signaling pathway in Lung Cancer | 2.33E−02 | | 9.13E−03 | | | | | | |
| Influence of smoking on activation of EGFR signaling in lung cancer cells | 2.33E−02 | | | | | | | | |
| Development_HGF signaling pathway | 2.33E−02 | 3.70E−02 | 2.33E−03 | | 2.93E−02 | | 0.0268 | | |
| Cardiac Hypertrophy_NF-AT signaling in Cardiac Hypertrophy | 2.33E−02 | | 4.65E−02 | | 2.64E−03 | | 2.98E−02 | 3.69E−02 | 0.00119 |
| Immune response_TLR signaling pathways | 2.36E−02 | | | 3.84E−03 | | | | 0.00521 | |
| Chemotaxis_Leukocyte chemotaxis | 2.47E−02 | 2.83E−02 | 1.36E−03 | 4.01E−03 | 4.21E−04 | | | | |
| Cytokine production by Th17 cells in CF | 2.52E−02 | | | | | | | | |
| Development_PACAP signaling in neural cells | 2.52E−02 | | | | | | | | |
| Translation _Regulation of EIF2 activity | 2.52E−02 | 7.33E−04 | | | 2.90E−03 | | | 0.0386 | 0.00153 |
| Cytoskeleton remodeling_FAK signaling | 2.62E−02 | 1.67E−03 | | | 4.89E−03 | | | 0.000356 | 0.0104 |
| Inhibition of apoptosis in pancreatic cancer | 2.62E−02 | | 7.84E−03 | | 4.89E−03 | | | | 0.0381 |
| Apoptosis and survival_Role of IAP-proteins in apoptosis | 2.65E−02 | | | | 2.66E−02 | 3.16E−03 | 0.0246 | 1.56E−02 | |
| Stem cells_Neovascularization of glioblastoma in response to hypoxia | 2.65E−02 | | 7.71E−04 | | | | | | |
| Stem cells_Embryonal epaxial myogenesis | 2.65E−02 | | | 1.32E−03 | | | | | |
| Inflammatory mechanisms of pancreatic cancerogenesis | 2.82E−02 | 4.84E−02 | 1.94E−03 | | | | | 0.000647 | |
| Sorafenib-induced inhibition of cell proliferation and angiogenesis in HCC | 2.84E−02 | 2.34E−02 | | | | | | | |
| IL-1 beta-dependent CFTR expression | 2.84E−02 | | | | | | | | |
| Role of IGH translocations in multiple myeloma | 2.87E−02 | 4.50E−03 | 1.49E−02 | | | 0.0114 | 0.0141 | | |
| Development_Role of Activin A in cell differentiation and proliferation | 2.87E−02 | | | | | | | | |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Stem cells_H3K27 de-methylases in differentiation of stem cells | 2.87E−02 | 4.50E−03 | | 4.20E−03 | | | | | |
| Reproduction_Progesterone-mediated oocyte maturation | 2.87E−02 | | | | | | | 0.0425 | |
| Stem cells_Regulation of endothelial progenitor cell differentiation from adult stem cells | 2.90E−02 | | 6.15E−04 | | | | 0.000215 | | |
| Bacterial infections in CF airways | 2.90E−02 | | | | | | | | |
| Cytokine production by Th17 cells in CF (Mouse model) | 2.93E−02 | 4.32E−02 | | | | | | | |
| Development_PEDF signaling | 2.93E−02 | | 3.71E−02 | | | | | | |
| Immune response_Bacterial infections in normal airways | 2.93E−02 | | | 4.27E−02 | | | | | |
| Apoptosis and survival_Granzyme B signaling | 3.06E−02 | 7.84E−03 | | | 2.96E−02 | 0.00373 | 0.0274 | | |
| Stem cells_Cooperation between Hedgehog, IGF-2 and HGF signaling pathways in medulloblastoma stem cells | 3.06E−02 | 3.61E−02 | 1.52E−04 | | | | 0.0274 | | |
| Proteolysis_Role of Parkin in the Ubiquitin-Proteasomal Pathway | 3.11E−02 | | | 1.10E−02 | | 5.01E−03 | 0.0101 | 2.67E−02 | |
| Immune response_Immunological synapse formation | 3.20E−02 | 2.83E−02 | 1.62E−04 | | | | | | |
| Stem cells_Muscle progenitor cell migration in hypaxial myogenesis | 3.24E−02 | | | | | | | | 0.0104 |
| Apoptosis and survival_Lymphotoxin-beta receptor signaling | 3.24E−02 | 2.19E−02 | | 4.68E−03 | | | | 0.0465 | |
| Immune response_Gastrin in inflammatory response | 3.38E−02 | 1.49E−03 | | | 4.23E−02 | | | 0.000434 | 0.00713 |
| DNA damage_Role of SUMO in p 53 regulation | 3.50E−02 | 3.80E−03 | | | | 4.55E−02 | | 0.00781 | |
| Transcription_Transcription factor Tubby signaling pathways | 3.50E−02 | | | | | | | 0.00781 | |
| Stem cells_EGF-induced proliferation of Type C cells in SVZ of adult brain | 3.51E−02 | | 5.80E−03 | 1.19E−03 | | | | | 0.0218 |
| Normal and pathological TGF-beta-mediated regulation of cell proliferation | 3.51E−02 | 8.95E−03 | | | | | | | 0.00624 |
| Chemotaxis_Inhibitory action of lipoxins on IL-8- and Leukotriene B4-induced neutrophil migration | 3.63E−02 | | | 1.10E−02 | | 6.36E−04 | | 0.0109 | 2.24E−04 |
| Mucin expression in CF via TLRs, EGFR signaling pathways | 3.63E−02 | 1.47E−02 | | | | | | 0.0109 | |
| Translation_Insulin regulation of translation | 3.64E−02 | 2.00E−04 | | | 4.24E−03 | 7.48E−04 | | 0.000783 | 1.15E−02 |
| Immune response_Neurotensin-induced activation of IL-8 in colonocytes | 3.64E−02 | 2.41E−02 | | | 4.24E−03 | | | | 0.0115 |
| Signal transduction_JNK pathway | 3.64E−02 | 2.41E−02 | | | | | | 0.0000233 | |
| Immune response_IL-23 signaling pathway | 3.66E−02 | | | | | 2.99E−02 | | 0.0306 | 4.69E−02 |
| Cytoskeleton remodeling_Neurofilaments | 3.66E−02 | | 2.89E−02 | 1.97E−03 | | | | 0.00619 | 0.0469 |
| Development_Thyroliberin signaling | 3.87E−02 | | | | | | | | |
| Transcription_PPAR Pathway | 3.87E−02 | | | | | | | | 0.000148 |
| Apoptosis and survival_Cytoplasmic/mitochondrial transport of proapoptotic proteins Bid, Bmf and Bim | 4.00E−02 | | | | | 1.61E−04 | 0.000178 | 2.27E−02 | |
| Stem cells_Role of PKR1 and ILK in cardiac progenitor cells | 4.00E−02 | | | | | | 0.0334 | 2.27E−02 | |

TABLE 10-continued

List of Enriched GeneGo Pathway Maps in Four Different Breast Epithelial Cell Types

| | p-values in Nulliparous | | | | | p-values in Parous | | | |
|---|---|---|---|---|---|---|---|---|---|
| Pathway maps | CD44+ | CD24+ | CD10+ | Stroma | rat | CD44+ | CD24+ | CD10+ | Stroma |
| Apoptosis and survival_Role of CDK5 in neuronal death and survival | 4.00E-02 | 4.38E-02 | 6.75E-03 | | 3.60E-02 | | 3.34E-02 | 5.28E-03 | 0.0241 |
| Development_CNTF receptor signaling | 4.00E-02 | | | | 3.60E-02 | | 3.34E-02 | 2.27E-02 | 0.00463 |
| wtCFTR and deltaF508 traffic/ Membrane expression (norm and CF) | 4.00E-02 | | 1.28E-02 | | | | | | |
| Chemotaxis_CXCR4 signaling pathway | 4.00E-02 | | 6.75E-03 | | 3.60E-02 | | | | 0.0241 |
| G-protein signaling_Proinsulin C-peptide signaling | 4.02E-02 | 4.45E-06 | 1.56E-02 | | 1.21E-02 | 1.17E-02 | 2.53E-03 | 7.75E-04 | 1.42E-03 |
| Apoptosis and survival_TNFR1 signaling pathway | 4.08E-02 | 6.48E-03 | | | | 1.61E-02 | 0.0189 | 1.66E-02 | |
| Immune response_IL-10 signaling pathway | 4.26E-02 | | 9.09E-03 | | 2.36E-03 | 3.41E-02 | | 0.0348 | |
| Neurophysiological process_Dopamine D2 receptor transactivation of PDGFR in CNS | 4.26E-02 | 1.80E-02 | 4.09E-02 | | 1.46E-02 | | 2.13E-03 | 3.48E-02 | 0.00136 |
| Stem cells_Insulin, IGF-1 and TNF-alpha in brown adipocyte differentiation | 4.43E-02 | | | | 1.26E-04 | 0.0129 | 2.83E-03 | | 9.70E-08 |
| Development_Angiopoietin-Tie2 signaling | 4.53E-02 | 1.15E-02 | 3.09E-02 | | 3.95E-02 | 0.00118 | 0.00805 | | |
| Anti-apoptotic action of Gastrin in pancreatic cancer | 4.53E-02 | 1.15E-02 | | | 8.88E-03 | 5.92E-03 | 3.66E-02 | 6.12E-03 | 2.65E-02 |
| Development_Regulation of telomere length and cellular immortalization | 4.53E-02 | | | | 8.88E-03 | 2.48E-02 | | 0.0255 | |
| Development_Flt3 signaling | 4.55E-02 | 2.88E-02 | 6.34E-03 | | 2.27E-02 | 1.79E-02 | 2.07E-02 | 1.08E-03 | 2.89E-03 |
| Pancreatic cancer cell resistance to Tarceva (erlotinib) | 4.91E-02 | 2.05E-02 | 4.61E-02 | | 2.81E-03 | 0.0385 | 0.00254 | | |
| Immune response_Signaling pathway mediated by IL-6 and IL-1 | 4.91E-02 | | | | | | | | |
| Apoptosis and survival_FAS signaling cascades | | 2.64E-02 | | | | 2.74E-05 | 0.000131 | 4.22E-03 | |
| TTP metabolism | | | | | | 0.0000608 | | | |
| Resistance of pancreatic cancer cells to death receptor signaling | | | | | | 1.29E-04 | 0.00105 | 4.53E-03 | |
| Transcription_Assembly of RNA Polymerase II preinitiation complex on TATA-less promoters | | | | | | 0.000136 | 0.0257 | | |
| Development_PIP3 signaling in cardiac myocytes | | 2.29E-03 | | | 4.70E-05 | 3.38E-04 | 1.39E-03 | 6.60E-05 | 1.24E-04 |
| HCV-dependent regulation of RNA polymerases leading to HCC | | | | | | 0.00035 | 0.0387 | | |
| Stem cells_H3K9 demethylases in pluripotency maintenance of stem cells | | | | | | 4.62E-04 | 4.36E-02 | 1.98E-02 | 3.37E-02 |
| Inhibition of apoptosis in gastric cancer | | | | | | 6.32E-04 | 0.00333 | 6.61E-04 | |
| Cell cycle_Start of DNA replication in early S phase | | 3.61E-02 | | | | 0.00067 | 0.000883 | | |
| Apoptosis and survival_Caspase cascade | | 1.64E-03 | | | | 0.000816 | 0.00105 | | |
| Immune response_BCR pathway | | | | | 7.76E-04 | 9.79E-04 | 1.29E-02 | 4.15E-03 | 8.06E-03 |
| Immune response_ICOS pathway in T-helper cell | | 9.01E-03 | | | 1.40E-03 | 1.40E-03 | 0.0246 | 6.19E-03 | |
| Cell cycle_The metaphase checkpoint | | | | | | 0.00141 | | | |
| Inhibitory action of Lipoxins on neutrophil migration | | | | | 1.85E-02 | 1.46E-03 | | 0.0194 | 4.90E-04 |
| DNA damage_NHEJ mechanisms of DSBs repair | | | | | 3.16E-02 | 1.67E-03 | 0.0297 | 1.18E-02 | |
| Cytoskeleton remodeling_Alpha-1A adrenergic receptor-dependent inhibition of PI3K | | | | | 5.17E-04 | 1.67E-03 | 2.97E-02 | 1.18E-02 | 2.89E-04 |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Regulation of metabolism_Triiodothyronine and Thyroxine signaling | | | | | | 0.00186 | | | |
| Cell cycle_Chromosome condensation in prometaphase | | | | | | 2.70E-03 | | 0.00000331 | |
| Development_IGF-1 receptor signaling | 2.47E-05 | | | 5.23E-04 | | 2.77E-03 | 9.87E-03 | 6.69E-04 | 2.24E-04 |
| dCTP/dUTP metabolism | | | | | | 0.003 | | | |
| dGTP metabolism | | | | | | 0.00332 | | | |
| Inhibition of RUNX3 signaling in gastric cancer | | | | 4.63E-02 | | 0.00336 | 0.00739 | | |
| Apoptosis and survival_Beta-2 adrenergic receptor anti-apoptotic action | | | | | | 0.00412 | 8.69E-03 | | 6.09E-03 |
| Signal transduction_Activin A signaling regulation | | | 1.15E-02 | | | 4.38E-03 | 0.00105 | 4.53E-03 | |
| Stem cells_Fetal brown fat cell differentiation | | | | 4.00E-03 | | 0.00447 | 1.41E-02 | | 8.81E-03 |
| Immune response_CXCR4 signaling via second messenger | 4.38E-02 | 6.75E-03 | | 3.60E-02 | | 5.11E-03 | 0.00711 | 5.28E-03 | |
| dATP/dITP metabolism | | | | | | 0.00573 | | | |
| Signal transduction_PTEN pathway | 2.01E-03 | | | 6.69E-03 | | 5.97E-03 | 0.0246 | 6.19E-03 | |
| Microsatellite instability in gastric cancer | | | | | | 0.00601 | 0.00177 | | |
| Inhibition of TGF-beta signaling in gastric cancer | | | | | | 6.01E-03 | 0.0117 | 3.06E-02 | |
| Immune response_Regulation of T cell function by CTLA-4 | | 3.44E-02 | | 1.90E-03 | | 6.82E-03 | 1.68E-03 | 2.85E-02 | 5.95E-03 |
| DNA damage_DNA-damage-induced responses | 4.67E-02 | | | | | 0.00747 | 0.00337 | | |
| Stem cells_Self-renewal of adult neural stem cells | | | | | | 0.00756 | 0.029 | | |
| Regulation of degradation of deltaF508 CFTR in CF | | | | 1.67E-02 | | 8.44E-03 | | 0.00869 | |
| Transcription_Sin3 and NuRD in transcription regulation | 3.46E-03 | | | | | 0.00892 | | | 3.47E-02 |
| Blood coagulation_GPIb-IX-V-dependent platelet activation | | | | | | 0.00952 | | | 1.11E-02 |
| Transcription_Receptor-mediated HIF regulation | 3.96E-03 | 1.32E-02 | | 5.03E-04 | | 1.01E-02 | | 0.00238 | 8.39E-03 |
| Stem cells_Signaling pathways in embryonic hepatocyte maturation | 5.00E-02 | 1.41E-02 | | | | 1.05E-02 | 0.0365 | 3.56E-02 | |
| Apoptosis and survival_nAChR in apoptosis inhibition and cell cycle progression | 2.61E-02 | | | 2.13E-02 | | 1.15E-02 | | 0.0118 | |
| Stem cells_Role of growth factors in the maintenance of embryonic stem cell pluripotency | | | | 3.23E-03 | | 0.0129 | 0.000583 | | |
| Apoptosis and survival_Anti-apoptotic TNFs/NF-kB/Bcl-2 pathway | 5.10E-03 | | 1.09E-06 | | | 1.29E-02 | 0.0156 | 6.61E-04 | |
| DNA damage_Role of Brca1 and Brca2 in DNA repair | 2.92E-02 | | | | | 0.0133 | | | |
| Translation IL-2 regulation of translation | 4.24E-02 | | | 3.62E-02 | | 0.0139 | 3.40E-02 | | 3.60E-03 |
| DNA damage_Mismatch repair | | | | | | 0.0139 | 0.00518 | | |
| Neurophysiological process_Olfactory transduction | | | | | | 0.0139 | | | |
| DNA damage_Inhibition of telomerase activity and cellular senescence | 7.04E-03 | | | 3.62E-02 | | 0.0139 | | | |
| Immune response_Role of DAP12 receptors in NK cells | | | | 4.91E-02 | | 0.0142 | 0.0451 | | |
| Immune response_CD28 signaling | 1.17E-03 | | | 1.44E-02 | | 1.42E-02 | 0.0451 | 1.47E-02 | |
| Immune response_PIP3 signaling in B lymphocytes | | | | | | 0.0144 | 1.72E-02 | | 1.15E-02 |
| Immune response_ETV3 affect on CSF1-promoted macrophage differentiation | | | | | | 0.0152 | | | |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Blood coagulation_GPVI-dependent platelet activation | | | | | 1.57E-02 | 0.0157 | 0.0482 | | |
| Inhibition of tumor suppressive pathways in pancreatic cancer | | 8.43E-03 | | | | 1.65E-02 | 0.0387 | 1.69E-02 | |
| Transcription_Ligand-Dependent Transcription of Retinoid-Target genes | | | | | | 0.0196 | | | |
| Development_Thrombopoietin-regulated cell processes | | | | | 2.48E-02 | 1.99E-02 | | 0.000252 | |
| Role of alpha-6/beta-4 integrins in carcinoma progression | | 1.77E-03 | | | 4.35E-06 | 0.0199 | | | 1.52E-02 |
| Chemotaxis_Lipoxin inhibitory action on fMLP-induced neutrophil chemotaxis | | | 2.10E-04 | | 6.69E-03 | 2.20E-02 | | 0.0226 | 3.63E-03 |
| Development_EGFR signaling via PIP3 | | 1.17E-02 | | | | 0.0226 | | | |
| Stem cells_Differentiation of natural regulatory T cells | | | | | | 0.0248 | 0.00805 | | |
| G-protein signaling_S1P2 receptor signaling | | | | | 8.88E-03 | 0.0248 | | | |
| Translation_Opioid receptors in regulation of translation | | | | | | 2.61E-02 | | 0.0267 | 9.24E-04 |
| Transport_RAB3 regulation pathway | | | | | | 0.0271 | | | |
| G-protein signaling_RAC1 in cellular process | | 2.61E-03 | | | 1.00E-02 | 0.0277 | | | |
| DNA damage_Nucleotide excision repair | | | | | | 0.0277 | | | |
| Immune response_Inhibitory action of lipoxins on superoxide production induced by IL-8 and Leukotriene B4 in neutrophils | | | | | 3.43E-02 | 2.91E-02 | | 0.0299 | |
| Inhibitory action of Lipoxins on Superoxide production in neutrophils | | | | | 3.43E-02 | 2.91E-02 | | 0.0299 | |
| wtCFTR and delta508-CFTR traffic/Generic schema (norm and CF) | | | | | | 0.0317 | | | 4.59E-07 |
| Apoptosis and survival_DNA-damage-induced apoptosis | | 2.03E-04 | | | | 0.0327 | 0.0155 | | |
| Apoptosis and survival_NGF signaling pathway | | | 9.09E-03 | | | 0.0341 | 0.0135 | | |
| Apoptosis and survival_APRIL and BAFF signaling | | | | 3.35E-03 | | 3.42E-02 | | 0.00921 | |
| Immune response_NFAT in immune response | | 5.00E-02 | | | 1.10E-02 | 0.0346 | 0.00987 | | |
| Apoptosis and survival_Anti-apoptotic TNFs/NF-kB/IAP pathway | | 3.70E-03 | | 5.59E-03 | | 3.85E-02 | | 0.0394 | |
| Immune response_TCR and CD28 co-stimulation in activation of NF-kB | | | | | | 0.0414 | | | |
| Immune response_Innate immune response to RNA viral infection | | | | 6.39E-03 | | 4.33E-02 | | 0.0102 | |
| Immune response _IFN gamma signaling pathway | | | | | 3.60E-03 | 0.044 | | | 1.77E-03 |
| Immune response_CD16 signaling in NK cells | | 1.88E-02 | 2.43E-03 | | 1.37E-02 | 0.0472 | 0.0121 | | |
| Immune response_Delta-type opioid receptor signaling in T-cells | | | | | 2.13E-02 | 4.84E-02 | | 0.000367 | 1.40E-02 |
| Apoptosis and survival_p 53-dependent apoptosis | | 1.14E-05 | | | | 0.0484 | 0.00352 | | |
| Effect of H. pylori infection on apoptosis in gastric epithelial cells | | 7.92E-04 | | | | | 0.0365 | | |
| Immune response_Histamine H1 receptor signaling in immune response | | 1.11E-02 | | | 3.18E-02 | 0.029 | | | |
| Immune response_IL-4-antiapoptotic action | | 5.92E-03 | | | | | | 0.0136 | 0.0158 |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Development_Angiotensin signaling via PYK2 | | 6.48E−03 | | | 2.07E−02 | | | 0.00422 | 0.0126 |
| Development_Alpha-2 adrenergic receptor activation of ERK | | | 3.91E−03 | | 7.77E−03 | | 1.68E−03 | | 0.000168 |
| Immune response_CCR5 signaling in macrophages and T lymphocytes | | | | | 1.26E−03 | | | 0.0212 | 0.00269 |
| Development_A3 receptor signaling | | 1.22E−02 | | | | | | 0.00222 | 0.0214 |
| G-protein signaling_N-RAS regulation pathway | | 8.95E−03 | | | | | | | |
| Immune response_Murine NKG2D signaling | | | 4.87E−03 | | 1.89E−02 | | | | |
| EML4/ALK fusion protein in nonsmoking-related lung cancer | | 1.39E−03 | | | | | 2.74E−02 | 1.78E−02 | 0.0196 |
| Transcription_NF-kB signaling pathway | | 1.79E−02 | | 3.76E−03 | | | | 0.00238 | |
| Development_ERBB-family signaling | | 3.96E−03 | | | | | | 0.0105 | 0.0377 |
| Fructose metabolism | | 7.89E−03 | | | | | | | |
| Apoptosis and survival_Apoptotic Activin A signaling | | | | | | | | 0.00619 | 0.0469 |
| Development_EPO-induced Jak-STAT pathway | | | | | | | | | 0.00526 |
| DNA damage_Role of NFBD1 in DNA damage response | | 1.30E−02 | | | | | | | |
| Mechanisms of K-RAS addiction in lung cancer cells | | 2.92E−02 | | | | | | | |
| Development_EDNRB signaling | | | | | 3.70E−02 | | | 0.00979 | 0.00553 |
| Immune response_Role of the Membrane attack complex in cell survival | | | | | | | | 0.00528 | 0.0241 |
| Regulation of lipid metabolism_Insulin regulation of fatty acid methabolism | | | | | 1.72E−02 | | | | 5.72E−06 |
| KLF6 and regulation of KLF6 alternative splicing in HCC | | | | | 1.33E−03 | | | 0.00424 | 0.0379 |
| Development_S1P1 receptor signaling via beta-arrestin | | | | | | | 3.03E−02 | | 0.0000769 |
| Cell cycle_Cell cycle (generic schema) | | 1.13E−03 | | | | | | 0.00278 | |
| Development_Regulation of epithelial-to-mesenchymal transition (EMT) | | | 1.59E−05 | | | | 0.000016 | | |
| Development_S1P4 receptor signaling pathway | | 9.99E−03 | | | 8.03E−03 | | | | 0.0337 |
| Signal transduction_IP3 signaling | | 4.32E−02 | | 4.27E−02 | 3.43E−02 | | 1.78E−03 | 4.92E−04 | 0.000988 |
| Development_Endothelin-1/ EDNRA transactivation of EGFR | | 9.01E−03 | | | 1.40E−03 | | | 0.00619 | 0.0166 |
| Cell cycle_Sister chromatid cohesion | | | | | | | | 0.0198 | |
| Glutathione metabolism/Rodent version | | 2.16E−02 | | | 1.00E−05 | | | | |
| Development_Beta-adrenergic receptors transactivation of EGFR | | | 2.32E−03 | | 4.70E−02 | | 3.10E−04 | | 0.000166 |
| Development_ACM2 and ACM4 activation of ERK | | 2.64E−02 | | | 4.78E−03 | | | | 0.0126 |
| Activation of pro-oncogenic TGF-beta potential in gastric cancer | | 2.60E−03 | | 2.89E−02 | | | | 0.0306 | |
| Stem cells_FGF10 in development of subcutaneous white adipose tissue in embryogenesis | | | | | 2.34E−02 | | 2.62E−04 | | 0.0168 |
| G-protein signaling_RhoA regulation pathway | | 1.02E−02 | 1.38E−03 | | 3.60E−02 | | | 0.0227 | |
| Immune response_IL-7 signaling in B lymphocytes | | | | | | | | 1.89E−02 | 0.0126 |
| G-protein signaling_Rap2B regulation pathway | | | 4.59E−02 | | | | | | |

TABLE 10-continued

List of Enriched GeneGo Pathway Maps in Four Different Breast Epithelial Cell Types

| Pathway maps | p-values in Nulliparous | | | | | p-values in Parous | | | |
| --- | --- | --- | --- | --- | --- | --- | --- | --- | --- |
| | CD44+ | CD24+ | CD10+ | Stroma | rat | CD44+ | CD24+ | CD10+ | Stroma |
| Development_Activation of ERK by Alpha-1 adrenergic receptors | | | | | | | | | 0.0152 |
| EGF-and HGF-dependent stimulation of metastasis in gastric cancer | | 1.42E−03 | | | 4.63E−02 | | | | |
| Cell cycle_Spindle assembly and chromosome separation | | 8.95E−03 | | | 3.27E−02 | | | | |
| Glycogen metabolism | | | | | | | | | 0.0377 |
| Neurophysiological process_Delta-type opioid receptor in the nervous system | | | | | | | | | 0.0408 |
| Fructose metabolism/Rodent version | | 1.65E−02 | | | | | | | |
| Inhibitory action of Lipoxins and Resolvin E1 on neutrophil functions | | | 4.20E−03 | | | | | 0.0425 | |
| Immune response_PGE2 in immune and neuroendocrine system interactions | | | 2.81E−02 | | | | | | |
| Development Dopamine D2 receptor transactivation of EGFR | | | 3.14E−02 | | 1.10E−02 | 1.01E−02 | 2.67E−02 | 0.0000955 | |
| Autophagy_Autophagy | | 7.84E−03 | 4.95E−03 | | | | | | |
| Regulation of lipid metabolism_RXR-dependent regulation of lipid metabolism via PPAR, RAR and VDR | | | | | | | | | 0.00264 |
| Development_A1 receptor signaling | | | | | | | 4.21E−02 | 8.94E−04 | 0.00736 |
| Cell cycle_Role of APC in cell cycle regulation | | | 4.95E−03 | | | | | | |
| Plasminogen activators signaling in pancreatic cancer | | 1.15E−02 | | | 3.95E−02 | | | | 0.0265 |
| NGF activation of NF-kB | | 5.10E−03 | 5.00E−04 | 9.65E−04 | | | 0.0197 | 2.29E−03 | |
| Immune response_IL-15 signaling | | 4.01E−02 | 4.33E−02 | | | | | 0.00347 | 0.00108 |
| Cell cycle_Role of SCF complex in cell cycle regulation | | 1.14E−05 | 5.00E−04 | | | | | | |
| Development_Gastrin in differentiation of the gastric mucosa | | | | | | | | 0.00921 | |
| Propionate metabolism p.1 | | | | | | | | | 0.0441 |
| Lysine metabolism | | | | | 1.42E−02 | | | | 0.00192 |
| CFTR folding and maturation (norm and CF) | | | | 5.69E−03 | | | | 0.00369 | |
| Development Keratinocyte differentiation | | 1.49E−03 | | | | | | | |
| Tryptophan metabolism/Rodent version | | | | | 4.11E−02 | | | | 0.00734 |
| G-protein signaling_H−RAS regulation pathway | | | 1.03E−02 | | | | | | |
| Normal wtCFTR traffic/Sorting endosome formation | | | 1.86E−04 | 1.18E−02 | | | | | |
| Apoptosis and survival_Regulation of Apoptosis by Mitochondrial Proteins | | 3.26E−02 | | | | | 0.0246 | | |
| Immune response_IL-4 signaling pathway | | 2.88E−02 | | | | | | | |
| Development_Cross-talk between VEGF and Angiopoietin 1 signaling pathways | | 1.80E−02 | 4.09E−02 | | | | | | |
| Cell cycle_ESR1 regulation of G1/S transition | | 3.98E−02 | 1.92E−04 | | | | | | |
| Development_Activation of ERK by Kappa-type opioid receptor | | 1.29E−02 | | | 4.32E−02 | | 4.01E−02 | 1.46E−03 | 0.00595 |
| HCV-dependent regulation of membrane receptors signaling in HCC | | | | | | | | 0.000227 | |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Delta508-CFTR traffic/Sorting endosome formation in CF | | | 8.14E−04 | 2.31E−02 | | | | | 0.000752 |
| Immune response_IL-13 signaling via PI3K-ERK | | 1.34E−02 | | | | | | | |
| G-protein signaling_G-Protein alpha-i signaling cascades | | | | | | | | | 0.0109 |
| Glycolysis and gluconeogenesis p. 1 | | 9.01E−03 | | | | | | | |
| Muscle contraction_Oxytocin signaling in uterus and mammary gland | | 3.05E−02 | | 2.26E−02 | 2.33E−02 | | | | |
| Development_Delta-and kappa-type opioid receptors signaling via beta-arrestin | | | 2.31E−02 | | | | | 0.000622 | 0.00609 |
| Glutathione metabolism | | 1.38E−02 | | | 3.85E−06 | | | | |
| Regulation of lipid metabolism_PPAR regulation of lipid metabolism | | | | | 1.30E−04 | | | | 0.0115 |
| Immune response PGE2 common pathways | | | | | | | | | 0.0269 |
| Immune response_HTR2A-induced activation of cPLA2 | | 6.48E−03 | | 2.81E−02 | | | | | 0.00257 |
| Mitochondrial unsaturated fatty acid beta-oxidation | | | | | 6.00E−03 | | | | 0.0152 |
| Development_Role of HDAC and calcium/calmodulin-dependent kinase (CaMK) in control of skeletal myogenesis | | | 5.64E−03 | | 3.60E−03 | | | | 0.00177 |
| Development_Growth hormone signaling via PI3K/AKT and MAPK cascades | | | | | | | 1.72E−02 | 3.69E−03 | 0.0115 |
| Neuropeptide signaling in pancreatic cancer | | 4.32E−02 | | | | | | | |
| Apoptosis and survival_NO synthesis and signaling | | | | | | | | 0.0162 | 0.0333 |
| Immune response_IL-15 signaling via JAK-STAT cascade | | | 2.73E−02 | | | | | | |
| Regulation of lipid metabolism_G-alpha(q) regulation of lipid metabolism | | | | | | | | | 0.0432 |
| Neurophysiological process_Long-term depression in cerebellum | | 4.32E−02 | | | | | | | |
| Apoptosis and survival_Anti-apoptotic action of membrane-bound ESR1 | | 4.80E−02 | | | | | | 0.00612 | |
| Development_Role of CDK5 in neuronal development | | 1.93E−03 | 2.76E−02 | | 3.60E−02 | | 3.34E−02 | | 0.00463 |
| Cell cycle_Nucleocytoplasmic transport of CDK/Cyclins | | 1.75E−03 | | | | | | 0.0276 | |
| Immune response_IL-5 signalling | | | 6.34E−03 | | 2.27E−02 | | | | 0.00289 |
| Development_Mu-type opioid receptor signaling | | 1.61E−02 | | | | | | 0.00204 | 0.00751 |
| Pentose phosphate pathway/Rodent version | | | | | | | | | 0.025 |
| Phenylalanine metabolism | | | | | 3.99E−02 | | | | 0.00161 |
| Glycolysis and gluconeogenesis (short map) | | 1.50E−02 | | | 6.87E−04 | | | | |
| WNT signaling in gastric cancer | | | 1.96E−03 | 3.61E−04 | | | 0.00908 | | |
| Stem cells_Transcription factors in segregation of hepatocytic lineage | | | | | | | 0.000615 | 4.59E−04 | |
| Development_G-Proteins mediated regulation MAPK-ERK signaling | | | | | 2.70E−02 | | | | 0.0166 |
| Development_EPO-induced PI3K/AKT pathway and Ca(2+) influx | | | | | 2.07E−02 | | 0.00425 | | |
| Development Angiotensin activation of Akt | | 3.41E−02 | | | 6.69E−03 | | | | 0.00363 |
| DNA damage_ATM/ATR regulation of G2/M checkpoint | | 1.80E−02 | | | | | | | |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Development_SSTR1 in regulation of cell proliferation and migration | | | | | | | | 0.0494 | |
| Cytoskeleton remodeling_ESR1 action on cytoskeleton remodeling and cell migration | | 4.24E-02 | | | | | | | |
| Immune response_TREM1 signaling pathway | | 2.25E-02 | | | | | | 0.00521 | |
| Stem cells_FGF signaling in pancreatic and hepatic differentiation of embryonic stem cells | | | | | | | | 0.0425 | |
| Tryptophan metabolism | | | | | 3.92E-02 | | | | 0.0069 |
| Triacylglycerol metabolism p.1 | | | | | 2.16E-02 | | | | 0.0123 |
| G-protein signaling_Rac3 regulation pathway | | 2.34E-02 | | | | | | | |
| Development_Growth hormone signaling via STATs and PLC/IP3 | | | 3.09E-02 | 2.50E-04 | | | | | |
| Regulation of lipid metabolism_Regulation of fatty acid synthesis: NLTP and EHHADH | | | | | | | | | 0.000219 |
| Oxidative stress_Angiotensin II-induced production of ROS | | 4.80E-02 | | 3.95E-02 | | | | | |
| Cholesterol and Sphingolipids transport/Recycling to plasma membrane in lung (normal and CF) | | | 2.73E-02 | | | | | | |
| Development_TGF-beta-induction of EMT via ROS | | | | | | | | | 0.0228 |
| Immune response_IL-22 signaling pathway | | 5.80E-03 | | 3.27E-02 | | | | | |
| Cell cycle_Transition and termination of DNA replication | | | | | | | | 0.00189 | |
| Stem cells_FGF2-induced self-renewal of adult neural stem cells | | | | | | | | 0.0118 | 0.0408 |
| Regulation of metabolism_Bile acids regulation of glucose and lipid metabolism via FXR | | | | | | | | | 0.0318 |
| Apoptosis and survival_NO signaling in survival | | | | | | | | 0.00515 | 0.0423 |
| Signal transduction_Activation of PKC via G-Protein coupled receptor | | 9.05E-04 | | 2.63E-03 | | | 1.08E-02 | 3.27E-03 | 0.0269 |
| Development_Hedgehog signaling | | 3.41E-02 | 2.02E-03 | 2.10E-04 | | 0.0246 | | | |
| Development_GDNF family signaling | | 2.01E-03 | | | | | | 0.00619 | 0.0166 |
| HBV-dependent transcription regulation leading to HCC | | | | | | | | | 0.0469 |
| Butanoate metabolism | | | | | 3.29E-02 | | | | 0.0192 |
| Development_ERK5 in cell proliferation and neuronal survival | | | 2.73E-02 | | | | | | |
| Development_FGFR signaling pathway | | 1.76E-02 | 5.02E-03 | 3.23E-03 | | | | 0.0134 | 0.029 |
| Multiple Myeloma (general scheme) | | | | | | | 0.0297 | | |
| Development_Angiotensin activation of ERK | | 3.98E-02 | | 1.19E-03 | | | | 0.0202 | 0.00406 |
| Leucune, isoleucine and valine metabolism/Rodent version | | | | | | | | | 0.000262 |
| Development_Mu-type opioid receptor signaling via Beta-arrestin | | | | | | | | | 0.0000955 |
| Immune response_Alternative complement pathway | | | 1.79E-05 | | | | | | |
| Development_Angiotensin signaling via beta-Arrestin | | | | 2.89E-02 | 1.27E-02 | | | 0.00619 | 0.00826 |

TABLE 10-continued

List of Enriched GeneGo Pathway Maps in Four Different Breast Epithelial Cell Types

| | p-values in Nulliparous | | | | | p-values in Parous | | | |
| --- | --- | --- | --- | --- | --- | --- | --- | --- | --- |
| Pathway maps | CD44+ | CD24+ | CD10+ | Stroma | rat | CD44+ | CD24+ | CD10+ | Stroma |
| Development_Transactivation of PDGFR in non-neuronal cells by Dopamine D2 receptor | | | | | | | 7.40E−04 | | 0.00306 |
| Development_Membrane-bound ESR1: interaction with growth factors signaling | | | | 2.07E−02 | | | | 0.00422 | |
| Transcription_Androgen Receptor nuclear signaling | | 3.14E−02 | | 6.99E−03 | | | 0.00535 | 2.05E−02 | |
| HBV regulation of DNA repair and apoptosis leading to HCC | | 1.61E−02 | | | | | | | |
| Regulation of lipid metabolism_Regulation of lipid metabolism via LXR, NF-Y and SREBP | | | | | | | | | 0.0347 |
| Immune response_IL-6 signaling pathway | | | | 4.25E−02 | | | | | |
| Immune response_Lectin induced complement pathway | | | 1.46E−04 | | | | | | |
| Arachidonic acid production | | 4.65E−02 | 1.27E−02 | | 3.70E−02 | | | | 0.0231 |
| G-protein signaling_Rap1A regulation pathway | | 1.98E−02 | | | | | | | |
| Stem cells_Dopamine-induced transactivation of EGFR in SVZ neural stem cells | | 3.26E−02 | | | | | | 0.0156 | 0.0176 |
| Immune response_Fc epsilon RI pathway | | 5.63E−03 | 2.08E−02 | | | | 1.41E−02 | 4.66E−03 | 0.00881 |
| FGF signaling in gastric cancer | | | 2.73E−02 | | | | 0.0489 | | |
| Development_FGF-family signaling | | | 3.09E−02 | | | | 0.00805 | | |
| Fatty Acid Omega Oxidation | | | | | | | | | 0.0241 |
| FGFR3 signaling in multiple myeloma | | | | | | | 4.37E−02 | | 0.00115 |
| Development_MicroRNA-dependent inhibition of EMT | | | | | | | 0.00468 | | |
| Cardiac Hypertrophy_Ca(2+)-dependent NF-AT signaling in Cardiac Hypertrophy | | | 1.85E−02 | 1.85E−02 | | | | | 0.0381 |
| Immune response_Role of integrins in NK cells cytotoxicity | | | | | | | | | 0.0347 |
| Stem cells_MMP-14-induced COX-2 expression in glioblastoma stem cells | | | 2.31E−02 | | | | | | |
| Hedgehog signaling in pancreatic cancer | | 2.52E−05 | | | | | | | |
| Neurophysiological process_GABA-A receptor life cycle | | | | | | | | | 0.00162 |
| HCV-dependent cytoplasmic signaling leading to HCC | | | 4.61E−02 | 1.67E−02 | | | | 0.000227 | 0.000193 |
| Neurophysiological process_NMDA-dependent post-synaptic long-term potentiation in CA1 hippocampal neurons | | | | | | | | 0.0148 | 0.0045 |
| Immune response_IL-12 signaling pathway | | | 2.31E−02 | | | | | 0.00424 | |
| Stem cells_Scheme: Histone H3 demethylases in stem cells | | | | | | | | 0.0156 | |
| Neurophysiological process_HTR1A receptor signaling in neuronal cells | | | | | | | | 0.0149 | 0.0475 |
| Atherosclerosis_Role of ZNF202 in regulation of expression of genes involved in Atherosclerosis | | 4.81E−02 | 2.00E−02 | 1.97E−04 | | | 0.0387 | 1.69E−02 | |
| Translation_Non-genomic (rapid) action of Androgen Receptor | | 4.50E−03 | | | | | 1.41E−02 | 1.18E−02 | 0.0408 |
| Immune response_Lipoxins and Resolvin E1 inhibitory action on neutrophil functions | | | | 2.31E−03 | | | | 0.0255 | |
| Cell cycle_Regulation of G1/S transition (part 2) | | 4.30E−04 | | | | | | 0.0348 | |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Anti-apoptotic action of Gastrin in gastric cancer | | 1.15E−02 | | | 8.88E−03 | | | 0.00612 | |
| Development_Activation of astroglial cells proliferation by ACM3 | | 1.64E−03 | 5.80E−03 | | 6.90E−03 | | | 0.0202 | |
| GTP metabolism | | | | | | | | | 0.0311 |
| Neurophysiological process_Thyroliberin in cell hyperpolarization and excitability | | 4.80E−02 | | | | | | | |
| Glutathione metabolism/ Human version | | 1.50E−02 | | | 4.55E−06 | | | | |
| Stem cells_FGF2 signaling during embryonic stem cell differentiation | | | | | | | | 0.0227 | |
| Proliferative action of Gastrin in gastric cancer | | 4.58E−03 | | 3.65E−05 | 4.59E−02 | | | | 0.0421 |
| Cell adhesion_Integrin inside-out signaling | | | 7.04E−03 | 3.84E−03 | 1.71E−02 | | | | 0.0356 |
| Tissue factor signaling in Lung Cancer | | | 3.14E−02 | | | | | | |
| Development_Prolactin receptor signaling | | 2.63E−02 | 8.70E−03 | | 2.00E−02 | | | | 0.0406 |
| Phenylalanine metabolism/Rodent version | | | | | 3.52E−02 | | | | 0.00559 |
| Development_SSTR2 in regulation of cell proliferation | | | | | | | | 0.00705 | 0.00595 |
| Immune response_CD137 signaling in immune cell | | | 7.26E−03 | | | | | 0.0118 | |
| Development_WNT5A signaling | | 9.01E−03 | 2.82E−02 | | | | 0.00597 | | |
| Translation_Translation regulation by Alpha-1 adrenergic receptors | | 1.03E−03 | | | 1.32E−02 | | | 0.0419 | 0.029 |
| Development_Gastrin in cell growth and proliferation | | 2.89E−03 | 3.91E−03 | | 2.69E−02 | 2.42E−02 | 2.79E−03 | 0.00394 | |
| Effect of H. pylori infection on gastric epithelial cell proliferation | | 2.63E−02 | 2.71E−02 | | | | | | |
| Chemotaxis_CCR4-induced leukocyte adhesion | | | | 4.63E−02 | 2.39E−02 | | | | |
| GTP-XTP metabolism | | 8.97E−03 | | | | | | | |
| Transcription_Ligand-dependent activation of the ESR1/SP pathway | | 2.92E−02 | | | | | | | |
| Immune response_TLR3 and TLR4 induce TICAM1-specific signaling pathway | | 4.24E−02 | | 1.58E−02 | | | | | |
| Development_Delta-type opioid receptor mediated cardioprotection | | | 1.03E−02 | | 4.70E−02 | | | 0.00808 | 0.000166 |
| Development_Mu-type opioid receptor regulation of proliferation | | | | | 1.89E−02 | | | | 0.00192 |
| Immune response IL-12-induced IFN-gamma production | | | | 2.63E−03 | | | | | 0.000259 |
| Proliferative action of Gastrin in pancreatic cancer | | 7.26E−03 | | | 2.27E−02 | | | | 0.00108 |
| Cell cycle_Regulation of G1/S transition (part 1) | | 3.46E−03 | 4.22E−02 | | | | 0.0000516 | 3.50E−02 | |
| Protein folding_Membrane trafficking and signal transduction of G-alpha (i) heterotrimeric G-protein | | | | 1.46E−03 | | | 2.97E−02 | | 0.00295 |
| Immune response_Classical complement pathway | | | 8.50E−06 | | | | | | |
| Transport_Rab-9 regulation pathway | | | | 2.84E−02 | 5.01E−03 | | | | |
| Development_Signaling of Beta-adrenergic receptors via Beta-arrestins | | | | | | | | 0.00736 | |
| Lysine metabolism/Rodent version | | | | | 4.82E−03 | | | | 0.00209 |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| G-protein signaling_G-Protein beta/gamma signaling cascades | | | | | | | | 0.00528 | 0.0241 |
| Immune response_Sialic-acid receptors (Siglecs) signaling | | | | | | | | 0.0179 | |
| Leucune, isoleucine and valine metabolism.p.2 | | | | | | | | | 0.000212 |
| Neurophysiological process_Kappa-type opioid receptor in transmission of nerve impulses | | | 4.63E−02 | | | | | | |
| Stem cells_Scheme: Adult neurogenesis in the Subventricular Zone | | | 1.37E−02 | | | | | | |
| Immune response_MIF-JAB1 signaling | | 2.14E−03 | 3.14E−02 | | | | | | |
| Immune response_Function of MEF2 in T lymphocytes | | 4.65E−02 | 1.27E−02 | | 3.70E−02 | | | | 0.00553 |
| Immune response_Human NKG2D signaling | | | 1.17E−02 | | | | | | |
| Aflatoxin B1-dependent induction of HCC | | 3.98E−02 | | | | | | | |
| Neurophysiological process_Role of CDK5 in pre-synaptic signaling | | | 3.88E−02 | | | | | 0.0442 | |
| Stem cells_mGluR3 signaling in glioblastoma stem cells | | | | | 4.28E−02 | | | 0.0386 | 0.0269 |
| G-protein signaling_G-Protein alpha-q signaling cascades | | 1.02E−02 | | | 3.60E−02 | | | 0.00103 | |
| DNA damage_ATM/ATR regulation of G1/S checkpoint | | 2.44E−07 | | | | | | 0.0178 | |
| Pentose phosphate pathway | | | | | | | | | 0.0269 |
| Immune response_MIF-the neuroendocrine-macrophage connector | | 3.41E−02 | 2.02E−03 | 3.50E−02 | 6.69E−03 | 0.00597 | | | |
| Immune response Antiviral actions of Interferons | | | | | 1.21E−02 | | | | |
| Glycolysis and gluconeogenesis p. 2/Human version | | | | | 2.53E−03 | | | | |
| Peroxisomal branched chain fatty acid oxidation | | | | | 3.41E−02 | | | | |
| Regulation of lipid metabolism_Alpha-1 adrenergic receptors signaling via arachidonic acid | | | | | 4.49E−02 | | | | |
| Development_Angiotensin signaling via STATs | | | | | 1.58E−06 | | | | |
| Triacylglycerol metabolism p.2 | | | | | 1.89E−02 | | | | |
| Glycolysis and gluconeogenesis p.3/Human version | | | | | 1.10E−02 | | | | |
| Immune response_T cell receptor signaling pathway | | | | | 2.90E−03 | | | | |
| Glycolysis and gluconeogenesis p.3 | | | | | 1.10E−02 | | | | |
| 2-Naphthylamine and 2-Nitronaphtalene metabolism | | | | | 3.79E−04 | | | | |
| Androstenedione and testosterone biosynthesis and metabolism p.2/Rodent version | | | | | 1.00E−02 | | | | |
| Retinol metabolism/Rodent version | | | | | 1.47E−02 | | | | |
| G-protein signaling_Regulation of CDC42 activity | | | | | 3.27E−02 | | | | |
| Mitochondrial long chain fatty acid beta-oxidation | | | | | 3.41E−02 | | | | |
| Pyruvate metabolism/Rodent version | | | | | 2.91E−03 | | | | |
| Neurophysiological process_Netrin-1 in regulation of axon guidance | | | | | 6.90E−04 | | | | |

TABLE 10-continued

List of Enriched GeneGo Pathway Maps in Four Different Breast Epithelial Cell Types

| Pathway maps | p-values in Nulliparous | | | | | p-values in Parous | | | |
|---|---|---|---|---|---|---|---|---|---|
| | CD44+ | CD24+ | CD10+ | Stroma | rat | CD44+ | CD24+ | CD10+ | Stroma |
| Regulation of lipid metabolism_Regulation of lipid metabolism by niacin and isoprenaline | | | | | 2.48E−02 | | | | |
| Stem cells_Scheme: Osteogenic and adipogenic differentiation of mesenchymal stem cells | | | | | 4.11E−02 | | | | |
| Pyruvate metabolism | | | | | 9.11E−03 | | | | |
| Naphthalene metabolism | | | | | 2.50E−02 | | | | |
| Transcription_Role of AP-1 in regulation of cellular metabolism | | | | | 1.26E−02 | | | | |
| 1-Naphthylamine and 1-Nitronaphtalene metabolism | | | | | 6.00E−03 | | | | |
| Muscle contraction_Regulation of eNOS activity in cardiomyocytes | | | | | 4.91E−02 | | | | |
| Retinol metabolism | | | | | 1.95E−02 | | | | |
| Androstenedione and testosterone biosynthesis and metabolism p.2 | | | | | 8.88E−03 | | | | |
| Acetaminophen metabolism | | | | | 3.90E−03 | | | | |
| Propionate metabolism p.2 | | | | | 1.70E−02 | | | | |

Furthermore, Table 10 lists only the pathways determined to be upregulated in CD44+ cells from nulliparous women relative to CD44+ cells from parous women, and Table 12 lists the pathways that were significantly upregulated in CD44+, CD24− breast epithelial cells of parous women relative to the same cell type in nulliparous women.

The most significant pathways highly active in parous samples in all of these three cell types included apoptosis, survival, and immune response, whereas stem cells and development-related pathways were enriched only in CD44+ cells from nulliparous women (FIG. 11) and Table 10, above, and Table 12, below). Pathways highly active in parous stroma were enriched in energy metabolism, fatty acid metabolism and adipocyte differentiation from stem cells, which is consistent with adipose tissue development and a decrease in breast density following pregnancy. Table 13, below shows a summary of GeneGo functional enrichment analysis by protein class for differentially expressed genes in CD44+, CD24+, CD10+ and stromal cell types isolated from nulliparous and parous normal human breast. Table 13 indicates the actual and expected number of network objects in the activated dataset for a given protein class, and the ratio of the actual and expected number. In the Table, "n" is the total number of genes in the list, "R" is the number of genes showing the indicated protein class in the background list, "N" is the total number of genes in the background list, the mean value for hypergeometric distribution is calculated by the formula: (n*R/N), the z-score is calculated using the formula: ((r-mean)/sqrt(variance)), and the p-value represents the probability to have the given value of r or higher (or lower for negative z-score). The functional categories of genes affected by parity were similar in all four cell types with receptors and enzymes representing the most enriched groups (FIG. 12 and Table 13).

TABLE 11

Pathways Upregulated in Nulliparous CD44+ Cells Relative to Parous CD44+ Cells

| Pathway maps | P-value in NP CD44+ |
|---|---|
| Cytoskeleton remodeling_Role of PKA in cytoskeleton reorganisation | 6.44E−07 |
| Development_MAG-dependent inhibition of neurite outgrowth | 1.54E−06 |
| Role of DNA methylation in progression of multiple myeloma | 2.40E−06 |
| Cell adhesion_Histamine H1 receptor signaling in the interruption of cell barrier integrity | 3.24E−06 |
| Stem cells_Response to hypoxia in glioblastoma stem cells | 4.22E−06 |
| Development_WNT signaling pathway. Part 2 | 5.42E−06 |
| Development_Slit-Robo signaling | 6.19E−06 |
| Cytoskeleton remodeling_Fibronectin-binding integrins in cell motility | 8.94E−06 |
| Oxidative phosphorylation | 9.31E−06 |
| Cell adhesion_Role of tetraspanins in the integrin-mediated cell adhesion | 1.02E−05 |
| Cell cycle_Role of Nek in cell cycle regulation | 1.27E−05 |
| Blood coagulation_Blood coagulation | 1.86E−05 |
| Cell adhesion_ECM remodeling | 2.09E−05 |
| Inhibitory action of Lipoxin A4 on PDGF, EGF and LTD4 signaling | 2.45E−05 |
| Stem cells_WNT/Beta-catenin and NOTCH in induction of osteogenesis | 2.48E−05 |
| HIF-1 in gastric cancer | 3.00E−05 |
| Cell adhesion_Plasmin signaling | 3.33E−05 |
| Development_Lipoxin inhibitory action on PDGF, EGF and LTD4 signaling | 3.33E−05 |

TABLE 11-continued

Pathways Upregulated in Nulliparous CD44+ Cells Relative to Parous CD44+ Cells

| Pathway maps | P-value in NP CD44+ |
|---|---|
| Cell adhesion_Integrin-mediated cell adhesion and migration | 3.84E−05 |
| Cytoskeleton remodeling_Reverse signaling by ephrin B | 5.92E−05 |
| Immune response_IL-1 signaling pathway | 7.06E−05 |
| Cell adhesion_Endothelial cell contacts by junctional mechanisms | 7.46E−05 |
| Signal transduction_cAMP signaling | 7.78E−05 |
| Role of stellate cells in progression of pancreatic cancer | 1.16E−04 |
| Stem cells_NOTCH1-induced self-renewal of glioblastoma stem cells | 1.30E−04 |
| Stem cells_Pancreatic cancer stem cells in tumor metastasis | 1.30E−04 |
| Tumor-stroma interactions in pancreatic cancer | 1.44E−04 |
| Stem cells_Regulation of lung epithelial progenitor cell differentiation | 1.66E−04 |
| LKB1 signaling pathway in lung cancer cells | 1.66E−04 |
| Immune response_CCR3 signaling in eosinophils | 1.68E−04 |
| Non-genomic signaling of ESR2 (membrane) in lung cancer cells | 1.76E−04 |
| Blood coagulation_GPCRs in platelet aggregation | 2.20E−04 |
| Cytoskeleton remodeling_Role of PDGFs in cell migration | 2.55E−04 |
| Stem cells_Role of BMP signaling in embryonic stem cell neural differentiation | 2.59E−04 |
| Development_Hedgehog and PTH signaling pathways in bone and cartilage development | 3.07E−04 |
| Stem cells_Hedgehog, BMP and Parathyroid hormone in osteogenesis | 3.25E−04 |
| IGF signaling in HCC | 3.94E−04 |
| Development_EGFR signaling via small GTPases | 4.43E−04 |
| Cell adhesion_Cadherin-mediated cell adhesion | 4.72E−04 |
| Stem cells_Differentiation of white adipocytes | 4.75E−04 |
| Apoptosis and survival_Endoplasmic reticulum stress response pathway | 4.75E−04 |
| Development_BMP signaling | 5.69E−04 |
| Development_TGF-beta-dependent induction of EMT via MAPK | 6.02E−04 |
| PGE2 pathways in cancer | 6.80E−04 |
| Immune response_Antigen presentation by MHC class I | 8.21E−04 |
| Muscle contraction_Regulation of eNOS activity in endothelial cells | 8.47E−04 |
| Development_Melanocyte development and pigmentation | 8.76E−04 |
| Stem cells_Extraembryonic differentiation of embryonic stem cells | 9.09E−04 |
| Stem cells_Astrocyte differentiation from adult stem cells | 9.09E−04 |
| Stem cells_Auditory hair cell differentiation in embryogenesis | 1.06E−03 |
| Effect of *H. pylori* infection on gastric epithelial cells motility | 1.12E−03 |
| Development_S1P3 receptor signaling pathway | 1.12E−03 |
| Development_Role of IL-8 in angiogenesis | 1.12E−03 |
| Immune response_IL-9 signaling pathway | 1.13E−03 |
| Cell adhesion_Gap junctions | 1.35E−03 |
| DNA damage_Brca1 as a transcription regulator | 1.35E−03 |
| Stem cells_Early embryonal hypaxial myogenesis | 1.40E−03 |
| Immune response_Oncostatin M signaling via MAPK in human cells | 1.40E−03 |
| Stem cells_Beta adrenergic receptors in brown adipocyte differentiation | 1.40E−03 |
| ENaC regulation in airways (normal and CF) | 1.48E−03 |
| EGFR family signaling in pancreatic cancer | 1.49E−03 |
| Cell adhesion_Endothelial cell contacts by non-junctional mechanisms | 1.52E−03 |
| Neurophysiological process_Glutamate regulation of Dopamine D1A receptor signaling | 1.62E−03 |
| Neurophysiological process_Receptor-mediated axon growth repulsion | 1.62E−03 |
| Role of cell adhesion molecules in progression of pancreatic cancer | 1.62E−03 |
| Immune response_Fc gamma R-mediated phagocytosis in macrophages | 1.62E−03 |
| Neurophysiological process_ACM regulation of nerve impulse | 1.93E−03 |
| Transcription_Transcription regulation of aminoacid metabolism | 1.98E−03 |
| G-protein signaling_Regulation of p38 and JNK signaling mediated by G-proteins | 2.08E−03 |
| Stem cells_Role of GSK3 beta in cardioprotection against myocardial infarction | 2.12E−03 |
| Development_NOTCH-induced EMT | 2.12E−03 |
| HCV-dependent transcription regulation leading to HCC | 2.12E−03 |
| Development_PDGF signaling via MAPK cascades | 2.29E−03 |
| Transport_Clathrin-coated vesicle cycle | 2.30E−03 |
| Stem cells_Stimulation of differentiation of mouse embryonic fibroblasts into adipocytes by extracellular factors | 2.30E−03 |
| Immune response_MIF in innate immunity response | 2.50E−03 |
| Development_S1P2 and S1P3 receptors in cell proliferation and differentiation | 2.54E−03 |
| Reproduction_GnRH signaling | 2.61E−03 |
| Regulation of lipid metabolism_Stimulation of Arachidonic acid production by ACM receptors | 2.61E−03 |
| Immune response_Oncostatin M signaling via JAK-Stat in human cells | 2.84E−03 |
| Development_WNT signaling pathway. Part 1. Degradation of beta-catenin in the absence WNT signaling | 2.84E−03 |
| Development_VEGF-family signaling | 3.00E−03 |
| Hypoxia-induced EMT in cancer and fibrosis | 3.01E−03 |
| Cell adhesion_Role of CDK5 in cell adhesion | 3.01E−03 |
| Mechanisms of drug resistance in multiple myeloma | 3.17E−03 |
| Activation of TGF-beta signaling in pancreatic cancer | 3.20E−03 |
| Development_NOTCH1-mediated pathway for NF-KB activity modulation | 3.20E−03 |
| Regulation of VEGF signaling in pancreatic cancer | 3.20E−03 |
| Possible pathway of TGF-beta 1-dependent inhibition of CFTR expression | 3.20E−03 |
| Signal transduction_Erk Interactions: Inhibition of Erk | 3.20E−03 |
| Muscle contraction_GPCRs in the regulation of smooth muscle tone | 3.51E−03 |

TABLE 11-continued

Pathways Upregulated in Nulliparous CD44+ Cells Relative to Parous CD44+ Cells

| Pathway maps | P-value in NP CD44+ |
|---|---|
| Stem cells_NOTCH in inhibition of WNT/Beta-catenin-induced osteogenesis | 3.56E-03 |
| Apoptosis and survival_Inhibition of ROS-induced apoptosis by 17beta-estradiol | 3.56E-03 |
| Development_TGF-beta receptor signaling | 3.70E-03 |
| TGF-beta 1-induced transactivation of membrane receptors signaling in HCC | 3.70E-03 |
| Beta-2 adrenergic-dependent CFTR expression | 3.87E-03 |
| Immune response_Oncostatin M signaling via MAPK in mouse cells | 3.88E-03 |
| Role of osteoblasts in bone lesions formation in multiple myeloma | 3.88E-03 |
| Mechanisms of CAM-DR in multiple myeloma | 3.88E-03 |
| Development_TGF-beta-dependent induction of EMT via SMADs | 3.88E-03 |
| Stem cells_WNT and Notch signaling in early cardiac myogenesis | 3.88E-03 |
| Some pathways of EMT in cancer cells | 4.30E-03 |
| Membrane-bound ESR1: interaction with G-proteins signaling | 4.30E-03 |
| Cell adhesion_Tight junctions | 4.66E-03 |
| Cytoskeleton remodeling_Keratin filaments | 4.66E-03 |
| IGF-1 signaling in pancreatic cancer | 4.66E-03 |
| Stem cells_Dopamine-induced expression of CNTF in adult neurogenesis | 4.79E-03 |
| Cell cycle_Role of 14-3-3 proteins in cell cycle regulation | 4.79E-03 |
| Development_Thrombopoetin signaling via JAK-STAT pathway | 4.79E-03 |
| Immune response_IL-17 signaling pathways | 4.82E-03 |
| Suppression of TGF-beta signaling in pancreatic cancer | 4.93E-03 |
| G-protein signaling_G-Protein alpha-12 signaling pathway | 5.57E-03 |
| G-protein signaling_Regulation of cAMP levels by ACM | 5.78E-03 |
| Cell adhesion_Ephrin signaling | 5.78E-03 |
| G-protein signaling_Cross-talk between Ras-family GTPases | 6.08E-03 |
| Proteolysis_Putative ubiquitin pathway | 6.08E-03 |
| Stem cells_Aberrant Wnt signaling in medulloblastoma stem cells | 6.08E-03 |
| Putative role of Estrogen receptor and Androgen receptor signaling in progression of lung cancer | 6.56E-03 |
| ERBB family and HGF signaling in gastric cancer | 6.56E-03 |
| Stem cells_Noncanonical WNT signaling in cardiac myogenesis | 6.59E-03 |
| G-protein signaling_Rap2A regulation pathway | 7.03E-03 |
| Transport_Macropinocytosis regulation by growth factors | 7.05E-03 |
| Development_EGFR signaling pathway | 7.05E-03 |
| Dual role of TGF-beta 1 in HCC | 7.59E-03 |
| Immune response_IFN alpha/beta signaling pathway | 7.59E-03 |
| Development_Glucocorticoid receptor signaling | 7.59E-03 |
| Cell adhesion_PLAU signaling | 7.76E-03 |
| Transcription_P53 signaling pathway | 7.76E-03 |
| Stem cells_BMP7 in brown adipocyte differentiation | 7.76E-03 |
| Development_Beta-adrenergic receptors regulation of ERK | 7.77E-03 |
| Role and regulation of Prostaglandin E2 in gastric cancer | 7.77E-03 |
| Development_Leptin signaling via PI3K-dependent pathway | 7.77E-03 |
| Transport_Alpha-2 adrenergic receptor regulation of ion channels | 7.77E-03 |
| Influence of bone marrow cell environment on progression of multiple myeloma | 7.77E-03 |
| Immune response_CD40 signaling | 7.95E-03 |
| Muscle contraction_ACM regulation of smooth muscle contraction | 8.52E-03 |
| Stem cells_H3K4 demethylases in stem cell maintenance | 8.73E-03 |
| Development_PDGF signaling via STATs and NF-kB | 8.73E-03 |
| Transition of HCC cells to invasive and migratory phenotype | 9.07E-03 |
| WNT signaling in HCC | 9.07E-03 |
| Development_Neurotrophin family signaling | 9.07E-03 |
| Ubiquinone metabolism | 9.10E-03 |
| Immune response_Oncostatin M signaling via JAK-Stat in mouse cells | 9.13E-03 |
| Androgen signaling in HCC | 9.13E-03 |
| Development_Leptin signaling via JAK/STAT and MAPK cascades | 9.37E-03 |
| Transport_RAB1A regulation pathway | 9.84E-03 |
| Cytoskeleton remodeling_Integrin outside-in signaling | 1.02E-02 |
| Role of metalloproteases and heparanase in progression of pancreatic cancer | 1.04E-02 |
| Cytoskeleton remodeling_Thyroliberin in Cytoskeleton remodeling | 1.04E-02 |
| Transport_ACM3 in salivary glands | 1.06E-02 |
| Transport_Intracellular cholesterol transport in norm | 1.10E-02 |
| Muscle contraction_Delta-type opioid receptor in smooth muscle contraction | 1.14E-02 |
| G-protein signaling_Ras family GTPases in kinase cascades (scheme) | 1.14E-02 |
| Development_Alpha-1 adrenergic receptors signaling via cAMP | 1.16E-02 |
| HCV-mediated liver damage and predisposition to HCC progression via p53 | 1.16E-02 |
| wtCFTR and delta508 traffic/Clathrin coated vesicles formation (norm and CF) | 1.16E-02 |
| Immune response_Histamine signaling in dendritic cells | 1.17E-02 |
| Development_GM-CSF signaling | 1.17E-02 |
| Development_A2B receptor: action via G-protein alpha s | 1.17E-02 |
| Angiogenesis in HCC | 1.17E-02 |
| Pro-inflammatory action of Gastrin in gastric cancer | 1.17E-02 |
| Oxidative stress_Role of ASK1 under oxidative stress | 1.22E-02 |
| Stem cells_BMP signaling in cardiac myogenesis | 1.22E-02 |
| Transcription_Role of VDR in regulation of genes involved in osteoporosis | 1.23E-02 |
| Stem cells_TNF-alpha, IL-1 alpha and WNT5A-dependent regulation of osteogenesis and adipogenesis in mesenchymal stem cells | 1.33E-02 |

TABLE 11-continued

Pathways Upregulated in Nulliparous CD44+ Cells Relative to Parous CD44+ Cells

| Pathway maps | P-value in NP CD44+ |
|---|---|
| Mitochondrial ketone bodies biosynthesis and metabolism | 1.38E−02 |
| Regulation of beta-adrenergic receptors signaling in pancreatic cancer | 1.40E−02 |
| Development_Notch Signaling Pathway | 1.40E−02 |
| Development_A2A receptor signaling | 1.40E−02 |
| Development_VEGF signaling and activation | 1.40E−02 |
| Apoptosis and survival_Anti-apoptotic action of Gastrin | 1.40E−02 |
| Neurophysiological process_Melatonin signaling | 1.40E−02 |
| Neurophysiological process_EphB receptors in dendritic spine morphogenesis and synaptogenesis | 1.43E−02 |
| Cytoskeleton remodeling_Role of Activin A in cytoskeleton remodeling | 1.46E−02 |
| Stem cells_H3K36 demethylation in stem cell maintenance | 1.46E−02 |
| Effect of *H. pylori* infection on inflammation in gastric epithelial cells | 1.54E−02 |
| Development_S1P1 signaling pathway | 1.60E−02 |
| Development_Ligand-independent activation of ESR1 and ESR2 | 1.60E−02 |
| CFTR-dependent regulation of ion channels in Airway Epithelium (norm and CF) | 1.60E−02 |
| Mechanisms of resistance to EGFR inhibitors in lung cancer | 1.60E−02 |
| Development_Regulation of CDK5 in CNS | 1.64E−02 |
| HGF signaling in pancreatic cancer | 1.64E−02 |
| E-cadherin signaling and its regulation in gastric cancer | 1.67E−02 |
| HBV signaling via protein kinases leading to HCC | 1.67E−02 |
| Development_Endothelin-1/EDNRA signaling | 1.69E−02 |
| Development_VEGF signaling via VEGFR2 - generic cascades | 1.82E−02 |
| Immune response_IL-13 signaling via JAK-STAT | 1.82E−02 |
| Signal transduction_Calcium signaling | 1.82E−02 |
| Cytoskeleton remodeling_ACM3 and ACM4 in keratinocyte migration | 1.92E−02 |
| Cholesterol and Sphingolipids transport/Distribution to the intracellular membrane compartments (normal and CF) | 1.94E−02 |
| Stem cells_Notch signaling in medulloblastoma stem cells | 1.94E−02 |
| Proteolysis_Putative SUMO-1 pathway | 1.94E−02 |
| Transcription_Role of heterochromatin protein 1 (HP1) family in transcriptional silencing | 2.18E−02 |
| Immune response_MIF-mediated glucocorticoid regulation | 2.18E−02 |
| Cell adhesion_Cell-matrix glycoconjugates | 2.21E−02 |
| Cytoskeleton remodeling_RalA regulation pathway | 2.28E−02 |
| Muscle contraction_S1P2 receptor-mediated smooth muscle contraction | 2.28E−02 |
| EGFR signaling pathway in Lung Cancer | 2.33E−02 |
| Influence of smoking on activation of EGFR signaling in lung cancer cells | 2.33E−02 |
| Development_HGF signaling pathway | 2.33E−02 |
| Cardiac Hypertrophy_NF-AT signaling in Cardiac Hypertrophy | 2.33E−02 |
| Immune response_TLR signaling pathways | 2.36E−02 |
| Chemotaxis_Leukocyte chemotaxis | 2.47E−02 |
| Cytokine production by Th17 cells in CF | 2.52E−02 |
| Development_PACAP signaling in neural cells | 2.52E−02 |
| Translation_Regulation of EIF2 activity | 2.52E−02 |
| Cytoskeleton remodeling_FAK signaling | 2.62E−02 |
| Inhibition of apoptosis in pancreatic cancer | 2.62E−02 |
| Stem cells_Neovascularization of glioblastoma in response to hypoxia | 2.65E−02 |
| Stem cells_Embryonal epaxial myogenesis | 2.65E−02 |
| Inflammatory mechanisms of pancreatic cancerogenesis | 2.82E−02 |
| Sorafenib-induced inhibition of cell proliferation and angiogenesis in HCC | 2.84E−02 |
| IL-1 beta-dependent CFTR expression | 2.84E−02 |
| Development_Role of Activin A in cell differentiation and proliferation | 2.87E−02 |
| Stem cells_H3K27 demethylases in differentiation of stem cells | 2.87E−02 |
| Reproduction_Progesterone-mediated oocyte maturation | 2.87E−02 |
| Stem cells_Regulation of endothelial progenitor cell differentiation from adult stem cells | 2.90E−02 |
| Bacterial infections in CF airways | 2.90E−02 |
| Cytokine production by Th17 cells in CF (Mouse model) | 2.93E−02 |
| Development_PEDF signaling | 2.93E−02 |
| Immune response_Bacterial infections in normal airways | 2.93E−02 |
| Stem cells_Cooperation between Hedgehog, IGF-2 and HGF signaling pathways in medulloblastoma stem cells | 3.06E−02 |
| Immune response_Immunological synapse formation | 3.20E−02 |
| Stem cells_Muscle progenitor cell migration in hypaxial myogenesis | 3.24E−02 |
| Apoptosis and survival_Lymphotoxin-beta receptor signaling | 3.24E−02 |
| Immune response_Gastrin in inflammatory response | 3.38E−02 |
| Transcription_Transcription factor Tubby signaling pathways | 3.50E−02 |
| Stem cells_EGF-induced proliferation of Type C cells in SVZ of adult brain | 3.51E−02 |
| Normal and pathological TGF-beta-mediated regulation of cell proliferation | 3.51E−02 |
| Mucin expression in CF via TLRs, EGFR signaling pathways | 3.63E−02 |
| Immune response_Neurotensin-induced activation of IL-8 in colonocytes | 3.64E−02 |
| Signal transduction_JNK pathway | 3.64E−02 |
| Cytoskeleton remodeling_Neurofilaments | 3.66E−02 |
| Development_Thyroliberin signaling | 3.87E−02 |
| Transcription_PPAR Pathway | 3.87E−02 |
| Stem cells_Role of PKR1 and ILK in cardiac progenitor cells | 4.00E−02 |
| Apoptosis and survival_Role of CDK5 in neuronal death and survival | 4.00E−02 |
| Development_CNTF receptor signaling | 4.00E−02 |

TABLE 11-continued

Pathways Upregulated in Nulliparous CD44+ Cells Relative to Parous CD44+ Cells

| Pathway maps | P-value in NP CD44+ |
|---|---|
| wtCFTR and deltaF508 traffic/Membrane expression (norm and CF) | 4.00E−02 |
| Chemotaxis_CXCR4 signaling pathway | 4.00E−02 |
| Neurophysiological process_Dopamine D2 receptor transactivation of PDGFR in CNS | 4.26E−02 |
| Immune response_Signaling pathway mediated by IL-6 and IL-1 | 4.91E−02 |
| Development_FGF2-dependent induction of EMT | 4.46E−04 |
| Transcription_ChREBP regulation pathway | 6.25E−04 |
| Regulation of lipid metabolism_Insulin regulation of glycogen metabolism | 2.76E−03 |
| Transport_Macropinocytosis | 9.84E−03 |
| Regulation of CFTR activity (norm and CF) | 7.82E−05 |
| Cell adhesion_Chemokines and adhesion | 2.69E−07 |
| Development_TGF-beta-dependent induction of EMT via RhoA, PI3K and ILK. | 1.13E−04 |
| K-RAS signaling in lung cancer | 6.72E−03 |
| Cell adhesion_Alpha-4 integrins in cell migration and adhesion | 3.71E−06 |
| Cytoskeleton remodeling_Cytoskeleton remodeling | 1.05E−09 |
| Muscle contraction_Relaxin signaling pathway | 8.94E−03 |
| Apoptosis and survival_BAD phosphorylation | 9.18E−04 |
| IL-6 signaling in multiple myeloma | 8.76E−04 |
| Apoptosis and survival_Apoptotic TNF-family pathways | 9.18E−04 |
| Immune response_IL-2 activation and signaling pathway | 3.17E−03 |
| Dual role of BMP signaling in gastric cancer | 3.50E−04 |
| Cytoskeleton remodeling_Regulation of actin cytoskeleton by Rho GTPases | 1.34E−09 |
| Cell cycle_Initiation of mitosis | 9.37E−03 |
| Transcription_CREB pathway | 1.35E−03 |
| Signal transduction_PKA signaling | 1.64E−05 |
| Stem cells_Endothelial differentiation during embryonic development | 3.25E−04 |
| Cytoskeleton remodeling_TGF, WNT and cytoskeletal remodeling | 1.88E−09 |
| HBV-dependent NF-kB and PI3K/AKT pathways leading to HCC | 8.76E−04 |
| Translation_Regulation of translation initiation | 6.27E−04 |
| Cell cycle_Influence of Ras and Rho proteins on G1/S Transition | 1.18E−04 |
| Apoptosis and survival_Granzyme A signaling | 1.35E−03 |

TABLE 12

Pathways Upregulated in Parous CD44+ Cells Relative to Nulliparous CD44+ Cells

| Pathway maps | P-val in P CD44+ |
|---|---|
| TTP metabolism | 0.0000608 |
| Resistance of pancreatic cancer cells to death receptor signaling | 1.29E−04 |
| Transcription_Assembly of RNA Polymerase II preinitiation complex on TATA-less promoters | 0.000136 |
| Development_PIP3 signaling in cardiac myocytes | 3.38E−04 |
| HCV-dependent regulation of RNA polymerases leading to HCC | 0.00035 |
| Stem cells_H3K9 demethylases in pluripotency maintenance of stem cells | 4.62E−04 |
| Inhibition of apoptosis in gastric cancer | 6.32E−04 |
| Cell cycle_Start of DNA replication in early S phase | 0.00067 |
| Apoptosis and survival_Caspase cascade | 0.000816 |
| Immune response_BCR pathway | 9.79E−04 |
| Immune response_ICOS pathway in T-helper cell | 1.40E−03 |
| Cell cycle_The metaphase checkpoint | 0.00141 |
| Inhibitory action of Lipoxins on neutrophil migration | 1.46E−03 |
| Cytoskeleton remodeling_Alpha-1A adrenergic receptor-dependent inhibition of PI3K | 1.67E−03 |
| DNA damage_NHEJ mechanisms of DSBs repair | 1.67E−03 |
| Regulation of metabolism_Triiodothyronine and Thyroxine signaling | 0.00186 |
| Cell cycle_Chromosome condensation in prometaphase | 2.70E−03 |
| Development_IGF-1 receptor signaling | 2.77E−03 |
| dCTP/dUTP metabolism | 0.003 |
| dGTP metabolism | 0.00332 |
| Inhibition of RUNX3 signaling in gastric cancer | 0.00336 |
| Apoptosis and survival_Beta-2 adrenergic receptor anti-apoptotic action | 0.00412 |
| Signal transduction_Activin A signaling regulation | 4.38E−03 |
| Stem cells_Fetal brown fat cell differentiation | 0.00447 |
| Immune response_CXCR4 signaling via second messenger | 5.11E−03 |
| dATP/dITP metabolism | 0.00573 |
| Signal transduction_PTEN pathway | 5.97E−03 |
| Microsatellite instability in gastric cancer | 0.00601 |
| Inhibition of TGF-beta signaling in gastric cancer | 6.01E−03 |
| Immune response_Regulation of T cell function by CTLA-4 | 6.82E−03 |
| DNA damage_DNA-damage-induced responses | 0.00747 |
| Stem cells_Self-renewal of adult neural stem cells | 0.00756 |
| Regulation of degradation of deltaF508 CFTR in CF | 8.44E−03 |
| Transcription_Sin3 and NuRD in transcription regulation | 0.00892 |

TABLE 12-continued

Pathways Upregulated in Parous CD44+ Cells Relative to Nulliparous CD44+ Cells

| Pathway maps | P-val in P CD44+ |
|---|---|
| Blood coagulation_GPIb-IX-V-dependent platelet activation | 0.00952 |
| Transcription_Receptor-mediated HIF regulation | 1.01E−02 |
| Stem cells_Signaling pathways in embryonic hepatocyte maturation | 1.05E−02 |
| Apoptosis and survival_nAChR in apoptosis inhibition and cell cycle progression | 1.15E−02 |
| Apoptosis and survival_Anti-apoptotic TNFs/NF-kB/Bcl-2 pathway | 1.29E−02 |
| DNA damage_Role of Brca1 and Brca2 in DNA repair | 0.0133 |
| Translation_IL-2 regulation of translation | 0.0139 |
| DNA damage_Inhibition of telomerase activity and cellular senescence | 0.0139 |
| DNA damage_Mismatch repair | 0.0139 |
| Neurophysiological process_Olfactory transduction | 0.0139 |
| Immune response_CD28 signaling | 1.42E−02 |
| Immune response_Role of DAP12 receptors in NK cells | 0.0142 |
| Immune response_PIP3 signaling in B lymphocytes | 0.0144 |
| Immune response_ETV3 affect on CSF1-promoted macrophage differentiation | 0.0152 |
| Blood coagulation_GPVI-dependent platelet activation | 0.0157 |
| Inhibition of tumor suppressive pathways in pancreatic cancer | 1.65E−02 |
| Transcription_Ligand-Dependent Transcription of Retinoid-Target genes | 0.0196 |
| Role of alpha-6/beta-4 integrins in carcinoma progression | 0.0199 |
| Development_Thrombopoietin-regulated cell processes | 1.99E−02 |
| Chemotaxis_Lipoxin inhibitory action on fMLP-induced neutrophil chemotaxis | 2.20E−02 |
| Development_EGFR signaling via PIP3 | 0.0226 |
| G-protein signaling_S1P2 receptor signaling | 0.0248 |
| Stem cells_Differentiation of natural regulatory T cells | 0.0248 |
| Translation_Opioid receptors in regulation of translation | 2.61E−02 |
| Transport_RAB3 regulation pathway | 0.0271 |
| G-protein signaling_RAC1 in cellular process | 0.0277 |
| DNA damage_Nucleotide excision repair | 0.0277 |
| Immune response_Inhibitory action of lipoxins on superoxide production induced by IL-8 and Leukotriene B4 in neutrophils | 2.91E−02 |
| Inhibitory action of Lipoxins on Superoxide production in neutrophils | 2.91E−02 |
| wtCFTR and delta508-CFTR traffic/Generic schema (norm and CF) | 0.0317 |
| Apoptosis and survival_DNA-damage-induced apoptosis | 0.0327 |
| Apoptosis and survival_NGF signaling pathway | 0.0341 |
| Apoptosis and survival_APRIL and BAFF signaling | 3.42E−02 |
| Immune response_NFAT in immune response | 0.0346 |
| Apoptosis and survival_Anti-apoptotic TNFs/NF-kB/IAP pathway | 3.85E−02 |
| Immune response_TCR and CD28 co-stimulation in activation of NF-kB | 0.0414 |
| Immune response_Innate immune response to RNA viral infection | 4.33E−02 |
| Immune response_IFN gamma signaling pathway | 0.044 |
| Immune response_CD16 signaling in NK cells | 0.0472 |
| Immune response_Delta-type opioid receptor signaling in T-cells | 4.84E−02 |
| Apoptosis and survival_p53-dependent apoptosis | 0.0484 |
| Stem cells_Role of growth factors in the maintenance of embryonic stem cell pluripotency | 0.0129 |
| Chemoresistance pathways mediated by constitutive activation of PI3K pathway and BCL-2 in small cell lung cancer | 2.20E−05 |
| Signal transduction_AKT signaling | 2.74E−05 |
| Immune response_Inhibitory action of Lipoxins on pro-inflammatory TNF-alpha signaling | 4.18E−05 |
| Apoptosis and survival_Cytoplasmic/mitochondrial transport of proapoptotic proteins Bid, Bmf and Bim | 1.61E−04 |
| Translation_Regulation of EIF4F activity | 1.81E−04 |
| PI3K signaling in gastric cancer | 6.36E−04 |
| Chemotaxis_Inhibitory action of lipoxins on IL-8- and Leukotriene B4-induced neutrophil migration | 6.36E−04 |
| Translation_Insulin regulation of translation | 7.48E−04 |
| Transcription_Role of Akt in hypoxia induced HIF1 activation | 1.49E−03 |
| Apoptosis and survival_Ceramides signaling pathway | 1.96E−03 |
| Apoptosis and survival_Role of IAP-proteins in apoptosis | 3.16E−03 |
| Proteolysis_Role of Parkin in the Ubiquitin-Proteasomal Pathway | 5.01E−03 |
| Anti-apoptotic action of Gastrin in pancreatic cancer | 5.92E−03 |

TABLE 13

GeneGo Functional Enrichment Analysis by Protein Class for Differentially Expressed Genes in CD44+, CD24+, CS10+ and Stromal Breast Epithelial Cell Types

| Protein class | Actual | n | R | N | Expected | Ratio | p-value | z-score |
|---|---|---|---|---|---|---|---|---|
| Protein class enriched in nulliparous CD44+ cells | | | | | | | | |
| phosphatases | 33 | 2078 | 230 | 22651 | 21.1 | 1.564 | 6.690E−03 | 2.732 |
| ligands | 67 | 2078 | 507 | 22651 | 46.51 | 1.44 | 1.524E−03 | 3.188 |
| kinases | 71 | 2078 | 650 | 22651 | 59.63 | 1.191 | 6.960E−02 | 1.567 |
| transcription | 101 | 2078 | 951 | 22651 | 87.24 | 1.158 | 6.627E−02 | 1.579 |

TABLE 13-continued

GeneGo Functional Enrichment Analysis by Protein Class for Differentially
Expressed Genes in CD44+, CD24+, CS10+ and Stromal Breast Epithelial Cell Types

| Protein class | Actual | n | R | N | Expected | Ratio | p-value | z-score |
|---|---|---|---|---|---|---|---|---|
| factors | | | | | | | | |
| enzymes | 286 | 2078 | 2693 | 22651 | 247.1 | 1.158 | 3.576E−03 | 2.77 |
| proteases | 57 | 2078 | 552 | 22651 | 50.64 | 1.126 | 1.896E−01 | 0.9493 |
| receptors | 97 | 2078 | 1492 | 22651 | 136.9 | 0.7087 | 6.932E−05 | −3.7 |
| other | 1374 | 2078 | 15628 | 22651 | 1434 | 0.9584 | 1.705E−03 | −2.972 |
| Protein class enriched in nulliparous CD10+ cells | | | | | | | | |
| proteases | 59 | 1491 | 552 | 22651 | 36.34 | 1.624 | 1.665E−04 | 3.938 |
| ligands | 53 | 1491 | 507 | 22651 | 33.37 | 1.588 | 5.912E−04 | 3.555 |
| enzymes | 218 | 1491 | 2693 | 22651 | 177.3 | 1.23 | 5.826E−04 | 3.372 |
| transcription | 68 | 1491 | 951 | 22651 | 62.6 | 1.086 | 2.531E−01 | 0.7215 |
| factors | | | | | | | | |
| phosphatases | 16 | 1491 | 230 | 22651 | 15.14 | 1.057 | 4.467E−01 | 0.2299 |
| kinases | 43 | 1491 | 650 | 22651 | 42.79 | 1.005 | 5.096E−01 | 0.03431 |
| receptors | 96 | 1491 | 1492 | 22651 | 98.21 | 0.9775 | 4.319E−01 | −0.2388 |
| other | 946 | 1491 | 15628 | 22651 | 1029 | 0.9196 | 1.294E−06 | −4.792 |
| Protein class enriched in nulliparous CD24+ cells | | | | | | | | |
| phosphatases | 23 | 1273 | 230 | 22651 | 12.93 | 1.779 | 5.428E−03 | 2.899 |
| enzymes | 213 | 1273 | 2693 | 22651 | 151.3 | 1.407 | 9.672E−08 | 5.495 |
| kinases | 45 | 1273 | 650 | 22651 | 36.53 | 1.232 | 8.715E−02 | 1.464 |
| transcription | 51 | 1273 | 951 | 22651 | 53.45 | 0.9542 | 3.967E−01 | −0.352 |
| factors | | | | | | | | |
| ligands | 25 | 1273 | 507 | 22651 | 28.49 | 0.8774 | 2.859E−01 | −0.6814 |
| proteases | 27 | 1273 | 552 | 22651 | 31.02 | 0.8703 | 2.598E−01 | −0.7526 |
| receptors | 46 | 1273 | 1492 | 22651 | 83.85 | 0.5486 | 1.417E−06 | −4.402 |
| other | 844 | 1273 | 15628 | 22651 | 878.3 | 0.9609 | 1.799E−02 | −2.14 |
| Protein class enriched in nulliparous stromal cells | | | | | | | | |
| ligands | 35 | 770 | 507 | 22651 | 17.24 | 2.031 | 6.543E−05 | 4.403 |
| proteases | 38 | 770 | 552 | 22651 | 18.76 | 2.025 | 3.424E−05 | 4.574 |
| kinases | 36 | 770 | 650 | 22651 | 22.1 | 1.629 | 2.994E−03 | 3.054 |
| transcription | 49 | 770 | 951 | 22651 | 32.33 | 1.516 | 2.625E−03 | 3.048 |
| factors | | | | | | | | |
| phosphatases | 11 | 770 | 230 | 22651 | 7.819 | 1.407 | 1.619E−01 | 1.163 |
| receptors | 53 | 770 | 1492 | 22651 | 50.72 | 1.045 | 3.891E−01 | 0.3371 |
| enzymes | 69 | 770 | 2693 | 22651 | 91.55 | 0.7537 | 4.980E−03 | −2.554 |
| other | 482 | 770 | 15628 | 22651 | 531.3 | 0.9073 | 7.001E−05 | −3.905 |
| Protein class enriched in parous CD44+ cells | | | | | | | | |
| phosphatases | 24 | 1820 | 230 | 22651 | 18.48 | 1.299 | 1.130E−01 | 1.346 |
| enzymes | 280 | 1820 | 2693 | 22651 | 216.4 | 1.294 | 1.994E−06 | 4.804 |
| kinases | 67 | 1820 | 650 | 22651 | 52.23 | 1.283 | 2.106E−02 | 2.163 |
| transcription | 88 | 1820 | 951 | 22651 | 76.41 | 1.152 | 9.018E−02 | 1.412 |
| factors | | | | | | | | |
| proteases | 39 | 1820 | 552 | 22651 | 44.35 | 0.8793 | 2.234E−01 | −0.8485 |
| ligands | 35 | 1820 | 507 | 22651 | 40.74 | 0.8592 | 1.949E−01 | −0.948 |
| receptors | 76 | 1820 | 1492 | 22651 | 119.9 | 0.634 | 3.035E−06 | −4.324 |
| other | 1215 | 1820 | 15628 | 22651 | 1256 | 0.9676 | 1.720E−02 | −2.151 |
| Protein class enriched in parous CD10+ cells | | | | | | | | |
| enzymes | 241 | 1721 | 2693 | 22651 | 204.6 | 1.178 | 3.179E−03 | 2.819 |
| kinases | 58 | 1721 | 650 | 22651 | 49.39 | 1.174 | 1.131E−01 | 1.294 |
| ligands | 41 | 1721 | 507 | 22651 | 38.52 | 1.064 | 3.611E−01 | 0.4202 |
| phosphatases | 17 | 1721 | 230 | 22651 | 17.48 | 0.9728 | 5.164E−01 | −0.1189 |
| transcription | 65 | 1721 | 951 | 22651 | 72.26 | 0.8996 | 2.004E−01 | −0.9072 |
| factors | | | | | | | | |
| proteases | 33 | 1721 | 552 | 22651 | 41.94 | 0.7868 | 8.152E−02 | −1.454 |
| receptors | 78 | 1721 | 1492 | 22651 | 113.4 | 0.6881 | 1.122E−04 | −3.575 |
| other | 1193 | 1721 | 15628 | 22651 | 1187 | 1.005 | 3.921E−01 | 0.3036 |
| Protein class enriched in parous CD24+ cells | | | | | | | | |
| phosphatases | 16 | 1173 | 230 | 22651 | 11.91 | 1.343 | 1.422E−01 | 1.223 |
| kinases | 42 | 1173 | 650 | 22651 | 33.66 | 1.248 | 8.280E−02 | 1.498 |
| enzymes | 170 | 1173 | 2693 | 22651 | 139.5 | 1.219 | 3.280E−03 | 2.829 |
| transcription | 58 | 1173 | 951 | 22651 | 49.25 | 1.178 | 1.104E−01 | 1.308 |
| factors | | | | | | | | |
| ligands | 28 | 1173 | 507 | 22651 | 26.26 | 1.066 | 3.900E−01 | 0.3536 |
| proteases | 28 | 1173 | 552 | 22651 | 28.59 | 0.9795 | 5.044E−01 | −0.1139 |
| receptors | 54 | 1173 | 1492 | 22651 | 77.26 | 0.6989 | 2.041E−03 | −2.812 |
| other | 780 | 1173 | 15628 | 22651 | 809.3 | 0.9638 | 3.152E−02 | −1.9 |
| Protein class enriched in parous stromal cells | | | | | | | | |
| enzymes | 228 | 950 | 2693 | 22651 | 112.9 | 2.019 | 1.785E−26 | 11.78 |
| kinases | 35 | 950 | 650 | 22651 | 27.26 | 1.284 | 7.908E−02 | 1.536 |

TABLE 13-continued

GeneGo Functional Enrichment Analysis by Protein Class for Differentially
Expressed Genes in CD44+, CD24+, CS10+ and Stromal Breast Epithelial Cell Types

| Protein class | Actual | n | R | N | Expected | Ratio | p-value | z-score |
|---|---|---|---|---|---|---|---|---|
| phosphatases | 9 | 950 | 230 | 22651 | 9.646 | 0.933 | 5.007E−01 | −0.2137 |
| ligands | 12 | 950 | 507 | 22651 | 21.26 | 0.5643 | 1.865E−02 | −2.076 |
| proteases | 13 | 950 | 552 | 22651 | 23.15 | 0.5615 | 1.370E−02 | −2.182 |
| transcription factors | 22 | 950 | 951 | 22651 | 39.89 | 0.5516 | 1.014E−03 | −2.956 |
| receptors | 29 | 950 | 1492 | 22651 | 62.58 | 0.4634 | 5.878E−07 | −4.487 |
| other | 603 | 950 | 15628 | 22651 | 655.5 | 0.92 | 1.188E−04 | −3.759 |
| Protein class enrichment for promoter hypermethylation in nulliparous CD44+ cells | | | | | | | | |
| kinases | 37 | 838 | 650 | 22651 | 24.05 | 1.539 | 6.593E−03 | 2.731 |
| transcription factors | 54 | 838 | 951 | 22651 | 35.18 | 1.535 | 1.240E−03 | 3.303 |
| enzymes | 134 | 838 | 2693 | 22651 | 99.63 | 1.345 | 1.970E−04 | 3.738 |
| proteases | 25 | 838 | 552 | 22651 | 20.42 | 1.224 | 1.745E−01 | 1.045 |
| ligands | 20 | 838 | 507 | 22651 | 18.76 | 1.066 | 4.165E−01 | 0.2958 |
| phosphatases | 9 | 838 | 230 | 22651 | 8.509 | 1.058 | 4.798E−01 | 0.1724 |
| receptors | 40 | 838 | 1492 | 22651 | 55.2 | 0.7247 | 1.541E−02 | −2.157 |
| other | 523 | 838 | 15628 | 22651 | 578.2 | 0.9046 | 2.087E−05 | −4.199 |
| Protein class enrichment for promoter hypermethylation in nulliparous CD44+ cells | | | | | | | | |
| transcription factors | 32 | 290 | 951 | 22651 | 12.18 | 2.628 | 6.665E−07 | 5.842 |
| ligands | 10 | 290 | 507 | 22651 | 6.491 | 1.541 | 1.180E−01 | 1.402 |
| proteases | 9 | 290 | 552 | 22651 | 7.067 | 1.273 | 2.774E−01 | 0.7408 |
| kinases | 10 | 290 | 650 | 22651 | 8.322 | 1.202 | 3.222E−01 | 0.594 |
| enzymes | 39 | 290 | 2693 | 22651 | 34.48 | 1.131 | 2.282E−01 | 0.8256 |
| receptors | 20 | 290 | 1492 | 22651 | 19.1 | 1.047 | 4.490E−01 | 0.2139 |
| phosphatases | 2 | 290 | 230 | 22651 | 2.945 | 0.6792 | 4.332E−01 | −0.5569 |
| other | 170 | 290 | 15628 | 22651 | 200.1 | 0.8496 | 1.099E−04 | −3.844 |
| Protein class enrichment for genebody hypermethylation in nulliparous CD44+ cells | | | | | | | | |
| transcription factors | 31 | 249 | 951 | 22651 | 10.45 | 2.965 | 6.726E−08 | 6.528 |
| phosphatases | 4 | 249 | 230 | 22651 | 2.528 | 1.582 | 2.474E−01 | 0.9354 |
| receptors | 18 | 249 | 1492 | 22651 | 16.4 | 1.097 | 3.762E−01 | 0.4107 |
| ligands | 6 | 249 | 507 | 22651 | 5.573 | 1.077 | 4.852E−01 | 0.1838 |
| kinases | 6 | 249 | 650 | 22651 | 7.145 | 0.8397 | 4.249E−01 | −0.4372 |
| enzymes | 21 | 249 | 2693 | 22651 | 29.6 | 0.7094 | 5.047E−02 | −1.694 |
| proteases | 4 | 249 | 552 | 22651 | 6.068 | 0.6592 | 2.712E−01 | −0.8547 |
| other | 160 | 249 | 15628 | 22651 | 171.8 | 0.9313 | 6.111E−02 | −1.625 |
| Protein class enrichment for genebody hypermethylation in parous CD44+ cells | | | | | | | | |
| transcription factors | 20 | 170 | 951 | 22651 | 7.137 | 2.802 | 3.207E−05 | 4.937 |
| phosphatases | 4 | 170 | 230 | 22651 | 1.726 | 2.317 | 9.542E−02 | 1.746 |
| kinases | 11 | 170 | 650 | 22651 | 4.878 | 2.255 | 1.018E−02 | 2.823 |
| proteases | 5 | 170 | 552 | 22651 | 4.143 | 1.207 | 3.995E−01 | 0.4279 |
| enzymes | 21 | 170 | 2693 | 22651 | 20.21 | 1.039 | 4.608E−01 | 0.1876 |
| receptors | 9 | 170 | 1492 | 22651 | 11.2 | 0.8037 | 3.107E−01 | −0.6821 |
| ligands | 3 | 170 | 507 | 22651 | 3.805 | 0.7884 | 4.700E−01 | −0.419 |
| other | 97 | 170 | 15628 | 22651 | 117.3 | 0.827 | 6.559E−04 | −3.377 |

The analysis was further focused on CD44+ cells, which showed the most pronounced differences between parous and nulliparous states. Pathways highly active in nulliparous samples are related to major developmental and tumorigenic pathways including cytoskeleton remodeling, chemokines and cell adhesion, and WNT signaling (FIG. 13 and Table 10), whereas pathways more active in parous samples include PI3K/AKT signaling and apoptosis (FIG. 14 and Table 10). Importantly, the highest scored pathway for genes highly expressed in nulliparous samples is four orders of magnitude more statistically significant than those for the genes highly expressed in parous samples, suggesting that downregulation of protumorigenic developmental pathways is a prominent feature of CD44+ cells from parous women. Interactome analysis also demonstrated a much larger number of overconnected proteins in nulliparous than in parous state in all four cell types, but particularly in CD44+ cells (FIG. 12). As the relative number of interactions (connectivity) is directly related to the functional activity of the dataset [Nikolsky, Y., et al. (2008) Cancer Res 68, 9532-9540], this result suggested that parous cells are overall substantially less active than nulliparous ones.

Because pregnancy-induced protection against breast cancer is also observed in rodents, it was investigated whether pathways altered by parity are conserved across species. Pathways in CD44+ cells were compared to that generated based on genes differentially expressed between virgin and parous rats [Blakely et al., 2006, supra; D'Cruz, C. M., and Chodosh, L. A. (2006) Cancer Res 66, 6421-6431]. Significant overlap was found between pathways highly active in nulliparous and virgin samples (thus, downregulated in parous), but almost nothing in common was found among those highly active in parous tissues. The top ranked pathways were all related to cytoskeleton remodeling and cell adhesion, known to be highly relevant in stem cells (FIG. 15A and FIG. 15B). Thus, pregnancy appears to induce similar alterations in the mammary epithelium regardless of species. A network built of the common pathways included a complete NOTCH pathway (including NOTCH1 (GenBank Accession no., AB209873, AF308602, AL592301, BC013208), NOTCH1-NICD, ADAM17 (GenBank Accession no., BM725368, BQ186514), gamma secretase complex (PSENEN, GenBank Accession no., AF220053, BQ222622), APH1A (GenBank Accession Nos. BC020590, BI760743, DC365601), and APH1B (GenBank Accession Nos. AC016207, AI693802)), IGF1 (GenBank Accession Nos. AB209184, AC010202), EGF (GenBank Accession No. AC004050, AC005509), CD44 (GenBank Accession No. BC004372), CD9 (GenBank Accession Nos. AI003581, BG291377), and ITGB1 (GenBank Accession Nos. AI261443, BM973433, BX537407) as "triggers" (ligands and receptors), c-Src (GenBank Accession Nos. AF272982, BC051270), PKC (GenBank Accession No. NM_212535), and FAK (GenBank Accession Nos. AB209083, AK304356) as major signaling kinases, and c-Jun (GenBank Accession Nos. BC002646, BC009874), p53 (GenBank Accession No. AK223026, DA453049), SNAIL1 (GenBank Accession Nos. BC012910, DA972913), and LEF1 (GenBank Accession Nos. AC097067, AC118062) as transcription factors.

Example 4: Cell Type-Specific Epigenetic Patterns Related to Parity and their Functional Relevance This example demonstrates that parity has a more pronounced long-term effect on DNA methylation than on H3 lysine 27 trimethylation (K27) patterns.

Reduction of breast cancer risk in postmenopausal women conferred by full-term pregnancy in early adulthood implies the induction of long-lasting changes such as alterations in cell type-specific epigenetic patterns. To investigate this hypothesis, the comprehensive DNA methylation and K27 profiles of CD24+ and CD44+ cells from nulliparous and parous women were analyzed using MSDKseq applied to high-throughput sequencing and ChIPseq, respectively. The data are summarized in Tables 14-17, below.

Figure 16:
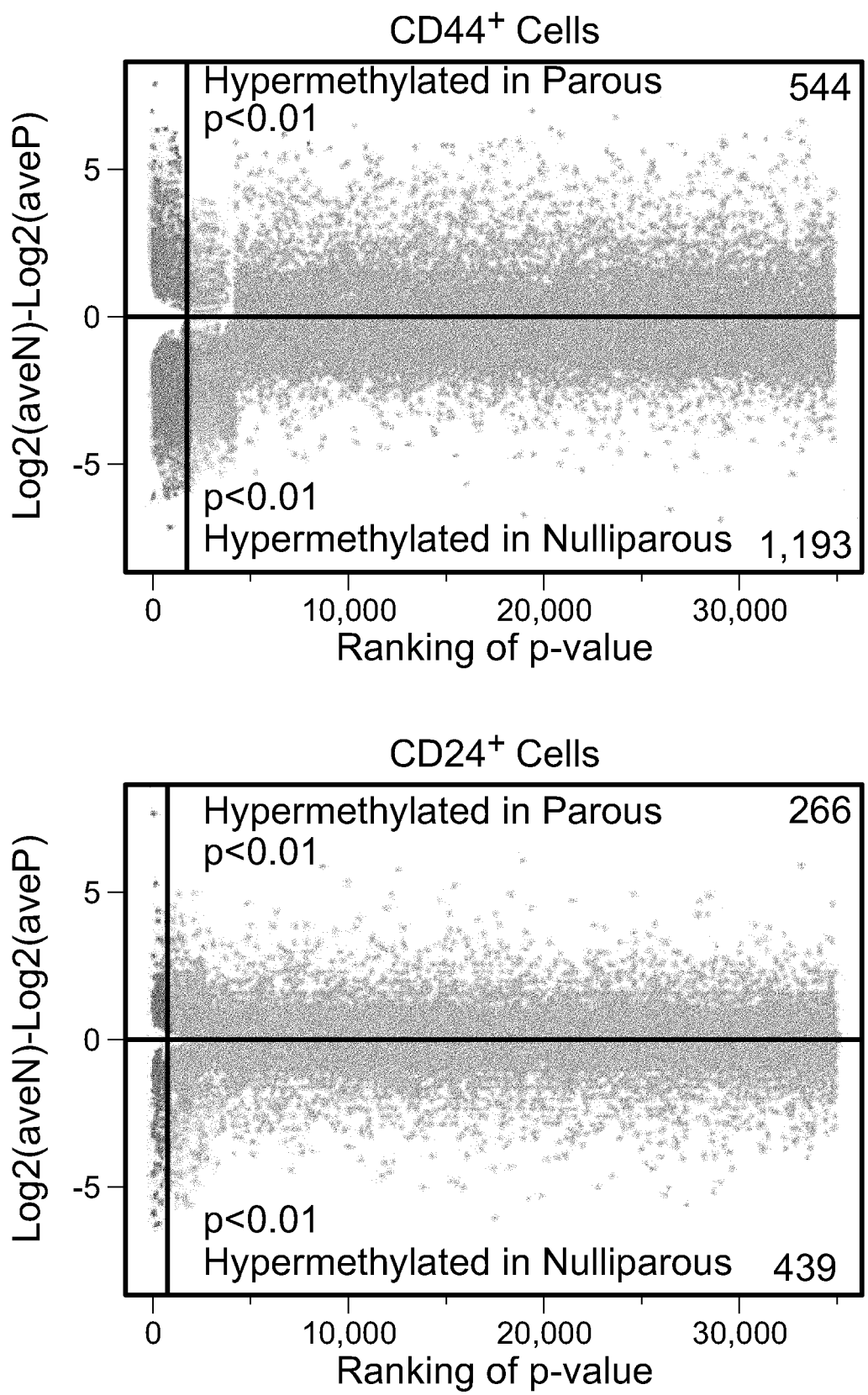
FIG. 16 contains dot plots showing a genome-wide view of differentially methylated genes in CD44+ (upper panel) and CD24+ (lower panel) cells between nulliparous and parous samples. All MSDK sites are plotted on the x-axis in the order of p-values of the difference between nulliparous and parous samples in CD44+ or CD24+ cells. Log ratios of averaged MSDK counts in three N and three P samples are plotted on the y-axis. Vertical lines indicate p=0.01 and the numbers of significant DMRs (p<0.01) are shown in the upper and lower right corners of the plots.

Comparison of MSDKseq libraries of nulliparous and parous samples within each cell type showed a higher number of significantly (p<0.05) differentially methylated regions (DMRs) in CD44+ cells and, in both cell types, more DMRs were hypermethylated in nulliparous than in parous cells (FIG. 16 and Table 14, below).

To validate differences in DNA methylation in additional samples and by other methods, quantitative methylation-specific PCR (qMSP) analyses of selected genes were performed using CD44+ cells from multiple nulliparous and parous cases. Despite some interpersonal variability, statistically significant differences were detected between nulliparous and parous groups that overall correlated with MSDKseq data (FIG. 6).

In Table 14, genes with DMR (hypermethylated in parous or nulliparous samples) in promoter region or genebody in CD44+ cells are listed. DMR pattern (hypermethylated in which sample in which region), gene symbol, RefSeq ID, gene description, chromosomal location, log 10 p-value (calculated by Poisson margin model), log ratio of averaged nulliparous and parous MSDK-tag counts, scaled MSDK-tag counts, chromosomal position of BssHII recognition sites, and distance between BssHII sites and TSS (plus and minus indicate downstream and upstream of TSS, respectively) are shown. The log 10 p-value and log ratio have a positive or negative sign which indicates DMR is hypermethylated in parous or nulliparous, respectively.

Global associations between differential gene expression and presence of DMRs were analyzed in CD44+ and CD24+ cells, but significant associations were not found, potentially due to the complex relationship between DNA methylation and transcript levels, as DNA methylation can both positively (e.g., in gene body) and negatively (e.g., in promoters) regulate gene expression, depending on the location relative to transcription start site.

The data from the analyses are summarized in Table 15 and Table 16, below, which list genes that are differentially methylated between nulliparous and parous CD44+ and CD24+ cells, respectively, along with SAGEseq, ChIPseq and MSDKseq data for the listed genes. Significant differences in genes enriched for H3K27mc3 mark were not detected in CD44+ or CD24+ cells from nulliparous and parous samples. However, genes highly expressed in CD44+ or CD24+ cells from nulliparous women were not K27-enriched in either parous or nulliparous cases, implying the potential lack of their regulation by the PRC2 complex that establishes this histone mark (see, Tables 15 and 16).

Overall it appears that parity may have a more pronounced long-term effect on DNA methylation than on K27 patterns.

Figure 17:
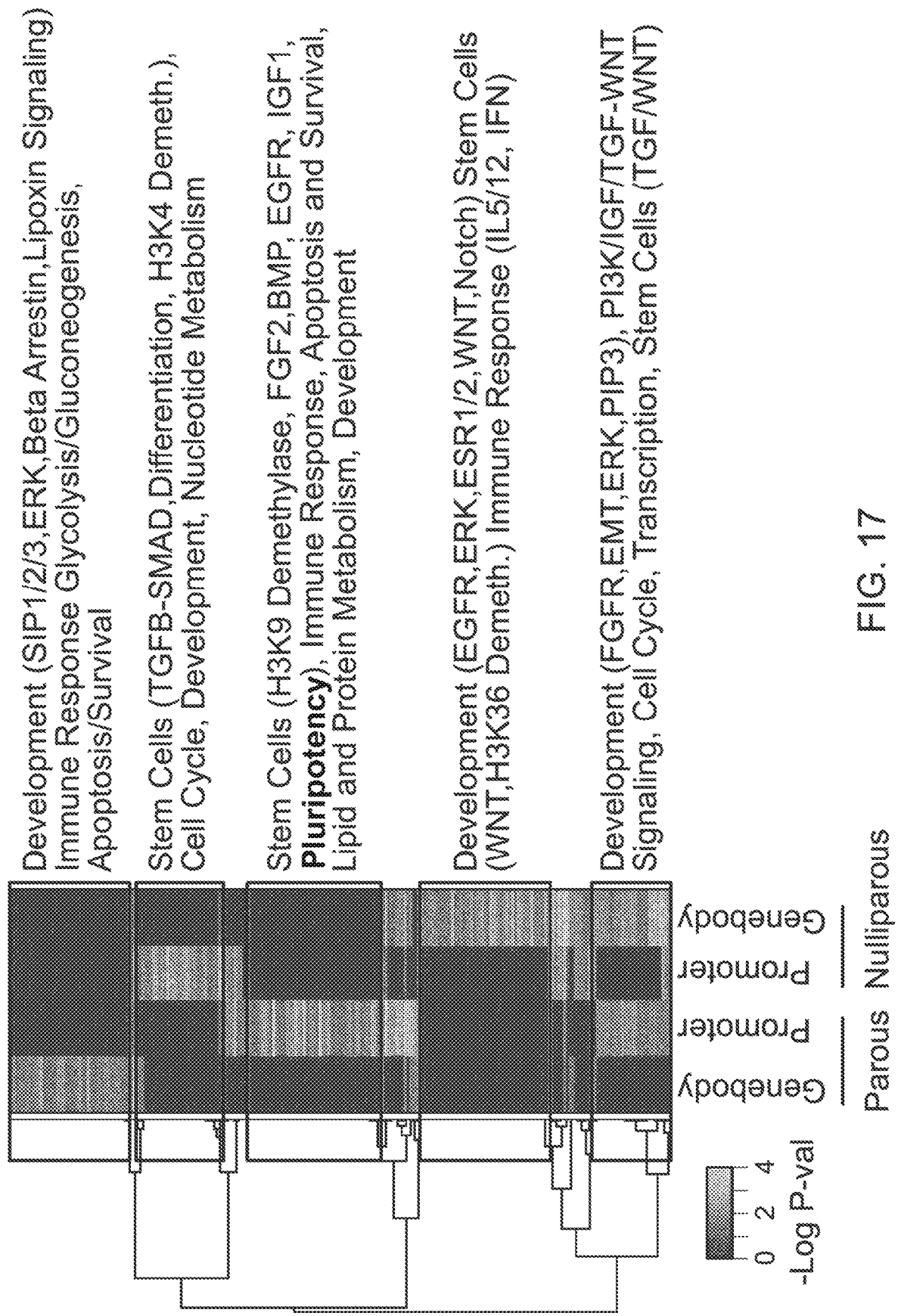
FIG. 17 is a heat map showing the pathways enriched by genes associated with gene body or promoter DMRs in CD44+ cells from nulliparous and parous samples.

To investigate pathways affected by parity-related epigenetic alterations, pathways enriched by genes associated with gene body or promoter DMRs were analyzed in CD44+ cells from nulliparous and parous samples. Very little overlap was found among the four distinct categories (FIG. 17). Relatively few pathways were significantly enriched in both expression and methylation data and most of these were related to development, TGFβ and WNT signaling.

The fraction of transcription factors (TFs) among differentially methylated genes was 2-3 fold higher than expected and what was observed among differentially expressed genes, implying that promoter methylation might be a preferred control mechanism of their expression. Similar to the expression data, DMRs in nulliparous samples had higher numbers of overconnected objects than in parous ones. Gene body DMRs in CD44+ nulliparous cells had the highest number of overconnected objects and transcription factors represented a significant fraction of overconnected objects in promoter hypermethylated DMRs in CD44+ nulliparous cells. Further, Table 17 lists enriched GeneGo pathway maps for differentially methylated regions (DMRs) in promoter (−5 to 2 kb) and gene body (+2 kb to end) in CD44+ cells from human breast epithelium. The table contains canonical pathway maps with p-values (<0.05) indicating significance of enrichment for differentially methylated genes (hypo/hyper methylated) in CD44+ progenitor-enriched cells from nulliparous or parous cases.

TABLE 14

Comprehensive DNA Methylation and K27 Profiles of CD44+ Nulliparous and Parous Breast Epithelial Cells

| Methylation | Location | Symbol | Accession | Official Full Name | Chromosome | log10 pval. |
|---|---|---|---|---|---|---|
| parous | promoter | HECTD1 | NM_015382 | HECT domain containing 1 | 14q12 | 4.2 |
| parous | promoter | CDX2 | NM_001265 | caudal type homeobox 2 | 13q12.2 | -4.3 |
| parous | promoter | CDX2 | NM_001265 | caudal type homeobox 2 | 13q12.2 | 5.6 |
| parous | promoter | CLMN | NM_024734 | calmin (calponin-like, transmembrane) | 14q32.2 | 16.9 |
| parous | promoter | C13orf18 | NM_025113 | chromosome 13 open reading frame 18 | 13q14.11 | 19.5 |
| parous | promoter | PCDHGB1 | NM_032095 | protocadherin gamma subfamily B, 1 | 5q31 | 9.6 |
| parous | promoter | UBE2Q2 | NM_173469 | ubiquitin-conjugating enzyme E2Q family member 2 | 15q24.2 | 4.7 |
| parous | promoter | MMP23B | NM_006983 | matrix metallopeptidase 23B | 1p36.3 | 4 |
| parous | promoter | PCDHGB5 | NM_032099 | protocadherin gamma subfamily B, 5 | 5q31 | 38 |
| parous | promoter | UBAC1 | NM_016172 | UBA domain containing 1 | 9q34.3 | 3.5 |
| parous | promoter | NKX2-6 | NM_001136271 | NK2 transcription factor related, locus 6 (Drosophila) | 8p21.2 | 128.4 |
| parous | promoter | GABRB2 | NM_021911 | gamma-aminobutyric acid (GABA) A receptor, beta 2 | 5q34 | 3.7 |
| parous | promoter | SLC30A3 | NM_003459 | solute carrier family 30 (zinc transporter), member 3 | 2p23.3 | 2.7 |
| parous | promoter | MGC3771 | NR_024167 | NA | NA | 3.5 |
| parous | promoter | SMG6 | NM_017575 | Smg-6 homolog, nonsense mediated mRNA decay factor (C. elegans) | 17p13.3 | 92.9 |
| parous | promoter | SMG6 | NM_017575 | Smg-6 homolog, nonsense mediated mRNA decay factor (C. elegans) | 17p13.3 | 92.9 |
| parous | promoter | EHD1 | NM_006795 | EH-domain containing 1 | 11q13 | 3.1 |
| parous | promoter | ZNF146 | NM_007145 | zinc finger protein 146 | 19q13.1 | 8.6 |
| parous | promoter | C11orf35 | NM_173573 | chromosome 11 open reading frame 35 | 11 | 2.3 |
| parous | promoter | CCDC96 | NM_153376 | coiled-coil domain containing 96 | 4p16.1 | 3.8 |
| parous | promoter | ADAMTS9 | NM_182920 | ADAM metallopeptidase with thrombospondin type 1 motif, 9 | 3p14.1 | 3.4 |
| parous | promoter | DHRS3 | NM_004753 | dehydrogenase/reductase (SDR family) member 3 | 1p36.1 | 2.7 |
| parous | promoter | DGCR6 | NM_005675 | DiGeorge syndrome critical region gene 6 | 22q11.21 | 17.8 |
| parous | promoter | LOC113230 | NR_024282 | NA | NA | 2.1 |
| parous | promoter | DLEU2 | NR_002612 | deleted in lymphocytic leukemia 2 (non-protein coding) | 13q14 | 10.3 |
| parous | promoter | DMTF1 | NM_021145 | cyclin D binding myb-like transcription factor 1 | 7q21 | 11.1 |
| parous | promoter | IRX3 | NM_024336 | iroquois homeobox 3 | 16q12.2 | 7.7 |
| parous | promoter | IREB2 | NM_004136 | iron-responsive element binding protein 2 | 15 | 11.3 |
| parous | promoter | CBLC | NM_001130852 | Cas-Br-M (murine) ecotropic retroviral transforming sequence c | 19q13.2 | 2.5 |
| parous | promoter | ZNF444 | NM_018337 | zinc finger protein 444 | 19q13.43 | 24.7 |
| parous | promoter | STK11 | NM_000455 | serine/threonine kinase 11 | 19p13.3 | 16.6 |
| parous | promoter | NF1 | NM_000267 | neurofibromin 1 | 17q11.2 | 24.8 |
| parous | promoter | SIRPA | NM_001040022 | signal-regulatory protein alpha | 20p13 | 96 |
| parous | promoter | FAM76B | NM_144664 | family with sequence similarity 76, member B | 11q21 | 23.5 |
| parous | promoter | ALOXE3 | NM_021628 | arachidonate lipoxygenase 3 | 17p13.1 | 214.5 |
| parous | promoter | COG1 | NM_018714 | component of oligomeric golgi complex 1 | 17q25.1 | 2.5 |
| parous | promoter | BCAT2 | NM_001190 | branched chain aminotransferase 2, mitochondrial | 19 | 36.9 |
| parous | promoter | EVX2 | NM_001080458 | even-skipped homeobox 2 | 2q31.1 | 13.6 |
| parous | promoter | WDR21C | NM_152418 | NA | NA | 29.2 |
| parous | promoter | PMS2 | NM_000535 | PMS2 postmeiotic segregation increased 2 (S. cerevisiae) | 7p22.1 | 2.6 |
| parous | promoter | LOC285548 | NR_015450 | NA | NA | 2.4 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | promoter | NKX6-2 | NM_177400 | NK6 homeobox 2 | 10q26.3 | 13.3 |
| parous | promoter | PDE8A | NM_002605 | phosphodiesterase 8A | 15q25.3 | 27.2 |
| parous | promoter | ADRA1A | NM_033303 | adrenergic, alpha-1A-, receptor | 8p21.2 | 3.6 |
| parous | promoter | ADRA1A | NM_033303 | adrenergic, alpha-1A-, receptor | 8p21.2 | 2 |
| parous | promoter | SYNCRIP | NM_006372 | synaptotagmin binding, cytoplasmic RNA interacting protein | 6q14-q15 | 10.2 |
| parous | promoter | KCTD11 | NM_001002914 | potassium channel tetramerisation domain containing 11 | 17p13.2 | 110.4 |
| parous | promoter | C19orf57 | NM_024323 | chromosome 19 open reading frame 57 | 19p13.12 | 2.6 |
| parous | promoter | LRP4 | NM_002334 | low density lipoprotein receptor-related protein 4 | 11p11.2 | 2.1 |
| parous | promoter | HERV-FRD | NM_207582 | NA | NA | 2.6 |
| parous | promoter | AKT1 | NM_005163 | v-akt murine thymoma viral oncogene homolog 1 | 14q32.32-q32.33 | 16.9 |
| parous | promoter | ZNF175 | NM_007147 | zinc finger protein 175 | 19q13.4 | 17.9 |
| parous | promoter | ROBO3 | NM_022370 | roundabout, axon guidance receptor, homolog 3 (Drosophila) | 11q24 | 2.5 |
| parous | promoter | GM2A | NM_000405 | GM2 ganglioside activator | 5 | 4.5 |
| parous | promoter | FA2H | NM_024306 | fatty acid 2-hydroxylase | 16q23 | 107.5 |
| parous | promoter | SYT6 | NM_205848 | synaptotagmin VI | 1p13.1 | 16.4 |
| parous | promoter | HBP1 | NM_012257 | HMG-box transcription factor 1 | 7q22-q31 | 2.4 |
| parous | promoter | CEP76 | NM_024899 | centrosomal protein 76 kDa | 18p11.21 | 2.3 |
| parous | promoter | CSMD1 | NM_033225 | CUB and Sushi multiple domains 1 | 8p23.2 | 18.1 |
| parous | promoter | RAB43 | NM_198490 | RAB43, member RAS oncogene family | 3q21.3 | 16.2 |
| parous | promoter | YEATS4 | NM_006530 | YEATS domain containing 4 | 12q13-q15 | 3.3 |
| parous | promoter | FST | NM_013409 | follistatin | 5q11.2 | 16.3 |
| parous | promoter | ZNF565 | NM_001042474 | zinc finger protein 565 | 19 | 8.6 |
| parous | promoter | CSRP2 | NM_001321 | cysteine and glycine-rich protein 2 | 12q21.1 | 4 |
| parous | promoter | LOC653319 | NM_001040715 | NA | NA | 25.5 |
| parous | promoter | MAL | NM_022439 | mal, T-cell differentiation protein | 2q11.1 | 19 |
| parous | promoter | HHIP | NM_022475 | hedgehog interacting protein | 4q31.21-q31.3 | 6.8 |
| parous | promoter | SNX3 | NM_003795 | sorting nexin 3 | 6q21 | -2.9 |
| parous | promoter | SNX3 | NM_003795 | sorting nexin 3 | 6q21 | 5.9 |
| parous | promoter | MMP15 | NM_002428 | matrix metallopeptidase 15 (membrane-inserted) | 16q13 | 2.8 |
| parous | promoter | ACSL1 | NM_001995 | acyl-CoA synthetase long-chain family member 1 | 4q35 | 3.4 |
| parous | promoter | MMP23A | NR_002946 | matrix metallopeptidase 23A (pseudogene) | 1p36.3 | 4 |
| parous | promoter | VPS11 | NM_021729 | vacuolar protein sorting 11 homolog (S. cerevisiae) | 11q23 | 3.1 |
| parous | promoter | ANO1 | NM_018043 | anoctamin 1, calcium activated chloride channel | 11q13.2 | 7.9 |
| parous | promoter | RASSF7 | NM_003475 | Ras association (RalGDS/AF-6) domain family (N-terminal) member 7 | 11p15.5 | 2.3 |
| parous | promoter | FMN2 | NM_020066 | formin 2 | 1q43 | 6.8 |
| parous | promoter | PDGFC | NM_016205 | platelet derived growth factor C | 4q32 | 12.9 |
| parous | promoter | CC2D1A | NM_017721 | coiled-coil and C2 domain containing 1A | 19p13.12 | 2.6 |
| parous | promoter | KREMEN2 | NM_024507 | kringle containing transmembrane protein 2 | 16p13.11 | 20.3 |
| parous | promoter | KLHDC5 | NM_020782 | kelch domain containing 5 | 12p11.22 | 3.7 |
| parous | promoter | CHKA | NM_001277 | choline kinase alpha | 11q13.1 | 7.2 |
| parous | promoter | CHKB | NM_152253 | choline kinase beta | 22q13.33 | 14.5 |
| parous | promoter | PPM1G | NM_177983 | protein phosphatase 1G (formerly 2C), magnesium-dependent, gamma isoform | 2p23.3 | 3.7 |
| parous | promoter | CYGB | NM_134268 | cytoglobin | 17q25 | 10.4 |
| parous | promoter | CHCHD6 | NM_032343 | coiled-coil-helix-coiled-coil-helix domain containing 6 | 3q21.3 | 2.6 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | promoter | ABCF2 | NM_005692 | ATP-binding cassette, sub-family F (GCN20), member 2 | 7q35-q36 | 5.8 |
| parous | promoter | USP45 | NM_001080481 | ubiquitin specific peptidase 45 | 6q16.2 | 4.1 |
| parous | promoter | SCO | NM_005063 | stearoyl-CoA desaturase (delta-9-desaturase) | 10q23-q24 | 41.1 |
| parous | promoter | TADA2B | NM_152293 | NA | NA | 3.8 |
| parous | promoter | JUN | NM_002228 | jun oncogene | 1p32-p31 | 2.1 |
| parous | promoter | TRPA1 | NM_007332 | transient receptor potential cation channel, subfamily A, member 1 | 8q13 | 37 |
| parous | promoter | UNC5B | NM_170744 | unc-5 homolog B (*C. elegans*) | 10q22.2 | -3.3 |
| parous | promoter | UNC5B | NM_170744 | unc-5 homolog B (*C. elegans*) | 10q22.2 | 15.6 |
| parous | promoter | NPC1 | NM_000271 | Niemann-Pick disease, type C1 | 18q11-q12 | 64.8 |
| parous | promoter | DGCR6L | NM_033257 | DiGeorge syndrome critical region | 22q11 | 8.6 |
| parous | promoter | CDC42BPA | NM_003607 | CDC42 binding protein kinase alpha (DMPK-like) | 1q42.11 | 20 |
| parous | promoter | PSMG2 | NM_020232 | proteasome (prosome, macropain) assembly chaperone 2 | 18p11.21 | 2.3 |
| parous | promoter | VSX2 | NM_182894 | visual system homeobox 2 | 14q24.3 | 2.8 |
| parous | promoter | VSX2 | NM_182894 | visual system homeobox 2 | 14q24.3 | 95.3 |
| parous | promoter | CRMP1 | NM_001313 | collapsin response mediator protein 1 | 4p16.1 | 4.1 |
| parous | promoter | SNX30 | NM_001012994 | sorting nexin family member 30 | 9q33.1 | 6.3 |
| parous | promoter | OSMR | NM_003999 | oncostatin M receptor | 5p13.2 | 25.3 |
| parous | promoter | TRPM2 | NM_003307 | transient receptor potential cation channel, subfamily M, member 2 | 21q22.3 | 7.2 |
| parous | promoter | GPR137 | NM_020155 | G protein-coupled receptor 137 | 11cen-q22.3 | 7.9 |
| parous | promoter | HOXB8 | NM_024016 | homeobox B8 | 17q21.32 | 32.8 |
| parous | promoter | PRKCB | NM_212535 | protein kinase C, beta | 16p12 | 9.3 |
| parous | promoter | GRP | NM_002091 | gastrin-releasing peptide | 18q21.1-q21.32 | 13.5 |
| parous | promoter | HOXB2 | NM_002145 | homeobox B2 | 17q21.32 | 14 |
| parous | promoter | FIBCD1 | NM_032843 | fibrinogen C domain containing 1 | 9q34.2 | -2.1 |
| parous | promoter | FIBCD1 | NM_032843 | fibrinogen C domain containing 1 | 9q34.2 | 19.8 |
| parous | promoter | TUBB3 | NM_006086 | tubulin, beta 3 | 16q24.3 | 28.9 |
| parous | promoter | TMEM95 | NM_198154 | transmembrane protein 95 | 17p13.1 | 110.4 |
| parous | promoter | RIMKLA | NM_173642 | ribosomal modification protein rimK-like family member A | 1p34.2 | 5.8 |
| parous | promoter | HIST1H2BF | NM_003522 | histone cluster 1, H2bf | 6p22.1 | 3.2 |
| parous | promoter | PCDHGA9 | NM_032089 | protocadherin gamma subfamily A, 9 | 5q31 | 38 |
| parous | promoter | PCDHGA9 | NM_032089 | protocadherin gamma subfamily A, 9 | 5q31 | -3.5 |
| parous | promoter | DDN | NM_015086 | dendrin | 12q13 | 3.9 |
| parous | promoter | PAPD5 | NM_001040284 | PAP associated domain containing 5 | 16q12.1 | 3 |
| parous | promoter | BRF2 | NM_018310 | BRF2, subunit of RNA polymerase III transcription initiation factor BRF1-like | 8p11.23 | 2.5 |
| parous | promoter | AMN1 | NM_001113402 | antagonist of mitotic exit network 1 homolog (*S. cerevisiae*) | 12p11.21 | 11.7 |
| parous | promoter | HOXB5 | NM_002147 | homeobox B5 | 17q21.32 | -2.9 |
| parous | promoter | HOXB5 | NM_002147 | homeobox B5 | 17q21.32 | 13.8 |
| parous | promoter | FGF2 | NM_002006 | fibroblast growth factor 2 (basic) | 4q26 | 2.7 |
| parous | promoter | BCAR3 | NM_003567 | breast cancer anti-estrogen resistance 3 | 1p22.1 | 2.1 |
| parous | promoter | CDC5L | NM_001253 | CDC5 cell division cycle 5-like (*S. pombe*) | 6p | 3.8 |
| parous | promoter | ZBTB42 | NM_001137601 | zinc finger and BTB domain containing 42 | 14q32.33 | 16.9 |
| parous | promoter | ETV5 | NM_004454 | ets variant 5 | 3q28 | 2.1 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | promoter | SEMA5B | NM_001031702 | sema domain, seven thrombospondin repeats (type 1 and type 1-like), transmembrane domain (TM) and short cytoplasmic domain, (semaphorin) 5B | 3q21.1 | 35.9 |
| parous | promoter | RNASEH2C | NM_032193 | ribonuclease H2, subunit C | 11q13.1 | 8.8 |
| parous | promoter | DSCR6 | NM_018962 | Down syndrome critical region gene 6 | 21q22.2 | 12 |
| parous | promoter | RAN | NM_006325 | RAN, member RAS oncogene family | 12 | 254.2 |
| parous | promoter | ELOVL2 | NM_017770 | elongation of very long chain fatty acids (FEN1/Elo2, SUR4/Elo3, yeast)-like 2 | 6p24.1 | 6.9 |
| parous | promoter | ELOVL3 | NM_152310 | elongation of very long chain fatty acids (FEN1/Elo2, SUR4/Elo3, yeast)-like 3 | 10q24 | 14.4 |
| parous | promoter | SERBP1 | NM_001018067 | SERPINE1 mRNA binding protein 1 | 1p31 | 205.7 |
| parous | promoter | EFCAB1 | NM_024593 | EF-hand calcium binding domain 1 | 8q11.21 | 3.5 |
| parous | promoter | ISLR2 | NM_001130136 | immunoglobulin superfamily containing leucine-rich repeat 2 | 15q24.1 | 3.9 |
| parous | promoter | ISLR2 | NM_001130136 | immunoglobulin superfamily containing leucine-rich repeat 2 | 15q24.1 | -2.4 |
| parous | promoter | TRIM7 | NM_203297 | tripartite motif-containing 7 | 5q35.3 | 4.7 |
| parous | promoter | HES7 | NM_032580 | hairy and enhancer of split 7 (Drosophila) | 17p13.1 | 214.5 |
| parous | promoter | LOC440396 | NR_002943 | NA | NA | 92.9 |
| parous | promoter | VBP1 | NM_003372 | von Hippel-Lindau binding protein 1 | Xq28 | 3.9 |
| parous | promoter | CHAD | NM_001267 | chondroadherin | 17q21.33 | 9.2 |
| parous | promoter | CAP2B | NM_004930 | capping protein (actin filament) muscle Z-line, beta | 1p36.1 | 7.4 |
| parous | promoter | CTDP1 | NM_004715 | CTD (carboxy-terminal domain, RNA polymerase II, polypeptide A) phosphatase, subunit 1 | 18q23 | 3.5 |
| parous | promoter | KIAA0586 | NM_014749 | KIAA0586 | 14q23.1 | 6.4 |
| parous | promoter | FBXO2 | NM_012168 | F-box protein 2 | 1p36.21 | 28.8 |
| parous | promoter | DMRT3 | NM_021240 | doublesex and mab-3 related transcription factor 3 | 9p24.3 | 113.6 |
| parous | promoter | ADAMTS15 | NM_139055 | ADAM metallopeptidase with thrombospondin type 1 motif, 15 | 11q25 | 34.7 |
| parous | promoter | IFI27L1 | NM_145249 | interferon, alpha-inducible protein 27-like 1 | 14q32.13 | 4.2 |
| parous | promoter | TBX4 | NM_018488 | T-box4 | 17q21-q22 | 5.1 |
| parous | promoter | COX7A1 | NM_001864 | cytochrome c oxidase subunit VIIa polypeptide 1 (muscle) | 19q13.1 | 3.1 |
| parous | promoter | FAM62C | NM_031913 | NA | NA | -2.5 |
| parous | promoter | FAM62C | NM_031913 | NA | NA | 44.8 |
| parous | promoter | PION | NM_017439 | pigeon homolog (Drosophila) | 7q11.23 | 15.4 |
| parous | promoter | GPR143 | NM_000273 | G protein-coupled receptor 143 | Xp22.3 | 46.4 |
| parous | promoter | CPXM2 | NM_198148 | carboxypeptidase X (M14 family), member 2 | 10q26 | 20.5 |
| parous | promoter | TPM2 | NM_213674 | tropomyosin 2 (beta) | 9p13 | 3.1 |
| parous | promoter | TPM1 | NM_001018006 | tropomyosin 1 (alpha) | 15q22.1 | 103.6 |
| parous | promoter | IQCH | NM_001031715 | IQ motif containing H | 15q23 | 4.8 |
| parous | promoter | PCDHGA4 | NM_032053 | protocadherin gamma subfamily A, 4 | 5q31 | 9.6 |
| parous | promoter | ACLY | NM_001096 | ATP citrate lyase | 17q21.2 | 3.2 |
| parous | promoter | OSBPL10 | NM_017784 | oxysterol binding protein-like 10 | 3p23 | 3.4 |
| parous | promoter | AP3D1 | NM_001077523 | adaptor-related protein complex 3, delta 1 subunit | 19p13.3 | 5.9 |
| parous | promoter | MORF4L2 | NM_012286 | mortality factor 4 like 2 | Xq22 | 6.8 |
| parous | promoter | FBXO44 | NM_183412 | F-box protein 44 | 1p36.21 | 28.8 |
| parous | promoter | BEND4 | NM_207406 | BEN domain containing 4 | 4p13 | 4.8 |
| parous | promoter | CGB8 | NM_033183 | chorionic gonadotropin, beta polypeptide 8 | 19q13.32 | 3 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | promoter | LRFN5 | leucine rich repeat and fibronectin type III domain containing 5 | NM_152447 | 14q21.1 | 5.7 |
| parous | promoter | EFNA4 | ephrin-A4 | NM_182690 | 1q21-q22 | 50.5 |
| parous | promoter | PAQR4 | progestin and adipoQ receptor family member IV | NM_152341 | 16p13 | 20.3 |
| parous | promoter | SRM | spermidine synthase | NM_003132 | 1p36-p22 | 3.4 |
| parous | promoter | SRR | serine racemase | NM_021947 | 17p13 | 92.9 |
| parous | promoter | SALL4 | sal-like 4 (*Drosophila*) | NM_020436 | 20q13.2 | 5.7 |
| parous | promoter | HOXB7 | homeobox B7 | NM_004502 | 17q21.32 | 43 |
| parous | promoter | FLJ11506 | NA | NM_024666 | NA | 4.8 |
| parous | promoter | MERTK | c-mer proto-oncogene tyrosine kinase | NM_006343 | 2q14.1 | −10 |
| parous | promoter | MERTK | c-mer proto-oncogene tyrosine kinase | NM_006343 | 2q14.1 | 6.2 |
| parous | promoter | GP5 | glycoprotein V (platelet) | NM_004488 | 3q29 | 7.5 |
| parous | promoter | HAP1 | huntingtin-associated protein 1 | NM_001079871 | 17q21.2-q21.3 | 54.3 |
| parous | promoter | LEF1 | lymphoid enhancer-binding factor 1 | NM_001130713 | 4q23-q25 | 2.8 |
| parous | promoter | ADM | adrenomedullin | NM_001124 | 11 | 2.3 |
| parous | promoter | OLIG2 | oligodendrocyte lineage transcription factor 2 | NM_005806 | 21q22.11 | 2.6 |
| parous | promoter | CSGLCA-T | NA | NM_019015 | NA | 5.8 |
| parous | promoter | VSX1 | visual system homeobox 1 | NM_014588 | 20p11.21 | −4.8 |
| parous | promoter | VSX1 | visual system homeobox 1 | NM_014588 | 20p11.21 | 3.2 |
| parous | promoter | TRAFD1 | TRAF-type zinc finger domain containing 1 | NM_006700 | 12q | 36.8 |
| parous | promoter | SCARF2 | scavenger receptor class F, member 2 | NM_153334 | 22q11.21 | 10.1 |
| parous | promoter | B3GALNT1 | beta-1,3-N-acetylgalactosaminyl transferase 1 (globoside blood group) | NM_033168 | 3q25 | 3 |
| parous | promoter | RAB11FIP4 | RAB11 family interacting protein 4 (class II) | NM_032932 | 17q11.2 | 13.4 |
| parous | promoter | NTN1 | netrin 1 | NM_004822 | 17p13-p12 | 8.4 |
| parous | promoter | NTN4 | netrin 4 | NM_021229 | 12q22 | 6 |
| parous | promoter | INSR | insulin receptor | NM_001079817 | 19p13.3-p13.2 | 4.8 |
| parous | promoter | BAD | BCL2-associated agonist of cell death | NM_032989 | 11q13.1 | 7.9 |
| parous | promoter | TCF7L1 | transcription factor 7-like 1 (T-cell specific, HMG-box) | NM_031283 | 2p11.2 | 12.1 |
| parous | promoter | C9orf75 | chromosome 9 open reading frame 75 | NM_173691 | 9q34.3 | 4.8 |
| parous | promoter | C3orf45 | chromosome 3 open reading frame 45 | NM_153215 | 3p21.31 | 6.2 |
| parous | promoter | NKX3-2 | NK3 homeobox 2 | NM_001189 | 4p16.3 | −2 |
| parous | promoter | NKX3-2 | NK3 homeobox 2 | NM_001189 | 4p16.3 | 2.4 |
| parous | promoter | OXTR | oxytocin receptor | NM_000916 | 3p25 | 5.6 |
| parous | promoter | SOCS5 | suppressor of cytokine signaling 5 | NM_014011 | 2p21 | 36.1 |
| parous | promoter | AMIGO2 | adhesion molecule with Ig-like domain 2 | NM_181847 | 12q13.11 | 5.5 |
| parous | promoter | LDLRAP1 | low density lipoprotein receptor adaptor protein 1 | NM_015627 | 1p36-p35 | 3.8 |
| parous | promoter | HMX2 | H6 family homeobox 2 | NM_005519 | 10q26.13 | 2.5 |
| parous | promoter | PHF10 | PHD finger protein 10 | NM_018288 | 6q27 | 3.2 |
| parous | promoter | TRIM71 | tripartite motif-containing 71 | NM_001039111 | 3p22.3 | 30.8 |
| parous | promoter | AKR1CL2 | NA | NM_001040177 | NA | 2.4 |
| parous | promoter | TCEB3 | transcription elongation factor B (SIII), polypeptide 3 (110 kDa, elongin A) | NM_003198 | 1p36.1 | 6.8 |
| parous | promoter | CEP57 | centrosomal protein 57 kDa | NM_014679 | 11q21 | 23.5 |
| parous | promoter | FLJ40125 | NA | NM_001080401 | NA | 4.7 |
| parous | promoter | C21orf66 | chromosome 21 open reading frame 66 | NM_016631 | 21q22.11 | 6 |
| parous | promoter | C17orf91 | chromosome 17 open reading frame 91 | NM_032895 | 17p13.3 | 28.7 |
| parous | promoter | TIMM9 | translocase of inner mitochondrial membrane 9 homolog (yeast) | NM_012460 | 14q22.3-q24 | 6.4 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | promoter | SLC33A1 | NM_004733 | solute carrier family 33 (acetyl-CoA transporter), member 1 | 3q | 2.3 |
| parous | promoter | MRPS17 | NM_015969 | mitochondrial ribosomal protein S17 | 7p11-q11.21 | 7.6 |
| parous | promoter | KANK4 | NM_181712 | KN motif and ankyrin repeat domains 4 | 1p31.3 | 9 |
| parous | promoter | SOX8 | NM_014587 | SRY (sex determining region Y)-box 8 | 16p13.3 | 2.9 |
| parous | promoter | SOX9 | NM_000346 | SRY (sex determining region Y)-box 9 | 17q23 | 3.6 |
| parous | promoter | MYLPF | NM_013292 | myosin light chain, phosphorylatable, fast skeletal muscle | 16p11.2 | 5 |
| parous | promoter | HIST1H2AD | NM_021065 | histone cluster 1, H2ad | 6p22.1 | 3.2 |
| parous | promoter | MOXD1 | NM_015529 | monooxygenase, DBH-like 1 | 6q23.2 | 3 |
| parous | promoter | GALNTL1 | NM_020692 | UDP-N-acetyl-alpha-D-galactosaminepolypeptide N-acetylgalactosaminyltransferase-like 1 | 14q24.1 | 3.4 |
| parous | promoter | SMARCA2 | NM_139045 | SWI/SNF related, matrix associated, actin dependent regulator of chromatin, subfamily a, member 2 | 9p24.3 | 2.9 |
| parous | promoter | FIBIN | NM_203371 | fin bud initiation factor homolog (zebrafish) | 11p14.2 | 2.6 |
| parous | promoter | CPSF1 | NM_013291 | cleavage and polyadenylation specific factor 1, 160 kDa | 8q24 | -7.8 |
| parous | promoter | CPSF1 | NM_013291 | cleavage and polyadenylation specific factor 1, 160 kDa | 8q24 | 2.6 |
| parous | promoter | FAM83D | NM_030919 | family with sequence similarity 83, member D | 20 | 2.7 |
| parous | promoter | SERTAD3 | NM_013368 | SERTA domain containing 3 | 19q13.2 | 6.3 |
| parous | promoter | ASAH1 | NM_177924 | N-acylsphingosine amidohydrolase (acid ceramidase) 1 | 8p22 | 7.2 |
| parous | promoter | RAD54L | NM_003579 | RAD54-like (S. cerevisiae) | 1p32 | 12.2 |
| parous | promoter | ZMYM5 | NM_001039649 | zinc finger, MYM-type 5 | 13q12 | 6.3 |
| parous | promoter | PTHLH | NM_198966 | parathyroid hormone-like hormone | 12p12.1-p11.2 | 4.8 |
| parous | promoter | ALX4 | NM_021926 | ALX homeobox 4 | 11p11.2 | 23.9 |
| parous | promoter | FOXRED2 | NM_024955 | FAD-dependent oxidoreductase domain containing 2 | 22q12.3 | 75.8 |
| parous | promoter | GAL | NM_015973 | galanin prepropeptide | 11q13.2 | 13.9 |
| parous | promoter | DOK6 | NM_152721 | docking protein 6 | 18q22.2 | 3.2 |
| parous | promoter | KCNS1 | NM_002251 | potassium voltage-gated channel, delayed-rectifier, subfamily S, member 1 | 20q12 | 4.1 |
| parous | promoter | CXCR4 | NM_003467 | chemokine (C-X-C motif) receptor 4 | 2q21 | 46.9 |
| parous | promoter | MSX1 | NM_002448 | msh homeobox 1 | 4p16.2 | 8.4 |
| parous | promoter | KLF9 | NM_001206 | Kruppel-like factor 9 | 9q21.11 | 25 |
| parous | promoter | HS3ST3B1 | NM_006041 | heparan sulfate (glucosamine) 3-O-sulfotransferase 3B1 | 17p12 | 12.5 |
| parous | promoter | CPT1A | NM_001876 | carnitine palmitoyltransferase 1A (liver) | 11q13.2 | 2.7 |
| parous | promoter | TFAP4 | NM_003223 | transcription factor AP-4 (activating enhancer binding protein 4) | 16p13 | 5.1 |
| parous | promoter | SNTA1 | NM_003098 | syntrophin, alpha 1 (dystrophin-assodated protein A1, 59 kDa, addic component) | 20q11.2 | 2.2 |
| parous | promoter | CPT1B | NM_152246 | carnitine palmitoyltransferase 1B (muscle) | 22q13.33 | 14.5 |
| parous | promoter | LOC100144603 | NR_021492 | NA | NA | 14.5 |
| parous | promoter | AP4M1 | NM_004722 | adaptor-related protein complex 4, mu 1 subunit | 7q22.1 | 3.2 |
| parous | promoter | RNF128 | NM_194463 | ring finger protein 128 | Xq22.3 | 3 |
| parous | promoter | MFSD5 | NM_032889 | major facilitator superfamily domain containing 5 | 12q13.13 | 8.7 |
| parous | promoter | RTN2 | NM_005619 | reticulon 2 | 19q13.2-q13.3 | 4.7 |
| parous | promoter | MCM7 | NM_182776 | minichromosome maintenance complex component 7 | 7q21.3-q22.1 | 3.2 |
| parous | promoter | FAM19A5 | NM_001082967 | family with sequence similarity 19 (chemokine (C-C motif)-like), member A5 | 22q13.32 | 2.4 |
| parous | promoter | HIST1H3D | NM_003530 | histone cluster 1, H3d | 6p22.1 | 3.2 |
| parous | promoter | CASC4 | NM_138423 | cancer susceptibility candidate 4 | 15q15. | 3.6 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | promoter | VCX | NM_013452 | variable charge, X-linked | Xp22.31 | 3.2 |
| parous | promoter | ZNF860 | NM_001137674 | zinc finger protein 860 | 3p24.1 | 3.4 |
| parous | promoter | VCX2 | NM_016378 | variable charge, X-linked 2 | Xp22.32 | 3.2 |
| parous | promoter | MEX3B | NM_032246 | mex-3 homolog B (C. elegans) | 15q25.1 | 9.3 |
| parous | promoter | SMOX | NM_175842 | spermine oxidase | 20p13 | 4.9 |
| parous | promoter | PTPRT | NM_007050 | protein tyrosine phosphatase, receptor type, T | 20q12-q13 | 2.4 |
| parous | promoter | VAMP5 | NM_006634 | vesicle-associated membrane protein 5 (myobrevin) | 2p11.2 | 7.7 |
| parous | promoter | SLC40A1 | NM_014585 | solute carrier family 40 (iron-regulated transporter), member 1 | 2q32 | 77.9 |
| parous | promoter | SPAST | NM_014946 | spastin | 2p24-p21 | 5.9 |
| parous | promoter | DDX24 | NM_020414 | DEAD (Asp-Glu-Ala-Asp) box polypeptide 24 | 14q32 | 4.2 |
| parous | promoter | SRRM2 | NM_016333 | serine/arginine repetitive matrix 2 | 16p13.3 | 2.1 |
| parous | promoter | NSUN7 | NM_024677 | NOL1/NOP2/Sun domain family, member 7 | 4p14 | 2.2 |
| parous | promoter | PRCD | NM_001077620 | progressive rod-cone degeneration | 17q25.1 | 10.4 |
| parous | promoter | PSAT1 | NM_058179 | phosphoserine aminotransferase 1 | 9q21.2 | 21.5 |
| parous | promoter | REC8 | NM_005132 | REC8 homolog (yeast) | 14q11.2-q12 | 165 |
| parous | promoter | SCN1B | NM_199037 | sodium channel, voltage-gated, type I, beta | 19 | 5.3 |
| parous | promoter | UBE3C | NM_014671 | ubiquitin protein ligase E3C | 7q36.3 | 7.5 |
| parous | promoter | TCTEX1D2 | NM_152773 | Tctex1 domain containing 2 | 3q29 | 2.1 |
| parous | promoter | BCL6 | NM_001130845 | B-cell CLL/lymphoma 6 | 3q27 | 2.9 |
| parous | promoter | TBC1D10B | NM_015527 | TBC1 domain family, member 10B | 16p11.2 | 5 |
| parous | promoter | PGAP1 | NM_024989 | post-GPI attachment to proteins 1 | 2q33.1 | -2.1 |
| nulliparous | promoter | ZCCHC11 | NM_001009881 | zinc finger, CCHC domain containing 11 | 1p32.3 | -3.6 |
| nulliparous | promoter | AGL | NM_000644 | amylo-1,6-glucosidase, 4-alpha-glucanotransferase | 1p21 | -5.7 |
| nulliparous | promoter | TMCO1 | NM_019026 | transmembrane and coiled-coil domains 1 | 1q22-q25 | -5.7 |
| nulliparous | promoter | LOC728024 | NR_003671 | NA | NA | -3.8 |
| nulliparous | promoter | B2M | NM_004048 | beta-2-microglobulin | 15q21- | -3.8 |
| nulliparous | promoter | RARS2 | NM_020320 | arginyl-tRNA synthetase 2, mitochondrial | 6q16.1 | -3.5 |
| nulliparous | promoter | SEMA4C | NM_017789 | sema domain, immunoglobulin domain (Ig), transmembrane domain (TM) and short cytoplasmic domain, (semaphorin) 4C | 2q11.2 | -2.4 |
| nulliparous | promoter | SEMA4F | NM_004263 | sema domain, immunoglobulin domain (Ig), transmembrane domain (TM) and short cytoplasmic domain, (semaphorin) 4F | 2p13.1 | -2.4 |
| nulliparous | promoter | C1orf123 | NM_017887 | chromosome 1 open reading frame 123 | 1p32.3 | -2.2 |
| nulliparous | promoter | SMG7 | NM_201569 | Smg-7 homolog, nonsense mediated mRNA decay factor (C. elegans) | 1q25 | -2.7 |
| nulliparous | promoter | SAMD12 | NM_001101676 | sterile alpha motif domain containing 12 | 8q24.12 | -2.8 |
| nulliparous | promoter | SAMD10 | NM_080621 | sterile alpha motif domain containing 10 | 20q13.33 | -3.9 |
| nulliparous | promoter | SQRDL | NM_021199 | sulfide quinone reductase-like (yeast) | 15q15 | -8.4 |
| nulliparous | promoter | PTGER4 | NM_000958 | prostaglandin E receptor 4 (subtype EP4) | 5p13.1 | -9.5 |
| nulliparous | promoter | NR0B1 | NM_000475 | nuclear receptor subfamily 0, group B, member 1 | Xp21.3 | -6.9 |
| nulliparous | promoter | COMMD7 | NM_001099339 | COMM domain containing 7 | 20q11 | -3 |
| nulliparous | promoter | SLC6A17 | NM_001010898 | solute carrier family 6, member 17 | 1p13.2 | -25.6 |
| nulliparous | promoter | C3orf14 | NM_020685 | chromosome 3 open reading frame | 3 | -2.2 |
| nulliparous | promoter | HEBP2 | NM_014320 | heme binding protein 2 | 6q24 | -8.1 |
| nulliparous | promoter | VAC14 | NM_018052 | Vac14 homolog (S. cerevisiae) | 16q22.1 | -2.6 |
| nulliparous | promoter | VAC14 | NM_018052 | Vac14 homolog (S. cerevisiae) | 16q22.1 | -5.4 |
| nulliparous | promoter | IL18 | NM_001562 | interleukin 18 (interferon-gamma-inducing factor) | 11q22.2-q22.3 | -3 |
| nulliparous | promoter | JRKL | NM_003772 | jerky homolog-like (mouse) | 11q21 | -16.4 |
| nulliparous | promoter | WIPI1 | NM_017983 | WD repeat domain, phosphoinositide interacting 1 | 17q24.2 | -5.2 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | ZNF687 | NM_020832 | zinc finger protein 687 | 1q21.2 | -32.1 |
| nulliparous | promoter | STK3 | NM_006281 | serine/threonine kinase 3 (STE20 homolog, yeast) | 8q22.2 | -2.1 |
| nulliparous | promoter | KHDC1 | NM_030568 | KH homology domain containing 1 | 6q13 | -2.8 |
| nulliparous | promoter | OCA2 | NM_000275 | oculocutaneous albinism II | 15q11.2-q12 | -6 |
| nulliparous | promoter | 38048 | NM_178450 | NA | NA | -2.1 |
| nulliparous | promoter | GATA2 | NM_032638 | GATA binding protein 2 | 3q21 | -3.6 |
| nulliparous | promoter | CXCL14 | NM_004887 | chemokine (C-X-C motif) ligand 14 | 5q31 | -2.2 |
| nulliparous | promoter | AKAP5 | NM_004857 | A kinase (PRKA) anchor protein 5 | 14q21-q24 | -3.3 |
| nulliparous | promoter | UBE4A | NM_004788 | ubiquitination factor E4A (UFD2 homolog, yeast) | 11q23.3 | -2.5 |
| nulliparous | promoter | TC2N | NM_001128595 | tandem C2 domains, nuclear | 14q32.12 | -23.5 |
| nulliparous | promoter | LECT1 | NM_001011705 | leukocyte cell derived chemotaxin 1 | 13q14-q21 | -2.3 |
| nulliparous | promoter | HCN3 | NM_020897 | hyperpolarization activated cyclic nucleotide-gated potassium channel 3 | 1q21.2 | -3.6 |
| nulliparous | promoter | C13orf27 | NM_138779 | chromosome 13 open reading frame 27 | 13q33.1 | -2.5 |
| nulliparous | promoter | TRAPPC5 | NM_001042462 | trafficking protein particle complex 5 | 19p13.3 | -4.8 |
| nulliparous | promoter | ARFRP1 | NM_001134758 | ADP-ribosylation factor related protein 1 | 20p13.3 | -4 |
| nulliparous | promoter | DDX47 | NM_016355 | DEAD (Asp-Glu-Ala-Asp) box polypeptide 47 | 12p13.2 | -3.5 |
| nulliparous | promoter | ZGPAT | NM_001083113 | zinc finger, CCCH-type with G patch domain | 20q13.33 | -4 |
| nulliparous | promoter | RHBDD3 | NM_012265 | rhomboid domain containing 3 | 22q12.2 | -6.3 |
| nulliparous | promoter | C6orf159 | NM_001009994 | NA | NA | -2.6 |
| nulliparous | promoter | EIF5A2 | NM_020390 | eukaryotic translation initiation | 3q26.2 | -15.4 |
| nulliparous | promoter | YBX1 | NM_004559 | Y box binding protein 1 | 1p34 | -2.7 |
| nulliparous | promoter | YBX2 | NM_015982 | Y box binding protein 2 | 17p13. | -3.2 |
| nulliparous | promoter | YBX2 | NM_015982 | Y box binding protein 2 | 17p13. | -3.3 |
| nulliparous | promoter | DIRAS1 | NM_145173 | DIRAS family, GTP-binding RAS-like 1 | 19p13.3 | -3.4 |
| nulliparous | promoter | HMGN1 | NM_004965 | high-mobility group nucleosome binding domain 1 | 21q22.3 | -2.9 |
| nulliparous | promoter | DTL | NM_016448 | denticleless homolog (Drosophila) | 1q32 | -6 |
| nulliparous | promoter | HACL1 | NM_012260 | 2-hydroxyacyl-CoA lyase 1 | 3p24.3 | -2.7 |
| nulliparous | promoter | RARRES2 | NM_002889 | retinoic acid receptor responder (tazarotene induced) 2 | 7q36.1 | -2.5 |
| nulliparous | promoter | POLR3A | NM_007055 | polymerase (RNA) III (DNA directed) polypeptide A, 155 kDa | 10q22-q23 | -3.8 |
| nulliparous | promoter | RAB6A | NM_198896 | RAB6A, member RAS oncogene family | 11q13.3 | -2.5 |
| nulliparous | promoter | KIAA1279 | NM_015634 | KIAA1279 | 10q22.1 | -2.5 |
| nulliparous | promoter | GTF3C3 | NM_012086 | general transcription factor IIIC, polypeptide 3, 102 kDa | 2q33.1 | -4.6 |
| nulliparous | promoter | MGST3 | NM_004528 | microsomal glutathione S-transferase 3 | 1q23 | -2.1 |
| nulliparous | promoter | POLR1C | NM_203290 | polymerase (RNA) I polypeptide C, 30 kDa | 6p21.1 | -4.7 |
| nulliparous | promoter | LOC100134229 | NR_024451 | NA | NA | -7.1 |
| nulliparous | promoter | ISCA1 | NM_030940 | iron-sulfur cluster assembly 1 homolog (S. cerevisiae) | 9q22.1 | -4.4 |
| nulliparous | promoter | SNORD68 | NR_002450 | small nucleolar RNA, C/D box 68 | 16q24.3 | -3.1 |
| nulliparous | promoter | PKHD1L1 | NM_177531 | polycystic kidney and hepatic disease 1 (autosomal recessive) like 1 | 8q23 | -2.9 |
| nulliparous | promoter | PANK1 | NM_148978 | pantothenate kinase 1 | 10q23.31 | -2.3 |
| nulliparous | promoter | CYP11A1 | NM_001099773 | cytochrome P450, family 11, subfamily A, polypeptide 1 | 15q23-q24 | -2.1 |
| nulliparous | promoter | LOC541473 | NR_003602 | NA | NA | -2.2 |
| nulliparous | promoter | SOX11 | NM_003108 | SRY (sex determining region Y)-box 11 | 2p25 | -5.6 |
| nulliparous | promoter | PCDHB11 | NM_018931 | protocadherin beta 11 | 5q31 | -7.1 |
| nulliparous | promoter | SOX17 | NM_022454 | SRY (sex determining region Y)-box 17 | 8q11.23 | -2.2 |
| nulliparous | promoter | BCDIN3D | NM_181708 | BCDIN3 domain containing | 12q13.13 | -3.9 |
| nulliparous | promoter | PAICS | NM_006452 | phosphoribosylaminoimidazole carboxylase, phosphoribosylaminoimidazole succinocarboxamide synthetase | 4pter-q21 | -4.5 |

TABLE 14-continued

Comprehensive DNA Methylation and K27 Profiles of CD44+ Nulliparous and Parous Breast Epithelial Cells

| | | | | | |
|---|---|---|---|---|---|
| nulliparous | promoter | EFTUD1 | NM_024580 | elongation factor Tu GTP binding domain containing 1 | 15q25.2 | −24.5 |
| nulliparous | promoter | RSBN1L | NM_198467 | round spermatid basic protein 1-like | 7q21.11 | −4.7 |
| nulliparous | promoter | DIO1 | NM_001039715 | deiodinase, iodothyronine, type I | 1p33-p32 | −2.1 |
| nulliparous | promoter | ANKS6 | NM_173551 | ankyrin repeat and sterile alpha motif domain containing 6 | 9q31.1 | −3.3 |
| nulliparous | promoter | DIO3 | NM_001362 | deiodinase, iodothyronine, type III | 14q32 | −7.7 |
| nulliparous | promoter | OPCML | NM_002545 | opioid binding protein/cell adhesion molecule-like | 11q25 | −2.2 |
| nulliparous | promoter | ZNF517 | NM_213605 | zinc finger protein 517 | 8q24.3 | −11.2 |
| nulliparous | promoter | PDLIM4 | NM_001131027 | PDZ and LIM domain 4 | 5q31.1 | −2.7 |
| nulliparous | promoter | CCDC53 | NM_016053 | coiled-coil domain containing 53 | 12q23.3 | −2.2 |
| nulliparous | promoter | UCK1 | NM_001135954 | uridine-cytidine kinase 1 | 9q34.1 | −4 |
| nulliparous | promoter | FIBCD1 | NM_032843 | fibrinogen C domain containing 1 | 9q34.2 | −2.1 |
| nulliparous | promoter | FIBCD1 | NM_032843 | fibrinogen C domain containing 1 | 9q34.2 | 19.8 |
| nulliparous | promoter | C8orf45 | NM_001136161 | chromosome 8 open reading frame 45 | 8q13.1 | −12.7 |
| nulliparous | promoter | KCNQ5 | NM_019842 | potassium voltage-gated channel, KQT-like subfamily, member 5 | 6q14 | −10.6 |
| nulliparous | promoter | KCNQ1 | NM_000218 | potassium voltage-gated channel, KQT-like subfamily, member 1 | 11p15.5 | −6 |
| nulliparous | promoter | NFASC | NM_015090 | neurofascin homolog (chicken) | 1q32.1 | −3.3 |
| nulliparous | promoter | HIST2H3C | NM_021059 | histone cluster 2, H3c | 1q21.2 | −5.3 |
| nulliparous | promoter | HIST2H3A | NM_001005464 | histone cluster 2, H3a | 1q21.2 | −5.3 |
| nulliparous | promoter | CNTFR | NM_001842 | ciliary neurotrophic factor receptor | 9p13 | −2.6 |
| nulliparous | promoter | RTTN | NM_173630 | rotatin | 18q22.1 | −2.2 |
| nulliparous | promoter | GARS | NM_002047 | glycyl-tRNA synthetase | 7p15 | −7.2 |
| nulliparous | promoter | C5orf13 | NM_004772 | chromosome 5 open reading frame 13 | 5q22.1 | −2.5 |
| nulliparous | promoter | ZDHHC3 | NM_001135179 | zinc finger, DHHC-type containing 3 | 3p21.31 | −7.1 |
| nulliparous | promoter | SAMD11 | NM_152486 | sterile alpha motif domain | 1p36.33 | −6 |
| nulliparous | promoter | ERMP1 | NM_024896 | endoplasmic reticulum metallopeptidase 1 | 9p24 | −2.6 |
| nulliparous | promoter | FBXO34 | NM_152231 | F-box protein 34 | 14q22.1 | −25.5 |
| nulliparous | promoter | ZNF703 | NM_025069 | zinc finger protein 703 | 8p12 | −2.4 |
| nulliparous | promoter | WDR37 | NM_014023 | WD repeat domain 37 | 10p15.3 | −2.3 |
| nulliparous | promoter | ZNF26 | NM_019591 | zinc finger protein 26 | 12q24.33 | −2.4 |
| nulliparous | promoter | FLNB | NM_001457 | filamin B, beta | 3p14.3 | −4.3 |
| nulliparous | promoter | MINPP1 | NM_004897 | multiple inositol polyphosphate histidine phosphatase, 1 | 10q23 | −2.1 |
| nulliparous | promoter | NAB2 | NM_005967 | NGFI-A binding protein 2 (EGR1 binding protein 2) | 12q13.3 | −4.3 |
| nulliparous | promoter | FLJ45244 | NR_015415 | NA | NA | −8.5 |
| nulliparous | promoter | SOAT1 | NM_003101 | sterol O acyltransferase 1 | 1q25 | 4 |
| nulliparous | promoter | FLJ45537 | NM_001001709 | NA | NA | −2.9 |
| nulliparous | promoter | SNORD74 | NR_002579 | small nucleolar RNA, C/D box 74 | 1q25.1 | −9.1 |
| nulliparous | promoter | SESN3 | NM_144665 | sestrin 3 | 11q21 | −2.7 |
| nulliparous | promoter | SNORD47 | NR_002746 | small nucleolar RNA, C/D box 47 | 1q25.1 | −9.1 |
| nulliparous | promoter | RCAN3 | NM_013441 | RCAN family member 3 | 1p35.3-p33 | −5.1 |
| nulliparous | promoter | VAPB | NM_004738 | VAMP (vesicle-associated membrane protein)-associated protein B and C | 20q13 | −2.6 |
| nulliparous | promoter | SMAD2 | NM_001003652 | SMAD family member 2 | 18q21 | −2.6 |
| nulliparous | promoter | SLC4A4 | NM_001098484 | solute carrier family 4, sodium bicarbonate cotransporter, member 4 | 4q21 | −3.3 |
| nulliparous | promoter | ZNF839 | NM_018335 | zinc finger protein 839 | 14q32.32 | −3.5 |
| nulliparous | promoter | NELL2 | NM_006159 | NEL-like 2 (chicken) | 12q12 | −6.9 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | SNORA62 | NR_002324 | small nucleolar RNA, H/ACA box 62 | 3p22 | −5.9 |
| nulliparous | promoter | HTRA3 | NM_053044 | HtrA serine peptidase 3 | 4p16.1 | −2.5 |
| nulliparous | promoter | GDAP1 | NM_018972 | ganglioside-induced differentiation-associated protein 1 | 8q13.3 | −13.8 |
| nulliparous | promoter | PLRG1 | NM_002669 | pleiotropic regulator 1 (PRL1 homolog, Arabidopsis) | 4q31.2-q32.1 | −4.8 |
| nulliparous | promoter | ASPH | NM_004318 | aspartate beta-hydroxylase | 8q12.1 | −4.9 |
| nulliparous | promoter | ARF5 | NM_001662 | ADP-ribosylation factor 5 | 7q31.3 | −4.8 |
| nulliparous | promoter | ACAT2 | NM_005891 | acetyl-Coenzyme A acetyltransferase 2 | 6q25.3-q26 | −2.4 |
| nulliparous | promoter | PCDHB10 | NM_018930 | protocadherin beta 10 | 5q31 | −7.1 |
| nulliparous | promoter | PBK | NM_018492 | PDZ binding kinase | 8p21.2 | −5.2 |
| nulliparous | promoter | TM9SF3 | NM_020123 | transmembrane 9 superfamily member 3 | 10q24.2 | −5.2 |
| nulliparous | promoter | PTTG1 | NM_004219 | pituitary tumor-transforming 1 | 5q35.1 | −6.8 |
| nulliparous | promoter | WBSCR17 | NM_022479 | Williams-Beuren syndrome chromosome region 17 | 7q11.23 | −2.4 |
| nulliparous | promoter | WBSCR16 | NM_030798 | Williams-Beuren syndrome chromosome region 16 | 7q11.23 | −2.9 |
| nulliparous | promoter | CLINT1 | NM_014666 | clathrin interactor 1 | 5q33.3 | −4 |
| nulliparous | promoter | CYP20A1 | NM_177538 | cytochrome P450, family 20, subfamily A, polypeptide 1 | 2q33 | −2.4 |
| nulliparous | promoter | TMEM26 | NM_178505 | transmembrane protein 26 | 10q21.3 | −2.2 |
| nulliparous | promoter | LTK | NM_002344 | leukocyte receptor tyrosine kinase | 15q15.1-q21.1 | −6.7 |
| nulliparous | promoter | DHFRL1 | NM_176815 | dihydrofolate reductase-like 1 | 3q11.2 | −3.1 |
| nulliparous | promoter | ANKRD20B | NR_003366 | ankyrin repeat domain 20B | 2q11.1 | −6 |
| nulliparous | promoter | TNFAIP8 | NM_001077654 | tumor necrosis factor, alpha-induced protein 8 | 5q23.1 | −7.7 |
| nulliparous | promoter | CAPZA2 | NM_006136 | capping protein (actin filament) muscle Z-line, alpha 2 | 7q31.2-q31.3 | −2.7 |
| nulliparous | promoter | TAF1A | NM_139352 | TATA box binding protein (TBP)-associated factor, RNA polymerase I, A, 48 kDa | 1q42 | −20.6 |
| nulliparous | promoter | GPR150 | NM_199243 | G protein-coupled receptor 150 | 5q15 | −11.5 |
| nulliparous | promoter | RAB33B | NM_031296 | RAB33B, member RAS oncogene family | 4q28 | −11.6 |
| nulliparous | promoter | MED30 | NM_080651 | mediator complex subunit 30 | 8q24.11 | −2.7 |
| nulliparous | promoter | LMO3 | NM_001001395 | LIM domain only 3 (rhombotin-like) | 12p13 | −3.7 |
| nulliparous | promoter | ABCA5 | NM_172232 | ATP-binding cassette, sub-family A (ABC1), member 5 | 17q21-q25 | −2.7 |
| nulliparous | promoter | CXXC4 | NM_025212 | CXXC finger 4 | 4q22-q24 | −2.9 |
| nulliparous | promoter | MYL6B | NM_002475 | myosin, light chain 6B, alkali, smooth muscle and non-muscle | 12q13.2 | −2.3 |
| nulliparous | promoter | TUBGCP5 | NM_001102610 | tubulin, gamma complex associated protein 5 | 15q11.1 | −6.3 |
| nulliparous | promoter | TUBGCP5 | NM_001102610 | tubulin, gamma complex associated protein 5 | 15q11.1 | −3.9 |
| nulliparous | promoter | CCBL2 | NM_019610 | cysteine conjugate-beta lyase 2 | 1p22.2 | −3.1 |
| nulliparous | promoter | RBM6 | NM_005777 | RNA binding motif protein 6 | 3p21.3 | −6.4 |
| nulliparous | promoter | CUEDC1 | NM_017949 | CUE domain containing 1 | 17q23.2 | −4 |
| nulliparous | promoter | ACTR10 | NM_018477 | actin-related protein 10 homolog (S. cerevisiae) | 14q22.3 | −3.3 |
| nulliparous | promoter | STT3A | NM_152713 | STT3, subunit of the oligosaccharyltransferase complex, homolog A (S. cerevisiae) | 11q23.3 | −5.1 |
| nulliparous | promoter | PIGY | NM_001042616 | phosphatidylinositol glycan anchor biosynthesis, class Y | 4q22.1 | −5.1 |
| nulliparous | promoter | TH1L | NM_198976 | TH1-like (Drosophila) | 20q13 | −2.2 |
| nulliparous | promoter | RBMXL2 | NM_014469 | RNA binding motif protein, X-linked-like 2 | 11p15 | −8.9 |
| nulliparous | promoter | EPS8 | NM_004447 | epidermal growth factor receptor pathway substrate 8 | 12p12.3 | −5.4 |
| nulliparous | promoter | TXNL4A | NM_006701 | thioredoxin-like 4A | 18q23 | −5 |
| nulliparous | promoter | RB1CC1 | NM_001083617 | RB1-inducible coiled-coil 1 | 8q11 | −7 |
| nulliparous | promoter | CPSF1 | NM_013291 | cleavage and polyadenylation specific factor 1,160 kDa | 8q24 | −7.8 |
| nulliparous | promoter | CPSF1 | NM_013291 | cleavage and polyadenylation specific factor 1,160 kDa | 8q24 | 2.6 |
| nulliparous | promoter | SIM1 | NM_005068 | single-minded homolog 1 (Drosophila) | 6q16.3-q21 | −3 |
| nulliparous | promoter | TOB1 | NM_005749 | transducer of ERBB2, 1 | 17q21 | −5.3 |
| nulliparous | promoter | TP53TG3 | NM_016212 | TP53 target 3 | 16p13 | −3.8 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | PPFIA1 | NM_177423 | protein tyrosine phosphatase, receptor type, f polypeptide (PTPRF), interacting protein (liprin), alpha 1 | 11q13.3 | -2.6 |
| nulliparous | promoter | TMEM41A | NM_080652 | transmembrane protein 41A | 3q27.2 | -4.1 |
| nulliparous | promoter | DPYS | NM_001385 | dihydropyrimidinase | 8q22 | -2.9 |
| nulliparous | promoter | NEO1 | NM_002499 | neogenin homolog 1 (chicken) | 15q22.3-q23 | -2.5 |
| nulliparous | promoter | CDCA7 | NM_031942 | cell division cycle associated 7 | 2q31.1 | -7.4 |
| nulliparous | promoter | GPR120 | NM_181745 | G protein-coupled receptor 120 | 10q23.33 | -4.4 |
| nulliparous | promoter | CLIP4 | NM_024692 | CAP-GLY domain containing linker protein family, member 4 | 2p23 | -2.6 |
| nulliparous | promoter | DYNLRB2 | NM_130897 | dynein, light chain, roadblock-type 2 | 16q23.3 | -3.2 |
| nulliparous | promoter | HSD17B4 | NM_000414 | hydroxysteroid (17-beta) dehydrogenase 4 | 5q2 | -G |
| nulliparous | promoter | CNOT6 | NM_015455 | CCR4-NOT transcription complex, subunit 6 | 5q35.3 | -7.5 |
| nulliparous | promoter | PCDH17 | NM_001040429 | protocadherin 17 | 13q21.1 | -5.4 |
| nulliparous | promoter | TTLL1 | NM_001008572 | tubulin tyrosine ligase-like family, member 1 | 22q13.1 | -6.1 |
| nulliparous | promoter | HEATR3 | NM_182922 | HEAT repeat containing 3 | 16q12.1 | -3.9 |
| nulliparous | promoter | NLGN4X | NM_020742 | neuroligin 4, X-linked | Xp22.33 | -7.6 |
| nulliparous | promoter | KIF18A | NM_031217 | kinesin family member 18A | 11p14.1 | -9.8 |
| nulliparous | promoter | PTGR1 | NM_012212 | prostaglandin reductase 1 | 9q32 | -2.7 |
| nulliparous | promoter | GAS1 | NM_002048 | growth arrest-specific 1 | 9q21.3-q22 | -5.2 |
| nulliparous | promoter | ATG4D | NM_032885 | ATG4 autophagy related 4 homolog D (S. cerevisiae) | 19p13.2 | -2.4 |
| nulliparous | promoter | MMP25 | NM_022468 | matrix metallopeptidase 25 | 16p13.3 | -2.7 |
| nulliparous | promoter | MEX3D | NM_203304 | mex-3 homolog D (C. elegans) | 19p13.3 | -4.9 |
| nulliparous | promoter | TRIP13 | NM_004237 | thyroid hormone receptor interactor 13 | 5p15 | -6.1 |
| nulliparous | promoter | HOXB13 | NM_006361 | homeobox B13 | 17q21.32 | -2.3 |
| nulliparous | promoter | SLC35F5 | NM_025181 | solute carrier family 35, member F5 | 2q14.1 | -4.3 |
| nulliparous | promoter | SNW1 | NM_012245 | SNW domain containing 1 | 14q22.1-q22.3 | -2.8 |
| nulliparous | promoter | WASF2 | NM_006990 | WAS protein family, member 2 | 1p36.11 | -3.5 |
| nulliparous | promoter | SLC35F2 | NM_017515 | solute carrier family 35, member F2 | 11q23.1 | -2.8 |
| nulliparous | promoter | YRDC | NM_024640 | yrdC domain containing (E. coli) | 1p34.3 | -3.3 |
| nulliparous | promoter | SLU7 | NM_006425 | SLU7 splicing factor homolog (S. cerevisiae) | 5q33.3 | -6.8 |
| nulliparous | promoter | COX15 | NM_004376 | COX15 homolog, cytochrome c oxidase assembly protein (yeast) | 10q24 | -4 |
| nulliparous | promoter | ZNF468 | NM_001008801 | zinc finger protein 468 | 19q13.41 | -10.5 |
| nulliparous | promoter | FUT4 | NM_002033 | fucosyltransferase 4 (alpha (1,3) fucosyltransferase, myeloid-specific) | 11q12-qter | -4.1 |
| nulliparous | promoter | FUT1 | NM_000148 | fucosyltransferase 1 (galactoside 2-alpha-L-fucosyltransferase, H blood group) | 19q13.1-qter | -5.5 |
| nulliparous | promoter | CMTM3 | NM_001048251 | CKLF-like MARVEL transmembrane domain containing 3 | 16q22.1-q22.3 | -2.3 |
| nulliparous | promoter | EWSR1 | NM_005243 | Ewing sarcoma breakpoint region 1 | 22q12.2 | -6.3 |
| nulliparous | promoter | IL1RL2 | NM_003854 | interleukin 1 receptor-like 2 | 2q12 | -2.1 |
| nulliparous | promoter | ATP5J2 | NM_004889 | ATP synthase, H+ transporting, mitochondrial F0 complex, subunit F2 | 7q22.1 | -6.3 |
| nulliparous | promoter | UFC1 | NM_016406 | ubiquitin-fold modifier conjugating enzyme 1 | 1q23.3 | -6.7 |
| nulliparous | promoter | HNRPLL | NM_138394 | heterogeneous nuclear ribonucleoprotein L-like | 2p22 | -5.3 |
| nulliparous | promoter | SFMBT1 | NM_001005159 | Scm-like with four mbt domains 1 | 3p21.31 | -2.7 |
| nulliparous | promoter | SFMBT2 | NM_001029880 | Scm-like with four mbt domains 2 | 10p15. | -3.3 |
| nulliparous | promoter | EHD4 | NM_139265 | EH-domain containing 4 | 15q11.1 | -11.2 |
| nulliparous | promoter | REXO4 | NM_020385 | REX4, RNA exonuclease 4 homolog (S. cerevisiae) | 9q34 | -3.6 |
| nulliparous | promoter | USP29 | NM_020903 | ubiquitin specific peptidase 29 | 19q13.4 | -6.4 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | RASAL1 | NM_004658 | RAS protein activator like 1 (GAP1 like) | 12q23-q24 | -3.4 |
| nulliparous | promoter | DEPDC1B | NM_018369 | DEP domain containing 1B | 5q12 | -2.1 |
| nulliparous | promoter | USP21 | NM_001014443 | ubiquitin specific peptidase 21 | 1q22 | -6.7 |
| nulliparous | promoter | PRPF6 | NM_012469 | PRP6 pre-mRNA processing factor 6 homolog (S. cerevisiae) | 20q13.33 | -3.9 |
| nulliparous | promoter | C20orf94 | NM_001009608 | chromosome 20 open reading frame 94 | 20p12 | -10.4 |
| nulliparous | promoter | NFE2L2 | NM_006164 | nuclear factor (erythroid-derived 2)-like 2 | 2q31 | -11.6 |
| nulliparous | promoter | ARHGEF5 | NM_005435 | Rho guanine nucleotide exchange factor (GEF) 5 | 7q33-q35 | -3.8 |
| nulliparous | promoter | EIF3E | NM_001568 | eukaryotic translation initiation factor 3, subunit E | 8q22-q23 | -4.1 |
| nulliparous | promoter | NDUFA11 | NM_175614 | NADH dehydrogenase (ubiquinone) 1 alpha subcomplex, 11, 14.7 kDa | 19p13.3 | -5.4 |
| nulliparous | promoter | WNK3 | NM_001002838 | WNK lysine deficient protein kinase 3 | Xp11.22 | -11.6 |
| nulliparous | promoter | MTMR7 | NM_004686 | myotubularin related protein 7 | 8p22 | -3.7 |
| nulliparous | promoter | MKKS | NM_170784 | McKusick-Kaufman syndrome | 20p12 | -10.4 |
| nulliparous | promoter | SPIN1 | NM_006717 | spindlin 1 | 9q22.1 | -4.4 |
| nulliparous | promoter | C2orf55 | NM_207362 | chromosome 2 open reading frame 55 | 2q11.2 | -3.9 |
| nulliparous | promoter | RSPO3 | NM_032784 | R-spondin 3 homolog (Xenopus laevis) | 6q22.33 | -2.4 |
| nulliparous | promoter | TBCCD1 | NM_018138 | TBCC domain containing 1 | 3q27.3 | -2.7 |
| nulliparous | promoter | LIPJ | NM_001010939 | lipase, family member J | 10q23.31 | -2.2 |
| nulliparous | promoter | RAMP3 | NM_005856 | receptor (G protein-coupled) activity modifying protein 3 | 7p13-p12 | -5.5 |
| nulliparous | promoter | WDR21A | NM_015604 | NA | NA | -2.8 |
| nulliparous | promoter | TNFRSF21 | NM_014452 | tumor necrosis factor receptor superfamily, member 21 | 6p21.1 | -6.6 |
| nulliparous | promoter | SSH2 | NM_033389 | slingshot homolog 2 (Drosophila) | 17q11.2 | -4.5 |
| nulliparous | promoter | HRK | NM_003806 | harakiri, BCL2 interacting protein (contains only BH3 domain) | 12q24.2 | -2.6 |
| nulliparous | promoter | SNAI2 | NM_003068 | snail homolog 2 (Drosophila) | 8q11.21 | -7.9 |
| nulliparous | promoter | SYT8 | NM_138567 | synaptotagmin VIII | 11p15.5 | -2.1 |
| nulliparous | promoter | SLC2A9 | NM_020041 | solute carrier family 2 (facilitated glucose transporter), member 9 | 4p16.1 | -9.5 |
| nulliparous | promoter | SLC2A8 | NM_014580 | solute carrier family 2 (facilitated glucose transporter), member 8 | 9q33.3 | -2.1 |
| nulliparous | promoter | SLC2A4 | NM_001042 | solute carrier family 2 (facilitated glucose transporter), member 4 | 17p13 | -7.5 |
| nulliparous | promoter | RCOR1 | NM_015156 | REST corepressor 1 | 14q32.33 | -2.8 |
| nulliparous | promoter | PLEKHA5 | NM_019012 | pleckstrin homology domain containing, family A member 5 | 12p12 | -5.8 |
| nulliparous | promoter | TIGD2 | NM_145715 | tigger transposable element derived 2 | 4q21.3 | -4.9 |
| nulliparous | promoter | FAM36A | NM_198076 | family with sequence similarity 36, member A | 1q44 | -3.4 |
| nulliparous | promoter | FAM36A | NM_198076 | family with sequence similarity 36, member A | 1q44 | -8.1 |
| nulliparous | promoter | HCRTR1 | NM_001525 | hypocretin (orexin) receptor 1 | 1p33 | -2.2 |
| nulliparous | promoter | YIPF3 | NM_015388 | Yip1 domain family, member 3 | 6p21.1 | -4.7 |
| nulliparous | promoter | TMEM42 | NM_144638 | transmembrane protein 42 | 3p21.31 | -4.9 |
| nulliparous | promoter | SNX3 | NM_003795 | sorting nexin 3 | 6q21 | -2.9 |
| nulliparous | promoter | SNX3 | NM_003795 | sorting nexin 3 | 6q21 | 5.9 |
| nulliparous | promoter | DMRT2 | NM_001130865 | doublesex and mab-3 related transcription factor 2 | 9p24.3 | -3.1 |
| nulliparous | promoter | ALG5 | NM_013338 | asparagine-linked glycosylation 5, dolichyl-phosphate beta-glucosyltransferase homolog (S. cerevisiae) | 13q13.1 | -2.7 |
| nulliparous | promoter | DHX38 | NM_014003 | DEAH (Asp-Glu-Ala-His) box polypeptide 38 | 16q22 | -2.9 |
| nulliparous | promoter | FAM73A | NM_198549 | family with sequence similarity 73, member A | 1p31.1 | -7.5 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | EXOSC8 | NM_181503 | exosome component 8 | 13q13. | −2.7 |
| nulliparous | promoter | SLC29A3 | NM_018344 | solute carrier family 29 (nucleoside transporters), member 3 | 10q22.2 | −3.8 |
| nulliparous | promoter | STAM | NM_003473 | signal transducing adaptor molecule (SH3 domain and ITAM motif) 1 | 10p14-p13 | −2.8 |
| nulliparous | promoter | EXOSC7 | NM_015004 | exosome component 7 | 3p21.32 | −7.1 |
| nulliparous | promoter | METTL5D1 | NM_152636 | methyltransferase 5 domain containing 1 | 11p14.1 | −9.8 |
| nulliparous | promoter | YPEL1 | NM_013313 | yippee-like 1 (Drosophila) | 22q11.2 | −4.2 |
| nulliparous | promoter | NEK3 | NM_002498 | NIMA (never in mitosis gene a)-related kinase 3 | 13q14.2-q21.1 | −9.2 |
| nulliparous | promoter | ADAMTSL5 | NM_213604 | ADAMTS-like 5 | 19p13.3 | −6.7 |
| nulliparous | promoter | FLJ22167 | NM_001077416 | NA | NA | −7.2 |
| nulliparous | promoter | TPTE | NM_199261 | transmembrane phosphatase with tensin homology | 21p11 | −2.1 |
| nulliparous | promoter | NID1 | NM_002508 | nidogen 1 | 1q43 | −2.7 |
| nulliparous | promoter | C10orf59 | NM_001031709 | NA | NA | −2.2 |
| nulliparous | promoter | GCC1 | NM_024523 | GRIP and coiled-coil domain containing 1 | 7q22.3 | −4.8 |
| nulliparous | promoter | LCN12 | NM_178536 | lipocalin 12 | 9q34 | −2.7 |
| nulliparous | promoter | TACSTD2 | NM_002353 | tumor-associated calcium signal transducer 2 | 1p32 | −4.2 |
| nulliparous | promoter | GPR160 | NM_014373 | G protein-coupled receptor 160 | 3q26.2-q27 | −3.6 |
| nulliparous | promoter | GPR161 | NM_153832 | G protein-coupled receptor 161 | 1q23.3 | −2.1 |
| nulliparous | promoter | PLXDC2 | NM_032812 | plexin domain containing 2 | 10p12.33 | −5 |
| nulliparous | promoter | TCF4 | NM_001083962 | transcription factor 4 | 18q21.1 | −3 |
| nulliparous | promoter | FABP5L3 | NR_002935 | fatty acid binding protein 5-like 3 (pseudogene) | 7q36.1 | −4.6 |
| nulliparous | promoter | ZNF746 | NM_152557 | zinc finger protein 746 | 7q36.1 | −3.2 |
| nulliparous | promoter | NUDT3 | NM_006703 | nudix (nucleoside diphosphate linked moiety X)-type motif 3 | 6p21.2 | −2.6 |
| nulliparous | promoter | MLLT10 | NM_004641 | myeloid/lymphoid or mixed-lineage leukemia (trithorax homolog, Drosophila); translocated to, 10 | 10p12 | −2.5 |
| nulliparous | promoter | UBE2E2 | NM_152653 | ubiquitin-conjugating enzyme E2E 2 (UBC4/5 homolog, yeast) | 3p24.2 | −8.4 |
| nulliparous | promoter | CNGA3 | NM_001298 | cyclic nucleotide gated channel alpha 3 | 2q11.2 | −3.1 |
| nulliparous | promoter | SNORD76 | NR_003942 | small nucleolar RNA, C/D box 76 | 1q25.1 | −9.1 |
| nulliparous | promoter | MANSC1 | NM_018050 | MANSC domain containing 1 | 12p13.2 | −4.1 |
| nulliparous | promoter | LOC256880 | NR_002799 | NA | NA | −2.1 |
| nulliparous | promoter | SNORD75 | NR_003941 | small nucleolar RNA, C/D box 75 | 1q25.1 | −9.1 |
| nulliparous | promoter | BLVRA | NM_000712 | biliverdin reductase A | 7p14-cen | −19 |
| nulliparous | promoter | SNORD79 | NR_003939 | small nucleolar RNA, C/D box 79 | 1q25.1 | −9.1 |
| nulliparous | promoter | C15orf24 | NM_020154 | chromosome 15 open reading frame 24 | 15q14 | −3.8 |
| nulliparous | promoter | PRRX2 | NM_016307 | paired related homeobox 2 | 9q34.11 | −3.1 |
| nulliparous | promoter | IRF7 | NM_004031 | interferon regulatory factor 7 | 11p15.5 | −2.5 |
| nulliparous | promoter | PAIP2B | NM_020459 | poly(A) binding protein interacting protein 2B | 2p13.3 | −6.4 |
| nulliparous | promoter | MPZL1 | NM_003953 | myelin protein zero-like 1 | 1q24.2 | −5 |
| nulliparous | promoter | COX18 | NM_173827 | COX18 cytochrome c oxidase assembly homolog (S. cerevisiae) | 4q13.3 | −4.7 |
| nulliparous | promoter | BTD | NM_000060 | biotinidase | 3p25 | −2.7 |
| nulliparous | promoter | PFN2 | NM_002628 | profilin 2 | 3q25.1 | −3.8 |
| nulliparous | promoter | HS6ST1 | NM_004807 | heparan sulfate 6-0-sulfotransferase 1 | 2q21 | −3.9 |
| nulliparous | promoter | DEPDC4 | NM_152317 | DEP domain containing 4 | 12q23 | −2.1 |
| nulliparous | promoter | SHISA3 | NM_001080505 | shisa homolog 3 (Xenopus laevis) | 4p13 | −3.8 |
| nulliparous | promoter | COX10 | NM_001303 | COX10 homolog, cytochrome c oxidase assembly protein, heme A:farnesyltransferase (yeast) | 17p12 | −2.6 |
| nulliparous | promoter | CLK2 | NM_003993 | CDC-like kinase 2 | 1q21 | −3.6 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | SCN5A | NM_198056 | sodium channel, voltage-gated, type V, alpha subunit | 3p21 | −5.2 |
| nulliparous | promoter | GAS5 | NR_002578 | growth arrest-specific 5 (non-protein coding) | 1q25.1 | −9.1 |
| nulliparous | promoter | ISLR2 | NM_001130136 | immunoglobulin superfamily containing leucine-rich repeat 2 | 15q24.1 | 3.9 |
| nulliparous | promoter | ISLR2 | NM_001130136 | immunoglobulin superfamily containing leucine-rich repeat 2 | 15q24.1 | −2.4 |
| nulliparous | promoter | SNORA6 | NR_002325 | small nucleolar RNA, H/ACA box 6 | 3p22.2 | −5.9 |
| nulliparous | promoter | ZNF334 | NM_018102 | zinc finger protein 334 | 20 | −6.2 |
| nulliparous | promoter | APIP | NM_015957 | APAF1 interacting protein | 11p13 | −13.1 |
| nulliparous | promoter | CUGBP2 | NM_006561 | CUG triplet repeat, RNA binding protein 2 | 10p13 | −3 |
| nulliparous | promoter | SCYL2 | NM_017900 | SCYHlke 2 (*S. cerevisiae*) | 12q23.1 | −2.1 |
| nulliparous | promoter | AHI1 | NM_001134830 | Abelson helper integration site 1 | 6q23.2 | −2.2 |
| nulliparous | promoter | TEX12 | NM_031275 | testis expressed 12 | 11 | −3 |
| nulliparous | promoter | TTBK2 | NM_173500 | tau tubulin kinase 2 | 15q15.2 | −6 |
| nulliparous | promoter | C21orf45 | NM_018944 | chromosome 21 open reading frame 45 | 21q22.11 | −2.1 |
| nulliparous | promoter | TMSB10 | NM_021103 | thymosin beta 10 | 2p11.2 | −14.2 |
| nulliparous | promoter | STXBP5 | NM_001127715 | syntaxin binding protein 5 (tomosyn) | 6q24.3 | −4.3 |
| nulliparous | promoter | PPA2 | NM_006903 | pyrophosphatase (inorganic) 2 | 4q25 | −3.8 |
| nulliparous | promoter | PPA2 | NM_006903 | pyrophosphatase (inorganic) 2 | 4q25 | −2.6 |
| nulliparous | promoter | OXSR1 | NM_005109 | oxidative-stress responsive 1 | 3p22.2 | −6.8 |
| nulliparous | promoter | CBX8 | NM_020649 | chromobox homolog 8 (Pc class homolog, *Drosophila*) | 17q25.3 | −8 |
| nulliparous | promoter | GPR78 | NM_080819 | G protein-coupled receptor 78 | 4p16.1 | −3.4 |
| nulliparous | promoter | ARHGAP29 | NM_004815 | Rho GTPase activating protein 29 | 1p22.1 | −6.6 |
| nulliparous | promoter | PION | NM_017439 | pigeon homolog (*Drosophila*) | 7q11.23 | −2.5 |
| nulliparous | promoter | PION | NM_017439 | pigeon homolog (*Drosophila*) | 7q11.23 | 15.4 |
| nulliparous | promoter | ALCAM | NM_001627 | activated leukocyte cell adhesion molecule | 3q13.1 | −2.9 |
| nulliparous | promoter | ALCAM | NM_001627 | activated leukocyte cell adhesion molecule | 3q13.1 | −4.7 |
| nulliparous | promoter | KIAA1958 | NM_133465 | KIAA1958 | 9q33.1 | −2.3 |
| nulliparous | promoter | CST3 | NM_000099 | cystatin C | 20p11.2 | −6.4 |
| nulliparous | promoter | E2F7 | NM_203394 | E2F transcription factor 7 | 12q21.1 | −3.4 |
| nulliparous | promoter | NTF3 | NM_001102654 | neurotrophin 3 | 12p13 | −2.2 |
| nulliparous | promoter | MTMR12 | NM_001040446 | myotubularin related protein 12 | 5p15.33 | −3.4 |
| nulliparous | promoter | SNORD77 | NR_003943 | small nucleolar RNA, C/D box 77 | 1q25.1 | −9.1 |
| nulliparous | promoter | DUSP5 | NM_004419 | dual specificity phosphatase 5 | 10q25 | −18.6 |
| nulliparous | promoter | ELMOD2 | NM_153702 | ELMO/CED-12 domain containing 2 | 4q31.1 | −9.5 |
| nulliparous | promoter | SND1 | NM_014390 | staphylococcal nuclease and tudor domain containing 1 | 7q31.3 | −3.2 |
| nulliparous | promoter | JOSD1 | NM_014876 | Josephin domain containing 1 | 22q13.1 | −3.3 |
| nulliparous | promoter | ALDH18A1 | NM_001017423 | aldehyde dehydrogenase 18 family, member A1 | 10q24.3-q24.6 | −4.6 |
| nulliparous | promoter | NAT11 | NM_024771 | N-acetyltransferase 11 (GCN5-related, putative) | 11q13.1 | −3.4 |
| nulliparous | promoter | SLMO1 | NM_006553 | slowmo homolog 1 (*Drosophila*) | 18p11.21 | −2.8 |
| nulliparous | promoter | PIP5K3 | NM_152671 | NA | NA | −2.4 |
| nulliparous | promoter | MLL3 | NM_170606 | myeloid/lymphoid or mixed-lineage leukemia 3 | 7q36 | −4.6 |
| nulliparous | promoter | KIF1B | NM_183416 | kinesin family member 1B | 1p36.22 | −3.8 |
| nulliparous | promoter | PIP5K1C | NM_012398 | phosphatidylinositol-4-phosphate 5-kinase, type I, gamma | 19p13.3 | −3.4 |
| nulliparous | promoter | GRIK1 | NM_175611 | glutamate receptor, ionotropic, kainate 1 | 21q22 | −2.2 |
| nulliparous | promoter | LRRC34 | NM_153353 | leucine rich repeat containing 34 | 3q26.2 | −4.4 |
| nulliparous | promoter | TFIP11 | NM_012143 | tuftelin interacting protein 11 | 22q12.1 | −5.4 |
| nulliparous | promoter | RNF149 | NM_173647 | ring finger protein 149 | 2q12.1 | −2.8 |
| nulliparous | promoter | HOXA5 | NM_019102 | homeobox A5 | 7p15.2 | −9.9 |
| nulliparous | promoter | PPAT | NM_002703 | phosphoribosyl pyrophosphate amidotransferase | 4q21 | −4.5 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | CKAP2L | NM_152515 | cytoskeleton associated protein 2-like | 2q13 | -4.9 |
| nulliparous | promoter | DKFZp434B0335 | NM_015395 | NA | NA | -3.1 |
| nulliparous | promoter | USP8 | NM_005154 | ubiquitin specific peptidase 8 | 15q21.1 | -4.3 |
| nulliparous | promoter | TGFB2 | NM_003238 | transforming growth factor, beta 2 | 1q41 | -4.3 |
| nulliparous | promoter | MGLL | NM_007283 | monoglyceride lipase | 3p13-q13.33 | -4.3 |
| nulliparous | promoter | LIMS3 | NM_033514 | LIM and senescent cell antigen-like domains 3 | 2q14-q21 | -3 |
| nulliparous | promoter | PRSS3 | NM_007343 | protease, serine, 3 | 9p13 | -4.2 |
| nulliparous | promoter | RNF38 | NM_022781 | ring finger protein 38 | 9p | -23.9 |
| nulliparous | promoter | LOC201229 | NM_001076680 | NA | NA | -2.1 |
| nulliparous | promoter | SMARCA5 | NM_003601 | SWI/SNF related, matrix associated, actin dependent regulator of chromatin, subfamily a, member 5 | 4q31.1-q31.2 | -6.6 |
| nulliparous | promoter | SIAH1 | NM_001006610 | seven in absentia homolog 1 (Drosophila) | 16q12 | -8.4 |
| nulliparous | promoter | CNIH3 | NM_152495 | cornichon homolog 3 (Drosophila) | 1q42.12 | -3.2 |
| nulliparous | promoter | UNC119 | NM_005148 | unc-119 homolog (C. elegans) | 17q11.2 | -10.7 |
| nulliparous | promoter | ICA1 | NM_022307 | islet cell autoantigen 1, 69 kDa | 7p22 | -3 |
| nulliparous | promoter | RND3 | NM_005168 | Rho family GTPase 3 | 2q23.3 | -4.9 |
| nulliparous | promoter | DNAJC10 | NM_018981 | DnaJ (Hsp40) homolog, subfamily C, member 10 | 2q32.1 | -4 |
| nulliparous | promoter | CEBPZ | NM_005760 | CCAAT/enhancer binding protein (C/EBP), zeta | 2p22.3 | -6.4 |
| nulliparous | promoter | NANS | NM_018946 | N-acetylneuraminic acid synthase | 9p24.1-p23 | -3.9 |
| nulliparous | promoter | C3orf38 | NM_173824 | chromosome 3 open reading frame 38 | 3p11.1 | -6.4 |
| nulliparous | promoter | CCT6A | NM_001009186 | chaperonin containing TCP1, subunit 6A (zeta 1) | 7p11.2 | -4.1 |
| nulliparous | promoter | GALNT11 | NM_022087 | UDP-N-acetyl-alpha-D-galactosamine:polypeptide N-acetylgalactosaminyltransferase 11 (GalNAc-T 11) | 7q36.1 | -3.7 |
| nulliparous | promoter | ST3GAL1 | NM_003033 | ST3 beta-galactoside alpha-2,3-sialyltransferase 1 | 8q24.22 | -9.4 |
| nulliparous | promoter | INTS7 | NM_015434 | integrator complex subunit 7 | 1q32.3 | -6 |
| nulliparous | promoter | ATAD3A | NM_018188 | ATPase family, AAA domain containing 3A | 1p36.33 | -3.2 |
| nulliparous | promoter | CDC42EP1 | NM_152243 | CDC42 effector protein (Rho GTPase binding) 1 | 22q13.1 | -11.1 |
| nulliparous | promoter | ZBTB8 | NM_001040441 | NA | NA | -2.4 |
| nulliparous | promoter | VCL | NM_014000 | vinculin | 10q22.1-q23 | -3.7 |
| nulliparous | promoter | CHRM2 | NM_000739 | cholinergic receptor, muscarinic 2 | 7q35-q36 | -6 |
| nulliparous | promoter | HIST1H3B | NM_003537 | histone cluster 1, H3b | 6p22.1 | -3.7 |
| nulliparous | promoter | MGAT1 | NM_002406 | mannosyl (alpha-1,3-)-glycoprotein beta-1,2-N-acetylglucosaminyltransferase | 5 | -2.7 |
| nulliparous | promoter | ORC3L | NM_012381 | origin recognition complex, subunit 3-like (yeast) | 6q | -3.5 |
| nulliparous | promoter | MTSS1 | NM_014751 | metastasis suppressor 1 | 8p22 | -2.5 |
| nulliparous | promoter | MTSS1 | NM_014751 | metastasis suppressor 1 | 8p22 | -3.5 |
| nulliparous | promoter | MGC16385 | NM_145039 | NA | NA | -2.2 |
| nulliparous | promoter | LOC389332 | NR_024418 | NA | NA | -2.1 |
| nulliparous | promoter | CADPS | NM_183393 | Ca++-dependent secretion activator | 3p21.1 | -2.9 |
| nulliparous | promoter | SLC16A9 | NM_194298 | solute carrier family 16, member 9 (monocarboxylic acid transporter 9) | 10q21.3 | -2.8 |
| nulliparous | promoter | BAI1 | NM_001702 | brain-specific angiogenesis inhibitor 1 | 8q24 | -2.3 |
| nulliparous | promoter | DDX21 | NM_004728 | DEAD (Asp-Glu-Ala-Asp) box polypeptide 21 | 10q21 | -2.5 |
| nulliparous | promoter | NSUN3 | NM_022072 | NOL1/NOP2/Sun domain family, member 3 | 3q11.2 | -3.1 |
| nulliparous | promoter | NRIP1 | NM_003489 | nuclear receptor interacting protein 1 | 21q11.2 | -8.4 |
| nulliparous | promoter | C20orf103 | NM_012261 | chromosome 20 open reading frame 103 | 20p12 | -7.8 |
| nulliparous | promoter | BTC | NM_001729 | betacellulin | 4q13-q21 | -4.4 |
| nulliparous | promoter | TWISTNB | NM_001002926 | TWIST neighbor | 7p15.3 | -2.4 |
| nulliparous | promoter | psiTPTE22 | NR_001591 | NA | NA | -6.8 |
| nulliparous | promoter | FLVCR2 | NM_017791 | feline leukemia virus subgroup C cellular receptor family, member 2 | 14q24.2 | 3 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | C1orf122 | NM_198446 | chromosome 1 open reading frame 122 | 1p34.3 | −3.3 |
| nulliparous | promoter | SLC6A6 | NM_001134368 | solute carrier family 6 (neurotransmitter transporter, taurine), member 6 | 3p26-p24 | −5.6 |
| nulliparous | promoter | SLC6A4 | NM_001045 | solute carrier family 6 (neurotransmitter transporter, serotonin), member 4 | 17q11.2 | −6.8 |
| nulliparous | promoter | RRP7B | NR_002184 | ribosomal RNA processing 7 homolog B (S. cerevisiae) | 22q13.2 | −2.3 |
| nulliparous | promoter | MCC26718 | NM_001029999 | NA | NA | −3.3 |
| nulliparous | promoter | C1orf74 | NM_152485 | chromosome 1 open reading frame 74 | 1q32.2 | −3.4 |
| nulliparous | promoter | CCNT1 | NM_001240 | cyclin T1 | 12q13.11 | −2.1 |
| nulliparous | promoter | SLC30A7 | NM_133496 | solute carrier family 30 (zinc transporter), member 7 | 1p21.1 | −5.1 |
| nulliparous | promoter | C7orf58 | NM_001105533 | chromosome 7 open reading frame 58 | 7q31.31 | −2.5 |
| nulliparous | promoter | TOMM5 | NM_001001790 | translocase of outer mitochondrial membrane 5 homolog (yeast) | 9p13.2 | −4 |
| nulliparous | promoter | SNORD78 | NR_003944 | small nucleolar RNA, C/D box 78 | 1q25.1 | −9.1 |
| nulliparous | promoter | THRB | NM_001128176 | thyroid hormone receptor, beta (erythroblastic leukemia viral (v-erb-a) oncogene homolog 2, avian) | 3p24.1-p22 | −13.5 |
| nulliparous | promoter | DCC | NM_005215 | deleted in colorectal carcinoma | 18q21.1 | −7.4 |
| nulliparous | promoter | PARD6A | NM_001037281 | par-6 partitioning defective 6 homolog alpha (C. elegans) | 16q22.1-q22.3 | −5.8 |
| nulliparous | promoter | SNORD44 | NR_002750 | small nucleolar RNA, C/D box 44 | 1q25.1 | −9.1 |
| nulliparous | promoter | KIAA1012 | NM_014939 | KIAA1012 | 18q12.1 | −2.1 |
| nulliparous | promoter | FAM110B | NM_147189 | family with sequence similarity 110, member B | 8q12.1 | −2.4 |
| nulliparous | promoter | NPAL2 | NM_024759 | NA | NA | −3.4 |
| nulliparous | promoter | ZNF577 | NR_024181 | zinc finger protein 577 | 19 | −4.1 |
| nulliparous | promoter | NUP214 | NM_005085 | nucleoporin 214 kDa | 9q34 | −17.6 |
| nulliparous | promoter | VSX1 | NM_014588 | visual system homeobox 1 | 20p11.21 | −4.8 |
| nulliparous | promoter | VSX1 | NM_014588 | visual system homeobox 1 | 20p11.21 | 3.2 |
| nulliparous | promoter | A1BG | NM_130786 | alpha-1-B glycoprotein | 19q | −2.3 |
| nulliparous | promoter | PNKP | NM_007254 | polynucleotide kinase 3'-phosphatase | 19q13.3-q13.4 | −4.8 |
| nulliparous | promoter | LRRC4 | NM_022143 | leucine rich repeat containing 4 | 7q31 | −4.5 |
| nulliparous | promoter | GUSB | NM_000181 | glucuronidase, beta | 7q11.21 | −5.8 |
| nulliparous | promoter | EXTL2 | NM_001439 | exostoses (multiple)-like 2 | 1p21 | −5.1 |
| nulliparous | promoter | DNAJB14 | NM_001031723 | DnaJ (Hsp40) homolog, subfamily B, member 14 | 4q23 | −2.1 |
| nulliparous | promoter | CDH24 | NM_022478 | cadherin-like 24 | 14q11.2 | −7.7 |
| nulliparous | promoter | LRRC1 | NM_018214 | leucine rich repeated containing 1 | 6p12.2 | −2.5 |
| nulliparous | promoter | RPL10 | NM_006013 | ribosomal protein L10 | Xq28 | −2.9 |
| nulliparous | promoter | BRD9 | NM_001009877 | bromodomain containing 9 | 5p15.33 | −6.1 |
| nulliparous | promoter | NUPL2 | NM_007342 | nucleoporin like 2 | 7p15 | −2.3 |
| nulliparous | promoter | RPL13 | NM_000977 | ribosomal protein L13 | 16q24.3 | −3.1 |
| nulliparous | promoter | EHHADH | NM_001966 | enoyl-Coenzyme A, hydratase/3-hydroxyacyl Coenzyme A dehydrogenase | 3q26.3-q28 | −2.7 |
| nulliparous | promoter | SETD7 | NM_030648 | SET domain containing (lysine methyltransferase) 7 | 4q31.1 | −3.2 |
| nulliparous | promoter | BRD3 | NM_007371 | bromodomain containing 3 | 9q34 | −10.1 |
| nulliparous | promoter | NME4 | NM_005009 | non-metastatic cells 4, protein expressed in | 16p13.3 | −6.3 |
| nulliparous | promoter | PLD5 | NM_152666 | phospholipase D family, member 5 | 1q43 | −8.2 |
| nulliparous | promoter | HEPN1 | NM_001037558 | HEPACAM opposite strand 1 | 11q24 | −3 |
| nulliparous | promoter | ORMDL1 | NM_016467 | ORM1-like 1 (S. cerevisiae) | 2q32 | −3.5 |
| nulliparous | promoter | LOC38767 | NR_039930 | NA | NA | −4.2 |
| nulliparous | promoter | TTC15 | NM_016030 | tetratricopeptide repeat domain 15 | 2p25.3 | −5.1 |
| nulliparous | promoter | TTC14 | NM_133462 | tetratricopeptide repeat domain 14 | 3q27.2 | −3.5 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | BMPR2 | NM_001204 | bone morphogenetic protein receptor, type II (serine/threonine kinase) | 2q33-q34 | -5.8 |
| nulliparous | promoter | KPNA1 | NM_002264 | karyopherin alpha 1 (importin alpha 5) | 3q21 | -3.5 |
| nulliparous | promoter | NCAPH | NM_015341 | non-SMC condensin I complex, subunit H | 2q11.2 | -2.2 |
| nulliparous | promoter | ZNF37A | NM_003421 | zinc finger protein 37A | 10p11.2 | -3.5 |
| nulliparous | promoter | METT10D | NM_024086 | methyltransferase 10 domain containing | 17p13.3 | -3.2 |
| nulliparous | promoter | TNR_C6B | NM_015088 | trinucleotide repeat containing 6B | 22q13 | -3.1 |
| nulliparous | promoter | FUNDC2 | NM_023934 | FUN 14 domain containing 2 | Xq28 | -4.6 |
| nulliparous | promoter | LOC283951 | NM_001010878 | NA | NA | -2.3 |
| nulliparous | promoter | YME1L1 | NM_014263 | YME1-like 1 (S. cerevisiae) | 10p14 | -5 |
| nulliparous | promoter | KAT2A | NM_021078 | K(lysine) acetyltransferase 2A | 17q12-q21 | -4.1 |
| nulliparous | promoter | LPCAT3 | NM_005768 | lysophosphatidylcholine acyltransferase 3 | 12p13.31 | -3.8 |
| nulliparous | promoter | NPTX2 | NM_002523 | neuronal pentraxin II | 7q21.3-q22.1 | -18.6 |
| nulliparous | promoter | MATR3 | NM_018834 | matrin 3 | 5q31.3 | -2.5 |
| nulliparous | promoter | PECI | NM_006117 | peroxisomal D3,D2-enoyl-CoA isomerase | 6p24.3 | -2.7 |
| nulliparous | promoter | ICOSLG | NM_015259 | inducible T-cell co-stimulator ligand | 21q22.3 | -3.5 |
| nulliparous | promoter | SMURF1 | NM_181349 | SMAD specific E3 ubiquitin protein ligase 1 | 7q21.1-q31.1 | -2.4 |
| nulliparous | promoter | AP2S1 | NM_021575 | adaptor-related protein complex 2, sigma 1 subunit | 19q13.2-q13.3 | -3.2 |
| nulliparous | promoter | C16orf81 | NR_024347 | chromosome 16 open reading frame 81 | 16q24.3 | -6 |
| nulliparous | promoter | PCDHB1 | NM_013340 | protocadherin beta 1 | 5q31 | -10 |
| nulliparous | promoter | EGR1 | NM_001964 | early growth response 1 | 5q23-q31 | -7.5 |
| nulliparous | promoter | PPM1J | NM_005167 | protein phosphatase 1J (PP2C domain containing) | 1p13.1 | -3.1 |
| nulliparous | promoter | USP43 | NM_153210 | ubiquitin specific peptidase 43 | 17p12 | -2.3 |
| nulliparous | promoter | PNPLA3 | NM_025225 | patatin-like phospholipase domain containing 3 | 22q13.31 | -2.3 |
| nulliparous | promoter | UNC5B | NM_170744 | unc-5 homolog B (C. elegans) | 10q22.2 | -3.3 |
| nulliparous | promoter | UNC5B | NM_170744 | unc-5 homolog B (C. elegans) | 10q22.2 | 15.6 |
| nulliparous | promoter | DNAJB11 | NM_016306 | DnaJ (Hsp40) homolog, subfamily B, member 11 | 3q27 | -2.7 |
| nulliparous | promoter | FBLN5 | NM_006329 | fibulin 5 | 14q31 | -2.6 |
| nulliparous | promoter | SLC30A5 | NM_024055 | solute carrier family 30 (zinc transporter), member 5 | 5q12.1 | -2.3 |
| nulliparous | promoter | SENP6 | NM_015571 | SUMO1/sentrin specific peptidase 6 | 6q13-q14.3 | -2.5 |
| nulliparous | promoter | C14orf178 | NM_174943 | chromosome 14 open reading frame 178 | 14q24.3 | -2.8 |
| nulliparous | promoter | FNDC3A | NM_001079673 | fibronectin type III domain containing 3A | 13q14.12 | -21.1 |
| nulliparous | promoter | TMEM74 | NM_153015 | transmembrane protein 74 | 8q23.1 | -8.2 |
| nulliparous | promoter | NPPC | NM_024409 | natriuretic peptide precursor C | 2q24-qter | -2.G |
| nulliparous | promoter | CISD2 | NM_001008388 | CDGSH iron sulfur domain 2 | 4q24 | -2.2 |
| nulliparous | promoter | UBXN2B | NM_001077619 | UBX domain protein 2B | 8q12.1 | -12.8 |
| nulliparous | promoter | RALGPS2 | NM_152663 | Ral GEF with PH domain and SH3 binding motif 2 | 1q24 | -7 |
| nulliparous | promoter | SEC13 | NM_183352 | SEC13 homolog (S. cerevisiae) | 3p25-p24 | -2.9 |
| nulliparous | promoter | FAM86C | NM_001099653 | family with sequence similarity 86, member C | 11q13.4 | -8.3 |
| nulliparous | promoter | FAM86D | NR_024241 | family with sequence similarity 86, member D | 3p12.3 | -3.7 |
| nulliparous | promoter | ZNF581 | NM_016535 | zinc finger protein 581 | 19 | -2.1 |
| nulliparous | promoter | HERC3 | NM_014606 | hect domain and RLD 3 | 4q21 | -3 |
| nulliparous | promoter | ABCD3 | NM_001122674 | ATP-binding cassette, sub-family D (ALD), member 3 | 1p22-p21 | -2.8 |
| nulliparous | promoter | TP53INP1 | NM_001135733 | tumor protein p53 inducible nuclear protein 1 | 8q22 | -2.3 |
| nulliparous | promoter | GPR89B | NM_016334 | G protein-coupled receptor 89B | 1q21.1 | -5.4 |
| nulliparous | promoter | GPR89A | NM_001097612 | G protein-coupled receptor 89A | 1q21.1 | -5.4 |
| nulliparous | promoter | RG9MTD1 | NM_017819 | RNA (guanine-9-) methyltransferase domain containing 1 | 3q12.3 | -15.6 |
| nulliparous | promoter | LMNB2 | NM_032737 | lamin B2 | 19p13.3 | -5.2 |
| nulliparous | promoter | SRrp35 | NM_080743 | NA | NA | -8.1 |
| nulliparous | promoter | MRPS23 | NM_016070 | mitochondrial ribosomal protein S23 | 17q22-q23 | -2.7 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | INSM1 | NM_002196 | insulinoma-associated 1 | 20p11.2 | -2.6 |
| nulliparous | promoter | PCDHGA9 | NM_032089 | protocadherin gamma subfamily A, 9 | 5q31 | 38 |
| nulliparous | promoter | PCDHGA9 | NM_032089 | protocadherin gamma subfamily A, 9 | 5q31 | -3.5 |
| nulliparous | promoter | EIF4EBP2 | NM_004096 | eukaryotic translation initiation factor 4E binding protein 2 | 10q21q22 | 3 |
| nulliparous | promoter | PHF6 | NM_032335 | PHD finger protein 6 | Xq26 | -2.9 |
| nulliparous | promoter | TESSP1 | NM_001135086 | NA | NA | -3.5 |
| nulliparous | promoter | NXNL2 | NM_145283 | nucleoredoxin-like 2 | 9q22.2 | -3.5 |
| nulliparous | promoter | UBE2W | NM_018299 | ubiquitin-conjugating enzyme E2W (putative) | 8q21.11 | -12.7 |
| nulliparous | promoter | FGF21 | NM_019113 | fibroblast growth factor 21 | 19q13.1-qter | -5.5 |
| nulliparous | promoter | NADK | NM_023018 | NAD kinase | 1p36.33 | -7.2 |
| nulliparous | promoter | VMAC | NM_001017921 | vimentin-type intermediate filament associated coiled-coil protein | 19p13.3 | -5.4 |
| nulliparous | promoter | VSTM2L | NM_080607 | V-set and transmembrane domain containing 2 like | 20q11.23 | -2.6 |
| nulliparous | promoter | PF4V1 | NM_002620 | platelet factor 4 variant 1 | 4q12-q21 | -4.9 |
| nulliparous | promoter | MYO1C | NM_033375 | myosin IC | 17p13.3 | -4.2 |
| nulliparous | promoter | B3GNT9 | NM_033309 | UDP-GlcNAc:betaGal beta-1,3-N-acetylglucosaminyl transferase 9 | 16q22.1 | -4.3 |
| nulliparous | promoter | CHST1 | NM_003654 | carbohydrate (keratan sulfate Gal-6) sulfotransferase 1 | 11p11.2 | -5.4 |
| nulliparous | promoter | ADAMTS13 | NM_139027 | ADAM metallopeptidase with thrombospondin type 1 motif, 13 | 9q34 | -3.6 |
| nulliparous | promoter | FBXO7 | NM_001103024 | F-box protein 7 | 22q11.2-qter | -3.3 |
| nulliparous | promoter | KCNA7 | NM_031886 | potassium voltage-gated channel, shaker-related subfamily, member 7 | 19q13.3 | -14 |
| nulliparous | promoter | BCAS4 | NM_198799 | breast carcinoma amplified sequence 4 | 20q13 | -22.1 |
| nulliparous | promoter | SNORD81 | NR_003938 | small nucleolar RNA, C/D box 81 | 1q25.1 | -9.1 |
| nulliparous | promoter | SNORD80 | NR_003940 | small nucleolar RNA, C/D box 80 | 1q25.1 | -9.1 |
| nulliparous | promoter | FAM62B | NM_020728 | NA | NA | -5.3 |
| nulliparous | promoter | FAM62C | NM_031913 | NA | NA | -2.5 |
| nulliparous | promoter | FAM62C | NM_031913 | NA | NA | 44.8 |
| nulliparous | promoter | PGBD4 | NM_152595 | piggyBac transposable element derived 4 | 15q13.1 | -3.8 |
| nulliparous | promoter | STAT1 | NM_007315 | signal transducer and activator of transcription 1, 91 kDa | 2q32.2-q32.3 | -31.2 |
| nulliparous | promoter | CHRNB1 | NM_000747 | cholinergic receptor, nicotinic, beta 1 (muscle) | 17p12-p11 | -2.7 |
| nulliparous | promoter | FAM54A | NM_138419 | family with sequence similarity 54, member A | 6q23.2 | -2.5 |
| nulliparous | promoter | ZHX1 | NM_007222 | zinc fingers and homeoboxes 1 | 8q24.13 | -4.4 |
| nulliparous | promoter | MASTL | NM_032844 | microtubule associated serine/threonine kinase-like | 10p12.1 | -5 |
| nulliparous | promoter | SIAE | NM_170601 | sialic acid acetylesterase | 11q24 | -5.2 |
| nulliparous | promoter | ING1 | NM_198217 | inhibitor of growth family, member 1 | 13q34 | -2.4 |
| nulliparous | promoter | PSMA3 | NM_002788 | proteasome (prosome, macropain) subunit, alpha type, 3 | 14q23 | -3 |
| nulliparous | promoter | LOC100131726 | NR_024479 | NA | NA | -3.7 |
| nulliparous | promoter | ATXN8OS | NR_002717 | ATXN8 opposite strand (non-protein coding) | 13q21 | -3.3 |
| nulliparous | promoter | FTH1 | NM_002032 | ferritin, heavy polypeptide 1 | 11q13 | -2.2 |
| nulliparous | promoter | HIST2H2AA4 | NM_001040874 | histone cluster 2, H2aa4 | 1q21.2 | -5.3 |
| nulliparous | promoter | NDUFA6 | NM_002490 | NADH dehydrogenase (ubiquinone) 1 alpha subcomplex, 6, 14 kDa | 22q13.2-q13.31 | -6 |
| nulliparous | promoter | ZDHHC1 | NM_013304 | zinc finger, DHHC-type containing 1 | 16q22.1 | -8.9 |
| nulliparous | promoter | RPS24 | NM_001026 | ribosomal protein S24 | 10q22 | -3.8 |
| nulliparous | promoter | GALNTL6 | NM_001034845 | UDP-N-acetyl-alpha-D-galactosamine:polypeptide N-acetylgalactosaminyltransferase-like 6 | 4q34.1 | -2.4 |
| nulliparous | promoter | PTP4A3 | NM_032611 | protein tyrosine phosphatase type IVA, member 3 | 8q24.3 | -6.4 |
| nulliparous | promoter | FBXO43 | NM_001077528 | F-box protein 43 | 8q22.3 | -4.5 |
| nulliparous | promoter | GPR64 | NM_001079859 | G protein-coupled receptor 64 | Xp22.13 | -3.3 |
| nulliparous | promoter | THY1 | NM_006288 | Thy-1 cell surface antigen | 11q23.3 | -3.9 |
| nulliparous | promoter | SALL1 | NM_002968 | sal-like 1 (Drosophila) | 16q12.1 | -3.7 |
| nulliparous | promoter | CS | NM_004077 | citrate synthase | 12q13.2 | -9.6 |
| | | | | | 7q31.3 | -4.8 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | FSCN3 | NM_020369 | (ascin homolog 3, actin-bundling protein, testicular (*Strongylocentrotus purpuratus*) | 12q22-q23.1 | -4.5 |
| nulliparous | promoter | NT5DC3 | NM_016575 | 5'-nucleotidase domain containing 3 | 6q22.31 | -2.2 |
| nulliparous | promoter | NT5DC1 | NM_152729 | 5'-nucleotidase domain containing 1 | 2q24-q31 | -5.3 |
| nulliparous | promoter | LRP2 | NM_004525 | low density lipoprotein-related protein 2 | 10q25.1 | -26.3 |
| nulliparous | promoter | C10orf78 | NM_145247 | chromosome 10 open reading frame 78 | 3p21.3 | -5.9 |
| nulliparous | promoter | RPSA | NM_002295 | ribosomal protein SA | 11q13.4 | -2.6 |
| nulliparous | promoter | LRP5 | NM_002335 | low density lipoprotein receptor-related protein 5 | 2p22.2 | -6.4 |
| nulliparous | promoter | C2orf56 | NM_144736 | chromosome 2 open reading frame 56 | 12p12.1 | -3.4 |
| nulliparous | promoter | KCNJ8 | NM_004982 | potassium inwardly-rectifying channel, subfamily J, member 8 | 12q24.1 | -7 |
| nulliparous | promoter | TDG | NM_003211 | thymine-DNA glycosylase | 6p21.3 | -11.8 |
| nulliparous | promoter | NFYA | NM_002505 | nuclear transcription factor Y, alpha | 5p13.2 | -5.9 |
| nulliparous | promoter | C5orf33 | NM_001085411 | chromosome 5 open reading frame 33 | 13q32.3 | -11.1 |
| nulliparous | promoter | TMTC4 | NM_001079669 | transmembrane and tetratricopeptide repeat containing 4 | 6q23.2 | -4.6 |
| nulliparous | promoter | SLC35D3 | NM_001008783 | solute carrier family 35, member D3 | 1p32 | -11.8 |
| nulliparous | promoter | PPIE | NM_006112 | peptidylprolyl isomerase E (cyclophilin E) | 7q36 | -6 |
| nulliparous | promoter | RHEB | NM_005614 | Ras homolog enriched in brain | 3p25.1 | -5.9 |
| nulliparous | promoter | TRNT1 | NM_182916 | tRNA nucleotidyl transferase, CCA-adding, 1 | 9q34.3 | -2.6 |
| nulliparous | promoter | CAMSAP1 | NM_015447 | calmodulin regulated spectrin-associated protein 1 | 7q11.23 | -2.2 |
| nulliparous | promoter | TRIM73 | NM_198924 | tripartite motif-containing 73 | 7q34 | -7.1 |
| nulliparous | promoter | JHDM1D | NM_030647 | jumonji C domain containing histone demethylase 1 homolog D (*S. cerevisiae*) | 10q24.31 | -4 |
| nulliparous | promoter | CUTC | NM_015960 | cutC copper transporter homolog (*E. coli*) | 11q22 | -15 |
| nulliparous | promoter | BIRC3 | NM_001166 | baculoviral IAP repeat-containing 3 | 12q13.11 | -4.9 |
| nulliparous | promoter | RPAP3 | NM_024604 | RNA polymerase II associated protein 3 | 7q22 | -2.1 |
| nulliparous | promoter | MOSPD3 | NM_001040097 | motile sperm domain containing 3 | 10q22.3 | -4.8 |
| nulliparous | promoter | BMPR1A | NM_004329 | bone morphogenetic protein receptor, type IA | 2q24.2 | -5.8 |
| nulliparous | promoter | RBMS1 | NM_002897 | RNA binding motif, single stranded interacting protein 1 | 2q24.2 | -9.5 |
| nulliparous | promoter | RBMS1 | NM_002897 | RNA binding motif, single stranded interacting protein 1 | 6q23.2 | -2.3 |
| nulliparous | promoter | MAP7 | NM_003980 | microtubule-associated protein 7 | 9p13.1 | -2.5 |
| nulliparous | promoter | GNE | NM_005476 | glucosamine (UDP-N-acetyl)-2-epimerase/N-acetylmannosamine kinase | 19q13.41 | -17.9 |
| nulliparous | promoter | ZNF813 | NM_001004301 | zinc finger protein 813 | 4q21.1-q21.21 | -18.4 |
| nulliparous | promoter | ANKRD17 | NM_032217 | ankyrin repeat domain 17 | 16q22.2 | -2.9 |
| nulliparous | promoter | TXNL4B | NM_017853 | thioredoxin-like 4B | NA | -5.9 |
| nulliparous | promoter | FLJ46082 | NM_207417 | NA | 17 | -2.5 |
| nulliparous | promoter | PPP1R1B | NM_032192 | protein phosphatase 1, regulatory (inhibitor) subunit 1B | 1p35 | -2.2 |
| nulliparous | promoter | RNU11 | NR_004407 | RNA, U11 small nuclear | 8p21 | -3.3 |
| nulliparous | promoter | NEFL | NM_006158 | neurofilament, light polypeptide | 5q31 | -4.1 |
| nulliparous | promoter | PCDHGA10 | NM_032090 | protocadherin gamma subfamily A, 10 | 4q32.3 | -2.1 |
| nulliparous | promoter | TMEM192 | NM_001100389 | transmembrane protein 192 | 21q22.2 | -2.1 |
| nulliparous | promoter | CBR3 | NM_001236 | carbonyl reductase 3 | 3q28 | -7.5 |
| nulliparous | promoter | SST | NM_001048 | somatostatin | 3p25.3-P25.2 | -2.5 |
| nulliparous | promoter | ATG7 | NM_001136031 | ATG7 autophagy related 7 homolog (*S. cerevisiae*) | 3q23 | -2.4 |
| nulliparous | promoter | CLSTN2 | NM_022131 | calsyntenin 2 | 4q27 | -7.4 |
| nulliparous | promoter | ANXA5 | NM_001154 | annexin A5 | 17q23.2 | -4.8 |
| nulliparous | promoter | MSI2 | NM_138962 | musashi homolog 2 (*Drosophila*) | 17p12-p11.2 | -2.9 |
| nulliparous | promoter | PIGL | NM_004278 | phosphatidylinositol glycan anchor biosynthesis, class L | 17q21 | -4.1 |
| nulliparous | promoter | HSPB9 | NM_033194 | heat shock protein, alpha-crystallin-related, B9 | 21q22.2 | -2.2 |
| nulliparous | promoter | PIGP | NM_153681 | phosphatidylinositol glycan anchor biosynthesis, class P | 16p13.3 | -7.7 |
| nulliparous | promoter | PIGQ | NM_148920 | phosphatidylinositol glycan anchor biosynthesis, class Q | 1p21 | -2.7 |
| nulliparous | promoter | GCLM | NM_002061 | glutamate-cysteine ligase, modifier subunit | 22q13.1 | -3.3 |
| nulliparous | promoter | GTPBP1 | NM_004286 | GTP binding protein 1 | 2q24.3 | -3.6 |
| nulliparous | promoter | STK39 | NM_013233 | serine threonine kinase 39 (STE20/SPS1 homolog, yeast) | 8q24 | -3.2 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | RNF139 | NM_007218 | ring finger protein 139 | 3q29 | -4.4 |
| nulliparous | promoter | PIGZ | NM_025163 | phosphatidylinositol glycan anchor biosynthesis, class Z | 14q11.2 | -6.8 |
| nulliparous | promoter | THTPA | NM_001126339 | thiamine triphosphatase | 7q21.13 | -2.8 |
| nulliparous | promoter | ZNF804B | NM_181646 | zinc finger protein 804B | 6p21.1 | -11.8 |
| nulliparous | promoter | C6orf130 | NM_145063 | chromosome 6 open reading frame 130 | 15q25.2 | -24.5 |
| nulliparous | promoter | FAM154B | NM_001008226 | family with sequence similarity 154, member B | 5q31 | -2.1 |
| nulliparous | promoter | PCDHA8 | NM_031856 | protocadherin alpha 8 | 5q31 | -2.1 |
| nulliparous | promoter | PCDHA9 | NM_014005 | protocadherin alpha 9 | 1p22 | -3.9 |
| nulliparous | promoter | FAM69A | NM_001006605 | family with sequence similarity 69, member A | 5q34-q35 | -2.8 |
| nulliparous | promoter | DRD1 | NM_000794 | dopamine receptor D1 | 2q31.1 | -3.9 |
| nulliparous | promoter | PDK1 | NM_002610 | pyruvate dehydrogenase kinase, isozyme 1 | 7p13 | -2.6 |
| nulliparous | promoter | PURB | NM_033224 | purine-rich element binding protein B | 3q12.1 | -4.4 |
| nulliparous | promoter | C3orf26 | NM_032359 | chromosome 3 open reading frame 26 | 4q21.2 | -3.5 |
| nulliparous | promoter | KLHL2 | NM_007246 | kelch-like 2, Mayven (Drosophila) | 19p13.2 | -2.1 |
| nulliparous | promoter | ILF3 | NM_001137673 | interleukin enhancer binding factor 3, 90 kDa | 10p15.1 | -6.2 |
| nulliparous | promoter | ASB13 | NM_024701 | ankyrin repeat and SOCS box-containing 13 | 13q12.2 | -4.3 |
| nulliparous | promoter | CDX2 | NM_001265 | caudal type homeobox 2 | 13q12.2 | 5.6 |
| nulliparous | promoter | CDX2 | NM_001265 | caudal type homeobox 2 | 3q27 | -2.2 |
| nulliparous | promoter | MCF2L2 | NM_015078 | MCF.2 cell line derived transforming sequence-like 2 | 16q24.3 | -2.2 |
| nulliparous | promoter | AFG3L1 | NR_003226 | AFG3 ATPase family gene 3-like 1 (S. cerevisiae) | 8q11.21 | -3.3 |
| nulliparous | promoter | KIAA0146 | NM_001080394 | KIAA0146 | 5q31 | -3.5 |
| nulliparous | promoter | PCDHGB6 | NM_032100 | protocadherin gamma subfamily B, 6 | 5q31 | -4.1 |
| nulliparous | promoter | PCDHGB6 | NM_032100 | protocadherin gamma subfamily B, 6 | 5p15 | -3 |
| nulliparous | promoter | POLS | NM_006999 | polymerase (DNA directed) sigma | 3p21.2 | -7 |
| nulliparous | promoter | WDR82 | NM_025222 | WD repeat domain 82 | 19q13.2 | -4.5 |
| nulliparous | promoter | TTC9B | NM_152479 | tetratricopeptide repeat domain 9B | 4p16.3 | -4.7 |
| nulliparous | promoter | ZNF141 | NM_003441 | zinc finger protein 141 | 4p16.3 | -4.6 |
| nulliparous | promoter | ABCA11P | NR_002451 | ATP-binding cassette, sub-family A (ABC1), member 11 (pseudogene) | 14q13.2 | -28.4 |
| nulliparous | promoter | MBIP | NM_016586 | MAP3K12 binding inhibitory protein 1 | 10q22 | -2.4 |
| nulliparous | promoter | NDST2 | NM_003635 | N-deacetylase/N-sulfotransferase (heparan glucosaminyl) 2 | 2q31 | -2.5 |
| nulliparous | promoter | CYBRD1 | NM_024843 | cytochrome b reductase 1 | 7q11.23 | -2.8 |
| nulliparous | promoter | SBDSP | NR_024109 | Shwachman-Bodian-Diamond syndrome pseudogene | 14q23.1 | -3.3 |
| nulliparous | promoter | TOMM20L | NM_207377 | translocase of outer mitochondrial membrane 20 homolog (yeast)-like | NA | -2.5 |
| nulliparous | promoter | EVI1 | NM_001105077 | NA | 19q13.42 | -2.7 |
| nulliparous | promoter | ZNF787 | NM_001002836 | zinc finger protein 787 | 16p11.2 | -2.2 |
| nulliparous | promoter | ZNF785 | NM_152458 | zinc finger protein 785 | 19q13.42 | -2.8 |
| nulliparous | promoter | ZNF784 | NM_203374 | zinc finger protein 784 | 9q34.11 | -2.8 |
| nulliparous | promoter | TTLL11 | NM_001139442 | tubulin tyrosine ligase-like family, member 11 | 20q11.23 | -2.1 |
| nulliparous | promoter | PPP1R16B | NM_015568 | protein phosphatase 1, regulatory (inhibitor) subunit 16B | 1p34 | -3.6 |
| nulliparous | promoter | EDN2 | NM_001956 | endothelin 2 | 12q24.33 | -4.7 |
| nulliparous | promoter | EP400NL | NR_003290 | EP400 N-terminal like | 19q13.1 | -3.2 |
| nulliparous | promoter | ZFP36 | NM_003407 | zinc finger protein 36, C3H type, homolog (mouse) | 12q24.1 | -3.8 |
| nulliparous | promoter | ISCU | NM_213595 | iron-sulfur cluster scaffold homolog (E. coli) | 16p13.13 | -5 |
| nulliparous | promoter | TXNDC11 | NM_015914 | thioredoxin domain containing 11 | 1p13.2 | -3.1 |
| nulliparous | promoter | FAM19A3 | NM_001004440 | family with sequence similarity 19 (chemokine (C-C motif)-like), member A3 | 12q15-q21 | -9.5 |
| nulliparous | promoter | TRHDE | NM_013381 | thyrotropin-releasing hormone degrading enzyme | 2p13 | -5.2 |
| nulliparous | promoter | HK2 | NM_000189 | hexokinase 2 | 10q21-q24 | -5.6 |
| nulliparous | promoter | HTR7 | NM_019860 | 5-hydroxytryptamine (serotonin) receptor 7 (adenylate cyclase-coupled) | 6p23-p22.3 | -2.4 |
| nulliparous | promoter | MYLIP | NM_013262 | myosin regulatory light chain interacting protein | 20 | -4.7 |
| nulliparous | promoter | RAE1 | NM_003610 | RAE1 RNA export 1 homolog (S. pombe) | 13q21 | -3.3 |
| nulliparous | promoter | KLHL1 | NM_020866 | kelch-like 1 (Drosophila) | 2q31-q33 | -3.5 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | PMS1 | NM_001128143 | PMS1 postmeiotic segregation increased 1 (*S. cerevisiae*) | 5q35.2 | −9.7 |
| nulliparous | promoter | MSX2 | NM_002449 | msh homeobox 2 | 1q42.2 | −2.5 |
| nulliparous | promoter | C1orf31 | NM_001012985 | chromosome 1 open reading frame 31 | 11q21 | −16.4 |
| nulliparous | promoter | CCDC82 | NM_024725 | coiled-coil domain containing 82 | 16q22.2 | −5.7 |
| nulliparous | promoter | FTSJD1 | NM_018348 | FtsJ methyltransferase domain containing 1 | 7p22.2 | −2.1 |
| nulliparous | promoter | RSPH10B | NM_173565 | radial spoke head 10 homolog B (*Chlamydomonas*) | 3q26.31 | −8.8 |
| nulliparous | promoter | TNIK | NM_015028 | TRAF2 and NCK interacting kinase | 4q23 | −2.1 |
| nulliparous | promoter | H2AFZ | NM_002106 | H2A histone family, member Z | 5q31.1-q31.3 | −2.9 |
| nulliparous | promoter | GFRA3 | NM_001496 | GDNF family receptor alpha 3 | 12q24.3 | −3.2 |
| nulliparous | promoter | UBC | NM_021009 | ubiquitin C | 6q25.3 | −4.5 |
| nulliparous | promoter | SERAC1 | NM_032861 | serine active site containing 1 | 19 | −2.9 |
| nulliparous | promoter | ZNF564 | NM_144976 | zinc finger protein 564 | 7p22.1 | −2.1 |
| nulliparous | promoter | RSPH10B2 | NM_001099697 | radial spoke head 10 homolog B2 (*Chlamydomonas*) | 12q13.13 | −2.7 |
| nulliparous | promoter | HOXC9 | NM_006897 | homeobox C9 | NA | −6.6 |
| nulliparous | promoter | LOC100125556 | NR_024250 | NA | 17p11.2 | −3.2 |
| nulliparous | promoter | RASD1 | NM_016084 | RAS, dexamethasone-induced 1 | 4q31 | −8 |
| nulliparous | promoter | NR3C2 | NM_000901 | nuclear receptor subfamily 3, group C, member 2 | 10q11.1 | −3.9 |
| nulliparous | promoter | RASSF4 | NM_032023 | Ras association (RalGDS/AF-6) domain family member 4 | 2p13 | −2.4 |
| nulliparous | promoter | EGR4 | NM_001965 | early growth response 4 | 8p21.2 | −4.2 |
| nulliparous | promoter | SLC25A37 | NM_016612 | solute carrier family 25, member 37 | 12q13.13 | −3 |
| nulliparous | promoter | SPRYD3 | NM_032840 | SPRY domain containing 3 | 1p36 | −3.7 |
| nulliparous | promoter | SSU72 | NM_014188 | SSU72 RNA polymerase II CTD phosphatase homolog (*S. cerevisiae*) | 19q13.32 | −2.2 |
| nulliparous | promoter | EML2 | NM_012155 | echinoderm microtubule associated protein like 2 | 7q31-q35 | −3.4 |
| nulliparous | promoter | LRRC61 | NM_023942 | leucine rich repeat containing 61 | 1q32.1 | −4 |
| nulliparous | promoter | NUCKS1 | NM_022731 | nuclear casein kinase and cyclin-dependent kinase substrate 1 | 7q32.3 | −20.1 |
| nulliparous | promoter | FAM40B | NM_001134336 | family with sequence similarity 40, member B | 12q12 | −4.6 |
| nulliparous | promoter | TMEM117 | NM_032256 | transmembrane protein 117 | 11pi3 | −13.1 |
| nulliparous | promoter | PDHX | NM_001135024 | pyruvate dehydrogenase complex, component X | 7 | −4.1 |
| nulliparous | promoter | C7orf36 | NM_020192 | chromosome 7 open reading frame 36 | 12q12 | −3.1 |
| nulliparous | promoter | LRRK2 | NM_198578 | leucine-rich repeat kinase 2 | 20q12 | −17.4 |
| nulliparous | promoter | CHD6 | NM_032221 | chromodomain helicase DNA binding protein 6 | 5q13 | −13.8 |
| nulliparous | promoter | THBS4 | NM_003248 | thrombospondin 4 | 2p24.1 | −3.7 |
| nulliparous | promoter | ASXL2 | NM_018263 | additional sex combs like 2 (*Drosophila*) | 3p25.2 | −4.6 |
| nulliparous | promoter | SNORA7A | NR_002582 | small nucleolar RNA, H/ACA box 7A | Xp21.1 | −2.1 |
| nulliparous | promoter | LANCL3 | NM_198511 | LanC lantibiotic synthetase component C-like 3 (bacterial) | 4q31.3-q33 | −2.9 |
| nulliparous | promoter | GUCY1A3 | NM_001130686 | guanylate cyclase 1, soluble, alpha 3 | 19q13.2-q13.4 | −2.8 |
| nulliparous | promoter | PVRL2 | NM_002856 | poliovirus receptor-related 2 (herpesvirus entry mediator B) | NA | −4.6 |
| nulliparous | promoter | LOC728854 | NR_003615 | NA | Xq23 | −2.5 |
| nulliparous | promoter | ZBTB33 | NM_006777 | zinc finger and BTB domain containing 33 | 11q22.3 | −2.3 |
| nulliparous | promoter | PTS | NM_000317 | 6-pyruvoyltetrahydropterin synthase | 1q24.2 | −9.1 |
| nulliparous | promoter | ZBTB37 | NM_032522 | zinc finger and BTB domain containing 37 | 17q21 | −12 |
| nulliparous | promoter | C1QL1 | NM_006688 | complement component 1, q subcomponent-like 1 | 17q25.3 | −2.1 |
| nulliparous | promoter | SIRT7 | NM_016538 | sirtuin (silent mating type information regulation 2 homolog) 7 (*S. cerevisiae*) | 3q13.2-21q22.2 | −3.2 |
| nulliparous | promoter | LSAMP | NM_002338 | limbic system-associated membrane protein | 22q12.1 | −2.2 |
| nulliparous | promoter | TTC3 | NM_001001894 | tetratricopeptide repeat domain 3 | 2p21 | −2.9 |
| nulliparous | promoter | MN1 | NM_002430 | meningioma (disrupted in balanced translocation) 1 | 3q22.2-q22.3 | −7.9 |
| nulliparous | promoter | RHOQ | NM_012249 | ras homolog gene family, member Q | 4q31.3 | −3.1 |
| nulliparous | promoter | STAG1 | NM_005862 | stromal antigen 1 | 19q13.12 | −2.3 |
| nulliparous | promoter | GLRB | NM_000824 | glycine receptor, beta | 1p33-p32.1 | −2.2 |
| nulliparous | promoter | ANKRD27 | NM_032139 | ankyrin repeat domain 27 (VPS9 domain) | 6p22.1 | −2.1 |
| nulliparous | promoter | YIPF1 | NM_018982 | Yip1 domain family, member 1 | | −8.2 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | HIST1H2BC | NM_003526 | histone cluster 1, H2bc | 12q24.11 | -3.8 |
| nulliparous | promoter | SART3 | NM_014706 | squamous cell carcinoma antigen recognized by T cells 3 | 11p15.1 | -5.3 |
| nulliparous | promoter | NELL1 | NM_006157 | NEL-like 1 (chicken) | 4q21 | -2.4 |
| nulliparous | promoter | FGF5 | NM_004464 | fibroblast growth factor 5 | 11q13.3 | -3.4 |
| nulliparous | promoter | FGF4 | NM_002007 | fibroblast growth factor 4 | 8q22 | -4.5 |
| nulliparous | promoter | POLR2K | NM_005034 | polymerase (RNA) II (DNA directed) polypeptide K, 7.0 kDa | Xq28 | -2.9 |
| nulliparous | promoter | SNORA70 | NR_000011 | small nucleolar RNA, H/ACA box 70 | 5q35.2 | -3 |
| nulliparous | promoter | CPLX2 | NM_006650 | complexin 2 | 17 | -3.1 |
| nulliparous | promoter | PLSCR3 | NM_020360 | phospholipid scramblase 3 | 1q32.1 | -2.7 |
| nulliparous | promoter | CR1L | NM_175710 | complement component (3b/4b) receptor 1-like | 1q41 | -2.2 |
| nulliparous | promoter | SUSD4 | NM_017982 | sushi domain containing 4 | 8p12 | -2.5 |
| nulliparous | promoter | RBPMS | NM_001008712 | RNA binding protein with multiple splicing | 6p22.3 | -3.4 |
| nulliparous | promoter | RBM24 | NM_153020 | RNA binding motif protein 24 | 22q13.1 | -2.6 |
| nulliparous | promoter | MGAT3 | NM_002409 | mannosyl (beta-1,4-)-glycoprotein beta-1,4-N-acetylglucosaminyl transferase | 20q13.12 | -2.7 |
| nulliparous | promoter | TOX2 | NM_001098797 | TOX high mobility group box family member 2 | 4q21.22 | -5.6 |
| nulliparous | promoter | LIN54 | NM_001115008 | lin-54 homolog (C. elegans) | 13q14.11 | -5.3 |
| nulliparous | promoter | KIAA0564 | NM_015058 | KIAA0564 | 6q21 | -2.7 |
| nulliparous | promoter | NR2E1 | NM_003269 | nuclear receptor subfamily 2, group E, member 1 | 2q | -3.8 |
| nulliparous | promoter | AGPS | NM_003659 | alkylglycerone phosphate synthase | 16q22 | -5.8 |
| nulliparous | promoter | ACD | NM_001082486 | adrenocortical dysplasia homolog (mouse) | Xq22 | -3.3 |
| nulliparous | promoter | XKRX | NM_212559 | XK, Kell blood group complex subunit-related, X-linked | 2q24.2 | -2.8 |
| nulliparous | promoter | CD302 | NM_014880 | CD302 molecule | 3q29 | -2.4 |
| nulliparous | promoter | FYTTD1 | NM_001011537 | forty-two-three domain containing 1 | Xp11.23 | -4.2 |
| nulliparous | promoter | GPKOW | NM_015698 | G patch domain and KOW motifs | 21q21 | -3 |
| nulliparous | promoter | NCAM2 | NM_004540 | neural cell adhesion molecule 2 | 7q21 | -2.5 |
| nulliparous | promoter | FZD1 | NM_003505 | frizzled homolog 1 (Drosophila) | 5q13.1 | -3.9 |
| nulliparous | promoter | TNPO1 | NM_002270 | transportin 1 | 15q13.1 | -3.8 |
| nulliparous | promoter | AVEN | NM_020371 | apoptosis, caspase activation inhibitor | 19q13.42 | -2.1 |
| nulliparous | promoter | CCDC106 | NM_013301 | coiled-coil domain containing 106 | 4q12 | -7.9 |
| nulliparous | promoter | SGCB | NM_000232 | sarcoglycan, beta (43 kDa dystrophin-associated glycoprotein) | 8q13.2 | -12.7 |
| nulliparous | promoter | KCNB2 | NM_004770 | potassium voltage-gated channel, Shab-related subfamily, member 2 | 11q24.2 | -5.2 |
| nulliparous | promoter | SPA17 | NM_017425 | sperm autoantigenic protein 17 | 10q11.23 | -3.1 |
| nulliparous | promoter | C10orf72 | NM_001031746 | chromosome 10 open reading frame 72 | 5q34 | -3.4 |
| nulliparous | promoter | FGF18 | NM_003862 | fibroblast growth factor 18 | 6q14 | -6.8 |
| nulliparous | promoter | PHIP | NM_017934 | pleckstrin homology domain interacting protein | 9q34.3 | -5.9 |
| nulliparous | promoter | TTF1 | NM_007344 | transcription termination factor, RNA polymerase I | 10q21.3 | -25.7 |
| nulliparous | promoter | REEP3 | NM_001001330 | receptor accessory protein 3 | 1q32 | -9.8 |
| nulliparous | promoter | CD55 | NM_001114752 | CD55 molecule, decay accelerating factor for complement (Cromer blood group) | 1q32 | -7.2 |
| nulliparous | promoter | PAQR9 | NM_198504 | progestin and adipoQ receptor family member IX | 3q23 | -2.8 |
| nulliparous | promoter | PFDN4 | NM_002623 | prefoldin subunit 4 | 20q13.2 | -2.9 |
| nulliparous | promoter | DTNB | NM_021907 | dystrobrevin, beta | 2p23.2 | -19.3 |
| nulliparous | promoter | GCAT | NM_014291 | glycine C-acetyltransferase (2-amino-3-ketobutyrate coenzyme A ligase) | 22q13.1 | -8.1 |
| nulliparous | promoter | HNRNPUL1 | NM_144732 | heterogeneous nuclear ribonucleoprotein U-like 1 | 19q13.31 | -6.2 |
| nulliparous | promoter | ZNF488 | NM_153034 | zinc finger protein 488 | 10q11.22 | -2.5 |
| nulliparous | promoter | GLB1L2 | NM_138342 | galactosidase, beta 1-like 2 | 11q25 | -5.3 |
| nulliparous | promoter | HIST2H2AA3 | NM_003516 | histone cluster 2, H2aa3 | 1q21.2 | -4.1 |
| nulliparous | promoter | EMILIN2 | NM_032048 | elastin microfibril interfacer 2 | 18p11.3 | -4.1 |
| nulliparous | promoter | PSPH | NM_004577 | phosphoserine phosphatase | 7p11.2 | -2.3 |
| nulliparous | promoter | PKD2 | NM_000297 | polycystic kidney disease 2 (autosomal dominant) | 4q21-q23 | -4.7 |
| nulliparous | promoter | SLAIN1 | NM_001040153 | SLAIN motif family, member 1 | 13q22.3 | -2.3 |
| nulliparous | promoter | RIN3 | NM_024832 | Ras and Rab interactor 3 | 14q32.13 | -7.7 |
| | | | | | 22q13.2 | |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | SREBF2 | NM_004599 | sterol regulatory element binding transcription factor 2 | 17q11.2 | −6.7 |
| nulliparous | promoter | STAT5B | NM_012448 | signal transducer and activator of transcription 5B | 16p13.3 | −6.3 |
| nulliparous | promoter | DECR2 | NM_020664 | 2,4-dienoyl CoA reductase 2, peroxisomal | 1p34 | −2.8 |
| nulliparous | promoter | HIVEP3 | NM_024503 | human immunodeficiency virus type I enhancer binding protein 3 | NA | −2.8 |
| nulliparous | promoter | MGC33894 | NM_152914 | NA | 15q22.31 | −2.4 |
| nulliparous | promoter | CLPX | NM_006660 | ClpX caseinolytic peptidase X homolog (E. coli) | 7q35 | −9.2 |
| nulliparous | promoter | FAM115A | NM_014719 | family with sequence similarity 115, member A | 18q21.1 | −3.4 |
| nulliparous | promoter | HDHD2 | NM_032124 | haloacid dehalogenase-like hydrolase domain containing 2 | NA | −3 |
| nulliparous | promoter | ATPBD3 | NM_145232 | NA | 6q16.2 | −2.8 |
| nulliparous | promoter | MANEA | NM_024641 | mannosidase, endo-alpha | 19p13.2 | −3.5 |
| nulliparous | promoter | JUND | NM_005354 | jun D proto-oncogene | 17q21.32 | −2.9 |
| nulliparous | promoter | HOXB5 | NM_002147 | homeobox B5 | 17q21.32 | 13.8 |
| nulliparous | promoter | HOXB5 | NM_002147 | homeobox B5 | 19q13.11 | −2.2 |
| nulliparous | promoter | RGS9BP | NM_207391 | regulator of G protein signaling 9 binding protein | 15q2 | −3.4 |
| nulliparous | promoter | ADAM10 | NM_001110 | ADAM metallopeptidase domain 10 | 11q22.3 | −2.2 |
| nulliparous | promoter | ZC3H12C | NM_033390 | zinc finger CCCH-type containing 12C | 4q21.3 | −6.5 |
| nulliparous | promoter | SEC31A | NM_014933 | SEC31 homolog A (S. cerevisiae) | 6p22.1 | −3.7 |
| nulliparous | promoter | HIST1H2AB | NM_003513 | histone cluster 1, H2ab | 20pter-q11.23 | −4.5 |
| nulliparous | promoter | ANKRD5 | NM_022096 | ankyrin repeat domain 5 | NA | −2.6 |
| nulliparous | promoter | FAM44A | NM_148894 | NA | 2q37.1 | −16.1 |
| nulliparous | promoter | HJURP | NM_018410 | Holliday junction recognition protein | | |
| nulliparous | promoter | KCNK5 | NM_003740 | potassium channel, subfamily K, member 5 | 6p21 | −8.7 |
| nulliparous | promoter | SVEP1 | NM_153366 | sushi, von Willebrand factor type A, EGF and pentraxin domain containing 1 | 9q31-q32 | −2.6 |
| nulliparous | promoter | PLCXD2 | NM_153268 | phosphatidylinositol-specific phospholipase C, X domain containing 2 | 3q13.2 | −2.2 |
| nulliparous | promoter | RPS19BP1 | NM_194326 | ribosomal protein S19 binding protein 1 | 22q13.1 | −6 |
| nulliparous | promoter | CEP97 | NM_024548 | centrosomal protein 97 kDa | 3q12.3 | −8.6 |
| nulliparous | promoter | MERTK | NM_006343 | c-mer proto-oncogene tyrosine kinase | 2q14.1 | −10 |
| nulliparous | promoter | MERTK | NM_006343 | c-mer proto-oncogene tyrosine kinase | 2q14.1 | 6.2 |
| nulliparous | promoter | LOC147727 | NR_024333 | NA | NA | −2.1 |
| nulliparous | promoter | MPPE1 | NM_023075 | metallophosphoesterase 1 | 18p11.21 | −2.6 |
| nulliparous | promoter | DAPK3 | NM_001348 | death-associated protein kinase 3 | 19p13.3 | −2.5 |
| nulliparous | promoter | DGKD | NM_152879 | diacylglycerol kinase, delta 130 kDa | 2q37 | −2.5 |
| nulliparous | promoter | DGKD | NM_152879 | diacylglycerol kinase, delta 130 kDa | 2q37 | −6.2 |
| nulliparous | promoter | TSSC1 | NM_003310 | tumor suppressing subtransferable candidate 1 | 2p25.3 | −5.1 |
| nulliparous | promoter | KCNJ12 | NM_021012 | potassium inwardly-rectifying channel, subfamily J, member 12 | 17p11.1 | −3.7 |
| nulliparous | promoter | NCOR1 | NM_006311 | nuclear receptor co-repressor 1 | 17p11.2 | −2.9 |
| nulliparous | promoter | HIST1H2AC | NM_003512 | histone cluster 1, H2ac | 6p22.1 | −8.2 |
| nulliparous | promoter | UBAP2 | NM_018449 | ubiquitin associated protein 2 | 9p11.2 | −4.6 |
| nulliparous | promoter | C1orf203 | NR_024126 | chromosome 1 open reading frame 203 | 1p13.1 | −2.1 |
| nulliparous | promoter | GTF2H5 | NM_207118 | general transcription factor IIH, polypeptide 5 | 6q25.3 | −4.5 |
| nulliparous | promoter | UAP1 | NM_003115 | UDP-N-acetylglucosamine pyrophosphorylase 1 | 1q23.2 | −5.2 |
| nulliparous | promoter | RTF1 | NM_015138 | Rtf1, Paf1RNA polymerase II complex component, homolog (S. cerevisiae) | 15q14 | −8 |
| nulliparous | promoter | FBF1 | NM_001080542 | Fas (TNFRSF6) binding factor 1 | 17q25.3 | −3 |
| nulliparous | promoter | FOXN4 | NM_213596 | forkhead box N4 | 12q24.12 | −3 |
| nulliparous | promoter | RASA2 | NM_006506 | RAS p21 protein activator 2 | 3q22-q23 | −2.9 |
| nulliparous | promoter | PCDH8 | NM_032949 | protocadherin 8 | 13q21.1 | −3.9 |
| nulliparous | promoter | SEC22B | NM_004892 | SEC22 vesicle trafficking protein homolog B (S. cerevisiae) | 1q21.1 | −5.1 |
| nulliparous | promoter | RPL38 | NM_001035258 | ribosomal protein L38 | 17q25.1 | −2.7 |
| nulliparous | promoter | TMEM22 | NM_001097599 | transmembrane protein 22 | 3q22.3 | −2.1 |
| nulliparous | promoter | RNF169 | NM_001098638 | ring finger protein 169 | 11q13.4 | −2.1 |
| nulliparous | promoter | RPL32 | NM_000994 | ribosomal protein L32 | 3q13.3-q21 | −4.6 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | PDCD6IP | NM_013374 | programmed cell death 6 interacting protein | 3p22.3 | -6.4 |
| nulliparous | promoter | NEDD4L | NM_015277 | neural precursor cell expressed, developmentally down-regulated 4-like | 18q21 | -6 |
| nulliparous | promoter | LGALS8 | NM_201544 | lectin, galactoside-binding, soluble, 8 | 1q43 | -2.2 |
| nulliparous | promoter | FAM130A1 | NM_030809 | NA | NA | -2.1 |
| nulliparous | promoter | PDPK1 | NM_002613 | 3-phosphoinositide dependent protein kinase-1 | 16p13.3 | -4.4 |
| nulliparous | promoter | LOC729355 | NM_001099687 | NA | NA | -3.8 |
| parous | gene body | RNF17 | NM_031277 | ring finger protein 17 | 13q12.13 | 3.7 |
| parous | gene body | TFAP2E | NM_178548 | transcription factor AP-2 epsilon (activating enhancer binding protein 2 epsilon) | 1p34.3 | 7.9 |
| parous | gene body | PCDHGB1 | NM_032095 | protocadherin gamma subfamily B, 1 | 5q31 | 9.6 |
| parous | gene body | IKBKG | NM_001099856 | inhibitor of kappa light polypeptide gene enhancer in B-cells, kinase gamma | Xq28 | 2.5 |
| parous | gene body | FBP2 | NM_003837 | fructose-1,6-bisphosphatase 2 | 9q22.3 | 9.6 |
| parous | gene body | A2BP1 | NM_018723 | NA | NA | 3.7 |
| parous | gene body | A2BP1 | NM_018723 | NA | NA | -3.5 |
| parous | gene body | RREB1 | NM_001003699 | ras responsive element binding protein 1 | 6p25 | -5.4 |
| parous | gene body | RREB1 | NM_001003699 | ras responsive element binding protein 1 | 6p25 | 3.8 |
| parous | gene body | GAPVD1 | NM_015635 | GTPase activating protein and VPS9 domains 1 | 9q34.11 | 9.6 |
| parous | gene body | LHX3 | NM_014564 | LIM homeobox 3 | 9q34.3 | 6.9 |
| parous | gene body | PRHOXNB | NM_001105577 | parahox cluster neighbor | 13q12.2 | 12.3 |
| parous | gene body | FLJ22536 | NR_015410 | NA | NA | 2.9 |
| parous | gene body | MDH2 | NM_005918 | malate dehydrogenase 2, NAD (mitochondrial) | 7cen-q22 | 5.2 |
| parous | gene body | ADAMTS9 | NM_182920 | ADAM metallopeptidase with thrombospondin type 1 motif, 9 | 3p14.1 | 3.4 |
| parous | gene body | RORB | NM_006914 | RAR-related orphan receptor B | 9q22 | 11.7 |
| parous | gene body | MIB2 | NM_080875 | mindbomb homolog 2 (Drosophila) | 1p36.33 | 4 |
| parous | gene body | DLGAP3 | NM_001080418 | discs, large (Drosophila) homolog-associated protein 3 | 1p35.3-p34.1 | 11.2 |
| parous | gene body | ACBD5 | NM_145698 | acyl-Coenzyme A binding domain containing 5 | 10p12.1 | 3.4 |
| parous | gene body | DLGAP1 | NM_004746 | discs, large (Drosophila) homolog-associated protein 1 | 18p11.3 | 4 |
| parous | gene body | CCDC13 | NM_144719 | coiled-coil domain containing 13 | 3p22.1 | 5.6 |
| parous | gene body | MEM | NM_152513 | meiosis inhibitor 1 | 22q13.2 | 6.3 |
| parous | gene body | GP5 | NM_004488 | glycoprotein V (platelet) | 3q29 | 7.5 |
| parous | gene body | PRPSAP2 | NM_002767 | phosphoribosyl pyrophosphate synthetase-associated protein 2 | 17p12-p11.2 | 33.9 |
| parous | gene body | SCN4B | NM_174934 | sodium channel, voltage-gated, type IV, beta | 11q23.3 | 17.8 |
| parous | gene body | NOL12 | NM_024313 | nucleolar protein 12 | 22q13.1 | 3.3 |
| parous | gene body | OSBPL10 | NM_017784 | oxysterol binding protein-like 10 | 3p23 | 3.4 |
| parous | gene body | ZNF205 | NM_001042428 | zinc finger protein 205 | 16p13.3 | 3.5 |
| parous | gene body | C2orf39 | NM_145038 | chromosome 2 open reading frame 39 | 2p23.3 | 5.6 |
| parous | gene body | DYSF | NM_001130978 | dysferlin, limb girdle muscular dystrophy 2B (autosomal recessive) | 2p13.3 | 2.8 |
| parous | gene body | SCAMP1 | NM_004866 | secretory carrier membrane protein 1 | 5q14.1 | 18.6 |
| parous | gene body | HMGCL | NM_000191 | 3-hydroxymethyl-3-methylglutaryl-Coenzyme A lyase | 1p36.1-p35 | 4.4 |
| parous | gene body | LRRC7 | NM_020794 | leucine rich repeat containing 7 | 1p31.1 | 3.3 |
| parous | gene body | WNK4 | NM_032387 | WNK lysine deficient protein kinase 4 | 17q21-q22 | 7 |
| parous | gene body | CRB2 | NM_173689 | crumbs homolog 2 (Drosophila) | 9q33.2 | 2.4 |
| parous | gene body | ANXA11 | NM_145868 | annexin A11 | 10q22.3 | 5 |
| parous | gene body | STK3 | NM_006281 | serine/threonine kinase 3 (STE20 homolog, yeast) | 8q22.2 | 2.1 |
| parous | gene body | ARRDC2 | NM_001025604 | arrestin domain containing 2 | 19p13.12 | 6.3 |
| parous | gene body | KIRREL2 | NM_199179 | kin of IRRE like 2 (Drosophila) | 19q13.13 | 9.4 |
| parous | gene body | USP34 | NM_014709 | ubiquitin specific peptidase 34 | 2p16.1- | 2.6 |
| parous | gene body | SETD4 | NM_017438 | SET domain containing 4 | 21q22.13 | 5.5 |
| parous | gene body | ADCY4 | NM_139247 | adenylate cyclase 4 | 14q11.2 | 4.2 |
| parous | gene body | CALN1 | NM_001017440 | calneuron 1 | 7q11 | 2.4 |
| parous | gene body | VCX2 | NM_016378 | variable charge, X-linked 2 | Xp22.32 | 3.2 |
| parous | gene body | HCN1 | NM_021072 | hyperpolarization activated cyclic nucleotide-gated potassium channel 1 | 5p12 | 8 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | gene body | HCN3 | NM_020897 | hyperpolanzation activated cyclic nucleotide-gated potassium channel 3 | 1q21.2 | 11 |
| parous | gene body | ITV1 | NM_006303 | NA | NA | 2.6 |
| parous | gene body | TM4SF19 | NM_138461 | transmembrane 4 L six family member 19 | 3q29 | 12.9 |
| parous | gene body | RNF216 | NM_207116 | ring finger protein 216 | 7p22.1 | 2.5 |
| parous | gene body | GGTA1 | NR_003191 | glycoprotein, alpha-galactosyltransferase 1 | 9q33.2 | 5.1 |
| parous | gene body | HSD17B14 | NM_016246 | hydroxysteroid (17-beta) dehydrogenase 14 | 19q13.33 | 36.9 |
| parous | gene body | DTL | NM_016448 | dentideless homolog (Drosophila) | 1q32 | 2.9 |
| parous | gene body | GRIK4 | NM_014619 | glutamate receptor, ionotropic, kainate 4 | 11q | 3.9 |
| parous | gene body | ATP6V1H | NM_213620 | ATPase, H+ transporting, lysosomal 50/57 kDa, V1 subunit H | 8q11.2 | 6.2 |
| parous | gene body | FMN2 | NM_020066 | formin 2 | 1q43 | 6.8 |
| parous | gene body | DNM2 | NM_004945 | dynamin 2 | 19p | 3.9 |
| parous | gene body | UBAP2 | NM_018449 | ubiquitin associated protein 2 | 9p11.2 | 2 |
| parous | gene body | UBAP2 | NM_018449 | ubiquitin associated protein 2 | 9p11.2 | 3.8 |
| parous | gene body | ESRRB | NM_004452 | estrogen-related receptor beta | 14q24.3 | -2.7 |
| parous | gene body | ESRRB | NM_004452 | estrogen-related receptor beta | 14q24.3 | 4.3 |
| parous | gene body | DNAJB13 | NM_153614 | DnaJ (Hsp40) related, subfamily B, member 13 | 11q13.3 | 9.9 |
| parous | gene body | VSX2 | NM_182894 | visual system homeobox 2 | 14q24.3 | 8.8 |
| parous | gene body | RNF220 | NM_018150 | ring finger protein 220 | 1p34.1 | 3.2 |
| parous | gene body | PTPRN2 | NM_130843 | protein tyrosine phosphatase, receptor type, N polypeptide 2 | 7q36 | 7.8 |
| parous | gene body | GRP | NM_002091 | gastrin-releasing peptide | 18q21.1-q21.32 | 13.5 |
| parous | gene body | UNC5B | NM_170744 | unc-5 homolog B (C. elegans) | 10q22.2 | 15.6 |
| parous | gene body | ACSF2 | NM_025149 | acyl-CoA synthetase (amily member 2 | 17q21.33 | 9.2 |
| parous | gene body | STAG1 | NM_005862 | stromal antigen 1 | 3q22.2-q22.3 | 3.7 |
| parous | gene body | HOXB6 | NM_018952 | homeobox B6 | 17q21.32 | 13.8 |
| parous | gene body | GTF2IRD1 | NM_016328 | GTF2I repeat domain containing 1 | 7q11.23 | 2.7 |
| parous | gene body | PAX5 | NM_016734 | paired box 5 | 9p13.2 | -4.3 |
| parous | gene body | PAX5 | NM_016734 | paired box 5 | 9p13.2 | 64.2 |
| parous | gene body | DDN | NM_015086 | dendrin | 12q13 | 3.9 |
| parous | gene body | SPEG | NM_005876 | SPEG complex locus | 2q35 | 3.1 |
| parous | gene body | ZNF28 | NM_006969 | zinc finger protein 28 | 19q13.41 | 15.4 |
| parous | gene body | LEPROTL1 | NM_015344 | leptin receptor overlapping transcript-like 1 | 8p21 | 5.5 |
| parous | gene body | PRDM12 | NM_021619 | PR domain containing 12 | 9q33-q34 | 39 |
| parous | gene body | EXOC3L | NM_178516 | exocyst complex component 3-like | 16q22.1 | 25.5 |
| parous | gene body | CBL | NM_005188 | Cas-Br-M (murine) ecotropic retroviral transforming sequence | 11q23.3-qter | 4.8 |
| parous | gene body | WDR37 | NM_014023 | WD repeat domain 37 | 10p15.3 | 3.7 |
| parous | gene body | HS3ST3B1 | NM_006041 | heparan sulfate (glucosamine) 3-O-sulfotransferase 3B1 | 17p12 | 12.5 |
| parous | gene body | HS3ST3B1 | NM_006041 | heparan sulfate (glucosamine) 3-O-sulfotransferase 3B1 | 17p12 | -4 |
| parous | gene body | GNAL | NM_182978 | guanine nucleotide binding protein (G protein), alpha activating activity polypeptide, olfactory type | 18p11.22-p11.21 | 4.5 |
| parous | gene body | FBXL20 | NM_032875 | F-box and leucine-rich repeat protein 20 | 17q21.2 | 3.4 |
| parous | gene body | GAS7 | NM_201433 | growth arrest-specific 7 | 17p13.1 | 3.1 |
| parous | gene body | HES7 | NM_032580 | hairy and enhancer of split 7 (Drosophila) | 17p13.1 | 214.5 |
| parous | gene body | PHOX2A | NM_005169 | paired-like homeobox 2a | 11q13.4 | 10.5 |
| parous | gene body | OLFM1 | NM_014279 | olfactomedin 1 | 9q34.3 | 2.3 |
| parous | gene body | OLFM1 | NM_014279 | olfactomedin 1 | 9q34.3 | -2.9 |
| parous | gene body | CSMD1 | NM_033225 | CUB and Sushi multiple domains 1 | 8p23.2 | 18.1 |
| parous | gene body | TBX4 | NM_018488 | T-box 4 | 17q21-q22 | 2.5 |
| parous | gene body | GABRA2 | NM_000807 | gamma-aminobutyric acid (GABA) A receptor, alpha 2 | 4p12 | 3 |
| parous | gene body | PSEN1 | NM_007318 | presenilin 1 | 14q24.3 | 2.1 |
| parous | gene body | SGCD | NM_172244 | sarcoglycan, delta (35 kDa dystrophin-associated glycoprotein) | 5q33-q34 | 2.3 |
| parous | gene body | FLJ45983 | NR_024255 | NA | NA | 9 |
| parous | gene body | PPP1R12C | NM_017607 | protein phosphatase 1, regulatory (inhibitor) subunit 12C | 19q13.42 | 3.8 |

TABLE 14-continued

Comprehensive DNA Methylation and K27 Profiles of CD44+ Nulliparous and Parous Breast Epithelial Cells

| | | | | | |
|---|---|---|---|---|---|
| parous | gene body | C22orf30 | NM_173566 | chromosome 22 open reading frame 30 | 22q12.2 | 6.5 |
| parous | gene body | DAGLA | NM_006133 | diacylglycerol lipase, alpha | 11q12.3 | 3 |
| parous | gene body | LYL1 | NM_005583 | lymphoblastic leukemia derived sequence 1 | 19p13.2 | 3.2 |
| parous | gene body | SIAH2 | NM_005067 | seven in absentia homolog 2 (Drosophila) | 3q25 | 16.2 |
| parous | gene body | ADAMTS13 | NM_139027 | ADAM metallopeptidase with thrombospondin type 1 motif, 13 | 9q34 | 5.5 |
| parous | gene body | GNB1 | NM_002074 | guanine nucleotide binding protein (G protein), beta polypeptide 1 | 1p36.33 | 4.8 |
| parous | gene body | LOC221710 | NM_001135575 | NA | NA | 2.6 |
| parous | gene body | SALL4 | NM_020436 | sal-like 4 (Drosophila) | 20q13.2 | 5.7 |
| parous | gene body | LDLR | NM_000527 | low density lipoprotein receptor | 19p13.3 | 6.1 |
| parous | gene body | FU34048 | NR_015448 | NA | NA | 111.1 |
| parous | gene body | GMEB2 | NM_012384 | glucocorticoid modulatory element binding protein 2 | 20q13.33 | 3.9 |
| parous | gene body | LEF1 | NM_001130713 | lymphoid enhancer-binding factor 1 | 4q23-q25 | 2.8 |
| parous | gene body | SEMA3B | NM_004636 | sema domain, immunoglobulin domain (Ig), short basic domain, secreted, (semaphorin) 3B | 3p21.3 | 6.2 |
| parous | gene body | GALNT13 | NM_052917 | UDP-N-acetyl-alpha-D-galactosamine:polypeptide N-acetylgalactosaminyltransferase 13 (GalNAc-T13) | 2q24.1 | 6.5 |
| parous | gene body | NTN1 | NM_004822 | netrin 1 | 17p13-p12 | 8.4 |
| parous | gene body | URM1 | NM_001135947 | ubiquitin related modifier 1 homolog (S. cerevisiae) | 9q34.13 | 3.5 |
| parous | gene body | ADARB2 | NM_018702 | adenosine deaminase, RNA-specific, B2 (RED2 homolog rat) | 10p15.3 | 8.7 |
| parous | gene body | SSTR1 | NM_001049 | somatostatin receptor 1 | 14q13 | 3.5 |
| parous | gene body | AGPAT3 | NM_020132 | 1-acylglycerol-3-phosphate O-acyltransferase 3 | 21q22.3 | 4.2 |
| parous | gene body | C18orf1 | NM_181482 | chromosome 18 open reading frame 1 | 18p11.21 | 30.1 |
| parous | gene body | SLC35D2 | NM_007001 | solute carrier family 35, member D2 | 9q22.33 | 16.2 |
| parous | gene body | PDE4B | NM_001037340 | phosphodiesterase 4B, cAMP-spedfic (phosphodiesterase E4 dunce homolog, Drosophila) | 1p31 | 10 |
| parous | gene body | ADAM15 | NM_207194 | ADAM metallopeptidase domain 15 | 1q21.3 | 50.5 |
| parous | gene body | KRT12 | NM_000223 | keratin 12 | 17q11-q12 | 14.8 |
| parous | gene body | LATS1 | NM_004690 | LATS, large tumor suppressor, homolog 1 (Drosophila) | 6q25.1 | 2.3 |
| parous | gene body | COG8 | NM_032382 | component of oligomeric golgi complex 8 | 16q22.1 | 13.7 |
| parous | gene body | GNAZ | NM_002073 | guanine nucleotide binding protein (G protein), alpha z polypeptide | 22q11.1-q11.2 | 7.2 |
| parous | gene body | ABAT | NM_020686 | 4-aminobutyrate aminotransferase | 16p13.2 | 2.8 |
| parous | gene body | HIST1H2AD | NM_153427 | histone cluster 1, H2ad | 6p22.1 | 3.2 |
| parous | gene body | PITX2 | NM_198836 | paired-like homeodomain 2 | 4q25 | 21.9 |
| parous | gene body | ACACA | NM_002653 | acetyl-Coenzyme A carboxylase alpha | 17q21 | 11.3 |
| parous | gene body | PITX1 | NM_001079843 | paired-like homeodomain 1 | 5q31.1 | 30.5 |
| parous | gene body | CASZ1 | NM_005044 | castor zinc finger 1 | 1p36.22 | 73.3 |
| parous | gene body | PRKX | NM_005044 | protein kinase, X-linked | Xp22.3 | 2.6 |
| parous | gene body | EEA1 | NM_003566 | early endosome antigen 1 | 12q22 | 2.6 |
| parous | gene body | PLOD3 | NM_001084 | procollagen-lysine, 2-oxoglutarate 5 dioxygenase 3 | 7q36 | 3.4 |
| parous | gene body | DGKO | NM_001347 | diacylglycerol kinase, theta 110 kDa | 4p16.3 | 25.9 |
| parous | gene body | N-PAC | NM_032569 | NA | NA | 15.2 |
| parous | gene body | SUPT3H | NM_003599 | suppressor of Ty 3 homolog (S. cerevisiae) | 6p21.1-p12.3 | 3.7 |
| parous | gene body | GGNBP2 | NM_024835 | gametogenetin binding protein 2 | 17q21.1 | 2.8 |
| parous | gene body | DOK6 | NM_152721 | docking protein 6 | 18q22.2 | 3.2 |
| parous | gene body | KCNS1 | NM_002251 | potassium voltage-gated channel, delayed-rectifier, subfamily S, member 1 | 20q12 | 4.1 |
| parous | gene body | PHOSPHO1 | NM_178500 | phosphatase, orphan 1 | 17q21.32 | 37.7 |
| parous | gene body | EFR3B | NM_014971 | EFR3 homolog B (S. cerevisiae) | 2p24.1 | 7.2 |
| parous | gene body | CPT1A | NM_001876 | carnitine palmitoyltransferase 1A (liver) | 11q13.2 | 2.7 |
| parous | gene body | SOX2OT | NR_004053 | SOX2 overlapping transcript (non-protein coding) | 3q26.3- | 9.6 |
| parous | gene body | KIAA1303 | NM_020761 | NA | NA | 3.3 |
| parous | gene body | ZBTB4 | NM_001128833 | zinc finger and BTB domain containing 4 | 17p13.2 | 12 |
| parous | gene body | MSI1 | NM_002442 | musashi homolog 1 (Drosophila) | 12q24 | 2.5 |
| parous | gene body | ACAP1 | NM_014716 | ArfGAP with coiled-coil, ankyrin repeat and PH domains 1 | 17p13.1 | 110.4 |
| parous | gene body | RTN3 | NM_006054 | reticulon 3 | 11q13 | 2.4 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | gene body | GTPBP5 | NM_015666 | GTP binding protein 5 (putative) | 20q13.33 | 2.1 |
| parous | gene body | NR2E1 | NM_003269 | nuclear receptor subfamily 2, group E, member 1 | 6q21 | 7.3 |
| parous | gene body | GPC6 | NM_005708 | glypican 6 | 13q32 | 4.2 |
| parous | gene body | VCX | NM_013452 | variable charge, X-linked | Xp22.31 | 3.2 |
| parous | gene body | CLTCL1 | NM_007098 | clathrin, heavy chain-like 1 | 22q11.2 | 5.5 |
| parous | gene body | IPPK | NM_022755 | inositol 1,3,4,5,6-pentakisphosphate 2-kinase | 9q22.31 | 2.8 |
| parous | gene body | SAMHD1 | NM_015474 | SAM domain and HD domain 1 | 20pter-q12 | 6.2 |
| parous | gene body | KDELR3 | NM_016657 | KDEL (Lys-Asp-Glu-Leu) endoplasmic reticulum protein retention receptor 3 | 22q13 | 2.3 |
| parous | gene body | RTDR1 | NM_014433 | rhabdoid tumor deletion region gene 1 | 22q11.2 | 7.2 |
| parous | gene body | MAP3K13 | NM_004721 | mitogen-activated protein kinase kinase kinase 13 | 3q27 | 2.3 |
| parous | gene body | CD163L1 | NM_174941 | CD 163 molecule-like 1 | 12p13.31 | 288.4 |
| parous | gene body | SFRS11 | NM_004768 | splicing factor, arginine/serine-rich 11 | 1p31.1 | 5.4 |
| parous | gene body | CDR2 | NM_001802 | cerebellar degeneration-related protein 2, 62 kDa | 16p13.1- | 2.3 |
| parous | gene body | NFIX | NM_002501 | nuclear factor I/X (CCAAT-binding transcription factor) | 19p13.3 | 3.2 |
| parous | gene body | POU2F2 | NM_002698 | POU class 2 homeobox 2 | 19q13.2 | 11 |
| nulliparous | gene body | SND1 | NM_014390 | staphylococcal nuclease and tudor domain containing 1 | 7q31.3 | -4.5 |
| nulliparous | gene body | GTF2IP1 | NR_002206 | general transcription factor IIi, pseudogene 1 | 7q11.23 | -2.1 |
| nulliparous | gene body | LTK | NM_002344 | leukocyte receptor tyrosine kinase | 15q15.1-q21.1 | -6.7 |
| nulliparous | gene body | C7orf50 | NM_032350 | chromosome 7 open reading frame 50 | 7p22.3 | -4.8 |
| nulliparous | gene body | LOC100130987 | NR_024469 | NA | NA | -17.1 |
| nulliparous | gene body | A2BP1 | NM_018723 | NA | NA | 3.7 |
| nulliparous | gene body | A2BP1 | NM_018723 | NA | NA | -3.5 |
| nulliparous | gene body | RREB1 | NM_001003699 | ras responsive element binding protein 1 | 6p25 | -5.4 |
| nulliparous | gene body | RREB1 | NM_001003699 | ras responsive element binding protein 1 | 6p25 | 3.8 |
| nulliparous | gene body | CACNA1H | NM_021098 | calcium channel, voltage-dependent, T type, alpha 1H subunit | 16p13.3 | -2.7 |
| nulliparous | gene body | SMG6 | NM_017575 | Smg-6 homolog, nonsense mediated mRNA decay (actor (C. elegans) | 17p13.3 | -2.1 |
| nulliparous | gene body | PEBP4 | NM_144962 | phosphatidylethanolamine-binding protein 4 | 8p21.3 | -2.7 |
| nulliparous | gene body | NTNG1 | NM_014917 | netrin G1 | 1p13.2-p13.1 | -9 |
| nulliparous | gene body | C12orf51 | NM_001109662 | chromosome 12 open reading frame 51 | 12q24.13 | -2.4 |
| nulliparous | gene body | PARD6G | NM_032510 | par-6 partitioning defective 6 homolog gamma (C. elegans) | 18q23 | -9 |
| nulliparous | gene body | CACNA1A | NM_001127221 | calcium channel, voltage-dependent, P/Q type, alpha 1A subunit | 19p13 | -2.2 |
| nulliparous | gene body | ARHGEF4 | NM_015320 | Rho guanine nucleotide exchange factor (GEF) 4 | 2q22 | -2.5 |
| nulliparous | gene body | SLC5A10 | NM_152351 | solute carrier family 5 (sodium/glucose cotransporter), member 10 | 17p11.2 | -3.8 |
| nulliparous | gene body | C12orf59 | NM_153022 | chromosome 12 open reading frame 59 | 12p13.2 | -8 |
| nulliparous | gene body | SLC12A5 | NM_001134771 | solute carrier family 12 (potassium-chloride transporter), member 5 | 20q13.12 | -4.4 |
| nulliparous | gene body | PCSK2 | NM_002594 | proprotein convertase subtilisin/kexin type 2 | 20p11.2 | -10 |
| nulliparous | gene body | LOC283951 | NM_001101878 | NA | NA | -2.3 |
| nulliparous | gene body | ZNF787 | NM_001002836 | zinc finger protein 787 | 19q13.42 | -2.7 |
| nulliparous | gene body | SPN | NM_001030288 | sialophorin | 16p11.2 | -2.3 |
| nulliparous | gene body | SPTLC1 | NM_006415 | serine palmitoyltransferase, long chain base subunit 1 | 9q22.31 | -2.1 |
| nulliparous | gene body | IRX1 | NM_024337 | iroquois homeobox 1 | 5p15.33 | -2.3 |
| nulliparous | gene body | ONECUT1 | NM_004498 | one cut homeobox 1 | 15q21.3 | -2.4 |
| nulliparous | gene body | LOC145783 | NR_015419 | NA | NA | -3.3 |
| nulliparous | gene body | ZNF43 | NM_003423 | zinc finger protein 43 | 19p13.1-p12 | -2.4 |
| nulliparous | gene body | TSC22D1 | NM_183422 | TSC22 domain family, member 1 | 13q14 | -5.7 |
| nulliparous | gene body | KCNAB1 | NM_172160 | potassium voltage-gated channel, shaker-related subfamily, beta member 1 | 3q26.1 | -3.3 |
| nulliparous | gene body | KCNAB1 | NM_172160 | potassium voltage-gated channel, shaker-related subfamily, beta member 1 | 3q26.1 | -2.3 |
| nulliparous | gene body | LOC100093631 | NR_003580 | NA | NA | -2.1 |
| nulliparous | gene body | SSH2 | NM_033389 | slingshot homolog 2 (Drosophila) | 17q11.2 | -2.5 |
| nulliparous | gene body | OPA3 | NM_001017989 | optic atrophy 3 (autosomal recessive, with chorea and spastic paraplegia) | 19q13.2-q13.3 | -2.7 |
| nulliparous | gene body | OCA2 | NM_000275 | oculocutaneous albinism II | 15q11.2- | -6 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | gene body | GATA6 | NM_005257 | GATA binding protein 6 | 18q11-q12 | -3.1 |
| nulliparous | gene body | ADRA1D | NM_000678 | adrenergic, alpha-1D-, receptor | 20p13 | -3.1 |
| nulliparous | gene body | FAM172A | NM_032042 | family with sequence similarity 172, member A | 5q15 | -5.1 |
| nulliparous | gene body | HEPN1 | NM_001037558 | HEPACAM opposite strand 1 | 11q24 | -3 |
| nulliparous | gene body | PDXDC1 | NM_015027 | pyridoxal-dependent decarboxylase domain containing 1 | 16p13.11 | -13.1 |
| nulliparous | gene body | CALD1 | NM_033157 | caldesmon 1 | 7q33 | -2.4 |
| nulliparous | gene body | RFX1 | NM_002918 | regulatory factor X, 1 (influences HLA class II expression) | 19p13.1 | -6.4 |
| nulliparous | gene body | 38238 | NM_001113491 | NA | NA | -2.4 |
| nulliparous | gene body | NR1I2 | NM_003889 | nuclear receptor subfamily 1, group I, member 2 | 3q12-q13.3 | -3.8 |
| nulliparous | gene body | RUNX1 | NM_001754 | runt-related transcription factor 1 | 21q22.3 | -8.1 |
| nulliparous | gene body | UBC | NM_021009 | ubiquitin C | 12q24.3 | -3.2 |
| nulliparous | gene body | PRRX1 | NM_006902 | paired related homeobox 1 | 1q24.3 | -2.7 |
| nulliparous | gene body | KLC3 | NM_177417 | kinesin light chain 3 | 19q13 | -2.5 |
| nulliparous | gene body | ATP9B | NM_198531 | ATPase, class II, type 9B | 18q23 | -5.9 |
| nulliparous | gene body | LGR6 | NM_001017403 | leucine-rich repeat-containing G protein-coupled receptor 6 | 1q32.1 | -2.1 |
| nulliparous | gene body | ST3GAL2 | NM_006927 | ST3 beta-galactoside alpha-2,3-sialyltransferase 2 | 16q22.3 | -2.4 |
| nulliparous | gene body | GLIS1 | NM_147193 | GLIS family zinc finger 1 | 1p32.3 | -3.1 |
| nulliparous | gene body | KCNQ1OT1 | NR_002728 | KCNQ1 overlapping transcript 1 (non-protein coding) | 11p15.5 | -4.9 |
| nulliparous | gene body | LOC100192378 | NR_024360 | NA | NA | -3.6 |
| nulliparous | gene body | MDGA1 | NM_153487 | MAM domain containing glycosylphosphatidylinositol anchor 1 | 6p21 | -2.8 |
| nulliparous | gene body | BAZ2A | NM_013449 | bromodomain adjacent to zinc finger domain, 2A | 12q13.3 | -2.5 |
| nulliparous | gene body | MNX1 | NM_005515 | motor neuron and pancreas homeobox 1 | 7q36 | -3.6 |
| nulliparous | gene body | CHIC2 | NM_012110 | cysteine-rich hydrophobic domain 2 | 4q11 | -6.4 |
| nulliparous | gene body | TRAP1 | NM_016292 | TNF receptor-associated protein 1 | 16p13.3 | -2.7 |
| nulliparous | gene body | TNRC18 | NM_001080495 | trinucleotide repeat containing 18 | 7p22.1 | -3.2 |
| nulliparous | gene body | JUN | NM_002228 | jun oncogene | 1p32-p31 | -11.1 |
| nulliparous | gene body | MEOX1 | NM_004527 | mesenchyme homeobox 1 | 17q21.31 | -2.6 |
| nulliparous | gene body | TMEM181 | NM_020823 | transmembrane protein 181 | 6q25.3 | -3.3 |
| nulliparous | gene body | AKT1S1 | NM_032375 | AKT1 substrate 1 (proline-rich) | 19q13.33 | -4.8 |
| nulliparous | gene body | PIK3R1 | NM_181523 | phosphoinositide-3-kinase, regulatory subunit 1 (alpha) | 5q13.1 | -2.1 |
| nulliparous | gene body | DIO3 | NM_001362 | deiodinase, iodothyronine, type III | 14q32 | -7.7 |
| nulliparous | gene body | GRM5 | NM_000842 | glutamate receptor, metabotropic 5 | 11q14.3 | -2.9 |
| nulliparous | gene body | KCNIP3 | NM_013434 | Kv channel interacting protein 3, calsenilin | 2q21.1 | -5.5 |
| nulliparous | gene body | TCF4 | NM_001083962 | transcription factor 4 | 18q21.1 | -2.4 |
| nulliparous | gene body | TFR2 | NM_003227 | transferrin receptor 2 | 7q22 | -3.4 |
| nulliparous | gene body | TFR2 | NM_003227 | transferrin receptor 2 | 7q22 | -2.2 |
| nulliparous | gene body | ITGAM | NM_000632 | integrin, alpha M (complement component 3 receptor 3 subunit) | 16p11.2 | -4.8 |
| nulliparous | gene body | POM121 | NM_172020 | POM121 membrane glycoprotein (rat) | 7p11.23 | -6.9 |
| nulliparous | gene body | KCNK15 | NM_022358 | potassium channel, subfamily K, member 15 | 20q13.12 | -4 |
| nulliparous | gene body | NLRP7 | NM_139176 | NLR family, pyrin domain containing 7 | 19q13.42 | -3.1 |
| nulliparous | gene body | KCNQ1 | NM_000218 | potassium voltage-gated channel, KQT-like subfamily, member 1 | 11p15.5 | -4.9 |
| nulliparous | gene body | KCNQ1 | NM_000218 | potassium voltage-gated channel, KQT-like subfamily, member 1 | 11p15.5 | -3.3 |
| nulliparous | gene body | PAX5 | NM_016734 | paired box 5 | 9p13.2 | -4.3 |
| nulliparous | gene body | PAX5 | NM_016734 | paired box 5 | 9p13.2 | 64.2 |
| nulliparous | gene body | CUX1 | NM_181552 | cut-like homeobox 1 | 7q22.1 | -2.1 |
| nulliparous | gene body | TP53INP1 | NM_001135733 | tumor protein p53 inducible nuclear protein 1 | 8q22 | -2.3 |
| nulliparous | gene body | ZMIZ2 | NM_031449 | zinc finger, MIZ-type containing 2 | 7p13 | -2.1 |
| nulliparous | gene body | NELL1 | NM_006157 | NEL-like 1 (chicken) | 11p15.1 | -5.3 |
| nulliparous | gene body | LMO3 | NM_001001395 | LIM domain only 3 (rhombotin-like 2) | 12p13 | -3.7 |
| nulliparous | gene body | ING1 | NM_198217 | inhibitor of growth family, member 1 | 13q34 | -2.4 |
| nulliparous | gene body | ANKRD29 | NM_173505 | ankyrin repeat domain 29 | 18q11.2 | -2.1 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | gene body | ZEB2 | NM_014795 | zinc finger E-box binding homeobox 2 | 2q22.3 | −2.2 |
| nulliparous | gene body | UBE2K | NM_005339 | ubiquitin-conjugating enzyme E2K (UBC1 homolog, yeast) | 4p14 | −3.7 |
| nulliparous | gene body | CIZ1 | NM_012127 | CDKN1A interacting zinc finger protein 1 | 9q34.1 | −2.9 |
| nulliparous | gene body | ERLIN2 | NM_007175 | ER lipid raft associated 2 | 8p11.2 | −3.8 |
| nulliparous | gene body | FLJ36208 | NM_176677 | NA | NA | −7.7 |
| nulliparous | gene body | HLCS | NM_000411 | holocarboxylase synthetase (biotin-(proprionyl-Coenzyme A-carboxylase (ATP-hydrolysing)) ligase) | 21q22.1 | −3.4 |
| nulliparous | gene body | LOC64643 | NM_001101401 | NA | NA | −6.4 |
| nulliparous | gene body | CAMKK2 | NM_153500 | calcium/calmodulin-dependent protein kinase kinase 2, beta | 12q24.2 | −2.6 |
| nulliparous | gene body | FTCD | NM_006657 | formiminotransferase cyclodeaminase | 21q22.3 | −2.6 |
| nulliparous | gene body | HECW1 | NM_015052 | HECT, C2 and WW domain containing E3 ubiquitin protein ligase 1 | 7p13 | −2.4 |
| nulliparous | gene body | RBM20 | NM_001134363 | RNA binding motif protein 20 | 10q25.3 | −4.5 |
| nulliparous | gene body | SHISA3 | NM_001080505 | shisa homolog 3 (Xenopus laevis) | 4p13 | −3.8 |
| nulliparous | gene body | C10orf47 | NM_153256 | chromosome 10 open reading frame 47 | 10p14 | −4.9 |
| nulliparous | gene body | BEST2 | NM_017682 | bestrophin 2 | 19p13.2-p13.12 | −2.6 |
| nulliparous | gene body | PRDM8 | NM_020226 | PR domain containing 8 | 4q21 | −2.1 |
| nulliparous | gene body | OBSCN | NM_052843 | obscurin, cytoskeletal calmodulin and titin-interacting RhoGEF | 1q42 | −3.8 |
| nulliparous | gene body | HS3ST3B1 | NM_006041 | heparan sulfate (glucosamine) 3-O-sulfotransferase 3B1 | 17p12 | 12.5 |
| nulliparous | gene body | HS3ST3B1 | NM_006041 | heparan sulfate (glucosamine) 3-O-sulfotransferase 3B1 | 17p12 | −4 |
| nulliparous | gene body | RASIP1 | NM_017805 | Ras interacting protein 1 | 19q13.33 | −3.7 |
| nulliparous | gene body | SORCS1 | NM_052918 | sortilin-related VPS 10 domain containing receptor 1 | 10q23-q25 | −5.6 |
| nulliparous | gene body | SLC32A1 | NM_080552 | solute carrier family 32 (GABA vesicular transporter), member 1 | 20q11 | −6.7 |
| nulliparous | gene body | MYO1D | NM_015194 | myosin ID | 17q11-q12 | −4.2 |
| nulliparous | gene body | TMEM161A | NM_017814 | transmembrane protein 161A | 19p13.11 | −2.1 |
| nulliparous | gene body | LOC285205 | NR_015394 | NA | NA | −4.6 |
| nulliparous | gene body | OLFM1 | NM_014279 | olfactomedin 1 | 9q34.3 | 2.3 |
| nulliparous | gene body | OLFM1 | NM_014279 | olfactomedin 1 | 9q34.3 | −2.9 |
| nulliparous | gene body | ADAMTS12 | NM_030955 | ADAM metallopeptidase with thrombospondin type 1 motif, 12 | 5q35 | −2.6 |
| nulliparous | gene body | CTNND2 | NM_001332 | catenin (cadherin-associated protein), delta 2 (neural plakophilin-related arm-repeat protein) | 5p15.2 | −6.2 |
| nulliparous | gene body | BBC3 | NM_014417 | BCL2 binding component 3 | 19q13.3-q13.4 | −2.6 |
| nulliparous | gene body | PIGY | NM_001042616 | phosphatidylinositol glycan anchor biosynthesis, class Y | 4q22.1 | −5.1 |
| nulliparous | gene body | GRASP | NM_181711 | GRP1 (general receptor for phosphoinositides 1)-associated scaffold protein | 12q | −3 |
| nulliparous | gene body | IGF2R | NM_000876 | insulin-like growth factor 2 receptor | 6q25-q27 | −2.9 |
| nulliparous | gene body | DOCK11 | NM_144658 | dedicator of cytokinesis 11 | Xq24 | −2 |
| nulliparous | gene body | DOCK11 | NM_144658 | dedicator of cytokinesis 11 | Xq24 | −2.5 |
| nulliparous | gene body | LHFPL2 | NM_005779 | lipoma HMGIC fusion partner-like 2 | 5q13 | −6 |
| nulliparous | gene body | GPRC5B | NM_016235 | G protein-coupled receptor, family C, group 5, member B | 16p12 | −3.9 |
| nulliparous | gene body | GREB1 | NM_014668 | growth regulation by estrogen in breast cancer 1 | 2p25.1 | −3 |
| nulliparous | gene body | NCOA1 | NM_147233 | nuclear receptor coactivator 1 | 2p23 | −2.8 |
| nulliparous | gene body | CCDC108 | NM_194302 | coiled-coil domain containing 108 | 2q35 | −2.1 |
| nulliparous | gene body | CBLN2 | NM_182511 | cerebellin 2 precursor | 18q22.3 | −3.1 |
| nulliparous | gene body | PBX3 | NM_006195 | pre-B-cell leukemia homeobox 3 | 9q33.3 | −2.8 |
| nulliparous | gene body | PCDHB10 | NM_018930 | protocadherin beta 10 | 5q31 | −7.1 |
| nulliparous | gene body | FANCC | NM_000136 | Fanconi anemia, complementation group C | 9q22.3 | −2.1 |
| nulliparous | gene body | CDGAP | NM_020754 | NA | NA | −7.1 |
| nulliparous | gene body | PHIP | NM_017934 | pleckstrin homology domain interacting protein | 6q14 | −6.8 |
| nulliparous | gene body | SLC8A1 | NM_001112802 | solute carrier family 8 (sodium/calcium exchanger), member 1 | 2p23-p22 | −3.1 |
| nulliparous | gene body | CYBRD1 | NM_024843 | cytochrome b reductase 1 | 2q31 | −2.5 |
| nulliparous | gene body | FGF11 | NM_004112 | fibroblast growth factor 11 | 17p13.1 | −2.7 |
| nulliparous | gene body | DLC1 | NM_182643 | deleted in liver cancer 1 | 8p22 | −2.1 |
| nulliparous | gene body | RANBP3 | NM_007320 | RAN binding protein 3 | 19p13.3 | −4.9 |
| nulliparous | gene body | C1orf150 | NM_145278 | chromosome 1 open reading frame 150 | 1q44 | −4.1 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | gene body | EPB41L3 | NM_012307 | erythrocyte membrane protein band 4.1-like 3 | 18p11.32 | -2.6 |
| nulliparous | gene body | H1F0 | NM_005318 | H1 histone family, member 0 | 22q13.1 | -19.3 |
| nulliparous | gene body | MINA | NM_001042533 | MYC induced nuclear antigen | 3q22.1 | -3.1 |
| nulliparous | gene body | HDLBP | NM_005336 | high density lipoprotein binding protein | 2q37.3 | -2.3 |
| nulliparous | gene body | PPEF2 | NM_006239 | protein phosphatase, EF-hand calcium binding domain 2 | 4q21.21 | -73.9 |
| nulliparous | gene body | EGLN1 | NM_022051 | egl nine homolog 1 (*C. elegans*) | 1q42.1 | -2.8 |
| nulliparous | gene body | COL5A1 | NM_000093 | collagen, type V, alpha 1 | 9q34.2-q34.3 | -3 |
| nulliparous | gene body | SH2B2 | NM_020979 | SH2B adaptor protein 2 | 7q22.1 | -2.7 |
| nulliparous | gene body | BCOR | NM_017745 | BCL6 co-repressor | Xp11.4 | -5.2 |
| nulliparous | gene body | GRAMD1C | NM_017577 | GRAM domain containing 1C | 3q13.31 | -4 |
| nulliparous | gene body | GRAMD1B | NM_020716 | GRAM domain containing 1B | 11q24.1 | -2.5 |
| nulliparous | gene body | MAPK8IP1 | NM_005456 | mitogen-activated protein kinase 8 interacting protein 1 | 11p11.2 | -14.8 |
| nulliparous | gene body | GIPR | NM_000164 | gastric inhibitory polypeptide receptor | 19q13.2-q13.3 | -3.4 |
| nulliparous | gene body | GPR153 | NM_207370 | G protein-coupled receptor 153 | 1p36.31 | -3.8 |
| nulliparous | gene body | BEGAIN | NM_020836 | brain-enriched guanylate kinase-associated homolog (rat) | 14q32.2 | -2.1 |
| nulliparous | gene body | SGK3 | NM_001033578 | serum/glucocorticoid regulated kinase family, member 3 | 8q12 | -2.5 |
| nulliparous | gene body | WNT10A | NM_025216 | wingless-type MMTV integration site family, member 10A | 2q35 | -3.2 |
| nulliparous | gene body | LRP5 | NM_002335 | low density lipoprotein receptor-related protein 5 | 11q13.4 | -2.9 |
| nulliparous | gene body | IFI6 | NM_002038 | interferon, alpha-inducible protein 6 | 1p35 | -2.8 |
| nulliparous | gene body | ACOX1 | NM_007292 | acyl-Coenzyme A oxidase 1, palmitoyl | 17q25.1 | -3 |
| nulliparous | gene body | LMO4 | NM_006769 | LIM domain only 4 | 1p22.3 | -5.6 |
| nulliparous | gene body | TEX14 | NM_031272 | testis expressed 14 | 17 | -4.1 |
| nulliparous | gene body | SREBF1 | NM_001005291 | sterol regulatory element binding transcription factor 1 | 17p11.2 | -3.7 |
| nulliparous | gene body | RILPL1 | NM_178314 | Rab interacting lysosomal protein-like 1 | 12q24.31 | -3.2 |
| nulliparous | gene body | MYO16 | NM_015011 | myosin XVI | 13q33.3 | -3.7 |
| nulliparous | gene body | REEP6 | NM_138393 | receptor accessory protein 6 | 19p13.3 | -2.3 |
| nulliparous | gene body | HIVEP2 | NM_006734 | human immunodeficiency virus type I enhancer binding protein 2 | 6q23-q24 | -17.2 |
| nulliparous | gene body | GNAS | NM_016592 | GNAS complex locus | 20q13.2-q13.3 | -2.6 |
| nulliparous | gene body | PTH1R | NM_000316 | parathyroid hormone 1 receptor | 3p22-p21.1 | -3.3 |
| nulliparous | gene body | PTH1R | NM_000316 | parathyroid hormone 1 receptor | 3p22-p21.1 | -2.2 |
| nulliparous | gene body | PTH1R | NM_000316 | parathyroid hormone 1 receptor | 3p22-p21.1 | -2.2 |
| nulliparous | gene body | SNTB2 | NM_006750 | syntrophin, beta 2 (dystrophin-associated protein A1, 59 kDa, basic component 2) | 16q22.1 | -4.3 |
| nulliparous | gene body | NEURL | NM_004210 | neuralized homolog (*Drosophila*) | 10q25.1 | -6.4 |
| nulliparous | gene body | CHMP4B | NM_176812 | chromatin modifying protein 4B | 20q11.22 | -3.8 |
| nulliparous | gene body | PHF19 | NM_015651 | PHD finger protein 19 | 9q34.11 | -5.3 |
| nulliparous | gene body | ZNF497 | NM_198458 | zinc finger protein 497 | 19q13.43 | -2.3 |
| nulliparous | gene body | SLC5A1 | NM_000343 | solute carrier family 5 (sodium/glucose cotransporter), member 1 | 22q12.3 | -6.2 |
| nulliparous | gene body | ODZ4 | NM_001098816 | odz, odd Oz/ten-m homolog 4 (*Drosophila*) | 11q13 | -3.6 |
| nulliparous | gene body | SMOC2 | NM_022138 | SPARC related modular calcium binding 2 | 6q27 | -3.3 |
| nulliparous | gene body | LRRC37B2 | NR_015341 | leucine rich repeat containing 37, member B2 | 17q11.2 | -3.9 |
| nulliparous | gene body | SPTBN4 | NM_020971 | spectrin, beta, non-erythrocytic 4 | 19q13.13 | -2.2 |
| nulliparous | gene body | SPTBN4 | NM_020971 | spectrin, beta, non-erythrocytic 4 | 19q13.13 | -3.2 |
| nulliparous | gene body | FAM83G | NM_001039999 | family with sequence similarity 83, member G | 17p11.2 | -3.8 |
| nulliparous | gene body | FAM83A | NM_207006 | family with sequence similarity 83, member A | 8q24.13 | -3.7 |
| nulliparous | gene body | HIST1H2AC | NM_003512 | histone cluster 1, H2ac | 6p22.1 | -8.2 |
| nulliparous | gene body | ZNF721 | NM_133474 | zinc finger protein 721 | 4p16.3 | -4.6 |
| nulliparous | gene body | PNLIPRP2 | NM_005396 | pancreatic lipase-related protein 2 | 10q26.12 | -3.8 |
| nulliparous | gene body | SUGT1P | NR_003667 | suppressor of G2 allele of SKP1 pseudogene (*S. cerevisiae*) | 9p12 | -2.1 |
| nulliparous | gene body | RAB31 | NM_006868 | RAB31, member RAS oncogene family | 18p11.3 | -2.3 |
| nulliparous | gene body | TOB2 | NM_016272 | transducer of ERBB2, 2 | 22q13.2 | -4.1 |
| nulliparous | gene body | NETO1 | NM_153181 | neuropilin (NRP) and tolloid (TLL)-like 1 | 18q22.2 | -3.2 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | gene body | SVEP1 | NM_153366 | sushi, von Willebrand factor type A, EGF and pentraxin domain containing 1 | 9q31-q32 | -7.5 |
| nulliparous | gene body | RB1 | NM_000321 | retinoblastoma 1 | 13q14.2 | -2.4 |
| nulliparous | gene body | FAM155A | NM_001080396 | family with sequence similarity 155, member A | 13q33.3 | -2.8 |
| nulliparous | gene body | RAI1 | NM_030665 | retinoic acid induced 1 | 17p11.2 | -2.5 |
| nulliparous | gene body | RAI1 | NM_030665 | retinoic acid induced 1 | 17p11.2 | -2.4 |
| nulliparous | gene body | PDZD4 | NM_032512 | PDZ domain containing 4 | Xq28 | -4.5 |
| nulliparous | gene body | SLIT3 | NM_003062 | slit homolog 3 (Drosophila) | 5q35 | -8.9 |
| nulliparous | gene body | GBE1 | NM_000158 | glucan (1,4-alpha-), branching enzyme 1 | 3 | -4.7 |
| nulliparous | gene body | SULF1 | NM_015170 | sulfatase 1 | 8q13.1 | -4.1 |
| nulliparous | gene body | CABLES1 | NR_023359 | Cdk5 and Abl enzyme substrate 1 | 18q11.2 | -3.7 |
| nulliparous | gene body | PACSIN1 | NM_020804 | protein kinase C and casein kinase substrate in neurons 1 | 6p21.3 | -3 |
| nulliparous | gene body | DGKG | NM_001080744 | diacylglycerol kinase, gamma 90 kDa | 3q27-q28 | -2.3 |
| nulliparous | gene body | YWHAE | NM_006761 | tyrosine 3-monooxygenase/tryptophan 5-monooxygenase activation protein, epsilon polypeptide | 17p13 | -2.3 |
| nulliparous | gene body | C13orf33 | NM_032849 | chromosome 13 open reading frame 33 | 13q12.3 | -3.6 |
| nulliparous | gene body | PRDM2 | NM_015866 | PR domain containing 2, with ZNF domain | 1p36 | -9.1 |
| nulliparous | gene body | ESRRB | NM_004452 | estrogen-related receptor beta | 14q24.3 | -2.7 |
| nulliparous | gene body | ESRRB | NM_004452 | estrogen-related receptor beta | 14q24.3 | 4.3 |
| nulliparous | gene body | TPO | NM_175722 | thyroid peroxidase | 2p25 | -5.1 |
| nulliparous | gene body | DAB2IP | NM_032552 | DAB2 interacting protein | 9q33.1-q33.3 | -3.9 |
| nulliparous | gene body | CHRM5 | NM_012125 | cholinergic receptor, muscarinic 5 | 15q26 | -3.8 |
| nulliparous | gene body | NLGN4X | NM_020742 | neuroliqin 4, X-linked | Xp22.33 | -7.6 |
| nulliparous | gene body | TANC1 | NM_033394 | tetratricopeptide repeat, ankyrin repeat and coiled-coil containing 1 | 2q24.2 | -7.3 |
| nulliparous | gene body | CHRM2 | NM_000739 | cholinergic receptor, muscarinic 2 | 7q35-q36 | -6 |
| nulliparous | gene body | LOC732275 | NR_024406 | NA | NA | -5.8 |
| nulliparous | gene body | PIP5K1C | NM_012398 | phosphatidylinositol-4-phosphate 5-kinase, type I, gamma | 19p13.3 | -3.3 |
| nulliparous | gene body | LRRC55 | NM_001052210 | leucine rich repeat containing 55 | 11q12.1 | -3 |
| nulliparous | gene body | LOC389332 | NR_024418 | NA | NA | -2.1 |
| nulliparous | gene body | USP18 | NM_017414 | ubiquitin specific peptidase 18 | 22q11.2 | -4.1 |
| nulliparous | gene body | SHANK3 | NM_001080420 | SH3 and multiple ankyrin repeat domains 3 | 22q13.3 | -3.6 |
| nulliparous | gene body | HM13 | NM_178582 | histocompatibility (minor) 13 | 20q11.21 | -3.2 |
| nulliparous | gene body | CTNNA2 | NM_004389 | catenin (cadherin-associated protein), alpha 2 | 2p12-p11.1 | -4.8 |
| nulliparous | gene body | CTNNA3 | NM_001127384 | catenin (cadherin-associated protein), alpha 3 | 10q21 | -11.8 |
| nulliparous | gene body | CACNG3 | NM_006539 | calcium channel, voltage-dependent, gamma subunit 3 | 16p12.1 | -2.2 |
| nulliparous | gene body | PACRG | NM_152410 | PARK2 co-regulated | 6q26 | -4.7 |
| nulliparous | gene body | RNU11 | NR_004407 | RNA, U11 small nuclear | 1p35 | -2.2 |
| nulliparous | gene body | MXI1 | NM_130439 | MAX interactor 1 | 10q24-q25 | -2.5 |
| nulliparous | gene body | ALCAM | NM_001627 | activated leukocyte cell adhesion molecule | 3q13.1 | -4.7 |
| nulliparous | gene body | CXorf41 | NM_173494 | chromosome X open reading frame 41 | Xq22.3 | -2.8 |
| nulliparous | gene body | C3orf21 | NM_152531 | chromosome 3 open reading frame 21 | 3q29 | -2.6 |
| nulliparous | gene body | ANK2 | NM_001127493 | ankyrin 2, neuronal | 4q25-q27 | -5 |
| nulliparous | gene body | PTPRB | NM_001109754 | protein tyrosine phosphatase, receptor type, B | 12q15-q21 | -2.2 |
| nulliparous | gene body | FUT1 | NM_000148 | fucosyltransferase 1 (galactoside 2-alpha-L-fucosyltransferase, H blood group) | 19q13.1-qter | -5.5 |
| nulliparous | gene body | ALPI | NM_001631 | alkaline phosphatase, intestinal | 2q37.1 | -3.2 |
| nulliparous | gene body | PPP1R13L | NM_006663 | protein phosphatase 1, regulatory (inhibitor) subunit 13 like | 19q13.32 | -8.5 |
| nulliparous | gene body | SLC2A9 | NM_020041 | solute carrier family 2 (facilitated glucose transporter), member 9 | 4p16.1 | -9.5 |
| nulliparous | gene body | LIMCH1 | NM_001112718 | LIM and calponin homology domains 1 | 4p13 | -2.5 |
| nulliparous | gene body | HEPACAM | NM_152722 | hepatocyte cell adhesion molecule | 11q24.2 | -3 |
| nulliparous | gene body | LOC100188947 | NR_024467 | NA | NA | -3.2 |
| nulliparous | gene body | LIN7B | NM_022165 | lin-7 homolog B (C. elegans) | 19q13.3 | -2.8 |
| nulliparous | gene body | ESPN | NM_031475 | espin | 1p36.31 | -11.2 |
| nulliparous | gene body | SFTPC | NM_003018 | surfactant protein C | 8p21 | -6.2 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | gene body | ISL1 | NM_002202 | ISL LIM homeobox 1 | 5q11.2 | -8.9 |
| nulliparous | gene body | GSC | NM_173849 | goosecoid homeobox | 14q32.13 | -2.4 |
| nulliparous | gene body | TNRC6B | NM_015088 | trinucleotide repeat containing 6B | 22q13 | -2.9 |
| nulliparous | gene body | A2BP1 | NM_018723 | NA | NA | -10.5 |
| nulliparous | gene body | MRC2 | NM_006039 | mannose receptor, C type 2 | 17q23 | -2.3 |
| nulliparous | gene body | LHX4 | NM_033343 | LIM homeobox 4 | 1q25.3 | -6.6 |
| nulliparous | gene body | FAM110A | NM_001042353 | family with sequence similarity 110, member A | 20p13 | -2.3 |
| nulliparous | gene body | FLII | NM_002018 | flightless I homolog (Drosophila) | 17p11.2 | -2.1 |
| nulliparous | gene body | IRX3 | NM_024336 | iroquois homeobox 3 | 16q12.2 | -2.9 |
| nulliparous | gene body | KCNAB1 | NM_172160 | potassium voltage-gated channel, shaker-related subfamily, beta member 1 | 3q26.1 | -7.7 |
| nulliparous | gene body | AHRR | NM_020731 | aryl-hydrocarbon receptor repressor | 5p15.33 | -2.4 |
| nulliparous | gene body | OCA2 | NM_000275 | oculocutaneous albinism II | 15q11.2-q12 | -6.8 |
| nulliparous | gene body | SOCS2 | NM_003877 | suppressor of cytokine signaling 2 | 12q | -2.8 |
| nulliparous | gene body | CNN2 | NM_004368 | calponin 2 | 19p13.3 | -2.5 |
| nulliparous | gene body | PLEKHA4 | NM_020904 | pleckstrin homology domain containing, family A (phosphoinositide binding specific) member 4 | 19q13.33 | -9.2 |
| nulliparous | gene body | RUNX1 | NM_001754 | runt-related transcription factor 1 | 21q22.3 | -2.5 |
| nulliparous | gene body | ZNF274 | NM_016324 | zinc finger protein 274 | 19q13.43 | -6.3 |
| nulliparous | gene body | MMP15 | NM_002428 | matrix metalloproteinase 15 (membrane-inserted) | 16q13 | -15.5 |
| nulliparous | gene body | PDXK | NM_003681 | pyridoxal (pyridoxine, vitamin B6) kinase | 21q22.3 | -4.8 |
| nulliparous | gene body | ELAVL2 | NM_004432 | ELAV (embryonic lethal, abnormal vision, Drosophila)-like 2 (Hu antigen B) | 9p21 | -3.4 |
| nulliparous | gene body | HLA-G | NM_002127 | major histocompatibility complex, class I, G | 6p21.3 | -3.9 |
| nulliparous | gene body | TBR1 | NM_006593 | T-box, brain, 1 | 2q24.2 | -5.7 |
| nulliparous | gene body | SLC25A37 | NM_016612 | solute carrier family 25, member 37 | 8p21.2 | -11.3 |
| nulliparous | gene body | MDGA1 | NM_153487 | MAM domain containing glycosylphosphatidylinositol anchor 1 | 6p21 | -3.5 |
| nulliparous | gene body | MAML3 | NM_001005464 | mastermind-like 3 (Drosophila) | 4q28 | -7.7 |
| nulliparous | gene body | TNRC18 | NM_001080495 | trinucleotide repeat containing 18 | 7p22.1 | -14 |
| nulliparous | gene body | PCDHB6 | NM_018939 | protocadherin beta 6 | 5q31 | -2.4 |
| nulliparous | gene body | NINJ2 | NM_016533 | ninjurin 2 | 12p13 | -4.1 |
| nulliparous | gene body | FLJ10490 | NM_018111 | NA | NA | -2.8 |
| nulliparous | gene body | HOXB4 | NM_024015 | homeobox B4 | 17q21.32 | -7.9 |
| nulliparous | gene body | LRRC37B2 | NR_015341 | leucine rich repeat containing 37, member B2 | 17q11.2 | -5.2 |
| nulliparous | gene body | HIST2H3C | NM_021059 | histone cluster 2, H3c | 1q21.2 | -3.1 |
| nulliparous | gene body | HIST2H3A | NM_001005464 | histone cluster 2, H3a | 1q21.2 | -3.1 |
| nulliparous | gene body | COX7A1 | NM_001864 | cytochrome c oxidase subunit VIIa polypeptide 1 (muscle) | 19q13.1 | -13.8 |
| nulliparous | gene body | EPS8L2 | NM_022772 | EPS8-like 2 | 11p15.5 | -2.3 |
| nulliparous | gene body | GDI1 | NM_001493 | GDP dissociation inhibitor 1 | Xq28 | -3.2 |
| nulliparous | gene body | C10orf140 | NM_207371 | chromosome 10 open reading frame 140 | 10p12.31 | -2.4 |
| nulliparous | gene body | UBE2K | NM_005339 | ubiquitin-conjugating enzyme E2K (UBC1 homolog, yeast) | 4p14 | -6.4 |
| nulliparous | gene body | FLJ36208 | NM_176677 | NA | NA | -6 |
| nulliparous | gene body | ASFMR1 | NR_024499 | NA | NA | -2.7 |
| nulliparous | gene body | SORT1 | NM_002959 | sortilin 1 | 1p13.3 | -3.1 |
| nulliparous | gene body | PRDM8 | NM_020226 | PR domain containing 8 | 4q21 | -2.4 |
| nulliparous | gene body | CTNND2 | NM_001332 | catenin (cadherin-associated protein), delta 2 (neural plakophilin-related arm-repeat protein) | 5p15.2 | -4.8 |
| nulliparous | gene body | ADCYAP1 | NM_001099733 | adenylate cyclase activating polypeptide 1 (pituitary) | 18p11 | -2.3 |
| nulliparous | gene body | GPRC5C | NM_022036 | G protein-coupled receptor, family C, group 5, member C | 17q25 | -33.1 |
| nulliparous | gene body | CCDC106 | NM_013301 | coiled-coil domain containing 106 | 19q13.42 | -5.1 |
| nulliparous | gene body | ALCAM | NM_001627 | activated leukocyte cell adhesion molecule | 3q13.1 | -3.6 |
| nulliparous | gene body | UNC5CL | NM_173561 | unc-5 homolog C (C. elegans)-like | 6p21.1 | -3 |
| nulliparous | gene body | PCDHB10 | NM_018930 | protocadherin beta 10 | 5q31 | -5.5 |
| nulliparous | gene body | CITED1 | NM_004143 | Cbp/p300-interacting transactivator, with Glu/Asp-rich carboxy-terminal domain, 1 | Xq13.1 | -2.1 |
| nulliparous | gene body | HIST2H2AA3 | NM_003516 | histone cluster 2, H2aa3 | 1q21.2 | -3.1 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | gene body | HIST2H2AA4 | NM_001040874 | histone cluster 2, H2aa4 | 1q21.2 | -3.1 |
| nulliparous | gene body | FLJ34048 | NR_015448 | NA | NA | -3.4 |
| nulliparous | gene body | LAMP2 | NM_002294 | lysosomal-associated membrane protein 2 | Xq24-q25 | -2.5 |
| nulliparous | gene body | SND1 | NM_014390 | staphylococcal nuclease and tudor domain containing 1 | 7q31.3 | -3.9 |
| nulliparous | gene body | FREQ | NM_014286 | frequenin homolog (Drosophila) | 9q34.11 | -2.9 |
| nulliparous | gene body | FRMD4A | NM_018027 | FERM domain containing 4A | 10p14 | -2.7 |
| nulliparous | gene body | ALOX12B | NM_001139 | arachidonate 12-lipoxygenase, 12R | 17p13.1 | -2.8 |
| nulliparous | gene body | ALOX12B | NM_001139 | arachidonate 12-lipoxygenase, 12R | 17p13.1 | 2.4 |
| nulliparous | gene body | LMO3 | NM_001001395 | LIM domain only 3 (rhombotin-like | 12p13 | -4.9 |
| nulliparous | gene body | MYO16 | NM_015011 | myosin XVI | 13q33.3 | -5.6 |
| nulliparous | gene body | MYO16 | NM_015011 | myosin XVI | 13q33.3 | 2.6 |
| nulliparous | gene body | PTH1R | NM_000316 | parathyroid hormone 1 receptor | 3p22-P21.1 | -4.9 |
| nulliparous | gene body | PTK7 | NM_002821 | PTK7 protein tyrosine kinase 7 | 6p21.1-p12.2 | -11.6 |
| nulliparous | gene body | JUNB | NM_002229 | jun B proto-oncogene | 19p13.13 | -7.8 |
| nulliparous | gene body | BIRC2 | NM_001166 | baculoviral IAP repeat-containing 2 | 11q22 | -9.6 |
| nulliparous | gene body | ZNF497 | NM_198458 | zinc finger protein 497 | 19q13.43 | -6.9 |
| nulliparous | gene body | SLC5A1 | NM_000343 | solute carrier family 5 (sodium/glucose cotransporter), member 1 | 22q12.3 | -10.1 |
| nulliparous | gene body | SMOC2 | NM_022138 | SPARC related modular calcium binding 2 | 6q27 | -3.3 |
| nulliparous | gene body | HIST1H2AC | NM_003512 | histone cluster 1, H2ac | 6p22.1 | -3.6 |
| nulliparous | gene body | PRICKLE1 | NM_153026 | prickle homolog 1 (Drosophila) | 12p11-q12 | -4.3 |
| nulliparous | gene body | RNU11 | NR_004407 | RNA, U11 small nuclear | 1p35 | -3 |
| nulliparous | gene body | LYPD1 | NM_001077427 | LY6/PLAUR domain containing 1 | 2q21.2 | -3.4 |
| nulliparous | gene body | RTBDN | NM_031429 | retbindin | 19p13 | -4.1 |
| nulliparous | gene body | C9orf66 | NM_152569 | chromosome 9 open reading frame 66 | 9p24.3 | -3.2 |
| nulliparous | gene body | LOC100130987 | NR_024469 | NA | NA | -3.2 |
| nulliparous | gene body | YWHAE | NM_006761 | tyrosine 3-monooxygenase/tryptophan 5-monooxygenase activation protein, epsilon polypeptide | 17p13 | -3.5 |
| nulliparous | gene body | HEATR1 | NM_018072 | HEAT repeat containing 1 | 1q43 | -2.8 |
| nulliparous | gene body | INTS9 | NM_018250 | integrator complex subunit 9 | 8p21.1 | -14.7 |
| nulliparous | gene body | EBF1 | NM_024007 | early B-cell factor 1 | 5q34 | -10.7 |
| nulliparous | gene body | TLX2 | NM_016170 | T-cell leukemia homeobox 2 | 2p13.1 | -6.4 |
| nulliparous | gene body | TSGA13 | NM_052933 | testis specific, 13 | 7q32 | -2.4 |
| nulliparous | gene body | BCL9 | NM_004326 | B-cell CLL/lymphoma 9 | 1q21 | -3.1 |
| nulliparous | gene body | FOLR2 | NM_000803 | folate receptor 2 (fetal) | 11q13.3-q14.1 | -3.6 |
| nulliparous | gene body | RECQL5 | NM_004259 | RecQ protein-like 5 | 17q25 | 2.1 |
| parous | gene body | VAV2 | NM_003371 | vav 2 guanine nucleotide exchange factor | 9q34.1 | 4.2 |
| parous | gene body | TNFAIP8L3 | NM_207381 | tumor necrosis factor, alpha-induced protein 8-like 3 | 15q21.2 | 2.1 |
| parous | gene body | C1orf106 | NM_018265 | chromosome 1 open reading frame 106 | 1q32.1 | 6.1 |
| parous | gene body | ONECUT2 | NM_004852 | one cut homeobox 2 | 18q21.31 | 3.8 |
| parous | gene body | DIP2C | NM_014974 | DIP2 disco-interacting protein 2 homolog C (Drosophila) | 10p 15.3 | 2.7 |
| parous | gene body | ZFHX3 | NM_006885 | zinc finger homeobox 3 | 16q22.3 | 3.8 |
| parous | gene body | BCL11B | NM_022898 | B-cell CLL/lymphoma 11B (zinc finger protein) | 14q32 | 3.7 |
| parous | gene body | TNFRSF14 | NM_003820 | tumor necrosis factor receptor superfamily, member 14 (herpesvirus entry mediator) | 1p36.32 | 4.4 |
| parous | gene body | ANKRD13B | NM_152345 | ankyrin repeat domain 13B | 17q11.2 | 2.2 |
| parous | gene body | B3GAT2 | NM_080742 | beta-1,3-glucuronyltransferase 2 (glucuronosyltransferase S) | 6q12 | 2.7 |
| parous | gene body | BMP8A | NM_181809 | bone morphogenetic protein 8a | 1p35-p32 | 2.8 |
| parous | gene body | GAPVD1 | NM_015635 | GTPase activating protein and VPS9 domains 1 | 9q34.11 | 5 |
| parous | gene body | RARG | NM_001042728 | retinoic acid receptor, gamma | 12q13 | 2.2 |
| parous | gene body | KIFC2 | NM_145754 | kinesin family member C2 | 8q24.3 | 3.6 |
| parous | gene body | THRA | NM_199334 | thyroid hormone receptor, alpha (erythroblastic leukemia viral (v-erb-a) oncogene homolog, avian) | 17q21.1 | 2.7 |
| parous | gene body | GPR124 | NM_032777 | G protein-coupled receptor 124 | 8p11.22 | 2.2 |
| parous | gene body | DLGAP4 | NM_014902 | discs, large (Drosophila) homolog-associated protein 4 | 20 | 2.6 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | gene body | TTLL12 | NM_015140 | tubulin tyrosine ligase-like family, member 12 | 22q13.31 | 4.9 |
| parous | gene body | ALOX12B | NM_001139 | arachidonate 12-lipoxygenase, 12R type | 17p13.1 | -2.8 |
| parous | gene body | ALOX12B | NM_001139 | arachidonate 12-lipoxygenase, 12R type | 17p13.1 | 2.4 |
| parous | gene body | ARHGEF10 | NM_014629 | Rho guanine nucleotide exchange factor (GEF) 10 | 8p23 | 2.7 |
| parous | gene body | PHACTR1 | NM_030948 | phosphatase and actin regulator 1 | 6p23 | 2.2 |
| parous | gene body | CASZ1 | NM_001079843 | castor zinc finger 1 | 1p36.22 | 21.3 |
| parous | gene body | BMP8B | NM_001720 | bone morphogenetic protein 8b | 1p35-p32 | 2.8 |
| parous | gene body | BRUNOL4 | NM_020180 | bruno-like 4, RNA binding protein (Drosophila) | 18q12 | 3.9 |
| parous | gene body | ACAP1 | NM_014716 | ArfGAP with coiled-coil, ankyrin repeat and PH domains 1 | 17p13.1 | 28.3 |
| parous | gene body | FLJ45983 | NR_024255 | NA | NA | 2.9 |
| parous | gene body | LOC643008 | NR_024379 | NA | NA | 2.1 |
| parous | gene body | KIF26B | NM_018012 | kinesin family member 26B | 1q44 | 2.4 |
| parous | gene body | CHRNA3 | NM_000743 | cholinergic receptor, nicotinic, alpha 3 | 15q24 | 24.3 |
| parous | gene body | FMN2 | NM_020066 | formin 2 | 1q43 | 21.9 |
| parous | gene body | RAB40C | NM_021168 | RAB40C, member RAS oncogene family | 16p13.3 | 5.2 |
| parous | gene body | SLC25A42 | NM_178526 | solute carrier family 25, member 42 | 19p13.11 | 2.6 |
| parous | gene body | MTHFSD | NM_022764 | methenyltetrahydrofolate synthetase domain containing | 16q24.1 | 16.3 |
| parous | gene body | EXOC3L | NM_178516 | exocyst complex component 3-like | 16q22.1 | 6.3 |
| parous | gene body | ASTN2 | NM_198186 | astrotactin 2 | 9q33 | 2.2 |
| parous | gene body | ANKFY1 | NM_016376 | ankyrin repeat and FYVE domain containing 1 | 17p13.3 | 4.4 |
| parous | gene body | LRRN4 | NM_152611 | leucine rich repeat neuronal 4 | 20p12.3 | 2.8 |
| parous | gene body | ERF | NM_006494 | Ets2 repressor factor | 19q13 | 4.1 |
| parous | gene body | ATPGD1 | NM_020811 | ATP-grasp domain containing 1 | 11q13.1 | 2.5 |
| parous | gene body | FLJ37453 | NR_024279 | NA | NA | 3.4 |
| parous | gene body | MYO16 | NM_015011 | myosin XVI | 13q33.3 | -5.6 |
| parous | gene body | MYO16 | NM_015011 | myosin XVI | 13q33.3 | 2.6 |
| parous | gene body | HES7 | NM_032580 | hairy and enhancer of split 7 (Drosophila) | 17p13.1 | 55.5 |
| nulliparous | promoter | DUOXA1 | NM_144565 | dual oxidase maturation factor 1 | 15q21.1 | -4.5 |
| nulliparous | promoter | HIST1H4G | NM_003547 | histone cluster 1, H4g | 6p22.1 | -2.5 |
| nulliparous | promoter | C17orf76 | NM_207387 | chromosome 17 open reading frame 76 | 17p11.2 | -2.3 |
| nulliparous | promoter | PARS2 | NM_152268 | prolyl-tRNA synthetase 2, mitochondrial (putative) | 1p32.2 | -4.6 |
| nulliparous | promoter | KIAA1012 | NM_014939 | KIAA1012 | 18q12.1 | -2.9 |
| nulliparous | promoter | OCA2 | NM_000275 | oculocutaneous albinism II | 15q11.2-q12 | -6.8 |
| nulliparous | promoter | HNRPLL | NM_138394 | heterogeneous nuclear ribonucleoprotein L-like | 2p22 | -5.7 |
| nulliparous | promoter | PCDHB6 | NM_018939 | protocadherin beta 6 | 5q31 | -2.4 |
| nulliparous | promoter | N4BP2L1 | NM_001079691 | NEDD4 binding protein 2-like 1 | 13q13.1 | -3.1 |
| nulliparous | promoter | GSC | NM_173849 | goosecoid homeobox | 14q32.13 | -2.4 |
| nulliparous | promoter | OAT | NM_000274 | ornithine aminotransferase (gyrate atrophy) | 10q26 | -2.6 |
| nulliparous | promoter | POLS | NM_006999 | polymerase (DNA directed) sigma | 5p15 | -4.7 |
| nulliparous | promoter | SEMA4C | NM_017789 | sema domain, immunoglobulin domain (Ig), transmembrane domain (TM) and short cytoplasmic domain, (semaphorin) 4C | 2q11.2 | -3.6 |
| nulliparous | promoter | SEMA4F | NM_004263 | sema domain, immunoglobulin domain (Ig), transmembrane domain (TM) and short cytoplasmic domain, (semaphorin) 4F | 2p13.1 | -3.8 |
| nulliparous | promoter | ACTG1 | NM_001614 | actin, gamma 1 | 17q25 | -5.2 |
| nulliparous | promoter | MRC2 | NM_006039 | mannose receptor, C type 2 | 17q23 | -2.3 |
| nulliparous | promoter | KIAA0564 | NM_015058 | KIAA0564 | 13q14.11 | -4.1 |
| nulliparous | promoter | DLG5 | NM_004747 | discs, large homolog 5 (Drosophila) | 10q23 | -12 |
| nulliparous | promoter | C6orf120 | NM_001029863 | chromosome 6 open reading frame 120 | 6q27 | -5.8 |
| nulliparous | promoter | MBIP | NM_016586 | MAP3K12 binding inhibitory protein 1 | 14q13.2 | -122.1 |
| nulliparous | promoter | SAMD11 | NM_152486 | sterile alpha motif domain containing 11 | 1p36.33 | -3.5 |
| nulliparous | promoter | FMNL3 | NM_198900 | formin-like 3 | 12q13.12 | -4.4 |
| nulliparous | promoter | BCLAF1 | NM_001077440 | BCL2-associated transcription factor 1 | 6q22-q23 | -5.8 |
| nulliparous | promoter | STAP2 | NM_017720 | signal transducing adaptor family member 2 | 19p13.3 | -3.3 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | N6AMT2 | NM_174928 | N-6 adenine-specific DNA methyltransferase 2 (putative) | 13q12.11 | -2.3 |
| nulliparous | promoter | ZNF574 | NM_022752 | zinc finger protein 574 | 19 | -4.7 |
| nulliparous | promoter | NDUFA11 | NM_175614 | NADH dehydrogenase (ubiquinone) 1 alpha subcomplex, 11, 14.7 kDa | 19p13.3 | -2.5 |
| nulliparous | promoter | FOXF2 | NM_001452 | forkhead box F2 | 6p25.3 | -5.6 |
| nulliparous | promoter | MTMR7 | NM_004686 | myotubularin related protein 7 | 8p22 | -3 |
| nulliparous | promoter | MBNL1 | NM_021038 | muscleblind-like (Drosophila) | 3q25 | -6 |
| nulliparous | promoter | HEBP2 | NM_014320 | heme binding protein 2 | 6q24 | -2.6 |
| nulliparous | promoter | C14orf151 | NM_032714 | NA | NA | -3.3 |
| nulliparous | promoter | ONECUT1 | NM_004498 | one cut homeobox 1 | 15q21.3 | -5.3 |
| nulliparous | promoter | IRX3 | NM_024336 | iroquois homeobox 3 | 16q12.2 | -2.9 |
| nulliparous | promoter | ZMPSTE24 | NM_005857 | zinc metallopeptidase (STE24 homolog, S. cerevisiae) | 1p34 | -4.5 |
| nulliparous | promoter | BAI1 | NM_001702 | brain-specific angiogenesis inhibitor 1 | 8q24 | -3.8 |
| nulliparous | promoter | WRB | NM_004627 | tryptophan rich basic protein | 21q22.3 | -2.5 |
| nulliparous | promoter | FAM19A3 | NM_001004440 | family with sequence similarity 19 (chemokine (C-C motif)-like), member A3 | 1p13.2 | -17.6 |
| nulliparous | promoter | PEX26 | NM_017929 | peroxisomal biogenesis factor 26 | 22q11.21 | -7.8 |
| nulliparous | promoter | PLD5 | NM_152666 | phospholipase D family, member 5 | 1q43 | -11.6 |
| nulliparous | promoter | LRRC4 | NM_022143 | leucine rich repeat containing 4 | 7q31 | -3.9 |
| nulliparous | promoter | SP1 | NM_138473 | Sp1 transcription factor | 12q13.1 | -6.8 |
| nulliparous | promoter | TSC22D3 | NM_001015881 | TSC22 domain family, member 3 | Xq22.3 | -2.1 |
| nulliparous | promoter | SP3 | NM_001017371 | Sp3 transcription factor | 2q31 | -3.3 |
| nulliparous | promoter | SP4 | NM_003112 | Sp4 transcription factor | 7p15 | -2.2 |
| nulliparous | promoter | ZNF687 | NM_020832 | zinc finger protein 687 | 1q21.2 | -34 |
| nulliparous | promoter | OSTF1 | NM_012383 | osteoclast stimulating factor 1 | 9q13-q21.2 | -3 |
| nulliparous | promoter | NKRF | NM_017544 | NFKB repressing factor | Xq24 | -2.2 |
| nulliparous | promoter | STK3 | NM_006281 | serine/threonine kinase 3 (STE20 homolog, yeast) | 8q22.2 | -5.9 |
| nulliparous | promoter | PIN4 | NM_006223 | protein (peptidylprolyl cis/trans isomerase) NIMA-interacting, 4 (parvulin) | Xq13.1 | -2.2 |
| nulliparous | promoter | RAE1 | NM_003610 | RAE1 RNA export 1 homolog (S. pombe) | 20 | -2.5 |
| nulliparous | promoter | ARRDC3 | NM_020801 | arrestin domain containing 3 | 5q14.3 | -4.8 |
| nulliparous | promoter | TMEM184B | NM_012264 | transmembrane protein 184B | 22q12 | -6.4 |
| nulliparous | promoter | ABHD6 | NM_020676 | abhydrolase domain containing 6 | 3p21.2 | -3.6 |
| nulliparous | promoter | CXCL16 | NM_022059 | chemokine (C-X-C motif) ligand 16 | 17p13 | -2.2 |
| nulliparous | promoter | SYNCRIP | NM_006372 | synaptotagmin binding, cytoplasmic RNA interacting protein | 6q14-q15 | -2.4 |
| nulliparous | promoter | SYNCRIP | NM_006372 | synaptotagmin binding, cytoplasmic RNA interacting protein | 6q14-q15 | 2.5 |
| nulliparous | promoter | ADCYAP1 | NM_001099733 | adenylate cyclase activating polypeptide 1 (pituitary) | 18p11 | -2.3 |
| nulliparous | promoter | C19orf50 | NM_024069 | chromosome 19 open reading frame 50 | 19p13.11 | -4.9 |
| nulliparous | promoter | TRIOBP | NM_138632 | TRIO and F-actin binding protein | 22q13.1 | -2.5 |
| nulliparous | promoter | BMP1 | NM_006128 | bone morphogenetic protein 1 | 8p21 | -6.2 |
| nulliparous | promoter | SLC2A8 | NM_014580 | solute carrier family 2 (facilitated glucose transporter), member 8 | 9q33.3 | -3.2 |
| nulliparous | promoter | C1orf31 | NM_001012985 | chromosome 1 open reading frame 31 | 1q42.2 | -2.8 |
| nulliparous | promoter | SLC2A4 | NM_001042 | solute carrier family 2 (facilitated glucose transporter), member 4 | 17p13 | -15.7 |
| nulliparous | promoter | PPFIA3 | NM_003660 | protein tyrosine phosphatase, receptor type, f polypeptide (PTPRF), interacting protein (liprin), alpha 3 | 19 | -2.8 |
| nulliparous | promoter | ZBTB34 | NM_001099270 | zinc finger and BTB domain containing 34 | 9q33.3 | -3.3 |
| nulliparous | promoter | TTC14 | NM_133462 | tetratricopeptide repeat domain 14 | 3q27.2 | -2.8 |
| nulliparous | promoter | C1orf203 | NR_024126 | chromosome 1 open reading frame 203 | 1 p13.1 | -3.1 |
| nulliparous | promoter | RHBDD3 | NM_012265 | rhomboid domain containing 3 | 22q12.2 | -5.3 |
| nulliparous | promoter | GFRA3 | NM_001496 | GDNF family receptor alpha 3 | 5q31.1-q31.3 | -2.9 |
| nulliparous | promoter | PRR15 | NM_175887 | proline rich 15 | 7p15.1 | -2.6 |
| nulliparous | promoter | YIPF1 | NM_018982 | Yip1 domain family, member 1 | 1p33-p32.1 | -2.1 |
| nulliparous | promoter | MTIF3 | NM_152912 | mitochondrial translational initiation factor 3 | 13q12.2 | -8.6 |
| nulliparous | promoter | ZNF37A | NM_003421 | zinc finger protein 37A | 10p11.2 | -2.5 |
| nulliparous | promoter | CEP78 | NM_032171 | centrosomal protein 78 kDa | 9q21.2 | -2.6 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | EPHB2 | NM_004442 | EPH receptor B2 | 1p36.1-P35 | -2.2 |
| nulliparous | promoter | DMRT2 | NM_001130865 | doublesex and mab-3 related transcription factor 2 | 9p24.3 | -4.5 |
| nulliparous | promoter | KCTD18 | NM_152387 | potassium channel tetramerisation domain containing 18 | 2q33.1 | -10.6 |
| nulliparous | promoter | OXSR1 | NM_005109 | oxidative-stress responsive 1 | 3p22.2 | -18.5 |
| nulliparous | promoter | HSD17B14 | NM_016246 | hydroxysteroid (17-beta) dehydrogenase 14 | 19q13.33 | -9.2 |
| nulliparous | promoter | NR3C2 | NM_000901 | nuclear receptor subfamily 3, group C, member 2 | 4q31 | -4 |
| nulliparous | promoter | ADORA1 | NM_000674 | adenosine A1 receptor | 1q32.1 | -2.2 |
| nulliparous | promoter | CSTF3 | NM_001033506 | cleavage stimulation factor, 3"pre-RNA, subunit 3, 77 kDa | 11 pi 3 | -3.6 |
| nulliparous | promoter | NUAK2 | NM_030952 | NUAK family, SNF1-like kinase, 2 | 1q32.1 | -3 |
| nulliparous | promoter | NFKBIA | NM_020529 | nuclear factor of kappa light polypeptide gene enhancer in B-cells inhibitor, alpha | 14q13 | -3.9 |
| nulliparous | promoter | HLA-G | NM_002127 | major histocompatibility complex, class 1, G | 6p21.3 | -5.7 |
| nulliparous | promoter | TBR1 | NM_006593 | T-box, brain, 1 | 2q24.2 | -2.4 |
| nulliparous | promoter | DGKD | NM_152879 | diacylglycerol kinase, delta 130 kDa | 2q37 | -3.1 |
| nulliparous | promoter | NAPRT1 | NM_145201 | nicotinate phosphoribosyltransferase domain containing 1 | 8q24.3 | -2.6 |
| nulliparous | promoter | C1QL4 | NM_001008223 | complement component 1, q subcomponent-like 4 | 12q13.12 | -3.2 |
| nulliparous | promoter | C9orf66 | NM_152569 | chromosome 9 open reading frame 66 | 9p24.3 | 3.2 |
| nulliparous | promoter | C9orf66 | NM_152569 | chromosome 9 open reading frame 66 | 9p24.3 | -24.9 |
| nulliparous | promoter | CEP97 | NM_024548 | centrosomal protein 97 kDa | 3q12.3 | -2.9 |
| nulliparous | promoter | PDHX | NM_001135024 | pyruvate dehydrogenase complex, component X | 11 pi 3 | -5.6 |
| nulliparous | promoter | GUSB | NM_000181 | glucuronidase, beta | 7q11.21 | -5.6 |
| nulliparous | promoter | GFER | NM_005262 | growth (actor, augmenter of liver regeneration | 16p13.3-P13.12 | -2.9 |
| nulliparous | promoter | SUMF1 | NM_182760 | sulfatase modifying factor 1 | 3p26.1 | -3.4 |
| nulliparous | promoter | RWDD2A | NM_033411 | RWD domain containing 2A | 6q15 | -14 |
| nulliparous | promoter | ATAD3A | NM_018188 | ATPase family, AAA domain containing 3A | 1p36.33 | -2.9 |
| nulliparous | promoter | LOC28422 | NM_001136503 | NA | NA | -5.1 |
| nulliparous | promoter | U2AF2 | NM_007279 | U2 small nuclear RNA auxiliary factor 2 | 19q13.43 | -8.2 |
| nulliparous | promoter | CLDND1 | NM_001040200 | daudin domain containing 1 | 3q12.1 | -17.6 |
| nulliparous | promoter | PPM1J | NM_005167 | protein phosphatase 1J (PP2C domain containing) | 1 p13.1 | -2.3 |
| nulliparous | promoter | C17orf68 | NM_025099 | chromosome 17 open reading frame 68 | 17p13.1 | -7.5 |
| nulliparous | promoter | ABCA5 | NM_172232 | ATP-binding cassette, sub-family A (ABC1), member 5 | 17q21-q25 | -2.1 |
| nulliparous | promoter | DIO1 | NM_001039715 | deiodinase, iodothyronine, type I | 1 p33-p32 | -3.1 |
| nulliparous | promoter | HIST2H2AA4 | NM_001040874 | histone cluster 2, H2aa4 | 1q21.2 | -6.5 |
| nulliparous | promoter | FNDC3A | NM_001079673 | fibronectin type III domain containing 3A | 13q14.12 | -4.1 |
| nulliparous | promoter | GPR161 | NM_153832 | G protein-coupled receptor 161 | 1q23.3 | -3.2 |
| nulliparous | promoter | NPEPPS | NM_006310 | aminopeptidase puromycin sensitive | 17q12-q21 | -3 |
| nulliparous | promoter | PLXDC2 | NM_032812 | plexin domain containing 2 | 10p12.33 | -5.1 |
| nulliparous | promoter | LZTS1 | NM_021020 | leucine zipper, putative tumor suppressor 1 | 8p22 | -4.2 |
| nulliparous | promoter | C16orf67 | NR_024034 | chromosome 16 open reading frame 67 | 16p11.2 | -9.5 |
| nulliparous | promoter | TCF4 | NM_001083962 | transcription factor 4 | 18q21. | -2.8 |
| nulliparous | promoter | FU10490 | NM_018111 | NA | NA | -3.2 |
| nulliparous | promoter | C1QL3 | NM_001010908 | complement component 1, q subcomponent-like 3 | 10p13 | -2.9 |
| nulliparous | promoter | FRAS1 | NM_025074 | Fraser syndrome 1 | 4q21 | -3.1 |
| nulliparous | promoter | XPOT | NM_007235 | exportin, tRNA (nuclear export receptor for tRNAs) | 12q14.1 | -7.9 |
| nulliparous | promoter | HOXB3 | NM_002146 | homeobox B3 | 17q21.32 | -2.3 |
| nulliparous | promoter | SPATA18 | NM_145263 | spermatogenesis associated 18 homolog (rat) | 4q11 | -7.9 |
| nulliparous | promoter | HOXB4 | NM_024015 | homeobox B4 | 17q21.32 | -3.4 |
| nulliparous | promoter | PGM3 | NM_015599 | phosphoglucomutase 3 | 6q14.1- | -4.4 |
| nulliparous | promoter | HERC3 | NM_014606 | hect domain and RLD 3 | 4q21 | -3.1 |
| nulliparous | promoter | HIST2H3C | NM_021059 | histone cluster 2, H3c | 1q21.2 | -3.1 |
| nulliparous | promoter | HIST2H3A | NM_001005464 | histone cluster 2, H3a | 1q21.2 | -3.6 |
| nulliparous | promoter | HIST1H2BC | NM_003526 | histone cluster 1, H2bc | 6p22.1 | |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | CHST1 | NM_003654 | carbohydrate (keratan sulfate Gal-6) sulfotransferase 1 | 11 p1 1.2 | −3.9 |
| nulliparous | promoter | COX7A1 | NM_001864 | cytochrome c oxidase subunit VIIa polypeptide 1 (muscle) | 19q13.1 | −13.8 |
| nulliparous | promoter | LMO3 | NM_001001395 | LIM domain only 3 (rhombotin-like 2) | 12p13 | −4.9 |
| nulliparous | promoter | HIST1H2BH | NM_003524 | histone cluster 1, H2bh | 6p21.3 | −2.5 |
| nulliparous | promoter | GARS | NM_002047 | glycyl-tRNA synthetase | 7p15 | −5.3 |
| nulliparous | promoter | TRIM41 | NM_033549 | tripartite motif-containing 41 | 5q35.3 | −11.1 |
| nulliparous | promoter | ZDHHC1 | NM_013304 | zinc finger, DHHC-type containing 1 | 16q22.1 | −4.1 |
| nulliparous | promoter | EPAS1 | NM_001430 | endothelial PAS domain protein 1 | 2p21-p16 | −5.2 |
| nulliparous | promoter | OLFML2A | NM_182487 | olfactomedin-like 2A | 9q34.11 | −10.7 |
| nulliparous | promoter | SRXN1 | NM_080725 | sulfiredoxin 1 homolog (S. cerevisiae) | 20p13 | −3.1 |
| nulliparous | promoter | FAM50A | NM_004699 | family with sequence similarity 50, member A | Xq28 | −3.2 |
| nulliparous | promoter | PEX6 | NM_000287 | peroxisomal biogenesis factor 6 | 6p22-p11 | −5 |
| nulliparous | promoter | CYP8B1 | NM_004391 | cytochrome P450, family 8, subfamily B, polypeptide 1 | 3p22.1 | −4.4 |
| nulliparous | promoter | HLCS | NM_000411 | holocarboxylase synthetase (biotin-(proprionyl-Coenzyme A-carboxylase (ATP-hydrolysing)) ligase) | 21q22.1 | −3.3 |
| nulliparous | promoter | ADFP | NM_001122 | NA | NA | −5.1 |
| nulliparous | promoter | INSM1 | NM_002196 | insulinoma-associated 1 | 20p11.2 | −3 |
| nulliparous | promoter | FBXO34 | NM_152231 | F-box protein 34 | 14q22.1 | −22.7 |
| nulliparous | promoter | HS6ST1 | NM_004807 | heparan sulfate 6-0-sulfotransferase 1 | 2q21 | −3.6 |
| nulliparous | promoter | MEF2D | NM_005920 | myocyte enhancer factor 2D | 1q12-q23 | −8.8 |
| nulliparous | promoter | NSD1 | NM_022455 | nuclear receptor binding SET domain protein 1 | 5q35 | −3.4 |
| nulliparous | promoter | FLNB | NM_001457 | filamin B, beta | 3p14.3 | −2.6 |
| nulliparous | promoter | SCN5A | NM_198056 | sodium channel, voltage-gated, tuna V/ alpha ciihmil | 3p21 | −2.1 |
| nulliparous | promoter | AGFG2 | NM_006076 | ArfGAP with FG repeats 2 | 7q22.1 | −7.1 |
| nulliparous | promoter | COX15 | NM_004376 | COX15 homolog, cytochrome c oxidase assembly protein (yeast) | 10q24 | −2.6 |
| nulliparous | promoter | PPP2R5B | NM_006244 | protein phosphatase 2, regulatory subunit B\ beta isoform | 11q12 | −3.9 |
| nulliparous | promoter | CYP26C1 | NM_183374 | cytochrome P450, family 26, subfamily C, polypeptide 1 | 10q23.33 | −9.3 |
| nulliparous | promoter | MGC33894 | NM_152914 | NA | NA | −2.8 |
| nulliparous | promoter | PKM2 | NM_182471 | pyruvate kinase, muscle | 15q22-qter | −2.1 |
| nulliparous | promoter | VMAC | NM_001017921 | vimentin-type intermediate filament associated coiled-coil protein | 19p13.3 | −2.5 |
| nulliparous | promoter | APIP | NM_015957 | APAF1 interacting protein | 11 p1 3 | −2.9 |
| nulliparous | promoter | CAP2B | NM_004930 | capping protein (actin filament) muscle Z-lme, beta | 1p36.1 | −4.4 |
| nulliparous | promoter | C8orf55 | NM_016647 | chromosome 8 open reading frame 55 | 8q24.3 | −4.7 |
| nulliparous | promoter | NOXO1 | NM_144603 | NADPH oxidase organizer 1 | 16p13.3 | −5.6 |
| nulliparous | promoter | UFD1L | NM_001035247 | ubiquitin fusion degradation 1 like | 22q11.2 | −15.1 |
| nulliparous | promoter | DHRS3 | NM_004753 | dehydrogenase/reductase (SDR family) member 3 | 1p36.1 | −5 |
| nulliparous | promoter | CYP20A1 | NM_177538 | cytochrome P450, family 20, subfamily A, polypeptide 1 | 2q33 | −4.2 |
| nulliparous | promoter | ZNF835 | NM_001005850 | zinc finger protein 835 | 19q13.43 | −2.8 |
| nulliparous | promoter | PPA2 | NM_006903 | pyrophosphatase (inorganic) 2 | 4q25 | −3.9 |
| nulliparous | promoter | REL | NM_002908 | v-rel reticuloendotheliosis viral oncogene homolog (avian) | 2p13-p12 | −9.7 |
| nulliparous | promoter | FBXO7 | NM_001033024 | F-box protein 7 | 22q11.2-gter | −7.1 |
| nulliparous | promoter | SNTB2 | NM_006750 | syntrophin, beta 2 (dystrophin-associated protein A1, 59 kDa, basic component 2) | 16q22.1 | −2.2 |
| nulliparous | promoter | GPKOW | NM_015698 | G patch domain and KOW motifs | Xp11.23 | −2.6 |
| nulliparous | promoter | INF2 | NM_022489 | inverted formin, FH2 and WH2 domain containing | 14q32.33 | −3.3 |
| nulliparous | promoter | GPRC5C | NM_022036 | G protein-coupled receptor, family C, group 5, member C | 17q25 | −33.1 |
| nulliparous | promoter | FNIP1 | NM_001008738 | folliculin interacting protein 1 | 5q23.3 | −5.2 |
| nulliparous | promoter | FZD2 | NM_001466 | frizzled homolog 2 (Drosophila) | 17p21.1 | −2.5 |
| nulliparous | promoter | SCRIB | NM_182706 | scribbled homolog (Drosophila) | 8q24.3 | −2.3 |
| nulliparous | promoter | NR6A1 | NM_033334 | nuclear receptor subfamily 6, group A, member 1 | 9q33.3 | −10.7 |
| nulliparous | promoter | PELI3 | NM_001098510 | pellino homolog 3 (Drosophila) | 11q13.2 | −13.1 |
| nulliparous | promoter | WDR27 | NM_182552 | WD repeat domain 27 | 6q27 | −5.8 |
| nulliparous | promoter | FLJ20433 | NM_017820 | NA | NA | −2.3 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | ALCAM | NM_001627 | activated leukocyte cell adhesion molecule | 3q13.1 | -3.6 |
| nulliparous | promoter | CUTC | NM_015960 | cutC copper transporter homolog (E. coli) | 10q24.31 | -2.6 |
| nulliparous | promoter | BMP2K | NM_017593 | BMP2 inducible kinase | 4q21.21 | -3.1 |
| nulliparous | promoter | PIK3R2 | NM_005027 | phosphoinositide-3-kinase, regulatory subunit 2 (beta) | 19q13.2-q13.4 | -3 |
| nulliparous | promoter | PCDHB11 | NM_018931 | protocadherin beta 11 | 5q31 | -5.5 |
| nulliparous | promoter | PCDHB10 | NM_018930 | protocadherin beta 10 | 5q31 | -5.5 |
| nulliparous | promoter | PCDHB17 | NR_001280 | protocadherin beta 17 pseudogene | 5q31 | -2.4 |
| nulliparous | promoter | PPP1R12C | NM_017607 | protein phosphatase 1, regulatory (inhibitor) subunit 12C | 19q13.42 | -2.1 |
| nulliparous | promoter | DUSP5 | NM_004419 | dual specificity phosphatase 5 | 10q25 | -2.3 |
| nulliparous | promoter | DUSP4 | NM_057158 | dual specificity phosphatase 4 | 8p12-p11 | -2.8 |
| nulliparous | promoter | CITED1 | NM_004143 | Cbp/p300-interacting transactivator, with Glu/Asp-rich carboxy-terminal domain, 1 | Xq13.1 | -2.1 |
| nulliparous | promoter | HIST2H2AA3 | NM_003516 | histone cluster 2, H2aa3 | 1q21.2 | -3.1 |
| nulliparous | promoter | PENK | NM_006211 | proenkephalin | 8q23-q24 | -2.2 |
| nulliparous | promoter | RAB14 | NM_016322 | RAB14, member RAS oncogene family | 9q32-q34.11 | -2.9 |
| nulliparous | promoter | CLIC4 | NM_013943 | chloride intracellular channel 4 | 1p | -3.1 |
| nulliparous | promoter | CEP55 | NM_018131 | centrosomal protein 55 kDa | 10q24.1 | -3.2 |
| nulliparous | promoter | KLHL21 | NM_014851 | kelch-like 21 (Drosophila) | 1p36 | -2.7 |
| nulliparous | promoter | WBSCR16 | NM_030798 | Williams-Beuren syndrome chromosome region 16 | 7q11.23 | -6.7 |
| nulliparous | promoter | ASCL2 | NM_005170 | achaete-scute complex homolog 2 (Drosophila) | 11p15.5 | -2.1 |
| nulliparous | promoter | PMP22 | NM_153321 | peripheral myelin protein 22 | 17p12 | -5 |
| nulliparous | promoter | DNAJC22 | NM_024902 | DnaJ (Hsp40) homolog, subfamily C, member 22 | 12q13.12 | -2.6 |
| nulliparous | promoter | BARX2 | NM_003658 | BARX homeobox 2 | 11q24.3 | -2.9 |
| nulliparous | promoter | IRX5 | NM_005853 | iroquois homeobox 5 | 16q12.2 | -2.1 |
| nulliparous | promoter | DCTN4 | NM_001135644 | dynactin 4 (p62) | 5q31-q32 | -2.5 |
| nulliparous | promoter | ELMOD2 | NM_153702 | ELMO/CED-12 domain containing 2 | 4q31.1 | -3.4 |
| nulliparous | promoter | DTNB | NM_021907 | dystrobrevin, beta | 2p23.2 | -3.5 |
| nulliparous | promoter | PRKAR1A | NM_212471 | protein kinase, cAMP-dependent, regulatory, type I, alpha (tissue specific extinguisher 1) | 17q23-q24 | -6.3 |
| nulliparous | promoter | IGF2BP1 | NM_006546 | insulin-like growth factor 2 mRNA binding protein 1 | 17q21.32 | -2.8 |
| nulliparous | promoter | KCNB2 | NM_004770 | potassium voltage-gated channel, Shab-related subfamily, member 2 | 8q13.2 | -10.7 |
| nulliparous | promoter | DUOX1 | NM_175940 | dual oxidase 1 | 15q21 | -4.5 |
| nulliparous | promoter | HEY2 | NM_012259 | hairy/enhancer-of-split related with YRPW motif 2 | 6q | -6.2 |
| nulliparous | promoter | HNRNPUL1 | NM_144732 | heterogeneous nuclear ribonucleoprotein U-like 1 | 19q13.31 | -5.7 |
| nulliparous | promoter | C14orf94 | NM_017815 | NA | NA | -2.7 |
| nulliparous | promoter | ZNF639 | NM_016331 | zinc finger protein 639 | 3q27.1 | -2.1 |
| nulliparous | promoter | KIF1B | NM_183416 | kinesin family member 1B | 1p36.22 | -4.5 |
| nulliparous | promoter | ZNF787 | NM_001002836 | zinc finger protein 787 | 19q13.42 | -3.1 |
| nulliparous | promoter | FAM20A | NM_017565 | family with sequence similarity 20, member A | 17q24.3 | -2.7 |
| nulliparous | promoter | GRIK3 | NM_000831 | glutamate receptor, ionotropic, kainate 3 | 1p34-p33 | -2.5 |
| nulliparous | promoter | NAB2 | NM_005967 | NGFI-A binding protein 2 (EGR1 binding protein 2) | 12q13.3 | -2.2 |
| nulliparous | promoter | ZFP36 | NM_003407 | zinc finger protein 36, C3H type, homolog (mouse) | 19q13.1 | -2.2 |
| nulliparous | promoter | NXT1 | NM_013248 | NTF2-like export factor 1 | 20p12-p11.2 | -2.8 |
| nulliparous | promoter | AATF | NM_012138 | apoptosis antagonizing transcription factor | 17q12 | -5.3 |
| nulliparous | promoter | PFAS | NM_012393 | phosphoribosylformylglycinamidine synthase | 17p13.1 | -2.3 |
| nulliparous | promoter | NKX3-1 | NM_006167 | NK3 homeobox 1 | 8p21.2 | -4.7 |
| nulliparous | promoter | DEM1 | NM_022774 | defects in morphology 1 homolog (S. cerevisiae) | 1p34.2 | -3 |
| nulliparous | promoter | MYL6B | NM_002475 | myosin, light chain 6B, alkali, smooth muscle and non-muscle | 12q13.2 | -3.1 |
| nulliparous | promoter | MAD2L2 | NM_006341 | MAD2 mitotic arrest deficient-like 2 | 1p36 | -2.8 |
| nulliparous | promoter | RBM6 | NM_005777 | RNA binding motif protein 6 | 3p21.3 | -4.8 |
| nulliparous | promoter | SPHK1 | NM_021972 | sphingosine kinase 1 | 17q25.2 | -4.2 |
| nulliparous | promoter | BTRC | NM_003939 | beta-transducin repeat containing | 10q24.32 | -5.9 |
| nulliparous | promoter | RBM3 | NM_006743 | RNA binding motif (RNP1, RRM) protein 3 | Xp11.2 | -3.9 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | EPS8 | NM_004447 | epidermal growth factor receptor pathway substrate 8 | 12p12.3 | -7.5 |
| nulliparous | promoter | CD55 | NM_001114752 | CD55 molecule, decay accelerating factor for complement (Cromer blood group) | 1q32 | -2.4 |
| nulliparous | promoter | A1BG | NM_130786 | alpha-1-B glycoprotein | 19q | -6.9 |
| nulliparous | promoter | FLJ40125 | NM_001080401 | NA | NA | -5.3 |
| nulliparous | promoter | JUNB | NM_002229 | jun B proto-oncogene | 19p13.13 | -7.8 |
| nulliparous | promoter | SCP2 | NM_001007098 | sterol carrier protein 2 | 1p32 | -5.8 |
| nulliparous | promoter | CPEB2 | NM_182485 | cytoplasmic polyadenytation element binding protein 2 | 4p15.33 | -3 |
| nulliparous | promoter | CBX8 | NM_020649 | chromobox homolog 8 (Pc class homolog, Drosophila) | 17q25.3 | -9.4 |
| nulliparous | promoter | NOXA1 | NM_006647 | NAD PH oxidase activator 1 | 9 | -2.3 |
| nulliparous | promoter | PRSS3 | NM_007343 | protease, serine, 3 | 9p13 | -2.1 |
| nulliparous | promoter | ZMYND15 | NM_001136046 | zinc finger, MYND-type containing 15 | 17p13.3 | -2.2 |
| nulliparous | promoter | MAP7 | NM_003980 | microtubule-associated protein 7 | 6q23.2 | -2.3 |
| nulliparous | promoter | WDR82 | NM_025222 | WD repeat domain 82 | 3p21.2 | -5.6 |
| nulliparous | promoter | N4BP3 | NM_015111 | NA | NA | -4.2 |
| nulliparous | promoter | ZNF813 | NM_001004301 | zinc finger protein 813 | 19q13.41 | -2.7 |
| nulliparous | promoter | DKK3 | NM_001018057 | dickkopf homolog 3 (Xenopus laevis) | 11 p15.3 | -2.4 |
| nulliparous | promoter | B3GNT9 | NM_033309 | UDP-GlcNAc:betaGal beta-1,3-N-acetylglucosaminyltransferase 9 | 16q22.1 | -6.7 |
| nulliparous | promoter | UIMC1 | NM_016290 | ubiquitin interaction motif containing 1 | 5q35.2 | -2.5 |
| nulliparous | promoter | C1orf187 | NM_198545 | chromosome 1 open reading frame 187 | 1p36.22 | -4.3 |
| nulliparous | promoter | ZNF721 | NM_133474 | zincfinger protein 721 | 4p16.3 | -18.9 |
| nulliparous | promoter | MEF2C | NM_002397 | myocyte enhancer factor 2C | 5q14 | -2.2 |
| nulliparous | promoter | PTPN21 | NM_007039 | protein tyrosine phosphatase, non-receptor type 21 | 14q31 | -3.4 |
| nulliparous | promoter | ERBB4 | NM_001042599 | v-erb-a erythroblastic leukemia viral oncogene homolog 4 (avian) | 2q33.3-q34 | -2.1 |
| nulliparous | promoter | INPPL1 | NM_001567 | inositol polyphosphate phosphatase-like 1 | 11q23 | -3.6 |
| nulliparous | promoter | LYPD1 | NM_001077427 | LY6/PLAUR domain containing 1 | 2q21.2 | -3.4 |
| nulliparous | promoter | EWSR1 | NM_005243 | Ewing sarcoma breakpoint region 1 | 22q12.2 | -5.3 |
| nulliparous | promoter | ODC1 | NM_002539 | ornithine decarboxylase 1 | 2p25 | -2.5 |
| nulliparous | promoter | GLI3 | NM_000168 | GLI family zinc finger 3 | 7p13 | -9.5 |
| nulliparous | promoter | KIF5C | NM_004522 | kinesin family member 5C | 2q23 | -2.6 |
| nulliparous | promoter | COPG2 | NM_012133 | coatomer protein complex, subunit gamma 2 | 7q32 | -2.4 |
| nulliparous | promoter | SGMS1 | NM_147156 | sphingomyelin synthase 1 | 10q11.2 | -2.3 |
| nulliparous | promoter | DNAJC10 | NM_018981 | DnaJ (Hsp40) homolog, subfamily C, member 10 | 2q32.1 | -2.5 |
| nulliparous | promoter | HOMER1 | NM_004272 | homer homolog 1 (Drosophila) | 5q14.2 | -2.7 |
| nulliparous | promoter | SLC35E2 | NM_182838 | solute carrier family 35, member E2 | 1p36.32 | -33.6 |
| nulliparous | promoter | SEMA6A | NM_020796 | sema domain, transmembrane domain (TM), and cytoplasmic domain, (semaphorin) 6A | 5q23 | -2.3 |
| nulliparous | promoter | VISA | NM_020746 | NA | NA | -7.6 |
| nulliparous | promoter | CISD2 | NM_001008388 | CDGSH iron sulfur domain 2 | 4q24 | -2.6 |
| nulliparous | promoter | MFSD9 | NM_032718 | major facilitator superfamily domain containing 9 | 2q12.1 | -2.5 |
| nulliparous | promoter | MPND | NM_032868 | MPN domain containing | 19p13.3 | -3.3 |
| nulliparous | promoter | CYR61 | NM_001554 | cysteine-rich, angiogenic inducer, 61 | 1p22.3 | -2.4 |
| nulliparous | promoter | HIST1H2AC | NM_003512 | histone cluster 1, H2ac | 6p22.1 | -3.6 |
| nulliparous | promoter | PIGG | NM_001127178 | phosphatidylinositol glycan anchor biosynthesis, class G | 4p16.3 | -18.9 |
| nulliparous | promoter | SUPT16H | NM_007192 | suppressor of Ty 16 homolog (S. cerevisiae) | 14q11.1 | -2.2 |
| nulliparous | promoter | TLX2 | NM_016170 | T-cell leukemia homeobox 2 | 2p13.1 | -6.4 |
| nulliparous | promoter | CDC42EP1 | NM_152243 | CDC42 effector protein (Rho GTPase binding) 1 | 22q13.1 | -60.5 |
| nulliparous | promoter | GLRB | NM_000824 | glycine receptor, beta | 4q31.3 | -5.6 |
| nulliparous | promoter | RTN2 | NM_005619 | reticulon 2 | 19q13.2-q13.3 | -5.3 |
| nulliparous | promoter | AP2S1 | NM_021575 | adaptor-related protein complex 2, sigma 1 subunit | 19q13.2-q13.3 | -19.7 |
| nulliparous | promoter | PIGQ | NM_148920 | phosphatidylinositol glycan anchor biosynthesis, class G | 16p13.3 | -6 |
| nulliparous | promoter | POU4F2 | NM_004575 | POU class 4 homeobox 2 | 4q31.22 | -2.8 |
| nulliparous | promoter | HIST1H3F | NM_021018 | histone cluster 1, H3f | 6p22.1 | -2.5 |

TABLE 14-continued

Comprehensive DNA Methylation and K27 Profiles of CD44+ Nulliparous and Parous Breast Epithelial Cells

| | | | | | | |
|---|---|---|---|---|---|---|
| nulliparous | promoter | PIGU | NM_080476 | phosphatidylinositol glycan anchor biosynthesis, class U | 20q11.22 | -3.2 |
| nulliparous | promoter | SLK | NM_014720 | STE20-like kinase (yeast) | 10q25.1 | -5.9 |
| nulliparous | promoter | VASP | NM_003370 | vasodilator-stimulated phosphoprotein | 19q13.2-q13.3 | -2.5 |
| nulliparous | promoter | ANKRD34B | NM_001004441 | ankyrin repeat domain 34B | 5q14.1 | -2.5 |
| nulliparous | promoter | MICALL2 | NM_182924 | MICAL-like 2 | 7p22.3 | -31.6 |
| nulliparous | promoter | FEZF1 | NM_001024613 | FEZ family zinc finger 1 | 7q31.32 | -6.2 |
| nulliparous | promoter | SLC35F5 | NM_025181 | solute carrier family 35, member F5 | 2q14.1 | -4.6 |
| nulliparous | promoter | SLC25A22 | NM_024698 | solute carrier family 25 (mitochondrial carrier;glutamate), member 22 | 11 | -2.9 |
| nulliparous | promoter | RNU11 | NR_004407 | RNA, U11 small nuclear | 1p35 | -3 |
| nulliparous | promoter | CLP1 | NM_006831 | CLP1, cleavage and polyadenylation factor 1 subunit, homolog (S. cerevisiae) | 11q12 | -3.3 |
| nulliparous | promoter | LGALS8 | NM_201544 | lectin, galactoside-binding, soluble, 8 | 1q43 | -3.1 |
| nulliparous | promoter | AARS | NM_001605 | alanyl-tRNA synthetase | 16q22 | -7.5 |
| nulliparous | promoter | DKK2 | NM_014421 | dickkopf homolog 2 (Xenopus laevis) | 4q25 | -7.8 |
| nulliparous | promoter | AGAP2 | NM_001122772 | ArfGAP with GTPase domain, ankyrin repeat and PH domain 2 | 12q13.2 | -3.1 |
| nulliparous | promoter | ELA2 | NM_001972 | NA | NA | -2.1 |
| nulliparous | promoter | LOC201229 | NM_001076680 | NA | NA | -7.1 |
| nulliparous | promoter | CREB3L2 | NM_194071 | cAMP responsive element binding protein 3-like 2 | 7q34 | -3 |
| nulliparous | promoter | NEDD4L | NM_015277 | neural precursor cell expressed, developmentally down-regulated 4-like | 18q21 | -2.1 |
| nulliparous | promoter | SFRS15 | NM_020706 | splicing factor, arginine/serine-rich 15 | 21q22.1 | -4.6 |
| nulliparous | promoter | RND3 | NM_005168 | Rho family GTPase 3 | 2q23.3 | -2.2 |
| nulliparous | promoter | PAX9 | NM_006194 | paired box 9 | 14q13.3 | -2.7 |
| nulliparous | promoter | ACTL6B | NM_016188 | actin-like 6B | 7q22 | -2.5 |
| nulliparous | promoter | C9orf95 | NM_017881 | chromosome 9 open reading frame 95 | 9q21.31 | -3 |
| nulliparous | promoter | CNN2 | NM_004368 | calponin 2 | 19p13.3 | -2.5 |
| nulliparous | promoter | CDC45L | NM_003504 | CDC45 cell division cycle 45-like (S. cerevisiae) | 22q11.21 | -15.1 |
| nulliparous | promoter | PICALM | NM_001008660 | phosphatidylinositol binding clathrin assembly protein | 11q14 | -2.8 |
| nulliparous | promoter | C1orf94 | NM_001134734 | chromosome 1 open reading frame 94 | 1p34.3 | -2.2 |
| nulliparous | promoter | ASB13 | NM_024701 | ankyrin repeat and SOCS box-containing 13 | 10p15.1 | 2.6 |
| parous | promoter | CRAMP1L | NM_020825 | Crm, cramped-like (Drosophila) | 16p13.3 | 2.1 |
| parous | promoter | HSPA8 | NM_006597 | heat shock 70 kDa protein 8 | 11q24.1 | 4.4 |
| parous | promoter | CDO1 | NM_001801 | cysteine dioxygenase, type I | 5q23.2 | 7.7 |
| parous | promoter | UBAC1 | NM_016172 | UBA domain containing 1 | 9q34.3 | 5 |
| parous | promoter | ATP2C2 | NM_014861 | ATPase, Ca++ transporting, type 2C, member 2 | 16q24.1 | 3.8 |
| parous | promoter | PRPF4 | NM_004697 | PRP4 pre-mRNA processing factor 4 homolog (yeast) | 9q31-q33 | 2.2 |
| parous | promoter | SLC30A3 | NM_003459 | solute carrier family 30 (zinc transporter), member 3 | 2p23.3 | 4.2 |
| parous | promoter | SAMD14 | NM_174920 | sterile alpha motif domain containing 14 | 17q21.33 | 2.9 |
| parous | promoter | C1orf174 | NM_207356 | chromosome 1 open reading frame 174 | 1p36.32 | 3 |
| parous | promoter | DSC2 | NM_024422 | desmocollin 2 | 18q12.1 | 2.6 |
| parous | promoter | NXPH3 | NM_007225 | neurexophilin 3 | 17q | 2.3 |
| parous | promoter | WHSC1L1 | NM_023034 | Wolf-Hirschhorn syndrome candidate 1-like 1 | 8p11.2 | 4.8 |
| parous | promoter | DGCR6 | NM_005675 | DiGeorge syndrome critical region gene 6 | 22q11.21 | 9.4 |
| parous | promoter | GUK1 | NM_000858 | guanylate kinase 1 | 1q32-q41 | 3.1 |
| parous | promoter | SYNCRIP | NM_006372 | synaptotagmin binding, cytoplasmic RNA interacting protein | 6q14-q15 | -2.4 |
| parous | promoter | SYNCRIP | NM_006372 | synaptotagmin binding, cytoplasmic RNA interacting protein | 6q14-q15 | 2.5 |
| parous | promoter | IRX2 | NM_001134222 | iroquois homeobox 2 | 5p15.33 | 2.7 |
| parous | promoter | BRP44 | NM_015415 | brain protein 44 | 1q24 | 5.3 |
| parous | promoter | ALOXE3 | NM_021628 | arachidonate lipoxygenase 3 | 17p13.1 | 55.5 |
| parous | promoter | KCTD11 | NM_001002914 | potassium channel tetramerisation domain containing 11 | 17p13.2 | 28.3 |
| parous | promoter | SCAND1 | NM_033630 | SCAN domain containing 1 | 20q11.1-q11.23 | 4.4 |
| parous | promoter | SHOX2 | NM_003030 | short stature homeobox 2 | 3q25.32 | 2.1 |
| parous | promoter | C7orf46 | NM_199136 | chromosome 7 open reading frame 46 | 7p15.3 | 4.4 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | promoter | LIME1 | NM_017806 | Lck interacting transmembrane adaptor 1 | 20q13.3 | 2.2 |
| parous | promoter | ZNF444 | NM_018337 | zinc finger protein 444 | 19q13.43 | 21.6 |
| parous | promoter | FAM76B | NM_144664 | family with sequence similarity 76, member B | 11q21 | 7.5 |
| parous | promoter | ACCN2 | NM_020039 | amiloride-sensitive cation channel 2, neuronal | 12q12 | 2.4 |
| parous | promoter | KCTD14 | NM_023930 | potassium channel tetramerisation domain containing 14 | 11q13.4 | 13.3 |
| parous | promoter | SYK | NM_003177 | spleen tyrosine kinase | 9q22 | 4 |
| parous | promoter | LOC100133_612 | NR_024455 | NA | NA | 3 |
| parous | promoter | PKIG | NM_007066 | protein kinase (cAMP-dependent, catalytic) inhibitor gamma | 20q13.12-q13.13 | 2.5 |
| parous | promoter | SHROOM1 | NM_133456 | shroom family member 1 | 5q31.1 | 13.5 |
| parous | promoter | FBXL7 | NM_012304 | F-box and leucine-rich repeat protein 7 | 5p15.1 | 2.4 |
| parous | promoter | NPB | NM_148896 | neuropeptide B | 17q25.3 | 5 |
| parous | promoter | CCND1 | NM_053056 | cyclin D1 | 11q13 | 2.1 |
| parous | promoter | SNHG1 | NR_003098 | small nucleolar RNA host gene 1 (non-protein coding) | 11q12.3 | 4.6 |
| parous | promoter | FAM36A | NM_198076 | family with sequence similarity 36, member A | 1q44 | 2.9 |
| parous | promoter | GNA12 | NM_007353 | guanine nucleotide binding protein (G protein) alpha 12 | 7p22.3 | 3.1 |
| parous | promoter | LOC653319 | NM_001040715 | NA | NA | 6.3 |
| parous | promoter | LGR5 | NM_003667 | leucine-rich repeat-containing G protein-coupled receptor 5 | 12q22-q23 | 3.3 |
| parous | promoter | ANKRD57 | NM_023016 | ankyrin repeat domain 57 | 2q13 | 2.9 |
| parous | promoter | CDKN1C | NM_000076 | cyclin-dependent kinase inhibitor 1C (p57, Kip2) | 11p15.5 | 2.3 |
| parous | promoter | GSTZ1 | NM_001513 | glutathione transferase zeta 1 | 14q24.3 | 2.7 |
| parous | promoter | SLC7A5 | NM_003486 | solute carrier family 7 (cationic amino acid transporter, y+ system), member 5 | 16q24.3 | 2.9 |
| parous | promoter | KAT2A | NM_021078 | K(lysine) acetyltransferase 2A | 17q12-q21 | 2.8 |
| parous | promoter | SERINC2 | NM_178865 | serine incorporator 2 | 1p35.1 | 2.1 |
| parous | promoter | SNED1 | NM_001080437 | sushi, nidogen and EGF-like | 2q37.3 | 2.1 |
| parous | promoter | LPPR4 | NM_014839 | NA | NA | 2.7 |
| parous | promoter | KREMEN2 | NM_024507 | kringle containing transmembrane protein 2 | 16p13.11 | 19.4 |
| parous | promoter | CTXN1 | NM_206833 | cortexin 1 | 19 | 2.9 |
| parous | promoter | GPRASP1 | NM_014710 | G protein-coupled receptor associated sorting protein 1 | Xq22.1 | 5.1 |
| parous | promoter | NT5M | NM_020201 | 5',3"-nucleotidase, mitochondrial | 17p11.2 | 5.1 |
| parous | promoter | USP48 | NM_032236 | ubiquitin specific peptidase 48 | 1p36.12 | 2.3 |
| parous | promoter | YPEL2 | NM_001005404 | yippee-like 2 (Drosophila) | 17q23 | 2.9 |
| parous | promoter | SCD | NM_005063 | stearoyl-CoA desaturase (delta-9-desaturase) | 10q23-q24 | 35.1 |
| parous | promoter | PPM1L | NM_139245 | protein phosphatase 1 (formerly 2C)-like | 3q26.1 | 2.2 |
| parous | promoter | NCRNA00092 | NR_024129 | non-protein coding RNA 92 | 9q22.32 | 2.8 |
| parous | promoter | LOC389634 | NR_024420 | NA | NA | 3.7 |
| parous | promoter | IFT122 | NM_018262 | intraflagellar transport 122 homolog (Chlamydomonas) | 3q21 | 4 |
| parous | promoter | CCL25 | NM_005624 | chemokine (C-C motif) ligand 25 | 19p13.2 | 3.8 |
| parous | promoter | EPM2A | NM_005670 | epilepsy, progressive myoclonus type 2A, Lafora disease (laforin) | 6q24 | 2.6 |
| parous | promoter | SH2D4A | NM_022071 | SH2 domain containing 4A | 8p21 | 6.3 |
| parous | promoter | EFS | NM_032459 | embryonal Fyn-assoaated substrate | 14q11.2- | 3.3 |
| parous | promoter | PHRF1 | NM_020901 | PHD and ring finger domains 1 | 11p15.5 | 2.9 |
| parous | promoter | DDT | NM_001084392 | D-dopachrome tautomerase | 22q11.23 | 3.9 |
| parous | promoter | CUX1 | NM_181552 | cut-like homeobox 1 | 7q22.1 | 2.4 |
| parous | promoter | SFPQ | NM_005066 | splicing factor proline/glutamine-rich (polypyTimidine tract binding protein associated) | 1p34.3 | 2.2 |
| parous | promoter | LOC85389 | NR_001453 | NA | NA | 4.4 |
| parous | promoter | CNTFR | NM_001842 | aliary neurotrophic factor receptor | 9p13 | 2.5 |
| parous | promoter | TMEM95 | NM_198154 | transmembrane protein 95 | 17p13.1 | 28.3 |
| parous | promoter | HIST1H2BI | NM_003525 | histone cluster 1, H2bi | 6p22.1 | 2.2 |
| parous | promoter | SEMA5B | NM_001031702 | sema domain, seven thrombospondin repeats (type 1 and type 1-like), transmembrane domain (TM) and short cytoplasmic domain, (semaphorin) 5B | 3q21.1 | 11.2 |
| parous | promoter | VASH1 | NM_014909 | vasohibin 1 | 14q24.3 | 2.5 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | promoter | SLC3A2 | NM_001012663 | solute carrier family 3 (activators of dibasic and neutral amino acid transport), member 2 | 11q12-q22 | 4.6 |
| parous | promoter | CDC26 | NM_139286 | cell division cycle 26 homolog (S. cerevisiae) | 9q32 | 2.2 |
| parous | promoter | SPOCK1 | NM_004598 | sparc/osteonectin, cwcv and kazal-like domains proteoglycan (testican) 1 | 5q31.2 | 2.3 |
| parous | promoter | SLC18A3 | NM_003055 | solute carrier family 18 (vesicular acetylcholine), member 3 | 10q11.2 | 4.7 |
| parous | promoter | ZNF114 | NM_153608 | zinc finger protein 114 | 19q13.32 | 2.4 |
| parous | promoter | POMT2 | NM_013382 | protein-O-mannosyltransferase 2 | 14q24 | 2.7 |
| parous | promoter | LCORL | NM_153686 | ligand dependent nuclear receptor corepressor-like | 4p15.32 | 3.8 |
| parous | promoter | HES7 | NM_032580 | hairy and enhancer of split 7 (Drosophila) | 17p13.1 | 55.5 |
| parous | promoter | GIGYF1 | NM_022574 | GRB10 interacting GYF protein 1 | 7q22 | 11.1 |
| parous | promoter | CCDC48 | NM_024768 | coiled-coil domain containing 48 | 3q21.3 | 2.1 |
| parous | promoter | HOXA13 | NM_000522 | homeobox A13 | 7p15.2 | 3.3 |
| parous | promoter | PAPD5 | NM_001040284 | PAP associated domain containing 5 | 16q12.1 | 3.6 |
| parous | promoter | LETM2 | NM_144652 | leucine zipper-EF-hand containing transmembrane protein 2 | 8p12 | 4.8 |
| parous | promoter | LOC85391 | NR_003125 | NA | NA | 4.4 |
| parous | promoter | SMPD4 | NM_017751 | sphingomyelin phosphodiesterase 4, neutral membrane (neutral sphingomyelinase-3) | 2q21.1 | 6.2 |
| parous | promoter | FBXO2 | NM_012168 | F-box protein 2 | 1p36.21 | 4.6 |
| parous | promoter | ADAMTS15 | NM_139055 | ADAM metallopeptidase with thrombospondin type 1 motif, 15 | 11q25 | 16.9 |
| parous | promoter | CHAT | NM_020549 | choline acetyltransferase | 10q11.2 | 4.7 |
| parous | promoter | LHFPL4 | NM_198560 | lipoma HMGIC fusion partner-like 4 | 3p25.3 | 2.5 |
| parous | promoter | PANX2 | NM_052839 | pannexin 2 | 22q13.33 | 5 |
| parous | promoter | LOC85390 | NR_001454 | NA | NA | 4.4 |
| parous | promoter | FLT3 | NM_004119 | fms-related tyrosine kinase 3 | 13q12 | 2.3 |
| parous | promoter | PODN | NM_153703 | podocan | 1p32.3 | 2.9 |
| parous | promoter | SBK1 | NM_001024401 | SH3-binding domain kinase 1 | 16p11.2 | 2.8 |
| parous | promoter | GAD1 | NM_013445 | glutamate decarboxylase 1 (brain, 67 kDa) | 2q31 | 2.4 |
| parous | promoter | FAM54B | NM_001099625 | family with sequence similarity 54, member B | 1 p36.11 | 20.9 |
| parous | promoter | CDT1 | NM_030928 | chromatin licensing and DNA replication factor 1 | 16q24.3 | 3.6 |
| parous | promoter | ZNF28 | NM_006969 | zinc finger protein 28 | 19q13.41 | 2.2 |
| parous | promoter | PCBD2 | NM_032151 | pterin-4 alpha-carbinolamine dehydratase/d imerization cofactor of hepatocyte nuclear factor 1 alpha (TCF1) 2 | 5q31.1 | 3.2 |
| parous | promoter | RIMS4 | NM_182970 | regulating synaptic membrane exocytosis 4 | 20q13.12 | 2.3 |
| parous | promoter | FBXO44 | NM_183412 | F-box protein 44 | 1p36.21 | 4.6 |
| parous | promoter | GPRIN1 | NM_052899 | G protein regulated inducer of neurite outgrowth 1 | 5q35.2 | 2.4 |
| parous | promoter | C5orf38 | NM_178569 | chromosome 5 open reading frame 38 | 5p15.33 | 2.7 |
| parous | promoter | MAP6 | NM_033063 | microtubule-associated protein 6 | 11q13.5 | 2.6 |
| parous | promoter | PAQR4 | NM_152341 | progestin and adipoQ receptor family member IV | 16p13 | 19.4 |
| parous | promoter | ASGR1 | NM_001671 | asialoglycoprotein receptor 1 | 17p13-p11 | 3.8 |
| parous | promoter | TPD52L2 | NM_003288 | tumor protein D52-like 2 | 20q13.2-q13.3 | 2.6 |
| parous | promoter | PRKAR1B | NM_002735 | protein kinase, cAMP-dependent, regulatory, type I, beta | 7pter-p22 | 2.3 |
| parous | promoter | CHRNA3 | NM_000743 | cholinergic receptor, nicotinic, alpha 3 | 15q24 | 24.3 |
| parous | promoter | GHSR | NM_198407 | growth hormone secretagogue receptor | 3q26.31 | 2.4 |
| parous | promoter | FMN2 | NM_020066 | formin 2 | 1q43 | 21.9 |
| parous | promoter | TRAFD1 | NM_006700 | TRAF-type zinc finger domain containing 1 | 12q | 17.3 |
| parous | promoter | KIF1A | NM_004321 | kinesin family member 1A | 2q37.2 | 2.5 |
| parous | promoter | SGK1 | NM_005627 | serum/glucocorticoid regulated kinase 1 | 6q23 | 2.6 |
| parous | promoter | RAB11FIP4 | NM_032932 | RAB11 family interacting protein 4 (class II) | 17q11.2 | 6.1 |
| parous | promoter | ATP6V1E1 | NM_001696 | ATPase, H+ transporting, lysosomal 31 kDa, V1 subunit E1 | 22pterq11.2 | 2.4 |
| parous | promoter | DDX51 | NM_175066 | DEAD (Asp-Glu-Ala-Asp) box polypeptide 51 | 12q24.33 | 6.3 |
| parous | promoter | PLXNA4 | NM_001105543 | plexin A4 | 7q32.3 | 3.5 |
| parous | promoter | FAM128B | NM_025029 | family with sequence similarity 128, member B | 2q21.1 | 6.2 |
| parous | promoter | TMTC4 | NM_001079669 | transmembrane and tetratricopeptide repeat containing 4 | 13q32.3 | 3.8 |
| parous | promoter | EMP2 | NM_001424 | epithelial membrane protein 2 | 16p13.2 | 2.6 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | promoter | DDTL | NM_001084393 | D-dopachrome tautomerase-like | 22q11.23 | 3.9 |
| parous | promoter | PDE4A | NM_001111307 | phosphodiesterase 4A, cAMP-specific (phosphodiesterase E2 dunce homolog, *Drosophila*) | 19p13.2 | 3.1 |
| parous | promoter | LOC729375 | NR_024252 | NA | NA | 5.4 |
| parous | promoter | AGGF1 | NM_018046 | angiogenic (actor with G patch and FHA domains 1 | 5q13.3 | 3.1 |
| parous | promoter | AKR1CL2 | NM_001040177 | NA | NA | 5.2 |
| parous | promoter | FLJ10661 | NR_024362 | NA | NA | 7.3 |
| parous | promoter | CEP57 | NM_014679 | centrosomal protein 57 kDa | 11q21 | 7.5 |
| parous | promoter | DIP2C | NM_014974 | DIP2 disco-interacting protein 2 homolog C (*Drosophila*) | 10p 15.3 | 2.8 |
| parous | promoter | IGSF3 | NM_001007237 | immunoglobulin superfamily, member 3 | 1p13 | 2.7 |
| parous | promoter | LRRC27 | NM_030626 | leucine rich repeat containing 27 | 10 | 6 |
| parous | promoter | ERF | NM_006494 | Ets2 repressor (actor | 19q13 | 4.1 |
| parous | promoter | PRELID1 | NM_013237 | PRELI domain containing 1 | 5q35.3 | 2.1 |
| parous | promoter | EZR | NM_003379 | ezrin | 6q25.3 | 2.6 |
| parous | promoter | BMP6 | NM_001718 | bone morphogenetic protein 6 | 6p24-p23 | 3 |
| parous | promoter | NOC4L | NM_024078 | nucleolar complex associated 4 homolog (*S. cerevisiae*) | 12q24.33 | 6.3 |
| parous | promoter | SEC31B | NM_015490 | SEC31 homolog B (*S. cerevisiae*) | 10q24.32 | 2.4 |
| parous | promoter | GPR135 | NM_022571 | G protein-coupled receptor 135 | 14q23.1 | 2.7 |
| parous | promoter | UCKL1 | N M_017859 | uridine-cytidine kinase 1-like 1 | 20 | 2.4 |
| parous | promoter | SNORD22 | NR_000008 | small nucleolar RNA, C/D box 22 | 11q13 | 4.6 |
| parous | promoter | SNORD25 | NR_002565 | small nucleolar RNA, C/D box 25 | 11q13 | 4.6 |
| parous | promoter | SNORD27 | NR_002563 | small nucleolar RNA, C/D box 27 | 11q12.3 | 4.6 |
| parous | promoter | SNORD26 | NR_002564 | small nucleolar RNA, C/D box 26 | 11q12.3 | 4.6 |
| parous | promoter | SNORD29 | NR_002559 | small nucleolar RNA, C/D box 29 | 11q12.3 | 4.6 |
| parous | promoter | IQWD1 | NM_001017977 | NA | NA | 5.3 |
| parous | promoter | SLC9A3R1 | NM_004252 | solute carrier family 9 (sodium/hydrogen exchanger), member 3 regulator 1 | 17q25.1 | 2.8 |
| parous | promoter | SCAMP1 | NM_004866 | secretory carrier membrane protein 1 | 5q14.1 | 2.4 |
| parous | promoter | TERC | NR_001566 | telomerase RNA component | 3q26.2 | 2.7 |
| parous | promoter | FOXRED2 | NM_024955 | FAD-dependent oxidoreductase domain containing 2 | 22q12.3 | 3.7 |
| parous | promoter | TMEM55B | NM_001100814 | transmembrane protein 55B | 14q11.1 | 2.8 |
| parous | promoter | C9orf66 | NM_152569 | chromosome 9 open reading frame 66 | 9p24.3 | -3.2 |
| parous | promoter | C9orf66 | NM_152569 | chromosome 9 open reading frame 66 | 9p24.3 | 3.2 |
| parous | promoter | MSX1 | NM_002448 | msh homeobox 1 | 4p16.2 | 2.7 |
| parous | promoter | MSX1 | NM_002448 | msh homeobox 1 | 4p16.2 | 2 |
| parous | promoter | 38239 | NM_144710 | NA | NA | 2.9 |
| parous | promoter | ULK1 | NM_003565 | unc-51-like kinase 1 (*C. elegans*) | 12q24.3 | 5.4 |
| parous | promoter | MAT2A | NM_005911 | methionine adenosyltransferase II, alpha | 2p11.2 | 4.1 |
| parous | promoter | CARD10 | NM_014550 | caspase recruitment domain family, member 10 | 22q13.1 | 4.8 |
| parous | promoter | MMD2 | NM_001100600 | monocyte to macrophage differentiation-associated 2 | 7p22 | 2.5 |
| parous | promoter | HSPB9 | NM_033194 | heat shock protein, alpha-crystallin-related, B9 | 17q21 | 2.8 |
| parous | promoter | CRLS1 | NM_019095 | cardiolipin synthase 1 | 20p13-p12.3 | 7.4 |
| parous | promoter | PRICKLE3 | NM_006150 | prickle homolog 3 (*Drosophila*) | Xp11.23 | 2.2 |
| parous | promoter | HIST1H3G | NM_003534 | histone cluster 1, H3g | 6p22.1 | 2.2 |
| parous | promoter | SLC7A5P1 | NR_002593 | solute carrier family 7 (cationic amino acid transporter, y+ system), member 5 pseudogene 1 | 16p11.2 | 2.6 |
| parous | promoter | TMBIM1 | NM_022152 | transmembrane BAX inhibitor motif containing 1 | 2q35 | 2.6 |
| parous | promoter | RAB24 | NM_130781 | RAB24, member RAS oncogene family | 5q35.3 | 2.1 |
| parous | promoter | FAM43A | NM_153690 | family with sequence similarity 43, member A | 3q29 | 2.2 |
| parous | promoter | SNORD30 | NR_002561 | small nucleolar RNA, C/D box 30 | 11q12.3 | 4.6 |
| parous | promoter | SNORD31 | NR_002560 | small nucleolar RNA, C/D box 31 | 11q12.3 | 4.6 |
| parous | promoter | SLC2A4RG | NM_020062 | SLC2A4 regulator | 20q13.33 | 2.2 |
| parous | promoter | MBD4 | NM_003925 | methyl-CpG binding domain protein 4 | 3q21.3 | 4 |
| parous | promoter | REC8 | NM_005132 | REC8 homolog (yeast) | 14q11.2- | 2.2 |

TABLE 14-continued

Comprehensive DNA Methylation and K27 Profiles of CD44+ Nulliparous and Parous Breast Epithelial Cells

| | | | | | | |
|---|---|---|---|---|---|---|
| parous | promoter | CREB3L1 | NM_052854 | cAMP responsive element binding protein 34 like 1 | 11q11 | 2.2 |
| parous | promoter | SCN1B | NM_199037 | sodium channel, voltage-gated, type I, beta | 19 | 3.8 |
| parous | promoter | ADARB2 | NM_018702 | adenosine deaminase, RNA-specific, B2 (RED2 homolog rat) | 10p15.3 | 3.3 |
| parous | promoter | SNORD28 | NR_002562 | small nucleolar RNA, C/D box 28 | 11q12.3 | 4.6 |
| parous | promoter | ATP6V1C2 | NM_144583 | ATPase, H+ transporting, lysosomal 42 kDa, V1 subunit C2 | 2p25.1 | 3.1 |
| parous | promoter | BZW1 | NM_014670 | basic leuine zipper and W2 domains 1 | 2q33 | 3.9 |

| log2 Ration | CD44+ NCC | CD44+ N35 | CD44+ N48 | CD44+ N37 | CD44+ N39 | CD44+ N40 | BssHII region | Distance from TSS |
|---|---|---|---|---|---|---|---|---|
| 4.07643837 | 94.7 | 32 | 16.7 | 1 | 3 | 4.5 | chr14:30744891-30744974 | 508 |
| -1.2390492 | 164.3 | 197.4 | 123 | 489.2 | 320.9 | 334 | chr13:27439454-27440249 | 1466 |
| 1.13421154 | 543.1 | 636.8 | 431 | 340.8 | 287.1 | 106 | chr13:27441173-27442153 | -346 |
| 2.13832149 | 794.7 | 742.5 | 368.2 | 211.2 | 138.8 | 82.8 | chr14:94855880-94856921 | -402 |
| 2.17130096 | 316.7 | 243.3 | 384.1 | 97 | 58.1 | 54.5 | chr13:45858089-45859877 | 653 |
| 2.45929043 | 211.6 | 104.3 | 195 | 33.1 | 38.6 | 21.2 | chr5:140711147-140713193 | 2159 |
| 1.4263989 | 296 | 300.3 | 143.1 | 97.5 | 91.3 | 86.3 | chr5:73923552-73924210 | 1027 |
| 2.60178012 | 56.2 | 32 | 32.6 | 4.9 | 2.4 | 12.6 | chr1:1554278-1555040 | -2763 |
| 1.86545184 | 953.1 | 878.7 | 789.2 | 200.8 | 420.6 | 97.9 | chr5:140756239-140758980 | -269 |
| 1.89932454 | 982.7 | 675.7 | 1927 | 185.5 | 594.3 | 181.2 | chr9:137992213-137993082 | 400 |
| 2.33723389 | 1707.8 | 1532.2 | 2029 | 432.8 | 522 | 87.8 | chr8:23622667-23624110 | -3521 |
| 2.11442989 | 59.2 | 37.5 | 41 | 17.3 | 5.9 | 8.6 | chr5:160905809-160906316 | 1646 |
| 1.71920847 | 381.8 | 314.2 | 644.4 | 99.4 | 272.9 | 34.8 | chr2:27340087-27341044 | -1101 |
| 4.33038967 | 26.6 | 12.5 | 29.3 | 1 | 2.4 | 0 | chr16:3108224-3110264 | -3644 |
| 2.20389436 | 6868.2 | 4561.9 | 4474 | 416 | 2939 | 96.9 | chr7:2153131-2155320 | -406 |
| 2.20389436 | 6868.2 | 4561.9 | 4474 | 416 | 2939 | 96.9 | chr7:2153131-2155320 | -406 |
| 0.39645801 | 642.3 | 481.1 | 512.2 | 432.3 | 415.2 | 395.1 | chr1:64402210-64403371 | -23 |
| 4.47638918 | 185 | 159.9 | 40.2 | 5.4 | 1.8 | 10.1 | chr14:41397170-41398384 | 434 |
| 0.94337798 | 1907.6 | 1704.6 | 1577 | 1491 | 881.4 | 326 | chr11:550320-551402 | -82 |
| 1.43517748 | 5065.7 | 3905.6 | 3787 | 963.6 | 3564 | 190.7 | chr4:7094697-7096949 | -194 |
| 2.90197131 | 668.9 | 743.9 | 138.9 | 64.3 | 101.4 | 41.9 | chr3:64646344-64647962 | 1252 |
| 0.43262445 | 396.6 | 344.8 | 378.3 | 311.6 | 288.9 | 229.1 | chr1:12598746-12602700 | -316 |
| 2.54457606 | 1851.3 | 869 | 1232 | 90.5 | 578.3 | 8.6 | chr22:17273887-17274766 | 591 |
| 1.21171866 | 674.8 | 748 | 417.6 | 379.4 | 330.4 | 84.8 | chr19:14044297-14045121 | -111 |
| 1.26728908 | 959 | 638.2 | 610.1 | 250.3 | 443.7 | 223 | chr13:49595808-49596680 | 1434 |
| 1.65526095 | 282.7 | 172.4 | 179.9 | 79.6 | 77.1 | 44.9 | chr7:86618712-86620894 | -56 |
| 2.54946382 | 219 | 201.6 | 534.8 | 27.2 | 116.3 | 19.7 | chr16:52879366-52881357 | -2482 |
| 3.26086657 | 646.7 | 399 | 124.7 | 48.5 | 53.4 | 20.2 | chr15:76517345-76518795 | 498 |
| 2.00727717 | 142.1 | 118.2 | 57.7 | 20.3 | 39.1 | 19.7 | chr19:49972190-49972604 | -568 |
| 2.19682886 | 1476.9 | 1608.7 | 619.3 | 354.2 | 356.5 | 97.4 | chr19:61344489-61345629 | 692 |
| 1.81184951 | 1553.9 | 1733.8 | 1020 | 283.4 | 736.7 | 206.9 | chr17:26445310-26446012 | 414 |
| 1.41955645 | 760.7 | 780 | 718.9 | 444.2 | 269.3 | 131.2 | chr1:1156511-1157912 | -459 |
| 2.48307962 | 1589.4 | 1001.1 | 1426 | 315.1 | 307.9 | 95.4 | chr20:1822037-1824093 | 253 |
| 1.74188805 | 2687.5 | 2205.2 | 2604 | 327 | 1654 | 259.9 | chr1:95161234-95165177 | -603 |
| 2.60142588 | 4319.8 | 3431.5 | 3107 | 314.1 | 1383 | 92.3 | chr7:7965768-7968799 | -4698 |
| 0.83682891 | 87.3 | 98.7 | 97.1 | 66.3 | 29.1 | 63.1 | chr7:68700084-68700700 | -375 |
| 1.96903854 | 2299.8 | 1878.4 | 2202 | 318.1 | 1237 | 74.2 | chr19:54006815-54008403 | -1496 |
| 2.41026826 | 396.6 | 386.5 | 183.3 | 72.7 | 85.4 | 23.7 | chr2:176656409-176657300 | 82 |
| 3.44955599 | 393.7 | 267 | 678.7 | 21.3 | 77.1 | 24.2 | chr8:88955805-88956373 | -677 |
| 3.28141294 | 25.2 | 16.7 | 84.5 | 4 | 6.5 | 2.5 | chr7:6019617-6020056 | -4573 |
| 3.10582705 | 358.1 | 162.7 | 60.3 | 18.3 | 42.1 | 7.1 | chr4:13159045-13160580 | -1266 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| 1.16376931 | 825.8 | 838.4 | 639.4 | 453.1 | 340.5 | 234.6 | chr10:134451511-134452709 | −2583 |
| 2.0801188 | 2514.3 | 1914.6 | 1249 | 377.4 | 841.7 | 123.6 | chr15:83326397-83327052 | 516 |
| 1.37066821 | 62.2 | 57 | 56.9 | 32.2 | 10.7 | 25.2 | chr8:26778401-26778599 | 339 |
| 1.91900676 | 739.9 | 818.9 | 231.8 | 203.8 | 188 | 81.7 | chr8:26779893-26781465 | −1840 |
| 0.96933569 | 338.9 | 357.3 | 379.1 | 221.6 | 112.1 | 215.5 | chr6:86409193-86410070 | 115 |
| 2.12151029 | 3809.3 | 2601.4 | 2759 | 440.8 | 1310 | 356.2 | chr7:7195418-7196997 | 276 |
| 0.43072969 | 334.5 | 390.7 | 393.3 | 307.2 | 296 | 226.6 | chr19:13877921-13878604 | −353 |
| 1.05428863 | 74 | 62.6 | 142.3 | 43.5 | 43.9 | 46.9 | chr11:46895205-46896504 | 798 |
| 2.75798674 | 77 | 34.8 | 97.9 | 6.4 | 19 | 5.6 | chr6:11222075-11222398 | −2291 |
| 1.89986521 | 3087.1 | 2073.1 | 3106 | 431.9 | 1628 | 154.9 | chr14:104332624-104334290 | −2474 |
| 4.73164059 | 930.9 | 731.3 | 104.6 | 28.2 | 26.7 | 11.6 | chr19:56766276-56767122 | 357 |
| 1.21744745 | 68.1 | 73.7 | 91.2 | 32.2 | 19.6 | 48.4 | chr11:124239737-124240683 | −281 |
| 0.88849082 | 467.6 | 511.7 | 395.8 | 322 | 287.1 | 133.7 | chr5:150612381-150613406 | 88 |
| 2.52531788 | 3386 | 1886.8 | 2763 | 415 | 824.5 | 156.4 | chr16:73365348-73366152 | 472 |
| 1.67023079 | 204.2 | 189.1 | 263.6 | 72.2 | 64.1 | 70.1 | chr1:114498910-114500564 | −1742 |
| 1.68455752 | 2589.8 | 1473.8 | 2362 | 504.6 | 1387 | 107.5 | chr7:106596535-106597485 | 315 |
| 0.77552029 | 541.6 | 574.2 | 610.9 | 358.1 | 497.7 | 152.9 | chr18:12691943-12692545 | 459 |
| 2.08205672 | 1589.4 | 1255.5 | 964.1 | 84.1 | 676.2 | 139.3 | chr8:4836951-4839344 | 1589 |
| 1.9452437 | 1531.7 | 679.9 | 1702 | 338.9 | 437.2 | 240.2 | chr3:130323020-130324063 | −232 |
| 1.2444307 | 229.4 | 169.6 | 157.3 | 88.5 | 118 | 28.3 | chr2:68038974-68040548 | −37 |
| 2.09287369 | 920.5 | 545 | 1146 | 152.4 | 328 | 131.7 | chr5:52810539-52812441 | −861 |
| 4.47638918 | 185 | 159.9 | 40.2 | 5.4 | 1.8 | 10.1 | chr19:41397170-41398384 | 49 |
| 1.41749963 | 156.9 | 154.3 | 333.9 | 48 | 106.2 | 87.3 | chr12:75796608-75797339 | −43 |
| 1.84665312 | 500.2 | 424.1 | 320.5 | 133.6 | 138.8 | 73.7 | chr6:65774170-65776940 | −171 |
| 1.18099437 | 692.6 | 709.1 | 672 | 440.8 | 328 | 145.8 | chr2:95055264-95056998 | 926 |
| 1.87751599 | 85.8 | 86.2 | 159.8 | 38.1 | 28.5 | 23.7 | chr4:145785057-145785855 | −1166 |
| −2.2871291 | 41.4 | 50.1 | 13.4 | 180.1 | 93.7 | 238.2 | chr6:108689120-108689745 | −276 |
| 1.86049551 | 423.3 | 408.8 | 215.9 | 89 | 147.1 | 52.5 | chr6:108689869-108690628 | −1092 |
| 2.18080261 | 620.1 | 560.3 | 197.5 | 161.8 | 83.6 | 58.5 | chr16:56616536-56617374 | 173 |
| 1.44405639 | 50.3 | 50.1 | 53.6 | 25.2 | 3.6 | 27.8 | chr4:185982474-185984829 | 558 |
| 2.60178012 | 56.2 | 32 | 32.6 | 4.9 | 2.4 | 12.6 | chr1:1554278-1555040 | −3362 |
| 0.75611816 | 133.2 | 162.7 | 143.9 | 97.9 | 57.5 | 105 | chr11:118443496-118444178 | 135 |
| 2.84251816 | 1472.5 | 1494.7 | 297.1 | 156.8 | 199.9 | 98.4 | chr11:69601192-69602727 | −96 |
| 0.94337798 | 1907.6 | 1704.6 | 1577 | 1491 | 881.4 | 326 | chr11:550320-551402 | −588 |
| 1.94914997 | 1561.3 | 1026.1 | 1633 | 152.4 | 851.2 | 89.3 | chr1:238322032-238324042 | 1230 |
| 2.51182312 | 152.4 | 93.2 | 106.3 | 25.7 | 17.8 | 18.2 | chr4:158111268-158113397 | −336 |
| 0.43072969 | 334.5 | 390.7 | 393.3 | 307.2 | 296 | 226.6 | chr19:13877921-13878604 | 211 |
| 1.9699138 | 4327.2 | 2620.9 | 3886 | 494.2 | 2065 | 205.9 | chr16:2954093-2955587 | 623 |
| 1.81899389 | 37 | 51.4 | 48.5 | 16.8 | 8.9 | 13.1 | chr12:27823552-27824530 | −412 |
| 2.09111406 | 312.3 | 216.9 | 212.6 | 29.7 | 132.3 | 12.1 | chr1:67649906-67650014 | −4526 |
| 1.82624974 | 2844.4 | 960.8 | 1552 | 499.6 | 688.1 | 322.9 | chr22:49368074-49369099 | −326 |
| 1.4556739 | 833.2 | 816.2 | 564.9 | 195.4 | 482.2 | 129.7 | chr2:27485791-27486387 | −89 |
| 1.07298049 | 951.6 | 948.2 | 697.1 | 526.8 | 447.2 | 260.4 | chr17:72045217-72046115 | −289 |
| 0.72977221 | 762.1 | 720.2 | 1005 | 669.3 | 642.4 | 188.2 | chr3:127906124-127906929 | 719 |
| 0.85005869 | 307.8 | 283.6 | 318.9 | 212.7 | 170.2 | 122.1 | chr7:150554475-150555913 | 56 |
| 1.21194376 | 189.4 | 201.6 | 127.2 | 87.6 | 86.6 | 49.5 | chr6:100069122-100069785 | 520 |
| 2.48581949 | 2394.5 | 1847.8 | 1270 | 110.8 | 768.7 | 104.5 | chr10:102096092-102098450 | 510 |
| 1.43517748 | 5065.7 | 3905.6 | 3787 | 963.6 | 3564 | 190.7 | chr4:7094697-7096949 | −233 |
| 1.31740081 | 119.9 | 139 | 313.8 | 108.8 | 74.1 | 46.9 | chr1:59021217-59022365 | 582 |
| 1.57311192 | 828.7 | 617.3 | 615.1 | 236.9 | 268.1 | 187.7 | chr8:73149260-73150642 | 422 |
| −3.9093338 | 10.4 | 1.4 | 0 | 24.2 | 35 | 118.1 | chr10:72638544-72639616 | −3223 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| 2.76749439 | 288.6 | 173.8 | 230.1 | 20.8 | 61.7 | 19.2 | chr10:72642748-72644383 | 1262 |
| 2.85613216 | 1127.7 | 666 | 1326 | 143.5 | 204 | 83.3 | chr18:19420303-19421136 | -251 |
| 0.86385674 | 611.2 | 731.3 | 528.9 | 397.7 | 272.3 | 358.3 | chr22:18687509-18688666 | -479 |
| 2.44791366 | 220.5 | 222.5 | 249.4 | 79.1 | 26.1 | 21.7 | chr1:225572365-225573595 | -531 |
| 0.77552029 | 541.6 | 574.2 | 610.9 | 358.1 | 497.7 | 152.9 | chr18:12691943-12692545 | -819 |
| 0.91407792 | 404 | 447.7 | 360.7 | 312.1 | 231.9 | 99.4 | chr4:73775715-73776242 | 51 |
| 2.28586402 | 2064.5 | 1619.8 | 1471 | 285.4 | 681 | 90.8 | chr14:73776242-73777614 | 1001 |
| 1.54977719 | 1508 | 1466.9 | 828.5 | 385.4 | 718.9 | 194.8 | chr4:5940892-5942077 | -268 |
| 1.24569492 | 537.2 | 479.7 | 524.7 | 380.4 | 207.6 | 62.1 | chr9:114552251-114553102 | -278 |
| 2.10586792 | 330 | 339.3 | 358.2 | 81.6 | 122.8 | 34.3 | chr5:38881231-38882812 | 129 |
| 2.98682461 | 79.9 | 50.1 | 44.4 | 14.8 | 4.7 | 2.5 | chr21:44598675-44599100 | 976 |
| 1.13670774 | 987.1 | 818.9 | 731.4 | 583.2 | 399.2 | 171.6 | chr11:63808414-63810217 | -591 |
| 2.78000667 | 449.9 | 439.4 | 323 | 126.6 | 29.7 | 20.2 | chr17:44051262-44052535 | -4598 |
| 2.54731521 | 167.2 | 84.8 | 69.5 | 16.8 | 13 | 25.2 | chr16:23755091-23755635 | 563 |
| 2.04626173 | 266.4 | 168.2 | 154.8 | 38.1 | 65.2 | 39.4 | chr18:55039466-55040756 | 1732 |
| 2.77760758 | 362.6 | 148.8 | 467.8 | 54.4 | 51.6 | 36.8 | chr17:43975912-43977270 | 801 |
| -1.9068906 | 20.7 | 43.1 | 31.8 | 86.6 | 74.1 | 197.8 | chr9:132803789-132804431 | -52 |
| 1.06518919 | 1314.1 | 1337.6 | 1214 | 745.5 | 872.5 | 229.6 | chr9:132804431-132805826 | -1070 |
| 2.28391404 | 668.9 | 421.3 | 775 | 162.3 | 170.2 | 50.5 | chr16:88516590-88518518 | 309 |
| 2.12151029 | 3809.3 | 2601.4 | 2759 | 440.8 | 1310 | 356.2 | chr17:7195418-7196997 | -3013 |
| 2.12681161 | 661.5 | 707.7 | 198.3 | 136 | 124 | 98.9 | chr1:42617768-42619192 | -574 |
| 2.47373108 | 171.7 | 175.2 | 53.6 | 25.7 | 13.6 | 32.8 | chr6:26306989-26307765 | -388 |
| 1.86545184 | 953.1 | 878.7 | 789.2 | 200.8 | 420.6 | 97.9 | chr5:140756239-140758980 | -5094 |
| -1.1049133 | 121.4 | 126.5 | 89.5 | 227.1 | 210 | 288.6 | chr5:140761789-140763388 | -115 |
| 1.75119667 | 3272.1 | 2379 | 1317 | 587.7 | 1185 | 297.2 | chr2:47676042-47678811 | 1929 |
| 2.50410904 | 788.8 | 774.4 | 171.6 | 90.5 | 80.1 | 135.2 | chr16:48744364-48745279 | -747 |
| 1.52158671 | 279.7 | 239.1 | 138.1 | 110.8 | 74.1 | 43.9 | chr8:37826043-37826778 | 159 |
| 0.91224573 | 848 | 880.1 | 950.7 | 643.6 | 613.3 | 166.5 | chr2:31772670-31773896 | 92 |
| -2.0401351 | 7.4 | 8.3 | 10 | 22.3 | 27.9 | 55.5 | chr17:44026267-44026444 | -253 |
| 1.57393048 | 1611.6 | 1205.5 | 843.6 | 405.1 | 611.6 | 212.9 | chr17:44029874-44032155 | -4912 |
| 0.88386206 | 130.2 | 143.2 | 163.2 | 109.8 | 61.7 | 65.1 | chr4:123966509-123967779 | -168 |
| 0.58584522 | 414.4 | 449.1 | 444.4 | 347.8 | 130.5 | 393.1 | chr1:99918903-93919866 | 589 |
| 1.04341537 | 180.5 | 194.7 | 205 | 144 | 72.4 | 65.1 | chr6:44463261-44464342 | 522 |
| 1.89986521 | 3087.1 | 2073.1 | 3106 | 431.9 | 1628 | 154.9 | chr14:104332624-104334290 | -4520 |
| 1.62512068 | 698.5 | 639.6 | 323 | 193.4 | 283.5 | 61.6 | chr3:187308365-187310526 | 150 |
| 2.30177332 | 1727 | 1796.4 | 812.6 | 316.6 | 447.2 | 115.6 | chr3:124228291-124230592 | -175 |
| 0.72788268 | 726.6 | 642.4 | 779.1 | 471.9 | 331.6 | 493.5 | chr11:65243960-65245318 | 346 |
| 0.87901977 | 544.6 | 511.7 | 499.6 | 167.7 | 335.7 | 342.6 | chr21:37299380-37300942 | -571 |
| 3.70501143 | 2977.6 | 1889.5 | 1423 | 161.8 | 301.3 | 19.2 | chr12:129922282-129922960 | 101 |
| 1.49057672 | 276.7 | 155.7 | 224.3 | 72.2 | 71.2 | 90.3 | chr6:11151240-11152144 | 918 |
| 1.5777593 | 185 | 179.4 | 195 | 72.7 | 65.8 | 48.9 | chr10:103976422-103977340 | 749 |
| 2.29805518 | 5696.1 | 4431.2 | 5054 | 806.8 | 2131 | 148.9 | chr17:67667921-67668569 | 466 |
| 2.13913692 | 65.1 | 48.7 | 27.6 | 9.4 | 10.1 | 12.6 | chr8:49810261-49811746 | -659 |
| 1.9316769 | 227.9 | 265.6 | 92.1 | 60.4 | 38.6 | 54.5 | chr15:72206613-72208128 | -1397 |
| -2.8981646 | 14.8 | 25 | 0 | 81.1 | 51.6 | 164 | chr15:72209713-72210145 | 1162 |
| 2.75595815 | 507.6 | 561.7 | 143.9 | 97.9 | 50.4 | 31.3 | chr5:180564714-180565750 | -4696 |
| 2.60142588 | 4319.8 | 3431.5 | 3107 | 314.1 | 1383 | 92.3 | chr17:7965768-7968799 | 844 |
| 2.20389436 | 6868.2 | 4561.9 | 4474 | 416 | 2939 | 96.9 | chr12:129922282-129922960 | -280 |
| 1.06354582 | 133.2 | 157.1 | 180.8 | 72.2 | 71.2 | 69.1 | chr7:2153131-2155320 | 236 |
| 1.42697024 | 463.2 | 424.1 | 237.7 | 97 | 128.1 | 147.3 | chrX:154097855-154098406 | -1316 |
| 1.70339858 | 205.7 | 236.4 | 131.4 | 74.2 | 46.9 | 55 | chr1:19683047-19683866 | 1123 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| 2.16557069 | 275.3 | 118.2 | 367.4 | 85.1 | 65.8 | 18.7 | chr18:75539612-75540344 | -810 |
| 1.84839911 | 193.9 | 130.7 | 249.4 | 72.7 | 70 | 16.7 | chr4:57962831-57964126 | -984 |
| 3.39394045 | 2088.1 | 1607.3 | 395.8 | 87.1 | 178.5 | 123.6 | chr1:11635345-11637981 | 663 |
| 2.52806174 | 3156.6 | 1966 | 1733 | 275 | 796 | 117.6 | chr9:9967202-968463 | 869 |
| 1.94240044 | 2065.9 | 1357 | 2189 | 411.1 | 835.2 | 213.9 | chr11:129824078-129825680 | 801 |
| 2.2347955 | 156.9 | 151.6 | 77 | 47 | 7.7 | 27.2 | chr4:93616732-93617847 | -102 |
| 1.86020332 | 159.8 | 79.3 | 69.5 | 25.2 | 22.5 | 37.3 | chr17:56886966-56887205 | -1503 |
| 1.65883881 | 37 | 45.9 | 39.3 | 14.8 | 4.7 | 19.2 | chr9:41335121-41336007 | 47 |
| -1.5669125 | 20.7 | 37.5 | 54.4 | 111.8 | 89.6 | 132.2 | chr3:139635893-139636261 | -27 |
| 2.25748849 | 6039.5 | 3655.3 | 8314 | 910.2 | 2649 | 206.9 | chr3:139636275-139637284 | 675 |
| 1.24581832 | 623 | 686.9 | 621 | 416.5 | 196.9 | 200.8 | chr7:76882921-76884267 | 59 |
| 1.79968206 | 4567 | 3129.8 | 3939 | 908.2 | 2186 | 248.3 | chrX:9693241-9693855 | 369 |
| 2.32050967 | 809.5 | 1142.9 | 385.8 | 159.8 | 202.3 | 106 | chr10:125640657-125641163 | 580 |
| 0.75421465 | 568.3 | 668.8 | 625.2 | 486.8 | 504.8 | 112.5 | chr9:35679812-35681616 | -661 |
| 2.2183302 | 2712.6 | 1772.7 | 1579 | 377.9 | 726 | 199.3 | chr15:61122420-61125530 | 1085 |
| 2.04275821 | 72.5 | 61.2 | 119.7 | 29.7 | 20.2 | 11.6 | chr15:65334288-65334669 | 237 |
| 2.45929043 | 211.6 | 104.3 | 195 | 33.1 | 38.6 | 21.2 | chr5:140711147-140713193 | -2781 |
| 2.6980816 | 296 | 243.3 | 72 | 48 | 18.4 | 27.8 | chr17:37327131-37328367 | 1049 |
| 1.63245893 | 62.2 | 47.3 | 41.8 | 23.2 | 13 | 12.6 | chr3:31996011-31996699 | 1887 |
| 1.04114917 | 267.9 | 333.7 | 308.8 | 198.9 | 120.4 | 123.1 | chr19:2101142-2102295 | 838 |
| 1.23999976 | 180.5 | 154.3 | 198.3 | 74.7 | 85.4 | 65.6 | chrX:102828048-102829797 | -670 |
| 3.39394045 | 2088.1 | 1607.3 | 395.8 | 87.1 | 178.5 | 123.6 | chr1:11635345-11637981 | -355 |
| 0.59582482 | 531.3 | 531.1 | 577.4 | 447.7 | 344.6 | 292.7 | chr4:41847913-41849449 | 971 |
| 2.23055678 | 41.4 | 27.8 | 102.1 | 11.4 | 12.5 | 12.6 | chr19:54246593-54247571 | -2902 |
| 2.50033503 | 745.9 | 867.6 | 184.1 | 125.2 | 110.3 | 82.2 | chr14:41146583-41147282 | 419 |
| 2.06077531 | 691.1 | 641 | 854.5 | 206.3 | 232.5 | 85.3 | chr15:153301679-153302468 | -763 |
| 1.9699138 | 4327.2 | 2620.9 | 3886 | 494.2 | 2065 | 205.9 | chr16:2954093-2955587 | -4502 |
| 1.36616782 | 50.3 | 54.2 | 56.1 | 27.7 | 8.9 | 25.7 | chr11:11042585-11043305 | -267 |
| 2.20389436 | 6868.2 | 4561.9 | 4474 | 416 | 2939 | 96.9 | chr7:2153131-2155320 | 228 |
| 1.07870444 | 288.6 | 328.1 | 456.9 | 219.6 | 163.1 | 125.6 | chr20:49849540-49852352 | 1509 |
| 2.27242259 | 1271.2 | 945.5 | 687.9 | 168.7 | 328.6 | 103.9 | chr7:44043085-44044174 | -247 |
| 2.04275821 | 72.5 | 61.2 | 119.7 | 29.7 | 20.2 | 11.6 | chr15:65334288-65334669 | -350 |
| -1.787393 | 149.5 | 115.4 | 231 | 901.8 | 413.4 | 396.6 | chr2:112371864-112373237 | -111 |
| 2.84533449 | 816.9 | 917.7 | 236 | 79.6 | 161.3 | 33.3 | chr2:112373237-112373765 | 840 |
| 2.77799286 | 100.6 | 64 | 49.4 | 17.3 | 5.3 | 8.6 | chr3:195598699-195599878 | 1996 |
| 2.94487347 | 704.4 | 800.9 | 415.1 | 134.6 | 89.6 | 25.2 | chr7:37143029-37145081 | 369 |
| 1.15267113 | 873.1 | 656.3 | 606.7 | 177.1 | 538 | 245.7 | chr4:109306498-109311084 | 236 |
| 1.98924842 | 1534.7 | 1660.1 | 668.7 | 238.9 | 608.6 | 125.6 | chr11:10282867-10284189 | 311 |
| 1.17894353 | 229.4 | 183.5 | 200.9 | 160.3 | 55.8 | 55 | chr21:33316924-33317777 | -2758 |
| 0.85005869 | 307.8 | 283.6 | 318.9 | 212.7 | 170.2 | 122.1 | chr7:150555447 75-150555913 | -5323 |
| -2.2333973 | 31.1 | 44.5 | 49.4 | 179.1 | 104.4 | 304.3 | chr20:25011377-25012103 | -973 |
| 1.96848238 | 700 | 685.5 | 221.8 | 176.1 | 175.6 | 59 | chr20:25012103-25014030 | -2299 |
| 2.56863691 | 1043.3 | 666 | 812.6 | 75.2 | 302.5 | 47.4 | chr12:111047454-111049040 | 484 |
| 1.15599585 | 726.6 | 614.6 | 697.1 | 456.1 | 296.6 | 162 | chr22:19122039-19123231 | -489 |
| 0.68198696 | 202.7 | 198.8 | 299.6 | 169.7 | 144.7 | 122.6 | chr3:162304916-162305903 | 445 |
| 2.16763812 | 976.7 | 931.6 | 392.5 | 248.3 | 164.9 | 98.9 | chr17:26741966-26743420 | -74 |
| 1.75701942 | 207.2 | 178 | 368.2 | 76.7 | 93.7 | 52.5 | chr17:8867042-8867962 | 1919 |
| 1.25161356 | 115.4 | 130.7 | 121.3 | 63.8 | 38 | 52.5 | chr12:94707039-94707815 | 1240 |
| 1.18737962 | 236.8 | 267 | 273.7 | 184 | 97.9 | 59.5 | chr19:7244255-7244900 | 434 |
| 1.13670774 | 987.1 | 818.9 | 731.4 | 583.2 | 399.2 | 171.6 | chr11:63808414-63810217 | -563 |
| 1.3609567 | 463.2 | 628.5 | 427.6 | 284.4 | 191 | 116.1 | chr2:85214318-85215155 | 492 |

TABLE 14-continued

Comprehensive DNA Methylation and K27 Profiles of CD44+ Nulliparous and Parous Breast Epithelial Cells

| | | | | | | |
|---|---|---|---|---|---|---|
| 1.2415136 | 109.5 | 101.5 | 100.4 | 48.5 | 23.7 | 59.5 | chr9:139213989-139214799 | 407 |
| 2.40091639 | 65.1 | 58.4 | 120.5 | 22.8 | 21.4 | 2 | chr3:50287467-50288535 | -3520 |
| -1.7012134 | 41.4 | 33.4 | 68.6 | 166.7 | 103.8 | 195.8 | chr4:13152439-13153795 | 2095 |
| 3.10582705 | 358.1 | 162.7 | 60.3 | 18.3 | 42.1 | 7.1 | chr4:13159045-13160580 | -4600 |
| 1.40227651 | 2261.3 | 1902.1 | 2087 | 481.3 | 1692 | 191.2 | chr3:8784871-8787042 | 344 |
| 2.09602155 | 1218 | 1070.6 | 1870 | 260.7 | 602.1 | 110 | chr2:46779245-46781433 | 737 |
| 1.80164475 | 639.3 | 279.5 | 228.5 | 106.8 | 160.2 | 62.1 | chr2:45758432-45761412 | -7 |
| 0.88108171 | 190.9 | 241.9 | 205 | 152.9 | 109.1 | 84.3 | chr1:25742221-25742776 | -164 |
| 0.76995337 | 337.4 | 383.7 | 315.5 | 274 | 117.4 | 216.5 | chr10:124897105-124897717 | -216 |
| 1.91191903 | 112.5 | 104.3 | 370.7 | 74.7 | 39.7 | 33.3 | chr6:169864746-169866148 | 584 |
| 1.69122658 | 1546.5 | 1220.8 | 1322 | 282 | 756.3 | 228.1 | chr3:32833995-32835585 | 277 |
| 0.98889619 | 48.8 | 48.7 | 83.7 | 32.6 | 27.9 | 30.8 | chr10:4859083-4859340 | 810 |
| 1.41435997 | 401.1 | 250.3 | 271.1 | 82.1 | 163.1 | 100.9 | chr1:23941806-23944229 | 575 |
| 1.74188805 | 2687.5 | 2205.2 | 2604 | 327 | 1654 | 259.8 | chr11:95161234-95165177 | -84 |
| 1.67137725 | 84.4 | 119.6 | 131.4 | 38.1 | 20.8 | 46.4 | chr19:50691921-50693804 | -708 |
| 1.23858572 | 267.9 | 311.4 | 367.4 | 198.4 | 118 | 84.8 | chr21:33065160-33065991 | 465 |
| 2.25607915 | 4379 | 2835 | 2135 | 274.5 | 1577 | 106 | chr7:1566619-1567126 | -618 |
| 1.84839911 | 193.9 | 130.7 | 249.4 | 72.7 | 70 | 16.7 | chr14:57962831-57964126 | 507 |
| 2.18851116 | 90.3 | 47.3 | 116.3 | 18.3 | 30.8 | 6.6 | chr3:157055534-157056622 | -1217 |
| 1.19944961 | 353.7 | 208.6 | 196.7 | 104.9 | 102 | 123.6 | chr7:55986676-55987737 | 102 |
| 1.31729452 | 180.5 | 179.4 | 184.1 | 87.6 | 33.8 | 96.9 | chr1:62556721-62557804 | 409 |
| 1.04756751 | 452.8 | 486.6 | 383.3 | 144 | 327.4 | 168.5 | chr16:969305-971932 | -1190 |
| 2.02500563 | 222 | 304.5 | 96.2 | 65.3 | 59.9 | 27.8 | chr7:67628159-67629148 | -102 |
| 1.44716025 | 281.2 | 235 | 142.3 | 95 | 68.8 | 77.7 | chr16:30289003-30290496 | -3874 |
| 2.47373108 | 171.7 | 175.2 | 53.6 | 25.7 | 13.6 | 32.8 | chr6:26306989-26307765 | 73 |
| 1.03198191 | 307.8 | 303.1 | 492.9 | 207.3 | 256.8 | 75.7 | chr6:132764049-132765197 | -266 |
| 0.75102549 | 1163.2 | 1180.4 | 1173 | 681.7 | 1059 | 348.7 | chr14:68795234-68796760 | -670 |
| 1.65438686 | 583.1 | 532.5 | 259.4 | 159.8 | 212.9 | 64.1 | chr9:2005543-2006563 | 712 |
| 1.23583153 | 461.7 | 222.5 | 185.8 | 89.5 | 150.7 | 129.2 | chr1:26971301-26972491 | -307 |
| -4.268098? | 7.4 | 8.3 | 0 | 77.2 | 55.8 | 169.5 | chr8:145604891-145605068 | 562 |
| 0.66181139 | 161.3 | 198.8 | 181.6 | 135 | 67.6 | 139.8 | chr8:145605348-145606127 | -196 |
| 1.06365864 | 127.3 | 69.5 | 81.2 | 46.5 | 39.1 | 47.4 | chr20:36988499-36989479 | 621 |
| 1.47159864 | 3989.8 | 3177 | 3401 | 566.9 | 2880 | 363.3 | chr19:45641104-45642413 | -1413 |
| 1.87276895 | 155.4 | 123.7 | 173.2 | 63.8 | 31.4 | 28.3 | chr8:17985236-17986889 | 97 |
| 1.49420029 | 966.4 | 750.8 | 443.5 | 251.8 | 290.1 | 225.1 | chr1:46485094-46486521 | -196 |
| 0.92389635 | 2043.7 | 1465.5 | 1557 | 1287 | 1070 | 313.4 | chr13:19334383-19336436 | 364 |
| 1.63989965 | 797.7 | 787 | 422.6 | 179.6 | 336.3 | 128.2 | chr12:28012760-28014392 | 585 |
| 2.3289587 | 756.2 | 324 | 647.7 | 118.7 | 126.3 | 98.9 | chr11:44288186-44289069 | -335 |
| 2.68207758 | 649.7 | 620.1 | 959.1 | 167.2 | 121.6 | 58.5 | chr22:35232041-35233363 | 334 |
| 1.83779266 | 198.3 | 225.2 | 199.2 | 75.2 | 81.3 | 17.7 | chr1:68208652-68209472 | 504 |
| 2.64365787 | 185 | 129.3 | 49.4 | 29.7 | 18.4 | 10.1 | chr18:65219460-65222228 | 1574 |
| 1.09532946 | 335.9 | 315.6 | 224.3 | 117.2 | 169.1 | 123.6 | chr20:43160197-43162341 | 1898 |
| 2.73812785 | 1817.3 | 1744.9 | 618.5 | 280.5 | 253.3 | 92.8 | chr2:136592242-136593646 | -749 |
| 4.25604016 | 202.7 | 68.1 | 50.2 | 1 | 14.8 | 1 | chr4:4906635-4908946 | -4502 |
| 1.75359627 | 5042 | 3683.1 | 4328 | 691.6 | 2939 | 240.2 | chr9:72217486-72218018 | 1641 |
| 1.73542064 | 1684.1 | 1320.9 | 1755 | 240.9 | 1026 | 163 | chr17:14146425-14148192 | 2078 |
| 2.272569 | 276.7 | 303.1 | 115.5 | 88.5 | 26.1 | 29.3 | chr11:68363183-68363990 | 2389 |
| 1.40151636 | 124.3 | 130.7 | 187.5 | 77.2 | 40.3 | 50 | chr16:4261521-4262200 | 1142 |
| 0.7321066 | 446.9 | 458.8 | 507.2 | 422.9 | 282.9 | 144.8 | chr20:31494693-31495530 | 248 |
| 1.82624974 | 2844.4 | 960.8 | 1552 | 499.6 | 688.1 | 322.9 | chr22:49368074-49369099 | -4842 |
| 1.82624974 | 2844.4 | 960.8 | 1552 | 499.6 | 688.1 | 322.9 | chr22:49368074-49369099 | 266 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| 0.77891688 | 476.5 | 501.9 | 391.7 | 323 | 329.2 | 146.3 | chr7:99536102-99537273 | −378 |
| 0.90597296 | 79.9 | 83.4 | 92.1 | 30.2 | 51.6 | 54.5 | chrX:105856061-105856799 | −119 |
| 3.05673701 | 204.2 | 127.9 | 269.5 | 10.4 | 56.9 | 5 | chr2:51929816-51930443 | −2017 |
| 1.67137725 | 84.4 | 119.6 | 131.4 | 38.1 | 20.8 | 46.4 | chr19:50691921-50693804 | −711 |
| 0.77891688 | 476.5 | 501.9 | 391.7 | 323 | 329.2 | 146.3 | chr7:99536102-99537273 | −371 |
| 0.3368634 | 244.2 | 257.2 | 263.6 | 219.1 | 213.5 | 173.1 | chr22:47264300-47265202 | 800 |
| 2.47373108 | 171.7 | 175.2 | 53.6 | 25.7 | 13.6 | 32.8 | chr6:26306989-26307765 | 66 |
| 0.7262329 | 596.4 | 600.6 | 503.8 | 429.9 | 427.1 | 171.1 | chr15:42366944-42368519 | −489 |
| 4.58757371 | 10.4 | 13.9 | 31 | 0 | 1.8 | 0.5 | chrX:7771050-7772712 | 1579 |
| 1.63245893 | 62.2 | 47.3 | 41.8 | 23.2 | 13 | 12.6 | chr3:31996011-31996699 | −1914 |
| 4.58757371 | 10.4 | 13.9 | 31 | 0 | 1.8 | 0.5 | chrX:8097040-8098876 | 1350 |
| 1.85398148 | 254.5 | 214.1 | 193.3 | 40.6 | 109.7 | 32.8 | chr15:80126971-80128058 | −2098 |
| 2.21623002 | 306.3 | 604.8 | 537.3 | 245.4 | 21.4 | 44.9 | chr20:40769554-40787555 | 305 |
| 1.99502232 | 1246.1 | 1355.6 | 523.1 | 191.4 | 467.4 | 125.1 | chr20:41250184-41251579 | 1090 |
| 1.3825098 | 310.8 | 325.4 | 390 | 219.6 | 84.2 | 89.8 | chr2:85664713-85665307 | −31 |
| 1.67029532 | 3963.2 | 3381.4 | 6928 | 2189 | 2064 | 231.1 | chr2:190153429-190154299 | −82 |
| 1.61496291 | 210.1 | 207.2 | 117.2 | 70.2 | 52.8 | 51.5 | chr2:32140852-32142662 | −426 |
| 2.2347955 | 156.9 | 151.6 | 77 | 47 | 7.7 | 27.2 | chr14:93616732-93617847 | 22 |
| 1.26279277 | 338.9 | 332.3 | 761.6 | 311.6 | 195.7 | 89.8 | chr16:2742252-2743058 | 325 |
| 0.99632621 | 71 | 55.6 | 69.5 | 40.1 | 21.4 | 36.8 | chr4:40446371-40446707 | −131 |
| 1.07298049 | 951.6 | 948.2 | 697.1 | 526.8 | 447.2 | 260.4 | chr17:72045217-72046115 | −2100 |
| 2.08079855 | 3024.9 | 2196.8 | 4282 | 479.8 | 1673 | 93.9 | chr9:80100901-80101946 | −455 |
| 5.06387833 | 1127.7 | 985.8 | 592.5 | 13.4 | 59.9 | 7.6 | chr14:23710566-23712370 | 395 |
| 1.56276333 | 2213.9 | 1313.9 | 1290 | 290.4 | 1126 | 213.9 | chr19:40212455-40213564 | −364 |
| 1.84173487 | 6043.9 | 4329.7 | 8054 | 1009 | 3936 | 195.8 | chr7:156624709-156625133 | 506 |
| 1.39812158 | 159.8 | 97.3 | 141.4 | 22.3 | 49.2 | 79.7 | chr3:197529835-197530820 | −785 |
| 1.64202021 | 130.2 | 107.1 | 67 | 24.7 | 44.5 | 28.3 | chr3:188937649-188939098 | −1394 |
| 1.44716025 | 281.2 | 235 | 142.3 | 95 | 68.8 | 77.7 | chr16:30289003-30290496 | −726 |
| −1.4538011 | 136.2 | 89 | 50.2 | 132.6 | 200.5 | 421.3 | chr2:197499583-197501762 | −973 |
| −2.6959639 | 8.9 | 22.2 | 28.5 | 136.5 | 60.5 | 189.2 | chr1:52790798-52791331 | 267 |
| −1.9737747 | 40 | 29.2 | 90.4 | 190.4 | 169.6 | 266.9 | chr1:100087764-100089040 | −230 |
| −1.7948032 | 84.4 | 115.4 | 92.1 | 298.8 | 223 | 491 | chr1:164004300-164005118 | 50 |
| −2.7253846 | 25.2 | 16.7 | 28.5 | 99.4 | 65.2 | 112.5 | chr8:37724678-37725235 | −277 |
| −2.2415483 | 34 | 55.6 | 32.6 | 153.3 | 111.5 | 293.7 | chr15:42789945-42790833 | −587 |
| −1.7125361 | 28.1 | 33.4 | 9.2 | 70.7 | 74.7 | 163 | chr6:88356392-88356605 | −44 |
| −2.4124052 | 26.6 | 36.2 | 9.2 | 158.8 | 67.6 | 156.9 | chr2:96902789-96904093 | −3979 |
| −1.9667017 | 116.9 | 137.6 | 0.8 | 277 | 208.2 | 512.7 | chr2:74733959-74736034 | 96 |
| −2.1824409 | 60.7 | 83.4 | 0 | 190.4 | 131.7 | 332 | chr15:34588333-53459554 | −316 |
| −1.9780905 | 38.5 | 37.5 | 28.5 | 108.8 | 75.3 | 227.6 | chr1:181708460-181708819 | 383 |
| −1.3461356 | 42.9 | 52.8 | 48.5 | 109.8 | 97.3 | 159.5 | chr8:119703258-119704030 | −279 |
| −2.5430489 | 8.9 | 13.9 | 22.6 | 83.6 | 52.8 | 128.2 | chr20:62083042-62083949 | −2056 |
| −2.5743021 | 16.3 | 25 | 40.2 | 128.6 | 108 | 248.8 | chr15:43713941-43714399 | −377 |
| −1.08127196 | 165.7 | 183.5 | 132.2 | 341.3 | 369.5 | 307.8 | chr5:40714928-40716852 | 102 |
| −4.0480561 | 4.4 | 11.1 | 0 | 70.7 | 57.5 | 128.2 | chrX:30237153-30237354 | 163 |
| −3.8957335 | 3 | 19.5 | 0 | 85.6 | 47.5 | 201.8 | chr20:30794237-30794802 | 956 |
| −2.8644835 | 37 | 11.1 | 43.5 | 149.4 | 250.3 | 267.4 | chr1:110494312-110496291 | 647 |
| −3.3497417 | 29.6 | 12.5 | 0 | 153.8 | 56.9 | 249.3 | chr3:62279212-62279887 | −886 |
| −1.9903927 | 94.7 | 141.8 | 0.8 | 308.7 | 290.1 | 344.1 | chr6:138766672-138767325 | −30 |
| −3.2204719 | 26.6 | 8.3 | 28.5 | 76.7 | 56.9 | 191.7 | chr16:69391947-69392302 | 438 |
| −2.8463161 | 13.3 | 25 | 28.5 | 159.3 | 75.9 | 245.2 | chr16:69392564-69393043 | −241 |
| −3.7202785 | 3 | 7 | 0 | 38.1 | 26.1 | 67.6 | chr11:111542666-111543583 | −3074 |

TABLE 14-continued

Comprehensive DNA Methylation and K27 Profiles of CD44+ Nulliparous and Parous Breast Epithelial Cells

| | | | | | | |
|---|---|---|---|---|---|---|
| -2.8853773 | 13.3 | 15.3 | 25.9 | 77.2 | 148.9 | 176.6 | chr11:95762164-95763183 | -788 |
| -3.3346552 | 16.3 | 15.3 | 0 | 91.5 | 59.3 | 168 | chr1:7:63965747-63966074 | -662 |
| -6.1267045 | 4.4 | 2.8 | 0 | 108.3 | 264.6 | 130.2 | chr1:149520663-149522254 | 44 |
| -0.7318629 | 91.8 | 118.2 | 158.2 | 216.7 | 220.7 | 174.1 | chr8:99906115-99906942 | 557 |
| -2.8517975 | 20.7 | 25 | 5.9 | 125.6 | 55.2 | 191.7 | chr6:74028901-74029941 | 207 |
| -1.5239364 | 116.9 | 121 | 113.8 | 351.7 | 234.3 | 425.4 | chr15:26015834-26016735 | 1769 |
| -2.0566458 | 69.6 | 64 | 0 | 149.9 | 112.7 | 293.2 | chr5:126393698-126394240 | 370 |
| -2.286055 | 56.2 | 26.4 | 47.7 | 144.9 | 112.7 | 377.9 | chr3:129698858-129699329 | -4375 |
| -1.5862985 | 66.6 | 68.1 | 45.2 | 158.8 | 110.9 | 270.5 | chr5:134942401-134943410 | -37 |
| -2.6542858 | 42.9 | 26.4 | 36 | 244.4 | 89 | 329.5 | chr14:64001509-64002315 | -57 |
| -3.1905686 | 4.4 | 19.5 | 0 | 40.6 | 43.9 | 133.7 | chr11:117735405-117735485 | -66 |
| -2.2264794 | 53.3 | 69.5 | 88.7 | 449.7 | 285.3 | 254.8 | chr14:91371420-91373025 | 380 |
| -2.5044726 | 17.8 | 23.6 | 5.9 | 107.3 | 48.6 | 112.5 | chr13:52211835-52212197 | -68 |
| -3.0331147 | 10.4 | 22.2 | 6.7 | 87.6 | 57.5 | 176.6 | chr1:153509278-153510155 | -4281 |
| -2.1747954 | 11.8 | 8.3 | 25.9 | 50 | 49.2 | 108.5 | chr13:102223594-102224494 | 106 |
| -2.7614797 | 35.5 | 38.9 | 0 | 134.6 | 94.9 | 275 | chr19:7651457-7652072 | 58 |
| -2.484353 | 53.3 | 66.7 | 0 | 200.3 | 131.1 | 340.1 | chr20:61808852-61810376 | 185 |
| -1.5444604 | 23.7 | 33.4 | 38.5 | 64.3 | 74.7 | 141.8 | chr12:128569050-128581112 | -15 |
| -2.484353 | 53.3 | 66.7 | 0 | 200.3 | 131.1 | 340.1 | chr20:61808852-61810376 | 377 |
| -2.2241089 | 20.7 | 15.3 | 36 | 120.7 | 89 | 126.7 | chr22:27993009-27995892 | -536 |
| -2.1971919 | 19.2 | 29.2 | 20.9 | 117.2 | 59.3 | 141.3 | chr6:84619854-84620297 | 372 |
| -1.5700563 | 108 | 130.7 | 169.9 | 354.7 | 366 | 492.5 | chr3:172108430-172109495 | 158 |
| -2.2375918 | 53.3 | 101.5 | 19.2 | 256.2 | 164.3 | 400.1 | chr1:42920823-42922548 | 1033 |
| -1.808338 | 59.2 | 43.1 | 44.4 | 148.9 | 112.1 | 252.8 | chr1:7:7140251-7140947 | -1999 |
| -2.4055018 | 32.6 | 66.7 | 11.7 | 120.2 | 122.8 | 345.1 | chr1:7:7141836-7142082 | -3359 |
| -1.9704483 | 112.5 | 123.7 | 32.6 | 376 | 204.6 | 472.8 | chr19:2671315-2672990 | 217 |
| -2.0666097 | 28.1 | 44.5 | 18.4 | 120.7 | 85.4 | 175.1 | chr21:39641527-39643725 | 291 |
| -2.7667582 | 17.8 | 25 | 9.2 | 85.6 | 80.1 | 188.2 | chr1:210275400-210275524 | -79 |
| -1.5351153 | 45.9 | 51.4 | 46 | 90.5 | 93.7 | 231.1 | chr3:156173312-15618368 | 294 |
| -1.8803624 | 31.1 | 33.4 | 31 | 115.3 | 65.2 | 171.1 | chr7:149669843-149670304 | -434 |
| -4.7359493 | 1.5 | 5.6 | 0 | 32.6 | 27.9 | 128.7 | chr10:79463176-79463665 | -4155 |
| -2.0983021 | 4.4 | 4.2 | 10.9 | 24.7 | 25.5 | 33.3 | chr1:73149849-73150451 | -301 |
| -3.6801197 | 3 | 1.4 | 0 | 20.3 | 15.4 | 20.7 | chr10:70417970-70418392 | -317 |
| -3.0807914 | 0 | 30.6 | 0 | 62.8 | 79.5 | 116.6 | chr2:197372578-197372782 | -10 |
| -1.1401093 | 51.8 | 72.3 | 51.9 | 83.6 | 115.1 | 189.2 | chr1:163866925-163868905 | 842 |
| -2.2207253 | 29.6 | 38.9 | 55.2 | 136.5 | 109.1 | 331 | chr6:43592521-43593651 | 318 |
| -2.0351505 | 50.3 | 64 | 41.8 | 232 | 156 | 251.8 | chr7:139521558-139523051 | -1225 |
| -2.6057853 | 20.7 | 20.9 | 22.6 | 120.2 | 61.7 | 208.9 | chr9:88085611-88087253 | 878 |
| -2.737987 | 17.8 | 16.7 | 0.8 | 52.9 | 46.9 | 135.7 | chr16:88153191-88154446 | -1520 |
| -1.604538 | 48.8 | 45.9 | 15.1 | 120.7 | 93.1 | 120.6 | chr8:110443381-110443803 | -289 |
| -2.9158667 | 19.2 | 27.8 | 0 | 109.3 | 55.2 | 190.2 | chr10:91395037-91395432 | -1607 |
| -1.4232114 | 63.6 | 109.8 | 86.2 | 234 | 165.5 | 296.5 | chr15:72444872-72445738 | 301 |
| -2.4094714 | 14.8 | 8.3 | 40.2 | 79.1 | 67 | 190.2 | chr7:74862754-74862842 | -154 |
| -3.4615119 | 13.3 | 5.6 | 0 | 35.6 | 61.1 | 111.5 | chr2:574878310-574978783 | -1203 |
| -3.121442 | 28.1 | 18.1 | 19.2 | 130.6 | 95.5 | 74.7 | chr5:140552873-140544755 | -5717 |
| -3.121945 | 8.9 | 12.5 | 0 | 45 | 30.3 | 111 | chr8:55530037-55530590 | -2734 |
| -2.2262759 | 51.8 | 68.1 | 44.4 | 267.1 | 132.3 | 369.4 | chr12:248522560-48523691 | 17 |
| -3.1308376 | 3 | 5.6 | 12.6 | 40.6 | 38.6 | 106.5 | chr4:56998081-56998128 | 1433 |
| -1.5854307 | 142.1 | 147.4 | 121.3 | 378.9 | 443.7 | 410.2 | chr15:80341774-80342275 | 135 |
| -2.1489325 | 40 | 55.6 | 6.7 | 116.7 | 121 | 216 | chr7:77163377-77165352 | 686 |
| -1.6207935 | 65.1 | 102.9 | 81.2 | 254.8 | 155.4 | 356.2 | chr1:54126633-54128453 | -4905 |

TABLE 14-continued

Comprehensive DNA Methylation and K27 Profiles of CD44+ Nulliparous and Parous Breast Epithelial Cells

| | | | | | | |
|---|---|---|---|---|---|---|
| -2.6426562 | 10.4 | 11.1 | 21.8 | 84.6 | 48 | 137.8 | chr9:100598247-100599247 | -132 |
| -2.1813572 | 44.4 | 47.3 | 32.6 | 151.4 | 132.9 | 279.5 | chr14:101098656-101100681 | 2228 |
| -2.1484847 | 65.1 | 68.1 | 53.6 | 266.6 | 111.5 | 450.1 | chr11:133218700-132319046 | -626 |
| -1.630144 | 82.9 | 83.4 | 94.6 | 273.6 | 227.2 | 306.8 | chr8:145994470-145995317 | -171 |
| -1.8473588 | 53.3 | 55.6 | 29.3 | 152.9 | 100.2 | 244.2 | chr5:131620879-131621455 | -82 |
| -2.6138813 | 37 | 36.2 | 5 | 160.8 | 67.6 | 250.3 | chr12:100979844-100980574 | -180 |
| -2.8379207 | 22.2 | 15.3 | 51.9 | 268.1 | 99.1 | 272 | chr9:133395830-133396543 | 297 |
| -1.9068906 | 20.7 | 43.1 | 31.8 | 86.6 | 74.1 | 197.8 | chr9:132803789-132804431 | -52 |
| 1.06518919 | 1314.1 | 1337.6 | 1214 | 745.5 | 872.5 | 229.6 | chr9:132804431-132805826 | -1070 |
| -3.0843051 | 22.2 | 4.2 | 30.1 | 137.5 | 119.2 | 222.5 | chr8:67945038-67945550 | -243 |
| -3.7061282 | 17.8 | 15.3 | 0 | 111.3 | 96.7 | 224 | chr6:73388743-73389623 | 628 |
| -2.2609262 | 34 | 65.3 | 23.4 | 164.7 | 148.9 | 274.5 | chr11:2421509-2422722 | -681 |
| -1.938117 | 20.7 | 32 | 32.6 | 78.2 | 70.6 | 177.1 | chr1:203063818-203064574 | -249 |
| -2.6813831 | 53.3 | 54.2 | 28.5 | 205.8 | 125.2 | 541.4 | chr1:148080887-148081129 | -1619 |
| -2.6813831 | 53.3 | 54.2 | 28.5 | 205.8 | 125.2 | 541.4 | chr1:148080887-148081129 | -1619 |
| -3.9696264 | 4.4 | 2.8 | 0 | 26.2 | 19 | 67.6 | chr9:34579052-34579100 | 646 |
| -1.6190175 | 54.8 | 90.4 | 41.8 | 159.3 | 140.6 | 274.5 | chr8:66023159-66024857 | -66 |
| -2.4533101 | 44.4 | 41.7 | 23.4 | 194.9 | 126.3 | 278.5 | chr7:30599934-30600992 | -242 |
| -1.2297287 | 40 | 32 | 56.9 | 80.1 | 92.5 | 129.7 | chr5:111120807-111123048 | -1073 |
| -2.4870209 | 45.9 | 44.5 | 25.9 | 170.7 | 128.1 | 353.2 | chr3:44991382-44992773 | 601 |
| -4.917469 | 1.5 | 13.9 | 0 | 124.7 | 58.1 | 282.6 | chr1:845867-846338 | -4881 |
| -1.4116885 | 99.2 | 109.8 | 92.9 | 288.4 | 173.2 | 341.6 | chr9:5822015-5823025 | 561 |
| -2.0414346 | 66.6 | 100.1 | 111.3 | 470.9 | 360.6 | 312.9 | chr14:54807584-54809084 | -290 |
| -2.0617245 | 13.3 | 33.4 | 36.8 | 80.6 | 64.1 | 203.9 | chr8:37670872-37671743 | -1151 |
| -1.8260984 | 17.8 | 25 | 15.1 | 102.4 | 50.4 | 52.5 | chr10:1091464-1091948 | -1069 |
| -1.4849001 | 29.6 | 50.1 | 37.7 | 55.4 | 103.2 | 170 | chr12:132073016-132073759 | 259 |
| -3.2564612 | 35.5 | 61.2 | 0 | 328 | 125.8 | 470.3 | chr3:57969514-57970738 | 960 |
| -1.6406732 | 105.1 | 109.8 | 62.8 | 369 | 164.9 | 332 | chr10:89254144-89255213 | 476 |
| -1.5825336 | 177.6 | 219.7 | 236.8 | 735.1 | 357.1 | 806.9 | chr12:55769321-55770349 | 892 |
| -2.0075021 | 72.5 | 97.3 | 26.8 | 142.5 | 386.1 | 261.9 | chr14:94691977-94693221 | -1178 |
| 2.3969833 | 14.8 | 18.1 | 25.9 | 89 | 58.7 | 162 | chr1:177529345-177530090 | 78 |
| -2.281746 | 41.4 | 29.2 | 22.6 | 130.6 | 81.9 | 240.7 | chr9:88953207-88953662 | 56 |
| -4.0096586 | 8.9 | 12.5 | 0 | 64.8 | 73 | 206.9 | chr1:172103567-172103939 | -247 |
| -1.9618023 | 94.7 | 93.2 | 2.5 | 216.2 | 156.6 | 368.9 | chr11:94603004-94604890 | -53 |
| -4.0096586 | 8.9 | 12.5 | 0 | 64.8 | 73 | 206.9 | chr1:172103567-172103939 | -3547 |
| -2.1869629 | 10.4 | 22.2 | 46.9 | 78.2 | 99.1 | 184.7 | chr12:24701231-24702280 | -218 |
| -2.3350996 | 31.1 | 18.1 | 18.4 | 74.2 | 63.5 | 203.4 | chr20:56396888-56397921 | -246 |
| -2.8344414 | 34 | 45.9 | 0 | 139.5 | 84.8 | 345.6 | chr18:43710648-43712144 | 114 |
| -1.9253192 | 84.4 | 82 | 23.4 | 244.9 | 149.5 | 326.5 | chr4:72271000-72272650 | -41 |
| -1.850333 | 47.4 | 57 | 29.3 | 161.3 | 110.9 | 209.9 | chr14:101850083-101851049 | -5282 |
| -2.409917 | 38.5 | 50.1 | 24.3 | 169.7 | 131.1 | 299.2 | chr12:43556773-43557299 | -631 |
| -2.7277158 | 54.8 | 25 | 0 | 164.7 | 261 | 102.9 | chr3:39422667-39423758 | -4336 |
| -1.4108514 | 57.7 | 87.6 | 66.1 | 179.6 | 141.8 | 240.7 | chr4:8322595-8323410 | 611 |
| -1.9752614 | 42.9 | 44.5 | 67 | 193.4 | 185.1 | 228.6 | chr8:75424631-75425755 | 21 |
| -3.4418161 | 23.7 | 16.7 | 0.8 | 87.1 | 70 | 290.6 | chr4:155690908-155691499 | -230 |
| -2.4777622 | 11.8 | 25 | 67 | 200.3 | 128.1 | 249.8 | chr8:62789059-62790516 | -231 |
| -2.6066576 | 32.6 | 33.4 | 0 | 89.5 | 85.4 | 227.1 | chr7:127015851-127017121 | 734 |
| NA | 0 | 0 | 0 | 7.9 | 9.5 | 15.6 | chr9:138967411-138967847 | 1041 |
| -1.1135045 | 232.3 | 223.9 | 118 | 595.6 | 333.4 | 313.4 | chr6:160102374-160103612 | 15 |
| -2.201442 | 28.1 | 18.1 | 19.2 | 130.6 | 95.5 | 74.7 | chr5:140552873-140554755 | 1679 |
| -1.4430158 | 142.1 | 122.4 | 216.8 | 593.6 | 449.6 | 265.4 | chr8:27750875-27751651 | 5 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| -2.712718 | 13.3 | 20.9 | 0 | 42.5 | 71.2 | 110.5 | chr10:98335662-98337300 | 318 |
| -2.1394614 | 14.8 | 19.5 | 22.6 | 80.6 | 74.7 | 95.4 | chr5:159781183-159782172 | 235 |
| -1.7355844 | 50.3 | 66.7 | 50.2 | 219.6 | 112.1 | 225.1 | chr7:70235521-70236197 | 135 |
| -2.8433243 | 19.2 | 11.1 | 41 | 222.6 | 74.1 | 215 | chr7:74126564-74128204 | 251 |
| -1.2125655 | 63.6 | 55.6 | 164.9 | 185 | 257.4 | 216 | chr5:157218545-157219489 | -271 |
| -2.6942611 | 7.4 | 12.5 | 1.7 | 56.4 | 31.4 | 52 | chr2:203812030-203812879 | 1046 |
| -2.362684 | 7.4 | 19.5 | 21.8 | 65.3 | 41.5 | 144.3 | chr10:62881728-62882247 | 1227 |
| -1.0676447 | 90.3 | 130.7 | 149.8 | 241.4 | 330.4 | 205.4 | chr15:39590471-39591694 | 2295 |
| -1.5728094 | 60.7 | 61.2 | 104.6 | 161.8 | 164.3 | 347.7 | chr3:95264136-95265419 | -427 |
| -2.6504632 | 7.4 | 12.5 | 16.7 | 71.7 | 55.2 | 102.9 | chr2:294886201-94886639 | 127 |
| -1.346422 | 59.2 | 79.3 | 146.5 | 185.5 | 329.8 | 209.4 | chr5:118632235-118633061 | 332 |
| -1.1961353 | 65.1 | 54.2 | 51 | 77.7 | 224.2 | 88.3 | chr1:116289294-116290518 | 108 |
| -3.5926906 | 42.9 | 8.3 | 0 | 166.2 | 215.3 | 236.2 | chr1:220829617-220830175 | -18 |
| -3.4315875 | 34 | 26.4 | 0 | 204.8 | 137.6 | 309.3 | chr5:94981499-94982948 | 488 |
| -2.6735513 | 25.2 | 33.4 | 29.3 | 157.8 | 133.5 | 269.5 | chr4:140593828-140594939 | -27 |
| -1.4532568 | 35.5 | 30.6 | 82.9 | 82.1 | 189.2 | 136.7 | chr8:118602467-118603205 | 691 |
| -2.2210314 | 60.7 | 66.7 | 54.4 | 329 | 127.5 | 391.1 | chr2:16650065-16650933 | 1792 |
| -1.9931463 | 74 | 111.2 | 46.9 | 358.6 | 177.9 | 387.5 | chr17:64834261-64835583 | -37 |
| -3.9203267 | 4.4 | 7 | 0 | 36.6 | 25.5 | 110.5 | chr4:105632151-105632406 | -362 |
| NA | 0 | 0 | 0 | 4.9 | 8.9 | 19.2 | chr12:54831332-54832506 | -682 |
| -3.039296 | 34 | 75.1 | 0 | 280.5 | 167.3 | 449.1 | chr15:20384462-20384965 | -122 |
| -1.8700955 | 50.3 | 58.4 | 74.5 | 189 | 130.5 | 350.2 | chr15:20385207-20385452 | 494 |
| -3.0515539 | 0 | 0 | 13.4 | 21.3 | 36.8 | 53 | chr1:89232018-89232557 | -1183 |
| -1.764454 | 22.2 | 12.5 | 36 | 62.3 | 89.6 | 88.3 | chr3:49952030-49953467 | 153 |
| -4.3696945 | 5.9 | 4.2 | 0 | 53.9 | 30.3 | 124.6 | chr7:53337537-53338027 | -2033 |
| -2.587414 | 19.2 | 13.9 | 15.9 | 87.6 | 51 | 155.9 | chr14:57736234-57736688 | -124 |
| -2.2573766 | 28.1 | 25 | 31 | 129.1 | 80.7 | 192.3 | chr11:124966863-124967170 | -932 |
| -2.3380478 | 19.2 | 22.2 | 20.9 | 69.7 | 68.2 | 177.1 | chr4:89661478-89663872 | 1303 |
| -2.1949972 | 20.7 | 22.2 | 45.2 | 137.5 | 73.6 | 192.3 | chr20:56989759-56990247 | 298 |
| -2.9619022 | 14.8 | 11.1 | 0 | 58.4 | 81.3 | 62.1 | chr1:7066190-7066927 | -182 |
| -3.1720406 | 14.8 | 5.6 | 32.6 | 188 | 78.3 | 211.4 | chr12:15833072-15833634 | 248 |
| -2.3041229 | 16.3 | 13.9 | 28.5 | 125.2 | 68.8 | 95.9 | chr8:75848816-75849264 | 480 |
| -2.0616079 | 38.5 | 44.5 | 40.2 | 147.9 | 122.2 | 244.2 | chr15:53789567-53790118 | -263 |
| -4.2680987 | 7.4 | 8.3 | 0 | 77.2 | 55.8 | 169.5 | chr8:145604891-145605068 | 562 |
| 0.66181139 | 161.3 | 198.8 | 181.6 | 135 | 67.6 | 139.8 | chr8:145605348-145606127 | -196 |
| -3.3864168 | 0 | 7 | 0 | 18.8 | 26.1 | 28.3 | chr6:101022426-101022771 | -4326 |
| -3.9632172 | 13.3 | 8.3 | 0 | 107.8 | 54 | 175.1 | chr17:46297064-46299593 | -1916 |
| -2.5729829 | 31.1 | 58.4 | 53.6 | 255.5 | 116.3 | 479.9 | chr6:32594631-32595090 | 694 |
| -3.0319025 | 22.2 | 34.8 | 1.7 | 167.7 | 68.2 | 244.2 | chr11:69793744-69795530 | 167 |
| -3.919849 | 13.3 | 0 | 0 | 70.7 | 46.3 | 84.3 | chr3:186699750-186700170 | -421 |
| -1.6935512 | 26.6 | 25 | 24.3 | 73.2 | 59.3 | 113 | chr8:105548115-105548561 | 115 |
| -1.5002813 | 32.6 | 33.4 | 60.3 | 124.2 | 97.9 | 135.2 | chr5:71130688-71133142 | -12 |
| -2.2884093 | 28.1 | 34.8 | 47.7 | 111.8 | 115.1 | 313.4 | chr2:173928132-173928795 | 657 |
| -0.7453209 | 103.6 | 83.4 | 98.8 | 133.1 | 191.6 | 154.4 | chr10:95315996-95316875 | 24 |
| -1.2767951 | 66.6 | 62.6 | 124.7 | 238.9 | 185.1 | 191.2 | chr2:29191202-29193138 | 349 |
| -0.8992998 | 193.9 | 54.2 | 172.4 | 188.5 | 347 | 248.8 | chr16:79131299-79133099 | -155 |
| -3.3607473 | 16.3 | 22.2 | 0 | 153.3 | 74.7 | 167.5 | chr5:118815804-118816169 | -60 |
| -2.200321 | 34 | 44.5 | 41 | 152.4 | 126.3 | 270.5 | chr5:179854004-179854913 | 436 |
| -1.9692242 | 75.5 | 69.5 | 61.1 | 264.2 | 161.3 | 381.5 | chr3:57103558-57105029 | 504 |
| -2.2040217 | 69.6 | 80.6 | 51.9 | 253.3 | 173.8 | 504.1 | chr22:41815151-41816176 | -290 |
| -1.2883509 | 71 | 62.6 | 59.4 | 115.3 | 137.6 | 218.5 | chr16:48656629-48657416 | -359 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| -2.1511678 | 54.8 | 61.2 | 87 | 329 | 179.1 | 393.6 | chrX:6153618-6154437 | 1861 |
| -1.8949432 | 56.2 | 97.3 | 49.4 | 185.5 | 236.1 | 333 | chr1:280861190-280872241 | -393 |
| -5.7944159 | 0 | 1.4 | 0 | 16.3 | 12.5 | 48.9 | chr9:113401932-113401954 | -411 |
| -2.7401465 | 14.8 | 26.4 | 10.9 | 93 | 76.5 | 178.6 | chr9:88751642-88752323 | -58 |
| -1.592736 | 69.6 | 73.7 | 60.3 | 246.8 | 121.6 | 245.7 | chr19:10515766-10516412 | 443 |
| -2.022861 | 65.1 | 80.6 | 34.3 | 312.1 | 135.8 | 283.6 | chr16:3036919-3037509 | 532 |
| -1.0517725 | 106.6 | 164.1 | 189.1 | 303.2 | 301.3 | 348.7 | chr19:1519055-1519950 | -445 |
| -1.5171492 | 90.3 | 83.4 | 75.3 | 290.4 | 192.2 | 230.1 | chr5:946113-946722 | 414 |
| -2.0518535 | 65.1 | 72.3 | 36.8 | 258.7 | 118 | 345.6 | chr17:44160972-44161930 | -341 |
| -1.8106503 | 74 | 76.5 | 61.9 | 312.6 | 148.9 | 283.6 | chr2:114230454-114231272 | 7 |
| -2.5803532 | 23.7 | 18.1 | 0 | 84.6 | 53.4 | 112 | chr4:77296463-77297457 | 290 |
| -1.4852356 | 44.4 | 37.5 | 25.9 | 106.4 | 92.5 | 102.9 | chr1:27688633-27689790 | 45 |
| -2.1891073 | 74 | 36.2 | 27.6 | 189.5 | 128.1 | 310.8 | chr11:107233656-107235586 | 243 |
| -1.242768 | 127.3 | 184.9 | 169.9 | 386.3 | 532.1 | 222.5 | chr1:38045876-38047629 | -300 |
| -2.1394614 | 14.8 | 19.5 | 22.6 | 80.6 | 74.7 | 95.4 | chr5:159781183-159782172 | -2931 |
| -2.1314992 | 77 | 76.5 | 43.5 | 306.7 | 148.3 | 408.2 | chr10:101481403-101482095 | 664 |
| -3.9010904 | 13.3 | 8.3 | 0 | 97.5 | 85.4 | 139.8 | chr19:58052574-58052991 | -68 |
| -1.9889773 | 28.1 | 43.1 | 56.9 | 176.6 | 106.8 | 225.1 | chr11:93916413-93917251 | 58 |
| -2.9635687 | 10.4 | 19.5 | 9.2 | 70.2 | 65.8 | 169 | chr19:53947059-53948851 | 2504 |
| -2.0958967 | 34 | 38.9 | 18.4 | 107.8 | 70.6 | 211.9 | chr16:65195422-65195747 | -118 |
| -2.2241089 | 20.7 | 15.3 | 36 | 120.7 | 89 | 126.7 | chr22:27993009-27995892 | 434 |
| NA | 0 | 0 | 0 | 4.5 | 16.6 | 8.6 | chr2:102169906-102170013 | 95 |
| -2.2364473 | 38.5 | 23.6 | 56.1 | 154.3 | 121.6 | 281.1 | chr7:98901245-98901838 | 203 |
| -3.180403 | 13.3 | 22.2 | 20.9 | 51 | 385.6 | 74.7 | chr1:159390152-159391397 | 617 |
| -1.5818765 | 29.6 | 65.3 | 61.1 | 117.2 | 142.4 | 207.4 | chr2:38684134-38686062 | -1570 |
| -1.1354154 | 128.8 | 148.8 | 112.1 | 296.8 | 227.8 | 331.5 | chr3:53053602-53055147 | -53 |
| -1.940563 | 34 | 47.3 | 1.7 | 115.3 | 94.3 | 109 | chr10:7494580-7496011 | -1839 |
| -1.3564264 | 100.6 | 115.4 | 174.9 | 392.3 | 341.7 | 266.9 | chr15:40051195-40051796 | 539 |
| -3.4743232 | 5.9 | 12.5 | 0 | 63.3 | 40.3 | 100.9 | chr9:135271877-135272157 | 968 |
| -4.4417585 | 0 | 5.6 | 0 | 26.7 | 51.6 | 43.4 | chr19:62322062-62322757 | -911 |
| -2.8213041 | 7.4 | 18.1 | 14.2 | 83.1 | 48.6 | 148.9 | chr12:112057719-112058059 | 515 |
| -2.0098133 | 29.6 | 37.5 | 61.1 | 118.2 | 94.3 | 303.8 | chr5:60031405-60031675 | 173 |
| -3.180403 | 13.3 | 22.2 | 20.9 | 51 | 385.6 | 74.7 | chr1:159390152-159391397 | -5103 |
| -2.5430489 | 8.9 | 13.9 | 22.6 | 83.6 | 52.8 | 128.2 | chr20:62083042-62083949 | 621 |
| -3.9864908 | 7.4 | 2.8 | 12.6 | 80.1 | 69.4 | 211.9 | chr20:10363667-10364109 | -62 |
| -1.4059221 | 155.4 | 207.2 | 296.3 | 518.9 | 820.9 | 406.2 | chr2:177836237-177837548 | 1213 |
| -1.493867 | 244.2 | 196 | 218.4 | 543.6 | 377.8 | 933.5 | chr7:143682946-143683511 | -193 |
| -3.6647718 | 14.8 | 16.7 | 0.8 | 134.6 | 51 | 213.9 | chr8:109330258-109330464 | -226 |
| -3.5555187 | 7.4 | 8.3 | 0.8 | 51.9 | 42.7 | 99.4 | chr19:5854880-5855114 | 28 |
| -2.7008184 | 5.9 | 12.5 | 40.2 | 106.8 | 176.8 | 97.4 | chrX:54399186-54401783 | 679 |
| -2.3289485 | 14.8 | 13.9 | 0 | 43 | 45.7 | 55.5 | chr8:17314343-173115170 | 451 |
| -3.9864908 | 7.4 | 2.8 | 12.6 | 80.1 | 69.4 | 211.9 | chr20:10363667-10364109 | -1022 |
| -3.2756344 | 20.7 | 7 | 0.8 | 55.4 | 61.7 | 158.9 | chr9:90193547-90194304 | 809 |
| -3.6088956 | 16.3 | 11.1 | 0 | 112.3 | 50.4 | 171.6 | chr2:98918248-98919697 | 144 |
| -2.5895304 | 23.7 | 23.6 | 0 | 109.3 | 49.8 | 125.6 | chr6:127482376-127482836 | 866 |
| -1.5604501 | 50.3 | 36.2 | 24.3 | 142.5 | 92.5 | 91.8 | chr3:187766910-187768400 | 180 |
| -3.7474471 | 3 | 4.2 | 0 | 30.2 | 16 | 50.5 | chr10:90332349-90332669 | -3989 |
| -2.3678306 | 59.2 | 80.6 | 42.7 | 300.8 | 167.9 | 473.3 | chr7:45163215-45163952 | -308 |
| -1.6233943 | 38.5 | 38.9 | 72 | 234 | 116.3 | 110 | chr14:72462792-72463642 | 380 |
| -2.422501 | 34 | 37.5 | 0.8 | 112.3 | 106.8 | 168.5 | chr6:47383784-47384655 | 1420 |
| -2.436975 | 32.6 | 41.7 | 13.4 | 141.5 | 96.7 | 236.7 | chr17:25281934-25282484 | -1065 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| -2.1113493 | 45.9 | 30.6 | 28.5 | 159.3 | 86 | 208.4 | chr12:115802341-115803349 | 770 |
| -3.7581776 | 22.2 | 7 | 0 | 66.8 | 89.6 | 238.7 | chr8:49996043-49997188 | -74 |
| -4.3968902 | 1.5 | 0 | 6.4 | | 10.1 | 15.1 | chr11:1808266-1808496 | -3868 |
| -1.5764978 | 183.5 | 233.6 | 403.4 | 1184 | 758.7 | 504.6 | chr4:9629353-9630427 | 2322 |
| -1.1518875 | 94.7 | 148.8 | 68.6 | 308.2 | 218.3 | 167 | chr9:129198581-129199330 | -330 |
| -2.5273936 | 25.2 | 12.5 | 32.6 | 231 | 102.6 | 71.7 | chr7:7125193-7126022 | -170 |
| -1.9804179 | 41.4 | 50.1 | 14.2 | 119.7 | 92.5 | 204.9 | chr14:102127332-102128435 | -1102 |
| -3.1202942 | 10.4 | 19.5 | 0 | 70.2 | 68.2 | 121.6 | chr14:19173364-19174000 | -312 |
| -2.7201632 | 22.2 | 26.4 | 8.4 | 89 | 74.7 | 211.9 | chr4:90251223-90252429 | -1164 |
| -2.2589937 | 25.2 | 15.3 | 17.6 | 48.5 | 61.1 | 168.5 | chr1:243064350-243066469 | -852 |
| -2.3641408 | 41.4 | 38.9 | 26.8 | 151.4 | 127.5 | 272.5 | chr1:243064848-243065452 | -111 |
| -2.0143553 | 29.6 | 27.8 | 12.6 | 79.1 | 56.9 | 146.8 | chr1:31855690-31857130 | -817 |
| -2.2207253 | 29.6 | 38.9 | 55.2 | 136.5 | 109.1 | 331 | chr6:43592521-43593651 | -406 |
| -2.3618121 | 32.6 | 38.9 | 18.4 | 135.5 | 95.5 | 231.1 | chr3:44877831-44878420 | -286 |
| -2.2871291 | 41.4 | 50.1 | 13.4 | 180.1 | 93.7 | 238.2 | chr6:108689120-108689745 | -276 |
| 1.86049551 | 423.3 | 408.8 | 215.9 | 89 | 147.1 | 52.5 | chr6:108689869-108690628 | -1092 |
| -1.6747981 | 25.2 | 54.2 | 69.5 | 188 | 116.3 | 171.1 | chr9:1039647-1040693 | -449 |
| -2.3204362 | 19.2 | 15.3 | 4.2 | 33.6 | 45.7 | 114 | chr13:36471442-36471693 | -90 |
| -3.5510621 | 4.4 | 7 | 0.8 | 26.2 | 25.5 | 91.3 | chr16:70684641-70685493 | -48 |
| -3.4443387 | 25.2 | 33.4 | 0.8 | 200.3 | 106.2 | 340.1 | chr1:78017928-78018723 | 429 |
| -2.3204362 | 19.2 | 15.3 | 4.2 | 33.6 | 45.7 | 114 | chr13:36471442-36471693 | -1349 |
| -2.0548009 | 16.3 | 52.8 | 36.8 | 151.4 | 107.4 | 181.2 | chr10:72748811-72749675 | -228 |
| -2.131884 | 28.1 | 23.6 | 24.3 | 97.9 | 61.1 | 174.1 | chr10:17725512-17725715 | -516 |
| -2.4870209 | 45.9 | 44.5 | 25.9 | 170.7 | 128.1 | 353.2 | chr3:44991382-44992773 | -667 |
| -1.8949432 | 56.2 | 97.3 | 49.4 | 185.5 | 236.1 | 333 | chr11:28086190-28087241 | 342 |
| -3.7975656 | 13.3 | 2.8 | 0.8 | 83.1 | 46.9 | 105 | chr22:20419465-20420148 | 265 |
| -3.1516533 | 45.9 | 61.2 | 21.8 | 328.5 | 169.1 | 647.9 | chr13:51630978-51632329 | 344 |
| -2.1455035 | 41.4 | 57 | 23.4 | 177.1 | 141.8 | 220 | chr19:1463495-1465231 | -344 |
| -2.168852 | 45.9 | 45.9 | 42.7 | 209.2 | 128.7 | 266.9 | chr16:74146623-74146977 | 837 |
| -0.6319974 | 128.8 | 136.3 | 147.1 | 140 | 206.4 | 292.7 | chr21:10011505-10013330 | 374 |
| -2.0814907 | 42.9 | 43.1 | 15.1 | 157.8 | 82.4 | 187.7 | chr1:234295000-234295508 | -150 |
| -3.7474471 | 3 | 4.2 | 0 | 30.2 | 16 | 50.5 | chr10:90332349-90332669 | 441 |
| -2.6066576 | 32.6 | 33.4 | 0 | 89.5 | 85.4 | 227.1 | chr7:127015851-127017121 | -3596 |
| NA | 0 | 0 | 0 | 13.9 | 16 | 68.6 | chr1:58815177-58815231 | 550 |
| -1.6179959 | 23.7 | 29.2 | 53.6 | 102.9 | 97.9 | 126.1 | chr3:171239048-171239586 | 889 |
| -1.9693865 | 66.6 | 112.6 | 128 | 622.8 | 182.1 | 398.1 | chr1:166371323-166371137 | 18 |
| -2.1956672 | 40 | 97.3 | 46 | 285.9 | 188 | 365.8 | chr10:20144047-20146014 | -347 |
| -2.1401184 | 57.7 | 54.2 | 23.4 | 229 | 108 | 259.4 | chr18:51405373-51406320 | 1012 |
| -1.8307694 | 37 | 44.5 | 67.8 | 232 | 127.5 | 171.6 | chr7:151762120-151763825 | -1940 |
| -1.4710977 | 47.4 | 47.3 | 200.9 | 185 | 383.2 | 251.3 | chr7:148824576-148825558 | 660 |
| -2.4509842 | 10.4 | 9.7 | 1.7 | 22.8 | 30.3 | 66.1 | chr6:34468947-34469244 | -676 |
| -1.9989567 | 63.6 | 82 | 61.9 | 303.7 | 134.6 | 391.1 | chr10:21863928-21864371 | 1042 |
| -1.7853881 | 45.9 | 55.6 | 31.8 | 97.5 | 204.6 | 157.4 | chr3:23219538-23220387 | 175 |
| -1.6241295 | 13.3 | 33.4 | 72 | 108.3 | 119.8 | 137.8 | chr2:9832871698330772 | 695 |
| -4.0096586 | 8.9 | 12.5 | 0 | 64.8 | 73 | 206.9 | chr1:172103567-172103939 | -1277 |
| -2.2297344 | 31.1 | 23.6 | 29.3 | 133.6 | 77.7 | 182.7 | chr2:12393999-12394751 | 61 |
| -1.7790991 | 31.1 | 45.9 | 51.9 | 137 | 81.9 | 223.5 | chr4:101089810-101091425 | -41 |
| -4.0096586 | 8.9 | 12.5 | 0 | 64.8 | 73 | 206.9 | chr1:172103567-172103939 | -1054 |
| -1.658687 | 90.3 | 150.2 | 195 | 598.6 | 441.3 | 335.1 | chr7:43764018-43765416 | -79 |
| -4.0096586 | 8.9 | 12.5 | 0 | 64.8 | 73 | 206.9 | chr1:172103567-172103939 | -2562 |
| -3.3630312 | 25.2 | 13.9 | 0 | 100.9 | 65.2 | 236.2 | chr15:32181330-32181477 | -58 |

TABLE 14-continued

Comprehensive DNA Methylation and K27 Profiles of CD44+ Nulliparous and Parous Breast Epithelial Cells

| | | | | | | |
|---|---|---|---|---|---|---|
| −2.3298566 | 63.6 | 62.6 | 22.6 | 278 | 116.9 | 353.2 | chr9:131467967-131469208 | 847 |
| −2.6183738 | 10.4 | 20.9 | 0 | 66.8 | 45.7 | 79.7 | chr1:605589-606370 | −251 |
| −2.3759453 | 34 | 27.8 | 22.6 | 90 | 101.4 | 246.7 | chr2:71307038-71308874 | −215 |
| −1.4950989 | 42.9 | 47.3 | 35.1 | 70.2 | 135.2 | 147.8 | chr1:165956555-165958258 | −425 |
| −2.7329385 | 14.8 | 13.9 | 0 | 41.1 | 52.8 | 96.9 | chr4:74154338-74154532 | −99 |
| −1.5351153 | 45.9 | 51.4 | 46 | 90.5 | 93.7 | 231.1 | chr3:15617312-15618368 | −418 |
| −1.8604783 | 32.6 | 47.3 | 43.5 | 115.3 | 99.7 | 233.1 | chr3:151170067-151172608 | 94 |
| NA | 0 | 0 | 0 | 15.8 | 14.8 | 34.8 | chr2:128792575-128792605 | 51 |
| −2.8409383 | 25.2 | 20.9 | 0 | 69.7 | 49.2 | 211.4 | chr2:99184511-99185061 | 202 |
| −3.2824159 | 17.8 | 7 | 0 | 33.1 | 83.6 | 124.6 | chr4:42095282-42096794 | 1426 |
| −2.1231863 | 34 | 38.9 | 47.7 | 197.9 | 81.3 | 246.2 | chr17:13912918-13914109 | 70 |
| −3.0331147 | 10.4 | 22.2 | 6.7 | 87.6 | 57.5 | 176.6 | chr1:153509278-153510155 | 189 |
| −3.4958916 | 11.8 | 11.1 | 31.8 | 190 | 75.9 | 351.2 | chr3:38665606-38666656 | 36 |
| −4.0096586 | 8.9 | 12.5 | 0 | 64.8 | 73 | 206.9 | chr1:172103567-172103939 | −5 |
| 1.9316769 | 227.9 | 265.6 | 92.1 | 60.4 | 38.6 | 54.5 | chr15:72206613-72208128 | −1397 |
| −2.8981646 | 14.8 | 25 | 0 | 81.1 | 51.6 | 164 | chr15:72209713-72210145 | 1162 |
| −2.7277158 | 54.8 | 25 | 0 | 164.7 | 261 | 102.9 | chr3:39422667-39423758 | −1673 |
| −1.4745615 | 32.6 | 23.6 | 62.8 | 96 | 132.3 | 102.4 | chr20:44575006-44575647 | 275 |
| −1.6367889 | 65.1 | 48.7 | 111.3 | 211.2 | 256.2 | 232.6 | chr1:34893820-34894405 | 403 |
| −1.6764378 | 56.2 | 48.7 | 0 | 105.6 | 133.7 | chr10:11099247-11100058 | −246 |
| −2.0409303 | 25.2 | 20.9 | 0 | 09.7 | 49.2 | 211.4 | chr2:99104511-99105001 | −093 |
| −3.6980252 | 5.9 | 12.5 | 0 | 71.2 | 30.3 | 137.3 | chr6:135860400-135860631 | 81 |
| −3.720785 | 3 | 7 | 0 | 38.1 | 26.1 | 67.6 | chr11:111542666-111543583 | −180 |
| −2.868668 | 5.9 | 7 | 46 | 128.1 | 103.8 | 198.3 | chr15:40999608-41000551 | 220 |
| −2.1370028 | 26.6 | 38.9 | 0 | 107.3 | 68.8 | 112 | chr21:32573336-32573892 | −367 |
| −1.7125208 | 72.5 | 77.9 | 72.8 | 220.1 | 237.9 | 273.5 | chr2:84985416-84986670 | −230 |
| −2.136215 | 20.7 | 11.1 | 29.3 | 78.7 | 65.8 | 124.1 | chr6:147567361-147567587 | 274 |
| −1.4365318 | 57.7 | 52.8 | 230.1 | 215.2 | 427.7 | 279 | chr4:106613497-106614654 | 601 |
| −4.9498606 | 1.5 | 2.8 | 0 | 26.7 | 15.4 | 90.8 | chr4:106614654-106614915 | −108 |
| −2.2209344 | 23.7 | 52.8 | 72 | 291.4 | 150.1 | 250.8 | chr3:38181780-38182371 | 46 |
| −1.5031882 | 77 | 86.2 | 120.5 | 360.6 | 233.7 | 209.9 | chr17:75386229-75387914 | −1586 |
| −2.0795742 | 44.4 | 57 | 0 | 127.1 | 110.3 | 191.2 | chr4:8632818-8653572 | 5 |
| −2.5686543 | 16.3 | 12.5 | 14.2 | 62.8 | 68.2 | 124.1 | chr1:94475184-94476492 | 57 |
| −2.3219281 | 8.9 | 11.1 | 0 | 45.5 | 30.3 | 24.2 | chr7:76882342-76882921 | 1022 |
| 1.24581832 | 623 | 686.9 | 621 | 416.5 | 196.9 | 200.8 | chr7:76882921-76884267 | 59 |
| −1.2462244 | 183.5 | 193.3 | 287.9 | 831.1 | 435.4 | 310.3 | chr3:106567340-106568558 | −453 |
| −2.6218455 | 94.7 | 105.7 | 26.8 | 521.4 | 196.9 | 680.2 | chr3:106568558-106570647 | 1200 |
| −0.9815 | 140.6 | 109.8 | 251.9 | 361.6 | 344.6 | 285.6 | chr9:114287901-114289752 | −242 |
| −4.3307731 | 10.4 | 8.3 | 0 | 112.3 | 54.6 | 209.4 | chr20:23565525-23566299 | 662 |
| −1.7131294 | 87.3 | 76.5 | 109.6 | 377.4 | 174.4 | 344.6 | chr2:75982378-75984033 | 286 |
| −2.6978863 | 14.8 | 12.5 | 7.5 | 65.8 | 34.4 | 125.6 | chr12:5411195-5411716 | −85 |
| −1.2483035 | 85.8 | 122.4 | 215.9 | 351.7 | 316.2 | 339.6 | chr5:32347774-32349013 | 478 |
| −4.0096586 | 8.9 | 12.5 | 0 | 64.8 | 73 | 206.9 | chr1:172103567-172103939 | −1621 |
| −1.4884374 | 122.8 | 129.3 | 154.8 | 418.5 | 440.1 | 283.1 | chr10:112246824-112247869 | −268 |
| −2.8089614 | 20.7 | 44.5 | 50.2 | 281.5 | 141.2 | 386 | chr4:141664301-141665581 | 140 |
| −0.8464267 | 273.8 | 282.2 | 159 | 523.9 | 441.3 | 320.4 | chr7:127078764-127079128 | −491 |
| −1.462698 | 177.6 | 162.7 | 72.8 | 330.4 | 279.4 | 528.8 | chr22:37426056-37427896 | −761 |
| −0.949674 | 190.9 | 283.6 | 126.4 | 365.6 | 444.3 | 350.7 | chr10:97406194-97407388 | −234 |
| −2.0886834 | 22.2 | 25 | 8.4 | 52.9 | 60.5 | 123.1 | chr1:63462085-63463032 | −459 |
| −1.9348127 | 53.3 | 19.5 | 23.4 | 107.3 | 98.5 | 162 | chr18:12397571-12398548 | 132 |
| −2.5305147 | 5.9 | 7 | 4.2 | 13.9 | 44.5 | 40.4 | chr2:208840098-208840675 | 1151 |

TABLE 14-continued

Comprehensive DNA Methylation and K27 Profiles of CD44+ Nulliparous and Parous Breast Epithelial Cells

| | | | | | | |
|---|---|---|---|---|---|---|
| -1.8307694 | 37 | 44.5 | 67.8 | 232 | 127.5 | 171.6 | chr7:151762120-151763825 | 1051 |
| -1.778318 | 42.9 | 47.3 | 121.3 | 254.8 | 195.7 | 275 | chr1:1092786-1094291 | 188 |
| -4.1079153 | 8.9 | 1.4 | 0 | 20.8 | 36.2 | 120.6 | chr19:3651386-3651728 | -112 |
| -2.6457843 | 14.8 | 18.1 | 0 | 37.6 | 39.1 | 129.2 | chr21:30233437-30233708 | 581 |
| -2.3302937 | 13.3 | 18.1 | 47.7 | 147.4 | 95.5 | 154.9 | chr3:171013028-171013375 | -195 |
| -2.9218742 | 34 | 23.6 | 31.8 | 247.3 | 93.1 | 337.1 | chr22:25238018-25239097 | -120 |
| -3.4518936 | 7.4 | 8.3 | 0 | 66.3 | 27.3 | 78.2 | chr2:101291260-101291480 | 214 |
| -4.0537973 | 16.3 | 20.9 | 0.8 | 176.1 | 96.7 | 358.3 | chr2:27149190-27149596 | 419 |
| -3.1308376 | 3 | 5.6 | 12.6 | 40.6 | 38.6 | 106.5 | chr4:56998081-56998128 | -1502 |
| -2.4948147 | 8.9 | 12.5 | 25.1 | 56.4 | 62.9 | 142.8 | chr2:113238644-113239469 | -331 |
| -1.9460659 | 34 | 38.9 | 0 | 50 | 147.1 | 83.8 | chr7:97718827-97719966 | 8 |
| -3.7933254 | 4.4 | 11.1 | 0 | 60.8 | 42.1 | 112 | chr15:48503299-48504969 | 264 |
| -2.7401378 | 22.2 | 22.2 | 3.3 | 130.1 | 63.5 | 125.1 | chr1:216584860-216586762 | -202 |
| -2.4367512 | 20.7 | 11.1 | 25.9 | 76.7 | 61.1 | 174.6 | chr3:129024106-129024512 | 82 |
| -3.4283268 | 13.3 | 30.6 | 0 | 125.2 | 65.8 | 281.6 | chr2:110013438-110013932 | 128 |
| -2.239784 | 28.1 | 37.5 | 25.1 | 121.2 | 87.2 | 220 | chr9:33740831-33741262 | 532 |
| -2.3343107 | 35.5 | 27.8 | 154.8 | 307.2 | 395.6 | 397.1 | chr9:36389998-36391748 | -577 |
| -1.8868475 | 20.7 | 16.7 | 25.9 | 47 | 151.8 | 35.3 | chr17:23243362-23244946 | 382 |
| -3.9093592 | 14.8 | 38.9 | 0.8 | 337.4 | 109.1 | 372.4 | chr4:144654023-144654527 | 210 |
| -1.0511445 | 224.9 | 222.5 | 185.8 | 445.2 | 422.9 | 444 | chr16:46956887-46958092 | -204 |
| -2.0925749 | 48.8 | 65.3 | 25.1 | 224.1 | 119.8 | 249.8 | chr1:222871529-222872188 | 1057 |
| -1.7283082 | 37 | 47.3 | 56.1 | 146.4 | 154.8 | 164 | chr17:23903038-23903700 | 401 |
| -1.3023925 | 32.6 | 41.7 | 40.2 | 89 | 82.4 | 111 | chr7:8267280-8267925 | 605 |
| -2.307602 | 32.6 | 58.4 | 77 | 232.5 | 143.5 | 455.7 | chr2:151051121-151051685 | 1023 |
| -0.8714545 | 143.5 | 118.2 | 117.2 | 211.7 | 243.8 | 237.7 | chr2:183288467-183289461 | -279 |
| -4.337035 | 7.4 | 9.7 | 0 | 81.6 | 51.6 | 212.4 | chr2:37312352-37312721 | -292 |
| -2.0957828 | 25.2 | 30.6 | 27.6 | 112.3 | 73.6 | 170.6 | chr9:99857722-99858516 | -660 |
| -2.5970877 | 59.2 | 90.4 | 30.1 | 282 | 192.2 | 613.1 | chr3:88281037-88281970 | -79 |
| -2.0429034 | 25.2 | 18.1 | 59.4 | 129.1 | 110.9 | 183.2 | chr7:56087164-56087941 | 681 |
| -1.9148984 | 57.7 | 68.1 | 33.5 | 201.8 | 129.9 | 269 | chr7:151352732-151354598 | -45 |
| -2.5141875 | 60.7 | 52.8 | 26.8 | 242.9 | 172.6 | 386 | chr8:134653155-134654277 | -351 |
| -2.7667582 | 17.8 | 25 | 9.2 | 85.6 | 80.1 | 188.2 | chr1:210275400-210275524 | 45 |
| -1.0931392 | 161.3 | 183.5 | 108.8 | 333.4 | 284.1 | 350.2 | chr1:1435936-1437511 | -694 |
| -2.7447405 | 31.1 | 26.4 | 176.6 | 649 | 653.7 | 266.4 | chr22:36285998-36287625 | 395 |
| -2.0097502 | 47.4 | 47.3 | 15.9 | 143.5 | 85.4 | 216.5 | chr1:32777439-32778375 | 549 |
| -2.0967773 | 45.9 | 43.1 | 0 | 113.3 | 97.9 | 169.5 | chr10:75427620-75428361 | 113 |
| -3.6196086 | 5.9 | 18.1 | 0 | 74.7 | 66.4 | 153.9 | chr7:136205910-136206410 | 1789 |
| -2.9504799 | 14.8 | 11.1 | 6.7 | 108.3 | 46.3 | 97.4 | chr6:26141366-26141941 | -1386 |
| -2.9556652 | 11.8 | 16.7 | 0 | 43.5 | 40.9 | 136.7 | chr5:180163617-180163727 | -1018 |
| -1.7125361 | 28.1 | 33.4 | 32.6 | 70.7 | 74.7 | 163 | chr6:88356392-88356605 | -63 |
| -2.5504276 | 22.2 | 23.6 | 56.9 | 100.4 | 49.8 | 118.1 | chr8:125808048-125808527 | 1624 |
| -1.4904368 | 57.7 | 61.2 | 92.1 | 105.4 | 117.4 | 209.9 | chr8:125809309-125810995 | -241 |
| -2.6669884 | 44.4 | 52.8 | 0 | 232.5 | 90.2 | 299.7 | chr16:88566501-88567348 | -481 |
| -1.2950533 | 28.1 | 25 | 0.8 | 65.3 | 54 | 141.3 | chr5:135554375-135556109 | 1508 |
| -1.6187265 | 31.1 | 58.4 | 56.9 | 156.8 | 105.6 | 187.2 | chr3:62835322-62836586 | 150 |
| -0.7675276 | 105.1 | 70.9 | 92.1 | 109.8 | 172 | 174.6 | chr10:61138081-61138866 | 1182 |
| -2.1970923 | 38.5 | 44.5 | 0 | 99.9 | 78.9 | 201.8 | chr8:143542496-143542810 | 275 |
| -3.1465151 | 8.9 | 12.5 | 35.1 | 74.7 | 32.6 | 82.2 | chr10:70386664-70387001 | 935 |
| -1.5728094 | 60.7 | 61.2 | 104.6 | 161.8 | 164.3 | 347.7 | chr3:95264136-95265419 | 233 |
| -1.0776169 | 131.7 | 158.5 | 143.1 | 300.8 | 318.5 | 295.2 | chr21:15358091-15360425 | -261 |
| -1.5262028 | 37 | 51.4 | 61.1 | 90 | 192.2 | 148.4 | chr20:9444510-9444914 | 1442 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| −2.6889745 | 10.4 | 44.5 | 20.9 | 126.6 | 100.8 | 261.4 | chr4:75937779-75939149 | 442 |
| −1.9098993 | 23.7 | 23.6 | 48.5 | 85.6 | 80.1 | 194.3 | chr7:19715162-19715215 | −3 |
| −1.9989632 | 38.5 | 55.6 | 114.7 | 294.8 | 215.3 | 324.5 | chr22:15462931-15464137 | 734 |
| 1.6694783 | 22.2 | 68.1 | 64.4 | 89.5 | 121 | 281.6 | chr14:75113003-75114372 | 1005 |
| −1.242768 | 127.3 | 184.9 | 169.9 | 386.3 | 532.1 | 222.5 | chr1:38045876-38047629 | 693 |
| NA | 0 | 0 | 0 | 33.1 | 22.5 | 138.3 | chr3:14418953-14418987 | −139 |
| −2.2522507 | 32.6 | 43.1 | 41.8 | 190 | 118 | 251.8 | chr17:25586887-25587359 | −282 |
| −2.5864981 | 10.4 | 20.9 | 0 | 39.1 | 43.9 | 105 | chr22:41308070-41308175 | −161 |
| −1.8706008 | 13.3 | 11.1 | 43.5 | 101.4 | 81.3 | 65.6 | chr18:14169393-14169835 | 519 |
| −1.8349177 | 25.2 | 41.7 | 75.3 | 156.3 | 127.5 | 223.5 | chr1:208024525-208025081 | −290 |
| −2.0358306 | 57.7 | 62.6 | 15.9 | 206.8 | 101.4 | 250.3 | chr2:47396582-47397684 | −85 |
| −0.7308628 | 253.1 | 265.6 | 267.8 | 525.3 | 449 | 331 | chr1:101133936-101134618 | 12 |
| −2.0474787 | 5.9 | 11.1 | 36.8 | 62.8 | 64.7 | 94.9 | chr7:120415693-120416161 | −753 |
| −2.7131396 | 35.5 | 16.7 | 0 | 111.8 | 84.2 | 146.3 | chr9:37581503-37583711 | 29 |
| −4.0096586 | 8.9 | 12.5 | 44.4 | 64.8 | 73 | 206.9 | chr1:172103567-172103939 | −2306 |
| −2.0598675 | 59.2 | 44.5 | 44.4 | 175.1 | 201.7 | 240.7 | chr3:24510811-24511296 | 217 |
| −2.7381929 | 25.2 | 44.5 | 0.8 | 121.7 | 125.2 | 223.5 | chr18:48121097-48122140 | 1050 |
| −1.0520518 | 100.6 | 132.1 | 102.1 | 246.3 | 249.1 | 198.8 | chr16:66252442-66252988 | 364 |
| −4.0096586 | 8.9 | 12.5 | 0 | 64.8 | 73 | 206.9 | chr1:172103567-172103939 | −1964 |
| −2.0871732 | 38.5 | 52.8 | 25.9 | 202.8 | 87.8 | 207.4 | chr18:27777050-27777589 | −230 |
| −1.50294 | 28.1 | 18.1 | 31 | 56.4 | 56.9 | 105.5 | chr8:59069082-59071335 | 542 |
| −1.2950287 | 42.9 | 32 | 37.7 | 80.1 | 90.2 | 106 | chr8:99375539-99376080 | −12 |
| −1.7515441 | 22.2 | 18.1 | 10.9 | 46 | 62.3 | 64.1 | chr19:57082732-57083410 | −70 |
| −3.1457486 | 28.1 | 29.2 | 34.3 | 311.6 | 162.5 | 336.6 | chr9:132990253-132990933 | −208 |
| −2.2333973 | 31.1 | 44.5 | 49.4 | 179.1 | 104.4 | 304.3 | chr20:25011377-25012103 | −973 |
| 1.96848238 | 700 | 685.5 | 221.8 | 176.1 | 175.6 | 59 | chr20:25012103-25014030 | −2299 |
| −0.4597895 | 269.3 | 268.3 | 268.6 | 343.3 | 472.8 | 292.7 | chr19:63559791-63561351 | −3894 |
| −1.9476723 | 31.1 | 19.5 | 25.9 | 52.9 | 155.4 | 86.8 | chr19:55063866-55065091 | −1848 |
| −1.4445973 | 171.7 | 175.2 | 77 | 485.8 | 293.6 | 374.4 | chr7:127458469-127460282 | −1137 |
| −3.1963634 | 25.2 | 47.3 | 5 | 294.3 | 117.4 | 298.7 | chr7:65083798-65084603 | 481 |
| −0.7308628 | 253.1 | 265.6 | 267.8 | 525.3 | 449 | 331 | chr1:101133936-101134618 | −1271 |
| −1.7790991 | 31.1 | 45.9 | 51.9 | 137 | 81.9 | 223.5 | chr4:101089810-101091425 | −3715 |
| −1.0934136 | 115.4 | 147.4 | 241 | 257.2 | 448.4 | 369.4 | chr14:22595311-22597072 | 396 |
| −3.8052503 | 13.3 | 1.4 | 0 | 49 | 34.4 | 122.1 | chr6:53767171-53767707 | −297 |
| −3.3375249 | 1.5 | 5.6 | 6.7 | 31.2 | 22.5 | 85.8 | chrX:153279810-153279891 | −61 |
| −1.5171492 | 90.3 | 83.4 | 75.3 | 290.4 | 192.2 | 230.1 | chr5:946113-946722 | −2014 |
| −2.8128405 | 3 | 19.5 | 0 | 54.4 | 42.1 | 61.6 | chr7:23188528-23188950 | 769 |
| −2.737987 | 17.8 | 16.7 | 0.8 | 52.9 | 46.9 | 135.7 | chr16:88153191-88154446 | −772 |
| −3.7946811 | 5.9 | 1.4 | 2.5 | 29.7 | 22.5 | 83.8 | chr3:186454502-186454716 | −78 |
| −2.462665 | 35.5 | 82 | 0 | 197.9 | 143.5 | 306.3 | chr4:140696739-140698095 | −390 |
| −1.5735942 | 116.9 | 73.7 | 81.2 | 204.8 | 275.2 | 329 | chr9:135922006-135922995 | 462 |
| −0.9998482 | 150.9 | 158.5 | 165.7 | 428.9 | 293.6 | 227.6 | chr16:387223-387870 | 354 |
| −2.8467375 | 3 | 2.8 | 108.8 | 262.7 | 392.7 | 169 | chr1:240753659-240753941 | 821 |
| −2.718571 | 13.3 | 12.5 | 25.9 | 78.7 | 52.2 | 209.4 | chr11:124296093-124296718 | 2050 |
| −2.1083366 | 37 | 33.4 | 7.5 | 91 | 81.9 | 163 | chr2:190356680-190357846 | 79 |
| −3.2311252 | 22.2 | 27.8 | 0 | 171.2 | 71.2 | 227.1 | chr10:29738004-29738472 | −268 |
| −2.5914465 | 5.9 | 11.1 | 38.5 | 64.8 | 86 | 183.7 | chr2:2362154-2363996 | 623 |
| −1.1813476 | 88.8 | 75.1 | 27.6 | 105.9 | 158.4 | 170 | chr3:181802743-181803619 | 570 |
| −2.7703211 | 48.8 | 45.9 | 0 | 239.4 | 121.6 | 285.1 | chr2:202948965-202949836 | 106 |
| −2.0605955 | 41.4 | 33.4 | 16.7 | 93.5 | 88.4 | 199.8 | chr3:123715709-123716656 | 292 |
| −4.1909599 | 5.9 | 2.8 | 0 | 49 | 19.6 | 90.3 | chr2:96364785-96365713 | 39 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| -0.9559283 | 145 | 84.8 | 175.7 | 238.9 | 342.3 | 205.4 | chr10:38423338-38424055 | 411 |
| -1.9296915 | 63.6 | 64 | 28.5 | 141 | 118.6 | 335.1 | chr17:2361764-2362095 | 21 |
| -1.9688431 | 31.1 | 30.6 | 16.7 | 78.7 | 68.2 | 160 | chr22:38904187-38904830 | 634 |
| -3.3142294 | 26.6 | 8.3 | 0.8 | 105.4 | 73.6 | 176.1 | chrX:153908041-153909217 | 372 |
| -2.4889934 | 5.9 | 4.2 | 0 | 15.8 | 20.2 | 20.7 | chr16:14172220-1417744 | 1864 |
| -4.712718 | 3 | 4.2 | 0 | 46.5 | 30.8 | 111.3 | chr10:27484116-27485589 | -1525 |
| -1.4735075 | 29.6 | 109.8 | 37.7 | 134.6 | 195.7 | 161.5 | chr17:37526941-37528539 | -832 |
| -3.8131489 | 5.9 | 8.3 | 0 | 59.9 | 33.2 | 106.5 | chr12:6995299-6995502 | 703 |
| -1.9179158 | 40 | 40.3 | 54.4 | 126.1 | 222.4 | 160.5 | chr5:138658388-138658937 | 1353 |
| -3.106071 | 20.7 | 8.3 | 0 | 53.9 | 46.9 | 148.9 | chr6:4079263-4080712 | 1409 |
| -1.0010979 | 102.1 | 158.5 | 67.8 | 169.2 | 241.4 | 246.7 | chr21:44486909-44487692 | 843 |
| -1.908232 | 79.9 | 73.7 | 18.4 | 147.9 | 146.5 | 351.2 | chr7:98578994-98579990 | -2038 |
| -1.2954559 | 19.2 | 19.5 | 25.1 | 64.8 | 46.9 | 44.9 | chr19:52050366-52050962 | 167 |
| -2.3703684 | 32.6 | 23.6 | 17.6 | 104.9 | 71.8 | 204.9 | chr6:87753177-87753527 | -4621 |
| -5.281957 | 1.5 | 2.8 | 0 | 50 | 32 | 85.3 | chr5:140410588-140412511 | 224 |
| -2.945192 | 32.6 | 34.8 | 0 | 137 | 125.8 | 256.3 | chr5:137829787-137830063 | 387 |
| -3.0063883 | 13.3 | 33.4 | 20.9 | 175.1 | 106.2 | 261.9 | chr1:113062737-113063644 | 846 |
| -1.7446192 | 54.8 | 87.6 | 64.4 | 280 | 150.1 | 262.9 | chr17:9490007-9491087 | -3717 |
| -1.1183238 | 40 | 69.5 | 38.5 | 105.4 | 114.5 | 101.4 | chr22:42651124-42651247 | 873 |
| -2.2098865 | 16.3 | 26.4 | 29.3 | 81.1 | 52.2 | 199.8 | chr10:72638544-72639616 | 234 |
| -3.9093338 | 10.4 | 1.4 | 0 | 24.2 | 35 | 118.1 | chr10:72642748-72644383 | -3223 |
| 2.76749439 | 288.6 | 173.8 | 230.1 | 20.8 | 61.7 | 19.2 | chr3:187766910-187768400 | 1262 |
| -1.5604501 | 50.3 | 36.2 | 24.3 | 142.5 | 92.5 | 91.8 | chr14:91483324-91484336 | -3505 |
| -2.017848 | 99.2 | 100.1 | 17.6 | 294.3 | 160.7 | 423.4 | chr5:68425788-68426984 | -31 |
| -0.9727208 | 121.4 | 148.8 | 122.2 | 234.5 | 220.7 | 314.9 | chr6:76368925-76369365 | 813 |
| -2.6478581 | 7.4 | 13.9 | 7.5 | 63.8 | 35 | 81.7 | chr14:77296463-77297457 | 804 |
| -2.5803532 | 23.7 | 18.1 | 0 | 84.6 | 53.4 | 112 | chr13:48447252-48448068 | 315 |
| -2.1643159 | 77 | 50.1 | 76.2 | 207.8 | 476.9 | 226.6 | chr8:109867923-109870180 | -388 |
| -2.4100839 | 26.6 | 30.6 | 28.5 | 138.5 | 105.6 | 211.4 | chr2:232490915-232499201 | -105 |
| -1.7790GG9 | 57.7 | 00.G | 55.2 | 193.9 | 134.1 | 33G.1 | chr4:104009348-104010163 | 145 |
| -2.402719 | 13.3 | 36.2 | 88.7 | 305.7 | 132.9 | 292.2 | chr8:59485934-59487777 | 180 |
| -1.3526772 | 106.6 | 100.1 | 107.1 | 180.1 | 396.2 | 225.1 | chr11:176960089-176962465 | 479 |
| -2.8022253 | 10.4 | 4.2 | 17.6 | 38.6 | 66.4 | 119.6 | chr3:10337001-10337734 | 355 |
| -2.8196376 | 19.2 | 20.9 | 0 | 87.6 | 49.2 | 146.3 | chr11:71176230-71176787 | 488 |
| -3.907805 | 19.2 | 12.5 | 0 | 158.8 | 85.4 | 231.6 | chr3:75566392-75566949 | 304 |
| -2.6577414 | 29.6 | 40.3 | 0 | 199.4 | 87.8 | 153.9 | chr19:60848043-60848339 | 286 |
| -4.5523946 | 0 | 2.8 | 0 | 7.9 | 35.6 | 22.2 | chr4:89731781-89733576 | 1394 |
| -1.1247508 | 108 | 136.3 | 156.5 | 299.3 | 233.1 | 341.6 | chr1:94656622-94657622 | 9 |
| -1.6699357 | 79.9 | 80.6 | 35.1 | 86.1 | 395 | 141.3 | chr8:96028586-96031576 | 602 |
| -0.3286991 | 248.6 | 248.9 | 272 | 298.3 | 368.9 | 299.2 | chr1:145867300-145868004 | 710 |
| -2.2007264 | 31.1 | 68.1 | 46 | 194.9 | 147.1 | 325.5 | chr1:144537553-144538257 | 523 |
| -2.2007264 | 31.1 | 68.1 | 46 | 194.9 | 147.1 | 325.5 | chr3:102762393-102763620 | 555 |
| -1.4956952 | 102.1 | 95.9 | 77 | 211.7 | 298.4 | 265.4 | chr19:2407869-2408631 | -395 |
| -2.1637662 | 19.2 | 33.4 | 10 | 115.8 | 89 | 75.7 | chr6:89883316-89884323 | -292 |
| -1.4126585 | 74 | 65.3 | 141.4 | 169.2 | 310.2 | 267.9 | chr7:53282368-53282654 | 700 |
| -2.3632947 | 31.1 | 68.1 | 33.5 | 213.2 | 117.4 | 352.2 | chr20:20294035-20294960 | -113 |
| -2.2393599 | 32.6 | 30.6 | 0.8 | 87.1 | 65.2 | 149.9 | chr5:140756239-140758980 | -2267 |
| 1.86545184 | 953.1 | 878.7 | 789.2 | 200.8 | 420.6 | 97.9 | chr5:140761789-140763388 | -5094 |
| -1.1049133 | 121.4 | 126.5 | 89.5 | 227.1 | 210 | 288.6 | chr10:71834257-71835136 | -115 |
| 3.1424816 | 40 | 16.7 | 17.6 | 196.4 | 80.7 | 379 | chrX:133334892-133336102 | 830 |
| -1.777551 | 54.8 | 51.4 | 0 | 110.3 | 101.4 | 152.4 | | 490 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| -3.4338965 | 1.5 | 4.2 | 17.8 | 26.1 | 17.7 | chr16:2778486-2789030 | 272 |
| -2.8310321 | 29.6 | 22.2 | 106.4 | 69.4 | 192.8 | chr9:90340169-90340415 | 453 |
| -1.8646013 | 34 | 52.8 | 127.1 | 179.7 | 198.3 | chr8:74953609-74954084 | -182 |
| -2.9635687 | 10.4 | 19.5 | 70.2 | 65.8 | 169 | chr19:53947059-53948851 | -3200 |
| -1.3047325 | 127.3 | 155.7 | 395.7 | 564.7 | 290.6 | chr1:1699790-1701349 | -800 |
| -3.5555187 | 7.4 | 8.3 | 51.9 | 42.7 | 99.4 | chr19:5854880-5855114 | -854 |
| -3.3219281 | 3 | 1.4 | 13.9 | 16 | 14.1 | chr20:35965520-35965800 | 748 |
| -1.9786723 | 29.6 | 26.4 | 93.5 | 83 | 192.8 | chr4:74938130-74938488 | 433 |
| -3.0942004 | 41.4 | 57 | 301.8 | 118.6 | 470.3 | chr17:1340737-1342143 | 282 |
| -2.3067644 | 63.6 | 77.9 | 406.1 | 150.7 | 474.8 | chr16:65741109-65742098 | 800 |
| -1.2270871 | 121.4 | 132.1 | 274.5 | 244.4 | 384 | chr1:45642072-45643505 | 960 |
| -3.4743232 | 5.9 | 12.5 | 63.3 | 40.3 | 100.9 | chr9:135271877-135272157 | -4923 |
| -3.0904422 | 7.4 | 9.7 | 104.9 | 35.6 | 126.1 | chr22:31200323-31200989 | -567 |
| -1.2409001 | 139.1 | 137.6 | 354.2 | 443.7 | 295.2 | chr19:54266199-54267652 | 1085 |
| -1.6503278 | 88.8 | 90.4 | 309.2 | 346.4 | 321.9 | chr20:48845060-48845888 | 601 |
| -4.0096586 | 8.9 | 12.5 | 64.8 | 73 | 206.9 | chr1:172103567-172103939 | -3775 |
| -4.0096586 | 8.9 | 12.5 | 64.8 | 73 | 206.9 | chr1:172103567-172103939 | -3089 |
| -2.7527823 | 5.9 | 5.6 | 56.9 | 100.8 | 184.7 | chr7:158313458-158316700 | 1 |
| -1.5669125 | 20.7 | 37.5 | 111.8 | 89.6 | 132.2 | chr3:139635893-139636261 | -27 |
| 2.25748849 | 6039.5 | 3655.3 | 910.2 | 2649 | 206.9 | chr3:139636275-139637284 | 675 |
| -3.3630312 | 25.2 | 13.9 | 100.9 | 65.2 | 236.2 | chr15:32181330-32181477 | -162 |
| -2.0570599 | 84.4 | 91.8 | 441.2 | 381.4 | 304.3 | chr2:191586479-191587593 | 185 |
| -2.0941274 | 69.6 | 68.1 | 162.7 | 121 | 340.1 | chr7:7288368-7289746 | -72 |
| -2.3149779 | 16.3 | 23.6 | 84.6 | 50.4 | 134.2 | chr6:136612674-136613128 | 241 |
| -0.9725796 | 186.5 | 194.7 | 375.5 | 318.5 | 343.1 | chr8:124354980-124356255 | 111 |
| -4.712718 | 3 | 4.2 | 46.5 | 30.8 | 111.5 | chr10:27484116-27485589 | 1130 |
| -2.4405062 | 25.2 | 32 | 85.6 | 86.6 | 138.3 | chr1:124048812-124049761 | -359 |
| -1.4475276 | 77 | 61.2 | 210.7 | 127.5 | 235.1 | chr13:110164497-110166567 | 2449 |
| -1.8200041 | 31.1 | 30.6 | 118.7 | 67 | 123.6 | chr14:57781183-57781483 | -12 |
| -2.5923195 | 7.4 | 5.6 | 20.3 | 52.8 | 25.2 | chr8:124287379-124288229 | -3640 |
| -2.2691407 | 7.4 | 20.9 | 95.5 | 73.6 | 152.9 | chr13:69579830-69580842 | 991 |
| -1.7898003 | 62.2 | 68.1 | 158.3 | 110.9 | 274 | chr1:61490350-61491360 | 853 |
| -2.6813831 | 53.3 | 54.2 | 205.8 | 125.2 | 541.4 | chr1:148080887-148081129 | -66 |
| -3.0202432 | 1.5 | 5.6 | 33.6 | 54.6 | 98.4 | chr22:40816884-40817452 | -334 |
| -2.4180856 | 41.4 | 43.1 | 307.2 | 145.3 | 321.4 | chr16:66007420-66008210 | 63 |
| -4.7359493 | 1.5 | 5.6 | 32.6 | 27.9 | 128.7 | chr10:79463176-79463665 | -159 |
| -2.6355364 | 35.5 | 59.8 | 162.7 | 102 | 327.5 | chr4:172971378-172972638 | 859 |
| -2.4130797 | 62.2 | 94.5 | 175.1 | 199.3 | 460.2 | chr1:142496878-142498014 | -3742 |
| -3.4535155 | 8.9 | 22.2 | 118.7 | 64.1 | 157.9 | chr8:101226755-101227488 | 131 |
| -2.7618798 | 53.3 | 109.8 | 316.6 | 184.5 | 610.6 | chrX:19049642-19051277 | 139 |
| -2.2502712 | 74 | 62.6 | 233 | 141.8 | 410.7 | chr11:118797083-118798977 | 1034 |
| -2.2323675 | 22.2 | 22.2 | 90.5 | 59.3 | 145.3 | chr16:49742807-49743196 | -317 |
| -2.9283302 | 11.8 | 11.1 | 99.4 | 84.8 | 175.1 | chr12:54980048-54980250 | 293 |
| -2.6066576 | 32.6 | 33.4 | 89.5 | 85.4 | 227.1 | chr7:127015851-127017121 | -4438 |
| -3.1212941 | 28.1 | 19.5 | 135 | 75.3 | 203.9 | chr2:102758182-102758906 | 370 |
| -1.5812139 | 72.5 | 48.7 | 191.9 | 117.4 | 113.5 | chr6:116528786-116528920 | 162 |
| -2.9776747 | 19.2 | 26.4 | 168.7 | 77.7 | 119.1 | chr2:169927538-169928162 | -482 |
| -1.7768229 | 87.3 | 93.2 | 258.2 | 425.3 | 445.6 | chr10:105871708-105872513 | 305 |
| -2.7277158 | 54.8 | 25 | 164.7 | 261 | 102.9 | chr3:39422667-39423758 | 5 |
| -1.1103379 | 103.6 | 148.8 | 206.8 | 225.4 | 291.7 | chr11:67836758-67837661 | 526 |
| -4.337035 | 7.4 | 9.7 | 81.6 | 51.6 | 212.4 | chr2:37312352-37312721 | 259 |

TABLE 14-continued

Comprehensive DNA Methylation and K27 Profiles of CD44+ Nulliparous and Parous Breast Epithelial Cells

| | | | | | | |
|---|---|---|---|---|---|---|
| −2.6674247 | 8.9 | 19.5 | 20.9 | 113.3 | 51 | 148.9 | chr12:21818823-21819383 | −89 |
| −2.8723649 | 20.7 | 29.2 | 0 | 77.2 | 94.9 | 193.3 | chr12:102882994-102884798 | 174 |
| −3.0181044 | 23.7 | 11.1 | 33.5 | 155.3 | 117.4 | 280.6 | chr6:41149163-41150185 | 990 |
| −2.0966165 | 62.2 | 66.7 | 39.3 | 268.6 | 150.1 | 300.7 | chr5:36277119-36278680 | −242 |
| −2.7136151 | 38.5 | 48.7 | 0 | 149.9 | 160.2 | 261.9 | chr13:100124173-100124784 | 626 |
| −1.462972 | 47.4 | 51.4 | 41.8 | 91.5 | 113.9 | 182.2 | chr6:137282974-137285565 | −825 |
| −3.6795932 | 19.2 | 11.1 | 0.8 | 129.1 | 107.4 | 162 | chr1:39976767-39977801 | 168 |
| −3.2052356 | 44.4 | 41.7 | 0 | 273.1 | 116.3 | 404.7 | chr7:150846378-150847378 | 1065 |
| −2.6375424 | 53.3 | 61.2 | 0 | 194.4 | 141.2 | 376.9 | chr3:3143593-3144306 | 350 |
| −2.6043858 | 41.4 | 25 | 0 | 100.9 | 78.9 | 224 | chr9:137937559-137938335 | 879 |
| −2.4094714 | 14.8 | 8.3 | 40.2 | 79.1 | 67 | 190.2 | chr7:74862754-74862842 | −40 |
| −2.0351505 | 50.3 | 64 | 41.8 | 232 | 156 | 251.8 | chr7:139521558-139523051 | 906 |
| −2.1314992 | 77 | 76.5 | 43.5 | 306.7 | 148.3 | 408.2 | chr10:101481403-101482095 | −198 |
| −4.0782756 | 22.2 | 5.6 | 0 | 94 | 132.9 | 242.7 | chr11:101722337-101723935 | −39 |
| −2.466318 | 10.4 | 12.5 | 15.1 | 51.4 | 48.6 | 110 | chr12:46385401-46386438 | 122 |
| −5.0288811 | 0 | 0 | 1.7 | 4.9 | 7.7 | 42.9 | chr7:100046015-100046665 | −1320 |
| −3.7173206 | 16.3 | 19.5 | 0.8 | 173.6 | 61.1 | 246.7 | chr10:88505346-88507361 | −22 |
| −2.7539468 | 11.8 | 13.9 | 36.8 | 110.8 | 87.8 | 223 | chr2:161057184-161058118 | 900 |
| −1.3996827 | 69.6 | 111.2 | 143.9 | 286.9 | 281.2 | 288.6 | chr2:161058118-161059112 | −64 |
| −1.336581 | 171.7 | 164.1 | 326.4 | 717.8 | 438.9 | 515.7 | chr6:136913237-136913751 | −9 |
| −2.9399278 | 22.2 | 25 | 0 | 144 | 52.2 | 166 | chr9:36247614-36248633 | 367 |
| −3.8823309 | 19.2 | 27.8 | 0 | 237.9 | 159 | 296.2 | chr19:58662506-58663652 | 279 |
| −3.8012329 | 23.7 | 11.1 | 29.3 | 259.7 | 156.6 | 477.3 | chr4:7434261 3-74344052 | 34 |
| −3.5510621 | 4.4 | 7 | 0.8 | 26.2 | 25.5 | 91.3 | chr16:70684641-70685493 | −52 |
| −2.8061331 | 35.5 | 32 | 0 | 78.2 | 99.7 | 294.2 | chr9:134272100-134272248 | −3257 |
| −1.9402461 | 31.1 | 44.5 | 31 | 167.7 | 81.9 | 159.5 | chr17:35036618-35037171 | 190 |
| −2.1347644 | 48.8 | 76.5 | 73.6 | 323 | 121.6 | 428.9 | chr1:28847331-28848288 | 111 |
| −2.6416674 | 31.1 | 37.5 | 0 | 133.6 | 79.5 | 215 | chr8:24869128-24869944 | 512 |
| −1.5180041 | 62.2 | 27.8 | 27.6 | 107.8 | 131.1 | 97.9 | chr5:140767137-140768305 | −5205 |
| −1.586849 | 37 | 30.6 | 34.3 | 99.9 | 66.4 | 139.8 | chr4:166252811-166253871 | 133 |
| −0.7305625 | 142.1 | 130.7 | 228.5 | 253.3 | 339.3 | 239.2 | chr21:36429360-36430629 | 862 |
| −3.0750303 | 20.7 | 36.2 | 0 | 143 | 110.9 | 225.6 | chr3:188870441-188871074 | 138 |
| −0.9638772 | 77 | 40.3 | 121.3 | 112.8 | 205.8 | 146.8 | chr3:112889 97-11289728 | 280 |
| −2.2973409 | 35.5 | 25 | 25.9 | 213.2 | 68.2 | 143.3 | chr3:141136631-141138302 | 750 |
| −2.8898019 | 29.6 | 34.8 | 10.9 | 98.9 | 108 | 351.2 | chr4:122837192-122838355 | −176 |
| −3.4816787 | 5.9 | 16.7 | 0.8 | 60.8 | 55.8 | 144.8 | chr17:52688575-52689878 | 297 |
| −1.7759241 | 65.1 | 77.9 | 67.8 | 246.3 | 133.5 | 342.1 | chr17:16059733-16060354 | −1190 |
| −1.4735075 | 29.6 | 109.8 | 37.7 | 134.6 | 195.7 | 161.5 | chr17:37526941-37528539 | −654 |
| −2.1036226 | 44.4 | 47.3 | 11.7 | 160.8 | 81.3 | 202.3 | chr21:37366517-37367021 | 204 |
| −2.2301657 | 75.5 | 64 | 21.8 | 266.1 | 183.9 | 306.8 | chr16:559119-560435 | −227 |
| −2.4262369 | 57.7 | 62.6 | 0 | 199.8 | 109.7 | 337.1 | chr1:94146578-94147305 | 659 |
| −1.462698 | 177.6 | 162.7 | 72.8 | 330.4 | 279.4 | 528.8 | chr22:37426056-37427896 | −4776 |
| −3.086201 | 40 | 54.2 | 0 | 241.4 | 108 | 450.6 | chr2:168812189-168812780 | −133 |
| −2.369396 | 14.8 | 13.9 | 0 | 40.1 | 42.1 | 66.1 | chr8:125556531-125556795 | 475 |
| −2.0176299 | 68.1 | 80.6 | 77 | 352.7 | 156 | 405.2 | chr3:198179529-198180549 | 62 |
| −3.4786949 | 34 | 43.1 | 0 | 345.3 | 118.6 | 395.6 | chr14:23095079-23095806 | 405 |
| −1.5904247 | 16.3 | 26.4 | 27.6 | 59.4 | 56.9 | 95.4 | chr7:88227226-88227535 | 692 |
| −3.0181044 | 23.7 | 11.1 | 33.5 | 155.3 | 117.4 | 280.6 | chr6:41149163-41150185 | −1508 |
| −1.5854307 | 142.1 | 147.4 | 121.3 | 378.9 | 443.7 | 410.2 | chr15:80341774-80342275 | −182 |
| −3.9259994 | 1.5 | 7 | 0 | 51 | 20.2 | 58 | chr5:140202264-140203050 | 1567 |
| −3.9259994 | 1.5 | 7 | 0 | 51 | 20.2 | 58 | chr5:140202264-140203050 | −4883 |

TABLE 14-continued

Comprehensive DNA Methylation and K27 Profiles of CD44+ Nulliparous and Parous Breast Epithelial Cells

| | | | | | | |
|---|---|---|---|---|---|---|
| -3.0042694 | 29.6 | 36.2 | 5.9 | 160.8 | 83 | 331.5 | chr1:93199572-93200087 | -162 |
| -1.2541206 | 60.7 | 86.2 | 108.8 | 164.7 | 166.7 | 278.5 | chr5:174803140-174804563 | -82 |
| -1.0608438 | 173.1 | 212.7 | 235.2 | 456.1 | 349.4 | 490 | chr2:173129298-173129874 | 562 |
| -1.6434677 | 34 | 44.5 | 55.2 | 134.1 | 91.3 | 192.3 | chr7:44890182-44891242 | 773 |
| -2.1718744 | 34 | 36.2 | 69.5 | 183.5 | 128.1 | 317.9 | chr3:101019136-101019893 | 144 |
| -2.4758841 | 16.3 | 38.9 | 20.1 | 115.3 | 83.6 | 220 | chr4:166347543-166348306 | -316 |
| -5.0495283 | 0 | 0 | 1.7 | 4.9 | 9.5 | 41.9 | chr19:10624744-10625488 | -820 |
| -2.6209908 | 35.5 | 36.2 | 0.8 | 136 | 102.6 | 207.4 | chr10:5747624-5748284 | 593 |
| -1.2390492 | 164.3 | 197.4 | 123 | 489.2 | 320.9 | 334 | chr13:27439454-27440249 | 1466 |
| 1.13421154 | 543.1 | 636.8 | 431 | 340.8 | 287.1 | 106 | chr13:27441173-27442153 | -346 |
| -2.5109782 | 81.4 | 41.7 | 32.6 | 237.9 | 129.9 | 519.7 | chr3:184628387-184629542 | -415 |
| -2.6669884 | 44.4 | 52.8 | 0.8 | 232.5 | 90.2 | 299.7 | chr16:88566501-88567348 | 436 |
| -2.821977 | 22.2 | 29.2 | 7.5 | 151.9 | 65.8 | 198.8 | chr8:48335679-48336716 | 103 |
| -1.1049133 | 121.4 | 126.5 | 89.5 | 227.1 | 210 | 288.6 | chr5:140761789-140763388 | -5365 |
| -1.518041 | 62.2 | 27.8 | 27.6 | 107.8 | 131.1 | 97.9 | chr5:140767137-140768305 | -232 |
| -1.998728 | 29.6 | 15.3 | 40.2 | 124.2 | 73.6 | 142.3 | chr5:6765119-6766185 | -2065 |
| -1.5568489 | 71 | 108.5 | 48.5 | 241.9 | 253.3 | 175.6 | chr3:52287415-52288201 | -109 |
| -4.2383379 | 1.5 | 11.1 | 1.7 | 98.9 | 43.3 | 127.7 | chr19:45414458-45416011 | 904 |
| -2.5787662 | 13.3 | 20.9 | 0.8 | 54.4 | 62.9 | 91.8 | chr4:320247-322161 | -391 |
| -3.9293454 | 7.4 | 2.8 | 11.7 | 27.7 | 37.4 | 90.3 | chr4:457393-458525 | 39 |
| -6.0382673 | 7.4 | 7 | 11.7 | 357.6 | 1233 | 125.1 | chr14:35858713-35859543 | 468 |
| -2.1375035 | 19.2 | 29.2 | 17.6 | 111.8 | 57.5 | 121.1 | chr10:75240511-75242139 | 23 |
| -1.7046444 | 66.6 | 70.9 | 25.9 | 138.5 | 118.6 | 275.5 | chr2:172087460-172089323 | 1280 |
| -1.5460566 | 65.1 | 48.7 | 87.9 | 193.9 | 138.8 | 256.3 | chr7:71937628-71938439 | 146 |
| -0.9968517 | 56.2 | 61.2 | 66.1 | 135.5 | 115.1 | 115.6 | chr14:57932746-57933153 | 553 |
| -2.5514567 | 25.2 | 11.1 | 0 | 53.4 | 53.4 | 106 | chr3:170348092-170348235 | -1402 |
| -0.8026708 | 309.3 | 328.1 | 415.9 | 781.1 | 622.8 | 433.4 | chr9:61323480-61324669 | 387 |
| -2.0103103 | 45.9 | 41.7 | 10 | 165.7 | 80.7 | 146.8 | chr16:30504431-30505558 | -483 |
| -2.8632507 | 32.6 | 48.7 | 16.7 | 245.4 | 90.8 | 376.9 | chr9:60827480-60828120 | -47 |
| -2.7206805 | 14.8 | 19.5 | 0 | 88.5 | 46.3 | 91.3 | chr9:123895516-123895954 | -29 |
| -2.8798875 | 16.3 | 13.9 | 0 | 72.7 | 35.6 | 114 | chr20:36868748-36869009 | 1117 |
| -2.1815735 | 1.5 | 4.2 | 17.6 | 29.2 | 42.7 | 33.8 | chr1:41722799-41723297 | -117 |
| -2.194594 | 17.8 | 18.1 | 42.7 | 92 | 90.2 | 177.6 | chr12:131134469-131135145 | -3 |
| -2.3763941 | 87.3 | 87.6 | 0.8 | 329.9 | 153 | 429.4 | chr19:44588464-44589366 | -411 |
| -2.4704646 | 13.3 | 8.3 | 23.4 | 67.8 | 53.4 | 128.2 | chr12:107478908-107479277 | -1331 |
| -1.2803564 | 69.6 | 66.7 | 68.6 | 210.7 | 147.7 | 139.3 | chr16:11742760-11743914 | 812 |
| -1.7446192 | 54.8 | 87.6 | 64.4 | 280 | 150.1 | 262.9 | chr1:113062737-113063644 | -1521 |
| -3.1860375 | 16.3 | 27.8 | 30.1 | 168.2 | 108.5 | 398.6 | chr12:70951068-70951795 | -1298 |
| -2.6817564 | 40 | 43.1 | 0 | 135.5 | 105 | 292.7 | chr2:74914496-74914771 | 1344 |
| -1.4865176 | 53.3 | 45.9 | 51.9 | 142.5 | 127.5 | 153.4 | chr10:92605767-92606896 | 1320 |
| -2.2396418 | 19.2 | 11.1 | 46.9 | 89 | 78.3 | 197.3 | chr6:16237532-16238190 | 566 |
| -5.9954845 | 1.5 | 0 | 0 | 31.2 | 23.1 | 41.4 | chr20:55356631-55357125 | -2673 |
| -2.2691407 | 7.4 | 20.9 | 38.5 | 95.5 | 73.6 | 152.9 | chr13:69579830-69580842 | 124 |
| -2.1083366 | 37 | 33.4 | 7.5 | 91 | 81.9 | 163 | chr2:190356680-190357846 | 208 |
| -3.2292112 | 54.8 | 23.6 | 0 | 241.9 | 164.3 | 329 | chr5:174083372-174084268 | -360 |
| -1.3255446 | 77 | 137.6 | 112.1 | 217.7 | 210 | 391.1 | chr1:232575375-232576461 | -133 |
| -2.8853773 | 13.3 | 15.3 | 25.9 | 77.2 | 148.9 | 176.6 | chr11:95762164-95763183 | 58 |
| -1.9202624 | 66.6 | 64 | 67 | 182 | 150.1 | 415.8 | chr6:69880068-69881260 | 346 |
| -1.4607323 | 69.6 | 66.7 | 55.2 | 241.9 | 112.1 | 173.1 | chr7:5976730-5977260 | -155 |
| -3.9728409 | 17.8 | 7 | 0 | 138 | 85.4 | 166 | chr3:172660843-172661907 | -829 |
| -1.7790991 | 31.1 | 45.9 | 51.9 | 137 | 81.9 | 223.5 | chr4:101089810-101091425 | -82 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| -1.819944 | 82.9 | 79.3 | 0.8 | 214.2 | 141.8 | 219.5 | chr5:137638010-137638805 | -255 |
| -1.843 0853 | 77 | 94.5 | 41 | 145.4 | 161.9 | 455.1 | chr12:123961556-123964857 | 2324 |
| -2.3381617 | 26.6 | 20.9 | 28.5 | 125.6 | 73 | 185.7 | chr6:158508581-158509933 | 0 |
| -2.0705279 | 99.2 | 111.2 | 87 | 475.4 | 180.9 | 592.9 | chr19:12522799-12524057 | -111 |
| -1.4607323 | 69.6 | 66.7 | 55.2 | 241.9 | 112.1 | 173.1 | chr7:5976730-5977260 | -155 |
| -3.3718314 | 16.3 | 19.5 | 0 | 126.6 | 45.7 | 198.3 | chr2:52674694-52675148 | -5222 |
| -2.2953531 | 208.7 | 237.8 | 125.5 | 993.8 | 412.2 | 1401.8 | chr3:127118156-127118714 | 302 |
| -1.8983647 | 40 | 47.3 | 71.1 | 230.5 | 119.8 | 240.2 | chr17:17340140-17341530 | -403 |
| -0.9205836 | 267.9 | 312.8 | 323.9 | 678.2 | 616.3 | 417.8 | chr4:149581871-149583135 | 590 |
| -2.2286979 | 69.6 | 89 | 48.5 | 408.6 | 162.5 | 399.6 | chr10:44774772-44775285 | -196 |
| -1.0091882 | 105.1 | 89 | 48.5 | 113.3 | 166.1 | 208.9 | chr2:73374306-73375017 | -480 |
| -1.7487279 | 41.4 | 41.7 | 58.6 | 172.1 | 110.3 | 193.8 | chr8:23442646-23443628 | 830 |
| -2.0498341 | 37 | 25 | 13.4 | 75.7 | 76.5 | 160 | chr2:51758666-51759945 | 100 |
| -2.6734437 | 22.2 | 13.9 | 0 | 49.5 | 58.7 | 122.1 | chr1:1499305-1499413 | 766 |
| -1.9773719 | 37 | 36.2 | 76.2 | 190 | 115.7 | 282.6 | chr19:50836671-50837312 | -2482 |
| -3.659749 | 7.4 | 5.6 | 0 | 34.6 | 30.3 | 99.4 | chr7:149651099-149651807 | -84 |
| -2.2080672 | 42.9 | 16.7 | 19.2 | 95.5 | 95.5 | 173.1 | chr1:203985722-203986645 | -199 |
| -1.1388178 | 355.2 | 440.8 | 410.9 | 938.9 | 1035 | 684.2 | chr7:128861549-128862809 | 670 |
| -2.4846689 | 37 | 50.1 | 82.9 | 318.1 | 149.5 | 483.9 | chr12:42515972-42516914 | 215 |
| -1.6367889 | 65.1 | 48.7 | 111.3 | 211.2 | 256.2 | 232.6 | chr11:34893820-34894405 | -140 |
| -2.8588336 | 4.4 | 9.7 | 20.9 | 74.7 | 51 | 128.2 | chr7:39571790-39572230 | -523 |
| -1.8815689 | 56.2 | 101.5 | 83.7 | 309.7 | 169.6 | 410.2 | chr2:38904210-38905163 | -393 |
| -2.7324813 | 26.6 | 23.6 | 36.8 | 223.1 | 157.8 | 197.3 | chr20:39679694-39680631 | 385 |
| -3.3819502 | 29.6 | 38.9 | 0 | 124.2 | 159 | 430.9 | chr5:79367723-79367116 | -327 |
| -1.9688717 | 22.2 | 25 | 30.1 | 179.6 | 63.5 | 59.5 | chr2:25955020-25955486 | -437 |
| -4.1541231 | 7.4 | 2.8 | 0 | 57.9 | 37.4 | 86.3 | chr3:12857617-12858180 | -949 |
| -0.5496052 | 174.6 | 184.9 | 181.6 | 308.7 | 279.4 | 203.9 | chrX:37316042-37317136 | 849 |
| -1.9310339 | 74 | 58.4 | 82.9 | 258.7 | 132.9 | 429.4 | chr4:156807807-156808813 | 999 |
| -2.2705897 | 11.8 | 5.6 | 31.8 | 59.4 | 59.9 | 118.1 | chr19:50039312-50040459 | -1347 |
| -2.4864106 | 72.5 | 89 | 0.8 | 279.5 | 170.8 | 459.2 | chr5:177234751-177235120 | 68 |
| -1.8467774 | 19.2 | 12.5 | 20.9 | 56.4 | 44.5 | 88.3 | chrX:119267968-119269954 | 327 |
| -3.4947647 | 14.8 | 2.8 | 0 | 58.9 | 35.6 | 103.9 | chr11:111601777-111603077 | 130 |
| -4.0096586 | 8.9 | 12.5 | 0 | 64.8 | 73 | 206.9 | chr1:172103567-172103939 | -362 |
| -1.7704203 | 54.8 | 41.7 | 56.1 | 180.1 | 198.7 | 141.8 | chr7:40402797-40404705 | -2581 |
| -3.0661832 | 11.8 | 11.1 | 0 | 64.8 | 29.1 | 97.9 | chr17:77468493-77469175 | 498 |
| -1.5497884 | 40 | 55.6 | 59.4 | 146.9 | 105.6 | 201.3 | chr3:117646108-117646566 | 731 |
| -2.1036226 | 44.4 | 47.3 | 11.7 | 160.8 | 81.3 | 202.3 | chr21:37366517-37367021 | -671 |
| -2.3595545 | 14.8 | 36.2 | 36.8 | 143.5 | 73 | 234.1 | chr22:26526064-26526337 | 1286 |
| -2.5082347 | 50.3 | 51.4 | 46 | 247.8 | 142.4 | 450.1 | chr2:46622965-46623555 | -110 |
| -1.7068907 | 56.2 | 48.7 | 41 | 143 | 106.2 | 227.1 | chr3:137953219-137954785 | -67 |
| -1.7288312 | 35.5 | 77.9 | 36 | 120.2 | 277.6 | 97.4 | chr4:158216229-158217600 | 188 |
| -3.4261311 | 10.4 | 13.9 | 0.8 | 46.5 | 32.6 | 190.7 | chr19:37859285-37859498 | -1449 |
| -1.6207935 | 65.1 | 102.9 | 81.2 | 254.8 | 155.4 | 356.2 | chr1:54126633-54128453 | 498 |
| -2.7876187 | 17.8 | 18.1 | 37.7 | 181.1 | 102.6 | 224.5 | chr6:26232360-26233141 | -639 |
| -2.4704646 | 13.3 | 8.3 | 23.4 | 67.8 | 53.4 | 128.2 | chr12:107479908-107479277 | 203 |
| -2.8374959 | 3 | 5.6 | 11.7 | 26.2 | 45.7 | 73.2 | chr11:20647906-20649745 | 1114 |
| -1.8711834 | 32.6 | 36.2 | 35.1 | 90 | 67.6 | 222.5 | chr4:81405699-81405953 | -939 |
| -2.2353198 | 41.4 | 33.4 | 11.7 | 93.5 | 87.2 | 226.6 | chr11:69299211-69300090 | -298 |
| -3.4535155 | 8.9 | 22.2 | 0 | 118.7 | 64.1 | 157.9 | chr8:101226755-101227488 | -4893 |
| -3.3375249 | 1.5 | 5.6 | 6.7 | 31.2 | 22.5 | 85.8 | chrX:153279810-153279891 | -1965 |
| -1.5677287 | 28.1 | 19.5 | 70.3 | 121.2 | 116.3 | 112 | chr5:175156069-175157735 | 687 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| -3.6679519 | 4.4 | 7 | 0 | 45.5 | 26.7 | 72.7 | chr17:7236777-7237477 | 1440 |
| -2.3823846 | 32.6 | 48.7 | 11.7 | 117.2 | 90.2 | 277.5 | chr1:205884553-205885068 | -270 |
| -2.8209218 | 22.2 | 13.9 | 1.7 | 28.7 | 55.2 | 183.2 | chr1:221603381-221604032 | 461 |
| -2.3401532 | 42.9 | 20.9 | 24.3 | 114.3 | 79.5 | 252.3 | chr8:30361098-30362317 | 222 |
| -2.2251955 | 47.4 | 33.4 | 0 | 96.5 | 96.1 | 185.2 | chr6:17387787-17390446 | -1794 |
| -1.4513208 | 81.4 | 68.1 | 15.9 | 118.2 | 135.8 | 198.3 | chr22:38182740-38184472 | 336 |
| -2.445424 | 14.8 | 33.4 | 39.3 | 158.8 | 70 | 247.8 | chr20:41976417-41976945 | -224 |
| -1.2886196 | 112.5 | 136.3 | 54.4 | 219.6 | 252.7 | 268.4 | chr4:84151681-84153879 | -1774 |
| -2.2767323 | 74 | 73.7 | 0.8 | 217.2 | 157.8 | 344.6 | chr13:41432575-41433086 | 391 |
| -1.5831258 | 31.1 | 37.5 | 10 | 48 | 73 | 114.5 | chr6:108594394-108594662 | 574 |
| -2.2052977 | 29.6 | 36.2 | 38.5 | 144.4 | 81.3 | 255.3 | chr21:177964891-177965633 | -454 |
| -1.0520518 | 100.6 | 132.1 | 102.1 | 246.3 | 249.1 | 198.8 | chr16:66252442-66252988 | -496 |
| -2.5828971 | 22.2 | 37.5 | 33.5 | 151.9 | 79.5 | 327 | chrX:100070290-100071239 | -210 |
| -2.49863 | 20.7 | 18.1 | 11.7 | 71.2 | 49.2 | 165 | chr2:160362953-160363420 | -174 |
| -4.4994663 | 0 | 4.2 | 0 | 21.8 | 17.2 | 56 | chr3:198962742-198962808 | 1696 |
| -2.2577978 | 42.9 | 50.1 | 24.3 | 201.3 | 107.4 | 252.3 | chrX:48866194-48867383 | 235 |
| -2.7021566 | 17.8 | 29.2 | 17.6 | 116.2 | 63.5 | 240.7 | chr21:21292277-21292752 | 11 |
| -2.0909654 | 37 | 51.4 | 32.6 | 140.5 | 91.9 | 283.1 | chr7:90731941-90732530 | 517 |
| -2.2039577 | 38.5 | 34.8 | 18.4 | 111.3 | 87.2 | 224 | chr5:72147536-72148832 | 11 |
| -2.3772882 | 10.4 | 8.3 | 17.6 | 51.9 | 43.9 | 92.8 | chr15:32117365-32119241 | 292 |
| -4.5523946 | 0 | 2.8 | 0 | 7.9 | 35.6 | 22.2 | chr19:60848043-60848339 | -2574 |
| -4.0502548 | 0 | 4.2 | 9.2 | 30.2 | 48 | 143.8 | chr4:52598495-52599828 | 81 |
| -3.1589382 | 20.7 | 19.5 | 30.1 | 208.3 | 116.3 | 303.3 | chr8:73610742-73612986 | -315 |
| -2.4405062 | 25.2 | 32 | 0 | 85.6 | 86.6 | 138.3 | chr11:124048812-124049761 | 337 |
| -3.1188984 | 11.8 | 12.5 | 0 | 66.8 | 36.8 | 107.5 | chr10:49992633-49994217 | 140 |
| -2.5370128 | 65.1 | 77.9 | 17.6 | 305.2 | 140 | 486.9 | chr5:170779763-170780551 | 886 |
| -1.2239849 | 133.2 | 164.1 | 220.1 | 458.1 | 366 | 384.5 | chr6:79842674-79843629 | 1557 |
| -2.8061331 | 35.5 | 32 | 0 | 78.2 | 99.7 | 294.2 | chr9:134272100-134272248 | -132 |
| -4.0479632 | 31.1 | 26.4 | 0 | 264.7 | 217.1 | 469.3 | chr10:64950569-64952947 | 630 |
| -3.6839242 | 25.2 | 16.7 | 0 | 172.1 | 108 | 258.4 | chr1:205561009-205561733 | -68 |
| -1.0887481 | 91.8 | 79.3 | 92.9 | 130.1 | 240.2 | 191.2 | chr3:144164866-144166138 | -634 |
| -1.7807547 | 26.6 | 36.2 | 32.6 | 89.5 | 71.8 | 166.5 | chr20:52257844-52258058 | 43 |
| -2.2590026 | 48.8 | 52.8 | 26.8 | 228 | 98.5 | 288.1 | chr2:225749099-25750442 | 237 |
| -3.0871809 | 20.7 | 23.6 | 15.9 | 115.8 | 156.6 | 239.2 | chr22:36533152-36534596 | -26 |
| -2.7800201 | 38.5 | 45.9 | 35.1 | 249.8 | 133.5 | 437.5 | chr19:46460953-46462066 | 1279 |
| -2.1296385 | 56.2 | 83.4 | 34.3 | 271.1 | 179.1 | 310.8 | chr10:47974459-47975643 | -43 |
| -4.0680454 | 4.4 | 0 | 0 | 11.9 | 19 | 42.9 | chr11:133705808-133706195 | -1017 |
| -2.6813831 | 53.3 | 54.2 | 28.5 | 205.8 | 125.2 | 541.4 | chr1:148080887-148081129 | -66 |
| -3.2603687 | 11.8 | 11.1 | 0.8 | 27.7 | 94.9 | 104.5 | chr18:2837585-2838645 | 1088 |
| -2.0429034 | 25.2 | 18.1 | 59.4 | 129.1 | 110.9 | 183.2 | chr7:56087164-56087941 | -790 |
| -1.7781928 | 41.4 | 57 | 35.1 | 156.8 | 96.7 | 204.4 | chr4:89147136-89147841 | -355 |
| -1.9838447 | 47.4 | 50.1 | 61.9 | 193.4 | 119.2 | 317.9 | chr13:77169846-77170859 | -118 |
| -0.9860966 | 38.5 | 41.7 | 76.2 | 92 | 116.9 | 100.9 | chr14:92050029-92050735 | 505 |
| -1.164522 | 96.2 | 90.4 | 158.2 | 190.9 | 359.5 | 222.5 | chr22:40558128-40559086 | -444 |
| -2.5614616 | 26.6 | 40.3 | 83.7 | 106.8 | 608.6 | 173.6 | chr13:37680220-37682237 | 722 |
| -0.9998482 | 150.9 | 158.5 | 165.7 | 428.9 | 293.6 | 227.6 | chr6:387223-387870 | -4312 |
| -2.1809278 | 31.1 | 40.3 | 36 | 178.6 | 78.3 | 230.1 | chr1:42155512-42156733 | 961 |
| -2.0958962 | 54.8 | 57 | 37.7 | 249.3 | 103.2 | 286.6 | chr7:21096315-21097801 | 113 |
| -1.8349927 | 20.7 | 55.6 | 92.1 | 186 | 138.8 | 276 | chr15:63264100-63265046 | 43 |
| -2.5188618 | 26.6 | 22.2 | 16.7 | 89.5 | 106.8 | 179.1 | chr7:143229351-143230930 | -35 |
| -0.4729213 | 256 | 397.7 | 455.3 | 402.7 | 626.4 | 510.1 | chr18:42930270-42932249 | -390 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| -1.99355 | 51.8 | 44.5 | 32.6 | 133.1 | 99.1 | 281.1 | chr19:56303541-56303721 | -3972 |
| -0.9097074 | 37 | 38.9 | 46.9 | 75.2 | 81.3 | 74.2 | chr6:96131373-96133147 | 127 |
| -4.7435398 | 3 | 1.4 | 0.8 | 13.4 | 59.3 | 66.6 | chr19:18253868-18254452 | -728 |
| -2.0401351 | 7.4 | 8.3 | 10 | 22.3 | 27.9 | 55.5 | chr17:44026267-44026444 | -253 |
| 1.57393048 | 1611.6 | 1205.5 | 843.6 | 405.1 | 611.6 | 212.9 | chr17:44029874-44032155 | -4912 |
| -3.4261311 | 10.4 | 13.9 | 0.8 | 46.5 | 32.6 | 190.7 | chr9:37859285-37859498 | 1239 |
| -2.5692198 | 10.4 | 11.1 | 0 | 44 | 36.2 | 47.4 | chr15:56829425-56829819 | -153 |
| -2.3358119 | 63.6 | 66.7 | 0 | 211.2 | 108.5 | 338.1 | chr11:109469127-109469708 | 121 |
| -3.206186 | 5.9 | 4.2 | 12.6 | 49.5 | 47.5 | 112.5 | chr4:84030719-84031944 | 93 |
| -2.9504799 | 14.8 | 11.1 | 6.7 | 108.3 | 46.3 | 97.4 | chr6:26141366-26141941 | 122 |
| -4.6871674 | 0 | 4.2 | 0 | 23.2 | 28.5 | 56.5 | chr20:9963751-9963987 | 173 |
| -1.9514257 | 45.9 | 41.7 | 38.5 | 146.9 | 86 | 254.8 | chr4:13237872-13238142 | 419 |
| -2.6274016 | 16.3 | 27.8 | 46.9 | 152.4 | 159.6 | 250.3 | chr2:234427862-234428784 | -372 |
| -1.152496 | 111 | 123.7 | 233.5 | 257.2 | 415.2 | 368.4 | chr6:39304972-39306510 | -512 |
| -1.9140268 | 31.1 | 22.2 | 43.5 | 101.9 | 74.7 | 188.2 | chr9:112380785-112381333 | 922 |
| -1.7588971 | 60.7 | 45.9 | 31.8 | 141 | 100.8 | 226.6 | chr3:112875335-112876411 | -323 |
| -3.2130816 | 4.4 | 4.2 | 7.5 | 34.6 | 38 | 76.7 | chr22:38257617-38258527 | 734 |
| -1.9938343 | 121.4 | 175.2 | 137.2 | 669.3 | 347 | 711.5 | chr3:102925478-102926579 | -155 |
| -1.787393 | 149.5 | 115.4 | 231 | 901.8 | 413.4 | 396.6 | chr2:112371864-112373237 | -111 |
| 2.84533449 | 816.9 | 917.7 | 236 | 79.6 | 161.3 | 33.3 | chr2:112373237-112373765 | 840 |
| -5.0495283 | 0 | 0 | 1.7 | 4.9 | 9.5 | 41.9 | chr19:10624744-10625488 | 432 |
| -2.8580831 | 19.2 | 27.8 | 1.7 | 133.1 | 57.5 | 162.5 | chr18:11898206-11899366 | -145 |
| -2.3856069 | 4.4 | 11.1 | 20.9 | 58.4 | 41.5 | 90.3 | chr19:3921632-3922906 | -1443 |
| -2.9654972 | 10.4 | 9.7 | 0 | 61.8 | 29.1 | 66.1 | chr2:233927361-233927769 | -326 |
| -1.7778865 | 23.7 | 48.7 | 56.9 | 145.9 | 123.4 | 174.1 | chr2:233927903-233929031 | 576 |
| -2.5914465 | 5.9 | 4.2 | 38.5 | 64.8 | 86 | 183.7 | chr2:3362154-3363996 | -2470 |
| -7.1443832 | 0 | 0 | 0.8 | 8.9 | 21.4 | 82.8 | chr7:21219998-21220024 | -280 |
| -1.7759241 | 65.1 | 77.9 | 67.8 | 246.3 | 133.5 | 342.1 | chr7:16059733-16060354 | -473 |
| -2.7876187 | 17.8 | 18.1 | 37.7 | 181.1 | 102.6 | 224.5 | chr6:26232360-26233141 | 399 |
| -1.3992193 | 102.1 | 182.1 | 27.6 | 214.2 | 304.9 | 303.3 | chr9:34037473-34039315 | 553 |
| -1.7473892 | 84.4 | 75.1 | 18.4 | 213.7 | 132.3 | 251.3 | chr1:116761528-116763132 | 374 |
| -2.3381617 | 26.6 | 20.9 | 28.5 | 125.6 | 73 | 185.7 | chr6:158508581-158509933 | -2231 |
| -3.3934814 | 11.8 | 23.6 | 0 | 126.6 | 71.8 | 173.6 | chr1:160796833-160797875 | -565 |
| -1.5269403 | 45.9 | 48.7 | 68.6 | 148.9 | 202.3 | 119.1 | chr15:39496132-39496605 | -225 |
| -2.7988875 | 13.3 | 1.4 | 26.8 | 111.3 | 53.4 | 124.1 | chr17:71448807-71449298 | -338 |
| -2.3889727 | 48.8 | 41.7 | 22.6 | 200.3 | 94.9 | 297.2 | chr12:108231685-108232560 | -714 |
| -1.4320353 | 74 | 62.6 | 42.7 | 171.2 | 129.9 | 182.7 | chr3:142687757-142688615 | -429 |
| -2.8175219 | 19.2 | 22.2 | 29.3 | 178.1 | 63.5 | 256.8 | chr13:52323266-52323984 | -2850 |
| -3.5422886 | 13.3 | 7 | 0 | 69.7 | 52.8 | 114 | chr1:143803275-143804052 | -4100 |
| -2.031007 | 22.2 | 26.4 | 28.5 | 109.3 | 56.4 | 149.4 | chr7:69711330-69711689 | 120 |
| -2.6288168 | 13.3 | 8.3 | 0 | 35.6 | 31.4 | 66.6 | chr3:138021278-138021937 | 1057 |
| -2.6372019 | 51.8 | 61.2 | 0 | 159.3 | 100.2 | 443.5 | chr1:74137480-74138270 | 315 |
| -4.1541231 | 7.4 | 2.8 | 0 | 57.9 | 37.4 | 86.3 | chr3:12857617-12858180 | 183 |
| -2.9816549 | 19.2 | 23.6 | 12.6 | 115.3 | 80.1 | 242.2 | chr3:33815224-33815917 | 1010 |
| -2.7201439 | 17.8 | 11.1 | 42.7 | 127.1 | 98.5 | 246.3 | chr8:53863398-53864045 | 944 |
| -2.4514823 | 68.1 | 62.6 | 0 | 284.9 | 112.1 | 317.9 | chr2:234753006-234754499 | 53 |
| -1.9339298 | 42.9 | 41.7 | 4.2 | 92.5 | 74.7 | 172.1 | chr2:249763752-49763941 | -246 |
| -2.197793 | 57.7 | 44.5 | 36.8 | 165.2 | 122.8 | 349.7 | chr6:2528114-2528990 | 582 |
| -2.5729829 | 31.1 | 58.4 | 53.6 | 255.3 | 116.3 | 479.9 | chr16:32594631-32595090 | 1519 |
| 4.04246151 | 74 | 45.9 | 290.4 | 3 | 21.9 | 0 | chr2:24284459-24284644 | 48251 |
| 1.96938973 | 467.6 | 255.8 | 241.9 | 81.6 | 154.8 | 10.1 | chr13:35814719-35816013 | 3809 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| 2.45929043 | 211.6 | 104.3 | 195 | 33.1 | 38.6 | 21.2 | chr5:140711147-140713193 | 2159 |
| 3.05332503 | 207.2 | 43.1 | 154.8 | 4 | 26.1 | 18.7 | chrX:153439831-153441906 | 17216 |
| 3.92957372 | 87.3 | 58.4 | 40.2 | 4.5 | 7.7 | 0 | chr9:96392385-96393336 | 3036 |
| 1.04953668 | 377.4 | 443.5 | 313.8 | 256.7 | 232.5 | 59 | chr16:6472977-6474186 | 464449 |
| -3.7315375 | 16.3 | 7 | 0 | 121.7 | 47.5 | 140.3 | chr16:7499687-7500433 | 1490928 |
| -3.5560009 | 14.8 | 8.3 | 0.8 | 71.2 | 57.5 | 152.4 | chr6:7085942-7086778 | 33174 |
| 3.38923803 | 32.6 | 20.9 | 16.7 | 2 | 4.7 | 0 | chr6:7182309-7182739 | 129338 |
| 6.36106649 | 25.2 | 68.1 | 71.1 | 1 | 0 | 1 | chr9:127100121-127100789 | 36524 |
| 0.8253504 | 2028.9 | 1903.4 | 2104 | 1684 | 1307 | 415.3 | chr9:138230587-138231397 | 3833 |
| 2.69726372 | 1255 | 859.3 | 245.2 | 138.5 | 116.3 | 109 | chr13:27451150-27451963 | 9218 |
| 5.58796499 | 7.4 | 5.6 | 35.1 | 0.5 | 0 | 0.5 | chr6:22123508-22123635 | 348918 |
| 3.16759995 | 19.2 | 23.6 | 19.2 | 1.5 | 2.4 | 3 | chr7:75522038-75522805 | 7093 |
| 2.90197131 | 668.9 | 743.9 | 138.9 | 64.3 | 101.4 | 41.9 | chr3:64646344-64647962 | 1252 |
| 1.43982839 | 599.4 | 557.5 | 310.5 | 183.5 | 187.4 | 170 | chr9:76304809-76306449 | 3558 |
| 2.60178012 | 56.2 | 32 | 32.6 | 4.9 | 2.4 | 12.6 | chr1:1554278-1555040 | 13913 |
| 0.99372028 | 750.3 | 732.7 | 626 | 458.6 | 409.3 | 191.2 | chr1:35103990-35105131 | 39011 |
| 5.71149491 | 14.8 | 8.3 | 29.3 | 1 | 0 | 0 | chr10:27527904-27528268 | 41728 |
| 3.15938262 | 115.4 | 58.4 | 139.8 | 5.4 | 29.7 | 0 | chr18:3709473-3709595 | 160601 |
| 3.62817457 | 38.5 | 19.5 | 33.5 | 2.5 | 2.4 | 2.5 | chr3:42786429-42787355 | 2857 |
| 3.18674262 | 87.3 | 44.5 | 49.4 | 4.9 | 13 | 2 | chr22:40460742-40461242 | 35529 |
| 2.77799286 | 100.6 | 64 | 49.4 | 17.3 | 5.3 | 8.6 | chr3:195598699-195599878 | 1996 |
| 3.02050108 | 1382.2 | 568.7 | 501.3 | 44.5 | 232.5 | 25.2 | chr17:18760004-18760619 | 58095 |
| 1.05119494 | 728.1 | 714.7 | 731.4 | 472.4 | 358.3 | 218.5 | chr11:117520934-117522907 | 6825 |
| 2.12444016 | 140.6 | 94.5 | 125.5 | 14.3 | 62.3 | 6.1 | chr22:36416143-36416574 | 4069 |
| 1.63245893 | 62.2 | 47.3 | 41.8 | 23.2 | 13 | 12.6 | chr3:31996011-31996699 | 1887 |
| 4.33038867 | 26.6 | 12.5 | 29.3 | 1 | 2.4 | 0 | chr16:3108224-3110264 | 6681 |
| 2.97131033 | 264.9 | 123.7 | 268.6 | 11.4 | 69.4 | 3 | chr2:26523645-26524093 | 45582 |
| 3.43348317 | 19.2 | 12.5 | 23.4 | 1 | 3.6 | 0.5 | chr5:71623497-71625298 | 90137 |
| 4.03673377 | 96.2 | 77.9 | 164 | 9.9 | 7.7 | 3 | chr5:77788553-77789791 | 97078 |
| 3.89279577 | 28.1 | 13.9 | 29.3 | 1.5 | 1.8 | 1.5 | chr1:24018666-24018847 | 5780 |
| 3.56985561 | 37 | 16.7 | 31.8 | 1.5 | 4.7 | 1 | chr1:70296011-70296480 | 297800 |
| 2.08720797 | 57.7 | 44.5 | 39.3 | 12.4 | 11.3 | 9.6 | chr17:38189308-38189723 | 3294 |
| 1.85174904 | 56.2 | 25 | 34.3 | 5.4 | 13 | 13.6 | chr9:125168181-125168911 | 10278 |
| 4 | 32.6 | 16.7 | 24.3 | 2.5 | 0.6 | 1.5 | chr10:81937268-81937978 | 17685 |
| 3.03204573 | 25.2 | 20.9 | 58.6 | 1.5 | 11.3 | 0 | chr8:99881482-99882031 | 25329 |
| 0.73203266 | 630.4 | 560.3 | 600 | 453.6 | 279.4 | 345.1 | chr19:17979619-17980555 | 7144 |
| 2.58193904 | 735.5 | 720.2 | 260.3 | 64.8 | 160.7 | 61.1 | chr19:41043623-41048879 | 5102 |
| 5.44017706 | 7.4 | 7.4 | 37.7 | 0 | 1.2 | 0 | chr2:61310980-61311724 | 240001 |
| 1.05180015 | 247.1 | 322.6 | 246.9 | 179.6 | 117.4 | 96.9 | chr21:36354004-36354319 | 4415 |
| 1.23743389 | 69.6 | 72.3 | 67 | 38.1 | 30.8 | 19.7 | chr14:23870417-23871673 | 2659 |
| 2.79219511 | 17.8 | 18.1 | 20.9 | 0.5 | 7.7 | 0.5 | chr7:71207389-71207693 | 232603 |
| 4.58757371 | 10.4 | 13.9 | 31 | 0 | 1.8 | 0.5 | chrX:8097040-8098876 | 1350 |
| 4.06855267 | 118.4 | 40.3 | 61.1 | 4.9 | 7.7 | 0.5 | chr5:45694197-45696170 | 36794 |
| 2.9211794 | 309.3 | 159.9 | 236 | 19.8 | 68.8 | 4.5 | chr1:153516508-153517006 | 2760 |
| 3.28141294 | 25.2 | 16.7 | 84.5 | 4 | 6.5 | 2.5 | chr7:6019617-6020056 | 4429 |
| 2.53922307 | 248.6 | 175.2 | 277.8 | 24.7 | 71.8 | 24.2 | chr3:197541284-197541828 | 8099 |
| NA | 13.3 | 16.7 | 3.3 | 0 | 0 | 0 | chr7:5742120-5743206 | 45155 |
| 1.95011314 | 93.2 | 80.6 | 82 | 15.3 | 40.3 | 10.6 | chr9:123288929-123289456 | 12935 |
| 1.96903854 | 2299.8 | 1878.4 | 2202 | 318.1 | 1237 | 74.2 | chr19:54006815-54008403 | 24137 |
| 2.79062245 | 45.9 | 38.9 | 69.5 | 1 | 20.8 | 0.5 | chr12:10300516-210300605 | 25019 |
| 2.08621796 | 233.8 | 140.4 | 205 | 22.8 | 94.9 | 18.7 | chr11:120076337-120076532 | 40197 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| 3.13137742 | 97.7 | 51.4 | 57.7 | 5.9 | 17.2 | 0.5 | chr8:54840330-54841282 | 77294 |
| 1.94914997 | 1561.3 | 1026.1 | 1633 | 152.4 | 851.2 | 89.3 | chr1:238322032-238324042 | 1230 |
| 2.08199337 | 233.8 | 140.4 | 205 | 23.2 | 94.9 | 18.7 | chr19:10772546-10773165 | 83101 |
| 1.70866022 | 85.8 | 43.1 | 42.7 | 15.8 | 29.1 | 7.6 | chr9:33964808-33965532 | 73777 |
| 2.29862591 | 145 | 93.2 | 118 | 9.9 | 56.9 | 5.6 | chr9:33975880-33977561 | 62227 |
| −1.9558474 | 62.2 | 61.2 | 25.9 | 237.4 | 109.7 | 232.1 | chr14:75912090-75912795 | 4964 |
| 4.56594527 | 25.2 | 16.7 | 41 | 0.5 | 3 | 0 | chr14:75924041-75924429 | 16757 |
| 2.51321216 | 263.4 | 116.8 | 210.1 | 13.9 | 42.1 | 47.4 | chr11:73346429-73348188 | 8297 |
| 1.8662751 | 1690 | 1140.1 | 687.1 | 290.9 | 524.9 | 148.9 | chr14:73787766-73788383 | 12147 |
| 2.20715791 | 60.7 | 30.6 | 34.3 | 14.3 | 5.3 | 7.6 | chr1:44656411-44657187 | 13253 |
| 1.69627682 | 606.8 | 649.3 | 456.9 | 165.2 | 335.1 | 28.3 | chr7:157173944-157175327 | 898608 |
| 2.04626173 | 266.4 | 168.2 | 154.8 | 38.1 | 65.2 | 39.4 | chr18:55039466-55040756 | 1732 |
| 2.76749439 | 288.6 | 173.8 | 230.1 | 20.8 | 61.7 | 19.2 | chr10:72642748-72644383 | 1262 |
| 1.42697024 | 463.2 | 424.1 | 237.7 | 143 | 128.1 | 147.3 | chr17:45901414-45903671 | 44025 |
| 3.62043407 | 22.2 | 18.1 | 54.4 | 1 | 4.7 | 2 | chr3:137709945-137711736 | 243095 |
| 1.57393048 | 1611.6 | 1205.5 | 843.6 | 405.1 | 611.6 | 212.9 | chr17:44029874-44032155 | 6319 |
| NA | 5.9 | 4.2 | 5 | 0 | 0 | 0 | chr7:73599695-73599904 | 93744 |
| −3.1784653 | 8.9 | 4.2 | 0 | 39.6 | 38.6 | 40.4 | chr9:36848224-36849892 | 175418 |
| 2.06105898 | 1770 | 1405.7 | 1947 | 385.8 | 691 | 150.9 | chr9:36975674-36976864 | 48207 |
| 1.75119667 | 3272.1 | 2379 | 1317 | 587.7 | 1185 | 297.2 | chr12:47676042-47678811 | 1929 |
| 2.5643635 | 1475.5 | 515.8 | 1548 | 81.6 | 453.2 | 63.6 | chr22:220020850-220022749 | 13856 |
| 3.72558537 | 149.5 | 94.5 | 126.4 | 7.9 | 19.6 | 0.5 | chr19:58011645-58011850 | 4950 |
| 2.57899213 | 127.3 | 84.8 | 125.5 | 5.9 | 41.5 | 9.1 | chr8:30077742-30077994 | 5405 |
| 1.79228249 | 3946.9 | 3150.6 | 3172 | 532.8 | 2284 | 147.8 | chr9:132547423-132548649 | 18235 |
| 1.84665312 | 500.2 | 424.1 | 320.5 | 133.6 | 138.8 | 73.7 | chr16:65774170-65776940 | 6053 |
| 6.42321143 | 62.2 | 22.2 | 10 | 0.5 | 0.6 | 0 | chr11:118621727-118622049 | 39689 |
| 5.2323119 | 42.9 | 30.6 | 9.2 | 1 | 1.2 | 0 | chr10:1110581-1111258 | 18144 |
| 1.75422064 | 1684.1 | 1320.9 | 1755 | 240.9 | 1026 | 163 | chr17:14146425-14148192 | 2078 |
| −2.6413964 | 54.8 | 37.5 | 25.1 | 274 | 113.9 | 344.6 | chr17:14152849-14154588 | 8488 |
| 2.61215319 | 81.4 | 58.4 | 128 | 10.9 | 27.3 | 5.6 | chr18:11811951-11812419 | 132921 |
| 2.06114029 | 51.8 | 55.6 | 85.4 | 13.9 | 27.3 | 5 | chr17:34742781-34743972 | 68026 |
| 2.48704874 | 25.2 | 20.9 | 25.1 | 2 | 7.7 | 3 | chr17:9976543-9976883 | 65880 |
| 2.60142588 | 4319.8 | 3431.5 | 3107 | 314.1 | 1383 | 92.3 | chr7:7965768-7968799 | 844 |
| 2.00295518 | 272.3 | 226.6 | 136.4 | 66.3 | 42.7 | 49.5 | chr11:71629757-71630807 | 2586 |
| 1.31051832 | 63.6 | 111.2 | 51.9 | 23.7 | 31.4 | 36.3 | chr9:137117803-137118470 | 11227 |
| −3.1593315 | 11.8 | 12.5 | 0 | 59.9 | 35.6 | 121.6 | chr9:137119704-137120123 | 13004 |
| 2.08205672 | 1589.4 | 1255.5 | 964.1 | 84.1 | 676.2 | 139.3 | chr8:48836951-48839344 | 1589 |
| 1.44768591 | 235.3 | 141.8 | 200.9 | 59.4 | 112.1 | 40.4 | chr17:56892825-56894391 | 5020 |
| 2.23055678 | 41.4 | 27.8 | 102.1 | 11.4 | 12.5 | 12.6 | chr4:46073396-46074958 | 12636 |
| NA | 10.4 | 7 | 2.5 | 0 | 0 | 0 | chr14:72698875-72698926 | 26005 |
| 1.81476893 | 79.9 | 147.4 | 94.6 | 61.8 | 13.6 | 16.1 | chr5:155977726-155978848 | 291943 |
| 2.46422198 | 81.4 | 105.7 | 174.9 | 17.8 | 26.1 | 21.7 | chr10:8131808-8133049 | 3025 |
| NA | 8.9 | 7 | 20.1 | 0 | 0 | 0 | chr19:60294221-60297549 | 24854 |
| 2.2993566 | 473.6 | 265.6 | 459.4 | 33.1 | 179.1 | 31.3 | chr22:30467099-30467593 | 8774 |
| 1.68537444 | 134.7 | 98.7 | 154.8 | 24.7 | 68.2 | 27.8 | chr11:61225565-61225967 | 21281 |
| 1.93077213 | 920.5 | 595.1 | 1076 | 79.1 | 525.5 | 75.2 | chr19:13067427-13070864 | 5536 |
| 2.27719601 | 398.1 | 280.9 | 381.6 | 60.8 | 128.7 | 29.3 | chr3:151946482-151946741 | 17342 |
| 2.41718259 | 5111.6 | 1676.8 | 5551 | 686.6 | 1482 | 141.3 | chr9:135283276-135284566 | 6981 |
| 2.44004151 | 28.1 | 23.6 | 25.9 | 4 | 5.3 | 5 | chr1:1743565-1743858 | 68644 |
| 2.75798674 | 77 | 34.8 | 97.9 | 6.4 | 19 | 5.6 | chr6:11222075-11222398 | 19985 |
| 1.07870444 | 288.6 | 328.1 | 456.9 | 219.6 | 163.1 | 125.6 | chr20:49849540-49852352 | 1509 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| 1.7122766 | 96.2 | 76.5 | 99.6 | 29.2 | 33.2 | 20.7 | chr19:11104821-11105603 | 44156 |
| 2.90088791 | 2137 | 1586.4 | 977.5 | 210.7 | 323.3 | 95.4 | chr7:9646613-9646242 | 15886 |
| 2.91405947 | 85.8 | 102.9 | 285.4 | 6.9 | 50.4 | 5.6 | chr20:61696690-61697341 | 24658 |
| 1.15267113 | 873.1 | 656.3 | 606.7 | 177.1 | 538 | 245.7 | chr4:109306498-109311084 | 236 |
| 2.40091639 | 65.1 | 58.4 | 120.5 | 22.8 | 21.4 | 2 | chr3:50287467-50288535 | 7958 |
| 4.6157999 | 28.1 | 22.2 | 15.9 | 1 | 1.2 | 0.5 | chr2:154883594-154884283 | 447267 |
| 1.75701942 | 207.2 | 178 | 368.2 | 76.7 | 93.7 | 52.5 | chr17:8867042-8867962 | 1919 |
| 2.41089539 | 51.8 | 33.4 | 88.7 | 8.4 | 14.2 | 10.1 | chr9:130180861-130181395 | 7710 |
| NA | 31.1 | 19.5 | 66.1 | 0 | 0 | 0 | chr10:1434299-1435081 | 335028 |
| 1.88031984 | 4167.4 | 2384.5 | 4361 | 596.1 | 2224 | 144.3 | chr14:37749098-37750866 | 3028 |
| 2.58684961 | 74 | 45.9 | 109.6 | 9.4 | 20.2 | 8.6 | chr21:44142300-44142990 | 33102 |
| 1.92235047 | 677.8 | 482.5 | 711.4 | 185 | 206.4 | 102.4 | chr18:13631176-13632816 | 423202 |
| 2.27719601 | 398.1 | 280.9 | 381.6 | 60.8 | 128.7 | 29.3 | chr9:98170751-98171022 | 14872 |
| 3.01653786 | 146.5 | 80.6 | 106.3 | 4.9 | 23.7 | 12.6 | chr1:66402621-66403132 | 171899 |
| 2.06077531 | 691.1 | 641 | 854.5 | 206.3 | 232.5 | 85.3 | chr1:153301679-153302468 | 11688 |
| 5.30245681 | 152.4 | 80.6 | 39.3 | 1.5 | 2.4 | 3 | chr17:36272140-36273263 | 4287 |
| 2.13873449 | 41.4 | 34.8 | 17.6 | 8.4 | 8.9 | 4 | chr6:150036783-150037103 | 44142 |
| 1.89435283 | 896.8 | 780 | 388.3 | 231.5 | 236.7 | 87.3 | chr16:67920297-67921972 | 9893 |
| 2.09526332 | 312.3 | 216.9 | 212.6 | 29.2 | 132.3 | 12.1 | chr22:21793006-21793969 | 50819 |
| 0.86887405 | 59.2 | 50.1 | 49.4 | 28.2 | 27.9 | 30.8 | chr16:8726473-8726884 | 50734 |
| 2.47373108 | 171.7 | 175.2 | 53.6 | 25.7 | 13.6 | 32.8 | chr6:26306989-26307765 | 73 |
| 2.84452851 | 762.1 | 428.2 | 637.7 | 33.1 | 205.8 | 15.6 | chr4:111772139-111775162 | 4307 |
| 2.91614137 | 260.5 | 171 | 256.9 | 13.4 | 75.3 | 2.5 | chr17:32546860-32547194 | 243145 |
| 2.00796713 | 2964.2 | 1846.4 | 2435 | 435.8 | 1271 | 94.9 | chr5:134391360-134392542 | 5912 |
| 2.68301234 | 2401.9 | 1560 | 1625 | 80.1 | 755.1 | 34.8 | chr1:10675646-10677556 | 102693 |
| 2.72338632 | 53.3 | 29.2 | 107.1 | 9.9 | 14.8 | 4 | chrX:3616044-3616302 | 25488 |
| 5.21958944 | 10.4 | 8.3 | 67 | 0 | 1.8 | 0.5 | chr1:291773259-91773475 | 73871 |
| 3.46195161 | 16.3 | 16.7 | 24.3 | 0.5 | 4.2 | 0.5 | chr7:100643664-100643854 | 3972 |
| 2.34521352 | 307.8 | 251.7 | 190 | 61.8 | 56.9 | 28.8 | chr4:951289-953356 | 5022 |
| 4.10364709 | 328.5 | 204.4 | 94.6 | 10.4 | 26.1 | 0 | chr16:4806803-4807220 | 30293 |
| 3.39689015 | 14.8 | 25 | 23.4 | 2.5 | 3 | 0.5 | chr6:45304253-45304499 | 149177 |
| 1.54508648 | 236.8 | 152.9 | 159.8 | 50.5 | 118.6 | 19.2 | chr17:32001957-32002456 | 27290 |
| 2.64365787 | 185 | 129.3 | 49.4 | 29.7 | 18.4 | 10.1 | chr18:65219460-65222228 | 1574 |
| 1.09532946 | 335.9 | 315.6 | 224.3 | 117.2 | 169.1 | 123.6 | chr20:43160197-43162341 | 1898 |
| 2.20503163 | 404 | 390.7 | 463.6 | 132.6 | 97.9 | 42.4 | chr17:44657195-44657887 | 5586 |
| 2.86754193 | 133.2 | 127.9 | 64.4 | 10.4 | 26.1 | 8.1 | chr22:25074420-25207885 | 89176 |
| 2.272569 | 276.7 | 303.1 | 115.5 | 88.5 | 26.1 | 29.3 | chr11:68363183-68363990 | 2389 |
| 2.44452413 | 682.2 | 500.5 | 969.1 | 18.3 | 348.2 | 28.8 | chr3:182902504-182904559 | 92687 |
| 2.20740949 | 293 | 168.2 | 314.7 | 34.6 | 126.3 | 7.1 | chr17:76488858-76488990 | 355705 |
| 2.80722082 | 463.2 | 189.1 | 423.5 | 53.9 | 84.2 | 15.6 | chr17:7308696-7308935 | 14853 |
| 2.00727717 | 142.1 | 118.2 | 57.7 | 20.3 | 39.1 | 19.7 | chr12:119268762-119269335 | 22293 |
| 2.12151029 | 3809.3 | 2601.4 | 2759 | 440.8 | 1310 | 356.2 | chr17:7195418-7196997 | 15611 |
| 2.72962074 | 44.4 | 36.2 | 174.1 | 10.9 | 21.4 | 6.1 | chr11:63218705-63219639 | 13675 |
| 1.39812158 | 159.8 | 97.3 | 141.4 | 22.3 | 49.2 | 79.7 | chr20:60210939-60211426 | 19707 |
| 3.06598218 | 768.1 | 606.2 | 142.3 | 83.1 | 51.6 | 46.4 | chr6:108603027-108604373 | 9746 |
| 2.03054954 | 482.4 | 247.5 | 439.4 | 52.4 | 187.4 | 46.4 | chr13:93721525-93721670 | 1044502 |
| 4.58757371 | 10.4 | 13.9 | 31 | 0 | 1.8 | 0.5 | chrX:7771050-7772712 | 1579 |
| 3.02414235 | 62.2 | 61.2 | 39.3 | 15.3 | 4.2 | 0.5 | chr22:17552383-17553039 | 106528 |
| 0.86887405 | 59.2 | 50.1 | 49.4 | 28.2 | 27.9 | 30.8 | chr9:94464364-94464444 | 7964 |
| 1.32124849 | 229.4 | 173.8 | 233.5 | 73.2 | 104.4 | 77.2 | chr20:34964199-34964948 | 49017 |
| 2.50545769 | 100.6 | 25 | 20.9 | 3.5 | 10.7 | 11.6 | chr22:37196987-37197511 | 3221 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| 2.09526332 | 312.3 | 216.9 | 212.6 | 29.2 | 132.3 | 12.1 | chr22:21793006-21793969 | 20754 |
| 3.20759542 | 28.1 | 15.3 | 53.6 | 2.5 | 6.5 | 1.5 | chr3:186643215-186643475 | 79682 |
| 3.50559695 | 1852.8 | 1611.5 | 1619 | 266.1 | 12.5 | 169 | chr2:7482934-7484335 | 4382 |
| 2.50956373 | 130.2 | 98.7 | 235.2 | 14.3 | 51.6 | 15.6 | chr1:70480097-70480711 | 36452 |
| 2.98644568 | 624.5 | 278.1 | 135.6 | 13.4 | 108.5 | 9.1 | chr16:22264126-22265574 | 28589 |
| 1.93077213 | 920.5 | 595.1 | 1076 | 79.1 | 525.5 | 75.2 | chr19:13067427-13070864 | 101562 |
| 4.62467478 | 77 | 43.1 | 141.4 | 4.9 | 4.7 | 1 | chr19:47323515-47323608 | 4909 |
| -1.4445973 | 171.7 | 175.2 | 77 | 485.8 | 293.6 | 374.4 | chr7:127458469-127460282 | 379938 |
| -1.2944505 | 81.4 | 164.1 | 105.4 | 407.1 | 236.1 | 217.5 | chr7:72217444-72217569 | 10545 |
| -1.0676447 | 90.3 | 130.7 | 149.8 | 241.4 | 330.4 | 205.4 | chr15:39590471-39591694 | 2295 |
| -5.8322873 | 0 | 4.2 | 0 | 67.3 | 29.7 | 142.3 | chr7:1005468-1006007 | 138682 |
| -1.6489885 | 121.4 | 97.3 | 61.9 | 231.5 | 345.2 | 303.3 | chr11:66867123-66867440 | 25396 |
| 1.04953668 | 377.4 | 443.5 | 313.8 | 256.7 | 232.5 | 59 | chr16:6472977-6474186 | 464449 |
| -3.7315375 | 16.3 | 7 | 0 | 121.7 | 47.5 | 140.3 | chr16:7499687-7500433 | 1490928 |
| -3.5560009 | 14.8 | 8.3 | 0.8 | 71.2 | 57.5 | 152.4 | chr6:7085942-7086778 | 33174 |
| 3.38923803 | 32.6 | 20.9 | 16.7 | 2 | 4.7 | 0 | chr6:7182309-7182739 | 129338 |
| -4.0208185 | 1.5 | 2.8 | 0 | 9.9 | 23.1 | 36.8 | chr16:1165012-1165289 | 21909 |
| -3.3796986 | 10.4 | 15.3 | 0 | 73.7 | 33.8 | 160 | chr17:2064980-2065372 | 88643 |
| -2.039347 | 75.5 | 107.1 | 10.9 | 140.5 | 172 | 482.9 | chr8:22777627-22780782 | 62162 |
| -2.1746021 | 31.1 | 25 | 22.6 | 73.2 | 155.4 | 126.7 | chr1:107824674-107825548 | 340844 |
| -2.1248515 | 10.4 | 5.6 | 1.7 | 24.7 | 30.3 | 22.2 | chr2:111127887-111127979 | 100488 |
| -4.648645 | 4.4 | 9.7 | 0 | 64.3 | 65.8 | 225.1 | chr18:76035838-76036231 | 70354 |
| -0.9570371 | 72.5 | 93.2 | 164.9 | 193.9 | 231.9 | 216 | chr19:13270425-13271002 | 207561 |
| -3.5085494 | 0 | 4.2 | 0 | 13.9 | 17.8 | 16.1 | chr1:131514481-131515026 | 124060 |
| -4.0522899 | 3 | 9.7 | 0 | 51.9 | 36.2 | 122.6 | chr7:18830932-18831311 | 34919 |
| -3.4489656 | 4.4 | 25 | 3.3 | 70.2 | 93.1 | 193.8 | chr2:102299337-102300453 | 7372 |
| -0.6463525 | 275.3 | 278.1 | 204.2 | 407.6 | 433.6 | 344.6 | chr20:44091390-44093403 | 8661 |
| -1.5955564 | 62.2 | 84.8 | 151.5 | 349.7 | 296.6 | 255.8 | chr20:17243509-17244509 | 88379 |
| -2.4889934 | 5.9 | 4.2 | 0 | 15.8 | 20.2 | 20.7 | chr16:1417220-1417744 | 1864 |
| -4.3198656 | 0 | 7 | 0 | 31.2 | 24.3 | 84.3 | chr19:61308947-61309423 | 15276 |
| -2.6498936 | 25.2 | 23.6 | 0.8 | 107.3 | 51.6 | 152.4 | chr6:29585317-29585667 | 3692 |
| -4.5435843 | 0 | 2.8 | 0 | 13.4 | 12.5 | 39.4 | chr9:9836606-9836981 | 80718 |
| NA | 0 | 0 | 0 | 4.9 | 12.5 | 14.1 | chr5:3652545-3652637 | 3424 |
| -2.1820233 | 20.7 | 15.3 | 1.7 | 64.3 | 45.7 | 61.1 | chr15:50859285-50860408 | 9655 |
| -2.774423 | 25.2 | 38.9 | 64.4 | 290.4 | 111.5 | 477.3 | chr15:54966165-54967426 | 31194 |
| -3.8604663 | 1.5 | 0 | 2.5 | 13.4 | 35.6 | 9.1 | chr19:21786811-21786969 | 23920 |
| -3.7256648 | 7.4 | 8.3 | 0 | 39.6 | 44.5 | 123.6 | chr13:43907174-43907434 | 141397 |
| -1.4980166 | 37 | 32 | 105.4 | 161.3 | 201.1 | 130.2 | chr15:157492068-157492600 | 171304 |
| -3.7640708 | 1.5 | 1.4 | 0 | 11.4 | 11.3 | 16.7 | chr3:157557633-157557935 | 236754 |
| -1.2944505 | 81.4 | 164.1 | 105.4 | 407.1 | 236.1 | 217.5 | chr7:72217444-72217569 | 10559 |
| -1.9584209 | 25.2 | 32 | 0 | 52.9 | 62.9 | 106.5 | chr7:25112110-25112347 | 168916 |
| -2.884348 | 4.4 | 4.2 | 0 | 19.3 | 29.1 | 15.1 | chr19:50748579-50748969 | 31188 |
| -1.5239364 | 116.9 | 121 | 113.8 | 351.7 | 234.3 | 425.4 | chr15:26015834-26016735 | 1769 |
| -2.2912313 | 1.5 | 4.2 | 0 | 15.3 | 20.8 | 19.7 | chr18:18010239-18011327 | 7370 |
| -2.3914548 | 41.4 | 54.2 | 0 | 160.8 | 102.6 | 238.2 | chr20:4149865-4150925 | 27264 |
| -3.697172 | 10.4 | 23.6 | 0 | 154.3 | 71.2 | 215.5 | chr5:92982051-92983483 | 490378 |
| -2.718571 | 13.3 | 12.5 | 25.9 | 78.7 | 52.2 | 209.4 | chr11:124296093-124296718 | 2050 |
| -1.9525675 | 57.7 | 64 | 87 | 254.3 | 215.9 | 337.6 | chr16:14990415-14992253 | 15001 |
| -4.8777442 | 1.5 | 0 | 0 | 11.9 | 23.1 | 9.1 | chr7:134120095-134120387 | 5531 |
| -2.8692344 | 25.2 | 25 | 0 | 102.4 | 84.8 | 179.6 | chr19:139550222-13951385 | 27294 |
| -2.3855283 | 5.9 | 8.3 | 0 | 27.7 | 24.3 | 22.2 | chr17:72917300-72917474 | 128301 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| −3.4989471 | 19.2 | 8.3 | 77.2 | 54.6 | 179.1 | chr3:121011805-121011854 | 29809 |
| −1.4017978 | 148 | 164.1 | 731.1 | 470.4 | 374.9 | chr21:35182255-35183105 | 160785 |
| −1.8430853 | 77 | 94.5 | 145.4 | 161.9 | 455.1 | chr2:123961556-123964857 | 2324 |
| −1.5432766 | 10.4 | 7 | 22.3 | 32 | 37.8 | chr1:168906840-168907436 | 7202 |
| −3.074854 | 4.4 | 12.5 | 14.2 | 32.6 | 72.7 | chr19:50543781-50544060 | 8083 |
| −2.2738544 | 40 | 30.6 | 37.1 | 111.5 | 165 | chr18:75106300-75108016 | 176774 |
| −1.8243798 | 44.4 | 62.6 | 68.8 | 102 | 204.4 | chr1:200450162-200450949 | 20815 |
| −2.2741932 | 35.5 | 44.5 | 130.6 | 80.7 | 341.6 | chr16:68971904-68972166 | 58457 |
| −3.3056113 | 14.8 | 18.1 | 34.3 | 46.3 | 173.1 | chr1:53782248-53782681 | 190001 |
| −4.5957855 | 0 | 8.3 | 0 | 39.7 | 113.5 | chr11:2652194-2652378 | 25518 |
| −2.329079 | 17.8 | 18.1 | 47.5 | 60.5 | 172.6 | chr8:77775671-77756046 | 2207 |
| −3.9745293 | 0 | 0 | 28.5 | 11.9 | 11.1 | chr6:37734540-37735013 | 38968 |
| NA | 0 | 0 | 90.5 | 16.3 | 6.6 | chr2:55277216-55277916 | 38864 |
| −1.0696073 | 56.2 | 45.9 | 83.6 | 112.1 | 99.4 | chr7:156490852-156491949 | 4708 |
| −4.6770231 | 3 | 5.6 | 16.3 | 41.5 | 126.1 | chr4:54592960-54593603 | 32264 |
| NA | 0 | 0 | 5.9 | 10.7 | 8.6 | chr16:3651874-3652057 | 55634 |
| −1.0931392 | 161.3 | 183.5 | 52.4 | 284.1 | 350.2 | chr7:5414272-5414620 | 15257 |
| −1.996363 | 53.3 | 65.3 | 333.4 | 191.6 | 281.6 | chr1:59020026-59020362 | 2179 |
| −1.800508 | 32.6 | 34.8 | 200.3 | 67.6 | 138.8 | chr17:39078391-39079439 | 15542 |
| −1.326782 | 60.7 | 77.9 | 98.4 | 139.4 | 201.3 | chr6:158900427-158903403 | 24460 |
| −1.9476723 | 31.1 | 19.5 | 91 | 155.4 | 86.8 | chr19:55063866-55065091 | 7912 |
| −2.7379812 | 7.4 | 13.9 | 52.9 | 32 | 62.1 | chr5:67619417-67619940 | 61461 |
| −2.1813572 | 44.4 | 47.3 | 48 | 132.9 | 279.5 | chr14:101098656-101100681 | 2228 |
| −1.9546817 | 19.2 | 23.6 | 151.4 | 53.4 | 147.8 | chr11:87881252-87881720 | 539352 |
| −2.7704799 | 28.1 | 11.1 | 58.9 | 83.6 | 225.6 | chr2:95374626-95375351 | 48190 |
| −2.7163399 | 16.3 | 8.3 | 135 | 43.3 | 166.5 | chr18:51241454-51241879 | 165192 |
| −3.0109787 | 20.7 | 15.3 | 100.4 | 54 | 161 | chr7:100061972-100062343 | 14952 |
| −2.2629306 | 19.2 | 19.5 | 75.2 | 41.5 | 121.6 | chr7:100068453-100069466 | 8150 |
| −3.5320769 | 7.4 | 13.9 | 114.8 | 50.4 | 127.2 | chr16:31250255-31250487 | 71583 |
| −2.5410242 | 23.7 | 29.2 | 68.8 | 109.7 | 295.2 | chr7:72033511-72034003 | 45886 |
| −3.089675 | 5.9 | 5.6 | 170.7 | 48 | 23.7 | chr20:42812230-42813325 | 4876 |
| −2.1076957 | 20.7 | 22.2 | 26.2 | 107.4 | 41.4 | chr19:60142324-60142967 | 8040 |
| −4.5957855 | 0 | 8.3 | 36.1 | 39.7 | 113.5 | chr11:2652194-2652378 | 229490 |
| −4.1973254 | 3 | 8.3 | 47.5 | 30.3 | 119.6 | chr1:1291603-1292038 | 269024 |
| −3.1784653 | 8.9 | 4.2 | 57.4 | 38.6 | 40.4 | chr9:36848224-36849892 | 175418 |
| −2.06105898 | 1770 | 1405.7 | 39.6 | 691 | 150.9 | chr9:36975674-36976864 | 48207 |
| −2.5667866 | 7.4 | 13.9 | 385.8 | 31.4 | 65.1 | chr7:101475320-101475612 | 227865 |
| −0.3286991 | 248.6 | 248.6 | 29.7 | 368.9 | 299.2 | chr8:96028586-96031576 | 710 |
| −3.6351968 | 4.4 | 8.3 | 298.3 | 22.5 | 112.5 | chr7:44774431-44774479 | 19401 |
| −2.8374959 | 3 | 5.6 | 22.8 | 45.7 | 73.2 | chr1:20647906-20649745 | 1114 |
| −2.2210314 | 60.7 | 66.7 | 26.2 | 127.5 | 391.1 | chr13:110164497-110166567 | 1792 |
| −1.4475276 | 77 | 61.2 | 329 | 127.5 | 235.1 | chr13:110164497-110166567 | 2449 |
| −2.7622715 | 34 | 38.9 | 210.7 | 68.8 | 270.5 | chr18:19453402-19453902 | 43195 |
| −4.3153554 | 0 | 1.4 | 155.3 | 27.3 | 8.1 | chr4:144863563-144863911 | 130649 |
| −3.3278992 | 8.9 | 2.8 | 8.4 | 35 | 119.6 | chr4:39420617-39420876 | 44688 |
| −3.1406731 | 1.5 | 1.4 | 63.3 | 30.8 | 75.7 | chr9:129994842-129995147 | 11489 |
| −2.7253846 | 25.2 | 16.7 | 30.2 | 65.2 | 112.5 | chr8:37724678-37725235 | 11702 |
| −2.2301657 | 75.5 | 64 | 99.4 | 183.9 | 306.8 | chr16:559119-560435 | 2745 |
| −2.076905 | 62.2 | 50.1 | 266.1 | 118.6 | 220 | chr21:37259532-37260806 | 24204 |
| −3.6672202 | 1.5 | 8.3 | 216.2 | 48 | 41.4 | chr19:60734340-60734693 | 4957 |
| −3.8477924 | 1.5 | 8.3 | 35.1 | 26.1 | 86.8 | chr12:120162807-120162859 | 57661 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| -4.054296 | 3 | 1.4 | 0 | 10.4 | 38 | 24.7 | chr21:46390160-46390978 | 9340 |
| NA | 0 | 0 | 5.9 | 12.4 | 8.3 | 25.2 | chr7:43309072-43309368 | 190498 |
| -1.9912298 | 42.9 | 66.7 | 0 | 103.4 | 135.8 | 220 | chr10:112421512-112422578 | 27901 |
| -3.2824159 | 17.8 | 7 | 0 | 33.1 | 83.6 | 124.6 | chr4:44209528-42096794 | 1426 |
| -2.4232916 | 5.9 | 7 | 17.6 | 67.8 | 56.9 | 38.9 | chr10:11951439-11952796 | 46715 |
| -3.1584977 | 4.4 | 12.5 | 0 | 43.5 | 33.2 | 74.2 | chr19:12729042-12729480 | 4855 |
| -2.5434432 | 7.4 | 9.7 | 1.7 | 16.3 | 74.1 | 19.2 | chr4:81328319-81329391 | 3408 |
| -1.4960597 | 108 | 127.9 | 33.5 | 229 | 216.5 | 314.4 | chr1:226466107-226467327 | 4234 |
| 1.73542064 | 1684.1 | 1320.9 | 1755 | 240.9 | 1026 | 163 | chr7:14146425-14148192 | 2078 |
| -2.6413964 | 54.8 | 37.5 | 25.1 | 274 | 113.9 | 344.6 | chr1:14152849-14154588 | 8488 |
| -3.8521428 | 0 | 11.1 | 0 | 24.2 | 49.8 | 86.3 | chr19:53923892-53924381 | 11646 |
| NA | 25.2 | 30.6 | 26.8 | 25.2 | 22.5 | 65.6 | chr10:108643984-108644110 | 270235 |
| -2.7325925 | 0 | 0 | 0 | 180.1 | 94.9 | 274 | chr20:36790132-36790453 | 3774 |
| NA | 0 | 0 | 0 | 12.4 | 16 | 47.9 | chr17:28145842-28146204 | 81992 |
| -3.7856235 | 1.5 | 2.8 | 0 | 7.9 | 13.6 | 37.8 | chr19:19106271-19106646 | 3809 |
| -2.5549993 | 16.3 | 12.5 | 38.5 | 115.3 | 82.4 | 197.8 | chr3:109129359-109129779 | 44828 |
| 1.31051832 | 63.6 | 111.2 | 51.9 | 23.7 | 31.4 | 36.3 | chr9:137117803-137118470 | 11227 |
| -3.1593315 | 11.8 | 12.5 | 0 | 59.9 | 35.6 | 121.6 | chr9:137119704-137120123 | 13004 |
| -5.0013795 | 1.5 | 8.3 | 0 | 67.3 | 26.1 | 220.5 | chr5:33644575-33644794 | 283197 |
| -2.7532674 | 22.2 | 9.7 | 20.9 | 140 | 77.7 | 138.3 | chr5:114366952-11438604 | 519332 |
| -1.7463128 | 45.9 | 38.9 | 55.2 | 132.6 | 91.9 | 245.2 | chr19:52421099-52422174 | 4655 |
| -2.3380478 | 19.2 | 22.2 | 20.9 | 69.7 | 68.2 | 177.1 | chr4:89661478-89663872 | 1303 |
| -2.5528825 | 7.4 | 7 | 0 | 27.7 | 35.6 | 21.2 | chr12:50694669-50695589 | 8115 |
| -3.7109252 | 7.4 | 4.2 | 0 | 51 | 26.7 | 74.2 | chr16:160347321-160347743 | 37412 |
| -1.9377157 | 5.9 | 7 | 8.4 | 23.7 | 19.6 | 38.3 | chrX:117652458-117653778 | 139219 |
| -4.4190573 | 0 | 2.8 | 0 | 15.3 | 14.8 | 29.8 | chrX:117659439-117660133 | 145887 |
| -2.8104329 | 23.7 | 30.6 | 5.9 | 148.9 | 90.2 | 183.2 | chr5:77854609-77855663 | 125268 |
| -2.6923754 | 7.4 | 5.6 | 0.8 | 24.2 | 33.2 | 31.8 | chr16:19780573-19781041 | 22845 |
| -4.186527 | 4.4 | 2.8 | 0 | 68.3 | 21.4 | 41.4 | chr2:11640679-11641552 | 49423 |
| -2.229913 | 5.9 | 5.6 | 0.8 | 14.8 | 23.7 | 19.2 | chr2:24742940-24743205 | 82223 |
| -3.0519121 | 4.4 | 1.4 | 0 | 10.9 | 16 | 21.2 | chr2:219590602-219590702 | 23837 |
| -4.8337625 | 4.4 | 1.4 | 0 | 40.6 | 21.9 | 102.9 | chr18:68359381-68360037 | 2994 |
| -2.8381683 | 31.1 | 66.7 | 0.8 | 257.7 | 116.9 | 330.5 | chr9:127691767-127692305 | 142599 |
| -2.201442 | 28.1 | 18.1 | 19.2 | 130.6 | 95.5 | 74.7 | chr5:140552873-140554755 | 1679 |
| -3.0459273 | 8.9 | 13.9 | 0 | 31.7 | 32 | 124.6 | chr9:97115477-97115553 | 4297 |
| -2.0505086 | 37 | 47.3 | 42.7 | 156.3 | 128.1 | 241.7 | chr3:120524029-120525082 | 28646 |
| -1.2239849 | 133.2 | 164.1 | 220.1 | 458.1 | 366 | 384.5 | chr6:79842674-79843629 | 1557 |
| -1.9269659 | 75.5 | 187.7 | 278.7 | 248.3 | 1506 | 306.3 | chr2:40531472-40534370 | 60158 |
| -1.7046444 | 66.6 | 70.9 | 25.9 | 138.5 | 118.6 | 275.5 | chr2:172087460-172089323 | 1280 |
| -2.0941274 | 69.6 | 68.1 | 8.4 | 162.7 | 121 | 340.1 | chr17:7288368-7289746 | 5645 |
| -1.4400663 | 34 | 37.5 | 33.5 | 75.7 | 66.4 | 142.8 | chr8:13178050-13178321 | 238581 |
| -3.9279412 | 3 | 9.7 | 0 | 38.6 | 42.7 | 112 | chr19:5894058-5894290 | 35146 |
| -2.4473008 | 7.4 | 7 | 0.8 | 21.8 | 34.4 | 26.7 | chr1:245792186-245792288 | 13164 |
| -3.2163686 | 8.9 | 8.3 | 0.8 | 39.1 | 27.3 | 100.9 | chr18:5446650-5447140 | 87091 |
| -3.0871809 | 20.7 | 23.6 | 15.9 | 115.8 | 156.6 | 239.2 | chr22:36533152-36534596 | 2815 |
| NA | 0 | 0 | 0 | 11.9 | 11.3 | 98.9 | chr3:39169188-99169425 | 4608 |
| -1.4743012 | 60.7 | 108.5 | 33.5 | 167.2 | 167.9 | 228.1 | chr2:241860033-241862325 | 42748 |
| -2.6242889 | 2290.9 | 2551.4 | 6474 | 27092 | 9757 | 32926 | chr4:77026252-77026585 | 16287 |
| -2.588867 | 13.3 | 26.4 | 21.8 | 112.3 | 56.9 | 200.8 | chr1:229623439-229623652 | 3868 |
| -3.0414951 | 19.2 | 12.5 | 0 | 48 | 48 | 165 | chr9:136800707-136801053 | 127408 |
| -2.9224133 | 0 | 5.6 | 20.9 | 36.6 | 42.7 | 121.6 | chr7:101730411-101730554 | 15317 |

TABLE 14-continued

Comprehensive DNA Methylation and K27 Profiles of CD44+ Nulliparous and Parous Breast Epithelial Cells

| | | | | | | |
|---|---|---|---|---|---|---|
| −2.7796099 | 31.1 | 33.4 | 0 | 144 | 89 | 209.9 | chrX:39835710-39837175 | 5221 |
| −5.9120339 | 0 | 1.4 | 0.8 | 11.9 | 32 | 40.4 | chr3:115114622-115116067 | 74974 |
| −3.4267916 | 4.4 | 13.9 | 0.8 | 53.9 | 34.4 | 117.1 | chr11:122936026-122936327 | 34439 |
| −2.8657293 | 51.8 | 30.6 | 33.5 | 271.1 | 196.3 | 377.4 | chr11:45876428-45879508 | 14191 |
| −3.9078521 | 3 | 7 | 0 | 23.7 | 28.5 | 97.9 | chr19:50876328-50877064 | 13355 |
| −2.3900632 | 26.6 | 22.2 | 10.9 | 70.7 | 67 | 118.1 | chr1:6231889-6233887 | 11234 |
| −2.4183126 | 0 | 5.6 | 0 | 29.7 | 40.3 | 18.2 | chr14:100082762-100082940 | 23033 |
| −1.6923184 | 50.3 | 50.1 | 24.3 | 103.9 | 90.2 | 208.9 | chr8:67850083-67850577 | 62886 |
| −2.2935487 | 51.8 | 54.2 | 55.2 | 359.1 | 103.2 | 328 | chr2:219465090-219465754 | 11924 |
| −2.3431967 | 4.4 | 12.5 | 3.3 | 34.1 | 35.6 | 32.8 | chr11:67961642-67962575 | 125425 |
| −1.8182641 | 26.6 | 8.3 | 91.2 | 139 | 195.2 | 110.5 | chr1:27868410-27868708 | 2752 |
| −2.7988875 | 13.3 | 1.4 | 26.8 | 111.3 | 53.4 | 124.1 | chr17:71448807-71449298 | 37987 |
| −1.2263219 | 118.4 | 144.6 | 166.5 | 492.2 | 277.6 | 235.1 | chr1:87569571-8570286 | 3190 |
| −5.5092352 | 4.4 | 0 | 0 | 54.9 | 27.9 | 117.6 | chr17:54090950-54091719 | 33081 |
| −3.8399036 | 7.4 | 7 | 0 | 45.5 | 32 | 128.7 | chr17:17656697-17656772 | 24316 |
| −5.2233122 | 0 | 1.4 | 0 | 9.9 | 30.8 | 11.6 | chr12:122569764-122569997 | 14338 |
| −3.1117027 | 5.9 | 8.3 | 22.6 | 118.7 | 51.6 | 147.8 | chr13:108366212-108366558 | 319885 |
| −5.7515441 | 0 | 0 | 0.8 | 10.9 | 26.1 | 6.1 | chr19:1447397-1447761 | 5415 |
| −3.3796038 | 29.6 | 9.7 | 31.8 | 148.9 | 163.7 | 427.4 | chr6:143289230-143289768 | 18532 |
| −2.3172364 | 13.3 | 12.5 | 5 | 31.2 | 35 | 87.3 | chr20:56907193-56907482 | 59148 |
| −1.897014 | 128.8 | 132.1 | 0 | 250.8 | 215.3 | 505.6 | chr3:46897666-46898382 | 3785 |
| −4.2177846 | 0 | 2.8 | 0 | 8.4 | 19 | 24.7 | chr3:46915137-46915186 | 20922 |
| −2.7180876 | 4.4 | 5.6 | 0 | 25.2 | 18.4 | 22.2 | chr3:46915207-46915895 | 21312 |
| −1.489464 | 45.9 | 51.4 | 27.6 | 115.8 | 110.3 | 124.6 | chr16:66780360-67880489 | 101874 |
| NA | 0 | 0 | 0 | 39.1 | 26.1 | 67.6 | chr10:105304629-105304813 | 60684 |
| −2.5606082 | 10.4 | 12.5 | 0 | 34.6 | 41.5 | 59 | chr20:31883475-31883656 | 20786 |
| −3.2110604 | 20.7 | 18.1 | 0 | 102.4 | 68.2 | 188.7 | chr9:122670528-122671670 | 8328 |
| −0.4597895 | 269.3 | 268.3 | 268.6 | 343.3 | 472.8 | 292.7 | chr19:63559791-63561351 | 5361 |
| −4.8851704 | 1.5 | 1.4 | 0 | 31.7 | 30.3 | 23.7 | chr22:30790298-30791085 | 21655 |
| −2.5327663 | 8.9 | 8.3 | 47.7 | 122.2 | 89.6 | 244.2 | chr11:78825938-78826664 | 3042 |
| −3.2234225 | 4.4 | 13.9 | 1.7 | 91 | 40.3 | 55.5 | chr6:168766285-168766802 | 181664 |
| −1.8599595 | 25.2 | 69.5 | 23.4 | 147.4 | 177.4 | 103.9 | chr1:25952008-25952634 | 24670 |
| −3.2575885 | 16.3 | 11.1 | 0.8 | 87.1 | 36.8 | 145.8 | chr19:45716955-45717527 | 52276 |
| −3.2601228 | 17.8 | 7 | 0 | 60.4 | 47.5 | 129.7 | chr19:45728035-45728896 | 63500 |
| −4.0522899 | 3 | 9.7 | 0 | 51.9 | 36.2 | 122.6 | chr17:18830932-18831311 | 17664 |
| −2.5923195 | 7.4 | 5.6 | 3.3 | 20.3 | 52.8 | 25.2 | chr18:124287379-124288229 | 23872 |
| −2.7876187 | 17.8 | 18.1 | 37.7 | 181.1 | 102.6 | 224.5 | chr6:26232360-26233141 | 399 |
| −3.9293454 | 7.4 | 2.8 | 0 | 27.7 | 37.4 | 90.3 | chr4:457393-458525 | 25483 |
| −0.8975728 | 100.6 | 118.2 | 154 | 241.4 | 240.2 | 212.9 | chr10:118377294-118377690 | 7038 |
| −3.0372071 | 32.6 | 34.8 | 25.9 | 216.7 | 62.3 | 486.9 | chr9:33280235-33280698 | 220581 |
| −1.3260797 | 16.3 | 50.1 | 37.7 | 59.9 | 86.6 | 114.5 | chr18:9798873-9799494 | 100956 |
| −6.1099177 | 1.5 | 0 | 0 | 14.8 | 20.2 | 68.6 | chr22:40170591-40170641 | 2357 |
| −2.100694 | 17.8 | 15.3 | 8.4 | 59.4 | 47.5 | 71.1 | chr18:68665064-68665182 | 18791 |
| −4.8116423 | 3 | 4.2 | 0 | 29.2 | 43.3 | 129.7 | chr9:112348133-112348929 | 33450 |
| −2.2994015 | 5.9 | 8.3 | 0 | 21.8 | 24.9 | 23.2 | chr13:47793006-47793664 | 17452 |
| −3.487622 | 13.3 | 12.5 | 0 | 85.1 | 36.8 | 167.5 | chr13:106655632-106656105 | 661216 |
| −4.7279205 | 0 | 1.4 | 0 | 7.4 | 13.6 | 16.1 | chr17:17530293-17530690 | 4980 |
| −3.5573767 | 3 | 1.4 | 0 | 15.3 | 14.8 | 21.7 | chr17:17585102-17585467 | 59773 |
| −1.595945 | 87.3 | 75.1 | 125.5 | 379.9 | 208.8 | 281.6 | chrX:152737583-152738455 | 11178 |
| −2.9821173 | 3 | 13.9 | 17.6 | 98.4 | 75.3 | 98.9 | chr5:168603463-168603936 | 57012 |
| NA | 0 | 0 | 0 | 29.2 | 18.4 | 18.2 | chr3:81795571-81795754 | 97978 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| −2.0320918 | 4.4 | 11.1 | 23.4 | 36.1 | 80.1 | 42.9 | chr8:70561693-70562617 | 20743 |
| −2.45899 | 19.2 | 9.7 | 0.8 | 36.1 | 54 | 73.2 | chr18:19094372-19094831 | 126076 |
| −1.8502992 | 17.8 | 12.5 | 18.4 | 40.6 | 45.7 | 89.3 | chr6:34602835-34603327 | 61199 |
| −1.6824209 | 26.6 | 38.9 | 31.8 | 100.4 | 70.6 | 141.3 | chr3:187394247-187394468 | 168360 |
| −5.082149 | 0 | 0 | 0.8 | 10.9 | 10.1 | 6.1 | chr17:1205814-1205898 | 44450 |
| −4.7944159 | 0 | 2.8 | 0 | 18.8 | 43.3 | 15.6 | chr13:30388565-30388732 | 10337 |
| −2.5453584 | 22.2 | 19.5 | 37.7 | 133.6 | 107.4 | 222.5 | chr1:13947801-13948119 | 44024 |
| −1.9558474 | 62.2 | 61.2 | 25.9 | 237.4 | 109.7 | 232.1 | chr14:75912090-75912795 | 4964 |
| 4.56594527 | 25.2 | 16.7 | 41 | 0.5 | 3 | 0 | chr14:75924041-75924429 | 16757 |
| −3.0588937 | 4.4 | 8.3 | 0.8 | 26.2 | 40.9 | 45.4 | chr2:1459410-1460493 | 63710 |
| −2.865387 | 22.2 | 30.6 | 0.8 | 169.7 | 73.6 | 147.3 | chr9:123538221-123538973 | 169378 |
| −2.3772882 | 10.4 | 8.3 | 17.6 | 51.9 | 43.9 | 92.8 | chr15:32117365-32119241 | 69923 |
| −2.1511678 | 54.8 | 61.2 | 87 | 329 | 179.1 | 393.6 | chrX:6153618-6154437 | 1861 |
| −4.0528418 | 5.9 | 7 | 0 | 82.1 | 49.8 | 82.2 | chr2:159659153-159659305 | 125838 |
| −3.6196086 | 5.9 | 18.1 | 0 | 74.7 | 66.4 | 153.9 | chr7:136205910-136206410 | 1789 |
| −2.5951644 | 23.7 | 29.2 | 29.3 | 126.6 | 86 | 284.1 | chr16:84931911-84932357 | 4652 |
| −2.0051433 | 13.3 | 13.9 | 0.8 | 25.7 | 46.3 | 40.4 | chr19:3638594-3639677 | 12310 |
| −4.3244134 | 4.4 | 1.4 | 0 | 27.2 | 21.4 | 67.6 | chr11:56708046-56708517 | 2485 |
| −2.2950533 | 28.1 | 25 | 0 | 65.3 | 54 | 141.3 | chr5:135554375-135556109 | 1508 |
| −2.2428855 | 17.8 | 36.2 | 27.6 | 130.6 | 84.2 | 166.5 | chr22:17019796-17020268 | 7275 |
| −2.5483117 | 25.2 | 43.1 | 0.8 | 124.2 | 90.8 | 189.2 | chr22:49505800-49506706 | 46318 |
| −2.3175199 | 23.7 | 32 | 3.3 | 121.2 | 70 | 102.9 | chr20:29571209-29571520 | 5463 |
| −1.9299415 | 34 | 30.6 | 33.5 | 111.8 | 88.4 | 173.6 | chr2:80402968-80403386 | 809544 |
| −1.9879885 | 51.8 | 70.9 | 55.2 | 193.9 | 207 | 304.8 | chr10:68816603-68817576 | 278333 |
| −3.5377479 | 3 | 1.4 | 0 | 8.9 | 22.5 | 19.7 | chr16:24280762-24281146 | 106578 |
| −3.544188 | 8.9 | 22.2 | 0 | 88.1 | 65.8 | 208.9 | chr6:163522586-163523523 | 454901 |
| −2.1347644 | 48.8 | 76.5 | 73.6 | 323 | 121.6 | 428.9 | chr1:28847331-28848288 | 111 |
| −2.0822272 | 41.4 | 48.7 | 20.9 | 163.2 | 87.8 | 221 | chr10:111960061-111960974 | 3165 |
| −2.6218455 | 94.7 | 105.7 | 26.8 | 521.4 | 196.9 | 680.2 | chr3:106568558-106570647 | 1200 |
| NA | 0 | 0 | 0 | 13.4 | 10.1 | 11.6 | chrX:106362295-106362783 | 26022 |
| −2.3552458 | 19.2 | 20.9 | 0 | 46.5 | 46.9 | 111.5 | chr3:196288944-196291552 | 182936 |
| −2.5016762 | 14.8 | 15.3 | 0.8 | 40.1 | 55.2 | 79.7 | chr4:114190180-114190467 | 231636 |
| −1.2963312 | 68.1 | 95.9 | 86.2 | 200.8 | 148.3 | 265.4 | chr2:69289849-69290881 | 27121 |
| −2.9635687 | 10.4 | 19.5 | 9.2 | 70.2 | 65.8 | 169 | chr19:53947059-53948851 | 2504 |
| −2.2739481 | 8.9 | 12.5 | 0 | 23.7 | 37.4 | 42.4 | chr2:233031314-233031918 | 2540 |
| −3.7044262 | 7.4 | 7 | 13.4 | 109.3 | 59.3 | 193.8 | chr19:50580778-50581330 | 19075 |
| −1.5764978 | 183.5 | 233.6 | 403.4 | 1184 | 758.7 | 504.6 | chr4:9629353-9630427 | 2322 |
| −1.8246361 | 71 | 58.4 | 25.9 | 188 | 120.4 | 241.7 | chr4:41340848-41341283 | 283505 |
| −2.718571 | 13.3 | 12.5 | 25.9 | 78.7 | 52.2 | 209.4 | chr11:124296093-124296718 | 15113 |
| −0.966236 | 88 | 92 | 101 | 131 | 166 | 252 | chr10:93158697-93160175 | 201761 |
| −0.6050452 | 346 | 442 | 615 | 678 | 782 | 674 | chr19:54312942-54315267 | 4675 |
| −0.9878253 | 138 | 140 | 198 | 327 | 320 | 297 | chr1:6423326-6424197 | 16327 |
| −0.7174128 | 281 | 224 | 327 | 497 | 460 | 411 | chr8:22077451-22078863 | 3029 |
| −0.7296675 | 146 | 146 | 144 | 234 | 238 | 251 | chr5:50720631-50721385 | 6294 |
| −0.8886952 | 177 | 187 | 269 | 304 | 456 | 412 | chr22:38958778-38959309 | 1562 |
| −4.9068906 | 1 | 0 | 0 | 11 | 13 | 6 | chr16:7292139-7294385 | 55169 |
| −0.7740585 | 343 | 408 | 470 | 624 | 853 | 611 | chr17:58058243-58060907 | 1284130 |
| −0.6875634 | 296 | 289 | 324 | 360 | 555 | 549 | chr17:178470736-178472648 | 1082 |
| −0.6037864 | 329 | 355 | 382 | 590 | 554 | 476 | chr2:772724-773447 | 5628 |
| −0.6484119 | 94 | 155 | 181 | 238 | 209 | 227 | chr20:772724-773447 | 10730 |
| −4.084628 | 1 | 1 | 0 | 11 | 5 | 18 | chr17:18091734-18092090 | 10868 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| -1.0299947 | 40 | 38 | 41 | 60 | 62 | 121 | chr16:52875001-52876808 | 1975 |
| -1.2625495 | 39 | 82 | 127 | 205 | 201 | 189 | chr3:157492068-157492600 | 171304 |
| -0.5625947 | 65 | 69 | 61 | 97 | 90 | 101 | chr5:375471-376424 | 18657 |
| -0.9716468 | 128 | 98 | 108 | 230 | 235 | 190 | chr15:26015834-26016735 | 1769 |
| -0.8760561 | 127 | 132 | 154 | 186 | 308 | 264 | chr12:92489760-92490804 | 2554 |
| -0.7738024 | 98 | 121 | 129 | 155 | 216 | 224 | chr19:9784490-980897 | 2396 |
| -2.8356995 | 18 | 10 | 8 | 72 | 52 | 133 | chr19:54031026-54032395 | 31960 |
| -1.1627408 | 294 | 171 | 385 | 773 | 701 | 429 | chr21:35182255-35183105 | 160785 |
| -0.7379535 | 101 | 105 | 92 | 170 | 166 | 161 | chr19:63406384-63407397 | 20683 |
| NA | 0 | 0 | 0 | 40 | 57 | 28 | chr16:56622641-56623136 | 6106 |
| -0.7067736 | 337 | 326 | 351 | 693 | 539 | 423 | chr21:43972622-43973933 | 9872 |
| -0.6924 | 202 | 205 | 119 | 256 | 297 | 297 | chr9:23810577-23812851 | 4349 |
| NA | 0 | 0 | 0 | 6 | 13 | 7 | chr6:29904116-29905129 | 1888 |
| -0.6354468 | 145 | 159 | 164 | 265 | 220 | 242 | chr2:161982831-161983691 | 2396 |
| -3.1799091 | 11 | 14 | 7 | 55 | 108 | 127 | chr8:23471936-23473038 | 30180 |
| -4.2094534 | 0 | 0 | 2 | 13 | 15 | 9 | chr6:37734540-37735013 | 38968 |
| -1.2911052 | 82 | 70 | 94 | 217 | 147 | 238 | chr4:140875374-140876951 | 418521 |
| -1.5360529 | 159 | 200 | 101 | 634 | 327 | 373 | chr7:5414272-5414620 | 15257 |
| -1.2016339 | 10 | 11 | 9 | 22 | 20 | 27 | chr5:140511060-140512468 | 1742 |
| -0.5906536 | 271 | 266 | 222 | 335 | 434 | 374 | chr2:549041-550046 | 93473 |
| -0.6050452 | 346 | 442 | 615 | 678 | 782 | 674 | chr19:54312942-54315267 | 105 |
| -1.092597 | 73 | 101 | 90 | 169 | 199 | 195 | chr17:44008257-44009194 | 2017 |
| -0.9682911 | 77 | 81 | 95 | 223 | 136 | 136 | chr7:25952008-25952634 | 24670 |
| -0.5693871 | 427 | 593 | 439 | 669 | 736 | 760 | chr1:148078259-148080734 | -107 |
| -0.5693871 | 427 | 593 | 439 | 669 | 736 | 760 | chr1:148078259-148080734 | -107 |
| -1.4180275 | 35 | 92 | 114 | 236 | 205 | 203 | chr19:41333556-41335121 | 1273 |
| -0.8624965 | 142 | 148 | 73 | 177 | 220 | 263 | chr1:71504 6-71 6308 | 19555 |
| -1.1205589 | 47 | 17 | 45 | 70 | 76 | 91 | chrX:153324890-153325776 | 6881 |
| -0.8472061 | 214 | 191 | 406 | 449 | 522 | 488 | chr10:21844539-21846611 | 9042 |
| -2.447459 | 6 | 1 | 15 | 42 | 37 | 41 | chr4:39420617-39420876 | 44688 |
| -1.3155018 | 115 | 95 | 105 | 172 | 337 | 275 | chr16:559119-560435 | 2745 |
| -1.0955777 | 30 | 16 | 27 | 46 | 57 | 53 | chrX:146800513-146800998 | 10613 |
| -1.5849625 | 6 | 5 | 6 | 16 | 16 | 19 | chr1:109716644-109717579 | 24975 |
| -1.0655883 | 106 | 100 | 138 | 165 | 297 | 258 | chr4:81337840-81339454 | 13200 |
| -1.0333862 | 107 | 77 | 115 | 160 | 195 | 257 | chr5:11436952-11438604 | 519332 |
| -0.5654489 | 345 | 419 | 551 | 602 | 746 | 598 | chr18:895438-897073 | 1312 |
| -1.7083964 | 107 | 167 | 185 | 621 | 502 | 377 | chr17:69939772-69941487 | 1368 |
| -0.640377 | 255 | 383 | 375 | 490 | 619 | 470 | chr19:60855675-60858282 | 6213 |
| -0.9767384 | 256 | 280 | 183 | 341 | 574 | 500 | chr3:106568558-106570647 | 1200 |
| -0.5862176 | 133 | 111 | 139 | 171 | 215 | 189 | chr6:41103721-41104213 | 10939 |
| -1.6679239 | 47 | 28 | 32 | 138 | 80 | 122 | chr5:140552873-140544755 | 1679 |
| -0.3396924 | 272 | 228 | 291 | 323 | 333 | 345 | chrX:71441053-71443548 | 1215 |
| -0.5693871 | 427 | 593 | 439 | 669 | 736 | 760 | chr1:148078259-148080734 | 1446 |
| -0.5693871 | 427 | 593 | 439 | 669 | 736 | 760 | chr1:148078259-148080734 | 1446 |
| -0.4114442 | 201 | 197 | 205 | 300 | 248 | 254 | chr7:96473579-96474427 | 7310 |
| -1.2223924 | 11 | 10 | 9 | 23 | 20 | 27 | chrX:119484171-119484644 | 2825 |
| -0.8132652 | 234 | 228 | 234 | 291 | 505 | 427 | chr7:127458469-127460282 | 379938 |
| -3.9385995 | 10 | 0 | 8 | 40 | 20 | 216 | chr9:131987344-131987998 | 12994 |
| -3.7004397 | 1 | 0 | 1 | 7 | 6 | 13 | chr10:14256710-14257223 | 155906 |
| -0.7187563 | 498 | 335 | 347 | 703 | 682 | 557 | chr17:7915705-7917269 | 15259 |
| 1.23250954 | 362 | 328 | 264 | 228 | 55 | 123 | chr17:7924044-7924513 | 7468 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| −0.7856743 | 140 | 125 | 166 | 219 | 285 | 239 | chr12:16650065-16650933 | 1792 |
| −1.7555813 | 33 | 17 | 27 | 65 | 107 | 88 | chr13:108366212-108366558 | 319885 |
| 2.7548875 | 24 | 16 | 14 | 6 | 1 | 1 | chr13:108398838-108398938 | 352388 |
| −1.6232325 | 15 | 23 | 24 | 49 | 69 | 73 | chr3:46915207-16915895 | 21312 |
| −5.3098553 | 2 | 1 | 0 | 28 | 60 | 31 | chr6:43192059-3192397 | 40222 |
| −0.5979221 | 363 | 458 | 435 | 663 | 653 | 585 | chr19:12764569-12766186 | 2068 |
| −4.2094534 | 4 | 0 | 2 | 35 | 48 | 28 | chr11:101749261-101751157 | 27034 |
| −2.6288168 | 27 | 34 | 47 | 147 | 437 | 84 | chr19:63559791-63561351 | 5361 |
| −6.2854022 | 1 | 0 | 0 | 35 | 20 | 23 | chr22:30790298-30791085 | 21655 |
| −1.9114633 | 10 | 4 | 7 | 27 | 31 | 21 | chr6:168766285-168766802 | 181664 |
| −0.8507942 | 81 | 70 | 78 | 114 | 135 | 164 | chr6:26232360-26233141 | 399 |
| −0.5541764 | 162 | 175 | 184 | 273 | 259 | 233 | chr12:41162428-41165585 | 105739 |
| −0.6900445 | 170 | 130 | 150 | 209 | 281 | 236 | chr1:28847331-28848288 | 111 |
| −0.9168061 | 265 | 213 | 218 | 319 | 503 | 492 | chr2:133142474-133145778 | 1414 |
| −0.9661664 | 24 | 63 | 64 | 96 | 102 | 97 | chr19:12796977-12798323 | 9580 |
| −1.1953476 | 60 | 86 | 54 | 118 | 151 | 189 | chr9:203667-204892 | 1614 |
| −1.4736887 | 127 | 42 | 69 | 274 | 225 | 162 | chr11:66867123-66867440 | 25396 |
| NA | 0 | 0 | 0 | 30 | 5 | 7 | chr17:1205814-1205898 | 44450 |
| −2.0696342 | 21 | 22 | 48 | 67 | 136 | 179 | chr1:234787094-234785577 | 46602 |
| −4.422532 | 4 | 0 | 5 | 40 | 62 | 91 | chr8:28901074-28691121 | 112751 |
| −0.8509037 | 189 | 189 | 228 | 365 | 397 | 331 | chr5:158456311-158456890 | 2766 |
| −1.2874397 | 33 | 44 | 50 | 96 | 86 | 128 | chr2:74596891-74597416 | 2035 |
| −0.3084734 | 336 | 309 | 303 | 380 | 394 | 400 | chr7:130003338-130004481 | 18037 |
| −0.570698 | 601 | 585 | 508 | 759 | 1084 | 673 | chr1:145537688-145539525 | 58801 |
| −0.8604486 | 199 | 172 | 193 | 248 | 409 | 367 | chr1:71610641-71613108 | 6408 |
| 0.73864217 | 85 | 117 | 85 | 67 | 63 | 42 | chr7:71147876-71148027 | 26909 |
| 1.40681699 | 52 | 65 | 58 | 28 | 24 | 14 | chr9:135697760-135698087 | 149344 |
| 0.55561854 | 137 | 177 | 124 | 103 | 97 | 98 | chr15:49173512-49173966 | 11026 |
| 2.5849625 | 47 | 36 | 61 | 11 | 7 | 6 | chr1:199151252-199151914 | 24292 |
| 0.46583751 | 738 | 726 | 906 | 633 | 603 | 480 | chr18:53258836-53261329 | 6168 |
| 2.26303441 | 21 | 36 | 15 | 0 | 8 | 7 | chr10:363618-364221 | 361689 |
| 1.40498383 | 39 | 60 | 44 | 20 | 14 | 20 | chr16:71386357-71386966 | 253114 |
| 1.90052107 | 344 | 478 | 873 | 283 | 2 | 169 | chr14:98782398-98783946 | 24403 |
| 1.93490497 | 19 | 23 | 23 | 5 | 6 | 6 | chr1:2482912-2483152 | 3581 |
| 4.32192809 | 13 | 4 | 3 | 0 | 1 | 0 | chr17:24963335-24963854 | 18942 |
| 0.90378468 | 51 | 57 | 66 | 34 | 25 | 34 | chr6:71721239-71721378 | 2201 |
| 0.74066008 | 129 | 138 | 124 | 67 | 67 | 98 | chr19:39753760-39753913 | 23932 |
| 4.36257008 | 18 | 63 | 63 | 4 | 3 | 0 | chr9:127100121-127100789 | 36524 |
| 2.12553088 | 20 | 16 | 12 | 5 | 6 | 0 | chr12:51896839-51897050 | 3473 |
| 0.82442844 | 99 | 132 | 109 | 54 | 70 | 68 | chr18:145668837-145668960 | 6353 |
| 0.58833584 | 193 | 226 | 221 | 139 | 129 | 159 | chr17:35478779-35479196 | 6399 |
| 0.94088691 | 78 | 111 | 74 | 35 | 44 | 58 | chr8:37818107-37818291 | 44618 |
| 0.73580166 | 122 | 171 | 120 | 83 | 69 | 96 | chr20:34498042-34498307 | 140458 |
| 4.03562391 | 21 | 46 | 15 | 0 | 4 | 1 | chr22:41900125-41900698 | 12640 |
| −0.7187563 | 498 | 335 | 347 | 703 | 682 | 557 | chr17:7915705-7917269 | 15259 |
| 1.23250954 | 362 | 328 | 264 | 228 | 55 | 123 | chr17:7924044-7924513 | 7468 |
| 0.70744651 | 84 | 95 | 79 | 45 | 54 | 59 | chr8:1828211-1828337 | 68719 |
| 0.76930158 | 274 | 276 | 217 | 187 | 96 | 167 | chr6:12857276-12858311 | 31975 |
| 1.64976283 | 779 | 720 | 459 | 272 | 165 | 187 | chr1:106756646-10677556 | 102693 |
| 0.74066008 | 129 | 138 | 124 | 67 | 69 | 98 | chr1:40008813-40008966 | 18231 |
| 1.51189904 | 24 | 23 | 30 | 9 | 9 | 9 | chr18:33108202-33108311 | 291742 |

TABLE 14-continued

Comprehensive DNA Methylation and K27 Profiles of CD44+ Nulliparous and Parous Breast Epithelial Cells

| | | | | | | | | | |
|---|---|---|---|---|---|---|---|---|---|
| 1.0957324 | 1200 | 1064 | 929 | 612 | 434 | 448 | chr17:7195418-7196997 | 15611 |
| 2.02553509 | 40 | 91 | 40 | 3 | 14 | 25 | chr10:8131808-8133049 | 3025 |
| 0.73864217 | 85 | 117 | 85 | 67 | 63 | 42 | chr17:71147876-71148027 | 6196 |
| 0.89249437 | 155 | 103 | 91 | 61 | 55 | 72 | chr1:243918014-243918554 | 533375 |
| 1.04663109 | 823 | 641 | 674 | 384 | 302 | 349 | chr15:76698191-76700189 | 1187 |
| 1.08934257 | 548 | 590 | 494 | 297 | 211 | 259 | chr1:238322032-238324042 | 1230 |
| 1.33184356 | 45 | 55 | 46 | 18 | 22 | 18 | chr16:612388-612706 | 32368 |
| 0.75691518 | 77 | 87 | 103 | 50 | 51 | 57 | chr19:19082265-19082415 | 46533 |
| 1.49391052 | 172 | 186 | 256 | 69 | 82 | 67 | chr16:85122622-85123400 | 23331 |
| 0.81740859 | 239 | 253 | 264 | 112 | 145 | 172 | chr16:65774170-65776940 | 6053 |
| 0.70577097 | 123 | 93 | 89 | 57 | 58 | 72 | chr9:118489195-118489340 | 727871 |
| 2.1183947 | 60 | 39 | 66 | 5 | 14 | 19 | chr17:4071950-4073112 | 41492 |
| 1.63226822 | 78 | 66 | 42 | 18 | 15 | 27 | chr20:5970632-5971425 | 11666 |
| 0.95015145 | 1638 | 1315 | 1655 | 1181 | 669 | 535 | chr19:47448945-47450989 | 1182 |
| 0.80132885 | 695 | 720 | 1213 | 458 | 635 | 415 | chr1:66945577-66945152 | 4640 |
| 0.89712282 | 150 | 182 | 128 | 96 | 56 | 95 | chr1:16034940-16035407 | 12056 |
| -1.7555813 | 33 | 17 | 27 | 65 | 107 | 88 | chr13:108366212-108366558 | 319885 |
| 2.7548875 | 24 | 16 | 14 | 6 | 1 | 1 | chr13:108398838-108398938 | 352388 |
| 1.28149092 | 992 | 1112 | 1027 | 522 | 406 | 360 | chr7:7965768-7968799 | 844 |
| -0.7467517 | 129 | 135 | 118 | 186 | 225 | 230 | chr15:43209226-43210016 | -272 |
| -1.1562618 | 134 | 96 | 159 | 189 | 353 | 325 | chr6:26358450-26360034 | -4058 |
| -0.602578 | 137 | 162 | 108 | 207 | 191 | 220 | chr7:16335205-16335859 | 673 |
| -0.5035618 | 342 | 349 | 348 | 576 | 470 | 427 | chr1:55001849-55003114 | 294 |
| -0.5569195 | 123 | 106 | 100 | 169 | 161 | 154 | chr18:27777050-27777589 | -230 |
| -0.9716468 | 128 | 98 | 108 | 230 | 235 | 190 | chr15:26015834-26016735 | 1769 |
| -1.7117196 | 45 | 37 | 114 | 165 | 204 | 273 | chr2:38684134-38686062 | -1570 |
| -1.2016339 | 10 | 11 | 9 | 22 | 20 | 27 | chr5:140511060-140512468 | 1742 |
| -0.4647179 | 144 | 143 | 134 | 188 | 179 | 214 | chr3:31899329-31900217 | 547 |
| -0.8886952 | 177 | 187 | 269 | 304 | 456 | 412 | chr4:94304135-94305246 | 1562 |
| -0.4623113 | 257 | 261 | 210 | 306 | 358 | 339 | chr10:126096670-126097915 | 217 |
| -1.330734 | 65 | 36 | 95 | 135 | 150 | 208 | chr5:6765119-6766185 | -2065 |
| -1.8783214 | 17 | 2 | 15 | 34 | 40 | 51 | chr2:96902789-96904093 | -3979 |
| -1.3801037 | 121 | 154 | 143 | 201 | 505 | 382 | chr2:74733959-74736034 | 96 |
| -1.0764708 | 51 | 84 | 113 | 161 | 157 | 205 | chr17:77094500-77095043 | -349 |
| -0.6875634 | 296 | 289 | 324 | 360 | 555 | 549 | chr17:58058243-58060907 | 1082 |
| -1.0666372 | 71 | 89 | 115 | 155 | 195 | 226 | chr13:41432575-41433086 | 391 |
| -1.2124256 | 57 | 98 | 94 | 205 | 183 | 189 | chr10:79356612-79357753 | -828 |
| -1.1298432 | 119 | 150 | 246 | 485 | 314 | 328 | chr6:169843597-169844480 | -143 |
| -4.5477959 | 32 | 18 | 27 | 1027 | 331 | 443 | chr14:35858713-35859543 | 468 |
| -1.8686282 | 0 | 36 | 99 | 132 | 175 | 186 | chr1:845867-846338 | -4881 |
| -1.6889135 | 23 | 49 | 44 | 213 | 80 | 81 | chr12:48386660-48387639 | 315 |
| -0.7486104 | 237 | 246 | 208 | 328 | 444 | 389 | chr6:136651729-136653369 | 133 |
| -1.1331493 | 33 | 69 | 79 | 106 | 143 | 148 | chr19:4294590-4295246 | -5071 |
| -0.3895106 | 285 | 261 | 238 | 358 | 323 | 346 | chr13:20245429-20246407 | 139 |
| -0.694587 | 71 | 230 | 159 | 298 | 357 | 329 | chr19:47272039-47273849 | 815 |
| -0.7578381 | 157 | 108 | 133 | 190 | 259 | 224 | chr19:5855901-5856864 | -828 |
| -0.6285039 | 247 | 237 | 234 | 324 | 411 | 375 | chr6:1334489-1335511 | -67 |
| -0.7460249 | 78 | 79 | 97 | 125 | 169 | 132 | chr8:17314343-17315170 | 451 |
| -0.9270685 | 138 | 127 | 90 | 201 | 237 | 237 | chr3:153469504-153470081 | 1274 |
| -0.560802 | 173 | 194 | 195 | 233 | 362 | 234 | chr6:138766672-138767325 | -30 |
| -0.4918008 | 199 | 234 | 180 | 286 | 293 | 283 | chr14:104226492-104227458 | -27 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| -1.1822033 | 66 | 100 | 94 | 151 | 210 | 229 | chr15:50869353-50869808 | -79 |
| -1.0299947 | 40 | 38 | 41 | 60 | 62 | 121 | chr6:52875001-52876808 | 1975 |
| -0.5727878 | 170 | 141 | 165 | 230 | 221 | 257 | chr1:40495876-40496530 | -116 |
| -2.2548139 | 15 | 4 | 3 | 34 | 30 | 41 | chr8:143542496-143542810 | 275 |
| -0.85639 | 143 | 97 | 198 | 326 | 229 | 238 | chr21:39673700-39674136 | -164 |
| -1.238587 | 133 | 125 | 109 | 328 | 250 | 288 | chr21:113062737-113063644 | -1521 |
| -0.8814657 | 260 | 164 | 324 | 497 | 459 | 422 | chr22:16940469-16941618 | 358 |
| -1.2715607 | 66 | 87 | 86 | 172 | 182 | 223 | chr7:240754207-240755099 | -32 |
| -0.8132652 | 234 | 228 | 234 | 291 | 505 | 427 | chr7:127458469-127460282 | -1137 |
| -0.8546453 | 314 | 203 | 349 | 645 | 480 | 441 | chr12:52058902-52059546 | -1021 |
| -0.5961031 | 60 | 81 | 74 | 118 | 101 | 106 | chrX:106845892-106846668 | 87 |
| -0.3958415 | 215 | 220 | 227 | 316 | 284 | 271 | chr2:174535510-174538190 | 343 |
| -0.4510444 | 202 | 214 | 227 | 256 | 312 | 311 | chr7:21432781-21433664 | -991 |
| -5.9264308 | 6 | 4 | 1 | 88 | 364 | 217 | chr1:149520663-149522254 | 44 |
| -0.4755907 | 181 | 166 | 157 | 221 | 253 | 227 | chrX:76892566-76893760 | -54 |
| -0.3955413 | 160 | 162 | 125 | 203 | 191 | 194 | chrX:118623499-118624681 | -249 |
| -0.60921 | 194 | 141 | 196 | 273 | 260 | 277 | chr8:99906115-99906942 | 557 |
| -0.803461 | 37 | 30 | 39 | 53 | 60 | 72 | chrX:71318931-71319388 | 909 |
| -1.9719856 | 1 | 7 | 5 | 18 | 16 | 17 | chr20:55356631-55357125 | -2673 |
| -1.2463771 | 64 | 39 | 93 | 144 | 130 | 191 | chr5:90714663-90715778 | -315 |
| -2.7693871 | 1 | 4 | 6 | 23 | 27 | 25 | chr22:36998846-36998977 | 51 |
| -0.6621304 | 337 | 309 | 264 | 401 | 579 | 460 | chr3:58197790-58199426 | 310 |
| -0.5839075 | 309 | 310 | 293 | 587 | 430 | 350 | chr7:4589887-4590592 | -267 |
| -0.5027242 | 120 | 130 | 129 | 160 | 174 | 203 | chr6:86408184-86408678 | 1315 |
| 0.78700628 | 371 | 390 | 295 | 256 | 167 | 189 | chr6:86409192-86410070 | 115 |
| -0.5654489 | 345 | 419 | 551 | 602 | 746 | 598 | chr18:895438-897073 | 1312 |
| -0.9516153 | 152 | 155 | 72 | 251 | 271 | 211 | chr19:18529112-18530488 | 197 |
| -0.6798563 | 181 | 130 | 194 | 225 | 286 | 298 | chr22:36471276-36472367 | -365 |
| -0.7174128 | 281 | 224 | 327 | 497 | 460 | 411 | chr8:22077451-22078863 | -462 |
| -0.6379477 | 224 | 182 | 191 | 351 | 308 | 270 | chr9:129198581-129199330 | -330 |
| -0.683716 | 199 | 180 | 195 | 240 | 349 | 333 | chr1:232575375-232576461 | -133 |
| -1.7424236 | 62 | 43 | 61 | 272 | 141 | 147 | chr7:7125193-7126022 | -170 |
| -0.6050452 | 346 | 442 | 615 | 678 | 782 | 674 | chr19:54312942-54315267 | -370 |
| -0.4936162 | 171 | 160 | 196 | 238 | 243 | 261 | chr9:128662327-128663537 | 168 |
| -0.8022116 | 100 | 91 | 90 | 130 | 127 | 233 | chr3:181802743-181803619 | 570 |
| -0.9614279 | 150 | 111 | 137 | 188 | 273 | 314 | chr1:116761528-1167632 | 374 |
| -1.0318489 | 76 | 71 | 77 | 118 | 160 | 180 | chr22:27993009-27995892 | -536 |
| -0.3783087 | 177 | 182 | 188 | 242 | 222 | 247 | chr5:137638010-137638805 | -255 |
| -0.7111211 | 126 | 135 | 122 | 168 | 193 | 266 | chr7:29569303-29571641 | 521 |
| -0.5503223 | 217 | 167 | 178 | 248 | 253 | 322 | chr1:54126633-54128453 | 498 |
| -0.893707 | 219 | 194 | 122 | 345 | 310 | 339 | chr13:26922366-26924091 | -517 |
| -0.9092023 | 252 | 148 | 182 | 487 | 315 | 291 | chr10:38423328-38424055 | 411 |
| -0.7497073 | 81 | 66 | 101 | 126 | 145 | 146 | chr9:80041086-80041511 | 488 |
| -0.5619892 | 136 | 140 | 146 | 170 | 236 | 217 | chr1:22909063-22910062 | -355 |
| -1.2319467 | 57 | 101 | 100 | 146 | 232 | 228 | chr9:1039647-1040693 | -449 |
| -0.8260155 | 323 | 263 | 237 | 497 | 511 | 451 | chr2:201081884-201083651 | 270 |
| -2.2020186 | 16 | 30 | 117 | 233 | 279 | 238 | chr3:38181780-38182371 | 46 |
| -2.8356995 | 18 | 10 | 8 | 72 | 52 | 133 | chr19:54031026-54032395 | 36 |
| -0.6760742 | 501 | 369 | 485 | 714 | 870 | 581 | chr4:149581871-149583135 | 590 |
| -1.2392909 | 33 | 26 | 38 | 61 | 87 | 81 | chr1:201364011-201364232 | 663 |
| -3.7004397 | 1 | 0 | 1 | 11 | 5 | 10 | chr11:33137755-33137902 | 1785 |

TABLE 14-continued

Comprehensive DNA Methylation and K27 Profiles of CD44+ Nulliparous and Parous Breast Epithelial Cells

| | | | | | | | | | |
|---|---|---|---|---|---|---|---|---|---|
| −0.8230082 | 162 | 183 | 205 | 250 | 365 | 358 | chr1:203557377-203558160 | −262 |
| −0.5955247 | 206 | 186 | 107 | 254 | 252 | 248 | chr14:34942730-34943491 | 601 |
| NA | 0 | 0 | 0 | 6 | 13 | 7 | chr6:29904116-29905129 | 1888 |
| −0.6354468 | 145 | 159 | 164 | 265 | 220 | 242 | chr2:161982831-161983691 | 2396 |
| −1.070627 | 91 | 74 | 124 | 149 | 220 | 238 | chr2:233927903-233929031 | 576 |
| −0.7412657 | 62 | 68 | 71 | 96 | 140 | 100 | chr8:144 731557-144 732196 | −220 |
| −0.4002638 | 199 | 235 | 204 | 277 | 274 | 291 | chr12:48021402-48023959 | −5442 |
| −1.1953476 | 60 | 86 | 54 | 118 | 151 | 189 | chr9:203667-204892 | 1614 |
| 0.92218047 | 156 | 135 | 124 | 77 | 46 | 96 | chr9:204976-205591 | 610 |
| −1.23 17466 | 213 | 187 | 171 | 503 | 442 | 396 | chr3:102925478-102926579 | −155 |
| −0.6579373 | 179 | 98 | 192 | 232 | 227 | 281 | chr11:34893820-34894405 | −140 |
| −0.7294604 | 147 | 122 | 155 | 242 | 250 | 211 | chr7:65083798-65084603 | 481 |
| −0.8995039 | 134 | 129 | 220 | 310 | 307 | 284 | chr16:1974220-1974874 | 397 |
| −0.6832152 | 56 | 58 | 61 | 83 | 96 | 102 | chr3:4483944-4484800 | −418 |
| −0.5340363 | 426 | 374 | 459 | 671 | 630 | 522 | chr6:83959178-83960889 | 283 |
| −1.5360529 | 159 | 200 | 101 | 634 | 327 | 373 | chr1:1435936-1437511 | −694 |
| −1.2459102 | 50 | 75 | 101 | 202 | 207 | 127 | chr19:3432929-3434399 | −2124 |
| −0.640377 | 255 | 383 | 375 | 490 | 619 | 470 | chr19:60855675-60858282 | −249 |
| −0.6532794 | 251 | 241 | 271 | 469 | 361 | 370 | chr3:99724331-99725242 | −186 |
| −1.238587 | 133 | 125 | 109 | 328 | 250 | 288 | chr1:113062737-113063644 | −3717 |
| −0.7050563 | 73 | 43 | 76 | 95 | 99 | 119 | chr7:8091196-8091552 | 764 |
| −0.6721144 | 221 | 184 | 232 | 336 | 312 | 367 | chr7:64834261-64835583 | −37 |
| −0.5503223 | 217 | 167 | 178 | 248 | 253 | 322 | chr1:54126633-54128453 | −4905 |
| −0.5693871 | 427 | 593 | 439 | 669 | 736 | 760 | chr1:148078259-148080734 | 1446 |
| −1.2816642 | 122 | 82 | 123 | 199 | 414 | 182 | chr13:48447252-48448068 | −388 |
| −0.8242168 | 321 | 248 | 233 | 598 | 385 | 437 | chr1:166371323-166373137 | 18 |
| −0.3288834 | 718 | 707 | 727 | 801 | 1100 | 802 | chr7:42963169-42964310 | 297 |
| −1.1666199 | 136 | 164 | 137 | 204 | 361 | 416 | chr10:20144404 7-20146014 | −347 |
| −3.6482884 | 6 | 2 | 5 | 22 | 45 | 96 | chr8:20155404-20156652 | 1055 |
| −2.0512253 | 9 | 10 | 64 | 107 | 93 | 144 | chr16:316190 67-31619974 | 86 |
| −1.1056618 | 129 | 95 | 105 | 211 | 231 | 266 | chr18:51405373-51406320 | 1012 |
| −0.6050452 | 346 | 442 | 615 | 678 | 782 | 674 | chr19:54312942-54315267 | 105 |
| −0.8788833 | 79 | 119 | 69 | 163 | 174 | 154 | chr10:16602981 -16604063 | 488 |
| −0.798097 | 85 | 70 | 113 | 155 | 140 | 171 | chr4:79196318-79198600 | −288 |
| −2.3058084 | 10 | 2 | 6 | 45 | 23 | 21 | chr12:63083826-63084298 | −437 |
| −1.092597 | 73 | 101 | 90 | 169 | 199 | 195 | chr17:44008257-44009194 | −1916 |
| −0.5064475 | 254 | 263 | 213 | 303 | 366 | 368 | chr4:52611354-52612883 | −231 |
| −1.092597 | 73 | 101 | 90 | 169 | 199 | 195 | chr17:44008257-44009194 | 2017 |
| −0.5340363 | 426 | 374 | 459 | 671 | 630 | 522 | chr6:83959178-83960889 | −379 |
| −0.7997527 | 216 | 138 | 244 | 302 | 334 | 405 | chr4:89731781 -89733576 | 9 |
| −0.5693871 | 427 | 593 | 439 | 669 | 736 | 760 | chr1:148078259-148080734 | −107 |
| −0.5693871 | 427 | 593 | 439 | 669 | 736 | 760 | chr1:148078259-148080734 | −107 |
| −0.8507942 | 81 | 70 | 78 | 114 | 135 | 164 | chr6:26232360-26233141 | −639 |
| −0.9693329 | 166 | 181 | 176 | 234 | 474 | 316 | chr11:45642072-45643505 | 960 |
| −1.4180275 | 35 | 92 | 114 | 236 | 205 | 203 | chr19:41333556-41335121 | 1273 |
| −0.7856743 | 140 | 125 | 166 | 219 | 285 | 239 | chr12:16650065-16650933 | 1792 |
| −1.1562618 | 134 | 96 | 159 | 189 | 353 | 325 | chr6:26358450-26360034 | −615 |
| −1.006223 | 128 | 77 | 142 | 196 | 238 | 263 | chr7:30599934-30600992 | −242 |
| −1.0302322 | 79 | 176 | 170 | 286 | 294 | 288 | chr5:180582673-180583620 | 235 |
| −0.4456082 | 203 | 166 | 203 | 258 | 256 | 265 | chr16:66007420-66008210 | 63 |
| −0.6376183 | 350 | 333 | 411 | 495 | 680 | 527 | chr2:46377228-46378728 | −88 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| -0.6429623 | 432 | 381 | 414 | 718 | 619 | 579 | chr9:126573587-126575123 | -4902 |
| -0.3801578 | 332 | 370 | 376 | 431 | 495 | 477 | chr20:581185-582809 | -107 |
| -1.1205589 | 47 | 17 | 45 | 70 | 76 | 91 | chrX:153324890-153325776 | -368 |
| -3.4594316 | 0 | 6 | 3 | 22 | 35 | 42 | chr6:43053760-43054864 | 647 |
| -0.605453 | 260 | 252 | 257 | 389 | 459 | 322 | chr3:42896923-42897952 | -4800 |
| -0.7023629 | 133 | 130 | 83 | 172 | 183 | 208 | chr21:37283946-37285188 | -194 |
| -1.1963972 | 61 | 65 | 42 | 169 | 112 | 104 | chr9:19118327-19119326 | -1253 |
| -0.7737241 | 130 | 124 | 56 | 190 | 162 | 178 | chr20:20293002-20294031 | -3248 |
| -1.2696308 | 266 | 221 | 204 | 713 | 497 | 456 | chr14:54807584-54809084 | -290 |
| -5.4918531 | 0 | 1 | 0 | 9 | 17 | 19 | chr2:128792575-128792605 | 51 |
| -0.9779737 | 279 | 273 | 174 | 390 | 563 | 477 | chr1:154735429-154738158 | 360 |
| -0.6103478 | 140 | 175 | 192 | 235 | 243 | 296 | chr5:176491360-176494008 | -754 |
| -0.6553084 | 205 | 178 | 144 | 243 | 276 | 311 | chr3:57969514-57970738 | 960 |
| -1.8172704 | 41 | 31 | 73 | 91 | 235 | 185 | chr3:38665606-38666656 | 36 |
| -0.8751703 | 185 | 148 | 228 | 401 | 322 | 306 | chr7:99974343-99975502 | 153 |
| -0.3885258 | 184 | 146 | 178 | 221 | 218 | 226 | chr10:101481403-101482095 | 664 |
| -0.954657 | 136 | 76 | 192 | 273 | 237 | 273 | chr1:64448164-64448915 | -216 |
| -0.8633653 | 145 | 175 | 178 | 272 | 342 | 292 | chr10:94809459-94811010 | -776 |
| -0.8132621 | 139 | 102 | 142 | 174 | 252 | 247 | chr7:21096315-21097801 | 113 |
| -0.5666568 | 273 | 326 | 247 | 365 | 507 | 381 | chr15:70309984-70311301 | 96 |
| -0.7578381 | 157 | 108 | 133 | 190 | 259 | 224 | chr19:5855901-5856864 | 531 |
| -0.6579373 | 179 | 98 | 192 | 232 | 227 | 281 | chr11:34893820-34894405 | 403 |
| -3.3219281 | 0 | 0 | 8 | 22 | 21 | 37 | chr1:19684517-19685466 | -412 |
| -2.4035156 | 55 | 0 | 0 | 90 | 99 | 102 | chr8:143805171-143805958 | -58 |
| -0.8995039 | 134 | 129 | 220 | 310 | 307 | 284 | chr16:1974220-1974874 | -3106 |
| -1.4486683 | 129 | 137 | 52 | 258 | 290 | 320 | chr22:17846606-17848701 | -927 |
| -0.3946614 | 268 | 274 | 278 | 351 | 348 | 379 | chr1:125987746-12602700 | -316 |
| -1.2425703 | 18 | 23 | 30 | 61 | 50 | 57 | chr2:203812030-203812879 | 1046 |
| -1.1938797 | 16 | 22 | 35 | 59 | 50 | 58 | chr19:61874170-61875174 | 1386 |
| -3.4353861 | 1 | 7 | 3 | 21 | 43 | 55 | chr4:106614654-106614915 | -108 |
| -0.9293311 | 130 | 123 | 134 | 214 | 302 | 221 | chr2:60963129-60963768 | 1193 |
| -2.835506 | 1 | 6 | 22 | 51 | 72 | 84 | chr22:31200323-31200989 | -567 |
| -1.4866246 | 18 | 30 | 38 | 52 | 77 | 112 | chr16:67778615-67779949 | 732 |
| -0.8886389 | 162 | 113 | 75 | 195 | 210 | 243 | chrX:488661194-48867383 | 235 |
| -0.4918008 | 199 | 234 | 180 | 286 | 293 | 283 | chr14:104226492-104227458 | -12 |
| -1.7083964 | 107 | 167 | 185 | 621 | 502 | 377 | chr17:69939772-69941487 | 1368 |
| -1.2136752 | 27 | 63 | 76 | 116 | 120 | 149 | chr5:131160590-131161256 | -268 |
| -0.5619949 | 461 | 392 | 350 | 668 | 596 | 512 | chr17:399889670-39990582 | -674 |
| -0.7410076 | 156 | 189 | 154 | 223 | 292 | 319 | chr8:144968190-144969528 | 678 |
| -0.6429623 | 432 | 381 | 414 | 718 | 619 | 579 | chr9:126573587-126575123 | -958 |
| -1.2593866 | 66 | 70 | 62 | 168 | 156 | 150 | chr11:65990598-65992847 | 811 |
| -1.1298432 | 119 | 150 | 246 | 485 | 314 | 328 | chr6:169843597-169844480 | 46 |
| -0.4250429 | 154 | 145 | 168 | 218 | 195 | 214 | chr9:139436440-139437802 | 414 |
| -0.9767384 | 256 | 280 | 183 | 341 | 574 | 500 | chr3:106568558-106570647 | 1200 |
| -0.3885258 | 184 | 146 | 178 | 221 | 218 | 226 | chr10:101481403-101482095 | -198 |
| -0.9428315 | 78 | 92 | 126 | 221 | 157 | 191 | chr4:79915651-79916721 | -369 |
| -0.5405684 | 142 | 140 | 125 | 178 | 182 | 232 | chr19:18124441-18125919 | 165 |
| -1.6679239 | 47 | 28 | 32 | 138 | 80 | 122 | chr5:140552873-140554755 | -5717 |
| -1.6679239 | 47 | 28 | 32 | 138 | 80 | 122 | chr5:140552873-140554755 | 1679 |
| -1.2016339 | 10 | 11 | 9 | 22 | 20 | 27 | chr5:140511060-140512468 | -3999 |
| -0.3938662 | 179 | 194 | 159 | 225 | 249 | 225 | chr19:60320068-60321423 | -6 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| −0.8120432 | 228 | 207 | 355 | 393 | 542 | 452 | chr10:112246824-112247869 | −268 |
| −0.6981731 | 73 | 118 | 103 | 150 | 154 | 173 | chr8:29263712-29265267 | −2248 |
| −0.3396924 | 272 | 228 | 291 | 323 | 333 | 345 | chrX:71441053-71443548 | 1215 |
| −0.5693871 | 427 | 593 | 439 | 669 | 736 | 760 | chr1:148078259-148080734 | 1446 |
| −0.3960722 | 129 | 134 | 139 | 162 | 168 | 199 | chr8:57521453-57523188 | −1173 |
| −0.9619165 | 170 | 198 | 131 | 241 | 366 | 365 | chr9:123002766-123004369 | 619 |
| −0.7909044 | 139 | 89 | 87 | 191 | 179 | 175 | chr1:24944631-24945506 | 722 |
| −0.5086673 | 192 | 193 | 178 | 240 | 249 | 312 | chr10:95245414-95246971 | −186 |
| −0.6461833 | 77 | 68 | 78 | 101 | 127 | 121 | chr1:6584303-6585042 | 844 |
| −0.9878764 | 80 | 81 | 78 | 137 | 157 | 180 | chr7:74126564-74128204 | 251 |
| −1.0425246 | 120 | 170 | 178 | 203 | 446 | 315 | chr1:2248554-2250318 | −678 |
| −0.696908 | 112 | 149 | 148 | 207 | 218 | 238 | chr17:15105877-15107151 | 100 |
| −0.4002638 | 199 | 235 | 204 | 277 | 274 | 291 | chr12:48021402-48023959 | −4627 |
| −0.6530515 | 98 | 68 | 103 | 153 | 129 | 141 | chr11:128747412-128748710 | −3029 |
| −1.025445 | 62 | 123 | 96 | 242 | 146 | 184 | chr16:53519496-53520577 | −2575 |
| −0.5202419 | 328 | 264 | 297 | 452 | 451 | 372 | chr5:150118559-150119414 | −711 |
| −1.2644565 | 112 | 77 | 149 | 187 | 302 | 323 | chr4:141664301 -141665581 | 140 |
| −0.7940153 | 85 | 122 | 150 | 195 | 187 | 237 | chr2:25749099-25750442 | 237 |
| −1.0610011 | 103 | 100 | 98 | 160 | 216 | 252 | chr17:64019028-64020947 | 283 |
| −0.5410454 | 120 | 129 | 129 | 167 | 161 | 222 | chr7:44429442-44430106 | 2 |
| −1.4927399 | 85 | 69 | 99 | 174 | 292 | 246 | chr8:73610742-73612986 | −315 |
| −0.7467517 | 129 | 135 | 118 | 186 | 225 | 230 | chr15:43209226-43210016 | 138 |
| −1.1460783 | 120 | 165 | 81 | 236 | 320 | 254 | chr6:126110899-126112654 | −648 |
| −1.1061726 | 124 | 123 | 100 | 182 | 301 | 264 | chr19:46460953-46462066 | 1279 |
| −0.7094099 | 193 | 200 | 125 | 240 | 314 | 293 | chr14:22495206-22496276 | 419 |
| −1.170379 | 198 | 171 | 337 | 687 | 530 | 372 | chr3:180522816-180524509 | −582 |
| −1.1495135 | 110 | 95 | 143 | 190 | 288 | 294 | chr1:10192786-10194291 | 188 |
| −0.648199 | 432 | 411 | 444 | 741 | 774 | 502 | chr19:61323480-61324669 | 387 |
| −0.5838765 | 166 | 146 | 131 | 201 | 239 | 224 | chr7:64107511 -64108400 | 735 |
| −1.0752881 | 98 | 102 | 164 | 194 | 267 | 306 | chr1:37271861-37273886 | −442 |
| −0.5917608 | 337 | 392 | 259 | 438 | 549 | 502 | chr12:55769321 -55770349 | 892 |
| −0.7835675 | 178 | 171 | 114 | 207 | 310 | 280 | chr19:44588464-44589366 | −411 |
| −0.7451197 | 90 | 91 | 66 | 135 | 118 | 161 | chr20:23279336-23279979 | 285 |
| −0.894023 | 187 | 119 | 167 | 380 | 250 | 249 | chr17:32380320-32381002 | 374 |
| −0.7050563 | 73 | 43 | 76 | 95 | 99 | 119 | chr17:8091196-8091552 | −1946 |
| −0.7379534 | 201 | 166 | 217 | 275 | 330 | 369 | chr8:23595241 -23596905 | 322 |
| −0.8897547 | 152 | 122 | 93 | 190 | 252 | 238 | chr1:40746249-40747435 | −177 |
| −4.3219281 | 0 | 0 | 2 | 8 | 12 | 20 | chr2:54831332-54832506 | −682 |
| −0.3758482 | 251 | 252 | 206 | 301 | 322 | 297 | chr1:11662839-11663585 | 646 |
| −1.6096246 | 40 | 31 | 45 | 75 | 117 | 162 | chr3:49952030-49953467 | 153 |
| −0.6828889 | 289 | 312 | 296 | 587 | 471 | 382 | chr17:71891524-71893964 | 448 |
| −0.808656 | 161 | 177 | 137 | 262 | 244 | 326 | chr10:103103373-103104800 | 272 |
| −0.7291762 | 87 | 86 | 87 | 124 | 149 | 158 | chrX:48317321-48318283 | 23 |
| −1.6208592 | 65 | 43 | 64 | 117 | 229 | 183 | chr12:15833072-15833634 | 248 |
| −1.7104934 | 37 | 25 | 81 | 101 | 194 | 173 | chr1:205561009-205561733 | −68 |
| −2.6288168 | 27 | 34 | 47 | 147 | 437 | 84 | chr19:63559791 -63561351 | −3894 |
| −0.6255362 | 236 | 292 | 255 | 375 | 453 | 380 | chr19:50694374-50695061 | 1147 |
| −0.5979221 | 363 | 458 | 435 | 663 | 653 | 585 | chr19:12764569-12766186 | 2068 |
| −1.6903155 | 10 | 15 | 19 | 55 | 41 | 46 | chr1:53166252-53166530 | 856 |
| −0.3837183 | 201 | 208 | 208 | 283 | 250 | 272 | chr4:14612382-14613671 | −1593 |
| −0.853977 | 181 | 151 | 203 | 297 | 336 | 334 | chr17:75386229-75387914 | −1586 |

TABLE 14-continued

Comprehensive DNA Methylation and K27 Profiles of CD44+ Nulliparous and Parous Breast Epithelial Cells

| | | | | | | | | | |
|---|---|---|---|---|---|---|---|---|---|
| -0.4250429 | 154 | 145 | 168 | 218 | 195 | 214 | chr9:139436440-139437802 | -546 |
| -0.9463313 | 50 | 46 | 82 | 102 | 99 | 142 | chr9:33740831-33741262 | 532 |
| -0.5839075 | 309 | 310 | 293 | 587 | 430 | 350 | chr17:4589887-4590592 | 172 |
| -0.7042288 | 350 | 276 | 310 | 592 | 542 | 391 | chr6:136913237-136913751 | -9 |
| -1.2988137 | 68 | 95 | 139 | 322 | 190 | 231 | chr3:52287415-52288201 | -109 |
| -1.1028999 | 86 | 96 | 75 | 138 | 215 | 199 | chr5:177472561-177473375 | -193 |
| -1.4884997 | 82 | 61 | 125 | 153 | 303 | 296 | chr19:58662506-58663652 | 279 |
| -0.4386958 | 470 | 412 | 373 | 606 | 575 | 520 | chr1:119864422-11987921 | -409 |
| -0.925539 | 172 | 184 | 219 | 295 | 438 | 359 | chr16:65741109-65742098 | 800 |
| -0.5461258 | 177 | 169 | 156 | 242 | 208 | 283 | chr5:176365206-176367019 | -63 |
| -0.4551014 | 239 | 237 | 252 | 310 | 307 | 381 | chr1:11673128-11676088 | 241 |
| -1.741688 | 30 | 60 | 93 | 201 | 202 | 209 | chr4:482714-483825 | 173 |
| -0.5070511 | 394 | 429 | 350 | 584 | 607 | 476 | chr5:88214660-88215585 | -64 |
| -0.953942 | 150 | 146 | 70 | 315 | 205 | 189 | chr14:88090262-88090871 | 310 |
| -0.3550364 | 152 | 159 | 137 | 193 | 194 | 186 | chr2:213111534-213112245 | -292 |
| -0.8604486 | 199 | 172 | 193 | 248 | 409 | 367 | chr11:71610641-71613108 | -1598 |
| -0.9168061 | 265 | 213 | 218 | 319 | 503 | 492 | chr2:1331424 74-133145778 | 1414 |
| -1.0318489 | 76 | 71 | 77 | 118 | 160 | 180 | chr22:27993009-27995892 | 434 |
| -1.2293385 | 51 | 58 | 39 | 79 | 106 | 162 | chr2:10505952-10507359 | -751 |
| -1.3105593 | 117 | 263 | 257 | 695 | 508 | 377 | chr7:42242650-42243241 | 198 |
| -0.4193376 | 244 | 236 | 190 | 308 | 305 | 283 | chr2:149348765-149350484 | 336 |
| -0.3084734 | 336 | 309 | 303 | 380 | 394 | 400 | chr7:130003338-130004481 | 229 |
| -0.3423723 | 355 | 337 | 331 | 497 | 403 | 397 | chr10:52052492-52053729 | 633 |
| -0.7320978 | 189 | 135 | 151 | 224 | 253 | 312 | chr2:183288467-183289461 | -279 |
| -0.6758253 | 232 | 258 | 233 | 304 | 398 | 453 | chr5:78844706-78846820 | -307 |
| -2.9311673 | 216 | 0 | 4 | 777 | 433 | 468 | chr1:1656660-1669241 | -159 |
| -0.8198916 | 80 | 124 | 107 | 152 | 192 | 205 | chr5:115939727-115940289 | -1558 |
| -1.0350469 | 94 | 77 | 73 | 155 | 169 | 176 | chr20:3775447-3776186 | 368 |
| -0.8160986 | 163 | 75 | 138 | 197 | 208 | 257 | chr4:104009348-104010163 | 180 |
| -0.4520182 | 102 | 113 | 122 | 153 | 146 | 162 | chr2:102719675-102720199 | -192 |
| -1.1331493 | 33 | 69 | 79 | 106 | 143 | 148 | chr19:4294590-4295246 | 343 |
| -0.7151362 | 306 | 349 | 224 | 396 | 536 | 511 | chr1:85814753-85816432 | -3439 |
| -0.8507942 | 81 | 70 | 78 | 114 | 135 | 164 | chr6:26232360-26233141 | 399 |
| -1.741688 | 30 | 60 | 93 | 201 | 202 | 209 | chr4:482714-483825 | 281 |
| -0.6731897 | 403 | 387 | 320 | 777 | 547 | 446 | chr14:20921619-20922486 | 213 |
| -1.2874397 | 33 | 44 | 50 | 96 | 86 | 128 | chr2:74596891-74597416 | 2035 |
| -3.1583776 | 16 | 28 | 179 | 682 | 851 | 458 | chr22:36285998-36287625 | 395 |
| -1.2658463 | 59 | 100 | 140 | 195 | 301 | 223 | chr4:158216229-158217600 | 188 |
| -0.6255362 | 236 | 292 | 255 | 375 | 453 | 380 | chr19:50694374-50695061 | -2566 |
| -3.245476 | 9 | 12 | 10 | 76 | 104 | 114 | chr19:52050366-52050962 | -4621 |
| -1.3155018 | 115 | 95 | 105 | 172 | 337 | 275 | chr16:559119-560435 | -227 |
| -0.4422996 | 260 | 234 | 253 | 357 | 355 | 303 | chr4:147778755-147779781 | -226 |
| -1.1562618 | 134 | 96 | 159 | 189 | 353 | 325 | chr6:26358450-26360034 | -428 |
| -0.8186348 | 39 | 70 | 73 | 111 | 97 | 113 | chr20:32727786-32728548 | 583 |
| -0.5897942 | 337 | 338 | 418 | 575 | 561 | 509 | chr10:105715269-105718020 | -815 |
| -0.7854955 | 114 | 134 | 132 | 165 | 196 | 294 | chr19:50701407-50702869 | -389 |
| -0.3782036 | 376 | 332 | 373 | 476 | 506 | 423 | chr5:79900812-79902260 | 318 |
| -3.2917042 | 14 | 26 | 42 | 476 | 178 | 149 | chr7:1465486-1466227 | -221 |
| -0.4115129 | 371 | 371 | 385 | 547 | 473 | 479 | chr7:121731725-121733798 | -926 |
| -0.5405684 | 188 | 193 | 158 | 264 | 251 | 269 | chr2:114230454-114231272 | 7 |
| -0.454637 | 199 | 184 | 165 | 247 | 237 | 267 | chr11:787114-788785 | -1728 |

TABLE 14-continued

Comprehensive DNA Methylation and K27 Profiles of CD44+ Nulliparous and Parous Breast Epithelial Cells

| | | | | | | | |
|---|---|---|---|---|---|---|---|
| -0.6900445 | 170 | 130 | 150 | 209 | 281 | 236 | chr1:28847331-28848288 | 111 |
| -0.7672952 | 347 | 364 | 108 | 428 | 514 | 452 | chr11:57181281-57182738 | 804 |
| -0.8951385 | 134 | 116 | 128 | 170 | 239 | 294 | chr1:234753006-234754499 | 53 |
| -0.7251828 | 146 | 140 | 132 | 245 | 215 | 231 | chr6:68880376-68880999 | 226 |
| -0.6448508 | 285 | 294 | 349 | 467 | 535 | 449 | chr4:108175006-108176027 | 1386 |
| -0.7962867 | 51 | 97 | 95 | 151 | 127 | 144 | chr2:56417662-56418294 | 318 |
| -0.8005142 | 32 | 60 | 59 | 78 | 92 | 93 | chr19:804003-804580 | 1001 |
| -1.7655347 | 30 | 25 | 35 | 71 | 74 | 161 | chr7:23243362-23244946 | 382 |
| -1.6234366 | 11 | 12 | 14 | 26 | 38 | 50 | chr7:137336989-137337895 | -56 |
| -0.5574341 | 127 | 156 | 105 | 184 | 192 | 195 | chr18:53861812-53862890 | -426 |
| -0.6962193 | 106 | 118 | 92 | 167 | 166 | 179 | chr21:32026135-32027025 | -447 |
| -0.5926059 | 205 | 127 | 170 | 265 | 256 | 236 | chr21:151051121-151051685 | 1023 |
| -1.2242648 | 28 | 49 | 33 | 70 | 76 | 111 | chr14:36193035-36194014 | -3008 |
| -0.4495699 | 286 | 252 | 236 | 328 | 369 | 360 | chr7:100091002-100092847 | 96 |
| -0.4755907 | 181 | 166 | 157 | 221 | 253 | 227 | chr9:76892566-76893760 | -210 |
| -0.7738024 | 98 | 121 | 129 | 155 | 216 | 224 | chr19:978490-980897 | 2396 |
| -1.4486683 | 129 | 137 | 52 | 258 | 290 | 320 | chr22:17846606-17848701 | 238 |
| -0.9678793 | 206 | 183 | 156 | 248 | 442 | 376 | chr11:85457366-85458376 | -115 |
| -0.5514099 | 224 | 219 | 137 | 316 | 256 | 278 | chr1:34414249-34415569 | -230 |
| 0.78669545 | 130 | 118 | 116 | 61 | 58 | 92 | chr10:5748284-5748518 | 146 |
| 0.61277435 | 133 | 149 | 137 | 75 | 88 | 111 | chr16:1603973-1604213 | -808 |
| 1.09085343 | 70 | 71 | 72 | 15 | 43 | 42 | chr11:122437240-122438400 | 234 |
| 1.48032896 | 72 | 85 | 69 | 23 | 25 | 33 | chr5:115179218-115179883 | 754 |
| 1.38755196 | 619 | 422 | 848 | 337 | 171 | 214 | chr9:137992213-137993082 | 400 |
| 0.81096618 | 164 | 194 | 142 | 83 | 95 | 107 | chr16:82959484-82959722 | -30 |
| 0.82579527 | 118 | 133 | 123 | 63 | 51 | 97 | chr9:115077683-115077844 | -31 |
| 1.15121881 | 210 | 203 | 200 | 151 | 93 | 32 | chr2:27340087-27341044 | -1101 |
| 3.36074734 | 83 | 38 | 105 | 22 | 0 | 0 | chr7:45562776-45563694 | -1069 |
| 0.98325674 | 82 | 73 | 102 | 38 | 41 | 51 | chr1:38807324-3807550 | -728 |
| 1.00998409 | 113 | 108 | 69 | 47 | 51 | 46 | chr18:26935930-26936675 | 84 |
| 0.75647825 | 140 | 138 | 119 | 96 | 62 | 77 | chr17:45008485-45009430 | 480 |
| 0.97182933 | 281 | 362 | 422 | 205 | 119 | 219 | chr8:38363348-38363624 | -4539 |
| 1.74768476 | 1160 | 653 | 1159 | 495 | 227 | 163 | chr22:17273887-17274766 | 591 |
| 0.61397095 | 131 | 149 | 147 | 80 | 98 | 101 | chr1:226394543-226395184 | 259 |
| -0.5027242 | 120 | 130 | 129 | 160 | 174 | 203 | chr6:86408184-86408678 | 1315 |
| 0.78700628 | 371 | 390 | 295 | 256 | 167 | 189 | chr6:86409192-86410070 | 115 |
| 0.67807191 | 121 | 175 | 120 | 94 | 74 | 92 | chr5:2804525-2805526 | -256 |
| 1.48112669 | 60 | 85 | 56 | 21 | 22 | 29 | chr1:166171964-166172050 | -150 |
| 1.28149092 | 992 | 1112 | 1027 | 522 | 406 | 360 | chr17:7965768-7968799 | -4698 |
| 1.0957324 | 1200 | 1064 | 929 | 612 | 434 | 448 | chr17:7195418-7196997 | 276 |
| 0.64341784 | 198 | 216 | 203 | 125 | 121 | 149 | chr20:34005027-34005915 | 371 |
| 1.63941028 | 21 | 21 | 39 | 3 | 13 | 10 | chr3:159304591-159304760 | -1155 |
| 1.5360529 | 89 | 154 | 105 | 26 | 58 | 36 | chr7:23686138-23687515 | 553 |
| 0.63148678 | 189 | 264 | 193 | 153 | 102 | 162 | chr20:61838942-61839996 | 1048 |
| 0.97239134 | 615 | 653 | 647 | 384 | 257 | 335 | chr19:61344489-61345629 | 692 |
| 0.60050736 | 1005 | 844 | 1086 | 571 | 665 | 693 | chr1:95161234-95165177 | -603 |
| 0.79970135 | 177 | 192 | 148 | 102 | 72 | 123 | chr2:48737132-48737875 | -250 |
| 1.67377177 | 315 | 189 | 166 | 54 | 69 | 87 | chr1:77411177-77411941 | 409 |
| 0.70143916 | 132 | 117 | 112 | 78 | 73 | 71 | chr9:92603631-92603791 | -121 |
| 0.98325674 | 82 | 73 | 102 | 38 | 41 | 51 | chr1:38807324-3807550 | 610 |
| NA | 9 | 4 | 5 | 0 | 0 | 0 | chr20:42590341-42591024 | -3167 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| 2.15959364 | 143 | 122 | 222 | 42 | 16 | 51 | chr5:132193549-132194720 | -4233 |
| 1.38082178 | 44 | 48 | 33 | 11 | 15 | 22 | chr5:15552531-15553771 | -153 |
| 1.52256596 | 72 | 57 | 52 | 26 | 9 | 28 | chr17:77453183-77453445 | -131 |
| 0.53859254 | 66 | 69 | 64 | 40 | 50 | 47 | chr11:69165352-69165427 | 336 |
| 1.30753187 | 129 | 127 | 93 | 59 | 30 | 52 | chr11:62380031-62380122 | -140 |
| 0.78174731 | 117 | 127 | 105 | 59 | 63 | 81 | chr1:243065639-243065788 | 452 |
| 1.02191478 | 69 | 59 | 71 | 26 | 33 | 39 | chr7:2849539-2850319 | 556 |
| 0.81740859 | 239 | 253 | 264 | 112 | 145 | 172 | chr6:65774170-65776940 | -171 |
| 1.72698151 | 73 | 53 | 66 | 15 | 10 | 33 | chr2:70119562-70120127 | -235 |
| 0.84036477 | 226 | 244 | 171 | 125 | 94 | 139 | chr2:109728691-109729896 | 94 |
| 1.07179068 | 30 | 38 | 35 | 15 | 15 | 19 | chr1:2864599-2864765 | -1111 |
| 1.10433666 | 60 | 46 | 66 | 26 | 30 | 24 | chr14:76857390-76857632 | 53 |
| 1.19125005 | 136 | 186 | 121 | 40 | 60 | 94 | chr16:86460527-86460816 | -70 |
| 0.803346101 | 174 | 219 | 162 | 100 | 86 | 132 | chr16:37526311-37526846 | 330 |
| 1.34889514 | 37 | 57 | 41 | 26 | 8 | 19 | chr1:31658699-31660054 | 827 |
| 0.75348805 | 114 | 112 | 96 | 63 | 50 | 78 | chr2:241586515-241586642 | -349 |
| 2.49476469 | 95 | 114 | 39 | 8 | 11 | 25 | chr1:99502593-99503144 | 381 |
| 0.98326483 | 1348 | 1198 | 1568 | 875 | 761 | 445 | chr16:2954093-2955587 | 623 |
| 1.58957913 | 99 | 157 | 57 | 38 | 30 | 36 | chr19:7896421-7896600 | 541 |
| 1.32027836 | 184 | 122 | 131 | 77 | 33 | 65 | chrX:101792123-101794534 | 379 |
| 0.92321877 | 101 | 111 | 99 | 39 | 61 | 64 | chr17:17147712-17148280 | 592 |
| 1.35453276 | 145 | 127 | 86 | 39 | 33 | 68 | chr1:21982035-21982304 | 106 |
| 0.85626452 | 68 | 76 | 66 | 34 | 35 | 47 | chr1:54763227-54764337 | -52 |
| 1.22831726 | 647 | 545 | 516 | 263 | 201 | 265 | chr10:102096092-102098450 | 510 |
| 0.70948486 | 80 | 102 | 78 | 47 | 50 | 62 | chr3:161955885-161956835 | -329 |
| 2.60203601 | 19 | 44 | 22 | 3 | 2 | 9 | chr9:97824691-97825096 | -1035 |
| 0.88896869 | 102 | 114 | 84 | 56 | 48 | 58 | chr12:84343499-84343620 | 131 |
| 1.34169135 | 43 | 43 | 61 | 16 | 19 | 23 | chr3:130641694-130641738 | 59 |
| 1.48377268 | 263 | 145 | 115 | 82 | 60 | 45 | chr19:8020835-8021781 | -2625 |
| 0.85895612 | 202 | 171 | 182 | 106 | 60 | 140 | chr6:146097340-146098325 | 852 |
| 1.84799691 | 53 | 60 | 49 | 5 | 18 | 22 | chr8:19216086-19216897 | 1005 |
| 0.7695792 | 456 | 664 | 416 | 293 | 248 | 360 | chr14:22904148-22905560 | -172 |
| 1.08861439 | 156 | 204 | 110 | 83 | 68 | 70 | chr11:566245-567005 | 140 |
| 0.65284497 | 261 | 234 | 310 | 145 | 185 | 182 | chr22:22645930-22646097 | 667 |
| 1.02126862 | 66 | 76 | 63 | 20 | 34 | 47 | chr7:101244064-101245314 | -2912 |
| 0.71318821 | 118 | 128 | 95 | 61 | 70 | 77 | chr14:35431494-35432145 | -489 |
| 1.09085343 | 70 | 71 | 72 | 15 | 43 | 42 | chr11:122437240-122438400 | -2430 |
| 0.85333035 | 80 | 87 | 104 | 40 | 50 | 60 | chr9:34579477-34579803 | 82 |
| 1.0957324 | 1200 | 1064 | 929 | 612 | 434 | 448 | chr17:7195418-7196997 | -3013 |
| 0.47212669 | 570 | 466 | 562 | 418 | 417 | 317 | chr6:26379249-26381182 | -967 |
| 0.83338977 | 726 | 606 | 653 | 439 | 245 | 430 | chr3:124228291-124230592 | -175 |
| 0.86302613 | 438 | 522 | 526 | 388 | 198 | 231 | chr14:76297922-76298830 | 389 |
| 1.30753187 | 129 | 127 | 93 | 59 | 30 | 52 | chr11:62380031-62380122 | -17 |
| 0.82579527 | 118 | 133 | 123 | 63 | 51 | 97 | chr9:115077683-115077844 | -73 |
| 1.12066253 | 197 | 180 | 134 | 110 | 43 | 82 | chr5:136861747-136863131 | 478 |
| 0.89649542 | 131 | 122 | 110 | 71 | 49 | 75 | chr10:50488433-50488647 | 188 |
| 0.61470984 | 168 | 215 | 156 | 129 | 94 | 129 | chr19:53466041-53467145 | 128 |
| 1.10433666 | 60 | 46 | 66 | 26 | 30 | 24 | chr14:76857390-76857632 | -533 |
| 0.82554922 | 250 | 268 | 260 | 198 | 126 | 115 | chr4:17632329-17633100 | -231 |
| 1.28149092 | 992 | 1112 | 1027 | 522 | 406 | 360 | chr17:7965768-7968799 | 844 |
| 1.34934686 | 384 | 379 | 804 | 250 | 157 | 208 | chr7:100126892-100128257 | -2768 |

TABLE 14-continued

Comprehensive DNA Methylation and K27 Profiles of CD44+ Nulliparous and Parous Breast Epithelial Cells

| | | | | | | | | |
|---|---|---|---|---|---|---|---|---|
| 0.81665448 | 130 | 176 | 122 | 101 | 53 | 89 | chr3:130228831-130229098 | -3017 |
| 1.78849589 | 22 | 26 | 28 | 3 | 11 | 8 | chr7:27208596-27209003 | -2549 |
| 1.59500617 | 415 | 418 | 176 | 136 | 80 | 118 | chr16:48744364-48745279 | -747 |
| 0.97182933 | 281 | 362 | 422 | 205 | 119 | 219 | chr8:38363348-38363624 | 310 |
| 1.09085343 | 70 | 71 | 72 | 15 | 43 | 42 | chr11:122437240-122438400 | -3652 |
| 0.69168818 | 462 | 363 | 346 | 264 | 207 | 254 | chr2:130655386-130656106 | 418 |
| 1.90399265 | 486 | 481 | 152 | 106 | 82 | 111 | chr1:11635345-11637981 | 663 |
| 0.89847836 | 926 | 892 | 747 | 530 | 426 | 420 | chr11:129824078-129825680 | 801 |
| 0.89649542 | 131 | 122 | 110 | 71 | 49 | 75 | chr10:50488433-50488647 | -3548 |
| 0.95518615 | 753 | 765 | 669 | 608 | 218 | 302 | chr3:9569696-9571131 | 73 |
| 1.28263896 | 167 | 203 | 119 | 65 | 55 | 81 | chr22:48951316-48951745 | 244 |
| 1.09085343 | 70 | 71 | 72 | 15 | 43 | 42 | chr11:122437240-122438400 | -2844 |
| 1.45169597 | 50 | 86 | 50 | 24 | 8 | 36 | chr13:27572645-27573636 | -411 |
| 1.26614032 | 107 | 111 | 61 | 40 | 33 | 43 | chr1:53300951-53301771 | 889 |
| 0.61218397 | 104 | 112 | 105 | 59 | 72 | 79 | chr16:28212027-28212234 | 790 |
| 0.90583329 | 134 | 123 | 84 | 55 | 62 | 65 | chr2:171381064-171382105 | 139 |
| 0.69079857 | 1231 | 1213 | 1154 | 670 | 873 | 686 | chr1:26018322-26020531 | 443 |
| 0.68236656 | 269 | 333 | 340 | 184 | 184 | 219 | chr16:87397740-87398345 | 356 |
| 0.76026221 | 144 | 137 | 156 | 111 | 73 | 74 | chr19:58016588-58016870 | -32 |
| 1.08138833 | 84 | 70 | 83 | 38 | 27 | 47 | chr5:134268268-134268809 | -170 |
| 1.45768184 | 232 | 250 | 136 | 63 | 49 | 113 | chr20:42871701-42872255 | 348 |
| 1.90399265 | 486 | 481 | 152 | 106 | 82 | 111 | chr1:11635345-11637981 | -355 |
| 0.75942044 | 86 | 93 | 80 | 50 | 41 | 62 | chr5:175969265-175969468 | 371 |
| 0.67807191 | 121 | 175 | 120 | 94 | 74 | 92 | chr5:2804525-2805526 | -236 |
| 1.08530731 | 157 | 156 | 105 | 81 | 60 | 56 | chr11:75055973-75057060 | 611 |
| 0.98326483 | 1348 | 1198 | 1568 | 875 | 761 | 445 | chr16:2954093-2955587 | -4502 |
| 1.0340932 | 438 | 248 | 256 | 195 | 107 | 158 | chr7:7021767-7022604 | 1422 |
| 0.63173319 | 240 | 241 | 193 | 161 | 117 | 157 | chr20:61966516-61966776 | -387 |
| 0.44170545 | 159 | 140 | 156 | 113 | 116 | 106 | chr7:717666-718276 | 688 |
| 1.04663109 | 823 | 641 | 674 | 384 | 302 | 349 | chr15:76698191-76700189 | 1187 |
| 1.00826762 | 76 | 50 | 49 | 30 | 22 | 35 | chr3:173647786-173648259 | 875 |
| 1.08934257 | 548 | 590 | 494 | 297 | 211 | 259 | chr2:238322032-238324042 | 1230 |
| 1.51402659 | 508 | 326 | 297 | 164 | 89 | 143 | chr12:111047454-111049040 | 484 |
| 1.4150375 | 95 | 128 | 65 | 39 | 21 | 48 | chr2:241408252-241409207 | -432 |
| 0.79851813 | 1004 | 931 | 954 | 853 | 434 | 374 | chr6:134540935-134541770 | -3625 |
| 0.82515472 | 411 | 518 | 437 | 318 | 167 | 286 | chr7:26741966-26743420 | -74 |
| 0.79585928 | 89 | 82 | 79 | 59 | 24 | 61 | chr22:16490793-16491191 | 596 |
| 1.07613107 | 130 | 170 | 128 | 62 | 59 | 82 | chr12:131194792-131194986 | -56 |
| 0.79501826 | 98 | 77 | 87 | 49 | 50 | 52 | chr7:131912984-131913173 | -1215 |
| 0.69168818 | 462 | 363 | 346 | 264 | 207 | 254 | chr2:130655386-130656106 | -426 |
| 0.93920832 | 126 | 132 | 137 | 62 | 53 | 91 | chr13:100124784-100125592 | -84 |
| 0.43568181 | 220 | 193 | 197 | 145 | 147 | 159 | chr16:10581752-10582511 | -91 |
| 0.65284497 | 261 | 234 | 310 | 145 | 185 | 182 | chr22:22639606-22639773 | 664 |
| 0.62890585 | 142 | 143 | 165 | 95 | 86 | 110 | chr19:10392320-10392440 | 48 |
| 1.0850361 | 114 | 97 | 86 | 45 | 42 | 53 | chr3:131312631-131313003 | 149 |
| 0.74639501 | 99 | 112 | 96 | 62 | 50 | 71 | chr5:76362205-76362347 | 289 |
| 1.43942166 | 60 | 68 | 51 | 25 | 27 | 14 | chr10:4859083-4859340 | 810 |
| 1.27665402 | 114 | 95 | 89 | 39 | 36 | 48 | chr8:8123536-8123907 | 220 |
| 0.60550736 | 1005 | 844 | 1086 | 571 | 665 | 693 | chr11:95161234-95165177 | -84 |
| 1.06667104 | 59 | 50 | 46 | 25 | 18 | 31 | chr10:724666-725492 | 529 |
| 0.91600991 | 213 | 342 | 179 | 133 | 107 | 149 | chr1:117010995-117012037 | 321 |

TABLE 14-continued

Comprehensive DNA Methylation and K27 Profiles of CD44+ Nulliparous and Parous Breast Epithelial Cells

| | | | | | | |
|---|---|---|---|---|---|---|
| 0.90098999 | 221 | 271 | 240 | 96 | 160 | 136 | chr10:133994726-133995657 | −502 |
| 0.95015145 | 1638 | 1315 | 1655 | 1181 | 669 | 535 | chr19:47448945-47450989 | 1182 |
| 0.53546054 | 162 | 184 | 141 | 109 | 108 | 119 | chr5:176662893-176663422 | −283 |
| 0.9090915 | 86 | 86 | 74 | 40 | 35 | 56 | chr6:159159334-159159497 | −87 |
| 1.28010792 | 148 | 119 | 73 | 34 | 53 | 53 | chr6:7673027-7673366 | 1187 |
| 1.07613107 | 130 | 170 | 128 | 62 | 59 | 82 | chr12:131194792-131194986 | −56 |
| 1.91358525 | 73 | 55 | 34 | 22 | 6 | 15 | chr10:102269034-102270305 | −84 |
| 0.57678857 | 135 | 161 | 144 | 92 | 95 | 108 | chr14:59000690-59000819 | 1058 |
| 1.01088832 | 52 | 41 | 40 | 20 | 19 | 27 | chr20:62058167-62058211 | 23 |
| 1.30753187 | 129 | 127 | 93 | 59 | 30 | 52 | chr11:62380031-62380122 | −2993 |
| 1.30753187 | 129 | 127 | 93 | 59 | 30 | 52 | chr11:62380031-62380122 | −397 |
| 1.30753187 | 129 | 127 | 93 | 59 | 30 | 52 | chr11:62380031-62380122 | −945 |
| 1.30753187 | 129 | 127 | 93 | 59 | 30 | 52 | chr11:62380031-62380122 | −662 |
| 1.30753187 | 129 | 127 | 93 | 59 | 30 | 52 | chr11:62380031-62380122 | −2060 |
| 1.48112669 | 60 | 85 | 56 | 21 | 22 | 29 | chr1:166171964-166172050 | −524 |
| 0.66209197 | 146 | 125 | 142 | 94 | 70 | 97 | chr17:70255807-70257051 | 51 |
| 1.13573804 | 126 | 237 | 127 | 68 | 54 | 101 | chr5:77692103-77692718 | 316 |
| 0.84883593 | 123 | 122 | 99 | 75 | 47 | 69 | chr3:170965093-170965688 | 152 |
| 0.79097263 | 334 | 379 | 294 | 240 | 114 | 228 | chr22:35232041-35233363 | 334 |
| 0.57044208 | 106 | 138 | 102 | 77 | 80 | 76 | chr14:19999322-19999533 | 50 |
| −1.1953476 | 60 | 86 | 54 | 118 | 151 | 189 | chr9:203667-204892 | 1614 |
| 0.92218047 | 156 | 135 | 124 | 77 | 46 | 96 | chr9:204976-205591 | 610 |
| 2.14886339 | 39 | 41 | 22 | 5 | 12 | 6 | chr4:4906635-4908946 | −4502 |
| 1.19264508 | 88 | 84 | 52 | 30 | 40 | 28 | chr4:4911756-4912477 | −176 |
| 0.84036477 | 226 | 244 | 171 | 125 | 94 | 139 | chr2:109728691-109729896 | −221 |
| 1.09153355 | 155 | 164 | 169 | 67 | 55 | 107 | chr12:130944720-130945499 | −122 |
| 1.52606881 | 73 | 85 | 58 | 24 | 16 | 35 | chr2:85620259-85620455 | 559 |
| 0.92599942 | 100 | 85 | 81 | 49 | 40 | 51 | chr22:36245151-36245781 | −310 |
| 0.95750792 | 648 | 466 | 1094 | 348 | 375 | 414 | chr7:4965186-4966721 | −583 |
| 0.80346101 | 174 | 219 | 162 | 100 | 86 | 132 | chr17:37526311-37526846 | −1816 |
| 1.30975338 | 87 | 125 | 83 | 37 | 38 | 44 | chr20:5934892-5935798 | 607 |
| 1.07528813 | 36 | 49 | 33 | 18 | 15 | 23 | chrX:48929692-48929843 | −47 |
| 0.47212669 | 570 | 466 | 562 | 418 | 417 | 317 | chr6:26379249-26381182 | −624 |
| 1.55393561 | 112 | 103 | 61 | 38 | 12 | 44 | chr6:29532460-29532749 | −65 |
| 0.87382289 | 133 | 143 | 96 | 65 | 64 | 74 | chr2:218865083-218865357 | 304 |
| 0.53546054 | 162 | 184 | 141 | 109 | 108 | 119 | chr5:176662893-176663422 | 193 |
| 0.88308225 | 89 | 118 | 101 | 42 | 54 | 71 | chr3:195889201-195889393 | 1387 |
| 1.30753187 | 129 | 127 | 93 | 59 | 30 | 52 | chr11:62380031-62380122 | −2296 |
| 0.63148678 | 189 | 264 | 193 | 153 | 102 | 162 | chr20:61838942-61839996 | −2635 |
| 1.34169135 | 43 | 43 | 61 | 16 | 19 | 23 | chr3:130641694-130641738 | −2185 |
| 3.20013961 | 287 | 241 | 51 | 37 | 7 | 19 | chr14:23710566-23712370 | −174 |
| 0.5071557 | 121 | 143 | 124 | 78 | 100 | 95 | chr11:46255944-46256479 | 395 |
| 0.78407526 | 498 | 541 | 1005 | 336 | 429 | 422 | chr19:40212455-40213564 | 408 |
| 1.6891735 | 93 | 129 | 65 | 27 | 18 | 44 | chr10:1769176-1769342 | −364 |
| 1.30753187 | 129 | 127 | 93 | 59 | 30 | 52 | chr11:62380031-62380122 | 459 |
| 1.17241455 | 185 | 146 | 104 | 77 | 48 | 68 | chr2:10778819-10779497 | −1333 |
| 0.80252177 | 366 | 403 | 274 | 221 | 168 | 209 | chr2:201384119-201384455 | −67 |
| | | | | | | | | −604 |

TABLE 15

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | Nulliparous (NP) | | | | Parous (P) | | | NP | | GeneBody NP Met | GeneBody Met | Pro-moter Met | Pro-moter Met |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | | | NP | P |
| LOC100128822 | high in NP | -4.9 | 0.049995909 | -1.3 | 12766 | 2 | 6 | 14 | 2 | 2 | 2 | NA | NA | N | N | N | N |
| PEX19 | high in NP | -2.3 | 0.049982271 | -1.3 | 12767 | 48 | 60 | 40 | 28 | 14 | 14 | N | N | N | N | N | N |
| HOPX | high in NP | -3.9 | 0.049959768 | -1.3 | 12768 | 350 | 49 | 39 | 7 | 8 | 33 | N | N | N | N | N | N |
| MSH6 | high in NP | -2.2 | 0.049939311 | -1.3 | 12769 | 24 | 83 | 45 | 19 | 15 | 19 | N | N | N | N | N | N |
| TNPO1 | high in NP | -3.2 | 0.049926355 | -1.3 | 12770 | 76 | 325 | 209 | 85 | 79 | 78 | N | N | N | N | N | N |
| PACRGL | high in NP | -4.8 | 0.04989226 | -1.3 | 12771 | 8 | 20 | 23 | 8 | 8 | 8 | N | N | N | N | N | N |
| ITGA7 | high in NP | -3.1 | 0.049863621 | -1.3 | 12772 | 288 | 207 | 86 | 58 | 35 | 64 | N | N | N | N | N | N |
| GTPBP8 | high in NP | -4.9 | 0.04979134 | -1.3 | 12773 | 4 | 8 | 20 | 4 | 4 | 4 | N | P | N | N | N | N |
| ATG4A | high in NP | -2.6 | 0.049777702 | -1.3 | 12774 | 12 | 16 | 19 | 6 | 8 | 6 | N | P | N | N | N | N |
| CHRDL1 | high in NP | -3.3 | 0.049734061 | -1.3 | 12775 | 152 | 172 | 75 | 36 | 20 | 67 | P | P | N | N | N | N |
| DDB2 | high in NP | -2.4 | 0.04962223 | -1.3 | 12776 | 42 | 33 | 17 | 8 | 8 | 13 | N | N | N | N | N | N |
| SBDSP | high in NP | -2.9 | 0.049466758 | -1.3 | 12777 | NA | NA | NA | NA | NA | NA | N | N | N | N | N | N |
| WAPAL | high in NP | -4.5 | 0.049459939 | -1.3 | 12778 | 38 | 231 | 180 | 35 | 38 | 51 | N | N | N | N | N | N |
| AHSA2 | high in NP | -2.8 | 0.04945312 | -1.3 | 12779 | 7 | 38 | 76 | 7 | 7 | 10 | N | N | N | N | N | N |
| KRAS | high in NP | -2.7 | 0.049425162 | -1.3 | 12780 | 121 | 288 | 262 | 85 | 104 | 96 | N | N | N | N | N | N |
| IRX6 | high in NP | -5.4 | 0.049380839 | -1.3 | 12781 | 3 | 11 | 6 | 3 | 3 | 3 | P | N | N | N | N | N |
| CHRAC1 | high in NP | -2.1 | 0.049366519 | -1.3 | 12782 | 153 | 251 | 208 | 105 | 68 | 88 | N | N | N | N | N | N |
| EEPD1 | high in NP | -2.5 | 0.049341971 | -1.3 | 12783 | 92 | 26 | 47 | 11 | 16 | 14 | N | N | N | N | N | N |
| CDC42BPB | high in NP | -2.2 | 0.049289465 | -1.3 | 12784 | 209 | 188 | 261 | 138 | 100 | 85 | N | N | N | N | N | N |
| TTC33 | high in NP | -2.9 | 0.049224003 | -1.3 | 12785 | 9 | 58 | 24 | 9 | 9 | 9 | N | N | N | N | N | N |
| GAB1 | high in NP | -1.9 | 0.049181043 | -1.3 | 12786 | 28 | 47 | 43 | 24 | 21 | 21 | N | N | N | N | N | N |
| FAM46B | high in NP | -2.6 | 0.049159223 | -1.3 | 12787 | 131 | 142 | 333 | 45 | 81 | 50 | N | N | N | N | N | N |
| MBTPS1 | high in NP | -2.8 | 0.049152404 | -1.3 | 12788 | 65 | 154 | 106 | 71 | 26 | 26 | N | N | N | N | N | N |
| SBNO1 | high in NP | -3.2 | 0.049106035 | -1.3 | 12789 | 19 | 71 | 56 | 15 | 13 | 21 | N | N | N | N | N | N |
| RNF152 | high in NP | -2.3 | 0.049099216 | -1.3 | 12790 | 47 | 68 | 94 | 29 | 17 | 25 | N | N | N | N | N | N |
| PPIA | high in NP | -2.5 | 0.049065803 | -1.3 | 12791 | 193 | 430 | 326 | 141 | 152 | 106 | N | N | N | N | N | N |
| SLC25A39 | high in NP | -2.9 | 0.048991476 | -1.3 | 12792 | 14 | 61 | 31 | 12 | 8 | 8 | P | P | N | N | N | N |
| SSNA1 | high in NP | -2.2 | 0.048975793 | -1.3 | 12793 | 148 | 128 | 160 | 68 | 60 | 22 | N | N | N | N | N | N |
| RPH3AL | high in NP | -3.0 | 0.048954654 | -1.3 | 12794 | 7 | 17 | 23 | 7 | 7 | 7 | N | N | N | N | N | N |
| PPM1K | high in NP | -2.6 | 0.048915786 | -1.3 | 12795 | 9 | 40 | 38 | 9 | 9 | 12 | N | N | N | N | N | N |
| TCF15 | high in NP | -3.3 | 0.048903512 | -1.3 | 12796 | 281 | 24 | 46 | 18 | 8 | 10 | P | P | N | N | N | N |
| CPVL | high in NP | -3.2 | 0.048881691 | -1.3 | 12797 | 3 | 53 | 11 | 3 | 3 | 3 | P | N | N | N | N | N |
| TMEM38A | high in NP | -5.1 | 0.048874872 | -1.3 | 12798 | 4 | 8 | 16 | 4 | 4 | 4 | N | N | N | N | N | N |
| CLDN8 | high in NP | -5.2 | 0.048861916 | -1.3 | 12799 | 2 | 7 | 11 | 2 | 2 | 2 | N | N | N | N | N | N |
| ZNF281 | high in NP | -4.2 | 0.048855097 | -1.3 | 12800 | 24 | 55 | 88 | 23 | 13 | 16 | N | N | N | N | N | N |
| HDGFRP3 | high in NP | -4.9 | 0.048844869 | -1.3 | 12801 | 19 | 63 | 66 | 12 | 11 | 6 | N | N | N | N | N | N |
| DDX50 | high in NP | -1.9 | 0.04883805 | -1.3 | 12802 | 13 | 32 | 20 | 6 | 6 | 6 | N | N | N | N | N | N |
| MRPS24 | high in NP | -3.0 | 0.048831231 | -1.3 | 12803 | 308 | 708 | 1048 | 234 | 223 | 171 | N | N | N | N | N | N |
| MLST8 | high in NP | -2.7 | 0.048812138 | -1.3 | 12804 | 18 | 19 | 23 | 10 | 6 | 6 | N | N | N | N | N | N |
| PIGK | high in NP | -3.9 | 0.048793045 | -1.3 | 12805 | 284 | 112 | 38 | 24 | 25 | 24 | NA | NA | N | N | N | N |
| PLTP | high in NP | -2.4 | 0.04877327 | -1.3 | 12806 | 1046 | 595 | 986 | 294 | 358 | 411 | N | N | N | N | N | N |
| EIF2S1 | high in NP | -3.6 | 0.048743948 | -1.3 | 12807 | 55 | 294 | 220 | 61 | 64 | 38 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
| --- | --- | --- | --- | --- | --- | --- | --- | --- | --- | --- | --- | --- | --- | --- | --- | --- | --- | --- |
| | | | | | | Nulliparous (NP) | | | | Parous (P) | | | NP | P | NP | P | Pro-moter | Pro-moter |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| GBP1 | high in NP | −3.0 | 0.048678486 | −1.3 | 12808 | 106 | 148 | 166 | 24 | 40 | 73 | N | N | N | N | N | N |
| ZNF292 | high in NP | −2.1 | 0.04866553 | −1.3 | 12809 | 110 | 77 | 119 | 41 | 35 | 53 | N | N | N | N | N | N |
| SSPN | high in NP | −2.6 | 0.048652574 | −1.3 | 12810 | 295 | 47 | 43 | 15 | 18 | 21 | N | N | N | N | N | N |
| ABCC1 | high in NP | −3.2 | 0.048638936 | −1.3 | 12811 | 88 | 296 | 213 | 69 | 84 | 52 | N | N | N | N | N | N |
| WDR45L | high in NP | −2.9 | 0.048632117 | −1.3 | 12812 | 317 | 637 | 899 | 288 | 194 | 214 | N | N | N | N | N | N |
| C18orf8 | high in NP | −6.5 | 0.048606205 | −1.3 | 12813 | 7 | 148 | 53 | 7 | 12 | 7 | N | N | N | N | N | N |
| CMTM3 | high in NP | −3.2 | 0.048555063 | −1.3 | 12814 | 693 | 472 | 235 | 99 | 221 | 131 | N | N | N | N | P | N |
| UTP14C | high in NP | −5.2 | 0.048527105 | −1.3 | 12815 | 9 | 14 | 19 | 9 | 9 | 9 | N | P | N | N | N | N |
| ALOX5 | high in NP | −5.1 | 0.048427549 | −1.3 | 12816 | 5 | 31 | 44 | 5 | 8 | 5 | N | N | N | N | N | N |
| CDC42EP4 | high in NP | −2.5 | 0.048347085 | −1.3 | 12817 | 1049 | 687 | 621 | 412 | 220 | 460 | N | N | N | N | N | N |
| ATRX | high in NP | −2.3 | 0.048254347 | −1.3 | 12818 | 163 | 123 | 138 | 101 | 54 | 59 | N | N | N | N | N | N |
| FAM176A | high in NP | −3.1 | 0.048210024 | −1.3 | 12819 | 6 | 20 | 16 | 6 | 6 | 6 | N | NA | N | N | N | N |
| DCAF11 | high in NP | −2.7 | 0.048177293 | −1.3 | 12820 | 83 | 67 | 71 | 45 | 23 | 21 | NA | N | N | N | N | N |
| CNNM2 | high in NP | −1.9 | 0.048170474 | −1.3 | 12821 | 225 | 207 | 229 | 104 | 92 | 93 | N | N | N | N | N | N |
| PRKD3 | high in NP | −2.3 | 0.048123423 | −1.3 | 12822 | 78 | 106 | 76 | 28 | 30 | 42 | N | P | N | N | N | N |
| CEACAM6 | high in NP | −5.4 | 0.048021821 | −1.3 | 12823 | 6 | 10 | 14 | 6 | 6 | 6 | P | P | N | N | N | N |
| UQCRQ | high in NP | −7.6 | 0.047956359 | −1.3 | 12824 | 27 | 290 | 225 | 30 | 18 | 13 | N | N | N | N | N | N |
| PSMB4 | high in NP | −4.2 | 0.0479209 | −1.3 | 12825 | 345 | 1407 | 1730 | 396 | 301 | 128 | N | P | N | N | N | N |
| SPIN3 | high in NP | −5.2 | 0.047889533 | −1.3 | 12826 | 12 | 30 | 15 | 12 | 12 | 12 | N | N | N | N | N | N |
| LPL | high in NP | −2.6 | 0.047869076 | −1.3 | 12827 | 187 | 93 | 145 | 71 | 24 | 47 | N | P | N | N | N | N |
| KIAA2013 | high in NP | −2.0 | 0.047767474 | −1.3 | 12828 | 324 | 185 | 190 | 87 | 92 | 73 | N | N | N | N | N | N |
| OXSR1 | high in NP | −7.0 | 0.0477408 | −1.3 | 12829 | 13 | 119 | 87 | 19 | 16 | 13 | N | N | N | P | N | N |
| FAM49A | high in NP | −4.9 | 0.047624275 | −1.3 | 12830 | 3 | 21 | 14 | 3 | 3 | 3 | N | N | N | N | N | N |
| LSM6 | high in NP | −8.4 | 0.047617457 | −1.3 | 12831 | 2 | 51 | 55 | 5 | 3 | 2 | N | N | N | N | N | N |
| TNFSF12 | high in NP | −3.3 | 0.047599727 | −1.3 | 12832 | 25 | 16 | 8 | 2 | 2 | 8 | P | N | N | N | N | N |
| FAM76A | high in NP | −3.0 | 0.047565632 | −1.3 | 12833 | 21 | 58 | 33 | 17 | 9 | 9 | N | N | N | N | N | N |
| ELF3 | high in NP | −5.9 | 0.047499489 | −1.3 | 12834 | 39 | 269 | 499 | 31 | 91 | 27 | N | N | N | N | N | N |
| ZNF99 | high in NP | −5.2 | 0.047485851 | −1.3 | 12835 | 1 | 5 | 18 | 1 | 1 | 1 | N | N | N | N | N | N |
| MAML1 | high in NP | −2.4 | 0.047464712 | −1.3 | 12836 | 34 | 135 | 82 | 28 | 38 | 34 | N | N | N | N | N | N |
| SCAMP1 | high in NP | −2.7 | 0.047394477 | −1.3 | 12837 | 105 | 85 | 65 | 24 | 24 | 40 | N | N | N | N | N | N |
| EXOC3 | high in NP | −2.8 | 0.047384248 | −1.3 | 12838 | 55 | 109 | 129 | 44 | 38 | 16 | N | N | N | N | N | N |
| STARD4 | high in NP | −2.6 | 0.047350835 | −1.3 | 12839 | 18 | 16 | 10 | 9 | 6 | 6 | N | N | N | N | N | N |
| MCFD2 | high in NP | −3.2 | 0.047306512 | −1.3 | 12840 | 64 | 176 | 183 | 56 | 39 | 51 | N | N | N | N | N | N |
| C19orf20 | high in NP | −3.3 | 0.047256052 | −1.3 | 12841 | 45 | 42 | 49 | 26 | 10 | 2 | N | N | N | N | N | N |
| RPPH1 | high in NP | −5.2 | 0.0471224 | −1.3 | 12842 | 34 | 7 | 14 | 10 | 2 | 2 | N | N | N | N | N | N |
| TNFAIP1 | high in NP | −3.2 | 0.047101262 | −1.3 | 12843 | 31 | 68 | 99 | 23 | 23 | 27 | N | N | N | N | N | N |
| POLR2C | high in NP | −3.3 | 0.047094443 | −1.3 | 12844 | 33 | 135 | 114 | 31 | 17 | 11 | N | N | N | N | N | N |
| SLU7 | high in NP | −2.6 | 0.047080805 | −1.3 | 12845 | 79 | 163 | 153 | 67 | 41 | 49 | N | N | N | N | P | N |
| UCHL5 | high in NP | −2.0 | 0.047022844 | −1.3 | 12846 | 13 | 15 | 24 | 7 | 7 | 7 | N | N | N | N | N | N |
| EARS2 | high in NP | −2.0 | 0.046947835 | −1.3 | 12847 | 30 | 22 | 24 | 13 | 11 | 8 | N | N | N | N | N | N |
| YY1 | high in NP | −3.4 | 0.046941016 | −1.3 | 12848 | 94 | 245 | 370 | 45 | 55 | 96 | N | N | N | N | N | N |
| RPL22L1 | high in NP | −5.1 | 0.046854415 | −1.3 | 12849 | 2 | 18 | 13 | 2 | 2 | 2 | N | N | N | N | N | N |
| LITV1 | high in NP | −8.6 | 0.046787589 | −1.3 | 12850 | 3 | 53 | 55 | 3 | 6 | 3 | N | N | N | N | N | N |
| GNL3 | high in NP | −5.4 | 0.046757586 | −1.3 | 12851 | 97 | 707 | 383 | 67 | 102 | 65 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
| | | | | | Nulliparous (NP) | | | Parous (P) | | | | NP | | P | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody NP Met | GeneBody Met | Pro-motor Met | Pro-motor Met |
|---|---|---|---|---|---|---|---|---|---|---|---|---|---|---|---|---|---|---|
| C15orf28 | high in NP | -5.1 | 0.046724855 | -1.3 | 12852 | 6 | 44 | 33 | 9 | 6 | 6 | NA | NA | N | N | N | N | N |
| ZXDB | high in NP | -3.5 | 0.046660075 | -1.3 | 12853 | 130 | 393 | 328 | 89 | 79 | 110 | N | N | N | N | N | N | N |
| CCL7 | high in NP | -5.4 | 0.046653256 | -1.3 | 12854 | 2 | 7 | 18 | 2 | 2 | 2 | N | N | N | N | N | N | N |
| MST1P2 | high in NP | -5.4 | 0.046598023 | -1.3 | 12855 | 1 | 5 | 20 | 1 | 1 | 1 | NA | NA | N | N | N | N | N |
| EHBP1 | high in NP | -2.5 | 0.046542789 | -1.3 | 12856 | 35 | 62 | 49 | 15 | 13 | 24 | N | N | N | N | N | N | N |
| ROR1 | high in NP | -2.2 | 0.046529151 | -1.3 | 12857 | 148 | 120 | 124 | 40 | 54 | 67 | N | N | N | N | N | N | N |
| OSBPL9 | high in NP | -5.4 | 0.046500511 | -1.3 | 12858 | 17 | 99 | 74 | 14 | 15 | 10 | N | N | N | N | N | N | N |
| BMP4 | high in NP | -2.8 | 0.046486874 | -1.3 | 12859 | 220 | 144 | 66 | 22 | 22 | 67 | N | P | N | N | N | N | N |
| MGC2752 | high in NP | -2.6 | 0.046456188 | -1.3 | 12860 | 41 | 143 | 106 | 59 | 25 | 22 | NA | NA | N | N | N | N | N |
| SELPLG | high in NP | -4.1 | 0.046443914 | -1.3 | 12861 | 27 | 50 | 15 | 11 | 11 | 14 | N | N | N | N | N | N | N |
| RMND5A | high in NP | -2.4 | 0.046430276 | -1.3 | 12862 | 111 | 179 | 220 | 50 | 62 | 99 | N | N | N | N | N | N | N |
| ITGAE | high in NP | -2.5 | 0.046387317 | -1.3 | 12863 | 8 | 28 | 36 | 8 | 8 | 8 | N | N | N | N | N | N | N |
| RB1CC1 | high in NP | -3.9 | 0.046377088 | -1.3 | 12864 | 20 | 160 | 117 | 32 | 26 | 28 | N | N | N | N | N | P | N |
| ZNF181 | high in NP | -3.1 | 0.046357995 | -1.3 | 12865 | 4 | 22 | 27 | 4 | 4 | 4 | N | N | N | N | N | N | N |
| IMMT | high in NP | -2.8 | 0.046342994 | -1.3 | 12866 | 20 | 67 | 53 | 20 | 12 | 12 | N | N | N | N | N | N | N |
| UBE2A | high in NP | -5.9 | 0.046320491 | -1.3 | 12867 | 16 | 123 | 76 | 18 | 19 | 19 | N | N | N | N | N | N | N |
| APLP2 | high in NP | -2.7 | 0.046313672 | -1.3 | 12868 | 7339 | 5798 | 3008 | 2381 | 1592 | 1704 | NA | NA | N | N | N | N | N |
| MAPKAPK5 | high in NP | -5.4 | 0.046291169 | -1.3 | 12869 | 8 | 127 | 58 | 10 | 8 | 11 | N | N | N | N | N | N | N |
| HNRNPR | high in NP | -4.8 | 0.046250256 | -1.3 | 12870 | 23 | 128 | 101 | 24 | 24 | 17 | N | N | N | N | N | N | N |
| STAP2 | high in NP | -12.5 | 0.046174565 | -1.3 | 12871 | 4 | 51 | 44 | 4 | 7 | 4 | N | N | N | N | N | N | N |
| GOLGA6D | high in NP | -6.4 | 0.046143198 | -1.3 | 12872 | 1 | 7 | 7 | 1 | 1 | 1 | NA | NA | N | N | N | N | N |
| DIABLO | high in NP | -2.5 | 0.04612956 | -1.3 | 12873 | 107 | 206 | 142 | 76 | 43 | 40 | N | N | N | N | N | N | N |
| MBD1 | high in NP | -3.2 | 0.046081827 | -1.3 | 12874 | 9 | 62 | 71 | 18 | 9 | 9 | N | N | N | N | N | N | N |
| ENY2 | high in NP | -11.5 | 0.046075009 | -1.3 | 12875 | 2 | 79 | 47 | 2 | 2 | 5 | N | N | N | N | N | N | N |
| EDIL3 | high in NP | -1.9 | 0.046027276 | -1.3 | 12876 | 15 | 17 | 14 | 9 | 9 | 9 | P | N | N | N | N | N | N |
| AIM1L | high in NP | -6.6 | 0.045922946 | -1.3 | 12877 | 6 | 13 | 11 | 2 | 6 | 6 | P | P | N | N | N | P | N |
| EGR4 | high in NP | -6.4 | 0.045916127 | -1.3 | 12878 | 2 | 10 | 7 | 2 | 2 | 2 | P | P | N | N | N | N | N |
| MIER2 | high in NP | -4.9 | 0.045893624 | -1.3 | 12879 | 30 | 62 | 107 | 13 | 21 | 24 | N | N | N | N | N | N | N |
| SULT1A2 | high in NP | -5.6 | 0.045880668 | -1.3 | 12880 | 3 | 29 | 7 | 3 | 3 | 3 | N | N | N | N | N | N | N |
| S100A10 | high in NP | -3.9 | 0.045765428 | -1.3 | 12881 | 355 | 2442 | 2149 | 163 | 534 | 194 | N | N | N | N | N | N | N |
| SAT1 | high in NP | -2.8 | 0.045703375 | -1.3 | 12882 | 3018 | 7687 | 6420 | 1966 | 1802 | 2366 | N | N | N | N | N | N | N |
| MBD2 | high in NP | -10.6 | 0.045696556 | -1.3 | 12883 | 40 | 377 | 403 | 27 | 34 | 34 | N | N | N | N | N | N | N |
| FMO5 | high in NP | -4.3 | 0.045689737 | -1.3 | 12884 | 13 | 52 | 74 | 7 | 14 | 7 | N | N | N | N | N | N | N |
| KLHL9 | high in NP | -2.0 | 0.0456761 | -1.3 | 12885 | 17 | 35 | 42 | 16 | 11 | 11 | N | N | N | N | N | N | N |
| LIN37 | high in NP | -5.3 | 0.045650188 | -1.3 | 12886 | 4 | 24 | 16 | 4 | 4 | 4 | N | N | N | N | N | N | N |
| TOR1AIP2 | high in NP | -2.0 | 0.045643369 | -1.3 | 12887 | 25 | 39 | 59 | 17 | 17 | 17 | N | N | N | N | N | N | N |
| WDR89 | high in NP | -3.2 | 0.045618138 | -1.3 | 12888 | 8 | 35 | 15 | 8 | 8 | 8 | N | N | N | N | N | N | N |
| TNIP1 | high in NP | -2.2 | 0.045590863 | -1.3 | 12889 | 498 | 570 | 740 | 387 | 265 | 145 | N | N | N | N | N | N | N |
| FASTKD1 | high in NP | -4.9 | 0.045584044 | -1.3 | 12890 | 7 | 36 | 38 | 9 | 9 | 7 | N | N | N | N | N | N | N |
| RHBDF1 | high in NP | -2.2 | 0.045471531 | -1.3 | 12891 | 93 | 108 | 173 | 51 | 43 | 33 | N | N | N | N | N | N | N |
| NINJ2 | high in NP | -1.9 | 0.045447665 | -1.3 | 12892 | 9 | 6 | 6 | 3 | 3 | 3 | N | N | N | N | N | N | N |
| EMP3 | high in NP | -3.3 | 0.045434027 | -1.3 | 12893 | 501 | 1325 | 1502 | 410 | 364 | 337 | N | N | N | N | N | N | N |
| METAP1 | high in NP | -2.1 | 0.045337879 | -1.3 | 12894 | 68 | 125 | 85 | 46 | 42 | 34 | N | N | N | N | N | N | N |
| FAM160A2 | high in NP | -2.7 | 0.045211047 | -1.3 | 12895 | 32 | 70 | 60 | 26 | 21 | 21 | N | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
| --- | --- | --- | --- | --- | --- | --- | --- | --- | --- | --- | --- | --- | --- | --- | --- | --- | --- |
| | | | | | | Nulliparous (NP) | | | | Parous (P) | | | NP | | P | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| KLK1 | high in NP | −6.5 | 0.04516536 | −1.3 | 12896 | 162 | 173 | 262 | 10 | 19 | 150 | N | P | N | N | N | N |
| RAB25 | high in NP | −6.3 | 0.045103307 | −1.3 | 12897 | 4 | 9 | 12 | 4 | 4 | 4 | N | N | N | N | N | N |
| SPATS2L | high in NP | −2.4 | 0.045096488 | −1.3 | 12898 | 103 | 357 | 195 | 70 | 79 | 72 | NA | NA | N | N | N | N |
| HAND2 | high in NP | −2.0 | 0.044981248 | −1.3 | 12899 | 22 | 21 | 18 | 6 | 8 | 9 | N | N | N | N | N | N |
| STAC | high in NP | −3.5 | 0.044878282 | −1.3 | 12900 | 31 | 11 | 19 | 5 | 13 | 5 | N | N | N | N | N | N |
| CTTNBP2NL | high in NP | −2.4 | 0.044718718 | −1.3 | 12901 | 17 | 48 | 59 | 17 | 20 | 17 | N | N | N | N | N | N |
| CNOT6L | high in NP | −2.8 | 0.044686669 | −1.3 | 12902 | 124 | 194 | 117 | 48 | 47 | 92 | N | N | N | N | N | N |
| ARL6IP1 | high in NP | −3.2 | 0.04467985 | −1.3 | 12903 | 651 | 1075 | 974 | 217 | 294 | 554 | N | N | N | N | N | N |
| BLOC1S3 | high in NP | −2.1 | 0.044657347 | −1.3 | 12904 | 90 | 109 | 110 | 51 | 37 | 27 | N | N | N | N | N | N |
| BRF2 | high in NP | −3.6 | 0.044650528 | −1.4 | 12905 | 15 | 47 | 78 | 15 | 4 | 4 | N | P | N | N | N | P |
| RICTOR | high in NP | −1.9 | 0.044614388 | −1.4 | 12906 | 27 | 45 | 58 | 25 | 20 | 20 | N | N | N | N | N | N |
| TMEM206 | high in NP | −5.5 | 0.044561882 | −1.4 | 12907 | 6 | 27 | 19 | 6 | 6 | 6 | N | N | N | N | N | N |
| PSMA4 | high in NP | −4.4 | 0.045122104 | −1.4 | 12908 | 58 | 268 | 208 | 53 | 35 | 22 | N | N | N | N | N | N |
| EML1 | high in NP | −2.0 | 0.044478691 | −1.4 | 12909 | 24 | 30 | 37 | 16 | 11 | 11 | N | N | N | N | N | N |
| C7orf64 | high in NP | −3.1 | 0.044465053 | −1.4 | 12910 | 6 | 28 | 41 | 6 | 6 | 6 | N | N | N | N | N | N |
| BNIP3L | high in NP | −4.3 | 0.044458234 | −1.4 | 12911 | 140 | 882 | 881 | 247 | 57 | 94 | N | N | N | N | N | N |
| ZNF585A | high in NP | −2.0 | 0.044416638 | −1.4 | 12912 | 10 | 8 | 8 | 4 | 4 | 4 | N | N | N | N | N | N |
| C2orf79 | high in NP | −2.5 | 0.044409819 | −1.4 | 12913 | 24 | 57 | 52 | 7 | 8 | 17 | N | N | N | N | N | N |
| FAM58A | high in NP | −7.1 | 0.044371633 | −1.4 | 12914 | 6 | 121 | 31 | 6 | 6 | 9 | N | N | N | N | N | N |
| PAAF1 | high in NP | −1.9 | 0.044364814 | −1.4 | 12915 | 12 | 8 | 7 | 6 | 6 | 6 | N | N | N | N | N | N |
| SERPINB13 | high in NP | −6.4 | 0.044263894 | −1.4 | 12916 | 6 | 17 | 11 | 6 | 6 | 7 | N | N | N | N | N | N |
| ISM1 | high in NP | −4.0 | 0.044257075 | −1.4 | 12917 | 23 | 24 | 9 | 7 | 7 | 9 | NA | NA | N | N | N | N |
| MAP3K13 | high in NP | −3.4 | 0.044241391 | −1.4 | 12918 | 9 | 19 | 44 | 9 | 9 | 9 | N | P | P | N | N | N |
| FOXA1 | high in NP | −2.9 | 0.044178657 | −1.4 | 12919 | 14 | 24 | 39 | 10 | 8 | 8 | P | P | N | N | N | N |
| FAM181B | high in NP | −3.3 | 0.044165019 | −1.4 | 12920 | 17 | 3 | 9 | 3 | 4 | 1 | N | N | N | N | N | N |
| ARL6IP5 | high in NP | −2.3 | 0.044150699 | −1.4 | 12921 | 414 | 264 | 223 | 107 | 145 | 147 | N | N | N | N | N | N |
| ATP1B2 | high in NP | −3.5 | 0.044112513 | −1.4 | 12922 | 421 | 139 | 88 | 67 | 19 | 53 | N | N | N | N | N | N |
| TMEM135 | high in NP | −2.5 | 0.044063416 | −1.4 | 12923 | 9 | 31 | 31 | 9 | 9 | 9 | N | N | N | N | N | N |
| WDR6 | high in NP | −3.6 | 0.044047733 | −1.4 | 12924 | 74 | 257 | 202 | 69 | 51 | 57 | N | N | N | N | N | N |
| GPX2 | high in NP | −7.3 | 0.043925673 | −1.4 | 12925 | 2 | 9 | 8 | 2 | 2 | 2 | N | N | N | N | N | N |
| BRAF | high in NP | −3.0 | 0.04390658 | −1.4 | 12926 | 7 | 19 | 19 | 7 | 7 | 7 | N | N | N | N | N | N |
| BRD7 | high in NP | −3.0 | 0.043899761 | −1.4 | 12927 | 14 | 74 | 34 | 10 | 11 | 8 | N | N | N | N | N | N |
| C10orf57 | high in NP | −6.1 | 0.043860211 | −1.4 | 12928 | 5 | 20 | 18 | 5 | 5 | 5 | N | N | N | N | N | N |
| TOLLIP | high in NP | −2.4 | 0.043833617 | −1.4 | 12929 | 197 | 341 | 319 | 117 | 143 | 129 | N | N | N | N | N | N |
| CHCHD5 | high in NP | −2.1 | 0.043826798 | −1.4 | 12930 | 38 | 28 | 55 | 13 | 11 | 10 | N | N | N | N | N | N |
| KIAA1826 | high in NP | −6.4 | 0.043749062 | −1.4 | 12931 | 6 | 17 | 10 | 6 | 6 | 6 | N | N | N | N | N | N |
| FLOT1 | high in NP | −2.1 | 0.043724514 | −1.4 | 12932 | 362 | 257 | 237 | 128 | 116 | 95 | N | N | N | N | N | N |
| CASP3 | high in NP | −3.3 | 0.043657006 | −1.4 | 12933 | 9 | 30 | 23 | 9 | 9 | 9 | N | N | N | N | N | N |
| GIPC1 | high in NP | −2.7 | 0.04363655 | −1.4 | 12934 | 142 | 137 | 194 | 56 | 88 | 27 | N | N | N | N | N | N |
| THAP1 | high in NP | −5.3 | 0.043629731 | −1.4 | 12935 | 2 | 35 | 14 | 2 | 2 | 2 | N | N | N | N | N | N |
| SAR1B | high in NP | −3.3 | 0.043614047 | −1.4 | 12936 | 6 | 33 | 22 | 6 | 6 | 6 | N | N | N | N | N | N |
| ACER3 | high in NP | −2.1 | 0.043584726 | −1.4 | 12937 | 53 | 87 | 74 | 26 | 36 | 33 | NA | NA | N | N | N | N |
| CRLS1 | high in NP | −4.0 | 0.043571088 | −1.4 | 12938 | 18 | 121 | 66 | 22 | 15 | 12 | N | N | N | N | N | N |
| CENPV | high in NP | −5.3 | 0.04355745 | −1.4 | 12939 | 4 | 44 | 16 | 4 | 4 | 4 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | Parous (P) | | | NP | | P | GeneBody Met | Pro-moter Met | Pro-moter Met |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | | | |
| FAM108B1 | high in NP | −2.6 | 0.043536311 | −1.4 | 12940 | 153 | 276 | 374 | 76 | 75 | 117 | N | N | N | N | N | N |
| FAM164A | high in NP | −2.0 | 0.043494715 | −1.4 | 12941 | 29 | 16 | 13 | 8 | 8 | 8 | N | N | N | N | N | N |
| CCNG2 | high in NP | −2.9 | 0.043475622 | −1.4 | 12942 | 255 | 162 | 142 | 52 | 39 | 100 | N | N | N | N | N | N |
| HSP90AA1 | high in NP | −3.1 | 0.043468803 | −1.4 | 12943 | 1908 | 7636 | 1864 | 929 | 722 | 1560 | N | N | N | N | N | N |
| ATAD1 | high in NP | −2.6 | 0.043453802 | −1.4 | 12944 | 135 | 109 | 104 | 72 | 38 | 32 | N | N | N | N | N | N |
| SELENBP1 | high in NP | −3.4 | 0.043419707 | −1.4 | 12945 | 323 | 68 | 78 | 17 | 28 | 37 | N | N | N | N | N | N |
| BBX | high in NP | −2.3 | 0.043412888 | −1.4 | 12946 | 156 | 112 | 115 | 74 | 52 | 65 | N | N | N | N | N | N |
| SAA4 | high in NP | −6.3 | 0.043402659 | −1.4 | 12947 | 3 | 8 | 16 | 3 | 3 | 3 | N | P | N | N | N | N |
| OPN1SW | high in NP | −6.3 | 0.043402659 | −1.4 | 12948 | 4 | 9 | 17 | 4 | 4 | 4 | N | N | N | N | N | N |
| PAPD7 | high in NP | −3.0 | 0.043321514 | −1.4 | 12949 | 110 | 337 | 194 | 42 | 74 | 99 | NA | NA | N | N | N | N |
| UBE2D1 | high in NP | −4.1 | 0.043300375 | −1.4 | 12950 | 86 | 279 | 367 | 38 | 44 | 79 | N | N | N | N | N | N |
| TMEM167B | high in NP | −2.1 | 0.043237641 | −1.4 | 12951 | 71 | 112 | 110 | 47 | 31 | 27 | N | N | N | N | N | N |
| SERPINB3 | high in NP | −6.4 | 0.043230822 | −1.4 | 12952 | 1 | 7 | 13 | 1 | 1 | 1 | N | N | N | N | N | N |
| TXNL4A | high in NP | −4.8 | 0.043224003 | −1.4 | 12953 | 35 | 225 | 130 | 29 | 22 | 17 | N | N | N | N | P | N |
| C9orf86 | high in NP | −2.4 | 0.043202182 | −1.4 | 12954 | 347 | 365 | 468 | 279 | 154 | 68 | N | N | N | N | N | N |
| ADAMTS6 | high in NP | −6.9 | 0.043171497 | −1.4 | 12955 | 4 | 14 | 9 | 4 | 4 | 4 | N | N | N | N | N | N |
| BRP44L | high in NP | −5.4 | 0.043164678 | −1.4 | 12956 | 6 | 51 | 19 | 6 | 6 | 6 | N | N | N | N | N | N |
| FZD1 | high in NP | −3.0 | 0.043157859 | −1.4 | 12957 | 134 | 135 | 98 | 34 | 42 | 68 | N | N | N | N | P | N |
| ASS1 | high in NP | −2.6 | 0.043151104 | −1.4 | 12958 | 147 | 151 | 274 | 65 | 96 | 16 | N | N | N | N | N | N |
| USP43 | high in NP | −3.1 | 0.043123082 | −1.4 | 12959 | 10 | 22 | 22 | 10 | 10 | 10 | N | N | N | N | P | N |
| MEST | high in NP | −4.2 | 0.043103989 | −1.4 | 12960 | 257 | 191 | 88 | 18 | 86 | 38 | N | P | N | N | N | N |
| TNNT3 | high in NP | −6.0 | 0.042986703 | −1.4 | 12961 | 32 | 91 | 50 | 6 | 11 | 26 | N | N | N | N | N | N |
| BIK | high in NP | −6.3 | 0.042951926 | −1.4 | 12962 | 6 | 11 | 22 | 6 | 6 | 6 | N | N | N | N | N | N |
| TPBG | high in NP | −2.5 | 0.042930788 | −1.4 | 12963 | 605 | 958 | 635 | 267 | 264 | 471 | N | P | N | N | N | N |
| FAM109B | high in NP | −2.3 | 0.042845551 | −1.4 | 12964 | 97 | 60 | 44 | 23 | 18 | 20 | N | N | N | N | N | N |
| CCDC51 | high in NP | −7.0 | 0.042818275 | −1.4 | 12965 | 3 | 10 | 11 | 3 | 3 | 3 | N | N | N | N | N | N |
| LOC389033 | high in NP | −6.4 | 0.042712581 | −1.4 | 12966 | 1 | 7 | 17 | 1 | 1 | 1 | N | N | N | N | N | N |
| CBX3 | high in NP | −5.0 | 0.042698943 | −1.4 | 12967 | 71 | 258 | 314 | 35 | 60 | 43 | NA | NA | N | N | N | N |
| FAM165B | high in NP | −2.6 | 0.042655302 | −1.4 | 12968 | 91 | 235 | 139 | 44 | 33 | 57 | N | N | N | N | N | N |
| ZC3HC1 | high in NP | −5.6 | 0.042484828 | −1.4 | 12969 | 5 | 37 | 17 | 5 | 5 | 5 | N | N | N | N | N | N |
| FLJ30679 | high in NP | −5.7 | 0.042451415 | −1.4 | 12970 | 4 | 30 | 17 | 4 | 4 | 4 | NA | NA | N | N | N | N |
| PBRM1 | high in NP | −2.1 | 0.042411865 | −1.4 | 12971 | 79 | 94 | 63 | 47 | 29 | 29 | N | N | N | N | N | N |
| NUDT16L1 | high in NP | −2.9 | 0.042384589 | −1.4 | 12972 | 16 | 20 | 20 | 7 | 5 | 8 | N | N | N | N | N | N |
| H2AFY | high in NP | −2.6 | 0.042348449 | −1.4 | 12973 | 528 | 718 | 709 | 306 | 402 | 141 | N | N | N | N | N | N |
| CBX4 | high in NP | −3.7 | 0.042237982 | −1.4 | 12974 | 123 | 124 | 137 | 16 | 27 | 77 | N | N | N | N | N | N |
| RGL1 | high in NP | −2.3 | 0.042225707 | −1.4 | 12975 | 79 | 63 | 52 | 28 | 30 | 21 | N | N | N | N | N | N |
| BATF3 | high in NP | −2.8 | 0.042218889 | −1.4 | 12976 | 14 | 27 | 23 | 3 | 8 | 3 | N | N | N | N | N | N |
| ARNTL | high in NP | −10.4 | 0.042218343 | −1.4 | 12977 | 12 | 96 | 114 | 12 | 15 | 15 | N | N | N | N | N | N |
| BOD1 | high in NP | −3.2 | 0.042176611 | −1.4 | 12978 | 18 | 115 | 61 | 17 | 15 | 15 | N | N | N | N | N | N |
| NKRF | high in NP | −3.6 | 0.042162973 | −1.4 | 12979 | 63 | 85 | 65 | 14 | 15 | 41 | NA | NA | N | N | N | N |
| TRIM47 | high in NP | −2.8 | 0.041991135 | −1.4 | 12980 | 62 | 186 | 186 | 59 | 27 | 32 | N | N | N | N | N | N |
| RNPS1 | high in NP | −6.5 | 0.041972042 | −1.4 | 12981 | 31 | 283 | 278 | 24 | 29 | 35 | N | N | N | N | N | N |
| NPHP3 | high in NP | −2.1 | 0.041956359 | −1.4 | 12982 | 15 | 47 | 59 | 15 | 18 | 15 | N | N | N | N | N | N |
| ELOVL3 | high in NP | −7.0 | 0.0419494 | −1.4 | 12983 | 4 | 10 | 14 | 4 | 4 | 4 | N | N | N | N | N | P |

TABLE 15-continued

Genes that Are Differentially Methylated between Nulliparous and Parous CD44+ Breast Epithelial Cells

| | | | | | SAGE-seq | | | | | | ChIP-seq | | | MSDK-seq | | |
| | | | | | Nulliparous (NP) | | | Parous (P) | | | NP | | P | | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
|---|---|---|---|---|---|---|---|---|---|---|---|---|---|---|---|---|---|
| TOP3B | high in NP | -3.5 | 0.041920218 | -1.4 | 12984 | 13 | 25 | 30 | 13 | 13 | 13 | N | N | N | N | N | N |
| SNX3 | high in NP | -19.9 | 0.041883396 | -1.4 | 12985 | 12 | 436 | 258 | 14 | 8 | 12 | N | N | N | N | P | P |
| KLHL12 | high in NP | -3.2 | 0.041869076 | -1.4 | 12986 | 13 | 39 | 37 | 11 | 7 | 7 | N | N | N | N | N | N |
| ATF4 | high in NP | -2.7 | 0.041862257 | -1.4 | 12987 | 1515 | 3348 | 3543 | 607 | 1265 | 944 | N | N | N | N | N | N |
| KIAA0114 | high in NP | -17.6 | 0.041855438 | -1.4 | 12988 | 3 | 124 | 178 | 7 | 3 | 3 | N | N | N | N | N | N |
| MTERFD1 | high in NP | -7.7 | 0.041811797 | -1.4 | 12989 | 2 | 12 | 10 | 2 | 2 | 2 | N | N | N | N | N | N |
| CARD16 | high in NP | -7.5 | 0.041804978 | -1.4 | 12990 | 2 | 9 | 11 | 2 | 2 | 2 | N | N | N | N | N | N |
| CCDC126 | high in NP | -3.6 | 0.041768155 | -1.4 | 12991 | 6 | 22 | 18 | 6 | 6 | 6 | N | N | N | N | N | N |
| PIK3CD | high in NP | -3.9 | 0.041708831 | -1.4 | 12992 | 45 | 116 | 147 | 39 | 28 | 28 | N | N | N | N | N | N |
| ARHGAP10 | high in NP | -3.5 | 0.041669962 | -1.4 | 12993 | 14 | 62 | 32 | 14 | 14 | 14 | N | N | N | N | N | N |
| RILPL2 | high in NP | -4.0 | 0.04164746 | -1.4 | 12994 | 14 | 119 | 42 | 7 | 2 | 8 | N | N | N | N | N | N |
| TTC14 | high in NP | -5.6 | 0.041640641 | -1.4 | 12995 | 9 | 44 | 47 | 11 | 9 | 9 | N | N | N | N | N | N |
| C2orf18 | high in NP | -3.3 | 0.041463348 | -1.4 | 12996 | 88 | 261 | 184 | 85 | 47 | 34 | N | N | N | N | P | N |
| MMD | high in NP | -2.3 | 0.041456529 | -1.4 | 12997 | 21 | 48 | 46 | 18 | 9 | 9 | N | N | N | N | N | N |
| DYNC1LI2 | high in NP | -2.3 | 0.041420389 | -1.4 | 12998 | 851 | 910 | 821 | 629 | 454 | 254 | N | N | N | N | N | N |
| SGPP1 | high in NP | -2.3 | 0.041380839 | -1.4 | 12999 | 21 | 87 | 25 | 9 | 9 | 13 | N | N | N | N | N | N |
| USP14 | high in NP | -8.0 | 0.041341289 | -1.4 | 13000 | 36 | 337 | 303 | 41 | 38 | 22 | N | N | N | N | N | N |
| HTATIP2 | high in NP | -3.3 | 0.041319468 | -1.4 | 13001 | 6 | 33 | 57 | 6 | 6 | 6 | N | P | N | N | N | P |
| RIOK2 | high in NP | -3.5 | 0.041274463 | -1.4 | 13002 | 9 | 44 | 26 | 9 | 9 | 9 | N | N | N | N | N | N |
| GNAQ | high in NP | -2.4 | 0.041260825 | -1.4 | 13003 | 26 | 25 | 31 | 12 | 12 | 15 | N | N | N | N | N | N |
| C16orf89 | high in NP | -7.4 | 0.041238323 | -1.4 | 13004 | 5 | 17 | 11 | 5 | 5 | 5 | N | P | N | N | N | N |
| PKDCC | high in NP | -3.3 | 0.041231504 | -1.4 | 13005 | 274 | 85 | 202 | 49 | 27 | 51 | NA | NA | N | N | N | N |
| PPPDE2 | high in NP | -6.9 | 0.041224685 | -1.4 | 13006 | 1 | 17 | 6 | 1 | 1 | 1 | NA | NA | N | N | N | N |
| MSH3 | high in NP | -2.4 | 0.041196727 | -1.4 | 13007 | 16 | 49 | 42 | 16 | 9 | 9 | N | N | N | N | N | N |
| MYBPC1 | high in NP | -7.0 | 0.041158541 | -1.4 | 13008 | 6 | 13 | 20 | 6 | 6 | 6 | N | N | N | N | N | N |
| SPAST | high in NP | -2.0 | 0.041151722 | -1.4 | 13009 | 18 | 53 | 31 | 14 | 12 | 12 | N | N | N | N | N | N |
| LPAR4 | high in NP | -2.1 | 0.041131265 | -1.4 | 13010 | 12 | 10 | 16 | 6 | 6 | 6 | N | N | N | N | N | N |
| MIER1 | high in NP | -2.5 | 0.041099898 | -1.4 | 13011 | 18 | 66 | 64 | 20 | 24 | 18 | P | N | N | N | N | N |
| KTN1 | high in NP | -3.2 | 0.041079441 | -1.4 | 13012 | 49 | 145 | 135 | 53 | 44 | 34 | N | N | N | N | N | N |
| ZNF75D | high in NP | -2.2 | 0.041046028 | -1.4 | 13013 | 10 | 9 | 21 | 4 | 4 | 4 | N | N | N | N | N | N |
| FAM45B | high in NP | -4.8 | 0.041004432 | -1.4 | 13014 | 22 | 6 | 3 | 5 | 1 | 1 | N | N | N | N | N | N |
| RBM11 | high in NP | -2.0 | 0.040853051 | -1.4 | 13015 | 13 | 20 | 14 | 7 | 7 | 7 | N | N | N | N | N | N |
| XPOT | high in NP | -2.7 | 0.040831913 | -1.4 | 13016 | 140 | 223 | 156 | 96 | 51 | 25 | N | N | N | N | N | N |
| TRIM69 | high in NP | -7.8 | 0.040825094 | -1.4 | 13017 | 4 | 12 | 14 | 4 | 4 | 4 | N | N | N | N | N | N |
| XCL2 | high in NP | -6.9 | 0.040810774 | -1.4 | 13018 | 1 | 22 | 6 | 1 | 1 | 1 | N | N | N | N | N | N |
| TCEAL4 | high in NP | -4.8 | 0.04079509 | -1.4 | 13019 | 20 | 75 | 108 | 12 | 10 | 13 | N | N | N | N | N | N |
| NOB1 | high in NP | -2.3 | 0.04074463 | -1.4 | 13020 | 57 | 92 | 63 | 28 | 33 | 21 | N | N | N | N | N | N |
| TEX10 | high in NP | -3.3 | 0.040715309 | -1.4 | 13021 | 129 | 323 | 459 | 37 | 80 | 97 | N | N | N | N | N | N |
| C6orf26 | high in NP | -3.9 | 0.040652574 | -1.4 | 13022 | 9 | 15 | 15 | 3 | 3 | 6 | N | N | N | N | N | N |
| LY6E | high in NP | -2.9 | 0.040589158 | -1.4 | 13023 | 1377 | 640 | 674 | 266 | 445 | 203 | N | N | N | N | N | N |
| LOC729176 | high in NP | -7.0 | 0.04057552 | -1.4 | 13024 | 1 | 7 | 18 | 1 | 1 | 1 | N | N | N | N | N | N |
| PCYOX1L | high in NP | -7.4 | 0.040568701 | -1.4 | 13025 | 3 | 11 | 14 | 3 | 3 | 3 | N | N | N | N | N | N |
| PPCS | high in NP | -6.7 | 0.040550972 | -1.4 | 13026 | 3 | 19 | 22 | 3 | 3 | 3 | N | N | N | N | N | N |
| TTC28 | high in NP | -2.3 | 0.040522332 | -1.4 | 13027 | 78 | 84 | 162 | 50 | 51 | 44 | NA | NA | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | Nulliparous (NP) | | | | Parous (P) | | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | NP CD44+ N74 | P CD44+ N66 | GeneBody NP Met | GeneBody Met | Pro-motor Met | Pro-moter Met |
| SCHIP1 | high in NP | −3.4 | 0.04050733 | −1.4 | 13028 | 114 | 123 | 119 | 35 | 76 | 24 | N | N | N | N | N | N |
| TSPYL4 | high in NP | −2.9 | 0.040457552 | −1.4 | 13029 | 17 | 38 | 31 | 11 | 11 | 14 | N | N | N | N | N | N |
| NECAB1 | high in NP | −3.5 | 0.040396181 | −1.4 | 13030 | 10 | 36 | 38 | 10 | 10 | 10 | N | N | N | N | N | N |
| ANKRD12 | high in NP | −2.3 | 0.04033822 | −1.4 | 13031 | 52 | 135 | 112 | 56 | 47 | 51 | N | N | N | N | N | N |
| MGC42105 | high in NP | −7.1 | 0.040322537 | −1.4 | 13032 | 1 | 8 | 18 | 1 | 1 | 1 | N | N | N | N | N | N |
| FCN3 | high in NP | −2.0 | 0.040257075 | −1.4 | 13033 | 9 | 5 | 6 | 3 | 3 | 3 | N | N | N | N | N | N |
| DPYD | high in NP | −3.1 | 0.040250256 | −1.4 | 13034 | 55 | 39 | 72 | 13 | 18 | 26 | N | N | N | N | N | N |
| PPA1 | high in NP | −4.8 | 0.040210024 | −1.4 | 13035 | 71 | 682 | 250 | 49 | 45 | 44 | N | N | N | N | N | N |
| ANXA7 | high in NP | −3.8 | 0.040102284 | −1.4 | 13036 | 99 | 264 | 226 | 93 | 38 | 20 | N | N | N | N | N | N |
| RPP38 | high in NP | −6.6 | 0.040084555 | −1.4 | 13037 | 2 | 27 | 16 | 2 | 2 | 2 | N | N | N | N | N | N |
| ASCC2 | high in NP | −2.9 | 0.040054552 | −1.4 | 13038 | 26 | 70 | 33 | 13 | 17 | 13 | N | N | N | N | N | N |
| GOLGA8B | high in NP | −7.3 | 0.040047733 | −1.4 | 13039 | 3 | 21 | 9 | 3 | 3 | 3 | N | N | N | N | N | N |
| RND3 | high in NP | −3.3 | 0.04002864 | −1.4 | 13040 | 284 | 535 | 641 | 194 | 193 | 208 | N | N | N | N | N | N |
| RPA3 | high in NP | −6.4 | 0.039970678 | −1.4 | 13041 | 3 | 20 | 29 | 3 | 3 | 3 | N | N | N | P | N | N |
| TRA2A | high in NP | −4.1 | 0.039927719 | −1.4 | 13042 | 146 | 478 | 410 | 88 | 71 | 121 | N | N | N | N | N | N |
| LEPROT | high in NP | −2.9 | 0.039902489 | −1.4 | 13043 | 405 | 351 | 255 | 244 | 122 | 93 | N | N | N | N | N | N |
| LOC728758 | high in NP | −8.8 | 0.039822707 | −1.4 | 13044 | 2 | 11 | 11 | 2 | 2 | 2 | N | N | N | N | N | N |
| HAT1 | high in NP | −7.1 | 0.039783157 | −1.4 | 13045 | 8 | 29 | 27 | 8 | 8 | 8 | N | N | N | N | N | N |
| RDX | high in NP | −2.6 | 0.039714286 | −1.4 | 13046 | 66 | 198 | 115 | 55 | 37 | 30 | N | N | N | N | N | N |
| RAB2A | high in NP | −2.4 | 0.039707467 | −1.4 | 13047 | 96 | 94 | 60 | 37 | 31 | 17 | N | N | N | N | N | N |
| ACVR1 | high in NP | −3.2 | 0.039685646 | −1.4 | 13048 | 398 | 272 | 489 | 211 | 112 | 70 | N | N | N | N | N | N |
| MRPL15 | high in NP | −23.4 | 0.039673372 | −1.4 | 13049 | 3 | 99 | 58 | 6 | 3 | 3 | N | N | N | N | N | N |
| OAT | high in NP | −2.2 | 0.039666553 | −1.4 | 13050 | 456 | 685 | 675 | 242 | 287 | 256 | N | N | N | N | N | N |
| FAM119B | high in NP | −2.2 | 0.039624275 | −1.4 | 13051 | 173 | 243 | 264 | 89 | 109 | 97 | P | N | N | N | N | N |
| CHORDC1 | high in NP | −3.8 | 0.039617457 | −1.4 | 13052 | 5 | 19 | 34 | 5 | 5 | 5 | N | N | N | N | N | N |
| CCBL2 | high in NP | −7.3 | 0.039610638 | −1.4 | 13053 | 3 | 29 | 9 | 3 | 3 | 3 | N | P | N | N | P | N |
| CLK1 | high in NP | −2.3 | 0.039548585 | −1.4 | 13054 | 543 | 1104 | 833 | 263 | 264 | 512 | N | N | N | N | N | N |
| DNAJC7 | high in NP | −6.3 | 0.039521309 | −1.4 | 13055 | 27 | 194 | 199 | 20 | 19 | 30 | N | N | N | N | N | N |
| EPB41L2 | high in NP | −2.7 | 0.039466076 | −1.4 | 13056 | 84 | 219 | 143 | 48 | 25 | 65 | N | N | N | N | N | N |
| CCND1 | high in NP | −3.7 | 0.039442891 | −1.4 | 13057 | 1140 | 390 | 139 | 121 | 125 | 65 | N | N | N | N | N | N |
| SLCO4C1 | high in NP | −2.2 | 0.039430617 | −1.4 | 13058 | 11 | 8 | 13 | 5 | 5 | 5 | N | N | N | N | N | N |
| COTL1 | high in NP | −8.9 | 0.039414934 | −1.4 | 13059 | 76 | 1066 | 888 | 41 | 106 | 59 | N | N | N | N | N | N |
| TRIAP1 | high in NP | −6.5 | 0.039389703 | −1.4 | 13060 | 5 | 40 | 21 | 5 | 5 | 5 | N | N | N | N | N | N |
| ACSS1 | high in NP | −3.2 | 0.039332424 | −1.4 | 13061 | 24 | 26 | 58 | 8 | 13 | 11 | P | N | N | N | N | N |
| NLK | high in NP | −2.4 | 0.039325605 | −1.4 | 13062 | 9 | 33 | 39 | 9 | 9 | 9 | N | N | N | N | N | N |
| PHF6 | high in NP | −3.1 | 0.039318786 | −1.4 | 13063 | 13 | 56 | 52 | 18 | 13 | 13 | N | N | N | N | P | N |
| THUMPD1 | high in NP | −6.4 | 0.039286055 | −1.4 | 13064 | 14 | 95 | 75 | 18 | 14 | 14 | N | N | N | N | N | N |
| ZNF300 | high in NP | −7.7 | 0.039272417 | −1.4 | 13065 | 2 | 22 | 12 | 5 | 5 | 5 | N | N | N | N | N | N |
| MRPL51 | high in NP | −18.4 | 0.039230822 | −1.4 | 13066 | 2 | 75 | 72 | 5 | 2 | 2 | N | N | N | N | N | N |
| C3orf21 | high in NP | −4.4 | 0.039196045 | −1.4 | 13067 | 68 | 57 | 20 | 12 | 9 | 9 | N | N | N | N | N | N |
| DOLPP1 | high in NP | −8.9 | 0.039052847 | −1.4 | 13068 | 29 | 37 | 41 | 16 | 8 | 3 | N | N | P | N | N | N |
| FAM134C | high in NP | −2.7 | 0.03901807 | −1.4 | 13069 | 266 | 556 | 676 | 208 | 120 | 185 | N | N | N | N | N | N |
| GPRASP1 | high in NP | −3.9 | 0.039011251 | −1.4 | 13070 | 13 | 35 | 27 | 13 | 13 | 13 | N | N | N | N | N | N |
| APTX | high in NP | −2.6 | 0.039004432 | −1.4 | 13071 | 13 | 29 | 38 | 9 | 7 | 7 | N | N | N | N | N | N |

TABLE 15-continued

Genes that Are Differentially Methylated between Nulliparous and Parous CD44+ Breast Epithelial Cells

| | | | | | | SAGE-seq | | | | | | | ChIP-seq | | | MSDK-seq | | |
|---|---|---|---|---|---|---|---|---|---|---|---|---|---|---|---|---|---|---|
| | | | | | | Nulliparous (NP) | | | | Parous (P) | | | NP | P | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| APPL2 | high in NP | −5.5 | 0.038960791 | −1.4 | 13072 | 14 | 72 | 67 | 12 | 11 | 8 | N | N | N | N | N | N |
| GK | high in NP | −3.9 | 0.03894238 | −1.4 | 13073 | 4 | 31 | 15 | 4 | 4 | 4 | N | N | N | N | N | N |
| GRINA | high in NP | −3.1 | 0.038935561 | −1.4 | 13074 | 562 | 566 | 519 | 392 | 147 | 165 | N | N | N | N | N | N |
| CSRP2BP | high in NP | −2.2 | 0.038786908 | −1.4 | 13075 | 18 | 12 | 10 | 6 | 6 | 6 | N | N | N | N | N | N |
| PRRX1 | high in NP | −2.6 | 0.038780089 | −1.4 | 13076 | 2155 | 1970 | 1032 | 1096 | 488 | 479 | N | N | N | N | N | N |
| ARAP3 | high in NP | −3.6 | 0.038745312 | −1.4 | 13077 | 16 | 47 | 64 | 6 | 16 | 16 | N | N | P | N | N | N |
| FAM133B | high in NP | −9.0 | 0.038717354 | −1.4 | 13078 | 6 | 19 | 15 | 6 | 6 | 6 | N | N | N | N | N | N |
| CKS1B | high in NP | −6.0 | 0.038632117 | −1.4 | 13079 | 6 | 69 | 53 | 6 | 6 | 9 | N | N | N | N | N | N |
| TRMT11 | high in NP | −3.9 | 0.038574838 | −1.4 | 13080 | 6 | 23 | 18 | 6 | 6 | 6 | N | N | N | N | N | N |
| RNF114 | high in NP | −2.4 | 0.0385612 | −1.4 | 13081 | 153 | 317 | 215 | 72 | 81 | 112 | N | N | N | N | N | N |
| NSMCE2 | high in NP | −7.2 | 0.038535288 | −1.4 | 13082 | 3 | 21 | 27 | 3 | 3 | 3 | N | N | N | N | N | N |
| C1orf123 | high in NP | −2.6 | 0.03850733 | −1.4 | 13083 | 48 | 41 | 38 | 10 | 4 | 17 | N | N | N | N | N | N |
| PDCD6 | high in NP | −8.4 | 0.038389362 | −1.4 | 13084 | 8 | 126 | 90 | 10 | 11 | 8 | P | N | N | N | P | N |
| CDH4 | high in NP | −4.4 | 0.038379134 | −1.4 | 13085 | 23 | 9 | 7 | 6 | 6 | 6 | N | N | N | N | N | N |
| IL1RAP | high in NP | −3.9 | 0.038360041 | −1.4 | 13086 | 16 | 53 | 48 | 16 | 16 | 16 | P | N | N | N | N | N |
| RNF6 | high in NP | −3.9 | 0.038339584 | −1.4 | 13087 | 9 | 33 | 46 | 9 | 9 | 9 | P | N | N | N | N | N |
| GTF3C6 | high in NP | −3.7 | 0.038321855 | −1.4 | 13088 | 5 | 20 | 18 | 5 | 5 | 5 | N | N | N | N | N | N |
| CTBS | high in NP | −3.2 | 0.038315036 | −1.4 | 13089 | 55 | 54 | 83 | 26 | 19 | 20 | N | N | N | N | N | N |
| COMMD3 | high in NP | −9.5 | 0.03827344 | −1.4 | 13090 | 2 | 14 | 11 | 2 | 2 | 2 | N | N | N | N | N | N |
| PRR3 | high in NP | −2.9 | 0.038210706 | −1.4 | 13091 | 28 | 50 | 21 | 13 | 7 | 7 | N | N | N | N | N | N |
| CA12 | high in NP | −3.5 | 0.038156154 | −1.4 | 13092 | 208 | 199 | 419 | 110 | 104 | 35 | N | N | N | N | N | N |
| COL5A2 | high in NP | −3.5 | 0.038133652 | −1.4 | 13093 | 1309 | 160 | 215 | 67 | 53 | 140 | N | P | N | N | N | N |
| STAT3 | high in NP | −2.2 | 0.038121377 | −1.4 | 13094 | 416 | 473 | 442 | 193 | 285 | 221 | N | N | N | N | N | N |
| FIGF | high in NP | −12.0 | 0.038103648 | −1.4 | 13095 | 406 | 137 | 19 | 8 | 8 | 21 | N | N | N | N | N | N |
| NFAT5 | high in NP | −2.2 | 0.038096829 | −1.4 | 13096 | 528 | 545 | 431 | 241 | 308 | 324 | N | N | N | N | N | N |
| PTTG1IP | high in NP | −3.4 | 0.038083873 | −1.4 | 13097 | 84 | 232 | 121 | 59 | 43 | 24 | N | N | N | N | N | N |
| PSMB10 | high in NP | −6.4 | 0.038042278 | −1.4 | 13098 | 9 | 21 | 60 | 5 | 2 | 2 | N | P | N | N | N | N |
| FAM129B | high in NP | −5.4 | 0.038007501 | −1.4 | 13099 | 131 | 569 | 776 | 108 | 156 | 56 | N | N | N | N | N | N |
| UGP2 | high in NP | −2.4 | 0.038000682 | −1.4 | 13100 | 107 | 360 | 123 | 55 | 44 | 36 | N | N | N | N | N | N |
| NUP153 | high in NP | −3.2 | 0.037980225 | −1.4 | 13101 | 255 | 733 | 569 | 126 | 147 | 228 | N | P | N | N | N | N |
| KHDRBS1 | high in NP | −2.8 | 0.037916127 | −1.4 | 13102 | 291 | 577 | 531 | 186 | 183 | 181 | N | N | N | N | N | N |
| FANCF | high in NP | −7.2 | 0.037909308 | −1.4 | 13103 | 5 | 23 | 33 | 5 | 5 | 5 | N | N | N | N | N | N |
| CPNE8 | high in NP | −3.8 | 0.037889533 | −1.4 | 13104 | 11 | 52 | 37 | 11 | 11 | 11 | N | N | N | N | N | N |
| ZNF211 | high in NP | −8.8 | 0.03787044 | −1.4 | 13105 | 3 | 18 | 11 | 3 | 3 | 3 | N | N | N | N | N | N |
| HSF2 | high in NP | −2.9 | 0.037815888 | −1.4 | 13106 | 6 | 37 | 34 | 6 | 6 | 6 | N | N | N | N | N | N |
| PAIP1 | high in NP | −4.8 | 0.037787249 | −1.4 | 13107 | 25 | 174 | 95 | 16 | 19 | 11 | N | N | N | N | N | N |
| TMED4 | high in NP | −2.3 | 0.037762018 | −1.4 | 13108 | 71 | 74 | 43 | 26 | 17 | 15 | N | N | N | N | N | N |
| TAF7 | high in NP | −2.8 | 0.037674736 | −1.4 | 13109 | 58 | 90 | 67 | 32 | 25 | 10 | N | N | N | N | N | N |
| C4orf43 | high in NP | −7.5 | 0.037641323 | −1.4 | 13110 | 4 | 33 | 20 | 4 | 4 | 4 | N | N | N | N | N | N |
| C8orf59 | high in NP | −14.8 | 0.037598363 | −1.4 | 13111 | 9 | 142 | 150 | 7 | 5 | 2 | N | N | N | N | N | N |
| ADAM9 | high in NP | −2.2 | 0.037494033 | −1.4 | 13112 | 157 | 185 | 204 | 96 | 89 | 43 | N | N | N | N | N | N |
| C17orf48 | high in NP | −8.4 | 0.037487214 | −1.4 | 13113 | 3 | 26 | 11 | 3 | 3 | 3 | N | N | N | N | N | N |
| TMCO1 | high in NP | −3.0 | 0.037473577 | −1.4 | 13114 | 53 | 183 | 97 | 33 | 30 | 17 | N | N | N | N | P | N |
| AP1S2 | high in NP | −3.0 | 0.037466758 | −1.4 | 13115 | 32 | 75 | 75 | 25 | 12 | 14 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | Parous (P) | | | NP | | P | NP | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| OLFML1 | high in NP | -9.9 | 0.037459939 | -1.4 | 13116 | 434 | 96 | 11 | 6 | 6 | 6 | N | N | N | N | N | N |
| CLIC4 | high in NP | -2.4 | 0.037393113 | -1.4 | 13117 | 680 | 1264 | 843 | 519 | 354 | 411 | N | N | N | N | N | N |
| OBFC2A | high in NP | -2.5 | 0.037371292 | -1.4 | 13118 | 22 | 68 | 61 | 18 | 19 | 21 | NA | NA | N | N | N | N |
| FAM192A | high in NP | -4.9 | 0.037349472 | -1.4 | 13119 | 16 | 70 | 87 | 12 | 15 | 13 | NA | NA | N | N | N | N |
| ELOVL7 | high in NP | -2.6 | 0.037272417 | -1.4 | 13120 | 37 | 38 | 23 | 15 | 11 | 11 | NA | NA | N | N | N | N |
| BHLHE41 | high in NP | -4.0 | 0.037181043 | -1.4 | 13121 | 38 | 195 | 91 | 21 | 20 | 21 | N | N | N | N | N | N |
| MRPL40 | high in NP | -2.2 | 0.037157859 | -1.4 | 13122 | 10 | 20 | 9 | 4 | 4 | 4 | N | N | N | N | N | N |
| GLS | high in NP | -2.5 | 0.037095124 | -1.4 | 13123 | 74 | 165 | 155 | 42 | 36 | 67 | N | N | N | N | N | N |
| TMEM131 | high in NP | -4.1 | 0.037051483 | -1.4 | 13124 | 17 | 74 | 72 | 21 | 17 | 17 | N | N | N | N | N | N |
| PALLD | high in NP | -2.7 | 0.037034436 | -1.4 | 13125 | 1282 | 844 | 676 | 347 | 532 | 257 | N | N | N | N | N | N |
| WSB1 | high in NP | -4.1 | 0.037005114 | -1.4 | 13126 | 10 | 60 | 33 | 10 | 10 | 10 | N | N | N | N | N | N |
| SLC9A7 | high in NP | -8.6 | 0.036938897 | -1.4 | 13127 | 7 | 16 | 33 | 7 | 7 | 7 | N | N | N | N | N | N |
| VAT1 | high in NP | -2.8 | 0.036926014 | -1.4 | 13128 | 1131 | 523 | 1096 | 435 | 228 | 300 | N | N | N | N | N | N |
| C19orf42 | high in NP | -2.3 | 0.036833958 | -1.4 | 13129 | 68 | 66 | 74 | 27 | 23 | 10 | N | N | N | N | N | N |
| CREB3L2 | high in NP | -3.8 | 0.036818275 | -1.4 | 13130 | 226 | 1038 | 694 | 251 | 98 | 193 | N | N | N | N | N | N |
| CTTN | high in NP | -2.6 | 0.036788953 | -1.4 | 13131 | 628 | 1211 | 888 | 367 | 455 | 245 | N | N | N | N | N | N |
| TSPAN1 | high in NP | -8.8 | 0.036782134 | -1.4 | 13132 | 4 | 14 | 26 | 4 | 4 | 4 | N | N | N | N | N | N |
| FJX1 | high in NP | -3.4 | 0.036775315 | -1.4 | 13133 | 74 | 139 | 65 | 13 | 34 | 27 | N | 4 N | N | N | N | N |
| CES1 | high in NP | -9.8 | 0.036728946 | -1.4 | 13134 | 6 | 17 | 19 | 6 | 6 | 6 | N | N | N | N | N | N |
| PPPDE1 | high in NP | -4.6 | 0.036709171 | -1.4 | 13135 | 20 | 122 | 97 | 23 | 20 | 17 | P | NA | N | N | N | N |
| FGB | high in NP | -9.9 | 0.036677804 | -1.4 | 13136 | 1 | 12 | 14 | 1 | 1 | 1 | P | P | N | N | N | N |
| POMC | high in NP | -9.1 | 0.036645755 | -1.4 | 13137 | 3 | 14 | 21 | 3 | 3 | 3 | P | P | N | N | N | N |
| NGFRAP1 | high in NP | -2.4 | 0.036623935 | -1.4 | 13138 | 17 | 13 | 18 | 6 | 8 | 6 | N | N | N | N | N | N |
| TGFBR1 | high in NP | -2.4 | 0.036617116 | -1.4 | 13139 | 117 | 231 | 131 | 61 | 48 | 77 | NA | NA | N | N | N | N |
| GTF2H2D | high in NP | -8.8 | 0.036570747 | -1.4 | 13140 | 1 | 11 | 27 | 1 | 1 | 1 | N | N | N | N | N | N |
| FAM83A | high in NP | -7.9 | 0.036531197 | -1.4 | 13141 | 5 | 27 | 37 | 5 | 5 | 5 | N | N | P | N | N | N |
| SLC16A1 | high in NP | -3.2 | 0.036490965 | -1.4 | 13142 | 28 | 106 | 75 | 29 | 22 | 28 | N | N | N | N | N | N |
| INPP1 | high in NP | -3.1 | 0.036470508 | -1.4 | 13143 | 73 | 29 | 35 | 6 | 18 | 11 | N | N | N | N | N | N |
| ANKRD30A | high in NP | -9.9 | 0.036435049 | -1.4 | 13144 | 6 | 17 | 21 | 6 | 6 | 6 | N | N | N | N | N | N |
| B4GALT3 | high in NP | -2.3 | 0.036424821 | -1.4 | 13145 | 254 | 382 | 370 | 149 | 76 | 140 | N | N | N | N | N | N |
| SUPT7L | high in NP | -2.3 | 0.036418002 | -1.4 | 13146 | 67 | 87 | 81 | 37 | 29 | 36 | N | N | N | N | N | N |
| EDC3 | high in NP | -3.1 | 0.036405728 | -1.4 | 13147 | 31 | 61 | 72 | 9 | 22 | 12 | N | N | N | N | N | N |
| S100P | high in NP | -9.1 | 0.036398909 | -1.4 | 13148 | 2 | 13 | 24 | 2 | 2 | 2 | N | N | N | N | N | N |
| CDK5RAP3 | high in NP | -7.0 | 0.036369587 | -1.4 | 13149 | 6 | 60 | 70 | 6 | 6 | 9 | N | N | N | N | N | N |
| USP6NL | high in NP | -2.2 | 0.036325946 | -1.4 | 13150 | 26 | 42 | 23 | 15 | 15 | 15 | N | N | N | N | N | N |
| C12orf53 | high in NP | -9.8 | 0.036253665 | -1.4 | 13151 | 4 | 15 | 20 | 4 | 4 | 4 | N | N | N | N | N | N |
| ABCE1 | high in NP | -2.2 | 0.036246846 | -1.4 | 13152 | 111 | 306 | 108 | 55 | 46 | 43 | N | N | N | N | N | N |
| OPN3 | high in NP | -4.0 | 0.036234572 | -1.4 | 13153 | 27 | 125 | 87 | 9 | 24 | 14 | N | N | N | N | N | N |
| SFRS4 | high in NP | -5.9 | 0.03620866 | -1.4 | 13154 | 165 | 1000 | 739 | 95 | 107 | 156 | N | N | N | N | N | N |
| ZNF117 | high in NP | -2.7 | 0.036151381 | -1.4 | 13155 | 29 | 34 | 32 | 19 | 13 | 13 | N | N | N | N | N | N |
| TXNDC5 | high in NP | -2.7 | 0.036144562 | -1.4 | 13156 | 149 | 558 | 128 | 56 | 65 | 53 | N | N | N | N | N | N |
| RNF111 | high in NP | -3.6 | 0.036130924 | -1.4 | 13157 | 23 | 106 | 105 | 29 | 26 | 29 | N | N | N | N | N | N |
| PA2G4 | high in NP | -4.3 | 0.03611865 | -1.4 | 13158 | 11 | 36 | 36 | 11 | 11 | 11 | N | N | N | N | N | N |
| CHD1L | high in NP | -2.5 | 0.03611865 | -1.4 | 13159 | 13 | 44 | 24 | 7 | 7 | 7 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | | Nulliparous (NP) | | | Parous (P) | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| CSTB | high in NP | -3.0 | 0.036106376 | -1.4 | 13160 | 305 | 656 | 822 | 205 | 193 | 123 | N | N | N | N | N | N |
| C10orf78 | high in NP | -3.3 | 0.036085919 | -1.4 | 13161 | 30 | 18 | 11 | 2 | 2 | 8 | N | N | N | N | P | N |
| UBE2N | high in NP | -3.6 | 0.036019775 | -1.4 | 13162 | 59 | 199 | 123 | 29 | 42 | 36 | N | N | N | N | N | N |
| C1orf128 | high in NP | -2.3 | 0.035976816 | -1.4 | 13163 | 262 | 676 | 387 | 154 | 111 | 148 | N | N | N | N | N | N |
| RAB3GAP1 | high in NP | -2.1 | 0.035954995 | -1.4 | 13164 | 168 | 179 | 183 | 71 | 90 | 76 | N | N | N | N | N | N |
| OSBPL5 | high in NP | -2.7 | 0.035934995 | -1.4 | 13165 | 192 | 307 | 166 | 113 | 66 | 55 | N | N | N | N | N | N |
| PARK7 | high in NP | -4.9 | 0.035900443 | -1.4 | 13166 | 58 | 104 | 95 | 39 | 16 | 8 | N | N | N | N | N | N |
| CPNE1 | high in NP | -2.5 | 0.035879986 | -1.4 | 13167 | 2143 | 1246 | 1567 | 890 | 586 | 666 | N | N | N | N | N | N |
| DNAJB6 | high in NP | -3.7 | 0.035873167 | -1.4 | 13168 | 600 | 1501 | 2032 | 309 | 436 | 558 | N | N | N | N | N | N |
| EMP2 | high in NP | -2.4 | 0.035866348 | -1.4 | 13169 | 454 | 550 | 603 | 264 | 178 | 332 | N | N | N | N | N | N |
| CRMP1 | high in NP | -3.6 | 0.035830208 | -1.4 | 13170 | 99 | 28 | 26 | 7 | 7 | 15 | N | N | N | N | N | N |
| TBC1D24 | high in NP | -4.4 | 0.035815206 | -1.4 | 13171 | 7 | 24 | 33 | 7 | 7 | 7 | P | N | N | N | N | N |
| PRR23A | high in NP | -3.0 | 0.035808387 | -1.4 | 13172 | 276 | 346 | 411 | 67 | 90 | 167 | NA | NA | N | N | N | N |
| EIF4A1 | high in NP | -14.6 | 0.035781793 | -1.4 | 13173 | 126 | 3866 | 2103 | 124 | 147 | 147 | N | N | N | N | P | N |
| TP53TG1 | high in NP | -5.4 | 0.035753836 | -1.4 | 13174 | 42 | 13 | 4 | 1 | 8 | 1 | N | N | N | N | N | N |
| CCDC90B | high in NP | -7.4 | 0.035740198 | -1.4 | 13175 | 32 | 41 | 30 | 21 | 6 | 6 | N | N | N | N | N | N |
| MTUS1 | high in NP | -3.0 | 0.035369792 | -1.4 | 13176 | 207 | 219 | 439 | 40 | 76 | 150 | N | N | N | N | N | N |
| RAD23B | high in NP | -2.4 | 0.035685646 | -1.4 | 13177 | 264 | 420 | 360 | 153 | 203 | 128 | N | N | N | N | N | N |
| HOMER1 | high in NP | -3.8 | 0.035678827 | -1.4 | 13178 | 20 | 85 | 68 | 23 | 20 | 24 | N | P | N | N | N | N |
| MGAT2 | high in NP | -4.2 | 0.035672008 | -1.4 | 13179 | 6 | 56 | 36 | 6 | 6 | 6 | N | N | N | N | N | N |
| ASB13 | high in NP | -11.4 | 0.035645414 | -1.4 | 13180 | 8 | 21 | 20 | 8 | 8 | 8 | P | P | N | N | N | N |
| LOXL1 | high in NP | -3.0 | 0.035622912 | -1.4 | 13181 | 766 | 252 | 148 | 74 | 56 | 77 | N | N | N | N | N | N |
| GSDMD | high in NP | -2.5 | 0.035572451 | -1.4 | 13182 | 95 | 89 | 72 | 31 | 33 | 20 | N | N | N | N | N | N |
| PRMT5 | high in NP | -8.6 | 0.034473577 | -1.5 | 13183 | 46 | 397 | 459 | 50 | 28 | 23 | N | N | N | N | N | N |
| NCRNA00095 | high in NP | -4.3 | 0.034431981 | -1.5 | 13184 | 138 | 507 | 509 | 107 | 80 | 102 | N | N | N | N | N | N |
| C12orf75 | high in NP | -5.0 | 0.034419707 | -1.5 | 13185 | 6 | 84 | 21 | 6 | 6 | 6 | NA | NA | N | N | N | N |
| IPO8 | high in NP | -4.7 | 0.035397204 | -1.5 | 13186 | 13 | 62 | 29 | 13 | 13 | 13 | NA | NA | N | N | N | N |
| CES8 | high in NP | -8.4 | 0.035386976 | -1.5 | 13187 | 6 | 29 | 43 | 6 | 6 | 6 | NA | P | N | N | N | N |
| PPP1R2P3 | high in NP | -10.2 | 0.035369928 | -1.5 | 13188 | 1 | 13 | 19 | 1 | 1 | 1 | N | N | N | N | N | N |
| CBX6 | high in NP | -2.6 | 0.035363109 | -1.5 | 13189 | 35 | 75 | 56 | 24 | 14 | 11 | N | N | N | N | N | N |
| RWDD1 | high in NP | -2.4 | 0.035340607 | -1.5 | 13190 | 378 | 474 | 291 | 133 | 177 | 105 | N | N | N | N | N | N |
| CAMK2D | high in NP | -2.7 | 0.035330583 | -1.5 | 13191 | 198 | 289 | 291 | 123 | 51 | 133 | N | N | N | N | N | N |
| TTC7B | high in NP | -3.5 | 0.035292192 | -1.5 | 13192 | 17 | 52 | 42 | 10 | 13 | 10 | N | N | N | N | N | N |
| HTRA2 | high in NP | -2.3 | 0.035281964 | -1.5 | 13193 | 66 | 120 | 88 | 38 | 28 | 34 | N | P | N | N | N | N |
| SLC26A3 | high in NP | -10.1 | 0.035275145 | -1.5 | 13194 | 2 | 15 | 22 | 2 | 2 | 2 | N | N | N | N | N | N |
| SH3YL1 | high in NP | -7.5 | 0.035262871 | -1.5 | 13195 | 6 | 63 | 74 | 6 | 8 | 6 | N | P | N | N | N | N |
| RSAD2 | high in NP | -3.1 | 0.035236959 | -1.5 | 13196 | 46 | 134 | 87 | 24 | 20 | 26 | N | N | N | N | N | N |
| RAB6C | high in NP | -44.0 | 0.035224685 | -1.5 | 13197 | 1 | 183 | 78 | 3 | 1 | 1 | N | P | N | N | N | N |
| PSMB1 | high in NP | -2.8 | 0.035206955 | -1.5 | 13198 | 136 | 1494 | 170 | 71 | 49 | 43 | N | P | N | N | N | N |
| NPDC1 | high in NP | -2.9 | 0.035200136 | -1.5 | 13199 | 448 | 167 | 292 | 81 | 84 | 83 | N | N | N | N | N | N |
| ZNF148 | high in NP | -2.2 | 0.035193317 | -1.5 | 13200 | 61 | 87 | 61 | 34 | 34 | 29 | N | N | N | N | N | N |
| C14orf132 | high in NP | -2.3 | 0.035146267 | -1.5 | 13201 | 53 | 43 | 51 | 20 | 20 | 20 | N | N | N | N | N | N |
| MYOF | high in NP | -2.0 | 0.035139448 | -1.5 | 13202 | 37 | 57 | 49 | 30 | 29 | 26 | NA | NA | N | N | N | N |
| LOC96610 | high in NP | -4.6 | 0.03512581 | -1.5 | 13203 | 6 | 30 | 23 | 6 | 6 | 6 | NA | NA | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
| | | | | | | Nulliparous (NP) | | | | Parous (P) | | | NP | P | NP | | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
|---|---|---|---|---|---|---|---|---|---|---|---|---|---|---|---|---|---|
| RBM7 | high in NP | -3.1 | 0.035118991 | -1.5 | 13204 | 90 | 118 | 166 | 32 | 17 | 56 | N | N | N | N | N | N |
| AGAP1 | high in NP | -2.4 | 0.035083532 | -1.5 | 13205 | 104 | 127 | 80 | 47 | 38 | 38 | N | N | N | N | N | N |
| MRPL35 | high in NP | -4.7 | 0.034998295 | -1.5 | 13206 | 6 | 20 | 41 | 6 | 6 | 6 | N | N | N | N | N | N |
| HMGB1 | high in NP | -6.3 | 0.034991476 | -1.5 | 13207 | 23 | 140 | 90 | 21 | 22 | 17 | N | N | N | N | N | N |
| SRGN | high in NP | -5.3 | 0.034984657 | -1.5 | 13208 | 144 | 1955 | 132 | 69 | 23 | 52 | N | N | N | N | N | N |
| KEAP1 | high in NP | -9.3 | 0.034965564 | -1.5 | 13209 | 21 | 211 | 315 | 23 | 24 | 18 | N | N | N | N | N | N |
| DSTN | high in NP | -6.6 | 0.034872145 | -1.5 | 13210 | 104 | 599 | 386 | 66 | 98 | 53 | N | N | N | N | N | N |
| COX6A1 | high in NP | -21.3 | 0.034828503 | -1.5 | 13211 | 8 | 398 | 218 | 12 | 8 | 11 | N | N | N | N | N | N |
| TMEM35 | high in NP | -2.5 | 0.034801909 | -1.5 | 13212 | 10 | 11 | 7 | 4 | 4 | 4 | N | N | N | N | N | N |
| NBL1 | high in NP | -3.6 | 0.034754177 | -1.5 | 13213 | 113 | 388 | 146 | 101 | 30 | 34 | N | N | N | N | N | N |
| WDR82 | high in NP | -2.8 | 0.034698943 | -1.5 | 13214 | 177 | 484 | 317 | 116 | 112 | 126 | N | N | N | N | N | N |
| MAGED1 | high in NP | -8.6 | 0.034678486 | -1.5 | 13215 | 6 | 72 | 25 | 6 | 6 | 6 | N | N | N | N | P | N |
| ARPC4 | high in NP | -2.8 | 0.034655984 | -1.5 | 13216 | 1102 | 705 | 580 | 450 | 263 | 94 | N | N | N | N | N | N |
| ARRDC3 | high in NP | -3.5 | 0.034634163 | -1.5 | 13217 | 475 | 1104 | 1574 | 220 | 290 | 524 | P | N | N | N | N | N |
| DEF6 | high in NP | -4.2 | 0.034612342 | -1.5 | 13218 | 21 | 59 | 50 | 7 | 12 | 10 | N | N | N | N | N | N |
| RASA1 | high in NP | -2.6 | 0.034578929 | -1.5 | 13219 | 79 | 54 | 84 | 33 | 27 | 24 | N | N | N | N | N | N |
| SHFM1 | high in NP | -28.2 | 0.034538698 | -1.5 | 13220 | 2 | 224 | 94 | 2 | 4 | 2 | P | P | N | N | N | N |
| RAB37 | high in NP | -2.3 | 0.034452506 | -1.5 | 13221 | 9 | 7 | 5 | 3 | 3 | 3 | N | N | N | N | N | N |
| H6PD | high in NP | -2.6 | 0.034511422 | -1.5 | 13222 | 146 | 176 | 92 | 72 | 39 | 30 | N | N | N | N | N | N |
| FAM101B | high in NP | -2.7 | 0.034504603 | -1.5 | 13223 | 99 | 173 | 67 | 42 | 32 | 21 | N | N | N | N | N | N |
| STX18 | high in NP | -4.8 | 0.03447119 | -1.5 | 13224 | 8 | 25 | 32 | 8 | 8 | 8 | P | N | N | N | N | N |
| ZNF137 | high in NP | -2.5 | 0.034446642 | -1.5 | 13225 | 9 | 12 | 6 | 3 | 3 | 3 | N | N | N | N | N | N |
| MRPL50 | high in NP | -10.5 | 0.034434823 | -1.5 | 13226 | 3 | 28 | 14 | 3 | 3 | 3 | P | N | N | N | N | N |
| RIN2 | high in NP | -3.5 | 0.034426185 | -1.5 | 13227 | 15 | 43 | 54 | 15 | 15 | 15 | N | N | N | N | N | N |
| PRKAA1 | high in NP | -2.4 | 0.034419366 | -1.5 | 13228 | 21 | 39 | 49 | 17 | 15 | 15 | N | N | N | N | N | N |
| TSPO | high in NP | -8.6 | 0.034396863 | -1.5 | 13229 | 7 | 162 | 123 | 7 | 7 | 13 | N | N | N | N | N | N |
| LOC100216001 | high in NP | -11.6 | 0.034373679 | -1.5 | 13230 | 3 | 23 | 16 | 3 | 3 | 3 | P | N | N | N | N | N |
| EPHX2 | high in NP | -5.6 | 0.034342994 | -1.5 | 13231 | 110 | 26 | 50 | 8 | 18 | 19 | N | N | N | N | N | N |
| CCL28 | high in NP | -8.8 | 0.034313672 | -1.5 | 13232 | 5 | 29 | 52 | 5 | 5 | 5 | N | N | N | N | N | N |
| DIAPH1 | high in NP | -3.4 | 0.034300034 | -1.5 | 13233 | 489 | 620 | 576 | 187 | 377 | 132 | N | N | N | N | N | N |
| TSPAN4 | high in NP | -3.3 | 0.034223662 | -1.5 | 13234 | 243 | 143 | 143 | 60 | 16 | 64 | N | N | N | N | N | N |
| C11orf1 | high in NP | -4.9 | 0.03419775 | -1.5 | 13235 | 118 | 586 | 105 | 23 | 71 | 41 | N | N | N | N | N | N |
| CLU | high in NP | -11.6 | 0.034170474 | -1.5 | 13236 | 30 | 37 | 45 | 16 | 13 | 11 | N | N | N | N | N | N |
| BBS10 | high in NP | -4.5 | 0.034147971 | -1.5 | 13237 | 15 | 42 | 26 | 9 | 9 | 9 | N | N | N | N | N | N |
| TIFA | high in NP | -2.7 | 0.034247528 | -1.5 | 13238 | 8 | 24 | 34 | 8 | 8 | 8 | N | N | N | N | N | N |
| C1orf210 | high in NP | -2.2 | 0.034240709 | -1.5 | 13239 | 77 | 74 | 41 | 25 | 27 | 22 | N | N | N | N | N | N |
| ALDH7A1 | high in NP | -4.8 | 0.03423389 | -1.5 | 13240 | 6 | 47 | 22 | 6 | 6 | 6 | N | N | N | N | N | N |
| B4GALT4 | high in NP | -3.3 | 0.034223662 | -1.5 | 13241 | 3 | 17 | 21 | 8 | 3 | 3 | N | N | N | N | N | N |
| C11orf1 | high in NP | -4.5 | 0.034117286 | -1.5 | 13242 | 8 | 29 | 29 | 8 | 8 | 8 | N | N | N | N | N | N |
| HELLS | high in NP | -2.8 | 0.034117286 | -1.5 | 13243 | 70 | 93 | 110 | 34 | 24 | 10 | N | N | N | N | N | N |
| C7orf30 | high in NP | -2.7 | 0.034076372 | -1.5 | 13244 | 72 | 42 | 59 | 26 | 30 | 23 | N | N | N | N | N | N |
| MYH10 | high in NP | -2.5 | 0.034064098 | -1.5 | 13245 | 25 | 56 | 55 | 13 | 16 | 19 | N | N | N | N | N | N |
| TRIM4 | high in NP | -3.6 | 0.034049096 | -1.5 | 13246 | 8275 | 2815 | 3566 | 1963 | 1018 | 916 | N | N | N | N | N | N |
| TUBB | high in NP | -2.2 | 0.034015684 | -1.5 | 13247 | 367 | 358 | 433 | 191 | 178 | 119 | N | N | N | N | N | N |
| PUF60 | | | | | | | | | | | | | | | | | |

TABLE 15-continued

Genes that Are Differentially Methylated between Nulliparous and Parous CD44+ Breast Epithelial Cells

| | | | | | | SAGE-seq | | | | | | | | ChIP-seq | | | | MSDK-seq | | |
| --- | --- | --- | --- | --- | --- | --- | --- | --- | --- | --- | --- | --- | --- | --- | --- | --- | --- | --- | --- | --- |
| | | | | | | | Nulliparous (NP) | | | | Parous (P) | | | NP | | P | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | NP | GeneBody Met | P | Pro-moter Met | NP | Pro-moter Met | P |
| WBP5 | high in NP | -8.5 | 0.033961132 | -1.5 | 13248 | 56 | 249 | 334 | 31 | 35 | 33 | N | N | N | N | N | N | N | N |
| ABT1 | high in NP | -2.9 | 0.033794749 | -1.5 | 13249 | 75 | 138 | 170 | 51 | 39 | 14 | N | P | N | N | N | N | N | N |
| PLEKHF2 | high in NP | -4.2 | 0.03376611 | -1.5 | 13250 | 28 | 71 | 116 | 19 | 17 | 7 | N | N | N | N | N | N | N | N |
| MAGEH1 | high in NP | -3.5 | 0.033759291 | -1.5 | 13251 | 50 | 77 | 63 | 26 | 3 | 14 | N | N | N | N | N | N | N | N |
| MT1F | high in NP | -5.1 | 0.033684964 | -1.5 | 13252 | 7 | 233 | 4 | 1 | 1 | 1 | N | N | N | N | N | N | N | N |
| LIMA1 | high in NP | -3.8 | 0.033664507 | -1.5 | 13253 | 65 | 221 | 59 | 21 | 40 | 21 | N | N | N | N | N | N | N | N |
| FKBP7 | high in NP | -3.5 | 0.033616093 | -1.5 | 13254 | 237 | 107 | 84 | 20 | 20 | 59 | N | N | N | N | N | N | N | N |
| SMARCD1 | high in NP | -3.5 | 0.033576543 | -1.5 | 13255 | 16 | 63 | 77 | 9 | 17 | 9 | N | N | N | N | N | N | N | N |
| GLUD2 | high in NP | -11.9 | 0.033547903 | -1.5 | 13256 | 2 | 25 | 15 | 2 | 2 | 2 | N | N | N | N | N | N | N | N |
| DST | high in NP | -3.4 | 0.03347835 | -1.5 | 13257 | 157 | 451 | 372 | 138 | 201 | 153 | N | N | N | N | N | N | N | N |
| PKN1 | high in NP | -3.3 | 0.03346712 | -1.5 | 13258 | 243 | 121 | 187 | 85 | 20 | 51 | N | N | N | N | N | N | N | N |
| TWSG1 | high in NP | -5.4 | 0.033449028 | -1.5 | 13259 | 31 | 220 | 112 | 16 | 23 | 21 | N | N | N | N | N | N | N | N |
| CNOT10 | high in NP | -3.6 | 0.033442209 | -1.5 | 13260 | 14 | 27 | 28 | 10 | 8 | 8 | N | N | N | N | N | N | N | N |
| NAA50 | high in NP | -8.4 | 0.033428571 | -1.5 | 13261 | 63 | 540 | 450 | 53 | 38 | 64 | N | N | N | N | N | N | N | N |
| HPS3 | high in NP | -5.0 | 0.033414934 | -1.5 | 13262 | 10 | 31 | 25 | 10 | 10 | 10 | NA | N | NA | N | N | N | N | N |
| OBFC1 | high in NP | -2.6 | 0.033401296 | -1.5 | 13263 | 63 | 76 | 92 | 40 | 25 | 22 | N | N | N | N | N | N | N | N |
| CLEC3B | high in NP | -4.8 | 0.033394477 | -1.5 | 13264 | 751 | 796 | 2609 | 120 | 323 | 473 | N | NA | N | N | N | N | N | N |
| ROBO1 | high in NP | -3.1 | 0.033387658 | -1.5 | 13265 | 22 | 76 | 48 | 16 | 16 | 19 | N | N | N | N | N | N | N | N |
| EFEMP2 | high in NP | -4.0 | 0.03337061 | -1.5 | 13266 | 1118 | 236 | 400 | 187 | 71 | 84 | N | N | N | N | N | N | N | N |
| PHKG2 | high in NP | -10.1 | 0.033316741 | -1.5 | 13267 | 7 | 46 | 35 | 7 | 7 | 7 | N | N | N | N | N | N | N | N |
| SHMT2 | high in NP | -6.7 | 0.033309922 | -1.5 | 13268 | 31 | 310 | 171 | 37 | 20 | 16 | N | N | N | N | N | N | N | N |
| TMEM158 | high in NP | -7.9 | 0.033297647 | -1.5 | 13269 | 6 | 71 | 77 | 9 | 6 | 6 | N | N | N | N | N | N | N | N |
| NRAS | high in NP | -5.0 | 0.033271735 | -1.5 | 13270 | 9 | 51 | 38 | 9 | 9 | 9 | N | N | N | N | N | N | N | N |
| LDLRAD3 | high in NP | -8.2 | 0.033264916 | -1.5 | 13271 | 25 | 228 | 189 | 13 | 16 | 22 | N | N | N | N | N | N | N | N |
| ATF6 | high in NP | -2.2 | 0.03323764 | -1.5 | 13272 | 164 | 182 | 198 | 80 | 42 | 76 | N | N | N | N | N | N | N | N |
| SLBP | high in NP | -3.3 | 0.033192636 | -1.5 | 13273 | 285 | 174 | 136 | 83 | 74 | 25 | N | N | N | N | N | N | N | N |
| DNALI1 | high in NP | -3.2 | 0.033164678 | -1.5 | 13274 | 117 | 364 | 71 | 36 | 38 | 23 | N | N | N | N | N | N | N | N |
| YEATS4 | high in NP | -5.7 | 0.033157859 | -1.5 | 13275 | 32 | 20 | 38 | 15 | 6 | 6 | N | N | N | N | N | N | N | N |
| MPV17 | high in NP | -11.2 | 0.033109444 | -1.5 | 13276 | 3 | 38 | 33 | 3 | 3 | 3 | N | N | N | N | N | N | N | N |
| NUCB1 | high in NP | -3.1 | 0.033096488 | -1.5 | 13277 | 371 | 249 | 122 | 66 | 53 | 64 | N | N | N | N | N | N | N | N |
| BAX | high in NP | -3.1 | 0.033089669 | -1.5 | 13278 | 41 | 60 | 100 | 21 | 11 | 14 | N | N | N | N | N | N | N | N |
| FSCN1 | high in NP | -7.8 | 0.033076713 | -1.5 | 13279 | 17 | 86 | 101 | 6 | 13 | 9 | N | N | N | N | N | N | N | N |
| GCLM | high in NP | -3.6 | 0.033037163 | -1.5 | 13280 | 870 | 275 | 369 | 70 | 111 | 197 | N | N | N | N | N | N | N | N |
| C13orf37 | high in NP | -4.2 | 0.033024889 | -1.5 | 13281 | 190 | 479 | 710 | 110 | 147 | 111 | N | N | N | N | N | P | N | N |
| NEK6 | high in NP | -4.8 | 0.03301807 | -1.5 | 13282 | 8 | 29 | 29 | 8 | 9 | 8 | N | N | N | N | N | N | N | N |
| SYNGR2 | high in NP | -2.3 | 0.03301251 | -1.5 | 13283 | 15 | 25 | 27 | 9 | 9 | 9 | N | N | N | N | N | N | N | N |
| RUSC2 | high in NP | -2.7 | 0.032988749 | -1.5 | 13284 | 377 | 374 | 243 | 154 | 128 | 44 | N | N | N | N | N | N | N | N |
| TIMM10 | high in NP | -3.0 | 0.032975111 | -1.5 | 13285 | 71 | 172 | 175 | 49 | 34 | 49 | N | N | N | N | N | N | N | N |
| SLC7A6OS | high in NP | -2.7 | 0.032988292 | -1.5 | 13286 | 126 | 146 | 220 | 43 | 69 | 26 | N | N | N | N | N | N | N | N |
| ZFR | high in NP | -12.7 | 0.03295329 | -1.5 | 13287 | 4 | 28 | 19 | 4 | 4 | 4 | N | N | N | N | N | N | N | N |
| SART3 | high in NP | -4.2 | 0.032867371 | -1.5 | 13288 | 85 | 215 | 240 | 62 | 43 | 43 | N | N | N | N | N | N | N | N |
| MAGI1 | high in NP | -4.3 | 0.032830549 | -1.5 | 13289 | 29 | 166 | 162 | 22 | 26 | 30 | N | N | N | N | N | P | N | N |
| KRR1 | high in NP | -2.7 | 0.032803955 | -1.5 | 13290 | 99 | 58 | 61 | 32 | 33 | 24 | N | N | N | N | N | N | N | N |
| | high in NP | -3.2 | 0.032790317 | -1.5 | 13291 | 65 | 115 | 138 | 30 | 37 | 34 | N | N | N | N | N | N | N | N |

TABLE 15-continued

Genes that Are Differentially Methylated between Nulliparous and Parous CD44+ Breast Epithelial Cells

| | | | | | SAGE-seq | | | | | | ChIP-seq | | | | MSDK-seq | | |
| --- | --- | --- | --- | --- | --- | --- | --- | --- | --- | --- | --- | --- | --- | --- | --- | --- | --- |
| | | | | | | Nulliparous (NP) | | | Parous (P) | | | NP | P | GeneBody NP Met | GeneBody Met | Pro-motor Met | Pro-moter Met |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | | | | |
| PRINS | high in NP | -3.0 | 0.032773952 | -1.5 | 13292 | 49 | 37 | 64 | 13 | 21 | 14 | N | N | N | N | N | N |
| C11orf2 | high in NP | -3.8 | 0.032711899 | -1.5 | 13293 | 7 | 57 | 71 | 7 | 7 | 10 | N | N | N | N | N | N |
| ZMYM2 | high in NP | -2.2 | 0.032698261 | -1.5 | 13294 | 21 | 47 | 56 | 19 | 15 | 15 | N | N | N | N | N | N |
| FBXO28 | high in NP | -2.5 | 0.03267985 | -1.5 | 13295 | 201 | 202 | 137 | 92 | 81 | 52 | N | N | N | N | N | N |
| LETMD1 | high in NP | -5.3 | 0.032673031 | -1.5 | 13296 | 11 | 33 | 33 | 11 | 11 | 11 | N | N | N | N | N | N |
| PSMD10 | high in NP | -4.9 | 0.032666212 | -1.5 | 13297 | 5 | 27 | 25 | 5 | 5 | 5 | N | N | N | N | N | N |
| CNIH | high in NP | -3.2 | 0.032659393 | -1.5 | 13298 | 24 | 65 | 44 | 16 | 12 | 15 | N | N | N | N | N | N |
| COQ2 | high in NP | -4.5 | 0.032652574 | -1.5 | 13299 | 23 | 14 | 4 | 7 | 2 | 2 | N | N | N | N | N | N |
| RADIL | high in NP | -3.4 | 0.032645755 | -1.5 | 13300 | 80 | 41 | 55 | 19 | 8 | 18 | N | N | N | N | N | N |
| CSTA | high in NP | -14.4 | 0.032632117 | -1.5 | 13301 | 2 | 22 | 18 | 2 | 2 | 2 | N | N | N | N | N | N |
| SERPINA3 | high in NP | -9.7 | 0.032613024 | -1.5 | 13302 | 88 | 1601 | 2333 | 30 | 235 | 38 | N | N | N | N | N | N |
| B9D1 | high in NP | -5.7 | 0.032606205 | -1.5 | 13303 | 9 | 18 | 21 | 6 | 3 | 3 | N | N | N | N | N | N |
| MRPL13 | high in NP | -12.3 | 0.032593249 | -1.5 | 13304 | 4 | 41 | 18 | 4 | 4 | 4 | N | N | N | N | N | N |
| KLF3 | high in NP | -2.4 | 0.032511422 | -1.5 | 13305 | 226 | 273 | 277 | 151 | 61 | 112 | N | N | N | N | N | N |
| API5 | high in NP | -7.8 | 0.032487555 | -1.5 | 13306 | 12 | 97 | 147 | 12 | 12 | 18 | N | N | N | N | N | N |
| SNX17 | high in NP | -2.8 | 0.032424821 | -1.5 | 13307 | 21 | 81 | 74 | 22 | 10 | 10 | N | N | N | N | N | N |
| C3orf17 | high in NP | -2.2 | 0.032403 | -1.5 | 13308 | 60 | 118 | 83 | 41 | 35 | 32 | N | N | N | N | N | N |
| ZNF770 | high in NP | -2.6 | 0.032396181 | -1.5 | 13309 | 127 | 169 | 255 | 71 | 59 | 82 | N | N | N | N | N | N |
| AHR | high in NP | -3.1 | 0.032375043 | -1.5 | 13310 | 343 | 852 | 662 | 267 | 225 | 240 | N | N | N | N | N | N |
| RAB33B | high in NP | -2.2 | 0.032368224 | -1.5 | 13311 | 34 | 46 | 57 | 20 | 21 | 21 | P | N | N | N | N | N |
| PLEKHA9 | high in NP | -14.3 | 0.03235254 | -1.5 | 13312 | 4 | 23 | 25 | 4 | 4 | 4 | N | N | N | N | N | N |
| RAB23 | high in NP | -12.0 | 0.032336856 | -1.5 | 13313 | 4 | 42 | 39 | 4 | 4 | 4 | N | N | N | N | N | N |
| LRRC8A | high in NP | -2.4 | 0.032323219 | -1.5 | 13314 | 1195 | 1025 | 1232 | 443 | 497 | 669 | N | N | N | N | N | N |
| ACTB | high in NP | -2.7 | 0.032309581 | -1.5 | 13315 | 148 | 267 | 186 | 71 | 114 | 38 | N | N | N | N | N | N |
| BOLA1 | high in NP | -2.5 | 0.032302762 | -1.5 | 13316 | 9 | 11 | 6 | 3 | 3 | 3 | N | N | N | N | N | N |
| LGALS3 | high in NP | -14.4 | 0.032295943 | -1.5 | 13317 | 33 | 786 | 526 | 29 | 28 | 36 | N | N | N | N | N | N |
| MED21 | high in NP | -5.6 | 0.03227344 | -1.5 | 13318 | 9 | 46 | 52 | 9 | 9 | 9 | N | N | N | N | N | N |
| RPS19 | high in NP | -13.9 | 0.032232526 | -1.5 | 13319 | 202 | 5679 | 2849 | 150 | 203 | 179 | N | N | N | N | N | N |
| AGK | high in NP | -14.3 | 0.032204569 | -1.5 | 13320 | 6 | 24 | 29 | 6 | 6 | 6 | N | N | N | N | N | N |
| UXT | high in NP | -3.2 | 0.032190931 | -1.5 | 13321 | 163 | 426 | 324 | 114 | 55 | 75 | N | N | N | N | N | N |
| PMVK | high in NP | -7.4 | 0.032158882 | -1.5 | 13322 | 13 | 54 | 35 | 7 | 10 | 7 | N | N | N | N | N | N |
| NFIA | high in NP | -3.9 | 0.032120696 | -1.5 | 13323 | 1042 | 358 | 244 | 256 | 70 | 134 | N | N | N | N | N | N |
| C1orf103 | high in NP | -3.6 | 0.032098875 | -1.5 | 13324 | 13 | 47 | 13 | 6 | 6 | 6 | N | N | N | N | N | N |
| HOOK2 | high in NP | -5.7 | 0.032071599 | -1.5 | 13325 | 11 | 47 | 48 | 11 | 11 | 11 | N | N | N | N | N | N |
| RHOT1 | high in NP | -2.9 | 0.032045687 | -1.5 | 13326 | 52 | 43 | 47 | 22 | 12 | 12 | N | N | N | N | N | N |
| CCNT1 | high in NP | -2.6 | 0.032038868 | -1.5 | 13327 | 24 | 45 | 21 | 8 | 11 | 8 | P | N | N | N | P | N |
| LOC388796 | high in NP | -8.5 | 0.032018411 | -1.5 | 13328 | 44 | 545 | 399 | 18 | 50 | 24 | N | N | N | N | N | N |
| ACSL3 | high in NP | -6.2 | 0.032003409 | -1.5 | 13329 | 51 | 273 | 268 | 27 | 47 | 37 | N | N | N | N | N | N |
| PLEKHH2 | high in NP | -4.8 | 0.031980907 | -1.5 | 13330 | 53 | 353 | 247 | 43 | 42 | 41 | N | N | N | N | N | N |
| ZNF71 | high in NP | -3.1 | 0.031974088 | -1.5 | 13331 | 29 | 18 | 16 | 10 | 6 | 6 | N | N | N | N | N | N |
| IFNGR1 | high in NP | -2.9 | 0.031967269 | -1.5 | 13332 | 47 | 120 | 102 | 39 | 26 | 22 | P | N | N | N | N | N |
| TMEM144 | high in NP | -2.9 | 0.031911354 | -1.5 | 13333 | 13 | 12 | 23 | 7 | 7 | 7 | N | N | N | N | N | N |
| SEC24A | high in NP | -3.3 | 0.03184818 | -1.5 | 13334 | 146 | 441 | 340 | 71 | 101 | 114 | N | N | N | N | N | N |
| SH3BP5 | high in NP | -3.9 | 0.031794749 | -1.5 | 13335 | 105 | 329 | 248 | 66 | 47 | 66 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | Parous (P) | | | NP | | P | | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| FSTL1 | high in NP | −2.9 | 0.031784521 | −1.5 | 13336 | 15169 | 5551 | 5318 | 2198 | 1792 | 3168 | N | N | N | N | N | N |
| FAM162A | high in NP | −16.9 | 0.031756563 | −1.5 | 13337 | 11 | 151 | 115 | 5 | 8 | 8 | N | N | N | N | N | N |
| N4BP2L1 | high in NP | −3.0 | 0.031723832 | −1.5 | 13338 | 48 | 26 | 42 | 15 | 11 | 14 | N | N | N | N | N | N |
| JAK1 | high in NP | −3.5 | 0.031717013 | −1.5 | 13339 | 134 | 349 | 190 | 83 | 52 | 108 | N | N | N | N | N | N |
| STAT1 | high in NP | −3.0 | 0.03170133 | −1.5 | 13340 | 212 | 190 | 215 | 121 | 62 | 53 | N | N | N | P | N | N |
| PRKACB | high in NP | −2.6 | 0.031625639 | −1.5 | 13341 | 123 | 35 | 44 | 15 | 11 | 355 | N | N | N | N | N | N |
| DUSP5 | high in NP | −2.6 | 0.031605182 | −1.5 | 13342 | 595 | 723 | 563 | 227 | 239 | 355 | N | N | N | P | N | N |
| COX5A | high in NP | −6.3 | 0.031556768 | −1.5 | 13343 | 43 | 211 | 281 | 20 | 31 | 25 | N | N | N | N | N | N |
| C11orf24 | high in NP | −3.7 | 0.031522673 | −1.5 | 13344 | 52 | 152 | 68 | 34 | 16 | 9 | N | N | N | N | N | N |
| EFNA4 | high in NP | −14.3 | 0.031505626 | −1.5 | 13345 | 5 | 23 | 33 | 5 | 5 | 5 | N | N | N | N | N | P |
| TMEM130 | high in NP | −5.6 | 0.031493352 | −1.5 | 13346 | 256 | 27 | 20 | 7 | 7 | 15 | N | N | N | N | N | N |
| LIMCH1 | high in NP | −3.7 | 0.031428571 | −1.5 | 13347 | 59 | 96 | 111 | 24 | 29 | 48 | N | N | N | N | N | N |
| SFPQ | high in NP | −3.3 | 0.031382203 | −1.5 | 13348 | 359 | 775 | 858 | 230 | 289 | 222 | N | N | N | N | N | N |
| SLC9A3R2 | high in NP | −2.9 | 0.031354245 | −1.5 | 13349 | 67 | 40 | 35 | 14 | 16 | 5 | N | N | N | N | N | N |
| LPHN3 | high in NP | −4.6 | 0.031347426 | −1.5 | 13350 | 173 | 25 | 12 | 8 | 8 | 8 | N | N | N | N | N | N |
| CKAP4 | high in NP | −3.7 | 0.031340607 | −1.5 | 13351 | 2102 | 1398 | 1743 | 1022 | 408 | 350 | N | N | N | N | N | N |
| CYP7B1 | high in NP | −15.1 | 0.031302421 | −1.5 | 13352 | 3 | 32 | 20 | 3 | 3 | 3 | N | N | N | N | N | N |
| MBOAT1 | high in NP | −3.6 | 0.031275145 | −1.5 | 13353 | 17 | 113 | 82 | 17 | 19 | 20 | N | N | N | N | N | N |
| SPCS1 | high in NP | −2.7 | 0.031268326 | −1.5 | 13354 | 673 | 458 | 441 | 259 | 169 | 69 | N | N | N | N | N | N |
| LMNA | high in NP | −3.3 | 0.031261507 | −1.5 | 13355 | 6193 | 4679 | 5860 | 1655 | 1468 | 3323 | N | N | N | N | N | N |
| LOC100233209 | high in NP | −2.7 | 0.031205592 | −1.5 | 13356 | 180 | 381 | 320 | 111 | 74 | 109 | NA | NA | N | N | N | N |
| ECHDC3 | high in NP | −11.7 | 0.031198773 | −1.5 | 13357 | 6 | 75 | 39 | 6 | 6 | 6 | N | N | N | N | N | N |
| CAPNS1 | high in NP | −2.4 | 0.031148312 | −1.5 | 13358 | 705 | 547 | 550 | 243 | 296 | 135 | N | N | N | N | N | N |
| PSPC1 | high in NP | −2.8 | 0.031117627 | −1.5 | 13359 | 22 | 53 | 37 | 9 | 15 | 9 | N | N | N | N | N | N |
| DERL2 | high in NP | −16.5 | 0.03109717 | −1.5 | 13360 | 5 | 195 | 166 | 7 | 5 | 8 | N | N | N | N | N | N |
| GSTP1 | high in NP | −2.3 | 0.031081487 | −1.5 | 13361 | 1608 | 1681 | 1873 | 816 | 683 | 282 | N | N | N | N | N | N |
| SLCO4A1 | high in NP | −2.9 | 0.031015343 | −1.5 | 13362 | 46 | 100 | 115 | 22 | 16 | 29 | N | N | N | N | N | N |
| ZSWIM4 | high in NP | −6.8 | 0.031001705 | −1.5 | 13363 | 13 | 149 | 157 | 16 | 21 | 13 | N | N | N | N | N | N |
| DEPDC6 | high in NP | −2.7 | 0.030979884 | −1.5 | 13364 | 17 | 18 | 28 | 10 | 10 | 10 | N | N | N | N | N | N |
| BRRF1 | high in NP | −7.2 | 0.030973065 | −1.5 | 13365 | 291 | 3460 | 2684 | 168 | 132 | 483 | N | N | N | N | N | N |
| PDGFB | high in NP | −2.3 | 0.030951926 | −1.5 | 13366 | 49 | 26 | 25 | 13 | 10 | 10 | N | P | N | N | N | N |
| RYK | high in NP | −2.3 | 0.030938288 | −1.5 | 13367 | 227 | 135 | 161 | 74 | 71 | 52 | N | N | N | N | N | N |
| RBBP5 | high in NP | −5.9 | 0.030916468 | −1.5 | 13368 | 9 | 46 | 30 | 9 | 9 | 9 | N | N | N | N | N | N |
| SUDS3 | high in NP | −2.4 | 0.030909649 | −1.5 | 13369 | 61 | 85 | 66 | 29 | 36 | 18 | N | N | N | N | N | N |
| ARL6IP4 | high in NP | −2.8 | 0.030880327 | −1.5 | 13370 | 187 | 404 | 367 | 145 | 73 | 73 | N | N | N | N | N | N |
| TMEM51 | high in NP | −3.1 | 0.030873508 | −1.5 | 13371 | 86 | 235 | 178 | 28 | 44 | 53 | N | N | N | N | N | N |
| POLR1D | high in NP | −4.5 | 0.030845551 | −1.5 | 13372 | 79 | 518 | 257 | 53 | 47 | 41 | N | N | N | N | N | N |
| C17orf81 | high in NP | −2.8 | 0.030816229 | −1.5 | 13373 | 37 | 68 | 65 | 18 | 20 | 17 | N | N | N | N | N | N |
| MOB3KL3 | high in NP | −6.2 | 0.030774633 | −1.5 | 13374 | 7 | 49 | 44 | 7 | 7 | 7 | N | N | N | N | N | N |
| GNPNAT1 | high in NP | −4.1 | 0.030748721 | −1.5 | 13375 | 20 | 153 | 51 | 13 | 16 | 13 | N | N | N | N | N | N |
| SLC25A28 | high in NP | −2.9 | 0.030707126 | −1.5 | 13376 | 74 | 278 | 139 | 47 | 38 | 38 | N | N | N | N | N | N |
| SUMO3 | high in NP | −2.8 | 0.030636891 | −1.5 | 13377 | 440 | 357 | 300 | 201 | 123 | 80 | N | N | N | N | N | N |
| ENSA | high in NP | −2.7 | 0.030614388 | −1.5 | 13378 | 85 | 122 | 166 | 67 | 36 | 40 | N | N | N | N | N | N |
| SRP68 | high in NP | −5.4 | 0.030607569 | −1.5 | 13379 | 27 | 160 | 149 | 28 | 9 | 13 | P | N | N | N | N | N |

TABLE 15-continued

Genes that Are Differentially Methylated between Nulliparous and Parous CD44+ Breast Epithelial Cells

| | | | | | SAGE-seq | | | | | | ChIP-seq | | MSDK-seq | | | |
|---|---|---|---|---|---|---|---|---|---|---|---|---|---|---|---|---|
| | | | | | Nulliparous (NP) | | | Parous (P) | | | NP | P | | NP | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| SGCE | high in NP | -3.2 | 0.030565292 | -1.5 | 13380 | 212 | 332 | 108 | 35 | 35 | 88 | N | N | N | N | N | N |
| SSBP1 | high in NP | -8.2 | 0.030524378 | -1.5 | 13381 | 11 | 60 | 40 | 5 | 5 | 8 | N | N | N | N | N | N |
| PPP1R15B | high in NP | -2.8 | 0.03051074 | -1.5 | 13382 | 2506 | 2264 | 1780 | 695 | 676 | 1261 | N | N | N | N | N | N |
| PSMC4 | high in NP | -8.7 | 0.030497102 | -1.5 | 13383 | 97 | 904 | 840 | 83 | 87 | 44 | N | N | N | N | N | N |
| DCP1A | high in NP | -2.3 | 0.030460961 | -1.5 | 13384 | 102 | 135 | 96 | 57 | 46 | 50 | N | N | N | N | N | N |
| STK32B | high in NP | -2.7 | 0.030385953 | -1.5 | 13385 | 16 | 29 | 32 | 9 | 9 | 9 | N | N | N | N | N | N |
| PLN | high in NP | -3.1 | 0.030372315 | -1.5 | 13386 | 9 | 18 | 8 | 3 | 3 | 3 | N | N | N | N | N | N |
| SRPK1 | high in NP | -3.4 | 0.030365496 | -1.5 | 13387 | 83 | 173 | 241 | 46 | 52 | 26 | N | N | N | N | N | N |
| BGN | high in NP | -4.6 | 0.030351858 | -1.5 | 13388 | 2295 | 3136 | 344 | 107 | 70 | 601 | N | N | N | N | N | N |
| MAL2 | high in NP | -3.5 | 0.030285032 | -1.5 | 13389 | 9 | 53 | 96 | 9 | 9 | 9 | N | N | N | N | N | N |
| MSTO1 | high in NP | -2.6 | 0.030232526 | -1.5 | 13390 | 8 | 8 | 2 | 2 | 2 | 2 | N | N | N | N | N | N |
| EIF3E | high in NP | -2.8 | 0.030225707 | -1.5 | 13391 | 56 | 94 | 105 | 23 | 31 | 29 | N | N | N | N | P | N |
| NEK5 | high in NP | -3.1 | 0.030196386 | -1.5 | 13392 | 60 | 260 | 81 | 25 | 20 | 15 | N | N | N | N | N | N |
| E2F5 | high in NP | -16.7 | 0.030182748 | -1.5 | 13393 | 6 | 29 | 39 | 2 | 6 | 6 | N | N | N | N | N | N |
| SSR4 | high in NP | -2.8 | 0.030152063 | -1.5 | 13394 | 408 | 775 | 461 | 265 | 145 | 113 | N | N | N | N | N | N |
| AXL | high in NP | -2.4 | 0.030145244 | -1.5 | 13395 | 1940 | 2302 | 2209 | 927 | 616 | 1143 | N | N | N | N | N | N |
| GYG1 | high in NP | -4.1 | 0.030138425 | -1.5 | 13396 | 253 | 286 | 84 | 55 | 47 | 23 | N | N | N | N | N | N |
| NDUFA11 | high in NP | -3.3 | 0.030084555 | -1.5 | 13397 | 412 | 444 | 278 | 171 | 114 | 53 | N | N | N | N | P | N |
| EHD4 | high in NP | -2.9 | 0.029987044 | -1.5 | 13398 | 27 | 71 | 45 | 17 | 17 | 14 | N | N | N | N | P | N |
| WASL | high in NP | -3.8 | 0.029937266 | -1.5 | 13399 | 64 | 230 | 159 | 66 | 26 | 35 | N | N | N | N | N | N |
| KRT6B | high in NP | -14.1 | 0.029890215 | -1.5 | 13400 | 120 | 1046 | 469 | 34 | 198 | 21 | N | N | N | N | N | N |
| TAF6 | high in NP | -5.9 | 0.029862257 | -1.5 | 13401 | 34 | 56 | 50 | 25 | 8 | 8 | N | N | N | N | N | N |
| LIMS1 | high in NP | -14.1 | 0.029855438 | -1.5 | 13402 | 3 | 62 | 40 | 3 | 3 | 3 | N | N | N | N | N | N |
| ATP1A1 | high in NP | -2.4 | 0.029848619 | -1.5 | 13403 | 1318 | 1974 | 2693 | 774 | 681 | 767 | N | N | N | N | N | N |
| S100A4 | high in NP | -8.1 | 0.029813161 | -1.5 | 13404 | 18 | 476 | 92 | 10 | 9 | 9 | P | N | N | N | N | N |
| TXNIP | high in NP | -6.1 | 0.029767474 | -1.5 | 13405 | 109 | 609 | 489 | 86 | 44 | 91 | N | N | N | N | N | N |
| CAV1 | high in NP | -3.9 | 0.029760655 | -1.5 | 13406 | 2594 | 2548 | 859 | 712 | 707 | 240 | N | N | N | N | N | N |
| CBLC | high in NP | -6.7 | 0.029747017 | -1.5 | 13407 | 6 | 32 | 74 | 6 | 6 | 6 | N | N | N | N | N | N |
| ARMCX1 | high in NP | -3.6 | 0.029674054 | -1.5 | 13408 | 89 | 153 | 243 | 33 | 26 | 52 | N | N | N | N | N | N |
| RPS15A | high in NP | -3.0 | 0.029625639 | -1.5 | 13409 | 837 | 1379 | 1512 | 230 | 409 | 531 | N | N | N | N | N | N |
| SLC35B3 | high in NP | -3.8 | 0.029588817 | -1.5 | 13410 | 41 | 18 | 39 | 11 | 5 | 5 | N | N | N | N | N | N |
| C1orf86 | high in NP | -2.4 | 0.029545176 | -1.5 | 13411 | 98 | 114 | 211 | 37 | 34 | 36 | N | N | N | N | N | N |
| C1orf77 | high in NP | -6.8 | 0.029538357 | -1.5 | 13412 | 16 | 96 | 104 | 9 | 5 | 10 | N | N | N | N | N | N |
| ZNF165 | high in NP | -2.9 | 0.029522673 | -1.5 | 13413 | 12 | 13 | 29 | 6 | 6 | 6 | N | N | N | N | N | N |
| RGS5 | high in NP | -6.2 | 0.029457211 | -1.5 | 13414 | 3925 | 1963 | 543 | 619 | 235 | 278 | N | N | N | N | N | N |
| COMMD10 | high in NP | -2.6 | 0.029419025 | -1.5 | 13415 | 9 | 4 | 8 | 3 | 3 | 3 | N | NA | N | N | N | N |
| SDHAF2 | high in NP | -2.7 | 0.029393113 | -1.5 | 13416 | 110 | 206 | 222 | 77 | 49 | 35 | NA | NA | N | N | N | N |
| MRPS30 | high in NP | -3.3 | 0.029363109 | -1.5 | 13417 | 81 | 96 | 86 | 20 | 36 | 18 | N | N | N | N | N | N |
| EHD2 | high in NP | -3.8 | 0.02935629 | -1.5 | 13418 | 7734 | 2327 | 1103 | 998 | 589 | 329 | N | N | N | N | N | N |
| GJC2 | high in NP | -2.5 | 0.029342653 | -1.5 | 13419 | 43 | 30 | 50 | 15 | 14 | 15 | N | N | N | N | N | N |
| SUGT1 | high in NP | -5.4 | 0.029301057 | -1.5 | 13420 | 23 | 109 | 73 | 13 | 5 | 9 | N | N | N | N | N | N |
| CYC1 | high in NP | -3.7 | 0.029271054 | -1.5 | 13421 | 14 | 69 | 71 | 8 | 13 | 8 | N | N | N | N | N | N |
| CASP7 | high in NP | -3.8 | 0.029156495 | -1.5 | 13422 | 34 | 85 | 56 | 29 | 13 | 13 | N | N | N | N | N | N |
| AHNAK | high in NP | -2.4 | 0.029133992 | -1.5 | 13423 | 218 | 236 | 282 | 112 | 158 | 122 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | | Nulliparous (NP) | | | | Parous (P) | | | NP | | P | | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-motor Met |
| GTF3C1 | high in NP | −2.4 | 0.029079441 | −1.5 | 13424 | 204 | 195 | 271 | 99 | 106 | 70 | N | N | N | N | N | N |
| SPINT1 | high in NP | −5.7 | 0.02904671 | −1.5 | 13425 | 75 | 398 | 507 | 38 | 77 | 13 | N | N | N | N | N | N |
| INPP5E | high in NP | −2.6 | 0.029031026 | −1.5 | 13426 | 24 | 42 | 32 | 10 | 14 | 8 | N | N | N | N | N | N |
| GNG5 | high in NP | −9.3 | 0.028986021 | −1.5 | 13427 | 50 | 366 | 435 | 37 | 24 | 19 | N | N | N | N | N | N |
| GGT5 | high in NP | −3.8 | 0.028911013 | −1.5 | 13428 | 1542 | 337 | 163 | 71 | 53 | 77 | N | N | N | N | N | N |
| C9orf21 | high in NP | −3.3 | 0.028904194 | −1.5 | 13429 | 433 | 520 | 232 | 133 | 106 | 112 | N | N | N | N | N | N |
| BLMH | high in NP | −2.8 | 0.02889192 | −1.5 | 13430 | 107 | 157 | 66 | 38 | 20 | 34 | N | N | N | N | N | N |
| PPP2R1A | high in NP | −3.1 | 0.028833958 | −1.5 | 13431 | 1087 | 724 | 748 | 377 | 369 | 183 | N | N | N | N | N | N |
| MAP1B | high in NP | −2.5 | 0.028813502 | −1.5 | 13432 | 1050 | 1094 | 1416 | 742 | 511 | 330 | N | N | N | N | N | N |
| UBE2Q2 | high in NP | −6.6 | 0.028792363 | −1.5 | 13433 | 6 | 110 | 60 | 6 | 6 | 6 | N | N | N | N | N | P |
| POMP | high in NP | −3.0 | 0.028785544 | −1.5 | 13434 | 620 | 962 | 1226 | 417 | 301 | 135 | N | N | N | N | N | N |
| FHL1 | high in NP | −3.6 | 0.028778725 | −1.5 | 13435 | 203 | 352 | 102 | 59 | 26 | 62 | N | N | N | N | N | N |
| HSPA5 | high in NP | −4.1 | 0.028763041 | −1.5 | 13436 | 1055 | 4599 | 5027 | 1252 | 423 | 352 | N | N | N | N | N | N |
| C7orf23 | high in NP | −17.4 | 0.028756222 | −1.5 | 13437 | 6 | 57 | 62 | 6 | 6 | 6 | N | N | N | N | N | N |
| DUSP4 | high in NP | −4.5 | 0.028749403 | −1.5 | 13438 | 33 | 153 | 119 | 16 | 33 | 19 | N | N | N | N | N | N |
| TIGD3 | high in NP | −3.0 | 0.028742584 | −1.5 | 13439 | 10 | 14 | 8 | 4 | 4 | 4 | N | N | N | N | N | N |
| TFF1 | high in NP | −14.7 | 0.028722128 | −1.5 | 13440 | 55 | 59 | 101 | 6 | 42 | 3 | P | P | N | N | N | N |
| SIK1 | high in NP | −2.6 | 0.028701671 | −1.5 | 13441 | 2391 | 3190 | 3111 | 1005 | 1266 | 1641 | NA | NA | N | N | N | N |
| MRPL9 | high in NP | −4.0 | 0.028608251 | −1.5 | 13442 | 9 | 40 | 11 | 3 | 3 | 3 | N | P | N | N | N | N |
| HBA1 | high in NP | −65.8 | 0.02852506 | −1.5 | 13443 | 28 | 14210 | 1814 | 20 | 13 | 19 | P | P | N | N | N | N |
| LOC100190939 | high in NP | −2.3 | 0.028500511 | −1.5 | 13444 | 165 | 168 | 209 | 63 | 81 | 59 | P | P | N | N | N | N |
| PM20D2 | high in NP | −3.0 | 0.028493692 | −1.5 | 13445 | 29 | 62 | 75 | 18 | 14 | 17 | N | N | N | N | N | N |
| ARIH2 | high in NP | −2.5 | 0.028467099 | −1.5 | 13446 | 217 | 367 | 320 | 132 | 153 | 96 | N | P | N | N | N | N |
| HTRA1 | high in NP | −4.2 | 0.02846028 | −1.5 | 13447 | 62 | 469 | 52 | 17 | 14 | 22 | P | N | N | N | N | N |
| RPLP1 | high in NP | −18.6 | 0.028453461 | −1.5 | 13448 | 97 | 3274 | 1202 | 62 | 55 | 82 | NA | NA | N | N | N | N |
| DCAF12 | high in NP | −3.8 | 0.028411865 | −1.5 | 13449 | 70 | 215 | 145 | 26 | 33 | 50 | N | P | N | N | N | N |
| NUP133 | high in NP | −3.5 | 0.028405046 | −1.5 | 13450 | 20 | 48 | 53 | 16 | 13 | 13 | N | N | N | N | N | N |
| C1orf198 | high in NP | −2.6 | 0.028391408 | −1.5 | 13451 | 2204 | 1219 | 1098 | 513 | 476 | 707 | N | N | N | N | N | N |
| H1ATL1 | high in NP | −2.7 | 0.028301398 | −1.5 | 13452 | 142 | 371 | 238 | 82 | 59 | 83 | N | N | N | N | N | N |
| RGS2 | high in NP | −3.8 | 0.028289124 | −1.5 | 13453 | 59 | 62 | 54 | 9 | 14 | 28 | N | N | N | N | N | N |
| PDGFC | high in NP | −2.8 | 0.0282373 | −1.5 | 13454 | 18 | 36 | 37 | 9 | 7 | 10 | N | N | N | N | N | N |
| ARAP1 | high in NP | −2.5 | 0.028230481 | −1.5 | 13455 | 49 | 94 | 67 | 27 | 22 | 28 | N | N | N | N | N | N |
| MRFAP1 | high in NP | −13.5 | 0.028195704 | −1.5 | 13456 | 12 | 224 | 106 | 14 | 12 | 12 | N | N | N | N | N | P |
| MRPL36 | high in NP | −21.1 | 0.028188885 | −1.5 | 13457 | 5 | 52 | 31 | 5 | 5 | 5 | N | N | N | N | N | N |
| SCNN1B | high in NP | −3.4 | 0.028182066 | −1.6 | 13458 | 13 | 13 | 23 | 6 | 6 | 6 | N | N | N | N | N | N |
| IL33 | high in NP | −4.4 | 0.028175247 | −1.6 | 13459 | 62 | 137 | 40 | 24 | 9 | 9 | N | P | N | N | N | N |
| KLHL13 | high in NP | −3.6 | 0.028147971 | −1.6 | 13460 | 16 | 61 | 28 | 9 | 9 | 9 | N | N | N | N | N | N |
| TC2N | high in NP | −3.9 | 0.02811524 | −1.6 | 13461 | 19 | 62 | 85 | 13 | 18 | 13 | N | P | N | N | P | N |
| EEF1E1 | high in NP | −18.6 | 0.028108421 | −1.6 | 13462 | 2 | 58 | 65 | 2 | 2 | 2 | N | N | N | N | N | N |
| EMP1 | high in NP | −3.2 | 0.028063416 | −1.6 | 13463 | 2727 | 5901 | 5107 | 823 | 1578 | 1842 | N | P | N | N | N | P |
| RC3H1 | high in NP | −3.3 | 0.028043641 | −1.6 | 13464 | 119 | 311 | 308 | 60 | 73 | 100 | N | N | N | N | N | N |
| FAM107B | high in NP | −2.5 | 0.028036822 | −1.6 | 13465 | 247 | 408 | 267 | 96 | 141 | 120 | N | N | N | N | N | N |
| ZNF706 | high in NP | −2.6 | 0.028023184 | −1.6 | 13466 | 186 | 316 | 317 | 84 | 89 | 108 | N | P | N | N | N | N |
| SRPRB | high in NP | −10.6 | 0.028010228 | −1.6 | 13467 | 41 | 429 | 249 | 30 | 21 | 20 | N | P | N | N | N | N |

TABLE 15-continued

Genes that Are Differentially Methylated between Nulliparous and Parous CD44+ Breast Epithelial Cells

| | | | | | | SAGE-seq | | | | | | | ChIP-seq | | | MSDK-seq | | |
| | | | | | | Nulliparous (NP) | | | | Parous (P) | | | NP | P | | NP | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
|---|---|---|---|---|---|---|---|---|---|---|---|---|---|---|---|---|---|
| SNHG6 | high in NP | −4.8 | 0.027996591 | −1.6 | 13468 | 196 | 780 | 748 | 84 | 101 | 144 | N | N | N | N | N | N |
| EREG | high in NP | −4.2 | 0.027984316 | −1.6 | 13469 | 17 | 105 | 75 | 14 | 13 | 13 | P | P | N | N | N | N |
| SURF1 | high in NP | −18.3 | 0.027977497 | −1.6 | 13470 | 2 | 69 | 55 | 2 | 2 | 2 | N | N | N | N | N | N |
| NAAA | high in NP | −4.0 | 0.027957041 | −1.6 | 13471 | 31 | 36 | 24 | 15 | 9 | 9 | N | N | N | N | N | N |
| C3orf31 | high in NP | −2.7 | 0.027916809 | −1.6 | 13472 | 11 | 6 | 9 | 5 | 5 | 5 | N | N | N | N | N | N |
| ARL8B | high in NP | −4.8 | 0.027869758 | −1.6 | 13473 | 188 | 544 | 672 | 106 | 127 | 139 | N | N | N | N | N | N |
| RBM9 | high in NP | −3.0 | 0.027862939 | −1.6 | 13474 | 889 | 610 | 582 | 377 | 201 | 331 | N | N | N | N | N | N |
| PPP1R2 | high in NP | −3.3 | 0.027833617 | −1.6 | 13475 | 50 | 113 | 92 | 25 | 26 | 15 | N | N | N | N | N | N |
| C6orf108 | high in NP | −3.6 | 0.027794068 | −1.6 | 13476 | 96 | 39 | 73 | 21 | 15 | 6 | N | N | N | N | N | N |
| ZWINT | high in NP | −3.0 | 0.027755199 | −1.6 | 13477 | 9 | 9 | 11 | 3 | 3 | 3 | N | N | N | N | N | N |
| CMPK2 | high in NP | −3.3 | 0.027728606 | −1.6 | 13478 | 47 | 48 | 17 | 13 | 8 | 10 | NA | NA | N | N | N | N |
| FAM198B | high in NP | −2.6 | 0.027721787 | −1.6 | 13479 | 249 | 405 | 186 | 67 | 87 | 99 | N | N | N | N | N | N |
| C20orf30 | high in NP | −3.0 | 0.027686328 | −1.6 | 13480 | 606 | 398 | 396 | 239 | 116 | 85 | N | N | N | N | N | N |
| GUK1 | high in NP | −2.4 | 0.027668599 | −1.6 | 13481 | 328 | 512 | 388 | 144 | 139 | 169 | N | N | N | N | N | N |
| UROD | high in NP | −4.2 | 0.027649506 | −1.6 | 13482 | 52 | 74 | 84 | 33 | 13 | 16 | N | N | N | N | N | N |
| SCAMP5 | high in NP | −4.6 | 0.027628367 | −1.6 | 13483 | 57 | 17 | 25 | 15 | 10 | 10 | N | N | N | N | N | N |
| FLNC | high in NP | −3.2 | 0.027621548 | −1.6 | 13484 | 101 | 149 | 258 | 29 | 37 | 78 | N | P | N | N | N | N |
| CCDC83 | high in NP | −8.3 | 0.027579952 | −1.6 | 13485 | 9 | 33 | 26 | 2 | 5 | 2 | N | N | N | N | N | N |
| SMARCD2 | high in NP | −2.8 | 0.0275574 | −1.6 | 13486 | 112 | 95 | 145 | 46 | 21 | 42 | N | N | N | N | N | N |
| UBTD2 | high in NP | −5.2 | 0.027544494 | −1.6 | 13487 | 141 | 590 | 554 | 78 | 61 | 120 | NA | NA | N | N | N | N |
| SIKE1 | high in NP | −2.9 | 0.027537675 | −1.6 | 13488 | 21 | 44 | 47 | 14 | 12 | 9 | N | N | N | N | N | N |
| SETD3 | high in NP | −3.0 | 0.027530856 | −1.6 | 13489 | 66 | 54 | 35 | 17 | 19 | 12 | N | N | N | N | N | N |
| TMEM205 | high in NP | −3.6 | 0.027524037 | −1.6 | 13490 | 58 | 224 | 108 | 35 | 22 | 14 | N | N | N | N | N | N |
| AQP1 | high in NP | −5.1 | 0.027508353 | −1.6 | 13491 | 200 | 599 | 79 | 30 | 57 | 39 | N | N | N | N | N | N |
| TNFRSF14 | high in NP | −2.5 | 0.027485851 | −1.6 | 13492 | 161 | 67 | 84 | 32 | 23 | 31 | N | P | N | N | P | N |
| ZNF217 | high in NP | −7.4 | 0.027438118 | −1.6 | 13493 | 71 | 389 | 428 | 48 | 30 | 51 | N | N | N | N | N | N |
| DNTTIP1 | high in NP | −20.6 | 0.027337197 | −1.6 | 13494 | 5 | 71 | 72 | 9 | 5 | 5 | N | N | N | N | P | N |
| COL21A1 | high in NP | −2.2 | 0.027324923 | −1.6 | 13495 | 20 | 23 | 26 | 9 | 9 | 9 | N | N | N | N | N | N |
| LIF | high in NP | −5.0 | 0.027295602 | −1.6 | 13496 | 479 | 2636 | 1933 | 423 | 453 | 184 | N | P | N | N | N | N |
| PTGDS | high in NP | −5.5 | 0.027268326 | −1.6 | 13497 | 93 | 487 | 337 | 47 | 24 | 76 | N | N | N | N | N | N |
| FNTA | high in NP | −2.8 | 0.027254688 | −1.6 | 13498 | 268 | 282 | 432 | 123 | 121 | 82 | N | N | N | N | N | N |
| GBP2 | high in NP | −4.7 | 0.027220593 | −1.6 | 13499 | 38 | 105 | 143 | 14 | 15 | 25 | N | N | N | N | N | N |
| GSPT1 | high in NP | −3.6 | 0.027213774 | −1.6 | 13500 | 128 | 439 | 235 | 71 | 117 | 65 | N | N | N | N | N | N |
| HERC3 | high in NP | −2.6 | 0.027162632 | −1.6 | 13501 | 30 | 64 | 46 | 16 | 16 | 19 | N | N | N | N | P | N |
| TCEB2 | high in NP | −3.7 | 0.02714013 | −1.6 | 13502 | 141 | 354 | 282 | 93 | 77 | 31 | N | N | N | N | N | N |
| JOSD1 | high in NP | −2.5 | 0.027133311 | −1.6 | 13503 | 302 | 513 | 476 | 126 | 142 | 192 | N | N | N | N | P | N |
| ARPC5L | high in NP | −4.0 | 0.02711149 | −1.6 | 13504 | 85 | 217 | 177 | 39 | 34 | 47 | N | N | N | N | N | N |
| SLC25A34 | high in NP | −3.3 | 0.027104671 | −1.6 | 13505 | 68 | 212 | 151 | 44 | 27 | 45 | N | N | N | N | N | N |
| TMEM184A | high in NP | −4.8 | 0.027085594 | −1.6 | 13506 | 57 | 197 | 230 | 18 | 48 | 29 | N | N | N | N | N | N |
| CEBPZ | high in NP | −3.9 | 0.027065803 | −1.6 | 13507 | 61 | 166 | 124 | 30 | 50 | 12 | N | N | N | N | N | N |
| SERPINE1 | high in NP | −4.4 | 0.027031708 | −1.6 | 13508 | 1133 | 2415 | 2172 | 950 | 280 | 520 | N | N | N | N | P | N |
| ZAK | high in NP | −4.2 | 0.026982612 | −1.6 | 13509 | 948 | 497 | 270 | 223 | 149 | 131 | N | N | N | N | N | N |
| RAB5C | high in NP | −3.4 | 0.026965564 | −1.6 | 13510 | 229 | 568 | 444 | 125 | 110 | 108 | N | N | N | N | N | N |
| MAP4K5 | high in NP | −4.4 | 0.026958745 | −1.6 | 13511 | 152 | 473 | 429 | 87 | 99 | 110 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | | Nulliparous (NP) | | | | Parous (P) | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| PGLS | high in NP | -3.3 | 0.026923969 | -1.6 | 13512 | 228 | 102 | 178 | 44 | 52 | 27 | N | N | N | N | N | N |
| FAM168B | high in NP | -2.7 | 0.026910331 | -1.6 | 13513 | 76 | 157 | 135 | 63 | 44 | 31 | N | N | N | N | N | N |
| PCBP2 | high in NP | -5.1 | 0.026903512 | -1.6 | 13514 | 735 | 3085 | 2305 | 550 | 603 | 503 | N | N | N | N | N | N |
| EDEM2 | high in NP | -2.9 | 0.026889874 | -1.6 | 13515 | 30 | 22 | 35 | 11 | 9 | 9 | N | N | N | N | N | N |
| GBAS | high in NP | -9.2 | 0.026850324 | -1.6 | 13516 | 9 | 69 | 70 | 9 | 9 | 9 | N | N | N | N | N | N |
| MLL5 | high in NP | -2.5 | 0.026843505 | -1.6 | 13517 | 239 | 207 | 213 | 103 | 67 | 127 | N | N | N | N | N | N |
| BDKRB2 | high in NP | -4.5 | 0.026836686 | -1.6 | 13518 | 32 | 49 | 82 | 22 | 14 | 14 | N | N | N | N | N | N |
| FLRT2 | high in NP | -3.3 | 0.026824412 | -1.6 | 13519 | 164 | 103 | 81 | 31 | 49 | 40 | N | N | N | N | N | N |
| C20orf199 | high in NP | -2.7 | 0.026810774 | -1.6 | 13520 | 869 | 906 | 1455 | 324 | 394 | 430 | N | N | N | N | N | N |
| WDR12 | high in NP | -2.9 | 0.026782816 | -1.6 | 13521 | 23 | 27 | 20 | 12 | 15 | 12 | N | N | N | N | N | N |
| PGD | high in NP | -8.7 | 0.026775997 | -1.6 | 13522 | 128 | 826 | 1295 | 123 | 64 | 76 | N | N | N | N | N | N |
| KIAA1522 | high in NP | -4.7 | 0.026749403 | -1.6 | 13523 | 72 | 246 | 353 | 27 | 67 | 35 | N | N | N | N | N | N |
| SLC2A3 | high in NP | -4.2 | 0.026663484 | -1.6 | 13524 | 5354 | 1714 | 1792 | 500 | 431 | 1246 | N | N | N | N | N | N |
| EPS8 | high in NP | -4.8 | 0.026649847 | -1.6 | 13525 | 98 | 468 | 251 | 75 | 45 | 41 | N | P | N | N | N | N |
| SEC22C | high in NP | -3.6 | 0.026563246 | -1.6 | 13526 | 40 | 80 | 47 | 24 | 8 | 11 | N | N | N | N | N | N |
| VIM | high in NP | -4.9 | 0.026525165 | -1.6 | 13527 | 8396 | 44363 | 4535 | 1550 | 1493 | 3364 | N | N | N | N | N | N |
| ZBTB41 | high in NP | -3.5 | 0.026505967 | -1.6 | 13528 | 59 | 47 | 48 | 14 | 23 | 12 | N | N | N | N | N | N |
| CCNY | high in NP | -3.3 | 0.026464371 | -1.6 | 13529 | 386 | 414 | 196 | 150 | 103 | 90 | N | N | N | N | N | N |
| C14orf126 | high in NP | -2.8 | 0.026457552 | -1.6 | 13530 | 13 | 13 | 18 | 6 | 6 | 6 | N | N | N | N | N | N |
| S100A8 | high in NP | -8.9 | 0.026403682 | -1.6 | 13531 | 3 | 66 | 117 | 3 | 3 | 3 | P | N | N | N | N | N |
| DPM1 | high in NP | -8.3 | 0.026370951 | -1.6 | 13532 | 3 | 44 | 41 | 3 | 3 | 3 | N | N | N | N | N | N |
| ANKRD46 | high in NP | -3.0 | 0.026358677 | -1.6 | 13533 | 58 | 45 | 29 | 13 | 13 | 6 | N | P | N | N | N | N |
| EGR1 | high in NP | -3.1 | 0.026330038 | -1.6 | 13534 | 17527 | 9490 | 11906 | 4125 | 3306 | 6159 | P | N | N | N | P | N |
| CHCHD3 | high in NP | -2.8 | 0.026233898 | -1.6 | 13535 | 97 | 136 | 83 | 43 | 27 | 18 | N | N | N | N | N | N |
| SSH1 | high in NP | -2.7 | 0.026227071 | -1.6 | 13536 | 313 | 422 | 310 | 196 | 134 | 91 | N | N | N | N | N | N |
| MAP3K7 | high in NP | -2.2 | 0.026199795 | -1.6 | 13537 | 34 | 40 | 34 | 16 | 15 | 12 | N | N | N | N | N | N |
| EN1 | high in NP | -2.6 | 0.026162291 | -1.6 | 13538 | 35 | 58 | 35 | 10 | 10 | 10 | P | N | N | N | N | N |
| TIMP3 | high in NP | -3.6 | 0.026121377 | -1.6 | 13539 | 2051 | 2961 | 869 | 917 | 376 | 545 | N | N | N | N | N | N |
| ZNF92 | high in NP | -3.3 | 0.026097511 | -1.6 | 13540 | 11 | 14 | 26 | 5 | 5 | 5 | N | N | N | N | N | N |
| ZNF32 | high in NP | -3.9 | 0.026090692 | -1.6 | 13541 | 64 | 90 | 42 | 23 | 12 | 5 | N | N | N | N | N | N |
| ADSS | high in NP | -3.9 | 0.026063416 | -1.6 | 13542 | 31 | 64 | 104 | 15 | 12 | 17 | N | N | N | N | N | N |
| NEIL1 | high in NP | -4.2 | 0.026051142 | -1.6 | 13543 | 11 | 31 | 72 | 5 | 5 | 5 | N | N | N | N | N | N |
| KRT10 | high in NP | -34.6 | 0.02602864 | -1.6 | 13544 | 2 | 54 | 50 | 2 | 2 | 2 | N | N | N | N | N | N |
| C19orf10 | high in NP | -7.3 | 0.026021821 | -1.6 | 13545 | 116 | 576 | 867 | 113 | 58 | 25 | N | N | N | N | N | N |
| NAA30 | high in NP | -3.3 | 0.025917491 | -1.6 | 13546 | 20 | 63 | 38 | 13 | 13 | 13 | NA | NA | P | N | N | N |
| EGLN1 | high in NP | -9.0 | 0.025875895 | -1.6 | 13547 | 101 | 647 | 829 | 74 | 37 | 93 | N | N | N | N | N | N |
| C16orf57 | high in NP | -4.5 | 0.025847937 | -1.6 | 13548 | 35 | 135 | 128 | 24 | 15 | 14 | N | N | N | N | N | N |
| BDKRB1 | high in NP | -3.3 | 0.02576611 | -1.6 | 13549 | 785 | 238 | 239 | 120 | 65 | 55 | N | N | N | N | N | N |
| KCNE4 | high in NP | -4.1 | 0.025759291 | -1.6 | 13550 | 643 | 2445 | 1211 | 315 | 317 | 481 | N | N | N | N | N | N |
| DCTN3 | high in NP | -3.5 | 0.025740198 | -1.6 | 13551 | 143 | 127 | 85 | 27 | 45 | 10 | N | P | N | N | N | N |
| IDH1 | high in NP | -3.4 | 0.025719741 | -1.6 | 13552 | 89 | 43 | 36 | 11 | 16 | 18 | N | N | N | N | N | N |
| PPAP2A | high in NP | -3.5 | 0.025712922 | -1.6 | 13553 | 110 | 176 | 67 | 30 | 26 | 35 | N | N | N | N | N | N |
| FLJ43663 | high in NP | -3.7 | 0.025676781 | -1.6 | 13554 | 16 | 44 | 26 | 9 | 9 | 9 | N | N | N | N | N | N |
| DCUN1D3 | high in NP | -4.6 | 0.025664507 | -1.6 | 13555 | 349 | 532 | 394 | 79 | 45 | 247 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | | Nulliparous (NP) | | | | Parous (P) | | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | NP | CD44+ N66 | P | GeneBody NP Met | NP | GeneBody Met | P | Pro-moter Met | NP | Pro-moter Met | P |

| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
|---|---|---|---|---|---|---|---|---|---|---|---|---|---|---|---|---|---|
| NUPL1 | high in NP | −5.1 | 0.025588135 | −1.6 | 13556 | 56 | 265 | 190 | 46 | 33 | 21 | N | N | N | N | N | N |
| C18orf32 | high in NP | −11.1 | 0.025558132 | −1.6 | 13557 | 14 | 115 | 83 | 7 | 7 | 5 | N | N | N | N | N | N |
| MORC3 | high in NP | −3.9 | 0.025533583 | −1.6 | 13558 | 64 | 202 | 132 | 47 | 23 | 24 | N | N | N | N | N | N |
| DCAF8 | high in NP | −5.0 | 0.025491306 | −1.6 | 13559 | 114 | 188 | 225 | 30 | 22 | 84 | NA | NA | N | N | N | N |
| OSBPL8 | high in NP | −3.7 | 0.025445619 | −1.6 | 13560 | 62 | 228 | 145 | 48 | 33 | 39 | N | N | N | N | N | N |
| FUCA2 | high in NP | −2.6 | 0.025411524 | −1.6 | 13561 | 41 | 117 | 44 | 15 | 14 | 9 | N | N | N | N | N | N |
| DAB2 | high in NP | −5.8 | 0.025397886 | −1.6 | 13562 | 278 | 1277 | 1424 | 177 | 181 | 260 | N | N | N | N | N | N |
| ITGB1 | high in NP | −3.0 | 0.025385612 | −1.6 | 13563 | 4287 | 6996 | 2650 | 1351 | 1541 | 820 | N | N | N | N | N | N |
| UBA2 | high in NP | −5.3 | 0.025378793 | −1.6 | 13564 | 79 | 308 | 239 | 43 | 43 | 30 | N | N | N | N | N | N |
| CXCL13 | high in NP | −4.8 | 0.025366519 | −1.6 | 13565 | 86 | 94 | 189 | 6 | 28 | 28 | N | N | N | N | N | N |
| HNRPDL | high in NP | −5.2 | 0.0253597 | −1.6 | 13566 | 88 | 413 | 270 | 41 | 51 | 53 | N | N | N | N | N | N |
| ZNF775 | high in NP | −3.3 | 0.025352881 | −1.6 | 13567 | 8 | 10 | 3 | 2 | 2 | 2 | N | N | N | N | N | N |
| PFDN5 | high in NP | −8.5 | 0.025346062 | −1.6 | 13568 | 183 | 1523 | 960 | 98 | 108 | 138 | N | N | N | N | N | N |
| SFRS12IP1 | high in NP | −2.8 | 0.025339243 | −1.6 | 13569 | 172 | 305 | 167 | 94 | 79 | 54 | N | N | N | N | N | N |
| ISCA1 | high in NP | −38.0 | 0.025332015 | −1.6 | 13570 | 3 | 68 | 57 | 3 | 3 | 3 | N | N | N | N | P | N |
| TMEM45A | high in NP | −10.5 | 0.025306512 | −1.6 | 13571 | 6 | 62 | 48 | 6 | 6 | 6 | N | N | N | N | N | N |
| SLC36A4 | high in NP | −2.4 | 0.025299693 | −1.6 | 13572 | 24 | 32 | 40 | 8 | 11 | 8 | N | N | N | N | N | N |
| ACPL2 | high in NP | −5.1 | 0.025273145 | −1.6 | 13573 | 13 | 51 | 10 | 7 | 7 | 7 | N | N | N | N | N | N |
| ZBTB2 | high in NP | −2.9 | 0.025268326 | −1.6 | 13574 | 100 | 131 | 75 | 29 | 20 | 39 | N | N | N | N | N | N |
| MYL6 | high in NP | −2.7 | 0.025214456 | −1.6 | 13575 | 2264 | 3915 | 2757 | 1071 | 1264 | 717 | N | N | N | N | N | N |
| TCF7L1 | high in NP | −2.7 | 0.025191954 | −1.6 | 13576 | 243 | 228 | 331 | 75 | 88 | 129 | N | N | N | N | N | N |
| HIC1 | high in NP | −4.5 | 0.025178316 | −1.6 | 13577 | 2715 | 195 | 359 | 69 | 72 | 92 | N | N | N | N | N | P |
| IMMP1L | high in NP | −2.7 | 0.025144221 | −1.6 | 13578 | 19 | 20 | 22 | 7 | 5 | 5 | N | N | N | N | N | N |
| NDNL2 | high in NP | −4.6 | 0.02510808 | −1.6 | 13579 | 36 | 128 | 106 | 22 | 12 | 13 | N | N | N | N | N | N |
| RPL22 | high in NP | −2.6 | 0.025101262 | −1.6 | 13580 | 2063 | 3138 | 2503 | 843 | 910 | 1194 | N | N | N | N | N | N |
| ERMAP | high in NP | −2.6 | 0.025094443 | −1.6 | 13581 | 29 | 20 | 30 | 8 | 11 | 8 | N | N | N | N | N | N |
| TPCN1 | high in NP | −3.0 | 0.0250610 | −1.6 | 13582 | 67 | 100 | 135 | 28 | 29 | 43 | N | N | N | N | N | N |
| NOTCH1 | high in NP | −3.7 | 0.025047392 | −1.6 | 13583 | 245 | 263 | 153 | 47 | 54 | 112 | N | N | N | N | N | N |
| PLIN3 | high in NP | −2.7 | 0.025024889 | −1.6 | 13584 | 409 | 679 | 627 | 230 | 155 | 245 | N | N | N | N | N | N |
| ASPH | high in NP | −4.0 | 0.02501807 | −1.6 | 13585 | 2267 | 1205 | 995 | 498 | 565 | 254 | N | N | N | N | N | N |
| ABCC9 | high in NP | −2.3 | 0.024866008 | −1.6 | 13586 | 54 | 117 | 74 | 26 | 25 | 21 | NA | NA | N | N | N | N |
| RBP1 | high in NP | −3.0 | 0.024859189 | −1.6 | 13587 | 75 | 54 | 33 | 15 | 16 | 12 | N | N | N | N | N | N |
| GPR89A | high in NP | −38.5 | 0.02485237 | −1.6 | 13588 | 2 | 85 | 56 | 2 | 2 | 2 | N | N | N | N | N | N |
| TNFRSF10B | high in NP | −2.9 | 0.024845551 | −1.6 | 13589 | 222 | 877 | 254 | 80 | 78 | 108 | N | N | N | N | P | N |
| FBLN2 | high in NP | −2.4 | 0.024786908 | −1.6 | 13590 | 85 | 92 | 107 | 32 | 31 | 40 | N | N | N | N | N | N |
| SCCPDH | high in NP | −2.7 | 0.024780089 | −1.6 | 13591 | 43 | 37 | 41 | 11 | 15 | 9 | N | N | N | N | P | N |
| RAB1A | high in NP | −10.0 | 0.024773 72 | −1.6 | 13592 | 111 | 1178 | 768 | 78 | 77 | 79 | N | N | N | N | N | N |
| VEGFA | high in NP | −4.4 | 0.024720082 | −1.6 | 13593 | 9787 | 4027 | 3474 | 934 | 1283 | 2484 | N | N | N | N | N | N |
| IARS2 | high in NP | −10.1 | 0.024703034 | −1.6 | 13594 | 11 | 66 | 66 | 11 | 11 | 11 | N | N | N | N | N | N |
| FOSL2 | high in NP | −3.0 | 0.024666894 | −1.6 | 13595 | 1420 | 537 | 592 | 234 | 198 | 345 | N | N | N | N | P | N |
| RB1 | high in NP | −2.4 | 0.024649847 | −1.6 | 13596 | 25 | 36 | 51 | 13 | 13 | 13 | P | N | N | N | N | N |
| LPXN | high in NP | −2.7 | 0.024585066 | −1.6 | 13597 | 67 | 86 | 71 | 16 | 22 | 30 | N | N | N | N | N | N |
| RNF103 | high in NP | −5.8 | 0.024578248 | −1.6 | 13598 | 31 | 180 | 167 | 12 | 17 | 25 | N | N | N | N | N | N |
| PLRG1 | high in NP | −7.3 | 0.024525742 | −1.6 | 13599 | 25 | 127 | 91 | 9 | 14 | 10 | N | N | N | N | P | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
| | | | | | | Nulliparous (NP) | | | | Parous (P) | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 NP | CD44+ N66 P | GeneBody NP Met NP | GeneBody Met P | Pro-moter Met NP | Pro-moter Met P |
|---|---|---|---|---|---|---|---|---|---|---|---|---|---|---|---|---|---|
| S1PR3 | high in NP | -4.1 | 0.024512104 | -1.6 | 13600 | 43 | 167 | 109 | 33 | 15 | 23 | N | N | N | N | N | N |
| GHITM | high in NP | -3.9 | 0.024491647 | -1.6 | 13601 | 46 | 181 | 188 | 50 | 16 | 20 | N | N | N | N | N | N |
| FLNB | high in NP | -4.1 | 0.024478009 | -1.6 | 13602 | 64 | 171 | 253 | 42 | 71 | 40 | N | N | N | N | P | N |
| KIAA1430 | high in NP | -3.2 | 0.0244719 | -1.6 | 13603 | 54 | 97 | 121 | 38 | 26 | 15 | N | N | N | N | N | N |
| RANBP3 | high in NP | -6.0 | 0.024460961 | -1.6 | 13604 | 35 | 182 | 159 | 30 | 25 | 20 | N | N | N | N | N | N |
| C16orf72 | high in NP | -3.6 | 0.024448687 | -1.6 | 13605 | 627 | 606 | 508 | 107 | 184 | 328 | N | N | P | N | N | N |
| UBE2G1 | high in NP | -3.6 | 0.024405046 | -1.6 | 13606 | 43 | 139 | 125 | 28 | 26 | 31 | N | N | N | N | N | N |
| PCNP | high in NP | -24.2 | 0.024398227 | -1.6 | 13607 | 8 | 225 | 218 | 8 | 8 | 11 | N | N | N | N | N | N |
| FPGS | high in NP | -3.3 | 0.024383225 | -1.6 | 13608 | 80 | 172 | 216 | 55 | 37 | 25 | N | N | N | N | N | N |
| TBC1D9 | high in NP | -2.5 | 0.024330719 | -1.6 | 13609 | 259 | 191 | 162 | 85 | 62 | 68 | N | N | N | N | N | N |
| CPEB2 | high in NP | -3.9 | 0.0243239 | -1.6 | 13610 | 194 | 647 | 168 | 43 | 47 | 99 | N | N | N | N | N | N |
| MFHAS1 | high in NP | -3.3 | 0.024317081 | -1.6 | 13611 | 149 | 124 | 73 | 32 | 31 | 39 | N | N | N | N | N | N |
| FAM36A | high in NP | -3.8 | 0.024310263 | -1.6 | 13612 | 76 | 225 | 195 | 32 | 52 | 30 | N | N | N | N | P | N |
| ARFIP1 | high in NP | -4.7 | 0.024289806 | -1.6 | 13613 | 36 | 109 | 132 | 21 | 21 | 13 | N | N | N | N | N | N |
| WISP2 | high in NP | -9.9 | 0.024255029 | -1.6 | 13614 | 25 | 329 | 245 | 9 | 16 | 25 | N | N | N | N | N | N |
| FAM82A2 | high in NP | -5.3 | 0.02424821 | -1.6 | 13615 | 41 | 73 | 54 | 9 | 26 | 9 | N | N | N | N | N | N |
| SNRNP27 | high in NP | -16.3 | 0.024225707 | -1.6 | 13616 | 16 | 213 | 271 | 9 | 12 | 5 | N | N | N | N | N | N |
| CLPP | high in NP | -4.1 | 0.024203205 | -1.6 | 13617 | 52 | 101 | 122 | 28 | 24 | 10 | N | N | N | N | N | N |
| PRPS2 | high in NP | -6.7 | 0.024162291 | -1.6 | 13618 | 18 | 105 | 56 | 7 | 12 | 7 | N | N | N | N | N | N |
| WDR83 | high in NP | -2.6 | 0.024111865 | -1.6 | 13619 | 17 | 19 | 41 | 6 | 6 | 6 | N | N | N | N | N | N |
| MRPL49 | high in NP | -3.0 | 0.024089328 | -1.6 | 13620 | 322 | 257 | 304 | 155 | 93 | 62 | N | N | N | N | N | N |
| C4orf46 | high in NP | -4.1 | 0.024082509 | -1.6 | 13621 | 197 | 243 | 116 | 41 | 30 | 82 | N | N | N | N | N | N |
| SLC25A32 | high in NP | -10.9 | 0.024060007 | -1.6 | 13622 | 24 | 281 | 137 | 15 | 12 | 6 | N | N | N | N | N | N |
| MPZL1 | high in NP | -3.0 | 0.02402523 | -1.6 | 13623 | 1347 | 1477 | 1131 | 808 | 525 | 307 | N | NA | N | N | N | N |
| BTG1 | high in NP | -3.8 | 0.024006137 | -1.6 | 13624 | 1867 | 2722 | 3041 | 622 | 517 | 1355 | N | N | N | N | P | N |
| SGMS2 | high in NP | -3.2 | 0.023999318 | -1.6 | 13625 | 187 | 403 | 157 | 51 | 78 | 68 | N | N | N | N | N | N |
| 8-Mar | high in NP | -11.7 | 0.023964541 | -1.6 | 13626 | 8 | 149 | 147 | 10 | 8 | 8 | NA | P | N | N | N | N |
| MTCH2 | high in NP | -4.1 | 0.023957722 | -1.6 | 13627 | 16 | 48 | 41 | 9 | 9 | 9 | N | NA | N | N | N | N |
| EBPL | high in NP | -11.5 | 0.023942039 | -1.6 | 13628 | 3 | 60 | 62 | 3 | 3 | 3 | NA | N | N | N | N | N |
| FAM60A | high in NP | -3.3 | 0.023832254 | -1.6 | 13629 | 643 | 495 | 417 | 191 | 325 | 98 | N | N | N | N | P | N |
| CRIP1 | high in NP | -3.7 | 0.023746335 | -1.6 | 13630 | 24 | 412 | 31 | 8 | 8 | 8 | N | N | N | N | N | N |
| KCNS3 | high in NP | -4.0 | 0.023723832 | -1.6 | 13631 | 13 | 16 | 16 | 6 | 6 | 6 | N | N | N | N | N | N |
| PRKCDBP | high in NP | -4.5 | 0.023717013 | -1.6 | 13632 | 163 | 571 | 702 | 139 | 128 | 81 | N | N | N | N | N | N |
| MYEOV2 | high in NP | -5.1 | 0.023675418 | -1.6 | 13633 | 213 | 43 | 24 | 13 | 6 | 3 | N | N | N | N | P | N |
| CAP1 | high in NP | -46.6 | 0.023656325 | -1.6 | 13634 | 5 | 131 | 71 | 5 | 5 | 5 | N | N | N | N | N | N |
| CAPZA2 | high in NP | -2.9 | 0.0236364 | -1.6 | 13635 | 881 | 1085 | 702 | 386 | 360 | 165 | N | N | N | N | N | N |
| C11orf58 | high in NP | -6.9 | 0.023618138 | -1.6 | 13636 | 46 | 329 | 209 | 20 | 41 | 18 | N | N | N | N | N | N |
| FOSB | high in NP | -3.0 | 0.023592226 | -1.6 | 13637 | 409 | 472 | 700 | 299 | 194 | 115 | N | N | N | N | N | N |
| FTO | high in NP | -3.8 | 0.023559495 | -1.6 | 13638 | 38850 | 13869 | 11723 | 2769 | 3514 | 7274 | N | N | N | N | N | N |
| CAB39 | high in NP | -5.4 | 0.023552676 | -1.6 | 13639 | 154 | 143 | 84 | 54 | 17 | 30 | N | N | N | N | P | N |
| MATR3 | high in NP | -3.6 | 0.023519945 | -1.6 | 13640 | 48 | 204 | 229 | 18 | 37 | 29 | N | N | N | N | N | N |
| LSM2 | high in NP | -2.9 | 0.0235199445 | -1.6 | 13641 | 257 | 531 | 422 | 135 | 109 | 166 | N | N | N | N | N | N |
| TMEM101 | high in NP | -4.0 | 0.023493352 | -1.6 | 13642 | 178 | 110 | 167 | 60 | 29 | 25 | N | N | N | N | N | N |
| | high in NP | | | -1.6 | 13643 | 118 | 114 | 133 | 60 | 22 | 11 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
| | | | | | | Nulliparous (NP) | | | Parous (P) | | | NP | | P | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
|---|---|---|---|---|---|---|---|---|---|---|---|---|---|---|---|---|---|
| PHF2 | high in NP | -2.6 | 0.02344971 | -1.6 | 13644 | 214 | 287 | 316 | 133 | 98 | 94 | N | N | N | N | N | N |
| HIGD2A | high in NP | -3.9 | 0.023414252 | -1.6 | 13645 | 83 | 180 | 230 | 40 | 29 | 36 | N | N | N | N | N | N |
| YWHAG | high in NP | -3.1 | 0.02338493 | -1.6 | 13646 | 1721 | 3410 | 2920 | 675 | 1007 | 1228 | N | N | N | N | N | N |
| ZMYND19 | high in NP | -13.7 | 0.023371292 | -1.6 | 13647 | 6 | 62 | 71 | 6 | 6 | 6 | N | P | N | N | N | N |
| NDRG4 | high in NP | -2.2 | 0.023364473 | -1.6 | 13648 | 24 | 31 | 26 | 13 | 6 | 13 | N | N | N | N | N | N |
| LOC550643 | high in NP | -7.1 | 0.023357654 | -1.6 | 13649 | 16 | 89 | 61 | 11 | 9 | 5 | N | N | N | N | N | N |
| METTL9 | high in NP | -4.4 | 0.023350835 | -1.6 | 13650 | 15 | 199 | 69 | 9 | 9 | 9 | N | N | N | N | N | N |
| MGMT | high in NP | -7.9 | 0.023290147 | -1.6 | 13651 | 19 | 43 | 55 | 11 | 6 | 3 | N | N | N | N | N | N |
| SRP19 | high in NP | -58.4 | 0.023283328 | -1.6 | 13652 | 3 | 92 | 94 | 3 | 3 | 3 | N | N | N | N | N | N |
| SLC39A14 | high in NP | -3.4 | 0.023276509 | -1.6 | 13653 | 501 | 1815 | 838 | 312 | 270 | 256 | NA | NA | N | N | N | N |
| C5orf62 | high in NP | -5.9 | 0.023243778 | -1.6 | 13654 | 170 | 1039 | 211 | 76 | 27 | 78 | N | N | N | N | N | N |
| ADAMTS1 | high in NP | -3.2 | 0.023191954 | -1.6 | 13655 | 236 | 537 | 367 | 154 | 79 | 140 | N | N | N | N | N | N |
| RIOK3 | high in NP | -6.3 | 0.023160586 | -1.6 | 13656 | 26 | 167 | 137 | 22 | 23 | 26 | N | N | N | N | N | N |
| GOLM1 | high in NP | -3.6 | 0.023153767 | -1.6 | 13657 | 322 | 213 | 159 | 35 | 65 | 70 | N | N | N | N | N | N |
| GLTSCR2 | high in NP | -5.8 | 0.023127855 | -1.6 | 13658 | 50 | 136 | 158 | 50 | 50 | 50 | N | N | N | N | N | N |
| FAT1 | high in NP | -4.8 | 0.023121036 | -1.6 | 13659 | 208 | 947 | 695 | 92 | 198 | 135 | N | N | N | N | N | N |
| COPS7A | high in NP | -2.9 | 0.023114218 | -1.6 | 13660 | 30 | 79 | 46 | 19 | 12 | 9 | N | N | N | N | N | N |
| C18orf10 | high in NP | -2.5 | 0.023107399 | -1.6 | 13661 | 39 | 51 | 67 | 20 | 14 | 14 | N | N | N | N | N | N |
| PXMP2 | high in NP | -3.0 | 0.023095124 | -1.6 | 13662 | 9 | 5 | 6 | 3 | 3 | 3 | N | N | N | N | N | N |
| SCPEP1 | high in NP | -4.2 | 0.023088305 | -1.6 | 13663 | 23 | 167 | 26 | 12 | 12 | 12 | N | N | N | N | N | N |
| NAP1L1 | high in NP | -3.5 | 0.023069212 | -1.6 | 13664 | 538 | 1309 | 1005 | 296 | 240 | 400 | NA | NA | N | N | N | N |
| PIM2 | high in NP | -5.4 | 0.023062393 | -1.6 | 13665 | 68 | 218 | 58 | 17 | 9 | 25 | N | N | N | N | N | N |
| CSRP1 | high in NP | -3.6 | 0.023026253 | -1.6 | 13666 | 3555 | 1728 | 2726 | 429 | 1061 | 517 | N | N | N | N | N | N |
| TMEM189 | high in NP | -7.3 | 0.022976475 | -1.6 | 13667 | 57 | 391 | 172 | 45 | 19 | 6 | N | N | N | N | N | N |
| BMI1 | high in NP | -6.1 | 0.022969656 | -1.6 | 13668 | 15 | 128 | 80 | 9 | 9 | 12 | N | N | N | N | N | N |
| NDUFAB1 | high in NP | -8.1 | 0.022941698 | -1.6 | 13669 | 23 | 159 | 87 | 15 | 11 | 6 | N | N | N | N | N | N |
| BACH1 | high in NP | -3.4 | 0.022912376 | -1.6 | 13670 | 85 | 210 | 213 | 43 | 45 | 66 | N | N | N | N | N | N |
| SAE1 | high in NP | -3.4 | 0.022898738 | -1.6 | 13671 | 268 | 258 | 235 | 119 | 51 | 61 | N | N | N | N | N | N |
| ZFX | high in NP | -3.3 | 0.022876236 | -1.6 | 13672 | 80 | 181 | 133 | 48 | 36 | 38 | N | N | N | N | N | N |
| AQP7P3 | high in NP | -2.7 | 0.022869417 | -1.6 | 13673 | 8 | 3 | 3 | 2 | 2 | 2 | NA | NA | N | N | N | N |
| COX6C | high in NP | -14.8 | 0.022846914 | -1.6 | 13674 | 14 | 258 | 247 | 6 | 3 | 11 | N | N | N | N | N | N |
| PCMTD2 | high in NP | -2.7 | 0.022840095 | -1.6 | 13675 | 90 | 64 | 64 | 30 | 18 | 14 | N | N | N | N | N | N |
| CSNK1G2 | high in NP | -2.7 | 0.022796454 | -1.6 | 13676 | 128 | 115 | 192 | 41 | 48 | 53 | N | N | N | N | N | N |
| SNX7 | high in NP | -5.6 | 0.022782816 | -1.6 | 13677 | 14 | 85 | 42 | 6 | 6 | 3 | N | N | N | N | N | N |
| TMED10 | high in NP | -2.9 | 0.022774463 | -1.6 | 13678 | 56 | 39 | 30 | 15 | 7 | 7 | N | N | N | N | N | N |
| JUP | high in NP | -4.1 | 0.022718718 | -1.6 | 13679 | 406 | 886 | 950 | 130 | 376 | 93 | N | N | N | N | N | N |
| LHFPL2 | high in NP | -2.4 | 0.022696215 | -1.6 | 13680 | 1757 | 2199 | 1963 | 867 | 770 | 992 | N | N | P | N | N | N |
| MPRIP | high in NP | -2.6 | 0.022689397 | -1.6 | 13681 | 403 | 477 | 452 | 142 | 217 | 157 | N | N | N | N | N | N |
| HSPA1B | high in NP | -8.3 | 0.022668258 | -1.6 | 13682 | 520 | 3199 | 3241 | 62 | 148 | 706 | N | N | N | N | N | N |
| C7orf68 | high in NP | -9.5 | 0.022661439 | -1.6 | 13683 | 5 | 111 | 207 | 5 | 5 | 5 | NA | NA | N | N | N | N |
| TMOD4 | high in NP | -2.9 | 0.02265462 | -1.6 | 13684 | 9 | 5 | 5 | 3 | 3 | 3 | N | N | N | N | N | N |
| SOCS4 | high in NP | -4.2 | 0.022647801 | -1.6 | 13685 | 18 | 101 | 81 | 18 | 18 | 18 | N | N | N | N | N | N |
| COL7A1 | high in NP | -2.7 | 0.022623253 | -1.6 | 13686 | 30 | 42 | 64 | 13 | 16 | 13 | N | N | N | N | N | N |
| COPZ2 | high in NP | -3.3 | 0.02261097 | -1.6 | 13687 | 231 | 56 | 47 | 15 | 18 | 13 | N | N | N | N | N | N |

TABLE 15-continued

Genes that Are Differentially Methylated between Nulliparous and Parous CD44+ Breast Epithelial Cells

| | | | | | | SAGE-seq | | | | | | | ChIP-seq | | | MSDK-seq | | | |
|---|---|---|---|---|---|---|---|---|---|---|---|---|---|---|---|---|---|---|---|
| | | | | | | Nulliparous (NP) | | | | Parous (P) | | | NP | | P | GeneBody NP Met | GeneBody Met | Pro-moter Met | Pro-moter Met |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | | CD44+ N74 | CD44+ N66 | | NP | P | NP | P |
| MYL12A | high in NP | -2.9 | 0.022569383 | -1.6 | 13688 | 1380 | 1540 | 1774 | 481 | 677 | 218 | | NA | NA | | N | N | N | N |
| CCDC80 | high in NP | -4.3 | 0.022515513 | -1.6 | 13689 | 2054 | 1160 | 1700 | 275 | 294 | 810 | | N | N | | N | N | N | N |
| ISPD | high in NP | -3.0 | 0.022486192 | -1.6 | 13690 | 15 | 10 | 11 | 9 | 9 | 9 | | NA | NA | | N | N | N | N |
| COX17 | high in NP | -71.3 | 0.022472554 | -1.6 | 13691 | 1 | 137 | 104 | 1 | 1 | 1 | | N | N | | N | N | N | N |
| MTMR11 | high in NP | -5.1 | 0.022378452 | -1.7 | 13692 | 141 | 42 | 46 | 25 | 11 | 14 | | N | N | | N | N | N | N |
| TMEM138 | high in NP | -4.8 | 0.023357995 | -1.7 | 13693 | 38 | 57 | 61 | 23 | 14 | 11 | | N | N | | N | N | N | N |
| NUDT4P1 | high in NP | -40.9 | 0.022299352 | -1.7 | 13694 | 14 | 475 | 166 | 5 | 2 | 8 | | N | N | | N | N | N | N |
| TFCP2L1 | high in NP | -3.3 | 0.022247528 | -1.7 | 13695 | 25 | 89 | 146 | 25 | 25 | 25 | | N | P | | N | N | N | N |
| GSTK1 | high in NP | -4.0 | 0.02218343 | -1.7 | 13696 | 90 | 173 | 249 | 16 | 53 | 33 | | N | N | | N | N | N | N |
| CRYZL1 | high in NP | -5.5 | 0.022155472 | -1.7 | 13697 | 13 | 36 | 19 | 6 | 6 | 6 | | N | N | | N | N | N | N |
| PRNP | high in NP | -3.6 | 0.022148653 | -1.7 | 13698 | 606 | 1403 | 743 | 182 | 288 | 355 | | N | N | | N | N | N | N |
| GULP1 | high in NP | -8.7 | 0.022057961 | -1.7 | 13699 | 8 | 111 | 195 | 8 | 8 | 8 | | N | N | | N | N | N | N |
| EFCAB4A | high in NP | -6.2 | 0.022051142 | -1.7 | 13700 | 15 | 21 | 54 | 4 | 4 | 7 | | N | N | | N | N | N | N |
| EIF4EBP2 | high in NP | -2.5 | 0.022031367 | -1.7 | 13701 | 462 | 659 | 526 | 301 | 243 | 245 | | N | N | | N | P | N | N |
| C11orf95 | high in NP | -3.1 | 0.022018411 | -1.7 | 13702 | 112 | 92 | 71 | 19 | 19 | 34 | | NA | NA | | N | N | N | N |
| STRAP | high in NP | -5.2 | 0.022006137 | -1.7 | 13703 | 265 | 978 | 816 | 111 | 123 | 165 | | N | N | | N | N | N | N |
| PIGN | high in NP | -2.2 | 0.021978179 | -1.7 | 13704 | 21 | 40 | 39 | 13 | 10 | 10 | | N | N | | N | N | N | N |
| DR1 | high in NP | -2.7 | 0.021944085 | -1.7 | 13705 | 138 | 205 | 118 | 46 | 37 | 54 | | N | N | | N | N | N | N |
| GPN1 | high in NP | -3.7 | 0.021937266 | -1.7 | 13706 | 23 | 24 | 11 | 7 | 7 | 7 | | N | N | | N | N | N | N |
| KRTAP4-12 | high in NP | -84.0 | 0.021930447 | -1.7 | 13707 | 1 | 171 | 125 | 1 | 1 | 1 | | N | N | | N | N | N | N |
| TMX1 | high in NP | -3.2 | 0.021916809 | -1.7 | 13708 | 92 | 93 | 133 | 25 | 21 | 42 | | NA | NA | | N | N | N | N |
| PTPRG | high in NP | -2.6 | 0.02190999 | -1.7 | 13709 | 102 | 125 | 134 | 57 | 40 | 36 | | N | N | | N | N | N | N |
| SLC17A5 | high in NP | -3.7 | 0.021897716 | -1.7 | 13710 | 64 | 135 | 70 | 26 | 27 | 14 | | N | N | | N | N | N | N |
| AMIGO2 | high in NP | -8.7 | 0.021849301 | -1.7 | 13711 | 100 | 175 | 262 | 33 | 69 | 24 | | NA | NA | | N | N | N | N |
| RASSF2 | high in NP | -4.8 | 0.021835663 | -1.7 | 13712 | 175 | 158 | 79 | 29 | 9 | 45 | | N | N | | N | N | N | N |
| ZBTB8A | high in NP | -2.6 | 0.021797477 | -1.7 | 13713 | 742 | 1120 | 1227 | 352 | 322 | 420 | | N | N | | N | N | N | N |
| MICAL2 | high in NP | -5.6 | 0.021754518 | -1.7 | 13714 | 80 | 177 | 84 | 18 | 48 | 17 | | NA | NA | | N | N | N | N |
| IQCK | high in NP | -3.9 | 0.021747699 | -1.7 | 13715 | 12 | 19 | 24 | 6 | 6 | 6 | | N | N | | N | N | N | N |
| PMP22 | high in NP | -4.1 | 0.021734061 | -1.7 | 13716 | 1687 | 2053 | 753 | 320 | 378 | 428 | | N | N | | N | N | N | N |
| CD200 | high in NP | -2.7 | 0.02166178 | -1.7 | 13717 | 29 | 69 | 30 | 10 | 10 | 10 | | N | N | | N | N | N | N |
| CYFIP2 | high in NP | -4.2 | 0.021654961 | -1.7 | 13718 | 37 | 50 | 26 | 8 | 6 | 14 | | N | N | | N | N | N | N |
| RWDD2B | high in NP | -3.8 | 0.021648142 | -1.7 | 13719 | 34 | 18 | 21 | 10 | 8 | 6 | | N | N | | N | N | N | N |
| LRP1 | high in NP | -3.6 | 0.021641323 | -1.7 | 13720 | 4343 | 2104 | 3277 | 958 | 532 | 1202 | | N | N | | N | N | N | N |
| TMEM127 | high in NP | -3.2 | 0.021590863 | -1.7 | 13721 | 495 | 832 | 551 | 351 | 192 | 151 | | N | N | | N | N | N | N |
| ZNF264 | high in NP | -3.0 | 0.021577225 | -1.7 | 13722 | 184 | 326 | 228 | 76 | 89 | 112 | | N | N | | N | N | N | N |
| FOXJ3 | high in NP | -3.2 | 0.021510399 | -1.7 | 13723 | 100 | 180 | 122 | 65 | 43 | 32 | | N | N | | N | N | N | N |
| TPM1 | high in NP | -6.0 | 0.02150358 | -1.7 | 13724 | 109 | 333 | 233 | 42 | 98 | 33 | | N | N | | N | N | N | N |
| C7orf42 | high in NP | -2.5 | 0.021496761 | -1.7 | 13725 | 2114 | 2218 | 1624 | 908 | 924 | 744 | | N | N | | N | N | N | N |
| NCOA7 | high in NP | -4.3 | 0.021483123 | -1.7 | 13726 | 184 | 408 | 494 | 90 | 104 | 115 | | N | N | | N | N | N | N |
| HMGCS1 | high in NP | -3.5 | 0.021449028 | -1.7 | 13727 | 69 | 122 | 151 | 43 | 30 | 27 | | N | N | | N | N | N | N |
| NDUFV2 | high in NP | -4.3 | 0.021442209 | -1.7 | 13728 | 90 | 242 | 228 | 49 | 44 | 29 | | N | N | | N | N | N | N |
| SRP14 | high in NP | -3.1 | 0.02143539 | -1.7 | 13729 | 76 | 118 | 89 | 36 | 8 | 20 | | N | N | | N | N | N | N |
| YWHAE | high in NP | -17.3 | 0.021428571 | -1.7 | 13730 | 49 | 943 | 552 | 28 | 29 | 39 | | P | N | | N | N | P | N |
| ANKRA2 | high in NP | -5.4 | 0.021405387 | -1.7 | 13731 | 11 | 16 | 19 | 5 | 5 | 5 | | N | N | | N | N | N | N |

TABLE 15-continued

Genes that Are Differentially Methylated between Nulliparous and Parous CD44+ Breast Epithelial Cells

| | | | | | SAGE-seq | | | | | | ChIP-seq | | | MSDK-seq | | |
|---|---|---|---|---|---|---|---|---|---|---|---|---|---|---|---|---|
| | | | | | | Nulliparous (NP) | | | Parous (P) | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 NP | CD44+ N66 P | GeneBody NP Met NP | GeneBody Met P | Pro-moter Met NP | Pro-moter Met P |
| EDF1 | high in NP | -3.9 | 0.021363791 | -1.7 | 13732 | 327 | 584 | 737 | 180 | 160 | 63 | N | N | N | N | N | N |
| DARC | high in NP | -6.9 | 0.021344698 | -1.7 | 13733 | 806 | 71 | 62 | 6 | 9 | 27 | N | N | N | N | N | N |
| RFC2 | high in NP | -6.0 | 0.021337879 | -1.7 | 13734 | 13 | 22 | 37 | 6 | 6 | 6 | N | N | N | N | N | N |
| C11orf73 | high in NP | -3.5 | 0.021292192 | -1.7 | 13735 | 55 | 56 | 26 | 15 | 12 | 9 | N | N | N | N | N | N |
| CNNM4 | high in NP | -3.6 | 0.021251279 | -1.7 | 13736 | 56 | 104 | 91 | 20 | 18 | 37 | N | N | N | N | N | N |
| NGFR | high in NP | -6.1 | 0.021237641 | -1.7 | 13737 | 2061 | 339 | 266 | 42 | 134 | 71 | N | N | N | N | N | N |
| NTRK2 | high in NP | -3.1 | 0.021183089 | -1.7 | 13738 | 110 | 166 | 97 | 49 | 61 | 52 | N | N | N | N | N | N |
| SMAD5 | high in NP | -2.7 | 0.02117627 | -1.7 | 13739 | 36 | 97 | 82 | 28 | 26 | 27 | N | N | N | N | N | N |
| F5 | high in NP | -2.6 | 0.021162632 | -1.7 | 13740 | 211 | 364 | 290 | 76 | 87 | 90 | N | P | N | N | N | N |
| RPS6KA1 | high in NP | -6.0 | 0.021142175 | -1.7 | 13741 | 17 | 64 | 67 | 11 | 11 | 11 | N | N | N | N | N | N |
| ZNF549 | high in NP | -4.9 | 0.021128537 | -1.7 | 13742 | 26 | 60 | 33 | 12 | 9 | 16 | N | N | N | N | N | N |
| B4GALT1 | high in NP | -2.7 | 0.021095124 | -1.7 | 13743 | 1180 | 1749 | 1244 | 438 | 528 | 622 | N | N | N | N | N | N |
| ZCCHC7 | high in NP | -2.6 | 0.021075349 | -1.7 | 13744 | 34 | 33 | 30 | 11 | 12 | 7 | N | N | N | N | N | N |
| ZNF805 | high in NP | -2.5 | 0.021060348 | -1.7 | 13745 | 43 | 119 | 84 | 29 | 28 | 28 | NA | N | N | N | N | N |
| EMILIN2 | high in NP | -3.7 | 0.020972383 | -1.7 | 13746 | 64 | 151 | 127 | 30 | 27 | 27 | N | NA | N | N | P | N |
| CRIM1 | high in NP | -7.2 | 0.0209567 | -1.7 | 13747 | 32 | 256 | 131 | 25 | 22 | 21 | N | N | N | N | N | N |
| TMED7 | high in NP | -10.8 | 0.020911695 | -1.7 | 13748 | 81 | 1043 | 355 | 71 | 22 | 30 | N | N | N | N | N | N |
| PPP1R1A | high in NP | -6.0 | 0.020904876 | -1.7 | 13749 | 13 | 22 | 31 | 6 | 6 | 2 | N | N | N | N | N | N |
| RBM15 | high in NP | -6.1 | 0.020878282 | -1.7 | 13750 | 21 | 97 | 46 | 9 | 9 | 12 | N | N | N | N | N | N |
| NDUFB11 | high in NP | -2.6 | 0.020871463 | -1.7 | 13751 | 156 | 157 | 141 | 59 | 41 | 41 | N | N | N | N | N | N |
| FMO1 | high in NP | -5.5 | 0.020772588 | -1.7 | 13752 | 488 | 37 | 55 | 6 | 9 | 17 | N | N | N | N | N | N |
| DPCD | high in NP | -7.9 | 0.020765769 | -1.7 | 13753 | 20 | 24 | 16 | 4 | 4 | 10 | N | N | N | N | N | N |
| SEC61B | high in NP | -127.1 | 0.020753495 | -1.7 | 13754 | 2 | 257 | 195 | 2 | 2 | 2 | NA | NA | N | N | N | N |
| CTSB | high in NP | -4.1 | 0.020746676 | -1.7 | 13755 | 926 | 1537 | 2749 | 732 | 344 | 316 | N | N | N | N | N | N |
| ADAM12 | high in NP | -4.2 | 0.020720764 | -1.7 | 13756 | 385 | 131 | 115 | 26 | 41 | 55 | N | N | N | N | N | N |
| PLOD2 | high in NP | -5.1 | 0.020683259 | -1.7 | 13757 | 14 | 118 | 214 | 14 | 14 | 17 | N | N | N | N | N | N |
| LMCD1 | high in NP | -4.3 | 0.020658711 | -1.7 | 13758 | 339 | 258 | 115 | 47 | 64 | 33 | N | N | N | N | N | N |
| SYTL2 | high in NP | -2.8 | 0.020636209 | -1.7 | 13759 | 107 | 41 | 39 | 20 | 17 | 17 | N | N | N | N | N | N |
| KIAA0090 | high in NP | -3.1 | 0.020620525 | -1.7 | 13760 | 36 | 86 | 64 | 13 | 19 | 18 | N | N | N | N | N | N |
| RALA | high in NP | -3.5 | 0.020613706 | -1.7 | 13761 | 187 | 316 | 341 | 88 | 102 | 86 | N | N | N | N | N | N |
| TNFRSF10D | high in NP | -5.6 | 0.020578248 | -1.7 | 13762 | 33 | 142 | 149 | 21 | 19 | 25 | N | N | N | N | N | N |
| NFU1 | high in NP | -4.9 | 0.020571429 | -1.7 | 13763 | 56 | 64 | 48 | 24 | 9 | 7 | N | N | N | N | N | N |
| CCDC120 | high in NP | -3.2 | 0.020524378 | -1.7 | 13764 | 156 | 318 | 290 | 80 | 88 | 43 | N | N | N | N | N | N |
| EI24 | high in NP | -3.4 | 0.020501875 | -1.7 | 13765 | 263 | 528 | 333 | 168 | 100 | 63 | N | N | N | N | N | N |
| HNRNPA1 | high in NP | -42.0 | 0.020468462 | -1.7 | 13766 | 11 | 484 | 241 | 9 | 5 | 5 | N | N | N | N | P | N |
| CTBP1 | high in NP | -2.8 | 0.020461643 | -1.7 | 13767 | 545 | 695 | 447 | 255 | 224 | 152 | N | N | N | N | N | N |
| TACSTD2 | high in NP | -8.6 | 0.020403682 | -1.7 | 13768 | 256 | 2584 | 3391 | 88 | 394 | 51 | P | N | N | N | N | N |
| TRAM1 | high in NP | -4.4 | 0.020279577 | -1.7 | 13769 | 608 | 620 | 427 | 257 | 128 | 73 | N | N | N | N | N | N |
| TRAPPC6B | high in NP | -2.9 | 0.020272758 | -1.7 | 13770 | 25 | 53 | 37 | 13 | 13 | 13 | N | N | N | N | N | N |
| TFPI | high in NP | -4.9 | 0.020250256 | -1.7 | 13771 | 473 | 3035 | 2259 | 665 | 115 | 156 | N | N | N | N | N | N |
| MRPL54 | high in NP | -5.7 | 0.020236618 | -1.7 | 13772 | 19 | 68 | 58 | 9 | 6 | 6 | N | N | N | N | N | N |
| MRPL21 | high in NP | -7.5 | 0.020214797 | -1.7 | 13773 | 16 | 61 | 43 | 9 | 5 | 5 | N | N | N | N | N | N |
| RAB5B | high in NP | -2.5 | 0.020171838 | -1.7 | 13774 | 757 | 649 | 637 | 318 | 214 | 269 | N | N | N | N | N | N |
| QARS | high in NP | -3.6 | 0.020096147 | -1.7 | 13775 | 34 | 142 | 68 | 15 | 14 | 10 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | | Nulliparous (NP) | | | Parous (P) | | | NP | | P | | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| TP53INP1 | high in NP | -3.6 | 0.020075009 | -1.7 | 13776 | 49 | 75 | 110 | 28 | 13 | 21 | N | N | P | N | P | N |
| ERH | high in NP | -56.1 | 0.020043641 | -1.7 | 13777 | 12 | 391 | 188 | 8 | 6 | 6 | N | N | N | N | N | N |
| RHOA | high in NP | -2.6 | 0.020023184 | -1.7 | 13778 | 3667 | 2648 | 3340 | 1373 | 1050 | 990 | N | N | N | N | N | N |
| RTN2 | high in NP | -3.7 | 0.019966587 | -1.7 | 13779 | 39 | 19 | 15 | 7 | 5 | 2 | N | N | N | N | N | P |
| ATP5F1 | high in NP | -6.3 | 0.01989226 | -1.7 | 13780 | 101 | 402 | 205 | 42 | 14 | 54 | N | N | N | N | N | N |
| THY1 | high in NP | -4.8 | 0.019885442 | -1.7 | 13781 | 491 | 444 | 150 | 45 | 71 | 89 | N | N | P | N | P | N |
| TMEM30A | high in NP | -4.2 | 0.019849301 | -1.7 | 13782 | 263 | 746 | 766 | 222 | 142 | 116 | N | N | N | N | N | N |
| PSMD8 | high in NP | -5.0 | 0.019734743 | -1.7 | 13783 | 366 | 1385 | 1008 | 256 | 205 | 88 | N | N | N | N | N | N |
| MAF | high in NP | -4.9 | 0.019727924 | -1.7 | 13784 | 1210 | 579 | 740 | 190 | 143 | 502 | N | N | N | N | N | N |
| SLC39A9 | high in NP | -2.8 | 0.019721105 | -1.7 | 13785 | 154 | 177 | 186 | 81 | 40 | 54 | N | N | N | N | N | N |
| ZC3H4 | high in NP | -2.9 | 0.019700648 | -1.7 | 13786 | 105 | 139 | 187 | 42 | 48 | 53 | N | N | N | N | N | N |
| ELF2 | high in NP | -2.7 | 0.019693829 | -1.7 | 13787 | 72 | 75 | 67 | 26 | 24 | 29 | N | N | N | N | N | N |
| EFR3A | high in NP | -2.9 | 0.01968701 | -1.7 | 13788 | 45 | 70 | 71 | 22 | 23 | 13 | N | N | N | N | N | N |
| C17orf85 | high in NP | -4.7 | 0.019641323 | -1.7 | 13789 | 28 | 107 | 76 | 14 | 20 | 12 | N | N | N | N | N | N |
| PNP | high in NP | -3.3 | 0.019592226 | -1.7 | 13790 | 992 | 644 | 677 | 258 | 295 | 140 | NA | NA | N | N | N | N |
| TOMM22 | high in NP | -6.8 | 0.019533583 | -1.7 | 13791 | 115 | 875 | 333 | 84 | 41 | 35 | N | N | N | N | N | N |
| AKR1B1 | high in NP | -12.3 | 0.019494033 | -1.7 | 13792 | 27 | 519 | 489 | 35 | 11 | 14 | N | N | N | N | P | N |
| CHRNB1 | high in NP | -2.7 | 0.019487214 | -1.7 | 13793 | 36 | 36 | 41 | 11 | 5 | 10 | N | N | N | N | N | N |
| TPM4 | high in NP | -4.9 | 0.01928571 | -1.7 | 13794 | 252 | 1358 | 655 | 171 | 159 | 76 | N | N | N | N | N | N |
| LZTFL1 | high in NP | -7.9 | 0.019421752 | -1.7 | 13795 | 11 | 40 | 25 | 5 | 5 | 5 | N | N | N | N | N | N |
| HBP1 | high in NP | -13.9 | 0.019401296 | -1.7 | 13796 | 21 | 424 | 396 | 23 | 15 | 21 | N | P | N | N | N | N |
| TBC1D10B | high in NP | -2.8 | 0.019387658 | -1.7 | 13797 | 105 | 181 | 136 | 57 | 39 | 51 | N | N | N | N | N | N |
| LAMP1 | high in NP | -3.5 | 0.019366519 | -1.7 | 13798 | 858 | 1284 | 727 | 493 | 216 | 214 | N | N | N | N | N | N |
| NDUFA12 | high in NP | -5.1 | 0.019307876 | -1.7 | 13799 | 26 | 68 | 66 | 9 | 8 | 3 | N | N | N | N | N | N |
| TFPI2 | high in NP | -2.8 | 0.019264916 | -1.7 | 13800 | 44 | 99 | 38 | 15 | 11 | 13 | N | N | N | N | N | N |
| NDUFA4 | high in NP | -13.4 | 0.019258098 | -1.7 | 13801 | 51 | 439 | 322 | 39 | 24 | 16 | N | N | N | N | N | N |
| F11R | high in NP | -5.1 | 0.01924446 | -1.7 | 13802 | 68 | 260 | 223 | 39 | 47 | 29 | N | N | N | N | N | N |
| WEE1 | high in NP | -2.9 | 0.019216502 | -1.7 | 13803 | 474 | 713 | 783 | 204 | 286 | 206 | N | N | N | N | N | N |
| ZHX2 | high in NP | -2.9 | 0.019209683 | -1.7 | 13804 | 85 | 123 | 90 | 37 | 32 | 21 | N | N | N | N | N | N |
| NEK3 | high in NP | -3.7 | 0.019196045 | -1.7 | 13805 | 20 | 6 | 8 | 4 | 4 | 4 | N | N | N | N | P | N |
| IRAK2 | high in NP | -4.1 | 0.019182407 | -1.7 | 13806 | 255 | 585 | 189 | 122 | 41 | 55 | N | N | N | N | N | N |
| RFC3 | high in NP | -8.3 | 0.019142857 | -1.7 | 13807 | 13 | 29 | 27 | 6 | 6 | 6 | NA | P | N | N | N | N |
| C10orf75 | high in NP | -3.3 | 0.019136038 | -1.7 | 13808 | 41 | 28 | 34 | 9 | 5 | 10 | NA | NA | N | N | N | N |
| EFEMP1 | high in NP | -5.4 | 0.01911149 | -1.7 | 13809 | 43 | 545 | 97 | 13 | 20 | 13 | N | N | N | N | N | N |
| SFRS2B | high in NP | -3.2 | 0.019091033 | -1.7 | 13810 | 65 | 161 | 102 | 39 | 20 | 26 | N | N | N | N | N | N |
| ITM2B | high in NP | -4.1 | 0.01907194 | -1.7 | 13811 | 2315 | 2259 | 962 | 487 | 430 | 554 | NA | NA | N | N | N | N |
| SLC25A17 | high in NP | -6.7 | 0.019065121 | -1.7 | 13812 | 13 | 64 | 30 | 6 | 6 | 6 | N | N | N | N | N | N |
| VPS37A | high in NP | -7.2 | 0.019042618 | -1.7 | 13813 | 20 | 187 | 100 | 14 | 14 | 14 | N | N | N | N | N | N |
| NCRNA00116 | high in NP | -4.9 | 0.01990358 | -1.7 | 13814 | 18 | 100 | 53 | 9 | 6 | 6 | N | N | N | N | N | N |
| SFRS2 | high in NP | -4.4 | 0.019028981 | -1.7 | 13815 | 894 | 2681 | 2304 | 357 | 584 | 511 | N | N | N | N | N | N |
| PLK2 | high in NP | -4.9 | 0.019016025 | -1.7 | 13816 | 43 | 198 | 144 | 19 | 19 | 34 | N | N | N | N | P | N |
| TACR1 | high in NP | -8.5 | 0.0189642 | -1.7 | 13817 | 17 | 35 | 42 | 11 | 11 | 11 | N | N | N | N | N | N |
| SLC39A1 | high in NP | -5.1 | 0.018951926 | -1.7 | 13818 | 124 | 402 | 329 | 78 | 55 | 19 | N | N | N | N | N | N |
| SOX17 | high in NP | -4.9 | 0.018938288 | -1.7 | 13819 | 238 | 54 | 35 | 15 | 7 | 7 | P | P | N | N | P | P |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | Nulliparous (NP) | | | | Parous (P) | | | NP | | P | | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| HERC4 | high in NP | -3.0 | 0.018882373 | -1.7 | 13820 | 24 | 53 | 61 | 15 | 13 | 13 | N | N | N | N | N | N |
| SH3BGR | high in NP | -8.8 | 0.018875554 | -1.7 | 13821 | 11 | 31 | 29 | 5 | 5 | 5 | N | N | N | N | N | N |
| TUBA1C | high in NP | -17.3 | 0.01882032 | -1.7 | 13822 | 118 | 2213 | 986 | 49 | 83 | 39 | N | N | N | N | N | N |
| ZFP36L2 | high in NP | -3.6 | 0.018806683 | -1.7 | 13823 | 3559 | 4435 | 3293 | 924 | 996 | 1902 | N | N | N | N | N | N |
| SCMH1 | high in NP | -3.1 | 0.018799864 | -1.7 | 13824 | 28 | 51 | 58 | 18 | 12 | 12 | N | N | N | N | N | N |
| PELI1 | high in NP | -3.1 | 0.018775997 | -1.7 | 13825 | 992 | 833 | 914 | 224 | 319 | 437 | N | N | N | N | N | N |
| PICALM | high in NP | -4.7 | 0.018762359 | -1.7 | 13826 | 212 | 677 | 455 | 88 | 127 | 83 | N | N | N | N | N | N |
| SPAG7 | high in NP | -2.9 | 0.01875554 | -1.7 | 13827 | 138 | 249 | 182 | 43 | 64 | 41 | N | N | N | N | N | N |
| C1orf43 | high in NP | -13.3 | 0.018748721 | -1.7 | 13828 | 23 | 223 | 211 | 15 | 11 | 6 | N | N | N | N | N | N |
| TAP1 | high in NP | -4.2 | 0.018728265 | -1.7 | 13829 | 309 | 318 | 151 | 63 | 33 | 76 | N | N | N | N | N | N |
| TWF2 | high in NP | -3.8 | 0.018713945 | -1.7 | 13830 | 86 | 30 | 66 | 15 | 9 | 6 | N | N | N | N | N | N |
| NFYC | high in NP | -3.9 | 0.018707126 | -1.7 | 13831 | 57 | 106 | 135 | 24 | 19 | 31 | N | N | N | N | N | N |
| PLEKHB2 | high in NP | -3.0 | 0.018686669 | -1.7 | 13832 | 512 | 797 | 720 | 274 | 261 | 280 | N | N | N | N | N | N |
| CPEB3 | high in NP | -4.3 | 0.018660757 | -1.7 | 13833 | 22 | 51 | 70 | 13 | 11 | 11 | N | N | N | N | N | N |
| XRN2 | high in NP | -5.3 | 0.018653938 | -1.7 | 13834 | 118 | 479 | 344 | 80 | 52 | 52 | N | N | N | N | N | N |
| SLC25A6 | high in NP | -2.9 | 0.018647119 | -1.7 | 13835 | 4226 | 3665 | 5231 | 1143 | 1763 | 1464 | N | N | N | N | N | N |
| TAC1 | high in NP | -12.0 | 0.0186403 | -1.7 | 13836 | 21 | 221 | 260 | 9 | 9 | 18 | N | N | N | N | N | N |
| SPOCK1 | high in NP | -4.2 | 0.018606205 | -1.7 | 13837 | 187 | 78 | 42 | 20 | 15 | 10 | N | N | N | N | N | N |
| SLIT3 | high in NP | -4.4 | 0.018592567 | -1.7 | 13838 | 297 | 199 | 80 | 39 | 20 | 31 | N | N | P | N | N | N |
| PDK3 | high in NP | -4.9 | 0.018554381 | -1.7 | 13839 | 17 | 48 | 36 | 8 | 6 | 6 | N | N | N | N | N | N |
| SHOC2 | high in NP | -2.6 | 0.018542107 | -1.7 | 13840 | 150 | 198 | 161 | 52 | 65 | 54 | N | N | N | N | N | N |
| UPP1 | high in NP | -4.6 | 0.018455506 | -1.7 | 13841 | 1882 | 723 | 2318 | 465 | 311 | 269 | P | N | N | N | N | N |
| APPL1 | high in NP | -2.9 | 0.018441868 | -1.7 | 13842 | 132 | 194 | 110 | 50 | 57 | 44 | N | N | N | N | N | N |
| GNPTG | high in NP | -3.3 | 0.018435049 | -1.7 | 13843 | 25 | 34 | 43 | 10 | 7 | 7 | N | N | N | N | N | N |
| STS | high in NP | -2.7 | 0.018409137 | -1.7 | 13844 | 37 | 29 | 33 | 11 | 11 | 11 | N | N | N | N | N | N |
| CASC4 | high in NP | -3.3 | 0.018351176 | -1.7 | 13845 | 1068 | 680 | 507 | 281 | 185 | 191 | N | P | N | N | N | P |
| FCGRT | high in NP | -2.7 | 0.018344357 | -1.7 | 13846 | 601 | 504 | 394 | 183 | 127 | 164 | N | N | N | N | N | N |
| THBS2 | high in NP | -5.5 | 0.018282987 | -1.7 | 13847 | 483 | 1965 | 1667 | 372 | 187 | 282 | N | N | N | N | N | N |
| SFRS3 | high in NP | -3.9 | 0.018276168 | -1.7 | 13848 | 794 | 1941 | 1398 | 536 | 377 | 383 | N | N | N | N | N | N |
| RAP2B | high in NP | -4.2 | 0.018260484 | -1.7 | 13849 | 326 | 933 | 920 | 113 | 235 | 144 | N | N | N | N | N | N |
| IGFBP7 | high in NP | -5.4 | 0.018253665 | -1.7 | 13850 | 543 | 2495 | 203 | 119 | 41 | 92 | N | N | N | N | N | N |
| SLC5A3 | high in NP | -3.4 | 0.018246846 | -1.7 | 13851 | 75 | 144 | 129 | 31 | 33 | 50 | N | N | N | N | N | N |
| MKRN2 | high in NP | -5.6 | 0.018212751 | -1.7 | 13852 | 30 | 105 | 116 | 20 | 17 | 17 | N | N | N | N | N | N |
| RDH14 | high in NP | -2.5 | 0.018205932 | -1.7 | 13853 | 73 | 68 | 73 | 23 | 23 | 14 | N | N | N | N | N | N |
| MIF | high in NP | -3.1 | 0.018175247 | -1.7 | 13854 | 23 | 45 | 59 | 10 | 6 | 6 | N | N | N | N | N | N |
| C1orf122 | high in NP | -4.0 | 0.018168428 | -1.7 | 13855 | 49 | 133 | 83 | 10 | 16 | 18 | N | N | N | N | N | N |
| SKP1 | high in NP | -6.2 | 0.018161609 | -1.7 | 13856 | 522 | 2190 | 2070 | 269 | 324 | 256 | N | N | N | N | P | N |
| RHOB | high in NP | -6.8 | 0.018149335 | -1.7 | 13857 | 484 | 2430 | 1527 | 369 | 228 | 220 | N | N | N | N | N | N |
| TIAL1 | high in NP | -7.7 | 0.018142516 | -1.7 | 13858 | 62 | 257 | 246 | 34 | 31 | 30 | N | N | N | N | N | N |
| PTGES3 | high in NP | -11.9 | 0.018102284 | -1.7 | 13859 | 374 | 3555 | 3437 | 229 | 169 | 287 | N | N | N | N | N | N |
| RRP1B | high in NP | -3.2 | 0.018095465 | -1.7 | 13860 | 68 | 266 | 142 | 24 | 35 | 34 | N | N | N | N | N | N |
| HECTD1 | high in NP | -4.6 | 0.018061371 | -1.7 | 13861 | 46 | 176 | 199 | 41 | 30 | 42 | N | N | N | N | N | N |
| SNX25 | high in NP | -11.1 | 0.018037504 | -1.7 | 13862 | 13 | 42 | 39 | 7 | 7 | 7 | N | N | N | N | N | N |
| GNAS | high in NP | -11.9 | 0.017954995 | -1.7 | 13863 | 419 | 3537 | 3082 | 244 | 270 | 230 | P | N | P | N | N | P |

TABLE 15-continued

Genes that Are Differentially Methylated between Nulliparous and Parous CD44+ Breast Epithelial Cells

| | | | | | SAGE-seq | | | | | | ChIP-seq | | | | MSDK-seq | | |
|---|---|---|---|---|---|---|---|---|---|---|---|---|---|---|---|---|---|
| | | | | | | Nulliparous (NP) | | | Parous (P) | | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| | | | | | | | | | | | | NP | P | NP | P | NP | P |
| DSC2 | high in NP | −7.6 | 0.01948176 | −1.7 | 13864 | 62 | 206 | 409 | 23 | 50 | 26 | N | P | N | N | N | N |
| SMAD7 | high in NP | −4.2 | 0.01929083 | −1.7 | 13865 | 111 | 513 | 148 | 34 | 30 | 48 | N | N | N | N | N | N |
| HEXIM1 | high in NP | −3.8 | 0.01901807 | −1.7 | 13866 | 209 | 400 | 193 | 46 | 52 | 101 | N | N | N | N | N | N |
| PAN3 | high in NP | −3.2 | 0.01788135 | −1.7 | 13867 | 180 | 337 | 348 | 80 | 110 | 63 | N | N | N | N | N | N |
| NAPA | high in NP | −3.0 | 0.01865667 | −1.7 | 13868 | 899 | 484 | 596 | 239 | 181 | 162 | NA | NA | N | N | N | N |
| TMX2 | high in NP | −5.1 | 0.01852029 | −1.7 | 13869 | 58 | 237 | 163 | 28 | 28 | 21 | N | N | N | N | N | N |
| RCN1 | high in NP | −4.3 | 0.01838391 | −1.7 | 13870 | 325 | 889 | 691 | 184 | 151 | 135 | N | N | N | N | N | N |
| GMCL1 | high in NP | −2.8 | 0.01823389 | −1.7 | 13871 | 15 | 5 | 6 | 2 | 2 | 2 | NA | N | N | N | N | N |
| RBBP4 | high in NP | −3.2 | 0.01802932 | −1.7 | 13872 | 256 | 399 | 540 | 151 | 130 | 149 | N | N | N | N | N | N |
| ANTXR2 | high in NP | −3.5 | 0.01774974 | −1.7 | 13873 | 115 | 92 | 117 | 27 | 29 | 39 | N | N | N | N | N | N |
| ANTXR1 | high in NP | −3.9 | 0.01774088 | −1.8 | 13874 | 354 | 180 | 121 | 45 | 47 | 59 | N | N | N | N | N | N |
| TMEM167A | high in NP | −2.7 | 0.01770133 | −1.8 | 13875 | 127 | 205 | 173 | 69 | 45 | 40 | N | N | N | N | N | N |
| KIAA1467 | high in NP | −6.5 | 0.01767235 | −1.8 | 13876 | 15 | 40 | 35 | 9 | 9 | 9 | N | N | N | N | N | N |
| RCOR3 | high in NP | −3.1 | 0.01767913 | −1.8 | 13877 | 66 | 60 | 47 | 17 | 20 | 24 | NA | NA | N | N | N | N |
| PGAP2 | high in NP | −2.8 | 0.01609956 | −1.8 | 13878 | 28 | 29 | 60 | 12 | 12 | 12 | N | N | N | N | N | N |
| BET1 | high in NP | −13.1 | 0.01569724 | −1.8 | 13879 | 11 | 43 | 66 | 5 | 5 | 5 | N | N | N | N | N | N |
| C2orf40 | high in NP | −9.6 | 0.01526764 | −1.8 | 13880 | 759 | 435 | 73 | 18 | 69 | 16 | N | N | N | N | N | N |
| MLF1 | high in NP | −5.7 | 0.01519945 | −1.8 | 13881 | 19 | 120 | 50 | 6 | 6 | 6 | N | N | N | N | N | N |
| CXCL6 | high in NP | −17.7 | 0.01513126 | −1.8 | 13882 | 81 | 982 | 1002 | 42 | 21 | 47 | N | N | N | N | N | N |
| SLC41A2 | high in NP | −4.0 | 0.01506308 | −1.8 | 13883 | 42 | 12 | 11 | 6 | 4 | 4 | N | N | N | N | N | N |
| TMEM69 | high in NP | −9.4 | 0.01465394 | −1.8 | 13884 | 39 | 28 | 29 | 13 | 3 | 3 | N | N | N | N | N | N |
| SMG7 | high in NP | −2.8 | 0.01450392 | −1.8 | 13885 | 64 | 69 | 63 | 32 | 19 | 20 | N | P | N | N | N | N |
| IMP3 | high in NP | −5.0 | 0.01443573 | −1.8 | 13886 | 106 | 283 | 195 | 52 | 41 | 21 | N | N | N | N | N | N |
| COL15A1 | high in NP | −4.4 | 0.01436754 | −1.8 | 13887 | 531 | 172 | 158 | 75 | 54 | 35 | N | N | N | N | N | N |
| OS9 | high in NP | −4.7 | 0.01363109 | −1.8 | 13888 | 89 | 228 | 134 | 14 | 33 | 31 | N | N | N | N | N | N |
| FBLN1 | high in NP | −4.2 | 0.01335152 | −1.8 | 13889 | 4078 | 4088 | 1501 | 506 | 752 | 912 | N | N | N | N | N | N |
| DYNLT3 | high in NP | −4.7 | 0.01318104 | −1.8 | 13890 | 57 | 214 | 163 | 42 | 12 | 15 | N | P | N | N | N | N |
| PREB | high in NP | −3.1 | 0.01266962 | −1.8 | 13891 | 49 | 58 | 108 | 20 | 15 | 14 | N | N | N | N | N | N |
| PARVA | high in NP | −3.0 | 0.01253324 | −1.8 | 13892 | 182 | 117 | 167 | 53 | 44 | 54 | N | N | N | N | N | N |
| ARPP19 | high in NP | −3.0 | 0.01230822 | −1.8 | 13893 | 790 | 1291 | 852 | 491 | 371 | 259 | NA | NA | N | N | N | N |
| LMAN1 | high in NP | −4.1 | 0.01203546 | −1.8 | 13894 | 48 | 141 | 154 | 43 | 20 | 24 | N | N | N | N | N | N |
| WIPF2 | high in NP | −2.7 | 0.01196727 | −1.8 | 13895 | 263 | 262 | 256 | 138 | 90 | 83 | N | N | N | N | N | N |
| RPL14 | high in NP | −2.9 | 0.01717627 | −1.8 | 13896 | 1652 | 2715 | 2418 | 638 | 781 | 804 | N | N | N | N | N | N |
| PSMD4 | high in NP | −3.7 | 0.01746949 | −1.8 | 13897 | 178 | 253 | 230 | 84 | 36 | 38 | N | N | N | N | N | N |
| CD59 | high in NP | −3.5 | 0.01712581 | −1.8 | 13898 | 1515 | 2640 | 4337 | 876 | 892 | 859 | N | N | N | N | N | N |
| NUMBL | high in NP | −3.1 | 0.01027617 | −1.8 | 13899 | 86 | 91 | 102 | 34 | 29 | 35 | N | N | N | N | N | N |
| INSIG2 | high in NP | −2.5 | 0.01020798 | −1.8 | 13900 | 83 | 96 | 143 | 43 | 17 | 13 | N | N | N | N | N | N |
| TIMELESS | high in NP | −4.5 | 0.00998295 | −1.8 | 13901 | 31 | 23 | 39 | 7 | 8 | 8 | N | N | N | N | N | N |
| SCN4B | high in NP | −3.0 | 0.00923287 | −1.8 | 13902 | 359 | 106 | 109 | 38 | 26 | 26 | N | N | P | N | N | N |
| CMC1 | high in NP | −3.6 | 0.00869417 | −1.8 | 13903 | 9 | 7 | 6 | 2 | 2 | 2 | N | N | N | N | N | N |
| GHDC | high in NP | −5.4 | 0.00855779 | −1.8 | 13904 | 66 | 32 | 43 | 10 | 8 | 11 | N | N | N | N | N | N |
| ZBTB38 | high in NP | −3.2 | 0.00842141 | −1.8 | 13905 | 67 | 72 | 105 | 37 | 22 | 22 | N | N | N | N | N | N |
| POTEE | high in NP | −5.6 | 0.00806001 | −1.8 | 13906 | 7 | 7 | 5 | 1 | 1 | 1 | NA | NA | N | N | N | N |
| TOB1 | high in NP | −3.5 | 0.00799182 | −1.8 | 13907 | 395 | 1057 | 476 | 140 | 136 | 196 | N | N | N | N | P | P |

TABLE 15-continued

Genes that Are Differentially Methylated between Nulliparous and Parous CD44+ Breast Epithelial Cells

| | | | | | | SAGE-seq | | | | | | | ChIP-seq | | | MSDK-seq | | |
|---|---|---|---|---|---|---|---|---|---|---|---|---|---|---|---|---|---|---|
| | | | | | | Nulliparous (NP) | | | | Parous (P) | | | NP | P | GeneBody | | Pro-moter | Pro-moter |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | Met | P | NP | Met | P |
| EIF1 | high in NP | −8.4 | 0.016778043 | −1.8 | 13908 | 701 | 5034 | 3840 | 251 | 302 | 532 | N | N | N | N | N | N | N |
| VPS35 | high in NP | −5.1 | 0.016737129 | −1.8 | 13909 | 88 | 173 | 270 | 37 | 42 | 24 | N | N | N | N | N | N | N |
| TUBA1B | high in NP | −39.8 | 0.016703716 | −1.8 | 13910 | 92 | 3226 | 2641 | 45 | 54 | 48 | N | N | N | N | N | N | N |
| EFNA3 | high in NP | −7.7 | 0.016623253 | −1.8 | 13911 | 17 | 31 | 18 | 11 | 11 | 11 | N | N | N | N | N | N | N |
| CAT | high in NP | −3.4 | 0.01660075 | −1.8 | 13912 | 95 | 74 | 55 | 25 | 12 | 18 | N | N | N | N | N | N | N |
| PPP3R1 | high in NP | −7.6 | 0.016587112 | −1.8 | 13913 | 50 | 248 | 209 | 22 | 29 | 35 | N | N | N | N | N | N | N |
| LOC728661 | high in NP | −4.2 | 0.016559154 | −1.8 | 13914 | NA | NA | NA | NA | NA | NA | NA | NA | N | N | N | N | N |
| PITRM1 | high in NP | −10.3 | 0.016552335 | −1.8 | 13915 | 29 | 121 | 167 | 17 | 20 | 17 | N | N | N | N | N | N | N |
| C7orf70 | high in NP | −7.9 | 0.016545517 | −1.8 | 13916 | 20 | 15 | 29 | 8 | 4 | 4 | N | N | N | N | N | N | N |
| CXCL12 | high in NP | −7.3 | 0.016505967 | −1.8 | 13917 | 3763 | 1378 | 637 | 150 | 166 | 503 | N | N | N | N | N | N | N |
| MYL12B | high in NP | −4.4 | 0.016492329 | −1.8 | 13918 | 1035 | 2175 | 1877 | 393 | 567 | 198 | N | N | N | N | N | N | N |
| DPAGT1 | high in NP | −4.0 | 0.016463689 | −1.8 | 13919 | 24 | 67 | 61 | 10 | 13 | 8 | N | N | N | N | N | N | N |
| C10orf46 | high in NP | −3.0 | 0.016390044 | −1.8 | 13920 | 109 | 155 | 136 | 54 | 55 | 34 | N | N | N | N | N | N | N |
| ZNF581 | high in NP | −4.2 | 0.016376406 | −1.8 | 13921 | 62 | 131 | 167 | 22 | 16 | 26 | N | N | N | N | P | N | N |
| CCDC111 | high in NP | −7.8 | 0.016353904 | −1.8 | 13922 | 13 | 15 | 22 | 6 | 6 | 6 | N | N | N | N | N | N | N |
| ACLY | high in NP | −3.4 | 0.016340266 | −1.8 | 13923 | 32 | 74 | 64 | 21 | 21 | 21 | N | N | N | N | N | N | N |
| ATG7 | high in NP | −3.4 | 0.016300716 | −1.8 | 13924 | 41 | 82 | 91 | 25 | 13 | 13 | N | N | N | N | N | N | N |
| PON2 | high in NP | −8.1 | 0.016293897 | −1.8 | 13925 | 18 | 84 | 58 | 6 | 6 | 9 | N | N | N | N | P | N | N |
| SIX4 | high in NP | −3.2 | 0.016278213 | −1.8 | 13926 | 47 | 72 | 55 | 21 | 21 | 27 | N | N | N | N | P | N | N |
| TMEM93 | high in NP | −19.2 | 0.016256393 | −1.8 | 13927 | 13 | 159 | 194 | 6 | 2 | 2 | N | N | N | N | N | N | N |
| CORO1C | high in NP | −5.4 | 0.016241391 | −1.8 | 13928 | 41 | 182 | 148 | 32 | 30 | 36 | N | N | N | N | N | N | N |
| CNN3 | high in NP | −3.2 | 0.016234572 | −1.8 | 13929 | 4139 | 2027 | 2375 | 790 | 772 | 1019 | N | N | N | N | N | N | N |
| IFFO2 | high in NP | −4.4 | 0.016214115 | −1.8 | 13930 | 327 | 375 | 419 | 68 | 176 | 81 | N | N | N | N | N | N | N |
| RAB28 | high in NP | −6.9 | 0.016164337 | −1.8 | 13931 | 10 | 10 | 9 | 4 | 4 | 4 | N | N | N | N | N | N | N |
| PTP4A3 | high in NP | −5.6 | 0.01606819 | −1.8 | 13932 | 329 | 91 | 74 | 14 | 34 | 12 | N | N | N | N | P | N | N |
| RAB10 | high in NP | −12.9 | 0.016061371 | −1.8 | 13933 | 53 | 585 | 579 | 31 | 35 | 32 | N | N | N | N | N | N | N |
| HERPUD1 | high in NP | −7.0 | 0.016004773 | −1.8 | 13934 | 174 | 765 | 660 | 110 | 83 | 45 | N | N | N | N | N | N | N |
| PRKAR1A | high in NP | −8.7 | 0.01598909 | −1.8 | 13935 | 823 | 4123 | 4704 | 606 | 296 | 464 | N | N | N | N | N | N | N |
| PARD3 | high in NP | −3.4 | 0.015975452 | −1.8 | 13936 | 26 | 41 | 37 | 15 | 15 | 15 | N | N | N | N | N | N | N |
| TAOK1 | high in NP | −2.8 | 0.015947494 | −1.8 | 13937 | 36 | 53 | 69 | 21 | 19 | 19 | N | N | N | N | N | N | N |
| CAP2 | high in NP | −3.9 | 0.015907944 | −1.8 | 13938 | 37 | 19 | 14 | 8 | 8 | 8 | N | N | N | N | N | N | N |
| BANF1 | high in NP | −4.9 | 0.015879304 | −1.8 | 13939 | 987 | 445 | 334 | 155 | 105 | 52 | N | N | N | N | N | N | N |
| LSM1 | high in NP | −3.0 | 0.015872486 | −1.8 | 13940 | 49 | 58 | 88 | 14 | 14 | 13 | N | N | N | N | N | N | N |
| BMPR2 | high in NP | −3.6 | 0.015829526 | −1.8 | 13941 | 206 | 174 | 127 | 59 | 53 | 56 | N | N | N | N | P | N | N |
| C2orf28 | high in NP | −4.0 | 0.015800205 | −1.8 | 13942 | 234 | 174 | 138 | 49 | 43 | 15 | N | N | N | N | N | N | N |
| MRPL22 | high in NP | −5.3 | 0.015786567 | −1.8 | 13943 | 24 | 28 | 13 | 7 | 3 | 3 | N | N | N | N | N | N | N |
| CEBPG | high in NP | −3.3 | 0.015764064 | −1.8 | 13944 | 101 | 259 | 159 | 34 | 49 | 42 | N | N | N | N | N | N | N |
| LOC339788 | high in NP | −4.8 | 0.015757245 | −1.8 | 13945 | 18 | 2 | 4 | 2 | 2 | 2 | N | N | N | N | N | N | N |
| CDKN2C | high in NP | −3.6 | 0.015714286 | −1.8 | 13946 | 37 | 44 | 65 | 9 | 5 | 13 | N | N | N | N | N | N | N |
| C11orf59 | high in NP | −4.4 | 0.015688574 | −1.8 | 13947 | 57 | 171 | 115 | 29 | 13 | 7 | N | N | N | N | N | N | N |
| CMTM8 | high in NP | −4.8 | 0.015567269 | −1.8 | 13948 | 152 | 50 | 68 | 12 | 20 | 8 | N | N | N | N | N | N | N |
| SELK | high in NP | −5.9 | 0.015659052 | −1.8 | 13949 | 320 | 1031 | 1037 | 171 | 119 | 138 | N | P | N | N | N | N | N |
| ZBED3 | high in NP | −9.2 | 0.015630413 | −1.8 | 13950 | 115 | 18 | 36 | 12 | 7 | 4 | N | N | N | N | N | N | N |
| AFAP1 | high in NP | −2.7 | 0.015574497 | −1.8 | 13951 | 110 | 118 | 97 | 36 | 32 | 39 | N | N | N | N | N | N | N |

TABLE 15-continued

Genes that Are Differentially Methylated between Nulliparous and Parous CD44+ Breast Epithelial Cells

| Gene Symbol | expression pattern | Fold Change | p-value | log10 (p-val.) | Ranking | SAGE-seq Nulliparous (NP) | | | | SAGE-seq Parous (P) | | | | ChIP-seq NP | ChIP-seq P | MSDK-seq NP | | MSDK-seq P | |
|---|---|---|---|---|---|---|---|---|---|---|---|---|---|---|---|---|---|---|---|
| | | | | | | CD44+ N48 | CD44+ N58 | CD44+ N43 | CD44+ N37 | CD44+ N39 | CD44+ N40 | | | CD44+ N74 | CD44+ N66 | GeneBody NP Met | GeneBody Met | Pro-motor Met | Pro-moter Met |
| TSPAN13 | high in NP | -12.5 | 0.015545176 | -1.8 | 13952 | 18 | 99 | 130 | 7 | 10 | 7 | N | N | N | N | N | N |
| COL5A1 | high in NP | -4.5 | 0.015516536 | -1.8 | 13953 | 3609 | 539 | 493 | 143 | 130 | 235 | N | N | P | N | N | N |
| BTG2 | high in NP | -4.6 | 0.015455847 | -1.8 | 13954 | 2157 | 911 | 450 | 205 | 138 | 230 | N | N | N | N | N | N |
| LEPR | high in NP | -3.1 | 0.015429935 | -1.8 | 13955 | 452 | 693 | 518 | 160 | 141 | 204 | N | N | N | N | N | N |
| HSD17B14 | high in NP | -2.9 | 0.015423116 | -1.8 | 13956 | 66 | 36 | 43 | 15 | 14 | 13 | N | N | N | N | N | N |
| FGFBP2 | high in NP | -4.9 | 0.015409478 | -1.8 | 13957 | 20 | 57 | 11 | 4 | 4 | 7 | N | N | N | P | N | N |
| TNFSF9 | high in NP | -4.3 | 0.015402659 | -1.8 | 13958 | 231 | 153 | 104 | 29 | 11 | 46 | N | N | N | N | N | N |
| SH3GL1 | high in NP | -3.2 | 0.01539584 | -1.8 | 13959 | 341 | 450 | 545 | 179 | 134 | 70 | N | P | N | N | N | N |
| TSC22D1 | high in NP | -3.5 | 0.015367883 | -1.8 | 13960 | 823 | 1620 | 1324 | 263 | 286 | 486 | N | P | N | N | N | N |
| IFI6 | high in NP | -3.5 | 0.015346744 | -1.8 | 13961 | 2617 | 1107 | 1497 | 505 | 303 | 431 | P | N | N | N | N | N |
| IL13RA1 | high in NP | -3.1 | 0.015314013 | -1.8 | 13962 | 196 | 207 | 155 | 43 | 73 | 46 | N | N | N | N | N | N |
| EGFL6 | high in NP | -8.8 | 0.015307194 | -1.8 | 13963 | 175 | 14 | 8 | 4 | 4 | 7 | N | P | N | N | N | N |
| MFAP5 | high in NP | -5.8 | 0.015293556 | -1.8 | 13964 | 345 | 383 | 93 | 15 | 27 | 54 | N | P | N | N | N | N |
| RNF2 | high in NP | -3.7 | 0.015279918 | -1.8 | 13965 | 128 | 208 | 93 | 20 | 31 | 33 | N | N | N | N | N | N |
| BBS1 | high in NP | -3.2 | 0.015253324 | -1.8 | 13966 | 34 | 34 | 55 | 13 | 16 | 13 | N | N | N | N | N | N |
| DUSP10 | high in NP | -6.8 | 0.015239686 | -1.8 | 13967 | 19 | 57 | 52 | 10 | 8 | 8 | N | N | N | N | N | N |
| ZHX1 | high in NP | -3.2 | 0.015148994 | -1.8 | 13968 | 92 | 86 | 65 | 27 | 14 | 25 | N | P | N | N | P | N |
| TMED3 | high in NP | -4.1 | 0.01510058 | -1.8 | 13969 | 194 | 198 | 116 | 52 | 19 | 32 | N | N | N | N | N | N |
| CBR1 | high in NP | -3.2 | 0.015093761 | -1.8 | 13970 | 130 | 129 | 143 | 49 | 30 | 30 | N | N | N | N | N | N |
| SEC62 | high in NP | -3.4 | 0.015086942 | -1.8 | 13971 | 279 | 667 | 395 | 179 | 139 | 102 | N | N | N | N | N | N |
| NFIL3 | high in NP | -4.3 | 0.015012615 | -1.8 | 13972 | 215 | 659 | 628 | 64 | 43 | 127 | N | N | P | N | N | N |
| MPST | high in NP | -3.4 | 0.014971701 | -1.8 | 13973 | 79 | 118 | 132 | 35 | 19 | 23 | N | N | N | N | N | N |
| SETD7 | high in NP | -3.6 | 0.014956018 | -1.8 | 13974 | 33 | 110 | 92 | 23 | 20 | 20 | N | N | N | N | P | N |
| ZDHHC4 | high in NP | -4.5 | 0.014949199 | -1.8 | 13975 | 99 | 65 | 44 | 20 | 10 | 13 | N | N | N | N | N | N |
| MUSTN1 | high in NP | -3.3 | 0.014933515 | -1.8 | 13976 | 23 | 36 | 25 | 4 | 4 | 7 | N | N | N | N | N | N |
| AMIGO1 | high in NP | -3.8 | 0.014926696 | -1.8 | 13977 | 15 | 5 | 10 | 4 | 4 | 4 | N | P | N | N | N | N |
| CBX1 | high in NP | -3.5 | 0.014911695 | -1.8 | 13978 | 90 | 152 | 278 | 23 | 35 | 31 | N | N | N | N | N | N |
| PROS1 | high in NP | -3.0 | 0.01489942 | -1.8 | 13979 | 55 | 126 | 43 | 18 | 17 | 17 | N | N | N | N | N | N |
| DAB2IP | high in NP | -3.8 | 0.014885782 | -1.8 | 13980 | 66 | 105 | 99 | 17 | 35 | 24 | N | N | P | N | N | N |
| PRDX2 | high in NP | -3.4 | 0.014868735 | -1.8 | 13981 | 157 | 226 | 140 | 55 | 34 | 18 | N | N | N | N | N | N |
| CIR1 | high in NP | -2.6 | 0.014861916 | -1.8 | 13982 | 36 | 41 | 54 | 14 | 12 | 13 | N | N | N | N | N | N |
| A2M | high in NP | -5.3 | 0.014836004 | -1.8 | 13983 | 576 | 817 | 246 | 85 | 109 | 106 | NA | NA | N | N | N | N |
| ZEAND1 | high in NP | -3.2 | 0.014771906 | -1.8 | 13984 | 57 | 88 | 49 | 21 | 17 | 14 | N | N | N | N | N | N |
| RFK | high in NP | -3.1 | 0.014758268 | -1.8 | 13985 | 19 | 27 | 22 | 8 | 8 | 8 | N | N | N | N | N | N |
| GADD45B | high in NP | -8.2 | 0.014751449 | -1.8 | 13986 | 11200 | 3350 | 3907 | 380 | 1063 | 1319 | NA | N | N | N | N | N |
| SH3BGRL3 | high in NP | -4.2 | 0.01474463 | -1.8 | 13987 | 587 | 875 | 1248 | 243 | 287 | 89 | N | N | N | N | N | N |
| EIF3G | high in NP | -4.0 | 0.014660757 | -1.8 | 13988 | 182 | 492 | 345 | 89 | 75 | 53 | N | N | N | N | N | N |
| CFDP1 | high in NP | -8.9 | 0.014620525 | -1.8 | 13989 | 26 | 74 | 123 | 10 | 7 | 4 | N | N | N | N | N | N |
| C7orf60 | high in NP | -6.0 | 0.014590522 | -1.8 | 13990 | 30 | 102 | 104 | 11 | 14 | 15 | N | N | N | N | N | N |
| CHMP2A | high in NP | -8.0 | 0.0145612 | -1.8 | 13991 | 81 | 359 | 436 | 39 | 19 | 37 | N | N | N | N | N | N |
| RPN2 | high in NP | -5.6 | 0.014527787 | -1.8 | 13992 | 131 | 493 | 400 | 78 | 41 | 27 | N | N | N | N | N | N |
| PITPNA | high in NP | -3.8 | 0.014520968 | -1.8 | 13993 | 98 | 160 | 195 | 48 | 34 | 32 | N | N | N | N | N | N |
| PDZRN3 | high in NP | -4.3 | 0.014443914 | -1.8 | 13994 | 71 | 228 | 83 | 20 | 19 | 30 | N | N | N | N | N | N |
| ADD3 | high in NP | -3.7 | 0.014423457 | -1.8 | 13995 | 88 | 117 | 63 | 20 | 21 | 30 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | Nulliparous (NP) | | | Parous (P) | | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| C1S | high in NP | -5.2 | 0.014370269 | -1.8 | 13996 | 331 | 1210 | 781 | 116 | 105 | 214 | N | N | N | N | N | N |
| C20orf11 | high in NP | -4.4 | 0.01436345 | -1.8 | 13997 | 186 | 405 | 405 | 99 | 72 | 71 | N | N | N | N | N | N |
| ECH1 | high in NP | -4.3 | 0.014328674 | -1.8 | 13998 | 132 | 87 | 68 | 17 | 29 | 17 | N | N | N | N | N | N |
| KLF4 | high in NP | -5.3 | 0.014321855 | -1.8 | 13999 | 346 | 1183 | 436 | 83 | 83 | 200 | N | N | N | N | N | N |
| DPH5 | high in NP | -3.9 | 0.014308899 | -1.8 | 14000 | 86 | 40 | 86 | 9 | 18 | 13 | N | N | N | N | N | N |
| SPRED2 | high in NP | -2.8 | 0.01430208 | -1.8 | 14001 | 73 | 134 | 100 | 32 | 25 | 31 | N | N | N | N | N | N |
| COBRA1 | high in NP | -3.2 | 0.014248892 | -1.8 | 14002 | 152 | 101 | 133 | 40 | 31 | 23 | N | N | N | N | N | N |
| MRPS34 | high in NP | -3.2 | 0.014235254 | -1.8 | 14003 | 140 | 145 | 107 | 42 | 35 | 23 | N | N | N | N | N | N |
| RPS5 | high in NP | -4.8 | 0.014216161 | -1.8 | 14004 | 3846 | 10762 | 6994 | 1457 | 1975 | 1442 | N | N | N | N | N | N |
| RNF146 | high in NP | -3.1 | 0.014171156 | -1.8 | 14005 | 113 | 158 | 174 | 40 | 28 | 44 | N | N | N | N | N | N |
| NFKBIL1 | high in NP | -4.1 | 0.014157518 | -1.8 | 14006 | 50 | 59 | 78 | 19 | 16 | 9 | N | N | N | N | N | N |
| IFT52 | high in NP | -5.3 | 0.014096829 | -1.9 | 14007 | 43 | 28 | 31 | 13 | 6 | 6 | N | N | N | N | N | N |
| KLHL21 | high in NP | -6.2 | 0.01409001 | -1.9 | 14008 | 889 | 2638 | 1696 | 121 | 265 | 562 | N | N | N | N | N | N |
| SAMD4B | high in NP | -2.8 | 0.014077054 | -1.9 | 14009 | 158 | 208 | 160 | 75 | 56 | 50 | N | N | N | N | N | N |
| DGCR2 | high in NP | -3.6 | 0.014035459 | -1.9 | 14010 | 112 | 186 | 198 | 61 | 40 | 21 | N | N | N | N | N | N |
| PMPCA | high in NP | -6.4 | 0.01402864 | -1.9 | 14011 | 72 | 229 | 235 | 34 | 36 | 21 | N | N | N | N | N | N |
| FAM110B | high in NP | -2.9 | 0.014021821 | -1.9 | 14012 | 49 | 71 | 54 | 23 | 15 | 13 | N | N | N | N | P | N |
| CCL26 | high in NP | -5.3 | 0.014015002 | -1.9 | 14013 | 13 | 19 | 20 | 2 | 2 | 5 | N | N | N | N | N | N |
| C6orf168 | high in NP | -3.6 | 0.014001364 | -1.9 | 14014 | 36 | 46 | 48 | 24 | 24 | 24 | N | N | N | N | N | N |
| RHOJ | high in NP | -3.6 | 0.01393993 | -1.9 | 14015 | 60 | 32 | 49 | 7 | 10 | 13 | N | N | N | N | N | N |
| SERPINF1 | high in NP | -4.9 | 0.013926355 | -1.9 | 14016 | 138 | 1183 | 174 | 31 | 26 | 46 | N | N | N | N | N | N |
| RPL30 | high in NP | -2.8 | 0.013855438 | -1.9 | 14017 | 9523 | 12544 | 9949 | 3084 | 3239 | 3833 | N | N | N | N | N | N |
| PLSCR3 | high in NP | -3.6 | 0.013848619 | -1.9 | 14018 | 185 | 139 | 172 | 50 | 36 | 14 | N | N | N | N | P | N |
| FAM20A | high in NP | -3.0 | 0.0138418 | -1.9 | 14019 | 83 | 113 | 72 | 33 | 24 | 28 | N | N | N | N | N | N |
| CDH1 | high in NP | -7.6 | 0.013815888 | -1.9 | 14020 | 432 | 935 | 1498 | 76 | 331 | 56 | N | N | N | N | N | N |
| FBXL5 | high in NP | -4.1 | 0.013772247 | -1.9 | 14021 | 34 | 118 | 48 | 17 | 17 | 17 | P | N | N | N | N | N |
| HOXC6 | high in NP | -6.4 | 0.013759973 | -1.9 | 14022 | 34 | 42 | 23 | 5 | 2 | 10 | N | N | N | N | N | N |
| PAIP2 | high in NP | -4.3 | 0.013753154 | -1.9 | 14023 | 358 | 804 | 240 | 109 | 70 | 72 | N | N | N | N | N | N |
| SMAD1 | high in NP | -3.3 | 0.013746335 | -1.9 | 14024 | 165 | 142 | 92 | 38 | 35 | 28 | N | N | N | N | N | N |
| SLFN11 | high in NP | -5.7 | 0.013721105 | -1.9 | 14025 | 100 | 141 | 42 | 15 | 10 | 18 | N | N | N | N | N | N |
| LARP4 | high in NP | -3.7 | 0.013710876 | -1.9 | 14026 | 36 | 103 | 64 | 22 | 20 | 20 | N | N | N | N | N | N |
| SLC25A5 | high in NP | -5.0 | 0.013704057 | -1.9 | 14027 | 521 | 1408 | 1509 | 191 | 274 | 236 | N | N | N | N | N | N |
| UBAC1 | high in NP | -30.2 | 0.013663144 | -1.9 | 14028 | 13 | 68 | 47 | 6 | 6 | 6 | N | N | N | N | N | P |
| PGM1 | high in NP | -4.9 | 0.013650869 | -1.9 | 14029 | 63 | 145 | 150 | 28 | 28 | 17 | N | N | N | N | N | N |
| ANXA3 | high in NP | -33.6 | 0.013624275 | -1.9 | 14030 | 17 | 59 | 87 | 11 | 11 | 11 | N | N | N | N | N | N |
| GNG11 | high in NP | -12.2 | 0.013591544 | -1.9 | 14031 | 114 | 136 | 80 | 29 | 8 | 3 | N | N | N | N | P | N |
| PABPC1 | high in NP | -9.3 | 0.013584726 | -1.9 | 14032 | 491 | 2907 | 2340 | 219 | 257 | 279 | N | N | N | N | N | N |
| GIMAP1 | high in NP | -3.8 | 0.013564269 | -1.9 | 14033 | 14 | 3 | 4 | 2 | 2 | 2 | N | N | N | N | N | N |
| USMG5 | high in NP | -12.3 | 0.01355745 | -1.9 | 14034 | 70 | 573 | 437 | 25 | 32 | 12 | N | N | N | N | P | N |
| UBE2E2 | high in NP | -4.3 | 0.013540402 | -1.9 | 14035 | 304 | 204 | 121 | 69 | 23 | 23 | N | N | N | N | N | N |
| EAF2 | high in NP | -4.2 | 0.013533583 | -1.9 | 14036 | 47 | 122 | 91 | 29 | 18 | 15 | N | N | N | N | N | N |
| H2AFX | high in NP | -3.4 | 0.013526764 | -1.9 | 14037 | 178 | 245 | 378 | 53 | 63 | 75 | N | N | N | N | N | N |
| BCL6B | high in NP | -2.8 | 0.01351449 | -1.9 | 14038 | 18 | 15 | 16 | 6 | 6 | 6 | N | N | N | N | N | N |
| CFL1 | high in NP | -3.7 | 0.013466076 | -1.9 | 14039 | 6197 | 7615 | 6422 | 1768 | 2567 | 1265 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | | MSDK-seq | | | |
|---|---|---|---|---|---|---|---|---|---|---|---|---|---|---|---|---|---|---|---|
| | | | | | | Nulliparous (NP) | | | | Parous (P) | | | NP | | P | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
|---|---|---|---|---|---|---|---|---|---|---|---|---|---|---|---|---|---|
| CHST14 | high in NP | -3.5 | 0.013411524 | -1.9 | 14040 | 70 | 56 | 40 | 11 | 12 | 7 | N | N | N | N | N | N |
| ANP32B | high in NP | -3.8 | 0.013369247 | -1.9 | 14041 | 252 | 457 | 469 | 137 | 101 | 98 | N | N | N | N | N | N |
| ZFP36L1 | high in NP | -7.7 | 0.01334879 | -1.9 | 14042 | 10556 | 7441 | 2836 | 1317 | 413 | 1470 | N | N | N | N | N | N |
| PC | high in NP | -4.9 | 0.013336516 | -1.9 | 14043 | 29 | 38 | 42 | 17 | 13 | 13 | N | N | N | N | N | N |
| SOD1 | high in NP | -9.4 | 0.013322878 | -1.9 | 14044 | 115 | 697 | 556 | 54 | 40 | 50 | N | N | N | N | N | N |
| DBC1 | high in NP | -5.7 | 0.0133092 | -1.9 | 14045 | 44 | 46 | 36 | 12 | 19 | 12 | P | N | N | N | N | N |
| COL12A1 | high in NP | -3.7 | 0.013259461 | -1.9 | 14046 | 135 | 343 | 276 | 50 | 46 | 83 | N | N | N | N | N | N |
| REST | high in NP | -6.0 | 0.013236959 | -1.9 | 14047 | 98 | 46 | 75 | 14 | 10 | 25 | N | N | N | N | N | N |
| CBX8 | high in NP | -4.0 | 0.013213774 | -1.9 | 14048 | 21 | 23 | 26 | 7 | 8 | 5 | P | P | N | N | P | N |
| LOC728640 | high in NP | -55.9 | 0.013206955 | -1.9 | 14049 | 7 | 86 | 81 | 1 | 1 | 1 | NA | NA | N | N | N | N |
| EEF1B2 | high in NP | -3.4 | 0.013172861 | -1.9 | 14050 | 83 | 119 | 99 | 31 | 18 | 22 | N | N | N | N | N | N |
| SPIN1 | high in NP | -3.9 | 0.013159223 | -1.9 | 14051 | 207 | 187 | 159 | 77 | 38 | 51 | N | N | N | N | P | N |
| C2CD2 | high in NP | -3.7 | 0.013137402 | -1.9 | 14052 | 124 | 270 | 175 | 65 | 51 | 34 | N | N | N | N | N | N |
| TRMT112 | high in NP | -7.0 | 0.013124446 | -1.9 | 14053 | 147 | 810 | 474 | 81 | 60 | 23 | NA | NA | N | N | P | N |
| TRPT1 | high in NP | -4.8 | 0.013110808 | -1.9 | 14054 | 25 | 49 | 63 | 10 | 7 | 4 | N | N | N | N | N | N |
| CYP51A1 | high in NP | -5.8 | 0.013084896 | -1.9 | 14055 | 128 | 444 | 310 | 74 | 38 | 28 | N | N | N | N | N | N |
| GNS | high in NP | -4.1 | 0.013067849 | -1.9 | 14056 | 644 | 865 | 439 | 217 | 73 | 161 | N | N | N | N | N | N |
| MPDU1 | high in NP | -5.3 | 0.01306103 | -1.9 | 14057 | 21 | 60 | 26 | 3 | 6 | 3 | N | N | N | N | N | N |
| ATP6AP2 | high in NP | -5.7 | 0.013040573 | -1.9 | 14058 | 119 | 142 | 67 | 35 | 9 | 9 | N | N | N | N | N | N |
| UBQLN2 | high in NP | -3.2 | 0.013020116 | -1.9 | 14059 | 284 | 443 | 328 | 119 | 100 | 79 | N | N | N | N | N | N |
| C13orf15 | high in NP | -6.5 | 0.013006478 | -1.9 | 14060 | 36 | 63 | 63 | 9 | 8 | 8 | N | P | N | N | N | N |
| C17orf95 | high in NP | -7.9 | 0.012972383 | -1.9 | 14061 | 19 | 51 | 50 | 9 | 3 | 3 | N | N | N | N | N | N |
| KCNH6 | high in NP | -9.2 | 0.012965564 | -1.9 | 14062 | 116 | 492 | 872 | 52 | 20 | 46 | N | P | N | N | N | N |
| PDE4A | high in NP | -4.8 | 0.012915786 | -1.9 | 14063 | 118 | 113 | 50 | 22 | 13 | 19 | P | P | N | N | N | N |
| THBS4 | high in NP | -8.8 | 0.012908967 | -1.9 | 14064 | 1860 | 407 | 130 | 38 | 40 | 38 | P | P | N | N | N | N |
| ARF4 | high in NP | -2.9 | 0.012883055 | -1.9 | 14065 | 1164 | 2043 | 1164 | 399 | 418 | 445 | N | N | N | N | N | N |
| IER2 | high in NP | -3.1 | 0.012872826 | -1.9 | 14066 | 4844 | 4819 | 5864 | 1356 | 1990 | 1543 | N | N | N | N | N | N |
| RNF166 | high in NP | -8.5 | 0.012853733 | -1.9 | 14067 | 41 | 35 | 25 | 3 | 3 | 12 | N | N | N | N | N | N |
| RPS27L | high in NP | -4.5 | 0.012829185 | -1.9 | 14068 | 332 | 470 | 430 | 164 | 73 | 61 | P | N | N | N | N | N |
| EIF4H | high in NP | -3.5 | 0.012822366 | -1.9 | 14069 | 2014 | 4235 | 3090 | 927 | 963 | 785 | N | N | N | N | N | N |
| TAGLN2 | high in NP | -5.5 | 0.012815547 | -1.9 | 14070 | 666 | 2439 | 1584 | 387 | 279 | 261 | N | N | N | N | N | N |
| MFAP3 | high in NP | -4.6 | 0.012801909 | -1.9 | 14071 | 410 | 218 | 209 | 87 | 55 | 39 | N | N | N | N | N | N |
| SMAD4 | high in NP | -3.4 | 0.012751449 | -1.9 | 14072 | 86 | 134 | 137 | 56 | 33 | 25 | N | N | N | N | N | N |
| DBI | high in NP | -7.7 | 0.012724173 | -1.9 | 14073 | 81 | 298 | 299 | 26 | 23 | 30 | N | N | N | N | N | N |
| GIMAP6 | high in NP | -3.5 | 0.012717354 | -1.9 | 14074 | 34 | 37 | 19 | 12 | 12 | 12 | N | N | N | N | N | N |
| SFRP2 | high in NP | -6.4 | 0.012710535 | -1.9 | 14075 | 613 | 157 | 71 | 19 | 15 | 17 | P | N | N | N | N | N |
| CANX | high in NP | -5.2 | 0.012646437 | -1.9 | 14076 | 1909 | 2894 | 2716 | 1178 | 547 | 421 | N | N | N | N | N | N |
| ARHGEF7 | high in NP | -4.8 | 0.012632799 | -1.9 | 14077 | 151 | 385 | 344 | 73 | 63 | 69 | N | N | N | N | N | N |
| FAM102A | high in NP | -3.2 | 0.01262598 | -1.9 | 14078 | 993 | 699 | 744 | 224 | 242 | 331 | N | N | N | N | N | N |
| NDUFAF1 | high in NP | -8.0 | 0.012599386 | -1.9 | 14079 | 15 | 33 | 20 | 4 | 7 | 4 | N | N | N | N | N | N |
| DCX | high in NP | -6.8 | 0.012585748 | -1.9 | 14080 | 508 | 77 | 123 | 14 | 14 | 28 | N | N | N | N | N | N |
| SLC2A4RG | high in NP | -4.0 | 0.01257211 | -1.9 | 14081 | 183 | 92 | 98 | 18 | 26 | 29 | N | N | N | N | N | N |
| ZNF773 | high in NP | -6.2 | 0.012565292 | -1.9 | 14082 | 12 | 20 | 21 | 3 | 1 | 1 | N | N | N | N | N | N |
| GPX7 | high in NP | -5.4 | 0.012544835 | -1.9 | 14083 | 57 | 61 | 33 | 17 | 8 | 8 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | | Nulliparous (NP) | | | | Parous (P) | | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 NP | CD44+ N66 P | GeneBody NP Met NP | GeneBody Met P | Pro-motor Met NP | Pro-moter Met P |
| MFN2 | high in NP | -7.7 | 0.001250528 | -1.9 | 14084 | 49 | 193 | 160 | 29 | 28 | 25 | N | N | N | N | N | N |
| SLC2A1 | high in NP | -4.4 | 0.001248414 | -1.9 | 14085 | 1314 | 1254 | 2322 | 450 | 491 | 247 | N | N | N | N | N | N |
| CHN1 | high in NP | -5.9 | 0.001241800 | -1.9 | 14086 | 30 | 79 | 57 | 14 | 4 | 4 | N | N | N | N | N | N |
| ITPA | high in NP | -14.7 | 0.001241118 | -1.9 | 14087 | 21 | 174 | 116 | 8 | 4 | 4 | N | N | N | N | N | N |
| ELOVL5 | high in NP | -3.6 | 0.00123920 | -1.9 | 14088 | 757 | 1647 | 1317 | 231 | 217 | 408 | N | N | N | N | N | N |
| GMPR | high in NP | -4.6 | 0.001235254 | -1.9 | 14089 | 19 | 30 | 22 | 6 | 6 | 3 | N | N | N | N | N | N |
| NIPSNAP1 | high in NP | -6.4 | 0.001232321 | -1.9 | 14090 | 91 | 40 | 36 | 10 | 9 | 4 | N | N | N | N | N | N |
| WDR25 | high in NP | -4.2 | 0.001228844 | -1.9 | 14091 | 40 | 23 | 27 | 8 | 7 | 4 | N | N | N | N | N | N |
| CD46 | high in NP | -6.8 | 0.001228162 | -1.9 | 14092 | 117 | 372 | 403 | 53 | 45 | 45 | N | N | N | N | N | N |
| ARID5B | high in NP | -6.8 | 0.001223320 | -1.9 | 14093 | 308 | 1593 | 1647 | 138 | 97 | 266 | N | N | N | N | N | N |
| LOC139201 | high in NP | -8.7 | 0.001222638 | -1.9 | 14094 | 12 | 22 | 31 | 1 | 4 | 1 | N | N | N | N | N | N |
| SFRP4 | high in NP | -5.3 | 0.00122195 | -1.9 | 14095 | 7279 | 2348 | 1578 | 674 | 404 | 394 | N | N | N | N | N | N |
| C19orf43 | high in NP | -3.2 | 0.001221275 | -1.9 | 14096 | 1346 | 1279 | 1530 | 320 | 413 | 483 | N | N | N | N | N | N |
| STT3A | high in NP | -6.3 | 0.001219911 | -1.9 | 14097 | 192 | 272 | 271 | 92 | 37 | 27 | N | N | N | N | P | N |
| DNAJC14 | high in NP | -5.0 | 0.001217865 | -1.9 | 14098 | 33 | 108 | 71 | 10 | 10 | 13 | N | N | N | N | N | N |
| IGFBP2 | high in NP | -5.4 | 0.001217183 | -1.9 | 14099 | 546 | 434 | 234 | 112 | 74 | 40 | N | N | N | N | N | N |
| APP | high in NP | -3.1 | 0.001217796 | -1.9 | 14100 | 2685 | 2995 | 3185 | 829 | 1181 | 899 | N | N | N | N | N | N |
| RSU1 | high in NP | -3.9 | 0.001211114 | -1.9 | 14101 | 221 | 161 | 119 | 39 | 48 | 24 | N | N | N | N | N | N |
| C11orf60 | high in NP | -3.2 | 0.00121043 | -1.9 | 14102 | NA | NA | NA | NA | NA | NA | NA | NA | N | N | N | N |
| RPL32 | high in NP | -5.1 | 0.001198636 | -1.9 | 14103 | 6867 | 16324 | 16728 | 1996 | 2473 | 3092 | N | N | N | N | N | N |
| RARB | high in NP | -3.6 | 0.001197954 | -1.9 | 14104 | 37 | 96 | 49 | 14 | 12 | 9 | N | N | N | N | P | N |
| PCDHB5 | high in NP | -3.3 | 0.001196590 | -1.9 | 14105 | 14 | 15 | 11 | 2 | 2 | 2 | N | N | N | N | N | N |
| DKK3 | high in NP | -5.7 | 0.001195908 | -1.9 | 14106 | 59 | 533 | 106 | 17 | 22 | 17 | N | N | N | N | N | N |
| CPNE3 | high in NP | -3.8 | 0.001195226 | -1.9 | 14107 | 95 | 107 | 62 | 17 | 29 | 15 | N | N | N | N | N | N |
| PIK3R2 | high in NP | -3.7 | 0.00119318 | -1.9 | 14108 | 69 | 52 | 63 | 13 | 18 | 18 | N | N | N | N | N | N |
| GOLGA4 | high in NP | -3.2 | 0.001191817 | -1.9 | 14109 | 49 | 93 | 77 | 27 | 18 | 30 | N | N | N | N | N | N |
| COPB2 | high in NP | -5.3 | 0.001185680 | -1.9 | 14110 | 85 | 188 | 265 | 45 | 27 | 21 | N | N | N | N | N | N |
| AKR1C3 | high in NP | -5.5 | 0.001182407 | -1.9 | 14111 | 479 | 644 | 1148 | 218 | 95 | 40 | N | N | N | N | N | N |
| FAM10A4 | high in NP | -38.1 | 0.001180361 | -1.9 | 14112 | 27 | 528 | 503 | 9 | 4 | 6 | N | N | N | N | N | N |
| TRIM52 | high in NP | -7.9 | 0.001179679 | -1.9 | 14113 | 280 | 939 | 1080 | 106 | 108 | 102 | N | N | N | N | N | N |
| C5orf32 | high in NP | -3.6 | 0.001178315 | -1.9 | 14114 | 405 | 659 | 662 | 183 | 157 | 143 | N | N | N | N | N | N |
| RRAS2 | high in NP | -3.8 | 0.00117627 | -1.9 | 14115 | 59 | 373 | 220 | 23 | 24 | 21 | N | N | N | N | N | N |
| PGCP | high in NP | -8.7 | 0.001174224 | -1.9 | 14116 | 68 | 135 | 27 | 6 | 6 | 13 | N | N | N | N | N | N |
| RAB40B | high in NP | -5.9 | 0.001173542 | -1.9 | 14117 | 64 | 82 | 88 | 8 | 23 | 14 | N | N | N | N | N | N |
| MAPK1IP1L | high in NP | -2.8 | 0.001172292 | -1.9 | 14118 | 280 | 374 | 390 | 131 | 154 | 118 | N | N | N | N | N | N |
| CTNND1 | high in NP | -5.4 | 0.001170610 | -1.9 | 14119 | 208 | 495 | 581 | 68 | 111 | 82 | N | N | N | N | N | N |
| DDAH1 | high in NP | -4.7 | 0.001168905 | -1.9 | 14120 | 309 | 186 | 103 | 35 | 31 | 22 | N | N | N | N | N | N |
| HNRNPAB | high in NP | -8.9 | 0.001168223 | -1.9 | 14121 | 348 | 2505 | 1517 | 123 | 157 | 146 | N | N | N | N | N | N |
| SH2B3 | high in NP | -5.0 | 0.001167541 | -1.9 | 14122 | 865 | 566 | 336 | 194 | 81 | 81 | N | N | N | N | N | N |
| ZNF669 | high in NP | -3.8 | 0.001166859 | -1.9 | 14123 | 71 | 100 | 62 | 9 | 16 | 15 | N | N | N | N | N | N |
| TMED2 | high in NP | -4.9 | 0.001162973 | -1.9 | 14124 | 773 | 2213 | 1733 | 449 | 325 | 194 | N | N | N | N | N | N |
| INSR | high in NP | -4.1 | 0.001161609 | -1.9 | 14125 | 63 | 193 | 166 | 46 | 34 | 32 | N | N | N | N | N | N |
| CHRNE | high in NP | -5.8 | 0.001158199 | -1.9 | 14126 | 73 | 34 | 29 | 11 | 6 | 6 | N | N | N | N | N | P |
| SNRPD2 | high in NP | -7.5 | 0.001154858 | -1.9 | 14127 | 236 | 932 | 819 | 115 | 74 | 60 | N | N | N | N | N | N |

TABLE 15-continued

Genes that Are Differentially Methylated between Nulliparous and Parous CD44+ Breast Epithelial Cells

| | | | | | | SAGE-seq | | | | | | | ChIP-seq | | | MSDK-seq | | |
|---|---|---|---|---|---|---|---|---|---|---|---|---|---|---|---|---|---|---|
| | | | | | | Nulliparous (NP) | | | Parous (P) | | | | NP | P | GeneBody NP Met | GeneBody Met | Pro-moter Met | Pro-moter Met |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | | | | NP | P |
| HP1BP3 | high in NP | −3.2 | 0.011483805 | −1.9 | 14128 | 622 | 637 | 678 | 215 | 199 | 282 | N | N | N | N | N | N | N |
| NAALADL2 | high in NP | −2.8 | 0.011476986 | −1.9 | 14129 | 21 | 22 | 21 | 10 | 10 | 10 | N | N | N | N | N | N | N |
| CS | high in NP | −2.9 | 0.011463348 | −1.9 | 14130 | 992 | 1179 | 900 | 450 | 405 | 353 | N | N | N | N | N | P | N |
| TBCB | high in NP | −5.6 | 0.01144971 | −1.9 | 14131 | 37 | 163 | 78 | 13 | 11 | 6 | N | N | N | N | N | N | N |
| MED28 | high in NP | −12.2 | 0.011418343 | −1.9 | 14132 | 27 | 165 | 148 | 6 | 8 | 13 | N | N | N | N | N | N | N |
| NR2F2 | high in NP | −8.9 | 0.011411524 | −1.9 | 14133 | 1866 | 898 | 554 | 353 | 32 | 94 | N | N | N | N | N | N | N |
| CDCA4 | high in NP | −4.7 | 0.011404705 | −1.9 | 14134 | 72 | 40 | 48 | 18 | 9 | 13 | N | N | N | N | N | N | N |
| TMEM173 | high in NP | −7.9 | 0.011397886 | −1.9 | 14135 | 41 | 57 | 9 | 4 | 4 | 4 | N | N | N | N | N | N | N |
| RBM24 | high in NP | −3.6 | 0.011362428 | −1.9 | 14136 | 28 | 34 | 26 | 8 | 8 | 6 | N | P | N | N | N | P | N |
| B3GALNT1 | high in NP | −3.7 | 0.011341971 | −1.9 | 14137 | 18 | 22 | 22 | 6 | 6 | 6 | N | N | N | N | N | N | P |
| YBX1 | high in NP | −40.2 | 0.011321514 | −1.9 | 14138 | 69 | 1383 | 1243 | 29 | 26 | 21 | N | N | N | N | N | N | N |
| DDIT4 | high in NP | −4.9 | 0.011189908 | −2.0 | 14139 | 224 | 52 | 44 | 6 | 9 | 10 | N | N | N | N | N | P | N |
| DNAJB9 | high in NP | −9.2 | 0.011115581 | −2.0 | 14140 | 95 | 633 | 394 | 40 | 19 | 37 | N | N | N | N | N | P | N |
| GLUL | high in NP | −5.6 | 0.011101943 | −2.0 | 14141 | 401 | 1383 | 868 | 181 | 139 | 216 | N | N | N | N | N | P | N |
| FLJ36031 | high in NP | −4.4 | 0.011095124 | −2.0 | 14142 | 94 | 403 | 72 | 15 | 19 | 17 | N | N | N | N | N | N | N |
| PPFIBP1 | high in NP | −4.4 | 0.01107194 | −2.0 | 14143 | 137 | 360 | 161 | 38 | 59 | 39 | N | N | N | N | N | N | N |
| UGDH | high in NP | −18.4 | 0.011051483 | −2.0 | 14144 | 193 | 3085 | 1322 | 79 | 69 | 76 | N | N | N | N | N | N | N |
| NCL | high in NP | −4.3 | 0.011024207 | −2.0 | 14145 | 651 | 1635 | 676 | 169 | 236 | 236 | N | N | N | N | N | N | N |
| PFKFB3 | high in NP | −4.0 | 0.011010569 | −2.0 | 14146 | 1852 | 2138 | 1264 | 344 | 411 | 611 | N | N | N | N | N | N | N |
| ABHD14B | high in NP | −6.2 | 0.010996931 | −2.0 | 14147 | 432 | 164 | 158 | 43 | 24 | 48 | N | N | N | N | N | N | N |
| AK3 | high in NP | −4.1 | 0.010950563 | −2.0 | 14148 | 208 | 153 | 115 | 51 | 25 | 34 | N | N | N | N | N | N | N |
| PCOLCE | high in NP | −6.0 | 0.010931469 | −2.0 | 14149 | 189 | 523 | 203 | 27 | 28 | 73 | N | P | N | N | N | N | N |
| DDB1 | high in NP | −4.8 | 0.010911013 | −2.0 | 14150 | 449 | 924 | 974 | 222 | 174 | 92 | N | N | N | N | N | N | N |
| SF3B14 | high in NP | −8.0 | 0.010895329 | −2.0 | 14151 | 108 | 361 | 408 | 25 | 39 | 36 | N | N | N | N | N | N | N |
| CMBL | high in NP | −3.4 | 0.010872826 | −2.0 | 14152 | 19 | 14 | 23 | 8 | 8 | 8 | N | N | N | N | N | N | N |
| FXYD1 | high in NP | −6.9 | 0.010866008 | −2.0 | 14153 | 45 | 144 | 31 | 6 | 4 | 10 | N | N | N | N | N | N | N |
| PSME1 | high in NP | −4.0 | 0.010859189 | −2.0 | 14154 | 918 | 778 | 638 | 304 | 144 | 145 | N | N | N | N | N | N | N |
| RPL31 | high in NP | −7.4 | 0.010845551 | −2.0 | 14155 | 1549 | 5906 | 6703 | 410 | 701 | 670 | N | P | N | N | N | N | N |
| EIF3D | high in NP | −3.5 | 0.010831913 | −2.0 | 14156 | 669 | 859 | 1159 | 281 | 277 | 190 | N | N | N | N | N | N | N |
| FGF13 | high in NP | −4.2 | 0.010803273 | −2.0 | 14157 | 28 | 9 | 14 | 6 | 6 | 6 | N | N | N | N | N | N | N |
| ARL1 | high in NP | −5.5 | 0.010772588 | −2.0 | 14158 | 152 | 149 | 109 | 46 | 23 | 12 | N | N | N | N | N | N | N |
| DFNA5 | high in NP | −5.6 | 0.010720082 | −2.0 | 14159 | 75 | 6 | 7 | 3 | 3 | 3 | N | N | N | N | N | N | N |
| REEP5 | high in NP | −8.4 | 0.010706444 | −2.0 | 14160 | 198 | 997 | 760 | 61 | 82 | 89 | N | N | N | N | N | N | N |
| NCBP2 | high in NP | −7.0 | 0.010660757 | −2.0 | 14161 | 73 | 369 | 203 | 26 | 26 | 16 | N | N | N | N | N | N | N |
| AGRN | high in NP | −4.7 | 0.010631435 | −2.0 | 14162 | 117 | 167 | 238 | 26 | 55 | 29 | N | N | N | N | N | N | N |
| FBN1 | high in NP | −4.3 | 0.010624616 | −2.0 | 14163 | 487 | 358 | 366 | 78 | 71 | 133 | N | N | N | N | N | N | N |
| PUM2 | high in NP | −3.9 | 0.010617797 | −2.0 | 14164 | 193 | 308 | 357 | 56 | 67 | 97 | N | N | N | N | N | N | N |
| TMC7 | high in NP | −3.6 | 0.010576202 | −2.0 | 14165 | 97 | 222 | 153 | 37 | 27 | 30 | N | N | N | N | N | N | N |
| HK2 | high in NP | −6.5 | 0.010555745 | −2.0 | 14166 | 292 | 847 | 1054 | 107 | 179 | 114 | N | P | N | N | N | P | N |
| SET | high in NP | −3.5 | 0.010516195 | −2.0 | 14167 | 1054 | 1595 | 1521 | 407 | 490 | 471 | N | N | N | N | N | N | N |
| TBC1D2B | high in NP | −3.2 | 0.010503921 | −2.0 | 14168 | 259 | 228 | 238 | 71 | 50 | 83 | N | N | N | N | N | N | N |
| SGK1 | high in NP | −10.1 | 0.01042073 | −2.0 | 14169 | 190 | 1156 | 895 | 58 | 84 | 79 | N | N | N | N | N | N | N |
| CSNK1A1 | high in NP | −3.5 | 0.010389362 | −2.0 | 14170 | 663 | 637 | 656 | 226 | 314 | 205 | N | N | N | N | N | N | N |
| PAM | high in NP | −4.6 | 0.01042073 | −2.0 | 14171 | 116 | 313 | 267 | 58 | 32 | 33 | N | N | N | N | N | N | N |

TABLE 15-continued

Genes that Are Differentially Methylated between Nulliparous and Parous CD44+ Breast Epithelial Cells

| | | | | | SAGE-seq | | | | | | | | ChIP-seq | | | MSDK-seq | | |
|---|---|---|---|---|---|---|---|---|---|---|---|---|---|---|---|---|---|---|
| | | | | | | Nulliparous (NP) | | | Parous (P) | | | | NP | P | GeneBody NP Met | GeneBody Met | Pro-moter Met | Pro-moter Met |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | | CD44+ N74 | CD44+ N66 | | | NP | P |
| HSD17B11 | high in NP | -6.6 | 0.010333447 | -2.0 | 14172 | 426 | 398 | 137 | 60 | 27 | 52 | | N | N | N | N | N | N |
| ETS2 | high in NP | -5.1 | 0.010326628 | -2.0 | 14173 | 420 | 1548 | 468 | 185 | 83 | 100 | | N | N | N | N | N | N |
| RBBP7 | high in NP | -5.5 | 0.010311299 | -2.0 | 14174 | 98 | 189 | 281 | 30 | 30 | 34 | | N | N | N | N | N | N |
| DOPEY2 | high in NP | -4.4 | 0.010287078 | -2.0 | 14175 | 218 | 413 | 496 | 85 | 45 | 86 | | N | N | N | N | N | N |
| C15orf44 | high in NP | -6.1 | 0.010267985 | -2.0 | 14176 | 46 | 134 | 140 | 21 | 17 | 9 | | N | N | N | N | N | N |
| RRBP1 | high in NP | -3.4 | 0.010248892 | -2.0 | 14177 | 144 | 166 | 213 | 42 | 36 | 53 | | N | N | N | N | N | N |
| NADSYN1 | high in NP | -5.6 | 0.010242073 | -2.0 | 14178 | 23 | 40 | 36 | 12 | 12 | 12 | | N | N | N | N | N | N |
| PPP2R2A | high in NP | -12.5 | 0.010228435 | -2.0 | 14179 | 59 | 456 | 325 | 19 | 24 | 24 | | N | N | N | N | N | N |
| PPP1R14A | high in NP | -9.2 | 0.010150699 | -2.0 | 14180 | 123 | 31 | 12 | 6 | 6 | 6 | | N | N | N | N | N | N |
| DDOST | high in NP | -12.0 | 0.010138425 | -2.0 | 14181 | 45 | 332 | 222 | 23 | 10 | 7 | | N | N | N | N | N | N |
| UBE2NL | high in NP | -39.2 | 0.010088646 | -2.0 | 14182 | 72 | 1269 | 56 | 1 | 8 | 9 | | N | N | N | N | N | N |
| PVRL4 | high in NP | -6.2 | 0.010081827 | -2.0 | 14183 | 59 | 74 | 133 | 12 | 25 | 12 | | N | N | N | N | N | N |
| RPL26 | high in NP | -28.0 | 0.01006819 | -2.0 | 14184 | 378 | 6791 | 4171 | 123 | 133 | 155 | | N | N | N | N | N | N |
| HBB | high in NP | -142.1 | 0.010018411 | -2.0 | 14185 | 378 | 193410 | 14939 | 181 | 82 | 70 | | N | N | N | N | N | N |
| LARGE | high in NP | -3.6 | 0.010006137 | -2.0 | 14186 | 61 | 118 | 67 | 20 | 17 | 17 | | N | N | N | N | N | N |
| HSD3B7 | high in NP | -5.0 | 0.009999318 | -2.0 | 14187 | 183 | 391 | 108 | 39 | 35 | 28 | | N | N | N | N | N | N |
| ADCY3 | high in NP | -4.3 | 0.009972042 | -2.0 | 14188 | 156 | 535 | 213 | 61 | 46 | 39 | | N | N | N | N | N | N |
| TRMT5 | high in NP | -39.7 | 0.009927037 | -2.0 | 14189 | 36 | 960 | 947 | 10 | 10 | 21 | | N | N | N | N | N | N |
| TJP2 | high in NP | -5.9 | 0.009920218 | -2.0 | 14190 | 61 | 144 | 161 | 27 | 21 | 22 | | N | N | N | N | N | N |
| ADAMTS4 | high in NP | -6.8 | 0.009913399 | -2.0 | 14191 | 4978 | 23897 | 2598 | 795 | 542 | 762 | | N | N | N | N | N | N |
| B4GALT5 | high in NP | -4.7 | 0.009874531 | -2.0 | 14192 | 367 | 1034 | 587 | 130 | 134 | 172 | | N | N | N | N | N | N |
| CXCL14 | high in NP | -10.2 | 0.009800886 | -2.0 | 14193 | 461 | 1855 | 187 | 32 | 77 | 73 | | N | N | N | N | N | N |
| TSC22D2 | high in NP | -5.4 | 0.009759973 | -2.0 | 14194 | 310 | 448 | 196 | 34 | 49 | 88 | | P | N | N | P | N | N |
| ATF1 | high in NP | -3.9 | 0.009732697 | -2.0 | 14195 | 89 | 67 | 101 | 18 | 21 | 9 | | N | N | N | N | N | N |
| MOBKL2A | high in NP | -6.5 | 0.00971224 | -2.0 | 14196 | 156 | 482 | 275 | 59 | 49 | 17 | | N | N | N | N | N | N |
| EGLN3 | high in NP | -4.8 | 0.009626321 | -2.0 | 14197 | 49 | 49 | 87 | 9 | 6 | 14 | | N | N | N | N | N | N |
| MTDH | high in NP | -5.5 | 0.009612683 | -2.0 | 14198 | 114 | 495 | 224 | 54 | 58 | 42 | | N | N | N | N | N | N |
| SLC2A14 | high in NP | -17.4 | 0.009605864 | -2.0 | 14199 | 336 | 74 | 85 | 14 | 2 | 13 | | P | N | N | N | N | N |
| CAMK2N1 | high in NP | -8.5 | 0.009566314 | -2.0 | 14200 | 140 | 428 | 233 | 44 | 17 | 47 | | N | N | N | N | N | N |
| SERPINH1 | high in NP | -4.4 | 0.009559495 | -2.0 | 14201 | 5457 | 6708 | 4077 | 1167 | 715 | 1627 | | N | N | N | N | N | N |
| SERPINF2 | high in NP | -3.0 | 0.009524719 | -2.0 | 14202 | 25 | 18 | 16 | 7 | 7 | 7 | | N | N | N | N | N | N |
| GADD45A | high in NP | -20.5 | 0.009498807 | -2.0 | 14203 | 64 | 727 | 407 | 10 | 20 | 27 | | N | N | N | N | N | N |
| CSRP2 | high in NP | -13.3 | 0.009491988 | -2.0 | 14204 | 16 | 93 | 43 | 5 | 5 | 5 | | N | N | N | N | N | N |
| YES1 | high in NP | -2.9 | 0.009450392 | -2.0 | 14205 | 277 | 247 | 262 | 90 | 110 | 88 | | N | N | N | N | N | N |
| F3 | high in NP | -13.4 | 0.009443573 | -2.0 | 14206 | 63 | 396 | 300 | 22 | 30 | 21 | | N | N | N | N | N | P |
| C4orf3 | high in NP | -3.6 | 0.009401296 | -2.0 | 14207 | 1260 | 1013 | 949 | 389 | 295 | 163 | | N | NA | N | N | N | N |
| ANO7 | high in NP | -4.0 | 0.009394477 | -2.0 | 14208 | 111 | 174 | 199 | 31 | 36 | 28 | | NA | NA | N | N | N | N |
| LRRN4CL | high in NP | -4.0 | 0.009346062 | -2.0 | 14209 | 47 | 75 | 55 | 9 | 14 | 12 | | N | N | N | N | N | N |
| CDYL | high in NP | -4.1 | 0.009332424 | -2.0 | 14210 | 62 | 111 | 78 | 23 | 14 | 12 | | N | N | N | N | N | N |
| CCDC47 | high in NP | -3.8 | 0.009318786 | -2.0 | 14211 | 345 | 737 | 380 | 104 | 138 | 106 | | N | N | N | N | N | N |
| TSPAN6 | high in NP | -4.9 | 0.00930583 | -2.0 | 14212 | 21 | 42 | 46 | 7 | 5 | 5 | | N | N | N | N | N | N |
| TES | high in NP | -7.3 | 0.009293556 | -2.0 | 14213 | 594 | 1410 | 1183 | 155 | 352 | 92 | | N | P | N | N | N | N |
| SALL2 | high in NP | -4.6 | 0.009243778 | -2.0 | 14214 | 62 | 38 | 48 | 11 | 11 | 6 | | N | P | N | N | N | N |
| AR | high in NP | -5.5 | 0.0092673 | -2.0 | 14215 | 94 | 40 | 33 | 11 | 10 | 7 | | N | N | N | N | N | N |

TABLE 15-continued

Genes that Are Differentially Methylated between Nulliparous and Parous CD44+ Breast Epithelial Cells

| | | | | | SAGE-seq | | | | | | | | ChIP-seq | | MSDK-seq | | | |
|---|---|---|---|---|---|---|---|---|---|---|---|---|---|---|---|---|---|---|
| | | | | | | Nulliparous (NP) | | | | Parous (P) | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| TANC1 | high in NP | -4.3 | 0.009213092 | -2.0 | 14216 | 105 | 204 | 154 | 34 | 44 | 35 | N | N | P | N | N | N |
| HIBADH | high in NP | -4.8 | 0.009166723 | -2.0 | 14217 | 130 | 39 | 27 | 9 | 9 | 6 | N | N | N | N | N | N |
| RAB7A | high in NP | -6.3 | 0.009159905 | -2.0 | 14218 | 1174 | 3607 | 2499 | 429 | 529 | 380 | P | N | N | N | N | N |
| ABLIM1 | high in NP | -4.6 | 0.009121718 | -2.0 | 14219 | 208 | 341 | 177 | 61 | 74 | 42 | N | N | N | N | N | N |
| NR3C1 | high in NP | -3.5 | 0.009108080 | -2.0 | 14220 | 165 | 201 | 156 | 52 | 31 | 56 | N | N | N | N | N | N |
| CHGA | high in NP | -3.8 | 0.009066485 | -2.0 | 14221 | 14 | 14 | 5 | 2 | 2 | 2 | N | N | N | N | N | N |
| PHF23 | high in NP | -6.6 | 0.009046028 | -2.0 | 14222 | 57 | 160 | 160 | 18 | 17 | 21 | N | N | N | N | N | N |
| TMEM64 | high in NP | -6.4 | 0.009039209 | -2.0 | 14223 | 288 | 780 | 392 | 65 | 63 | 136 | N | N | N | N | N | N |
| MAP2K4 | high in NP | -12.4 | 0.009023525 | -2.0 | 14224 | 26 | 110 | 131 | 7 | 8 | 8 | N | N | N | N | N | N |
| EPAS1 | high in NP | -8.3 | 0.009016706 | -2.0 | 14225 | 2124 | 3770 | 796 | 495 | 265 | 200 | N | N | N | N | N | N |
| BRD7P3 | high in NP | -12.4 | 0.009009887 | -2.0 | 14226 | 25 | 148 | 62 | 4 | 11 | 4 | N | N | N | N | N | N |
| C4orf34 | high in NP | -3.1 | 0.008982612 | -2.0 | 14227 | 21 | 16 | 11 | 4 | 4 | 4 | N | N | N | N | N | N |
| RPL15 | high in NP | -6.1 | 0.008923287 | -2.0 | 14228 | 1898 | 6251 | 4413 | 804 | 704 | 777 | N | N | N | N | N | N |
| DPYSL2 | high in NP | -4.3 | 0.008896011 | -2.0 | 14229 | 693 | 656 | 470 | 191 | 59 | 163 | N | N | N | N | N | N |
| SLC35B2 | high in NP | -6.4 | 0.008885987 | -2.0 | 14230 | 98 | 183 | 232 | 21 | 8 | 33 | N | N | N | N | N | N |
| FKBP1A | high in NP | -7.6 | 0.008825776 | -2.1 | 14231 | 647 | 2942 | 2492 | 382 | 168 | 173 | N | N | N | N | N | N |
| C9orf16 | high in NP | -6.6 | 0.008785544 | -2.1 | 14232 | 97 | 148 | 133 | 15 | 31 | 10 | N | N | N | N | N | N |
| RPS29 | high in NP | -57.7 | 0.008744463 | -2.1 | 14233 | 192 | 7469 | 5361 | 32 | 44 | 96 | N | N | N | N | N | N |
| NME7 | high in NP | -5.7 | 0.008730992 | -2.1 | 14234 | 56 | 60 | 58 | 15 | 9 | 7 | N | N | N | N | N | N |
| RPS8 | high in NP | -14.4 | 0.008683259 | -2.1 | 14235 | 591 | 3818 | 4459 | 143 | 232 | 256 | N | N | N | N | N | N |
| ATP1B1 | high in NP | -18.7 | 0.008668258 | -2.1 | 14236 | 56 | 387 | 474 | 17 | 25 | 20 | N | N | N | N | N | N |
| RAB8B | high in NP | -8.5 | 0.008661439 | -2.1 | 14237 | 107 | 397 | 420 | 46 | 19 | 39 | N | N | N | N | N | N |
| AZIN1 | high in NP | -8.7 | 0.008613706 | -2.1 | 14238 | 171 | 665 | 552 | 65 | 59 | 52 | N | N | N | N | N | N |
| COX5B | high in NP | -6.9 | 0.008598023 | -2.1 | 14239 | 51 | 225 | 67 | 14 | 7 | 7 | N | N | N | N | N | N |
| PSMA6 | high in NP | -5.3 | 0.008509376 | -2.1 | 14240 | 238 | 613 | 634 | 112 | 42 | 38 | N | N | N | N | N | N |
| CYB5B | high in NP | -4.5 | 0.0084821 | -2.1 | 14241 | 126 | 196 | 150 | 39 | 41 | 16 | N | N | N | N | N | N |
| PROP | high in NP | -4.7 | 0.008454824 | -2.1 | 14242 | 113 | 85 | 78 | 22 | 17 | 10 | N | P | N | N | N | N |
| HDAC11 | high in NP | -5.2 | 0.008425503 | -2.1 | 14243 | 74 | 42 | 40 | 14 | 8 | 8 | N | N | N | N | N | N |
| FAM96A | high in NP | -8.4 | 0.008418684 | -2.1 | 14244 | 14 | 27 | 36 | 3 | 3 | 3 | N | N | N | N | N | N |
| CLIC1 | high in NP | -5.1 | 0.008398227 | -2.1 | 14245 | 562 | 1275 | 1142 | 229 | 212 | 205 | NA | NA | N | N | N | N |
| ZFYVE9 | high in NP | -4.2 | 0.008336345 | -2.1 | 14246 | 50 | 39 | 36 | 16 | 13 | 16 | N | N | N | N | N | N |
| RPL13AP5 | high in NP | -3.8 | 0.008349812 | -2.1 | 14247 | 236 | 429 | 315 | 64 | 67 | 65 | N | N | N | N | N | N |
| GNAI3 | high in NP | -11.4 | 0.008322537 | -2.1 | 14248 | 98 | 360 | 368 | 35 | 31 | 27 | N | N | N | N | N | N |
| ARSB | high in NP | -3.9 | 0.008295261 | -2.1 | 14249 | 83 | 146 | 73 | 22 | 20 | 17 | N | N | N | N | N | N |
| PJA2 | high in NP | -3.6 | 0.008288442 | -2.1 | 14250 | 344 | 300 | 300 | 112 | 65 | 73 | N | N | N | N | N | N |
| USP33 | high in NP | -4.6 | 0.008274804 | -2.1 | 14251 | 83 | 198 | 156 | 40 | 22 | 25 | N | N | N | N | N | N |
| RPL10A | high in NP | -3.9 | 0.008252983 | -2.1 | 14252 | 9210 | 8776 | 13610 | 1809 | 2581 | 2461 | N | N | N | N | N | N |
| TRIP10 | high in NP | -3.8 | 0.008218889 | -2.1 | 14253 | 148 | 204 | 169 | 26 | 43 | 35 | N | N | N | N | N | N |
| LPPR2 | high in NP | -3.3 | 0.00821207 | -2.1 | 14254 | 428 | 377 | 491 | 131 | 116 | 119 | N | N | N | N | N | N |
| CPZ | high in NP | -8.9 | 0.008205251 | -2.1 | 14255 | 475 | 184 | 70 | 14 | 16 | 8 | N | N | N | N | N | N |
| NEK7 | high in NP | -3.9 | 0.008198432 | -2.1 | 14256 | 206 | 294 | 307 | 66 | 64 | 72 | N | N | N | N | N | N |
| ZFP91 | high in NP | -3.6 | 0.008171156 | -2.1 | 14257 | 779 | 889 | 849 | 318 | 149 | 276 | P | N | N | N | N | N |
| IL6 | high in NP | -8.9 | 0.008164337 | -2.1 | 14258 | 47342 | 37086 | 11728 | 3886 | 2766 | 3724 | N | N | N | N | N | N |
| RCAN1 | high in NP | -5.9 | 0.008148653 | -2.1 | 14259 | 46 | 210 | 86 | 17 | 15 | 18 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | Nulliparous (NP) | | | Parous (P) | | | NP | P | NP | | P | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| RRP7A | high in NP | -10.6 | 0.008141834 | -2.1 | 14260 | 23 | 110 | 43 | 7 | 2 | 2 | N | N | N | N | N | N |
| PSAP | high in NP | -4.2 | 0.008135015 | -2.1 | 14261 | 1010 | 2332 | 1722 | 423 | 278 | 404 | N | N | N | N | N | N |
| CBFB | high in NP | -5.0 | 0.008121377 | -2.1 | 14262 | 241 | 601 | 369 | 69 | 58 | 84 | N | N | N | N | N | N |
| SHQ1 | high in NP | -5.4 | 0.0081077 | -2.1 | 14263 | 25 | 42 | 40 | 7 | 7 | 7 | N | N | N | N | N | N |
| RPL27 | high in NP | -14.1 | 0.008060826 | -2.1 | 14264 | 461 | 3529 | 2353 | 155 | 140 | 146 | N | N | N | N | N | N |
| KIAA0247 | high in NP | -6.4 | 0.008060007 | -2.1 | 14265 | 1542 | 1082 | 579 | 322 | 197 | 124 | N | N | N | N | N | N |
| TBC1D20 | high in NP | -5.2 | 0.00803955 | -2.1 | 14266 | 316 | 615 | 622 | 143 | 99 | 107 | N | N | N | N | N | N |
| CD8B | high in NP | -5.9 | 0.008032731 | -2.1 | 14267 | 72 | 29 | 18 | 6 | 6 | 6 | N | N | N | N | N | N |
| HCFC1 | high in NP | -3.1 | 0.008019093 | -2.1 | 14268 | 338 | 415 | 424 | 139 | 126 | 138 | N | N | N | N | N | N |
| CHP | high in NP | -4.3 | 0.008012274 | -2.1 | 14269 | 1113 | 1027 | 633 | 229 | 220 | 199 | N | N | N | N | N | N |
| RBPJ | high in NP | -6.5 | 0.007982953 | -2.1 | 14270 | 50 | 183 | 68 | 18 | 16 | 16 | N | N | N | N | N | N |
| GPM6B | high in NP | -5.2 | 0.007976134 | -2.1 | 14271 | 113 | 154 | 175 | 42 | 29 | 18 | N | N | N | N | N | N |
| SCAND1 | high in NP | -5.3 | 0.007955677 | -2.1 | 14272 | 141 | 220 | 289 | 41 | 40 | 19 | N | N | N | N | N | N |
| CNKSR3 | high in NP | -7.3 | 0.007948858 | -2.1 | 14273 | 39 | 107 | 66 | 13 | 14 | 14 | N | N | N | N | N | N |
| LRP12 | high in NP | -9.0 | 0.007942039 | -2.1 | 14274 | 33 | 135 | 69 | 12 | 12 | 15 | N | N | N | N | N | N |
| BACE2 | high in NP | -6.8 | 0.007916127 | -2.1 | 14275 | 38 | 90 | 112 | 10 | 15 | 10 | N | N | N | N | N | N |
| HOXD8 | high in NP | -7.4 | 0.007902489 | -2.1 | 14276 | 29 | 59 | 32 | 2 | 2 | 8 | N | N | N | N | N | N |
| NUPR1 | high in NP | -3.5 | 0.007789567 | -2.1 | 14277 | 497 | 569 | 643 | 193 | 141 | 133 | N | N | N | N | N | N |
| ARF3 | high in NP | -4.4 | 0.007869758 | -2.1 | 14278 | 1107 | 795 | 821 | 285 | 252 | 138 | N | N | N | N | N | N |
| GABARAPL2 | high in NP | -5.1 | 0.007837027 | -2.1 | 14279 | 69 | 124 | 117 | 13 | 21 | 9 | N | N | N | N | N | N |
| SPIN4 | high in NP | -4.1 | 0.00781657 | -2.1 | 14280 | 25 | 31 | 27 | 7 | 7 | 7 | N | N | N | N | N | N |
| PIK3IP1 | high in NP | -5.6 | 0.007809751 | -2.1 | 14281 | 59 | 119 | 84 | 18 | 13 | 14 | N | P | N | N | N | N |
| SS18 | high in NP | -4.5 | 0.007789294 | -2.1 | 14282 | 288 | 428 | 480 | 126 | 57 | 63 | N | N | N | N | N | N |
| TRAPPC3 | high in NP | -6.8 | 0.007762018 | -2.1 | 14283 | 81 | 132 | 188 | 23 | 14 | 5 | N | N | N | N | N | N |
| SERPING1 | high in NP | -4.2 | 0.007727924 | -2.1 | 14284 | 214 | 522 | 191 | 47 | 44 | 50 | N | N | N | N | N | N |
| ARL5B | high in NP | -6.4 | 0.007721105 | -2.1 | 14285 | 134 | 93 | 83 | 9 | 9 | 22 | N | N | N | N | N | N |
| NGRN | high in NP | -4.3 | 0.007707467 | -2.1 | 14286 | 43 | 297 | 264 | 12 | 14 | 9 | N | N | N | N | N | N |
| C16orf42 | high in NP | -4.9 | 0.007700648 | -2.1 | 14287 | 70 | 157 | 148 | 22 | 15 | 10 | N | N | N | N | N | N |
| STOM | high in NP | -5.9 | 0.00768701 | -2.1 | 14288 | 13672 | 6612 | 3593 | 1315 | 817 | 937 | N | N | N | N | N | N |
| NDRG1 | high in NP | -5.2 | 0.007660416 | -2.1 | 14289 | 4859 | 3253 | 4736 | 876 | 422 | 1070 | N | N | N | N | N | N |
| CD2AP | high in NP | -4.8 | 0.007643369 | -2.1 | 14290 | 44 | 75 | 69 | 19 | 19 | 17 | N | N | N | N | N | N |
| UBAC2 | high in NP | -4.6 | 0.007635655 | -2.1 | 14291 | 33 | 19 | 30 | 10 | 10 | 10 | N | N | N | N | N | N |
| TNN | high in NP | -4.8 | 0.007584726 | -2.1 | 14292 | 529 | 430 | 395 | 29 | 78 | 110 | N | N | N | N | N | N |
| IGFBP4 | high in NP | -4.4 | 0.007533583 | -2.1 | 14293 | 1613 | 2106 | 1570 | 415 | 267 | 557 | N | N | N | N | N | N |
| SLC15A4 | high in NP | -4.2 | 0.007526764 | -2.1 | 14294 | 70 | 116 | 81 | 23 | 21 | 13 | N | N | N | N | N | N |
| ETV5 | high in NP | -4.8 | 0.007511763 | -2.1 | 14295 | 152 | 149 | 245 | 35 | 25 | 49 | N | N | N | N | N | N |
| CHMP2B | high in NP | -9.1 | 0.007504944 | -2.1 | 14296 | 53 | 254 | 240 | 10 | 10 | 21 | N | N | N | N | N | N |
| SCOC | high in NP | -4.6 | 0.007460621 | -2.1 | 14297 | 28 | 36 | 66 | 6 | 6 | 6 | N | N | N | N | N | N |
| FN1 | high in NP | -8.0 | 0.007446983 | -2.1 | 14298 | 1397 | 2181 | 568 | 93 | 168 | 226 | N | N | N | N | N | N |
| TMEM66 | high in NP | -17.8 | 0.007440164 | -2.1 | 14299 | 79 | 698 | 346 | 14 | 8 | 27 | N | N | N | N | N | N |
| SLC27A1 | high in NP | -4.0 | 0.007406069 | -2.1 | 14300 | 155 | 147 | 161 | 37 | 37 | 17 | N | N | N | N | N | N |
| CCDC82 | high in NP | -6.3 | 0.007390385 | -2.1 | 14301 | 23 | 71 | 45 | 7 | 7 | 7 | N | N | N | P | N | N |
| ELL | high in NP | -4.9 | 0.007383566 | -2.1 | 14302 | 939 | 1042 | 1023 | 196 | 210 | 364 | N | N | N | N | N | N |
| PI16 | high in NP | -10.0 | 0.007369928 | -2.1 | 14303 | 452 | 903 | 234 | 14 | 39 | 82 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | | Nulliparous (NP) | | | Parous (P) | | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 NP | CD44+ N66 P | GeneBody NP Met NP | GeneBody Met P | Pro-moter Met NP | Pro-moter Met P |
| ISG15 | high in NP | -8.3 | 0.007363109 | -2.1 | 14304 | 305 | 57 | 122 | 14 | 10 | 8 | N | N | N | N | N | N |
| FBXO7 | high in NP | -16.8 | 0.007349472 | -2.1 | 14305 | 43 | 259 | 223 | 17 | 13 | 10 | N | N | N | N | P | N |
| C8orf58 | high in NP | -4.3 | 0.007329697 | -2.1 | 14306 | 18 | 16 | 15 | 7 | 7 | 7 | N | N | N | N | N | N |
| EIF6 | high in NP | -9.5 | 0.007322878 | -2.1 | 14307 | 194 | 759 | 741 | 69 | 66 | 31 | N | N | N | N | N | N |
| LILRB3 | high in NP | -11.4 | 0.007316059 | -2.1 | 14308 | 76 | 359 | 269 | 22 | 18 | 8 | N | N | N | N | N | N |
| CMPK1 | high in NP | -6.4 | 0.007246505 | -2.1 | 14309 | 385 | 896 | 589 | 142 | 116 | 44 | N | N | N | N | N | N |
| COLEC12 | high in NP | -4.4 | 0.007226048 | -2.1 | 14310 | 37 | 72 | 76 | 9 | 9 | 13 | N | N | N | N | N | N |
| NCOA4 | high in NP | -3.9 | 0.007198773 | -2.1 | 14311 | 499 | 553 | 398 | 133 | 140 | 92 | N | N | N | N | N | N |
| VASP | high in NP | -12.0 | 0.007183089 | -2.1 | 14312 | 114 | 423 | 180 | 33 | 40 | 21 | N | N | N | N | N | N |
| RBM14 | high in NP | -5.9 | 0.00717627 | -2.1 | 14313 | 172 | 527 | 341 | 68 | 52 | 57 | N | N | N | N | N | N |
| SF1 | high in NP | -4.5 | 0.007152404 | -2.1 | 14314 | 2366 | 4624 | 3661 | 776 | 1102 | 993 | N | N | N | N | N | N |
| CCNI | high in NP | -11.6 | 0.007145585 | -2.1 | 14315 | 271 | 2899 | 854 | 93 | 33 | 65 | N | N | N | N | N | N |
| C10orf116 | high in NP | -6.5 | 0.007131947 | -2.1 | 14316 | 788 | 906 | 374 | 59 | 119 | 105 | N | N | N | N | N | N |
| CHSY1 | high in NP | -4.1 | 0.007118309 | -2.1 | 14317 | 1292 | 1106 | 782 | 311 | 269 | 352 | N | N | N | N | P | N |
| LRRC61 | high in NP | -8.5 | 0.00711149 | -2.1 | 14318 | 54 | 28 | 32 | 2 | 5 | 8 | N | N | N | N | N | N |
| EIF3H | high in NP | -4.6 | 0.007104671 | -2.1 | 14319 | 387 | 646 | 870 | 86 | 130 | 119 | N | N | N | N | N | N |
| MXRA7 | high in NP | -5.2 | 0.007082168 | -2.1 | 14320 | 1185 | 1265 | 582 | 278 | 210 | 205 | N | N | N | N | N | N |
| FAM150B | high in NP | -4.1 | 0.007075349 | -2.1 | 14321 | 14 | 11 | 12 | 3 | 3 | 3 | N | N | N | N | N | N |
| CHMP5 | high in NP | -17.5 | 0.007048074 | -2.1 | 14322 | 88 | 364 | 425 | 22 | 5 | 18 | N | N | N | N | N | N |
| KCNMB4 | high in NP | -15.4 | 0.007020798 | -2.2 | 14323 | 99 | 9 | 20 | 5 | 2 | 2 | N | N | N | N | N | N |
| SPTLC1 | high in NP | -7.1 | 0.007013979 | -2.2 | 14324 | 49 | 119 | 137 | 17 | 17 | 15 | N | N | N | N | N | N |
| YIPF5 | high in NP | -4.1 | 0.006993522 | -2.2 | 14325 | 118 | 166 | 148 | 38 | 28 | 32 | P | N | N | N | N | N |
| PRPF31 | high in NP | -6.6 | 0.006966246 | -2.2 | 14326 | 27 | 85 | 55 | 8 | 8 | 6 | N | N | N | N | N | N |
| KIAA1715 | high in NP | -3.4 | 0.006945789 | -2.2 | 14327 | 144 | 133 | 140 | 43 | 34 | 29 | N | N | N | N | N | N |
| SC4MOL | high in NP | -13.5 | 0.006932151 | -2.2 | 14328 | 112 | 656 | 587 | 45 | 30 | 16 | N | N | N | N | N | N |
| MXRA5 | high in NP | -6.8 | 0.006906239 | -2.2 | 14329 | 490 | 177 | 165 | 33 | 27 | 48 | N | N | N | N | N | N |
| SPARCL1 | high in NP | -7.2 | 0.00685807 | -2.2 | 14330 | 281 | 1115 | 184 | 39 | 42 | 33 | N | N | N | N | N | N |
| C22orf13 | high in NP | -5.3 | 0.006843505 | -2.2 | 14331 | 448 | 643 | 567 | 187 | 98 | 78 | N | N | N | N | N | N |
| CDK9 | high in NP | -3.2 | 0.006788953 | -2.2 | 14332 | 482 | 580 | 570 | 164 | 171 | 173 | N | N | N | N | N | N |
| FUS | high in NP | -13.0 | 0.006782134 | -2.2 | 14333 | 309 | 1898 | 1354 | 138 | 74 | 82 | N | N | N | N | N | N |
| OLFML2A | high in NP | -7.3 | 0.006768496 | -2.2 | 14334 | 419 | 340 | 148 | 25 | 22 | 49 | N | N | N | N | N | N |
| GPAA1 | high in NP | -4.2 | 0.006728265 | -2.2 | 14335 | 216 | 161 | 206 | 51 | 35 | 36 | N | N | N | N | N | N |
| LOC552889 | high in NP | -3.8 | 0.006721446 | -2.2 | 14336 | NA | NA | NA | NA | NA | NA | N | N | N | N | N | N |
| MYO1B | high in NP | -4.0 | 0.006709171 | -2.2 | 14337 | 207 | 258 | 304 | 86 | 67 | 59 | N | N | N | N | N | N |
| CCL2 | high in NP | -7.6 | 0.006695534 | -2.2 | 14338 | 6445 | 2848 | 1112 | 366 | 385 | 244 | N | N | N | N | N | N |
| CDIPT | high in NP | -6.5 | 0.006668258 | -2.2 | 14339 | 169 | 295 | 283 | 56 | 12 | 31 | N | N | N | N | N | N |
| PIN1 | high in NP | -4.8 | 0.006661439 | -2.2 | 14340 | 142 | 93 | 105 | 26 | 12 | 15 | N | N | N | N | N | N |
| HES1 | high in NP | -8.0 | 0.006642346 | -2.2 | 14341 | 215 | 338 | 447 | 84 | 23 | 35 | N | N | N | N | N | N |
| PRSS23 | high in NP | -7.0 | 0.006563928 | -2.2 | 14342 | 193 | 291 | 102 | 36 | 15 | 18 | N | N | N | N | N | N |
| TGIF2 | high in NP | -8.2 | 0.006543471 | -2.2 | 14343 | 1156 | 604 | 330 | 60 | 51 | 127 | N | N | N | N | N | N |
| SPP1 | high in NP | -3.7 | 0.006536652 | -2.2 | 14344 | 37 | 49 | 57 | 11 | 14 | 11 | N | N | N | N | N | N |
| GEM | high in NP | -12.3 | 0.006529833 | -2.2 | 14345 | 433 | 1496 | 1034 | 38 | 71 | 207 | N | N | N | N | N | N |
| FBXL20 | high in NP | -4.2 | 0.006461643 | -2.2 | 14346 | 27 | 32 | 23 | 6 | 6 | 6 | N | N | P | N | N | N |
| FEN1 | high in NP | -8.5 | 0.006454824 | -2.2 | 14347 | 22 | 62 | 65 | 6 | 6 | 6 | N | N | N | N | N | N |

TABLE 15-continued

Genes that Are Differentially Methylated between Nulliparous and Parous CD44+ Breast Epithelial Cells

| | | | | | | SAGE-seq | | | | | | ChIP-seq | | | MSDK-seq | | |
| | | | | | | | Nulliparous (NP) | | | Parous (P) | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
|---|---|---|---|---|---|---|---|---|---|---|---|---|---|---|---|---|---|
| ID4 | high in NP | -11.4 | 0.000434368 | -2.2 | 14348 | 58 | 542 | 119 | 17 | 15 | 15 | N | N | N | N | N | N |
| PTPRS | high in NP | -5.6 | 0.00642073 | -2.2 | 14349 | 817 | 374 | 551 | 116 | 62 | 116 | N | N | N | N | N | N |
| THBS1 | high in NP | -9.4 | 0.006398227 | -2.2 | 14350 | 1332 | 3715 | 4223 | 136 | 534 | 440 | N | N | N | N | N | N |
| TMEM50A | high in NP | -4.2 | 0.006383225 | -2.2 | 14351 | 69 | 93 | 94 | 24 | 14 | 17 | N | NA | N | N | N | N |
| LOC653566 | high in NP | -32.0 | 0.006362768 | -2.2 | 14352 | 48 | 397 | 451 | 9 | 1 | 9 | NA | NA | N | N | N | N |
| CLDND1 | high in NP | -3.6 | 0.006342312 | -2.2 | 14353 | 875 | 841 | 774 | 195 | 217 | 251 | N | N | N | N | N | N |
| PPP2CA | high in NP | -4.5 | 0.006308217 | -2.2 | 14354 | 542 | 957 | 926 | 165 | 192 | 205 | N | N | N | N | N | N |
| RPL10 | high in NP | -3.8 | 0.006301398 | -2.2 | 14355 | 25828 | 21030 | 26439 | 4688 | 6158 | 5983 | N | N | N | N | N | N |
| CAPN6 | high in NP | -8.0 | 0.006294579 | -2.2 | 14356 | 333 | 66 | 79 | 8 | 8 | 14 | P | P | N | N | N | N |
| HIF1A | high in NP | -6.2 | 0.00628776 | -2.2 | 14357 | 1200 | 1311 | 746 | 331 | 135 | 117 | N | N | N | N | N | N |
| TMEM11 | high in NP | -41.4 | 0.006268667 | -2.2 | 14358 | 15 | 131 | 63 | 4 | 4 | 4 | N | N | N | N | N | N |
| CYBA | high in NP | -3.8 | 0.00624821 | -2.2 | 14359 | 176 | 225 | 210 | 44 | 51 | 36 | N | N | N | N | N | N |
| KCTD9 | high in NP | -16.6 | 0.006234572 | -2.2 | 14360 | 124 | 654 | 725 | 28 | 22 | 40 | N | N | N | N | N | N |
| MGAT4B | high in NP | -4.7 | 0.006220934 | -2.2 | 14361 | 235 | 327 | 438 | 82 | 60 | 59 | P | N | N | N | N | N |
| RAP2A | high in NP | -6.0 | 0.006200477 | -2.2 | 14362 | 137 | 243 | 243 | 40 | 15 | 39 | N | N | N | N | N | N |
| DUSP16 | high in NP | -6.8 | 0.006186839 | -2.2 | 14363 | 20 | 51 | 52 | 4 | 4 | 4 | N | N | N | N | N | N |
| PKIG | high in NP | -6.5 | 0.00618002 | -2.2 | 14364 | 1246 | 792 | 687 | 246 | 86 | 105 | N | N | N | N | N | N |
| TMEM106B | high in NP | -4.5 | 0.006152745 | -2.2 | 14365 | 79 | 124 | 177 | 24 | 19 | 20 | N | P | N | N | N | N |
| MBNL2 | high in NP | -5.8 | 0.006139107 | -2.2 | 14366 | 268 | 544 | 258 | 46 | 49 | 83 | N | N | N | N | N | N |
| YIF1A | high in NP | -7.8 | 0.006117286 | -2.2 | 14367 | 297 | 198 | 268 | 54 | 25 | 9 | N | N | N | N | N | N |
| USP22 | high in NP | -4.9 | 0.006103648 | -2.2 | 14368 | 757 | 1575 | 1297 | 330 | 227 | 242 | N | N | N | N | N | N |
| YAP1 | high in NP | -7.1 | 0.006091374 | -2.2 | 14369 | 298 | 1016 | 679 | 118 | 87 | 97 | N | N | N | N | N | N |
| OLFML3 | high in NP | -7.2 | 0.006077054 | -2.2 | 14370 | 159 | 179 | 55 | 10 | 10 | 22 | N | N | N | N | N | N |
| COL14A1 | high in NP | -6.2 | 0.000670235 | -2.2 | 14371 | 1086 | 437 | 260 | 47 | 67 | 71 | N | N | N | N | N | N |
| PLAT | high in NP | -5.0 | 0.006063416 | -2.2 | 14372 | 110 | 387 | 149 | 32 | 23 | 25 | N | N | N | N | N | N |
| LATS2 | high in NP | -7.4 | 0.006034095 | -2.2 | 14373 | 444 | 1053 | 1673 | 111 | 141 | 163 | N | N | N | N | N | N |
| PSMA2 | high in NP | -13.1 | 0.006013638 | -2.2 | 14374 | 166 | 746 | 719 | 49 | 42 | 32 | N | N | N | N | N | N |
| STK10 | high in NP | -4.1 | 0.005986362 | -2.2 | 14375 | 115 | 196 | 203 | 34 | 45 | 36 | N | N | N | N | N | N |
| NCRNA00188 | high in NP | -68.7 | 0.00593181 | -2.2 | 14376 | 125 | 3915 | 2656 | 33 | 24 | 33 | NA | NA | N | N | N | N |
| SFRS9 | high in NP | -13.7 | 0.005863621 | -2.2 | 14377 | 287 | 1266 | 1442 | 86 | 83 | 63 | N | N | N | N | N | N |
| SNAPC3 | high in NP | -5.1 | 0.005853392 | -2.2 | 14378 | 55 | 42 | 96 | 13 | 12 | 9 | N | N | N | N | N | N |
| MAP2K3 | high in NP | -5.4 | 0.005839755 | -2.2 | 14379 | 3194 | 4138 | 3236 | 360 | 1009 | 606 | N | N | N | N | N | N |
| TPT1 | high in NP | -26.0 | 0.005819298 | -2.2 | 14380 | 615 | 6782 | 4709 | 116 | 161 | 217 | N | N | N | N | N | N |
| C6orf62 | high in NP | -8.7 | 0.005580566 | -2.2 | 14381 | 262 | 856 | 626 | 92 | 50 | 68 | N | N | N | N | N | N |
| RNF130 | high in NP | -9.3 | 0.005798841 | -2.2 | 14382 | 48 | 104 | 64 | 10 | 6 | 11 | N | N | N | N | N | N |
| SLC39A7 | high in NP | -6.9 | 0.005792022 | -2.2 | 14383 | 152 | 399 | 278 | 53 | 35 | 18 | N | N | N | N | N | N |
| RPL35 | high in NP | -5.6 | 0.005785203 | -2.2 | 14384 | 4546 | 7634 | 9373 | 1123 | 1453 | 1034 | N | N | N | N | N | N |
| OTUD1 | high in NP | -9.4 | 0.005778384 | -2.2 | 14385 | 82 | 385 | 153 | 16 | 9 | 23 | NA | NA | N | N | N | N |
| AZGP1 | high in NP | -19.2 | 0.005771565 | -2.2 | 14386 | 65 | 238 | 444 | 20 | 30 | 18 | P | P | N | N | P | N |
| DCAKD | high in NP | -6.8 | 0.005751108 | -2.2 | 14387 | 59 | 55 | 32 | 7 | 12 | 10 | N | N | N | N | N | N |
| NAMPT | high in NP | -10.4 | 0.005744289 | -2.2 | 14388 | 359 | 1604 | 980 | 144 | 86 | 72 | N | N | N | N | N | N |
| TRA2B | high in NP | -5.8 | 0.005730651 | -2.2 | 14389 | 151 | 257 | 313 | 56 | 30 | 34 | NA | NA | N | N | N | N |
| HABP4 | high in NP | -4.3 | 0.005723832 | -2.2 | 14390 | 44 | 49 | 34 | 10 | 8 | 11 | N | N | N | N | N | N |
| GYPC | high in NP | -8.9 | 0.005682919 | -2.2 | 14391 | 544 | 522 | 285 | 101 | 37 | 27 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | Parous (P) | | | NP | | P | NP | | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| ATXN10 | high in NP | -8.4 | 0.005669281 | -2.2 | 14392 | 65 | 189 | 190 | 19 | 14 | 10 | N | N | N | N | N | N |
| LAPTM4B | high in NP | -11.7 | 0.005662462 | -2.2 | 14393 | 142 | 595 | 525 | 46 | 38 | 38 | N | N | N | N | N | N |
| ARAF | high in NP | -4.0 | 0.005643369 | -2.2 | 14394 | 39 | 74 | 56 | 15 | 13 | 13 | N | N | N | N | N | N |
| MRC2 | high in NP | -9.0 | 0.005610638 | -2.3 | 14395 | 1897 | 1494 | 979 | 70 | 133 | 322 | N | N | N | N | N | N |
| SH3KBP1 | high in NP | -5.9 | 0.005603819 | -2.3 | 14396 | 156 | 117 | 168 | 35 | 13 | 11 | N | N | N | N | N | N |
| RPL27A | high in NP | -58.0 | 0.005597 | -2.3 | 14397 | 252 | 6766 | 5664 | 46 | 49 | 92 | N | N | N | N | N | N |
| C14orf1 | high in NP | -5.1 | 0.005590181 | -2.3 | 14398 | 35 | 21 | 37 | 6 | 4 | 4 | N | N | N | N | N | N |
| SPTBN1 | high in NP | -5.3 | 0.005583362 | -2.3 | 14399 | 996 | 574 | 533 | 189 | 106 | 143 | N | N | N | N | N | N |
| TM9SF3 | high in NP | -6.1 | 0.005576543 | -2.3 | 14400 | 538 | 1128 | 1217 | 223 | 188 | 107 | N | N | N | N | P | N |
| ELK3 | high in NP | -4.4 | 0.005569724 | -2.3 | 14401 | 110 | 115 | 78 | 20 | 20 | 12 | N | N | N | N | N | N |
| AP1AR | high in NP | -7.0 | 0.005552881 | -2.3 | 14402 | 75 | 175 | 196 | 17 | 18 | 26 | NA | NA | N | N | N | N |
| PPME1 | high in NP | -6.5 | 0.005463348 | -2.3 | 14403 | 112 | 202 | 346 | 40 | 27 | 28 | N | N | N | N | N | N |
| NAB2 | high in NP | -5.0 | 0.005456529 | -2.3 | 14404 | 125 | 76 | 68 | 11 | 14 | 14 | N | N | N | N | N | N |
| LOXL2 | high in NP | -8.6 | 0.005436072 | -2.3 | 14405 | 357 | 311 | 421 | 103 | 28 | 32 | N | N | N | N | P | N |
| STC1 | high in NP | -8.3 | 0.005541016 | -2.3 | 14406 | 6046 | 894 | 733 | 174 | 117 | 89 | N | N | N | N | N | N |
| LGMN | high in NP | -4.4 | 0.005396522 | -2.3 | 14407 | 290 | 471 | 366 | 75 | 54 | 88 | N | N | N | N | N | N |
| SUB1 | high in NP | -7.7 | 0.005382884 | -2.3 | 14408 | 113 | 281 | 238 | 41 | 23 | 13 | P | N | N | N | N | N |
| PPP1CB | high in NP | -5.0 | 0.005367201 | -2.3 | 14409 | 698 | 1411 | 979 | 287 | 247 | 188 | N | P | N | N | P | N |
| STAU1 | high in NP | -5.0 | 0.005318786 | -2.3 | 14410 | 169 | 267 | 256 | 34 | 56 | 44 | N | N | N | N | N | N |
| C14orf129 | high in NP | -7.9 | 0.005279918 | -2.3 | 14411 | 23 | 23 | 18 | 6 | 6 | 9 | N | N | N | N | N | N |
| YPEL2 | high in NP | -6.1 | 0.005273099 | -2.3 | 14412 | 381 | 612 | 366 | 91 | 36 | 92 | N | N | N | N | N | N |
| CD44 | high in NP | -4.4 | 0.005239004 | -2.3 | 14413 | 5212 | 9345 | 5153 | 1493 | 1191 | 1330 | N | N | N | N | N | N |
| TNPO2 | high in NP | -4.3 | 0.005196045 | -2.3 | 14414 | 391 | 382 | 477 | 109 | 75 | 116 | N | N | N | N | N | N |
| GPR124 | high in NP | -6.6 | 0.005168769 | -2.3 | 14415 | 369 | 164 | 104 | 17 | 19 | 22 | N | N | N | N | N | N |
| LAPTM4A | high in NP | -6.9 | 0.005155131 | -2.3 | 14416 | 5692 | 9698 | 4858 | 1531 | 613 | 762 | N | N | N | N | N | N |
| RPS18 | high in NP | -15.2 | 0.005148312 | -2.3 | 14417 | 4106 | 21524 | 17358 | 795 | 1250 | 1049 | NA | NA | N | N | N | N |
| DYRK1A | high in NP | -4.5 | 0.005127855 | -2.3 | 14418 | 452 | 894 | 653 | 172 | 152 | 136 | N | N | N | N | N | N |
| TMEM8B | high in NP | -4.9 | 0.005121036 | -2.3 | 14419 | 43 | 58 | 37 | 9 | 9 | 13 | N | N | N | N | N | N |
| MARCKSL1 | high in NP | -4.7 | 0.00510058 | -2.3 | 14420 | 435 | 526 | 440 | 64 | 117 | 94 | N | N | N | N | N | N |
| CXorf38 | high in NP | -3.8 | 0.005031708 | -2.3 | 14421 | 14 | 6 | 6 | 3 | 3 | 3 | N | N | N | N | N | N |
| INSIG1 | high in NP | -7.3 | 0.004990794 | -2.3 | 14422 | 344 | 214 | 245 | 30 | 27 | 69 | N | N | N | N | N | N |
| IRF2BP2 | high in NP | -7.0 | 0.004983975 | -2.3 | 14423 | 532 | 1543 | 1120 | 130 | 108 | 227 | N | N | N | N | N | N |
| CCS | high in NP | -4.1 | 0.0049567 | -2.3 | 14424 | 31 | 18 | 19 | 5 | 5 | 5 | N | N | N | N | N | N |
| CTSK | high in NP | -5.9 | 0.004936243 | -2.3 | 14425 | 37 | 101 | 42 | 8 | 8 | 6 | N | N | N | N | N | N |
| DYNLRB1 | high in NP | -8.2 | 0.004915786 | -2.3 | 14426 | 173 | 357 | 265 | 47 | 23 | 10 | N | N | N | N | N | N |
| ETV6 | high in NP | -6.4 | 0.004908967 | -2.3 | 14427 | 252 | 242 | 241 | 41 | 72 | 38 | N | N | N | N | N | N |
| ARF6 | high in NP | -9.6 | 0.004881691 | -2.3 | 14428 | 976 | 3467 | 2706 | 165 | 279 | 331 | N | N | N | N | N | N |
| PCDH18 | high in NP | -6.1 | 0.004868053 | -2.3 | 14429 | 207 | 149 | 248 | 23 | 20 | 45 | N | N | N | N | N | N |
| C3orf58 | high in NP | -3.7 | 0.004840777 | -2.3 | 14430 | 57 | 70 | 67 | 15 | 18 | 13 | N | N | N | N | N | N |
| MRPL44 | high in NP | -19.6 | 0.004808046 | -2.3 | 14431 | 140 | 773 | 835 | 27 | 20 | 34 | N | N | N | N | N | N |
| GPNMB | high in NP | -7.9 | 0.004801227 | -2.3 | 14432 | 1330 | 1214 | 583 | 63 | 134 | 162 | N | N | N | N | N | N |
| DLK1 | high in NP | -6.9 | 0.004773952 | -2.3 | 14433 | 32 | 53 | 69 | 5 | 8 | 5 | N | N | N | N | N | N |
| VEGFB | high in NP | -7.0 | 0.004760314 | -2.3 | 14434 | 404 | 250 | 239 | 68 | 30 | 27 | N | N | N | N | N | N |
| CLEC11A | high in NP | -8.2 | 0.004739857 | -2.3 | 14435 | 81 | 68 | 26 | 5 | 10 | 5 | N | N | N | N | N | N |

TABLE 15-continued

Genes that Are Differentially Methylated between Nulliparous and Parous CD44+ Breast Epithelial Cells

| | | | | | | SAGE-seq | | | | | | | ChIP-seq | | | MSDK-seq | | |
|---|---|---|---|---|---|---|---|---|---|---|---|---|---|---|---|---|---|---|
| | | | | | | Nulliparous (NP) | | | Parous (P) | | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| RNF19B | high in NP | -5.6 | 0.0047194 | -2.3 | 14436 | 171 | 322 | 266 | 29 | 47 | 43 | N | N | N | N | N | N |
| FBLN7 | high in NP | -4.8 | 0.004705762 | -2.3 | 14437 | 105 | 79 | 84 | 21 | 11 | 14 | N | N | N | N | N | N |
| C19orf56 | high in NP | -7.8 | 0.004666212 | -2.3 | 14438 | 254 | 722 | 511 | 74 | 47 | 54 | N | N | N | N | N | N |
| HNRNPUL1 | high in NP | -12.6 | 0.004659393 | -2.3 | 14439 | 172 | 785 | 558 | 44 | 27 | 47 | N | N | N | N | P | N |
| LOXL3 | high in NP | -9.8 | 0.004645755 | -2.3 | 14440 | 73 | 37 | 34 | 10 | 6 | 6 | N | N | N | N | N | N |
| PCDHB14 | high in NP | -8.8 | 0.004638936 | -2.3 | 14441 | 26 | 26 | 13 | 5 | 5 | 8 | N | N | N | N | N | N |
| TPM3 | high in NP | -3.6 | 0.004618479 | -2.3 | 14442 | 907 | 1029 | 794 | 303 | 255 | 289 | N | N | N | N | N | N |
| H3F3C | high in NP | -12.7 | 0.00461166 | -2.3 | 14443 | 322 | 1555 | 959 | 97 | 44 | 51 | NA | NA | N | N | N | N |
| MFGE8 | high in NP | -4.3 | 0.004577566 | -2.3 | 14444 | 2411 | 2004 | 2087 | 536 | 582 | 417 | N | N | N | N | N | N |
| PHLDA3 | high in NP | -8.6 | 0.004577047 | -2.3 | 14445 | 28 | 98 | 64 | 7 | 7 | 7 | N | N | N | N | N | N |
| FBXO21 | high in NP | -4.5 | 0.004543471 | -2.3 | 14446 | 136 | 218 | 181 | 42 | 29 | 29 | N | N | N | N | N | N |
| CAMLG | high in NP | -10.6 | 0.004529833 | -2.3 | 14447 | 58 | 184 | 285 | 11 | 14 | 14 | N | N | N | N | N | N |
| H1FX | high in NP | -16.9 | 0.004523014 | -2.3 | 14448 | 549 | 1309 | 2068 | 199 | 27 | 56 | N | N | N | N | N | N |
| ZC3H11A | high in NP | -7.3 | 0.004516195 | -2.3 | 14449 | 224 | 565 | 446 | 78 | 40 | 52 | N | N | N | N | N | N |
| C14orf147 | high in NP | -16.2 | 0.004488919 | -2.3 | 14450 | 284 | 1313 | 1364 | 61 | 73 | 79 | N | N | N | N | N | N |
| LOC154761 | high in NP | -8.6 | 0.0044821 | -2.3 | 14451 | 83 | 28 | 50 | 6 | 9 | 6 | N | N | N | N | N | N |
| HHAT | high in NP | -4.9 | 0.004468462 | -2.3 | 14452 | 31 | 21 | 15 | 9 | 9 | 9 | N | N | N | N | N | N |
| CCPG1 | high in NP | -4.5 | 0.004461643 | -2.3 | 14453 | 82 | 79 | 89 | 21 | 19 | 25 | N | N | N | N | N | N |
| CCDC53 | high in NP | -9.6 | 0.004448005 | -2.3 | 14454 | 45 | 59 | 29 | 7 | 3 | 3 | N | N | N | N | P | N |
| PGF | high in NP | -4.3 | 0.004441186 | -2.3 | 14455 | 49 | 63 | 51 | 15 | 13 | 16 | N | N | N | N | N | N |
| CTDSP1 | high in NP | -6.3 | 0.004411865 | -2.4 | 14456 | 1205 | 890 | 567 | 188 | 75 | 77 | N | N | N | N | N | N |
| ST8SIA2 | high in NP | -10.3 | 0.004370951 | -2.4 | 14457 | 73 | 117 | 39 | 17 | 19 | 17 | P | N | N | N | N | N |
| GBE1 | high in NP | -10.9 | 0.004364132 | -2.4 | 14458 | 53 | 156 | 175 | 18 | 15 | 12 | N | N | N | N | N | N |
| CSRNP2 | high in NP | -8.2 | 0.004357313 | -2.4 | 14459 | 101 | 320 | 141 | 24 | 16 | 24 | NA | NA | N | N | N | N |
| DYRK3 | high in NP | -8.8 | 0.004343675 | -2.4 | 14460 | 33 | 146 | 40 | 7 | 7 | 7 | N | N | N | N | N | N |
| AKIRIN1 | high in NP | -4.2 | 0.004323219 | -2.4 | 14461 | 463 | 427 | 354 | 101 | 86 | 99 | N | N | N | N | N | N |
| TMED9 | high in NP | -5.3 | 0.004304125 | -2.4 | 14462 | 33 | 50 | 36 | 9 | 6 | 6 | N | N | N | N | N | N |
| C1orf55 | high in NP | -11.3 | 0.004290488 | -2.4 | 14463 | 192 | 1257 | 427 | 44 | 41 | 40 | N | N | P | N | N | N |
| PHC2 | high in NP | -5.8 | 0.004283669 | -2.4 | 14464 | 1407 | 2009 | 1359 | 431 | 256 | 183 | N | N | N | N | N | N |
| MRPL24 | high in NP | -6.3 | 0.004256393 | -2.4 | 14465 | 81 | 102 | 125 | 13 | 14 | 5 | P | P | N | N | N | N |
| PLP1 | high in NP | -6.3 | 0.004246164 | -2.4 | 14466 | 60 | 31 | 50 | 8 | 8 | 8 | N | N | N | N | N | N |
| MXRA8 | high in NP | -11.1 | 0.004218889 | -2.4 | 14467 | 2351 | 992 | 1337 | 59 | 100 | 273 | P | P | N | N | P | N |
| PFN2 | high in NP | -4.6 | 0.004184794 | -2.4 | 14468 | 311 | 365 | 395 | 99 | 58 | 56 | N | N | N | N | N | N |
| GNAI2 | high in NP | -6.6 | 0.004171156 | -2.4 | 14469 | 1154 | 824 | 446 | 157 | 78 | 122 | P | N | N | N | N | N |
| BMP3 | high in NP | -10.6 | 0.004152063 | -2.4 | 14470 | 52 | 192 | 158 | 8 | 11 | 11 | N | N | N | N | N | N |
| MRPS11 | high in NP | -7.9 | 0.004145244 | -2.4 | 14471 | 20 | 21 | 29 | 4 | 7 | 4 | N | N | N | N | N | N |
| TMEM185A | high in NP | -6.8 | 0.00413297 | -2.4 | 14472 | 138 | 134 | 109 | 32 | 20 | 16 | P | P | N | N | N | N |
| AKIRIN1 | high in NP | -4.7 | 0.004098875 | -2.4 | 14473 | 239 | 344 | 333 | 73 | 66 | 60 | P | P | N | N | N | N |
| LUC7L2 | high in NP | -4.8 | 0.004085237 | -2.4 | 14474 | 95 | 135 | 113 | 26 | 15 | 17 | N | N | N | N | N | N |
| C10orf32 | high in NP | -15.3 | 0.004071599 | -2.4 | 14475 | 96 | 588 | 272 | 21 | 9 | 9 | P | P | N | N | N | N |
| DAP | high in NP | -6.5 | 0.004051142 | -2.4 | 14476 | 96 | 116 | 65 | 9 | 3 | 11 | N | N | N | N | N | N |
| ARL4D | high in NP | -20.4 | 0.004044323 | -2.4 | 14477 | 99 | 376 | 626 | 16 | 24 | 17 | N | N | N | N | N | N |
| SLC38A5 | high in NP | -7.7 | 0.003989772 | -2.4 | 14478 | 296 | 671 | 664 | 90 | 44 | 32 | N | N | N | N | N | N |
| STOML2 | high in NP | -4.6 | 0.003982953 | -2.4 | 14479 | 1502 | 1911 | 1939 | 592 | 436 | 370 | N | N | N | N | N | N |
| CDC42 | | | | | | | | | | | | | | | | | |

TABLE 15-continued

Genes that Are Differentially Methylated between Nulliparous and Parous CD44+ Breast Epithelial Cells

| | | | | | SAGE-seq | | | | | | | ChIP-seq | | | | MSDK-seq | | |
|---|---|---|---|---|---|---|---|---|---|---|---|---|---|---|---|---|---|---|
| | | | | | | Nulliparous (NP) | | | | Parous (P) | | | NP | | P | | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-motor Met |
| PHLPP1 | high in NP | −7.5 | 0.003976134 | −2.4 | 14480 | 103 | 227 | 204 | 27 | 29 | 20 | NA | NA | N | N | N | N |
| DUSP6 | high in NP | −9.6 | 0.003969315 | −2.4 | 14481 | 224 | 571 | 630 | 59 | 56 | 47 | N | N | N | N | N | N |
| C7orf50 | high in NP | −7.6 | 0.003948858 | −2.4 | 14482 | 51 | 35 | 45 | 8 | 4 | 4 | N | N | N | N | N | N |
| TMEM176B | high in NP | −7.7 | 0.003914081 | −2.4 | 14483 | 523 | 482 | 236 | 39 | 48 | 54 | N | N | P | N | N | N |
| GTF2H5 | high in NP | −6.1 | 0.003907262 | −2.4 | 14484 | 158 | 307 | 199 | 53 | 30 | 35 | N | N | N | N | N | N |
| C2orf76 | high in NP | −9.0 | 0.003893624 | −2.4 | 14485 | 13 | 15 | 11 | 2 | 2 | 2 | N | N | N | N | P | N |
| EID1 | high in NP | −7.0 | 0.003886805 | −2.4 | 14486 | 315 | 473 | 344 | 47 | 16 | 56 | N | N | N | N | N | N |
| PPP1CA | high in NP | −21.9 | 0.003864985 | −2.4 | 14487 | 56 | 340 | 398 | 18 | 9 | 9 | N | N | N | N | N | N |
| RPLP2 | high in NP | −10.8 | 0.003851347 | −2.4 | 14488 | 10732 | 34769 | 28806 | 2330 | 2613 | 2517 | N | N | N | N | N | N |
| IMPDH2 | high in NP | −8.1 | 0.003844528 | −2.4 | 14489 | 229 | 530 | 597 | 47 | 54 | 53 | N | N | N | N | N | N |
| APH1A | high in NP | −8.3 | 0.003817252 | −2.4 | 14490 | 281 | 668 | 834 | 74 | 65 | 44 | N | N | N | N | N | N |
| KDM5B | high in NP | −7.2 | 0.003810433 | −2.4 | 14491 | 44 | 75 | 81 | 18 | 18 | 18 | NA | NA | N | N | N | N |
| CHST15 | high in NP | −7.2 | 0.003803614 | −2.4 | 14492 | 698 | 895 | 787 | 121 | 88 | 212 | NA | NA | N | N | N | N |
| MMGT1 | high in NP | −10.0 | 0.003776338 | −2.4 | 14493 | 77 | 250 | 159 | 22 | 13 | 13 | NA | NA | N | N | N | N |
| PMAIP1 | high in NP | −25.2 | 0.0037627 | −2.4 | 14494 | 34 | 162 | 171 | 6 | 9 | 6 | N | P | N | N | N | N |
| ELF1 | high in NP | −7.0 | 0.003755881 | −2.4 | 14495 | 294 | 436 | 316 | 43 | 27 | 71 | N | N | N | N | N | N |
| FAH | high in NP | −5.0 | 0.003742243 | −2.4 | 14496 | 57 | 47 | 68 | 12 | 12 | 9 | N | N | N | N | N | N |
| RAB32 | high in NP | −22.5 | 0.003728606 | −2.4 | 14497 | 43 | 218 | 265 | 11 | 10 | 7 | N | N | N | N | N | N |
| SLC7A3 | high in NP | −12.8 | 0.00366178 | −2.4 | 14498 | 86 | 20 | 8 | 4 | 4 | 4 | N | P | N | N | N | N |
| WDR33 | high in NP | −7.8 | 0.003654961 | −2.4 | 14499 | 140 | 330 | 401 | 46 | 48 | 51 | N | N | N | N | N | N |
| IGFBP3 | high in NP | −4.6 | 0.003641323 | −2.4 | 14500 | 309 | 337 | 279 | 88 | 58 | 58 | N | N | N | N | N | N |
| HEBP1 | high in NP | −6.5 | 0.003605182 | −2.4 | 14501 | 24 | 58 | 47 | 3 | 3 | 3 | N | N | N | N | N | N |
| KDELR2 | high in NP | −7.2 | 0.003586089 | −2.4 | 14502 | 1015 | 2478 | 1834 | 367 | 208 | 194 | N | N | N | N | N | N |
| ORAI3 | high in NP | −6.3 | 0.003558814 | −2.4 | 14503 | 78 | 76 | 48 | 13 | 9 | 6 | N | N | N | N | N | N |
| ALKBH7 | high in NP | −5.3 | 0.003545176 | −2.5 | 14504 | 264 | 183 | 271 | 37 | 37 | 37 | N | N | N | N | N | N |
| SAR1A | high in NP | −7.6 | 0.003538357 | −2.5 | 14505 | 411 | 1104 | 762 | 120 | 64 | 98 | N | N | N | N | N | N |
| RPS27 | high in NP | −10.6 | 0.003510399 | −2.5 | 14506 | 10291 | 32526 | 25541 | 1523 | 1776 | 2899 | N | N | N | N | N | N |
| GLT8D2 | high in NP | −23.2 | 0.003496761 | −2.5 | 14507 | 117 | 181 | 118 | 6 | 6 | 22 | N | N | N | N | N | N |
| C7orf55 | high in NP | −10.6 | 0.003489942 | −2.5 | 14508 | 20 | 44 | 36 | 6 | 4 | 4 | NA | NA | N | N | N | N |
| HADH | high in NP | −5.7 | 0.003476304 | −2.5 | 14509 | 105 | 76 | 154 | 18 | 16 | 17 | N | N | N | N | N | N |
| GNB2L1 | high in NP | −8.6 | 0.003469485 | −2.5 | 14510 | 2477 | 6443 | 6171 | 623 | 618 | 684 | N | N | N | N | N | N |
| MARCKS | high in NP | −8.8 | 0.003408115 | −2.5 | 14511 | 4872 | 3429 | 2529 | 789 | 216 | 404 | P | N | N | N | N | N |
| KCNA6 | high in NP | −5.0 | 0.003380839 | −2.5 | 14512 | 21 | 18 | 31 | 5 | 5 | 5 | N | N | N | N | N | N |
| RNF138P1 | high in NP | −6.3 | 0.003324241 | −2.5 | 14513 | 60 | 159 | 82 | 13 | 16 | 12 | N | N | N | N | N | N |
| BBS9 | high in NP | −6.3 | 0.003310603 | −2.5 | 14514 | 18 | 12 | 13 | 6 | 6 | 6 | N | N | N | N | N | N |
| SDCBP | high in NP | −6.7 | 0.003243096 | −2.5 | 14515 | 1011 | 2122 | 2036 | 283 | 202 | 266 | N | N | N | N | N | N |
| RPL11 | high in NP | −9.1 | 0.003236277 | −2.5 | 14516 | 4755 | 9919 | 12311 | 937 | 1017 | 1290 | N | N | N | N | N | N |
| TP53 | high in NP | −8.7 | 0.003229458 | −2.5 | 14517 | 106 | 202 | 180 | 22 | 24 | 12 | N | N | N | N | N | N |
| COL1A1 | high in NP | −40.5 | 0.003196045 | −2.5 | 14518 | 19342 | 4514 | 2059 | 61 | 183 | 422 | N | N | N | N | N | N |
| GLT25D1 | high in NP | −6.7 | 0.003168769 | −2.5 | 14519 | 149 | 328 | 293 | 45 | 37 | 36 | N | N | N | N | N | N |
| LDHA | high in NP | −14.6 | 0.003155131 | −2.5 | 14520 | 901 | 4676 | 2750 | 179 | 240 | 132 | N | N | N | N | N | N |
| LOC93622 | high in NP | −6.9 | 0.003134674 | −2.5 | 14521 | 132 | 256 | 184 | 21 | 13 | 28 | NA | NA | N | N | N | N |
| MFAP2 | high in NP | −6.1 | 0.003121036 | −2.5 | 14522 | 45 | 28 | 47 | 4 | 4 | 4 | N | N | N | N | N | N |
| EIF2S3 | high in NP | −9.0 | 0.003086942 | −2.5 | 14523 | 359 | 856 | 798 | 101 | 90 | 72 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | Parous (P) | | | NP | P | GeneBody | GeneBody | Pro-motor | Pro-moter |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | NP Met | Met | Met | Met |
| HSPC159 | high in NP | -6.1 | 0.003025571 | -2.5 | 14524 | 27 | 50 | 26 | 6 | 6 | 6 | N | N | N | N | N | N |
| ACAT1 | high in NP | -6.6 | 0.003018752 | -2.5 | 14525 | 54 | 118 | 71 | 11 | 10 | 7 | N | N | N | N | N | N |
| KHSRP | high in NP | -12.3 | 0.003011933 | -2.5 | 14526 | 417 | 1834 | 1182 | 77 | 98 | 82 | N | N | N | N | N | N |
| CUTA | high in NP | -5.3 | 0.002991476 | -2.5 | 14527 | 455 | 482 | 664 | 75 | 103 | 80 | P | N | N | N | N | N |
| MSX1 | high in NP | -12.1 | 0.0029642 | -2.5 | 14528 | 1505 | 1619 | 869 | 61 | 100 | 209 | N | N | N | N | N | P |
| SH3BGRL | high in NP | -8.8 | 0.002957382 | -2.5 | 14529 | 105 | 236 | 91 | 10 | 15 | 16 | N | N | N | N | N | N |
| MMP14 | high in NP | -6.6 | 0.002950563 | -2.5 | 14530 | 490 | 272 | 318 | 72 | 38 | 41 | N | N | N | N | N | N |
| EIF3K | high in NP | -7.6 | 0.002916468 | -2.5 | 14531 | 407 | 853 | 826 | 88 | 83 | 90 | N | N | N | N | N | N |
| LGALS3BP | high in NP | -9.6 | 0.002909649 | -2.5 | 14532 | 316 | 316 | 107 | 29 | 32 | 28 | N | N | N | N | N | N |
| RPL13 | high in NP | -5.8 | 0.002859874 | -2.5 | 14533 | 13811 | 27322 | 19338 | 2730 | 2989 | 3131 | N | N | N | N | N | N |
| ITPRIPL2 | high in NP | -10.1 | 0.002803273 | -2.6 | 14534 | 402 | 1321 | 772 | 116 | 83 | 83 | N | N | N | N | N | N |
| TGFBI | high in NP | -7.7 | 0.002780771 | -2.6 | 14535 | 673 | 858 | 392 | 66 | 43 | 100 | N | N | N | N | N | N |
| PYGO2 | high in NP | -4.5 | 0.002746676 | -2.6 | 14536 | 109 | 107 | 125 | 26 | 20 | 21 | N | N | N | N | P | N |
| YWHAH | high in NP | -5.9 | 0.0027194 | -2.6 | 14537 | 620 | 1120 | 999 | 129 | 173 | 98 | N | N | N | N | N | N |
| TBL1XR1 | high in NP | -5.6 | 0.002705762 | -2.6 | 14538 | 439 | 378 | 296 | 73 | 63 | 88 | N | N | N | N | N | N |
| PTPLAD2 | high in NP | -9.2 | 0.002652574 | -2.6 | 14539 | 19 | 44 | 28 | 3 | 3 | 3 | N | N | N | N | N | N |
| RAB13 | high in NP | -13.1 | 0.002613024 | -2.6 | 14540 | 131 | 436 | 360 | 28 | 6 | 12 | N | N | N | N | N | N |
| IL28RA | high in NP | -9.3 | 0.002599386 | -2.6 | 14541 | 26 | 36 | 51 | 10 | 10 | 10 | N | N | N | N | N | N |
| TMEM59 | high in NP | -4.2 | 0.002592567 | -2.6 | 14542 | 2296 | 2116 | 2083 | 530 | 464 | 494 | N | N | N | N | N | N |
| GALT | high in NP | -8.0 | 0.002558473 | -2.6 | 14543 | 46 | 47 | 23 | 12 | 12 | 13 | N | N | N | N | N | N |
| VAPA | high in NP | -5.5 | 0.002551654 | -2.6 | 14544 | 372 | 530 | 557 | 100 | 104 | 86 | N | N | N | N | N | N |
| EEF1A1 | high in NP | -10.7 | 0.002515513 | -2.6 | 14545 | 405 | 1066 | 1126 | 86 | 52 | 98 | N | N | N | N | N | N |
| DULLARD | high in NP | -8.1 | 0.002488237 | -2.6 | 14546 | 153 | 310 | 225 | 33 | 16 | 21 | N | N | N | N | N | N |
| DCN | high in NP | -16.3 | 0.002474599 | -2.6 | 14547 | 2533 | 15623 | 4229 | 288 | 269 | 501 | N | N | N | N | N | N |
| ANKRD10 | high in NP | -7.6 | 0.002461643 | -2.6 | 14548 | 308 | 432 | 598 | 75 | 35 | 58 | N | N | N | N | N | N |
| PCBP1 | high in NP | -31.4 | 0.002454824 | -2.6 | 14549 | 365 | 2451 | 2638 | 59 | 46 | 64 | NA | N | N | N | N | N |
| GABARAP | high in NP | -25.7 | 0.002434368 | -2.6 | 14550 | 161 | 989 | 1046 | 35 | 14 | 18 | N | N | N | N | N | N |
| RPSAP58 | high in NP | -11.4 | 0.002415274 | -2.6 | 14551 | 3040 | 9770 | 7188 | 454 | 552 | 725 | NA | NA | N | N | N | N |
| RPL37 | high in NP | -25.7 | 0.002392772 | -2.6 | 14552 | 1487 | 9047 | 8412 | 132 | 256 | 294 | N | N | N | N | N | N |
| PPP6C | high in NP | -15.3 | 0.002358677 | -2.6 | 14553 | 191 | 702 | 617 | 44 | 40 | 23 | N | N | N | N | N | N |
| DLC1 | high in NP | -6.4 | 0.002331401 | -2.6 | 14554 | 100 | 152 | 145 | 23 | 23 | 26 | N | N | N | N | N | N |
| RAC1 | high in NP | -5.3 | 0.002324582 | -2.6 | 14555 | 2983 | 3756 | 2825 | 669 | 558 | 391 | N | N | N | N | N | N |
| PUM1 | high in NP | -5.3 | 0.00230208 | -2.6 | 14556 | 211 | 285 | 316 | 63 | 65 | 59 | N | N | N | N | N | N |
| FGFR1OP2 | high in NP | -8.1 | 0.002288442 | -2.6 | 14557 | 64 | 100 | 130 | 16 | 7 | 13 | N | N | N | N | N | N |
| CD9 | high in NP | -46.3 | 0.002207296 | -2.6 | 14558 | 112 | 1072 | 681 | 6 | 13 | 11 | N | N | N | N | N | N |
| CSTF1 | high in NP | -16.5 | 0.002166383 | -2.7 | 14559 | 27 | 42 | 68 | 6 | 8 | 6 | N | N | N | N | N | N |
| HEPH | high in NP | -9.7 | 0.002152745 | -2.7 | 14560 | 141 | 57 | 49 | 18 | 18 | 18 | N | N | N | N | N | N |
| PPP1CC | high in NP | -9.4 | 0.002139107 | -2.7 | 14561 | 357 | 787 | 458 | 39 | 73 | 52 | N | N | N | N | N | N |
| TMSB10 | high in NP | -17.9 | 0.002125469 | -2.7 | 14562 | 1375 | 5031 | 5667 | 142 | 280 | 239 | N | N | N | P | P | N |
| CD164 | high in NP | -9.3 | 0.002106376 | -2.7 | 14563 | 203 | 382 | 412 | 42 | 30 | 35 | N | N | N | N | N | N |
| GJA1 | high in NP | -9.0 | 0.002085919 | -2.7 | 14564 | 4604 | 4973 | 6353 | 280 | 535 | 828 | N | N | N | N | N | N |
| TMEM9 | high in NP | -6.6 | 0.002051824 | -2.7 | 14565 | 46 | 64 | 68 | 7 | 7 | 7 | N | N | P | N | N | N |
| CCNG1 | high in NP | -13.4 | 0.002038186 | -2.7 | 14566 | 70 | 182 | 178 | 9 | 12 | 6 | N | N | N | N | N | N |
| ISCU | high in NP | -10.2 | 0.002017729 | -2.7 | 14567 | 103 | 211 | 273 | 15 | 15 | 15 | N | N | N | N | P | N |

TABLE 15-continued

Genes that Are Differentially Methylated between Nulliparous and Parous CD44+ Breast Epithelial Cells

| | | | | | SAGE-seq | | | | | | ChIP-seq | | | MSDK-seq | | |
|---|---|---|---|---|---|---|---|---|---|---|---|---|---|---|---|---|
| | | | | | | Nulliparous (NP) | | | Parous (P) | | | NP | | P | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| VKORC1 | high in NP | -12.8 | 0.00201091 | -2.7 | 14568 | 72 | 269 | 92 | 9 | 5 | 5 | N | N | N | N | N | N |
| CDK2AP1 | high in NP | -9.4 | 0.001956359 | -2.7 | 14569 | 696 | 1067 | 1112 | 157 | 103 | 49 | N | N | N | N | N | N |
| COL3A1 | high in NP | -71.2 | 0.001935902 | -2.7 | 14570 | 49181 | 3991 | 3601 | 55 | 155 | 254 | N | N | N | N | N | N |
| EPHB4 | high in NP | -4.7 | 0.001873849 | -2.7 | 14571 | 136 | 158 | 133 | 28 | 28 | 25 | N | N | N | N | N | N |
| SCP2 | high in NP | -5.4 | 0.001860211 | -2.7 | 14572 | 58 | 57 | 61 | 11 | 14 | 11 | N | N | N | N | N | N |
| PPT2 | high in NP | -8.6 | 0.001832936 | -2.7 | 14573 | 46 | 71 | 33 | 10 | 10 | 10 | N | N | N | N | N | N |
| VEZT | high in NP | -9.5 | 0.001826117 | -2.7 | 14574 | 88 | 207 | 179 | 13 | 14 | 14 | N | N | N | N | N | N |
| SEMA3G | high in NP | -5.4 | 0.00180566 | -2.7 | 14575 | 135 | 108 | 128 | 22 | 20 | 18 | N | N | N | N | N | N |
| LUM | high in NP | -38.6 | 0.001785203 | -2.7 | 14576 | 604 | 9203 | 1447 | 31 | 20 | 68 | N | N | N | N | N | N |
| TUBA1A | high in NP | -13.9 | 0.001717565 | -2.7 | 14577 | 329 | 1079 | 846 | 21 | 59 | 30 | N | N | N | N | N | N |
| C17orf106 | high in NP | -6.9 | 0.001764746 | -2.8 | 14578 | 25 | 35 | 39 | 4 | 4 | 4 | N | N | N | N | N | N |
| COL1A2 | high in NP | -16.5 | 0.00172656 | -2.8 | 14579 | 14735 | 3963 | 2750 | 265 | 162 | 391 | NA | NA | N | N | N | N |
| PAPSS1 | high in NP | -9.9 | 0.001719741 | -2.8 | 14580 | 149 | 105 | 82 | 14 | 15 | 9 | N | N | N | N | N | N |
| ATPIF1 | high in NP | -13.4 | 0.001692465 | -2.8 | 14581 | 71 | 193 | 163 | 13 | 11 | 11 | N | N | N | N | N | N |
| HSP90AB1 | high in NP | -14.9 | 0.001672008 | -2.8 | 14582 | 7016 | 20056 | 18444 | 771 | 1175 | 1102 | N | N | N | N | N | N |
| LASP1 | high in NP | -12.5 | 0.00165837 | -2.8 | 14583 | 357 | 558 | 341 | 27 | 17 | 52 | N | N | N | N | N | N |
| P4HA2 | high in NP | -11.7 | 0.001651551 | -2.8 | 14584 | 33 | 56 | 71 | 7 | 7 | 7 | N | N | N | N | N | N |
| KDELR1 | high in NP | -7.1 | 0.001603819 | -2.8 | 14585 | 1036 | 1838 | 1303 | 256 | 181 | 171 | N | N | N | N | N | N |
| TIMP2 | high in NP | -12.3 | 0.001569724 | -2.8 | 14586 | 5246 | 8059 | 2692 | 249 | 230 | 553 | N | N | N | N | N | N |
| HSPA2 | high in NP | -29.4 | 0.00152881 | -2.8 | 14587 | 59 | 126 | 69 | 12 | 8 | 8 | N | N | N | N | N | N |
| MYL9 | high in NP | -21.2 | 0.001481077 | -2.8 | 14588 | 735 | 1281 | 298 | 26 | 51 | 18 | N | N | N | N | N | N |
| RBM3 | high in NP | -15.7 | 0.001467439 | -2.8 | 14589 | 462 | 1306 | 1466 | 80 | 76 | 37 | N | N | N | N | N | N |
| AP2A1 | high in NP | -8.7 | 0.001453802 | -2.8 | 14590 | 143 | 334 | 254 | 30 | 16 | 13 | N | N | N | N | N | N |
| BMS1P5 | high in NP | -18.8 | 0.001433345 | -2.8 | 14591 | 27 | 41 | 72 | 3 | 1 | 1 | N | N | N | N | N | N |
| PLSCR4 | high in NP | -8.5 | 0.001406069 | -2.9 | 14592 | 124 | 206 | 209 | 19 | 19 | 22 | N | N | N | N | N | N |
| NCSTN | high in NP | -13.4 | 0.001392431 | -2.9 | 14593 | 132 | 334 | 122 | 15 | 9 | 15 | N | N | N | N | N | N |
| RPL7 | high in NP | -30.6 | 0.001385612 | -2.9 | 14594 | 1545 | 8408 | 8184 | 141 | 231 | 201 | N | N | N | N | N | N |
| LGALS1 | high in NP | -10.3 | 0.001365155 | -2.9 | 14595 | 2501 | 2584 | 1259 | 231 | 160 | 222 | N | N | N | N | N | N |
| PVRL2 | high in NP | -9.9 | 0.001281282 | -2.9 | 14596 | 892 | 447 | 787 | 75 | 87 | 58 | N | P | N | N | N | N |
| FOS | high in NP | -17.8 | 0.001260825 | -2.9 | 14597 | 2439 | 8583 | 9563 | 192 | 298 | 556 | N | N | N | N | N | N |
| PTGS2 | high in NP | -13.9 | 0.001254006 | -2.9 | 14598 | 760 | 1829 | 2139 | 61 | 61 | 153 | N | N | N | N | N | N |
| SPARC | high in NP | -16.8 | 0.001219911 | -2.9 | 14599 | 7437 | 8035 | 2291 | 376 | 343 | 462 | N | N | N | N | N | N |
| GOLPH3 | high in NP | -8.0 | 0.001213092 | -2.9 | 14600 | 783 | 908 | 820 | 171 | 76 | 102 | N | N | N | N | N | N |
| IGFBP6 | high in NP | -6.6 | 0.001183817 | -2.9 | 14601 | 624 | 589 | 455 | 83 | 56 | 80 | N | N | N | N | N | N |
| C19orf40 | high in NP | -6.4 | 0.001138084 | -2.9 | 14602 | 446 | 495 | 509 | 84 | 49 | 61 | N | N | N | N | N | N |
| C3orf14 | high in NP | -8.8 | 0.001124446 | -2.9 | 14603 | 19 | 13 | 28 | 3 | 3 | 3 | N | N | N | N | P | N |
| PTP4A2 | high in NP | -14.0 | 0.001117627 | -3.0 | 14604 | 715 | 2541 | 1707 | 118 | 93 | 112 | N | N | N | N | N | N |
| MRPS33 | high in NP | -11.1 | 0.001083532 | -3.0 | 14605 | 23 | 49 | 33 | 2 | 2 | 2 | N | P | N | N | P | N |
| ZDHHC1 | high in NP | -6.5 | 0.001049437 | -3.0 | 14606 | 64 | 49 | 65 | 9 | 7 | 7 | N | N | N | N | N | N |
| VCL | high in NP | -7.8 | 0.0010358 | -3.0 | 14607 | 1484 | 1251 | 927 | 154 | 186 | 128 | N | N | N | N | P | N |
| NDUFB4 | high in NP | -40.5 | 0.001015343 | -3.0 | 14608 | 172 | 678 | 872 | 19 | 9 | 5 | N | N | N | N | P | N |
| SCARA5 | high in NP | -7.8 | 0.001008524 | -3.0 | 14609 | 168 | 274 | 160 | 21 | 14 | 20 | N | N | N | N | N | N |
| INS-IGF2 | high in NP | -24.8 | 0.000994886 | -3.0 | 14610 | 1220 | 562 | 534 | 14 | 14 | 57 | N | N | N | N | N | N |
| ITPKB | high in NP | -7.3 | 0.000919877 | -3.0 | 14611 | 135 | 236 | 173 | 24 | 18 | 21 | N | N | N | N | N | N |

TABLE 15-continued

Genes that Are Differentially Methylated between Nulliparous and Parous CD44+ Breast Epithelial Cells

| Gene Symbol | expression pattern | Fold Change | p-value | log10 (p-val.) | Ranking | SAGE-seq Nulliparous (NP) CD44+ N48 | CD44+ N58 | CD44+ N43 | SAGE-seq Parous (P) CD44+ N37 | CD44+ N39 | CD44+ N40 | ChIP-seq CD44+ N74 | CD44+ N66 | MSDK-seq GeneBody NP Met | GeneBody Met | Pro-motor Met | Pro-moter Met |
|---|---|---|---|---|---|---|---|---|---|---|---|---|---|---|---|---|---|
| CPE | high in NP | -12.7 | 0.000913058 | -3.0 | 14612 | 475 | 846 | 357 | 42 | 26 | 52 | N | N | N | N | N | N |
| NPC2 | high in NP | -7.7 | 0.000872145 | -3.1 | 14613 | 685 | 901 | 669 | 65 | 101 | 101 | N | N | N | N | N | N |
| PNRC1 | high in NP | -21.8 | 0.000858507 | -3.1 | 14614 | 1377 | 4940 | 4447 | 226 | 91 | 188 | N | N | N | N | N | N |
| POSTN | high in NP | -8.3 | 0.000778043 | -3.1 | 14615 | 147 | 249 | 139 | 19 | 19 | 19 | N | N | N | N | N | N |
| COL6A1 | high in NP | -9.7 | 0.0007711224 | -3.1 | 14616 | 1969 | 3021 | 1328 | 268 | 184 | 222 | N | N | N | N | N | N |
| CENPH | high in NP | -13.8 | 0.000737129 | -3.1 | 14617 | 119 | 289 | 215 | 10 | 10 | 5 | N | N | N | N | N | N |
| LY96 | high in NP | -12.4 | 0.000723491 | -3.1 | 14618 | 59 | 18 | 12 | 2 | 2 | 2 | N | N | N | N | N | N |
| LOC649330 | high in NP | -7.1 | 0.000682578 | -3.2 | 14619 | 268 | 370 | 291 | 31 | 27 | 35 | NA | NA | N | N | N | N |
| PPP1R15A | high in NP | -14.3 | 0.000675759 | -3.2 | 14620 | 798 | 2037 | 1813 | 86 | 115 | 137 | N | N | N | N | N | N |
| RCN2 | high in NP | -25.1 | 0.000613706 | -3.2 | 14621 | 62 | 167 | 135 | 12 | 9 | 9 | N | N | N | N | N | N |
| ERO1L | high in NP | -20.6 | 0.000568701 | -3.2 | 14622 | 254 | 698 | 701 | 32 | 23 | 16 | N | N | N | N | N | N |
| TMEM14C | high in NP | -23.9 | 0.000555063 | -3.3 | 14623 | 95 | 303 | 159 | 8 | 5 | 5 | N | N | N | N | N | N |
| COX8A | high in NP | -11.1 | 0.000534606 | -3.3 | 14624 | 592 | 1150 | 1065 | 89 | 68 | 69 | N | N | N | N | N | N |
| EEF1G | high in NP | -22.0 | 0.000520968 | -3.3 | 14625 | 4404 | 12125 | 13529 | 351 | 565 | 447 | N | N | N | N | N | N |
| XPNPEP2 | high in NP | -7.7 | 0.000458234 | -3.3 | 14626 | 27 | 29 | 26 | 6 | 6 | 6 | N | N | N | N | N | N |
| RPS20 | high in NP | -14.8 | 0.000437777 | -3.4 | 14627 | 2467 | 7995 | 3850 | 234 | 281 | 250 | N | N | N | N | N | N |
| C5orf13 | high in NP | -15.9 | 0.000430958 | -3.4 | 14628 | 541 | 174 | 183 | 9 | 9 | 9 | N | N | N | P | N | N |
| TCN2 | high in NP | -26.6 | 0.000390044 | -3.4 | 14629 | 76 | 51 | 45 | 9 | 9 | 13 | N | N | N | N | N | N |
| HNRNPA0 | high in NP | -10.6 | 0.000369587 | -3.4 | 14630 | 1350 | 2790 | 1614 | 180 | 140 | 169 | N | N | N | N | N | N |
| SCARB2 | high in NP | -11.1 | 0.000330038 | -3.5 | 14631 | 307 | 523 | 360 | 37 | 23 | 26 | N | N | N | N | N | N |
| C11orf10 | high in NP | -13.6 | 0.0003164 | -3.5 | 14632 | 1250 | 1290 | 1456 | 138 | 85 | 68 | P | N | N | N | N | N |
| CDKN1B | high in NP | -14.6 | 0.000295943 | -3.5 | 14633 | 148 | 158 | 164 | 10 | 8 | 14 | N | N | N | N | N | N |
| SEPP1 | high in NP | -18.3 | 0.00024821 | -3.6 | 14634 | 471 | 524 | 572 | 11 | 21 | 28 | N | N | N | N | N | N |
| HMGCL | high in NP | -16.8 | 0.000200477 | -3.7 | 14635 | 35 | 16 | 25 | 3 | 3 | 3 | N | N | N | N | N | N |
| LRRC41 | high in NP | -14.9 | 0.000186839 | -3.7 | 14636 | 1046 | 2170 | 1490 | 90 | 102 | 68 | N | N | N | N | N | N |
| ALKBH5 | high in NP | -28.8 | 0.000167064 | -3.8 | 14637 | 934 | 2589 | 2079 | 93 | 53 | 48 | N | N | N | N | N | N |
| CUL4B | high in NP | -16.8 | 0.000153427 | -3.8 | 14638 | 117 | 123 | 85 | 17 | 15 | 15 | N | N | N | N | N | N |
| SEP2 | high in NP | -27.3 | 0.000146608 | -3.8 | 14639 | 1162 | 1330 | 1283 | 93 | 44 | 39 | NA | NA | N | N | N | N |
| ITM2A | high in NP | -50.4 | 0.000139789 | -3.9 | 14640 | 1640 | 3240 | 2971 | 27 | 35 | 102 | N | N | N | N | N | N |
| LITAF | high in NP | -17.1 | 0.000126151 | -3.9 | 14641 | 1397 | 3139 | 1979 | 107 | 115 | 119 | N | N | N | N | N | N |
| ACTG1 | high in NP | -22.7 | 0.000112513 | -3.9 | 14642 | 16540 | 18348 | 12824 | 607 | 948 | 494 | N | N | N | N | N | N |
| KLK3 | high in NP | -28.6 | 7.16E-05 | -4.1 | 14643 | 50 | 43 | 51 | 3 | 3 | 3 | P | P | N | N | N | N |
| SS18L2 | high in P | 28.4 | 7.84E-05 | 4.1 | 1 | 127 | 108 | 170 | 3241 | 3173 | 4378 | N | N | N | N | N | N |
| PUS7L | high in P | 22.1 | 8.52E-05 | 4.1 | 2 | 7 | 7 | 7 | 24 | 32 | 35 | N | N | N | N | N | N |
| INTS12 | high in P | 15.9 | 9.21E-05 | 4.0 | 3 | 23 | 18 | 15 | 278 | 357 | 220 | N | N | N | N | N | N |
| CCT2 | high in P | 16.1 | 9.89E-05 | 4.0 | 4 | 905 | 888 | 1060 | 14970 | 19937 | 15800 | N | N | N | N | N | N |
| CECR6 | high in P | 16.7 | 0.000105694 | 4.0 | 5 | 7 | 7 | 8 | 24 | 23 | 35 | P | P | N | N | N | N |
| LEAP2 | high in P | 12.6 | 0.000119332 | 3.9 | 6 | 1 | 1 | 1 | 14 | 14 | 18 | N | N | N | N | N | N |
| NME2P1 | high in P | 24.0 | 0.000160245 | 3.8 | 7 | 2 | 2 | 3 | 48 | 69 | 77 | N | N | N | N | N | N |
| QRSL1 | high in P | 22.9 | 0.000173883 | 3.8 | 8 | 44 | 25 | 46 | 648 | 939 | 700 | N | N | N | N | N | N |
| RAB39 | high in P | 18.8 | 0.000207296 | 3.7 | 9 | 2 | 2 | 3 | 27 | 29 | 15 | N | N | N | N | N | N |
| PRICKLE3 | high in P | 14.7 | 0.000214115 | 3.7 | 10 | 7 | 17 | 23 | 241 | 316 | 388 | P | P | N | N | N | N |
| AIPL1 | high in P | 20.5 | 0.000220934 | 3.7 | 11 | 9 | 2 | 3 | 54 | 47 | 43 | P | P | N | N | N | N |
| ZNF93 | high in P | 21.1 | 0.000227753 | 3.6 | 12 | 4 | 7 | 6 | 106 | 70 | 136 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | Nulliparous (NP) | | | Parous (P) | | | NP | | P | NP | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| HPVC1 | high in P | 11.1 | 0.000234572 | 3.6 | 13 | 2 | 2 | 3 | 14 | 14 | 18 | N | N | N | N | N | N |
| MAP1S | high in P | 16.1 | 0.000241391 | 3.6 | 14 | 277 | 158 | 375 | 4509 | 5657 | 4396 | N | N | N | N | N | N |
| LRRC10 | high in P | 13.5 | 0.000255029 | 3.6 | 15 | 5 | 5 | 5 | 16 | 27 | 20 | N | N | N | N | N | N |
| ACTR5 | high in P | 19.0 | 0.000261848 | 3.6 | 16 | 16 | 32 | 43 | 649 | 698 | 502 | P | P | N | N | N | N |
| CCDC13 | high in P | 14.3 | 0.000268667 | 3.6 | 17 | 2 | 2 | 2 | 16 | 25 | 13 | P | P | N | N | N | N |
| C12orf59 | high in P | 20.5 | 0.000275486 | 3.6 | 18 | 11 | 5 | 6 | 40 | 50 | 61 | P | N | N | N | N | N |
| RGPD1 | high in P | 23.9 | 0.000282305 | 3.5 | 19 | 5 | 7 | 5 | 131 | 162 | 111 | N | N | N | N | N | N |
| ZNF692 | high in P | 17.0 | 0.000289124 | 3.5 | 20 | 37 | 17 | 34 | 433 | 479 | 618 | N | N | P | P | N | N |
| DCXR | high in P | 29.4 | 0.000302762 | 3.5 | 21 | 87 | 92 | 268 | 3532 | 4763 | 2673 | N | N | N | N | N | N |
| GPATCH2 | high in P | 17.9 | 0.000323219 | 3.5 | 22 | 10 | 15 | 18 | 111 | 219 | 225 | N | N | N | N | N | N |
| C15orf48 | high in P | 43.5 | 0.000336856 | 3.5 | 23 | 14 | 9 | 3 | 151 | 295 | 230 | N | N | N | N | N | N |
| POLR3E | high in P | 11.8 | 0.000349131 | 3.5 | 24 | 28 | 47 | 57 | 367 | 557 | 610 | N | N | N | N | N | N |
| PPP4R1L | high in P | 19.9 | 0.000355595 | 3.4 | 25 | 4 | 4 | 4 | 36 | 27 | 27 | N | N | N | N | N | N |
| PRO0628 | high in P | 28.4 | 0.000362768 | 3.4 | 26 | 9 | 2 | 4 | 76 | 65 | 110 | N | N | N | N | N | N |
| ZNF619 | high in P | 26.7 | 0.000376406 | 3.4 | 27 | NA | NA | NA | NA | NA | NA | NA | NA | N | N | N | N |
| ACCN3 | high in P | 19.3 | 0.000383225 | 3.4 | 28 | 7 | 8 | 18 | 171 | 258 | 323 | N | N | N | N | N | N |
| MESTIT1 | high in P | 18.8 | 0.000396863 | 3.4 | 29 | 20 | 9 | 20 | 266 | 215 | 408 | N | N | N | N | N | N |
| C5orf60 | high in P | 12.2 | 0.000403682 | 3.4 | 30 | 2 | 3 | 3 | 32 | 14 | 15 | N | N | N | N | N | N |
| PTPN23 | high in P | 21.8 | 0.000410501 | 3.4 | 31 | 197 | 112 | 294 | 4663 | 4370 | 2429 | N | N | N | N | N | N |
| SLC45A4 | high in P | 14.2 | 0.000424139 | 3.4 | 32 | 19 | 25 | 25 | 224 | 311 | 262 | N | N | N | N | N | N |
| BCL2L12 | high in P | 14.2 | 0.000444596 | 3.4 | 33 | 31 | 27 | 54 | 391 | 380 | 416 | N | N | N | N | N | N |
| MAGI2 | high in P | 10.2 | 0.000451415 | 3.3 | 34 | 32 | 32 | 46 | 266 | 224 | 300 | N | N | N | N | N | N |
| XRCC6 | high in P | 11.2 | 0.000465053 | 3.3 | 35 | 1742 | 1343 | 2659 | 21489 | 22306 | 18279 | N | N | N | N | N | N |
| SMURF1 | high in P | 18.4 | 0.000471872 | 3.3 | 36 | 303 | 101 | 394 | 5495 | 6799 | 5795 | N | N | N | N | P | N |
| KRBA1 | high in P | 22.9 | 0.000478691 | 3.3 | 37 | 16 | 20 | 33 | 405 | 554 | 205 | P | N | N | N | N | N |
| KCNK3 | high in P | 14.8 | 0.000485551 | 3.3 | 38 | 9 | 13 | 11 | 256 | 94 | 69 | P | P | N | N | N | N |
| RINT1 | high in P | 16.2 | 0.000492329 | 3.3 | 39 | 23 | 13 | 27 | 321 | 235 | 152 | N | N | N | N | N | N |
| C21orf88 | high in P | 8.6 | 0.000499148 | 3.3 | 40 | 99 | 77 | 99 | 665 | 728 | 848 | NA | NA | N | N | N | N |
| SLC16A13 | high in P | 12.3 | 0.000514149 | 3.3 | 41 | 1 | 1 | 1 | 12 | 17 | 9 | N | N | N | N | N | N |
| CFP | high in P | 12.5 | 0.000527787 | 3.3 | 42 | 24 | 9 | 9 | 147 | 113 | 175 | NA | NA | N | N | N | N |
| ANAPC1 | high in P | 14.9 | 0.000541425 | 3.3 | 43 | 70 | 25 | 48 | 663 | 682 | 702 | NA | NA | N | N | N | N |
| RMND5B | high in P | 16.5 | 0.000548244 | 3.3 | 44 | 47 | 20 | 26 | 733 | 511 | 296 | N | N | N | N | N | N |
| GPR37L1 | high in P | 15.2 | 0.000561882 | 3.3 | 45 | 14 | 9 | 22 | 147 | 228 | 289 | N | N | N | N | N | N |
| LOC493754 | high in P | 15.1 | 0.00057552 | 3.2 | 46 | 370 | 202 | 458 | 3476 | 4487 | 6672 | NA | NA | N | N | N | N |
| ZNF836 | high in P | 14.0 | 0.000582339 | 3.2 | 47 | 2 | 4 | 4 | 56 | 34 | 36 | N | N | N | N | N | N |
| CD101 | high in P | 43.6 | 0.000589158 | 3.2 | 48 | 7 | 7 | 9 | 50 | 208 | 240 | N | N | N | N | N | N |
| PLAC8L1 | high in P | 15.3 | 0.000620525 | 3.2 | 49 | 1 | 1 | 1 | 16 | 19 | 28 | NA | NA | N | N | N | N |
| SKA1 | high in P | 7.5 | 0.000627344 | 3.2 | 50 | 3 | 3 | 3 | 9 | 10 | 14 | NA | NA | N | N | N | N |
| METTL2B | high in P | 29.8 | 0.000634163 | 3.2 | 51 | 2 | 2 | 4 | 42 | 61 | 39 | NA | NA | N | N | N | N |
| CASP8 | high in P | 11.7 | 0.000640982 | 3.2 | 52 | 39 | 28 | 42 | 287 | 462 | 510 | N | N | N | N | N | N |
| ADRB3 | high in P | 8.0 | 0.000647801 | 3.2 | 53 | 29 | 30 | 25 | 198 | 157 | 211 | P | N | N | N | N | N |
| NASP | high in P | 11.8 | 0.00065462 | 3.2 | 54 | 148 | 184 | 330 | 1941 | 2047 | 2985 | N | N | N | N | N | N |
| FAM83E | high in P | 14.4 | 0.00066894 | 3.2 | 55 | 41 | 14 | 37 | 349 | 376 | 493 | N | N | N | N | N | N |
| RAGE | high in P | 15.9 | 0.000689397 | 3.2 | 56 | 15 | 20 | 30 | 240 | 299 | 281 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | Nulliparous (NP) | | | Parous (P) | | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| SDR39U1 | high in P | 10.3 | 0.000696215 | 3.2 | 57 | 228 | 207 | 364 | 2331 | 1969 | 2789 | NA | NA | N | N | N | N |
| SNORA21 | high in P | 19.4 | 0.000703034 | 3.2 | 58 | 1 | 1 | 2 | 22 | 22 | 33 | N | N | N | N | N | N |
| TIMM17B | high in P | 9.2 | 0.000709853 | 3.1 | 59 | 39 | 30 | 50 | 453 | 346 | 261 | N | N | N | N | N | N |
| ZSCAN20 | high in P | 9.3 | 0.000716672 | 3.1 | 60 | 3 | 3 | 4 | 13 | 17 | 11 | N | N | N | N | N | N |
| TSEN54 | high in P | 14.0 | 0.00073031 | 3.1 | 61 | 48 | 22 | 45 | 337 | 576 | 384 | N | N | N | N | N | N |
| HPDL | high in P | 52.9 | 0.000743948 | 3.1 | 62 | 1 | 1 | 6 | 118 | 205 | 65 | N | N | N | N | N | N |
| DPH3B | high in P | 7.4 | 0.000750767 | 3.1 | 63 | 2 | 3 | 3 | 18 | 25 | 15 | N | N | N | N | N | N |
| MTERFD2 | high in P | 7.0 | 0.000764405 | 3.1 | 64 | 16 | 24 | 19 | 203 | 116 | 121 | N | N | N | N | N | N |
| LOC642313 | high in P | 20.5 | 0.000784862 | 3.1 | 65 | 9 | 3 | 5 | 46 | 48 | 70 | N | N | N | N | N | N |
| BCAN | high in P | 15.8 | 0.000791681 | 3.1 | 66 | 22 | 8 | 23 | 245 | 180 | 312 | N | N | N | N | N | N |
| FCER1G | high in P | 38.4 | 0.0007985 | 3.1 | 67 | 2 | 2 | 2 | 74 | 12 | 45 | N | N | N | N | N | N |
| PECR | high in P | 26.1 | 0.000805319 | 3.1 | 68 | 2 | 2 | 4 | 52 | 29 | 45 | N | N | N | N | N | N |
| C17orf67 | high in P | 27.3 | 0.000812138 | 3.1 | 69 | 13 | 2 | 9 | 146 | 136 | 224 | N | N | N | N | N | N |
| C9orf45 | high in P | 14.7 | 0.000818957 | 3.1 | 70 | 6 | 6 | 7 | 18 | 22 | 61 | N | N | N | N | N | N |
| ZNF33A | high in P | 12.5 | 0.000825776 | 3.1 | 71 | 13 | 16 | 20 | 123 | 220 | 118 | NA | NA | N | N | N | N |
| LRWD1 | high in P | 9.2 | 0.000832595 | 3.1 | 72 | 11 | 20 | 17 | 158 | 160 | 113 | N | N | N | N | N | N |
| COX18 | high in P | 20.8 | 0.000839414 | 3.1 | 73 | 21 | 11 | 13 | 183 | 164 | 210 | N | N | N | N | N | N |
| ZNF767 | high in P | 14.8 | 0.000865326 | 3.1 | 74 | 28 | 14 | 34 | 272 | 331 | 276 | N | N | N | N | P | N |
| ATP6V1B1 | high in P | 13.8 | 0.000864964 | 3.1 | 75 | 15 | 6 | 11 | 74 | 169 | 75 | N | N | N | N | N | N |
| NCF4 | high in P | 12.8 | 0.000885782 | 3.1 | 76 | 3 | 9 | 15 | 80 | 199 | 201 | P | N | N | N | N | N |
| SNORD22 | high in P | 15.5 | 0.000892601 | 3.0 | 77 | 22 | 5 | 21 | 156 | 311 | 230 | N | N | N | N | N | N |
| NRBP1 | high in P | 7.1 | 0.00089942 | 3.0 | 78 | 384 | 413 | 351 | 3673 | 2470 | 2225 | N | N | N | N | N | N |
| ATP6V0B | high in P | 7.3 | 0.000906239 | 3.0 | 79 | 386 | 487 | 514 | 4121 | 2580 | 3346 | NA | NA | N | N | N | N |
| ZNF570 | high in P | 15.4 | 0.000926696 | 3.0 | 80 | 2 | 2 | 4 | 39 | 27 | 59 | N | N | N | N | N | N |
| PIK3CG | high in P | 14.2 | 0.000933515 | 3.0 | 81 | 6 | 6 | 6 | 22 | 22 | 22 | N | N | N | N | N | N |
| HLA-DOB | high in P | 10.9 | 0.000947153 | 3.0 | 82 | 6 | 6 | 6 | 22 | 34 | 24 | N | N | N | N | N | N |
| NPB | high in P | 12.6 | 0.000953972 | 3.0 | 83 | 1 | 2 | 1 | 14 | 21 | 24 | N | N | N | N | N | N |
| B3GNT3 | high in P | 7.3 | 0.000974429 | 3.0 | 84 | 23 | 18 | 29 | 137 | 160 | 175 | P | N | N | N | N | N |
| ZIK1 | high in P | 26.2 | 0.000981248 | 3.0 | 85 | 2 | 2 | 2 | 30 | 33 | 10 | N | N | N | N | N | N |
| C8orf86 | high in P | 16.9 | 0.000988067 | 3.0 | 86 | 39 | 32 | 91 | 674 | 949 | 498 | NA | NA | N | N | N | N |
| NOC4L | high in P | 11.8 | 0.001001705 | 3.0 | 87 | 93 | 64 | 129 | 1166 | 1499 | 720 | N | N | N | N | N | N |
| SHARPIN | high in P | 13.2 | 0.001022162 | 3.0 | 88 | 116 | 41 | 72 | 1090 | 898 | 532 | N | N | N | N | N | N |
| TCP11L1 | high in P | 7.7 | 0.001028981 | 3.0 | 89 | 57 | 49 | 44 | 466 | 395 | 280 | N | N | N | N | N | N |
| METTL2A | high in P | 8.1 | 0.001042618 | 3.0 | 90 | 32 | 37 | 22 | 155 | 224 | 245 | N | N | N | N | N | N |
| FAM166B | high in P | 6.9 | 0.001056256 | 3.0 | 91 | 4 | 4 | 4 | 10 | 9 | 12 | N | N | N | N | N | N |
| TMEM213 | high in P | 11.1 | 0.001063075 | 3.0 | 92 | 44 | 25 | 20 | 208 | 239 | 340 | P | N | N | N | N | N |
| ZSCAN16 | high in P | 16.5 | 0.001076713 | 3.0 | 93 | 2 | 2 | 2 | 56 | 28 | 15 | N | P | N | N | N | N |
| ZNF844 | high in P | 16.7 | 0.001090351 | 3.0 | 94 | 3 | 3 | 4 | 43 | 19 | 51 | N | N | N | N | N | N |
| PHB | high in P | 9.4 | 0.00109717 | 3.0 | 95 | 24 | 18 | 13 | 89 | 203 | 99 | N | N | N | N | N | N |
| CTPS | high in P | 10.4 | 0.001103989 | 3.0 | 96 | 47 | 78 | 31 | 640 | 710 | 478 | NA | NA | N | N | N | N |
| PLEKHM1P | high in P | 87.8 | 0.001110808 | 3.0 | 97 | 2 | 3 | 25 | 330 | 360 | 349 | N | N | N | N | N | N |
| NRN1L | high in P | 26.1 | 0.001131265 | 2.9 | 98 | 11 | 5 | 8 | 82 | 41 | 64 | N | N | N | N | N | N |
| SPSB2 | high in P | 34.1 | 0.001144903 | 2.9 | 99 | 1 | 1 | 4 | 130 | 40 | 51 | N | N | N | N | N | N |
| SNX5 | high in P | 8.0 | 0.001151722 | 2.9 | 100 | 191 | 97 | 176 | 1110 | 1440 | 1306 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | Nulliparous (NP) | | | Parous (P) | | | NP | | P | | GeneBody | Pro-moter | Pro-moter |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | NP Met | Met | P Met |
| C9orf142 | high in P | 11.9 | 0.00158541 | 2.9 | 101 | 31 | 16 | 37 | 230 | 270 | 183 | N | N | N | N | N | N | N |
| PHKG1 | high in P | 12.5 | 0.00116536 | 2.9 | 102 | 6 | 6 | 6 | 17 | 38 | 40 | N | N | N | N | N | N | N |
| INHA | high in P | 10.8 | 0.000172179 | 2.9 | 103 | 3 | 3 | 3 | 42 | 12 | 14 | N | N | N | N | N | N | N |
| FAM153B | high in P | 8.5 | 0.000178998 | 2.9 | 104 | 15 | 22 | 18 | 126 | 157 | 136 | N | N | N | N | N | N | N |
| TMCO7 | high in P | 8.1 | 0.000192636 | 2.9 | 105 | 13 | 17 | 22 | 115 | 114 | 100 | N | N | N | N | N | N | N |
| SMARCA4 | high in P | 16.8 | 0.000199454 | 2.9 | 106 | 99 | 155 | 365 | 2609 | 3972 | 2048 | NA | NA | N | N | N | N | N |
| LOC100288730 | high in P | 9.0 | 0.000206273 | 2.9 | 107 | 9 | 4 | 8 | 75 | 56 | 83 | N | N | N | N | N | N | N |
| POLG | high in P | 7.5 | 0.000122673 | 2.9 | 108 | 278 | 275 | 404 | 1883 | 1908 | 2851 | N | N | N | N | N | N | N |
| C1orf51 | high in P | 19.7 | 0.000233549 | 2.9 | 109 | 20 | 35 | 67 | 406 | 646 | 653 | N | N | N | N | N | N | N |
| SIN3A | high in P | 11.5 | 0.000240368 | 2.9 | 110 | 354 | 213 | 239 | 2699 | 2038 | 4280 | N | N | N | N | N | N | N |
| SECISBP2 | high in P | 13.2 | 0.000247187 | 2.9 | 111 | 128 | 36 | 87 | 1504 | 1084 | 816 | N | N | N | N | N | N | N |
| AMZ1 | high in P | 6.0 | 0.000267644 | 2.9 | 112 | 20 | 19 | 16 | 90 | 74 | 68 | N | N | N | N | N | N | N |
| RBM19 | high in P | 9.5 | 0.000274463 | 2.9 | 113 | 64 | 48 | 84 | 619 | 781 | 478 | N | N | N | N | N | N | N |
| DDX51 | high in P | 8.1 | 0.000296966 | 2.9 | 114 | 50 | 31 | 50 | 417 | 482 | 395 | N | N | N | N | N | N | N |
| USP45 | high in P | 10.2 | 0.000303785 | 2.9 | 115 | 44 | 27 | 30 | 193 | 187 | 335 | N | N | N | N | N | N | P |
| ZBTB7B | high in P | 11.2 | 0.000310603 | 2.9 | 116 | 106 | 46 | 70 | 736 | 868 | 554 | N | N | N | N | N | N | N |
| SCNM1 | high in P | 13.3 | 0.000317422 | 2.9 | 117 | 2 | 13 | 7 | 174 | 103 | 91 | N | N | N | N | N | N | N |
| ACOX3 | high in P | 14.3 | 0.000324241 | 2.9 | 118 | 9 | 20 | 25 | 160 | 188 | 230 | N | N | N | N | N | N | N |
| ZNF554 | high in P | 7.4 | 0.00133106 | 2.9 | 119 | 26 | 20 | 35 | 217 | 192 | 212 | N | N | N | N | N | N | N |
| SPC25 | high in P | 10.8 | 0.000337879 | 2.9 | 120 | 2 | 2 | 2 | 13 | 9 | 22 | N | N | N | N | N | N | N |
| KIAA0562 | high in P | 8.9 | 0.000344698 | 2.9 | 121 | 91 | 52 | 68 | 558 | 584 | 444 | N | N | N | N | N | N | N |
| TDGF1 | high in P | 12.3 | 0.000351517 | 2.9 | 122 | 4 | 4 | 4 | 15 | 32 | 12 | N | N | N | N | N | N | N |
| CSNK2A1P | high in P | 9.8 | 0.000358336 | 2.9 | 123 | 177 | 58 | 144 | 1383 | 1587 | 1165 | N | N | N | N | N | N | N |
| SPEG | high in P | 22.9 | 0.000371974 | 2.9 | 124 | 23 | 17 | 17 | 78 | 294 | 116 | NA | NA | N | N | N | N | N |
| DEXI | high in P | 12.0 | 0.000378793 | 2.9 | 125 | 542 | 163 | 440 | 5214 | 4984 | 3872 | NA | NA | N | P | N | N | N |
| CCBP2 | high in P | 9.1 | 0.000139925 | 2.9 | 126 | 26 | 33 | 63 | 272 | 350 | 298 | NA | NA | N | N | N | N | N |
| ZNF384 | high in P | 12.2 | 0.000412888 | 2.8 | 127 | 219 | 81 | 108 | 1288 | 1373 | 1238 | N | N | N | N | N | N | N |
| CYB5R2 | high in P | 11.3 | 0.000419707 | 2.8 | 128 | 40 | 36 | 83 | 664 | 783 | 342 | P | N | N | N | N | N | N |
| LOC100128640 | high in P | 6.3 | 0.000426526 | 2.8 | 129 | 8 | 11 | 16 | 62 | 49 | 71 | N | N | N | N | N | N | N |
| SLC23A3 | high in P | 28.8 | 0.000440164 | 2.8 | 130 | 6 | 6 | 6 | 29 | 40 | 211 | N | N | N | N | N | N | N |
| CTU2 | high in P | 8.4 | 0.000446983 | 2.8 | 131 | 53 | 40 | 65 | 368 | 492 | 320 | N | N | N | N | N | N | N |
| FAM32A | high in P | 4.9 | 0.000460621 | 2.8 | 132 | 208 | 239 | 227 | 1273 | 1068 | 1077 | P | N | N | N | N | N | N |
| MRPL34 | high in P | 14.5 | 0.000474258 | 2.8 | 133 | 142 | 38 | 120 | 2032 | 1512 | 957 | NA | NA | N | N | N | N | N |
| NOL6 | high in P | 24.8 | 0.000487896 | 2.8 | 134 | 29 | 20 | 45 | 305 | 955 | 521 | NA | NA | N | N | N | N | N |
| SMCR8 | high in P | 8.8 | 0.000494715 | 2.8 | 135 | 105 | 69 | 103 | 847 | 551 | 840 | N | N | N | N | N | N | N |
| RAB34 | high in P | 13.9 | 0.000501534 | 2.8 | 136 | 825 | 248 | 469 | 10393 | 6267 | 4575 | N | N | N | N | N | N | N |
| G6PD | high in P | 17.2 | 0.000508353 | 2.8 | 137 | 227 | 174 | 569 | 7318 | 4141 | 2816 | N | N | N | N | N | N | N |
| ACSL4 | high in P | 5.5 | 0.000515172 | 2.8 | 138 | 76 | 79 | 96 | 523 | 451 | 411 | P | P | N | N | N | N | N |
| ANKRD34C | high in P | 25.1 | 0.000521991 | 2.8 | 139 | 2 | 2 | 3 | 33 | 60 | 32 | NA | NA | N | N | N | N | N |
| TCHP | high in P | 11.1 | 0.000535629 | 2.8 | 140 | 30 | 12 | 20 | 203 | 233 | 222 | N | N | N | N | N | N | N |
| UPK3B | high in P | 43.2 | 0.000542448 | 2.8 | 141 | 12 | 6 | 33 | 250 | 204 | 309 | N | N | N | N | N | N | N |
| ST7L | high in P | 9.8 | 0.000549267 | 2.8 | 142 | 12 | 14 | 20 | 103 | 106 | 68 | P | N | N | N | N | N | N |
| FADS6 | high in P | 7.9 | 0.000556086 | 2.8 | 143 | 5 | 5 | 5 | 20 | 23 | 22 | P | P | N | N | N | N | N |
| ATP2A3 | high in P | 7.7 | 0.000562905 | 2.8 | 144 | 49 | 30 | 29 | 333 | 203 | 292 | N | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | | MSDK-seq | | |
| --- | --- | --- | --- | --- | --- | --- | --- | --- | --- | --- | --- | --- | --- | --- | --- | --- | --- | --- |
| | | | | | | Nulliparous (NP) | | | | Parous (P) | | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | NP | CD44+ N66 | P | GeneBody NP Met | GeneBody Met | Pro-moter Met | Pro-moter Met |
| | | | | | | | | | | | | | | | | NP | P | NP | P |
| IL2RA | high in P | 8.0 | 0.001576543 | 2.8 | 145 | 112 | 58 | 99 | 670 | 641 | 903 | N | N | N | NA | N | N | N | N |
| LOC401127 | high in P | 10.9 | 0.001583362 | 2.8 | 146 | 15 | 7 | 12 | 72 | 76 | 152 | NA | N | N | N | N | N | N | N |
| FGFR2 | high in P | 7.9 | 0.001590181 | 2.8 | 147 | 67 | 64 | 82 | 348 | 498 | 684 | N | N | P | N | N | N | N | N |
| KAT2A | high in P | 10.8 | 0.001610638 | 2.8 | 148 | 111 | 103 | 203 | 1060 | 964 | 2006 | P | N | P | N | N | N | P | N |
| ATP1B4 | high in P | 6.3 | 0.001620866 | 2.8 | 149 | 2 | 2 | 2 | 9 | 7 | 7 | P | N | P | N | N | N | N | N |
| XKR6 | high in P | 6.3 | 0.001620866 | 2.8 | 150 | 6 | 6 | 6 | 13 | 11 | 11 | N | N | N | N | N | N | N | N |
| NUDT12 | high in P | 17.0 | 0.001631094 | 2.8 | 151 | 3 | 3 | 4 | 24 | 46 | 21 | N | N | NA | N | N | N | N | N |
| PAPL | high in P | 7.7 | 0.001637913 | 2.8 | 152 | 176 | 112 | 246 | 1339 | 1246 | 1774 | N | N | N | N | N | N | N | N |
| PRKDC | high in P | 11.3 | 0.001644732 | 2.8 | 153 | 151 | 104 | 242 | 2180 | 1746 | 1086 | N | N | N | N | N | N | N | N |
| LGSN | high in P | 12.3 | 0.001665189 | 2.8 | 154 | 7 | 7 | 8 | 19 | 34 | 25 | N | N | N | N | N | N | N | N |
| RECQL4 | high in P | 14.2 | 0.001678827 | 2.8 | 155 | 14 | 15 | 25 | 93 | 160 | 282 | N | N | N | N | N | N | N | N |
| FAM73B | high in P | 5.4 | 0.001685646 | 2.8 | 156 | 56 | 48 | 72 | 319 | 295 | 295 | N | N | N | N | N | N | N | N |
| DECR2 | high in P | 19.1 | 0.001699284 | 2.8 | 157 | 15 | 30 | 74 | 334 | 543 | 519 | N | N | N | N | N | N | N | N |
| PRDM11 | high in P | 14.7 | 0.001706103 | 2.8 | 158 | 3 | 3 | 4 | 9 | 19 | 28 | N | N | P | N | N | N | P | N |
| NHLRC1 | high in P | 9.6 | 0.001733379 | 2.8 | 159 | 3 | 3 | 4 | 28 | 32 | 33 | N | N | N | N | N | N | N | N |
| PGS1 | high in P | 17.4 | 0.001745653 | 2.8 | 160 | 83 | 16 | 44 | 1055 | 708 | 465 | N | N | N | N | N | N | N | N |
| CYP2D6 | high in P | 10.3 | 0.001757927 | 2.8 | 161 | 2 | 2 | 2 | 15 | 13 | 7 | N | N | N | N | N | N | N | N |
| KLC2 | high in P | 9.8 | 0.001778384 | 2.8 | 162 | 101 | 46 | 143 | 1023 | 1093 | 874 | N | N | N | N | N | N | N | N |
| DUSP9 | high in P | 8.9 | 0.001792022 | 2.7 | 163 | 10 | 4 | 4 | 12 | 17 | 15 | N | P | N | N | N | N | N | N |
| ZFP41 | high in P | 9.2 | 0.001798841 | 2.7 | 164 | 21 | 7 | 13 | 126 | 107 | 88 | N | N | N | N | N | N | N | N |
| MGC16384 | high in P | 22.3 | 0.001812479 | 2.7 | 165 | 5 | 8 | 5 | 33 | 37 | 43 | N | N | NA | N | N | N | N | N |
| FBXO27 | high in P | 10.7 | 0.001819298 | 2.7 | 166 | 61 | 21 | 38 | 276 | 357 | 377 | N | N | N | N | N | N | N | N |
| PRDX6 | high in P | 7.0 | 0.001839755 | 2.7 | 167 | 1633 | 1342 | 1357 | 14135 | 7418 | 9299 | N | N | N | N | N | N | N | N |
| CHST9 | high in P | 7.9 | 0.001846573 | 2.7 | 168 | 12 | 13 | 13 | 33 | 38 | 35 | P | N | P | N | N | N | N | N |
| DNAH12 | high in P | 6.9 | 0.001855392 | 2.7 | 169 | 13 | 14 | 15 | 64 | 78 | 68 | NA | N | NA | N | N | N | N | N |
| FAM127A | high in P | 6.1 | 0.00186703 | 2.7 | 170 | 13 | 8 | 10 | 45 | 16 | 37 | N | N | N | N | N | N | N | N |
| ERP27 | high in P | 8.8 | 0.001880668 | 2.7 | 171 | 2 | 2 | 3 | 27 | 16 | 18 | N | N | N | N | N | N | N | N |
| TTC32 | high in P | 6.5 | 0.001887487 | 2.7 | 172 | 30 | 13 | 16 | 139 | 88 | 98 | N | N | N | N | N | N | N | N |
| KDM5C | high in P | 10.9 | 0.001894306 | 2.7 | 173 | 137 | 58 | 81 | 815 | 854 | 807 | NA | N | NA | N | N | N | N | N |
| MAK | high in P | 14.5 | 0.00190658 | 2.7 | 174 | 11 | 11 | 12 | 61 | 54 | 48 | N | N | N | N | N | N | N | N |
| DCLRE1C | high in P | 11.5 | 0.001913399 | 2.7 | 175 | 42 | 22 | 23 | 275 | 192 | 278 | N | N | N | N | N | N | N | N |
| TBC1D26 | high in P | 12.3 | 0.001920218 | 2.7 | 176 | 2 | 2 | 3 | 14 | 41 | 39 | N | N | N | N | N | N | N | N |
| SIRPB2 | high in P | 72.0 | 0.001942721 | 2.7 | 177 | 3 | 5 | 26 | 302 | 154 | 308 | N | N | N | N | N | N | N | N |
| C14orf73 | high in P | 7.8 | 0.00194954 | 2.7 | 178 | 2 | 2 | 3 | 20 | 29 | 38 | P | N | P | N | N | N | N | N |
| VPS16 | high in P | 5.6 | 0.001963178 | 2.7 | 179 | 38 | 45 | 40 | 314 | 197 | 174 | NA | N | NA | N | N | N | N | N |
| RDH16 | high in P | 12.2 | 0.001969997 | 2.7 | 180 | 1 | 1 | 1 | 25 | 12 | 6 | N | N | N | N | N | N | N | N |
| TMEM222 | high in P | 6.8 | 0.001976816 | 2.7 | 181 | 272 | 171 | 176 | 1912 | 1709 | 1124 | N | N | N | N | N | N | N | N |
| TSPYL2 | high in P | 11.4 | 0.001983635 | 2.7 | 182 | 1299 | 724 | 1755 | 16874 | 7957 | 24816 | N | P | N | P | N | N | N | N |
| RGS12 | high in P | 12.9 | 0.001990453 | 2.7 | 183 | 69 | 34 | 94 | 543 | 1017 | 1179 | P | N | P | N | N | N | N | N |
| GPR83 | high in P | 9.0 | 0.001997272 | 2.7 | 184 | 6 | 7 | 10 | 58 | 53 | 94 | N | N | N | N | N | N | N | N |
| SPHK2 | high in P | 7.5 | 0.002004091 | 2.7 | 185 | 61 | 31 | 63 | 469 | 336 | 332 | P | N | P | N | N | N | N | N |
| TMEM169 | high in P | 11.5 | 0.002024548 | 2.7 | 186 | 5 | 5 | 5 | 40 | 16 | 30 | N | N | N | N | N | N | N | N |
| TMEM212 | high in P | 7.0 | 0.002031367 | 2.7 | 187 | 67 | 52 | 66 | 345 | 471 | 742 | NA | N | NA | N | N | N | N | N |
| YIF1B | high in P | 6.1 | 0.002045005 | 2.7 | 188 | 13 | 17 | 17 | 61 | 76 | 44 | N | N | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | Nulliparous (NP) | | | Parous (P) | | | | NP | P | | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| NHLH1 | high in P | 8.6 | 0.000205643 | 2.7 | 189 | 4 | 5 | 6 | 25 | 51 | 34 | N | N | N | N | N | N |
| TNFRSF4 | high in P | 16.1 | 0.00020562 | 2.7 | 190 | 94 | 19 | 74 | 924 | 557 | 1415 | N | N | N | N | N | N |
| LRRC27 | high in P | 8.1 | 0.0002079791 | 2.7 | 191 | 90 | 51 | 102 | 525 | 721 | 792 | N | N | N | N | N | N |
| CACNB1 | high in P | 15.4 | 0.00020999557 | 2.7 | 192 | 46 | 35 | 121 | 539 | 769 | 1139 | N | N | N | N | N | N |
| MRTO4 | high in P | 10.2 | 0.000218665 | 2.7 | 193 | 88 | 96 | 206 | 1211 | 1926 | 938 | N | N | N | N | N | N |
| YJEFN3 | high in P | 7.2 | 0.000213288 | 2.7 | 194 | 11 | 13 | 13 | 37 | 31 | 48 | N | N | N | N | N | N |
| HNRNPU | high in P | 6.6 | 0.000215926 | 2.7 | 195 | 667 | 766 | 1090 | 4497 | 6277 | 7157 | N | N | N | N | N | N |
| KRT27 | high in P | 5.4 | 0.000219564 | 2.7 | 196 | 1 | 1 | 1 | 7 | 6 | 6 | P | N | N | N | N | N |
| PLK1S1 | high in P | 12.3 | 0.000213202 | 2.7 | 197 | 6 | 9 | 7 | 27 | 20 | 39 | NA | NA | N | N | N | N |
| ANKRD45 | high in P | 8.9 | 0.000216839 | 2.7 | 198 | 13 | 6 | 8 | 54 | 44 | 51 | N | P | N | N | N | N |
| CYP2R1 | high in P | 7.0 | 0.000219658 | 2.7 | 199 | 20 | 18 | 19 | 74 | 151 | 86 | N | N | N | N | N | N |
| C18orf25 | high in P | 6.5 | 0.000200477 | 2.7 | 200 | 79 | 61 | 59 | 376 | 450 | 587 | N | N | N | N | N | N |
| C5orf44 | high in P | 9.3 | 0.000214115 | 2.7 | 201 | 16 | 15 | 26 | 113 | 82 | 161 | N | N | N | N | N | N |
| LOC729799 | high in P | 9.5 | 0.000220934 | 2.7 | 202 | 4 | 4 | 4 | 32 | 11 | 15 | NA | NA | N | N | N | N |
| RPAP2 | high in P | 10.5 | 0.000227753 | 2.7 | 203 | 5 | 8 | 6 | 82 | 94 | 31 | N | N | N | N | N | N |
| ANKRD11 | high in P | 7.4 | 0.000234572 | 2.7 | 204 | 212 | 224 | 410 | 1624 | 2078 | 1867 | N | N | N | N | N | N |
| NONO | high in P | 6.3 | 0.000241391 | 2.7 | 205 | 332 | 393 | 437 | 2236 | 3456 | 2119 | N | N | N | N | N | N |
| VN1R2 | high in P | 6.9 | 0.000224821 | 2.7 | 206 | 3 | 4 | 5 | 25 | 29 | 22 | N | N | N | N | N | N |
| INVS | high in P | 9.3 | 0.000267985 | 2.6 | 207 | 5 | 5 | 5 | 15 | 14 | 22 | N | N | N | N | N | N |
| ZWILCH | high in P | 14.6 | 0.000274804 | 2.6 | 208 | 13 | 6 | 7 | 78 | 27 | 42 | N | P | N | N | N | N |
| FLJ25006 | high in P | 7.6 | 0.000281623 | 2.6 | 209 | 3 | 6 | 8 | 50 | 31 | 60 | N | N | N | N | N | N |
| EVPL | high in P | 28.2 | 0.000317763 | 2.6 | 210 | 8 | 9 | 12 | 44 | 220 | 58 | N | N | N | N | N | N |
| MTMR15 | high in P | 12.3 | 0.00023822 | 2.6 | 211 | 11 | 11 | 13 | 51 | 87 | 39 | N | N | N | N | N | N |
| SLC1A5 | high in P | 21.8 | 0.000345039 | 2.6 | 212 | 1032 | 599 | 3953 | 24288 | 32600 | 22375 | N | N | N | N | N | N |
| SLC37A1 | high in P | 8.8 | 0.000365496 | 2.6 | 213 | 40 | 17 | 59 | 315 | 426 | 331 | N | N | N | N | N | N |
| LAT | high in P | 19.0 | 0.000379134 | 2.6 | 214 | 35 | 10 | 47 | 346 | 302 | 865 | N | N | N | N | N | N |
| DRG1 | high in P | 37.4 | 0.000385953 | 2.6 | 215 | 2 | 6 | 36 | 331 | 275 | 167 | N | N | N | N | N | N |
| YPEL1 | high in P | 6.3 | 0.000422093 | 2.6 | 216 | 16 | 28 | 28 | 118 | 195 | 151 | N | N | N | N | N | N |
| TNFAIP8L1 | high in P | 5.4 | 0.000441186 | 2.6 | 217 | 195 | 130 | 198 | 930 | 1026 | 1042 | N | N | N | P | N | N |
| IDO1 | high in P | 15.0 | 0.000495056 | 2.6 | 218 | 3 | 4 | 4 | 20 | 36 | 105 | NA | NA | N | N | N | N |
| IKBKB | high in P | 4.9 | 0.000508694 | 2.6 | 219 | 47 | 63 | 78 | 325 | 344 | 419 | N | N | N | N | N | N |
| KIAA0406 | high in P | 7.5 | 0.000529151 | 2.6 | 220 | 18 | 27 | 10 | 126 | 164 | 109 | N | N | N | N | N | N |
| GATSL3 | high in P | 7.0 | 0.000544835 | 2.6 | 221 | 32 | 26 | 38 | 131 | 163 | 235 | NA | NA | N | N | N | N |
| C7orf43 | high in P | 6.8 | 0.000585748 | 2.6 | 222 | 47 | 111 | 63 | 370 | 432 | 464 | N | N | N | N | N | N |
| TRIP4 | high in P | 8.8 | 0.000606205 | 2.6 | 223 | 49 | 19 | 23 | 348 | 231 | 133 | N | N | N | N | N | N |
| SNORD36C | high in P | 15.3 | 0.000619843 | 2.6 | 224 | 134 | 94 | 397 | 1362 | 3410 | 3114 | N | N | N | N | N | N |
| HCCS | high in P | 5.5 | 0.000626662 | 2.6 | 225 | 70 | 60 | 83 | 492 | 373 | 308 | NA | NA | N | N | N | N |
| ANAPC2 | high in P | 12.6 | 0.000633481 | 2.6 | 226 | 51 | 24 | 18 | 326 | 175 | 329 | N | N | N | N | N | N |
| SQLE | high in P | 5.8 | 0.000645755 | 2.6 | 227 | 13 | 13 | 16 | 87 | 55 | 65 | N | N | N | N | N | N |
| NHEJ1 | high in P | 5.8 | 0.000659393 | 2.6 | 228 | 65 | 44 | 87 | 371 | 390 | 365 | N | N | N | N | N | N |
| CYP2B7P1 | high in P | 10.1 | 0.000666212 | 2.6 | 229 | 4 | 4 | 4 | 31 | 13 | 15 | N | P | N | N | N | N |
| ZBTB5 | high in P | 8.0 | 0.000673031 | 2.6 | 230 | 36 | 24 | 40 | 207 | 156 | 266 | N | N | N | N | N | N |
| LSM10 | high in P | 5.1 | 0.000685305 | 2.6 | 231 | 39 | 24 | 36 | 202 | 166 | 139 | N | N | N | N | N | N |
| TSPAN31 | high in P | 5.2 | 0.000692124 | 2.6 | 232 | 51 | 47 | 48 | 240 | 166 | 265 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | | Nulliparous (NP) | | | | Parous (P) | | | CD44+ | CD44+ | GeneBody | GeneBody | Pro-motor | Pro-moter |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | N74 | N66 | NP Met | Met | Met | Met |
| | | | | | | | | | | | | NP | P | NP | P | NP | P |
| CYP27C1 | high in P | 6.8 | 0.002698943 | 2.6 | 233 | 38 | 22 | 35 | 219 | 193 | 214 | N | N | N | N | N | N |
| HTR7P | high in P | 8.6 | 0.002712581 | 2.6 | 234 | NA | NA | NA | NA | NA | NA | N | N | N | N | N | N |
| CEP192 | high in P | 8.6 | 0.002726219 | 2.6 | 235 | 21 | 10 | 15 | 42 | 46 | 53 | N | N | N | N | N | N |
| HAX1 | high in P | 7.7 | 0.002733038 | 2.6 | 236 | 295 | 143 | 139 | 1295 | 1359 | 1078 | N | N | N | N | N | N |
| GZF1 | high in P | 9.1 | 0.002739857 | 2.6 | 237 | 40 | 19 | 55 | 300 | 272 | 368 | N | N | N | N | N | N |
| RABL3 | high in P | 11.9 | 0.002753495 | 2.6 | 238 | 58 | 23 | 74 | 815 | 601 | 293 | N | N | N | N | N | N |
| ACHE | high in P | 6.3 | 0.002760314 | 2.6 | 239 | 13 | 10 | 8 | 48 | 58 | 49 | N | N | N | N | N | N |
| FAM115A | high in P | 7.9 | 0.002767133 | 2.6 | 240 | 148 | 92 | 162 | 703 | 1203 | 1616 | P | N | N | N | N | N |
| NUDT16 | high in P | 6.2 | 0.002773952 | 2.6 | 241 | 23 | 23 | 17 | 164 | 74 | 83 | N | N | N | N | N | N |
| C21orf99 | high in P | 7.9 | 0.002787589 | 2.6 | 242 | 2 | 1 | 2 | 15 | 18 | 10 | NA | NA | N | N | N | N |
| LOC100216545 | high in P | 10.2 | 0.002810092 | 2.6 | 243 | 20 | 6 | 15 | 132 | 87 | 179 | NA | NA | N | N | N | N |
| TCEA2 | high in P | 7.7 | 0.002825776 | 2.5 | 244 | 106 | 46 | 88 | 624 | 582 | 966 | N | N | N | N | N | N |
| SFRS8 | high in P | 7.7 | 0.002832595 | 2.5 | 245 | 127 | 232 | 126 | 1023 | 1013 | 1065 | N | N | N | N | N | N |
| CXorf15 | high in P | 13.6 | 0.002839414 | 2.5 | 246 | NA | NA | NA | NA | NA | NA | N | N | N | N | N | N |
| RFPL3S | high in P | 10.1 | 0.002846233 | 2.5 | 247 | 3 | 8 | 4 | 38 | 40 | 51 | N | N | N | N | N | N |
| ZNF274 | high in P | 6.3 | 0.002853051 | 2.5 | 248 | 75 | 45 | 73 | 531 | 418 | 268 | N | N | N | N | N | N |
| NXNL2 | high in P | 7.8 | 0.002866689 | 2.5 | 249 | 11 | 9 | 17 | 92 | 65 | 72 | N | N | N | N | P | N |
| MFSD7 | high in P | 14.9 | 0.002873508 | 2.5 | 250 | 35 | 16 | 66 | 361 | 345 | 279 | N | N | N | N | N | N |
| UTP6 | high in P | 5.9 | 0.002880327 | 2.5 | 251 | 59 | 81 | 42 | 290 | 409 | 320 | N | N | N | N | N | N |
| MXD3 | high in P | 9.4 | 0.002887146 | 2.5 | 252 | 28 | 11 | 23 | 166 | 238 | 141 | N | N | N | N | N | N |
| BNIP2 | high in P | 4.3 | 0.00290283 | 2.5 | 253 | 71 | 62 | 67 | 296 | 295 | 234 | N | N | N | N | N | N |
| KPTN | high in P | 10.1 | 0.002923287 | 2.5 | 254 | 73 | 25 | 64 | 293 | 507 | 607 | N | N | N | N | N | N |
| DBF4B | high in P | 5.8 | 0.002930106 | 2.5 | 255 | 272 | 190 | 229 | 1009 | 1214 | 1531 | N | P | N | N | N | N |
| RBBP9 | high in P | 11.9 | 0.002936925 | 2.5 | 256 | 23 | 18 | 37 | 128 | 194 | 113 | N | N | N | N | N | N |
| DOCK9 | high in P | 14.5 | 0.002943744 | 2.5 | 257 | 56 | 28 | 24 | 260 | 214 | 307 | N | N | N | N | N | N |
| NEDD4 | high in P | 5.4 | 0.002971019 | 2.5 | 258 | 12 | 13 | 15 | 52 | 53 | 42 | N | N | N | N | N | N |
| ASF1A | high in P | 5.1 | 0.002977838 | 2.5 | 259 | 68 | 57 | 88 | 353 | 342 | 400 | N | N | N | N | N | N |
| KCNRG | high in P | 6.8 | 0.002984657 | 2.5 | 260 | 2 | 2 | 3 | 18 | 12 | 18 | N | N | N | N | N | N |
| REEP4 | high in P | 7.0 | 0.002998295 | 2.5 | 261 | 46 | 16 | 40 | 278 | 285 | 183 | N | N | N | N | N | N |
| WFDC8 | high in P | 10.4 | 0.003005114 | 2.5 | 262 | 9 | 3 | 6 | 39 | 23 | 30 | N | N | N | N | N | N |
| SLFN13 | high in P | 6.6 | 0.00303239 | 2.5 | 263 | 18 | 22 | 32 | 143 | 140 | 190 | N | N | N | N | N | N |
| SPPL2B | high in P | 10.1 | 0.003039209 | 2.5 | 264 | 175 | 41 | 146 | 1181 | 1465 | 1668 | P | P | N | N | N | N |
| FGF5 | high in P | 6.8 | 0.003052847 | 2.5 | 265 | 33 | 21 | 37 | 165 | 126 | 215 | N | N | N | N | N | N |
| EXTL3 | high in P | 17.4 | 0.003059666 | 2.5 | 266 | 107 | 33 | 78 | 2127 | 1033 | 482 | N | N | N | N | N | N |
| SNORA57 | high in P | 16.9 | 0.003066485 | 2.5 | 267 | 7 | 5 | 1 | 24 | 33 | 104 | N | N | N | N | P | N |
| JRK | high in P | 5.4 | 0.003073304 | 2.5 | 268 | 34 | 36 | 32 | 150 | 135 | 166 | N | N | N | N | N | N |
| DDHD2 | high in P | 7.0 | 0.003080123 | 2.5 | 269 | 25 | 25 | 20 | 136 | 123 | 99 | N | N | N | N | N | N |
| CCNJ | high in P | 5.2 | 0.003093761 | 2.5 | 270 | 15 | 21 | 23 | 92 | 64 | 61 | N | N | N | N | N | N |
| KIAA1161 | high in P | 9.6 | 0.0030100058 | 2.5 | 271 | 11 | 17 | 37 | 128 | 159 | 189 | N | N | N | N | N | N |
| DHX8 | high in P | 9.2 | 0.003107399 | 2.5 | 272 | 92 | 23 | 77 | 586 | 806 | 640 | N | N | N | N | N | N |
| USP54 | high in P | 18.2 | 0.003114218 | 2.5 | 273 | 1 | 3 | 8 | 46 | 134 | 67 | N | N | N | N | N | N |
| NPW | high in P | 5.6 | 0.003127855 | 2.5 | 274 | 45 | 35 | 54 | 208 | 217 | 153 | N | N | N | N | N | N |
| C5orf56 | high in P | 8.9 | 0.003141493 | 2.5 | 275 | 8 | 8 | 8 | 29 | 27 | 39 | NA | NA | N | N | N | N |
| TYMP | high in P | 8.0 | 0.003148312 | 2.5 | 276 | 701 | 552 | 696 | 17914 | 4646 | 4081 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | | Nulliparous (NP) | | | | Parous (P) | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 NP | CD44+ N66 P | GeneBody NP Met NP | GeneBody Met P | Pro-motor Met NP | Pro-moter Met P |
| LRCH4 | high in P | 10.4 | 0.00316195 | 2.5 | 277 | 141 | 50 | 208 | 1038 | 1520 | 1674 | N | N | N | N | N | N |
| BRF1 | high in P | 8.8 | 0.003175588 | 2.5 | 278 | 98 | 28 | 78 | 678 | 603 | 748 | N | N | N | N | N | N |
| SETD8 | high in P | 8.6 | 0.003182407 | 2.5 | 279 | 277 | 181 | 476 | 1698 | 2329 | 2560 | N | N | N | N | N | N |
| WDR45 | high in P | 6.4 | 0.003189226 | 2.5 | 280 | 279 | 149 | 248 | 1854 | 1275 | 1196 | N | N | N | N | N | N |
| NCAPD3 | high in P | 8.9 | 0.003209001 | 2.5 | 281 | 10 | 25 | 12 | 89 | 114 | 70 | N | N | N | N | N | N |
| MOCS3 | high in P | 4.9 | 0.00321582 | 2.5 | 282 | 20 | 15 | 17 | 57 | 45 | 70 | N | N | N | N | N | N |
| RPL9 | high in P | 5.2 | 0.003222639 | 2.5 | 283 | 8530 | 8736 | 11346 | 47216 | 64079 | 39995 | N | N | N | N | N | N |
| CDH24 | high in P | 10.4 | 0.003249915 | 2.5 | 284 | 17 | 7 | 21 | 79 | 148 | 116 | N | N | N | N | N | N |
| C12orf10 | high in P | 6.3 | 0.003256734 | 2.5 | 285 | 301 | 196 | 185 | 1843 | 1213 | 1120 | N | P | N | N | N | N |
| RNF208 | high in P | 6.1 | 0.003263553 | 2.5 | 286 | 3 | 9 | 6 | 53 | 37 | 27 | N | N | N | N | N | N |
| DNM1L | high in P | 4.6 | 0.003270372 | 2.5 | 287 | 73 | 122 | 131 | 644 | 606 | 547 | N | N | N | N | N | N |
| LAMP3 | high in P | 6.5 | 0.003277191 | 2.5 | 288 | 9 | 14 | 11 | 44 | 67 | 75 | N | N | N | N | N | N |
| METT11D1 | high in P | 7.9 | 0.003290147 | 2.5 | 289 | 208 | 102 | 163 | 1185 | 1293 | 705 | N | N | N | N | N | N |
| DGKZ | high in P | 6.7 | 0.002296966 | 2.5 | 290 | 56 | 39 | 53 | 222 | 354 | 415 | N | N | N | N | N | N |
| PHF5A | high in P | 4.5 | 0.003303785 | 2.5 | 291 | 97 | 96 | 126 | 583 | 521 | 385 | N | N | N | N | N | N |
| PPIF | high in P | 5.4 | 0.003317422 | 2.5 | 292 | 285 | 360 | 532 | 1764 | 2404 | 1966 | N | N | N | N | N | N |
| POM121 | high in P | 5.6 | 0.00333106 | 2.5 | 293 | 38 | 24 | 27 | 118 | 148 | 144 | N | N | N | N | N | N |
| SLC14A1 | high in P | 10.3 | 0.003346744 | 2.5 | 294 | 43 | 22 | 69 | 249 | 443 | 447 | N | N | N | N | N | N |
| IL1RL1 | high in P | 10.2 | 0.003353563 | 2.5 | 295 | 91 | 445 | 245 | 2681 | 3356 | 2140 | N | N | N | N | N | N |
| ZFAND2B | high in P | 8.8 | 0.003360382 | 2.5 | 296 | 20 | 26 | 51 | 221 | 161 | 211 | P | P | N | N | N | N |
| DDX39 | high in P | 6.6 | 0.003367201 | 2.5 | 297 | 479 | 279 | 704 | 3368 | 2639 | 4105 | N | P | N | P | N | N |
| TIPIN | high in P | 5.0 | 0.00337402 | 2.5 | 298 | 14 | 5 | 8 | 38 | 35 | 30 | N | N | N | N | N | N |
| KREMEN1 | high in P | 4.9 | 0.003387658 | 2.5 | 299 | 33 | 36 | 51 | 203 | 204 | 227 | N | N | N | N | N | N |
| MPHOSPH6 | high in P | 10.2 | 0.003394477 | 2.5 | 300 | 23 | 52 | 49 | 325 | 543 | 246 | P | N | N | N | N | N |
| MZF1 | high in P | 6.5 | 0.003401296 | 2.5 | 301 | 46 | 46 | 78 | 267 | 308 | 274 | N | N | N | N | N | N |
| TRIM14 | high in P | 6.8 | 0.003414934 | 2.5 | 302 | 33 | 24 | 20 | 81 | 123 | 150 | P | N | N | N | N | N |
| MTHFR | high in P | 9.2 | 0.003428571 | 2.5 | 303 | 190 | 75 | 141 | 1324 | 912 | 2174 | N | N | N | N | N | N |
| RNASEH2C | high in P | 10.9 | 0.00343539 | 2.5 | 304 | 10 | 10 | 13 | 104 | 56 | 31 | N | N | N | N | N | N |
| DAXX | high in P | 6.5 | 0.003442209 | 2.5 | 305 | 544 | 237 | 515 | 2686 | 3549 | 2728 | P | P | N | N | N | P |
| HHIPL1 | high in P | 12.4 | 0.003449028 | 2.5 | 306 | 23 | 7 | 10 | 168 | 98 | 98 | N | N | N | N | N | N |
| SNX22 | high in P | 6.2 | 0.003455847 | 2.5 | 307 | 25 | 37 | 47 | 172 | 212 | 326 | N | N | N | N | N | N |
| SLC25A1 | high in P | 11.6 | 0.003462666 | 2.5 | 308 | 211 | 69 | 97 | 1390 | 1139 | 726 | N | N | N | N | N | N |
| HOXB6 | high in P | 6.5 | 0.003483123 | 2.5 | 309 | 17 | 4 | 9 | 74 | 40 | 49 | P | P | N | N | N | N |
| KRBA2 | high in P | 6.1 | 0.003524719 | 2.5 | 310 | 161 | 65 | 119 | 697 | 709 | 718 | N | N | N | N | N | N |
| PARP8 | high in P | 4.6 | 0.003531538 | 2.5 | 311 | 18 | 24 | 18 | 70 | 65 | 86 | N | P | P | N | N | N |
| LMAN2L | high in P | 9.5 | 0.003551995 | 2.5 | 312 | 124 | 27 | 63 | 491 | 585 | 561 | N | N | N | N | N | N |
| PNLDC1 | high in P | 5.2 | 0.003565632 | 2.4 | 313 | 19 | 7 | 10 | 49 | 31 | 53 | N | N | N | N | N | N |
| ITGA10 | high in P | 5.8 | 0.003572451 | 2.4 | 314 | 13 | 44 | 43 | 141 | 163 | 209 | N | N | N | N | N | N |
| SCRIB | high in P | 12.1 | 0.00357927 | 2.4 | 315 | 104 | 30 | 133 | 1078 | 1323 | 998 | N | N | N | N | N | N |
| CBLL1 | high in P | 5.1 | 0.003598363 | 2.4 | 316 | 99 | 68 | 78 | 393 | 407 | 344 | N | N | N | N | N | N |
| IRF3 | high in P | 9.2 | 0.003612001 | 2.4 | 317 | 51 | 18 | 26 | 224 | 209 | 238 | N | N | N | N | N | N |
| CHMP6 | high in P | 10.4 | 0.003648142 | 2.4 | 318 | 48 | 14 | 35 | 384 | 316 | 139 | N | N | N | N | N | N |
| HOXC11 | high in P | 19.4 | 0.003668599 | 2.4 | 319 | 2 | 2 | 2 | 23 | 8 | 55 | P | P | N | N | N | N |
| C2orf15 | high in P | 5.5 | 0.003675418 | 2.4 | 320 | 170 | 100 | 143 | 629 | 767 | 880 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
| --- | --- | --- | --- | --- | --- | --- | --- | --- | --- | --- | --- | --- | --- | --- | --- | --- | --- |
| | | | | | | Nulliparous (NP) | | | Parous (P) | | | NP | P | GeneBody NP Met | GeneBody Met | Pro-moter Met | Pro-moter Met |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | | | | |
| PRC1 | high in P | 11.3 | 0.003682237 | 2.4 | 321 | 17 | 6 | 8 | 59 | 30 | 54 | N | N | N | N | N | N |
| TNFRSF1B | high in P | 8.8 | 0.003694511 | 2.4 | 322 | 696 | 154 | 745 | 4534 | 5317 | 6637 | N | N | N | N | N | N |
| FLVCR1 | high in P | 9.4 | 0.00370133 | 2.4 | 323 | 13 | 25 | 14 | 59 | 124 | 122 | N | N | N | N | N | N |
| DNAJC8 | high in P | 6.7 | 0.003708149 | 2.4 | 324 | 224 | 195 | 415 | 1951 | 1473 | 1411 | N | N | N | N | N | N |
| RASSF4 | high in P | 10.4 | 0.003714968 | 2.4 | 325 | 76 | 14 | 64 | 534 | 393 | 742 | N | N | N | P | N | N |
| STEAP3 | high in P | 9.9 | 0.003721787 | 2.4 | 326 | 10 | 12 | 14 | 65 | 250 | 51 | N | N | N | N | N | N |
| RPS19BP1 | high in P | 9.4 | 0.003735424 | 2.4 | 327 | 79 | 25 | 24 | 431 | 467 | 185 | N | N | N | P | N | N |
| EFHC1 | high in P | 4.4 | 0.003749062 | 2.4 | 328 | 45 | 50 | 46 | 192 | 261 | 261 | N | N | N | N | N | N |
| RASSF7 | high in P | 11.4 | 0.003769519 | 2.4 | 329 | 23 | 23 | 58 | 151 | 599 | 503 | N | N | N | N | N | N |
| DDA1 | high in P | 5.7 | 0.003783157 | 2.4 | 330 | 586 | 379 | 610 | 3335 | 4052 | 2377 | N | N | N | N | N | P |
| GFER | high in P | 8.8 | 0.003789976 | 2.4 | 331 | 85 | 38 | 47 | 480 | 293 | 370 | N | N | N | N | N | N |
| SFRS14 | high in P | 6.5 | 0.003796795 | 2.4 | 332 | 56 | 35 | 47 | 229 | 377 | 255 | N | N | N | N | N | N |
| MNAT1 | high in P | 14.1 | 0.003824071 | 2.4 | 333 | 47 | 8 | 21 | 470 | 325 | 139 | N | N | N | N | N | N |
| MGC12982 | high in P | 17.8 | 0.00383089 | 2.4 | 334 | 3 | 3 | 5 | 82 | 15 | 86 | N | N | N | N | N | N |
| C19orf76 | high in P | 13.5 | 0.003837709 | 2.4 | 335 | 47 | 28 | 63 | 192 | 584 | 801 | NA | NA | N | N | N | N |
| YTHDF2 | high in P | 5.0 | 0.003858166 | 2.4 | 336 | 869 | 448 | 932 | 3988 | 4335 | 4175 | NA | NA | N | N | N | N |
| FBXW5 | high in P | 11.7 | 0.003879986 | 2.4 | 337 | 497 | 141 | 417 | 6147 | 3497 | 2061 | N | N | N | N | N | N |
| ZNF169 | high in P | 7.2 | 0.003900443 | 2.4 | 338 | 4 | 4 | 4 | 23 | 15 | 12 | N | N | N | N | N | N |
| EIF4ENIF1 | high in P | 5.5 | 0.0039209 | 2.4 | 339 | 69 | 41 | 57 | 229 | 328 | 276 | N | N | N | N | N | N |
| APPBP2 | high in P | 4.6 | 0.003927719 | 2.4 | 340 | 46 | 54 | 61 | 229 | 215 | 331 | N | N | N | N | N | N |
| LOC100170939 | high in P | 8.6 | 0.003942039 | 2.4 | 341 | 8 | 2 | 2 | 22 | 15 | 22 | N | N | N | N | N | N |
| ADORA3 | high in P | 8.8 | 0.003955677 | 2.4 | 342 | 3 | 3 | 4 | 20 | 10 | 26 | N | N | N | N | N | N |
| ITGB7 | high in P | 18.5 | 0.003030409 | 2.4 | 343 | 28 | 10 | 12 | 55 | 176 | 492 | N | N | N | N | N | N |
| MRPL32 | high in P | 5.8 | 0.004010228 | 2.4 | 344 | 599 | 396 | 366 | 1948 | 2932 | 2223 | NA | N | N | N | N | N |
| SMUG1 | high in P | 4.6 | 0.004017047 | 2.4 | 345 | 20 | 19 | 21 | 76 | 82 | 59 | N | N | N | N | N | N |
| MYO19 | high in P | 4.6 | 0.004023866 | 2.4 | 346 | 37 | 51 | 67 | 252 | 322 | 178 | N | N | N | N | N | N |
| CCDC127 | high in P | 12.5 | 0.004030685 | 2.4 | 347 | 15 | 33 | 87 | 416 | 518 | 381 | N | N | N | N | N | N |
| ADC | high in P | 11.4 | 0.004037504 | 2.4 | 348 | 37 | 31 | 47 | 143 | 396 | 492 | NA | N | N | N | N | N |
| RPL23AP82 | high in P | 7.9 | 0.004057961 | 2.4 | 349 | 2 | 2 | 2 | 10 | 10 | 13 | NA | N | N | N | N | N |
| SRRD | high in P | 6.0 | 0.00406478 | 2.4 | 350 | 52 | 26 | 26 | 159 | 217 | 111 | N | N | N | N | N | N |
| INSL3 | high in P | 11.5 | 0.004078418 | 2.4 | 351 | 2 | 2 | 3 | 14 | 16 | 41 | P | N | N | N | N | N |
| GCHFR | high in P | 12.5 | 0.004092056 | 2.4 | 352 | 2 | 11 | 14 | 135 | 87 | 133 | N | N | N | N | N | N |
| RNF26 | high in P | 5.6 | 0.004105694 | 2.4 | 353 | 115 | 50 | 103 | 651 | 497 | 435 | N | N | N | N | N | N |
| KIAA1919 | high in P | 9.3 | 0.004112513 | 2.4 | 354 | 28 | 8 | 17 | 92 | 118 | 107 | NA | N | N | N | N | N |
| RRN3P3 | high in P | 5.1 | 0.004119332 | 2.4 | 355 | 442 | 266 | 585 | 2623 | 2245 | 2282 | N | N | N | N | N | N |
| MRPL14 | high in P | 6.7 | 0.004126151 | 2.4 | 356 | 406 | 267 | 144 | 1647 | 2323 | 1514 | NA | N | N | N | N | N |
| UPF3B | high in P | 4.6 | 0.004158882 | 2.4 | 357 | 62 | 30 | 50 | 219 | 250 | 218 | N | N | N | N | N | N |
| AFG3L1 | high in P | 6.0 | 0.004177975 | 2.4 | 358 | 25 | 18 | 41 | 203 | 129 | 129 | N | N | N | P | N | N |
| PSMG4 | high in P | 5.1 | 0.004191613 | 2.4 | 359 | 53 | 34 | 32 | 159 | 253 | 258 | N | N | N | N | N | N |
| NDOR1 | high in P | 4.6 | 0.004198432 | 2.4 | 360 | 56 | 33 | 59 | 272 | 244 | 246 | N | N | N | N | N | N |
| PLXNB1 | high in P | 6.7 | 0.00421207 | 2.4 | 361 | 116 | 126 | 180 | 892 | 1702 | 545 | N | N | N | N | N | N |
| C6orf145 | high in P | 7.0 | 0.004225707 | 2.4 | 362 | 1195 | 970 | 2144 | 9400 | 6242 | 14625 | N | N | N | N | N | N |
| FBXL8 | high in P | 13.1 | 0.004239345 | 2.4 | 363 | 23 | 2 | 5 | 130 | 76 | 77 | N | N | N | N | N | N |
| SLC39A13 | high in P | 9.0 | 0.004263212 | 2.4 | 364 | 429 | 142 | 217 | 1818 | 2212 | 1575 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
| | | | | | | Nulliparous (NP) | | | Parous (P) | | | NP | P | | NP | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
|---|---|---|---|---|---|---|---|---|---|---|---|---|---|---|---|---|---|
| DNAJC9 | high in P | 4.8 | 0.004270031 | 2.4 | 365 | 15 | 11 | 9 | 45 | 50 | 32 | N | N | N | N | N | N |
| NSMCE1 | high in P | 16.0 | 0.004277685 | 2.4 | 366 | 29 | 8 | 16 | 200 | 200 | 83 | N | N | N | N | N | N |
| NCOR2 | high in P | 10.6 | 0.004297307 | 2.4 | 367 | 218 | 128 | 102 | 1276 | 875 | 1658 | NA | NA | N | N | N | N |
| FLJ14107 | high in P | 8.8 | 0.004310944 | 2.4 | 368 | 4 | 4 | 4 | 21 | 29 | 10 | NA | NA | N | N | N | N |
| MECR | high in P | 4.4 | 0.004330038 | 2.4 | 369 | 27 | 32 | 45 | 160 | 147 | 107 | N | N | N | N | N | N |
| CCDC61 | high in P | 7.7 | 0.004336856 | 2.4 | 370 | 3 | 4 | 8 | 71 | 40 | 24 | NA | NA | N | N | N | N |
| ZSCAN5A | high in P | 12.3 | 0.004350494 | 2.4 | 371 | 4 | 4 | 5 | 34 | 17 | 17 | N | N | N | N | N | N |
| C19orf77 | high in P | 8.2 | 0.00437777 | 2.4 | 372 | 3 | 3 | 4 | 15 | 26 | 11 | NA | NA | N | N | N | N |
| GIGYF1 | high in P | 5.1 | 0.004384589 | 2.4 | 373 | 173 | 146 | 267 | 1066 | 956 | 989 | N | N | N | N | N | N |
| NOL12 | high in P | 5.3 | 0.004391408 | 2.4 | 374 | 44 | 23 | 27 | 167 | 134 | 126 | N | N | N | N | P | N |
| NCAPH | high in P | 6.3 | 0.004398227 | 2.4 | 375 | 13 | 6 | 6 | 16 | 14 | 12 | N | N | N | N | N | N |
| TMEM229B | high in P | 10.1 | 0.004405046 | 2.4 | 376 | 6 | 6 | 6 | 34 | 22 | 12 | N | N | N | N | N | N |
| SURF2 | high in P | 8.5 | 0.004434368 | 2.4 | 377 | 2 | 2 | 3 | 23 | 19 | 8 | N | N | N | N | N | N |
| C9orf80 | high in P | 5.8 | 0.004454824 | 2.4 | 378 | 57 | 18 | 43 | 253 | 246 | 232 | N | N | N | N | P | N |
| CYP8B1 | high in P | 8.4 | 0.004475281 | 2.4 | 379 | 3 | 6 | 6 | 35 | 30 | 51 | N | N | N | N | N | N |
| COPS7B | high in P | 7.2 | 0.004495738 | 2.3 | 380 | 10 | 8 | 10 | 64 | 24 | 66 | N | N | N | N | N | N |
| WDR43 | high in P | 5.9 | 0.004502557 | 2.3 | 381 | 228 | 242 | 207 | 890 | 1956 | 1366 | N | N | N | N | N | N |
| POM121L8P | high in P | 5.2 | 0.004509376 | 2.3 | 382 | 24 | 26 | 20 | 82 | 82 | 112 | N | N | P | N | N | N |
| FUT5 | high in P | 7.1 | 0.004536652 | 2.3 | 383 | 16 | 6 | 7 | 33 | 40 | 73 | NA | NA | N | N | N | N |
| COLQ | high in P | 5.8 | 0.0045029 | 2.3 | 384 | 8 | 18 | 20 | 55 | 55 | 92 | N | N | N | N | N | N |
| LRRC37A3 | high in P | 14.8 | 0.004557109 | 2.3 | 385 | 28 | 2 | 4 | 85 | 93 | 164 | N | N | N | N | N | N |
| ABCB4 | high in P | 17.7 | 0.004563928 | 2.3 | 386 | 2 | 4 | 9 | 25 | 83 | 61 | N | N | N | N | N | N |
| ABCC13 | high in P | 4.0 | 0.004584385 | 2.3 | 387 | 24 | 14 | 14 | 63 | 60 | 67 | N | P | P | N | N | N |
| UCN | high in P | 14.5 | 0.004591204 | 2.3 | 388 | 2 | 8 | 3 | 55 | 39 | 23 | N | P | N | N | N | N |
| LAMC3 | high in P | 8.6 | 0.004598023 | 2.3 | 389 | 187 | 101 | 173 | 901 | 1369 | 3215 | N | N | N | N | N | N |
| NOL7 | high in P | 25.9 | 0.004604841 | 2.3 | 390 | 9 | 9 | 9 | 96 | 74 | 15 | P | N | N | N | N | N |
| SLC13A3 | high in P | 5.8 | 0.004625298 | 2.3 | 391 | 9 | 14 | 10 | 41 | 52 | 42 | N | N | N | N | N | N |
| THPO | high in P | 7.1 | 0.004632117 | 2.3 | 392 | 2 | 3 | 6 | 35 | 20 | 32 | N | N | N | N | N | N |
| ARL16 | high in P | 7.4 | 0.004652574 | 2.3 | 393 | 191 | 111 | 232 | 920 | 1629 | 828 | N | N | N | N | N | N |
| KCNH3 | high in P | 7.7 | 0.004673031 | 2.3 | 394 | 21 | 13 | 22 | 68 | 122 | 53 | N | N | N | N | N | N |
| SETDB1 | high in P | 7.4 | 0.004680585 | 2.3 | 395 | 17 | 26 | 47 | 171 | 164 | 110 | N | N | N | N | N | N |
| GPR137 | high in P | 6.8 | 0.004686669 | 2.3 | 396 | 87 | 45 | 157 | 768 | 567 | 539 | N | N | N | N | N | N |
| PLCH2 | high in P | 12.3 | 0.004712581 | 2.3 | 397 | 17 | 17 | 17 | 23 | 52 | 30 | N | N | N | N | N | N |
| TRABD | high in P | 3.6 | 0.004726219 | 2.3 | 398 | 167 | 225 | 198 | 687 | 760 | 772 | N | N | N | N | N | N |
| KIAA0664 | high in P | 8.7 | 0.004733038 | 2.3 | 399 | 105 | 187 | 51 | 811 | 1477 | 1065 | N | N | N | N | N | N |
| SFI1 | high in P | 6.9 | 0.004746676 | 2.3 | 400 | 17 | 14 | 26 | 81 | 120 | 66 | N | N | N | N | N | N |
| MTFMT | high in P | 4.1 | 0.004753495 | 2.3 | 401 | 19 | 13 | 11 | 60 | 51 | 37 | N | N | N | N | N | N |
| STEAP1 | high in P | 7.0 | 0.004767133 | 2.3 | 402 | 68 | 32 | 49 | 898 | 328 | 209 | N | N | N | N | N | N |
| DDR2 | high in P | 11.8 | 0.004787589 | 2.3 | 403 | 113 | 28 | 35 | 889 | 467 | 312 | N | N | N | N | N | N |
| TMCO2 | high in P | 7.1 | 0.00482032 | 2.3 | 404 | 1 | 1 | 1 | 7 | 6 | 24 | N | N | N | N | N | N |
| C15orf57 | high in P | 4.6 | 0.004794408 | 2.3 | 405 | 42 | 27 | 28 | 144 | 190 | 120 | N | N | N | N | N | N |
| MYNN | high in P | 4.1 | 0.004827139 | 2.3 | 406 | 47 | 39 | 48 | 211 | 139 | 175 | N | N | N | N | N | N |
| IL17RA | high in P | 4.1 | 0.00482032 | 2.3 | 407 | 47 | 44 | 57 | 207 | 207 | 164 | N | N | N | N | N | N |
| HN1L | high in P | 5.3 | 0.004833958 | 2.3 | 408 | 347 | 225 | 352 | 1285 | 2190 | 1566 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | | Parous (P) | | | NP | P | NP | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| ZNF18 | high in P | 15.5 | 0.004847596 | 2.3 | 409 | 6 | 7 | 9 | 122 | 28 | 36 | N | N | N | N | N | N |
| CAPG | high in P | 5.0 | 0.004854415 | 2.3 | 410 | 133 | 105 | 182 | 599 | 616 | 857 | N | N | N | N | N | N |
| KDM2A | high in P | 4.8 | 0.004861234 | 2.3 | 411 | 591 | 391 | 578 | 3097 | 2242 | 2961 | NA | NA | N | N | N | N |
| LOC442421 | high in P | 9.2 | 0.004874872 | 2.3 | 412 | 9 | 9 | 9 | 59 | 27 | 37 | P | P | N | N | N | N |
| PI4K2A | high in P | 6.6 | 0.004888851 | 2.3 | 413 | 754 | 746 | 1594 | 4234 | 6022 | 9886 | N | N | N | N | N | N |
| RAB4B | high in P | 6.0 | 0.004895329 | 2.3 | 414 | 14 | 12 | 11 | 43 | 27 | 24 | N | N | N | N | N | N |
| CHMP1A | high in P | 5.6 | 0.004902148 | 2.3 | 415 | 502 | 276 | 449 | 2803 | 2664 | 1708 | N | N | N | N | N | N |
| ALDOC | high in P | 3.9 | 0.004922605 | 2.3 | 416 | 31 | 40 | 35 | 107 | 122 | 136 | N | N | N | N | N | N |
| ARPM1 | high in P | 5.7 | 0.004929424 | 2.3 | 417 | 6 | 6 | 6 | 13 | 19 | 13 | N | N | N | N | N | N |
| LETM2 | high in P | 7.2 | 0.004943062 | 2.3 | 418 | 3 | 4 | 9 | 22 | 36 | 38 | N | N | N | N | N | N |
| RNF123 | high in P | 5.0 | 0.004963519 | 2.3 | 419 | 83 | 54 | 59 | 447 | 322 | 237 | N | N | N | N | N | N |
| PYCRL | high in P | 6.0 | 0.004970338 | 2.3 | 420 | 39 | 21 | 31 | 102 | 166 | 148 | N | N | N | N | N | N |
| ZNF425 | high in P | 8.1 | 0.004977156 | 2.3 | 421 | 98 | 26 | 36 | 320 | 310 | 405 | N | N | N | N | N | N |
| WDR81 | high in P | 11.7 | 0.004997613 | 2.3 | 422 | 75 | 58 | 102 | 2165 | 321 | 964 | NA | NA | N | N | N | N |
| SULT1A4 | high in P | 10.2 | 0.005004432 | 2.3 | 423 | 27 | 72 | 96 | 339 | 713 | 780 | N | N | N | N | N | N |
| TEP1 | high in P | 5.3 | 0.005011251 | 2.3 | 424 | 60 | 50 | 75 | 312 | 360 | 199 | N | N | N | N | N | N |
| FAM164C | high in P | 5.9 | 0.00501807 | 2.3 | 425 | 4 | 4 | 5 | 17 | 24 | 20 | N | N | N | N | N | N |
| SRRT | high in P | 6.0 | 0.005024889 | 2.3 | 426 | 435 | 261 | 746 | 2548 | 3421 | 2779 | NA | NA | N | N | N | N |
| ERLIN1 | high in P | 7.5 | 0.005038527 | 2.3 | 427 | 251 | 55 | 298 | 1917 | 1424 | 1856 | N | N | N | N | N | N |
| WDR90 | high in P | 4.3 | 0.005045346 | 2.3 | 428 | 16 | 24 | 21 | 79 | 60 | 52 | N | N | N | N | N | N |
| BTN2A2 | high in P | 10.2 | 0.005052165 | 2.3 | 429 | 32 | 6 | 10 | 143 | 68 | 161 | NA | NA | N | N | N | N |
| NXF1 | high in P | 15.5 | 0.005065803 | 2.3 | 430 | 1779 | 992 | 1695 | 5615 | 10060 | 12393 | N | N | N | N | N | N |
| TMEM63A | high in P | 6.3 | 0.005072622 | 2.3 | 431 | 31 | 18 | 27 | 203 | 167 | 156 | N | N | N | N | N | N |
| SF3B2 | high in P | 7.2 | 0.005093761 | 2.3 | 432 | 269 | 245 | 261 | 1743 | 1448 | 872 | N | N | N | N | N | N |
| ZNF592 | high in P | 5.3 | 0.005107399 | 2.3 | 433 | 90 | 87 | 128 | 568 | 417 | 608 | P | N | N | N | N | N |
| C8orf33 | high in P | 4.5 | 0.005114218 | 2.3 | 434 | 129 | 183 | 205 | 894 | 745 | 775 | N | N | N | N | N | N |
| C15orf61 | high in P | 3.9 | 0.005134674 | 2.3 | 435 | 99 | 23 | 60 | 375 | 417 | 387 | N | N | N | N | N | N |
| CROCCL1 | high in P | 6.9 | 0.005141493 | 2.3 | 436 | 44 | 40 | 12 | 337 | 154 | 283 | NA | NA | N | N | N | N |
| GTF2IRD1 | high in P | 8.0 | 0.00516195 | 2.3 | 437 | 63 | 68 | 123 | 378 | 503 | 334 | NA | NA | N | N | N | N |
| VHL | high in P | 6.4 | 0.005175588 | 2.3 | 438 | 228 | 138 | 256 | 1150 | 824 | 923 | N | N | N | N | N | N |
| FBXL14 | high in P | 4.6 | 0.005182407 | 2.3 | 439 | 13 | 7 | 8 | 22 | 22 | 55 | N | N | N | N | N | N |
| AKNA | high in P | 5.5 | 0.005189226 | 2.3 | 440 | 376 | 102 | 721 | 2930 | 3808 | 6079 | N | N | N | N | N | N |
| C9orf41 | high in P | 9.4 | 0.005202864 | 2.3 | 441 | 28 | 8 | 29 | 132 | 168 | 268 | N | N | N | N | N | N |
| ZNF493 | high in P | 8.3 | 0.005218548 | 2.3 | 442 | 194 | 150 | 188 | 766 | 651 | 1007 | N | N | N | N | N | N |
| NLE1 | high in P | 4.6 | 0.005232185 | 2.3 | 443 | 127 | 59 | 98 | 470 | 915 | 414 | N | N | N | N | N | N |
| CHST6 | high in P | 7.5 | 0.005245823 | 2.3 | 444 | 85 | 71 | 49 | 339 | 392 | 463 | N | N | N | N | N | N |
| RPS6KB2 | high in P | 5.6 | 0.005252642 | 2.3 | 445 | 7 | 12 | 14 | 39 | 71 | 32 | N | N | N | P | N | N |
| RRP7B | high in P | 5.3 | 0.005259461 | 2.3 | 446 | 13 | 11 | 15 | 39 | 116 | 87 | N | N | N | N | N | N |
| ZNF77 | high in P | 7.6 | 0.00526628 | 2.3 | 447 | 12 | 13 | 6 | 33 | 36 | 28 | N | N | N | N | N | N |
| SHF | high in P | 9.1 | 0.005290147 | 2.3 | 448 | 98 | 34 | 72 | 332 | 363 | 532 | N | N | P | P | N | N |
| C16orf54 | high in P | 5.9 | 0.005296966 | 2.3 | 449 | 12 | 23 | 17 | 63 | 58 | 65 | N | N | N | N | N | N |
| SHKBP1 | high in P | 4.1 | 0.005311967 | 2.3 | 450 | 80 | 77 | 112 | 1082 | 410 | 386 | N | N | N | N | N | N |
| CYP2B6 | high in P | 5.8 | 0.005339925 | 2.3 | 451 | 6 | 7 | 8 | 29 | 27 | 30 | N | N | N | N | N | N |
| MYOM1 | high in P | 5.2 | 0.005346744 | 2.3 | 452 | 17 | 11 | 13 | 35 | 75 | 126 | P | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | | MSDK-seq | | |
|---|---|---|---|---|---|---|---|---|---|---|---|---|---|---|---|---|---|---|
| | | | | | | Nulliparous (NP) | | | | Parous (P) | | | NP | | P | NP | | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| C10orf118 | high in P | 5.5 | 0.005360382 | 2.3 | 453 | 31 | 43 | 62 | 174 | 183 | 212 | N | N | N | N | N | N |
| PIK3R1 | high in P | 6.5 | 0.005389703 | 2.3 | 454 | 341 | 201 | 160 | 2483 | 1648 | 991 | N | N | P | N | N | N |
| FBXO40 | high in P | 5.7 | 0.005403341 | 2.3 | 455 | 5 | 5 | 5 | 15 | 12 | 18 | N | N | N | N | N | N |
| POP4 | high in P | 8.9 | 0.005416979 | 2.3 | 456 | 11 | 5 | 8 | 79 | 45 | 25 | N | NA | N | N | N | N |
| CACNA1G | high in P | 26.5 | 0.005423798 | 2.3 | 457 | 219 | 54 | 169 | 1317 | 1261 | 9394 | NA | NA | N | N | N | N |
| LOC440944 | high in P | 4.0 | 0.00544971 | 2.3 | 458 | 40 | 56 | 72 | 208 | 214 | 266 | NA | N | N | N | N | N |
| ZNF321 | high in P | 5.7 | 0.005475622 | 2.3 | 459 | 125 | 111 | 223 | 604 | 759 | 938 | N | N | N | N | N | N |
| SGK269 | high in P | 13.1 | 0.005482441 | 2.3 | 460 | 140 | 104 | 254 | 745 | 2411 | 3389 | N | N | N | N | N | N |
| KCNK6 | high in P | 5.6 | 0.00548926 | 2.3 | 461 | 12 | 15 | 17 | 50 | 55 | 86 | N | N | N | N | N | N |
| XPO5 | high in P | 5.3 | 0.005496079 | 2.3 | 462 | 42 | 68 | 63 | 293 | 292 | 152 | N | N | N | N | N | N |
| MON1A | high in P | 4.8 | 0.005502898 | 2.3 | 463 | 19 | 19 | 13 | 41 | 43 | 42 | N | N | N | N | N | N |
| ST7OT1 | high in P | 5.1 | 0.005515172 | 2.3 | 464 | 38 | 15 | 16 | 131 | 93 | 72 | N | N | N | N | N | N |
| ADCK5 | high in P | 11.8 | 0.005521991 | 2.3 | 465 | 32 | 6 | 16 | 213 | 121 | 164 | N | N | N | N | N | N |
| RNMTL1 | high in P | 4.4 | 0.005535629 | 2.3 | 466 | 44 | 56 | 29 | 231 | 170 | 166 | N | N | N | N | N | N |
| FOXP3 | high in P | 8.0 | 0.005542448 | 2.3 | 467 | 3 | 3 | 3 | 16 | 22 | 16 | N | N | N | N | N | N |
| PCMT1 | 8 high in P | 5.4 | 0.005549267 | 2.3 | 468 | 572 | 329 | 316 | 2368 | 1849 | 1651 | N | N | N | N | N | N |
| FAM41C | high in P | 9.0 | 0.005556086 | 2.3 | 469 | 34 | 18 | 66 | 201 | 350 | 259 | N | N | N | N | N | N |
| KLHDC9 | high in P | 8.9 | 0.005562905 | 2.3 | 470 | 1 | 1 | 2 | 9 | 27 | 33 | NA | NA | N | N | N | N |
| BTG3 | high in P | 14.6 | 0.005617457 | 2.3 | 471 | 55 | 11 | 17 | 268 | 192 | 185 | N | N | N | N | N | N |
| OSTF1 | high in P | 11.4 | 0.005629731 | 2.2 | 472 | 259 | 58 | 60 | 1097 | 646 | 1305 | P | N | N | N | N | N |
| MGC3771 | high in P | 6.3 | 0.00563655 | 2.2 | 473 | 3 | 3 | 3 | 11 | 9 | 14 | N | N | N | N | N | N |
| HIP1R | high in P | 10.3 | 0.005650188 | 2.2 | 474 | 125 | 56 | 180 | 537 | 2207 | 1277 | NA | NA | N | N | N | N |
| NCS1 | high in P | 4.0 | 0.0056761 | 2.2 | 475 | 594 | 425 | 569 | 2061 | 2661 | 2177 | N | NA | N | N | N | N |
| APOL1 | high in P | 5.9 | 0.005689737 | 2.2 | 476 | 8 | 9 | 8 | 21 | 19 | 25 | N | N | N | N | N | N |
| PARP10 | high in P | 8.8 | 0.005696556 | 2.2 | 477 | 128 | 20 | 93 | 682 | 597 | 1108 | N | N | N | N | N | N |
| CXCL1 | high in P | 6.0 | 0.005703375 | 2.2 | 478 | 158 | 305 | 384 | 1067 | 1886 | 1701 | N | N | N | N | N | N |
| ZNF530 | high in P | 3.9 | 0.005710194 | 2.2 | 479 | 6 | 7 | 9 | 19 | 35 | 26 | N | N | N | N | N | N |
| MDH1 | high in P | 4.1 | 0.005717013 | 2.2 | 480 | 242 | 221 | 203 | 1028 | 863 | 1023 | P | N | N | N | N | N |
| PTPRCAP | high in P | 9.6 | 0.00573747 | 2.2 | 481 | 19 | 11 | 33 | 117 | 83 | 682 | N | N | N | N | N | N |
| SCFD2 | high in P | 5.2 | 0.005757927 | 2.2 | 482 | 9 | 16 | 9 | 54 | 54 | 315 | N | N | N | N | N | N |
| PAOX | high in P | 6.5 | 0.005812479 | 2.2 | 483 | 4 | 4 | 4 | 17 | 11 | 62 | N | P | N | N | N | N |
| TIPRL | high in P | 4.9 | 0.005826117 | 2.2 | 484 | 105 | 109 | 72 | 609 | 412 | 10 | N | N | N | N | N | N |
| STX1A | high in P | 6.6 | 0.005832936 | 2.2 | 485 | 20 | 30 | 58 | 114 | 270 | 385 | N | N | N | N | N | N |
| AATK | high in P | 12.6 | 0.005846573 | 2.2 | 486 | 7 | 8 | 10 | 26 | 35 | 240 | N | N | N | N | N | N |
| MBD4 | high in P | 3.9 | 0.005877259 | 2.2 | 487 | 308 | 195 | 258 | 1028 | 996 | 23 | N | N | N | N | N | N |
| USF1 | high in P | 6.8 | 0.005884078 | 2.2 | 488 | 4 | 4 | 7 | 33 | 25 | 1023 | P | N | N | N | N | N |
| CSTF3 | high in P | 5.4 | 0.005890897 | 2.2 | 489 | 19 | 12 | 9 | 45 | 62 | 48 | N | N | N | N | N | N |
| TAF10 | high in P | 5.7 | 0.005904535 | 2.2 | 490 | 435 | 144 | 294 | 1564 | 1828 | 85 | N | N | N | N | N | N |
| SNAI3 | high in P | 11.9 | 0.005911354 | 2.2 | 491 | 3 | 3 | 5 | 26 | 56 | 1506 | N | N | N | N | N | N |
| TAF1C | high in P | 9.3 | 0.005918173 | 2.2 | 492 | 40 | 61 | 161 | 525 | 505 | 510 | N | N | N | N | N | N |
| GFM1 | high in P | 5.7 | 0.005924991 | 2.2 | 493 | 55 | 53 | 41 | 300 | 340 | 583 | N | N | N | N | N | N |
| DPF2 | high in P | 5.7 | 0.005938629 | 2.2 | 494 | 66 | 38 | 106 | 381 | 360 | 147 | N | N | N | N | N | N |
| MPHOSPH10 | high in P | 4.2 | 0.005959086 | 2.2 | 495 | 100 | 120 | 164 | 614 | 629 | 404 | N | N | N | N | N | N |
| FAM3A | high in P | 7.0 | 0.005965905 | 2.2 | 496 | 77 | 99 | 222 | 1227 | 626 | 599 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | Nulliparous (NP) | | | | Parous (P) | | | NP | | P | NP | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| PVT1 | high in P | 12.9 | 0.005972724 | 2.2 | 497 | 138 | 85 | 87 | 511 | 4208 | 1098 | N | N | N | N | N | N |
| CENPA | high in P | 6.3 | 0.005993181 | 2.2 | 498 | 4 | 4 | 5 | 14 | 11 | 10 | N | N | N | N | N | N |
| C9orf78 | high in P | 5.1 | 0.006 | 2.2 | 499 | 118 | 198 | 131 | 831 | 605 | 653 | N | N | N | N | N | N |
| TKTL1 | high in P | 18.6 | 0.006027276 | 2.2 | 500 | 3 | 5 | 16 | 73 | 36 | 117 | N | N | N | N | N | N |
| ZNF394 | high in P | 5.6 | 0.006049778 | 2.2 | 501 | 4 | 5 | 6 | 20 | 22 | 15 | N | N | N | N | N | N |
| SLC35B1 | high in P | 7.1 | 0.006056597 | 2.2 | 502 | 220 | 132 | 275 | 2799 | 1586 | 766 | N | N | N | N | N | N |
| SCT | high in P | 12.9 | 0.006110467 | 2.2 | 503 | 2 | 2 | 3 | 8 | 20 | 45 | N | N | N | N | N | N |
| TRMT61B | high in P | 4.9 | 0.006132288 | 2.2 | 504 | 17 | 17 | 7 | 54 | 67 | 50 | NA | NA | N | N | N | N |
| RPL18 | high in P | 4.8 | 0.006145926 | 2.2 | 505 | 3490 | 2432 | 5137 | 16900 | 16128 | 21500 | N | N | N | N | N | N |
| STOML1 | high in P | 7.7 | 0.006159564 | 2.2 | 506 | 19 | 8 | 14 | 41 | 61 | 38 | N | N | N | N | N | N |
| ISOC2 | high in P | 4.9 | 0.006166383 | 2.2 | 507 | 86 | 81 | 113 | 536 | 490 | 270 | N | N | N | N | N | N |
| SLC43A2 | high in P | 7.7 | 0.006173202 | 2.2 | 508 | 204 | 103 | 78 | 873 | 538 | 725 | N | N | N | N | N | N |
| LOC285456 | high in P | 6.0 | 0.006193658 | 2.2 | 509 | 3 | 5 | 7 | 20 | 21 | 31 | NA | NA | N | N | N | N |
| C4orf52 | high in P | 6.1 | 0.006207296 | 2.2 | 510 | 5 | 5 | 7 | 20 | 16 | 30 | N | N | N | N | N | N |
| UCKL1 | high in P | 6.1 | 0.006214115 | 2.2 | 511 | 238 | 83 | 217 | 1423 | 1035 | 806 | NA | NA | N | N | N | N |
| LOC100133991 | high in P | 4.7 | 0.006227753 | 2.2 | 512 | 9 | 7 | 4 | 18 | 20 | 32 | N | N | N | N | N | N |
| CCDC71 | high in P | 5.1 | 0.006241391 | 2.2 | 513 | 65 | 32 | 56 | 256 | 218 | 143 | N | N | N | N | N | N |
| MED11 | high in P | 5.8 | 0.006255029 | 2.2 | 514 | 55 | 25 | 20 | 247 | 214 | 89 | N | N | N | N | N | N |
| INPP5K | high in P | 6.3 | 0.006274486 | 2.2 | 515 | 20 | 39 | 30 | 167 | 91 | 269 | N | N | N | N | N | N |
| ZGPAT | high in P | 8.3 | 0.006315036 | 2.2 | 516 | 36 | 11 | 20 | 149 | 134 | 150 | N | N | N | N | N | N |
| C1orf84 | high in P | 6.0 | 0.006321855 | 2.2 | 517 | 25 | 5 | 20 | 118 | 83 | 124 | N | N | N | N | N | N |
| CAPZB | high in P | 7.7 | 0.006328674 | 2.2 | 518 | 2249 | 597 | 1035 | 14132 | 7767 | 6290 | N | N | N | N | N | N |
| ZNF845 | high in P | 8.4 | 0.006335493 | 2.2 | 519 | 2 | 2 | 2 | 33 | 15 | 15 | P | P | N | N | N | P |
| HTATSF1 | high in P | 3.8 | 0.006349131 | 2.2 | 520 | 8 | 14 | 14 | 44 | 49 | 54 | NA | NA | N | N | N | N |
| CRCP | high in P | 5.4 | 0.00635595 | 2.2 | 521 | 39 | 29 | 28 | 98 | 158 | 198 | NA | NA | N | P | N | N |
| FLJ39582 | high in P | 6.3 | 0.006369587 | 2.2 | 522 | 36 | 7 | 28 | 179 | 123 | 125 | NA | NA | N | N | N | N |
| RHOD | high in P | 6.8 | 0.006408456 | 2.2 | 523 | 55 | 23 | 39 | 244 | 694 | 147 | N | N | N | N | N | N |
| ZNF397OS | high in P | 4.8 | 0.006427549 | 2.2 | 524 | 18 | 13 | 26 | 75 | 68 | 107 | N | N | N | N | N | N |
| MTAP | high in P | 3.3 | 0.006441186 | 2.2 | 525 | 49 | 55 | 63 | 150 | 166 | 148 | NA | NA | N | N | N | N |
| PARD6A | high in P | 7.0 | 0.006468462 | 2.2 | 526 | 6 | 6 | 6 | 19 | 11 | 23 | N | P | N | P | N | N |
| SNRPA | high in P | 5.6 | 0.0064821 | 2.2 | 527 | 438 | 168 | 407 | 2663 | 1438 | 1924 | N | N | N | N | N | N |
| LOC643008 | high in P | 7.1 | 0.006488919 | 2.2 | 528 | 15 | 10 | 13 | 63 | 49 | 73 | N | N | N | N | N | N |
| LOC146880 | high in P | 7.9 | 0.006495738 | 2.2 | 529 | 4 | 5 | 18 | 49 | 82 | 43 | N | N | N | N | N | N |
| FANCB | high in P | 44.2 | 0.006502557 | 2.2 | 530 | 28 | 2 | 2 | 55 | 53 | 68 | N | N | N | N | N | N |
| DPP3 | high in P | 6.0 | 0.006516195 | 2.2 | 531 | 23 | 23 | 29 | 172 | 121 | 63 | N | N | N | N | N | N |
| S100A13 | high in P | 8.9 | 0.006523014 | 2.2 | 532 | 10 | 10 | 12 | 18 | 28 | 28 | N | N | N | N | N | N |
| C6orf59 | high in P | 6.8 | 0.0065529 | 2.2 | 533 | 9 | 3 | 3 | 9 | 8 | 16 | NA | NA | N | N | N | N |
| C19orf24 | high in P | 5.4 | 0.006557109 | 2.2 | 534 | 21 | 32 | 15 | 110 | 156 | 80 | N | N | N | N | N | N |
| CD79A | high in P | 8.6 | 0.006579611 | 2.2 | 535 | 3 | 3 | 4 | 11 | 17 | 35 | N | N | N | N | N | N |
| DMXL1 | high in P | 7.8 | 0.00658643 | 2.2 | 536 | 63 | 34 | 37 | 311 | 158 | 173 | N | N | N | N | N | N |
| GPRIN1 | high in P | 7.0 | 0.006593249 | 2.2 | 537 | 5 | 10 | 17 | 65 | 66 | 59 | N | N | N | N | N | N |
| PSMB2 | high in P | 7.6 | 0.006600068 | 2.2 | 538 | 409 | 522 | 458 | 3924 | 3308 | 1423 | N | N | N | N | N | N |
| KPNA5 | high in P | 4.6 | 0.006600068 | 2.2 | 539 | 6 | 11 | 14 | 29 | 39 | 59 | N | N | N | N | N | N |
| OXT | high in P | 14.3 | 0.006606887 | 2.2 | 540 | 1 | 1 | 4 | 14 | 19 | 26 | P | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | Parous (P) | | | NP | | P | NP | | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| MYLPF | high in P | 8.2 | 0.000613706 | 2.2 | 541 | 1 | 5 | 2 | 24 | 46 | 16 | N | N | N | N | N | P |
| GRID1 | high in P | 17.4 | 0.000623935 | 2.2 | 542 | 128 | 23 | 29 | 738 | 307 | 384 | N | N | N | N | N | N |
| C6orf136 | high in P | 4.2 | 0.00065462 | 2.2 | 543 | 29 | 28 | 42 | 128 | 113 | 113 | N | N | N | N | N | N |
| ZSCAN21 | high in P | 4.5 | 0.000675077 | 2.2 | 544 | 5 | 11 | 17 | 68 | 59 | 33 | NA | NA | N | N | N | N |
| LOC283314 | high in P | 6.5 | 0.000681896 | 2.2 | 545 | 45 | 32 | 38 | 159 | 197 | 211 | NA | NA | N | N | N | N |
| C8orf75 | high in P | 5.2 | 0.000688715 | 2.2 | 546 | 9 | 2 | 3 | 7 | 12 | 10 | N | N | N | N | N | N |
| FBXL15 | high in P | 5.1 | 0.000702353 | 2.2 | 547 | 68 | 41 | 90 | 460 | 244 | 264 | N | N | N | N | N | N |
| TULP2 | high in P | 13.2 | 0.000741221 | 2.2 | 548 | 15 | 4 | 4 | 34 | 17 | 79 | N | N | N | N | N | N |
| C20orf4 | high in P | 7.8 | 0.000754859 | 2.2 | 549 | 6 | 60 | 51 | 432 | 469 | 298 | N | N | N | N | N | N |
| SLC25A10 | high in P | 3.7 | 0.000761677 | 2.2 | 550 | 12 | 12 | 10 | 45 | 32 | 29 | N | N | N | N | N | N |
| PKP4 | high in P | 7.0 | 0.000775315 | 2.2 | 551 | 444 | 219 | 359 | 1551 | 3685 | 1578 | N | N | N | N | N | N |
| EEF1A2 | high in P | 8.5 | 0.000795772 | 2.2 | 552 | 7 | 13 | 30 | 193 | 247 | 52 | N | N | N | N | N | N |
| FAM50B | high in P | 14.6 | 0.000802591 | 2.2 | 553 | 32 | 6 | 8 | 98 | 79 | 92 | N | N | N | N | N | N |
| FGFRL1 | high in P | 6.1 | 0.00080941 | 2.2 | 554 | 71 | 129 | 158 | 476 | 1357 | 812 | N | N | N | N | N | N |
| SLC25A22 | high in P | 4.7 | 0.000823048 | 2.2 | 555 | 18 | 9 | 16 | 61 | 76 | 52 | N | N | N | N | N | N |
| DGKE | high in P | 4.5 | 0.000829867 | 2.2 | 556 | 94 | 93 | 128 | 402 | 459 | 672 | N | P | N | N | N | N |
| IDH3G | high in P | 4.7 | 0.000836686 | 2.2 | 557 | 97 | 82 | 60 | 451 | 402 | 250 | N | N | N | N | N | N |
| FANCC | high in P | 8.5 | 0.000865326 | 2.2 | 558 | 24 | 18 | 43 | 96 | 218 | 273 | N | N | N | N | N | N |
| PHB2 | high in P | 5.4 | 0.000872145 | 2.2 | 559 | 2195 | 780 | 3065 | 13187 | 13962 | 9947 | N | N | P | N | N | N |
| ATP5J2 | high in P | 4.7 | 0.000878964 | 2.2 | 560 | 35 | 26 | 22 | 118 | 173 | 71 | N | N | N | N | N | N |
| NSFL1C | high in P | 5.9 | 0.000885782 | 2.2 | 561 | 297 | 376 | 642 | 3476 | 3640 | 1508 | N | N | N | N | N | N |
| CSF3R | high in P | 10.1 | 0.000892601 | 2.2 | 562 | 9 | 9 | 12 | 28 | 47 | 214 | N | N | N | N | N | N |
| TAF3 | high in P | 9.0 | 0.00089942 | 2.2 | 563 | 148 | 50 | 42 | 475 | 390 | 467 | N | P | N | N | N | N |
| PLIN5 | high in P | 6.5 | 0.000918513 | 2.2 | 564 | 22 | 9 | 25 | 81 | 166 | 99 | NA | NA | N | N | N | N |
| SART1 | high in P | 4.5 | 0.000925332 | 2.2 | 565 | 257 | 171 | 327 | 1136 | 1350 | 829 | N | P | N | N | N | N |
| ZNF500 | high in P | 5.1 | 0.00093897 | 2.2 | 566 | 18 | 11 | 19 | 63 | 91 | 53 | N | N | N | N | N | N |
| CHTF18 | high in P | 10.2 | 0.000959427 | 2.2 | 567 | 94 | 22 | 41 | 277 | 390 | 863 | N | N | N | N | N | N |
| TYMS | high in P | 10.6 | 0.000973065 | 2.2 | 568 | 12 | 6 | 6 | 29 | 57 | 28 | N | N | N | N | N | N |
| HSD11B1 | high in P | 13.7 | 0.000986703 | 2.2 | 569 | 31 | 56 | 187 | 766 | 515 | 715 | N | P | N | N | N | N |
| GGT8P | high in P | 6.4 | 0.000700716 | 2.2 | 570 | 15 | 4 | 5 | 30 | 15 | 24 | N | N | N | N | N | N |
| TBRG4 | high in P | 7.1 | 0.007027617 | 2.2 | 571 | 119 | 179 | 411 | 1675 | 1805 | 827 | N | P | N | N | N | N |
| DNHD1 | high in P | 9.8 | 0.007034436 | 2.2 | 572 | 49 | 32 | 43 | 305 | 185 | 208 | N | N | N | N | N | N |
| DPY19L2P2 | high in P | 7.5 | 0.007041255 | 2.2 | 573 | 28 | 12 | 12 | 49 | 49 | 40 | N | N | N | N | N | N |
| FBXO10 | high in P | 16.5 | 0.007054893 | 2.2 | 574 | 59 | 13 | 20 | 204 | 188 | 272 | N | N | N | N | N | N |
| HMOX2 | high in P | 7.0 | 0.007061712 | 2.2 | 575 | 350 | 106 | 285 | 1877 | 2048 | 1043 | N | N | N | N | N | N |
| AES | high in P | 6.4 | 0.007068531 | 2.1 | 576 | 3213 | 806 | 1852 | 10796 | 11526 | 11735 | N | N | N | N | N | N |
| GSC | high in P | 6.9 | 0.007088987 | 2.1 | 577 | 49 | 14 | 50 | 341 | 132 | 275 | N | N | N | N | N | N |
| MDM4 | high in P | 4.1 | 0.007138766 | 2.1 | 578 | 69 | 85 | 143 | 697 | 534 | 468 | N | N | N | N | N | N |
| GP5 | high in P | 6.4 | 0.007159223 | 2.1 | 579 | 6 | 6 | 6 | 17 | 11 | 26 | N | N | N | N | N | P |
| SLAMF6 | high in P | 6.1 | 0.007166042 | 2.1 | 580 | 5 | 5 | 5 | 11 | 10 | 14 | N | N | N | P | N | N |
| SBF1 | high in P | 6.3 | 0.007205592 | 2.1 | 581 | 26 | 38 | 109 | 309 | 423 | 425 | N | N | N | N | N | N |
| CNGB1 | high in P | 5.6 | 0.007212411 | 2.1 | 582 | 17 | 11 | 12 | 21 | 24 | 31 | N | N | N | N | N | N |
| SLED1 | high in P | 15.1 | 0.007219229 | 2.1 | 583 | 2 | 3 | 12 | 29 | 49 | 169 | N | N | N | N | N | N |
| PANK4 | high in P | 9.6 | 0.007232867 | 2.1 | 584 | 109 | 86 | 348 | 880 | 1066 | 1039 | N | P | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | | Nulliparous (NP) | | | | Parous (P) | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| LOC654433 | high in P | 16.2 | 0.007239686 | 2.1 | 585 | 11 | 12 | 14 | 126 | 271 | 27 | N | N | N | N | N | N |
| SLC7A5P2 | high in P | 5.0 | 0.007260143 | 2.1 | 586 | 13 | 27 | 35 | 85 | 80 | 127 | NA | NA | N | N | N | N |
| INPP5D | high in P | 7.3 | 0.007290147 | 2.1 | 587 | 16 | 12 | 17 | 51 | 61 | 294 | N | N | N | N | N | N |
| GPC2 | high in P | 7.8 | 0.007302421 | 2.1 | 588 | 5 | 5 | 5 | 18 | 19 | 15 | N | N | N | N | N | N |
| ABCD1 | high in P | 5.1 | 0.007309240 | 2.1 | 589 | 59 | 43 | 58 | 178 | 166 | 296 | N | N | N | N | N | N |
| USP13 | high in P | 3.4 | 0.007342653 | 2.1 | 590 | 76 | 75 | 76 | 269 | 321 | 255 | N | N | N | N | N | N |
| UNC13D | high in P | 5.5 | 0.007356290 | 2.1 | 591 | 18 | 32 | 56 | 121 | 143 | 283 | N | N | N | N | N | N |
| B3GAT1 | high in P | 17.7 | 0.007412888 | 2.1 | 592 | 9 | 9 | 9 | 17 | 148 | 45 | P | P | N | N | N | N |
| DUOX2 | high in P | 9.3 | 0.007419707 | 2.1 | 593 | 7 | 9 | 8 | 17 | 73 | 25 | P | P | N | N | N | N |
| AVPI1 | high in P | 5.6 | 0.007426526 | 2.1 | 594 | 60 | 20 | 26 | 144 | 129 | 220 | N | N | N | N | N | N |
| DNASE1 | high in P | 3.4 | 0.007433345 | 2.1 | 595 | 30 | 34 | 36 | 98 | 92 | 102 | N | N | N | N | N | N |
| NDUFV3 | high in P | 6.7 | 0.007467439 | 2.1 | 596 | 164 | 56 | 72 | 1182 | 1005 | 334 | N | N | N | N | N | N |
| LXN | high in P | 8.8 | 0.007474258 | 2.1 | 597 | 9 | 17 | 6 | 68 | 40 | 56 | N | N | N | N | N | N |
| RBM15B | high in P | 4.3 | 0.007481077 | 2.1 | 598 | 117 | 199 | 118 | 765 | 647 | 571 | NA | N | N | N | N | N |
| TRMT2A | high in P | 4.2 | 0.007487896 | 2.1 | 599 | 9 | 44 | 25 | 122 | 133 | 94 | N | N | N | N | N | N |
| PSMD1 | high in P | 5.9 | 0.007494715 | 2.1 | 600 | 282 | 460 | 664 | 5035 | 2790 | 1741 | N | N | N | N | N | N |
| LOC344967 | high in P | 7.5 | 0.007540402 | 2.1 | 601 | 169 | 51 | 69 | 425 | 517 | 480 | NA | NA | N | N | N | N |
| THAP4 | high in P | 6.9 | 0.007547221 | 2.1 | 602 | 409 | 135 | 235 | 1542 | 1652 | 997 | N | N | N | N | N | N |
| PSKH1 | high in P | 4.4 | 0.007555404 | 2.1 | 603 | 11 | 30 | 23 | 69 | 73 | 82 | N | N | N | N | N | N |
| ERCC8 | high in P | 5.3 | 0.007569042 | 2.1 | 604 | 6 | 6 | 6 | 15 | 23 | 18 | N | N | N | N | N | N |
| ZNF623 | high in P | 6.3 | 0.007609274 | 2.1 | 605 | 21 | 7 | 9 | 53 | 37 | 69 | P | P | N | N | N | N |
| SNX8 | high in P | 8.0 | 0.007616093 | 2.1 | 606 | 45 | 65 | 150 | 629 | 511 | 317 | N | N | N | N | N | N |
| LOC284578 | high in P | 8.0 | 0.007629731 | 2.1 | 607 | 13 | 15 | 15 | 133 | 39 | 47 | NA | NA | N | N | N | N |
| PRRG2 | high in P | 10.3 | 0.007653597 | 2.1 | 608 | 2 | 8 | 19 | 42 | 114 | 80 | N | N | N | N | N | N |
| TUBB2C | high in P | 5.8 | 0.007693829 | 2.1 | 609 | 1698 | 2331 | 2731 | 6216 | 13417 | 15417 | N | N | N | N | N | N |
| CKB | high in P | 8.1 | 0.007714286 | 2.1 | 610 | 664 | 255 | 829 | 2078 | 5123 | 6352 | N | N | N | N | N | N |
| C14orf182 | high in P | 9.9 | 0.007734743 | 2.1 | 611 | 12 | 6 | 6 | 19 | 44 | 24 | NA | NA | N | N | N | N |
| NCRNA00085 | high in P | 5.1 | 0.007774838 | 2.1 | 612 | 21 | 12 | 11 | 23 | 38 | 42 | N | N | N | N | N | N |
| TSG101 | high in P | 5.8 | 0.007755199 | 2.1 | 613 | 319 | 177 | 338 | 4256 | 1757 | 935 | N | N | N | N | N | N |
| HPS6 | high in P | 4.1 | 0.007768837 | 2.1 | 614 | 32 | 34 | 29 | 191 | 106 | 76 | N | N | N | N | N | N |
| ADAT3 | high in P | 5.8 | 0.007775656 | 2.1 | 615 | 109 | 27 | 118 | 484 | 642 | 600 | N | N | N | N | N | N |
| C6orf1 | high in P | 4.4 | 0.007782475 | 2.1 | 616 | 50 | 32 | 41 | 246 | 208 | 110 | N | N | N | N | N | N |
| EDNRB | high in P | 4.6 | 0.007802932 | 2.1 | 617 | 3549 | 2410 | 3053 | 30925 | 10365 | 12704 | P | P | N | N | N | N |
| ATP6V0D2 | high in P | 3.9 | 0.007823389 | 2.1 | 618 | 114 | 65 | 126 | 378 | 387 | 377 | N | N | N | N | N | N |
| DISP1 | high in P | 3.1 | 0.007843846 | 2.1 | 619 | 49 | 44 | 47 | 127 | 141 | 131 | N | N | N | N | N | N |
| C15orf17 | high in P | 4.1 | 0.007862939 | 2.1 | 620 | 132 | 86 | 90 | 347 | 531 | 439 | P | P | N | N | N | N |
| PPP1R3F | high in P | 6.3 | 0.007888851 | 2.1 | 621 | 98 | 35 | 50 | 452 | 220 | 284 | P | P | N | N | N | N |
| PLD6 | high in P | 8.3 | 0.007909308 | 2.1 | 622 | 36 | 15 | 15 | 114 | 116 | 142 | N | N | N | N | N | N |
| NELF | high in P | 4.8 | 0.007962496 | 2.1 | 623 | 235 | 282 | 496 | 1365 | 1751 | 1114 | N | N | N | N | N | N |
| SGIP1 | high in P | 4.8 | 0.007969315 | 2.1 | 624 | 20 | 19 | 9 | 73 | 44 | 71 | N | N | N | N | N | N |
| HMX3 | high in P | 6.9 | 0.007989772 | 2.1 | 625 | 7 | 1 | 2 | 25 | 14 | 9 | P | P | N | N | N | N |
| GPR25 | high in P | 5.3 | 0.007996591 | 2.1 | 626 | 22 | 6 | 12 | 34 | 65 | 83 | P | P | N | N | N | N |
| PPM1D | high in P | 8.8 | 0.008025912 | 2.1 | 627 | 48 | 22 | 15 | 138 | 123 | 419 | N | N | N | N | N | N |
| KPNB1 | high in P | 3.6 | 0.008046369 | 2.1 | 628 | 476 | 474 | 585 | 1483 | 2171 | 1740 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | | Parous (P) | | | NP | P | NP | P | Pro-moter Met |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| EIF2B4 | high in P | 3.5 | 0.008073645 | 2.1 | 629 | 95 | 137 | 99 | 458 | 412 | 323 | N | N | N | N | N | N |
| C17orf63 | high in P | 5.0 | 0.008080464 | 2.1 | 630 | 92 | 90 | 118 | 604 | 675 | 310 | N | N | N | N | N | N |
| CHEK1 | high in P | 4.7 | 0.008100921 | 2.1 | 631 | 29 | 16 | 25 | 62 | 107 | 75 | N | N | N | N | N | N |
| TM2D2 | high in P | 4.7 | 0.008114558 | 2.1 | 632 | 51 | 33 | 54 | 262 | 191 | 137 | N | N | N | N | N | N |
| PIGL | high in P | 4.6 | 0.008128196 | 2.1 | 633 | 41 | 15 | 26 | 110 | 86 | 110 | N | N | N | N | P | N |
| POP1 | high in P | 10.7 | 0.008177975 | 2.1 | 634 | 13 | 13 | 14 | 47 | 81 | 42 | N | N | N | N | N | N |
| SLC4A3 | high in P | 10.5 | 0.008184794 | 2.1 | 635 | 70 | 18 | 17 | 119 | 330 | 189 | N | N | N | N | N | N |
| FAAH | high in P | 7.0 | 0.008191613 | 2.1 | 636 | 17 | 16 | 28 | 56 | 70 | 59 | N | N | N | N | N | N |
| RBM39 | high in P | 6.4 | 0.008225707 | 2.1 | 637 | 667 | 997 | 697 | 4293 | 2312 | 6218 | N | N | N | N | N | N |
| RFXANK | high in P | 4.8 | 0.008232526 | 2.1 | 638 | 151 | 62 | 97 | 729 | 447 | 371 | N | N | N | N | N | N |
| PROCA1 | high in P | 5.4 | 0.008239345 | 2.1 | 639 | 3 | 3 | 4 | 15 | 8 | 14 | N | N | N | N | N | N |
| LOC283663 | high in P | 10.6 | 0.008246164 | 2.1 | 640 | 6 | 7 | 37 | 149 | 87 | 268 | N | N | N | N | N | N |
| LAMA4 | high in P | 5.2 | 0.008281623 | 2.1 | 641 | 1660 | 465 | 1265 | 7394 | 4865 | 6145 | N | N | N | N | N | N |
| MAP7D1 | high in P | 5.0 | 0.008302208 | 2.1 | 642 | 1285 | 606 | 2301 | 6853 | 9335 | 6496 | N | N | N | N | N | N |
| ARHGAP11A | high in P | 4.3 | 0.008308899 | 2.1 | 643 | 8 | 13 | 10 | 44 | 29 | 26 | N | N | N | N | N | N |
| MAGEA1 | high in P | 4.7 | 0.008315718 | 2.1 | 644 | 2 | 2 | 2 | 6 | 7 | 5 | N | N | N | N | N | N |
| C2orf52 | high in P | 7.5 | 0.008329356 | 2.1 | 645 | 4 | 8 | 10 | 52 | 51 | 27 | N | P | N | N | N | N |
| CUL2 | high in P | 3.5 | 0.008336175 | 2.1 | 646 | 74 | 56 | 68 | 187 | 212 | 207 | N | N | N | N | N | N |
| TP53I13 | high in P | 5.0 | 0.008391408 | 2.1 | 647 | 132 | 57 | 203 | 978 | 548 | 639 | N | N | N | N | N | N |
| IRF2BP1 | high in P | 5.1 | 0.008411865 | 2.1 | 648 | 114 | 37 | 83 | 422 | 457 | 317 | P | N | N | N | N | N |
| DDN | high in P | 7.1 | 0.008432322 | 2.1 | 649 | 3 | 3 | 4 | 9 | 21 | 28 | P | N | N | P | N | N |
| MMP17 | high in P | 6.4 | 0.008448005 | 2.1 | 650 | 6 | 10 | 31 | 95 | 65 | 77 | N | N | N | N | N | N |
| ZDHHC14 | high in P | 3.8 | 0.008461643 | 2.1 | 651 | 168 | 139 | 116 | 418 | 618 | 529 | P | N | N | N | N | P |
| MMEL1 | high in P | 7.6 | 0.008468462 | 2.1 | 652 | 4 | 4 | 7 | 25 | 41 | 15 | P | N | N | N | N | N |
| TUBE1 | high in P | 5.2 | 0.008475281 | 2.1 | 653 | 25 | 36 | 39 | 262 | 186 | 92 | N | N | N | N | N | N |
| VILL | high in P | 5.8 | 0.008488919 | 2.1 | 654 | 39 | 17 | 21 | 98 | 67 | 142 | N | P | N | N | N | N |
| PBX4 | high in P | 9.0 | 0.008495738 | 2.1 | 655 | 92 | 27 | 34 | 695 | 160 | 910 | N | N | N | N | N | N |
| REPIN1 | high in P | 12.7 | 0.008502557 | 2.1 | 656 | 439 | 76 | 117 | 1578 | 1633 | 922 | P | N | N | N | N | N |
| OVGP1 | high in P | 8.7 | 0.008516195 | 2.1 | 657 | 17 | 15 | 13 | 23 | 62 | 57 | N | N | N | N | N | N |
| PELI3 | high in P | 5.9 | 0.008523014 | 2.1 | 658 | 38 | 20 | 32 | 212 | 102 | 87 | N | P | N | N | N | N |
| APOL3 | high in P | 6.8 | 0.008529833 | 2.1 | 659 | 136 | 32 | 104 | 998 | 509 | 443 | N | N | N | N | N | N |
| SCARF1 | high in P | 8.8 | 0.008536652 | 2.1 | 660 | 19 | 8 | 12 | 47 | 76 | 79 | NA | NA | N | N | N | N |
| PPP2CB | high in P | 3.9 | 0.008543471 | 2.1 | 661 | 1814 | 2047 | 2552 | 5778 | 7211 | 9626 | N | N | N | N | N | N |
| HEBP2 | high in P | 5.0 | 0.008557109 | 2.1 | 662 | 44 | 25 | 29 | 211 | 196 | 82 | NA | P | N | N | P | N |
| MUDENG | high in P | 4.1 | 0.008563928 | 2.1 | 663 | 12 | 18 | 10 | 59 | 43 | 41 | N | N | N | N | N | N |
| ZNF496 | high in P | 4.0 | 0.008570747 | 2.1 | 664 | 57 | 23 | 35 | 145 | 133 | 169 | N | P | N | N | N | N |
| FOXD1 | high in P | 6.8 | 0.008584385 | 2.1 | 665 | 9 | 6 | 3 | 32 | 14 | 80 | P | N | N | N | N | N |
| GVIN1 | high in P | 5.8 | 0.008591204 | 2.1 | 666 | 6 | 6 | 6 | 10 | 11 | 17 | N | P | N | N | N | N |
| PNCK | high in P | 7.9 | 0.008620525 | 2.1 | 667 | 4 | 4 | 4 | 8 | 11 | 31 | N | N | N | N | N | N |
| SEC31A | high in P | 5.3 | 0.008627344 | 2.1 | 668 | 1213 | 514 | 656 | 4684 | 3455 | 3076 | P | N | N | N | P | N |
| HIRA | high in P | 4.6 | 0.008634163 | 2.1 | 669 | 69 | 50 | 51 | 184 | 311 | 224 | N | N | N | N | N | N |
| C11orf84 | high in P | 8.9 | 0.008640982 | 2.1 | 670 | 104 | 55 | 112 | 900 | 285 | 2057 | N | N | N | N | P | N |
| ENDOG | high in P | 4.1 | 0.008865462 | 2.1 | 671 | 107 | 62 | 83 | 329 | 362 | 228 | N | N | N | N | N | N |
| TIMM17A | high in P | 4.2 | 0.008690078 | 2.1 | 672 | 576 | 391 | 569 | 2474 | 2770 | 1589 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | Nulliparous (NP) | | | | Parous (P) | | | NP | CD44+ N74 | CD44+ N66 | GeneBody NP Met | GeneBody Met | Pro-moter Met | Pro-moter Met |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | | | P | NP | P | NP | P |
| DGCR8 | high in P | 4.2 | 0.008696897 | 2.1 | 673 | 89 | 92 | 105 | 436 | 641 | 270 | N | N | N | N | N | N | N |
| VMO1 | high in P | 10.7 | 0.008724173 | 2.1 | 674 | 2 | 3 | 7 | 59 | 13 | 72 | P | N | N | N | N | N | N |
| LRCH1 | high in P | 4.8 | 0.008737811 | 2.1 | 675 | 362 | 204 | 285 | 986 | 1175 | 1939 | N | N | N | N | N | N | N |
| PREX2 | high in P | 6.6 | 0.008751449 | 2.1 | 676 | 13 | 13 | 17 | 38 | 34 | 67 | N | N | N | N | N | N | N |
| GSDMA | high in P | 3.0 | 0.008758268 | 2.1 | 677 | 56 | 49 | 53 | 134 | 119 | 138 | NA | NA | N | N | N | N | N |
| PSORS1C3 | high in P | 5.5 | 0.008765087 | 2.1 | 678 | 13 | 2 | 3 | 11 | 22 | 14 | N | N | N | N | N | N | N |
| C4orf42 | high in P | 3.9 | 0.008771906 | 2.1 | 679 | NA | NA | NA | NA | NA | NA | NA | N | N | N | N | N | N |
| SP4 | high in P | 4.9 | 0.008778725 | 2.1 | 680 | 46 | 35 | 24 | 136 | 125 | 243 | N | N | N | N | N | N | N |
| BAZ1B | high in P | 4.4 | 0.008792363 | 2.1 | 681 | 134 | 134 | 245 | 694 | 858 | 1033 | N | N | N | N | N | N | N |
| RDH5 | high in P | 5.1 | 0.008799182 | 2.1 | 682 | 76 | 17 | 43 | 232 | 178 | 200 | N | N | N | N | N | N | N |
| EIF4G3 | high in P | 3.8 | 0.008818957 | 2.1 | 683 | 30 | 46 | 40 | 99 | 111 | 140 | N | N | N | N | N | N | N |
| MRPS18C | high in P | 9.4 | 0.008832595 | 2.1 | 684 | 4 | 33 | 11 | 153 | 106 | 79 | N | N | N | N | N | N | N |
| MAP4K4 | high in P | 3.9 | 0.008853051 | 2.1 | 685 | 370 | 575 | 757 | 2458 | 2288 | 3270 | N | N | N | N | N | N | N |
| FOXD2 | high in P | 8.8 | 0.008875554 | 2.1 | 686 | 3 | 4 | 6 | 38 | 12 | 56 | P | N | N | N | N | N | N |
| ANKFY1 | high in P | 9.3 | 0.008882373 | 2.1 | 687 | 137 | 38 | 58 | 564 | 465 | 411 | N | N | N | N | N | N | N |
| LOC728606 | high in P | 4.7 | 0.008889192 | 2.1 | 688 | 7 | 20 | 19 | 51 | 62 | 83 | N | N | N | N | N | N | N |
| LOC652276 | high in P | 4.2 | 0.008896283 | 2.1 | 689 | 17 | 22 | 12 | 67 | 55 | 71 | N | N | N | N | N | N | N |
| FRG2 | high in P | 4.5 | 0.008916468 | 2.1 | 690 | 3 | 4 | 3 | 13 | 8 | 11 | P | N | N | N | N | N | N |
| REL | high in P | 6.3 | 0.008930106 | 2.0 | 691 | 498 | 190 | 216 | 1543 | 1167 | 3314 | N | N | N | N | N | N | N |
| ZNF563 | high in P | 5.3 | 0.008934238 | 2.0 | 692 | 19 | 9 | 9 | 21 | 24 | 42 | P | P | N | N | N | N | N |
| UTS2D | high in P | 4.7 | 0.008949199 | 2.0 | 693 | 7 | 10 | 17 | 52 | 25 | 55 | N | N | N | N | N | N | N |
| SEC31B | high in P | 5.9 | 0.008956018 | 2.0 | 694 | 33 | 22 | 28 | 101 | 95 | 124 | N | P | N | N | N | N | N |
| LOC100128675 | high in P | 5.2 | 0.008968974 | 2.0 | 695 | 11 | 12 | 19 | 54 | 39 | 52 | NA | NA | N | N | N | N | N |
| COG1 | high in P | 4.9 | 0.008975793 | 2.0 | 696 | 85 | 29 | 47 | 324 | 193 | 188 | NA | N | N | N | N | N | N |
| KIAA1984 | high in P | 8.2 | 0.008989431 | 2.0 | 697 | 6 | 8 | 16 | 28 | 58 | 40 | NA | P | N | N | N | N | N |
| SP9 | high in P | 8.6 | 0.008999625 | 2.0 | 698 | 8 | 3 | 10 | 26 | 22 | 72 | NA | N | N | N | N | N | N |
| PEX16 | high in P | 5.1 | 0.009003069 | 2.0 | 699 | 52 | 59 | 94 | 558 | 389 | 212 | N | N | N | N | N | N | N |
| TMEM53 | high in P | 5.5 | 0.009059666 | 2.0 | 700 | 29 | 20 | 94 | 385 | 464 | 339 | N | N | N | N | N | N | N |
| SCAND2 | high in P | 3.8 | 0.009082168 | 2.0 | 701 | 69 | 43 | 66 | 192 | 234 | 203 | N | N | N | N | N | N | N |
| CCDC24 | high in P | 6.0 | 0.009094443 | 2.0 | 702 | 37 | 4 | 6 | 39 | 59 | 15 | N | P | N | N | N | N | N |
| NAP1L4 | high in P | 6.8 | 0.009101262 | 2.0 | 703 | 14 | 2 | 2 | 8 | 12 | 5 | P | N | N | N | N | N | N |
| INCENP | high in P | 4.5 | 0.009114899 | 2.0 | 704 | 723 | 350 | 1703 | 3828 | 6504 | 4906 | N | N | N | N | N | N | N |
| C16orf68 | high in P | 5.8 | 0.009128537 | 2.0 | 705 | 18 | 9 | 10 | 35 | 54 | 39 | N | N | N | N | N | N | N |
| TMOD1 | high in P | 7.2 | 0.009135356 | 2.0 | 706 | 52 | 38 | 98 | 363 | 305 | 188 | N | N | N | N | N | N | N |
| OSBPL7 | high in P | 6.7 | 0.009114763 | 2.0 | 707 | 29 | 27 | 41 | 491 | 246 | 95 | N | P | N | N | N | N | N |
| RBM41 | high in P | 7.1 | 0.009173542 | 2.0 | 708 | 36 | 11 | 26 | 126 | 116 | 282 | N | N | N | N | N | N | N |
| MS4A7 | high in P | 4.1 | 0.009180361 | 2.0 | 709 | 2 | 2 | 2 | 8 | 12 | 5 | N | N | N | N | N | N | N |
| CD40 | high in P | 7.3 | 0.009192636 | 2.0 | 710 | 35 | 33 | 57 | 153 | 117 | 136 | N | P | N | N | N | N | N |
| GMFG | high in P | 12.5 | 0.009199454 | 2.0 | 711 | 237 | 118 | 40 | 1319 | 606 | 872 | N | N | N | N | N | N | N |
| ALPP | high in P | 5.8 | 0.009206273 | 2.0 | 712 | 34 | 2 | 54 | 509 | 205 | 340 | N | N | N | N | N | N | N |
| ZNF765 | high in P | 4.6 | 0.009219911 | 2.0 | 713 | 324 | 178 | 315 | 827 | 1185 | 1490 | N | P | N | N | N | N | N |
| RNH1 | high in P | 4.5 | 0.009233549 | 2.0 | 714 | 46 | 40 | 56 | 161 | 329 | 126 | N | N | N | N | N | N | N |
| ALKBH6 | high in P | 5.3 | 0.009250597 | 2.0 | 715 | 1167 | 601 | 809 | 7645 | 4037 | 2701 | N | N | N | N | N | P | N |
| RASA2 | high in P | 4.6 | 0.009257416 | 2.0 | 716 | 27 | 15 | 12 | 66 | 68 | 42 | N | N | N | N | N | N | N |
| | high in P | 5.1 | | 2.0 | | 6 | 6 | 6 | 16 | 16 | 24 | N | N | N | N | N | N | N |

TABLE 15-continued

Genes that Are Differentially Methylated between Nulliparous and Parous CD44+ Breast Epithelial Cells

| | | | | | SAGE-seq | | | | | | ChIP-seq | | | | MSDK-seq | | |
|---|---|---|---|---|---|---|---|---|---|---|---|---|---|---|---|---|---|
| | | | | | Nulliparous (NP) | | | | Parous (P) | | | NP | | P | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| APOA1 | high in P | 9.9 | 0.000927644 | 2.0 | 717 | 22 | 5 | 7 | 24 | 92 | 136 | N | N | N | N | N | N |
| CIB2 | high in P | 9.5 | 0.000925605 | 2.0 | 718 | 129 | 9 | 45 | 431 | 381 | 665 | N | N | N | N | N | N |
| BEGAIN | high in P | 6.8 | 0.000935881 | 2.0 | 719 | 39 | 50 | 55 | 125 | 373 | 327 | N | N | N | N | N | N |
| UBE4B | high in P | 4.0 | 0.000968565 | 2.0 | 720 | 366 | 159 | 307 | 1089 | 1487 | 1212 | N | N | P | N | N | N |
| ARF1 | high in P | 4.0 | 0.000980839 | 2.0 | 721 | 7338 | 4258 | 7770 | 37639 | 23386 | 20252 | N | N | N | N | N | N |
| GNAL | high in P | 7.9 | 0.000987658 | 2.0 | 722 | 6 | 6 | 7 | 14 | 14 | 45 | N | N | N | N | N | N |
| MVK | high in P | 5.2 | 0.000429935 | 2.0 | 723 | 27 | 23 | 55 | 199 | 138 | 93 | N | N | N | N | N | N |
| REXO2 | high in P | 2.9 | 0.000436754 | 2.0 | 724 | 389 | 322 | 373 | 1093 | 1081 | 979 | N | N | N | N | N | N |
| TNFRSF6B | high in P | 6.0 | 0.000457211 | 2.0 | 725 | 76 | 18 | 64 | 362 | 402 | 170 | N | N | N | N | N | N |
| DIO3 | high in P | 8.0 | 0.000472895 | 2.0 | 726 | 11 | 5 | 6 | 16 | 18 | 37 | N | N | N | N | N | N |
| EPR1 | high in P | 16.2 | 0.000479714 | 2.0 | 727 | 34 | 3 | 23 | 57 | 325 | 446 | N | N | N | N | N | P |
| MCM7 | high in P | 4.6 | 0.000505626 | 2.0 | 728 | 160 | 136 | 199 | 470 | 749 | 1183 | N | N | N | N | N | N |
| PPP2R3B | high in P | 5.2 | 0.0095179 | 2.0 | 729 | 23 | 8 | 24 | 55 | 72 | 102 | N | N | N | N | N | N |
| FAM178A | high in P | 3.8 | 0.000542448 | 2.0 | 730 | 28 | 30 | 32 | 95 | 61 | 95 | N | N | N | N | N | N |
| SFRS13B | high in P | 4.9 | 0.000573133 | 2.0 | 731 | 6 | 6 | 7 | 28 | 22 | 21 | NA | NA | N | N | N | N |
| ZBTB39 | high in P | 4.3 | 0.000579952 | 2.0 | 732 | 14 | 20 | 23 | 94 | 60 | 51 | N | N | N | N | N | N |
| HTR3B | high in P | 11.0 | 0.000586771 | 2.0 | 733 | 114 | 6 | 31 | 288 | 339 | 430 | N | P | P | N | N | N |
| B3GAT3 | high in P | 7.2 | 0.000959359 | 2.0 | 734 | 144 | 47 | 58 | 490 | 548 | 330 | N | N | N | N | N | N |
| NES | high in P | 8.1 | 0.000638895 | 2.0 | 735 | 653 | 204 | 560 | 1452 | 5263 | 5161 | N | N | N | N | N | N |
| TGFB1I1 | high in P | 10.4 | 0.000664414 | 2.0 | 736 | 1179 | 125 | 587 | 6602 | 5731 | 3015 | N | N | N | N | N | N |
| NFE2L1 | high in P | 10.5 | 0.000652233 | 2.0 | 737 | 766 | 156 | 524 | 8888 | 2921 | 2172 | N | N | N | N | N | N |
| ZNF208 | high in P | 3.2 | 0.000659052 | 2.0 | 738 | 19 | 29 | 30 | 66 | 73 | 53 | N | N | N | N | N | N |
| GPATCH3 | high in P | 11.1 | 0.000665871 | 2.0 | 739 | 23 | 25 | 96 | 289 | 256 | 195 | N | N | N | N | N | N |
| ZNF579 | high in P | 3.3 | 0.000667269 | 2.0 | 740 | 43 | 55 | 48 | 133 | 171 | 145 | N | N | N | N | N | N |
| SIDT2 | high in P | 4.8 | 0.000679509 | 2.0 | 741 | 129 | 61 | 78 | 377 | 320 | 582 | N | N | N | N | N | N |
| SGTA | high in P | 11.9 | 0.000686328 | 2.0 | 742 | 339 | 24 | 792 | 2996 | 3949 | 7198 | P | N | N | N | N | N |
| TFIP11 | high in P | 3.5 | 0.000698602 | 2.0 | 743 | 102 | 173 | 132 | 455 | 421 | 363 | N | N | N | N | P | N |
| CARD6 | high in P | 3.1 | 0.000705421 | 2.0 | 744 | 391 | 319 | 442 | 1218 | 1048 | 1230 | N | N | N | N | N | N |
| ZNF525 | high in P | 3.8 | 0.000719059 | 2.0 | 745 | 31 | 26 | 27 | 73 | 132 | 86 | N | N | N | N | N | N |
| CCDC57 | high in P | 4.5 | 0.000723878 | 2.0 | 746 | 59 | 43 | 73 | 171 | 278 | 171 | N | N | N | N | N | N |
| C3orf42 | high in P | 6.6 | 0.000739516 | 2.0 | 747 | 3 | 8 | 35 | 55 | 94 | 113 | NA | NA | N | N | N | N |
| TTC21A | high in P | 7.1 | 0.000766792 | 2.0 | 748 | 4 | 4 | 6 | 10 | 17 | 24 | NA | NA | N | N | N | N |
| TECR | high in P | 5.9 | 0.000773611 | 2.0 | 749 | 640 | 200 | 286 | 1675 | 1849 | 1641 | NA | NA | N | N | N | N |
| SPSB3 | high in P | 13.2 | 0.000978043 | 2.0 | 750 | 345 | 96 | 10 | 1258 | 976 | 2140 | N | N | N | N | N | N |
| ALKBH4 | high in P | 6.4 | 0.000787249 | 2.0 | 751 | 441 | 89 | 214 | 1510 | 1261 | 1329 | N | N | N | N | N | N |
| TMEM176A | high in P | 5.3 | 0.000815888 | 2.0 | 752 | 6 | 8 | 6 | 26 | 22 | 45 | N | N | N | N | N | N |
| DAZAP2 | high in P | 4.4 | 0.000822707 | 2.0 | 753 | 1770 | 1069 | 1239 | 9567 | 4655 | 4250 | N | N | N | N | N | N |
| CCDC146 | high in P | 3.8 | 0.000829526 | 2.0 | 754 | 6 | 8 | 15 | 39 | 27 | 31 | N | N | N | N | N | N |
| PQLC2 | high in P | 7.2 | 0.000984521 | 2.0 | 755 | 2 | 2 | 6 | 21 | 27 | 13 | N | N | N | N | N | N |
| SESN1 | high in P | 6.3 | 0.000852029 | 2.0 | 756 | 140 | 79 | 46 | 613 | 261 | 626 | N | N | N | N | N | N |
| TTL | high in P | 3.9 | 0.000858848 | 2.0 | 757 | 97 | 43 | 89 | 344 | 326 | 300 | N | N | N | N | N | N |
| GABBR1 | high in P | 4.2 | 0.000888169 | 2.0 | 758 | 203 | 141 | 248 | 730 | 608 | 893 | N | N | N | N | N | N |
| ZNF70 | high in P | 4.1 | 0.000898398 | 2.0 | 759 | 6 | 6 | 8 | 24 | 32 | 21 | N | N | N | N | N | N |
| SNORD34 | high in P | 13.5 | 0.0094954 | 2.0 | 760 | 2 | 3 | 10 | 17 | 53 | 56 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | | Parous (P) | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 NP | CD44+ N66 P | GeneBody NP Met NP | GeneBody Met P | Pro-moter Met NP | Pro-moter Met P |
| BCL2L11 | high in P | 4.7 | 0.009965223 | 2.0 | 761 | 467 | 286 | 539 | 1701 | 1423 | 2633 | N | N | N | N | N | N |
| MBOAT2 | high in P | 4.2 | 0.009978861 | 2.0 | 762 | 75 | 46 | 39 | 182 | 190 | 171 | N | N | N | N | N | N |
| RNF217 | high in P | 9.5 | 0.00998568 | 2.0 | 763 | 4 | 7 | 5 | 12 | 53 | 52 | N | N | N | N | N | N |
| TBP | high in P | 4.5 | 0.009992499 | 2.0 | 764 | 33 | 29 | 55 | 213 | 194 | 122 | N | N | N | N | N | N |
| C6orf120 | high in P | 8.5 | 0.01002523 | 2.0 | 765 | 119 | 33 | 45 | 361 | 382 | 377 | N | NA | N | N | N | N |
| TRPV1 | high in P | 4.4 | 0.010040914 | 2.0 | 766 | 6 | 7 | 9 | 17 | 34 | 26 | N | N | N | N | N | N |
| KHNYN | high in P | 4.3 | 0.010047733 | 2.0 | 767 | 171 | 93 | 266 | 776 | 1049 | 881 | NA | NA | N | N | N | N |
| PRELID1 | high in P | 4.2 | 0.010054552 | 2.0 | 768 | 85 | 92 | 100 | 347 | 407 | 205 | N | N | N | N | N | N |
| RPS11 | high in P | 6.8 | 0.010075009 | 2.0 | 769 | 32527 | 10403 | 13181 | 193390 | 127672 | 78612 | N | N | N | N | N | N |
| CCDC55 | high in P | 3.2 | 0.010095465 | 2.0 | 770 | 181 | 216 | 221 | 638 | 696 | 902 | N | N | N | N | N | N |
| ZNF335 | high in P | 4.8 | 0.010115922 | 2.0 | 771 | 89 | 76 | 187 | 444 | 509 | 429 | N | N | N | N | N | N |
| LYSMD2 | high in P | 4.9 | 0.010131606 | 2.0 | 772 | 25 | 19 | 19 | 86 | 117 | 42 | N | N | N | N | N | N |
| KIAA0467 | high in P | 3.5 | 0.010166383 | 2.0 | 773 | 47 | 43 | 55 | 147 | 114 | 108 | N | N | N | N | N | N |
| ERAL1 | high in P | 5.2 | 0.01018002 | 2.0 | 774 | 24 | 45 | 31 | 336 | 150 | 90 | N | N | N | N | N | N |
| PDE4D | high in P | 4.0 | 0.010193658 | 2.0 | 775 | 51 | 92 | 65 | 351 | 215 | 419 | N | N | N | N | N | N |
| TIMM13 | high in P | 5.5 | 0.01020047 | 2.0 | 776 | 321 | 231 | 610 | 1775 | 3123 | 1348 | N | N | N | N | N | N |
| COMMD2 | high in P | 4.8 | 0.010235254 | 2.0 | 777 | 14 | 5 | 6 | 29 | 28 | 14 | N | N | N | N | N | N |
| MPPE1 | high in P | 5.8 | 0.010255711 | 2.0 | 778 | 24 | 13 | 39 | 84 | 128 | 132 | N | N | N | N | P | N |
| SLC22A9 | high in P | 15.4 | 0.010274804 | 2.0 | 779 | 3 | 3 | 3 | 6 | 21 | 19 | N | N | N | N | N | N |
| PHF20 | high in P | 4.7 | 0.010293897 | 2.0 | 780 | 147 | 108 | 65 | 710 | 504 | 471 | N | N | N | N | N | N |
| IQCE | high in P | 9.0 | 0.010345721 | 2.0 | 781 | 43 | 18 | 21 | 117 | 126 | 116 | N | N | N | N | N | N |
| C2orf14 | high in P | 6.7 | 0.01035254 | 2.0 | 782 | 8 | 23 | 28 | 104 | 138 | 156 | N | N | N | N | N | N |
| MCM2 | high in P | 5.9 | 0.010366178 | 2.0 | 783 | 45 | 15 | 34 | 189 | 118 | 78 | N | N | N | N | N | N |
| RC3H2 | high in P | 4.3 | 0.010405046 | 2.0 | 784 | 23 | 60 | 87 | 262 | 203 | 301 | N | N | N | N | N | N |
| SYNGR3 | high in P | 8.5 | 0.010434368 | 2.0 | 785 | 3 | 4 | 6 | 15 | 17 | 49 | P | N | N | N | N | N |
| MPPE1 alt / PAPPA | high in P | 5.9 | 0.010456188 | 2.0 | 786 | 47 | 12 | 23 | 113 | 146 | 108 | N | N | N | N | P | N |
| PAPPA | high in P | 7.0 | 0.010463007 | 2.0 | 787 | 120 | 293 | 121 | 4321 | 1168 | 762 | N | N | N | N | N | N |
| SLC6A7 | high in P | 4.9 | 0.010469826 | 2.0 | 788 | 6 | 6 | 7 | 10 | 18 | 14 | N | N | N | N | N | N |
| ATRIP | high in P | 5.1 | 0.010476645 | 2.0 | 789 | 53 | 10 | 35 | 165 | 216 | 117 | N | N | N | N | N | N |
| WDHD1 | high in P | 7.2 | 0.010483464 | 2.0 | 790 | 8 | 8 | 8 | 27 | 11 | 21 | N | N | N | N | N | N |
| E2F4 | high in P | 4.8 | 0.010490283 | 2.0 | 791 | 4 | 9 | 18 | 59 | 100 | 36 | N | N | N | N | N | N |
| SHROOM2 | high in P | 5.6 | 0.010497102 | 2.0 | 792 | 6 | 7 | 9 | 22 | 33 | 17 | N | N | N | N | N | N |
| PARG | high in P | 4.4 | 0.010528469 | 2.0 | 793 | 20 | 23 | 17 | 87 | 44 | 96 | N | N | N | N | N | P |
| MFSD5 | high in P | 3.2 | 0.010535288 | 2.0 | 794 | 91 | 82 | 85 | 354 | 257 | 212 | N | N | N | N | N | N |
| SNRNP25 | high in P | 6.3 | 0.010542107 | 2.0 | 795 | 46 | 9 | 14 | 76 | 96 | 66 | N | P | N | N | N | N |
| FLJ10213 | high in P | 5.7 | 0.010562564 | 2.0 | 796 | 3 | 3 | 3 | 16 | 6 | 16 | N | N | N | N | N | N |
| LTB4R | high in P | 6.4 | 0.010569383 | 2.0 | 797 | 13 | 16 | 22 | 87 | 70 | 29 | N | N | N | N | N | N |
| GYS1 | high in P | 7.1 | 0.010583021 | 2.0 | 798 | 50 | 75 | 218 | 1095 | 681 | 356 | N | N | N | N | N | N |
| UGGT2 | high in P | 6.1 | 0.010647119 | 2.0 | 799 | 29 | 21 | 44 | 249 | 161 | 60 | N | N | N | N | N | N |
| TRAF4 | high in P | 5.0 | 0.010667576 | 2.0 | 800 | 1125 | 559 | 1098 | 2791 | 8537 | 5085 | N | NA | N | N | N | N |
| ST20 | high in P | 5.2 | 0.010681214 | 2.0 | 801 | 2 | 2 | 2 | 6 | 9 | 12 | N | N | N | N | N | N |
| LOC283731 | high in P | 8.3 | 0.010688033 | 2.0 | 802 | 8 | 2 | 4 | 9 | 18 | 34 | NA | NA | N | N | N | N |
| KLC1 | high in P | 6.7 | 0.010713263 | 2.0 | 803 | 454 | 235 | 889 | 3478 | 3374 | 2015 | N | N | N | N | N | N |
| PTRH1 | high in P | 5.3 | 0.010741221 | 2.0 | 804 | 42 | 70 | 113 | 448 | 523 | 192 | N | N | N | N | N | N |

TABLE 15-continued

Genes that Are Differentially Methylated between Nulliparous and Parous CD44+ Breast Epithelial Cells

| | SAGE-seq | | | | | | | | | | | ChIP-seq | | MSDK-seq | | | |
|---|---|---|---|---|---|---|---|---|---|---|---|---|---|---|---|---|---|
| | | | | | | Nulliparous (NP) | | | Parous (P) | | | NP | P | GeneBody | GeneBody | Pro-motor | Pro-moter |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | NP Met | Met | Met | Met |
| WDR5 | high in P | 4.6 | 0.010765769 | 2.0 | 805 | 17 | 37 | 28 | 127 | 150 | 61 | N | N | N | N | N | N |
| FIBP | high in P | 4.2 | 0.010784862 | 2.0 | 806 | 119 | 44 | 150 | 616 | 455 | 388 | N | N | N | N | N | N |
| ZC3H12B | high in P | 5.6 | 0.010838732 | 2.0 | 807 | 9 | 11 | 11 | 32 | 21 | 62 | N | P | N | N | N | N |
| C19orf44 | high in P | 4.0 | 0.01085237 | 2.0 | 808 | 20 | 15 | 23 | 72 | 41 | 57 | N | N | N | N | N | N |
| USP35 | high in P | 3.2 | 0.010888851 | 2.0 | 809 | 6 | 8 | 9 | 20 | 16 | 24 | N | N | N | N | N | N |
| MRPL12 | high in P | 6.3 | 0.010917832 | 2.0 | 810 | 204 | 157 | 144 | 1101 | 1159 | 371 | N | P | N | N | N | N |
| MCOLN2 | high in P | 8.9 | 0.010924651 | 2.0 | 811 | 63 | 20 | 49 | 177 | 222 | 636 | N | N | N | N | N | N |
| DNER | high in P | 4.5 | 0.010938288 | 2.0 | 812 | 7 | 17 | 35 | 108 | 68 | 64 | N | P | N | N | N | N |
| ALG3 | high in P | 4.2 | 0.010957382 | 2.0 | 813 | 229 | 115 | 137 | 1015 | 905 | 425 | N | P | N | N | N | N |
| MKLN1 | high in P | 3.9 | 0.0109642 | 2.0 | 814 | 229 | 165 | 271 | 713 | 936 | 1341 | P | P | N | N | N | N |
| ZGLP1 | high in P | 4.4 | 0.010976475 | 2.0 | 815 | 10 | 5 | 6 | 12 | 17 | 25 | N | N | N | N | N | N |
| IDUA | high in P | 5.2 | 0.010983294 | 2.0 | 816 | 141 | 68 | 101 | 307 | 510 | 1063 | NA | NA | N | N | N | N |
| RAB17 | high in P | 3.7 | 0.010990113 | 2.0 | 817 | 6 | 8 | 10 | 22 | 28 | 21 | N | N | N | N | N | N |
| WFIKKN1 | high in P | 6.8 | 0.01100375 | 2.0 | 818 | 5 | 5 | 7 | 15 | 40 | 69 | N | N | N | N | N | N |
| CCDC93 | high in P | 3.4 | 0.011017388 | 2.0 | 819 | 24 | 35 | 38 | 84 | 102 | 102 | N | N | N | N | N | N |
| CD58 | high in P | 3.7 | 0.011037845 | 2.0 | 820 | 16 | 23 | 15 | 56 | 43 | 79 | N | N | N | N | N | N |
| COG2 | high in P | 6.2 | 0.011044664 | 2.0 | 821 | 27 | 15 | 21 | 144 | 105 | 38 | N | N | N | N | N | N |
| DKFZp761E198 | high in P | 4.0 | 0.011058302 | 2.0 | 822 | 101 | 125 | 176 | 1155 | 519 | 501 | N | N | N | N | N | N |
| ACP1 | high in P | 6.0 | 0.011065121 | 2.0 | 823 | 60 | 34 | 80 | 395 | 620 | 157 | N | N | N | N | N | N |
| ZC3H7B | high in P | 6.1 | 0.011088305 | 2.0 | 824 | 77 | 43 | 51 | 290 | 208 | 183 | NA | NA | N | N | N | N |
| NCRNA00169 | high in P | 5.4 | 0.011127855 | 2.0 | 825 | 6 | 8 | 11 | 22 | 23 | 35 | N | N | N | N | N | N |
| CDKN2A | high in P | 6.5 | 0.011143539 | 2.0 | 826 | 122 | 31 | 43 | 431 | 208 | 256 | P | P | N | N | N | N |
| ZC3H18 | high in P | 3.3 | 0.011150358 | 2.0 | 827 | 74 | 40 | 53 | 166 | 165 | 200 | N | N | N | N | N | N |
| HSPBP1 | high in P | 4.5 | 0.011157177 | 2.0 | 828 | 126 | 88 | 84 | 1031 | 322 | 353 | N | N | N | N | N | N |
| OPLAH | high in P | 3.9 | 0.011169451 | 2.0 | 829 | 112 | 47 | 110 | 386 | 372 | 302 | N | N | N | N | N | N |
| QPCTL | high in P | 5.6 | 0.011183089 | 2.0 | 830 | 3 | 3 | 4 | 34 | 13 | 11 | N | N | N | N | N | N |
| DDTL | high in P | 6.1 | 0.011196727 | 2.0 | 831 | 9 | 18 | 35 | 74 | 140 | 78 | P | P | N | N | N | N |
| SNORA24 | high in P | 5.4 | 0.011206955 | 2.0 | 832 | 1 | 1 | 1 | 3 | 6 | 9 | N | N | N | N | N | N |
| PLB1 | high in P | 5.4 | 0.011206955 | 2.0 | 833 | 7 | 7 | 7 | 9 | 12 | 15 | P | N | N | N | N | N |
| CBS | high in P | 10.0 | 0.011226048 | 1.9 | 834 | 34 | 26 | 9 | 235 | 320 | 52 | P | P | N | N | N | N |
| WAS | high in P | 7.5 | 0.011232867 | 1.9 | 835 | 3 | 9 | 6 | 24 | 22 | 142 | NA | NA | N | N | N | N |
| SNORA80B | high in P | 7.9 | 0.011239686 | 1.9 | 836 | 1 | 4 | 1 | 12 | 23 | 9 | N | N | N | N | N | N |
| POLA1 | high in P | 6.2 | 0.011246505 | 1.9 | 837 | 9 | 9 | 11 | 69 | 19 | 27 | N | N | N | N | N | N |
| ZNF484 | high in P | 4.9 | 0.011260143 | 1.9 | 838 | 4 | 4 | 4 | 15 | 11 | 7 | N | N | N | N | N | N |
| TTLL4 | high in P | 4.6 | 0.011266962 | 1.9 | 839 | 46 | 110 | 184 | 463 | 678 | 433 | N | N | N | N | N | N |
| C7orf63 | high in P | 5.3 | 0.011273781 | 1.9 | 840 | 13 | 16 | 25 | 70 | 40 | 44 | N | N | N | N | N | N |
| RAB2B | high in P | 3.6 | 0.0112806 | 1.9 | 841 | 35 | 25 | 37 | 115 | 88 | 119 | N | N | N | N | N | N |
| ZNF490 | high in P | 5.7 | 0.011287419 | 1.9 | 842 | 28 | 17 | 22 | 74 | 133 | 146 | N | N | N | N | N | N |
| HUWE1 | high in P | 2.8 | 0.011294238 | 1.9 | 843 | 176 | 222 | 204 | 576 | 602 | 627 | N | N | N | N | N | N |
| NNT | high in P | 3.3 | 0.011301057 | 1.9 | 844 | 9 | 10 | 12 | 28 | 23 | 20 | N | N | N | N | N | N |
| FRG1 | high in P | 4.6 | 0.011328333 | 1.9 | 845 | 29 | 46 | 18 | 147 | 132 | 71 | N | N | N | N | N | N |
| CARS | high in P | 6.7 | 0.011335152 | 1.9 | 846 | 294 | 172 | 318 | 2088 | 1976 | 642 | N | N | N | N | N | N |
| C2orf60 | high in P | 5.2 | 0.011334879 | 1.9 | 847 | 37 | 20 | 19 | 101 | 66 | 78 | N | N | N | N | N | N |
| YRDC | high in P | 3.5 | 0.011355609 | 1.9 | 848 | 83 | 44 | 68 | 251 | 205 | 156 | N | N | N | P | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | Nulliparous (NP) | | | Parous (P) | | | | NP | P | NP | P | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| PSENEN | high in P | 4.0 | 0.011369247 | 1.9 | 849 | 189 | 189 | 142 | 817 | 697 | 396 | N | N | N | N | N | N |
| CES3 | high in P | 5.8 | 0.011384248 | 1.9 | 850 | 10 | 15 | 11 | 27 | 56 | 67 | N | N | N | N | N | N |
| SCN11A | high in P | 4.9 | 0.011391067 | 1.9 | 851 | 40 | 18 | 22 | 101 | 86 | 63 | N | N | N | N | N | N |
| PMS2 | high in P | 3.6 | 0.011442891 | 1.9 | 852 | 39 | 36 | 53 | 114 | 164 | 106 | N | P | N | N | N | P |
| APOBEC3G | high in P | 5.9 | 0.011456529 | 1.9 | 853 | 19 | 17 | 10 | 35 | 86 | 201 | N | N | N | N | N | N |
| FZD5 | high in P | 5.3 | 0.011521309 | 1.9 | 854 | 75 | 70 | 123 | 251 | 447 | 768 | N | N | N | N | N | N |
| SPATA5L1 | high in P | 4.3 | 0.011533583 | 1.9 | 855 | 23 | 15 | 28 | 51 | 85 | 57 | N | N | N | N | N | N |
| CRTC2 | high in P | 4.3 | 0.011555404 | 1.9 | 856 | 45 | 96 | 137 | 421 | 347 | 594 | N | N | N | N | N | N |
| ITGB5 | high in P | 6.7 | 0.011562223 | 1.9 | 857 | 2795 | 822 | 2029 | 18375 | 12811 | 5593 | N | N | N | N | N | N |
| BET1L | high in P | 4.2 | 0.011575179 | 1.9 | 858 | 34 | 28 | 32 | 200 | 82 | 96 | N | N | N | N | N | N |
| BMS1 | high in P | 4.3 | 0.011588817 | 1.9 | 859 | 57 | 43 | 85 | 240 | 287 | 196 | N | N | N | N | N | N |
| REV1 | high in P | 3.7 | 0.011595636 | 1.9 | 860 | 76 | 74 | 72 | 198 | 344 | 330 | N | N | N | N | N | N |
| FCHSD1 | high in P | 3.9 | 0.011609274 | 1.9 | 861 | 7 | 13 | 18 | 60 | 40 | 84 | N | N | N | N | N | N |
| CHMP4A | high in P | 4.5 | 0.011622912 | 1.9 | 862 | 69 | 24 | 57 | 299 | 169 | 175 | N | N | N | N | N | N |
| SHROOM1 | high in P | 6.7 | 0.01163655 | 1.9 | 863 | 52 | 15 | 29 | 178 | 170 | 98 | N | N | N | N | N | N |
| MRPL41 | high in P | 8.8 | 0.011650188 | 1.9 | 864 | 129 | 63 | 349 | 1125 | 1043 | 599 | N | N | N | N | N | N |
| C20orf200 | high in P | 8.4 | 0.011699284 | 1.9 | 865 | NA | NA | NA | NA | NA | NA | P | P | N | N | N | N |
| APOOL | high in P | 3.7 | 0.011728606 | 1.9 | 866 | 66 | 41 | 55 | 178 | 110 | 201 | N | N | N | N | N | N |
| APEH | high in P | 7.0 | 0.011749062 | 1.9 | 867 | 262 | 48 | 133 | 1195 | 892 | 507 | N | N | N | N | N | N |
| RBM44 | high in P | 7.6 | 0.011755881 | 1.9 | 868 | 7 | 14 | 7 | 28 | 35 | 20 | N | N | N | N | N | N |
| ALG13 | high in P | 6.0 | 0.011769519 | 1.9 | 869 | 3 | 7 | 17 | 40 | 67 | 28 | N | P | N | N | N | N |
| C9orf114 | high in P | 5.1 | 0.011776338 | 1.9 | 870 | 8 | 14 | 18 | 102 | 60 | 31 | N | N | N | N | N | N |
| TRIM26 | high in P | 3.6 | 0.011810433 | 1.9 | 871 | 342 | 190 | 392 | 940 | 1189 | 1328 | N | N | N | N | N | N |
| MYO10 | high in P | 5.7 | 0.011817252 | 1.9 | 872 | 265 | 127 | 152 | 625 | 864 | 864 | P | N | N | N | N | N |
| C1orf163 | high in P | 4.2 | 0.011836345 | 1.9 | 873 | 6 | 18 | 24 | 67 | 80 | 52 | N | N | N | N | N | N |
| WDR54 | high in P | 6.9 | 0.011843164 | 1.9 | 874 | 26 | 7 | 14 | 161 | 47 | 51 | N | N | N | N | N | N |
| HLA-B | high in P | 4.2 | 0.011849983 | 1.9 | 875 | 14413 | 5271 | 7525 | 49708 | 27420 | 32526 | N | N | N | N | N | N |
| S100A7 | high in P | 8.7 | 0.011863621 | 1.9 | 876 | 1 | 14 | 37 | 143 | 264 | 94 | N | P | N | N | N | N |
| SLC25A38 | high in P | 3.5 | 0.011877259 | 1.9 | 877 | 148 | 125 | 63 | 419 | 506 | 368 | N | N | N | N | N | N |
| ANKMY1 | high in P | 8.0 | 0.011884078 | 1.9 | 878 | 20 | 13 | 16 | 94 | 65 | 24 | N | N | N | N | N | N |
| MUC16 | high in P | 10.1 | 0.011890897 | 1.9 | 879 | 51 | 55 | 51 | 74 | 232 | 104 | P | P | N | N | N | N |
| DNAI2 | high in P | 8.9 | 0.011897716 | 1.9 | 880 | 3 | 3 | 4 | 11 | 12 | 201 | N | N | N | N | N | N |
| BCKDK | high in P | 4.5 | 0.011911354 | 1.9 | 881 | 285 | 173 | 304 | 1815 | 1012 | 730 | N | N | N | N | N | N |
| LOC100130776 | high in P | 6.6 | 0.011924991 | 1.9 | 882 | 9 | 14 | 27 | 92 | 83 | 55 | NA | NA | N | N | N | N |
| KIAA0368 | high in P | 4.1 | 0.011945448 | 1.9 | 883 | 297 | 392 | 715 | 1427 | 1730 | 2335 | NA | NA | N | N | N | N |
| INCA1 | high in P | 7.3 | 0.011972724 | 1.9 | 884 | 14 | 3 | 4 | 9 | 32 | 24 | NA | NA | N | N | N | N |
| ISM2 | high in P | 5.8 | 0.011993181 | 1.9 | 885 | 9 | 2 | 3 | 7 | 19 | 23 | N | N | N | N | N | N |
| PDHA1 | high in P | 3.2 | 0.012 | 1.9 | 886 | 182 | 170 | 170 | 751 | 599 | 453 | N | N | N | N | N | N |
| LOC286467 | high in P | 5.6 | 0.012006819 | 1.9 | 887 | 6 | 22 | 34 | 73 | 115 | 109 | N | N | N | N | N | N |
| BLOC1S1 | high in P | 5.2 | 0.012013638 | 1.9 | 888 | 350 | 168 | 326 | 1765 | 1085 | 781 | N | N | N | N | N | N |
| TMED10P | high in P | 4.5 | 0.012020457 | 1.9 | 889 | NA | NA | NA | NA | NA | NA | N | N | N | N | N | N |
| GPR133 | high in P | 5.3 | 0.012027276 | 1.9 | 890 | 24 | 24 | 46 | 226 | 84 | 160 | N | N | N | N | N | N |
| C8orf80 | high in P | 3.5 | 0.012034095 | 1.9 | 891 | 16 | 35 | 32 | 106 | 66 | 94 | N | N | N | N | N | N |
| RPS6KA4 | high in P | 4.9 | 0.012040914 | 1.9 | 892 | 102 | 55 | 203 | 489 | 691 | 436 | N | P | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | Parous (P) | | | NP | P | GeneBody NP Met | GeneBody Met | Pro-moter Met | Pro-moter Met |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | | | | |
| QTRT1 | high in P | 4.5 | 0.012047733 | 1.9 | 893 | 114 | 79 | 226 | 581 | 478 | 674 | N | N | N | N | N | N |
| PNPLA2 | high in P | 4.0 | 0.012054552 | 1.9 | 894 | 493 | 237 | 313 | 1152 | 1839 | 1399 | N | N | N | N | N | N |
| MRPL20 | high in P | 4.2 | 0.012090692 | 1.9 | 895 | 22 | 72 | 43 | 210 | 298 | 144 | N | N | N | N | N | N |
| AP4S1 | high in P | 4.3 | 0.012097511 | 1.9 | 896 | 171 | 218 | 173 | 484 | 715 | 1440 | N | N | N | N | N | N |
| C22orf30 | high in P | 5.1 | 0.012151381 | 1.9 | 897 | 20 | 28 | 36 | 177 | 108 | 53 | N | N | N | P | N | N |
| C1orf135 | high in P | 5.4 | 0.0121582 | 1.9 | 898 | 903 | 597 | 1820 | 4926 | 5020 | 3504 | N | N | N | N | N | N |
| SLC17A9 | high in P | 4.5 | 0.012165019 | 1.9 | 899 | 9 | 11 | 12 | 31 | 37 | 25 | NA | NA | N | N | N | N |
| SIRT3 | high in P | 3.3 | 0.012192295 | 1.9 | 900 | 1164 | 705 | 1455 | 3839 | 4001 | 3212 | N | N | N | N | N | N |
| PTPN6 | high in P | 12.5 | 0.012205932 | 1.9 | 901 | 54 | 9 | 14 | 79 | 127 | 207 | N | N | N | N | N | N |
| CWF19L1 | high in P | 4.9 | 0.012240027 | 1.9 | 902 | 26 | 15 | 13 | 99 | 70 | 47 | N | N | N | N | N | N |
| ERI3 | high in P | 5.7 | 0.012304125 | 1.9 | 903 | 242 | 87 | 206 | 1360 | 954 | 475 | NA | NA | N | N | N | N |
| CEACAM5 | high in P | 3.4 | 0.012310944 | 1.9 | 904 | 241 | 146 | 283 | 697 | 696 | 895 | N | P | N | N | N | N |
| KRTCAP3 | high in P | 5.0 | 0.012330038 | 1.9 | 905 | 8 | 7 | 2 | 14 | 49 | 19 | P | N | N | N | N | N |
| APEX2 | high in P | 7.4 | 0.012336856 | 1.9 | 906 | 74 | 16 | 35 | 270 | 222 | 103 | P | N | N | N | N | N |
| PDDC1 | high in P | 3.7 | 0.012359359 | 1.9 | 907 | 16 | 28 | 30 | 88 | 98 | 131 | N | N | N | N | N | N |
| BIRC5 | high in P | 7.9 | 0.012375043 | 1.9 | 908 | 7 | 7 | 9 | 13 | 40 | 57 | N | N | N | N | N | N |
| ZNF662 | high in P | 3.0 | 0.012433686 | 1.9 | 909 | 18 | 24 | 16 | 47 | 46 | 51 | N | N | N | N | N | N |
| INO80 | high in P | 3.7 | 0.012461643 | 1.9 | 910 | 107 | 76 | 134 | 472 | 301 | 338 | N | N | N | N | N | N |
| UBE3C | high in P | 4.3 | 0.012468462 | 1.9 | 911 | 271 | 167 | 250 | 1035 | 1299 | 585 | N | N | N | N | N | N |
| MAST2 | high in P | 5.8 | 0.012520968 | 1.9 | 912 | 288 | 144 | 510 | 1118 | 1302 | 3016 | N | N | N | N | N | N |
| SETMAR | high in P | 3.6 | 0.012527787 | 1.9 | 913 | 16 | 26 | 24 | 63 | 70 | 48 | N | N | N | N | N | N |
| MLH1 | high in P | 4.6 | 0.012534606 | 1.9 | 914 | 21 | 8 | 8 | 62 | 23 | 39 | N | N | N | N | N | N |
| IKZF2 | high in P | 4.0 | 0.012551654 | 1.9 | 915 | 19 | 33 | 23 | 53 | 68 | 135 | N | N | N | N | N | N |
| LILRB1 | high in P | 3.6 | 0.012558473 | 1.9 | 916 | 55 | 35 | 49 | 120 | 111 | 164 | N | N | N | N | N | N |
| DDX19A | high in P | 4.3 | 0.012578929 | 1.9 | 917 | 6 | 7 | 7 | 17 | 11 | 21 | N | N | N | N | N | N |
| FKBPL | high in P | 6.4 | 0.012592567 | 1.9 | 918 | 42 | 11 | 10 | 55 | 81 | 120 | N | N | N | N | N | N |
| XPC | high in P | 5.6 | 0.012613024 | 1.9 | 919 | 123 | 47 | 54 | 627 | 233 | 263 | N | N | N | N | N | N |
| KDM4D | high in P | 9.5 | 0.012639618 | 1.9 | 920 | 24 | 6 | 7 | 35 | 22 | 47 | NA | NA | N | N | N | N |
| GIT1 | high in P | 6.3 | 0.012670985 | 1.9 | 921 | 72 | 18 | 47 | 245 | 271 | 279 | N | N | N | N | N | N |
| TPRKB | high in P | 4.3 | 0.012683259 | 1.9 | 922 | 57 | 49 | 81 | 345 | 236 | 136 | N | N | N | N | N | N |
| ERMP1 | high in P | 11.8 | 0.012690078 | 1.9 | 923 | 31 | 15 | 17 | 75 | 89 | 49 | N | N | N | N | P | N |
| MFSD9 | high in P | 11.4 | 0.012696897 | 1.9 | 924 | 13 | 13 | 13 | 50 | 40 | 16 | N | N | N | N | N | N |
| FAU | high in P | 3.0 | 0.012703716 | 1.9 | 925 | 9780 | 6709 | 12149 | 27418 | 30489 | 27432 | N | N | N | N | N | N |
| NXPH4 | high in P | 5.6 | 0.012730992 | 1.9 | 926 | 11 | 6 | 10 | 20 | 36 | 18 | N | P | N | N | N | N |
| NCRNA00105 | high in P | 13.2 | 0.012737811 | 1.9 | 927 | 17 | 12 | 19 | 28 | 193 | 220 | NA | NA | N | N | N | N |
| FOXF2 | high in P | 5.0 | 0.012767133 | 1.9 | 928 | 146 | 119 | 149 | 721 | 319 | 1167 | P | P | N | N | N | N |
| PMF1 | high in P | 5.4 | 0.012773952 | 1.9 | 929 | 198 | 84 | 79 | 474 | 513 | 392 | N | N | N | N | N | N |
| UBE2I1 | high in P | 3.9 | 0.012780771 | 1.9 | 930 | 506 | 308 | 304 | 2581 | 1384 | 1282 | P | N | N | N | N | N |
| FOXC2 | high in P | 4.2 | 0.012808728 | 1.9 | 931 | 20 | 17 | 50 | 160 | 189 | 66 | P | P | N | N | N | N |
| KCTD2 | high in P | 2.7 | 0.012846914 | 1.9 | 932 | 112 | 103 | 111 | 303 | 314 | 261 | N | N | N | N | N | N |
| UBA5 | high in P | 3.7 | 0.012860552 | 1.9 | 933 | 117 | 74 | 74 | 440 | 316 | 212 | P | N | N | N | N | N |
| TAT | high in P | 5.0 | 0.012889874 | 1.9 | 934 | 163 | 39 | 76 | 371 | 361 | 402 | N | N | N | N | N | N |
| SCNN1D | high in P | 5.9 | 0.012902148 | 1.9 | 935 | 31 | 11 | 18 | 38 | 91 | 125 | N | N | N | N | N | N |
| DOT1L | high in P | 4.9 | 0.012922605 | 1.9 | 936 | 572 | 321 | 1116 | 3072 | 3245 | 2614 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | | Nulliparous (NP) | | | Parous (P) | | | NP | P | | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met | |
| KRTAP2-4 | high in P | 7.9 | 0.001292942 | 1.9 | 937 | 1 | 1 | 1 | 3 | 21 | 9 | N | P | N | N | N | N | |
| TMUB1 | high in P | 4.8 | 0.001294510 | 1.9 | 938 | 160 | 38 | 239 | 1040 | 765 | 579 | N | N | N | N | N | N | |
| BPNT1 | high in P | 3.5 | 0.001295192 | 1.9 | 939 | 2506 | 1758 | 1852 | 8708 | 5450 | 5960 | N | N | N | N | N | N | |
| FKSG83 | high in P | 5.2 | 0.001297920 | 1.9 | 940 | 2 | 2 | 2 | 6 | 4 | 12 | NA | NA | N | N | N | N | |
| CDK16 | high in P | 3.7 | 0.001298602 | 1.9 | 941 | 977 | 315 | 750 | 3024 | 3235 | 2814 | NA | NA | N | N | N | N | |
| PDE4C | high in P | 8.8 | 0.001299284 | 1.9 | 942 | 17 | 17 | 19 | 108 | 72 | 137 | P | P | N | N | N | N | |
| LDLR | high in P | 6.7 | 0.001302693 | 1.9 | 943 | 2243 | 594 | 1273 | 9193 | 10636 | 3798 | N | N | N | N | N | N | |
| RAB11FIP5 | high in P | 3.6 | 0.001303375 | 1.9 | 944 | 35 | 30 | 32 | 132 | 89 | 157 | N | N | N | N | N | N | |
| TCEB3 | high in P | 3.6 | 0.001304739 | 1.9 | 945 | 217 | 302 | 354 | 789 | 1561 | 1147 | N | N | N | N | N | N | |
| PLAGL2 | high in P | 3.3 | 0.001305421 | 1.9 | 946 | 189 | 284 | 184 | 648 | 923 | 692 | N | N | N | N | N | P | |
| WWTR1 | high in P | 6.3 | 0.001307466 | 1.9 | 947 | 519 | 196 | 411 | 1023 | 2585 | 4943 | N | N | N | N | N | N | |
| TMEM184B | high in P | 3.1 | 0.001309171 | 1.9 | 948 | 154 | 118 | 178 | 591 | 516 | 423 | N | N | N | N | N | N | |
| USP8 | high in P | 2.9 | 0.001310398 | 1.9 | 949 | 90 | 76 | 68 | 270 | 194 | 210 | N | N | N | N | N | N | |
| ACTL7B | high in P | 4.7 | 0.001311762 | 1.9 | 950 | 1 | 1 | 1 | 9 | 6 | 4 | N | P | N | N | P | N | |
| ANKLE1 | high in P | 3.8 | 0.001316604 | 1.9 | 951 | 46 | 56 | 32 | 155 | 96 | 184 | N | N | N | N | N | N | |
| CD3E | high in P | 21.5 | 0.00131796 | 1.9 | 952 | 59 | 2 | 4 | 63 | 123 | 680 | N | N | N | N | N | N | |
| ORC2L | high in P | 3.3 | 0.001318649 | 1.9 | 953 | 6 | 8 | 13 | 47 | 36 | 41 | N | P | N | N | N | N | |
| C17orf69 | high in P | 6.8 | 0.001320013 | 1.9 | 954 | 9 | 9 | 9 | 21 | 24 | 23 | NA | NA | N | N | N | N | |
| LOC644669 | high in P | 7.2 | 0.0132662 | 1.9 | 955 | 1 | 6 | 22 | 51 | 54 | 106 | NA | NA | N | N | N | N | |
| ECD | high in P | 3.8 | 0.001328196 | 1.9 | 956 | 156 | 135 | 261 | 521 | 586 | 619 | N | N | P | N | N | N | |
| IL10 | high in P | 5.1 | 0.001328878 | 1.9 | 957 | 97 | 31 | 54 | 196 | 227 | 469 | N | N | N | N | N | N | |
| SH2B2 | high in P | 4.8 | 0.001329560 | 1.9 | 958 | 50 | 13 | 41 | 108 | 166 | 232 | N | N | N | N | N | N | |
| MCM5 | high in P | 6.8 | 0.001330242 | 1.9 | 959 | 225 | 43 | 98 | 643 | 468 | 594 | N | N | N | N | N | N | |
| CECR7 | high in P | 4.0 | 0.001331605 | 1.9 | 960 | 9 | 12 | 16 | 27 | 27 | 57 | P | P | N | N | N | N | |
| TDRD7 | high in P | 4.0 | 0.001332969 | 1.9 | 961 | 15 | 13 | 12 | 50 | 23 | 37 | N | N | N | N | N | N | |
| ABI1 | high in P | 3.4 | 0.001335560 | 1.9 | 962 | 243 | 314 | 404 | 905 | 1404 | 1244 | N | P | N | N | N | N | |
| DOM3Z | high in P | 4.5 | 0.001336242 | 1.9 | 963 | 49 | 41 | 85 | 210 | 172 | 147 | N | N | N | N | N | N | |
| HDAC3 | high in P | 2.9 | 0.001337606 | 1.9 | 964 | 13 | 27 | 23 | 64 | 51 | 48 | N | N | N | N | N | N | |
| POLH | high in P | 2.8 | 0.001341834 | 1.9 | 965 | 74 | 136 | 109 | 376 | 336 | 453 | N | P | N | N | N | N | |
| PRDM7 | high in P | 6.3 | 0.001343198 | 1.9 | 966 | 8 | 8 | 8 | 18 | 21 | 24 | P | P | N | N | N | N | |
| RHCG | high in P | 4.1 | 0.0013438 | 1.9 | 967 | 6 | 22 | 11 | 79 | 28 | 67 | N | P | N | N | N | N | |
| ZNF167 | high in P | 11.1 | 0.001345243 | 1.9 | 968 | 12 | 6 | 6 | 28 | 26 | 9 | P | P | N | N | N | N | |
| AP1S1 | high in P | 6.0 | 0.001345925 | 1.9 | 969 | 79 | 21 | 21 | 296 | 129 | 104 | P | P | N | N | N | N | |
| DGCR11 | high in P | 4.3 | 0.001348107 | 1.9 | 970 | 6 | 7 | 10 | 28 | 15 | 23 | P | P | N | N | N | N | |
| RNPC3 | high in P | 3.3 | 0.001349335 | 1.9 | 971 | 7 | 14 | 17 | 43 | 38 | 38 | N | P | N | N | N | N | |
| GDAP1 | high in P | 6.3 | 0.001354722 | 1.9 | 972 | 30 | 14 | 9 | 62 | 54 | 43 | P | P | N | N | N | N | |
| RDBP | high in P | 6.2 | 0.001357108 | 1.9 | 973 | 281 | 136 | 74 | 1370 | 961 | 498 | P | P | N | N | P | N | |
| NCBP1 | high in P | 4.8 | 0.001357790 | 1.9 | 974 | 35 | 21 | 24 | 51 | 131 | 87 | N | P | N | N | N | N | |
| POU3F1 | high in P | 5.5 | 0.001359836 | 1.9 | 975 | 21 | 13 | 21 | 48 | 71 | 241 | N | P | N | N | N | N | |
| ATP6V0C | high in P | 4.1 | 0.001360859 | 1.9 | 976 | 2651 | 2197 | 4251 | 9050 | 12301 | 11753 | N | P | N | N | N | N | |
| C10orf140 | high in P | 7.6 | 0.001363723 | 1.9 | 977 | 10 | 10 | 11 | 53 | 26 | 51 | N | N | N | N | N | N | |
| DGKA | high in P | 4.5 | 0.0013644 | 1.9 | 978 | 83 | 19 | 55 | 181 | 202 | 264 | N | N | N | N | P | N | |
| TNFSF10 | high in P | 3.5 | 0.001366996 | 1.9 | 979 | 816 | 329 | 588 | 2004 | 1899 | 2455 | N | N | N | N | N | N | |
| PDLIM4 | high in P | 4.5 | 0.01368356 | 1.9 | 980 | 1187 | 899 | 1788 | 3993 | 9631 | 3740 | N | N | N | N | P | N | |

TABLE 15-continued

Genes that Are Differentially Methylated between Nulliparous and Parous CD44+ Breast Epithelial Cells

| | | | | | | SAGE-seq | | | | | | | ChIP-seq | | | MSDK-seq | | |
| | | | | | | Nulliparous (NP) | | | Parous (P) | | | NP | | P | GeneBody NP Met | GeneBody Met | Pro-moter Met | Pro-moter Met |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | | | | | |
|---|---|---|---|---|---|---|---|---|---|---|---|---|---|---|---|---|---|---|
| EXOC6B | high in P | 4.5 | 0.013690419 | 1.9 | 981 | 8 | 8 | 8 | 18 | 11 | 14 | N | N | N | N | N | N | N |
| IGSF21 | high in P | 15.0 | 0.013697238 | 1.9 | 982 | 2 | 2 | 3 | 19 | 7 | 85 | P | P | N | N | N | N | N |
| RHBDL3 | high in P | 6.6 | 0.013779066 | 1.9 | 983 | 11 | 13 | 21 | 66 | 80 | 256 | N | N | N | N | N | N | N |
| FST | high in P | 6.4 | 0.013809069 | 1.9 | 984 | 759 | 484 | 994 | 6757 | 5599 | 1692 | N | N | N | N | N | N | P |
| S100A3 | high in P | 7.5 | 0.013822707 | 1.9 | 985 | 33 | 7 | 8 | 71 | 228 | 36 | N | N | N | N | N | N | N |
| GOLGB1 | high in P | 3.5 | 0.013829526 | 1.9 | 986 | 136 | 141 | 191 | 737 | 366 | 732 | N | N | N | N | N | N | N |
| DNAJB13 | high in P | 3.5 | 0.013862257 | 1.9 | 987 | 4 | 5 | 6 | 17 | 29 | 12 | N | N | N | N | N | N | N |
| KTELC1 | high in P | 4.2 | 0.013869076 | 1.9 | 988 | 95 | 42 | 49 | 314 | 223 | 166 | N | N | N | P | N | N | N |
| FERMT1 | high in P | 12.3 | 0.013875895 | 1.9 | 989 | 6 | 6 | 6 | 18 | 107 | 9 | N | N | N | N | N | N | N |
| UPP2 | high in P | 5.6 | 0.013891579 | 1.9 | 990 | 5 | 34 | 44 | 86 | 166 | 170 | N | N | N | N | N | N | N |
| TPRG1L | high in P | 4.2 | 0.013898398 | 1.9 | 991 | 317 | 151 | 257 | 1429 | 854 | 785 | N | N | N | N | N | N | N |
| MIIP | high in P | 6.0 | 0.013905217 | 1.9 | 992 | 81 | 24 | 15 | 139 | 184 | 134 | NA | NA | N | N | N | N | N |
| SPHK1 | high in P | 3.9 | 0.013919536 | 1.9 | 993 | 735 | 795 | 1581 | 2517 | 5576 | 4815 | N | N | N | N | N | N | N |
| HAPLN2 | high in P | 4.7 | 0.013933174 | 1.9 | 994 | 1 | 1 | 1 | 11 | 6 | 4 | N | P | N | N | N | N | N |
| OFD1 | high in P | 3.5 | 0.013953631 | 1.9 | 995 | 88 | 96 | 109 | 254 | 459 | 432 | N | N | N | N | N | N | N |
| C20orf29 | high in P | 3.8 | 0.01396045 | 1.9 | 996 | 21 | 19 | 15 | 174 | 60 | 39 | N | N | N | N | N | N | N |
| RUNDC2C | high in P | 4.2 | 0.013980907 | 1.9 | 997 | 23 | 26 | 29 | 43 | 92 | 96 | N | N | N | N | N | N | N |
| VPS25 | high in P | 4.5 | 0.013987726 | 1.9 | 998 | 145 | 93 | 118 | 1134 | 508 | 285 | N | N | N | N | N | N | N |
| SHOX2 | high in P | 4.6 | 0.013994545 | 1.9 | 999 | 141 | 89 | 91 | 516 | 274 | 844 | N | N | N | N | N | N | N |
| ZFAT | high in P | 4.7 | 0.014008183 | 1.9 | 1000 | 19 | 19 | 16 | 81 | 31 | 51 | N | N | N | N | N | N | N |
| E2F2 | high in P | 3.5 | 0.014057961 | 1.9 | 1001 | 6 | 7 | 10 | 31 | 20 | 19 | N | N | N | N | N | N | N |
| SIRPB1 | high in P | 12.2 | 0.01406478 | 1.9 | 1002 | 19 | 2 | 3 | 18 | 31 | 35 | P | P | N | N | N | N | N |
| DHX9 | high in P | 3.0 | 0.014103648 | 1.9 | 1003 | 223 | 315 | 362 | 810 | 787 | 985 | N | N | N | N | N | N | N |
| USP32 | high in P | 4.7 | 0.014137061 | 1.8 | 1004 | 14 | 16 | 16 | 24 | 34 | 50 | N | N | N | N | N | N | N |
| HAVCR2 | high in P | 6.3 | 0.01414388 | 1.8 | 1005 | 20 | 4 | 11 | 62 | 27 | 95 | N | N | N | N | N | N | N |
| ILF3 | high in P | 3.8 | 0.014177975 | 1.8 | 1006 | 302 | 284 | 236 | 869 | 1389 | 1795 | N | N | P | N | N | N | N |
| HIST1H1C | high in P | 29.7 | 0.014188203 | 1.8 | 1007 | 7 | 1 | 1 | 87 | 48 | 4 | N | N | N | N | N | N | N |
| SRGAP2 | high in P | 4.3 | 0.014209342 | 1.8 | 1008 | 122 | 76 | 132 | 504 | 293 | 841 | N | N | N | N | N | N | N |
| ZBTB40 | high in P | 4.3 | 0.014222298 | 1.8 | 1009 | 125 | 83 | 141 | 365 | 499 | 780 | N | N | N | N | N | N | N |
| UNC45A | high in P | 4.1 | 0.014255711 | 1.8 | 1010 | 255 | 112 | 186 | 1091 | 566 | 579 | N | N | N | N | N | N | N |
| KLHDC4 | high in P | 3.2 | 0.014295261 | 1.8 | 1011 | 13 | 13 | 18 | 29 | 54 | 34 | N | N | N | N | N | N | N |
| CD22 | high in P | 4.2 | 0.014340948 | 1.8 | 1012 | 3 | 7 | 5 | 15 | 13 | 32 | N | N | N | N | N | N | N |
| PEBP4 | high in P | 4.8 | 0.014377088 | 1.8 | 1013 | 18 | 2 | 8 | 28 | 36 | 45 | N | N | N | N | N | N | N |
| CCDC86 | high in P | 3.2 | 0.014397545 | 1.8 | 1014 | 204 | 262 | 201 | 589 | 1219 | 634 | N | N | N | N | N | N | N |
| AKT1 | high in P | 3.9 | 0.014409819 | 1.8 | 1015 | 578 | 302 | 602 | 2393 | 1652 | 1548 | N | N | N | N | N | N | N |
| HDAC6 | high in P | 4.5 | 0.014430276 | 1.8 | 1016 | 86 | 44 | 84 | 220 | 219 | 411 | P | P | N | N | N | N | N |
| MLXIPL | high in P | 3.4 | 0.014437095 | 1.8 | 1017 | 24 | 35 | 39 | 69 | 86 | 130 | N | N | N | N | N | N | N |
| ALG12 | high in P | 4.6 | 0.014468462 | 1.8 | 1018 | 55 | 32 | 45 | 291 | 193 | 90 | N | N | N | N | N | N | N |
| PSPH | high in P | 17.4 | 0.014490965 | 1.8 | 1019 | 27 | 6 | 6 | 45 | 47 | 31 | N | N | N | N | N | P | N |
| RAVER2 | high in P | 6.0 | 0.014514149 | 1.8 | 1020 | 22 | 11 | 12 | 30 | 62 | 31 | N | N | N | N | N | N | N |
| PCBD2 | high in P | 6.3 | 0.014541425 | 1.8 | 1021 | 58 | 22 | 26 | 167 | 143 | 190 | N | N | N | N | N | N | N |
| CHD3 | high in P | 4.9 | 0.014548244 | 1.8 | 1022 | 473 | 128 | 284 | 1509 | 1028 | 2421 | N | N | N | N | N | N | N |
| LOC100272228 | high in P | 4.7 | 0.014571429 | 1.8 | 1023 | 6 | 6 | 6 | 9 | 11 | 17 | NA | NA | N | N | N | N | N |
| C10orf11 | high in P | 4.7 | 0.014571429 | 1.8 | 1024 | 4 | 4 | 4 | 6 | 9 | 15 | N | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
| | | | | | Nulliparous (NP) | | | Parous (P) | | | | NP | P | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
|---|---|---|---|---|---|---|---|---|---|---|---|---|---|---|---|---|---|
| MLX | high in P | 5.2 | 0.014606205 | 1.8 | 1025 | 249 | 76 | 97 | 823 | 755 | 365 | N | N | N | N | N | N |
| RAD52 | high in P | 5.5 | 0.014633481 | 1.8 | 1026 | 13 | 6 | 7 | 14 | 18 | 36 | N | N | N | N | N | N |
| DCTN2 | high in P | 4.0 | 0.0146403 | 1.8 | 1027 | 673 | 383 | 497 | 2806 | 2148 | 1227 | P | N | N | N | N | N |
| CLDND2 | high in P | 7.1 | 0.014647119 | 1.8 | 1028 | 3 | 3 | 5 | 9 | 12 | 16 | N | P | N | N | N | N |
| RHBDL1 | high in P | 4.2 | 0.014653938 | 1.8 | 1029 | 6 | 18 | 11 | 30 | 30 | 56 | P | N | N | N | N | N |
| NMUR1 | high in P | 3.5 | 0.014667576 | 1.8 | 1030 | 15 | 15 | 22 | 45 | 73 | 61 | N | N | N | N | N | N |
| TBC1D10C | high in P | 4.3 | 0.014704398 | 1.8 | 1031 | 6 | 7 | 7 | 15 | 15 | 56 | P | N | N | N | N | N |
| LOC150381 | high in P | 3.7 | 0.014737811 | 1.8 | 1032 | 44 | 14 | 37 | 117 | 124 | 71 | NA | NA | N | N | N | N |
| NT5DC3 | high in P | 5.7 | 0.014765087 | 1.8 | 1033 | 195 | 201 | 112 | 380 | 1578 | 965 | N | N | N | N | P | N |
| TCIRG1 | high in P | 3.9 | 0.014794408 | 1.8 | 1034 | 251 | 117 | 226 | 1072 | 581 | 713 | N | N | N | N | N | N |
| C11orf53 | high in P | 5.6 | 0.01480941 | 1.8 | 1035 | 4 | 12 | 16 | 64 | 49 | 34 | N | N | N | N | N | N |
| ZC3H6 | high in P | 3.6 | 0.014816229 | 1.8 | 1036 | 161 | 166 | 362 | 775 | 874 | 718 | N | N | N | N | N | N |
| CEP250 | high in P | 5.8 | 0.014823048 | 1.8 | 1037 | 50 | 24 | 27 | 143 | 64 | 107 | N | N | N | N | N | N |
| OR52R1 | high in P | 4.0 | 0.014848278 | 1.8 | 1038 | 2 | 2 | 3 | 17 | 9 | 10 | N | P | N | N | N | N |
| C12orf76 | high in P | 3.9 | 0.014855097 | 1.8 | 1039 | 25 | 16 | 8 | 49 | 29 | 54 | NA | NA | N | N | N | N |
| C9orf23 | high in P | 3.1 | 0.014892601 | 1.8 | 1040 | 61 | 18 | 57 | 163 | 142 | 148 | N | N | N | N | N | N |
| GINS1 | high in P | 6.0 | 0.014985339 | 1.8 | 1041 | 14 | 10 | 13 | 19 | 67 | 65 | N | N | N | N | N | N |
| DYNLL1 | high in P | 5.0 | 0.014992158 | 1.8 | 1042 | 1669 | 758 | 1854 | 3758 | 5898 | 9528 | N | N | N | N | N | N |
| ZDHHC19 | high in P | 4.7 | 0.015002387 | 1.8 | 1043 | 5 | 2 | 2 | 7 | 5 | 13 | N | N | N | N | N | N |
| FAM186B | high in P | 4.7 | 0.015002387 | 1.8 | 1044 | 5 | 5 | 5 | 9 | 8 | 15 | N | N | N | N | N | N |
| DZIP1L | high in P | 5.9 | 0.015028299 | 1.8 | 1045 | 24 | 12 | 41 | 56 | 119 | 99 | N | N | N | N | N | N |
| MRPL48 | high in P | 6.2 | 0.015052847 | 1.8 | 1046 | 55 | 10 | 20 | 143 | 120 | 60 | N | N | N | N | N | N |
| RABL2B | high in P | 5.7 | 0.015066485 | 1.8 | 1047 | 5 | 5 | 5 | 7 | 10 | 18 | N | N | N | N | N | N |
| TROVE2 | high in P | 3.2 | 0.015073304 | 1.8 | 1048 | 172 | 165 | 245 | 633 | 631 | 748 | N | N | N | N | N | N |
| YTHDC1 | high in P | 4.0 | 0.015112854 | 1.8 | 1049 | 814 | 477 | 850 | 2560 | 1926 | 3847 | N | N | N | N | N | N |
| GALNT6 | high in P | 3.5 | 0.015119673 | 1.8 | 1050 | 24 | 31 | 28 | 74 | 91 | 43 | P | P | N | N | N | N |
| PRPF4 | high in P | 3.3 | 0.015126492 | 1.8 | 1051 | 70 | 76 | 109 | 336 | 236 | 208 | N | N | N | N | N | N |
| MRPS25 | high in P | 4.7 | 0.015167405 | 1.8 | 1052 | 124 | 81 | 93 | 292 | 476 | 1230 | N | N | N | N | N | N |
| CHST2 | high in P | 3.8 | 0.015193317 | 1.8 | 1053 | 18 | 19 | 39 | 141 | 52 | 91 | N | N | N | N | N | N |
| CRX | high in P | 4.4 | 0.015205592 | 1.8 | 1054 | 17 | 24 | 46 | 103 | 108 | 74 | N | N | N | N | N | N |
| ACOT7 | high in P | 5.9 | 0.015226048 | 1.8 | 1055 | 346 | 52 | 255 | 721 | 1515 | 1434 | N | P | N | N | N | N |
| MCF2L | high in P | 5.2 | 0.015232867 | 1.8 | 1056 | 50 | 24 | 25 | 198 | 95 | 92 | N | N | N | N | N | N |
| DUS1L | high in P | 4.8 | 0.015273099 | 1.8 | 1057 | 134 | 80 | 226 | 715 | 897 | 367 | N | N | N | N | N | N |
| ZNF709 | high in P | 2.9 | 0.015333788 | 1.8 | 1058 | 27 | 14 | 23 | 49 | 46 | 50 | N | N | N | N | N | N |
| DHX34 | high in P | 3.6 | 0.015374702 | 1.8 | 1059 | 14 | 18 | 28 | 55 | 91 | 76 | N | N | N | N | N | N |
| OGFOD2 | high in P | 4.7 | 0.015389021 | 1.8 | 1060 | 30 | 18 | 51 | 134 | 112 | 72 | N | N | N | N | N | N |
| H2AFZ | high in P | 4.5 | 0.015416297 | 1.8 | 1061 | 1735 | 1197 | 3300 | 4751 | 8710 | 13578 | N | N | N | N | P | N |
| FAM185A | high in P | 5.0 | 0.015436754 | 1.8 | 1062 | 4 | 4 | 4 | 8 | 22 | 15 | NA | NA | N | N | N | N |
| MBLAC1 | high in P | 3.2 | 0.015462666 | 1.8 | 1063 | 14 | 8 | 12 | 23 | 25 | 23 | NA | NA | N | N | N | N |
| ABCF1 | high in P | 3.7 | 0.01547835 | 1.8 | 1064 | 169 | 166 | 342 | 831 | 991 | 585 | N | N | N | N | N | N |
| RIC8B | high in P | 3.7 | 0.015485169 | 1.8 | 1065 | 67 | 47 | 65 | 155 | 162 | 298 | NA | N | N | N | N | N |
| LOC284551 | high in P | 17.2 | 0.015500852 | 1.8 | 1066 | 2 | 15 | 2 | 21 | 27 | 23 | NA | NA | N | N | N | N |
| WDR19 | high in P | 3.9 | 0.015523355 | 1.8 | 1067 | 9 | 48 | 32 | 118 | 80 | 97 | N | N | N | N | N | N |
| SOX5 | high in P | 11.3 | 0.015538357 | 1.8 | 1068 | 36 | 9 | 10 | 52 | 29 | 160 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | Nulliparous (NP) | | | | Parous (P) | | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 NP | CD44+ N66 P | GeneBody NP Met NP | GeneBody Met P | Pro-moter Met NP | Pro-moter Met P |
| ZNF296 | high in P | 5.6 | 0.015560859 | 1.8 | 1069 | 35 | 9 | 20 | 59 | 91 | 84 | N | N | N | N | N | N |
| EIF3J | high in P | 4.6 | 0.015594954 | 1.8 | 1070 | 276 | 370 | 600 | 1013 | 2819 | 2233 | N | N | N | N | N | N |
| GUF1 | high in P | 3.9 | 0.015616775 | 1.8 | 1071 | 26 | 29 | 12 | 94 | 95 | 56 | N | N | N | N | N | N |
| CCR7 | high in P | 7.7 | 0.015623594 | 1.8 | 1072 | 6 | 33 | 23 | 166 | 47 | 645 | N | N | N | N | N | N |
| WIPI1 | high in P | 3.8 | 0.01564405 | 1.8 | 1073 | 18 | 25 | 45 | 130 | 81 | 96 | N | N | N | N | P | N |
| CREB3 | high in P | 3.7 | 0.015665871 | 1.8 | 1074 | 122 | 136 | 232 | 699 | 644 | 423 | N | N | N | N | N | N |
| PP2R5B | high in P | 4.5 | 0.015700648 | 1.8 | 1075 | 175 | 65 | 81 | 510 | 449 | 285 | N | N | N | N | N | N |
| KIAA0355 | high in P | 2.9 | 0.015707467 | 1.8 | 1076 | 279 | 139 | 280 | 921 | 822 | 764 | N | N | N | N | N | N |
| SAPS1 | high in P | 4.5 | 0.015721105 | 1.8 | 1077 | 321 | 192 | 629 | 1444 | 1529 | 1296 | N | N | N | N | N | N |
| PPIL5 | high in P | 4.7 | 0.015736788 | 1.8 | 1078 | 8 | 13 | 11 | 23 | 55 | 19 | N | N | N | N | N | N |
| CNTN4 | high in P | 8.6 | 0.015743607 | 1.8 | 1079 | 26 | 10 | 5 | 10 | 35 | 79 | N | N | N | N | N | N |
| PIWIL4 | high in P | 4.6 | 0.015750426 | 1.8 | 1080 | 4 | 4 | 5 | 12 | 13 | 31 | N | N | N | N | N | N |
| PPOX | high in P | 4.1 | 0.015770883 | 1.8 | 1081 | 4 | 5 | 5 | 12 | 20 | 20 | N | N | N | N | N | N |
| PYCR1 | high in P | 7.0 | 0.015793386 | 1.8 | 1082 | 290 | 58 | 178 | 1175 | 1278 | 435 | N | N | N | N | N | P |
| NEURL2 | high in P | 5.7 | 0.015807024 | 1.8 | 1083 | 35 | 6 | 8 | 43 | 44 | 130 | N | N | N | N | N | N |
| RACGAP1 | high in P | 4.3 | 0.01584521 | 1.8 | 1084 | 31 | 38 | 41 | 78 | 104 | 225 | N | N | N | N | N | N |
| ARFGAP1 | high in P | 4.7 | 0.015852029 | 1.8 | 1085 | 8 | 11 | 25 | 133 | 86 | 38 | N | N | N | N | N | N |
| N4BP1 | high in P | 4.0 | 0.015858848 | 1.8 | 1086 | 57 | 38 | 42 | 196 | 187 | 110 | N | N | N | N | N | N |
| UBE2G2 | high in P | 3.1 | 0.015865667 | 1.8 | 1087 | 237 | 363 | 509 | 1060 | 1302 | 1112 | N | N | N | N | N | N |
| PAK1 | high in P | 3.9 | 0.015892942 | 1.8 | 1088 | 23 | 57 | 64 | 126 | 198 | 223 | N | N | N | N | N | N |
| HSD17B10 | high in P | 4.2 | 0.015927037 | 1.8 | 1089 | 302 | 130 | 246 | 1261 | 1177 | 490 | N | N | N | N | N | N |
| CEP57 | high in P | 4.1 | 0.015933856 | 1.8 | 1090 | 74 | 32 | 44 | 163 | 131 | 191 | N | N | N | N | N | N |
| SNHG10 | high in P | 4.9 | 0.015940675 | 1.8 | 1091 | 6 | 20 | 18 | 59 | 31 | 79 | N | N | N | N | N | N |
| CABLES1 | high in P | 7.3 | 0.01598271 | 1.8 | 1092 | 34 | 14 | 16 | 67 | 55 | 91 | N | N | N | N | N | N |
| TRPM7 | high in P | 2.9 | 0.016023866 | 1.8 | 1093 | 65 | 89 | 93 | 210 | 187 | 286 | N | N | P | N | N | N |
| BCAM | high in P | 22.3 | 0.016047733 | 1.8 | 1094 | 307 | 23 | 29 | 342 | 2658 | 522 | N | N | N | N | N | N |
| FBXL6 | high in P | 4.0 | 0.016054552 | 1.8 | 1095 | 29 | 17 | 10 | 58 | 47 | 42 | N | N | N | N | N | N |
| SLC26A6 | high in P | 6.8 | 0.016075009 | 1.8 | 1096 | 84 | 15 | 47 | 266 | 115 | 444 | N | N | N | N | N | N |
| TRIM16 | high in P | 3.6 | 0.016081827 | 1.8 | 1097 | 536 | 264 | 839 | 1757 | 2228 | 1935 | N | N | N | N | N | N |
| TMPRSS11B | high in P | 3.4 | 0.016088646 | 1.8 | 1098 | 23 | 25 | 23 | 66 | 43 | 91 | N | N | N | N | N | N |
| REC8 | high in P | 5.3 | 0.016110477 | 1.8 | 1099 | 26 | 34 | 45 | 70 | 159 | 325 | N | N | N | N | N | P |
| SPG7 | high in P | 3.7 | 0.016128196 | 1.8 | 1100 | 274 | 124 | 187 | 576 | 667 | 996 | N | N | N | N | N | N |
| C12orf48 | high in P | 3.4 | 0.016135015 | 1.8 | 1101 | 3 | 4 | 11 | 24 | 32 | 19 | N | N | N | N | N | N |
| DMRTA1 | high in P | 5.1 | 0.016150699 | 1.8 | 1102 | 14 | 2 | 3 | 10 | 10 | 23 | N | N | N | N | N | N |
| KCTD17 | high in P | 4.7 | 0.016171156 | 1.8 | 1103 | 5 | 12 | 5 | 43 | 25 | 20 | N | N | N | N | N | N |
| PLSCR2 | high in P | 3.3 | 0.016184794 | 1.8 | 1104 | 14 | 7 | 9 | 21 | 24 | 54 | N | N | N | N | N | N |
| POMT2 | high in P | 3.5 | 0.016191613 | 1.8 | 1105 | 74 | 71 | 93 | 356 | 273 | 165 | N | N | N | N | N | N |
| GSS | high in P | 4.7 | 0.016198432 | 1.8 | 1106 | 107 | 26 | 74 | 410 | 312 | 188 | N | N | N | N | N | N |
| ANKS3 | high in P | 3.7 | 0.016220934 | 1.8 | 1107 | 31 | 33 | 63 | 131 | 145 | 87 | N | N | N | N | N | N |
| ABCD4 | high in P | 2.7 | 0.016227753 | 1.8 | 1108 | 8 | 13 | 16 | 32 | 24 | 28 | N | N | N | N | N | N |
| C17orf73 | high in P | 3.7 | 0.016307535 | 1.8 | 1109 | 55 | 33 | 74 | 153 | 178 | 163 | N | N | N | N | N | N |
| HSF4 | high in P | 5.2 | 0.016326628 | 1.8 | 1110 | 18 | 9 | 19 | 26 | 56 | 139 | NA | NA | N | N | N | N |
| CYP46A1 | high in P | 4.7 | 0.016347085 | 1.8 | 1111 | 3 | 3 | 4 | 6 | 8 | 14 | N | N | N | N | N | N |
| ABHD8 | high in P | 9.6 | 0.016360723 | 1.8 | 1112 | 88 | 13 | 22 | 250 | 151 | 127 | N | N | N | N | N | N |

TABLE 15-continued

Genes that Are Differentially Methylated between Nulliparous and Parous CD44+ Breast Epithelial Cells

| | | | | | SAGE-seq | | | | | | ChIP-seq | | MSDK-seq | | | |
| | | | | | | Nulliparous (NP) | | | Parous (P) | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
|---|---|---|---|---|---|---|---|---|---|---|---|---|---|---|---|---|---|
| FPR3 | high in P | 5.8 | 0.016833225 | 1.8 | 1113 | 3 | 3 | 3 | 7 | 6 | 21 | N | P | N | N | N | N |
| RPS6 | high in P | 5.7 | 0.016396863 | 1.8 | 1114 | 20377 | 9556 | 36974 | 127693 | 193466 | 64100 | N | N | N | N | N | N |
| RIPK1 | high in P | 6.7 | 0.016403682 | 1.8 | 1115 | 237 | 64 | 60 | 704 | 544 | 400 | N | N | N | N | N | N |
| C6orf129 | high in P | 9.1 | 0.01645687 | 1.8 | 1116 | 3 | 22 | 59 | 260 | 177 | 103 | P | N | N | N | N | N |
| KLF8 | high in P | 3.4 | 0.016478691 | 1.8 | 1117 | 40 | 62 | 34 | 152 | 95 | 178 | N | N | N | N | N | N |
| SLC23A2 | high in P | 5.9 | 0.0164851 | 1.8 | 1118 | 86 | 39 | 42 | 198 | 231 | 183 | N | N | N | N | N | N |
| TBX2 | high in P | 23.4 | 0.016499148 | 1.8 | 1119 | 572 | 89 | 16 | 2600 | 690 | 1962 | N | N | N | N | N | N |
| KIF9 | high in P | 4.2 | 0.016512786 | 1.8 | 1120 | 12 | 30 | 15 | 44 | 59 | 40 | N | N | N | N | N | N |
| PPP4C | high in P | 3.2 | 0.016519605 | 1.8 | 1121 | 49 | 35 | 39 | 125 | 121 | 89 | N | N | N | N | N | N |
| SNORA8 | high in P | 3.2 | 0.016531879 | 1.8 | 1122 | 17 | 6 | 12 | 24 | 29 | 28 | N | N | N | N | N | N |
| ANXA5 | high in P | 3.1 | 0.016580293 | 1.8 | 1123 | 140 | 252 | 253 | 908 | 675 | 716 | N | N | N | N | N | N |
| BEAR | high in P | 2.8 | 0.016593931 | 1.8 | 1124 | 40 | 23 | 34 | 94 | 71 | 93 | N | N | N | N | N | N |
| C17orf68 | high in P | 2.7 | 0.016607569 | 1.8 | 1125 | 24 | 37 | 47 | 101 | 90 | 111 | N | N | N | N | N | N |
| LOC388588 | high in P | 4.5 | 0.01665462 | 1.8 | 1126 | 14 | 3 | 6 | 18 | 16 | 32 | N | P | N | N | N | N |
| INTU | high in P | 8.3 | 0.016681214 | 1.8 | 1127 | 19 | 9 | 12 | 16 | 43 | 74 | N | N | N | N | N | N |
| ASAP2 | high in P | 3.4 | 0.016696897 | 1.8 | 1128 | 49 | 42 | 41 | 131 | 111 | 123 | N | N | N | N | N | N |
| DTNBP1 | high in P | 3.8 | 0.016710535 | 1.8 | 1129 | 43 | 11 | 60 | 145 | 129 | 171 | N | N | N | N | N | N |
| C14orf105 | high in P | 4.2 | 0.016723491 | 1.8 | 1130 | 5 | 5 | 5 | 15 | 13 | 8 | N | N | N | N | N | N |
| MGC70857 | high in P | 4.9 | 0.016757586 | 1.8 | 1131 | 147 | 17 | 104 | 651 | 494 | 293 | N | N | N | N | N | N |
| PATL1 | high in P | 3.6 | 0.016764405 | 1.8 | 1132 | 398 | 204 | 179 | 1233 | 603 | 1457 | N | N | N | N | N | N |
| REEP1 | high in P | 4.6 | 0.016771224 | 1.8 | 1133 | 7 | 7 | 7 | 13 | 21 | 13 | P | N | N | N | N | N |
| KIF1A | high in P | 10.1 | 0.01681282 | 1.8 | 1134 | 21 | 35 | 34 | 49 | 292 | 83 | P | P | N | N | N | N |
| LOC286359 | high in P | 3.1 | 0.016823048 | 1.8 | 1135 | 14 | 15 | 12 | 39 | 22 | 34 | NA | NA | N | N | N | N |
| STK11 | high in P | 3.1 | 0.016829867 | 1.8 | 1136 | 102 | 50 | 108 | 282 | 288 | 368 | N | N | N | N | N | N |
| LRRC57 | high in P | 5.6 | 0.016862598 | 1.8 | 1137 | 23 | 7 | 11 | 52 | 43 | 71 | N | N | N | N | N | P |
| PRPSAP2 | high in P | 6.1 | 0.016876236 | 1.8 | 1138 | 179 | 54 | 35 | 920 | 202 | 447 | N | N | N | N | N | N |
| SHE | high in P | 5.9 | 0.016883055 | 1.8 | 1139 | 17 | 23 | 20 | 99 | 93 | 143 | N | N | P | N | N | N |
| ZC3H3 | high in P | 3.5 | 0.016898738 | 1.8 | 1140 | 107 | 57 | 159 | 409 | 476 | 280 | N | N | N | N | N | N |
| MIF4GD | high in P | 3.2 | 0.016930106 | 1.8 | 1141 | 36 | 37 | 18 | 75 | 62 | 93 | N | N | N | N | N | N |
| PQLC1 | high in P | 4.2 | 0.016936925 | 1.8 | 1142 | 761 | 367 | 759 | 1578 | 2492 | 4201 | NA | NA | N | N | N | N |
| LOC284232 | high in P | 3.3 | 0.016943744 | 1.8 | 1143 | 233 | 155 | 179 | 614 | 651 | 846 | NA | NA | N | N | N | N |
| TCTEX1D4 | high in P | 5.3 | 0.016950563 | 1.8 | 1144 | 3 | 3 | 4 | 19 | 8 | 9 | N | N | N | N | N | N |
| LLGL2 | high in P | 4.5 | 0.016957382 | 1.8 | 1145 | 14 | 21 | 49 | 79 | 200 | 77 | N | N | N | N | N | N |
| CLPB | high in P | 5.1 | 0.016972383 | 1.8 | 1146 | 11 | 11 | 12 | 46 | 20 | 19 | N | N | N | N | N | N |
| SCO1 | high in P | 3.9 | 0.016985339 | 1.8 | 1147 | 65 | 45 | 26 | 167 | 170 | 102 | N | N | N | N | N | N |
| ZNF589 | high in P | 4.3 | 0.017013979 | 1.8 | 1148 | 33 | 13 | 27 | 64 | 39 | 106 | N | N | N | N | P | N |
| VPS72 | high in P | 5.1 | 0.017041937 | 1.8 | 1149 | 191 | 46 | 156 | 770 | 772 | 324 | N | N | N | N | N | N |
| DHX38 | high in P | 7.6 | 0.01705762 | 1.8 | 1150 | 234 | 68 | 44 | 828 | 304 | 1060 | N | N | N | N | N | N |
| PLEKHF1 | high in P | 3.6 | 0.017069894 | 1.8 | 1151 | 181 | 99 | 153 | 337 | 668 | 484 | N | N | P | N | P | N |
| POLR2I | high in P | 3.7 | 0.017096488 | 1.8 | 1152 | 51 | 54 | 69 | 220 | 234 | 98 | N | N | N | N | N | N |
| RHBDD3 | high in P | 3.4 | 0.017112172 | 1.8 | 1153 | 64 | 29 | 43 | 132 | 127 | 113 | N | N | N | N | N | N |
| NR5A2 | high in P | 4.4 | 0.017118991 | 1.8 | 1154 | 30 | 18 | 13 | 63 | 64 | 81 | P | P | N | N | P | N |
| NUP214 | high in P | 3.5 | 0.017169451 | 1.8 | 1155 | 51 | 104 | 60 | 195 | 192 | 220 | N | N | N | N | P | N |
| CCR6 | high in P | 3.8 | 0.017183089 | 1.8 | 1156 | 16 | 8 | 19 | 22 | 52 | 59 | N | P | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
| --- | --- | --- | --- | --- | --- | --- | --- | --- | --- | --- | --- | --- | --- | --- | --- | --- | --- |
| | | | | | Nulliparous (NP) | | | | Parous (P) | | | NP | | P | | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| C19orf21 | high in P | 9.5 | 0.017218548 | 1.8 | 1157 | 6 | 11 | 16 | 39 | 132 | 26 | N | N | N | N | N | N |
| SUV420H2 | high in P | 3.6 | 0.017246505 | 1.8 | 1158 | 23 | 25 | 33 | 77 | 70 | 277 | N | N | N | N | N | N |
| PLCD4 | high in P | 4.4 | 0.017273781 | 1.8 | 1159 | 11 | 11 | 6 | 15 | 18 | 30 | N | N | N | N | N | N |
| SCN4A | high in P | 7.1 | 0.0172806 | 1.8 | 1160 | 37 | 27 | 154 | 247 | 247 | 365 | N | N | N | N | N | N |
| ZNF251 | high in P | 5.0 | 0.017324923 | 1.8 | 1161 | 17 | 21 | 6 | 56 | 40 | 53 | N | N | N | N | N | N |
| AHNAK2 | high in P | 6.9 | 0.017341971 | 1.8 | 1162 | 46 | 22 | 24 | 49 | 112 | 259 | N | N | N | N | N | N |
| PPARD | high in P | 4.1 | 0.017386976 | 1.8 | 1163 | 390 | 66 | 279 | 940 | 1655 | 1132 | N | N | N | N | N | N |
| SLC10A7 | high in P | 9.1 | 0.017400614 | 1.8 | 1164 | 26 | 10 | 11 | 38 | 28 | 40 | N | N | N | N | N | N |
| C8orf46 | high in P | 4.6 | 0.017407433 | 1.8 | 1165 | 27 | 12 | 8 | 40 | 40 | 36 | N | N | N | N | N | N |
| ZXDC | high in P | 3.1 | 0.017421071 | 1.8 | 1166 | 188 | 115 | 163 | 736 | 474 | 473 | N | N | N | N | N | N |
| SDHAP2 | high in P | 5.7 | 0.017487214 | 1.8 | 1167 | 14 | 17 | 46 | 91 | 61 | 216 | NA | NA | N | N | N | N |
| IYD | high in P | 9.5 | 0.017494033 | 1.8 | 1168 | 29 | 8 | 10 | 56 | 31 | 67 | N | N | N | N | N | N |
| RAPGEFL1 | high in P | 6.0 | 0.017533583 | 1.8 | 1169 | 44 | 13 | 24 | 189 | 115 | 56 | N | N | N | N | N | N |
| ASAP3 | high in P | 8.4 | 0.017540402 | 1.8 | 1170 | 30 | 13 | 14 | 58 | 30 | 95 | N | N | N | N | N | N |
| WHSC1 | high in P | 3.4 | 0.017576543 | 1.8 | 1171 | 70 | 88 | 59 | 279 | 314 | 270 | N | N | N | N | N | N |
| PJA1 | high in P | 15.5 | 0.017590181 | 1.8 | 1172 | 158 | 14 | 21 | 336 | 265 | 282 | N | N | N | N | N | N |
| ZNF7 | high in P | 5.1 | 0.017625639 | 1.8 | 1173 | 4 | 4 | 5 | 25 | 11 | 15 | N | N | N | N | N | N |
| ILK | high in P | 3.9 | 0.017644732 | 1.8 | 1174 | 1034 | 222 | 660 | 2486 | 2454 | 2712 | N | N | N | N | N | N |
| CCDC117 | high in P | 2.9 | 0.017660416 | 1.8 | 1175 | 58 | 80 | 56 | 224 | 137 | 221 | N | N | N | N | N | N |
| GTF2B | high in P | 4.1 | 0.017679509 | 1.8 | 1176 | 120 | 123 | 253 | 489 | 468 | 588 | N | N | N | N | N | N |
| CDK2AP2 | high in P | 5.7 | 0.017686328 | 1.8 | 1177 | 229 | 115 | 358 | 2279 | 616 | 841 | N | N | N | N | N | N |
| CHCHD6 | high in P | 5.4 | 0.017711558 | 1.8 | 1178 | 79 | 16 | 40 | 195 | 183 | 106 | N | N | N | N | N | P |
| DCPS | high in P | 6.7 | 0.017725196 | 1.8 | 1179 | 68 | 4 | 25 | 224 | 168 | 88 | N | N | N | N | N | N |
| DFFA | high in P | 3.3 | 0.017747699 | 1.8 | 1180 | 29 | 32 | 41 | 110 | 167 | 60 | N | N | N | N | N | N |
| LOC283174 | high in P | 5.5 | 0.017761337 | 1.8 | 1181 | 12 | 17 | 15 | 25 | 95 | 62 | N | N | N | N | N | N |
| SULT2B1 | high in P | 7.4 | 0.017768155 | 1.8 | 1182 | 4 | 4 | 4 | 17 | 137 | 7 | N | N | N | N | N | N |
| ACAP1 | high in P | 3.8 | 0.017781793 | 1.8 | 1183 | 12 | 17 | 24 | 55 | 48 | 286 | P | P | N | N | N | N |
| ZNF625 | high in P | 4.9 | 0.017809751 | 1.8 | 1184 | 16 | 12 | 28 | 63 | 46 | 37 | N | N | N | N | N | N |
| RNF216 | high in P | 2.9 | 0.01781657 | 1.7 | 1185 | 57 | 59 | 99 | 251 | 280 | 201 | N | N | N | N | N | N |
| OSTC | high in P | 3.9 | 0.01784521 | 1.7 | 1186 | 5 | 5 | 5 | 11 | 12 | 13 | NA | NA | N | N | N | N |
| KIAA0649 | high in P | 7.9 | 0.017888169 | 1.7 | 1187 | 53 | 15 | 15 | 85 | 85 | 60 | N | N | N | N | N | N |
| DNAJB7 | high in P | 5.5 | 0.017894988 | 1.7 | 1188 | 5 | 5 | 7 | 22 | 23 | 10 | NA | NA | N | N | N | N |
| RBM23 | high in P | 3.2 | 0.017908626 | 1.7 | 1189 | 255 | 87 | 204 | 825 | 566 | 526 | N | N | N | N | N | N |
| SLC27A5 | high in P | 5.0 | 0.017969997 | 1.7 | 1190 | 43 | 11 | 41 | 111 | 178 | 75 | N | N | N | N | N | N |
| DAK | high in P | 8.3 | 0.017976816 | 1.7 | 1191 | 150 | 28 | 38 | 287 | 410 | 213 | N | N | N | N | N | N |
| KAT5 | high in P | 6.6 | 0.017983635 | 1.7 | 1192 | 58 | 53 | 12 | 376 | 145 | 112 | N | N | N | N | N | N |
| L2HGDH | high in P | 2.9 | 0.017990453 | 1.7 | 1193 | 45 | 112 | 94 | 264 | 286 | 316 | NA | NA | N | N | N | N |
| MRPS7 | high in P | 3.9 | 0.018002728 | 1.7 | 1194 | 196 | 85 | 132 | 614 | 621 | 316 | N | N | N | N | N | N |
| ZNF814 | high in P | 3.9 | 0.018015002 | 1.7 | 1195 | 20 | 22 | 26 | 55 | 76 | 41 | N | N | N | N | N | N |
| CCHCR1 | high in P | 3.7 | 0.018030685 | 1.7 | 1196 | 35 | 17 | 17 | 69 | 29 | 61 | NA | NA | N | N | N | N |
| DRAM1 | high in P | 3.1 | 0.01806819 | 1.7 | 1197 | 69 | 104 | 91 | 281 | 185 | 310 | N | N | N | N | N | N |
| LOC92659 | high in P | 3.2 | 0.018088646 | 1.7 | 1198 | 124 | 62 | 111 | 265 | 265 | 359 | N | N | N | N | N | P |
| PDPK1 | high in P | 4.1 | 0.018182066 | 1.7 | 1199 | 106 | 64 | 58 | 269 | 225 | 326 | N | N | N | N | P | N |
| ACADS | high in P | 3.7 | 0.018188885 | 1.7 | 1200 | 45 | 32 | 32 | 179 | 67 | 86 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | Nulliparous (NP) | | | Parous (P) | | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| WWOX | high in P | 2.8 | 0.018233208 | 1.7 | 1201 | 18 | 17 | 21 | 51 | 33 | 31 | N | N | N | N | N | N |
| CNPY3 | high in P | 4.3 | 0.018240027 | 1.7 | 1202 | 273 | 65 | 268 | 1144 | 893 | 537 | N | N | N | N | N | N |
| ARPC3 | high in P | 4.7 | 0.018306853 | 1.7 | 1203 | 3 | 6 | 7 | 48 | 26 | 11 | N | N | N | N | N | N |
| PRPSAP1 | high in P | 4.3 | 0.0183239 | 1.7 | 1204 | 82 | 30 | 37 | 104 | 367 | 376 | N | N | N | N | N | N |
| PRR12 | high in P | 6.8 | 0.018395499 | 1.7 | 1205 | 99 | 29 | 40 | 343 | 166 | 201 | N | N | N | N | N | N |
| NUFIP1 | high in P | 4.4 | 0.018402318 | 1.7 | 1206 | 20 | 26 | 37 | 165 | 102 | 50 | N | N | N | N | N | N |
| STK32C | high in P | 3.8 | 0.018415956 | 1.7 | 1207 | 17 | 8 | 21 | 33 | 36 | 40 | N | N | N | N | N | N |
| EPS8L1 | high in P | 5.2 | 0.01842823 | 1.7 | 1208 | 20 | 11 | 10 | 33 | 153 | 22 | N | N | N | N | N | N |
| ADNP | high in P | 3.1 | 0.018448687 | 1.7 | 1209 | 58 | 106 | 129 | 305 | 246 | 391 | N | N | N | N | N | N |
| ST6GALNAC4 | high in P | 6.0 | 0.018462325 | 1.7 | 1210 | 276 | 51 | 170 | 1730 | 755 | 448 | N | N | N | N | N | N |
| DGKQ | high in P | 6.4 | 0.018487555 | 1.7 | 1211 | 51 | 13 | 22 | 87 | 125 | 75 | NA | NA | N | N | N | N |
| BAT2L1 | high in P | 2.8 | 0.018494374 | 1.7 | 1212 | 1182 | 809 | 1508 | 3109 | 3508 | 3735 | N | N | N | N | N | N |
| LMTK2 | high in P | 2.9 | 0.018514831 | 1.7 | 1213 | 138 | 178 | 206 | 520 | 613 | 631 | N | N | N | N | N | N |
| USP40 | high in P | 5.3 | 0.018852165 | 1.7 | 1214 | 134 | 35 | 60 | 308 | 282 | 281 | N | N | N | P | N | N |
| C3orf62 | high in P | 3.6 | 0.018528469 | 1.7 | 1215 | 44 | 25 | 36 | 97 | 106 | 144 | N | N | N | N | N | N |
| ABCF3 | high in P | 3.1 | 0.018535288 | 1.7 | 1216 | 68 | 73 | 116 | 201 | 240 | 214 | N | N | N | N | N | N |
| PANX2 | high in P | 2.8 | 0.0185612 | 1.7 | 1217 | 12 | 28 | 41 | 103 | 71 | 80 | N | N | N | N | N | N |
| SHISA4 | high in P | 6.5 | 0.018585748 | 1.7 | 1218 | 77 | 15 | 22 | 152 | 92 | 134 | N | N | N | N | N | N |
| TBKBP1 | high in P | 3.2 | 0.018626662 | 1.7 | 1219 | 20 | 15 | 22 | 42 | 44 | 37 | N | N | N | N | N | N |
| FZR1 | high in P | 2.7 | 0.018633481 | 1.7 | 1220 | 58 | 45 | 62 | 148 | 163 | 173 | N | N | N | N | N | N |
| DUS3L | high in P | 5.3 | 0.018667576 | 1.7 | 1221 | 99 | 57 | 228 | 600 | 897 | 293 | N | N | N | N | N | N |
| OBSCN | high in P | 5.2 | 0.018674395 | 1.7 | 1222 | 108 | 79 | 126 | 193 | 436 | 535 | N | N | P | N | N | N |
| CLEC17A | high in P | 4.5 | 0.018693488 | 1.7 | 1223 | 4 | 8 | 4 | 14 | 11 | 24 | N | N | N | N | N | N |
| OGDH | high in P | 4.9 | 0.018700307 | 1.7 | 1224 | 319 | 107 | 176 | 977 | 854 | 515 | N | N | N | N | N | N |
| C2orf68 | high in P | 2.9 | 0.018741902 | 1.7 | 1225 | 111 | 91 | 48 | 364 | 265 | 256 | N | N | N | N | N | N |
| RPS10 | high in P | 6.8 | 0.018769178 | 1.7 | 1226 | 9 | 9 | 9 | 23 | 30 | 21 | N | N | N | N | N | N |
| CTDP1 | high in P | 3.0 | 0.018789635 | 1.7 | 1227 | 91 | 49 | 75 | 199 | 245 | 151 | N | N | N | N | N | P |
| KIF21B | high in P | 10.0 | 0.018813502 | 1.7 | 1228 | 48 | 16 | 18 | 45 | 111 | 142 | N | N | N | N | N | N |
| GRM2 | high in P | 4.9 | 0.018841459 | 1.7 | 1229 | 2 | 2 | 2 | 13 | 4 | 24 | N | N | N | N | N | N |
| CLDN4 | high in P | 10.6 | 0.018855097 | 1.7 | 1230 | 157 | 59 | 32 | 462 | 401 | 263 | N | N | N | N | N | N |
| TMEM86B | high in P | 4.9 | 0.018926014 | 1.7 | 1231 | 7 | 11 | 8 | 38 | 17 | 71 | N | N | N | N | N | N |
| CENPT | high in P | 3.8 | 0.018945107 | 1.7 | 1232 | 106 | 131 | 249 | 425 | 596 | 424 | N | N | N | N | N | N |
| ATR | high in P | 3.8 | 0.018977838 | 1.7 | 1233 | 36 | 25 | 39 | 108 | 113 | 54 | N | N | N | N | N | N |
| CENPM | high in P | 4.1 | 0.018984657 | 1.7 | 1234 | 2 | 5 | 6 | 12 | 27 | 13 | N | N | N | N | N | N |
| CCDC41 | high in P | 2.7 | 0.018991476 | 1.7 | 1235 | 6 | 12 | 12 | 27 | 47 | 23 | N | N | N | N | N | N |
| XRCC2 | high in P | 3.6 | 0.019009206 | 1.7 | 1236 | 674 | 476 | 971 | 2481 | 1625 | 2383 | N | N | N | N | N | N |
| AFMID | high in P | 2.7 | 0.019049437 | 1.7 | 1237 | 9 | 22 | 18 | 38 | 44 | 72 | N | N | N | N | N | N |
| PAK6 | high in P | 9.5 | 0.019078759 | 1.7 | 1238 | 9 | 14 | 14 | 42 | 158 | 19 | N | N | N | N | N | N |
| PTCD3 | high in P | 3.1 | 0.019149676 | 1.7 | 1239 | 74 | 91 | 100 | 201 | 405 | 281 | N | N | N | N | N | N |
| METTL11A | high in P | 3.2 | 0.019156495 | 1.7 | 1240 | 263 | 190 | 111 | 620 | 547 | 515 | N | N | N | N | N | N |
| PDCD11 | high in P | 3.1 | 0.019166723 | 1.7 | 1241 | 56 | 97 | 66 | 177 | 253 | 171 | N | N | N | N | N | N |
| HAUS5 | high in P | 4.4 | 0.019202864 | 1.7 | 1242 | 71 | 24 | 45 | 162 | 183 | 174 | NA | NA | N | N | N | N |
| TMC8 | high in P | 5.8 | 0.019223321 | 1.7 | 1243 | 17 | 5 | 11 | 14 | 42 | 134 | N | N | N | N | N | N |
| TUBGCP5 | high in P | 5.5 | 0.019251279 | 1.7 | 1244 | 43 | 21 | 27 | 120 | 62 | 111 | N | N | N | N | P | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | | Nulliparous (NP) | | | Parous (P) | | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 NP | CD44+ N66 P | GeneBody NP Met NP | GeneBody Met P | Pro-motor Met NP | Pro-moter Met P |
|---|---|---|---|---|---|---|---|---|---|---|---|---|---|---|---|---|---|
| SLC29A1 | high in P | 4.3 | 0.019285373 | 1.7 | 1245 | 645 | 183 | 394 | 1556 | 1980 | 1082 | N | N | N | N | N | N |
| SEC16A | high in P | 3.5 | 0.019292192 | 1.7 | 1246 | 220 | 162 | 378 | 840 | 1045 | 645 | N | N | N | N | N | N |
| GATS | high in P | 21.9 | 0.019314695 | 1.7 | 1247 | 88 | 9 | 12 | 235 | 74 | 174 | N | N | N | N | N | N |
| LYPD3 | high in P | 4.2 | 0.019321514 | 1.7 | 1248 | 47 | 59 | 84 | 152 | 711 | 182 | N | N | N | N | N | N |
| PLOD3 | high in P | 3.9 | 0.019350835 | 1.7 | 1249 | 275 | 121 | 178 | 667 | 731 | 464 | N | N | N | N | N | N |
| APOO | high in P | 5.7 | 0.019394934 | 1.7 | 1250 | 2 | 9 | 2 | 23 | 12 | 15 | N | NA | N | N | N | N |
| DHRS12 | high in P | 4.2 | 0.019414934 | 1.7 | 1251 | 43 | 12 | 23 | 84 | 63 | 140 | N | N | N | N | N | N |
| TFRC | high in P | 3.0 | 0.019441527 | 1.7 | 1252 | 188 | 265 | 276 | 528 | 1069 | 743 | N | N | N | P | N | N |
| NNL | high in P | 3.2 | 0.019448346 | 1.7 | 1253 | 8 | 9 | 9 | 16 | 13 | 21 | N | N | N | N | N | N |
| FAM48A | high in P | 3.0 | 0.019480395 | 1.7 | 1254 | 9 | 37 | 34 | 105 | 73 | 68 | NA | N | N | N | N | N |
| TNIK | high in P | 3.1 | 0.019500852 | 1.7 | 1255 | 15 | 17 | 24 | 26 | 38 | 42 | N | N | N | N | N | N |
| TTC38 | high in P | 2.6 | 0.019507671 | 1.7 | 1256 | 29 | 26 | 21 | 83 | 61 | 58 | N | N | N | N | N | N |
| CHST5 | high in P | 8.2 | 0.019521309 | 1.7 | 1257 | 23 | 6 | 7 | 31 | 42 | 22 | N | N | N | N | P | N |
| HIVEP3 | high in P | 6.2 | 0.019540402 | 1.7 | 1258 | 124 | 108 | 129 | 237 | 690 | 954 | N | N | N | N | N | N |
| ZSWIM7 | high in P | 3.1 | 0.019555404 | 1.7 | 1259 | 12 | 9 | 18 | 49 | 53 | 33 | N | N | N | N | N | N |
| RNF112 | high in P | 7.1 | 0.019562223 | 1.7 | 1260 | 23 | 6 | 8 | 43 | 18 | 79 | N | N | N | N | P | N |
| DYRK1B | high in P | 2.4 | 0.019602455 | 1.7 | 1261 | 36 | 46 | 44 | 77 | 85 | 82 | N | N | N | N | N | N |
| ITCH | high in P | 2.7 | 0.019614729 | 1.7 | 1262 | 35 | 48 | 41 | 150 | 103 | 84 | N | N | N | N | N | N |
| GCDH | high in P | 3.5 | 0.019634504 | 1.7 | 1263 | 65 | 35 | 44 | 201 | 149 | 110 | N | N | N | N | N | N |
| EIF2B5 | high in P | 4.4 | 0.019653597 | 1.7 | 1264 | 99 | 108 | 309 | 594 | 833 | 414 | N | N | N | N | N | N |
| FASN | high in P | 2.7 | 0.019660416 | 1.7 | 1265 | 89 | 127 | 183 | 355 | 477 | 433 | N | N | N | N | N | N |
| SNAPC4 | high in P | 3.6 | 0.019667235 | 1.7 | 1266 | 23 | 32 | 58 | 95 | 148 | 88 | N | N | N | N | N | N |
| C16orf46 | high in P | 2.9 | 0.019680191 | 1.7 | 1267 | 4 | 6 | 5 | 14 | 11 | 10 | N | N | N | N | N | N |
| RUFY1 | high in P | 3.9 | 0.019707467 | 1.7 | 1268 | 105 | 43 | 60 | 250 | 202 | 179 | P | N | N | N | N | N |
| EIF4G1 | high in P | 3.2 | 0.019714286 | 1.7 | 1269 | 196 | 139 | 237 | 645 | 783 | 423 | N | N | N | N | N | N |
| ZNF544 | high in P | 3.3 | 0.019741562 | 1.7 | 1270 | 22 | 21 | 32 | 89 | 113 | 50 | N | N | N | N | N | N |
| SMG6 | high in P | 4.8 | 0.019757245 | 1.7 | 1271 | 327 | 53 | 157 | 674 | 655 | 863 | N | N | P | N | N | N |
| HES6 | high in P | 4.5 | 0.019769519 | 1.7 | 1272 | 69 | 13 | 29 | 170 | 101 | 121 | N | N | N | N | N | N |
| FAM70B | high in P | 5.7 | 0.019785203 | 1.7 | 1273 | 27 | 1 | 4 | 52 | 33 | 24 | N | N | N | N | N | N |
| GALNTL2 | high in P | 2.5 | 0.019800886 | 1.7 | 1274 | 24 | 64 | 58 | 149 | 157 | 151 | N | N | N | N | N | N |
| ZNF792 | high in P | 10.8 | 0.019811657 | 1.7 | 1275 | 21 | 5 | 5 | 26 | 16 | 15 | N | N | N | N | N | N |
| CCDC154 | high in P | 4.5 | 0.019835663 | 1.7 | 1276 | 2 | 9 | 14 | 39 | 20 | 37 | NA | NA | N | N | N | N |
| RAB4A | high in P | 3.2 | 0.019858612 | 1.7 | 1277 | 119 | 109 | 82 | 209 | 395 | 332 | N | N | N | N | N | N |
| SV2A | high in P | 4.5 | 0.019871804 | 1.7 | 1278 | 64 | 48 | 32 | 495 | 179 | 82 | N | N | N | N | N | N |
| SUV420H1 | high in P | 3.0 | 0.019913399 | 1.7 | 1279 | 30 | 33 | 25 | 54 | 75 | 100 | N | N | N | N | N | N |
| PLCD3 | high in P | 2.8 | 0.019925673 | 1.7 | 1280 | 434 | 334 | 465 | 952 | 988 | 1233 | N | N | N | N | N | N |
| ATG4B | high in P | 3.0 | 0.019932492 | 1.7 | 1281 | 238 | 120 | 259 | 674 | 584 | 764 | N | N | N | N | N | N |
| TMEM43 | high in P | 3.4 | 0.019939311 | 1.7 | 1282 | 385 | 209 | 316 | 1056 | 1470 | 766 | N | N | N | N | N | N |
| PDIA3 | high in P | 3.4 | 0.019982271 | 1.7 | 1283 | 49 | 28 | 38 | 142 | 73 | 82 | N | N | N | N | N | N |
| SMC1A | high in P | 3.1 | 0.019995909 | 1.7 | 1284 | 63 | 93 | 82 | 291 | 241 | 155 | N | N | N | N | N | N |
| RPS17 | high in P | 2.6 | 0.020002728 | 1.7 | 1285 | 7393 | 6281 | 7884 | 19271 | 16888 | 16116 | N | N | N | N | N | N |
| SRP72 | high in P | 5.3 | 0.020030003 | 1.7 | 1286 | 259 | 176 | 82 | 1331 | 474 | 513 | N | N | N | N | N | N |
| CHDH | high in P | 2.4 | 0.020036822 | 1.7 | 1287 | 33 | 28 | 37 | 69 | 72 | 59 | N | N | N | N | N | N |
| FRY | high in P | 3.3 | 0.020050046 | 1.7 | 1288 | 49 | 37 | 23 | 96 | 88 | 69 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | | Nulliparous (NP) | | | Parous (P) | | | NP | | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met | |
| LRG1 | high in P | 9.9 | 0.020111831 | 1.7 | 1289 | 51 | 8 | 49 | 51 | 466 | 453 | N | N | N | N | N | N | |
| HSF1 | high in P | 3.7 | 0.020111865 | 1.7 | 1290 | 461 | 337 | 787 | 1559 | 2711 | 1261 | N | N | N | N | N | N | |
| ADPRHL1 | high in P | 6.8 | 0.020123469 | 1.7 | 1291 | 7 | 7 | 8 | 27 | 19 | 30 | N | N | N | N | N | N | |
| SLC25A26 | high in P | 3.0 | 0.020141152 | 1.7 | 1292 | 196 | 130 | 108 | 328 | 502 | 412 | N | N | N | N | N | N | |
| C21orf2 | high in P | 5.8 | 0.020165019 | 1.7 | 1293 | 282 | 26 | 118 | 890 | 760 | 502 | N | N | N | N | N | N | |
| SLC24A2 | high in P | 4.0 | 0.020178657 | 1.7 | 1294 | 2 | 2 | 3 | 8 | 5 | 5 | N | P | N | N | N | N | |
| COX10 | high in P | 2.8 | 0.020185476 | 1.7 | 1295 | 11 | 16 | 13 | 30 | 37 | 24 | N | N | N | N | N | N | |
| ITK | high in P | 5.7 | 0.020192295 | 1.7 | 1296 | 15 | 10 | 5 | 14 | 29 | 152 | N | N | N | N | N | N | |
| GDH | high in P | 9.0 | 0.020207978 | 1.7 | 1297 | 260 | 40 | 61 | 547 | 406 | 516 | N | N | N | N | N | N | |
| SNORD100 | high in P | 3.9 | 0.020243437 | 1.7 | 1298 | 9 | 15 | 22 | 32 | 81 | 48 | N | N | N | N | N | N | |
| ADAMTS2 | high in P | 2.7 | 0.020265939 | 1.7 | 1299 | 23 | 30 | 27 | 68 | 62 | 53 | N | N | N | N | N | N | |
| TOM1 | high in P | 6.0 | 0.020324582 | 1.7 | 1300 | 189 | 176 | 53 | 1261 | 398 | 481 | N | N | N | N | N | N | |
| FMNL3 | high in P | 4.5 | 0.020331401 | 1.7 | 1301 | 259 | 100 | 96 | 790 | 432 | 1332 | N | N | N | N | N | N | |
| DPP9 | high in P | 4.3 | 0.020396863 | 1.7 | 1302 | 293 | 125 | 280 | 1486 | 1002 | 488 | N | N | N | N | N | N | |
| MRPL4 | high in P | 2.9 | 0.020422093 | 1.7 | 1303 | 33 | 96 | 97 | 258 | 290 | 273 | N | N | N | N | N | N | |
| IL1B | high in P | 8.2 | 0.020444186 | 1.7 | 1304 | 97 | 43 | 38 | 323 | 96 | 920 | N | N | N | N | N | N | |
| SULT1B1 | high in P | 2.7 | 0.020448005 | 1.7 | 1305 | 1 | 1 | 1 | 3 | 4 | 6 | N | N | N | N | N | N | |
| ODF3B | high in P | 3.7 | 0.0204821 | 1.7 | 1306 | 100 | 77 | 179 | 287 | 408 | 337 | N | N | N | N | N | N | |
| GGNBP2 | high in P | 3.3 | 0.020517559 | 1.7 | 1307 | 214 | 179 | 350 | 651 | 796 | 1079 | N | N | N | P | N | N | |
| PLAU | high in P | 5.9 | 0.02066553 | 1.7 | 1308 | 1131 | 323 | 467 | 6871 | 3924 | 1175 | N | N | N | N | N | N | |
| ARHGAP27 | high in P | 4.1 | 0.020707126 | 1.7 | 1309 | 46 | 20 | 90 | 172 | 238 | 140 | N | N | N | N | N | N | |
| SUSD5 | high in P | 2.7 | 0.020713945 | 1.7 | 1310 | 20 | 24 | 23 | 62 | 48 | 40 | N | N | N | N | N | N | |
| SPHAR | high in P | 4.4 | 0.020739857 | 1.7 | 1311 | 14 | 5 | 2 | 16 | 19 | 8 | N | N | N | N | N | N | |
| TEX264 | high in P | 3.7 | 0.020795772 | 1.7 | 1312 | 297 | 62 | 184 | 862 | 542 | 620 | N | P | N | N | N | N | |
| PPFIA4 | high in P | 3.6 | 0.0208041 | 1.7 | 1313 | 26 | 10 | 10 | 52 | 20 | 31 | N | N | N | N | N | N | |
| GPT2 | high in P | 4.9 | 0.020838732 | 1.7 | 1314 | 42 | 18 | 21 | 72 | 320 | 49 | N | N | N | N | N | N | |
| HYAL3 | high in P | 3.3 | 0.020859189 | 1.7 | 1315 | 4 | 4 | 5 | 10 | 18 | 10 | N | N | N | N | N | N | |
| TMEM81 | high in P | 5.6 | 0.020885101 | 1.7 | 1316 | 2 | 3 | 4 | 7 | 14 | 41 | N | N | N | N | N | N | |
| CLIC6 | high in P | 3.9 | 0.020939652 | 1.7 | 1317 | 8 | 8 | 8 | 10 | 13 | 11 | P | P | N | N | N | N | |
| POLB | high in P | 3.9 | 0.020939652 | 1.7 | 1318 | 6 | 6 | 6 | 8 | 11 | 9 | N | N | N | N | N | N | |
| ZNF414 | high in P | 3.4 | 0.020979202 | 1.7 | 1319 | 6 | 16 | 12 | 76 | 31 | 19 | N | N | N | N | N | N | |
| KDM6B | high in P | 4.1 | 0.020986021 | 1.7 | 1320 | 3244 | 2398 | 4696 | 8013 | 13700 | 27971 | NA | NA | N | N | N | N | |
| CDH13 | high in P | 2.9 | 0.020998295 | 1.7 | 1321 | 43 | 36 | 29 | 63 | 88 | 80 | P | P | N | N | N | N | |
| MPP6 | high in P | 3.3 | 0.021013297 | 1.7 | 1322 | 27 | 14 | 12 | 27 | 55 | 54 | N | N | N | N | N | N | |
| TSC1 | high in P | 2.7 | 0.021020116 | 1.7 | 1323 | 32 | 52 | 50 | 100 | 92 | 132 | N | N | N | N | N | N | |
| APOBEC3H | high in P | 3.9 | 0.021026935 | 1.7 | 1324 | 2 | 2 | 3 | 5 | 8 | 16 | N | N | N | N | N | N | |
| SLC5A5 | high in P | 3.9 | 0.021045346 | 1.7 | 1325 | 34 | 60 | 78 | 154 | 137 | 289 | N | P | N | N | N | N | |
| FGFR3 | high in P | 4.9 | 0.021101943 | 1.7 | 1326 | 41 | 24 | 39 | 58 | 151 | 458 | N | N | N | N | N | N | |
| NIPAL1 | high in P | 3.1 | 0.021114899 | 1.7 | 1327 | 17 | 7 | 15 | 25 | 24 | 36 | NA | N | N | N | N | N | |
| AAAS | high in P | 3.1 | 0.021121718 | 1.7 | 1328 | 63 | 39 | 43 | 192 | 123 | 91 | NA | N | N | N | N | N | |
| CUL9 | high in P | 4.0 | 0.021135356 | 1.7 | 1329 | 75 | 25 | 51 | 126 | 147 | 253 | NA | NA | N | N | N | N | |
| GPAT2 | high in P | 5.3 | 0.021155813 | 1.7 | 1330 | 41 | 10 | 18 | 211 | 88 | 35 | NA | NA | N | N | N | N | |
| KDM1B | high in P | 3.6 | 0.021189908 | 1.7 | 1331 | 7 | 7 | 8 | 11 | 10 | 15 | NA | NA | N | N | N | N | |
| PIGP | high in P | 3.7 | 0.021224003 | 1.7 | 1332 | 78 | 27 | 29 | 155 | 86 | 118 | N | N | N | N | N | P | |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | | Nulliparous (NP) | | | Parous (P) | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| HPX | high in P | 4.8 | 0.02124446 | 1.7 | 1333 | 9 | 12 | 19 | 31 | 22 | 39 | N | N | N | N | N | N |
| PRRT1 | high in P | 8.5 | 0.021285373 | 1.7 | 1334 | 52 | 6 | 10 | 63 | 72 | 115 | N | N | N | N | N | N |
| ATG2B | high in P | 3.1 | 0.021304466 | 1.7 | 1335 | 41 | 52 | 52 | 134 | 79 | 124 | N | N | N | N | N | N |
| CCDC149 | high in P | 3.2 | 0.021311285 | 1.7 | 1336 | 15 | 20 | 25 | 42 | 43 | 79 | N | N | N | N | N | N |
| CST7 | high in P | 6.0 | 0.021318104 | 1.7 | 1337 | 82 | 94 | 25 | 242 | 142 | 548 | N | N | N | N | N | N |
| SAPS2 | high in P | 2.3 | 0.02133106 | 1.7 | 1338 | 38 | 49 | 54 | 109 | 93 | 101 | N | N | N | N | N | N |
| TRAF6 | high in P | 2.5 | 0.021351517 | 1.7 | 1339 | 9 | 13 | 14 | 25 | 21 | 32 | N | N | N | N | N | N |
| ARGFX | high in P | 5.3 | 0.021376065 | 1.7 | 1340 | 14 | 16 | 17 | 55 | 41 | 39 | N | N | N | N | N | N |
| C21orf94 | high in P | 3.7 | 0.021391749 | 1.7 | 1341 | 3 | 6 | 3 | 7 | 17 | 11 | N | N | N | N | N | N |
| FIP1L1 | high in P | 3.3 | 0.021398568 | 1.7 | 1342 | 16 | 10 | 27 | 40 | 79 | 54 | NA | NA | N | N | N | N |
| ANKRD13B | high in P | 3.4 | 0.021415615 | 1.7 | 1343 | 60 | 75 | 82 | 137 | 269 | 242 | N | N | N | N | N | N |
| CTRC | high in P | 8.4 | 0.021455847 | 1.7 | 1344 | 29 | 3 | 6 | 26 | 66 | 49 | N | N | N | N | N | N |
| STK39 | high in P | 4.6 | 0.021470167 | 1.7 | 1345 | 135 | 13 | 62 | 284 | 509 | 249 | N | N | N | N | N | N |
| TATDN3 | high in P | 3.5 | 0.021489942 | 1.7 | 1346 | 9 | 20 | 31 | 94 | 62 | 42 | N | P | N | N | N | N |
| CTSS | high in P | 2.8 | 0.021526083 | 1.7 | 1347 | 23 | 27 | 17 | 63 | 54 | 40 | N | N | N | N | N | N |
| MARS | high in P | 5.2 | 0.021532901 | 1.7 | 1348 | 579 | 490 | 370 | 3447 | 2426 | 858 | N | N | N | N | N | N |
| AARSD1 | high in P | 2.7 | 0.021560177 | 1.7 | 1349 | 22 | 34 | 35 | 70 | 51 | 77 | N | N | N | N | N | N |
| ZFPM1 | high in P | 3.9 | 0.021570406 | 1.7 | 1350 | 59 | 23 | 30 | 121 | 182 | 74 | N | N | N | N | N | N |
| RIMS1 | high in P | 4.2 | 0.021584044 | 1.7 | 1351 | 13 | 13 | 14 | 23 | 19 | 16 | N | N | N | N | N | N |
| MRPS15 | high in P | 3.0 | 0.021597682 | 1.7 | 1352 | 84 | 47 | 38 | 215 | 183 | 93 | NA | NA | N | N | N | N |
| LOC100271831 | high in P | 5.7 | 0.021604501 | 1.7 | 1353 | 7 | 2 | 9 | 48 | 12 | 14 | N | N | N | N | N | N |
| POLR3D | high in P | 2.5 | 0.021616775 | 1.7 | 1354 | 18 | 17 | 18 | 34 | 32 | 48 | N | N | N | N | N | N |
| ABCF2 | high in P | 2.3 | 0.021634504 | 1.7 | 1355 | 625 | 504 | 713 | 1590 | 1536 | 1440 | NA | NA | N | N | N | P |
| TRIM11 | high in P | 2.2 | 0.021668599 | 1.7 | 1356 | 91 | 82 | 76 | 193 | 170 | 189 | N | N | N | N | N | N |
| NICN1 | high in P | 5.3 | 0.021686328 | 1.7 | 1357 | 34 | 15 | 22 | 65 | 79 | 104 | N | N | N | N | N | N |
| SFXN2 | high in P | 2.4 | 0.021702012 | 1.7 | 1358 | 12 | 9 | 10 | 20 | 17 | 21 | NA | NA | N | N | N | N |
| NUDT22 | high in P | 4.8 | 0.02174088 | 1.7 | 1359 | 16 | 20 | 12 | 132 | 62 | 23 | N | N | N | N | N | N |
| TSSC1 | high in P | 4.9 | 0.021769519 | 1.7 | 1360 | 16 | 8 | 6 | 53 | 40 | 13 | N | N | N | N | N | N |
| C19orf6 | high in P | 3.4 | 0.021804296 | 1.7 | 1361 | 924 | 306 | 1515 | 3355 | 3483 | 2937 | N | N | N | N | N | N |
| CARD10 | high in P | 7.3 | 0.021842482 | 1.7 | 1362 | 79 | 24 | 31 | 116 | 574 | 99 | N | N | N | N | N | N |
| ZNF737 | high in P | 3.2 | 0.021923628 | 1.7 | 1363 | 41 | 28 | 43 | 90 | 120 | 140 | NA | NA | N | N | N | N |
| RBM5 | high in P | 3.5 | 0.021956359 | 1.7 | 1364 | 104 | 196 | 398 | 689 | 640 | 1281 | N | N | N | N | N | N |
| TNFRSF9 | high in P | 3.6 | 0.02197136 | 1.7 | 1365 | 10 | 15 | 7 | 38 | 23 | 60 | N | N | N | N | N | N |
| NFIC | high in P | 5.6 | 0.022038186 | 1.7 | 1366 | 830 | 183 | 238 | 2526 | 1203 | 1265 | P | P | N | N | P | N |
| HSPA1L | high in P | 6.0 | 0.02211877 | 1.7 | 1367 | 4 | 6 | 14 | 28 | 15 | 186 | N | N | N | N | N | N |
| BAIAP2L1 | high in P | 5.3 | 0.022134333 | 1.7 | 1368 | 159 | 70 | 136 | 376 | 2406 | 400 | NA | NA | N | N | N | N |
| DKFZp686O24166 | high in P | 2.9 | 0.022214115 | 1.7 | 1369 | 12 | 17 | 14 | 29 | 22 | 31 | N | N | N | N | N | N |
| RPS6KL1 | high in P | 3.7 | 0.022220934 | 1.7 | 1370 | 17 | 13 | 16 | 53 | 53 | 21 | N | N | N | N | N | N |
| TRPV4 | high in P | 5.8 | 0.022259802 | 1.7 | 1371 | 10 | 4 | 4 | 14 | 29 | 7 | N | N | N | N | N | N |
| SIRT7 | high in P | 3.7 | 0.02227344 | 1.7 | 1372 | 31 | 71 | 53 | 105 | 180 | 170 | N | N | N | N | P | N |
| RHEBL1 | high in P | 5.4 | 0.022315036 | 1.7 | 1373 | 10 | 29 | 6 | 34 | 41 | 72 | N | N | N | N | N | N |
| CLEC4E | high in P | 4.1 | 0.022332083 | 1.7 | 1374 | 4 | 12 | 14 | 49 | 20 | 208 | N | N | N | N | N | N |
| SPRYD4 | high in P | 6.0 | 0.022338902 | 1.7 | 1375 | 59 | 15 | 16 | 107 | 81 | 78 | N | N | N | N | N | N |
| BMS1P1 | high in P | 4.0 | 0.022364814 | 1.7 | 1376 | 2 | 5 | 9 | 20 | 15 | 34 | NA | NA | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | | Nulliparous (NP) | | | | Parous (P) | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 NP | CD44+ N66 P | GeneBody NP Met NP | GeneBody Met P | Pro-motor Met NP | Pro-moter Met P |
| MPND | high in P | 2.5 | 0.02239209 | 1.6 | 1377 | 30 | 15 | 25 | 49 | 53 | 42 | N | N | N | N | N | N |
| PATE4 | high in P | 5.3 | 0.024213229 | 1.6 | 1378 | 5 | 27 | 9 | 46 | 50 | 39 | NA | NA | N | N | N | N |
| ANKRD9 | high in P | 2.8 | 0.024420048 | 1.6 | 1379 | 163 | 67 | 113 | 365 | 304 | 298 | N | N | N | N | N | N |
| XRCC3 | high in P | 3.3 | 0.024435049 | 1.6 | 1380 | 6 | 7 | 10 | 27 | 25 | 14 | N | N | N | N | N | N |
| RNF125 | high in P | 5.3 | 0.02445687 | 1.6 | 1381 | 33 | 18 | 15 | 70 | 58 | 75 | N | N | N | N | N | N |
| C4orf14 | high in P | 4.6 | 0.022479373 | 1.6 | 1382 | 193 | 32 | 74 | 303 | 473 | 311 | N | N | N | N | N | N |
| UNC50 | high in P | 2.7 | 0.022501875 | 1.6 | 1383 | 105 | 70 | 61 | 233 | 174 | 161 | N | N | N | N | N | N |
| SLMAP | high in P | 4.1 | 0.022508694 | 1.6 | 1384 | 30 | 49 | 90 | 192 | 177 | 138 | N | N | N | N | N | N |
| DPP7 | high in P | 2.6 | 0.022531197 | 1.6 | 1385 | 176 | 96 | 201 | 443 | 454 | 435 | N | N | N | N | N | N |
| B3GALT4 | high in P | 3.3 | 0.022541425 | 1.6 | 1386 | 3 | 11 | 13 | 29 | 34 | 28 | N | N | N | N | N | N |
| SDF4 | high in P | 4.4 | 0.022555745 | 1.6 | 1387 | 1254 | 406 | 650 | 3664 | 2755 | 1754 | N | N | N | N | N | N |
| LRRC56 | high in P | 6.8 | 0.022576202 | 1.6 | 1388 | 24 | 9 | 9 | 35 | 35 | 108 | N | N | N | N | N | N |
| CXCL17 | high in P | 7.0 | 0.022588476 | 1.6 | 1389 | 3 | 15 | 13 | 55 | 113 | 21 | N | N | N | N | N | N |
| TMEM149 | high in P | 5.4 | 0.022595295 | 1.6 | 1390 | 29 | 2 | 9 | 51 | 31 | 50 | N | N | N | N | N | N |
| FAM55C | high in P | 6.7 | 0.022635527 | 1.6 | 1391 | 149 | 50 | 38 | 234 | 271 | 365 | N | N | N | N | N | N |
| HSPB1 | high in P | 9.8 | 0.022703034 | 1.6 | 1392 | 105 | 23 | 376 | 390 | 630 | 3417 | N | N | N | N | N | N |
| C5AR1 | high in P | 3.6 | 0.022725537 | 1.6 | 1393 | 13 | 9 | 8 | 22 | 14 | 36 | N | N | N | N | N | N |
| NAIP | high in P | 3.0 | 0.022732356 | 1.6 | 1394 | 30 | 35 | 50 | 82 | 71 | 156 | N | P | N | N | N | N |
| MUC2 | high in P | 2.7 | 0.022754859 | 1.6 | 1395 | 3 | 3 | 3 | 6 | 6 | 11 | N | N | N | N | N | N |
| NAPSA | high in P | 2.7 | 0.022754859 | 1.6 | 1396 | 1 | 1 | 1 | 3 | 4 | 9 | N | N | N | N | N | N |
| AATF | high in P | 2.9 | 0.022862598 | 1.6 | 1397 | 28 | 92 | 76 | 224 | 208 | 171 | N | N | N | N | N | N |
| MAP3K4 | high in P | 2.6 | 0.022883055 | 1.6 | 1398 | 31 | 86 | 83 | 202 | 163 | 193 | P | P | N | N | N | N |
| CNTD2 | high in P | 7.1 | 0.022953972 | 1.6 | 1399 | 66 | 10 | 34 | 62 | 210 | 546 | P | N | N | N | N | N |
| UBE3B | high in P | 2.8 | 0.022988749 | 1.6 | 1400 | 21 | 29 | 24 | 81 | 50 | 63 | N | N | N | N | N | N |
| CACNA2D3 | high in P | 3.9 | 0.023010569 | 1.6 | 1401 | 14 | 8 | 8 | 10 | 17 | 16 | N | N | N | N | N | N |
| RASA4P | high in P | 4.4 | 0.023039891 | 1.6 | 1402 | 128 | 36 | 72 | 254 | 183 | 540 | N | P | N | N | N | N |
| RFPL1S | high in P | 3.7 | 0.023081487 | 1.6 | 1403 | 44 | 15 | 21 | 64 | 77 | 46 | N | N | N | N | N | N |
| WDR44 | high in P | 2.8 | 0.023134674 | 1.6 | 1404 | 61 | 43 | 59 | 117 | 129 | 237 | N | P | N | N | N | N |
| CLDN15 | high in P | 3.3 | 0.023207637 | 1.6 | 1405 | 9 | 21 | 22 | 44 | 55 | 54 | N | N | N | N | N | N |
| PPAPDC2 | high in P | 8.7 | 0.023221275 | 1.6 | 1406 | 24 | 12 | 12 | 59 | 47 | 29 | N | N | N | N | N | N |
| MYST3 | high in P | 3.0 | 0.023236959 | 1.6 | 1407 | 519 | 241 | 500 | 1164 | 1396 | 1829 | N | N | N | N | N | N |
| XPO4 | high in P | 2.5 | 0.023257416 | 1.6 | 1408 | 20 | 38 | 30 | 80 | 90 | 54 | N | N | N | N | N | N |
| PIGS | high in P | 4.3 | 0.023326969 | 1.6 | 1409 | 192 | 68 | 81 | 578 | 319 | 296 | N | N | N | N | N | N |
| LOC646851 | high in P | 4.7 | 0.023296966 | 1.6 | 1410 | 133 | 62 | 66 | 249 | 317 | 262 | NA | NA | N | N | N | N |
| ZFP28 | high in P | 2.9 | 0.023303785 | 1.6 | 1411 | 19 | 12 | 10 | 27 | 17 | 27 | N | N | N | N | N | N |
| BID | high in P | 2.6 | 0.023310603 | 1.6 | 1412 | 79 | 143 | 158 | 309 | 409 | 355 | N | N | N | N | N | N |
| ZNF121 | high in P | 2.6 | 0.023378111 | 1.6 | 1413 | 7 | 11 | 11 | 32 | 30 | 18 | N | P | N | N | N | N |
| ZFYVE26 | high in P | 4.0 | 0.023400614 | 1.6 | 1414 | 17 | 20 | 19 | 59 | 36 | 48 | N | N | N | N | N | N |
| CLPTM1 | high in P | 2.3 | 0.023407433 | 1.6 | 1415 | 339 | 373 | 402 | 902 | 854 | 726 | N | N | N | N | N | N |
| HEATR2 | high in P | 7.3 | 0.023434027 | 1.6 | 1416 | 26 | 12 | 9 | 36 | 50 | 50 | N | P | N | N | N | N |
| SOCS7 | high in P | 3.3 | 0.023585407 | 1.6 | 1417 | 9 | 3 | 4 | 7 | 15 | 11 | N | N | N | N | N | N |
| MOSPD3 | high in P | 4.0 | 0.023599045 | 1.6 | 1418 | 25 | 6 | 20 | 87 | 56 | 25 | N | N | N | N | P | N |
| MT1L | high in P | 6.2 | 0.023624957 | 1.6 | 1419 | 14 | 44 | 47 | 71 | 130 | 278 | N | N | N | N | N | N |
| MARK4 | high in P | 3.2 | 0.023663144 | 1.6 | 1420 | 176 | 115 | 130 | 355 | 658 | 342 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | Nulliparous (NP) | | | Parous (P) | | | NP | | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| C17orf77 | high in P | 4.2 | 0.023691101 | 1.6 | 1421 | 5 | 5 | 5 | 9 | 10 | 16 | P | P | N | N | N | N |
| CDKN2BAS | high in P | 3.9 | 0.023704739 | 1.6 | 1422 | 7 | 8 | 7 | 9 | 12 | 18 | NA | NA | N | N | N | N |
| PURA | high in P | 2.7 | 0.023730651 | 1.6 | 1423 | 28 | 31 | 31 | 85 | 72 | 50 | N | N | N | N | N | N |
| ZNF143 | high in P | 2.5 | 0.02379134 | 1.6 | 1424 | 27 | 49 | 45 | 80 | 99 | 84 | N | N | N | N | N | N |
| KIAA1530 | high in P | 3.0 | 0.023818616 | 1.6 | 1425 | 56 | 36 | 52 | 111 | 127 | 136 | N | N | N | N | N | N |
| C13orf34 | high in P | 3.2 | 0.023825435 | 1.6 | 1426 | 5 | 8 | 14 | 35 | 18 | 32 | N | N | N | N | N | N |
| THUMPD3 | high in P | 5.0 | 0.023890215 | 1.6 | 1427 | 10 | 12 | 10 | 30 | 40 | 13 | N | N | N | N | N | N |
| SF3B4 | high in P | 3.2 | 0.02393522 | 1.6 | 1428 | 584 | 477 | 335 | 1990 | 1275 | 1085 | N | N | N | N | N | N |
| OTX2OS1 | high in P | 2.6 | 0.023992499 | 1.6 | 1429 | 6 | 7 | 10 | 23 | 20 | 28 | N | N | N | N | N | N |
| NLRX1 | high in P | 8.1 | 0.024032049 | 1.6 | 1430 | 41 | 9 | 11 | 64 | 40 | 34 | N | N | N | N | N | N |
| CNTFR | high in P | 6.2 | 0.024053188 | 1.6 | 1431 | 100 | 14 | 30 | 162 | 110 | 230 | N | N | N | N | P | N |
| PARN | high in P | 3.2 | 0.024066826 | 1.6 | 1432 | 98 | 77 | 79 | 386 | 212 | 145 | N | N | N | N | N | N |
| FGF17 | high in P | 3.8 | 0.024096147 | 1.6 | 1433 | 3 | 8 | 10 | 13 | 19 | 33 | N | N | N | N | N | N |
| GJB2 | high in P | 3.7 | 0.02411831 | 1.6 | 1434 | 3 | 8 | 8 | 29 | 47 | 14 | P | P | N | N | N | N |
| ZNF516 | high in P | 3.3 | 0.024181384 | 1.6 | 1435 | 48 | 45 | 72 | 237 | 103 | 262 | N | N | N | N | N | N |
| IFI30 | high in P | 4.6 | 0.024210024 | 1.6 | 1436 | 32 | 85 | 52 | 120 | 150 | 467 | N | P | N | N | N | N |
| DUS2L | high in P | 5.5 | 0.024261848 | 1.6 | 1437 | 5 | 10 | 7 | 45 | 48 | 11 | N | N | N | N | N | N |
| PIH1D1 | high in P | 2.6 | 0.024282987 | 1.6 | 1438 | 155 | 158 | 138 | 854 | 314 | 370 | N | N | N | N | N | N |
| PPAN | high in P | 3.4 | 0.02403444 | 1.6 | 1439 | 107 | 47 | 92 | 173 | 328 | 213 | N | N | N | N | N | N |
| KIAA1875 | high in P | 2.6 | 0.024369587 | 1.6 | 1440 | 959 | 531 | 1294 | 2535 | 2665 | 2467 | N | N | N | N | N | N |
| LRRC4B | high in P | 6.1 | 0.024376406 | 1.6 | 1441 | 43 | 8 | 19 | 168 | 33 | 93 | N | N | N | N | N | N |
| RNASEH1 | high in P | 4.5 | 0.02442073 | 1.6 | 1442 | 84 | 26 | 29 | 294 | 110 | 92 | N | N | N | N | N | N |
| ARRB2 | high in P | 3.1 | 0.024441868 | 1.6 | 1443 | 18 | 17 | 11 | 42 | 28 | 59 | P | N | N | N | N | N |
| IRX1 | high in P | 3.7 | 0.024484828 | 1.6 | 1444 | 71 | 96 | 132 | 307 | 1693 | 202 | N | P | N | N | N | N |
| DLG4 | high in P | 2.8 | 0.024498466 | 1.6 | 1445 | 16 | 30 | 39 | 77 | 51 | 87 | N | N | N | N | N | N |
| TMEM63B | high in P | 3.3 | 0.024571429 | 1.6 | 1446 | 106 | 102 | 253 | 332 | 564 | 530 | N | N | N | N | N | N |
| KCNE1L | high in P | 5.3 | 0.024598704 | 1.6 | 1447 | 2 | 3 | 5 | 5 | 16 | 18 | N | N | N | N | N | N |
| INTS9 | high in P | 3.2 | 0.024643028 | 1.6 | 1448 | 46 | 24 | 33 | 66 | 94 | 53 | N | N | N | N | N | N |
| TRIM38 | high in P | 2.6 | 0.024662121 | 1.6 | 1449 | 16 | 29 | 24 | 43 | 48 | 66 | N | N | N | N | N | N |
| NME4 | high in P | 3.3 | 0.024675759 | 1.6 | 1450 | 128 | 84 | 170 | 450 | 363 | 260 | N | N | P | N | N | N |
| HADHA | high in P | 3.6 | 0.024682578 | 1.6 | 1451 | 793 | 351 | 438 | 1739 | 1722 | 1233 | N | N | N | N | N | N |
| POLL | high in P | 5.2 | 0.024689397 | 1.6 | 1452 | 69 | 10 | 28 | 137 | 109 | 116 | N | N | N | N | N | N |
| RPS6KA5 | high in P | 3.2 | 0.024696215 | 1.6 | 1453 | 34 | 47 | 48 | 57 | 74 | 95 | N | N | N | N | N | N |
| ORC6L | high in P | 3.1 | 0.024709853 | 1.6 | 1454 | 50 | 37 | 13 | 142 | 66 | 126 | N | N | N | N | N | N |
| SLC9A5 | high in P | 3.1 | 0.024726901 | 1.6 | 1455 | 21 | 17 | 17 | 33 | 38 | 32 | N | N | N | N | N | N |
| C17orf55 | high in P | 5.3 | 0.024757586 | 1.6 | 1456 | 6 | 7 | 11 | 49 | 12 | 81 | N | N | N | N | N | N |
| AGGF1 | high in P | 3.2 | 0.02477327 | 1.6 | 1457 | 14 | 13 | 10 | 43 | 29 | 31 | P | N | N | N | N | N |
| LIG4 | high in P | 5.2 | 0.024816911 | 1.6 | 1458 | 13 | 38 | 30 | 149 | 103 | 41 | N | N | N | N | N | N |
| MURC | high in P | 3.5 | 0.024890556 | 1.6 | 1459 | 7 | 10 | 11 | 21 | 21 | 72 | N | N | N | N | N | N |
| MEFV | high in P | 4.0 | 0.024897375 | 1.6 | 1460 | 5 | 5 | 6 | 9 | 8 | 18 | N | P | N | N | N | N |
| STAT4 | high in P | 8.7 | 0.024904194 | 1.6 | 1461 | 66 | 8 | 9 | 82 | 54 | 270 | N | P | N | N | N | N |
| NTN5 | high in P | 3.8 | 0.024911013 | 1.6 | 1462 | 5 | 5 | 7 | 13 | 10 | 22 | NA | NA | N | N | N | N |
| ZNF134 | high in P | 3.0 | 0.024924651 | 1.6 | 1463 | 7 | 11 | 8 | 23 | 12 | 18 | NA | N | N | N | N | N |
| GLO1 | high in P | 3.6 | 0.024938288 | 1.6 | 1464 | 1633 | 586 | 842 | 5786 | 4437 | 1892 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | Nulliparous (NP) | | | | Parous (P) | | | NP | | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| SYNRG | high in P | 3.1 | 0.024945107 | 1.6 | 1465 | 33 | 39 | 61 | 88 | 110 | 202 | NA | NA | N | N | N | N |
| LOC55908 | high in P | 4.0 | 0.024972383 | 1.6 | 1466 | 3 | 3 | 4 | 7 | 6 | 14 | N | N | N | N | N | N |
| TARBP2 | high in P | 3.2 | 0.025011251 | 1.6 | 1467 | 24 | 37 | 29 | 106 | 53 | 52 | N | N | N | N | N | N |
| ADCY2 | high in P | 4.5 | 0.025031708 | 1.6 | 1468 | 46 | 21 | 45 | 77 | 93 | 196 | N | N | N | N | N | N |
| SMYD4 | high in P | 5.8 | 0.025054211 | 1.6 | 1469 | 142 | 24 | 41 | 203 | 199 | 286 | NA | NA | N | N | N | N |
| MTPAP | high in P | 3.2 | 0.025067849 | 1.6 | 1470 | 571 | 493 | 996 | 1851 | 2042 | 1905 | N | N | N | N | N | N |
| ZC3H8 | high in P | 3.6 | 0.025087624 | 1.6 | 1471 | 4 | 14 | 5 | 20 | 32 | 20 | NA | NA | N | N | N | N |
| SLC35C2 | high in P | 4.1 | 0.025114899 | 1.6 | 1472 | 123 | 58 | 100 | 730 | 252 | 202 | N | N | N | N | N | N |
| TCAM1 | high in P | 4.0 | 0.025121718 | 1.6 | 1473 | NA | NA | NA | NA | NA | NA | N | N | N | N | N | N |
| DONSON | high in P | 3.0 | 0.025128537 | 1.6 | 1474 | 12 | 11 | 9 | 17 | 34 | 23 | N | P | N | N | N | N |
| DLGAP3 | high in P | 3.2 | 0.025151104 | 1.6 | 1475 | 4 | 4 | 5 | 17 | 9 | 10 | N | N | N | N | N | N |
| HSCB | high in P | 2.6 | 0.025164678 | 1.6 | 1476 | 51 | 59 | 81 | 158 | 142 | 211 | N | N | N | N | N | N |
| ADRA2C | high in P | 4.0 | 0.025185135 | 1.6 | 1477 | 97 | 84 | 85 | 2125 | 321 | 182 | N | N | N | P | N | N |
| ACY1 | high in P | 3.3 | 0.025207637 | 1.6 | 1478 | 118 | 40 | 88 | 240 | 355 | 168 | N | N | N | N | N | N |
| RBAK | high in P | 3.0 | 0.025233549 | 1.6 | 1479 | 15 | 25 | 29 | 56 | 40 | 104 | N | N | N | N | N | N |
| BAT3 | high in P | 3.6 | 0.025240368 | 1.6 | 1480 | 1574 | 652 | 814 | 4512 | 3260 | 2233 | N | N | N | N | N | N |
| FLJ13197 | high in P | 4.4 | 0.025256052 | 1.6 | 1481 | 6 | 6 | 6 | 11 | 13 | 22 | NA | NA | N | N | N | N |
| SRRM3 | high in P | 5.0 | 0.025326969 | 1.6 | 1482 | 6 | 7 | 17 | 21 | 19 | 42 | NA | NA | N | N | N | N |
| ZMIZ2 | high in P | 3.4 | 0.025425844 | 1.6 | 1483 | 201 | 86 | 310 | 576 | 820 | 720 | N | N | P | N | N | N |
| FLJ25363 | high in P | 3.1 | 0.025466758 | 1.6 | 1484 | 9 | 17 | 9 | 25 | 23 | 30 | P | P | N | N | N | N |
| ATMIN | high in P | 3.3 | 0.025484487 | 1.6 | 1485 | 102 | 45 | 72 | 306 | 227 | 188 | N | N | N | N | N | N |
| ALPK3 | high in P | 2.7 | 0.02550358 | 1.6 | 1486 | 20 | 24 | 37 | 83 | 52 | 54 | N | N | N | N | N | N |
| OTUD4 | high in P | 3.4 | 0.025510399 | 1.6 | 1487 | 970 | 765 | 790 | 1647 | 3026 | 3983 | N | N | N | N | N | N |
| NBEAL2 | high in P | 3.9 | 0.025551313 | 1.6 | 1488 | 77 | 51 | 108 | 146 | 297 | 383 | N | N | N | N | N | N |
| ELP2P | high in P | 3.9 | 0.025619502 | 1.6 | 1489 | 6 | 6 | 6 | 8 | 14 | 24 | NA | NA | N | N | N | N |
| RP1-177G6.2 | high in P | 2.9 | 0.025635186 | 1.6 | 1490 | 27 | 18 | 25 | 57 | 32 | 69 | N | P | N | N | N | N |
| LOC642587 | high in P | 4.8 | 0.025645414 | 1.6 | 1491 | 307 | 126 | 98 | 525 | 3189 | 432 | N | N | N | N | N | N |
| ZBTB32 | high in P | 8.6 | 0.025657688 | 1.6 | 1492 | 2 | 2 | 3 | 5 | 14 | 30 | N | N | N | N | N | N |
| SERPINC1 | high in P | 2.9 | 0.025691783 | 1.6 | 1493 | 3 | 11 | 4 | 15 | 15 | 24 | NA | NA | N | N | N | N |
| RAI1 | high in P | 3.0 | 0.025698602 | 1.6 | 1494 | 305 | 195 | 258 | 519 | 782 | 973 | N | N | P | N | N | N |
| TAF1D | high in P | 2.6 | 0.025733379 | 1.6 | 1495 | 311 | 270 | 392 | 708 | 730 | 951 | N | N | N | N | N | N |
| SLC12A3 | high in P | 2.8 | 0.02579134 | 1.6 | 1496 | 5 | 6 | 7 | 13 | 16 | 10 | N | N | N | N | N | N |
| FLJ45445 | high in P | 5.3 | 0.025806342 | 1.6 | 1497 | 243 | 106 | 6 | 545 | 497 | 495 | NA | NA | N | N | N | N |
| MCRS1 | high in P | 3.2 | 0.02581998 | 1.6 | 1498 | 61 | 41 | 33 | 208 | 105 | 78 | N | N | N | N | N | N |
| TRIM68 | high in P | 4.5 | 0.025897034 | 1.6 | 1499 | 12 | 6 | 6 | 22 | 11 | 26 | N | N | N | N | N | N |
| LSG1 | high in P | 3.9 | 0.025903853 | 1.6 | 1500 | 28 | 13 | 17 | 42 | 48 | 68 | N | N | N | N | N | N |
| ATP5S | high in P | 4.8 | 0.025910672 | 1.6 | 1501 | 6 | 8 | 14 | 20 | 18 | 22 | N | N | N | N | N | N |
| LOC400043 | high in P | 5.4 | 0.025942039 | 1.6 | 1502 | 370 | 98 | 111 | 608 | 545 | 681 | NA | NA | N | N | N | N |
| UBXN11 | high in P | 3.1 | 0.025976816 | 1.6 | 1503 | 33 | 27 | 53 | 63 | 115 | 100 | N | N | N | N | N | N |
| CCDC17 | high in P | 3.8 | 0.025983635 | 1.6 | 1504 | 12 | 7 | 8 | 21 | 19 | 52 | N | N | N | N | N | N |
| MYH14 | high in P | 3.4 | 0.026035459 | 1.6 | 1505 | 21 | 29 | 40 | 68 | 415 | 63 | N | P | N | N | N | N |
| C11orf92 | high in P | 4.0 | 0.026184112 | 1.6 | 1506 | 10 | 10 | 10 | 13 | 13 | 35 | NA | NA | N | N | N | N |
| STX4 | high in P | 3.1 | 0.026263212 | 1.6 | 1507 | 541 | 460 | 915 | 1650 | 1365 | 2331 | N | N | N | N | N | N |
| CLDN14 | high in P | 2.6 | 0.026270031 | 1.6 | 1508 | 4 | 12 | 7 | 14 | 23 | 17 | P | P | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | Nulliparous (NP) | | | | Parous (P) | | | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 NP | CD44+ N66 P | GeneBody NP Met NP | GeneBody Met P | Pro-moter Met NP | Pro-moter Met P |
|---|---|---|---|---|---|---|---|---|---|---|---|---|---|---|---|---|---|
| FAM189B | high in P | 3.4 | 0.026288442 | 1.6 | 1509 | 73 | 55 | 142 | 299 | 228 | 196 | NA | NA | N | N | N | N |
| SERTAD3 | high in P | 2.9 | 0.026308899 | 1.6 | 1510 | 33 | 16 | 29 | 45 | 63 | 78 | N | N | N | N | N | P |
| RAD1 | high in P | 2.6 | 0.026345721 | 1.6 | 1511 | 40 | 38 | 25 | 92 | 123 | 89 | N | N | N | N | N | N |
| PCNT | high in P | 3.0 | 0.026435049 | 1.6 | 1512 | 95 | 39 | 151 | 348 | 277 | 411 | N | N | N | N | N | N |
| CASP9 | high in P | 3.3 | 0.026441868 | 1.6 | 1513 | 84 | 11 | 62 | 157 | 181 | 254 | N | N | N | N | N | N |
| ADSSL1 | high in P | 5.6 | 0.026570065 | 1.6 | 1514 | 40 | 9 | 6 | 32 | 45 | 177 | N | N | N | N | N | N |
| KIAA1949 | high in P | 7.6 | 0.026576884 | 1.6 | 1515 | 6446 | 953 | 888 | 7209 | 7145 | 18747 | N | N | N | N | N | N |
| MAPKSP1 | high in P | 2.8 | 0.02662939 | 1.6 | 1516 | 72 | 191 | 176 | 374 | 522 | 413 | N | N | N | N | N | N |
| ATP2A1 | high in P | 5.4 | 0.026656666 | 1.6 | 1517 | 5 | 9 | 5 | 26 | 10 | 13 | N | N | N | N | N | N |
| WDR4 | high in P | 3.5 | 0.026670303 | 1.6 | 1518 | 40 | 31 | 25 | 54 | 120 | 143 | N | N | N | N | N | N |
| TEAD4 | high in P | 2.8 | 0.026756222 | 1.6 | 1519 | 124 | 144 | 204 | 281 | 536 | 473 | N | N | N | N | N | N |
| FAM116B | high in P | 3.2 | 0.026763041 | 1.6 | 1520 | 34 | 12 | 23 | 44 | 77 | 40 | N | N | N | N | N | N |
| DHX37 | high in P | 3.2 | 0.026857143 | 1.6 | 1521 | 39 | 64 | 117 | 204 | 361 | 160 | N | N | N | N | N | N |
| LOC348926 | high in P | 4.2 | 0.026863962 | 1.6 | 1522 | 6 | 6 | 6 | 22 | 11 | 9 | N | N | N | N | N | N |
| RNF215 | high in P | 3.2 | 0.02691715 | 1.6 | 1523 | 55 | 11 | 25 | 116 | 69 | 65 | N | N | N | N | N | N |
| FGR | high in P | 4.6 | 0.026939652 | 1.6 | 1524 | 18 | 6 | 18 | 36 | 20 | 68 | N | N | N | N | N | N |
| CD300C | high in P | 4.2 | 0.026975793 | 1.6 | 1525 | 2 | 2 | 5 | 14 | 8 | 30 | P | N | N | N | N | N |
| RRAGD | high in P | 2.9 | 0.027003069 | 1.6 | 1526 | 49 | 84 | 43 | 191 | 180 | 97 | N | N | N | N | N | N |
| MCCC2 | high in P | 3.7 | 0.027058984 | 1.6 | 1527 | 183 | 72 | 90 | 420 | 406 | 233 | N | N | N | N | N | N |
| LOC401093 | high in P | 2.8 | 0.027079441 | 1.6 | 1528 | 49 | 36 | 34 | 67 | 81 | 94 | NA | NA | N | N | N | N |
| MED19 | high in P | 2.9 | 0.027118309 | 1.6 | 1529 | 220 | 181 | 87 | 672 | 401 | 535 | N | N | N | N | N | N |
| CCDC22 | high in P | 3.4 | 0.027184453 | 1.6 | 1530 | 55 | 22 | 30 | 156 | 83 | 74 | N | N | N | N | N | N |
| ZNF323 | high in P | 3.9 | 0.027198091 | 1.6 | 1531 | 6 | 6 | 6 | 8 | 8 | 9 | N | N | N | N | N | N |
| NDUFB1 | high in P | 3.9 | 0.027198091 | 1.6 | 1532 | 4 | 4 | 4 | 6 | 7 | 7 | NA | NA | N | N | N | N |
| SLC19A1 | high in P | 3.2 | 0.027239686 | 1.6 | 1533 | 56 | 35 | 35 | 102 | 131 | 87 | N | N | N | N | N | N |
| LOC283856 | high in P | 2.8 | 0.027281964 | 1.6 | 1534 | 26 | 38 | 65 | 102 | 101 | 140 | P | P | N | N | N | N |
| NPM3 | high in P | 3.6 | 0.027288783 | 1.6 | 1535 | 347 | 101 | 167 | 600 | 855 | 486 | NA | NA | N | N | N | N |
| THAP7 | high in P | 3.4 | 0.027318104 | 1.6 | 1536 | 86 | 150 | 21 | 422 | 283 | 202 | N | N | N | N | N | N |
| RRAGA | high in P | 3.4 | 0.027384248 | 1.6 | 1537 | 896 | 382 | 461 | 2747 | 1546 | 1357 | NA | NA | N | N | N | N |
| EXD2 | high in P | 5.4 | 0.027431299 | 1.6 | 1538 | 84 | 18 | 18 | 165 | 121 | 69 | N | N | N | N | N | N |
| ISLR2 | high in P | 2.7 | 0.027444937 | 1.6 | 1539 | 48 | 32 | 28 | 93 | 61 | 75 | N | N | N | N | N | N |
| RANBP2 | high in P | 3.0 | 0.027451756 | 1.6 | 1540 | 39 | 50 | 41 | 91 | 86 | 136 | N | N | N | N | N | P |
| RHOF | high in P | 5.0 | 0.027586771 | 1.6 | 1541 | 15 | 13 | 17 | 21 | 101 | 84 | N | N | N | N | N | N |
| C6orf203 | high in P | 7.9 | 0.027599045 | 1.6 | 1542 | 2 | 2 | 2 | 18 | 14 | 10 | N | N | N | N | N | N |
| ZNF558 | high in P | 3.3 | 0.027635186 | 1.6 | 1543 | 3 | 27 | 18 | 78 | 46 | 40 | N | N | N | N | P | N |
| APBB3 | high in P | 6.5 | 0.027693147 | 1.6 | 1544 | 61 | 14 | 15 | 64 | 52 | 117 | N | N | N | N | N | N |
| LOC254559 | high in P | 6.0 | 0.027699966 | 1.6 | 1545 | 19 | 8 | 8 | 120 | 13 | 33 | N | N | N | N | N | N |
| MYLK3 | high in P | 3.3 | 0.027741562 | 1.6 | 1546 | 36 | 26 | 27 | 78 | 58 | 96 | P | P | N | N | N | N |
| DDX46 | high in P | 2.2 | 0.02774838 | 1.6 | 1547 | 72 | 97 | 86 | 215 | 201 | 159 | N | N | N | N | N | N |
| POMGNT1 | high in P | 3.9 | 0.02778043 | 1.6 | 1548 | 139 | 53 | 86 | 451 | 319 | 163 | N | N | N | N | N | N |
| MTA3 | high in P | 2.7 | 0.02781998 | 1.6 | 1549 | 169 | 62 | 127 | 272 | 316 | 396 | N | N | N | N | N | N |
| KIAA0101 | high in P | 2.9 | 0.027826798 | 1.6 | 1550 | 3 | 3 | 3 | 6 | 21 | 6 | N | N | N | N | P | N |
| WDR27 | high in P | 5.3 | 0.027903171 | 1.6 | 1551 | 9 | 14 | 9 | 55 | 14 | 65 | N | N | N | N | N | N |
| RAB3A | high in P | 8.7 | 0.028003409 | 1.6 | 1552 | 101 | 14 | 7 | 76 | 119 | 364 | N | N | N | N | N | N |

TABLE 15-continued

Genes that Are Differentially Methylated between Nulliparous and Parous CD44+ Breast Epithelial Cells

| Gene Symbol | expression pattern | Fold Change | p-value | log10 (p-val.) | Ranking | SAGE-seq Nulliparous (NP) CD44+ N48 | SAGE-seq Nulliparous (NP) CD44+ N58 | SAGE-seq Nulliparous (NP) CD44+ N43 | SAGE-seq Parous (P) CD44+ N37 | SAGE-seq Parous (P) CD44+ N39 | SAGE-seq Parous (P) CD44+ N40 | ChIP-seq NP CD44+ N74 | ChIP-seq P CD44+ N66 | MSDK-seq GeneBody NP Met | MSDK-seq GeneBody Met | MSDK-seq Pro-motor Met NP | MSDK-seq Pro-moter Met P |
|---|---|---|---|---|---|---|---|---|---|---|---|---|---|---|---|---|---|
| IDH3A | high in P | 2.5 | 0.028030003 | 1.6 | 1553 | 46 | 87 | 71 | 175 | 148 | 126 | N | N | N | N | N | N |
| RGS14 | high in P | 3.7 | 0.02805046 | 1.6 | 1554 | 62 | 15 | 17 | 45 | 142 | 153 | N | N | N | N | N | N |
| DENND1A | high in P | 3.8 | 0.028127514 | 1.6 | 1555 | 182 | 39 | 91 | 755 | 322 | 271 | N | N | N | N | N | N |
| KCTD13 | high in P | 3.0 | 0.028141152 | 1.6 | 1556 | 112 | 60 | 81 | 282 | 248 | 173 | N | N | N | N | N | N |
| FAM40B | high in P | 3.2 | 0.028160245 | 1.6 | 1557 | 28 | 17 | 23 | 37 | 59 | 57 | N | N | N | N | N | N |
| PARP16 | high in P | 3.6 | 0.028223662 | 1.5 | 1558 | 58 | 9 | 22 | 64 | 59 | 142 | P | N | N | N | P | N |
| DPYSL4 | high in P | 3.7 | 0.028275486 | 1.5 | 1559 | 95 | 36 | 58 | 125 | 195 | 244 | N | N | N | N | N | N |
| C19orf47 | high in P | 2.9 | 0.028282305 | 1.5 | 1560 | 18 | 15 | 30 | 38 | 41 | 57 | N | N | N | N | N | N |
| LOC339047 | high in P | 3.9 | 0.028351858 | 1.5 | 1561 | 8 | 21 | 93 | 32 | 57 | 87 | N | NA | N | N | N | N |
| RPTOR | high in P | 3.5 | 0.028418684 | 1.5 | 1562 | 77 | 30 | 93 | 203 | 290 | 148 | NA | N | N | N | N | N |
| RHD | high in P | 2.9 | 0.028555063 | 1.5 | 1563 | 75 | 63 | 107 | 190 | 172 | 185 | N | N | N | N | N | N |
| KIAA1755 | high in P | 3.0 | 0.028580293 | 1.5 | 1564 | 28 | 20 | 23 | 50 | 46 | 39 | N | N | N | N | N | N |
| C8orf73 | high in P | 10.2 | 0.028601432 | 1.5 | 1565 | 43 | 8 | 8 | 42 | 56 | 74 | N | N | N | N | N | N |
| MDK | high in P | 7.1 | 0.02861507 | 1.5 | 1566 | 650 | 86 | 233 | 641 | 1531 | 1894 | N | N | N | N | N | N |
| CCNL1 | high in P | 2.5 | 0.028630753 | 1.5 | 1567 | 542 | 393 | 581 | 1127 | 1415 | 2121 | N | N | N | N | N | N |
| POLD1 | high in P | 3.7 | 0.028637572 | 1.5 | 1568 | 36 | 12 | 28 | 84 | 73 | 63 | N | N | N | N | N | N |
| EHMT2 | high in P | 4.9 | 0.028644391 | 1.5 | 1569 | 176 | 25 | 61 | 492 | 222 | 250 | N | N | N | N | N | N |
| SLAMF1 | high in P | 3.0 | 0.02870849 | 1.5 | 1570 | 27 | 18 | 24 | 61 | 40 | 121 | N | N | N | N | N | N |
| SYN2 | high in P | 4.1 | 0.028715309 | 1.5 | 1571 | 25 | 13 | 19 | 32 | 64 | 53 | N | N | N | N | N | N |
| ASF1B | high in P | 4.5 | 0.028728946 | 1.5 | 1572 | 3 | 3 | 4 | 7 | 21 | 6 | N | N | N | N | N | N |
| HUNK | high in P | 3.5 | 0.028735765 | 1.5 | 1573 | 95 | 30 | 57 | 194 | 150 | 159 | N | N | N | N | N | N |
| FLJ42627 | high in P | 3.7 | 0.02882032 | 1.5 | 1574 | 42 | 40 | 52 | 104 | 119 | 128 | N | N | N | N | N | N |
| PPP1R9B | high in P | 5.2 | 0.028827139 | 1.5 | 1575 | 573 | 85 | 219 | 705 | 1045 | 1592 | N | N | N | N | N | N |
| FTSJ3 | high in P | 2.7 | 0.028840777 | 1.5 | 1576 | 66 | 116 | 98 | 284 | 189 | 284 | N | N | N | N | N | N |
| GDAP2 | high in P | 5.2 | 0.028941016 | 1.5 | 1577 | 52 | 27 | 35 | 104 | 119 | 93 | N | N | N | N | N | N |
| NHEDC2 | high in P | 4.4 | 0.02895329 | 1.5 | 1578 | 122 | 30 | 45 | 234 | 178 | 173 | N | N | N | N | N | N |
| NCOR1 | high in P | 2.6 | 0.028960109 | 1.5 | 1579 | 127 | 75 | 116 | 314 | 258 | 269 | N | P | N | N | P | N |
| AKIRIN2 | high in P | 2.3 | 0.028979202 | 1.5 | 1580 | 653 | 571 | 659 | 1341 | 1380 | 1964 | N | N | N | N | N | N |
| INPP5F | high in P | 2.4 | 0.029008524 | 1.5 | 1581 | 72 | 54 | 57 | 141 | 94 | 128 | N | N | N | N | N | N |
| IQCC | high in P | 2.7 | 0.029015343 | 1.5 | 1582 | 19 | 25 | 25 | 34 | 43 | 47 | N | N | N | N | N | N |
| SFRS16 | high in P | 3.7 | 0.029072622 | 1.5 | 1583 | 70 | 42 | 125 | 252 | 245 | 177 | N | N | N | N | N | N |
| PAFAH1B3 | high in P | 2.6 | 0.029095124 | 1.5 | 1584 | 25 | 14 | 24 | 47 | 49 | 34 | N | N | N | N | N | N |
| CYP2E1 | high in P | 3.1 | 0.029101943 | 1.5 | 1585 | 10 | 4 | 4 | 6 | 9 | 10 | N | P | N | N | N | N |
| GGA3 | high in P | 3.0 | 0.029140811 | 1.5 | 1586 | 12 | 24 | 41 | 71 | 78 | 50 | N | N | N | N | N | N |
| ASH1L | high in P | 2.7 | 0.029168769 | 1.5 | 1587 | 110 | 84 | 116 | 317 | 219 | 419 | N | N | N | N | N | N |
| UBE2Q1 | high in P | 2.6 | 0.029182407 | 1.5 | 1588 | 114 | 70 | 70 | 296 | 308 | 148 | N | N | N | N | N | N |
| SLC4A2 | high in P | 2.8 | 0.029221957 | 1.5 | 1589 | 65 | 115 | 62 | 311 | 172 | 184 | N | N | N | N | N | N |
| HM13 | high in P | 3.2 | 0.029237641 | 1.5 | 1590 | 206 | 110 | 145 | 758 | 493 | 299 | N | N | P | N | N | N |
| ADNP2 | high in P | 2.5 | 0.029253324 | 1.5 | 1591 | 80 | 73 | 109 | 217 | 197 | 240 | N | N | N | N | N | N |
| SLC22A23 | high in P | 3.8 | 0.029307876 | 1.5 | 1592 | 145 | 64 | 94 | 646 | 228 | 247 | N | N | N | N | N | N |
| POLN | high in P | 2.9 | 0.029329697 | 1.5 | 1593 | 5 | 5 | 5 | 9 | 10 | 8 | N | N | N | N | N | N |
| GPCPD1 | high in P | 2.5 | 0.029349472 | 1.5 | 1594 | 32 | 64 | 48 | 99 | 100 | 127 | N | N | N | N | N | N |
| CNBP | high in P | 3.1 | 0.029403341 | 1.5 | 1595 | 567 | 268 | 269 | 1039 | 975 | 1519 | NA | NA | N | N | N | N |
| RNF121 | high in P | 3.1 | 0.029425844 | 1.5 | 1596 | 9 | 14 | 11 | 41 | 23 | 19 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | Parous (P) | | | NP | | P | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| C3orf74 | high in P | 5.5 | 0.029441527 | 1.5 | 1597 | 18 | 7 | 8 | 29 | 21 | 18 | N | N | N | N | N | N |
| RELB | high in P | 2.8 | 0.029472895 | 1.5 | 1598 | 516 | 262 | 707 | 1596 | 1136 | 1560 | N | N | N | N | N | N |
| RANBP9 | high in P | 4.6 | 0.029551995 | 1.5 | 1599 | 471 | 128 | 192 | 917 | 575 | 1214 | N | N | N | N | N | N |
| DEF8 | high in P | 2.4 | 0.029573133 | 1.5 | 1600 | 139 | 142 | 158 | 376 | 284 | 435 | N | N | N | N | N | N |
| XIRP1 | high in P | 6.4 | 0.029601091 | 1.5 | 1601 | 16 | 40 | 55 | 46 | 213 | 306 | N | N | N | N | N | N |
| MRE11A | high in P | 4.2 | 0.029613365 | 1.5 | 1602 | 8 | 8 | 8 | 16 | 13 | 11 | N | N | N | N | N | N |
| SFRS2IP | high in P | 2.2 | 0.029687692 | 1.5 | 1603 | 32 | 84 | 94 | 196 | 178 | 198 | N | N | N | N | N | N |
| LAS1L | high in P | 2.5 | 0.029694511 | 1.5 | 1604 | 128 | 115 | 175 | 323 | 370 | 244 | N | N | N | N | N | N |
| FSD1 | high in P | 42.9 | 0.02972315 | 1.5 | 1605 | 5 | 5 | 5 | 56 | 5 | 61 | N | P | N | N | N | N |
| PPP1R13L | high in P | 3.2 | 0.029826798 | 1.5 | 1606 | 158 | 252 | 375 | 531 | 1985 | 765 | N | N | N | N | N | N |
| ZNF740 | high in P | 3.8 | 0.029924991 | 1.5 | 1607 | 19 | 15 | 14 | 43 | 29 | 24 | N | N | N | N | N | N |
| HNRNPH3 | high in P | 3.7 | 0.029993863 | 1.5 | 1608 | 587 | 413 | 560 | 1967 | 877 | 4395 | N | N | N | N | N | N |
| BTBD3 | high in P | 2.8 | 0.030000682 | 1.5 | 1609 | 14 | 9 | 12 | 29 | 24 | 18 | N | N | N | N | N | N |
| C20orf12 | high in P | 2.8 | 0.030077736 | 1.5 | 1610 | 7 | 13 | 8 | 28 | 21 | 18 | N | N | N | N | N | N |
| MLEC | high in P | 3.6 | 0.030105694 | 1.5 | 1611 | 777 | 295 | 303 | 1309 | 1113 | 1854 | N | N | N | N | N | N |
| FHL3 | high in P | 3.5 | 0.030112513 | 1.5 | 1612 | 400 | 78 | 258 | 662 | 935 | 865 | N | N | N | N | N | N |
| TNKS2 | high in P | 3.4 | 0.030189567 | 1.5 | 1613 | 101 | 103 | 105 | 184 | 417 | 387 | N | N | N | N | N | N |
| USP20 | high in P | 3.1 | 0.030203205 | 1.5 | 1614 | 20 | 51 | 37 | 105 | 61 | 111 | N | N | P | N | N | N |
| LIME1 | high in P | 3.7 | 0.030210024 | 1.5 | 1615 | 30 | 9 | 46 | 64 | 53 | 105 | N | N | N | N | N | N |
| BTBD10 | high in P | 2.3 | 0.030291851 | 1.5 | 1616 | 94 | 39 | 69 | 161 | 158 | 146 | N | N | N | N | N | N |
| DGKD | high in P | 3.2 | 0.030305489 | 1.5 | 1617 | 114 | 85 | 143 | 252 | 511 | 275 | N | N | N | N | N | N |
| TUFM | high in P | 3.5 | 0.030312308 | 1.5 | 1618 | 574 | 607 | 102 | 2098 | 1196 | 1408 | N | N | N | N | P | N |
| ZNF248 | high in P | 3.7 | 0.030333447 | 1.5 | 1619 | 13 | 16 | 36 | 57 | 38 | 133 | N | N | N | N | N | N |
| ATAD3A | high in P | 4.2 | 0.030358677 | 1.5 | 1620 | 45 | 51 | 119 | 212 | 248 | 147 | N | N | N | N | P | N |
| MLL4 | high in P | 3.1 | 0.030379134 | 1.5 | 1621 | 137 | 73 | 123 | 269 | 455 | 356 | N | N | N | N | N | N |
| LOH12CR2 | high in P | 2.9 | 0.030398227 | 1.5 | 1622 | 15 | 5 | 9 | 33 | 30 | 20 | N | N | N | N | N | N |
| APOD | high in P | 2.6 | 0.030405046 | 1.5 | 1623 | 19469 | 15851 | 20460 | 37057 | 50152 | 194951 | N | N | N | N | N | N |
| UBL4A | high in P | 4.2 | 0.030411865 | 1.5 | 1624 | 182 | 19 | 70 | 480 | 265 | 226 | N | N | N | N | N | N |
| GPATCH8 | high in P | 2.7 | 0.030447324 | 1.5 | 1625 | 22 | 34 | 40 | 91 | 94 | 99 | N | N | N | N | N | N |
| SLC13A4 | high in P | 3.3 | 0.030454143 | 1.5 | 1626 | 9 | 22 | 11 | 22 | 29 | 41 | P | P | N | N | N | N |
| LONP2 | high in P | 2.4 | 0.03046778 | 1.5 | 1627 | 55 | 60 | 74 | 114 | 121 | 157 | P | N | N | N | N | N |
| SEPX1 | high in P | 3.5 | 0.030474599 | 1.5 | 1628 | 52 | 44 | 31 | 242 | 133 | 57 | N | N | N | N | N | N |
| USH1G | high in P | 3.0 | 0.030503921 | 1.5 | 1629 | 9 | 13 | 19 | 22 | 45 | 35 | N | P | N | N | N | N |
| POU2F2 | high in P | 4.7 | 0.030531197 | 1.5 | 1630 | 11 | 32 | 23 | 145 | 35 | 193 | N | P | N | N | N | N |
| FAM110A | high in P | 3.5 | 0.030543471 | 1.5 | 1631 | 39 | 16 | 45 | 75 | 142 | 65 | N | N | N | N | N | N |
| ABHD3 | high in P | 4.1 | 0.030578929 | 1.5 | 1632 | 6 | 29 | 12 | 27 | 45 | 93 | N | N | N | N | N | N |
| LAYN | high in P | 2.8 | 0.03060675 | 1.5 | 1633 | 21 | 25 | 14 | 40 | 51 | 29 | N | N | N | N | N | N |
| RNF40 | high in P | 3.6 | 0.030621207 | 1.5 | 1634 | 34 | 23 | 28 | 107 | 71 | 69 | N | N | N | N | N | N |
| CSK | high in P | 2.6 | 0.03064371 | 1.5 | 1635 | 429 | 356 | 454 | 1212 | 1277 | 849 | N | N | N | N | N | N |
| FAM184B | high in P | 3.3 | 0.030656666 | 1.5 | 1636 | 442 | 330 | 625 | 993 | 1024 | 1933 | N | N | N | N | N | N |
| NFXL1 | high in P | 3.9 | 0.030713945 | 1.5 | 1637 | 10 | 15 | 19 | 48 | 48 | 18 | N | N | N | N | N | N |
| POLR2A | high in P | 4.3 | 0.030741902 | 1.5 | 1638 | 1476 | 600 | 466 | 3089 | 2098 | 2598 | N | N | N | N | N | N |
| THAP3 | high in P | 3.0 | 0.030767815 | 1.5 | 1639 | 5 | 22 | 35 | 63 | 92 | 43 | N | N | N | N | N | N |
| MRPS16 | high in P | 2.4 | 0.03080941 | 1.5 | 1640 | 129 | 112 | 158 | 312 | 410 | 319 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
| --- | --- | --- | --- | --- | --- | --- | --- | --- | --- | --- | --- | --- | --- | --- | --- | --- | --- |
| | | | | | Nulliparous (NP) | | | | Parous (P) | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| LOC284276 | high in P | 2.9 | 0.030831913 | 1.5 | 1641 | 4 | 4 | 4 | 15 | 7 | 13 | N | N | N | N | N | N |
| MAD2L1BP | high in P | 4.4 | 0.030855987 | 1.5 | 1642 | 43 | 11 | 48 | 250 | 58 | 152 | N | N | N | N | N | N |
| TMEM63C | high in P | 3.7 | 0.030866689 | 1.5 | 1643 | 6 | 6 | 8 | 11 | 27 | 14 | P | N | N | N | N | N |
| PCYOX1 | high in P | 8.7 | 0.03090283 | 1.5 | 1644 | 127 | 27 | 21 | 215 | 163 | 148 | N | N | N | N | N | N |
| HSPBAP1 | high in P | 4.7 | 0.030923287 | 1.5 | 1645 | 8 | 21 | 52 | 86 | 75 | 60 | N | N | N | N | N | N |
| PSPN | high in P | 3.4 | 0.030945107 | 1.5 | 1646 | 2 | 5 | 11 | 17 | 15 | 36 | N | N | N | N | N | N |
| TELO2 | high in P | 2.7 | 0.031008524 | 1.5 | 1647 | 27 | 35 | 55 | 139 | 92 | 64 | N | N | N | N | N | N |
| INPP4A | high in P | 2.8 | 0.031074668 | 1.5 | 1648 | 95 | 63 | 99 | 178 | 268 | 418 | N | N | N | N | N | N |
| MTMR10 | high in P | 2.9 | 0.031110808 | 1.5 | 1649 | 203 | 63 | 145 | 457 | 336 | 397 | N | N | N | N | N | N |
| HAPLN4 | high in P | 5.3 | 0.031124446 | 1.5 | 1650 | 7 | 7 | 7 | 33 | 28 | 7 | N | N | N | N | N | N |
| ALDOA | high in P | 2.7 | 0.031155131 | 1.5 | 1651 | 4194 | 3317 | 6045 | 16150 | 12581 | 8407 | N | N | N | N | N | N |
| TAF1A | high in P | 3.4 | 0.031248551 | 1.5 | 1652 | 13 | 10 | 5 | 35 | 15 | 14 | N | N | N | N | N | N |
| LIPE | high in P | 4.8 | 0.031289465 | 1.5 | 1653 | 25 | 13 | 17 | 53 | 43 | 21 | N | N | N | N | N | N |
| AGFG2 | high in P | 2.3 | 0.031318104 | 1.5 | 1654 | 25 | 19 | 23 | 57 | 41 | 42 | N | P | N | N | N | N |
| DENND5A | high in P | 2.8 | 0.031333788 | 1.5 | 1655 | 580 | 367 | 235 | 1092 | 922 | 1561 | N | N | N | N | N | N |
| LOC440335 | high in P | 6.8 | 0.031366519 | 1.5 | 1656 | 19 | 31 | 93 | 121 | 839 | 87 | NA | NA | N | N | N | N |
| C1orf9 | high in P | 2.5 | 0.031440846 | 1.5 | 1657 | 30 | 59 | 57 | 142 | 104 | 79 | N | N | N | N | N | N |
| PRRX2 | high in P | 3.3 | 0.03145312 | 1.5 | 1658 | 777 | 168 | 515 | 1487 | 1086 | 2633 | N | N | N | N | N | N |
| FXYD2 | high in P | 4.2 | 0.031459939 | 1.5 | 1659 | 19 | 9 | 13 | 70 | 47 | 24 | N | N | N | N | P | N |
| CYTH2 | high in P | 3.0 | 0.031466758 | 1.5 | 1660 | 610 | 349 | 304 | 1076 | 1304 | 1002 | N | N | N | N | N | N |
| CINP | high in P | 3.1 | 0.031486533 | 1.5 | 1661 | 60 | 18 | 28 | 80 | 151 | 60 | N | N | N | N | N | N |
| KIAA0892 | high in P | 2.3 | 0.031529492 | 1.5 | 1662 | 209 | 166 | 190 | 734 | 528 | 379 | N | N | N | N | N | N |
| LPAR2 | high in P | 3.1 | 0.03154313 | 1.5 | 1663 | 51 | 42 | 34 | 117 | 110 | 74 | N | N | N | N | N | N |
| QPRT | high in P | 3.1 | 0.03161882 | 1.5 | 1664 | 52 | 19 | 16 | 97 | 51 | 90 | N | N | N | N | N | N |
| BALAP2 | high in P | 3.6 | 0.031641323 | 1.5 | 1665 | 233 | 314 | 546 | 732 | 1388 | 2118 | N | N | N | N | N | N |
| WDR77 | high in P | 2.4 | 0.031749744 | 1.5 | 1666 | 103 | 85 | 103 | 231 | 489 | 187 | N | N | N | N | N | N |
| RNF207 | high in P | 4.2 | 0.031801568 | 1.5 | 1667 | 17 | 17 | 13 | 49 | 23 | 68 | NA | NA | N | N | N | N |
| CHIC1 | high in P | 2.8 | 0.031828162 | 1.5 | 1668 | 19 | 26 | 18 | 31 | 54 | 47 | N | N | N | N | N | N |
| EXOSC2 | high in P | 2.8 | 0.031834981 | 1.5 | 1669 | 51 | 98 | 66 | 141 | 151 | 153 | N | N | N | N | N | N |
| PKLR | high in P | 4.7 | 0.031918173 | 1.5 | 1670 | 4 | 4 | 5 | 6 | 15 | 10 | N | N | N | N | N | N |
| TRAPPC2 | high in P | 3.4 | 0.03196045 | 1.5 | 1671 | 17 | 12 | 12 | 20 | 33 | 51 | N | N | N | N | N | N |
| TMBIM1 | high in P | 3.0 | 0.031996591 | 1.5 | 1672 | 1506 | 931 | 2171 | 6123 | 3645 | 3117 | NA | N | N | N | N | N |
| ESRP2 | high in P | 3.1 | 0.03202523 | 1.5 | 1673 | 12 | 18 | 31 | 37 | 275 | 59 | N | N | N | N | N | N |
| EP400 | high in P | 2.4 | 0.032059325 | 1.5 | 1674 | 120 | 124 | 83 | 226 | 246 | 293 | NA | NA | N | N | N | N |
| CENPBD1 | high in P | 3.2 | 0.032078418 | 1.5 | 1675 | 9 | 9 | 13 | 15 | 18 | 22 | NA | NA | N | N | N | N |
| PTAR1 | high in P | 2.1 | 0.032092056 | 1.5 | 1676 | 114 | 117 | 122 | 274 | 217 | 260 | N | N | N | N | N | N |
| SSR2 | high in P | 3.0 | 0.032105694 | 1.5 | 1677 | 1275 | 506 | 735 | 3714 | 2036 | 1816 | NA | NA | N | N | N | N |
| HIVEP1 | high in P | 3.2 | 0.032136379 | 1.5 | 1678 | 66 | 45 | 26 | 102 | 81 | 176 | N | N | N | N | N | N |
| RRP15 | high in P | 2.2 | 0.032143198 | 1.5 | 1679 | 51 | 50 | 49 | 110 | 122 | 103 | N | N | N | N | N | N |
| ZNF222 | high in P | 6.4 | 0.032177293 | 1.5 | 1680 | 2 | 14 | 2 | 22 | 18 | 12 | N | P | N | N | N | N |
| SBFIP1 | high in P | 2.5 | 0.03219775 | 1.5 | 1681 | 252 | 96 | 186 | 415 | 522 | 413 | NA | NA | N | N | N | N |
| ZNF614 | high in P | 4.2 | 0.03225162 | 1.5 | 1682 | 13 | 45 | 17 | 59 | 73 | 53 | N | N | N | N | N | N |
| TRAF7 | high in P | 3.3 | 0.032289124 | 1.5 | 1683 | 707 | 247 | 274 | 1630 | 1509 | 859 | N | N | N | N | N | N |
| WDR34 | high in P | 4.4 | 0.03241802 | 1.5 | 1684 | 73 | 15 | 40 | 155 | 160 | 69 | N | N | N | N | N | N |

TABLE 15-continued

Genes that Are Differentially Methylated between Nulliparous and Parous CD44+ Breast Epithelial Cells

| | | | | | SAGE-seq | | | | | | | | ChIP-seq | | | | MSDK-seq | | |
|---|---|---|---|---|---|---|---|---|---|---|---|---|---|---|---|---|---|---|---|
| | | | | | | Nulliparous (NP) | | | | Parous (P) | | | | NP | | P | | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
|---|---|---|---|---|---|---|---|---|---|---|---|---|---|---|---|---|---|
| LOC100128239 | high in P | 2.8 | 0.03243164 | 1.5 | 1685 | 5 | 5 | 5 | 13 | 8 | 15 | NA | NA | N | N | N | N |
| PCDHB19P | high in P | 8.4 | 0.032446642 | 1.5 | 1686 | 24 | 8 | 8 | 28 | 24 | 34 | N | N | N | N | N | N |
| GCET2 | high in P | 3.9 | 0.032497784 | 1.5 | 1687 | 8 | 8 | 8 | 10 | 24 | 11 | N | P | N | N | N | N |
| UMPS | high in P | 3.2 | 0.032504603 | 1.5 | 1688 | 5 | 41 | 20 | 54 | 81 | 83 | P | N | N | N | N | N |
| SDS | high in P | 8.8 | 0.032540061 | 1.5 | 1689 | 3 | 13 | 8 | 26 | 12 | 161 | N | N | N | N | N | N |
| PBX3 | high in P | 5.0 | 0.032555745 | 1.5 | 1690 | 36 | 27 | 12 | 40 | 93 | 109 | N | N | N | N | N | N |
| ANKS4B | high in P | 3.0 | 0.03258643 | 1.5 | 1691 | 282 | 238 | 490 | 856 | 1072 | 637 | N | N | N | N | N | N |
| SLC43A1 | high in P | 3.5 | 0.032638936 | 1.5 | 1692 | 47 | 31 | 67 | 145 | 80 | 212 | N | N | P | N | N | N |
| DIO3OS | high in P | 4.6 | 0.03270508 | 1.5 | 1693 | 3 | 3 | 7 | 24 | 6 | 32 | N | N | N | N | N | N |
| PTBP1 | high in P | 5.8 | 0.032730992 | 1.5 | 1694 | 1454 | 212 | 327 | 2014 | 2158 | 2010 | N | N | N | N | N | N |
| VEZF1 | high in P | 2.3 | 0.032737811 | 1.5 | 1695 | 250 | 219 | 221 | 517 | 567 | 817 | N | N | N | N | N | N |
| PDK1 | high in P | 2.2 | 0.03260314 | 1.5 | 1696 | 70 | 58 | 72 | 155 | 123 | 104 | N | N | N | N | N | N |
| MINA | high in P | 3.3 | 0.032767133 | 1.5 | 1697 | 103 | 63 | 29 | 185 | 167 | 183 | N | N | P | N | P | N |
| PPP3CC | high in P | 3.4 | 0.032797136 | 1.5 | 1698 | 270 | 117 | 140 | 639 | 439 | 357 | N | N | N | N | N | N |
| TAF11 | high in P | 2.6 | 0.032842823 | 1.5 | 1699 | 165 | 169 | 92 | 394 | 252 | 395 | N | N | N | N | N | N |
| SH2D3A | high in P | 2.9 | 0.032895329 | 1.5 | 1700 | 25 | 34 | 27 | 44 | 81 | 109 | N | N | N | N | N | N |
| UBE2Q2P3 | high in P | 6.2 | 0.032902148 | 1.5 | 1701 | NA | NA | NA | NA | NA | NA | NA | NA | N | N | N | N |
| SRFBP1 | high in P | 2.7 | 0.03298193 | 1.5 | 1702 | 17 | 30 | 19 | 53 | 67 | 43 | N | N | N | N | N | N |
| CTNS | high in P | 4.5 | 0.033004432 | 1.5 | 1703 | 71 | 22 | 29 | 152 | 123 | 69 | N | N | N | N | N | N |
| THG1L | high in P | 3.2 | 0.033043982 | 1.5 | 1704 | 14 | 15 | 18 | 81 | 45 | 21 | N | N | N | N | N | N |
| CADPS2 | high in P | 4.0 | 0.033138084 | 1.5 | 1705 | 17 | 16 | 12 | 26 | 37 | 46 | N | N | N | N | N | N |
| MAN1A1 | high in P | 3.4 | 0.03315104 | 1.5 | 1706 | 104 | 39 | 51 | 177 | 146 | 255 | N | N | N | N | N | N |
| MOV10L1 | high in P | 2.7 | 0.033171497 | 1.5 | 1707 | 1 | 1 | 1 | 3 | 14 | 4 | P | N | N | N | N | N |
| C6orf173 | high in P | 3.3 | 0.033178316 | 1.5 | 1708 | NA | NA | NA | NA | NA | NA | NA | NA | N | N | N | N |
| NPHP4 | high in P | 3.0 | 0.033325559 | 1.5 | 1709 | 31 | 17 | 37 | 57 | 50 | 76 | N | N | N | N | N | N |
| SERPINB6 | high in P | 2.9 | 0.033490624 | 1.5 | 1710 | 489 | 144 | 391 | 1450 | 778 | 864 | N | N | N | N | N | N |
| ARHGEF2 | high in P | 2.4 | 0.03353222 | 1.5 | 1711 | 127 | 130 | 204 | 333 | 358 | 481 | N | N | N | N | N | N |
| ALOXE3 | high in P | 2.8 | 0.033562905 | 1.5 | 1712 | 9 | 9 | 10 | 12 | 37 | 15 | N | N | N | N | N | N |
| PRDX3 | high in P | 3.9 | 0.033569724 | 1.5 | 1713 | 460 | 136 | 224 | 2080 | 859 | 496 | P | N | N | N | N | N |
| PPP1R16B | high in P | 6.1 | 0.033643369 | 1.5 | 1714 | 61 | 15 | 19 | 57 | 58 | 382 | N | N | N | N | N | N |
| UHRF1 | high in P | 3.2 | 0.033678145 | 1.5 | 1715 | 35 | 17 | 37 | 46 | 79 | 104 | N | P | P | N | P | N |
| CR1 | high in P | 3.7 | 0.033691783 | 1.5 | 1716 | 5 | 6 | 8 | 31 | 14 | 10 | P | N | N | N | N | N |
| SLC15A2 | high in P | 3.5 | 0.03378793 | 1.5 | 1717 | 13 | 15 | 18 | 41 | 25 | 38 | N | N | N | N | N | N |
| IVD | high in P | 2.8 | 0.033837709 | 1.5 | 1718 | 35 | 36 | 45 | 128 | 95 | 76 | NA | NA | N | N | N | N |
| SEC22B | high in P | 2.8 | 0.033869076 | 1.5 | 1719 | 207 | 78 | 137 | 617 | 354 | 295 | P | N | N | N | P | N |
| BCAT2 | high in P | 3.1 | 0.033897034 | 1.5 | 1720 | 181 | 79 | 207 | 365 | 350 | 590 | P | N | N | N | N | N |
| ATP5L2 | high in P | 3.9 | 0.033978861 | 1.5 | 1721 | 9 | 2 | 3 | 8 | 10 | 5 | NA | NA | N | N | N | N |
| 10-Sep | high in P | 2.9 | 0.033988568 | 1.5 | 1722 | 3583 | 1238 | 2858 | 10496 | 7420 | 4915 | NA | NA | N | N | N | N |
| HELB | high in P | 5.0 | 0.034042278 | 1.5 | 1723 | 14 | 8 | 8 | 16 | 29 | 18 | N | N | N | N | N | N |
| TCEA3 | high in P | 2.8 | 0.034083191 | 1.5 | 1724 | 6 | 13 | 16 | 22 | 26 | 38 | N | N | N | N | N | N |
| UBL7 | high in P | 3.2 | 0.034110467 | 1.5 | 1725 | 87 | 29 | 73 | 272 | 140 | 124 | N | N | N | N | N | N |
| DFFB | high in P | 3.4 | 0.034124105 | 1.5 | 1726 | 6 | 24 | 8 | 39 | 22 | 31 | N | N | N | N | N | N |
| RAI14 | high in P | 4.1 | 0.034216843 | 1.5 | 1727 | 367 | 91 | 125 | 741 | 926 | 353 | N | N | N | N | N | N |
| C17orf80 | high in P | 4.2 | 0.0348776 | 1.5 | 1728 | 40 | 11 | 18 | 33 | 50 | 55 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | Nulliparous (NP) | | | | Parous (P) | | | | NP | P | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met | P |
| KLHL26 | high in P | 2.8 | 0.034306853 | 1.5 | 1729 | 25 | 35 | 47 | 84 | 60 | 222 | N | N | N | N | N | N | N |
| ALDH1L2 | high in P | 3.2 | 0.034336175 | 1.5 | 1730 | 52 | 25 | 31 | 70 | 83 | 72 | N | N | N | N | N | N | N |
| KLB | high in P | 4.9 | 0.034357995 | 1.5 | 1731 | 9 | 11 | 16 | 17 | 33 | 86 | N | N | N | N | N | N | N |
| C14orf79 | high in P | 3.7 | 0.034412547 | 1.5 | 1732 | 21 | 11 | 6 | 52 | 32 | 15 | N | N | N | N | N | N | N |
| FCGBP | high in P | 5.3 | 0.034433004 | 1.5 | 1733 | 8 | 8 | 21 | 34 | 15 | 109 | N | P | N | N | N | N | N |
| SSSCA1 | high in P | 2.7 | 0.034488919 | 1.5 | 1734 | 102 | 105 | 200 | 479 | 521 | 210 | N | N | N | N | N | N | N |
| CRBN | high in P | 2.1 | 0.034585748 | 1.5 | 1735 | 36 | 48 | 46 | 84 | 74 | 100 | N | N | N | N | N | N | N |
| TULP4 | high in P | 2.7 | 0.034627344 | 1.5 | 1736 | 67 | 59 | 94 | 151 | 240 | 164 | N | N | N | N | N | N | N |
| MEGF8 | high in P | 3.7 | 0.03477327 | 1.5 | 1737 | 53 | 36 | 43 | 151 | 113 | 81 | N | N | N | N | N | N | N |
| IL23A | high in P | 4.9 | 0.034786226 | 1.5 | 1738 | 11 | 23 | 43 | 96 | 40 | 100 | N | N | N | N | N | N | N |
| C15orf63 | high in P | 2.7 | 0.034814183 | 1.5 | 1739 | 121 | 301 | 185 | 420 | 654 | 478 | NA | NA | N | N | N | N | N |
| KIAA2018 | high in P | 4.6 | 0.034884419 | 1.5 | 1740 | 190 | 87 | 42 | 418 | 260 | 326 | N | N | N | N | N | N | N |
| ZNF276 | high in P | 3.1 | 0.034951926 | 1.5 | 1741 | 54 | 40 | 51 | 95 | 141 | 166 | N | N | N | N | N | N | N |
| ASB16 | high in P | 4.0 | 0.034958745 | 1.5 | 1742 | 10 | 5 | 8 | 43 | 35 | 10 | N | N | N | N | N | N | N |
| ARID3B | high in P | 2.8 | 0.034977838 | 1.5 | 1743 | 9 | 11 | 13 | 26 | 23 | 17 | N | P | N | N | N | N | N |
| STARD5 | high in P | 4.3 | 0.035016706 | 1.5 | 1744 | 51 | 5 | 15 | 52 | 41 | 127 | N | N | N | N | N | N | N |
| C1orf21 | high in P | 2.8 | 0.035045346 | 1.5 | 1745 | 423 | 228 | 241 | 682 | 725 | 854 | N | N | N | N | N | N | N |
| FAM159A | high in P | 4.5 | 0.035058984 | 1.5 | 1746 | 2 | 2 | 3 | 7 | 5 | 39 | N | N | N | N | N | N | N |
| NCRNA00114 | high in P | 6.5 | 0.035071258 | 1.5 | 1747 | 18 | 2 | 2 | 36 | 26 | 7 | NA | NA | N | N | N | N | N |
| FBXL18 | high in P | 4.0 | 0.035112172 | 1.5 | 1748 | 39 | 39 | 38 | 91 | 95 | 147 | N | N | N | N | N | N | N |
| MFSD11 | high in P | 5.2 | 0.035132629 | 1.5 | 1749 | 146 | 26 | 42 | 215 | 170 | 209 | N | N | N | N | N | N | N |
| TUSC4 | high in P | 2.8 | 0.035256052 | 1.5 | 1750 | NA | NA | NA | NA | NA | NA | NA | N | N | N | N | N | N |
| ZNF668 | high in P | 4.0 | 0.035299011 | 1.5 | 1751 | 35 | 29 | 92 | 122 | 115 | 117 | N | N | N | N | N | N | N |
| NDUFA3 | high in P | 3.6 | 0.035324923 | 1.5 | 1752 | 301 | 99 | 145 | 1062 | 766 | 258 | P | N | N | N | N | N | N |
| C10orf67 | high in P | 3.2 | 0.035347426 | 1.5 | 1753 | 9 | 9 | 9 | 29 | 14 | 12 | P | P | N | N | N | N | N |
| USF2 | high in P | 4.0 | 0.0354388 | 1.5 | 1754 | 205 | 62 | 73 | 397 | 236 | 309 | N | N | N | N | N | N | N |
| ABRA | high in P | 4.4 | 0.035466758 | 1.5 | 1755 | 28 | 3 | 22 | 22 | 89 | 72 | N | N | N | N | N | N | N |
| ZBTB8OS | high in P | 5.2 | 0.035487214 | 1.5 | 1756 | 11 | 19 | 14 | 83 | 37 | 18 | N | N | N | N | N | N | N |
| LOC100133957 | high in P | 3.4 | 0.035511763 | 1.5 | 1757 | 69 | 19 | 34 | 132 | 72 | 100 | NA | NA | N | N | N | N | N |
| PCYT1A | high in P | 2.8 | 0.035563632 | 1.4 | 1758 | 5 | 5 | 6 | 9 | 10 | 30 | N | N | N | N | N | N | N |
| BRSK2 | high in P | 3.6 | 0.035610638 | 1.4 | 1759 | 4 | 4 | 5 | 31 | 15 | 7 | P | N | N | N | N | N | N |
| HARS | high in P | 2.6 | 0.035629731 | 1.4 | 1760 | 131 | 85 | 171 | 297 | 421 | 244 | N | N | N | N | N | N | N |
| MRPS26 | high in P | 2.7 | 0.035652233 | 1.4 | 1761 | 288 | 288 | 177 | 569 | 737 | 451 | N | N | N | N | N | N | N |
| CLASP1 | high in P | 2.5 | 0.035659052 | 1.4 | 1762 | 63 | 69 | 96 | 313 | 153 | 184 | N | N | N | N | N | N | N |
| TAF8 | high in P | 3.1 | 0.035801568 | 1.4 | 1763 | 20 | 54 | 25 | 87 | 65 | 71 | N | N | N | N | N | N | N |
| BBS4 | high in P | 2.4 | 0.035837027 | 1.4 | 1764 | 21 | 14 | 19 | 38 | 23 | 28 | N | N | N | N | N | N | N |
| MSH5 | high in P | 2.8 | 0.035843846 | 1.4 | 1765 | 7 | 7 | 8 | 14 | 10 | 18 | N | N | N | N | N | N | N |
| NFYA | high in P | 2.6 | 0.035907262 | 1.4 | 1766 | 342 | 129 | 177 | 645 | 500 | 773 | N | N | N | N | N | P | N |
| FAM125A | high in P | 3.3 | 0.035938629 | 1.4 | 1767 | 59 | 33 | 73 | 236 | 112 | 89 | N | N | N | N | N | N | N |
| PPIL2 | high in P | 2.8 | 0.035969997 | 1.4 | 1768 | 80 | 36 | 102 | 238 | 208 | 121 | N | N | N | N | N | N | N |
| ZDHHC11 | high in P | 3.0 | 0.035983635 | 1.4 | 1769 | 6 | 17 | 13 | 27 | 18 | 36 | N | P | N | N | N | N | N |
| CLIC2 | high in P | 2.4 | 0.035990453 | 1.4 | 1770 | 84 | 78 | 92 | 211 | 163 | 572 | N | N | N | N | N | N | P |
| SLAMF7 | high in P | 3.8 | 0.036006137 | 1.4 | 1771 | 4 | 4 | 6 | 21 | 7 | 20 | N | P | N | N | N | N | P |
| SLC34A2 | high in P | 5.5 | 0.036026594 | 1.4 | 1772 | 13 | 70 | 126 | 259 | 2106 | 129 | P | P | N | N | N | N | P |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | | Nulliparous (NP) | | | | Parous (P) | | | NP | | P | | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-motor Met |
| PPEF2 | high in P | 3.2 | 0.036033413 | 1.4 | 1773 | 4 | 12 | 5 | 14 | 13 | 22 | N | N | P | N | N | N |
| PSCA | high in P | 8.4 | 0.036062734 | 1.4 | 1774 | 4 | 4 | 4 | 4 | 46 | 12 | N | N | N | N | N | N |
| CUL4A | high in P | 3.4 | 0.036092738 | 1.4 | 1775 | 206 | 159 | 458 | 631 | 910 | 943 | N | N | N | N | N | N |
| ASZ1 | high in P | 3.5 | 0.036099557 | 1.4 | 1776 | 20 | 15 | 40 | 61 | 53 | 47 | N | N | N | N | N | N |
| HOXC8 | high in P | 3.5 | 0.036137743 | 1.4 | 1777 | 194 | 51 | 38 | 654 | 102 | 550 | N | N | N | N | N | N |
| TAOK2 | high in P | 2.5 | 0.036260484 | 1.4 | 1778 | 113 | 80 | 137 | 243 | 366 | 280 | N | N | N | N | N | N |
| C4orf10 | high in P | 3.7 | 0.03645687 | 1.4 | 1779 | 53 | 18 | 21 | 80 | 48 | 96 | N | N | N | N | N | N |
| TMC5 | high in P | 2.6 | 0.036477327 | 1.4 | 1780 | 34 | 36 | 60 | 85 | 94 | 82 | N | N | N | N | N | N |
| HCN2 | high in P | 2.9 | 0.036497784 | 1.4 | 1781 | 7 | 8 | 10 | 11 | 19 | 83 | P | P | N | N | N | N |
| XAF1 | high in P | 4.0 | 0.036563928 | 1.4 | 1782 | 36 | 22 | 25 | 46 | 46 | 133 | N | N | N | N | N | N |
| BRSK1 | high in P | 3.1 | 0.036610297 | 1.4 | 1783 | 43 | 20 | 22 | 141 | 41 | 86 | N | N | N | N | N | N |
| IRF5 | high in P | 2.7 | 0.036638936 | 1.4 | 1784 | 194 | 88 | 123 | 319 | 348 | 299 | N | N | N | N | N | N |
| RHBDF2 | high in P | 2.8 | 0.036664848 | 1.4 | 1785 | 9 | 12 | 16 | 23 | 53 | 22 | NA | NA | N | N | N | N |
| KRT80 | high in P | 3.9 | 0.036702353 | 1.4 | 1786 | 25 | 50 | 90 | 100 | 445 | 164 | N | N | N | N | N | N |
| NCRNA00174 | high in P | 3.2 | 0.036722128 | 1.4 | 1787 | 13 | 14 | 14 | 22 | 20 | 31 | N | N | N | N | N | N |
| TLN2 | high in P | 2.7 | 0.036768496 | 1.4 | 1788 | 25 | 39 | 27 | 88 | 47 | 96 | NA | NA | N | N | N | N |
| PELP1 | high in P | 2.5 | 0.036869417 | 1.4 | 1789 | 368 | 347 | 234 | 828 | 1113 | 553 | N | N | N | N | N | N |
| ABCA7 | high in P | 2.7 | 0.036975793 | 1.4 | 1790 | 28 | 32 | 37 | 66 | 56 | 62 | N | N | N | N | N | N |
| HNRPLL | high in P | 2.2 | 0.036982612 | 1.4 | 1791 | 126 | 98 | 109 | 256 | 221 | 401 | N | N | N | N | N | N |
| FAM38A | high in P | 2.9 | 0.036998295 | 1.4 | 1792 | 155 | 283 | 513 | 672 | 976 | 1109 | NA | NA | N | N | N | N |
| NLRP1 | high in P | 4.3 | 0.037011933 | 1.4 | 1793 | 39 | 17 | 17 | 60 | 58 | 93 | N | N | N | N | N | N |
| SPATA2 | high in P | 2.2 | 0.037041255 | 1.4 | 1794 | 161 | 134 | 105 | 340 | 286 | 296 | N | N | N | N | N | N |
| FLJ44635 | high in P | 3.1 | 0.037110808 | 1.4 | 1795 | 6 | 9 | 11 | 14 | 20 | 22 | N | P | N | P | N | N |
| RNF145 | high in P | 2.4 | 0.037131947 | 1.4 | 1796 | 368 | 507 | 318 | 814 | 958 | 1316 | N | N | N | N | N | N |
| TBCD | high in P | 2.6 | 0.037138766 | 1.4 | 1797 | 13 | 21 | 30 | 55 | 35 | 71 | N | N | N | N | N | N |
| PSMB7 | high in P | 3.2 | 0.037284691 | 1.4 | 1798 | 445 | 850 | 264 | 2201 | 945 | 1448 | N | N | N | N | N | N |
| TMEM104 | high in P | 3.1 | 0.037306512 | 1.4 | 1799 | 32 | 25 | 35 | 134 | 81 | 38 | N | N | N | N | N | N |
| FAM100A | high in P | 3.4 | 0.03732015 | 1.4 | 1800 | 98 | 168 | 368 | 415 | 630 | 935 | N | N | N | N | N | N |
| NLRP12 | high in P | 2.4 | 0.037326969 | 1.4 | 1801 | 31 | 27 | 38 | 58 | 55 | 78 | N | N | N | N | N | N |
| MANBA | high in P | 4.7 | 0.037333788 | 1.4 | 1802 | 7 | 7 | 7 | 15 | 7 | 18 | N | N | N | N | N | N |
| PER1 | high in P | 3.1 | 0.037364473 | 1.4 | 1803 | 960 | 691 | 2345 | 5071 | 2194 | 5545 | NA | NA | N | N | N | N |
| CCDC136 | high in P | 2.8 | 0.03745312 | 1.4 | 1804 | 31 | 20 | 27 | 34 | 33 | 61 | N | N | N | N | N | N |
| CSPP1 | high in P | 3.5 | 0.037480395 | 1.4 | 1805 | 17 | 58 | 52 | 63 | 164 | 161 | N | N | N | N | N | N |
| LRRC33 | high in P | 4.0 | 0.037569724 | 1.4 | 1806 | 3 | 3 | 4 | 9 | 6 | 24 | N | N | N | N | N | N |
| PLCB3 | high in P | 5.1 | 0.037617457 | 1.4 | 1807 | 24 | 8 | 9 | 38 | 17 | 28 | N | N | N | N | N | N |
| ZBTB7C | high in P | 6.0 | 0.037648142 | 1.4 | 1808 | 97 | 22 | 18 | 50 | 138 | 201 | N | P | N | N | N | N |
| VAMP1 | high in P | 2.7 | 0.037699284 | 1.4 | 1809 | 22 | 20 | 15 | 34 | 24 | 45 | N | N | N | N | N | N |
| PER1 | high in P | 2.9 | 0.037739516 | 1.4 | 1810 | 59 | 38 | 36 | 90 | 83 | 309 | N | N | N | N | N | N |
| LOC349196 | high in P | 3.3 | 0.037800205 | 1.4 | 1811 | 33 | 19 | 50 | 82 | 100 | 45 | N | N | N | N | N | N |
| NOL11 | high in P | 4.3 | 0.037939993 | 1.4 | 1812 | 6 | 6 | 6 | 11 | 15 | 6 | NA | NA | N | N | N | N |
| TTC39A | high in P | 6.5 | 0.037946812 | 1.4 | 1813 | 246 | 13 | 58 | 424 | 256 | 306 | N | N | N | N | N | N |
| TIE1 | high in P | 4.0 | 0.037987044 | 1.4 | 1814 | 40 | 25 | 17 | 165 | 33 | 77 | N | P | N | N | N | N |
| PORCN | high in P | 2.9 | 0.038035459 | 1.4 | 1815 | 6 | 12 | 7 | 22 | 18 | 12 | N | N | N | N | N | N |
| NUAK2 | high in P | 3.7 | 0.038057961 | 1.4 | 1816 | 34 | 27 | 32 | 64 | 64 | 59 | N | N | N | N | N | N |
| MACC1 | | | | | | | | | | | | | | | | | |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | Nulliparous (NP) | | | | Parous (P) | | | NP | P | | NP | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| EMR1 | high in P | 8.6 | 0.03806478 | 1.4 | 1817 | 2 | 2 | 2 | 10 | 2 | 117 | N | P | N | N | N | N |
| C7orf40 | high in P | 2.1 | 0.038071599 | 1.4 | 1818 | 792 | 646 | 751 | 1278 | 1693 | 1595 | N | N | N | N | N | N |
| R3HDM1 | high in P | 3.7 | 0.038162973 | 1.4 | 1819 | 17 | 11 | 12 | 20 | 40 | 18 | N | N | N | N | N | N |
| SLC25A3 | high in P | 3.2 | 0.038169792 | 1.4 | 1820 | 275 | 90 | 155 | 539 | 477 | 338 | N | N | N | N | N | N |
| DOCK7 | high in P | 2.5 | 0.038176611 | 1.4 | 1821 | 26 | 39 | 52 | 66 | 91 | 73 | N | N | N | N | N | N |
| THTPA | high in P | 3.9 | 0.038226389 | 1.4 | 1822 | 30 | 6 | 10 | 82 | 35 | 20 | N | N | N | N | N | N |
| DYSFIP1 | high in P | 4.7 | 0.038280259 | 1.4 | 1823 | 2 | 2 | 3 | 7 | 4 | 17 | N | N | N | N | N | N |
| GPN2 | high in P | 3.2 | 0.038295943 | 1.4 | 1824 | 17 | 34 | 29 | 52 | 93 | 46 | N | N | N | N | N | N |
| PCDHB15 | high in P | 3.0 | 0.038308217 | 1.4 | 1825 | 32 | 7 | 5 | 41 | 17 | 47 | N | N | N | N | N | N |
| POLR2L | high in P | 2.5 | 0.038346403 | 1.4 | 1826 | 365 | 447 | 599 | 1928 | 959 | 937 | N | N | N | N | N | N |
| SLC25A25 | high in P | 3.4 | 0.038356686 | 1.4 | 1827 | 1108 | 418 | 451 | 1421 | 1426 | 3004 | N | N | N | N | N | N |
| IPP | high in P | 3.7 | 0.038396181 | 1.4 | 1828 | 35 | 15 | 18 | 64 | 46 | 50 | N | N | N | N | N | N |
| HOOK1 | high in P | 3.8 | 0.038451415 | 1.4 | 1829 | 29 | 32 | 17 | 39 | 75 | 33 | N | N | N | N | N | N |
| C16orf67 | high in P | 3.4 | 0.038542107 | 1.4 | 1830 | 6 | 21 | 15 | 41 | 54 | 21 | P | N | N | N | N | N |
| RIC8A | high in P | 2.8 | 0.038548926 | 1.4 | 1831 | 170 | 95 | 154 | 504 | 330 | 242 | N | N | N | N | N | N |
| FOXO1 | high in P | 2.9 | 0.038625298 | 1.4 | 1832 | 412 | 396 | 267 | 1630 | 635 | 1297 | N | P | N | N | N | N |
| POLE3 | high in P | 2.4 | 0.038645755 | 1.4 | 1833 | 30 | 31 | 41 | 73 | 67 | 101 | N | N | N | N | N | N |
| MCM4 | high in P | 2.2 | 0.038710535 | 1.4 | 1834 | 18 | 29 | 29 | 50 | 62 | 36 | N | N | N | N | N | N |
| RASSF6 | high in P | 3.2 | 0.038733038 | 1.4 | 1835 | 84 | 37 | 50 | 142 | 129 | 86 | N | P | N | N | N | N |
| RPF1 | high in P | 3.3 | 0.038793727 | 1.4 | 1836 | 44 | 48 | 121 | 202 | 135 | 168 | NA | NA | N | N | N | N |
| CC2D1A | high in P | 4.2 | 0.038821684 | 1.4 | 1837 | 16 | 18 | 19 | 66 | 57 | 21 | N | N | N | N | N | N |
| MUS81 | high in P | 2.7 | 0.038833958 | 1.4 | 1838 | 78 | 88 | 161 | 271 | 252 | 190 | N | N | N | N | N | N |
| FAM173A | high in P | 4.2 | 0.038908967 | 1.4 | 1839 | 105 | 33 | 26 | 113 | 120 | 127 | N | N | N | N | N | N |
| LTA | high in P | 3.6 | 0.038990794 | 1.4 | 1840 | 4 | 4 | 5 | 6 | 7 | 12 | N | N | N | N | N | N |
| ILF2 | high in P | 2.2 | 0.039141493 | 1.4 | 1841 | 786 | 1076 | 929 | 1586 | 2312 | 1984 | N | N | N | N | N | N |
| TRMU | high in P | 2.6 | 0.039169451 | 1.4 | 1842 | 25 | 33 | 16 | 56 | 43 | 38 | N | N | N | N | N | N |
| LASS1 | high in P | 6.4 | 0.039208319 | 1.4 | 1843 | 7 | 1 | 2 | 3 | 19 | 28 | N | N | N | N | N | N |
| PTDSS2 | high in P | 3.8 | 0.039215138 | 1.4 | 1844 | 132 | 57 | 45 | 247 | 144 | 187 | N | N | N | N | N | N |
| GMPS | high in P | 2.4 | 0.039404705 | 1.4 | 1845 | 139 | 86 | 87 | 322 | 324 | 153 | N | N | N | N | N | N |
| FAM189A2 | high in P | 3.8 | 0.039459257 | 1.4 | 1846 | 28 | 13 | 11 | 27 | 127 | 18 | NA | NA | N | N | N | N |
| POM121L10P | high in P | 3.3 | 0.039511449 | 1.4 | 1847 | 24 | 21 | 25 | 38 | 63 | 62 | NA | NA | N | N | N | N |
| PIAS3 | high in P | 2.3 | 0.039534947 | 1.4 | 1848 | 151 | 81 | 115 | 379 | 234 | 229 | N | N | N | N | N | N |
| ATOX1 | high in P | 4.4 | 0.039560859 | 1.4 | 1849 | 377 | 84 | 162 | 843 | 755 | 332 | N | N | N | N | N | N |
| AP2S1 | high in P | 4.0 | 0.039590863 | 1.4 | 1850 | 765 | 175 | 307 | 3204 | 1354 | 655 | N | N | N | P | N | N |
| ADAT2 | high in P | 6.4 | 0.039603819 | 1.4 | 1851 | 50 | 16 | 17 | 48 | 63 | 77 | N | N | N | N | N | N |
| CDK5R1 | high in P | 2.3 | 0.039692465 | 1.4 | 1852 | 21 | 28 | 32 | 50 | 46 | 58 | N | N | N | N | N | N |
| SHROOM3 | high in P | 2.8 | 0.039729969 | 1.4 | 1853 | 91 | 93 | 154 | 252 | 897 | 219 | N | N | N | N | N | N |
| CASKIN1 | high in P | 2.4 | 0.039774838 | 1.4 | 1854 | 102 | 80 | 116 | 302 | 237 | 171 | N | N | N | N | N | N |
| LOX | high in P | 3.3 | 0.039760655 | 1.4 | 1855 | 184 | 80 | 163 | 732 | 556 | 222 | N | N | N | N | N | N |
| DPY19L3 | high in P | 2.8 | 0.039776338 | 1.4 | 1856 | 13 | 25 | 43 | 129 | 54 | 46 | N | N | N | N | N | N |
| SRCRB4D | high in P | 3.5 | 0.03980225 | 1.4 | 1857 | 9 | 5 | 9 | 8 | 27 | 15 | N | N | N | N | N | N |
| RSL1D1 | high in P | 2.3 | 0.039912717 | 1.4 | 1858 | 66 | 116 | 91 | 202 | 214 | 299 | N | N | N | N | N | N |
| ACRBP | high in P | 15.4 | 0.039998568 | 1.4 | 1859 | 2 | 2 | 2 | 21 | 2 | 18 | N | N | N | N | N | N |
| IPO13 | high in P | 2.9 | 0.040009547 | 1.4 | 1860 | 28 | 27 | 52 | 50 | 104 | 116 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | Nulliparous (NP) | | | | Parous (P) | | | NP | | P | NP | P | NP | P |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| MT1A | high in P | 3.0 | 0.040035459 | 1.4 | 1861 | 88 | 75 | 277 | 187 | 610 | 747 | N | N | N | N | N | N |
| IRX4 | high in P | 4.2 | 0.040131606 | 1.4 | 1862 | 7 | 36 | 50 | 98 | 186 | 39 | N | N | N | N | N | N |
| NCRNA00115 | high in P | 7.6 | 0.040216843 | 1.4 | 1863 | 2 | 3 | 5 | 24 | 4 | 61 | N | N | N | N | N | N |
| SAPS3 | high in P | 2.2 | 0.040484828 | 1.4 | 1864 | 299 | 246 | 270 | 633 | 509 | 966 | NA | NA | N | N | N | N |
| RPL21P44 | high in P | 3.9 | 0.040582339 | 1.4 | 1865 | 9 | 11 | 15 | 14 | 37 | 39 | NA | NA | N | N | N | N |
| PAQR7 | high in P | 2.7 | 0.040606887 | 1.4 | 1866 | 386 | 97 | 240 | 656 | 672 | 594 | N | N | N | N | N | N |
| PPAP2B | high in P | 3.3 | 0.040619161 | 1.4 | 1867 | 2532 | 2360 | 1241 | 14204 | 4339 | 4068 | N | N | N | N | N | N |
| FARS2 | high in P | 4.1 | 0.040751449 | 1.4 | 1868 | 36 | 11 | 29 | 114 | 43 | 39 | N | N | N | N | N | N |
| C19orf25 | high in P | 2.7 | 0.040777361 | 1.4 | 1869 | 62 | 31 | 60 | 152 | 157 | 75 | N | N | N | N | N | N |
| PPP1R14B | high in P | 2.3 | 0.04085987 | 1.4 | 1870 | 2 | 4 | 5 | 19 | 19 | 8 | N | N | N | N | N | N |
| TRIM8 | high in P | 3.0 | 0.040878964 | 1.4 | 1871 | 1254 | 707 | 440 | 2605 | 1370 | 3539 | N | N | N | N | N | N |
| MIR132 | high in P | 4.7 | 0.040934197 | 1.4 | 1872 | 1 | 1 | 2 | 3 | 6 | 31 | N | N | N | N | N | N |
| OSBPL3 | high in P | 3.9 | 0.040941016 | 1.4 | 1873 | 24 | 35 | 42 | 43 | 107 | 135 | N | N | N | N | N | N |
| TMC4 | high in P | 3.8 | 0.041011251 | 1.4 | 1874 | 94 | 32 | 108 | 106 | 621 | 309 | N | N | N | N | N | N |
| PHF1 | high in P | 3.6 | 0.041039209 | 1.4 | 1875 | 565 | 381 | 781 | 2151 | 931 | 3180 | N | N | N | N | N | N |
| TGFB2 | high in P | 5.3 | 0.041052847 | 1.4 | 1876 | 142 | 149 | 157 | 208 | 899 | 1230 | N | N | N | N | N | N |
| PLAG1 | high in P | 4.7 | 0.041115581 | 1.4 | 1877 | 6 | 6 | 6 | 11 | 6 | 16 | P | N | N | N | P | N |
| C20orf96 | high in P | 4.4 | 0.041144903 | 1.4 | 1878 | 93 | 19 | 33 | 87 | 125 | 124 | N | N | N | N | N | N |
| FAM118A | high in P | 2.7 | 0.04116536 | 1.4 | 1879 | 30 | 18 | 23 | 46 | 38 | 47 | N | P | N | N | N | N |
| RELL2 | high in P | 8.6 | 0.041267644 | 1.4 | 1880 | 4 | 4 | 4 | 54 | 4 | 20 | N | N | N | N | N | N |
| SERHL | high in P | 3.8 | 0.041286737 | 1.4 | 1881 | 8 | 2 | 12 | 13 | 20 | 14 | N | N | N | N | N | N |
| LGR5 | high in P | 6.5 | 0.04130583 | 1.4 | 1882 | 4 | 4 | 4 | 4 | 24 | 10 | N | P | N | N | N | N |
| ADAMTS10 | high in P | 3.6 | 0.041312649 | 1.4 | 1883 | 223 | 39 | 102 | 235 | 357 | 726 | P | N | N | N | N | N |
| TTF2 | high in P | 2.0 | 0.0413597 | 1.4 | 1884 | 18 | 24 | 28 | 47 | 37 | 38 | N | N | N | N | N | N |
| TUBGCP6 | high in P | 2.4 | 0.04141357 | 1.4 | 1885 | 70 | 70 | 136 | 212 | 218 | 186 | N | N | N | N | N | N |
| GRB7 | high in P | 4.3 | 0.041442891 | 1.4 | 1886 | 35 | 87 | 142 | 251 | 865 | 120 | P | N | N | N | N | N |
| SH3RF2 | high in P | 2.7 | 0.04144971 | 1.4 | 1887 | 20 | 16 | 22 | 32 | 80 | 29 | N | N | N | N | N | N |
| PODNL1 | high in P | 4.5 | 0.041524719 | 1.4 | 1888 | 9 | 9 | 9 | 15 | 14 | 22 | N | N | N | N | N | N |
| LOC400891 | high in P | 3.3 | 0.041536993 | 1.4 | 1889 | 12 | 12 | 13 | 18 | 18 | 21 | P | N | N | N | N | N |
| TUBGCP2 | high in P | 3.4 | 0.041570406 | 1.4 | 1890 | 247 | 70 | 169 | 898 | 464 | 273 | N | N | N | N | N | N |
| GNAZ | high in P | 3.5 | 0.041605182 | 1.4 | 1891 | 24 | 39 | 30 | 55 | 204 | 49 | N | N | N | N | N | N |
| METTL14 | high in P | 2.8 | 0.041663144 | 1.4 | 1892 | 11 | 6 | 7 | 24 | 10 | 13 | NA | NA | N | N | N | N |
| MGAT5B | high in P | 3.1 | 0.041676781 | 1.4 | 1893 | 6 | 8 | 7 | 10 | 20 | 34 | P | N | P | P | N | N |
| TAOK3 | high in P | 2.5 | 0.041721105 | 1.4 | 1894 | 58 | 134 | 112 | 302 | 202 | 286 | N | N | N | N | N | N |
| LDHC | high in P | 5.7 | 0.041774974 | 1.4 | 1895 | 3 | 3 | 3 | 3 | 18 | 9 | N | N | N | N | N | N |
| ACVRL1 | high in P | 3.5 | 0.041798159 | 1.4 | 1896 | 192 | 57 | 66 | 573 | 181 | 322 | N | N | N | N | N | N |
| C10orf35 | high in P | 5.3 | 0.042049096 | 1.4 | 1897 | 9 | 19 | 21 | 85 | 224 | 14 | P | N | N | N | N | N |
| BCL2L1 | high in P | 2.8 | 0.042070235 | 1.4 | 1898 | 617 | 329 | 573 | 2313 | 1358 | 857 | P | N | N | N | N | N |
| TOPORS | high in P | 3.1 | 0.042098875 | 1.4 | 1899 | 32 | 95 | 69 | 131 | 144 | 277 | N | N | N | N | N | N |
| GPRC5C | high in P | 3.0 | 0.042119332 | 1.4 | 1900 | 65 | 34 | 116 | 215 | 171 | 138 | NA | NA | N | N | N | N |
| ARAP2 | high in P | 4.8 | 0.042169792 | 1.4 | 1901 | 28 | 12 | 14 | 18 | 90 | 35 | NA | NA | N | N | N | N |
| FAM122B | high in P | 2.8 | 0.04221207 | 1.4 | 1902 | 43 | 28 | 21 | 123 | 58 | 50 | P | N | N | N | N | N |
| DHCR7 | high in P | 2.6 | 0.042244801 | 1.4 | 1903 | 95 | 47 | 50 | 276 | 233 | 85 | N | N | N | N | N | N |
| HEATR1 | high in P | 2.7 | 0.042281623 | 1.4 | 1904 | 66 | 135 | 79 | 171 | 374 | 182 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | Nulliparous (NP) | | | | Parous (P) | | | | | | | | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 NP | CD44+ N66 P | GeneBody NP Met NP | GeneBody Met P | Pro-motor Met NP | Pro-moter Met P |
| GRPEL1 | high in P | 2.5 | 0.042294579 | 1.4 | 1905 | 296 | 479 | 220 | 684 | 1071 | 1003 | N | N | N | N | N | N |
| ADAM32 | high in P | 4.9 | 0.042310263 | 1.4 | 1906 | 5 | 5 | 5 | 5 | 16 | 10 | N | N | N | N | N | N |
| PIGZ | high in P | 2.3 | 0.042317081 | 1.4 | 1907 | 26 | 27 | 26 | 35 | 45 | 47 | N | N | N | N | P | N |
| PIPOX | high in P | 3.5 | 0.042330038 | 1.4 | 1908 | 12 | 13 | 7 | 11 | 22 | 26 | P | N | N | N | N | N |
| AHCTF1 | high in P | 2.1 | 0.04237777 | 1.4 | 1909 | 62 | 78 | 59 | 129 | 123 | 99 | N | N | N | N | N | N |
| PHPT1 | high in P | 2.6 | 0.042418684 | 1.4 | 1910 | 520 | 305 | 481 | 1387 | 1276 | 685 | N | N | N | N | N | N |
| ADAM15 | high in P | 3.7 | 0.042553017 | 1.4 | 1911 | 43 | 96 | 148 | 143 | 470 | 377 | N | N | N | N | N | N |
| LOC440896 | high in P | 2.9 | 0.042569383 | 1.4 | 1912 | 16 | 34 | 70 | 183 | 71 | 80 | N | N | N | N | N | N |
| ACADVL | high in P | 3.7 | 0.042636209 | 1.4 | 1913 | 1194 | 1064 | 3511 | 6572 | 4787 | 3742 | N | N | P | N | N | N |
| MICALL1 | high in P | 3.6 | 0.042643028 | 1.4 | 1914 | 109 | 38 | 117 | 339 | 423 | 128 | N | N | N | N | N | N |
| SNF8 | high in P | 3.0 | 0.042724855 | 1.4 | 1915 | 155 | 93 | 253 | 742 | 368 | 302 | N | N | N | N | N | N |
| RGL3 | high in P | 3.8 | 0.042731674 | 1.4 | 1916 | 13 | 16 | 18 | 62 | 47 | 17 | N | N | N | N | N | N |
| ACTR8 | high in P | 2.5 | 0.042750767 | 1.4 | 1917 | 37 | 28 | 27 | 85 | 46 | 48 | N | N | N | N | N | N |
| HGS | high in P | 2.4 | 0.042763723 | 1.4 | 1918 | 450 | 425 | 580 | 2221 | 1169 | 818 | N | N | N | N | N | N |
| ERC1 | high in P | 2.2 | 0.042788953 | 1.4 | 1919 | 151 | 129 | 179 | 418 | 324 | 281 | N | N | N | N | N | N |
| VSTM2L | high in P | 2.2 | 0.042795772 | 1.4 | 1920 | 4 | 4 | 4 | 6 | 7 | 7 | N | N | N | N | P | N |
| AP1G2 | high in P | 2.3 | 0.04285237 | 1.4 | 1921 | 27 | 50 | 67 | 88 | 131 | 85 | N | N | N | N | N | N |
| RAC3 | high in P | 2.6 | 0.042864644 | 1.4 | 1922 | 16 | 4 | 4 | 11 | 17 | 9 | N | N | N | N | N | N |
| TBK1 | high in P | 2.2 | 0.042937607 | 1.4 | 1923 | 13 | 33 | 44 | 100 | 57 | 63 | N | N | N | N | N | N |
| EML3 | high in P | 2.6 | 0.043279918 | 1.4 | 1924 | 186 | 48 | 113 | 486 | 240 | 265 | N | N | N | N | N | N |
| GLG1 | high in P | 4.3 | 0.043429935 | 1.4 | 1925 | 1397 | 245 | 491 | 3377 | 1452 | 2422 | N | N | N | N | N | N |
| CD96 | high in P | 3.1 | 0.043440164 | 1.4 | 1926 | 19 | 11 | 9 | 16 | 18 | 33 | N | P | N | N | N | N |
| TRIM3 | high in P | 2.8 | 0.043446983 | 1.4 | 1927 | 69 | 57 | 157 | 241 | 193 | 243 | N | N | N | N | N | N |
| DUSP2 | high in P | 3.2 | 0.043564269 | 1.4 | 1928 | 583 | 209 | 188 | 401 | 1841 | 1780 | N | N | N | N | N | N |
| ZCCHC10 | high in P | 2.8 | 0.043591544 | 1.4 | 1929 | 17 | 23 | 11 | 30 | 30 | 23 | P | N | N | N | N | N |
| TMEM132E | high in P | 4.7 | 0.043643369 | 1.4 | 1930 | 3 | 6 | 8 | 28 | 8 | 35 | P | N | N | N | N | N |
| PCNA | high in P | 2.6 | 0.043650188 | 1.4 | 1931 | 243 | 123 | 168 | 404 | 418 | 311 | N | N | N | N | N | N |
| C21orf91 | high in P | 6.2 | 0.043681555 | 1.4 | 1932 | 157 | 25 | 33 | 198 | 194 | 186 | N | N | N | N | N | N |
| NUBP2 | high in P | 2.9 | 0.043705421 | 1.4 | 1933 | 6 | 30 | 9 | 41 | 39 | 22 | N | N | N | N | N | N |
| STMN1 | high in P | 2.8 | 0.043717695 | 1.4 | 1934 | 201 | 123 | 282 | 379 | 588 | 750 | N | P | N | N | N | N |
| SMC3 | high in P | 2.4 | 0.043755881 | 1.4 | 1935 | 45 | 93 | 54 | 190 | 135 | 106 | N | N | N | N | N | N |
| EMILIN3 | high in P | 3.0 | 0.0437627 | 1.4 | 1936 | 18 | 7 | 8 | 20 | 11 | 24 | N | N | N | N | N | N |
| DGKI | high in P | 3.4 | 0.043804296 | 1.4 | 1937 | 5 | 5 | 5 | 9 | 12 | 5 | P | N | N | N | N | N |
| MSI2 | high in P | 2.2 | 0.04386703 | 1.4 | 1938 | 56 | 46 | 32 | 79 | 75 | 99 | N | N | N | N | N | N |
| RANGAP1 | high in P | 2.0 | 0.043913399 | 1.4 | 1939 | 276 | 366 | 362 | 653 | 747 | 813 | N | N | N | N | P | N |
| NDE1 | high in P | 3.2 | 0.043932492 | 1.4 | 1940 | 51 | 34 | 20 | 87 | 57 | 86 | N | N | N | N | N | N |
| ZNF329 | high in P | 3.0 | 0.043939311 | 1.4 | 1941 | 41 | 23 | 16 | 48 | 68 | 40 | N | N | N | N | N | N |
| LEPRE1 | high in P | 2.7 | 0.043982953 | 1.4 | 1942 | 15 | 20 | 11 | 46 | 33 | 37 | N | N | N | N | N | N |
| C8orf41 | high in P | 2.9 | 0.044019775 | 1.4 | 1943 | 11 | 27 | 52 | 151 | 54 | 64 | N | N | N | N | N | N |
| NOG | high in P | 6.2 | 0.044032049 | 1.4 | 1944 | 13 | 11 | 7 | 9 | 91 | 49 | N | N | N | N | N | N |
| STRN4 | high in P | 2.5 | 0.044077736 | 1.4 | 1945 | 328 | 143 | 498 | 735 | 1004 | 872 | P | N | N | N | N | N |
| KLRC3 | high in P | 6.6 | 0.044091374 | 1.4 | 1946 | 2 | 2 | 4 | 5 | 10 | 39 | N | N | N | N | N | N |
| KCNMB1 | high in P | 4.9 | 0.044098193 | 1.4 | 1947 | 26 | 15 | 9 | 27 | 84 | 20 | N | N | N | N | N | N |
| LRRC1 | high in P | 3.1 | 0.04414388 | 1.4 | 1948 | 10 | 11 | 18 | 23 | 80 | 22 | N | N | N | N | P | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | | |
|---|---|---|---|---|---|---|---|---|---|---|---|---|---|---|---|---|---|---|
| | | | | | Nulliparous (NP) | | | | Parous (P) | | | NP | | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
| AP1M1 | high in P | 3.5 | 0.044270713 | 1.4 | 1949 | 513 | 163 | 226 | 1856 | 960 | 420 | N | N | N | N | N | N |
| ARHGDIA | high in P | 3.2 | 0.044298867 | 1.4 | 1950 | 2110 | 889 | 2731 | 6672 | 7314 | 3065 | N | N | N | N | N | N |
| UGT2B10 | high in P | 12.2 | 0.044333788 | 1.4 | 1951 | 2 | 2 | 2 | 16 | 14 | 2 | N | N | N | N | N | N |
| XIST | high in P | 2.0 | 0.044381862 | 1.4 | 1952 | 468 | 545 | 637 | 1243 | 1242 | 1420 | N | N | N | N | N | N |
| NAT10 | high in P | 2.4 | 0.044437777 | 1.4 | 1953 | 100 | 185 | 109 | 269 | 388 | 236 | N | N | N | N | N | N |
| AKR7A3 | high in P | 2.1 | 0.044444596 | 1.4 | 1954 | 19 | 8 | 11 | 19 | 20 | 15 | N | N | N | N | N | N |
| TGDS | high in P | 4.5 | 0.044451415 | 1.4 | 1955 | 4 | 14 | 6 | 67 | 24 | 10 | N | N | N | N | N | N |
| C12orf5 | high in P | 3.1 | 0.044579611 | 1.4 | 1956 | 72 | 52 | 36 | 114 | 121 | 117 | N | N | N | N | N | N |
| MSL3 | high in P | 2.8 | 0.044600075 | 1.4 | 1957 | 78 | 35 | 40 | 105 | 99 | 186 | N | N | N | N | N | N |
| RARRES3 | high in P | 3.6 | 0.044630072 | 1.4 | 1958 | 157 | 50 | 81 | 120 | 447 | 533 | N | N | N | N | N | N |
| LOC284100 | high in P | 2.8 | 0.044699625 | 1.4 | 1959 | 4 | 9 | 10 | 23 | 20 | 12 | N | N | N | N | N | N |
| EBF4 | high in P | 3.8 | 0.044711899 | 1.3 | 1960 | 147 | 45 | 66 | 210 | 255 | 176 | N | N | N | N | N | N |
| RXRB | high in P | 2.4 | 0.044778725 | 1.3 | 1961 | 175 | 149 | 274 | 423 | 390 | 549 | N | N | N | N | N | N |
| LOC90784 | high in P | 3.5 | 0.044893965 | 1.3 | 1962 | 26 | 33 | 24 | 90 | 157 | 28 | NA | NA | N | N | N | N |
| PYGO1 | high in P | 7.1 | 0.044900784 | 1.3 | 1963 | 3 | 3 | 4 | 3 | 21 | 70 | N | N | N | N | N | N |
| NKTR | high in P | 2.2 | 0.044914422 | 1.3 | 1964 | 122 | 130 | 189 | 624 | 315 | 328 | N | N | N | N | N | N |
| C2orf54 | high in P | 4.7 | 0.044994886 | 1.3 | 1965 | 66 | 32 | 18 | 41 | 319 | 104 | N | N | N | N | N | N |
| C1orf216 | high in P | 3.8 | 0.045181043 | 1.3 | 1966 | 108 | 36 | 34 | 139 | 114 | 137 | N | N | N | N | N | N |
| CD55 | high in P | 2.7 | 0.045260143 | 1.3 | 1967 | 209 | 522 | 315 | 1022 | 763 | 882 | N | N | N | N | N | N |
| SGSM2 | high in P | 2.7 | 0.045457893 | 1.3 | 1968 | 135 | 77 | 229 | 294 | 571 | 327 | N | N | N | N | P | N |
| IL10RA | high in P | 3.9 | 0.045498125 | 1.3 | 1969 | 49 | 19 | 10 | 68 | 41 | 158 | P | N | N | N | N | N |
| DNAJC22 | high in P | 2.0 | 0.045561541 | 1.3 | 1970 | 110 | 93 | 105 | 170 | 164 | 230 | N | N | N | N | N | N |
| GMPPB | high in P | 3.8 | 0.04556836 | 1.3 | 1971 | 58 | 34 | 39 | 292 | 131 | 47 | N | N | N | N | N | N |
| RRP9 | high in P | 2.9 | 0.045657006 | 1.3 | 1972 | 43 | 115 | 272 | 307 | 663 | 271 | N | N | N | N | N | N |
| MRPL16 | high in P | 4.8 | 0.045663825 | 1.3 | 1973 | 148 | 21 | 23 | 296 | 192 | 87 | N | N | N | N | N | N |
| CLCN5 | high in P | 2.7 | 0.045682919 | 1.3 | 1974 | 44 | 30 | 33 | 82 | 56 | 59 | N | P | N | N | N | N |
| PRIC285 | high in P | 2.9 | 0.045719059 | 1.3 | 1975 | 21 | 21 | 38 | 50 | 75 | 79 | N | P | N | N | N | N |
| CENPL | high in P | 2.5 | 0.045789976 | 1.3 | 1976 | 9 | 15 | 21 | 25 | 26 | 22 | N | N | N | N | N | N |
| CCT4 | high in P | 2.2 | 0.045841118 | 1.3 | 1977 | 39 | 19 | 25 | 50 | 68 | 49 | N | N | N | N | N | N |
| CCNF | high in P | 2.5 | 0.045966587 | 1.3 | 1978 | 31 | 14 | 31 | 41 | 70 | 47 | N | P | N | N | N | N |
| PPFIA1 | high in P | 1.9 | 0.046034095 | 1.3 | 1979 | 221 | 227 | 241 | 453 | 569 | 404 | N | N | N | N | N | N |
| SP140L | high in P | 2.4 | 0.046040914 | 1.3 | 1980 | 134 | 37 | 109 | 258 | 237 | 207 | N | N | N | N | N | N |
| RBM43 | high in P | 3.3 | 0.046094102 | 1.3 | 1981 | 20 | 13 | 9 | 47 | 20 | 26 | P | N | N | N | N | N |
| PITPNM3 | high in P | 4.2 | 0.046297988 | 1.3 | 1982 | 36 | 12 | 20 | 34 | 62 | 63 | N | N | N | N | N | N |
| TSEN2 | high in P | 2.2 | 0.04632731 | 1.3 | 1983 | 8 | 9 | 9 | 12 | 13 | 17 | N | N | N | N | N | N |
| MTL5 | high in P | 2.1 | 0.046370269 | 1.3 | 1984 | 11 | 15 | 24 | 44 | 34 | 29 | N | N | N | N | N | N |
| C9orf9 | high in P | 4.3 | 0.046423457 | 1.3 | 1985 | 34 | 2 | 4 | 16 | 19 | 48 | N | N | N | N | N | N |
| PLA2G4C | high in P | 2.7 | 0.046471872 | 1.3 | 1986 | 39 | 46 | 76 | 114 | 82 | 177 | N | P | P | N | N | N |
| TNRC18 | high in P | 4.2 | 0.04650733 | 1.3 | 1987 | 453 | 80 | 157 | 981 | 442 | 606 | N | N | N | N | P | N |
| C6orf41 | high in P | 3.1 | 0.046572792 | 1.3 | 1988 | 2 | 15 | 9 | 29 | 33 | 14 | N | N | N | N | N | N |
| C9orf95 | high in P | 2.6 | 0.046579611 | 1.3 | 1989 | 39 | 11 | 8 | 62 | 20 | 53 | N | N | N | N | N | N |
| FAM50A | high in P | 2.9 | 0.046622571 | 1.3 | 1990 | 102 | 97 | 227 | 471 | 256 | 332 | N | N | N | N | N | N |
| NAA10 | high in P | 2.9 | 0.046666894 | 1.3 | 1991 | 350 | 152 | 335 | 1248 | 911 | 392 | NA | NA | N | N | N | N |
| ZSWIM1 | high in P | 3.2 | 0.046794408 | 1.3 | 1992 | 13 | 19 | 34 | 38 | 35 | 84 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | MSDK-seq | | | |
|---|---|---|---|---|---|---|---|---|---|---|---|---|---|---|---|---|---|
| | | | | | Nulliparous (NP) | | | | Parous (P) | | | NP | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-motor Met | Pro-moter Met |
| ATL1 | high in P | 3.2 | 0.046826458 | 1.3 | 1993 | 21 | 11 | 12 | 21 | 23 | 22 | N | N | N | N | N | N |
| SLC24A6 | high in P | 3.3 | 0.046867371 | 1.3 | 1994 | 68 | 110 | 248 | 337 | 339 | 326 | N | N | N | N | N | N |
| LTC4S | high in P | 5.4 | 0.046901466 | 1.3 | 1995 | 29 | 3 | 3 | 16 | 27 | 20 | NA | NA | N | N | N | N |
| DCAF15 | high in P | 3.7 | 0.046927378 | 1.3 | 1996 | 13 | 6 | 10 | 39 | 27 | 9 | N | N | N | N | N | N |
| E4F1 | high in P | 5.3 | 0.046934197 | 1.3 | 1997 | 10 | 10 | 11 | 33 | 29 | 22 | N | N | N | N | N | N |
| STAG3L1 | high in P | 2.2 | 0.04699284 | 1.3 | 1998 | 18 | 28 | 19 | 70 | 31 | 40 | N | N | N | N | N | N |
| CLN6 | high in P | 3.4 | 0.047060348 | 1.3 | 1999 | 33 | 55 | 154 | 177 | 295 | 170 | N | N | N | N | N | N |
| TMEM91 | high in P | 3.2 | 0.047073986 | 1.3 | 2000 | 42 | 19 | 20 | 39 | 57 | 130 | N | N | N | N | N | N |
| CEBPD | high in P | 2.8 | 0.047087624 | 1.3 | 2001 | 2787 | 4101 | 5050 | 5651 | 11363 | 15003 | N | N | N | N | N | N |
| MASTL | high in P | 2.7 | 0.047434708 | 1.3 | 2002 | 41 | 52 | 21 | 87 | 55 | 121 | N | N | N | N | N | N |
| HBS1L | high in P | 3.9 | 0.047441527 | 1.3 | 2003 | 65 | 32 | 34 | 99 | 82 | 104 | N | N | N | N | N | N |
| MFSD10 | high in P | 2.6 | 0.047549949 | 1.3 | 2004 | 834 | 312 | 745 | 1795 | 2196 | 1034 | N | N | N | N | N | N |
| KIAA0495 | high in P | 2.4 | 0.047572451 | 1.3 | 2005 | 29 | 30 | 20 | 81 | 46 | 43 | N | N | N | N | N | N |
| PTMS | high in P | 3.0 | 0.04764746 | 1.3 | 2006 | 2526 | 693 | 1383 | 3896 | 3356 | 3972 | N | N | N | N | N | N |
| ZC3H10 | high in P | 2.8 | 0.047718377 | 1.3 | 2007 | 17 | 6 | 6 | 22 | 11 | 11 | N | N | N | N | N | N |
| SNX32 | high in P | 2.6 | 0.047747699 | 1.3 | 2008 | 4 | 4 | 4 | 8 | 9 | 4 | N | N | N | N | N | N |
| C1orf174 | high in P | 2.6 | 0.04781657 | 1.3 | 2009 | 6 | 7 | 7 | 18 | 14 | 9 | P | N | N | N | N | N |
| LRRC20 | high in P | 3.3 | 0.047829526 | 1.3 | 2010 | 50 | 5 | 15 | 33 | 52 | 127 | N | N | N | N | N | N |
| WDR67 | high in P | 3.0 | 0.047875895 | 1.3 | 2011 | 7 | 7 | 7 | 13 | 7 | 13 | N | N | N | N | N | N |
| RNF167 | high in P | 3.9 | 0.047882714 | 1.3 | 2012 | 501 | 119 | 184 | 802 | 690 | 556 | N | N | N | N | N | N |
| MAP2K5 | high in P | 2.4 | 0.047896352 | 1.3 | 2013 | 58 | 20 | 58 | 109 | 67 | 115 | N | N | N | N | N | N |
| TRAT1 | high in P | 5.8 | 0.047914081 | 1.3 | 2014 | 2 | 2 | 2 | 6 | 2 | 93 | N | N | N | N | N | N |
| EFNB3 | high in P | 6.2 | 0.04802864 | 1.3 | 2015 | 190 | 38 | 18 | 153 | 202 | 278 | N | N | N | N | N | N |
| WDR20 | high in P | 2.2 | 0.048062734 | 1.3 | 2016 | 31 | 48 | 43 | 77 | 67 | 90 | N | N | N | N | N | N |
| FOXE3 | high in P | 12.8 | 0.048160586 | 1.3 | 2017 | 1 | 1 | 1 | 18 | 19 | 1 | P | N | N | N | N | N |
| FITM1 | high in P | 3.8 | 0.048291851 | 1.3 | 2018 | 10 | 5 | 13 | 12 | 17 | 17 | NA | NA | N | N | N | N |
| CLDN10 | high in P | 3.7 | 0.0483164 | 1.3 | 2019 | 5 | 6 | 7 | 7 | 21 | 15 | NA | NA | N | N | N | N |
| C14orf176 | high in P | 4.2 | 0.048331401 | 1.3 | 2020 | 4 | 8 | 4 | 6 | 23 | 84 | NA | NA | N | N | N | N |
| FNIP1 | high in P | 2.1 | 0.048372315 | 1.3 | 2021 | 124 | 192 | 195 | 538 | 366 | 515 | N | P | N | N | N | N |
| APLN | high in P | 3.3 | 0.048393454 | 1.3 | 2022 | 17 | 10 | 13 | 40 | 31 | 13 | N | N | N | N | N | N |
| ANKRD42 | high in P | 4.3 | 0.048461643 | 1.3 | 2023 | 18 | 7 | 8 | 23 | 12 | 28 | N | N | N | N | N | N |
| LOC100129550 | high in P | 2.6 | 0.048488237 | 1.3 | 2024 | 14 | 17 | 22 | 48 | 36 | 22 | N | N | N | N | N | N |
| CHMP7 | high in P | 2.1 | 0.048508012 | 1.3 | 2025 | 9 | 18 | 11 | 27 | 23 | 20 | N | N | N | N | N | N |
| ATP6V0A1 | high in P | 3.1 | 0.048570747 | 1.3 | 2026 | 152 | 84 | 307 | 610 | 349 | 724 | N | N | N | N | N | N |
| POLD2 | high in P | 2.6 | 0.048577566 | 1.3 | 2027 | 50 | 111 | 70 | 378 | 186 | 105 | N | N | N | N | N | N |
| ZNF529 | high in P | 4.4 | 0.048613024 | 1.3 | 2028 | 33 | 37 | 29 | 50 | 98 | 90 | N | N | N | N | N | N |
| SFRS6 | high in P | 2.0 | 0.048750767 | 1.3 | 2029 | 253 | 152 | 298 | 584 | 563 | 624 | N | N | N | N | N | N |
| LOC100190938 | high in P | 3.1 | 0.048766451 | 1.3 | 2030 | 18 | 32 | 14 | 42 | 30 | 40 | N | N | N | N | N | N |
| MAST3 | high in P | 5.4 | 0.048805319 | 1.3 | 2031 | 112 | 24 | 12 | 260 | 41 | 348 | N | N | N | N | N | N |
| HCST | high in P | 5.4 | 0.049029662 | 1.3 | 2032 | 13 | 7 | 14 | 9 | 38 | 113 | N | P | N | N | N | N |
| C1orf144 | high in P | 2.1 | 0.049112854 | 1.3 | 2033 | 143 | 208 | 194 | 579 | 500 | 355 | N | P | N | N | N | N |
| UBE2M | high in P | 2.7 | 0.049187862 | 1.3 | 2034 | 11 | 15 | 19 | 38 | 43 | 18 | N | N | N | N | N | N |
| CEP135 | high in P | 3.5 | 0.049210365 | 1.3 | 2035 | 11 | 11 | 11 | 27 | 19 | 11 | N | N | N | N | N | N |
| C19orf39 | high in P | 2.4 | 0.049217184 | 1.3 | 2036 | 6 | 29 | 21 | 42 | 30 | 40 | N | N | N | N | N | N |

TABLE 15-continued

Genes that Are Differentially Methylated between Nulliparous and Parous CD44+ Breast Epithelial Cells

| | | | | | SAGE-seq | | | | | | | ChIP-seq | | | MSDK-seq | | |
| | | | | | Nulliparous (NP) | | | Parous (P) | | | NP | | P | NP | | P | |
| Gene Symbol | expression pattern | Fold Change | p-value | log10 (p-val.) | Ranking | CD44+ N48 | CD44+ N58 | CD44+ N43 | CD44+ N37 | CD44+ N39 | CD44+ N40 | CD44+ N74 | CD44+ N66 | GeneBody NP Met | GeneBody Met | Pro-moter Met | Pro-moter Met |
|---|---|---|---|---|---|---|---|---|---|---|---|---|---|---|---|---|---|
| NPAT | high in P | 2.6 | 0.049515854 | 1.3 | 2037 | 14 | 40 | 17 | 38 | 55 | 77 | N | N | N | N | N | N |
| UBE2Z | high in P | 2.4 | 0.049556086 | 1.3 | 2038 | 1184 | 956 | 853 | 2981 | 1542 | 2744 | N | N | N | N | N | N |
| VARS2 | high in P | 2.2 | 0.049608592 | 1.3 | 2039 | 66 | 65 | 90 | 126 | 123 | 108 | N | N | N | N | N | N |
| FLII | high in P | 3.3 | 0.049629049 | 1.3 | 2040 | 204 | 335 | 65 | 892 | 804 | 344 | N | N | N | N | N | N |
| SNCG | high in P | 3.4 | 0.04964405 | 1.3 | 2041 | 56 | 13 | 19 | 37 | 117 | 57 | N | N | N | N | N | N |
| ARSD | high in P | 2.1 | 0.049650869 | 1.3 | 2042 | 143 | 175 | 155 | 359 | 276 | 403 | N | N | N | N | N | N |
| RBM10 | high in P | 2.3 | 0.049691101 | 1.3 | 2043 | 489 | 307 | 369 | 865 | 680 | 1119 | N | N | N | N | N | N |
| POT1 | high in P | 3.0 | 0.049723832 | 1.3 | 2044 | 9 | 9 | 10 | 11 | 21 | 17 | N | N | N | N | N | N |
| IFFO1 | high in P | 3.3 | 0.049755836 | 1.3 | 2045 | 171 | 21 | 72 | 245 | 166 | 418 | N | P | N | N | N | N |
| EN2 | high in P | 2.9 | 0.049784521 | 1.3 | 2046 | 17 | 55 | 38 | 56 | 91 | 166 | P | N | N | N | N | N |
| LOC374443 | high in P | 3.4 | 0.049812479 | 1.3 | 2047 | 6 | 12 | 7 | 12 | 11 | 39 | N | N | N | N | N | N |
| SNHG12 | high in P | 2.9 | 0.049905898 | 1.3 | 2048 | 5 | 12 | 15 | 16 | 29 | 35 | N | N | N | N | N | N |
| C1orf59 | high in P | 2.9 | 0.049919536 | 1.3 | 2049 | 5 | 6 | 5 | 15 | 8 | 13 | N | N | N | N | N | N |
| MICA | high in P | 2.5 | 0.04994613 | 1.3 | 2050 | 113 | 133 | 84 | 280 | 140 | 422 | N | N | N | N | N | N |

TABLE 16

Genes that Are Differentially Methylated between Nulliparous and Parous CD24+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | log10 | | Nulliparous (NP) | | | | Parous (P) | | | | | | | |
| Gene Symbol | expression pattern | Fold Change | p-value | (P-val.) | Rank-ing | CD24+ N48 | CD24+ N58 | CD24+ N43 | CD24+ N37 | CD24+ N39 | CD24+ N40 | NP | CD24+ N74 | CD24+ N66 | GeneBody NP | GeneBody Met P | Pro-moter Met NP | Pro-moter Met P |
| C9orf16 | high in NP | -2.4 | 0.0499928 | -1.3 | 13183 | 168 | 86 | 177 | 33 | 66 | 91 | N | N | N | N | N | N | N |
| TRIM56 | high in NP | -2.0 | 0.049894062 | -1.3 | 13184 | 31 | 84 | 34 | 26 | 17 | 24 | N | N | N | N | N | N | N |
| MED25 | high in NP | -1.7 | 0.049988789 | -1.3 | 13185 | 135 | 87 | 56 | 47 | 49 | 33 | N | N | N | N | N | N | N |
| ENOSF1 | high in NP | -2.0 | 0.049828922 | -1.3 | 13186 | 126 | 229 | 161 | 104 | 115 | 66 | N | NA | NA | N | N | N | N |
| LPPR3 | high in NP | -1.8 | 0.049768582 | -1.3 | 13187 | 6 | 17 | 17 | 6 | 6 | 6 | N | N | N | N | N | N | N |
| NDUFA9 | high in NP | -1.8 | 0.049752811 | -1.3 | 13188 | 478 | 586 | 575 | 316 | 424 | 217 | N | N | N | N | N | N | N |
| LOC151162 | high in NP | -1.7 | 0.04972607 | -1.3 | 13189 | 49 | 63 | 43 | 30 | 31 | 33 | N | N | N | N | N | N | N |
| NAT15 | high in NP | -2.1 | 0.049577276 | -1.3 | 13190 | 57 | 198 | 82 | 30 | 46 | 49 | N | N | N | N | N | N | N |
| TTYH1 | high in NP | -3.4 | 0.049514194 | -1.3 | 13191 | 247 | 132 | 545 | 37 | 88 | 151 | N | N | N | N | N | N | N |
| SLC25A5 | high in NP | -2.6 | 0.049416827 | -1.3 | 13192 | 799 | 594 | 383 | 146 | 329 | 340 | N | N | N | N | N | N | N |
| ERCC1 | high in NP | -2.0 | 0.049267348 | -1.3 | 13193 | 333 | 672 | 373 | 197 | 201 | 304 | N | N | N | N | N | N | N |
| INPP5E | high in NP | -2.2 | 0.049237863 | -1.3 | 13194 | 16 | 38 | 27 | 8 | 8 | 19 | N | N | N | N | N | N | N |
| ABCB8 | high in NP | -1.8 | 0.049168609 | -1.3 | 13195 | 102 | 112 | 76 | 65 | 52 | 50 | N | N | N | N | N | N | N |
| ROBO3 | high in NP | -2.1 | 0.049137068 | -1.3 | 13196 | 135 | 158 | 228 | 63 | 91 | 110 | N | N | N | N | N | N | N |
| COX6C | high in NP | -2.7 | 0.04912404 | -1.3 | 13197 | 91 | 35 | 34 | 11 | 31 | 16 | N | N | N | N | N | N | N |
| CCDC9 | high in NP | -1.8 | 0.049100041 | -1.3 | 13198 | 94 | 72 | 129 | 37 | 58 | 49 | N | N | N | N | N | N | N |
| ISCU | high in NP | -2.1 | 0.048993075 | -1.3 | 13199 | 60 | 63 | 30 | 27 | 24 | 29 | N | N | N | N | N | N | N |
| NIT1 | high in NP | -1.7 | 0.048807255 | -1.3 | 13200 | 30 | 35 | 21 | 16 | 16 | 15 | N | N | N | N | N | N | N |
| BAD | high in NP | -2.5 | 0.048801083 | -1.3 | 13201 | 97 | 174 | 280 | 92 | 69 | 58 | N | N | N | N | N | N | N |
| SCO2 | high in NP | -2.6 | 0.048753771 | -1.3 | 13202 | 261 | 456 | 127 | 99 | 115 | 112 | N | N | N | N | N | N | N |
| GOLM1 | high in NP | -2.4 | 0.0487476 | -1.3 | 13203 | 398 | 604 | 216 | 192 | 192 | 137 | N | N | N | N | N | N | N |
| HINT1 | high in NP | -1.6 | 0.048741429 | -1.3 | 13204 | 99 | 108 | 83 | 70 | 43 | 59 | N | N | N | N | N | N | N |
| ANTXR1 | high in NP | -2.0 | 0.048635148 | -1.3 | 13205 | 30 | 52 | 28 | 21 | 24 | 21 | N | N | N | N | N | N | N |
| RP9P | high in NP | -2.0 | 0.048583722 | -1.3 | 13206 | 6 | 13 | 11 | 6 | 6 | 6 | N | N | N | N | N | N | N |
| RHBDL2 | high in NP | -1.6 | 0.048535038 | -1.3 | 13207 | 623 | 856 | 816 | 441 | 537 | 474 | N | P | N | N | N | N | N |
| NACC1 | high in NP | -1.7 | 0.048389674 | -1.3 | 13208 | 181 | 232 | 203 | 123 | 162 | 81 | N | N | N | N | N | N | N |
| APH1A | high in NP | -1.7 | 0.048331391 | -1.3 | 13209 | 134 | 322 | 197 | 120 | 95 | 113 | N | N | N | N | N | N | N |
| MAGED2 | high in NP | -2.3 | 0.048278593 | -1.3 | 13210 | 799 | 1109 | 453 | 412 | 360 | 378 | N | N | N | N | N | N | N |
| CCT8 | high in NP | -2.2 | 0.04796455 | -1.3 | 13211 | 471 | 1414 | 829 | 402 | 346 | 457 | N | N | N | N | N | N | N |
| VASP | high in NP | -2.8 | 0.047947408 | -1.3 | 13212 | 53 | 132 | 152 | 40 | 53 | 55 | N | N | N | N | N | P | N |
| C9orf86 | high in NP | -2.3 | 0.047941237 | -1.3 | 13213 | 222 | 940 | 480 | 226 | 226 | 178 | N | N | N | N | N | N | N |
| NDST2 | high in NP | -4.2 | 0.04788364 | -1.3 | 13214 | 45 | 174 | 205 | 41 | 59 | 36 | N | N | N | N | N | N | N |
| PGAP2 | high in NP | -1.6 | 0.047853 | -1.3 | 13215 | 67 | 34 | 31 | 18 | 15 | 15 | N | NA | NA | N | N | N | N |
| SLC22A17 | high in NP | -2.0 | 0.047821242 | -1.3 | 13216 | 242 | 255 | 330 | 108 | 141 | 213 | N | N | N | N | N | N | N |
| CDIPT | high in NP | -1.6 | 0.047701934 | -1.3 | 13217 | 60 | 64 | 47 | 33 | 40 | 31 | N | N | N | N | N | N | N |
| TNKS1BP1 | high in NP | -2.3 | 0.047627194 | -1.3 | 13218 | 612 | 1585 | 1185 | 432 | 455 | 710 | N | P | N | N | N | N | N |
| KIAA0652 | high in NP | -2.4 | 0.047621023 | -1.3 | 13219 | 116 | 115 | 53 | 44 | 32 | 42 | N | N | N | N | N | N | N |
| C19orf22 | high in NP | -1.9 | 0.047589482 | -1.3 | 13220 | 1430 | 2004 | 3103 | 803 | 1192 | 1270 | N | N | N | N | N | N | N |
| C14orf28 | high in NP | -2.3 | 0.047535998 | -1.3 | 13221 | 15 | 24 | 16 | 14 | 6 | 6 | N | N | N | N | N | N | N |
| MBIP | high in NP | -1.7 | 0.047476344 | -1.3 | 13222 | 62 | 55 | 36 | 29 | 28 | 26 | N | N | N | N | N | N | N |
| PRKCI | high in NP | -1.7 | 0.047448917 | -1.3 | 13223 | 93 | 121 | 107 | 34 | 64 | 71 | N | N | N | N | N | P | N |
| SMG1 | high in NP | -2.4 | 0.047395433 | -1.3 | 13224 | 244 | 208 | 132 | 88 | 82 | 134 | N | N | N | N | N | N | N |

TABLE 16-continued

Genes that Are Differentially Methylated between Nulliparous and Parous CD24+ Breast Epithelial Cells

| | | | | SAGE-seq | Nulliparous (NP) | | | | Parous (P) | | | | ChIP-seq | | | MSDK-seq | | |
|---|---|---|---|---|---|---|---|---|---|---|---|---|---|---|---|---|---|---|
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | P GeneBody Met | NP Pro-moter Met | P Pro-moter Met |
|---|---|---|---|---|---|---|---|---|---|---|---|---|---|---|---|---|---|
| H6PD | high in NP | -1.6 | 0.047362521 | -1.3 | 13225 | 51 | 118 | 64 | 43 | 44 | 36 | N | N | N | N | N | N |
| RBM42 | high in NP | -2.0 | 0.04735155 | -1.3 | 13226 | 93 | 98 | 75 | 15 | 56 | 38 | N | N | N | N | N | N |
| NCRNA00095 | high in NP | -3.4 | 0.047328922 | -1.3 | 13227 | 468 | 455 | 148 | 117 | 112 | 158 | N | N | N | N | N | N |
| ZNF134 | high in NP | -1.6 | 0.047296695 | -1.3 | 13228 | 42 | 25 | 19 | 17 | 17 | 18 | N | N | N | N | N | N |
| SFRS17A | high in NP | -3.8 | 0.047290524 | -1.3 | 13229 | 245 | 77 | 142 | 49 | 83 | 45 | N | N | N | N | N | N |
| CTBP2 | high in NP | -1.5 | 0.047233612 | -1.3 | 13230 | 71 | 58 | 57 | 37 | 42 | 39 | N | N | N | N | N | N |
| KCTD5 | high in NP | -1.9 | 0.047144473 | -1.3 | 13231 | 10 | 18 | 12 | 10 | 6 | 6 | N | N | N | N | N | N |
| SLC7A8 | high in NP | -1.9 | 0.04713076 | -1.3 | 13232 | 120 | 203 | 172 | 96 | 118 | 64 | N | N | N | N | N | N |
| LOC100190939 | high in NP | -2.2 | 0.046869515 | -1.3 | 13233 | 512 | 313 | 184 | 85 | 156 | 168 | N | N | N | N | N | N |
| ATF6 | high in NP | -1.8 | 0.046625411 | -1.3 | 13234 | 17 | 22 | 13 | 9 | 9 | 12 | N | N | N | N | N | N |
| LOC100144603 | high in NP | -4.1 | 0.046612383 | -1.3 | 13235 | 1 | 3 | 5 | 1 | 1 | 1 | N | N | N | N | N | N |
| HEXIM2 | high in NP | -1.8 | 0.046516388 | -1.3 | 13236 | 7 | 6 | 4 | 5 | 2 | 2 | N | N | N | N | N | N |
| WDR6 | high in NP | -1.9 | 0.046505417 | -1.3 | 13237 | 157 | 170 | 150 | 54 | 84 | 120 | N | N | N | N | N | N |
| ADAM11 | high in NP | -1.8 | 0.046479361 | -1.3 | 13238 | 14 | 12 | 14 | 9 | 9 | 9 | N | N | N | N | N | N |
| TGM4 | high in NP | -4.3 | 0.046466333 | -1.3 | 13239 | 1 | 4 | 4 | 1 | 1 | 1 | N | P | N | N | N | N |
| PYGM | high in NP | -2.7 | 0.046403936 | -1.3 | 13240 | 24 | 23 | 34 | 12 | 12 | 23 | N | N | N | N | N | N |
| AURKAIP1 | high in NP | -4.1 | 0.046323025 | -1.3 | 13241 | 200 | 756 | 848 | 192 | 235 | 147 | N | N | N | N | N | N |
| LOC642361 | high in NP | -5.8 | 0.046170118 | -1.3 | 13242 | 4 | 18 | 33 | 4 | 4 | 4 | NA | NA | N | N | N | N |
| EPHA10 | high in NP | -1.6 | 0.046128291 | -1.3 | 13243 | 14 | 25 | 16 | 9 | 9 | 9 | N | P | N | N | N | N |
| UPK3A | high in NP | -9.1 | 0.045874589 | -1.3 | 13244 | 2 | 73 | 35 | 5 | 2 | 2 | NA | P | N | N | N | N |
| CDCA4 | high in NP | -2.2 | 0.045861561 | -1.3 | 13245 | 50 | 74 | 33 | 17 | 17 | 38 | N | N | N | N | N | N |
| SRPR | high in NP | -2.1 | 0.045784078 | -1.3 | 13246 | 448 | 827 | 350 | 290 | 338 | 243 | N | N | N | N | N | N |
| PHLDA3 | high in NP | -1.9 | 0.045772422 | -1.3 | 13247 | 27 | 17 | 18 | 13 | 10 | 10 | N | N | N | N | N | N |
| TRAF5 | high in NP | -1.9 | 0.045642828 | -1.3 | 13248 | 35 | 34 | 27 | 16 | 25 | 16 | N | N | N | N | N | N |
| USP53 | high in NP | -2.0 | 0.045610601 | -1.3 | 13249 | 795 | 378 | 324 | 216 | 273 | 206 | N | N | N | N | N | N |
| CCDC89 | high in NP | -4.3 | 0.045502263 | -1.3 | 13250 | 2 | 5 | 8 | 2 | 2 | 2 | N | N | N | N | N | N |
| C9orf21 | high in NP | -2.7 | 0.045543294 | -1.3 | 13251 | 113 | 185 | 118 | 45 | 35 | 105 | N | N | N | N | N | N |
| PLIN3 | high in NP | -1.8 | 0.045416552 | -1.3 | 13252 | 675 | 1578 | 777 | 470 | 447 | 563 | NA | NA | N | N | N | N |
| YPEL3 | high in NP | -1.7 | 0.045295187 | -1.3 | 13253 | 194 | 361 | 270 | 169 | 146 | 175 | N | N | N | N | N | N |
| TMC6 | high in NP | -2.0 | 0.045275302 | -1.3 | 13254 | 106 | 231 | 198 | 105 | 84 | 96 | N | N | N | N | N | N |
| NDUFB2 | high in NP | -1.7 | 0.045207419 | -1.3 | 13255 | 311 | 484 | 389 | 238 | 278 | 153 | N | N | N | N | N | N |
| AP1B1 | high in NP | -1.6 | 0.045161478 | -1.3 | 13256 | 147 | 155 | 157 | 113 | 101 | 54 | N | N | N | N | N | N |
| ATP6V1C2 | high in NP | -3.2 | 0.045051769 | -1.3 | 13257 | 113 | 62 | 24 | 18 | 26 | 20 | N | N | N | N | N | N |
| GBAS | high in NP | -2.9 | 0.044963316 | -1.3 | 13258 | 48 | 35 | 13 | 9 | 9 | 9 | N | P | N | N | N | N |
| PALLD | high in NP | -1.9 | 0.044903662 | -1.3 | 13259 | 1425 | 1438 | 1244 | 664 | 845 | 1049 | N | N | N | N | N | N |
| CHRNA10 | high in NP | -4.6 | 0.044835093 | -1.3 | 13260 | 4 | 8 | 7 | 4 | 4 | 4 | N | N | N | N | N | P |
| VPS28 | high in NP | -2.2 | 0.044828922 | -1.3 | 13261 | 623 | 1258 | 1394 | 586 | 560 | 408 | N | N | N | N | N | N |
| CCNY | high in NP | -1.7 | 0.044809037 | -1.3 | 13262 | 145 | 171 | 130 | 108 | 81 | 89 | N | N | N | N | N | N |
| TM9SF3 | high in NP | -2.0 | 0.044709613 | -1.3 | 13263 | 257 | 634 | 228 | 163 | 146 | 159 | N | N | N | N | N | N |
| GGT5 | high in NP | -2.1 | 0.04466093 | -1.4 | 13264 | 41 | 58 | 76 | 38 | 30 | 23 | N | N | N | N | N | N |
| NUP93 | high in NP | -4.4 | 0.044574534 | -1.4 | 13265 | 30 | 201 | 172 | 16 | 47 | 28 | N | N | N | N | N | N |
| TMEM168 | high in NP | -1.9 | 0.044532021 | -1.4 | 13266 | 47 | 79 | 54 | 38 | 23 | 35 | N | N | N | N | N | N |
| CCDC90A | high in NP | -1.8 | 0.044501166 | -1.4 | 13267 | 13 | 11 | 25 | 7 | 5 | 8 | N | N | N | N | N | N |
| CCDC157 | high in NP | -3.6 | 0.044371572 | -1.4 | 13268 | 13 | 40 | 68 | 8 | 15 | 11 | NA | NA | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | | | MSDK-seq | | |
|---|---|---|---|---|---|---|---|---|---|---|---|---|---|---|---|---|---|---|---|
| | | | | | | Nulliparous (NP) | | | | Parous (P) | | | | | | | | | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP | CD24+ N74 | CD24+ N66 | NP | GeneBody | GeneBody Met | P | Pro-moter Met | Pro-moter Met P |
| PACS2 | high in NP | −2.3 | 0.044331116 | −1.4 | 13269 | 411 | 349 | 757 | 231 | 349 | 204 | N | N | N | NP | N | N | N | N | N |
| C14orf2 | high in NP | −2.7 | 0.04425432 | −1.4 | 13270 | 199 | 115 | 66 | 27 | 64 | 52 | N | N | N | N | N | N | N | N | N |
| AP15 | high in NP | −2.0 | 0.044216607 | −1.4 | 13271 | 35 | 59 | 29 | 18 | 20 | 26 | N | N | N | N | N | N | N | N | N |
| KIAA0753 | high in NP | −2.5 | 0.044203579 | −1.4 | 13272 | 17 | 26 | 22 | 9 | 19 | 9 | N | N | N | N | N | N | N | N | N |
| THBS3 | high in NP | −2.8 | 0.044188494 | −1.4 | 13273 | 170 | 102 | 310 | 85 | 61 | 74 | N | N | N | N | N | N | N | N | N |
| ATP6V0E2 | high in NP | −1.9 | 0.044063014 | −1.4 | 13274 | 87 | 118 | 128 | 80 | 32 | 54 | N | N | N | N | N | N | N | N | N |
| EEF2 | high in NP | −1.9 | 0.043843596 | −1.4 | 13275 | 27618 | 57739 | 47767 | 17418 | 23556 | 24703 | N | N | N | N | N | N | N | N | N |
| SOX13 | high in NP | −1.6 | 0.043715373 | −1.4 | 13276 | 31 | 55 | 58 | 29 | 29 | 27 | N | N | N | N | N | N | N | N | N |
| ZNF454 | high in NP | −1.9 | 0.043567951 | −1.4 | 13277 | 48 | 91 | 78 | 29 | 26 | 48 | N | N | N | N | N | N | N | N | N |
| PARVB | high in NP | −2.2 | 0.043487041 | −1.4 | 13278 | 100 | 168 | 120 | 54 | 101 | 46 | N | N | N | N | N | N | N | N | N |
| MMP11 | high in NP | −4.6 | 0.043477441 | −1.4 | 13279 | 6 | 13 | 9 | 6 | 6 | 6 | N | N | N | N | N | N | N | N | N |
| FAM20A | high in NP | −2.4 | 0.043464413 | −1.4 | 13280 | 58 | 55 | 31 | 21 | 27 | 30 | N | N | N | N | N | N | N | N | N |
| S100A2 | high in NP | −2.8 | 0.0434363 | −1.4 | 13281 | 125 | 302 | 291 | 34 | 110 | 123 | N | N | N | N | N | N | N | N | N |
| RPPH1 | high in NP | −3.1 | 0.043421901 | −1.4 | 13282 | 14 | 4 | 4 | 5 | 2 | 6 | N | N | N | N | N | N | N | P | N |
| IER5 | high in NP | −2.6 | 0.043349904 | −1.4 | 13283 | 1101 | 3072 | 2147 | 688 | 736 | 1221 | N | N | N | N | N | N | N | N | N |
| VAPA | high in NP | −2.0 | 0.043213453 | −1.4 | 13284 | 279 | 262 | 171 | 93 | 86 | 167 | N | N | N | N | N | N | N | N | N |
| KIF1C | high in NP | −2.0 | 0.043176426 | −1.4 | 13285 | 191 | 329 | 411 | 141 | 229 | 118 | N | N | N | N | N | N | N | N | N |
| HIF1A | high in NP | −2.0 | 0.043046146 | −1.4 | 13286 | 312 | 613 | 258 | 243 | 141 | 176 | N | N | N | N | N | N | N | N | N |
| C21orf34 | high in NP | −5.9 | 0.042984435 | −1.4 | 13287 | 53 | 10 | 32 | 9 | 14 | 12 | N | N | N | N | N | N | N | N | N |
| POLR2D | high in NP | −2.3 | 0.042930952 | −1.4 | 13288 | 45 | 100 | 121 | 39 | 35 | 39 | N | N | N | N | N | N | N | N | N |
| LHPP | high in NP | −1.9 | 0.04290901 | −1.4 | 13289 | 72 | 59 | 100 | 32 | 45 | 41 | N | N | N | N | N | N | N | N | N |
| KLF13 | high in NP | −1.7 | 0.042888439 | −1.4 | 13290 | 288 | 256 | 198 | 153 | 154 | 130 | N | N | N | N | N | N | N | N | N |
| RAB13 | high in NP | −2.2 | 0.042875411 | −1.4 | 13291 | 58 | 121 | 37 | 32 | 24 | 28 | N | N | N | N | N | N | N | N | N |
| KCNAB3 | high in NP | −3.1 | 0.042769816 | −1.4 | 13292 | 28 | 58 | 44 | 13 | 29 | 7 | N | N | N | N | N | N | N | N | N |
| SRPRB | high in NP | −5.2 | 0.042707419 | −1.4 | 13293 | 25 | 214 | 89 | 22 | 12 | 33 | N | N | N | N | N | N | N | N | N |
| LOC390595 | high in NP | −5.6 | 0.042656679 | −1.4 | 13294 | 6 | 35 | 57 | 6 | 8 | 6 | N | N | NA | NA | N | N | N | N | N |
| GSTA1 | high in NP | −4.7 | 0.042650507 | −1.4 | 13295 | 13 | 43 | 25 | 1 | 14 | 7 | N | N | N | N | N | N | N | N | N |
| MAGOH | high in NP | −2.8 | 0.04262308 | −1.4 | 13296 | 260 | 207 | 839 | 70 | 160 | 140 | N | N | N | N | N | N | N | N | N |
| FAM128A | high in NP | −3.5 | 0.042546284 | −1.4 | 13297 | 13 | 3 | 15 | 1 | 8 | 1 | N | N | N | N | N | N | N | N | N |
| ZNF250 | high in NP | −2.3 | 0.042455088 | −1.4 | 13298 | 135 | 90 | 88 | 38 | 38 | 74 | N | N | N | N | N | N | N | N | N |
| BRD2 | high in NP | −2.0 | 0.042412575 | −1.4 | 13299 | 1208 | 1023 | 650 | 568 | 460 | 577 | N | N | N | N | N | N | N | N | N |
| HDAC10 | high in NP | −2.6 | 0.042392691 | −1.4 | 13300 | 249 | 121 | 307 | 82 | 125 | 59 | N | N | N | N | N | N | N | N | N |
| NR1H2 | high in NP | −2.1 | 0.042354292 | −1.4 | 13301 | 672 | 1349 | 1383 | 572 | 654 | 360 | N | N | N | N | N | N | N | N | N |
| DSP | high in NP | −2.4 | 0.042328922 | −1.4 | 13302 | 1087 | 560 | 541 | 261 | 374 | 403 | N | N | N | N | N | N | N | N | N |
| NDEL1 | high in NP | −1.6 | 0.042307666 | −1.4 | 13303 | 35 | 33 | 37 | 23 | 17 | 18 | N | N | N | N | N | N | N | N | N |
| PHF12 | high in NP | −1.6 | 0.04225624 | −1.4 | 13304 | 252 | 336 | 234 | 156 | 177 | 183 | N | N | N | N | N | N | N | N | N |
| GPX4 | high in NP | −1.9 | 0.042203442 | −1.4 | 13305 | 6044 | 4408 | 7181 | 2246 | 3535 | 3302 | N | N | N | N | N | N | N | N | N |
| CA13 | high in NP | −1.8 | 0.042173958 | −1.4 | 13306 | 93 | 94 | 82 | 36 | 42 | 63 | N | N | N | N | N | N | N | N | N |
| F5 | high in NP | −3.0 | 0.042158873 | −1.4 | 13307 | 303 | 821 | 153 | 117 | 83 | 154 | N | N | N | N | N | N | N | N | N |
| RABGEF1 | high in NP | −1.8 | 0.042079334 | −1.4 | 13308 | 325 | 436 | 843 | 207 | 287 | 239 | N | N | N | N | N | N | N | N | N |
| CYP51A1 | high in NP | −2.5 | 0.042003223 | −1.4 | 13309 | 262 | 151 | 88 | 94 | 59 | 39 | N | N | N | N | N | N | N | N | N |
| FAM116B | high in NP | −1.8 | 0.041983338 | −1.4 | 13310 | 88 | 110 | 204 | 56 | 68 | 53 | N | N | N | N | N | N | N | N | N |
| NDUFS6 | high in NP | −2.7 | 0.041942197 | −1.4 | 13311 | 353 | 1089 | 760 | 308 | 347 | 279 | N | N | N | N | N | N | N | N | N |
| ANAPC11 | high in NP | −2.2 | 0.041901742 | −1.4 | 13312 | 669 | 1092 | 1482 | 567 | 605 | 331 | N | N | N | N | N | N | N | N | N |

TABLE 16-continued

Genes that Are Differentially Methylated between Nulliparous and Parous CD24+ Breast Epithelial Cells

| | | | SAGE-seq | | | | | | | | ChIP-seq | | MSDK-seq | | |
| --- | --- | --- | --- | --- | --- | --- | --- | --- | --- | --- | --- | --- | --- | --- | --- |
| | | | | | Nulliparous (NP) | | | | Parous (P) | | | | | | |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | P GeneBody Met | NP Pro-moter Met | P Pro-moter Met |
| DNAJC30 | high in NP | -1.8 | 0.041864715 | -1.4 | 13313 | 72 | 114 | 101 | 62 | 62 | 41 | N | N | NP | N | N | N |
| YEATS4 | high in NP | -2.6 | 0.041851001 | -1.4 | 13314 | 11 | 25 | 6 | 3 | 6 | 3 | N | N | N | N | N | N |
| LRRC16B | high in NP | -3.9 | 0.041810546 | -1.4 | 13315 | 11 | 45 | 20 | 12 | 6 | 6 | N | N | N | N | N | N |
| FAM167B | high in NP | -5.3 | 0.041796832 | -1.4 | 13316 | 2 | 6 | 6 | 2 | 2 | 2 | N | N | N | N | N | N |
| RPN2 | high in NP | -2.3 | 0.041765291 | -1.4 | 13317 | 141 | 200 | 94 | 72 | 90 | 65 | N | N | N | N | N | N |
| UBE3A | high in NP | -2.1 | 0.041752912 | -1.4 | 13318 | 98 | 241 | 180 | 60 | 65 | 125 | N | N | N | N | N | N |
| PLXNB2 | high in NP | -2.1 | 0.041752948 | -1.4 | 13319 | 1037 | 1963 | 1846 | 861 | 904 | 870 | N | N | N | N | N | N |
| NUMBL | high in NP | -3.0 | 0.041734435 | -1.4 | 13320 | 64 | 43 | 122 | 19 | 17 | 41 | N | N | N | N | N | N |
| TRIO | high in NP | -1.5 | 0.041707008 | -1.4 | 13321 | 493 | 851 | 626 | 417 | 422 | 391 | N | N | N | N | N | N |
| CDK5RAP3 | high in NP | -2.6 | 0.041674095 | -1.4 | 13322 | 153 | 51 | 27 | 12 | 17 | 26 | N | N | N | N | N | N |
| SLAMF8 | high in NP | -1.9 | 0.041626783 | -1.4 | 13323 | 40 | 18 | 21 | 12 | 12 | 11 | N | N | N | N | N | N |
| CNOT4 | high in NP | -2.1 | 0.041537644 | -1.4 | 13324 | 98 | 102 | 59 | 28 | 47 | 55 | N | N | N | N | N | N |
| TNFSF14 | high in NP | -2.9 | 0.041495132 | -1.4 | 13325 | 1660 | 1447 | 597 | 470 | 436 | 595 | N | N | N | N | N | N |
| IRAK1 | high in NP | -2.7 | 0.041485532 | -1.4 | 13326 | 322 | 1019 | 747 | 275 | 399 | 211 | N | N | N | N | N | N |
| PKN1 | high in NP | -2.5 | 0.041465647 | -1.4 | 13327 | 114 | 281 | 209 | 125 | 84 | 52 | N | N | N | N | N | N |
| STK32C | high in NP | -2.1 | 0.0414144302 | -1.4 | 13328 | 48 | 88 | 135 | 29 | 38 | 38 | N | N | N | N | N | N |
| FSD1L | high in NP | -1.8 | 0.041332625 | -1.4 | 13329 | 13 | 12 | 14 | 8 | 11 | 8 | N | N | N | N | N | N |
| DVL1 | high in NP | -2.1 | 0.041130314 | -1.4 | 13330 | 123 | 81 | 143 | 36 | 50 | 62 | N | N | N | N | N | N |
| NDUFAB1 | high in NP | -4.2 | 0.041258571 | -1.4 | 13331 | 15 | 81 | 42 | 13 | 14 | 12 | N | P | N | N | N | N |
| LOC643719 | high in NP | -5.3 | 0.041245543 | -1.4 | 13332 | 1 | 6 | 5 | 1 | 1 | 1 | NA | NA | N | N | N | N |
| CWC25 | high in NP | -1.7 | 0.041235943 | -1.4 | 13333 | 58 | 46 | 38 | 28 | 22 | 28 | NA | NA | N | N | N | N |
| MAML3 | high in NP | -2.6 | 0.041176975 | -1.4 | 13334 | 17 | 65 | 52 | 21 | 19 | 17 | N | N | N | N | N | N |
| CS | high in NP | -2.8 | 0.041170804 | -1.4 | 13335 | 1222 | 1933 | 665 | 458 | 550 | 645 | N | N | N | N | N | N |
| MRPL21 | high in NP | -3.4 | 0.041164632 | -1.4 | 13336 | 36 | 20 | 10 | 5 | 10 | 14 | N | N | N | N | N | N |
| NUP85 | high in NP | -3.1 | 0.041070008 | -1.4 | 13337 | 34 | 100 | 50 | 12 | 31 | 27 | N | N | N | N | N | N |
| PI15 | high in NP | -1.5 | 0.041008297 | -1.4 | 13338 | 32 | 37 | 33 | 28 | 28 | 28 | N | N | N | N | N | N |
| C1QTNF6 | high in NP | -1.7 | 0.040925329 | -1.4 | 13339 | 24 | 28 | 27 | 12 | 15 | 15 | N | N | N | N | N | N |
| MAP2K3 | high in NP | -2.6 | 0.040842704 | -1.4 | 13340 | 2453 | 4001 | 1526 | 934 | 1100 | 1486 | N | N | N | N | N | N |
| MAOA | high in NP | -2.9 | 0.040826591 | -1.4 | 13341 | 50 | 27 | 20 | 19 | 11 | 17 | N | N | N | N | N | N |
| SH3BGRL | high in NP | -2.8 | 0.04082042 | -1.4 | 13342 | 99 | 98 | 40 | 19 | 36 | 29 | N | P | N | N | N | N |
| DYRK4 | high in NP | -2.2 | 0.040814248 | -1.4 | 13343 | 13 | 33 | 33 | 9 | 15 | 8 | NA | N | N | N | N | N |
| INTS7 | high in NP | -3.0 | 0.04075528 | -1.4 | 13344 | 290 | 398 | 125 | 100 | 59 | 141 | N | N | N | N | N | N |
| C1orf210 | high in NP | -2.5 | 0.040734709 | -1.4 | 13345 | 52 | 34 | 31 | 10 | 23 | 19 | N | N | N | N | N | N |
| LATS2 | high in NP | -2.3 | 0.040670941 | -1.4 | 13346 | 218 | 231 | 127 | 56 | 85 | 119 | N | N | N | N | N | N |
| LRPAP1 | high in NP | -2.8 | 0.040652427 | -1.4 | 13347 | 19 | 44 | 27 | 12 | 18 | 16 | N | N | N | N | N | N |
| FBRSL1 | high in NP | -2.6 | 0.040593459 | -1.4 | 13348 | 209 | 448 | 514 | 145 | 231 | 178 | NA | NA | N | N | N | N |
| SH2B1 | high in NP | -2.2 | 0.040535176 | -1.4 | 13349 | 48 | 133 | 116 | 42 | 25 | 53 | N | N | N | N | N | N |
| ING3 | high in NP | -2.1 | 0.040483064 | -1.4 | 13350 | 30 | 55 | 65 | 25 | 14 | 26 | N | N | N | N | N | N |
| RAD51L3 | high in NP | -1.9 | 0.040406267 | -1.4 | 13351 | 24 | 21 | 21 | 10 | 10 | 16 | N | N | N | N | N | N |
| MPPED2 | high in NP | -2.1 | 0.040356212 | -1.4 | 13352 | 29 | 23 | 19 | 13 | 19 | 13 | N | N | N | N | N | N |
| NEIL1 | high in NP | -4.4 | 0.040350041 | -1.4 | 13353 | 144 | 34 | 35 | 7 | 22 | 23 | N | N | N | N | N | N |
| RUSC2 | high in NP | -1.9 | 0.040212219 | -1.4 | 13354 | 58 | 53 | 64 | 26 | 38 | 31 | N | N | N | N | N | N |
| PDE4A | high in NP | -3.3 | 0.040199877 | -1.4 | 13355 | 13 | 70 | 36 | 13 | 16 | 13 | N | P | N | N | P | P |
| TMEM66 | high in NP | -2.3 | 0.040184106 | -1.4 | 13356 | 228 | 99 | 68 | 31 | 45 | 55 | N | N | N | N | N | N |

TABLE 16-continued

Genes that Are Differentially Methylated between Nulliparous and Parous CD24+ Breast Epithelial Cells

| | | | | SAGE-seq | Nulliparous (NP) | | | | Parous (P) | | | ChIP-seq | | | MSDK-seq | | |
|---|---|---|---|---|---|---|---|---|---|---|---|---|---|---|---|---|---|
| Gene Symbol | expression pattern | Fold Change | p-value | log10 (P-val.) Rank-ing | CD24+ N48 | CD24+ N58 | CD24+ N43 | CD24+ N37 | CD24+ N39 | CD24+ N40 | NP CD24+ N74 | P CD24+ N66 | GeneBody NP | GeneBody Met P | Pro-moter Met NP | Pro-moter Met P |
| ZFYVE27 | high in NP | -3.0 | 0.040171078 | -1.4 | 13357 | 20 | 82 | 59 | 23 | 19 | 18 | N | N | NP | N | N | N | N |
| PFKFB3 | high in NP | -1.8 | 0.040153936 | -1.4 | 13358 | 463 | 254 | 204 | 171 | 128 | 143 | N | N | N | N | N | N | N |
| HABP4 | high in NP | -1.9 | 0.040125137 | -1.4 | 13359 | 13 | 46 | 17 | 10 | 8 | 8 | N | N | N | N | N | N | N |
| CCDC106 | high in NP | -2.5 | 0.040065483 | -1.4 | 13360 | 17 | 52 | 47 | 11 | 8 | 21 | N | N | P | N | N | N | N |
| HGD | high in NP | -4.6 | 0.040041484 | -1.4 | 13361 | 17 | 6 | 4 | 1 | 8 | 1 | N | N | N | N | N | N | N |
| C12orf45 | high in NP | -2.4 | 0.040035313 | -1.4 | 13362 | 119 | 76 | 129 | 23 | 60 | 58 | N | N | N | N | N | N | N |
| MAPK8 | high in NP | -1.8 | 0.039977715 | -1.4 | 13363 | 10 | 14 | 11 | 6 | 6 | 9 | N | N | N | N | N | N | N |
| ANXA11 | high in NP | -1.6 | 0.039771325 | -1.4 | 13364 | 835 | 1315 | 937 | 620 | 706 | 610 | N | N | N | N | N | N | N |
| DNAJC17 | high in NP | -3.2 | 0.039728812 | -1.4 | 13365 | 41 | 118 | 232 | 19 | 37 | 35 | N | N | N | N | N | N | N |
| C6orf72 | high in NP | -2.3 | 0.039698642 | -1.4 | 13366 | 39 | 67 | 44 | 6 | 24 | 27 | N | N | N | N | N | N | N |
| RPL28 | high in NP | -4.9 | 0.039619789 | -1.4 | 13367 | 11337 | 15308 | 2908 | 2169 | 2333 | 3339 | N | N | N | N | N | N | N |
| TOM1L2 | high in NP | -2.0 | 0.039613618 | -1.4 | 13368 | 137 | 124 | 189 | 64 | 86 | 81 | N | N | N | N | N | N | N |
| WBSCR26 | high in NP | -3.9 | 0.039586876 | -1.4 | 13369 | 22 | 15 | 45 | 11 | 9 | 2 | NA | NA | N | N | N | N | N |
| CTNNBL1 | high in NP | -2.0 | 0.039573848 | -1.4 | 13370 | 81 | 225 | 111 | 57 | 45 | 71 | N | N | N | N | N | N | N |
| MSRA | high in NP | -3.0 | 0.039499794 | -1.4 | 13371 | 30 | 100 | 65 | 30 | 26 | 18 | N | N | N | N | N | N | N |
| NUDC | high in NP | -2.3 | 0.039493623 | -1.4 | 13372 | 941 | 1960 | 3253 | 639 | 825 | 824 | N | N | N | N | N | N | N |
| CARKD | high in NP | -1.8 | 0.039455911 | -1.4 | 13373 | 42 | 117 | 66 | 35 | 36 | 35 | NA | P | N | N | N | N | N |
| HLA-DOA | high in NP | -2.6 | 0.039295461 | -1.4 | 13374 | 19 | 12 | 20 | 10 | 10 | 10 | N | N | N | N | N | N | N |
| CDK7 | high in NP | -1.8 | 0.039263234 | -1.4 | 13375 | 44 | 53 | 29 | 19 | 23 | 29 | N | N | N | N | N | N | N |
| RICS | high in NP | -1.7 | 0.039206322 | -1.4 | 13376 | NA | NA | NA | NA | NA | NA | N | N | N | N | N | N | N |
| MTMR14 | high in NP | -2.3 | 0.039017759 | -1.4 | 13377 | 45 | 42 | 23 | 9 | 21 | 18 | N | N | N | N | N | N | N |
| OSCP1 | high in NP | -1.5 | 0.038966333 | -1.4 | 13378 | 63 | 59 | 53 | 37 | 40 | 36 | NA | NA | N | N | N | N | N |
| PCBP1 | high in NP | -1.9 | 0.038800398 | -1.4 | 13379 | 356 | 203 | 138 | 81 | 106 | 103 | N | N | N | N | N | N | N |
| CLIP1 | high in NP | -2.0 | 0.038720173 | -1.4 | 13380 | 191 | 175 | 108 | 64 | 86 | 84 | N | N | N | N | N | N | N |
| CXorf21 | high in NP | -2.3 | 0.038710573 | -1.4 | 13381 | 41 | 35 | 25 | 25 | 14 | 13 | N | N | N | N | N | N | N |
| IARS | high in NP | -2.5 | 0.038605664 | -1.4 | 13382 | 646 | 604 | 292 | 248 | 257 | 223 | N | N | N | N | N | N | N |
| ZNF773 | high in NP | -6.2 | 0.038599493 | -1.4 | 13383 | 1 | 12 | 7 | 1 | 1 | 1 | N | N | N | N | N | N | N |
| FAM174A | high in NP | -2.3 | 0.038546009 | -1.4 | 13384 | 119 | 156 | 257 | 99 | 87 | 58 | N | N | N | N | N | N | N |
| DLAPH1 | high in NP | -2.1 | 0.038327962 | -1.4 | 13385 | 525 | 1507 | 539 | 286 | 320 | 405 | N | N | N | N | N | N | N |
| CHERP | high in NP | -2.5 | 0.038179169 | -1.4 | 13386 | 217 | 393 | 590 | 142 | 166 | 224 | N | N | N | N | N | N | N |
| BOK | high in NP | -3.8 | 0.038061917 | -1.4 | 13387 | 52 | 183 | 253 | 44 | 50 | 49 | N | N | N | N | N | N | N |
| RELA | high in NP | -2.3 | 0.038018719 | -1.4 | 13388 | 794 | 641 | 466 | 322 | 301 | 415 | N | N | N | N | N | N | N |
| RCE1 | high in NP | -4.6 | 0.037842499 | -1.4 | 13389 | 34 | 254 | 141 | 33 | 31 | 24 | N | N | N | N | N | N | N |
| SIPA1L1 | high in NP | -1.8 | 0.037830156 | -1.4 | 13390 | 153 | 231 | 149 | 124 | 94 | 82 | N | N | N | N | N | N | N |
| TSPAN9 | high in NP | -2.5 | 0.037692334 | -1.4 | 13391 | 35 | 39 | 69 | 28 | 21 | 15 | N | N | N | N | N | N | N |
| FAM114A2 | high in NP | -1.6 | 0.037761828 | -1.4 | 13392 | 10 | 10 | 8 | 6 | 6 | 6 | N | N | N | N | N | N | N |
| PSME1 | high in NP | -2.0 | 0.037566854 | -1.4 | 13393 | 768 | 651 | 439 | 311 | 338 | 348 | N | N | N | N | N | N | N |
| CES2 | high in NP | -2.5 | 0.037560683 | -1.4 | 13394 | 43 | 116 | 70 | 47 | 34 | 18 | N | N | N | N | N | N | N |
| LOC113230 | high in NP | -6.7 | 0.037531884 | -1.4 | 13395 | 1 | 7 | 8 | 1 | 1 | 1 | N | N | N | N | N | N | N |
| SMPDL3B | high in NP | -3.6 | 0.037451659 | -1.4 | 13396 | 18 | 30 | 25 | 16 | 12 | 6 | N | N | N | N | N | N | N |
| GPX7 | high in NP | -2.7 | 0.037451659 | -1.4 | 13397 | 21 | 28 | 33 | 5 | 19 | 11 | N | N | N | N | N | N | N |
| VLDLR | high in NP | -2.1 | 0.037404347 | -1.4 | 13398 | 19 | 34 | 29 | 15 | 17 | 7 | N | N | N | N | N | N | N |
| B9D2 | high in NP | -2.3 | 0.037238412 | -1.4 | 13399 | 22 | 24 | 21 | 17 | 8 | 9 | N | N | N | N | N | N | N |
| ZFP91 | high in NP | -2.7 | 0.037197957 | -1.4 | 13400 | 358 | 578 | 257 | 173 | 143 | 243 | N | N | N | N | N | N | N |

TABLE 16-continued

Genes that Are Differentially Methylated between Nulliparous and Parous CD24+ Breast Epithelial Cells

| | | | | SAGE-seq | | Nulliparous (NP) | | | | Parous (P) | | | ChIP-seq | | | | MSDK-seq | | |
|---|---|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | NP | P | GeneBody NP | GeneBody Met | Pro-moter Met | NP | P |
| | | | | | | | | | | | | | NP | P | | | | Pro-moter Met | Pro-moter Met |
| SETD1A | high in NP | −2.1 | 0.037012137 | −1.4 | 13401 | 31 | 67 | 58 | 17 | 28 | 28 | N | N | N | N | N | N | N | N | N |
| LOC644165 | high in NP | −7.4 | 0.036979909 | −1.4 | 13402 | 2 | 22 | 8 | 2 | 2 | 2 | N | N | N | N | N | N | N | N | N |
| CRIP1 | high in NP | −2.1 | 0.036855801 | −1.4 | 13403 | 13 | 31 | 9 | 8 | 8 | 8 | N | N | N | N | N | N | N | N | N |
| HLA-F | high in NP | −3.3 | 0.036804375 | −1.4 | 13404 | 5725 | 11712 | 14618 | 5609 | 3587 | 727 | N | N | N | N | N | N | N | N | N |
| GRTP1 | high in NP | −2.6 | 0.036745406 | −1.4 | 13405 | 41 | 20 | 50 | 17 | 12 | 16 | N | N | N | N | N | N | N | N | N |
| CYP4F11 | high in NP | −2.2 | 0.036672895 | −1.4 | 13406 | 73 | 48 | 29 | 22 | 24 | 28 | N | P | N | N | N | N | N | N | N |
| USP33 | high in NP | −1.7 | 0.036698094 | −1.4 | 13407 | 60 | 131 | 65 | 49 | 38 | 39 | N | N | N | N | N | N | N | N | N |
| CYB561D2 | high in NP | −2.7 | 0.036624726 | −1.4 | 13408 | 44 | 114 | 47 | 29 | 32 | 16 | N | N | N | N | N | N | N | N | N |
| CALY | high in NP | −7.4 | 0.036506788 | −1.4 | 13409 | 3 | 13 | 10 | 3 | 3 | 3 | N | N | N | N | N | N | N | N | N |
| ST5 | high in NP | −2.4 | 0.036500617 | −1.4 | 13410 | 231 | 613 | 405 | 280 | 151 | 187 | N | N | N | N | N | N | N | N | N |
| SEMA3G | high in NP | −3.2 | 0.036487589 | −1.4 | 13411 | 81 | 33 | 37 | 13 | 13 | 31 | N | N | N | N | N | N | N | N | N |
| GNMT | high in NP | −3.4 | 0.036436163 | −1.4 | 13412 | 53 | 14 | 26 | 3 | 11 | 14 | N | N | N | N | N | N | N | N | N |
| MLST8 | high in NP | −2.1 | 0.036421078 | −1.4 | 13413 | 37 | 61 | 82 | 33 | 26 | 27 | N | NA | N | N | N | N | N | N | N |
| ZFX | high in NP | −2.7 | 0.036355252 | −1.4 | 13414 | 52 | 77 | 32 | 28 | 32 | 17 | N | N | N | N | N | N | N | N | N |
| MMP10 | high in NP | −3.0 | 0.036333331 | −1.4 | 13415 | 6 | 17 | 16 | 6 | 6 | 6 | N | N | N | N | N | N | N | N | N |
| CDK4 | high in NP | −1.7 | 0.036301083 | −1.4 | 13416 | 29 | 42 | 33 | 13 | 22 | 23 | N | N | N | N | N | N | N | N | N |
| CCDC130 | high in NP | −3.0 | 0.036274342 | −1.4 | 13417 | 117 | 350 | 274 | 92 | 117 | 76 | P | P | N | N | N | N | N | N | N |
| CPB1 | high in NP | −7.4 | 0.036242428 | −1.4 | 13418 | 1 | 14 | 7 | 1 | 3 | 3 | N | N | N | N | N | N | N | N | N |
| CDK10 | high in NP | −3.8 | 0.036139948 | −1.4 | 13419 | 16 | 58 | 92 | 12 | 16 | 17 | N | N | N | N | N | N | N | N | N |
| SIGIRR | high in NP | −2.5 | 0.036098121 | −1.4 | 13420 | 128 | 346 | 220 | 93 | 97 | 103 | P | P | N | N | N | N | N | N | N |
| CXorf26 | high in NP | −1.8 | 0.035991155 | −1.4 | 13421 | 9 | 10 | 6 | 4 | 4 | 4 | N | N | N | N | N | N | N | N | N |
| GALNT3 | high in NP | −1.7 | 0.035930129 | −1.4 | 13422 | 100 | 72 | 58 | 40 | 38 | 46 | N | NA | N | N | N | N | N | N | N |
| C7orf36 | high in NP | −8.1 | 0.035626371 | −1.4 | 13423 | 2 | 12 | 9 | 2 | 2 | 2 | N | N | N | N | N | N | N | N | N |
| PRKCD | high in NP | −2.3 | 0.035467293 | −1.5 | 13424 | 295 | 211 | 214 | 46 | 103 | 163 | N | N | N | N | N | N | N | N | N |
| TRAPPC3 | high in NP | −1.7 | 0.035461122 | −1.5 | 13425 | 85 | 112 | 105 | 38 | 59 | 67 | N | N | N | N | N | N | N | N | N |
| KDELR1 | high in NP | −2.0 | 0.035444398 | −1.5 | 13426 | 434 | 567 | 333 | 278 | 237 | 238 | P | P | N | N | N | N | N | N | N |
| C18orf21 | high in NP | −2.3 | 0.035424095 | −1.5 | 13427 | 16 | 21 | 11 | 4 | 11 | 7 | N | N | N | N | N | N | N | N | N |
| ZNHIT2 | high in NP | −2.4 | 0.035417924 | −1.5 | 13428 | 35 | 42 | 33 | 20 | 3 | 16 | N | N | N | N | N | N | N | N | N |
| F11R | high in NP | −2.6 | 0.035386382 | −1.5 | 13429 | 402 | 375 | 212 | 188 | 108 | 166 | N | N | N | N | N | N | N | N | N |
| INTS1 | high in NP | −2.1 | 0.035337404 | −1.5 | 13430 | 542 | 486 | 868 | 251 | 403 | 280 | N | N | N | N | N | N | N | N | N |
| FTO | high in NP | −1.9 | 0.035329471 | −1.5 | 13431 | 97 | 70 | 64 | 47 | 33 | 31 | N | N | N | N | N | N | N | N | N |
| USP36 | high in NP | −2.6 | 0.035299986 | −1.5 | 13432 | 233 | 344 | 390 | 91 | 150 | 218 | N | N | N | N | N | N | N | N | N |
| GNL3 | high in NP | −2.4 | 0.035260217 | −1.5 | 13433 | 135 | 200 | 113 | 50 | 63 | 106 | N | N | N | N | N | N | N | N | N |
| RNASET2 | high in NP | −3.1 | 0.035128566 | −1.5 | 13434 | 438 | 407 | 1950 | 138 | 238 | 270 | N | N | N | N | N | N | N | N | N |
| XRCC1 | high in NP | −2.2 | 0.035017485 | −1.5 | 13435 | 31 | 76 | 60 | 30 | 16 | 20 | N | N | N | N | N | N | N | N | N |
| UBAP2 | high in NP | −1.7 | 0.035011314 | −1.5 | 13436 | 23 | 56 | 49 | 19 | 25 | 18 | N | N | N | N | N | N | N | N | N |
| C19orf42 | high in NP | −2.1 | 0.034990058 | −1.5 | 13437 | 108 | 115 | 93 | 63 | 55 | 16 | N | N | N | N | N | N | N | N | N |
| 40790 | high in NP | −5.1 | 0.034983886 | −1.5 | 13438 | 58 | 19 | 101 | 8 | 13 | 24 | N | N | N | N | N | N | N | N | N |
| SUCLG1 | high in NP | −1.8 | 0.034920804 | −1.5 | 13439 | 584 | 445 | 417 | 250 | 274 | 309 | N | NA | N | N | N | N | N | N | N |
| PLRG1 | high in NP | −1.8 | 0.034822751 | −1.5 | 13440 | 34 | 46 | 25 | 19 | 22 | 15 | N | N | N | N | N | N | N | N | N |
| TRAF3 | high in NP | −1.8 | 0.03478641 | −1.5 | 13441 | 39 | 67 | 45 | 27 | 25 | 34 | N | N | N | N | N | N | N | N | N |
| NCBP2 | high in NP | −2.1 | 0.034678641 | −1.5 | 13442 | 38 | 80 | 47 | 20 | 25 | 34 | N | N | N | N | N | N | N | N | N |
| TACO1 | high in NP | −5.8 | 0.034610189 | −1.5 | 13443 | 20 | 99 | 97 | 13 | 20 | 12 | N | NA | N | N | N | N | N | N | N |
| ZCCHC7 | high in NP | −3.2 | 0.034604018 | −1.5 | 13444 | 15 | 45 | 17 | 7 | 7 | 15 | N | N | N | N | N | N | N | N | N |

TABLE 16-continued

Genes that Are Differentially Methylated between Nulliparous and Parous CD24+ Breast Epithelial Cells

| | | | | SAGE-seq | | | | | | | | ChIP-seq | | | MSDK-seq | | |
|---|---|---|---|---|---|---|---|---|---|---|---|---|---|---|---|---|---|
| | | | log10 | | Nulliparous (NP) | | | | Parous (P) | | | NP | P | | | | |
| Gene Symbol | expression pattern | Fold Change | p-value | (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | GeneBody Met | Pro-moter Met | Pro-moter Met |
| MAST4 | high in NP | -2.2 | 0.034572477 | -1.5 | 13445 | 164 | 439 | 287 | 131 | 140 | 172 | N | N | N | N | N | N |
| NRAS | high in NP | -2.7 | 0.034524479 | -1.5 | 13446 | 134 | 481 | 144 | 110 | 60 | 63 | N | N | N | N | N | N |
| UFC1 | high in NP | -1.9 | 0.034518308 | -1.5 | 13447 | 1525 | 1119 | 1526 | 777 | 737 | 805 | N | N | N | N | N | N |
| G6PC | high in NP | -4.2 | 0.034512137 | -1.5 | 13448 | 28 | 55 | 81 | 21 | 22 | 4 | N | N | N | N | N | N |
| KIAA0895 | high in NP | -2.3 | 0.03430506 | -1.5 | 13449 | 33 | 51 | 62 | 10 | 19 | 29 | N | N | N | N | N | N |
| BACE2 | high in NP | -1.8 | 0.034276947 | -1.5 | 13450 | 27 | 52 | 24 | 18 | 16 | 10 | N | N | N | N | N | N |
| TUT1 | high in NP | -2.4 | 0.034244035 | -1.5 | 13451 | 12 | 11 | 19 | 6 | 9 | 4 | N | N | N | N | N | N |
| COMMD9 | high in NP | -1.9 | 0.034101413 | -1.5 | 13452 | 144 | 114 | 132 | 79 | 87 | 56 | N | N | N | N | N | N |
| ZNF211 | high in NP | -9.7 | 0.034095241 | -1.5 | 13453 | 3 | 30 | 12 | 3 | 3 | 3 | N | N | N | N | N | N |
| UXT | high in NP | -2.9 | 0.033989646 | -1.5 | 13454 | 544 | 292 | 197 | 75 | 140 | 163 | N | N | N | N | N | N |
| KDM1A | high in NP | -3.2 | 0.033918335 | -1.5 | 13455 | 136 | 166 | 57 | 50 | 48 | 41 | N | N | N | N | N | N |
| TAF5L | high in NP | -1.9 | 0.033905307 | -1.5 | 13456 | 57 | 81 | 48 | 38 | 29 | 36 | N | N | N | N | N | N |
| FBXO7 | high in NP | -2.6 | 0.033899136 | -1.5 | 13457 | 26 | 54 | 27 | 25 | 10 | 13 | N | N | N | N | N | N |
| NLRP8 | high in NP | -1.8 | 0.033797655 | -1.5 | 13458 | 434 | 401 | 293 | 227 | 173 | 237 | N | N | N | N | N | N |
| C11orf59 | high in NP | -3.0 | 0.033775713 | -1.5 | 13459 | 40 | 95 | 47 | 27 | 28 | 14 | N | N | N | N | N | N |
| ATP1A1 | high in NP | -2.3 | 0.033769542 | -1.5 | 13460 | 1457 | 3000 | 1085 | 687 | 553 | 923 | N | N | N | N | N | N |
| CMPK2 | high in NP | -2.2 | 0.033763371 | -1.5 | 13461 | 17 | 33 | 26 | 13 | 15 | 11 | N | N | N | N | N | N |
| KIAA0922 | high in NP | -2.9 | 0.033652976 | -1.5 | 13462 | 72 | 39 | 22 | 16 | 19 | 22 | N | N | N | N | N | N |
| CCL28 | high in NP | -2.2 | 0.033633091 | -1.5 | 13463 | 37 | 35 | 16 | 7 | 18 | 11 | N | N | N | N | N | N |
| EFCAB4A | high in NP | -4.4 | 0.033563151 | -1.5 | 13464 | 423 | 112 | 224 | 22 | 42 | 131 | N | N | N | N | N | N |
| PINX1 | high in NP | -9.8 | 0.033454813 | -1.5 | 13465 | 3 | 23 | 13 | 3 | 3 | 3 | N | N | N | N | N | N |
| STAT6 | high in NP | -2.5 | 0.0333636 | -1.5 | 13466 | 499 | 1316 | 966 | 420 | 400 | 466 | N | N | N | N | N | N |
| FBXO36 | high in NP | -1.7 | 0.033316991 | -1.5 | 13467 | 39 | 42 | 28 | 22 | 24 | 21 | N | N | N | P | N | N |
| ATP5F1 | high in NP | -4.0 | 0.03331082 | -1.5 | 13468 | 249 | 239 | 71 | 66 | 36 | 66 | N | N | N | N | N | N |
| ESRRA | high in NP | -4.0 | 0.033304649 | -1.5 | 13469 | 219 | 728 | 755 | 203 | 220 | 169 | N | N | N | N | N | N |
| RAB17 | high in NP | -2.6 | 0.033268308 | -1.5 | 13470 | 144 | 284 | 338 | 172 | 64 | 59 | N | N | N | N | N | N |
| CMAH | high in NP | -2.5 | 0.033239509 | -1.5 | 13471 | 26 | 19 | 11 | 6 | 13 | 6 | N | N | N | N | N | N |
| RDH13 | high in NP | -2.3 | 0.033114715 | -1.5 | 13472 | 86 | 60 | 71 | 24 | 39 | 40 | N | N | N | N | N | N |
| PTGES2 | high in NP | -1.7 | 0.033101001 | -1.5 | 13473 | 12 | 19 | 21 | 9 | 10 | 7 | N | N | N | N | N | N |
| CCDC112 | high in NP | -1.8 | 0.033085916 | -1.5 | 13474 | 10 | 11 | 7 | 5 | 5 | 5 | P | N | N | N | N | N |
| FGFR1OP2 | high in NP | -2.5 | 0.033042032 | -1.5 | 13475 | 15 | 37 | 10 | 9 | 7 | 10 | N | N | N | N | N | N |
| ARMC6 | high in NP | -3.6 | 0.033015976 | -1.5 | 13476 | 63 | 169 | 242 | 41 | 48 | 64 | N | N | N | N | N | N |
| SLC1A4 | high in NP | -1.8 | 0.032957693 | -1.5 | 13477 | 36 | 79 | 51 | 34 | 26 | 16 | N | N | N | N | N | N |
| BMP7 | high in NP | -2.2 | 0.032865126 | -1.5 | 13478 | 323 | 211 | 361 | 165 | 124 | 159 | P | N | N | N | N | N |
| SNRPD2 | high in NP | -2.9 | 0.032747189 | -1.5 | 13479 | 546 | 288 | 285 | 88 | 164 | 207 | N | P | N | N | N | N |
| RMND5A | high in NP | -1.6 | 0.032741018 | -1.5 | 13480 | 87 | 111 | 119 | 72 | 77 | 60 | N | N | N | N | N | N |
| ZNF20 | high in NP | -1.9 | 0.032673821 | -1.5 | 13481 | 24 | 18 | 13 | 12 | 7 | 10 | N | N | N | N | N | N |
| C11orf60 | high in NP | -2.1 | 0.032646393 | -1.5 | 13482 | NA | NA | NA | NA | NA | NA | N | N | N | N | N | N |
| HSD3B7 | high in NP | -3.6 | 0.032259312 | -1.5 | 13483 | 36 | 149 | 136 | 40 | 31 | 29 | N | N | N | N | N | N |
| PXN | high in NP | -2.0 | 0.032546284 | -1.5 | 13484 | 148 | 110 | 106 | 54 | 67 | 75 | N | N | N | N | N | N |
| IMPDH1 | high in NP | -1.8 | 0.032459888 | -1.5 | 13485 | 298 | 413 | 666 | 190 | 228 | 237 | P | P | N | N | N | N |
| VSIG2 | high in NP | -2.4 | 0.032441374 | -1.5 | 13486 | 25 | 114 | 42 | 18 | 18 | 13 | P | N | N | N | N | N |
| PMCHL2 | high in NP | -2.1 | 0.032348807 | -1.5 | 13487 | 7 | 5 | 3 | 2 | 2 | 2 | N | N | N | N | N | N |
| WDFY2 | high in NP | -2.0 | 0.032239207 | -1.5 | 13488 | 93 | 73 | 95 | 46 | 48 | 49 | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | MSDK-seq | | |
| --- | --- | --- | --- | --- | --- | --- | --- | --- | --- | --- | --- | --- | --- | --- | --- | --- | --- |
| | | | | | | Nulliparous (NP) | | | | Parous (P) | | | NP | P | GeneBody | Pro-moter | Pro-moter |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | CD24+ N74 | CD24+ N66 | GeneBody | Met | Met | Met |
| NDUFAF3 | high in NP | -2.0 | 0.032237726 | -1.5 | 13489 | 62 | 156 | 95 | 45 | 48 | 51 | NA | NA | N | N | N | N |
| TMEM160 | high in NP | -2.6 | 0.032195214 | -1.5 | 13490 | 78 | 144 | 252 | 71 | 53 | 40 | N | N | N | N | N | N |
| CUL4B | high in NP | -2.2 | 0.032130074 | -1.5 | 13491 | 44 | 43 | 27 | 15 | 25 | 21 | N | N | N | N | N | N |
| MCL1 | high in NP | -2.2 | 0.032060134 | -1.5 | 13492 | 2162 | 1719 | 1318 | 625 | 752 | 1172 | N | N | N | N | N | N |
| C6orf154 | high in NP | -12.4 | 0.032053963 | -1.5 | 13493 | 2 | 19 | 15 | 2 | 2 | 2 | N | N | N | N | N | N |
| ROPN1 | high in NP | -2.5 | 0.031975795 | -1.5 | 13494 | 9 | 2 | 6 | 1 | 2 | 4 | N | N | N | N | N | N |
| CD276 | high in NP | -2.7 | 0.031957282 | -1.5 | 13495 | 223 | 538 | 495 | 190 | 178 | 197 | N | N | N | N | N | N |
| FAF2 | high in NP | -2.0 | 0.03193534 | -1.5 | 13496 | 52 | 65 | 36 | 28 | 22 | 18 | N | N | N | N | N | N |
| SLC2A4RG | high in NP | -2.2 | 0.031857858 | -1.5 | 13497 | 40 | 67 | 47 | 20 | 36 | 14 | N | N | N | N | N | P |
| METTL9 | high in NP | -2.3 | 0.031820831 | -1.5 | 13498 | 53 | 32 | 17 | 9 | 14 | 14 | N | N | N | N | N | N |
| LEMD2 | high in NP | -2.2 | 0.031805746 | -1.5 | 13499 | 120 | 261 | 182 | 87 | 82 | 113 | P | N | N | N | N | N |
| NR3C2 | high in NP | -2.0 | 0.031765976 | -1.5 | 13500 | 36 | 47 | 27 | 18 | 19 | 22 | N | N | N | N | N | N |
| TSC22D4 | high in NP | -2.2 | 0.031726207 | -1.5 | 13501 | 116 | 235 | 178 | 102 | 50 | 80 | N | N | N | P | N | N |
| HOOK2 | high in NP | -1.8 | 0.031689180 | -1.5 | 13502 | 56 | 49 | 65 | 23 | 26 | 33 | N | N | N | N | N | N |
| SSNA1 | high in NP | -5.0 | 0.031654210 | -1.5 | 13503 | 100 | 456 | 565 | 98 | 113 | 37 | N | N | N | N | N | N |
| MRPL55 | high in NP | -2.1 | 0.031630211 | -1.5 | 13504 | 369 | 316 | 583 | 176 | 246 | 189 | N | N | N | N | N | N |
| ATP10A | high in NP | -1.9 | 0.031593870 | -1.5 | 13505 | 40 | 99 | 45 | 26 | 30 | 24 | N | N | N | N | N | N |
| UBE2E2 | high in NP | -2.9 | 0.031587699 | -1.5 | 13506 | 122 | 133 | 53 | 41 | 43 | 43 | N | N | N | N | N | N |
| ARHGEF5 | high in NP | -2.5 | 0.031574671 | -1.5 | 13507 | 435 | 474 | 957 | 202 | 223 | 365 | N | N | N | N | N | N |
| TMEM110 | high in NP | -13.4 | 0.031538330 | -1.5 | 13508 | 4 | 22 | 18 | 4 | 4 | 4 | N | N | N | N | N | N |
| RETSAT | high in NP | -1.7 | 0.031485532 | -1.5 | 13509 | 220 | 193 | 223 | 122 | 136 | 121 | N | N | N | N | N | N |
| MRPS12 | high in NP | -3.9 | 0.031456733 | -1.5 | 13510 | 44 | 265 | 107 | 31 | 41 | 25 | N | N | N | N | N | N |
| DBNDD1 | high in NP | -3.0 | 0.031450562 | -1.5 | 13511 | 113 | 383 | 341 | 129 | 85 | 58 | N | N | N | N | N | N |
| CASZ1 | high in NP | -1.5 | 0.031402564 | -1.5 | 13512 | 1006 | 901 | 1063 | 725 | 748 | 745 | NA | NA | N | N | N | N |
| SAP30BP | high in NP | -2.4 | 0.031396393 | -1.5 | 13513 | 13 | 5 | 5 | 5 | 4 | 1 | NA | NA | N | N | N | N |
| UPF3A | high in NP | -3.2 | 0.031275713 | -1.5 | 13514 | 138 | 408 | 297 | 95 | 107 | 136 | N | N | N | N | N | N |
| C11orf66 | high in NP | -2.3 | 0.031233886 | -1.5 | 13515 | 88 | 121 | 63 | 51 | 46 | 24 | N | N | N | N | N | N |
| PRR23A | high in NP | -2.0 | 0.031134462 | -1.5 | 13516 | 22 | 32 | 56 | 15 | 15 | 11 | N | N | N | N | N | N |
| DSC2 | high in NP | -4.8 | 0.031100178 | -1.5 | 13517 | 1071 | 366 | 214 | 41 | 85 | 243 | NA | NA | N | N | N | N |
| CDC42BPG | high in NP | -3.7 | 0.031041895 | -1.5 | 13518 | 859 | 733 | 306 | 195 | 239 | 287 | N | N | P | N | N | N |
| UQCR11 | high in NP | -1.6 | 0.031013782 | -1.5 | 13519 | 15 | 20 | 22 | 12 | 10 | 10 | N | N | N | N | N | P |
| RAP1GAP | high in NP | -2.5 | 0.030998012 | -1.5 | 13520 | 494 | 359 | 1337 | 221 | 288 | 223 | NA | NA | N | N | N | N |
| LIN7B | high in NP | -3.1 | 0.03097127 | -1.5 | 13521 | 139 | 83 | 201 | 32 | 53 | 69 | N | N | N | N | N | N |
| FCH01 | high in NP | -3.4 | 0.030911615 | -1.5 | 13522 | 14 | 34 | 49 | 9 | 9 | 10 | N | N | N | N | N | N |
| MYH9 | high in NP | -2.0 | 0.030864989 | -1.5 | 13523 | 17 | 10 | 16 | 6 | 11 | 6 | N | N | N | N | N | N |
| SF1 | high in NP | -1.7 | 0.030840304 | -1.5 | 13524 | 3281 | 2568 | 4229 | 2052 | 2271 | 1716 | N | N | N | N | N | N |
| PPP1R1A | high in NP | -2.0 | 0.030818363 | -1.5 | 13525 | 1199 | 1595 | 1232 | 648 | 835 | 949 | N | N | N | N | N | N |
| ALOXE3 | high in NP | -2.6 | 0.030778593 | -1.5 | 13526 | 46 | 23 | 37 | 14 | 18 | 15 | P | N | P | N | N | N |
| CCNE2 | high in NP | -2.0 | 0.030741566 | -1.5 | 13527 | 78 | 124 | 111 | 44 | 43 | 71 | N | N | N | N | N | N |
| CABP5 | high in NP | -2.5 | 0.030668884 | -1.5 | 13528 | 11 | 7 | 4 | 3 | 3 | 3 | N | P | N | N | N | P |
| ABCC8 | high in NP | -4.7 | 0.030639399 | -1.5 | 13529 | 22 | 15 | 7 | 9 | 5 | 2 | P | P | N | N | N | N |
| IPO5 | high in NP | -2.0 | 0.030618829 | -1.5 | 13530 | 19 | 20 | 41 | 11 | 10 | 7 | N | P | N | N | N | N |
| TCTN3 | high in NP | -2.1 | 0.030518719 | -1.5 | 13531 | 388 | 256 | 211 | 115 | 125 | 158 | N | N | N | N | N | N |
| | high in NP | -2.3 | 0.03050912 | -1.5 | 13532 | 51 | 98 | 68 | 27 | 50 | 25 | N | N | N | N | N | N |

TABLE 16-continued

Genes that Are Differentially Methylated between Nulliparous and Parous CD24+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| Gene Symbol | expression pattern | Fold Change | p-value | log10 (P-val.) | Rank-ing | Nulliparous (NP) CD24+ N48 | CD24+ N58 | CD24+ N43 | CD24+ N37 | Parous (P) CD24+ N39 | CD24+ N40 | NP CD24+ N74 | P CD24+ N66 | NP GeneBody | P GeneBody Met | NP Pro-moter Met | P Pro-moter Met |
|---|---|---|---|---|---|---|---|---|---|---|---|---|---|---|---|---|---|
| ARIH2 | high in NP | −1.8 | 0.030446037 | −1.5 | 13533 | 183 | 255 | 197 | 102 | 134 | 141 | N | N | N | N | N | N |
| ZNF600 | high in NP | 4.6 | 0.030419295 | −1.5 | 13534 | 9 | 6 | 4 | 1 | 6 | 1 | N | N | N | N | N | N |
| APEX1 | high in NP | −2.2 | 0.030365812 | −1.5 | 13535 | 56 | 20 | 15 | 8 | 9 | 12 | N | N | N | N | N | N |
| OTUB1 | high in NP | −3.6 | 0.03021359 | −1.5 | 13536 | 116 | 595 | 297 | 107 | 93 | 82 | N | N | N | N | N | N |
| RPL27A | high in NP | −4.3 | 0.030207419 | −1.5 | 13537 | 1260 | 255 | 368 | 98 | 102 | 234 | N | N | N | N | N | N |
| LOC100131496 | high in NP | −1.6 | 0.030151193 | −1.5 | 13538 | 67 | 73 | 54 | 36 | 38 | 45 | NA | NA | N | N | N | N |
| FAM86B2 | high in NP | −15.4 | 0.030145022 | −1.5 | 13539 | 1 | 31 | 18 | 1 | 1 | 1 | NA | NA | N | N | N | N |
| DCAF8 | high in NP | −2.8 | 0.030026399 | −1.5 | 13540 | 150 | 200 | 128 | 31 | 64 | 100 | N | N | N | N | N | N |
| ANKK1 | high in NP | −2.5 | 0.029940688 | −1.5 | 13541 | 237 | 218 | 120 | 86 | 89 | 95 | N | N | N | N | N | N |
| PPP1R8 | high in NP | −1.9 | 0.029896119 | −1.5 | 13542 | 32 | 60 | 29 | 19 | 22 | 17 | N | N | N | N | N | N |
| ARGLU1 | high in NP | −3.1 | 0.029854978 | −1.5 | 13543 | 186 | 113 | 71 | 35 | 36 | 75 | N | N | N | N | N | N |
| FGL1 | high in NP | −2.9 | 0.029789838 | −1.5 | 13544 | 40 | 5 | 5 | 2 | 5 | 2 | N | N | N | N | N | N |
| HIGD2A | high in NP | −2.7 | 0.029743212 | −1.5 | 13545 | 188 | 110 | 224 | 79 | 62 | 94 | N | N | N | N | N | N |
| CYBA | high in NP | −2.2 | 0.029720584 | −1.5 | 13546 | 132 | 214 | 274 | 95 | 114 | 72 | N | N | N | N | N | N |
| TMED2 | high in NP | −3.5 | 0.029710985 | −1.5 | 13547 | 965 | 1415 | 417 | 347 | 303 | 337 | N | N | N | N | N | N |
| NTRK3 | high in NP | −1.8 | 0.029533393 | −1.5 | 13548 | 20 | 22 | 24 | 15 | 15 | 18 | N | N | N | N | N | N |
| PAPSS1 | high in NP | −2.7 | 0.029359915 | −1.5 | 13549 | 71 | 110 | 39 | 40 | 23 | 25 | N | N | N | N | N | N |
| IL11 | high in NP | −2.8 | 0.029320145 | −1.5 | 13550 | 19 | 22 | 39 | 13 | 7 | 13 | N | N | N | N | N | N |
| HS1BP3 | high in NP | −2.4 | 0.02927489 | −1.5 | 13551 | 22 | 44 | 19 | 19 | 14 | 6 | N | N | N | N | N | N |
| ADPRHL2 | high in NP | −2.1 | 0.029235806 | −1.5 | 13552 | 32 | 77 | 40 | 19 | 27 | 23 | N | N | N | N | N | N |
| STUB1 | high in NP | −2.7 | 0.029071928 | −1.5 | 13553 | 42 | 171 | 76 | 31 | 29 | 37 | N | N | N | N | N | N |
| FER1L4 | high in NP | −2.0 | 0.029007474 | −1.5 | 13554 | 21 | 35 | 45 | 16 | 16 | 19 | N | N | N | N | N | N |
| BAHCC1 | high in NP | −2.1 | 0.028988961 | −1.5 | 13555 | 34 | 76 | 55 | 33 | 27 | 23 | N | N | N | N | N | N |
| TNF | high in NP | −2.8 | 0.028959476 | −1.5 | 13556 | 2902 | 1444 | 3897 | 862 | 1260 | 1087 | N | N | N | N | N | N |
| LOC400927 | high in NP | −2.8 | 0.028944391 | −1.5 | 13557 | 9 | 9 | 6 | 3 | 6 | 1 | N | N | N | N | N | N |
| SAP130 | high in NP | −2.5 | 0.02886348 | −1.5 | 13558 | 48 | 66 | 28 | 28 | 18 | 21 | N | N | N | N | N | N |
| SHCBP1 | high in NP | −3.7 | 0.028827825 | −1.5 | 13559 | 417 | 698 | 197 | 115 | 131 | 192 | N | P | N | N | N | N |
| CHMP4B | high in NP | −1.9 | 0.028739372 | −1.5 | 13560 | 527 | 532 | 456 | 214 | 297 | 352 | N | P | N | N | N | N |
| ENGASE | high in NP | −2.4 | 0.028710573 | −1.5 | 13561 | 92 | 193 | 373 | 47 | 79 | 77 | NA | N | N | N | N | N |
| AKAP8L | high in NP | −2.2 | 0.028690003 | −1.5 | 13562 | 249 | 483 | 423 | 181 | 224 | 187 | N | N | N | N | N | N |
| TRAFD1 | high in NP | −2.8 | 0.028651604 | −1.5 | 13563 | 676 | 680 | 319 | 271 | 219 | 224 | N | N | N | N | N | N |
| ARFRP1 | high in NP | −4.1 | 0.028639262 | −1.5 | 13564 | 32 | 207 | 85 | 24 | 20 | 33 | N | N | N | N | N | N |
| CFL1 | high in NP | −2.2 | 0.02862692 | −1.5 | 13565 | 7586 | 8998 | 7159 | 3350 | 5608 | 2876 | N | N | N | N | N | N |
| TNIP2 | high in NP | −2.1 | 0.028613892 | −1.5 | 13566 | 26 | 52 | 30 | 21 | 12 | 15 | N | N | N | N | N | N |
| NCSTN | high in NP | −2.0 | 0.028580979 | −1.5 | 13567 | 45 | 95 | 43 | 30 | 31 | 23 | N | N | N | N | N | N |
| VARS2 | high in NP | −2.7 | 0.028574808 | −1.5 | 13568 | 149 | 352 | 328 | 113 | 136 | 120 | N | N | N | N | N | N |
| CLDN3 | high in NP | −2.7 | 0.02855218 | −1.5 | 13569 | 4115 | 1290 | 2238 | 865 | 918 | 770 | N | N | N | N | N | N |
| FAM108A1 | high in NP | −3.7 | 0.028413673 | −1.5 | 13570 | 204 | 533 | 854 | 163 | 235 | 130 | N | N | N | N | N | N |
| PTHLH | high in NP | 5.2 | 0.028407501 | −1.5 | 13571 | 284 | 1123 | 956 | 198 | 308 | 34 | P | P | N | N | N | N |
| C7orf63 | high in NP | −2.3 | 0.028314248 | −1.5 | 13572 | 77 | 65 | 33 | 28 | 21 | 27 | N | N | N | N | N | N |
| WAPAL | high in NP | −2.3 | 0.028279964 | −1.5 | 13573 | 63 | 116 | 82 | 30 | 42 | 57 | N | N | N | N | N | N |
| ORMDL2 | high in NP | −2.3 | 0.028264879 | −1.5 | 13574 | 93 | 168 | 183 | 46 | 88 | 49 | N | N | N | N | N | N |
| ZFP57 | high in NP | −4.2 | 0.028205911 | −1.5 | 13575 | 27 | 50 | 114 | 21 | 17 | 6 | N | N | N | N | P | N |
| MRPS34 | high in NP | −2.7 | 0.028182597 | −1.6 | 13576 | 68 | 260 | 118 | 68 | 47 | 30 | N | N | N | N | N | N |

TABLE 16-continued

Genes that Are Differentially Methylated between Nulliparous and Parous CD24+ Breast Epithelial Cells

| | | | | | SAGE-seq | Nulliparous (NP) | | | | Parous (P) | | | ChIP-seq | | | MSDK-seq | | |
|---|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody | Pro-moter Met | GeneBody Met | Pro-moter Met | 
| | | | | | | | | | | | | NP | P | NP | P | NP | P |
| OSGEP | high in NP | −2.6 | 0.028144885 | −1.6 | 13577 | 22 | 34 | 28 | 14 | 5 | 14 | N | N | N | N | N | N |
| CCDC142 | high in NP | −2.0 | 0.028106487 | −1.6 | 13578 | 46 | 28 | 24 | 17 | 15 | 18 | N | N | N | N | N | N |
| LAGE3 | high in NP | −2.5 | 0.028048204 | −1.6 | 13579 | 17 | 11 | 6 | 5 | 5 | 5 | N | N | N | N | N | N |
| RPL7L1 | high in NP | −1.6 | 0.027885697 | −1.6 | 13580 | 14 | 9 | 8 | 6 | 6 | 6 | N | N | N | N | N | N |
| NWD1 | high in NP | −4.0 | 0.027769131 | −1.6 | 13581 | 20 | 14 | 16 | 6 | 6 | 15 | N | N | N | N | N | N |
| OBFC1 | high in NP | −1.9 | 0.027699877 | −1.6 | 13582 | 123 | 230 | 115 | 78 | 86 | 62 | N | N | N | N | N | N |
| OASL | high in NP | −4.4 | 0.027653936 | −1.6 | 13583 | 26 | 12 | 3 | 2 | 2 | 2 | N | N | N | N | N | N |
| LYPLAL1 | high in NP | −2.2 | 0.027647765 | −1.6 | 13584 | 13 | 13 | 7 | 5 | 5 | 5 | N | N | N | N | N | N |
| AQP3 | high in NP | −3.3 | 0.027663268 | −1.6 | 13585 | 95 | 726 | 178 | 47 | 57 | 75 | N | N | N | N | N | N |
| GTF2H4 | high in NP | −3.4 | 0.027479087 | −1.6 | 13586 | 63 | 121 | 257 | 30 | 56 | 33 | N | N | N | N | N | N |
| C19orf60 | high in NP | −1.7 | 0.027392691 | −1.6 | 13587 | 94 | 113 | 191 | 66 | 64 | 56 | N | N | N | N | N | N |
| SLC9A8 | high in NP | −2.2 | 0.027386519 | −1.6 | 13588 | 61 | 148 | 97 | 65 | 43 | 34 | N | N | N | N | N | N |
| FLJ45079 | high in NP | −3.2 | 0.027348121 | −1.6 | 13589 | 57 | 40 | 30 | 9 | 28 | 11 | N | N | N | N | N | N |
| PPP1R1B | high in NP | −3.4 | 0.027314523 | −1.6 | 13590 | 159 | 69 | 122 | 18 | 27 | 65 | N | P | N | N | N | N |
| C14orf179 | high in NP | −3.7 | 0.027254183 | −1.6 | 13591 | 18 | 9 | 3 | 2 | 2 | 2 | N | N | N | N | N | N |
| YIPF1 | high in NP | −2.5 | 0.027219213 | −1.6 | 13592 | 15 | 22 | 9 | 7 | 7 | 7 | N | N | N | N | N | N |
| KIAA0240 | high in NP | −1.8 | 0.027178758 | −1.6 | 13593 | 46 | 54 | 41 | 32 | 25 | 22 | N | N | N | P | N | N |
| RBMX | high in NP | −2.1 | 0.027166093 | −1.6 | 13594 | 15 | 10 | 15 | 9 | 7 | 7 | N | N | N | N | N | N |
| KCNH6 | high in NP | −4.8 | 0.027156133 | −1.6 | 13595 | 130 | 164 | 64 | 30 | 9 | 61 | N | N | N | N | N | N |
| RBM14 | high in NP | −2.1 | 0.027097847 | −1.6 | 13596 | 70 | 143 | 150 | 51 | 50 | 71 | N | N | N | N | N | N |
| C19orf63 | high in NP | −3.7 | 0.027041621 | −1.6 | 13597 | 367 | 1198 | 1124 | 350 | 300 | 289 | N | N | N | N | N | N |
| TSPAN4 | high in NP | −2.4 | 0.026943568 | −1.6 | 13598 | 58 | 73 | 154 | 31 | 31 | 42 | N | N | N | N | N | N |
| OR7E156P | high in NP | −2.6 | 0.026903799 | −1.6 | 13599 | 12 | 11 | 51 | 4 | 7 | 4 | N | N | N | N | N | N |
| GAS2L1 | high in NP | −2.1 | 0.026845516 | −1.6 | 13600 | 75 | 98 | 81 | 43 | 31 | 60 | N | N | N | N | N | N |
| CHD2 | high in NP | −2.3 | 0.02675912 | −1.6 | 13601 | 3611 | 2845 | 2773 | 907 | 1322 | 2122 | N | N | N | N | N | N |
| PEBP1 | high in NP | −2.0 | 0.026747463 | −1.6 | 13602 | 1170 | 2263 | 1162 | 631 | 794 | 620 | N | N | N | N | N | N |
| STCML2 | high in NP | −2.8 | 0.026737863 | −1.6 | 13603 | 163 | 807 | 230 | 91 | 79 | 133 | N | N | N | N | N | N |
| ALOX15B | high in NP | −3.0 | 0.026584956 | −1.6 | 13604 | 611 | 262 | 484 | 239 | 121 | 169 | N | N | N | N | N | N |
| RPL37 | high in NP | −4.8 | 0.026548615 | −1.6 | 13605 | 7054 | 1501 | 1587 | 338 | 791 | 926 | N | N | N | N | N | N |
| SUDS3 | high in NP | −2.3 | 0.026532159 | −1.6 | 13606 | 56 | 92 | 42 | 30 | 28 | 25 | N | N | N | N | N | N |
| TTC27 | high in NP | −1.8 | 0.026519131 | −1.6 | 13607 | 47 | 40 | 32 | 19 | 25 | 17 | N | N | N | N | N | N |
| PABPC4 | high in NP | −2.7 | 0.02647319 | −1.6 | 13608 | 221 | 612 | 268 | 101 | 150 | 163 | N | N | N | N | N | N |
| PSME2 | high in NP | −2.9 | 0.026453991 | −1.6 | 13609 | 135 | 400 | 227 | 58 | 134 | 89 | N | N | N | N | N | N |
| KIAA0247 | high in NP | −2.4 | 0.026379937 | −1.6 | 13610 | 492 | 614 | 379 | 229 | 251 | 313 | N | N | N | N | N | N |
| C7orf20 | high in NP | −2.1 | 0.026237315 | −1.6 | 13611 | NA | NA | NA | NA | NA | NA | N | N | N | N | N | N |
| HBXIP | high in NP | −2.2 | 0.026187946 | −1.6 | 13612 | 495 | 499 | 313 | 153 | 248 | 233 | N | N | N | N | N | N |
| TMEM9 | high in NP | −2.5 | 0.026137891 | −1.6 | 13613 | 47 | 46 | 25 | 21 | 15 | 7 | N | N | N | N | N | N |
| GPR160 | high in NP | −3.3 | 0.026094007 | −1.6 | 13614 | 11 | 9 | 3 | 2 | 2 | 2 | N | N | N | N | N | N |
| PPL | high in NP | −1.9 | 0.026080979 | −1.6 | 13615 | 60 | 113 | 66 | 35 | 41 | 40 | N | N | N | N | N | N |
| ZSWIM4 | high in NP | −2.0 | 0.025940414 | −1.6 | 13616 | 80 | 95 | 56 | 29 | 33 | 43 | N | N | N | N | N | N |
| CSNK2B | high in NP | −1.8 | 0.025927386 | −1.6 | 13617 | 946 | 2011 | 1094 | 639 | 632 | 551 | N | N | N | N | N | N |
| SF4 | high in NP | −2.8 | 0.025881445 | −1.6 | 13618 | 21 | 45 | 22 | 7 | 15 | 13 | N | N | N | N | N | N |
| C17orf81 | high in NP | −1.7 | 0.025792307 | −1.6 | 13619 | 35 | 38 | 39 | 19 | 24 | 18 | N | N | N | N | N | N |
| EEPD1 | high in NP | −2.7 | 0.025732652 | −1.6 | 13620 | 45 | 20 | 34 | 11 | 12 | 20 | N | N | N | N | N | N |

TABLE 16-continued

Genes that Are Differentially Methylated between Nulliparous and Parous CD24+ Breast Epithelial Cells

| | | | | SAGE-seq | | Nulliparous (NP) | | | | Parous (P) | | | ChIP-seq | | | | MSDK-seq | | |
|---|---|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | GeneBody Met | P GeneBody Met | NP Pro-moter | Pro-moter Met | P Pro-moter Met |
| STX18 | high in NP | −2.2 | 0.025683969 | −1.6 | 13621 | 25 | 14 | 14 | 10 | 11 | 14 | N | N | N | N | N | N | N | N |
| DNTTIP2 | high in NP | −1.6 | 0.025672312 | −1.6 | 13622 | 147 | 143 | 147 | 86 | 102 | 82 | N | N | N | N | N | N | N | N |
| MMP24 | high in NP | −2.9 | 0.025265517 | −1.6 | 13623 | 17 | 22 | 30 | 8 | 8 | 16 | N | N | N | N | N | N | N | N |
| ACSL3 | high in NP | −2.5 | 0.025611972 | −1.6 | 13624 | 167 | 133 | 77 | 35 | 61 | 54 | N | N | N | N | N | N | N | N |
| CTR9 | high in NP | −2.5 | 0.025601001 | −1.6 | 13625 | 93 | 149 | 65 | 40 | 42 | 52 | N | N | N | N | N | N | N | N |
| C11orf68 | high in NP | −3.2 | 0.025555506 | −1.6 | 13626 | 611 | 290 | 703 | 116 | 217 | 228 | N | N | N | N | N | N | N | N |
| SNAPC5 | high in NP | −1.8 | 0.025548889 | −1.6 | 13627 | 10 | 8 | 18 | 5 | 5 | 5 | N | N | N | N | N | N | N | N |
| UQCRC1 | high in NP | −1.8 | 0.025533118 | −1.6 | 13628 | 718 | 897 | 674 | 530 | 422 | 376 | N | N | N | N | N | N | N | N |
| DHPS | high in NP | −2.1 | 0.025518719 | −1.6 | 13629 | 59 | 65 | 61 | 17 | 31 | 38 | N | N | N | N | N | N | N | N |
| CLDND1 | high in NP | −2.3 | 0.025427523 | −1.6 | 13630 | 309 | 558 | 335 | 128 | 176 | 241 | N | N | N | N | N | P | N | N |
| ZNF408 | high in NP | −2.9 | 0.025382268 | −1.6 | 13631 | 50 | 95 | 244 | 37 | 33 | 23 | N | N | N | N | N | N | N | N |
| ATAD3B | high in NP | −3.6 | 0.02534387 | −1.6 | 13632 | 51 | 69 | 133 | 19 | 34 | 38 | N | N | N | N | N | N | N | N |
| ARRB2 | high in NP | −1.9 | 0.025286958 | −1.6 | 13633 | 50 | 67 | 111 | 34 | 31 | 32 | N | N | N | N | N | N | N | N |
| B3GALT6 | high in NP | −2.8 | 0.025232104 | −1.6 | 13634 | 93 | 217 | 193 | 81 | 73 | 63 | N | N | N | N | N | N | N | N |
| FANK1 | high in NP | −2.2 | 0.025221133 | −1.6 | 13635 | 18 | 28 | 23 | 11 | 12 | 5 | N | N | N | N | N | N | N | N |
| B3GALNT2 | high in NP | −1.9 | 0.025195762 | −1.6 | 13636 | 63 | 165 | 89 | 44 | 47 | 45 | N | N | N | N | N | N | N | N |
| RNF126 | high in NP | −1.8 | 0.025106624 | −1.6 | 13637 | 58 | 78 | 108 | 43 | 40 | 34 | N | N | N | N | N | N | N | N |
| GJC2 | high in NP | −2.5 | 0.025033941 | −1.6 | 13638 | 15 | 19 | 31 | 9 | 7 | 13 | N | N | N | N | N | N | N | N |
| CENPT | high in NP | −2.2 | 0.025018856 | −1.6 | 13639 | 602 | 1020 | 1139 | 446 | 445 | 463 | N | N | N | N | N | N | N | N |
| CEACAM19 | high in NP | −2.9 | 0.024979087 | −1.6 | 13640 | 97 | 236 | 352 | 43 | 86 | 83 | N | N | N | N | N | N | N | N |
| C1orf126 | high in NP | −2.3 | 0.024934517 | −1.6 | 13641 | 67 | 89 | 52 | 38 | 33 | 34 | NA | NA | N | N | N | N | N | N |
| TMEM93 | high in NP | −3.3 | 0.024928346 | −1.6 | 13642 | 22 | 22 | 17 | 2 | 7 | 13 | N | N | N | N | N | N | N | N |
| CD3EAP | high in NP | −2.1 | 0.024922175 | −1.6 | 13643 | 76 | 131 | 156 | 45 | 65 | 60 | N | N | N | N | N | N | N | N |
| ATG16L2 | high in NP | −3.5 | 0.024855664 | −1.6 | 13644 | 47 | 76 | 161 | 24 | 14 | 34 | N | N | N | N | N | N | N | N |
| HNRNPAO | high in NP | −2.6 | 0.024831665 | −1.6 | 13645 | 270 | 606 | 258 | 114 | 151 | 187 | N | N | N | N | N | N | N | N |
| PLAT | high in NP | −2.3 | 0.024796009 | −1.6 | 13646 | 142 | 390 | 243 | 121 | 110 | 67 | N | N | N | N | N | N | N | N |
| PSMD7 | high in NP | −2.1 | 0.024785038 | −1.6 | 13647 | 173 | 278 | 143 | 96 | 108 | 94 | N | N | N | N | N | N | N | N |
| SCYL1 | high in NP | −2.6 | 0.024763782 | −1.6 | 13648 | 1119 | 1027 | 3637 | 477 | 681 | 475 | N | N | N | N | N | N | N | N |
| ZNF32 | high in NP | −3.0 | 0.024736355 | −1.6 | 13649 | 30 | 72 | 64 | 17 | 16 | 26 | N | N | N | N | N | N | N | N |
| SLC16A5 | high in NP | −2.6 | 0.024730184 | −1.6 | 13650 | 27 | 62 | 33 | 22 | 15 | 10 | NA | NA | N | N | N | N | N | N |
| PLK1 | high in NP | −1.8 | 0.024683557 | −1.6 | 13651 | 11 | 20 | 11 | 7 | 6 | 6 | N | N | N | N | N | N | N | N |
| ZNF117 | high in NP | −1.9 | 0.024551906 | −1.6 | 13652 | 33 | 32 | 26 | 21 | 16 | 13 | N | N | N | N | N | N | N | N |
| GPR89A | high in NP | −2.5 | 0.024466882 | −1.6 | 13653 | 22 | 18 | 6 | 4 | 9 | 5 | N | N | N | N | N | N | N | N |
| KLHL17 | high in NP | −2.6 | 0.024446071 | −1.6 | 13654 | 39 | 38 | 101 | 18 | 16 | 13 | N | N | N | N | N | N | N | N |
| RPS15A | high in NP | −3.6 | 0.024412713 | −1.6 | 13655 | 4216 | 1142 | 1767 | 332 | 758 | 751 | N | N | N | N | N | N | N | N |
| GGT7 | high in NP | −2.8 | 0.024285861 | −1.6 | 13656 | 90 | 150 | 183 | 34 | 62 | 72 | N | N | N | N | N | N | N | N |
| ZNF32 | high in NP | −2.1 | 0.024228264 | −1.6 | 13657 | 45 | 74 | 95 | 32 | 34 | 40 | N | N | N | N | N | N | N | N |
| SENP3 | high in NP | −2.1 | 0.024200837 | −1.6 | 13658 | 315 | 434 | 370 | 226 | 209 | 88 | N | N | N | N | N | N | N | N |
| SEC14L2 | high in NP | −2.6 | 0.024157639 | −1.6 | 13659 | 21 | 61 | 51 | 20 | 13 | 11 | NA | NA | N | N | N | N | N | N |
| LOC93622 | high in NP | −3.1 | 0.024140496 | −1.6 | 13660 | 222 | 557 | 529 | 134 | 201 | 189 | N | N | N | N | N | N | N | N |
| PUF60 | high in NP | −2.1 | 0.023846338 | −1.6 | 13661 | 38 | 77 | 42 | 27 | 27 | 20 | N | N | N | N | N | N | N | N |
| FAM108C1 | high in NP | −2.0 | 0.023788741 | −1.6 | 13662 | 30 | 40 | 40 | 20 | 11 | 18 | N | N | N | N | N | N | N | N |
| CHRNB1 | high in NP | −2.5 | 0.023721544 | −1.6 | 13663 | 283 | 143 | 100 | 67 | 54 | 55 | N | N | N | N | N | N | N | N |
| TPD52 | high in NP | −2.1 | 0.023660518 | −1.6 | 13664 | 45 | 21 | 19 | 12 | 9 | 9 | N | N | N | N | N | N | N | N |
| TESK2 | | | | | | | | | | | | | | | | | | | |

TABLE 16-continued

Genes that Are Differentially Methylated between Nulliparous and Parous CD24+ Breast Epithelial Cells

| | | | | SAGE-seq | | | | | | | | | ChIP-seq | | | MSDK-seq | | |
|---|---|---|---|---|---|---|---|---|---|---|---|---|---|---|---|---|---|---|
| | | | | | Nulliparous (NP) | | | | Parous (P) | | | | NP | | P | | | |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | CD24+ N74 | CD24+ N66 | GeneBody | GeneBody Met | Pro-moter Met | Pro-moter Met |
| DCUN1D2 | high in NP | -2.2 | 0.023635834 | -1.6 | 13665 | 42 | 45 | 88 | 24 | 28 | 20 | N | N | NP | N | N | N |
| DHRS13 | high in NP | -2.3 | 0.023629663 | -1.6 | 13666 | 104 | 47 | 53 | 24 | 29 | 22 | N | N | N | N | N | N |
| PKIA | high in NP | -5.5 | 0.023580293 | -1.6 | 13667 | 18 | 14 | 2 | 2 | 2 | 2 | N | P | N | N | N | N |
| C1orf170 | high in NP | -2.1 | 0.023570694 | -1.6 | 13668 | 7 | 4 | 5 | 4 | 2 | 2 | NA | NA | N | N | N | N |
| PIK3R2 | high in NP | -3.1 | 0.023558352 | -1.6 | 13669 | 52 | 140 | 27 | 13 | 23 | 21 | N | N | N | N | N | N |
| LUC7L2 | high in NP | -3.7 | 0.023528867 | -1.6 | 13670 | 67 | 203 | 174 | 44 | 63 | 52 | N | N | N | P | N | N |
| PPIH | high in NP | -2.5 | 0.023510354 | -1.6 | 13671 | 24 | 8 | 6 | 4 | 4 | 4 | N | N | N | N | N | N |
| NKIRAS2 | high in NP | -2.1 | 0.023500754 | -1.6 | 13672 | 102 | 180 | 92 | 72 | 48 | 57 | N | N | N | N | N | N |
| SLC39A6 | high in NP | -2.3 | 0.023417101 | -1.6 | 13673 | 116 | 261 | 126 | 62 | 63 | 83 | N | N | N | N | N | N |
| MRPL45 | high in NP | -1.8 | 0.023398587 | -1.6 | 13674 | 221 | 308 | 245 | 142 | 177 | 132 | N | N | N | N | N | N |
| GPLD1 | high in NP | -2.3 | 0.023335059 | -1.6 | 13675 | 16 | 28 | 15 | 12 | 8 | 8 | N | N | N | N | N | N |
| ARL4D | high in NP | -1.8 | 0.023263508 | -1.6 | 13676 | 15 | 21 | 10 | 7 | 8 | 6 | N | N | N | N | N | N |
| SLC37A3 | high in NP | -2.5 | 0.023237452 | -1.6 | 13677 | 139 | 191 | 92 | 40 | 38 | 85 | N | N | N | N | N | N |
| BMP3 | high in NP | -2.2 | 0.023218939 | -1.6 | 13678 | 41 | 29 | 19 | 15 | 8 | 12 | N | P | N | N | N | N |
| ARL4A | high in NP | -3.0 | 0.023171626 | -1.6 | 13679 | 55 | 27 | 43 | 24 | 18 | 21 | N | N | N | N | N | N |
| RFC2 | high in NP | -2.1 | 0.023140771 | -1.6 | 13680 | 11 | 17 | 8 | 6 | 6 | 6 | N | N | N | N | N | N |
| TMEM30A | high in NP | -1.9 | 0.023067403 | -1.6 | 13681 | 374 | 701 | 447 | 261 | 257 | 307 | N | N | N | N | N | N |
| FAM36A | high in NP | -2.3 | 0.023020776 | -1.6 | 13682 | 131 | 110 | 70 | 48 | 41 | 41 | N | N | N | N | N | N |
| SNORD10 | high in NP | -5.5 | 0.022974835 | -1.6 | 13683 | 48 | 9 | 17 | 5 | 1 | 9 | N | N | N | N | N | N |
| FXN | high in NP | -1.9 | 0.022959975 | -1.6 | 13684 | 118 | 119 | 134 | 68 | 72 | 53 | N | N | N | N | N | N |
| KRI | high in NP | -2.3 | 0.022946037 | -1.6 | 13685 | 25 | 37 | 16 | 9 | 14 | 9 | N | N | N | N | N | N |
| SMTN | high in NP | -3.8 | 0.022930952 | -1.6 | 13686 | 1357 | 592 | 1975 | 236 | 336 | 562 | N | N | N | N | N | N |
| FLJ35220 | high in NP | -2.2 | 0.022917924 | -1.6 | 13687 | 17 | 49 | 33 | 9 | 9 | 17 | N | N | N | N | N | N |
| MRPS24 | high in NP | -1.9 | 0.022897353 | -1.6 | 13688 | 742 | 1195 | 891 | 467 | 463 | 590 | N | N | N | N | N | N |
| PRSS22 | high in NP | -2.8 | 0.022887754 | -1.6 | 13689 | 556 | 1047 | 1400 | 276 | 415 | 525 | N | N | N | N | N | N |
| PDGFB | high in NP | -1.9 | 0.022881583 | -1.6 | 13690 | 26 | 28 | 28 | 12 | 19 | 13 | N | N | N | N | N | N |
| CCNDBP1 | high in NP | -1.9 | 0.022875411 | -1.6 | 13691 | 26 | 29 | 17 | 14 | 14 | 15 | N | N | N | N | N | N |
| ATP5D | high in NP | -2.3 | 0.022806843 | -1.6 | 13692 | 676 | 1158 | 1153 | 566 | 528 | 318 | N | N | N | N | N | N |
| BTBD1 | high in NP | -1.9 | 0.022791072 | -1.6 | 13693 | 42 | 88 | 51 | 24 | 36 | 19 | N | N | N | N | N | N |
| CIB1 | high in NP | -490.3 | 0.022732789 | -1.6 | 13694 | 8 | 1577 | 2030 | 8 | 8 | 8 | N | N | N | N | N | N |
| DUSP19 | high in NP | -2.0 | 0.022726618 | -1.6 | 13695 | 328 | 395 | 329 | 187 | 157 | 239 | N | N | N | N | N | N |
| PSMC4 | high in NP | -2.5 | 0.022669021 | -1.6 | 13696 | 110 | 292 | 100 | 45 | 70 | 57 | N | N | N | N | N | N |
| RARA | high in NP | -2.3 | 0.022644336 | -1.6 | 13697 | 746 | 457 | 773 | 241 | 322 | 406 | N | N | N | N | N | N |
| LMNA | high in NP | -3.0 | 0.022638165 | -1.6 | 13698 | 11730 | 10406 | 10785 | 3647 | 3091 | 7906 | N | NA | N | N | N | N |
| SFRS9 | high in NP | -1.8 | 0.022616223 | -1.6 | 13699 | 179 | 299 | 171 | 98 | 109 | 114 | N | N | N | N | N | N |
| LPHN3 | high in NP | -1.7 | 0.022610052 | -1.6 | 13700 | 13 | 24 | 14 | 8 | 8 | 9 | N | N | N | N | N | N |
| MKI67IP | high in NP | -3.2 | 0.022540112 | -1.6 | 13701 | 49 | 116 | 119 | 20 | 45 | 29 | N | N | N | N | N | N |
| ABCE1 | high in NP | -2.9 | 0.022525027 | -1.6 | 13702 | 105 | 208 | 89 | 33 | 61 | 54 | N | N | N | N | N | N |
| TULP3 | high in NP | -1.9 | 0.022427766 | -1.6 | 13703 | 134 | 162 | 127 | 46 | 79 | 78 | N | N | N | N | N | N |
| LPCAT3 | high in NP | 4.8 | 0.022398176 | -1.6 | 13704 | 112 | 376 | 394 | 101 | 83 | 74 | N | N | N | N | N | N |
| EPCAM | high in NP | -2.9 | 0.022350178 | -1.7 | 13705 | 147 | 85 | 111 | 25 | 56 | 54 | N | NA | N | N | N | N |
| RPL26L1 | high in NP | -2.2 | 0.022309723 | -1.7 | 13706 | 59 | 75 | 63 | 22 | 44 | 31 | N | N | N | N | N | N |
| PRCP | high in NP | -3.0 | 0.022279553 | -1.7 | 13707 | 19 | 52 | 34 | 18 | 13 | 10 | N | N | N | N | N | N |
| PDRG1 | high in NP | -2.2 | 0.022267211 | -1.7 | 13708 | 59 | 70 | 65 | 20 | 31 | 41 | N | P | N | N | N | P |

TABLE 16-continued

Genes that Are Differentially Methylated between Nulliparous and Parous CD24+ Breast Epithelial Cells

| | | | | SAGE-seq | | Nulliparous (NP) | | | | Parous (P) | | | | ChIP-seq | | MSDK-seq | | | |
|---|---|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | NP | P | GeneBody Met | GeneBody Met | Pro-moter Met | Pro-moter Met |
| | | | | | | | | | | | | | | NP | P | NP | P | NP | P |
| ITPR2 | high in NP | −2.2 | 0.022223327 | −1.7 | 13709 | 186 | 269 | 220 | 159 | 95 | 99 | N | N | NP | NP | N | N | N | N |
| CTTN | high in NP | −2.7 | 0.022110189 | −1.7 | 13710 | 716 | 1707 | 1306 | 511 | 489 | 606 | N | N | N | N | N | N | N | N |
| ZNF585A | high in NP | −1.8 | 0.022072477 | −1.7 | 13711 | 9 | 13 | 9 | 6 | 4 | 4 | N | N | N | N | N | N | N | N |
| MAP1LC3B | high in NP | −2.1 | 0.022017622 | −1.7 | 13712 | 646 | 336 | 346 | 228 | 183 | 179 | N | N | N | N | N | N | N | N |
| FLJ36031 | high in NP | −2.0 | 0.021946997 | −1.7 | 13713 | 22 | 32 | 19 | 9 | 12 | 14 | N | N | N | N | N | N | N | N |
| ANXA4 | high in NP | −1.8 | 0.021927112 | −1.7 | 13714 | 93 | 167 | 83 | 51 | 57 | 54 | N | N | N | N | N | N | N | N |
| FANCL | high in NP | −2.2 | 0.021908598 | −1.7 | 13715 | 7 | 10 | 6 | 2 | 5 | 2 | N | N | N | N | N | N | N | N |
| C20orf54 | high in NP | −2.5 | 0.021902247 | −1.7 | 13716 | 13 | 38 | 29 | 5 | 10 | 11 | N | N | N | N | N | N | N | N |
| P2RX4 | high in NP | −3.3 | 0.021859229 | −1.7 | 13717 | 241 | 220 | 522 | 67 | 122 | 142 | N | N | N | N | N | N | N | N |
| MFGE8 | high in NP | −3.0 | 0.021853058 | −1.7 | 13718 | 4419 | 2442 | 11624 | 982 | 1616 | 1964 | N | N | N | N | N | N | N | N |
| PTP4A2 | high in NP | −4.1 | 0.021818088 | −1.7 | 13719 | 345 | 709 | 178 | 108 | 100 | 155 | N | N | N | N | N | N | N | N |
| DUSP15 | high in NP | −2.3 | 0.021775576 | −1.7 | 13720 | 7 | 11 | 6 | 2 | 2 | 6 | N | N | N | N | N | N | N | N |
| FOXH1 | high in NP | −2.0 | 0.021760491 | −1.7 | 13721 | 9 | 11 | 21 | 4 | 4 | 4 | N | N | N | N | N | N | N | N |
| USP7 | high in NP | −2.5 | 0.021715922 | −1.7 | 13722 | 394 | 892 | 798 | 208 | 272 | 407 | N | N | N | N | N | N | N | N |
| FAM40A | high in NP | −3.3 | 0.021170975 | −1.7 | 13723 | 43 | 77 | 33 | 11 | 26 | 22 | N | N | N | N | N | N | N | N |
| EXOC7 | high in NP | −2.9 | 0.021678895 | −1.7 | 13724 | 272 | 499 | 867 | 201 | 251 | 158 | N | N | N | N | N | N | N | N |
| ELF3 | high in NP | −3.0 | 0.021634325 | −1.7 | 13725 | 1303 | 1051 | 622 | 331 | 365 | 521 | N | N | N | N | N | N | N | N |
| SLC39A4 | high in NP | −3.3 | 0.021509531 | −1.7 | 13726 | 55 | 65 | 103 | 17 | 34 | 34 | N | N | N | N | N | N | N | N |
| TTC33 | high in NP | −1.8 | 0.02150336 | −1.7 | 13727 | 14 | 18 | 12 | 9 | 9 | 9 | N | N | N | N | N | N | N | N |
| REST | high in NP | −2.9 | 0.021476618 | −1.7 | 13728 | 22 | 59 | 22 | 16 | 10 | 13 | N | N | N | N | N | N | N | N |
| LRRK1 | high in NP | −1.9 | 0.021446448 | −1.7 | 13729 | 50 | 62 | 59 | 18 | 29 | 32 | N | N | N | N | N | N | N | N |
| FAM129B | high in NP | −2.0 | 0.021395022 | −1.7 | 13730 | 392 | 406 | 723 | 237 | 333 | 214 | N | N | N | N | N | N | N | N |
| PPP1R15A | high in NP | −3.0 | 0.021344967 | −1.7 | 13731 | 376 | 258 | 288 | 75 | 116 | 198 | N | N | NA | NA | N | N | N | N |
| MPG | high in NP | −2.5 | 0.021338796 | −1.7 | 13732 | 216 | 373 | 543 | 150 | 174 | 125 | N | N | N | N | N | N | N | N |
| FAM83A | high in NP | −1.8 | 0.021332625 | −1.7 | 13733 | 10 | 22 | 10 | 5 | 5 | 5 | N | N | N | N | N | N | N | N |
| SAPS2 | high in NP | −2.1 | 0.021326454 | −1.7 | 13734 | 144 | 192 | 288 | 82 | 108 | 107 | N | N | N | N | N | N | N | N |
| PRKCZ | high in NP | −3.0 | 0.021303826 | −1.7 | 13735 | 73 | 143 | 194 | 47 | 62 | 43 | N | N | N | N | N | N | N | N |
| C1orf152 | high in NP | −1.9 | 0.021297655 | −1.7 | 13736 | 8 | 7 | 15 | 3 | 3 | 3 | N | N | N | N | N | N | N | N |
| RNF149 | high in NP | −2.0 | 0.021246914 | −1.7 | 13737 | 261 | 192 | 168 | 88 | 98 | 118 | N | N | N | N | N | N | N | N |
| SERPINA1 | high in NP | −6.7 | 0.021131034 | −1.7 | 13738 | 397 | 389 | 74 | 42 | 72 | 31 | N | N | NA | NA | N | N | N | N |
| CCDC85C | high in NP | −2.3 | 0.021104292 | −1.7 | 13739 | 198 | 238 | 190 | 42 | 104 | 121 | N | N | NA | NA | N | N | N | N |
| MYBBP1A | high in NP | −2.4 | 0.02105218 | −1.7 | 13740 | 93 | 262 | 166 | 51 | 75 | 77 | N | N | N | N | N | N | N | N |
| C18orf26 | high in NP | −2.3 | 0.021035038 | −1.7 | 13741 | 20 | 28 | 16 | 13 | 8 | 10 | N | N | N | N | N | N | N | N |
| C14orf1 | high in NP | −3.2 | 0.020893102 | −1.7 | 13742 | 16 | 34 | 12 | 10 | 7 | 4 | N | N | N | N | N | N | N | N |
| VCP | high in NP | −2.1 | 0.020877331 | −1.7 | 13743 | 336 | 494 | 600 | 289 | 256 | 196 | N | N | N | N | N | N | N | N |
| GINS2 | high in NP | −2.1 | 0.020854704 | −1.7 | 13744 | 9 | 9 | 10 | 4 | 4 | 7 | N | N | N | N | N | N | N | N |
| FAM192A | high in NP | −2.0 | 0.020747737 | −1.7 | 13745 | 39 | 36 | 26 | 14 | 15 | 18 | N | N | NA | NA | N | N | N | N |
| RPL17 | high in NP | −2.2 | 0.020716196 | −1.7 | 13746 | 18736 | 32515 | 26257 | 12765 | 12776 | 15180 | N | N | N | N | N | N | N | N |
| NDUFV2 | high in NP | −2.4 | 0.020703854 | −1.7 | 13747 | 227 | 674 | 189 | 104 | 104 | 112 | N | N | N | N | N | N | N | N |
| GSTP1 | high in NP | −2.5 | 0.020646942 | −1.7 | 13748 | 1062 | 3853 | 1765 | 726 | 753 | 576 | P | N | N | N | N | N | N | N |
| CD14 | high in NP | −5.7 | 0.0206298 | −1.7 | 13749 | 131 | 477 | 627 | 92 | 58 | 121 | N | N | N | N | N | N | N | N |
| ZBTB47 | high in NP | −2.6 | 0.020550261 | −1.7 | 13750 | 31 | 93 | 65 | 27 | 28 | 18 | N | N | N | N | N | N | N | N |
| PIP | high in NP | −2.7 | 0.020544089 | −1.7 | 13751 | 23 | 5 | 3 | 2 | 2 | 2 | N | N | N | N | N | N | N | N |
| BEND2 | high in NP | −2.6 | 0.020505005 | −1.7 | 13752 | 44 | 51 | 93 | 28 | 26 | 20 | N | N | N | N | N | N | N | N |

TABLE 16-continued

Genes that Are Differentially Methylated between Nulliparous and Parous CD24+ Breast Epithelial Cells

| | | | | SAGE-seq | | | | | | | | ChIP-seq | | | MSDK-seq | | |
|---|---|---|---|---|---|---|---|---|---|---|---|---|---|---|---|---|---|
| | | | | | Nulliparous (NP) | | | | Parous (P) | | | | | | | | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP | CD24+ N74 | CD24+ N66 | NP GeneBody | GeneBody Met | P | Pro-moter Met | P | Pro-moter Met | P |
|---|---|---|---|---|---|---|---|---|---|---|---|---|---|---|---|---|---|---|---|---|---|
| C22orf28 | high in NP | −2.8 | 0.020484435 | −1.7 | 13753 | 182 | 100 | 59 | 27 | 44 | 31 | P | N | N | N | N | N | N | N | N |
| MIA | high in NP | −3.1 | 0.020472093 | −1.7 | 13754 | 118 | 117 | 184 | 26 | 70 | 59 | N | N | N | N | N | N | N | N | N |
| ZNF777 | high in NP | −3.6 | 0.020461122 | −1.7 | 13755 | 31 | 88 | 92 | 15 | 25 | 25 | N | N | N | N | N | N | N | N | N |
| THOC4 | high in NP | −2.2 | 0.020454951 | −1.7 | 13756 | 22 | 22 | 22 | 10 | 17 | 10 | N | N | N | N | N | N | N | N | N |
| ZW10 | high in NP | −2.9 | 0.020417924 | −1.7 | 13757 | 26 | 76 | 57 | 16 | 14 | 22 | N | N | N | N | N | N | N | N | N |
| C1orf86 | high in NP | −2.6 | 0.020411753 | −1.7 | 13758 | 128 | 183 | 209 | 47 | 103 | 66 | N | N | N | N | N | N | N | N | N |
| CYFIP2 | high in NP | −3.0 | 0.020321242 | −1.7 | 13759 | 29 | 14 | 10 | 6 | 8 | 6 | N | N | N | N | N | N | N | N | N |
| MAP1B | high in NP | −2.8 | 0.020289015 | −1.7 | 13760 | 351 | 712 | 390 | 268 | 261 | 157 | N | N | N | N | N | N | N | N | N |
| VEGFB | high in NP | −2.5 | 0.020243075 | −1.7 | 13761 | 99 | 92 | 58 | 43 | 18 | 38 | N | NA | N | N | N | N | N | N | N |
| BTBD19 | high in NP | −5.3 | 0.020230732 | −1.7 | 13762 | 11 | 11 | 7 | 2 | 2 | 8 | N | NA | N | N | N | N | N | N | N |
| MND1 | high in NP | −3.0 | 0.020016285 | −1.7 | 13763 | 6 | 2 | 2 | 3 | 1 | 1 | N | NA | N | N | N | N | N | N | N |
| ZNF138 | high in NP | −1.8 | 0.020142965 | −1.7 | 13764 | 12 | 6 | 6 | 4 | 4 | 4 | N | N | N | N | N | N | N | N | N |
| TMX1 | high in NP | −2.0 | 0.020126509 | −1.7 | 13765 | 42 | 93 | 37 | 23 | 20 | 23 | N | NA | N | N | N | N | N | N | N |
| TIA1 | high in NP | −1.7 | 0.020079882 | −1.7 | 13766 | 30 | 43 | 35 | 16 | 22 | 17 | N | NA | N | N | N | N | N | N | N |
| CSNK1G2 | high in NP | −2.3 | 0.020044912 | −1.7 | 13767 | 92 | 122 | 105 | 49 | 45 | 70 | N | NA | N | N | N | N | N | N | N |
| PSMD2 | high in NP | −2.4 | 0.019985943 | −1.7 | 13768 | 384 | 825 | 653 | 321 | 296 | 262 | N | N | N | N | N | N | N | N | N |
| NAA25 | high in NP | −2.3 | 0.019979772 | −1.7 | 13769 | 346 | 233 | 243 | 113 | 143 | 155 | N | N | N | N | N | N | N | N | N |
| TFEB | high in NP | −2.0 | 0.019939317 | −1.7 | 13770 | 30 | 41 | 39 | 22 | 24 | 13 | N | NA | N | N | N | N | N | N | N |
| UBA1 | high in NP | −2.2 | 0.019911189 | −1.7 | 13771 | 598 | 484 | 791 | 314 | 287 | 375 | N | P | N | N | N | N | N | N | N |
| STX3 | high in NP | −3.4 | 0.019895433 | −1.7 | 13772 | 226 | 188 | 98 | 59 | 62 | 77 | N | N | N | N | N | N | N | N | N |
| RPL7 | high in NP | −3.7 | 0.019882405 | −1.7 | 13773 | 3008 | 1081 | 756 | 232 | 417 | 524 | N | N | N | N | N | N | N | N | N |
| RRBP1 | high in NP | −3.1 | 0.019795324 | −1.7 | 13774 | 163 | 305 | 101 | 59 | 66 | 57 | N | N | N | N | N | N | N | N | N |
| ATP1B1 | high in NP | −3.8 | 0.019763782 | −1.7 | 13775 | 430 | 426 | 176 | 142 | 117 | 101 | N | N | N | N | N | N | N | N | N |
| CDK5RAP2 | high in NP | −2.5 | 0.019757611 | −1.7 | 13776 | 83 | 89 | 136 | 52 | 33 | 48 | N | N | N | N | N | N | N | N | N |
| SNRPB | high in NP | −2.3 | 0.019742526 | −1.7 | 13777 | 2153 | 4645 | 2298 | 1028 | 1113 | 1430 | N | N | N | N | N | N | N | N | N |
| HMG20B | high in NP | −2.3 | 0.019736355 | −1.7 | 13778 | 320 | 333 | 282 | 153 | 112 | 204 | N | N | N | N | N | N | N | N | N |
| LMX1B | high in NP | −2.1 | 0.019656816 | −1.7 | 13779 | 59 | 101 | 87 | 44 | 48 | 26 | N | N | N | N | N | N | N | N | N |
| ANOS | high in NP | −3.2 | 0.019647216 | −1.7 | 13780 | 45 | 156 | 143 | 27 | 26 | 43 | N | N | N | N | N | N | N | N | N |
| ENO1 | high in NP | −2.2 | 0.019455811 | −1.7 | 13781 | 1523 | 2303 | 1550 | 961 | 1030 | 704 | N | N | N | N | N | N | N | N | N |
| SNRNP200 | high in NP | −2.2 | 0.019421626 | −1.7 | 13782 | 305 | 252 | 249 | 107 | 126 | 177 | N | N | N | N | N | N | N | N | N |
| COMMD6 | high in NP | −2.4 | 0.019398313 | −1.7 | 13783 | 1043 | 519 | 565 | 215 | 277 | 349 | N | N | N | N | N | N | N | N | N |
| GLI4 | high in NP | −3.2 | 0.019392142 | −1.7 | 13784 | 29 | 18 | 35 | 4 | 11 | 13 | N | N | N | N | N | N | N | N | N |
| STX5 | high in NP | −3.0 | 0.019385971 | −1.7 | 13785 | 1171 | 722 | 1696 | 442 | 432 | 505 | N | N | N | N | N | N | N | N | N |
| PSMA2 | high in NP | −3.4 | 0.019345516 | −1.7 | 13786 | 196 | 153 | 71 | 28 | 59 | 42 | N | N | N | N | N | N | N | N | N |
| IRS1 | high in NP | −2.0 | 0.019324259 | −1.7 | 13787 | 64 | 61 | 65 | 32 | 30 | 28 | N | N | N | N | N | N | N | N | N |
| DUSP16 | high in NP | −3.6 | 0.019318088 | −1.7 | 13788 | 39 | 21 | 11 | 10 | 4 | 4 | N | N | N | N | N | N | N | N | N |
| ETNK2 | high in NP | −2.9 | 0.019297518 | −1.7 | 13789 | 158 | 54 | 33 | 20 | 21 | 19 | N | N | N | N | N | N | N | N | N |
| DYNLRB1 | high in NP | −5.1 | 0.019275576 | −1.7 | 13790 | 57 | 324 | 155 | 35 | 38 | 46 | N | N | N | N | N | N | N | N | N |
| TXNDC11 | high in NP | −3.1 | 0.019085642 | −1.7 | 13791 | 51 | 53 | 21 | 19 | 12 | 13 | N | N | N | N | N | N | N | N | N |
| C12orf57 | high in NP | −1.8 | 0.019067128 | −1.7 | 13792 | 1991 | 1687 | 1757 | 1016 | 967 | 1158 | N | N | N | N | N | N | N | N | N |
| NDUFB3 | high in NP | −2.9 | 0.019046558 | −1.7 | 13793 | 7 | 8 | 11 | 2 | 5 | 2 | N | N | N | N | N | N | N | N | N |
| ECH1 | high in NP | −2.2 | 0.01903353 | −1.7 | 13794 | 102 | 91 | 68 | 32 | 42 | 50 | N | N | N | N | N | N | N | N | N |
| FAM160A2 | high in NP | −5.8 | 0.019010902 | −1.7 | 13795 | 37 | 178 | 187 | 20 | 29 | 34 | N | N | N | N | N | N | N | N | N |
| HSD11B1L | high in NP | −2.1 | 0.018996503 | −1.7 | 13796 | 54 | 47 | 70 | 29 | 22 | 27 | N | N | N | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | | MSDK-seq | | |
|---|---|---|---|---|---|---|---|---|---|---|---|---|---|---|---|---|---|---|
| | | | | | | Nulliparous (NP) | | | | Parous (P) | | | | | | | | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | P GeneBody Met | NP Pro-moter | P Pro-moter Met |
| ARSJ | high in NP | -2.2 | 0.018951248 | -1.7 | 13797 | 44 | 67 | 78 | 25 | 32 | 34 | N | N | N | N | N | N |
| RIF1 | high in NP | -2.2 | 0.01886828 | -1.7 | 13798 | 61 | 111 | 57 | 31 | 39 | 34 | N | N | N | N | N | N |
| SLC17A5 | high in NP | -2.3 | 0.01882234 | -1.7 | 13799 | 35 | 74 | 28 | 17 | 19 | 17 | N | N | N | N | N | N |
| PPEF2 | high in NP | -2.2 | 0.018816168 | -1.7 | 13800 | 24 | 16 | 23 | 10 | 11 | 15 | N | N | N | N | N | N |
| CDT1 | high in NP | -2.2 | 0.01880314 | -1.7 | 13801 | 16 | 12 | 17 | 6 | 6 | 6 | N | N | N | N | P | N |
| DOPEY2 | high in NP | -2.5 | 0.01878257 | -1.7 | 13802 | 203 | 387 | 141 | 74 | 100 | 92 | N | N | N | N | N | N |
| LOC374491 | high in NP | -3.4 | 0.018776399 | -1.7 | 13803 | 35 | 10 | 7 | 6 | 4 | 4 | N | N | N | N | N | N |
| MPHOSPH8 | high in NP | -2.4 | 0.018754457 | -1.7 | 13804 | 124 | 223 | 239 | 103 | 75 | 102 | N | N | N | N | N | N |
| RPL27 | high in NP | -2.8 | 0.018699602 | -1.7 | 13805 | 911 | 894 | 426 | 224 | 240 | 379 | N | N | N | N | N | N |
| RTN2 | high in NP | -6.5 | 0.01866189 | -1.7 | 13806 | 22 | 71 | 198 | 10 | 17 | 8 | N | N | N | P | N | N |
| TP53 | high in NP | -2.3 | 0.018572751 | -1.7 | 13807 | 51 | 131 | 53 | 26 | 31 | 31 | N | N | N | N | N | N |
| SLA2 | high in NP | -3.0 | 0.018557666 | -1.7 | 13808 | 9 | 9 | 6 | 4 | 4 | 7 | N | N | N | N | N | N |
| INO80B | high in NP | -2.9 | 0.018525439 | -1.7 | 13809 | 105 | 50 | 110 | 18 | 41 | 29 | N | N | N | N | N | N |
| HNRNPUL1 | high in NP | -2.9 | 0.018513097 | -1.7 | 13810 | 149 | 156 | 77 | 42 | 63 | 45 | N | N | N | P | N | P |
| KIAA0427 | high in NP | -3.3 | 0.018467841 | -1.7 | 13811 | 181 | 398 | 558 | 130 | 159 | 144 | N | N | N | N | N | N |
| LIPH | high in NP | -3.2 | 0.018438357 | -1.7 | 13812 | 26 | 22 | 20 | 5 | 15 | 5 | N | N | N | N | N | N |
| RBMXL1 | high in NP | -1.7 | 0.018391045 | -1.7 | 13813 | 20 | 18 | 14 | 8 | 8 | 8 | NA | NA | N | N | N | N |
| PHF23 | high in NP | -2.9 | 0.018375274 | -1.7 | 13814 | 51 | 89 | 72 | 20 | 23 | 44 | N | N | N | N | N | N |
| ICA1 | high in NP | -2.7 | 0.018365675 | -1.7 | 13815 | 429 | 482 | 911 | 216 | 324 | 175 | N | N | N | N | N | N |
| CUEDC1 | high in NP | -3.0 | 0.018349904 | -1.7 | 13816 | 22 | 59 | 17 | 6 | 12 | 6 | N | N | N | N | N | N |
| ALDH2 | high in NP | -1.7 | 0.018334819 | -1.7 | 13817 | 183 | 170 | 178 | 95 | 115 | 99 | N | N | N | N | N | N |
| GART | high in NP | -2.9 | 0.018276536 | -1.7 | 13818 | 58 | 85 | 90 | 32 | 49 | 34 | N | N | N | N | N | N |
| IER2 | high in NP | -2.0 | 0.018225795 | -1.7 | 13819 | 4591 | 4675 | 7169 | 2562 | 2260 | 3110 | N | N | N | N | N | N |
| MRPL42 | high in NP | -2.9 | 0.018212767 | -1.7 | 13820 | 257 | 337 | 150 | 120 | 97 | 91 | N | N | N | N | N | N |
| DYNC1L2 | high in NP | -2.4 | 0.018203168 | -1.7 | 13821 | 994 | 1233 | 783 | 560 | 445 | 504 | N | N | N | N | N | N |
| PABPC1L | high in NP | -3.7 | 0.018162713 | -1.7 | 13822 | 128 | 77 | 79 | 21 | 40 | 44 | NA | NA | N | N | N | N |
| DTWD1 | high in NP | -2.2 | 0.018103058 | -1.7 | 13823 | 15 | 21 | 12 | 7 | 7 | 10 | N | N | N | N | N | N |
| SALL2 | high in NP | -4.0 | 0.018057117 | -1.7 | 13824 | 10 | 15 | 14 | 8 | 8 | 6 | P | P | N | N | N | N |
| ZBTB8A | high in NP | -2.3 | 0.018050946 | -1.8 | 13825 | 1070 | 725 | 755 | 282 | 359 | 520 | NA | NA | N | N | N | N |
| CLPP | high in NP | -3.4 | 0.018037918 | -1.8 | 13826 | 42 | 113 | 159 | 31 | 26 | 34 | N | N | N | N | N | N |
| ALKBH5 | high in NP | -2.6 | 0.018002948 | -1.8 | 13827 | 132 | 177 | 91 | 44 | 48 | 78 | N | N | N | N | N | N |
| YBX1 | high in NP | -4.7 | 0.017986492 | -1.8 | 13828 | 93 | 247 | 102 | 12 | 64 | 39 | N | N | N | N | N | N |
| HPCAL1 | high in NP | -3.0 | 0.017915867 | -1.8 | 13829 | 1424 | 853 | 1808 | 521 | 617 | 471 | NA | N | N | N | N | N |
| LOC100294362 | high in NP | -2.6 | 0.017861698 | -1.8 | 13830 | 451 | 349 | 441 | 186 | 134 | 245 | NA | N | N | N | N | N |
| DYNC2LI1 | high in NP | -3.4 | 0.017841127 | -1.8 | 13831 | 21 | 21 | 15 | 12 | 5 | 8 | N | N | N | N | N | N |
| MKRN2 | high in NP | -3.1 | 0.017828785 | -1.8 | 13832 | 30 | 80 | 46 | 14 | 17 | 27 | N | N | N | N | N | N |
| ARHGAP30 | high in NP | -2.1 | 0.017793815 | -1.8 | 13833 | 94 | 78 | 60 | 28 | 45 | 32 | N | N | N | N | N | N |
| GRASP | high in NP | -3.3 | 0.017736903 | -1.8 | 13834 | 31 | 50 | 102 | 21 | 19 | 10 | N | N | N | N | N | N |
| MCAT | high in NP | -2.8 | 0.017714962 | -1.8 | 13835 | 87 | 170 | 225 | 74 | 57 | 48 | N | N | N | N | N | N |
| RPS15 | high in NP | -3.7 | 0.017679992 | -1.8 | 13836 | 166 | 78 | 183 | 42 | 57 | 45 | N | N | N | N | N | N |
| PYGB | high in NP | -2.2 | 0.017550398 | -1.8 | 13837 | 595 | 603 | 416 | 272 | 282 | 293 | N | N | N | N | N | N |
| FKBP11 | high in NP | -3.1 | 0.017499657 | -1.8 | 13838 | 334 | 707 | 818 | 266 | 248 | 260 | N | N | N | N | N | N |
| SFPQ | high in NP | -2.8 | 0.017486629 | -1.8 | 13839 | 263 | 837 | 464 | 132 | 182 | 205 | N | N | N | N | P | P |
| PICK1 | high in NP | -2.2 | 0.017429717 | -1.8 | 13840 | 240 | 233 | 441 | 102 | 120 | 144 | N | N | N | N | N | N |

TABLE 16-continued

Genes that Are Differentially Methylated between Nulliparous and Parous CD24+ Breast Epithelial Cells

| | | | | SAGE-seq | | | | | | | | ChIP-seq | | | MSDK-seq | | |
|---|---|---|---|---|---|---|---|---|---|---|---|---|---|---|---|---|---|
| | | | | | Nulliparous (NP) | | | | Parous (P) | | | | | GeneBody | | Pro-moter | |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody NP | P Met | NP Pro-moter Met | P Pro-moter Met |
| ZBTB48 | high in NP | −3.6 | 0.017400233 | −1.8 | 13841 | 45 | 152 | 112 | 25 | 32 | 35 | N | N | N | N | N | N |
| ORMDL1 | high in NP | −2.7 | 0.017385148 | −1.8 | 13842 | 83 | 89 | 43 | 25 | 32 | 27 | N | N | N | N | N | N |
| C14orf101 | high in NP | −1.7 | 0.017378977 | −1.8 | 13843 | 20 | 26 | 26 | 14 | 12 | 15 | N | N | N | N | N | N |
| LRRC4 | high in NP | −1.7 | 0.017358406 | −1.8 | 13844 | 53 | 71 | 57 | 30 | 35 | 34 | N | N | N | N | N | N |
| SPEN | high in NP | −2.9 | 0.017323437 | −1.8 | 13845 | 488 | 585 | 476 | 196 | 242 | 352 | N | N | N | N | P | N |
| DGCR2 | high in NP | −3.0 | 0.017296009 | −1.8 | 13846 | 84 | 250 | 171 | 66 | 73 | 49 | N | N | N | N | N | N |
| FAM3D | high in NP | −7.9 | 0.017271325 | −1.8 | 13847 | 13 | 19 | 8 | 1 | 1 | 9 | N | N | N | N | N | N |
| XRN2 | high in NP | −4.1 | 0.017265154 | −1.8 | 13848 | 214 | 285 | 101 | 63 | 80 | 61 | N | N | N | N | N | N |
| DECR1 | high in NP | −2.4 | 0.017258982 | −1.8 | 13849 | 115 | 143 | 82 | 66 | 53 | 35 | N | N | N | N | N | N |
| ENTPD4 | high in NP | −2.5 | 0.017230184 | −1.8 | 13850 | 21 | 33 | 18 | 12 | 14 | 3 | N | N | N | N | N | N |
| PHGR1 | high in NP | −10.3 | 0.017167101 | −1.8 | 13851 | 274 | 47 | 330 | 31 | 33 | 16 | N | N | N | N | N | N |
| GPR108 | high in NP | −3.1 | 0.01716093 | −1.8 | 13852 | 200 | 420 | 497 | 149 | 162 | 132 | N | N | N | N | N | N |
| CASP6 | high in NP | −2.1 | 0.017154759 | −1.8 | 13853 | 28 | 37 | 32 | 17 | 18 | 11 | N | N | N | N | N | N |
| RRP7A | high in NP | −8.9 | 0.017148587 | −1.8 | 13854 | 22 | 25 | 11 | 2 | 2 | 13 | N | N | N | N | N | N |
| SPAG16 | high in NP | −2.2 | 0.017137617 | −1.8 | 13855 | 119 | 80 | 88 | 48 | 43 | 35 | N | N | N | N | N | N |
| CHCHD2 | high in NP | −2.8 | 0.01707042 | −1.8 | 13856 | 3382 | 5073 | 11130 | 1730 | 2347 | 1631 | NA | NA | N | N | N | N |
| DMAP1 | high in NP | −3.2 | 0.017023793 | −1.8 | 13857 | 135 | 200 | 331 | 109 | 61 | 57 | N | N | N | N | N | N |
| NAA50 | high in NP | −2.0 | 0.016986081 | −1.8 | 13858 | 86 | 120 | 98 | 50 | 51 | 65 | N | N | N | N | N | N |
| SDHAP1 | high in NP | −1.6 | 0.016967567 | −1.8 | 13859 | 9 | 7 | 6 | 4 | 4 | 4 | NA | NA | N | N | N | N |
| RPS20 | high in NP | −6.7 | 0.016961396 | −1.8 | 13860 | 2154 | 3077 | 556 | 267 | 373 | 494 | N | N | N | N | N | N |
| FBP1 | high in NP | −2.6 | 0.016945625 | −1.8 | 13861 | 132 | 115 | 86 | 63 | 40 | 26 | N | N | N | N | N | N |
| LRRC41 | high in NP | −8.0 | 0.01691477 | −1.8 | 13862 | 130 | 1186 | 516 | 63 | 84 | 116 | N | N | N | N | N | N |
| TIMM44 | high in NP | −1.8 | 0.01680506 | −1.8 | 13863 | 355 | 428 | 424 | 199 | 237 | 257 | N | N | N | N | N | N |
| LOC728640 | high in NP | −5.1 | 0.016798889 | −1.8 | 13864 | 43 | 45 | 12 | 3 | 8 | 14 | NA | NA | N | N | N | N |
| ERCC2 | high in NP | −3.1 | 0.01677489 | −1.8 | 13865 | 47 | 28 | 47 | 16 | 9 | 9 | N | N | N | N | N | N |
| PGR | high in NP | −1.8 | 0.016629526 | −1.8 | 13866 | 31 | 44 | 42 | 27 | 23 | 26 | N | N | N | N | N | N |
| CHAD | high in NP | −2.9 | 0.016623354 | −1.8 | 13867 | 69 | 17 | 15 | 5 | 6 | 3 | N | P | N | N | N | N |
| ZNF12 | high in NP | −2.7 | 0.016613755 | −1.8 | 13868 | 87 | 105 | 61 | 33 | 30 | 52 | N | N | N | N | N | N |
| ELF2 | high in NP | −2.7 | 0.016547244 | −1.8 | 13869 | 50 | 82 | 37 | 16 | 13 | 29 | N | N | N | N | N | N |
| FAM102A | high in NP | −2.6 | 0.016527359 | −1.8 | 13870 | 1589 | 3416 | 1192 | 798 | 560 | 706 | N | N | N | N | N | N |
| CBY1 | high in NP | −2.6 | 0.016515016 | −1.8 | 13871 | 99 | 202 | 141 | 73 | 57 | 56 | N | N | N | N | N | N |
| PITPNM1 | high in NP | −1.8 | 0.016504046 | −1.8 | 13872 | 92 | 101 | 108 | 52 | 56 | 62 | N | N | N | N | N | N |
| RING1 | high in NP | −2.5 | 0.016469076 | −1.8 | 13873 | 1050 | 780 | 697 | 297 | 440 | 431 | N | N | N | N | N | N |
| UBE2R2 | high in NP | −2.0 | 0.016417649 | −1.8 | 13874 | 2313 | 1818 | 1756 | 912 | 991 | 1191 | N | N | N | N | N | N |
| RUNX1 | high in NP | −2.1 | 0.01637788 | −1.8 | 13875 | 1630 | 1478 | 1997 | 983 | 995 | 1265 | P | N | N | N | N | N |
| ACAD8 | high in NP | −3.4 | 0.016371709 | −1.8 | 13876 | 55 | 72 | 25 | 14 | 19 | 16 | N | N | N | N | N | N |
| ING5 | high in NP | −2.4 | 0.016345653 | −1.8 | 13877 | 56 | 71 | 69 | 21 | 41 | 25 | N | N | N | N | N | N |
| NME7 | high in NP | −3.4 | 0.016339482 | −1.8 | 13878 | 147 | 120 | 50 | 26 | 42 | 34 | N | N | N | N | N | N |
| NOB1 | high in NP | −2.2 | 0.01633331 | −1.8 | 13879 | 41 | 50 | 64 | 27 | 29 | 22 | N | N | N | N | N | N |
| ABCB9 | high in NP | −2.3 | 0.016203716 | −1.8 | 13880 | 32 | 31 | 19 | 13 | 11 | 11 | N | N | N | N | N | N |
| PRMT5 | high in NP | −2.5 | 0.016152976 | −1.8 | 13881 | 32 | 71 | 45 | 15 | 29 | 18 | N | N | N | N | N | N |
| GFOD2 | high in NP | −1.9 | 0.016127606 | −1.8 | 13882 | 268 | 313 | 372 | 179 | 177 | 203 | N | N | N | N | N | N |
| TMX2 | high in NP | −2.8 | 0.016090579 | −1.8 | 13883 | 60 | 167 | 44 | 26 | 27 | 16 | NA | NA | N | N | N | N |
| METTL12 | high in NP | −2.4 | 0.016064523 | −1.8 | 13884 | 27 | 14 | 19 | 9 | 8 | 11 | NA | NA | N | N | N | N |

TABLE 16-continued

Genes that Are Differentially Methylated between Nulliparous and Parous CD24+ Breast Epithelial Cells

| | | | | SAGE-seq | | | | | | | ChIP-seq | | | MSDK-seq | | |
|---|---|---|---|---|---|---|---|---|---|---|---|---|---|---|---|---|
| | | | | | Nulliparous (NP) | | | | Parous (P) | | | NP | P | | | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | GeneBody Met | Pro-moter Met | Pro-moter Met |
| HDAC11 | high in NP | -2.5 | 0.016058352 | -1.8 | 13885 | 35 | 39 | 32 | 23 | 13 | 14 | N | N | N | N | N | N |
| MAPKBP1 | high in NP | -3.1 | 0.01605218 | -1.8 | 13886 | 267 | 150 | 332 | 66 | 73 | 125 | N | N | N | N | N | N |
| TIMM50 | high in NP | -2.4 | 0.016009668 | -1.8 | 13887 | 162 | 402 | 162 | 76 | 100 | 73 | N | N | N | N | N | N |
| AGR2 | high in NP | -3.6 | 0.01599664 | -1.8 | 13888 | 21 | 160 | 26 | 5 | 10 | 5 | N | N | N | P | N | N |
| NKRF | high in NP | -2.3 | 0.015965784 | -1.8 | 13889 | 38 | 46 | 29 | 22 | 13 | 19 | N | N | N | N | N | N |
| COQ4 | high in NP | -2.2 | 0.015947271 | -1.8 | 13890 | 321 | 501 | 526 | 171 | 240 | 226 | N | N | N | N | N | N |
| GLIPR1 | high in NP | -2.3 | 0.015926015 | -1.8 | 13891 | 1023 | 934 | 1112 | 321 | 516 | 589 | N | N | N | N | N | N |
| RPS18 | high in NP | -3.1 | 0.01584579 | -1.8 | 13892 | 9710 | 9856 | 5270 | 1741 | 3155 | 3905 | N | N | N | N | N | N |
| NOP14 | high in NP | -2.7 | 0.015779964 | -1.8 | 13893 | 79 | 114 | 126 | 24 | 42 | 59 | N | N | N | N | N | N |
| AIMP1 | high in NP | -2.3 | 0.015696311 | -1.8 | 13894 | 171 | 241 | 161 | 56 | 87 | 102 | NA | NA | N | N | N | N |
| AP2A1 | high in NP | -2.7 | 0.01569014 | -1.8 | 13895 | 22 | 55 | 45 | 20 | 16 | 17 | N | N | N | N | N | N |
| PPIA | high in NP | -2.4 | 0.015648313 | -1.8 | 13896 | 405 | 282 | 236 | 157 | 115 | 124 | N | N | N | N | N | N |
| PLD2 | high in NP | -2.1 | 0.015635971 | -1.8 | 13897 | 82 | 112 | 127 | 51 | 37 | 59 | N | N | N | N | N | N |
| HNRNPUL2 | high in NP | -2.7 | 0.015601687 | -1.8 | 13898 | 26 | 55 | 49 | 19 | 20 | 15 | N | N | N | N | N | N |
| GLT25D1 | high in NP | -2.6 | 0.015586602 | -1.8 | 13899 | 80 | 276 | 109 | 38 | 41 | 52 | N | N | N | N | N | N |
| DDR1 | high in NP | -2.4 | 0.015543404 | -1.8 | 13900 | 1958 | 4923 | 1938 | 859 | 922 | 1162 | N | N | N | N | N | N |
| STBD1 | high in NP | -2.5 | 0.01549472 | -1.8 | 13901 | 60 | 87 | 84 | 22 | 29 | 46 | N | N | N | N | N | N |
| CDC37 | high in NP | -1.9 | 0.01540901 | -1.8 | 13902 | 1616 | 2114 | 2014 | 822 | 1093 | 1156 | P | N | N | N | N | N |
| VAMP8 | high in NP | -2.8 | 0.015677869 | -1.8 | 13903 | 407 | 1480 | 350 | 159 | 163 | 181 | N | N | N | N | N | N |
| PEX14 | high in NP | -2.2 | 0.015330156 | -1.8 | 13904 | 45 | 56 | 42 | 18 | 28 | 21 | N | N | N | N | N | N |
| TFE3 | high in NP | -1.9 | 0.015323985 | -1.8 | 13905 | 110 | 116 | 149 | 58 | 69 | 70 | N | N | N | N | N | N |
| FGF13 | high in NP | -2.4 | 0.015317814 | -1.8 | 13906 | 27 | 18 | 20 | 8 | 13 | 9 | P | P | N | N | N | N |
| SNORD36A | high in NP | 5.3 | 0.01528353 | -1.8 | 13907 | 9 | 11 | 8 | 1 | 1 | 7 | N | N | N | N | N | N |
| NUP88 | high in NP | -3.7 | 0.015159421 | -1.8 | 13908 | 193 | 194 | 78 | 48 | 61 | 52 | N | N | N | N | N | N |
| C21orf49 | high in NP | -2.1 | 0.015126509 | -1.8 | 13909 | 108 | 96 | 109 | 57 | 61 | 42 | NA | NA | N | N | N | N |
| STK10 | high in NP | -2.4 | 0.015080568 | -1.8 | 13910 | 54 | 172 | 97 | 33 | 41 | 39 | P | P | N | N | N | N |
| RCVRN | high in NP | -2.9 | 0.015062054 | -1.8 | 13911 | 10 | 16 | 14 | 5 | 8 | 5 | N | P | N | N | N | N |
| ARRDC2 | high in NP | -3.3 | 0.014957145 | -1.8 | 13912 | 80 | 161 | 82 | 22 | 39 | 48 | N | N | N | N | N | N |
| HSPB8 | high in NP | -3.4 | 0.014892005 | -1.8 | 13913 | 57 | 155 | 151 | 38 | 31 | 54 | N | N | N | N | N | N |
| ILVBL | high in NP | -2.6 | 0.014862521 | -1.8 | 13914 | 84 | 45 | 46 | 15 | 26 | 16 | P | N | N | N | N | N |
| LGALS8 | high in NP | -2.1 | 0.014721956 | -1.8 | 13915 | 115 | 100 | 113 | 54 | 57 | 50 | N | N | N | N | P | N |
| DALRD3 | high in NP | -2.4 | 0.014693157 | -1.8 | 13916 | 264 | 475 | 235 | 133 | 125 | 146 | N | N | N | N | N | N |
| EEF1D | high in NP | -2.6 | 0.01463502 | -1.8 | 13917 | 2745 | 6312 | 6667 | 1183 | 1490 | 2313 | N | N | N | N | N | N |
| SLC38A10 | high in NP | -2.2 | 0.014612246 | -1.8 | 13918 | 80 | 147 | 100 | 66 | 47 | 44 | N | N | N | N | N | N |
| POLR2G | high in NP | -2.9 | 0.014489619 | -1.8 | 13919 | 146 | 228 | 90 | 70 | 59 | 45 | N | N | N | N | N | N |
| ATAD1 | high in NP | -2.2 | 0.014512137 | -1.8 | 13920 | 147 | 113 | 81 | 42 | 50 | 45 | N | N | N | N | N | N |
| CPLX1 | high in NP | -4.2 | 0.014466196 | -1.8 | 13921 | 187 | 96 | 218 | 49 | 63 | 19 | P | N | N | N | N | N |
| CCNG1 | high in NP | -4.2 | 0.014456596 | -1.8 | 13922 | 95 | 79 | 27 | 16 | 14 | 21 | N | N | N | N | N | N |
| P4HB | high in NP | -3.1 | 0.014422998 | -1.8 | 13923 | 2979 | 4808 | 1866 | 1478 | 1091 | 760 | N | N | N | N | N | N |
| MIB2 | high in NP | -3.2 | 0.014393513 | -1.8 | 13924 | 287 | 211 | 842 | 111 | 93 | 106 | N | N | N | P | P | N |
| CDC42BPB | high in NP | -3.3 | 0.0143654 | -1.8 | 13925 | 171 | 458 | 292 | 87 | 99 | 160 | N | N | N | N | N | N |
| RECQL5 | high in NP | -2.6 | 0.014350315 | -1.8 | 13926 | 651 | 647 | 389 | 253 | 241 | 277 | N | N | P | N | N | N |
| HDAC2 | high in NP | -2.3 | 0.014340716 | -1.8 | 13927 | 133 | 111 | 126 | 46 | 59 | 67 | N | N | N | N | N | N |
| KCNMA1 | high in NP | -2.0 | 0.014313974 | -1.8 | 13928 | 125 | 174 | 173 | 89 | 95 | 57 | N | P | N | N | N | N |

TABLE 16-continued

Genes that Are Differentially Methylated between Nulliparous and Parous CD24+ Breast Epithelial Cells

| | | | | SAGE-seq | | | | | | | | ChIP-seq | | | MSDK-seq | | | |
|---|---|---|---|---|---|---|---|---|---|---|---|---|---|---|---|---|---|---|
| | | | | | | Nulliparous (NP) | | | | Parous (P) | | | | | | | | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | NP | GeneBody | GeneBody Met | Pro-moter | Pro-moter Met | P |
| RBM12 | high in NP | −2.8 | 0.014307803 | −1.8 | 13929 | 215 | 300 | 186 | 49 | 116 | 102 | N | N | NP | NP | N | N | N | N |
| GYLTL1B | high in NP | −3.4 | 0.014298204 | −1.8 | 13930 | 26 | 19 | 44 | 9 | 9 | 13 | N | N | N | N | N | N | N | N |
| LMF2 | high in NP | −4.3 | 0.014191237 | −1.8 | 13931 | 162 | 492 | 471 | 94 | 99 | 121 | N | N | N | N | N | N | N | N |
| CHKB | high in NP | −3.3 | 0.014185066 | −1.8 | 13932 | 83 | 140 | 98 | 19 | 33 | 59 | N | N | N | N | N | N | N | N |
| DYRK3 | high in NP | −2.1 | 0.014178895 | −1.8 | 13933 | 15 | 11 | 10 | 9 | 7 | 7 | N | N | N | N | N | N | N | N |
| EPB41L5 | high in NP | −2.1 | 0.014162438 | −1.8 | 13934 | 21 | 46 | 32 | 16 | 16 | 16 | N | N | N | N | N | N | N | N |
| CAD | high in NP | −2.8 | 0.014156267 | −1.8 | 13935 | 134 | 157 | 475 | 71 | 59 | 53 | N | N | N | N | N | N | N | N |
| IGFBP2 | high in NP | −4.0 | 0.014117183 | −1.8 | 13936 | 74 | 125 | 85 | 31 | 25 | 59 | N | N | N | N | N | N | N | N |
| IL13RA1 | high in NP | −5.2 | 0.014101413 | −1.8 | 13937 | 111 | 527 | 348 | 84 | 85 | 57 | N | N | N | N | N | N | N | N |
| EHBP1L1 | high in NP | −2.2 | 0.014030787 | −1.8 | 13938 | 82 | 152 | 147 | 67 | 55 | 51 | N | N | N | N | N | N | N | N |
| ALDH4A1 | high in NP | −3.2 | 0.013997189 | −1.8 | 13939 | 88 | 109 | 323 | 40 | 49 | 28 | N | N | N | N | N | N | N | N |
| GRK6 | high in NP | −2.4 | 0.013975247 | −1.9 | 13940 | 134 | 204 | 324 | 77 | 83 | 87 | N | N | N | N | N | N | N | N |
| CBX6 | high in NP | −2.7 | 0.013965647 | −1.9 | 13941 | 37 | 51 | 37 | 15 | 27 | 11 | N | N | N | N | N | N | N | N |
| PRAGMIN | high in NP | −2.2 | 0.013887479 | −1.9 | 13942 | NA | NA | NA | NA | NA | NA | N | N | N | N | N | N | N | N |
| NCAPH2 | high in NP | −2.9 | 0.013874451 | −1.9 | 13943 | 314 | 297 | 465 | 71 | 123 | 187 | N | N | N | N | N | N | N | N |
| TTRAP | high in NP | −3.4 | 0.01386828 | −1.9 | 13944 | 22 | 24 | 14 | 12 | 6 | 10 | N | N | N | N | N | N | N | N |
| TOLLIP | high in NP | −2.1 | 0.01380794 | −1.9 | 13945 | 198 | 376 | 295 | 120 | 154 | 147 | N | N | N | N | N | N | N | N |
| CTDSP1 | high in NP | −5.0 | 0.013728401 | −1.9 | 13946 | 155 | 804 | 331 | 118 | 78 | 72 | N | N | N | N | N | N | N | N |
| RPL29 | high in NP | −2.8 | 0.013716059 | −1.9 | 13947 | 188 | 81 | 116 | 41 | 43 | 36 | N | N | N | N | N | N | N | N |
| MAPK8IP1 | high in NP | −2.3 | 0.0163172 | −1.9 | 13948 | 19 | 9 | 6 | 3 | 3 | 3 | N | N | N | N | N | N | N | N |
| DHX29 | high in NP | −2.0 | 0.013558352 | −1.9 | 13949 | 34 | 40 | 27 | 18 | 13 | 19 | N | N | N | N | N | N | N | N |
| C7orf53 | high in NP | −2.7 | 0.013548752 | −1.9 | 13950 | 39 | 26 | 22 | 8 | 8 | 14 | N | N | N | N | N | N | N | N |
| C1orf77 | high in NP | −5.0 | 0.013526125 | −1.9 | 13951 | 85 | 86 | 25 | 11 | 5 | 23 | N | N | N | N | N | N | N | N |
| CFDP1 | high in NP | −3.7 | 0.013481555 | −1.9 | 13952 | 47 | 41 | 50 | 10 | 12 | 28 | N | N | N | N | N | N | N | N |
| RPSAP58 | high in NP | −3.2 | 0.013468527 | −1.9 | 13953 | 6862 | 4967 | 3444 | 738 | 1582 | 2047 | N | NA | N | N | N | N | N | N |
| ZDHHC4 | high in NP | −3.7 | 0.013448642 | −1.9 | 13954 | 192 | 104 | 88 | 28 | 61 | 20 | NA | NA | N | N | N | N | N | N |
| IFRD2 | high in NP | −7.4 | 0.013442471 | −1.9 | 13955 | 95 | 439 | 480 | 36 | 75 | 70 | N | N | N | N | N | N | N | N |
| IMPS | high in NP | −2.9 | 0.01338076 | −1.9 | 13956 | 66 | 175 | 61 | 36 | 35 | 26 | N | N | N | N | N | N | N | N |
| CD1D | high in NP | −1.8 | 0.013362246 | −1.9 | 13957 | 9 | 9 | 6 | 4 | 4 | 4 | P | P | N | N | N | N | N | N |
| SCAMP4 | high in NP | −1.9 | 0.013343047 | −1.9 | 13958 | 70 | 107 | 81 | 46 | 44 | 37 | N | N | N | N | N | N | N | N |
| ARAF | high in NP | −5.4 | 0.013331391 | −1.9 | 13959 | 40 | 201 | 110 | 20 | 38 | 13 | N | N | N | N | N | N | N | N |
| MC1R | high in NP | −3.8 | 0.013295049 | −1.9 | 13960 | 21 | 71 | 40 | 11 | 12 | 17 | N | N | N | N | N | N | N | N |
| TCEB2 | high in NP | −2.1 | 0.013276536 | −1.9 | 13961 | 188 | 250 | 379 | 123 | 102 | 116 | N | N | N | N | N | N | N | N |
| STRC | high in NP | −2.6 | 0.013233338 | −1.9 | 13962 | 23 | 22 | 13 | 7 | 7 | 10 | N | N | N | N | N | N | N | N |
| TOP1MT | high in NP | −4.4 | 0.013227167 | −1.9 | 13963 | 23 | 22 | 6 | 5 | 5 | 2 | N | N | N | N | N | N | N | N |
| ADRM1 | high in NP | −3.8 | 0.013181226 | −1.9 | 13964 | 358 | 1024 | 804 | 248 | 296 | 223 | N | N | N | N | N | N | N | N |
| PROCA1 | high in NP | −3.0 | 0.013063289 | −1.9 | 13965 | 8 | 5 | 7 | 5 | 3 | 3 | N | N | N | N | N | N | N | N |
| SPTAN1 | high in NP | −2.5 | 0.013006377 | −1.9 | 13966 | 146 | 193 | 184 | 80 | 61 | 105 | N | N | N | N | N | N | N | N |
| THAP9 | high in NP | −2.1 | 0.012974835 | −1.9 | 13967 | 14 | 15 | 11 | 8 | 8 | 6 | N | N | N | N | N | N | N | N |
| HCFC1 | high in NP | −3.2 | 0.012962493 | −1.9 | 13968 | 179 | 523 | 353 | 123 | 107 | 143 | N | N | N | N | N | N | N | N |
| WDR18 | high in NP | −2.6 | 0.012942608 | −1.9 | 13969 | 69 | 142 | 136 | 46 | 54 | 28 | N | N | N | N | N | N | N | N |
| NFKBIL1 | high in NP | −2.8 | 0.012931637 | −1.9 | 13970 | 56 | 55 | 70 | 22 | 22 | 35 | N | N | N | N | N | N | N | N |
| GAK | high in NP | −2.4 | 0.012916552 | −1.9 | 13971 | 972 | 1302 | 1555 | 458 | 679 | 573 | N | N | N | N | N | N | N | N |
| TMEM51 | high in NP | −3.0 | 0.012901467 | −1.9 | 13972 | 173 | 220 | 108 | 63 | 40 | 75 | N | N | N | N | N | N | N | N |

TABLE 16-continued

Genes that Are Differentially Methylated between Nulliparous and Parous CD24+ Breast Epithelial Cells

| | | | | SAGE-seq | Nulliparous (NP) | | | | Parous (P) | | | ChIP-seq | | | MSDK-seq | | |
|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | P GeneBody Met | NP Pro-moter Met | P Pro-moter Met |
| TRPM4 | high in NP | -1.7 | 0.01288364 | -1.9 | 13973 | 34 | 52 | 46 | 23 | 21 | 22 | N | N | NP | N | N | N |
| NAT14 | high in NP | -4.5 | 0.012868555 | -1.9 | 13974 | 37 | 56 | 103 | 19 | 20 | 7 | N | N | N | N | N | N |
| NQO1 | high in NP | -1.9 | 0.012825357 | -1.9 | 13975 | 61 | 85 | 59 | 37 | 43 | 30 | N | N | N | N | N | N |
| PLA2G2A | high in NP | -2.6 | 0.012782159 | -1.9 | 13976 | 12 | 12 | 6 | 6 | 4 | 4 | N | N | N | N | N | N |
| SLC35A4 | high in NP | -5.3 | 0.012767074 | -1.9 | 13977 | 74 | 390 | 193 | 57 | 42 | 38 | N | N | N | N | N | N |
| CD2AP | high in NP | -3.4 | 0.012750617 | -1.9 | 13978 | 107 | 85 | 47 | 34 | 27 | 28 | N | N | N | N | N | N |
| SIGLEC8 | high in NP | -2.9 | 0.012738275 | -1.9 | 13979 | 106 | 78 | 78 | 24 | 27 | 48 | N | P | N | N | N | N |
| PSPC1 | high in NP | -2.8 | 0.012719761 | -1.9 | 13980 | 30 | 70 | 22 | 12 | 12 | 9 | N | N | N | N | N | N |
| ATN1 | high in NP | -1.8 | 0.012705362 | -1.9 | 13981 | 865 | 1042 | 1404 | 696 | 678 | 659 | N | N | N | N | N | N |
| DOST | high in NP | -3.3 | 0.01268342 | -1.9 | 13982 | 55 | 208 | 61 | 24 | 17 | 28 | N | N | N | N | N | N |
| SFT2D1 | high in NP | -3.5 | 0.012677249 | -1.9 | 13983 | 58 | 57 | 42 | 15 | 31 | 10 | N | N | N | N | N | N |
| ESRP1 | high in NP | -2.3 | 0.012671078 | -1.9 | 13984 | 78 | 45 | 43 | 19 | 18 | 12 | N | N | N | N | N | N |
| C19orf40 | high in NP | -3.2 | 0.012664845 | -1.9 | 13985 | 229 | 273 | 101 | 41 | 43 | 86 | NA | NA | N | N | N | N |
| RAD9A | high in NP | -2.7 | 0.012642279 | -1.9 | 13986 | 131 | 179 | 94 | 38 | 53 | 68 | N | N | N | N | N | N |
| PILRB | high in NP | -3.5 | 0.012600453 | -1.9 | 13987 | 84 | 232 | 180 | 40 | 58 | 64 | N | N | N | N | N | N |
| EIF3D | high in NP | -3.8 | 0.01258811 | -1.9 | 13988 | 592 | 1768 | 1012 | 299 | 309 | 458 | N | N | N | N | N | N |
| SEMA3B | high in NP | -3.7 | 0.01256754 | -1.9 | 13989 | 3043 | 2995 | 7471 | 817 | 1890 | 1088 | N | N | N | N | N | N |
| BAP1 | high in NP | -3.4 | 0.012483886 | -1.9 | 13990 | 205 | 519 | 392 | 129 | 156 | 124 | N | N | N | N | N | N |
| PKN3 | high in NP | -3.5 | 0.012474287 | -1.9 | 13991 | 63 | 87 | 82 | 43 | 24 | 12 | N | N | N | N | N | N |
| MAP3K11 | high in NP | -3.9 | 0.012456459 | -1.9 | 13992 | 130 | 385 | 386 | 107 | 80 | 61 | N | N | N | N | N | N |
| SDHAF2 | high in NP | -4.4 | 0.01244206 | -1.9 | 13993 | 96 | 303 | 277 | 50 | 76 | 43 | NA | NA | N | N | N | N |
| YIF1A | high in NP | -6.1 | 0.012406404 | -1.9 | 13994 | 95 | 274 | 528 | 33 | 77 | 48 | P | P | N | N | N | N |
| CAPN8 | high in NP | -3.4 | 0.01238789 | -1.9 | 13995 | 521 | 1912 | 525 | 216 | 284 | 172 | NA | NA | N | N | N | N |
| FAH | high in NP | -2.2 | 0.012376234 | -1.9 | 13996 | 30 | 55 | 23 | 15 | 15 | 15 | N | N | N | N | N | N |
| ITPA | high in NP | -2.9 | 0.012363206 | -1.9 | 13997 | 40 | 39 | 21 | 8 | 18 | 10 | N | N | N | N | N | N |
| RBM3 | high in NP | -4.0 | 0.012344693 | -1.9 | 13998 | 402 | 444 | 245 | 55 | 129 | 161 | N | N | N | N | N | N |
| SCPEP1 | high in NP | -2.3 | 0.01231178 | -1.9 | 13999 | 20 | 25 | 17 | 14 | 12 | 12 | N | N | N | N | P | N |
| ZC3HC1 | high in NP | -1.8 | 0.012299438 | -1.9 | 14000 | 10 | 13 | 8 | 5 | 5 | 5 | N | N | N | N | N | N |
| MAD1L1 | high in NP | -4.3 | 0.012269953 | -1.9 | 14001 | 43 | 129 | 155 | 29 | 31 | 22 | N | N | N | N | N | N |
| MCM9 | high in NP | -3.0 | 0.012256925 | -1.9 | 14002 | 9 | 10 | 9 | 4 | 4 | 7 | P | P | N | N | N | N |
| MIDN | high in NP | -2.2 | 0.012224013 | -1.9 | 14003 | 1673 | 2081 | 1830 | 871 | 730 | 1160 | N | N | N | N | N | N |
| MED22 | high in NP | -2.5 | 0.012206185 | -1.9 | 14004 | 51 | 89 | 91 | 23 | 40 | 31 | N | N | N | N | N | N |
| PLA2G2D | high in NP | -2.4 | 0.0121911 | -1.9 | 14005 | 281 | 261 | 165 | 94 | 108 | 111 | N | N | N | N | N | N |
| CXCL5 | high in NP | -5.1 | 0.012171215 | -1.9 | 14006 | 35 | 92 | 39 | 8 | 24 | 4 | N | N | N | N | N | N |
| TMEM88 | high in NP | -3.7 | 0.012121116 | -1.9 | 14007 | 136 | 80 | 132 | 16 | 46 | 41 | N | N | N | N | N | N |
| LRP5 | high in NP | -2.1 | 0.012114989 | -1.9 | 14008 | 65 | 84 | 65 | 21 | 34 | 32 | N | N | N | N | N | N |
| ABT1 | high in NP | -2.6 | 0.012108818 | -1.9 | 14009 | 66 | 197 | 92 | 36 | 32 | 39 | P | P | N | N | N | N |
| SMAD3 | high in NP | -2.6 | 0.012064248 | -1.9 | 14010 | 707 | 1532 | 1124 | 367 | 511 | 510 | N | N | N | N | N | N |
| WDR59 | high in NP | -2.7 | 0.012042307 | -1.9 | 14011 | 97 | 114 | 62 | 25 | 41 | 37 | N | N | N | N | N | N |
| SNRNP70 | high in NP | -4.3 | 0.012007337 | -1.9 | 14012 | 514 | 1907 | 1717 | 223 | 251 | 461 | N | N | N | N | N | N |
| ARL8A | high in NP | -2.6 | 0.011957282 | -1.9 | 14013 | 625 | 1388 | 921 | 365 | 389 | 437 | N | P | N | N | N | N |
| AR | high in NP | -2.4 | 0.011951111 | -1.9 | 14014 | 19 | 40 | 16 | 9 | 7 | 10 | N | N | N | N | N | N |
| MAPK8IP3 | high in NP | -3.1 | 0.011883914 | -1.9 | 14015 | 394 | 659 | 952 | 258 | 234 | 307 | P | P | N | N | N | N |
| SH3D20 | high in NP | -4.5 | 0.011845516 | -1.9 | 14016 | 32 | 31 | 47 | 10 | 1 | 9 | NA | NA | N | N | N | N |

TABLE 16-continued

Genes that Are Differentially Methylated between Nulliparous and Parous CD24+ Breast Epithelial Cells

| | | | | | SAGE-seq | | | | | | | ChIP-seq | | | MSDK-seq | | |
|---|---|---|---|---|---|---|---|---|---|---|---|---|---|---|---|---|---|
| | | | | | | Nulliparous (NP) | | | Parous (P) | | | NP | P | GeneBody | GeneBody Met | Pro-moter Met | Pro-moter Met |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | CD24+ N74 | CD24+ N66 | NP | P | NP | P |
| TXNDC16 | high in NP | -2.6 | 0.011827002 | -1.9 | 14017 | 37 | 42 | 22 | 16 | 16 | 22 | N | N | N | N | N | N |
| C8orf58 | high in NP | -2.3 | 0.011765291 | -1.9 | 14018 | 19 | 26 | 27 | 13 | 7 | 10 | N | N | N | N | N | N |
| XPOT | high in NP | -2.2 | 0.011170975 | -1.9 | 14019 | 104 | 148 | 105 | 61 | 69 | 43 | N | N | N | N | P | N |
| SYCE1 | high in NP | -3.9 | 0.011686437 | -1.9 | 14020 | 51 | 27 | 20 | 4 | 7 | 15 | P | N | N | N | N | N |
| ADIPOR1 | high in NP | -2.4 | 0.011665867 | -1.9 | 14021 | 277 | 343 | 214 | 106 | 152 | 145 | N | N | N | N | N | N |
| CAPN1 | high in NP | -3.1 | 0.011647353 | -1.9 | 14022 | 565 | 1932 | 760 | 387 | 284 | 226 | N | P | N | N | N | N |
| SCMH1 | high in NP | -2.7 | 0.011641182 | -1.9 | 14023 | 32 | 57 | 44 | 12 | 17 | 23 | N | N | N | N | N | N |
| C22orf13 | high in NP | -3.4 | 0.011554786 | -1.9 | 14024 | 198 | 745 | 398 | 146 | 123 | 96 | N | N | N | N | N | N |
| CES8 | high in NP | -4.2 | 0.011467019 | -1.9 | 14025 | 54 | 24 | 38 | 6 | 6 | 20 | N | NA | N | N | N | N |
| R3HCC1 | high in NP | -4.4 | 0.011453991 | -1.9 | 14026 | 129 | 234 | 376 | 53 | 97 | 53 | N | N | N | N | N | N |
| WDR13 | high in NP | -2.2 | 0.011438906 | -1.9 | 14027 | 302 | 337 | 439 | 156 | 175 | 198 | N | N | N | N | N | N |
| ZNF625 | high in NP | -1.9 | 0.011426563 | -1.9 | 14028 | 40 | 56 | 46 | 20 | 27 | 21 | N | N | N | N | N | N |
| CCND1 | high in NP | -2.9 | 0.011319845 | -1.9 | 14029 | 421 | 1118 | 445 | 200 | 242 | 159 | N | N | N | N | N | N |
| SETD3 | high in NP | -4.3 | 0.011319597 | -1.9 | 14030 | 48 | 80 | 36 | 12 | 15 | 29 | N | N | N | N | N | N |
| AMFR | high in NP | -3.1 | 0.011313426 | -1.9 | 14031 | 182 | 433 | 410 | 160 | 74 | 96 | N | N | N | N | N | N |
| RPL36 | high in NP | -2.4 | 0.011255828 | -1.9 | 14032 | 47455 | 30557 | 28913 | 13016 | 13760 | 16986 | P | N | N | N | N | N |
| ZNF667 | high in NP | -2.3 | 0.011229087 | -1.9 | 14033 | 26 | 20 | 18 | 9 | 12 | 9 | N | N | N | N | N | N |
| FAM65A | high in NP | -3.1 | 0.011222916 | -1.9 | 14034 | 295 | 915 | 524 | 185 | 199 | 207 | N | N | N | N | N | N |
| ACSF3 | high in NP | -2.6 | 0.011199602 | -1.9 | 14035 | 93 | 138 | 224 | 60 | 54 | 42 | P | N | N | N | N | N |
| RASSF3 | high in NP | -2.7 | 0.011115709 | -2.0 | 14036 | 10 | 24 | 13 | 5 | 5 | 5 | N | N | N | N | N | N |
| DEF6 | high in NP | -3.4 | 0.011072065 | -2.0 | 14037 | 40 | 38 | 30 | 11 | 21 | 13 | N | N | N | N | N | N |
| CYTSA | high in NP | -2.2 | 0.011102681 | -2.0 | 14038 | 196 | 323 | 295 | 136 | 152 | 112 | NA | N | N | N | N | N |
| TSC2 | high in NP | -2.2 | 0.010989098 | -2.0 | 14039 | 151 | 259 | 233 | 137 | 109 | 102 | N | NA | N | N | N | N |
| CCS | high in NP | -5.2 | 0.010899959 | -2.0 | 14040 | 21 | 66 | 83 | 15 | 8 | 11 | N | N | N | N | N | N |
| GIPC1 | high in NP | -2.9 | 0.010801221 | -2.0 | 14041 | 544 | 970 | 413 | 156 | 272 | 209 | P | N | N | N | N | N |
| PRDM2 | high in NP | -2.7 | 0.010779279 | -2.0 | 14042 | 242 | 263 | 169 | 94 | 104 | 110 | N | N | N | N | N | N |
| SDHAF1 | high in NP | -3.9 | 0.010753223 | -2.0 | 14043 | 20 | 52 | 51 | 10 | 11 | 12 | NA | N | N | N | N | N |
| LRRC8A | high in NP | -2.4 | 0.010734709 | -2.0 | 14044 | 751 | 823 | 1035 | 405 | 321 | 556 | N | N | N | N | N | N |
| GCN1L1 | high in NP | -2.5 | 0.010723738 | -2.0 | 14045 | 155 | 221 | 198 | 50 | 104 | 71 | N | N | N | N | N | N |
| SPAG7 | high in NP | -3.8 | 0.010676426 | -2.0 | 14046 | 205 | 154 | 326 | 52 | 102 | 40 | N | P | N | N | N | N |
| SND1 | high in NP | -2.1 | 0.010670255 | -2.0 | 14047 | 668 | 981 | 993 | 418 | 466 | 434 | N | N | N | N | N | N |
| SERPINA3 | high in NP | -4.1 | 0.010631857 | -2.0 | 14048 | 2963 | 7386 | 1626 | 512 | 863 | 922 | N | N | P | N | N | N |
| C17orf101 | high in NP | -4.2 | 0.010591402 | -2.0 | 14049 | 17 | 54 | 49 | 7 | 8 | 13 | NA | N | N | N | N | N |
| LGALS1 | high in NP | -2.7 | 0.010581523 | -2.0 | 14050 | 349 | 197 | 164 | 96 | 72 | 86 | N | N | N | N | N | N |
| MIF | high in NP | -2.1 | 0.010547518 | -2.0 | 14051 | 2533 | 3575 | 4063 | 1762 | 1621 | 1290 | NA | N | N | N | N | N |
| E2F1 | high in NP | -2.4 | 0.010541347 | -2.0 | 14052 | 17 | 19 | 21 | 7 | 10 | 11 | N | N | N | N | N | N |
| HAGHL | high in NP | -3.0 | 0.010510491 | -2.0 | 14053 | 10 | 21 | 23 | 5 | 5 | 5 | N | N | N | N | N | N |
| NHS | high in NP | -2.1 | 0.010496092 | -2.0 | 14054 | 41 | 41 | 43 | 21 | 28 | 26 | N | P | N | N | N | N |
| RHOT2 | high in NP | -5.4 | 0.010459065 | -2.0 | 14055 | 149 | 436 | 589 | 97 | 96 | 80 | N | N | N | N | N | N |
| IL17RD | high in NP | -3.1 | 0.010452894 | -2.0 | 14056 | 64 | 120 | 75 | 39 | 53 | 41 | N | N | N | N | N | N |
| NDUFB7 | high in NP | -2.7 | 0.010416552 | -2.0 | 14057 | 113 | 165 | 167 | 62 | 79 | 36 | N | N | N | N | N | N |
| ACADM | high in NP | -2.8 | 0.010403524 | -2.0 | 14058 | 67 | 63 | 95 | 39 | 24 | 26 | N | N | N | N | N | N |
| TMC7 | high in NP | -2.8 | 0.010397353 | -2.0 | 14059 | 98 | 170 | 72 | 44 | 37 | 35 | N | N | N | N | N | N |
| PLA2G15 | high in NP | -4.7 | 0.010378154 | -2.0 | 14060 | 38 | 98 | 159 | 25 | 20 | 16 | N | N | N | N | N | N |

TABLE 16-continued

Genes that Are Differentially Methylated between Nulliparous and Parous CD24+ Breast Epithelial Cells

| | | | | SAGE-seq | | Nulliparous (NP) | | | Parous (P) | | | ChIP-seq | | | | MSDK-seq | | |
|---|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | P GeneBody Met | NP Pro-moter Met | P Pro-moter Met |
| HOXB2 | high in NP | -5.6 | 0.010371983 | -2.0 | 14061 | 33 | 18 | 7 | 6 | 2 | 5 | N | N | NP | N | N | N |
| ZNF512B | high in NP | -3.9 | 0.010362383 | -2.0 | 14062 | 130 | 298 | 370 | 78 | 106 | 67 | N | N | N | N | N | N |
| CYB5RL | high in NP | -2.4 | 0.010356212 | -2.0 | 14063 | 163 | 143 | 98 | 59 | 48 | 67 | NA | NA | N | N | N | N |
| PSMD8 | high in NP | -2.1 | 0.010339756 | -2.0 | 14064 | 366 | 689 | 462 | 228 | 206 | 222 | N | N | N | N | N | N |
| GADD45B | high in NP | -4.8 | 0.01019302 | -2.0 | 14065 | 5166 | 2141 | 3205 | 432 | 672 | 1515 | N | N | N | N | N | N |
| TMEM134 | high in NP | -3.5 | 0.010173821 | -2.0 | 14066 | 152 | 196 | 436 | 67 | 88 | 49 | N | N | N | N | N | N |
| KRTAP1-1 | high in NP | -3.0 | 0.010161478 | -2.0 | 14067 | 7 | 5 | 5 | 4 | 2 | 2 | N | N | N | N | N | N |
| DAZAP1 | high in NP | -3.6 | 0.010083996 | -2.0 | 14068 | 551 | 1425 | 1052 | 318 | 386 | 307 | N | N | N | N | N | N |
| TCEAL4 | high in NP | -5.0 | 0.010077825 | -2.0 | 14069 | 54 | 69 | 47 | 12 | 4 | 25 | N | N | N | N | N | N |
| MAP2K2 | high in NP | -2.4 | 0.010071654 | -2.0 | 14070 | 879 | 1322 | 1143 | 499 | 599 | 389 | N | N | N | N | N | N |
| C1AO1 | high in NP | -2.8 | 0.010065483 | -2.0 | 14071 | 254 | 254 | 157 | 79 | 71 | 107 | N | N | N | N | N | N |
| CSTF1 | high in NP | -5.7 | 0.010055883 | -2.0 | 14072 | 41 | 66 | 49 | 10 | 26 | 6 | N | N | N | N | N | N |
| ANKRD30A | high in NP | -2.7 | 0.01004217 | -2.0 | 14073 | 19 | 81 | 20 | 6 | 6 | 6 | N | N | N | N | N | N |
| DCAF11 | high in NP | -3.0 | 0.010022285 | -2.0 | 14074 | 141 | 93 | 110 | 53 | 38 | 36 | NA | NA | N | N | N | N |
| TSPAN13 | high in NP | -5.1 | 0.009989372 | -2.0 | 14075 | 78 | 85 | 24 | 7 | 12 | 19 | N | N | N | N | N | N |
| C1orf122 | high in NP | -6.4 | 0.009924232 | -2.0 | 14076 | 83 | 200 | 67 | 14 | 39 | 6 | N | N | N | N | N | N |
| ATM | high in NP | -2.0 | 0.009896119 | -2.0 | 14077 | 56 | 61 | 49 | 31 | 28 | 34 | N | N | N | N | N | N |
| SF3B14 | high in NP | -2.4 | 0.009883777 | -2.0 | 14078 | 128 | 211 | 107 | 48 | 57 | 69 | N | N | N | N | N | N |
| GHDC | high in NP | -3.6 | 0.009871434 | -2.0 | 14079 | 20 | 62 | 50 | 8 | 15 | 11 | N | N | N | N | N | N |
| TTLL3 | high in NP | -2.4 | 0.009856349 | -2.0 | 14080 | 303 | 269 | 297 | 89 | 147 | 149 | N | N | N | N | N | N |
| GFOD1 | high in NP | -3.3 | 0.009817951 | -2.0 | 14081 | 109 | 57 | 48 | 26 | 26 | 20 | N | N | N | N | N | N |
| PEX1 | high in NP | -2.2 | 0.009770639 | -2.0 | 14082 | 32 | 55 | 36 | 18 | 21 | 14 | N | N | N | N | N | N |
| GRINA | high in NP | -2.8 | 0.009649273 | -2.0 | 14083 | 331 | 708 | 570 | 218 | 225 | 228 | N | N | N | N | N | N |
| EIF4EBP1 | high in NP | -2.8 | 0.009643102 | -2.0 | 14084 | 388 | 603 | 305 | 212 | 165 | 132 | N | N | N | N | N | N |
| TARSL2 | high in NP | -4.6 | 0.009636931 | -2.0 | 14085 | 12 | 35 | 24 | 7 | 7 | 7 | N | N | N | N | N | N |
| EID1 | high in NP | -2.1 | 0.009623903 | -2.0 | 14086 | 122 | 90 | 79 | 40 | 43 | 41 | N | N | N | N | N | N |
| C11orf31 | high in NP | -1.9 | 0.009611561 | -2.0 | 14087 | 345 | 315 | 307 | 181 | 186 | 157 | N | N | N | N | N | N |
| UGDH | high in NP | -4.6 | 0.009575219 | -2.0 | 14088 | 307 | 228 | 120 | 57 | 76 | 49 | N | N | N | N | N | N |
| GTPBP6 | high in NP | -2.0 | 0.009489509 | -2.0 | 14089 | 185 | 171 | 167 | 95 | 84 | 108 | N | N | N | N | N | N |
| CAPS | high in NP | -2.8 | 0.009479909 | -2.0 | 14090 | 22 | 54 | 35 | 11 | 8 | 14 | N | N | N | N | N | N |
| ARL6IP4 | high in NP | -2.2 | 0.009464824 | -2.0 | 14091 | 220 | 358 | 217 | 139 | 120 | 122 | N | N | N | N | N | N |
| THAP1 | high in NP | -3.4 | 0.009440826 | -2.0 | 14092 | 7 | 20 | 7 | 2 | 2 | 2 | N | N | N | N | N | N |
| CD9 | high in NP | -4.9 | 0.009418884 | -2.0 | 14093 | 336 | 272 | 117 | 74 | 29 | 59 | N | N | N | N | N | N |
| HOMER2 | high in NP | -5.1 | 0.009412713 | -2.0 | 14094 | 118 | 453 | 297 | 32 | 67 | 76 | N | N | N | N | N | N |
| SH3GLB2 | high in NP | -2.2 | 0.009372257 | -2.0 | 14095 | 746 | 1141 | 1051 | 503 | 398 | 495 | N | N | N | N | N | N |
| STAP2 | high in NP | -4.4 | 0.009337287 | -2.0 | 14096 | 92 | 56 | 119 | 6 | 30 | 20 | N | N | N | N | P | N |
| FAM22A | high in NP | -5.5 | 0.009315346 | -2.0 | 14097 | 12 | 29 | 32 | 4 | 4 | 10 | N | N | N | N | N | N |
| MLPH | high in NP | -3.8 | 0.009309174 | -2.0 | 14098 | 106 | 73 | 42 | 26 | 15 | 16 | N | N | N | N | N | N |
| SVOPL | high in NP | -2.7 | 0.009281747 | -2.0 | 14099 | 11 | 7 | 9 | 3 | 6 | 3 | N | N | N | N | N | N |
| PPP2R1A | high in NP | -3.4 | 0.009246777 | -2.0 | 14100 | 613 | 2051 | 986 | 380 | 333 | 278 | N | N | N | N | N | N |
| MOSC1 | high in NP | -2.5 | 0.009211122 | -2.0 | 14101 | 10 | 9 | 14 | 6 | 6 | 6 | N | N | N | N | N | N |
| ALDH5A1 | high in NP | -2.3 | 0.009165181 | -2.0 | 14102 | 29 | 35 | 27 | 15 | 13 | 18 | N | N | N | N | N | N |
| PTPRF | high in NP | -3.0 | 0.009111012 | -2.0 | 14103 | 924 | 1221 | 1470 | 515 | 350 | 660 | N | N | N | N | N | N |
| ARRDC1 | high in NP | -4.5 | 0.009072614 | -2.0 | 14104 | 246 | 718 | 590 | 142 | 170 | 121 | N | N | N | N | N | N |

TABLE 16-continued

Genes that Are Differentially Methylated between Nulliparous and Parous CD24+ Breast Epithelial Cells

| | | | | | SAGE-seq | Nulliparous (NP) | | | | Parous (P) | | | | ChIP-seq | | | MSDK-seq | | |
|---|---|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | NP | P | GeneBody NP | GeneBody Met | Pro-moter Met | NP | P | Pro-moter Met |
| TTC18 | high in NP | -2.4 | 0.009066443 | -2.0 | 14105 | 15 | 15 | 13 | 7 | 10 | 7 | NA | NA | N | N | N | N | N | N |
| SBF1P1 | high in NP | -3.2 | 0.009060272 | -2.0 | 14106 | 1280 | 727 | 1037 | 230 | 428 | 347 | NA | NA | N | N | N | N | N | N |
| KIAA1683 | high in NP | -2.8 | 0.009011588 | -2.0 | 14107 | 32 | 26 | 31 | 16 | 16 | 16 | N | N | N | N | N | N | N | N |
| TMEM184A | high in NP | -2.7 | 0.009005417 | -2.0 | 14108 | 196 | 179 | 377 | 85 | 83 | 78 | N | N | N | N | N | N | N | N |
| CHSY1 | high in NP | -3.3 | 0.008999246 | -2.0 | 14109 | 188 | 231 | 182 | 79 | 51 | 105 | N | N | N | N | N | N | N | N |
| KRT10 | high in NP | -4.7 | 0.008993075 | -2.0 | 14110 | 22 | 83 | 36 | 8 | 12 | 11 | N | N | N | N | N | N | N | N |
| TP53TG1 | high in NP | -3.2 | 0.008986903 | -2.0 | 14111 | 70 | 62 | 52 | 23 | 19 | 7 | N | N | N | N | N | N | N | N |
| VEZT | high in NP | -3.7 | 0.008969761 | -2.0 | 14112 | 98 | 214 | 58 | 24 | 33 | 30 | N | N | N | N | N | N | N | N |
| ZER1 | high in NP | -2.3 | 0.008935477 | -2.0 | 14113 | 334 | 454 | 568 | 216 | 231 | 171 | N | N | N | N | N | N | N | N |
| DTX2 | high in NP | -3.1 | 0.008895708 | -2.0 | 14114 | 143 | 271 | 161 | 48 | 93 | 56 | N | N | N | N | N | N | N | N |
| PUM1 | high in NP | -3.1 | 0.008831253 | -2.0 | 14115 | 157 | 394 | 156 | 68 | 75 | 86 | N | N | N | N | N | N | N | N |
| NARFL | high in NP | -3.3 | 0.008818911 | -2.1 | 14116 | 17 | 62 | 37 | 11 | 9 | 9 | N | N | N | N | N | N | N | N |
| SEMG2 | high in NP | -3.2 | 0.008790798 | -2.1 | 14117 | 21 | 2 | 2 | 1 | 1 | 1 | N | N | N | N | N | N | N | N |
| OUTA | high in NP | -3.9 | 0.00877297 | -2.1 | 14118 | 822 | 346 | 410 | 93 | 143 | 178 | N | N | N | N | N | N | N | N |
| BLOC1S3 | high in NP | -2.2 | 0.008751714 | -2.1 | 14119 | 32 | 44 | 30 | 14 | 17 | 11 | N | N | N | N | N | N | N | N |
| ACAD11 | high in NP | -3.7 | 0.008738686 | -2.1 | 14120 | 185 | 97 | 173 | 56 | 47 | 42 | N | N | N | N | N | N | N | N |
| TWF2 | high in NP | -5.4 | 0.008703031 | -2.1 | 14121 | 50 | 186 | 152 | 33 | 24 | 16 | N | N | N | N | N | N | N | N |
| PSMAG | high in NP | -2.6 | 0.00869686 | -2.1 | 14122 | 303 | 637 | 269 | 118 | 146 | 145 | N | N | N | N | N | N | N | N |
| UQCRH | high in NP | -2.3 | 0.008671489 | -2.1 | 14123 | 2207 | 2263 | 1610 | 912 | 830 | 1058 | N | N | N | N | N | N | N | N |
| MAPK7 | high in NP | -2.4 | 0.008659147 | -2.1 | 14124 | 117 | 123 | 132 | 54 | 62 | 31 | N | N | N | N | N | N | N | N |
| ANO10 | high in NP | -2.7 | 0.008646119 | -2.1 | 14125 | 111 | 175 | 181 | 75 | 64 | 38 | N | N | N | N | N | N | N | N |
| C10orf57 | high in NP | -2.0 | 0.008585779 | -2.1 | 14126 | 13 | 14 | 10 | 5 | 5 | 5 | N | N | N | N | N | N | N | N |
| CDK2 | high in NP | -3.0 | 0.008548066 | -2.1 | 14127 | 96 | 126 | 147 | 27 | 49 | 54 | N | N | N | N | N | N | N | N |
| COPB2 | high in NP | -3.5 | 0.008511039 | -2.1 | 14128 | 122 | 145 | 60 | 41 | 28 | 22 | N | N | N | N | N | N | N | N |
| RNF166 | high in NP | -8.2 | 0.008467156 | -2.1 | 14129 | 11 | 48 | 50 | 7 | 3 | 3 | N | N | N | N | N | N | N | N |
| NUCB2 | high in NP | -3.4 | 0.008439043 | -2.1 | 14130 | 188 | 377 | 123 | 64 | 61 | 58 | N | N | N | N | N | N | N | N |
| ZDHHC8P | high in NP | -2.1 | 0.008407501 | -2.1 | 14131 | NA | NA | NA | NA | NA | NA | N | N | N | N | N | N | N | N |
| TRIM45 | high in NP | -3.7 | 0.00830602 | -2.1 | 14132 | 22 | 13 | 24 | 6 | 12 | 6 | N | N | N | N | N | N | N | N |
| SLU7 | high in NP | -2.3 | 0.008293678 | -2.1 | 14133 | 136 | 211 | 134 | 65 | 81 | 68 | N | N | N | N | N | N | N | N |
| MST1P2 | high in NP | -7.5 | 0.008243623 | -2.1 | 14134 | 62 | 40 | 56 | 1 | 14 | 9 | N | N | N | N | N | N | N | N |
| ZNF506 | high in NP | -2.5 | 0.008229224 | -2.1 | 14135 | 13 | 11 | 13 | 5 | 8 | 5 | N | N | N | N | N | N | N | N |
| GGA1 | high in NP | -3.4 | 0.008198368 | -2.1 | 14136 | 323 | 301 | 521 | 194 | 96 | 97 | N | N | N | N | N | N | N | N |
| RNASEK | high in NP | -2.7 | 0.00818534 | -2.1 | 14137 | 1604 | 2599 | 3311 | 957 | 982 | 708 | N | N | N | N | N | N | N | N |
| LOC139201 | high in NP | -3.3 | 0.008166827 | -2.1 | 14138 | 55 | 38 | 28 | 7 | 19 | 12 | N | N | N | N | N | N | N | N |
| ZNF44 | high in NP | -3.7 | 0.008140085 | -2.1 | 14139 | 52 | 63 | 36 | 12 | 26 | 14 | N | N | N | N | N | N | N | N |
| TMEM101 | high in NP | -2.9 | 0.008103744 | -2.1 | 14140 | 114 | 213 | 183 | 44 | 81 | 45 | N | N | N | N | N | N | N | N |
| TNPO2 | high in NP | -2.7 | 0.008059174 | -2.1 | 14141 | 148 | 425 | 196 | 89 | 82 | 68 | N | N | N | N | N | N | N | N |
| GUK1 | high in NP | -3.3 | 0.008027633 | -2.1 | 14142 | 810 | 709 | 393 | 170 | 227 | 236 | N | N | N | N | N | N | N | N |
| STK36 | high in NP | -2.6 | 0.008021462 | -2.1 | 14143 | 38 | 45 | 25 | 12 | 13 | 16 | N | N | N | N | N | N | N | N |
| RRAGC | high in NP | -2.4 | 0.00800912 | -2.1 | 14144 | 337 | 283 | 266 | 133 | 107 | 157 | N | N | N | N | N | N | N | N |
| PCBP4 | high in NP | -5.3 | 0.008002948 | -2.1 | 14145 | 112 | 68 | 194 | 39 | 21 | 25 | N | N | N | N | N | N | N | N |
| EGFL8 | high in NP | -2.8 | 0.007996777 | -2.1 | 14146 | 32 | 37 | 62 | 14 | 15 | 18 | N | N | N | N | N | N | N | P |
| RAD54L2 | high in NP | -2.3 | 0.007949465 | -2.1 | 14147 | 72 | 153 | 100 | 47 | 44 | 41 | N | NA | N | N | N | N | N | N |
| METRN | high in NP | -3.5 | 0.00793438 | -2.1 | 14148 | 117 | 283 | 232 | 58 | 59 | 46 | N | P | N | N | N | N | P | N |

TABLE 16-continued

Genes that Are Differentially Methylated between Nulliparous and Parous CD24+ Breast Epithelial Cells

| | | | | SAGE-seq | | | | | | | | ChIP-seq | | | | MSDK-seq | | |
|---|---|---|---|---|---|---|---|---|---|---|---|---|---|---|---|---|---|---|
| | | | | | Nulliparous (NP) | | | | Parous (P) | | | NP | | CD24+ | P | | | Pro-moter |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | GeneBody Met | Pro-moter Met | Pro-moter Met | P |
|---|---|---|---|---|---|---|---|---|---|---|---|---|---|---|---|---|---|---|
| RPL41 | high in NP | -1.9 | 0.007928209 | -2.1 | 14149 | 127927 | 78691 | 78650 | 47221 | 47238 | 47213 | N | N | N | N | N | N | N |
| STAC3 | high in NP | -3.0 | 0.007889125 | -2.1 | 14150 | 7 | 3 | 6 | 2 | 2 | 2 | N | N | N | N | N | N | N |
| MAP2K7 | high in NP | -2.1 | 0.007882954 | -2.1 | 14151 | 481 | 483 | 564 | 292 | 279 | 322 | N | N | N | N | N | N | N |
| U2AF2 | high in NP | -3.7 | 0.007876783 | -2.1 | 14152 | 605 | 696 | 1291 | 199 | 331 | 300 | N | N | N | N | N | N | N |
| ZNF124 | high in NP | -2.5 | 0.007847984 | -2.1 | 14153 | 11 | 9 | 9 | 2 | 5 | 2 | N | N | N | N | N | N | N |
| RAB15 | high in NP | -2.2 | 0.007793815 | -2.1 | 14154 | 132 | 164 | 167 | 70 | 75 | 92 | N | N | N | N | N | P | N |
| PPFIBP2 | high in NP | -2.7 | 0.007787644 | -2.1 | 14155 | 47 | 47 | 30 | 18 | 13 | 21 | N | N | N | N | N | N | N |
| BRMS1 | high in NP | -3.7 | 0.007781473 | -2.1 | 14156 | 32 | 41 | 19 | 13 | 9 | 14 | N | N | N | N | N | N | N |
| ZNF771 | high in NP | -4.6 | 0.007775302 | -2.1 | 14157 | 40 | 25 | 49 | 9 | 14 | 5 | N | N | N | N | N | N | N |
| MAFK | high in NP | -4.1 | 0.007769131 | -2.1 | 14158 | 2443 | 1607 | 4697 | 410 | 648 | 869 | N | N | N | N | N | N | N |
| FAM63B | high in NP | -2.5 | 0.007756788 | -2.1 | 14159 | 53 | 71 | 73 | 39 | 28 | 30 | N | N | N | N | N | N | N |
| RPL13AP5 | high in NP | -4.3 | 0.007735532 | -2.1 | 14160 | 400 | 203 | 295 | 44 | 66 | 122 | N | NA | NA | N | N | N | N |
| MAPT | high in NP | -3.6 | 0.007647765 | -2.1 | 14161 | 302 | 137 | 133 | 59 | 51 | 38 | N | N | N | N | N | N | N |
| BRD9 | high in NP | -4.1 | 0.007636794 | -2.1 | 14162 | 125 | 239 | 283 | 37 | 74 | 67 | N | N | P | N | N | N | N |
| TCTN2 | high in NP | -4.0 | 0.007630623 | -2.1 | 14163 | 72 | 43 | 98 | 12 | 9 | 24 | N | N | N | N | N | N | N |
| TRPT1 | high in NP | -3.0 | 0.007624451 | -2.1 | 14164 | 24 | 16 | 15 | 8 | 4 | 4 | N | N | N | N | N | N | N |
| SMARCD2 | high in NP | -2.8 | 0.007613481 | -2.1 | 14165 | 106 | 182 | 178 | 71 | 60 | 44 | N | N | N | N | N | N | N |
| SAFB | high in NP | -2.5 | 0.007577825 | -2.1 | 14166 | 60 | 93 | 55 | 28 | 26 | 33 | N | N | N | N | N | N | N |
| CSRP1 | high in NP | -4.3 | 0.007565483 | -2.1 | 14167 | 10059 | 5673 | 10812 | 1130 | 2470 | 3089 | N | N | N | N | N | N | N |
| MLH3 | high in NP | -1.9 | 0.007550398 | -2.1 | 14168 | 48 | 62 | 55 | 26 | 29 | 30 | N | N | N | N | N | N | N |
| EIF2C2 | high in NP | -3.0 | 0.007535313 | -2.1 | 14169 | 181 | 220 | 231 | 69 | 77 | 113 | N | N | N | N | N | N | N |
| PKIG | high in NP | -4.1 | 0.007501714 | -2.1 | 14170 | 121 | 188 | 99 | 47 | 49 | 17 | N | NA | N | N | N | N | N |
| AMBP | high in NP | -2.1 | 0.007495543 | -2.1 | 14171 | 7 | 6 | 4 | 2 | 2 | 2 | N | N | N | N | N | N | N |
| FLJ23867 | high in NP | -2.3 | 0.007475658 | -2.1 | 14172 | 69 | 102 | 73 | 44 | 34 | 29 | N | NA | NA | N | N | N | N |
| NTAN1 | high in NP | -4.0 | 0.007469487 | -2.1 | 14173 | 11 | 28 | 10 | 3 | 3 | 6 | N | N | N | N | N | N | N |
| ZNF689 | high in NP | -3.5 | 0.007454402 | -2.1 | 14174 | 15 | 28 | 14 | 5 | 8 | 3 | N | N | N | N | N | N | N |
| ANKRD52 | high in NP | -3.3 | 0.007420804 | -2.1 | 14175 | 183 | 433 | 358 | 136 | 106 | 113 | N | N | N | N | N | N | N |
| FEZ2 | high in NP | -2.9 | 0.007414632 | -2.1 | 14176 | 140 | 218 | 175 | 49 | 89 | 68 | N | N | N | N | N | N | N |
| GDPD3 | high in NP | -3.0 | 0.007382405 | -2.1 | 14177 | 58 | 59 | 132 | 19 | 22 | 25 | N | N | N | N | N | N | N |
| KATNAL2 | high in NP | -3.2 | 0.007376234 | -2.1 | 14178 | 12 | 6 | 5 | 4 | 4 | 4 | N | N | N | N | N | N | N |
| LRRFIP2 | high in NP | -3.3 | 0.007341264 | -2.1 | 14179 | 2058 | 1702 | 1957 | 505 | 662 | 1021 | N | N | N | N | N | N | N |
| RILPL2 | high in NP | -3.3 | 0.007335093 | -2.1 | 14180 | 27 | 21 | 11 | 2 | 2 | 8 | N | N | N | N | N | N | N |
| LOC100130872 | high in NP | -2.0 | 0.007215099 | -2.1 | 14181 | 16 | 17 | 18 | 11 | 11 | 11 | N | NA | NA | N | N | N | N |
| TBC1D10B | high in NP | -3.1 | 0.007208928 | -2.1 | 14182 | 84 | 107 | 126 | 29 | 57 | 35 | N | N | N | N | N | N | N |
| PPM1G | high in NP | -2.7 | 0.007202756 | -2.1 | 14183 | 854 | 1240 | 1749 | 550 | 566 | 462 | N | N | N | N | N | N | N |
| ABHD14A | high in NP | -2.7 | 0.00715133 | -2.1 | 14184 | 15 | 22 | 18 | 9 | 9 | 10 | N | N | N | N | N | N | N |
| SRP19 | high in NP | -3.0 | 0.007132131 | -2.1 | 14185 | 8 | 7 | 4 | 3 | 3 | 3 | N | N | N | N | N | N | N |
| IMPDH2 | high in NP | -3.9 | 0.007112596 | -2.1 | 14186 | 383 | 368 | 200 | 56 | 106 | 110 | N | N | N | N | N | N | N |
| MRPS33 | high in NP | -9.6 | 0.007119789 | -2.1 | 14187 | 64 | 49 | 42 | 4 | 23 | 5 | N | N | N | N | N | N | N |
| MMP14 | high in NP | -3.1 | 0.007105389 | -2.1 | 14188 | 49 | 109 | 84 | 36 | 29 | 25 | N | N | N | N | N | N | N |
| AKIRIN1 | high in NP | -4.5 | 0.007099218 | -2.1 | 14189 | 453 | 347 | 267 | 75 | 76 | 168 | N | N | N | N | N | N | N |
| LNX2 | high in NP | -2.9 | 0.007008619 | -2.1 | 14190 | 30 | 81 | 44 | 17 | 12 | 15 | N | N | N | N | N | N | N |
| PNP | high in NP | -2.9 | 0.007018308 | -2.2 | 14191 | 626 | 494 | 529 | 179 | 193 | 292 | N | NA | NA | N | N | N | N |
| EBPL | high in NP | -2.7 | 0.00699568 | -2.2 | 14192 | 23 | 12 | 11 | 8 | 6 | 6 | N | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | | MSDK-seq | | |
|---|---|---|---|---|---|---|---|---|---|---|---|---|---|---|---|---|---|---|
| | | | | | | Nulliparous (NP) | | | | Parous (P) | | | NP | | P | NP | | P |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody | GeneBody Met | Pro-moter Met | Pro-moter Met |
| LENG9 | high in NP | -5.1 | 0.000948368 | -2.2 | 14193 | 298 | 205 | 228 | 43 | 49 | 111 | N | N | NP | N | N | N | N |
| MYO9B | high in NP | -3.3 | 0.000908398 | -2.2 | 14194 | 296 | 184 | 307 | 76 | 95 | 84 | N | N | N | N | N | N | N |
| KDM4B | high in NP | -2.4 | 0.000877743 | -2.2 | 14195 | 74 | 72 | 54 | 23 | 28 | 26 | NA | NA | N | N | N | N | N |
| PHRF1 | high in NP | -2.8 | 0.000871572 | -2.2 | 14196 | 294 | 433 | 596 | 166 | 191 | 164 | N | N | N | N | N | N | P |
| PHC2 | high in NP | -5.3 | 0.000856487 | -2.2 | 14197 | 214 | 1141 | 431 | 84 | 110 | 116 | N | N | N | N | N | N | N |
| UQCRQ | high in NP | -3.2 | 0.000840716 | -2.2 | 14198 | 143 | 159 | 99 | 33 | 66 | 44 | N | N | N | N | N | N | N |
| CHI3L2 | high in NP | -4.2 | 0.000834545 | -2.2 | 14199 | 980 | 2894 | 1117 | 474 | 371 | 261 | N | N | N | N | N | N | N |
| ASH2L | high in NP | -4.7 | 0.00081946 | -2.2 | 14200 | 26 | 104 | 50 | 13 | 11 | 6 | N | N | N | N | N | N | N |
| FCGRT | high in NP | -2.8 | 0.000813289 | -2.2 | 14201 | 214 | 359 | 247 | 83 | 101 | 127 | N | N | N | N | N | N | N |
| C14orf93 | high in NP | -2.3 | 0.000774205 | -2.2 | 14202 | 13 | 11 | 14 | 8 | 8 | 8 | N | N | N | N | N | N | N |
| SCUBE2 | high in NP | -6.3 | 0.000768033 | -2.2 | 14203 | 182 | 99 | 65 | 22 | 14 | 37 | N | N | N | N | N | N | N |
| KRT18 | high in NP | -3.9 | 0.000761862 | -2.2 | 14204 | 54 | 52 | 74 | 11 | 25 | 10 | N | N | N | N | N | N | N |
| RHOG | high in NP | -2.4 | 0.000669398 | -2.2 | 14205 | 340 | 469 | 319 | 137 | 197 | 165 | N | N | N | N | N | N | N |
| ARTN | high in NP | -6.2 | 0.000687809 | -2.2 | 14206 | 68 | 51 | 333 | 7 | 15 | 11 | N | N | N | N | N | N | N |
| PPP1CC | high in NP | -3.6 | 0.000676152 | -2.2 | 14207 | 113 | 303 | 156 | 41 | 57 | 64 | N | N | N | N | N | N | N |
| H1FX | high in NP | -4.7 | 0.00061924 | -2.2 | 14208 | 1398 | 525 | 516 | 256 | 173 | 132 | N | N | N | N | N | N | N |
| CUL7 | high in NP | -2.8 | 0.000591813 | -2.2 | 14209 | 60 | 110 | 103 | 32 | 37 | 37 | N | N | N | N | N | N | N |
| SF3A2 | high in NP | -2.8 | 0.000550672 | -2.2 | 14210 | 468 | 590 | 773 | 211 | 243 | 302 | N | N | N | N | N | N | N |
| EMID1 | high in NP | -4.1 | 0.000544501 | -2.2 | 14211 | 85 | 44 | 58 | 14 | 21 | 11 | N | N | N | N | N | N | N |
| ZC3H11A | high in NP | -4.0 | 0.000486218 | -2.2 | 14212 | 91 | 286 | 150 | 55 | 41 | 49 | N | N | N | N | N | N | N |
| SLC25A6 | high in NP | -2.8 | 0.000471133 | -2.2 | 14213 | 5807 | 4314 | 4211 | 1404 | 2138 | 2115 | N | N | N | N | N | N | N |
| NEDD4L | high in NP | -2.9 | 0.000450562 | -2.2 | 14214 | 1435 | 1120 | 1047 | 374 | 514 | 599 | N | N | N | N | N | P | N |
| C3orf49 | high in NP | -4.6 | 0.000444391 | -2.2 | 14215 | 26 | 4 | 4 | 14 | 16 | 13 | NA | NA | N | N | N | N | N |
| TRIM28 | high in NP | -2.6 | 0.00043822 | -2.2 | 14216 | 1807 | 2423 | 3631 | 758 | 942 | 1055 | N | N | N | N | N | N | N |
| HSD17B3 | high in NP | -3.0 | 0.000413535 | -2.2 | 14217 | 7 | 7 | 11 | 2 | 2 | 2 | N | N | N | N | N | N | N |
| BUD31 | high in NP | -2.8 | 0.000407364 | -2.2 | 14218 | 37 | 68 | 34 | 15 | 17 | 20 | N | N | N | N | N | N | N |
| ASCC2 | high in NP | -5.7 | 0.000359366 | -2.2 | 14219 | 26 | 78 | 82 | 14 | 16 | 13 | N | N | N | N | N | N | N |
| TPX2 | high in NP | -8.8 | 0.000309312 | -2.2 | 14220 | 45 | 25 | 44 | 5 | 14 | 2 | N | N | N | N | N | N | N |
| ENSA | high in NP | -2.5 | 0.000224973 | -2.2 | 14221 | 204 | 179 | 147 | 56 | 70 | 72 | N | N | N | N | N | N | N |
| LIG1 | high in NP | -3.0 | 0.000218801 | -2.2 | 14222 | 36 | 46 | 57 | 18 | 12 | 18 | N | N | N | N | N | N | N |
| DAP | high in NP | -3.4 | 0.000621263 | -2.2 | 14223 | 105 | 80 | 49 | 19 | 25 | 15 | N | N | N | N | N | N | N |
| TINF2 | high in NP | -2.3 | 0.000619602 | -2.2 | 14224 | 22 | 38 | 23 | 11 | 12 | 12 | N | N | N | N | N | N | N |
| PLXND1 | high in NP | -4.3 | 0.000618832 | -2.2 | 14225 | 74 | 189 | 180 | 52 | 42 | 30 | N | N | N | N | N | N | N |
| INPP5J | high in NP | -3.4 | 0.000164632 | -2.2 | 14226 | 33 | 57 | 81 | 20 | 16 | 19 | N | N | N | N | N | N | N |
| TMEM38A | high in NP | -2.4 | 0.000155033 | -2.2 | 14227 | 9 | 12 | 10 | 4 | 4 | 4 | N | N | N | N | N | N | N |
| IFI27L1 | high in NP | -2.1 | 0.000148862 | -2.2 | 14228 | 8 | 6 | 5 | 3 | 3 | 3 | N | N | N | N | N | N | N |
| 40788 | high in NP | -4.3 | 0.000129663 | -2.2 | 14229 | 284 | 437 | 178 | 65 | 84 | 98 | N | N | N | N | N | N | N |
| DDB1 | high in NP | -2.9 | 0.000076865 | -2.2 | 14230 | 297 | 517 | 517 | 158 | 188 | 189 | N | N | N | N | N | N | N |
| MGAT4B | high in NP | -6.1 | 0.000070694 | -2.2 | 14231 | 215 | 770 | 458 | 93 | 93 | 130 | N | N | N | N | N | N | N |
| FBX021 | high in NP | -4.5 | 0.000064523 | -2.2 | 14232 | 76 | 324 | 128 | 32 | 37 | 27 | N | N | N | N | N | N | N |
| B3GALNT1 | high in NP | -2.8 | 0.000038467 | -2.2 | 14233 | 19 | 23 | 12 | 8 | 8 | 6 | N | N | N | N | N | N | N |
| C17orf70 | high in NP | -3.9 | 0.000022696 | -2.2 | 14234 | NA | NA | NA | NA | NA | NA | NA | NA | N | N | N | N | N |
| DUSP4 | high in NP | -3.8 | 0.000016525 | -2.2 | 14235 | 246 | 203 | 121 | 59 | 63 | 66 | N | N | N | N | N | P | P |
| COX4NB | high in NP | -2.1 | 0.005983612 | -2.2 | 14236 | 154 | 200 | 209 | 109 | 98 | 86 | N | N | N | N | N | N | N |

TABLE 16-continued

Genes that Are Differentially Methylated between Nulliparous and Parous CD24+ Breast Epithelial Cells

| | | | SAGE-seq | | | | | | | | ChIP-seq | | | MSDK-seq | | |
|---|---|---|---|---|---|---|---|---|---|---|---|---|---|---|---|---|
| | | | | Nulliparous (NP) | | | | Parous (P) | | | NP | | P | NP | | P |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | GeneBody Met P | Pro-moter Met NP | Pro-moter Met P |
| CILP2 | high in NP | -3.7 | 0.005945214 | -2.2 | 14237 | 14 | 24 | 27 | 6 | 8 | 6 | N | N | N | N | N | N |
| SUSD2 | high in NP | -2.9 | 0.005939043 | -2.2 | 14238 | 35 | 48 | 77 | 15 | 18 | 14 | N | N | N | N | N | N |
| FAM82A2 | high in NP | -4.7 | 0.005917101 | -2.2 | 14239 | 46 | 154 | 100 | 21 | 27 | 24 | N | N | N | N | N | N |
| EPN1 | high in NP | -6.6 | 0.005902016 | -2.2 | 14240 | 132 | 411 | 514 | 82 | 73 | 66 | N | N | N | N | N | N |
| CENPH | high in NP | -4.4 | 0.005874589 | -2.2 | 14241 | 83 | 85 | 28 | 19 | 8 | 11 | N | N | N | N | N | N |
| CDH1 | high in NP | -2.7 | 0.005848533 | -2.2 | 14242 | 3398 | 3140 | 2082 | 923 | 1211 | 1161 | N | N | N | N | N | N |
| ATAD2 | high in NP | -2.6 | 0.005763508 | -2.2 | 14243 | 54 | 42 | 39 | 24 | 18 | 20 | N | N | N | N | N | N |
| URM1 | high in NP | -2.2 | 0.005755337 | -2.2 | 14244 | 33 | 55 | 41 | 19 | 17 | 16 | N | N | N | N | N | N |
| JOSD1 | high in NP | -2.4 | 0.005746366 | -2.2 | 14245 | 418 | 334 | 442 | 154 | 149 | 198 | N | N | N | N | N | N |
| COBRA1 | high in NP | -10.7 | 0.005690014 | -2.2 | 14246 | 86 | 487 | 379 | 41 | 53 | 24 | N | N | N | N | N | N |
| ABHD14B | high in NP | -4.5 | 0.005658598 | -2.2 | 14247 | 271 | 184 | 303 | 37 | 75 | 90 | N | N | N | N | N | N |
| CEP290 | high in NP | -3.0 | 0.005652427 | -2.2 | 14248 | 24 | 23 | 22 | 10 | 14 | 8 | N | N | N | N | N | N |
| ZNF775 | high in NP | -7.2 | 0.005637342 | -2.2 | 14249 | 7 | 9 | 26 | 2 | 2 | 2 | N | N | N | N | N | N |
| CEBPG | high in NP | -2.4 | 0.005607172 | -2.2 | 14250 | 95 | 130 | 82 | 42 | 47 | 45 | N | N | N | N | N | N |
| PDK2 | high in NP | -2.6 | 0.005590716 | -2.2 | 14251 | 37 | 44 | 52 | 22 | 18 | 13 | N | N | N | N | N | N |
| EEF1A1 | high in NP | -5.5 | 0.005584545 | -2.3 | 14252 | 518 | 589 | 362 | 85 | 126 | 212 | N | N | N | N | N | N |
| SLC25A14 | high in NP | -2.5 | 0.005544089 | -2.3 | 14253 | 17 | 15 | 11 | 6 | 6 | 6 | N | N | N | N | N | N |
| PM20D2 | high in NP | -2.5 | 0.005531747 | -2.3 | 14254 | 48 | 80 | 44 | 25 | 22 | 18 | N | N | N | N | N | N |
| CCNB2 | high in NP | -4.6 | 0.005525576 | -2.3 | 14255 | 13 | 5 | 8 | 5 | 5 | 5 | N | N | N | N | N | N |
| ACBD4 | high in NP | -5.3 | 0.005519405 | -2.3 | 14256 | 26 | 52 | 83 | 11 | 6 | 11 | N | N | N | N | N | N |
| ANXA3 | high in NP | -5.1 | 0.005507063 | -2.3 | 14257 | 137 | 234 | 191 | 86 | 49 | 30 | N | N | N | N | N | N |
| PRDX2 | high in NP | -2.7 | 0.005449472 | -2.3 | 14258 | 270 | 278 | 191 | 88 | 116 | 77 | N | N | N | N | N | N |
| PHYHD1 | high in NP | -2.8 | 0.005479635 | -2.3 | 14259 | 86 | 86 | 114 | 33 | 31 | 43 | N | N | N | N | N | N |
| SNX17 | high in NP | -3.3 | 0.005452208 | -2.3 | 14260 | 42 | 38 | 60 | 17 | 21 | 16 | N | N | N | N | N | N |
| NUP188 | high in NP | -5.3 | 0.005430266 | -2.3 | 14261 | 101 | 361 | 232 | 53 | 49 | 59 | N | N | N | N | N | N |
| NIT2 | high in NP | -2.8 | 0.005424095 | -2.3 | 14262 | 182 | 279 | 221 | 58 | 99 | 88 | N | N | N | N | N | N |
| FGFBP3 | high in NP | -2.2 | 0.005401467 | -2.3 | 14263 | 13 | 10 | 10 | 5 | 5 | 9 | N | N | N | N | N | N |
| LOC643763 | high in NP | -2.1 | 0.005374726 | -2.3 | 14264 | 19 | 25 | 19 | 11 | 9 | 9 | NA | NA | N | N | N | N |
| CRYZL1 | high in NP | -2.9 | 0.005352784 | -2.3 | 14265 | 15 | 36 | 15 | 6 | 6 | 6 | N | N | N | N | N | N |
| CMTM3 | high in NP | -3.1 | 0.005346613 | -2.3 | 14266 | 325 | 538 | 401 | 121 | 173 | 188 | N | N | N | N | N | N |
| FAM195B | high in NP | -4.6 | 0.005331014 | -2.3 | 14267 | 481 | 845 | 1610 | 137 | 197 | 244 | NA | NA | N | N | N | N |
| ZNF682 | high in NP | -2.1 | 0.005306843 | -2.3 | 14268 | 12 | 9 | 10 | 7 | 7 | 7 | N | N | N | N | N | N |
| PLCB4 | high in NP | -3.5 | 0.005300672 | -2.3 | 14269 | 75 | 46 | 36 | 21 | 17 | 17 | N | N | N | N | N | N |
| CCDC53 | high in NP | -3.8 | 0.005294501 | -2.3 | 14270 | 27 | 23 | 14 | 5 | 3 | 9 | N | N | N | N | N | N |
| DDAH2 | high in NP | -2.7 | 0.005275987 | -2.3 | 14271 | 1276 | 1195 | 2113 | 577 | 474 | 519 | N | N | N | N | N | N |
| MTMR11 | high in NP | -3.5 | 0.005269816 | -2.3 | 14272 | 75 | 95 | 63 | 36 | 25 | 19 | N | N | N | N | N | N |
| EIF3K | high in NP | -5.0 | 0.005249931 | -2.3 | 14273 | 750 | 356 | 465 | 66 | 113 | 174 | N | N | N | N | N | N |
| SNRNP35 | high in NP | -2.9 | 0.005214276 | -2.3 | 14274 | 25 | 43 | 40 | 13 | 14 | 8 | N | N | N | N | N | N |
| HSD17B8 | high in NP | -3.9 | 0.005201934 | -2.3 | 14275 | 31 | 27 | 25 | 4 | 7 | 12 | N | N | N | N | N | N |
| E2F5 | high in NP | -3.6 | 0.005195762 | -2.3 | 14276 | 22 | 27 | 15 | 6 | 12 | 6 | N | N | N | N | N | N |
| VAV3 | high in NP | -8.6 | 0.005165592 | -2.3 | 14277 | 105 | 381 | 444 | 32 | 51 | 55 | N | N | N | N | N | N |
| LRRC48 | high in NP | -5.3 | 0.005159421 | -2.3 | 14278 | 32 | 16 | 35 | 8 | 8 | 11 | N | N | N | N | N | N |
| POLR1E | high in NP | -3.3 | 0.005091539 | -2.3 | 14279 | 196 | 147 | 117 | 39 | 53 | 60 | N | N | N | N | N | N |
| RPS9 | high in NP | -4.5 | 0.005085368 | -2.3 | 14280 | 5630 | 9393 | 13402 | 1601 | 1939 | 2952 | N | N | N | N | N | N |

TABLE 16-continued

Genes that Are Differentially Methylated between Nulliparous and Parous CD24+ Breast Epithelial Cells

| | | | SAGE-seq | | Nulliparous (NP) | | | | Parous (P) | | | ChIP-seq | | | MSDK-seq | | |
|---|---|---|---|---|---|---|---|---|---|---|---|---|---|---|---|---|---|
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | P GeneBody Met | NP Pro-moter Met | P Pro-moter Met |
|---|---|---|---|---|---|---|---|---|---|---|---|---|---|---|---|---|---|
| EEF1G | high in NP | -5.1 | 0.005047655 | -2.3 | 14281 | 8602 | 4514 | 3281 | 679 | 1112 | 1547 | N | N | N | N | N | N |
| GTPBP2 | high in NP | -3.7 | 0.005035513 | -2.3 | 14282 | 349 | 418 | 196 | 87 | 77 | 109 | N | N | N | N | N | N |
| FAM76A | high in NP | -2.8 | 0.00497703 | -2.3 | 14283 | 31 | 30 | 22 | 12 | 15 | 9 | N | N | N | N | N | N |
| MOGS | high in NP | -2.8 | 0.004944117 | -2.3 | 14284 | 77 | 124 | 132 | 28 | 40 | 38 | NA | NA | N | N | N | N |
| CYP2J2 | high in NP | -2.0 | 0.004937946 | -2.3 | 14285 | 8 | 9 | 7 | 3 | 3 | 3 | N | N | N | N | N | N |
| PMPCA | high in NP | -11.3 | 0.004931775 | -2.3 | 14286 | 81 | 298 | 431 | 22 | 21 | 53 | N | N | N | N | N | N |
| ACTN4 | high in NP | -2.4 | 0.004925603 | -2.3 | 14287 | 3166 | 4447 | 4144 | 1575 | 2055 | 1480 | N | N | N | N | N | N |
| PPP2R5C | high in NP | -3.1 | 0.004913261 | -2.3 | 14288 | 219 | 151 | 195 | 64 | 84 | 72 | N | N | N | N | N | N |
| NAPA | high in NP | -3.1 | 0.004900919 | -2.3 | 14289 | 458 | 1075 | 432 | 187 | 174 | 148 | N | N | N | N | N | N |
| ZHX1 | high in NP | -2.5 | 0.004885834 | -2.3 | 14290 | 46 | 54 | 38 | 20 | 19 | 17 | N | N | N | N | N | N |
| MPST | high in NP | -5.4 | 0.004879663 | -2.3 | 14291 | 208 | 247 | 593 | 83 | 82 | 46 | N | N | N | N | N | N |
| CTSB | high in NP | -2.4 | 0.004844693 | -2.3 | 14292 | 1749 | 2528 | 2027 | 1001 | 1070 | 854 | N | N | N | N | N | N |
| DIS3L | high in NP | -2.7 | 0.004833722 | -2.3 | 14293 | 927 | 922 | 621 | 315 | 307 | 376 | N | N | N | N | N | N |
| INPPL1 | high in NP | -2.7 | 0.004815894 | -2.3 | 14294 | 419 | 825 | 439 | 216 | 183 | 186 | N | N | N | N | P | N |
| AHSA2 | high in NP | -5.6 | 0.004794638 | -2.3 | 14295 | 76 | 39 | 32 | 9 | 7 | 18 | N | N | N | N | N | N |
| C17orf28 | high in NP | -2.5 | 0.004778867 | -2.3 | 14296 | 462 | 573 | 698 | 288 | 305 | 192 | N | N | N | N | N | N |
| HINT2 | high in NP | -4.7 | 0.004766525 | -2.3 | 14297 | 82 | 96 | 118 | 37 | 20 | 13 | N | N | N | N | N | N |
| C12orf11 | high in NP | -6.8 | 0.004755554 | -2.3 | 14298 | 108 | 109 | 91 | 20 | 49 | 22 | N | N | N | N | N | N |
| GSTZ1 | high in NP | -5.2 | 0.00472744l | -2.3 | 14299 | 29 | 41 | 66 | 12 | 14 | 6 | N | N | N | N | N | N |
| WDR33 | high in NP | -2.6 | 0.00472127 | -2.3 | 14300 | 125 | 153 | 117 | 47 | 51 | 56 | N | N | N | N | N | N |
| BARD1 | high in NP | -3.2 | 0.004702756 | -2.3 | 14301 | 18 | 14 | 9 | 5 | 5 | 5 | N | N | N | N | N | N |
| SLC37A4 | high in NP | -3.6 | 0.004696585 | -2.3 | 14302 | 16 | 36 | 26 | 10 | 8 | 8 | N | N | N | N | N | N |
| PLSCR3 | high in NP | -4.8 | 0.004679443 | -2.3 | 14303 | 111 | 368 | 211 | 49 | 41 | 54 | N | N | N | N | N | N |
| FTSJD2 | high in NP | -5.6 | 0.004665816 | -2.3 | 14304 | 117 | 286 | 312 | 47 | 66 | 50 | N | N | N | N | N | N |
| TMEM214 | high in NP | -2.6 | 0.004650645 | -2.3 | 14305 | 241 | 386 | 337 | 118 | 155 | 122 | N | N | N | N | N | N |
| ACAD10 | high in NP | -3.1 | 0.004463556 | -2.3 | 14306 | 55 | 48 | 62 | 18 | 12 | 21 | N | N | N | N | N | N |
| SFRS2 | high in NP | -3.4 | 0.004609504 | -2.3 | 14307 | 1371 | 1662 | 1336 | 331 | 499 | 662 | N | N | N | N | N | N |
| CCDC101 | high in NP | -8.2 | 0.004567677 | -2.3 | 14308 | 70 | 149 | 182 | 11 | 38 | 19 | N | N | N | N | P | P |
| S100A14 | high in NP | -3.3 | 0.004561506 | -2.3 | 14309 | 7828 | 11973 | 13611 | 3256 | 4411 | 2385 | N | N | N | N | N | N |
| COX5B | high in NP | -3.5 | 0.004555335 | -2.3 | 14310 | 66 | 103 | 53 | 21 | 27 | 13 | N | N | N | N | N | N |
| C2orf81 | high in NP | -5.8 | 0.004549163 | -2.3 | 14311 | 36 | 19 | 17 | 5 | 5 | 11 | N | N | N | N | N | N |
| TRIP6 | high in NP | -3.3 | 0.004542992 | -2.3 | 14312 | 543 | 799 | 1227 | 261 | 297 | 220 | NA | NA | N | N | N | N |
| CYP2D7P1 | high in NP | -5.0 | 0.004515565 | -2.3 | 14313 | 10 | 14 | 14 | 4 | 2 | 5 | N | N | N | N | N | N |
| APOBEC3C | high in NP | -2.5 | 0.004498423 | -2.3 | 14314 | 39 | 39 | 36 | 15 | 14 | 20 | N | N | N | N | N | N |
| KATNB1 | high in NP | -5.0 | 0.004455225 | -2.4 | 14315 | 112 | 173 | 243 | 53 | 44 | 23 | N | N | N | N | N | N |
| PMAIP1 | high in NP | -5.8 | 0.004433969 | -2.4 | 14316 | 295 | 189 | 140 | 22 | 34 | 66 | N | N | N | N | N | N |
| SIN3B | high in NP | -4.1 | 0.004386657 | -2.4 | 14317 | 319 | 847 | 500 | 144 | 181 | 129 | N | P | N | N | N | N |
| EREG | high in NP | -9.6 | 0.004377057 | -2.4 | 14318 | 113 | 210 | 45 | 25 | 10 | 10 | P | N | N | N | N | N |
| RHPN1 | high in NP | -3.2 | 0.004358544 | -2.4 | 14319 | 223 | 197 | 347 | 68 | 93 | 76 | N | P | N | N | N | P |
| ZNF580 | high in NP | -3.4 | 0.00434003 | -2.4 | 14320 | 99 | 99 | 81 | 42 | 30 | 20 | N | N | N | N | N | N |
| NDUFA11 | high in NP | -4.5 | 0.004308489 | -2.4 | 14321 | 355 | 881 | 472 | 157 | 179 | 98 | N | N | N | N | N | N |
| DULLARD | high in NP | -3.9 | 0.004298889 | -2.4 | 14322 | 59 | 130 | 60 | 14 | 23 | 21 | N | N | N | N | P | N |
| AUH | high in NP | -2.6 | 0.004286547 | -2.4 | 14323 | 24 | 20 | 21 | 11 | 8 | 9 | N | N | N | N | N | N |
| JOSD2 | high in NP | -6.1 | 0.004274205 | -2.4 | 14324 | 58 | 138 | 216 | 24 | 22 | 22 | N | N | N | N | N | N |

TABLE 16-continued

Genes that Are Differentially Methylated between Nulliparous and Parous CD24+ Breast Epithelial Cells

| | | | | SAGE-seq | | | | | | | | ChIP-seq | | | MSDK-seq | | |
|---|---|---|---|---|---|---|---|---|---|---|---|---|---|---|---|---|---|
| | | | | | Nulliparous (NP) | | | | Parous (P) | | | NP | | P | GeneBody | GeneBody | Pro-moter |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | Met | Pro-moter Met | NP | Pro-moter Met | P |
| CRB3 | high in NP | -9.2 | 0.004261862 | -2.4 | 14325 | 62 | 216 | 266 | 24 | 20 | 27 | N | N | N | N | N | N |
| GSDMD | high in NP | -6.8 | 0.004255691 | -2.4 | 14326 | 70 | 236 | 250 | 27 | 42 | 22 | N | N | N | N | N | N |
| ACSF2 | high in NP | -2.7 | 0.00424952 | -2.4 | 14327 | 129 | 158 | 182 | 65 | 73 | 53 | N | N | N | N | N | N |
| COL9A2 | high in NP | -3.6 | 0.004243349 | -2.4 | 14328 | 54 | 86 | 126 | 21 | 17 | 28 | N | N | N | N | N | N |
| PFKL | high in NP | -2.7 | 0.004223464 | -2.4 | 14329 | 1203 | 1359 | 1963 | 502 | 571 | 588 | N | N | N | N | N | N |
| NFRKB | high in NP | -2.8 | 0.004217293 | -2.4 | 14330 | 210 | 308 | 339 | 109 | 137 | 124 | N | N | N | N | N | N |
| ZNF385B | high in NP | -6.0 | 0.004211122 | -2.4 | 14331 | 31 | 9 | 23 | 3 | 3 | 3 | N | N | N | N | N | N |
| UBAC2 | high in NP | -3.2 | 0.004158324 | -2.4 | 14332 | 30 | 33 | 19 | 10 | 10 | 10 | N | N | N | N | N | N |
| VPS37D | high in NP | -5.6 | 0.004130897 | -2.4 | 14333 | 35 | 31 | 40 | 13 | 7 | 7 | N | N | N | N | N | N |
| ZDHHC7 | high in NP | -2.5 | 0.004110326 | -2.4 | 14334 | 686 | 927 | 739 | 309 | 397 | 307 | N | N | N | N | N | N |
| CDK9 | high in NP | -5.1 | 0.004096613 | -2.4 | 14335 | 280 | 695 | 620 | 120 | 153 | 148 | N | N | N | N | N | N |
| H2AFX | high in NP | -3.4 | 0.004059586 | -2.4 | 14336 | 144 | 194 | 138 | 35 | 58 | 68 | N | N | N | N | N | N |
| FXYD3 | high in NP | -2.3 | 0.004047244 | -2.4 | 14337 | 2773 | 2341 | 3264 | 1340 | 1097 | 1167 | N | N | N | N | N | N |
| C19orf20 | high in NP | -3.6 | 0.004041072 | -2.4 | 14338 | 34 | 57 | 61 | 10 | 17 | 14 | N | N | N | N | N | N |
| APH1B | high in NP | -3.0 | 0.004402873 | -2.4 | 14339 | 61 | 115 | 109 | 37 | 28 | 24 | N | N | N | N | N | N |
| NUP160 | high in NP | -3.2 | 0.004006103 | -2.4 | 14340 | 35 | 64 | 52 | 17 | 22 | 20 | N | N | N | N | N | N |
| LGALS3BP | high in NP | -3.0 | 0.003999931 | -2.4 | 14341 | 76 | 156 | 99 | 42 | 45 | 35 | N | N | N | N | N | N |
| ATP6AP1 | high in NP | -2.6 | 0.00399376 | -2.4 | 14342 | 180 | 265 | 265 | 80 | 110 | 79 | N | N | N | N | N | N |
| POM121L1P | high in NP | -6.1 | 0.003944391 | -2.4 | 14343 | 36 | 3 | 6 | 1 | 1 | 1 | NA | NA | N | N | N | N |
| ECHS1 | high in NP | -2.9 | 0.003925878 | -2.4 | 14344 | 70 | 59 | 79 | 25 | 30 | 22 | N | N | N | N | N | N |
| SLC27A1 | high in NP | -2.6 | 0.003888165 | -2.4 | 14345 | 85 | 92 | 67 | 30 | 37 | 25 | N | N | N | N | N | N |
| COPE | high in NP | -3.4 | 0.003869652 | -2.4 | 14346 | 337 | 703 | 459 | 166 | 179 | 127 | N | N | N | N | N | N |
| TMEM5 | high in NP | -2.7 | 0.003863481 | -2.4 | 14347 | 45 | 42 | 37 | 12 | 19 | 16 | N | N | N | N | N | N |
| GLTPD2 | high in NP | -6.0 | 0.00380794 | -2.4 | 14348 | 6 | 6 | 14 | 1 | 1 | 1 | N | N | N | N | N | N |
| ULK3 | high in NP | -2.5 | 0.003764742 | -2.4 | 14349 | 60 | 69 | 47 | 26 | 26 | 25 | N | N | N | N | N | N |
| LOC646999 | high in NP | -8.9 | 0.003733886 | -2.4 | 14350 | 22 | 34 | 46 | 6 | 8 | 11 | N | N | N | N | N | N |
| C8orf45 | high in NP | -3.3 | 0.003713316 | -2.4 | 14351 | 18 | 20 | 15 | 12 | 9 | 9 | N | N | N | N | N | N |
| CRIP2 | high in NP | -3.3 | 0.003697545 | -2.4 | 14352 | 674 | 625 | 527 | 132 | 250 | 221 | N | N | N | N | N | N |
| TSPAN1 | high in NP | -4.8 | 0.00368832 | -2.4 | 14353 | 56 | 96 | 57 | 21 | 11 | 4 | N | N | N | N | N | N |
| RPL35 | high in NP | -5.8 | 0.00367766 | -2.4 | 14354 | 10276 | 5563 | 14219 | 1073 | 1743 | 2477 | N | N | N | N | N | N |
| BANF1 | high in NP | -3.1 | 0.003671489 | -2.4 | 14355 | 265 | 441 | 390 | 148 | 140 | 139 | N | N | N | N | N | N |
| SYNGR2 | high in NP | -4.6 | 0.003609092 | -2.4 | 14356 | 1017 | 2699 | 819 | 288 | 323 | 242 | N | N | N | N | N | N |
| KHSRP | high in NP | -3.2 | 0.003585093 | -2.4 | 14357 | 294 | 265 | 200 | 92 | 93 | 101 | N | N | N | N | N | N |
| SF3B5 | high in NP | -3.0 | 0.003534353 | -2.4 | 14358 | 1081 | 1294 | 1247 | 375 | 572 | 430 | N | N | N | N | N | N |
| TICAM1 | high in NP | -3.1 | 0.003506925 | -2.5 | 14359 | 328 | 375 | 253 | 111 | 95 | 133 | N | N | N | N | N | N |
| NR2E3 | high in NP | -3.3 | 0.003484298 | -2.5 | 14360 | 11 | 16 | 13 | 2 | 2 | 6 | N | N | N | N | N | N |
| TAGLN2 | high in NP | -3.3 | 0.003478127 | -2.5 | 14361 | 1278 | 1373 | 915 | 515 | 465 | 421 | N | N | N | N | N | N |
| MUSTN1 | high in NP | -5.3 | 0.003471956 | -2.5 | 14362 | 10 | 9 | 7 | 2 | 2 | 5 | N | N | N | N | N | N |
| ZFPL1 | high in NP | -3.0 | 0.003465784 | -2.5 | 14363 | 89 | 141 | 100 | 44 | 35 | 26 | N | N | N | N | N | N |
| RPL11 | high in NP | -5.0 | 0.003453442 | -2.5 | 14364 | 10281 | 5707 | 8868 | 1134 | 1775 | 2591 | N | N | N | N | N | N |
| PLEKHA8 | high in NP | -3.0 | 0.003434929 | -2.5 | 14365 | 8 | 4 | 4 | 3 | 3 | 3 | N | N | N | N | N | N |
| ZNF238 | high in NP | -2.9 | 0.003402016 | -2.5 | 14366 | 81 | 73 | 55 | 26 | 24 | 26 | N | N | N | N | N | N |
| ZBTB22 | high in NP | -2.9 | 0.003382817 | -2.5 | 14367 | 42 | 71 | 75 | 18 | 25 | 22 | N | N | N | N | N | N |
| LOC729176 | high in NP | -5.3 | 0.003370474 | -2.5 | 14368 | 9 | 9 | 5 | 1 | 4 | 1 | N | N | N | N | N | N |

TABLE 16-continued

Genes that Are Differentially Methylated between Nulliparous and Parous CD24+ Breast Epithelial Cells

| | | | SAGE-seq | | Nulliparous (NP) | | | | Parous (P) | | | ChIP-seq | | | MSDK-seq | | |
|---|---|---|---|---|---|---|---|---|---|---|---|---|---|---|---|---|---|
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | P GeneBody Met | NP Pro-moter Met | P Pro-moter Met |
|---|---|---|---|---|---|---|---|---|---|---|---|---|---|---|---|---|---|
| MAP2K4 | high in NP | −2.3 | 0.000360875 | −2.5 | 14369 | 60 | 56 | 47 | 21 | 25 | 27 | N | N | N | N | N | N |
| NPHP4 | high in NP | −4.5 | 0.000354704 | −2.5 | 14370 | 75 | 67 | 86 | 16 | 27 | 27 | N | P | N | N | N | N |
| OTUD5 | high in NP | −5.8 | 0.000299163 | −2.5 | 14371 | 194 | 429 | 497 | 69 | 97 | 95 | N | N | N | N | N | N |
| EXOC3 | high in NP | −6.7 | 0.000286821 | −2.5 | 14372 | 98 | 342 | 212 | 39 | 34 | 45 | N | N | N | N | N | N |
| BMS1P5 | high in NP | −9.8 | 0.000265565 | −2.5 | 14373 | 58 | 64 | 25 | 3 | 4 | 14 | N | N | N | N | N | N |
| LRRC29 | high in NP | −2.4 | 0.000236081 | −2.5 | 14374 | 7 | 6 | 6 | 2 | 2 | 2 | N | N | N | N | N | N |
| SPTBN1 | high in NP | −5.1 | 0.000229909 | −2.5 | 14375 | 358 | 1055 | 390 | 108 | 106 | 152 | N | N | N | N | N | N |
| VKORC1 | high in NP | −5.6 | 0.000199054 | −2.5 | 14376 | 44 | 34 | 22 | 5 | 12 | 5 | N | N | N | N | N | N |
| ZNF598 | high in NP | −3.7 | 0.000170941 | −2.5 | 14377 | 855 | 2099 | 1193 | 347 | 319 | 397 | N | N | N | N | N | N |
| RANGRF | high in NP | −3.5 | 0.000155856 | −2.5 | 14378 | 23 | 21 | 11 | 3 | 6 | 3 | N | N | N | N | N | N |
| LOC100233209 | high in NP | −2.7 | 0.000137342 | −2.5 | 14379 | 228 | 254 | 213 | 102 | 84 | 104 | NA | NA | N | N | N | N |
| RAE1 | high in NP | −3.9 | 0.000131171 | −2.5 | 14380 | 43 | 35 | 24 | 8 | 11 | 14 | N | N | N | N | N | N |
| CNTROB | high in NP | −4.2 | 0.0003125 | −2.5 | 14381 | 69 | 84 | 164 | 18 | 27 | 19 | N | N | N | N | N | N |
| PPME1 | high in NP | −3.6 | 0.000118829 | −2.5 | 14382 | 87 | 176 | 125 | 31 | 33 | 49 | N | N | N | N | N | N |
| GPAA1 | high in NP | −12.1 | 0.000109229 | −2.5 | 14383 | 132 | 533 | 606 | 52 | 65 | 48 | N | N | N | N | N | N |
| COQ10A | high in NP | −4.4 | 0.000103058 | −2.5 | 14384 | 26 | 22 | 20 | 6 | 12 | 6 | N | N | N | N | N | N |
| DUSP10 | high in NP | −5.4 | 0.000083173 | −2.5 | 14385 | 93 | 41 | 27 | 12 | 11 | 11 | N | N | N | N | N | N |
| U2AF1L4 | high in NP | −3.8 | 0.000070831 | −2.5 | 14386 | 84 | 62 | 64 | 23 | 24 | 15 | N | N | N | N | N | N |
| SAE1 | high in NP | −3.6 | 0.000049575 | −2.5 | 14387 | 159 | 277 | 218 | 85 | 67 | 56 | N | N | N | N | N | N |
| TIMM10 | high in NP | −2.7 | 0.000012548 | −2.5 | 14388 | 129 | 126 | 97 | 43 | 50 | 36 | N | N | N | N | N | N |
| NUMA1 | high in NP | −2.9 | 0.000000206 | −2.5 | 14389 | 638 | 945 | 635 | 264 | 241 | 328 | N | N | N | N | N | N |
| REEP6 | high in NP | −3.1 | 0.000994035 | −2.5 | 14390 | 142 | 170 | 149 | 51 | 50 | 24 | N | N | N | N | N | N |
| RPN1 | high in NP | −3.7 | 0.000297895 | −2.5 | 14391 | 437 | 505 | 277 | 100 | 123 | 138 | N | N | N | N | N | N |
| RALGDS | high in NP | −4.3 | 0.000963865 | −2.5 | 14392 | 2154 | 2172 | 1668 | 436 | 551 | 797 | N | N | N | N | N | N |
| CLCN7 | high in NP | −7.3 | 0.000957693 | −2.5 | 14393 | 215 | 636 | 640 | 94 | 111 | 78 | N | N | N | N | N | N |
| MGMT | high in NP | −6.7 | 0.000942608 | −2.5 | 14394 | 38 | 87 | 96 | 13 | 15 | 14 | N | N | N | N | N | N |
| TLCD1 | high in NP | −2.8 | 0.000915867 | −2.5 | 14395 | 17 | 19 | 11 | 7 | 5 | 5 | N | N | N | N | N | N |
| C14orf142 | high in NP | −3.5 | 0.000893925 | −2.5 | 14396 | 25 | 17 | 13 | 5 | 8 | 5 | N | N | N | N | N | N |
| TNFAIP1 | high in NP | −2.7 | 0.000881583 | −2.5 | 14397 | 101 | 161 | 157 | 65 | 59 | 45 | N | N | N | N | N | N |
| C9orf16 | high in NP | −10.6 | 0.000856898 | −2.5 | 14398 | 21 | 13 | 2 | 1 | 1 | 1 | N | N | N | N | N | N |
| UBXN1 | high in NP | −3.8 | 0.000823985 | −2.5 | 14399 | 540 | 617 | 640 | 213 | 181 | 269 | N | N | N | N | N | N |
| ZNF232 | high in NP | −9.7 | 0.000802729 | −2.6 | 14400 | 8 | 16 | 12 | 3 | 3 | 3 | N | N | N | N | N | N |
| MTA1 | high in NP | −5.4 | 0.000774616 | −2.6 | 14401 | 316 | 626 | 324 | 58 | 124 | 99 | N | N | N | N | N | N |
| CONK | high in NP | −2.9 | 0.000762274 | −2.6 | 14402 | 166 | 219 | 247 | 96 | 85 | 80 | N | N | N | N | N | N |
| C1orf35 | high in NP | −4.0 | 0.000725247 | −2.6 | 14403 | 219 | 164 | 302 | 72 | 64 | 67 | N | N | N | N | N | N |
| ALKBH7 | high in NP | −5.7 | 0.000719076 | −2.6 | 14404 | 477 | 326 | 709 | 64 | 72 | 142 | N | N | N | N | N | N |
| BATF | high in NP | −3.5 | 0.000712905 | −2.6 | 14405 | 546 | 636 | 839 | 154 | 264 | 181 | N | N | N | N | N | N |
| MRPS30 | high in NP | −3.0 | 0.000695077 | −2.6 | 14406 | 59 | 85 | 51 | 21 | 23 | 30 | N | N | N | N | N | N |
| ZNF581 | high in NP | −2.8 | 0.000653936 | −2.6 | 14407 | 79 | 87 | 94 | 24 | 34 | 34 | N | N | N | N | N | N |
| ACTR10 | high in NP | −2.3 | 0.000647765 | −2.6 | 14408 | 54 | 45 | 38 | 20 | 22 | 24 | N | N | N | N | N | N |
| SPINT1 | high in NP | −3.7 | 0.000623766 | −2.6 | 14409 | 1031 | 1587 | 914 | 438 | 315 | 329 | N | N | N | N | N | N |
| SEMA4B | high in NP | −3.8 | 0.000617595 | −2.6 | 14410 | 1142 | 1871 | 2192 | 522 | 527 | 333 | N | N | N | N | N | N |
| PBX2 | high in NP | −2.9 | 0.000599081 | −2.6 | 14411 | 326 | 478 | 486 | 193 | 148 | 170 | N | N | N | N | N | N |
| STARD10 | high in NP | −3.9 | 0.000579882 | −2.6 | 14412 | 40 | 29 | 43 | 11 | 12 | 8 | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | MSDK-seq | | | |
|---|---|---|---|---|---|---|---|---|---|---|---|---|---|---|---|---|---|---|
| | | | | | | Nulliparous (NP) | | | | Parous (P) | | | NP | P | GeneBody | P | GeneBody | Pro-moter |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody | Met | Pro-moter Met | GeneBody | Pro-moter Met |
| HYAL2 | high in NP | −7.0 | 0.002523656 | −2.6 | 14413 | 26 | 75 | 58 | 12 | 13 | 10 | N | N | NP | N | N | N | N |
| PREB | high in NP | −5.6 | 0.002512685 | −2.6 | 14414 | 65 | 202 | 116 | 29 | 21 | 24 | N | N | NP | N | N | N | N |
| EFEMP2 | high in NP | −3.5 | 0.002506514 | −2.6 | 14415 | 144 | 139 | 203 | 44 | 44 | 57 | N | N | NP | N | N | N | N |
| SUSD3 | high in NP | −18.3 | 0.002500343 | −2.6 | 14416 | 23 | 164 | 91 | 3 | 6 | 3 | N | N | NP | N | N | N | N |
| TEX10 | high in NP | −3.4 | 0.002494172 | −2.6 | 14417 | 107 | 161 | 143 | 29 | 49 | 44 | N | N | NP | N | N | N | N |
| DCTN3 | high in NP | −4.8 | 0.002466059 | −2.6 | 14418 | 115 | 212 | 218 | 27 | 46 | 55 | N | N | NP | N | N | N | N |
| CAPNS1 | high in NP | −5.1 | 0.002459888 | −2.6 | 14419 | 1544 | 1674 | 1414 | 315 | 636 | 350 | N | N | NP | N | N | N | N |
| C10orf116 | high in NP | −3.5 | 0.002450288 | −2.6 | 14420 | 316 | 558 | 502 | 155 | 146 | 161 | N | N | NP | N | N | N | N |
| CBX8 | high in NP | −6.0 | 0.002437946 | −2.6 | 14421 | 21 | 25 | 37 | 9 | 5 | 5 | N | N | NP | N | N | N | N |
| POP5 | high in NP | −4.6 | 0.002405719 | −2.6 | 14422 | 27 | 16 | 11 | 5 | 6 | 3 | N | N | NP | P | N | N | N |
| ELF1 | high in NP | −8.0 | 0.002399547 | −2.6 | 14423 | 320 | 470 | 152 | 32 | 37 | 72 | N | N | NP | N | N | N | N |
| PLEKHG3 | high in NP | −3.5 | 0.002387205 | −2.6 | 14424 | 251 | 208 | 224 | 61 | 93 | 63 | N | N | NP | N | N | N | N |
| EXOSC5 | high in NP | −4.5 | 0.002365949 | −2.6 | 14425 | 46 | 65 | 75 | 14 | 11 | 19 | N | N | NP | N | N | N | N |
| BAI2 | high in NP | −3.6 | 0.002359778 | −2.6 | 14426 | 60 | 54 | 34 | 17 | 19 | 19 | N | N | NP | N | N | N | N |
| SLC35B2 | high in NP | −5.1 | 0.002319323 | −2.6 | 14427 | 82 | 176 | 102 | 17 | 35 | 24 | N | N | NP | N | N | N | N |
| TSTD1 | high in NP | −3.1 | 0.00230698 | −2.6 | 14428 | 206 | 303 | 218 | 77 | 106 | 70 | N | N | NP | N | N | N | N |
| DPM2 | high in NP | −4.9 | 0.002287095 | −2.6 | 14429 | 171 | 337 | 255 | 82 | 59 | 40 | NA | NA | NP | N | N | N | N |
| CCDC104 | high in NP | −3.2 | 0.002274753 | −2.6 | 14430 | 51 | 49 | 29 | 13 | 14 | 15 | N | N | NP | N | N | N | N |
| FBX034 | high in NP | −2.3 | 0.002254183 | −2.6 | 14431 | 32 | 46 | 33 | 15 | 15 | 14 | N | N | NP | N | N | N | N |
| ELMO2 | high in NP | −2.5 | 0.002229498 | −2.6 | 14432 | 31 | 36 | 35 | 14 | 12 | 15 | N | N | NP | N | N | N | N |
| RPL13 | high in NP | −4.2 | 0.002223327 | −2.6 | 14433 | 17982 | 15100 | 16762 | 3263 | 4470 | 6736 | N | N | NP | N | N | N | N |
| TMED3 | high in NP | −2.6 | 0.002192471 | −2.6 | 14434 | 264 | 309 | 229 | 119 | 99 | 104 | N | N | NP | N | N | N | N |
| ZFYVE28 | high in NP | −3.1 | 0.002162301 | −2.6 | 14435 | 21 | 33 | 39 | 9 | 9 | 9 | P | P | NP | N | N | N | N |
| DEGS2 | high in NP | −4.0 | 0.002143788 | −2.6 | 14436 | 58 | 40 | 42 | 13 | 14 | 10 | N | N | NP | N | N | N | N |
| C19orf43 | high in NP | −3.2 | 0.002137617 | −2.7 | 14437 | 1084 | 1722 | 1336 | 378 | 465 | 512 | N | N | NP | N | N | N | N |
| PXMP2 | high in NP | −6.1 | 0.00208619 | −2.7 | 14438 | 8 | 12 | 8 | 3 | 3 | 3 | N | N | NP | N | N | N | N |
| RPLP2 | high in NP | −5.0 | 0.002080019 | −2.7 | 14439 | 18281 | 18281 | 12128 | 2072 | 4166 | 4308 | N | N | NP | N | N | N | N |
| UBE2A | high in NP | −2.8 | 0.002073848 | −2.7 | 14440 | 32 | 51 | 37 | 16 | 19 | 16 | N | N | NP | N | N | N | N |
| CHRNE | high in NP | −4.5 | 0.002067677 | −2.7 | 14441 | 45 | 46 | 23 | 8 | 8 | 9 | N | N | NP | N | N | N | N |
| EDF1 | high in NP | −2.7 | 0.002016251 | −2.7 | 14442 | 542 | 762 | 669 | 231 | 286 | 243 | N | N | NP | N | N | N | N |
| CHMP2B | high in NP | −6.9 | 0.001985395 | −2.7 | 14443 | 148 | 101 | 50 | 18 | 18 | 23 | N | N | NP | N | N | N | N |
| DDX11 | high in NP | −7.1 | 0.001974424 | −2.7 | 14444 | 25 | 25 | 20 | 4 | 9 | 5 | N | N | NP | N | N | N | N |
| C16orf89 | high in NP | −5.9 | 0.001964824 | −2.7 | 14445 | 25 | 55 | 52 | 5 | 10 | 5 | N | N | NP | N | N | N | N |
| UROD | high in NP | −4.8 | 0.001958653 | −2.7 | 14446 | 60 | 86 | 99 | 16 | 29 | 19 | N | N | NP | N | N | N | N |
| LOC728448 | high in NP | −4.2 | 0.001946311 | −2.7 | 14447 | NA | NA | NA | NA | NA | NA | N | N | NP | N | N | N | N |
| NPDC1 | high in NP | −3.7 | 0.00194014 | −2.7 | 14448 | 1125 | 967 | 884 | 182 | 276 | 334 | NA | NA | NP | N | N | N | N |
| MIER2 | high in NP | −5.6 | 0.001933969 | −2.7 | 14449 | 45 | 99 | 95 | 13 | 19 | 22 | N | N | NP | N | N | N | N |
| MTX1 | high in NP | −4.8 | 0.001927798 | −2.7 | 14450 | 230 | 458 | 288 | 83 | 98 | 55 | N | N | NP | N | N | N | N |
| CBLC | high in NP | −3.8 | 0.001915455 | −2.7 | 14451 | 84 | 88 | 66 | 11 | 21 | 24 | N | N | NP | N | N | N | N |
| RPL10 | high in NP | −4.4 | 0.001898999 | −2.7 | 14452 | 31854 | 26541 | 23996 | 5360 | 8922 | 9492 | N | N | NP | N | N | N | N |
| LOC389033 | high in NP | −10.6 | 0.001892828 | −2.7 | 14453 | 17 | 13 | 52 | 1 | 4 | 1 | NA | NA | NP | N | N | N | N |
| NCRNA00116 | high in NP | −5.2 | 0.001880485 | −2.7 | 14454 | 26 | 60 | 47 | 10 | 9 | 6 | NA | NA | NP | N | N | N | N |
| CTBS | high in NP | −3.0 | 0.001874314 | −2.7 | 14455 | 87 | 106 | 112 | 40 | 32 | 35 | N | N | NP | N | N | N | N |
| KIF7 | high in NP | −7.2 | 0.001845516 | −2.7 | 14456 | 21 | 16 | 15 | 9 | 9 | 12 | N | N | NP | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | | MSDK-seq | | |
|---|---|---|---|---|---|---|---|---|---|---|---|---|---|---|---|---|---|---|
| | | | | | Nulliparous (NP) | | | | Parous (P) | | | | NP | P | | P | | P |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | GeneBody Met | Pro-moter Met | Pro-moter Met |
| SRP14 | high in NP | −4.3 | 0.001839344 | −2.7 | 14457 | 120 | 98 | 81 | 23 | 33 | 16 | N | N | N | N | N | N |
| TRPC4AP | high in NP | −3.8 | 0.001827002 | −2.7 | 14458 | 756 | 1103 | 1224 | 240 | 355 | 300 | N | N | N | N | N | N |
| SLC22A18 | high in NP | −5.4 | 0.001181466 | −2.7 | 14459 | 236 | 135 | 233 | 33 | 53 | 31 | N | N | N | N | N | N |
| TACSTD2 | high in NP | −4.2 | 0.001792718 | −2.7 | 14460 | 4291 | 4010 | 2521 | 1034 | 1038 | 1017 | N | N | N | N | N | N |
| RAB40B | high in NP | −5.1 | 0.001786547 | −2.7 | 14461 | 86 | 52 | 71 | 16 | 23 | 14 | N | N | N | N | N | N |
| TRIM52 | high in NP | −4.5 | 0.001725521 | −2.8 | 14462 | 372 | 861 | 366 | 97 | 108 | 131 | N | N | N | N | N | N |
| ARVCF | high in NP | −5.4 | 0.001171935 | −2.8 | 14463 | 58 | 133 | 102 | 16 | 18 | 23 | N | N | N | N | N | N |
| C6orf57 | high in NP | −4.1 | 0.001677523 | −2.8 | 14464 | 6 | 3 | 6 | 1 | 1 | 1 | N | N | N | N | N | N |
| TFF3 | high in NP | −40.6 | 0.001626097 | −2.8 | 14465 | 1232 | 977 | 583 | 28 | 126 | 11 | N | N | N | N | N | N |
| TSSC4 | high in NP | −4.7 | 0.001582213 | −2.8 | 14466 | 111 | 143 | 179 | 26 | 28 | 45 | N | N | N | N | N | N |
| WBP1 | high in NP | −3.4 | 0.001569871 | −2.8 | 14467 | 200 | 219 | 277 | 70 | 89 | 84 | N | N | N | N | N | N |
| ZAP70 | high in NP | −6.0 | 0.0015541 | −2.8 | 14468 | 10 | 11 | 11 | 6 | 6 | 6 | N | N | N | N | N | N |
| ZNF669 | high in NP | −7.8 | 0.001547929 | −2.8 | 14469 | 40 | 106 | 78 | 15 | 10 | 8 | N | N | N | N | N | N |
| AP1AR | high in NP | −3.4 | 0.001514331 | −2.8 | 14470 | 43 | 60 | 38 | 16 | 21 | 15 | NA | NA | N | N | N | N |
| PPP10A | high in NP | −4.5 | 0.001501988 | −2.8 | 14471 | 74 | 123 | 93 | 32 | 20 | 23 | N | N | N | N | N | N |
| OR2H1 | high in NP | −2.7 | 0.001474561 | −2.8 | 14472 | 10 | 6 | 5 | 2 | 2 | 2 | N | N | N | N | N | N |
| VCL | high in NP | −6.9 | 0.00146839 | −2.8 | 14473 | 1766 | 2370 | 967 | 184 | 318 | 296 | N | N | N | N | N | N |
| KIAA1324 | high in NP | −4.9 | 0.001456048 | −2.8 | 14474 | 1354 | 1401 | 799 | 285 | 319 | 311 | N | N | N | N | N | N |
| MRPS11 | high in NP | −13.0 | 0.001449877 | −2.8 | 14475 | 16 | 49 | 41 | 4 | 4 | 7 | N | N | N | N | N | N |
| SERPINA11 | high in NP | −19.8 | 0.001443705 | −2.8 | 14476 | 52 | 18 | 97 | 2 | 5 | 2 | N | N | N | N | N | N |
| ACTG1 | high in NP | −5.8 | 0.001437534 | −2.8 | 14477 | 22394 | 28860 | 12299 | 3092 | 3700 | 5753 | N | N | N | N | N | N |
| C6orf59 | high in NP | −3.7 | 0.001431363 | −2.8 | 14478 | 8 | 6 | 6 | 3 | 3 | 3 | NA | NA | N | N | N | N |
| B4GALNT4 | high in NP | −4.4 | 0.001410107 | −2.9 | 14479 | 559 | 639 | 1079 | 153 | 165 | 196 | N | N | N | N | N | N |
| C1orf159 | high in NP | −5.0 | 0.001395022 | −2.9 | 14480 | 147 | 243 | 254 | 50 | 63 | 34 | NA | NA | N | N | N | N |
| ARHGEF7 | high in NP | −5.3 | 0.001346338 | −2.9 | 14481 | 186 | 302 | 267 | 37 | 66 | 68 | P | P | N | N | N | N |
| HSP90AB1 | high in NP | −7.9 | 0.001271599 | −2.9 | 14482 | 5431 | 11454 | 7412 | 517 | 922 | 1471 | N | N | N | N | N | N |
| HES4 | high in NP | −4.6 | 0.001259257 | −2.9 | 14483 | 1408 | 1675 | 3319 | 377 | 448 | 448 | N | N | N | N | N | N |
| C12orf70 | high in NP | −8.3 | 0.001243486 | −2.9 | 14484 | 14 | 17 | 25 | 2 | 2 | 5 | NA | NA | N | N | N | N |
| EIF3G | high in NP | −4.9 | 0.001237315 | −2.9 | 14485 | 350 | 605 | 524 | 84 | 128 | 140 | N | N | N | N | N | N |
| PODXL2 | high in NP | −8.7 | 0.001224973 | −2.9 | 14486 | 159 | 94 | 211 | 21 | 27 | 17 | N | N | N | N | N | N |
| EIF6 | high in NP | −16.5 | 0.001218801 | −2.9 | 14487 | 388 | 2109 | 1121 | 84 | 106 | 83 | N | N | N | N | N | N |
| CDK20 | high in NP | −2.9 | 0.001206459 | −2.9 | 14488 | 17 | 26 | 27 | 6 | 2 | 6 | N | N | N | N | N | N |
| ZNF467 | high in NP | −8.9 | 0.001200288 | −2.9 | 14489 | 39 | 55 | 46 | 12 | 4 | 4 | N | N | N | N | N | N |
| HPX | high in NP | −6.7 | 0.001187946 | −2.9 | 14490 | 492 | 500 | 549 | 123 | 87 | 39 | N | N | N | N | N | N |
| ENY2 | high in NP | −8.7 | 0.001159833 | −2.9 | 14491 | 27 | 24 | 7 | 2 | 2 | 2 | N | N | N | N | N | N |
| FPGS | high in NP | −3.0 | 0.001093321 | −2.9 | 14492 | 115 | 171 | 150 | 49 | 51 | 50 | N | N | N | N | N | N |
| GCAT | high in NP | −2.6 | 0.001063837 | −3.0 | 14493 | 15 | 14 | 12 | 6 | 6 | 6 | N | N | N | N | N | N |
| ZNF783 | high in NP | −2.7 | 0.001057666 | −3.0 | 14494 | NA | NA | NA | NA | NA | NA | NA | NA | N | N | N | N |
| NCRNA00173 | high in NP | 5.9 | 0.001051495 | −3.0 | 14495 | 23 | 14 | 25 | 2 | 2 | 6 | NA | NA | N | N | N | N |
| TRAP1 | high in NP | −3.9 | 0.001045324 | −3.0 | 14496 | 456 | 461 | 433 | 88 | 152 | 124 | N | N | N | N | N | N |
| ABCA11P | high in NP | −3.1 | 0.001023382 | −3.0 | 14497 | 7 | 5 | 3 | 2 | 2 | 2 | N | N | N | N | N | N |
| AGR3 | high in NP | −13.3 | 0.001004868 | −3.0 | 14498 | 179 | 173 | 85 | 5 | 22 | 15 | N | N | N | N | N | N |
| PGLS | high in NP | −6.2 | 0.000992226 | −3.0 | 14499 | 322 | 469 | 846 | 91 | 81 | 65 | N | N | N | N | N | N |
| KRT86 | high in NP | −4.2 | 0.000967841 | −3.0 | 14500 | 20 | 18 | 19 | 5 | 3 | 6 | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | MSDK-seq | | | |
|---|---|---|---|---|---|---|---|---|---|---|---|---|---|---|---|---|---|---|
| | | | | | | Nulliparous (NP) | | | | Parous (P) | | | NP | P | NP | | P | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody | GeneBody Met | Pro-moter Met | Pro-moter Met |
| REEP5 | high in NP | -7.8 | 0.000939728 | -3.0 | 14501 | 221 | 563 | 416 | 81 | 70 | 72 | N | N | NP | N | N | N |
| POMP | high in NP | -4.5 | 0.000921215 | -3.0 | 14502 | 1115 | 1875 | 1124 | 285 | 374 | 271 | N | N | NP | N | N | N |
| RHOA | high in NP | -3.3 | 0.000899959 | -3.0 | 14503 | 3764 | 4685 | 3685 | 1024 | 1334 | 1215 | N | N | NP | N | N | N |
| TNFRSF14 | high in NP | -4.3 | 0.000893788 | -3.0 | 14504 | 170 | 165 | 207 | 38 | 43 | 59 | N | N | NP | N | N | N |
| CYP4F12 | high in NP | -3.1 | 0.000864646 | -3.1 | 14505 | 7 | 5 | 4 | 2 | 2 | 2 | N | N | NP | P | N | N |
| GOLGA6L10 | high in NP | -3.1 | 0.000864646 | -3.1 | 14506 | 7 | 4 | 3 | 2 | 2 | 2 | NA | NA | NP | N | N | N |
| TMSB15A | high in NP | -5.8 | 0.000792992 | -3.1 | 14507 | 22 | 7 | 6 | 2 | 2 | 2 | NA | NA | NP | N | N | N |
| SH3GL1 | high in NP | -3.7 | 0.000777222 | -3.1 | 14508 | 606 | 584 | 579 | 132 | 207 | 168 | N | N | NP | N | N | N |
| SELENBP1 | high in NP | -9.0 | 0.000764879 | -3.1 | 14509 | 387 | 258 | 336 | 30 | 45 | 69 | N | N | NP | N | N | N |
| ZNF204P | high in NP | -2.9 | 0.000758708 | -3.1 | 14510 | 24 | 30 | 23 | 12 | 12 | 12 | NA | NA | NP | N | N | N |
| LASP1 | high in NP | -6.8 | 0.000752537 | -3.1 | 14511 | 184 | 316 | 138 | 38 | 34 | 35 | N | N | NP | N | N | N |
| PVRL4 | high in NP | -5.8 | 0.000692883 | -3.2 | 14512 | 658 | 923 | 475 | 133 | 150 | 144 | N | N | NP | N | N | N |
| UBR4 | high in NP | -3.3 | 0.000686711 | -3.2 | 14513 | 753 | 915 | 834 | 312 | 360 | 283 | N | N | NP | N | N | N |
| MARCKSL1 | high in NP | -6.7 | 0.000674369 | -3.2 | 14514 | 964 | 1732 | 1447 | 188 | 222 | 327 | N | N | NP | N | N | N |
| TOMM34 | high in NP | -5.6 | 0.000655856 | -3.2 | 14515 | 105 | 185 | 121 | 20 | 24 | 35 | N | N | NP | N | N | N |
| LRGUK | high in NP | -6.0 | 0.000640771 | -3.2 | 14516 | 20 | 19 | 17 | 4 | 7 | 4 | N | N | NP | N | N | N |
| AZGP1 | high in NP | -1.4.0 | 0.000628428 | -3.2 | 14517 | 1365 | 4611 | 1039 | 124 | 169 | 109 | N | N | NP | N | N | N |
| TMEM199 | high in NP | -4.2 | 0.0006154 | -3.2 | 14518 | 17 | 27 | 16 | 4 | 4 | 4 | N | N | NP | N | N | N |
| NUDT16L1 | high in NP | -4.2 | 0.000592087 | -3.2 | 14519 | 13 | 13 | 15 | 5 | 5 | 5 | N | N | NP | N | N | N |
| C19orf48 | high in NP | -8.2 | 0.000579745 | -3.2 | 14520 | 477 | 437 | 597 | 58 | 119 | 74 | N | N | NP | N | N | N |
| NDUFS3 | high in NP | -4.4 | 0.000573574 | -3.2 | 14521 | 191 | 213 | 140 | 34 | 42 | 52 | N | N | NP | N | N | N |
| C2orf63 | high in NP | -3.7 | 0.000558489 | -3.3 | 14522 | 15 | 8 | 9 | 6 | 6 | 6 | N | N | NP | N | N | N |
| C17orf106 | high in NP | -5.6 | 0.000545461 | -3.3 | 14523 | 47 | 42 | 33 | 6 | 9 | 4 | NA | NA | NP | N | N | N |
| LILRB3 | high in NP | -7.5 | 0.000533118 | -3.3 | 14524 | 96 | 183 | 121 | 14 | 27 | 23 | N | N | NP | N | N | N |
| CCDC74A | high in NP | -20.5 | 0.000520776 | -3.3 | 14525 | 13 | 28 | 44 | 1 | 1 | 1 | N | N | NP | N | N | N |
| RAB11B | high in NP | -5.6 | 0.000509805 | -3.3 | 14526 | 324 | 675 | 345 | 85 | 74 | 77 | N | N | NP | N | N | N |
| DDX41 | high in NP | -4.1 | 0.000503634 | -3.3 | 14527 | 218 | 326 | 211 | 63 | 71 | 66 | N | N | NP | N | N | N |
| JUP | high in NP | -6.6 | 0.000497463 | -3.3 | 14528 | 3946 | 6065 | 8196 | 690 | 985 | 968 | N | N | NP | N | N | N |
| C11orf10 | high in NP | -6.9 | 0.000491292 | -3.3 | 14529 | 840 | 1016 | 546 | 98 | 122 | 161 | N | N | NP | N | N | N |
| C19orf10 | high in NP | -6.7 | 0.000485121 | -3.3 | 14530 | 493 | 565 | 372 | 73 | 114 | 71 | N | N | NP | N | N | N |
| ATHL1 | high in NP | -14.5 | 0.000478985 | -3.3 | 14531 | 1481 | 2074 | 772 | 89 | 177 | 112 | N | P | NP | N | N | N |
| SCAND1 | high in NP | -9.1 | 0.000472778 | -3.3 | 14532 | 220 | 354 | 524 | 49 | 42 | 37 | N | N | NP | N | N | N |
| LOC440957 | high in NP | -3.3 | 0.000444094 | -3.3 | 14533 | 99 | 105 | 106 | 26 | 31 | 30 | N | N | NP | N | N | N |
| NDUFB4 | high in NP | -13.0 | 0.000428209 | -3.4 | 14534 | 194 | 397 | 146 | 13 | 26 | 20 | N | N | NP | N | N | N |
| C7orf50 | high in NP | -31.8 | 0.000409696 | -3.4 | 14535 | 39 | 164 | 120 | 4 | 4 | 4 | N | N | NP | N | N | N |
| ARHGEF10L | high in NP | -6.0 | 0.000397353 | -3.4 | 14536 | 540 | 592 | 751 | 110 | 133 | 149 | N | N | NP | N | N | N |
| FUS | high in NP | -7.2 | 0.00037884 | -3.4 | 14537 | 426 | 705 | 448 | 84 | 101 | 113 | N | N | NP | N | N | N |
| COX8A | high in NP | -7.9 | 0.000360326 | -3.4 | 14538 | 792 | 1217 | 597 | 93 | 134 | 131 | N | N | NP | N | N | N |
| HMGCL | high in NP | -7.3 | 0.000354155 | -3.5 | 14539 | 23 | 31 | 24 | 3 | 6 | 3 | N | N | NP | N | N | N |
| RPL10A | high in NP | -9.2 | 0.000347984 | -3.5 | 14540 | 25349 | 23535 | 33127 | 2343 | 4115 | 4882 | N | N | NP | N | N | N |
| MGAT3 | high in NP | -4.6 | 0.000341813 | -3.5 | 14541 | 18 | 21 | 13 | 6 | 6 | 6 | N | N | NP | N | N | N |
| LGMN | high in NP | -5.9 | 0.000328785 | -3.5 | 14542 | 161 | 256 | 173 | 39 | 33 | 45 | N | N | NP | N | N | N |
| PRINS | high in NP | -6.4 | 0.0003137 | -3.5 | 14543 | 40 | 69 | 52 | 10 | 8 | 11 | N | N | NP | N | N | N |
| RAB32 | high in NP | -4.7 | 0.000301358 | -3.5 | 14544 | 110 | 113 | 123 | 25 | 32 | 30 | N | N | NP | N | N | N |

TABLE 16-continued

Genes that Are Differentially Methylated between Nulliparous and Parous CD24+ Breast Epithelial Cells

| Gene Symbol | expression pattern | Fold Change | p-value | log10 (p-val.) | Ranking | SAGE-seq Nulliparous (NP) CD24+ N48 | CD24+ N58 | CD24+ N43 | Parous (P) CD24+ N37 | CD24+ N39 | CD24+ N40 | ChIP-seq NP CD24+ N74 | P CD24+ N66 | MSDK-seq GeneBody Met NP | GeneBody Met P | Pro-moter Met NP | Pro-moter Met P |
|---|---|---|---|---|---|---|---|---|---|---|---|---|---|---|---|---|---|
| FUZ | high in NP | -7.0 | 0.000295187 | -3.5 | 14545 | 41 | 69 | 53 | 10 | 11 | 9 | N | N | N | N | N | N |
| GOLGA6L1 | high in NP | -5.3 | 0.000282844 | -3.5 | 14546 | 9 | 3 | 7 | 1 | 1 | 1 | N | NA | N | N | N | N |
| FAM150B | high in NP | -7.2 | 0.000276673 | -3.6 | 14547 | 15 | 10 | 6 | 3 | 3 | 3 | N | P | N | N | N | N |
| SYTL1 | high in NP | -7.0 | 0.000251988 | -3.6 | 14548 | 111 | 109 | 177 | 15 | 20 | 19 | N | N | N | N | N | N |
| PIN1 | high in NP | -6.6 | 0.000239646 | -3.6 | 14549 | 117 | 178 | 176 | 28 | 20 | 28 | N | N | N | N | N | N |
| MRPL54 | high in NP | -8.6 | 0.000217704 | -3.7 | 14550 | 134 | 141 | 158 | 11 | 24 | 16 | N | N | N | N | N | N |
| EGR4 | high in NP | -5.3 | 0.000205362 | -3.7 | 14551 | 11 | 5 | 7 | 2 | 2 | 2 | N | N | N | N | N | N |
| PTPRS | high in NP | -7.5 | 0.000199191 | -3.7 | 14552 | 121 | 150 | 143 | 38 | 42 | 32 | N | P | N | N | N | N |
| C5orf38 | high in NP | -16.5 | 0.000019302 | -3.7 | 14553 | 33 | 22 | 42 | 4 | 2 | 2 | N | P | N | N | N | P |
| TMSB10 | high in NP | -8.4 | 0.000179992 | -3.7 | 14554 | 2539 | 4007 | 2574 | 309 | 483 | 360 | N | P | N | N | N | N |
| TFF1 | high in NP | -21.3 | 0.000155307 | -3.8 | 14555 | 3263 | 4094 | 1861 | 148 | 252 | 106 | N | P | N | N | N | N |
| CHCHD5 | high in NP | -7.7 | 0.000134051 | -3.9 | 14556 | 158 | 154 | 220 | 20 | 27 | 22 | N | N | N | N | N | N |
| RNF126P1 | high in NP | -8.9 | 0.000012788 | -3.9 | 14557 | 294 | 229 | 327 | 38 | 39 | 38 | N | N | N | N | N | N |
| MRPL24 | high in NP | -9.5 | 0.000114166 | -3.9 | 14558 | 159 | 146 | 101 | 14 | 16 | 13 | N | N | N | N | N | N |
| ITIH4 | high in NP | -7.6 | 9.29E-05 | -4.0 | 14559 | 44 | 52 | 48 | 11 | 9 | 9 | N | N | N | N | N | N |
| LILRA5 | high in NP | -7.1 | 8.67E-05 | -4.1 | 14560 | 19 | 21 | 20 | 3 | 3 | 3 | N | N | N | N | N | N |
| PVRL2 | high in NP | -18.3 | 8.06E-05 | -4.1 | 14561 | 1422 | 2284 | 2051 | 162 | 145 | 146 | N | N | N | N | N | N |
| PRDM1 | high in P | 15.2 | 0.000107995 | 4.0 | 1 | 46 | 45 | 48 | 694 | 415 | 493 | N | N | N | N | N | N |
| ANXA5 | high in P | 6.6 | 0.000140222 | 3.9 | 2 | 71 | 62 | 74 | 387 | 395 | 315 | P | N | N | N | N | N |
| EDNRB | high in P | 86.1 | 0.000161478 | 3.8 | 3 | 25 | 24 | 36 | 1531 | 659 | 374 | N | N | N | N | N | N |
| OGN | high in P | 6.2 | 0.000167649 | 3.8 | 4 | 6 | 6 | 6 | 16 | 14 | 15 | N | N | N | N | N | N |
| CACNA1G | high in P | 22.8 | 0.000173821 | 3.8 | 5 | 15 | 15 | 18 | 141 | 73 | 124 | P | N | N | N | N | N |
| HSD11B1 | high in P | 8.7 | 0.000211533 | 3.7 | 6 | 119 | 132 | 173 | 1340 | 832 | 841 | P | N | N | N | N | N |
| CCT2 | high in P | 6.5 | 0.000223875 | 3.6 | 7 | 2173 | 2572 | 3724 | 15795 | 16912 | 15199 | N | N | N | N | N | N |
| SRGAP2 | high in P | 7.9 | 0.000233475 | 3.6 | 8 | 39 | 59 | 57 | 422 | 283 | 213 | N | N | N | N | N | N |
| USP45 | high in P | 5.4 | 0.000245817 | 3.6 | 9 | 16 | 20 | 15 | 87 | 96 | 66 | N | N | N | N | N | N |
| PGS1 | high in P | 4.4 | 0.000289015 | 3.5 | 10 | 48 | 63 | 50 | 207 | 159 | 171 | N | N | N | N | N | N |
| INPP5D | high in P | 6.9 | 0.000307529 | 3.5 | 11 | 109 | 112 | 157 | 826 | 763 | 555 | N | N | N | N | N | N |
| BCAM | high in P | 7.9 | 0.000366498 | 3.4 | 12 | 14 | 12 | 18 | 77 | 83 | 102 | N | NA | N | N | N | N |
| C15orf61 | high in P | 13.8 | 0.000372669 | 3.4 | 13 | 246 | 159 | 356 | 3133 | 3572 | 1650 | N | NA | N | N | N | N |
| FST | high in P | 4.6 | 0.000385011 | 3.4 | 14 | 109 | 91 | 84 | 337 | 395 | 371 | N | NA | N | N | N | N |
| SLC25A1 | high in P | 39.9 | 0.000391182 | 3.4 | 15 | 7 | 34 | 15 | 391 | 270 | 602 | N | N | N | N | N | N |
| TSG101 | high in P | 5.3 | 0.000403524 | 3.4 | 16 | 247 | 259 | 341 | 1410 | 1214 | 1092 | N | N | N | N | N | N |
| MIIP | high in P | 5.1 | 0.000418867 | 3.4 | 17 | 616 | 747 | 780 | 4713 | 3568 | 2757 | N | NA | N | N | N | N |
| RPL9 | high in P | 7.2 | 0.000422038 | 3.4 | 18 | 51 | 32 | 33 | 294 | 274 | 169 | P | P | N | N | N | N |
| PUS7L | high in P | 5.1 | 0.00043438 | 3.4 | 19 | 17882 | 12321 | 16131 | 64070 | 57350 | 57363 | N | N | N | N | N | N |
| RPL23P8 | high in P | 7.4 | 0.000466607 | 3.3 | 20 | 7 | 14 | 13 | 63 | 79 | 50 | N | N | N | N | N | N |
| ID3 | high in P | 4.6 | 0.000526947 | 3.3 | 21 | 6 | 1 | 2 | 12 | 12 | 14 | N | NA | N | N | N | N |
| SOX11 | high in P | 5.6 | 0.00053929 | 3.3 | 22 | 75 | 78 | 90 | 490 | 293 | 321 | N | P | N | N | N | N |
| NRBP1 | high in P | 5.7 | 0.000585916 | 3.3 | 23 | 16 | 29 | 21 | 86 | 100 | 64 | N | N | N | N | N | N |
| NUDT16 | high in P | 4.6 | 0.0006346 | 3.2 | 24 | 732 | 563 | 517 | 2513 | 2431 | 2151 | N | N | N | N | N | N |
| REPIN1 | high in P | 4.0 | 0.000662027 | 3.2 | 25 | 25 | 35 | 31 | 121 | 104 | 78 | N | N | N | N | N | N |
| KIAA1324L | high in P | 5.2 | 0.000668198 | 3.2 | 26 | 508 | 618 | 685 | 4331 | 2842 | 2106 | N | N | N | N | N | N |
| | high in P | 4.0 | 0.00068054 | 3.2 | 27 | 18 | 20 | 17 | 50 | 58 | 56 | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | | MSDK-seq | | |
|---|---|---|---|---|---|---|---|---|---|---|---|---|---|---|---|---|---|---|
| | | | | | Nulliparous (NP) | | | | Parous (P) | | | | NP | | P | GeneBody | GeneBody | Pro-moter |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | Met P | Met NP | Pro-moter Met | Pro-moter Met P |
| NFIC | high in P | 6.1 | 0.000707968 | 3.1 | 28 | 494 | 398 | 427 | 3122 | 2437 | 1529 | N | N | N | N | N | N | N |
| TLX3 | high in P | 5.0 | 0.000719624 | 3.1 | 29 | 2 | 2 | 2 | 24 | 14 | 18 | P | P | N | N | N | N | N |
| LOX | high in P | 9.9 | 0.000725795 | 3.1 | 30 | 170 | 79 | 150 | 1540 | 941 | 934 | N | N | N | N | N | N | N |
| ZNF425 | high in P | 3.7 | 0.000736766 | 3.1 | 31 | 90 | 103 | 117 | 351 | 314 | 287 | N | N | N | N | N | N | N |
| LOC387763 | high in P | 22.3 | 0.000742937 | 3.1 | 32 | NA | NA | NA | NA | NA | NA | NA | NA | N | N | N | N | N |
| XRCC6 | high in P | 6.3 | 0.000777105 | 3.1 | 33 | 3799 | 4173 | 6237 | 24188 | 27428 | 17331 | NA | NA | N | N | N | N | N |
| SLC17A9 | high in P | 4.8 | 0.000783393 | 3.1 | 34 | 9 | 11 | 13 | 39 | 35 | 55 | N | N | N | N | N | N | N |
| SP4 | high in P | 6.5 | 0.000799163 | 3.1 | 35 | 19 | 27 | 16 | 112 | 69 | 77 | N | N | N | P | N | N | N |
| SCN4A | high in P | 10.5 | 0.000814248 | 3.1 | 36 | 20 | 21 | 26 | 128 | 71 | 72 | N | N | N | N | N | N | N |
| CBR3 | high in P | 5.5 | 0.000823848 | 3.1 | 37 | 10 | 12 | 11 | 63 | 98 | 45 | N | N | N | N | N | N | N |
| ERLIN1 | high in P | 7.6 | 0.000830019 | 3.1 | 38 | 199 | 264 | 430 | 1377 | 1691 | 1679 | N | N | N | N | N | N | N |
| TULP2 | high in P | 9.5 | 0.0008361 | 3.1 | 39 | 4 | 4 | 4 | 13 | 16 | 51 | N | N | N | N | N | N | N |
| TACC1 | high in P | 8.9 | 0.000842361 | 3.1 | 40 | 52 | 60 | 57 | 471 | 330 | 190 | N | N | N | N | N | N | N |
| PJA1 | high in P | 5.9 | 0.000848533 | 3.1 | 41 | 71 | 47 | 91 | 342 | 349 | 299 | N | N | N | N | N | N | N |
| CSN1S1 | high in P | 42.7 | 0.000873903 | 3.1 | 42 | 4 | 4 | 5 | 109 | 140 | 1191 | N | N | N | N | N | N | N |
| TIPRL | high in P | 3.1 | 0.000887617 | 3.1 | 43 | 129 | 145 | 149 | 453 | 378 | 337 | N | N | N | N | N | N | N |
| ZBTB7B | high in P | 3.4 | 0.00090613 | 3.0 | 44 | 399 | 508 | 579 | 1511 | 1545 | 1387 | N | N | N | N | N | N | N |
| RMND5B | high in P | 8.5 | 0.000927386 | 3.0 | 45 | 101 | 92 | 189 | 831 | 735 | 562 | N | N | N | N | N | N | N |
| PCMT1 | high in P | 4.9 | 0.000933557 | 3.0 | 46 | 549 | 452 | 574 | 2725 | 2900 | 1623 | N | N | N | N | N | N | N |
| C6orf41 | high in P | 5.4 | 0.000961617 | 3.0 | 47 | 14 | 28 | 15 | 86 | 92 | 105 | N | N | N | N | N | N | N |
| ITPRIP | high in P | 3.6 | 0.000974013 | 3.0 | 48 | 20 | 22 | 19 | 45 | 57 | 51 | N | N | N | N | N | N | N |
| MAP4K4 | high in P | 2.8 | 0.000980184 | 3.0 | 49 | 305 | 438 | 392 | 1031 | 928 | 991 | N | N | N | N | N | N | N |
| DSG2 | high in P | 5.2 | 0.000986355 | 3.0 | 50 | 1023 | 1043 | 740 | 4373 | 3649 | 5812 | N | N | N | N | N | N | N |
| DUOX2 | high in P | 10.2 | 0.000998697 | 3.0 | 51 | 7 | 10 | 9 | 86 | 56 | 30 | P | P | N | N | N | N | N |
| FLJ39653 | high in P | 5.0 | 0.001011039 | 3.0 | 52 | 10 | 11 | 13 | 32 | 33 | 43 | NA | NA | N | N | N | N | N |
| ANKRD40 | high in P | 4.2 | 0.001017211 | 3.0 | 53 | 288 | 335 | 220 | 985 | 1207 | 881 | N | N | N | N | N | N | N |
| MRPL32 | high in P | 3.1 | 0.001039152 | 3.0 | 54 | 468 | 522 | 394 | 1193 | 1355 | 1205 | N | N | N | N | N | N | N |
| KCNK3 | high in P | 6.7 | 0.001070008 | 3.0 | 55 | 9 | 10 | 11 | 45 | 27 | 28 | P | P | N | N | N | N | N |
| RARRES2 | high in P | 6.9 | 0.001076179 | 3.0 | 56 | 2 | 6 | 3 | 21 | 25 | 30 | N | N | N | N | N | N | N |
| DIAPH3 | high in P | 2.7 | 0.00108715 | 3.0 | 57 | 4 | 8 | 8 | 21 | 22 | 20 | N | N | N | N | N | N | N |
| DNM1L | high in P | 3.1 | 0.001099493 | 3.0 | 58 | 191 | 197 | 160 | 488 | 500 | 484 | N | N | N | N | N | N | N |
| HNRNPU | high in P | 4.1 | 0.001114578 | 3.0 | 59 | 1042 | 932 | 631 | 3689 | 3576 | 4205 | N | N | N | N | N | N | N |
| ASF1A | high in P | 6.5 | 0.001127606 | 2.9 | 60 | 57 | 75 | 88 | 481 | 415 | 225 | N | N | N | N | N | N | N |
| COX18 | high in P | 11.2 | 0.001133777 | 2.9 | 61 | 26 | 38 | 31 | 388 | 285 | 115 | N | N | N | N | N | N | N |
| SNAI3 | high in P | 10.8 | 0.001148862 | 2.9 | 62 | 3 | 3 | 7 | 30 | 30 | 34 | P | P | N | N | N | N | N |
| PCY0X1 | high in P | 3.2 | 0.001166004 | 2.9 | 63 | 45 | 63 | 52 | 187 | 129 | 129 | N | N | N | N | N | N | N |
| CXCL17 | high in P | 17.6 | 0.001172175 | 2.9 | 64 | 46 | 98 | 143 | 2147 | 662 | 720 | N | N | N | N | N | N | N |
| LMAN2L | high in P | 17.4 | 0.001194117 | 2.9 | 65 | 54 | 63 | 192 | 771 | 799 | 706 | N | N | N | N | N | N | N |
| METTL11A | high in P | 3.3 | 0.00121263 | 2.9 | 66 | 167 | 180 | 147 | 615 | 475 | 433 | N | N | N | N | N | N | N |
| MTERFD2 | high in P | 5.4 | 0.001231144 | 2.9 | 67 | 21 | 58 | 35 | 226 | 148 | 143 | N | N | N | N | N | N | N |
| NHEJ1 | high in P | 4.5 | 0.001253086 | 2.9 | 68 | 98 | 98 | 143 | 344 | 387 | 377 | NA | NA | N | N | N | N | N |
| AKR1E2 | high in P | 2.8 | 0.001265428 | 2.9 | 69 | 4 | 5 | 5 | 12 | 11 | 12 | N | N | N | N | N | N | N |
| LAMA4 | high in P | 13.6 | 0.00127777 | 2.9 | 70 | 50 | 49 | 76 | 767 | 436 | 214 | NA | NA | N | N | N | N | N |
| PARG | high in P | 2.6 | 0.001292855 | 2.9 | 71 | 43 | 58 | 50 | 122 | 115 | 135 | N | N | N | N | N | N | N |

TABLE 16-continued

Genes that Are Differentially Methylated between Nulliparous and Parous CD24+ Breast Epithelial Cells

| | | | | SAGE-seq | | | | | | | | | ChIP-seq | | | | MSDK-seq | | |
|---|---|---|---|---|---|---|---|---|---|---|---|---|---|---|---|---|---|---|---|
| | | | | | | Nulliparous (NP) | | | | Parous (P) | | | | NP | | | | | |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | CD24+ N74 | CD24+ N66 | NP | GeneBody NP | GeneBody Met | Pro-moter Met | NP Met | Pro-moter Met |
| C8orf33 | high in P | 3.8 | 0.001299026 | 2.9 | 72 | 163 | 130 | 141 | 552 | 393 | 524 | N | N | N | N | N | N | N | N |
| LDB2 | high in P | 3.3 | 0.001305197 | 2.9 | 73 | 14 | 15 | 12 | 33 | 27 | 30 | N | N | N | N | N | N | N | N |
| SLC43A1 | high in P | 5.5 | 0.001333996 | 2.9 | 74 | 19 | 16 | 14 | 90 | 73 | 42 | N | N | N | N | N | N | N | N |
| MYLK | high in P | 14.3 | 0.001340167 | 2.9 | 75 | 70 | 76 | 52 | 327 | 241 | 908 | N | N | N | N | N | N | N | N |
| RGS5 | high in P | 5.6 | 0.001135251 | 2.9 | 76 | 17 | 18 | 17 | 81 | 45 | 49 | N | N | N | N | N | N | N | N |
| TGFB2 | high in P | 5.3 | 0.001367595 | 2.9 | 77 | 172 | 101 | 165 | 536 | 674 | 752 | N | N | N | N | N | N | N | N |
| SIN3A | high in P | 3.8 | 0.001373766 | 2.9 | 78 | 304 | 385 | 489 | 1609 | 1068 | 1496 | N | N | N | N | N | N | N | N |
| SHF | high in P | 5.4 | 0.001379937 | 2.9 | 79 | 22 | 41 | 48 | 202 | 164 | 133 | N | N | N | N | N | N | N | N |
| NPTN | high in P | 2.8 | 0.001416278 | 2.9 | 80 | 355 | 352 | 299 | 849 | 819 | 948 | N | N | N | N | N | N | N | N |
| RACGAP1 | high in P | 4.4 | 0.001462219 | 2.8 | 81 | 36 | 16 | 29 | 127 | 118 | 98 | N | N | N | N | N | N | N | N |
| C18orf25 | high in P | 4.5 | 0.001489646 | 2.8 | 82 | 115 | 87 | 76 | 327 | 265 | 387 | N | N | N | N | N | N | N | N |
| LOC285375 | high in P | 5.8 | 0.001495817 | 2.8 | 83 | 3 | 3 | 3 | 20 | 11 | 9 | NA | N | N | N | N | N | N | N |
| TIE1 | high in P | 15.3 | 0.001150816 | 2.8 | 84 | 13 | 27 | 36 | 438 | 193 | 112 | N | N | N | N | N | N | N | N |
| B3GAT1 | high in P | 23.6 | 0.001532844 | 2.8 | 85 | 9 | 16 | 13 | 50 | 208 | 258 | P | NA | N | N | N | N | N | N |
| SLC1A5 | high in P | 14.8 | 0.001560272 | 2.8 | 86 | 617 | 1024 | 2753 | 16550 | 15441 | 8601 | N | N | N | N | N | N | N | N |
| AES | high in P | 5.4 | 0.001576042 | 2.8 | 87 | 2329 | 3777 | 5620 | 18818 | 16607 | 13627 | N | N | N | N | N | N | N | N |
| NHEDC2 | high in P | 3.1 | 0.001588385 | 2.8 | 88 | 65 | 51 | 59 | 155 | 164 | 159 | N | N | N | N | N | N | N | N |
| SYNPO | high in P | 2.9 | 0.001594556 | 2.8 | 89 | 28 | 61 | 51 | 117 | 93 | 113 | N | N | N | N | N | N | N | N |
| ZFAND2B | high in P | 3.0 | 0.001600727 | 2.8 | 90 | 143 | 136 | 116 | 324 | 333 | 420 | N | N | N | N | N | N | N | N |
| FOXO1 | high in P | 3.5 | 0.001606898 | 2.8 | 91 | 135 | 216 | 182 | 577 | 413 | 593 | N | N | N | N | N | N | N | N |
| LXN | high in P | 9.3 | 0.001619926 | 2.8 | 92 | 19 | 18 | 7 | 161 | 64 | 79 | N | N | N | N | N | N | N | N |
| RRAGD | high in P | 4.4 | 0.001632268 | 2.8 | 93 | 72 | 136 | 74 | 305 | 260 | 331 | N | N | N | N | N | N | N | N |
| C10orf118 | high in P | 2.9 | 0.001638439 | 2.8 | 94 | 61 | 58 | 67 | 164 | 152 | 132 | N | N | N | N | N | N | N | N |
| PI4K2A | high in P | 5.9 | 0.001164941 | 2.8 | 95 | 235 | 325 | 516 | 1933 | 1635 | 1287 | N | N | N | N | N | N | N | N |
| SLC43A2 | high in P | 7.7 | 0.001655581 | 2.8 | 96 | 61 | 197 | 107 | 828 | 647 | 464 | N | N | N | N | N | N | N | N |
| WDR45 | high in P | 3.7 | 0.001661753 | 2.8 | 97 | 312 | 482 | 442 | 1788 | 1403 | 1079 | P | N | N | N | N | N | N | N |
| PLEKHF1 | high in P | 4.0 | 0.001671352 | 2.8 | 98 | 358 | 228 | 264 | 951 | 1076 | 940 | N | N | N | N | N | N | N | N |
| SOX10 | high in P | 5.8 | 0.001683694 | 2.8 | 99 | 436 | 273 | 224 | 1729 | 1345 | 1187 | N | N | N | N | N | N | N | N |
| IL17RA | high in P | 3.3 | 0.001689866 | 2.8 | 100 | 51 | 54 | 53 | 147 | 168 | 123 | N | N | N | N | N | N | N | N |
| C15orf48 | high in P | 17.0 | 0.001696037 | 2.8 | 101 | 142 | 77 | 17 | 892 | 949 | 638 | N | N | N | N | N | N | N | N |
| GRPEL1 | high in P | 2.4 | 0.001774205 | 2.8 | 102 | 279 | 343 | 361 | 702 | 790 | 759 | N | N | N | N | N | N | N | N |
| MLX | high in P | 3.5 | 0.001780376 | 2.7 | 103 | 251 | 302 | 368 | 1185 | 896 | 758 | N | N | N | N | N | N | N | N |
| SOBP | high in P | 7.2 | 0.001798889 | 2.7 | 104 | 27 | 30 | 27 | 51 | 55 | 110 | P | N | N | N | N | N | N | N |
| SIX5 | high in P | 4.7 | 0.001180506 | 2.7 | 105 | 105 | 75 | 57 | 330 | 299 | 234 | N | N | N | N | N | N | N | N |
| PRDX6 | high in P | 2.7 | 0.001820831 | 2.7 | 106 | 1138 | 1219 | 1136 | 3911 | 2960 | 2647 | N | N | N | N | N | N | N | N |
| MID1IP1 | high in P | 2.7 | 0.001833173 | 2.7 | 107 | 107 | 135 | 97 | 262 | 239 | 268 | N | N | N | N | N | N | N | N |
| LAMC3 | high in P | 4.9 | 0.001851687 | 2.7 | 108 | 17 | 17 | 18 | 48 | 35 | 40 | P | N | N | N | N | N | N | N |
| ZNF507 | high in P | 3.2 | 0.001857858 | 2.7 | 109 | 31 | 33 | 27 | 83 | 72 | 77 | N | N | N | N | N | N | N | N |
| MRPS18C | high in P | 4.1 | 0.001886657 | 2.7 | 110 | 24 | 25 | 35 | 115 | 87 | 88 | N | N | N | N | N | N | N | N |
| ZNF384 | high in P | 4.2 | 0.001921626 | 2.7 | 111 | 277 | 269 | 439 | 1074 | 1177 | 1024 | N | N | N | N | N | N | N | N |
| SRPX | high in P | 10.8 | 0.001952482 | 2.7 | 112 | 9 | 9 | 9 | 39 | 22 | 14 | P | N | N | N | N | N | N | N |
| AIPL1 | high in P | 5.5 | 0.001991566 | 2.7 | 113 | 18 | 8 | 15 | 74 | 97 | 45 | N | N | N | N | N | N | N | N |
| VNN3 | high in P | 8.8 | 0.001997737 | 2.7 | 114 | 23 | 131 | 81 | 838 | 533 | 516 | N | N | N | N | N | N | N | N |
| KIAA0649 | high in P | 2.8 | 0.002003908 | 2.7 | 115 | 88 | 85 | 77 | 178 | 194 | 188 | N | N | N | N | N | N | N | N |

TABLE 16-continued

Genes that Are Differentially Methylated between Nulliparous and Parous CD24+ Breast Epithelial Cells

| | | | | SAGE-seq | | | | | | | | | ChIP-seq | | | MSDK-seq | | |
|---|---|---|---|---|---|---|---|---|---|---|---|---|---|---|---|---|---|---|
| | | | | | Nulliparous (NP) | | | | Parous (P) | | | | NP | CD24+ N74 | CD24+ N66 | GeneBody | GeneBody Met | Pro-moter Met |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | | P | P | | NP | P | P |
| APPBP2 | high in P | 4.3 | 0.00201008 | 2.7 | 116 | 77 | 65 | 59 | 195 | 193 | 246 | N | N | N | NP | N | N | N |
| FERMT1 | high in P | 14.4 | 0.0020022422 | 2.7 | 117 | 15 | 8 | 9 | 108 | 219 | 44 | N | P | N | N | N | N | N |
| RNH1 | high in P | 3.5 | 0.002028593 | 2.7 | 118 | 927 | 1125 | 1491 | 5032 | 4942 | 3313 | N | N | N | N | N | N | N |
| PIK3R1 | high in P | 5.5 | 0.002034764 | 2.7 | 119 | 70 | 203 | 128 | 680 | 508 | 408 | N | N | N | N | N | N | N |
| CYB5R2 | high in P | 8.0 | 0.002040935 | 2.7 | 120 | 257 | 291 | 707 | 2627 | 1871 | 2182 | N | N | N | N | N | N | N |
| FBXO27 | high in P | 4.4 | 0.002061506 | 2.7 | 121 | 66 | 49 | 61 | 283 | 164 | 189 | N | N | N | N | N | N | N |
| G10orf90 | high in P | 2.6 | 0.002092361 | 2.7 | 122 | 11 | 10 | 10 | 30 | 24 | 29 | N | N | N | N | N | N | N |
| SLC29A1 | high in P | 3.2 | 0.002131445 | 2.7 | 123 | 392 | 274 | 347 | 1129 | 1020 | 918 | N | N | N | N | N | N | N |
| LRTOMT | high in P | 3.9 | 0.002149959 | 2.7 | 124 | 22 | 16 | 18 | 46 | 48 | 44 | NA | NA | N | N | N | N | N |
| TCHP | high in P | 5.5 | 0.002154613 | 2.7 | 125 | 77 | 63 | 132 | 318 | 395 | 336 | N | N | N | N | N | N | N |
| ADI1 | high in P | 3.0 | 0.002173272 | 2.7 | 126 | 51 | 45 | 52 | 167 | 114 | 126 | N | N | N | N | N | N | N |
| ELTD1 | high in P | 10.7 | 0.002179443 | 2.7 | 127 | 11 | 58 | 27 | 393 | 174 | 164 | N | N | N | N | N | N | N |
| PDE4C | high in P | 3.4 | 0.002198642 | 2.7 | 128 | 25 | 30 | 38 | 84 | 71 | 94 | N | P | N | N | N | N | N |
| UIMC1 | high in P | 3.0 | 0.002204813 | 2.7 | 129 | 52 | 53 | 37 | 109 | 114 | 139 | N | N | N | N | P | N | N |
| IRX1 | high in P | 9.1 | 0.002210985 | 2.7 | 130 | 106 | 123 | 292 | 740 | 831 | 1192 | P | P | N | N | N | N | N |
| ETV7 | high in P | 8.7 | 0.002217156 | 2.7 | 131 | 12 | 25 | 36 | 257 | 172 | 105 | N | N | N | N | N | N | N |
| PSPH | high in P | 9.9 | 0.002235669 | 2.7 | 132 | 6 | 10 | 25 | 112 | 98 | 59 | N | N | N | N | N | N | N |
| GFER | high in P | 3.9 | 0.002248184 | 2.6 | 133 | 70 | 78 | 103 | 362 | 246 | 210 | N | N | N | N | P | N | N |
| KREMEN1 | high in P | 3.7 | 0.002248012 | 2.6 | 134 | 30 | 71 | 76 | 178 | 206 | 160 | N | N | N | N | N | N | N |
| TTC32 | high in P | 4.7 | 0.002265154 | 2.6 | 135 | 53 | 26 | 27 | 157 | 160 | 102 | N | N | N | N | N | N | N |
| NEDD4 | high in P | 3.9 | 0.002280924 | 2.6 | 136 | 17 | 25 | 33 | 72 | 68 | 81 | N | N | N | N | N | N | N |
| CCND2 | high in P | 7.4 | 0.002293267 | 2.6 | 137 | 35 | 49 | 38 | 113 | 101 | 273 | P | P | N | N | N | N | N |
| MESTIT1 | high in P | 5.5 | 0.002313151 | 2.6 | 138 | 62 | 19 | 56 | 241 | 280 | 230 | N | N | N | N | N | N | N |
| TAF11 | high in P | 2.4 | 0.002332351 | 2.6 | 139 | 156 | 184 | 147 | 331 | 316 | 359 | N | N | N | N | N | N | N |
| BRF1 | high in P | 3.5 | 0.002338522 | 2.6 | 140 | 186 | 128 | 177 | 436 | 530 | 537 | N | P | N | N | N | N | N |
| HLA-B | high in P | 2.9 | 0.002348121 | 2.6 | 141 | 13384 | 16928 | 17858 | 43892 | 36932 | 30507 | P | P | N | N | N | N | N |
| RUNX3 | high in P | 2.6 | 0.002381034 | 2.6 | 142 | 85 | 129 | 128 | 259 | 286 | 257 | P | P | N | N | N | N | N |
| FMNL3 | high in P | 7.2 | 0.002393376 | 2.6 | 143 | 39 | 50 | 93 | 261 | 180 | 271 | N | N | N | N | P | N | N |
| DAZAP2 | high in P | 4.2 | 0.002444117 | 2.6 | 144 | 2079 | 1741 | 880 | 8614 | 7088 | 6069 | N | N | N | N | N | N | N |
| C14orf167 | high in P | 4.5 | 0.002479087 | 2.6 | 145 | 27 | 26 | 32 | 101 | 130 | 66 | N | N | N | N | N | N | N |
| IL2RA | high in P | 4.1 | 0.002554512 | 2.6 | 146 | 130 | 164 | 239 | 640 | 563 | 485 | N | P | N | N | N | N | N |
| ST6GALNAC5 | high in P | 3.4 | 0.002559291 | 2.6 | 147 | 14 | 8 | 11 | 27 | 40 | 35 | N | N | N | N | N | N | N |
| SERPINB7 | high in P | 5.5 | 0.002605252 | 2.6 | 148 | 3 | 23 | 10 | 67 | 81 | 59 | N | N | N | N | N | N | N |
| RBM27 | high in P | 2.9 | 0.002611423 | 2.6 | 149 | 49 | 108 | 72 | 241 | 250 | 162 | N | N | N | N | N | N | N |
| KIAA1949 | high in P | 4.0 | 0.002641594 | 2.6 | 150 | 1155 | 1074 | 1666 | 4602 | 3992 | 7057 | P | N | N | N | P | N | N |
| MMP3 | high in P | 9.8 | 0.002675878 | 2.6 | 151 | 20 | 30 | 29 | 327 | 133 | 66 | N | N | N | N | N | N | N |
| RAB34 | high in P | 6.2 | 0.002688906 | 2.6 | 152 | 243 | 406 | 607 | 3242 | 2485 | 1335 | N | N | N | N | N | N | N |
| SFRP4 | high in P | 5.5 | 0.002701248 | 2.6 | 153 | 16 | 18 | 18 | 61 | 29 | 44 | P | N | N | N | N | N | N |
| HIRIP3 | high in P | 4.2 | 0.002731418 | 2.6 | 154 | 2 | 3 | 3 | 13 | 12 | 22 | N | N | N | N | N | N | N |
| C15orf57 | high in P | 4.9 | 0.002737589 | 2.6 | 155 | 26 | 36 | 41 | 148 | 189 | 90 | N | N | N | N | N | N | N |
| AHNAK2 | high in P | 5.3 | 0.002743776 | 2.6 | 156 | 38 | 54 | 85 | 189 | 174 | 211 | N | P | N | N | N | N | N |
| SULT1B1 | high in P | 6.5 | 0.002768445 | 2.6 | 157 | 1 | 1 | 1 | 12 | 17 | 7 | N | N | N | N | N | N | N |
| STEAP1 | high in P | 4.9 | 0.002780787 | 2.6 | 158 | 194 | 231 | 159 | 904 | 872 | 451 | N | N | N | N | N | N | N |
| TSHZ3 | high in P | 2.9 | 0.002817814 | 2.6 | 159 | 23 | 27 | 21 | 42 | 46 | 39 | P | P | N | N | N | N | N |

TABLE 16-continued

Genes that Are Differentially Methylated between Nulliparous and Parous CD24+ Breast Epithelial Cells

| | | | | | SAGE-seq | | | | | | | | | ChIP-seq | | | | MSDK-seq | | |
|---|---|---|---|---|---|---|---|---|---|---|---|---|---|---|---|---|---|---|---|---|
| | | | | | | Nulliparous (NP) | | | | Parous (P) | | | | | | | | | | |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | NP | CD24+ N74 | CD24+ N66 | NP | GeneBody | GeneBody Met | P | Pro-moter Met | NP | Pro-moter Met | P |
| UPF3B | high in P | 3.6 | 0.000830156 | 2.5 | 160 | 98 | 60 | 61 | 202 | 186 | 211 | | NA | P | | N | N | N | N | N | N |
| C17orf103 | high in P | 5.9 | 0.002841127 | 2.5 | 161 | 60 | 67 | 61 | 472 | 271 | 152 | | NA | NA | | N | N | N | N | N | N |
| SS18L2 | high in P | 6.4 | 0.002863069 | 2.5 | 162 | 616 | 207 | 359 | 2156 | 2955 | 1519 | | N | N | | N | N | N | N | N | N |
| C1R | high in P | 4.5 | 0.0028692 | 2.5 | 163 | 168 | 351 | 202 | 1261 | 756 | 643 | | N | P | | N | N | N | N | N | N |
| CNRIP1 | high in P | 5.7 | 0.002875411 | 2.5 | 164 | 5 | 11 | 7 | 48 | 36 | 29 | | P | P | | N | N | N | N | N | N |
| BTG3 | high in P | 3.7 | 0.002887754 | 2.5 | 165 | 28 | 55 | 47 | 157 | 110 | 109 | | NA | NA | | N | N | N | N | N | N |
| IDO1 | high in P | 12.3 | 0.002927523 | 2.5 | 166 | 3 | 26 | 11 | 71 | 102 | 299 | | N | N | | N | N | N | N | N | N |
| SHROOM2 | high in P | 3.4 | 0.003006377 | 2.5 | 167 | 34 | 42 | 30 | 169 | 102 | 84 | | N | N | | N | N | N | N | N | N |
| LOC283174 | high in P | 5.8 | 0.003027633 | 2.5 | 168 | 12 | 13 | 13 | 28 | 55 | 59 | | N | N | | N | N | N | N | N | N |
| KLF15 | high in P | 3.7 | 0.003055746 | 2.5 | 169 | 8 | 10 | 8 | 15 | 19 | 21 | | N | N | | N | N | N | N | N | N |
| C9orf123 | high in P | 2.3 | 0.003077002 | 2.5 | 170 | 133 | 166 | 115 | 279 | 313 | 278 | | N | N | | N | N | N | N | N | N |
| C2orf15 | high in P | 2.9 | 0.003143513 | 2.5 | 171 | 246 | 193 | 227 | 630 | 597 | 491 | | N | N | | N | N | N | N | N | N |
| ATP8B2 | high in P | 6.7 | 0.003149685 | 2.5 | 172 | 27 | 53 | 29 | 107 | 89 | 174 | | N | N | | N | N | N | N | N | N |
| PDPN | high in P | 4.2 | 0.003186711 | 2.5 | 173 | 10 | 13 | 10 | 28 | 20 | 31 | | P | P | | N | N | N | N | N | N |
| HAX1 | high in P | 3.9 | 0.003192883 | 2.5 | 174 | 651 | 442 | 582 | 2015 | 2954 | 1440 | | N | N | | N | N | N | N | N | N |
| BCL2L11 | high in P | 3.9 | 0.003214139 | 2.5 | 175 | 309 | 310 | 381 | 2689 | 1141 | 967 | | N | N | | N | N | N | N | N | N |
| CD93 | high in P | 6.5 | 0.003223738 | 2.5 | 176 | 19 | 43 | 29 | 325 | 102 | 94 | | P | P | | N | N | N | N | N | N |
| PIP4K2B | high in P | 2.7 | 0.003229992 | 2.5 | 177 | 32 | 39 | 35 | 79 | 59 | 76 | | N | N | | N | N | N | N | N | N |
| TMOD1 | high in P | 7.0 | 0.003305335 | 2.5 | 178 | 18 | 33 | 45 | 116 | 307 | 105 | | P | P | | N | N | N | N | N | N |
| UBFD1 | high in P | 2.9 | 0.003311506 | 2.5 | 179 | 85 | 75 | 96 | 252 | 217 | 188 | | N | N | | N | N | N | N | N | N |
| PRRG1 | high in P | 2.8 | 0.003376646 | 2.5 | 180 | 55 | 68 | 82 | 153 | 140 | 156 | | N | N | | N | N | N | N | N | N |
| HSPA12B | high in P | 27.6 | 0.003395845 | 2.5 | 181 | 9 | 9 | 20 | 102 | 86 | 45 | | N | N | | N | N | N | N | N | N |
| FOXF2 | high in P | 10.6 | 0.003408187 | 2.5 | 182 | 6 | 7 | 6 | 54 | 14 | 34 | | N | P | | N | N | N | P | N | N |
| IFITM3 | high in P | 4.0 | 0.003428758 | 2.5 | 183 | 254 | 400 | 456 | 1751 | 1303 | 886 | | N | P | | N | N | N | N | N | N |
| NDUFV3 | high in P | 5.5 | 0.0034411 | 2.5 | 184 | 314 | 173 | 285 | 1581 | 1627 | 685 | | N | N | | P | N | N | N | N | N |
| GZF1 | high in P | 5.6 | 0.003447271 | 2.5 | 185 | 38 | 50 | 89 | 169 | 212 | 220 | | P | P | | N | N | N | N | N | N |
| ZNF3970S | high in P | 3.0 | 0.003459613 | 2.5 | 186 | 50 | 42 | 34 | 128 | 112 | 88 | | N | P | | N | N | N | N | N | N |
| CXorf15 | high in P | 5.1 | 0.003500754 | 2.5 | 187 | NA | NA | NA | NA | NA | NA | | P | P | | N | N | N | N | N | N |
| FAM110A | high in P | 3.1 | 0.00352201 | 2.5 | 188 | 87 | 141 | 93 | 241 | 258 | 290 | | N | N | | N | N | N | N | N | N |
| SMYD4 | high in P | 2.6 | 0.003528182 | 2.5 | 189 | 74 | 77 | 92 | 179 | 165 | 203 | | N | N | | N | N | N | N | N | N |
| C1orf51 | high in P | 6.8 | 0.003546009 | 2.5 | 190 | 77 | 24 | 109 | 580 | 331 | 447 | | N | N | | N | N | N | N | N | N |
| POU3F1 | high in P | 3.8 | 0.00356658 | 2.5 | 191 | 20 | 13 | 17 | 31 | 35 | 48 | | P | P | | N | N | N | N | N | N |
| SPARC | high in P | 3.8 | 0.003572751 | 2.4 | 192 | 36 | 43 | 37 | 141 | 74 | 92 | | N | N | | N | N | N | N | N | N |
| DNAJC6 | high in P | 5.3 | 0.003578922 | 2.4 | 193 | 18 | 24 | 17 | 98 | 41 | 73 | | N | N | | N | N | N | N | N | N |
| USH1G | high in P | 3.8 | 0.003591264 | 2.4 | 194 | 17 | 27 | 38 | 72 | 90 | 96 | | N | N | | N | N | N | N | N | N |
| LHFP | high in P | 6.5 | 0.003624863 | 2.4 | 195 | 14 | 12 | 11 | 42 | 26 | 99 | | N | N | | N | N | N | N | N | N |
| ITCH | high in P | 3.2 | 0.003631034 | 2.4 | 196 | 54 | 45 | 53 | 122 | 132 | 122 | | N | N | | N | N | N | N | N | N |
| GLG1 | high in P | 3.8 | 0.003637205 | 2.4 | 197 | 485 | 430 | 578 | 1680 | 1304 | 1024 | | N | N | | N | N | N | N | N | N |
| SMC4 | high in P | 2.5 | 0.003652976 | 2.4 | 198 | 23 | 31 | 24 | 49 | 53 | 67 | | N | N | | N | N | N | N | N | N |
| ASAP3 | high in P | 5.7 | 0.003659147 | 2.4 | 199 | 18 | 15 | 16 | 112 | 40 | 65 | | N | N | | N | N | N | N | N | N |
| CWF19L1 | high in P | 5.1 | 0.003665318 | 2.4 | 200 | 17 | 22 | 29 | 87 | 132 | 53 | | N | N | | N | N | N | N | N | N |
| KRTAP3-2 | high in P | 5.8 | 0.003703716 | 2.4 | 201 | 1 | 1 | 1 | 8 | 8 | 4 | | N | N | | N | N | N | N | N | N |
| RGMA | high in P | 2.8 | 0.003740058 | 2.4 | 202 | 96 | 136 | 88 | 265 | 302 | 203 | | N | N | | N | N | N | N | N | N |
| EPR1 | high in P | 20.6 | 0.003770913 | 2.4 | 203 | 11 | 2 | 30 | 87 | 160 | 183 | | N | N | | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | | | MSDK-seq | | |
|---|---|---|---|---|---|---|---|---|---|---|---|---|---|---|---|---|---|---|---|
| | | | | | | Nulliparous (NP) | | | | Parous (P) | | | | | | | | | |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | NP | CD24+ N74 | CD24+ N66 | NP | GeneBody | GeneBody Met | P | Pro-moter Met | P |
| KLHL7 | high in P | 2.7 | 0.003857309 | 2.4 | 204 | 21 | 31 | 27 | 49 | 65 | 63 | N | N | N | N | N | N | N | N | N |
| INPP5K | high in P | 2.9 | 0.003875823 | 2.4 | 205 | 47 | 105 | 75 | 222 | 192 | 159 | N | N | N | N | N | N | N | N | N |
| ST6GALNAC4 | high in P | 6.2 | 0.003881994 | 2.4 | 206 | 85 | 110 | 187 | 972 | 634 | 332 | N | N | N | N | N | N | N | N | N |
| PARD6G | high in P | 2.3 | 0.003894336 | 2.4 | 207 | 31 | 36 | 36 | 60 | 68 | 74 | N | N | N | N | N | N | N | N | N |
| ZNF33A | high in P | 3.8 | 0.003932049 | 2.4 | 208 | 124 | 135 | 107 | 401 | 554 | 242 | N | N | N | N | N | N | N | N | N |
| OR7E91P | high in P | 2.8 | 0.003393822 | 2.4 | 209 | 10 | 6 | 7 | 17 | 28 | 25 | N | N | N | N | N | N | N | N | N |
| DDR2 | high in P | 5.2 | 0.003978675 | 2.4 | 210 | 29 | 16 | 21 | 142 | 87 | 51 | N | N | N | N | N | N | N | N | N |
| NME2P1 | high in P | 4.7 | 0.004034901 | 2.4 | 211 | 14 | 5 | 6 | 55 | 44 | 23 | N | N | N | N | N | N | N | N | N |
| OSTF1 | high in P | 3.6 | 0.004053415 | 2.4 | 212 | 157 | 268 | 223 | 1033 | 712 | 487 | N | N | N | N | N | N | N | P | N |
| UBE2Q1 | high in P | 3.3 | 0.004079471 | 2.4 | 213 | 65 | 124 | 101 | 290 | 351 | 197 | N | N | N | N | N | N | N | N | N |
| DBF4B | high in P | 2.7 | 0.004085642 | 2.4 | 214 | 580 | 408 | 479 | 1315 | 1108 | 1229 | N | N | N | N | N | N | N | N | N |
| ARHGEF5L | high in P | 3.7 | 0.004137068 | 2.4 | 215 | NA | NA | NA | NA | NA | NA | NA | NA | NA | N | N | N | N | N | N |
| ACSL4 | high in P | 4.6 | 0.004152153 | 2.4 | 216 | 52 | 28 | 36 | 132 | 131 | 97 | N | N | N | N | N | N | N | N | N |
| KLHL26 | high in P | 3.6 | 0.004171352 | 2.4 | 217 | 9 | 11 | 13 | 47 | 25 | 27 | N | N | N | N | N | N | N | N | N |
| TSEN54 | high in P | 3.2 | 0.004177523 | 2.4 | 218 | 83 | 141 | 141 | 360 | 400 | 258 | N | N | N | N | N | N | N | N | N |
| PARP10 | high in P | 4.8 | 0.004196037 | 2.4 | 219 | 227 | 106 | 314 | 967 | 966 | 833 | N | N | N | N | N | N | N | N | N |
| MYO10 | high in P | 2.2 | 0.004268033 | 2.4 | 220 | 311 | 349 | 327 | 710 | 700 | 619 | N | N | N | N | N | N | N | N | N |
| ODAM | high in P | 4.5 | 0.004280376 | 2.4 | 221 | 2 | 2 | 2 | 22 | 7 | 13 | N | N | N | N | N | N | N | N | N |
| CD58 | high in P | 2.8 | 0.004292718 | 2.4 | 222 | 33 | 26 | 26 | 70 | 63 | 77 | N | N | N | N | N | N | N | N | N |
| INTS12 | high in P | 4.4 | 0.004320145 | 2.4 | 223 | 120 | 99 | 218 | 450 | 510 | 465 | N | N | N | N | N | N | N | N | N |
| FBLN5 | high in P | 10.0 | 0.004364715 | 2.4 | 224 | 239 | 673 | 126 | 2555 | 1311 | 2097 | N | N | N | N | N | N | N | N | N |
| TMEM106A | high in P | 3.0 | 0.004370886 | 2.4 | 225 | 30 | 34 | 47 | 91 | 96 | 87 | N | N | N | N | N | N | N | N | N |
| OPLAH | high in P | 4.4 | 0.004392828 | 2.4 | 226 | 204 | 129 | 338 | 785 | 864 | 811 | N | N | N | N | N | N | N | N | N |
| ANKRD45 | high in P | 3.6 | 0.004418884 | 2.4 | 227 | 11 | 14 | 17 | 43 | 46 | 33 | N | N | N | N | N | N | N | N | N |
| SHE | high in P | 2.6 | 0.004449054 | 2.4 | 228 | 31 | 36 | 43 | 80 | 75 | 70 | P | P | N | N | N | N | N | N | N |
| ERAL1 | high in P | 3.9 | 0.004461396 | 2.4 | 229 | 77 | 171 | 84 | 419 | 317 | 262 | P | P | N | N | N | N | N | N | N |
| PLCB3 | high in P | 3.4 | 0.004509394 | 2.3 | 230 | 13 | 28 | 16 | 73 | 51 | 43 | N | N | N | N | N | N | N | N | N |
| DNER | high in P | 9.3 | 0.004521736 | 2.3 | 231 | 2 | 9 | 34 | 78 | 110 | 241 | P | P | N | N | N | N | N | N | N |
| LCC401127 | high in P | 3.0 | 0.004527907 | 2.3 | 232 | 21 | 25 | 28 | 78 | 65 | 51 | NA | NA | NA | N | N | N | N | N | N |
| EGFLAM | high in P | 3.5 | 0.004620474 | 2.3 | 233 | 24 | 18 | 18 | 43 | 45 | 35 | P | P | P | N | N | N | N | N | N |
| GRID1 | high in P | 12.5 | 0.004666415 | 2.3 | 234 | 12 | 12 | 12 | 52 | 42 | 18 | P | P | P | N | N | N | N | N | N |
| TRIM5 | high in P | 2.6 | 0.004685614 | 2.3 | 235 | 62 | 52 | 40 | 129 | 111 | 115 | N | N | N | N | N | N | N | N | N |
| DGKE | high in P | 2.5 | 0.004753612 | 2.3 | 236 | 139 | 138 | 191 | 337 | 361 | 328 | N | N | N | N | N | N | N | N | N |
| STEAP3 | high in P | 8.4 | 0.004739783 | 2.3 | 237 | 62 | 75 | 246 | 706 | 693 | 439 | N | N | N | N | N | N | N | N | N |
| HOXC8 | high in P | 6.0 | 0.004772696 | 2.3 | 238 | 9 | 22 | 31 | 98 | 58 | 93 | P | P | P | N | N | N | N | N | N |
| ADAMTS5 | high in P | 3.9 | 0.004788467 | 2.3 | 239 | 37 | 37 | 37 | 61 | 47 | 66 | N | N | N | N | N | N | N | N | N |
| EYA2 | high in P | 3.6 | 0.004809723 | 2.3 | 240 | 208 | 118 | 261 | 765 | 664 | 549 | P | P | P | N | N | N | N | N | N |
| PRPSAP2 | high in P | 3.4 | 0.004850864 | 2.3 | 241 | 125 | 152 | 188 | 760 | 384 | 405 | N | N | N | N | N | N | N | N | N |
| CYGB | high in P | 4.9 | 0.004873491 | 2.3 | 242 | 24 | 22 | 36 | 185 | 89 | 69 | N | N | N | N | N | N | N | N | N |
| PDGFRB | high in P | 9.8 | 0.004907090 | 2.3 | 243 | 28 | 31 | 39 | 192 | 68 | 68 | N | N | N | N | N | N | N | N | N |
| SV2A | high in P | 3.7 | 0.004919432 | 2.3 | 244 | 16 | 19 | 24 | 48 | 35 | 64 | N | N | N | N | N | N | N | N | N |
| C21orf91 | high in P | 7.0 | 0.004958516 | 2.3 | 245 | 34 | 154 | 50 | 315 | 313 | 400 | N | N | N | N | N | N | N | N | N |
| PLIN2 | high in P | 4.6 | 0.004992115 | 2.3 | 246 | 57 | 127 | 107 | 526 | 326 | 218 | NA | NA | NA | N | N | N | N | N | N |
| SLC39A13 | high in P | 2.9 | 0.004998286 | 2.3 | 247 | 300 | 515 | 688 | 1366 | 1609 | 1361 | N | N | N | N | N | N | N | N | N |

TABLE 16-continued

Genes that Are Differentially Methylated between Nulliparous and Parous CD24+ Breast Epithelial Cells

| | | | | SAGE-seq | | | | | | | ChIP-seq | | | MSDK-seq | | |
|---|---|---|---|---|---|---|---|---|---|---|---|---|---|---|---|---|
| | | | | | Nulliparous (NP) | | | Parous (P) | | | NP | | | GeneBody Met | Pro-moter Met | Pro-moter Met |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | CD24+ N74 | CD24+ N66 | GeneBody | | |
| YIPF4 | high in P | 2.5 | 0.005004457 | 2.3 | 248 | 88 | 106 | 52 | 182 | 210 | 199 | N | N | NP | P | P |
| PDE7B | high in P | 2.6 | 0.005022297 | 2.3 | 249 | 14 | 21 | 17 | 27 | 32 | 30 | N | N | N | N | N |
| CD40 | high in P | 5.9 | 0.005029142 | 2.3 | 250 | 27 | 56 | 25 | 280 | 135 | 91 | N | N | N | N | N |
| SETD8 | high in P | 6.4 | 0.005041484 | 2.3 | 251 | 433 | 353 | 1135 | 2298 | 2660 | 2636 | N | N | N | N | N |
| BCAN | high in P | 4.4 | 0.005053826 | 2.3 | 252 | 52 | 27 | 77 | 215 | 158 | 191 | N | N | N | N | N |
| TMEM204 | high in P | 11.3 | 0.005010251 | 2.3 | 253 | 10 | 11 | 32 | 156 | 90 | 67 | N | N | N | N | N |
| RAB6C | high in P | 4.0 | 0.005114166 | 2.3 | 254 | 1 | 1 | 1 | 5 | 6 | 12 | N | N | N | N | N |
| PIGP | high in P | 3.4 | 0.005129251 | 2.3 | 255 | 93 | 65 | 101 | 317 | 217 | 195 | N | N | N | N | N |
| SHC1 | high in P | 3.0 | 0.005179992 | 2.3 | 256 | 54 | 108 | 71 | 218 | 173 | 149 | N | N | N | N | N |
| FABP5 | high in P | 7.3 | 0.005186163 | 2.3 | 257 | 2 | 5 | 14 | 50 | 41 | 33 | P | N | N | N | N |
| GOLGB1 | high in P | 2.5 | 0.005208105 | 2.3 | 258 | 243 | 272 | 223 | 621 | 468 | 572 | N | N | N | N | N |
| MMP12 | high in P | 7.8 | 0.005256103 | 2.3 | 259 | 8 | 27 | 18 | 152 | 87 | 70 | N | N | N | N | N |
| HUNK | high in P | 3.1 | 0.005282159 | 2.3 | 260 | 17 | 20 | 23 | 32 | 34 | 35 | N | N | N | N | N |
| CFP | high in P | 3.9 | 0.005228833 | 2.3 | 261 | 11 | 12 | 19 | 45 | 40 | 45 | N | N | N | N | N |
| CCNC | high in P | 2.7 | 0.005439866 | 2.3 | 262 | 62 | 61 | 61 | 159 | 140 | 100 | N | N | N | N | N |
| SGK196 | high in P | 2.9 | 0.005446037 | 2.3 | 263 | 4 | 4 | 4 | 8 | 10 | 10 | N | N | N | N | N |
| INHBA | high in P | 7.6 | 0.005500891 | 2.3 | 264 | 9 | 62 | 23 | 147 | 168 | 112 | P | P | N | N | N |
| C17orf63 | high in P | 3.2 | 0.005513234 | 2.3 | 265 | 390 | 227 | 302 | 785 | 827 | 824 | N | N | N | N | N |
| CHST9 | high in P | 3.4 | 0.005537918 | 2.3 | 266 | 17 | 13 | 20 | 45 | 39 | 44 | P | N | N | N | N |
| LCLAT1 | high in P | 3.9 | 0.005566031 | 2.3 | 267 | 52 | 122 | 78 | 363 | 234 | 184 | NA | NA | N | N | N |
| ADRB3 | high in P | 6.0 | 0.005613343 | 2.3 | 268 | 31 | 54 | 38 | 246 | 215 | 87 | NA | P | N | N | N |
| PSMB2 | high in P | 4.4 | 0.005666477 | 2.3 | 269 | 565 | 798 | 1053 | 4756 | 4023 | 1681 | P | N | N | N | N |
| KIAA0562 | high in P | 5.6 | 0.005677798 | 2.2 | 270 | 81 | 159 | 313 | 816 | 609 | 619 | N | P | N | N | N |
| LOC440944 | high in P | 3.6 | 0.005683969 | 2.2 | 271 | 112 | 72 | 113 | 243 | 236 | 352 | NA | N | N | N | N |
| FAM126A | high in P | 2.8 | 0.005696311 | 2.2 | 272 | 34 | 39 | 37 | 45 | 54 | 60 | NA | N | N | N | N |
| ESRP2 | high in P | 2.3 | 0.005734709 | 2.2 | 273 | 90 | 132 | 116 | 198 | 262 | 225 | NA | N | N | N | N |
| ATMIN | high in P | 2.7 | 0.005787507 | 2.2 | 274 | 66 | 132 | 94 | 276 | 222 | 183 | N | N | N | N | N |
| PPP1R3F | high in P | 8.1 | 0.005793678 | 2.2 | 275 | 10 | 21 | 50 | 146 | 111 | 96 | P | P | N | N | N |
| FADS6 | high in P | 4.3 | 0.005808763 | 2.2 | 276 | 5 | 7 | 7 | 16 | 27 | 18 | P | N | N | N | N |
| COPS7B | high in P | 3.5 | 0.005814934 | 2.2 | 277 | 35 | 15 | 18 | 79 | 60 | 62 | N | N | N | N | N |
| QRSL1 | high in P | 5.8 | 0.005821105 | 2.2 | 278 | 244 | 129 | 420 | 1330 | 1293 | 802 | N | N | N | N | N |
| CIB2 | high in P | 5.6 | 0.005827276 | 2.2 | 279 | 87 | 27 | 109 | 512 | 406 | 237 | N | N | N | N | N |
| C1orf74 | high in P | 3.5 | 0.005842361 | 2.2 | 280 | 5 | 7 | 5 | 11 | 22 | 18 | N | N | N | N | N |
| WFDC5 | high in P | 16.8 | 0.005854704 | 2.2 | 281 | 1 | 5 | 31 | 96 | 235 | 94 | N | N | N | N | N |
| FAM115A | high in P | 3.0 | 0.005888076 | 2.2 | 282 | 298 | 154 | 279 | 754 | 741 | 647 | N | P | N | N | N |
| STK25 | high in P | 2.1 | 0.005895845 | 2.2 | 283 | 92 | 135 | 125 | 201 | 231 | 224 | N | N | N | N | N |
| USP40 | high in P | 3.4 | 0.005928072 | 2.2 | 284 | 96 | 175 | 191 | 594 | 470 | 296 | N | N | N | N | N |
| TMLHE | high in P | 3.5 | 0.005960299 | 2.2 | 285 | 21 | 20 | 40 | 80 | 91 | 70 | N | N | N | N | N |
| CDKN2A | high in P | 3.9 | 0.005996647 | 2.2 | 286 | 41 | 45 | 32 | 129 | 157 | 69 | P | N | N | N | N |
| OSGIN2 | high in P | 3.7 | 0.005977441 | 2.2 | 287 | 22 | 24 | 21 | 85 | 86 | 38 | N | N | N | N | N |
| FGFR2 | high in P | 3.4 | 0.006028867 | 2.2 | 288 | 176 | 102 | 128 | 330 | 369 | 492 | N | N | N | N | N |
| TXN | high in P | 3.1 | 0.006058352 | 2.2 | 289 | 20 | 10 | 12 | 29 | 35 | 33 | N | N | N | N | N |
| MAP3K4 | high in P | 2.5 | 0.006010155 | 2.2 | 290 | 42 | 47 | 44 | 91 | 75 | 110 | N | N | N | N | N |
| SIRPB2 | high in P | 4.1 | 0.006107721 | 2.2 | 291 | 57 | 26 | 89 | 262 | 207 | 200 | N | N | N | N | N |

TABLE 16-continued

Genes that Are Differentially Methylated between Nulliparous and Parous CD24+ Breast Epithelial Cells

| | | | | | | SAGE-seq | | | | | | ChIP-seq | | | | MSDK-seq | | |
|---|---|---|---|---|---|---|---|---|---|---|---|---|---|---|---|---|---|---|
| | | | | | | Nulliparous (NP) | | | Parous (P) | | | NP | P | | NP | | P | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | GeneBody Met | Pro-moter Met | Pro-moter Met |
| NFE2L1 | high in P | 5.2 | 0.006113892 | 2.2 | 292 | 646 | 895 | 1046 | 6677 | 4367 | 1782 | N | N | N | N | N | N |
| GPATCH2 | high in P | 3.9 | 0.006123491 | 2.2 | 293 | 154 | 86 | 85 | 248 | 404 | 350 | N | N | N | N | N | N |
| LOC349196 | high in P | 2.4 | 0.006142691 | 2.2 | 294 | 40 | 48 | 44 | 95 | 73 | 99 | NA | NA | N | N | N | N |
| MAST3 | high in P | 3.1 | 0.006249657 | 2.2 | 295 | 25 | 39 | 36 | 182 | 85 | 76 | N | N | N | N | N | N |
| ZEB2 | high in P | 8.8 | 0.006255828 | 2.2 | 296 | 21 | 21 | 22 | 62 | 55 | 27 | P | P | N | N | N | N |
| DRAM1 | high in P | 4.7 | 0.006303114 | 2.2 | 297 | 38 | 65 | 28 | 230 | 127 | 98 | NA | NA | N | N | N | N |
| CTPS | high in P | 3.8 | 0.006329196 | 2.2 | 298 | 149 | 314 | 169 | 533 | 611 | 553 | N | NA | N | N | N | N |
| LOC84740 | high in P | 4.3 | 0.006340167 | 2.2 | 299 | 7 | 7 | 7 | 18 | 22 | 40 | NA | NA | N | N | N | N |
| WDR27 | high in P | 3.8 | 0.006353195 | 2.2 | 300 | 17 | 17 | 29 | 98 | 50 | 74 | N | N | N | N | N | N |
| C13orf34 | high in P | 3.6 | 0.006391594 | 2.2 | 301 | 5 | 15 | 9 | 39 | 29 | 29 | N | N | N | N | P | N |
| ALKBH4 | high in P | 4.6 | 0.006397765 | 2.2 | 302 | 610 | 275 | 294 | 1588 | 1277 | 1025 | N | N | N | N | N | N |
| C11orf57 | high in P | 2.6 | 0.006419707 | 2.2 | 303 | 41 | 63 | 32 | 110 | 108 | 88 | N | N | N | N | N | N |
| IKZF2 | high in P | 3.8 | 0.006425878 | 2.2 | 304 | 31 | 41 | 24 | 72 | 81 | 56 | N | N | N | N | N | N |
| ERMP1 | high in P | 10.9 | 0.006432049 | 2.2 | 305 | 35 | 42 | 75 | 704 | 376 | 110 | N | N | N | N | N | N |
| CH25H | high in P | 4.2 | 0.006497874 | 2.2 | 306 | 3 | 3 | 5 | 9 | 13 | 22 | N | N | N | N | N | N |
| CCL4 | high in P | 7.1 | 0.006514331 | 2.2 | 307 | 2 | 10 | 2 | 24 | 21 | 50 | N | N | N | N | N | N |
| RPS11 | high in P | 5.1 | 0.006520502 | 2.2 | 308 | 43897 | 16111 | 19270 | 103882 | 103882 | 64055 | N | N | N | N | N | N |
| DNAJC8 | high in P | 2.6 | 0.006526673 | 2.2 | 309 | 366 | 338 | 508 | 899 | 951 | 912 | N | N | N | N | N | N |
| SSBP3 | high in P | 3.5 | 0.006533833 | 2.2 | 310 | 26 | 21 | 26 | 50 | 58 | 81 | N | N | N | N | N | N |
| C17orf77 | high in P | 3.4 | 0.006579471 | 2.2 | 311 | 5 | 6 | 7 | 18 | 16 | 43 | N | N | N | N | N | N |
| POLL | high in P | 2.8 | 0.006585642 | 2.2 | 312 | 134 | 88 | 105 | 261 | 243 | 277 | N | N | N | N | N | N |
| RAB4A | high in P | 3.1 | 0.006597984 | 2.2 | 313 | 196 | 132 | 115 | 316 | 376 | 419 | P | N | N | N | N | N |
| CEBPB | high in P | 2.5 | 0.006604155 | 2.2 | 314 | 6405 | 8486 | 5876 | 12334 | 14427 | 20157 | N | N | N | N | N | N |
| C2orf60 | high in P | 2.6 | 0.006625411 | 2.2 | 315 | 32 | 50 | 57 | 127 | 118 | 79 | N | N | N | N | N | N |
| FOXC2 | high in P | 5.4 | 0.006666381 | 2.2 | 316 | 4 | 15 | 28 | 73 | 131 | 69 | N | P | N | N | N | N |
| GBGT1 | high in P | 2.6 | 0.006669981 | 2.2 | 317 | 25 | 19 | 21 | 59 | 59 | 40 | N | N | N | N | N | N |
| NASP | high in P | 2.9 | 0.006700151 | 2.2 | 318 | 389 | 213 | 293 | 749 | 759 | 863 | N | P | N | N | N | N |
| DDHD2 | high in P | 2.5 | 0.006706322 | 2.2 | 319 | 39 | 48 | 52 | 101 | 114 | 75 | P | P | N | N | N | N |
| TBX2 | high in P | 8.8 | 0.006717293 | 2.2 | 320 | 20 | 29 | 12 | 158 | 48 | 70 | N | P | N | N | N | N |
| UBQLNL | high in P | 4.2 | 0.006723464 | 2.2 | 321 | 2 | 2 | 2 | 7 | 13 | 7 | N | N | N | N | N | N |
| TBC1D10A | high in P | 2.8 | 0.006779635 | 2.2 | 322 | 34 | 24 | 20 | 65 | 60 | 52 | N | N | N | N | N | N |
| AIP | high in P | 3.3 | 0.006785176 | 2.2 | 323 | 6 | 18 | 15 | 42 | 51 | 30 | N | P | N | N | N | N |
| CD34 | high in P | 5.7 | 0.006807117 | 2.2 | 324 | 15 | 19 | 23 | 191 | 74 | 43 | P | P | N | N | N | N |
| DENND1A | high in P | 4.7 | 0.006846887 | 2.2 | 325 | 25 | 94 | 147 | 570 | 511 | 228 | N | P | N | N | N | N |
| FAM3C | high in P | 2.5 | 0.006896256 | 2.2 | 326 | 120 | 47 | 49 | 84 | 107 | 101 | N | N | N | N | N | N |
| UNC45A | high in P | 2.2 | 0.006902427 | 2.2 | 327 | 22 | 353 | 368 | 750 | 607 | 633 | N | N | N | N | N | N |
| ADC | high in P | 8.2 | 0.006923683 | 2.2 | 328 | 238 | 45 | 114 | 206 | 265 | 427 | N | N | N | N | N | N |
| CSF1 | high in P | 2.8 | 0.006938769 | 2.2 | 329 | 22 | 40 | 42 | 122 | 106 | 95 | N | N | N | N | N | N |
| LSM11 | high in P | 2.7 | 0.006954539 | 2.2 | 330 | 49 | 3 | 4 | 9 | 13 | 9 | N | N | N | N | N | N |
| ABHD3 | high in P | 4.0 | 0.006976481 | 2.2 | 331 | 3 | 4 | 4 | 9 | 9 | 28 | N | N | N | N | N | N |
| LOC100170939 | high in P | 2.9 | 0.006982652 | 2.2 | 332 | 6 | 6 | 12 | 33 | 27 | 41 | N | N | N | N | N | N |
| NSL1 | high in P | 2.4 | 0.007001851 | 2.2 | 333 | 10 | 6 | 11 | 29 | 22 | 75 | N | N | N | N | N | N |
| RABL3 | high in P | 5.5 | 0.007029279 | 2.2 | 334 | 43 | 54 | 50 | 73 | 98 | 411 | N | N | N | N | N | N |
| SULT2B1 | high in P | 4.0 | 0.00703545 | 2.2 | 335 | 87 | 124 | 276 | 761 | 932 | 174 | N | N | N | N | N | N |

TABLE 16-continued

Genes that Are Differentially Methylated between Nulliparous and Parous CD24+ Breast Epithelial Cells

| | | | | | SAGE-seq | Nulliparous (NP) | | | | Parous (P) | | | | ChIP-seq | | | MSDK-seq | | |
|---|---|---|---|---|---|---|---|---|---|---|---|---|---|---|---|---|---|---|---|
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | CD24+ N74 | CD24+ N66 | NP | P | GeneBody NP | GeneBody Met P | Pro-moter Met NP | Pro-moter Met P |
| HSPA1L | high in P | 5.0 | 0.007047106 | 2.2 | 336 | 9 | 5 | 12 | 28 | 24 | 51 | N | N | N | N | N | N | N | N |
| LZTS1 | high in P | 3.3 | 0.007062877 | 2.2 | 337 | 23 | 18 | 25 | 37 | 46 | 59 | P | N | N | N | N | N | P | N |
| ZNF331 | high in P | 3.0 | 0.007069048 | 2.2 | 338 | 48 | 33 | 40 | 102 | 77 | 122 | N | N | N | N | N | N | N | N |
| NUFIP1 | high in P | 2.1 | 0.007075219 | 2.2 | 339 | 37 | 42 | 33 | 72 | 89 | 71 | N | N | N | N | N | N | N | N |
| KCNH8 | high in P | 2.9 | 0.007141731 | 2.1 | 340 | 18 | 23 | 17 | 28 | 42 | 45 | N | N | N | N | N | N | N | N |
| NRG1 | high in P | 5.4 | 0.007166415 | 2.1 | 341 | 28 | 51 | 66 | 89 | 183 | 231 | P | N | N | N | N | N | N | P |
| DDX51 | high in P | 3.9 | 0.007224184 | 2.1 | 342 | 118 | 92 | 234 | 409 | 530 | 427 | P | P | N | N | N | N | N | N |
| MSC | high in P | 11.3 | 0.007248012 | 2.1 | 343 | 6 | 7 | 9 | 77 | 24 | 22 | N | N | N | N | N | N | N | N |
| TAF3 | high in P | 4.3 | 0.007306295 | 2.1 | 344 | 22 | 81 | 63 | 254 | 150 | 190 | N | P | N | N | N | N | N | N |
| C11orf52 | high in P | 2.5 | 0.007370063 | 2.1 | 345 | 53 | 57 | 44 | 191 | 98 | 118 | N | N | N | N | N | N | N | N |
| PLVAP | high in P | 4.8 | 0.007388577 | 2.1 | 346 | 17 | 21 | 23 | 89 | 49 | 33 | N | N | N | N | N | N | N | N |
| RSAD1 | high in P | 2.4 | 0.007448231 | 2.1 | 347 | 9 | 14 | 10 | 20 | 26 | 20 | N | N | N | N | N | N | N | N |
| RUNDC2C | high in P | 3.2 | 0.007507885 | 2.1 | 348 | 23 | 25 | 30 | 47 | 68 | 49 | N | N | N | N | N | N | N | N |
| DEXI | high in P | 9.2 | 0.007524342 | 2.1 | 349 | 279 | 469 | 1501 | 3839 | 4137 | 2691 | N | N | N | N | N | N | N | N |
| LOC93432 | high in P | 5.6 | 0.007596338 | 2.1 | 350 | 2 | 8 | 3 | 48 | 25 | 17 | N | N | N | N | N | N | N | N |
| NFXL1 | high in P | 2.5 | 0.00760251 | 2.1 | 351 | 19 | 22 | 13 | 38 | 41 | 34 | N | N | N | N | N | N | N | N |
| NOLC1 | high in P | 2.8 | 0.007524342 | 2.1 | 352 | 69 | 73 | 67 | 108 | 167 | 169 | N | N | N | N | N | N | N | N |
| CBX7 | high in P | 2.5 | 0.00772319 | 2.1 | 353 | 44 | 65 | 44 | 162 | 101 | 99 | N | N | N | N | N | N | N | N |
| POM121 | high in P | 2.6 | 0.007729361 | 2.1 | 354 | 30 | 24 | 29 | 60 | 87 | 51 | N | N | N | N | N | N | N | N |
| NFYA | high in P | 2.4 | 0.007762959 | 2.1 | 355 | 303 | 264 | 399 | 614 | 679 | 798 | N | N | N | N | N | N | N | N |
| LOC440896 | high in P | 3.5 | 0.007814386 | 2.1 | 356 | 33 | 15 | 24 | 48 | 82 | 94 | N | N | N | N | N | N | N | N |
| ZNF619 | high in P | 4.5 | 0.007834956 | 2.1 | 357 | NA | NA | NA | NA | NA | NA | NA | NA | N | N | N | N | N | N |
| GPATCH3 | high in P | 2.9 | 0.007895296 | 2.1 | 358 | 80 | 69 | 102 | 262 | 211 | 155 | N | N | N | N | N | N | N | N |
| PAPL | high in P | 2.5 | 0.007901467 | 2.1 | 359 | 453 | 355 | 527 | 1294 | 1096 | 862 | N | NA | N | N | N | N | N | N |
| COMT | high in P | 4.1 | 0.007922038 | 2.1 | 360 | 19 | 45 | 65 | 149 | 150 | 88 | N | N | N | N | N | N | N | N |
| SNTB2 | high in P | 2.5 | 0.007990606 | 2.1 | 361 | 143 | 150 | 186 | 291 | 287 | 366 | N | N | N | N | N | N | N | N |
| PRRG2 | high in P | 4.7 | 0.008015291 | 2.1 | 362 | 67 | 72 | 169 | 445 | 313 | 256 | N | P | N | N | N | N | P | N |
| MPPE1 | high in P | 3.4 | 0.008053003 | 2.1 | 363 | 54 | 90 | 96 | 235 | 331 | 146 | N | N | N | N | N | N | N | N |
| MTMR9 | high in P | 2.1 | 0.008074945 | 2.1 | 364 | 25 | 53 | 53 | 105 | 85 | 80 | N | N | N | N | N | N | N | N |
| C6orf145 | high in P | 5.1 | 0.008081116 | 2.1 | 365 | 902 | 752 | 2016 | 4967 | 3523 | 4878 | N | P | N | N | N | N | N | N |
| WFDC6 | high in P | 6.2 | 0.008151056 | 2.1 | 366 | 1 | 1 | 1 | 17 | 4 | 9 | N | N | N | N | N | N | N | N |
| COL4A3BP | high in P | 2.1 | 0.008157227 | 2.1 | 367 | 31 | 39 | 32 | 61 | 52 | 68 | N | N | N | N | N | N | N | N |
| BOC | high in P | 5.4 | 0.008172998 | 2.1 | 368 | 60 | 44 | 67 | 149 | 124 | 354 | N | N | N | N | N | N | N | N |
| AIDA | high in P | 3.4 | 0.008179169 | 2.1 | 369 | 42 | 104 | 90 | 288 | 185 | 181 | N | N | N | N | N | N | N | N |
| UTP6 | high in P | 3.3 | 0.008204539 | 2.1 | 370 | 138 | 112 | 77 | 207 | 307 | 410 | N | N | N | N | N | N | N | N |
| MAP1S | high in P | 4.3 | 0.008257337 | 2.1 | 371 | 1790 | 707 | 2481 | 8901 | 7833 | 5168 | N | N | N | N | N | N | N | N |
| ANKRD49 | high in P | 3.0 | 0.008299849 | 2.1 | 372 | 12 | 24 | 11 | 32 | 59 | 61 | N | N | N | N | N | N | N | N |
| LOC100133920 | high in P | 3.1 | 0.008413673 | 2.1 | 373 | 7 | 7 | 7 | 13 | 15 | 10 | N | N | N | N | N | N | N | N |
| HPS6 | high in P | 3.1 | 0.008445214 | 2.1 | 374 | 79 | 79 | 43 | 209 | 194 | 121 | N | N | N | N | N | N | N | N |
| HTR3B | high in P | 3.2 | 0.008451385 | 2.1 | 375 | 110 | 57 | 120 | 360 | 317 | 214 | N | N | N | N | N | N | N | N |
| DHX8 | high in P | 3.0 | 0.008517211 | 2.1 | 376 | 172 | 194 | 328 | 753 | 763 | 456 | N | N | N | N | N | N | N | N |
| MCM2 | high in P | 2.8 | 0.00852681 | 2.1 | 377 | 76 | 59 | 87 | 211 | 179 | 137 | N | N | N | N | N | N | N | N |
| MNAT1 | high in P | 2.7 | 0.008532981 | 2.1 | 378 | 131 | 146 | 223 | 569 | 479 | 309 | N | N | N | N | N | N | N | N |
| RAB36 | high in P | 2.5 | 0.008605664 | 2.1 | 379 | 25 | 20 | 19 | 41 | 47 | 33 | N | N | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | MSDK-seq | | | |
|---|---|---|---|---|---|---|---|---|---|---|---|---|---|---|---|---|---|---|
| | | | | log10 | Nulliparous (NP) | | | | Parous (P) | | | | | | GeneBody | GeneBody | Pro-moter | Pro-moter |
| Gene Symbol | expression pattern | Fold Change | p-value | (P-val.) | Rank-ing | CD24+ N48 | CD24+ N58 | CD24+ N43 | CD24+ N37 | CD24+ N39 | CD24+ N40 | CD24+ N74 | CD24+ N66 | NP | NP | P | NP | P |
| | | | | | | | | | | | | | | | Met | Met | Met | Met |
| GTF2B | high in P | 2.1 | 0.008611835 | 2.1 | 380 | 189 | 211 | 251 | 479 | 451 | 364 | N | N | N | N | N | N | N |
| FANCB | high in P | 4.7 | 0.008621434 | 2.1 | 381 | 22 | 4 | 9 | 50 | 48 | 29 | N | N | N | N | N | N | N |
| EXOSC7 | high in P | 2.0 | 0.008627606 | 2.1 | 382 | 31 | 36 | 34 | 66 | 56 | 77 | N | N | N | N | N | N | N |
| C6orf211 | high in P | 3.1 | 0.008633777 | 2.1 | 383 | 27 | 23 | 15 | 142 | 50 | 59 | N | N | N | N | N | N | N |
| THBD | high in P | 3.3 | 0.008639948 | 2.1 | 384 | 14 | 24 | 25 | 88 | 42 | 41 | N | N | N | N | N | N | N |
| KIAA2026 | high in P | 2.0 | 0.008665318 | 2.1 | 385 | 42 | 52 | 35 | 78 | 82 | 86 | N | P | N | N | N | N | N |
| BMF | high in P | 7.0 | 0.008709202 | 2.1 | 386 | 9 | 51 | 20 | 256 | 145 | 58 | N | N | N | N | N | N | N |
| PAPPA | high in P | 6.6 | 0.008715373 | 2.1 | 387 | 27 | 57 | 42 | 232 | 154 | 63 | N | N | N | N | N | N | N |
| G9orf80 | high in P | 2.4 | 0.008766799 | 2.1 | 388 | 97 | 72 | 112 | 255 | 202 | 190 | P | N | N | N | N | N | N |
| SLC25A43 | high in P | 2.3 | 0.008803826 | 2.1 | 389 | 93 | 132 | 110 | 194 | 282 | 197 | N | N | N | N | N | N | N |
| PRPS1 | high in P | 4.3 | 0.008825082 | 2.1 | 390 | 28 | 65 | 37 | 81 | 134 | 186 | N | N | N | N | N | N | N |
| BNIP2 | high in P | 4.0 | 0.008880623 | 2.1 | 391 | 124 | 55 | 58 | 257 | 210 | 198 | N | N | N | N | N | N | N |
| GMFG | high in P | 6.8 | 0.008901879 | 2.1 | 392 | 2 | 3 | 11 | 86 | 42 | 18 | N | NA | N | N | N | N | N |
| SFXN1 | high in P | 2.7 | 0.008916964 | 2.0 | 393 | 30 | 53 | 54 | 138 | 92 | 102 | N | NA | N | N | N | N | N |
| BAZ1B | high in P | 3.0 | 0.008950562 | 2.0 | 394 | 93 | 184 | 251 | 417 | 518 | 434 | N | NA | N | N | N | N | N |
| RRN3P3 | high in P | 2.6 | 0.008975933 | 2.0 | 395 | 987 | 1008 | 979 | 2961 | 2394 | 1615 | P | P | N | N | N | N | N |
| EGR2 | high in P | 3.9 | 0.009030787 | 2.0 | 396 | 18 | 30 | 21 | 47 | 68 | 158 | N | P | N | N | N | N | N |
| SFRS2IP | high in P | 2.4 | 0.009036958 | 2.0 | 397 | 71 | 75 | 99 | 186 | 179 | 140 | N | NA | N | N | N | N | N |
| SLC30A4 | high in P | 2.4 | 0.009047929 | 2.0 | 398 | 12 | 22 | 15 | 38 | 25 | 39 | N | N | N | N | N | N | N |
| CST7 | high in P | 10.2 | 0.0090541 | 2.0 | 399 | 4 | 8 | 31 | 79 | 73 | 69 | N | NA | N | N | N | N | N |
| CROCCL1 | high in P | 4.1 | 0.009085642 | 2.0 | 400 | 82 | 174 | 58 | 288 | 235 | 389 | N | N | N | N | N | N | N |
| PITPNB | high in P | 2.9 | 0.009091813 | 2.0 | 401 | 205 | 195 | 341 | 554 | 539 | 829 | N | P | N | N | N | N | N |
| LRRC1 | high in P | 3.0 | 0.009097984 | 2.0 | 402 | 31 | 62 | 80 | 222 | 143 | 150 | N | N | N | N | N | N | N |
| FGL2 | high in P | 2.7 | 0.009150096 | 2.0 | 403 | 33 | 21 | 27 | 58 | 55 | 52 | N | P | N | N | N | N | N |
| HEATR1 | high in P | 2.8 | 0.009171352 | 2.0 | 404 | 58 | 129 | 71 | 163 | 247 | 180 | N | N | N | N | N | N | N |
| DOCK9 | high in P | 5.0 | 0.009177523 | 2.0 | 405 | 26 | 54 | 79 | 310 | 133 | 126 | N | P | N | N | N | N | N |
| RAB3A | high in P | 6.6 | 0.009183694 | 2.0 | 406 | 47 | 7 | 14 | 90 | 119 | 82 | N | P | N | N | N | N | N |
| EPB41L3 | high in P | 3.7 | 0.009198779 | 2.0 | 407 | 11 | 19 | 13 | 33 | 38 | 24 | N | P | N | N | N | N | N |
| BCS1L | high in P | 2.3 | 0.009204951 | 2.0 | 408 | 6 | 8 | 7 | 25 | 16 | 15 | N | P | N | N | N | N | N |
| SESN1 | high in P | 3.6 | 0.009234435 | 2.0 | 409 | 150 | 93 | 66 | 251 | 256 | 372 | N | P | N | N | N | N | N |
| IGFL1 | high in P | 18.6 | 0.009240606 | 2.0 | 410 | 3 | 65 | 41 | 825 | 514 | 100 | N | P | N | N | N | N | N |
| POMGNT1 | high in P | 2.4 | 0.009252948 | 2.0 | 411 | 211 | 306 | 340 | 653 | 607 | 521 | N | P | N | N | N | N | N |
| C4orf14 | high in P | 4.9 | 0.009270776 | 2.0 | 412 | 352 | 162 | 150 | 617 | 620 | 603 | N | P | N | N | N | N | N |
| HCCS | high in P | 2.3 | 0.009287918 | 2.0 | 413 | 257 | 160 | 234 | 492 | 509 | 488 | N | P | N | N | N | N | N |
| LRCH1 | high in P | 2.9 | 0.009294089 | 2.0 | 414 | 368 | 364 | 661 | 1024 | 1038 | 1461 | N | P | N | N | N | N | N |
| MGAT4A | high in P | 2.2 | 0.009331116 | 2.0 | 415 | 33 | 47 | 33 | 82 | 61 | 71 | N | P | N | N | N | N | N |
| SLC28A3 | high in P | 2.4 | 0.009521736 | 2.0 | 416 | 23 | 18 | 18 | 55 | 54 | 37 | N | P | N | N | N | N | N |
| C17orf67 | high in P | 13.3 | 0.009545735 | 2.0 | 417 | 10 | 6 | 54 | 169 | 120 | 85 | N | P | N | N | N | N | N |
| MAPRE2 | high in P | 2.3 | 0.009564248 | 2.0 | 418 | 16 | 20 | 26 | 46 | 41 | 50 | N | P | N | N | N | N | N |
| SENP1 | high in P | 2.8 | 0.009581391 | 2.0 | 419 | 33 | 70 | 40 | 121 | 106 | 85 | N | P | N | N | N | N | N |
| INPP5A | high in P | 2.6 | 0.009605389 | 2.0 | 420 | 38 | 99 | 63 | 179 | 139 | 150 | N | P | N | N | N | N | N |
| SULT1A4 | high in P | 3.7 | 0.009617732 | 2.0 | 421 | 135 | 234 | 344 | 526 | 702 | 937 | N | P | N | N | N | N | N |
| ATP10D | high in P | 3.8 | 0.009664358 | 2.0 | 422 | 13 | 24 | 15 | 49 | 27 | 60 | N | P | N | N | N | N | N |
| PDE1B | high in P | 5.9 | 0.009670529 | 2.0 | 423 | 8 | 8 | 10 | 79 | 31 | 16 | N | P | N | N | N | P | N |

TABLE 16-continued

Genes that Are Differentially Methylated between Nulliparous and Parous CD24+ Breast Epithelial Cells

| | | | | | SAGE-seq | | | | | | | | ChIP-seq | | | MSDK-seq | | |
|---|---|---|---|---|---|---|---|---|---|---|---|---|---|---|---|---|---|---|
| | | | | log10 | | Nulliparous (NP) | | | | Parous (P) | | | NP | | | | | |
| Gene Symbol | expression pattern | Fold Change | p-value | (P-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | GeneBody Met | Pro-moter Met | NP Pro-moter Met | P Pro-moter Met |
| ZBTB7C | high in P | 2.6 | 0.009690414 | 2.0 | 424 | 31 | 67 | 42 | 100 | 88 | 84 | N | N | N | N | N | N | N |
| PPM1H | high in P | 3.6 | 0.009713727 | 2.0 | 425 | 16 | 45 | 19 | 138 | 61 | 56 | N | N | N | N | N | N | N |
| PQLC1 | high in P | 2.8 | 0.009725384 | 2.0 | 426 | 409 | 646 | 1017 | 1705 | 1635 | 1908 | N | N | N | N | N | N | N |
| FLVCR1 | high in P | 2.2 | 0.009731555 | 2.0 | 427 | 33 | 32 | 36 | 60 | 71 | 52 | N | N | N | N | N | N | N |
| METTL5 | high in P | 3.2 | 0.009741155 | 2.0 | 428 | 51 | 38 | 21 | 100 | 108 | 68 | N | N | N | N | N | N | N |
| PATH | high in P | 3.2 | 0.009754183 | 2.0 | 429 | 450 | 408 | 362 | 1196 | 671 | 1399 | N | N | N | N | N | N | N |
| FAM43A | high in P | 3.2 | 0.00977681 | 2.0 | 430 | 184 | 90 | 164 | 564 | 395 | 354 | N | N | N | N | N | N | P |
| GSTCD | high in P | 2.5 | 0.009798752 | 2.0 | 431 | 24 | 23 | 18 | 41 | 41 | 44 | N | N | N | N | N | N | N |
| DYNLL1 | high in P | 2.7 | 0.009808352 | 2.0 | 432 | 2113 | 1381 | 2830 | 6119 | 4751 | 7380 | N | N | N | N | N | N | N |
| ZNF121 | high in P | 3.6 | 0.009824122 | 2.0 | 433 | 7 | 8 | 14 | 28 | 27 | 23 | N | N | N | N | N | N | N |
| SLC25A22 | high in P | 2.4 | 0.009830293 | 2.0 | 434 | 34 | 26 | 27 | 84 | 88 | 51 | N | N | N | N | N | N | N |
| GPR56 | high in P | 2.6 | 0.009877606 | 2.0 | 435 | 16 | 20 | 24 | 31 | 42 | 37 | N | N | N | N | N | N | N |
| SLC25A3 | high in P | 2.8 | 0.009889948 | 2.0 | 436 | 167 | 155 | 138 | 407 | 433 | 240 | N | N | N | N | N | P | N |
| ZEB1 | high in P | 3.0 | 0.009918061 | 2.0 | 437 | 14 | 25 | 15 | 53 | 33 | 36 | N | N | N | N | N | N | N |
| CARD10 | high in P | 2.3 | 0.009946174 | 2.0 | 438 | 163 | 185 | 240 | 348 | 403 | 480 | N | N | N | N | N | N | N |
| ZNF18 | high in P | 4.0 | 0.009970858 | 2.0 | 439 | 14 | 25 | 19 | 89 | 58 | 36 | N | N | N | N | N | N | N |
| SDK1 | high in P | 4.1 | 0.010009942 | 2.0 | 440 | 24 | 25 | 26 | 62 | 48 | 32 | N | N | N | N | N | N | N |
| ZNF836 | high in P | 4.1 | 0.010016114 | 2.0 | 441 | 7 | 7 | 18 | 35 | 47 | 31 | N | N | N | N | N | N | N |
| TTL | high in P | 2.3 | 0.010137479 | 2.0 | 442 | 98 | 164 | 137 | 311 | 241 | 217 | N | N | N | N | N | N | N |
| MRPS6 | high in P | 3.5 | 0.010143651 | 2.0 | 443 | 22 | 28 | 42 | 115 | 86 | 65 | N | N | N | N | N | N | N |
| ENC1 | high in P | 4.5 | 0.010155307 | 2.0 | 444 | 62 | 39 | 30 | 113 | 115 | 97 | N | N | N | N | N | N | N |
| TNFRSF4 | high in P | 13.6 | 0.010167649 | 2.0 | 445 | 7 | 2 | 35 | 270 | 155 | 39 | N | P | N | N | N | N | N |
| CSNK2A1P | high in P | 4.4 | 0.010186849 | 2.0 | 446 | 289 | 223 | 669 | 1654 | 1169 | 1028 | N | P | N | N | N | N | N |
| VHL | high in P | 3.6 | 0.010199191 | 2.0 | 447 | 247 | 607 | 356 | 1232 | 1163 | 807 | N | N | N | N | N | N | N |
| LOC493754 | high in P | 3.7 | 0.010205362 | 2.0 | 448 | 783 | 221 | 513 | 1565 | 1805 | 2135 | N | N | N | N | N | N | N |
| UGP2 | high in P | 3.0 | 0.01021839 | 2.0 | 449 | 62 | 77 | 40 | 109 | 134 | 179 | N | N | N | N | N | N | N |
| SLC23A2 | high in P | 2.0 | 0.010238275 | 2.0 | 450 | 62 | 76 | 76 | 118 | 162 | 113 | N | N | N | N | N | N | N |
| FUT6 | high in P | 2.8 | 0.010244446 | 2.0 | 451 | 3 | 4 | 4 | 22 | 11 | 9 | N | N | N | N | N | N | N |
| RIPK1 | high in P | 4.1 | 0.010273245 | 2.0 | 452 | 32 | 87 | 81 | 317 | 251 | 129 | N | N | N | N | N | N | N |
| TNFRSF6B | high in P | 4.9 | 0.010279416 | 2.0 | 453 | 55 | 205 | 96 | 679 | 584 | 223 | P | NA | N | N | N | N | N |
| NHLRC1 | high in P | 2.4 | 0.010422724 | 2.0 | 454 | 11 | 16 | 16 | 61 | 111 | 152 | NA | N | N | N | N | N | N |
| CCDC117 | high in P | 3.7 | 0.010285587 | 2.0 | 455 | 17 | 17 | 17 | 25 | 29 | 21 | N | N | N | N | N | N | N |
| ZNF691 | high in P | 3.9 | 0.01003185 | 2.0 | 456 | 32 | 54 | 72 | 241 | 129 | 115 | N | N | N | N | N | N | N |
| CRISPLD2 | high in P | 4.1 | 0.010333585 | 2.0 | 457 | 4 | 5 | 4 | 8 | 11 | 15 | N | N | N | N | N | N | N |
| MTHFD2L | high in P | 4.1 | 0.010384325 | 2.0 | 458 | 87 | 131 | 238 | 803 | 460 | 306 | P | N | N | N | N | N | N |
| MRVI1 | high in P | 3.9 | 0.010422724 | 2.0 | 459 | 19 | 37 | 47 | 61 | 111 | 152 | NA | N | N | N | N | N | N |
| GPATCH8 | high in P | 3.7 | 0.010428895 | 2.0 | 460 | 17 | 16 | 17 | 25 | 29 | 21 | N | N | N | N | N | N | N |
| PLOD3 | high in P | 2.3 | 0.010465236 | 2.0 | 461 | 22 | 41 | 53 | 70 | 70 | 78 | N | N | N | N | N | N | N |
| FABP3 | high in P | 4.7 | 0.010526262 | 2.0 | 462 | 138 | 215 | 452 | 788 | 764 | 694 | N | N | N | N | N | N | N |
| TPD52L2 | high in P | 7.0 | 0.01053689 | 2.0 | 463 | 4 | 4 | 14 | 22 | 31 | 82 | N | N | N | N | N | N | N |
| FBXL14 | high in P | 2.0 | 0.010597573 | 2.0 | 464 | 787 | 1340 | 1298 | 2467 | 2286 | 2474 | N | N | N | N | N | N | N |
| DAGLA | high in P | 3.5 | 0.010603744 | 2.0 | 465 | 6 | 14 | 8 | 24 | 20 | 22 | N | N | N | N | N | N | N |
| BTRC | high in P | 2.3 | 0.010618829 | 2.0 | 466 | 34 | 49 | 29 | 64 | 59 | 69 | N | N | N | N | N | P | P |
| ATP5E | high in P | 3.1 | 0.010707968 | 2.0 | 467 | 17 | 46 | 52 | 79 | 112 | 127 | N | N | N | N | N | N | N |
| | high in P | 2.4 | 0.010715567 | 2.0 | | 2 | 2 | 2 | 6 | 5 | 10 | N | N | N | N | N | N | N |

TABLE 16-continued

Genes that Are Differentially Methylated between Nulliparous and Parous CD24+ Breast Epithelial Cells

| | | | | | SAGE-seq | | | | | | | | | ChIP-seq | | | MSDK-seq | | |
|---|---|---|---|---|---|---|---|---|---|---|---|---|---|---|---|---|---|---|---|
| | | | | | | Nulliparous (NP) | | | | Parous (P) | | | | | | GeneBody | | Pro-moter | |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | NP | CD24+ N74 | CD24+ N66 | NP | GeneBody Met | P | Pro-moter Met | P |
| C2orf68 | high in P | 3.8 | 0.01074088 | 2.0 | 468 | 30 | 156 | 184 | 614 | 489 | 342 | N | N | N | N | N | N | N | N |
| DCLRE1C | high in P | 3.5 | 0.010747052 | 2.0 | 469 | 49 | 43 | 92 | 240 | 224 | 108 | N | N | N | N | N | N | N | N |
| SPR | high in P | 2.7 | 0.015295872 | 1.8 | 602 | 23 | 40 | 31 | 95 | 89 | 46 | N | N | N | N | N | N | N | N |
| PRO0628 | high in P | 6.2 | 0.015422038 | 1.8 | 603 | 37 | 5 | 10 | 105 | 74 | 38 | N | N | N | N | N | N | N | N |
| VWF | high in P | 4.7 | 0.015431637 | 1.8 | 604 | 43 | 43 | 73 | 236 | 105 | 91 | N | P | N | N | N | N | N | N |
| CASP8 | high in P | 2.5 | 0.015450837 | 1.8 | 605 | 93 | 253 | 233 | 450 | 540 | 432 | N | N | N | N | N | N | N | N |
| DGKZ | high in P | 2.0 | 0.015479635 | 1.8 | 606 | 195 | 190 | 204 | 296 | 419 | 356 | N | N | N | N | N | N | N | N |
| CHRDL2 | high in P | 4.9 | 0.015549575 | 1.8 | 607 | 3 | 14 | 3 | 16 | 21 | 38 | N | N | N | N | N | N | N | N |
| HMGB1L1 | high in P | 5.3 | 0.015555746 | 1.8 | 608 | NA | NA | NA | NA | NA | NA | N | NA | NA | N | N | N | N | N |
| CXCL12 | high in P | 1.9 | 0.015642142 | 1.8 | 609 | 22 | 31 | 25 | 38 | 37 | 36 | N | N | N | N | N | N | N | N |
| CACNB1 | high in P | 5.4 | 0.01572031 | 1.8 | 610 | 59 | 94 | 219 | 264 | 335 | 478 | N | N | N | N | N | N | N | N |
| LRRC37A3 | high in P | 7.4 | 0.015731281 | 1.8 | 611 | 7 | 12 | 54 | 86 | 103 | 90 | N | N | N | N | N | N | N | N |
| SNAI2 | high in P | 5.1 | 0.01575528 | 1.8 | 612 | 17 | 14 | 13 | 37 | 19 | 73 | N | N | N | N | N | N | N | N |
| SNX5 | high in P | 2.7 | 0.015764879 | 1.8 | 613 | 538 | 267 | 400 | 975 | 1074 | 780 | N | N | N | N | N | N | N | N |
| RNF26 | high in P | 3.7 | 0.015801906 | 1.8 | 614 | 115 | 208 | 321 | 695 | 613 | 394 | N | N | N | N | N | N | N | N |
| APOLD1 | high in P | 4.8 | 0.015821791 | 1.8 | 615 | 27 | 95 | 60 | 351 | 123 | 146 | N | N | N | N | N | N | N | N |
| GGNBP2 | high in P | 2.3 | 0.015827962 | 1.8 | 616 | 566 | 406 | 346 | 835 | 843 | 1031 | N | N | N | N | N | N | N | N |
| ZC3H7B | high in P | 3.3 | 0.015851961 | 1.8 | 617 | 85 | 105 | 218 | 314 | 309 | 275 | N | N | N | N | N | N | N | N |
| AASDHPPT | high in P | 2.5 | 0.01588556 | 1.8 | 618 | 49 | 65 | 31 | 87 | 126 | 106 | N | N | N | N | N | N | N | N |
| POLH | high in P | 2.2 | 0.015932186 | 1.8 | 619 | 120 | 131 | 195 | 345 | 304 | 242 | N | N | N | N | N | N | N | N |
| ZNF516 | high in P | 2.7 | 0.015953442 | 1.8 | 620 | 50 | 41 | 30 | 84 | 86 | 83 | N | P | N | N | N | N | N | N |
| C11orf75 | high in P | 2.3 | 0.015984984 | 1.8 | 621 | 16 | 16 | 20 | 32 | 36 | 53 | N | N | N | N | N | N | N | N |
| GPIHBP1 | high in P | 7.0 | 0.016239372 | 1.8 | 622 | 8 | 16 | 41 | 145 | 79 | 55 | N | P | N | N | N | N | N | N |
| KCTD12 | high in P | 2.3 | 0.016245543 | 1.8 | 623 | 52 | 55 | 34 | 92 | 84 | 110 | N | N | N | N | N | N | N | N |
| FRG1 | high in P | 2.7 | 0.016283256 | 1.8 | 624 | 46 | 68 | 60 | 171 | 149 | 87 | N | N | N | N | N | N | N | N |
| COL6A2 | high in P | 3.1 | 0.016314111 | 1.8 | 625 | 830 | 3095 | 2054 | 4077 | 5768 | 8389 | P | P | N | N | N | N | N | N |
| N4BP1 | high in P | 1.7 | 0.016358681 | 1.8 | 626 | 189 | 266 | 226 | 375 | 351 | 325 | N | N | N | N | N | N | N | N |
| MY019 | high in P | 1.9 | 0.016395022 | 1.8 | 627 | 146 | 141 | 120 | 207 | 236 | 262 | N | N | N | N | N | N | N | N |
| MST1R | high in P | 2.4 | 0.016448505 | 1.8 | 628 | 48 | 53 | 33 | 76 | 99 | 97 | N | N | N | N | N | N | N | N |
| SLC37A1 | high in P | 2.5 | 0.016459476 | 1.8 | 629 | 230 | 499 | 450 | 1089 | 902 | 666 | N | N | N | N | N | N | N | N |
| KIAA0196 | high in P | 2.8 | 0.016482104 | 1.8 | 630 | 8 | 10 | 12 | 28 | 15 | 22 | N | NA | NA | N | N | N | N | N |
| POLR3E | high in P | 5.5 | 0.016521188 | 1.8 | 631 | 73 | 84 | 263 | 363 | 391 | 393 | N | N | N | N | N | N | N | N |
| RAB2B | high in P | 2.4 | 0.016553415 | 1.8 | 632 | 47 | 29 | 60 | 134 | 97 | 98 | N | P | P | N | N | N | N | N |
| WNK1 | high in P | 2.0 | 0.016559586 | 1.8 | 633 | 242 | 302 | 279 | 486 | 412 | 557 | N | N | N | N | N | N | N | N |
| EFNB3 | high in P | 2.7 | 0.016586327 | 1.8 | 634 | 88 | 76 | 135 | 222 | 178 | 218 | N | N | N | N | N | N | N | N |
| NAA15 | high in P | 2.7 | 0.016645982 | 1.8 | 635 | 50 | 71 | 75 | 92 | 168 | 163 | N | NA | NA | N | N | N | N | N |
| LRG1 | high in P | 5.1 | 0.016666552 | 1.8 | 636 | 51 | 198 | 404 | 775 | 800 | 665 | N | N | N | N | N | N | N | N |
| FHL1 | high in P | 2.5 | 0.016686437 | 1.8 | 637 | 11 | 11 | 11 | 21 | 14 | 14 | N | P | P | N | N | N | N | N |
| CHST6 | high in P | 2.2 | 0.016702208 | 1.8 | 638 | 135 | 94 | 149 | 276 | 291 | 215 | N | N | N | N | N | N | N | N |
| YY1AP1 | high in P | 2.4 | 0.016730321 | 1.8 | 639 | 241 | 245 | 177 | 391 | 408 | 743 | N | N | N | N | N | N | N | N |
| TCEB3 | high in P | 2.0 | 0.01673992 | 1.8 | 640 | 179 | 352 | 339 | 624 | 540 | 567 | N | N | N | N | N | N | N | N |
| LRG1 | high in P | 3.1 | 0.016759805 | 1.8 | 641 | 106 | 180 | 144 | 807 | 400 | 219 | N | N | N | N | N | N | N | N |
| MMAA | high in P | 2.8 | 0.016781061 | 1.8 | 642 | 16 | 31 | 15 | 46 | 34 | 77 | N | N | N | N | N | N | N | N |
| ZBTB5 | high in P | 2.5 | 0.016787233 | 1.8 | 643 | 216 | 102 | 168 | 352 | 367 | 397 | N | N | N | N | N | N | N | N |

TABLE 16-continued

Genes that Are Differentially Methylated between Nulliparous and Parous CD24+ Breast Epithelial Cells

| | | | | | | SAGE-seq | | | | | | | ChIP-seq | | MSDK-seq | | | |
|---|---|---|---|---|---|---|---|---|---|---|---|---|---|---|---|---|---|---|
| | | | | | | Nulliparous (NP) | | | | Parous (P) | | | NP | P | NP | | P | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | GeneBody Met | Pro-moter Met | GeneBody Met | Pro-moter Met |
| PPP3CC | high in P | 2.2 | 0.010811231 | 1.8 | 644 | 86 | 140 | 141 | 195 | 230 | 273 | N | N | NP | N | N | N | N |
| RAD 18 | high in P | 2.0 | 0.010872943 | 1.8 | 645 | 46 | 74 | 79 | 109 | 136 | 105 | N | N | NP | N | N | N | N |
| PRSS36 | high in P | 3.3 | 0.010816306 | 2.0 | 470 | 31 | 16 | 15 | 85 | 54 | 39 | N | N | NP | N | N | N | N |
| C4orf32 | high in P | 2.4 | 0.010830019 | 2.0 | 471 | 23 | 29 | 18 | 49 | 36 | 65 | N | N | NP | N | N | N | N |
| RASD2 | high in P | 2.9 | 0.010845104 | 2.0 | 472 | 20 | 12 | 13 | 45 | 28 | 32 | N | N | NP | N | N | N | N |
| TRIM16 | high in P | 4.5 | 0.010851275 | 2.0 | 473 | 844 | 909 | 2910 | 7373 | 6954 | 3662 | N | N | NP | N | N | N | N |
| GDAP1 | high in P | 2.7 | 0.010878703 | 2.0 | 474 | 21 | 23 | 17 | 57 | 57 | 32 | N | N | NP | N | N | N | N |
| PPM1D | high in P | 5.2 | 0.010884874 | 2.0 | 475 | 92 | 43 | 22 | 184 | 133 | 163 | N | N | NP | N | N | N | N |
| DLL4 | high in P | 2.6 | 0.010929443 | 2.0 | 476 | 7 | 8 | 7 | 11 | 12 | 18 | N | N | NP | N | N | N | N |
| UBA5 | high in P | 3.1 | 0.010959613 | 2.0 | 477 | 162 | 159 | 135 | 405 | 540 | 238 | N | N | NP | N | N | N | N |
| ASCC1 | high in P | 2.5 | 0.010970584 | 2.0 | 478 | 110 | 127 | 108 | 424 | 257 | 190 | N | N | NP | N | N | N | N |
| TWIST1 | high in P | 6.2 | 0.011065894 | 2.0 | 479 | 7 | 7 | 7 | 36 | 21 | 10 | N | N | NP | N | N | N | N |
| SLC44A1 | high in P | 2.9 | 0.01108715 | 2.0 | 480 | 223 | 426 | 278 | 1068 | 643 | 590 | N | N | NP | N | N | N | N |
| JAM2 | high in P | 2.6 | 0.011093321 | 2.0 | 481 | 2 | 4 | 2 | 10 | 8 | 11 | N | N | NP | N | N | N | N |
| PODXL | high in P | 4.6 | 0.011123491 | 2.0 | 482 | 542 | 191 | 277 | 1520 | 809 | 1005 | N | N | NP | N | N | N | N |
| TOPORS | high in P | 2.7 | 0.011179032 | 2.0 | 483 | 45 | 69 | 28 | 105 | 90 | 123 | N | N | NP | N | N | N | N |
| SPRY2 | high in P | 4.7 | 0.011244172 | 2.0 | 484 | 92 | 45 | 31 | 191 | 126 | 210 | N | N | NP | N | N | N | N |
| RAB4B | high in P | 2.8 | 0.011261999 | 1.9 | 485 | 16 | 24 | 13 | 55 | 46 | 29 | N | N | NP | N | N | N | N |
| CP | high in P | 5.3 | 0.011289427 | 1.9 | 486 | 21 | 26 | 11 | 101 | 62 | 38 | N | N | NP | N | N | N | N |
| NXF1 | high in P | 2.2 | 0.011299026 | 1.9 | 487 | 1433 | 2024 | 2428 | 4578 | 3821 | 4692 | N | N | NP | N | N | N | N |
| DPY30 | high in P | 2.6 | 0.011404622 | 1.9 | 488 | 47 | 88 | 48 | 126 | 121 | 113 | N | N | NP | N | N | N | N |
| FAM50B | high in P | 5.6 | 0.011432735 | 1.9 | 489 | 14 | 37 | 53 | 167 | 158 | 72 | P | N | NP | N | N | N | N |
| ACOX3 | high in P | 3.3 | 0.011491018 | 1.9 | 490 | 153 | 125 | 252 | 612 | 513 | 313 | N | N | NP | N | N | N | N |
| EFNB1 | high in P | 4.1 | 0.011497189 | 1.9 | 491 | 42 | 103 | 99 | 671 | 313 | 154 | N | N | NP | N | N | N | N |
| ABCB4 | high in P | 4.0 | 0.01150336 | 1.9 | 492 | 2 | 4 | 3 | 14 | 8 | 18 | P | N | NP | N | N | N | N |
| C15orf17 | high in P | 2.5 | 0.011578785 | 1.9 | 493 | 155 | 179 | 220 | 295 | 409 | 472 | P | P | NP | N | N | N | N |
| ASXL1 | high in P | 2.6 | 0.011628784 | 1.9 | 494 | 87 | 70 | 88 | 155 | 171 | 208 | N | N | NP | N | N | N | N |
| MMP2 | high in P | 5.4 | 0.011635011 | 1.9 | 495 | 20 | 20 | 29 | 131 | 45 | 46 | P | N | NP | N | N | N | N |
| C13orf27 | high in P | 3.3 | 0.011715922 | 1.9 | 496 | 3 | 29 | 17 | 64 | 54 | 72 | N | N | NP | N | N | N | N |
| ZNF93 | high in P | 3.6 | 0.011752948 | 1.9 | 497 | 81 | 65 | 37 | 322 | 126 | 143 | N | N | NP | N | N | N | N |
| AARSD1 | high in P | 3.1 | 0.011775912 | 1.9 | 498 | 62 | 36 | 37 | 120 | 111 | 85 | N | N | NP | N | N | N | N |
| VWDE | high in P | 3.5 | 0.011808489 | 1.9 | 499 | 6 | 6 | 6 | 29 | 19 | 11 | N | N | NP | N | N | N | N |
| RBM23 | high in P | 2.0 | 0.01181466 | 1.9 | 500 | 289 | 342 | 408 | 660 | 708 | 560 | N | N | NP | N | N | N | N |
| HSPG2 | high in P | 2.7 | 0.011820831 | 1.9 | 501 | 232 | 275 | 374 | 508 | 594 | 852 | N | N | NP | N | N | N | N |
| ZNF692 | high in P | 2.7 | 0.011864029 | 1.9 | 502 | 373 | 155 | 395 | 893 | 815 | 1012 | P | N | NP | N | N | N | N |
| XPO1 | high in P | 3.1 | 0.0118702 | 1.9 | 503 | 496 | 489 | 255 | 909 | 952 | 1518 | N | N | NP | N | N | N | N |
| MUC16 | high in P | 3.4 | 0.011913398 | 1.9 | 504 | 72 | 319 | 500 | 853 | 786 | 978 | P | N | NP | N | N | N | N |
| VPS25 | high in P | 2.9 | 0.011938083 | 1.9 | 505 | 370 | 532 | 483 | 2213 | 1294 | 761 | N | N | NP | N | N | N | N |
| SORBS2 | high in P | 4.2 | 0.011963453 | 1.9 | 506 | 43 | 93 | 30 | 307 | 196 | 99 | N | N | NP | N | N | N | N |
| PCDHB15 | high in P | 2.5 | 0.011969624 | 1.9 | 507 | 1 | 1 | 1 | 8 | 4 | 4 | N | N | NP | N | N | N | N |
| FGFRL1 | high in P | 3.2 | 0.011975795 | 1.9 | 508 | 156 | 179 | 282 | 376 | 797 | 590 | P | N | NP | N | N | N | N |
| COL2A1 | high in P | 2.6 | 0.012032707 | 1.9 | 509 | 7 | 7 | 9 | 15 | 12 | 13 | N | N | NP | N | N | N | N |
| ABI2 | high in P | 2.3 | 0.012048478 | 1.9 | 510 | 33 | 36 | 41 | 98 | 64 | 59 | N | N | NP | N | N | N | N |
| C14orf19 | high in P | 1.9 | 0.012087562 | 1.9 | 511 | 8 | 20 | 19 | 29 | 33 | 30 | N | N | NP | N | N | N | N |

TABLE 16-continued

Genes that Are Differentially Methylated between Nulliparous and Parous CD24+ Breast Epithelial Cells

| | | | | SAGE-seq | | Nulliparous (NP) | | | | Parous (P) | | | | ChIP-seq | | | | MSDK-seq | | |
|---|---|---|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | | CD24+ N74 | CD24+ N66 | | GeneBody | GeneBody Met | | Pro-moter Met | | Pro-moter Met |
| | | | | | | | | | | | | NP | | P | NP | P | NP | | NP | P |
| GLIPR1L2 | high in P | 2.3 | 0.012102647 | 1.9 | 512 | 16 | 14 | 17 | 38 | 25 | 39 | N | N | N | NP | N | N | NP | N | N | N |
| C10orf54 | high in P | 3.2 | 0.012217841 | 1.9 | 513 | 29 | 33 | 46 | 91 | 63 | 59 | N | N | N | NP | N | N | NP | N | N | N |
| NPTX2 | high in P | 4.4 | 0.012230184 | 1.9 | 514 | 6 | 15 | 7 | 28 | 22 | 23 | N | N | P | NP | N | N | NP | N | N | N |
| CXCR7 | high in P | 12.3 | 0.012236355 | 1.9 | 515 | 9 | 38 | 44 | 407 | 208 | 78 | N | P | N | NP | N | N | NP | N | N | N |
| SERPINB6 | high in P | 3.1 | 0.012305609 | 1.9 | 516 | 411 | 565 | 952 | 2632 | 1810 | 1215 | N | P | N | NP | N | N | NP | N | N | N |
| PPID | high in P | 2.8 | 0.012330293 | 1.9 | 517 | 14 | 12 | 19 | 34 | 30 | 58 | N | N | N | NP | N | N | NP | N | N | N |
| BST2 | high in P | 2.0 | 0.012350864 | 1.9 | 518 | 251 | 188 | 278 | 476 | 486 | 487 | N | N | N | NP | N | N | NP | N | N | N |
| ARF1 | high in P | 2.2 | 0.012357035 | 1.9 | 519 | 7837 | 11722 | 11046 | 23407 | 21071 | 16056 | N | N | N | NP | N | N | NP | N | N | N |
| PLD6 | high in P | 3.8 | 0.012421489 | 1.9 | 520 | 14 | 25 | 40 | 111 | 61 | 75 | N | N | NA | NP | N | N | NP | N | N | N |
| TECR | high in P | 2.4 | 0.012242766 | 1.9 | 521 | 949 | 793 | 1241 | 2926 | 2464 | 1664 | N | NA | N | NP | N | N | NP | N | N | N |
| TIPIN | high in P | 2.3 | 0.01246263 | 1.9 | 522 | 11 | 12 | 9 | 28 | 29 | 18 | N | N | N | NP | N | N | NP | N | N | N |
| SMARCA4 | high in P | 4.5 | 0.012536684 | 1.9 | 523 | 899 | 778 | 2839 | 5587 | 6092 | 3534 | N | N | N | NP | N | N | NP | N | N | N |
| HEXA | high in P | 4.2 | 0.012577139 | 1.9 | 524 | 102 | 38 | 46 | 173 | 165 | 164 | N | N | N | NP | N | N | NP | N | N | N |
| EGFL7 | high in P | 7.5 | 0.012594281 | 1.9 | 525 | 9 | 25 | 62 | 265 | 124 | 116 | N | P | N | NP | N | N | NP | N | N | N |
| SLC45A4 | high in P | 4.5 | 0.012610052 | 1.9 | 526 | 24 | 37 | 72 | 165 | 146 | 92 | N | N | NA | NP | N | N | NP | N | N | N |
| CAPZB | high in P | 2.6 | 0.012699191 | 1.9 | 527 | 2967 | 2802 | 3278 | 9702 | 8022 | 5373 | N | N | N | NP | N | N | NP | N | N | N |
| SENP7 | high in P | 2.7 | 0.012744446 | 1.9 | 528 | 11 | 13 | 13 | 25 | 21 | 29 | N | N | P | NP | N | N | NP | P | N | N |
| FTSJ3 | high in P | 3.9 | 0.01278833 | 1.9 | 529 | 13 | 77 | 41 | 158 | 100 | 141 | N | N | N | NP | N | N | NP | N | N | N |
| SART1 | high in P | 2.5 | 0.012803415 | 1.9 | 530 | 404 | 253 | 542 | 943 | 1093 | 867 | N | N | P | NP | N | N | NP | N | N | N |
| AATF | high in P | 2.4 | 0.012956322 | 1.9 | 531 | 46 | 104 | 67 | 151 | 152 | 159 | N | P | P | NP | N | N | NP | P | N | N |
| LOC150381 | high in P | 3.0 | 0.012968664 | 1.9 | 532 | 117 | 96 | 177 | 364 | 334 | 233 | N | NA | NA | NP | N | N | NP | N | N | N |
| ZXDC | high in P | 1.9 | 0.012981007 | 1.9 | 533 | 250 | 281 | 348 | 591 | 490 | 475 | N | N | N | NP | N | N | NP | P | N | N |
| CRTC2 | high in P | 4.2 | 0.013017348 | 1.9 | 534 | 95 | 86 | 229 | 388 | 413 | 274 | N | P | N | NP | N | N | NP | N | N | N |
| SDF4 | high in P | 2.9 | 0.013057117 | 1.9 | 535 | 524 | 1003 | 741 | 2677 | 1987 | 1270 | N | N | N | NP | N | N | NP | N | N | N |
| ATR | high in P | 2.4 | 0.013096887 | 1.9 | 536 | 40 | 54 | 68 | 140 | 100 | 86 | N | P | N | NP | N | N | NP | N | N | N |
| LALBA | high in P | 10.1 | 0.013110601 | 1.9 | 537 | 2 | 2 | 3 | 6 | 16 | 140 | N | NA | N | NP | N | N | NP | N | N | N |
| REC8 | high in P | 2.2 | 0.013116772 | 1.9 | 538 | 44 | 58 | 57 | 90 | 93 | 118 | N | N | N | NP | N | N | NP | N | N | N |
| TNFRSF1B | high in P | 8.6 | 0.013148313 | 1.9 | 539 | 220 | 590 | 1581 | 5134 | 4626 | 1846 | N | P | N | NP | N | N | NP | N | N | N |
| TIMM17B | high in P | 3.0 | 0.013161341 | 1.9 | 540 | 338 | 161 | 247 | 703 | 668 | 508 | N | NA | N | NP | N | N | NP | N | N | N |
| MRPL34 | high in P | 5.8 | 0.013248423 | 1.9 | 541 | 286 | 184 | 759 | 2776 | 2178 | 807 | N | N | N | NP | N | N | NP | N | N | N |
| ACTR5 | high in P | 3.8 | 0.013254594 | 1.9 | 542 | 59 | 107 | 193 | 324 | 327 | 287 | N | N | N | NP | N | N | NP | N | N | N |
| ARHGAP23 | high in P | 2.3 | 0.013282707 | 1.9 | 543 | 111 | 197 | 161 | 337 | 241 | 306 | N | N | NA | NP | N | N | NP | N | N | N |
| RIN1 | high in P | 2.9 | 0.013288878 | 1.9 | 544 | 71 | 93 | 42 | 185 | 181 | 112 | N | P | N | NP | N | N | NP | N | N | N |
| POLR2A | high in P | 2.4 | 0.013325219 | 1.9 | 545 | 582 | 810 | 445 | 1778 | 1203 | 1186 | N | N | NA | NP | N | N | NP | N | N | N |
| FAM114A1 | high in P | 2.4 | 0.013349218 | 1.9 | 546 | 19 | 28 | 16 | 63 | 37 | 40 | N | N | N | NP | N | N | NP | N | N | N |
| ZNF521 | high in P | 3.3 | 0.013386931 | 1.9 | 547 | 16 | 20 | 16 | 42 | 26 | 30 | N | N | N | NP | N | N | NP | N | N | N |
| KDM5C | high in P | 3.9 | 0.013393102 | 1.9 | 548 | 357 | 169 | 186 | 674 | 603 | 516 | N | NA | NA | NP | N | N | NP | N | N | N |
| KCNH3 | high in P | 2.9 | 0.0134315 | 1.9 | 549 | 10 | 14 | 15 | 28 | 24 | 28 | N | P | P | NP | N | N | NP | N | N | N |
| CNBP | high in P | 4.0 | 0.01350144 | 1.9 | 550 | 334 | 214 | 150 | 679 | 503 | 306 | N | N | N | NP | N | N | NP | N | N | N |
| LOC100133957 | high in P | 2.2 | 0.013512411 | 1.9 | 551 | 49 | 38 | 27 | 70 | 67 | 667 | N | N | NA | NP | N | N | NP | N | N | N |
| ACTL6A | high in P | 4.9 | 0.013564523 | 1.9 | 552 | 5 | 29 | 7 | 53 | 29 | 83 | N | N | N | NP | N | N | NP | N | N | N |
| DCTN2 | high in P | 3.8 | 0.013593321 | 1.9 | 553 | 2191 | 1284 | 670 | 6078 | 4682 | 3236 | N | P | P | NP | N | N | NP | N | N | P |
| IFITM1 | high in P | 4.0 | 0.013606349 | 1.9 | 554 | 79 | 195 | 65 | 564 | 277 | 220 | N | N | NA | NP | N | N | NP | N | N | N |
| EFNA1 | high in P | 3.2 | 0.013666004 | 1.9 | 555 | 1363 | 784 | 645 | 2067 | 2338 | 2282 | N | N | N | NP | N | N | NP | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | MSDK-seq | | | |
|---|---|---|---|---|---|---|---|---|---|---|---|---|---|---|---|---|---|---|
| | | | | | | Nulliparous (NP) | | | | Parous (P) | | | | | | | | |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | NP | CD24+ N74 | CD24+ N66 | GeneBody NP | GeneBody Met | Pro-moter Met | NP Pro-moter Met | P Pro-moter Met |
| KANK2 | high in P | 2.6 | 0.013685889 | 1.9 | 556 | 16 | 19 | 16 | 29 | 29 | 24 | N | N | N | N | N | N | N | N |
| LPCAT1 | high in P | 3.3 | 0.01369206 | 1.9 | 557 | 69 | 123 | 203 | 370 | 259 | 336 | N | N | N | N | N | N | N | N |
| CALU | high in P | 2.4 | 0.01372223 | 1.9 | 558 | 492 | 382 | 370 | 1165 | 967 | 650 | N | N | N | N | N | N | N | N |
| HTATSF1 | high in P | 2.5 | 0.013750343 | 1.9 | 559 | 13 | 11 | 16 | 37 | 28 | 26 | P | N | N | N | N | N | N | N |
| SHROOM3 | high in P | 4.7 | 0.013759942 | 1.9 | 560 | 1510 | 657 | 500 | 3867 | 2748 | 1952 | N | N | N | N | N | N | N | N |
| CLCN5 | high in P | 2.3 | 0.013776399 | 1.9 | 561 | 19 | 23 | 20 | 31 | 31 | 34 | N | N | N | N | N | N | N | N |
| HLA-DOB | high in P | 3.7 | 0.01378257 | 1.9 | 562 | 15 | 6 | 6 | 39 | 24 | 16 | N | N | N | N | N | N | N | N |
| CRABP2 | high in P | 2.0 | 0.013838796 | 1.9 | 563 | 5826 | 3425 | 6730 | 10149 | 11163 | 10924 | N | N | N | N | N | N | N | N |
| IDE | high in P | 2.8 | 0.013844967 | 1.9 | 564 | 79 | 149 | 111 | 286 | 346 | 171 | N | N | N | N | N | N | N | N |
| MCOLN2 | high in P | 2.6 | 0.013902564 | 1.9 | 565 | 45 | 56 | 89 | 139 | 113 | 144 | N | N | N | N | N | N | N | N |
| ABLIM2 | high in P | 3.2 | 0.013981418 | 1.9 | 566 | 8 | 13 | 14 | 73 | 33 | 21 | P | N | N | N | N | N | N | N |
| NT5DC3 | high in P | 3.3 | 0.013987589 | 1.9 | 567 | 187 | 176 | 143 | 325 | 370 | 1043 | N | N | N | N | N | N | N | N |
| C15orf24 | high in P | 2.7 | 0.014010217 | 1.9 | 568 | 91 | 121 | 53 | 230 | 227 | 147 | N | N | N | N | N | N | N | N |
| TMEM213 | high in P | 2.9 | 0.014075357 | 1.9 | 569 | 133 | 76 | 76 | 269 | 184 | 193 | N | N | N | N | N | N | N | N |
| ISOC2 | high in P | 2.6 | 0.014095241 | 1.9 | 570 | 90 | 170 | 182 | 364 | 379 | 248 | N | N | N | N | N | N | N | N |
| SLC10A7 | high in P | 3.0 | 0.014141182 | 1.8 | 571 | 26 | 12 | 19 | 56 | 41 | 48 | N | N | N | N | N | N | N | N |
| HSPE1 | high in P | 7.5 | 0.014272148 | 1.8 | 572 | 11 | 11 | 44 | 55 | 175 | 69 | N | N | N | N | N | N | N | N |
| HADHA | high in P | 1.9 | 0.014278319 | 1.8 | 573 | 934 | 1112 | 1329 | 2174 | 1866 | 2063 | N | N | N | N | N | N | N | N |
| SMCR8 | high in P | 2.9 | 0.014387342 | 1.8 | 574 | 101 | 243 | 252 | 634 | 422 | 434 | N | N | N | N | N | N | N | N |
| KLF11 | high in P | 4.4 | 0.014416827 | 1.8 | 575 | 192 | 52 | 202 | 757 | 388 | 550 | N | N | N | N | N | N | N | N |
| SLC25A25 | high in P | 6.4 | 0.014432597 | 1.8 | 576 | 761 | 250 | 193 | 1319 | 951 | 1743 | N | N | N | N | N | N | N | N |
| ZBTB39 | high in P | 2.6 | 0.014477852 | 1.8 | 577 | 14 | 25 | 27 | 58 | 32 | 51 | N | N | N | N | N | N | N | N |
| CHMP4C | high in P | 2.2 | 0.014492937 | 1.8 | 578 | 117 | 94 | 94 | 321 | 196 | 166 | N | P | N | N | N | N | N | N |
| SEC22B | high in P | 2.3 | 0.014505965 | 1.8 | 579 | 136 | 171 | 134 | 402 | 304 | 219 | N | N | N | N | N | N | N | N |
| EVPL | high in P | 4.3 | 0.014551906 | 1.8 | 580 | 200 | 138 | 491 | 727 | 874 | 779 | P | N | N | N | N | N | N | N |
| MAP1A | high in P | 2.8 | 0.014580019 | 1.8 | 581 | 20 | 22 | 22 | 30 | 26 | 39 | N | N | N | N | N | N | N | N |
| GEN1 | high in P | 2.6 | 0.01461841 | 1.8 | 582 | 20 | 24 | 26 | 54 | 37 | 35 | P | N | N | N | N | N | N | N |
| C13orf | high in P | 2.0 | 0.014650645 | 1.8 | 583 | 55 | 55 | 41 | 118 | 73 | 86 | N | N | N | N | N | N | N | N |
| PMS2 | high in P | 3.1 | 0.014680129 | 1.8 | 584 | 50 | 43 | 79 | 129 | 138 | 109 | N | N | N | N | N | N | N | N |
| PTAR1 | high in P | 2.3 | 0.014715784 | 1.8 | 585 | 126 | 116 | 76 | 207 | 259 | 202 | N | N | N | N | N | N | N | N |
| PLLP | high in P | 2.8 | 0.01475281 | 1.8 | 586 | 80 | 60 | 35 | 146 | 136 | 98 | N | P | N | N | N | N | N | N |
| C11orf54 | high in P | 2.3 | 0.014777496 | 1.8 | 587 | 63 | 108 | 94 | 258 | 144 | 166 | N | N | N | N | N | N | N | N |
| TNFSF10 | high in P | 2.3 | 0.014804238 | 1.8 | 588 | 554 | 443 | 607 | 1459 | 1035 | 887 | N | N | N | N | N | N | N | N |
| C6orf15 | high in P | 5.3 | 0.014829608 | 1.8 | 589 | 10 | 15 | 38 | 108 | 189 | 41 | N | N | N | N | N | N | N | N |
| TMTC1 | high in P | 2.2 | 0.014849493 | 1.8 | 590 | 73 | 53 | 56 | 89 | 95 | 119 | P | N | N | N | N | N | N | N |
| GATS | high in P | 2.6 | 0.014898176 | 1.8 | 591 | 26 | 69 | 56 | 144 | 120 | 94 | N | N | N | N | N | N | N | N |
| PPP2R5B | high in P | 2.7 | 0.01497223 | 1.8 | 592 | 819 | 451 | 523 | 1159 | 1325 | 1559 | N | N | N | N | N | N | N | N |
| SHKBP1 | high in P | 4.7 | 0.014978401 | 1.8 | 593 | 99 | 210 | 374 | 1629 | 1025 | 410 | P | N | N | P | N | N | N | N |
| NDUFS2 | high in P | 2.1 | 0.015040112 | 1.8 | 594 | 14 | 15 | 19 | 108 | 31 | 26 | N | N | N | N | N | N | N | N |
| FZD5 | high in P | 6.2 | 0.015090167 | 1.8 | 595 | 38 | 87 | 228 | 407 | 365 | 295 | N | N | N | N | N | N | N | N |
| ELN | high in P | 3.5 | 0.015211533 | 1.8 | 596 | 12 | 12 | 14 | 18 | 25 | 48 | P | N | N | N | N | N | N | N |
| PCBD2 | high in P | 2.1 | 0.015236218 | 1.8 | 597 | 71 | 61 | 64 | 139 | 140 | 101 | N | N | N | N | N | N | N | P |
| LCORL | high in P | 2.0 | 0.015242389 | 1.8 | 598 | 13 | 24 | 17 | 30 | 31 | 24 | N | N | N | N | N | N | N | N |
| SYT12 | high in P | 2.3 | 0.015257474 | 1.8 | 599 | 20 | 50 | 37 | 76 | 56 | 86 | N | N | N | N | N | N | N | N |

TABLE 16-continued

Genes that Are Differentially Methylated between Nulliparous and Parous CD24+ Breast Epithelial Cells

| | | | | | | SAGE-seq | | | | | | | ChIP-seq | | | MSDK-seq | | |
|---|---|---|---|---|---|---|---|---|---|---|---|---|---|---|---|---|---|---|
| | | | | | | Nulliparous (NP) | | | Parous (P) | | | NP | | P | GeneBody | | Promoter | |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | CD24+ N74 | CD24+ N66 | GeneBody Met | P | Promoter Met | NP | P |
| SLC22A9 | high in P | 2.6 | 0.015263645 | 1.8 | 600 | 3 | 4 | 3 | 9 | 8 | 6 | N | P | NP | N | N | N | N |
| MEIS3P1 | high in P | 2.1 | 0.015289701 | 1.8 | 601 | 22 | 37 | 25 | 50 | 45 | 59 | N | N | N | N | N | N | N |
| GMPS | high in P | 2.9 | 0.016879114 | 1.8 | 646 | 177 | 110 | 80 | 258 | 299 | 234 | N | N | N | N | N | N | N |
| BID | high in P | 2.3 | 0.01701008 | 1.8 | 647 | 311 | 215 | 249 | 435 | 532 | 581 | N | N | N | N | N | N | N |
| POLG | high in P | 2.3 | 0.017123903 | 1.8 | 648 | 820 | 723 | 1286 | 1830 | 2241 | 1900 | N | N | N | N | N | N | N |
| SORBS1 | high in P | 2.0 | 0.017180129 | 1.8 | 649 | 86 | 191 | 193 | 315 | 299 | 345 | N | N | N | N | N | N | N |
| PGBD2 | high in P | 2.0 | 0.0171863 | 1.8 | 650 | 9 | 9 | 9 | 13 | 12 | 12 | N | N | N | N | N | N | N |
| CLECAE | high in P | 2.5 | 0.01730218 | 1.8 | 651 | 4 | 5 | 5 | 39 | 11 | 12 | N | N | N | N | N | N | N |
| RANBP9 | high in P | 2.7 | 0.017317265 | 1.8 | 652 | 375 | 262 | 205 | 776 | 493 | 590 | N | N | N | N | N | N | N |
| HTRA4 | high in P | 2.3 | 0.017338522 | 1.8 | 653 | 79 | 60 | 43 | 122 | 111 | 99 | N | N | N | N | N | N | N |
| GPX3 | high in P | 3.4 | 0.017450288 | 1.8 | 654 | 17 | 58 | 67 | 168 | 136 | 74 | N | N | N | N | N | N | N |
| ADAMTS9 | high in P | 2.5 | 0.017463316 | 1.8 | 655 | 146 | 175 | 103 | 297 | 250 | 355 | N | N | N | N | N | N | N |
| RAD52 | high in P | 3.2 | 0.017538055 | 1.8 | 656 | 6 | 15 | 9 | 18 | 24 | 37 | N | N | N | N | N | N | N |
| CBARA1 | high in P | 2.1 | 0.017544227 | 1.8 | 657 | 136 | 102 | 116 | 238 | 232 | 181 | N | N | N | N | N | N | N |
| PPAPDC2 | high in P | 2.7 | 0.017555997 | 1.8 | 658 | 20 | 62 | 39 | 136 | 101 | 69 | N | N | N | N | N | N | N |
| SLC2A3 | high in P | 5.4 | 0.017588796 | 1.8 | 659 | 17 | 22 | 33 | 97 | 33 | 131 | N | N | N | N | N | N | N |
| CETN2 | high in P | 2.8 | 0.017604567 | 1.8 | 660 | 362 | 298 | 170 | 688 | 685 | 508 | N | N | N | N | N | N | N |
| RRAGA | high in P | 2.2 | 0.017664907 | 1.8 | 661 | 430 | 691 | 638 | 1508 | 1197 | 922 | N | N | N | N | N | N | N |
| CUL2 | high in P | 2.7 | 0.017705362 | 1.8 | 662 | 185 | 123 | 106 | 266 | 336 | 240 | N | N | N | N | N | N | N |
| TMEM212 | high in P | 3.9 | 0.017724561 | 1.8 | 663 | 353 | 105 | 197 | 648 | 666 | 515 | N | NA | N | N | N | N | N |
| FCHO2 | high in P | 3.0 | 0.017730732 | 1.8 | 664 | 15 | 19 | 24 | 53 | 30 | 82 | N | N | N | N | N | N | N |
| CSGALNACT1 | high in P | 4.5 | 0.017762274 | 1.8 | 665 | 28 | 48 | 27 | 225 | 123 | 47 | N | NA | N | N | N | N | N |
| C12orf5 | high in P | 1.8 | 0.017817814 | 1.7 | 666 | 55 | 55 | 68 | 104 | 100 | 96 | N | N | N | N | N | N | N |
| S100A7 | high in P | 49.4 | 0.017834956 | 1.7 | 667 | 1 | 63 | 398 | 3939 | 2152 | 417 | N | N | N | N | N | N | N |
| PSMA7 | high in P | 2.0 | 0.017847298 | 1.7 | 668 | 2189 | 2813 | 1923 | 4958 | 5050 | 3959 | P | N | N | N | N | N | N |
| DRG1 | high in P | 7.3 | 0.017909696 | 1.7 | 669 | 26 | 48 | 139 | 274 | 281 | 148 | N | N | N | N | N | N | N |
| TCFL5 | high in P | 2.0 | 0.017922038 | 1.7 | 670 | 17 | 22 | 21 | 29 | 44 | 33 | N | N | N | N | N | N | N |
| TIMP4 | high in P | 3.5 | 0.017970721 | 1.7 | 671 | 6 | 6 | 6 | 26 | 11 | 11 | P | N | N | N | N | N | N |
| DLAT | high in P | 3.4 | 0.017980321 | 1.7 | 672 | 35 | 129 | 79 | 289 | 257 | 138 | N | N | N | N | N | N | N |
| OLFM2 | high in P | 4.4 | 0.01800912 | 1.7 | 673 | 36 | 42 | 112 | 148 | 154 | 138 | N | N | N | N | N | N | N |
| TM2D2 | high in P | 3.6 | 0.018072202 | 1.7 | 674 | 45 | 104 | 206 | 365 | 282 | 279 | N | N | N | N | N | N | N |
| NT5C2 | high in P | 2.3 | 0.018125 | 1.7 | 675 | 221 | 188 | 119 | 360 | 334 | 396 | N | N | N | N | N | N | N |
| RTN4RL2 | high in P | 5.1 | 0.01815037 | 1.7 | 676 | 14 | 61 | 128 | 236 | 242 | 254 | N | N | N | N | N | N | N |
| NOL6 | high in P | 12.1 | 0.018156541 | 1.7 | 677 | 17 | 52 | 249 | 213 | 498 | 498 | N | N | N | N | N | N | N |
| TSR1 | high in P | 2.4 | 0.018824088 | 1.7 | 678 | 43 | 41 | 34 | 95 | 82 | 54 | N | N | N | N | N | N | N |
| CCDC55 | high in P | 2.6 | 0.018247052 | 1.7 | 679 | 257 | 170 | 299 | 684 | 550 | 421 | N | N | N | N | N | N | N |
| ADO | high in P | 2.6 | 0.018270365 | 1.7 | 680 | 39 | 106 | 116 | 189 | 220 | 214 | N | N | N | N | N | N | N |
| VCAN | high in P | 2.9 | 0.018359504 | 1.7 | 681 | 28 | 29 | 28 | 58 | 33 | 36 | N | N | N | N | N | N | N |
| ANAPC1 | high in P | 6.1 | 0.018384874 | 1.7 | 682 | 97 | 157 | 452 | 562 | 691 | 727 | N | N | N | N | N | N | N |
| GSN | high in P | 1.9 | 0.018415044 | 1.7 | 683 | 871 | 1456 | 1695 | 3492 | 2692 | 2550 | N | N | N | N | N | N | N |
| RDH16 | high in P | 4.1 | 0.018519268 | 1.7 | 684 | 1 | 4 | 2 | 25 | 14 | 9 | N | P | N | N | N | N | N |
| REV1 | high in P | 2.7 | 0.018578922 | 1.7 | 685 | 77 | 88 | 142 | 203 | 215 | 168 | N | N | N | N | N | N | N |
| GNG4 | high in P | 3.3 | 0.018606349 | 1.7 | 686 | 13 | 28 | 33 | 64 | 63 | 42 | N | N | N | N | N | P | N |
| MLH1 | high in P | 2.2 | 0.018640634 | 1.7 | 687 | 21 | 47 | 29 | 68 | 57 | 77 | N | N | N | N | N | N | N |

TABLE 16-continued

Genes that Are Differentially Methylated between Nulliparous and Parous CD24+ Breast Epithelial Cells

| | | | | SAGE-seq | | | | | | | ChIP-seq | | | MSDK-seq | | |
| | | | | | Nulliparous (NP) | | | | Parous (P) | | | | | | | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | P GeneBody Met | NP Pro-moter Met | P Pro-moter Met |
|---|---|---|---|---|---|---|---|---|---|---|---|---|---|---|---|---|---|
| CTCF | high in P | 2.5 | 0.018655719 | 1.7 | 688 | 38 | 93 | 47 | 189 | 114 | 95 | N | N | N | N | N | N |
| STARD3NL | high in P | 2.0 | 0.018862109 | 1.7 | 689 | 150 | 179 | 135 | 295 | 368 | 219 | N | N | N | N | N | N |
| ZDHHC2 | high in P | 2.0 | 0.018896393 | 1.7 | 690 | 15 | 18 | 12 | 26 | 32 | 23 | N | N | N | N | N | N |
| COX 11 | high in P | 1.8 | 0.018912164 | 1.7 | 691 | 15 | 23 | 18 | 28 | 38 | 28 | N | N | N | N | N | N |
| NCRNA00201 | high in P | 2.1 | 0.018925192 | 1.7 | 692 | 25 | 30 | 22 | 39 | 47 | 46 | NA | NA | N | N | N | N |
| AP4S1 | high in P | 5.0 | 0.018945077 | 1.7 | 693 | 435 | 131 | 141 | 591 | 529 | 863 | N | N | N | N | N | N |
| CSor78 | high in P | 2.6 | 0.018962905 | 1.7 | 694 | 111 | 311 | 193 | 567 | 408 | 442 | N | N | N | N | N | N |
| ZFP41 | high in P | 2.9 | 0.01897799 | 1.7 | 695 | 25 | 24 | 48 | 102 | 70 | 63 | N | N | N | N | N | N |
| FAM70B | high in P | 5.4 | 0.019052729 | 1.7 | 696 | 1 | 2 | 3 | 34 | 8 | 12 | N | P | N | N | N | N |
| CLEC17A | high in P | 3.5 | 0.019009867 | 1.7 | 697 | 4 | 4 | 6 | 8 | 16 | 34 | P | P | N | N | N | N |
| SNHG10 | high in P | 2.9 | 0.019113755 | 1.7 | 698 | 18 | 11 | 11 | 32 | 25 | 60 | N | N | N | N | N | N |
| KTELC1 | high in P | 3.0 | 0.019119926 | 1.7 | 699 | 32 | 55 | 69 | 188 | 160 | 75 | N | N | N | N | N | N |
| ABL1 | high in P | 2.2 | 0.019157639 | 1.7 | 700 | 280 | 585 | 402 | 813 | 834 | 714 | N | N | N | N | N | N |
| PIGS | high in P | 2.4 | 0.01916381 | 1.7 | 701 | 156 | 195 | 107 | 461 | 370 | 225 | N | N | N | N | N | N |
| GGA2 | high in P | 2.5 | 0.019258434 | 1.7 | 702 | 98 | 73 | 88 | 213 | 151 | 176 | N | N | N | N | N | N |
| ADORA2A | high in P | 3.3 | 0.019264605 | 1.7 | 703 | 29 | 99 | 61 | 160 | 114 | 261 | N | N | N | N | N | P |
| PODN | high in P | 5.1 | 0.01933043 | 1.7 | 704 | 12 | 12 | 13 | 27 | 15 | 35 | N | N | N | N | N | N |
| PSMC6 | high in P | 1.8 | 0.019376371 | 1.7 | 705 | 523 | 536 | 320 | 813 | 878 | 800 | N | P | N | N | N | N |
| DDTL | high in P | 4.5 | 0.019415455 | 1.7 | 706 | 45 | 18 | 42 | 77 | 168 | 74 | N | N | N | N | N | N |
| MLXIPL | high in P | 2.7 | 0.019470996 | 1.7 | 707 | 16 | 37 | 51 | 127 | 71 | 69 | N | N | N | N | N | P |
| ZNF570 | high in P | 4.4 | 0.019477167 | 1.7 | 708 | 2 | 8 | 11 | 36 | 35 | 20 | N | N | N | N | N | P |
| SECISBP2 | high in P | 4.5 | 0.019548478 | 1.7 | 709 | 213 | 486 | 986 | 2100 | 1904 | 1135 | N | N | N | N | N | N |
| SERPINH1 | high in P | 2.8 | 0.019582762 | 1.7 | 710 | 126 | 252 | 205 | 330 | 370 | 596 | N | N | N | N | N | N |
| GPR115 | high in P | 2.8 | 0.019588933 | 1.7 | 711 | 4 | 4 | 4 | 12 | 11 | 7 | N | N | N | N | N | N |
| RNMTL1 | high in P | 2.0 | 0.019632131 | 1.7 | 712 | 65 | 124 | 116 | 209 | 167 | 203 | N | N | N | N | N | N |
| KCNQ5 | high in P | 2.1 | 0.019684243 | 1.7 | 713 | 5 | 5 | 5 | 7 | 10 | 8 | N | N | N | N | N | N |
| LOC642587 | high in P | 4.1 | 0.019690414 | 1.7 | 714 | 399 | 937 | 2184 | 3499 | 3776 | 3439 | N | N | N | N | N | N |
| GCDH | high in P | 2.4 | 0.019696585 | 1.7 | 715 | 52 | 79 | 109 | 200 | 164 | 134 | N | N | N | N | N | N |
| C6orf120 | high in P | 3.4 | 0.019779553 | 1.7 | 716 | 180 | 111 | 241 | 356 | 674 | 355 | N | N | N | N | N | N |
| SMURF1 | high in P | 5.2 | 0.019826179 | 1.7 | 717 | 1096 | 917 | 4042 | 6959 | 6504 | 4522 | N | N | N | P | N | N |
| AVPH | high in P | 2.2 | 0.019835779 | 1.7 | 718 | 99 | 72 | 77 | 215 | 161 | 120 | N | N | N | N | N | N |
| KRT14 | high in P | 4.3 | 0.019918061 | 1.7 | 719 | 397 | 1245 | 777 | 1621 | 2899 | 14028 | N | N | N | N | N | N |
| CBLL1 | high in P | 2.1 | 0.019933146 | 1.7 | 720 | 124 | 126 | 181 | 296 | 241 | 215 | N | N | N | N | N | N |
| AFTPH | high in P | 2.5 | 0.019948917 | 1.7 | 721 | 513 | 356 | 267 | 668 | 744 | 1118 | N | N | N | N | N | N |
| KIAA1919 | high in P | 1.8 | 0.019996743 | 1.7 | 722 | 19 | 45 | 28 | 75 | 71 | 47 | N | N | N | N | N | N |
| C1orf27 | high in P | 1.8 | 0.019973601 | 1.7 | 723 | 121 | 142 | 117 | 199 | 268 | 184 | N | N | N | N | N | N |
| PREPL | high in P | 1.8 | 0.019999871 | 1.7 | 724 | 28 | 35 | 36 | 47 | 59 | 69 | N | N | N | N | N | N |
| ROBO4 | high in P | 3.0 | 0.020008571 | 1.7 | 725 | 14 | 13 | 9 | 62 | 22 | 20 | P | N | N | N | N | N |
| C6orf64 | high in P | 2.0 | 0.020091539 | 1.7 | 726 | 60 | 118 | 98 | 191 | 178 | 145 | N | N | N | N | N | N |
| TNRC6B | high in P | 2.1 | 0.02009771 | 1.7 | 727 | 103 | 126 | 105 | 280 | 217 | 156 | P | P | P | N | N | N |
| RAP1GDS1 | high in P | 3.1 | 0.020195077 | 1.7 | 728 | 12 | 37 | 33 | 64 | 83 | 46 | N | N | N | N | N | N |
| PDZRN3 | high in P | 2.2 | 0.020236903 | 1.7 | 729 | 19 | 17 | 16 | 22 | 24 | 30 | N | N | N | N | N | N |
| BTBD10 | high in P | 2.0 | 0.020282844 | 1.7 | 730 | 78 | 138 | 149 | 205 | 278 | 229 | N | N | N | N | N | N |
| TCF4 | high in P | 3.3 | 0.020478264 | 1.7 | 731 | 28 | 51 | 34 | 287 | 100 | 49 | P | P | N | P | N | P |

TABLE 16-continued

Genes that Are Differentially Methylated between Nulliparous and Parous CD24+ Breast Epithelial Cells

| | | | | SAGE-seq | | Nulliparous (NP) | | | | Parous (P) | | | | ChIP-seq | | | MSDK-seq | | |
|---|---|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | P GeneBody Met | NP Pro-moter | P Pro-moter Met |
|---|---|---|---|---|---|---|---|---|---|---|---|---|---|---|---|---|---|
| ITGAL | high in P | 3.1 | 0.020498834 | 1.7 | 732 | 6 | 7 | 13 | 27 | 27 | 15 | N | N | N | N | N | N |
| PLB1 | high in P | 2.8 | 0.020528319 | 1.7 | 733 | 7 | 15 | 16 | 43 | 42 | 20 | N | N | N | N | N | N |
| IFI16 | high in P | 3.4 | 0.020575631 | 1.7 | 734 | 66 | 203 | 168 | 320 | 277 | 527 | N | N | N | N | N | N |
| CKB | high in P | 2.1 | 0.020600315 | 1.7 | 735 | 1444 | 758 | 1606 | 2764 | 2914 | 3474 | N | N | N | N | N | N |
| TMEM169 | high in P | 2.2 | 0.020640771 | 1.7 | 736 | 21 | 20 | 15 | 46 | 33 | 28 | N | N | N | N | N | N |
| LOC554202 | high in P | 3.9 | 0.020665997 | 1.7 | 737 | 11 | 11 | 12 | 15 | 16 | 39 | NA | NA | N | N | N | N |
| CHIC1 | high in P | 3.5 | 0.020676426 | 1.7 | 738 | 13 | 35 | 18 | 46 | 35 | 45 | N | N | N | N | N | N |
| ALOX12P2 | high in P | 2.3 | 0.020682597 | 1.7 | 739 | 7 | 16 | 13 | 49 | 23 | 20 | N | N | N | N | N | N |
| REEP4 | high in P | 2.6 | 0.020697682 | 1.7 | 740 | 104 | 124 | 209 | 289 | 392 | 243 | N | N | N | N | N | N |
| TMEM81 | high in P | 4.6 | 0.020710025 | 1.7 | 741 | 2 | 7 | 4 | 14 | 12 | 33 | NA | N | N | N | N | N |
| LOC642313 | high in P | 5.6 | 0.020722367 | 1.7 | 742 | 3 | 6 | 15 | 32 | 24 | 34 | NA | NA | N | N | N | N |
| HIVEP3 | high in P | 2.9 | 0.020758708 | 1.7 | 743 | 139 | 283 | 369 | 414 | 653 | 890 | N | N | N | N | N | N |
| MAF | high in P | 2.4 | 0.020764879 | 1.7 | 744 | 34 | 34 | 36 | 62 | 44 | 55 | N | N | N | N | N | N |
| GOS2 | high in P | 5.6 | 0.020779964 | 1.7 | 745 | 102 | 75 | 35 | 105 | 324 | 687 | P | N | N | N | N | N |
| MRPL14 | high in P | 2.1 | 0.020800535 | 1.7 | 746 | 1495 | 1085 | 1115 | 2389 | 2675 | 1945 | N | N | N | N | N | N |
| PKP4 | high in P | 3.3 | 0.020819048 | 1.7 | 747 | 984 | 484 | 1447 | 3887 | 3319 | 1735 | NA | N | N | N | N | N |
| CLDN10 | high in P | 2.7 | 0.020899273 | 1.7 | 748 | 5 | 8 | 5 | 42 | 16 | 11 | P | N | N | N | N | N |
| RASSF4 | high in P | 7.1 | 0.020911093 | 1.7 | 749 | 96 | 58 | 332 | 1103 | 595 | 300 | N | N | N | N | N | N |
| MRPL33 | high in P | 2.1 | 0.020917101 | 1.7 | 750 | 1023 | 792 | 823 | 2476 | 1701 | 1340 | N | N | N | N | N | N |
| SFRS13A | high in P | 2.2 | 0.02104121 | 1.7 | 751 | 184 | 107 | 164 | 275 | 321 | 332 | NA | N | N | N | N | N |
| RBM15B | high in P | 2.4 | 0.021166004 | 1.7 | 752 | 150 | 216 | 324 | 567 | 477 | 362 | N | N | N | N | N | N |
| CEP170 | high in P | 2.2 | 0.021172175 | 1.7 | 753 | 13 | 15 | 13 | 25 | 22 | 18 | N | N | N | N | N | N |
| MDM4 | high in P | 2.0 | 0.021178346 | 1.7 | 754 | 178 | 177 | 269 | 452 | 394 | 312 | N | N | N | N | N | N |
| SFRS8 | high in P | 2.8 | 0.021205088 | 1.7 | 755 | 237 | 285 | 557 | 817 | 634 | 952 | P | N | N | N | N | N |
| PRKDC | high in P | 3.4 | 0.021240743 | 1.7 | 756 | 349 | 553 | 1101 | 1640 | 2109 | 1228 | N | N | N | N | N | N |
| PSMD1 | high in P | 2.5 | 0.021261314 | 1.7 | 757 | 848 | 1659 | 1223 | 4364 | 3093 | 1956 | N | N | N | N | N | N |
| FGF5 | high in P | 2.3 | 0.021358681 | 1.7 | 758 | 47 | 30 | 56 | 80 | 97 | 93 | P | P | N | N | N | N |
| C6orf136 | high in P | 2.0 | 0.021378566 | 1.7 | 759 | 110 | 95 | 78 | 168 | 171 | 148 | N | N | N | N | N | N |
| TUSC1 | high in P | 2.5 | 0.021414221 | 1.7 | 760 | 165 | 307 | 178 | 475 | 400 | 409 | P | N | N | N | N | N |
| FUCA1 | high in P | 3.5 | 0.021460848 | 1.7 | 761 | 8 | 34 | 12 | 61 | 48 | 43 | N | N | N | N | N | N |
| IGF1 | high in P | 3.2 | 0.021554786 | 1.7 | 762 | 50 | 66 | 105 | 167 | 135 | 133 | N | N | N | N | N | N |
| UBLCP1 | high in P | 2.7 | 0.021575357 | 1.7 | 763 | 33 | 19 | 13 | 80 | 37 | 54 | N | N | N | N | N | N |
| CTU2 | high in P | 3.1 | 0.021588385 | 1.7 | 764 | 85 | 102 | 200 | 247 | 294 | 265 | NA | N | N | N | N | N |
| CCDC115 | high in P | 2.3 | 0.021640496 | 1.7 | 765 | 62 | 74 | 26 | 140 | 95 | 129 | N | N | N | N | N | N |
| NOC4L | high in P | 3.2 | 0.021650096 | 1.7 | 766 | 227 | 311 | 598 | 875 | 1057 | 660 | N | N | N | N | N | N |
| TRIM26 | high in P | 2.0 | 0.021725521 | 1.7 | 767 | 633 | 736 | 1023 | 1283 | 1838 | 1410 | N | N | N | N | N | N |
| PDGFA | high in P | 3.2 | 0.021725521 | 1.7 | 768 | 31 | 87 | 49 | 100 | 119 | 203 | P | N | N | N | N | N |
| UNC50 | high in P | 3.8 | 0.021781747 | 1.7 | 769 | 15 | 96 | 39 | 180 | 121 | 138 | N | N | N | N | N | N |
| TROVE2 | high in P | 1.8 | 0.021829059 | 1.7 | 770 | 241 | 355 | 408 | 582 | 723 | 587 | N | N | N | N | N | N |
| RAGE | high in P | 2.2 | 0.021833523 | 1.7 | 771 | 143 | 103 | 116 | 299 | 267 | 171 | N | N | N | N | N | N |
| NUDT21 | high in P | 2.2 | 0.021846887 | 1.7 | 772 | 234 | 187 | 152 | 432 | 332 | 298 | N | N | N | N | N | N |
| PIWIL4 | high in P | 4.5 | 0.0218798 | 1.7 | 773 | 4 | 4 | 6 | 10 | 11 | 10 | N | N | N | N | N | P |
| SHISA9 | high in P | 2.0 | 0.02191477 | 1.7 | 774 | 22 | 22 | 19 | 30 | 29 | 28 | NA | NA | N | N | N | N |
| APOL1 | high in P | 2.4 | 0.021920941 | 1.7 | 775 | 8 | 15 | 16 | 35 | 28 | 24 | N | N | N | N | N | N |

TABLE 16-continued

Genes that Are Differentially Methylated between Nulliparous and Parous CD24+ Breast Epithelial Cells

| | | | | SAGE-seq | | Nulliparous (NP) | | | | Parous (P) | | | | ChIP-seq | | | | MSDK-seq | | | |
|---|---|---|---|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP | CD24+ N74 P | CD24+ N66 P | NP | GeneBody GeneBody NP Met | | P | NP | GeneBody Met | Pro-moter Met | Pro-moter P |
|---|---|---|---|---|---|---|---|---|---|---|---|---|---|---|---|---|---|---|---|---|---|
| FAM103A1 | high in P | 1.5 | 0.021994995 | 1.7 | 776 | 51 | 59 | 55 | 77 | 75 | 76 | N | N | N | N | N | N | N | N | N | N |
| TUBE1 | high in P | 3.5 | 0.022023793 | 1.7 | 777 | 79 | 53 | 54 | 197 | 247 | 81 | N | N | N | N | N | N | N | N | N | N |
| CCDC86 | high in P | 2.4 | 0.022078648 | 1.7 | 778 | 132 | 226 | 310 | 409 | 517 | 463 | N | N | N | N | N | N | N | N | N | N |
| PRIC285 | high in P | 1.7 | 0.022084819 | 1.7 | 779 | 26 | 31 | 38 | 51 | 52 | 51 | N | N | N | N | N | N | N | N | N | N |
| ZSWIM7 | high in P | 2.0 | 0.022139674 | 1.7 | 780 | 32 | 36 | 35 | 69 | 73 | 49 | N | N | N | N | N | N | N | N | N | N |
| GCHFR | high in P | 3.9 | 0.022145845 | 1.7 | 781 | 41 | 43 | 119 | 417 | 216 | 110 | N | N | N | N | N | N | N | N | N | N |
| CSF3R | high in P | 3.8 | 0.022172586 | 1.7 | 782 | 70 | 67 | 199 | 439 | 262 | 216 | N | N | N | N | N | N | N | N | N | N |
| TOR1B | high in P | 1.6 | 0.022182186 | 1.7 | 783 | 83 | 113 | 108 | 154 | 143 | 148 | N | N | N | N | N | N | N | N | N | N |
| LOC100216545 | high in P | 2.6 | 0.022195214 | 1.7 | 784 | 44 | 17 | 59 | 107 | 90 | 101 | N | NA | N | N | N | N | N | N | N | N |
| ABCD1 | high in P | 3.7 | 0.022213727 | 1.7 | 785 | 33 | 62 | 109 | 174 | 119 | 161 | N | N | N | N | N | N | N | N | N | N |
| C19orf70 | high in P | 2.3 | 0.022273382 | 1.7 | 786 | 291 | 219 | 433 | 638 | 677 | 569 | N | N | N | N | N | N | N | N | N | N |
| ARPC3 | high in P | 3.7 | 0.022315894 | 1.7 | 787 | 11 | 14 | 39 | 57 | 75 | 38 | N | N | N | N | N | N | N | N | N | N |
| RNASEH2C | high in P | 3.0 | 0.022322065 | 1.7 | 788 | 22 | 28 | 47 | 84 | 59 | 56 | N | N | N | N | N | N | N | N | N | N |
| RHOF | high in P | 5.5 | 0.022363206 | 1.7 | 789 | 14 | 16 | 50 | 65 | 80 | 52 | N | N | N | N | N | N | N | N | N | N |
| RFXANK | high in P | 2.7 | 0.022470858 | 1.6 | 790 | 241 | 229 | 531 | 1308 | 1188 | 513 | N | N | N | N | N | N | N | N | N | N |
| EAPP | high in P | 2.5 | 0.022489372 | 1.6 | 791 | 111 | 223 | 125 | 324 | 291 | 243 | N | N | N | N | N | N | N | N | N | N |
| FRK | high in P | 1.8 | 0.022655993 | 1.6 | 792 | 5 | 8 | 7 | 11 | 12 | 17 | N | N | N | N | N | N | N | N | N | N |
| TEAD4 | high in P | 2.0 | 0.022675192 | 1.6 | 793 | 150 | 222 | 258 | 337 | 389 | 480 | N | N | N | N | N | N | N | N | N | N |
| METT11D1 | high in P | 2.7 | 0.022681363 | 1.6 | 794 | 424 | 499 | 839 | 1195 | 1103 | 1142 | N | N | N | N | N | N | N | N | N | N |
| CYP2R1 | high in P | 2.9 | 0.022271359 | 1.6 | 795 | 101 | 87 | 174 | 274 | 293 | 191 | N | N | N | N | N | N | N | N | N | N |
| SBSN | high in P | 2.4 | 0.022275536 | 1.6 | 796 | 13 | 25 | 35 | 41 | 65 | 53 | N | N | N | N | N | N | N | N | N | N |
| NEK9 | high in P | 2.6 | 0.022797244 | 1.6 | 797 | 39 | 32 | 70 | 117 | 83 | 143 | N | N | N | N | N | N | N | N | N | N |
| PPP1R13L | high in P | 2.3 | 0.022903524 | 1.6 | 798 | 1627 | 712 | 1233 | 2620 | 2270 | 3716 | N | N | N | N | N | N | N | N | N | N |
| PIK3CA | high in P | 2.1 | 0.023026947 | 1.6 | 799 | 43 | 56 | 27 | 81 | 68 | 89 | N | N | N | N | N | N | N | N | N | N |
| MEG3 | high in P | 11.4 | 0.023146942 | 1.6 | 800 | 9 | 37 | 29 | 68 | 76 | 271 | N | N | N | N | N | N | N | N | N | N |
| MIF4GD | high in P | 2.5 | 0.023284078 | 1.6 | 801 | 59 | 59 | 57 | 138 | 182 | 77 | N | N | N | N | N | N | N | N | N | N |
| C10orf104 | high in P | 1.9 | 0.023239025 | 1.6 | 802 | NA | NA | NA | NA | NA | NA | N | N | N | N | N | N | N | N | N | N |
| UCA1 | high in P | 3.0 | 0.023392416 | 1.6 | 803 | 8 | 12 | 11 | 38 | 29 | 14 | N | N | N | N | N | N | N | N | N | N |
| ATP6V1E1 | high in P | 3.3 | 0.023423272 | 1.6 | 804 | 64 | 89 | 178 | 248 | 396 | 191 | N | N | N | N | N | N | N | N | N | N |
| ZNF844 | high in P | 3.5 | 0.023460299 | 1.6 | 805 | 31 | 8 | 11 | 39 | 36 | 43 | N | N | N | N | N | N | N | N | N | N |
| TRPS1 | high in P | 2.0 | 0.023548752 | 1.6 | 806 | 236 | 233 | 253 | 528 | 466 | 325 | N | N | N | N | N | N | N | N | N | N |
| FAIM2 | high in P | 5.9 | 0.023564523 | 1.6 | 807 | 7 | 9 | 8 | 71 | 38 | 10 | N | NA | NA | N | N | N | N | N | N | N |
| CHCHD8 | high in P | 2.0 | 0.023618692 | 1.6 | 808 | 56 | 87 | 48 | 93 | 141 | 109 | N | N | N | N | N | N | N | N | N | N |
| CBX5 | high in P | 2.4 | 0.023755143 | 1.6 | 809 | 64 | 61 | 64 | 120 | 110 | 95 | N | N | N | N | N | N | N | N | N | N |
| SPSB3 | high in P | 3.7 | 0.023761314 | 1.6 | 810 | 1124 | 629 | 194 | 2038 | 1621 | 1974 | N | N | N | N | N | N | N | N | N | N |
| DPY19L3 | high in P | 1.8 | 0.023822234 | 1.6 | 811 | 31 | 31 | 21 | 45 | 43 | 50 | N | N | N | N | N | N | N | N | N | N |
| LOC284232 | high in P | 1.7 | 0.023869652 | 1.6 | 812 | 301 | 326 | 344 | 539 | 494 | 582 | N | NA | NA | N | N | N | N | N | N | P |
| ACBD6 | high in P | 3.5 | 0.023921078 | 1.6 | 813 | 11 | 19 | 11 | 52 | 39 | 20 | N | N | N | N | N | N | N | N | N | N |
| ANKLE1 | high in P | 2.4 | 0.023971818 | 1.6 | 814 | 94 | 58 | 56 | 144 | 108 | 142 | N | P | N | N | N | N | N | N | N | N |
| MORF4L1 | high in P | 2.0 | 0.023977799 | 1.6 | 815 | 1867 | 1636 | 818 | 3506 | 3058 | 2848 | N | N | N | N | N | N | N | N | N | N |
| EIF2AK2 | high in P | 2.3 | 0.023988961 | 1.6 | 816 | 21 | 51 | 26 | 75 | 66 | 48 | N | P | N | N | N | N | N | N | N | N |
| S100A8 | high in P | 2.9 | 0.024004046 | 1.6 | 817 | 3 | 21 | 21 | 63 | 47 | 50 | N | P | N | N | N | N | N | N | N | N |
| S100A3 | high in P | 5.3 | 0.02403833 | 1.6 | 818 | 14 | 48 | 76 | 234 | 202 | 83 | N | N | N | N | N | N | N | N | N | N |
| LOC729603 | high in P | 3.0 | 0.0240589 | 1.6 | 819 | 219 | 140 | 74 | 500 | 253 | 331 | N | N | N | N | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | | MSDK-seq | | |
|---|---|---|---|---|---|---|---|---|---|---|---|---|---|---|---|---|---|---|
| | | | | | | Nulliparous (NP) | | | | Parous (P) | | | NP | P | | NP | P | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody | GeneBody Met | Pro-moter Met | GeneBody | GeneBody Met | Pro-moter Met |
| SPEG | high in P | 3.7 | 0.024144668 | 1.6 | 820 | 121 | 81 | 258 | 266 | 573 | 427 | P | P | NP | N | N | N | N | N |
| COX10 | high in P | 1.8 | 0.024251577 | 1.6 | 821 | 11 | 16 | 22 | 28 | 27 | 32 | N | N | N | N | N | N | N | N |
| ABCF1 | high in P | 2.0 | 0.024298889 | 1.6 | 822 | 274 | 294 | 439 | 520 | 666 | 648 | N | N | N | N | N | N | N | N |
| MGC16384 | high in P | 1.9 | 0.0243846 | 1.6 | 823 | 36 | 20 | 25 | 45 | 47 | 61 | NA | NA | N | N | N | N | N | N |
| KRBA2 | high in P | 2.6 | 0.024473053 | 1.6 | 824 | 322 | 197 | 456 | 1041 | 759 | 541 | N | N | N | N | N | N | N | N |
| CYP27C1 | high in P | 2.4 | 0.024566991 | 1.6 | 825 | 51 | 68 | 116 | 186 | 168 | 114 | N | N | N | N | N | N | N | N |
| FAM134B | high in P | 3.9 | 0.024619789 | 1.6 | 826 | 92 | 33 | 32 | 194 | 127 | 93 | N | N | N | N | N | N | N | N |
| GLO1 | high in P | 2.2 | 0.02462596 | 1.6 | 827 | 2808 | 2863 | 4254 | 8465 | 8275 | 5162 | N | N | N | N | N | N | N | N |
| CWorf12 | high in P | 2.0 | 0.02463556 | 1.6 | 828 | 81 | 130 | 72 | 146 | 187 | 159 | N | N | N | N | N | N | N | N |
| CPNE2 | high in P | 2.2 | 0.024665044 | 1.6 | 829 | 154 | 533 | 570 | 1036 | 1131 | 956 | N | N | N | N | N | N | N | N |
| POU2F2 | high in P | 3.1 | 0.024689728 | 1.6 | 830 | 11 | 39 | 57 | 98 | 68 | 95 | N | N | N | N | N | N | N | N |
| DOCK4 | high in P | 1.6 | 0.0246959 | 1.6 | 831 | 17 | 26 | 21 | 31 | 30 | 29 | N | N | N | N | N | N | N | N |
| RAB6A | high in P | 2.2 | 0.024769953 | 1.6 | 832 | 21 | 68 | 55 | 127 | 114 | 106 | N | N | N | N | N | N | N | N |
| GLDC | high in P | 2.1 | 0.02480218 | 1.6 | 833 | 5 | 5 | 5 | 7 | 10 | 13 | N | N | N | N | N | N | N | N |
| ARPC5 | high in P | 2.4 | 0.024876234 | 1.6 | 834 | 76 | 216 | 129 | 382 | 243 | 275 | N | N | N | N | N | N | N | N |
| NDUFA4L2 | high in P | 4.6 | 0.024889262 | 1.6 | 835 | 10 | 8 | 15 | 67 | 40 | 16 | N | N | N | N | N | N | N | N |
| GPR180 | high in P | 2.3 | 0.025073025 | 1.6 | 836 | 7 | 35 | 32 | 50 | 71 | 47 | P | N | N | N | N | N | N | N |
| GRK4 | high in P | 2.6 | 0.02508811 | 1.6 | 837 | 5 | 9 | 9 | 12 | 18 | 36 | N | N | N | N | N | N | N | N |
| HSPB2 | high in P | 2.8 | 0.025130623 | 1.6 | 838 | 10 | 6 | 6 | 11 | 16 | 37 | N | N | N | N | N | N | N | N |
| SHISA4 | high in P | 5.8 | 0.025165285 | 1.6 | 839 | 4 | 42 | 43 | 227 | 113 | 60 | N | N | N | N | N | N | N | N |
| USP8 | high in P | 2.2 | 0.025241703 | 1.6 | 840 | 70 | 147 | 81 | 233 | 206 | 141 | N | N | N | N | N | N | N | N |
| FAM153B | high in P | 2.4 | 0.025247874 | 1.6 | 841 | 81 | 47 | 113 | 206 | 150 | 161 | N | N | N | N | N | N | N | N |
| SCRIB | high in P | 6.1 | 0.025508214 | 1.6 | 842 | 220 | 280 | 1186 | 1263 | 1677 | 1304 | N | P | N | N | N | N | N | N |
| NRM | high in P | 2.3 | 0.025317814 | 1.6 | 843 | 34 | 31 | 41 | 127 | 56 | 61 | N | N | N | N | N | N | N | N |
| COX7B | high in P | 2.1 | 0.025323985 | 1.6 | 844 | 66 | 77 | 39 | 104 | 131 | 99 | N | N | N | N | N | N | N | N |
| EBF3 | high in P | 2.5 | 0.025561231 | 1.6 | 845 | 12 | 12 | 12 | 27 | 21 | 15 | P | N | N | N | N | N | N | N |
| SLC14A1 | high in P | 2.4 | 0.025577002 | 1.6 | 846 | 216 | 108 | 265 | 373 | 428 | 577 | P | P | N | N | N | N | N | N |
| SH3PXD2A | high in P | 3.4 | 0.025661341 | 1.6 | 847 | 158 | 84 | 102 | 259 | 182 | 318 | N | N | N | N | N | N | N | N |
| SERPINB8 | high in P | 1.6 | 0.025707968 | 1.6 | 848 | 99 | 122 | 108 | 165 | 148 | 193 | N | N | N | N | N | N | N | N |
| SF3B2 | high in P | 2.4 | 0.025760765 | 1.6 | 849 | 574 | 538 | 498 | 1318 | 1349 | 714 | N | P | N | N | N | N | N | N |
| LOC285550 | high in P | 2.7 | 0.025766936 | 1.6 | 850 | NA | NA | NA | NA | NA | NA | NA | NA | N | N | N | N | N | N |
| SIDT2 | high in P | 2.9 | 0.025808763 | 1.6 | 851 | 302 | 126 | 174 | 442 | 435 | 433 | N | N | N | N | N | N | N | N |
| HERC5 | high in P | 2.1 | 0.025827962 | 1.6 | 852 | 6 | 8 | 6 | 10 | 16 | 15 | N | N | N | N | N | N | N | N |
| VTI1B | high in P | 1.6 | 0.025875274 | 1.6 | 853 | 93 | 115 | 97 | 148 | 162 | 134 | N | N | N | N | N | N | N | N |
| FBXL8 | high in P | 3.7 | 0.025975384 | 1.6 | 854 | 11 | 42 | 60 | 129 | 150 | 72 | N | N | N | N | N | N | N | N |
| NONO | high in P | 2.1 | 0.025995269 | 1.6 | 855 | 1240 | 524 | 1368 | 2916 | 2768 | 1955 | N | NA | N | N | N | N | N | N |
| AP3S1 | high in P | 2.2 | 0.02612212 | 1.6 | 856 | 5 | 9 | 5 | 11 | 18 | 13 | N | N | N | N | N | N | N | N |
| UPP2 | high in P | 2.2 | 0.026163261 | 1.6 | 857 | 78 | 91 | 91 | 113 | 193 | 181 | N | N | N | N | N | N | N | N |
| ZNF350 | high in P | 2.5 | 0.026181775 | 1.6 | 858 | 15 | 8 | 5 | 22 | 14 | 18 | N | N | N | N | N | N | N | N |
| DGKA | high in P | 1.7 | 0.026194117 | 1.6 | 859 | 179 | 166 | 205 | 284 | 334 | 268 | N | N | N | N | N | N | N | N |
| DCP1B | high in P | 2.9 | 0.026200288 | 1.6 | 860 | 4 | 24 | 18 | 47 | 60 | 27 | N | N | N | N | N | N | N | N |
| PATE4 | high in P | 1.9 | 0.026318911 | 1.6 | 861 | 21 | 19 | 12 | 30 | 25 | 33 | NA | NA | N | N | N | N | N | N |
| TRPM7 | high in P | 2.2 | 0.026325082 | 1.6 | 862 | 100 | 121 | 67 | 162 | 144 | 203 | N | N | N | N | N | N | N | N |
| MUT | high in P | 2.5 | 0.026342224 | 1.6 | 863 | 9 | 13 | 22 | 35 | 22 | 40 | N | N | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | | MSDK-seq | | |
|---|---|---|---|---|---|---|---|---|---|---|---|---|---|---|---|---|---|---|
| | | | | | | Nulliparous (NP) | | | | Parous (P) | | | | | | | | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody | GeneBody Met | P | Pro-moter Met | NP | Pro-moter Met | P |
| JRK | high in P | 2.7 | 0.026348396 | 1.6 | 864 | 58 | 112 | 151 | 161 | 232 | 255 | N | N | NP | N | N | N | N | N |
| MTA3 | high in P | 2.3 | 0.026395022 | 1.6 | 865 | 303 | 226 | 430 | 703 | 651 | 525 | N | N | N | N | N | N | N | N |
| NCOR2 | high in P | 2.1 | 0.026401193 | 1.6 | 866 | 119 | 336 | 354 | 483 | 564 | 592 | N | N | N | N | N | N | N | N |
| ZNF407 | high in P | 1.9 | 0.026407364 | 1.6 | 867 | 21 | 34 | 31 | 40 | 40 | 46 | N | N | N | N | N | N | N | N |
| NSMCE1 | high in P | 9.4 | 0.026413535 | 1.6 | 868 | 39 | 49 | 311 | 439 | 384 | 304 | N | N | N | N | N | N | N | N |
| ZNF167 | high in P | 3.2 | 0.026482789 | 1.6 | 869 | 6 | 20 | 9 | 21 | 26 | 31 | N | P | N | N | N | N | N | N |
| ZSCAN16 | high in P | 3.0 | 0.026512959 | 1.6 | 870 | 22 | 26 | 53 | 102 | 88 | 53 | N | N | N | N | N | N | N | N |
| RHEBL1 | high in P | 2.5 | 0.026567128 | 1.6 | 871 | 12 | 11 | 14 | 17 | 27 | 39 | N | N | N | N | N | N | N | N |
| LAT | high in P | 8.2 | 0.026596613 | 1.6 | 872 | 20 | 34 | 178 | 204 | 214 | 220 | N | N | N | N | N | N | N | N |
| NLRP1 | high in P | 1.7 | 0.026602784 | 1.6 | 873 | 19 | 28 | 29 | 41 | 51 | 35 | N | N | N | N | N | N | N | N |
| USP2 | high in P | 2.0 | 0.026665181 | 1.6 | 874 | 39 | 22 | 30 | 55 | 55 | 54 | N | N | N | N | N | N | N | N |
| SLFN13 | high in P | 1.8 | 0.026716607 | 1.6 | 875 | 73 | 53 | 67 | 107 | 118 | 111 | N | N | N | N | N | N | N | N |
| CACHD1 | high in P | 1.7 | 0.026731692 | 1.6 | 876 | 37 | 42 | 34 | 50 | 52 | 78 | N | N | N | N | N | N | N | N |
| INHA | high in P | 3.3 | 0.026765291 | 1.6 | 877 | 23 | 9 | 3 | 61 | 26 | 29 | N | N | N | N | N | N | N | N |
| SLCO4A1 | high in P | 2.2 | 0.026787233 | 1.6 | 878 | 9 | 20 | 12 | 53 | 27 | 20 | N | N | N | N | N | N | N | N |
| FGFBP1 | high in P | 3.1 | 0.026802318 | 1.6 | 879 | 220 | 646 | 739 | 830 | 1714 | 2176 | N | N | N | N | N | N | N | N |
| HMGN4 | high in P | 1.9 | 0.026981281 | 1.6 | 880 | 174 | 235 | 136 | 313 | 356 | 290 | N | N | N | N | N | N | N | N |
| PIP4K2A | high in P | 2.4 | 0.026987452 | 1.6 | 881 | 19 | 42 | 61 | 75 | 101 | 73 | N | N | N | N | N | N | N | N |
| POLDIP3 | high in P | 2.6 | 0.027091676 | 1.6 | 882 | 431 | 262 | 174 | 584 | 549 | 659 | N | N | N | N | N | N | N | N |
| ITGB7 | high in P | 6.6 | 0.027107447 | 1.6 | 883 | 15 | 25 | 89 | 78 | 120 | 181 | N | N | N | N | N | N | N | N |
| LRRC47 | high in P | 2.4 | 0.027113618 | 1.6 | 884 | 13 | 65 | 71 | 154 | 133 | 95 | N | N | N | N | N | N | N | N |
| PCBD1 | high in P | 3.0 | 0.027167101 | 1.6 | 885 | 59 | 23 | 43 | 132 | 125 | 67 | N | N | N | N | N | N | N | N |
| ABCC13 | high in P | 2.7 | 0.027213042 | 1.6 | 886 | 23 | 10 | 15 | 32 | 72 | 29 | N | N | N | N | N | N | N | N |
| KLHL15 | high in P | 2.9 | 0.027263782 | 1.6 | 887 | 60 | 30 | 34 | 77 | 68 | 95 | N | N | N | N | N | N | N | N |
| FXYD5 | high in P | 3.3 | 0.027380348 | 1.6 | 888 | 93 | 458 | 256 | 808 | 730 | 504 | N | N | N | N | N | N | N | N |
| YTHDF2 | high in P | 2.2 | 0.027426975 | 1.6 | 889 | 1056 | 1984 | 2784 | 5319 | 4357 | 3730 | N | NA | N | N | N | N | N | N |
| SEC31A | high in P | 2.0 | 0.027433146 | 1.6 | 890 | 1808 | 975 | 1452 | 2391 | 3882 | 2951 | N | NA | N | N | N | N | N | N |
| LOC283314 | high in P | 3.5 | 0.027448917 | 1.6 | 891 | 66 | 46 | 116 | 253 | 243 | 109 | NA | NA | N | N | N | N | N | N |
| MRTO4 | high in P | 2.9 | 0.027472916 | 1.6 | 892 | 133 | 247 | 475 | 636 | 518 | 528 | N | N | N | N | N | N | N | N |
| TGFB1I1 | high in P | 10.6 | 0.027522285 | 1.6 | 893 | 27 | 208 | 1046 | 1697 | 1065 | 910 | N | N | N | N | N | N | N | N |
| KDM2A | high in P | 2.0 | 0.027594967 | 1.6 | 894 | 1032 | 891 | 847 | 2319 | 1579 | 1451 | N | NA | N | N | N | N | N | N |
| ZC3H12B | high in P | 1.9 | 0.027660107 | 1.6 | 895 | 9 | 10 | 9 | 13 | 15 | 13 | N | P | N | N | N | N | N | N |
| C9orf5 | high in P | 2.7 | 0.027714962 | 1.6 | 896 | 70 | 99 | 163 | 247 | 206 | 175 | N | N | N | N | N | N | N | N |
| TCEA2 | high in P | 2.7 | 0.027730732 | 1.6 | 897 | 202 | 96 | 307 | 520 | 518 | 423 | N | N | N | N | N | N | N | N |
| LOC652276 | high in P | 1.8 | 0.027762959 | 1.6 | 898 | 27 | 28 | 22 | 39 | 47 | 39 | N | N | N | N | N | N | N | N |
| ZNF626 | high in P | 2.3 | 0.027775302 | 1.6 | 899 | 16 | 36 | 46 | 68 | 61 | 48 | N | N | N | N | N | N | N | N |
| ABHD8 | high in P | 3.7 | 0.027805472 | 1.6 | 900 | 38 | 122 | 105 | 362 | 219 | 128 | N | N | N | N | N | N | N | N |
| DECR2 | high in P | 2.5 | 0.027839756 | 1.6 | 901 | 229 | 284 | 484 | 594 | 785 | 577 | N | N | N | N | N | N | N | N |
| MAPKSP1 | high in P | 2.5 | 0.027879526 | 1.6 | 902 | 329 | 167 | 220 | 530 | 420 | 480 | N | P | N | N | N | N | N | N |
| PAK6 | high in P | 3.6 | 0.027907639 | 1.6 | 903 | 17 | 40 | 45 | 140 | 115 | 44 | N | N | N | N | N | N | N | N |
| IQCA1 | high in P | 2.4 | 0.027951522 | 1.6 | 904 | 9 | 10 | 9 | 15 | 19 | 25 | N | N | N | N | N | N | N | N |
| PKP2 | high in P | 4.1 | 0.027957693 | 1.6 | 905 | 32 | 29 | 79 | 129 | 116 | 71 | N | N | N | N | N | N | N | N |
| TRIT1 | high in P | 1.8 | 0.027989235 | 1.6 | 906 | 35 | 39 | 27 | 53 | 70 | 45 | N | N | N | N | N | N | N | N |
| KCNMB1 | high in P | 3.6 | 0.028035861 | 1.6 | 907 | 9 | 15 | 21 | 23 | 39 | 87 | N | P | N | N | N | N | N | N |

TABLE 16-continued

Genes that Are Differentially Methylated between Nulliparous and Parous CD24+ Breast Epithelial Cells

| | | | | SAGE-seq | | | | | | | | ChIP-seq | | | MSDK-seq | | |
|---|---|---|---|---|---|---|---|---|---|---|---|---|---|---|---|---|---|
| | | | | | Nulliparous (NP) | | | | Parous (P) | | | | | | | | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | GeneBody Met | P GeneBody Met | NP Pro-moter Met | P Pro-moter Met |
| FAM178A | high in P | 2.7 | 0.028042032 | 1.6 | 908 | 20 | 69 | 60 | 94 | 145 | 90 | N | N | NP | N | N | N | N |
| ID1 | high in P | 1.6 | 0.028112658 | 1.6 | 909 | 323 | 271 | 341 | 507 | 479 | 518 | N | N | N | N | N | N | N |
| TTLL4 | high in P | 2.5 | 0.028151056 | 1.6 | 910 | 751 | 427 | 377 | 1414 | 1079 | 847 | N | N | N | N | N | N | N |
| TUBB2B | high in P | 3.5 | 0.028162713 | 1.6 | 911 | 115 | 56 | 26 | 144 | 143 | 168 | N | N | N | N | N | N | N |
| AS3MT | high in P | 2.4 | 0.02821551 | 1.5 | 912 | 10 | 15 | 19 | 27 | 24 | 26 | N | N | N | N | N | N | N |
| RDH5 | high in P | 5.6 | 0.028225528 | 1.5 | 913 | 28 | 22 | 107 | 125 | 143 | 123 | N | N | N | N | N | N | N |
| MET | high in P | 2.5 | 0.028291621 | 1.5 | 914 | 22 | 71 | 37 | 83 | 70 | 79 | N | N | N | N | N | N | N |
| RIPK4 | high in P | 2.5 | 0.028356761 | 1.5 | 915 | 52 | 39 | 45 | 88 | 60 | 109 | N | N | N | N | N | N | N |
| PROSC | high in P | 1.8 | 0.02836636 | 1.5 | 916 | 50 | 79 | 74 | 124 | 99 | 121 | N | N | N | N | N | N | N |
| ATP5J2 | high in P | 2.8 | 0.028419844 | 1.5 | 917 | 95 | 48 | 165 | 232 | 417 | 187 | N | N | N | N | N | N | N |
| LOC400043 | high in P | 3.4 | 0.028426015 | 1.5 | 918 | 42 | 113 | 220 | 282 | 343 | 291 | NA | NA | N | N | N | N | N |
| LOC286359 | high in P | 2.4 | 0.028519953 | 1.5 | 919 | 32 | 15 | 15 | 37 | 39 | 40 | NA | NA | N | N | N | N | N |
| SDF2 | high in P | 2.4 | 0.028542581 | 1.5 | 920 | 21 | 56 | 36 | 57 | 76 | 101 | N | N | N | N | N | N | N |
| FAM91A1 | high in P | 1.7 | 0.028596064 | 1.5 | 921 | 96 | 145 | 111 | 171 | 185 | 191 | N | N | N | N | N | N | N |
| SIP1 | high in P | 2.3 | 0.028633091 | 1.5 | 922 | 22 | 42 | 32 | 83 | 56 | 53 | N | N | N | N | N | N | N |
| FBXO10 | high in P | 3.9 | 0.028645433 | 1.5 | 923 | 18 | 40 | 90 | 107 | 113 | 123 | N | N | N | N | N | N | N |
| HMOX1 | high in P | 4.0 | 0.028683832 | 1.5 | 924 | 140 | 802 | 894 | 1404 | 1606 | 3584 | N | N | N | N | N | N | N |
| JAGN1 | high in P | 2.3 | 0.028848396 | 1.5 | 925 | 138 | 304 | 298 | 653 | 515 | 391 | N | P | N | N | N | N | N |
| SNORD22 | high in P | 3.7 | 0.028877194 | 1.5 | 926 | 100 | 33 | 25 | 113 | 98 | 229 | N | N | N | N | N | N | N |
| SMG6 | high in P | 3.2 | 0.02891285 | 1.5 | 927 | 84 | 219 | 403 | 606 | 542 | 496 | N | N | N | N | N | N | N |
| C7orf54 | high in P | 2.1 | 0.028929306 | 1.5 | 928 | 7 | 8 | 8 | 9 | 15 | 13 | N | N | N | N | N | N | N |
| SLC25A26 | high in P | 2.5 | 0.028970447 | 1.5 | 929 | 304 | 214 | 170 | 393 | 437 | 448 | N | N | N | N | N | N | N |
| ALG13 | high in P | 2.6 | 0.029027359 | 1.5 | 930 | 46 | 35 | 31 | 80 | 102 | 48 | N | P | N | N | N | N | N |
| ATP2A3 | high in P | 2.0 | 0.029065757 | 1.5 | 931 | 55 | 100 | 122 | 167 | 152 | 217 | N | N | N | N | N | N | N |
| ACVRL1 | high in P | 6.6 | 0.029097984 | 1.5 | 932 | 16 | 19 | 19 | 120 | 70 | 19 | N | N | N | N | N | N | N |
| SLC34A2 | high in P | 3.6 | 0.02914461 | 1.5 | 933 | 543 | 2644 | 3885 | 9720 | 9403 | 4870 | N | N | N | N | N | N | N |
| PRR12 | high in P | 3.3 | 0.029157639 | 1.5 | 934 | 55 | 128 | 213 | 423 | 342 | 198 | N | N | N | N | N | N | N |
| SLC13A3 | high in P | 2.1 | 0.029229635 | 1.5 | 935 | 18 | 14 | 25 | 45 | 32 | 30 | N | N | N | N | N | N | N |
| VCAM1 | high in P | 2.3 | 0.029263234 | 1.5 | 936 | 7 | 15 | 12 | 17 | 23 | 28 | N | N | N | N | N | N | N |
| GNAZ | high in P | 2.2 | 0.0293750 | 1.5 | 937 | 11 | 32 | 22 | 46 | 39 | 52 | N | N | N | N | N | N | N |
| BTN2A2 | high in P | 3.0 | 0.029388028 | 1.5 | 938 | 167 | 99 | 61 | 427 | 168 | 271 | N | P | N | N | N | N | N |
| KIAA1632 | high in P | 1.9 | 0.029412027 | 1.5 | 939 | 36 | 58 | 58 | 79 | 65 | 102 | N | N | N | N | N | N | N |
| DFFB | high in P | 2.3 | 0.029470996 | 1.5 | 940 | 11 | 14 | 24 | 41 | 29 | 31 | N | N | N | N | N | N | N |
| GYS1 | high in P | 3.1 | 0.029484024 | 1.5 | 941 | 450 | 241 | 532 | 1526 | 1543 | 555 | N | N | N | N | N | N | N |
| RAB14 | high in P | 1.8 | 0.029527222 | 1.5 | 942 | 1157 | 1882 | 1740 | 3428 | 2642 | 2769 | N | N | N | P | N | N | N |
| SHISA5 | high in P | 2.0 | 0.029554649 | 1.5 | 943 | 363 | 686 | 438 | 1030 | 976 | 714 | N | N | N | N | N | N | N |
| PLAU | high in P | 7.9 | 0.029634874 | 1.5 | 944 | 221 | 3397 | 1353 | 14594 | 10109 | 2348 | N | N | N | N | N | N | N |
| NCBP1 | high in P | 3.2 | 0.029810409 | 1.5 | 945 | 88 | 44 | 42 | 99 | 149 | 136 | N | N | N | N | N | N | N |
| NID1 | high in P | 3.3 | 0.029934517 | 1.5 | 946 | 15 | 15 | 15 | 53 | 25 | 18 | N | P | N | N | N | N | N |
| ZNF828 | high in P | 2.1 | 0.029998971 | 1.5 | 947 | 13 | 13 | 12 | 25 | 21 | 16 | N | N | N | N | N | N | N |
| C13orf33 | high in P | 3.4 | 0.030035998 | 1.5 | 948 | 16 | 22 | 16 | 44 | 21 | 32 | N | P | N | N | N | N | N |
| LMTK2 | high in P | 2.1 | 0.030129937 | 1.5 | 949 | 334 | 168 | 274 | 607 | 521 | 470 | N | N | N | N | N | N | N |
| NSMCE4A | high in P | 1.9 | 0.03019302 | 1.5 | 950 | 4 | 4 | 5 | 14 | 9 | 7 | N | N | N | N | N | N | N |
| LOC147804 | high in P | 2.4 | 0.030237589 | 1.5 | 951 | 15 | 16 | 25 | 46 | 37 | 26 | N | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | MSDK-seq | | | |
|---|---|---|---|---|---|---|---|---|---|---|---|---|---|---|---|---|---|---|
| | | | | | | Nulliparous (NP) | | | | Parous (P) | | | NP | P | GeneBody | GeneBody | Pro-moter | Pro-moter |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | NP | Met | Met | Met | Met |
| CAMK2D | high in P | 2.3 | 0.030271873 | 1.5 | 952 | 73 | 46 | 36 | 128 | 70 | 124 | N | N | N | N | N | N | N |
| PRDX3 | high in P | 3.2 | 0.030337013 | 1.5 | 953 | 1067 | 368 | 539 | 1991 | 1659 | 11169 | N | N | N | N | N | N | N |
| wwOX | high in P | 3.5 | 0.030390496 | 1.5 | 954 | 15 | 20 | 42 | 64 | 58 | 46 | N | N | N | N | N | N | N |
| FABP4 | high in P | 3.7 | 0.030396668 | 1.5 | 955 | 6 | 20 | 17 | 33 | 25 | 101 | N | N | N | N | N | N | N |
| AKAP11 | high in P | 2.0 | 0.030439866 | 1.5 | 956 | 18 | 27 | 24 | 60 | 35 | 29 | N | N | N | N | N | N | N |
| C10orf35 | high in P | 3.2 | 0.030457693 | 1.5 | 957 | 142 | 90 | 248 | 531 | 497 | 224 | N | N | N | N | N | N | N |
| NSFL1C | high in P | 2.6 | 0.030538604 | 1.5 | 958 | 1161 | 978 | 2653 | 5488 | 4855 | 2303 | N | N | N | N | N | N | N |
| TFIP11 | high in P | 1.8 | 0.030574259 | 1.5 | 959 | 164 | 214 | 269 | 387 | 456 | 297 | N | N | N | N | N | N | N |
| LSS | high in P | 2.3 | 0.030580431 | 1.5 | 960 | 33 | 28 | 31 | 62 | 44 | 59 | N | N | N | N | N | N | N |
| SCNM1 | high in P | 6.7 | 0.030597573 | 1.5 | 961 | 11 | 17 | 81 | 167 | 148 | 56 | N | N | N | N | N | N | N |
| ADAMTS1 | high in P | 3.0 | 0.030692883 | 1.5 | 962 | 32 | 28 | 28 | 41 | 41 | 59 | N | N | N | N | N | N | N |
| NIN | high in P | 1.8 | 0.030735395 | 1.5 | 963 | 67 | 72 | 73 | 125 | 97 | 103 | N | N | N | N | N | N | N |
| ITGB5 | high in P | 3.7 | 0.03076008 | 1.5 | 964 | 793 | 2008 | 4089 | 7176 | 7228 | 3969 | N | N | N | N | N | N | N |
| ACO1 | high in P | 1.9 | 0.030824534 | 1.5 | 965 | 49 | 75 | 40 | 89 | 78 | 96 | N | N | N | N | N | N | N |
| LOC254559 | high in P | 2.2 | 0.030846476 | 1.5 | 966 | 8 | 11 | 9 | 38 | 18 | 14 | N | N | N | N | N | N | N |
| PDE4D | high in P | 2.8 | 0.030852647 | 1.5 | 967 | 17 | 18 | 18 | 33 | 31 | 23 | N | N | N | N | N | N | N |
| MAD2L1BP | high in P | 3.5 | 0.030858818 | 1.5 | 968 | 53 | 25 | 51 | 221 | 70 | 100 | N | N | N | N | N | N | N |
| NARG2 | high in P | 1.7 | 0.030893102 | 1.5 | 969 | 17 | 20 | 23 | 32 | 26 | 28 | N | N | N | N | N | N | N |
| SOAT1 | high in P | 2.2 | 0.030927386 | 1.5 | 970 | 16 | 41 | 23 | 53 | 46 | 39 | N | N | N | N | N | N | N |
| PAG1 | high in P | 2.6 | 0.030965099 | 1.5 | 971 | 40 | 36 | 37 | 108 | 73 | 46 | N | N | N | N | N | N | N |
| OXR1 | high in P | 1.8 | 0.031028867 | 1.5 | 972 | 114 | 131 | 122 | 168 | 193 | 285 | N | P | N | N | N | N | N |
| MRPS7 | high in P | 2.1 | 0.031063837 | 1.5 | 973 | 266 | 367 | 477 | 687 | 922 | 551 | N | N | N | N | N | N | N |
| UBASH3B | high in P | 3.5 | 0.031070008 | 1.5 | 974 | 44 | 132 | 148 | 168 | 216 | 398 | N | P | N | N | N | N | N |
| USP13 | high in P | 2.4 | 0.031076179 | 1.5 | 975 | 48 | 107 | 170 | 198 | 216 | 260 | N | N | N | N | N | N | N |
| USP54 | high in P | 6.5 | 0.031140634 | 1.5 | 976 | 639 | 141 | 102 | 812 | 509 | 1363 | N | P | N | N | N | N | N |
| ENDOG | high in P | 3.5 | 0.031255828 | 1.5 | 977 | 108 | 99 | 165 | 513 | 368 | 153 | N | P | N | N | N | N | N |
| C20orf20 | high in P | 2.0 | 0.031288741 | 1.5 | 978 | 74 | 58 | 51 | 103 | 90 | 102 | N | N | N | N | N | N | N |
| ADNP | high in P | 3.8 | 0.031343596 | 1.5 | 979 | 224 | 108 | 84 | 318 | 256 | 304 | N | P | N | N | N | N | N |
| DSC3 | high in P | 3.4 | 0.031364852 | 1.5 | 980 | 34 | 89 | 107 | 260 | 220 | 105 | P | P | N | N | N | N | N |
| CNGB1 | high in P | 1.8 | 0.031390222 | 1.5 | 981 | 16 | 16 | 11 | 21 | 25 | 22 | N | N | N | N | N | N | N |
| RBM19 | high in P | 3.8 | 0.031462905 | 1.5 | 982 | 105 | 102 | 304 | 422 | 377 | 323 | P | P | N | N | N | N | N |
| DDA1 | high in P | 2.4 | 0.031509531 | 1.5 | 983 | 1113 | 1381 | 2923 | 5968 | 6884 | 2528 | N | N | N | N | N | N | N |
| KIAA2018 | high in P | 1.7 | 0.031565071 | 1.5 | 984 | 142 | 160 | 162 | 368 | 224 | 225 | N | N | N | N | N | N | N |
| FAM76B | high in P | 1.8 | 0.031660381 | 1.5 | 985 | 51 | 45 | 27 | 72 | 71 | 65 | N | N | N | N | N | N | N |
| SYNGR1 | high in P | 2.3 | 0.031698779 | 1.5 | 986 | 131 | 79 | 203 | 406 | 304 | 232 | N | N | N | N | N | P | P |
| GPR143 | high in P | 1.8 | 0.031710436 | 1.5 | 987 | 3 | 3 | 4 | 7 | 6 | 6 | P | P | N | N | N | N | N |
| RTKN2 | high in P | 2.1 | 0.031716607 | 1.5 | 988 | 18 | 16 | 24 | 29 | 35 | 42 | N | N | N | N | N | N | N |
| TGDS | high in P | 2.3 | 0.031732378 | 1.5 | 989 | 12 | 13 | 20 | 36 | 29 | 27 | N | N | N | N | N | N | N |
| F12 | high in P | 2.5 | 0.031741978 | 1.5 | 990 | 100 | 48 | 71 | 165 | 187 | 104 | N | N | N | N | N | N | N |
| FAM83E | high in P | 4.7 | 0.031759805 | 1.5 | 991 | 47 | 55 | 218 | 344 | 320 | 177 | N | N | N | N | N | N | N |
| C4orf52 | high in P | 2.8 | 0.031839344 | 1.5 | 992 | 13 | 11 | 26 | 32 | 35 | 39 | NA | NA | N | N | N | N | N |
| HSD11B2 | high in P | 3.0 | 0.031922998 | 1.5 | 993 | 57 | 24 | 31 | 54 | 98 | 157 | N | N | N | N | N | N | N |
| CNTFR | high in P | 8.9 | 0.031929169 | 1.5 | 994 | 8 | 8 | 19 | 19 | 19 | 45 | N | N | N | N | N | P | P |
| CENPO | high in P | 2.4 | 0.031929169 | 1.5 | 995 | 4 | 29 | 31 | 73 | 63 | 47 | N | N | N | N | N | N | N |

TABLE 16-continued

Genes that Are Differentially Methylated between Nulliparous and Parous CD24+ Breast Epithelial Cells

| | | | | | SAGE-seq | | | | | | | | ChIP-seq | | MSDK-seq | | | |
|---|---|---|---|---|---|---|---|---|---|---|---|---|---|---|---|---|---|---|
| | | | | | | Nulliparous (NP) | | | | Parous (P) | | | NP | P | GeneBody | | Pro-moter | |
| Gene Symbol | expression pattern | Fold Change | p-value | log10 (P-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | Met P | Pro-moter NP | Met P |
| IL1B | high in P | 3.7 | 0.031963453 | 1.5 | 996 | 5 | 5 | 5 | 7 | 14 | 18 | P | P | NP | N | N | N | N |
| AKNA | high in P | 4.6 | 0.031969624 | 1.5 | 997 | 271 | 313 | 1350 | 1987 | 2027 | 1157 | N | N | N | N | N | N | N |
| DAB2 | high in P | 1.7 | 0.032025165 | 1.5 | 998 | 52 | 74 | 57 | 87 | 92 | 133 | N | N | N | N | N | N | N |
| AKAP8 | high in P | 2.3 | 0.032044792 | 1.5 | 999 | 126 | 207 | 287 | 459 | 413 | 307 | N | N | N | N | N | N | N |
| MAPK14 | high in P | 2.0 | 0.032080705 | 1.5 | 1000 | 57 | 65 | 47 | 118 | 73 | 101 | N | N | N | N | N | N | N |
| ASRGL1 | high in P | 2.7 | 0.032097161 | 1.5 | 1001 | 53 | 122 | 41 | 174 | 138 | 113 | N | P | N | N | N | N | N |
| SYDE1 | high in P | 2.0 | 0.032185614 | 1.5 | 1002 | 21 | 28 | 22 | 63 | 29 | 44 | N | N | N | N | N | N | N |
| EXD2 | high in P | 1.6 | 0.032267896 | 1.5 | 1003 | 144 | 151 | 171 | 260 | 246 | 194 | NA | NA | N | N | N | N | N |
| UTS2D | high in P | 2.0 | 0.032395433 | 1.5 | 1004 | 7 | 17 | 19 | 38 | 30 | 28 | N | N | N | N | N | N | N |
| PTPN14 | high in P | 2.2 | 0.032401604 | 1.5 | 1005 | 17 | 17 | 17 | 21 | 22 | 20 | N | N | N | N | N | N | N |
| NR2C1 | high in P | 1.8 | 0.032488001 | 1.5 | 1006 | 17 | 21 | 20 | 25 | 45 | 26 | N | N | N | N | N | N | N |
| NON | high in P | 3.2 | 0.032506514 | 1.5 | 1007 | 7 | 9 | 11 | 28 | 15 | 20 | N | N | N | N | N | N | N |
| ERP27 | high in P | 5.8 | 0.032516114 | 1.5 | 1008 | 2 | 3 | 17 | 23 | 27 | 18 | N | N | N | N | N | N | N |
| FRY | high in P | 2.2 | 0.032572319 | 1.5 | 1009 | 40 | 47 | 26 | 152 | 73 | 48 | N | N | N | N | N | N | N |
| VAC14 | high in P | 2.3 | 0.032734846 | 1.5 | 1010 | 16 | 23 | 33 | 44 | 43 | 38 | N | N | N | N | N | N | N |
| MTHFR | high in P | 1.8 | 0.032797244 | 1.5 | 1011 | 451 | 383 | 541 | 1107 | 898 | 646 | N | N | N | N | N | N | N |
| TEX264 | high in P | 2.9 | 0.032871297 | 1.5 | 1012 | 204 | 240 | 716 | 2032 | 1164 | 538 | N | N | N | N | N | N | N |
| APCDD1 | high in P | 2.5 | 0.032882268 | 1.5 | 1013 | 15 | 20 | 16 | 68 | 36 | 22 | N | N | N | N | N | N | N |
| KIAA0892 | high in P | 2.0 | 0.032912438 | 1.5 | 1014 | 169 | 392 | 415 | 721 | 724 | 551 | N | N | N | N | N | N | N |
| C20orf27 | high in P | 3.4 | 0.032951522 | 1.5 | 1015 | 78 | 125 | 235 | 352 | 367 | 233 | N | N | N | N | N | N | N |
| SMTNL2 | high in P | 4.5 | 0.032963865 | 1.5 | 1016 | 3 | 3 | 12 | 59 | 21 | 11 | N | N | N | N | N | N | N |
| UBE2I1 | high in P | 1.8 | 0.033009805 | 1.5 | 1017 | 842 | 610 | 774 | 1820 | 1344 | 1056 | N | N | N | N | N | N | N |
| MGC12982 | high in P | 3.4 | 0.033035861 | 1.5 | 1018 | 3 | 5 | 12 | 20 | 16 | 22 | NA | NA | N | N | N | N | N |
| ACAP2 | high in P | 2.0 | 0.033136657 | 1.5 | 1019 | 27 | 43 | 36 | 42 | 60 | 81 | NA | NA | N | N | N | N | N |
| SHOX2 | high in P | 5.2 | 0.033233338 | 1.5 | 1020 | 6 | 6 | 6 | 37 | 19 | 6 | N | N | N | N | N | N | N |
| BRP44 | high in P | 2.3 | 0.033253223 | 1.5 | 1021 | 3 | 4 | 4 | 9 | 6 | 14 | N | P | N | N | N | N | N |
| PLEKHM1P | high in P | 9.9 | 0.033395049 | 1.5 | 1022 | 40 | 28 | 281 | 300 | 355 | 269 | NA | P | N | N | N | N | P |
| DCTD | high in P | 1.7 | 0.033393102 | 1.5 | 1023 | 59 | 71 | 46 | 84 | 107 | 94 | N | N | N | N | N | N | N |
| ADRA2C | high in P | 9.2 | 0.033448642 | 1.5 | 1024 | 4 | 17 | 53 | 128 | 124 | 44 | P | P | N | N | N | N | N |
| COLQ | high in P | 2.2 | 0.033582351 | 1.5 | 1025 | 35 | 13 | 26 | 41 | 62 | 53 | N | P | N | N | N | N | N |
| C9orf45 | high in P | 2.3 | 0.033606349 | 1.5 | 1026 | 22 | 22 | 37 | 42 | 46 | 73 | NA | NA | N | N | N | N | N |
| WDR81 | high in P | 3.8 | 0.033639262 | 1.5 | 1027 | 31 | 126 | 279 | 686 | 350 | 265 | NA | NA | N | N | N | N | N |
| C8orf46 | high in P | 3.0 | 0.033721544 | 1.5 | 1028 | 6 | 14 | 28 | 36 | 51 | 38 | N | N | N | N | N | N | N |
| TMEM185B | high in P | 1.9 | 0.033750343 | 1.5 | 1029 | 9 | 11 | 10 | 15 | 15 | 18 | N | N | N | N | N | N | N |
| METTL2A | high in P | 2.7 | 0.033791484 | 1.5 | 1030 | 173 | 71 | 90 | 254 | 221 | 193 | N | N | N | N | N | N | N |
| MOXD1 | high in P | 2.2 | 0.033803826 | 1.5 | 1031 | 7 | 7 | 7 | 11 | 10 | 13 | N | P | N | N | N | N | N |
| C20orf4 | high in P | 2.5 | 0.033849081 | 1.5 | 1032 | 61 | 58 | 139 | 300 | 233 | 127 | N | N | N | N | N | N | N |
| CHD7 | high in P | 1.9 | 0.033855252 | 1.5 | 1033 | 87 | 145 | 110 | 144 | 185 | 222 | N | N | N | N | N | N | N |
| C8orf37 | high in P | 3.0 | 0.033983475 | 1.5 | 1034 | 41 | 28 | 33 | 261 | 99 | 46 | N | N | N | N | N | N | N |
| PHB2 | high in P | 3.1 | 0.033997532 | 1.5 | 1035 | 4056 | 2754 | 9298 | 11952 | 14955 | 9259 | N | N | N | N | N | N | N |
| CHEK1 | high in P | 2.4 | 0.034017759 | 1.5 | 1036 | 26 | 51 | 45 | 110 | 85 | 53 | N | N | N | N | N | N | N |
| PTPN6 | high in P | 3.6 | 0.034060957 | 1.5 | 1037 | 42 | 92 | 183 | 492 | 278 | 153 | N | N | N | N | N | N | N |
| PABPN1 | high in P | 2.3 | 0.034067128 | 1.5 | 1038 | 1041 | 570 | 743 | 1310 | 1573 | 1778 | N | N | N | N | N | N | N |
| CWF19L2 | high in P | 2.6 | 0.034113069 | 1.5 | 1039 | 57 | 71 | 25 | 142 | 97 | 78 | N | N | N | N | N | N | N |

TABLE 16-continued

Genes that Are Differentially Methylated between Nulliparous and Parous CD24+ Breast Epithelial Cells

| | | | | | SAGE-seq | Nulliparous (NP) | | | | Parous (P) | | | | ChIP-seq | | MSDK-seq | | |
|---|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | GeneBody Met | P GeneBody Met | NP Pro-moter Met | P Pro-moter Met |
| NRN1 | high in P | 2.4 | 0.034143239 | 1.5 | 1040 | 5 | 10 | 7 | 16 | 12 | 21 | P | P | N | N | N | N | N |
| HLA-DRB5 | high in P | 17.0 | 0.034289975 | 1.5 | 1041 | 3 | 292 | 29 | 1046 | 418 | 133 | N | N | N | N | N | N | N |
| SCAPER | high in P | 2.2 | 0.034361286 | 1.5 | 1042 | 18 | 18 | 24 | 29 | 28 | 36 | N | N | N | N | N | N | N |
| THOC2 | high in P | 1.7 | 0.034457282 | 1.5 | 1043 | 30 | 42 | 29 | 55 | 59 | 42 | N | N | N | N | N | N | N |
| FIP1L1 | high in P | 2.5 | 0.034463453 | 1.5 | 1044 | 5 | 32 | 37 | 65 | 55 | 65 | N | N | N | N | N | N | N |
| SHARPIN | high in P | 7.7 | 0.034469624 | 1.5 | 1045 | 78 | 243 | 950 | 1694 | 1485 | 699 | N | N | N | N | N | N | N |
| SYNE2 | high in P | 2.2 | 0.03453065 | 1.5 | 1046 | 134 | 239 | 138 | 376 | 232 | 338 | N | N | N | N | N | N | N |
| KRT71 | high in P | 2.8 | 0.034544364 | 1.5 | 1047 | 11 | 5 | 7 | 11 | 24 | 55 | N | N | N | N | N | N | N |
| LDLR | high in P | 2.9 | 0.034582076 | 1.5 | 1048 | 4198 | 3717 | 9555 | 11174 | 10997 | 11576 | N | N | N | N | N | N | N |
| ZNF37A | high in P | 1.9 | 0.034657501 | 1.5 | 1049 | 29 | 52 | 41 | 50 | 68 | 72 | N | N | N | N | N | P | N |
| EIF2AK4 | high in P | 2.1 | 0.034678072 | 1.5 | 1050 | 18 | 40 | 24 | 54 | 42 | 37 | N | N | N | N | N | N | N |
| C12orf34 | high in P | 2.1 | 0.034693157 | 1.5 | 1051 | 8 | 13 | 18 | 23 | 28 | 22 | N | N | N | N | N | N | N |
| CEBPD | high in P | 2.5 | 0.034699328 | 1.5 | 1052 | 1983 | 3003 | 6209 | 7677 | 7243 | 7347 | N | P | N | N | N | N | N |
| NOG | high in P | 2.6 | 0.03477681 | 1.5 | 1053 | 6 | 6 | 6 | 9 | 12 | 34 | N | N | N | N | N | N | N |
| DES | high in P | 1.9 | 0.034806295 | 1.5 | 1054 | 4 | 13 | 10 | 16 | 23 | 23 | P | P | N | N | N | N | N |
| DDRGK1 | high in P | 1.9 | 0.034909147 | 1.5 | 1055 | 178 | 289 | 218 | 523 | 388 | 308 | N | N | N | N | N | N | N |
| LOC643008 | high in P | 2.1 | 0.034931775 | 1.5 | 1056 | 19 | 15 | 15 | 24 | 28 | 40 | N | N | N | N | P | N | N |
| BMPR1A | high in P | 1.9 | 0.034968801 | 1.5 | 1057 | 53 | 105 | 57 | 158 | 135 | 96 | N | N | N | N | N | N | N |
| DCAF6 | high in P | 2.1 | 0.034996229 | 1.5 | 1058 | 76 | 63 | 48 | 107 | 93 | 151 | NA | NA | N | N | P | N | N |
| SNX10 | high in P | 2.2 | 0.035035313 | 1.5 | 1059 | 16 | 26 | 7 | 49 | 36 | 27 | N | N | N | N | N | N | N |
| MAPK1 | high in P | 2.1 | 0.035049712 | 1.5 | 1060 | 34 | 78 | 68 | 80 | 97 | 133 | N | N | N | N | N | N | N |
| H1FO | high in P | 6.1 | 0.035122394 | 1.5 | 1061 | 764 | 306 | 178 | 6877 | 879 | 897 | N | N | N | N | N | N | N |
| RNF160 | high in P | 2.3 | 0.035143651 | 1.5 | 1062 | 81 | 59 | 47 | 107 | 88 | 118 | NA | NA | N | N | N | N | N |
| BMP2 | high in P | 2.4 | 0.035149822 | 1.5 | 1063 | 81 | 68 | 30 | 194 | 124 | 93 | P | N | N | N | N | N | N |
| PTGER2 | high in P | 1.8 | 0.035191648 | 1.5 | 1064 | 6 | 9 | 11 | 20 | 19 | 12 | N | N | N | N | N | N | N |
| PANX2 | high in P | 2.2 | 0.035210162 | 1.5 | 1065 | 47 | 63 | 41 | 105 | 115 | 60 | N | N | N | N | N | N | P |
| CSPP1 | high in P | 1.8 | 0.035247189 | 1.5 | 1066 | 53 | 51 | 48 | 65 | 96 | 82 | N | N | N | N | N | N | N |
| RNF123 | high in P | 2.1 | 0.035310957 | 1.5 | 1067 | 187 | 220 | 360 | 482 | 528 | 372 | N | N | N | N | N | N | N |
| FAM55C | high in P | 2.0 | 0.035317128 | 1.5 | 1068 | 153 | 91 | 144 | 296 | 218 | 212 | N | N | N | N | N | N | N |
| ZNF222 | high in P | 2.2 | 0.0353233 | 1.5 | 1069 | 14 | 4 | 8 | 20 | 13 | 25 | N | N | N | N | N | N | N |
| C1GALT1C1 | high in P | 3.4 | 0.035367869 | 1.5 | 1070 | 3 | 21 | 9 | 45 | 20 | 31 | N | N | N | N | N | N | N |
| EIF4E3 | high in P | 1.8 | 0.03540181 | 1.5 | 1071 | 22 | 38 | 26 | 38 | 44 | 50 | N | N | N | N | N | N | N |
| FBXW5 | high in P | 2.0 | 0.035496092 | 1.5 | 1072 | 7268 | 8189 | 12575 | 25579 | 18307 | 12782 | N | N | N | N | N | N | N |
| LIMS3 | high in P | 4.0 | 0.035514605 | 1.4 | 1073 | 1731 | 1055 | 4435 | 7056 | 7774 | 3959 | N | N | N | N | N | N | N |
| TYW3 | high in P | 2.5 | 0.035611286 | 1.4 | 1074 | 50 | 10 | 24 | 88 | 57 | 62 | N | N | N | N | N | N | N |
| IKBKB | high in P | 1.8 | 0.035651056 | 1.4 | 1075 | 40 | 91 | 69 | 136 | 109 | 96 | N | N | N | N | N | N | N |
| MRPS35 | high in P | 1.8 | 0.035716196 | 1.4 | 1076 | 290 | 264 | 252 | 464 | 403 | 580 | N | N | N | N | N | N | N |
| SLC31A1 | high in P | 1.9 | 0.035722367 | 1.4 | 1077 | 190 | 202 | 269 | 376 | 359 | 320 | N | N | N | N | N | N | N |
| RPL12 | high in P | 2.5 | 0.035753566 | 1.4 | 1078 | 25 | 32 | 31 | 59 | 33 | 59 | N | N | N | N | N | N | N |
| C6orf48 | high in P | 2.8 | 0.035764194 | 1.4 | 1079 | 26399 | 10589 | 17402 | 30861 | 50250 | 44261 | N | N | N | N | N | N | N |
| AKAP5 | high in P | 2.0 | 0.035807392 | 1.4 | 1080 | 769 | 454 | 548 | 909 | 1013 | 1516 | N | N | N | N | N | N | N |
| PCDH1 | high in P | 2.0 | 0.035822477 | 1.4 | 1081 | 7 | 9 | 11 | 20 | 12 | 18 | N | N | N | N | N | N | N |
| PCDH1 | high in P | 2.0 | 0.035822477 | 1.4 | 1082 | 170 | 215 | 349 | 471 | 464 | 348 | N | N | N | N | N | N | N |
| LRWD1 | high in P | 1.9 | 0.035828648 | 1.4 | 1083 | 25 | 79 | 71 | 121 | 107 | 125 | N | N | N | N | N | N | N |

TABLE 16-continued

Genes that Are Differentially Methylated between Nulliparous and Parous CD24+ Breast Epithelial Cells

| | | | | SAGE-seq | | Nulliparous (NP) | | | Parous (P) | | | ChIP-seq | | | MSDK-seq | | |
|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | P GeneBody Met | Pro-moter Met | Pro-moter Met |
| DCN | high in P | 4.1 | 0.035923958 | 1.4 | 1084 | 31 | 31 | 31 | 45 | 40 | 31 | N | P | NP | N | N | N |
| ATF7IP | high in P | 1.9 | 0.035958928 | 1.4 | 1085 | 19 | 26 | 21 | 34 | 45 | 27 | N | N | N | N | N | N |
| VANGL2 | high in P | 2.0 | 0.035997326 | 1.4 | 1086 | 105 | 99 | 99 | 328 | 172 | 131 | N | N | N | N | N | N |
| FBN2 | high in P | 1.8 | 0.036015839 | 1.4 | 1087 | 9 | 9 | 9 | 14 | 12 | 12 | N | N | N | N | N | N |
| RAB3IP | high in P | 1.9 | 0.036070008 | 1.4 | 1088 | 43 | 108 | 93 | 160 | 113 | 107 | N | N | N | N | N | N |
| EXTL3 | high in P | 7.4 | 0.036149547 | 1.4 | 1089 | 122 | 369 | 1394 | 2564 | 2242 | 1032 | N | N | N | N | N | N |
| CD74 | high in P | 2.6 | 0.036176289 | 1.4 | 1090 | 222 | 158 | 128 | 453 | 594 | 222 | N | N | N | N | N | N |
| MX2 | high in P | 2.1 | 0.036312054 | 1.4 | 1091 | 9 | 11 | 14 | 20 | 18 | 20 | N | N | N | N | N | N |
| C14orf73 | high in P | 3.1 | 0.036318225 | 1.4 | 1092 | 2 | 18 | 8 | 49 | 30 | 18 | N | N | N | N | N | N |
| ST7L | high in P | 2.8 | 0.036344281 | 1.4 | 1093 | 12 | 39 | 46 | 84 | 86 | 49 | N | N | N | N | N | N |
| FLT1 | high in P | 1.7 | 0.036375823 | 1.4 | 1094 | 28 | 40 | 32 | 46 | 41 | 46 | N | P | N | N | N | N |
| DSE | high in P | 2.4 | 0.036444234 | 1.4 | 1095 | 32 | 34 | 18 | 57 | 38 | 62 | N | N | N | N | N | N |
| C16orf54 | high in P | 1.8 | 0.036570557 | 1.4 | 1096 | 37 | 17 | 28 | 62 | 48 | 52 | N | N | N | N | N | N |
| C3orf1 | high in P | 2.7 | 0.036640496 | 1.4 | 1097 | 185 | 95 | 84 | 288 | 260 | 196 | N | N | N | N | N | N |
| RUVBL1 | high in P | 1.8 | 0.036646668 | 1.4 | 1098 | 36 | 71 | 49 | 84 | 78 | 81 | N | N | N | N | N | N |
| KRT5 | high in P | 2.9 | 0.036751577 | 1.4 | 1099 | 1288 | 3829 | 3293 | 3939 | 7495 | 14672 | N | N | N | N | N | N |
| PIK3C2B | high in P | 1.9 | 0.036773519 | 1.4 | 1100 | 26 | 29 | 21 | 46 | 33 | 34 | N | N | N | N | N | N |
| PDP1 | high in P | 1.7 | 0.036777969 | 1.4 | 1101 | 17 | 24 | 22 | 36 | 33 | 26 | N | NA | N | N | N | N |
| EFNA5 | high in P | 4.3 | 0.036792032 | 1.4 | 1102 | 32 | 198 | 73 | 322 | 257 | 158 | N | N | N | N | N | N |
| HBS1L | high in P | 1.8 | 0.036798204 | 1.4 | 1103 | 65 | 45 | 71 | 110 | 102 | 127 | N | N | N | N | N | N |
| FLJ20184 | high in P | 1.8 | 0.036893513 | 1.4 | 1104 | NA | NA | NA | NA | NA | NA | NA | NA | N | N | N | N |
| C5orf75 | high in P | 2.5 | 0.036911341 | 1.4 | 1105 | NA | NA | NA | NA | NA | NA | NA | NA | N | N | N | N |
| ZNF518B | high in P | 2.7 | 0.036951111 | 1.4 | 1106 | 32 | 22 | 27 | 53 | 60 | 36 | P | P | N | N | N | N |
| PPAP2B | high in P | 5.4 | 0.037066991 | 1.4 | 1107 | 60 | 778 | 222 | 1648 | 962 | 724 | N | N | N | N | N | N |
| SNX8 | high in P | 2.2 | 0.037115675 | 1.4 | 1108 | 168 | 133 | 219 | 341 | 440 | 233 | P | N | N | N | N | N |
| IFITM2 | high in P | 4.2 | 0.037142416 | 1.4 | 1109 | 241 | 903 | 697 | 4035 | 1618 | 860 | N | P | N | N | N | N |
| LRCH4 | high in P | 2.3 | 0.037186986 | 1.4 | 1110 | 368 | 343 | 937 | 1654 | 1538 | 723 | N | P | N | N | N | N |
| STAC | high in P | 2.8 | 0.037232241 | 1.4 | 1111 | 5 | 12 | 5 | 12 | 15 | 34 | N | N | N | N | N | N |
| MDK | high in P | 2.1 | 0.037270639 | 1.4 | 1112 | 967 | 517 | 1435 | 1856 | 2080 | 2331 | P | N | N | N | N | N |
| RPS19BP1 | high in P | 3.8 | 0.037322065 | 1.4 | 1113 | 72 | 116 | 248 | 367 | 422 | 211 | P | P | N | N | N | N |
| LIG4 | high in P | 1.6 | 0.037335093 | 1.4 | 1114 | 101 | 112 | 89 | 195 | 130 | 135 | N | P | N | N | N | N |
| CBS | high in P | 4.4 | 0.037341264 | 1.4 | 1115 | 101 | 162 | 120 | 479 | 583 | 146 | N | N | N | N | N | N |
| MRPS25 | high in P | 2.3 | 0.037424918 | 1.4 | 1116 | 220 | 101 | 165 | 302 | 334 | 311 | P | N | N | N | N | N |
| TSPYL2 | high in P | 2.4 | 0.037436574 | 1.4 | 1117 | 2051 | 703 | 1691 | 4972 | 2342 | 4236 | N | P | N | N | N | N |
| XPO7 | high in P | 2.4 | 0.037516799 | 1.4 | 1118 | 26 | 23 | 28 | 44 | 49 | 33 | N | N | N | N | N | N |
| CEP63 | high in P | 1.6 | 0.037645708 | 1.4 | 1119 | 22 | 35 | 32 | 44 | 43 | 37 | N | N | N | N | N | N |
| ZNF623 | high in P | 1.6 | 0.037645708 | 1.4 | 1120 | 44 | 34 | 45 | 61 | 67 | 68 | N | P | N | N | N | N |
| TAL1 | high in P | 2.0 | 0.037750617 | 1.4 | 1121 | 6 | 7 | 7 | 18 | 9 | 12 | P | N | N | N | N | N |
| HTR7P | high in P | 2.7 | 0.037836327 | 1.4 | 1122 | NA | NA | NA | NA | NA | NA | N | N | N | N | N | N |
| TGFBI | high in P | 1.9 | 0.037852098 | 1.4 | 1123 | 13 | 15 | 16 | 37 | 19 | 22 | P | N | N | N | N | N |
| SAP30L | high in P | 2.1 | 0.037858269 | 1.4 | 1124 | 26 | 56 | 38 | 72 | 65 | 50 | N | NA | N | N | N | N |
| LOC401093 | high in P | 1.7 | 0.037941923 | 1.4 | 1125 | 41 | 42 | 48 | 61 | 57 | 63 | NA | NA | N | N | N | N |
| GINS1 | high in P | 3.9 | 0.037954951 | 1.4 | 1126 | 20 | 11 | 31 | 28 | 65 | 59 | N | N | N | N | N | N |
| HOXC11 | high in P | 2.2 | 0.037961122 | 1.4 | 1127 | 2 | 6 | 7 | 12 | 19 | 16 | P | P | N | N | N | N |

TABLE 16-continued

Genes that Are Differentially Methylated between Nulliparous and Parous CD24+ Breast Epithelial Cells

| | | | | | SAGE-seq | Nulliparous (NP) | | | | Parous (P) | | | ChIP-seq | | | | MSDK-seq | | |
|---|---|---|---|---|---|---|---|---|---|---|---|---|---|---|---|---|---|---|---|
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | NP | P | GeneBody Met | GeneBody Met | Pro-moter Met | Pro-moter Met |
| | | | | | | | | | | | | | NP | P | NP | P | NP | P |
| NAGK | high in P | 2.1 | 0.038802489 | 1.4 | 1128 | 66 | 161 | 101 | 195 | 166 | 209 | N | N | N | N | N | N | N | N |
| ACCN3 | high in P | 5.3 | 0.038090716 | 1.4 | 1129 | 39 | 22 | 163 | 135 | 186 | 256 | N | N | N | N | N | N | N | N |
| SLC25A37 | high in P | 2.3 | 0.038172998 | 1.4 | 1130 | 752 | 1900 | 770 | 1697 | 2675 | 3129 | N | N | P | N | N | N | N | N |
| KLC1 | high in P | 3.6 | 0.038231967 | 1.4 | 1131 | 1091 | 718 | 3585 | 4153 | 4170 | 4084 | N | N | N | N | N | N | N | N |
| SYT8 | high in P | 6.9 | 0.038423272 | 1.4 | 1132 | 21 | 19 | 34 | 31 | 86 | 548 | N | N | N | N | N | N | N | N |
| GLRX | high in P | 2.2 | 0.038632405 | 1.4 | 1133 | 634 | 390 | 321 | 749 | 740 | 965 | N | N | N | N | N | N | N | N |
| NUDT4 | high in P | 4.7 | 0.03866669 | 1.4 | 1134 | 45 | 101 | 226 | 578 | 364 | 167 | N | N | N | N | N | N | N | N |
| ADAM15 | high in P | 3.0 | 0.038704402 | 1.4 | 1135 | 103 | 128 | 294 | 308 | 299 | 435 | N | N | N | N | N | N | N | N |
| GPAT2 | high in P | 2.1 | 0.038749657 | 1.4 | 1136 | 11 | 19 | 20 | 27 | 43 | 26 | NA | NA | N | N | N | N | N | N |
| EIF3J | high in P | 2.1 | 0.038755828 | 1.4 | 1137 | 445 | 859 | 1259 | 1383 | 2188 | 1755 | N | N | N | N | N | N | N | N |
| TYMP | high in P | 3.0 | 0.038893651 | 1.4 | 1138 | 1968 | 4763 | 6110 | 18330 | 9400 | 6361 | N | N | N | N | N | N | N | N |
| MUC20 | high in P | 2.2 | 0.038899822 | 1.4 | 1139 | 29 | 31 | 35 | 83 | 55 | 42 | N | N | N | N | N | N | N | N |
| CCND3 | high in P | 2.3 | 0.038935477 | 1.4 | 1140 | 223 | 855 | 551 | 1351 | 902 | 1241 | N | N | N | N | N | N | N | N |
| LRRC27 | high in P | 2.8 | 0.038986903 | 1.4 | 1141 | 171 | 366 | 641 | 900 | 953 | 627 | N | N | N | N | N | N | N | P |
| ALDH1L2 | high in P | 1.9 | 0.039036958 | 1.4 | 1142 | 35 | 35 | 46 | 62 | 64 | 48 | N | N | N | N | N | N | N | N |
| FBX025 | high in P | 1.8 | 0.039148039 | 1.4 | 1143 | 79 | 106 | 62 | 145 | 151 | 100 | N | N | N | N | N | N | N | N |
| CTSL1 | high in P | 2.9 | 0.039163124 | 1.4 | 1144 | 33 | 92 | 35 | 138 | 78 | 87 | N | N | N | N | N | N | N | N |
| ZNF512 | high in P | 2.3 | 0.039186437 | 1.4 | 1145 | 99 | 47 | 41 | 118 | 85 | 196 | N | N | N | N | N | N | N | N |
| FAM40B | high in P | 2.1 | 0.039239235 | 1.4 | 1146 | 20 | 19 | 39 | 52 | 47 | 42 | N | N | N | N | N | N | N | N |
| GPT2 | high in P | 2.0 | 0.039318774 | 1.4 | 1147 | 72 | 95 | 167 | 277 | 309 | 142 | N | N | N | N | N | N | N | N |
| CENPM | high in P | 2.9 | 0.03935443 | 1.4 | 1148 | 7 | 11 | 28 | 40 | 33 | 33 | N | N | N | N | N | N | N | N |
| POLD4 | high in P | 2.0 | 0.039470996 | 1.4 | 1149 | 180 | 164 | 113 | 273 | 272 | 204 | N | N | N | N | N | N | N | N |
| SMC3 | high in P | 2.8 | 0.039514879 | 1.4 | 1150 | 54 | 57 | 53 | 126 | 154 | 61 | N | N | N | N | N | N | N | N |
| SLC22A23 | high in P | 1.9 | 0.039599904 | 1.4 | 1151 | 136 | 185 | 243 | 318 | 270 | 324 | N | N | N | N | N | N | N | N |
| C1orf16 | high in P | 1.6 | 0.03962596 | 1.4 | 1152 | 103 | 109 | 98 | 165 | 158 | 123 | P | P | N | N | N | N | N | N |
| NUDT9 | high in P | 2.0 | 0.039678758 | 1.4 | 1153 | 6 | 7 | 6 | 10 | 22 | 11 | N | N | N | N | N | N | N | N |
| PAR5 | high in P | 2.7 | 0.03979121 | 1.4 | 1154 | 50 | 32 | 61 | 74 | 164 | 88 | N | N | N | N | N | N | N | N |
| SLC25A38 | high in P | 2.2 | 0.040047655 | 1.4 | 1155 | 61 | 183 | 217 | 289 | 348 | 319 | N | N | N | N | N | N | N | N |
| TTC1 | high in P | 1.8 | 0.040081939 | 1.4 | 1156 | 153 | 175 | 122 | 272 | 288 | 189 | N | N | N | N | N | N | N | N |
| ACOT7 | high in P | 3.4 | 0.040147765 | 1.4 | 1157 | 116 | 266 | 575 | 739 | 770 | 599 | N | N | N | N | N | N | N | N |
| HSPBP1 | high in P | 2.0 | 0.040164907 | 1.4 | 1158 | 218 | 259 | 360 | 630 | 348 | 548 | N | N | N | N | N | N | N | N |
| SDK2 | high in P | 2.6 | 0.040193705 | 1.4 | 1159 | 23 | 26 | 23 | 31 | 28 | 63 | NA | NA | N | N | N | N | N | N |
| LOC344967 | high in P | 2.0 | 0.040206048 | 1.4 | 1160 | 238 | 128 | 190 | 371 | 394 | 271 | NA | NA | P | N | N | N | N | N |
| DNM1P35 | high in P | 1.7 | 0.040332213 | 1.4 | 1161 | 14 | 18 | 17 | 26 | 19 | 25 | NA | NA | N | N | N | N | N | N |
| RIT1 | high in P | 2.1 | 0.04034387 | 1.4 | 1162 | 234 | 169 | 106 | 307 | 291 | 360 | N | N | N | N | N | N | N | N |
| PHB | high in P | 3.9 | 0.040417924 | 1.4 | 1163 | 16 | 61 | 127 | 174 | 218 | 129 | N | N | N | N | N | N | N | N |
| IRF5 | high in P | 2.2 | 0.040451522 | 1.4 | 1164 | 73 | 170 | 220 | 308 | 273 | 324 | P | N | P | N | N | N | N | N |
| ZNF497 | high in P | 2.5 | 0.040461122 | 1.4 | 1165 | 6 | 6 | 6 | 15 | 11 | 9 | N | N | N | N | N | N | N | N |
| ZNF500 | high in P | 2.1 | 0.040508434 | 1.4 | 1166 | 7 | 24 | 24 | 47 | 38 | 28 | N | N | N | N | N | N | N | N |
| DAK | high in P | 2.7 | 0.040640771 | 1.4 | 1167 | 88 | 148 | 235 | 321 | 330 | 225 | N | N | N | N | N | N | N | N |
| THEM4 | high in P | 2.1 | 0.040683969 | 1.4 | 1168 | 28 | 47 | 46 | 118 | 83 | 49 | N | N | N | N | N | N | N | N |
| RAPGEFL1 | high in P | 1.7 | 0.040699054 | 1.4 | 1169 | 43 | 61 | 61 | 81 | 112 | 72 | N | N | N | N | N | N | N | N |
| FANCC | high in P | 2.2 | 0.040712767 | 1.4 | 1170 | 56 | 38 | 62 | 118 | 154 | 63 | N | N | N | N | N | N | N | N |
| NAA20 | high in P | 2.6 | 0.040862932 | 1.4 | 1171 | 133 | 249 | 101 | 326 | 322 | 237 | NA | NA | N | N | N | N | N | N |

TABLE 16-continued

Genes that Are Differentially Methylated between Nulliparous and Parous CD24+ Breast Epithelial Cells

| | | | | SAGE-seq | | | | | | | | ChIP-seq | | | MSDK-seq | | |
|---|---|---|---|---|---|---|---|---|---|---|---|---|---|---|---|---|---|
| | | | | | Nulliparous (NP) | | | | Parous (P) | | | NP | | | | | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | CD24+ N74 | CD24+ N66 | GeneBody NP | GeneBody Met | Pro-moter Met | NP | Pro-moter Met P |
| ZNRF1 | high in P | 2.0 | 0.040869103 | 1.4 | 1172 | 324 | 437 | 339 | 834 | 474 | 603 | N | N | NP | N | N | N | N |
| MTMR15 | high in P | 2.5 | 0.0409363 | 1.4 | 1173 | 107 | 60 | 54 | 124 | 157 | 116 | N | N | N | N | N | N | N |
| SLC25A46 | high in P | 2.4 | 0.040985669 | 1.4 | 1174 | 10 | 36 | 21 | 44 | 77 | 30 | N | N | N | N | N | N | N |
| SURF2 | high in P | 2.4 | 0.041054238 | 1.4 | 1175 | 7 | 6 | 11 | 15 | 31 | 16 | N | N | N | N | N | N | N |
| RGS16 | high in P | 2.2 | 0.041060409 | 1.4 | 1176 | 15 | 64 | 36 | 69 | 69 | 69 | N | N | N | N | N | N | N |
| ICAM1 | high in P | 2.6 | 0.041126234 | 1.4 | 1177 | 566 | 1686 | 754 | 1846 | 1682 | 3435 | N | N | N | N | N | N | N |
| HINT3 | high in P | 3.7 | 0.041264742 | 1.4 | 1178 | 148 | 65 | 24 | 188 | 201 | 157 | N | N | N | N | N | N | N |
| IL10RA | high in P | 2.3 | 0.041296969 | 1.4 | 1179 | 6 | 6 | 7 | 14 | 9 | 10 | N | P | N | N | N | N | N |
| GDI1 | high in P | 4.8 | 0.041569871 | 1.4 | 1180 | 368 | 78 | 119 | 376 | 434 | 517 | P | N | N | N | N | N | N |
| TMEM43 | high in P | 2.9 | 0.041790661 | 1.4 | 1181 | 261 | 330 | 800 | 821 | 1094 | 832 | N | N | N | N | N | N | N |
| SETDB1 | high in P | 2.1 | 0.041948368 | 1.4 | 1182 | 87 | 139 | 161 | 241 | 243 | 175 | N | N | N | N | N | N | N |
| PTPN23 | high in P | 3.8 | 0.042180129 | 1.4 | 1183 | 650 | 656 | 3076 | 4719 | 4087 | 2117 | N | N | N | N | N | N | N |
| SLC16A13 | high in P | 3.9 | 0.0421863 | 1.4 | 1184 | 1 | 18 | 27 | 96 | 70 | 29 | N | N | N | N | N | N | N |
| NCRNA00081 | high in P | 1.8 | 0.042192471 | 1.4 | 1185 | 6 | 8 | 6 | 10 | 15 | 11 | N | N | N | N | N | N | N |
| METTL7A | high in P | 2.3 | 0.042243897 | 1.4 | 1186 | 200 | 124 | 127 | 314 | 262 | 228 | N | N | N | N | N | N | N |
| PPP2CB | high in P | 1.9 | 0.042250069 | 1.4 | 1187 | 3222 | 2155 | 3089 | 3906 | 6120 | 7060 | N | N | N | N | N | N | N |
| ZMAT3 | high in P | 2.5 | 0.042262411 | 1.4 | 1188 | 24 | 143 | 112 | 250 | 166 | 299 | N | N | N | N | N | N | N |
| RPP30 | high in P | 2.7 | 0.042295324 | 1.4 | 1189 | 15 | 19 | 33 | 44 | 46 | 31 | N | N | N | N | N | N | N |
| HELB | high in P | 3.1 | 0.042301495 | 1.4 | 1190 | 8 | 10 | 10 | 29 | 11 | 27 | N | N | N | N | N | N | N |
| MKLN1 | high in P | 1.8 | 0.042322751 | 1.4 | 1191 | 354 | 181 | 377 | 538 | 588 | 639 | N | N | N | N | N | N | N |
| PIP5K1C | high in P | 2.1 | 0.042376234 | 1.4 | 1192 | 54 | 271 | 199 | 354 | 365 | 380 | N | N | N | N | N | N | N |
| ST3GAL1 | high in P | 2.2 | 0.0424976 | 1.4 | 1193 | 204 | 705 | 483 | 961 | 1133 | 841 | N | N | N | N | N | N | N |
| PUS10 | high in P | 1.8 | 0.04256274 | 1.4 | 1194 | 10 | 16 | 13 | 16 | 20 | 26 | N | N | N | N | N | N | N |
| SEMA6B | high in P | 1.9 | 0.042600453 | 1.4 | 1195 | 13 | 17 | 18 | 113 | 27 | 27 | N | N | N | N | N | N | N |
| IPP | high in P | 2.0 | 0.04271359 | 1.4 | 1196 | 19 | 18 | 28 | 52 | 45 | 30 | P | N | N | N | N | N | N |
| CXCL3 | high in P | 4.0 | 0.042751988 | 1.4 | 1197 | 25 | 17 | 13 | 19 | 54 | 68 | N | N | N | N | N | N | N |
| HN1L | high in P | 1.8 | 0.042782844 | 1.4 | 1198 | 861 | 1378 | 1293 | 2260 | 1796 | 2130 | N | P | N | N | N | N | N |
| TMEM100 | high in P | 2.2 | 0.042806843 | 1.4 | 1199 | 5 | 5 | 5 | 9 | 8 | 11 | N | N | N | N | N | N | N |
| PECR | high in P | 3.7 | 0.042813014 | 1.4 | 1200 | 14 | 7 | 19 | 75 | 39 | 18 | N | N | N | N | N | N | N |
| TRIM8 | high in P | 2.5 | 0.042826042 | 1.4 | 1201 | 287 | 694 | 706 | 1678 | 876 | 999 | N | N | N | N | N | N | N |
| LAMB3 | high in P | 2.2 | 0.042968664 | 1.4 | 1202 | 125 | 348 | 267 | 436 | 518 | 595 | N | N | N | N | N | N | N |
| NCF4 | high in P | 9.4 | 0.042978264 | 1.4 | 1203 | 3 | 45 | 197 | 455 | 315 | 111 | N | N | N | N | N | N | N |
| TSPAN31 | high in P | 2.7 | 0.043039975 | 1.4 | 1204 | 108 | 56 | 93 | 261 | 131 | 140 | P | P | N | N | N | N | N |
| NCRNA00174 | high in P | 2.0 | 0.043207282 | 1.4 | 1205 | 13 | 18 | 13 | 28 | 22 | 18 | NA | NA | N | N | N | N | N |
| YRDC | high in P | 1.8 | 0.043605664 | 1.4 | 1206 | 128 | 141 | 90 | 244 | 222 | 151 | N | N | N | N | N | N | N |
| ST3GAL5 | high in P | 2.4 | 0.043611835 | 1.4 | 1207 | 10 | 10 | 12 | 25 | 23 | 16 | N | N | N | N | N | N | N |
| DCPS | high in P | 3.1 | 0.04368726 | 1.4 | 1208 | 40 | 82 | 137 | 295 | 272 | 102 | N | N | N | N | N | N | N |
| GDF11 | high in P | 1.8 | 0.043849767 | 1.4 | 1209 | 10 | 14 | 13 | 28 | 21 | 16 | N | N | N | N | N | N | N |
| FAM117B | high in P | 2.0 | 0.043855938 | 1.4 | 1210 | 27 | 23 | 17 | 45 | 29 | 31 | NA | NA | N | N | N | N | N |
| PLK1S1 | high in P | 4.0 | 0.043995132 | 1.4 | 1211 | 6 | 6 | 8 | 24 | 12 | 10 | N | N | N | N | N | N | N |
| ZNF586 | high in P | 2.0 | 0.044017759 | 1.4 | 1212 | 19 | 13 | 20 | 22 | 32 | 38 | NA | NA | N | N | N | N | N |
| ZNF436 | high in P | 1.7 | 0.044402393 | 1.4 | 1213 | 42 | 54 | 57 | 78 | 69 | 85 | N | N | N | N | N | N | N |
| PPP2R5A | high in P | 2.3 | 0.044078099 | 1.4 | 1214 | 98 | 213 | 101 | 258 | 201 | 253 | N | N | N | N | N | N | N |
| FIGN | high in P | 2.9 | 0.04408427 | 1.4 | 1215 | 6 | 6 | 6 | 10 | 16 | 6 | N | N | N | N | N | N | N |

TABLE 16-continued

Genes that Are Differentially Methylated between Nulliparous and Parous CD24+ Breast Epithelial Cells

| | | | | SAGE-seq | | | | | | | | | ChIP-seq | | | | MSDK-seq | | |
|---|---|---|---|---|---|---|---|---|---|---|---|---|---|---|---|---|---|---|---|
| | | | | | Nulliparous (NP) | | | | Parous (P) | | | | NP | CD24+ N74 | CD24+ N66 | | GeneBody | Pro-moter | Pro-moter |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | | | P | | NP GeneBody | Met | Met | P Met |
|---|---|---|---|---|---|---|---|---|---|---|---|---|---|---|---|---|---|---|---|
| SLED1 | high in P | 4.3 | 0.044222778 | 1.4 | 1216 | 86 | 2 | 38 | 269 | 158 | 90 | N | N | N | N | N | N | N | N |
| HDHD2 | high in P | 2.0 | 0.04422895 | 1.4 | 1217 | 16 | 35 | 27 | 41 | 44 | 61 | N | N | N | N | N | N | N | N |
| RCN3 | high in P | 2.6 | 0.04423992 | 1.4 | 1218 | 13 | 17 | 15 | 55 | 18 | 26 | N | N | N | N | N | N | N | N |
| RARRES1 | high in P | 3.7 | 0.044260491 | 1.4 | 1219 | 21 | 144 | 46 | 418 | 223 | 83 | N | N | N | N | N | N | N | N |
| KCTD18 | high in P | 3.0 | 0.044294089 | 1.4 | 1220 | 51 | 56 | 19 | 135 | 69 | 65 | N | N | N | N | N | N | N | N |
| ACBD3 | high in P | 1.6 | 0.044303689 | 1.4 | 1221 | 256 | 263 | 188 | 379 | 369 | 327 | N | N | N | N | N | P | N | N |
| TFRC | high in P | 3.2 | 0.044413398 | 1.4 | 1222 | 255 | 114 | 86 | 230 | 355 | 370 | N | N | N | N | N | N | N | N |
| WDR1 | high in P | 1.8 | 0.044419569 | 1.4 | 1223 | 2362 | 3332 | 2237 | 4780 | 4838 | 4245 | N | N | N | N | N | N | N | N |
| TIMM17A | high in P | 1.8 | 0.044519679 | 1.4 | 1224 | 1050 | 882 | 1248 | 2047 | 2198 | 1401 | N | N | N | N | N | N | N | N |
| YTHDF3 | high in P | 2.1 | 0.044525885 | 1.4 | 1225 | 207 | 191 | 98 | 337 | 249 | 336 | N | N | N | N | N | N | N | N |
| ANGPTL2 | high in P | 3.0 | 0.044538193 | 1.4 | 1226 | 17 | 21 | 20 | 37 | 24 | 30 | N | N | N | N | N | N | N | N |
| PIK3CG | high in P | 4.1 | 0.044779896 | 1.4 | 1227 | 11 | 7 | 8 | 30 | 22 | 10 | N | N | N | N | N | N | N | N |
| PSD | high in P | 2.7 | 0.044841264 | 1.4 | 1228 | 6 | 7 | 14 | 15 | 24 | 20 | P | N | P | N | N | N | N | N |
| CYTSB | high in P | 1.5 | 0.044957145 | 1.3 | 1229 | 6 | 12 | 10 | 14 | 16 | 13 | NA | NA | NA | N | N | N | N | N |
| ZC3HAV1 | high in P | 1.9 | 0.044988686 | 1.3 | 1230 | 45 | 92 | 60 | 129 | 80 | 97 | N | N | N | N | N | N | N | N |
| UGGT1 | high in P | 2.3 | 0.044994857 | 1.3 | 1231 | 56 | 62 | 45 | 99 | 118 | 69 | N | NA | NA | N | N | N | N | N |
| POM121L8P | high in P | 3.7 | 0.04507234 | 1.3 | 1232 | 29 | 28 | 82 | 99 | 89 | 78 | N | NA | NA | N | N | N | N | N |
| HEATR2 | high in P | 1.9 | 0.045094281 | 1.3 | 1233 | 26 | 34 | 14 | 51 | 35 | 45 | N | NA | NA | N | N | N | N | N |
| PAOX | high in P | 2.0 | 0.04511828 | 1.3 | 1234 | 4 | 8 | 5 | 10 | 31 | 10 | N | N | N | N | N | N | N | N |
| MVK | high in P | 2.6 | 0.045124451 | 1.3 | 1235 | 119 | 95 | 216 | 380 | 301 | 203 | N | N | N | N | N | N | N | N |
| CD164L2 | high in P | 2.7 | 0.045174506 | 1.3 | 1236 | 29 | 11 | 58 | 72 | 58 | 129 | N | N | N | N | N | N | N | N |
| SMOC1 | high in P | 2.9 | 0.04521359 | 1.3 | 1237 | 7 | 28 | 44 | 99 | 63 | 40 | N | P | N | N | N | N | N | N |
| SAA1 | high in P | 3.6 | 0.045402839 | 1.3 | 1238 | 2981 | 16504 | 6016 | 34767 | 17846 | 11326 | N | NA | NA | N | N | N | N | N |
| RANBP2 | high in P | 1.9 | 0.045461807 | 1.3 | 1239 | 62 | 72 | 47 | 81 | 112 | 86 | N | N | N | N | N | N | N | N |
| RASAL1 | high in P | 2.3 | 0.045540661 | 1.3 | 1240 | 73 | 27 | 51 | 130 | 113 | 71 | N | N | N | N | N | N | N | N |
| TBP | high in P | 3.0 | 0.045566031 | 1.3 | 1241 | 34 | 56 | 131 | 179 | 125 | 135 | N | N | N | N | N | N | N | N |
| ZNF767 | high in P | 4.1 | 0.045572202 | 1.3 | 1242 | 20 | 78 | 179 | 175 | 237 | 222 | N | N | N | N | N | N | N | N |
| APOBEC3F | high in P | 1.7 | 0.045723738 | 1.3 | 1243 | 59 | 62 | 94 | 111 | 141 | 108 | N | P | N | N | N | N | N | N |
| JKAMP | high in P | 3.1 | 0.045755337 | 1.3 | 1244 | 25 | 110 | 40 | 166 | 106 | 92 | NA | N | N | N | N | N | N | N |
| PDDC1 | high in P | 1.8 | 0.045827962 | 1.3 | 1245 | 43 | 82 | 88 | 94 | 114 | 132 | N | N | N | N | N | N | N | N |
| DDN | high in P | 1.8 | 0.045834133 | 1.3 | 1246 | 11 | 8 | 9 | 16 | 13 | 24 | P | N | N | N | N | N | N | N |
| MBD4 | high in P | 1.8 | 0.045845104 | 1.3 | 1247 | 507 | 408 | 499 | 989 | 716 | 626 | N | N | N | N | N | N | N | N |
| C1orf21 | high in P | 2.7 | 0.045958928 | 1.3 | 1248 | 484 | 239 | 278 | 514 | 624 | 679 | N | N | N | N | N | N | N | N |
| TMEM9B | high in P | 2.7 | 0.045986355 | 1.3 | 1249 | 69 | 193 | 77 | 262 | 223 | 171 | N | N | N | N | N | N | N | N |
| RNF144A | high in P | 1.8 | 0.046106349 | 1.3 | 1250 | 13 | 24 | 16 | 46 | 22 | 27 | N | N | N | N | N | N | N | N |
| CSTB | high in P | 2.0 | 0.04611732 | 1.3 | 1251 | 364 | 374 | 210 | 696 | 575 | 435 | N | N | N | N | N | N | N | N |
| ADAT3 | high in P | 3.4 | 0.046148176 | 1.3 | 1252 | 117 | 142 | 454 | 635 | 540 | 369 | N | N | N | N | N | N | N | N |
| ZNF484 | high in P | 2.0 | 0.046227715 | 1.3 | 1253 | 4 | 6 | 4 | 12 | 7 | 10 | N | N | N | N | N | N | N | N |
| RPAP2 | high in P | 1.8 | 0.046240743 | 1.3 | 1254 | 59 | 53 | 58 | 76 | 104 | 91 | N | N | N | N | N | N | N | N |
| C15orf40 | high in P | 1.6 | 0.046294227 | 1.3 | 1255 | 33 | 35 | 36 | 51 | 71 | 47 | N | N | N | N | N | N | N | N |
| C8orf41 | high in P | 1.8 | 0.046329196 | 1.3 | 1256 | 13 | 61 | 46 | 88 | 78 | 79 | N | N | N | N | N | N | N | N |
| FBXL18 | high in P | 1.7 | 0.046364166 | 1.3 | 1257 | 60 | 50 | 67 | 94 | 97 | 122 | N | N | N | N | N | N | N | N |
| SOCS6 | high in P | 1.8 | 0.04638062 | 1.3 | 1258 | 47 | 42 | 49 | 81 | 65 | 77 | N | N | N | N | N | N | N | N |
| SLCO3A1 | high in P | 3.2 | 0.046499246 | 1.3 | 1259 | 22 | 157 | 66 | 193 | 143 | 198 | P | N | N | N | N | N | N | N |

TABLE 16-continued

Genes that Are Differentially Methylated between Nulliparous and Parous CD24+ Breast Epithelial Cells

| | | | | SAGE-seq | | | | | | | | ChIP-seq | | | MSDK-seq | | |
|---|---|---|---|---|---|---|---|---|---|---|---|---|---|---|---|---|---|
| | | | log10 | | Nulliparous (NP) | | | | Parous (P) | | | NP | | | | | |
| Gene Symbol | expression pattern | Fold Change | p-value | (p-val.) | Rank-ing | CD24+ N48 | CD24+ N58 | CD24+ N43 | CD24+ N37 | CD24+ N39 | CD24+ N40 | | CD24+ N74 | CD24+ N66 | GeneBody | GeneBody Met | Pro-moter | Pro-moter Met |
| AVEN | high in P | 2.4 | 0.046578099 | 1.3 | 1260 | 3 | 15 | 7 | 18 | 34 | 14 | N | N | N | N | N | N | N |
| TCIRG1 | high in P | 2.3 | 0.046641868 | 1.3 | 1261 | 226 | 477 | 581 | 1174 | 955 | 558 | N | N | N | N | N | N | N |
| CXorf36 | high in P | 2.1 | 0.046669981 | 1.3 | 1262 | 25 | 22 | 25 | 41 | 30 | 37 | N | N | P | N | N | N | N |
| RNF145 | high in P | 2.5 | 0.046685752 | 1.3 | 1263 | 979 | 559 | 453 | 1308 | 1119 | 1385 | N | N | N | N | N | N | N |
| ZCCHC17 | high in P | 2.2 | 0.046740606 | 1.3 | 1264 | 312 | 435 | 296 | 906 | 704 | 438 | N | N | N | N | N | N | N |
| ORC4L | high in P | 2.0 | 0.046853744 | 1.3 | 1265 | 33 | 25 | 30 | 43 | 38 | 57 | N | N | N | N | N | N | N |
| ZBTB40 | high in P | 2.3 | 0.046859915 | 1.3 | 1266 | 93 | 139 | 217 | 256 | 262 | 250 | N | N | N | N | N | N | N |
| LOC388692 | high in P | 1.6 | 0.046894199 | 1.3 | 1267 | 101 | 109 | 118 | 173 | 145 | 160 | N | N | NA | N | N | N | N |
| LRP1 | high in P | 1.9 | 0.046994995 | 1.3 | 1268 | 64 | 78 | 86 | 101 | 92 | 93 | N | N | N | N | N | N | N |
| CCNL1 | high in P | 2.0 | 0.047162987 | 1.3 | 1269 | 708 | 492 | 436 | 921 | 848 | 1214 | N | N | N | N | N | N | N |
| REM1 | high in P | 2.3 | 0.047210985 | 1.3 | 1270 | 2 | 7 | 9 | 15 | 14 | 23 | N | N | N | N | N | N | N |
| C5orf24 | high in P | 1.7 | 0.04724664 | 1.3 | 1271 | 39 | 52 | 35 | 75 | 67 | 48 | N | N | N | N | N | N | N |
| POLR2I4 | high in P | 2.2 | 0.047345378 | 1.3 | 1272 | 17 | 22 | 17 | 43 | 29 | 22 | N | N | N | N | N | N | N |
| GOPC | high in P | 1.9 | 0.047368692 | 1.3 | 1273 | 17 | 61 | 37 | 56 | 61 | 86 | N | N | N | N | N | N | N |
| SOD2 | high in P | 1.6 | 0.047424918 | 1.3 | 1274 | 406 | 485 | 540 | 847 | 695 | 685 | N | N | N | N | N | N | N |
| PPP1R3A | high in P | 3.4 | 0.047501714 | 1.3 | 1275 | 895 | 642 | 300 | 1047 | 1016 | 3142 | N | N | N | N | N | N | N |
| ANKRD17 | high in P | 2.3 | 0.047570968 | 1.3 | 1276 | 122 | 303 | 180 | 371 | 330 | 337 | N | N | NA | N | N | N | N |
| LOC90784 | high in P | 2.3 | 0.047752674 | 1.3 | 1277 | 15 | 32 | 34 | 66 | 51 | 33 | N | N | NA | N | N | N | N |
| TLN2 | high in P | 2.0 | 0.047777359 | 1.3 | 1278 | 63 | 40 | 47 | 113 | 76 | 69 | N | N | N | N | N | N | N |
| VILL | high in P | 2.3 | 0.047841127 | 1.3 | 1279 | 39 | 31 | 60 | 102 | 109 | 57 | N | N | N | N | N | N | N |
| KHNYN | high in P | 1.8 | 0.04789941 | 1.3 | 1280 | 242 | 527 | 529 | 691 | 859 | 669 | N | N | N | N | N | N | N |
| MAFF | high in P | 1.9 | 0.047919295 | 1.3 | 1281 | 436 | 126 | 414 | 658 | 707 | 780 | N | N | N | N | N | N | N |
| CNNM3 | high in P | 2.2 | 0.048000206 | 1.3 | 1282 | 20 | 74 | 52 | 108 | 107 | 64 | N | N | N | N | N | N | N |
| EFHC1 | high in P | 2.3 | 0.048074945 | 1.3 | 1283 | 64 | 58 | 121 | 202 | 172 | 99 | N | N | N | N | N | N | N |
| MRPL16 | high in P | 1.8 | 0.048090716 | 1.3 | 1284 | 163 | 139 | 179 | 335 | 296 | 194 | N | N | P | N | N | N | N |
| YTHDC1 | high in P | 3.2 | 0.048096887 | 1.3 | 1285 | 2133 | 810 | 608 | 2480 | 2165 | 3027 | N | N | N | N | N | N | N |
| CYP1A1 | high in P | 7.0 | 0.048227167 | 1.3 | 1286 | 14 | 44 | 25 | 200 | 116 | 27 | N | P | P | N | N | N | N |
| CLDN4 | high in P | 6.5 | 0.048358132 | 1.3 | 1287 | 4341 | 766 | 280 | 20015 | 1394 | 10767 | N | P | P | N | N | N | N |
| HLA-G | high in P | 3.7 | 0.0484315 | 1.3 | 1288 | 5 | 5 | 6 | 28 | 21 | 5 | N | P | P | N | N | N | N |
| GATSL3 | high in P | 1.9 | 0.048528867 | 1.3 | 1289 | 97 | 60 | 141 | 217 | 175 | 157 | N | NA | P | P | N | N | N |
| DHX33 | high in P | 2.0 | 0.048568637 | 1.3 | 1290 | 13 | 33 | 20 | 51 | 31 | 30 | N | N | NA | N | N | N | N |
| LONRF2 | high in P | 2.9 | 0.04859675 | 1.3 | 1291 | 37 | 32 | 31 | 55 | 51 | 45 | N | N | N | N | N | N | N |
| RCCD1 | high in P | 1.8 | 0.048648176 | 1.3 | 1292 | 18 | 30 | 36 | 39 | 46 | 51 | N | N | N | N | N | N | N |
| L2HGDH | high in P | 1.7 | 0.048718801 | 1.3 | 1293 | 199 | 146 | 172 | 276 | 253 | 313 | N | N | P | N | N | N | N |
| RPL23AP82 | high in P | 1.9 | 0.048735258 | 1.3 | 1294 | 2 | 2 | 4 | 6 | 5 | 8 | N | NA | NA | N | N | N | N |
| MBP | high in P | 1.9 | 0.04887308 | 1.3 | 1295 | 66 | 126 | 96 | 128 | 167 | 173 | N | N | N | N | S | N | N |
| TREX1 | high in P | 2.0 | 0.048893651 | 1.3 | 1296 | 141 | 98 | 126 | 266 | 184 | 172 | N | N | N | N | N | N | N |
| FAM32A | high in P | 2.2 | 0.048908736 | 1.3 | 1297 | 282 | 573 | 562 | 1192 | 993 | 621 | N | N | N | N | N | N | N |
| SEPW1 | high in P | 2.1 | 0.048925878 | 1.3 | 1298 | 722 | 1299 | 598 | 1513 | 1510 | 1372 | N | N | N | N | N | N | N |
| APOD | high in P | 2.2 | 0.049015016 | 1.3 | 1299 | 953 | 558 | 220 | 1937 | 1066 | 1074 | N | N | N | N | N | N | N |
| DCBLD2 | high in P | 1.8 | 0.049041072 | 1.3 | 1300 | 31 | 81 | 47 | 92 | 64 | 92 | N | N | N | N | N | N | N |
| HGFAC | high in P | 2.0 | 0.049225521 | 1.3 | 1301 | 15 | 31 | 13 | 43 | 26 | 43 | N | N | N | N | N | N | N |
| MRPL48 | high in P | 2.4 | 0.049231692 | 1.3 | 1302 | 121 | 77 | 161 | 307 | 300 | 151 | N | N | N | N | N | N | N |
| PPP40 | high in P | 3.9 | 0.04930986 | 1.3 | 1303 | 39 | 27 | 108 | 146 | 168 | 81 | N | N | N | N | N | N | N |

TABLE 16-continued

Genes that Are Differentially Methylated between Nulliparous and Parous CD24+ Breast Epithelial Cells

| | | | | SAGE-seq | | | | | | | | ChIP-seq | | | | MSDK-seq | |
| --- | --- | --- | --- | --- | --- | --- | --- | --- | --- | --- | --- | --- | --- | --- | --- | --- | --- |
| | | | | | Nulliparous (NP) | | | Parous (P) | | | | | | | | | |
| Gene Symbol | expression pattern | Fold Change | p-value | log10 (p-val.) | Rank-ing | CD24+ N48 | CD24+ N58 | CD24+ N43 | CD24+ N37 | CD24+ N39 | CD24+ N40 | NP CD24+ N74 | P CD24+ N66 | NP GeneBody | P GeneBody Met | NP Pro-moter Met | P Pro-moter Met |
| RAB11FIP5 | high in P | 1.6 | 0.049486766 | 1.3 | 1304 | 59 | 65 | 70 | 121 | 91 | 81 | N | N | N | N | N | N |
| CILP | high in P | 1.9 | 0.04952585 | 1.3 | 1305 | 17 | 20 | 22 | 24 | 29 | 33 | N | N | N | N | N | N |
| PIGY | high in P | 1.6 | 0.049558077 | 1.3 | 1306 | 124 | 135 | 117 | 204 | 198 | 158 | N | N | N | N | N | N |
| AKIRIN2 | high in P | 2.3 | 0.049571105 | 1.3 | 1307 | 1090 | 494 | 618 | 1247 | 1330 | 1563 | N | N | N | N | N | N |
| ANKFY1 | high in P | 1.7 | 0.049612246 | 1.3 | 1308 | 118 | 328 | 335 | 459 | 509 | 459 | N | N | N | N | N | N |
| CHD3 | high in P | 1.7 | 0.049645159 | 1.3 | 1309 | 575 | 424 | 806 | 936 | 926 | 1271 | N | N | N | P | N | N |
| CLN5 | high in P | 2.2 | 0.049684243 | 1.3 | 1310 | 40 | 123 | 72 | 154 | 113 | 142 | N | N | N | N | N | N |
| MYH14 | high in P | 1.9 | 0.049774753 | 1.3 | 1311 | 454 | 629 | 907 | 1104 | 1307 | 993 | N | N | N | N | N | N |
| EHMT2 | high in P | 2.8 | 0.049780924 | 1.3 | 1312 | 165 | 119 | 341 | 699 | 463 | 288 | N | N | N | N | N | N |
| PLXNB1 | high in P | 1.8 | 0.049813151 | 1.3 | 1313 | 713 | 861 | 1344 | 1400 | 1704 | 1898 | N | N | N | N | N | N |
| TTC4 | high in P | 1.5 | 0.049822751 | 1.3 | 1314 | 19 | 24 | 21 | 38 | 28 | 30 | N | N | N | N | N | N |
| STARD7 | high in P | 3.7 | 0.049859092 | 1.3 | 1315 | 156 | 48 | 61 | 176 | 214 | 178 | N | N | N | N | N | N |
| BOP1 | high in P | 2.4 | 0.049865263 | 1.3 | 1316 | 88 | 177 | 107 | 139 | 310 | 333 | N | N | N | N | N | N |

TABLE 17

Enriched GeneGo Pathway Maps for DMRs in Promoter and Gene Body in CD44+ Cells

| Pathway maps | Promoter hypermethylated | | Genebody hyper methylated | |
|---|---|---|---|---|
| | Nulliparous | Parous | Nulliparous | Parous |
| Stem cells_H3K9 demethylases in pluripotency maintenance of stem cells | | 7.04E−05 | | |
| Development_VEGF signaling and activation | | 7.82E−05 | | |
| Development_VEGF signaling via VEGFR2 - generic cascades | | 9.77E−05 | | |
| HCV-dependent cytoplasmic signaling leading to HCC | 2.18E−02 | 1.62E−04 | 2.30E−03 | |
| Stem cells_Cooperation between Hedgehog, IGF-2 and HGF signaling pathways in medulloblastoma stem cells | 3.41E−02 | 3.20E−04 | 3.76E−03 | 1.64E−02 |
| HBV signaling via protein kinases leading to HCC | | 5.07E−04 | 4.90E−02 | |
| Cytoskeleton remodeling_Alpha-1A adrenergic receptor-dependent inhibition of PI3K | | 9.44E−04 | | |
| Development_FGF2-dependent induction of EMT | | 1.10E−03 | 1.64E−02 | |
| Signal transduction_PTEN pathway | | 1.30E−03 | 1.04E−02 | 3.24E−02 |
| Development_TGF-beta-dependent induction of EMT via RhoA, PI3K and ILK. | 3.49E−03 | 1.30E−03 | | |
| Development_Leptin signaling via PI3K-dependent pathway | | 1.41E−03 | | 3.37E−02 |
| IL-6 signaling in multiple myeloma | | 1.65E−03 | 1.24E−02 | |
| Stem cells_Insulin, IGF-1 and TNF-alpha in brown adipocyte differentiation | | 2.20E−03 | | |
| Regulation of lipid metabolism_Insulin regulation of fatty acid methabolism | | 2.31E−03 | 1.15E−02 | |
| Immune response_BCR pathway | | 2.36E−03 | | |
| Muscle contraction_Oxytocin signaling in uterus and mammary gland | | 3.47E−03 | | |
| Regulation of lipid metabolism_RXR-dependent regulation of lipid metabolism via PPAR, RAR and VDR | | 3.64E−03 | | |
| Unsaturated fatty acid biosynthesis | | 3.91E−03 | | |
| Development_Regulation of epithelial-to-mesenchymal transition (EMT) | | 4.38E−03 | 3.61E−03 | |
| Cell cycle_Role of Nek in cell cycle regulation | | 4.38E−03 | 3.96E−02 | |
| Stem cells_Self-renewal and pluripotency maintenance of human embryonic stem cells | | 4.79E−03 | | |
| Apoptosis and survival_Role of CDK5 in neuronal death and survival | | 5.21E−03 | 4.42E−02 | |
| Stem cells_Role of PKR1 and ILK in cardiac progenitor cells | | 5.21E−03 | | 1.84E−02 |
| Immune response_Oncostatin M signaling via MAPK in mouse cells | | 5.65E−03 | 4.66E−02 | |
| Immune response_Oncostatin M signaling via MAPK in human cells | | 6.61E−03 | | |
| Stem cells_Early embryonal hypaxial myogenesis | 4.93E−02 | 6.61E−03 | | 2.16E−02 |
| Apoptosis and survival_Ceramides signaling pathway | | 7.13E−03 | 6.14E−03 | |
| Immune response_Human NKG2D signaling | | 7.13E−03 | 6.14E−03 | |
| Transcription_Role of AP-1 in regulation of cellular metabolism | | 7.13E−03 | | |
| Development_Gastrin in differentiation of the gastric mucosa | | 7.13E−03 | | |
| Stem cells_FGF signaling in pancreatic and hepatic differentiation of embryonic stem cells | | 8.22E−03 | | |
| Stem cells_FGF2-induced self-renewal of adult neural stem cells | | 8.22E−03 | | |
| Immune response_Murine NKG2D signaling | | 9.41E−03 | 8.12E−03 | |
| Apoptosis and survival_BAD phosphorylation | | 9.41E−03 | 8.12E−03 | |
| Regulation of lipid metabolism_PPAR regulation of lipid metabolism | | 9.41E−03 | | |
| Development_A2A receptor signaling | | 1.00E−02 | 8.66E−03 | |
| Apoptosis and survival_Anti-apoptotic action of Gastrin | | 1.00E−02 | | |
| Immune response_IL-1 signaling pathway | | 1.07E−02 | 8.96E−04 | |
| Development_Flt3 signaling | | 1.07E−02 | | |
| Development_Thrombopoietin-regulated cell processes | | 1.14E−02 | 9.82E−03 | |
| Development_Activation of ERK by Alpha-1 adrenergic receptors | | 1.14E−02 | 9.82E−03 | |
| Development_PIP3 signaling in cardiac myocytes | | 1.28E−02 | 1.11E−02 | |
| Regulation of lipid metabolism_Insulin signaling:generic cascades | 2.06E−02 | 1.28E−02 | | |
| EGFR signaling pathway in Lung Cancer | | 1.28E−02 | | |
| Stem cells_Scheme: FGF signaling in embryonic stem cell self-renewal and differentiation | 2.06E−02 | 1.28E−02 | | |
| Transcription_Transcription factor Tubby signaling pathways | | 1.32E−02 | | |
| Cytoskeleton remodeling_Integrin outside-in signaling | | 1.43E−02 | 1.24E−02 | |
| HBV-dependent NF-kB and PI3K/AKT pathways leading to HCC | | 1.43E−02 | | |
| Neuropeptide signaling in pancreatic cancer | | 1.43E−02 | | |
| Immune response_IL-2 activation and signaling pathway | 2.36E−02 | 1.43E−02 | | |
| Development_Melanocyte development and pigmentation | | 1.43E−02 | | |
| Pro-inflammatory action of Gastrin in gastric cancer | | 1.51E−02 | 1.31E−02 | |
| Development_GM-CSF signaling | | 1.51E−02 | | |
| PI3K signaling in gastric cancer | | 1.60E−02 | 1.56E−03 | |
| Mucin expression in CF via TLRs, EGFR signaling pathways | | 1.60E−02 | | |
| Stem cells_Scheme: Adult neurogenesis in the Subventricular Zone | | 1.64E−02 | | |
| IGF signaling in HCC | 2.87E−02 | 1.68E−02 | 1.46E−02 | |
| Development_WNT signaling pathway. Part 2 | 1.12E−03 | 1.77E−02 | 1.25E−05 | 4.19E−02 |
| Development_FGFR signaling pathway | | 1.77E−02 | 1.53E−02 | |
| Proliferative action of Gastrin in gastric cancer | | 1.77E−02 | | |
| Development_Role of HDAC and calcium/calmodulin-dependent kinase (CaMK) in control of skeletal myogenesis | | 1.86E−02 | 1.94E−03 | |
| Immune response_CD28 signaling | | 1.86E−02 | 1.61E−02 | |
| ERBB family and HGF signaling in gastric cancer | | 1.86E−02 | 1.61E−02 | |
| PGE2 pathways in cancer | 1.37E−03 | 1.95E−02 | 1.69E−02 | 3.47E−04 |
| Transcription_Role of VDR in regulation of genes involved in osteoporosis | | 2.35E−02 | | |
| Stem cells_Aberrant Wnt signaling in medulloblastoma stem cells | 1.41E−02 | 2.36E−02 | 1.43E−03 | |

TABLE 17-continued

Enriched GeneGo Pathway Maps for DMRs in Promoter and Gene Body in CD44+ Cells

| Pathway maps | Promoter hypermethylated | | Genebody hyper methylated | |
|---|---|---|---|---|
| | Nulliparous | Parous | Nulliparous | Parous |
| Regulation of lipid metabolism_Regulation of acetyl-CoA carboxylase 2 activity in muscle | | 2.36E−02 | | |
| Role of stellate cells in progression of pancreatic cancer | | 2.45E−02 | | |
| Apoptosis and survival_NO signaling in survival | | 2.56E−02 | | |
| Development_Gastrin in cell growth and proliferation | | 2.67E−02 | 3.50E−04 | |
| Transcription_Transcription regulation of aminoacid metabolism | 1.77E−02 | 2.77E−02 | 2.50E−02 | |
| Dual role of BMP signaling in gastric cancer | 2.14E−03 | 2.77E−02 | | |
| Development_EGFR signaling pathway | | 2.78E−02 | | |
| Cytoskeleton remodeling_TGF, WNT and cytoskeletal remodeling | 3.40E−03 | 2.86E−02 | 7.77E−04 | |
| Muscle contraction_Regulation of eNOS activity in endothelial cells | | 2.90E−02 | 3.61E−03 | |
| n-3 Polyunsaturated fatty acid biosynthesis | | 2.90E−02 | | |
| n-6 Polyunsaturated fatty acid biosynthesis | | 2.90E−02 | | |
| Cell cycle_Regulation of G1/S transition (part 2) | | 2.98E−02 | 2.69E−02 | |
| Immune response_IL-10 signaling pathway | 1.97E−02 | 2.98E−02 | | |
| Apoptosis and survival_NGF signaling pathway | | 2.98E−02 | | |
| Transcription_Role of Akt in hypoxia induced HIF1 activation | | 3.19E−02 | 2.89E−02 | |
| Inflammatory mechanisms of pancreatic cancerogenesis | | 3.26E−02 | | |
| Immune response_Antigen presentation by MHC class I | | 3.42E−02 | | |
| Immune response_Delta-type opioid receptor signaling in T-cells | | 3.64E−02 | | |
| Apoptosis and survival_p53-dependent apoptosis | | 3.64E−02 | | |
| Hedgehog signaling in gastric cancer | 2.64E−02 | 3.64E−02 | | |
| Glycine, serine, cysteine and threonine metabolism | | 3.85E−02 | | |
| Immune response_IL-4 - antiapoptotic action | | 3.88E−02 | | |
| Stem cells_Role of BMP signaling in embryonic stem cell neural differentiation | | 3.88E−02 | | |
| Mechanisms of K-RAS addiction in lung cancer cells | | 3.88E−02 | | |
| Apoptosis and survival_Granzyme A signaling | | 3.88E−02 | | |
| Cell adhesion_Gap junctions | | 3.88E−02 | | |
| Reproduction_GnRH signaling | | 3.91E−02 | 3.41E−02 | |
| Glycine, serine, cysteine and threonine metabolism/Rodent version | | 4.04E−02 | | |
| Stem cells_Scheme: Histone H3 demethylases in stem cells | | 4.12E−02 | | |
| Stem cells_Dopamine-induced transactivation of EGFR in SVZ neural stem cells | | 4.12E−02 | | |
| Stem cells_Role of GSK3 beta in cardioprotection against myocardial infarction | | 4.36E−02 | 3.96E−02 | |
| Stem cells_H3K4 demethylases in stem cell maintenance | 6.61E−04 | 4.36E−02 | | |
| Signal transduction_Activin A signaling regulation | 7.85E−05 | 4.61E−02 | 4.18E−02 | |
| Mucin expression in CF via IL-6, IL-17 signaling pathways | | 4.87E−02 | 4.42E−02 | |
| Stem cells_FGF2 signaling during embryonic stem cell differentiation | | 4.87E−02 | | |
| Immune response_Role of the Membrane attack complex in cell survival | | 4.87E−02 | | |
| Immune response_CXCR4 signaling via second messenger | | 4.87E−02 | | |
| Signal transduction_Erk Interactions: Inhibition of Erk | | 4.87E−02 | | |
| WNT signaling in gastric cancer | 1.15E−03 | | 2.50E−05 | |
| Stem cells_Fetal brown fat cell differentiation | 7.54E−03 | | 1.99E−04 | |
| Development_Role of IL-8 in angiogenesis | 1.80E−03 | | 2.56E−04 | 5.35E−03 |
| E-cadherin signaling and its regulation in gastric cancer | 4.61E−02 | | 4.13E−04 | |
| WNT signaling in HCC | 1.19E−02 | | 6.21E−04 | |
| Regulation of lipid metabolism_Regulation of fatty acid synthase activity in hepatocytes | | | 8.07E−04 | |
| Transcription_CREB pathway | | | 8.96E−04 | |
| Development_WNT signaling pathway. Part 1. Degradation of beta-catenin in the absence WNT signaling | 9.54E−03 | | 9.42E−04 | |
| Development_WNT5A signaling | | | 1.06E−03 | |
| Neurophysiological process_ACM regulation of nerve impulse | | | 1.06E−03 | |
| immune response_MIF-JAB1 signaling | | | 1.63E−03 | |
| G-protein signaling_Proinsulin C-peptide signaling | | | 1.68E−03 | |
| Neurophysiological process_Kappa-type opioid receptor in transmission of nerve impulses | | | 3.13E−03 | |
| Cell adhesion_Role of CDK5 in cell adhesion | | | 3.32E−03 | |
| Cardiac Hypertrophy_NF-AT signaling in Cardiac Hypertrophy | | | 3.82E−03 | |
| G-protein signaling_Regulation of CDC42 activity | | | 4.11E−03 | |
| Cell cycle_ESR1 regulation of G1/S transition | | | 4.11E−03 | |
| Development_Role of CDK5 in neuronal development | | | 4.48E−03 | |
| Stem cells_Stimulation of differentiation of mouse embryonic fibroblasts into adipocytes by extracellular factors | 2.12E−02 | | 5.24E−03 | |
| Development_Beta-adrenergic receptors transactivation of EGFR | | | 5.69E−03 | |
| Regulation of lipid metabolism_Regulation of lipid metabolism via LXR, NF-Y and SREBP | 9.95E−03 | | 6.14E−03 | 2.27E−02 |
| Stem cells_Regulation of lung epithelial progenitor cell differentiation | 1.30E−02 | | 7.59E−03 | |
| Development_Ligand-dependent activation of the ESR1/AP-1 pathway | | | 8.14E−03 | |
| Development_Ligand-independent activation of ESR1 and ESR2 | | | 9.23E−03 | |
| Immune response_IL-5 signalling | | | 9.23E−03 | |
| Role of DNA methylation in progression of multiple myeloma | 1.65E−02 | | 9.23E−03 | |
| G-protein signaling_Regulation of cAMP levels by ACM | | | 9.82E−03 | 3.11E−02 |
| HIF-1 in gastric cancer | | | 1.11E−02 | |
| Development_PDGF signaling via MAPK cascades | | | 1.11E−02 | |

TABLE 17-continued

Enriched GeneGo Pathway Maps for DMRs in Promoter and Gene Body in CD44+ Cells

| Pathway maps | Promoter hypermethylated | | Genebody hyper methylated | |
|---|---|---|---|---|
| | Nulliparous | Parous | Nulliparous | Parous |
| Development_HGF signaling pathway | | | 1.11E−02 | |
| Regulation of metabolism_Triiodothyronine and Thyroxine signaling | 2.21E−02 | | 1.17E−02 | |
| immune response_Function of MEF2 in T lymphocytes | | | 1.31E−02 | |
| Transcription_Assembly of RNA Polymerase II preinitiation complex on TATA-less promoters | | | 1.33E−02 | |
| Stem cells_Signaling pathways in embryonic hepatocyte maturation | | | 1.38E−02 | |
| HCV-mediated liver damage and predisposition to HCC progression via p53 | | | 1.48E−02 | |
| Development_Endothelin-1/EDNRA signaling | | | 1.53E−02 | 4.19E−02 |
| Stem cells_Differentiation of white adipocytes | | | 1.53E−02 | |
| Stem cells_H3K36 demethylation in stem cell maintenance | | | 1.64E−02 | |
| Cell adhesion_Chemokines and adhesion | | | 1.70E−02 | |
| Cytoskeleton remodeling_Cytoskeleton remodeling | | | 1.82E−02 | |
| Transcription_Role of heterochromatin protein 1 (HP1) family in transcriptional silencing | | | 1.96E−02 | |
| Delta508-CFTR traffic / Sorting endosome formation in CF | | | 2.14E−02 | |
| Apoptosis and survival_Beta-2 adrenergic receptor anti-apoptotic action | | | 2.14E−02 | |
| Immune response_IL-12 signaling pathway | | | 2.14E−02 | |
| Transcription_PPAR Pathway | | | 2.23E−02 | |
| Development_Alpha-2 adrenergic receptor activation of ERK | | | 2.32E−02 | |
| Immune response_IFN alpha/beta signaling pathway | | | 2.32E−02 | |
| Development_Glucocorticoid receptor signaling | | | 2.32E−02 | |
| Inhibition of TGF-beta signaling in gastric cancer | 2.14E−03 | | 2.50E−02 | |
| Immune response_CD16 signaling in NK cells | | | 3.06E−02 | |
| HGF signaling in pancreatic cancer | | | 3.09E−02 | |
| Proteolysis_Putative SUMO-1 pathway | | | 3.30E−02 | |
| NGF activation of NF-kB | | | 3.30E−02 | |
| Apoptosis and survival_nAChR in apoptosis inhibition and cell cycle progression | 2.64E−02 | | 3.30E−02 | |
| Development_Slit-Robo signaling | | | 3.51E−02 | |
| Development_Osteopontin signaling in osteoclasts | | | 3.51E−02 | |
| Stem cells_Neovascularization of glioblastoma in response to hypoxia | | | 3.73E−02 | |
| EGFR family signaling in pancreatic cancer | | | 3.91E−02 | |
| Stem cells_WNT and Notch signaling in early cardiac myogenesis | | | 4.66E−02 | |
| Role of osteoblasts in bone lesions formation in multiple myeloma | | | 4.66E−02 | |
| Muscle contraction- GPCRs in the regulation of smooth muscle tone | | | 4.87E−02 | |
| Development_SSTR2 in regulation of cell proliferation | | | 4.90E−02 | |
| G-protein signaling_RAC1 in cellular process | 4.61E−02 | | 4.90E−02 | |
| Immune response_Regulation of T cell function by CTLA-4 | | | 4.90E−02 | |
| ENaC regulation in airways (normal and CF) | 2.87E−02 | | | |
| ATP/ITP metabolism | 2.13E−02 | | | |
| Translation_Opioid receptors in regulation of translation | 1.59E−02 | | | |
| Delta508-CFTR traffic/ER-to-Golgi in CF | 2.68E−03 | | | |
| GTP-XTP metabolism | 3.97E−03 | | | |
| Transport_Aldosterone-mediated regulation of ENaC sodium transport | 2.89E−02 | | | |
| Immune response_IL-7 signaling in T lymphocytes | 9.95E−03 | | | |
| wtCFTR and delta508-CFTR traffic/Generic schema (norm and CF) | 2.53E−02 | | | |
| Cell adhesion_Tight junctions | 4.61E−02 | | | 2.05E−02 |
| CTP/UTP metabolism | 6.86E−04 | | | |
| Mechanisms of CAM-DR in multiple myeloma | 7.44E−03 | | | |
| Apoptosis and survival_Role of IAP-proteins in apoptosis | 4.79E−03 | | | |
| Development_BMP signaling | 6.02E−03 | | | |
| Neurophysiological process_Netrin-1 in regulation of axon guidance | 1.30E−02 | | | 2.61E−02 |
| Immune response_IL-7 signaling in B lymphocytes | 1.53E−02 | | | |
| Cell cycle_Sister chromatid cohesion | 1.25E−02 | | | |
| Development_TGF-beta-dependent induction of EMT via SMADs | 7.44E−03 | | | |
| Normal wtCFTR traffic/ER-to-Golgi | 2.68E−03 | | | |
| Transport_RAN regulation pathway | 7.05E−03 | | | |
| Immune response_IL-23 signaling pathway | 1.77E−02 | | | |
| Transition of HCC cells to invasive and migratory phenotype | 1.19E−02 | | | |
| Development_Regulation of CDK5 in CNS | 2.40E−02 | | | |
| Development_CNTF receptor signaling | 3.99E−02 | | | |
| Stem cells_Scheme: SMAD-dependent TGF-beta family signaling in embryonic stem cells | 1.59E−02 | | | |
| Cell cycle_Spindle assembly and chromosome separation | 6.02E−03 | | | |
| Stem cells_Extraembryonic differentiation of embryonic stem cells | 4.29E−02 | | | |
| FGFR3 signaling in multiple myeloma | 4.93E−02 | | | |
| Stem cells_Trophectoderm differentiation | 1.77E−02 | | | |
| Development_PEDF signaling | 2.36E−02 | | | |
| Signal transduction_PKA signaling | 2.69E−02 | | | 3.72E−03 |
| Stem cells_mGluR3 signaling in glioblastoma stem cells | | | | 4.05E−02 |
| Stem cells_Embryonal epaxial myogenesis | | | | 1.54E−02 |
| Blood coagulation_GPCRs in platelet aggregation | | | | 9.37E−03 |
| Non-genomic signaling of ESR2 (membrane) in lung cancer cells | | | | 3.50E−02 |

TABLE 17-continued

Enriched GeneGo Pathway Maps for DMRs in Promoter and Gene Body in CD44+ Cells

| Pathway maps | Promoter hypermethylated | | Genebody hyper methylated | |
|---|---|---|---|---|
| | Nulliparous | Parous | Nulliparous | Parous |
| Glycolysis and gluconeogenesis p. 1 | | | | 3.24E−02 |
| G-protein signaling_Regulation of p38 and JNK signaling mediated by G-proteins | | | | 2.38E−02 |
| Membrane-bound ESR1: interaction with G-proteins signaling | | | | 3.91E−02 |
| Inhibitory action of Lipoxin A4 on PDGF, EGF and LTD4 signaling | | | | 1.84E−02 |
| Apoptosis and survival_Anti-apoptotic TNFs/NF-kB/Bcl-2 pathway | | | | 2.61E−02 |
| Development_Beta-adrenergic receptors regulation of ERK | | | | 3.37E−02 |
| Development_S1P1 receptor signaling via beta-arrestin | | | | 1.74E−02 |
| Regulation of lipid metabolism_Regulation of acetyl-CoA carboxylase 1 activity in lipogenic tissue | | | | 4.76E−03 |
| Signal transduction_cAMP signaling | | | | 1.60E−03 |
| Immune response_PGE2 common pathways | | | | 4.05E−02 |
| Muscle contraction_Relaxin signaling pathway | | | | 3.50E−02 |
| Regulation of beta-adrenergic receptors signaling in pancreatic cancer | | | | 2.86E−02 |
| Immune response_Histamine signaling in dendritic cells | | | | 3.77E−02 |
| Regulation of lipid metabolism_Regulation of lipid metabolism by niacin and isoprenaline | | | | 3.11E−02 |
| Development_Mu-type opioid receptor signaling via Beta-arrestin | | | | 9.40E−03 |
| Glycolysis and gluconeogenesis (short map) | | | | 7.67E−03 |
| Protein folding_Membrane trafficking and signal transduction of G-alpha (i) heterotrimeric G-protein | | | | 5.94E−03 |
| Development S_1P3 receptor signaling pathway | | | | 2.86E−02 |
| Regulation of CFTR activity (norm and CF) | | | | 4.93E−02 |
| Angiogenesis in HCC | | | | 3.77E−02 |
| Neurophysiological process_Dopamine D2 receptor signaling in CNS | | | | 3.37E−02 |
| Development_Lipoxin inhibitory action on PDGF, EGF and LTD4 signaling | | | | 1.94E−02 |
| Regulation of lipid metabolism_Regulation of acetyl-CoA carboxylase 1 activity in keratinocytes | | | | 4.76E−03 |
| Neurophysiological process_Melatonin signaling | | | | 2.86E−02 |
| Blood coagulation_GPVI-dependent platelet activation | | | | 4.48E−02 |
| Development_Role of Activin A in cell differentiation and proliferation | | | | 1.85E−02 |
| G-protein signaling_S1P2 receptor signaling | | | | 1.94E−02 |
| Apoptosis and survival_HTR1A signaling | | | | 3.77E−02 |
| Immune response_TREM1 signaling pathway | | | | 4.63E−02 |
| Muscle contraction_Role of kappa-type opioid receptor in heart | | | | 1.74E−02 |
| Development_ERBB-family signaling | | | | 2.38E−02 |
| Cholesterol and Sphingolipids transport/Influx to the early endosome in lung (normal and CF) | | | | 1.45E−02 |
| Propionate metabolism p.2 | | | | 9.74E−03 |
| Regulation of metabolism_Bile acids regulation of glucose and lipid metabolism via FXR | | | | 2.16E−02 |
| Reproduction_Progesterone-mediated oocyte maturation | | | | 2.50E−02 |
| Apoptosis and survival_APRIL and BAFF signaling | | | | 2.27E−02 |
| Chemotaxis_CXCR4 signaling pathway | | | | 1.84E−02 |
| Neurophysiological process_HTR1A receptor signaling in neuronal cells | | | | 2.73E−02 |
| Neurophysiological process_GABAergic neurotransmission | | | | 3.77E−02 |
| Development_S1P1 signaling pathway | | | | 2.98E−02 |
| Development_Delta- and kappa-type opioid receptors signaling via beta-arrestin | | | | 8.65E−03 |
| Neurophysiological process_Mu-type opioid receptor-mediated analgesia | | | | 1.45E−02 |

Example 5: Persistent Parity-Related Decrease of p27+ Cells

This example demonstrates that the number of p27+ and Ki67+ cells are significantly lower in parous than in nulliparous breast tissues.

As discussed in Example CDKN1B encoding for p27, was one of the most significantly differentially expressed genes in CD44+ cells from nulliparous and parous (high in nulliparous) and also from control and BRCA1/2 parous tissues (high in BRCA1/2).

Figure 19:
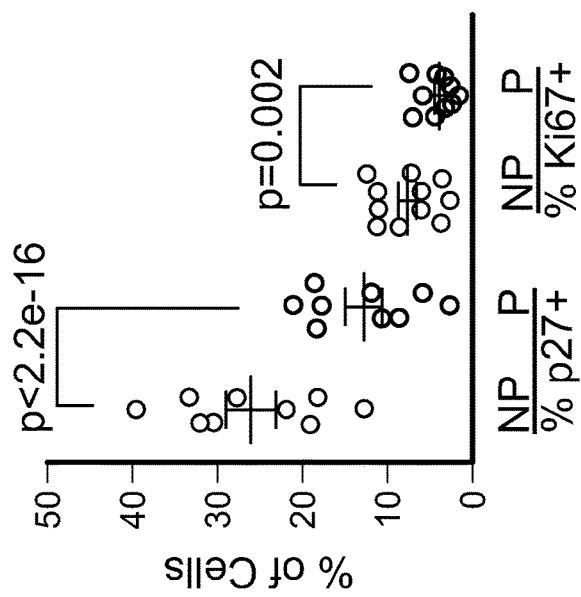
FIG. 19 is a graph showing the frequencies (% of total breast epithelial cells) of p27+ and Ki67+ cells in nulliparous (NP) and parous (P) breast tissue samples. Horizontal bars indicate the median, vertical bars indicate SEM, and p-values of differences between nulliparous and parous groups are indicated.

The global profiling results were validated in intact breast epithelium at the single cell level using multicolor immunofluorescence assays for the combined detection of CD24, CD44, and top differentially expressed genes. Genes were selected based on significance of difference between nulliparous and parous groups and antibody availability. A marked decrease was found in the expression of p27, Sox17, and Cox2 in parous compared to nulliparous samples. The levels of expression of these markers were lower in breast epithelial cells of parous women compared to nulliparous women (FIG. 18 and FIG. 19).

p27 has been reported to affect the number and proliferation of stem cells and progenitors in several organs. Thus, the decrease of p27+ cells in parous tissues may indicate that the number or proliferative potential of breast epithelial progenitors is decreased. To investigate this issue, immunofluorescence analysis was performed for Ki67, a proliferation marker expressed in cycling cells, alone and in combination with p27. Using this approach it was observed that the number of Ki67+ cells was significantly lower in parous samples and a small subset of cells was Ki67+p27+(FIG. 19).

Figure 20:
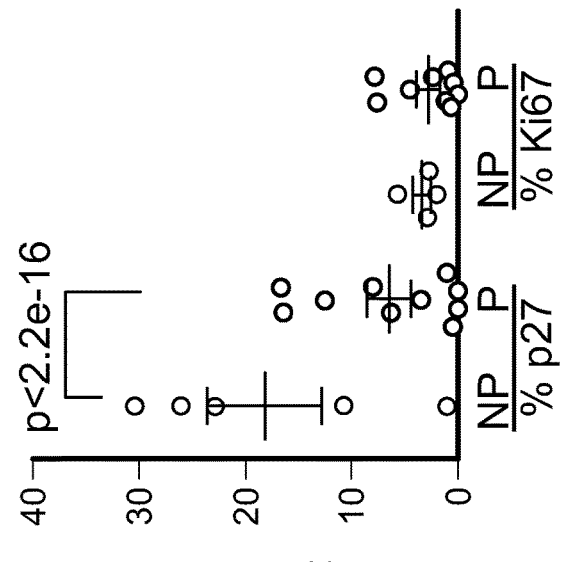
FIG. 20 contains graphs quantifying the expression of p27 (in arbitrary units) and the frequencies (% of total breast epithelial cells) of p27+ and Ki67+ cells in CD44+ and CD24+ breast epithelial cells in postmenopausal nulliparous (NP) and parous (P) women (FIG. 20)

The tissue samples used for the global profiling studies above (Example 3) were obtained from premenopausal women, since the protective effects of pregnancy against breast cancer are likely to be established early, even though they are manifested after menopause. However, to confirm that the parity-related differences detected in premenopausal women were maintained and could be detected even after menopause, the expression of p27, Sox17, and Cox2 was analyzed by immunofluorescence and immunohistochemistry in breast tissue samples from postmenopausal women. Although the observed differences between nulliparous and parous postmenopausal samples were less pronounced, the number of p27+ and Ki67+ cells were still significantly lower in parous than in nulliparous tissues (FIG. 20). This observation also suggested that the differences in the number of p27+ and Ki67+ cells between parous and nulliparous tissues in premenopausal women was not likely due to differences in the phase of the menstrual cycle between groups, as postmenopausal tissues showed similar differences for these markers.

Example 6: Link Between Parity-Related Differences and Mammographic Density

This example demonstrates that p27+ cells are a marker of both parity status and mammographic density, and a strong marker for breast cancer risk prediction.

Figure 21:
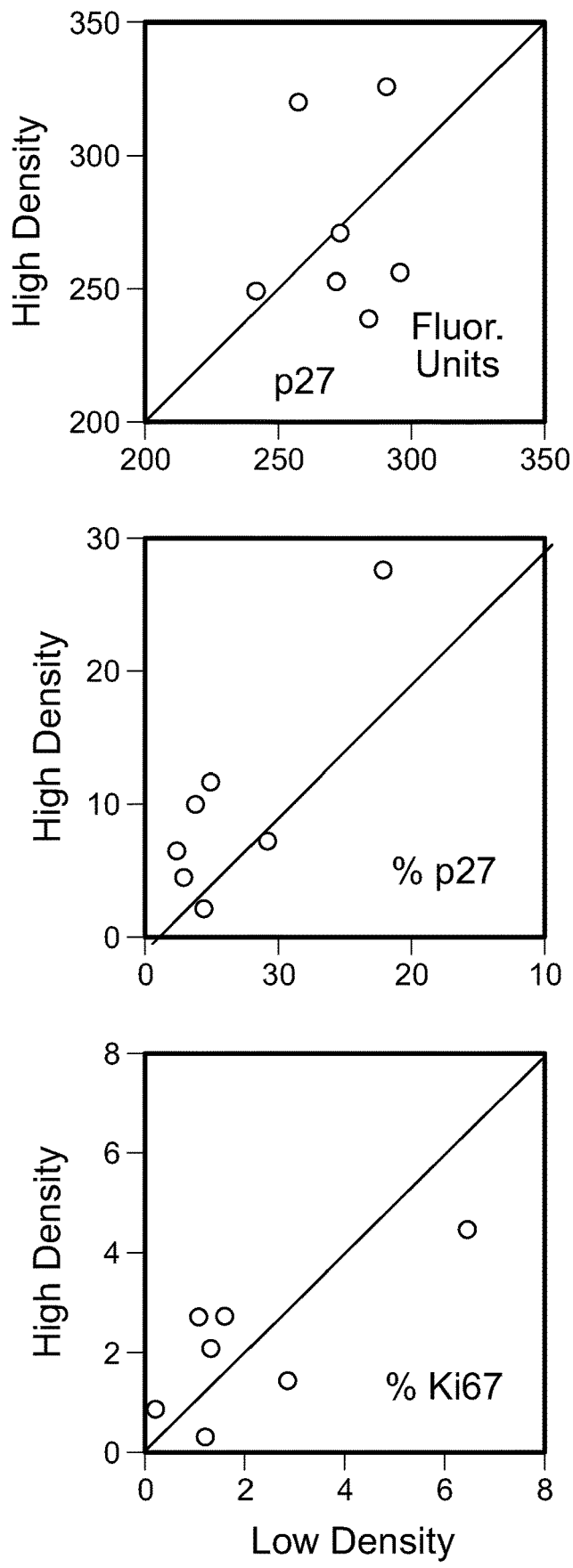
FIG. 21 contains graphs quantifying the expression of p27 (in arbitrary units) and the frequencies (% of total breast epithelial cells) of p27+ and Ki67+ cells in high and low density areas of the same breast from premenopausal parous women.

Mammographic density is one of the most significant risk factors for breast cancer, yet its molecular basis is unknown. Mammographic density is higher in nulliparous women and declines after pregnancy, thus, some of the parity-related differences detected may also be linked to differences in mammographic density. To test this hypothesis, the expression levels of p27, Sox17, Cox2, and Ki67 were analyzed in biopsy samples obtained from high and low density areas of the same breast [Lin, et al. (2011) Breast Cancer Res Treat 128, 505-516]. The overall expression of Sox17, Cox2, p27, and Ki67 were not significantly different between low and high-density areas, but the number of p27+ cells was higher in high-density areas (FIG. 21). Thus, the number of p27+ cells is a marker of both parity status and mammographic density, and because both of these are linked to breast cancer risk, it can be used for breast cancer risk prediction.

Example 7: p27$^+$ Cells are Quiescent Hormone-Responsive Cells with Progenitor Features This example demonstrates that a subset of p27+ cells may represent quiescent hormone-responsive progenitors that are the potential cell-of-origin of breast cancer.

Figure 22:
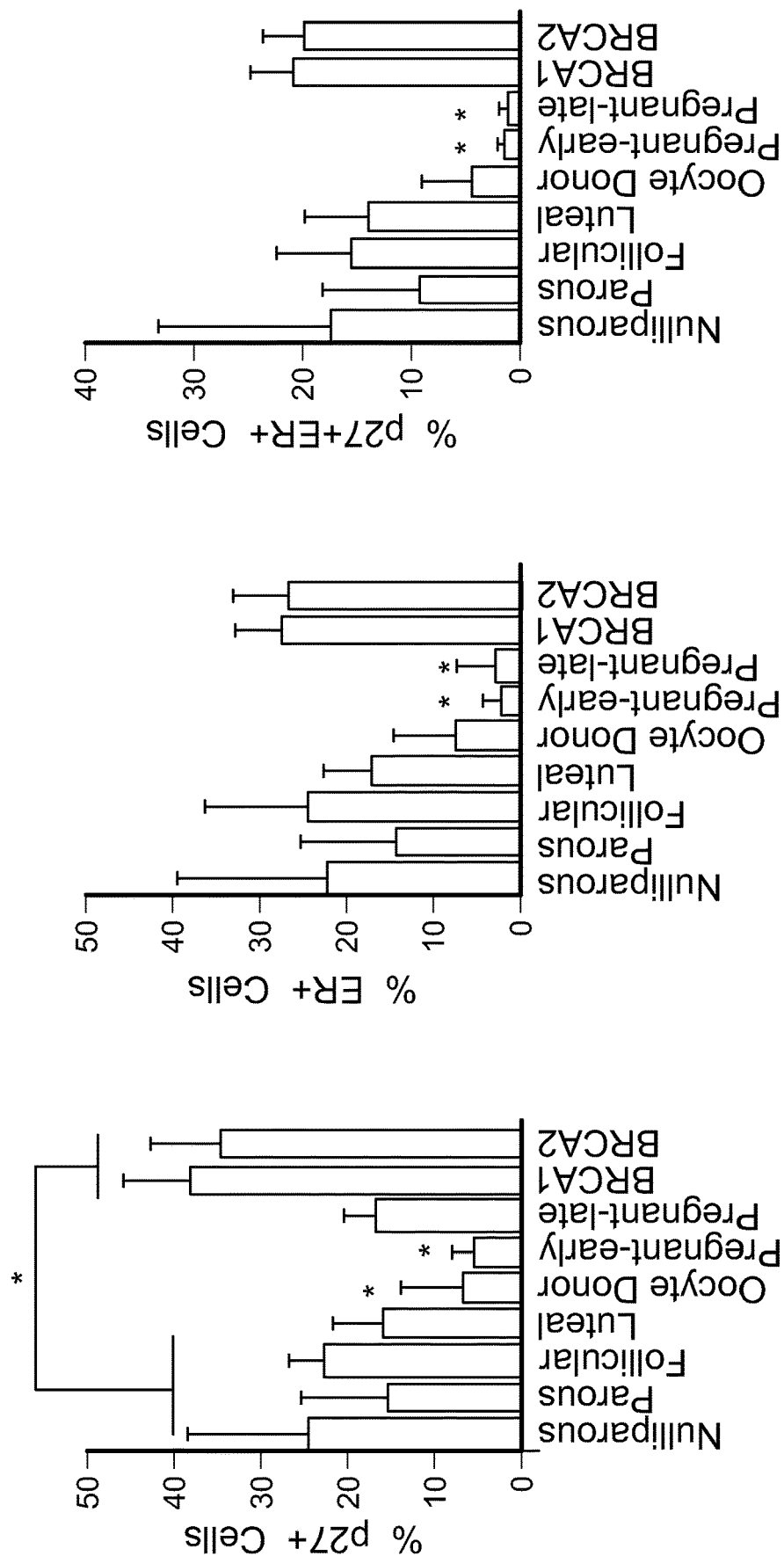
FIG. 22 contains bar graphs quantifying the frequencies (% of total breast epithelial cells) of p27+ and ER+ cells in each group of samples (nulliparous, parous, women in follicular or luteal phase of menstrual cycle, oocyte donor, early pregnancy, late pregnancy, BRCA1+ mutation carriers and BRCA-2 mutation carriers). Horizontal bars indicate the median, vertical bars mark the SEM, and asterisks indicate significant (p≤0.05, t-test or Fisher exact test) differences between groups of 4-8 samples.
Figure 23A:
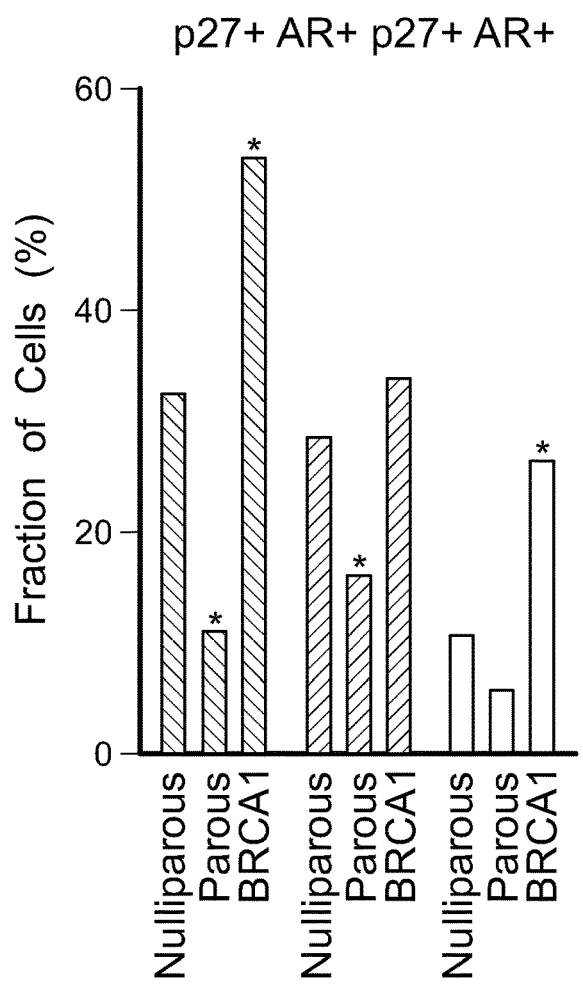
FIG. 23A is a bar graph quantifying frequencies (fraction (%) of total breast epithelial cells) of p27+, androgen receptor (AR)+, and p27+AR+ cells in each set of samples (nulliparous, parous, and BRCA1+ mutation carriers).
Figure 23B:
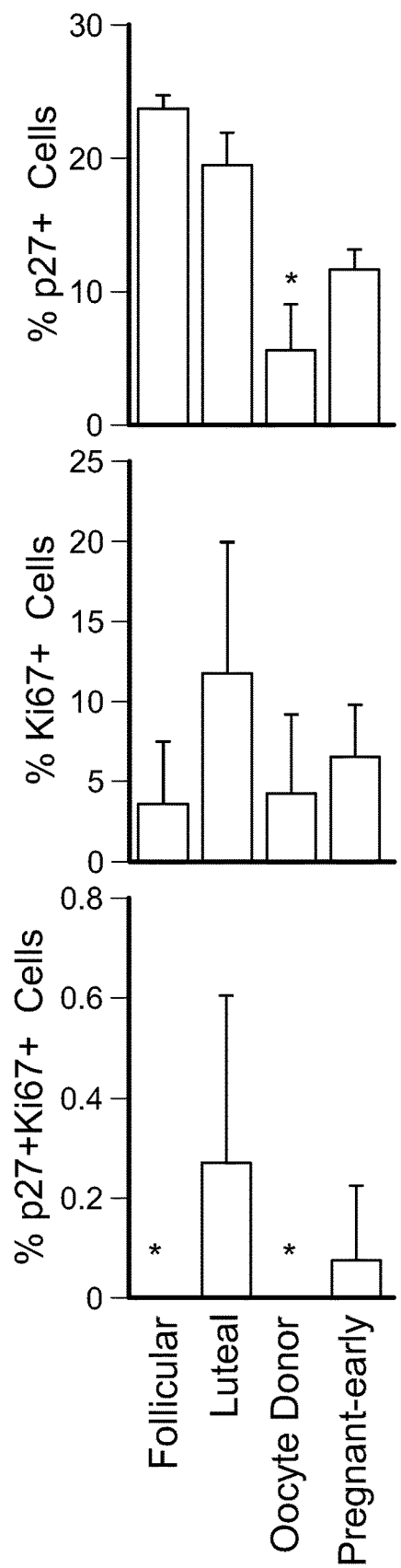
FIG. 23B contains bar graphs quantifying frequencies (% of total breast epithelial cells) of p27+, Ki67+, and p27+ Ki67+ cells in each set of samples (sample collected from women in the follicular or luteal phase of the menstrual cycle, oocyte donor and women in early pregnancy).

The mutually exclusive expression of Ki67 and p27 in breast epithelial cells with their concomitant decrease in parous compared to nulliparous women implied coordinated regulation and that they may represent actively cycling and quiescent cells with proliferative potential, respectively. Ovarian hormones are the best-understood regulators of breast epithelial cell proliferation and also breast cancer risk. Correlating with this, the gene expression data (Example 2) indicated a decrease in androgen receptor (AR) and AR targets in CD44$^+$ cells from parous women (Table 4) and prior studies implied a decrease in ER+ breast epithelial cells in parous compared to nulliparous women. To explore the potential hormonal regulation of p27+ breast epithelial cells, the expression of ER, AR, and p27 was analyzed in breast tissue samples from women with varying parity and hormonal status. These included control nulliparous and parous women, BRCA1/2 mutation carriers, breast biopsy tissues from women in early (8-10 weeks) and late (22-26 weeks) stage of pregnancy, and premenopausal women in the follicular and luteal phases of the menstrual cycle or from women undergoing ovarian hyperstimulation prior to oocyte collection for in vitro fertilization (samples are collected at the time of oocyte collection). For each case, multiple different regions of the same slide or breast tissue sample were analyzed in order to minimize differences due to the known tissue heterogeneity even in the same woman. Interestingly, it was found that nearly all p27+ cells were also ER+, and their numbers were the highest in BRCA1/2 mutation carriers and the lowest in biopsy samples from pregnant women and after ovarian hyperstimulation, where both ovarian hormone and hCG (human choriogonadotropin) levels are the highest (FIG. 22). The frequencies of p27+ cells, ER+ cells, and p27+ER+ cells were also higher in control nulliparous compared to parous women and in follicular relative to luteal phase of the menstrual cycle (FIG. 22). Overall similar observations were made for AR (FIG. 23A), although the overlap between p27 and AR was less pronounced compared to that between p27 and ER (FIG. 23B). The high fraction of AR+ cells in BRCA1 mutation carriers is particularly interesting since AR is a genetic modifier of BRCA1-associated breast cancer risk.

Figure 23C:
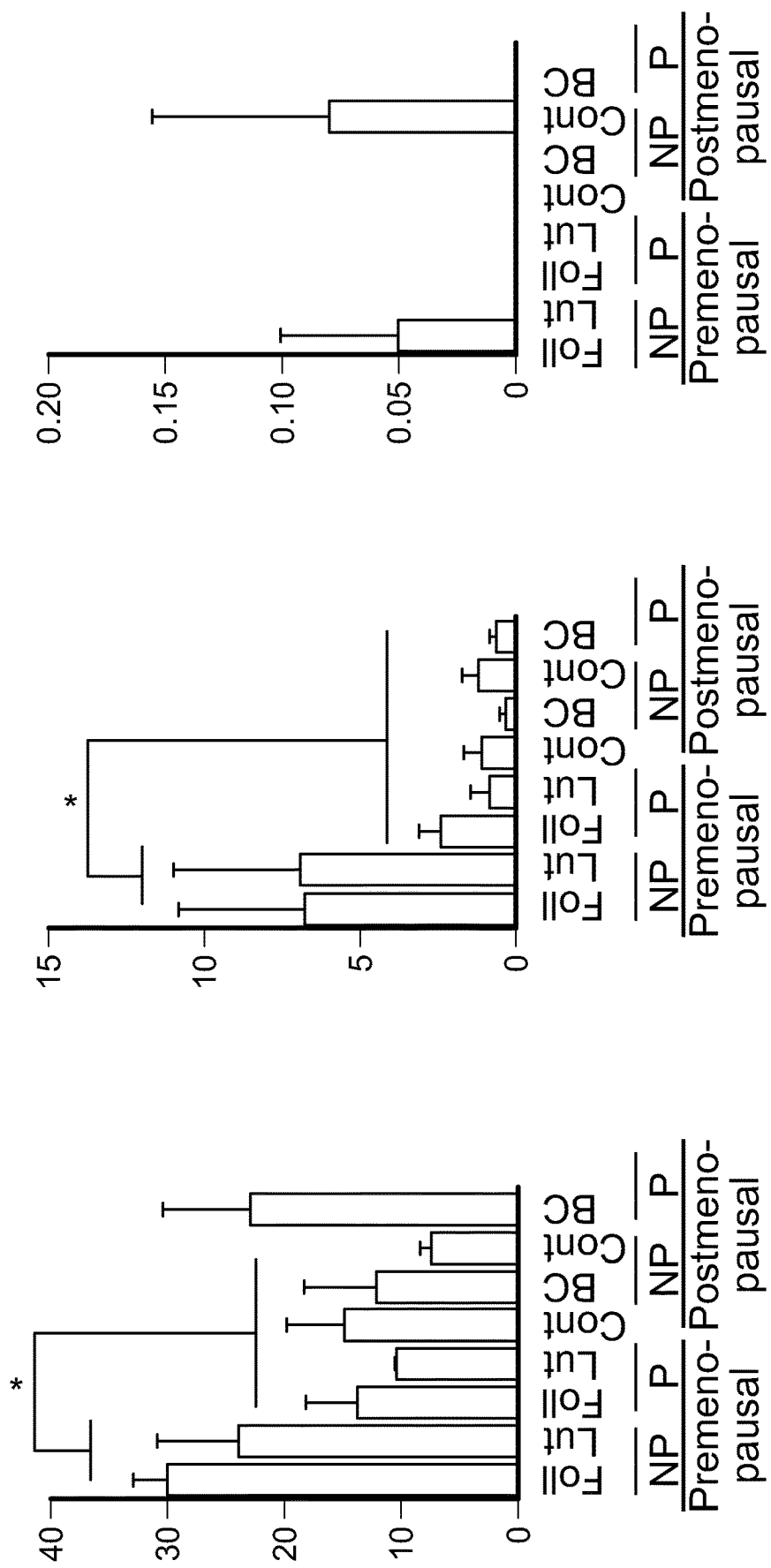
FIG. 23C contains bar graphs quantifying the frequency of p27+, Ki67+, and p27+Ki67+ cells in the breast tissue of premenopausal and postmenopausal nulliparous (NP) or parous (P) women in different phases of the menstrual cycle (i.e., follicular ("Foll") and luteal ("Lut")) or with breast cancer (BC) or without (cont); asterisks mark p≤0.05.

To further investigate the relationship between the numbers of p27$^+$ cells and ovarian hormone-induced breast epithelial cell proliferation, immunofluorescence analysis for p27 and Ki67 was performed in tissue samples with the highest differences in hormone levels. Correlating with prior data, the frequency of Ki67 cells was the highest in the luteal phase of the menstrual cycle when both estrogen and progesterone levels are high (FIG. 23B). Samples from early pregnancy had a lower fraction of proliferating Ki67$^+$ cells and the numbers of these cells was the lowest in the follicular phase. The frequency of p27$^+$ cells displayed an inverse correlation with that of Ki67$^+$ cells: it was the highest in the follicular phase and lowest in biopsies from oocyte donors (breast tissue biopsies were taken at the time of oocyte collection) (FIG. 23B). Interestingly, a low but detectable fraction of p27$^+$ cells was also Ki67$^+$ in the luteal phase and early pregnancy, potentially marking proliferating progenitors in early G1 phase of the cell cycle when p27 and Ki67 can overlap. The differences in the frequency of p27$^+$ and Ki67$^+$ cells between the follicular and luteal phases was less significant in parous compared to nulliparous women in part due to the lower overall fractions of these cells in parous cases (FIG. 23C).

These results show that a subset of p27$^+$ cells represent quiescent hormone-responsive luminal progenitors and that their frequency relates to the risk of breast cancer.

Example 8: Functional Validation of Parity-Related Differences in Signaling Pathways This example demonstrates that the decreased activity of stem cell-related pathways following pregnancy lead to decreased Ki67+ and p27+ cells in parous women.

Figure 11:
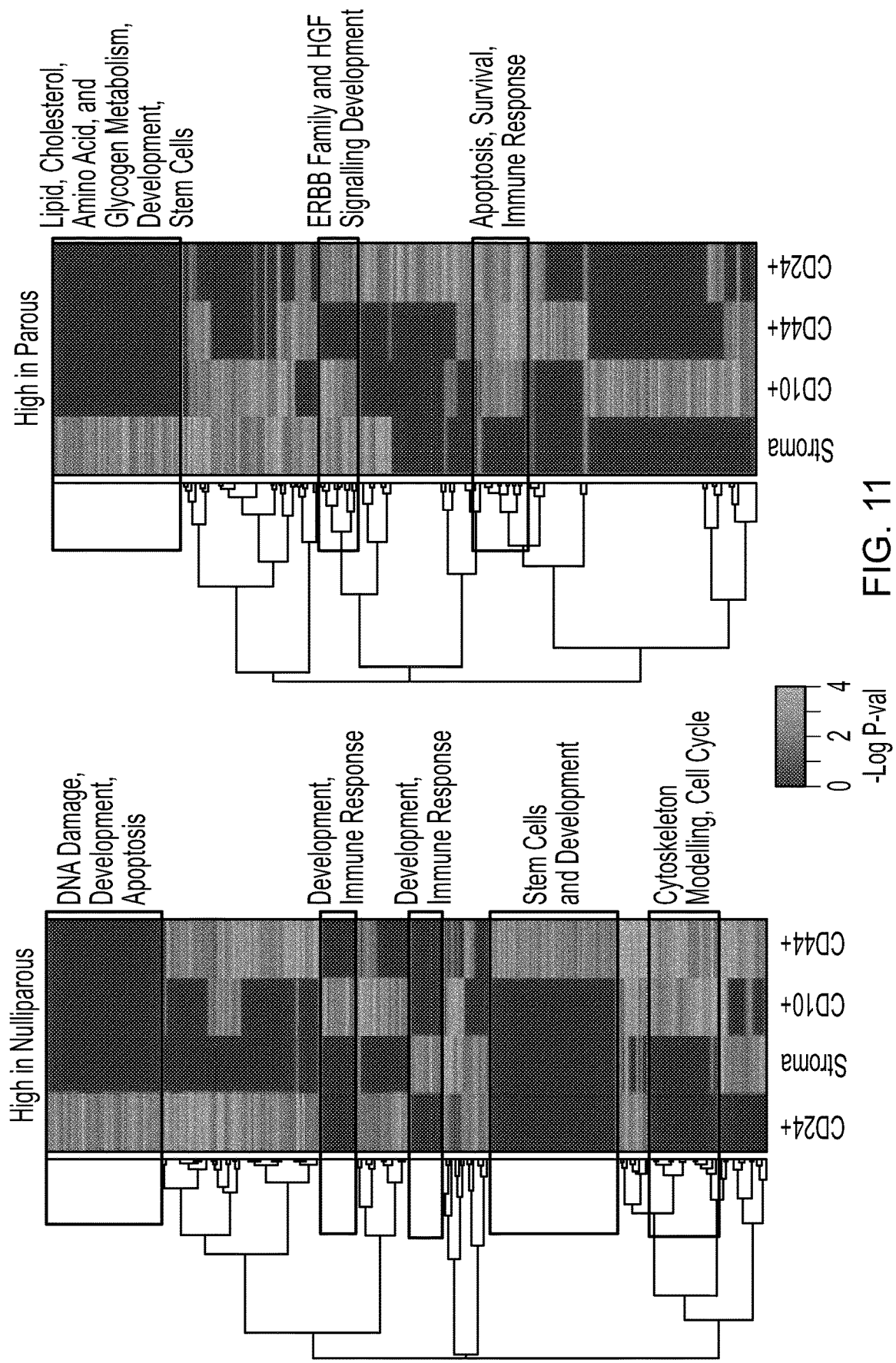
FIG. 11 is a heat map depicting unsupervised clustering of signaling pathways significantly down- or upregulated in parous compared to nulliparous samples in any of the four cell types (stromal fibroblasts ("stroma"), CD10+, CD44+ and CD24+ breast epithelial cells) analyzed. Gray scale indicates −log p value of enrichment. Rectangles highlight cell type-specific or common altered pathways.
Figure 12:
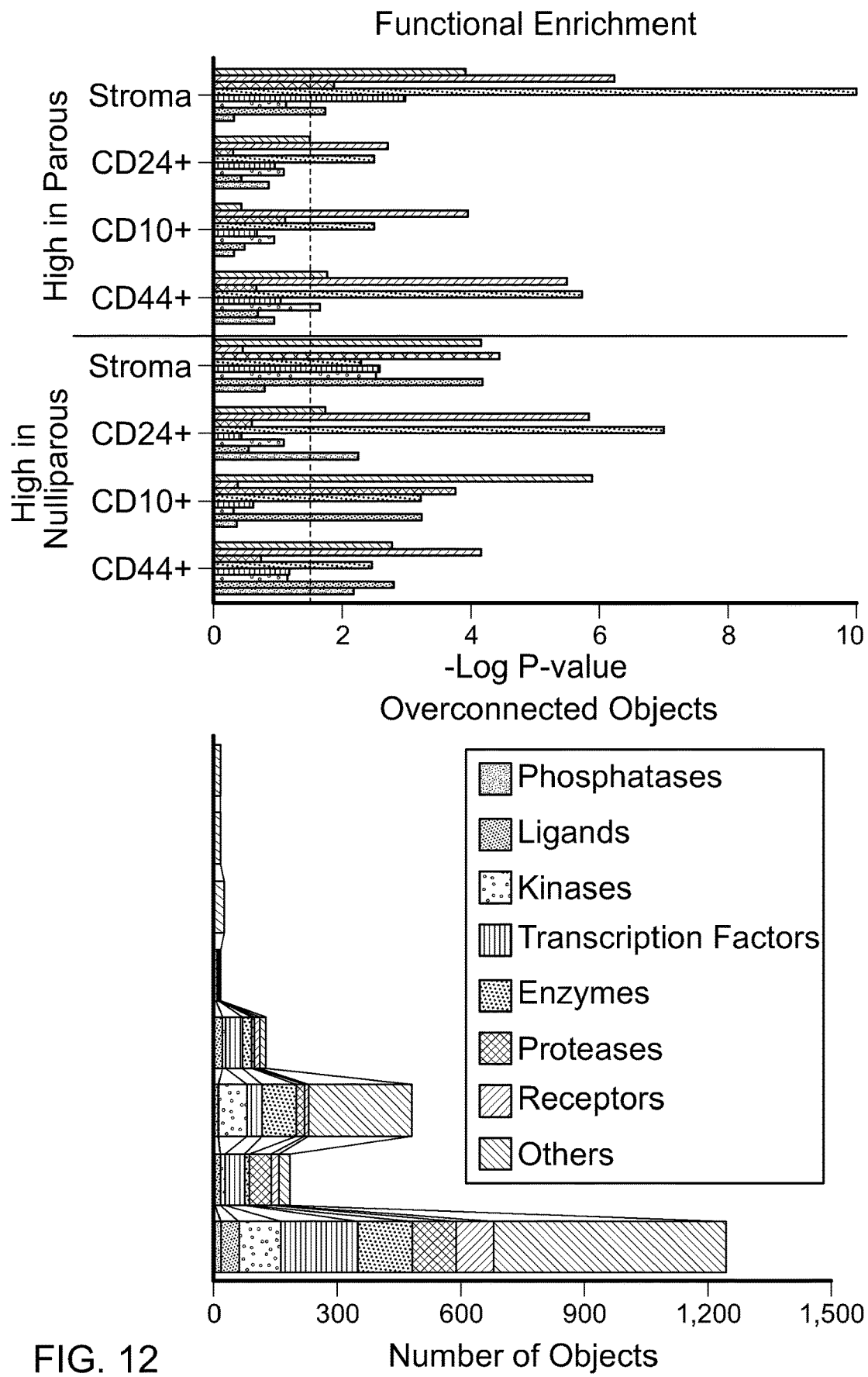
FIG. 12 contains graphs showing the relative enrichment (left panel) and relative connectivity (right panel) of the indicated protein classes in nulliparous and parous samples in each of the four cells types (stromal fibroblasts ("stroma"), CD10+, CD44+ and CD24+ breast epithelial cells) analyzed. X-axes indicate −log 10 p-values for enrichment (left panel) with the listed protein classes and the number of overconnected objects, defined as proteins with higher than expected number of interactions, in each functional category within each group (right panel), respectively.

Several signaling pathways less active in CD44+ parous cells were related to stem cell maintenance and cell proliferation (FIG. 11). To investigate if inhibition of these pathways affects the number of proliferating cells, normal breast tissues were incubated in a tissue explant culture model with inhibitors or agonists of selected pathways (e.g., cAMP, EGFR, Cox2, Hh, TGFβ, Wnt, and IGFR) for 8-10 days. Inhibitors of irrelevant pathways (e.g., PARP inhibitor) as additional negative controls were also tested. For each case, three different pieces of breast tissue taken from different regions of the same breast were cultured, to minimize variability due to tissue heterogeneity. The number of p27+ cells and cellular proliferation based on bromodeoxyuridine (BrdU) incorporation (marks cells in S phase of the cell cycle) and Ki67 expression (marks cycling cells irrespective of cell cycle phase) was then assessed.

Tissue architecture and cellular viability were maintained and p27+, Ki67+, and BrdU+ cells were detected in all conditions. It was found that inhibition of cAMP, EGFR, Cox2, Hh, and IGFR signaling significantly (p<0.05) decreased the number of cells incorporating BrdU whereas the TGFBR inhibitor had the opposite effect (FIG. 24) Inhibition of EGFR and Cox2, and, to a lesser degree, Wnt and IGFR, decreased the fraction of Ki67+ cells, whereas the frequency of p27+ cells most pronouncedly decreased following IGFR and TGFBR inhibitor treatment. It was also confirmed that the compounds effectively inhibited the activity of the intended pathways (FIG. 25 and FIG. 26) and that the selected pathways were active in p27+ cells.

Figure 26A:
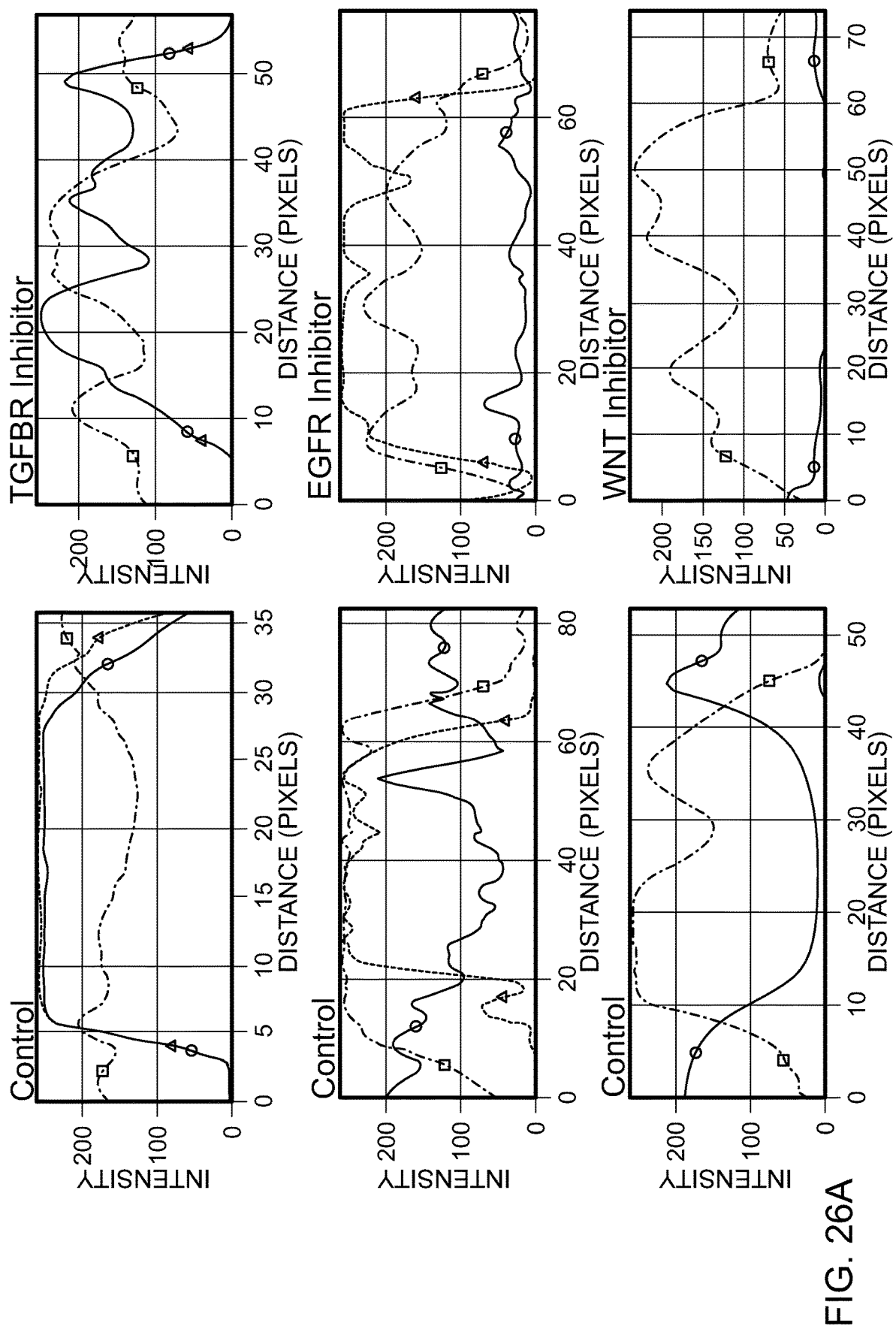
FIG. 26A contains line graphs plotting the RGB spectra demonstrating overlap between the expression of p27 and the indicated marker (in the top panels: circles mark the line for pSMAD2, triangles mark the line for p27, and squares mark the line for DAPI; in the middle panels: circles mark the line for pEGFR, triangles mark the line for p27, squares mark the line for DAPI; in the lower panel: circles mark the line for axin2 and squares mark the line for DAPI); left graphs are control groups and right graphs are treated with the indicated inhibitor. In all graphs, intensity is plotted on the y-axis and distance (in pixels) in plotted on the x-axis.

To determine whether the numbers and the proliferation of p27+ cells are regulated by ER and estrogen signaling, the fraction of p27+ and Ki67+ cells in tissue slices treated with varying concentrations of ovarian hormones or tamoxifen were analyzed. To correlate the tissue slices data with that was observed under physiologic conditions (FIG. 22), estrogen, progesterone, prolactin, and hCG hormone levels that mimic serum levels in the follicular or luteal phases of the menstrual cycle or in mid-pregnancy were used. It was observed that the numbers of p27+ cells were high in sections treated with concentrations of estrogen present in follicular phase and also following tamoxifen treatment, whereas it decreased following IGFR and TGFBR inhibitor treatment (FIG. 24). Cultures incubated with luteal phase and pregnancy level hormones (FIG. 26B and FIG. 26C). These data further demonstrated that a subset of p27+ cells are hormone-responsive luminal progenitors.

Figure 25:
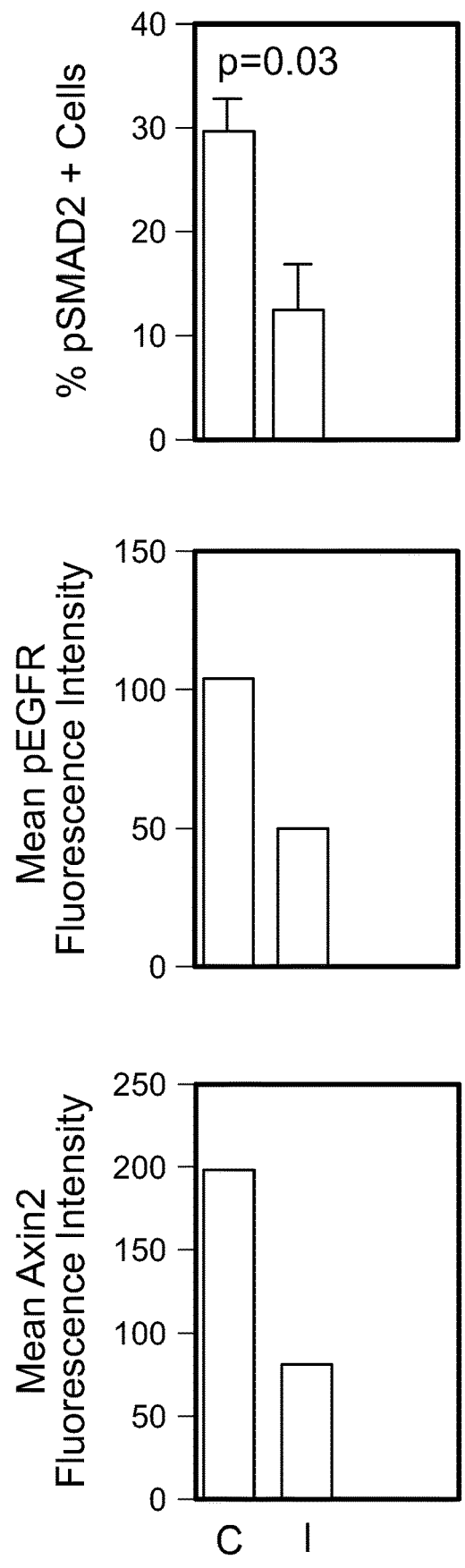
FIG. 25 contains bar graphs quantifying the frequency (% of total breast epithelial cells) of pSMAD2+ cells, or the mean fluorescence intensity of pEGFR and Axin 2 in breast epithelial tissue treated with control (C) or inhibitor (I) (inhibitor of TGFb, EGFR or Wnt, from top graph to bottom graph).

Most importantly, the expression of phosphoSmad2 (pSmad2), a key mediator of TGFβ signaling, demonstrated a nearly complete overlap with that of p27, implying that TGFβ is essential for maintaining these cells in quiescent stage possibly via modulating p27 (FIG. 25). These results imply that the decreased activity of these stem cell-related pathways following pregnancy may lead to decreased Ki67+ and p27+ cells in parous women. Furthermore, the data also suggested a direct role for these signaling pathways in regulating breast epithelial cell proliferation where TGF acts as a growth inhibitor and the other pathways are mitogenic.

Example 9: Relevance of Parity to Breast Cancer Risk and Prognosis

The present example demonstrates that parity influences both the risk and prognosis of ER+ breast tumors.

Based on the profiling data above (Example 3), it is presently demonstrated that breast epithelial cells with progenitor features are different in nulliparous and parous women. If these cells serve as cell-of-origin for breast cancer then breast tumors developing in parous and nulliparous women might also be different, and this might impact their gene expression profiles and clinical outcome. To test these hypotheses, the effect of parity on breast cancer-specific survival was investigated in the Nurses' Health Study (NHS). Overall, Kaplan Meier curves showed that there was no significant association between parity and breast cancer-specific survival (p=0.29). However, when the analysis was limited to ER+ tumors, it was found that nulliparous women had a suggestive worse survival compared with parous women (FIG. 27). In multivariate analysis there was still a marginally significant association among women with ER+ tumors, with nulliparous women having a nearly 30% increased risk of death from their disease (HR: 1.29, 95% CI: 0.98, 1.70; p=0.06). Assessing associations between age at first pregnancy and number of pregnancies gave similar results. In contrast, among women with ER− tumors, parity was not associated with breast cancer-specific survival (p=0.51). Thus, parity influences both the risk and prognosis of ER+ breast tumors.

Figure 29B:
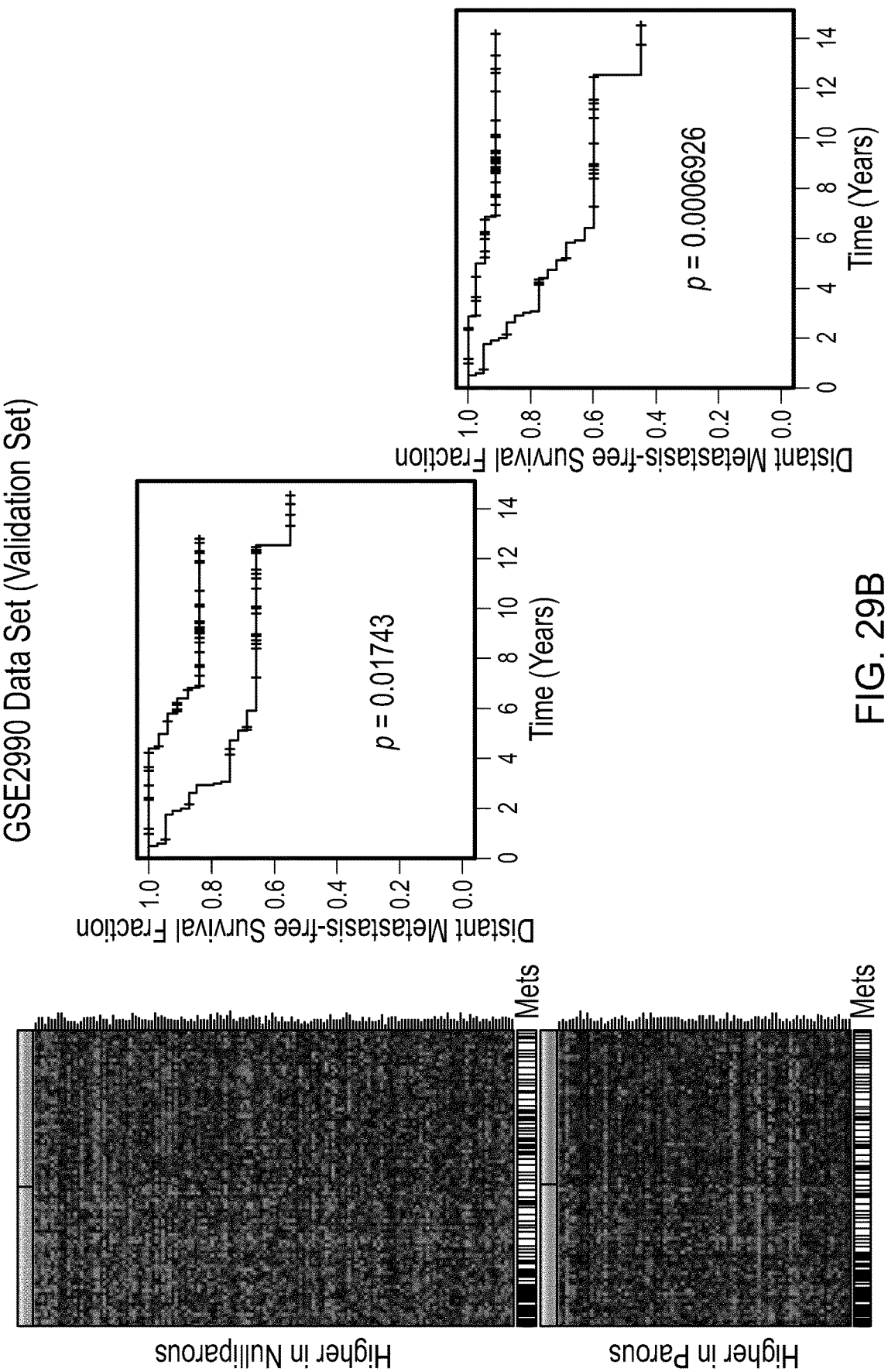
Figure 29C:
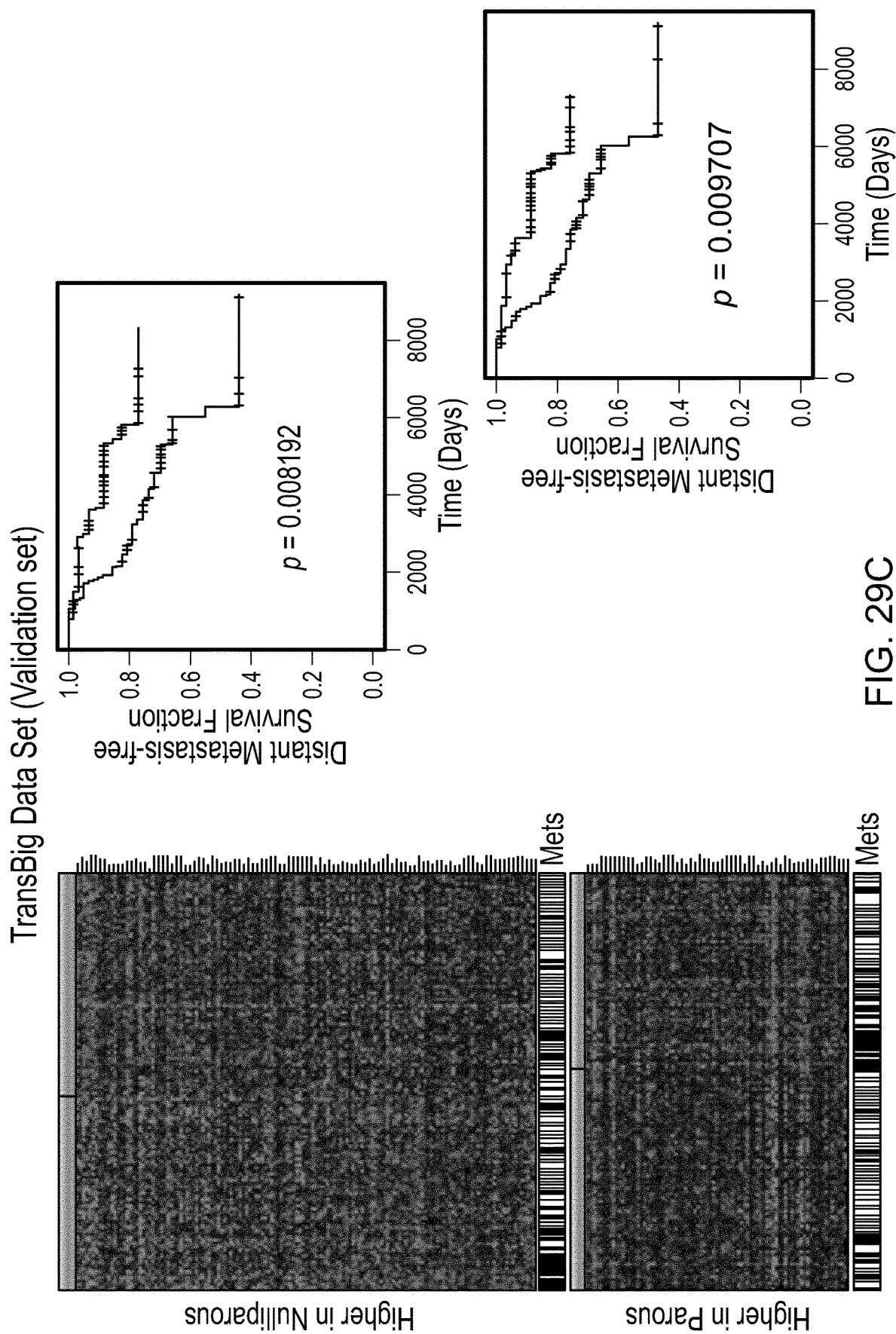

Because pregnancy may not induce the same epigenetic and gene expression changes in all women, due to germline variations, it was next investigated if the parity-related gene expression signature (PAGES) in CD44+ cells might be a more useful prognostic marker than parity status alone. Thus, the expression of PAGES was analyzed in public breast cancer gene expression data with clinical outcome. The supervised principle component analysis (SPCA) was applied on one of the cohorts (Wang) as a training set (FIG. 28) to identify the subset of the PAGES with prognostic value followed by validation in three other cohorts (Desmedt et al., supra; Sotiriou et al., supra; van de Vijver et al., supra), the data for which are shown in FIGS. 29A-C ( ). In each dataset ER+ tumors, the tumor subtype affected by parity, and cases without systemic therapy were selected in order to avoid differences due to treatment. All patients in the training set had small (<2 cm), lymph node negative tumors at the time of diagnosis. Using this approach, parity/nulliparity-related gene signatures were identified that split patients into two distinct groups with significant survival difference. The genes included in the prognostic signature are summarized in Table 18, which shows the gene symbol, gene description, gene expression pattern (i.e., high in parous and nulliparous samples), and prognostic values (good or bad prognosis) for each of the genes. Interestingly, such prognostic signature was found among genes highly expressed in both nulliparous and parous samples and each set of genes could be further separated into good and bad signatures. These results reflect the complex relationship between pregnancy and breast cancer that involves both protective and tumor-promoting effects.

TABLE 18

Genes Included In Prognostic Parity/Nulliparity Gene Signature

| Gene Symbol | Description | Expression | Prognosis |
| --- | --- | --- | --- |
| A2M | alpha-2-macroglobulin | nulliparous | bad |
| ABLIM1 | actin binding LIM protein 1 | nulliparous | bad |
| ADNP | activity-dependent neuroprotector homeobox | parous | bad |
| APPBP2 | amyloid beta precursor protein (cytoplasmic tail) binding protein 2 | parous | bad |
| AQP1 | aquaporin 1 (Colton blood group) | nulliparous | bad |
| ARID5B | AT rich interactive domain 5B (MRF1-like) | nulliparous | bad |

TABLE 18-continued

Genes Included In Prognostic Parity/Nulliparity Gene Signature

| Gene Symbol | Description | Expression | Prognosis |
|---|---|---|---|
| ASF1B | ASF1 anti-silencing function 1 homolog B (*S. cerevisiae*) | parous | bad |
| AZGP1 | alpha-2-glycoprotein 1, zinc-binding pseudogene 1; alpha-2-glycoprotein 1, zinc-binding | nulliparous | bad |
| B3GNT2 | UDP-GlcNAc:betaGal beta-1,3-N-acetylglucosaminyltransferase 1; UDP-GlcNAc:betaGal beta-1,3-N-acetylglucosaminyltransferase 2 | nulliparous | bad |
| BACE2 | beta-site APP-cleaving enzyme 2 | nulliparous | bad |
| BIRC5 | baculoviral IAP repeat-containing 5 | parous | bad |
| C11orf60 | chromosome 11 open reading frame 60 | nulliparous | bad |
| C12orf48 | chromosome 12 open reading frame 48 | parous | bad |
| C19orf56 | chromosome 19 open reading frame 56 | nulliparous | bad |
| CCDC101 | coiled-coil domain containing 101 | nulliparous | bad |
| CCL2 | chemokine (C-C motif) ligand 2 | nulliparous | bad |
| CCNI | cyclin I | nulliparous | bad |
| CCT2 | chaperonin containing TCP1, subunit 2 (beta) | parous | bad |
| CD44 | CD44 molecule (Indian blood group) | nulliparous | bad |
| CENPA | centromere protein A | parous | bad |
| CHEK1 | CHK1 checkpoint homolog (*S. pombe*) | parous | bad |
| CIR1 | corepressor interacting with RBPJ | nulliparous | bad |
| CLPB | ClpB caseinolytic peptidase B homolog (*E. coli*) | parous | bad |
| CNN3 | calponin 3, acidic | nulliparous | bad |
| CSTB | cystatin B (stefin B) | nulliparous | bad |
| CTDSP1 | CTD (carboxy-terminal domain, RNA polymerase II, polypeptide A) small phosphatase 1 | nulliparous | bad |
| CTDSPL | CTD (carboxy-terminal domain, RNA polymerase II, polypeptide A) small phosphatase-like | nulliparous | bad |
| CTPS | CTP synthase | parous | bad |
| CXCL12 | chemokine (C-X-C motif) ligand 12 (stromal cell-derived factor 1) | nulliparous | bad |
| DARC | Duffy blood group, chemokine receptor | nulliparous | bad |
| DDX39 | DEAD (Asp-Glu-Ala-Asp) box polypeptide 39 | parous | bad |
| DEF6 | differentially expressed in FDCP 6 homolog (mouse) | nulliparous | bad |
| DULLARD | dullard homolog (*Xenopus laevis*) | nulliparous | bad |
| DUSP4 | dual specificity phosphatase 4 | nulliparous | bad |
| EEF1A2 | eukaryotic translation elongation factor 1 alpha 2 | parous | bad |
| EFNA4 | ephrin-A4 | nulliparous | bad |
| EIF3G | eukaryotic translation initiation factor 3, subunit G | nulliparous | bad |
| F3 | coagulation factor III (thromboplastin, tissue factor) | nulliparous | bad |
| FBLN1 | fibulin 1 | nulliparous | bad |
| FBXO7 | F-box protein 7 | nulliparous | bad |
| FBXW4 | F-box and WD repeat domain containing 4 | nulliparous | bad |
| FLOT1 | flotillin 1 | nulliparous | bad |
| FTO | fat mass and obesity associated | nulliparous | bad |
| GAPVD1 | GTPase activating protein and VPS9 domains 1 | parous | bad |
| GGT5 | gamma-glutamyltransferase 5 | nulliparous | bad |
| GINS1 | GINS complex subunit 1 (Psf1 homolog) | parous | bad |
| GNB2L1 | guanine nucleotide binding protein (G protein), beta polypeptide 2-like 1 | nulliparous | bad |
| GOLM1 | golgi membrane protein 1 | nulliparous | bad |
| GSTK1 | glutathione S-transferase kappa 1 | nulliparous | bad |
| GSTP1 | glutathione S-transferase pi 1 | nulliparous | bad |
| GYPC | glycophorin C (Gerbich blood group) | nulliparous | bad |
| HEATR2 | HEAT repeat containing 2 | parous | bad |
| HIGD2A | HIG1 hypoxia inducible domain family, member 2A | nulliparous | bad |
| HLA-DPA1 | major histocompatibility complex, class II, DP alpha 1 | nulliparous | bad |
| HNRNPA0 | heterogeneous nuclear ribonucleoprotein A0 | nulliparous | bad |
| IGFBP4 | insulin-like growth factor binding protein 4 | nulliparous | bad |
| IMP3 | IMP3, U3 small nucleolar ribonucleoprotein, homolog (yeast) | nulliparous | bad |
| INPP1 | inositol polyphosphate-1-phosphatase | nulliparous | bad |
| ITM2A | integral membrane protein 2A | nulliparous | bad |
| JOSD1 | Josephin domain containing 1 | nulliparous | bad |
| KIAA0101 | KIAA0101 | parous | bad |
| KIAA0406 | KIAA0406 | parous | bad |
| LITAF | lipopolysaccharide-induced TNF factor | nulliparous | bad |
| LRIG1 | leucine-rich repeats and immunoglobulin-like domains 1 | nulliparous | bad |
| LSM2 | LSM2 homolog, U6 small nuclear RNA associated (*S. cerevisiae*) | nulliparous | bad |
| MCF2L | MCF.2 cell line derived transforming sequence-like | parous | bad |
| MGMT | O-6-methylguanine-DNA methyltransferase | nulliparous | bad |
| MNAT1 | menage a trois homolog 1, cyclin H assembly factor (*Xenopus laevis*) | parous | bad |
| NAP1L1 | nucleosome assembly protein 1-like 1 | nulliparous | bad |
| NFYC | nuclear transcription factor Y, gamma | nulliparous | bad |
| NUPR1 | nuclear protein, transcriptional regulator, 1 | nulliparous | bad |
| PALM | paralemmin | nulliparous | bad |
| PIK3IP1 | phosphoinositide-3-kinase interacting protein 1 | nulliparous | bad |
| PNRC1 | proline-rich nuclear receptor coactivator 1 | nulliparous | bad |
| POP1 | processing of precursor 1, ribonuclease P/MRP subunit (*S. cerevisiae*) | parous | bad |
| PPM1D | protein phosphatase 1D magnesium-dependent, delta isoform | parous | bad |
| PRC1 | protein regulator of cytokinesis 1 | parous | bad |

TABLE 18-continued

Genes Included In Prognostic Parity/Nulliparity Gene Signature

| Gene Symbol | Description | Expression | Prognosis |
|---|---|---|---|
| PSAP | prosaposin | nulliparous | bad |
| PYCRL | pyrroline-5-carboxylate reductase-like | parous | bad |
| RACGAP1 | Rac GTPase activating protein 1 pseudogene; Rac GTPase activating protein 1 | parous | bad |
| RCOR3 | REST corepressor 3 | nulliparous | bad |
| RECQL4 | RecQ protein-like 4 | parous | bad |
| RNF146 | ring finger protein 146 | nulliparous | bad |
| RPL15 | ribosomal protein L15 pseudogene 22; ribosomal protein L15 pseudogene 18; ribosomal protein L15 pseudogene 17; ribosomal protein L15 pseudogene 3; ribosomal protein L15 pseudogene 7; ribosomal protein L15 | nulliparous | bad |
| RPL22 | ribosomal protein L22 pseudogene 11; ribosomal protein L22 | nulliparous | bad |
| RPLP2 | ribosomal protein, large, P2 pseudogene 3; ribosomal protein, large, P2 | nulliparous | bad |
| RPS6KA1 | ribosomal protein S6 kinase, 90 kDa, polypeptide 1 | nulliparous | bad |
| RRP15 | ribosomal RNA processing 15 homolog (S. cerevisiae) | parous | bad |
| SCRIB | scribbled homolog (Drosophila) | parous | bad |
| SEPP1 | selenoprotein P, plasma, 1 | nulliparous | bad |
| SLC17A9 | solute carrier family 17, member 9 | parous | bad |
| SLC25A28 | solute carrier family 25, member 28 | nulliparous | bad |
| SLC25A6 | solute carrier family 25 (mitochondrial carrier; adenine nucleotide translocator), member 6 | nulliparous | bad |
| SLC35B1 | solute carrier family 35, member B1 | parous | bad |
| SPC25 | SPC25, NDC80 kinetochore complex component, homolog (S. cerevisiae) | parous | bad |
| SRGAP2 | SLIT-ROBO Rho GTPase activating protein 2 | parous | bad |
| STMN1 | stathmin 1 | parous | bad |
| SYNGR3 | synaptogyrin 3 | parous | bad |
| TIMM17A | translocase of inner mitochondrial membrane 17 homolog A (yeast) | parous | bad |
| TNFRSF11 | tumor necrosis factor receptor superfamily, member 11b | nulliparous | bad |
| TNNT3 | troponin T type 3 (skeletal, fast) | nulliparous | bad |
| TPT1 | similar to tumor protein, translationally-controlled 1; tumor protein, translationally-controlled 1 | nulliparous | bad |
| TRIP10 | thyroid hormone receptor interactor 10 | nulliparous | bad |
| TSPAN7 | tetraspanin 7 | nulliparous | bad |
| TXNIP | thioredoxin interacting protein | nulliparous | bad |
| UBE3C | ubiquitin protein ligase E3C | parous | bad |
| UCKL1 | uridine-cytidine kinase 1-like 1 | parous | bad |
| USP32 | similar to TBC1 domain family, member 3; ubiquitin specific peptidase 32 | parous | bad |
| YWHAH | tyrosine 3-monooxygenase/tryptophan 5-monooxygenase activation protein, eta polypeptide | nulliparous | bad |
| ZC3H3 | zinc finger CCCH-type containing 3 | parous | bad |
| ZFP36L1 | zinc finger protein 36, C3H type-like 1 | nulliparous | bad |
| ZFP36L2 | zinc finger protein 36, C3H type-like 2 | nulliparous | bad |
| ACY1 | aminoacylase 1 | parous | good |
| AGGF1 | angiogenic factor with G patch and FHA domains 1 | parous | good |
| AGK | acylglycerol kinase | nulliparous | good |
| AMIGO2 | adhesion molecule with Ig-like domain 2 | nulliparous | good |
| ANKRD46 | ankyrin repeat domain 46 | nulliparous | good |
| APOD | apolipoprotein D | parous | good |
| APOL1 | apolipoprotein L, 1 | parous | good |
| APOL3 | apolipoprotein L, 3 | parous | good |
| ARHGAP1 | Rho GTPase activating protein 11B; Rho GTPase activating protein 11A | parous | good |
| ATG4B | ATG4 autophagy related 4 homolog B (S. cerevisiae) | parous | good |
| AZIN1 | antizyme inhibitor 1 | nulliparous | good |
| B3GALNT1 | beta-1,3-N-acetylgalactosaminyltransferase 1 (globoside blood group) | nulliparous | good |
| C13orf34 | chromosome 13 open reading frame 34 | parous | good |
| CBX3 | similar to chromobox homolog 3; chromobox homolog 3 | nulliparous | good |
| CD79A | CD79a molecule, immunoglobulin-associated alpha | parous | good |
| CEACAM5 | carcinoembryonic antigen-related cell adhesion molecule 5 | parous | good |
| CHCHD3 | coiled-coil-helix-coiled-coil-helix domain containing 3 | nulliparous | good |
| CNBP | CCHC-type zinc finger, nucleic acid binding protein | parous | good |
| CNIH | cornichon homolog (Drosophila) | nulliparous | good |
| COBRA1 | cofactor of BRCA1 | nulliparous | good |
| COQ2 | coenzyme Q2 homolog, prenyltransferase (yeast) | nulliparous | good |
| COX6A1 | cytochrome c oxidase subunit VIa polypeptide 1 | nulliparous | good |
| CSTF1 | cleavage stimulation factor, 3' pre-RNA, subunit 1, 50 kDa | nulliparous | good |
| CYC1 | cytochrome c-1 | nulliparous | good |
| DCPS | decapping enzyme, scavenger | parous | good |
| DPM1 | dolichyl-phosphate mannosyltransferase polypeptide 1, catalytic subunit | nulliparous | good |
| DYNLL1 | dynein, light chain, LC8-type 1 | parous | good |
| E2F5 | E2F transcription factor 5, p130-binding | nulliparous | good |
| EFR3A | EFR3 homolog A (S. cerevisiae) | nulliparous | good |
| EIF3J | eukaryotic translation initiation factor 3, subunit J | parous | good |
| ERO1L | ERO1-like (S. cerevisiae) | nulliparous | good |
| FAM164A | family with sequence similarity 164, member A | nulliparous | good |
| FAM55C | family with sequence similarity 55, member C | parous | good |
| FEN1 | flap structure-specific endonuclease 1 | nulliparous | good |
| FLRT3 | fibronectin leucine rich transmembrane protein 3 | nulliparous | good |

TABLE 18-continued

Genes Included In Prognostic Parity/Nulliparity Gene Signature

| Gene Symbol | Description | Expression | Prognosis |
|---|---|---|---|
| GLG1 | golgi apparatus protein 1 | parous | good |
| GUF1 | GUF1 GTPase homolog (*S. cerevisiae*) | parous | good |
| HAUS5 | HAUS augmin-like complex, subunit 5 | parous | good |
| HDGFRP3 | hepatoma-derived growth factor, related protein 3 | nulliparous | good |
| HLA-B | major histocompatibility complex, class I, C; major histocompatibility complex, class I, B | parous | good |
| HLA-DOB | major histocompatibility complex, class II, DO beta | parous | good |
| HMGB2 | high-mobility group box 2 | nulliparous | good |
| INPP5D | inositol polyphosphate-5-phosphatase, 145 kDa | parous | good |
| INVS | inversin | parous | good |
| ITCH | itchy E3 ubiquitin protein ligase homolog (mouse) | parous | good |
| KCNG2 | potassium voltage-gated channel, subfamily G, member 2 | parous | good |
| KDELR2 | KDEL (Lys-Asp-Glu-Leu) endoplasmic reticulum protein retention receptor 2 | nulliparous | good |
| KIAA0391 | KIAA0391 | nulliparous | good |
| LAPTM4B | lysosomal protein transmembrane 4 beta | nulliparous | good |
| LARP4 | La ribonucleoprotein domain family, member 4 | nulliparous | good |
| LILRB1 | leukocyte immunoglobulin-like receptor, subfamily B (with TM and ITIM domains), member 1 | parous | good |
| MAP3K7IP | mitogen-activated protein kinase kinase kinase 7 interacting protein 1 | parous | good |
| METT11D1 | methyltransferase 11 domain containing 1; similar to methyltransferase 11 domain containing 1 isoform 2 | parous | good |
| MLLT11 | myeloid/lymphoid or mixed-lineage leukemia (trithorax homolog, *Drosophila*); translocated to, 11 | nulliparous | good |
| MLX | MAX-like protein X | parous | good |
| MTDH | metadherin | nulliparous | good |
| NDRG4 | NDRG family member 4 | nulliparous | good |
| NDUFA4 | NADH dehydrogenase (ubiquinone) 1 alpha subcomplex, 4, 9 kDa | nulliparous | good |
| NFS1 | NFS1 nitrogen fixation 1 homolog (*S. cerevisiae*) | nulliparous | good |
| NRAS | neuroblastoma RAS viral (v-ras) oncogene homolog | nulliparous | good |
| P4HA2 | prolyl 4-hydroxylase, alpha polypeptide II | nulliparous | good |
| PHF1 | PHD finger protein 1 | parous | good |
| PIK3CG | phosphoinositide-3-kinase, catalytic, gamma polypeptide | parous | good |
| PLEKHF2 | pleckstrin homology domain containing, family F (with FYVE domain) member 2 | nulliparous | good |
| PLOD3 | procollagen-lysine, 2-oxoglutarate 5-dioxygenase 3 | parous | good |
| PNP | nucleoside phosphorylase | nulliparous | good |
| PNPLA2 | patatin-like phospholipase domain containing 2 | parous | good |
| PPP1CC | protein phosphatase 1, catalytic subunit, gamma isoform | nulliparous | good |
| PPP3R1 | protein phosphatase 3 (formerly 2B), regulatory subunit B, alpha isoform | nulliparous | good |
| PRPF31 | PRP31 pre-mRNA processing factor 31 homolog (*S. cerevisiae*) | nulliparous | good |
| PSMA2 | proteasome (prosome, macropain) subunit, alpha type, 2 | nulliparous | good |
| PSMA3 | proteasome (prosome, macropain) subunit, alpha type, 3 | nulliparous | good |
| PSMA4 | proteasome (prosome, macropain) subunit, alpha type, 4 | nulliparous | good |
| PSMA6 | proteasome (prosome, macropain) subunit, alpha type, 6 | nulliparous | good |
| PSMD4 | proteasome (prosome, macropain) 26S subunit, non-ATPase, 4 | nulliparous | good |
| PUF60 | poly-U binding splicing factor 60 KDa | nulliparous | good |
| RALA | v-ral simian leukemia viral oncogene homolog A (ras related) | nulliparous | good |
| RBBP7 | retinoblastoma binding protein 7 | nulliparous | good |
| RFC3 | replication factor C (activator 1) 3, 38 kDa | nulliparous | good |
| RHBDL1 | rhomboid, veinlet-like 1 (*Drosophila*) | parous | good |
| RINT1 | RAD50 interactor 1 | parous | good |
| RNASEH1 | ribonuclease H1 | parous | good |
| RNF125 | ring finger protein 125 | parous | good |
| RPS11 | ribosomal protein S11 pseudogene 5; ribosomal protein S11 | parous | good |
| RPS6 | ribosomal protein S6 pseudogene 25; ribosomal protein S6; ribosomal protein S6 pseudogene 1 | parous | good |
| RRAGA | Ras-related GTP binding A | parous | good |
| SAPS3 | SAPS domain family, member 3 | parous | good |
| SCNN1B | sodium channel, nonvoltage-gated 1, beta | nulliparous | good |
| SHMT2 | serine hydroxymethyltransferase 2 (mitochondrial) | nulliparous | good |
| SKA1 | chromosome 18 open reading frame 24 | parous | good |
| SLC25A32 | solute carrier family 25, member 32 | nulliparous | good |
| SRP19 | signal recognition particle 19 kDa | nulliparous | good |
| ST20 | suppressor of tumorigenicity 20 | parous | good |
| STAU1 | staufen, RNA binding protein, homolog 1 (*Drosophila*) | nulliparous | good |
| STX3 | syntaxin 3 | nulliparous | good |
| THAP4 | THAP domain containing 4 | parous | good |
| TIMELESS | timeless homolog (*Drosophila*) | nulliparous | good |
| TMCO1 | transmembrane and coiled-coil domains 1 | nulliparous | good |
| TMED9 | transmembrane emp24 protein transport domain containing 9 | nulliparous | good |
| TMEM158 | transmembrane protein 158 | nulliparous | good |
| TMEM222 | transmembrane protein 222 | parous | good |
| TOB1 | transducer of ERBB2, 1 | nulliparous | good |
| TSPAN13 | tetraspanin 13 | nulliparous | good |
| TTC38 | tetratricopeptide repeat domain 38 | parous | good |
| TUBA1C | tubulin, alpha 1c | nulliparous | good |
| TXNDC9 | thioredoxin domain containing 9 | nulliparous | good |

TABLE 18-continued

Genes Included In Prognostic Parity/Nulliparity Gene Signature

| Gene Symbol | Description | Expression | Prognosis |
|---|---|---|---|
| UBA2 | ubiquitin-like modifier activating enzyme 2 | nulliparous | good |
| UQCRB | similar to ubiquinol-cytochrome c reductase binding protein | nulliparous | good |
| WDR12 | WD repeat domain 12 | nulliparous | good |
| XPOT | exportin, tRNA (nuclear export receptor for tRNAs); similar to Exportin-T (tRNA exportin) (Exportin(tRNA)) | nulliparous | good |
| YEATS4 | YEATS domain containing 4 | nulliparous | good |
| YIF1A | Yip1 interacting factor homolog A (S. cerevisiae) | nulliparous | good |
| ZDHHC14 | zinc finger, DHHC-type containing 14 | parous | good |
| ZFAND1 | zinc finger, AN1-type domain 1 | nulliparous | good |
| ZNF217 | zinc finger protein 217 | nulliparous | good |
| ZNF264 | zinc finger protein 264 | nulliparous | good |
| ZNF304 | zinc finger protein 304 | nulliparous | good |
| ZNF706 | zinc finger protein 706 | nulliparous | good |
| ZWINT | ZW10 interactor | nulliparous | good |

Example 10: Parity-Associated Decrease in Mammary Epithelial Progenitors and Breast Tumor Initiation The data described in the Examples above support the hypothesis that a decrease in the number and proliferative potential of luminal progenitors in parous women directly relates to a decrease in breast cancer risk for both ER+ and ER− breast cancers, and that this effect is dependent on the age at first full-term pregnancy. A mathematical model of the dynamics of proliferating mammary epithelial cells was designed that can accumulate the changes leading to cancer initiation. In the model, described in detail below, two types of cells were considered: (1) a self-renewing population of stem cells and, (2) a population of proliferating hormone-responsive luminal progenitors that result from the differentiation of these stem cells.

Figure 30:
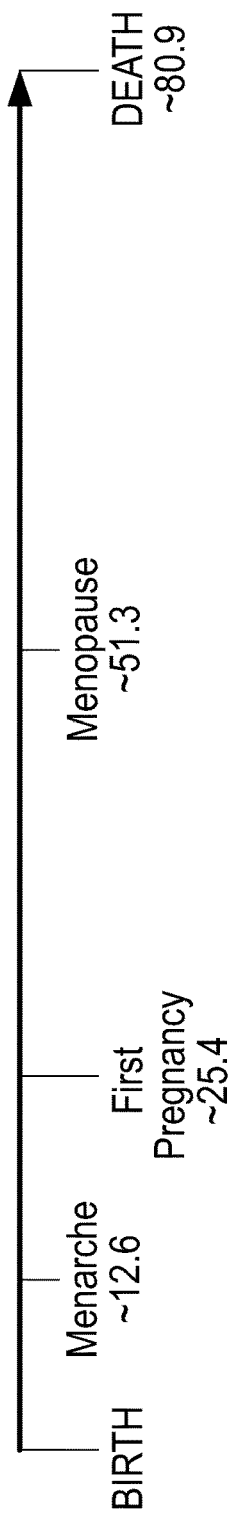
FIG. 30 contains a diagram showing the timeline for simulations in a mathematical model of the dynamics of proliferating mammary epithelial cells that can accumulate the changes leading to cancer initiation, run from the time of menarche at 12.6 years through cancer initiation or death at 80.9 years. The earliest time of pregnancy is at menarche; the latest time is right before menopause at 51.3 years.

Mathematical Modeling:

Simulations were initiated at menarche and continued until cancer initiation or death, as depicted in the timeline in FIG. 30. The effect of pregnancy at varying times from menarche through right before menopause on cancer initiation was tested and compared against the nulliparous cancer initiation risk. The robustness of the simulation over varying numbers of stem cells per terminal end duct, additional proliferative capacities resulting from pregnancy, and rates of asymmetric stem cell division were then tested.

The dynamics of stem cells in the breast ductal system was first studied. Given the population structure inherent to breast ducts, it was assumed that the stem cells in each duct act independently. As such, the dynamics of a single duct within the breast was investigated since the total probability of cancer initiation is given by the probability per niche times the number of niches. Thus, the relative likelihood of cancer initiation is not altered by considering only one niche. The overall number of stem cells in the breast is on the order of 5 to 10 cells per duct, and this number was denoted by N. A fundamental time step of this system to be dictated by the division time of stem cells, $t_{step}$, which varies during pregnancy, was defined. In previously published in vivo experiments, the mean cell cycle length of benign breast hyperplasia cells was approximately 162 hours per cell. It was assumed that even benign breast hyperplasia cells divide faster than stem cells; thus, using $t_{step}$=162 hours as the average stem cell cycle length when not pregnant may be an overestimation of the number of stem cell divisions that occur in the normal breast. Within a duct, a single stem cell is randomly chosen to divide during each time step proportional to the fitness of the cell, following a stochastic process known as the Moran model (see, Moran, P. A. P. (1962). The statistical processes of evolutionary theory (Oxford: Clarendon Press). National Center for Health Statistics (US) (2012). Health, United States, 2011: With Special Feature on Socioeconomic Status and Health (Hyattsville, Md.)). According to this model, the divided cell is replaced by one of the daughter cells of the division, while the other daughter replaces another stem cell that was randomly selected from the population. Use of this model ensured preservation of homeostasis in the normal breast cell population. For each cell division, a single mutation was allowed to arise in one of the two daughter cells of the division.

Figure 34:
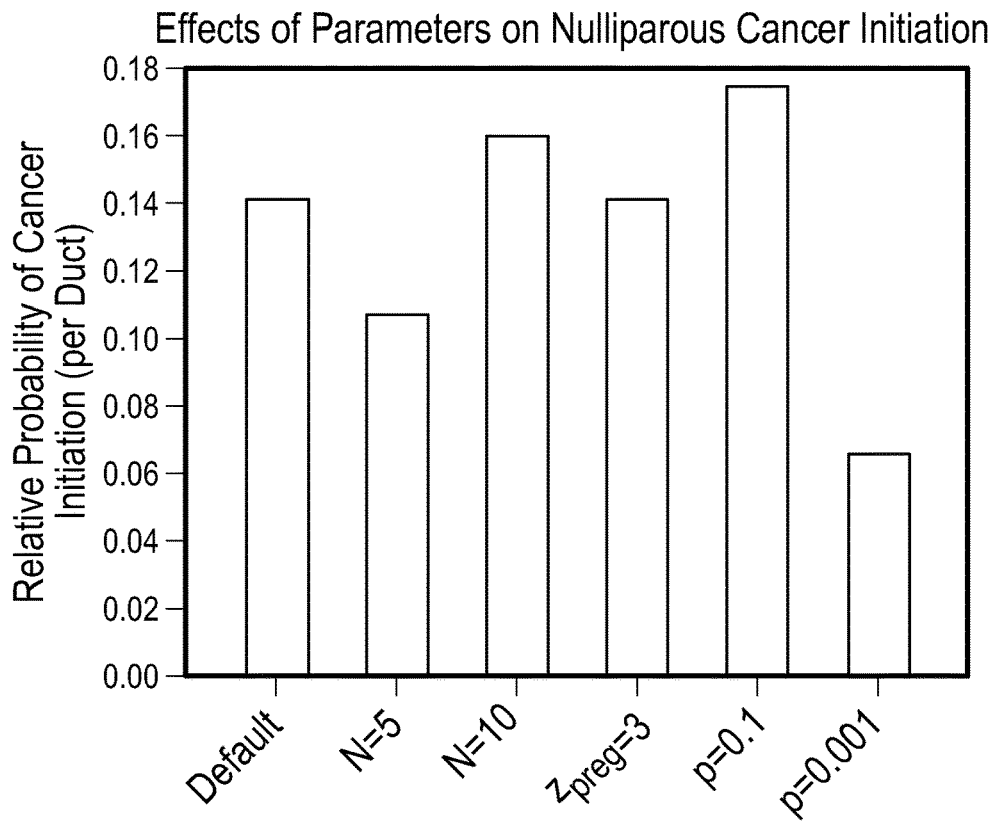
FIG. 34 is a bar graph quantifying the effect the indicated parameters of the mathematical model described in Example 10 (N value, Zpreg, and p) have on the relative probability of cancer initiation (per duct) relative to nulliparous women. The default values were: N=8, p=$10^{-2}$, $z_{preg}$=2.

In the mature breast, stem cells divide primarily to maintain cellular integrity. However, differentiating events do occur, although rarely. In this model, with probability p, cell division in the current time step was allowed to be asymmetric, producing one stem daughter cell to maintain the stem cell population and one progenitor daughter. Since the exact rate of differentiation is unknown, $p=10^{-1}$ to $10^{-3}$ was tested. With the remaining 1−p probability, the stem cell division is symmetric and followed the usual Moran division dynamics. In each time step thereafter, all of the cells resulting from the progenitor daughter divided and differentiated further until a total of z cell divisions were accumulated. We set z=10, to fit data from mouse fat pad depletion experiments (see, Kordon, E. C., and Smith, G. H. (1998). An entire functional mammary gland may comprise the progeny from a single cell. Development 125, 1921-1930.) After $z_{pre}$ divisions, the cells were considered differentiated and, at this point, they were no longer included in the cells considered in the mathematical model. Thus, in the wild-type system, there were N stem cells per duct and $2^{z+1}-1$ progenitor cells per differentiation cascade. FIG. 34 describes the temporal dynamics of the system.

During each cell division, genetic alterations contributing to cancer initiation may arise. A number $n_{mut}$ of mutations were considered that, when combined, result in a single cell leading to cancer initiation. These mutations could be any of the many mutations commonly found in breast cancer with initiation potential; however, it was assumed that only a single mutational hit was necessary to (in)activate the gene. The simulation was tested with mutation rates on the order of $10^{-5}$ mutations per gene per cell division to limit the required number of simulations for detection to a reasonable number; however, results remained consistent even at lower mutation rates. The following mutational effects were assumed for each mutation: in stem cells, mutant cells had a relative fitness of $f_{mut}=1.1$, i.e. a fitness increase of 10%, resulting in an increased probability of dividing, while mutant progenitor cells divided an additional $z_{mut}=1$ times (FIG. 34). Since the number of stem cells per duct is small, the fitness of mutant alleles has little effect on cancer initiation probabilities, as the fixation time of mutations is much smaller than the mutation accumulation time (see, Hambardzumyan, D., Cheng, Y. K., Haeno, H., Holland, E. C., and Michor, F. (2011). The probable cell of origin of NF1- and PDGF-driven glioblastomas. PLoS One 6, e24454). Thus, ignoring the specific value of $f_{mut}$ is justified. These assumptions presume that the mutations primarily act to increase the proliferation rate of cells. Mutant fitness values were considered to be multiplicative while mutant progenitor division capacity was considered to be additive. Thus, the relative fitness of a stem cell with in mutations was $f_{mut}^n$ and the number of divisions a mutant progenitor with n mutations was $z+n*z_{mut}$. Additionally, progenitor cells must accumulate some propensity towards self-renewal: a parameter $\gamma=\gamma_{base}-i*\gamma_{step}$ was defined as the probability of a progenitor cell at differentiation level $0 \leq i \leq z+n*z_{mut}$ acquiring self-renewal. Cancer initiation was defined as a single cell that accumulated all required mutations and either retained or acquired the ability to self-renew, either through being a stem cell or through acquiring a genetic or epigenetic self-renewal event.

The phenotypic alterations that occur in the breast during pregnancy and as a result of pregnancy were considered. For the purposes of this simulation, the 280 day period of time for the pregnancy itself was considered as the time period during which parameters are altered by pregnancy. It has been previously published that pregnancy results in terminal differentiation of progenitor cells into milk producing cells as well as increased proliferation of cells. To model these effects, further differentiation of progenitor cells during pregnancy by an additional $z_{preg}$ differentiation levels, and a decrease in the cell cycle length of stem cells was allowed (FIG. 34). According to several groups, there is a 4.5 to 8.5-fold increase in Ki67+ cells during pregnancy. Thus, a 4-fold to 8-fold increase in progenitor cells during pregnancy was allowed, corresponding to $p_{preg}=2$ to 3. The remaining ~1.1 fold increase in proliferation was modeled as a decrease in stem cell cycle length to $t_{step,preg}=147$ hours. Additionally, as described in the Examples, above, there was also a decrease in the number of proliferative progenitors after pregnancy: this change was simulated in population structure by decreasing the number of differentiation levels in the progenitor hierarchy by $z_{post}$. The experiments showed a 2-3 fold drop in p27+ expressing progenitor cells, which would correspond to $z_{post}=1$.

The simulation spanned from menarche to death or initiation of cancer within the duct. As such, the total simulation time was calculated from the average women's life expectancy in the United States, which was 80.9 years in 2009, and the average age of menarche, which ranged between 12.4-12.7 years of age for differing age groups in 2002 (FIG. 34). The mean age of menarche between the groups was used, which was 12.6 years, and thus resulted in a total of 68.3 years of simulation time. The effects of pregnancy occurring at four roughly equidistant time points, $t_{preg}$ was tested: immediately following menarche, time of first pregnancy at the average age of 25.4 in 2010, immediately before menopause at the average age of 51.3 in 1998, and halfway between average first pregnancy and menopause at the age of 38.3. All time points were tabulated from the most recent government-provided data. The effects of varying the simulation parameters independently for each pregnancy age $t_{preg}$ were tested. All fixed value parameters and the values of all other parameters are listed in the tables below.

TABLE 19

Fixed parameter values

| $t_{total}$ (years) | $f_{mut}$ | $\gamma$ | $\gamma_{step}$ | $\mu$ | $t_{step}$ (h) | $t_{step,preg}$ (h) | z | $z_{mut}$ | $z_{post}$ |
|---|---|---|---|---|---|---|---|---|---|
| 68.3 | 1.1 | 0.1 | 0.005 | $2 \times 10^{-5}$ | 162 | 147 | 10 | 1 | −1 |

Legend: Parameters that remained unchanged throughout all simulations are shown.

TABLE 20

Range of parameter values investigated

| $t_{preg}$ | N | $n_{mut}$ | p | $z_{preg}$ |
|---|---|---|---|---|
| 0 | 5 | 1 | $10^{-3}$ | 2 |
| 12.8 | 8 | 2 | $10^{-2}$ | 3 |
| 25.7 | 10 | | $10^{-1}$ | |
| 38.7 | | | | |

Legend: For each parameter of interest, multiple values were tested. Values defaulted to the numbers in bold.

Figure 31:
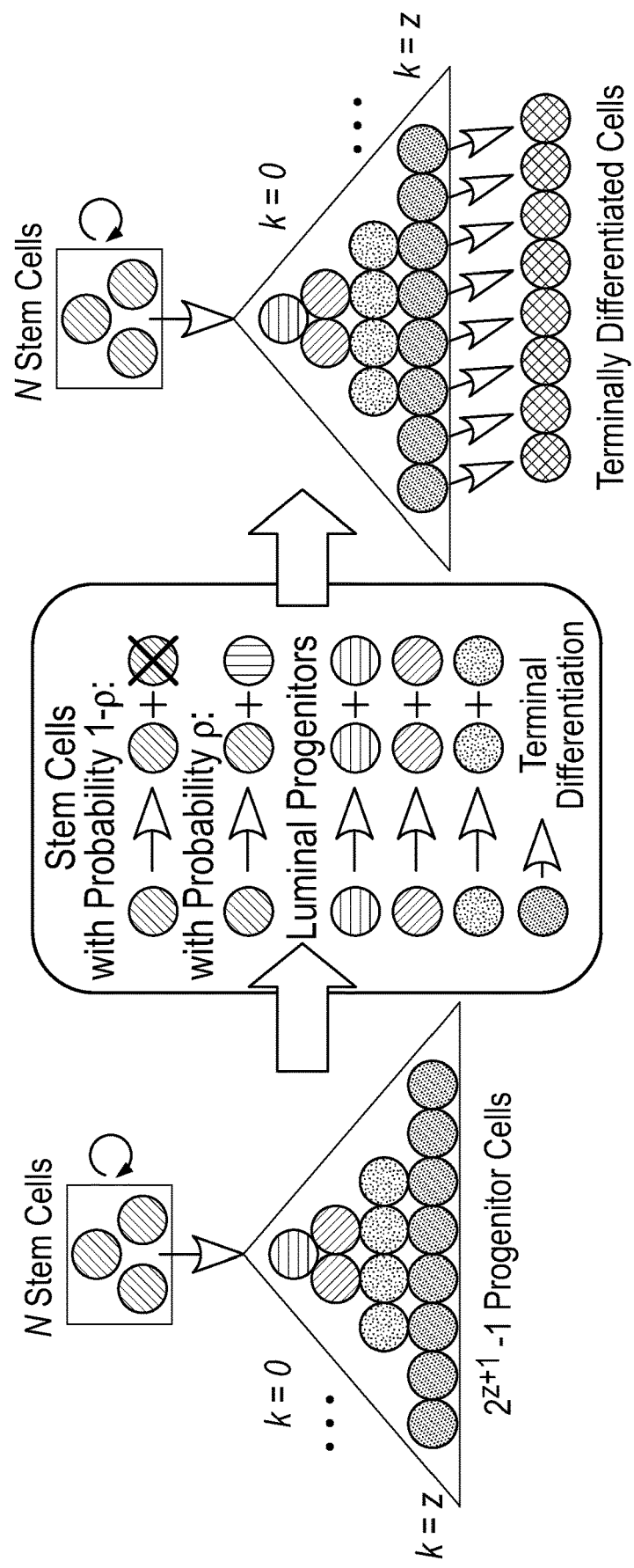
FIGS. 31-33 are schematic representations of a mathematical model of the dynamics of proliferating mammary epithelial cells that can accumulate the changes leading to cancer initiation.

In the schematic depicted in FIG. 31, initially, there are N wild-type stem cells (top of schematic), which give rise to a differentiation cascade of $2^{z+1}-1$ wild-type luminal progenitor cells (triangular, lower region). At each time step, all progenitor cells as well as one randomly selected stem cell divide. With probability α, the stem cell divides symmetrically and one daughter cell replaces another randomly chosen stem cell. With probability 1−α, the stem cell divides asymmetrically and one daughter cell remains a stem cell while the other daughter cell becomes committed to the progenitor population. Regardless of the dividing stem cell's fate, all existing progenitor cells divide symmetrically for a total of z times to give rise to successively more differentiated cells (progressively darker shades of gray) before becoming terminally differentiated. Darkening gray gradations refer to successively more differentiated cells and serve to clarify a single time step of the stochastic process.

Figure 32:
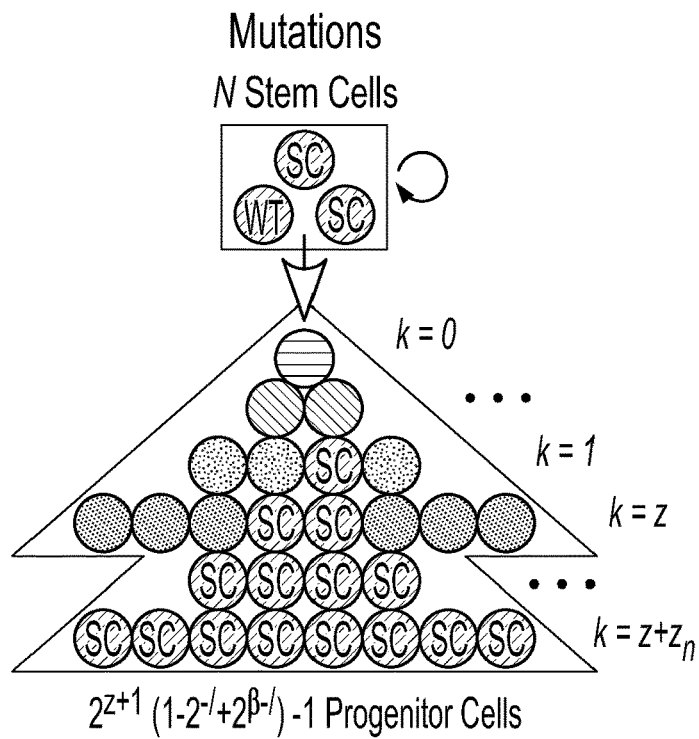

In FIG. 32, the acquisition of mutations leading to breast cancer initiation all result in an increased relative fitness (i.e., growth rate) $f_{mut}$ in stem cells ("SC") as compared to wild-type cells ("WT") and an additional number of divisions $z_{mut}$ progenitor cells can undergo before terminally differentiating.

Figure 33:
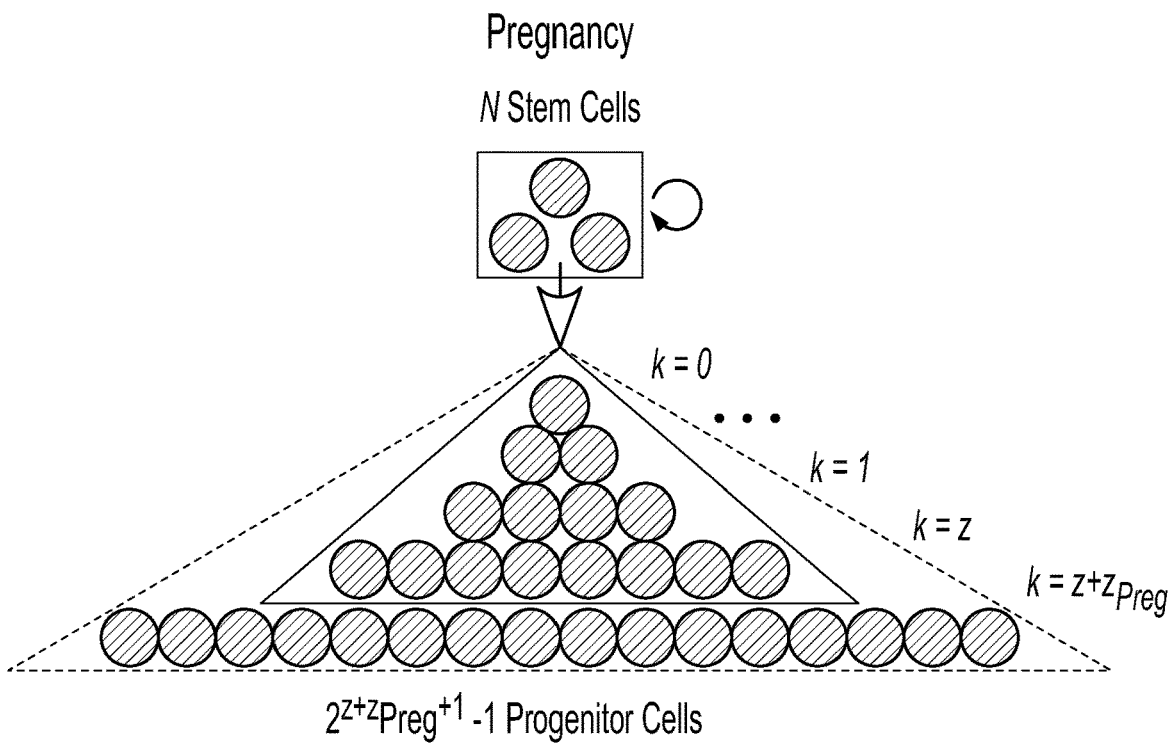

In FIG. 33, during pregnancy, progenitor cells experience an expansion in proliferative capacity through an additional number of division $z_{preg}$ in order to form terminally differentiated milk-producing cells (dotted triangle) and a decrease in cell cycle length.

Figure 35:
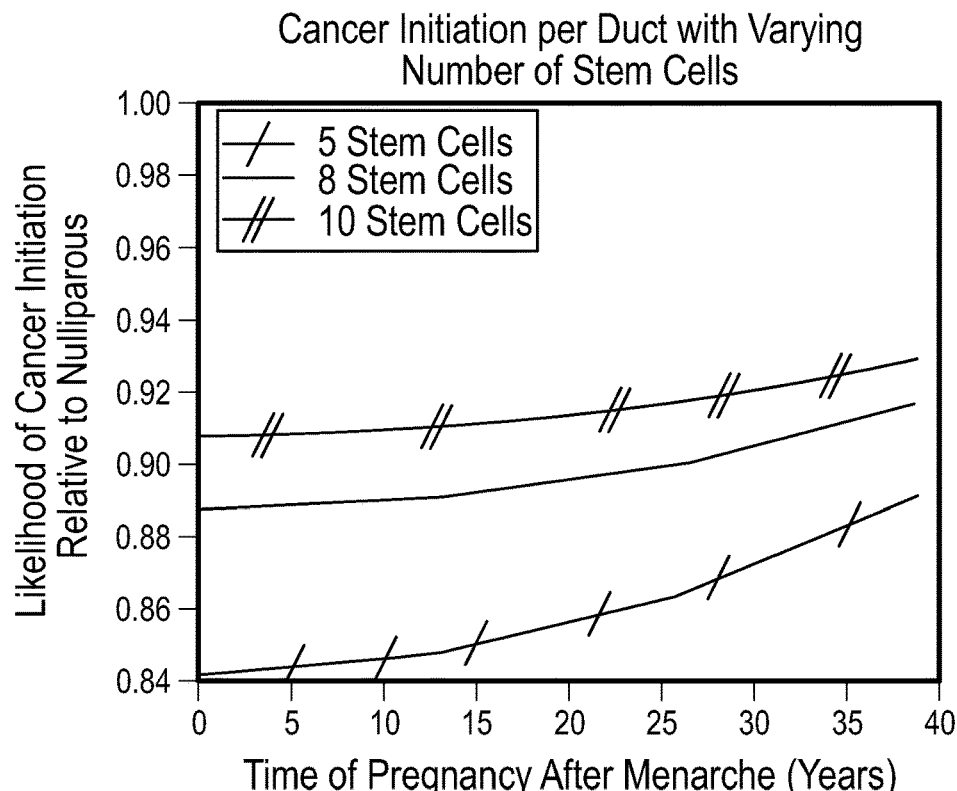
FIG. 35 is a line graph plotting the likelihood (relative probability) of cancer initiation relative to nulliparous (y-axis) against time of first pregnancy after menarche (years) on the x-axis for the indicated starting number of stem cells (N=5, N=8, and N=10).
Figure 36:
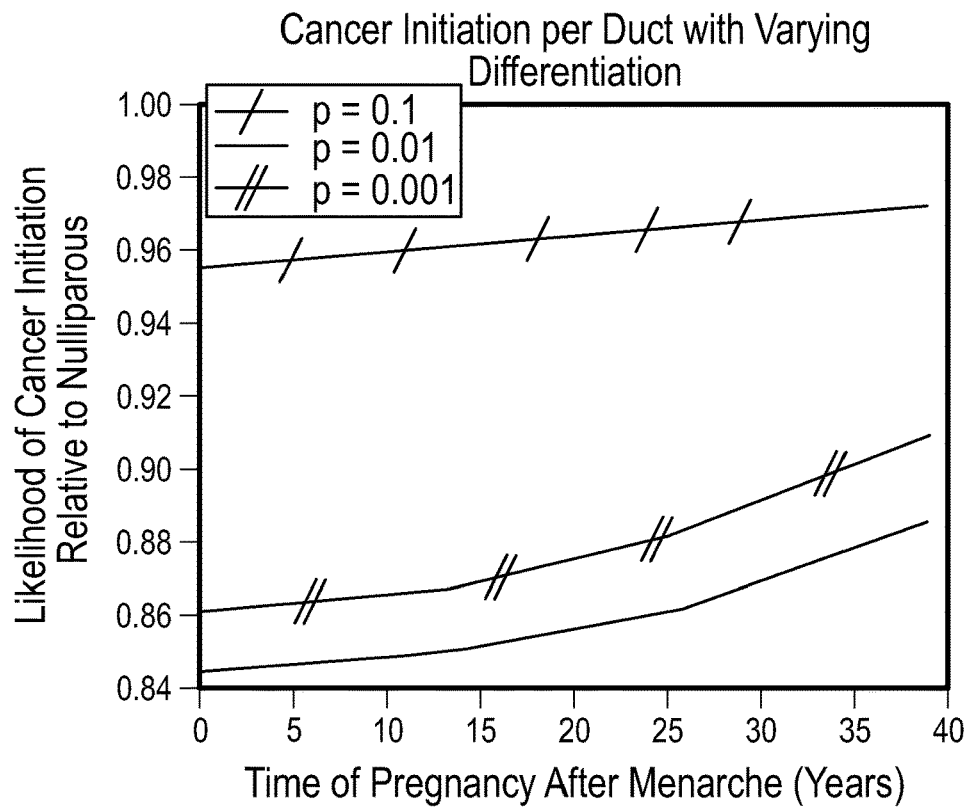
FIG. 36 is a line graph plotting the likelihood (relative probability) of cancer initiation relative to nulliparous (y-axis) against time of first pregnancy after menarche (years) on the x-axis for the indicated probabilities of stem cell differentiation (p=0.1, p=0.01, and p=0.001)
Figure 37:
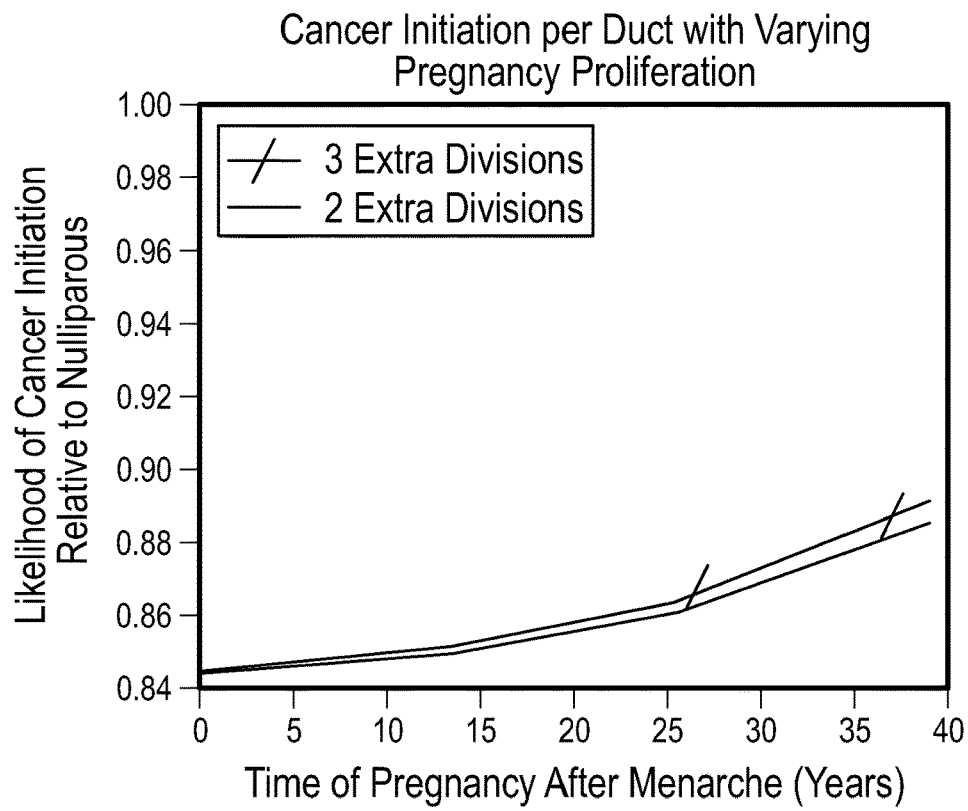
FIG. 37 is a line graph plotting the likelihood (relative probability) of cancer initiation relative to nulliparous (y-axis) against time of first pregnancy after menarche (years) on the x-axis for the indicated number of additional cell divisions during pregnancy (3 and 2).

The effect of pregnancy on breast cancer per duct (expressed as the relative probability of cancer initiation) as compared to nulliparous simulations initiation at varying times after menarche was tested and compared to the risk of tumor initiation in nulliparous women. Default values were N=8, $p=10^{-2}$, $z_{preg}=2$ (FIG. 34). It was observed that the relative likelihood of initiation increased with later pregnancy. The robustness of the simulation over varying numbers of stem cells per terminal end duct, additional proliferative capacities resulting from pregnancy, and rates of asymmetric stem cell division were tested (FIGS. 35-37). The relative likelihood of cancer initiation was then compared with pregnancy occurring at four different time points during childbearing years as compared to nulliparous simulations. It was found that the probability of cancer initiation in a duct increases as the age at first pregnancy increases. Furthermore, these simulations showed that differences in the numbers of luminal epithelial progenitors with proliferative potential is the most probable explanation for differences in breast cancer risk due to reproductive (e.g., parity) and genetic (e.g., BRCA1/2 germline mutation) factors.

In summary, it was found that both increasing numbers of stem cells per duct and increasing rates of asymmetric stem cell division increase the rate of cancer initiation per duct. Also, as expected, changes in the proliferative capacity of progenitor cells during pregnancy had no effect in the nulliparous state. The relative likelihood of cancer initiation was then compared with pregnancy occurring at four different time points during a woman's childbearing years as compared to the nulliparous simulations. It was found that the probability of cancer initiation in a duct increases as the age of first pregnancy increases within the range of all simulated parameters. Additionally, the probability of cancer initiation is greater in nulliparous situations than in all pregnancy simulations. Interestingly, cancer initiation from the stem cell population decreases with age of first pregnancy while initiation from progenitors increases. Some of the cancers that were considered as initiated from the progenitor population may potentially have had a stem initiation event occur afterwards, and simulations where progenitor initiation occurred are also those where fixation of the first mutation in the stem population was likely.

A number of embodiments of the invention have been described. Nevertheless, it will be understood that various modifications may be made without departing from the spirit and scope of the invention. It is further to be understood that all values are approximate, and are provided for description. Accordingly, other embodiments are within the scope of the following claims.

What is claimed is:

1. A method of treating a human subject who has not been diagnosed with breast cancer, wherein the method comprises:
   (a) providing a first breast tissue sample from a first human subject who has not been diagnosed with breast cancer and has not undergone a therapy for treatment of breast cancer;
   (b) measuring a relative frequency of p27+ breast epithelial cells and a relative frequency of Ki67+ breast epithelial cells in the first breast tissue sample from the first human subject, wherein a relative frequency is calculated as number or % of cells positive for a given marker compared to all breast epithelial cells counted; and
   (c) administering a prophylaxis, performing diagnostic assays, and/or periodically monitoring the health of the first human subject having a higher relative frequency of p27+ breast epithelial cells and a higher relative frequency of Ki67+ breast epithelial cells in the first breast tissue sample as compared to a second human subject having a lower relative frequency of p27+ breast epithelial cells and a lower relative frequency of Ki67+ breast epithelial cells in a second breast tissue sample, wherein the second human subject is a control subject known to not have or develop a breast cancer.

2. The method of claim 1, wherein the first human subject has a BRCA1 mutation.

3. The method of claim 1, wherein the first human subject has a BRCA2 mutation.

4. The method of claim 1, further comprising administering to the first human subject a composition comprising an inhibitor of a pathway active in p27+ and/or Ki67+ normal breast epithelial cells.

5. The method of claim 4, wherein the pathway is selected from the group consisting of cytoskeleton remodeling, chemokines, androgen signaling, cell adhesion, and Wnt signaling.

6. The method of claim 5, wherein the pathway includes a mediator molecule selected from the group consisting of cyclic AMP (cAMP), epidermal growth factor receptor (EGFR), cyclooxygenase-2 (Cox2), Hedgehog (Hh), Transforming growth factor β receptor (TGFBR), and insulin growth factor receptor (IGFR).

7. The method of claim 5, wherein the inhibitor selectively targets p27+ breast epithelial cells and/or Ki67+ breast epithelial cells in normal breast tissue.

8. The method of claim 7, wherein the cells selectively targeted by the inhibitor are also ER+.

9. The method of claim 1, wherein the first human subject has not been diagnosed with an ER+ breast cancer.

10. The method of claim 1, wherein the diagnostic assay that is performed on the first human subject in step (c) comprises clinical breast exam, mammography, or MRI.

* * * * *

UNITED STATES PATENT AND TRADEMARK OFFICE
CERTIFICATE OF CORRECTION

| | | |
|---|---|---|
| PATENT NO. | : 11,644,466 B2 | Page 1 of 1 |
| APPLICATION NO. | : 16/704941 | |
| DATED | : May 9, 2023 | |
| INVENTOR(S) | : Polyak et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 382 days.

Signed and Sealed this
Thirty-first Day of December, 2024

Derrick Brent
*Acting Director of the United States Patent and Trademark Office*

SEQUENCE LISTING

<160> NUMBER OF SEQ ID NOS: 54

<210> SEQ ID NO 1
<211> LENGTH: 1151
<212> TYPE: DNA
<213> ORGANISM: Homo sapiens

<400> SEQUENCE: 1

```
gccggagcca gcggttctcc aagcacccag catcctgcta gacgcgccgc gcaccgacgg      60
aggggacatg ggcagagcaa tggtggccag gctcgggctg gggctgctgc tgctggcact     120
gctcctaccc acgcagattt attccagtga aacaacaact ggaacttcaa gtaactcctc     180
ccagagtact tccaactctg ggttggcccc aaatccaact aatgccacca ccaaggcggc     240
tggtggtgcc ctgcagtcaa cagccagtct cttcgtggtc tcactctctc ttctgcatct     300
ctactcttaa gagactcagg ccaagaaacg tcttctaaat ttccccatct tctaaaccca     360
atccaaatgg cgtctggaag tccaatgtgg caaggaaaaa caggtcttca tcgaatctac     420
taattccaca cctttttattg acacagaaaa tgttgagaat cccaaatttg attgatttga    480
agaacatgtg agaggtttga ctagatgatg gatgccaata ttaaatctgc tggagtttca     540
tgtacaagat gaaggagagg cagcatccaa aaaatagtta agacatgatt tccttgaatg     600
tggttgagaa atatggacac ttaatactac cttgaaaata agaatagaaa taaggatggg     660
atcgtggact ggagatcagg tttccattgg ggttcattaa ttctataagg cctaaaacag     720
gtcatcataa aaggtcccat gaattctatc catatgtcca tgagaaggaa cttccaggtg     780
ttactgtaat tctcaaggta ttgtttcgac agcactagtt caatggcgaa taatcaaatg     840
cgttcccatg gtgaaccgag gggggcgaca tgggaaacgg aaccaacttc cttccgtgaa     900
ggcctcggga ttgacattgg attcgaacat tccggtgtaa tggcaagtgc caggacagaa     960
gtaatgaagt tgtccccaca aaaatttgaa cagtgcattc tctgagaaag ggaaacaaca    1020
acacgtgctt atcacgagaa ttatatagcg cacaatatct agccactacg tgatctaaac    1080
aaactcgaca ggagtgtcca tagtctctct tgctcattct acactattgt tccttctctt    1140
ctctgtgctg t                                                        1151
```

<210> SEQ ID NO 2
<211> LENGTH: 80
<212> TYPE: PRT

<213> ORGANISM: Homo sapiens

<400> SEQUENCE: 2

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
                20                  25                  30

Thr Ser Ser Asn Ser Ser Gln Ser Thr Ser Asn Ser Gly Leu Ala Pro
            35                  40                  45

Asn Pro Thr Asn Ala Thr Thr Lys Ala Ala Gly Gly Ala Leu Gln Ser
        50                  55                  60

Thr Ala Ser Leu Phe Val Val Ser Leu Ser Leu Leu His Leu Tyr Ser
65                  70                  75                  80
```

<210> SEQ ID NO 3
<211> LENGTH: 5710
<212> TYPE: DNA
<213> ORGANISM: Homo sapiens

<400> SEQUENCE: 3

| | | | | | |
|---|---|---|---|---|---|
| cgtcaggttg | gctcttcagg | ttcatttcca | tagttccctg | cggcctctgc | cttggggagt | 60 |
| tatgttttgt | taccgagatc | cgcgctacca | gattgcaccg | gggctgattt | ggggggctggg | 120 |
| aatttgccat | tctgctgtac | agacactgat | ttttttttct | tcttttttaaa | aagcaagatt | 180 |
| ttaggtgatg | ggcaagtcag | aaagtcagat | ggatataact | gatatcaaca | ctccaaagcc | 240 |
| aaagaagaaa | cagcgatgga | ctccactgga | gatcagcctc | tcggtccttg | tcctgctcct | 300 |
| caccatcata | gctgtgacaa | tgatcgcact | ctatgcaacc | tacgatgatg | gtatttgcaa | 360 |
| gtcatcagac | tgcataaaat | cagctgctcg | actgatccaa | acatggatg | ccaccactga | 420 |
| gccttgtaca | gactttttca | aatatgcttg | cggaggctgg | ttgaaacgta | atgtcattcc | 480 |
| cgagaccagc | tcccgttacg | gcaactttga | cattttaaga | gatgaactag | aagtcgtttt | 540 |
| gaaagatgtc | cttcaagaac | ccaaaactga | agatatagta | gcagtgcaga | aagcaaaagc | 600 |
| attgtacagg | tcttgtataa | atgaatctgc | tattgatagc | agaggtggag | aacctctact | 660 |
| caaactgtta | ccagacatat | atgggtggcc | agtagcaaca | gaaaactggg | agcaaaaata | 720 |
| tggtgcttct | tggacagctg | aaaaagctat | tgcacaactg | aattctaaat | atgggaaaaa | 780 |
| agtccttatt | aatttgtttg | ttggcactga | tgataagaat | tctgtgaatc | atgtaattca | 840 |
| tattgaccaa | cctcgacttg | gcctcccttc | tagagattac | tatgaatgca | ctggaatcta | 900 |
| taaagaggct | tgtacagcat | atgtggattt | tatgatttct | gtggccagat | tgattcgtca | 960 |
| ggaagaaaga | ttgcccatcg | atgaaaacca | gcttgctttg | gaaatgaata | aagttatgga | 1020 |
| attggaaaaa | gaaattgcca | atgctacggc | taaacctgaa | gatcgaaatg | atccaatgct | 1080 |
| tctgtataac | aagatgacat | tggcccagat | ccaaaataac | ttttcactag | agatcaatgg | 1140 |
| gaagccattc | agctggttga | atttcacaaa | tgaaatcatg | tcaactgtga | atattagtat | 1200 |
| tacaaatgag | gaagatgtgg | ttgtttatgc | tccagaatat | ttaaccaaac | ttaagcccat | 1260 |
| tcttaccaaa | tattctgcca | gagatcttca | aaatttaatg | tcctggagat | tcataatgga | 1320 |
| tcttgtaagc | agcctcagcc | gaacctacaa | ggagtccaga | aatgctttcc | gcaaggccct | 1380 |
| ttatggtaca | acctcagaaa | cagcaacttg | gagacgttgt | gcaaactatg | tcaatgggaa | 1440 |
| tatggaaaat | gctgtgggga | ggcttttatgt | ggaagcagca | tttgctggag | agagtaaaca | 1500 |
| tgtggtcgag | gatttgattg | cacagatccg | agaagttttt | attcagactt | tagatgacct | 1560 |

```
cacttggatg gatgccgaga caaaaaagag agctgaagaa aaggccttag caattaaaga   1620
aaggatcggc tatcctgatg acattgtttc aaatgataac aaactgaata atgagtacct   1680
cgagttgaac tacaaagaag atgaatactt cgagaacata attcaaaatt tgaaattcag   1740
ccaaagtaaa caactgaaga agctccgaga aaaggtggac aaagatgagt ggataagtgg   1800
agcagctgta gtcaatgcat tttactcttc aggaagaaat cagatagtct tcccagccgg   1860
cattctgcag cccccttct ttagtgccca gcagtccaac tcattgaact atggggcat    1920 cggcatggtc ataggacacg aaatcaccca tggcttcgat gacaatggca gaaactttaa   1980
caaagatgga gacctcgttg actggtggac tcaacagtct gcaagtaact ttaaggagca   2040
atcccagtgc atggtgtatc agtatggaaa cttttcctgg gacctggcag gtggacagca   2100
ccttaatgga attaatacac tgggagaaaa cattgctgat aatggaggtc ttggtcaagc   2160
atacagagcc tatcagaatt atattaaaaa gaatggcgaa gaaaaattac ttcctggact   2220
tgacctaaat cacaaacaac tattttctt gaactttgca caggtgtggt gtggaaccta    2280
taggccagag tatgcggtta actccattaa aacagatgtg cacagtccag gcaatttcag   2340
gattattggg actttgcaga actctgcaga gttttcagaa gcctttcact gccgcaagaa   2400
ttcatacatg aatccagaaa agaagtgccg ggtttggtga tcttcaaaag aagcattgca   2460
gcccttggct agacttgcca acaccacaga aatggggaat tctctaatcg aaagaaaatg   2520
ggccctaggg tcactgtac tgacttgagg gtgattaaca gagagggcac catcacaata    2580
cagataacat taggttgtcc tagaaagggt gtggagggag aagggggtc taaggtctat    2640 caagtcaatc atttctcact gtgtacataa tgcttaattt ctaaagataa tattactgtt   2700
tatttctgtt tctcatatgg tctaccagtt tgctgatgtc cctagaaaac aatgcaaaac   2760
cttggaggta gaccaggatt tctaatcaaa agggaaaaga agatgttgaa gaatacagtt   2820
aggcaccaga agaacagtag gtgacactat agtttaaaac acattgccta actactagtt   2880
tttactttta tttgcaacat ttacagtcct tcaaaatcct tccaaagaat tcttatacac   2940
attggggcct tggagcttac atagttttaa actcatttt gccatacatc agttattcat    3000
tctgtgatca tttatttaa gcactcttaa agcaaaaaat gaatgtctaa aattgttttt    3060
tgttgtacct gctttgactg atgctgagat tcttcaggct tcctgcaatt ttctaagcaa   3120
tttcttgctc tatctctcaa aacttggtat ttttcagaga tttatataaa tgtaaaaata   3180
ataattttta tatttaatta ttaactacat ttatgagtaa ctattattat aggtaatcaa   3240
tgaatattga agtttcagct taaaataaac agttgtgaac caagatctat aaagcgatat   3300
acagatgaaa atttgagact atttaaactt ataaatcata ttgatgaaaa gatttaagca   3360
caaactttag ggtaaaaatt gccattggac agttgtctag agatatatat acttgtggtt   3420
ttcaaattgg actttcaaaa ttaaatctgt ccctgagagt gtctctgata aagggcaaa    3480 tctgcaccta tgtagctctg catctcctgt cttttcaggt ttgtcatcag atggaaatat   3540
tttgataata aattgaaatt gtgaactcat tgctccctaa gactgtgaca actgtctaac   3600
tttagaagtg catttctgaa tagaaatggg aggcctctga tggaccttct agaattataa   3660
gtcacaaaga gttctggaaa agaactgttt actgcttgat aggaattcat cttttgaggc   3720
ttctgttcct ctctttcct gttgtattga ctattttcgt tcattacttg attaagattt    3780
tacaaaagag gagcacttcc aaaattctta tttttcctaa caaagatgaa agcagggaa    3840 tttctatcta aatgatgagt attagttccc tgtctcttga aaaatgccca tttgccttta   3900
aaaaaaaaag ttacagaaat actataacat atgtacataa attgcataaa gcataagtat   3960
```

-continued

```
acagttcaat aaacttaact ttaactgaac aatggccctg tagccagcac ctgtaagaaa    4020
cagagcagta ccagcgctct aaaagcacct ccttgtcact ttattactcc cagaacaaca    4080
actatcctga cttctaatat cattcactag ctttgcctgg ttttgtcttt tatgcagata    4140
gaatcaatca gtatgtattc ttttgtgcct ggcttctttc tctcagcctt acatttgtga    4200
gattcctctg tattgtgctg attgtggatc ttttcattct cattgcagaa taatgttcta    4260
ttgtgggact tattacaatt tgttcatcct attgttgatg ggcacttgag aacttttccat   4320 tttggcgcta ttacaaatag tgcaactatg aatgtactgc atgttaccat cttacttgag    4380
cctttaatgg acttatttct tcaaatcctt ccaaaaatta ttataagcat tgaaattata    4440
gtttcaagcc aactgtggat acccttaccc tttcctcctt tatcacaacc accgttacaa    4500
gtatacttat atttccctaa aatacattta aaacttacct aagtgacatt tgtagttgga    4560
gtaataggag cttccagctc taataaaaca gctgtctcta acttatttta tttccatcat    4620
gtcagagcag gtgaagagcc agaagtgaag agtgactagt acaaattata aaaagccact    4680
agactcttca ctgttagctt tttaaaacat taggctccca tccctatgga ggaacaactc    4740
tccagtgcct ggatcccctc tgtctacaaa tataagattt tctgggccta aggatagat    4800 caaagtcaaa aatagcaatg cctccctatc cctcacacat ccagacatca tgaattttac    4860
atggtactct tgttgagttc tgtagagcct tctgatgtct ctaaagcact accgattctt    4920
tggagttgtc acatcagata agacatatct ctaattccat ccataaatcc agttctacta    4980
tggctgagtt ctggtcaaag aaagaaagtt tagaagctga gacacaaagg gttgggagct    5040
gatgaaactc acaaatgatg gtaggaagaa gctctcgaca ataccgttg gcaaggagtc     5100 tgcctccatg ctgcagtgtt cgagtggatt gtaggtgcaa gatggaaagg attgtaggtg    5160
caagctgtcc agagaaaaga gtccttgttc cagccctatt ctgccactcc tgacagggtg    5220
accttgggta tttgcaatat tcctttgggc ctctgcttct ctcacctaaa aaagagaat    5280 tagattatat tggtggttct cagcaagaga aggagtatgt gtccaatgct gccttcccat    5340
gaatctgtct cccagttatg aatcagtggg caggataaac tgaaaactcc catttacgtg    5400
tctgaatcga gtgagacaaa attttagtcc aaataacaag taccaaagtt ttatcaagtt    5460
tgggtctgtg ctgctgttac tgttaaccat ttaagtgggg caaaaccttg ctaattttct    5520
caaaagcatt tatcattctt gttgccacag ctggagctct caaactaaaa gacatttgtt    5580
attttggaaa gaagaaagac tctattctca aagtttccta atcagaaatt tttatcagtt    5640
tccagtctca aaaatacaaa ataaaaacaa acgttttaa tactattgct tttatgccta    5700
gtcaactctg                                                          5710
```

<210> SEQ ID NO 4
<211> LENGTH: 750
<212> TYPE: PRT
<213> ORGANISM: Homo sapiens

<400> SEQUENCE: 4

```
Met Gly Lys Ser Glu Ser Gln Met Asp Ile Thr Asp Ile Asn Thr Pro
1               5                   10                  15

Lys Pro Lys Lys Lys Gln Arg Trp Thr Pro Leu Glu Ile Ser Leu Ser
            20                  25                  30

Val Leu Val Leu Leu Leu Thr Ile Ile Ala Val Thr Met Ile Ala Leu
        35                  40                  45

Tyr Ala Thr Tyr Asp Asp Gly Ile Cys Lys Ser Ser Asp Cys Ile Lys
```

-continued

```
                50                  55                  60
Ser Ala Ala Arg Leu Ile Gln Asn Met Asp Ala Thr Thr Glu Pro Cys
 65                  70                  75                  80

Thr Asp Phe Phe Lys Tyr Ala Cys Gly Gly Trp Lys Arg Asn Val
                 85                  90                  95

Ile Pro Glu Thr Ser Ser Arg Tyr Gly Asn Phe Asp Ile Leu Arg Asp
                    100                 105                 110

Glu Leu Glu Val Val Leu Lys Asp Val Leu Gln Glu Pro Lys Thr Glu
                115                 120                 125

Asp Ile Val Ala Val Gln Lys Ala Lys Ala Leu Tyr Arg Ser Cys Ile
                130                 135                 140

Asn Glu Ser Ala Ile Asp Ser Arg Gly Gly Glu Pro Leu Leu Lys Leu
145                 150                 155                 160

Leu Pro Asp Ile Tyr Gly Trp Pro Val Ala Thr Glu Asn Trp Glu Gln
                165                 170                 175

Lys Tyr Gly Ala Ser Trp Thr Ala Glu Lys Ala Ile Ala Gln Leu Asn
                180                 185                 190

Ser Lys Tyr Gly Lys Lys Val Leu Ile Asn Leu Phe Val Gly Thr Asp
                195                 200                 205

Asp Lys Asn Ser Val Asn His Val Ile His Ile Asp Gln Pro Arg Leu
                210                 215                 220

Gly Leu Pro Ser Arg Asp Tyr Tyr Glu Cys Thr Gly Ile Tyr Lys Glu
225                 230                 235                 240

Ala Cys Thr Ala Tyr Val Asp Phe Met Ile Ser Val Ala Arg Leu Ile
                245                 250                 255

Arg Gln Glu Glu Arg Leu Pro Ile Asp Glu Asn Gln Leu Ala Leu Glu
                260                 265                 270

Met Asn Lys Val Met Glu Leu Glu Lys Glu Ile Ala Asn Ala Thr Ala
                275                 280                 285

Lys Pro Glu Asp Arg Asn Asp Pro Met Leu Leu Tyr Asn Lys Met Thr
                290                 295                 300

Leu Ala Gln Ile Gln Asn Asn Phe Ser Leu Glu Ile Asn Gly Lys Pro
305                 310                 315                 320

Phe Ser Trp Leu Asn Phe Thr Asn Glu Ile Met Ser Thr Val Asn Ile
                325                 330                 335

Ser Ile Thr Asn Glu Glu Asp Val Val Val Tyr Ala Pro Glu Tyr Leu
                340                 345                 350

Thr Lys Leu Lys Pro Ile Leu Thr Lys Tyr Ser Ala Arg Asp Leu Gln
                355                 360                 365

Asn Leu Met Ser Trp Arg Phe Ile Met Asp Leu Val Ser Ser Leu Ser
                370                 375                 380

Arg Thr Tyr Lys Glu Ser Arg Asn Ala Phe Arg Lys Ala Leu Tyr Gly
385                 390                 395                 400

Thr Thr Ser Glu Thr Ala Thr Trp Arg Arg Cys Ala Asn Tyr Val Asn
                405                 410                 415

Gly Asn Met Glu Asn Ala Val Gly Arg Leu Tyr Val Glu Ala Ala Phe
                420                 425                 430

Ala Gly Glu Ser Lys His Val Val Glu Asp Leu Ile Ala Gln Ile Arg
                435                 440                 445

Glu Val Phe Ile Gln Thr Leu Asp Asp Leu Thr Trp Met Asp Ala Glu
                450                 455                 460

Thr Lys Lys Arg Ala Glu Glu Lys Ala Leu Ala Ile Lys Glu Arg Ile
465                 470                 475                 480
```

```
Gly Tyr Pro Asp Asp Ile Val Ser Asn Asp Asn Lys Leu Asn Asn Glu
            485                 490                 495

Tyr Leu Glu Leu Asn Tyr Lys Glu Asp Glu Tyr Phe Glu Asn Ile Ile
        500                 505                 510

Gln Asn Leu Lys Phe Ser Gln Ser Lys Gln Leu Lys Lys Leu Arg Glu
    515                 520                 525

Lys Val Asp Lys Asp Glu Trp Ile Ser Gly Ala Ala Val Asn Ala
530                 535                 540

Phe Tyr Ser Ser Gly Arg Asn Gln Ile Val Phe Pro Ala Gly Ile Leu
545                 550                 555                 560

Gln Pro Pro Phe Phe Ser Ala Gln Ser Asn Ser Leu Asn Tyr Gly
                565                 570                 575

Gly Ile Gly Met Val Ile Gly His Glu Ile Thr His Gly Phe Asp Asp
                580                 585                 590

Asn Gly Arg Asn Phe Asn Lys Asp Gly Asp Leu Val Asp Trp Trp Thr
                595                 600                 605

Gln Gln Ser Ala Ser Asn Phe Lys Glu Gln Ser Gln Cys Met Val Tyr
    610                 615                 620

Gln Tyr Gly Asn Phe Ser Trp Asp Leu Ala Gly Gly Gln His Leu Asn
625                 630                 635                 640

Gly Ile Asn Thr Leu Gly Glu Asn Ile Ala Asp Asn Gly Gly Leu Gly
                645                 650                 655

Gln Ala Tyr Arg Ala Tyr Gln Asn Tyr Ile Lys Lys Asn Gly Glu Glu
            660                 665                 670

Lys Leu Leu Pro Gly Leu Asp Leu Asn His Lys Gln Leu Phe Phe Leu
        675                 680                 685

Asn Phe Ala Gln Val Trp Cys Gly Thr Tyr Arg Pro Glu Tyr Ala Val
    690                 695                 700

Asn Ser Ile Lys Thr Asp Val His Ser Pro Gly Asn Phe Arg Ile Ile
705                 710                 715                 720

Gly Thr Leu Gln Asn Ser Ala Glu Phe Ser Glu Ala Phe His Cys Arg
                725                 730                 735

Lys Asn Ser Tyr Met Asn Pro Glu Lys Lys Cys Arg Val Trp
            740                 745                 750

<210> SEQ ID NO 5
<211> LENGTH: 2387
<212> TYPE: DNA
<213> ORGANISM: Homo sapiens

<400> SEQUENCE: 5
cctcgtgccg cggaccccag cctctgccag gttcggtccg ccatcctcgt cccgtcctcc      60
gccggcccct gccccgcgcc cagggatcct ccagctcctt tcgcccgcgc cctccgttcg     120
ctccggacac catggacaag ttttggtggc acgcagcctg ggactctgc ctcgtgccgc      180 tgagcctggc gcagatcgat ttgaatataa cctgccgctt tgcaggtgta ttccacgtgg     240
agaaaaatgg tcgctacagc atctctcgga cggaggccgc tgacctctgc aaggctttca     300
atagcacctt gccacaatg gcccagatgg agaaagctct gagcatcgga tttgagacct      360
gcaggtatgg gttcatagaa gggcatgtgg tgattcccg gatccacccc aactccatct      420
gtgcagcaaa caacaggg gtgtacatcc tcacatccaa cacctcccag tatgacacat       480
attgcttcaa tgcttcagct ccacctgaag aagattgtac atcagtcaca gacctgccca      540
atgcctttga tggaccaatt accataacta ttgttaaccg tgatggcacc cgctatgtcc     600
```

```
agaaaggaga atacagaacg aatcctgaag acatctaccc cagcaaccct actgatgatg    660
acgtgagcag cggctcctcc agtgaaagga gcagcacttc aggaggttac atcttttaca    720 cctttttctac tgtacacccc atcccagacg aagacagtcc ctggatcacc gacagcacag   780
acagaatccc tgctaccagt acgtcttcaa ataccatctc agcaggctgg gagccaaatg    840
aagaaaatga agatgaaaga cacagacacc tcagtttttc tggatcaggc attgatgatg    900
atgaagattt tatctccagc accatttcaa ccacaccacg ggcttttgac cacacaaaac   960
agaaccagga ctggacccag tggaacccaa gccattcaaa tccggaagtg ctacttcaga   1020
caaccacaag gatgactgat gtagacagaa atggcaccac tgcttatgaa ggaaactgga   1080
acccagaagc acaccctccc ctcattcacc atgagcatca tgaggaagaa gagaccccac   1140
attctacaag cacaatccag gcaactccta gtagtacaac ggaagaaaca gctacccaga   1200
aggaacagtg gtttggcaac agatggcatg agggatatcg ccaaacaccc agagaagact   1260
cccattcgac aacagggaca gctgcagcct cagctcatac cagccatcca atgcaaggaa   1320
ggacaacacc aagcccagag gacagttcct ggactgattt cttcaaccca atctcacacc   1380
ccatgggacg aggtcatcaa gcaggaagaa ggatggatat ggactccagt catagtacaa   1440
cgcttcagcc tactgcaaat ccaaacacag gtttggtgga agatttggac aggacaggac   1500
ctctttcaat gacaacgcag cagagtaatt ctcagagctt ctctacatca catgaaggct   1560
tggaagaaga taaagaccat ccaacaactt ctactctgac atcaagcaat aggaatgatg   1620
tcacaggtgg aagaagagac ccaaatcatt ctgaaggctc aactacttta ctggaaggtt   1680
atacctctca ttacccacac acgaaggaaa gcaggacctt catcccagtg acctcagcta   1740
agactgggtc ctttggagtt actgcagtta ctgttggaga ttccaactct aatgtcaatc   1800
gttccttatc aggagaccaa gacacattcc accccagtgg ggggtcccat accactcatg   1860
gatctgaatc agatggacac tcacatggga gtcaagaagg tggagcaaac acaacctctg   1920
gtcctataag gacaccccaa attccagaat ggctgatcat cttggcatcc ctcttggcct   1980
tggctttgat tcttgcagtt tgcattgcag tcaacagtcg aagaaggtgt gggcagaaga   2040
aaaagctagt gatcaacagt ggcaatggag ctgtggagga cagaaagcca agtggactca   2100
acggagaggc cagcaagtct caggaaatgg tgcatttggt gaacaaggag tcgtcagaaa   2160
ctccagacca gtttatgaca gctgatgaga caaggaacct gcagaatgtg acatgaaga    2220 ttggggtgta acacctacac cattatcttg gaaagaaaca accgttggaa acataaccat   2280
tacagggagc tgggacactt aacagatgca atgtgctact gattgtttca ttgcgaatct   2340
tttttagcat aaaatttct actcttaaaa aaaaaaaaa aaaaaa                    2387
```

<210> SEQ ID NO 6
<211> LENGTH: 43
<212> TYPE: PRT
<213> ORGANISM: Homo sapiens

<400> SEQUENCE: 6

Thr Leu Met Ser Thr Ser Ala Thr Ala Thr Glu Thr Ala Thr Lys Arg
1               5                   10                  15

Gln Glu Thr Trp Asp Trp Phe Ser Trp Leu Phe Leu Pro Ser Glu Ser
            20                  25                  30

Lys Asn His Leu His Thr Thr Thr Gln Met Ala
        35                  40

```
<210> SEQ ID NO 7
<211> LENGTH: 2334
<212> TYPE: DNA
<213> ORGANISM: Homo sapiens

<400> SEQUENCE: 7
cttgctcacg gctctgcgac tccgacgccg gcaaggtttg gagagcggct gggttcgcgg      60
gacccgcggg cttgcacccg cccagactcg gacgggcttt gccaccctct ccgcttgcct     120
ggtcccctct cctctccgcc ctcccgctcg ccagtccatt tgatcagcgg agactcggcg     180
gccgggccgg ggcttccccg cagcccctgc gcgctcctag agctcgggcc gtggctcgtc     240
ggggtctgtg tcttttggct ccgagggcag tcgctgggct tccgagaggg gttcgggccg     300
cgtaggggcg ctttgttttg ttcggttttg ttttttttgag agtgcgagag aggcggtcgt     360
gcagacccgg gagaaagatg tcaaacgtgc gagtgtctaa cggagcccct agcctggagc     420
ggatggacgc caggcaggcg gagcacccca agccctcggc ctgcaggaac ctcttcggcc     480
cggtggacca cgaagagtta acccgggact tggagaagca ctgcagagac atggaagagg     540
cgagccagcg caagtggaat tcgattttc agaatcacaa accctagag ggcaagtacg     600 agtggcaaga ggtggagaag ggcagcttgc ccgagttcta ctacagaccc ccgcggcccc     660
ccaaaggtgc ctgcaaggtg ccggcgcagg agagccagga tggcagcggg agccgcccgg     720
cggcgccttt aattggggct ccggctaact ctgaggacac gcattggtg gacccaaaga     780 ctgatccgtc ggacagccag acggggttag cggagcaatg cgcaggaata aggaagcgac     840
ctgcaaccga cgattcttct actcaaaaca aagagccaa cagaacagaa gaaaatgttt     900
cagacggttc cccaaatgcc ggttctgtgg agcagacgcc caagaagcct ggcctcagaa     960
gacgtcaaac gtaaacagct cgaattaaga atatgtttcc ttgtttatca gatacatcac    1020
tgcttgatga agcaaggaag atatacatga aaatttttaaa aatacatatc gctgacttca    1080
tggaatggac atcctgtata agcactgaaa acaacaaca caataacact aaaattttag    1140
gcactcttaa atgatctgcc tctaaaagcg ttggatgtag cattatgcaa ttaggttttt    1200
ccttatttgc ttcattgtac tacctgtgta tatagttttt acctttatg tagcacataa    1260 actttgggga agggagggca gggtggggct gaggaactga cgtggagcgg ggtatgaaga    1320
gcttgctttg atttacagca agtagataaa tatttgactt gcatgaagag aagcaatttt    1380
ggggaagggt ttgaattgtt ttctttaaag atgtaatgtc ccttcagag acagctgata    1440 cttcatttaa aaaatcaca aaatttgaa cactggctaa agataattgc tatttatttt    1500
tacaagaagt ttattctcat ttgggagatc tggtgatctc ccaagctatc taagtttgt     1560 tagatagctg catgtggctt ttttaaaaaa gcaacagaaa cctatcctca ctgccctccc    1620
cagtctctct taaagttgga atttaccagt taattactca gcagaatggt gatcactcca    1680
ggtagtttgg ggcaaaaatc cgaggtgctt gggagttttg aatgttaaga attgaccatc    1740
tgcttttatt aaatttgttg acaaaatttt ctcatttct tttcacttcg ggctgtgtaa    1800
acacagtcaa ataattcta aatccctcga tattttaaa gatctgtaag taacttcaca    1860
ttaaaaaatg aaatattttt taatttaaag cttactctgt ccatttatcc acaggaaagt    1920
gttattttta aaggaaggtt catgtagaga aaagcacact tgtaggataa gtgaaatgga    1980
tactacatct ttaaacagta tttcattgcc tgtgtatgga aaaccatttt gaagtgtacc    2040
tgtgtacata actctgtaaa aacactgaaa aattatacta acttatttat gttaaaagat    2100 ttttttaat ctagacaata tacaagccaa agtggcatgt tttgtgcatt tgtaaatgct    2160
```

-continued

```
gtgttgggta gaataggttt tcccctcttt tgttaaataa tatggctatg cttaaaaggt    2220
tgcatactga gccaagtata attttttgta atgtgtgaaa aagatgccaa ttattgttac    2280
acattaagta atcaataaag aaaacttcca tagctaaaaa aaaaaaaaaa aaaa          2334
```

```
<210> SEQ ID NO 8
<211> LENGTH: 198
<212> TYPE: PRT
<213> ORGANISM: Homo sapiens

<400> SEQUENCE: 8
```

| | | | | | | | | | | | | | | |
|---|---|---|---|---|---|---|---|---|---|---|---|---|---|---|
| Met | Ser | Asn | Val | Arg | Val | Ser | Asn | Gly | Ser | Pro | Ser | Leu | Glu | Arg | Met |
| 1 | | | | 5 | | | | | 10 | | | | | 15 | |
| Asp | Ala | Arg | Gln | Ala | Glu | His | Pro | Lys | Pro | Ser | Ala | Cys | Arg | Asn | Leu |
| | | | 20 | | | | | 25 | | | | | 30 | | |
| Phe | Gly | Pro | Val | Asp | His | Glu | Glu | Leu | Thr | Arg | Asp | Leu | Glu | Lys | His |
| | | 35 | | | | | 40 | | | | | 45 | | | |
| Cys | Arg | Asp | Met | Glu | Glu | Ala | Ser | Gln | Arg | Lys | Trp | Asn | Phe | Asp | Phe |
| | 50 | | | | | 55 | | | | | 60 | | | | |
| Gln | Asn | His | Lys | Pro | Leu | Glu | Gly | Lys | Tyr | Glu | Trp | Gln | Val | Glu |
| 65 | | | | | 70 | | | | | 75 | | | | | 80 |
| Lys | Gly | Ser | Leu | Pro | Glu | Phe | Tyr | Tyr | Arg | Pro | Pro | Arg | Pro | Pro | Lys |
| | | | | 85 | | | | | 90 | | | | | 95 | |
| Gly | Ala | Cys | Lys | Val | Pro | Ala | Gln | Glu | Ser | Gln | Asp | Val | Ser | Gly | Ser |
| | | | 100 | | | | | 105 | | | | | 110 | | |
| Arg | Pro | Ala | Ala | Pro | Leu | Ile | Gly | Ala | Pro | Ala | Asn | Ser | Glu | Asp | Thr |
| | | | 115 | | | | | 120 | | | | | 125 | | |
| His | Leu | Val | Asp | Pro | Lys | Thr | Asp | Pro | Ser | Asp | Ser | Gln | Thr | Gly | Leu |
| | | 130 | | | | | 135 | | | | | 140 | | | |
| Ala | Glu | Gln | Cys | Ala | Gly | Ile | Arg | Lys | Arg | Pro | Ala | Thr | Asp | Asp | Ser |
| 145 | | | | | 150 | | | | | 155 | | | | | 160 |
| Ser | Thr | Gln | Asn | Lys | Arg | Ala | Asn | Arg | Thr | Glu | Glu | Asn | Val | Ser | Asp |
| | | | | 165 | | | | | 170 | | | | | 175 | |
| Gly | Ser | Pro | Asn | Ala | Gly | Ser | Val | Glu | Gln | Thr | Pro | Lys | Lys | Pro | Gly |
| | | | 180 | | | | | 185 | | | | | 190 | | |
| Leu | Arg | Arg | Arg | Gln | Thr |
| | | | 195 | | |

```
<210> SEQ ID NO 9
<211> LENGTH: 541
<212> TYPE: DNA
<213> ORGANISM: Homo sapiens
<220> FEATURE:
<221> NAME/KEY: modified_base
<222> LOCATION: (381)..(381)
<223> OTHER INFORMATION: a, c, t, g, unknown or other
<220> FEATURE:
<221> NAME/KEY: modified_base
<222> LOCATION: (385)..(385)
<223> OTHER INFORMATION: a, c, t, g, unknown or other
<220> FEATURE:
<221> NAME/KEY: modified_base
<222> LOCATION: (445)..(445)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
<220> FEATURE:
<221> NAME/KEY: modified_base
<222> LOCATION: (525)..(525)
<223> OTHER INFORMATION: a, c, t, g, unknown or other
```

```
<400> SEQUENCE: 9
gcattcattc agcaagtatt tatgatgtca cctggctccc cgccagacac tggggaaaca      60
aacgtggaga cggggcactg cccgcacagg gcacattttg gggacagct accctgtctg     120
gtgcaccatc ctcacctgca cctggcaagg tgggtgaatg gggaggaatc cagacaggtg    180
acctggggga tggcgggcta ttctctgatt tggggaacac agagaggaca gggggcaaag    240
tggaaagtaa atgaagatga acgagttata tctacaagtc tgaagctgga gaaagatgtc    300
tgggcttcaa aggagatttc ggaggcagcg gctcacaagg aaacgatcct gaaatcgtgg    360
cttaaagtgc tgagtgctca ntctnttcaa ggatgatgat gctttacaga gtactggtgt    420
cactttctgt acttgggtgg cattnggctt gccagataga gtcagaaaga aaacaggccg    480
gaaccaagcc cgtaacttcc naactttaat gaccggaaac tgganatttg gacccatttg    540
g                                                                    541

<210> SEQ ID NO 10
<211> LENGTH: 46
<212> TYPE: PRT
<213> ORGANISM: Homo sapiens

<400> SEQUENCE: 10

Met Trp Pro Thr Arg Arg Leu Val Thr Ile Lys Arg Ser Gly Val Asp
1               5                   10                  15
Gly Pro His Phe Pro Leu Ser Leu Ser Thr Cys Leu Phe Gly Arg Arg
            20                  25                  30
Lys Cys Val Leu Gln Cys Thr Glu Cys Ser Lys Thr Ala Ile
        35                  40                  45

<210> SEQ ID NO 11
<211> LENGTH: 2350
<212> TYPE: DNA
<213> ORGANISM: Homo sapiens

<400> SEQUENCE: 11
gcagtgtcac taggccggct gggggccctg ggtacgctgt agaccagacc gcgacaggcc     60
agaacacggg cggcggcttc gggccgggag accccgcgcag ccctcggggc atctcagtgc   120
ctcactcccc accccctccc ccgggtcggg ggaggcggcg cgtccggcgg agggttgagg    180
ggagcggggc aggcctggag cgccatgagc agcccggatg cgggatacgc cagtgacgac    240
cagagccaga cccagagcgc gctgcccgcg gtgatggccg ggctgggccc ctgcccctgg    300
gccgagtcgc tgagccccat cggggacatg aaggtgaagg cgaggcgcc ggcgaacagc     360
ggagcaccgg ccggggccgc gggccgagcc aagggcgagt cccgtatccg gcggccgatg    420
aacgctttca tggtgtgggc taaggacgag cgcaagcggc tggcgcagca gaatccagac    480
ctgcacaacg ccgagttgag caagatgctg ggcaagtcgt ggaaggcgct gacgctggcg    540
gagaagcggc ccttcgtgga ggaggcagag cggctgcgcg tgcagcacat gcaggaccac    600
cccaactaca agtaccggcc gcggcggcgc aagcaggtga gcggctgaa gcgggtggag      660
ggcggcttcc tgcacggcct ggctgagccg caggcggccg cgctgggccc cgagggcggc    720
cgcgtggcca tggacggcct gggcctccag ttccccgagc agggcttccc cgccggcccg    780
ccgctgctgc ctccgcacat gggcggccac taccgcgact gccagagtct gggcgcgcct    840
ccgctcgacg gctacccgtt gcccacgccc gacacgtccc cgctgacgg cgtggacccc    900
gacccggctt tcttcgccgc cccgatgccc ggggactgcc cggcggccgg cacctacagc    960
```

```
tacgcgcagg tctcggacta cgctggcccc ccggagcctc ccgccggtcc catgcacccc    1020
cgactcggcc cagagcccgc gggtccctcg attccgggcc tcctggcgcc acccagcgcc    1080
cttcacgtgt actacggcgc gatgggctcg cccggggcgg gcggcgggcg cggcttccag    1140
atgcagccgc aacaccagca ccagcaccag caccagcacc accccccggg ccccggacag    1200
ccgtcgcccc ctccggaggc actgccctgc cgggacggca cggaccccag tcagcccgcc    1260
gagctcctcg gggaggtgga ccgcacggaa tttgaacagt atctgcactt cgtgtgcaag    1320
cctgagatgg gcctcccta ccaggggcat gactccggtg tgaatctccc cgacagccac    1380
ggggccattt cctcggtggt gtccgacgcc agctccgcgg tatattactg caactatcct    1440
gacgtgtgac aggtccctga tccgcccag cctgcaggcc agaagcagtg ttacacactt    1500
cctggaggag ctaaggaaat cctcagactc ctgggttttt gttgttgctg ttgttgtttt    1560
ttaaaaggtg tgttggcata taatttatgg taatttattt tgtctgccac ttgaacagtt    1620
tgggggggtg aggtttcatt taaaatttgt tcagagattt gttcccata gttggattgt    1680
caaaacccta tttccaagtt caagttaact agctttgaat gtgtcccaaa acagcttcct    1740
ccatttcctg aaagtttatt gatcaaagaa atgttgtcct gggtgtgttt tttcaatctt    1800
ctaaaaaata aaatctggaa tcctgctttt ttgctctact agtacctctg tcacactagt    1860
cttatcaaaa accagttctt aagatcaatg ttaagtttat tagttaatgt aaatttctca    1920
tcctcgaaaa gggtgaacat aaatgccttt aaggagtata tctaaaaata aacattagga    1980
tatctaagtt tgatgtaatt gtttcaggaa ggaaaaaaga aaagcattct ggaatgagcc    2040
tacttcaagt aatcttagtt tctaaaacta acagttaata ttttcaattc cagtatatca    2100
ctttaagtag aaggggatgt ccaagtaatt ttggttttct aactgttgaa tcataagctt    2160
gacctgcccc cagaggcttt ttggatgttt ttatctgtgt tttgccatct ctttacactc    2220
ctcgacattc agtttacctt aatcttcaca tttttacacc ttgggaagtg gcaagcatcg    2280
ctgggtttaa gataaaggag tcacaaaaac taatcaaaat aaaatttgca ttatgacaac    2340
ttttaataca                                                           2350
```

<210> SEQ ID NO 12
<211> LENGTH: 414
<212> TYPE: PRT
<213> ORGANISM: Homo sapiens

<400> SEQUENCE: 12

Met Ser Ser Pro Asp Ala Gly Tyr Ala Ser Asp Asp Gln Ser Gln Thr
1               5                   10                  15

Gln Ser Ala Leu Pro Ala Val Met Ala Gly Leu Gly Pro Cys Pro Trp
            20                  25                  30

Ala Glu Ser Leu Ser Pro Ile Gly Asp Met Lys Val Lys Gly Glu Ala
        35                  40                  45

Pro Ala Asn Ser Gly Ala Pro Ala Gly Ala Ala Gly Arg Ala Lys Gly
    50                  55                  60

Glu Ser Arg Ile Arg Arg Pro Met Asn Ala Phe Met Val Trp Ala Lys
65                  70                  75                  80

Asp Glu Arg Lys Arg Leu Ala Gln Gln Asn Pro Asp Leu His Asn Ala
                85                  90                  95

Glu Leu Ser Lys Met Leu Gly Lys Ser Trp Lys Ala Leu Thr Leu Ala
            100                 105                 110

Glu Lys Arg Pro Phe Val Glu Glu Ala Glu Arg Leu Arg Val Gln His
        115                 120                 125

Met Gln Asp His Pro Asn Tyr Lys Tyr Arg Pro Arg Arg Lys Gln
        130                 135                 140

Val Lys Arg Leu Lys Arg Val Glu Gly Gly Phe Leu His Gly Leu Ala
145                 150                 155                 160

Glu Pro Gln Ala Ala Leu Gly Pro Glu Gly Gly Arg Val Ala Met
                165                 170                 175

Asp Gly Leu Gly Leu Gln Phe Pro Glu Gln Gly Phe Pro Ala Gly Pro
                180                 185                 190

Pro Leu Leu Pro Pro His Met Gly Gly His Tyr Arg Asp Cys Gln Ser
            195                 200                 205

Leu Gly Ala Pro Pro Leu Asp Gly Tyr Pro Leu Pro Thr Pro Asp Thr
210                 215                 220

Ser Pro Leu Asp Gly Val Asp Pro Asp Pro Ala Phe Phe Ala Ala Pro
225                 230                 235                 240

Met Pro Gly Asp Cys Pro Ala Ala Gly Thr Tyr Ser Tyr Ala Gln Val
                245                 250                 255

Ser Asp Tyr Ala Gly Pro Pro Glu Pro Pro Ala Gly Pro Met His Pro
                260                 265                 270

Arg Leu Gly Pro Glu Pro Ala Gly Pro Ser Ile Pro Gly Leu Leu Ala
            275                 280                 285

Pro Pro Ser Ala Leu His Val Tyr Tyr Gly Ala Met Gly Ser Pro Gly
290                 295                 300

Ala Gly Gly Gly Arg Gly Phe Gln Met Gln Pro Gln His Gln His Gln
305                 310                 315                 320

His Gln His Gln His His Pro Pro Gly Pro Gly Gln Pro Ser Pro Pro
                325                 330                 335

Pro Glu Ala Leu Pro Cys Arg Asp Gly Thr Asp Pro Ser Gln Pro Ala
                340                 345                 350

Glu Leu Leu Gly Glu Val Asp Arg Thr Glu Phe Glu Gln Tyr Leu His
            355                 360                 365

Phe Val Cys Lys Pro Glu Met Gly Leu Pro Tyr Gln Gly His Asp Ser
370                 375                 380

Gly Val Asn Leu Pro Asp Ser His Gly Ala Ile Ser Ser Val Val Ser
385                 390                 395                 400

Asp Ala Ser Ser Ala Val Tyr Tyr Cys Asn Tyr Pro Asp Val
                405                 410

<210> SEQ ID NO 13
<211> LENGTH: 4507
<212> TYPE: DNA
<213> ORGANISM: Homo sapiens

<400> SEQUENCE: 13

```
gaccaattgt catacgactt gcagtgagcg tcaggagcac gtccaggaac tcctcagcag    60
cgcctccttc agctccacag ccagacgccc tcagacagca agcctacccc cgcgccgcg    120
ccctgcccgc cgctgcgatg ctcgcccgcg ccctgctgct gtgcgcggtc ctggcgctca    180
gccatacagc aaatccttgc tgttcccacc catgtcaaaa ccgaggtgta tgtatgagtg    240
tgggatttga ccagtataag tgcgattgta cccggacagg attctatgga gaaaactgct    300
caacaccgga atttttgaca agaataaaat tatttctgaa acccactcca aacacagtgc    360
actacatact tacccacttc aagggatttt ggaacgttgt gaataacatt cccttccttc    420
gaaatgcaat tatgagttat gtgttgacat ccagatcaca tttgattgac agtccaccaa    480
```

-continued

```
cttacaatgc tgactatggc tacaaaagct gggaagcctt ctctaacctc tcctattata    540
ctagagccct tcctcctgtg cctgatgatt gcccgactcc cttgggtgtc aaaggtaaaa    600
agcagcttcc tgattcaaat gagattgtgg aaaaattgct tctaagaaga aagttcatcc    660
ctgatcccca gggctcaaac atgatgtttg cattctttgc ccagcacttc acgcatcagt    720
ttttcaagac agatcataag cgagggccag cttteaccaa cgggctgggc catggggtgg    780
acttaaatca tatttacggt gaaactctgg ctagacagcg taaactgcgc cttttcaagg    840
atggaaaaat gaaatatcag ataattgatg gagagatgta tcctcccaca gtcaaagata    900
ctcaggcaga gatgatctac cctcctcaag tccctgagca tctacggttt gctgtggggc    960
aggaggtctt tggtctggtg cctggtctga tgatgtatgc cacaatctgg ctgcgggaac   1020
acaacagagt atgcgatgtg cttaaacagg agcatcctga atggggtgat gagcagttgt   1080
tccagacaag caggctaata ctgataggag agactattaa gattgtgatt gaagattatg   1140
tgcaacactt gagtggctat cacttcaaac tgaaatttga cccagaacta cttttcaaca   1200
aacaattcca gtaccaaaat cgtattgctg ctgaatttaa caccctctat cactggcatc   1260
cccttctgcc tgacaccttt caaattcatg accagaaata caactatcaa cagtttatct   1320
acaacaactc tatattgctg gaacatggaa ttacccagtt tgttgaatca ttcaccaggc   1380
aaattgctgg cagggttgct ggtggtagga atgttccacc cgcagtacag aaagtatcac   1440
aggcttccat tgaccagagc aggcagatga ataccagtc ttttaatgag taccgcaaac   1500
gctttatgct gaagccctat gaatcatttg aagaacttac aggagaaaag gaaatgtctg   1560
cagagttgga agcactctat ggtgacatcg atgctgtgga gctgtatcct gcccttctgg   1620
tagaaaagcc tcggccagat gccatctttg gtgaaaccat ggtagaagtt ggagcaccat   1680
tctccttgaa aggactatg ggtaatgtta tatgttctcc tgcctactgg aagccaagca   1740
cttttggtgg agaagtgggt tttcaaatca tcaacactgc ctcaattcag tctctcatct   1800
gcaataacgt gaagggctgt ccctttactt cattcagtgt tccagatcca gagctcatta   1860
aaacagtcac catcaatgca agttcttccc gctccggact agatgatatc aatcccacag   1920
tactactaaa agaacgttcg actgaactgt agaagtctaa tgatcatatt tatttattta   1980
tatgaaccat gtctattaat ttaattattt aataatattt atattaaact ccttatgtta   2040
cttaacatct tctgtaacag aagtcagtac tcctgttgcg gagaaaggag tcatacttgt   2100
gaagactttt atgtcactac tctaaagatt ttgctgttgc tgttaagttt ggaaaacagt   2160
ttttattctg ttttataaac cagagagaaa tgagttttga cgtcttttta cttgaatttc   2220
aacttatatt ataagaacga agtaaagat gtttgaatac ttaaacactg tcacaagatg   2280
gcaaaatgct gaaagttttt acactgtcga tgtttccaat gcatcttcca tgatgcatta   2340
gaagtaacta atgtttgaaa ttttaaagta cttttggtta tttttctgtc atcaaacaaa   2400
aacaggtatc agtgcattat taaatgaata tttaaattag acattaccag taatttcatg   2460 tctactttt aaaatcagca atgaaacaat aatttgaaat ttctaaattc atagggtaga   2520
atcacctgta aaagcttgtt tgatttctta agttattaa acttgtacat ataccaaaaa   2580
gaagctgtct tggatttaaa tctgtaaaat cagtagaaat tttactacaa ttgcttgtta   2640
aaatatttta taagtgatgt tcctttttca ccaagagtat aaaccttttt agtgtgactg   2700
ttaaaacttc cttttaaatc aaaatgccaa atttattaag gtggtggagc cactgcagtg   2760
ttatcttaaa ataagaatat tttgttgaga tattccagaa tttgtttata tggctggtaa   2820
catgtaaaat ctatatcagc aaaagggtct acctttaaaa taagcaataa caaagaagaa   2880
```

-continued

| | |
|---|---|
| aaccaaatta ttgttcaaat ttaggtttaa acttttgaag caaacttttt tttatccttg | 2940 |
| tgcactgcag gcctggtact cagattttgc tatgaggtta atgaagtacc aagctgtgct | 3000 |
| tgaataatga tatgttttct cagattttct gttgtacagt ttaatttagc agtccatatc | 3060 |
| acattgcaaa agtagcaatg acctcataaa atacctcttc aaaatgctta aattcatttc | 3120 |
| acacattaat tttatctcag tcttgaagcc aattcagtag gtgcattgga atcaagcctg | 3180 |
| gctacctgca tgctgttcct tttcttttct tcttttagcc attttgctaa gagacacagt | 3240 |
| cttctcatca cttcgtttct cctattttgt tttactagtt ttaagatcag agttcacttt | 3300 |
| ctttggactc tgcctatatt ttcttacctg aacttttgca agttttcagg taaacctcag | 3360 |
| ctcaggactg ctatttagct cctcttaaga agattaaaag agaaaaaaaa aggccctttt | 3420 |
| aaaaatagta tacacttatt ttaagtgaaa agcagagaat tttatttata gctaatttta | 3480 |
| gctatctgta accaagatgg atgcaaagag gctagtgcct cagagagaac tgtacggggt | 3540 |
| ttgtgactgg aaaagttac gttcccattc taattaatgc cctttcttat ttaaaaacaa | 3600 |
| aaccaaatga tatctaagta gttctcagca ataataataa tgacgataat acttctttc | 3660 |
| cacatctcat tgtcactgac atttaatggt actgtatatt acttaattta ttgaagatta | 3720 |
| ttatttatgt cttattagga cactatggtt ataaactgtg tttaagccta caatcattga | 3780 |
| ttttttttg ttatgtcaca atcagtatat cttctttggg gttacctctc tgaatattat | 3840 |
| gtaaacaatc caagaaatg attgtattaa gatttgtgaa taaattttta gaaatctgat | 3900 |
| tggcatattg agatatttaa ggttgaatgt ttgtccttag gataggccta tgtgctagcc | 3960 |
| cacaaagaat attgtctcat tagcctgaat gtgccataag actgaccttt taaaatgttt | 4020 |
| tgagggatct gtggatgctt cgttaatttg ttcagccaca atttattgag aaaatattct | 4080 |
| gtgtcaagca ctgtgggttt taatattttt aaatcaaacg ctgattacag ataatagtat | 4140 |
| ttatataaat aattgaaaaa aattttcttt tgggaagagg gagaaaatga aataaatatc | 4200 |
| attaaagata actcaggaga atcttcttta caattttacg tttagaatgt ttaaggttaa | 4260 |
| gaaagaaata gtcaatatgc ttgtataaaa cactgttcac tgtttttttt aaaaaaaaaa | 4320 |
| cttgatttgt tattaacatt gatctgctga caaaacctgg gaatttgggt tgtgtatgcg | 4380 |
| aatgtttcag tgcctcagac aaatgtgtat ttaacttatg taaaagataa gtctggaaat | 4440 |
| aaatgtctgt ttattttttgt actatttaaa aattgacaga tcttttctga agaaaaaaaa | 4500 |
| aaaaaaa | 4507 |

<210> SEQ ID NO 14
<211> LENGTH: 604
<212> TYPE: PRT
<213> ORGANISM: Homo sapiens

<400> SEQUENCE: 14

Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

```
Phe Lys Gly Phe Trp Asn Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
            115                 120                 125

Ser Asn Leu Ser Tyr Tyr Thr Arg Ala Leu Pro Pro Val Pro Asp Asp
130             135                 140

Cys Pro Thr Pro Leu Gly Val Lys Gly Lys Lys Gln Leu Pro Asp Ser
145             150                 155                 160

Asn Glu Ile Val Glu Lys Leu Leu Arg Arg Lys Phe Ile Pro Asp
                165                 170                 175

Pro Gln Gly Ser Asn Met Met Phe Ala Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
        210                 215                 220

Ala Arg Gln Arg Lys Leu Arg Leu Phe Lys Asp Gly Lys Met Lys Tyr
225             230                 235                 240

Gln Ile Ile Asp Gly Glu Met Tyr Pro Pro Thr Val Lys Asp Thr Gln
            245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
            275                 280                 285

Thr Ile Trp Leu Arg Glu His Asn Arg Val Cys Asp Val Leu Lys Gln
        290                 295                 300

Glu His Pro Glu Trp Gly Asp Glu Gln Leu Phe Gln Thr Ser Arg Leu
305             310                 315                 320

Ile Leu Ile Gly Glu Thr Ile Lys Ile Val Ile Glu Asp Tyr Val Gln
            325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
            355                 360                 365

Thr Leu Tyr His Trp His Pro Leu Leu Pro Asp Thr Phe Gln Ile His
        370                 375                 380

Asp Gln Lys Tyr Asn Tyr Gln Gln Phe Ile Tyr Asn Asn Ser Ile Leu
385             390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
            435                 440                 445

Phe Asn Glu Tyr Arg Lys Arg Phe Met Leu Lys Pro Tyr Glu Ser Phe
450             455                 460

Glu Glu Leu Thr Gly Glu Lys Glu Met Ser Ala Glu Leu Glu Ala Leu
465             470                 475                 480

Tyr Gly Asp Ile Asp Ala Val Glu Leu Tyr Pro Ala Leu Leu Val Glu
            485                 490                 495
```

Lys Pro Arg Pro Asp Ala Ile Phe Gly Glu Thr Met Val Glu Val Gly
                500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
                595                 600

<210> SEQ ID NO 15
<211> LENGTH: 5616
<212> TYPE: DNA
<213> ORGANISM: Homo sapiens

<400> SEQUENCE: 15
ccccggcgca gcgcggccgc agcagcctcc gccccccgca cggtgtgagc gcccgacgcg      60
gccgaggcgg ccggagtccc gagctagccc cggcggccgc cgccgcccag accgacgac      120 aggccacctc gtcggcgtcc gcccgagtcc ccgcctcgcc gccaacgcca caaccaccgc     180
gcacggcccc ctgactccgt ccagtattga tcgggagagc cggagcgagc tcttcgggga     240
gcagcgatgc gaccctccgg gacggccggg gcagcgctcc tggcgctgct ggctgcgctc     300
tgcccggcga gtcgggctct ggaggaaaag aaagtttgcc aaggcacgag taacaagctc     360
acgcagttgg cacttttga agatcatttt ctcagcctcc agaggatgtt caataactgt     420
gaggtggtcc ttgggaattt ggaaattacc tatgtgcaga ggaattatga tctttccttc     480
ttaaagacca tccaggaggt ggctggttat gtcctcattg ccctcaacac agtggagcga     540
attcctttgg aaaacctgca gatcatcaga ggaaatatgt actacgaaaa ttcctatgcc     600
ttagcagtct tatctaacta tgatgcaaat aaaaccggac tgaaggagct gcccatgaga     660
aatttacagg aaatcctgca tggcgccgtg cggttcagca caacccctgc cctgtgcaac     720
gtggagagca tccagtggcg ggacatagtc agcagtgact ttctcagcaa catgtcgatg     780
gacttccaga ccacctgggc agctgccaa agtgtgatc caagctgtcc caatgggagc     840 tgctgggtg caggagagga gaactgccag aaactgacca aatcatctg tgcccagcag     900 tgctccgggc gctgccgtgg caagtccccc agtgactgct gccacaacca gtgtgctgca     960
ggctgcacag gccccgggga gcgactgctg gtctgcc gcaaattccg agacgaagcc    1020
acgtgcaagg acacctgccc cccactcatg ctctacaacc ccaccacgta ccagatggat    1080
gtgaaccccg agggcaaata cagctttggt gccacctgcg tgaagaagtg tccccgtaat    1140
tatgtggtga cagatcacgg ctcgtgcgtc cgagcctgtg gggccgacag ctatgagatg    1200
gaggaagacg gcgtccgcaa gtgtaagaag tgcgaagggc cttgccgcaa agtgtgtaac    1260
ggaataggta ttggtgaatt taaagactca ctctccataa atgctacgaa tattaaacac    1320
ttcaaaaact gcacctccat cagtggcgat ctccacatcc tgccggtggc atttaggggt    1380
gactccttca cacatactcc tcctctggat ccacaggaac tggatattct gaaaaccgta    1440
aaggaaatca cagggttttt gctgattcag gcttggcctg aaaacaggac ggacctccat    1500

```
gcctttgaga acctagaaat catacgcggc aggaccaagc aacatggtca gttttctctt    1560
gcagtcgtca gcctgaacat aacatccttg ggattacgct ccctcaagga gataagtgat    1620
ggagatgtga taatttcagg aaacaaaaat ttgtgctatg caaatacaat aaactggaaa    1680
aaactgtttg ggacctccgg tcagaaaacc aaaattataa gcaacagagg tgaaaacagc    1740
tgcaaggcca caggccaggt ctgccatgcc ttgtgctccc ccgagggctg ctggggcccg    1800
gagcccaggg actgcgtctc ttgccggaat gtcagccgag gcaggaatg cgtgacaag     1860 tgcaaccttc tggagggtga gccaagggag tttgtggaga actctgagtg catacagtgc    1920
cacccagagt gcctgcctca ggccatgaac atcacctgca caggacgggg accagacaac    1980
tgtatccagt gtgcccacta cattgacggc ccccactgcg tcaagacctg cccggcagga    2040
gtcatgggag aaaacaacac cctggtctgg aagtacgcag acgccggcca tgtgtgccac    2100
ctgtgccatc caaactgcac ctacggatgc actgggccag gtcttgaagg ctgtccaacg    2160
aatgggccta agatcccgtc catcgccact gggatggtgg gggccctcct cttgctgctg    2220
gtggtggccc tggggatcgg cctcttcatg cgaaggcgcc acatcgttcg gaagcgcacg    2280
ctgcggaggc tgctgcagga gagggagctt gtggagcctc ttacacccag tggagaagct    2340
cccaaccaag ctctcttgag gatcttgaag gaaactgaat tcaaaaagat caagtgctg     2400 ggctccggtg cgttcggcac ggtgtataag ggactctgga tcccagaagg tgagaaagtt    2460
aaaattcccg tcgctatcaa ggaattaaga gaagcaacat ctccgaaagc caacaaggaa    2520
atcctcgatg aagcctacgt gatggccagc gtggacaacc cccacgtgtg ccgcctgctg    2580
ggcatctgcc tcacctccac cgtgcagctc atcacgcagc tcatgccctt cggctgcctc    2640
ctggactatg tccgggaaca caaagacaat attggctccc agtacctgct caactggtgt    2700
gtgcagatcg caaagggcat gaactacttg gaggaccgtc gcttggtgca ccgcgacctg    2760
gcagccagga acgtactggt gaaaacaccg cagcatgtca agatcacaga ttttgggctg    2820
gccaaactgc tgggtgcgga agagaagaa taccatgcag aaggaggcaa agtgcctatc     2880
aagtggatgg cattggaatc aattttacac agaatctata cccaccagag tgatgtctgg    2940
agctacgggg tgaccgtttg ggagttgatg acctttggat ccaagccata tgacggaatc    3000
cctgccagcg agatctcctc catcctggag aaaggagaac gcctccctca gccacccata    3060
tgtaccatcg atgtctacat gatcatggtc aagtgctgga tgatagacgc agatagtcgc    3120
ccaaagttcc gtgagttgat catcgaattc tccaaaatgg cccgagaccc ccagcgctac    3180
cttgtcattc aggggatga aagaatgcat ttgccaagtc ctacagactc caacttctac     3240
cgtgccctga tggatgaaga agacatggac gacgtggtgg atgccgacga gtacctcatc    3300
ccacagcagg gcttcttcag cagccccctc acgtcacgga ctcccctcct gagctctctg    3360
agtgcaacca gcaacaattc caccgtggct tgcattgata gaaatgggct gcaaagctgt    3420
cccatcaagg aagacagctt cttgcagcga tacagctcag accccacagg cgccttgact    3480
gaggacagca tagacgacac cttcctccca gtgcctgaat acataaacca gtccgttccc    3540
aaaaggcccg ctggctctgt gcagaatcct gtctatcaca atcagcctct gaaccccgcg    3600
cccagcagag acccacacta ccaggacccc cacagcactg cagtgggcaa ccccgagtat    3660
ctcaacactg tccagcccac ctgtgtcaac agcacattcg acagccctgc ccactgggcc    3720
cagaaaggca gccaccaaat tagcctggac aaccctgact accagcagga cttctttccc    3780
aaggaagcca agccaaatgg catctttaag ggctccacag ctgaaaatgc agaataccta    3840
agggtcgcgc cacaaagcag tgaatttatt ggagcatgac cacggaggat agtatgagcc    3900
```

| | |
|---|---|
| ctaaaaatcc agactctttc gatacccagg accaagccac agcaggtcct ccatcccaac | 3960 |
| agccatgccc gcattagctc ttagacccac agactggttt tgcaacgttt acaccgacta | 4020 |
| gccaggaagt acttccacct cgggcacatt ttgggaagtt gcattccttt gtcttcaaac | 4080 |
| tgtgaagcat ttacagaaac gcatccagca agaatattgt cccttTgagc agaaatttat | 4140 |
| ctttcaaaga ggtatatttg aaaaaaaaaa aaagtatatg tgaggatttt tattgattgg | 4200 |
| ggatcttgga gttttTcatt gtcgctattg attTtTacTT caatgggcTc TTccaacaag | 4260 |
| gaagaagctt gctggtagca cttgctaccc tgagttcatc caggcccaac tgtgagcaag | 4320 |
| gagcacaagc cacaagtctt ccagaggatg cttgattcca gtggttctgc ttcaaggctt | 4380 |
| ccactgcaaa acactaaaga tccaagaagg ccttcatggc cccagcaggc cggatcggta | 4440 |
| ctgtatcaag tcatggcagg tacagtagga taagccactc tgtcccttcc tgggcaaaga | 4500 |
| agaaacggag gggatggaat tcttccttag acttactttt gtaaaaatgt ccccacggta | 4560 |
| cttactcccc actgatggac cagtggtttc cagtcatgag cgttagactg acttgtttgt | 4620 |
| cttccattcc attgttttga aactcagtat gctgcccctg tcttgctgtc atgaaatcag | 4680 |
| caagagagga tgacacatca ataataact cggattccag cccacattgg attcatcagc | 4740 |
| atttggacca atagcccaca gctgagaatg tggaatacct aaggatagca ccgcttttgt | 4800 |
| tctcgcaaaa acgtatctcc taatttgagg ctcagatgaa atgcatcagg tcctttgggg | 4860 |
| catagatcag aagactacaa aaatgaagct gctctgaaat ctcctttagc catcacccca | 4920 |
| accccccaaa attagtttgt gttacttatg aagatagtt ttctccttTt acttcacttc | 4980 |
| aaaagctttt tactcaaaga gtatatgttc cctccaggtc agctgccccc aaaccccctc | 5040 |
| cttacgcttt gtcacacaaa aagtgtctct gccttgagtc atctattcaa gcacttacag | 5100 |
| ctctggccac aacagggcat tttacaggtg cgaatgacag tagcattatg agtagtgtgg | 5160 |
| aattcaggta gtaaatatga aactagggtt tgaaattgat aatgctttca caacatttgc | 5220 |
| agatgtttta gaaggaaaaa agttccttcc taaaataatt tctctacaat tggaagattg | 5280 |
| gaagattcag ctagttagga gcccacctTT ttTcctaatc tgtgtgtgcc ctgtaacctg | 5340 |
| actggttaac agcagtcctt tgtaaacagt gttttaaact ctcctagtca atatccaccc | 5400 |
| catccaattt atcaaggaag aaatggttca gaaaatattt tcagcctaca gttatgttca | 5460 |
| gtcacacaca catacaaaat gttccttttg cttttaaagt aattttttgac tcccagatca | 5520 |
| gtcagagccc ctacagcatt gttaagaaag tatttgattt ttgtctcaat gaaaataaaa | 5580 |
| ctatattcat ttccactcta aaaaaaaaaa aaaaaa | 5616 |

<210> SEQ ID NO 16
<211> LENGTH: 2239
<212> TYPE: DNA
<213> ORGANISM: Homo sapiens

<400> SEQUENCE: 16

| | |
|---|---|
| cccccggcgca gcgcggccgc agcagcctcc gcccccgca cggtgtgagc gcccgacgcg | 60 |
| gccgaggcgg ccggagtccc gagctagccc cggcggccgc cgccgcccag accggacgac | 120 |
| aggccacctc gtcggcgtcc gcccgagtcc ccgcctcgcc gccaacgcca caaccaccgc | 180 |
| gcacggcccc ctgactccgt ccagtattga tcgggagagc cggagcgagc tcttcgggga | 240 |
| gcagcgatgc gaccctccgg gacggccggg gcagcgctcc tggcgctgct ggctgcgctc | 300 |
| tgcccggcga gtcgggctct ggaggaaaag aaagtttgcc aaggcacgag taacaagctc | 360 |

| | |
|---|---|
| acgcagttgg gcactttga agatcatttt ctcagcctcc agaggatgtt caataactgt | 420 |
| gaggtggtcc ttgggaattt ggaaattacc tatgtgcaga ggaattatga tctttccttc | 480 |
| ttaaagacca tccaggaggt ggctggttat gtcctcattg ccctcaacac agtggagcga | 540 |
| attcctttgg aaaacctgca gatcatcaga ggaaatatgt actacgaaaa ttcctatgcc | 600 |
| ttagcagtct tatctaacta tgatgcaaat aaaaccggac tgaaggagct gcccatgaga | 660 |
| aatttacagg aaatcctgca tggcgccgtg cggttcagca caaccctgc cctgtgcaac | 720 |
| gtggagagca tccagtggcg ggacatagtc agcagtgact ttctcagcaa catgtcgatg | 780 |
| gacttccaga accacctggg cagctgccaa aagtgtgatc caagctgtcc caatgggagc | 840 |
| tgctggggtg caggagagga gaactgccag aaactgacca aaatcatctg tgcccagcag | 900 |
| tgctccgggc gctgccgtgg caagtccccc agtgactgct gccacaacca gtgtgctgca | 960 |
| ggctgcacag gccccgggga gagcgactgc ctggtctgcc gcaaattccg agacgaagcc | 1020 |
| acgtgcaagg acacctgccc cccactcatg ctctacaacc ccaccacgta ccagatggat | 1080 |
| gtgaaccccg agggcaaata cagctttggt gccacctgcg tgaagaagtg tccccgtaat | 1140 |
| tatgtggtga cagatcacgg ctcgtgcgtc cgagcctgtg gggccgacag ctatgagatg | 1200 |
| gaggaagacg gcgtccgcaa gtgtaagaag tgcgaagggc cttgccgcaa agtgtgtaac | 1260 |
| ggaataggta ttggtgaatt taaagactca ctctccataa atgctacgaa tattaaacac | 1320 |
| ttcaaaaact gcacctccat cagtggcgat ctccacatcc tgccggtggc atttagggggt | 1380 |
| gactccttca cacatactcc tcctctggat ccacaggaac tggatattct gaaaaccgta | 1440 |
| aaggaaatca caggggttttt gctgattcag gcttggcctg aaaacaggac ggacctccat | 1500 |
| gcctttgaga acctagaaat catacgcggc aggaccaagc aacatggtca gttttctctt | 1560 |
| gcagtcgtca gcctgaacat aacatccttg ggattacgct ccctcaagga gataagtgat | 1620 |
| ggagatgtga taatttcagg aaacaaaaat ttgtgctatg caaatacaat aaactggaaa | 1680 |
| aaactgtttg gaacctccgg tcagaaaacc aaaattataa gcaacagagg tgaaaacagc | 1740 |
| tgcaaggcca caggccaggt ctgccatgcc ttgtgctccc cgagggctg ctggggcccg | 1800 |
| gagcccaggg actgcgtctc ttgccggaat gtcagccgag caggaatg cgtggacaag | 1860 |
| tgcaaccttc tggagggtga gccaagggag tttgtggaga actctgagtg catacagtgc | 1920 |
| cacccagagt gcctgcctca ggccatgaac atcacctgca caggacgggg accagacaac | 1980 |
| tgtatccagt gtgcccacta cattgacggc ccccactgcg tcaagacctg cccggcagga | 2040 |
| gtcatgggag aaaacaacac cctggtctgg aagtacgcag acgccggcca tgtgtgccac | 2100 |
| ctgtgccatc caaactgcac ctacgggtcc taataaatct tcactgtctg actttagtct | 2160 |
| cccactaaaa ctgcatttcc tttctacaat ttcaatttct cccttttgctt caaataaagt | 2220 |
| cctgacacta ttcatttga | 2239 |

<210> SEQ ID NO 17
<211> LENGTH: 1595
<212> TYPE: DNA
<213> ORGANISM: Homo sapiens

<400> SEQUENCE: 17

| | |
|---|---|
| ccccggcgca gcgcggccgc agcagcctcc gcccccgca cggtgtgagc gcccgacgcg | 60 |
| gccgaggcgg ccggagtccc gagctagccc cggcggccgc cgccgcccag accggacgac | 120 |
| aggccacctc gtcggcgtcc gcccgagtcc ccgcctcgcc gccaacgcca caaccaccgc | 180 |
| gcacggcccc ctgactccgt ccagtattga tcgggagagc cggagcgagc tcttcgggga | 240 |

```
gcagcgatgc gaccctccgg gacggccggg gcagcgctcc tggcgctgct ggctgcgctc      300
tgcccggcga gtcgggctct ggaggaaaag aaagtttgcc aaggcacgag taacaagctc      360
acgcagttgg gcacttttga agatcatttt ctcagcctcc agaggatgtt caataactgt      420
gaggtggtcc ttgggaattt ggaaattacc tatgtgcaga ggaattatga tctttccttc      480
ttaaagacca tccaggaggt ggctggttat gtcctcattg ccctcaacac agtggagcga      540
attcctttgg aaaacctgca gatcatcaga ggaaatatgt actacgaaaa ttcctatgcc      600
ttagcagtct tatctaacta tgatgcaaat aaaaccggac tgaaggagct gcccatgaga      660
aatttacagg aaatcctgca tggcgccgtg cggttcagca acaaccctgc cctgtgcaac      720
gtggagagca tccagtggcg ggacatagtc agcagtgact ttctcagcaa catgtcgatg      780
gacttccaga accacctggg cagctgccaa aagtgtgatc caagctgtcc caatgggagc      840
tgctggggtg caggagagga gaactgccag aaactgacca aaatcatctg tgcccagcag      900
tgctccgggc gctgccgtgg caagtccccc agtgactgct gccacaacca gtgtgctgca      960
ggctgcacag gccccgggga gagcgactgc ctggtctgcc gcaaattccg agacgaagcc     1020
acgtgcaagg acacctgccc cccactcatg ctctacaacc ccaccacgta ccagatggat     1080
gtgaaccccg agggcaaata cagctttggt gccacctgcg tgaagaagtg tccccgtaat     1140
tatgtggtga cagatcacgg ctcgtgcgtc cgagcctgtg gggccgacag ctatgagatg     1200
gaggaagacg gcgtccgcaa gtgtaagaag tgcgaagggc cttgccgcaa agtgtgtaac     1260
ggaataggta ttggtgaatt taaagactca ctctccataa atgctacgaa tattaaacac     1320
ttcaaaaact gcacctccat cagtggcgat ctccacatcc tgccggtggc atttagggt      1380 gactccttca cacatactcc tcctctggat ccacaggaac tggatattct gaaaaccgta     1440
aaggaaatca caggtttgag ctgaattatc acatgaatat aaatgggaaa tcagtgtttt     1500
agagagagaa cttttcgaca tatttcctgt tcccttggaa taaaaacatt tcttctgaaa     1560
ttttaccgtt aaaaaaaaaa aaaaaaaaaa aaaaa                                1595

<210> SEQ ID NO 18
<211> LENGTH: 2865
<212> TYPE: DNA
<213> ORGANISM: Homo sapiens

<400> SEQUENCE: 18
ccccggcgca gcgcggccgc agcagcctcc gccccccgca cggtgtgagc gcccgacgcg       60
gccgaggcgg ccggagtccc gagctagccc cggcggccgc cgccgcccag accggacgac      120
aggccacctc gtcggcgtcc gcccgagtcc ccgcctcgcc gccaacgcca caaccaccgc      180
gcacggcccc ctgactccgt ccagtattga tcggagagc cggagcgagc tcttcgggga      240
gcagcgatgc gaccctccgg gacggccggg gcagcgctcc tggcgctgct ggctgcgctc      300
tgcccggcga gtcgggctct ggaggaaaag aaagtttgcc aaggcacgag taacaagctc      360
acgcagttgg gcacttttga agatcatttt ctcagcctcc agaggatgtt caataactgt      420
gaggtggtcc ttgggaattt ggaaattacc tatgtgcaga ggaattatga tctttccttc      480
ttaaagacca tccaggaggt ggctggttat gtcctcattg ccctcaacac agtggagcga      540
attcctttgg aaaacctgca gatcatcaga ggaaatatgt actacgaaaa ttcctatgcc      600
ttagcagtct tatctaacta tgatgcaaat aaaaccggac tgaaggagct gcccatgaga      660
aatttacagg aaatcctgca tggcgccgtg cggttcagca acaaccctgc cctgtgcaac      720
```

| | |
|---|---|
| gtggagagca tccagtggcg ggacatagtc agcagtgact ttctcagcaa catgtcgatg | 780 |
| gacttccaga accacctggg cagctgccaa aagtgtgatc caagctgtcc caatgggagc | 840 |
| tgctggggtg caggagagga gaactgccag aaactgacca aaatcatctg tgcccagcag | 900 |
| tgctccgggc gctgccgtgg caagtcccc agtgactgct gccacaacca gtgtgctgca | 960 |
| ggctgcacag gcccccggga gagcgactgc ctggtctgcc gcaaattccg agacgaagcc | 1020 |
| acgtgcaagg acacctgccc cccactcatg ctctacaacc ccaccacgta ccagatggat | 1080 |
| gtgaaccccg agggcaaata cagctttggt gccacctgcg tgaagaagtg tccccgtaat | 1140 |
| tatgtggtga cagatcacgg ctcgtgcgtc cgagcctgtg gggccgacag ctatgagatg | 1200 |
| gaggaagacg gcgtccgcaa gtgtaagaag tgcgaagggc cttgccgcaa agtgtgtaac | 1260 |
| ggaataggta ttggtgaatt taaagactca ctctccataa atgctacgaa tattaaacac | 1320 |
| ttcaaaaact gcacctccat cagtggcgat ctccacatcc tgccggtggc atttaggggt | 1380 |
| gactccttca cacatactcc tcctctggat ccacaggaac tggatattct gaaaaccgta | 1440 |
| aaggaaatca cagggttttt gctgattcag gcttggcctg aaaacaggac ggacctccat | 1500 |
| gcctttgaga acctagaaat catacgcggc aggaccaagc aacatggtca gttttctctt | 1560 |
| gcagtcgtca gcctgaacat aacatccttg ggattacgct ccctcaagga gataagtgat | 1620 |
| ggagatgtga tatttcagg aaacaaaaat ttgtgctatg caaatacaat aaactggaaa | 1680 |
| aaactgtttg gacctccgg tcagaaaacc aaaattataa gcaacagagg tgaaaacagc | 1740 |
| tgcaaggcca caggccaggt ctgccatgcc ttgtgctccc ccgagggctg ctggggcccg | 1800 |
| gagcccaggg actgcgtctc ttgccggaat gtcagccgag gcagggaatg cgtggacaag | 1860 |
| tgcaaccttc tggagggtga gccaagggag tttgtggaga actctgagtg catacagtgc | 1920 |
| cacccagagt gcctgcctca ggccatgaac atcacctgca caggacgggg accagacaac | 1980 |
| tgtatccagt gtgcccacta cattgacggc ccccactgcg tcaagacctg cccggcagga | 2040 |
| gtcatgggag aaaacaacac cctggtctgg aagtacgcag acgccggcca tgtgtgccac | 2100 |
| ctgtgccatc caaactgcac ctacgggcca ggaaatgaga gtctcaaagc catgttattc | 2160 |
| tgccttttta actatcatc ctgtaatcaa agtaatgatg cagcgtgtc ccaccagagc | 2220 |
| gggagcccag ctgctcagga gtcatgctta ggatggatcc cttctcttct gccgtcagag | 2280 |
| tttcagctgg gttggggtgg atgcagccac ctccatgcct ggccttctgc atctgtgatc | 2340 |
| atcacggcct cctcctgcca ctgagcctca tgccttcacg tgtctgttcc cccgcttttt | 2400 |
| cctttctgcc acccctgcac gtgggccgcc aggttcccaa gagtatccta cccatttcct | 2460 |
| tccttccact ccctttgcca gtgcctctca ccccaactag tagctaacca tcaccccag | 2520 |
| gactgacctc ttcctcctcg ctgccagatg attgttcaaa gcacagaatt tgtcagaaac | 2580 |
| ctgcagggac tccatgctgc cagccttctc cgtaattagc atggcccag tccatgcttc | 2640 |
| tagccttggt tccttctgcc cctctgtttg aaattctaga gccagctgtg gacaattat | 2700 |
| ctgtgtcaaa agccagatgt gaaaacatct caataacaaa ctggctgctt tgttcaatgc | 2760 |
| tagaacaacg cctgtcacag agtagaaact caaaatatt tgctgagtga atgaacaaat | 2820 |
| gaataaatgc ataataaata attaaccacc aatccaacat ccaga | 2865 |

<210> SEQ ID NO 19
<211> LENGTH: 1210
<212> TYPE: PRT
<213> ORGANISM: Homo sapiens

<400> SEQUENCE: 19

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
        260                 265                 270

Thr Thr Tyr Gln Met Asp Val Asn Pro Glu Gly Lys Tyr Ser Phe Gly
    275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
        340                 345                 350

Ala Thr Asn Ile Lys His Phe Lys Asn Cys Thr Ser Ile Ser Gly Asp
    355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415
```

-continued

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro

```
                835                 840                 845
Gln His Val Lys Ile Thr Asp Phe Gly Leu Ala Lys Leu Leu Gly Ala
    850                 855                 860
Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
                900                 905                 910
Lys Pro Tyr Asp Gly Ile Pro Ala Ser Glu Ile Ser Ser Ile Leu Glu
                915                 920                 925
Lys Gly Glu Arg Leu Pro Gln Pro Pro Ile Cys Thr Ile Asp Val Tyr
            930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
Thr Asp Ser Asn Phe Tyr Arg Ala Leu Met Asp Glu Glu Asp Met Asp
            995                1000                1005
Asp Val Val Asp Ala Asp Glu Tyr Leu Ile Pro Gln Gln Gly Phe
    1010                1015                1020
Phe Ser Ser Pro Ser Thr Ser Arg Thr Pro Leu Leu Ser Ser Leu
    1025                1030                1035
Ser Ala Thr Ser Asn Asn Ser Thr Val Ala Cys Ile Asp Arg Asn
    1040                1045                1050
Gly Leu Gln Ser Cys Pro Ile Lys Glu Asp Ser Phe Leu Gln Arg
    1055                1060                1065
Tyr Ser Ser Asp Pro Thr Gly Ala Leu Thr Glu Asp Ser Ile Asp
    1070                1075                1080
Asp Thr Phe Leu Pro Val Pro Glu Tyr Ile Asn Gln Ser Val Pro
    1085                1090                1095
Lys Arg Pro Ala Gly Ser Val Gln Asn Pro Val Tyr His Asn Gln
    1100                1105                1110
Pro Leu Asn Pro Ala Pro Ser Arg Asp Pro His Tyr Gln Asp Pro
    1115                1120                1125
His Ser Thr Ala Val Gly Asn Pro Glu Tyr Leu Asn Thr Val Gln
    1130                1135                1140
Pro Thr Cys Val Asn Ser Thr Phe Asp Ser Pro Ala His Trp Ala
    1145                1150                1155
Gln Lys Gly Ser His Gln Ile Ser Leu Asp Asn Pro Asp Tyr Gln
    1160                1165                1170
Gln Asp Phe Phe Pro Lys Glu Ala Lys Pro Asn Gly Ile Phe Lys
    1175                1180                1185
Gly Ser Thr Ala Glu Asn Ala Glu Tyr Leu Arg Val Ala Pro Gln
    1190                1195                1200
Ser Ser Glu Phe Ile Gly Ala
    1205                1210

<210> SEQ ID NO 20
<211> LENGTH: 628
<212> TYPE: PRT
<213> ORGANISM: Homo sapiens
```

```
<400> SEQUENCE: 20

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
```

```
                    405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Ser
625

<210> SEQ ID NO 21
<211> LENGTH: 405
<212> TYPE: PRT
<213> ORGANISM: Homo sapiens

<400> SEQUENCE: 21

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140
```

-continued

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
            165                 170                 175

Ser Met Asp Phe Gln Asn His Leu Gly Ser Cys Gln Lys Cys Asp Pro
        180                 185                 190

Ser Cys Pro Asn Gly Ser Cys Trp Gly Ala Gly Glu Glu Asn Cys Gln
    195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
        260                 265                 270

Thr Thr Tyr Gln Met Asp Val Asn Pro Glu Gly Lys Tyr Ser Phe Gly
    275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
        340                 345                 350

Ala Thr Asn Ile Lys His Phe Lys Asn Cys Thr Ser Ile Ser Gly Asp
    355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Leu Ser
            405

<210> SEQ ID NO 22
<211> LENGTH: 705
<212> TYPE: PRT
<213> ORGANISM: Homo sapiens

<400> SEQUENCE: 22

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
            85                  90                  95

Glu Arg Ile Pro Leu Glu Asn Leu Gln Ile Ile Arg Gly Asn Met Tyr
        100                 105                 110

-continued

```
Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525
```

```
                                     -continued

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Pro Ala Ala Gln Glu Ser Cys Leu Gly Trp Ile Pro
            660                 665                 670

Ser Leu Leu Pro Ser Glu Phe Gln Leu Gly Trp Gly Gly Cys Ser His
        675                 680                 685

Leu His Ala Trp Pro Ser Ala Ser Val Ile Ile Thr Ala Ser Ser Cys
    690                 695                 700

His
705

<210> SEQ ID NO 23
<211> LENGTH: 1576
<212> TYPE: DNA
<213> ORGANISM: Homo sapiens

<400> SEQUENCE: 23
gcgaggcagc cagcgaggga gagagcgagc gggcgagccg gagcgaggaa gggaaagcgc      60
aagagagagc gcacacgcac acacccgccg cgcgcactcg cgcacggacc cgcacgggga     120
cagctcggaa gtcatcagtt ccatgggcga gatgctgctg ctggcgagat gtctgctgct     180
agtcctcgtc tcctcgctgc tggtatgctc gggactggcg tgcggaccgg caggggggtt     240
cgggaagagg aggcacccca aaaagctgac ccctttagcc tacaagcagt ttatccccaa     300
tgtggccgag aagaccctag gcgccagcgg aaggtatgaa gggaagatct ccagaaactc     360
cgagcgattt aaggaactca cccccaatta caaccccgac atcatattta aggatgaaga     420
aaacaccgga gcggacaggc tgatgactca gaggtgtaag gacaagttga acgctttggc     480
catctcggtg atgaaccagt ggccaggagt gaaactgcgg gtgaccgagg ctgggacga     540 agatggccac cactcagagg agtctctgca ctacgagggc gcgcagtgg acatcaccac      600 gtctgaccgc gaccgcagca gtacggcat gctggcccgc ctggcggtgg aggccggctt      660
cgactgggtg tactacgagt ccaaggcaca tatccactgc tcggtgaaag cagagaactc     720
ggtggcggcc aaatcgggag gctgcttccc gggctcggcc acggtgcacc tggagcaggg     780
cggcaccaag ctggtgaagg acctgagccc cggggaccgc gtgctggcgg cggacgacca     840
gggccggctg ctctacagcg acttcctcac tttcctggac cgcgacgacg cgccaagaa      900 ggtcttctac gtgatcgaga cgcgggagcg cgcgagcgc ctgctgctca ccgccgcgca     960
cctgctcttt gtggcgccgc acaacgactc ggccaccggg gagcccgagg cgtcctcggg    1020
ctcggggccg ccttccgggg gcgcactggg gcctcgggcg ctgttcgcca gccgcgtgcg    1080
```

-continued

```
cccgggccag cgcgtgtacg tggtggccga gcgtgacggg gaccgccggc tcctgcccgc    1140
cgctgtgcac agcgtgaccc taagcgagga ggccgcgggc gcctacgcgc cgctcacggc    1200
ccagggcacc attctcatca accgggtgct ggcctcgtgc tacgcggtca tcgaggagca    1260
cagctgggcg caccgggcct tcgcgccctt ccgcctggcg cacgcgctcc tggctgcact    1320
ggcgcccgcg cgcacggacc gcggcgggga cagcggcggc ggggaccgcg ggggcggcgg    1380
cggcagagta gccctaaccg ctccaggtgc tgccgacgct ccgggtgcgg gggccaccgc    1440
gggcatccac tggtactcgc agctgctcta ccaaataggc acctggctcc tggacagcga    1500
ggccctgcac ccgctgggca tggcggtcaa gtccagctga agccggggg ccggggagg     1560 ggcgcgggag ggggcg                                                     1576
```

<210> SEQ ID NO 24
<211> LENGTH: 462
<212> TYPE: PRT
<213> ORGANISM: Homo sapiens

<400> SEQUENCE: 24

```
Met Leu Leu Leu Ala Arg Cys Leu Leu Leu Val Leu Val Ser Ser Leu
1               5                   10                  15

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
```

-continued

```
                        275                 280                 285
Ser Gly Ser Gly Pro Ser Gly Gly Ala Leu Gly Pro Arg Ala Leu
    290                 295                 300

Phe Ala Ser Arg Val Arg Pro Gly Gln Arg Val Tyr Val Ala Glu
305                 310                 315                 320

Arg Asp Gly Asp Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
            355                 360                 365

Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
                405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
            435                 440                 445

Ser Glu Ala Leu His Pro Leu Gly Met Ala Val Lys Ser Ser
    450                 455                 460
```

<210> SEQ ID NO 25
<211> LENGTH: 11242
<212> TYPE: DNA
<213> ORGANISM: Homo sapiens

<400> SEQUENCE: 25

| | | |
|---|---|---|
| tttttttttt tttttttga gaaaggggaa tttcatccca aataaaagga atgaagtctg | 60 |
| gctccggagg agggtcccg acctcgctgt gggggctcct gtttctctcc gccgcgctct | 120 |
| cgctctggcc gacgagtgga gaaatctgcg ggccaggcat cgacatccgc aacgactatc | 180 |
| agcagctgaa gcgcctggag aactgcacgg tgatcgaggg ctacctccac atcctgctca | 240 |
| tctccaaggc cgaggactac cgcagctacc gcttccccaa gctcacggtc attaccgagt | 300 |
| acttgctgct gttccgagtg gctggcctcg agagcctcgg agacctcttc ccaaccctca | 360 |
| cggtcatccg cggctggaaa ctcttctaca actacgccct ggtcatcttc gagatgacca | 420 |
| atctcaagga tattgggctt acaacctga ggaacattac tcgggggggcc atcaggattg | 480 |
| agaaaaatgc tgacctctgt tacctctcca ctgtggactg gtccctgatc ctggatgcgg | 540 |
| tgtccaataa ctacattgtg gggaataagc ccccaaagga atgtggggac ctgtgtccag | 600 |
| ggaccatgga ggagaagccg atgtgtgaga agaccaccat caacaatgag tacaactacc | 660 |
| gctgctggac cacaaaccgc tgccagaaaa tgtgcccaag cacgtgtggg aagcgggcgt | 720 |
| gcaccgagaa caatgagtgc tgccaccccg agtgcctggg cagctgcagc gcgcctgaca | 780 |
| acgacacggc ctgtgtagct tgccgccact actactatgc cggtgtctgt gtgcctgcct | 840 |
| gcccgcccaa cacctacagg tttgagggct ggcgctgtgt ggaccgtgac ttctgcgcca | 900 |
| acatcctcag cgccgagagc agcgactccg aggggtttgt gatccacgac ggcgagtgca | 960 |
| tgcaggagtg ccctctcggc ttcatccgca acggcagcca gagcatgtac tgcatccctt | 1020 |
| gtgaaggtcc ttgcccgaag gtctgtgagg aagaaaagaa aacaaagacc attgattctg | 1080 |

```
ttacttctgc tcagatgctc caaggatgca ccatcttcaa gggcaatttg ctcattaaca    1140
tccgacgggg gaataacatt gcttcagagc tggagaactt catggggctc atcgaggtgg    1200
tgacgggcta cgtgaagatc cgccattctc atgccttggt ctccttgtcc ttcctaaaaa    1260
accttcgcct catcctagga gaggagcagc tagaagggaa ttactccttc tacgtcctcg    1320
acaaccagaa cttgcagcaa ctgtgggact gggaccaccg caacctgacc atcaaagcag    1380
ggaaaatgta ctttgctttc aatcccaaat tatgtgtttc cgaaatttac cgcatggagg    1440
aagtgacggg gactaaaggg cgccaaagca aggggacat aaacaccagg aacaacgggg     1500
agagagcctc ctgtgaaagt gacgtcctgc atttcacctc caccaccacg tcgaagaatc    1560
gcatcatcat aacctggcac cggtaccggc cccctgacta cagggatctc atcagcttca    1620
ccgtttacta caaggaagca ccctttaaga atgtcacaga gtatgatggg caggatgcct    1680
gcggctccaa cagctggaac atggtggacg tggacctccc gcccaacaag gacgtggagc    1740
ccggcatctt actacatggg ctgaagccct ggactcagta cgccgtttac gtcaaggctg    1800
tgacccteae catggtggag aacgaccata tccgtggggc caagagtgag atcttgtaca    1860
ttcgcaccaa tgcttcagtt ccttccattc ccttggacgt tctttcagca tcgaactcct    1920
cttctcagtt aatcgtgaag tggaaccctc cctctctgcc caacggcaac ctgagttact    1980
acattgtgcg ctggcagcgg cagcctcagg acggctacct ttaccggcac aattactgct    2040
ccaaagacaa aatccccatc aggaagtatg ccgacgcac catcgacatt gaggaggtca    2100
cagagaaccc caagactgag gtgtgtggtg gggagaaagg gccttgctgc gcctgcccca    2160
aaactgaagc cgaaagcag gccgagaagg aggaggctga ataccgcaaa gtctttgaga    2220
atttcctgca caactccatc ttcgtgccca gacctgaaag gaagcggaga gatgtcatgc    2280
aagtggccaa caccaccatg tccagccgaa gcaggaacac cacggccgca gacacctaca    2340
acatcaccga cccggaagag ctggagacag agtaccettt ctttgagagc agagtggata    2400
acaaggagag aactgtcatt tctaaccttc ggcctttcac attgtaccgc atcgatatcc    2460
acagctgcaa ccacgaggct gagaagctgg gctgcagcgc ctccaacttc gtctttgcaa    2520
ggactatgcc cgcagaagga gcagatgaca ttcctgggcc agtgacctgg gagccaaggc    2580
ctgaaaactc catctttta aagtggccgg aacctgagaa tcccaatgga ttgattctaa    2640
tgtatgaaat aaaatacgga tcacaagttg aggatcagcg agaatgtgtg tccagacagg    2700
aatacaggaa gtatggaggg gccaagctaa accggctaaa ccegggaac tacacagccc     2760
ggattcaggc cacatctctc tctgggaatg ggtcgtggac agatcctgtg ttcttctatg    2820
tccaggccaa aacaggatat gaaaacttca tccatctgat catcgctctg cccgtcgctg    2880
tcctgttgat cgtgggaggg ttggtgatta tgctgtacgt cttccataga aagagaaata    2940
acagcaggct ggggaatgga gtgctgtatg cctctgtgaa cccggagtac ttcagcgctg    3000
ctgatgtgta cgttcctgat gagtgggagg tggctcggga agatcacc atgagccggg     3060
aacttgggca ggggtcgttt gggatggtct atgaaggagt tgccaagggt gtggtgaaag    3120
atgaacctga aaccagagtg gccattaaaa cagtgaacga ggccgcaagc atgcgtgaga    3180
ggattgagtt tctcaacgaa gcttctgtga tgaaggagtt caattgtcac catgtggtgc    3240
gattgctggg tgtggtgtcc caaggccagc caacactggt catcatggaa ctgatgacac    3300
ggggcgatct caaaagttat ctccggtctc tgaggccaga aatggagaat aatccagtcc    3360
tagcacctcc aagcctgagc aagatgattc agatggccgg agagattgca gacggcatgg    3420
cataccteaa cgccaataag ttcgtccaca gagaccttgc tgcccggaat tgcatggtag    3480
```

-continued

```
ccgaagattt cacagtcaaa atcggagatt ttggtatgac gcgagatatc tatgagacag    3540
actattaccg gaaaggaggg aaagggctgc tgcccgtgcg ctggatgtct cctgagtccc    3600
tcaaggatgg agtcttcacc acttactcgg acgtctggtc cttcggggtc gtcctctggg    3660
agatcgccac actggccgag cagccctacc agggcttgtc caacgagcaa gtccttcgct    3720
tcgtcatgga gggcggcctt ctggacaagc cagacaactg tcctgacatg ctgtttgaac    3780
tgatgcgcat gtgctggcag tataaccca agatgaggcc ttccttcctg agatcatca     3840 gcagcatcaa agaggagatg agcctggct tccgggaggt ctccttctac tacagcgagg     3900
agaacaagct gcccgagccg gaggagctgg acctggagcc agagaacatg gagagcgtcc    3960
ccctggaccc ctcggcctcc tcgtcctccc tgccactgcc cgacagacac tcaggacaca    4020
aggccgagaa cggccccggc cctggggtgc tggtcctccg cgccagcttc gacgagagac    4080
agccttacgc ccacatgaac gggggccgca agaacgagcg ggccttgccg ctgccccagt    4140
cttcgacctg ctgatccttg gatcctgaat ctgtgcaaac agtaacgtgt gcgcacgcgc    4200
agcggggtgg gggggagag agagttttaa caatccattc acaagcctcc tgtacctcag     4260
tggatcttca gaactgccct tgctgcccgc gggagacagc ttctctgcag taaaacacat    4320
ttgggatgtt cctttttca atatgcaagc agcttttat tccctgccca aacccttaac      4380
tgacatgggc ctttaagaac cttaatgaca acacttaata gcaacagagc acttgagaac    4440
cagtctcctc actctgtccc tgtccttccc tgttctccct ttctctctcc tctctgcttc    4500
ataacggaaa aataattgcc acaagtccag ctgggaagcc ctttttatca gtttgaggaa    4560
gtggctgtcc ctgtggcccc atccaaccac tgtacacacc cgcctgacac cgtgggtcat    4620
tacaaaaaaa cacgtgggaga tggaaatttt tacctttatc tttcacctttt ctagggacat   4680 gaaatttaca aagggccatc gttcatccaa ggctgttacc attttaacgc tgcctaatttt   4740 tgccaaaatc ctgaactttc tccctcatcg gcccggcgct gattcctcgt gtccggaggc   4800
atgggtgagc atggcagctg gttgctccat ttgagagaca cgctggcgac acactccgtc   4860
catccgactg cccctgctgt gctgctcaag gccacaggca cacaggtctc attgcttctg   4920
actagattat tatttggggg aactggacac aataggtctt tctctcagtg aaggtgggga   4980
gaagctgaac cggcttccct gccctgcctc cccagccccc tgcccaaccc ccaagaatct    5040
ggtggccatg ggccccgaag cagcctggcg gacaggcttg gagtcaaggg gccccatgcc   5100
tgcttctctc ccagccccag ctcccccgcc cgccccaag gacacagatg ggaaggggtt    5160
tccagggact cagccccact gttgatgcag gtttgcaagg aaagaaattc aaacaccaca    5220
acagcagtaa gaagaaaagc agtcaatgga ttcaagcatt ctaagctttg ttgacatttt    5280
ctctgttcct aggacttctt catgggtctt acagttctat gttagaccat gaaacatttg    5340
catacacatc gtcttttaatg tcacttttat aactttttta cggttcagat attcatctat    5400
acgtctgtac agaaaaaaaa aagctgctat ttttttttgtt cttgatcttt gtggatttaa   5460
tctatgaaaa ccttcaggtc caccctctcc cctttctgct cactccaaga aacttcttat    5520
gctttgtact agagtgcgtg actttcttcc tcttttcccg gtaatggata cttctatcac    5580
ataatttgcc atgaactgtt ggatgccttt ttataaatac atccccatc cctgctccca    5640 cctgcccctt tagttgtttt ctaacccgta ggctctctgg gcacgaggca gaaagcaggc    5700
cgggcaccca tcctgagagg gccgcgctcc tctcccagc ctgccctcac agcattggag    5760
cctgttacag tgcaagacat gatacaaact caggtcagaa aaacaaaggt taaatatttc    5820
```

```
acacgtcttt gttcagtgtt tccactcacc gtggttgaga agcctcaccc tctctttccc    5880
ttgcctttgc ttaggttgtg acacacatat atatatattt ttttaattct tgggtacaac    5940
agcagtgtta accgcagaca ctaggcattt ggattactat ttttcttaat ggctatttaa    6000
tccttccatc ccacgaaaaa cagctgctga gtccaaggga gcagcagagc gtggtccggc    6060
agggcctgtt gtggccctcg ccaccccct caccggaccg actgacctgt ctttggaacc    6120
agaacatccc aagggaactc cttcgcactg gcgttgagtg ggaccccggg atccaggctg    6180
gcccagggcg gcaccctcag ggctgtgccc gctggagtgc taggtggagg cagcacagac    6240
gccacggtgg cccaagagcc cctttgcttc ttgctggggg accagggctg tggtgctggc    6300
ccactttccc tcggccagga atccaggtcc ttggggccca ggggtcttgt cttgtttcat    6360
ttttagcact tctcaccaga gagatgacag cacaagagtt gcttctggga tagaaatgtt    6420
taggagtaag aacaaagctg ggatacggtg attgctagtt gtgactgaag attcaacaca    6480
gaaaagaaag tttatacggc ttttttgctg gtcagcagtt tgtcccactg ctttctctag    6540
tctctatccc atagcgtgtt ccctttaaaa aaaaaaaaaa ggtattatat gtaggagttt    6600
tcttttaatt tattttgtga taaattacca gtttcaatca ctgtagaaaa gccccattat    6660
gaatttaaat ttcaaggaaa gggtgtgtgt gtgtgtatgt gtggggtgtg tgtgtgtgag    6720
agtgatggga cagttcttga tttttggggt tttttttccc ccaaacattt atctacctca    6780
ctcttatttt ttatatgtgt atatagacaa aagaatacat ctcacctttc tcagcacctg    6840
acaataggcc gttgatactg gtaacctcat ccacgccaca ggcgccacac ccaggtgatg    6900
caggggggaag ccaggctgta ttccggggtc aaagcaacac taactcacct ctctgctcat    6960
ttcagacagc ttgccttttt ctgagatgtc ctgttttgtg ttgcttttt tgttttgttt    7020
tctatcttgg ttttccaccaa ggtgttagat ttctcctcct cctagccagg tggccctgtg    7080
aggccaacga gggcaccaga gcacacctgg gggagccacc aggctgtccc tggctggttg    7140
tctttggaac aaactgcttc tgtgcagatg gaatgaccaa cacatttcgt ccttaagaga    7200
gcagtggttc ctcaggttct gaggagagga aggtgtccag gcagcaccat ctctgtgcga    7260
atccccaggg taaaggcgtg gggcattggg tttgctcccc ttgctgctgc tccatccctg    7320
caggaggctc gcgctgaggc aggaccgtgc ggccatggct gctgcattca ttgagcacaa    7380
aggtgcagct gcagcagcag ctggagagca agagtcaccc agcctgtgcg ccagaatgca    7440
gaggctcctg acctcacagc cagtccctga tagaacacac gcaggagcag agtcccctcc    7500
ccctccaggc tgccctctca acttctccct cacctccttc cctagggta gacagagatg    7560
taccaaacct tccggctgga aagcccagtg gccggcgccg aggctcgtgg cgtcacgccc    7620
cccccgccag ggctgtacct ccgtctccct ggtcctgctg ctcacaggac agacggctcg    7680
ctcccctctt ccagcagctg ctcttacagg cactgatgat ttcgctggga agtgtggcgg    7740
gcagctttgc ctaagcgtgg atggctcctc ggcaattcca gcctaagtga aggcgctcag    7800
gagcctcctg ctggaacgcg acccatctct cccaggaccc cggggatctt aaggtcattg    7860
agaaatactg ttggatcagg gttttgttct tccacactgt aggtgacccc ttggaataac    7920
ggcctctcct ctcgtgcaca tacctaccgg tttccacaac tggatttcta cagatcattc    7980
agctggttat aagggttttg tttaaactgt ccgagttact gatgtcattt tgttttgtt    8040
ttatgtaggt agcttttaag tagaaaacac taacagtgta gtgcccatca tagcaaatgc    8100
ttcagaaaca cctcaataaa agagaaaact tggcttgtgt gatggtgcag tcactttact    8160
ggaccaaccc acccaccttg actataccaa ggcatcatct atccacagtt ctagcctaac    8220
```

-continued

```
ttcatgctga tttctctgcc tcttgatttt tctctgtgtg ttccaaataa tcttaagctg    8280
agttgtggca ttttccatgc aacctccttc tgccagcagc tcacactgct tgaagtcata    8340
tgaaccactg aggcacatca tggaattgat gtgagcatta agacgttctc ccacacagcc    8400
cttccctgag gcagcaggag ctggtgtgta ctggagacac tgttgaactt gatcaagacc    8460
cagaccaccc caggtctcct tcgtgggatg tcatgacgtt tgacataccT ttggaacgag    8520
cctcctcctt ggaagatgga agaccgtgtt cgtggccgac ctggcctctc ctggcctgtt    8580
tcttaagatg cggagtcaca tttcaatggt acgaaaagtg gcttcgtaaa atagaagagc    8640
agtcactgtg gaactaccaa atggcgagat gctcggtgca cattggggtg ctttgggata    8700
aaagatttat gagccaacta ttctctggca ccagattcta ggccagtttg ttccactgaa    8760
gcttttccca cagcagtcca cctctgcagg ctggcagccg aatggcttgc cagtggctct    8820
gtggcaagat cacactgaga tcgatgggtg agaaggctag gatgcttgtc tagtgttctt    8880
agctgtcacg ttggctcctt ccagggtggc cagacggtgt tggccactcc cttctaaaac    8940
acaggcgccc tcctggtgac agtgacccgc cgtggtatgc cttggcccat tccagcagtc    9000
ccagttatgc atttcaagtt tggggtttgt tcttttcgtt aatgttcctc tgtgttgtca    9060
gctgtcttca tttcctgggc taagcagcat tgggagatgt ggaccagaga tccactcctt    9120
aagaaccagt ggcgaaagac actttctttc ttcactctga agtagctggt ggtacaaatg    9180
agaacttcaa gagaggatgt tatttagact gaacctctgt tgccagagat gctgaagata    9240
cagaccttgg acaggtcaga gggtttcatt tttggccttc atcttagatg actggttgcg    9300
tcatttggag aagtgagtgc tccttgatgg tggaatgacc gggtggtggg tacagaacca    9360
ttgtcacagg gatcctggca cagagaagag ttacgagcag cagggtgcag ggcttggaag    9420
gaatgtgggc aaggttttga acttgattgt tcttgaagct atcagaccac atcgaggctc    9480
agcagtcatc cgtgggcatt tggtttcaac aaagaaacct aacatcctac tctggaaact    9540
gatctcggag ttaaggcgaa ttgttcaaga acacaaacta catcgcactc gtcagttgtc    9600
agttctgggg catgacttta gcgttttgtt tctgcgagaa cataacgatc actcattttt    9660
atgtcccacg tgtgtgtgtc cgcatctttc tggtcaacat tgttttaact agtcactcat    9720
tagcgttttc aatagggctc ttaagtccag tagattacgg gtagtcagtt gacgaagatc    9780
tggtttacaa gaactaatta aatgtttcat tgcattttg taagaacaga ataatttat    9840 aaaatgtttg tagtttataa ttgccgaaaa taatttaaag acactttttt tttctctgtg    9900
tgtgcaaatg tgtgtttgtg atccattttt tttttttttt tttaggacac ctgttttacta    9960 gctagcttta caatatgcca aaaaggatt tctccctgac ccatccgtg gttcaccctc     10020 ttttccccccc atgcttttg ccctagttta aacaaagga atgatgatga tttaaaaagt     10080
agttctgtat cttcagtatc ttggtcttcc agaaccctct ggttgggaag gggatcattt     10140
tttactggtc atttcccttt ggagtgtagc tactttaaca gatggaaaga acctcattgg     10200
ccatggaaac agccgaggtg ttggagccca gcagtgcatg gcaccgttcg gcatctggct     10260
tgattggtct ggctgccgtc attgtcagca cagtgccatg gcatgggaa gacttgactg      10320 cacagccaat ggttttcatg atgattacag catacacagt gatcacataa acgatgacag     10380
ctatggggca cacaggccat ttgcttacat gcctcgtatc atgactgatt actgctttgt     10440
tagaacacag aagagaccct atttttattta aggcagaacc ccgaagatac gtatttccaa    10500
tacagaaaag aattttttaat aaaaactata acatacacaa aaattggttt taaagttgac    10560
```

-continued

```
tccacttcct ctaactccag tggattgttg gccatgtctc cccaactcca caatatctct    10620
atcatgggaa acacctgggg ttttttgcgct acataggaga aagatctgga aactatttgg   10680
gttttgtttt caacttttca tttggatgtt tggcgttgca cacacacatc caccggtgga    10740
agagacgccc ggtgaaaaca cctgtctgct ttctaagcca gtgaggttga ggtgagaggt    10800
ttgccagagt ttgtctacct ctgggtatcc ctttgtctgg gataaaaaaa atcaaaccag    10860
aaggcgggat ggaatggatg caccgcaaat aatgcatttt ctgagttttc ttgttaaaaa    10920 aaaattttt taagtaagaa aaaaaaggt aataacatgg ccaatttgtt acataaaatg      10980
actttctgtg tataaattat tcctaaaaaa tcctgtttat ataaaaaatc agtagatgaa    11040
aaaaatttca aaatgttttt gtatattctg ttgtaagaat ttattcctgt tattgcgata    11100
tactctggat tctttacata atggaaaaaa gaaactgtct attttgaatg gctgaagcta    11160
aggcaacgtt agtttctctt actctgcttt tttctagtaa agtactacat ggtttaagtt    11220
aaataaaata attctgtatg ca                                             11242
```

<210> SEQ ID NO 26
<211> LENGTH: 1367
<212> TYPE: PRT
<213> ORGANISM: Homo sapiens

<400> SEQUENCE: 26

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

-continued

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
            290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
            370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
            405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
            485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
            645                 650                 655

Leu Tyr Arg His Asn Tyr Cys Ser Lys Asp Lys Ile Pro Ile Arg Lys
            660                 665                 670

-continued

```
Tyr Ala Asp Gly Thr Ile Asp Ile Glu Glu Val Thr Glu Asn Pro Lys
            675                 680                 685

Thr Glu Val Cys Gly Gly Glu Lys Gly Pro Cys Cys Ala Cys Pro Lys
690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
    770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
    930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
        995                 1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Arg Leu Leu Gly Val
    1055                1060                1065

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Met
```

| | | | | | | | | | |
|---|---|---|---|---|---|---|---|---|---|
| | 1085 | | | 1090 | | | 1095 | | |
| Glu | Asn | Asn | Pro | Val | Leu | Ala | Pro | Pro | Ser | Leu | Ser | Lys | Met | Ile |
| | 1100 | | | | 1105 | | | | 1110 | |

Glu Asn Asn Pro Val Leu Ala Pro Pro Ser Leu Ser Lys Met Ile
    1100                1105                1110

Gln Met Ala Gly Glu Ile Ala Asp Gly Met Ala Tyr Leu Asn Ala
    1115                1120                1125

Asn Lys Phe Val His Arg Asp Leu Ala Ala Arg Asn Cys Met Val
    1130                1135                1140

Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Ile Lys Glu Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His Ser Gly His
    1310                1315                1320

Lys Ala Glu Asn Gly Pro Gly Pro Gly Val Leu Val Leu Arg Ala
    1325                1330                1335

Ser Phe Asp Glu Arg Gln Pro Tyr Ala His Met Asn Gly Gly Arg
    1340                1345                1350

Lys Asn Glu Arg Ala Leu Pro Leu Pro Gln Ser Ser Thr Cys
    1355                1360                1365

<210> SEQ ID NO 27
<211> LENGTH: 6475
<212> TYPE: DNA
<213> ORGANISM: Homo sapiens

<400> SEQUENCE: 27

| | | |
|---|---|---|
| ggcgaggcga ggtttgctgg ggtgaggcag cggcgcggcc gggccgggcc gggccacagg | 60 |
| cggtggcggc gggaccatgg aggcggcggt cgctgctccg cgtccccggc tgctcctcct | 120 |
| cgtgctggcg gcggcggcgg cggcggcggc ggcgctgctc ccgggggcga cggcgttaca | 180 |
| gtgtttctgc cacctctgta caaaagacaa ttttacttgt gtgacagatg ggctctgctt | 240 |
| tgtctctgtc acagagacca cagacaaagt tatacacaac agcatgtgta tagctgaaat | 300 |
| tgacttaatt cctcgagata ggccgtttgt atgtgcaccc tcttcaaaaa ctgggtctgt | 360 |
| gactacaaca tattgctgca atcaggacca ttgcaataaa atagaacttc caactactgt | 420 |
| aaagtcatca cctggccttg gtcctgtgga actggcagct gtcattgctg accagtgtg | 480 |

-continued

```
cttcgtctgc atctcactca tgttgatggt ctatatctgc cacaaccgca ctgtcattca    540
ccatcgagtg ccaaatgaag aggacccttc attagatcgc ccttttattt cagagggtac    600
tacgttgaaa gacttaattt atgatatgac aacgtcaggt tctggctcag gtttaccatt    660
gcttgttcag agaacaattg cgagaactat tgtgttacaa gaaagcattg caaaggtcg     720 atttggagaa gtttggagag gaaagtggcg gggagaagaa gttgctgtta agatattctc    780
ctctagagaa gaacgttcgt ggttccgtga ggcagagatt tatcaaactg taatgttacg    840
tcatgaaaac atcctgggat ttatagcagc agacaataaa gacaatggta cttggactca    900
gctctggttg gtgtcagatt atcatgagca tggatccctt tttgattact aaaacagata    960
cacagttact gtggaaggaa tgataaaact tgctctgtcc acggcgagcg gtcttgccca   1020
tcttcacatg gagattgttg gtacccaagg aaagccagcc attgctcata gagatttgaa   1080
atcaaagaat atcttggtaa agaagaatgg aacttgctgt attgcagact taggactggc   1140
agtaagacat gattcagcca cagataccat tgatattgct ccaaaccaca gagtgggaac   1200
aaaaaggtac atggcccctg aagttctcga tgattccata aatatgaaac attttgaatc   1260
cttcaaacgt gctgacatct atgcaatggg cttagtattc tgggaaattg ctcgacgatg   1320
ttccattggt ggaattcatg aagattacca actgccttat tatgatcttg taccttctga   1380
cccatcagtt gaagaaatga gaaaagttgt ttgtgaacag aagttaaggc aaatatccc    1440 aaacagatgg cagagctgtg aagccttgag agtaatggct aaaattatga gagaatgttg   1500
gtatgccaat ggagcagcta ggcttacagc attgcggatt aagaaaacat tatcgcaact   1560
cagtcaacag gaaggcatca aaatgtaatt ctacagcttt gcctgaactc tccttttttc   1620
ttcagatctg ctcctgggtt ttaatttggg aggtcaattg ttctacctca ctgagaggga   1680
acagaaggat attgcttcct tttgcagcag tgtaataaag tcaattaaaa acttcccagg   1740
attctcttgg acccaggaaa cagccatgtg ggtccttctt gtgcactatg aacgcttctt   1800
tcccaggaca gaaaatgtgt agtctacctt tatttttat taacaaaact tgttttttaa   1860
aaagatgatt gctggtctta actttaggta actctgctgt gctggagatc atctttaagg   1920
gcaaaggagt tggattgctg aattacaatg aaacatgtct tattactaaa gaaagtgatt   1980
tactcctggt tagtacattc tcagaggatt ctgaaccact agagtttcct tgattcagac   2040
tttgaatgta ctgttctata gttttttcagg atcttaaaac taacacttat aaaactctta   2100
tcttgagtct aaaaatgacc tcatatagta gtgaggaaca taattcatgc aattgtattt   2160
tgtatactat tattgttctt tcacttattc agaacattac atgccttcaa aatgggattg   2220
tactatacca gtaagtgcca cttctgtgtc tttctaatgg aaatgagtag aattgctgaa   2280
agtctctatg ttaaaaccta tagtgtttga attcaaaaag cttatttatc tgggtaaccc   2340 aaacttttc tgttttgttt ttggaagggt ttttgtggta tgtcatttgg tattctattc    2400
tgaaaatgcc tttctcctac caaaatgtgc ttaagccact aaagaaatga agtggcatta   2460
attagtaaat tattagcatg gtcatgtttg aatattctca catcaagctt ttgcatttta   2520
attgtgttgt ctaagtatac tttaaaaaa tcaagtggca ctctagatgc ttatagtact   2580
ttaatatttg tagcatacag actaatttt ctaaaaggga agtctgtct agctgcttgt    2640 gaaaagttat gtggtattct gtaagccatt ttttcttta tctgttcaaa gacttatttt    2700
ttaagacatg aattacattt aaaattagaa tatggttaat attaaataat aggccttttt   2760
ctaggaaggc gaaggtagtt aataatttga atagataaca gatgtgcaag aaagtcacat   2820
```

```
ttgttatgta tgtaggagta aacgttcggt ggatcctctg tctttgtaac tgaggttaga    2880
gctagtgtgg ttttgaggtc tcactacact ttgaggaagg cagcttttaa ttcagtgttt    2940
ccttatgtgt gcgtacattg caactgctta catgtaattt atgtaatgca ttcagtgcac    3000
ccttgttact tgggagaggt ggtagctaaa gaacattctg agtataggtt tttctccatt    3060
tacagatgtc tttggtcaaa tattgaaagc aaacttgtca tggtcttctt acattaagtt    3120
gaaactagct tataataact ggtttttact tccaatgcta tgaagtctct gcagggcttt    3180
tacagttttc gaagtccttt tatcactgtg atcttattct gaggggagaa aaaactatca    3240
tagctctgag gcaagacttc gactttatag tgctatcagt tccccgatac agggtcagag    3300
taacccatac agtattttgg tcaggaagag aaagtggcca tttacactga atgagttgca    3360
ttctgataat gtcttatctc ttatacgtag aataaatttg aaagactatt tgatcttaaa    3420
accaaagtaa ttttagaatg agtgacatat tacataggaa tttagtgtca atttcatgtg    3480
tttaaaaaca tcatgggaaa aatgcttaga ggttactatt ttgactacaa agttgagttt    3540
ttttctgtag ttaccataat ttcattgaag caaatgaatg agtttgagag gtttgttttt    3600
atagttgtgt tgtattactt gtttaataat aatctctaat tctgtgatca ggtacttttt    3660
ttgtgggggt tttttttttg tttttttttt tttgttgttg ttttttgggcc atttctaagc    3720 ctaccagatc tgctttatga aatccagggg accaatgcat tttatcacta aaactatttt    3780
tatataattt taagaatata ccaaaagttg tctgatttaa agttgtaata catgatttct    3840
cactttcatg taaggttatc cactttttgct gaagatattt tttattgaat caaagattga    3900
gttacaatta tactttttctt acctaagtgg ataaaatgta cttttgatga atcagggaat    3960 tttttttaaag ttggagttta gttctaaatt gactttacgt attactgcag ttaattcctt    4020
ttttggctag ggatggtttg ataaaccaca attggctgat attgaaaatg aaagaaactt    4080
aaaaggtggg atggatcatg attactgtcg ataactgcag ataaatttga ttagagtaat    4140
aattttgtca tttaaaaaca cagttgttta tactgcccat cctaggatgc tcaccttcca    4200
agattcaacg tggctaaaac atcttctggt aaattgtgcg tccatattca ttttgtcagt    4260
agccaggaga aatggggatg ggggaaatac gacttagtga ggcatagaca tccctggtcc    4320
atcctttctg tctccagctg tttcttggaa cctgctctcc tgcttgctgg tccctgacgc    4380
agagaccgtt gcctccccca cagccgtttg actgaaggct gctctggaga cctagagtaa    4440
aacggctgat ggaagttgtg ggacccactt ccatttcctt cagtcattag aggtggaagg    4500 gagggggtctc caagtttgga gattgagcag atgaggcttg ggatgcccct gctttgactt    4560
cagccatgga tgaggagtgg gatggcagca aggtggctcc tgtggcagtg gagttgtgcc    4620
agaaacagtg gccagttgta tcgcctataa gacagggtaa ggtctgaaga gctgagcctg    4680
taattctgct gtaataatga tagtgctcaa gaagtgcctt gagttggtgt acagtgccat    4740
ggccatcaag aatcccagat ttcaggtttt attacaaaat gtaagtggtc acttggcgat    4800
tttgtagtac atgcatgagt tacctttttt ctctatgtct gagaactgtc agattaaaac    4860
aagatggcaa agagatcgtt agagtgcaca acaaaatcac tatcccatta gacacatcat    4920
caaaagctta ttttattct tgcactgtaa gaatcgtaag tcaactgttt cttgaccatg    4980
gcagtgttct ggctccaaat ggtagtgatt ccaataatg gttctgttaa cactttggca    5040
gaaaatgcca gctcagatat tttgagatac taaggattat cttggacat gtactgcagc    5100 ttcttgtctc tgttttggat tactggaata cccatgggcc ctctcaagag tgctggactt    5160
ctaggacatt aagatgattg tcagtacatt aaactttttca atcccattat gcaatcttgt    5220
```

| | | | | |
|---|---|---|---|---|
| ttgtaaatgt | aaacttctaa | aaatatggtt | aataacattc | aacctgttta ttacaactta | 5280 |
| aaaggaactt | cagtgaattt | gtttttattt | tttaacaaga | tttgtgaact gaatatcatg | 5340 |
| aaccatgttt | tgatacccct | ttttcacgtt | gtgccaacgg | aatagggtgt tgatatttc | 5400 |
| ttcatatgtt | aaggagatgc | ttcaaaatgt | caattgcttt | aaacttaaat tacctctcaa | 5460 |
| gagaccaagg | tacatttacc | tcattgtgta | tataatgttt | aatatttgtc agagcattct | 5520 |
| ccaggtttgc | agttttattt | ctataaagta | tgggtattat | gttgctcagt tactcaaatg | 5580 |
| gtactgtatt | gtttatattt | gtaccccaaa | taacatcgtc | tgtactttct gttttctgta | 5640 |
| ttgtatttgt | gcaggattct | ttaggcttta | tcagtgtaat | ctctgccttt taagatatgt | 5700 |
| acagaaaatg | tccatataaa | tttccattga | agtcgaatga | tactgagaag cctgtaaaga | 5760 |
| ggagaaaaaa | acataagctg | tgtttcccca | taagttttt | taaattgtat attgtatttg | 5820 |
| tagtaatatt | ccaaaagaat | gtaaatagga | aatagaagag | tgatgcttat gttaagtcct | 5880 |
| aacactacag | tagaagaatg | gaagcagtgc | aaataaatta | cattttttccc aagtgccagt | 5940 |
| ggcatatttt | aaaataaagt | gtatacgttg | gaatgagtca | tgccatatgt agttgctgta | 6000 |
| gatggcaact | agaaccctttg | agttacaaga | gtctttagaa | gttttctaac cctgcctagt | 6060 |
| gcaagttaca | atattatagc | gtgttcgggg | agtgccctcc | tgtctgcagg tgtgtctctg | 6120 |
| tgcctggggg | cttttctcca | catgcttagg | ggtgtgggtc | ttccattggg gcatgatgga | 6180 |
| cctgtctaca | ggtgatctct | gttgcctttg | ggtcagcaca | tttgttagtc tcctggggt | 6240 |
| gaaaacttgg | cttacaagag | aactggaaaa | atgatgagat | gtggtcccca aacccttgat | 6300 |
| tgactctggg | gagggcttt | gtgaatagga | ttgctctcac | attaaagata gttacttcaa | 6360 |
| tttgaaggct | ggatttaggg | attttttttt | ttccttataa | caaagacatc accaggatat | 6420 |
| gaagcttttg | ttgaaagttg | gaaaaaagt | gaaattaaag | acattcccag acaaa | 6475 |

<210> SEQ ID NO 28
<211> LENGTH: 6244
<212> TYPE: DNA
<213> ORGANISM: Homo sapiens

<400> SEQUENCE: 28

| | | | | |
|---|---|---|---|---|
| ggcgaggcga | ggtttgctgg | ggtgaggcag | cggcgcggcc | gggccgggcc gggccacagg | 60 |
| cggtggcggc | gggaccatgg | aggcggcggt | cgctgctccg | cgtccccggc tgctcctcct | 120 |
| cgtgctggcg | gcggcggcgg | cggcggcggc | ggcgctgctc | ccgggggcga cggcgttaca | 180 |
| gtgtttctgc | cacctctgta | caaaagacaa | ttttacttgt | gtgacagatg ggctctgctt | 240 |
| tgtctctgtc | acagagacca | cagacaaagt | tatacacaac | agcatgtgta tagctgaaat | 300 |
| tgacttaatt | cctcgagata | ggccgttttgt | atgtgcaccc | tcttcaaaaa ctgggtctgt | 360 |
| gactacaaca | tattgctgca | atcaggacca | ttgcaataaa | atagaacttc caactactgg | 420 |
| tttaccattg | cttgttcaga | gaacaattgc | gagaactatt | gtgttacaag aaagcattgg | 480 |
| caaaggtcga | tttggagaag | tttggagagg | aaagtggcgg | ggagaagaag ttgctgttaa | 540 |
| gatattctcc | tctagagaag | aacgttcgtg | gttccgtgag | gcagagattt atcaaactgt | 600 |
| aatgttacgt | catgaaaaca | tcctgggatt | tatagcagca | gacaataaag acaatggtac | 660 |
| ttggactcag | ctctggttgg | tgtcagatta | tcatgagcat | ggatccccttt ttgattactt | 720 |
| aaacagatac | acagttactg | tggaaggaat | gataaaactt | gctctgtcca cggcgagcgg | 780 |
| tcttgcccat | cttcacatgg | agattgttgg | tacccaagga | aagccagcca ttgctcatag | 840 |

-continued

```
agatttgaaa tcaaagaata tcttggtaaa gaagaatgga acttgctgta ttgcagactt      900
aggactggca gtaagacatg attcagccac agataccatt gatattgctc caaaccacag      960
agtgggaaca aaaaggtaca tggcccctga agttctcgat gattccataa atatgaaaca     1020
ttttgaatcc ttcaaacgtg ctgacatcta tgcaatgggc ttagtattct gggaaattgc     1080
tcgacgatgt tccattggtg gaattcatga agattaccaa ctgccttatt atgatcttgt     1140
accttctgac ccatcagttg aagaaatgag aaaagttgtt tgtgaacaga agttaaggcc     1200
aaatatccca aacagatggc agagctgtga agccttgaga gtaatggcta aaattatgag     1260
agaatgttgg tatgccaatg gagcagctag gcttacagca ttgcggatta agaaaacatt     1320
atcgcaactc agtcaacagg aaggcatcaa aatgtaattc tacagctttg cctgaactct     1380
cctttttttct tcagatctgc tcctgggttt taatttggga ggtcaattgt tctacctcac     1440
tgagagggaa cagaaggata ttgcttcctt ttgcagcagt gtaataaagt caattaaaaa     1500
cttcccagga tttctttgga cccaggaaac agccatgtgg gtcctttctg tgcactatga     1560
acgcttcttt cccaggacag aaaatgtgta gtctaccttt attttttatt aacaaaactt     1620
gttttttaaa aagatgattg ctggtcttaa ctttaggtaa ctctgctgtg ctggagatca     1680
tctttaaggg caaaggagtt ggattgctga attacaatga acatgtctt attactaaag     1740
aaagtgattt actcctggtt agtacattct cagaggattc tgaaccacta gagtttcctt     1800
gattcagact ttgaatgtac tgttctatag tttttcagga tcttaaaact aacacttata     1860
aaactcttat cttgagtcta aaaatgacct catatagtag tgaggaacat aattcatgca     1920
attgtatttt gtatactatt attgttcttt cacttattca gaacattaca tgccttcaaa     1980
atgggattgt actataccag taagtgccac ttctgtgtct ttctaatgga aatgagtaga     2040
attgctgaaa gtctctatgt taaaacctat agtgtttgaa ttcaaaaagc ttatttatct     2100
gggtaaccca aacttttttct gttttgtttt tggaagggtt tttgtggtat gtcatttggt     2160
attctattct gaaaatgcct ttctcctacc aaaatgtgct taagccacta agaaatgaa      2220
gtggcattaa ttagtaaatt attagcatgg tcatgtttga atattctcac atcaagcttt     2280
tgcattttaa ttgtgttgtc taagtatact tttaaaaaat caagtggcac tctagatgct     2340
tatagtactt taatatttgt agcatacaga ctaattttttc taaaagggaa agtctgtcta     2400
gctgcttgtg aaaagttatg tggtattctg taagccattt ttttctttat ctgttcaaag     2460
acttattttt taagacatga attacattta aaattagaat atggttaata ttaaataata     2520
ggccttttttc taggaaggcg aaggtagtta ataatttgaa tagataacag atgtgcaaga     2580
aagtcacatt tgttatgtat gtaggagtaa acgttcggtg gatcctctgt ctttgtaact     2640
gaggttagag ctagtgtggt tttgaggtct cactacactt tgaggaaggc agcttttaat     2700
tcagtgtttc cttatgtgtg cgtacattgc aactgcttac atgtaattta tgtaatgcat     2760
tcagtgcacc cttgttactt gggagaggtg gtagctaaag aacattctga gtataggttt     2820
ttctccattt acagatgtct ttggtcaaat attgaaagca aacttgtcat ggtcttctta     2880
cattaagttg aaactagctt ataataactg gttttttactt ccaatgctat gaagtctctg     2940
cagggctttt acagttttcg aagtcctttt atcactgtga tcttattctg aggggagaaa     3000
aaactatcat agctctgagg caagacttcg actttatagt gctatcagtt ccccgataca     3060
gggtcagagt aacccataca gtattttggt caggaagaga aagtggccat ttacactgaa     3120
tgagttgcat tctgataatg tcttatctct tatacgtaga ataaatttga aagactattt     3180
gatcttaaaa ccaaagtaat tttagaatga gtgacatatt acataggaat ttagtgtcaa     3240
```

-continued

```
tttcatgtgt ttaaaaacat catgggaaaa atgcttagag gttactatttt tgactacaaa    3300
gttgagttttt tttctgtagt taccataatt tcattgaagc aaatgaatga gtttgagagg    3360
tttgttttta tagttgtgtt gtattacttg tttaataata atctctaatt ctgtgatcag    3420
gtactttttt tgtgggggtt ttttttttgt tttttttttt ttgttgttgt ttttgggcca    3480
tttctaagcc taccagatct gctttatgaa atccagggga ccaatgcatt ttatcactaa    3540
aactattttt atataatttt aagaatatac caaaagttgt ctgatttaaa gttgtaatac    3600
atgatttctc actttcatgt aaggttatcc acttttgctg aagatatttt ttattgaatc    3660
aaagattgag ttacaattat acttttctta cctaagtgga taaaatgtac ttttgatgaa    3720
tcagggaatt ttttttaaagt tggagtttag ttctaaattg actttacgta ttactgcagt    3780
taattccttt tttggctagg gatggtttga taaaccacaa ttggctgata ttgaaaatga    3840
aagaaactta aaaggtggga tggatcatga ttactgtcga taactgcaga taaatttgat    3900
tagagtaata attttgtcat ttaaaaacac agttgtttat actgcccatc ctaggatgct    3960
caccttccaa gattcaacgt ggctaaaaca tcttctggta aattgtgcgt ccatattcat    4020
tttgtcagta gccaggagaa atggggatgg gggaaatacg acttagtgag catagacat    4080
ccctggtcca tcctttctgt ctccagctgt ttcttggaac ctgctctcct gcttgctggt    4140
ccctgacgca gagaccgttg cctcccccac agccgtttga ctgaaggctg ctctggagac    4200
ctagagtaaa acggctgatg gaagttgtgg gacccacttc catttccttc agtcattaga    4260
ggtggaaggg aggggtctcc aagtttggag attgagcaga tgaggcttgg gatgcccctg    4320
ctttgacttc agccatggat gaggagtggg atggcagcaa ggtggctcct gtggcagtgg    4380
agttgtgcca gaaacagtgg ccagttgtat cgcctataag acagggtaag gtctgaagag    4440
ctgagcctgt aattctgctg taataatgat agtgctcaag aagtgccttg agttggtgta    4500
cagtgccatg gccatcaaga atcccagatt tcaggtttta ttacaaaatg taagtggtca    4560
cttggcgatt ttgtagtaca tgcatgagtt accttttttc tctatgtctg agaactgtca    4620
gattaaaaca agatggcaaa gagatcgtta gagtgcacaa caaaatcact atcccattag    4680
acacatcatc aaaagcttat ttttattctt gcactggaag aatcgtaagt caactgtttc    4740
ttgaccatgg cagtgttctg gctccaaatg gtagtgattc caaataatgg ttctgttaac    4800
actttggcag aaaatgccag ctcagatatt ttgagatact aaggattatc tttgacatg    4860
tactgcagct tcttgtctct gttttggatt actggaatac ccatgggccc tctcaagagt    4920
gctggacttc taggacatta agatgattgt cagtacatta aacttttcaa tcccattatg    4980
caatcttgtt tgtaaatgta aacttctaaa aatatggtta ataacattca acctgtttat    5040
tacaacttaa aaggaacttc agtgaatttg ttttttatttt ttaacaagat ttgtgaactg    5100
aatatcatga accatgtttt gatacccctt tttcacgttg tgccaacgga atagggtgtt    5160
tgatatttct tcatatgtta aggagatgct tcaaaatgtc aattgcttta aacttaaatt    5220
acctctcaag agaccaaggt acatttacct cattgtgtat ataatgttta atatttgtca    5280
gagcattctc caggttttgca gttttatttc tataaagtat gggtattatg ttgctcagtt    5340
actcaaatgg tactgtattg tttatatttg taccccaaat aacatcgtct gtactttctg    5400
ttttctgtat tgtatttgtg caggattctt taggctttat cagtgtaatc tctgccttttt    5460
aagatatgta cagaaaatgt ccatataaat ttccattgaa gtcgaatgat actgagaagc    5520
ctgtaaagag gagaaaaaaa cataagctgt gtttcccat aagttttttt aaattgtata    5580
```

-continued

```
ttgtatttgt agtaatattc caaaagaatg taaataggaa atagaagagt gatgcttatg    5640
ttaagtccta acactacagt agaagaatgg aagcagtgca aataaattac atttttccca    5700
agtgccagtg gcatatttta aaataaagtg tatacgttgg aatgagtcat gccatatgta    5760
gttgctgtag atggcaacta gaacctttga gttacaagag tctttagaag ttttctaacc    5820
ctgcctagtg caagttacaa tattatagcg tgttcgggga gtgccctcct gtctgcaggt    5880
gtgtctctgt gcctgggggc ttttctccac atgcttaggg gtgtgggtct tccattgggg    5940
catgatggac ctgtctacag gtgatctctg ttgcctttgg gtcagcacat ttgttagtct    6000
cctgggggtg aaaacttggc ttacaagaga actggaaaaa tgatgagatg tggtccccaa    6060
acccttgatt gactctgggg aggggctttg tgaataggat tgctctcaca ttaaagatag    6120
ttacttcaat ttgaaggctg gatttaggga tttttttttt tccttataac aaagacatca    6180
ccaggatatg aagcttttgt tgaaagttgg aaaaaaagtg aaattaaaga cattcccaga    6240
caaa                                                                 6244
```

<210> SEQ ID NO 29
<211> LENGTH: 503
<212> TYPE: PRT
<213> ORGANISM: Homo sapiens
<400> SEQUENCE: 29

```
Met Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
        50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
    210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255
```

```
Glu Asn Ile Leu Gly Phe Ile Ala Ala Asp Asn Lys Asp Asn Gly Thr
                260                 265                 270

Trp Thr Gln Leu Trp Leu Val Ser Asp Tyr His Glu His Gly Ser Leu
            275                 280                 285

Phe Asp Tyr Leu Asn Arg Tyr Thr Val Thr Val Glu Gly Met Ile Lys
        290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Asn Gly Thr Cys Cys Ile Ala Asp Leu
            340                 345                 350

Gly Leu Ala Val Arg His Asp Ser Ala Thr Asp Thr Ile Asp Ile Ala
        355                 360                 365

Pro Asn His Arg Val Gly Thr Lys Arg Tyr Met Ala Pro Glu Val Leu
370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
        435                 440                 445

Lys Leu Arg Pro Asn Ile Pro Asn Arg Trp Gln Ser Cys Glu Ala Leu
450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
            500

<210> SEQ ID NO 30
<211> LENGTH: 426
<212> TYPE: PRT
<213> ORGANISM: Homo sapiens

<400> SEQUENCE: 30

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
        50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Gly Leu Pro Leu Leu Val Gln Arg Thr Ile Ala Arg Thr Ile
```

```
                115                 120                 125
        Val Leu Gln Glu Ser Ile Gly Lys Gly Arg Phe Gly Glu Val Trp Arg
            130                 135                 140
        Gly Lys Trp Arg Gly Glu Val Ala Val Lys Ile Phe Ser Ser Arg
        145                 150                 155                 160
        Glu Glu Arg Ser Trp Phe Arg Glu Ala Glu Ile Tyr Gln Thr Val Met
                            165                 170                 175
        Leu Arg His Glu Asn Ile Leu Gly Phe Ile Ala Ala Asp Asn Lys Asp
                        180                 185                 190
        Asn Gly Thr Trp Thr Gln Leu Trp Leu Val Ser Asp Tyr His Glu His
                    195                 200                 205
        Gly Ser Leu Phe Asp Tyr Leu Asn Arg Tyr Thr Val Thr Val Glu Gly
                210                 215                 220
        Met Ile Lys Leu Ala Leu Ser Thr Ala Ser Gly Leu Ala His Leu His
        225                 230                 235                 240
        Met Glu Ile Val Gly Thr Gln Gly Lys Pro Ala Ile Ala His Arg Asp
                            245                 250                 255
        Leu Lys Ser Lys Asn Ile Leu Val Lys Lys Asn Gly Thr Cys Cys Ile
                        260                 265                 270
        Ala Asp Leu Gly Leu Ala Val Arg His Asp Ser Ala Thr Asp Thr Ile
                    275                 280                 285
        Asp Ile Ala Pro Asn His Arg Val Gly Thr Lys Arg Tyr Met Ala Pro
                290                 295                 300
        Glu Val Leu Asp Asp Ser Ile Asn Met Lys His Phe Glu Ser Phe Lys
        305                 310                 315                 320
        Arg Ala Asp Ile Tyr Ala Met Gly Leu Val Phe Trp Glu Ile Ala Arg
                            325                 330                 335
        Arg Cys Ser Ile Gly Gly Ile His Glu Asp Tyr Gln Leu Pro Tyr Tyr
                        340                 345                 350
        Asp Leu Val Pro Ser Asp Pro Ser Val Glu Glu Met Arg Lys Val Val
                    355                 360                 365
        Cys Glu Gln Lys Leu Arg Pro Asn Ile Pro Asn Arg Trp Gln Ser Cys
                370                 375                 380
        Glu Ala Leu Arg Val Met Ala Lys Ile Met Arg Glu Cys Trp Tyr Ala
        385                 390                 395                 400
        Asn Gly Ala Ala Arg Leu Thr Ala Leu Arg Ile Lys Lys Thr Leu Ser
                            405                 410                 415
        Gln Leu Ser Gln Gln Glu Gly Ile Lys Met
                        420                 425

<210> SEQ ID NO 31
<211> LENGTH: 6330
<212> TYPE: DNA
<213> ORGANISM: Homo sapiens

<400> SEQUENCE: 31
aggagctggc ggagggcgtt cgtcctggga ctgcacttgc tcccgtcggg tcgcccggct    60
tcaccggacc cgcaggctcc cggggcaggg ccggggccag agctcgcgtg tcggcgggac   120
atgcgctgcg tcgcctctaa cctcgggctg tgctcttttt ccaggtggcc cgccggtttc   180
tgagccttct gccctgcggg gacacggtct gcaccctgcc cgcggccacg gaccatgacc   240
atgaccctcc acaccaaagc atctgggatg gccctactgc atcagatcca agggaacgag   300
ctggagcccc tgaaccgtcc gcagctcaag atccccctgg agcggcccct gggcgaggtg   360
```

-continued

```
tacctggaca gcagcaagcc cgccgtgtac aactacccccg agggcgccgc ctacgagttc     420
aacgccgcgg ccgccgccaa cgcgcaggtc tacggtcaga ccggcctccc ctacggcccc     480
gggtctgagg ctgcggcgtt cggctccaac ggcctggggg gtttcccccc actcaacagc     540
gtgtctccga gcccgctgat gctactgcac ccgccgccgc agctgtcgcc tttcctgcag     600
ccccacggcc agcaggtgcc ctactacctg gagaacgagc ccagcggcta cacggtgcgc     660
gaggccggcc cgccggcatt ctacaggcca aattcagata tcgacgcca gggtggcaga      720 gaaagattgg ccagtaccaa tgacaaggga agtatggcta tggaatctgc caaggagact     780
cgctactgtg cagtgtgcaa tgactatgct tcaggctacc attatggagt ctggtcctgt     840
gagggctgca aggccttctt caagagaagt attcaaggac ataacgacta tatgtgtcca     900
gccaccaacc agtgcaccat tgataaaaac aggaggaaga gctgccaggc ctgccggctc     960
cgcaaatgct acgaagtggg aatgatgaaa ggtgggatac gaaaagaccg aagaggaggg    1020
agaatgttga acacaagcg ccagagagat gatggggagg gcaggggtga agtggggtct     1080
gctggagaca tgagagctgc caaccttttgg ccaagcccgc tcatgatcaa cgctctaag    1140 aagaacagcc tggccttgtc cctgacggcc gaccagatgg tcagtgcctt gttggatgct    1200 gagccccca tactctattc cgagtatgat cctaccagac ccttcagtga agcttcgatg    1260
atgggcttac tgaccaacct ggcagacagg gagctggttc acatgatcaa ctgggcgaag   1320
agggtgccag gctttgtgga tttgacccctc catgatcagg tccaccttct agaatgtgcc   1380
tggctagaga tcctgatgat tggtctcgtc tggcgctcca tggagcaccc agggaagcta   1440
ctgtttgctc ctaacttgct cttggacagg aaccagggaa atgtgtaga gggcatggtg    1500 gagatcttcg acatgctgct ggctacatca tctcggttcc gcatgatgaa tctgcaggga   1560
gaggagtttg tgtgcctcaa atctattatt ttgcttaatt ctggagtgta cacatttctg    1620
tccagcaccc tgaagtctct ggaagagaag gaccatatcc accgagtcct ggacaagatc   1680
acagacactt tgatccacct gatggccaag gcaggcctga ccctgcagca gcagcaccag   1740
cggctggccc agctcctcct catcctctcc cacatcaggc acatgagtaa caaaggcatg   1800
gagcatctgt acagcatgaa gtgcaagaac gtggtgcccc tctatgacct gctgctggag   1860
atgctggacg cccaccgcct acatgcgccc actagccgtg gagggcatc cgtggaggag    1920 acggaccaaa gccacttggc cactgcgggc tctacttcat cgcattcctt gcaaaagtat   1980
tacatcacgg gggaggcaga gggtttccct gccacggtct gagagctccc tggctcccac   2040
acggttcaga taatccctgc tgcatttttac cctcatcatg caccacttta gccaaattct   2100
gtctcctgca tacactccgg catgcatcca acaccaatgg cttttctagat gagtggccat   2160 tcatttgctt gctcagttct tagtggcaca tcttctgtct tctgttggga acagccaaag   2220
ggattccaag gctaaatctt tgtaacagct ctctttcccc cttgctatgt tactaagcgt   2280
gaggattccc gtagctcttc acagctgaac tcagtctatg ggttggggct cagataactc   2340
tgtgcattta agctacttgt agagacccag gcctggagag tagacatttt gcctctgata   2400 agcactttttt aaatggctct aagaataagc cacagcaaag aatttaaagt ggctccttta  2460
attggtgact tggagaaagc taggtcaagg gtttattata gcaccctctt gtattcctat    2520
ggcaatgcat cctttttatga aagtggtaca ccttaaagct tttatatgac tgtagcagag  2580
tatctggtga ttgtcaattc attcccccta taggaataca aggggcacac agggaaggca   2640
gatcccctag ttggcaagac tattttaact tgatacactg cagattcaga tgtgctgaaa   2700
gctctgcctc tggctttccg gtcatggggtt ccagttaatt catgcctccc atggacctat  2760
```

```
ggagagcagc aagttgatct tagttaagtc tccctatatg agggataagt tcctgatttt   2820
tgtttttatt tttgtgttac aaaagaaagc cctccctccc tgaacttgca gtaaggtcag   2880
cttcaggacc tgttccagtg ggcactgtac ttggatcttc ccggcgtgtg tgtgccttac   2940
acaggggtga actgttcact gtggtgatgc atgatgaggg taaatggtag ttgaaaggag   3000
caggggccct ggtgttgcat ttagccctgg ggcatggagc tgaacagtac ttgtgcagga   3060
ttgttgtggc tactagagaa caagagggaa agtagggcag aaactggata cagttctgag   3120
gcacagccag acttgctcag ggtggccctg ccacaggctg cagctaccta ggaacattcc   3180
ttgcagaccc cgcattgccc tttggggtg ccctgggatc cctggggtag tccagctctt    3240
cttcatttcc cagcgtggcc ctggttggaa gaagcagctg tcacagctgc tgtagacagc   3300
tgtgttccta caattggccc agcacccttgg ggcacgggag aagggtgggg accgttgctg  3360
tcactactca ggctgactgg ggcctggtca gattacgtat gcccttggtg gtttagagat   3420
aatccaaaat cagggtttgg tttggggaag aaaatcctcc cccttcctcc cccgccccgt   3480
tccctaccgc ctccactcct gccagctcat ttccttcaat ttcctttgac ctataggcta   3540
aaaaagaaag gctcattcca gccacagggc agccttccct gggcctttgc ttctctagca   3600
caattatggg ttacttcctt tttcttaaca aaaagaatg tttgatttcc tctgggtgac    3660
cttattgtct gtaattgaaa ccctattgag aggtgatgtc tgtgttagcc aatgacccag   3720
gtgagctgct cgggcttctc ttggtatgtc ttgtttggaa aagtggattt cattcatttc   3780
tgattgtcca gttaagtgat caccaaagga ctgagaatct gggagggcaa aaaaaaaaa    3840
aaagttttta tgtgcactta aatttgggga caattttatg tatctgtgtt aaggatatgt   3900
ttaagaacat aattctttg ttgctgtttg tttaagaagc accttagttt gtttaagaag    3960
caccttatat agtataatat atattttttt gaaattacat tgcttgttta tcagacaatt   4020
gaatgtagta attctgttct ggatttaatt tgactgggtt aacatgcaaa accaaggaa    4080
aaatatttag ttttttttt tttttttgta tacttttcaa gctaccttgt catgtataca    4140
gtcatttatg cctaaagcct ggtgattatt catttaaatg aagatcacat ttcatatcaa   4200
cttttgtatc cacagtagac aaaatagcac taatccagat gcctattgtt ggatactgaa   4260
tgacagacaa tcttatgtag caaagattat gcctgaaaag gaaaattatt cagggcagct   4320
aattttgctt ttaccaaaat atcagtagta atatttttgg acagtagcta atgggtcagt   4380
gggttctttt taatgtttat acttagattt tcttttaaaa aaattaaaat aaaacaaaaa   4440
aaaatttcta ggactagacg atgtaatacc agctaaagcc aaacaattat acagtggaag   4500
gttttacatt attcatccaa tgtgtttcta ttcatgttaa gatactacta catttgaagt   4560
gggcagagaa catcagatga ttgaaatgtt cgcccagggg tctccagcaa ctttgaaat    4620
ctctttgtat ttttacttga agtgccacta atggacagca gatatttct ggctgatgtt    4680
ggtattgggt gtaggaacat gatttaaaaa aaaactcttg cctctgcttt cccccactct   4740
gaggcaagtt aaaatgtaaa agatgtgatt tatctggggg gctcaggtat ggtggggaag   4800
tggattcagg aatctgggga atggcaaata tattaagaag agtattgaaa gtatttggag   4860
gaaaatggtt aattctgggt gtgcaccagg gttcagtaga gtccacttct gccctggaga   4920
ccacaaatca actagctcca tttacagcca tttctaaaat ggcagcttca gttctagaga   4980
agaaagaaca acatcagcag taaagtccat ggaatagcta gtggtctgtg tttctttcg    5040
ccattgccta gcttgccgta atgattctat aatgccatca tgcagcaatt atgagaggct   5100
```

-continued

```
aggtcatcca aagagaagac cctatcaatg taggttgcaa aatctaaccc ctaaggaagt      5160
gcagtctttg atttgatttc cctagtaacc ttgcagatat gtttaaccaa gccatagccc      5220
atgccttttg agggctgaac aaataaggga cttactgata atttactttt gatcacatta      5280
aggtgttctc accttgaaat cttatacact gaaatggcca ttgatttagg ccactggctt      5340
agagtactcc ttcccctgca tgacactgat tacaaatact ttcctattca tactttccaa      5400
ttatgagatg gactgtgggt actgggagtg atcactaaca ccatagtaat gtctaatatt      5460
cacaggcaga tctgcttggg gaagctagtt atgtgaaagg caaatagagt catacagtag      5520
ctcaaaaggc aaccataatt ctctttggtg caggtcttgg gagcgtgatc tagattacac      5580
tgcaccattc ccaagttaat cccctgaaaa cttactctca actggagcaa atgaactttg      5640
gtcccaaata tccatctttt cagtagcgtt aattatgctc tgtttccaac tgcatttcct      5700
ttccaattga attaaagtgt ggcctcgttt ttagtcattt aaaattgttt tctaagtaat      5760
tgctgcctct attatggcac ttcaattttg cactgtcttt tgagattcaa gaaaaatttc      5820
tattcttttt tttgcatcca attgtgcctg aacttttaaa atatgtaaat gctgccatgt      5880
tccaaaccca tcgtcagtgt gtgtgtttag agctgtgcac cctagaaaca acatattgtc      5940
ccatgagcag gtgcctgaga cacagacccc tttgcattca cagagaggtc attggttata      6000
gagacttgaa ttaataagtg acattatgcc agtttctgtt ctctcacagg tgataaacaa      6060 tgcttttgt gcactacata ctcttcagtg tagagctctt gtttttatggg aaaaggctca      6120
```
```
aatgccaaat tgtgtttgat ggattaatat gccctttgc cgatgcatac tattactgat       6180
gtgactcggt tttgtcgcag ctttgctttg tttaatgaaa cacacttgta aacctctttt      6240
gcactttgaa aaagaatcca gcgggatgct cgagcacctg taaacaattt tctcaaccta      6300
tttgatgttc aaataaagaa ttaaactaaa                                       6330
```

<210> SEQ ID NO 32
<211> LENGTH: 6357
<212> TYPE: DNA
<213> ORGANISM: Homo sapiens

<400> SEQUENCE: 32

```
gacaaacaga gatatatcgg agtctggcac ggggcacata aggcagcaca ttagagaaag        60
ccggcccctg gatccgtctt tcgcgtttat tttaagccca gtcttccctg ggccaccttt       120
agcagatcct cgtgcgcccc cgcccctggg ccgtgaaact cagcctctat ccagcagcga       180
cgacaagtaa agtggcccgc cggtttctga gccttctgcc ctgcggggac acggtctgca       240
ccctgcccgc ggccacggac catgaccatg accctccaca ccaaagcatc tgggatggcc       300
ctactgcatc agatccaagg gaacgagctg agcccctga accgtccgca gctcaagatc       360
cccctggagc ggcccctggg cgaggtgtac ctggacagca gcaagcccgc cgtgtacaac       420
taccccgagg gcgccgccta cgagttcaac gccgcggccg ccgccaacgc gcaggtctac       480
ggtcagaccg gcctcccta cggccccggg tctgaggctg cggcgttcgg ctccaacggc       540 ctgggggtt tcccccact caacagcgtg tctccgagcc cgctgatgct actgcacccg       600
ccgccgcagc tgtcgccttt cctgcagccc acggccagc aggtgcccta ctacctggag       660
aacgagccca gcggctacac ggtgcgcgag gccggcccgc cggcattcta caggccaaat       720
tcagataatc gacgccaggg tggcagaaa agattggcca gtaccaatga caagggaagt       780
atggctatgg aatctgccaa ggagactcgc tactgtgcag tgtgcaatga ctatgcttca       840
ggctaccatt atggagtctg gtcctgtgag ggctgcaagg ccttcttcaa gagaagtatt       900
```

```
caaggacata acgactatat gtgtccagcc accaaccagt gcaccattga taaaaacagg     960
aggaagagct gccaggcctg ccggctccgc aaatgctacg aagtgggaat gatgaaaggt    1020
gggatacgaa aagaccgaag aggagggaga atgttgaaac acaagcgcca gagagatgat    1080
ggggagggca ggggtgaagt ggggtctgct ggagacatga gagctgccaa cctttggcca    1140
agcccgctca tgatcaaacg ctctaagaag aacagcctgg ccttgtccct gacggccgac    1200
cagatggtca gtgccttgtt ggatgctgag cccccatac tctattccga gtatgatcct     1260
accagaccct tcagtgaagc ttcgatgatg ggcttactga ccaacctggc agacagggag    1320
ctggttcaca tgatcaactg ggcgaagagg gtgccaggct tgtggatttt gaccctccat    1380
gatcaggtcc accttctaga atgtgcctgg ctagagatcc tgatgattgg tctcgtctgg    1440
cgctccatgg agcacccagg gaagctactg tttgctccta acttgctctt ggacaggaac    1500
cagggaaaat gtgtagaggg catggtggag atcttcgaca tgctgctggc tacatcatct    1560
cggttccgca tgatgaatct gcagggagag gagtttgtgt gcctcaaatc tattattttg    1620
cttaattctg gagtgtacac atttctgtcc agcaccctga agtctctgga agagaaggac    1680
catatccacc gagtcctgga caagatcaca gacactttga tccacctgat ggccaaggca    1740
ggcctgaccc tgcagcagca gcaccagcgg ctggcccagc tcctcctcat cctctcccac    1800
atcaggcaca tgagtaacaa aggcatggag catctgtaca gcatgaagtg caagaacgtg    1860
gtgcccctct atgacctgct gctggagatg ctggacgccc accgcctaca tgcgcccact    1920
agccgtggag gggcatccgt ggaggagacg gaccaaagcc acttggccac tgcgggctct    1980
acttcatcgc attccttgca aaagtattac atcacggggg aggcagaggg tttccctgcc    2040
acggtctgag agctccctgg ctcccacacg gttcagataa tccctgctgc attttaccct    2100
catcatgcac cactttagcc aaattctgtc tcctgcatac actccggcat gcatccaaca    2160
ccaatggctt tctagatgag tggccattca tttgcttgct cagttcttag tggcacatct    2220
tctgtcttct gttgggaaca gccaaaggga ttccaaggct aaatctttgt aacagctctc    2280
tttcccccctt gctatgttac taagcgtgag gattcccgta gctcttcaca gctgaactca    2340
gtctatgggt tggggctcag ataactctgt gcatttaagc tacttgtaga gacccaggcc    2400
tggagagtag acattttgcc tctgataagc acttttttaaa tggctctaag aataagccac    2460
agcaaagaat ttaaagtggc tccttttaatt ggtgacttgg agaaagctag gtcaagggtt    2520
tattatagca ccctcttgta ttcctatggc aatgcatcct tttatgaaag tggtacacct    2580
taaagctttt atatgactgt agcagagtat ctggtgattg tcaattcatt cccctatag     2640
gaatacaagg ggcacacagg gaaggcagat cccctagttg gcaagactat tttaacttga    2700
tacactgcag attcagatgt gctgaaagct ctgcctctgg cttccggtc atgggttcca    2760
gttaattcat gcctcccatg gacctatgga gagcagcaag ttgatcttag ttaagtctcc    2820
ctatatgagg ataagttcc tgattttttgt ttttatttt gtgttacaaa agaaagccct    2880
ccctccctga acttgcagta aggtcagctt caggacctgt tccagtgggc actgtacttg    2940
gatcttcccg gcgtgtgtgt gccttacaca ggggtgaact gttcactgtg gtgatgcatg    3000
atgagggtaa atggtagttg aaaggagcag ggggcctggt gttgcattta gccctggggc    3060
atggagctga acagtacttg tgcaggattg ttgtggctac tagagaacaa gagggaaagt    3120
agggcagaaa ctggatacag ttctgaggca cagccagact tgctcagggt ggccctgcca    3180
caggctgcag ctacctagga acattccttg cagacccgc attgcccttt gggggtgccc      3240
```

```
tgggatccct ggggtagtcc agctcttctt catttcccag cgtggccctg gttggaagaa    3300
gcagctgtca cagctgctgt agacagctgt gttcctacaa ttggcccagc accctggggc    3360
acgggagaag ggtggggacc gttgctgtca ctactcaggc tgactggggc ctggtcagat    3420
tacgtatgcc cttggtggtt tagagataat ccaaaatcag ggtttggttt ggggaagaaa    3480 atcctcccccc ttcctcccccc gccccgttcc ctaccgcctc cactcctgcc agctcatttc    3540
cttcaatttc cttttgaccta taggctaaaa aagaaaggct cattccagcc acagggcagc    3600
cttccctggg cctttgcttc tctagcacaa ttatgggtta cttccttttt cttaacaaaa    3660
aagaatgttt gatttcctct gggtgacctt attgtctgta attgaaaccc tattgagagg    3720
tgatgtctgt gttagccaat gacccaggtg agctgctcgg gcttctcttg gtatgtcttg    3780
tttggaaaag tggatttcat tcatttctga ttgtccagtt aagtgatcac caaaggactg    3840
agaatctggg agggcaaaaa aaaaaaaaaa gttttttatgt gcacttaaat ttggggacaa    3900
ttttatgtat ctgtgttaag gatatgttta agaacataat tcttttgttg ctgtttgttt    3960
aagaagcacc ttagtttgtt taagaagcac cttatatagt ataatatata ttttttttgaa    4020 attacattgc ttgtttatca gacaattgaa tgtagtaatt ctgttctgga tttaatttga    4080
ctgggttaac atgcaaaaac caaggaaaaa tatttagtttt tttttttttt ttttgtatac    4140
ttttcaagct accttgtcat gtatacagtc atttatgcct aaagcctggt gattattcat    4200
ttaaatgaag atcacatttc atatcaactt ttgtatccac agtagacaaa atagcactaa    4260
tccagatgcc tattgttgga tactgaatga cagacaatct tatgtagcaa agattatgcc    4320
tgaaaaggaa aattattcag ggcagctaat tttgctttta ccaaaatatc agtagtaata    4380 ttttttggaca gtagctaatg ggtcagtggg ttcttttttaa tgtttatact tagattttct    4440
tttaaaaaaa ttaaaataaa acaaaaaaaa atttctagga ctagacgatg taataccagc    4500
taaagccaaa caattataca gtggaaggtt ttacattatt catccaatgt gtttctattc    4560
atgttaagat actactacat ttgaagtggg cagagaacat cagatgattg aaatgttcgc    4620
ccaggggtct ccagcaactt tggaaatctc tttgtatttt tacttgaagt gccactaatg    4680
gacagcagat attttctggc tgatgttggt attgggtgta ggaacatgat ttaaaaaaaa    4740
actcttgcct ctgctttccc ccactctgag gcaagttaaa atgtaaaaga tgtgatttat    4800 ctgggggggct caggtatggt ggggaagtgg attcaggaat ctggggaatg gcaaatatat    4860
taagaagagt attgaaagta tttggaggaa aatggttaat tctgggtgtg caccagggtt    4920
cagtagagtc cacttctgcc ctggagacca caaatcaact agctccattt acagccattt    4980
ctaaaatggc agcttcagtt ctagagaaga aagaacaaca tcagcagtaa agtccatgga    5040
atagctagtg gtctgtgttt cttttcgcca ttgcctagct tgccgtaatg attctataat    5100
gccatcatgc agcaattatg agaggctagg tcatccaaag agaagaccct atcaatgtag    5160
gttgcaaaat ctaaccccta aggaagtgca gtctttgatt tgatttccct agtaaccttg    5220
cagatatgtt taaccaagcc atagcccatg ccttttgagg gctgaacaaa taagggactt    5280
actgataatt tacttttgat cacattaagg tgttctcacc ttgaaatctt atacactgaa    5340
atggccattg atttaggcca ctggcttaga gtactccttc ccctgcatga cactgattac    5400
aaatactttc ctattcatac tttccaatta tgagatggac tgtgggtact gggagtgatc    5460
actaacacca tagtaatgtc taatattcac aggcagatct gcttgggaa gctagttatg    5520 tgaaaggcaa atagagtcat acagtagctc aaaaggcaac cataattctc tttggtgcag    5580
gtcttgggag cgtgatctag attacactgc accattccca agttaatccc ctgaaaactt    5640
```

| | |
|---|---:|
| actctcaact ggagcaaatg aactttggtc ccaaatatcc atcttttcag tagcgttaat | 5700 |
| tatgctctgt ttccaactgc atttcctttc caattgaatt aaagtgtggc ctcgttttta | 5760 |
| gtcatttaaa attgttttct aagtaattgc tgcctctatt atggcacttc aattttgcac | 5820 |
| tgtcttttga gattcaagaa aaatttctat tctttttttt gcatccaatt gtgcctgaac | 5880 |
| ttttaaaata tgtaaatgct gccatgttcc aaacccatcg tcagtgtgtg tgtttagagc | 5940 |
| tgtgcaccct agaaacaaca tattgtccca tgagcaggtg cctgagacac agacccctttt | 6000 |
| gcattcacag agaggtcatt ggttatagag acttgaatta ataagtgaca ttatgccagt | 6060 |
| ttctgttctc tcacaggtga taaacaatgc ttttttgtgca ctacatactc ttcagtgtag | 6120 |
| agctcttgtt ttatgggaaa aggctcaaat gccaaattgt gtttgatgga ttaatatgcc | 6180 |
| cttttgccga tgcatactat tactgatgtg actcggtttt gtcgcagctt tgctttgttt | 6240 |
| aatgaaacac acttgtaaac ctcttttgca ctttgaaaaa gaatccagcg ggatgctcga | 6300 |
| gcacctgtaa acaatttttct caacctattt gatgttcaaa taagaattaa aactaaa | 6357 |

<210> SEQ ID NO 33
<211> LENGTH: 6314
<212> TYPE: DNA
<213> ORGANISM: Homo sapiens

<400> SEQUENCE: 33

| | |
|---|---:|
| aaacacatcc acacactctc tctgcctagt tcacacactg agccactcgc acatgcgagc | 60 |
| acattccttc cttccttctc actctctcgg cccttgactt ctacaagccc atggaacatt | 120 |
| tctggaaaga cgttcttgat ccagcagggt ggcccgccgg tttctgagcc ttctgccctg | 180 |
| cggggacacg gtctgcaccc tgcccgcggc cacggaccat gaccatgacc ctccacacca | 240 |
| aagcatctgg gatggcccta ctgcatcaga tccaagggaa cgagctggag cccctgaacc | 300 |
| gtccgcagct caagatcccc ctggagcggc cctgggcga ggtgtacctg acagcagca | 360 |
| agcccgccgt gtacaactac cccgagggcg ccgcctacga gttcaacgcc gcggccgccg | 420 |
| ccaacgcgca ggtctacggt cagaccggcc tcccctacgg ccccgggtct gaggctgcgg | 480 |
| cgttcggctc caacggcctg gggggtttcc cccactcaa cagcgtgtct ccgagcccgc | 540 |
| tgatgctact gcacccgccg ccgcagctgt cgccttttcct gcagcccac ggccagcagg | 600 |
| tgccctacta cctggagaac gagcccagcg gctacacggt gcgcgaggcc ggcccgccgg | 660 |
| cattctacag gccaaattca gataatcgac gccagggtgg cagagaaaga ttggccagta | 720 |
| ccaatgacaa gggaagtatg gctatggaat ctgccaagga gactcgctac tgtgcagtgt | 780 |
| gcaatgacta tgcttcaggc taccattatg gagtctggtc ctgtgagggc tgcaaggcct | 840 |
| tcttcaagag aagtattcaa ggacataacg actatatgtg tccagccacc aaccagtgca | 900 |
| ccattgataa aaacaggagg aagagctgcc aggcctgccg gctccgcaaa tgctacgaag | 960 |
| tgggaatgat gaaaggtggg atacgaaaag accgaagagg agggagaatg ttgaaacaca | 1020 |
| agcgccagag agatgatggg gagggcaggg gtgaagtggg gtctgctgga gacatgagag | 1080 |
| ctgccaacct ttggccaagc ccgctcatga tcaaacgctc taagaagaac agcctggcct | 1140 |
| tgtccctgac ggccgaccag atggtcagtg ccttgttgga tgctgagccc ccatactctt | 1200 |
| attccgagta tgatcctacc agacccttca gtgaagcttc gatgatgggc ttactgacca | 1260 |
| acctggcaga cagggagctg gttcacatga tcaactgggc gaagagggtg ccaggctttg | 1320 |
| tggatttgac cctccatgat caggtccacc ttctagaatg tgcctggcta gagatcctga | 1380 |

```
tgattggtct cgtctggcgc tccatggagc acccagggaa gctactgttt gctcctaact   1440
tgctcttgga caggaaccag ggaaaatgtg tagagggcat ggtggagatc ttcgacatgc   1500
tgctggctac atcatctcgg ttccgcatga tgaatctgca gggagaggag tttgtgtgcc   1560
tcaaatctat tattttgctt aattctggag tgtacacatt tctgtccagc accctgaagt   1620
ctctggaaga gaaggaccat atccaccgag tcctggacaa gatcacagac actttgatcc   1680
acctgatggc caaggcaggc ctgaccctgc agcagcagca ccagcggctg gcccagctcc   1740
tcctcatcct ctcccacatc aggcacatga gtaacaaagg catggagcat ctgtacagca   1800
tgaagtgcaa gaacgtggtg cccctctatg acctgctgct ggagatgctg gacgcccacc   1860
gcctacatgc gcccactagc cgtggagggg catccgtgga ggagacggac caaagccact   1920
tggccactgc gggctctact tcatcgcatt ccttgcaaaa gtattacatc acggggagg    1980 cagagggttt ccctgccacg gtctgagagc tccctggctc ccacacggtt cagataatcc   2040
ctgctgcatt ttaccctcat catgcaccac tttagccaaa ttctgtctcc tgcatacact   2100
ccggcatgca tccaacacca atggctttct agatgagtgg ccattcattt gcttgctcag   2160
ttcttagtgg cacatcttct gtcttctgtt gggaacagcc aaagggattc caaggctaaa   2220
tctttgtaac agctctcttt ccccccttgct atgttactaa gcgtgaggat tcccgtagct   2280
cttcacagct gaactcagtc tatgggttgg ggctcagata actctgtgca tttaagctac   2340
ttgtagagac ccaggcctgg agagtagaca ttttgcctct gataagcact ttttaaatgg   2400
ctctaagaat aagccacagc aaagaattta agtggctcc tttaattggt gacttggaga    2460
aagctaggtc aagggtttat tatagcaccc tcttgtattc ctatggcaat gcatcctttt   2520
atgaaagtgg tacaccttaa agcttttata tgactgtagc agagtatctg gtgattgtca   2580
attcattccc cctataggaa tacaagggc acacagggaa ggcagatccc ctagttggca    2640
agactatttt aacttgatac actgcagatt cagatgtgct gaaagctctg cctctggctt   2700
tccggtcatg ggttccagtt aattcatgcc tcccatggac ctatggagag cagcaagttg   2760
atcttagtta agtctcccta tatgagggat aagttcctga ttttgttttt tattttgtg    2820 ttacaaaaga aagcccctccc tccctgaact tgcagtaagg tcagcttcag gacctgttcc   2880
agtgggcact gtacttggat cttcccggcg tgtgtgtgcc ttacacaggg gtgaactgtt   2940
cactgtggtg atgcatgatg agggtaaatg gtagttgaaa ggagcagggg ccctggtgtt   3000
gcatttagcc ctggggcatg gagctgaaca gtacttgtgc aggattgttg tggctactag   3060
agaacaagag ggaaagtagg gcagaaactg gatacagttc tgaggcacag ccagacttgc   3120
tcagggtggc cctgccacag gctgcagcta cctaggaaca ttccttgcag accccgcatt   3180
gccctttggg ggtgccctgg gatccctggg gtagtccagc tcttcttcat ttcccagcgt   3240
ggccctggtt ggaagaagca gctgtcacag ctgctgtaga cagctgtgtt cctacaattg   3300
gcccagcacc ctggggcacg ggagaagggt ggggaccgtt gctgtcacta ctcaggctga   3360
ctggggcctg gtcagattac gtatgccctt ggtggtttag agataatcca aaatcagggt   3420
ttggtttggg gaagaaaatc ctccccctttc ctccccccgcc ccgttcccta ccgcctccac  3480
tcctgccagc tcatttcctt caatttcctt tgacctatag gctaaaaaag aaaggctcat   3540
tccagccaca gggcagcctt ccctgggcct ttgcttctct agcacaatta tgggttactt   3600 ccttttctt aacaaaaaag aatgtttgat ttcctctggg tgaccttatt gtctgtaatt    3660
gaaaccctat tgagaggtga tgtctgtgtt agccaatgac ccaggtgagc tgctcggct    3720 tctcttggta tgtcttgttt ggaaaagtgg atttcattca tttctgattg tccagttaag   3780
```

-continued

```
tgatcaccaa aggactgaga atctgggagg gcaaaaaaaa aaaaaaagtt tttatgtgca    3840
cttaaatttg gggacaattt tatgtatctg tgttaaggat atgtttaaga acataattct    3900
tttgttgctg tttgtttaag aagcaccttta gtttgtttaa gaagcacctt atatagtata    3960
atatatattt ttttgaaatt acattgcttg tttatcagac aattgaatgt agtaattctg    4020
ttctggattt aatttgactg ggttaacatg caaaaaccaa ggaaaaatat ttagttttt    4080
tttttttttt tgtatacttt tcaagctacc ttgtcatgta tacagtcatt tatgcctaaa    4140
gcctggtgat tattcattta aatgaagatc acatttcata tcaacttttg tatccacagt    4200
agacaaaata gcactaatcc agatgcctat tgttggatac tgaatgacag acaatcttat    4260
gtagcaaaga ttatgcctga aaggaaaat tattcagggc agctaatttt gcttttacca    4320
aaatatcagt agtaatattt ttggacagta gctaatgggt cagtgggttc tttttaatgt    4380
ttatacttag attttctttt aaaaaaatta aaataaaaca aaaaaaatt tctaggacta    4440
gacgatgtaa taccagctaa agccaaacaa ttatacagtg gaaggtttta cattattcat    4500
ccaatgtgtt tctattcatg ttaagatact actacatttg aagtgggcag agaacatcag    4560
atgattgaaa tgttcgccca ggggtctcca gcaactttgg aaatctcttt gtattttac    4620
ttgaagtgcc actaatggac agcagatatt ttctggctga tgttggtatt gggtgtagga    4680
acatgattta aaaaaaaact cttgcctctg ctttcccca ctctgaggca agttaaaatg    4740
taaagatgt gatttatctg gggggctcag gtatggtggg gaagtggatt caggaatctg    4800
gggaatggca aatatattaa gaagagtatt gaaagtattt ggaggaaaat ggttaattct    4860
gggtgtgcac cagggttcag tagagtccac ttctgccctg gagaccacaa atcaactagc    4920
tccatttaca gccatttcta aaatggcagc ttcagttcta gagaagaaag aacaacatca    4980
gcagtaaagt ccatggaata gctagtggtc tgtgtttctt ttcgccattg cctagcttgc    5040
cgtaatgatt ctataatgcc atcatgcagc aattatgaga ggctaggtca tccaaagaga    5100
agaccctatc aatgtaggtt gcaaaatcta accctaagg aagtgcagtc tttgatttga    5160
tttccctagt aaccttgcag atatgtttaa ccaagccata gcccatgcct tttgagggct    5220
gaacaaataa gggacttact gataaatttac ttttgatcac attaaggtgt tctcaccttg    5280
aaatcttata cactgaaatg gccattgatt taggccactg gcttagagta ctccttcccc    5340
tgcatgacac tgattacaaa tactttccta ttcatacttt ccaattatga gatggactgt    5400
gggtactggg agtgatcact aacaccatag taatgtctaa tattcacagg cagatctgct    5460
tggggaagct agttatgtga aaggcaaata gagtcataca gtagctcaaa aggcaaccat    5520
aattctcttt ggtgcaggtc ttgggagcgt gatctagatt acactgcacc attcccaagt    5580
taatcccctg aaaacttact ctcaactgga gcaaatgaac tttggtccca aatatccatc    5640
ttttcagtag cgttaattat gctctgtttc caactgcatt tccttccaa ttgaattaaa    5700
gtgtggcctc gttttagtc atttaaaatt gttttctaag taattgctgc ctctattatg    5760
gcacttcaat tttgcactgt cttttgagat tcaagaaaaa tttctattct ttttttttgca   5820
tccaattgtg cctgaacttt taaaatatgt aaaatgctgcc atgttccaaa cccatcgtca   5880
gtgtgtgtgt ttagagctgt gcaccctaga acaacatat tgtcccatga gcaggtgcct    5940
gagacacaga ccccctttgca ttcacagaga ggtcattggt tatagagact tgaattaata   6000
agtgacatta tgccagtttc tgttctctca caggtgataa acaatgcttt ttgtgcacta   6060
catactcttc agtgtagagc tcttgttta tgggaaaagg ctcaaatgcc aaattgtgtt    6120
```

```
tgatggatta atatgcccctt tgccgatgc atactattac tgatgtgact cggttttgtc    6180
gcagctttgc tttgtttaat gaaacacact tgtaaacctc ttttgcactt tgaaaaagaa    6240
tccagcggga tgctcgagca cctgtaaaca attttctcaa cctatttgat gttcaaataa    6300
agaattaaac taaa                                                      6314

<210> SEQ ID NO 34
<211> LENGTH: 6466
<212> TYPE: DNA
<213> ORGANISM: Homo sapiens

<400> SEQUENCE: 34
atggtcataa cagcctcctg tctaccgact cagaacggat tttaccaaaa ctgaaaatgc      60
aggctccatg ctcagaagct ctttaacagg ctcgaaaggt ccatgctcct ttctcctgcc     120
cattctatag cataagaaga cagtctctga gtgataatct tctcttcaag aagaagaaaa     180
ctaggaagga gtaagcacaa agatctcttc acattctccg ggactgcggt accaaatatc     240
agcacagcac ttcttgaaaa aggatgtaga ttttaatctg aactttgaac catcactgag     300
gtggcccgcc ggtttctgag ccttctgccc tgcgggaca cggtctgcac cctgcccgcg      360
gccacggacc atgaccatga ccctccacac caaagcatct gggatggccc tactgcatca     420
gatccaaggg aacgagctgg agccctgaa ccgtccgcag ctcaagatcc cctggagcg       480 gcccctgggc gaggtgtacc tggacagcag caagcccgcc gtgtacaact ccccgaggg      540 cgccgcctac gagttcaacg ccgcggccgc cgccaacgcg caggtctacg gtcagaccgg    600
cctcccctac ggccccgggt ctgaggctgc ggcgttcggc tccaacggcc tgggggggttt    660 ccccccactc aacagcgtgt ctccgagccc gctgatgcta ctgcacccgc cgccgcagct     720
gtcgcctttc ctgcagcccc acggccagca ggtgccctac tacctggaga cgagcccag     780 cggctacacg gtgcgcgagg ccggcccgcc ggcattctac aggccaaatt cagataatcg    840 acgcagggt ggcagagaaa gattggccag taccaatgac aagggaagta tggctatgga    900
atctgccaag gagactcgct actgtgcagt gtgcaatgac tatgcttcag ctaccatta     960 tggagtctgg tcctgtgagg gctgcaaggc cttcttcaag agaagtattc aaggacataa    1020
cgactatatg tgtccagcca ccaaccagtg caccattgat aaaaacagga ggaagagctg    1080
ccaggcctgc cggctccgca aatgctacga agtgggaatg atgaaaggtg ggatacgaaa    1140
agaccgaaga ggagggagaa tgttgaaaca caagcgccag agagatgatg ggagggcag    1200 gggtgaagtg gggtctgctg gagacatgag agctgccaac cttggccaa gcccgctcat    1260 gatcaaacgc tctaagaaga cagcctggc cttgtccctg acggccgacc agatggtcag    1320
tgccttgttg gatgctgagc ccccatact ctattccgag tatgatccta ccagaccctt    1380
cagtgaagct tcgatgatgg gcttactgac caacctggca gacagggagc tggttcacat    1440
gatcaactgg gcgaagaggg tgccaggctt tgtggatttg accctccatg atcaggtcca    1500
ccttctagaa tgtgcctggc tagagatcct gatgattggt ctcgtctggc gctccatgga    1560
gcacccaggg aagctactgt ttgctcctaa cttgctcttg gacaggaacc agggaaaatg    1620
tgtagagggc atggtggaga tcttcgacat gctgctggct acatcatctc ggttccgcat    1680
gatgaatctg caggggagg agtttgtgtg cctcaaatct attattttgc ttaattctgg    1740
agtgtacaca tttctgtcca gcacctgaa gtctctggaa gagaaggacc atatccaccg    1800
agtcctggac aagatcacag acactttgat ccacctgatg gccaaggcag cctgaccct    1860 gcagcagcag caccagcggc tggcccagct cctcctcatc ctctcccaca tcaggcacat    1920
```

```
gagtaacaaa ggcatggagc atctgtacag catgaagtgc aagaacgtgg tgcccctcta      1980
tgacctgctg ctggagatgc tggacgccca ccgcctacat gcgcccacta gccgtggagg      2040
ggcatccgtg gaggagacgg accaaagcca cttggccact gcgggctcta cttcatcgca      2100
ttccttgcaa aagtattaca tcacggggga ggcagagggt ttccctgcca cggtctgaga      2160
gctccctggc tcccacacgg ttcagataat ccctgctgca ttttaccctc atcatgcacc      2220
actttagcca aattctgtct cctgcataca ctccggcatg catccaacac caatggcttt      2280
ctagatgagt ggccattcat ttgcttgctc agttcttagt ggcacatctt ctgtcttctg      2340
ttgggaacag ccaaagggat tccaaggcta atctttgta acagctctct ttccccttg       2400 ctatgttact aagcgtgagg attcccgtag ctcttcacag ctgaactcag tctatgggtt      2460
ggggctcaga taactctgtg catttaagct acttgtagag acccaggcct ggagagtaga     2520
cattttgcct ctgataagca cttttttaaat ggctctaaga ataagccaca gcaaagaatt     2580
taaagtggct cctttaattg gtgacttgga gaaagctagg tcaagggttt attatagcac      2640
cctcttgtat tcctatggca atgcatcctt ttatgaaagt ggtacacctt aaagctttta     2700
tatgactgta gcagagtatc tggtgattgt caattcattc cccctatagg aatacaaggg    2760
gcacacaggg aaggcagatc ccctagttgg caagactatt ttaacttgat acactgcaga    2820
ttcagatgtg ctgaaagctc tgcctctggc tttccggtca tgggttccag ttaattcatg    2880
cctcccatgg acctatggag agcagcaagt tgatcttagt taagtctccc tatatgaggg     2940
ataagttcct gattttttgtt tttatttttg tgttacaaaa gaaagccctc cctccctgaa    3000
cttgcagtaa ggtcagcttc aggacctgtt ccagtgggca ctgtacttgg atcttcccgg    3060
cgtgtgtgtg ccttacacag gggtgaactg ttcactgtgg tgatgcatga tgagggtaaa    3120
tggtagttga aaggagcagg ggccctggtg ttgcatttag ccctggggca tggagctgaa    3180
cagtacttgt gcaggattgt tgtggctact agagaacaag agggaaagta gggcagaaac    3240
tggatacagt tctgaggcac agccagactt gctcagggtg gccctgccac aggctgcagc    3300
tacctaggaa cattccttgc agaccccgca ttgcccttg ggggtgccct gggatccctg      3360
gggtagtcca gctcttcttc atttcccagc gtggccctgg ttggaagaag cagctgtcac    3420
agctgctgta gacagctgtg ttcctacaat tgcccagca ccctggggca cgggagaagg     3480
gtggggaccg ttgctgtcac tactcaggct gactggggcc tggtcagatt acgtatgccc    3540
ttggtggttt agagataatc caaaatcagg gtttggtttg gggaagaaaa tcctcccct    3600 tcctccccg ccccgttccc taccgcctcc actcctgcca gctcatttcc ttcaatttcc      3660
tttgacctat aggctaaaaa agaaaggctc attccagcca cagggcagcc ttccctgggc    3720
ctttgcttct ctagcacaat tatgggttac ttccttttc ttaacaaaaa agaatgtttg     3780
atttcctctg ggtgacctta ttgtctgtaa ttgaaaccct attgagaggt gatgtctgtg     3840
ttagccaatg acccaggtga gctgctcggg cttctcttgg tatgtcttgt ttggaaaagt   3900
ggatttcatt catttctgat tgtccagtta agtgatcacc aaaggactga gaatctggga   3960
gggcaaaaaa aaaaaaaaag ttttatgtg cacttaaatt tggggacaat tttatgtatc     4020
tgtgttaagg atatgtttaa gaacataatt cttttgttgc tgtttgttta agaagcacct     4080
tagtttgttt aagaagcacc ttatatagta taatatatat ttttttgaaa ttacattgct    4140
tgtttatcag acaattgaat gtagtaattc tgttctggat ttaatttgac tgggttaaca    4200
tgcaaaaacc aaggaaaaat atttagtttt ttttttttt tttgtatact tttcaagcta    4260
```

-continued

```
ccttgtcatg tatacagtca tttatgccta aagcctggtg attattcatt taaatgaaga      4320
tcacatttca tatcaacttt tgtatccaca gtagacaaaa tagcactaat ccagatgcct      4380
attgttggat actgaatgac agacaatctt atgtagcaaa gattatgcct gaaaaggaaa      4440
attattcagg gcagctaatt ttgcttttac caaaatatca gtagtaatat ttttggacag      4500
tagctaatgg gtcagtgggt tctttttaat gtttatactt agattttctt ttaaaaaaat      4560
taaaataaaa caaaaaaaaa tttctaggac tagacgatgt aataccagct aaagccaaac      4620
aattatacag tggaaggttt tacattattc atccaatgtg tttctattca tgttaagata      4680
ctactacatt tgaagtgggc agagaacatc agatgattga aatgttcgcc caggggtctc      4740
cagcaacttt ggaaatctct ttgtattttt acttgaagtg ccactaatgg acagcagata      4800
ttttctggct gatgttggta ttgggtgtag aacatgatt taaaaaaaaa ctcttgcctc       4860
tgctttcccc cactctgagg caagttaaaa tgtaaagat gtgatttatc tgggggggctc      4920 aggtatggtg gggaagtgga ttcaggaatc tggggaatgg caaatatatt aagaagagta      4980
ttgaaagtat ttggaggaaa atggttaatt ctgggtgtgc accagggttc agtagagtcc      5040
acttctgccc tggagaccac aaatcaacta gctccattta cagccatttc taaaatggca      5100
gcttcagttc tagagaagaa agaacaacat cagcagtaaa gtccatggaa tagctagtgg      5160
tctgtgtttc ttttcgccat tgcctagctt gccgtaatga ttctataatg ccatcatgca      5220
gcaattatga gaggctaggt catccaaaga gaagaccta tcaatgtagg ttgcaaaatc       5280
taacccctaa ggaagtgcag tctttgattt gatttcccta gtaaccttgc agatatgttt      5340
aaccaagcca tagcccatgc cttttgaggg ctgaacaaat aagggactta ctgataattt      5400
acttttgatc acattaaggt gttctcacct tgaaatctta tacactgaaa tggccattga      5460
tttaggccac tggcttagag tactccttcc cctgcatgac actgattaca aatactttcc      5520
tattcatact ttccaattat gagatggact gtgggtactg ggagtgatca ctaacaccat      5580
agtaatgtct aatattcaca ggcagatctg cttggggaag ctagttatgt gaaaggcaaa      5640
tagagtcata cagtagctca aaaggcaacc ataattctct ttggtgcagg tcttgggagc      5700
gtgatctaga ttacactgca ccattcccaa gttaatcccc tgaaaactta ctctcaactg      5760
gagcaaatga actttggtcc caaatatcca tcttttcagt agcgttaatt atgctctgtt      5820
tccaactgca tttcctttcc aattgaatta aagtgtggcc tcgtttttag tcatttaaaa      5880
ttgttttcta agtaattgct gcctctatta tggcacttca attttgcact gtcttttgag      5940
attcaagaaa aatttctatt cttttttttg catccaattg tgcctgaact tttaaaatat      6000
gtaaatgctg ccatgttcca aacccatcgt cagtgtgtgt gtttagagct gtgcaccta       6060 gaaacaacat attgtcccat gagcaggtgc ctgagacaca gacccctttg cattcacaga      6120
gaggtcattg gttatagaga cttgaattaa taagtgacat tatgccagtt tctgttctct      6180
cacaggtgat aaacaatgct ttttgtgcac tacatactct tcagtgtaga gctcttgttt      6240
tatgggaaaa ggctcaaatg ccaaattgtg tttgatggat taatatgccc ttttgccgat      6300
gcatactatt actgatgtga ctcggttttg tcgcagcttt gctttgttta atgaaacaca      6360
cttgtaaacc tcttttgcac tttgaaaaag aatccagcgg gatgctcgag cacctgtaaa      6420 caatttctc aacctatttg atgttcaaat aaagaattaa actaaa                      6466
```

<210> SEQ ID NO 35
<211> LENGTH: 595
<212> TYPE: PRT
<213> ORGANISM: Homo sapiens

<400> SEQUENCE: 35

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
                115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
            275                 280                 285

Ala Asn Leu Trp Pro Ser Pro Leu Met Ile Lys Arg Ser Lys Lys Asn
        290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
            355                 360                 365

Asp Leu Thr Leu His Asp Gln Val His Leu Leu Glu Cys Ala Trp Leu
        370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys

```
                        405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
            435                 440                 445
Lys Ser Ile Ile Leu Leu Asn Ser Gly Val Tyr Thr Phe Leu Ser Ser
            450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                        485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
            515                 520                 525
Lys Cys Lys Asn Val Val Pro Leu Tyr Asp Leu Leu Leu Glu Met Leu
            530                 535                 540
Asp Ala His Arg Leu His Ala Pro Thr Ser Arg Gly Gly Ala Ser Val
545                 550                 555                 560
Glu Glu Thr Asp Gln Ser His Leu Ala Thr Ala Gly Ser Thr Ser Ser
                        565                 570                 575
His Ser Leu Gln Lys Tyr Tyr Ile Thr Gly Glu Ala Glu Gly Phe Pro
            580                 585                 590
Ala Thr Val
    595

<210> SEQ ID NO 36
<211> LENGTH: 595
<212> TYPE: PRT
<213> ORGANISM: Homo sapiens

<400> SEQUENCE: 36

Met Thr Met Thr Leu His Thr Lys Ala Ser Gly Met Ala Leu Leu His
1               5                   10                  15
Gln Ile Gln Gly Asn Glu Leu Glu Pro Leu Asn Arg Pro Gln Leu Lys
            20                  25                  30
Ile Pro Leu Glu Arg Pro Leu Gly Glu Val Tyr Leu Asp Ser Ser Lys
            35                  40                  45
Pro Ala Val Tyr Asn Tyr Pro Glu Gly Ala Ala Tyr Glu Phe Asn Ala
            50                  55                  60
Ala Ala Ala Ala Asn Ala Gln Val Tyr Gly Gln Thr Gly Leu Pro Tyr
65                  70                  75                  80
Gly Pro Gly Ser Glu Ala Ala Ala Phe Gly Ser Asn Gly Leu Gly Gly
            85                  90                  95
Phe Pro Pro Leu Asn Ser Val Ser Pro Ser Pro Leu Met Leu Leu His
            100                 105                 110
Pro Pro Pro Gln Leu Ser Pro Phe Leu Gln Pro His Gly Gln Gln Val
            115                 120                 125
Pro Tyr Tyr Leu Glu Asn Glu Pro Ser Gly Tyr Thr Val Arg Glu Ala
            130                 135                 140
Gly Pro Pro Ala Phe Tyr Arg Pro Asn Ser Asp Asn Arg Arg Gln Gly
145                 150                 155                 160
Gly Arg Glu Arg Leu Ala Ser Thr Asn Asp Lys Gly Ser Met Ala Met
                        165                 170                 175
```

```
Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
            195                 200                 205

Phe Lys Arg Ser Ile Gln Gly His Asn Asp Tyr Met Cys Pro Ala Thr
        210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
                275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
                355                 360                 365

Asp Leu Thr Leu His Asp Gln Val His Leu Leu Glu Cys Ala Trp Leu
                370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
                435                 440                 445

Lys Ser Ile Ile Leu Leu Asn Ser Gly Val Tyr Thr Phe Leu Ser Ser
                450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
                515                 520                 525

Lys Cys Lys Asn Val Val Pro Leu Tyr Asp Leu Leu Leu Glu Met Leu
                530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
                580                 585                 590

Ala Thr Val
```

-continued

595

<210> SEQ ID NO 37
<211> LENGTH: 595
<212> TYPE: PRT
<213> ORGANISM: Homo sapiens

<400> SEQUENCE: 37

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365
```

```
Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
            435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595

<210> SEQ ID NO 38
<211> LENGTH: 595
<212> TYPE: PRT
<213> ORGANISM: Homo sapiens

<400> SEQUENCE: 38

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
            115                 120                 125

Pro Tyr Tyr Leu Glu Asn Glu Pro Ser Gly Tyr Thr Val Arg Glu Ala
        130                 135                 140
```

```
Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
            165                 170                 175

Glu Ser Ala Lys Glu Thr Arg Tyr Cys Ala Val Cys Asn Asp Tyr Ala
        180                 185                 190

Ser Gly Tyr His Tyr Gly Val Trp Ser Cys Glu Gly Cys Lys Ala Phe
    195                 200                 205

Phe Lys Arg Ser Ile Gln Gly His Asn Asp Tyr Met Cys Pro Ala Thr
210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
530                 535                 540

Asp Ala His Arg Leu His Ala Pro Thr Ser Arg Gly Gly Ala Ser Val
545                 550                 555                 560
```

Glu Glu Thr Asp Gln Ser His Leu Ala Thr Ala Gly Ser Thr Ser Ser
            565                 570                 575

His Ser Leu Gln Lys Tyr Tyr Ile Thr Gly Glu Ala Glu Gly Phe Pro
        580                 585                 590

Ala Thr Val
        595

<210> SEQ ID NO 39
<211> LENGTH: 7224
<212> TYPE: DNA
<213> ORGANISM: Homo sapiens

<400> SEQUENCE: 39

```
gtaccttgat tcgtattct gagaggctgc tgcttagcgg tagccccttg gtttccgtgg     60
caacggaaaa gcgcgggaat tacagataaa ttaaaactgc gactgcgcgg cgtgagctcg    120
ctgagacttc ctggacgggg gacaggctgt ggggtttctc agataactgg gcccctgcgc    180
tcaggaggcc ttcaccctct gctctgggta aagttcattg gaacagaaag aaatggattt    240
atctgctctt cgcgttgaag aagtacaaaa tgtcattaat gctatgcaga aaatcttaga    300
gtgtcccatc tgtctggagt tgatcaagga acctgtctcc acaaagtgtg accacatatt    360
ttgcaaattt tgcatgctga aacttctcaa ccagaagaaa gggccttcac agtgtccttt    420
atgtaagaat gatataacca aaaggagcct acaagaaagt acgagattta gtcaacttgt    480
tgaagagcta ttgaaaatca tttgtgcttt tcagcttgac acaggtttgg agtatgcaaa    540
cagctataat tttgcaaaaa aggaaaataa ctctcctgaa catctaaaag atgaagtttc    600
tatcatccaa agtatgggct acagaaaccg tgccaaaaga cttctacaga gtgaacccga    660
aaatccttcc ttgcaggaaa ccagtctcag tgtccaactc tctaaccttg aactgtgag    720 aactctgagg acaaagcagc ggatacaacc tcaaaagacg tctgtctaca ttgaattggg    780
atctgattct tctgaagata ccgttaataa ggcaacttat gcagtgtgg gagatcaaga    840 attgttacaa atcaccctc aaggaaccag ggatgaaatc agtttggatt ctgcaaaaaa    900
ggctgcttgt gaatttctg agacggatgt aacaaatact gaacatcatc aacccagtaa    960
taatgatttg aacaccactg agaagcgtgc agctgagagg catccagaaa agtatcaggg   1020
tagttctgtt tcaaacttgc atgtggagcc atgtggcaca aatactcatg ccagctcatt   1080
acagcatgag aacagcagtt tattactcac taaagacaga atgaatgtag aaaaggctga   1140
attctgtaat aaaagcaaac agcctggctt agcaaggagc aacataaca gatgggctgg   1200 aagtaaggaa acatgtaatg ataggcggac tcccagcaca gaaaaaaagg tagatctgaa   1260
tgctgatccc ctgtgtgaga gaaaagaatg gaataagcag aaactgccat gctcagagaa   1320
tcctagagat actgaagatg ttccttggat aacactaaat agcagcattc agaaagttaa   1380
tgagtggttt tccagaagtg atgaactgtt aggttctgat gactcacatg atggggagtc   1440
tgaatcaaat gccaaagtag ctgatgtatt ggacgttcta aatgaggtag atgaatattc   1500
tggttcttca gagaaaatag acttactggc cagtgatcct catgaggctt taatatgtaa   1560
aagtgaaaga gttcactcca atcagtaga gagtaatatt gaagacaaaa tatttgggaa   1620
aacctatcgg aagaaggcaa gcctccccaa cttaagccat gtaactgaaa atctaattat   1680
aggagcattt gttactgagc cacagataat acaagagcgt cccctcacaa ataaattaaa   1740
gcgtaaaagg agacctacat caggccttca tcctgaggat tttatcaaga aagcagattt   1800
ggcagttcaa aagactcctg aaatgataaa tcagggaact aaccaaacgg agcagaatgg   1860
```

```
tcaagtgatg aatattacta atagtggtca tgagaataaa acaaaaggtg attctattca    1920
gaatgagaaa aatcctaacc caatagaatc actcgaaaaa gaatctgctt tcaaaacgaa    1980
agctgaacct ataagcagca gtataagcaa tatggaactc gaattaaata tccacaattc    2040
aaaagcacct aaaaagaata ggctgaggag gaagtcttct accaggcata ttcatgcgct    2100
tgaactagta gtcagtagaa atctaagccc acctaattgt actgaattgc aaattgatag    2160
ttgttctagc agtgaagaga taagaaaaaa aagtacaac caaatgccag tcaggcacag    2220
cagaaaccta caactcatgg aaggtaaaga acctgcaact ggagccaaga agagtaacaa    2280
gccaaatgaa cagacaagta aaagacatga cagcgatact ttcccagagc tgaagttaac    2340
aaatgcacct ggttctttta ctaagtgttc aaataccagt gaacttaaag aatttgtcaa    2400
tcctagcctt ccaagagaag aaaaagaaga gaaactagaa acagttaaag tgtctaataa    2460
tgctgaagac cccaaagatc tcatgttaag tggagaaagg gttttgcaaa ctgaaagatc    2520
tgtagagagt agcagtattt cattggtacc tggtactgat tatggcactc aggaaagtat    2580
ctcgttactg gaagttagca ctctagggaa ggcaaaaaca gaaccaaata aatgtgtgag    2640
tcagtgtgca gcatttgaaa accccaaggg actaattcat ggttgttcca agataaatag    2700
aaatgacaca gaaggcttta gtatccatt gggacatgaa gttaaccaca gtcgggaaac    2760
aagcatagaa atggaagaaa gtgaacttga tgctcagtat ttgcagaata cattcaaggt    2820
ttcaaagcgc cagtcatttg ctccgttttc aaatccagga aatgcagaag aggaatgtgc    2880
aacattctct gcccactctg ggtccttaaa gaaacaaagt ccaaaagtca cttttgaatg    2940
tgaacaaaag gaagaaaatc aaggaaagaa tgagtctaat atcaagcctg tacagacagt    3000
taatatcact gcaggctttc ctgtggttgg tcagaaagat aagccagttg ataatgccaa    3060
atgtagtatc aaaggaggct ctaggttttg tctatcatct cagttcagag gcaacgaaac    3120
tggactcatt actccaaata acatggact tttacaaaac ccatatcgta taccaccact    3180
tttcccatc aagtcatttg ttaaaactaa atgtaagaaa atctgctag aggaaaactt    3240
tgaggaacat tcaatgtcac ctgaaagaga aatgggaaat gagaacattc caagtacagt    3300
gagcacaatt agccgtaata acattagaga aaatgttttt aaagaagcca gctcaagcaa    3360
tattaatgaa gtaggttcca gtactaatga agtgggctcc agtattaatg aaataggttc    3420
cagtgatgaa acattcaag cagaactagg tagaaacaga gggccaaaat tgaatgctat    3480
gcttagatta ggggttttgc aacctgaggt ctataaacaa agtcttcctg gaagtaattg    3540
taagcatcct gaaataaaaa agcaagaata tgaagaagta gttcagactg ttaatacaga    3600
tttctctcca tatctgattt cagataactt agaacagcct atgggaagta gtcatgcatc    3660
tcaggttgt tctgagacac ctgatgacct gttagatgat ggtgaaataa aggaagatac    3720
tagttttgct gaaaatgaca ttaaggaaag ttctgctgtt tttagcaaaa gcgtccagaa    3780
aggagagctt agcaggagtc ctagcccttt cacccataca catttggctc agggttaccg    3840
aagagggcc aagaaattag agtcctcaga agagaactta tctagtgagg atgaagagct    3900
tcctgcttc caacacttgt tatttggtaa agtaaacaat ataccttctc agtctactag    3960
gcatagcacc gttgctaccg agtgtctgtc taagaacaca gaggagaatt tattatcatt    4020
gaagaatagc ttaaatgact gcagtaacca ggtaatattg gcaaaggcat ctcaggaaca    4080
tcaccttagt gaggaaacaa aatgttctg tagcttgttt tcttcacagt gcagtgaatt    4140
ggaagacttg actgcaaata caaacaccca ggatcctttc ttgattggtt cttccaaaca    4200
aatgaggcat cagtctgaaa gccagggagt tggtctgagt gacaaggaat tggtttcaga    4260
```

```
tgatgaagaa agaggaacgg gcttggaaga aaataatcaa gaagagcaaa gcatggattc      4320
aaacttaggt gaagcagcat ctgggtgtga gagtgaaaca agcgtctctg aagactgctc      4380
agggctatcc tctcagagtg acattttaac cactcagcag agggatacca tgcaacataa      4440
cctgataaag ctccagcagg aaatggctga actagaagct gtgttagaac agcatgggag      4500
ccagccttct aacagctacc cttccatcat aagtgactct tctgcccttg aggacctgcg      4560
aaatccagaa caaagcacat cagaaaaagc agtattaact tcacagaaaa gtagtgaata      4620
ccctataagc cagaatccag aaggcctttc tgctgacaag tttgaggtgt ctgcagatag      4680
ttctaccagt aaaaataaag aaccaggagt ggaaaggtca tccccttcta aatgcccatc      4740
attagatgat aggtggtaca tgcacagttg ctctgggagt cttcagaata gaaactaccc      4800
atctcaagag gagctcatta aggttgttga tgtggaggag caacagctgg aagagtctgg      4860
gccacacgat ttgacggaaa catcttactt gccaaggcaa gatctagagg gaacccctta      4920 cctgaatct ggaatcagcc tcttctctga tgaccctgaa tctgatcctt ctgaagacag      4980
agccccagag tcagctcgtg ttggcaacat accatcttca acctctgcat gaaagttcc      5040 ccaattgaaa gttgcagaat ctgcccagag tccagctgct gctcatacta ctgatactgc      5100
tgggtataat gcaatggaag aaagtgtgag cagggagaag ccagaattga cagcttcaac      5160
agaaagggtc aacaaagaa tgtccatggt ggtgtctggc ctgaccccag aagaatttat      5220
gctcgtgtac aagtttgcca gaaaacacca catcactta actaatctaa ttactgaaga      5280
gactactcat gttgttatga aaacagatgc tgagttgtg tgtgaacgga cactgaaata      5340
ttttctagga attgcgggag gaaaatgggt agttagctat ttctgggtga cccagtctat      5400
taaagaaaga aaaatgctga atgagcatga ttttgaagtc agaggagatg tggtcaatgg      5460
aagaaaccac caaggtccaa agcgagcaag agaatcccag gacagaaaga tcttcagggg      5520
gctagaaatc tgttgctatg ggcccttcac caacatgccc acagatcaac tggaatggat      5580
ggtacagctg tgtggtgctt ctgtggtgaa ggagctttca tcattcaccc ttggcacagg      5640
tgtccaccca attgtggttg tgcagccaga tgcctggaca gaggacaatg gcttccatgc      5700
aattgggcag atgtgtgagg cacctgtggt gacccgagag tgggtgttgg acagtgtagc      5760
actctaccag tgccaggagc tggacaccta cctgatacc cagatccccc acagccacta      5820
ctgactgcag ccagccacag gtacagagcc acaggacccc aagaatgagc ttacaaagtg      5880 gccttccag gccctgggag ctcctctcac tcttcagtcc ttctactgtc ctggctacta      5940 aatatttat gtacatcagc ctgaaaagga cttctggcta tgcaagggtc ccttaaagat      6000
tttctgcttg aagtctccct tggaaatctg ccatgagcac aaaattatgg taatttttca      6060
cctgagaaga ttttaaaacc atttaaacgc caccaattga gcaagatgct gattcattat      6120
ttatcagccc tattctttct attcaggctg ttgttggctt agggctggaa gcacagagtg      6180
gcttggcctc aagagaatag ctggtttccc taagttact tctctaaaac cctgtgttca      6240
caaaggcaga gagtcagacc cttcaatgga aggagagtgc ttgggatcga ttatgtgact      6300
taaagtcaga atagtccttg ggcagttctc aaatgttgga gtggaacatt ggggaggaaa      6360
ttctgaggca ggtattagaa atgaaaagga aacttgaaac ctgggcatgg tggctcacgc      6420
ctgtaatccc agcactttgg gaggccaagg tgggcagatc actggaggtc aggagttcga      6480
aaccagcctg gccaacatgg tgaaaccca tctctactaa aaatacagaa attagccggt      6540
catggtggtg gacacctgta atcccagcta ctcaggtggc taaggcagga gaatcacttc      6600
```

| | |
|---|---:|
| agcccgggag gtggaggttg cagtgagcca agatcatacc acggcactcc agcctgggtg | 6660 |
| acagtgagac tgtggctcaa aaaaaaaaaa aaaaaaagga aaatgaaact agaagagatt | 6720 |
| tctaaaagtc tgagatatat ttgctagatt tctaaagaat gtgttctaaa acagcagaag | 6780 |
| attttcaaga accggtttcc aaagacagtc ttctaattcc tcattagtaa taagtaaaat | 6840 |
| gtttattgtt gtagctctgg tatataatcc attcctctta aaatataaga cctctggcat | 6900 |
| gaatatttca tatctataaa atgacagatc ccaccaggaa ggaagctgtt gctttctttg | 6960 |
| aggtgatttt tttcctttgc tccctgttgc tgaaaccata cagcttcata ataattttg | 7020 |
| cttgctgaag gaagaaaaag tgttttcat aaacccatta ccaggactg tttatagctg | 7080 |
| ttggaaggac taggtcttcc ctagcccccc cagtgtgcaa gggcagtgaa gacttgattg | 7140 |
| tacaaaatac gttttgtaaa tgttgtgctg ttaacactgc aaataaactt ggtagcaaac | 7200 |
| acttccaaaa aaaaaaaaaa aaaa | 7224 |

<210> SEQ ID NO 40
<211> LENGTH: 7287
<212> TYPE: DNA
<213> ORGANISM: Homo sapiens

<400> SEQUENCE: 40

| | |
|---|---:|
| gtaccttgat ttcgtattct gagaggctgc tgcttagcgg tagccccttg gtttccgtgg | 60 |
| caacggaaaa gcgcgggaat tacagataaa ttaaaactgc gactgcgcgg cgtgagctcg | 120 |
| ctgagacttc ctggacgggg acaggctgt ggggtttctc agataactgg gcccctgcgc | 180 |
| tcaggaggcc ttcaccctct gctctgggta aagttcattg gaacagaaag aaatggattt | 240 |
| atctgctctt cgcgttgaag aagtacaaaa tgtcattaat gctatgcaga aaatcttaga | 300 |
| gtgtcccatc tgtctggagt tgatcaagga acctgtctcc acaaagtgtg accacatatt | 360 |
| ttgcaaattt tgcatgctga aacttctcaa ccagaagaaa gggccttcac agtgtccttt | 420 |
| atgtaagaat gatataacca aaaggagcct acaagaaagt acgagattta gtcaacttgt | 480 |
| tgaagagcta ttgaaaatca tttgtgcttt tcagcttgac acaggtttgg agtatgcaaa | 540 |
| cagctataat tttgcaaaaa aggaaaataa ctctcctgaa catctaaaag atgaagtttc | 600 |
| tatcatccaa agtatgggct acagaaaccg tgccaaaaga cttctacaga gtgaacccga | 660 |
| aaatccttcc ttgcaggaaa ccagtctcag tgtccaactc tctaaccttg gaactgtgag | 720 |
| aactctgagg acaaagcagc ggatacaacc tcaaaagacg tctgtctaca ttgaattggg | 780 |
| atctgattct tctgaagata ccgttaataa ggcaacttat tgcagtgtgg agatcaaga | 840 |
| attgttacaa atcaccccctc aaggaaccag ggatgaaatc agtttggatt ctgcaaaaaa | 900 |
| ggctgcttgt gaattttctg agacggatgt aacaaatact gaacatcatc aacccagtaa | 960 |
| taatgatttg aacaccactg agaagcgtgc agctgagagg catccagaaa agtatcaggg | 1020 |
| tagttctgtt tcaaacttgc atgtggagcc atgtggcaca aatactcatg ccagctcatt | 1080 |
| acagcatgag aacagcagtt tattactcac taaagacaga atgaatgtag aaaaggctga | 1140 |
| attctgtaat aaaagcaaac agcctggctt agcaaggagc caacataaca gatgggctgg | 1200 |
| aagtaaggaa acatgtaatg ataggcggac tcccagcaca gaaaaaaagg tagatctgaa | 1260 |
| tgctgatccc ctgtgtgaga aaagaatg gaataagcag aaactgccat gctcagagaa | 1320 |
| tcctagagat actgaagatg ttccttggat aacactaaat agcagcattc agaaagttaa | 1380 |
| tgagtggttt tccagaagtg atgaactgtt aggttctgat gactcacatg atggggagtc | 1440 |
| tgaatcaaat gccaaagtag ctgatgtatt ggacgttcta aatgaggtag atgaatattc | 1500 |

```
tggttcttca gagaaaatag acttactggc cagtgatcct catgaggctt taatatgtaa    1560
aagtgaaaga gttcactcca aatcagtaga gagtaatatt gaagacaaaa tatttgggaa    1620
aacctatcgg aagaaggcaa gcctccccaa cttaagccat gtaactgaaa atctaattat    1680
aggagcattt gttactgagc cacagataat acaagagcgt cccctcacaa ataaattaaa    1740
gcgtaaaagg agacctacat caggccttca tcctgaggat tttatcaaga aagcagattt    1800
ggcagttcaa aagactcctg aaatgataaa tcagggaact aaccaaacgg agcagaatgg    1860
tcaagtgatg aatattacta atagtggtca tgagaataaa acaaaaggtg attctattca    1920
gaatgagaaa aatcctaacc caatagaatc actcgaaaaa gaatctgctt tcaaaacgaa    1980
agctgaacct ataagcagca gtataagcaa tatggaactc gaattaaata tccacaattc    2040
aaaagcacct aaaaagaata ggctgaggag gaagtcttct accaggcata ttcatgcgct    2100
tgaactagta gtcagtagaa atctaagccc acctaattgt actgaattgc aaattgatag    2160
ttgttctagc agtgaagaga taaagaaaaa aaagtacaac caaatgccag tcaggcacag    2220
cagaaaccta caactcatgg aaggtaaaga acctgcaact ggagccaaga agagtaacaa    2280
gccaaatgaa cagacaagta aaagacatga cagcgatact ttcccagagc tgaagttaac    2340
aaatgcacct ggttctttta ctaagtgttc aaataccagt gaacttaaag aatttgtcaa    2400
tcctagcctt ccaagagaag aaaaagaaga gaaactagaa acagttaaag tgtctaataa    2460
tgctgaagac cccaaagatc tcatgttaag tggagaaagg gttttgcaaa ctgaaagatc    2520
tgtagagagt agcagtattt cattggtacc tggtactgat tatggcactc aggaaagtat    2580
ctcgttactg gaagttagca ctctagggaa ggcaaaaaca gaaccaaata aatgtgtgag    2640
tcagtgtgca gcatttgaaa accccaaggg actaattcat ggttgttcca agataaatag    2700
aaatgacaca gaaggcttta agtatccatt gggacatgaa gttaaccaca gtcgggaaac    2760
aagcatagaa atggaagaaa gtgaacttga tgctcagtat ttgcagaata cattcaaggt    2820
ttcaaagcgc cagtcatttg ctccgttttc aaatccagga aatgcagaag aggaatgtgc    2880
aacattctct gcccactctg ggtccttaaa gaaacaaagt ccaaaagtca cttttgaatg    2940
tgaacaaaag gaagaaaatc aaggaaagaa tgagtctaat atcaagcctg tacagacagt    3000
taatatcact gcaggctttc ctgtggttgg tcagaaagat aagccagttg ataatgccaa    3060
atgtagtatc aaaggaggct ctaggttttg tctatcatct cagttcagag caacgaaac    3120 tggactcatt actccaaata acatggact tttacaaaac ccatatcgta taccaccact    3180
ttttcccatc aagtcatttg ttaaaactaa atgtaagaaa atctgctag aggaaaactt    3240 tgaggaacat tcaatgtcac ctgaaagaga aatgggaaat gagaacattc caagtacagt    3300
gagcacaatt agccgtaata acattagaga aaatgttttt aaagaagcca gctcaagcaa    3360
tattaatgaa gtaggttcca gtactaatga agtgggctcc agtattaatg aaataggttc    3420
cagtgatgaa acattcaag cagaactagg tagaaacaga gggccaaaat tgaatgctat    3480
gcttagatta ggggttttgc aacctgaggt ctataaacaa agtcttcctg gaagtaattg    3540
taagcatcct gaaataaaaa agcaagaata tgaagaagta gttcagactg ttaatacaga    3600
tttctctcca tatctgattt cagataactt agaacagcct atgggaagta gtcatgcatc    3660
tcaggtttgt tctgagacac ctgatgacct gttagatgat ggtgaaataa aggaagatac    3720
tagttttgct gaaaatgaca ttaaggaaag ttctgctgtt tttagcaaaa gcgtccagaa    3780
aggagagctt agcaggagtc ctagcccttt cacccataca catttggctc agggttaccg    3840
```

```
aagaggggcc aagaaattag agtcctcaga agagaactta tctagtgagg atgaagagct   3900
tccctgcttc caacacttgt tatttggtaa agtaaacaat ataccttctc agtctactag   3960
gcatagcacc gttgctaccg agtgtctgtc taagaacaca gaggagaatt tattatcatt   4020
gaagaatagc ttaaatgact gcagtaacca ggtaatattg gcaaaggcat ctcaggaaca   4080
tcaccttagt gaggaaacaa aatgttctgc tagcttgttt tcttcacagt gcagtgaatt   4140
ggaagacttg actgcaaata caaacaccca ggatcctttc ttgattggtt cttccaaaca   4200
aatgaggcat cagtctgaaa gccagggagt tggtctgagt gacaaggaat tggtttcaga   4260
tgatgaagaa agaggaacgg gcttggaaga aaataatcaa gaagagcaaa gcatggattc   4320
aaacttaggt gaagcagcat ctgggtgtga gagtgaaaca agcgtctctg aagactgctc   4380
agggctatcc tctcagagtg acattttaac cactcagcag agggatacca tgcaacataa   4440
cctgataaag ctccagcagg aaatggctga actagaagct gtgttagaac agcatgggag   4500
ccagccttct aacagctacc cttccatcat aagtgactct tctgcccttg aggacctgcg   4560
aaatccagaa caaagcacat cagaaaaaga ttcgcatata catggccaaa ggaacaactc   4620
catgttttct aaaaggccta gagaacatat atcagtatta acttcacaga aaagtagtga   4680
atacccctata agccagaatc cagaaggcct ttctgctgac aagtttgagg tgtctgcaga   4740
tagttctacc agtaaaaata aagaaccagg agtggaaagg tcatcccctt ctaaatgccc   4800
atcattagat gataggtggt acatgcacag ttgctctggg agtcttcaga atagaaacta   4860
cccatctcaa gaggagctca ttaaggttgt tgatgtggag agcaacagc tggaagagtc   4920
tgggccacac gatttgacgg aaacatctta cttgccaagg caagatctag agggaacccc   4980
ttacctggaa tctggaatca gcctcttctc tgatgaccct gaatctgatc cttctgaaga   5040
cagagcccca gagtcagctc gtgttggcaa cataccatct tcaacctctg cattgaaagt   5100
tccccaattg aaagttgcag aatctgccca gagtccagct gctgctcata ctactgatac   5160
tgctgggtat aatgcaatgg aagaaagtgt gagcagggag aagccagaat tgacagcttc   5220
aacagaaagg gtcaacaaaa gaatgtccat ggtggtgtct ggcctgaccc cagaagaatt   5280
tatgctcgtg tacaagtttg ccagaaaaca ccacatcact ttaactaatc taattactga   5340
agagactact catgttgtta tgaaaacaga tgctgagttt gtgtgtgaac ggacactgaa   5400
atattttcta ggaattgcgg gaggaaaatg ggtagttagc tatttctggg tgacccagtc   5460
tattaaagaa agaaaaatgc tgaatgagca tgattttgaa gtcagaggag atgtggtcaa   5520
tggaagaaac caccaaggtc caaagcgagc aagagaatcc caggacagaa agatcttcag   5580
ggggctagaa atctgttgct atgggccctt caccaacatg cccacagatc aactggaatg   5640
gatggtacag ctgtgtggtg cttctgtggt gaaggagctt tcatcattca cccttggcac   5700
aggtgtccac ccaattgtgg ttgtgcagcc agatgcctgg acagaggaca atggcttcca   5760
tgcaattggg cagatgtgtg aggcacctgt ggtgacccga gagtgggtgt tggacagtgt   5820
agcactctac cagtgccagg agctggacac ctacctgata ccccagatcc cccacagcca   5880
ctactgactg cagccagcca caggtacaga gccacaggac cccaagaatg agcttacaaa   5940
gtggcctttc caggccctgg gagctcctct cactcttcag tccttctact gtcctggcta   6000
ctaaatattt tatgtacatc agcctgaaaa ggacttctgg ctatgcaagg gtcccttaaa   6060
gattttctgc ttgaagtctc ccttggaaat ctgccatgag cacaaaatta tggtaatttt   6120
tcacctgaga agatttttaaa accatttaaa cgccaccaat tgagcaagat gctgattcat   6180
tatttatcag cccctattctt tctattcagg ctgttgttgg cttagggctg gaagcacaga   6240
```

-continued

| | |
|---|---|
| gtggcttggc ctcaagagaa tagctggttt ccctaagttt acttctctaa aaccctgtgt | 6300 |
| tcacaaaggc agagagtcag acccttcaat ggaaggagag tgcttgggat cgattatgtg | 6360 |
| acttaaagtc agaatagtcc ttgggcagtt ctcaaatgtt ggagtggaac attggggagg | 6420 |
| aaattctgag gcaggtatta gaaatgaaaa ggaaacttga aacctgggca tggtggctca | 6480 |
| cgcctgtaat cccagcactt tgggaggcca aggtgggcag atcactggag gtcaggagtt | 6540 |
| cgaaccagc ctggccaaca tggtgaaacc ccatctctac taaaaataca gaaattagcc | 6600 |
| ggtcatggtg gtggacacct gtaatcccag ctactcaggt ggctaaggca ggagaatcac | 6660 |
| ttcagcccgg gaggtggagg ttgcagtgag ccaagatcat accacggcac tccagcctgg | 6720 |
| gtgacagtga gactgtggct caaaaaaaaa aaaaaaaaa ggaaaatgaa actagaagag | 6780 |
| atttctaaaa gtctgagata tatttgctag atttctaaag aatgtgttct aaaacagcag | 6840 |
| aagattttca agaaccggtt tccaaagaca gtcttctaat tcctcattag taataagtaa | 6900 |
| aatgtttatt gttgtagctc tggtatataa tccattcctc ttaaaatata agacctctgg | 6960 |
| catgaatatt tcatatctat aaaatgacag atcccaccag gaaggaagct gttgctttct | 7020 |
| ttgaggtgat tttttccctt tgctccctgt tgctgaaacc atacagcttc ataaataatt | 7080 |
| ttgcttgctg aaggaagaaa aagtgttttt cataaaccca ttatccagga ctgtttatag | 7140 |
| ctgttggaag gactaggtct tccctagccc ccccagtgtg caagggcagt gaagacttga | 7200 |
| ttgtacaaaa tacgttttgt aaatgttgtg ctgttaacac tgcaaataaa cttggtagca | 7260 |
| aacacttcca aaaaaaaaaa aaaaaaa | 7287 |

<210> SEQ ID NO 41
<211> LENGTH: 7132
<212> TYPE: DNA
<213> ORGANISM: Homo sapiens

<400> SEQUENCE: 41

| | |
|---|---|
| cttagcggta gcccccttggt ttccgtggca acggaaaagc gcgggaatta cagataaatt | 60 |
| aaaactgcga ctgcgcggcg tgagctcgct gagacttcct ggacggggga caggctgtgg | 120 |
| ggtttctcag ataactgggc ccctgcgctc aggaggcctt caccctctgc tctggttcat | 180 |
| tggaacagaa agaaatggat ttatctgctc ttcgcgttga agaagtacaa aatgtcatta | 240 |
| atgctatgca gaaaatctta gagtgtccca tctgattttg catgctgaaa cttctcaacc | 300 |
| agaagaaagg gccttcacag tgtcctttat gtaagaatga tataaccaaa aggagcctac | 360 |
| aagaaagtac gagatttagt caacttgttg aagagctatt gaaaatcatt tgtgcttttc | 420 |
| agcttgacac aggtttggag tatgcaaaca gctataattt tgcaaaaaag gaaaataact | 480 |
| ctcctgaaca tctaaaagat gaagtttcta tcatccaaag tatgggctac agaaccgtg | 540 |
| ccaaaagact tctacagagt gaacccgaaa tccttccctt gcaggaaacc agtctcagtg | 600 |
| tccaactctc taaccttgga actgtgagaa ctctgaggac aaagcagcgg atacaacctc | 660 |
| aaaagacgtc tgtctacatt gaattgggat ctgattcttc tgaagatacc gttaataagg | 720 |
| caacttattg cagtgtggga gatcaagaat tgttacaaat caccccctcaa ggaaccaggg | 780 |
| atgaaatcag tttggattct gcaaaaaagg ctgcttgtga attttctgag acggatgtaa | 840 |
| caaatactga acatcatcaa cccagtaata atgatttgaa caccactgag aagcgtgcag | 900 |
| ctgagaggca tccagaaaag tatcagggta ttctgtttc aaacttgcat gtggagccat | 960 |
| gtggcacaaa tactcatgcc agctcattac agcatgagaa cagcagttta ttactcacta | 1020 |

```
aagacagaat gaatgtagaa aaggctgaat tctgtaataa aagcaaacag cctggcttag   1080
caaggagcca acataacaga tgggctggaa gtaaggaaac atgtaatgat aggcggactc   1140
ccagcacaga aaaaaggta gatctgaatg ctgatcccct gtgtgagaga aaagaatgga    1200
ataagcagaa actgccatgc tcagagaatc ctagagatac tgaagatgtt ccttggataa   1260
cactaaatag cagcattcag aaagttaatg agtggttttc cagaagtgat gaactgttag   1320
gttctgatga ctcacatgat ggggagtctg aatcaaatgc caaagtagct gatgtattgg   1380
acgttctaaa tgaggtagat gaatattctg gttcttcaga gaaaatagac ttactggcca   1440
gtgatcctca tgaggcttta atatgtaaaa gtgaaagagt tcactccaaa tcagtagaga   1500
gtaatattga agacaaaata tttgggaaaa cctatcggaa gaaggcaagc ctccccaact   1560
taagccatgt aactgaaaat ctaattatag gagcatttgt tactgagcca cagataatac   1620
aagagcgtcc cctcacaaat aaattaaagc gtaaaaggag acctacatca ggccttcatc   1680
ctgaggattt tatcaagaaa gcagatttgg cagttcaaaa gactcctgaa atgataaatc   1740
agggaactaa ccaaacggag cagaatggtc aagtgatgaa tattactaat agtggtcatg   1800
agaataaaac aaaaggtgat tctattcaga atgagaaaaa tcctaaccca atagaatcac   1860 tcgaaaaga atctgctttc aaaacgaaag ctgaacctat aagcagcagt ataagcaata   1920
tggaactcga attaaatatc cacaattcaa aagcacctaa aaagaatagg ctgaggagga   1980
agtcttctac caggcatatt catgcgcttg aactagtagt cagtagaaat ctaagcccac   2040
ctaattgtac tgaattgcaa attgatagtt gttctagcag tgaagagata aagaaaaaaa   2100
agtacaacca aatgccagtc aggcacagca gaaacctaca actcatggaa ggtaaagaac   2160
ctgcaactgg agccaagaag agtaacaagc caaatgaaca gacaagtaaa agacatgaca   2220
gcgatacttt cccagagctg aagttaacaa atgcacctgg ttcttttact aagtgttcaa   2280
ataccagtga acttaaagaa tttgtcaatc ctagccttcc aagagaagaa aaagaagaga   2340
aactagaaac agttaaagtg tctaataatg ctgaagaccc caaagatctc atgttaagtg   2400
gagaaagggt tttgcaaact gaaagatctg tagagagtag cagtatttca ttggtacctg   2460
gtactgatta tggcactcag gaaagtatct cgttactgga agttagcact ctagggaagg   2520
caaaaacaga accaaataaa tgtgtgagtc agtgtgcagc atttgaaaac cccaagggac   2580
taattcatgt tgttccaaa gataatagaa atgacacaga aggctttaag tatccattgg    2640
gacatgaagt taaccacagt cgggaaacaa gcatagaaat ggaagaaagt gaacttgatg   2700
ctcagtattt gcagaataca ttcaaggttt caaagcgcca gtcatttgct ccgttttcaa   2760
atccaggaaa tgcagaagag gaatgtgcaa cattctctgc ccactctggg tccttaaaga   2820
aacaaagtcc aaaagtcact tttgaatgtg aacaaaagga agaaatcaa ggaaagaatg    2880 agtctaatat caagcctgta cagacagtta atatcactgc aggctttcct gtggttggtc   2940
agaaagataa gccagttgat aatgccaaat gtagtatcaa aggaggctct aggttttgtc   3000
tatcatctca gttcagaggc aacgaaactg gactcattac tccaaataaa catgactttt   3060
tacaaaaccc atatcgtata ccaccacttt ttcccatcaa gtcatttgtt aaaactaaat   3120
gtaagaaaaa tctgctagag gaaaactttg aggaacattc aatgtcacct gaaagagaaa   3180
tgggaaatga gaacattcca agtacagtga gcacaattag ccgtaataac attagagaaa   3240 atgttttaa agaagccagc tcaagcaata ttaatgaagt aggttccagt actaatgaag    3300
tgggctccag tattaatgaa ataggttcca gtgatgaaaa cattcaagca gaactaggta   3360
gaaacagagg gccaaaattg aatgctatgc ttagattagg ggttttgcaa cctgaggtct   3420
```

```
ataaacaaag tcttcctgga agtaattgta agcatcctga aataaaaaag caagaatatg   3480
aagaagtagt tcagactgtt aatacagatt tctctccata tctgatttca gataacttag   3540
aacagcctat gggaagtagt catgcatctc aggtttgttc tgagacacct gatgacctgt   3600
tagatgatgg tgaaataaag gaagatacta gttttgctga aaatgacatt aaggaaagtt   3660
ctgctgtttt tagcaaaagc gtccagaaag gagagcttag caggagtcct agccctttca   3720
cccatacaca tttggctcag ggttaccgaa gaggggccaa gaaattagag tcctcagaag   3780
agaacttatc tagtgaggat gaagagcttc cctgcttcca acacttgtta tttggtaaag   3840
taaacaatat accttctcag tctactaggc atagcaccgt tgctaccgag tgtctgtcta   3900
agaacacaga ggagaattta ttatcattga agaatagctt aaatgactgc agtaaccagg   3960
taatattggc aaaggcatct caggaacatc accttagtga ggaaacaaaa tgttctgcta   4020
gcttgttttc ttcacagtgc agtgaattgg aagacttgac tgcaaataca aacacccagg   4080
atcctttctt gattggttct tccaaacaaa tgaggcatca gtctgaaagc cagggagttg   4140
gtctgagtga caaggaattg gtttcagatg atgaagaaag aggaacgggc ttggaagaaa   4200
ataatcaaga agagcaaagc atggattcaa acttaggtga agcagcatct gggtgtgaga   4260
gtgaaacaag cgtctctgaa gactgctcag ggctatcctc tcagagtgac atttttaacca   4320 ctcagcagag ggataccatg caacataacc tgataaagct ccagcaggaa atggctgaac   4380
tagaagctgt gttagaacag catgggagcc agccttctaa cagctaccct tccatcataa   4440
gtgactcttc tgcccttgag gacctgcgaa atccagaaca agcacatca gaaaaagcag   4500 tattaacttc acagaaaagt agtgaatacc ctataagcca gaatccagaa ggcctttctg   4560
ctgacaagtt tgaggtgtct gcagatagtt ctaccagtaa aaataaagaa ccaggagtgg   4620
aaaggtcatc cccttctaaa tgcccatcat tagatgatag gtggtacatg cacagttgct   4680
ctgggagtct tcagaataga aactacccat ctcaagagga gctcattaag gttgttgatg   4740
tggaggagca acagctggaa gagtctgggc cacacgattt gacggaaaca tcttacttgc   4800
caaggcaaga tctagaggga accccttacc tggaatctgg aatcagcctc ttctctgatg   4860
accctgaatc tgatccttct gaagacagag ccccagagtc agctcgtgtt ggcaacatac   4920
catcttcaac ctctgcattg aaagttcccc aattgaaagt tgcagaatct gcccagagtc   4980
cagctgctgc tcatactact gatactgctg gtataatgc aatggaagaa agtgtgagca   5040
gggagaagcc agaattgaca gcttcaacag aaagggtcaa caaaagaatg tccatggtgg   5100
tgtctggcct gaccccagaa gaatttatgc tcgtgtacaa gtttgccaga aaacaccaca   5160
tcactttaac taatctcaatt actgaagaga ctactcatgt tgttatgaaa acagatgctg   5220
agtttgtgtg tgaacggaca ctgaaatatt ttctaggaat tgcgggagga aaatgggtag   5280
ttagctattt ctgggtgacc cagtctatta agaaagaaa aatgctgaat gagcatgatt   5340
ttgaagtcag aggagatgtg gtcaatgaaa gaaaccacca aggtccaaag cgagcaagag   5400
aatcccagga cagaaagatc ttcaggggc tagaaatctg ttgctatggg cccttcacca   5460
acatgcccac agatcaactg gaatggatgg tacagctgtg tggtgcttct gtggtgaagg   5520
agctttcatc attcacccctt ggcacaggtg tccacccaat tgtggttgtg cagccagatg   5580
cctggacaga ggacaatggc ttccatgcaa ttgggcagat gtgtgaggca cctgtggtga   5640
cccgagagtg ggtgttggac agtgtagcac tctaccagtg ccaggagctg gacacctacc   5700 tgataccca gatcccccac agccactact gactgcagcc agccacaggt acagagccac   5760
```

| | |
|---|---|
| aggaccccaa gaatgagctt acaaagtggc ctttccaggc cctgggagct cctctcactc | 5820 |
| ttcagtcctt ctactgtcct ggctactaaa tattttatgt acatcagcct gaaaaggact | 5880 |
| tctggctatg caagggtccc ttaaagattt tctgcttgaa gtctcccttg gaaatctgcc | 5940 |
| atgagcacaa aattatggta attttcacc tgagaagatt ttaaaaccat ttaaacgcca | 6000 |
| ccaattgagc aagatgctga ttcattattt atcagcccta ttctttctat tcaggctgtt | 6060 |
| gttggcttag gctggaagc acagagtggc ttggcctcaa gagaatagct ggtttccta | 6120 |
| agtttacttc tctaaaaccc tgtgttcaca aaggcagaga gtcagaccct tcaatggaag | 6180 |
| gagagtgctt gggatcgatt atgtgactta aagtcagaat agtccttggg cagttctcaa | 6240 |
| atgttggagt ggaacattgg ggaggaaatt ctgaggcagg tattagaaat gaaaggaaa | 6300 |
| cttgaaacct gggcatgtgt gctcacgcct gtaatcccag cactttggga ggccaaggtg | 6360 |
| ggcagatcac tggaggtcag gagttcgaaa ccagcctggc caacatggtg aaaccccatc | 6420 |
| tctactaaaa atacagaaat tagccggtca tggtggtgga cacctgtaat cccagctact | 6480 |
| caggtggcta aggcaggaga atcacttcag cccgggaggt ggaggttgca gtgagccaag | 6540 |
| atcataccac ggcactccag cctgggtgac agtgagactg tggctcaaaa aaaaaaaaa | 6600 |
| aaaaaggaaa atgaaactag aagagatttc taaaagtctg agatatattt gctagatttc | 6660 |
| taaagaatgt gttctaaaac agcagaagat tttcaagaac cggtttccaa agacagtctt | 6720 |
| ctaattcctc attagtaata agtaaaatgt ttattgttgt agctctggta tataatccat | 6780 |
| tcctcttaaa atataagacc tctggcatga atatttcata tctataaaat gacagatccc | 6840 |
| accaggaagg aagctgttgc tttctttgag gtgattttt tcctttgctc cctgttgctg | 6900 |
| aaaccataca gcttcataaa taattttgct tgctgaagga agaaaaagtg ttttcataa | 6960 |
| acccattatc caggactgtt tatagctgtt ggaaggacta ggtcttccct agcccccca | 7020 |
| gtgtgcaagg gcagtgaaga cttgattgta caaaatacgt tttgtaaatg ttgtgctgtt | 7080 |
| aacactgcaa ataaacttgg tagcaaacac ttccaaaaaa aaaaaaaaaa aa | 7132 |

<210> SEQ ID NO 42
<211> LENGTH: 3699
<212> TYPE: DNA
<213> ORGANISM: Homo sapiens

<400> SEQUENCE: 42

| | |
|---|---|
| ttcattggaa cagaaagaaa tggatttatc tgctcttcgc gttgaagaag tacaaaatgt | 60 |
| cattaatgct atgcagaaaa tcttagagtg tcccatctgt ctggagttga tcaaggaacc | 120 |
| tgtctccaca aagtgtgacc acatattttg caaattttgc atgctgaaac ttctcaacca | 180 |
| gaagaaaggg ccttcacagt gtccttatg taagaatgat ataaccaaaa ggagcctaca | 240 |
| agaaagtacg agatttagtc aacttgttga agagctattg aaaatcattt gtgcttttca | 300 |
| gcttgacaca ggtttggagt atgcaaacag ctataatttt gcaaaaaagg aaaataactc | 360 |
| tcctgaacat ctaaaagatg aagtttctat catccaaagt atgggctaca gaaaccgtgc | 420 |
| caaaagactt ctacagagtg aacccgaaaa tccttccttg caggaaacca gtctcagtgt | 480 |
| ccaactctct aaccttggaa ctgtgagaac tctgaggaca aagcagcgga tacaacctca | 540 |
| aaagacgtct gtctacattg aattgggatc tgattcttct gaagataccg ttaataaggc | 600 |
| aacttattgc agtgtgggag atcaagaatt gttacaaatc accctcaag gaaccaggga | 660 |
| tgaaatcagt ttggattctg caaaaaaggc tgcttgtgaa ttttctgaga cggatgtaac | 720 |
| aaatactgaa catcatcaac ccagtaataa tgatttgaac accactgaga agcgtgcagc | 780 |

```
tgagaggcat ccagaaaagt atcagggtga agcagcatct gggtgtgaga gtgaaacaag      840
cgtctctgaa gactgctcag ggctatcctc tcagagtgac attttaacca ctcagcagag      900
ggataccatg caacataacc tgataaagct ccagcaggaa atggctgaac tagaagctgt      960
gttagaacag catgggagcc agccttctaa cagctaccct tccatcataa gtgactcttc     1020
tgcccttgag gacctgcgaa atccagaaca agcacatca gaaaagtat taacttcaca      1080 gaaaagtagt gaatacccta taagccagaa tccagaaggc ctttctgctg acaagtttga     1140
ggtgtctgca gatagttcta ccagtaaaaa taaagaacca ggagtggaaa ggtcatcccc     1200
ttctaaatgc ccatcattag atgataggtg gtacatgcac agttgctctg ggagtcttca     1260
gaatagaaac tacccatctc aagaggagct cattaaggtt gttgatgtgg aggagcaaca     1320
gctggaagag tctgggccac acgatttgac ggaaacatct tacttgccaa ggcaagatct     1380
agagggaacc ccttacctgg aatctggaat cagcctcttc tctgatgacc ctgaatctga     1440
tccttctgaa gacagagccc cagagtcagc tcgtgttggc aacataccat cttcaacctc     1500
tgcattgaaa gttccccaat tgaaagttgc agaatctgcc cagagtccag ctgctgctca     1560
tactactgat actgctgggt ataatgcaat ggaagaaagt gtgagcaggg agaagccaga     1620
attgacagct tcaacagaaa gggtcaacaa agaatgtcc atggtggtgt ctggcctgac     1680
cccagaagaa tttatgctcg tgtacaagtt tgccagaaaa caccacatca ctttaactaa     1740
tctaattact gaagagacta ctcatgttgt tatgaaaaca gatgctgagt ttgtgtgtga     1800
acggacactg aaatattttc taggaattgc gggaggaaaa tgggtagtta gctatttctg     1860
ggtgacccag tctattaaag aaagaaaaat gctgaatgag catgattttg aagtcagagg     1920
agatgtggtc aatggaagaa accaccaagg tccaaagcga gcaagagaat cccaggacag     1980
aaagatcttc aggggctag aaatctgttg ctatgggccc ttcaccaaca tgcccacaga     2040
tcaactggaa tggatggtac agctgtgtgg tgcttctgtg gtgaaggagc tttcatcatt     2100 caccccttggc acaggtgtcc acccaattgt ggttgtgcag ccagatgcct ggacagagga     2160
caatggcttc catgcaattg ggcagatgtg tgaggcacct gtggtgaccc gagagtgggt     2220
gttggacagt gtagcactct accagtgcca ggagctggac acctacctga tacccccagat     2280 ccccccacagc cactactgac tgcagccagc cacaggtaca gagccacagg accccaagaa     2340
tgagcttaca aagtggcctt tccaggcct gggagctcct ctcactcttc agtccttcta     2400
ctgtcctggc tactaaatat tttatgtaca tcagcctgaa aaggacttct ggctatgcaa     2460
gggtccctta agattttct gcttgaagtc tcccttggaa atctgccatg agcacaaaat     2520
tatggtaatt tttcacctga gaagatttta aaaccattta aacgccacca attgagcaag     2580
atgctgattc attatttatc agccctattc tttctattca ggctgttgtt ggcttagggc     2640
tggaagcaca gagtggcttg gcctcaagag aatagctggt ttccctaagt ttacttctct     2700
aaaaccctgt gttcacaaag gcagagagtc agacccttca atggaaggag agtgcttggg     2760
atcgattatg tgacttaaag tcagaatagt ccttgggcag ttctcaaatg ttggagtgga     2820
acattgggga ggaaattctg aggcaggtat tagaaatgaa aaggaaactt gaaacctggg     2880
catggtggct cacgcctgta atcccagcac tttgggaggc caaggtgggc agatcactgg     2940
aggtcaggag ttcgaaacca gcctggccaa catggtgaaa ccccatctct actaaaaata     3000
cagaaattag ccggtcatgg tggtggacac ctgtaatccc agctactcag gtggctaagg     3060
caggagaatc acttcagccc gggaggtgga ggttgcagtg agccaagatc ataccacggc     3120
```

```
actccagcct gggtgacagt gagactgtgg ctcaaaaaaa aaaaaaaaa aaggaaaatg    3180 aaactagaag agatttctaa aagtctgaga tatatttgct agatttctaa agaatgtgtt    3240
ctaaaacagc agaagatttt caagaaccgg tttccaaaga cagtcttcta attcctcatt    3300
agtaataagt aaaatgttta ttgttgtagc tctggtatat aatccattcc tcttaaaata    3360
taagacctct ggcatgaata tttcatatct ataaaatgac agatcccacc aggaaggaag    3420
ctgttgcttt ctttgaggtg atttttttcc tttgctccct gttgctgaaa ccatacagct    3480
tcataaataa ttttgcttgc tgaaggaaga aaaagtgttt ttcataaacc cattatccag    3540
gactgtttat agctgttgga aggactaggt cttccctagc cccccagtg tgcaagggca    3600 gtgaagactt gattgtacaa aatacgtttt gtaaatgttg tgctgttaac actgcaaata    3660
aacttggtag caaacacttc caaaaaaaaa aaaaaaaa                          3699
```

`<210>` SEQ ID NO 43
`<211>` LENGTH: 3800
`<212>` TYPE: DNA
`<213>` ORGANISM: Homo sapiens

`<400>` SEQUENCE: 43

```
cttagcggta gccccttggt ttccgtggca acggaaaagc gcgggaatta cagataaatt      60
aaaactgcga ctgcgcggcg tgagctcgct gagacttcct ggacgggga caggctgtgg     120 ggtttctcag ataactgggc ccctgcgctc aggaggcctt caccctctgc tctggttcat     180
tggaacagaa agaaatggat ttatctgctc ttcgcgttga agaagtacaa aatgtcatta     240
atgctatgca gaaaatctta gagtgtccca tctgtctgga gttgatcaag gaacctgtct     300
ccacaaagtg tgaccacata tttgcaaat tttgcatgct gaaacttctc aaccagaaga     360
aagggccttc acagtgtcct ttatgtaaga atgatataac caaaggagc ctacaagaaa     420 gtacgagatt tagtcaactt gttgaagagc tattgaaaat catttgtgct tttcagcttg     480
acacaggttt ggagtatgca aacagctata atttgcaaa aaaggaaaat aactctcctg     540
aacatctaaa agatgaagtt tctatcatcc aaagtatggg ctacagaaac cgtgccaaaa     600
gacttctaca gagtgaaccc gaaaatcctt ccttgcagga aaccagtctc agtgtccaac     660
tctctaacct tggaactgtg agaactctga ggacaaagca gcggatacaa cctcaaaaga     720
cgtctgtcta cattgaattg ggatctgatt cttctgaaga taccgttaat aaggcaactt     780
attgcagtgt gggagatcaa gaattgttac aaatcacccc tcaaggaacc agggatgaaa     840
tcagtttgga ttctgcaaaa aaggctgctt gtgaattttc tgagacggat gtaacaaata     900
ctgaacatca tcaacccagt aataatgatt tgaacaccac tgagaagcgt gcagctgaga     960
ggcatccaga aaagtatcag ggtgaagcag catctgggtg tgagagtgaa acaagcgtct    1020
ctgaagactg ctcagggcta tcctctcaga gtgacatttt aaccactcag cagagggata    1080
ccatgcaaca taacctgata aagctccagc aggaaatggc tgaactagaa gctgtgttag    1140
aacagcatgg gagccagcct tctaacagct acccttccat cataagtgac tcttctgccc    1200
ttgaggacct gcgaaatcca gaacaaagca catcagaaaa agtattaact tcacagaaaa    1260
gtagtgaata ccctataagc cagaatccag aaggcctttc tgctgacaag tttgaggtgt    1320
ctgcagatag ttctaccagt aaaaataaag aaccaggagt ggaaaggtca tccccttcta    1380
aatgcccatc attagatgat aggtggtaca tgcacagttg ctctgggagt cttcagaata    1440
gaaactaccc atctcaagag gagctcatta aggttgttga tgtggaggag caacagctgg    1500
aagagtctgg gccacacgat ttgacggaaa catcttactt gccaaggcaa gatctagagg    1560
```

```
gaaccccctta cctggaatct ggaatcagcc tcttctctga tgaccctgaa tctgatcctt    1620
ctgaagacag agccccagag tcagctcgtg ttggcaacat accatcttca acctctgcat    1680
tgaaagttcc ccaattgaaa gttgcagaat ctgcccagag tccagctgct gctcatacta    1740
ctgatactgc tgggtataat gcaatggaag aaagtgtgag cagggagaag ccagaattga    1800
cagcttcaac agaaagggtc aacaaaagaa tgtccatggt ggtgtctggc ctgaccccag    1860
aagaatttat gctcgtgtac aagtttgcca gaaaacacca catcacttta actaatctaa    1920
ttactgaaga gactactcat gttgttatga aaacagatgc tgagtttgtg tgtgaacgga    1980
cactgaaata ttttctagga attgcgggag gaaaatggga gttagctat ttctgggtga     2040 cccagtctat taaagaaaga aaaatgctga atgagcatga ttttgaagtc agaggagatg    2100
tggtcaatgg aagaaaccac caaggtccaa agcgagcaag agaatcccag acagaaaga    2160 tcttcagggg gctagaaatc tgttgctatg ggcccttcac caacatgccc acagggtgtc    2220
cacccaattg tggttgtgca gccagatgcc tggacagagg acaatggctt ccatgcaatt    2280
gggcagatgt gtgaggcacc tgtggtgacc cgagagtggg tgttggacag tgtagcactc    2340
taccagtgcc aggagctgga cacctacctg atacccagca tccccacag ccactactga     2400 ctgcagccag ccacaggtac agagccacag gaccccaaga atgagcttac aaagtggcct    2460
ttccaggccc tgggagctcc tctcactctt cagtccttct actgtcctgg ctactaaata    2520
ttttatgtac atcagcctga aaaggacttc tggctatgca agggtccctt aaagattttc    2580
tgcttgaagt ctcccttgga aatctgccat gagcacaaaa ttatggtaat ttttcacctg    2640
agaagatttt aaaaccattt aaacgccacc aattgagcaa gatgctgatt cattatttat    2700
cagccctatt ctttctattc aggctgttgt tggcttaggg ctggaagcac agagtggctt    2760
ggcctcaaga gaatagctgg tttccctaag tttacttctc taaaaccctg tgttcacaaa    2820
ggcagagagt cagacccttc aatggaagga gagtgcttgg gatcgattat gtgacttaaa    2880
gtcagaatag tccttgggca gttctcaaat gttggagtgg aacattgggg aggaaattct    2940
gaggcaggta ttagaaatga aaaggaaact tgaaacctgg gcatggtggc tcacgcctgt    3000
aatcccagca ctttgggagg ccaaggtggg cagatcactg gaggtcagga gttcgaaacc    3060
agcctggcca acatggtgaa accccatctc tactaaaaat acagaaatta gccggtcatg    3120
gtggtggaca cctgtaatcc cagctactca ggtggctaag gcaggagaat cacttcagcc    3180
cgggaggtgg aggttgcagt gagccaagat cataccacgg cactccagcc tgggtgacag    3240
tgagactgtg gctcaaaaaa aaaaaaaaa aaaggaaaat gaaactagaa gagatttcta    3300
aaagtctgag atatatttgc tagatttcta aagaatgtgt tctaaaacag cagaagattt    3360
tcaagaaccg gtttccaaag acagtcttct aattcctcat tagtaataag taaaatgttt    3420
attgttgtag ctctggtata taatccattc ctcttaaaat ataagacctc tggcatgaat    3480
atttcatatc tataaaatga cagatcccac caggaaggaa gctgttgctt tctttgaggt    3540
gatttttttc ctttgctccc tgttgctgaa accatacagc ttcataaata attttgcttg    3600
ctgaaggaag aaaagtgtt tttcataaac ccattatcca ggactgttta tagctgttgg     3660
aaggactagg tcttccctag ccccccagt gtgcaaggc agtgaagact tgattgtaca      3720
aaatacgttt tgtaaatgtt gtgctgttaa cactgcaaat aaacttggta gcaaacactt    3780
ccaaaaaaaa aaaaaaaaa                                                 3800
```

<210> SEQ ID NO 44

```
<211> LENGTH: 1863
<212> TYPE: PRT
<213> ORGANISM: Homo sapiens

<400> SEQUENCE: 44
```

| | | | | | | | | | | | | | | |
|---|---|---|---|---|---|---|---|---|---|---|---|---|---|---|
| Met | Asp | Leu | Ser | Ala | Leu | Arg | Val | Glu | Glu | Val | Gln | Asn | Val | Ile | Asn |
| 1 | | | | 5 | | | | | 10 | | | | | 15 | |
| Ala | Met | Gln | Lys | Ile | Leu | Glu | Cys | Pro | Ile | Cys | Leu | Glu | Leu | Ile | Lys |
| | | | 20 | | | | | 25 | | | | | 30 | | |
| Glu | Pro | Val | Ser | Thr | Lys | Cys | Asp | His | Ile | Phe | Cys | Lys | Phe | Cys | Met |
| | | | 35 | | | | | 40 | | | | | 45 | | |
| Leu | Lys | Leu | Leu | Asn | Gln | Lys | Lys | Gly | Pro | Ser | Gln | Cys | Pro | Leu | Cys |
| | 50 | | | | | 55 | | | | | 60 | | | | |
| Lys | Asn | Asp | Ile | Thr | Lys | Arg | Ser | Leu | Gln | Glu | Ser | Thr | Arg | Phe | Ser |
| 65 | | | | | 70 | | | | | 75 | | | | | 80 |
| Gln | Leu | Val | Glu | Glu | Leu | Leu | Lys | Ile | Ile | Cys | Ala | Phe | Gln | Leu | Asp |
| | | | | 85 | | | | | 90 | | | | | 95 | |
| Thr | Gly | Leu | Glu | Tyr | Ala | Asn | Ser | Tyr | Asn | Phe | Ala | Lys | Lys | Glu | Asn |
| | | | 100 | | | | | 105 | | | | | 110 | | |
| Asn | Ser | Pro | Glu | His | Leu | Lys | Asp | Glu | Val | Ser | Ile | Ile | Gln | Ser | Met |
| | | | 115 | | | | | 120 | | | | | 125 | | |
| Gly | Tyr | Arg | Asn | Arg | Ala | Lys | Arg | Leu | Leu | Gln | Ser | Glu | Pro | Glu | Asn |
| | 130 | | | | | 135 | | | | | 140 | | | | |
| Pro | Ser | Leu | Gln | Glu | Thr | Ser | Leu | Ser | Val | Gln | Leu | Ser | Asn | Leu | Gly |
| 145 | | | | | 150 | | | | | 155 | | | | | 160 |
| Thr | Val | Arg | Thr | Leu | Arg | Thr | Lys | Gln | Arg | Ile | Gln | Pro | Gln | Lys | Thr |
| | | | | 165 | | | | | 170 | | | | | 175 | |
| Ser | Val | Tyr | Ile | Glu | Leu | Gly | Ser | Asp | Ser | Ser | Glu | Asp | Thr | Val | Asn |
| | | | 180 | | | | | 185 | | | | | 190 | | |
| Lys | Ala | Thr | Tyr | Cys | Ser | Val | Gly | Asp | Gln | Glu | Leu | Leu | Gln | Ile | Thr |
| | | | 195 | | | | | 200 | | | | | 205 | | |
| Pro | Gln | Gly | Thr | Arg | Asp | Glu | Ile | Ser | Leu | Asp | Ser | Ala | Lys | Lys | Ala |
| | 210 | | | | | 215 | | | | | 220 | | | | |
| Ala | Cys | Glu | Phe | Ser | Glu | Thr | Asp | Val | Thr | Asn | Thr | Glu | His | His | Gln |
| 225 | | | | | 230 | | | | | 235 | | | | | 240 |
| Pro | Ser | Asn | Asn | Asp | Leu | Asn | Thr | Thr | Glu | Lys | Arg | Ala | Ala | Glu | Arg |
| | | | | 245 | | | | | 250 | | | | | 255 | |
| His | Pro | Glu | Lys | Tyr | Gln | Gly | Ser | Ser | Val | Ser | Asn | Leu | His | Val | Glu |
| | | | 260 | | | | | 265 | | | | | 270 | | |
| Pro | Cys | Gly | Thr | Asn | Thr | His | Ala | Ser | Ser | Leu | Gln | His | Glu | Asn | Ser |
| | | | 275 | | | | | 280 | | | | | 285 | | |
| Ser | Leu | Leu | Leu | Thr | Lys | Asp | Arg | Met | Asn | Val | Glu | Lys | Ala | Glu | Phe |
| | 290 | | | | | 295 | | | | | 300 | | | | |
| Cys | Asn | Lys | Ser | Lys | Gln | Pro | Gly | Leu | Ala | Arg | Ser | Gln | His | Asn | Arg |
| 305 | | | | | 310 | | | | | 315 | | | | | 320 |
| Trp | Ala | Gly | Ser | Lys | Glu | Thr | Cys | Asn | Asp | Arg | Arg | Thr | Pro | Ser | Thr |
| | | | | 325 | | | | | 330 | | | | | 335 | |
| Glu | Lys | Lys | Val | Asp | Leu | Asn | Ala | Asp | Pro | Leu | Cys | Glu | Arg | Lys | Glu |
| | | | 340 | | | | | 345 | | | | | 350 | | |
| Trp | Asn | Lys | Gln | Lys | Leu | Pro | Cys | Ser | Glu | Asn | Pro | Arg | Asp | Thr | Glu |
| | | | 355 | | | | | 360 | | | | | 365 | | |
| Asp | Val | Pro | Trp | Ile | Thr | Leu | Asn | Ser | Ser | Ile | Gln | Lys | Val | Asn | Glu |
| | 370 | | | | | 375 | | | | | 380 | | | | |
| Trp | Phe | Ser | Arg | Ser | Asp | Glu | Leu | Leu | Gly | Ser | Asp | Asp | Ser | His | Asp |

```
            385                 390                 395                 400
Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Glu Arg Val His
                435                 440                 445

Ser Lys Ser Val Glu Ser Asn Ile Glu Asp Lys Ile Phe Gly Lys Thr
                450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Gln Glu Arg
                485                 490                 495

Pro Leu Thr Asn Lys Leu Lys Arg Lys Arg Pro Thr Ser Gly Leu
                500                 505                 510

His Pro Glu Asp Phe Ile Lys Lys Ala Asp Leu Ala Val Gln Lys Thr
                515                 520                 525

Pro Glu Met Ile Asn Gln Gly Thr Asn Gln Thr Glu Gln Asn Gly Gln
                530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
                580                 585                 590

Asn Met Glu Leu Glu Leu Asn Ile His Asn Ser Lys Ala Pro Lys Lys
                595                 600                 605

Asn Arg Leu Arg Arg Lys Ser Ser Thr Arg His Ile His Ala Leu Glu
                610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
                660                 665                 670

Glu Pro Ala Thr Gly Ala Lys Lys Ser Asn Lys Pro Asn Glu Gln Thr
                675                 680                 685

Ser Lys Arg His Asp Ser Asp Thr Phe Pro Glu Leu Lys Leu Thr Asn
                690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
                740                 745                 750

Ser Gly Glu Arg Val Leu Gln Thr Glu Arg Ser Val Glu Ser Ser Ser
                755                 760                 765

Ile Ser Leu Val Pro Gly Thr Asp Tyr Gly Thr Gln Glu Ser Ile Ser
                770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815
```

```
Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val
    1010                1015                1020

Ser Thr Ile Ser Arg Asn Asn Ile Arg Glu Asn Val Phe Lys Glu
    1025                1030                1035

Ala Ser Ser Ser Asn Ile Asn Glu Val Gly Ser Ser Thr Asn Glu
    1040                1045                1050

Val Gly Ser Ser Ile Asn Glu Ile Gly Ser Ser Asp Glu Asn Ile
    1055                1060                1065

Gln Ala Glu Leu Gly Arg Asn Arg Gly Pro Lys Leu Asn Ala Met
    1070                1075                1080

Leu Arg Leu Gly Val Leu Gln Pro Glu Val Tyr Lys Gln Ser Leu
    1085                1090                1095

Pro Gly Ser Asn Cys Lys His Pro Glu Ile Lys Lys Gln Glu Tyr
    1100                1105                1110

Glu Glu Val Val Gln Thr Val Asn Thr Asp Phe Ser Pro Tyr Leu
    1115                1120                1125

Ile Ser Asp Asn Leu Glu Gln Pro Met Gly Ser Ser His Ala Ser
    1130                1135                1140

Gln Val Cys Ser Glu Thr Pro Asp Asp Leu Leu Asp Asp Gly Glu
    1145                1150                1155

Ile Lys Glu Asp Thr Ser Phe Ala Glu Asn Asp Ile Lys Glu Ser
    1160                1165                1170

Ser Ala Val Phe Ser Lys Ser Val Gln Lys Gly Glu Leu Ser Arg
    1175                1180                1185

Ser Pro Ser Pro Phe Thr His Thr His Leu Ala Gln Gly Tyr Arg
    1190                1195                1200

Arg Gly Ala Lys Lys Leu Glu Ser Ser Glu Glu Asn Leu Ser Ser
    1205                1210                1215
```

```
Glu Asp Glu Glu Leu Pro Cys Phe Gln His Leu Leu Phe Gly Lys
1220                1225                1230

Val Asn Asn Ile Pro Ser Gln Ser Thr Arg His Ser Thr Val Ala
    1235                1240                1245

Thr Glu Cys Leu Ser Lys Asn Thr Glu Glu Asn Leu Leu Ser Leu
1250                1255                1260

Lys Asn Ser Leu Asn Asp Cys Ser Asn Gln Val Ile Leu Ala Lys
1265                1270                1275

Ala Ser Gln Glu His His Leu Ser Glu Glu Thr Lys Cys Ser Ala
1280                1285                1290

Ser Leu Phe Ser Ser Gln Cys Ser Glu Leu Glu Asp Leu Thr Ala
1295                1300                1305

Asn Thr Asn Thr Gln Asp Pro Phe Leu Ile Gly Ser Ser Lys Gln
1310                1315                1320

Met Arg His Gln Ser Glu Ser Gln Gly Val Gly Leu Ser Asp Lys
1325                1330                1335

Glu Leu Val Ser Asp Asp Glu Glu Arg Gly Thr Gly Leu Glu Glu
1340                1345                1350

Asn Asn Gln Glu Glu Gln Ser Met Asp Ser Asn Leu Gly Glu Ala
1355                1360                1365

Ala Ser Gly Cys Glu Ser Glu Thr Ser Val Ser Glu Asp Cys Ser
1370                1375                1380

Gly Leu Ser Ser Gln Ser Asp Ile Leu Thr Thr Gln Gln Arg Asp
1385                1390                1395

Thr Met Gln His Asn Leu Ile Lys Leu Gln Gln Glu Met Ala Glu
1400                1405                1410

Leu Glu Ala Val Leu Glu Gln His Gly Ser Gln Pro Ser Asn Ser
1415                1420                1425

Tyr Pro Ser Ile Ile Ser Asp Ser Ser Ala Leu Glu Asp Leu Arg
1430                1435                1440

Asn Pro Glu Gln Ser Thr Ser Glu Lys Ala Val Leu Thr Ser Gln
1445                1450                1455

Lys Ser Ser Glu Tyr Pro Ile Ser Gln Asn Pro Glu Gly Leu Ser
1460                1465                1470

Ala Asp Lys Phe Glu Val Ser Ala Asp Ser Ser Thr Ser Lys Asn
1475                1480                1485

Lys Glu Pro Gly Val Glu Arg Ser Ser Pro Ser Lys Cys Pro Ser
1490                1495                1500

Leu Asp Asp Arg Trp Tyr Met His Ser Cys Ser Gly Ser Leu Gln
1505                1510                1515

Asn Arg Asn Tyr Pro Ser Gln Glu Glu Leu Ile Lys Val Val Asp
1520                1525                1530

Val Glu Glu Gln Gln Leu Glu Glu Ser Gly Pro His Asp Leu Thr
1535                1540                1545

Glu Thr Ser Tyr Leu Pro Arg Gln Asp Leu Glu Gly Thr Pro Tyr
1550                1555                1560

Leu Glu Ser Gly Ile Ser Leu Phe Ser Asp Asp Pro Glu Ser Asp
1565                1570                1575

Pro Ser Glu Asp Arg Ala Pro Glu Ser Ala Arg Val Gly Asn Ile
1580                1585                1590

Pro Ser Ser Thr Ser Ala Leu Lys Val Pro Gln Leu Lys Val Ala
1595                1600                1605

Glu Ser Ala Gln Ser Pro Ala Ala Ala His Thr Thr Asp Thr Ala
```

-continued

```
                    1610                1615                1620

Gly Tyr Asn Ala Met Glu Glu Ser Val Ser Arg Glu Lys Pro Glu
                1625                1630                1635

Leu Thr Ala Ser Thr Glu Arg Val Asn Lys Arg Met Ser Met Val
            1640                1645                1650

Val Ser Gly Leu Thr Pro Glu Glu Phe Met Leu Val Tyr Lys Phe
        1655                1660                1665

Ala Arg Lys His His Ile Thr Leu Thr Asn Leu Ile Thr Glu Glu
    1670                1675                1680

Thr Thr His Val Val Met Lys Thr Asp Ala Glu Phe Val Cys Glu
1685                1690                1695

Arg Thr Leu Lys Tyr Phe Leu Gly Ile Ala Gly Gly Lys Trp Val
    1700                1705                1710

Val Ser Tyr Phe Trp Val Thr Gln Ser Ile Lys Glu Arg Lys Met
    1715                1720                1725

Leu Asn Glu His Asp Phe Glu Val Arg Gly Asp Val Val Asn Gly
    1730                1735                1740

Arg Asn His Gln Gly Pro Lys Arg Ala Arg Glu Ser Gln Asp Arg
    1745                1750                1755

Lys Ile Phe Arg Gly Leu Glu Ile Cys Cys Tyr Gly Pro Phe Thr
    1760                1765                1770

Asn Met Pro Thr Asp Gln Leu Glu Trp Met Val Gln Leu Cys Gly
    1775                1780                1785

Ala Ser Val Val Lys Glu Leu Ser Ser Phe Thr Leu Gly Thr Gly
    1790                1795                1800

Val His Pro Ile Val Val Val Gln Pro Asp Ala Trp Thr Glu Asp
    1805                1810                1815

Asn Gly Phe His Ala Ile Gly Gln Met Cys Glu Ala Pro Val Val
    1820                1825                1830

Thr Arg Glu Trp Val Leu Asp Ser Val Ala Leu Tyr Gln Cys Gln
    1835                1840                1845

Glu Leu Asp Thr Tyr Leu Ile Pro Gln Ile Pro His Ser His Tyr
    1850                1855                1860
```

<210> SEQ ID NO 45
<211> LENGTH: 1884
<212> TYPE: PRT
<213> ORGANISM: Homo sapiens

<400> SEQUENCE: 45

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110
```

-continued

```
Asn Ser Pro Glu His Leu Lys Asp Glu Val Ser Ile Ile Gln Ser Met
            115                 120                 125
Gly Tyr Arg Asn Arg Ala Lys Arg Leu Leu Gln Ser Glu Pro Glu Asn
        130                 135                 140
Pro Ser Leu Gln Glu Thr Ser Leu Ser Val Gln Leu Ser Asn Leu Gly
145                 150                 155                 160
Thr Val Arg Thr Leu Arg Thr Lys Gln Arg Ile Gln Pro Gln Lys Thr
                165                 170                 175
Ser Val Tyr Ile Glu Leu Gly Ser Asp Ser Ser Glu Asp Thr Val Asn
            180                 185                 190
Lys Ala Thr Tyr Cys Ser Val Gly Asp Gln Glu Leu Leu Gln Ile Thr
        195                 200                 205
Pro Gln Gly Thr Arg Asp Glu Ile Ser Leu Asp Ser Ala Lys Lys Ala
210                 215                 220
Ala Cys Glu Phe Ser Glu Thr Asp Val Thr Asn Thr Glu His His Gln
225                 230                 235                 240
Pro Ser Asn Asn Asp Leu Asn Thr Thr Glu Lys Arg Ala Ala Glu Arg
                245                 250                 255
His Pro Glu Lys Tyr Gln Gly Ser Ser Val Ser Asn Leu His Val Glu
            260                 265                 270
Pro Cys Gly Thr Asn Thr His Ala Ser Ser Leu Gln His Glu Asn Ser
        275                 280                 285
Ser Leu Leu Leu Thr Lys Asp Arg Met Asn Val Glu Lys Ala Glu Phe
290                 295                 300
Cys Asn Lys Ser Lys Gln Pro Gly Leu Ala Arg Ser Gln His Asn Arg
305                 310                 315                 320
Trp Ala Gly Ser Lys Glu Thr Cys Asn Asp Arg Arg Thr Pro Ser Thr
                325                 330                 335
Glu Lys Lys Val Asp Leu Asn Ala Asp Pro Leu Cys Glu Arg Lys Glu
            340                 345                 350
Trp Asn Lys Gln Lys Leu Pro Cys Ser Glu Asn Pro Arg Asp Thr Glu
        355                 360                 365
Asp Val Pro Trp Ile Thr Leu Asn Ser Ser Ile Gln Lys Val Asn Glu
370                 375                 380
Trp Phe Ser Arg Ser Asp Glu Leu Leu Gly Ser Asp Asp Ser His Asp
385                 390                 395                 400
Gly Glu Ser Glu Ser Asn Ala Lys Val Ala Asp Val Leu Asp Val Leu
                405                 410                 415
Asn Glu Val Asp Glu Tyr Ser Gly Ser Ser Glu Lys Ile Asp Leu Leu
            420                 425                 430
Ala Ser Asp Pro His Glu Ala Leu Ile Cys Lys Ser Glu Arg Val His
        435                 440                 445
Ser Lys Ser Val Glu Ser Asn Ile Glu Asp Lys Ile Phe Gly Lys Thr
450                 455                 460
Tyr Arg Lys Lys Ala Ser Leu Pro Asn Leu Ser His Val Thr Glu Asn
465                 470                 475                 480
Leu Ile Ile Gly Ala Phe Val Thr Glu Pro Gln Ile Ile Gln Glu Arg
                485                 490                 495
Pro Leu Thr Asn Lys Leu Lys Arg Lys Arg Arg Pro Thr Ser Gly Leu
            500                 505                 510
His Pro Glu Asp Phe Ile Lys Lys Ala Asp Leu Ala Val Gln Lys Thr
        515                 520                 525
Pro Glu Met Ile Asn Gln Gly Thr Asn Gln Thr Glu Gln Asn Gly Gln
```

```
            530                 535                 540
Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
                580                 585                 590

Asn Met Glu Leu Glu Leu Asn Ile His Asn Ser Lys Ala Pro Lys Lys
            595                 600                 605

Asn Arg Leu Arg Arg Lys Ser Ser Thr Arg His Ile His Ala Leu Glu
        610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
                660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
        690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
                740                 745                 750

Ser Gly Glu Arg Val Leu Gln Thr Glu Arg Ser Val Glu Ser Ser Ser
            755                 760                 765

Ile Ser Leu Val Pro Gly Thr Asp Tyr Gly Thr Gln Glu Ser Ile Ser
        770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
                820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
        850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
                900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
        930                 935                 940

Ser Ile Lys Gly Gly Ser Arg Phe Cys Leu Ser Ser Gln Phe Arg Gly
945                 950                 955                 960
```

-continued

```
Asn Glu Thr Gly Leu Ile Thr Pro Asn Lys His Gly Leu Leu Gln Asn
            965                 970                 975
Pro Tyr Arg Ile Pro Pro Leu Phe Pro Ile Lys Ser Phe Val Lys Thr
            980                 985                 990
Lys Cys Lys Lys Asn Leu Leu Glu Glu Asn Phe Glu Glu His Ser Met
            995                 1000                1005
Ser Pro Glu Arg Glu Met Gly Asn Glu Asn Ile Pro Ser Thr Val
        1010                1015                1020
Ser Thr Ile Ser Arg Asn Asn Ile Arg Glu Asn Val Phe Lys Glu
        1025                1030                1035
Ala Ser Ser Ser Asn Ile Asn Glu Val Gly Ser Ser Thr Asn Glu
        1040                1045                1050
Val Gly Ser Ser Ile Asn Glu Ile Gly Ser Ser Asp Glu Asn Ile
        1055                1060                1065
Gln Ala Glu Leu Gly Arg Asn Arg Gly Pro Lys Leu Asn Ala Met
        1070                1075                1080
Leu Arg Leu Gly Val Leu Gln Pro Glu Val Tyr Lys Gln Ser Leu
        1085                1090                1095
Pro Gly Ser Asn Cys Lys His Pro Glu Ile Lys Lys Gln Glu Tyr
        1100                1105                1110
Glu Glu Val Val Gln Thr Val Asn Thr Asp Phe Ser Pro Tyr Leu
        1115                1120                1125
Ile Ser Asp Asn Leu Glu Gln Pro Met Gly Ser Ser His Ala Ser
        1130                1135                1140
Gln Val Cys Ser Glu Thr Pro Asp Asp Leu Leu Asp Asp Gly Glu
        1145                1150                1155
Ile Lys Glu Asp Thr Ser Phe Ala Glu Asn Asp Ile Lys Glu Ser
        1160                1165                1170
Ser Ala Val Phe Ser Lys Ser Val Gln Lys Gly Glu Leu Ser Arg
        1175                1180                1185
Ser Pro Ser Pro Phe Thr His Thr His Leu Ala Gln Gly Tyr Arg
        1190                1195                1200
Arg Gly Ala Lys Lys Leu Glu Ser Ser Glu Glu Asn Leu Ser Ser
        1205                1210                1215
Glu Asp Glu Glu Leu Pro Cys Phe Gln His Leu Leu Phe Gly Lys
        1220                1225                1230
Val Asn Asn Ile Pro Ser Gln Ser Thr Arg His Ser Thr Val Ala
        1235                1240                1245
Thr Glu Cys Leu Ser Lys Asn Thr Glu Glu Asn Leu Leu Ser Leu
        1250                1255                1260
Lys Asn Ser Leu Asn Asp Cys Ser Asn Gln Val Ile Leu Ala Lys
        1265                1270                1275
Ala Ser Gln Glu His His Leu Ser Glu Glu Thr Lys Cys Ser Ala
        1280                1285                1290
Ser Leu Phe Ser Ser Gln Cys Ser Glu Leu Glu Asp Leu Thr Ala
        1295                1300                1305
Asn Thr Asn Thr Gln Asp Pro Phe Leu Ile Gly Ser Ser Lys Gln
        1310                1315                1320
Met Arg His Gln Ser Glu Ser Gln Gly Val Gly Leu Ser Asp Lys
        1325                1330                1335
Glu Leu Val Ser Asp Asp Glu Glu Arg Gly Thr Gly Leu Glu Glu
        1340                1345                1350
```

```
Asn Asn Gln Glu Glu Gln Ser Met Asp Ser Asn Leu Gly Glu Ala
    1355                1360                1365

Ala Ser Gly Cys Glu Ser Glu Thr Ser Val Ser Glu Asp Cys Ser
    1370                1375                1380

Gly Leu Ser Ser Gln Ser Asp Ile Leu Thr Thr Gln Gln Arg Asp
    1385                1390                1395

Thr Met Gln His Asn Leu Ile Lys Leu Gln Gln Glu Met Ala Glu
    1400                1405                1410

Leu Glu Ala Val Leu Glu Gln His Gly Ser Gln Pro Ser Asn Ser
    1415                1420                1425

Tyr Pro Ser Ile Ile Ser Asp Ser Ser Ala Leu Glu Asp Leu Arg
    1430                1435                1440

Asn Pro Glu Gln Ser Thr Ser Glu Lys Asp Ser His Ile His Gly
    1445                1450                1455

Gln Arg Asn Asn Ser Met Phe Ser Lys Arg Pro Arg Glu His Ile
    1460                1465                1470

Ser Val Leu Thr Ser Gln Lys Ser Ser Glu Tyr Pro Ile Ser Gln
    1475                1480                1485

Asn Pro Glu Gly Leu Ser Ala Asp Lys Phe Glu Val Ser Ala Asp
    1490                1495                1500

Ser Ser Thr Ser Lys Asn Lys Glu Pro Gly Val Glu Arg Ser Ser
    1505                1510                1515

Pro Ser Lys Cys Pro Ser Leu Asp Asp Arg Trp Tyr Met His Ser
    1520                1525                1530

Cys Ser Gly Ser Leu Gln Asn Arg Asn Tyr Pro Ser Gln Glu Glu
    1535                1540                1545

Leu Ile Lys Val Val Asp Val Glu Glu Gln Gln Leu Glu Glu Ser
    1550                1555                1560

Gly Pro His Asp Leu Thr Glu Thr Ser Tyr Leu Pro Arg Gln Asp
    1565                1570                1575

Leu Glu Gly Thr Pro Tyr Leu Glu Ser Gly Ile Ser Leu Phe Ser
    1580                1585                1590

Asp Asp Pro Glu Ser Asp Pro Ser Glu Asp Arg Ala Pro Glu Ser
    1595                1600                1605

Ala Arg Val Gly Asn Ile Pro Ser Ser Thr Ser Ala Leu Lys Val
    1610                1615                1620

Pro Gln Leu Lys Val Ala Glu Ser Ala Gln Ser Pro Ala Ala Ala
    1625                1630                1635

His Thr Thr Asp Thr Ala Gly Tyr Asn Ala Met Glu Glu Ser Val
    1640                1645                1650

Ser Arg Glu Lys Pro Glu Leu Thr Ala Ser Thr Glu Arg Val Asn
    1655                1660                1665

Lys Arg Met Ser Met Val Val Ser Gly Leu Thr Pro Glu Glu Phe
    1670                1675                1680

Met Leu Val Tyr Lys Phe Ala Arg Lys His His Ile Thr Leu Thr
    1685                1690                1695

Asn Leu Ile Thr Glu Glu Thr Thr His Val Val Met Lys Thr Asp
    1700                1705                1710

Ala Glu Phe Val Cys Glu Arg Thr Leu Lys Tyr Phe Leu Gly Ile
    1715                1720                1725

Ala Gly Gly Lys Trp Val Val Ser Tyr Phe Trp Val Thr Gln Ser
    1730                1735                1740

Ile Lys Glu Arg Lys Met Leu Asn Glu His Asp Phe Glu Val Arg
```

```
            1745                1750                1755
Gly Asp Val Val Asn Gly Arg Asn His Gln Gly Pro Lys Arg Ala
        1760                1765                1770

Arg Glu Ser Gln Asp Arg Lys Ile Phe Arg Gly Leu Glu Ile Cys
        1775                1780                1785

Cys Tyr Gly Pro Phe Thr Asn Met Pro Thr Asp Gln Leu Glu Trp
        1790                1795                1800

Met Val Gln Leu Cys Gly Ala Ser Val Val Lys Glu Leu Ser Ser
        1805                1810                1815

Phe Thr Leu Gly Thr Gly Val His Pro Ile Val Val Gln Pro
        1820                1825                1830

Asp Ala Trp Thr Glu Asp Asn Gly Phe His Ala Ile Gly Gln Met
        1835                1840                1845

Cys Glu Ala Pro Val Val Thr Arg Glu Trp Val Leu Asp Ser Val
        1850                1855                1860

Ala Leu Tyr Gln Cys Gln Glu Leu Asp Thr Tyr Leu Ile Pro Gln
        1865                1870                1875

Ile Pro His Ser His Tyr
        1880

<210> SEQ ID NO 46
<211> LENGTH: 1816
<212> TYPE: PRT
<213> ORGANISM: Homo sapiens

<400> SEQUENCE: 46

Met Leu Lys Leu Leu Asn Gln Lys Lys Gly Pro Ser Gln Cys Pro Leu
1               5                   10                  15

Cys Lys Asn Asp Ile Thr Lys Arg Ser Leu Gln Glu Ser Thr Arg Phe
            20                  25                  30

Ser Gln Leu Val Glu Glu Leu Leu Lys Ile Ile Cys Ala Phe Gln Leu
        35                  40                  45

Asp Thr Gly Leu Glu Tyr Ala Asn Ser Tyr Asn Phe Ala Lys Lys Glu
    50                  55                  60

Asn Asn Ser Pro Glu His Leu Lys Asp Glu Val Ser Ile Ile Gln Ser
65                  70                  75                  80

Met Gly Tyr Arg Asn Arg Ala Lys Arg Leu Leu Gln Ser Glu Pro Glu
                85                  90                  95

Asn Pro Ser Leu Gln Glu Thr Ser Leu Ser Val Gln Leu Ser Asn Leu
            100                 105                 110

Gly Thr Val Arg Thr Leu Arg Thr Lys Gln Arg Ile Gln Pro Gln Lys
        115                 120                 125

Thr Ser Val Tyr Ile Glu Leu Gly Ser Asp Ser Ser Glu Asp Thr Val
    130                 135                 140

Asn Lys Ala Thr Tyr Cys Ser Val Gly Asp Gln Glu Leu Leu Gln Ile
145                 150                 155                 160

Thr Pro Gln Gly Thr Arg Asp Glu Ile Ser Leu Asp Ser Ala Lys Lys
                165                 170                 175

Ala Ala Cys Glu Phe Ser Glu Thr Asp Val Thr Asn Thr Glu His His
            180                 185                 190

Gln Pro Ser Asn Asn Asp Leu Asn Thr Thr Glu Lys Arg Ala Ala Glu
        195                 200                 205

Arg His Pro Glu Lys Tyr Gln Gly Ser Ser Val Ser Asn Leu His Val
    210                 215                 220
```

-continued

Glu Pro Cys Gly Thr Asn Thr His Ala Ser Ser Leu Gln His Glu Asn
225                 230                 235                 240

Ser Ser Leu Leu Leu Thr Lys Asp Arg Met Asn Val Glu Lys Ala Glu
            245                 250                 255

Phe Cys Asn Lys Ser Lys Gln Pro Gly Leu Ala Arg Ser Gln His Asn
        260                 265                 270

Arg Trp Ala Gly Ser Lys Glu Thr Cys Asn Asp Arg Arg Thr Pro Ser
    275                 280                 285

Thr Glu Lys Lys Val Asp Leu Asn Ala Asp Pro Leu Cys Glu Arg Lys
290                 295                 300

Glu Trp Asn Lys Gln Lys Leu Pro Cys Ser Glu Asn Pro Arg Asp Thr
305                 310                 315                 320

Glu Asp Val Pro Trp Ile Thr Leu Asn Ser Ser Ile Gln Lys Val Asn
                325                 330                 335

Glu Trp Phe Ser Arg Ser Asp Glu Leu Leu Gly Ser Asp Asp Ser His
            340                 345                 350

Asp Gly Glu Ser Glu Ser Asn Ala Lys Val Ala Asp Val Leu Asp Val
        355                 360                 365

Leu Asn Glu Val Asp Glu Tyr Ser Gly Ser Ser Glu Lys Ile Asp Leu
370                 375                 380

Leu Ala Ser Asp Pro His Glu Ala Leu Ile Cys Lys Ser Glu Arg Val
385                 390                 395                 400

His Ser Lys Ser Val Glu Ser Asn Ile Glu Asp Lys Ile Phe Gly Lys
                405                 410                 415

Thr Tyr Arg Lys Lys Ala Ser Leu Pro Asn Leu Ser His Val Thr Glu
            420                 425                 430

Asn Leu Ile Ile Gly Ala Phe Val Thr Glu Pro Gln Ile Ile Gln Glu
        435                 440                 445

Arg Pro Leu Thr Asn Lys Leu Lys Arg Lys Arg Arg Pro Thr Ser Gly
    450                 455                 460

Leu His Pro Glu Asp Phe Ile Lys Lys Ala Asp Leu Ala Val Gln Lys
465                 470                 475                 480

Thr Pro Glu Met Ile Asn Gln Gly Thr Asn Gln Thr Glu Gln Asn Gly
                485                 490                 495

Gln Val Met Asn Ile Thr Asn Ser Gly His Glu Asn Lys Thr Lys Gly
            500                 505                 510

Asp Ser Ile Gln Asn Glu Lys Asn Pro Asn Pro Ile Glu Ser Leu Glu
        515                 520                 525

Lys Glu Ser Ala Phe Lys Thr Lys Ala Glu Pro Ile Ser Ser Ser Ile
530                 535                 540

Ser Asn Met Glu Leu Glu Leu Asn Ile His Asn Ser Lys Ala Pro Lys
545                 550                 555                 560

Lys Asn Arg Leu Arg Arg Lys Ser Ser Thr Arg His Ile His Ala Leu
                565                 570                 575

Glu Leu Val Val Ser Arg Asn Leu Ser Pro Pro Asn Cys Thr Glu Leu
            580                 585                 590

Gln Ile Asp Ser Cys Ser Ser Ser Glu Glu Ile Lys Lys Lys Lys Tyr
        595                 600                 605

Asn Gln Met Pro Val Arg His Ser Arg Asn Leu Gln Leu Met Glu Gly
610                 615                 620

Lys Glu Pro Ala Thr Gly Ala Lys Lys Ser Asn Lys Pro Asn Glu Gln
625                 630                 635                 640

Thr Ser Lys Arg His Asp Ser Asp Thr Phe Pro Glu Leu Lys Leu Thr

-continued

```
            645                 650                 655
Asn Ala Pro Gly Ser Phe Thr Lys Cys Ser Asn Thr Ser Glu Leu Lys
            660                 665                 670

Glu Phe Val Asn Pro Ser Leu Pro Arg Glu Glu Lys Glu Glu Lys Leu
            675                 680                 685

Glu Thr Val Lys Val Ser Asn Ala Glu Asp Pro Lys Asp Leu Met
            690                 695                 700

Leu Ser Gly Arg Val Leu Gln Thr Glu Arg Ser Val Glu Ser Ser
705                 710                 715                 720

Ser Ile Ser Leu Val Pro Gly Thr Asp Tyr Gly Thr Gln Glu Ser Ile
            725                 730                 735

Ser Leu Leu Glu Val Ser Thr Leu Gly Lys Ala Lys Thr Glu Pro Asn
            740                 745                 750

Lys Cys Val Ser Gln Cys Ala Ala Phe Glu Asn Pro Lys Gly Leu Ile
            755                 760                 765

His Gly Cys Ser Lys Asp Asn Arg Asn Asp Thr Glu Gly Phe Lys Tyr
            770                 775                 780

Pro Leu Gly His Glu Val Asn His Ser Arg Glu Thr Ser Ile Glu Met
785                 790                 795                 800

Glu Glu Ser Glu Leu Asp Ala Gln Tyr Leu Gln Asn Thr Phe Lys Val
            805                 810                 815

Ser Lys Arg Gln Ser Phe Ala Pro Phe Ser Asn Pro Gly Asn Ala Glu
            820                 825                 830

Glu Glu Cys Ala Thr Phe Ser Ala His Ser Gly Ser Leu Lys Lys Gln
            835                 840                 845

Ser Pro Lys Val Thr Phe Glu Cys Glu Gln Lys Glu Glu Asn Gln Gly
            850                 855                 860

Lys Asn Glu Ser Asn Ile Lys Pro Val Gln Thr Val Asn Ile Thr Ala
865                 870                 875                 880

Gly Phe Pro Val Val Gly Gln Lys Asp Lys Pro Val Asp Asn Ala Lys
            885                 890                 895

Cys Ser Ile Lys Gly Gly Ser Arg Phe Cys Leu Ser Ser Gln Phe Arg
            900                 905                 910

Gly Asn Glu Thr Gly Leu Ile Thr Pro Asn Lys His Gly Leu Leu Gln
            915                 920                 925

Asn Pro Tyr Arg Ile Pro Pro Leu Phe Pro Ile Lys Ser Phe Val Lys
            930                 935                 940

Thr Lys Cys Lys Lys Asn Leu Leu Glu Glu Asn Phe Glu Glu His Ser
945                 950                 955                 960

Met Ser Pro Glu Arg Glu Met Gly Asn Glu Asn Ile Pro Ser Thr Val
            965                 970                 975

Ser Thr Ile Ser Arg Asn Asn Ile Arg Glu Asn Val Phe Lys Glu Ala
            980                 985                 990

Ser Ser Ser Asn Ile Asn Glu Val Gly Ser Ser Thr Asn Glu Val Gly
            995                 1000                1005

Ser Ser Ile Asn Glu Ile Gly Ser Ser Asp Glu Asn Ile Gln Ala
            1010                1015                1020

Glu Leu Gly Arg Asn Arg Gly Pro Lys Leu Asn Ala Met Leu Arg
            1025                1030                1035

Leu Gly Val Leu Gln Pro Glu Val Tyr Lys Gln Ser Leu Pro Gly
            1040                1045                1050

Ser Asn Cys Lys His Pro Glu Ile Lys Lys Gln Glu Tyr Glu Glu
            1055                1060                1065
```

```
Val Val Gln Thr Val Asn Thr Asp Phe Ser Pro Tyr Leu Ile Ser
    1070            1075             1080

Asp Asn Leu Glu Gln Pro Met Gly Ser Ser His Ala Ser Gln Val
    1085            1090             1095

Cys Ser Glu Thr Pro Asp Asp Leu Leu Asp Asp Gly Glu Ile Lys
    1100            1105             1110

Glu Asp Thr Ser Phe Ala Glu Asn Asp Ile Lys Glu Ser Ser Ala
    1115            1120             1125

Val Phe Ser Lys Ser Val Gln Lys Gly Glu Leu Ser Arg Ser Pro
    1130            1135             1140

Ser Pro Phe Thr His Thr His Leu Ala Gln Gly Tyr Arg Arg Gly
    1145            1150             1155

Ala Lys Lys Leu Glu Ser Ser Glu Glu Asn Leu Ser Ser Glu Asp
    1160            1165             1170

Glu Glu Leu Pro Cys Phe Gln His Leu Leu Phe Gly Lys Val Asn
    1175            1180             1185

Asn Ile Pro Ser Gln Ser Thr Arg His Ser Thr Val Ala Thr Glu
    1190            1195             1200

Cys Leu Ser Lys Asn Thr Glu Glu Asn Leu Leu Ser Leu Lys Asn
    1205            1210             1215

Ser Leu Asn Asp Cys Ser Asn Gln Val Ile Leu Ala Lys Ala Ser
    1220            1225             1230

Gln Glu His His Leu Ser Glu Glu Thr Lys Cys Ser Ala Ser Leu
    1235            1240             1245

Phe Ser Ser Gln Cys Ser Glu Leu Glu Asp Leu Thr Ala Asn Thr
    1250            1255             1260

Asn Thr Gln Asp Pro Phe Leu Ile Gly Ser Ser Lys Gln Met Arg
    1265            1270             1275

His Gln Ser Glu Ser Gln Gly Val Gly Leu Ser Asp Lys Glu Leu
    1280            1285             1290

Val Ser Asp Asp Glu Glu Arg Gly Thr Gly Leu Glu Glu Asn Asn
    1295            1300             1305

Gln Glu Glu Gln Ser Met Asp Ser Asn Leu Gly Glu Ala Ala Ser
    1310            1315             1320

Gly Cys Glu Ser Glu Thr Ser Val Ser Glu Asp Cys Ser Gly Leu
    1325            1330             1335

Ser Ser Gln Ser Asp Ile Leu Thr Thr Gln Gln Arg Asp Thr Met
    1340            1345             1350

Gln His Asn Leu Ile Lys Leu Gln Gln Glu Met Ala Glu Leu Glu
    1355            1360             1365

Ala Val Leu Glu Gln His Gly Ser Gln Pro Ser Asn Ser Tyr Pro
    1370            1375             1380

Ser Ile Ile Ser Asp Ser Ser Ala Leu Glu Asp Leu Arg Asn Pro
    1385            1390             1395

Glu Gln Ser Thr Ser Glu Lys Ala Val Leu Thr Ser Gln Lys Ser
    1400            1405             1410

Ser Glu Tyr Pro Ile Ser Gln Asn Pro Glu Gly Leu Ser Ala Asp
    1415            1420             1425

Lys Phe Glu Val Ser Ala Asp Ser Ser Thr Ser Lys Asn Lys Glu
    1430            1435             1440

Pro Gly Val Glu Arg Ser Ser Pro Ser Lys Cys Pro Ser Leu Asp
    1445            1450             1455
```

```
Asp Arg Trp Tyr Met His Ser Cys Ser Gly Ser Leu Gln Asn Arg
    1460                1465                1470

Asn Tyr Pro Ser Gln Glu Glu Leu Ile Lys Val Val Asp Val Glu
    1475                1480                1485

Glu Gln Gln Leu Glu Glu Ser Gly Pro His Asp Leu Thr Glu Thr
    1490                1495                1500

Ser Tyr Leu Pro Arg Gln Asp Leu Glu Gly Thr Pro Tyr Leu Glu
    1505                1510                1515

Ser Gly Ile Ser Leu Phe Ser Asp Asp Pro Glu Ser Asp Pro Ser
    1520                1525                1530

Glu Asp Arg Ala Pro Glu Ser Ala Arg Val Gly Asn Ile Pro Ser
    1535                1540                1545

Ser Thr Ser Ala Leu Lys Val Pro Gln Leu Lys Val Ala Glu Ser
    1550                1555                1560

Ala Gln Ser Pro Ala Ala Ala His Thr Thr Asp Thr Ala Gly Tyr
    1565                1570                1575

Asn Ala Met Glu Glu Ser Val Ser Arg Glu Lys Pro Glu Leu Thr
    1580                1585                1590

Ala Ser Thr Glu Arg Val Asn Lys Arg Met Ser Met Val Val Ser
    1595                1600                1605

Gly Leu Thr Pro Glu Glu Phe Met Leu Val Tyr Lys Phe Ala Arg
    1610                1615                1620

Lys His His Ile Thr Leu Thr Asn Leu Ile Thr Glu Glu Thr Thr
    1625                1630                1635

His Val Val Met Lys Thr Asp Ala Glu Phe Val Cys Glu Arg Thr
    1640                1645                1650

Leu Lys Tyr Phe Leu Gly Ile Ala Gly Gly Lys Trp Val Val Ser
    1655                1660                1665

Tyr Phe Trp Val Thr Gln Ser Ile Lys Glu Arg Lys Met Leu Asn
    1670                1675                1680

Glu His Asp Phe Glu Val Arg Gly Asp Val Val Asn Gly Arg Asn
    1685                1690                1695

His Gln Gly Pro Lys Arg Ala Arg Glu Ser Gln Asp Arg Lys Ile
    1700                1705                1710

Phe Arg Gly Leu Glu Ile Cys Cys Tyr Gly Pro Phe Thr Asn Met
    1715                1720                1725

Pro Thr Asp Gln Leu Glu Trp Met Val Gln Leu Cys Gly Ala Ser
    1730                1735                1740

Val Val Lys Glu Leu Ser Ser Phe Thr Leu Gly Thr Gly Val His
    1745                1750                1755

Pro Ile Val Val Val Gln Pro Asp Ala Trp Thr Glu Asp Asn Gly
    1760                1765                1770

Phe His Ala Ile Gly Gln Met Cys Glu Ala Pro Val Val Thr Arg
    1775                1780                1785

Glu Trp Val Leu Asp Ser Val Ala Leu Tyr Gln Cys Gln Glu Leu
    1790                1795                1800

Asp Thr Tyr Leu Ile Pro Gln Ile Pro His Ser His Tyr
    1805                1810                1815

<210> SEQ ID NO 47
<211> LENGTH: 759
<212> TYPE: PRT
<213> ORGANISM: Homo sapiens

<400> SEQUENCE: 47
```

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Glu Ala Ala Ser Gly Cys Glu Ser Glu
            260                 265                 270

Thr Ser Val Ser Glu Asp Cys Ser Gly Leu Ser Ser Gln Ser Asp Ile
        275                 280                 285

Leu Thr Thr Gln Gln Arg Asp Thr Met Gln His Asn Leu Ile Lys Leu
290                 295                 300

Gln Gln Glu Met Ala Glu Leu Glu Ala Val Leu Glu Gln His Gly Ser
305                 310                 315                 320

Gln Pro Ser Asn Ser Tyr Pro Ser Ile Ile Ser Asp Ser Ser Ala Leu
                325                 330                 335

Glu Asp Leu Arg Asn Pro Glu Gln Ser Thr Ser Glu Lys Val Leu Thr
            340                 345                 350

Ser Gln Lys Ser Ser Glu Tyr Pro Ile Ser Gln Asn Pro Glu Gly Leu
        355                 360                 365

Ser Ala Asp Lys Phe Glu Val Ser Ala Asp Ser Ser Thr Ser Lys Asn
370                 375                 380

Lys Glu Pro Gly Val Glu Arg Ser Ser Pro Ser Lys Cys Pro Ser Leu
385                 390                 395                 400

Asp Asp Arg Trp Tyr Met His Ser Cys Ser Gly Ser Leu Gln Asn Arg
                405                 410                 415
```

Asn Tyr Pro Ser Gln Glu Leu Ile Lys Val Val Asp Val Glu Glu
            420                 425                 430

Gln Gln Leu Glu Glu Ser Gly Pro His Asp Leu Thr Glu Thr Ser Tyr
        435                 440                 445

Leu Pro Arg Gln Asp Leu Glu Gly Thr Pro Tyr Leu Glu Ser Gly Ile
450                 455                 460

Ser Leu Phe Ser Asp Asp Pro Glu Ser Asp Pro Ser Glu Asp Arg Ala
465                 470                 475                 480

Pro Glu Ser Ala Arg Val Gly Asn Ile Pro Ser Ser Thr Ser Ala Leu
                485                 490                 495

Lys Val Pro Gln Leu Lys Val Ala Glu Ser Ala Gln Ser Pro Ala Ala
            500                 505                 510

Ala His Thr Thr Asp Thr Ala Gly Tyr Asn Ala Met Glu Glu Ser Val
        515                 520                 525

Ser Arg Glu Lys Pro Glu Leu Thr Ala Ser Thr Glu Arg Val Asn Lys
        530                 535                 540

Arg Met Ser Met Val Val Ser Gly Leu Thr Pro Glu Glu Phe Met Leu
545                 550                 555                 560

Val Tyr Lys Phe Ala Arg Lys His His Ile Thr Leu Thr Asn Leu Ile
                565                 570                 575

Thr Glu Glu Thr Thr His Val Val Met Lys Thr Asp Ala Glu Phe Val
            580                 585                 590

Cys Glu Arg Thr Leu Lys Tyr Phe Leu Gly Ile Ala Gly Gly Lys Trp
        595                 600                 605

Val Val Ser Tyr Phe Trp Val Thr Gln Ser Ile Lys Glu Arg Lys Met
        610                 615                 620

Leu Asn Glu His Asp Phe Glu Val Arg Gly Asp Val Val Asn Gly Arg
625                 630                 635                 640

Asn His Gln Gly Pro Lys Arg Ala Arg Glu Ser Gln Asp Arg Lys Ile
                645                 650                 655

Phe Arg Gly Leu Glu Ile Cys Cys Tyr Gly Pro Phe Thr Asn Met Pro
            660                 665                 670

Thr Asp Gln Leu Glu Trp Met Val Gln Leu Cys Gly Ala Ser Val Val
        675                 680                 685

Lys Glu Leu Ser Ser Phe Thr Leu Gly Thr Gly Val His Pro Ile Val
        690                 695                 700

Val Val Gln Pro Asp Ala Trp Thr Glu Asp Asn Gly Phe His Ala Ile
705                 710                 715                 720

Gly Gln Met Cys Glu Ala Pro Val Val Thr Arg Glu Trp Val Leu Asp
                725                 730                 735

Ser Val Ala Leu Tyr Gln Cys Gln Glu Leu Asp Thr Tyr Leu Ile Pro
            740                 745                 750

Gln Ile Pro His Ser His Tyr
        755

<210> SEQ ID NO 48
<211> LENGTH: 699
<212> TYPE: PRT
<213> ORGANISM: Homo sapiens

<400> SEQUENCE: 48

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

-continued

```
Glu Pro Val Ser Thr Lys Cys Asp His Ile Phe Cys Lys Phe Cys Met
         35                  40                  45

Leu Lys Leu Leu Asn Gln Lys Lys Gly Pro Ser Gln Cys Pro Leu Cys
 50                  55                  60

Lys Asn Asp Ile Thr Lys Arg Ser Leu Gln Glu Ser Thr Arg Phe Ser
 65                  70                  75                  80

Gln Leu Val Glu Glu Leu Leu Lys Ile Ile Cys Ala Phe Gln Leu Asp
                 85                  90                  95

Thr Gly Leu Glu Tyr Ala Asn Ser Tyr Asn Phe Ala Lys Lys Glu Asn
                100                 105                 110

Asn Ser Pro Glu His Leu Lys Asp Glu Val Ser Ile Ile Gln Ser Met
                115                 120                 125

Gly Tyr Arg Asn Arg Ala Lys Arg Leu Leu Gln Ser Glu Pro Glu Asn
130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
                180                 185                 190

Lys Ala Thr Tyr Cys Ser Val Gly Asp Gln Glu Leu Leu Gln Ile Thr
                195                 200                 205

Pro Gln Gly Thr Arg Asp Glu Ile Ser Leu Asp Ser Ala Lys Lys Ala
                210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Glu Ala Ala Ser Gly Cys Glu Ser Glu
                260                 265                 270

Thr Ser Val Ser Glu Asp Cys Ser Gly Leu Ser Ser Gln Ser Asp Ile
                275                 280                 285

Leu Thr Thr Gln Gln Arg Asp Thr Met Gln His Asn Leu Ile Lys Leu
                290                 295                 300

Gln Gln Glu Met Ala Glu Leu Glu Ala Val Leu Glu Gln His Gly Ser
305                 310                 315                 320

Gln Pro Ser Asn Ser Tyr Pro Ser Ile Ile Ser Asp Ser Ser Ala Leu
                325                 330                 335

Glu Asp Leu Arg Asn Pro Glu Gln Ser Thr Ser Glu Lys Val Leu Thr
                340                 345                 350

Ser Gln Lys Ser Ser Glu Tyr Pro Ile Ser Gln Asn Pro Glu Gly Leu
                355                 360                 365

Ser Ala Asp Lys Phe Glu Val Ser Ala Asp Ser Ser Thr Ser Lys Asn
370                 375                 380

Lys Glu Pro Gly Val Glu Arg Ser Ser Pro Ser Lys Cys Pro Ser Leu
385                 390                 395                 400

Asp Asp Arg Trp Tyr Met His Ser Cys Ser Gly Ser Leu Gln Asn Arg
                405                 410                 415

Asn Tyr Pro Ser Gln Glu Glu Leu Ile Lys Val Val Asp Val Glu Glu
                420                 425                 430

Gln Gln Leu Glu Glu Ser Gly Pro His Asp Leu Thr Glu Thr Ser Tyr
                435                 440                 445
```

-continued

```
Leu Pro Arg Gln Asp Leu Glu Gly Thr Pro Tyr Leu Glu Ser Gly Ile
450                 455                 460

Ser Leu Phe Ser Asp Asp Pro Glu Ser Asp Pro Ser Glu Asp Arg Ala
465                 470                 475                 480

Pro Glu Ser Ala Arg Val Gly Asn Ile Pro Ser Ser Thr Ser Ala Leu
                485                 490                 495

Lys Val Pro Gln Leu Lys Val Ala Glu Ser Ala Gln Ser Pro Ala Ala
            500                 505                 510

Ala His Thr Thr Asp Thr Ala Gly Tyr Asn Ala Met Glu Glu Ser Val
                515                 520                 525

Ser Arg Glu Lys Pro Glu Leu Thr Ala Ser Thr Glu Arg Val Asn Lys
530                 535                 540

Arg Met Ser Met Val Val Ser Gly Leu Thr Pro Glu Glu Phe Met Leu
545                 550                 555                 560

Val Tyr Lys Phe Ala Arg Lys His His Ile Thr Leu Thr Asn Leu Ile
                565                 570                 575

Thr Glu Glu Thr Thr His Val Val Met Lys Thr Asp Ala Glu Phe Val
                580                 585                 590

Cys Glu Arg Thr Leu Lys Tyr Phe Leu Gly Ile Ala Gly Gly Lys Trp
            595                 600                 605

Val Val Ser Tyr Phe Trp Val Thr Gln Ser Ile Lys Glu Arg Lys Met
610                 615                 620

Leu Asn Glu His Asp Phe Glu Val Arg Gly Asp Val Val Asn Gly Arg
625                 630                 635                 640

Asn His Gln Gly Pro Lys Arg Ala Arg Glu Ser Gln Asp Arg Lys Ile
                645                 650                 655

Phe Arg Gly Leu Glu Ile Cys Cys Tyr Gly Pro Phe Thr Asn Met Pro
            660                 665                 670

Thr Gly Cys Pro Pro Asn Cys Gly Cys Ala Ala Arg Cys Leu Asp Arg
        675                 680                 685

Gly Gln Trp Leu Pro Cys Asn Trp Ala Asp Val
    690                 695

<210> SEQ ID NO 49
<211> LENGTH: 11386
<212> TYPE: DNA
<213> ORGANISM: Homo sapiens

<400> SEQUENCE: 49
gtggcgcgag cttctgaaac taggcggcag aggcggagcc gctgtggcac tgctgcgcct      60
ctgctgcgcc tcgggtgtct tttgcggcgg tgggtcgccg ccgggagaag cgtgagggga     120
cagatttgtg accggcgcgg tttttgtcag cttactccgg ccaaaaaaga actgcacctc     180
tggagcggac ttatttacca agcattggag gaatatcgta ggtaaaaatg cctattggat     240
ccaaagagag gccaacattt tttgaaattt ttaagacacg ctgcaacaaa gcagatttag     300
gaccaataag tcttaattgg tttgaagaac tttcttcaga agctccaccc tataattctg     360
aacctgcaga agaatctgaa cataaaaaca caattacga accaaaccta tttaaaactc      420
cacaaaggaa accatcttat aatcagctgg cttcaactcc aataatattc aaagagcaag     480
ggctgactct gccgctgtac caatctcctg taaagaatt agataaattc aaattagact      540
taggaaggaa tgttcccaat agtagacata aagtcttcg cacagtgaaa actaaaatgg     600
atcaagcaga tgatgtttcc tgtccacttc taaattcttg tcttagtgaa agtcctgttg     660
ttctacaatg tacacatgta acaccacaaa gagataagtc agtggtatgt gggagtttgt     720
```

```
ttcatacacc aaagtttgtg aagggtcgtc agacaccaaa acatatttct gaaagtctag    780
gagctgaggt ggatcctgat atgtcttggt caagttcttt agctacacca cccacccttta   840 gttctactgt gctcatagtc agaaatgaag aagcatctga aactgtattt cctcatgata    900
ctactgctaa tgtgaaaagc tattttttcca atcatgatga aagtctgaag aaaaatgata   960
gatttatcgc ttctgtgaca gacagtgaaa acacaaatca agagaagct gcaagtcatg    1020 gatttggaaa aacatcaggg aattcattta agtaaatag ctgcaaagac acattggaa     1080 agtcaatgcc aaatgtccta aagatgaag tatatgaaac agttgtagat acctctgaag    1140
aagatagttt ttcattatgt ttttctaaat gtagaacaaa aaatctacaa aaagtaagaa    1200
ctagcaagac taggaaaaaa attttccatg aagcaaacgc tgatgaatgt gaaaaatcta    1260 aaaccaagt gaaagaaaaa tactcatttg tatctgaagt ggaaccaaat gatactgatc     1320
cattagattc aaatgtagca aatcagaagc cctttgagag tggaagtgac aaaatctcca    1380
aggaagttgt accgtctttg gcctgtgaat ggtctcaact aacccttttca ggtctaaatg   1440 gagcccagat ggagaaaata cccctattgc atatttcttc atgtgaccaa atatttcag    1500 aaaaagacct attagacaca gagaacaaaa gaaagaaaga ttttcttact tcagagaatt   1560
ctttgccacg tatttctagc ctaccaaaat cagagaagcc attaaatgag gaaacagtgg   1620
taaataagag agatgaagag cagcatcttg aatctcatac agactgcatt cttgcagtaa   1680
agcaggcaat atctggaact tctccagtgg cttcttcatt tcagggtatc aaaaagtcta   1740
tattcagaat aagagaatca cctaaagaga ctttcaatgc aagttttttca ggtcatatga   1800 ctgatccaaa ctttaaaaaa gaaactgaag cctctgaaag tggactggaa atacatactg   1860
tttgctcaca gaaggaggac tccttatgtc caaatttaat tgataatgga agctggccag   1920
ccaccaccac acagaattct gtagctttga agaatgcagg tttaatatcc actttgaaaa   1980
agaaaacaaa taagtttatt tatgctatac atgatgaaac atcttataaa ggaaaaaaaa   2040
taccgaaaga ccaaaaatca gaactaatta actgttcagc ccagtttgaa gcaaatgctt   2100
ttgaagcacc acttacattt gcaaatgctg attcaggtttt attgcattct tctgtgaaaa  2160
gaagctgttc acagaatgat tctgaagaac caactttgtc cttaactagc tcttttggga   2220
caattctgag gaaatgttct agaaatgaaa catgttctaa taatacagta atctctcagg   2280
atcttgatta taaagaagca aaatgtaata aggaaaaact acagttattt attaccccag   2340
aagctgattc tctgtcatgc ctgcaggaag acagtgtga aaatgatcca aaaagcaaaa    2400
aagtttcaga tataaaagaa gaggtcttgg ctgcagcatg tcacccagta caacattcaa   2460
aagtggaata cagtgatact gactttcaat cccagaaaag tcttttatat gatcatgaaa   2520
atgccagcac tcttatttta actcctactt ccaaggatgt tctgtcaaac ctagtcatga   2580
tttctagagg caaagaatca tacaaaatgt cagacaagct caaaggtaac aattatgaat   2640
ctgatgttga attaaccaaa atattcccca tggaaaagaa tcaagatgta tgtgctttaa   2700
atgaaaatta taaaacgtt gagctgttgc cacctgaaaa atacatgaga gtagcatcac    2760
cttcaagaaa ggtacaattc aaccaaaaca caaatctaag agtaatccaa aaaaatcaag   2820
aagaaactac ttcaatttca aaaataactg tcaatccaga ctctgaagaa cttttctcag   2880
acaatgagaa taattttgtc ttccaagtag ctaatgaaag gaataatctt gctttaggaa   2940
atactaagga acttcatgaa acagacttga cttgtgtaaa cgaacccatt ttcaagaact   3000
ctaccatggt tttatatgga gacacaggtg ataaacaagc aacccaagtg tcaattaaaa   3060
```

```
aagatttggt ttatgttctt gcagaggaga acaaaaatag tgtaaagcag catataaaaa    3120
tgactctagg tcaagattta aaatcggaca tctccttgaa tatagataaa ataccagaaa    3180
aaaataatga ttacatgaac aaatgggcag gactcttagg tccaatttca aatcacagtt    3240
ttggaggtag cttcagaaca gcttcaaata aggaaatcaa gctctctgaa cataacatta    3300
agaagagcaa aatgttcttc aaagatattg aagaacaata tcctactagt ttagcttgtg    3360
ttgaaattgt aaataccttg gcattagata atcaaaagaa actgagcaag cctcagtcaa    3420
ttaatactgt atctgcacat ttacagagta gtgtagttgt ttctgattgt aaaaatagtc    3480
atataacccc tcagatgtta ttttccaagc aggattttaa ttcaaaccat aatttaacac    3540
ctagccaaaa ggcagaaatt acagaacttt ctactatatt agaagaatca ggaagtcagt    3600
ttgaatttac tcagtttaga aaaccaagct acatattgca gaagagtaca tttgaagtgc    3660
ctgaaaacca gatgactatc ttaaagacca cttctgagga atgcagagat gctgatcttc    3720
atgtcataat gaatgcccca tcgattggtc aggtagacag cagcaagcaa tttgaaggta    3780
cagttgaaat taaacggaag tttgctggcc tgttgaaaaa tgactgtaac aaaagtgctt    3840
ctggttattt aacagatgaa aatgaagtgg ggtttagggg cttttattct gctcatggca    3900
caaaactgaa tgtttctact gaagctctgc aaaaagctgt gaaactgttt agtgatattg    3960
agaatattag tgaggaaact tctgcagagg tacatccaat aagtttatct tcaagtaaat    4020
gtcatgattc tgttgtttca atgtttaaga tagaaaatca taatgataaa actgtaagtg    4080
aaaaaaataa taaatgccaa ctgatattac aaaataatat tgaaatgact actggcactt    4140
ttgttgaaga aattactgaa aattacaaga gaaatactga aaatgaagat aacaaatata    4200
ctgctgccag tagaaattct cataacttag aatttgatgg cagtgattca agtaaaaatg    4260
atactgtttg tattcataaa gatgaaacgg acttgctatt tactgatcag cacaacatat    4320
gtcttaaatt atctggccag tttatgaagg agggaaacac tcagattaaa aagatttgt     4380
cagatttaac ttttttggaa gttgcgaaag ctcaagaagc atgtcatggt aatacttcaa    4440
ataaagaaca gttaactgct actaaaacgg agcaaaatat aaaagatttt gagacttctg    4500
atacattttt tcagactgca agtgggaaaa atattagtgt cgccaaagag tcatttaata    4560
aaattgtaaa tttctttgat cagaaaccag aagaattgca taacttttcc ttaaattctg    4620
aattacattc tgcacataaga aagaacaaaa tggacattct aagttatgag gaaacagaca    4680
tagttaaaca caaaatactg aaagaaagtg tcccagttgg tactggaaat caactagtga    4740
ccttccaggg acaacccgaa cgtgatgaaa agatcaaaga acctactcta ttgggttttc    4800
atacagctag cgggaaaaaa gttaaaattg caaaggaatc tttggacaaa gtgaaaaacc    4860
tttttgatga aaaagagcaa ggtactagtg aaatcaccag ttttagccat caatgggcaa    4920
agaccctaaa gtacagagag gcctgtaaag accttgaatt agcatgtgag accattgaga    4980
tcacagctgc cccaaagtgt aaagaaatgc agaattctct caataatgat aaaaaccttg    5040
tttctattga gactgtggtg ccacctaagc tcttaagtga taatttatgt agacaaactg    5100
aaaatctcaa acatcaaaa agtatctttt tgaaagttaa agtacatgaa aatgtagaaa      5160
aagaaacagc aaaaagtcct gcaacttgtt acacaaatca gtcccctttat tcagtcattg    5220
aaaattcagc cttagctttt tacacaagtt gtagtagaaa aacttctgtg agtcagactt     5280
cattacttga agcaaaaaaa tggcttagag aaggaatatt tgatggtcaa ccagaaagaa    5340
taaatactgc agattatgta ggaaattatt tgtatgaaaa taattcaaac agtactatag     5400
ctgaaaatga caaaaatcat ctctccgaaa aacaagatac ttatttaagt aacagtagca    5460
```

-continued

| | |
|---|---|
| tgtctaacag ctattcctac cattctgatg aggtatataa tgattcagga tatctctcaa | 5520 |
| aaaataaact tgattctggt attgagccag tattgaagaa tgttgaagat caaaaaaaca | 5580 |
| ctagtttttc caaagtaata tccaatgtaa aagatgcaaa tgcataccca caaactgtaa | 5640 |
| atgaagatat ttgcgttgag gaacttgtga ctagctcttc accctgcaaa aataaaaatg | 5700 |
| cagccattaa attgtccata tctaatagta ataattttga ggtagggcca cctgcattta | 5760 |
| ggatagccag tggtaaaatc gtttgtgttt cacatgaaac aattaaaaaa gtgaaagaca | 5820 |
| tatttacaga cagtttcagt aaagtaatta aggaaaacaa cgagaataaa tcaaaaattt | 5880 |
| gccaaacgaa aattatggca ggttgttacg aggcattgga tgattcagag gatattcttc | 5940 |
| ataactctct agataatgat gaatgtagca cgcattcaca taaggttttt gctgacattc | 6000 |
| agagtgaaga aattttacaa cataaccaaa atatgtctgg attggagaaa gtttctaaaa | 6060 |
| tatcaccttg tgatgttagt ttggaaactt cagatatatg taaatgtagt atagggaagc | 6120 |
| ttcataagtc agtctcatct gcaaatactt gtgggatttt tagcacagca agtggaaaat | 6180 |
| ctgtccaggt atcagatgct tcattacaaa acgcaagaca agtgttttct gaaatagaag | 6240 |
| atagtaccaa gcaagtcttt tccaaagtat tgtttaaaag taacgaacat tcagaccagc | 6300 |
| tcacaagaga agaaaatact gctatacgta ctccagaaca tttaatatcc caaaaaggct | 6360 |
| tttcatataa tgtggtaaat tcatctgctt tctctggatt tagtacagca agtggaaagc | 6420 |
| aagtttccat tttagaaagt tccttacaca agttaaggg agtgttagag gaatttgatt | 6480 |
| taatcagaac tgagcatagt cttcactatt cacctacgtc tagacaaaat gtatcaaaaa | 6540 |
| tacttcctcg tgttgataag agaaacccag agcactgtgt aaactcagaa atggaaaaaa | 6600 |
| cctgcagtaa agaatttaaa ttatcaaata acttaaatgt tgaaggtggt tcttcagaaa | 6660 |
| ataatcactc tattaaagtt tctccatatc tctctcaatt tcaacaagac aaacaacagt | 6720 |
| tggtattagg aaccaaagtg tcacttgttg agaacattca tgttttggga aaagaacagg | 6780 |
| cttcacctaa aaacgtaaaa atggaaattg gtaaaactga aacttttttct gatgttcctg | 6840 |
| tgaaaacaaa tatagaagtt tgttctactt actccaaaga ttcagaaaac tactttgaaa | 6900 |
| cagaagcagt agaaattgct aaagcttta tggaagatga tgaactgaca gattctaaac | 6960 |
| tgccaagtca tgccacacat tctcttttta catgtcccga aaatgaggaa atggttttgt | 7020 |
| caaattcaag aattggaaaa agaagaggag agccccttat cttagtggga gaaccctcaa | 7080 |
| tcaaagaaa cttattaaat gaatttgaca ggataataga aaatcaagaa aaatccttaa | 7140 |
| aggcttcaaa aagcactcca gatggcacaa taaaagatcg aagattgttt atgcatcatg | 7200 |
| tttctttaga gccgattacc tgtgtaccct ttcgcacaac taaggaacgt caagagatac | 7260 |
| agaatccaaa ttttaccgca cctggtcaag aatttctgtc taaatctcat ttgtatgaac | 7320 |
| atctgacttt ggaaaaatct tcaagcaatt tagcagtttc aggacatcca ttttatcaag | 7380 |
| tttctgctac aagaaatgaa aaaatgagac acttgattac tacaggcaga ccaaccaaag | 7440 |
| tctttgttcc acctttaaa actaaatcac attttcacag agttgaacag tgtgttagga | 7500 |
| atattaactt ggaggaaaac agacaaaagc aaaacattga tggacatggc tctgatgata | 7560 |
| gtaaaaataa gattaatgac aatgagattc atcagtttaa caaaaacaac tccaatcaag | 7620 |
| cagcagctgt aactttcaca aagtgtgaag aagaaccttt agatttaatt acaagtcttc | 7680 |
| agaatgccag agatatacag gatatgcgaa ttaagaagaa acaaaggcaa cgcgtctttc | 7740 |
| cacagccagg cagtctgtat cttgcaaaaa catccactct gcctcgaatc tctctgaaag | 7800 |

-continued

```
cagcagtagg aggccaagtt ccctctgcgt gttctcataa acagctgtat acgtatggcg   7860
tttctaaaca ttgcataaaa attaacagca aaaatgcaga gtcttttcag tttcacactg   7920
aagattattt tggtaaggaa agtttatgga ctggaaaagg aatacagttg gctgatggtg   7980
gatggctcat accctccaat gatggaaagg ctggaaaaga agaattttat agggctctgt   8040
gtgacactcc aggtgtggat ccaaagctta tttctagaat ttgggtttat aatcactata   8100
gatggatcat atgaaactg gcagctatgg aatgtgcctt tcctaaggaa tttgctaata   8160
gatgcctaag cccagaaagg gtgcttcttc aactaaaata cagatatgat acggaaattg   8220
atagaagcag aagatcggct ataaaaaaga taatggaaag ggatgacaca gctgcaaaaa   8280
cacttgttct ctgtgtttct gacataattt cattgagcgc aaatatatct gaaacttcta   8340
gcaataaaac tagtagtgca gatacccaaa agtggccat tattgaactt acagatgggt   8400
ggtatgctgt taaggcccag ttagatcctc ccctcttagc tgtcttaaag aatggcagac   8460
tgacagttgg tcagaagatt attcttcatg gagcagaact ggtgggctct cctgatgcct   8520
gtacacctct tgaagcccca gaatctctta tgttaaagat ttctgctaac agtactcggc   8580
ctgctcgctg gtataccaaa cttggattct ttcctgaccc tagaccttt cctctgccct   8640 tatcatcgct tttcagtgat ggaggaaatg ttggttgtgt tgatgtaatt attcaaagag   8700 catacctat acagtggatg gagaagacat catctggatt atacatattt cgcaatgaaa   8760
gagaggaaga aaaggaagca gcaaaatatg tggaggccca acaaaagaga ctagaagcct   8820
tattcactaa aattcaggag gaatttgaag aacatgaaga aaacacaaca aaaccatatt   8880
taccatcacg tgcactaaca agacagcaag ttcgtgcttt gcaagatggt gcagagcttt   8940
atgaagcagt gaagaatgca gcagacccag cttaccttga gggttatttc agtgaagagc   9000
agttaagagc cttgaataat cacaggcaaa tgttgaatga taagaaacaa gctcagatcc   9060
agttggaaat taggaaggcc atggaatctg ctgaacaaaa ggaacaaggt ttatcaaggg   9120
atgtcacaac cgtgtggaag ttgcgtattg taagctattc aaaaaaagaa aaagattcag   9180
ttatactgag tatttggcgt ccatcatcag atttatattc tctgttaaca aaggaaaga   9240 gatacagaat ttatcatctt gcaacttcaa aatctaaaag taaatctgaa agagctaaca   9300
tacagttagc agcgacaaaa aaaactcagt atcaacaact accggtttca gatgaaattt   9360
tatttcagat ttaccagcca cgggagcccc ttcacttcag caattttta gatccagact   9420 ttcagccatc ttgttctgag gtggacctaa taggatttgt cgtttctgtt gtgaaaaaaa   9480
caggacttgc ccctttcgtc tatttgtcag acgaatgtta caatttactg gcaataaagt   9540
tttggataga ccttaatgag gacattatta agcctcatat gttaattgct gcaagcaacc   9600
tccagtggcg accagaatcc aaatcaggcc ttcttacttt atttgctgga gatttttctg   9660
tgttttctgc tagtccaaaa gagggccact ttcaagagac attcaacaaa atgaaaaata   9720
ctgttgagaa tattgacata ctttgcaatg aagcagaaaa caagcttatg catatactgc   9780
atgcaaatga tcccaagtgg tccacccaa ctaaagactg tacttcaggg ccgtacactg   9840
ctcaaatcat tcctggtaca ggaaacaagc ttctgatgtc ttctcctaat tgtgagatat   9900
attatcaaag tccttatca ctttgtatgg ccaaaggaa gtctgtttcc acctgtct   9960 cagcccagat gacttcaaag tcttgtaaag gggagaaaga gattgatgac caaaagaact   10020
gcaaaaagag aagagccttg gatttcttga gtagactgcc tttacctcca cctgttagtc   10080
ccatttgtac atttgtttct ccggctgcac agaaggcatt tcagccacca aggagttgtg   10140
gcaccaaata cgaaacaccc ataaagaaaa aagaactgaa ttctcctcag atgactccat   10200
```

-continued

```
ttaaaaaatt caatgaaatt tctcttttgg aaagtaattc aatagctgac gaagaacttg    10260
cattgataaa tacccaagct cttttgtctg gttcaacagg agaaaaacaa tttatatctg    10320
tcagtgaatc cactaggact gctcccacca gttcagaaga ttatctcaga ctgaaacgac    10380
gttgtactac atctctgatc aaagaacagg agagttccca ggccagtacg aagaatgtg     10440 agaaaaataa gcaggacaca attacaacta aaaatatat ctaagcattt gcaaaggcga     10500
caataaatta ttgacgctta acctttccag tttataagac tggaatataa tttcaaacca    10560
cacattagta cttatgttgc acaatgagaa aagaaattag tttcaaattt acctcagcgt    10620
ttgtgtatcg ggcaaaaatc gttttgcccg attccgtatt ggtatacttt tgcttcagtt    10680
gcatatctta aaactaaatg taatttatta actaatcaag aaaaacatct ttggctgagc    10740
tcggtggctc atgcctgtaa tcccaacact ttgagaagct gaggtgggag gagtgcttga    10800
ggccaggagt tcaagaccag cctgggcaac atagggagac ccccatcttt acaaagaaaa    10860
aaaaaagggg aaaagaaaat cttttaaatc tttggatttg atcactacaa gtattatttt    10920
acaagtgaaa taaacatacc attttctttt agattgtgtc attaaatgga atgaggtctc    10980
ttagtacagt tattttgatg cagataattc cttttagttt agctactatt ttaggggatt    11040 tttttagag gtaactcact atgaaatagt tctccttaat gcaaatatgt tggttctgct     11100
atagttccat cctgttcaaa agtcaggatg aatatgaaga gtggtgtttc cttttgagca    11160
attcttcatc cttaagtcag catgattata agaaaaatag aaccctcagt gtaactctaa    11220
ttccttttta ctattccagt gtgatctctg aaattaaatt acttcaacta aaaattcaaa    11280
tactttaaat cagaagattt catagttaat ttatttttt tttcaacaaa atggtcatcc     11340
aaactcaaac ttgagaaaat atcttgcttt caaattggca ctgatt                   11386
```

<210> SEQ ID NO 50
<211> LENGTH: 3418
<212> TYPE: PRT
<213> ORGANISM: Homo sapiens

<400> SEQUENCE: 50

| Met<br>1 | Pro | Ile | Gly | Ser<br>5 | Lys | Glu | Arg | Pro | Thr<br>10 | Phe | Phe | Glu | Ile | Phe<br>15 | Lys |
|---|---|---|---|---|---|---|---|---|---|---|---|---|---|---|---|
| Thr | Arg | Cys | Asn<br>20 | Lys | Ala | Asp | Leu | Gly<br>25 | Pro | Ile | Ser | Leu | Asn<br>30 | Trp | Phe |
| Glu | Glu | Leu<br>35 | Ser | Ser | Glu | Ala | Pro<br>40 | Pro | Tyr | Asn | Ser | Glu<br>45 | Pro | Ala | Glu |
| Glu | Ser<br>50 | Glu | His | Lys | Asn | Asn<br>55 | Asn | Tyr | Glu | Pro | Asn<br>60 | Leu | Phe | Lys | Thr |
| Pro<br>65 | Gln | Arg | Lys | Pro | Ser<br>70 | Tyr | Asn | Gln | Leu | Ala<br>75 | Ser | Thr | Pro | Ile | Ile<br>80 |
| Phe | Lys | Glu | Gln | Gly<br>85 | Leu | Thr | Leu | Pro | Leu<br>90 | Tyr | Gln | Ser | Pro | Val<br>95 | Lys |
| Glu | Leu | Asp | Lys<br>100 | Phe | Lys | Leu | Asp | Leu<br>105 | Gly | Arg | Asn | Val | Pro<br>110 | Asn | Ser |
| Arg | His | Lys<br>115 | Ser | Leu | Arg | Thr | Val<br>120 | Lys | Thr | Lys | Met | Asp<br>125 | Gln | Ala | Asp |
| Asp | Val<br>130 | Ser | Cys | Pro | Leu | Leu<br>135 | Asn | Ser | Cys | Leu | Ser<br>140 | Glu | Ser | Pro | Val |
| Val<br>145 | Leu | Gln | Cys | Thr | His<br>150 | Val | Thr | Pro | Gln | Arg<br>155 | Asp | Lys | Ser | Val | Val<br>160 |

-continued

```
Cys Gly Ser Leu Phe His Thr Pro Lys Phe Val Lys Gly Arg Gln Thr
            165                 170                 175
Pro Lys His Ile Ser Glu Ser Leu Gly Ala Glu Val Asp Pro Asp Met
        180                 185                 190
Ser Trp Ser Ser Ser Leu Ala Thr Pro Pro Thr Leu Ser Ser Thr Val
    195                 200                 205
Leu Ile Val Arg Asn Glu Glu Ala Ser Glu Thr Val Phe Pro His Asp
210                 215                 220
Thr Thr Ala Asn Val Lys Ser Tyr Phe Ser Asn His Asp Glu Ser Leu
225                 230                 235                 240
Lys Lys Asn Asp Arg Phe Ile Ala Ser Val Thr Asp Ser Glu Asn Thr
                245                 250                 255
Asn Gln Arg Glu Ala Ala Ser His Gly Phe Gly Lys Thr Ser Gly Asn
            260                 265                 270
Ser Phe Lys Val Asn Ser Cys Lys Asp His Ile Gly Lys Ser Met Pro
        275                 280                 285
Asn Val Leu Glu Asp Glu Val Tyr Glu Thr Val Val Asp Thr Ser Glu
    290                 295                 300
Glu Asp Ser Phe Ser Leu Cys Phe Ser Lys Cys Arg Thr Lys Asn Leu
305                 310                 315                 320
Gln Lys Val Arg Thr Ser Lys Thr Arg Lys Lys Ile Phe His Glu Ala
                325                 330                 335
Asn Ala Asp Glu Cys Glu Lys Ser Lys Asn Gln Val Lys Glu Lys Tyr
            340                 345                 350
Ser Phe Val Ser Glu Val Glu Pro Asn Asp Thr Asp Pro Leu Asp Ser
        355                 360                 365
Asn Val Ala Asn Gln Lys Pro Phe Glu Ser Gly Ser Asp Lys Ile Ser
    370                 375                 380
Lys Glu Val Val Pro Ser Leu Ala Cys Glu Trp Ser Gln Leu Thr Leu
385                 390                 395                 400
Ser Gly Leu Asn Gly Ala Gln Met Glu Lys Ile Pro Leu Leu His Ile
                405                 410                 415
Ser Ser Cys Asp Gln Asn Ile Ser Glu Lys Asp Leu Leu Asp Thr Glu
            420                 425                 430
Asn Lys Arg Lys Lys Asp Phe Leu Thr Ser Glu Asn Ser Leu Pro Arg
        435                 440                 445
Ile Ser Ser Leu Pro Lys Ser Glu Lys Pro Leu Asn Glu Glu Thr Val
    450                 455                 460
Val Asn Lys Arg Asp Glu Glu Gln His Leu Glu Ser His Thr Asp Cys
465                 470                 475                 480
Ile Leu Ala Val Lys Gln Ala Ile Ser Gly Thr Ser Pro Val Ala Ser
                485                 490                 495
Ser Phe Gln Gly Ile Lys Lys Ser Ile Phe Arg Ile Arg Glu Ser Pro
            500                 505                 510
Lys Glu Thr Phe Asn Ala Ser Phe Ser Gly His Met Thr Asp Pro Asn
        515                 520                 525
Phe Lys Lys Glu Thr Glu Ala Ser Glu Ser Gly Leu Glu Ile His Thr
    530                 535                 540
Val Cys Ser Gln Lys Glu Asp Ser Leu Cys Pro Asn Leu Ile Asp Asn
545                 550                 555                 560
Gly Ser Trp Pro Ala Thr Thr Thr Gln Asn Ser Val Ala Leu Lys Asn
                565                 570                 575
Ala Gly Leu Ile Ser Thr Leu Lys Lys Lys Thr Asn Lys Phe Ile Tyr
```

-continued

```
            580                 585                 590
Ala Ile His Asp Glu Thr Ser Tyr Lys Gly Lys Lys Ile Pro Lys Asp
                595                 600                 605

Gln Lys Ser Glu Leu Ile Asn Cys Ser Ala Gln Phe Glu Ala Asn Ala
        610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
                645                 650                 655

Leu Ser Leu Thr Ser Ser Phe Gly Thr Ile Leu Arg Lys Cys Ser Arg
            660                 665                 670

Asn Glu Thr Cys Ser Asn Asn Thr Val Ile Ser Gln Asp Leu Asp Tyr
        675                 680                 685

Lys Glu Ala Lys Cys Asn Lys Glu Lys Leu Gln Leu Phe Ile Thr Pro
    690                 695                 700

Glu Ala Asp Ser Leu Ser Cys Leu Gln Glu Gly Gln Cys Glu Asn Asp
705                 710                 715                 720

Pro Lys Ser Lys Lys Val Ser Asp Ile Lys Glu Val Leu Ala Ala
                725                 730                 735

Ala Cys His Pro Val Gln His Ser Lys Val Glu Tyr Ser Asp Thr Asp
            740                 745                 750

Phe Gln Ser Gln Lys Ser Leu Leu Tyr Asp His Glu Asn Ala Ser Thr
        755                 760                 765

Leu Ile Leu Thr Pro Thr Ser Lys Asp Val Leu Ser Asn Leu Val Met
    770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
                805                 810                 815

Lys Asn Gln Asp Val Cys Ala Leu Asn Glu Asn Tyr Lys Asn Val Glu
            820                 825                 830

Leu Leu Pro Pro Glu Lys Tyr Met Arg Val Ala Ser Pro Ser Arg Lys
        835                 840                 845

Val Gln Phe Asn Gln Asn Thr Asn Leu Arg Val Ile Gln Lys Asn Gln
    850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
                885                 890                 895

Glu Arg Asn Asn Leu Ala Leu Gly Asn Thr Lys Glu Leu His Glu Thr
            900                 905                 910

Asp Leu Thr Cys Val Asn Glu Pro Ile Phe Lys Asn Ser Thr Met Val
        915                 920                 925

Leu Tyr Gly Asp Thr Gly Asp Lys Gln Ala Thr Gln Val Ser Ile Lys
    930                 935                 940

Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
                965                 970                 975

Leu Asn Ile Asp Lys Ile Pro Glu Lys Asn Asn Asp Tyr Met Asn Lys
            980                 985                 990

Trp Ala Gly Leu Leu Gly Pro Ile Ser Asn His Ser Phe Gly Gly Ser
        995                 1000                1005
```

-continued

Phe Arg Thr Ala Ser Asn Lys Glu Ile Lys Leu Ser Glu His Asn
    1010            1015            1020

Ile Lys Lys Ser Lys Met Phe Phe Lys Asp Ile Glu Glu Gln Tyr
    1025            1030            1035

Pro Thr Ser Leu Ala Cys Val Glu Ile Val Asn Thr Leu Ala Leu
    1040            1045            1050

Asp Asn Gln Lys Lys Leu Ser Lys Pro Gln Ser Ile Asn Thr Val
    1055            1060            1065

Ser Ala His Leu Gln Ser Ser Val Val Val Ser Asp Cys Lys Asn
    1070            1075            1080

Ser His Ile Thr Pro Gln Met Leu Phe Ser Lys Gln Asp Phe Asn
    1085            1090            1095

Ser Asn His Asn Leu Thr Pro Ser Gln Lys Ala Glu Ile Thr Glu
    1100            1105            1110

Leu Ser Thr Ile Leu Glu Glu Ser Gly Ser Gln Phe Glu Phe Thr
    1115            1120            1125

Gln Phe Arg Lys Pro Ser Tyr Ile Leu Gln Lys Ser Thr Phe Glu
    1130            1135            1140

Val Pro Glu Asn Gln Met Thr Ile Leu Lys Thr Thr Ser Glu Glu
    1145            1150            1155

Cys Arg Asp Ala Asp Leu His Val Ile Met Asn Ala Pro Ser Ile
    1160            1165            1170

Gly Gln Val Asp Ser Ser Lys Gln Phe Glu Gly Thr Val Glu Ile
    1175            1180            1185

Lys Arg Lys Phe Ala Gly Leu Leu Lys Asn Asp Cys Asn Lys Ser
    1190            1195            1200

Ala Ser Gly Tyr Leu Thr Asp Glu Asn Glu Val Gly Phe Arg Gly
    1205            1210            1215

Phe Tyr Ser Ala His Gly Thr Lys Leu Asn Val Ser Thr Glu Ala
    1220            1225            1230

Leu Gln Lys Ala Val Lys Leu Phe Ser Asp Ile Glu Asn Ile Ser
    1235            1240            1245

Glu Glu Thr Ser Ala Glu Val His Pro Ile Ser Leu Ser Ser Ser
    1250            1255            1260

Lys Cys His Asp Ser Val Val Ser Met Phe Lys Ile Glu Asn His
    1265            1270            1275

Asn Asp Lys Thr Val Ser Glu Lys Asn Asn Lys Cys Gln Leu Ile
    1280            1285            1290

Leu Gln Asn Asn Ile Glu Met Thr Thr Gly Thr Phe Val Glu Glu
    1295            1300            1305

Ile Thr Glu Asn Tyr Lys Arg Asn Thr Glu Asn Glu Asp Asn Lys
    1310            1315            1320

Tyr Thr Ala Ala Ser Arg Asn Ser His Asn Leu Glu Phe Asp Gly
    1325            1330            1335

Ser Asp Ser Ser Lys Asn Asp Thr Val Cys Ile His Lys Asp Glu
    1340            1345            1350

Thr Asp Leu Leu Phe Thr Asp Gln His Asn Ile Cys Leu Lys Leu
    1355            1360            1365

Ser Gly Gln Phe Met Lys Glu Gly Asn Thr Gln Ile Lys Glu Asp
    1370            1375            1380

Leu Ser Asp Leu Thr Phe Leu Glu Val Ala Lys Ala Gln Glu Ala
    1385            1390            1395

```
Cys His Gly Asn Thr Ser Asn Lys Glu Gln Leu Thr Ala Thr Lys
1400                1405                1410

Thr Glu Gln Asn Ile Lys Asp Phe Glu Thr Ser Asp Thr Phe Phe
1415                1420                1425

Gln Thr Ala Ser Gly Lys Asn Ile Ser Val Ala Lys Glu Ser Phe
1430                1435                1440

Asn Lys Ile Val Asn Phe Phe Asp Gln Lys Pro Glu Glu Leu His
1445                1450                1455

Asn Phe Ser Leu Asn Ser Glu Leu His Ser Asp Ile Arg Lys Asn
1460                1465                1470

Lys Met Asp Ile Leu Ser Tyr Glu Glu Thr Asp Ile Val Lys His
1475                1480                1485

Lys Ile Leu Lys Glu Ser Val Pro Val Gly Thr Gly Asn Gln Leu
1490                1495                1500

Val Thr Phe Gln Gly Gln Pro Glu Arg Asp Glu Lys Ile Lys Glu
1505                1510                1515

Pro Thr Leu Leu Gly Phe His Thr Ala Ser Gly Lys Lys Val Lys
1520                1525                1530

Ile Ala Lys Glu Ser Leu Asp Lys Val Lys Asn Leu Phe Asp Glu
1535                1540                1545

Lys Glu Gln Gly Thr Ser Glu Ile Thr Ser Phe Ser His Gln Trp
1550                1555                1560

Ala Lys Thr Leu Lys Tyr Arg Glu Ala Cys Lys Asp Leu Glu Leu
1565                1570                1575

Ala Cys Glu Thr Ile Glu Ile Thr Ala Ala Pro Lys Cys Lys Glu
1580                1585                1590

Met Gln Asn Ser Leu Asn Asn Asp Lys Asn Leu Val Ser Ile Glu
1595                1600                1605

Thr Val Val Pro Pro Lys Leu Leu Ser Asp Asn Leu Cys Arg Gln
1610                1615                1620

Thr Glu Asn Leu Lys Thr Ser Lys Ser Ile Phe Leu Lys Val Lys
1625                1630                1635

Val His Glu Asn Val Glu Lys Glu Thr Ala Lys Ser Pro Ala Thr
1640                1645                1650

Cys Tyr Thr Asn Gln Ser Pro Tyr Ser Val Ile Glu Asn Ser Ala
1655                1660                1665

Leu Ala Phe Tyr Thr Ser Cys Ser Arg Lys Thr Ser Val Ser Gln
1670                1675                1680

Thr Ser Leu Leu Glu Ala Lys Lys Trp Leu Arg Glu Gly Ile Phe
1685                1690                1695

Asp Gly Gln Pro Glu Arg Ile Asn Thr Ala Asp Tyr Val Gly Asn
1700                1705                1710

Tyr Leu Tyr Glu Asn Asn Ser Asn Ser Thr Ile Ala Glu Asn Asp
1715                1720                1725

Lys Asn His Leu Ser Glu Lys Gln Asp Thr Tyr Leu Ser Asn Ser
1730                1735                1740

Ser Met Ser Asn Ser Tyr Ser Tyr His Ser Asp Glu Val Tyr Asn
1745                1750                1755

Asp Ser Gly Tyr Leu Ser Lys Asn Lys Leu Asp Ser Gly Ile Glu
1760                1765                1770

Pro Val Leu Lys Asn Val Glu Asp Gln Lys Asn Thr Ser Phe Ser
1775                1780                1785

Lys Val Ile Ser Asn Val Lys Asp Ala Asn Ala Tyr Pro Gln Thr
```

-continued

```
                     1790                1795                1800
        Val Asn Glu Asp Ile Cys Val Glu Glu Leu Val Thr Ser Ser Ser
            1805                1810                1815
        Pro Cys Lys Asn Lys Asn Ala Ala Ile Lys Leu Ser Ile Ser Asn
            1820                1825                1830
        Ser Asn Asn Phe Glu Val Gly Pro Pro Ala Phe Arg Ile Ala Ser
            1835                1840                1845
        Gly Lys Ile Val Cys Val Ser His Glu Thr Ile Lys Lys Val Lys
            1850                1855                1860
        Asp Ile Phe Thr Asp Ser Phe Ser Lys Val Ile Lys Glu Asn Asn
            1865                1870                1875
        Glu Asn Lys Ser Lys Ile Cys Gln Thr Lys Ile Met Ala Gly Cys
            1880                1885                1890
        Tyr Glu Ala Leu Asp Asp Ser Glu Asp Ile Leu His Asn Ser Leu
            1895                1900                1905
        Asp Asn Asp Glu Cys Ser Thr His Ser His Lys Val Phe Ala Asp
            1910                1915                1920
        Ile Gln Ser Glu Glu Ile Leu Gln His Asn Gln Asn Met Ser Gly
            1925                1930                1935
        Leu Glu Lys Val Ser Lys Ile Ser Pro Cys Asp Val Ser Leu Glu
            1940                1945                1950
        Thr Ser Asp Ile Cys Lys Cys Ser Ile Gly Lys Leu His Lys Ser
            1955                1960                1965
        Val Ser Ser Ala Asn Thr Cys Gly Ile Phe Ser Thr Ala Ser Gly
            1970                1975                1980
        Lys Ser Val Gln Val Ser Asp Ala Ser Leu Gln Asn Ala Arg Gln
            1985                1990                1995
        Val Phe Ser Glu Ile Glu Asp Ser Thr Lys Gln Val Phe Ser Lys
            2000                2005                2010
        Val Leu Phe Lys Ser Asn Glu His Ser Asp Gln Leu Thr Arg Glu
            2015                2020                2025
        Glu Asn Thr Ala Ile Arg Thr Pro Glu His Leu Ile Ser Gln Lys
            2030                2035                2040
        Gly Phe Ser Tyr Asn Val Val Asn Ser Ser Ala Phe Ser Gly Phe
            2045                2050                2055
        Ser Thr Ala Ser Gly Lys Gln Val Ser Ile Leu Glu Ser Ser Leu
            2060                2065                2070
        His Lys Val Lys Gly Val Leu Glu Glu Phe Asp Leu Ile Arg Thr
            2075                2080                2085
        Glu His Ser Leu His Tyr Ser Pro Thr Ser Arg Gln Asn Val Ser
            2090                2095                2100
        Lys Ile Leu Pro Arg Val Asp Lys Arg Asn Pro Glu His Cys Val
            2105                2110                2115
        Asn Ser Glu Met Glu Lys Thr Cys Ser Lys Glu Phe Lys Leu Ser
            2120                2125                2130
        Asn Asn Leu Asn Val Glu Gly Gly Ser Ser Glu Asn Asn His Ser
            2135                2140                2145
        Ile Lys Val Ser Pro Tyr Leu Ser Gln Phe Gln Gln Asp Lys Gln
            2150                2155                2160
        Gln Leu Val Leu Gly Thr Lys Val Ser Leu Val Glu Asn Ile His
            2165                2170                2175
        Val Leu Gly Lys Glu Gln Ala Ser Pro Lys Asn Val Lys Met Glu
            2180                2185                2190
```

-continued

```
Ile Gly Lys Thr Glu Thr Phe Ser Asp Val Pro Val Lys Thr Asn
2195                2200                2205

Ile Glu Val Cys Ser Thr Tyr Ser Lys Asp Ser Glu Asn Tyr Phe
2210                2215                2220

Glu Thr Glu Ala Val Glu Ile Ala Lys Ala Phe Met Glu Asp Asp
2225                2230                2235

Glu Leu Thr Asp Ser Lys Leu Pro Ser His Ala Thr His Ser Leu
2240                2245                2250

Phe Thr Cys Pro Glu Asn Glu Glu Met Val Leu Ser Asn Ser Arg
2255                2260                2265

Ile Gly Lys Arg Arg Gly Glu Pro Leu Ile Leu Val Gly Glu Pro
2270                2275                2280

Ser Ile Lys Arg Asn Leu Leu Asn Glu Phe Asp Arg Ile Ile Glu
2285                2290                2295

Asn Gln Glu Lys Ser Leu Lys Ala Ser Lys Ser Thr Pro Asp Gly
2300                2305                2310

Thr Ile Lys Asp Arg Arg Leu Phe Met His His Val Ser Leu Glu
2315                2320                2325

Pro Ile Thr Cys Val Pro Phe Arg Thr Thr Lys Glu Arg Gln Glu
2330                2335                2340

Ile Gln Asn Pro Asn Phe Thr Ala Pro Gly Gln Glu Phe Leu Ser
2345                2350                2355

Lys Ser His Leu Tyr Glu His Leu Thr Leu Glu Lys Ser Ser Ser
2360                2365                2370

Asn Leu Ala Val Ser Gly His Pro Phe Tyr Gln Val Ser Ala Thr
2375                2380                2385

Arg Asn Glu Lys Met Arg His Leu Ile Thr Thr Gly Arg Pro Thr
2390                2395                2400

Lys Val Phe Val Pro Pro Phe Lys Thr Lys Ser His Phe His Arg
2405                2410                2415

Val Glu Gln Cys Val Arg Asn Ile Asn Leu Glu Glu Asn Arg Gln
2420                2425                2430

Lys Gln Asn Ile Asp Gly His Gly Ser Asp Asp Ser Lys Asn Lys
2435                2440                2445

Ile Asn Asp Asn Glu Ile His Gln Phe Asn Lys Asn Asn Ser Asn
2450                2455                2460

Gln Ala Ala Ala Val Thr Phe Thr Lys Cys Glu Glu Glu Pro Leu
2465                2470                2475

Asp Leu Ile Thr Ser Leu Gln Asn Ala Arg Asp Ile Gln Asp Met
2480                2485                2490

Arg Ile Lys Lys Lys Gln Arg Gln Arg Val Phe Pro Gln Pro Gly
2495                2500                2505

Ser Leu Tyr Leu Ala Lys Thr Ser Thr Leu Pro Arg Ile Ser Leu
2510                2515                2520

Lys Ala Ala Val Gly Gly Gln Val Pro Ser Ala Cys Ser His Lys
2525                2530                2535

Gln Leu Tyr Thr Tyr Gly Val Ser Lys His Cys Ile Lys Ile Asn
2540                2545                2550

Ser Lys Asn Ala Glu Ser Phe Gln Phe His Thr Glu Asp Tyr Phe
2555                2560                2565

Gly Lys Glu Ser Leu Trp Thr Gly Lys Gly Ile Gln Leu Ala Asp
2570                2575                2580
```

| | | | | | | | | | | | |
|---|---|---|---|---|---|---|---|---|---|---|---|
| Gly | Gly | Trp | Leu | Ile | Pro | Ser | Asn | Asp | Gly | Lys | Ala | Gly | Lys | Glu |
| 2585 | | | | | 2590 | | | | | 2595 | | | | |
| Glu | Phe | Tyr | Arg | Ala | Leu | Cys | Asp | Thr | Pro | Gly | Val | Asp | Pro | Lys |
| 2600 | | | | | 2605 | | | | | 2610 | | | | |
| Leu | Ile | Ser | Arg | Ile | Trp | Val | Tyr | Asn | His | Tyr | Arg | Trp | Ile | Ile |
| 2615 | | | | | 2620 | | | | | 2625 | | | | |
| Trp | Lys | Leu | Ala | Ala | Met | Glu | Cys | Ala | Phe | Pro | Lys | Glu | Phe | Ala |
| 2630 | | | | | 2635 | | | | | 2640 | | | | |
| Asn | Arg | Cys | Leu | Ser | Pro | Glu | Arg | Val | Leu | Leu | Gln | Leu | Lys | Tyr |
| 2645 | | | | | 2650 | | | | | 2655 | | | | |
| Arg | Tyr | Asp | Thr | Glu | Ile | Asp | Arg | Ser | Arg | Arg | Ser | Ala | Ile | Lys |
| 2660 | | | | | 2665 | | | | | 2670 | | | | |
| Lys | Ile | Met | Glu | Arg | Asp | Asp | Thr | Ala | Ala | Lys | Thr | Leu | Val | Leu |
| 2675 | | | | | 2680 | | | | | 2685 | | | | |
| Cys | Val | Ser | Asp | Ile | Ile | Ser | Leu | Ser | Ala | Asn | Ile | Ser | Glu | Thr |
| 2690 | | | | | 2695 | | | | | 2700 | | | | |
| Ser | Ser | Asn | Lys | Thr | Ser | Ser | Ala | Asp | Thr | Gln | Lys | Val | Ala | Ile |
| 2705 | | | | | 2710 | | | | | 2715 | | | | |
| Ile | Glu | Leu | Thr | Asp | Gly | Trp | Tyr | Ala | Val | Lys | Ala | Gln | Leu | Asp |
| 2720 | | | | | 2725 | | | | | 2730 | | | | |
| Pro | Pro | Leu | Leu | Ala | Val | Leu | Lys | Asn | Gly | Arg | Leu | Thr | Val | Gly |
| 2735 | | | | | 2740 | | | | | 2745 | | | | |
| Gln | Lys | Ile | Ile | Leu | His | Gly | Ala | Glu | Leu | Val | Gly | Ser | Pro | Asp |
| 2750 | | | | | 2755 | | | | | 2760 | | | | |
| Ala | Cys | Thr | Pro | Leu | Glu | Ala | Pro | Glu | Ser | Leu | Met | Leu | Lys | Ile |
| 2765 | | | | | 2770 | | | | | 2775 | | | | |
| Ser | Ala | Asn | Ser | Thr | Arg | Pro | Ala | Arg | Trp | Tyr | Thr | Lys | Leu | Gly |
| 2780 | | | | | 2785 | | | | | 2790 | | | | |
| Phe | Phe | Pro | Asp | Pro | Arg | Pro | Phe | Pro | Leu | Pro | Leu | Ser | Ser | Leu |
| 2795 | | | | | 2800 | | | | | 2805 | | | | |
| Phe | Ser | Asp | Gly | Gly | Asn | Val | Gly | Cys | Val | Asp | Val | Ile | Ile | Gln |
| 2810 | | | | | 2815 | | | | | 2820 | | | | |
| Arg | Ala | Tyr | Pro | Ile | Gln | Trp | Met | Glu | Lys | Thr | Ser | Ser | Gly | Leu |
| 2825 | | | | | 2830 | | | | | 2835 | | | | |
| Tyr | Ile | Phe | Arg | Asn | Glu | Arg | Glu | Glu | Glu | Lys | Glu | Ala | Ala | Lys |
| 2840 | | | | | 2845 | | | | | 2850 | | | | |
| Tyr | Val | Glu | Ala | Gln | Gln | Lys | Arg | Leu | Glu | Ala | Leu | Phe | Thr | Lys |
| 2855 | | | | | 2860 | | | | | 2865 | | | | |
| Ile | Gln | Glu | Glu | Phe | Glu | Glu | His | Glu | Glu | Asn | Thr | Thr | Lys | Pro |
| 2870 | | | | | 2875 | | | | | 2880 | | | | |
| Tyr | Leu | Pro | Ser | Arg | Ala | Leu | Thr | Arg | Gln | Gln | Val | Arg | Ala | Leu |
| 2885 | | | | | 2890 | | | | | 2895 | | | | |
| Gln | Asp | Gly | Ala | Glu | Leu | Tyr | Glu | Ala | Val | Lys | Asn | Ala | Ala | Asp |
| 2900 | | | | | 2905 | | | | | 2910 | | | | |
| Pro | Ala | Tyr | Leu | Glu | Gly | Tyr | Phe | Ser | Glu | Glu | Gln | Leu | Arg | Ala |
| 2915 | | | | | 2920 | | | | | 2925 | | | | |
| Leu | Asn | Asn | His | Arg | Gln | Met | Leu | Asn | Asp | Lys | Lys | Gln | Ala | Gln |
| 2930 | | | | | 2935 | | | | | 2940 | | | | |
| Ile | Gln | Leu | Glu | Ile | Arg | Lys | Ala | Met | Glu | Ser | Ala | Glu | Gln | Lys |
| 2945 | | | | | 2950 | | | | | 2955 | | | | |
| Glu | Gln | Gly | Leu | Ser | Arg | Asp | Val | Thr | Thr | Val | Trp | Lys | Leu | Arg |
| 2960 | | | | | 2965 | | | | | 2970 | | | | |
| Ile | Val | Ser | Tyr | Ser | Lys | Lys | Glu | Lys | Asp | Ser | Val | Ile | Leu | Ser |

-continued

```
             2975                2980                2985

Ile Trp  Arg Pro Ser Ser  Asp Leu Tyr Ser  Leu Leu Thr Glu Gly
       2990                2995                3000

Lys Arg  Tyr Arg Ile Tyr  His Leu Ala Thr  Ser Lys Ser Lys Ser
       3005                3010                3015

Lys Ser  Glu Arg Ala Asn  Ile Gln Leu Ala  Ala Thr Lys Lys Thr
       3020                3025                3030

Gln Tyr  Gln Gln Leu Pro  Val Ser Asp Glu  Ile Leu Phe Gln Ile
       3035                3040                3045

Tyr Gln  Pro Arg Glu Pro  Leu His Phe Ser  Lys Phe Leu Asp Pro
       3050                3055                3060

Asp Phe  Gln Pro Ser Cys  Ser Glu Val Asp  Leu Ile Gly Phe Val
       3065                3070                3075

Val Ser  Val Val Lys Lys  Thr Gly Leu Ala  Pro Phe Val Tyr Leu
       3080                3085                3090

Ser Asp  Glu Cys Tyr Asn  Leu Leu Ala Ile  Lys Phe Trp Ile Asp
       3095                3100                3105

Leu Asn  Glu Asp Ile Ile  Lys Pro His Met  Leu Ile Ala Ala Ser
       3110                3115                3120

Asn Leu  Gln Trp Arg Pro  Glu Ser Lys Ser  Gly Leu Leu Thr Leu
       3125                3130                3135

Phe Ala  Gly Asp Phe Ser  Val Phe Ser Ala  Ser Pro Lys Glu Gly
       3140                3145                3150

His Phe  Gln Glu Thr Phe  Asn Lys Met Lys  Asn Thr Val Glu Asn
       3155                3160                3165

Ile Asp  Ile Leu Cys Asn  Glu Ala Glu Asn  Lys Leu Met His Ile
       3170                3175                3180

Leu His  Ala Asn Asp Pro  Lys Trp Ser Thr  Pro Thr Lys Asp Cys
       3185                3190                3195

Thr Ser  Gly Pro Tyr Thr  Ala Gln Ile Ile  Pro Gly Thr Gly Asn
       3200                3205                3210

Lys Leu  Leu Met Ser Ser  Pro Asn Cys Glu  Ile Tyr Tyr Gln Ser
       3215                3220                3225

Pro Leu  Ser Leu Cys Met  Ala Lys Arg Lys  Ser Val Ser Thr Pro
       3230                3235                3240

Val Ser  Ala Gln Met Thr  Ser Lys Ser Cys  Lys Gly Glu Lys Glu
       3245                3250                3255

Ile Asp  Asp Gln Lys Asn  Cys Lys Lys Arg  Arg Ala Leu Asp Phe
       3260                3265                3270

Leu Ser  Arg Leu Pro Leu  Pro Pro Pro Val  Ser Pro Ile Cys Thr
       3275                3280                3285

Phe Val  Ser Pro Ala Ala  Gln Lys Ala Phe  Gln Pro Pro Arg Ser
       3290                3295                3300

Cys Gly  Thr Lys Tyr Glu  Thr Pro Ile Lys  Lys Lys Glu Leu Asn
       3305                3310                3315

Ser Pro  Gln Met Thr Pro  Phe Lys Lys Phe  Asn Glu Ile Ser Leu
       3320                3325                3330

Leu Glu  Ser Asn Ser Ile  Ala Asp Glu Glu  Leu Ala Leu Ile Asn
       3335                3340                3345

Thr Gln  Ala Leu Leu Ser  Gly Ser Thr Gly  Glu Lys Gln Phe Ile
       3350                3355                3360

Ser Val  Ser Glu Ser Thr  Arg Thr Ala Pro  Thr Ser Ser Glu Asp
       3365                3370                3375
```

```
Tyr Leu Arg Leu Lys Arg Arg Cys Thr Thr Ser Leu Ile Lys Glu
    3380            3385                3390

Gln Glu Ser Ser Gln Ala Ser Thr Glu Glu Cys Glu Lys Asn Lys
    3395            3400                3405

Gln Asp Thr Ile Thr Thr Lys Lys Tyr Ile
    3410            3415

<210> SEQ ID NO 51
<211> LENGTH: 10661
<212> TYPE: DNA
<213> ORGANISM: Homo sapiens

<400> SEQUENCE: 51
cgagatcccg gggagccagc ttgctgggag agcgggacgg tccggagcaa gcccagaggc      60
agaggaggcg acagagggaa aaagggccga gctagccgct ccagtgctgt acaggagccg     120
aagggacgca ccacgccagc cccagcccgg ctccagcgac agccaacgcc tcttgcagcg     180
cggcggcttc gaagccgccg cccggagctg ccctttcctc ttcggtgaag ttttaaaag      240 ctgctaaaga ctcggaggaa gcaaggaaag tgcctggtag gactgacggc tgcctttgtc     300
ctcctcctct ccaccccgcc tcccccacce ctgccttccc ccctcccccc gtcttctctc     360
ccgcagctgc ctcagtcggc tactctcagc caacccccct caccaccctt ctccccaccc     420 gccccccgc ccccgtcggc ccagcgctgc cagcccgagt tgcagagag gtaactccct       480 ttggctgcga gcgggcgagc tagctgcaca ttgcaaagaa ggctcttagg agccaggcga     540
ctggggagcg gcttcagcac tgcagccacg acccgcctgg ttaggctgca cgcggagaga     600
accctctgtt ttcccccact ctctctccac ctcctcctgc cttccccacc ccgagtgcgg     660
agccagagat caaagatga aaaggcagtc aggtcttcag tagccaaaaa acaaaacaaa      720 caaaacaaa aaagccgaaa taaagaaaa agataataac tcagttctta tttgcaccta      780
cttcagtgga cactgaattt ggaaggtgga ggatttttgtt ttttctttt aagatctggg     840 catcttttga atctacccct caagtattaa gagacagact gtgagcctag cagggcagat     900
cttgtccacc gtgtgtcttc ttctgcacga gactttgagg ctgtcagagc gcttttttgcg   960 tggttgctcc cgcaagttc cttctctgga gcttcccgca ggtgggcagc tagctgcagc    1020
gactaccgca tcatcacagc ctgttgaact cttctgagca agagaagggg aggcggggta    1080
agggaagtag gtggaagatt cagccaagct caaggatgga agtgcagtta gggctgggaa    1140
gggtctaccc tcggccgccg tccaagacct accgaggagc tttccagaat ctgttccaga    1200
gcgtgcgcga agtgatccag aacccgggcc ccaggcaccc agaggccgcg agcgcagcac    1260
ctcccggcgc cagtttgctg ctgctgcagc agcagcagca gcagcagcag cagcagcagc    1320
agcagcagca gcagcagcag cagcagcagc agcaagagac tagccccagg cagcagcagc    1380
agcagcaggg tgaggatggt tctccccaag cccatcgtag aggccccaca ggctacctgg    1440
tcctggatga ggaacagcaa ccttcacagc cgcagtcggc cctggagtgc caccccgaga    1500
gaggttgcgt cccagagcct ggagccgccg tggccgccag caagggctg ccgcagcagc     1560 tgccagcacc tccggacgag gatgactcag ctgccccatc cacgttgtcc ctgctgggcc    1620
ccactttccc cggcttaagc agctgctccg ctgaccttaa agacatcctg agcgaggca    1680 gcaccatgca actccttcag caacagcagc aggaagcagt atccgaaggc agcagcagcg    1740
ggagagcgag ggaggcctcg ggggctccca cttcctccaa ggacaattac ttaggggca    1800 cttcgaccat ttctgacaac gccaaggagt tgtgtaaggc agtgtcggtg tccatgggcc    1860
```

-continued

```
tgggtgtgga ggcgttggag catctgagtc caggggaaca gcttcggggg gattgcatgt   1920
acgccccact tttgggagtt ccacccgctg tgcgtcccac tccttgtgcc ccattggccg   1980
aatgcaaagg ttctctgcta gacgacagcg caggcaagag cactgaagat actgctgagt   2040
attccccttt caaggaggt tacaccaaag gctagaagg cgagagccta ggctgctctg     2100
gcagcgctgc agcagggagc tccgggacac ttgaactgcc gtctaccctg tctctctaca   2160
agtccggagc actggacgag gcagctgcgt accagagtcg cgactactac aactttccac   2220
tggctctggc cggaccgccg cccctccgc cgcctcccca tccccacgct cgcatcaagc    2280
tggagaaccc gctggactac ggcagcgcct gggcggctgc ggcggcgcag tgccgctatg   2340
gggacctggc gagcctgcat ggcgcgggtg cagcgggacc cggttctggg tcaccctcag   2400
ccgccgcttc ctcatcctgg cacactctct tcacagccga agaaggccag ttgtatggac   2460
cgtgtggtgg tggtgggggt ggtggcggcg gcggcggcgg cggcggcggc ggcggcggcg   2520
gcggcggcgg cggcgaggcg ggagctgtag cccctacgg ctacactcgg cccctcagg    2580
ggctggcggg ccaggaaagc gacttcaccg cacctgatgt gtggtaccct ggcggcatgg   2640
tgagcagagt gccctatccc agtcccactt gtgtcaaaag cgaaatgggc cctggatgg    2700
atagctactc cggaccttac ggggacatgc gtttggagac tgccagggac catgttttgc   2760
ccattgacta ttactttcca ccccagaaga cctgcctgat ctgtggagat gaagcttctg   2820
ggtgtcacta tggagctctc acatgtggaa gctgcaaggt cttcttcaaa agagccgctg   2880
aagggaaaca gaagtacctg tgcgccagca gaaatgattg cactattgat aaattccgaa   2940
ggaaaaattg tccatcttgt cgtcttcgga atgttatga agcagggatg actctgggag    3000
cccggaagct gaagaaactt ggtaatctga aactacagga ggaaggagag gcttccagca   3060
ccaccagccc cactgaggag acaacccaga agctgacagt gtcacacatt gaaggctatg   3120
aatgtcagcc catcttttctg aatgtcctgg aagccattga gccaggtgta gtgtgtgctg  3180
gacacgacaa caaccagccc gactcctttg cagccttgct ctctagcctc aatgaactgg   3240
gagagagaca gcttgtacac gtggtcaagt gggccaaggc cttgcctggc ttccgcaact   3300
tacacgtgga cgaccagatg gctgtcattc agtactcctg gatggggctc atggtgtttg   3360
ccatgggctg gcgatccttc accaatgtca actccaggat gctctacttc gcccctgatc   3420
tggttttcaa tgagtaccgc atgcacaagt cccggatgta cagccagtgt gtccgaatga   3480
ggcacctctc tcaagagttt ggatggctcc aaatcacccc ccaggaattc ctgtgcatga   3540
aagcactgct actcttcagc attattccag tggatgggag gaaaaatcaa aaattctttg   3600
atgaacttcg aatgaactac atcaaggaac tcgatcgtat cattgcatgc aaaagaaaaa   3660
atcccacatc ctgctcaaga cgcttctacc agctcaccaa gctcctggac tccgtgcagc   3720
ctattgcgag agagctgcat cagttcactt ttgacctgct aatcaagtca cacatggtga   3780
gcgtggactt tccggaaatg atggcagaga tcatctctgt gcaagtgccc aagatccttt   3840
ctgggaaagt caagcccatc tatttccaca cccagtgaag cattggaaac cctatttccc   3900
cacccccagct catgccccct ttcagatgtc ttctgcctgt tataactctg cactactcct  3960
ctgcagtgcc ttggggaatt tcctctattg atgtacagtc tgtcatgaac atgttcctga   4020
attctatttg ctgggctttt tttttctctt tctctccttt cttttttcttc ttccctccct   4080
atctaaccct cccatggcac cttcagactt tgcttcccat tgtggctcct atctgtgttt   4140
tgaatggtgt tgtatgcctt taaatctgtg atgatcctca tatggcccag tgtcaagttg   4200
```

-continued

```
tgcttgttta cagcactact ctgtgccagc cacacaaacg tttacttatc ttatgccacg   4260
ggaagtttag agagctaaga ttatctgggg aaatcaaaac aaaaacaagc aaacaaaaaa   4320
aaaaagcaaa aacaaaacaa aaaataagcc aaaaaacctt gctagtgttt tttcctcaaa   4380
aataaataaa taaataaata aatacgtaca tacatacaca catacataca aacatataga   4440
aatccccaaa gaggccaata gtgacgagaa ggtgaaaatt gcaggcccat ggggagttac   4500 tgatttttc atctcctccc tccacgggag actttatttt ctgccaatgg ctattgccat   4560
tagagggcag agtgaccccca gagctgagtt gggcagggggg gtggacagag aggagaggac   4620
aaggagggca atggagcatc agtacctgcc cacagccttg gtccctgggg gctagactgc   4680
tcaactgtgg agcaattcat tatactgaaa atgtgcttgt tgttgaaaat ttgtctgcat   4740
gttaatgcct cacccccaaa ccctttttctc tctcactctc tgcctccaac ttcagattga   4800 cttttcaatag ttttttctaag acctttgaac tgaatgttct cttcagccaa aacttggcga   4860
cttccacaga aaagtctgac cactgagaag aaggagagca gagatttaac cctttgtaag   4920 gcccccatttg gatccaggtc tgctttctca tgtgtgagtc agggaggagc tggagccaga   4980
ggagaagaaa atgatagctt ggctgttctc ctgcttagga cactgactga atagttaaac   5040
tctcactgcc actacctttt ccccacccttt aaaagacctg aatgaagttt tctgccaaac   5100
tccgtgaagc cacaagcacc ttatgtcctc ccttcagtgt tttgtgggcc tgaatttcat   5160
cacactgcat ttcagccatg gtcatcaagc ctgtttgctt cttttgggca tgttcacaga   5220
ttctctgtta agagcccccca ccaccaagaa ggttagcagg ccaacagctc tgacatctat   5280
ctgtagatgc cagtagtcac aaagattcct taccaactct cagatcgctg gagcccttag   5340
acaaactgga agaaggcat caaagggatc aggcaagctg ggcgtcttgc ccttgtcccc   5400
cagagatgat accctcccag caagtggaga agttctcact tccttcttta gagcagctaa   5460
aggggctacc cagatcaggg ttgaagagaa aactcaatta ccagggtggg aagaatgaag   5520 gcactagaaac cagaaaccct gcaaatgctc ttccttgtcac ccagcatatc cacctgcaga   5580
agtcatgaga agagagaagg aacaaagagg agactctgac tactgaatta aaatcttcag   5640
cggcaaagcc taaagccaga tggacaccat ctggtgagtt tactcatcat cctcctctgc   5700
tgctgattct gggctctgac attgcccata ctcactcaga ttccccacct tgttgctgc    5760 ctcttagtca gagggaggcc aaaccattga gactttctac agaaccatgg cttctttcgg   5820
aaaggtctgg ttggtgtggc tccaatactt tgccacccat gaactcaggg tgtgccctgg   5880
gacactggtt ttatatagtc ttttggcaca cctgtgttct gttgacttcg ttcttcaagc   5940
ccaagtgcaa gggaaaatgt ccacctactt tctcatcttg gcctctgcct ccttacttag   6000
ctcttaatct catctgttga actcaagaaa tcaagggcca gtcatcaagc tgcccatttt   6060
aattgattca ctctgtttgt tgagaggata gtttctgagt gacatgatat gatccacaag   6120 ggttccttc cctgatttct gcattgatat taatagccaa acgaacttca aaacagcttt   6180
aaataacaag ggagagggga acctaagatg agtaatatgc caatccaaga ctgctggaga   6240
aaactaaagc tgacaggttc ccttttgggg gtgggataga catgttctgg ttttctttat   6300
tattacacaa tctggctcat gtacaggatc acttttagct gttttaaaca gaaaaaaata   6360
tccaccactc ttttcagtta cactaggtta cattttaata ggtcctttac atctgttttg   6420
gaatgatttt catcttttgt gatacacaga ttgaattata tcattttcat atctctcctt   6480
gtaaatacta gaagctctcc tttacattc tctatcaaat ttttcatctt tatgggtttc   6540
ccaattgtga ctcttgtctt catgaatata tgttttcat ttgcaaaagc caaaaatcag   6600
```

-continued

```
tgaaacagca gtgtaattaa aagcaacaac tggattactc caaatttcca aatgacaaaa    6660
ctagggaaaa atagcctaca caagccttta ggcctactct ttctgtgctt gggtttgagt    6720
gaacaaagga gattttagct tggctctgtt ctcccatgga tgaaaggagg aggattttt     6780 ttttcttttg gccattgatg ttctagccaa tgtaattgac agaagtctca ttttgcatgc    6840
gctctgctct acaaacagag ttggtatggt tggtatactg tactcacctg tgagggactg    6900
gccactcaga cccacttagc tggtgagcta agagatgagg atcactcact ggaaaagtca    6960
caaggaccat ctccaaacaa gttggcagtg ctcgatgtgg acgaagagtg aggaagagaa    7020
aaagaaggag caccagggag aaggctccgt ctgtgctggg cagcagacag ctgccaggat    7080
cacgaactct gtagtcaaag aaaagagtcg tgtggcagtt tcagctctcg ttcattgggc    7140
agctcgccta ggcccagcct ctgagctgac atgggagttg ttggattctt tgtttcatag    7200 cttttttctat gccataggca atattgttgt tcttggaaag tttattattt ttttaactcc    7260
cttactctga gaaagggata ttttgaagga ctgtcatata tctttgaaaa aagaaaatct    7320
gtaatacata tatttttatg tatgttcact ggcactaaaa aatatagaga gcttcattct    7380
gtcctttggg tagttgctga ggtaattgtc caggttgaaa ataatgtgc tgatgctaga     7440 gtccctctct gtccatactc tacttctaaa tacatatagg catacatagc aagttttatt    7500
tgacttgtac tttaagagaa aatatgtcca ccatccacat gatgcacaaa tgagctaaca    7560
ttgagcttca agtagcttct aagtgtttgt ttcattaggc acagcacaga tgtggccttt    7620
ccccccttct ctcccttgat atctggcagg gcataaaggc ccaggccact tcctctgccc    7680
cttcccagcc ctgcaccaaa gctgcatttc aggagactct ctccagacag cccagtaact    7740
acccgagcat ggcccctgca tagccctgga aaaataagag gctgactgtc tacgaattat    7800
cttgtgccag ttgcccaggt gagagggcac tgggccaagg gagtggtttt catgtttgac    7860
ccactacaag gggtcatggg aatcaggaat gccaaagcac cagatcaaat ccaaaactta    7920
aagtcaaaat aagccattca gcatgttcag tttcttggaa aaggaagttt ctaccctga    7980 tgcctttgta ggcagatctg ttctcaccat taatctttt gaaatctttt taaagcagtt    8040
tttaaaaaga gagatgaaag catcacatta tataaccaaa gattacattg tacctgctaa    8100
gataccaaaa ttcataaggg cagggggga gcaagcatta gtgcctcttt gataagctgt    8160
ccaaagacag actaaaggac tctgctggtg actgactatt aagagctttg tgggttttt    8220 tttccctaat aatatacatg tttagaagaa ttgaaaataa tttcgggaaa atgggattat    8280
gggtccttca ctaagtgatt ttataagcag aactggcttt ccttttctct agtagttgct    8340
gagcaaattg ttgaagctcc atcattgcat ggttggaaat ggagctgttc ttagccactg    8400
tgtttgctag tgcccatgtt agcttatctg aagatgtgaa acccttgctg ataagggagc    8460
atttaaagta ctagattttg cactagaggg acagcaggca gaaatcctta tttctgccca    8520
ctttggatgg cacaaaaagt tatctgcagt tgaaggcaga aagttgaaat acattgtaaa    8580
tgaatatttg tatccatgtt tcaaaattga aatatatata tatatatata tatatatata    8640
tatatatata tagtgtgtgt gtgtgttctg atagctttaa cttttctctgc atctttatat   8700 ttggttccag atcacacctg atgccatgta cttgtgagag aggatgcagt tttgttttgg    8760
aagctctctc agaacaaaca agacacctgg attgatcagt taactaaaag ttttctcccc    8820
tattgggttt gacccacagg tcctgtgaag gagcagaggg ataaaaagag tagaggacat    8880
gatacattgt actttactag ttcaagacag atgaatgtgg aaagcataaa aactcaatgg    8940
```

```
aactgactga gatttaccac agggaaggcc caaacttggg gccaaaagcc tacccaagtg    9000
attgaccagt ggcccccctaa tgggacctga gctgttggaa gaagagaact gttccttggt   9060
cttcaccatc cttgtgagag aagggcagtt tcctgcattg gaacctggag caagcgctct    9120
atctttcaca caaattccct cacctgagat tgaggtgctc ttgttactgg gtgtctgtgt    9180
gctgtaattc tggttttgga tatgttctgt aaagattttg acaaatgaaa atgtgttttt    9240
ctctgttaaa acttgtcaga gtactagaag ttgtatctct gtaggtgcag gtccatttct    9300
gcccacaggt agggtgtttt tctttgatta agagattgac acttctgttg cctaggacct    9360
cccaactcaa ccatttctag gtgaaggcag aaaaatccac attagttact cctcttcaga    9420
catttcagct gagataacaa atcttttgga attttttcac ccatagaaag agtggtagat    9480
atttgaattt gcaggtggga gtttcatagt aaaaacagct tttgactcag ctttgattta    9540
tcctcatttg atttggccag aaagtaggta atatgcattg attggcttct gattccaatt    9600
cagtatagca aggtgctagg ttttttcctt tccccacctg tctcttagcc tggggaatta    9660
aatgagaagc cttagaatgg gtggcccttg tgacctgaaa cacttcccac ataagctact    9720
taacaagatt gtcatggagc tgcagattcc attgcccacc aaagactaga acacacacat    9780
atccatacac caaaggaaag acaattctga atgctgtttt ctctggtggt tccctctctg    9840
gctgctgcct cacagtatgg gaacctgtac tctgcagagg tgacaggcca gatttgcatt    9900
atctcacaac cttagccctt ggtgctaact gtcctacagt gaagtgcctg gggggttgtc    9960
ctatcccata agccacttgg atgctgacag cagccaccat cagaatgacc cacgcaaaaa    10020
aaagaaaaaa aaaattaaaa agtcccctca caacccagtg cacctttct gctttcctct     10080 agactggaac attgattagg gagtgcctca gacatgacat tcttgtgctg tccttggaat    10140
taatctggca gcaggaggga gcagactatg taaacagaga taaaaattaa ttttcaatat    10200
tgaaggaaaa aagaaataag aagagagaga gaaagaaagc atcacacaaa gattttctta    10260
aaagaaacaa ttttgcttga aatctctttta gatggggctc attctcacg gtggcacttg     10320 gcctccactg ggcagcagga ccagctccaa gcgctagtgt tctgttctct ttttgtaatc    10380
ttggaatctt ttgttgctct aaatacaatt aaaaatggca gaaacttgtt tgttggacta    10440
catgtgtgac tttgggtctg tctctgcctc tgctttcaga aatgtcatcc attgtgtaaa    10500
atattggctt actggtctgc cagctaaaac ttggccacat cccctgttat ggctgcagga    10560
tcgagttatt gttaacaaag agacccaaga aaagctgcta atgtcctctt atcattgttg    10620
ttaatttgtt aaaacataaa gaatctaaa atttcaaaaa a                         10661
```

<210> SEQ ID NO 52
<211> LENGTH: 8112
<212> TYPE: DNA
<213> ORGANISM: Homo sapiens

<400> SEQUENCE: 52

```
gctgcgagca gagagggatt cctcggaggt catctgttcc atcttcttgc ctatgcaaat     60
gcctgcctga agctgctgga ggctggcttt gtaccggact ttgtacaggg aaccagggaa    120
acgaatgcag agtgctcctg acattgcctg tcacttttc ccatgatact ctggcttcac    180
agtttggaga ctgccaggga ccatgttttg cccattgact attactttcc accccagaag   240
acctgcctga tctgtggaga tgaagcttct gggtgtcact atggagctct cacatgtgga   300
agctgcaagg tcttcttcaa aagagccgct gaagggaaac agaagtacct gtgcgccagc   360
agaaatgatt gcactattga taaattccga aggaaaaatt gtccatcttg tcgtcttcgg   420
```

-continued

```
aaatgttatg aagcagggat gactctggga gcccggaagc tgaagaaact tggtaatctg      480
aaactacagg aggaaggaga ggcttccagc accaccagcc ccactgagga gacaacccag      540
aagctgacag tgtcacacat tgaaggctat gaatgtcagc ccatctttct gaatgtcctg      600
gaagccattg agccaggtgt agtgtgtgct ggacacgaca caaccagcc cgactccttt       660 gcagccttgc tctctagcct caatgaactg ggagagagac agcttgtaca cgtggtcaag      720
tgggccaagg ccttgcctgg cttccgcaac ttacacgtgg acgaccagat ggctgtcatt      780
cagtactcct ggatggggct catggtgttt gccatgggct ggcgatcctt caccaatgtc      840
aactccagga tgctctactt cgcccctgat ctggttttca atgagtaccg catgcacaag      900
tcccggatgt acagccagtg tgtccgaatg aggcacctct ctcaagagtt tggatggctc      960
caaatcaccc cccaggaatt cctgtgcatg aaagcactgc tactcttcag cattattcca     1020
gtggatgggc tgaaaaatca aaaattcttt gatgaacttc gaatgaacta catcaaggaa     1080
ctcgatcgta tcattgcatg caaaagaaaa atcccacat cctgctcaag acgcttctac      1140
cagctcacca agctcctgga ctccgtgcag cctattgcga gagagctgca tcagttcact     1200
tttgacctgc taatcaagtc acacatggtg agcgtggact ttccggaaat gatggcagag     1260
atcatctctg tgcaagtgcc caagatcctt tctgggaaag tcaagcccat ctatttccac     1320
acccagtgaa gcattggaaa ccctatttcc caccccagc tcatgccccc tttcagatgt      1380
cttctgcctg ttataactct gcactactcc tctgcagtgc cttggggaat ttcctctatt     1440
gatgtacagt ctgtcatgaa catgttcctg aattctattt gctgggcttt ttttttctct     1500
ttctctcctt tcttttctt cttccctccc tatctaaccc tcccatggca ccttcagact      1560
ttgcttccca ttgtggctcc tatctgtgtt ttgaatggtg ttgtatgcct ttaaatctgt     1620
gatgatcctc atatggccca gtgtcaagtt gtgcttgttt acagcactac tctgtgccag     1680
ccacacaaac gtttacttat cttatgccac gggaagttta gagagctaag attatctggg     1740
gaaatcaaaa caaaaacaag caaacaaaaa aaaaagcaa aaacaaaaca aaaataagc       1800 caaaaaccct tgctagtgtt ttttcctcaa aaataaataa ataaataaat aaatacgtac     1860
atacatacac acatacatac aaacatatag aaatccccaa agaggccaat agtgacgaga     1920
aggtgaaaat tgcaggccca tggggagtta ctgatttttt catctcctcc ctccacggga     1980
gactttattt tctgccaatg gctattgcca ttagagggca gagtgacccc agagctgagt     2040
tgggcagggg ggtggacaga gaggagagga caaggagggc aatggagcat cagtacctgc     2100
ccacagcctt ggtccctggg ggctagactg ctcaactgtg gagcaattca ttatactgaa     2160
aatgtgcttg ttgttgaaaa tttgtctgca tgttaatgcc tcaccccaa acccttttct      2220 ctctcactct ctgcctccaa cttcagattg actttcaata gttttctaa gacctttgaa      2280 ctgaatgttc tcttcagcca aaacttggcg acttccacag aaaagtctga ccactgagaa     2340
gaaggagagc agagatttaa ccctttgtaa ggcccatttt ggatccaggt ctgctttctc     2400
atgtgtgagt cagggaggag ctggagccag aggagaagaa aatgatagct tggctgttct     2460
cctgcttagg acactgactg aatagttaaa ctctcactgc cactaccttt tccccacctt     2520
taaaagacct gaatgaagtt ttctgccaaa ctccgtgaag ccacaagcac cttatgtcct     2580
cccttcagtg ttttgtgggc ctgaatttca tcacactgca tttcagccat ggtcatcaag     2640
cctgtttgct tcttttgggc atgttcacag attctctgtt aagagccccc accaccaaga     2700
aggttagcag gccaacagct ctgacatcta tctgtagatg ccagtagtca caaagatttc     2760
```

```
ttaccaactc tcagatcgct ggagcccttac gacaaactgg aaagaaggca tcaaagggat    2820
caggcaagct gggcgtcttg cccttgtccc ccagagatga taccctccca gcaagtggag    2880
aagttctcac ttccttcttt agagcagcta aaggggctac ccagatcagg gttgaagaga    2940
aaactcaatt accagggtgg gaagaatgaa ggcactagaa ccagaaaccc tgcaaatgct    3000
cttcttgtca cccagcatat ccacctgcag aagtcatgag aagagagaag gaacaaagag    3060
gagactctga ctactgaatt aaaatcttca gcggcaaagc ctaaagccag atggacacca    3120
tctggtgagt ttactcatca tcctcctctg ctgctgattc tgggctctga cattgcccat    3180
actcactcag attccccacc tttgttgctg cctcttagtc agagggaggc caaaccattg    3240
agactttcta cagaaccatg gcttctttcg gaaaggtctg gttggtgtgg ctccaatact    3300
ttgccaccca tgaactcagg gtgtgccctg ggacactggt tttatatagt cttttggcac    3360
acctgtgttc tgttgacttc gttcttcaag cccaagtgca agggaaaatg tccacctact    3420
ttctcatctt ggcctctgcc tccttactta gctcttaatc tcatctgttg aactcaagaa    3480
atcaagggcc agtcatcaag ctgcccattt taattgattc actctgtttg ttgagaggat    3540
agtttctgag tgacatgata tgatccacaa gggtttcctt ccctgatttc tgcattgata    3600
ttaatagcca aacgaacttc aaaacagctt taaataacaa gggagagggg aacctaagat    3660
gagtaatatg ccaatccaag actgctggag aaaactaaag ctgacaggtt cccttttggg    3720
ggtgggatag acatgttctg gttttctttta ttattacaca atctggctca tgtacaggat    3780 cactttagc tgttttaaac agaaaaaaat atccaccact cttttcagtt acactaggtt    3840
acattttaat aggtcccttta catctgtttt ggaatgattt tcatcttttg tgatacacag    3900
attgaattat atcattttca tatctctcct tgtaaatact agaagctctc ctttacattt    3960
ctctatcaaa ttttttcatct ttatgggttt cccaattgtg actcttgtct tcatgaatat    4020 atgttttca tttgcaaaag ccaaaaatca gtgaaacagc agtgtaatta aaagcaacaa    4080
ctggattact ccaaatttcc aaatgacaaa actagggaaa aatagcctac acaagccttt    4140
aggcctactc tttctgtgct tgggtttgag tgaacaaagg agattttagc ttggctctgt    4200
tctcccatgg atgaaaggag gaggattttt ttttcttttt ggccattgat gttctagcca    4260
atgtaattga cagaagtctc atttttgcatg cgctctgctc tacaaacaga gttggtatgg    4320
ttggtatact gtactcacct gtgagggact ggccactcag acccacttag ctggtgagct    4380
agaagatgag gatcactcac tggaaaagtc acaaggacca tctccaaaca agttggcagt    4440
gctcgatgtg gacgaagagt gaggaagaga aaagaaggga gcaccaggga gaaggctccg    4500
tctgtgctgg gcagcagaca gctgccagga tcacgaactc tgtagtcaaa gaaaagagtc    4560
gtgtggcagt ttcagctctc gttcattggg cagctcgcct aggcccagcc tctgagctga    4620
catgggagtt gttggattct tgtttcata gcttttttcta tgccataggc aatattgttg    4680
ttcttggaaa gtttattatt ttttttaactc ccttactctg agaaagggat attttgaagg    4740
actgtcatat atctttgaaa aaagaaaatc tgtaatacat atattttttat gtatgttcac    4800 tggcactaaa aaatatagag agcttcattc tgtcctttgg gtagttgctg aggtaattgt    4860
ccaggttgaa aaataatgtg ctgatgctag agtccctctc tgtccatact ctacttctaa    4920
atacatatag gcatacatag caagttttat ttgacttgta ctttaagaga aaatatgtcc    4980
accatccaca tgatgcacaa atgagctaac attgagcttc aagtagcttc taagtgtttg    5040
tttcattagg cacagcacag atgtggcctt tccccccttc tctcccttga tatctggcag    5100
ggcataaagg cccaggccac ttcctctgcc ccttcccagc cctgcaccaa agctgcattt    5160
```

-continued

```
caggagactc tctccagaca gcccagtaac tacccgagca tggcccctgc atagccctgg    5220
aaaaataaga ggctgactgt ctacgaatta tcttgtgcca gttgcccagg tgagagggca    5280
ctgggccaag ggagtggttt tcatgtttga cccactacaa ggggtcatgg gaatcaggaa    5340
tgccaaagca ccagatcaaa tccaaaactt aaagtcaaaa taagccattc agcatgttca    5400
gtttcttgga aaaggaagtt tctacccctg atgcctttgt aggcagatct gttctcacca    5460
ttaatctttt tgaaaatctt ttaaagcagt ttttaaaaag agagatgaaa gcatcacatt    5520
atataaccaa agattacatt gtacctgcta agataccaaa attcataagg gcaggggggg    5580
agcaagcatt agtgcctctt tgataagctg tccaaagaca gactaaagga ctctgctggt    5640
gactgactta aagagctttt gtgggttttt ttttcccctaa taatatacat gtttagaaga    5700
attgaaaata atttcgggaa aatgggatta tgggtccttc actaagtgat tttataagca    5760
gaactggctt tccttttctc tagtagttgc tgagcaaatt gttgaagctc catcattgca    5820
tggttggaaa tggagctgtt cttagccact gtgtttgcta gtgcccatgt tagcttatct    5880
gaagatgtga aacccttgct gataagggag catttaaagt actagatttt gcactagagg    5940
gacagcaggc agaaatcctt atttctgccc actttggatg gcacaaaaag ttatctgcag    6000
ttgaaggcag aaagttgaaa tacattgtaa atgaatattt gtatccatgt ttcaaaattg    6060
aaatatatat atatatatat atatatatat atatatatat atagtgtgtg tgtgtgttct    6120
gatagcttta actttctctg catctttata tttggttcca gatcacacct gatgccatgt    6180
acttgtgaga gaggatgcag ttttgttttg gaagctctct cagaacaaac aagacacctg    6240
gattgatcag ttaactaaaa gttttctccc ctattgggtt tgacccacag gtcctgtgaa    6300
ggagcagagg gataaaaaga gtagaggaca tgatacattg tactttacta gttcaagaca    6360
gatgaatgtg gaaagcataa aaactcaatg gaactgactg agatttacca cagggaaggc    6420
ccaaacttgg ggccaaaagc ctacccaagt gattgaccag tggccccta atgggacctg    6480 agctgttgga agaagagaac tgttccttgg tcttcaccat ccttgtgaga aagggcagt     6540 ttcctgcatt ggaacctgga gcaagcgctc tatctttcac acaaattccc tcacctgaga    6600
ttgaggtgct cttgttactg ggtgtctgtg tgctgtaatt ctggttttgg atatgttctg    6660
taaagatttt gacaaatgaa atgtgttttt tctctgttaa aacttgtcag agtactagaa    6720
gttgtatctc tgtaggtgca ggtccatttc tgcccacagg tagggtgttt ttctttgatt    6780
aagagattga cacttctgtt gcctaggacc tcccaactca accatttcta ggtgaaggca    6840
gaaaaatcca cattagttac tcctcttcag acatttcagc tgagataaca aatcttttgg    6900
aattttttca cccatagaaa gagtggtaga tatttgaatt tagcaggtgg agtttcatag    6960
taaaaacagc ttttgactca gctttgattt atcctcattt gatttggcca gaaagtaggt    7020
aatatgcatt gattggcttc tgattccaat tcagtatagc aaggtgctag gttttttcct    7080
ttccccacct gtctcttagc ctggggaatt aaatgagaag ccttagaatg ggtggccctt    7140
gtgacctgaa acacttccca cataagctac ttaacaagat tgtcatggag ctgcagattc    7200
cattgcccac caaagactag aacacacaca tatccataca ccaaaggaaa gacaattctg    7260
aaatgctgtt tctctggtgg ttccctctct ggctgctgcc tcacagtatg ggaacctgta    7320
ctctgcagag gtgacaggcc agatttgcat tatctcacaa ccttagccct tggtgctaac    7380
tgtcctacag tgaagtgcct gggggttgt cctatcccat aagccacttg gatgctgaca    7440
gcagccacca tcagaatgac ccacgcaaaa aaagaaaaa aaaattaaa aagtcccctc     7500
```

-continued

```
acaacccagt gacacctttc tgctttcctc tagactggaa cattgattag ggagtgcctc      7560
agacatgaca ttcttgtgct gtccttggaa ttaatctggc agcaggaggg agcagactat      7620
gtaaacagag ataaaaatta attttcaata ttgaaggaaa aagaaataa gaagagagag       7680 agaaagaaag catcacacaa agattttctt aaaagaaaca attttgcttg aaatctcttt      7740
agatggggct catttctcac ggtggcactt ggcctccact gggcagcagg accagctcca      7800
agcgctagtg ttctgttctc tttttgtaat cttggaatct tttgttgctc taaatacaat      7860
taaaaatggc agaaacttgt tgttggact acatgtgtga ctttgggtct gtctctgcct       7920
ctgctttcag aaatgtcatc cattgtgtaa aatattggct tactggtctg ccagctaaaa      7980
cttggccaca tcccctgtta tggctgcagg atcgagttat tgttaacaaa gagacccaag      8040
aaaagctgct aatgtcctct tatcattgtt gttaatttgt taaaacataa agaaatctaa      8100
aatttcaaaa aa                                                         8112
```

<210> SEQ ID NO 53
<211> LENGTH: 920
<212> TYPE: PRT
<213> ORGANISM: Homo sapiens

<400> SEQUENCE: 53

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
```

-continued

```
            260                 265                 270
Leu Gly Val Pro Pro Ala Val Arg Pro Thr Pro Cys Ala Pro Leu Ala
            275                 280                 285
Glu Cys Lys Gly Ser Leu Leu Asp Asp Ser Ala Gly Lys Ser Thr Glu
            290                 295                 300
Asp Thr Ala Glu Tyr Ser Pro Phe Lys Gly Tyr Thr Lys Gly Leu
305                 310                 315                 320
Glu Gly Glu Ser Leu Gly Cys Ser Gly Ser Ala Ala Gly Ser Ser
            325                 330                 335
Gly Thr Leu Glu Leu Pro Ser Thr Leu Ser Leu Tyr Lys Ser Gly Ala
            340                 345                 350
Leu Asp Glu Ala Ala Ala Tyr Gln Ser Arg Asp Tyr Asn Phe Pro
            355                 360                 365
Leu Ala Leu Ala Gly Pro Pro Pro Pro Pro Pro His Pro His
            370                 375                 380
Ala Arg Ile Lys Leu Glu Asn Pro Leu Asp Tyr Gly Ser Ala Trp Ala
385                 390                 395                 400
Ala Ala Ala Ala Gln Cys Arg Tyr Gly Asp Leu Ala Ser Leu His Gly
            405                 410                 415
Ala Gly Ala Ala Gly Pro Gly Ser Gly Ser Pro Ser Ala Ala Ala Ser
            420                 425                 430
Ser Ser Trp His Thr Leu Phe Thr Ala Glu Glu Gly Gln Leu Tyr Gly
            435                 440                 445
Pro Cys Gly Gly Gly Gly Gly Gly Gly Gly Gly Gly Gly Gly
            450                 455                 460
Gly Gly Gly Gly Gly Gly Gly Gly Glu Ala Gly Ala Val Ala Pro
465                 470                 475                 480
Tyr Gly Tyr Thr Arg Pro Pro Gln Gly Leu Ala Gly Gln Glu Ser Asp
            485                 490                 495
Phe Thr Ala Pro Asp Val Trp Tyr Pro Gly Gly Met Val Ser Arg Val
            500                 505                 510
Pro Tyr Pro Ser Pro Thr Cys Val Lys Ser Glu Met Gly Pro Trp Met
            515                 520                 525
Asp Ser Tyr Ser Gly Pro Tyr Gly Asp Met Arg Leu Glu Thr Ala Arg
            530                 535                 540
Asp His Val Leu Pro Ile Asp Tyr Tyr Phe Pro Pro Gln Lys Thr Cys
545                 550                 555                 560
Leu Ile Cys Gly Asp Glu Ala Ser Gly Cys His Tyr Gly Ala Leu Thr
            565                 570                 575
Cys Gly Ser Cys Lys Val Phe Phe Lys Arg Ala Ala Glu Gly Lys Gln
            580                 585                 590
Lys Tyr Leu Cys Ala Ser Arg Asn Asp Cys Thr Ile Asp Lys Phe Arg
            595                 600                 605
Arg Lys Asn Cys Pro Ser Cys Arg Leu Arg Lys Cys Tyr Glu Ala Gly
            610                 615                 620
Met Thr Leu Gly Ala Arg Lys Leu Lys Lys Leu Gly Asn Leu Lys Leu
625                 630                 635                 640
Gln Glu Glu Gly Glu Ala Ser Ser Thr Thr Ser Pro Thr Glu Glu Thr
            645                 650                 655
Thr Gln Lys Leu Thr Val Ser His Ile Glu Gly Tyr Glu Cys Gln Pro
            660                 665                 670
Ile Phe Leu Asn Val Leu Glu Ala Ile Glu Pro Gly Val Val Cys Ala
            675                 680                 685
```

```
Gly His Asp Asn Asn Gln Pro Asp Ser Phe Ala Ala Leu Leu Ser Ser
    690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
        755                 760                 765

Leu Val Phe Asn Glu Tyr Arg Met His Lys Ser Arg Met Tyr Ser Gln
770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
        835                 840                 845

Asn Pro Thr Ser Cys Ser Arg Arg Phe Tyr Gln Leu Thr Lys Leu Leu
850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920

<210> SEQ ID NO 54
<211> LENGTH: 388
<212> TYPE: PRT
<213> ORGANISM: Homo sapiens

<400> SEQUENCE: 54

Met Ile Leu Trp Leu His Ser Leu Glu Thr Ala Arg Asp His Val Leu
1               5                   10                  15

Pro Ile Asp Tyr Tyr Phe Pro Pro Gln Lys Thr Cys Leu Ile Cys Gly
            20                  25                  30

Asp Glu Ala Ser Gly Cys His Tyr Gly Ala Leu Thr Cys Gly Ser Cys
        35                  40                  45

Lys Val Phe Phe Lys Arg Ala Ala Glu Gly Lys Gln Lys Tyr Leu Cys
    50                  55                  60

Ala Ser Arg Asn Asp Cys Thr Ile Asp Lys Phe Arg Arg Lys Asn Cys
65                  70                  75                  80

Pro Ser Cys Arg Leu Arg Lys Cys Tyr Glu Ala Gly Met Thr Leu Gly
                85                  90                  95

Ala Arg Lys Leu Lys Lys Leu Gly Asn Leu Lys Leu Gln Glu Glu Gly
            100                 105                 110

Glu Ala Ser Ser Thr Thr Ser Pro Thr Glu Glu Thr Thr Gln Lys Leu
        115                 120                 125

Thr Val Ser His Ile Glu Gly Tyr Glu Cys Gln Pro Ile Phe Leu Asn
```

-continued

```
            130                 135                 140
Val Leu Glu Ala Ile Glu Pro Gly Val Val Cys Ala Gly His Asp Asn
145                 150                 155                 160

Asn Gln Pro Asp Ser Phe Ala Ala Leu Leu Ser Ser Leu Asn Glu Leu
                165                 170                 175

Gly Glu Arg Gln Leu Val His Val Val Lys Trp Ala Lys Ala Leu Pro
                180                 185                 190

Gly Phe Arg Asn Leu His Val Asp Asp Gln Met Ala Val Ile Gln Tyr
            195                 200                 205

Ser Trp Met Gly Leu Met Val Phe Ala Met Gly Trp Arg Ser Phe Thr
            210                 215                 220

Asn Val Asn Ser Arg Met Leu Tyr Phe Ala Pro Asp Leu Val Phe Asn
225                 230                 235                 240

Glu Tyr Arg Met His Lys Ser Arg Met Tyr Ser Gln Cys Val Arg Met
                245                 250                 255

Arg His Leu Ser Gln Glu Phe Gly Trp Leu Gln Ile Thr Pro Gln Glu
            260                 265                 270

Phe Leu Cys Met Lys Ala Leu Leu Leu Phe Ser Ile Ile Pro Val Asp
            275                 280                 285

Gly Leu Lys Asn Gln Lys Phe Phe Asp Glu Leu Arg Met Asn Tyr Ile
        290                 295                 300

Lys Glu Leu Asp Arg Ile Ile Ala Cys Lys Arg Lys Asn Pro Thr Ser
305                 310                 315                 320

Cys Ser Arg Arg Phe Tyr Gln Leu Thr Lys Leu Leu Asp Ser Val Gln
                325                 330                 335

Pro Ile Ala Arg Glu Leu His Gln Phe Thr Phe Asp Leu Leu Ile Lys
                340                 345                 350

Ser His Met Val Ser Val Asp Phe Pro Glu Met Met Ala Glu Ile Ile
            355                 360                 365

Ser Val Gln Val Pro Lys Ile Leu Ser Gly Lys Val Lys Pro Ile Tyr
        370                 375                 380

Phe His Thr Gln
385
```